(12) United States Patent
Esaki et al.

(10) Patent No.: US 9,487,517 B2
(45) Date of Patent: *Nov. 8, 2016

(54) SPIROIMIDAZOLONE DERIVATIVE

(71) Applicant: Chugai Seiyaku Kabushiki Kaisha, Kita-ku, Tokyo (JP)

(72) Inventors: Toru Esaki, Shizuoka (JP); Yoshikazu Nishimura, Shizuoka (JP); Yoshiaki Isshiki, Shizuoka (JP); Naoki Okamoto, Shizuoka (JP); Yoshiyuki Furuta, Shizuoka (JP); Akemi Mizutani, Shizuoka (JP); Masateru Ohta, Shizuoka (JP); Wayne Wen Lai, Wuxi (CN); Tomoya Kotake, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/857,005

(22) Filed: Sep. 17, 2015

(65) Prior Publication Data

US 2016/0016956 A1    Jan. 21, 2016

Related U.S. Application Data

(63) Continuation of application No. 13/266,517, filed as application No. PCT/JP2010/057432 on Apr. 27, 2010, now Pat. No. 9,169,254.

(30) Foreign Application Priority Data

Apr. 28, 2009 (JP) ................... 2009-109256

(51) Int. Cl.
| | |
|---|---|
| *C07D 471/10* | (2006.01) |
| *C07D 471/20* | (2006.01) |
| *C07D 491/107* | (2006.01) |
| *C07D 513/20* | (2006.01) |
| *C07D 513/22* | (2006.01) |
| *C07D 515/20* | (2006.01) |

(52) U.S. Cl.
CPC ........... *C07D 471/10* (2013.01); *C07D 471/20* (2013.01); *C07D 491/107* (2013.01); *C07D 513/20* (2013.01); *C07D 513/22* (2013.01); *C07D 515/20* (2013.01)

(58) Field of Classification Search
CPC ............ C07D 487/10; C07D 491/107; A61K 31/5377; A61K 31/4545
USPC .................................................... 546/20, 14
See application file for complete search history.

(56) References Cited

U.S. PATENT DOCUMENTS

| | | | |
|---|---|---|---|
| 7,666,892 B2 | 2/2010 | Eriksson et al. | |
| 7,981,904 B2 | 7/2011 | Chang et al. | |
| 8,476,286 B2 | 7/2013 | Beerli et al. | |
| 8,513,193 B2 | 8/2013 | Rosier et al. | |
| 9,169,254 B2 * | 10/2015 | Esaki .................. | C07D 471/10 |
| 2005/0101574 A1 | 5/2005 | Ishizuka et al. | |
| 2007/0099940 A1 | 5/2007 | Spearing | |
| 2007/0123548 A1 | 5/2007 | Cowan et al. | |
| 2012/0270838 A1 | 10/2012 | Esaki et al. | |
| 2015/0274727 A1 | 10/2015 | Nishimura et al. | |

FOREIGN PATENT DOCUMENTS

| | | |
|---|---|---|
| CN | 1516587 A | 7/2004 |
| EP | 1321141 A1 | 6/2003 |
| JP | 11-035470 A | 2/1999 |
| JP | 2004-523583 A | 8/2004 |
| JP | 2005-502605 A | 1/2005 |
| JP | 2007-522214 A | 8/2007 |
| JP | 2007-522215 A | 8/2007 |
| JP | 2008-515895 A | 5/2008 |
| WO | WO 00/35885 A1 | 6/2000 |
| WO | WO 02/17911 A1 | 3/2002 |
| WO | WO 02/074751 A1 | 9/2002 |
| WO | WO 02/102782 A2 | 12/2002 |
| WO | WO 2005/077918 A1 | 8/2005 |
| WO | WO 2005/077959 A1 | 8/2005 |
| WO | WO 2006/041830 A2 | 4/2006 |
| WO | WO 2007/135417 A1 | 11/2007 |
| WO | WO 2007/149873 A2 | 12/2007 |
| WO | WO 2008/148689 A1 | 12/2008 |
| WO | WO 2009/074575 A2 | 6/2009 |

OTHER PUBLICATIONS

Mittal et al., "Newer anabolic therapies in osteoporosis," Indian J. Endocrinol. Metab., Dec. 2012, 16(Supp2):S279-S281.
Rejnmark et al., "PTH replacement therapy of hypoparathyroidism," Osteoporos. Int., May 2013, epub Nov. 27, 2012, 24:1529-1536.
Rickard et al., "Intermittent treatment with parathyroid hormone (PTH) as well as a non-peptide small molecule agonist of the PTH1 receptor inhibits adipocyte differentiation in human bone marrow stromal cells," Bone, Dec. 2006, epub Aug. 10, 2006, 39(6):1361-1372.

(Continued)

*Primary Examiner* — Rita Desai
(74) *Attorney, Agent, or Firm* — Foley & Lardner LLP

(57) ABSTRACT

The present invention relates to a compound represented by the following formula (1):

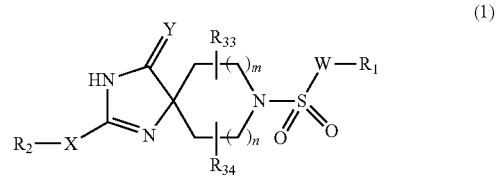

wherein W, X, Y, $R_1$, $R_2$, $R_{33}$, $R_{34}$, m and n are as defined in the claims, or a pharmacologically acceptable salt thereof.

7 Claims, No Drawings

(56) References Cited

OTHER PUBLICATIONS

Winer et al., "Long-Term Treatment of Hypoparathyroidism: A Randomized Controlled Study Comparing Parathyroid Hormone-(1-34) Versus Calcitriol and Calcium," The Journal of Clinical Endocrinology & Metabolism, Sep. 2003, 88(9):4214-4220.

Abou-Samra et al., "Expression cloning of a common receptor for parathyroid hormone and parathyroid hormone-related peptide from rat osteoblast-like cells: A single receptor stimulates intracellular accumulation of both cAMP and inositol trisphosphates and increases intracellular free calcium," Proc. Nat. Acad. Sci. USA, Apr. 1992, 89(7):2732-2736.

Bergwitz et al., "Full Activation of Chimeric Receptors by Hybrids between Parathyroid Hormone and Calcitonin," J. Biol. Chem., Oct. 25, 1996, 271(43):26469-26472.

Bringhurst et al., "Cloned, Stably Expressed Parathyroid Hormone (PTH)/PTH-Related Peptide Receptors Activate Multiple Messenger Signals and Biological Responses in LLC-$PK_1$ Kidney Cells," Endocrinology, May 1993, 132(5):2090-2098.

Broadus et al., "Parathyroid Hormone-Related Protein," The Parathyroids, J.P. Bilezikian et al., Eds., 1994, Chapter 17, 259-294.

Greenspan et al., "Effect of Recombinant Human Parathyroid Hormone (1-84) on Vertebral Fracture and Bone Mineral Density in Postmenopausal Women with Osteoporosis," Annals of Internal Medicine, Mar. 6, 2007, 146(5):326-339.

Hoare, Sam R.J., "Mechanisms of peptide and nonpeptide ligand binding to Class B G-protein-coupled receptors," Drug Discovery Today, Mar. 15, 2005, 10(6):417-427.

Ishihara et al., "Molecular cloning and expression of a cDNA encoding the secretin receptor," The EMBO Journal, Jul. 1991, 10(7):1635-1641.

Jelinek et al., "Expression Cloning and Signaling Properties of the Rat Glucagon Receptor," Science, Mar. 12, 1993, 259(5101):1614-1616.

Karaplis et al., "Letah skeletal dysplasia from targeted disruption of the parathyroid hormone-related peptide gene," Genes & Development, Feb. 1, 1994, 8(3):277-289.

Kolakowski, Lee F., Jr., "GCRDb: A G-Protein-Coupled Receptor Database," Receptors and Channels, 1994, 2(1):1-7.

Kronenberg et al,. "Parathyroid Hormone: Biosynthesis, Secretion, Chemistry, and Action," Handbook of Experimental Pharmacology: Physiology and Pharmacology of Bone, 1993, 507-567.

Lanske et al., "PTH/PTHrP Receptor in Early Development and Indian Hedgehog-Regulated Bone Growth," Science, Aug. 2, 1996, 273(5275):663-666.

Lin et al., "Expression Cloning of an Adenylate Cyclase-Coupled Calcitonin Receptor," Science, Nov. 15, 1991, 254(5034):1022-1024.

Neer et al., "Effect of Parathyroid Hormone (1-34) on Fractures and Bone Mineral Density in Postmenopausal Women with Osteoporosis," New England Journal of Medicine, May 10, 2001, 344(19):1434-1441.

Tashjian et al.,. "Perspective: Teriparatide [Human PTH(1-34)]: 2.5 Years of Experience on the Use and Safety of the Drug for the Treatment of Osteoporosis," Journal of Bone and Mineral Research, Mar. 2006, 21(3):354-365, Epub Nov. 11, 2005.

Urena et al., "Regulation of Parathyroid Hormone (PTH)/PTH-Related Peptide Receptor Messenger Ribonucleic Acid by Glucocorticoids and PTH in ROS 17/2.8 and OK Cells," Endocrinology, Jan. 1994, 134(1):451-456.

Usdin et al., "Identification and Functional Expression of a Receptor Selectively Recognizing Parathyroid Hormone, the PTH2 Receptor," J. Biol. Chem., Jun. 30, 1995, 270(26):15455-15458.

Cross et al., Cerebrovasodilatation through selective inhibition of the enzymes carbonic Anhydrase, 1978.

Patani et al., 1996, Bioisoterism.

Bleicher et al., "Parallel solution- and solid-phase synthesis of spirohydantoin derivatives as neurokinin-1 receptor ligands," CAplus, Chemical Abstracts, Mar. 24, 2003, 138(12):138:170128h.

Dörwald, Florencio Z., Side Reactions in Organic Synthesis, 2005, Wiley: VCH, Weinheim, p. IX of Preface.

\* cited by examiner

SPIROIMIDAZOLONE DERIVATIVE

CROSS-REFERENCE TO RELATED APPLICATIONS

This application is a Continuation of U.S. Ser. No. 13/266,517, which is the U.S. National Stage application of PCT/JP2010/057432, filed Apr. 27, 2010, which claims priority from Japanese application JP 2009-109256, filed Apr. 28, 2009.

TECHNICAL FIELD

The present invention relates to spiroimidazolone derivatives and use thereof.

BACKGROUND ART

Parathyroid hormone (PTH) is a major regulator of calcium homeostasis and its main target organs are considered to be the bones and kidneys. Native human parathyroid hormone is a polypeptide consisting of 84 amino acids. This hormone is secreted from the parathyroid gland in response to low blood calcium levels, and acts on osteoblasts (bone-building cells) in the bones and tubular epithelial cells in the kidneys. This hormone interacts with a cell surface receptor molecule called PTH-1 receptor or PTH/PTHrP receptor, which is expressed by both osteoblasts and renal tubular cells.

PTHrP (PTH-related protein), the major cause of humoral hypercalcemia of malignancy (HHM), also has normal functions including developmental roles. PTHrP has 141 amino acids, although mutants also occur that result from alternative gene splicing mechanisms. PTHrP plays a key role in the formation of the skeleton through a process that also involves binding to the PTH-1 receptor (Non Patent Literature 1, Non Patent Literature 2).

Regulation of calcium concentrations is necessary for normal functions of the gastrointestinal system, skeletal system, nervous system, neuromuscular system and cardiovascular system. Synthesis and release of PTH are primarily controlled by the serum calcium level. Synthesis and release of PTH are stimulated at low serum calcium levels, and synthesis and release of PTH are suppressed at high serum calcium levels. PTH, in turn, maintains the serum calcium level by directly or indirectly promoting calcium entry into the blood at three calcium exchange sites: intestine, bone and kidney. PTH contributes to net gastrointestinal absorption of calcium by assisting in the renal synthesis of active vitamin D. PTH promotes calcium mobilization from the bone to serum by stimulating differentiation of osteoclasts that are bone-resorbing cells. This also mediates at least three main effects in the kidney (stimulation of tubular calcium resorption; enhancement of phosphate clearance; and promotion of an increase in the enzyme that completes the synthesis of active vitamin D). PTH is considered to exert these effects primarily through receptor-mediated activation of adenylate cyclase and/or phospholipase C.

Disruption of calcium homeostasis may produce many clinical disorders (e.g., serious bone disease, anemia, renal dysfunction, ulcers, myopathy and neuropathy), and this usually results from conditions that produce an alteration in the level of parathyroid hormone. Hypercalcemia is a condition characterized by an elevated serum calcium level. This is often associated with primary hyperparathyroidism in which excessive PTH production occurs as a result of parathyroid gland lesions (e.g., adenoma, hyperplasia or carcinoma). Humoral hypercalcemia of malignancy (HHM), another type of hypercalcemia, is the most common paraneoplastic syndrome. This appears to result in most instances from the production of a certain protein hormone that shares amino acid homology with PTH by tumors (e.g., squamous cell carcinoma, renal carcinoma, ovarian carcinoma or bladder carcinoma). These PTHrPs appear to mimic the effects of PTH on the kidney and skeleton in some degree, and are considered to interact with the PTH receptor in these tissues. PTHrP is usually found at low levels in many tissues including keratinocytes, brain, pituitary gland, parathyroid gland, adrenal cortex, medulla, fetal liver, osteoblast-like cells and lactating mammary tissues. For many HHM malignant tumors, high levels of PTHrP are observed in the circulatory system, and this leads to elevated calcium levels associated with HHM.

The pharmacological profiles of PTH and PTHrP are nearly identical in most in vitro assay systems, and elevated blood levels of PTH (i.e., primary hyperparathyroidism) or PTHrP (i.e., HHM) have comparable effects on inorganic ion homeostasis (Non Patent Literature 3, Non Patent Literature 4). The similarities in the biological activities of the two ligands can be explained by their interaction with the PTH/PTHrP receptor, a common receptor expressed abundantly in the bones and kidneys (Non Patent Literature 5).

The PTH-1 receptor is homologous in primary structure to some other receptors binding to peptide hormones, such as secretin (Non Patent Literature 6), calcitonin (Non Patent Literature 7) and glucagon (Non Patent Literature 8); these receptors together form a distinct family called receptor family B (Non Patent Literature 9). Within this family, the PTH-1 receptor is unique in that it binds to two peptide ligands and thereby regulates two separate biological processes. A recently identified PTH receptor subtype called PTH-2 receptor binds to PTH but not to PTHrP (Non Patent Literature 10). This finding has implied that the structural differences in the PTH and PTHrP ligands determine the selectivity for interaction with the PTH-2 receptor. The PTH-2 receptor has been detected by RNA methods in the brain, pancreas and vasculature; however, its biological functions have not been determined (Non Patent Literature 10). The family B receptors are assumed to use a common molecular mechanism for engagement with their own cognate peptide hormone (Non Patent Literature 11).

The PTH-1 receptor binds to both PTH and PTHrP and causes not only intracellular cAMP accumulation and adenyl cyclase (AC) activation but also signal transduction to phospholipase C (PLC), thereby leading to the production of inositol trisphosphate (IP3), diacylglycerol (DAG) and intracellular calcium ($iCa^{2+}$) (Non Patent Literature 12, Non Patent Literature 13).

Osteoporosis is a potentially crippling bone disease and is observed in a substantial portion of the elderly population, in pregnant women and even in juveniles. The term "osteoporosis" refers to a group of disorders consisting of different constituents. Osteoporosis is clinically classified into type I and type II. Type I osteoporosis occurs primarily in middle-aged women and is associated with menopausal estrogen loss, while type II osteoporosis is associated with the elderly. Patients with osteoporosis are considered to benefit from novel therapies designed to promote fracture repair, or therapies designed to prevent or reduce fractures associated with the disease.

This disease is characterized by reduced bone mass, decreased bone mineral density (BMD), decreased bone strength and an increased risk of fracture. Currently, there is no effective cure for osteoporosis, although estrogen, calcitonin, and etidronate and alendronate that are bisphosphonates are used to treat the disease with various levels of success. These agents act to decrease bone resorption.

PTH(1-34) (teriparatide) has a strong bone anabolic effect and induces significant increases in bone mineral density and bone strength. Subcutaneous administration of human PTH(1-34) increased the spine bone mineral density (BMD) by 8% in one year and decreased the risks of vertebral fracture and nonvertebral fracture by 65% and 55% in two years, respectively (Non Patent Literature 14). Subcutaneous administration of human PTH(1-84) also increased the spine bone mineral density (BMD) by 6.9% in 18 months and decreased the risk of vertebral fracture by 58% (Non Patent Literature 15). Parathyroid hormone is currently believed to be one of the most effective treatments for osteoporosis (Non Patent Literature 16). Importantly, hPTH (1-34) must be administered in a pulsed manner (e.g., subcutaneous injection once daily) to achieve its bone-forming effect. Longer administration of PTH(1-34) such as by use of a continuous infusion pump mechanism activates bone-resorptive responses mediated by osteoclasts much stronger than bone-forming responses mediated by osteoblasts, and thus PTH(1-34) exerts a net degradation effect on the bone.

Although parathyroid hormone is believed to be one of the most effective treatments for osteoporosis, only less than 1% of patients with osteoporosis use teriparatide and the average duration of teriparatide is 12 months (Non Patent Literature 16). Teriparatide must be administered by self-injection. The fact that it is difficult to use a pen-type device for self-administration is the principal cause of the low compliance of teriparatide-administered patients. It is obvious that noninvasively, preferably orally, available compounds having a PTH-like effect with clinical efficacy in osteoporosis similar to that of parathyroid hormone can considerably improve the compliance of patients with regard to the administration, and that the compounds can be the most useful therapeutic option for patients with osteoporosis.

There are many low molecular weight agonists for the GPCR family A; however, only a limited number of low molecular weight ligands for the GPCR family B have been reported (Non Patent Literature 17). Low molecular weight agonists have been reported for the GLP-1 receptor, calcitonin receptor and PTH1 receptor belonging to the GPCR family B; however, there is no compound used in clinical applications for the treatment of diseases.

CITATION LIST

Non Patent Literature

[Non Patent Literature 1] Karaplis, A. C. et al., Genes and Dev. 8:277-289 (1994)
[Non Patent Literature 2] Lanske, B. et al., Science 273: 663-666 (1996)
[Non Patent Literature 3] Broadus, A. E. & Stewart, A. F., "Parathyroid hormone-related protein: Structure, processing and physiological actions," in Basic and Clinical Concepts, Bilzikian, J. P. et al., eds., Raven Press, New York (1994), pp. 259-294
[Non Patent Literature 4] Kronenberg, H. M. et al., "Parathyroid hormone: Biosynthesis, secretion, chemistry and action," in Handbook of Experimental Pharmacology, Mundy, G. R. & Martin, T. J., eds., Springer-Verlag, Heidelberg (1993), pp. 185-201
[Non Patent Literature 5] Urena, P. et al., Endocrinology 134:451-456 (1994)
[Non Patent Literature 6] Ishihara, T. et al., EMBO J. 10:1635-1641 (1991)
[Non Patent Literature 7] Lin, H. Y. et al., Science 254: 1022-1024 (1991)
[Non Patent Literature 8] Jelinek, L. J. et al., Science 259:1614-1616 (1993)
[Non Patent Literature 9] Kolakowski, L. F., Receptors and Channels 2:1-7 (1994)
[Non Patent Literature 10] Usdin, T. et al., J. Biol. Chem. 270:15455-15458 (1995)
[Non Patent Literature 11] Bergwitz, C. et al., J. Biol. Chem. 271:26469-26472 (1996)
[Non Patent Literature 12] Abou-Samra, A. B et al., Pro. Natl. Acad. Sci. USA, 89:2732-2736, 1992
[Non Patent Literature 13] Bringhurst F. R. et al., Endocrinology 132:2090-2098, 1993
[Non Patent Literature 14] Neer R M et al., N. Eng. J. Med. 344:1434-1441, 2003
[Non Patent Literature 15] Greenspan S L et al., Ann of Intern Med. 146:326-339, 2007
[Non Patent Literature 16] Tashjian and Gagel, J. Bone Miner. Res 21:354-365 (2006)
[Non Patent Literature 17] Hoare S R J. et al., Drug Discov. Today 10:417-427 (2005)

SUMMARY OF THE INVENTION

Problems to Solved by the Invention

An object of the present invention is to provide a noninvasively, preferably orally, available low molecular weight compound having a parathyroid hormone-like effect involving bone anabolism which can considerably improve the compliance of patients as compared with a parathyroid hormone peptide agonist.

Means for Solving the Problems

Specifically, the present invention includes:
[1]
A compound represented by the following general formula (1):

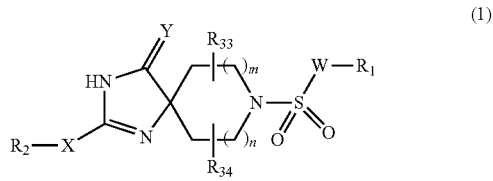

[wherein
W is selected from:
1) a single bond,
2) C1-C10 alkylene optionally containing a carbonyl group, wherein the alkylene is optionally substituted with a halogen atom(s) and/or a hydroxyl group(s),
3) C2-C10 alkenylene optionally substituted with a halogen atom(s),
4) C2-C10 alkynylene,
5) arylene optionally substituted with a halogen atom(s),
6) heteroarylene optionally substituted with a halogen atom(s), 7) C1-C10 heteroalkylene optionally substituted with a halogen atom(s),
8) —NH—, —NHCH$_2$— or —NHCH$_2$CH$_2$—,
9) cycloalkylene and
10) -(cycloalkylene)-CH$_2$—;
X is selected from the following bond or groups:
1) a single bond,
2) C1-C10 alkylene optionally substituted with a halogen atom(s) or cycloalkyl,
3) C2-C10 alkenylene optionally substituted with a halogen atom(s),
4) C2-C10 alkynylene optionally substituted with a halogen atom(s),
5) C1-10 oxyalkylene optionally substituted with a halogen atom(s) and
6) —NR$_{47}$—
wherein R$_{47}$ is selected from:
   i) a hydrogen atom and
   ii) C1-C10 alkyl optionally substituted with a halogen atom(s);
Y is selected from:
1) an oxygen atom,
2) a sulfur atom and
3) =NR$_{37}$,
or 4) Y is —NR$_{38}$R$_{39}$ shown in the following formula (A):

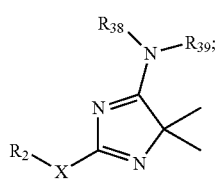

(A)

which can be tautomeric;
R$_{37}$ is selected from:
1) hydrogen,
2) hydroxy and
3) C1-C10 alkoxy;
R$_{38}$ and R$_{39}$ are independently selected from hydrogen or C1-C10 alkyl optionally substituted with cycloalkyl, or R$_{38}$ and R$_{39}$ may be bonded to each other to form a ring selected from the group consisting of azetidinyl, pyrrolidinyl, piperidinyl, piperazinyl and morpholinyl, and the ring is optionally substituted with C1-C10 alkyl;
m represents an integer of 0 to 2;
n represents an integer of 0 to 2;
R$_1$ is selected from:
1) hydrogen,
2) cycloalkyl optionally substituted with a group(s) selected from R$_4$, R$_5$ and R$_6$,
3) a heterocycle optionally substituted with a group(s) selected from R$_{25}$, R$_4$, R$_5$ and R$_6$,
4) aryl optionally substituted with a group(s) selected from R$_3$, R$_4$, R$_5$ and R$_6$ and
5) heteroaryl optionally substituted with a group(s) selected from R$_{25}$, R$_4$, R$_5$ and R$_6$;
R$_3$ is selected from:
1) —CONR$_7$R$_8$,
2) —OR$_9$,
3) —NR$_9$R$_{10}$,
4) —N(R$_9$) COR$_{11}$,
5) —N(R$_9$) SO$_2$R$_{12}$,
6) —SO$_2$R$_{15}$,
7) C1-10 alkyl optionally substituted with a group(s) independently selected from a halogen atom, a hydroxyl group, —COR$_{16}$ and —NR$_{13}$R$_{14}$,
8) heteroaryl optionally having C1-10 alkyl and/or C1-10 alkoxy as a substituent and
9) —N(R$_9$) CSR$_{11}$;
R$_4$ is selected from:
1) a halogen atom,
2) cyano,
3) nitro,
4) amino,
5) —NHCOR$_{26}$,
6) C1-C10 alkyl optionally substituted with a group(s) independently selected from hydroxycarbonyl, C1-C10 alkoxycarbonyl and aminocarbonyl,
7) C1-C10 haloalkyl,
8) C1-C10 alkoxy,
9) C1-C10 haloalkylcarbonyl,
10) —COR$_{16}$,
11) C1-C10 hydroxyalkyl and
12) C1-C10 heteroalkyl;
R$_5$ is selected from a halogen atom, C1-C10 alkyl, C1-C10 haloalkyl and C1-C10 alkoxy;
R$_6$ is selected from a halogen atom, C1-C10 alkyl and C1-C10 haloalkyl;
R$_7$ is selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —(CH$_2$)$_L$COR$_{16}$ (wherein L represents an integer of 1 to 4),
12) C1-C10 alkoxy,
13) C2-C10 alkenyl and
14) —NR$_{40}$R$_{41}$;
R$_{40}$ and R$_{41}$ are independently selected from hydrogen, C1-C10 alkyl and C1-C10 alkylcarbonyl, or R$_{40}$ and R$_{41}$ may be bonded to each other to form a ring selected from azetidinyl, pyrrolidinyl, piperidinyl, piperazinyl and morpholinyl, and the heterocycle is optionally substituted with C1-C10 alkyl;
R$_8$ is selected from hydrogen and C1-C10 alkyl optionally substituted with a halogen atom(s) and/or a hydroxyl group(s);
R$_7$ and R$_8$ may be bonded to form a 4- to 7-membered heterocycle optionally containing an additional element(s) or group(s) independently selected from O, N, S, SO and SO$_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent,
3) C1-C10 haloalkyl,
4) a hydroxyl group,
5) C1-C10 hydroxyalkyl, 6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl optionally substituted with C1-C10 alkyl,
11) heterocyclyl C1-C10 alkyl,
12) —$COR_{16}$,
13) —$NR_{19}R_{20}$,
14) —$SO_2R_{21}$,
15) C1-C10 alkoxy-C1-C10 alkyl optionally having a hydroxyl group(s) as a substituent(s) and
16) C1-C10 hydroxyalkyloxy, wherein the hydrogen atom of the hydroxyl group is optionally replaced by C1-C10 hydroxyalkyl, and
the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl;
$R_{16}$ is selected from:
1) a hydroxyl group,
2) C1-C10 alkoxy,
3) $NR_{17}R_{18}$ and
4) C1-C10 alkyl optionally substituted with a substituent(s) selected from a halogen atom, a hydroxyl group, C1-C10 alkoxycarbonyl or C1-C10 alkylamino;
$R_{17}$ is selected from:
1) hydrogen,
2) C1-C10 alkyl optionally substituted with a group(s) selected from aryl, amino, C1-C10 alkylamino, C1-C10 alkylcarbonylamino and a hydroxyl group,
3) heteroaryl and
4) C1-C10 alkoxy;
$R_{18}$ is selected from hydrogen, C1-C10 alkyl and C1-C10 hydroxyalkyl;
$R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl;
$R_{19}$ is selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl;
$R_{20}$ is selected from hydrogen and C1-C10 alkyl;
$R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;
$R_{21}$ is selected from:
1) C1-C10 alkyl optionally substituted with aryl,
2) amino,
3) C1-C10 alkylamino and
4) aryl optionally substituted with C1-C10 alkyl;
$R_9$ is selected from:
1) hydrogen,
2) C1-C10 alkyl optionally substituted with a group(s) independently selected from $R_{23}$, 3) aryl optionally substituted with a group(s) selected from a halogen atom, a hydroxyl group, amino and C1-C10 alkylamino,
4) cycloalkyl optionally substituted with a halogen atom(s) or a hydroxyl group(s),
5) a heterocycle optionally substituted with a group(s) independently selected from C1-C10 alkyl, C1-C10 alkylcarbonyl, C1-C10 alkoxy, C1-C10 alkoxycarbonyl, amino and a halogen atom,
6) C1-C10 heteroalkyl optionally substituted with a group(s) independently selected from a halogen atom and a hydroxyl group,
7) heteroaryl optionally substituted with a group(s) selected from C1-C10 alkyl, C1-C10 alkylcarbonyl, C1-C10 alkoxycarbonyl and a halogen atom and
8) cycloalkenyl optionally substituted with a group(s) selected from C1-C10 alkoxy, C1-C10 alkylamino, amino, a hydroxyl group and a halogen atom, wherein the cycloalkenyl optionally contains a carbonyl group;
$R_{23}$ is independently selected from:
1) a halogen atom,
2) a hydroxyl group,
3) a C1-C10 alkylcarbonyloxy group,
4) —$COR_{16}$,
5) amino,
6) C1-C10 alkylamino,
7) a heterocycle optionally substituted with a group(s) selected from C1-C10 alkyl, C1-C10 alkylcarbonyl, C1-C10 alkoxycarbonyl and a halogen atom and
8) cyano;
$R_{10}$ is selected from:
1) hydrogen and
2) C1-C10 alkyl optionally substituted with a group(s) selected from a halogen atom, a hydroxyl group and aryl;
$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$;
$R_{24}$ is independently selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) independently selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl,
11) heterocyclyl C1-C10 alkyl,
12) —$COR_{16}$,
13) —$NR_{19}R_{20}$ and
14) —$SO_2R_{21}$;

$R_{11}$ is selected from:
1) C1-C10 alkyl optionally substituted with a group(s) independently selected from:
   i) a hydroxyl group,
   ii) —$NR_{17}R_{18}$,
   iii) a C1-C10 alkoxy group,
   iv) a halogen atom,
   v) C1-C10 alkoxycarbonyl,
   vi) aminocarbonyl and
   vii) aryl optionally substituted with a group(s) independently selected from a halogen atom, a hydroxyl group, C1-C10 alkoxy, amino, C1-C10 alkylamino and —$COR_{22}$,
2) aryl optionally substituted with a group(s) independently selected from a halogen atom, a hydroxyl group, C1-C10 alkoxy, amino, C1-C10 alkylamino and —$COR_{22}$,
3) cycloalkyl optionally substituted with a halogen atom(s),
4) a heterocycle optionally substituted with a group(s) selected from C1-C10 alkyl, C1-C10 alkylcarbonyl, C1-C10 alkoxycarbonyl and a halogen atom,
5) C1-C10 alkoxy, wherein the alkyl group is optionally substituted with a group(s) independently selected from C1-C10 alkylcarbonylamino, amino, C1-C10 alkylamino and a hydroxyl group,
6) amino,
7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
8) C2-C10 alkenyl;
$R_{22}$ is selected from C1-C10 alkoxy, a hydroxyl group, amino and C1-C10 alkylamino;
$R_{12}$ is selected from:
1) C1-C10 alkyl,
2) amino and
3) C1-C10 alkylamino, wherein the alkyl group is optionally substituted with a group(s) independently selected from amino, C1-C10 alkylamino and a hydroxyl group;
$R_{13}$ is selected from:
1) hydrogen,
2) C1-C10 alkyl,
3) C1-C10 alkylcarbonyl, wherein the alkyl is optionally substituted with a hydroxyl group(s),
4) C1-C10 alkoxycarbonyl,
5) aminocarbonyl,
6) C1-C10 alkylaminocarbonyl and
7) heterocyclic carbonyl optionally substituted with C1-C10 alkyl;
$R_{14}$ is selected from:
1) hydrogen and
2) C1-C10 alkyl optionally substituted with a group(s) independently selected from a halogen atom, a hydroxyl group, amino and C1-C10 alkylamino;
$R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl;
$R_{15}$ is selected from:
1) C1-C10 alkyl and
2) —$NR_{35}R_{36}$;
$R_{35}$ is selected from:
1) hydrogen,
2) C1-C10 alkyl optionally substituted with a group(s) independently selected from:
   i) a halogen atom,
   ii) a hydroxyl group,
   iii) C1-C10 alkylcarbonylamino,
   iv) —$COR_{16}$,
   v) amino,
   vi) C1-C10 alkylamino,
   vii) C1-C10 alkoxy optionally substituted with a halogen atom(s),
   viii) heteroaryl optionally substituted with a C1-C10 alkyl group(s) and
   ix) a heterocycle,
3) aryl optionally substituted with a group(s) independently selected from a halogen atom, a hydroxyl group, amino and C1-C10 alkylamino,
4) cycloalkyl optionally substituted with a group(s) independently selected from a halogen atom and a hydroxyl group,
5) a heterocycle optionally substituted with a group(s) independently selected from C1-C10 alkyl, a halogen atom and aryl C1-C10 alkyl,
6) heteroaryl optionally substituted with C1-C10 alkyl and
7) C1-C10 alkylcarbonyl;
$R_{36}$ is selected from:
1) hydrogen and
2) C1-C10 alkyl optionally substituted with a group(s) independently selected from a halogen atom, a hydroxyl group and aryl;
$R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom;
$R_{25}$ is selected from:
1) a halogen atom,
2) C1-C10 alkyl optionally substituted with a group(s) independently selected from:
   i) a halogen atom,
   ii) aryl,
   iii) heteroaryl,
   iv) a heterocycle optionally substituted with a C1-C10 alkyl group(s),
   v) —$COR_{16}$,
   vi) —$NR_{13}R_{14}$ and
   vii) —$SO_2R_{21}$,
3) C1-C10 heteroalkyl optionally substituted with a hydroxyl group(s),
4) C1-C10 hydroxyalkyl, wherein each hydroxyl group may be independently substituted with a group(s) selected from C1-C10 alkyl, aryl C1-C10 alkyl and C1-C10 alkylcarbonyl,
5) —$COR_{16}$,
6) —$SO_2R_{21}$,
7) aryl and
8) cyano;
$R_2$ is selected from:
1) C1-C10 alkyl optionally substituted with a halogen atom(s), wherein the alkyl group is optionally further substituted with a substituent(s) independently selected from $R_{42}$,
2) C2-C10 alkenyl optionally substituted with a halogen atom(s), wherein the alkenyl group is optionally further substituted with a substituent(s) independently selected from $R_{42}$,
3) C2-C10 alkynyl optionally substituted with a halogen atom(s), wherein the alkynyl group is optionally further substituted with a substituent(s) independently selected from $R_{42}$,
4) cycloalkyl optionally substituted with a group(s) independently selected from:
   i) a halogen atom,
   ii) C2-C10 alkenyl or C1-C10 alkyl, iii) aryl optionally substituted with 1 to 3 substituents independently selected from C1-C10 alkyl, a halogen atom, C1-C10 alkoxy, C1-C10 alkylamino and C1-C10 alkylcarbonyl,
  iv) cycloalkyl,
  v) C2-C10 alkenyl optionally substituted with halogen,
  vi) C1-C10 alkylidene, wherein the alkylidene is bonded to the cycloalkyl by a double bond and the alkylidene is optionally substituted with a halogen atom(s),
  vii) C1-C10 alkoxy optionally substituted with a halogen atom(s),
  viii) C1-C10 alkyl optionally substituted with a group(s) independently selected from a halogen atom or C1-C10 alkoxy optionally substituted with a halogen atom(s),
  ix) C2-C10 alkynyl and
  x) —Si($R_{43}$)$_3$,
5) a heterocycle, wherein the heterocycle is optionally substituted with a group(s) independently selected from:
  i) a C1-C10 alkyl group,
  ii) C1-C10 alkylcarbonyl, wherein the alkyl group is optionally substituted with $R_{27}$,
  iii) arylcarbonyl, wherein the aryl group is optionally substituted with a group(s) independently selected from a halogen atom, C1-C10 alkyl and C1-C10 alkoxy,
  iv) heteroarylcarbonyl,
  v) C1-C10 alkoxycarbonyl, wherein the alkyl group is optionally substituted with a group(s) independently selected from a halogen atom, aryl and C1-C10 alkoxy,
  vi) aryloxycarbonyl, wherein the aryl group is optionally substituted with a halogen atom(s) and/or C1-C10 alkyl,
  vii) —CONR$_{28}$R$_{29}$,
  viii) —SO$_2$R$_{21}$,
  ix) a halogen atom,
  x) cycloalkylcarbonyl optionally fused with an aryl group and
  xi) C2-C10 alkenylcarbonyl, wherein the alkenyl group is optionally substituted with aryl, wherein the aryl is optionally substituted with a group(s) independently selected from a halogen atom, C1-C10 alkyl or C1-C10 alkoxy,
6) aryl optionally substituted with a group(s) independently selected from $R_{44}$,
7) heteroaryl optionally substituted with a group(s) independently selected from:
  i) a halogen atom,
  ii) C1-C10 alkyl and
  iii) C1-C10 alkoxy;
8) C1-C10 alkoxy optionally substituted with a halogen atom(s), wherein the alkoxy group is optionally further substituted with a substituent(s) independently selected from $R_{42}$,
9) —S(O)$_q$R$_{43}$ (wherein q is an integer of 0 to 2) and
10) cycloalkenyl optionally substituted with C1-C10 alkyl;
$R_{44}$ is selected from:
1) a halogen atom,
2) cyano,
3) C1-C10 alkyl optionally substituted with a group(s) independently selected from:
  i) a hydroxyl group,
  ii) —OR$_{26}$,
  iii) cyano,
  iv) aryloxy optionally substituted with a group(s) independently selected from a halogen atom, C1-C10 alkyl optionally substituted with a halogen atom(s) or C1-C10 alkoxy optionally substituted with a halogen atom(s) and
  v) a halogen atom, 4) cycloalkyl optionally substituted with a group(s) independently selected from a halogen atom or C1-C10 alkyl optionally substituted with a halogen atom(s),
5) C1-C10 alkoxy optionally substituted with a halogen atom(s) or a C2-C6 alkenyl group,
6) —COR$_{30}$,
7) C1-C10 alkylcarbonylamino,
8) C1-C10 alkoxycarbonylamino, wherein the alkoxy group is optionally substituted with aryl,
9) C1-C10 heteroalkyl optionally substituted with a halogen atom(s),
10) aryl optionally substituted with a substituent(s) independently selected from:
  i) a halogen atom,
  ii) C1-C10 alkyl,
  iii) C1-C10 alkoxy and
  iv) aryl optionally substituted with aryl optionally substituted with C1-C10 alkyl,
11) heteroaryl optionally substituted with a C1-C10 alkyl group(s),
12) —SO$_2$R$_{43}$,
13) —SOR$_{43}$,
14) C1-C10 alkylthio optionally substituted with a halogen atom(s),
15) —Si($R_{43}$)$_3$ and
16) —SF$_5$;
$R_{42}$ is selected from:
1) hydrogen,
2) aryl optionally substituted with a group(s) independently selected from C1-C10 alkyl optionally substituted with halogen, a halogen atom and C1-C10 alkoxy,
3) hydroxycarbonyl,
4) C1-C10 alkoxycarbonyl,
5) aminocarbonyl,
6) C1-C10 alkylaminocarbonyl,
7) C1-C10 alkoxycarbonylamino,
8) amino,
9) a hydroxyl group and
10) oxetane, tetrahydrofuran or tetrahydropyran optionally substituted with C1-C10 alkyl;
$R_{43}$ represents a C1-C10 alkyl group;
$R_{26}$ is aryl, or C1-C10 alkyl optionally substituted with a halogen atom(s);
$R_{27}$ is selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) a hydroxyl group,
4) amino,
5) C1-C10 alkylamino,
6) hydroxycarbonyl,
7) heteroaryl optionally substituted with a group(s) independently selected from C1-C10 alkyl and/or aryl, and
8) heteroaryloxy;
$R_{28}$ is selected from hydrogen or C1-C10 alkyl optionally substituted with aryl;
$R_{29}$ is selected from hydrogen or C1-C10 alkyl optionally substituted with aryl;
$R_{28}$ and $R_{29}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;
$R_{30}$ is selected from a hydroxyl group, C1-C10 alkoxy and —NR$_{31}$R$_{32}$;

$R_{31}$ and $R_{32}$ are independently selected from:
1) hydrogen,
2) C1-C10 alkyl optionally substituted with aryl and
3) aryl;
$R_{31}$ and $R_{32}$ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl; and $R_{33}$ and $R_{34}$ are independently selected from:
1) hydrogen and
2) C1-C10 alkyl], or a pharmacologically acceptable salt thereof;
or
a compound represented by the following general formula (2):

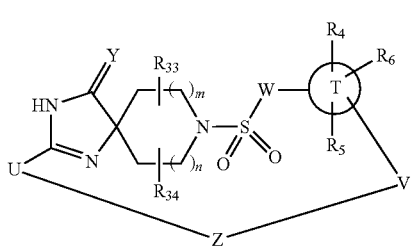

(2)

[wherein W, Y, m, n, $R_4$, $R_5$, $R_6$, $R_7$, $R_{11}$, $R_{16}$, $R_{19}$, $R_{20}$, $R_{21}$, $R_{33}$, $R_{34}$ and $R_{44}$ are as defined for the formula (1);
U represents a bond, C1-C10 alkylene or any group selected from groups represented by the following formula:

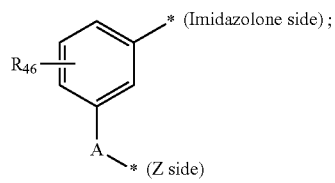

A is selected from O, NH and $CH_2$;
$R_{46}$ is selected from hydrogen or $R_{44}$;
T is selected from aryl and heteroaryl;
V is selected from:

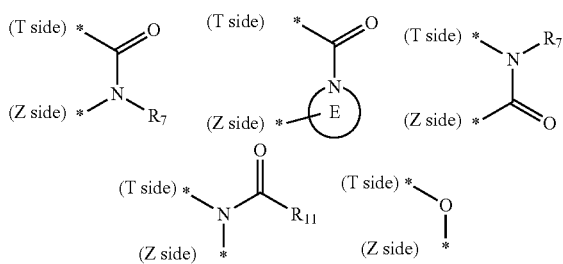

E is a 4- to 7-membered heterocycle optionally containing an additional element(s) or group(s) selected from O, N, S, $SO_2$ and $SO_2$, and the heterocycle is optionally substituted with a group(s) selected from:
1) hydrogen,
2) a halogen atom, 3) C1-C10 alkyl optionally having a group(s) independently selected from C1-C10 alkylamino, a halogen atom and a hydroxyl group,
4) a hydroxyl group,
5) C1-C10 alkoxy optionally substituted with a group(s) independently selected from a halogen atom, a hydroxyl group, amino and C1-C10 alkylamino,
6) aryl optionally substituted with a group(s) independently selected from a halogen atom, a hydroxyl group, amino and C1-C10 alkylamino,
7) C1-C10 heteroalkyl optionally substituted with a group(s) independently selected from a halogen atom, a hydroxyl group, amino and C1-C10 alkylamino,
8) a heterocycle optionally substituted with C1-C10 alkyl,
9) heteroaryl optionally substituted with C1-C10 alkyl,
10) heterocyclyl C1-C10 alkyl,
11) —$COR_{16}$,
12) —$NR_{19}R_{20}$ and
13) —$SO_2R_{21}$;
Z is a divalent group selected from:
1) C1-C10 alkylene or C1-C10 heteroalkylene optionally substituted with a halogen atom(s) and/or a hydroxyl group(s), wherein the carbon atom(s) may be oxidized to form carbonyl;
2) C2-C10 alkenylene or C2-C10 heteroalkenylene optionally substituted with a halogen atom(s) and/or a hydroxyl group(s), wherein the carbon atom(s) may be oxidized to form carbonyl; and
3) a group selected from:

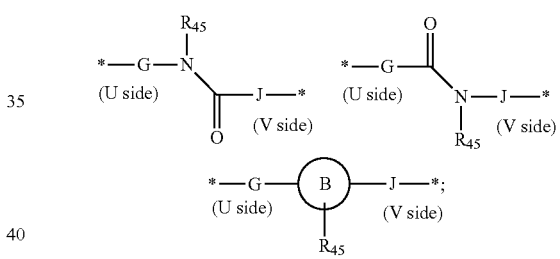

G is a divalent group selected from:
1) C1-C10 alkylene or C1-C10 heteroalkylene optionally substituted with a halogen atom(s); and
2) C2-C10 alkenylene or C2-C10 heteroalkenylene optionally substituted with a halogen atom(s);
J is a divalent group selected from:
1) C1-C10 alkylene or C1-C10 heteroalkylene optionally substituted with a halogen atom(s); and
2) C2-C10 alkenylene or C2-C10 heteroalkenylene optionally substituted with a halogen atom(s);
B is selected from a heterocycle or heteroaryl; and
$R_{45}$ is selected from hydrogen or C1-C10 alkyl], or a pharmacologically acceptable salt thereof.
[2]
The compound or a pharmacologically acceptable salt thereof according to [1], wherein
W is selected from:
1) a single bond,
2) C1-C10 alkylene optionally containing a carbonyl group, wherein the alkylene is optionally substituted with a halogen atom(s) or hydroxy,
3) C2-C10 alkenylene optionally substituted with a halogen atom(s),
4) C2-C10 alkynylene,
5) arylene, 6) heteroarylene,
7) —NH—, —NHCH$_2$— or —NHCH$_2$CH$_2$—,
8) cycloalkylene and
9) -(cycloalkylene)-CH$_2$—;
X is selected from the following bond or groups:
1) a single bond,
2) C1-C10 alkylene optionally substituted with cycloalkyl,
3) C2-C10 alkenylene,
4) C2-C10 alkynylene and
5) C1-C10 oxyalkylene;
R$_1$ is selected from:
1) hydrogen,
2) cycloalkyl optionally substituted with a group selected from R$_4$,
3) a heterocycle optionally substituted with a group(s) selected from R$_{25}$ and R$_4$,
4) aryl optionally substituted with a group(s) selected from R$_3$, R$_4$, R$_5$ and R$_6$ and
5) heteroaryl optionally substituted with a group(s) selected from R$_{25}$, R$_4$ and R$_5$;
R$_9$ is selected from:
1) hydrogen,
2) C1-C10 alkyl optionally substituted with a group(s) independently selected from R$_{23}$,
3) cycloalkyl optionally substituted with a halogen atom(s) or a hydroxyl group(s),
4) a heterocycle optionally substituted with a group(s) selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) selected from a halogen atom and a hydroxyl group,
6) heteroaryl optionally substituted with a group(s) independently selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, 1 to 3 hydroxyl groups and 1 to 4 halogen atoms, wherein the cycloalkenyl optionally contains a carbonyl group;
R$_{10}$ is selected from:
1) hydrogen and
2) C1-C10 alkyl optionally substituted with a group(s) independently selected from a halogen atom, a hydroxyl group and aryl;
R$_9$ and R$_{10}$ may be bonded to form a 4- to 7-membered heterocycle optionally containing an additional element(s) or group(s) independently selected from N, O, S, SO, SO$_2$, carbonyl and thiocarbonyl, and the heterocycle is optionally substituted with a substituent(s) independently selected from R$_{24}$;
R$_{24}$ is selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with 1 to 2 groups selected from a halogen atom, a hydroxyl group, amino and C1-C10 alkylamino,
9) —COR$_{16}$ and
10) —NR$_{19}$R$_{20}$;

R$_{11}$ is selected from:
1) C1-C10 alkyl optionally substituted with 1 to 3 substituents independently selected from:
  i) a hydroxyl group,
  ii) —NR$_{17}$R$_{18}$,
  iii) a C1-C10 alkoxy group,
  iv) a halogen atom,
  v) C1-C10 alkoxycarbonyl and
  vi) aminocarbonyl,
2) aryl,
3) aryl C1-C10 alkyl,
4) cycloalkyl optionally substituted with a halogen atom(s),
5) a heterocycle optionally substituted with C1-C10 alkyl,
6) C1-C10 alkoxy, wherein the alkyl group is optionally substituted with a group(s) independently selected from C1-C10 alkylcarbonylamino, amino, C1-C10 alkylamino and a hydroxyl group,
7) amino,
8) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
9) C2-C10 alkenyl; and
R$_{33}$ and R$_{34}$ are hydrogen,
wherein R$_3$, R$_4$, R$_5$, R$_6$, R$_{16}$, R$_{17}$, R$_{18}$, R$_{19}$, R$_{20}$, R$_{23}$ and R$_{25}$ are as defined in [1], respectively.
[3]
The compound or a pharmacologically acceptable salt thereof according to [1] or [2], wherein
W is selected from:
1) a single bond,
2) C1-C10 alkylene optionally substituted with a halogen atom(s),
3) C2-C10 alkenylene,
4) C2-C10 alkynylene and
5) heteroarylene,
X is selected from the following bond or groups:
1) a single bond,
2) C1-C10 alkylene,
3) C2-C10 alkenylene,
4) C2-C10 alkynylene and
5) C1-C10 oxyalkylene, wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene;
R$_1$ is selected from:
1) aryl optionally substituted with a group(s) selected from R$_3$, R$_4$ and R$_5$ and
2) heteroaryl optionally substituted with a group(s) selected from R$_{25}$ and R$_4$;
R$_3$ is selected from:
1) —CONR$_7$R$_8$,
2) —OR$_9$,
3) —NR$_9$R$_{10}$,
4) —N(R$_9$) COR$_{11}$,
5) —N(R$_9$) SO$_2$R$_{12}$,
6) —SO$_2$R$_{15}$,
7) C1-C10 alkyl optionally substituted with a group(s) selected from —COR$_{16}$ and —NR$_{13}$R$_{14}$ and
8) —N(R$_9$)CSNH$_2$;
R$_4$ is selected from:
1) halogen,
2) cyano,
3) amino,
4) C1-C10 alkyl,
5) C1-C10 haloalkyl, 6) C1-C10 alkoxy,
7) C1-C10 haloalkylcarbonyl,
8) —$COR_{16}$ and
9) C1-C10 heteroalkyl;
$R_2$ is selected from:
1) C1-C10 alkyl optionally substituted with a halogen atom(s), wherein the alkyl group is optionally further substituted with a group selected from $R_{42}$,
2) C2-C10 alkenyl optionally substituted with a halogen atom(s), wherein the alkenyl group is optionally further substituted with a group selected from $R_{42}$,
3) C2-C10 alkynyl optionally substituted with a halogen atom(s), wherein the alkynyl group is optionally further substituted with a group selected from $R_{42}$,
4) cycloalkyl optionally substituted with a group(s) independently selected from:
  i) a halogen atom,
  ii) C2-C10 alkenyl or C1-C10 alkyl,
  iii) aryl optionally substituted with a group(s) independently selected from C1-C10 alkyl, a halogen atom and C1-C10 alkoxy,
  iv) cycloalkyl,
  v) C2-C10 haloalkenyl or C1-C10 haloalkyl,
  vi) C1-C10 alkylidene, wherein the alkylidene is bonded to the cycloalkyl by a double bond and the alkylidene is optionally substituted with a halogen atom(s),
  vii) C1-C10 alkoxy optionally substituted with a halogen atom(s),
  viii) C1-C10 alkyl substituted with C1-C10 alkoxy, wherein the alkyl and/or the alkyl in the alkoxy is optionally substituted with a halogen atom(s),
  ix) C2-C10 alkynyl and
  x) —$Si(R_{43})_3$,
5) a heterocycle, wherein the heterocycle is optionally substituted with a group(s) selected from:
  i) a C1-C10 alkyl group,
  ii) C1-C10 alkylcarbonyl, wherein the alkyl group is optionally substituted with $R_{27}$,
  iii) arylcarbonyl, wherein the aryl group is optionally substituted with a group(s) independently selected from a halogen atom, C1-C10 alkyl and C1-C10 alkoxy,
  iv) heteroarylcarbonyl,
  v) C1-C10 alkoxycarbonyl, wherein the alkyl group is optionally substituted with a group(s) independently selected from a halogen atom, aryl and C1-C10 alkoxy,
  vi) aryloxycarbonyl, wherein the aryl group is optionally substituted with a halogen atom(s) and/or C1-C10 alkyl,
  vii) —$CONR_{28}R_{29}$ and
  viii) —$SO_2R_{21}$,
6) aryl optionally substituted with a group(s) independently selected from $R_{44}$,
7) heteroaryl optionally substituted with any of the following groups:
  i) C1-C10 alkyl,
8) C1-C10 alkoxy optionally substituted with a halogen atom(s), wherein the alkoxy group is optionally further substituted with a group selected from $R_{42}$,
9) —$S(O)_q(R_{43}$ (wherein q is an integer of 0 to 2) and
10) cycloalkenyl optionally substituted with C1-C10 alkyl,
$R_{44}$ is selected from:
1) a halogen atom,
2) cyano,
3) C1-C10 alkyl optionally substituted with any of the following groups:
  i) a hydroxyl group,
  ii) —$OR_{26}$,
  iii) cyano and
  iv) aryloxy optionally substituted with a group(s) selected from a halogen atom, C1-C10 alkyl, C1-C10 haloalkyl or C1-C10 haloalkoxy,
4) C1-C10 haloalkyl,
5) cycloalkyl optionally substituted with a group(s) selected from a halogen atom and C1-C10 haloalkyl,
6) C1-C10 alkoxy optionally substituted with a halogen atom(s) or a C2-C6 alkenyl group,
7) —$COR_{30}$,
8) C1-C10 heteroalkyl optionally substituted with a halogen atom(s),
9) aryl optionally substituted with a group(s) independently selected from:
  i) C1-C10 alkyl and
  ii) aryl,
10) heteroaryl optionally substituted with a C1-C10 alkyl group(s),
11) —$SO_2R_{43}$,
12) C1-C10 alkylthio optionally substituted with a halogen atom(s),
13) —$Si(R_{43})_3$ and
14) —$SF_5$; and
$R_{27}$ is selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) heteroaryl optionally substituted with a group(s) independently selected from C1-C10 alkyl and aryl and
4) heteroaryloxy,
wherein $R_5$, $R_7$, $R_8$, $R_9$, $R_{10}$, $R_{11}$, $R_{12}$, $R_{13}$, $R_{14}$, $R_{15}$, $R_{16}$, $R_{21}$, $R_{25}$, $R_{26}$, $R_{28}$, $R_{29}$, $R_{30}$, $R_{42}$ and $R_{43}$ are as defined in [1] or [2] from which [3] depends, respectively.
[4]
The compound or a pharmacologically acceptable salt thereof according to any of [1] to [3], wherein
W is selected from:
1) C1-C6 alkylene optionally substituted with a fluorine atom(s),
2) C1-C6 alkenylene and
3) thiophene,
X is selected from the following bond or groups:
1) a single bond,
2) C1-C6 alkylene and
3) C1-C6 oxyalkylene optionally substituted with a halogen atom(s), wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene;
Y represents an oxygen atom;
m represents 1; and
n represents 1.
[5]
The compound or a pharmacologically acceptable salt thereof according to any of [1] to [4], wherein
W is selected from:
1) ethylene,
2) vinylene and
3) thiophene,
X represents a single bond;
$R_3$ is selected from:
1) —$CONR_7R_8$,
2) —$OR_9$,
3) —$NR_9R_{10}$,
4) —$N(R_9) COR_{31}$, 5) —N(R$_9$) SO$_2$R$_{12}$,
6) —SO$_2$R$_{15}$ and
7) C1-C6 alkyl optionally substituted with a group(s) selected from —COR$_{16}$ and —NR$_{13}$R$_{14}$;

R$_2$ is selected from:
1) C1-C10 alkyl optionally substituted with a halogen atom(s), wherein the alkyl group is optionally further substituted with a group selected from R$_{42}$,
2) C2-C10 alkenyl optionally substituted with a halogen atom(s), wherein the alkenyl group is optionally further substituted with a group selected from R$_{42}$,
3) C2-C10 alkynyl optionally substituted with a halogen atom(s), wherein the alkynyl group is optionally further substituted with a group selected from R$_{42}$,
4) cycloalkyl optionally substituted with a group(s) independently selected from:
  i) a halogen atom,
  ii) C2-C6 alkenyl or C1-C6 alkyl,
  iii) aryl optionally substituted with a group(s) independently selected from C1-C6 alkyl, a halogen atom, C1-C6 alkoxy, C1-C6 alkylamino and C1-C6 alkylcarbonyl,
  iv) cycloalkyl,
  v) C2-C6 haloalkenyl or C1-C6 haloalkyl,
  vi) C1-C6 alkylidene, wherein the alkylidene is bonded to the cycloalkyl by a double bond and the alkylidene is optionally substituted with a halogen atom(s),
  vii) C1-C6 alkoxy optionally substituted with a halogen atom(s),
  viii) C1-C6 alkyl substituted with C1-C6 alkoxy, wherein the alkyl and/or the alkyl in the alkoxy is optionally substituted with halogen,
  ix) C2-C6 alkynyl and
  x) —Si(R$_{43}$)$_3$,
5) a group represented by the following general formula (B)

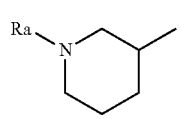

(B)

(wherein Ra represents a group selected from:
  i) C1-C6 alkylcarbonyl, wherein the alkyl group is optionally substituted with R$_{27}$,
  ii) arylcarbonyl, wherein the aryl group is optionally substituted with a group(s) independently selected from a halogen atom, C1-C6 alkyl and C1-C6 alkoxy,
  iii) C1-C6 alkoxycarbonyl, wherein the alkyl group is optionally substituted with a group(s) selected from a halogen atom, aryl and C1-C6 alkoxy,
  iv) aryloxycarbonyl, wherein the aryl group is optionally substituted with a halogen atom(s) or C1-C6 alkyl,
  v) —CONR$_{28}$R$_{29}$ and
  vi) —SO$_2$R$_{21}$),
6) aryl optionally substituted with a group(s) independently selected from R$_{44}$,
7) heteroaryl optionally substituted with any of the following groups:
  i) a halogen atom,
  ii) C1-C6 alkyl and
  iii) C1-C6 alkoxy;
8) C1-C6 alkoxy optionally substituted with a halogen atom(s), wherein the alkoxy group is optionally further substituted with a group selected from R$_{42}$,
9) —S(O)$_q$R$_{43}$ (wherein q is an integer of 0 to 2) and
10) cycloalkenyl optionally substituted with C1-C6 alkyl; and R$_{44}$ is selected from:
1) a halogen atom,
2) cyano,
3) C1-C6 alkyl optionally substituted with any of the following groups:
  i) a hydroxyl group,
  ii) —OR$_{26}$,
  iii) cyano and
  iv) aryloxy optionally substituted with a group(s) selected from a halogen atom, C1-C6 alkyl, C1-C6 haloalkyl or C1-C6 haloalkoxy,
4) C1-C6 haloalkyl,
5) cycloalkyl optionally substituted with a group(s) selected from a halogen atom and C1-C6 haloalkyl,
6) C1-C6 alkoxy optionally substituted with a halogen atom(s),
7) —COR$_{30}$,
8) C1-C6 heteroalkyl optionally substituted with a halogen atom(s),
9) aryl optionally substituted with a group(s) independently selected from:
  i) C1-C6 alkyl and
  ii) aryl,
10) heteroaryl optionally substituted with a C1-C6 alkyl group(s),
11) —SO$_2$R$_{43}$,
12) C1-C6 alkylthio optionally substituted with a halogen atom(s),
13) —Si(R$_{43}$)$_3$ and
14) —SF$_5$,
wherein R$_7$, R$_8$, R$_9$, R$_{10}$, R$_{11}$, R$_{12}$, R$_{13}$, R$_{14}$, R$_{15}$, R$_{16}$, R$_{21}$, R$_{26}$, R$_{27}$, R$_{28}$, R$_{29}$, R$_{30}$, R$_{42}$ and R$_{43}$ are as defined in [1] to [4] from which [5] depends, respectively.

[6]
The compound or a pharmacologically acceptable salt thereof according to [3], wherein R$_1$ is a group represented by the following general formula (3):

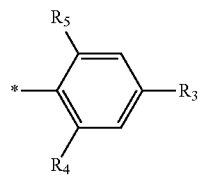

(3)

wherein R$_3$, R$_4$ and R$_5$ are as defined for R$_3$, R$_4$ and R$_5$ in [3].

[7]
The compound or a pharmacologically acceptable salt thereof according to [3], wherein R$_1$ is a group represented by the following general formula (4):

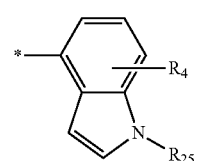

(4)

wherein R$_4$ and R$_{25}$ are as defined for R$_4$ and R$_{25}$ in [3].

[8]

The compound or a pharmacologically acceptable salt thereof according to [5], wherein $R_1$ is a group represented by the following general formula (3):

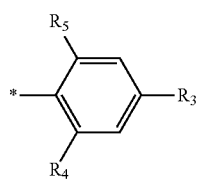

(3)

wherein $R_3$, $R_4$ and $R_5$ are as defined for $R_3$, $R_4$ and $R_5$ in [5].

[9]

The compound or a pharmacologically acceptable salt thereof according to [5], wherein $R_1$ is a group represented by the following general formula (4):

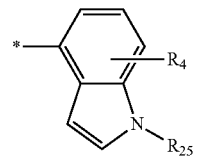

(4)

wherein $R_4$ and $R_{25}$ are as defined for $R_4$ and $R_{25}$ in [5].

[10]

Compounds of Compound Nos. (1) to (1446) described herein or pharmacologically acceptable salts thereof.

[11]

The compound or a pharmacologically acceptable salt thereof according to any of [1] to [5], wherein U represents C1-C6 alkylene or any group selected from groups represented by the following formula:

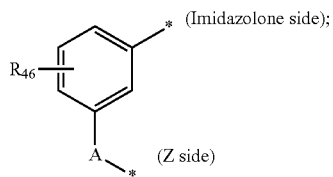

A is O;
$R_{46}$ is selected from hydrogen, C1-C10 alkyl, C1-C10 haloalkyl and C1-C10 hydroxyalkyl;
V is selected from:

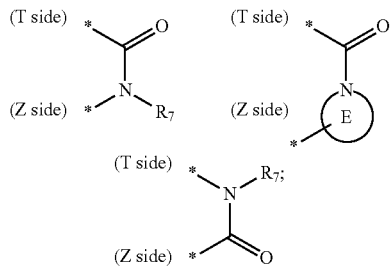

E is pyrrolidine or piperidine optionally substituted with a hydroxyl group(s); and
$R_7$ is selected from:
1) hydrogen,
2) C1-C10 alkyl and
3) C1-C10 hydroxyalkyl.

[12]

A pharmaceutical composition comprising the compound or a pharmacologically acceptable salt thereof according to any of [1] to [11] as an active ingredient.

[13]

A pharmaceutical composition for activating intracellular cAMP response, comprising the compound or a pharmacologically acceptable salt thereof according to any of [1] to [11] as an active ingredient.

[14]

A prophylactic or therapeutic agent for osteoporosis, fracture, osteomalacia, arthritis, thrombocytopenia, hypoparathyroidism, hyperphosphatemia or tumoral calcinosis, or a stem cell mobilizing agent, comprising the compound or a pharmacologically acceptable salt thereof according to any of [1] to [11] as an active ingredient.

[15]

A method for the prevention or treatment of osteoporosis, fracture, osteomalacia, arthritis, thrombocytopenia, hypoparathyroidism, hyperphosphatemia or tumoral calcinosis, or stem cell mobilization, comprising administering a pharmaceutically effective amount of a composition comprising the compound or a pharmacologically acceptable salt thereof according to any of [1] to [11] to a patient in need of prevention or treatment of the disease or stem cell mobilization.

[16]

Use of the compound or a pharmacologically acceptable salt thereof according to any of [1] to [11] for the manufacture of a prophylactic or therapeutic agent for osteoporosis, fracture, osteomalacia, arthritis, thrombocytopenia, hypoparathyroidism, hyperphosphatemia or tumoral calcinosis, or a stem cell mobilizing agent.

[17]

The compound or a pharmacologically acceptable salt thereof according to any of [1] to [11] for the treatment or prevention of osteoporosis, fracture, osteomalacia, arthritis, thrombocytopenia, hypoparathyroidism, hyperphosphatemia or tumoral calcinosis, or stem cell mobilization.

In the description of each claim, a substituent not particularly defined is as defined for the same substituent in another claim from which the claim depends.

In the present specification and claims translated into languages such as English, description with indefinite articles (e.g., "a", "an" in English), definite articles (e.g., "the" in English) and the like includes singular and plural aspects unless otherwise defined. For example, "a group" in English includes one or more groups.

Advantageous Effects of Invention

The compounds or pharmacologically acceptable salts thereof according to the present invention have a parathyroid hormone-like effect involving bone anabolism which can considerably improve the compliance of patients as compared with parathyroid hormone peptide agonists.

DESCRIPTION OF EMBODIMENTS

The present invention relates to spiroimidazolone derivatives and use thereof. The present inventors have synthesized a compound represented by the above formula (1) or (2) or a pharmacologically acceptable salt thereof for the first time and have found that the compound or a salt thereof is a compound having a parathyroid hormone (PTH)-like effect.

The "alkyl" herein refers to a monovalent group derived by removing any one hydrogen atom from an aliphatic hydrocarbon, and covers a subset of hydrocarbyl or hydrocarbon group structures not containing a heteroatom or an unsaturated carbon-carbon bond and containing hydrogen and carbon atoms in the backbone. Examples of the alkyl group include those of linear or branched structures. The alkyl group is preferably an alkyl group having 1 to 10 carbon atoms (C1-C10; "Cp-Cq" hereinafter means that the group has p to q carbon atoms), more preferably a C1-C6 alkyl group. In particular, it is preferably a C1-C3 alkyl group in $R_{38}$ and $R_{39}$, a C1-C3 alkyl group in $R_3$, a C1-C3 alkyl group in $R_4$, a C1-C3 alkyl group in $R_5$, a C1-C3 alkyl group in $R_6$, a C1-C3 alkyl group in $R_7$, a C1-C3 alkyl group in $R_{40}$ and $R_{41}$, a C1-C3 alkyl group in $R_8$, a C1-C3 alkyl group in a substituent on a heterocycle where $R_7$ and $R_8$ are bonded to each other to form the heterocycle or a substituent on a spiro ring where the spiro ring is formed with the heterocycle, a C1-C3 alkyl group in $R_{16}$, a C1-C5 alkyl group in $R_{17}$, a C1-C3 alkyl group in $R_{16}$, a C1-C3 alkyl group in a substituent on a heterocycle where $R_{17}$ and $R_{18}$ are bonded to each other to form the heterocycle, a C1-C3 alkyl group in $R_{19}$, a C1-C3 alkyl group in $R_{20}$, a C1-C3 alkyl group in $R_{21}$, a C1-C4 alkyl group in $R_9$, a C1-C3 alkyl group in $R_{23}$, a C1-C3 alkyl group in $R_{10}$, a C1-C3 alkyl group in $R_{24}$, a C1-C4 alkyl group in $R_{11}$, a C1-C3 alkyl group in $R_{12}$, a C1-C3 alkyl group in $R_{13}$, a C1-C4 alkyl group in $R_{14}$, a C1-C3 alkyl group in a substituent on a heterocycle where $R_{13}$ and $R_{14}$ are bonded to each other to form the heterocycle, a C1-C3 alkyl group in $R_{15}$, a C1-C4 alkyl group in $R_{35}$, a C1-C3 alkyl group in $R_{36}$, a C1-C4 alkyl group in $R_{25}$, a C1-C13 alkyl group in $R_2$, a C1-C5 alkyl group in $R_{44}$, a C1-C3 alkyl group in $R_{42}$, a C1-C3 alkyl group in $R_{43}$, a C1-C3 alkyl group in $R_{26}$, a C1-C3 alkyl group in $R_{27}$ and a C1-C6 alkyl group in $R_{28}$.

Specific examples of the alkyl include a methyl group, an ethyl group, an n-propyl group, an isopropyl group, an n-butyl group, an isobutyl group, an s-butyl group, a t-butyl group, a pentyl group, an isopentyl group, a 2,3-dimethylpropyl group, a 3,3-dimethylbutyl group, a hexyl group, a 2,3-dimethylhexyl group, a 1,1-dimethylpentyl group, a heptyl group and an octyl group.

The "alkenyl" herein refers to a monovalent group having at least one double bond (two adjacent SP2 carbon atoms). Depending on the configuration of the double bond and the substituent (if present), the geometry of the double bond can be an entgegen (E) or zuzammen (Z) configuration or a cis or trans configuration. Examples of the alkenyl group include linear or branched groups, including straight chains that include internal olefins. Preferred examples include C2-C10 alkenyl groups, and more preferred examples include C2-C6 alkenyl groups. In particular, it is preferably a C2-C5 alkenyl group in $R_7$ and a C1-C9 alkenyl group in $R_2$.

Specific examples of such alkenyl include a vinyl group, an allyl group, a 1-propenyl group, a 2-propenyl group, a 1-butenyl group, a 2-butenyl group (including cis and trans), a 3-butenyl group, a pentenyl group and a hexenyl group.

The "alkynyl" herein refers to a monovalent group having at least one triple bond (two adjacent SP carbon atoms). Examples include linear or branched alkynyl groups, including internal alkylenes. Preferred examples include C2-C10 alkynyl groups, and more preferred examples include C2-C6 alkynyl groups. In particular, it is preferably a C2-C9 alkynyl group in $R_2$.

Specific examples of the alkynyl include an ethynyl group, a 1-propynyl group, a propargyl group, a 3-butynyl group, a pentynyl group, a hexynyl group, a 3-phenyl-2-propynyl group, a 3-(2'-fluorophenyl)-2-propynyl group, a 2-hydroxy-2-propynyl group, a 3-(3-fluorophenyl)-2-propynyl group and a 3-methyl-(5-phenyl)-4-pentynyl group.

The alkenyl or alkynyl can have one or more double bonds or triple bonds, respectively.

The "cycloalkyl" herein refers to a saturated cyclic monovalent aliphatic hydrocarbon group and includes single rings, fused rings, bicyclo rings and spiro rings. Preferred examples include C3-C10 cycloalkyl groups. Specific examples of the cycloalkyl group include a cyclopropyl group, a cyclobutyl group, a cyclopentyl group, a cyclohexyl group, a cycloheptyl group, a cyclooctyl group and a bicyclo[2.2.1]heptyl group.

The "cycloalkenyl" herein refers to a cyclic aliphatic hydrocarbon group having at least one double bond and includes single rings, fused rings, bicyclo rings and spiro rings. Preferred examples include C3-C10 cycloalkynyl groups, and more preferred examples include C3-C6 alkenyl groups. It is preferably C3-C5 cycloalkenyl in $R_9$. Specific examples of the cycloalkenyl group include a cyclopropenyl group, a cyclobutenyl group, a cyclopentenyl group, a cyclohexenyl group, a cycloheptenyl group, a cyclooctenyl group and a tetralinyl group.

The "heteroatom" herein refers to a nitrogen atom (N), an oxygen atom (O) or a sulfur atom (S).

The "halogen atom" herein refers to a fluorine atom, a chlorine atom, a bromine atom or an iodine atom.

The "haloalkyl" herein represents a group in which preferably 1 to 9, more preferably 1 to 5, of the same or different above "halogen atoms" are bonded to the above "alkyl". The haloalkyl is preferably C1-C10 haloalkyl, more preferably C1-C6 haloalkyl. In particular, it is preferably C1-C3 haloalkyl in $R_4$ and C1-C3 haloalkyl in $R_{44}$.

Specific examples include a fluoromethyl group, a difluoromethyl group and a trifluoromethyl group.

The "haloalkenyl" herein represents a group in which preferably 1 to 9, more preferably 1 to 5, of the same or different above "halogen atoms" are bonded to the above "alkenyl".

The "alkylcarbonyl" herein refers to a carbonyl group to which the above-defined "alkyl" is bonded, and is preferably C1-C10 alkylcarbonyl, more preferably C1-C6 alkylcarbonyl. In particular, it is preferably C1-C3 alkylcarbonyl in $R_{40}$ and $R_{41}$, C1-C3 alkylcarbonyl in $R_{19}$, C1-C3 alkylcarbonyl in $R_9$, C1-C3 alkylcarbonyl in $R_{23}$, C1-C3 alkylcarbonyl in $R_{12}$, C1-C3 alkylcarbonyl in $R_{35}$ and C1-C5 alkylcarbonyl in $R_2$.

The "Cn-Cm alkylcarbonyl" herein means that the alkyl therein is a "Cn-Cm" alkyl in terms of the number of carbon atoms. Hereinafter, the same applies to a group containing "alkylcarbonyl".

Specific examples include an acetyl group, an ethylcarbonyl group, a 1-propylcarbonyl group, a 2-propylcarbonyl group and a 2,2-dimethylpropylcarbonyl group.

The "haloalkylcarbonyl" herein refers to a carbonyl group to which the above-defined "haloalkyl" is bonded. The haloalkylcarbonyl is preferably C1-C10 haloalkylcarbonyl, more preferably C1-C6 haloalkylcarbonyl. In particular, it is preferably C1-C3 haloalkylcarbonyl in $R_4$.

The "cycloalkylcarbonyl" herein refers to a carbonyl group to which the above-defined "cycloalkyl" is bonded.

The "alkenylcarbonyl" herein refers to a carbonyl group to which the above-defined "alkenyl" is bonded, and is preferably C2-C10 alkenyl, more preferably C2-C6 alkenylcarbonyl. In particular, it is preferably C2-C3 alkenylcarbonyl in $R_2$.

The "Cn-Cm alkenylcarbonyl" herein means that it includes an alkenyl having "Cn-Cm" carbon atoms. Hereinafter, the same applies to a group containing "alkenylcarbonyl".

The "alkoxy" herein refers to an oxy group to which the above-defined "alkyl" is bonded, and is preferably a C1-C10 alkoxy group, more preferably a C1-C6 alkoxy group. In particular, it is preferably a C1-C3 alkoxy group in $R_{37}$, a C1-C3 alkoxy group in $R_3$, a C1-C3 alkoxy group in $R_4$, a C1-C3 alkoxy group in $R_5$, a C1-C3 alkoxy group in $R_7$, a C1-C3 alkoxy group in a substituent on a heterocycle where $R_7$ and $R_8$ are bonded to each other to form the heterocycle, a C1-C4 alkoxy group in $R_{16}$, a C1-C3 alkoxy group in $R_{17}$, a C1-C3 alkoxy group in $R_{11}$, a C1-C4 alkoxy group in $R_2$ and a C1-C4 alkoxy group in $R_{27}$. Specific examples include a methoxy group, an ethoxy group, a 1-propoxy group, a 2-propoxy group, an n-butoxy group, an i-butoxy group, a sec-butoxy group, a t-butoxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group and a 1-methyl-cyclopropylmethoxy group.

The "alkylcarbonyloxy" herein refers to an oxy group to which the above-defined "alkylcarbonyl" is bonded, and is preferably a C1-C10 alkylcarbonyloxy group, more preferably a C1-C6 alkylcarbonyloxy group. In particular, it is preferably a C1-C3 alkylcarbonyloxy group in $R_{23}$.

The "alkoxycarbonyl" herein refers to a carbonyl group to which the above-defined "alkoxy" is bonded. The alkoxycarbonyl is preferably C1-C10 alkoxycarbonyl, more preferably C1-C6 alkoxycarbonyl. It is preferably C1-C3 alkoxycarbonyl in $R_4$, C1-C3 alkoxycarbonyl in $R_{16}$, C1-C4 alkoxycarbonyl in $R_{19}$, C1-C4 alkoxycarbonyl in $R_9$, C1-C3 alkoxycarbonyl in $R_{23}$, C1-C3 alkoxycarbonyl in $R_{11}$, C1-C4 alkoxycarbonyl in $R_{13}$, C1-C5 alkoxycarbonyl in $R_2$ and C1-C3 alkoxycarbonyl in $R_{42}$. Examples include —CO$_2$tBu (t-butoxycarbonyl) and —CO$_2$Me (methoxycarbonyl).

The "Cn-Cm alkoxycarbonyl" herein means that the alkyl in the alkoxy is a "Cn-Cm" alkyl in terms of the number of carbon atoms. Hereinafter, the same applies to a group containing "alkoxycarbonyl".

The "heteroalkyl" herein refers to a group containing preferably 1 to 5 heteroatoms in the above-defined "alkyl" backbone and is preferably C1-C10 heteroalkyl, more preferably C1-C6 heteroalkyl. In particular, it is preferably C1-C5 heteroalkyl in $R_9$, C1-C5 heteroalkyl in $R_{11}$ and C1-C6 heteroalkyl in $R_{25}$. Examples include —CH$_2$OCH$_3$, —CH$_2$OCH$_2$CH$_3$, —CH(Me)OCH$_3$ and —CH$_2$CH$_2$NMe$_2$.

The "heteroalkenyl" herein refers to a group containing preferably 1 to 5 heteroatoms in the above-defined "alkenyl" backbone.

The "alkylene" herein refers to a divalent group having a basic skeleton represented by —(CH$_2$)n- (preferably n=1 to 10), and may contain a branched chain. Specific examples include C1-C5 alkylene (n=1 to 5). More specific examples include a methylene group, a dimethylmethylene group, an ethylene group, a propylene group, a butylene group and a pentamethylene group. In particular, it is preferably C2-C5 alkylene in W, C1-C9 alkylene in X, C1-C10 alkylene in U, C1-C10 alkylene in Z and C1-C5 alkylene in G.

The "alkylidene" herein refers to a divalent group produced by removing two hydrogen atoms from the same carbon atom of a ring, the free valencies of which are part of a double bond. The geometry of the double bond can be an entgegen (E) or zuzammen (Z) configuration or a cis or trans configuration. Examples of the alkylidene include linear or branched groups. Preferred examples include C1-C10 alkylidene, and more preferred examples include C1-C6 alkylidene. In particular, it is preferably C1-C4 alkylidene in $R_2$. Specific examples include methylene (=CH$_2$), ethylidene (=CHCH$_3$), isopropylidene (=C(CH$_3$)$_2$) and propylidene (=CHCH$_2$CH$_3$).

The "alkenylene" herein refers to a divalent group having at least one double bond (two adjacent SP2 carbon atoms). Depending on the configuration of the double bond and the substituent (if present), the geometry of the double bond can be an entgegen (E) or zuzammen (Z) configuration or a cis or trans configuration. Examples of the alkenylene include linear or branched groups. Preferred examples include C2-C10 alkenylene, and more preferred examples include C2-C6 alkenylene. Specific examples include a vinylene group, a 1-propenylene group, a 1-butenylene group and a 1-pentenylene group. In particular, it is preferably C2-C5 alkenylene in W, C2-C9 alkenylene in X, C2-C10 alkenylene in Z and C2-C5 alkenylene in G.

The "alkynylene" herein refers to a divalent group having at least one triple bond (two adjacent SP carbon atoms). Examples include linear or branched alkynylenes. Preferred examples include C2-C10 alkynylene, and more preferred examples include C2-C6 alkynylene. In particular, it is preferably C2-C5 alkynylene in W and C2-C9 alkynylene in X.

The "cycloalkylene" herein refers to a saturated cyclic divalent aliphatic hydrocarbon group and includes single rings, bicyclo rings and spiro rings. Preferred examples include C3-C10 cycloalkylene. Specific examples of the cycloalkyl group include a cyclopropylene group, a cyclobutylene group, a cyclopentylene group, a cyclohexylene group, a cycloheptylene group, a cyclooctylene group and a bicyclo[2.2.1]heptylene group.

The "oxyalkylene" herein refers to a divalent C1-C10 group in which one end of the above-defined alkylene is an oxygen atom. Examples include —CH$_2$O—, —C(Me)$_2$O—, —CH$_2$CH$_2$O—, —CH$_2$CH(Me)O— and —CH$_2$C(Me)$_2$O—. In X, the oxyalkylene is preferably bonded to a 1,3,8-triaza-spiro[4.5]dec-1-en-4-one ring or a 1,3,8-triaza-spiro[4.5]dec-1-ene-4-thione ring through a carbon atom in the oxyalkylene. In particular, it is preferably C1-C5 oxyalkylene in X.

The "heteroalkylene" herein refers to a divalent, preferably C1-C10, group containing preferably 1 to 5 heteroatoms in the above-defined "alkylene" backbone, and may contain a branched chain. Examples include —CH$_2$OCH$_2$—, —CH$_2$OCH$_2$CH$_2$—, —CH(Me)OCH$_2$—, —CH$_2$CH$_2$NHCH$_2$— and —CH$_2$CH$_2$N(Me)CH$_2$—. In particular, it is preferably C2-C5 heteroalkylene in W, C1-C8 heteroalkylene in Z and C1-C4 heteroalkylene in G.

The "heteroalkenylene" herein refers to a divalent, preferably C1-C10, group containing preferably 1 to 5 heteroatoms in the above-defined "alkenylene" backbone, and may contain a branched chain. In particular, it is preferably C2-C8 heteroalkenylene in Z.

The "aryl" herein refers to a monovalent aromatic hydrocarbon ring, and may be partially saturated insofar as it is aromatic. Preferred examples include C6-C10 aryl. Specific examples of the aryl include a phenyl group, a naphthyl group (e.g., a 1-naphthyl group, a 2-naphthyl group) and a tetrahydronaphthyl group.

The "heteroaryl" herein refers to a monovalent group of an aromatic ring containing preferably 1 to 5 heteroatoms in the ring-forming atoms, and may be partially saturated. The saturated carbon atom(s) may be oxidized to form carbonyl. The ring may be a single ring or two fused rings (e.g., a bicyclic heteroaryl obtained by fusion with a benzene ring or monocyclic heteroaryl ring). The number of the ring-forming carbon atoms is preferably 1 to 10 (C1-C10 heteroaryl).

Specific examples of the heteroaryl include a furyl group, a thienyl group, a pyrrolyl group, an imidazolyl group, a pyrazolyl group, a triazolyl group, an isothiazolyl group, an oxazolyl group, an isoxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzoxazolyl group, a benzoxadiazolyl group, a benzimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolizinyl group and an imidazopyridyl group.

The "arylene" herein refers to a divalent group derived by further removing any one hydrogen atom from the above-defined "aryl". Preferred examples include C6-C10 arylene. Specific examples include a 1,3-phenylene group and a 1,4-phenylene group.

The "heteroarylene" herein refers to a divalent group derived by further removing any one hydrogen atom from the above-defined "heteroaryl". Specific examples include a 2,5-thiophenediyl group and a 2,6-pyridinediyl group.

The "heterocycle" herein refers to a C1-10 nonaromatic cycloalkyl, wherein the cycloalkyl is a monovalent group containing preferably 1 to 5 heteroatoms in the ring-forming atoms, the cycloalkyl may have a double bond in the ring, the carbon atom(s) may be oxidized to form carbonyl, the heteroatoms may form an oxo group, and the cycloalkyl may contain two fused rings. Specific examples of the heterocycle include azetidinyl, pyrrolidinyl, piperidinyl, piperazinyl, morpholinyl, oxazolidone, a 1,4-benzodioxanyl group, a tetrahydropyranyl group, a 1,3-dioxolanyl group, a 1,3-thiazolidinyl group, a hydantoyl group, a benzoxazolinonyl group, a benzothiazolonyl group, a 2,4-(1H,3H)quinazolinedionyl group, an indolinyl group, an oxindolyl group, a 1,3-benzoxolyl group, an imidazolidinyl group, a pyrazolidinyl group, an oxazolidinyl group, an isoxazolidinyl group, a thiomorpholinyl group, a dihydrothiazolyl group, an oxetanyl group, a 2-oxa-6-aza-spiro[3.3]heptanyl group, a 1,2,3,4-tetrahydroquinolyl group, an imidazolidonyl group, a pyrazolidonyl group, an oxazolidonyl group, a succinimidyl group, a 2-azetidinoyl group, a 2-oxopiperazinyl group, a 3,5-dioxomorpholinyl group, a 2-oxomorpholinyl group, a 2,5-dehydrouracinyl group, a 2-pyrrolidonyl group, a 2-piperidonyl group, a 4-piperidonyl group, a 1,1,3-trioxo[1,2,5]thiadiazolidinone group, a 1,1-dioxo-1$\lambda^6$-thiomorphonyl group and an imidazolidine-2,4-dione group. In these groups, the carbon atom(s) may be oxidized to form carbonyl, and the heteroatoms may have an oxo group.

The "heterocyclic carbonyl" herein refers to a carbonyl group to which the above-defined "heterocycle" is bonded.

The "alkylamino" herein refers to an amino group to which one or two of the above-defined "alkyl" groups are bonded. Preferred examples include C1-C10 monoalkylamino and C1-C10 dialkylamino, and more preferred examples include C1-C6 monoalkylamino and C1-C6 dialkylamino. Two alkyl groups in the dialkylamino may be the same or different. In particular, it is preferably C1-C3 monoalkylamino or C1-C3 dialkylamino in $R_7$, C1-C3 monoalkylamino or dialkylamino in a substituent on a heterocycle where $R_7$ and $R_8$ are bonded to each other to form the heterocycle, C1-C3 monoalkylamino or C1-C3 dialkylamino in $R_{16}$, C1-C3 monoalkylamino or C1-C3 dialkylamino in $R_{17}$, C1-C3 monoalkylamino or C1-C3 dialkylamino in $R_{21}$, C1-C3 monoalkylamino or C1-C3 dialkylamino in $R_{23}$, C1-C3 monoalkylamino or C1-C3 dialkylamino in $R_{24}$, C1-C3 monoalkylamino or C1-C3 dialkylamino in $R_{11}$, C1-C3 monoalkylamino or C1-C3 dialkylamino in $R_{12}$, C1-C3 monoalkylamino or C1-C3 dialkylamino in $R_{14}$ and C1-C3 monoalkylamino or C1-C3 dialkylamino in $R_{35}$. The "alkyl" in the alkylamino may have the above-defined "aryl" as a substituent(s). Examples of the alkylamino include —NHCH$_3$, —N(CH$_3$)$_2$, —N(CH$_3$)CH$_2$CH$_3$ and —NHCH$_2$Ph.

The "amino" herein refers to a monovalent group having two hydrogen atoms on a nitrogen atom (a group represented by —NH$_2$).

The "arylalkyl" herein refers to a group in which any hydrogen atom in the above-defined "alkyl" is replaced by the above-defined "aryl". Preferred examples of the arylalkyl include C6-C10 aryl C1-C10 alkyl. In particular, it is preferably C6-C10 aryl C1-C3 alkyl in $R_{21}$, C6-C10 aryl C1-C3 alkyl in $R_{35}$ and C6-C10 aryl C1-C3 alkyl in $R_{25}$. Specific examples include a benzyl group, a phenethyl group and a 3-phenyl-1-propyl group.

The "heterocyclic alkyl" herein refers to a group in which any hydrogen atom in the above-defined "alkyl" is replaced by the above-defined "heterocycle". Specific examples include a morpholin-4-yl-methyl group, a 2-(morpholin-4-yl)ethyl group, a 4-hydroxy-piperidin-1-yl-methyl group, a 2-(4-hydroxy-piperidin-1-yl)ethyl group, a 4-methyl-piperazin-1-yl-methyl group and a 2-(4-methyl-piperazin-1-yl-)ethyl group.

The "hydroxyalkyl" herein refers to a group in which any hydrogen atom(s) in the above-defined "alkyl" is replaced by preferably 1 to 4 hydroxyl groups, and it is preferably a C1-C10 hydroxyalkyl group, more preferably a C1-C6 hydroxyalkyl group. In particular, it is preferably a C1-C4 hydroxyalkyl group in $R_{25}$. Specific examples include hydroxymethyl, 2-hydroxyethyl, 3-hydroxypropyl and 2,3-dihydroxypropyl.

The "alkylcarbonylamino" herein refers to an amino group to which one or two of the above-defined "alkylcarbonyl" groups are bonded. Preferred examples include C1-C10 monoalkylcarbonylamino and C1-C10 dialkylcarbonylamino, and more preferred examples include C1-C6 monoalkylcarbonylamino and C1-C6 dialkylcarbonylamino. Two alkyl groups in the dialkylcarbonylamino may be the same or different. In particular, it is preferably C1-C3 alkylcarbonylamino in $R_{17}$, C1-C3 alkylcarbonylamino in $R_{24}$ and C1-C3 alkylcarbonylamino in $R_{35}$. Examples include CH$_3$CONH—.

The "alkoxycarbonylamino" herein refers to an amino group to which one or two of the above-defined "alkoxycarbonyl" groups are bonded. Preferred examples include C1-C10 monoalkoxycarbonylamino and C1-C10 dialkoxycarbonylamino. Two alkoxy groups in the dialkoxycarbonylamino may be the same or different. In particular, it is preferably C1-C4 monoalkoxycarbonyl or C1-C4 dialkoxycarbonylamino in $R_{42}$.

The "alkylaminocarbonyl" herein refers to a carbonyl group to which the above-defined "alkylamino" is bonded, and is preferably C1-C10 alkylaminocarbonyl, more preferably C1-C6 alkylaminocarbonyl. In particular, it is preferably C1-C3 alkylaminocarbonyl in $R_{13}$. Examples include $CH_3NHCO—$.

The "Cn-Cm alkylaminocarbonyl" herein means that the alkyl therein is a "Cn-Cm" alkyl in terms of the number of carbon atoms. Hereinafter, the same applies to a group containing "alkylaminocarbonyl".

The "arylcarbonyl" herein refers to a carbonyl group to which the above-defined "aryl" is bonded.

The "aryloxy" herein refers to an oxy group to which the above-defined "aryl" is bonded.

The "aryloxycarbonyl" herein refers to a carbonyl group to which the above-defined "aryloxy" is bonded.

The "heteroaryloxy" herein refers to an oxy group to which the above-defined "heteroaryl" is bonded.

The "heteroarylcarbonyl" herein refers to a carbonyl group to which the above-defined "heteroaryl" is bonded.

The "hydroxycarbonyl" herein refers to $—CO_2H$(carboxyl).

The "aminocarbonyl" herein refers to a carbonyl group to which the above-defined "amino" is bonded.

The "hydroxyalkylamino" herein refers to an amino group to which one or two of the above-defined "hydroxyalkyl" groups are bonded. Examples include mono(hydroxyalkyl) amino and di(hydroxyalkyl)amino. Two hydroxyalkyl groups in the di(hydroxyalkyl)amino may be the same or different. "—$NHCH_2$— or —$NHCH_2CH_2$—" in W herein is preferably bonded through the nitrogen atom to the sulfonyl group in the formula (1).

The "hydroxyalkylaminoalkyl" herein refers to a group in which any hydrogen atom in the above-defined "alkyl" is replaced by the above-defined "hydroxyalkylamino".

The "alkoxyalkyl" herein refers to a group in which any hydrogen atom in the above-defined "alkyl" is replaced by the above-defined "alkoxy", and is preferably C1-C10 alkoxy-C1-C10 alkyl, more preferably C1-C6 alkoxy-C1-C6 alkyl. In particular, it is preferably C1-C3 alkoxy-C1-C3 alkyl in a substituent on a heterocycle where $R_7$ and $R_8$ are bonded to each other to form the heterocycle.

The "hydroxyalkyloxy" herein refers to a group in which any hydrogen atom in the above-defined "alkoxy" is replaced by a hydroxyl group, and is preferably C1-C10 hydroxyalkyloxy, more preferably C1-C6 hydroxyalkyloxy.

The "thiocarbonyl" herein refers to a group represented by C=S.

The "alkylthio" herein refers to a thio group to which the above-defined "alkyl" is bonded, and is preferably a C1-C10 alkylthio group, more preferably a C1-C6 alkylthio group.

The "B optionally substituted with A" herein denotes that any hydrogen atom(s) in B may be replaced with any number of As.

In the present invention, the number of substituents is not limited unless otherwise indicated. For example, the number of substituents may be 1 to 7, 1 to 4, 1 to 3, 1 to 2, or 1.

The "PTH-like effect" herein refers to activity of increasing intracellular cAMP (cAMP: cyclic adenosine monophosphate) by action on the PTH receptor or action on the signal transduction pathway through the PTH receptor.

Herein, "*" in a chemical formula denotes a bonding position.

The compounds according to the present invention, whether free forms or pharmacologically acceptable salts, are included in the present invention. Examples of such "salts" include inorganic acid salts, organic acid salts, inorganic base salts, organic base salts and acidic or basic amino acid salts.

Preferred examples of the inorganic acid salts include hydrochlorides, hydrobromides, sulfates, nitrates and phosphates. Preferred examples of the organic acid salts include acetates, succinates, fumarates, maleates, tartrates, citrates, lactates, stearates, benzoates, methanesulfonates and p-toluenesulfonates.

Preferred examples of the inorganic base salts include alkali metal salts such as sodium salts and potassium salts, alkaline earth metal salts such as calcium salts and magnesium salts, aluminum salts and ammonium salts. Preferred examples of the organic base salts include diethylamine salts, diethanolamine salts, meglumine salts and N,N-dibenzylethylenediamine salts.

Preferred examples of the acidic amino acid salts include aspartates and glutamates. Preferred examples of the basic amino acid salts include arginine salts, lysine salts and ornithine salts.

The compounds of the present invention may absorb moisture, have adsorbed water or form hydrates when left in the air. Such hydrates are also included in the salts of the present invention.

Further, the compounds I of the present invention may absorb certain other solvents to form solvates. Such salts are also encompassed in the present invention as salts of the compounds of the formula (1) or (2).

Herein, a structural formula of a compound may represent a certain isomer for the sake of convenience. However, the compounds of the present invention include all isomers such as geometric isomers, optical isomers based on asymmetric carbons, stereoisomers and tautomers as well as mixtures of these isomers which occur due to the structures of the compounds, without being limited to the formulas described for the sake of convenience, and may be either one of isomers or a mixture thereof. Thus, the compounds of the present invention may have an asymmetric carbon atom in the molecule and may be present as optically active forms and racemates, but the present invention is not limited to either of them and includes both of them.

The present invention includes all isotopes of the compounds represented by the formula (1) or (2). In the isotopes of the compounds of the present invention, at least one atom is replaced by an atom having the same atomic number (proton number) but having a different mass number (sum of the number of protons and the number of neutrons). Examples of the isotopes contained in the compounds of the present invention include a hydrogen atom, a carbon atom, a nitrogen atom, an oxygen atom, a phosphorus atom, a sulfur atom, a fluorine atom and a chlorine atom, including 2H, 3H, 13C, 14C, 15N, 17O, 18O, 31P, 32P, 35S, 18F and 36Cl, respectively. In particular, radioisotopes that decay by emitting radioactivity such as 3H and 14C are useful in body tissue distribution tests for pharmaceuticals or compounds. Stable isotopes do not decay, are almost equal in abundance and do not emit radioactivity, and thus they can be used safely. The isotopes of the compounds of the present invention can be converted according to conventional methods by substituting a reagent containing a corresponding isotope for a reagent used for synthesis.

The compounds according to the present invention may exhibit crystalline polymorphism, but are not particularly limited to any one of these, but may be in any one of these crystal forms or exist as a mixture of two or more crystal forms.

The compounds according to the present invention include prodrugs thereof. The prodrugs are derivatives of the compounds of the present invention which have chemically or metabolically decomposable groups and are converted back to the original compounds after administration in vivo to exhibit their original efficacy, including complexes not formed with covalent bonds, and salts.

The compounds represented by the above formula (1) or (2) according to the present invention are preferably as follows.

W is preferably selected from:
1) a single bond,
2) C1-C10 alkylene optionally containing a carbonyl group, wherein the alkylene is optionally substituted with a halogen atom(s) and/or a hydroxyl group(s),
3) C2-C10 alkenylene optionally substituted with a halogen atom(s),
4) C2-C10 alkynylene,
5) arylene optionally substituted with a halogen atom(s),
6) heteroarylene optionally substituted with a halogen atom(s),
7) C1-C10 heteroalkylene optionally substituted with a halogen atom(s),
8) —NH—, —NHCH$_2$— or —NHCH$_2$CH$_2$—,
9) cycloalkylene and
10) -(cycloalkylene)-CH$_2$—.

More preferably, the above W is selected from:
1) a single bond,
2) C1-C10 alkylene optionally containing a carbonyl group, wherein the alkylene is optionally substituted with a halogen atom(s) or hydroxy,
3) C2-C10 alkenylene optionally substituted with a halogen atom(s),
4) C2-C10 alkynylene,
5) arylene,
6) heteroarylene,
7) —NH—, —NHCH$_2$— or —NHCH$_2$CH$_2$—,
8) cycloalkylene and
9) -(cycloalkylene)-CH$_2$—.

Still more preferably, the above W is selected from:
1) a single bond,
2) C1-C10 alkylene optionally substituted with a halogen atom(s),
3) C2-C10 alkenylene,
4) C2-C10 alkynylene and
5) heteroarylene.

Particularly preferably, the above W is selected from:
1) C1-C6 alkylene optionally substituted with a fluorine atom(s),
2) C1-C6 alkenylene and
3) thiophene.

More particularly preferably, the above W is selected from:
1) ethylene,
2) vinylene and
3) thiophene.

The above X is preferably selected from the following bond or groups:
1) a single bond,
2) C1-C10 alkylene optionally substituted with a halogen atom(s) or cycloalkyl,
3) C2-C10 alkenylene optionally substituted with a halogen atom(s),
4) C2-C10 alkynylene optionally substituted with a halogen atom(s),
5) C1-10 oxyalkylene optionally substituted with a halogen atom(s) and
6) —NR$_{47}$—
   wherein R$_{47}$ is selected from:
   i) a hydrogen atom and
   ii) C1-C10 alkyl optionally substituted with a halogen atom(s).

More preferably, the above X is selected from the following bond or groups:
1) a single bond,
2) C1-C10 alkylene optionally substituted with cycloalkyl,
3) C2-C10 alkenylene,
4) C2-C10 alkynylene and
5) C1-C10 oxyalkylene.

Still more preferably, the above X is selected from the following bond or groups:
1) a single bond,
2) C1-C10 alkylene,
3) C2-C10 alkenylene,
4) C2-C10 alkynylene and
5) C1-C10 oxyalkylene, wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene.

Particularly preferably, the above X is selected from the following bond or groups:
1) a single bond,
2) C1-C6 alkylene and
3) C1-C6 oxyalkylene optionally substituted with a halogen atom(s), wherein the oxyalkylene is bonded to a 1,3,8-triaza-spiro[4.5]dec-1-en-4-one ring or a 1,3,8-triaza-spiro[4.5]dec-1-ene-4-thione ring through a carbon atom in the oxyalkylene.

More particularly preferably, the above X is a single bond.

The above Y is preferably selected from:
1) an oxygen atom,
2) a sulfur atom and
3) =NR$_{37}$,
or 4) Y is —NR$_{38}$R$_{39}$ represented by the following formula (A):

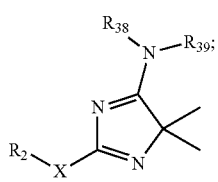

and can form tautomers;
R$_{37}$ is selected from:
1) hydrogen,
2) hydroxy and
3) C1-C10 alkoxy; and
R$_{38}$ and R$_{39}$ are independently selected from hydrogen or C1-C10 alkyl optionally substituted with cycloalkyl, or R$_{38}$ and $R_{39}$ may be bonded to each other to form a ring selected from the group consisting of azetidinyl, pyrrolidinyl, piperidinyl, piperazinyl and morpholinyl, and the ring is optionally substituted with C1-C10 alkyl.

More preferably, the above Y is an oxygen atom.

The above m is preferably an integer of 0 to 2, more preferably 1.

The above n is preferably an integer of 0 to 2, more preferably 1.

The above $R_1$ is preferably selected from:
1) hydrogen,
2) cycloalkyl optionally substituted with a group(s) selected from $R_4$, $R_5$ and $R_6$,
3) a heterocycle optionally substituted with a group(s) selected from $R_{25}$, $R_4$, $R_5$ and $R_6$,
4) aryl optionally substituted with a group(s) selected from $R_3$, $R_4$, $R_5$ and $R_6$ and
5) heteroaryl optionally substituted with a group(s) selected from $R_{25}$, $R_4$, $R_5$ and $R_6$.

More preferably, the above $R_1$ is selected from:
1) hydrogen,
2) cycloalkyl optionally substituted with a group selected from $R_4$,
3) a heterocycle optionally substituted with a group(s) selected from $R_{25}$ and $R_4$,
4) aryl optionally substituted with a group(s) selected from $R_3$, $R_4$, $R_5$ and $R_6$ and
5) heteroaryl optionally substituted with a group(s) selected from $R_{25}$, $R_4$ and $R_5$.

Still more preferably, the above $R_1$ is selected from:
1) aryl optionally substituted with a group(s) selected from $R_3$, $R_4$ and $R_5$ and
2) heteroaryl optionally substituted with a group(s) selected from $R_{25}$ and $R_4$.

Particularly preferably, the above $R_1$ is the following general formula (3) or (4).

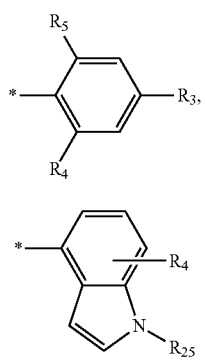

The above $R_3$ is preferably selected from:
1) —$CONR_7R_8$,
2) —$OR_9$,
3) —$NR_9R_{10}$,
4) —$N(R_9) COR_{11}$,
5) —$N(R_9) SO_2R_{12}$,
6) —$SO_2R_{15}$,
7) C1-10 alkyl optionally substituted with a group(s) independently selected from a halogen atom, a hydroxyl group, —$COR_{16}$ and —$NR_{13}R_{14}$,
8) heteroaryl having C1-10 alkyl and/or C1-10 alkoxy as a substituent(s) and
9) —$N(R_9)CSR_{11}$.

More preferably, the above $R_3$ is selected from:
1) —$CONR_7R_8$,
2) —$OR_9$,
3) —$NR_9R_{10}$,
4) —$N(R_9) COR_{11}$,
5) —$N(R_9) SO_2R_{12}$,
6) —$SO_2R_{15}$,
7) C1-C10 alkyl optionally substituted with a group(s) selected from —$COR_{16}$ and —$NR_{13}R_{14}$ and
8) —$N(R_9)CSNH_2$.

Still more preferably, the above $R_3$ is selected from:
1) —$CONR_7R_8$,
2) —$OR_9$,
3) —$NR_9R_{10}$,
4) —$N(R_9) COR_{11}$,
5) —$N(R_9) SO_2R_{12}$,
6) —$SO_2R_{15}$ and
7) C1-C6 alkyl optionally substituted with a group(s) selected from —$COR_{16}$ and —$NR_{13}R_{14}$.

The above $R_4$ is preferably selected from:
1) halogen,
2) cyano,
3) nitro,
4) amino,
5) —$NHCOR_{26}$,
6) C1-C10 alkyl optionally substituted with a group(s) independently selected from hydroxycarbonyl, C1-C10 alkoxycarbonyl and aminocarbonyl,
7) C1-C10 haloalkyl,
8) C1-C10 alkoxy,
9) C1-C10 haloalkylcarbonyl,
10) —$COR_{16}$,
11) C1-C10 hydroxyalkyl and
12) C1-C10 heteroalkyl.

More preferably, the above $R_4$ is selected from:
1) halogen,
2) cyano,
3) amino,
4) C1-C10 alkyl,
5) C1-C10 haloalkyl,
6) C1-C10 alkoxy,
7) C1-C10 haloalkylcarbonyl,
8) —$COR_{16}$ and
9) C1-C10 heteroalkyl.

The above $R_5$ is preferably selected from a halogen atom, C1-C10 alkyl, C1-C10 haloalkyl and C1-C10 alkoxy.

The above $R_6$ is preferably selected from a halogen atom, C1-C10 alkyl and C1-C10 haloalkyl.

The above $R_7$ is preferably selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —$(CH_2)_LCOR_{16}$ (wherein L represents an integer of 1 to 4),
12) C1-C10 alkoxy,
13) C2-C10 alkenyl and
14) —$NR_{40}R_{41}$; and $R_{40}$ and $R_{41}$ are independently selected from hydrogen, C1-C10 alkyl and C1-C10 alkylcarbonyl, or $R_{40}$ and $R_{41}$ may be bonded to each other to form a ring selected from azetidinyl, pyrrolidinyl, piperidinyl, piperazinyl and morpholinyl, and the heterocycle is optionally substituted with C1-C10 alkyl.

The above $R_8$ is preferably selected from hydrogen and C1-C10 alkyl optionally substituted with a halogen atom(s) and/or a hydroxyl group(s).

The above $R_7$ and $R_8$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent(s),
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl optionally substituted with C1-C10 alkyl,
11) heterocyclyl C1-C10 alkyl,
12) —$COR_{16}$,
13) —$NR_{19}R_{20}$,
14) —$SO_2R_{21}$,
15) C1-C10 alkoxy-C1-C10 alkyl optionally having a hydroxyl group(s) as a substituent(s) and
16) C1-C10 hydroxyalkyloxy, wherein the hydrogen atom of the hydroxyl group may be replaced by C1-C10 hydroxyalkyl, and
the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl.

The above $R_{16}$ is preferably selected from:
1) a hydroxyl group,
2) C1-C10 alkoxy,
3) $NR_{17}R_{18}$ and
4) C1-C10 alkyl optionally substituted with a substituent(s) selected from a halogen atom, a hydroxyl group, C1-C10 alkoxycarbonyl or C1-C10 alkylamino.

The above $R_{17}$ is preferably selected from:
1) hydrogen,
2) C1-C10 alkyl optionally substituted with a group(s) selected from aryl, amino, C1-C10 alkylamino, C1-C10 alkylcarbonylamino and a hydroxyl group,
3) heteroaryl and
4) C1-C10 alkoxy.

The above $R_{18}$ is preferably selected from hydrogen, C1-C10 alkyl and C1-C10 hydroxyalkyl.

The above $R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl.

The above $R_{19}$ is preferably selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl.

The above $R_{20}$ is preferably selected from hydrogen and C1-C10 alkyl.

The above $R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{21}$ is preferably selected from:
1) C1-C10 alkyl optionally substituted with aryl,
2) amino,
3) C1-C10 alkylamino and
4) aryl optionally substituted with C1-C10 alkyl.

The above $R_9$ is preferably selected from:
1) hydrogen,
2) C1-C10 alkyl optionally substituted with a group(s) independently selected from $R_{23}$,
3) aryl optionally substituted with a group(s) selected from a halogen atom, a hydroxyl group, amino and C1-C10 alkylamino,
4) cycloalkyl optionally substituted with a halogen atom(s) or a hydroxyl group(s),
5) a heterocycle optionally substituted with a group(s) independently selected from C1-C10 alkyl, C1-C10 alkylcarbonyl, C1-C10 alkoxy, C1-C10 alkoxycarbonyl, amino and a halogen atom,
6) C1-C10 heteroalkyl optionally substituted with a group(s) independently selected from a halogen atom and a hydroxyl group,
7) heteroaryl optionally substituted with a group(s) selected from C1-C10 alkyl, C1-C10 alkylcarbonyl, C1-C10 alkoxycarbonyl and a halogen atom and
8) cycloalkenyl optionally substituted with a group(s) selected from C1-C10 alkoxy, C1-C10 alkylamino, amino, a hydroxyl group and a halogen atom, wherein the cycloalkenyl may contain a carbonyl group.

More preferably, the above $R_9$ is selected from:
1) hydrogen,
2) C1-C10 alkyl optionally substituted with a group(s) independently selected from $R_{23}$,
3) cycloalkyl optionally substituted with a halogen atom(s) or a hydroxyl group(s),
4) a heterocycle optionally substituted with a group(s) selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) selected from a halogen atom and a hydroxyl group,
6) heteroaryl optionally substituted with a group(s) independently selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, 1 to 3 hydroxyl groups and 1 to 4 halogen atoms, wherein the cycloalkenyl may contain a carbonyl group.

The above $R_{23}$ is preferably selected from:
1) a halogen atom,
2) a hydroxyl group,
3) a C1-C10 alkylcarbonyloxy group,
4) —$COR_{16}$,
5) amino,
6) C1-C10 alkylamino, 7) a heterocycle optionally substituted with a group(s) selected from C1-C10 alkyl, C1-C10 alkylcarbonyl, C1-C10 alkoxycarbonyl and a halogen atom and
8) cyano.

The above $R_{10}$ is preferably selected from:
1) hydrogen and
2) C1-C10 alkyl optionally substituted with a group(s) selected from a halogen atom, a hydroxyl group and aryl.

$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$.

The above $R_{24}$ is preferably selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) independently selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl,
11) heterocyclyl C1-C10 alkyl,
12) —$COR_{16}$,
13) —$NR_{19}R_{20}$ and
14) —$SO_2R_{21}$.

More preferably, the above $R_{24}$ is selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with one to two types of groups selected from a halogen atom, a hydroxyl group, amino and C1-C10 alkylamino,
9) —$COR_{16}$ and
10) —$NR_{19}R_{20}$.

The above $R_{11}$ is preferably selected from:
1) C1-C10 alkyl optionally substituted with a group(s) independently selected from:
  i) a hydroxyl group,
  ii) —$NR_{17}R_{18}$,
  iii) a C1-C10 alkoxy group,
  iv) a halogen atom,
  v) C1-C10 alkoxycarbonyl,
  vi) aminocarbonyl and
  vii) aryl optionally substituted with a group(s) independently selected from a halogen atom, a hydroxyl group, C1-C10 alkoxy, amino, C1-C10 alkylamino and —$COR_{22}$,
2) aryl optionally substituted with a group(s) independently selected from a halogen atom, a hydroxyl group, C1-C10 alkoxy, amino, C1-C10 alkylamino and —$COR_{22}$,
3) cycloalkyl optionally substituted with a halogen atom(s),
4) a heterocycle optionally substituted with a group(s) selected from C1-C10 alkyl, C1-C10 alkylcarbonyl, C1-C10 alkoxycarbonyl and a halogen atom,
5) C1-C10 alkoxy, wherein the alkyl group is optionally substituted with a group(s) independently selected from C1-C10 alkylcarbonylamino, amino, C1-C10 alkylamino and a hydroxyl group,
6) amino,
7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
8) C2-C10 alkenyl.

More preferably, the above $R_{11}$ is selected from:
1) C1-C10 alkyl optionally substituted with 1 to 3 substituents independently selected from:
  i) a hydroxyl group,
  ii) —$NR_{17}R_{18}$,
  iii) a C1-C10 alkoxy group,
  iv) a halogen atom,
  v) C1-C10 alkoxycarbonyl and
  vi) aminocarbonyl,
2) aryl,
3) aryl C1-C10 alkyl,
4) cycloalkyl optionally substituted with a halogen atom(s),
5) a heterocycle optionally substituted with C1-C10 alkyl,
6) C1-C10 alkoxy, wherein the alkyl group is optionally substituted with a group(s) independently selected from C1-C10 alkylcarbonylamino, amino, C1-C10 alkylamino and a hydroxyl group,
7) amino,
8) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
9) C2-C10 alkenyl.

The above $R_{22}$ is preferably selected from C1-C10 alkoxy, a hydroxyl group, amino and C1-C10 alkylamino.

The above $R_{12}$ is preferably selected from:
1) C1-C10 alkyl,
2) amino and
3) C1-C10 alkylamino, wherein the alkyl group is optionally substituted with a group(s) independently selected from amino, C1-C10 alkylamino and a hydroxyl group.

The above $R_{13}$ is preferably selected from:
1) hydrogen,
2) C1-C10 alkyl,
3) C1-C10 alkylcarbonyl, wherein the alkyl is optionally substituted with a hydroxyl group(s),
4) C1-C10 alkoxycarbonyl,
5) aminocarbonyl,
6) C1-C10 alkylaminocarbonyl and
7) heterocyclic carbonyl optionally substituted with C1-C10 alkyl.

The above $R_{14}$ is preferably selected from:
1) hydrogen and
2) C1-C10 alkyl optionally substituted with a group(s) independently selected from a halogen atom, a hydroxyl group, amino and C1-C10 alkylamino.

Further, $R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl.

The above $R_{15}$ is preferably selected from:
1) C1-C10 alkyl and
2) —$NR_{35}R_{36}$.

The above $R_{35}$ is preferably selected from:
1) hydrogen,
2) C1-C10 alkyl optionally substituted with a group(s) independently selected from:
   i) a halogen atom,
   ii) a hydroxyl group,
   iii) C1-C10 alkylcarbonylamino,
   iv) —$COR_{16}$,
   v) amino,
   vi) C1-C10 alkylamino,
   vii) C1-C10 alkoxy optionally substituted with a halogen atom(s),
   viii) heteroaryl optionally substituted with a C1-C10 alkyl group(s) and
   ix) a heterocycle,
3) aryl optionally substituted with a group(s) independently selected from a halogen atom, a hydroxyl group, amino and C1-C10 alkylamino,
4) cycloalkyl optionally substituted with a group(s) independently selected from a halogen atom and a hydroxyl group,
5) a heterocycle optionally substituted with a group(s) independently selected from C1-C10 alkyl, a halogen atom and aryl C1-C10 alkyl,
6) heteroaryl optionally substituted with C1-C10 alkyl and
7) C1-C10 alkylcarbonyl.

The above $R_{36}$ is preferably selected from:
1) hydrogen and
2) C1-C10 alkyl optionally substituted with a group(s) independently selected from a halogen atom, a hydroxyl group and aryl.

The above $R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{25}$ is preferably selected from:
1) a halogen atom,
2) C1-C10 alkyl optionally substituted with a group(s) independently selected from:
   i) a halogen atom,
   ii) aryl,
   iii) heteroaryl,
   iv) a heterocycle optionally substituted with a C1-C10 alkyl group(s),
   v) —$COR_{16}$,
   vi) —$NR_{13}R_{14}$ and
   vii) —$SO_2R_{21}$,
3) C1-C10 heteroalkyl optionally substituted with a hydroxyl group(s),
4) C1-C10 hydroxyalkyl, wherein each hydroxyl group may be independently substituted with a group(s) selected from C1-C10 alkyl, aryl C1-C10 alkyl and C1-C10 alkylcarbonyl,
5) —$COR_{16}$,
6) —$SO_2R_{21}$,
7) aryl and
8) cyano.

The above $R_2$ is preferably selected from:
1) C1-C10 alkyl optionally substituted with a halogen atom (s), wherein the alkyl group is optionally further substituted with a substituent(s) independently selected from $R_{42}$,
2) C2-C10 alkenyl optionally substituted with a halogen atom(s), wherein the alkenyl group is optionally further substituted with a substituent(s) independently selected from $R_{42}$,
3) C2-C10 alkynyl optionally substituted with a halogen atom(s), wherein the alkynyl group is optionally further substituted with a substituent(s) independently selected from $R_{42}$,
4) cycloalkyl optionally substituted with a group(s) independently selected from:
   i) a halogen atom,
   ii) C2-C10 alkenyl or C1-C10 alkyl,
   iii) aryl optionally substituted with 1 to 3 substituents independently selected from C1-C10 alkyl, a halogen atom, C1-C10 alkoxy, C1-C10 alkylamino and C1-C10 alkylcarbonyl,
   iv) cycloalkyl,
   v) C2-C10 alkenyl optionally substituted with halogen,
   vi) C1-C10 alkylidene, wherein the alkylidene is bonded to the cycloalkyl by a double bond and the alkylidene is optionally substituted with a halogen atom(s),
   vii) C1-C10 alkoxy optionally substituted with a halogen atom(s),
   viii) C1-C10 alkyl optionally substituted with a group(s) independently selected from a halogen atom or C1-C10 alkoxy optionally substituted with a halogen atom(s),
   ix) C2-C10 alkynyl and
   x) —$Si(R_{43})_3$,
5) a heterocycle, wherein the heterocycle is optionally substituted with a group(s) independently selected from:
   i) a C1-C10 alkyl group,
   ii) C1-C10 alkylcarbonyl, wherein the alkyl group is optionally substituted with $R_{27}$,
   iii) arylcarbonyl, wherein the aryl group is optionally substituted with a group(s) independently selected from a halogen atom, C1-C10 alkyl and C1-C10 alkoxy,
   iv) heteroarylcarbonyl,
   v) C1-C10 alkoxycarbonyl, wherein the alkyl group is optionally substituted with a group(s) independently selected from a halogen atom, aryl and C1-C10 alkoxy,
   vi) aryloxycarbonyl, wherein the aryl group is optionally substituted with a halogen atom(s) and/or C1-C10 alkyl,
   vii) —$CONR_{28}R_{29}$,
   viii) —$SO_2R_{21}$,
   ix) a halogen atom,
   x) cycloalkylcarbonyl optionally fused with an aryl group and
   xi) C2-C10 alkenylcarbonyl, wherein the alkenyl group is optionally substituted with aryl, wherein the aryl is optionally substituted with a group(s) independently selected from a halogen atom, C1-C10 alkyl or C1-C10 alkoxy,
6) aryl optionally substituted with a group(s) independently selected from $R_{44}$,
7) heteroaryl optionally substituted with a group(s) independently selected from:
   i) a halogen atom,
   ii) C1-C10 alkyl and
   iii) C1-C10 alkoxy;
8) C1-C10 alkoxy optionally substituted with a halogen atom(s), wherein the alkoxy group is optionally further substituted with a substituent(s) independently selected from $R_{42}$,
9) —$S(O)_qR_{43}$ (wherein q is an integer of 0 to 2) and
10) cycloalkenyl optionally substituted with C1-C10 alkyl.

More preferably, the above $R_2$ is selected from:
1) C1-C10 alkyl optionally substituted with a halogen atom(s), wherein the alkyl group is optionally further substituted with a group selected from $R_{42}$,
2) C2-C10 alkenyl optionally substituted with a halogen atom(s), wherein the alkenyl group is optionally further substituted with a group selected from $R_{42}$,
3) C2-C10 alkynyl optionally substituted with a halogen atom(s), wherein the alkynyl group is optionally further substituted with a group selected from $R_{42}$,
4) cycloalkyl optionally substituted with a group(s) independently selected from:
   i) a halogen atom,
   ii) C2-C10 alkenyl or C1-C10 alkyl,
   iii) aryl optionally substituted with a group(s) independently selected from C1-C10 alkyl, a halogen atom and C1-C10 alkoxy,
   iv) cycloalkyl,
   v) C2-C10 haloalkenyl or C1-C10 haloalkyl,
   vi) C1-C10 alkylidene, wherein the alkylidene is bonded to the cycloalkyl by a double bond and the alkylidene is optionally substituted with a halogen atom(s),
   vii) C1-C10 alkoxy optionally substituted with a halogen atom(s),
   viii) C1-C10 alkyl substituted with C1-C10 alkoxy, wherein the alkyl and/or the alkyl in the alkoxy is optionally substituted with a halogen atom(s),
   ix) C2-C10 alkynyl and
   x) —Si($R_{43}$)$_3$,
5) a heterocycle, wherein the heterocycle is optionally substituted with a group(s) selected from:
   i) a C1-C10 alkyl group,
   ii) C1-C10 alkylcarbonyl, wherein the alkyl group is optionally substituted with $R_{27}$,
   iii) arylcarbonyl, wherein the aryl group is optionally substituted with a group(s) independently selected from a halogen atom, C1-C10 alkyl and C1-C10 alkoxy,
   iv) heteroarylcarbonyl,
   v) C1-C10 alkoxycarbonyl, wherein the alkyl group is optionally substituted with a group(s) independently selected from a halogen atom, aryl and C1-C10 alkoxy,
   vi) aryloxycarbonyl, wherein the aryl group is optionally substituted with a halogen atom(s) and/or C1-C10 alkyl,
   vii) —CONR$_{28}$R$_{29}$ and
   viii) —SO$_2$R$_{21}$,
6) aryl optionally substituted with a group(s) independently selected from $R_{44}$,
7) heteroaryl optionally substituted with any of the following groups:
   i) C1-C10 alkyl,
8) C1-C10 alkoxy optionally substituted with a halogen atom(s), wherein the alkoxy group is optionally further substituted with a group selected from $R_{42}$,
9) —S(O)$_q$R$_{43}$ (wherein q is an integer of 0 to 2) and
10) cycloalkenyl optionally substituted with C1-C10 alkyl.
   Still more preferably, the above $R_2$ is selected from:
1) C1-C13 alkyl optionally substituted with a halogen atom(s), wherein the alkyl group is optionally further substituted with a group selected from $R_{42}$,
2) C2-C13 alkenyl optionally substituted with a halogen atom(s), wherein the alkenyl group is optionally further substituted with a group selected from $R_{42}$,
3) C2-C13 alkynyl optionally substituted with a halogen atom(s), wherein the alkynyl group is optionally further substituted with a group selected from $R_{42}$,
4) cycloalkyl optionally substituted with a group(s) independently selected from:
   i) a halogen atom,
   ii) C2-C6 alkenyl or C1-C6 alkyl,
   iii) aryl optionally substituted with a group(s) independently selected from C1-C6 alkyl, a halogen atom, C1-C6 alkoxy, C1-C6 alkylamino and C1-C6 alkylcarbonyl,
   iv) cycloalkyl,
   v) C2-C6 haloalkenyl or C1-C6 haloalkyl,
   vi) C1-C6 alkylidene, wherein the alkylidene is bonded to the cycloalkyl by a double bond and the alkylidene is optionally substituted with a halogen atom(s),
   vii) C1-C6 alkoxy optionally substituted with a halogen atom(s),
   viii) C1-C6 alkyl substituted with C1-C6 alkoxy, wherein the alkyl and/or the alkyl in the alkoxy is optionally substituted with halogen,
   ix) C2-C6 alkynyl and
   x) —Si($R_{43}$)$_3$,
5) a group represented by the following general formula (B)

(wherein Ra represents a group selected from:
   i) C1-C6 alkylcarbonyl, wherein the alkyl group is optionally substituted with $R_{27}$,
   ii) arylcarbonyl, wherein the aryl group is optionally substituted with a group(s) independently selected from a halogen atom, C1-C6 alkyl and C1-C6 alkoxy,
   iii) C1-C6 alkoxycarbonyl, wherein the alkyl group is optionally substituted with a group(s) selected from a halogen atom, aryl and C1-C6 alkoxy,
   iv) aryloxycarbonyl, wherein the aryl group is optionally substituted with a halogen atom(s) or C1-C6 alkyl,
   v) —CONR$_{28}$R$_{29}$ and
   vi) —SO$_2$R$_{21}$),
6) aryl optionally substituted with a group(s) independently selected from $R_{44}$,
7) heteroaryl optionally substituted with any of the following groups:
   i) a halogen atom,
   ii) C1-C6 alkyl and
   iii) C1-C6 alkoxy;
8) C1-C6 alkoxy optionally substituted with a halogen atom(s), wherein the alkoxy group is optionally further substituted with a group selected from $R_{42}$,
9) —S(O)$_q$R$_{43}$ (wherein q is an integer of 0 to 2) and
10) cycloalkenyl optionally substituted with C1-C6 alkyl.
   When the above $R_2$ is a "cycloalkyl optionally substituted with 1 to 3 substituents" and the substituent is "alkylidene (wherein the alkylidene is bonded to the cycloalkyl by a double bond and the alkylidene is optionally substituted with 1 to 5 halogen atoms)", examples of the $R_2$ include the following groups.

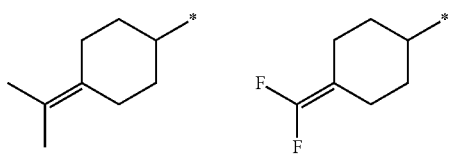

-continued

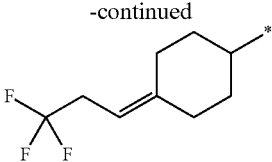

$R_{44}$ is preferably selected from:
1) a halogen atom,
2) cyano,
3) C1-C10 alkyl optionally substituted with a group(s) independently selected from:
  i) a hydroxyl group,
  ii) —$OR_{26}$,
  iii) cyano,
  iv) aryloxy optionally substituted with a group(s) independently selected from a halogen atom, C1-C10 alkyl optionally substituted with a halogen atom(s) or C1-C10 alkoxy optionally substituted with a halogen atom(s) and
  v) a halogen atom,
4) cycloalkyl optionally substituted with a group(s) independently selected from a halogen atom or C1-C10 alkyl optionally substituted with a halogen atom(s),
5) C1-C10 alkoxy optionally substituted with a halogen atom(s) or a C2-C6 alkenyl group(s),
6) —$COR_{30}$,
7) C1-C10 alkylcarbonylamino,
8) C1-C10 alkoxycarbonylamino, wherein the alkoxy group is optionally substituted with aryl,
9) C1-C10 heteroalkyl optionally substituted with a halogen atom(s),
10) aryl optionally substituted with a substituent(s) independently selected from:
  i) a halogen atom,
  ii) C1-C10 alkyl,
  iii) C1-C10 alkoxy and
  iv) aryl optionally substituted with aryl optionally substituted with C1-C10 alkyl,
11) heteroaryl optionally substituted with a C1-C10 alkyl group(s),
12) —$SO_2R_{43}$,
13) —$SOR_{43}$,
14) C1-C10 alkylthio optionally substituted with a halogen atom(s),
15) —$Si(R_{43})_3$ and
16) —$SF_5$.

More preferably, $R_{44}$ is selected from:
1) a halogen atom,
2) cyano,
3) C1-C10 alkyl optionally substituted with any of the following groups:
  i) a hydroxyl group,
  ii) —$OR_{26}$,
  iii) cyano and
  iv) aryloxy optionally substituted with a group(s) selected from a halogen atom, C1-C10 alkyl, C1-C10 haloalkyl or C1-C10 haloalkoxy,
4) C1-C10 haloalkyl,
5) cycloalkyl optionally substituted with a group(s) selected from a halogen atom and C1-C10 haloalkyl,
6) C1-C10 alkoxy optionally substituted with a halogen atom(s) or a C2-C6 alkenyl group(s),
7) —$COR_{30}$,
8) C1-C10 heteroalkyl optionally substituted with a halogen atom(s),
9) aryl optionally substituted with a group(s) independently selected from:
  i) C1-C10 alkyl and
  ii) aryl,
10) heteroaryl optionally substituted with a C1-C10 alkyl group(s),
11) —$SO_2R_{43}$,
12) C1-C10 alkylthio optionally substituted with a halogen atom(s),
13) —$Si(R_{43})_3$ and
14) —$SF_5$.

Still more preferably, $R_{44}$ is selected from:
1) a halogen atom,
2) cyano,
3) C1-C6 alkyl optionally substituted with any of the following groups:
  i) a hydroxyl group,
  ii) —$OR_{26}$,
  iii) cyano and
  iv) aryloxy optionally substituted with a group(s) selected from a halogen atom, C1-C6 alkyl, C1-C6 haloalkyl or C1-C6 haloalkoxy,
4) C1-C6 haloalkyl,
5) cycloalkyl optionally substituted with a group(s) selected from a halogen atom and C1-C6 haloalkyl,
6) C1-C6 alkoxy optionally substituted with a halogen atom(s),
7) —$COR_{30}$,
8) C1-C6 heteroalkyl optionally substituted with a halogen atom(s),
9) aryl optionally substituted with a group(s) independently selected from:
  i) C1-C6 alkyl and
  ii) aryl,
10) heteroaryl optionally substituted with a C1-C6 alkyl group(s),
11) —$SO_2R_{43}$,
12) C1-C6 alkylthio optionally substituted with a halogen atom(s),
13) —$Si(R_{43})_3$ and
14) —$SF_5$.

$R_{42}$ is preferably selected from:
1) hydrogen,
2) aryl optionally substituted with a group(s) independently selected from C1-C10 alkyl optionally substituted with halogen, a halogen atom and C1-C10 alkoxy,
3) hydroxycarbonyl,
4) C1-C10 alkoxycarbonyl,
5) aminocarbonyl,
6) C1-C10 alkylaminocarbonyl,
7) C1-C10 alkoxycarbonylamino,
8) amino,
9) a hydroxyl group and
10) oxetane, tetrahydrofuran or tetrahydropyran optionally substituted with C1-C10 alkyl.

$R_{43}$ preferably represents a C1-C10 alkyl group.

$R_{26}$ is preferably aryl, or C1-C10 alkyl optionally substituted with a halogen atom(s).

$R_{27}$ is preferably selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) a hydroxyl group,
4) amino,
5) C1-C10 alkylamino, 6) hydroxycarbonyl,
7) heteroaryl optionally substituted with a group(s) independently selected from C1-C10 alkyl and/or aryl, and
8) heteroaryloxy.

More preferably, $R_{27}$ is selected from:
1) aryl optionally substituted with a group(s) independently selected from a halogen atom, C1-C10 alkyl and C1-C10 alkoxy,
2) C1-C10 alkoxy, wherein the alkyl group is optionally substituted with aryl,
3) heteroaryl optionally substituted with a group(s) independently selected from C1-C10 alkyl and aryl and
4) heteroaryloxy.

The above $R_{28}$ is preferably selected from hydrogen or C1-C10 alkyl optionally substituted with aryl.

The above $R_{29}$ is preferably selected from hydrogen or C1-C10 alkyl optionally substituted with aryl.

The above $R_{28}$ and $R_{29}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom.

The above $R_{30}$ is preferably selected from a hydroxyl group, C1-C10 alkoxy and —$NR_{31}R_{32}$.

Preferably, the above $R_{31}$ and $R_{32}$ are independently selected from:
1) hydrogen,
2) C1-C10 alkyl optionally substituted with aryl and
3) aryl.

The above $R_{31}$ and $R_{32}$ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl.

Preferably, the above $R_{33}$ and $R_{34}$ are independently selected from:
1) hydrogen and
2) C1-C10 alkyl.

More preferably, the above $R_{33}$ and $R_{34}$ are hydrogen.

In the above formula (2), U preferably represents a bond, C1-C10 alkylene or any group selected from groups represented by the following formula.

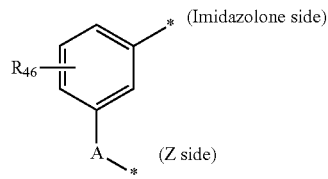

More preferably, U is C1-C6 alkylene or any group selected from groups represented by the following formula.

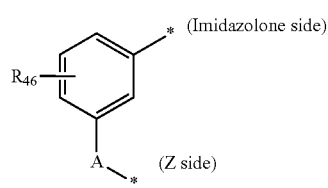

A is preferably selected from O, NH and $CH_2$ and is more preferably O.

$R_{46}$ is preferably selected from hydrogen or $R_{44}$, more preferably selected from hydrogen, C1-C10 alkyl, C1-C10 haloalkyl and C1-C10 hydroxyalkyl, and still more preferably selected from C1-C10 alkyl, C1-C10 haloalkyl and C1-C10 hydroxyalkyl.

T is preferably selected from aryl and heteroaryl.

V is preferably selected from:

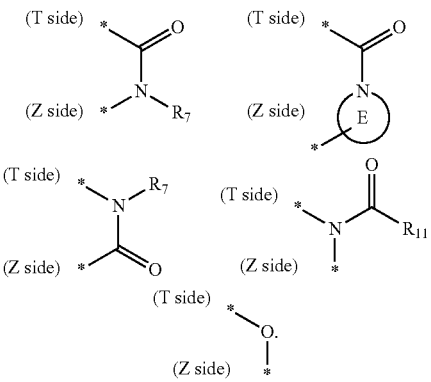

More preferably, V is selected from:

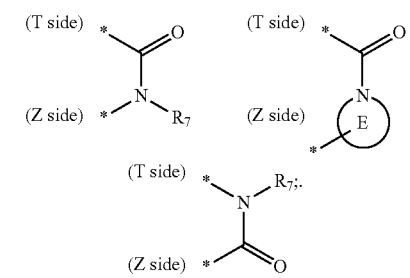

E is preferably a 4- to 7-membered heterocycle optionally containing 1 to 2 additional elements or groups selected from O, N, S, SO and $SO_2$, and the heterocycle is optionally substituted with one substituent selected from:
1) hydrogen,
2) a halogen atom,
3) C1-C10 alkyl optionally having a group(s) independently selected from C1-C10 alkylamino, a halogen atom and a hydroxyl group,
4) a hydroxyl group,
5) C1-C10 alkoxy optionally substituted with a group(s) independently selected from a halogen atom, a hydroxyl group, amino and C1-C10 alkylamino,
6) aryl optionally substituted with a group(s) independently selected from a halogen atom, a hydroxyl group, amino and C1-C10 alkylamino,
7) C1-C10 heteroalkyl optionally substituted with a group(s) independently selected from a halogen atom, a hydroxyl group, amino and C1-C10 alkylamino,
8) a heterocycle optionally substituted with C1-C10 alkyl,
9) heteroaryl optionally substituted with C1-C10 alkyl,
10) heterocyclyl C1-C10 alkyl,
11) —$COR_{16}$,
12) —$NR_{19}R_{20}$ and
13) —$SO_2R_{21}$.

More preferably, E is pyrrolidine or piperidine optionally substituted with a hydroxyl group.

Z is preferably a divalent group selected from:
1) C1-C10 alkylene or C1-C10 heteroalkylene optionally substituted with a halogen atom(s) and/or a hydroxyl group(s), wherein the carbon atom(s) may be oxidized to form carbonyl;
2) C1-C10 alkenylene or C1-C10 heteroalkenylene optionally substituted with a halogen atom(s) and/or a hydroxyl group(s), wherein the carbon atom(s) may be oxidized to form carbonyl; and
3) a group selected from:

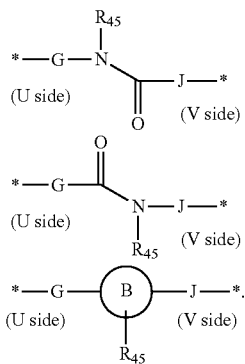

G is preferably a divalent group selected from:
1) C1-C10 alkylene or C1-C10 heteroalkylene optionally substituted with a halogen atom(s); and
2) C1-C10 alkenylene or a C1-C10 heteroalkenylene optionally substituted with a halogen atom(s).
J is preferably a divalent group selected from:
1) C1-C10 alkylene or C1-C10 heteroalkylene optionally substituted with a halogen atom(s); and
2) C1-C10 alkenylene or a C1-C10 heteroalkenylene optionally substituted with a halogen atom(s).
B is preferably selected from a heterocycle or heteroaryl.
$R_{45}$ is preferably selected from hydrogen or C1-C10 alkyl.
$R_7$ is preferably selected from:
1) hydrogen,
2) C1-C10 alkyl optionally substituted with a group(s) independently selected from amino and C1-C10 alkylamino,
3) C1-C10 hydroxyalkyl,
4) C1-C10 heteroalkyl,
5) C1-C10 heteroalkyl optionally substituted with 1 to 3 groups selected from a hydroxyl group, C1-C10 alkylamino and C2-C10 alkenyl,
6) aryl,
7) heteroaryl,
8) aryl C1-C10 alkyl,
9) a heterocycle optionally substituted with C1-C10 alkyl,
10) —(CH$_2$)$_L$COR$_{16}$ (wherein L represents an integer of 1 to 4),
11) C1-C10 alkoxy,
12) C2-C10 alkenyl and
13) —NR$_{40}$R$_{41}$.
More preferably, $R_7$ is selected from:
1) hydrogen,
2) C1-C10 alkyl and
3) C1-C10 hydroxyalkyl.
Specific examples of the compound represented by the formula (1) according to the present invention include the following compounds:
(1) 8-(3-chloro-benzenesulfonyl)-2-cyclohexyl-1,3,8-triaza-spiro[4.5]dec-1-en-4-one;
(2) 8-(3-chloro-benzenesulfonyl)-2-pyridin-4-yl-1,3,8-triaza-spiro[4.5]dec-1-en-4-one;
(3) 8-(3-chloro-benzenesulfonyl)-2-propyl-1,3,8-triaza-spiro[4.5]dec-1-en-4-one;
(4) 8-(3-chloro-benzenesulfonyl)-2-isopropyl-1,3,8-triaza-spiro[4.5]dec-1-en-4-one;
(5) 8-(3-chloro-benzenesulfonyl)-2-(3-methoxy-phenyl)-1,3,8-triaza-spiro[4.5]dec-1-en-4-one;
(6) 8-(3-chloro-benzenesulfonyl)-2-(3-chloro-phenyl)-1,3,8-triaza-spiro[4.5]dec-1-en-4-one;
(7) 2-benzyl-8-(3-chloro-benzenesulfonyl)-1,3,8-triaza-spiro[4.5]dec-1-en-4-one;
(8) 8-(3-chloro-benzenesulfonyl)-2-methyl-1,3,8-triaza-spiro[4.5]dec-1-en-4-one;
(10) 2-biphenyl-2-yl-8-(3-chloro-benzenesulfonyl)-1,3,8-triaza-spiro[4.5]dec-1-en-4-one;
(11) 8-(3-chloro-benzenesulfonyl)-2-o-tolyl-1,3,8-triaza-spiro[4.5]dec-1-en-4-one;
(12) 8-(3-chloro-benzenesulfonyl)-2-(4-trifluoromethyl-phenyl)-1,3,8-triaza-spiro[4.5]dec-1-en-4-one;
(13) 8-(3-chloro-benzenesulfonyl)-2-(3-trifluoromethoxy-phenyl)-1,3,8-triaza-spiro[4.5]dec-1-en-4-one;
(14) 8-(3-chloro-benzenesulfonyl)-2-(1-methyl-cyclohexyl)-1,3,8-triaza-spiro[4.5]dec-1-en-4-one;
(15) 2-(1-acetyl-piperidin-4-yl)-8-(3-chloro-benzenesulfonyl)-1,3,8-triaza-spiro[4.5]dec-1-en-4-one;
(16) 2-tert-butyl-8-(3-chloro-benzenesulfonyl)-1,3,8-triaza-spiro[4.5]dec-1-en-4-one;
(17) 8-(3-chloro-benzenesulfonyl)-2-(4-trifluoromethyl-cyclohexyl)-1,3,8-triaza-spiro[4.5]dec-1-en-4-one;
(18) 3-[8-(3-chloro-benzenesulfonyl)-4-oxo-1,3,8-triaza-spiro[4.5]dec-1-en-2-yl]-piperidine-1-carboxylic acid tert-butyl ester;
(19) 8-(3-chloro-benzenesulfonyl)-2-(3-methyl-cyclohexyl)-1,3,8-triaza-spiro[4.5]dec-1-en-4-one;
(20) 8-(3-chloro-benzenesulfonyl)-2-(2-methyl-cyclohexyl)-1,3,8-triaza-spiro[4.5]dec-1-en-4-one;
(21) 8-(3-chloro-benzenesulfonyl)-2-(4-propyl-cyclohexyl)-1,3,8-triaza-spiro[4.5]dec-1-en-4-one;
(22) 2-(1R,2S,4S)-bicyclo[2.2.1]hept-2-yl-8-(3-chloro-benzenesulfonyl)-1,3,8-triaza-spiro[4.5]dec-1-en-4-one;
(23) 2-(1R,2R,4S)-bicyclo[2.2.1]hept-2-yl-8-(3-chloro-benzenesulfonyl)-1,3,8-triaza-spiro[4.5]dec-1-en-4-one;
(24) 8-(3-chloro-benzenesulfonyl)-2-(4-methoxy-cyclohexyl)-1,3,8-triaza-spiro[4.5]dec-1-en-4-one;
(25) 8-(3-chloro-benzenesulfonyl)-2-(4-methoxy-cyclohexyl)-1,3,8-triaza-spiro[4.5]dec-1-en-4-one;
(26) 2-(4-tert-butyl-cyclohexyl)-8-(3-chloro-benzenesulfonyl)-1,3,8-triaza-spiro[4.5]dec-1-en-4-one;
(27) 8-(3-chloro-benzenesulfonyl)-2-(4-fluoromethyl-cyclohexyl)-1,3,8-triaza-spiro[4.5]dec-1-en-4-one;
(28) 8-(3-chloro-benzenesulfonyl)-2-cyclohexylmethyl-1,3,8-triaza-spiro[4.5]dec-1-en-4-one;
(29) 8-(3-chloro-benzenesulfonyl)-2-phenethyl-1,3,8-triaza-spiro[4.5]dec-1-en-4-one;
(30) 8-(3-chloro-benzenesulfonyl)-2-(2-cyclohexyl-ethyl)-1,3,8-triaza-spiro[4.5]dec-1-en-4-one;
(31) 8-(3-chloro-benzenesulfonyl)-2-(3-trifluoromethyl-phenyl)-1,3,8-triaza-spiro[4.5]dec-1-en-4-one;
(32) 8-(3-chloro-benzenesulfonyl)-2-(3-methanesulfonyl-phenyl)-1,3,8-triaza-spiro[4.5]dec-1-en-4-one;
(33) 8-(3-chloro-benzenesulfonyl)-2-(1-phenyl-cyclohexyl)-1,3,8-triaza-spiro[4.5]dec-1-en-4-one;
(34) 8-(3-chloro-benzenesulfonyl)-2-(2-naphthalen-1-yl-ethyl)-1,3,8-triaza-spiro[4.5]dec-1-en-4-one;
(35) 8-(2-naphthalen-1-yl-ethanesulfonyl)-2-(3-trifluoromethyl-phenyl)-1,3,8-triaza-spiro[4.5]dec-1-en-4-one;

(36) 2-tert-butyl-8-(2-naphthalen-1-yl-ethanesulfonyl) 1,3, 8-triaza-spiro[4.5]dec-1-en-4-one;
(37) 8-(2-naphthalen-1-yl-ethanesulfonyl)-2-(4-trifluoromethyl-cyclohexyl)-1,3,8-triaza-spiro[4.5]dec-1-en-4-one;
(38) 3-[8-(2-naphthalen-1-yl-ethanesulfonyl)-4-oxo-1,3,8-triaza-spiro[4.5]dec-1-en-2-yl]-piperidine-1-carboxylic acid tert-butyl ester;
(39) 8-(2-naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one;
(40) 8-(3-chloro-benzenesulfonyl)-2-[1-(propane-1-sulfonyl)-piperidin-3-yl]-1,3,8-triaza-spiro[4.5]dec-en-4-one;
(41) 2-(1-benzenesulfonyl-piperidin-3-yl)-8-(3-chloro-benzenesulfonyl)-1,3,8-triaza-spiro[4.5]dec-1-en-4-one;
(42) 8-(3-chloro-benzenesulfonyl)-2-(1-phenylmethanesulfonyl-piperidin-3-yl)-1,3,8-triaza-spiro[4.5]dec-1-en-4-one;
(43) 8-(2-naphthalen-1-yl-ethanesulfonyl)-2-(1-phenylmethanesulfonyl-piperidin-3-yl)-1,3,8-triaza-spiro[4.5]dec-1-en-4-one;
(44) 8-(4-chloro-benzenesulfonyl)-2-(2,4-dichloro-phenyl)-1,3,8-triaza-spiro[4.5]dec-1-en-4-one;
(45) 2-(2,4-dichloro-phenyl)-8-(2-trifluoromethyl-benzenesulfonyl)-1,3,8-triaza-spiro[4.5]dec-1-en-4-one;
(46) 8-(butane-1-sulfonyl)-2-(2,4-dichloro-phenyl)-1,3,8-triaza-spiro[4.5]dec-1-en-4-one;
(47) 2-(2,4-dichloro-phenyl)-8-(2-naphthalen-1-yl-ethanesulfonyl)-1,3,8-triaza-spiro[4.5]dec-1-en-4-one;
(48) 2-(2,4-dichloro-phenyl)-8-(quinoline-8-sulfonyl)-1,3,8-triaza-spiro[4.5]dec-1-en-4-one;
(49) 8-(3-chloro-4-fluoro-benzenesulfonyl)-2-(2,4-dichlorophenyl)-1,3,8-triaza-spiro[4.5]dec-1-en-4-one;
(50) 8-(3-chloro-benzenesulfonyl)-2-(2,4-dichloro-phenyl)-1,3,8-triaza-spiro[4.5]dec-1-en-4-one;
(51) 2-(2-cyclohexyl-4-oxo-1,3,8-triaza-spiro[4.5]dec-1-ene-8-sulfonyl)-benzoic acid methyl ester;
(52) 2-cyclohexyl-8-(5-methyl-3-phenyl-isoxazole-4-sulfonyl)-1,3,8-triaza-spiro[4.5]dec-1-en-4-one;
(53) 8-(benzo[b]thiophene-3-sulfonyl)-2-cyclohexyl-1,3,8-triaza-[4.5]dec-1-en-4-one;
(54) 8-(benzo[b]thiophene-2-sulfonyl)-2-cyclohexyl-1,3,8-triaza-spiro[4.5]dec-1-en-4-one;
(55) 8-(5-chloro-thiophene-2-sulfonyl)-2-cyclohexyl-1,3,8-triaza-spiro[4.5]dec-1-en-4-one;
(56) 2-cyclohexyl-8-(thiophene-2-sulfonyl)-1,3,8-triaza-spiro[4.5]dec-1-en-4-one;
(57) 2-cyclohexyl-8-(naphthalene-1-sulfonyl)-1,3,8-triaza-spiro[4.5]dec-1-en-4-one;
(58) 2-cyclohexyl-8-(2,4-dimethyl-thiazole-5-sulfonyl)-1,3,8-triaza-spiro[4.5]dec-1-en-4-one;
(59) 2-cyclohexyl-8-(3,5-dimethyl-isoxazole-4-sulfonyl)-1,3,8-triaza-spiro[4.5]dec-1-en-4-one;
(60) 2-cyclohexyl-8-(2,3-dihydro-benzo[1,4]dioxine-6-sulfonyl)-1,3,8-triaza-spiro[4.5]dec-1-en-4-one;
(61) 2-cyclohexyl-8-(2-naphthalen-1-yl-ethanesulfonyl)-1,3,8-triaza-spiro[4.5]dec-1-en-4-one;
(62) 3-(2-cyclohexyl-4-oxo-1,3,8-triaza-spiro[4.5]dec-1-ene-8-sulfonyl)-thiophene-2-carboxylic acid methyl ester;
(63) 5-(2-cyclohexyl-4-oxo-1,3,8-triaza-spiro[4.5]dec-1-ene-8-sulfonyl)-4-methyl-thiophene-2-carboxylic acid methyl ester;
(64) 2-cyclohexyl-8-(2,5-dimethyl-thiophene-3-sulfonyl)-1,3,8-triaza-spiro[4.5]dec-1-en-4-one;
(65) 8-(5-bromo-thiophene-2-sulfonyl)-2-cyclohexyl-1,3,8-triaza-spiro-[4.5]dec-1-en-4-one;
(66) 8-(5-chloro-thiophene-2-sulfonyl)-2-(3-trifluoromethyl-phenyl)-1,3,8-triaza-spiro[4.5]dec-1-en-4-one;
(67) 8-(naphthalene-2-sulfonyl)-2-(3-trifluoromethyl-phenyl)-1,3,8-triaza-spiro[4.5]dec-1-en-4-one;
(68) 8-(benzo[b]thiophene-2-sulfonyl)-2-(3-trifluoromethyl-phenyl)-1,3,8-triaza-spiro[4.5]dec-1-en-4-one;
(69) 8-(5-bromo-thiophene-2-sulfonyl)-2-(3-trifluoromethyl-phenyl)-1,3,8-triaza-spiro[4.5]dec-1-en-4-one;
(70) 8-(3-chloro-benzenesulfonyl)-2-cyclohexyl-1,3,8-triaza-spiro[4.6]undec-1-en-4-one;
(71) 7-(3-chloro-benzenesulfonyl)-2-cyclohexyl-1,3,7-triaza-spiro[4.5]dec-1-en-4-one;
(72) 7-(3-chloro-benzenesulfonyl)-2-cyclohexyl-1,3,7-triaza-spiro[4.4]non-1-en-4-one;
(73) 4-{2-[2-(2,4-dichloro-phenyl)-4-oxo-1,3,8-triaza-spiro[4.5]dec-1-ene-8-sulfonyl]-ethyl}-3,N,N-trimethyl-benzamide;
(74) 4-[2-(2-tert-butyl-4-oxo-1,3,8-triaza-spiro[4.5]dec-1-ene-8-sulfonyl)-ethyl]-3,N,N-trimethyl-benzamide;
(75) 3,N,N-trimethyl-4-{2-[4-oxo-2-(4-trifluoromethyl-phenyl)-1,3,8-triaza-spiro[4.5]dec-1-ene-8-sulfonyl]-ethyl}-benzamide;
(76) 3,N,N-trimethyl-4-{2-[2-(4-methyl-cyclohexyl)-4-1,3,8-triaza-spiro[4.5]dec-1-ene-8-sulfonyl]-ethyl}-benzamide;
(77) 4-[2-(2-cyclopentyl-4-oxo-1,3,8-triaza-spiro[4.5]dec-1-ene-8-sulfonyl)-ethyl]-3,N,N-trimethyl-benzamide;
(78) 4-{2-[2-(2,6-difluoro-phenyl)-4-oxo-1,3,8-triaza-spiro[4.5]dec-1-ene-8-sulfonyl]-ethyl}-3,N,N-trimethyl-benzamide;
(79) 4-{2-[2-(2,6-dimethoxy-phenyl)-4-oxo-1,3,8-triaza-spiro[4.5]dec-1-ene-8-sulfonyl]-ethyl}-3,N,N-trimethyl-benzamide;
(80) 4-{2-[2-(3-methoxy-phenyl)-4-oxo-1,3,8-triaza-spiro[4.5]dec-1-ene-8-sulfonyl]-ethyl}-3,N,N-trimethyl-benzamide;
(81) 4-{2-[2-(3-chloro-phenyl)-4-oxo-1,3,8-triaza-spiro[4.5]dec-1-ene-8-sulfonyl]-ethyl}-3,N,N-trimethyl-benzamide;
(82) 4-{2-[2-(3,5-bis-trifluoromethyl-phenyl)-4-oxo-1,3,8-triaza-spiro[4.5]dec-1-ene-8-sulfonyl]-ethyl}-3,N,N-trimethyl-benzamide;
(83) 4-[2-(2-benzyl-4-oxo-1,3,8-triaza-spiro[4.5]dec-1-ene-8-sulfonyl)-ethyl]-3,N,N-trimethyl-benzamide;
(84) 3,N,N-trimethyl-4-[2-(4-oxo-2-m-tolyl-1,3,8-triaza-spiro[4.5]dec-1-ene-8-sulfonyl)-ethyl]-benzamide;
(85) 4-{2-[2-(2-chloro-5-trifluoromethyl-phenyl)-4-oxo-1,3,8-triaza-spiro[4.5]dec-1-ene-8-sulfonyl]-ethyl}-3,N,N-trimethyl-benzamide;
(86) 3,N,N-trimethyl-4-{2-[4-oxo-2-(3-trifluoromethyl-phenyl)-1,3,8-triaza-spiro[4.5]dec-1-ene-8-sulfonyl]ethyl}-benzamide;
(87) 4-{2-[2-(4-chloro-phenyl)-4-oxo-1,3,8-triaza-spiro[4.5]dec-1-ene-8-sulfonyl]-ethyl}-3,N,N-trimethyl-benzamide;
(88) 4-{2-[2-(2,3-dichloro-phenyl)-4-oxo-1,3,8-triaza-spiro[4.5]dec-1-ene-8-sulfonyl]-ethyl}-3,N,N-trimethyl-benzamide;
(89) 4-{2-[2-(3-chloro-4-fluoro-phenyl)-4-oxo-1,3,8-triaza-spiro[4.5]dec-1-ene-8-sulfonyl]-ethyl}-3,N,N-trimethyl-benzamide;
(90) 4-{2-[2-(2-chloro-4-fluoro-phenyl)-4-oxo-1,3,8-triaza-spiro[4.5]dec-1-ene-8-sulfonyl]-ethyl}-3,N,N-trimethyl-benzamide;
(91) 4-{2-[2-(3-bromo-phenyl)-4-oxo-1,3,8-triaza-spiro[4.5]dec-1-ene-8-sulfonyl]-ethyl}-3,N,N-trimethyl-benzamide;

(92) 4-{2-[2-(2,2-difluoro-benzo[1,3]dioxol-4-yl)-4-1,3,8-triaza-spiro[4.5]dec-1-ene-8-sulfonyl]-ethyl}-3,N,N-trimethyl-benzamide;

(93) 4-{2-[2-(3-chloro-2-fluoro-phenyl)-4-oxo-1,3,8-triaza-spiro[4.5]dec-1-ene-8-sulfonyl]-ethyl}-3,N,N-trimethyl-benzamide;

(94) 3,N,N-trimethyl-4-(2-{4-oxo-2-[4-(1,1,2,2-tetrafluoro-ethoxy)-phenyl]-1,3,8-triaza-spiro[4.5]dec-1-ene-8-sulfonyl}-ethyl)-benzamide;

(95) 4-{2-[2-(4-chloro-3-methyl-phenyl)-4-oxo-1,3,8-triaza-spiro[4.5]dec-1-ene-8-sulfonyl]-ethyl}-3,N,N-trimethyl-benzamide;

(96) 4-{2-[2-(3-fluoro-4-trifluoromethyl-phenyl)-4-oxo-1,3,8-triaza-spiro[4.5]dec-1-ene-8-sulfonyl]-ethyl}-3,N,N-trimethyl-benzamide;

(97) 3,N,N-trimethyl-4-{2-[2-(6-methyl-pyridin-2-yl)-oxo-1,3,8-triaza-spiro[4.5]dec-1-ene-8-sulfonyl]-ethyl}-benzamide;

(98) 4-{2-[2-(3,4-dichloro-phenyl)-4-oxo-1,3,8-triaza-spiro[4.5]dec-1-ene-8-sulfonyl]-ethyl}-3,N,N-trimethyl-benzamide;

(99) 3,N,N-trimethyl-4-{2-[4-oxo-2-(3-trifluoromethoxy-phenyl)-1,3,8-triaza-spiro[4.5]dec-1-ene-8-sulfonyl]-ethyl}-benzamide;

(100) 4-{2-[2-(2,4-bis-trifluoromethyl-phenyl)-4-oxo-1,3,8-triaza-spiro[4.5]dec-1-ene-8-sulfonyl]-ethyl}-3,N,N-trimethyl-benzamide;

(101) 3,N,N-trimethyl-4-[2-(4-oxo-2-phenethyl-1,3,8-triaza-spiro[4.5]dec-1-ene-8-sulfonyl)-ethyl]-benzamide;

(102) 4-{2-[2-(2,4-dimethyl-thiazol-5-yl)-4-oxo-1,3,8-triaza-spiro[4.5]dec-1-ene-8-sulfonyl]-ethyl}-3,N,N-trimethyl-benzamide;

(103) 4-[2-(2-cyclohexylmethyl-4-oxo-1,3,8-triaza-spiro[4.5]dec-1-ene-8-sulfonyl)-ethyl]-3,N,N-trimethyl-benzamide;

(104) 3,N,N-trimethyl-4-{2-[4-oxo-2-(4-trifluoromethyl-cyclohexyl)-1,3,8-triaza-spiro[4.5]dec-1-ene-8-sulfonyl]-ethyl}-benzamide;

(105) 3,N,N-trimethyl-4-{2-[4-oxo-2-(2-trifluoromethoxy-phenyl)-1,3,8-triaza-spiro[4.5]dec-1-ene-8-sulfonyl]-ethyl}-benzamide;

(106) 3,N,N-trimethyl-4-{2-[4-oxo-2-(4-trifluoromethoxy-phenyl)-1,3,8-triaza-spiro[4.5]dec-1-ene-8-sulfonyl]-ethyl}-benzamide;

(107) 4-{2-[2-(4-fluoro-3-trifluoromethyl-phenyl)-4-oxo-1,3,8-triaza-spiro[4.5]dec-1-ene-8-sulfonyl]-ethyl}-3,N,N-trimethyl-benzamide;

(108) 4-{2-[2-(2-cyclohexyl-ethyl)-4-oxo-1,3,8-triaza-spiro[4.5]dec-1-ene-8-sulfonyl]-ethyl}-3,N,N-trimethyl-benzamide;

(109) 4-{2-[2-(3-fluoro-phenyl)-4-oxo-1,3,8-triaza-spiro[4.5]dec-1-ene-8-sulfonyl]-ethyl}-3,N,N-trimethyl-benzamide;

(110) 4-{2-[2-(3-methanesulfonyl-phenyl)-4-oxo-1,3,8-triaza-spiro[4.5]dec-1-ene-8-sulfonyl]-ethyl}-3,N,N-trimethyl-benzamide;

(111) 3,N,N-trimethyl-4-{2-[2-(2-methyl-3-trifluoromethyl-phenyl)-4-oxo-1,3,8-triaza-spiro[4.5]dec-1-ene-8-sulfonyl]-ethyl}-benzamide;

(112) 3,N,N-trimethyl-4-{2-[2-(2-methyl-5-trifluoromethyl-phenyl)-4-oxo-1,3,8-triaza-spiro[4.5]dec-1-ene-8-sulfonyl]-ethyl}-benzamide;

(113) 4-{2-[2-(2,3-dimethyl-phenyl)-4-oxo-1,3,8-triaza-spiro[4.5]dec-1-ene-8-sulfonyl]-ethyl}-3,N,N-trimethyl-benzamide;

(114) 4-{2-[2-(3-fluoro-2-methyl-phenyl)-4-oxo-1,3,8-triaza-spiro[4.5]dec-1-ene-8-sulfonyl]-ethyl}-3,N,N-trimethyl-benzamide;

(115) 4-{2-[2-(3-fluoro-5-trifluoromethyl-phenyl)-4-oxo-1,3,8-triaza-spiro[4.5]dec-1-ene-8-sulfonyl]-ethyl}-3,N,N-trimethyl-benzamide;

(116) 4-{2-[2-(2-fluoro-3-trifluoromethyl-phenyl)-4-oxo-1,3,8-triaza-spiro[4.5]dec-1-ene-8-sulfonyl]-ethyl}-3,N,N-trimethyl-benzamide;

(117) 4-{2-[2-(4-fluoro-3-methyl-phenyl)-4-oxo-1,3,8-triaza-spiro[4.5]dec-1-ene-8-sulfonyl]-ethyl}-3,N,N-trimethyl-benzamide;

(118) 4-{2-[2-(4-difluoromethoxy-phenyl)-4-oxo-1,3,8-triaza-spiro[4.5]dec-1-ene-8-sulfonyl]-ethyl}-3,N,N-trimethyl-benzamide;

(119) 4-{2-[2-(2-methoxy-pyridin-4-yl)-4-oxo-1,3,8-triaza-spiro[4.5]dec-1-ene-8-sulfonyl]-ethyl}-3,N,N-trimethyl-benzamide;

(120) 3,N,N-trimethyl-4-{2-[2-(5-methyl-pyrazin-2-yl)-4-oxo-1,3,8-triaza-spiro[4.5]dec-1-ene-8-sulfonyl]-ethyl}-benzamide;

(121) 3,N,N-trimethyl-4-[2-(4-oxo-2-thiazol-4-yl-1,3,8-triaza-spiro[4.5]dec-1-ene-8-sulfonyl)-ethyl]-benzamide;

(122) 3,N,N-trimethyl-4-{2-[2-(l-methyl-1H-imidazol-2-yl)-4-oxo-1,3,8-triaza-spiro[4.5]dec-1-ene-8-sulfonyl]-ethyl}-benzamide;

(123) 3,N,N-trimethyl-4-{2-[4-oxo-2-(tetrahydro-pyran-4-yl)-1,3,8-triaza-spiro[4.5]dec-1-ene-8-sulfonyl]-ethyl}-benzamide;

(124) 4-{2-[2-(4-chloro-phenoxymethyl)-4-oxo-1,3,8-triaza-spiro[4.5]dec-1-ene-8-sulfonyl]-ethyl}-3,N,N-trimethyl-benzamide;

(125) 4-{2-[2-(4-fluoro-phenoxymethyl)-4-oxo-1,3,8-triaza-spiro[4.5]dec-1-ene-8-sulfonyl]-ethyl}-3,N,N-trimethyl-benzamide;

(126) 4-{2-[2-(4-chloro-3-trifluoromethyl-phenyl)-4-oxo-1,3,8-triaza-spiro[4.5]dec-1-ene-8-sulfonyl]-ethyl}-3,N,N-trimethyl-benzamide;

(127) 4-{2-[2-(3-chloro-5-trifluoromethyl-phenyl)-4-oxo-1,3,8-triaza-spiro[4.5]dec-1-ene-8-sulfonyl]-ethyl}-3,N,N-trimethyl-benzamide;

(128) 4-{2-[2-(4-chloro-2-methyl-phenyl)-4-oxo-1,3,8-triaza-spiro[4.5]dec-1-ene-8-sulfonyl]-ethyl}-3,N,N-trimethyl-benzamide;

(129) 4-{2-[2-(4-chloro-2-fluoro-phenyl)-4-oxo-1,3,8-triaza-spiro[4.5]dec-1-ene-8-sulfonyl]-ethyl}-3,N,N-trimethyl-benzamide;

(130) 4-{2-[2-(3-isopropoxymethyl-phenyl)-4-oxo-1,3,8-triaza-spiro[4.5]dec-1-ene-8-sulfonyl]-ethyl}-3,N,N-trimethyl-benzamide;

(131) 4-{2-[2-(2,4-dichloro-phenoxymethyl)-4-oxo-1,3,8-triaza-spiro[4.5]dec-1-ene-8-sulfonyl]-ethyl}-3,N,N-trimethyl-benzamide;

(133) 4-{2-[2-(3-chloro-2-methyl-phenyl)-4-oxo-1,3,8-triaza-spiro[4.5]dec-1-ene-8-sulfonyl]-ethyl}-3,N,N-trimethyl-benzamide;

(134) 4-{2-[2-(2,4-dichloro-benzyl)-4-oxo-1,3,8-triaza-spiro[4.5]dec-1-ene-8-sulfonyl]-ethyl}-3,N,N-trimethyl-benzamide;

(135) 3,N,N-trimethyl-4-{2-[4-oxo-2-(3-trifluoromethyl-benzyl)-1,3,8-triaza-spiro[4.5]dec-1-ene-8-sulfonyl]-ethyl}-benzamide;

(136) 3,N,N-trimethyl-4-{2-[4-oxo-2-(1-trifluoromethyl-cyclopropyl)-1,3,8-triaza-spiro[4.5]dec-1-ene-8-sulfonyl]-ethyl}-benzamide;

(137) 3,N,N-trimethyl-4-{2-[4-oxo-2-(1-trifluoromethyl-cyclobutyl)-1,3,8-triaza-spiro[4.5]dec-1-ene-8-sulfonyl]-ethyl}-benzamide;
(138) 3,N,N-trimethyl-4-{2-[4-oxo-2-(1-trifluoromethyl-cyclopentyl)-1,3,8-triaza-spiro[4.5]dec-1-ene-8-sulfonyl]-ethyl}-benzamide;
(139) 4-{2-[2-(2-fluoro-4-trifluoromethyl-phenyl)-4-oxo-1,3,8-triaza-spiro[4.5]dec-1-ene-8-sulfonyl]-ethyl}-3,N,N-trimethyl-benzamide;
(140) 3,N,N-trimethyl-4-(2-{4-oxo-2-[3-(1,1,2,2-tetrafluoro-ethoxy)-phenyl]-1,3,8-triaza-spiro[4.5]dec-1-ene-8-sulfonyl]-ethyl)-benzamide;
(141) 3,N,N-trimethyl-4-{2-[4-oxo-2-((E)-propenyl)-1,3,8-triaza-spiro[4.5]dec-1-ene-8-sulfonyl]-ethyl}-benzamide;
(142) 3,N,N-trimethyl-4-{2-[4-oxo-2-((E)-styryl)-1,3,8-triaza-spiro[4.5]dec-1-ene-8-sulfonyl]-ethyl}-benzamide;
(143) 4-[2-(2-benzothiazol-6-yl-4-oxo-1,3,8-triaza-spiro[4.5]dec-1-ene-8-sulfonyl)-ethyl]-3,N,N-trimethyl-benzamide;
(144) 4-{2-[2-(4-methoxy-3-trifluoromethyl-phenyl)-4-oxo-1,3,8-triaza-spiro[4.5]dec-1-ene-8-sulfonyl]-ethyl}-3,N,N-trimethyl-benzamide;
(145) N-{3-methyl-4-[2-(4-oxo-2-m-tolyl-1,3,8-triaza-spiro[4.5]dec-1-ene-8-sulfonyl)-ethyl]-phenyl}-acetamide;
(146) N-(4-{2-[2-(2,3-dimethyl-phenyl)-4-oxo-1,3,8-triaza-spiro[4.5]dec-1-ene-8-sulfonyl]-ethyl}-3-methyl-phenyl)-acetamide;
(147) N-(4-{2-[2-(2,3-dichloro-phenyl)-4-oxo-1,3,8-triaza-spiro[4.5]dec-1-ene-8-sulfonyl]-ethyl}-3-methyl-phenyl)-acetamide;
(148) N-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;
(149) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(150) acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester;
(151) acetic acid (S)-1-acetoxymethyl-2-[acetyl-(3-methyl-4-{2-[4-oxo-2-(4-trifluoromethyl-phenyl)-1,3,8-triaza-spiro[4.5]dec-1-ene-8-sulfonyl]-ethyl}-phenyl)-amino]-ethyl ester;
(152) acetic acid (S)-1-acetoxymethyl-2-[acetyl-(3-methyl-4-{2-[4-oxo-2-(4-trifluoromethoxy-phenyl)-1,3,8-triaza-spiro[4.5]dec-1-ene-8-sulfonyl]-ethyl}-phenyl)-amino]-ethyl ester;
(153) acetic acid (S)-1-acetoxymethyl-2-[acetyl-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-amino]-ethyl ester;
(154) 8-{2-[4-((S)-2,3-dihydroxy-propylamino)-2-methyl-phenyl]-ethanesulfonyl}-2-(4-trifluoromethyl-phenyl)-1,3,8-triaza-spiro[4.5]dec-1-en-4-one;
(155) 8-{2-[4-((S)-2,3-dihydroxy-propylamino)-2-methyl-phenyl]-ethanesulfonyl}-2-(3-trifluoromethyl-phenyl)-1,3,8-triaza-spiro[4.5]dec-1-en-4-one;
(156) 8-{2-[4-((S)-2,3-dihydroxy-propylamino)-2-methyl-phenyl]-ethanesulfonyl}-2-(4-trifluoromethoxy-phenyl)-1,3,8-triaza-spiro[4.5]dec-1-en-4-one;
(157) 2-(3-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;
(158) 2-(4-chloro-phenyl)-8-{2-[4-((S)-2,3-dihydroxy-propylamino)-2-methyl-phenyl]-ethanesulfonyl}-1,3,8-triaza-spiro[4.5]dec-1-en-4-one;
(159) 8-{2-[4-(2-hydroxy-ethylamino)-2-methyl-phenyl]-ethanesulfonyl}-2-(3-trifluoromethoxy-phenyl)-1,3,8-triaza-spiro[4.5]dec-1-en-4-one;
(160) 8-{2-[4-(2-hydroxy-ethylamino)-2-methyl-phenyl]-ethanesulfonyl}-2-(3-trifluoromethyl-phenyl)-1,3,8-triaza-spiro[4.5]dec-1-en-4-one;
(161) 8-{2-[4-(2-hydroxy-ethylamino)-2-methyl-phenyl]-ethanesulfonyl}-2-(4-trifluoromethyl-phenyl)-1,3,8-triaza-spiro[4.5]dec-1-en-4-one;
(162) {4-[2-(2-tert-butyl-4-oxo-1,3,8-triaza-spiro[4.5]dec-1-ene-8-sulfonyl)-ethyl]-3-methyl-benzyl}-carbamic acid tert-butyl ester;
(163) (4-{2-[2-(4,4-difluoro-cyclohexyl)-4-oxo-1,3,8-triaza-spiro[4.5]dec-1-ene-8-sulfonyl]-ethyl}-3-methyl-benzyl)-carbamic acid tert-butyl ester;
(164) (4-{2-[2-(4-fluoro-3-trifluoromethyl-phenyl)-4-oxo-1,3,8-triaza-spiro[4.5]dec-1-ene-8-sulfonyl]-ethyl}-3-methyl-benzyl)-carbamic acid tert-butyl ester;
(165) (3-methyl-4-{2-[4-oxo-2-(tetrahydro-pyran-4-yl)-1,3,8-triaza-spiro[4.5]dec-1-ene-8-sulfonyl]-ethyl}-benzyl)-carbamic acid tert-butyl ester;
(166) 8-[2-(3-amino-phenyl)-ethanesulfonyl]-2-cyclohexyl-1,3,8-triaza-spiro[4.5]dec-1-en-4-one;
(167) N-{4-[2-(2-cyclohexyl-4-oxo-1,3,8-triaza-spiro[4.5]dec-1-ene-8-sulfonyl)-ethyl]-phenyl}-acetamide;
(168) 3,N,N-trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide;
(169) 4-(2-{2-[3-(2,2-difluoro-ethoxymethyl)-phenyl]-4-oxo-1,3,8-triaza-spiro[4.5]dec-1-ene-8-sulfonyl}-ethyl)-3,N,N-trimethyl-benzamide;
(170) 3,N,N-trimethyl-4-(2-{4-oxo-2-[3-(2,2,3,3-tetrafluoro-propoxymethyl)-phenyl]-1,3,8-triaza-spiro[4.5]dec-1-ene-8-sulfonyl}-ethyl)-benzamide;
(171) 4-(2-{2-[3-(3,5-dimethyl-isoxazol-4-yl)-phenyl]-4-oxo-1,3,8-triaza-spiro[4.5]dec-1-ene-8-sulfonyl}-ethyl)-3,N,N-trimethyl-benzamide;
(172) 4-[2-(2-biphenyl-3-yl-4-oxo-1,3,8-triaza-spiro[4.5]dec-1-ene-8-sulfonyl)-ethyl]-3,N,N-trimethyl-benzamide;
(173) 3,N,N-trimethyl-4-{2-[4-oxo-2-(3-pyridin-3-yl-phenyl)-1,3,8-triaza-spiro[4.5]dec-1-ene-8-sulfonyl]-ethyl}-benzamide;
(174) 3-{8-[2-(4-dimethylcarbamoyl-2-methyl-phenyl)-ethanesulfonyl]-4-oxo-1,3,8-triaza-spiro[4.5]dec-1-en-2-yl}-benzoic acid methyl ester;
(175) 4-(2-{2-[1-(2,4-dichloro-phenoxy)-1-methyl-ethyl]-4-oxo-1,3,8-triaza-spiro[4.5]dec-1-ene-8-sulfonyl}-ethyl)-3,N,N-trimethyl-benzamide;
(176) 3,N,N-trimethyl-4-{2-[4-oxo-2-(2,3,4-trifluoro-phenoxymethyl)-1,3,8-triaza-spiro[4.5]dec-1-ene-8-sulfonyl]-ethyl}-benzamide;
(177) 2-cyclohexyl-4-oxo-1,3,8-triaza-spiro[4.5]dec-1-ene-8-sulfonic acid (3-ethyl-phenyl)-amide;
(178) 2-cyclohexyl-8-[(E)-2-(1H-indol-5-yl)-ethenesulfonyl]-1,3,8-triaza-spiro[4.5]dec-1-en-4-one;
(179) 2-cyclohexyl-8-[(E)-2-(2-trifluoromethyl-phenyl)-ethenesulfonyl]-1,3,8-triaza-spiro[4.5]dec-1-en-4-one;
(180) 2-cyclohexyl-8-[(E)-2-(3-methoxy-phenyl)-ethenesulfonyl]-1,3,8-triaza-spiro[4.5]dec-1-en-4-one;
(181) 2-cyclohexyl-8-[(E)-2-(2-methoxy-phenyl)-ethenesulfonyl]-1,3,8-triaza-spiro[4.5]dec-1-en-4-one;
(182) 2-cyclohexyl-8-[(E)-2-(1H-indol-4-yl)-ethenesulfonyl]-1,3,8-triaza-spiro[4.5]dec-1-en-4-one;
(183) 2-cyclohexyl-8-[(E)-2-(2-fluoro-6-trifluoromethyl-phenyl)-ethenesulfonyl]-1,3,8-triaza-spiro[4.5]dec-1-en-4-one;

(184) 2-cyclohexyl-8-[(E)-2-(2,3-difluoro-phenyl)-ethenesulfonyl]-1,3,8-triaza-spiro[4.5]dec-1-en-4-one;
(185) 2-cyclohexyl-8-[(E)-2-(3-fluoro-2-trifluoromethyl-phenyl)-ethenesulfonyl]-1,3,8-triaza-spiro[4.5]dec-1-en-4-one;
(186) 2-cyclohexyl-8-((E)-2-o-tolyl-ethenesulfonyl)-1,3,8-triaza-spiro[4.5]dec-1-en-4-one;
(187) 2-cyclohexyl-8-{(E)-2-[4-(2-hydroxy-ethyl)-phenyl]-ethenesulfonyl}-1,3,8-triaza-spiro[4.5]dec-1-en-4-one;
(188) 2-cyclohexyl-8-[(E)-2-(2-oxo-2,3-dihydro-benzoxazol-7-yl)-ethenesulfonyl]-1,3,8-triaza-spiro[4.5]dec-1-en-4-one;
(189) 4-[(E)-2-(2-cyclohexyl-4-oxo-1,3,8-triaza-spiro[4.5]dec-1-ene-8-sulfonyl)-vinyl]-indole-1-carboxylic acid dimethylamide;
(190) N-{2-[(E)-2-(2-cyclohexyl-4-oxo-1,3,8-triaza-spiro[4.5]dec-1-ene-8-sulfonyl)-vinyl]-3-methyl-phenyl}-acetamide;
(191) 2-cyclohexyl-8-{(E)-2-[1-((S)-2,3-dihydroxy-propyl)-1H-indol-4-yl]-ethenesulfonyl}-1,3,8-triaza-spiro[4.5]dec-1-en-4-one;
(192) 2-cyclohexyl-8-{(E)-2-[1-(2-morpholin-4-yl-ethyl)-1H-indol-4-yl]-ethenesulfonyl}-1,3,8-triaza-spiro[4.5]dec-1-en-4-one;
(193) 2-{4-[(E)-2-(2-cyclohexyl-4-oxo-1,3,8-triaza-spiro[4.5]dec-1-ene-8-sulfonyl)-vinyl]-indol-1-yl}-N,N-dimethyl-acetamide;
(194) 3-{4-[(E)-2-(2-cyclohexyl-4-oxo-1,3,8-triaza-spiro[4.5]dec-1-ene-8-sulfonyl)-vinyl]-3-trifluoromethyl-phenyl}-1,1-dimethyl-urea;
(195) cyclopropanecarboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;
(196) N-{4-[(E)-2-(2-cyclohexyl-4-oxo-1,3,8-triaza-spiro[4.5]dec-1-ene-8-sulfonyl)-vinyl]-3-trifluoromethyl-phenyl}-2-hydroxy-acetamide;
(197) {3-[(E)-2-(2-cyclohexyl-4-oxo-1,3,8-triaza-spiro[4.5]dec-1-ene-8-sulfonyl)-vinyl]-4-methyl-phenyl}-carbamic acid methyl ester;
(198) 1-{4-[(E)-2-(2-cyclohexyl-4-oxo-1,3,8-triaza-spiro[4.5]dec-1-ene-8-sulfonyl)-vinyl]-3-trifluoromethyl-phenyl}-3-(2-hydroxy-ethyl)-urea;
(199) 2-cyclohexyl-8-{(E)-2-[5-(2-hydroxy-ethylamino)-2-methyl-phenyl]-ethenesulfonyl}-1,3,8-triaza-spiro[4.5]dec-1-en-4-one;
(200) 2-cyclohexyl-8-{(E)-2-[2-(2-hydroxy-ethylamino)-6-methyl-phenyl]-ethenesulfonyl}-1,3,8-triaza-spiro[4.5]dec-1-en-4-one;
(201) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N,N-dimethyl-acetamide;
(202) 2-cyclohexyl-8-{(E)-2-[1-((S)-2,2-dimethyl-[1,3]dioxolan-4-ylmethyl)-3-fluoro-1H-indol-4-yl]-ethenesulfonyl}-1,3,8-triaza-spiro[4.5]dec-1-en-4-one;
(203) 2-cyclohexyl-8-{(E)-2-[2-methyl-4-(3,3,4,4-tetrafluoro-pyrrolidine-1-carbonyl)-phenyl]-ethenesulfonyl}-1,3,8-triaza-spiro[4.5]dec-1-en-4-one;
(204) N-{4-[(E)-2-(2-cyclohexyl-4-oxo-1,3,8-triaza-spiro[4.5]dec-1-ene-8-sulfonyl)-vinyl]-3,5-dimethyl-phenyl}-acetamide;
(205) {4-[(E)-2-(2-cyclohexyl-4-oxo-1,3,8-triaza-spiro[4.5]dec-1-ene-8-sulfonyl)-vinyl]-3-trifluoromethyl-benzyl}-carbamic acid tert-butyl ester;
(206) 2-cyclohexyl-8-{(E)-2-[4-((R)-2,3-dihydroxy-propoxy)-2,6-dimethyl-phenyl]-ethenesulfonyl}-1,3,8-triaza-spiro[4.5]dec-1-en-4-one;
(207) 2-cyclohexyl-8-((E)-2-{2-methyl-4-[(2-oxo-oxazolidin-5-ylmethyl)-amino]-phenyl}-ethenesulfonyl)-1,3,8-triaza-spiro[4.5]dec-1-en-4-one;
(208) 2-{4-[(E)-2-(2-cyclohexyl-4-oxo-1,3,8-triaza-spiro[4.5]dec-1-ene-8-sulfonyl)-vinyl]-phenyl}-N-(2-dimethylamino-ethyl)-acetamide;
(209) 3-{(E)-2-[2-(4-methyl-cyclohexyl)-4-oxo-1,3,8-triaza-spiro[4.5]dec-1-ene-8-sulfonyl]-vinyl}-benzonitrile;
(210) 8-{(E)-2-[4-(3,4-dihydroxy-butoxy)-2-methyl-phenyl]-ethenesulfonyl}-2-(3-trifluoromethyl-phenyl)-1,3,8-triaza-spiro[4.5]dec-1-en-4-one;
(211) 8-{(E)-2-[4-(2-hydroxy-ethylamino)-2-trifluoromethyl-phenyl]-ethenesulfonyl}-2-(3-trifluoromethyl-phenyl)-1,3,8-triaza-spiro[4.5]dec-1-en-4-one;
(212) 8-{(E)-2-[2-methyl-4-(pyrrolidine-1-carbonyl)-phenyl]-ethenesulfonyl}-2-(3-trifluoromethyl-phenyl)-1,3,8-triaza-spiro[4.5]dec-1-en-4-one;
(213) 3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;
(214) N-(2-hydroxy-ethyl)-3,N-dimethyl-4-{(E)-2-[4-oxo-2-(3-trifluoromethyl-phenyl)-1,3,8-triaza-spiro[4.5]dec-1-ene-8-sulfonyl]-vinyl}-benzamide;
(215) N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide;
(216) 8-{(E)-2-[2-methyl-4-(4-methyl-piperazine-1-carbonyl)-phenyl]-ethenesulfonyl}-2-(3-trifluoromethyl-phenyl)-1,3,8-triaza-spiro[4.5]dec-1-en-4-one;
(217) 3-methyl-4-{(E)-2-[4-oxo-2-(3-trifluoromethyl-phenyl)-1,3,8-triaza-spiro[4.5]dec-1-ene-8-sulfonyl]-vinyl}-N-(2,2,2-trifluoro-ethyl)-benzenesulfonamide;
(218) 3-methyl-N-(2-morpholin-4-yl-ethyl)-4-{(E)-2-[4-oxo-2-(3-trifluoromethyl-phenyl)-1,3,8-triaza-spiro[4.5]dec-1-ene-8-sulfonyl]-vinyl}-benzenesulfonamide;
(219) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-yl-benzenesulfonamide;
(220) 8-{(E)-2-[4-((R)-4-hydroxy-2-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;
(221) 8-{(E)-2-[4-((R)-2-hydroxymethyl-5-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one;
(222) 8-{(E)-2-[4-((R)-5-hydroxymethyl-2-oxo-oxazolidin-3-yl)-2-methyl-phenyl]-ethenesulfonyl}-2-(3-trifluoromethyl-phenyl)-1,3,8-triaza-spiro[4.5]dec-1-en-4-one;
(223) 8-((E)-2-{4-[3-(3-dimethylamino-propoxy)-azetidine-1-carbonyl]-2,6-dimethyl-phenyl}-ethenesulfonyl)-2-(3-trifluoromethyl-phenyl)-1,3,8-triaza-spiro[4.5]dec-1-en-4-one;
(224) N-(4-hydroxy-butyl)-3-methyl-4-{(E)-2-[4-oxo-2-trifluoromethoxy-phenyl)-1,3,8-triaza-spiro[4.5]dec-1-ene-8-sulfonyl]-vinyl}-benzenesulfonamide;
(225) N-methyl-N-(4-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(226) 8-[(E)-2-(3-hydroxy-2-methyl-phenyl)-ethenesulfonyl]-2-(3-trifluoromethoxy-phenyl)-1,3,8-triaza-spiro[4.5]dec-1-en-4-one;
(227) 8-[(E)-2-(5-hydroxy-2-methyl-phenyl)-ethenesulfonyl]-2-(3-trifluoromethoxy-phenyl)-1,3,8-triaza-spiro[4.5]dec-1-en-4-one;
(228) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(1-methyl-piperidin-4-yl)-acetamide;

(229) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(230) 8-{(E)-2-[4-(4-hydroxy-piperidine-1-carbonyl)-2-methyl-phenyl]-ethenesulfonyl}-2-(3-trifluoromethoxy-phenyl)-1,3,8-triaza-spiro[4.5]dec-1-en-4-one;

(231) 3,N,N-trimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(232) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(233) 3-fluoro-N,N-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(234) 8-{(E)-2-[2,5-dichloro-4-(3,4-dihydroxy-butoxy)-phenyl]-ethenesulfonyl}-2-(3-trifluoromethoxy-phenyl)-1,3,8-triaza-spiro[4.5]dec-1-en-4-one;

(235) 8-{(E)-2-[4-(3-dimethylamino-propoxy)-2-methyl-phenyl]-ethenesulfonyl}-2-(3-trifluoromethoxy-phenyl)-1,3,8-triaza-spiro[4.5]dec-1-en-4-one;

(236) N-methyl-N-(2-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(237) N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(238) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(239) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;

(240) 2-cycloheptyl-8-{(E)-2-[1-((S)-2,3-dihydroxy-propyl)-1H-indol-4-yl]-ethenesulfonyl}-1,3,8-triaza-spiro[4.5]dec-1-en-4-one;

(241) 2-(4,4-difluoro-cyclohexyl)-8-{(E)-2-[1-((S)-2,3-dihydroxy-propyl)-1H-indol-4-yl]-ethenesulfonyl}-1,3, triaza-spiro[4.5]dec-1-en-4-one;

(242) 8-{(E)-2-[4-((R)-2,3-dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(243) 8-{(E)-2-[4-((R)-2,3-dihydroxy-propoxy)-2,6-dimethyl-phenyl]-ethenesulfonyl}-2-(2-fluoro-3-trifluoromethyl-phenyl)-1,3,8-triaza-spiro[4.5]dec-1-en-4-one;

(244) 2-(2-fluoro-3-trifluoromethyl-phenyl)-8-{(E)-2-(4-hydroxy-piperidine-1-carbonyl)-2,6-dimethyl-phenyl ethenesulfonyl}-1,3,8-triaza-spiro[4.5]dec-1-en-4-one;

(245) 8-{(E)-2-[1-((S)-2,2-dimethyl-[1,3]dioxolan-4-ylmethyl)-1H-indol-4-yl]-ethenesulfonyl}-2-(4-trifluoromethyl-cyclohexyl)-1,3,8-triaza-spiro[4.5]dec-1-en-4-one;

(246) 8-{(E)-2-[1-(2,2-dimethyl-[1,3]dioxolan-4-ylmethyl)-1H-indol-4-yl]-ethenesulfonyl}-2-(tetrahydro-pyran-4-yl)-1,3,8-triaza-spiro[4.5]dec-1-en-4-one;

(247) 8-{(E)-2-[4-(3,4-dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one;

(248) 2-(2-fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one;

(249) 2-(2,4-dichloro-phenyl)-8-{(E)-2-[1-((S)-2,3-dihydroxy-propyl)-1H-indol-4-yl]-ethenesulfonyl}-1,3,8-triaza-spiro[4.5]dec-1-en-4-one;

(250) 2-(4-chloro-phenyl)-8-{(E)-2-[1-((S)-2,3-dihydroxy-propyl)-1H-indol-4-yl]-ethenesulfonyl}-1,3,8-triaza-spiro[4.5]dec-1-en-4-one;

(251) 2-cyclohexyl-8-[(E)-4-(1H-indol-4-yl)-but-3-ene-1-sulfonyl]-1,3,8-triaza-spiro[4.5]dec-1-en-4-one;

(252) 2-cyclohexyl-8-[(E)-5-(1H-indol-4-yl)-pent-4-ene-1-sulfonyl]-1,3,8-triaza-spiro[4.5]dec-1-en-4-one;

(253) 2-cyclohexyl-8-{(E)-3-[1-(2,3-dihydroxy-propyl)-1H-indol-4-yl]-prop-2-ene-1-sulfonyl}-1,3,8-triaza-spiro[4.5]dec-1-en-4-one;

(254) 8-{(E)-2-[3-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(255) 8-{(E)-2-[5-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;

(256) 8-{(E)-2-[3-(2-hydroxy-ethoxy)-2-methyl-phenyl]-ethenesulfonyl}-2-(3-trifluoromethoxy-phenyl)-1,3,8-triaza-spiro[4.5]dec-1-en-4-one;

(257) N-(2-hydroxy-ethyl)-N-(4-methyl-3-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(258) 8-{(E)-2-[4-((R)-2-hydroxymethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(259) N-(4-{(E)-2-[2-(2-fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide;

(260) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide;

(261) 2-cyclohexyl-8-[2-(2-oxo-2,3-dihydro-benzoxazol-7-yl)-ethanesulfonyl]-1,3,8-triaza-spiro[4.5]dec-1-en-4-one;

(262) 2-cyclohexyl-8-[5-(1H-indol-4-yl)-pentane-1-sulfonyl]-1,3,8-triaza-spiro[4.5]dec-1-en-4-one;

(263) 2-cyclohexyl-8-[4-(1H-indol-4-yl)-butane-1-sulfonyl]-1,3,8-triaza-spiro[4.5]dec-1-en-4-one;

(264) N-methyl-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(265) N-methyl-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;

(266) 8-{2-[3-(3,4-dihydroxy-butoxy)-2-methyl-phenyl]-ethanesulfonyl}-2-(3-trifluoromethoxy-phenyl)-1,3,8-triaza-spiro[4.5]dec-1-en-4-one;

(267) 8-{2-[5-(3,4-dihydroxy-butoxy)-2-methyl-phenyl]-ethanesulfonyl}-2-(3-trifluoromethoxy-phenyl)-1,3,8-triaza-spiro[4.5]dec-1-en-4-one;

(268) 8-{2-[4-((R)-2-hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;

(269) 2-cyclohexyl-8-[2-(1H-indol-5-yl)-ethanesulfonyl]-1,3,8-triaza-spiro[4.5]dec-1-en-4-one;

(270) 2-{4-[2-(2-cyclohexyl-4-oxo-1,3,8-triaza-spiro[4.5]dec-1-ene-8-sulfonyl)-ethyl]-3-trifluoromethyl-phenylamino}-N, N-dimethyl-acetamide;

(271) cyclopropanecarboxylic acid {4-[2-(2-cyclohexyl-4-oxo-1,3,8-triaza-spiro[4.5]dec-1-ene-8-sulfonyl)-ethyl]-3-trifluoromethyl-phenyl}-amide;

(272) {4-[2-(2-cyclohexyl-4-oxo-1,3,8-triaza-spiro[4.5]dec-1-ene-8-sulfonyl)-ethyl]-3-trifluoromethyl-benzyl}-carbamic acid tert-butyl ester;

(273) 3-{4-[2-(2-cyclohexyl-4-oxo-1,3,8-triaza-spiro[4.5]dec-1-ene-8-sulfonyl)-ethyl]-3-trifluoromethyl-phenyl}-1,1-dimethyl-urea;

(274) {3-[2-(2-cyclohexyl-4-oxo-1,3,8-triaza-spiro[4.5]dec-1-ene-8-sulfonyl)-ethyl]-4-methyl-phenyl}-carbamic acid methyl ester;
(275) 2-cyclohexyl-8-{2-[5-(2-hydroxy-ethylamino)-2-methyl-phenyl]-ethanesulfonyl}-1,3,8-triaza-spiro[4.5]dec-1-en-4-one;
(276) N-{2-[2-(2-cyclohexyl-4-oxo-1,3,8-triaza-spiro[4.5]dec-1-ene-8-sulfonyl)-ethyl]-3-methyl-phenyl}-acetamide;
(277) 2-cyclohexyl-8-(2-o-tolyl-ethanesulfonyl)-1,3,8-triaza-spiro[4.5]dec-1-en-4-one;
(278) 1-{4-[2-(2-cyclohexyl-4-oxo-1,3,8-triaza-spiro[4.5]dec-1-ene-8-sulfonyl)-ethyl]-3-trifluoromethyl-phenyl}-3-(2-hydroxy-ethyl)-urea;
(279) 2-cyclohexyl-8-{2-[4-((R)-2,3-dihydroxy-propoxy)-2,6-dimethyl-phenyl]-ethanesulfonyl}-1,3,8-triaza-spiro[4.5]dec-1-en-4-one;
(280) 2-cyclohexyl-8-{2-[4-(2-hydroxy-ethyl)-phenyl]-ethanesulfonyl}-1,3,8-triaza-spiro[4.5]dec-1-en-4-one;
(281) 2-cyclohexyl-8-(2-{2-methyl-4-[(2-oxo-oxazolidin-5-ylmethyl)-amino]-phenyl}-ethanesulfonyl)-1,3,8-triaza-spiro[4.5]dec-1-en-4-one;
(282) 2-{4-[2-(2-cyclohexyl-4-oxo-1,3,8-triaza-spiro[4.5]dec-1-ene-8-sulfonyl)-ethyl]-phenyl}-N-(2-dimethyl-amino-ethyl)-acetamide;
(283) 2-cyclohexyl-8-{2-[2-methyl-4-(3,3,4,4-tetrafluoro-pyrrolidine-1-carbonyl)-phenyl]-ethanesulfonyl}-1,3,8-triaza-spiro[4.5]dec-1-en-4-one;
(284) 8-{2-[4-(3,4-dihydroxy-butoxy)-2-methyl-phenyl]-ethanesulfonyl}-2-(3-trifluoromethyl-phenyl)-1,3,8-triaza-spiro[4.5]dec-1-en-4-one;
(285) 8-{2-[4-(4-hydroxy-piperidine-1-carbonyl)-2-methyl-phenyl]-ethanesulfonyl}-2-(3-trifluoromethoxy-phenyl)-1,3,8-triaza-spiro[4.5]dec-1-en-4-one;
(286) 8-{2-[4-(2-hydroxy-ethylamino)-2-trifluoromethyl-phenyl]-ethanesulfonyl}-2-(3-trifluoromethyl-phenyl)-1,3,8-triaza-spiro[4.5]dec-1-en-4-one;
(287) N-(4-hydroxy-butyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;
(288) 8-{2-[2-methyl-4-(pyrrolidine-1-carbonyl)-phenyl]-ethanesulfonyl}-2-(3-trifluoromethyl-phenyl)-1,3,8-triaza-spiro[4.5]dec-1-en-4-one;
(289) 8-{2-[2-methyl-4-(4-methyl-piperazine-1-carbonyl)-phenyl]-ethanesulfonyl}-2-(3-trifluoromethyl-phenyl)-1,3,8-triaza-spiro[4.5]dec-1-en-4-one;
(290) 3-methyl-4-{2-[4-oxo-2-(3-trifluoromethyl-phenyl)-1,3,8-triaza-spiro[4.5]dec-1-ene-8-sulfonyl]-ethyl}-N(2,2,2-trifluoro-ethyl)-benzenesulfonamide;
(291) 3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;
(292) 3-methyl-N-(2-morpholin-4-yl-ethyl)-4-{2-[4-oxo-2-(3-trifluoromethyl-phenyl)-1,3,8-triaza-spiro[4.5]dec-1-ene-8-sulfonyl]-ethyl}-benzenesulfonamide;
(293) 3-fluoro-N,N-dimethyl-4-{2-[4-oxo-2-(3-trifluoromethoxy-phenyl)-1,3,8-triaza-spiro[4.5]dec-1-ene-8-sulfonyl]-ethyl}-benzamide;
(294) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-yl-benzenesulfonamide;
(295) 8-{2-[4-(3-dimethylamino-propoxy)-2-methyl-phenyl]-ethanesulfonyl}-2-(3-trifluoromethoxy-phenyl)-1,3,8-triaza-spiro[4.5]dec-1-en-4-one;
(296) 8-{2-[4-((R)-5-hydroxymethyl-2-oxo-oxazolidin-3-yl)-2-methyl-phenyl]-ethanesulfonyl}-2-(3-trifluoromethyl-phenyl)-1,3,8-triaza-spiro[4.5]dec-1-en-4-one;
(297) 8-{2-[4-((R)-4-hydroxy-2-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one;
(298) N-(3-methyl-4-{2-[4-oxo-2-(3-trifluoromethyl-phenyl)-1,3,8-triaza-spiro[4.5]dec-1-ene-8-sulfonyl]-ethyl}-phenyl)-acetamide;
(299) N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(300) 2-hydroxy-N-methyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(301) 1-methyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;
(302) N-{4-[2-(2-cyclohexyl-4-oxo-1,3,8-triaza-spiro[4.5]dec-1-ene-8-sulfonyl)-ethyl]-3,5-dimethyl-phenyl}-acetamide;
(303) 2-cyclohexyl-8-[2-(1H-indol-4-yl)-ethanesulfonyl]-1,3,8-triaza-spiro[4.5]dec-1-en-4-one;
(304) 2-(3-trifluoromethoxy-phenyl)-8-[2-(2-trifluoromethyl-phenyl)-ethanesulfonyl]-1,3,8-triaza-spiro[4.5]dec-1-en-4-one;
(305) 8-[2-(1H-indol-4-yl)-ethanesulfonyl]-2-(3-trifluoromethyl-phenyl)-1,3,8-triaza-spiro[4.5]dec-1-en-4-one;
(306) 8-[2-(1H-indol-4-yl)-ethanesulfonyl]-2-(4-methyl-cyclohexyl)-1,3,8-triaza-spiro[4.5]dec-1-en-4-one;
(307) 8-[2-(2,2-difluoro-benzo[1,3]dioxol-4-yl)-ethanesulfonyl]-2-(3-trifluoromethoxy-phenyl)-1,3,8-triaza-spiro[4.5]dec-1-en-4-one;
(308) 8-[2-(1-methyl-1H-indol-7-yl)-ethanesulfonyl]-2-(3-trifluoromethoxy-phenyl)-1,3,8-triaza-spiro[4.5]dec-1-en-4-one;
(309) 2-cyclohexyl-8-{2-[1-((S)-2,3-dihydroxy-propyl)-1H-indol-4-yl]-ethanesulfonyl}-1,3,8-triaza-spiro[4.5]dec-1-en-4-one;
(310) 4-[2-(2-cyclohexyl-4-oxo-1,3,8-triaza-spiro[4.5]dec-1-ene-8-sulfonyl)-ethyl]-indole-1-carboxylic acid dimethylamide;
(311) 8-[3-(1H-indol-4-yl)-propane-1-sulfonyl]-2-(4-methyl-cyclohexyl)-1,3,8-triaza-spiro[4.5]dec-1-en-4-one;
(312) 2-cyclohexyl-8-[2-(1-methanesulfonyl-1H-indol-4-yl)-ethanesulfonyl]-1,3,8-triaza-spiro[4.5]dec-1-en-4-one;
(313) 2-cyclohexyl-8-{2-[1-(2-dimethylamino-ethyl)-1H-indol-4-yl]-ethanesulfonyl}-1,3,8-triaza-spiro[4.5]dec-1-en-4-one;
(314) 8-[2-(4-amino-2-trifluoromethyl-phenyl)-ethanesulfonyl]-2-cyclohexyl-1,3,8-triaza-spiro[4.5]dec-1-en-4-one;
(315) 2-cyclohexyl-8-[3-(3-trifluoromethyl-phenyl)-propane-1-sulfonyl]-1,3,8-triaza-spiro[4.5]dec-1-en-4-one;
(316) 2-cyclohexyl-8-(3-m-tolyl-propane-1-sulfonyl)-1,3,8-triaza-spiro[4.5]dec-1-en-4-one;
(317) 2-cyclohexyl-8-[3-(3-hydroxy-phenyl)-propane-1-sulfonyl]-1,3,8-triaza-spiro[4.5]dec-1-en-4-one;
(318) 2-cyclohexyl-8-[3-(2-hydroxy-phenyl)-propane-1-sulfonyl]-1,3,8-triaza-spiro[4.5]dec-1-en-4-one;
(319) 8-(2-benzo[b]thiophen-3-yl-ethanesulfonyl)-2-cyclohexyl-1,3,8-triaza-spiro[4.5]dec-1-en-4-one;
(320) 2-cyclohexyl-8-(2-isoquinolin-5-yl-ethanesulfonyl)-1,3,8-triaza-spiro[4.5]dec-1-en-4-one;
(321) 2-cyclohexyl-8-{2-[4-((S)-2,3-dihydroxy-propylamino)-2-methyl-phenyl]-ethanesulfonyl}-1,3,8-triaza-spiro[4.5]dec-1-en-4-one;

(322) 8-{2-[1-((S)-2,3-dihydroxy-propyl)-1H-indol-4-yl]-ethanesulfonyl}-2-(4-trifluoromethyl-cyclohexyl)-1,3,8-triaza-spiro[4.5]dec-1-en-4-one;
(323) 2-cyclohexyl-8-[2-(2-trifluoromethyl-phenyl)-ethanesulfonyl]-1,3,8-triaza-spiro[4.5]dec-1-en-4-one;
(324) 4-[3-(2-cyclohexyl-4-oxo-1,3,8-triaza-spiro[4.5]dec-1-ene-8-sulfonyl)-propyl]-N,N-dimethyl-benzamide;
(325) 8-{2-[4-((R)-2,3-dihydroxy-propoxy)-2-methyl-phenyl]-ethanesulfonyl}-2-(3-trifluoromethoxy-phenyl)-1,3,8-triaza-spiro[4.5]dec-1-en-4-one;
(326) N-(2-hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;
(327) N-(2-hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide;
(328) 8-[3-(3-amino-phenyl)-propane-1-sulfonyl]-2-cyclohexyl-1,3,8-triaza-spiro[4.5]dec-1-en-4-one;
(329) N,N-dimethyl-4-{5-[4-oxo-2-(3-trifluoromethyl-phenyl)-1,3,8-triaza-spiro[4.5]dec-1-ene-8-sulfonyl]-thiophen-2-yl}-benzamide;
(330) N,N-dimethyl-3-{5-[4-oxo-2-(3-trifluoromethyl-phenyl)-1,3,8-triaza-spiro[4.5]dec-1-ene-8-sulfonyl]-thiophen-2-yl}-benzamide;
(331) 3,N,N-trimethyl-4-{5-[4-oxo-2-(3-trifluoromethyl-phenyl)-1,3,8-triaza-spiro[4.5]dec-1-ene-8-sulfonyl]-thiophen-2-yl}-benzamide;
(332) N-{4-[5-(2-cyclohexyl-4-oxo-1,3,8-triaza-spiro[4.5]dec-1-ene-8-sulfonyl)-thiophen-2-yl]-3-methyl-phenyl}-acetamide;
(333) 4-{5-[2-(4-fluoro-3-trifluoromethyl-phenyl)-4-oxo-1,3,8-triaza-spiro[4.5]dec-1-ene-8-sulfonyl]-thiophen-2-yl}-3,N,N-trimethyl-benzamide;
(334) 3-{5-[2-(4-fluoro-3-trifluoromethyl-phenyl)-4-oxo-1,3,8-triaza-spiro[4.5]dec-1-ene-8-sulfonyl]-thiophen-2-yl}-4,N,N-trimethyl-benzamide;
(335) 2-methyl-3'-[4-oxo-2-(3-trifluoromethoxy-phenyl)-1,3,8-triaza-spiro[4.5]dec-1-ene-8-sulfonyl]-biphenyl-4-carboxylic acid dimethylamide;
(336) 2-methyl-4'-[4-oxo-2-(3-trifluoromethoxy-phenyl)-1,3,8-triaza-spiro[4.5]dec-1-ene-8-sulfonyl]-biphenyl-4-carboxylic acid dimethylamide;
(337) 3,N,N-trimethyl-4-{6-[4-oxo-2-(3-trifluoromethoxy-phenyl)-1,3,8-triaza-spiro[4.5]dec-1-ene-8-sulfonyl]-pyridin-2-yl}-benzamide;
(338) 2-cyclohexyl-8-{2-[2-(3,5-dimethyl-isoxazol-4-yl)-phenyl]-ethanesulfonyl}-1,3,8-triaza-spiro[4.5]dec-1-en-4-one;
(339) 2-cyclohexyl-8-{2-[2-(6-methoxy-pyridin-3-yl)-phenyl]-ethanesulfonyl}-1,3,8-triaza-spiro[4.5]dec-1-en-4-one;
(340) 2-cyclohexyl-8-{2-[2-(1-methyl-1H-pyrazol-4-yl)-phenyl]-ethanesulfonyl}-1,3,8-triaza-spiro[4.5]dec-1-en-4-one;
(341) 8-{5-[4-(3,4-dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one;
(342) N-(4-{5-[2-(4-fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxy-ethyl)-acetamide;
(343) 2-cyclohexyl-8-((E)-2-thiazol-2-yl-ethenesulfonyl)-1,3,8-triaza-spiro[4.5]dec-1-en-4-one;
(344) 2-cyclohexyl-8-((E)-2-cyclopentyl-ethenesulfonyl)-1,3,8-triaza-spiro[4.5]dec-1-en-4-one;
(345) 2-cyclohexyl-8-(2-thiazol-2-yl-ethanesulfonyl)-1,3,8-triaza-spiro[4.5]dec-1-en-4-one;
(346) 2-cyclohexyl-8-[3-(4-methoxy-phenyl)-propane-1-sulfonyl]-1,3,8-triaza-spiro[4.5]dec-1-en-4-one;
(347) N-benzyl-2-(2-cyclohexyl-4-oxo-1,3,8-triaza-spiro[4.5]dec-1-ene-8-sulfonyl)-benzamide;
(348) 8-(3-chloro-benzenesulfonyl)-2-[3-(morpholine-4-carbonyl)-phenyl]-1,3,8-triaza-spiro[4.5]dec-1-en-4-one;
(349) 3-[8-(3-chloro-benzenesulfonyl)-4-oxo-1,3,8-triaza-spiro[4.5]dec-1-en-2-yl]-N-methyl-N-phenyl-benzamide;
(350) N-benzyl-3-[8-(3-chloro-benzenesulfonyl)-4-oxo-1,3,8-triaza-spiro[4.5]dec-1-en-2-yl]-benzamide;
(351) 3-[8-(3-chloro-benzenesulfonyl)-4-oxo-1,3,8-triaza-spiro[4.5]dec-1-en-2-yl]-N,N-dimethyl-benzamide;
(352) 8-{2-[4-(4-methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one;
(353) N—[(R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidin-3-yl]-acetamide;
(354) 8-{2-[2-methyl-4-((S)-2-trifluoromethyl-pyrrolidine-1-carbonyl)-phenyl]-ethanesulfonyl}-2-(3-trifluoromethyl-phenyl)-1,3,8-triaza-spiro[4.5]dec-1-en-4-one;
(355) 8-{2-[4-((R)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(356) 8-{2-[4-((S)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;
(357) 8-(2-{4-[4-(2-hydroxy-ethyl)-piperidine-1-carbonyl]-2-methyl-phenyl}-ethanesulfonyl)-2-(3-trifluoromethyl-phenyl)-1,3,8-triaza-spiro[4.5]dec-1-en-4-one;
(358) 8-(2-{2-methyl-4-[4-(3-methyl-[1,2,4]oxadiazol-5-yl)-piperidine-1-carbonyl]-phenyl}-ethanesulfonyl)-2-(3-trifluoromethyl-phenyl)-1,3,8-triaza-spiro[4.5]dec-1-en-4-one;
(359) 8-{2-[2-methyl-4-(4-pyrimidin-2-yl-piperazine-1-carbonyl)-phenyl]-ethanesulfonyl}-2-(3-trifluoromethyl-phenyl)-1,3,8-triaza-spiro[4.5]dec-1-en-4-one;
(360) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-sulfonic acid dimethylamide;
(361) 8-{2-[2-methyl-4-(4-pyridin-2-yl-piperazine-1-carbonyl)-phenyl]-ethanesulfonyl}-2-(3-trifluoromethyl-phenyl)-1,3,8-triaza-spiro[4.5]dec-1-en-4-one;
(362) 8-[2-(4-{4-[2-(2-hydroxy-ethoxy)-ethyl]-piperazine-1-carbonyl}-2-methyl-phenyl)-ethanesulfonyl]-2-(3-trifluoromethyl-phenyl)-1,3,8-triaza-spiro[4.5]dec-1-en-4-one;
(363) 8-(2-{2-methyl-4-[4-(2-morpholin-4-yl-ethyl)-piperazine-1-carbonyl]-phenyl}-ethanesulfonyl)-2-(3-trifluoromethyl-phenyl)-1,3,8-triaza-spiro[4.5]dec-1-en-4-one;
(364) 8-{2-[2-methyl-4-(4-thiazol-2-yl-piperazine-1-carbonyl)-phenyl]-ethanesulfonyl}-2-(3-trifluoromethyl-phenyl)-1,3,8-triaza-spiro[4.5]dec-1-en-4-one;
(365) 8-{2-[4-(4,4-difluoro-piperidine-1-carbonyl)-2-methyl-phenyl]-ethanesulfonyl}-2-(3-trifluoromethyl-phenyl)-1,3,8-triaza-spiro[4.5]dec-1-en-4-one;
(366) 8-(2-{4-[4-(3-hydroxy-propyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;
(367) (S)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;
(368) 8-{2-[2-methyl-4-(3,3,4,4-tetrafluoro-pyrrolidine-1-carbonyl)-phenyl]-ethanesulfonyl}-2-(3-trifluoromethyl-phenyl)-1,3,8-triaza-spiro[4.5]dec-1-en-4-one;

(369) (R)-1-(3-methyl-4-{2-[4-oxo-2-(3-trifluoromethyl-phenyl)-1,3,8-triaza-spiro[4.5]dec-1-ene-8-sulfonyl]-ethyl}-benzoyl)-pyrrolidine-2-carboxylic acid amide;

(370) 8-{2-[4-((S)-3-hydroxy-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(371) 8-{2-[4-((R)-2-hydroxymethyl-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(372) 8-{2-[4-((S)-3-dimethylamino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one;

(373) 8-{2-[4-(4-tert-butyl-piperazine-1-carbonyl)-2-methyl-phenyl]-ethanesulfonyl}-2-(3-trifluoromethyl-phenyl)-1,3,8-triaza-spiro[4.5]dec-1-en-4-one;

(374) 8-(2-{4-[4-(3-dimethylamino-propyl)-piperazine-carbonyl]-2-methyl-phenyl}-ethanesulfonyl)-2-(3-trifluoromethyl-phenyl)-1,3,8-triaza-spiro[4.5]dec-1-en-4-one;

(375) 8-(2-{4-[4-(4-fluoro-phenyl)-piperazine-1-carbonyl]-2-methyl-phenyl}-ethanesulfonyl)-2-(3-trifluoromethyl-phenyl)-1,3,8-triaza-spiro[4.5]dec-1-en-4-one;

(376) 8-{2-[4-(4-isopropyl-piperazine-1-carbonyl)-2-methyl-phenyl]-ethanesulfonyl}-2-(3-trifluoromethyl-phenyl)-1,3,8-triaza-spiro[4.5]dec-1-en-4-one;

(377) 8-{2-[4-(3-hydroxy-azetidine-1-carbonyl)-2-meth phenyl]-ethanesulfonyl}-2-(3-trifluoromethyl-phenyl)-1,3,8-triaza-spiro[4.5]dec-1-en-4-one;

(378) 8-{2-[4-(3-fluoro-pyrrolidine-1-carbonyl)-2-met phenyl]-ethanesulfonyl}-2-(3-trifluoromethyl-phenyl)-1,3,8-triaza-spiro[4.5]dec-1-en-4-one;

(379) 8-{2-[4-(3-fluoro-azetidine-1-carbonyl)-2-methyl-phenyl]-ethanesulfonyl}-2-(3-trifluoromethyl-phenyl)-1,3,8-triaza-spiro[4.5]dec-1-en-4-one;

(380) 8-{2-[2-methyl-4-(piperidine-1-carbonyl)-phenyl]-ethanesulfonyl}-2-(3-trifluoromethyl-phenyl)-1,3,8-triaza-spiro[4.5]dec-1-en-4-one;

(381) 8-{2-[4-(azetidine-1-carbonyl)-2-methyl-phenyl]ethanesulfonyl}-2-(3-trifluoromethyl-phenyl)-1,3,8-triaza-spiro[4.5]dec-1-en-4-one;

(382) 4-(3-methyl-4-{2-[4-oxo-2-(3-trifluoromethyl-phenyl)-1,3,8-triaza-spiro[4.5]dec-1-ene-8-sulfonyl]-ethyl}-benzoyl)-piperazine-1-carboxylic acid dimethylamide;

(383) 3,5,N,N-tetramethyl-4-{(E)-2-[4-oxo-2-(3-trifluoromethyl-phenyl)-1,3,8-triaza-spiro[4.5]dec-1-ene-8-sulfonyl]-vinyl}-benzamide;

(384) 8-{(E)-2-[4-(4-hydroxy-piperidine-1-carbonyl)-2-dimethyl-phenyl]-ethenesulfonyl}-2-(3-trifluoromethyl phenyl)-1,3,8-triaza-spiro[4.5]dec-1-en-4-one;

(385) 8-{(E)-2-[4-(3-hydroxy-azetidine-1-carbonyl)-2,6-dimethyl-phenyl]-ethenesulfonyl}-2-(3-trifluoromethyl phenyl)-1,3,8-triaza-spiro[4.5]dec-1-en-4-one;

(386) 8-{(E)-2-[4-(4-hydroxy-4-hydroxymethyl-piperidine-1-carbonyl)-2,6-dimethyl-phenyl]-ethenesulfonyl}-2-(3 trifluoromethyl-phenyl)-1,3,8-triaza-spiro[4.5]dec-1-en-4-one;

(387) 8-{(E)-2-[4-((3R,4R)-3-dimethylamino-4-hydroxy-pyrrolidine-1-carbonyl)-2,6-dimethyl-phenyl]-ethenesulfonyl}-2-(3-trifluoromethyl-phenyl)-1,3,8-triaza-spiro[4.5]dec-1-en-4-one;

(388) 8-{(E)-2-[2,6-dimethyl-4-(pyrrolidine-1-carbonyl)-phenyl]-ethenesulfonyl}-2-(3-trifluoromethyl-phenyl)-1,3,8-triaza-spiro[4.5]dec-1-en-4-one;

(389) N-(3-hydroxy-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(390) N-(2-dimethylamino-ethyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(391) N-(3-dimethylamino-propyl)-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(392) N-carbamoylmethyl-3,5,N-trimethyl-4-{(E)-2-[4-oxo-2-(3-trifluoromethyl-phenyl)-1,3,8-triaza-spiro[4.5]dec-1-ene-8-sulfonyl]-vinyl}-benzamide;

(393) 3,5,N-trimethyl-N-(1-methyl-piperidin-4-yl)-4-{(E)-2-[4-oxo-2-(3-trifluoromethyl-phenyl)-1,3,8-triaza-spiro[4.5]dec-1-ene-8-sulfonyl]-vinyl}-benzamide;

(394) 8-{(E)-2-[4-(4-acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(395) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid dimethylamide;

(396) 4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazine-1-carboxylic acid amide;

(397) 8-((E)-2-{4-[4-(3-dimethylamino-propyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(398) 8-{(E)-2-[2,6-dimethyl-4-((R)-3-methylamino-pyrrolidine-1-carbonyl)-phenyl]-ethenesulfonyl}-2-(3-trifluoromethoxy-phenyl)-1,3,8-triaza-spiro[4.5]dec-1-en-4-one;

(399) 8-{(E)-2-[4-((R)-3-dimethylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(400) 8-{(E)-2-[4-(4-hydroxy-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(401) 8-{(E)-2-[4-((R)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(402) 8-{(E)-2-[4-((S)-3-hydroxy-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(403) 8-{(E)-2-[4-(4-hydroxy-4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(404) 8-{(E)-2-[4-((R)-3-amino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(405) 8-{(E)-2-[4-(4-dimethylamino-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(406) 8-{(E)-2-[4-((3S,4S)-3-hydroxy-4-isopropylamino-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(407) 8-((E)-2-{4-[4-(2-dimethylamino-ethoxy)-piperidine-1-carbonyl]-2,6-dimethyl-phenyl}-ethenesulfonyl)-2-(3-trifluoromethoxy-phenyl)-1,3,8-triaza-spiro[4.5]dec-1-en-4-one;

(408) 8-{(E)-2-[4-(3-hydroxy-azetidine-1-carbonyl)-2, dimethyl-phenyl]-ethenesulfonyl}-2-(3-trifluoromethoxy-phenyl)-1,3,8-triaza-spiro[4.5]dec-1-en-4-one;
(409) 2,N,N-trimethyl-3-{2-[4-oxo-2-(3-trifluoromethoxy-phenyl)-1,3,8-triaza-spiro[4.5]dec-1-ene-8-sulfonyl]-ethyl}-benzamide;
(410) 2-methyl-3-{2-[4-oxo-2-(3-trifluoromethoxy-phenyl)-1,3,8-triaza-spiro[4.5]dec-1-ene-sulfonyl]-ethyl}-benzamide;
(411) 8-{2-[2-methyl-3-(morpholine-4-carbonyl)-phenyl]-ethanesulfonyl}-2-(3-trifluoromethoxy-phenyl)-1,3,8-triaza-spiro[4.5]dec-1-en-4-one;
(412) 4,N,N-trimethyl-3-{2-[4-oxo-2-(3-trifluoromethoxy-phenyl)-1,3,8-triaza-spiro[4.5]dec-1-ene-8-sulfonyl]-ethyl}-benzamide;
(413) N-(2-hydroxy-ethyl)-4,N-dimethyl-3-{2-[4-oxo-2-trifluoromethoxy-phenyl)-1,3,8-triaza-spiro[4.5]dec-1-ene-8-sulfonyl]-ethyl}-benzamide;
(414) 8-{2-[2-methyl-5-(4-methyl-piperazine-1-carbonyl)-phenyl]-ethanesulfonyl}-2-(3-trifluoromethoxy-phenyl)-1,3,8-triaza-spiro[4.5]dec-1-en-4-one;
(415) 4,N-dimethyl-3-{2-[4-oxo-2-(3-trifluoromethoxy-phenyl)-1,3,8-triaza-spiro[4.5]dec-1-ene-8-sulfonyl]-ethyl}-benzamide;
(416) 8-(2-{4-[4-(2-hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-4-one;
(417) 8-{2-[2-methyl-4-(thiazolidine-3-carbonyl)-phenyl]-ethanesulfonyl}-2-(3-trifluoromethoxy-phenyl)-1,3,8-triaza-spiro[4.5]dec-1-en-4-one;
(418) 2-fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide;
(419) 8-{2-[5-fluoro-4-(4-hydroxy-piperidine-1-carbonyl)-2-methyl-phenyl]-ethanesulfonyl}-2-(3-trifluoromethyl-phenyl)-1,3,8-triaza-spiro[4.5]dec-1-en-4-one;
(420) N-benzyl-2-{4-[2-(2-cyclohexyl-4-oxo-1,3,8-triaza-spiro[4.5]dec-1-ene-8-sulfonyl)-ethyl]-1H-indol-3-yl}-acetamide;
(421) 2-[2-(2-cyclohexyl-4-oxo-1,3,8-triaza-spiro[4.5]dec-1-ene-8-sulfonyl)-ethyl]-N-methyl-benzamide;
(422) 3-[2-(2-cyclohexyl-4-oxo-1,3,8-triaza-spiro[4.5]dec-1-ene-8-sulfonyl)-ethyl]-N-pyridin-4-yl-benzamide;
(423) 8-(3-chloro-benzenesulfonyl)-2-[1-(3,3-dimethyl-butyryl)-piperidin-3-yl]-1,3,8-triaza-spiro[4.5]dec-1-en-4-one;
(424) 8-(3-chloro-benzenesulfonyl)-2-[1-(2-hydroxy-acetyl)-piperidin-3-yl]-1,3,8-triaza-spiro[4.5]dec-1-en-4-one;
(425) 8-(3-chloro-benzenesulfonyl)-2-[1-(4-chloro-benzoyl)-piperidin-3-yl]-1,3,8-triaza-spiro[4.5]dec-1-en-4-one;
(426) 8-(3-chloro-benzenesulfonyl)-2-[1-(3-methoxy-benzoyl)-piperidin-3-yl]-1,3,8-triaza-spiro[4.5]dec-1-en-4-one;
(428) 2-[1-(1H-indole-5-carbonyl)-piperidin-3-yl]-8-(2-naphthalen-1-yl-ethanesulfonyl)-1,3,8-triaza-spiro[4.5]dec-1-en-4-one;
(429) 8-(2-naphthalen-1-yl-ethanesulfonyl)-2-[1-(3-phenyl-propionyl)-piperidin-3-yl]-1,3,8-triaza-spiro[4.5]dec-1-en-4-one;
(430) 8-(2-naphthalen-1-yl-ethanesulfonyl)-2-[1-(1,2,3,4-tetrahydro-naphthalene-2-carbonyl)-piperidin-3-yl]-1,3,8-triaza-spiro[4.5]dec-1-en-4-one;
(431) 8-(2-naphthalen-1-yl-ethanesulfonyl)-2-[1-(quinoline-6-carbonyl)-piperidin-3-yl]-1,3,8-triaza-spiro[4.5]dec-1-en-4-one;
(432) 2-[1-(2-3H-imidazol-4-yl-acetyl)-piperidin-3-yl]-8-(2-naphthalen-1-yl-ethanesulfonyl)-1,3,8-triaza-spiro[4.5]dec-1-en-4-one;
(433) 2-{1-[2-(2,5-dimethyl-thiazol-4-yl)-acetyl]-piperidin-3-yl}-8-(2-naphthalen-1-yl-ethanesulfonyl)-1,3,8-triaza-spiro[4.5]dec-1-en-4-one;
(434) 2-{1-[2-(5-methyl-2-phenyl-oxazol-4-yl)-acetyl]-piperidin-3-yl}-8-(2-naphthalen-1-yl-ethanesulfonyl)-1,3,8-triaza-spiro[4.5]dec-1-en-4-one;
(435) 8-(2-naphthalen-1-yl-ethanesulfonyl)-2-[1-(2-pyridin-2-yl-acetyl)-piperidin-3-yl]-1,3,8-triaza-spiro[4.5]dec-1-en-4-one;
(436) 2-[1-(4-benzyloxy-butyryl)-piperidin-3-yl]-8-(2-naphthalen-1-yl-ethanesulfonyl)-1,3,8-triaza-spiro[4.5]dec-1-en-4-one;
(437) 8-(2-naphthalen-1-yl-ethanesulfonyl)-2-[1-(4-phenyl-butyryl)-piperidin-3-yl]-1,3,8-triaza-spiro[4.5]dec-1-en-4-one;
(438) 8-(2-naphthalen-1-yl-ethanesulfonyl)-2-[1-(2-pyridin-4-yl-acetyl)-piperidin-3-yl]-1,3,8-triaza-spiro[4.5]dec-1-en-4-one;
(439) 2-[1-(2-tert-butoxy-acetyl)-piperidin-3-yl]-8-(2-naphthalen-1-yl-ethanesulfonyl)-1,3,8-triaza-spiro[4.5]dec-1-en-4-one;
(441) 8-(2-naphthalen-1-yl-ethanesulfonyl)-2-{1-[(E)-(3-phenyl-acryloyl)]-piperidin-3-yl}-1,3,8-triaza-spiro[4.5]dec-1-en-4-one;
(442) 2-[1-(2-amino-acetyl)-piperidin-3-yl]-8-(3-chloro-benzenesulfonyl)-1,3,8-triaza-spiro[4.5]dec-1-en-4-one;
(444) 8-{2-[2-methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one;
(445) 8-{2-[4-(3-amino-pyrrolidine-1-carbonyl)-2-methyl-phenyl]-ethanesulfonyl}-2-(3-trifluoromethyl-phenyl)-1,3,8-triaza-spiro[4.5]dec-1-en-4-one hydrochloride;
(446) 8-{(E)-2-[2,6-dimethyl-4-(piperazine-1-carbonyl)-phenyl]-ethenesulfonyl}-2-(3-trifluoromethoxy-phenyl)-1,3,8-triaza-spiro[4.5]dec-1-en-4-one hydrochloride;
(447) 8-((E)-2-{4-[4-(2-hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;
(448) 4-[4-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzoyl)-piperazin-1-yl]-4-oxo-butyric acid methyl ester;
(449) 8-((E)-2-{4-[4-(4-dimethylamino-butyryl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one;
(450) 2-methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(451) 2-hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(452) [(3,5-dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid;
(453) 8-(3-chloro-benzenesulfonyl)-2-[1-(3,3-dimethyl-butyl)-piperidin-3-yl]-1,3,8-triaza-spiro[4.5]dec-1-en-4-one;
(454) 3-[8-(3-chloro-benzenesulfonyl)-4-oxo-1,3,8-triaza-spiro[4.5]dec-1-en-2-yl]-piperidine-1-carboxylic acid tert-butylamide;

(455) 3-[8-(2-naphthalen-1-yl-ethanesulfonyl)-4-oxo-1,3,8-triaza-spiro[4.5]dec-1-en-2-yl]-piperidine-1-carboxylic acid phenethyl-amide;

(456) 8-(3-chloro-benzenesulfonyl)-2-[1-(piperidine-1-carbonyl)-piperidin-3-yl]-1,3,8-triaza-spiro[4.5]dec-1-en-4-one;

(457) 3-(2-dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(458) 1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(459) 1-{3-[2-(2-cyclohexyl-4-oxo-1,3,8-triaza-spiro[4.5]dec-1-ene-8-sulfonyl)-ethyl]-2-methyl-phenyl}-3-methyl-urea;

(460) 3-[8-(3-chloro-benzenesulfonyl)-4-oxo-1,3,8-triaza-spiro[4.5]dec-1-en-2-yl]-piperidine-1-carboxylic acid 2-methoxy-ethyl ester;

(461) 3-[8-(3-chloro-benzenesulfonyl)-4-oxo-1,3,8-triaza-spiro[4.5]dec-1-en-2-yl]-piperidine-1-carboxylic acid benzyl ester;

(462) 3-[8-(3-chloro-benzenesulfonyl)-4-oxo-1,3,8-triaza-spiro[4.5]dec-1-en-2-yl]-piperidine-1-carboxylic acid isobutyl ester;

(463) 3-[8-(3-chloro-benzenesulfonyl)-4-oxo-1,3,8-triaza-spiro[4.5]dec-1-en-2-yl]-piperidine-1-carboxylic acid methyl ester;

(464) 3-[8-(2-naphthalen-1-yl-ethanesulfonyl)-4-oxo-1,3,8-triaza-spiro[4.5]dec-1-en-2-yl]-piperidine-1-carboxylic acid benzyl ester;

(465) 3-[8-(2-naphthalen-1-yl-ethanesulfonyl)-4-oxo-1,3,8-triaza-spiro[4.5]dec-1-en-2-yl]-piperidine-1-carboxylic acid 2,2-dimethyl-propyl ester;

(466) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester;

(467) methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid methyl ester;

(468) methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester;

(469) 2-cyclohexyl-8-(2-o-tolyl-ethanesulfonyl)-1,3,8-triaza-spiro[4.5]dec-1-ene-4-thione;

(470) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;

(471) 1-(3,5-dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea;

(472) 1-(3,5-dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea;

(474) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea;

(475) 8-{2-[2,6-dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one;

(476) {4-[(E)-2-(2-cyclohexyl-4-oxo-1,3,8-triaza-spiro[4.5]dec-1-ene-8-sulfonyl)-vinyl]-indol-1-yl}-acetic acid methyl ester;

(477) 2-cyclohexyl-8-{(E)-2-[1-(morpholine-4-carbonyl)-1H-indol-4-yl]-ethenesulfonyl}-1,3,8-triaza-spiro[4.5]dec-1-en-4-one;

(478) 2-cyclohexyl-8-{(E)-2-[1-(4-hydroxy-butyl)-1H-indol-4-yl]-ethenesulfonyl}-1,3,8-triaza-spiro[4.5]dec-1-en-4-one;

(479) 2-cyclohexyl-8-[(E)-2-(1H-indol-7-yl)-ethenesulfonyl]-1,3,8-triaza-spiro[4.5]dec-1-en-4-one;

(480) 2-cyclohexyl-8-{(E)-2-[1-(3,4-dihydroxy-butyl)-1H-indol-4-yl]-ethenesulfonyl}-1,3,8-triaza-spiro[4.5]dec-1-en-4-one;

(481) N-(2-{4-[(E)-2-(2-cyclohexyl-4-oxo-1,3,8-triaza-spiro[4.5]dec-1-ene-8-sulfonyl)-vinyl]-phenyl}-ethyl)-acetamide;

(482) N-(1-{4-[(E)-2-(2-cyclohexyl-4-oxo-1,3,8-triaza-spiro[4.5]dec-1-ene-8-sulfonyl)-vinyl]-phenyl}-ethyl)-acetamide;

(483) 2-cyclohexyl-8-[(E)-2-(1-thiazol-2-ylmethyl-1H-indol-4-yl)-ethenesulfonyl]-1,3,8-triaza-spiro[4.5]dec-1-en-4-one;

(484) 3-{4-[(E)-2-(2-cyclohexyl-4-oxo-1,3,8-triaza-spiro[4.5]dec-1-ene-8-sulfonyl)-vinyl]-indol-1-yl}-propane-1-sulfonic acid amide;

(485) 4-methyl-piperazine-1-carboxylic acid {4-[(E)-2-(2-cyclohexyl-4-oxo-1,3,8-triaza-spiro[4.5]dec-1-ene-8-sulfonyl)-vinyl]-3-trifluoromethyl-phenyl}-amide;

(486) {4-[(E)-2-(2-cyclohexyl-4-oxo-1,3,8-triaza-spiro[4.5]dec-1-ene-8-sulfonyl)-vinyl]-benzyl}-carbamic acid isobutyl ester;

(487) 2-cyclohexyl-8-((E)-2-{1-[2-(2-hydroxy-ethoxy)-ethyl]-1H-indol-5-yl}-ethenesulfonyl)-1,3,8-triaza-spiro[4.5]dec-1-en-4-one;

(488) 2-cyclohexyl-8-[(E)-2-(6-methyl-1H-indol-5-yl)-ethenesulfonyl]-1,3,8-triaza-spiro[4.5]dec-1-en-4-one;

(489) N-{4-[(E)-2-(2-cyclohexyl-4-oxo-1,3,8-triaza-spiro[4.5]dec-1-ene-8-sulfonyl)-vinyl]-benzyl}-2-hydroxy-acetamide;

(490) 3-(2-{4-[(E)-2-(2-cyclohexyl-4-oxo-1,3,8-triaza-spiro[4.5]dec-1-ene-8-sulfonyl)-vinyl]-phenyl}-ethyl)-1,1-dimethyl-urea;

(491) 8-[(E)-2-(4-amino-2,6-bis-trifluoromethyl-phenyl)-ethenesulfonyl]-2-cyclohexyl-1,3,8-triaza-spiro[4.5]dec-1-en-4-one;

(492) 2-cyclohexyl-8-[(E)-2-(6-trifluoromethyl-1H-indol-5-yl)-ethenesulfonyl]-1,3,8-triaza-spiro[4.5]dec-1-en-4-one;

(493) {4-[(E)-2-(2-cyclohexyl-4-oxo-1,3,8-triaza-spiro[4.5]dec-1-ene-8-sulfonyl)-vinyl]-3-trifluoromethyl-phenylamino}-acetic acid methyl ester;

(494) 2-{4-[(E)-2-(2-cyclohexyl-4-oxo-1,3,8-triaza-spiro[4.5]dec-1-ene-8-sulfonyl)-vinyl]-3-trifluoromethyl-phenylamino}-N-(2-hydroxy-ethyl)-acetamide;

(495) 4-[(E)-2-(2-cyclohexyl-4-oxo-1,3,8-triaza-spiro[4.5]dec-1-ene-8-sulfonyl)-vinyl]-N-(2-hydroxy-ethyl)-N-methyl-3-trifluoromethyl-benzenesulfonamide;

(496) 4-[(E)-2-(2-cyclohexyl-4-oxo-1,3,8-triaza-spiro[4.5]dec-1-ene-8-sulfonyl)-vinyl]-N,N-bis-(2-hydroxy-ethyl)-3-trifluoromethyl-benzenesulfonamide;

(497) 2-cyclohexyl-8-{(E)-2-[4-(2-dimethylamino-ethylamino)-2-methyl-phenyl]-ethenesulfonyl}-1,3,8-triaza-spiro[4.5]dec-1-en-4-one;

(498) N-(2-acetylamino-ethyl)-2-{4-[(E)-2-(2-cyclohexyl-4-oxo-1,3,8-triaza-spiro[4.5]dec-1-ene-8-sulfonyl)-vinyl]-3-trifluoromethyl-phenylamino}-acetamide;

(499) 2-cyclohexyl-8-[(E)-2-(6-trifluoromethyl-1H-benzimidazol-5-yl)-ethenesulfonyl]-1,3,8-triaza-spiro[4.5]dec-1-en-4-one;

(500) 2-cyclohexyl-8-{(E)-2-[1-((S)-2,2-dimethyl-[1,3]dioxolan-4-ylmethyl)-5-fluoro-1H-indol-4-yl]-ethenesulfonyl}-1,3,8-triaza-spiro[4.5]dec-1-en-4-one;

(501) 2-cyclohexyl-8-((E)-2-{4-[(2-hydroxy-ethyl)-methyl-amino]-2-trifluoromethyl-phenyl}-ethenesulfonyl)-1,3,8-triaza-spiro[4.5]dec-1-en-4-one;
(502) 2-cyclohexyl-8-{(E)-2-[4-(1,1-dioxo-1λ⁶-thiomorpholine-4-carbonyl)-2-methyl-phenyl]-ethenesulfonyl}-1,3,8-triaza-spiro[4.5]dec-1-en-4-one;
(503) 4-[(E)-2-(2-cyclohexyl-4-oxo-1,3,8-triaza-spiro[4.5]dec-1-ene-8-sulfonyl)-vinyl]-N-(2-dimethylamino-ethyl)-3-methyl-benzenesulfonamide;
(504) 3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;
(505) 1-methyl-3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;
(506) N-(3-isopropoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(507) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-5,5-dimethyl-imidazolidine-2,4-dione;
(508) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1,5,5-trimethyl-imidazolidine-2,4-dione;
(509) N-(3-ethoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(510) N-(3-ethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(511) 5,5-dimethyl-3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;
(512) N-(3-methoxymethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(513) 2-(4-methyl-cyclohexyl)-8-{(E)-2-[2-methyl-4-(2-oxo-oxazolidin-3-yl)-phenyl]-ethenesulfonyl}-1,3,8-triaza-spiro[4.5]dec-1-en-4-one;
(514) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-N-(2-methoxy-ethyl)-acetamide;
(515) 8-{(E)-2-[2,6-dimethyl-4-(3-oxo-morpholin-4-yl)-phenyl]-ethenesulfonyl}-2-(4-methyl-cyclohexyl)-1,3,8-triaza-spiro[4.5]dec-1-en-4-one;
(516) 8-{(E)-2-[2,6-dimethyl-4-(2-oxo-piperidin-1-yl)-phenyl]-ethenesulfonyl}-2-(4-methyl-cyclohexyl)-1,3,8-triaza-spiro[4.5]dec-1-en-4-one;
(517) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-N-methyl-acetamide;
(518) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-imidazolidine-2,4-dione;
(519) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-5,5-dimethyl-imidazolidine-2,4-dione;
(520) 8-{(E)-2-[2,6-dimethyl-4-(2-oxo-pyrrolidin-1-ylmethyl)-phenyl]-ethenesulfonyl}-2-(4-methyl-cyclohexyl)-1,3,8-triaza-spiro[4.5]dec-1-en-4-one;
(521) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-pyrrolidine-2,5-dione;
(522) N-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-acetamide;
(523) N-(3,5-difluoro-4-{(E)-2-[2-(4-methyl-cyclohexyl)-4-oxo-1,3,8-triaza-spiro[4.5]dec-1-ene-8-sulfonyl]-vinyl}-phenyl)-N-methyl-acetamide;
(524) 8-{(E)-2-[1-((S)-2,3-dihydroxy-propyl)-1H-indol-4-yl]-ethenesulfonyl}-2-(3-trifluoromethyl-phenyl)-1,3,8-triaza-spiro[4.5]dec-1-en-4-one;
(525) [(S)-1-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-2,5-dioxo-pyrrolidin-3-yl]-carbamic acid tert-butyl ester;
(526) 8-{(E)-2-[1-((S)-2,3-dihydroxy-propyl)-1H-indol-4-yl]-ethenesulfonyl}-2-(3-trifluoromethoxy-phenyl)-1,3,8-triaza-spiro[4.5]dec-1-en-4-one;
(527) 8-{(E)-2-[2-methyl-4-(4-methyl-piperazine-1-carbonyl)-phenyl]-ethenesulfonyl}-2-(3-trifluoromethoxy-phenyl)-1,3,8-triaza-spiro[4.5]dec-1-en-4-one;
(528) 8-((E)-2-{2-methyl-4-[2-(4-methyl-piperazin-1-yl)-2-oxo-ethylamino]-phenyl}-ethenesulfonyl)-2-(3-trifluoromethoxy-phenyl)-1,3,8-triaza-spiro[4.5]dec-1-en-4-one;
(529) 2-(3-methyl-4-{(E)-2-[4-oxo-2-(3-trifluoromethoxy-phenyl)-1,3,8-triaza-spiro[4.5]dec-1-ene-8-sulfonyl]-vinyl}-phenylamino)-acetamide;
(530) 3-methyl-4-{(E)-2-[4-oxo-2-(3-trifluoromethoxy-phenyl)-1,3,8-triaza-spiro[4.5]dec-1-ene-8-sulfonyl]-vinyl}-N-pyridin-4-yl-benzenesulfonamide;
(531) 8-{(E)-2-[4-(3,4-dihydroxy-butoxy)-2-methyl-phenyl]-ethenesulfonyl}-2-(3-trifluoromethoxy-phenyl)-1,3,8-triaza-spiro[4.5]dec-1-en-4-one;
(532) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-urea;
(533) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-bis-(2-hydroxy-ethyl)-3-methyl-urea;
(534) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-methanesulfonamide;
(535) 2-(4-fluoro-3-trifluoromethyl-phenyl)-8-{(E)-2-(4-hydroxy-piperidine-1-carbonyl)-2,6-dimethyl-phenyl ethenesulfonyl}-1,3,8-triaza-spiro[4.5]dec-1-en-4-one
(536) 3-{3-methyl-4-[(E)-2-(2-nonyl-4-oxo-1,3,8-triaza-spiro[4.5]dec-1-ene-8-sulfonyl)-vinyl]-phenyl}-imidazolidine-2,4-dione;
(537) 3-{4-[(E)-2-(2-nonyl-4-oxo-1,3,8-triaza-spiro[4.5]dec-1-ene-8-sulfonyl)-vinyl]-3-trifluoromethyl-phenyl}-imidazolidine-2,4-dione;
(538) 4-{3-methyl-4-[(E)-2-(2-nonyl-4-oxo-1,3,8-triaza-spiro[4.5]dec-1-ene-8-sulfonyl)-vinyl]-phenyl}-morpholine-3,5-dione;
(539) 3-{3,5-dimethyl-4-[(E)-2-(2-nonyl-4-oxo-1,3,8-triaza-spiro[4.5]dec-1-ene-8-sulfonyl)-vinyl]-phenyl}imidazolidine-2,4-dione;
(540) 5,5-dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione;
(541) 8-{(E)-2-[1-((R)-2,3-dihydroxy-propyl)-1H-indol-4-yl]-ethenesulfonyl}-2-[4-(3,3,3-trifluoro-propyl)-cyclohexyl]-1,3,8-triaza-spiro[4.5]dec-1-en-4-one;
(542) N-(2-methoxy-ethyl)-N-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-acetamide;

(543) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-(2-methoxy-ethyl)-acetamide;

(544) N-[2-(2-hydroxy-ethoxy)-ethyl]-N-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]acetamide;

(545) N-[2-(2-fluoro-ethoxy)-ethyl]-N-[3-methyl-4-((E {4-oxo-2-[4-(3,3,3-trifluoro-propyl)-cyclohexyl]-1,3,8 triaza-spiro[4.5]dec-1-ene-8-sulfonyl}-vinyl)-phenyl]acetamide;

(546) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-methyl-acetamide;

(547) 3,5-dimethyl-4-((E)-2-{4-oxo-2-[4-(3,3,3-trifluoro-propyl)-cyclohexyl]-1,3,8-triaza-spiro[4.5]dec-1-ene-sulfonyl}-vinyl)-benzoic acid;

(548) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-imidazolidine-2,4-dione;

(549) 8-((E)-2-{4-[4-(2-fluoro-ethyl)-piperazine-1-carbonyl]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;

(550) 8-{(E)-2-[2,6-dimethyl-4-(3-oxo-morpholin-4-yl)-phenyl]-ethenesulfonyl}-2-[4-(3,3,3-trifluoro-propyl)-cyclohexyl]-1,3,8-triaza-spiro[4.5]dec-1-en-4-one;

(551) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-fluoro-ethoxy)-ethyl]-acetamide;

(552) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid N'-acetyl-hydrazide;

(553) 8-[(E)-2-(4-hydroxymethyl-2,6-dimethyl-phenyl)-ethenesulfonyl]-2-[4-(3,3,3-trifluoro-propyl)-cyclohexyl]-1,3,8-triaza-spiro[4.5]dec-1-en-4-one;

(554) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-imidazolidine-2,4-dione;

(555) 3-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-5,5-dimethyl-imidazolidine-2,4-dione;

(556) 8-{(E)-2-[2,6-dimethyl-4-(2-oxo-pyrrolidin-1-ylmethyl)-phenyl]-ethenesulfonyl}-2-[4-(3,3,3-trifluoro-propyl)-cyclohexyl]-1,3,8-triaza-spiro[4.5]dec-1-en-4-one;

(557) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-pyrrolidine-2,5-dione;

(558) N-[3,5-dimethyl-4-((E)-2-{4-oxo-2-[4-(3,3,3-trifluoro-propyl)-cyclohexyl]-1,3,8-triaza-spiro[4.5]1-ene-8-sulfonyl}-vinyl)-benzyl]-acetamide;

(559) N-[3,5-dimethyl-4-((E)-2-{4-oxo-2-[4-(3,3,3-trifluoro-propyl)-cyclohexyl]-1,3,8-triaza-spiro[4.5]1-ene-8-sulfonyl}-vinyl)-benzyl]-N-methyl-acetamide;

(560) 3-(4-{(E)-2-[2-(4-butyl-cyclohexyl)-4-oxo-1,3,8 triaza-spiro[4.5]dec-1-ene-8-sulfonyl]-vinyl}-3-methyl-phenyl)-imidazolidine-2,4-dione;

(561) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-methoxy-ethoxy)-ethyl]-acetamide;

(562) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-fluoro-ethoxy)-ethyl]-acetamide;

(563) 3-(4-{(E)-2-[2-(4-isopropyl-cyclohexyl)-4-oxo-1,3,8-triaza-spiro[4.5]dec-1-ene-8-sulfonyl]-vinyl}-3-methyl-phenyl)-imidazolidine-2,4-dione;

(564) 3-(4-{(E)-2-[2-(4-isopropyl-cyclohexyl)-4-oxo-1,3,8-triaza-spiro[4.5]dec-1-ene-8-sulfonyl]-vinyl}-3,5-dimethyl-phenyl)-imidazolidine-2,4-dione;

(565) 3-{4-[(E)-2-(2-cyclohexyl-4-oxo-1,3,8-triaza-spiro[4.5]dec-1-ene-8-sulfonyl)-vinyl]-benzyl}-1,1-dimethyl-urea;

(566) (2-{4-[(E)-2-(2-cyclohexyl-4-oxo-1,3,8-triaza-spiro[4.5]dec-1-ene-8-sulfonyl)-vinyl]-phenyl}-ethyl)-carbamic acid methyl ester;

(567) 4-methyl-piperazine-1-carboxylic acid 4-[(E)-2-(2-cyclohexyl-4-oxo-1,3,8-triaza-spiro[4.5]dec-1-ene-8-sulfonyl)-vinyl]-benzylamide;

(568) N-{4-[(E)-2-(2-cyclohexyl-4-oxo-1,3,8-triaza-spiro[4.5]dec-1-ene-8-sulfonyl)-vinyl]-3-methyl-phenyl}-N',N'-dimethyl-sulfamide;

(569) {4-[(E)-2-(2-cyclohexyl-4-oxo-1,3,8-triaza-spiro[4.5]dec-1-ene-8-sulfonyl)-vinyl]-3-methyl-benzyl}-(3-dimethylamino-propyl)-carbamic acid tert-butyl ester;

(570) 2-{4-[(E)-2-(2-cyclohexyl-4-oxo-1,3,8-triaza-spiro[4.5]dec-1-ene-8-sulfonyl)-vinyl]-phenyl}-N-(2,2-dimethyl-propyl)-acetamide;

(571) 2-{4-[(E)-2-(2-cyclohexyl-4-oxo-1,3,8-triaza-spiro[4.5]dec-1-ene-8-sulfonyl)-vinyl]-phenyl}-N-(2-diisopropylamino-ethyl)-acetamide;

(572) 2-cyclohexyl-8-{(E)-2-[2-methyl-4-(2-oxo-azetidin-1-yl)-phenyl]-ethenesulfonyl}-1,3,8-triaza-spiro[4.5]dec-1-en-4-one;

(573) 2-cyclohexyl-8-{(E)-2-[2,6-dimethyl-4-(thiazol-2-ylamino)-phenyl]-ethenesulfonyl}-1,3,8-triaza-spiro[4.5]dec-1-en-4-one;

(574) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(3-methyl-oxetan-3-ylmethyl)-acetamide;

(575) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(576) N-(3-ethoxymethyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(577) 2-(4-methyl-cyclohexyl)-8-{(E)-2-[2-methyl-4-(4-oxo-oxazolidin-3-yl)-phenyl]-ethenesulfonyl}-1,3,8-triaza-spiro[4.5]dec-1-en-4-one;

(578) 4-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-3-oxo-piperazine-1-carboxylic acid tert-butyl ester;

(579) 2-(4-methyl-cyclohexyl)-8-{(E)-2-[2-methyl-4-(4-methyl-2-oxo-oxazolidin-3-yl)-phenyl]-ethenesulfonyl}-1,3,8-triaza-spiro[4.5]dec-1-en-4-one;

(580) 2-(4-methyl-cyclohexyl)-8-{(E)-2-[2-methyl-4-(3-oxo-isoxazolidin-2-yl)-phenyl]-ethenesulfonyl}-1,3,8-triaza-spiro[4.5]dec-1-en-4-one;

(581) 3-(2,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(582) 3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-5-methyl-imidazolidine-2,4-dione;

(583) 3-(2,6-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;

(584) N-(2,6-dimethyl-4-{(E)-2-[2-(4-methyl-cyclohexyl)-4-oxo-1,3,8-triaza-spiro[4.5]dec-1-ene-8-sulfonyl]-vinyl}-phenyl)-N-methyl-acetamide;

(585) 8-[(E)-2-(3-methoxy-2-methyl-phenyl)-ethenesulfonyl]-2-(4-methyl-cyclohexyl)-1,3,8-triaza-spiro[4.5]dec-1-en-4-one;
(586) 8-((E)-2-{4-[(1H-imidazol-2-yl)-methyl-amino]-2,6-dimethyl-phenyl}-ethenesulfonyl)-2-(4-methyl-cyclohexyl)-1,3,8-triaza-spiro[4.5]dec-1-en-4-one;
(587) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-dihydro-pyrimidine-2,4-dione;
(588) 2-(4-methyl-cyclohexyl)-8-{(E)-2-[2-methyl-4-(5-oxo-pyrazolidin-1-yl)-phenyl]-ethenesulfonyl}-1,3,8-triaza-spiro[4.5]dec-1-en-4-one;
(589) 5-tert-butoxymethyl-3-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione;
(590) N,N-dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide;
(591) 3-methyl-4-{(E)-2-[4-oxo-2-(3-trifluoromethyl-phenyl)-1,3,8-triaza-spiro[4.5]dec-1-ene-8-sulfonyl]-vinyl}-N-pyridin-3-ylmethyl-benzenesulfonamide;
(592) N-(4-hydroxy-cyclohexyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;
(593) 8-[(E)-2-(4-methanesulfonyl-2-methyl-phenyl)-ethenesulfonyl]-2-(3-trifluoromethyl-phenyl)-1,3,8-triaza-spiro[4.5]dec-1-en-4-one;
(594) N-acetyl-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;
(595) N-(2-hydroxy-1,1-bis-hydroxymethyl-ethyl)-3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonamide;
(596) N-(1-benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;
(597) 8-{(E)-2-[1-((S)-2,3-dihydroxy-propyl)-1H-indol-5-yl]-ethenesulfonyl}-2-(3-trifluoromethoxy-phenyl)-1,3,8-triaza-spiro[4.5]dec-1-en-4-one;
(598) 8-{(E)-2-[4-(4-isopropyl-piperazine-1-carbonyl)-2-methyl-phenyl]-ethenesulfonyl}-2-(3-trifluoromethoxy-phenyl)-1,3,8-triaza-spiro[4.5]dec-1-en-4-one;
(599) N—((R)-2,3-dihydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide;
(600) 8-{(E)-2-[4-(3,4-dihydroxy-butoxy)-3,5-difluoro-phenyl]-ethenesulfonyl}-2-(3-trifluoromethoxy-phenyl)-1,3,8-triaza-spiro[4.5]dec-1-en-4-one;
(601) 8-{(E)-2-[4-(3,4-dihydroxy-butoxy)-3,5-dimethyl-phenyl]-ethenesulfonyl}-2-(3-trifluoromethoxy-phenyl)-1,3,8-triaza-spiro[4.5]dec-1-en-4-one;
(602) 4-(3-methyl-4-{(E)-2-[4-oxo-2-(3-trifluoromethoxy-phenyl)-1,3,8-triaza-spiro[4.5]dec-1-ene-8-sulfonyl]-vinyl}-phenoxy)-piperidine-1-carboxylic acid tert-butyl ester;
(603) N-isopropyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(604) 4-[acetyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-amino]-piperidine-1-carboxylic acid tert-butyl ester;
(605) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-urea;
(606) 8-((E)-2-{4-[(R)-2-(isopropylamino-methyl)-5-oxo-pyrrolidin-1-yl]-2,6-dimethyl-phenyl}-ethenesulfonyl)-2-(3-trifluoromethoxy-phenyl)-1,3,8-triaza-spiro[4.5]dec-1-en-4-one;
(607) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(608) 2-dimethylamino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;
(609) N-(2-dimethylamino-ethyl)-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;
(610) N—[(R)-1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5-oxo-pyrrolidin-2-ylmethyl]-acetamide;
(611) 8-{(E)-2-[4-((R)-2-dimethylaminomethyl-5-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;
(612) N-cyanomethyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;
(613) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2,2,2-trifluoro-ethyl)-acetamide;
(614) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,5,5-trimethyl-imidazolidine-2,4-dione;
(615) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-5,5-dimethyl-imidazolidine-2,4-dione;
(616) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(tetrahydro-pyran-4-acetamide;
(617) 8-{(E)-2-[2-methyl-4-(3-oxo-morpholin-4-yl)-phenyl]-ethenesulfonyl}-2-(3-trifluoromethoxy-phenyl) 1,3,8-triaza-spiro[4.5]dec-1-en-4-one;
(618) 3-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione;
(619) 2-(4-fluoro-3-trifluoromethyl-phenyl)-8-{(E)-[2-methyl-4-(pyrrolidine-1-carbonyl)-phenyl]-ethenesulfonyl}-1,3,8-triaza-spiro[4.5]dec-1-en-4-one;
(620) 2-(4-fluoro-3-trifluoromethyl-phenyl)-8-{(E)-2-[4-((R)-2-hydroxymethyl-5-oxo-pyrrolidin-1-yl)-2-methyl-phenyl]-ethenesulfonyl}-1,3,8-triaza-spiro[4.5]dec-1-en-4-one;
(621) 2-(4-fluoro-3-trifluoromethyl-phenyl)-8-{(E)-2-[4-((S)-2-hydroxymethyl-5-oxo-pyrrolidin-1-yl)-2-methyl-phenyl]-ethenesulfonyl}-1,3,8-triaza-spiro[4.5]dec-1-en-4-one;
(622) 8-{(E)-2-[1-((S)-2,3-dihydroxy-propyl)-1H-indol-4-yl]-ethenesulfonyl}-2-(9,9,9-trifluoro-nonyl)-1,3,8-triaza-spiro[4.5]dec-1-en-4-one;
(623) 8-{(E)-2-[1-((S)-2,3-dihydroxy-propyl)-1H-indol-4-yl]-ethenesulfonyl}-2-(8,8,9,9,9-pentafluoro-nonyl)-1,3,8-triaza-spiro[4.5]dec-1-en-4-one;

(624) 1-(4-{(E)-2-[2-(4-ethyl-cyclohexyl)-4-oxo-1,3,8-tri-aza-spiro[4.5]dec-1-ene-8-sulfonyl]-vinyl}-3-methyl-phenyl)-imidazolidine-2,4-dione;

(625) 1-(4-{(E)-2-[2-(4-ethyl-cyclohexyl)-4-oxo-1,3,8-tri-aza-spiro[4.5]dec-1-ene-8-sulfonyl]-vinyl}-3-methyl-phenyl)-5-methyl-imidazolidine-2,4-dione;

(626) 1-(4-{(E)-2-[2-(4-ethyl-cyclohexyl)-4-oxo-1,3,8-tri-aza-spiro[4.5]dec-1-ene-8-sulfonyl]-vinyl}-3-methyl-phenyl)-5,5-dimethyl-imidazolidine-2,4-dione;

(627) 8-{(E)-2-[4-(3,4-dihydroxy-butoxy)-2,6-dimethyl-phenyl]-ethenesulfonyl}-2-nonyl-1,3,8-triaza-spiro[4.5]dec-1-en-4-one;

(628) 3,5-dimethyl-4-[(E)-2-(2-nonyl-4-oxo-1,3,8-triaza-spiro[4.5]dec-1-ene-8-sulfonyl)-vinyl]-benzoic acid;

(629) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide;

(630) 8-{(E)-2-[1-((R)-2,3-dihydroxy-propyl)-4,6-dim-ethyl-1H-indol-5-yl]-ethenesulfonyl}-2-[4-(3,3,3-trif-luoro-propyl)-cyclohexyl]-1,3,8-triaza-spiro[4.5]dec-1-en-4-one;

(631) 3-(4-{(E)-2-[2-(4-butyl-cyclohexyl)-4-oxo-1,3,8-tri-aza-spiro[4.5]dec-1-ene-8-sulfonyl]-vinyl}-3,5-dimethyl-phenyl)-imidazolidine-2,4-dione;

(632) N-(4-{(E)-2-[2-(4-butyl-cyclohexyl)-4-oxo-1,3,8-tri-aza-spiro[4.5]dec-1-ene-8-sulfonyl]-vinyl}-3,5-dimethyl-phenyl)-N-(3-methyl-oxetan-3-ylmethyl)-acetamide;

(633) 2-cyclohexyl-8-((E)-2-quinolin-8-yl-ethenesulfonyl)-1,3,8-triaza-spiro[4.5]dec-1-en-4-one;

(634) 2-cyclohexyl-8-[(E)-2-(2-oxo-2,3-dihydro-1H-indol-4-yl)-ethenesulfonyl]-1,3,8-triaza-spiro[4.5]dec-1-en-4-one;

(635) 3-(3,5-dimethyl-4-{(E)-2-[4-oxo-2-(3-trifluo-romethoxy-phenyl)-1,3,8-triaza-spiro[4.5]dec-1-ene-8-sulfonyl]-vinyl}-phenyl)-imidazolidine-2,4-dione;

(636) 3-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione;

(637) 2-cyclohexyl-8-[(E)-2-(2-methyl-1H-indol-4-yl)-ethenesulfonyl]-1,3,8-triaza-spiro[4.5]dec-1-en-4-one;

(638) 2-cyclohexyl-8-[(E)-2-(1-methyl-1,2,3,4-tetrahydro-quinolin-5-yl)-ethenesulfonyl]-1,3,8-triaza-spiro[4.5]dec-1-en-4-one;

(639) 8-{(E)-2-[4-(3,4-dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one;

(640) (4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-[1,1,1-$^2$H$_3$]methyl-carbamic acid tert-butyl ester;

(641) 8-{(E)-2-[4-(4-fluoromethyl-4-hydroxy-piperidine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(642) 2-(4-fluoro-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(643) 8-{(E)-2-[1-((S)-2,3-dihydroxy-propyl)-1H-indol-4-yl]-ethenesulfonyl}-2-(4-fluoro-3-trifluoromethyl-phe-nyl)-1,3,8-triaza-spiro[4.5]dec-1-en-4-one;

(644) 8-{(E)-2-[2,6-dimethyl-4-(2-oxa-7-aza-spiro[3.5]nonane-7-carbonyl)-phenyl]-ethenesulfonyl}-2-(4-fluoro-3-trifluoromethyl-phenyl)-1,3,8-triaza-spiro[4.5]dec-1-en-4-one;

(645) 2-cyclohexyl-8-[2-(1,2,3,4-tetrahydro-quinolin-5-yl)-ethanesulfonyl]-1,3,8-triaza-spiro[4.5]dec-1-en-4-one;

(646) 4-[2-(2-cyclohexyl-4-oxo-1,3,8-triaza-spiro[4.5]dec-1-ene-8-sulfonyl)-ethyl]-1H-indole-3-carbonitrile;

(647) 7-[2-(2-cyclohexyl-4-oxo-1,3,8-triaza-spiro[4.5]dec-1-ene-8-sulfonyl)-ethyl]-indole-1-carboxylic acid dim-ethylamide;

(648) 2-cyclohexyl-8-(2-quinolin-5-yl-ethanesulfonyl)-1,3,8-triaza-spiro[4.5]dec-1-en-4-one;

(649) 2-cyclohexyl-8-{2-[3-(2,2,2-trifluoro-acetyl)-1H-in-dol-4-yl]-ethanesulfonyl}-1,3,8-triaza-spiro[4.5]dec-1-en-4-one;

(650) 2-cyclohexyl-8-[2-(1-isopropyl-1H-indol-4-yl)-eth-anesulfonyl]-1,3,8-triaza-spiro[4.5]dec-1-en-4-one;

(651) 2-cyclohexyl-8-{2-[1-(4-hydroxy-butyl)-1H-indol-4-yl]-ethanesulfonyl}-1,3,8-triaza-spiro[4.5]dec-1-en-4-one;

(652) N-{3-cyano-4-[2-(2-cyclohexyl-4-oxo-1,3,8-triaza-spiro[4.5]dec-1-ene-8-sulfonyl)-ethyl]-phenyl}-acet-amide;

(653) 8-(2-isoquinolin-5-yl-ethanesulfonyl)-2-(3-trifluo-romethoxy-phenyl)-1,3,8-triaza-spiro[4.5]dec-1-en-4-one;

(654) 8-(2-quinolin-5-yl-ethanesulfonyl)-2-(3-trifluo-romethoxy-phenyl)-1,3,8-triaza-spiro[4.5]dec-1-en-4-one;

(655) N-(3-methoxy-4-{2-[2-(4-methyl-cyclohexyl)-4-oxo-1,3,8-triaza-spiro[4.5]dec-1-ene-8-sulfonyl]-ethyl}-phe-nyl)-acetamide;

(656) 8-{2-[4-(3,3-dimethyl-1,1,4-trioxo-1λ$^6$-[1,2,5]thiadi-azolidin-2-yl)-2,6-dimethyl-phenyl]-ethanesulfonyl}-2-(4-methyl-cyclohexyl)-1,3,8-triaza-spiro[4.5]dec-1-en-4-one;

(657) 8-{2-[2-methyl-4-(3-oxo-morpholin-4-yl)-phenyl]-ethanesulfonyl}-2-nonyl-1,3,8-triaza-spiro[4.5]dec-1-en-4-one;

(658) {4-[2-(2-cyclohexyl-4-oxo-1,3,8-triaza-spiro[4.5]dec-1-ene-8-sulfonyl)-ethyl]-benzyl}-carbamic acid isobutyl ester;

(659) N-{4-[2-(2-cyclohexyl-4-oxo-1,3,8-triaza-spiro[4.5]dec-1-ene-8-sulfonyl)-ethyl]-benzyl}-2-hydroxy-acet-amide;

(660) 2-{4-[2-(2-cyclohexyl-4-oxo-1,3,8-triaza-spiro[4.5]dec-1-ene-8-sulfonyl)-ethyl]-3-trifluoromethyl-phe-nylamino}-N-(4-hydroxy-butyl)-acetamide;

(661) {4-[2-(2-cyclohexyl-4-oxo-1,3,8-triaza-spiro[4.5]dec-1-ene-8-sulfonyl)-ethyl]-3-trifluoromethyl-phenyl}-car-bamic acid isobutyl ester;

(662) N-{4-[2-(2-cyclohexyl-4-oxo-1,3,8-triaza-spiro[4.5]dec-1-ene-8-sulfonyl)-ethyl]-3-trifluoromethyl-phenyl}-benzamide;

(663) 2-cyclohexyl-8-[2-(2-oxo-2,3-dihydro-benzothiazol-6-yl)-ethanesulfonyl]-1,3,8-triaza-spiro[4.5]dec-1-en-4-one;

(664) N-(2-{4-[2-(2-cyclohexyl-4-oxo-1,3,8-triaza-spiro[4.5]dec-1-ene-8-sulfonyl)-ethyl]-3-methyl-benzenesul-fonylamino}-ethyl)-acetamide;

(665) N-(2-dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;

(666) 8-{2-[4-((2R,6S)-2,6-dimethyl-morpholine-4-carbo-nyl)-2-methyl-phenyl]-ethanesulfonyl}-2-(3-trifluo-romethoxy-phenyl)-1,3,8-triaza-spiro[4.5]dec-1-en-4-one;

(667) N-(2,2,3,3,4,4,4-heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(668) 8-[2-(3-methoxy-2-methyl-phenyl)-ethanesulfonyl]-2-(4-methyl-cyclohexyl)-1,3,8-triaza-spiro[4.5]dec-1-en-4-one;
(669) (2-methoxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-carbamic acid tert-butyl ester;
(670) 8-{2-[4-((S)-2-hydroxymethyl-5-oxo-pyrrolidin-1-yl)-2-methyl-phenyl]-ethanesulfonyl}-2-nonyl-1,3,8-triaza-spiro[4.5]dec-1-en-4-one;
(671) 8-[2-(5,7-dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one;
(672) (2-{4-[2-(2-cyclohexyl-4-oxo-1,3,8-triaza-spiro[4.5]dec-1-ene-8-sulfonyl)-ethyl]-phenyl}-ethyl)-carbamic acid methyl ester;
(673) {4-[2-(2-cyclohexyl-4-oxo-1,3,8-triaza-spiro[4.5]dec-1-ene-8-sulfonyl)-ethyl]-3-methyl-benzyl}-methyl-carbamic acid tert-butyl ester;
(674) 8-(2-{4-[3-(2-hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one;
(675) 2-(3-methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide;
(676) 8-{2-[4-(3,4-dihydroxy-butoxy)-2,6-dimethyl-phenyl]-ethanesulfonyl}-2-(3-trifluoromethoxy-phenyl)-1,3,8-triaza-spiro[4.5]dec-1-en-4-one;
(677) 3-(4-{2-[2-(4-butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione;
(678) N-cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(679) 1-(2,3-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(680) 1-(2,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(681) {4-[2-(2-cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester;
(682) 1-(3-methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(683) 1-(3-chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(684) 1-(2-methoxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(685) 5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione;
(686) 8-{(E)-2-[1-(2-amino-ethyl)-1H-indol-4-yl]-ethenesulfonyl}-2-cyclohexyl-1,3,8-triaza-spiro[4.5]dec-1-en-4-one;
(687) 8-[(E)-2-(4-aminomethyl-phenyl)-ethenesulfonyl]-2-cyclohexyl-1,3,8-triaza-spiro[4.5]dec-1-en-4-one;
(688) (S)-2-amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide;
(689) N-(3,5-dimethyl-4-{(E)-2-[4-oxo-2-(3-trifluoromethyl-phenyl)-1,3,8-triaza-spiro[4.5]dec-1-ene-8-sulfonyl]-vinyl}-phenyl)-N-piperidin-4-yl-methanesulfonamide;
(690) 8-[(E)-2-(2,6-dimethyl-4-methylamino-phenyl)-ethenesulfonyl]-2-(9,9,9-trifluoro-nonyl)-1,3,8-triaza-spiro[4.5]dec-1-en-4-one;
(691) 8-[(E)-2-(2,6-dimethyl-4-methylamino-phenyl)-ethenesulfonyl]-2-(8,8,9,9,9-pentafluoro-nonyl)-1,3,8-triaza-spiro[4.5]dec-1-en-4-one;
(692) 1-{3,5-dimethyl-4-[(E)-2-(2-nonyl-4-oxo-1,3,8-triaza-spiro[4.5]dec-1-ene-8-sulfonyl)-vinyl]-phenyl}-1-methyl-urea;
(693) 1-(2-methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;
(694) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea;
(695) 1-(3-chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;
(696) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea;
(697) 8-{(E)-2-[4-((R)-2,3-dihydroxy-propoxy)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;
(698) 8-((E)-2-{4-[2-((R)-2,3-dihydroxy-propoxy)-ethoxy]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;
(699) N-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide;
(700) N-[2-(2-hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide;
(701) N-{3,5-dimethyl-4-[(E)-2-(2-nonyl-4-oxo-1,3,8-triaza-spiro[4.5]dec-1-ene-8-sulfonyl)-vinyl]-phenyl}-N-(2-hydroxy-ethyl)-acetamide;
(702) 2-cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one;
(704) 8-((E)-2-{1-[2-((S)-2,3-dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one;
(705) 8-{(E)-2-[2,6-dimethyl-4-((2S,3S)-2,3,4-trihydroxy-butoxy)-phenyl]-ethenesulfonyl}-2-[4-(3,3,3-trifluoro-propyl)-cyclohexyl]-1,3,8-triaza-spiro[4.5]dec-1-en-4-one;
(706) 2-[4-(3,3,3-trifluoro-propyl)-cyclohexyl]-8-((E)-2-{1-[2-((2S,3S)-2,3,4-trihydroxy-butoxy)-ethyl]-H-indol-4-yl}-ethenesulfonyl)-1,3,8-triaza-spiro[4.5]dec-1-en-4-one;
(707) N—((S)-2,3-dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide;
(708) {4-[(E)-2-(2-cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester;
(709) N-{4-[(E)-2-(2-cyclohexyl-4-oxo-1,3,8-triaza-spiro[4.5]dec-1-ene-8-sulfonyl)-vinyl]-3,5-dimethyl-phenyl}-N-(4-hydroxy-cyclohexyl)-acetamide;
(710) 2-cyclohexyl-8-((E)-2-{4-[(R)-2-(2-hydroxy-ethoxymethyl)-5-oxo-pyrrolidin-1-yl]-2,6-dimethyl-phenyl}-ethenesulfonyl)-1,3,8-triaza-spiro[4.5]dec-1-en-4-one;

(711) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide;

(712) 8-{(E)-2-[4-((R)-5-hydroxymethyl-3,3-dimethyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(713) 8-{(E)-2-[4-((R)-5-hydroxymethyl-3-methyl-2-oxo-pyrrolidin-1-yl)-2,6-dimethyl-phenyl]-ethenesulfonyl}-2-(3-trifluoromethoxy-phenyl)-1,3,8-triaza-spiro[4.5]dec-1-en-4-one;

(714) 3-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2-hydroxy-ethyl)-5,5-dimethyl-imidazolidine-2,4-dione;

(715) N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(4-hydroxy-cyclohexyl)methanesulfonamide;

(716) N-(4-{(E)-2-[2-(4-butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide;

(717) N-(2-fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide;

(718) N-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide;

(719) N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide;

(720) N-(2-hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide;

(721) N-(4-{2-[2-(4-fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide;

(722) 2-hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(723) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea;

(724) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea;

(725) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-methoxy-ethyl)-urea;

(726) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea;

(727) 1-(3-ethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(728) 1-(3-methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea;

(729) 1-cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(730) 1-cyclopentyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea;

(731) 1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea;

(732) 1-(4-{2-[2-(4-ethyl-cyclohexyl)-4-oxo-1,3,8-triaza-spiro[4.5]dec-1-ene-8-sulfonyl]-ethyl}-3,5-dimethyl-phenyl)-1-methyl-urea;

(733) 1-((S)-2,3-dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea;

(734) N-{4-[(E)-2-(2-cyclohexyl-4-oxo-1,3,8-triaza-spiro[4.5]dec-1-ene-8-sulfonyl)-vinyl]-3-methyl-phenyl}-N-cyclopentyl-acetamide;

(735) (S)-2-amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide;

(736) 2-{4-[(E)-2-(2-cyclohexyl-4-oxo-1,3,8-triaza-spiro[4.5]dec-1-ene-8-sulfonyl)-vinyl]-indol-1-yl}-N-pyridin-4-yl-acetamide;

(737) 2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;

(738) 2-cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one;

(739) 2-cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one;

(740) 1-(3,5-dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea;

(741) 1-(3,5-dimethyl-4-{(E)-1-methyl-2-[2-(4-methyl-cyclohexyl)-4-oxo-1,3,8-triaza-spiro[4.5]dec-1-ene-8-sulfonyl]-vinyl}-phenyl)-1-methyl-urea;

(742) N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(743) N-(3-hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide;

(744) N-methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide;

(745) 2-cyclohexyl-8-[2-(2-methyl-1H-indol-4-yl)-ethanesulfonyl]-1,3,8-triaza-spiro[4.5]dec-1-en-4-one;

(746) 8-{2-[1-((S)-2,3-dihydroxy-propyl)-1H-indol-4-yl]-ethanesulfonyl}-2-(3-trifluoromethoxy-phenyl)-1,3,8-triaza-spiro[4.5]dec-1-en-4-one;

(747) 2-cyclohexyl-8-[2-(1-methyl-1,2,3,4-tetrahydro-quinolin-5-yl)-ethanesulfonyl]-1,3,8-triaza-spiro[4.5]dec-1-en-4-one;

(748) 2-cyclohexyl-8-{2-[1-(3,4-dihydroxy-butyl)-1H-indol-4-yl]-ethanesulfonyl}-1,3,8-triaza-spiro[4.5]dec-1-en-4-one;

(749) 3-(2,6-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(750) 2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(751) N-(3-ethoxy-4-{2-[2-(4-methyl-cyclohexyl)-4-oxo-1,3,8-triaza-spiro[4.5]dec-1-ene-8-sulfonyl]-ethyl}-phenyl)-acetamide;

(752) N-(3-ethyl-4-{2-[2-(4-methyl-cyclohexyl)-4-oxo-1,3,8-triaza-spiro[4.5]dec-1-ene-8-sulfonyl]-ethyl}-phenyl)-acetamide;

(753) N-(3-ethoxymethyl-4-{2-[2-(4-methyl-cyclohexyl)-4-oxo-1,3,8-triaza-spiro[4.5]dec-1-ene-8-sulfonyl]-ethyl}-phenyl)-acetamide;

(754) N-(3-methoxymethyl-4-{2-[2-(4-methyl-cyclohexyl)-4-oxo-1,3,8-triaza-spiro[4.5]dec-1-ene-8-sulfonyl]-ethyl}-phenyl)-acetamide;

(755) N-(2-methoxy-ethyl)-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-acetamide;

(756) N-[3,5-dimethyl-4-(2-{4-oxo-2-[4-(3,3,3-trifluoro-propyl)-cyclohexyl]-1,3,8-triaza-spiro[4.5]dec-1-ene-sulfonyl}-ethyl)-phenyl]-N-(2-methoxy-ethyl)-acetamide;

(757) N-[2-(2-fluoro-ethoxy)-ethyl]-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]acetamide;

(758) N-[2-(2-hydroxy-ethoxy)-ethyl]-N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]acetamide;

(759) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-methyl-acetamide;

(760) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-imidazolidine-2,4-dione;

(761) 8-(2-{4-[4-(2-fluoro-ethyl)-piperazine-1-carbonyl]-2,6-dimethyl-phenyl}-ethanesulfonyl)-2-[4-(3,3,3-trifluoro-propyl)-cyclohexyl]-1,3,8-triaza-spiro[4.5]dec-1-en-4-one;

(764) 8-{2-[2,6-dimethyl-4-(3-oxo-morpholin-4-yl)-phenyl]-ethanesulfonyl}-2-[4-(3,3,3-trifluoro-propyl)-cyclohexyl]-1,3,8-triaza-spiro[4.5]dec-1-en-4-one;

(765) 8-{2-[2,6-dimethyl-4-(3-oxo-morpholin-4-yl)-phenyl]-ethanesulfonyl}-2-(4-methyl-cyclohexyl)-1,3,8-triaza-spiro[4.5]dec-1-en-4-one;

(766) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-[2-(2-fluoro-ethoxy)-ethyl] acetamide;

(767) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5-methyl-imidazolidine-2,4-dione;

(768) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid;

(769) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N'-acetyl-hydrazide;

(770) 8-[2-(4-hydroxymethyl-2,6-dimethyl-phenyl)-ethanesulfonyl]-2-[4-(3,3,3-trifluoro-propyl)-cyclohexyl]-1,3,8-triaza-spiro[4.5]dec-1-en-4-one;

(771) 8-{2-[2,6-dimethyl-4-(2-oxo-piperidin-1-yl)-phenyl]-ethanesulfonyl}-2-(4-methyl-cyclohexyl)-1,3,8-triaza-spiro[4.5]dec-1-en-4-one;

(772) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide;

(773) N-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-acetamide;

(774) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-imidazolidine-2,4-dione;

(775) 3-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-5,5-dimethyl-imidazolidine-2,4-dione;

(776) 8-{2-[2,6-dimethyl-4-(2-oxo-pyrrolidin-1-ylmethyl)-phenyl]-ethanesulfonyl}-2-[4-(3,3,3-trifluoro-propyl)-cyclohexyl]-1,3,8-triaza-spiro[4.5]dec-1-en-4-one;

(777) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-pyrrolidine-2,5-dione;

(778) 3-(2,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(779) 3-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-imidazolidine-2,4-dione;

(780) 3-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-5,5-dimethyl-imidazolidine-2,4-dione;

(781) 8-{2-[2,6-dimethyl-4-(2-oxo-pyrrolidin-1-ylmethyl)-phenyl]-ethanesulfonyl}-2-(4-methyl-cyclohexyl)-1,3,8-triaza-spiro[4.5]dec-1-en-4-one;

(782) 1-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-pyrrolidine-2,5-dione;

(783) N-(2,6-dimethyl-4-{2-[2-(4-methyl-cyclohexyl)-4-oxo-1,3,8-triaza-spiro[4.5]dec-1-ene-8-sulfonyl]-ethyl}-phenyl)-N-methyl-acetamide;

(784) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-N-methyl-acetamide;

(785) N-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-N-methyl-acetamide;

(786) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-dihydro-pyrimidine-2,4-dione;

(787) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid trimethylhydrazide;

(788) 8-{2-[1-((S)-2,3-dihydroxy-propyl)-1H-indol-4-yl]-ethanesulfonyl}-2-(8,8,9,9,9-pentafluoro-nonyl)-1,3,8-triaza-spiro-[4.5]dec-1-en-4-one;

(789) 8-{2-[1-((S)-2,3-dihydroxy-propyl)-1H-indol-4-yl]-ethanesulfonyl}-2-(9,9,9-trifluoro-nonyl)-1,3,8-triaza-spiro[4.5]dec-1-en-4-one;

(790) 3-{3-methyl-4-[2-(2-nonyl-4-oxo-1,3,8-triaza-spiro[4.5]dec-1-ene-8-sulfonyl)-ethyl]-phenyl}-imidazolidine-2,4-dione;

(791) 8-{2-[1-((R)-2,3-dihydroxy-propyl)-4,6-dimethyl-1H-indol-5-yl]-ethanesulfonyl}-2-[4-(3,3,3-trifluoro-propyl)-cyclohexyl]-1,3,8-triaza-spiro[4.5]dec-1-en-4-one;

(792) 3-(3-methyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;

(793) 8-{2-[2-methyl-4-(3-oxo-morpholin-4-yl)-phenyl]-ethanesulfonyl}-2-(3-trifluoromethoxy-phenyl)-1,3,8-triaza-spiro[4.5]dec-1-en-4-one;

(794) N-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-N-(2-hydroxy-ethyl)-acetamide;

(795) 3-{4-[2-(2-nonyl-4-oxo-1,3,8-triaza-spiro[4.5]dec-1-ene-8-sulfonyl)-ethyl]-3-trifluoromethyl-phenyl}-imidazolidine-2,4-dione;

(796) 3,5-dimethyl-4-[2-(2-nonyl-4-oxo-1,3,8-triaza-spiro[4.5]dec-1-ene-8-sulfonyl)-ethyl]-benzoic acid;
(797) 2-(4-fluoro-3-trifluoromethyl-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;
(798) 8-{2-[4-(3,4-dihydroxy-butoxy)-2,6-dimethyl-phenyl]-ethanesulfonyl}-2-nonyl-1,3,8-triaza-spiro[4.5]dec-1-en-4-one;
(799) 3-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-imidazolidine-2,4-dione;
(800) 3-(4-{2-[2-(4-fluoro-3-trifluoromethyl-phenyl)-oxo-1,3,8-triaza-spiro[4.5]dec-1-ene-8-sulfonyl]-ethyl}-3,5-dimethyl-phenyl)-imidazolidine-2,4-dione;
(801) 8-{2-[4-(3,4-dihydroxy-butoxy)-2,6-dimethyl-phenyl]-ethanesulfonyl}-2-(4-fluoro-3-trifluoromethyl phenyl)-1,3,8-triaza-spiro[4.5]dec-1-en-4-one;
(802) 8-{2-[4-(4-fluoromethyl-4-hydroxy-piperidine-1-carbonyl)-2,6-dimethyl-phenyl]-ethanesulfonyl}-2-(4-fluoro-3-trifluoromethyl-phenyl)-1,3,8-triaza-spiro[4.5]dec-1-en-4-one;
(803) 2-(4-fluoro-3-trifluoromethyl-phenyl)-8-{2-[4-(hydroxy-4-methyl-piperidine-1-carbonyl)-2,6-dimethyl-phenyl]-ethanesulfonyl}-1,3,8-triaza-spiro[4.5]dec-1-en-4-one;
(804) 8-{2-[2,6-dimethyl-4-(2-oxa-7-aza-spiro[3.5]nonane-7-carbonyl)-phenyl]-ethanesulfonyl}-2-(4-fluoro-3-trifluoromethyl-phenyl)-1,3,8-triaza-spiro[4.5]dec-1-en-4-one;
(812) N-(3-isopropoxy-4-{2-[2-(4-methyl-cyclohexyl)-4-oxo-1,3,8-triaza-spiro[4.5]dec-1-ene-8-sulfonyl]-ethyl}-phenyl)-acetamide;
(817) 1-{3,5-dimethyl-4-[2-(2-nonyl-4-oxo-1,3,8-triaza-spiro[4.5]dec-1-ene-8-sulfonyl)-ethyl]-phenyl}-1-methyl-urea;
(818) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-(2-fluoro-ethyl)-urea;
(820) N-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-N-[2-(2-hydroxy-ethoxy)-ethyl]-acetamide;
(821) 8-{2-[4-((R)-2,3-dihydroxy-propoxy)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;
(822) 8-(2-{1-[2-((S)-2,3-dihydroxy-propoxy)-ethyl]-1H-indol-4-yl}-ethanesulfonyl)-2-[4-(3,3,3-trifluoro-propyl)-cyclohexyl]-1,3,8-triaza-spiro[4.5]dec-1-en-4-one;
(823) 2-[4-(3,3,3-trifluoro-propyl)-cyclohexyl]-8-(2-{1-[2-((2S,3S)-2,3,4-trihydroxy-butoxy)-ethyl]-1H-indol-4-yl}-ethanesulfonyl)-1,3,8-triaza-spiro[4.5]dec-1-en-4-one;
(824) N—((S)-2,3-dihydroxy-propyl)-N-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-acetamide;
(825) N-[2-(2-hydroxy-ethoxy)-ethyl]-N-{3-methyl-4-[2-(2-nonyl-4-oxo-1,3,8-triaza-spiro[4.5]dec-1-ene-8-sulfonyl)-ethyl]-phenyl}-acetamide;
(826) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-[2-(2-hydroxy-ethoxy)-ethyl]-urea;
(827) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-(2-methoxy-ethyl)-urea;
(828) 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-isopropyl-urea;
(829) 1-(3-ethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea;
(830) 1-((S)-2,3-dihydroxy-propyl)-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-urea;
(831) 8-{2-[4-(4-hydroxy-4-hydroxymethyl-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;
(832) 3-{3,5-dimethyl-4-[2-(2-nonyl-4-oxo-1,3,8-triaza-spiro[4.5]dec-1-ene-8-sulfonyl)-ethyl]-phenyl}-imidazolidine-2,4-dione;
(833) 5-tert-butoxymethyl-3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;
(834) 2-(4-methyl-cyclohexyl)-8-{2-[2-methyl-4-(5-oxo-pyrazolidin-1-yl)-phenyl]-ethanesulfonyl}-1,3,8-triaza-spiro[4.5]dec-1-en-4-one;
(835) 2-cyclohexyl-8-[2-(1H-indol-7-yl)-ethanesulfonyl]-1,3,8-triaza-spiro[4.5]dec-1-en-4-one;
(836) 2-cyclohexyl-8-[2-(6-trifluoromethyl-1H-indol-5-yl)-ethanesulfonyl]-1,3,8-triaza-spiro[4.5]dec-1-en-4-one;
(837) 2-cyclohexyl-8-[2-(6-methyl-1H-indol-5-yl)-ethanesulfonyl]-1,3,8-triaza-spiro[4.5]dec-1-en-4-one;
(838) 2-cyclohexyl-8-(2-{1-[2-(2-hydroxy-ethoxy)-ethyl]-1H-indol-5-yl}-ethanesulfonyl)-1,3,8-triaza-spiro[4.5]dec-1-en-4-one;
(839) 2-cyclohexyl-8-[2-(6-trifluoromethyl-1H-benzimidazol-5-yl)-ethanesulfonyl]-1,3,8-triaza-spiro[4.5]dec-1-en-4-one;
(840) 8-{2-[1-((S)-2,3-dihydroxy-propyl)-1H-indol-4-yl]-ethanesulfonyl}-2-(3-trifluoromethyl-phenyl)-1,3,8-triaza-spiro[4.5]dec-1-en-4-one;
(841) 2-cyclohexyl-8-{2-[4-(1,1-dioxo-1$\lambda^6$-thiomorpholine-4-carbonyl)-2-methyl-phenyl]-ethanesulfonyl}-1,3,8-triaza-spiro[4.5]dec-1-en-4-one;
(842) 2-cyclohexyl-8-{2-[4-(2-dimethylamino-ethylamino)-2-methyl-phenyl]-ethanesulfonyl}-1,3,8-triaza-spiro[4.5]dec-1-en-4-one;
(843) 8-{2-[2-methyl-4-(4-methyl-piperazine-1-carbonyl)-phenyl]-ethanesulfonyl}-2-(3-trifluoromethoxy-phenyl) 1,3,8-triaza-spiro[4.5]dec-1-en-4-one;
(844) 4-[2-(2-cyclohexyl-4-oxo-1,3,8-triaza-spiro[4.5]dec-1-ene-8-sulfonyl)-ethyl]-N-(2-dimethylamino-ethyl)-3-methyl-benzenesulfonamide;
(845) 8-(2-{2-methyl-4-[2-(4-methyl-piperazin-1-yl)-2-oxo-ethylamino]-phenyl}-ethanesulfonyl)-2-(3-trifluoromethoxy-phenyl)-1,3,8-triaza-spiro[4.5]dec-1-en-4-one;
(846) 3-methyl-4-{2-[4-oxo-2-(3-trifluoromethoxy-phenyl)-1,3,8-triaza-spiro[4.5]dec-1-ene-8-sulfonyl]-ethyl}-N-pyridin-4-yl-benzenesulfonamide;
(847) 2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide;
(848) N-(1-benzyl-piperidin-4-yl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;
(849) 8-{2-[4-(4-isopropyl-piperazine-1-carbonyl)-2-methyl-phenyl]-ethanesulfonyl}-2-(3-trifluoromethoxy-phenyl)-1,3,8-triaza-spiro[4.5]dec-1-en-4-one;

(850) 8-{2-[1-((S)-2,3-dihydroxy-propyl)-1H-indol-5-yl]-ethanesulfonyl}-2-(3-trifluoromethoxy-phenyl)-1,3,8-triaza-spiro[4.5]dec-1-en-4-one;

(851) N—((R)-2,3-dihydroxy-propyl)-3-methyl-4-{2-[4-oxo-2-(3-trifluoromethoxy-phenyl)-1,3,8-triaza-spiro[4.5]dec-1-ene-8-sulfonyl]-ethyl}-benzenesulfonamide;

(852) 3-methyl-4-{2-[4-oxo-2-(3-trifluoromethyl-phenyl)-1,3,8-triaza-spiro[4.5]dec-1-ene-8-sulfonyl]-ethyl}-N-pyridin-3-ylmethyl-benzenesulfonamide;

(853) N-(4-hydroxy-cyclohexyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(854) N-(2-hydroxy-1,1-bis-hydroxymethyl-ethyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide;

(855) 8-{2-[4-(3,4-dihydroxy-butoxy)-3,5-dimethyl-phenyl]-ethanesulfonyl}-2-(3-trifluoromethoxy-phenyl)-1,3,8-triaza-spiro[4.5]dec-1-en-4-one;

(856) 2-(4-fluoro-3-trifluoromethyl-phenyl)-8-{2-[2-methyl-4-(pyrrolidine-1-carbonyl)-phenyl]-ethanesulfonyl}-1,3,8-triaza-spiro[4.5]dec-1-en-4-one;

(857) 2-(4-fluoro-3-trifluoromethyl-phenyl)-8-{2-[4-((R)-2-hydroxymethyl-5-oxo-pyrrolidin-1-yl)-2-methyl-phenyl]-ethanesulfonyl}-1,3,8-triaza-spiro[4.5]dec-1-en-4-one;

(858) 2-(4-fluoro-3-trifluoromethyl-phenyl)-8-{2-[4-((S)-2-hydroxymethyl-5-oxo-pyrrolidin-1-yl)-2-methyl-phenyl]-ethanesulfonyl}-1,3,8-triaza-spiro[4.5]dec-1-en-4-one;

(859) 4-(3-methyl-4-{2-[4-oxo-2-(3-trifluoromethoxy-phenyl)-1,3,8-triaza-spiro[4.5]dec-1-ene-8-sulfonyl]-ethyl}-phenoxy)-piperidine-1-carboxylic acid tert-butyl ester;

(860) 8-{2-[4-(3,4-dihydroxy-butoxy)-3,5-difluoro-phenyl]-ethanesulfonyl}-2-(3-trifluoromethoxy-phenyl)-1,3,8-triaza-spiro[4.5]dec-1-en-4-one;

(861) 2-cyclohexyl-8-{2-[2-methyl-4-(2-oxo-azetidin-1-yl)-phenyl]-ethanesulfonyl}-1,3,8-triaza-spiro[4.5]dec-1-en-4-one;

(862) 1-methyl-3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(863) 5,5-dimethyl-3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(864) 5,5-dimethyl-3-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione;

(865) 2-(4-methyl-cyclohexyl)-8-{2-[2-methyl-4-(2-oxo-oxazolidin-3-yl)-phenyl]-ethanesulfonyl}-1,3,8-triaza-spiro[4.5]dec-1-en-4-one;

(866) 2-(4-methyl-cyclohexyl)-8-{2-[2-methyl-4-(4-oxo-oxazolidin-3-yl)-phenyl]-ethanesulfonyl}-1,3,8-triaza-spiro[4.5]dec-1-en-4-one;

(867) 8-{2-[1-((R)-2,3-dihydroxy-propyl)-1H-indol-4-yl]-ethanesulfonyl}-2-[4-(3,3,3-trifluoro-propyl)-cyclohexyl]-1,3,8-triaza-spiro[4.5]dec-1-en-4-one;

(868) 8-(2-{4-[(1H-imidazol-2-yl)-methyl-amino]-2,6-dimethyl-phenyl}-ethanesulfonyl)-2-(4-methyl-cyclohex 1,3,8-triaza-spiro[4.5]dec-1-en-4-one;

(869) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5,5-dimethyl-imidazolidine-2,4-dione;

(870) 2-(4-methyl-cyclohexyl)-8-{2-[2-methyl-4-(2-ox-piperazin-1-yl)-phenyl]-ethanesulfonyl}-1,3,8-triaza-spiro[4.5]dec-1-en-4-one;

(872) 2-cyclohexyl-8-{2-[1-((S)-2,3-dihydroxy-propyl)indol-5-yl]-ethanesulfonyl}-1,3,8-triaza-spiro[4.5]dec-1-en-4-one;

(873) N-(2-fluoro-5-methyl-4-{2-[4-oxo-2-(3-trifluoromethoxy-phenyl)-1,3,8-triaza-spiro[4.5]dec-1-ene-8-sulfonyl]-ethyl}-phenyl)-N-(2-hydroxy-ethyl)-acetamide;

(874) N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(875) N-(3-hydroxy-propyl)-N'-(3-methyl-4-{2-[4-oxo-2-(3-trifluoromethoxy-phenyl)-1,3,8-triaza-spiro[4.5]dec-1-ene-8-sulfonyl]-ethyl}-phenyl)-sulfamide;

(876) 1-cyanomethyl-1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-urea;

(877) 1-(3-methyl-4-{2-[4-oxo-2-(3-trifluoromethoxy-phenyl)-1,3,8-triaza-spiro[4.5]dec-1-ene-8-sulfonyl]-ethyl}-phenyl)-1-(2,2,2-trifluoro-ethyl)-urea;

(878) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-imidazolidine-2,4-dione;

(879) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-5-methyl-imidazolidine-2,4-dione;

(880) 3-(4-{2-[2-(4-butyl-cyclohexyl)-4-oxo-1,3,8-triaza-spiro[4.5]dec-1-ene-8-sulfonyl]-ethyl}-3-methyl-phenyl)-imidazolidine-2,4-dione;

(881) 3-(3-methyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(882) 3-(4-{2-[2-(4-isopropyl-cyclohexyl)-4-oxo-1,3,8-triaza-spiro[4.5]dec-1-ene-8-sulfonyl]-ethyl}-3-methyl-phenyl)-imidazolidine-2,4-dione;

(883) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-imidazolidine-2,4-dione;

(884) 3-(4-{2-[2-(4-isopropyl-cyclohexyl)-4-oxo-1,3,8-triaza-spiro[4.5]dec-1-ene-8-sulfonyl]-ethyl}-3,5-dimethyl-phenyl)-imidazolidine-2,4-dione;

(885) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1,5,5-trimethyl-imidazolidine-2,4-dione;

(886) (S)-2-amino-3-hydroxy-N-(3-methyl-4-{2-[4-oxo-2-(3-trifluoromethyl-phenyl)-1,3,8-triaza-spiro[4.5]dec-1-ene-8-sulfonyl]-ethyl}-phenyl)-propionamide;

(887) 1-(4-{2-[2-(4-ethyl-cyclohexyl)-4-oxo-1,3,8-triaza-spiro[4.5]dec-1-ene-8-sulfonyl]-ethyl}-3-methyl-phenyl)-5,5-dimethyl-imidazolidine-2,4-dione;

(888) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide;

(889) 8-{2-[2-methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride;

(890) 4-{2-[2-(4,4-difluoro-cyclohexyl)-4-oxo-1,3,8-triaza-spiro[4.5]dec-1-ene-8-sulfonyl]-ethyl}-3,N,N-trimethyl-benzamide;

(891) 4-{2-[2-(4-methanesulfonyl-phenyl)-4-oxo-1,3,8-triaza-spiro[4.5]dec-1-ene-8-sulfonyl]-ethyl}-3,N,N-trimethyl-benzamide;

(892) 3,N,N-trimethyl-4-(2-{4-oxo-2-[(E)-2-(3-trifluoromethyl-phenyl)-vinyl]-1,3,8-triaza-spiro[4.5]dec-1-ene-8-sulfonyl}-ethyl)-benzamide;

(893) 3,N,N-trimethyl-4-[2-(4-oxo-2-phenylethynyl-1,3,8-triaza-spiro[4.5]dec-1-ene-8-sulfonyl)-ethyl]-benzamide;

(894) 4-{2-[2-(4-butyl-cyclohexyl)-4-oxo-1,3,8-triaza-spiro[4.5]dec-1-ene-8-sulfonyl]-ethyl}-3,N,N-trimethyl-benzamide;
(895) 4-{2-[2-(4-tert-butyl-cyclohexyl)-4-oxo-1,3,8-triaza-spiro[4.5]dec-1-ene-8-sulfonyl]-ethyl}-3,N,N-trimethyl-benzamide;
(896) 4-{2-[2-(4-ethyl-cyclohexyl)-4-oxo-1,3,8-triaza-spiro[4.5]dec-1-ene-8-sulfonyl]-ethyl}-3,N,N-trimethyl-benzamide;
(897) 3,N,N-trimethyl-4-(2-{4-oxo-2-[4-(4,4,4-trifluoro-butyl)-cyclohexyl]-1,3,8-triaza-spiro[4.5]dec-1-ene-8-sulfonyl}-ethyl)-benzamide;
(898) 4-{2-[4-(cyclohexylmethyl-amino)-2-(3-trifluoromethoxy-phenyl)-1,3,8-triaza-spiro[4.5]deca-1,3-diene-8-sulfonyl]-ethyl}-3,N,N-trimethyl-benzamide;
(899) 4-{2-[4-dimethylamino-2-(3-trifluoromethoxy-phenyl)-1,3,8-triaza-spiro[4.5]deca-1,3-diene-8-sulfonyl]-ethyl}-3,N,N-trimethyl-benzamide;
(900) 4-{2-[4-[(Z)-hydroxyimino]-2-(3-trifluoromethoxy-phenyl)-1,3,8-triaza-spiro[4.5]dec-1-ene-8-sulfonyl]-ethyl}-3,N,N-trimethyl-benzamide;
(901) 4-{2-[4-[(Z)-methoxyimino]-2-(3-trifluoromethoxy-phenyl)-1,3,8-triaza-spiro[4.5]dec-1-ene-8-sulfonyl]-ethyl}-3,N,N-trimethyl-benzamide;
(902) 4-(2-{2-[4-(2-methoxy-ethyl)-cyclohexyl]-4-oxo-1,3,8-triaza-spiro[4.5]dec-1-ene-8-sulfonyl}-ethyl)-3,N,N-trimethyl-benzamide;
(903) N-{4-[2-(2-cyclopentyl-4-oxo-1,3,8-triaza-spiro[4.5]dec-1-ene-8-sulfonyl)-ethyl]-3-methyl-phenyl}-acetamide;
(904) N-(3-methyl-4-{2-[4-oxo-2-(4-trifluoromethyl-cyclohexyl)-1,3,8-triaza-spiro[4.5]dec-1-ene-8-sulfonyl]-ethyl}-phenyl)-acetamide;
(905) N-(4-{2-[2-(4-butyl-cyclohexyl)-4-oxo-1,3,8-triaza-spiro[4.5]dec-1-ene-8-sulfonyl]-ethyl}-3-methyl-phenyl)-acetamide;
(906) N-(4-{2-[2-(4-cyano-phenyl)-4-oxo-1,3,8-triaza-spiro[4.5]dec-1-ene-8-sulfonyl]-ethyl}-3-methyl-phenyl)-acetamide;
(907) N-(4-{2-[2-(3-cyano-phenyl)-4-oxo-1,3,8-triaza-spiro[4.5]dec-1-ene-8-sulfonyl]-ethyl}-3-methyl-phenyl)-acetamide;
(908) N-(4-{2-[2-(2-cyano-phenyl)-4-oxo-1,3,8-triaza-spiro[4.5]dec-1-ene-8-sulfonyl]-ethyl}-3-methyl-phenyl)-acetamide;
(909) N-(4-{2-[2-(4-tert-butyl-cyclohexyl)-4-oxo-1,3,8-triaza-spiro[4.5]dec-1-ene-8-sulfonyl]-ethyl}-3-methyl-phenyl)-acetamide;
(910) N-(4-{2-[2-(4-ethoxymethyl-cyclohexyl)-4-oxo-1,3,8-triaza-spiro[4.5]dec-1-ene-8-sulfonyl]-ethyl}-3-methyl-phenyl)-acetamide;
(911) N-(3-methyl-4-{2-[4-oxo-2-(4-propoxy-cyclohexyl)-1,3,8-triaza-spiro[4.5]dec-1-ene-8-sulfonyl]-ethyl}-phenyl)-acetamide;
(912) N-(4-{2-[2-(4-butoxy-cyclohexyl)-4-oxo-1,3,8-triaza-spiro[4.5]dec-1-ene-8-sulfonyl]-ethyl}-3-methyl-phenyl)-acetamide;
(913) N-(4-{2-[2-(4-isopropoxymethyl-cyclohexyl)-4-oxo-1,3,8-triaza-spiro[4.5]dec-1-ene-8-sulfonyl]-ethyl}-3-methyl-phenyl)-acetamide;
(914) N-[4-(2-{2-[4-(3-fluoro-propoxy)-cyclohexyl]-4-oxo-1,3,8-triaza-spiro[4.5]dec-1-ene-8-sulfonyl}-ethyl)-3-methyl-phenyl]-acetamide;
(915) N-[4-(2-{2-[4-(3-fluoro-propoxy)-cyclohexyl]-4-oxo-1,3,8-triaza-spiro[4.5]dec-1-ene-8-sulfonyl}-ethyl)-3-methyl-phenyl]-acetamide;
(916) N-[4-(2-{2-[4-((E)-3,3-difluoro-propenyl)-cyclohexyl]-4-oxo-1,3,8-triaza-spiro[4.5]dec-1-ene-8-sulfonyl}-ethyl)-3-methyl-phenyl]-acetamide;
(917) N-{4-[2-(2-cycloheptyl-4-oxo-1,3,8-triaza-spiro[4.5]dec-1-ene-8-sulfonyl)-ethyl]-3-methyl-phenyl}-acetamide;
(918) N-{4-[2-(2-adamantan-1-yl-4-oxo-1,3,8-triaza-spiro[4.5]dec-1-ene-8-sulfonyl)-ethyl]-3-methyl-phenyl}-acetamide;
(919) N-[3-methyl-4-(2-{4-oxo-2-[4-(2,2,2-trifluoro-ethoxymethyl)-cyclohexyl]-1,3,8-triaza-spiro[4.5]dec-1-ene-8-sulfonyl}-ethyl)-phenyl]-acetamide;
(920) N-[4-(2-{2-[4-(4-chloro-phenyl)-cyclohexyl]-4-oxo-1,3,8-triaza-spiro[4.5]dec-1-ene-8-sulfonyl}-ethyl)-3-methyl-phenyl]-acetamide;
(921) N-[3-methyl-4-(2-{4-oxo-2-[4-(3,3,3-trifluoro-propoxy)-cyclohexyl]-1,3,8-triaza-spiro[4.5]dec-1-ene-8-sulfonyl}-ethyl)-phenyl]-acetamide;
(922) N-[3-methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-acetamide;
(923) N-(3-methyl-4-{2-[4-oxo-2-((1S,3R)-3-propyl-cyclohexyl)-1,3,8-triaza-spiro[4.5]dec-1-ene-8-sulfonyl]-ethyl}-phenyl)-acetamide;
(924) N-(3-methyl-4-{2-[2-((1S,3R)-3-methyl-cyclohexyl)-4-oxo-1,3,8-triaza-spiro[4.5]dec-1-ene-8-sulfonyl]-ethyl}-phenyl)-acetamide;
(925) N-(4-{2-[2-(4,4-dimethyl-cyclohexyl)-4-oxo-1,3,8-triaza-spiro[4.5]dec-1-ene-8-sulfonyl]-ethyl}-3-methyl-phenyl)-acetamide;
(926) N-(3-methyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-acetamide;
(927) N-[4-(2-{2-[4-(2-methoxy-ethyl)-cyclohexyl]-4-oxo-1,3,8-triaza-spiro[4.5]dec-1-ene-8-sulfonyl}-ethyl)-3-methyl-phenyl]-acetamide;
(928) [3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester;
(929) N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide;
(930) 2-hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide;
(931) N-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide;
(932) N-(3,5-dimethyl-4-{2-[2-((1S,3R)-3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide;
(933) N-(3,5-dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-2,2,2-trifluoro-N-methyl-acetamide;
(934) 1-{4-[2-(2-cycloheptyl-4-oxo-1,3,8-triaza-spiro[4.5]dec-1-ene-8-sulfonyl)-ethyl]-3,5-dimethyl-phenyl}-1-methyl-urea;
(935) 1-(3,5-dimethyl-4-{2-[4-oxo-2-(3-trifluoromethoxy-phenyl)-1,3,8-triaza-spiro[4.5]dec-1-ene-8-sulfonyl]-ethyl}-phenyl)-1-methyl-urea;
(936) 1-[3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea;
(937) 1-[2-chloro-3,5-dimethyl-4-(2-{4-oxo-2-[4-(2,2,trifluoro-ethyl)-cyclohexyl]-1,3,8-triaza-spiro[4.5]dec-1-ene-8-sulfonyl}-ethyl)-phenyl]-1-methyl-urea;

(938) 1-(4-{2-[2-(4,4-dimethyl-cyclohexyl)-4-oxo-1,3, triaza-spiro[4.5]dec-1-ene-8-sulfonyl]-ethyl}-3,5-dimethyl-phenyl)-1-methyl-urea;

(939) 1-[3,5-dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea;

(940) 1-[4-(2-{2-[4-(3,3-difluoro-allyl)-cyclohexyl]-4-oxo-1,3,8-triaza-spiro[4.5]dec-1-ene-8-sulfonyl}-ethyl)-3,5-dimethyl-phenyl]-1-methyl-urea;

(941) 1-(3,5-dimethyl-4-{2-[8-oxo-6-(3-trifluoromethoxy-phenyl)-2,5,7-triaza-spiro[3.4]oct-5-ene-2-sulfonyl]-ethyl}-phenyl)-1-methyl-urea;

(942) N-(4-{(E)-1-fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide;

(943) 3-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione;

(944) 3-[3-methyl-4-(2-{4-oxo-2-[4-(4,4,4-trifluoro-butyl)-cyclohexyl]-1,3,8-triaza-spiro[4.5]dec-1-ene-8-sulfonyl}-ethyl)-phenyl]-imidazolidine-2,4-dione;

(945) 3-[4-(2-{2-[4-((E)-3,3-difluoro-propenyl)-cyclohexyl]-4-oxo-1,3,8-triaza-spiro[4.5]dec-1-ene-8-sulfonyl}-ethyl)-3-methyl-phenyl]-imidazolidine-2,4-dione;

(946) 3-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-imidazolidine-2,4-dione;

(947) 3-(3-methyl-4-{2-[4-oxo-2-(4-trifluoromethyl-cyclohexyl)-1,3,8-triaza-spiro[4.5]dec-1-ene-8-sulfonyl]-ethyl}-phenyl)-imidazolidine-2,4-dione;

(948) 3-[3-methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione;

(949) 3-(3-methyl-4-{2-[4-oxo-2-((1S,3R)-3-propyl-cyclohexyl)-1,3,8-triaza-spiro[4.5]dec-1-ene-8-sulfonyl]-ethyl}-phenyl)-imidazolidine-2,4-dione;

(950) 3-(3-methyl-4-{2-[2-((1S,3R)-3-methyl-cyclohexyl)-4-oxo-1,3,8-triaza-spiro[4.5]dec-1-ene-8-sulfonyl]-ethyl}-phenyl)-imidazolidine-2,4-dione;

(951) 3-(4-{2-[2-(4,4-dimethyl-cyclohexyl)-4-oxo-1,3,8-triaza-spiro[4.5]dec-1-ene-8-sulfonyl]-ethyl}-3-methyl-phenyl)-imidazolidine-2,4-dione;

(952) 3-(3-methyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-imidazolidine-2,4-dione;

(953) N-(2-chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide;

(954) N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide;

(955) N-[4-(2-{2-[4-(3,3-difluoro-propyl)-cyclohexyl]-4-oxo-1,3,8-triaza-spiro[4.5]dec-1-ene-8-sulfonyl}-ethyl)-3-methyl-phenyl]-acetamide;

(956) 3-[4-(2-{2-[4-(3,3-difluoro-propyl)-cyclohexyl]oxo-1,3,8-triaza-spiro[4.5]dec-1-ene-8-sulfonyl}-ethyl) 3-methyl-phenyl]-imidazolidine-2,4-dione;

(957) 2-(2-cyclohexyl-4-oxo-1,3,8-triaza-spiro[4.5]dec-1-ene-8-sulfonyl)-N-phenyl-benzamide;

(958) 8-(2-{2-methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-4-one;

(959) 8-{(E)-2-[4-((R)-3-fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(960) 8-{(E)-2-[4-(4-hydroxymethyl-piperidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(961) 3,5,N,N-tetramethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(962) 3,5-dimethyl-4-{(E)-2-[4-oxo-2-(3-trifluoromethoxy-phenyl)-1,3,8-triaza-spiro[4.5]dec-1-ene-8-sulfonyl]-vinyl}-benzamide;

(963) 8-{(E)-2-[4-(3-fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one;

(964) 8-{2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(965) 8-{2-[4-(3-hydroxy-azetidine-1-carbonyl)-2,6-dimethyl-phenyl]-ethanesulfonyl}-2-(3-trifluoromethoxy-phenyl)-1,3,8-triaza-spiro[4.5]dec-1-en-4-one;

(966) 8-{2-[4-(4-hydroxymethyl-piperidine-1-carbonyl) 2,6-dimethyl-phenyl]-ethanesulfonyl}-2-(3-trifluoromethoxy-phenyl)-1,3,8-triaza-spiro[4.5]dec-1-en-4-one;

(967) 8-{(E)-2-[2,6-dimethyl-4-(2-oxa-6-aza-spiro[3.3]heptane-6-carbonyl)-phenyl]-ethenesulfonyl}(4-fluoro-3-trifluoromethyl-phenyl)-1,3,8-triaza-spiro[4.5]dec-1-en-4-one;

(968) 8-{(E)-2-[2,6-dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one;

(969) 8-{(E)-2-[4-((3R,5S)-3,5-dimethyl-piperazine-1-carbonyl)-2,6-dimethyl-phenyl]-ethenesulfonyl}-2-(4-fluoro-3-trifluoromethyl-phenyl)-1,3,8-triaza-spiro[4.5]dec-1-en-4-one;

(970) 2-(4-fluoro-3-trifluoromethyl-phenyl)-8-{(E)-2-[4-(3-hydroxy-3-methyl-azetidine-1-carbonyl)-2,6-dimethyl-phenyl]-ethenesulfonyl}-1,3,8-triaza-spiro[4.5]dec-1-en-4-one;

(971) 2-(4-fluoro-3-trifluoromethyl-phenyl)-8-{(E)-2-[4-(4-hydroxy-4-hydroxymethyl-piperidine-1-carbonyl)-2,6-dimethyl-phenyl]-ethenesulfonyl}-1,3,8-triaza-spiro[4.5]dec-1-en-4-one;

(972) 8-{(E)-2-[2,6-dimethyl-4-(4-oxo-piperidine-1-carbonyl)-phenyl]-ethenesulfonyl}-2-(4-fluoro-3-trifluoromethyl-phenyl)-1,3,8-triaza-spiro[4.5]dec-1-en-4-one;

(973) 2-[4-(3,3-difluoro-allyl)-cyclohexyl]-8-{2-[4-(fluoro-4-hydroxymethyl-piperidine-1-carbonyl)-2-methyl-phenyl]-ethanesulfonyl}-1,3,8-triaza-spiro[4.5]dec-1-en-4-one;

(974) 2-[4-(3,3-difluoro-allyl)-cyclohexyl]-8-{2-[4-(4-fluoromethyl-4-hydroxy-piperidine-1-carbonyl)-2-methyl-phenyl]-ethanesulfonyl}-1,3,8-triaza-spiro[4.5]dec-1-en-4-one;

(975) 2-(4-ethyl-cyclohexyl)-8-(2-{4-[4-(2-fluoro-ethyl)-piperazine-1-carbonyl]-2-methyl-phenyl}-ethanesulfonyl)-1,3,8-triaza-spiro[4.5]dec-1-en-4-one;

(976) 2-(4-ethyl-cyclohexyl)-8-{2-[2-methyl-4-(4-oxetan-3-yl-piperazine-1-carbonyl)-phenyl]-ethanesulfonyl}-1,3,8-triaza-spiro[4.5]dec-1-en-4-one;

(977) 8-{2-[2-methyl-4-(pyrrolidine-1-carbonyl)-phenyl]-ethanesulfonyl}-2-nonyl-1,3,8-triaza-spiro[4.5]dec-1-en-4-one;

(978) 8-{2-[4-(azetidine-1-carbonyl)-2-methyl-phenyl]-ethanesulfonyl}-2-nonyl-1,3,8-triaza-spiro[4.5]dec-1-en-4-one;

(979) 8-{2-[4-((R)-3-hydroxy-pyrrolidine-1-carbonyl)-2-methyl-phenyl]-ethanesulfonyl}-2-nonyl-1,3,8-triaza-spiro[4.5]dec-1-en-4-one;
(980) 8-{2-[2,6-dimethyl-4-(pyrrolidine-1-carbonyl)-phenyl]-ethanesulfonyl}-2-nonyl-1,3,8-triaza-spiro[4.5]dec-1-en-4-one;
(981) 8-{2-[4-((R)-3-hydroxy-pyrrolidine-1-carbonyl)-2,6-dimethyl-phenyl]-ethanesulfonyl}-2-nonyl-1,3,8-triaza-spiro[4.5]dec-1-en-4-one;
(982) 8-{2-[4-(azetidine-1-carbonyl)-2,6-dimethyl-phenyl]-ethanesulfonyl}-2-nonyl-1,3,8-triaza-spiro[4.5]dec-1-en-4-one;
(983) 8-{2-[2,6-dimethyl-4-(piperidine-1-carbonyl)-phenyl]-ethanesulfonyl}-2-nonyl-1,3,8-triaza-spiro[4.5]dec-1-en-4-one;
(984) 8-{2-[4-(4-hydroxy-piperidine-1-carbonyl)-2,6-dimethyl-phenyl]-ethanesulfonyl}-2-nonyl-1,3,8-triaza-spiro[4.5]dec-1-en-4-one;
(985) 8-{2-[4-(3-hydroxy-azetidine-1-carbonyl)-2,6-dimethyl-phenyl]-ethanesulfonyl}-2-nonyl-1,3,8-triaza-spiro[4.5]dec-1-en-4-one;
(986) 8-{2-[2,6-dimethyl-4-(4-methyl-piperazine-1-carbonyl)-phenyl]-ethanesulfonyl}-2-nonyl-1,3,8-triaza-spiro[4.5]dec-1-en-4-one;
(987) N,N-dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(988) N-methoxy-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide;
(989) 8-{(E)-2-[4-(4-hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;
(990) 8-{(E)-2-[4-(4-fluoromethyl-4-hydroxy-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;
(991) 8-{(E)-2-[2,6-dimethyl-4-(4-methyl-piperazine-1-carbonyl)-phenyl]-ethenesulfonyl}-2-[4-(3,3,3-trifluoro-propyl)-cyclohexyl]-1,3,8-triaza-spiro[4.5]dec-1-en-4-one;
(992) 8-{(E)-2-[4-(isoxazolidine-2-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one;
(993) 8-((E)-2-{4-[4-((R)-2,3-dihydroxy-propoxy)-piperidine-1-carbonyl]-2,6-dimethyl-phenyl}-ethenesulfonyl)-2-[4-(3,3,3-trifluoro-propyl)-cyclohexyl]-1,3,8-triaza-spiro[4.5]dec-1-en-4-one;
(994) 3,5,N,N-tetramethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzamide;
(995) 8-{2-[2,6-dimethyl-4-(4-methyl-piperazine-1-carbonyl)-phenyl]-ethanesulfonyl}-2-[4-(3,3,3-trifluoro-propyl)-cyclohexyl]-1,3,8-triaza-spiro[4.5]dec-1-en-4-one;
(996) 3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide;
(997) 8-{(E)-2-[2,6-dimethyl-4-(pyrazolidine-1-carbonyl)-phenyl]-ethenesulfonyl}-2-[4-(3,3,3-trifluoro-propyl)-cyclohexyl]-1,3,8-triaza-spiro[4.5]dec-1-en-4-one;
(998) N-methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide;
(999) 8-{(E)-2-[4-(4-hydroxy-4-methyl-piperidine-1-carbonyl)-2,6-dimethyl-phenyl]-ethenesulfonyl}-2-(4-methyl-cyclohexyl)-1,3,8-triaza-spiro[4.5]dec-1-en-4-one;
(1000) 8-{(E)-2-[4-(4-fluoromethyl-4-hydroxy-piperidine-1-carbonyl)-2,6-dimethyl-phenyl]-ethenesulfonyl}-2-(4-methyl-cyclohexyl)-1,3,8-triaza-spiro[4.5]dec-1-en-4-one;
(1001) 8-{(E)-2-[4-(isoxazolidine-2-carbonyl)-2,6-dimethyl-phenyl]-ethenesulfonyl}-2-(4-methyl-cyclohexyl)-1,3,8-triaza-spiro[4.5]dec-1-en-4-one;
(1002) 8-{(E)-2-[4-(1,1-dioxo-1$\lambda^6$-thiomorpholine-4-carbonyl)-2,6-dimethyl-phenyl]-ethenesulfonyl}-2-(4-methyl-cyclohexyl)-1,3,8-triaza-spiro[4.5]dec-1-en-4-one;
(1003) 3,5,N,N-tetramethyl-4-{(E)-2-[2-(4-methyl-cyclohexyl)-4-oxo-1,3,8-triaza-spiro[4.5]dec-1-ene-8-sulfonyl]-vinyl}-benzamide;
(1006) 2-cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one;
(1007) 2-cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one;
(1008) 2-(4-butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one;
(1009) 2-(4-butyl-cyclohexyl)-8-[(E)-2-(4-{4-[2-(2-hydroxy-ethoxy)-ethoxy]-piperidine-1-carbonyl}-2,6-dimethyl-phenyl)-ethenesulfonyl]-1,3,8-triaza-spiro[4.5]dec-1-en-4-one;
(1010) 8-((E)-2-{4-[4-((R)-2,3-dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one;
(1011) 2-amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide;
(1012) (3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester;
(1013) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea;
(1014) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3-dimethyl-urea;
(1015) 1-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-methyl-urea;
(1016) 8-[(E)-2-(2,6-dimethyl-4-methylamino-phenyl)-ethenesulfonyl]-2-(3-trifluoromethylsulfanyl-phenyl)-1,3,8-triaza-spiro[4.5]dec-1-en-4-one;
(1017) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;
(1018) 1-[3,5-dimethyl-4-((E)-2-{4-oxo-2-[3-(1,1,2,2-tetrafluoro-ethoxy)-phenyl]-1,3,8-triaza-spiro[4.5]dec-1-ene-8-sulfonyl}-vinyl)-phenyl]-1-methyl-urea;
(1019) 1-[3,5-dimethyl-4-((E)-2-{4-oxo-2-[3-(4,4,4-trifluoro-butoxy)-phenyl]-1,3,8-triaza-spiro[4.5]dec-1-ene-8-sulfonyl}-vinyl)-phenyl]-1-methyl-urea;
(1020) 1-[3,5-dimethyl-4-((E)-2-{4-oxo-2-[4-(4,4,4-trifluoro-butoxy)-phenyl]-1,3,8-triaza-spiro[4.5]dec-1-ene-8-sulfonyl}-vinyl)-phenyl]-1-methyl-urea;
(1021) 1-(3,5-dimethyl-4-{(E)-2-[4-oxo-2-(4-pentyl-phenyl)-1,3,8-triaza-spiro[4.5]dec-1-ene-8-sulfonyl]-vinyl}-phenyl)-1-methyl-urea;
(1022) 1-(3,5-dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea;

(1023) 1-[3,5-dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea;

(1024) 1-{3,5-dimethyl-4-[(E)-2-(2-non-4-ynyl-4-oxo-1,3,8-triaza-spiro[4.5]dec-1-ene-8-sulfonyl)-vinyl]-phenyl}-1-methyl-urea;

(1025) 1-{3,5-dimethyl-4-[(E)-2-(2-non-3-ynyl-4-oxo-1,3,8-triaza-spiro[4.5]dec-1-ene-8-sulfonyl)-vinyl]-phenyl}-1-methyl-urea;

(1026) 1-[3,5-dimethyl-4-((E)-2-{2-[10-(3-methyl-oxetan-3-yl)-decyl]-4-oxo-1,3,8-triaza-spiro[4.5]dec-1-ene-8-sulfonyl}-vinyl)-phenyl]-1-methyl-urea;

(1027) 1-{3,5-dimethyl-4-[(E)-2-(2-non-1-ynyl-4-oxo-1,3,8-triaza-spiro[4.5]dec-1-ene-8-sulfonyl)-vinyl]-phenyl}-1-methyl-urea;

(1028) 1-(4-{2-[2-(4-fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea;

(1029) 1-(4-{2-[2-(2,2-difluoro-benzo[1,3]dioxol-5-yl)-4-oxo-1,3,8-triaza-spiro[4.5]dec-1-ene-8-sulfonyl]-ethyl}-3,5-dimethyl-phenyl)-1-methyl-urea;

(1030) 1-(4-{2-[2-(4-tert-butyl-phenyl)-4-oxo-1,3,8-triaza-spiro[4.5]dec-1-ene-8-sulfonyl]-ethyl}-3,5-dimethyl-phenyl)-1-methyl-urea;

(1031) 1-[3,5-dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea;

(1032) 1-[3,5-dimethyl-4-(2-{2-[10-(3-methyl-oxetan-3-yl)-decyl]-4-oxo-1,3,8-triaza-spiro[4.5]dec-1-ene-8-sulfonyl}-ethyl)-phenyl]-1-methyl-urea;

(1033) 2-(8-{2-[4-(tert-butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester;

(1034) (4-{2-[2-(1,1-difluoro-ethyl)-4-oxo-1,3,8-triaza-spiro[4.5]dec-1-ene-8-sulfonyl]-ethyl}-3,5-dimethyl-phenyl)-methyl-carbamic acid tert-butyl ester;

(1035) 8-[2-(2,6-dimethyl-4-methylamino-phenyl)-ethanesulfonyl]-2-(8,8,9,9,9-pentafluoro-nonyl)-1,3,8-triaza-spiro[4.5]dec-1-en-4-one;

(1036) 8-[2-(2,6-dimethyl-4-methylamino-phenyl)-ethanesulfonyl]-2-(3-trifluoromethylsulfanyl-phenyl)-1,3,8-triaza-spiro[4.5]dec-1-en-4-one;

(1037) 8-[2-(2,6-dimethyl-4-methylamino-phenyl)-ethanesulfonyl]-2-(4-isopropylidene-cyclohexyl)-1,3,8-triaza-spiro[4.5]dec-1-en-4-one;

(1038) 1-[3,5-dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea;

(1039) 1-(3,5-dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea;

(1040) 1-(4-{2-[2-((1S,3S,5R)-3,5-dimethyl-cyclohexyl)-4-oxo-1,3,8-triaza-spiro[4.5]dec-1-ene-8-sulfonyl]-ethyl}-3,5-dimethyl-phenyl)-1-methyl-urea;

(1041) 1-(3,5-dimethyl-4-{2-[4-oxo-2-(1-propyl-butyl)-1,3,8-triaza-spiro[4.5]dec-1-ene-8-sulfonyl]-ethyl}-phenyl)-1-methyl-urea;

(1042) 1-[3,5-dimethyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-1-methyl-urea;

(1043) 1-(3,5-dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea;

(1044) N-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide;

(1045) 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea;

(1046) 1-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-1-methyl-urea;

(1047) N-(3,5-dimethyl-4-{2-[4-oxo-2-(9,9,9-trifluoro-nonyl)-1,3,8-triaza-spiro[4.5]dec-1-ene-8-sulfonyl]-ethyl}-phenyl)-N-methyl-acetamide;

(1048) 1-[3,5-dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea;

(1050) 1-(3,5-dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea;

(1051) 1-(4-{2-[2-(cis-3,4-dimethyl-cyclopentyl)-4-oxo-1,3,8-triaza-spiro[4.5]dec-1-ene-8-sulfonyl]-ethyl}-3,5-dimethyl-phenyl)-1-methyl-urea;

(1052) 1-{4-[2-(2-dicyclopropylmethyl-4-oxo-1,3,8-triaza-spiro[4.5]dec-1-ene-8-sulfonyl)-ethyl]-3,5-dimethyl-phenyl}-1-methyl-urea;

(1053) 1-{4-[2-(2-bicyclo[3.3.1]non-9-yl-4-oxo-1,3,8-triaza-spiro[4.5]dec-1-ene-8-sulfonyl)-ethyl]-3,5-dimethyl-phenyl}-1-methyl-urea;

(1054) 1-{4-[2-(2-((1R,5S)-2-bicyclo[3.2.1]oct-3-yl-4-oxo-1,3,8-triaza-spiro[4.5]dec-1-ene-8-sulfonyl]-ethyl]-3,5-dimethyl-phenyl}-1-methyl-urea;

(1055) 1-(3,5-dimethyl-4-{2-[2-(3-methyl-cyclopentyl)-4-oxo-1,3,8-triaza-spiro[4.5]dec-1-ene-8-sulfonyl]-ethyl}-phenyl)-1-methyl-urea;

(1056) 1-{4-[2-(2-bicyclo[2.2.1]hept-7-yl-4-oxo-1,3,8-triaza-spiro[4.5]dec-1-ene-8-sulfonyl)-ethyl]-3,5-dimethyl-phenyl}-1-methyl-urea;

(1057) 1-(4-{2-[2-((1S,2S)-2-hexyl-cyclohexyl)-4-oxo-1,3,8-triaza-spiro[4.5]dec-1-ene-8-sulfonyl]-ethyl}-3,5-dimethyl-phenyl)-1-methyl-urea;

(1058) 1-{3,5-dimethyl-4-[2-(4-oxo-2-spiro[2.5]oct-6-yl-1,3,8-triaza-spiro[4.5]dec-1-ene-8-sulfonyl)-ethyl]-phenyl}-1-methyl-urea;

(1059) 1-(4-{2-[2-(4-difluoromethylene-cyclohexyl)-4-oxo-1,3,8-triaza-spiro[4.5]dec-1-ene-8-sulfonyl]-ethyl}-3,5-dimethyl-phenyl)-1-methyl-urea;

(1060) N-[4-(2-{2-[4-(2,2-difluoro-ethyl)-cyclohexyl]-4-oxo-1,3,8-triaza-spiro[4.5]dec-1-ene-8-sulfonyl}-ethyl)-3-methyl-phenyl]-acetamide;

(1061) N-[4-(2-{2-[4-(2-fluoro-ethyl)-cyclohexyl]-4-oxo-1,3,8-triaza-spiro[4.5]dec-1-ene-8-sulfonyl}-ethyl)-3-methyl-phenyl]-acetamide;

(1062) N-(4-{2-[2-(4-butyl-4-fluoro-cyclohexyl)-4-oxo-1,3,8-triaza-spiro[4.5]dec-1-ene-8-sulfonyl]-ethyl}-3-methyl-phenyl)-acetamide;

(1063) N-[4-(2-{2-[4-((E)-3-fluoro-propenyl)-cyclohexyl]-4-oxo-1,3,8-triaza-spiro[4.5]dec-1-ene-8-sulfonyl}-ethyl)-3-methyl-phenyl]-acetamide;

(1064) N-[4-(2-{2-[4-(3-fluoro-propyl)-cyclohexyl]-4-oxo-1,3,8-triaza-spiro[4.5]dec-1-ene-8-sulfonyl}-ethyl)-3-methyl-phenyl]-acetamide;

(1065) N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide;

(1066) N-[4-(2-{2-[4-(3-fluoro-propylidene)-cyclohexyl]-4-oxo-1,3,8-triaza-spiro[4.5]dec-1-ene-8-sulfonyl}-ethyl)-3-methyl-phenyl]-acetamide;

(1067) N-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-acetamide;

(1068) N-[4-(2-{2-[4-(3,3-difluoro-allyl)-cyclohexyl]-4-oxo-1,3,8-triaza-spiro[4.5]dec-1-ene-8-sulfonyl}-ethyl)-3-methyl-phenyl]-acetamide;
(1069) N-[3-methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide;
(1070) N-[4-(2-{2-[4-((E)-3-fluoro-allyl)-cyclohexyl]-4-oxo-1,3,8-triaza-spiro[4.5]dec-1-ene-8-sulfonyl}-ethyl)-3-methyl-phenyl]-acetamide;
(1071) N-[4-(2-{2-[4-(2,2-difluoro-ethyl)-cyclohexyl]-4-oxo-1,3,8-triaza-spiro[4.5]dec-1-ene-8-sulfonyl}-ethyl)-3-methyl-phenyl]-acetamide;
(1072) N-[4-(2-{2-[4-(2-fluoro-ethyl)-cyclohexyl]-4-oxo-1,3,8-triaza-spiro[4.5]dec-1-ene-8-sulfonyl}-ethyl)-3-methyl-phenyl]-acetamide;
(1073) N-[4-(2-{2-[4-fluoro-4-(3-fluoro-propyl)-cyclohexyl]-4-oxo-1,3,8-triaza-spiro[4.5]dec-1-ene-8-sulfonyl}-ethyl)-3-methyl-phenyl]-acetamide;
(1074) N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide;
(1075) N-(4-{2-[2-(4-difluoromethyl-cyclohexyl)-4-oxo-1,3,8-triaza-spiro[4.5]dec-1-ene-8-sulfonyl]-ethyl}-3-methyl-phenyl)-acetamide;
(1076) N-[4-(2-{2-[4-(3,3-difluoro-propylidene)-cyclohexyl]-4-oxo-1,3,8-triaza-spiro[4.5]dec-1-ene-8-sulfonyl}-ethyl)-3-methyl-phenyl]-acetamide;
(1077) N-[4-(2-{2-[4-(2-fluoro-propyl)-cyclohexyl]-4-oxo-1,3,8-triaza-spiro[4.5]dec-1-ene-8-sulfonyl}-ethyl)-3-methyl-phenyl]-acetamide;
(1078) N-[4-(2-{2-[4-(1-fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide;
(1079) N-(4-{2-[2-(4-butylidene-cyclohexyl)-4-oxo-1,3,8-triaza-spiro[4.5]dec-1-ene-8-sulfonyl]-ethyl}-3-methyl-phenyl)-acetamide;
(1080) N-[3-methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide;
(1081) 1-{3,5-dimethyl-4-[2-(2-non-4-ynyl-4-oxo-1,3,8-triaza-spiro[4.5]dec-1-ene-8-sulfonyl)-ethyl]-phenyl}-1-methyl-urea;
(1082) 1-{3,5-dimethyl-4-[2-(2-non-3-ynyl-4-oxo-1,3,8-triaza-spiro[4.5]dec-1-ene-8-sulfonyl)-ethyl]-phenyl}-1-methyl-urea;
(1083) 1-{3,5-dimethyl-4-[2-(2-non-1-ynyl-4-oxo-1,3,8-triaza-spiro[4.5]dec-1-ene-8-sulfonyl)-ethyl]-phenyl}-1-methyl-urea;
(1084) 1-(3,5-dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea;
(1085) 1-(4-{2,2-difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea;
(1086) 1-{4-[2,2-difluoro-2-(2-nonyl-4-oxo-1,3,8-triaza-spiro[4.5]dec-1-ene-8-sulfonyl)-ethyl]-3,5-dimethyl-phenyl}-1-methyl-urea;
(1087) 1-{3,5-dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea;
(1088) 1-[3,5-dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea;
(1089) 1-[3,5-dimethyl-4-((E)-2-{4-oxo-2-[3-(4,4,4-trifluoro-butyl)-phenyl]-1,3,8-triaza-spiro[4.5]dec-1-ene-8-sulfonyl}-vinyl)-phenyl]-1-methyl-urea;
(1090) 1-(3,5-dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea;
(1091) 2-[4-fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one;
(1092) 2-[4-fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1093) 2-(4-chloro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1094) 2-(3-fluoro-4-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1095) 2-(3,4-bis-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1096) 8-{(E)-2-[4-(4-hydroxy-4-methyl-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;
(1097) 8-{(E)-2-[4-(4-hydroxy-4-methyl-piperidine-1-carbonyl)-2,6-dimethyl-phenyl]-ethenesulfonyl}-2-[3-(2,2,2-trifluoro-ethyl)-phenyl]-1,3,8-triaza-spiro[4.5]dec-1-en-4-one;
(1098) 2-(4-fluoro-3-methyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1099) 2-(4-fluoro-3-trifluoromethoxy-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1100) 8-{(E)-2-[4-(4-hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one;
(1101) 8-{1,1-difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one;
(1102) 2-(4-fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one;
(1103) 8-{(E)-2-[4-((R)-2,3-dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;
(1104) 6-(4-methyl-cyclohexyl)-2-(2-naphthalen-1-yl-ethanesulfonyl)-2,5,7-triaza-spiro[3.4]oct-5-en-8-one;
(1106) (11-{8-[(E)-2-(2,6-dimethyl-4-methylamino-phenyl)-ethenesulfonyl]-4-oxo-1,3,8-triaza-spiro[4.5]dec-1-en-2-yl}-undecyl)-carbamic acid tert-butyl ester;
(1107) 8-[(E)-2-(2,6-dimethyl-4-methylamino-phenyl)-ethenesulfonyl]-2-(9-hydroxy-nonyl)-1,3,8-triaza-spiro[4.5]dec-1-en-4-one;
(1108) 1-(3,5-dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea;

(1109) 14-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-tetradecanoic acid;

(1110) 1-(3,5-dimethyl-4-{(E)-2-[2-(4-[1,1,1-$^2$H$_3$]methyl-[4-$^2$H$_1$]cyclohexyl)-4-oxo-1,3,8-triaza-spiro[4.5]dec-1-ene-8-sulfonyl]-vinyl}-phenyl)-1-methyl-urea;

(1111) 1-(4-{(E)-2-[2-(4-fluoro-3-trifluoromethoxy-phenyl)-4-oxo-1,3,8-triaza-spiro[4.5]dec-1-ene-8-sulfonyl]-vinyl}-3,5-dimethyl-phenyl)-1-methyl-urea;

(1112) 1-(3,5-dimethyl-4-{(E)-2-[2-(3-nonafluorobutyl-phenyl)-4-oxo-1,3,8-triaza-spiro[4.5]dec-1-ene-8-sulfonyl]-vinyl}-phenyl)-1-methyl-urea;

(1113) 1-(4-{(E)-2-[2-(4-chloro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea;

(1114) 1-(3,5-dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea;

(1115) 1-(4-{(E)-2-[2-(6-ethoxy-hexyl)-4-oxo-1,3,8-triaza-spiro[4.5]dec-1-ene-8-sulfonyl]-vinyl}-3,5-dimethyl-phenyl)-1-methyl-urea;

(1116) 1-[3,5-dimethyl-4-((E)-2-{4-oxo-2-[3-(6,6,6-trifluoro-hexyl)-phenyl]-1,3,8-triaza-spiro[4.5]dec-1-ene-8-sulfonyl}-vinyl)-phenyl]-1-methyl-urea;

(1117) 1-[3,5-dimethyl-4-((E)-2-{4-oxo-2-[4-(6,6,6-trifluoro-hexyl)-phenyl]-1,3,8-triaza-spiro[4.5]dec-1-ene-8-sulfonyl}-vinyl)-phenyl]-1-methyl-urea;

(1118) 1-(4-{(E)-2-[2-(11-fluoro-undecyl)-4-oxo-1,3,8-triaza-spiro[4.5]dec-1-ene-8-sulfonyl]-vinyl}-3,5-dimethyl-phenyl)-1-methyl-urea;

(1119) 1-{4-[(E)-2-(2-hex-5-enyl-4-oxo-1,3,8-triaza-spiro[4.5]dec-1-ene-8-sulfonyl)-vinyl]-3,5-dimethyl-phenyl}-1-methyl-urea;

(1120) 1-(3,5-dimethyl-4-{(E)-2-[4-oxo-2-((E)-6-phenyl-hex-5-enyl)-1,3,8-triaza-spiro[4.5]dec-1-ene-8-sulfonyl]-vinyl}-phenyl)-1-methyl-urea;

(1121) 1-(3,5-dimethyl-4-{(E)-2-[4-oxo-2-((E)-9-phenyl-non-8-enyl)-1,3,8-triaza-spiro[4.5]dec-1-ene-8-sulfonyl]-vinyl}-phenyl)-1-methyl-urea;

(1122) 1-(3,5-dimethyl-4-{(E)-2-[4-oxo-2-(5-propylsulfanyl-pentyl)-1,3,8-triaza-spiro[4.5]dec-1-ene-8-sulfonyl]-vinyl}-phenyl)-1-methyl-urea;

(1123) 1-(4-{(E)-2-[2-(7-methoxy-heptyl)-4-oxo-1,3,8-triaza-spiro[4.5]dec-1-ene-8-sulfonyl]-vinyl}-3,5-dimethyl-phenyl)-1-methyl-urea;

(1124) 1-(3,5-dimethyl-4-{(E)-2-[4-oxo-2-(5-propoxy-pentyl)-1,3,8-triaza-spiro[4.5]dec-1-ene-8-sulfonyl]-vinyl}-phenyl)-1-methyl-urea;

(1125) 1-(4-{(E)-2-[2-(11,11-difluoro-undecyl)-4-oxo-1,3,8-triaza-spiro[4.5]dec-1-ene-8-sulfonyl]-vinyl}-3,5-dimethyl-phenyl)-1-methyl-urea;

(1126) 1-(3,5-dimethyl-4-{(E)-2-[4-oxo-2-(3-propyl-nonyl)-1,3,8-triaza-spiro[4.5]dec-1-ene-8-sulfonyl]-vinyl}-phenyl)-1-methyl-urea;

(1127) 1-(3,5-dimethyl-4-{(E)-2-[4-oxo-2-(2-propyl-benzofuran-6-yl)-1,3,8-triaza-spiro[4.5]dec-1-ene-8-sulfonyl]-vinyl}-phenyl)-1-methyl-urea;

(1128) 1-(4-{(E)-2-[2-(3-methoxy-4-pentyl-phenyl)-4-oxo-1,3,8-triaza-spiro[4.5]dec-1-ene-8-sulfonyl]-vinyl}-3,5-dimethyl-phenyl)-1-methyl-urea;

(1129) 1-(4-{(E)-2-[2-(4-[1,1,2,2,2-$^2$H$_5$]ethyl-cyclohex-3-enyl)-4-oxo-1,3,8-triaza-spiro[4.5]dec-1-ene-8-sulfonyl]-vinyl}-3,5-dimethyl-phenyl)-1-methyl-urea;

(1130) 1-(4-{(E)-2-[2-(4-[1,1,2,2,2-$^2$H$_5$]ethyl-[4-$^2$H$_1$]cyclohexyl)-4-oxo-1,3,8-triaza-spiro[4.5]dec-1-ene-8-sulfonyl]-vinyl}-3,5-dimethyl-phenyl)-1-methyl-urea;

(1131) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid;

(1132) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid ethyl ester;

(1133) 1-(3,5-dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea;

(1134) 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea;

(1135) 1-[3,5-dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea;

(1136) 1-(3,5-dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea;

(1137) 1-(3,5-dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea;

(1138) 1-(4-{2-[2-((1R,3R,5S)-3,5-bis-trifluoromethyl-cyclohexyl)-4-oxo-1,3,8-triaza-spiro[4.5]dec-1-ene-8-sulfonyl]-ethyl}-3,5-dimethyl-phenyl)-1-methyl-urea;

(1139) 1-(3,5-dimethyl-4-{2-[4-oxo-2-(4-trimethylsilanyl-phenyl)-1,3,8-triaza-spiro[4.5]dec-1-ene-8-sulfonyl]-ethyl}-phenyl)-1-methyl-urea;

(1140) 1-{3,5-dimethyl-4-[2-(4-oxo-2-tridecyl-1,3,8-triaza-spiro[4.5]dec-1-ene-8-sulfonyl)-ethyl]-phenyl}-1-methyl-urea;

(1141) 1-{3,5-dimethyl-4-[2-(4-oxo-2-undecyl-1,3,8-triaza-spiro[4.5]dec-1-ene-8-sulfonyl)-ethyl]-phenyl}-1-methyl-urea;

(1142) 1-{3,5-dimethyl-4-[2-(2-octyl-4-oxo-1,3,8-triaza-spiro[4.5]dec-1-ene-8-sulfonyl)-ethyl]-phenyl}-1-methyl-urea;

(1143) 1-(4-{2-[2-((1S,3R)-3-hexyl-cyclohexyl)-4-oxo-1,3,8-triaza-spiro[4.5]dec-1-ene-8-sulfonyl]-ethyl}-3,5-dimethyl-phenyl)-1-methyl-urea;

(1144) 1-[3,5-dimethyl-4-(2-{2-[3-(3-methyl-butyl)-phenyl]-4-oxo-1,3,8-triaza-spiro[4.5]dec-1-ene-8-sulfonyl}-ethyl)-phenyl]-1-methyl-urea;

(1145) 1-(4-{2-[2-((1S,3R)-3-butyl-cyclohexyl)-4-oxo-1,3,8-triaza-spiro[4.5]dec-1-ene-8-sulfonyl]-ethyl}-3,5-dimethyl-phenyl)-1-methyl-urea;

(1146) 1-[3,5-dimethyl-4-(2-{2-[(1S,3S)-3-(3-methyl-butyl)-cyclohexyl]-4-oxo-1,3,8-triaza-spiro[4.5]dec-1-ene-8-sulfonyl}-ethyl)-phenyl]-1-methyl-urea;

(1147) 1-(3,5-dimethyl-4-{2-[4-oxo-2-(3,3,9,9,9-pentafluoro-nonyl)-1,3,8-triaza-spiro[4.5]dec-1-ene-8-sulfonyl]-ethyl}-phenyl)-1-methyl-urea;

(1148) 1-(4-{2-[2-(4-[1,1,2,2,2-$^2$H$_5$]ethyl-[4-$^2$H$_1$]cyclohexyl)-4-oxo-1,3,8-triaza-spiro[4.5]dec-1-ene-8-sulfonyl]-ethyl}-3,5-dimethyl-phenyl)-1-methyl-urea;

(1149) 1-(4-{2-[2-(4-[1,1,2,2,2-$^2$H$_5$]ethyl-cyclohex-3-enyl)-4-oxo-1,3,8-triaza-spiro[4.5]dec-1-ene-8-sulfonyl]-ethyl}-3,5-dimethyl-phenyl)-1-methyl-urea;

(1150) 1-(4-{2-[2-(4-chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea;

(1151) 1-(3,5-dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea;

(1152) 1-(3,5-dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea;

(1153) 1-(4-{2-[2-(11-fluoro-undecyl)-4-oxo-1,3,8-triaza-spiro[4.5]dec-1-ene-8-sulfonyl]-ethyl}-3,5-dimethyl-phenyl)-1-methyl-urea;

(1154) 1-(4-{2-[2-(6-ethylsulfanyl-hexyl)-4-oxo-1,3,8-triaza-spiro[4.5]dec-1-ene-8-sulfonyl]-ethyl}-3,5-dimethyl-phenyl)-1-methyl-urea;

(1155) 1-{3,5-dimethyl-4-[2-(4-oxo-2-[1,1';3',1"]terphenyl-3-yl-1,3,8-triaza-spiro[4.5]dec-1-ene-8-sulfonyl)-ethyl]-phenyl}-1-methyl-urea;

(1156) 1-(4-{2-[2-(11,11-difluoro-undecyl)-4-oxo-1,3,8-triaza-spiro[4.5]dec-1-ene-8-sulfonyl]-ethyl}-3,5-dimethyl-phenyl)-1-methyl-urea;

(1157) 1-{3,5-dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea;

(1158) 8-{(E)-2-[4-(4-hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one;

(1159) 2-(4-fluoro-3-trifluoromethoxy-phenyl)-8-{(E)-[4-(4-hydroxy-piperidine-1-carbonyl)-2,6-dimethyl-phenyl]-ethenesulfonyl}-1,3,8-triaza-spiro[4.5]dec-1-en-4-one;

(1160) 2-(2,2-difluoro-benzo[1,3]dioxol-5-yl)-8-{(E)-[4-(4-hydroxy-piperidine-1-carbonyl)-2,6-dimethyl-phenyl]-ethenesulfonyl}-1,3,8-triaza-spiro[4.5]dec-1-en-4-one;

(1161) 2-(4-fluoro-3-trifluoromethoxy-phenyl)-8-{(E)-[4-(4-hydroxymethyl-piperidine-1-carbonyl)-2,6-dimeth phenyl]-ethenesulfonyl}-1,3,8-triaza-spiro[4.5]dec-1-en-4-one;

(1162) 2-(4-fluoro-3-trifluoromethyl-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-4-one;

(1163) 2-(2,2-difluoro-benzo[1,3]dioxol-5-yl)-8-{(E)-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1164) 8-{(E)-2-[4-((R)-2,3-dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one;

(1165) 2-(2,2-difluoro-benzo[1,3]dioxol-5-yl)-8-{(E)-2-[4-((R)-2,3-dihydroxy-propoxy)-2,6-dimethyl-phenyl]-ethenesulfonyl}-1,3,8-triaza-spiro[4.5]dec-1-en-4-one;

(1166) 8-{(E)-2-[4-(3,4-dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one;

(1167) 2-(2,2-difluoro-benzo[1,3]dioxol-5-yl)-8-{(E)-2-[4-(3,4-dihydroxy-butoxy)-2-methyl-phenyl]-ethenesulfonyl}-1,3,8-triaza-spiro[4.5]dec-1-en-4-one;

(1168) {4-[(E)-2-(2-cyclohexyl-4-oxo-1,3,8-triaza-spiro[4.5]dec-1-ene-8-sulfonyl)-vinyl]-indol-1-yl}-acetic acid;

(1169) [3-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-ureido]-acetic acid;

(1170) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid;

(1171) 10-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-decanoic acid;

(1172) 10-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-decanoic acid amide;

(1173) 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid amide;

(1174) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid amide;

(1175) 14-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-tetradecanoic acid amide;

(1176) 14-(8-{2-[2,6-dimethyl-4-(1-methyl-ureido)-phenyl]-ethanesulfonyl}-4-oxo-1,3,8-triaza-spiro[4.5]dec-1-en-2-yl)-tetradecanoic acid amide;

(1178) 8-[2-(2-amino-5,7-dimethyl-benzoxazol-6-yl)-ethanesulfonyl]-2-(4-methyl-cyclohexyl)-1,3,8-triaza-spiro[4.5]dec-1-en-4-one;

(1179) 2-cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one;

(1180) N-methoxy-3,5,N-trimethyl-4-{2-[2-(4-methyl-cyclohexyl)-4-oxo-1,3,8-triaza-spiro[4.5]dec-1-ene-8-sulfonyl]-ethyl}-benzamide;

(1181) 8-{2-[4-(isoxazolidine-2-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1182) 8-{2-[4-(isoxazolidine-2-carbonyl)-2,6-dimethyl-phenyl]-ethanesulfonyl}-2-(4-methyl-cyclohexyl)-1,3,8-triaza-spiro[4.5]dec-1-en-4-one;

(1183) 8-{2-[4-(1,1-dioxo-1$\lambda^6$-thiomorpholine-4-carbonyl)-2,6-dimethyl-phenyl]-ethanesulfonyl}-2-(4-methyl-cyclohexyl)-1,3,8-triaza-spiro[4.5]dec-1-en-4-one;

(1184) 8-(2-{4-[((R)-2,3-dihydroxy-propoxy)-piperidine-1-carbonyl]-2,6-dimethyl-phenyl}-ethanesulfonyl)-2-(9,9,9-trifluoro-nonyl)-1,3,8-triaza-spiro[4.5]dec-1-en-4-one;

(1185) 2-(3,4-dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1186) 2-(3-chloro-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1187) [3-(8-{(E)-2-[4-(4-hydroxy-4-methyl-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1188) 2-(3-chloro-4-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1189) 8-{(E)-2-[4-(4-hydroxy-4-methyl-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;

(1190) 8-{(E)-2-[4-(4-hydroxy-4-methyl-piperidine-1-carbonyl)-2,6-dimethyl-phenyl]-ethenesulfonyl}-2-(3-pentafluorosulfanyl-phenyl)-1,3,8-triaza-spiro[4.5]dec-1-en-4-one;

(1191) 8-{(E)-2-[4-(4-hydroxy-4-methyl-piperidine-1-carbonyl)-2,6-dimethyl-phenyl]-ethenesulfonyl}-2-[4-(3-trifluoromethyl-phenoxymethyl)-phenyl]-1,3,8-triaza-spiro[4.5]dec-1-en-4-one;

(1192) 2-(4-fluoro-2,3-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1193) 8-{(E)-2-[4-(4-hydroxy-4-methyl-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;

(1194) 2-benzo[1,3]dioxol-5-yl-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1195) 8-{(E)-2-[4-(4-hydroxy-4-methyl-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;

(1196) 8-{(E)-2-[4-(4-hydroxy-4-methyl-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;

(1197) 8-{(E)-2-[4-(4-hydroxy-4-methyl-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1198) 8-{(E)-2-[4-(4-hydroxy-4-methyl-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1199) 8-{(E)-2-[4-(4-hydroxy-4-methyl-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;

(1200) 8-{(E)-2-[4-(4-hydroxy-4-methyl-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;

(1201) 2-[3-chloro-4-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1202) 8-{(E)-2-[4-(4-hydroxy-4-methyl-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;

(1203) 8-{(E)-2-[4-(4-hydroxy-4-methyl-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;

(1204) 8-{(E)-2-[4-(4-hydroxy-4-methyl-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;

(1205) 8-{(E)-2-[4-(4-hydroxy-4-methyl-piperidine-1-carbonyl)-2,6-dimethyl-phenyl]-ethenesulfonyl}-2-[3-(3-trifluoromethyl-phenoxymethyl)-phenyl]-1,3,8-triaza-spiro[4.5]dec-1-en-4-one;

(1206) 2-[3-(1,1-difluoro-ethyl)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1207) 2-[3-fluoro-4-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1208) 8-{(E)-2-[4-(4-hydroxy-4-methyl-piperidine-1-carbonyl)-2,6-dimethyl-phenyl]-ethenesulfonyl}-2-(1H-indol-6-yl)-1,3,8-triaza-spiro[4.5]dec-1-en-4-one;

(1209) 8-{(E)-2-[4-(4-hydroxy-4-methyl-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1210) 2-[4-chloro-3-(2,2,2-trifluoro-1,1-dimethyl-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1211) 2-(3-[1,1,2,2,3,3,4,4,4-$^2$H$_9$]butoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1212) 8-{(E)-2-[4-(4-hydroxy-4-methyl-piperidine-1-carbonyl)-2,6-dimethyl-phenyl]-ethenesulfonyl}-2-(2,2,3,3-tetrafluoro-2,3-dihydro-benzo[1,4]dioxin-6-yl)-1,3,8-triaza-spiro[4.5]dec-1-en-4-one;

(1213) 8-{(E)-2-[4-(4-hydroxy-4-methyl-piperidine-1-carbonyl)-2,6-dimethyl-phenyl]-ethenesulfonyl}-2-[4-(1,1,2,2-tetrafluoro-ethoxy)-phenyl]-1,3,8-triaza-spiro[4.5]dec-1-en-4-one;

(1214) 8-{(E)-2-[4-(4-hydroxy-4-methyl-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1215) 2-[4-fluoro-3-(3-fluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1216) 2-[3-chloro-4-(2,2,2-trifluoro-ethoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1217) 2-(3-difluoromethyl-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1218) 2-[4-fluoro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1219) 2-(4-difluoromethyl-3-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1220) 2-(4-[1,1,2,2,3,3,4,4,4-$^2$H$_9$]butoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1221) 2-(4-[1,1,2,2,2-$^2$H$_5$]ethoxy-3-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1222) 8-{(E)-2-[4-(4-hydroxy-4-methyl-piperidine-1-carbonyl)-2,6-dimethyl-phenyl]-ethenesulfonyl}-2-(4-[1,2,2,2,2,2-$^2$H$_7$]isopropoxy-3-trifluoromethyl-phenyl)-1,3,8-triaza-spiro[4.5]dec-1-en-4-one;

(1223) 8-{(E)-2-[4-(4-hydroxy-4-methyl-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1224) 2-(3-[1,1,2,2,2-$^2$H$_5$]ethoxy-4-fluoro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1225) 2-(4-fluoro-3-[1,2,2,2,2,2,2-$^2$H$_7$]isopropoxyphenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;

(1226) 8-{(E)-2-[4-(4-hydroxy-4-methyl-piperidine-1-carbonyl)-2,6-dimethyl-phenyl]-ethenesulfonyl}-2-[3-(2,2, (1227) 2-[4-chloro-3-(4,4,4-trifluoro-butoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1228) 8-{(E)-2-[4-(4-hydroxy-4-methyl-piperidine-1-carbonyl)-2,6-dimethyl-phenyl]-ethenesulfonyl}-2-[3-(2,2,3,3,3-pentafluoro-propoxy)-4-trifluoromethyl-phenyl]-1,3,8-triaza-spiro[4.5]dec-1-en-4-one;
(1229) 2-[4-chloro-3-(2,2,3,3-tetrafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1230) 2-[4-chloro-3-(2,2,3,3,3-pentafluoro-propoxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1231) 2-(3-[1,1,2,2,3,3,4,4,4-$^2$H$_9$]butoxy-4-chloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1232) 8-{(E)-2-[4-(4-hydroxy-4-methyl-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;
(1233) 2-(3-[1,1,2,2,3,3,4,4,4-$^2$H$_9$]butoxy-5-trifluoromethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1234) 8-{2-[4-(4-hydroxy-4-methyl-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;
(1235) 8-{2-[4-(4-hydroxy-4-methyl-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;
(1236) 2-(3-chloro-4-trifluoromethyl-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;
(1237) 2-(3,4-dimethyl-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1238) 8-{(E)-2-[4-(4-hydroxy-4-methyl-piperidine-1-carbonyl)-2,6-dimethyl-phenyl]-ethenesulfonyl}-2-(4-methoxy-3-methyl-phenyl)-1,3,8-triaza-spiro[4.5]dec-1-en-4-one;
(1239) 2-(4-fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1240) 2-(4-fluoro-2,3-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1241) 2-(3-chloro-4-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1242) 2-(3-chloro-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1243) 8-{(E)-2-[4-(4-fluoromethyl-4-hydroxy-piperidine-1-carbonyl)-2,6-dimethyl-phenyl]-ethenesulfonyl}-2-(3-pentafluoroethyl-phenyl)-1,3,8-triaza-spiro[4.5]dec-1-en-4-one;
(1244) 8-{(E)-2-[4-(4-fluoromethyl-4-hydroxy-piperidine-1-carbonyl)-2,6-dimethyl-phenyl]-ethenesulfonyl}-2-(4-pentafluoroethyl-phenyl)-1,3,8-triaza-spiro[4.5]dec-1-en-4-one;
(1245) 8-{(E)-2-[4-(4-fluoromethyl-4-hydroxy-piperidine-1-carbonyl)-2,6-dimethyl-phenyl]-ethenesulfonyl}-2-(4-pentafluorosulfanyl-phenyl)-1,3,8-triaza-spiro[4.5]dec-1-en-4-one;
(1246) 2-[3-chloro-4-(2,2,2-trifluoro-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1247) 2-[3-chloro-4-(2,2,3,3-tetrafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1248) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-ethoxy)-3-trifluoromethyl-phenyl]-1,3,8-triaza-spiro[4.5]dec-1-en-4-one;
(1249) 8-{(E)-2-[4-(4-fluoromethyl-4-hydroxy-piperidine-1-carbonyl)-2,6-dimethyl-phenyl]-ethenesulfonyl}-2-[4-(2,2,3,3,3-pentafluoro-propoxy)-3-trifluoromethyl-phenyl]-1,3,8-triaza-spiro[4.5]dec-1-en-4-one;
(1250) 8-{(E)-2-[4-(4-fluoromethyl-4-hydroxy-piperidine-1-carbonyl)-2,6-dimethyl-phenyl]-ethenesulfonyl}-2-[4-(4,4,4-trifluoro-butoxy)-3-trifluoromethyl-phenyl]-1,3,8-triaza-spiro[4.5]dec-1-en-4-one;
(1251) 8-{(E)-2-[4-(4-fluoromethyl-4-hydroxy-piperidine-1-carbonyl)-2,6-dimethyl-phenyl]-ethenesulfonyl}-2-[4-(2,2,3,3-tetrafluoro-propoxy)-3-trifluoromethyl-phenyl]-1,3,8-triaza-spiro[4.5]dec-1-en-4-one;
(1252) 8-{(E)-2-[4-(4-fluoromethyl-4-hydroxy-piperidine-1-carbonyl)-2,6-dimethyl-phenyl]-ethenesulfonyl}-2-[4-(4,4,5,5,5-pentafluoro-pentyloxy)-3-trifluoromethyl-phenyl]-1,3,8-triaza-spiro[4.5]dec-1-en-4-one;
(1253) 2-(4-[1,1,2,2,2-$^2$H$_5$]ethoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1254) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethyl-phenyl)-1,3,8-triaza-spiro[4.5]dec-1-en-4-one;
(1255) 2-(4-difluoromethyl-3-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1256) 2-(3-difluoromethyl-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1257) 2-(3,4-dichloro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;
(1258) 8-{(E)-2-[4-(4-fluoromethyl-4-hydroxy-piperidine-1-carbonyl)-2,6-dimethyl-phenyl]-ethenesulfonyl}-2-(3-methyl-4-trifluoromethoxy-phenyl)-1,3,8-triaza-spiro[4.5]dec-1-en-4-one;

(1259) 8-{(E)-2-[4-(4-fluoromethyl-4-hydroxy-piperidine-1-carbonyl)-2,6-dimethyl-phenyl]-ethenesulfonyl}-2-(2-methyl-4-trifluoromethyl-phenyl)-1,3,8-triaza-spiro[4.5]dec-1-en-4-one;

(1260) 8-{(E)-2-[4-(4-fluoromethyl-4-hydroxy-piperidine-1-carbonyl)-2,6-dimethyl-phenyl]-ethenesulfonyl}-2-[3-fluoro-4-(2,2,2-trifluoro-ethoxy)-phenyl]-1,3,8-triaza-spiro[4.5]dec-1-en-4-one;

(1261) 2-(4-[1,1,2,2,3,3,4,4,4-$^2$H$_9$]butoxy-3-trifluoromethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1262) 8-{(E)-2-[4-(4-fluoromethyl-4-hydroxy-piperidine-1-carbonyl)-2,6-dimethyl-phenyl]-ethenesulfonyl}-2-(4-[1,2,2,2,2,2,2-$^2$H$_7$]isopropoxy-3-trifluoromethyl-phenyl)-1,3,8-triaza-spiro[4.5]dec-1-en-4-one;

(1263) 8-{(E)-2-[4-(4-fluoromethyl-4-hydroxy-piperidine-1-carbonyl)-2,6-dimethyl-phenyl]-ethenesulfonyl}-2-[4-fluoro-3-(4,4,5,5,5-pentafluoro-pentyloxy)-phenyl]-1,3,8-triaza-spiro-[4.5]dec-1-en-4-one;

(1264) 2-[4-fluoro-3-(3-fluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1265) 8-{(E)-2-[4-(4-fluoromethyl-4-hydroxy-piperidine-1-carbonyl)-2,6-dimethyl-phenyl]-ethenesulfonyl}-2-[4-(2,2,2-trifluoro-1,1-dimethyl-ethoxy)-3-trifluoromethyl-phenyl]-1,3,8-triaza-spiro[4.5]dec-1-en-4-one;

(1266) 8-{(E)-2-[4-(4-fluoromethyl-4-hydroxy-piperidine-1-carbonyl)-2,6-dimethyl-phenyl]-ethenesulfonyl}-2-[3-(2,2,2-trifluoro-1,1-dimethyl-ethoxy)-4-trifluoromethyl-phenyl]-1,3,8-triaza-spiro[4.5]dec-1-en-4-one;

(1267) 2-[3-(1,1-difluoro-ethyl)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1268) 8-{(E)-2-[4-(4-fluoromethyl-4-hydroxy-piperidine-1-carbonyl)-2,6-dimethyl-phenyl]-ethenesulfonyl}-2-(1H-indol-6-yl)-1,3,8-triaza-spiro[4.5]dec-1-en-4-one;

(1269) 8-{(E)-2-[4-(4-fluoromethyl-4-hydroxy-piperidine-1-carbonyl)-2,6-dimethyl-phenyl]-ethenesulfonyl}-2-(4-trifluoromethoxy-phenyl)-1,3,8-triaza-spiro[4.5]dec-1-en-4-one;

(1270) 2-[4-chloro-3-(2,2,3,3,3-pentafluoro-propoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1271) 2-[4-chloro-3-(2,2,2-trifluoro-1,1-dimethyl-ethoxy)-phenyl]-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1272) 2-(3-[1,1,2,2,2-$^2$H$_5$]ethoxy-4-fluoro-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1273) 8-{(E)-2-[4-(4-fluoromethyl-4-hydroxy-piperidine-1-carbonyl)-2,6-dimethyl-phenyl]-ethenesulfonyl}-2-[3-(4,4,4-trifluoro-butoxy)-4-trifluoromethoxy-phenyl]-1,3,8-triaza-spiro[4.5]dec-1-en-4-one;

(1274) 8-{(E)-2-[4-(4-fluoromethyl-4-hydroxy-piperidine-1-carbonyl)-2,6-dimethyl-phenyl]-ethenesulfonyl}-2-[3-(2,2,3,3-tetrafluoro-propoxy)-4-trifluoromethyl-phenyl]-1,3,8-triaza-spiro[4.5]dec-1-en-4-one;

(1275) 2-(2,2-difluoro-benzo[1,3]dioxol-5-yl)-8-{2-[4-(4-fluoromethyl-4-hydroxy-piperidine-1-carbonyl)-2,6-dimethyl-phenyl]-ethanesulfonyl}-1,3,8-triaza-spiro[4.5]dec-1-en-4-one;

(1276) 8-{2-[4-(4-fluoromethyl-4-hydroxy-piperidine-1-carbonyl)-2,6-dimethyl-phenyl]-ethanesulfonyl}-2-(4-trifluoromethoxy-phenyl)-1,3,8-triaza-spiro[4.5]dec-1-en-4-one;

(1277) 8-{2-[4-(4-fluoromethyl-4-hydroxy-piperidine-1-carbonyl)-2,6-dimethyl-phenyl]-ethanesulfonyl}-2-(3-methyl-4-trifluoromethyl-phenyl)-1,3,8-triaza-spiro[4.5]dec-1-en-4-one;

(1278) 2-(3-chloro-4-trifluoromethyl-phenyl)-8-{2-[4-(4-fluoromethyl-4-hydroxy-piperidine-1-carbonyl)-2,6-dimethyl-phenyl]-ethanesulfonyl}-1,3,8-triaza-spiro[4.5]dec-1-en-4-one;

(1279) 8-{2-[4-(4-fluoromethyl-4-hydroxy-piperidine-1-carbonyl)-2,6-dimethyl-phenyl]-ethanesulfonyl}-2-[3-(2,2,3,3-tetrafluoro-propoxy)-4-trifluoromethyl-phenyl]-1,3,8-triaza-spiro[4.5]dec-1-en-4-one;

(1280) 2-(2,2-difluoro-benzo[1,3]dioxol-5-yl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one;

(1281) 8-{2-[4-(4-fluoromethyl-4-hydroxy-piperidine-1-carbonyl)-2,6-dimethyl-phenyl]-ethanesulfonyl}-2-(2,2,3,3-tetrafluoro-2,3-dihydro-benzo[1,4]dioxin-6-yl)-1,3,8-triaza-spiro[4.5]dec-1-en-4-one;

(1282) [3-(8-{(E)-2-[4-(4-hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile;

(1283) 8-{(E)-2-[2-methyl-4-(piperidin-4-yloxy)-phenyl]-ethenesulfonyl}-2-(3-trifluoromethoxy-phenyl)-1,3,8-triaza-spiro[4.5]dec-1-en-4-one;

(1284) 8-[2-(4-aminomethyl-2-methyl-phenyl)-ethanesulfonyl]-2-[4-(3,3,3-trifluoro-propyl)-cyclohexyl]-1,3,8-triaza-spiro[4.5]dec-1-en-4-one;

(1285) 2-(4-methyl-cyclohexyl)-8-{(E)-2-[2-methyl-4-(2-oxo-piperazin-1-yl)-phenyl]-ethenesulfonyl}-1,3,8-triaza-spiro[4.5]dec-1-en-4-one;

(1286) 8-[2-(2,6-dimethyl-4-methylamino-phenyl)-ethanesulfonyl]-2-pyrrolidin-2-yl-1,3,8-triaza-spiro[4.5]dec-1-en-4-one hydrochloride;

(1287) 2-(1,1-difluoro-ethyl)-8-[2-(2,6-dimethyl-4-methylamino-phenyl)-ethanesulfonyl]-1,3,8-triaza-spiro[4.5]dec-1-en-4-one hydrochloride;

(1288) 8-[(E)-2-(2,6-dimethyl-4-[1,1,1-$^2$H$_3$]methylamino-phenyl)-ethenesulfonyl]-2-(4-fluoro-3-trifluoromethyl-phenyl)-1,3,8-triaza-spiro[4.5]dec-1-en-4-one hydrochloride;

(1289) 8-[(E)-2-(2,6-dimethyl-4-methylaminomethyl-phenyl)-ethenesulfonyl]-2-(4-methyl-cyclohexyl)-1,3,8-triaza-spiro[4.5]dec-1-en-4-one;

(1290) 8-[(E)-2-(4-aminomethyl-2,6-dimethyl-phenyl)-ethenesulfonyl]-2-[4-(3,3,3-trifluoro-propyl)-cyclohexyl]-1,3,8-triaza-spiro[4.5]dec-1-en-4-one;

(1291) 8-[(E)-2-(4-aminomethyl-2,6-dimethyl-phenyl)-ethenesulfonyl]-2-(4-methyl-cyclohexyl)-1,3,8-triaza-spiro[4.5]dec-1-en-4-one;

(1292) 8-[(E)-2-(2,6-dimethyl-4-methylaminomethyl-phenyl)-ethenesulfonyl]-2-[4-(3,3,3-trifluoro-propyl)-cyclohexyl]-1,3,8-triaza-spiro[4.5]dec-1-en-4-one;

(1293) 8-[2-(4-amino-3-chloro-2-methyl-phenyl)-ethanesulfonyl]-2-(4-ethyl-cyclohexyl)-1,3,8-triaza-spiro[4.5]dec-1-en-4-one;

(1294) N-(1-acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide;

(1295) 8-{2-[4-(4,5-dihydro-thiazol-2-ylamino)-2-methyl-phenyl]-ethanesulfonyl}-2-(4-ethyl-cyclohexyl)-1,3,8-triaza-spiro[4.5]dec-1-en-4-one;

(1296) N-[4-(2-{2-[4-(4-fluoro-butyl)-cyclohexyl]-4-oxo-1,3,8-triaza-spiro[4.5]dec-1-ene-8-sulfonyl}-ethyl)-3-methyl-phenyl]-acetamide;

(1297) 1-(3,5-dimethyl-4-{2-[2-((1S,3R)-3-methyl-cyclohexyl)-4-oxo-1,3,8-triaza-spiro[4.5]dec-1-ene-8-sulfonyl]-ethyl}-phenyl)-1-methyl-urea;

(1298) 1-(3,5-dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea;

(1299) 3-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione;

(1300) 1-[3,5-dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea;

(1301) 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-benzyl)-1-methyl-urea;

(1302) 1-(3,5-dimethyl-4-{2-[4-oxo-2-(8,8,9,9,9-pentafluoro-nonyl)-1,3,8-triaza-spiro[4.5]dec-1-ene-8-sulfonyl]-ethyl}-phenyl)-1-methyl-urea;

(1303) 1-(3,5-dimethyl-4-{(E)-2-[4-oxo-2-(8,8,9,9,9-pentafluoro-nonyl)-1,3,8-triaza-spiro[4.5]dec-1-ene-8-sulfonyl]-vinyl}-phenyl)-1-methyl-urea;

(1304) 1-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-1-methyl-urea;

(1305) 1-(3,5-dimethyl-4-{(E)-2-[4-oxo-2-(3-trifluoromethylsulfanyl-phenyl)-1,3,8-triaza-spiro[4.5]dec-1-ene-8-sulfonyl]-vinyl}-phenyl)-1-methyl-urea;

(1306) 1-(3,5-dimethyl-4-{2-[4-oxo-2-(3-trifluoromethylsulfanyl-phenyl)-1,3,8-triaza-spiro[4.5]dec-1-ene-8-sulfonyl]-ethyl}-phenyl)-1-methyl-urea;

(1307) 1-(4-{(E)-2-[2-(11-hydroxy-undecyl)-4-oxo-1,3,8-triaza-spiro[4.5]dec-1-ene-8-sulfonyl]-vinyl}-3,5-dimethyl-phenyl)-1-methyl-urea;

(1308) [11-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-undecyl]-carbamic acid tert-butyl ester;

(1309) 1-(4-{(E)-2-[2-(9-hydroxy-nonyl)-4-oxo-1,3,8-triaza-spiro[4.5]dec-1-ene-8-sulfonyl]-vinyl}-3,5-dimethyl-phenyl)-1-methyl-urea;

(1310) 1-(4-{2-[2-(4-isopropylidene-cyclohexyl)-4-oxo-1,3,8-triaza-spiro[4.5]dec-1-ene-8-sulfonyl]-ethyl}-3,5-dimethyl-phenyl)-1-methyl-urea;

(1311) 1-(4-{2-[2-(1,1-difluoro-ethyl)-4-oxo-1,3,8-triaza-spiro[4.5]dec-1-ene-8-sulfonyl]-ethyl}-3,5-dimethyl-phenyl)-1-methyl-urea;

(1312) 1-(4-{(E)-2-[2-(4-fluoro-3-trifluoromethyl-phenyl)-4-oxo-1,3,8-triaza-spiro[4.5]dec-1-ene-8-sulfonyl]-vinyl}-3,5-dimethyl-phenyl)-1-[,1,1-$^2$H$_3$]methyl-urea;

(1313) [3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea;

(1314) (3,5-dimethyl-4-{2-[2-(4-methyl-cyclohexyl)-4-oxo-1,3,8-triaza-spiro[4.5]dec-1-ene-8-sulfonyl]-ethyl}-benzyl)-urea;

(1315) 1-(4-{(E)-2-[2-(11-amino-undecyl)-4-oxo-1,3,8-triaza-spiro[4.5]dec-1-ene-8-sulfonyl]-vinyl}-3,5-dimethyl-phenyl)-1-methyl-urea;

(1316) 1-[3,5-dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea;

(1317) 1-(4-{2-[2-(6-ethanesulfinyl-hexyl)-4-oxo-1,3,8-triaza-spiro[4.5]dec-1-ene-8-sulfonyl]-ethyl}-3,5-dimethyl-phenyl)-1-methyl-urea;

(1318) 1-[3,5-dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea;

(1319) 1-(4-{(E)-2-[2-(7-methanesulfonyl-heptyl)-4-oxo-1,3,8-triaza-spiro[4.5]dec-1-ene-8-sulfonyl]-vinyl}-3,5-dimethyl-phenyl)-1-methyl-urea;

(1320) 1-(4-{2-[2-(6-ethanesulfonyl-hexyl)-4-oxo-1,3,8-triaza-spiro[4.5]dec-1-ene-8-sulfonyl]-ethyl}-3,5-dimethyl-phenyl)-1-methyl-urea;

(1321) 1-(4-{(E)-2-[2-(9,9-difluoro-nonyl)-4-oxo-1,3,8-triaza-spiro[4.5]dec-1-ene-8-sulfonyl]-vinyl}-3,5-dimethyl-phenyl)-1-methyl-urea;

(1322) 1-(4-{2-[2-(9-hydroxy-nonyl)-4-oxo-1,3,8-triaza-spiro[4.5]dec-1-ene-8-sulfonyl]-ethyl}-3,5-dimethyl-phenyl)-1-methyl-urea;

(1323) 1-(4-{2-[2-(9,9-difluoro-nonyl)-4-oxo-1,3,8-triaza-spiro[4.5]dec-1-ene-8-sulfonyl]-ethyl}-3,5-dimethyl-phenyl)-1-methyl-urea;

(1324) 1-(4-{2-[2-(9-amino-nonyl)-4-oxo-1,3,8-triaza-spiro[4.5]dec-1-ene-8-sulfonyl]-ethyl}-3,5-dimethyl-phenyl)-1-methyl-urea;

(1325) 1-(4-{(E)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea;

(1326) 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea;

(1327) 1-(4-{2-[2-(9-fluoro-nonyl)-4-oxo-1,3,8-triaza-spiro[4.5]dec-1-ene-8-sulfonyl]-ethyl}-3,5-dimethyl-phenyl)-1-methyl-urea;

(1328) 8-{2-[4-((R)-2,3-dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one;

(1329) 8-{2-[4-((R)-2,3-dihydroxy-propoxy)-2,6-dimethyl-phenyl]-ethanesulfonyl}-2-(4-fluoro-3-trifluoromethoxy-phenyl)-1,3,8-triaza-spiro[4.5]dec-1-en-4-one;

(1330) 2-(2,2-difluoro-benzo[1,3]dioxol-5-yl)-8-{2-[4-((R)-2,3-dihydroxy-propoxy)-2,6-dimethyl-phenyl]-ethanesulfonyl}-1,3,8-triaza-spiro[4.5]dec-1-en-4-one;

(1331) 2-(2,2-difluoro-benzo[1,3]dioxol-5-yl)-8-{2-[4-(3,4-dihydroxy-butoxy)-2-methyl-phenyl]-ethanesulfonyl}-1,3,8-triaza-spiro[4.5]dec-1-en-4-one;

(1332) 8-{2-[4-(3,4-dihydroxy-butoxy)-2-methyl-phenyl]-ethanesulfonyl}-2-(4-fluoro-3-trifluoromethoxy-phenyl)-1,3,8-triaza-spiro[4.5]dec-1-en-4-one;

(1333) 2-(2,2-difluoro-benzo[1,3]dioxol-5-yl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(1334) 2-(4-fluoro-3-trifluoromethoxy-phenyl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;

(1335) 2-(4-fluoro-3-trifluoromethoxy-phenyl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1336) 2-(2,2-difluoro-benzo[1,3]dioxol-5-yl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;

(1337) 2-(4-fluoro-3-trifluoromethoxy-phenyl)-8-{2-[4-(3-hydroxy-azetidine-1-carbonyl)-2,6-dimethyl-phenyl]-ethanesulfonyl}-1,3,8-triaza-spiro[4.5]dec-1-en-4-one;

(1338) 1-[3,5-dimethyl-4-(2-{4-oxo-2-[3-(4,4,4-trifluoro-butoxy)-phenyl]-1,3,8-triaza-spiro[4.5]dec-1-ene-8-sulfonyl}-ethyl)-phenyl]-1-methyl-urea;

(1339) 1-[3,5-dimethyl-4-(2-{4-oxo-2-[4-(4,4,4-trifluoro-butoxy)-phenyl]-1,3,8-triaza-spiro[4.5]dec-1-ene-8-sulfonyl}-ethyl)-phenyl]-1-methyl-urea;

(1340) 1-(3,5-dimethyl-4-{2-[4-oxo-2-(5-phenyl-pentyl)-1,3,8-triaza-spiro[4.5]dec-1-ene-8-sulfonyl]-ethyl}-phenyl)-1-methyl-urea;

(1341) 1-(3,5-dimethyl-4-{2-[2-(3-nonafluorobutyl-phenyl)-4-oxo-1,3,8-triaza-spiro[4.5]dec-1-ene-8-sulfonyl]-ethyl}-phenyl)-1-methyl-urea;

(1342) 1-(3,5-dimethyl-4-{2-[4-oxo-2-(4-pentyl-phenyl)-1,3,8-triaza-spiro[4.5]dec-1-ene-8-sulfonyl]-ethyl}-phenyl)-1-methyl-urea;

(1343) 1-(3,5-dimethyl-4-{2-[4-oxo-2-((1S,3R)-3-propyl-cyclohexyl)-1,3,8-triaza-spiro[4.5]dec-1-ene-8-sulfonyl]-ethyl}-phenyl)-1-methyl-urea;

(1344) 1-(4-{2-[2-(6-ethoxy-hexyl)-4-oxo-1,3,8-triaza-spiro[4.5]dec-1-ene-8-sulfonyl]-ethyl}-3,5-dimethyl-phenyl)-1-methyl-urea;

(1345) 1-[3,5-dimethyl-4-(2-{4-oxo-2-[3-(6,6,6-trifluoro-hexyl)-phenyl]-1,3,8-triaza-spiro[4.5]dec-1-ene-8-sulfonyl}-ethyl)-phenyl]-1-methyl-urea;

(1346) 1-[3,5-dimethyl-4-(2-{4-oxo-2-[4-(6,6,6-trifluoro-hexyl)-phenyl]-1,3,8-triaza-spiro[4.5]dec-1-ene-8-sulfonyl}-ethyl)-phenyl]-1-methyl-urea;

(1347) 12-(8-{2-[2,6-dimethyl-4-(1-methyl-ureido)-phenyl]-ethanesulfonyl}-4-oxo-1,3,8-triaza-spiro[4.5]dec-1-en-2-yl)-dodecanoic acid ethyl ester;

(1348) 1-(3,5-dimethyl-4-{2-[4-oxo-2-(9-phenyl-nonyl)-1,3,8-triaza-spiro[4.5]dec-1-ene-8-sulfonyl]-ethyl}-phenyl)-1-methyl-urea;

(1349) 1-(3,5-dimethyl-4-{2-[4-oxo-2-(6-phenyl-hexyl)-1,3,8-triaza-spiro[4.5]dec-1-ene-8-sulfonyl]-ethyl}-phenyl)-1-methyl-urea;

(1350) 14-(8-{2-[2,6-dimethyl-4-(1-methyl-ureido)-phenyl]-ethanesulfonyl}-4-oxo-1,3,8-triaza-spiro[4.5]dec-1-en-2-yl)-tetradecanoic acid;

(1351) 1-(4-{2-[2-(7-methoxy-heptyl)-4-oxo-1,3,8-triaza-spiro[4.5]dec-1-ene-8-sulfonyl]-ethyl}-3,5-dimethyl-phenyl)-1-methyl-urea;

(1352) 1-(3,5-dimethyl-4-{2-[4-oxo-2-(5-propoxy-pentyl)-1,3,8-triaza-spiro[4.5]dec-1-ene-8-sulfonyl]-ethyl}-phenyl)-1-methyl-urea;

(1353) 1-(3,5-dimethyl-4-{2-[4-oxo-2-(3-propyl-nonyl)-1,3,8-triaza-spiro[4.5]dec-1-ene-8-sulfonyl]-ethyl}-phenyl)-1-methyl-urea;

(1354) 1-(4-{2-[2-(3-methoxy-4-pentyl-phenyl)-4-oxo-1,3,8-triaza-spiro[4.5]dec-1-ene-8-sulfonyl]-ethyl}-3,5-dimethyl-phenyl)-1-methyl-urea;

(1355) 1-(3,5-dimethyl-4-{2-[4-oxo-2-(2-propyl-benzofuran-6-yl)-1,3,8-triaza-spiro[4.5]dec-1-ene-8-sulfonyl]-ethyl}-phenyl)-1-methyl-urea;

(1356) 1-[3,5-dimethyl-4-(2-{4-oxo-2-[5-(propane-1-sulfonyl)-pentyl]-1,3,8-triaza-spiro[4.5]dec-1-ene-8-sulfonyl}-ethyl)-phenyl]-1-methyl-urea;

(1357) 1-(4-{2-[2-(7-methanesulfonyl-heptyl)-4-oxo-1,3,8-triaza-spiro[4.5]dec-1-ene-8-sulfonyl]-ethyl}-3,5-dimethyl-phenyl)-1-methyl-urea;

(1358) 1-[3,5-dimethyl-4-(2-{4-oxo-2-[4-(4,4,4-trifluoro-butyl)-phenyl]-1,3,8-triaza-spiro[4.5]dec-1-ene-8-sulfonyl}-ethyl)-phenyl]-1-methyl-urea;

(1359) 1-[3,5-dimethyl-4-(2-{4-oxo-2-[3-(4,4,4-trifluoro-butyl)-phenyl]-1,3,8-triaza-spiro[4.5]dec-1-ene-8-sulfonyl}-ethyl)-phenyl]-1-methyl-urea;

(1360) [11-(8-{2-[2,6-dimethyl-4-(1-methyl-ureido)-phenyl]-ethanesulfonyl}-4-oxo-1,3,8-triaza-spiro[4.5]dec-1-en-2-yl)-undecyl]-carbamic acid tert-butyl ester;

(1361) 1-(4-{2-[2-(11-hydroxy-undecyl)-4-oxo-1,3,8-triaza-spiro[4.5]dec-1-ene-8-sulfonyl]-ethyl}-3,5-dimethyl-phenyl)-1-methyl-urea;

(1362) 10-(8-{2-[2,6-dimethyl-4-(1-methyl-ureido)-phenyl]-ethanesulfonyl}-4-oxo-1,3,8-triaza-spiro[4.5]dec-1-en-2-yl)-decanoic acid;

(1363) 10-(8-{2-[2,6-dimethyl-4-(1-methyl-ureido)-phenyl]-ethanesulfonyl}-4-oxo-1,3,8-triaza-spiro[4.5]dec-1-en-2-yl)-decanoic acid amide;

(1364) 1-(3,5-dimethyl-4-{2-[2-(4-[1,1,1-$^2$H$_3$]-methyl-[4-$^2$H$_1$]cyclohexyl)-4-oxo-1,3,8-triaza-spiro[4.5]dec-1-ene-8-sulfonyl]-ethyl}-phenyl)-1-methyl-urea;

(1365) 1-(3,5-dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea;

(1366) 1-(4-{2-[2-(11-amino-undecyl)-4-oxo-1,3,8-triaza-spiro[4.5]dec-1-ene-8-sulfonyl]-ethyl}-3,5-dimethyl-phenyl)-1-methyl-urea;

(1367) 3-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione;

(1368) 3-amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione;

(1369) 3-dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione;

(1370) N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide;

(1371) 1-(4-{2-[4-[(Z)-hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea;

(1372) 2-(4-methyl-cyclohexyl)-4-oxo-1,3,8-triaza-spiro[4.5]dec-1-ene-8-sulfonic acid 2-methyl-benzylamide;

(1373) 2-(4-methyl-cyclohexyl)-4-oxo-1,3,8-triaza-spiro[4.5]dec-1-ene-8-sulfonic acid (2-o-tolyl-ethyl)-amide;

(1374) 2-cyclohexyl-8-{2-[1-((S)-2,3-dihydroxy-propyl)-1H-indol-4-yl]-2-hydroxy-ethanesulfonyl}-1,3,8-triaza-spiro[4.5]dec-1-en-4-one;

(1375) 2-cyclohexyl-8-(2-oxo-2-o-tolyl-ethanesulfonyl)-1,3,8-triaza-spiro[4.5]dec-1-en-4-one;

(1376) 2-cyclohexyl-8-(2-o-tolyl-ethynesulfonyl)-1,3,8-triaza-spiro[4.5]dec-1-en-4-one;

(1377) 2-cyclohexyl-8-[2-(1H-indol-4-yl)-ethynesulfonyl]-1,3,8-triaza-spiro[4.5]dec-1-en-4-one;

(1378) 3,5,N,N-tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide;

(1379) 3,5,N,N-tetramethyl-4-{2-[2-(4-methyl-cyclohexyl)-4-oxo-1,3,8-triaza-spiro[4.5]dec-1-ene-8-sulfonyl]-ethyl}-benzamide;

(1380) 8-{2-[4-(4-hydroxy-4-methyl-piperidine-1-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1381) 8-{2-[4-(4-fluoromethyl-4-hydroxy-piperidine-1-carbonyl)-2,6-dimethyl-phenyl]-ethanesulfonyl}-2-[4-(3,3,3-trifluoro-propyl)-cyclohexyl]-1,3,8-triaza-spiro[4.5]dec-1-en-4-one;

(1382) 8-{2-[4-(4-hydroxy-4-methyl-piperidine-1-carbonyl)-2,6-dimethyl-phenyl]-ethanesulfonyl}-2-(4-methyl-cyclohexyl)-1,3,8-triaza-spiro[4.5]dec-1-en-4-one;

(1383) 8-{2-[4-(4-fluoromethyl-4-hydroxy-piperidine-1-carbonyl)-2,6-dimethyl-phenyl]-ethanesulfonyl}-2-(4-methyl-cyclohexyl)-1,3,8-triaza-spiro[4.5]dec-1-en-4-one;

(1384) 8-(2-{4-[4-((R)-2,3-dihydroxy-propoxy)-piperidine-1-carbonyl]-2,6-dimethyl-phenyl}-ethanesulfonyl)-2-[4-(3,3,3-trifluoro-propyl)-cyclohexyl]-1,3,8-triaza-spiro[4.5]dec-1-en-4-one;

(1385) 3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid hydrazide;

(1386) 8-{2-[2,6-dimethyl-4-(pyrazolidine-1-carbonyl)-phenyl]-ethanesulfonyl}-2-[4-(3,3,3-trifluoro-propyl)-cyclohexyl]-1,3,8-triaza-spiro[4.5]dec-1-en-4-one;

(1387) N,N-dimethyl-2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(1388) N-methoxy-2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide;

(1389) 1-[3,5-dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-1-methyl-urea;

(1390) 1-(3,5-dimethyl-4-{2-[2-(4-methyl-cyclohexyl)-4-oxo-1,3,8-triaza-spiro[4.5]dec-1-ene-8-sulfonyl]-ethyl}-benzyl)-1-methyl-urea;

(1391) 1-(4-{2-[2-(4-fluoro-3-trifluoromethyl-phenyl)-4-oxo-1,3,8-triaza-spiro[4.5]dec-1-ene-8-sulfonyl]-ethyl}-3,5-dimethyl-phenyl)-1-[1,1,1-$^2$H$_3$]methyl-urea;

(1392) 2-cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one;

(1393) 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one;

(1394) N-[3-methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide;

(1395) 3,N,N-trimethyl-4-{2-[4-oxo-2-(3-trifluoromethyl-phenylamino)-1,3,8-triaza-spiro[4.5]dec-1-ene-8-sulfonyl]-ethyl}-benzamide;

(1396) 3,N,N-trimethyl-4-{2-[4-oxo-2-(4-trifluoromethyl-phenylamino)-1,3,8-triaza-spiro[4.5]dec-1-ene-8-sulfonyl]-ethyl}-benzamide;

(1397) 3,N,N-trimethyl-4-{2-[2-(methyl-phenyl-amino)-4-oxo-1,3,8-triaza-spiro[4.5]dec-1-ene-8-sulfonyl]-ethyl}-benzamide;

(1398) 4-{2-[2-(benzyl-methyl-amino)-4-oxo-1,3,8-triaza-spiro[4.5]dec-1-ene-8-sulfonyl]-ethyl}-3,N,N-trimethyl-benzamide;

(1399) 4-{2-[2-(cyclohexylmethyl-amino)-4-oxo-1,3,8-triaza-spiro[4.5]dec-1-ene-8-sulfonyl]-ethyl}-3,N,N-trimethyl-benzamide;

(1400) 3,N,N-trimethyl-4-(2-{2-[methyl-(4-trifluoromethyl-phenyl)-amino]-4-oxo-1,3,8-triaza-spiro[4.5]dec-1-ene-8-sulfonyl}-ethyl)-benzamide;

(1401) N-(3-methyl-4-{2-[4-oxo-2-(4-trifluoromethyl-phenylamino)-1,3,8-triaza-spiro[4.5]dec-1-ene-8-sulfonyl]-ethyl}-phenyl)-acetamide;

(1402) N-(3-methyl-4-{2-[4-oxo-2-(3-trifluoromethyl-phenylamino)-1,3,8-triaza-spiro[4.5]dec-1-ene-8-sulfonyl]-ethyl}-phenyl)-acetamide;

(1403) 4-{2-[2-(4-butyl-piperidin-1-yl)-4-oxo-1,3,8-triaza-spiro[4.5]dec-1-ene-8-sulfonyl]-ethyl}-3,N,N-trimethyl-benzamide;

(1404) 4-{2-[2-(4-butyl-cyclohexylamino)-4-oxo-1,3,8-triaza-spiro[4.5]dec-1-ene-8-sulfonyl]-ethyl}-3,N,N-trimethyl-benzamide;

(1405) 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide;

(1419) N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide;

(1443) dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide; or (1446) hept-6-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide, or a pharmacologically acceptable salt thereof.

Such compounds represented by the above formula (1) or pharmacologically acceptable salts thereof according to the present invention are useful as compounds having a PTH-like effect, preferably PTH1 receptor agonists, and are useful for the prevention and/or treatment of osteoporosis, fracture, osteomalacia, arthritis, thrombocytopenia, hypoparathyroidism, hyperphosphatemia, tumoral calcinosis or the like, or stem cell mobilization.

The compounds or salts thereof according to the present invention can be formulated by conventional methods into tablets, powders, fine granules, granules, coated tablets, capsules, syrups, troches, inhalations, suppositories, injections, ointments, ophthalmic ointments, ophthalmic preparations, nasal preparations, ear preparations, cataplasms, lotions and the like. Commonly used excipients, binders, lubricants, colorants, correctives, and as necessary, stabilizers, emulsifiers, absorption promoters, surfactants, pH adjusters, preservatives, antioxidants and the like can be used for formulation, and they are blended with ingredients commonly used as raw materials of pharmaceutical preparations and formulated by conventional methods.

For example, oral preparations are manufactured by adding, to the compound or a pharmacologically acceptable salt thereof according to the present invention, an excipient, and as necessary, a binder, a disintegrant, a lubricant, a colorant, a corrective and the like and then formulating them into powder, fine granules, granules, tablets, coated tablets, capsules and the like by a conventional method.

Examples of these ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water.

Examples of the excipients include lactose, corn starch, white soft sugar, glucose, mannitol, sorbitol, microcrystalline cellulose and silicon dioxide.

Examples of the binders include polyvinyl alcohol, polyvinyl ether, methylcellulose, ethylcellulose, acacia, tragacanth, gelatin, shellac, hydroxypropylmethylcellulose, hydroxypropylcellulose, polyvinylpyrrolidone, a polypropylene glycol-polyoxyethylene block polymer and meglumine.

Examples of the disintegrants include starch, agar, gelatin powder, microcrystalline cellulose, calcium carbonate, sodium bicarbonate, calcium citrate, dextrin, pectin and carboxymethylcellulose calcium.

Examples of the lubricants include magnesium stearate, talc, polyethylene glycol, silica and hydrogenated vegetable oil.

Colorants used are those approved as additives to pharmaceuticals. Correctives used are cocoa powder, peppermint camphor, empasm, mentha oil, borneol, powdered cinnamon bark and the like.

Obviously, these tablets and granules may be sugar-coated or otherwise coated appropriately as necessary. Liquid preparations such as syrups and injectable preparations are manufactured by adding a pH adjuster, a solubilizer, a tonicity adjusting agent and the like, and as necessary, a solubilizing agent, a stabilizer and the like to the compound or a pharmacologically acceptable salt thereof according to the present invention and formulating them by a conventional method.

The method of manufacturing external preparations is not limited and they can be manufactured by conventional methods. Specifically, various raw materials commonly used for pharmaceuticals, quasi drugs, cosmetics and the like can be used as base materials for formulation. Specific examples of the base materials used include raw materials such as animal and vegetable oils, mineral oils, ester oils, waxes, higher alcohols, fatty acids, silicone oil, surfactants, phospholipids, alcohols, polyhydric alcohols, water-soluble polymers, clay minerals and purified water. Further, pH adjusters, antioxidants, chelators, preservatives and fungicides, colorants, flavors and the like may be added as necessary. The base materials for external preparations according to the present invention are not limited to these materials.

Ingredients such as ingredients having a differentiation-inducing effect, blood flow promoters, bactericides, anti-inflammatory agents, cell activators, vitamins, amino acids, humectants and keratolytic agents may also be blended as necessary. The aforementioned base materials are added in an amount corresponding to the concentration usually chosen for the manufacture of external preparations.

The mode of administration of the compounds or salts thereof, or hydrates of the compounds or salts according to the present invention is not particularly limited, and they may be orally or parenterally administered by methods commonly used. For example, they can be formulated into preparations such as tablets, powders, granules, capsules, syrups, troches, inhalations, suppositories, injections, ointments, ophthalmic ointments, ophthalmic preparations, nasal preparations, ear preparations, cataplasms and lotions and administered.

The dosage of the medicine according to the present invention can be appropriately selected depending on the severity of the symptom, the age, the sex, the body weight, the mode of administration, the type of the salt, the specific type of the disease, and the like.

Although the dosage significantly varies according to the type of the disease and the severity of the symptom of the patient, the age of the patient, the sex difference and the difference in sensitivity to drugs between the patients, and the like, the dosage is usually about 0.03 to 1000 mg, preferably 0.1 to 500 mg and more preferably 0.1 to 100 mg per day for adults and is administered divided into one to several doses a day. For injections, the dosage is usually about 1 μg/kg to 3000 μg/kg, preferably about 3 μg/kg to 1000 μg/kg.

In the manufacture of the compounds of the present invention represented by the above formula (1), raw material compounds and various reagents may form salts, hydrates or solvates, all vary according to the starting material, the solvent used, and the like, and are not particularly limited insofar as they do not inhibit the reaction.

The solvent used also varies according to the starting material, the reagent and the like, and is not particularly limited insofar as it does not inhibit the reaction and dissolves the starting material to a certain extent, obviously.

Various isomers (e.g., geometric isomers, optical isomers based on asymmetric carbons, rotamers, stereoisomers and tautomers) can be purified and isolated using common separation means, e.g., recrystallization, diastereomeric salt methods, enzymatic resolution methods and various chromatography methods (e.g., thin-layer chromatography, column chromatography, high performance liquid chromatography and gas chromatography).

The compounds according to the present invention obtained as free forms can be converted to salts that may be formed by the compounds or to hydrates of the compounds according to conventional methods. The compounds according to the present invention obtained as salts or hydrates of the compounds can also be converted to free forms of the compounds according to conventional methods.

The compounds according to the present invention can be isolated and purified by applying common chemical operations such as extraction, concentration, evaporation, crystallization, filtration, recrystallization and various chromatography methods.

All prior art documents cited herein are hereby incorporated by reference.

General manufacturing methods for the compounds of the present invention and examples will be shown below.

General Synthesis Methods

The compounds of the present invention can be synthesized by various methods, some of which will be described with reference to the following schemes. The schemes are illustrative and the present invention is not limited only by the chemical reactions and conditions explicitly indicated. Although some substituents are excluded in the following schemes for the sake of clarity, such exclusion is not intended to limit the disclosure of the schemes. Representative compounds of the present invention can be synthesized using appropriate intermediates, known compounds, and reagents. $R_1$, $R_2$, $R_{33}$, $R_{34}$, W, X, Y, m and n in the formulas in the following general synthesis methods are as defined for $R_1$, $R_2$, $R_{33}$, $R_{34}$, W, X, Y, m and n in the compounds represented by the above general formula (1) (compounds represented by the formula I in the following general synthesis methods).

The compounds of the general formula (1) according to the present invention can be synthesized by the manufacturing methods shown below.

Scheme 1 (Method A)

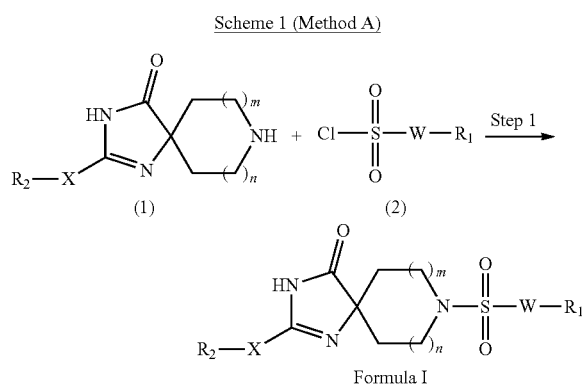

Scheme 1 (Method A) is a method of reacting a spiro-amine derivative (1) with various sulfonyl chlorides (2) in an appropriate solvent such as dichloromethane or tetrahydrofuran in the presence of an appropriate base such as triethylamine or pyridine. The reaction temperature is 0° C. to room temperature, for example, and the reaction time is 0.5 to 24 hours. The resulting sulfonamide derivative (formula I) is isolated by a common technique and, if necessary, may be purified by crystallization or chromatography.

The spiro-amine derivative (1) shown in Scheme 1 can be synthesized from an acylamino-nitrile derivative (3) or acylamino-amide derivative (4). Scheme 2 shows a method of synthesizing the spiro-amine derivative (1).

in the presence of an aqueous sodium hydroxide solution and aqueous hydrogen peroxide solution. The reaction temperature is reflux temperature, for example, and the reaction time is 1 to 24 hours. The resulting cyclized derivative (5) is isolated by a common technique and, if necessary, may be purified by crystallization or chromatography.

The cyclized derivative (5) can also be synthesized by two-step reaction (Step 3, Step 4). Step 3 is a method of converting the nitrile group to an amido group under basic hydrolysis conditions in the presence of hydrogen peroxide. (This reaction can be performed with reference to Chemistry—A European Journal (2002), 8(2), 439-450, for example.) Step 4 is a method of cyclizing an acylamino-amide derivative (4) in an appropriate solvent such as ethanol, tert-butanol or dimethyl sulfoxide in the presence of an appropriate base such as an aqueous sodium hydroxide solution or potassium t-butoxide. The reaction temperature is room temperature to reflux temperature, for example, and the reaction time is 1 to 24 hours. The resulting cyclized derivative (5) is isolated by a common technique and, if necessary, may be purified by crystallization or chromatography.

Step 5 is a reaction of deprotecting the t-butoxycarbonyl group with an appropriate acid such as trifluoroacetic acid or hydrochloric acid in an appropriate solvent such as dichloromethane, dioxane or methanol. (This reaction can be performed with reference to Protective Groups in Organic Synthesis, Wiley-Interscience, for example.)

The acylamino-nitrile derivative (3) or acylamino-amide derivative (4) shown in Scheme 2 can be synthesized from an amino-nitrile derivative (8a) or amino-amide derivative

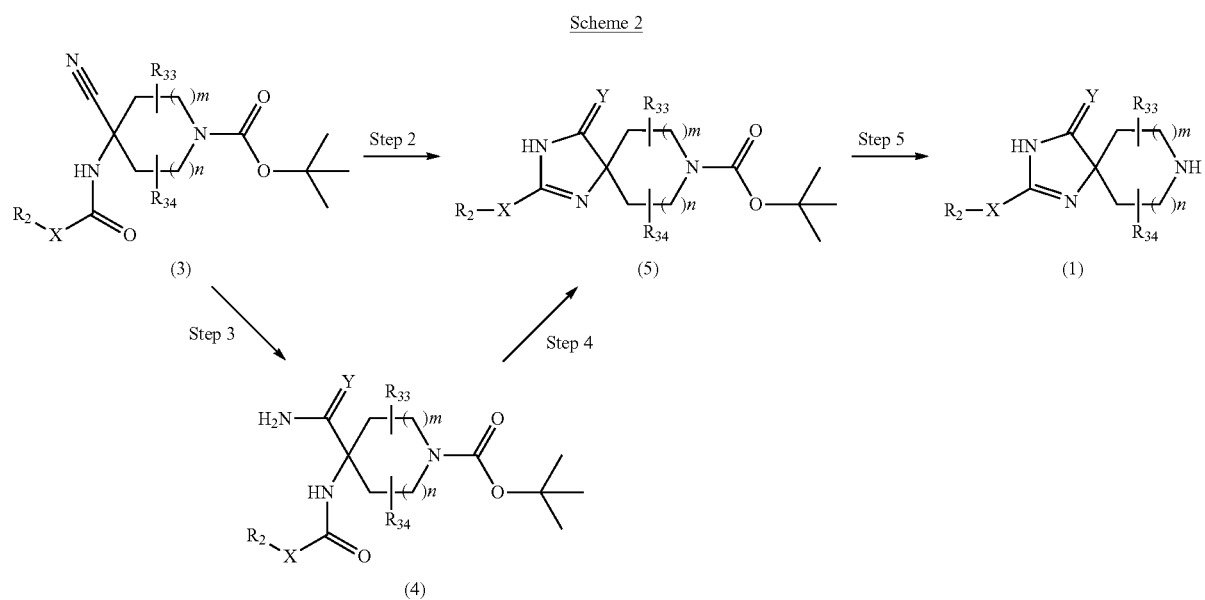

(In the scheme, Y = O.)

Step 2 is a method of cyclizing an acylamino-nitrile derivative (3) in an appropriate solvent such as an aqueous ethanol solution or an aqueous dimethyl sulfoxide solution (8b). Scheme 3 shows a method of synthesizing the acylamino-nitrile derivative (3) or acylamino-amide derivative (4).

Scheme 3

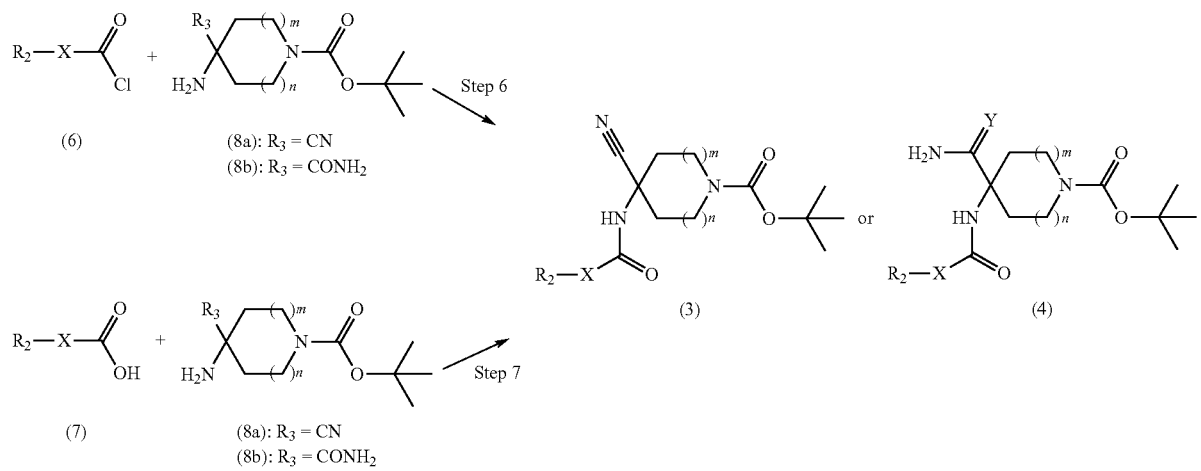

(In the scheme, Y = O.)

Step 6 is a method of reacting an acid chloride derivative (6) with an amino-nitrile derivative (8a) or amino-amide derivative (8b), respectively, in an appropriate solvent such as dichloromethane or tetrahydrofuran in the presence of an appropriate base such as triethylamine or pyridine. The reaction temperature is 0° C. to room temperature, for example, and the reaction time is 0.5 to 24 hours. The resulting acylamino-nitrile derivative (3) or acylamino-amide derivative (4) is isolated by a common technique and, if necessary, may be purified by crystallization or chromatography. The acid chloride derivative (6) used for the reaction can be purchased or can be synthesized from a carboxylic acid derivative (7) by the method described in March, Advanced Organic Chemistry, 5$^{th}$ Edition, John Wiley and Sons, New York, P 523-P 524, for example.

Step 7 is a method of reacting a carboxylic acid derivative (7) with amino-nitrile (8a) or amino-amide (8b). Examples of the coupling reagent include N,N'-dicyclohexylcarbodiimide (DCC), 1-ethyl-3-(3-dimethylaminopropyl)carbodiimide hydrochloride (EDC), 0-(7-azabenzotriazol-1-yl)-1,1,3,3-tetramethyluronium hexafluorophosphate (HATU) and 4-(4,6-dimethoxy-1,3,5-triazin-2-yl)-4-methylmorpholinium chloride n-hydrate (DMT-MM). Examples of the base include triethylamine or N,N-diisopropylethylamine. If necessary, 4-(dimethylamino)pyridine (DMAP) may be used as a catalyst. Examples of the appropriate solvent include dichloromethane or N,N-dimethylformamide. Examples of the appropriate solvent used in the case of DMT-MM include methanol, ethanol and acetonitrile. The reaction temperature is 0° C. to room temperature, for example, and the reaction time is 0.5 to 24 hours. The resulting acylamino-nitrile derivative (3) or acylamino-amide derivative (4) is isolated by a common technique and, if necessary, may be purified by crystallization or chromatography.

The sulfonyl chloride derivative (2) shown in Scheme 1 can be purchased or can be synthesized as shown in Scheme 4a and Scheme 4b.

Scheme 4a

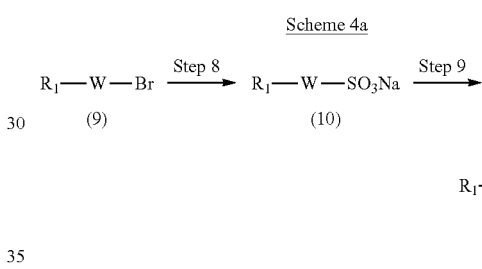

Scheme 4a is a method of synthesizing a sulfonyl chloride derivative (2) from a bromide derivative (9) through a sodium salt derivative of sulfonic acid (10). This method of providing a sulfonyl chloride can be performed with reference to J. Org. Chem. 1985, 50(12), 2066-2073 or J. Org. Chem. 1984, 49(26), 5124-5131, for example.

Scheme 4b

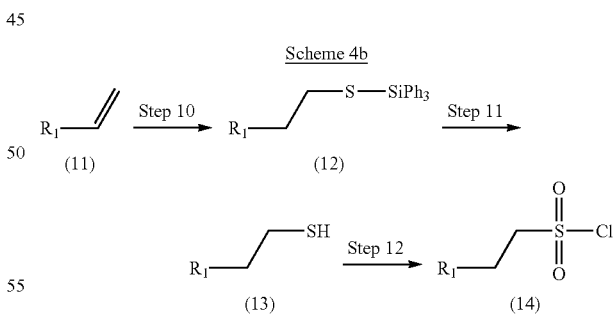

Scheme 4b is a method of synthesizing a sulfonyl chloride derivative, in particular, an ethylsulfonyl chloride derivative (14) from a styrene derivative (11). This reaction can be performed with reference to Tetrahedron Lett., Vol 35, 1837-1840 (1994) or Chemistry Lett., 1483-1486 (1992), for example.

The spiro-amine structure of the formula I can be synthesized by cyclization of an amide derivative such as (15) or (16) of Scheme 5 (Method B).

Scheme 5 (Method B)

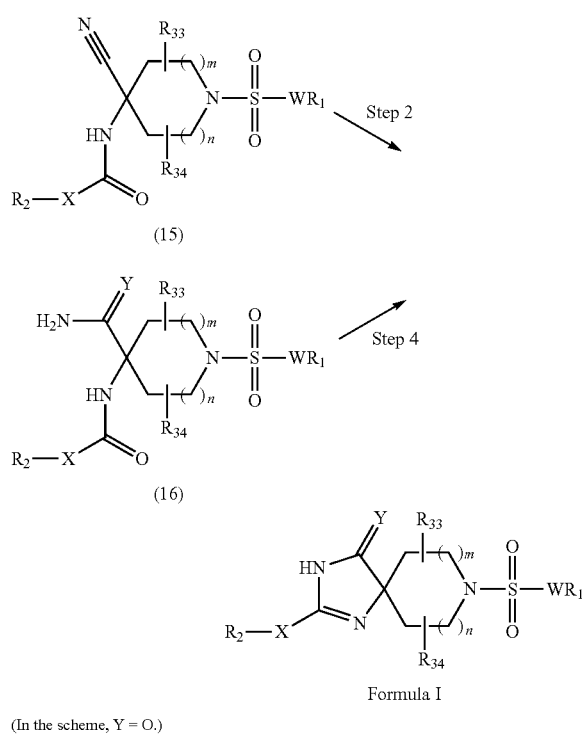

(In the scheme, Y = O.)

The compound I is synthesized by cyclizing an amide derivative represented by (15) or (16) using the above-described method of Step 2 or Step 4.

The amide derivative ((15) or (16)) shown in Scheme 5 can be derived from a keto-amine derivative (17). Scheme 6 shows a method of synthesizing the amide derivative ((15) or (16)).

Scheme 6

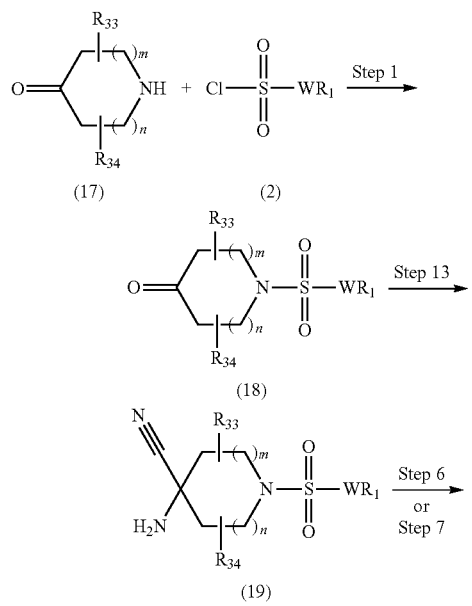

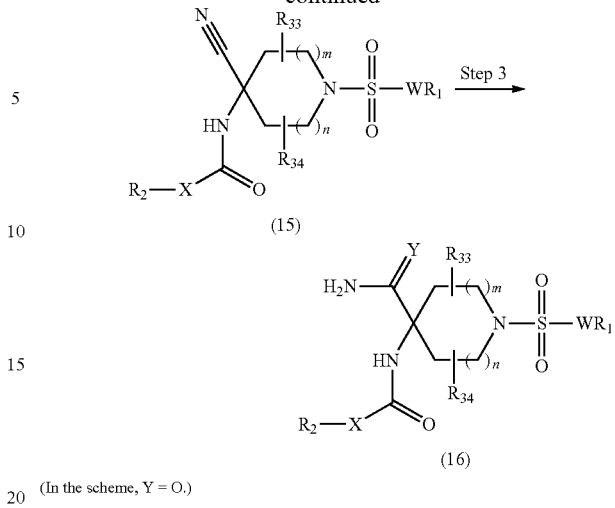

(In the scheme, Y = O.)

Step 1 is a method of reacting a keto-amine derivative (17) with a sulfonyl chloride derivative (2). Step 13 is a Strecker synthesis of converting a ketone derivative (18) to an amino-nitrile derivative (19). Specifically, this is a method of reacting a ketone derivative (18) with sodium cyanide or potassium cyanide and ammonium chloride or ammonium acetate in an appropriate solvent such as methanol, ethanol or tetrahydrofuran in the presence/absence of water. The reaction temperature is room temperature to 80° C., for example, and the reaction time is 2 to 72 hours. The resulting amino-nitrile derivative (19) is isolated by a common technique and, if necessary, may be purified by crystallization or chromatography.

The cyano-amide derivative (15) can be synthesized by the same method as in Step 6 or Step 7 in Scheme 3. Step 3 is a method of synthesizing an amido-amide compound (16) by hydrolysis of the cyano-amide derivative (15).

The spiro-amine derivative of the formula I, in particular, the aryl-ethenylsulfonamide derivative of the formula II (o=0) and the aryl-propenylsulfonamide derivative of the formula II (o=1), can be synthesized by a Heck reaction of an olefinated sulfonamide derivative (20) with an aryl halide (21) in Scheme 7.

Scheme 7 (Method C)

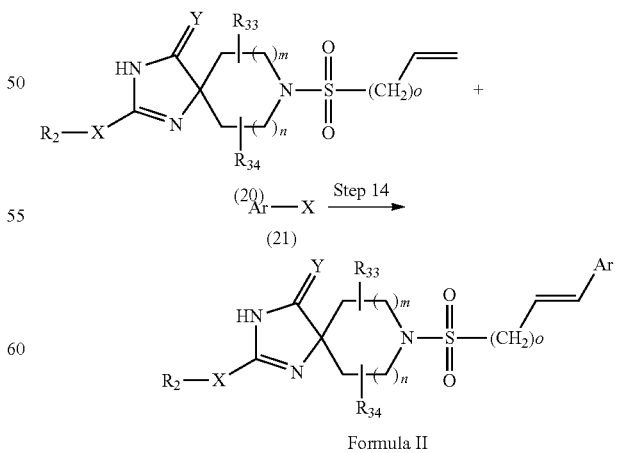

(In the scheme, Y = O.)

Step 14 is a method of synthesizing an arylethenylsulfonamide derivative (formula II) by coupling an olefinated sulfonamide derivative (20) with an aryl halide derivative (21) in an appropriate solvent such as N,N-dimethylacetamide (DMA), N,N-dimethylformamide (DMF) or 1,4-dioxane in the presence of a palladium catalyst such as palladium(II) acetate (Pd(OAc)$_2$) or tetrakis(triphenylphosphine)palladium(0) (Pd(PPh$_3$)$_4$), in the presence or absence of a phosphine ligand such as triphenylphosphine (PPh$_2$) or tri-o-tolylphosphine ((o-tol)$_3$P) and in the presence of an appropriate base such as triethylamine, respectively, in an N$_2$ atmosphere. The reaction temperature is 90° C. to reflux temperature. This reaction can be performed under microwave irradiation. The resulting arylethenylsulfonamide derivative (formula II) is isolated by a common technique and, if necessary, may be purified by crystallization or chromatography.

The spiro-amine derivative (formula I), in particular, the ethenylsulfonamide derivative (formula III), can also be synthesized by coupling a Horner-Wadsworth-Emmons reagent with an aldehyde derivative (24) as shown in Scheme 8.

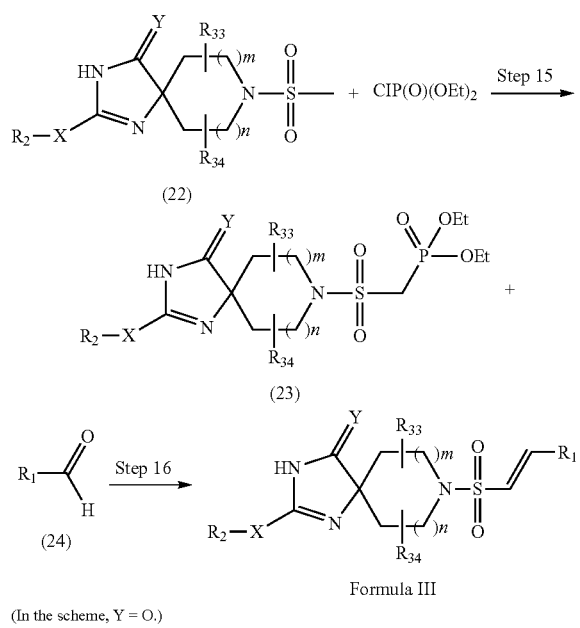

Scheme 8 (Method D)

(In the scheme, Y = O.)

Step 15 is a method of synthesizing a Horner-Wadsworth-Emmons reagent (23) by coupling a methanesulfonamide derivative (22) with diethyl chlorophosphate in an appropriate solvent such as tetrahydrofuran or diethyl ether in the presence of a base such as lithium hexamethyldisilazide (LHMDS) or lithium diisopropylamide (LDA). The reaction is performed at −78° C. to room temperature for 1 to 24 hours in an N$_2$ atmosphere. The resulting Horner-Wadsworth-Emmons reagent (23) is isolated by a common technique and, if necessary, may be purified by crystallization or chromatography. This reaction can be performed with reference to Tetrahedron 2001, 57(37), 7899-7907, for example.

Step 16 is a method of synthesizing an ethenylsulfonamide derivative (formula III) by reacting the Horner-Wadsworth-Emmons reagent (23) with an aldehyde derivative (24) under Horner-Wadsworth-Emmons reaction conditions. This reaction can be performed with reference to Synlett 2005, 5, 834-838; Tetrahedron 2001, 57(37), 7899-7907, for example.

The spiro-amine derivative (formula I), in particular, the aryl-alkylsulfonamide derivative (formula IV), can be synthesized by reduction of an olefin of the formula II in Scheme 9.

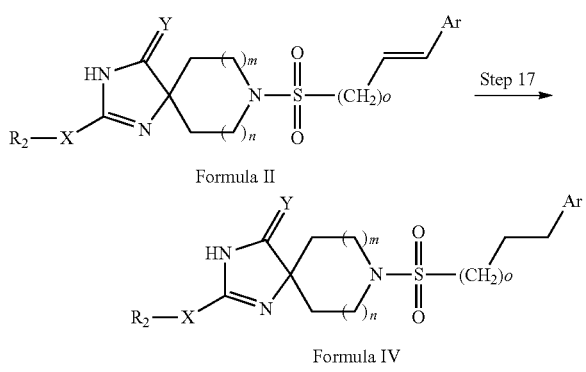

Scheme 9 (Method E)

(In the scheme, Y = O.)

Step 17 is a method of hydrogenating an olefin of the formula II in an inert solvent such as methanol, ethanol, dimethylformamide or dimethylacetamide in the presence of a catalyst such as palladium carbon or palladium hydroxide carbon, respectively, under an H$_2$ atmosphere. The reaction temperature is room temperature to 80° C., and the reaction may be performed under pressure. The resulting aryl-alkylsulfonamide derivative (formula IV) is isolated by a common technique and, if necessary, may be purified by crystallization or chromatography.

The cyclized derivative (5) amide used in the above reaction can be converted to a thioamide (Step 18) and used for the reaction of Step 5 or Step 1. This reaction can be performed with reference to March, Advanced Organic Chemistry, 5$^{th}$ Edition, for example.

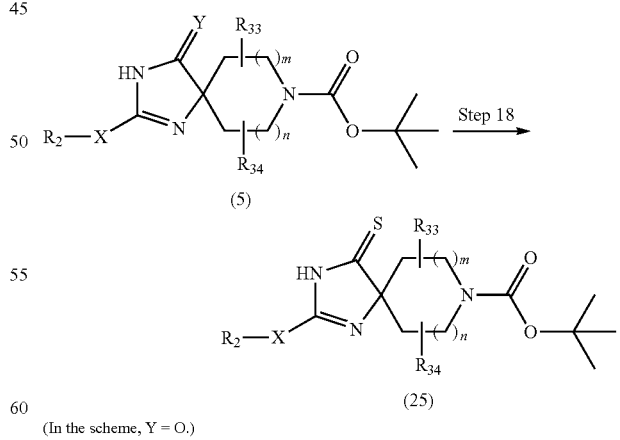

Scheme 10

(In the scheme, Y = O.)

The ketone derivative (18) shown in Scheme 6 can be derived from a keto-amine derivative (17) through an ethenesulfonamide derivative (26). It can also be derived from a ketal-amine derivative (27) through a ketal-ethenesulfonamide derivative (28).

Scheme 11

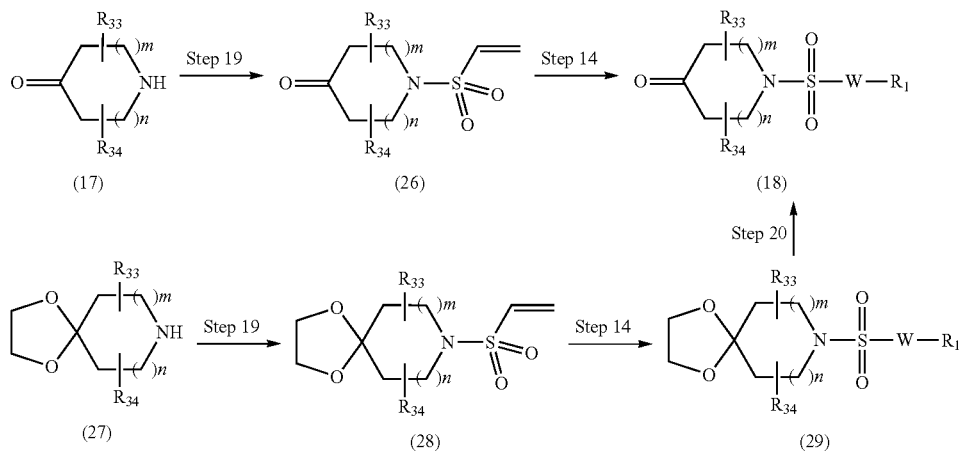

Step 19 is a method of reacting a keto-amine derivative (17) or ketal-amine derivative (27) with chloroethanesulfonyl chloride in an appropriate solvent such as dichloromethane in the presence of an appropriate base such as triethylamine. The reaction temperature is 0° C. to 40° C., for example, and the reaction time is 0.1 to 1 hour. The resulting ethenesulfonamide derivative (26) or ketal-ethenesulfonamide derivative (28) is isolated by a common technique and, if necessary, may be purified by crystallization or chromatography.

The ketone derivative (18) can be synthesized from the ethenesulfonamide derivative (26) by the same method as in Step 14 in Scheme 7.

The ketone derivative (18) can also be synthesized by converting the ketal-ethenesulfonamide derivative (28) to a ketal-sulfonamide derivative (29) by the same method as in Step 14 in Scheme 7 and then deprotecting the ketal by the method of Step 20. Step 20 is a method of reacting the ketal-sulfonamide derivative (29) with an acid such as trifluoroacetic acid or hydrochloric acid in an appropriate solvent such as aqueous acetone or aqueous ethanol. The reaction temperature is 55° C. to 80° C. (boiling point of the solvent), for example, and the reaction time is 1 to 24 hours. The resulting ketone derivative (18) is isolated by a common technique and, if necessary, may be purified by crystallization or chromatography.

The olefinated sulfonamide derivative (20) shown in Scheme 7 can be derived from a spiro-amine derivative (1).

Scheme 12

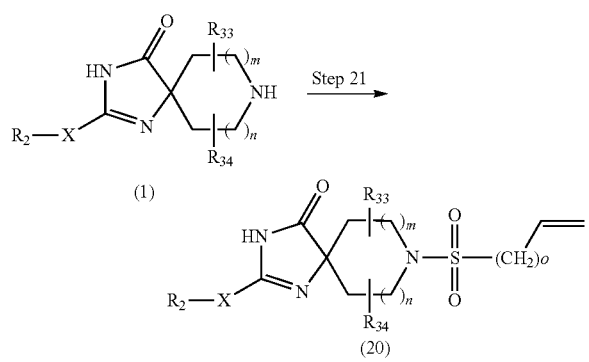

Step 21 is a method of reacting a spiro-amine derivative (1) with a sulfonyl chloride reagent (e.g., chloroethanesulfonyl chloride or 2-propene-1-sulfonyl chloride) in an appropriate solvent such as dichloromethane in the presence of an appropriate base such as triethylamine. The reaction temperature is 0° C. to 40° C., for example, and the reaction time is 0.1 to 1 hour. The resulting olefinated sulfonamide derivative (20) is isolated by a common technique and, if necessary, may be purified by crystallization or chromatography.

The methanesulfonamide derivative (22) shown in Scheme 8 can be derived from a spiro-amine derivative (1).

Scheme 13

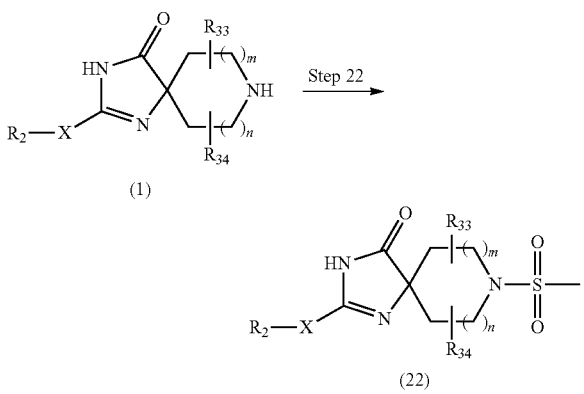

Step 22 is a method of reacting a spiro-amine derivative (1) with methanesulfonyl chloride in an appropriate solvent such as dichloromethane in the presence of an appropriate base such as triethylamine. The reaction temperature is 0° C. to room temperature, for example, and the reaction time is 0.1 to 1 hour. The methanesulfonamide derivative (22) is isolated by a common technique and, if necessary, may be purified by crystallization or chromatography.

The compound of the general formula (1) wherein Y is a sulfur atom (formula VI) can be synthesized from a thioamide intermediate (25) in Scheme 10 by the reactions of Step 5-Step 1 as in the case of the compound wherein Y is an oxygen atom, for example. It can also be synthesized from an amide derivative wherein Y is an oxygen atom (formula V) by Step 18.

Scheme 14

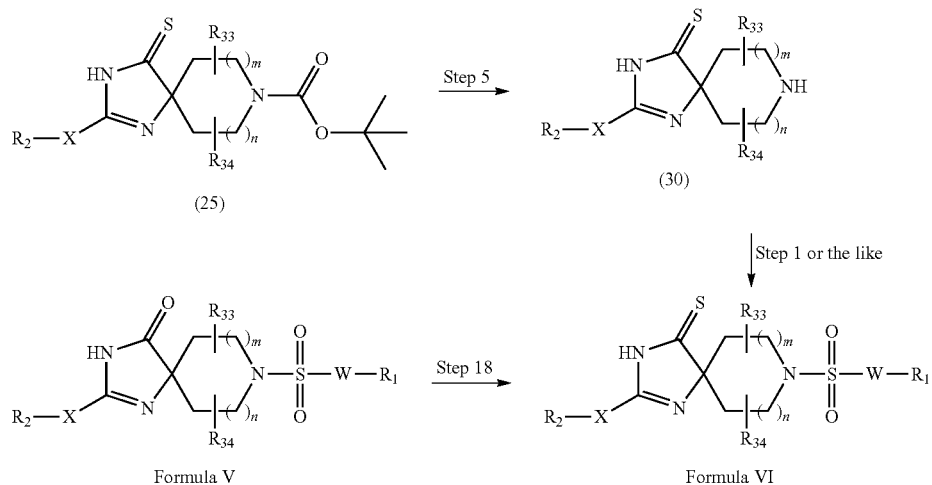

Step 18 is a method of reacting an amide derivative (formula V) with a Lawesson's reagent in an appropriate solvent such as toluene. The reaction temperature is room temperature to the boiling point of the solvent, for example, and the reaction time is several hours to 24 hours. The thioamide derivative (formula VI) is isolated by a common technique and, if necessary, may be purified by crystallization or chromatography. This conversion reaction of carbonyl to thiocarbonyl can be performed with reference to March, Advanced Organic Chemistry, 5$^{th}$ Edition, for example.

The compound of the general formula (1) wherein Y is a nitrogen atom (formula VII, formula VIII) can be synthesized by converting the thioamido group of a thioamide intermediate (25) to an amidino group (step 23) to provide an amidino intermediate (31, 32) and then subjecting the intermediate to the reactions of Step 5 and subsequent Step 1 as in the case of the compound of the general formula (1) wherein Y is an oxygen atom, for example.

Scheme 15

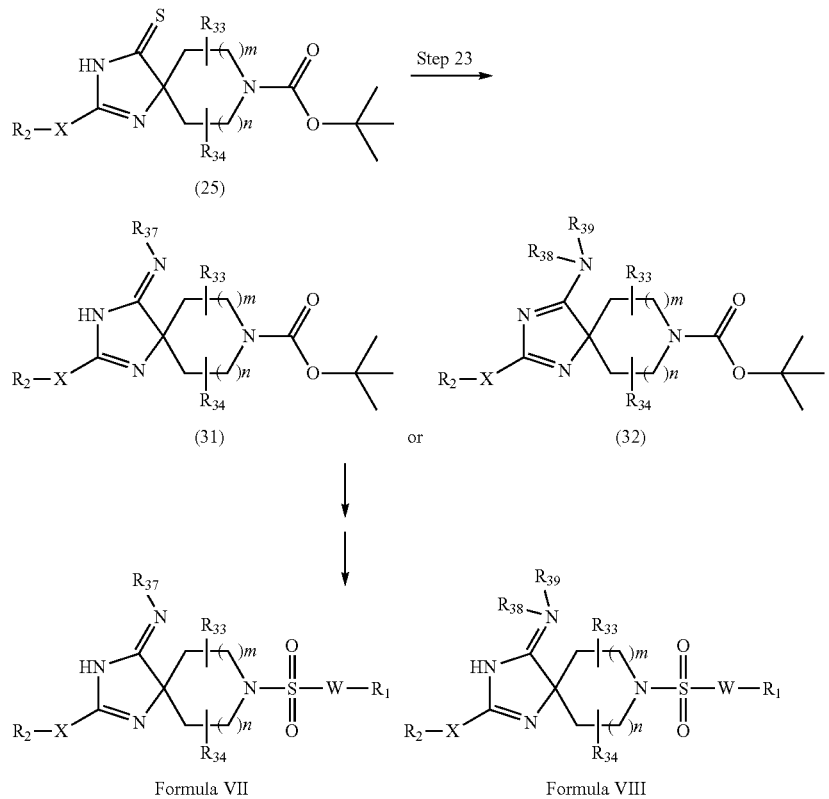

Step 23 is a method of reacting a thioamide intermediate (25) with a primary amine or secondary amine in an appropriate solvent such as methanol. The reaction temperature is room temperature to the boiling point of the solvent, for example, and the reaction time is several hours to 24 hours. The amidino intermediate (31, 32) is isolated by a common technique and, if necessary, may be purified by crystallization or chromatography.

The derivative of the general formula (1) wherein X is a single bond and $R_2$ is optionally substituted aryl or heteroaryl (formula IX) can also be synthesized from a thiohydantoin derivative (33).

Scheme 16

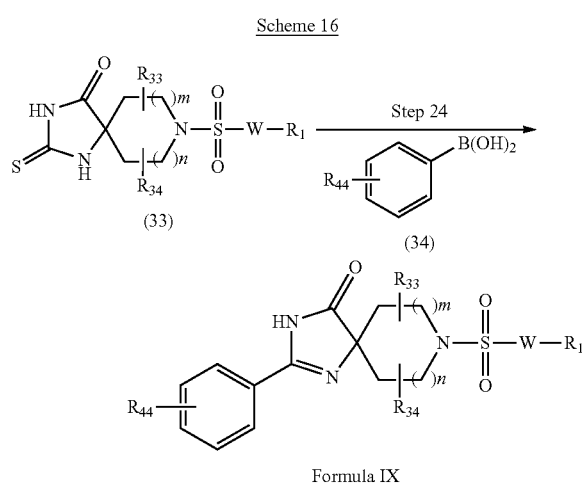

Formula IX

Step 24 is a method of reacting a thiohydantoin derivative (33) with an optionally substituted arylboronic acid (34) in an appropriate solvent such as N-methylpyrolidone in the presence of a copper catalyst such as CuTC or a palladium catalyst such as tetrakis(triphenylphosphine)palladium(0). The reaction temperature is room temperature to the boiling point of the solvent, for example, and the reaction time is 0.5 to 24 hours. The substituted phenyl derivative (formula IX) is isolated by a common technique and, if necessary, may be purified by crystallization or chromatography.

The thiohydantoin derivative (33) can be synthesized from an amino-nitrile derivative (19) through Step 3 and Step 25.

Scheme 17

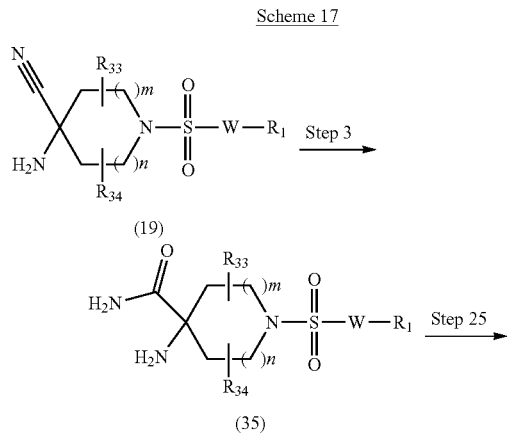

Step 3 is a method of synthesizing an amino-amide derivative (35) by hydrolyzing an amino-nitrile derivative (19). Step 25 is a reaction of converting the amino-amide derivative (35) to a thiohydantoin derivative (33). Step 25 is a method of reacting the amino-amide derivative (35) with a thiocarbonylating reagent such as di(2-pyridyl)thionocarbonate in an appropriate solvent such as tetrahydrofuran. The reaction temperature is 0° C. to room temperature, for example, and the reaction time is 0.5 hour to several hours. The thiohydantoin derivative (33) is isolated by a common technique and, if necessary, may be purified by crystallization or chromatography.

The alkynyl derivative of the general formula (1) wherein W is acetylene and $R_1$ is optionally substituted aryl or heteroaryl (formula XI) can be synthesized through an acetophenone derivative (formula X).

Scheme 18

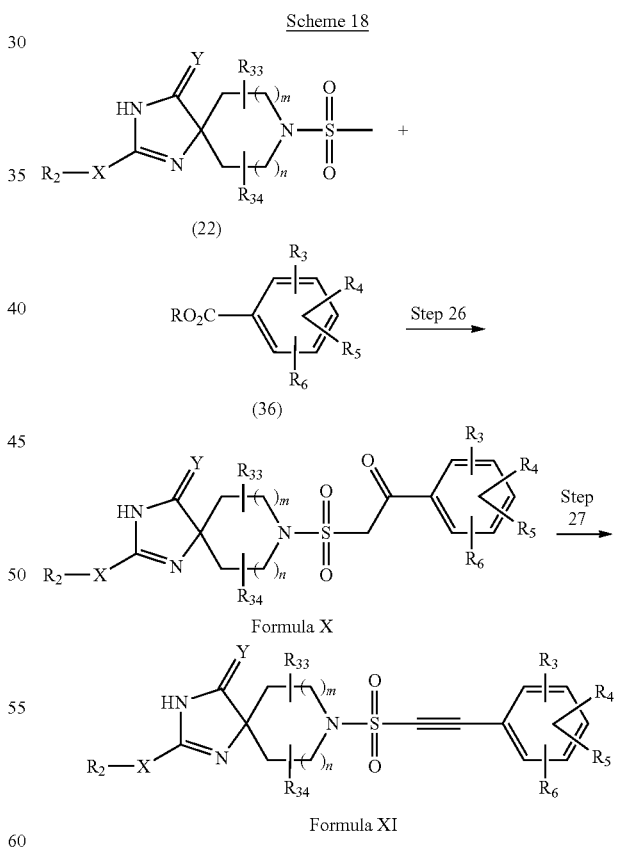

Formula XI

Step 26 is a method of condensation with an aryl ester (36) in an appropriate solvent such as tetrahydrofuran or diethyl ether in the presence of a base such as lithium hexamethyldisilazide (LHMDS) or lithium diisopropylamide (LDA) preferably with the addition of DMPU. The reaction is performed at −78° C. to room temperature for 1 to 24 hours in an N$_2$ atmosphere. The resulting acetophenone derivative (formula X) is isolated by a common technique and, if necessary, may be purified by crystallization or chromatography.

Step 27 is a method of synthesizing an alkynyl derivative (formula XI) by subjecting the acetophenone derivative (formula X) to dehydration reaction. Specifically, 1 to 10 equivalents of a dehydrating agent, preferably 2-chloro-1-methyl-pyridinium iodide, and an appropriate base, preferably triethylamine, are added and reacted in an appropriate solvent such as dichloromethane at 0° C. to a temperature under heating. The resulting alkynyl derivative (formula XI) is isolated by a common technique and, if necessary, may be purified by crystallization or chromatography.

The substituted alkylene derivative of the general formula (1) wherein W is branched alkylene or haloalkylene (formula XII) can be synthesized as follows, for example.

The substituted alkylene derivative (formula XII) can be obtained by nucleophilic substitution reaction with a ketal-sulfonamide derivative (37) as a raw material to introduce an alkyl group or a halogen atom onto the carbon adjacent to the sulfonyl group (Step 28), ketal deprotection reaction (Step 20) and the steps shown in Schemes 5 and 6.

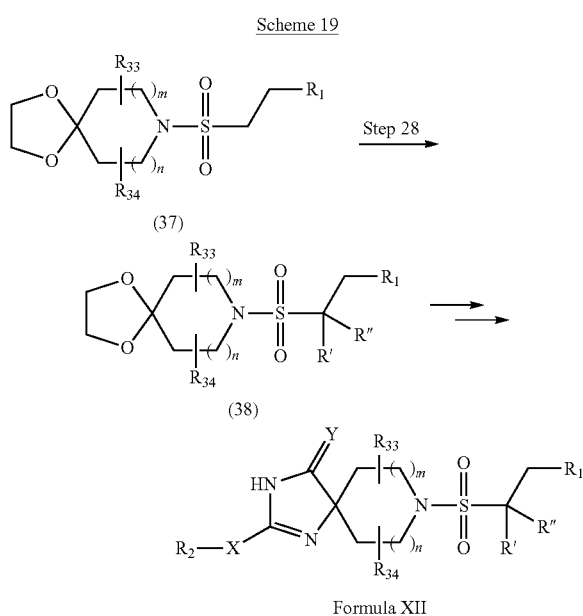

Step 28 is a reaction of a ketal-alkylenesulfonamide derivative (37) with an electrophilic reagent such as an alkyl halide or NFSI (N-fluorodibenzenesulfonimide) in an appropriate solvent such as tetrahydrofuran in the presence of a base such as n-butyllithium or lithium diisopropylamide. The reaction temperature is −78° C. to room temperature, for example, and the reaction time is 0.5 hour to several hours. The ketal-sulfonamide derivative (38) is isolated by a common technique and, if necessary, may be purified by crystallization or chromatography. In this reaction, one or two substituents are introduced onto the carbon atom adjacent to the sulfonyl group, and the equivalents of the base are controlled according to need. In the introduction of two substituents, two substituents can be introduced all at once using an excess of a base; however, it is desirable to once obtain a compound having one substituent introduced thereinto by purification and then introduce the other substituent.

The guanidine derivative of the general formula (1) wherein X is a nitrogen atom (formula XIII) can be synthesized through a guanidine intermediate (41).

The guanidine intermediate (41) can be synthesized from a thiohydantoin derivative (39) through an isothiourea derivative (40). The guanidine derivative (formula XIII) can be synthesized from the guanidine intermediate (41) by the reactions of Step 5 and subsequent Step 1, for example.

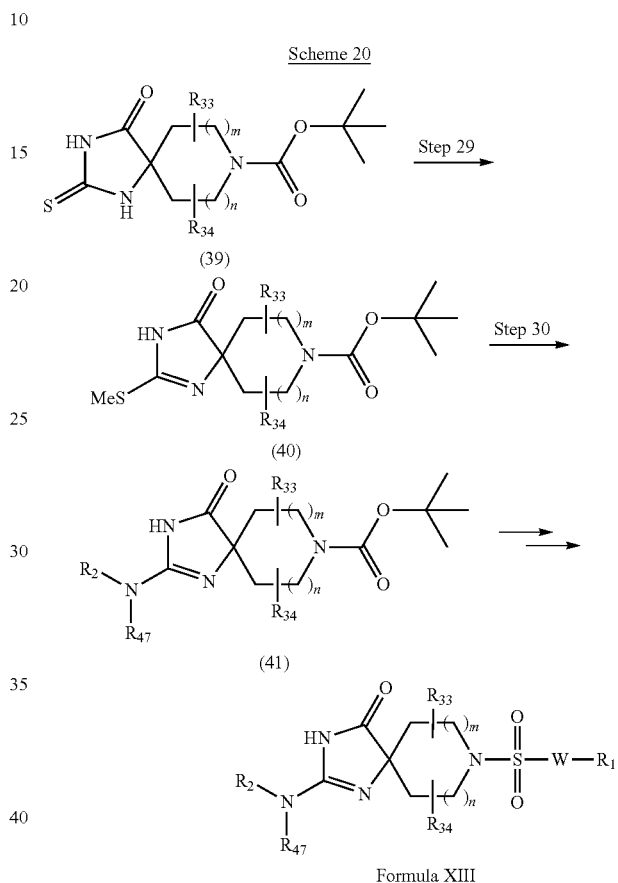

Step 29 is S-alkylation reaction of a thiohydantoin derivative (39). Specifically, this is a method of reacting a thiohydantoin derivative (39) with an alkyl halide reagent such as methyl iodide in an appropriate solvent such as methanol in the presence of a base such as sodium hydroxide. The reaction temperature is room temperature to the boiling point of the solvent, for example, and the reaction time is several hours to 24 hours. The isothiourea derivative (40) is isolated by a common technique and, if necessary, may be purified by crystallization or chromatography.

Step 30 is a reaction of converting isothiourea to guanidine. Specifically, this is a method of reacting the isothiourea derivative (40) with a substituted primary amine or substituted secondary amine in an appropriate solvent such as dimethylacetamide in the presence of an acid catalyst such as acetic acid. The reaction temperature is room temperature to the boiling point of the solvent, for example, and the reaction time is 0.5 hour to several hours. The guanidine derivative (41) is isolated by a common technique and, if necessary, may be purified by crystallization or chromatography.

The derivative compound represented by the general formula (2), wherein Z includes alkenylene, can be synthesized from a diolefin derivative (formula XIV) by olefin metathesis reaction (Step 31).

Scheme 21

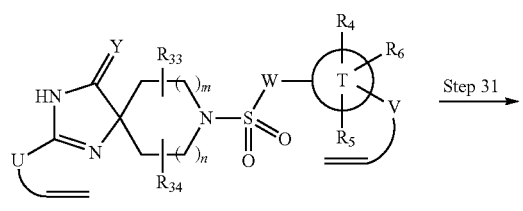

Formula XIV

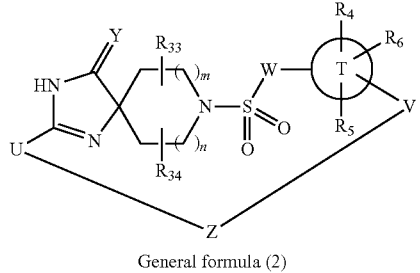

General formula (2)

Step 31 is a method of cyclizing a diolefin derivative (formula XIV) using a Grubbs reagent in an appropriate solvent such as dichloroethane. The reaction temperature is room temperature to the boiling point of the solvent, for example, and the reaction time is several hours to 24 hours. The macrocyclic derivative (formula (2)) is isolated by a common technique and, if necessary, may be purified by crystallization or chromatography.

The derivative compound represented by the general formula (2), wherein Z includes an amido group, can also be synthesized from a derivative having a primary amine or secondary amine at one end of the compound and a carboxylic acid at the other end (formula XV) by amidation reaction (Step 7).

Scheme 22

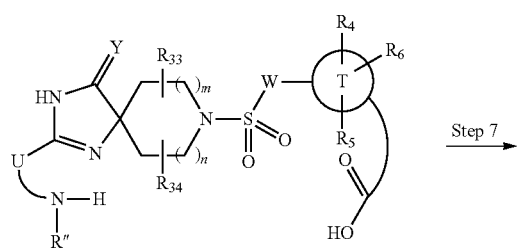

Formula XV

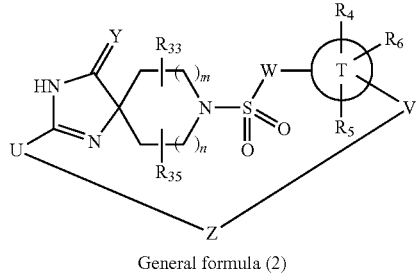

General formula (2)

The compound of the formula (2) is synthesized by cyclizing a derivative having an amine and a carboxylic acid at the ends (formula XV) using the above-described method of Step 7.

The derivative compound represented by the general formula (2), wherein Z includes triazole, can also be synthesized from a derivative (42) having an alkyne at one end of the compound and an azide at the other end using click chemistry (Step 32).

Scheme 23

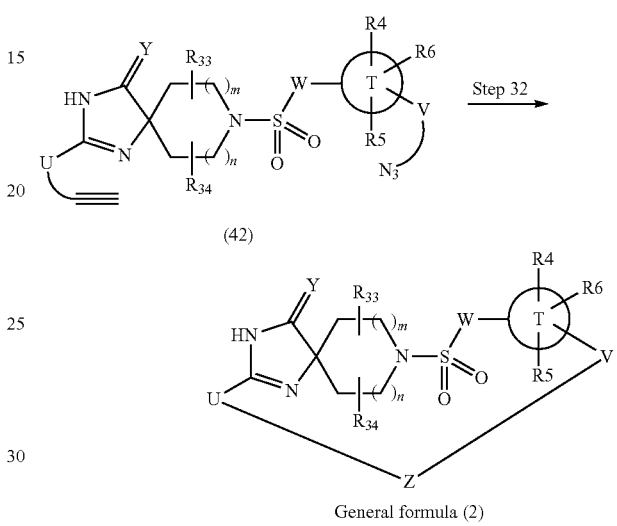

Step 32 is a method of reacting an azide and an alkyne in a derivative (42) having the alkyne and the azide at the ends in an appropriate solvent such as acetonitrile or tetrahydrofuran in the presence of a copper catalyst such as CuI with the addition of a base such as diisopropylethylamine or 2,6-lutidine and ascorbic acid if necessary. The reaction temperature is room temperature to the boiling point of the solvent, for example, and the reaction time is 1 to 24 hours. The derivative represented by the general formula (2) is isolated by a common technique and, if necessary, may be purified by crystallization or chromatography.

Derivatives can be synthesized from compounds obtained in Schemes 21, 22 and 23 by olefin hydrogenation reaction, olefin oxidation reaction, sulfur atom oxidation reaction, deprotection reaction of various protecting groups and the like as necessary.

Compounds containing functional groups such as alkenyl, amine, carboxylic acid, alkynyl and azido functional groups at the ends, the raw materials used in Schemes 21, 22 and 23 and the like for synthesizing the general formula (2), may be synthesized by previously introducing these functional groups into a carboxylic acid derivative (7), a bromide derivative (9), a styrene derivative (11), an aryl halide derivative (21), an aldehyde derivative (24), a substituted phenylboronic acid (34) and the like and subjecting them to the same method as the method of manufacturing the general formula (1), or may be synthesized by synthesizing intermediates of the general formula (1), in which functional groups such as carboxylic acid and phenol functional groups are introduced into $R_1$ or $R_2$, and introducing the functional groups from these intermediates into these derivatives by an appropriate reaction.

If the functional groups introduced at the ends are previously introduced into a carboxylic acid derivative (7), a bromide derivative (9), a styrene derivative (11), an aryl halide derivative (21), an aldehyde derivative (24), a substituted phenylboronic acid (34) and the like, then these functional groups are protected and deprotected by an appropriate method as necessary in a process of synthesis by the same method as the method of manufacturing the general formula (1).

If the functional groups introduced at the ends are introduced into these derivatives by synthesizing intermediates of the general formula (1), in which a functional group such as carboxylic acid and phenol functional groups is introduced into $R_1$ or $R_2$, and introducing the functional groups from these intermediates by an appropriate reaction, then amidation, Mitsunobu reaction or the like is preferred as such an appropriate reaction. The functional groups are protected and deprotected by an appropriate method as necessary. For example, to introduce alkenyl or azido into $R_1$, amidation reaction is performed between a compound of the general formula (1), in which carboxylic acid is introduced into $R_1$, and an alkylamine with alkenyl or azido bonded thereto. To introduce alkenyl or alkynyl into $R_2$, Mitsunobu reaction is performed between a compound of the general formula (1), in which phenol is introduced into $R_2$, and an alkylamine with alkenyl, alkynyl or a protected amine bonded thereto. Raw materials for synthesizing the general formula (2) can be synthesized by combining these reactions of introducing functional groups into $R_1$ or $R_2$.

The compound (7), compound (9), compound (11), compound (21), compound (24) or compound (34) used in the above reactions can be synthesized from known compounds using appropriate reagents and reactions. For example, an amino group, if present in $R_1$ or $R_2$, may be alkylated, acylated, carbamated, converted to ureas or sulfonamidated from known compounds. Carboxylic acids or esters, if present, may be amidated under general conditions. Sulfonyl chlorides, if present, may be condensed with amines and sulfonamidated. Alcohols, if present, may be etherified or carbamated. Aryl halides, if present, may be coupled with arylboric acids or aryl boronates under general Suzuki conditions. Olefins, if present, may be reduced or converted to diols. Thioether groups, if present, may be oxidized to sulfoxides or sulfones. If ketones or carbonyl groups are present, the carbon chain may be extended by Wittig reaction, Horner-Wadsworth-Emmons reaction, aldol reaction or the like. In the introduction of fluorine atoms, reagents containing fluorine atoms may be introduced by these reactions, or aldehydes, ketones or carboxylic acids may be reacted with diethylaminosulfur trifluoride, for example.

The techniques for introducing these groups can be performed with reference to March, Advanced Organic Chemistry, $5^{th}$ Edition, John Wiley and Sons, New York; J. Med. Chem., 2005, 48, 6066-6083; Organic Syntheses (1951), 31, 8-11; Bioorg. Med. Chem. Lett., 2003, 13, 837-840; Chem. Rev. 2002, 102, 1359; J. Organomet. Chem. 1999, 576, 147; Chem. Rev. 1995, 95, 2457, for example. These groups may be protected with protecting groups under general conditions, if necessary. This can be performed with reference to Protective Groups in Organic Synthesis, Wiley-Interscience, for example.

Some of the compounds of the present invention are useful not only as compounds having a PTH-like effect but also as intermediates for the synthesis of additional compounds of the present invention. For example, amines may be alkylated, acylated, carbamated, converted to ureas, sulfonamidated or sulfamidated under general conditions. Carboxylic acid and ester moieties may be converted to amides under general conditions. Amido groups may be converted to thioamido groups. Olefins may be reduced or converted to diols. Thioether groups, if present, may be oxidized to sulfoxides or sulfones. The techniques for introducing these groups can be performed with reference to March, Advanced Organic Chemistry, $5^{th}$ Edition, John Wiley and Sons, New York; J. Med. Chem., 2005, 48, 6066-6083; Organic Syntheses (1951), 31, 8-11; Bioorg. Med. Chem. Lett., 2003, 13, 837-840, for example. Protecting groups may be deprotected under general conditions. This can be performed with reference to Protective Groups in Organic Synthesis, Wiley-Interscience, for example. Aryl halides may be coupled with arylboric acids or aryl boronates under general Suzuki conditions. This can be performed with reference to Chem. Rev. 2002, 102, 1359; J. Organomet. Chem. 1999, 576, 147; Chem. Rev. 1995, 95, 2457, for example.

EXAMPLES

The content of the present invention will be described in more detail by the following examples and test example; however, the present invention is not limited to the content of the examples and test example. All starting materials and reagents were obtained from commercial suppliers or synthesized using known methods. $^1$H-NMR spectra were measured using EX270 (manufactured by JEOL), Mercury300 (manufactured by Varian), ARX-3000 (manufactured by Bruker), ECP-400 (manufactured by JEOL) or 400-MR (manufactured by Varian) with or without $Me_4Si$ as the internal standard (s=singlet, d=doublet, t=triplet, brs=broad singlet, m=multiplet). Mass spectrometry measurement was performed using a mass spectrometer, LCQ Classic (manufactured by Thermo Electron), ZQ2000 (manufactured by Waters), 3100 (manufactured by Waters), ZMD4000 (manufactured by Waters), SQD (manufactured by Waters) or 2020 (manufactured by Shimazu). Microwave irradiation was performed using Initiator™ (manufactured by Biotage). In LCMS and HPLC, measurement of the retention time and mass spectrometry were performed by the following apparatuses and analysis conditions.

TABLE 1

| LCMS, HPLC condition No. | Apparatus | Column (I.D. × length) (mm) | Mobile phase | Gradient (A/B) | Flow rate | Column temperature (° C.) | Wavelength |
| --- | --- | --- | --- | --- | --- | --- | --- |
| LCMS-A-1 | Agilent 1100/ LCQ Classic | Cadenza CD-C18 3 um (3.0 × 30) | A) 0.05% TFA, H2O B) 0.05% TFA, MeCN | 95/5 => 0/100 (3.5 min) 0/100 (1 min) | 1.5 mL/min | 35 | 210-400 nm PDA total |
| LCMS-A-2 | Agilent 1100/ LCQ Classic | Cadenza CD-C18 3 um (3.0 × 30) | A) 0.05% TFA, H2O B) 0.05% TFA, MeCN | 95/5 => 0/100 (9.5 min) 0/100 (2.5 min) | 1.0 mL/min | 35 | 210-400 nm PDA total |

TABLE 1-continued

| LCMS, HPLC condition No. | Apparatus | Column (I.D. × length) (mm) | Mobile phase | Gradient (A/B) | Flow rate | Column temperature (° C.) | Wavelength |
|---|---|---|---|---|---|---|---|
| LCMS-B-1 | Alliance 2795 HT/ 996 PDA/ ZMD4000 | Cadenza CD-C18 3 um (3.0 × 30) | A) 0.05% TFA, H2O B) 0.05% TFA, MeCN | 95/5 => 0/100 (3.5 min) 0/100 (1 min) | 1.5 mL/min | 35 | 210-400 nm PDA total |
| LCMS-C-1 | 2525 BGM/ 2996 PDA/ ZQ2000 | Chromolith Flash RP-18e (4.6 × 25) | A) 10 mM AcONH4, H2O B) MeOH | 95/5 => 0/100 (3 min) 0/100 (2 min) | 2.0 mL/min | Room temperature | 210-400 nm PDA total |
| LCMS-C-2 | 2525 BGM/ 2996 PDA/ ZQ2000 | Chromolith Flash RP-18e (4.6 × 25) | A) 10 mM AcONH4, H2O B) MeOH | 95/5 => 0/100 (3 min) 0/100 (2 min) | 2.0 mL/min | Room temperature | 210-400 nm PDA total |
| LCMS-C-3 | 2525 BGM/ 2996 PDA/ ZQ2000 | Chromolith Flash RP-18e (4.6 × 25) | A) 10 mM AcONH4, H2O B) MeOH | 50/50 => 0/100 (3 min) 0/100 (2 min) | 2.0 mL/min | Room temperature | 210-400 nm PDA total |
| LCMS-D-1 | 2545 BGM/ 2996 PDA/ 3100 | SunfireTM C18 5 um (4.6 × 50) | A) 0.05% TFA, H2O B) 0.05% TFA, MeCN | 90/10 => 10/90 (5 min) | 4.0 mL/min | 25 | 210-400 nm PDA total |
| LCMS-E-1 | Agilent 1100 | Waters X-Bridge C18 5 um (2.1 × 50) | A) 0.01% NH3, H2O B) 0.01% NH3, MeCN | 95/5 => 5/95 (5 min) | 1.2 mL/min | 40 | 190-400 nm PDA total |
| LCMS-E-2 | Alliance 2795/ ZQ2000 | Waters X-Bridge C18 5 um (2.1 × 50) | A) 0.1% TFA, H2O B) 0.1% TFA, MeCN | 95/5 => 35/65 (5 min) | 1.2 mL/min | 40 | 190-400 nm PDA total |
| LCMS-E-3 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 5/95 (5 min) | 1.2 mL/min | 45 | 190-400 nm PDA total |
| LCMS-E-4 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 5/95 (5 min) | 1.2 mL/min | 45 | 190-400 nm PDA total |
| LCMS-E-5 | Alliance 2795/ ZQ2000 | Waters X-Bridge C18 5 um (2.1 × 50) | A) 0.01% NH3, H2O B) 0.01% NH3, MeCN | 95/5 (0 min) => 95/5 (0.5 min) => 35/65 (5 min) => 5/95 (5.5 min) | 1.2 mL/min | 45 | 190-400 nm PDA total |
| LCMS-E-6 | Alliance 2795/ ZQ2000 | Waters X-Bridge C18 5 um (2.1 × 50) | A) 0.1% TFA, H2O B) 0.1% TFA, MeCN | 95/5 => 5/95 (5 min) | 1.2 mL/min | 40 | 190-400 nm PDA total |
| LCMS-E-7 | Alliance 2795/ ZQ2000 | Waters X-Bridge C18 3.5 um (2.1 × 50) | A) 0.1% TFA, H2O B) 0.1% TFA, MeCN | 95/5 (0 min) => 95/5 (3 min) | 1.2 mL/min | 45 | 190-400 nm PDA total |
| LCMS-E-8 | Alliance 2795/ ZQ2000 | Waters X-Bridge C18 5 um (2.1 × 50) | A) 0.1% TFA, H2O B) 0.1% TFA, MeCN | 95/5 (0 min) => 95/5 (0.5 min) => 35/65 (5 min) => 5/95 (5.5 min) | 1.2 mL/min | 45 | 190-400 nm PDA total |
| LCMS-F-1 | Acquity/ SQD | Ascentis Express C18 (2.1 × 50) | A) 10 mM AcONH4, H2O B) MeOH | 95/5 => 0/100 (1 min) 0/100 (0.4 min) | 1.0 mL/min | 35 | 210-400 nm PDA total |
| LCMS-F-2 | Acquity/ SQD | Ascentis Express C18 (2.1 × 50) | A) 0.1% HCO2H, H2O B) 0.1% HCO2H, MeCN | 95/5 => 0/100 (1 min) 0/100 (0.4 min) | 1.0 mL/min | 35 | 210-400 nm PDA total |
| LCMS-G-1 | UFLC XR/2020 | Acquity (2.1 × 50) | A) 0.1% TFA, H2O B) 0.1% TFA, MeCN | 95/5 => 0/100 (1.5 min) 0/100 (0.5 min) | 1.0 mL/min | 35 | 305 nm, bandwidth 95 nm |
| HPLC-A-1 | LC-2010A (SHIMAZU) | YMC-ODSA (6.0 × 150) | A) 0.1% TFA, H2O B) 0.1% TFA, MeCN | 90/20 => 10/80 (40 min) | 1.0 mL/min | 25 | UV 254, 225 nm |
| HPLC-A-2 | LC-2010A (SHIMAZU) | YMC-ODSA (6.0 × 150) | A) 0.1% TFA, H2O B) 0.1% TFA, MeCN | 90/30 => 10/70 (40 min) | 1.0 mL/min | 25 | UV 254, 225 nm |
| HPLC-A-3 | LC-2010A (SHIMAZU) | YMC-ODSA (6.0 × 150) | A) 0.1% TFA, H2O B) 0.1% TFA, MeCN | 90/10 => 10/90 (25 min) | 1.0 mL/min | 25 | UV 254, 225 nm |

Example 1

8-(3-Chloro-benzenesulfonyl)-2-cyclohexyl-1,3,8-triaza-spiro[4.5]dec-1-en-4-one (Compound 1)

(Reaction 1-1)

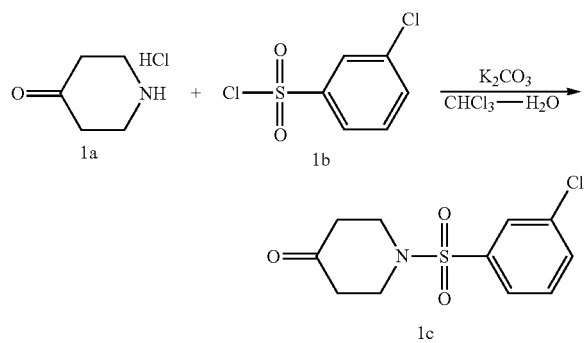

Potassium carbonate (13.96 g, 101.1 mmol) and 3-chlorobenzenesulfonyl chloride were continuously added to a two-phase solution of 4-piperidone hydrochloride hydrate (6.06 g, 39.48 mmol) in chloroform (47.4 mL) and water (47.4 mL), and the mixture was stirred at room temperature. A saturated aqueous sodium bicarbonate solution was added, and the organic layer and the aqueous layer were separated. The aqueous layer was then further extracted with dichloromethane. The organic layers were combined, dried over anhydrous sodium sulfate and then concentrated under reduced pressure. The resulting solid was washed with n-hexane and then collected by filtration and dried under reduced pressure to give 1-(3-chloro-benzenesulfonyl)-piperidin-4-one as a white solid (10.5 g, 97%).

$^1$H-NMR (300 MHz, CDCl$_3$) δ 2.55 (4H, t, J=6.3 Hz), 3.42 (4H, t, J=6.0 Hz), 7.48 (1H, t, J=8.0 Hz), 7.58 (1H, dt, J=8.0, 1.7 Hz), 7.67 (1H, dt, J=7.7, 1.7 Hz), 7.77 (1H, t, J=1.9 Hz).

(Reaction 1-2)

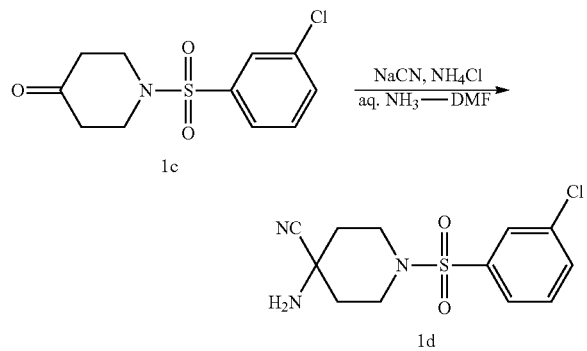

Ammonium chloride (790 mg, 14.77 mmol) and a 28% aqueous ammonia solution (2.2 mL) were added to a solution of 1-(3-chloro-benzenesulfonyl)-piperidin-4-one (3.11 g, 11.36 mmol) in dimethylformamide (15 mL), and the mixture was stirred at room temperature for one hour. Thereafter, sodium cyanide (724 mg, 14.77 mmol) was added, and the mixture was further stirred for 17 hours and then quenched with a saturated aqueous sodium carbonate solution. The organic layer and the aqueous layer were separated, and the aqueous layer was then further extracted with ethyl acetate:n-hexane (4:1). The organic layers were combined, washed with water (×4), and then dried over anhydrous sodium sulfate and concentrated under reduced pressure. The residue was purified by silica gel column chromatography (n-hexane:ethyl acetate=1:3) to give 4-amino-1-(3-chloro-benzenesulfonyl)-piperidine-4-carbonitrile as a white solid (2.41 g, 71%).

$^1$H-NMR (300 MHz, CDCl$_3$) δ 1.75 (2H, s), 1.80-1.90 (2H, m), 2.11-2.14 (2H, m), 2.87-2.96 (2H, m), 3.54-3.62 (2H, m), 7.47 (1H, t, J=8.1 Hz), 7.58-7.66 (2H, m), 7.75 (1H, t, J=1.8 Hz).

(Reaction 1-3)

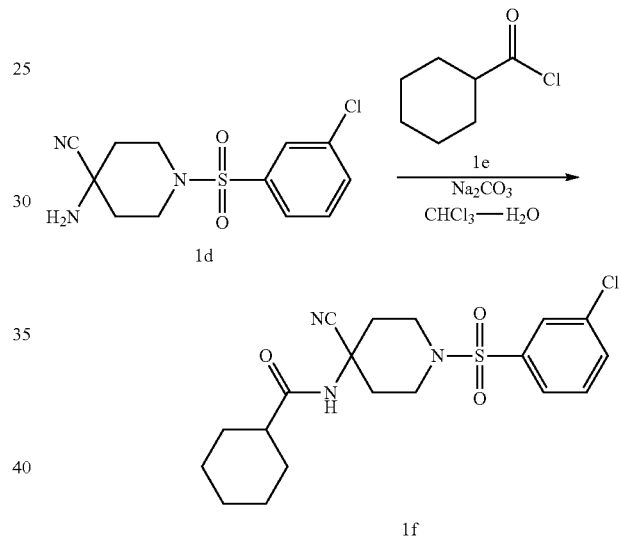

A solution of cyclohexanecarbonyl chloride (118 μL, 0.880 mmol) in chloroform (0.25 mL) was added to a mixed solution of 4-amino-1-(3-chloro-benzenesulfonyl)-piperidine-4-carbonitrile (120 mg, 0.400 mmol) in chloroform (1.25 mL) and a saturated aqueous sodium carbonate solution (1.25 mL), and the mixture was vigorously stirred at room temperature for 16 hours. Cyclohexanecarbonyl chloride (51 μL) was further added and the mixture was stirred for 2.5 hours. The organic layer and the aqueous layer were then separated, and the aqueous layer was further extracted with chloroform. The organic layers were combined, dried over anhydrous sodium sulfate and then concentrated under reduced pressure. The residue was washed with n-hexane to give cyclohexanecarboxylic[1-(3-chloro-benzenesulfonyl)-4-cyano-piperidin-4-yl]-amide as a white solid. This was used in the next step without further purification.

$^1$H-NMR (300 MHz, CDCl$_3$) δ 1.20-1.96 (14H, m), 2.04-2.14 (1H, m), 2.55 (2H, brd, J=13 Hz), 2.76-2.87 (2H, m), 5.58 (1H, s), 7.51 (1H, t, J=7.9 Hz), 7.60-7.66 (2H, m), 7.75 (1H, t, J=1.8 Hz). MS (ESI) m/z=410 (M+H)+.

(Reaction 1-4)

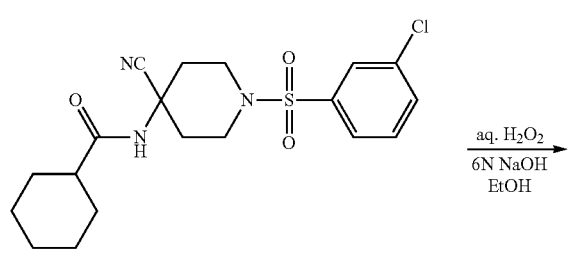

1f

Compound 1

A 6 M aqueous sodium hydroxide solution (0.74 mL) and a 30% aqueous hydrogen peroxide solution (0.25 mL) were added to a solution of cyclohexanecarboxylic[1-(3-chloro-benzenesulfonyl)-4-cyano-piperidin-4-yl]-amide (100 mg, 0.244 mmol) in ethanol (1.60 mL), and the mixture was heated under reflux for 4.5 hours. The reaction mixture was cooled to room temperature and water was then added, followed by concentration under reduced pressure. The residue was neutralized with a saturated aqueous ammonium chloride solution, followed by extraction with dichloromethane. The organic layer was dried over anhydrous sodium sulfate and concentrated under reduced pressure. The residue was purified by silica gel column chromatography (dichloromethane:methanol=90:10) to give 8-(3-chloro-benzenesulfonyl)-2-cyclohexyl-1,3,8-triaza-spiro[4.5]dec-1-en-4-one as a white solid (52 mg, 52%).

$^1$H-NMR (270 MHz, CDCl$_3$) δ 1.13-1.40 (7H, m), 1.54-1.75 (7H, m), 2.22-2.30 (1H, m), 2.72-2.80 (2H, m), 3.53-3.59 (2H, m), 7.67-7.85 (4H, m), 10.80 (1H, s). MS (ESI) m/z=410 (M+H)+.

The example compounds shown below were synthesized by operations similar to those in Example 1 using appropriate reagents and starting materials.

TABLE 2

| Compound | Structure | LCMS or HPLC condition | Retention time (min) | MS (m/z) |
|---|---|---|---|---|
| 2 | 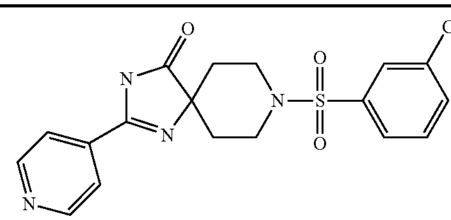 | LCMS-A-1 | 1.92 | 405 (M + H)+ |
| 3 | 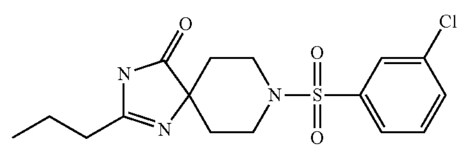 [SMILES: CCCC1=NC2(CCN(S(=O)(=O)c3cccc(Cl)c3)CC2)C(=O)N1] | LCMS-A-1 | 1.9 | 370 (M + H)+ |
| 4 | 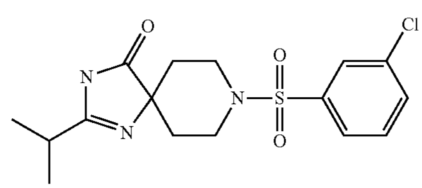 [SMILES: CC(C)C1=NC2(CCN(S(=O)(=O)c3cccc(Cl)c3)CC2)C(=O)N1] | LCMS-A-1 | 1.87 | 370 (M + H)+ |
| 5 | 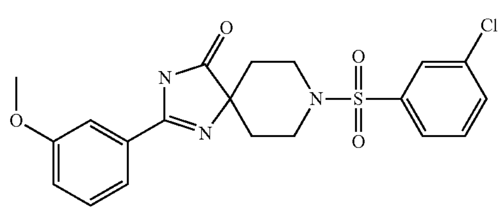 [SMILES: COc1cccc(C2=NC3(CCN(S(=O)(=O)c4cccc(Cl)c4)CC3)C(=O)N2)c1] | LCMS-A-1 | 2.32 | 434 (M + H)+ |
| 6 | 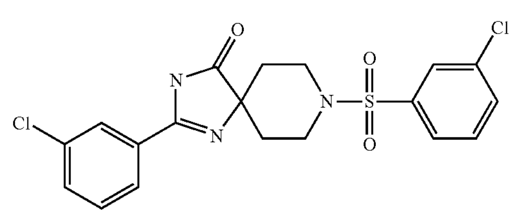 [SMILES: O=C1NC(c2cccc(Cl)c2)=NC12CCN(S(=O)(=O)c1cccc(Cl)c1)CC2] | LCMS-A-1 | 2.65 | 438 (M + H)+ |

TABLE 2-continued

| Compound | Structure | LCMS or HPLC condition | Retention time (min) | MS (m/z) |
| --- | --- | --- | --- | --- |
| 7 | 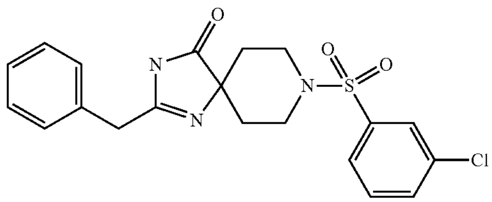 [SMILES: O=C1NC(Cc2ccccc2)=NC12CCN(S(=O)(=O)c1cccc(Cl)c1)CC2] | LCMS-A-1 | 2.22 | 418 (M + H)+ |
| 8 | 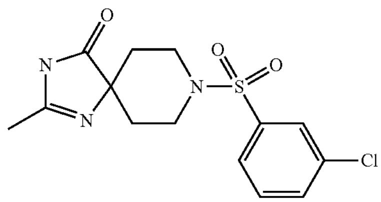 [SMILES: CC1=NC2(CCN(S(=O)(=O)c3cccc(Cl)c3)CC2)C(=O)N1] | LCMS-A-1 | 1.79 | 342 (M + H)+ |
| 10 | 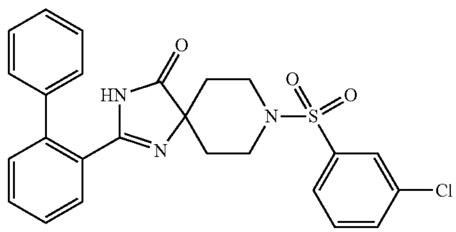 [SMILES: O=C1NC(c2ccccc2-c2ccccc2)=NC12CCN(S(=O)(=O)c1cccc(Cl)c1)CC2] | LCMS-C-1 | 2.82 | 480 (M + H)+ |
| 11 | 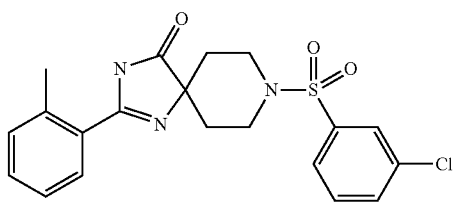 [SMILES: Cc1ccccc1C1=NC2(CCN(S(=O)(=O)c3cccc(Cl)c3)CC2)C(=O)N1] | LCMS-C-1 | 2.66 | 418 (M + H)+ |
| 12 | 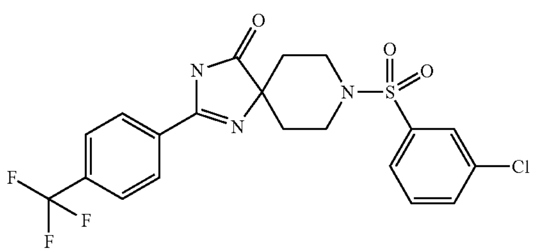 [SMILES: O=C1NC(c2ccc(C(F)(F)F)cc2)=NC12CCN(S(=O)(=O)c1cccc(Cl)c1)CC2] | LCMS-C-1 | 2.89 | 472 (M + H)+ |
| 13 | 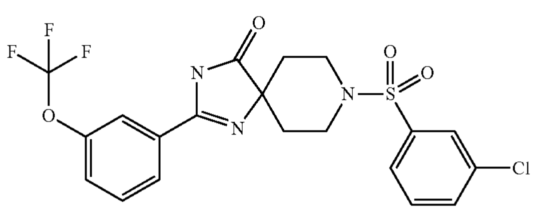 [SMILES: O=C1NC(c2cccc(OC(F)(F)F)c2)=NC12CCN(S(=O)(=O)c1cccc(Cl)c1)CC2] | LCMS-A-1 | 2.82 | 488 (M + H)+ |
| 14 | 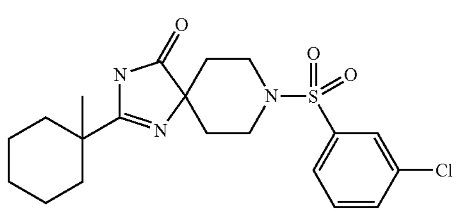 [SMILES: CC1(C2=NC3(CCN(S(=O)(=O)c4cccc(Cl)c4)CC3)C(=O)N2)CCCCC1] | LCMS-C-1 | 2.86 | 424 (M + H)+ |

TABLE 2-continued

| Compound | Structure | LCMS or HPLC condition | Retention time (min) | MS (m/z) |
|---|---|---|---|---|
| 15 | 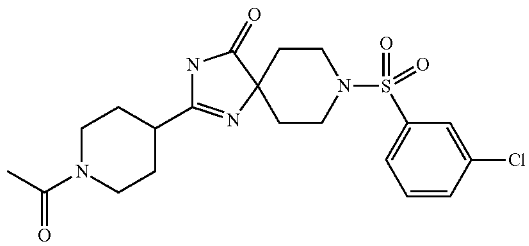 [SMILES: CC(=O)N1CCC(C2=NC3(CCN(S(=O)(=O)c4cccc(Cl)c4)CC3)C(=O)N2)CC1] | LCMS-A-1 | 1.84 | 453 (M + H)+ |
| 16 | 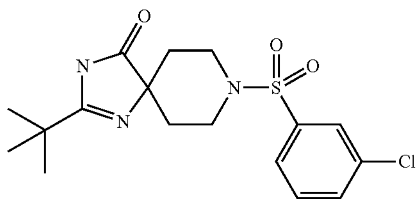 [SMILES: CC(C)(C)C1=NC2(CCN(S(=O)(=O)c3cccc(Cl)c3)CC2)C(=O)N1] | LCMS-A-1 | 1.97 | 384 (M + H)+ |
| 17 | 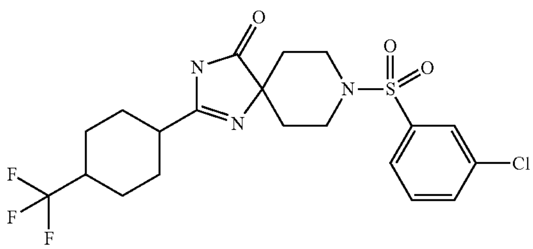 [SMILES: O=C1NC(C2CCC(C(F)(F)F)CC2)=NC12CCN(S(=O)(=O)c1cccc(Cl)c1)CC2] | LCMS-C-1 | 2.81 | 478 (M + H)+ |
| 18 | 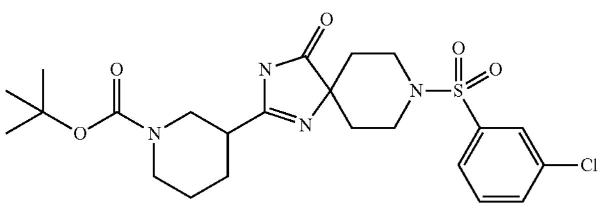 [SMILES: CC(C)(C)OC(=O)N1CCCC(C2=NC3(CCN(S(=O)(=O)c4cccc(Cl)c4)CC3)C(=O)N2)C1] | LCMS-C-1 | 2.8 | 511 (M + H)+ |
| 19 | 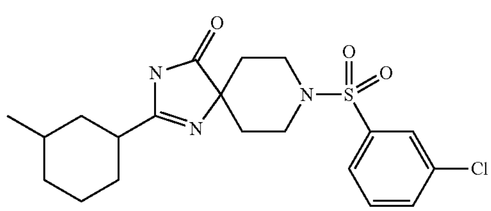 [SMILES: CC1CCCC(C2=NC3(CCN(S(=O)(=O)c4cccc(Cl)c4)CC3)C(=O)N2)C1] | LCMS-A-1 | 2.22 | 424 (M + H)+ |
| 20 | 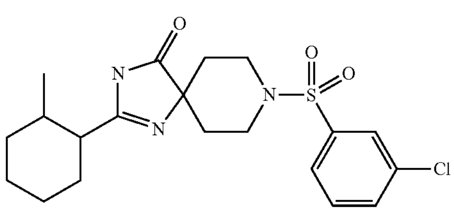 [SMILES: CC1CCCCC1C1=NC2(CCN(S(=O)(=O)c3cccc(Cl)c3)CC2)C(=O)N1] | LCMS-C-1 | 2.78 | 424 (M + H)+ |
| 21 | 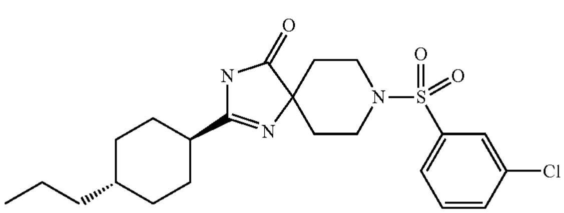 [SMILES: CCC[C@H]1CC[C@H](C2=NC3(CCN(S(=O)(=O)c4cccc(Cl)c4)CC3)C(=O)N2)CC1] | LCMS-C-1 | 3.1 | 452 (M + H)+ |

TABLE 2-continued

| Compound | Structure | LCMS or HPLC condition | Retention time (min) | MS (m/z) |
| --- | --- | --- | --- | --- |
| 22 | 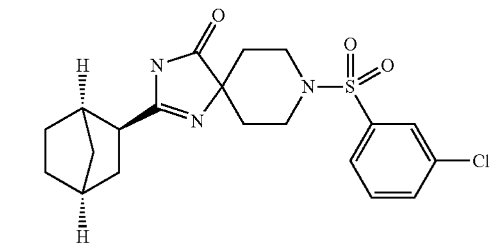 [SMILES: O=C1NC([C@H]2C[C@H]3CC[C@@H]2C3)=NC12CCN(S(=O)(=O)c1cccc(Cl)c1)CC2] | LCMS-C-1 | 2.76 | 422 (M + H)+ |
| 23 | 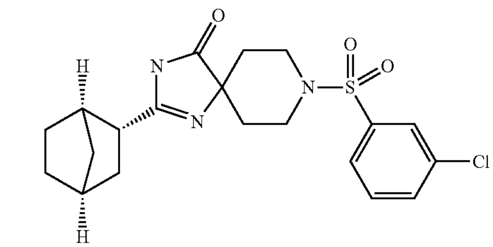 [SMILES: O=C1NC([C@@H]2C[C@H]3CC[C@@H]2C3)=NC12CCN(S(=O)(=O)c1cccc(Cl)c1)CC2] | LCMS-C-1 | 2.74 | 422 (M + H)+ |
| 24 | 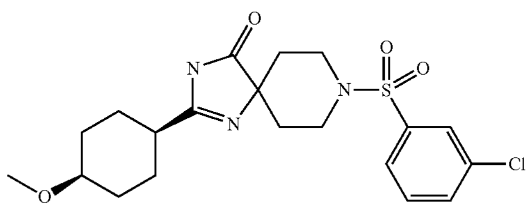 [SMILES: CO[C@H]1CC[C@@H](C2=NC3(CCN(S(=O)(=O)c4cccc(Cl)c4)CC3)C(=O)N2)CC1] | LCMS-C-1 | 2.47 | 440 (M + H)+ |
| 25 | 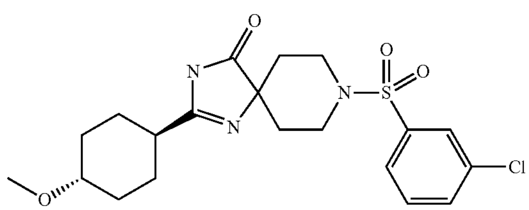 [SMILES: CO[C@H]1CC[C@H](C2=NC3(CCN(S(=O)(=O)c4cccc(Cl)c4)CC3)C(=O)N2)CC1] | LCMS-C-1 | 2.45 | 440 (M + H)+ |
| 26 | 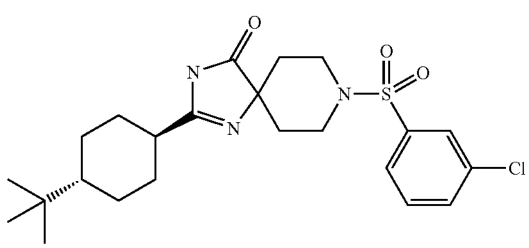 [SMILES: CC(C)(C)[C@H]1CC[C@H](C2=NC3(CCN(S(=O)(=O)c4cccc(Cl)c4)CC3)C(=O)N2)CC1] | LCMS-C-1 | 3.14 | 466 (M + H)+ |
| 27 | 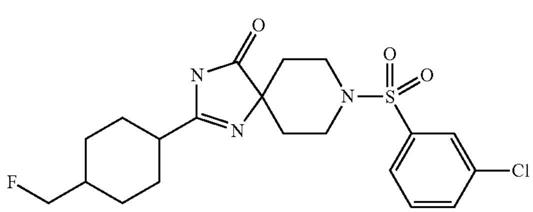 [SMILES: O=C1NC(C2CCC(CF)CC2)=NC12CCN(S(=O)(=O)c1cccc(Cl)c1)CC2] | LCMS-C-1 | 2.61 | 442 (M + H)+ |
| 28 | 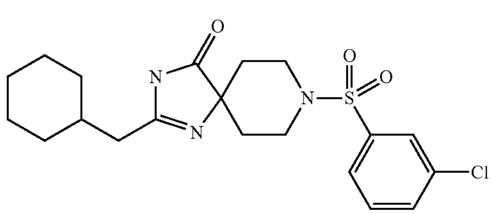 [SMILES: O=C1NC(CC2CCCCC2)=NC12CCN(S(=O)(=O)c1cccc(Cl)c1)CC2] | LCMS-C-1 | 2.81 | 424 (M + H)+ |

TABLE 2-continued

| Compound | Structure | LCMS or HPLC condition | Retention time (min) | MS (m/z) |
|---|---|---|---|---|
| 29 | 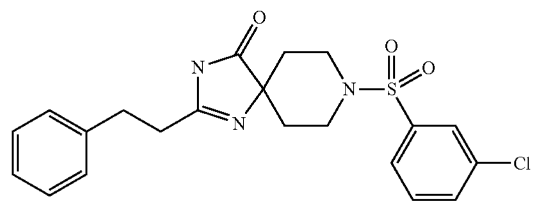 [SMILES: O=C1NC(CCc2ccccc2)=NC12CCN(S(=O)(=O)c1cccc(Cl)c1)CC2] | LCMS-C-1 | 2.65 | 432 (M + H)+ |
| 30 | 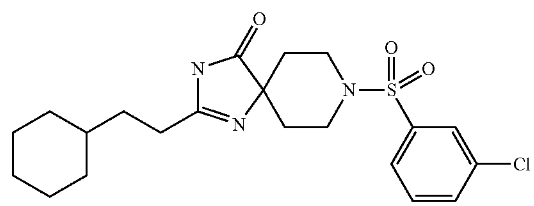 [SMILES: O=C1NC(CCC2CCCCC2)=NC12CCN(S(=O)(=O)c1cccc(Cl)c1)CC2] | LCMS-A-1 | 2.4 | 438 (M + H)+ |
| 31 | 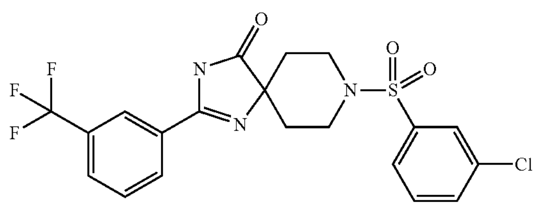 [SMILES: O=C1NC(c2cccc(C(F)(F)F)c2)=NC12CCN(S(=O)(=O)c1cccc(Cl)c1)CC2] | LCMS-A-1 | 2.79 | 472 (M + H)+ |
| 32 | 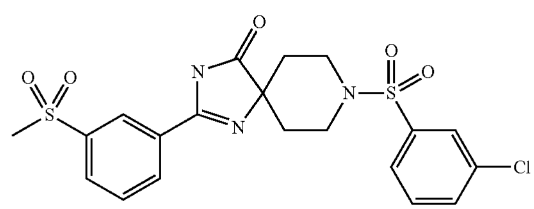 [SMILES: CS(=O)(=O)c1cccc(C2=NC3(CCN(S(=O)(=O)c4cccc(Cl)c4)CC3)C(=O)N2)c1] | LCMS-C-1 | 2.3 | 482 (M + H)+ |
| 33 | 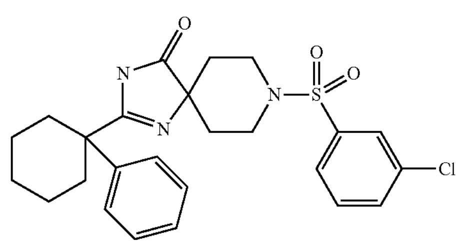 [SMILES: O=C1NC(C2(c3ccccc3)CCCCC2)=NC12CCN(S(=O)(=O)c1cccc(Cl)c1)CC2] | LCMS-C-1 | 3.08 | 486 (M + H)+ |
| 34 | 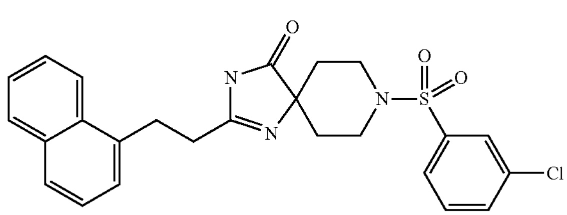 [SMILES: O=C1NC(CCc2cccc3ccccc23)=NC12CCN(S(=O)(=O)c1cccc(Cl)c1)CC2] | LCMS-C-1 | 2.87 | 482 (M + H)+ |

Example 2

8-(2-Naphthalen-1-yl-ethanesulfonyl)-2-(3-trifluoromethyl-phenyl)-1,3,8-triaza-spiro[4.5]dec-1-en-4-one (Compound 35)

(Reaction 2-1)

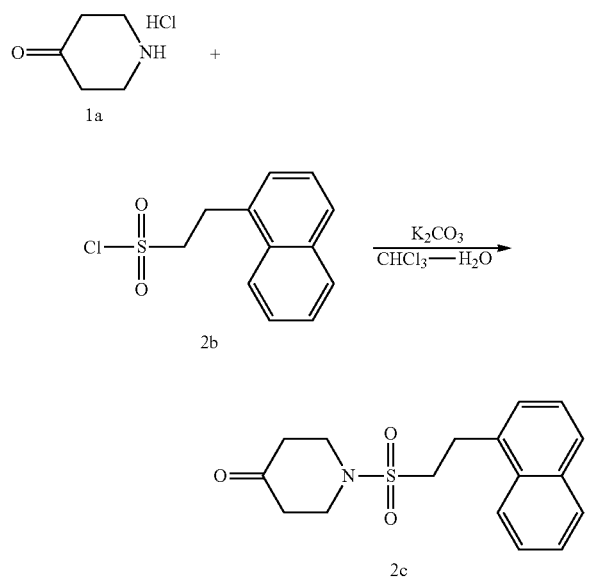

1-(2-Naphthalen-1-yl-ethanesulfonyl)-piperidin-4-one was synthesized by the procedure described in Reaction 1-1 of Example 1 using 2-naphthalen-1-yl-ethanesulfonyl chloride as a reagent.

MS (ESI) m/z=318 (M+H)+.

(Reaction 2-2)

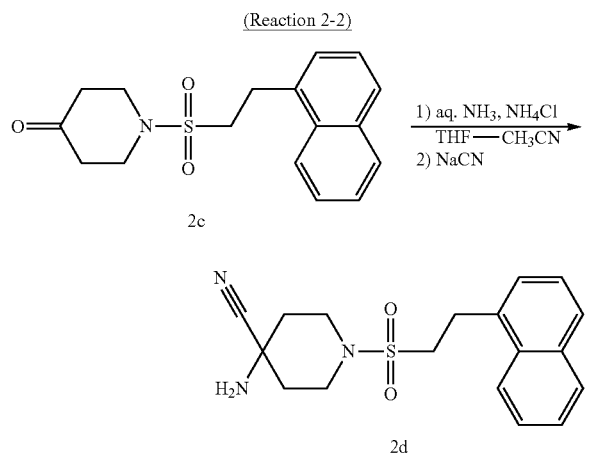

4-Amino-1-(2-naphthalen-1-yl-ethanesulfonyl)-piperidine-4-carbonitrile was synthesized by operations similar to those in Reaction 1-2 of Example 1 using THF-CH₃CN as a solvent and using appropriate reagents and starting material.

MS (ESI) m/z=344 (M+H)+.

(Reaction 2-3)

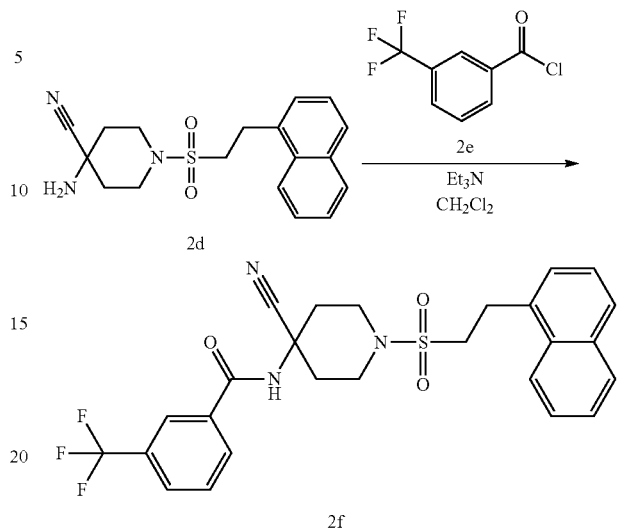

3-Trifluoromethyl-benzoyl chloride (57 µL, 0.378 mmol) was added to a solution of 4-amino-1-(2-naphthalen-1-yl-ethanesulfonyl)-piperidine-4-carbonitrile (100 mg, 0.291 mmol) and Et₃N (61 µL) in CH₂Cl₂ (3 mL). The reaction mixture was stirred at room temperature for four hours and then diluted with CH₂Cl₂, and the organic layer was washed with water. The organic layer was dried over anhydrous sodium sulfate and then concentrated under reduced pressure. The residue was used in the next step without further purification.

MS (ESI) m/z=516 (M+H)+.

(Reaction 2-4)

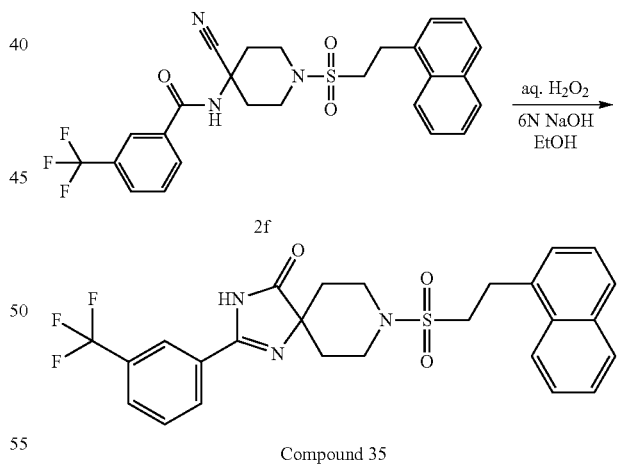

Compound 35

8-(2-Naphthalen-1-yl-ethanesulfonyl)-2-(3-trifluoromethyl-phenyl)-1,3,8-triaza-spiro[4.5]dec-1-en-4-one was synthesized by operations similar to those in Reaction 1-4 of Example 1 using appropriate reagents and starting material.

$^1$H-NMR (400 MHz, CDCl₃) δ 1.65-1.75 (2H, m), 2.07-2.16 (2H, m), 3.32-3.38 (2H, m), 3.42-3.55 (2H, m), 3.63-3.70 (2H, m), 3.82-3.90 (2H, m), 7.40-7.47 (2H, m), 7.50-7.55 (1H, m), 7.56-7.65 (2H, m), 7.77-7.7.82 (2H, m), 7.90 (1H, d, J=4.0 Hz), 8.02-8.10 (2H, m), 8.18 (1H, s); MS (ESI) m/z=516 (M+H)+.

The example compounds shown below were synthesized by operations similar to those in Example 2 using appropriate reagents and starting materials.

TABLE 3

| Compound | Structure | LCMS or HPLC condition | Retention time (min) | MS (m/z) |
|---|---|---|---|---|
| 36 | 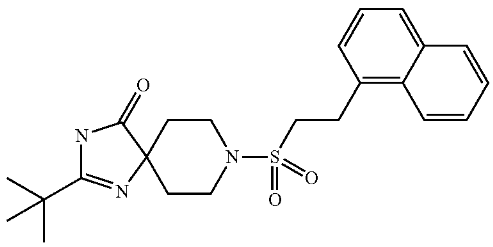 [SMILES: CC(C)(C)C1=NC2(CCN(S(=O)(=O)CCc3cccc4ccccc34)CC2)C(=O)N1] | LCMS-A-1 | 2.24 | 428 (M + H)+ |
| 37 | 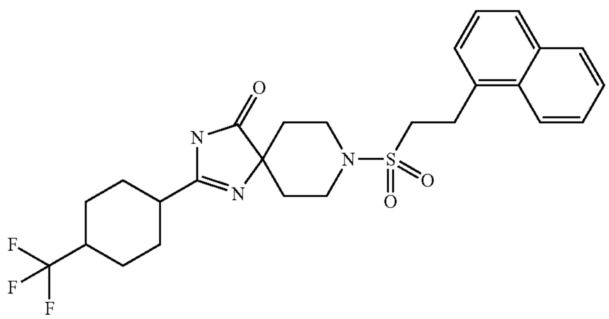 [SMILES: O=C1NC(C2CCC(C(F)(F)F)CC2)=NC12CCN(S(=O)(=O)CCc1cccc3ccccc13)CC2] | LCMS-A-1 | 2.55 | 522 (M + H)+ |

Example 3

3-[8-(2-Naphthalen-1-yl-ethanesulfonyl)-4-oxo-1,3,8-triaza-spiro[4.5]dec-1-en-2-yl]-piperidine-1-carboxylic acid tert-butyl ester (Compound 38)

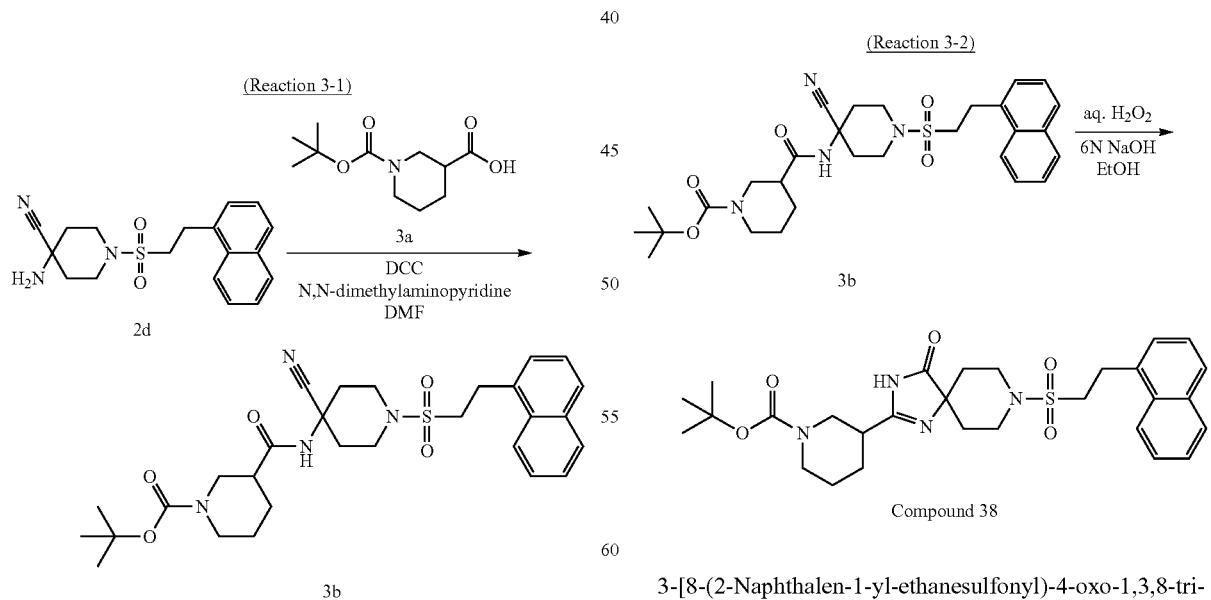

DCC (1.3 eq) and DMAP (5 mol %) were added to a mixture of 4-amino-1-(2-naphthalen-1-yl-ethanesulfonyl)-piperidine-4-carbonitrile and piperidine-1,3-dicarboxylic acid 1-tert-butyl ester (1.3 eq) in DMF, and the mixture was stirred at room temperature overnight. Ethyl acetate was added to the reaction solution, and the organic layer was then sequentially washed with 1 N NaOH, water and saturated brine. The organic layer was dried over anhydrous sodium sulfate and then concentrated under reduced pressure. The residue was used in the next step without further purification.

3-[8-(2-Naphthalen-1-yl-ethanesulfonyl)-4-oxo-1,3,8-triaza-spiro[4.5]dec-1-en-2-yl]-piperidine-1-carboxylic acid tert-butyl ester was synthesized by operations similar to those in Reaction 1-4 of Example 1 using appropriate reagents and starting material.

MS (ESI) m/z=555 (M+H)+.

Example 4

8-(2-Naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one (Compound 39)

(Reaction 4-1)

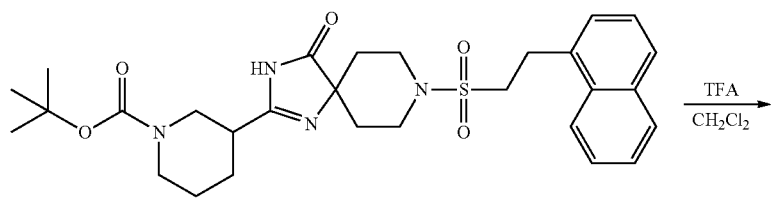

Compound 38

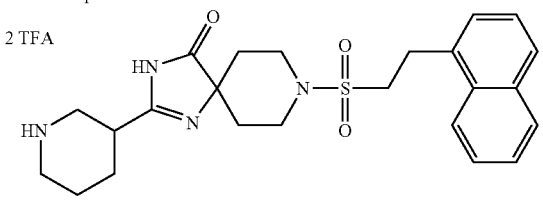

4a

Trifluoroacetic acid (10 eq) was added dropwise to a solution of 3-[8-(2-naphthalen-1-yl-ethanesulfonyl)-4-oxo-1,3,8-triaza-spiro[4.5]dec-1-en-2-yl]-piperidine-1-carboxylic acid tert-butyl ester in $CH_2Cl_2$. The reaction mixture was stirred at room temperature overnight and then concentrated under reduced pressure to give 8-(2-naphthalen-1-yl-ethanesulfonyl)-2-piperidin-3-yl-1,3,8-triaza-spiro[4.5]dec-1-en-4-one ditrifluoroacetate as a pale yellow form (70%).

$^1$H-NMR (400 MHz, CD3OD) δ 0.98 (3H, t), 1.15-1.22 (1H, m), 1.44-1.52 (2H, m), 1.56-1.67 (2H, m), 1.69-1.82 (2H, m), 1.86-2.03 (3H, m), 2.63-2.71 (1H, m), 2.79-2.85 (2H, m), 2.86-3.05 (3H, m), 3.49-3.65 (3H, m), 3.65-3.76 (2H, m), 7.44 (1H, t, J=7.83 Hz), 7.50-7.55 (1H, m), 7.61 (1H, d, J=8.08 Hz), 7.71 (1H, t, J=1.77 Hz). MS (ESI) m/z=517 (M+H)+.

(Reaction 4-2)

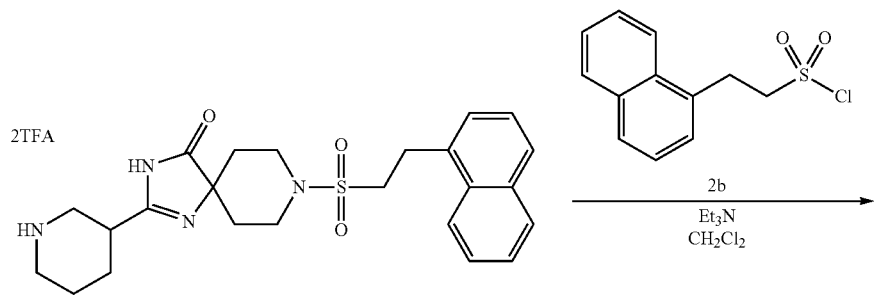

4a

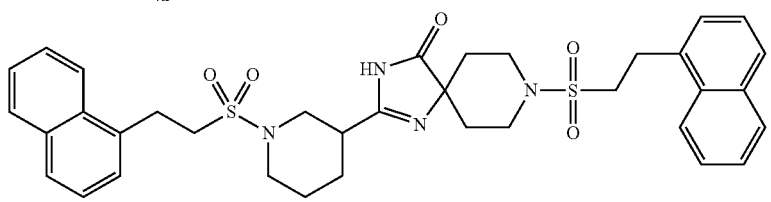

Compound 39

8-(2-Naphthalen-1-yl-ethanesulfonyl)-2-[1-(2-naphthalen-1-yl-ethanesulfonyl)-piperidin-3-yl]-1,3,8-triaza-spiro[4.5]dec-1-en-4-one was synthesized by operations similar to those in Reaction 2-3 of Example 2 using appropriate reagents and starting material.

MS (ESI) m/z=673 (M+H)+.

The example compounds shown below were synthesized by operations similar to those in Example 3 and Example 4 using appropriate reagents and starting materials.

TABLE 4

| Compound | Structure | LCMS or HPLC condition | Retention time (min) | MS (m/z) |
|---|---|---|---|---|
| 40 | 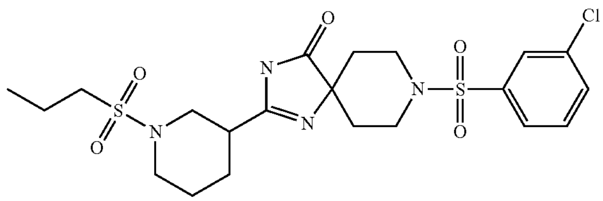 [SMILES: CCCS(=O)(=O)N1CCCC(C2=NC3(CCN(S(=O)(=O)c4cccc(Cl)c4)CC3)C(=O)N2)C1] | LCMS-E-2 | 3.76 | 517 (M + H)+ |
| 41 | 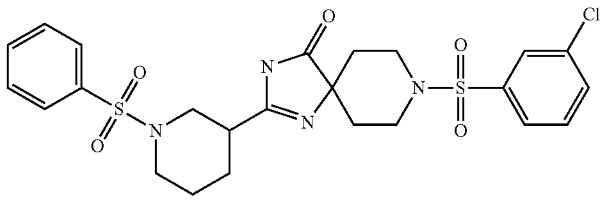 [SMILES: O=C1NC(C2CCCN(S(=O)(=O)c3ccccc3)C2)=NC12CCN(S(=O)(=O)c1cccc(Cl)c1)CC2] | LCMS-E-2 | 4.13 | 551 (M + H)+ |
| 42 | 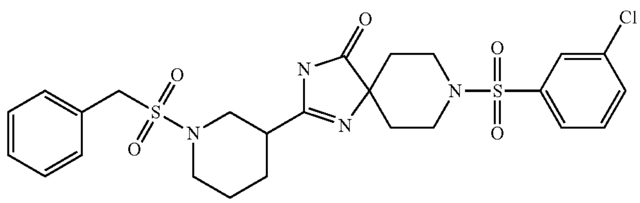 [SMILES: O=C1NC(C2CCCN(S(=O)(=O)Cc3ccccc3)C2)=NC12CCN(S(=O)(=O)c1cccc(Cl)c1)CC2] | LCMS-E-2 | 4.11 | 565 (M + H)+ |
| 43 | 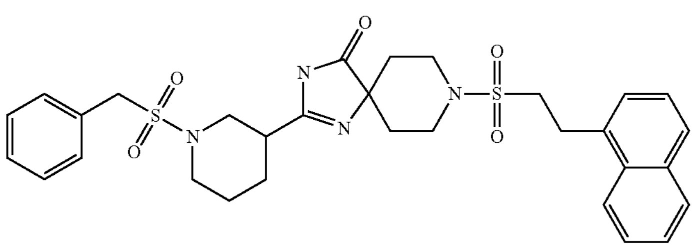 [SMILES: O=C1NC(C2CCCN(S(=O)(=O)Cc3ccccc3)C2)=NC12CCN(S(=O)(=O)CCc1cccc3ccccc13)CC2] | LCMS-E-2 | 3.58 | 609 (M + H)+ |

Example 5

8-(4-Chloro-benzenesulfonyl)-2-(2,4-dichloro-phenyl)-1,3,8-triaza-spiro[4.5]dec-1-en-4-one (Compound 44)

(Reaction 5-1)

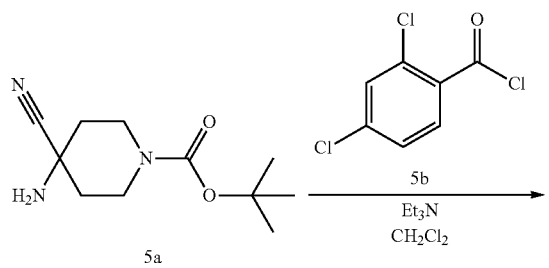

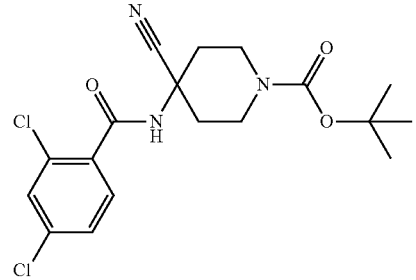

4-Cyano-4-(2,4-dichloro-benzoylamino)-piperidine-1-carboxylic acid tert-butyl ester was synthesized by operations similar to those in Reaction 2-3 of Example 2 using appropriate reagents and starting material.

$^1$H-NMR (400 MHz, CDCl$_3$) δ 1.47 (9H, s), 1.87-1.97 (2H, m), 2.45-2.55 (2H, m), 3.32-3.43 (2H, m), 3.90-4.05 (2H, m), 6.48 (1H, brs), 7.38 (1H, dd, J=8.4, 2.0 Hz), 7.45 (1H, d, J=2.0 Hz), 7.78 (1H, d, J=8.4 Hz).

(Reaction 5-2)

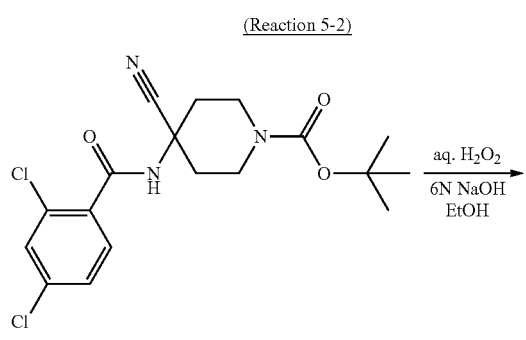

2-(2,4-Dichloro-phenyl)-4-oxo-1,3,8-triaza-spiro[4.5]dec-1-ene-8-carboxylic acid tert-butyl ester was synthesized by operations similar to those in Reaction 1-4 of Example 1 using appropriate reagents and starting material.

MS (ESI) m/z=490 (M+H)+.

(Reaction 5-3)

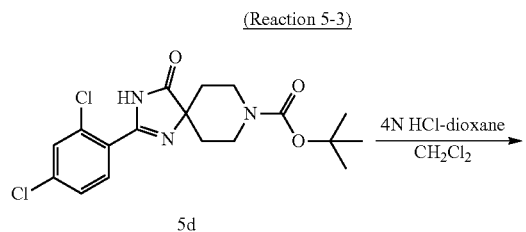

4 N HCl-dioxane (20 ml, 80 mmol) was added to a solution of 2-(2,4-dichloro-phenyl)-4-oxo-1,3,8-triaza-spiro[4.5]dec-1-ene-8-carboxylic acid tert-butyl ester (3.11 g, 7.81 mmol) in CH$_2$Cl$_2$ (60 mL), and the mixture was stirred at room temperature for four hours. The reaction mixture was diluted with CH$_2$Cl$_2$-hexane, and the precipitated solid was then filtered. The resulting solid was washed with ethyl acetate and then dried under reduced pressure to give 2-(2,4-dichloro-phenyl)-1,3,8-triaza-spiro[4.5]dec-1-en-4-one dihydrochloride (3.18 g) as a colorless solid.

MS (ESI) m/z=298 (M+H)+.

(Reaction 5-4)

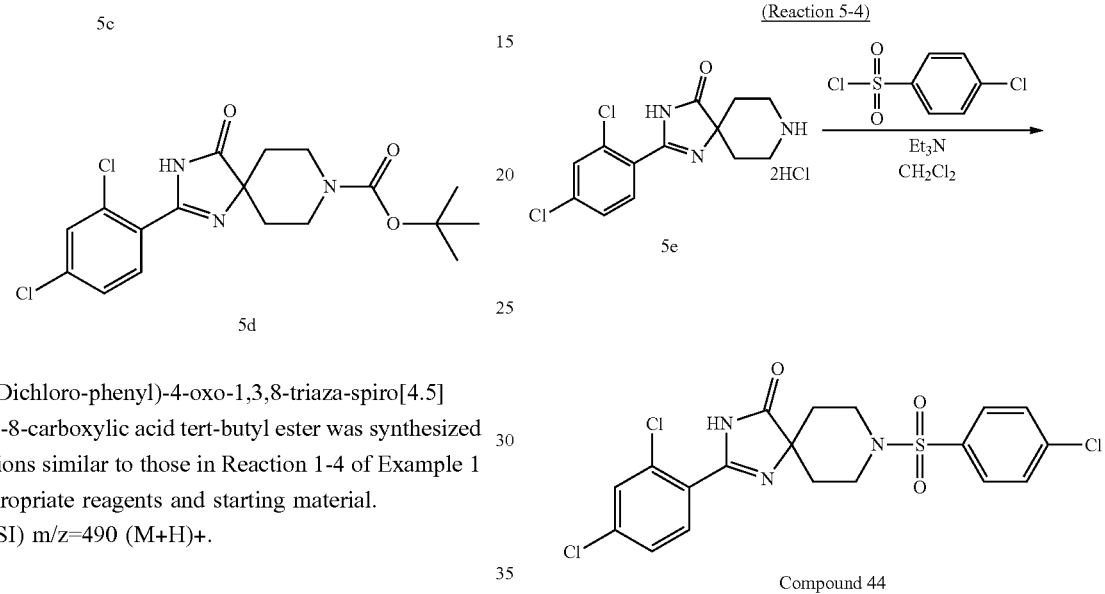

Compound 44

Triethylamine (88 µl, 0.632 mmol) and 4-chlorobenzenesulfonyl chloride (70 mg, 0.332 mmol) were added to a mixed solution of 2-(2,4-dichloro-phenyl)-1,3,8-triaza-spiro[4.5]dec-1-en-4-one dihydrochloride (100 mg, 0.299 mmol) in dichloromethane (3 ml). The reaction solution was stirred at room temperature for 16 hours and then diluted with dichloromethane, and the organic layer was washed with water. The organic layer was dried over sodium sulfate and then concentrated under reduced pressure. The resulting residue was purified by silica gel column chromatography (ethyl acetate:hexane) to give 8-(4-chloro-benzenesulfonyl)-2-(2,4-dichloro-phenyl)-1,3,8-triaza-spiro[4.5]dec-1-en-4-one (70.8 mg, 96%).

$^1$H-NMR (400 MHz, DMSO-d6) δ 1.57-1.67 (2H, m), 1.85-1.95 (2H, m), 2.74-2.83 (2H, m), 3.64-3.72 (2H, m), 7.57-7.60 (1H, m), 7.61-7.65 (1H, m), 7.75-7.79 (2H, m), 7.81-7.86 (3H, m), 11.5 (1H, brs). MS (ESI) m/z=472 (M+H)+.

The example compounds shown below were synthesized by operations similar to those in Example 5 using appropriate reagents and starting materials.

TABLE 5

| Compound | Structure | LCMS or HPLC condition | Retention time (min) | MS (m/z) |
|---|---|---|---|---|
| 45 | 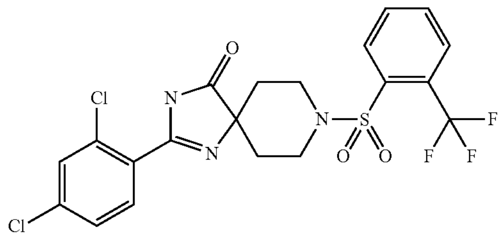 [SMILES: O=C1NC(c2ccc(Cl)cc2Cl)=NC12CCN(S(=O)(=O)c1ccccc1C(F)(F)F)CC2] | LCMS-C-3 | 4.59 | 468, 470 (M + H)+ |
| 46 | 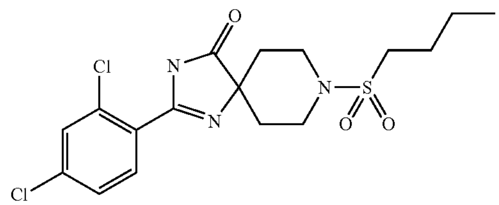 [SMILES: CCCCS(=O)(=O)N1CCC2(CC1)N=C(c1ccc(Cl)cc1Cl)NC2=O] | LCMS-A-1 | 2.45 | 418 (M + H)+ |
| 47 | 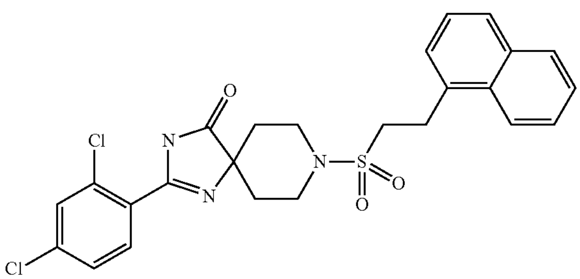 [SMILES: O=C1NC(c2ccc(Cl)cc2Cl)=NC12CCN(S(=O)(=O)CCc1cccc3ccccc13)CC2] | LCMS-A-1 | 2.94 | 516 (M + H)+ |

Example 6

2-(2,4-Dichloro-phenyl)-8-(quinoline-8-sulfonyl)-1,3,8-triaza-spiro[4.5]dec-1-en-4-one (Compound 48)

(Reaction 6-1)

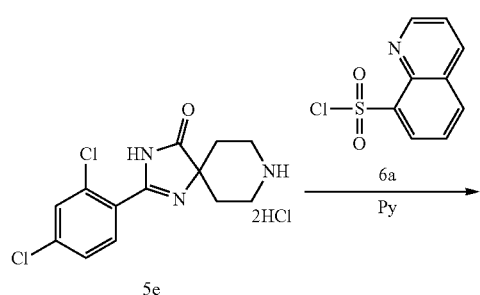

-continued

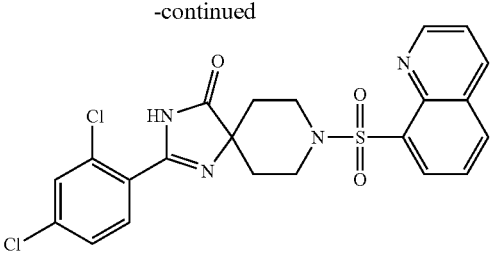

Compound 48

2-(2,4-Dichloro-phenyl)-8-(quinoline-8-sulfonyl)-1,3,8-triaza-spiro[4.5]dec-1-en-4-one was synthesized by operations similar to those in Reaction 4-2 of Example 4 using appropriate reagents and starting material and using pyridine as a base and solvent.

MS (ESI) m/z=490 (M+H)+.

The example compounds shown below were synthesized by operations similar to those in Example 6 using appropriate reagents and starting materials.

TABLE 6

| Compound | Structure | LCMS or HPLC condition | Retention time (min) | MS (m/z) |
|---|---|---|---|---|
| 49 | 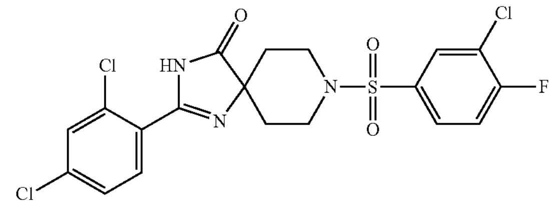 [SMILES: O=C1NC(c2ccc(Cl)cc2Cl)=NC12CCN(S(=O)(=O)c1ccc(F)c(Cl)c1)CC2] | LCMS-C-1 | 9.77 | 490 (M + H)+ |
| 50 | 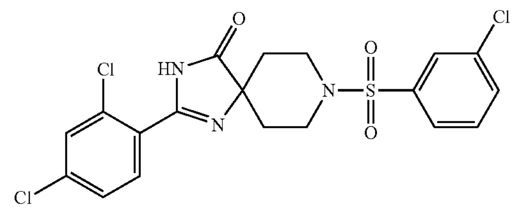 [SMILES: O=C1NC(c2ccc(Cl)cc2Cl)=NC12CCN(S(=O)(=O)c1cccc(Cl)c1)CC2] | LCMS-C-1 | 9.57 | 472 (M + H)+ |

Example 7

2-(2-Cyclohexyl-4-oxo-1,3,8-triaza-spiro[4.5]dec-1-ene-8-sulfonyl)-benzoic acid methyl ester (Compound 51)

2-Cyclohexyl-4-oxo-1,3,8-triaza-spiro[4.5]dec-1-ene-8-carboxylic acid tert-butyl ester was synthesized by operations similar to those in Reaction 5-1 and Reaction 5-2 of Example 5 using appropriate reagents and starting material.

MS (ESI) m/z=358 (M+Na)+.

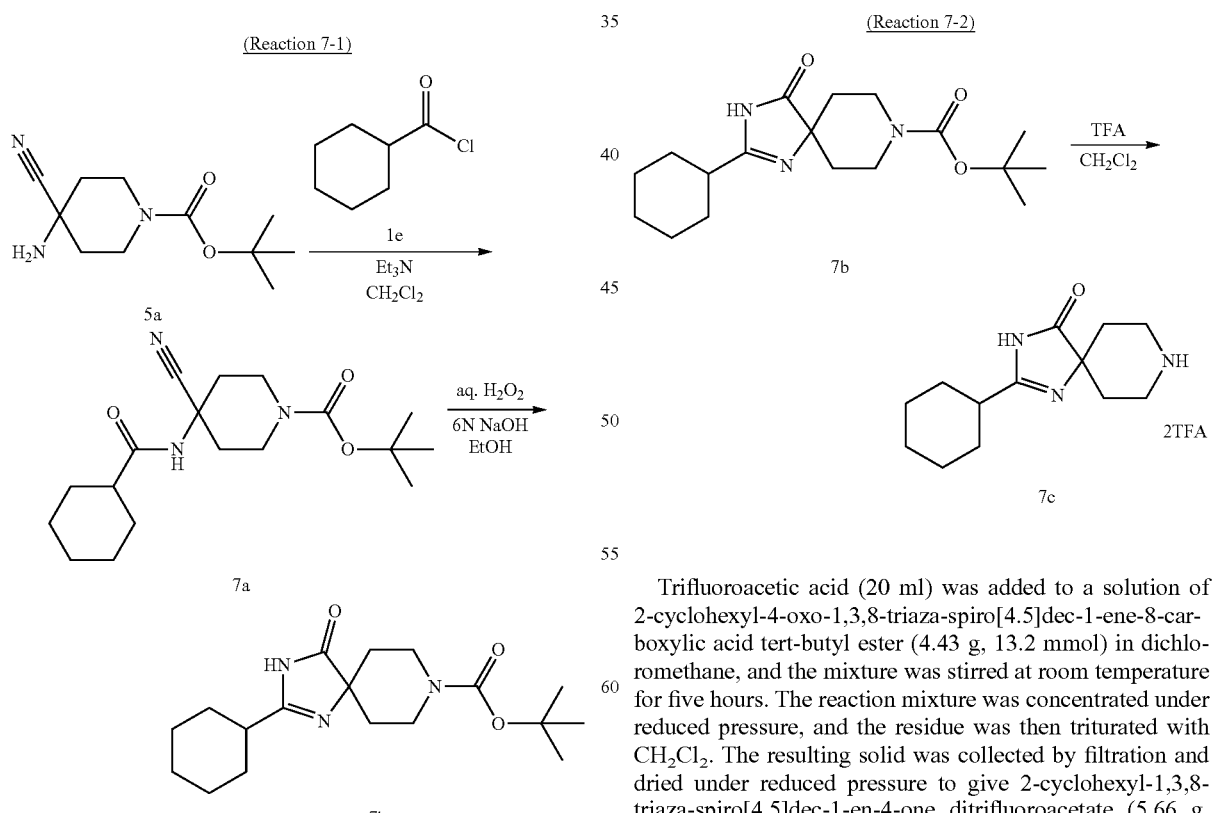

Trifluoroacetic acid (20 ml) was added to a solution of 2-cyclohexyl-4-oxo-1,3,8-triaza-spiro[4.5]dec-1-ene-8-carboxylic acid tert-butyl ester (4.43 g, 13.2 mmol) in dichloromethane, and the mixture was stirred at room temperature for five hours. The reaction mixture was concentrated under reduced pressure, and the residue was then triturated with CH$_2$Cl$_2$. The resulting solid was collected by filtration and dried under reduced pressure to give 2-cyclohexyl-1,3,8-triaza-spiro[4.5]dec-1-en-4-one ditrifluoroacetate (5.66 g, 92%).

MS (ESI) m/z=236 (M+H)+.

(Reaction 7-3)

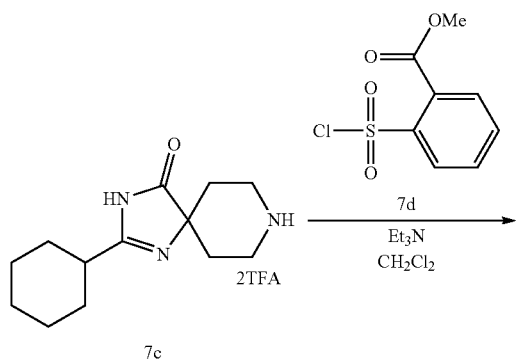

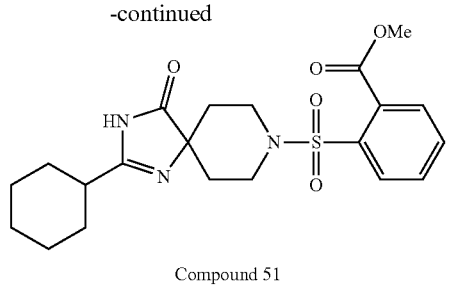

Compound 51

2-(2-Cyclohexyl-4-oxo-1,3,8-triaza-spiro[4.5]dec-1-ene-8-sulfonyl)-benzoic acid methyl ester was synthesized by operations similar to those in Reaction 5-4 of Example 5 using appropriate reagents and starting material.

MS (ESI) m/z=434 (M+H)+.

The example compounds shown below were synthesized by operations similar to those in Example 7 using appropriate reagents and starting materials.

TABLE 7

| Compound | Structure | LCMS or HPLC condition | Retention time (min) | MS (m/z) |
|---|---|---|---|---|
| 52 | 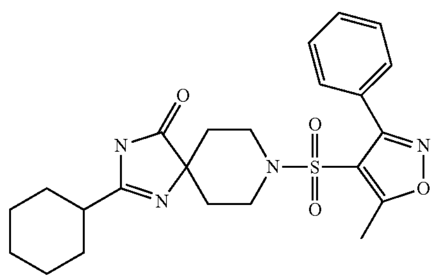 [SMILES: Cc1onc(-c2ccccc2)c1S(=O)(=O)N1CCC2(CC1)N=C(C1CCCCC1)NC2=O] | LCMS-E-1 | 3.584 | 458 (M + H)+ |
| 53 | 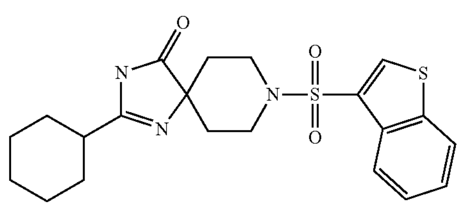 [SMILES: O=C1NC(C2CCCCC2)=NC12CCN(S(=O)(=O)c1csc3ccccc13)CC2] | LCMS-E-1 | 3.587 | 433 (M + H)+ |
| 54 | 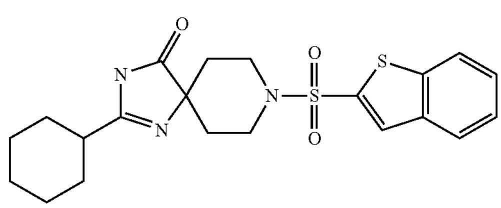 [SMILES: O=C1NC(C2CCCCC2)=NC12CCN(S(=O)(=O)c1cc3ccccc3s1)CC2] | LCMS-E-1 | 3.727 | 433 (M + H)+ |
| 55 | 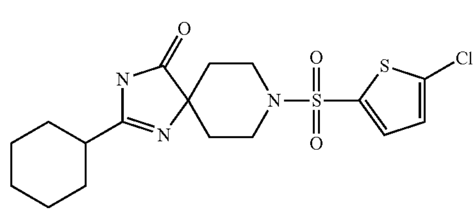 [SMILES: O=C1NC(C2CCCCC2)=NC12CCN(S(=O)(=O)c1ccc(Cl)s1)CC2] | LCMS-E-1 | 3.585 | 416 (M + H)+ |

TABLE 7-continued

| Compound | Structure | LCMS or HPLC condition | Retention time (min) | MS (m/z) |
|---|---|---|---|---|
| 56 | 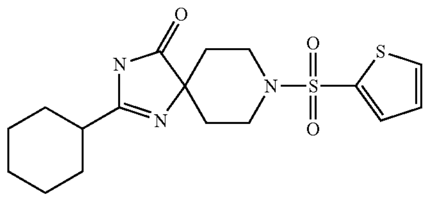 [SMILES: O=C1NC(C2CCCCC2)=NC12CCN(S(=O)(=O)c1cccs1)CC2] | LCMS-E-1 | 3.143 | 382 (M + H)+ |
| 57 | 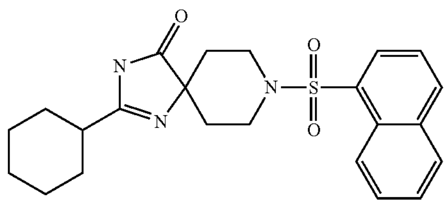 [SMILES: O=C1NC(C2CCCCC2)=NC12CCN(S(=O)(=O)c1cccc3ccccc13)CC2] | LCMS-E-1 | 3.604 | 427 (M + H)+ |
| 58 | 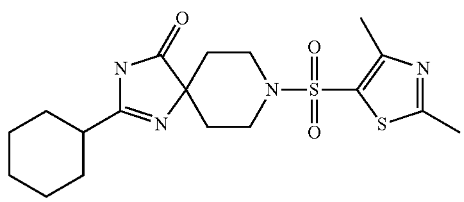 [SMILES: Cc1nc(C)c(S(=O)(=O)N2CCC3(CC2)N=C(C2CCCCC2)NC3=O)s1] | LCMS-E-2 | 1.22 | 411 (M + H)+ |
| 59 | 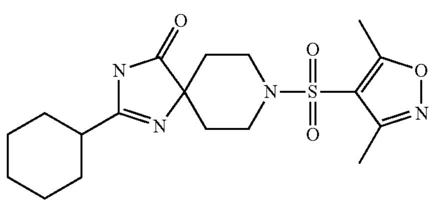 [SMILES: Cc1noc(C)c1S(=O)(=O)N1CCC2(CC1)N=C(C1CCCCC1)NC2=O] | LCMS-E-1 | 3.065 | 396 (M + H)+ |
| 60 | 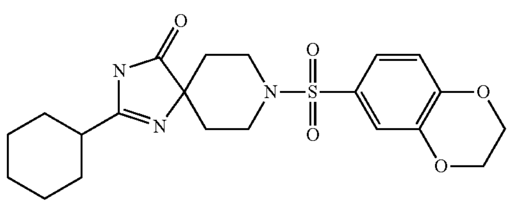 [SMILES: O=C1NC(C2CCCCC2)=NC12CCN(S(=O)(=O)c1ccc3c(c1)OCCO3)CC2] | LCMS-E-1 | 3.141 | 434 (M + H)+ |
| 61 | 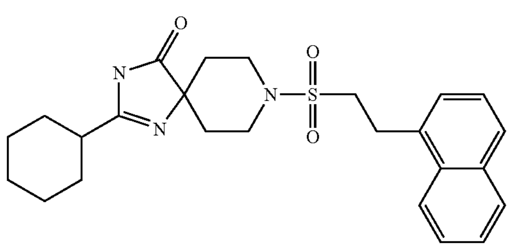 [SMILES: O=C1NC(C2CCCCC2)=NC12CCN(S(=O)(=O)CCc1cccc3ccccc13)CC2] | LCMS-E-1 | 3.782 | 454 (M + H)+ |
| 62 | 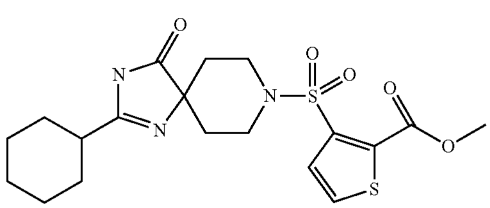 [SMILES: COC(=O)c1sccc1S(=O)(=O)N1CCC2(CC1)N=C(C1CCCCC1)NC2=O] | LCMS-C-1 | 2.35 | 440 (M + H)+ |

TABLE 7-continued

| Compound | Structure | LCMS or HPLC condition | Retention time (min) | MS (m/z) |
|---|---|---|---|---|
| 63 | 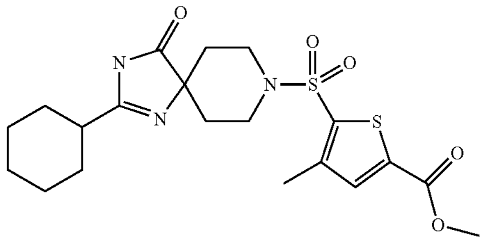 [SMILES: COC(=O)c1cc(C)c(S(=O)(=O)N2CCC3(CC2)N=C(C2CCCCC2)NC3=O)s1] | LCMS-C-1 | 2.64 | 454 (M + H)+ |
| 64 | 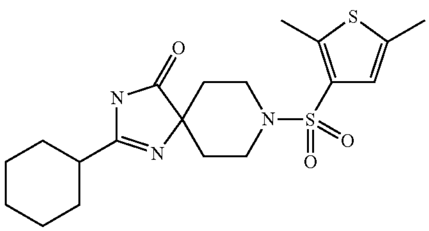 | LCMS-A-1 | 2.00 | 470 (M + H)+ |
| 65 | 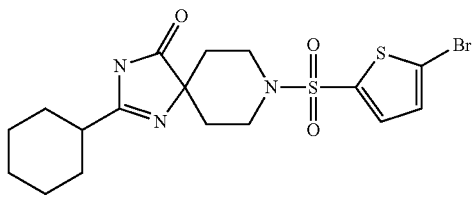 [SMILES: O=C1NC(C2CCCCC2)=NC12CCN(S(=O)(=O)c1ccc(Br)s1)CC2] | LCMS-C-2 | 2.13 | 461 (M + H)+ |

Example 8

8-(5-Chloro-thiophene-2-sulfonyl)-2-(3-trifluoromethyl-phenyl)-1,3,8-triaza-spiro[4.5]dec-1-en-4-one (Compound 66)

(Reaction 8-1)

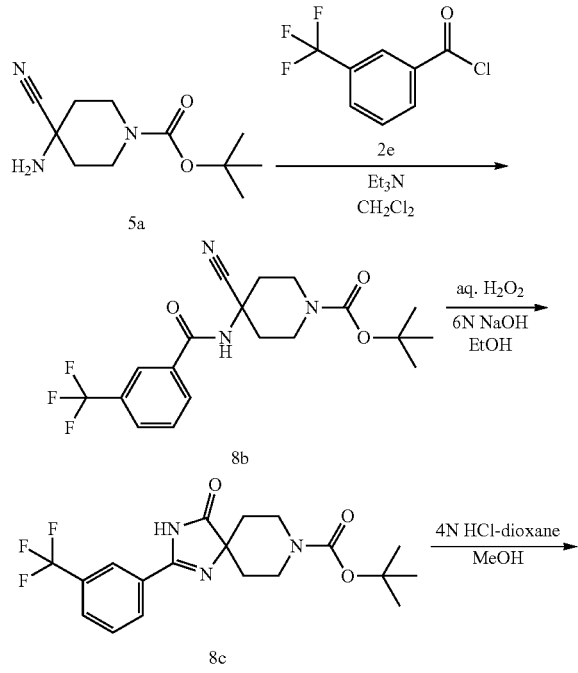

8-(5-Chloro-thiophene-2-sulfonyl)-2-(3-trifluoromethyl-phenyl)-1,3,8-triaza-spiro[4.5]dec-1-en-4-one was synthesized by operations similar to those in Example 5 using appropriate reagents and starting material.

MS (ESI) m/z=478 (M+H)+.

The example compounds shown below were synthesized by operations similar to those in Example 8 using appropriate reagents and starting materials.

TABLE 8
| Compound | Structure | LCMS or HPLC condition | Retention time (min) | MS (m/z) |
|---|---|---|---|---|
| 67 | 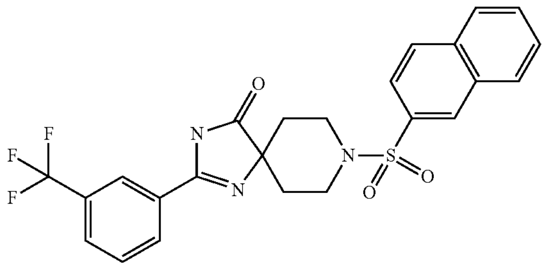 [SMILES: O=C1NC(c2cccc(C(F)(F)F)c2)=NC12CCN(S(=O)(=O)c1ccc3ccccc3c1)CC2] | LCMS-C-1 | 2.90 | 488 (M + H)+ |
| 68 | 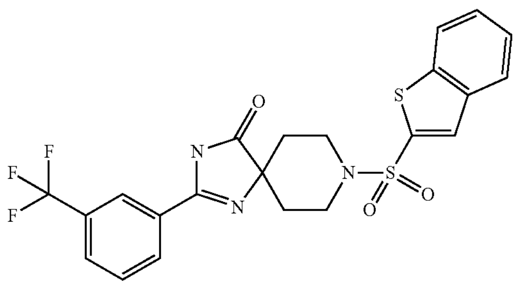 [SMILES: O=C1NC(c2cccc(C(F)(F)F)c2)=NC12CCN(S(=O)(=O)c1cc3ccccc3s1)CC2] | LCMS-C-1 | 2.92 | 494 (M + H)+ |
| 69 | 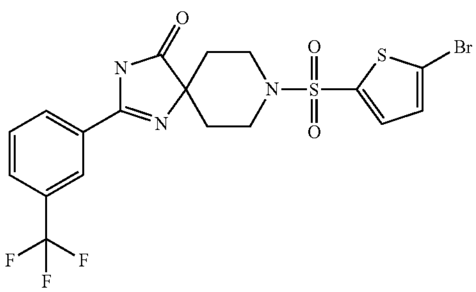 [SMILES: O=C1NC(c2cccc(C(F)(F)F)c2)=NC12CCN(S(=O)(=O)c1ccc(Br)s1)CC2] | LCMS-C-2 | 2.38 | 523 (M + H)+ |
Example 9
8-(3-Chloro-benzenesulfonyl)-2-cyclohexyl-1,3,8-triaza-spiro[4.6]undec-1-en-4-one (Compound 70)
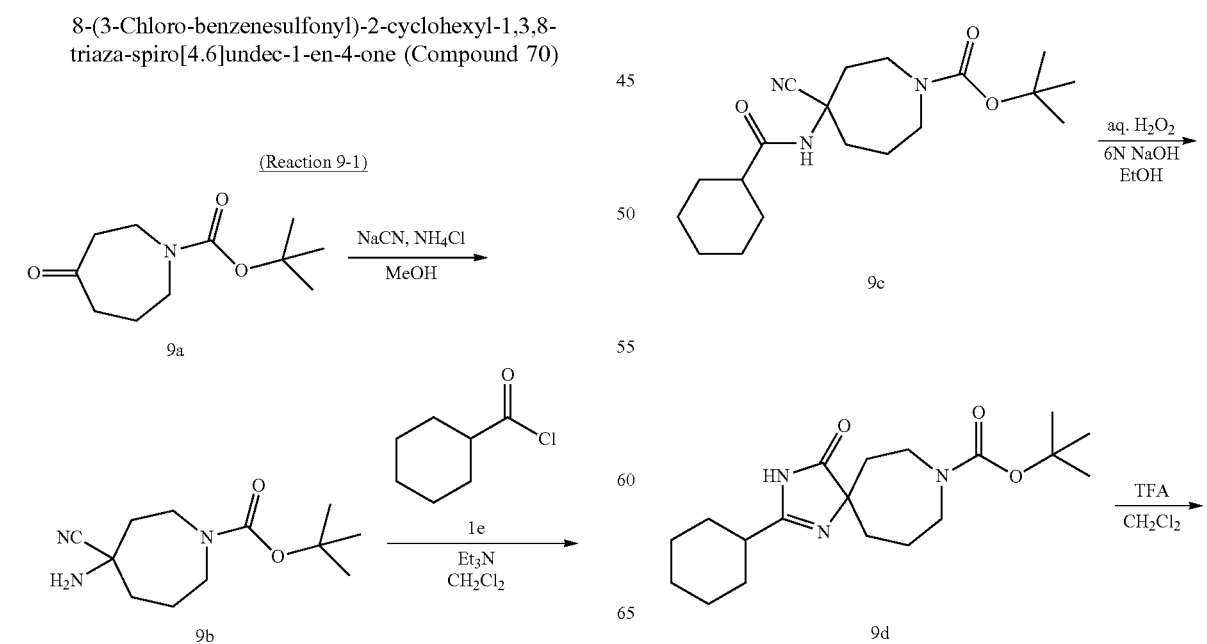
(Reaction 9-1)

Example 10

4-{2-[2-(2,4-Dichloro-phenyl)-4-oxo-1,3,8-triaza-spiro[4.5]dec-1-ene-8-sulfonyl]-ethyl}-3,N,N-trimethyl-benzamide (Compound 73)

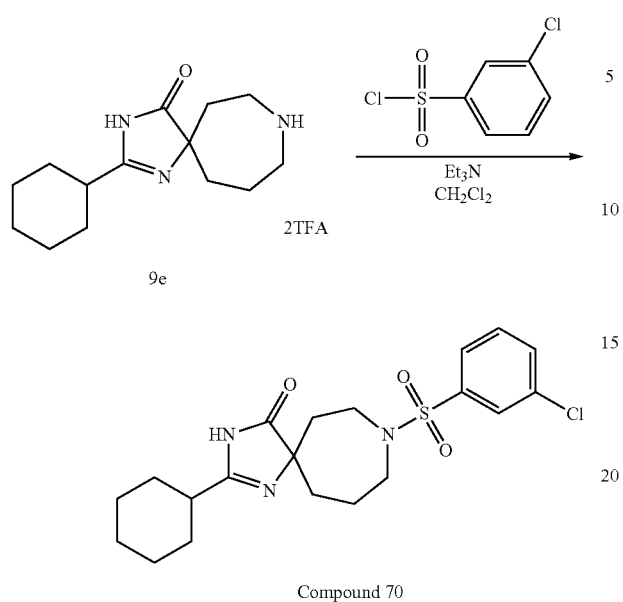

Compound 70

8-(3-Chloro-benzenesulfonyl)-2-cyclohexyl-1,3,8-triazaspiro[4.6]undec-1-en-4-one was synthesized by operations similar to those in Reaction 1-2 of Example 1 and Example 7 using appropriate reagents and starting material.

MS (ESI) m/z=424 (M+H)+.

The example compounds shown below were synthesized by operations similar to those in Example 9 using appropriate reagents and starting materials.

(Reaction 10-1)

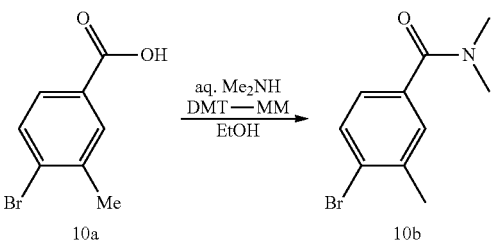

4-(4,6-Dimethoxy-1,3,5-triazin-2-yl)-4-methylmorpholinium chloride n-hydrate (n=about 2.7) (2.42 g, 7.53 mmol) was added to a mixture of 4-bromo-3-methylbenzoic acid (1.58 g, 7.37 mmol), EtOH (26 ml) and a 40% aqueous dimethylamine solution (0.75 ml, 7.4 mmol), and the mixture was stirred at room temperature for 24 hours. The reaction mixture was concentrated under reduced pressure, and the resulting residue was then dissolved in ethyl acetate. The organic layer was washed with water, and then dried over MgSO$_4$ and concentrated under reduced pressure. The resulting residue was purified by silica gel column chromatography (hexane/ethyl acetate=2/1) to give 4-bromo-3,N,N-trimethyl-benzamide as a colorless solid (1.16 g, 65%).

$^1$H-NMR (300 MHz) (CDCl$_3$) δ 2.42 (3H, s), 2.98 (3H, br s), 3.10 (3H, br s), 7.08 (1H, dd, J=8.4 and 2.1 Hz), 7.30 (1H, d, J=2.1 Hz), 7.55 (1H, d, J=8.4 Hz). MS (ESI) m/z=243 (M+H)+.

TABLE 9

| Compound | Structure | LCMS or HPLC condition | Retention time (min) | MS (m/z) |
| --- | --- | --- | --- | --- |
| 71 | (structure) | LCMS-E-2 | 2.78 | 410 (M + H)+ |
| 72 | (structure) | LCMS-E-2 | 2.81 | 396 (M + H)+ |

(Reaction 10-2)

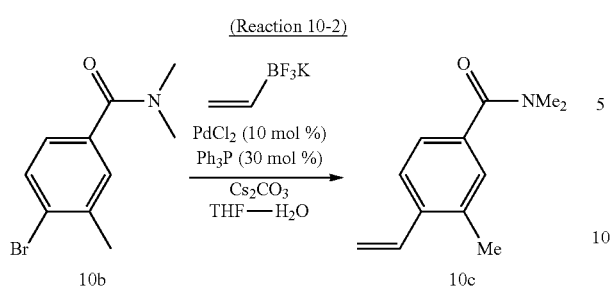

A mixture of 4-bromo-3,N,N-trimethyl-benzamide (798 mg, 3.30 mmol), potassium vinyltrifluoroborate (579 mg, 4.32 mmol), PdCl$_2$ (59.0 mg, 0.333 mmol), PPh$_3$ (265 mg, 1.01 mmol) and Cs$_2$CO$_3$ (3.22 g, 9.90 mmol) in THF (6.5 ml)-H$_2$O (0.65 ml) was heated with stirring at 85° C. for 21 hours in a sealed test tube in an N$_2$ atmosphere. The reaction mixture was cooled to room temperature and then extracted with ether. The organic layer was washed with water, and then dried over MgSO$_4$ and concentrated under reduced pressure. The resulting residue was purified by silica gel column chromatography (hexane/ethyl acetate=2/1) to give 3,N,N-trimethyl-4-vinyl-benzamide (565 mg, 90%).

$^1$H-NMR (400 MHz) (CDCl$_3$) δ 2.36 (3H, s), 3.00 (3H, br s), 3.10 (3H, br s), 5.35 (1H, dd, J=11.0 and 1.0 Hz), 5.68 (1H, dd, J=17.5 and 1.0 Hz), 6.93 (1H, dd, J=17.5 and 11.0 Hz), 7.21 (1H, d, J=8.0 Hz), 7.22 (1H, s), 7.48 (1H, d, J=8.0 Hz). MS (ESI) m/z=190 (M+H)+.

(Reaction 10-3)

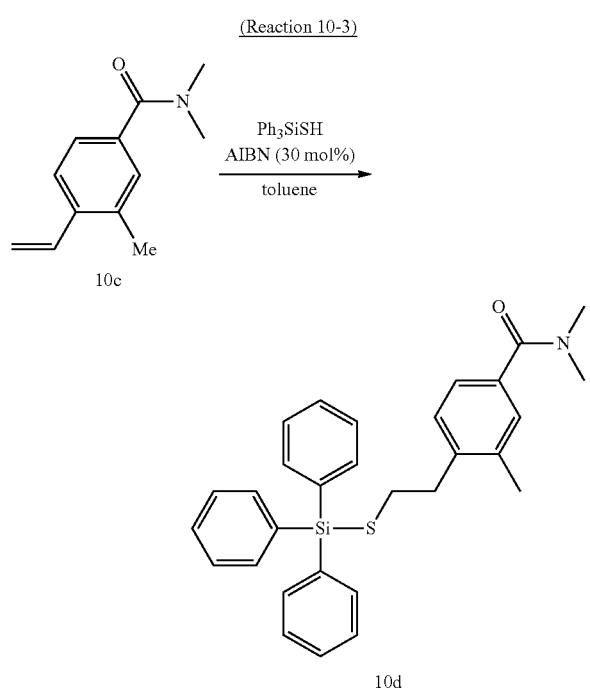

A mixture of 3,N,N-trimethyl-4-vinyl-benzamide (706 mg, 3.73 mmol), triphenylsilanethiol (1.76 g, 6.00 mmol) and AIBN (185 mg, 1.13 mmol) in toluene (16 ml) was heated with stirring at 88° C. for two hours in a sealed test tube in an N$_2$ atmosphere. The reaction mixture was cooled to room temperature and then concentrated under reduced pressure. The resulting residue was purified by silica gel column chromatography (hexane/ethyl acetate=2/1) to give 3,N,N-trimethyl-4-(2-triphenylsilanylsulfanyl-ethyl)-benzamide (1.24 g, 69%).

$^1$H-NMR (400 MHz) (CDCl$_3$) δ 2.08 (3H, s), 2.61 (2H, m), 2.75 (2H, m), 2.95 (3H, br s), 3.07 (3H, br s), 6.89 (1H, d, J=7.8 Hz), 7.08 (1H, d, J=7.8 Hz), 7.12 (1H, s), 7.37-7.47 (9H, m), 7.66-7.69 (6H, m). MS (ESI) m/z=482 (M+H)+.

(Reaction 10-4)

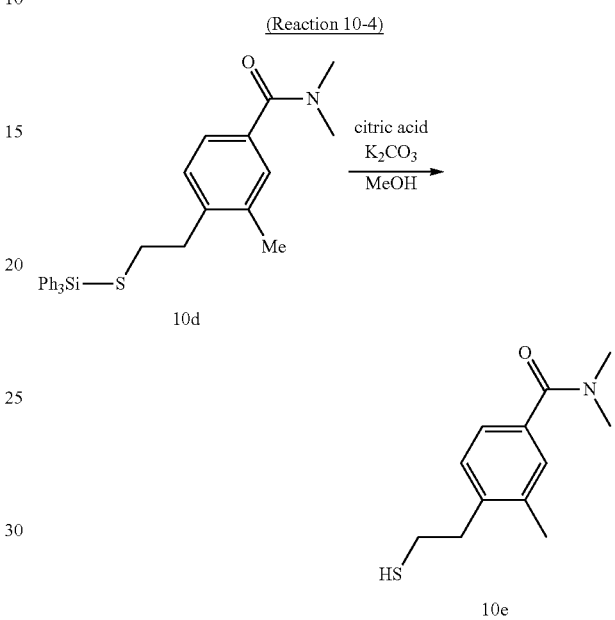

Citric acid monohydrate (110 mg, 0.523 mmol) and potassium carbonate (52.8 mg, 0.382 mmol) were added to a solution of 3,N,N-trimethyl-4-(2-triphenylsilanylsulfanyl-ethyl)-benzamide (767 mg, 1.59 mmol) in MeOH (27 ml) at room temperature, and the mixture was stirred for one hour. The reaction mixture was concentrated under reduced pressure, and the residue was then dissolved in dichloromethane. The organic layer was washed with water, and then dried over MgSO$_4$ and concentrated under reduced pressure. The resulting residue was purified by silica gel column chromatography (hexane/ethyl acetate=2/1) to give 4-(2-mercapto-ethyl)-3,N,N-trimethyl-benzamide (351 mg, 99%).

$^1$H-NMR (400 MHz) (CDCl$_3$) δ 2.33 (3H, s), 2.74 (2H, dt, J=7.5 and 7.5 Hz), 2.94 (2H, t, J=7.5 Hz), 2.99 (3H, br s), 3.10 (3H, br s), 7.16 (1H, d, J=7.8 Hz), 7.18 (1H, d, J=7.8 Hz), 7.23 (1H, s). MS (ESI) m/z=224 (M+H)+.

(Reaction 10-5)

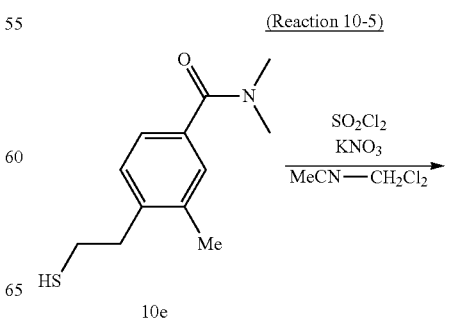

-continued

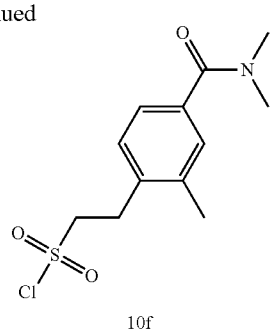

10f

Potassium nitrate (583 mg, 5.77 mmol) was added to a solution of 4-(2-mercapto-ethyl)-3,N,N-trimethyl-benzamide (514 mg, 2.30 mmol) in MeCN (23 ml) at room temperature. The mixture was cooled to −40° C., and sulfuryl chloride (1.68 M solution in dichloromethane, 3.46 ml, 5.81 mmol) was then added dropwise over 15 minutes. After stirring at −40° C. to −20° C. for 2.5 hours, the reaction mixture was diluted with dichloromethane (80 ml) and quenched with a saturated aqueous sodium bicarbonate solution (20 ml). The organic layer and the aqueous layer were separated, and the organic layer was then washed with a saturated aqueous sodium chloride solution (30 ml), dried over MgSO$_4$ and concentrated under reduced pressure. The resulting residue was purified by silica gel column chromatography (hexane/ethyl acetate=1/1→1/2) to give 2-(4-dimethylcarbamoyl-2-methyl-phenyl)-ethanesulfonyl chloride as a colorless solid (491 mg, 74%).

$^1$H-NMR (300 MHz) (CDCl$_3$) δ 2.39 (3H, s), 2.99 (3H, br s), 3.11 (3H, br s), 3.36 (2H, m), 3.83 (2H, m), 7.19 (1H, d, J=7.5 Hz), 7.23 (1H, dd, J=7.5 and 1.5 Hz), 7.28 (1H, d, J=1.5 Hz). MS (ESI) m/z=290 (M+H)+.

(Reaction 10-6)

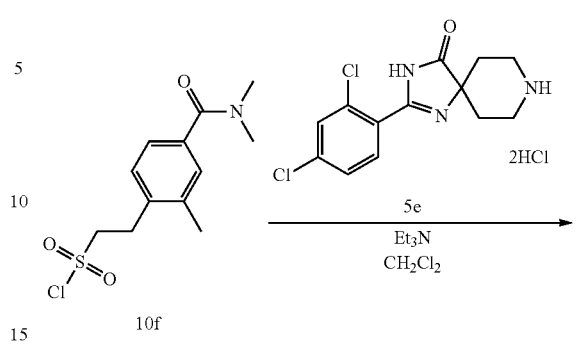

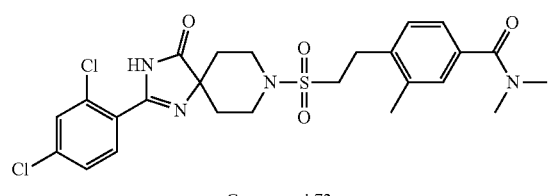

Compound 73

4-{2-[2-(2,4-Dichloro-phenyl)-4-oxo-1,3,8-triaza-spiro[4.5]dec-1-ene-8-sulfonyl]-ethyl}-3,N,N-trimethyl-benzamide was synthesized by operations similar to those in Reaction 5-4 of Example 5 using appropriate reagents and starting material.

MS (ESI) m/z=551 (M+H)+.

The example compounds shown below were synthesized by operations similar to those in Example 10 using appropriate reagents and starting materials.

Compounds 74 to 144

TABLE 10

| Compound | Structure | LCMS or HPLC condition | Retention time (min) | MS (m/z) |
|---|---|---|---|---|
| 74 | 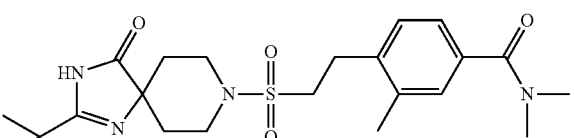 | LCMS-C-2 | 1.57 | 463 (M + H)+ |
| 75 | 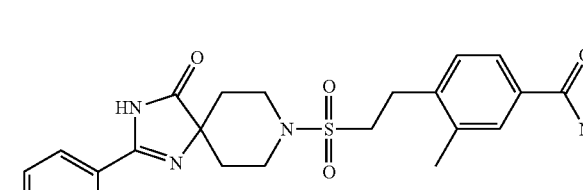 | LCMS-C-1 | 2.58 | 551 (M + H)+ |

TABLE 10-continued

| Compound | Structure | LCMS or HPLC condition | Retention time (min) | MS (m/z) |
|---|---|---|---|---|
| 76 | 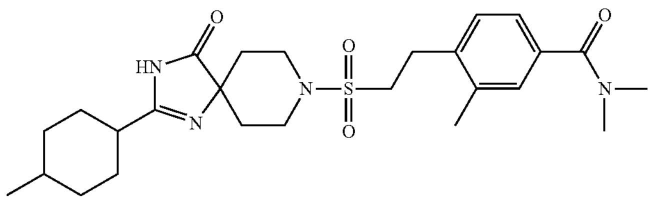 | LCMS-C-1 | 2.50 | 503 (M + H)+ |
| 77 | 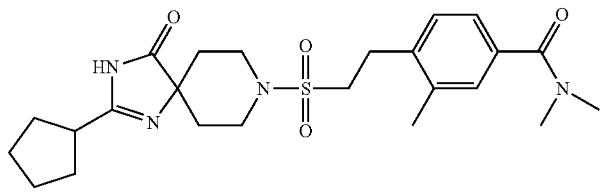 [SMILES: Cc1cc(C(=O)N(C)C)ccc1CCS(=O)(=O)N1CCC2(CC1)N=C(C1CCCC1)NC2=O] | LCMS-C-1 | 2.22 | 475 (M + H)+ |
| 78 | 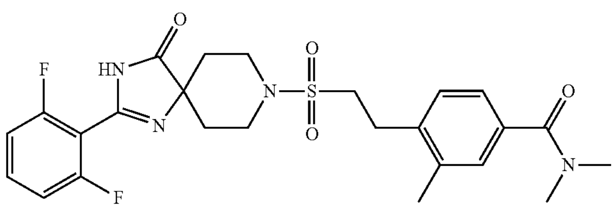 [SMILES: Cc1cc(C(=O)N(C)C)ccc1CCS(=O)(=O)N1CCC2(CC1)N=C(c1c(F)cccc1F)NC2=O] | LCMS-C-1 | 2.13 | 519 (M + H)+ |
| 79 | 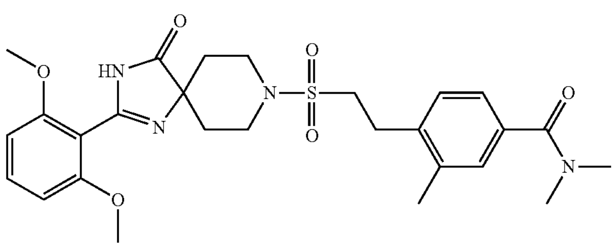 [SMILES: COc1cccc(OC)c1C1=NC2(CCN(S(=O)(=O)CCc3ccc(C(=O)N(C)C)cc3C)CC2)C(=O)N1] | LCMS-A-1 | 1.88 | 543 (M + H)+ |
| 80 | 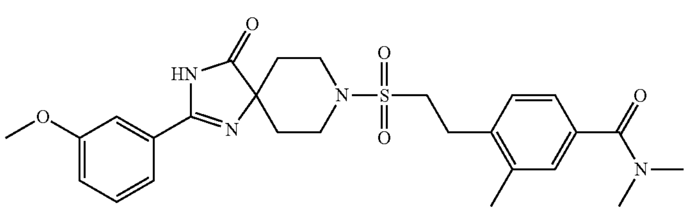 | LCMS-C-1 | 2.32 | 513 (M + H)+ |
| 81 | 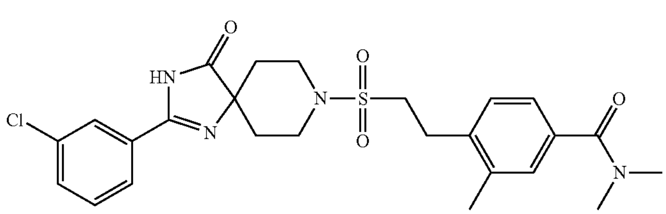 [SMILES: Cc1cc(C(=O)N(C)C)ccc1CCS(=O)(=O)N1CCC2(CC1)N=C(c1cccc(Cl)c1)NC2=O] | LCMS-C-1 | 2.50 | 517 (M + H)+ |

TABLE 10-continued

| Compound | Structure | LCMS or HPLC condition | Retention time (min) | MS (m/z) |
|---|---|---|---|---|
| 82 | 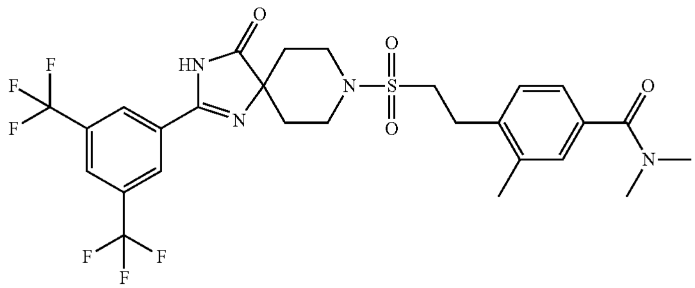 [SMILES: Cc1cc(C(=O)N(C)C)ccc1CCS(=O)(=O)N1CCC2(CC1)N=C(c1cc(C(F)(F)F)cc(C(F)(F)F)c1)NC2=O] | LCMS-A-1 | 2.72 | 619 (M + H)+ |
| 83 | 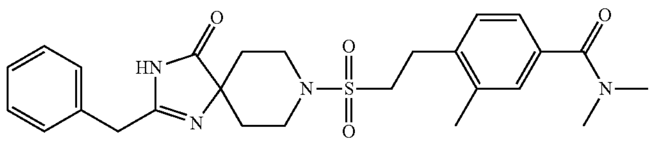 [SMILES: Cc1cc(C(=O)N(C)C)ccc1CCS(=O)(=O)N1CCC2(CC1)N=C(Cc1ccccc1)NC2=O] | LCMS-C-1 | 2.23 | 497 (M + H)+ |
| 84 | 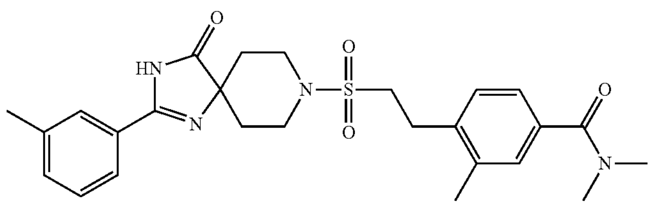 | LCQ-01 | 2.01 | 497 (M + H)+ |
| 85 | 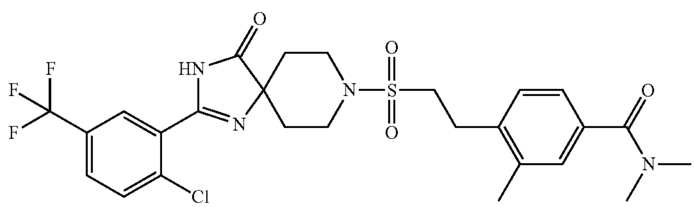 [SMILES: Cc1cc(C(=O)N(C)C)ccc1CCS(=O)(=O)N1CCC2(CC1)N=C(c1cc(C(F)(F)F)ccc1Cl)NC2=O] | LCMS-C-1 | 2.47 | 585 (M + H)+ |
| 86 | 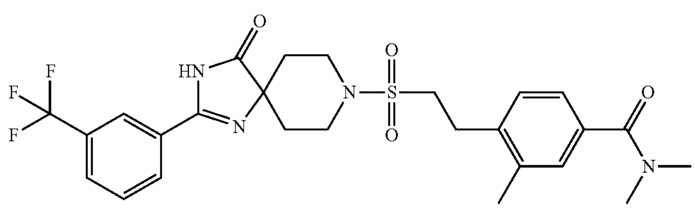 [SMILES: Cc1cc(C(=O)N(C)C)ccc1CCS(=O)(=O)N1CCC2(CC1)N=C(c1cccc(C(F)(F)F)c1)NC2=O] | LCMS-C-1 | 2.57 | 551 (M + H)+ |
| 87 | 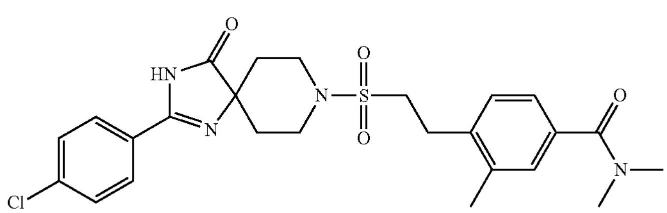 [SMILES: Cc1cc(C(=O)N(C)C)ccc1CCS(=O)(=O)N1CCC2(CC1)N=C(c1ccc(Cl)cc1)NC2=O] | LCMS-C-1 | 2.48 | 517 (M + H)+ |
| 88 | 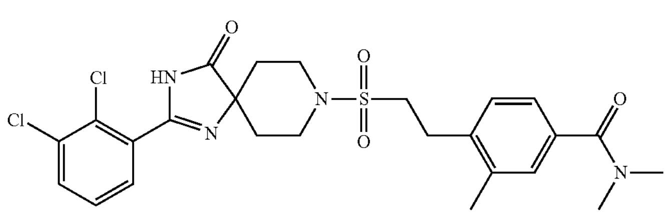 | LCMS-C-1 | 2.43 | 551 (M + H)+ |

TABLE 10-continued

| Compound | Structure | LCMS or HPLC condition | Retention time (min) | MS (m/z) |
|---|---|---|---|---|
| 89 | 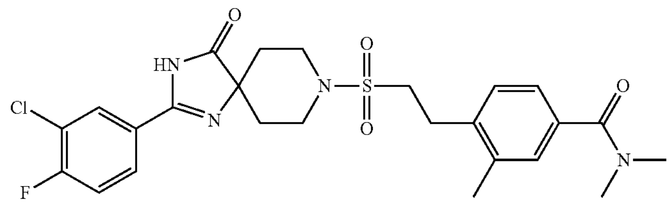 [SMILES: Cc1cc(C(=O)N(C)C)ccc1CCS(=O)(=O)N1CCC2(CC1)N=C(c1ccc(F)c(Cl)c1)NC2=O] | LCMS-C-1 | 2.53 | 535 (M + H)+ |
| 90 | 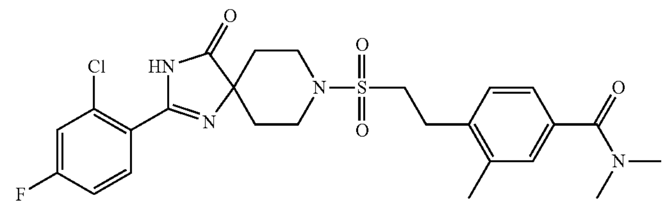 [SMILES: Cc1cc(C(=O)N(C)C)ccc1CCS(=O)(=O)N1CCC2(CC1)N=C(c1ccc(F)cc1Cl)NC2=O] | LCMS-C-1 | 2.30 | 535 (M + H)+ |
| 91 | 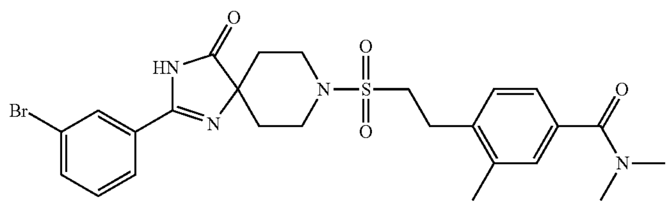 | LCMS-B-1 | 2.01 | 561 (M + H)+ |
| 92 | 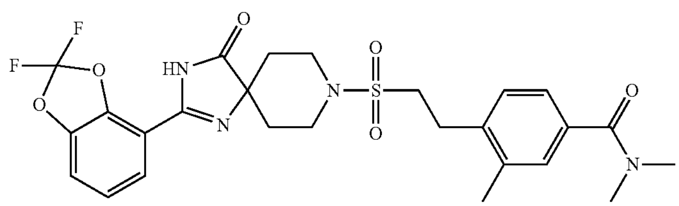 [SMILES: Cc1cc(C(=O)N(C)C)ccc1CCS(=O)(=O)N1CCC2(CC1)N=C(c1cccc3c1OC(F)(F)O3)NC2=O] | LCMS-C-2 | 1.87 | 563 (M + H)+ |
| 93 | 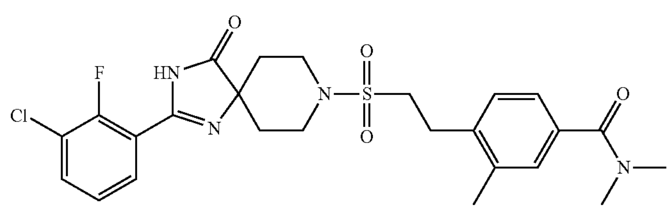 [SMILES: Cc1cc(C(=O)N(C)C)ccc1CCS(=O)(=O)N1CCC2(CC1)N=C(c1cccc(Cl)c1F)NC2=O] | LCMS-B-1 | 1.97 | 535 (M + H)+ |
| 94 | 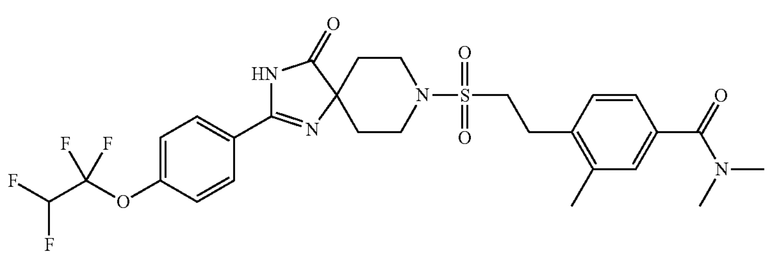 [SMILES: Cc1cc(C(=O)N(C)C)ccc1CCS(=O)(=O)N1CCC2(CC1)N=C(c1ccc(OC(F)(F)C(F)F)cc1)NC2=O] | LCMS-C-1 | 2.52 | 599 (M + H)+ |
| 95 | 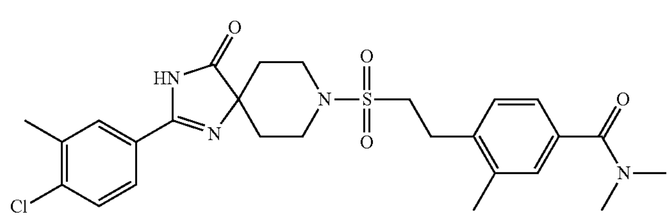 | LCMS-C-1 | 2.60 | 531 (M + H)+ |

TABLE 10-continued

| Compound | Structure | LCMS or HPLC condition | Retention time (min) | MS (m/z) |
|---|---|---|---|---|
| 96 | 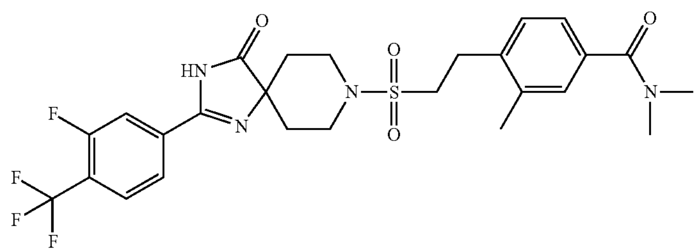 [SMILES: Cc1cc(C(=O)N(C)C)ccc1CCS(=O)(=O)N1CCC2(CC1)N=C(c1ccc(C(F)(F)F)c(F)c1)NC2=O] | LCMS-C-1 | 2.38 | 569 (M + H)+ |
| 97 | 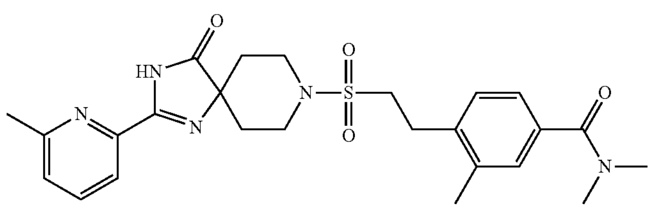 | LCMS-C-1 | 2.22 | 498 (M + H)+ |
| 98 | 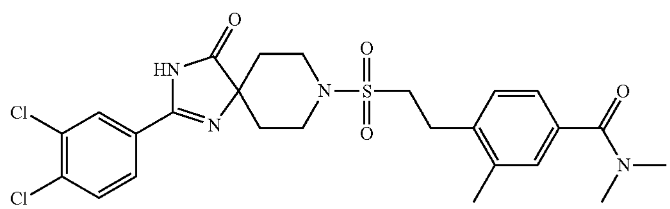 | LCMS-C-1 | 2.67 | 551 (M + H)+ |
| 99 | 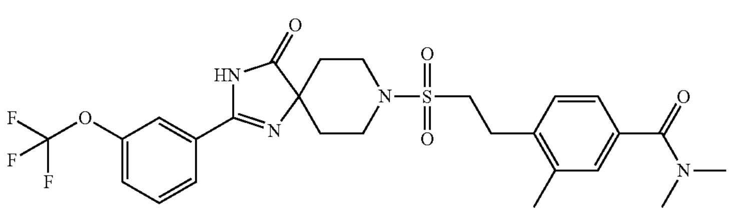 [SMILES: Cc1cc(C(=O)N(C)C)ccc1CCS(=O)(=O)N1CCC2(CC1)N=C(c1cccc(OC(F)(F)F)c1)NC2=O] | LCMS-C-1 | 2.60 | 567 (M + H)+ |
| 100 | 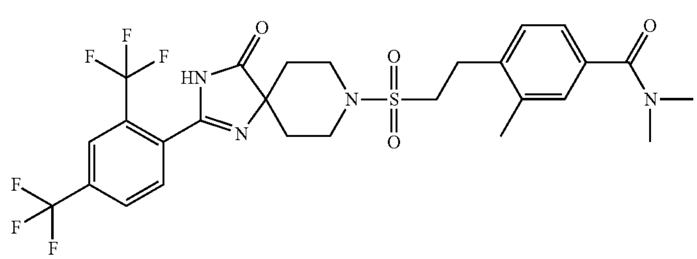 [SMILES: Cc1cc(C(=O)N(C)C)ccc1CCS(=O)(=O)N1CCC2(CC1)N=C(c1ccc(C(F)(F)F)cc1C(F)(F)F)NC2=O] | LCMS-C-1 | 2.63 | 619 (M + H)+ |
| 101 | 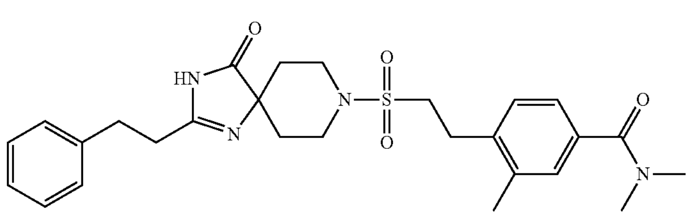 [SMILES: Cc1cc(C(=O)N(C)C)ccc1CCS(=O)(=O)N1CCC2(CC1)N=C(CCc1ccccc1)NC2=O] | LCMS-C-1 | 2.33 | 511 (M + H)+ |

TABLE 10-continued

| Compound | Structure | LCMS or HPLC condition | Retention time (min) | MS (m/z) |
|---|---|---|---|---|
| 102 | 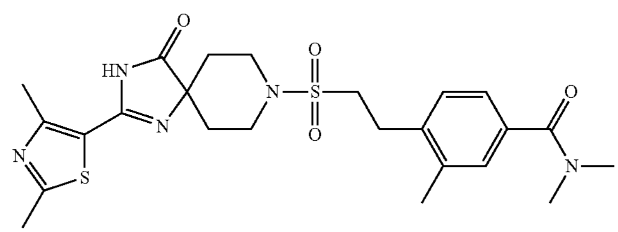 [SMILES: Cc1nc(C)c(C2=NC3(CCN(S(=O)(=O)CCc4ccc(C(=O)N(C)C)cc4C)CC3)C(=O)N2)s1] | LCMS-C-1 | 2.07 | 518 (M + H)+ |
| 103 | 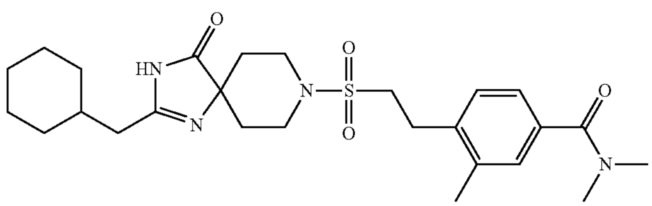 [SMILES: Cc1cc(C(=O)N(C)C)ccc1CCS(=O)(=O)N1CCC2(CC1)N=C(CC1CCCCC1)NC2=O] | LCMS-A-1 | 2.02 | 503 (M + H)+ |
| 104 | 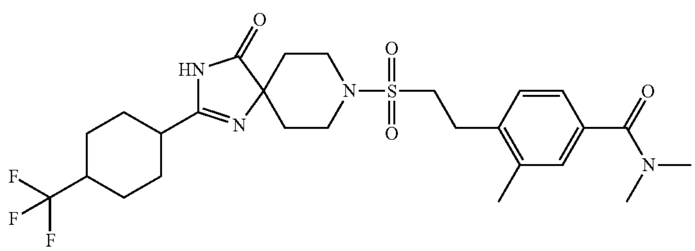 [SMILES: Cc1cc(C(=O)N(C)C)ccc1CCS(=O)(=O)N1CCC2(CC1)N=C(C1CCC(C(F)(F)F)CC1)NC2=O] | LCMS-A-1 | 2.12 | 557 (M + H)+ |
| 105 | 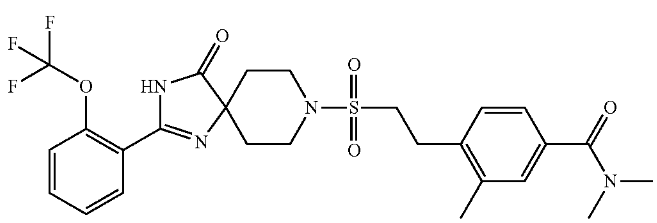 [SMILES: Cc1cc(C(=O)N(C)C)ccc1CCS(=O)(=O)N1CCC2(CC1)N=C(c1ccccc1OC(F)(F)F)NC2=O] | LCMS-C-1 | 2.40 | 567 (M + H)+ |
| 106 | 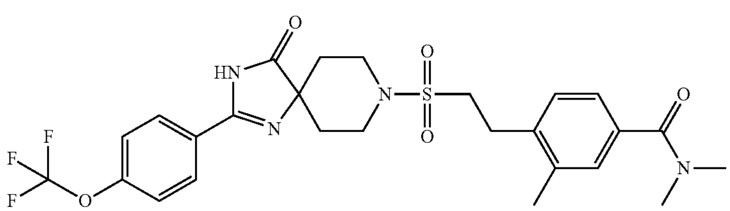 [SMILES: Cc1cc(C(=O)N(C)C)ccc1CCS(=O)(=O)N1CCC2(CC1)N=C(c1ccc(OC(F)(F)F)cc1)NC2=O] | LCMS-C-1 | 2.62 | 567 (M + H)+ |
| 107 | 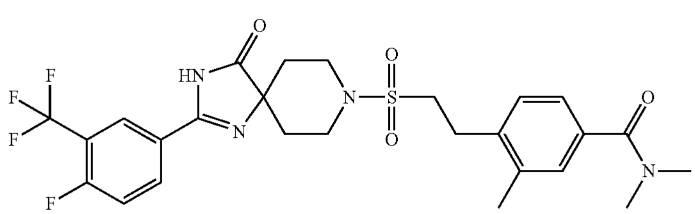 [SMILES: Cc1cc(C(=O)N(C)C)ccc1CCS(=O)(=O)N1CCC2(CC1)N=C(c1ccc(F)c(C(F)(F)F)c1)NC2=O] | LCMS-C-2 | 1.97 | 569 (M + H)+ |

TABLE 10-continued

| Compound | Structure | LCMS or HPLC condition | Retention time (min) | MS (m/z) |
|---|---|---|---|---|
| 108 | 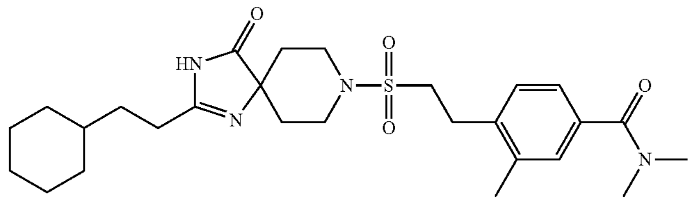 [SMILES: Cc1cc(C(=O)N(C)C)ccc1CCS(=O)(=O)N1CCC2(CC1)N=C(CCC1CCCCC1)NC2=O] | LCMS-C-1 | 2.65 | 517 (M + H)+ |
| 109 | 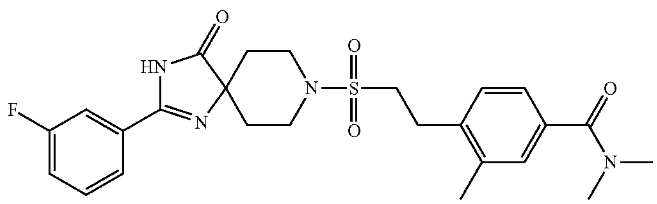 [SMILES: Cc1cc(C(=O)N(C)C)ccc1CCS(=O)(=O)N1CCC2(CC1)N=C(c1cccc(F)c1)NC2=O] | LCMS-A-1 | 2.10 | 501 (M + H)+ |
| 110 | 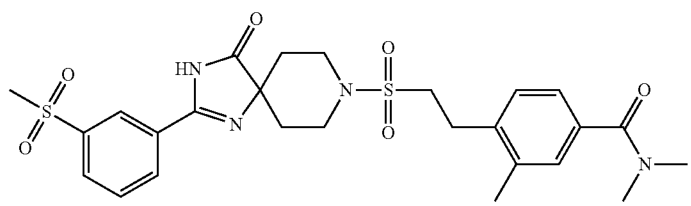 | LCMS-A-1 | 1.96 | 561 (M + H)+ |
| 111 | 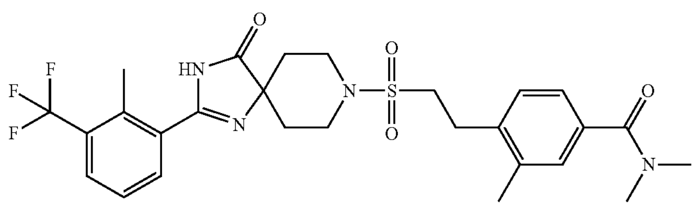 [SMILES: Cc1cc(C(=O)N(C)C)ccc1CCS(=O)(=O)N1CCC2(CC1)N=C(c1cccc(C(F)(F)F)c1C)NC2=O] | LCMS-C-1 | 2.52 | 565 (M + H)+ |
| 112 | 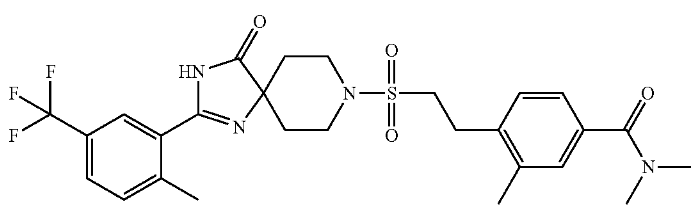 [SMILES: Cc1cc(C(=O)N(C)C)ccc1CCS(=O)(=O)N1CCC2(CC1)N=C(c1cc(C(F)(F)F)ccc1C)NC2=O] | LCMS-C-1 | 2.52 | 565 (M + H)+ |
| 113 | 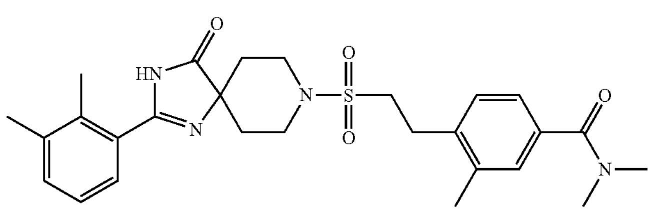 | LCMS-B-1 | 1.78 | 511 (M + H)+ |
| 114 | 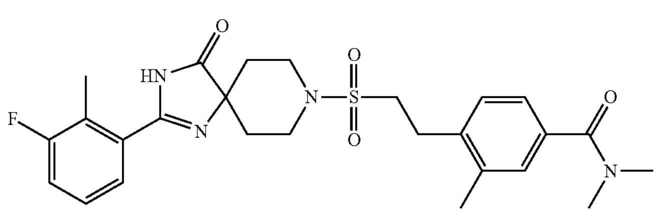 [SMILES: Cc1cc(C(=O)N(C)C)ccc1CCS(=O)(=O)N1CCC2(CC1)N=C(c1cccc(F)c1C)NC2=O] | LCMS-B-1 | 1.87 | 515 (M + H)+ |

TABLE 10-continued

| Compound | Structure | LCMS or HPLC condition | Retention time (min) | MS (m/z) |
|---|---|---|---|---|
| 115 | 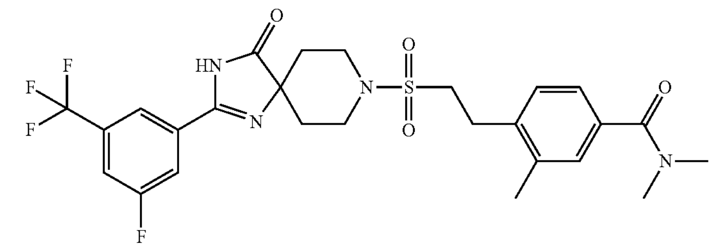 | LCMS-C-1 | 2.67 | 569 (M + H)+ |
| 116 | 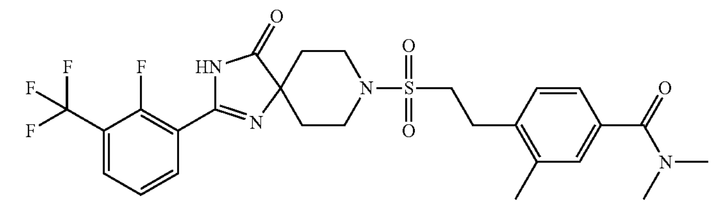 [SMILES: Cc1cc(C(=O)N(C)C)ccc1CCS(=O)(=O)N1CCC2(CC1)N=C(c1cccc(C(F)(F)F)c1F)NC2=O] | LCMS-C-1 | 2.50 | 569 (M + H)+ |
| 117 | 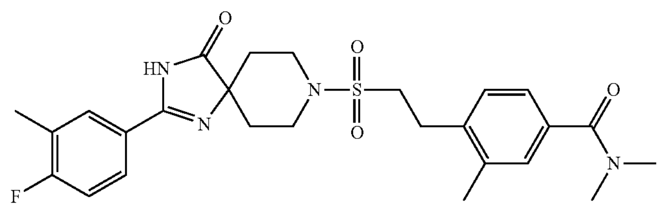 | LCMS-A-1 | 2.12 | 515 (M + H)+ |
| 118 | 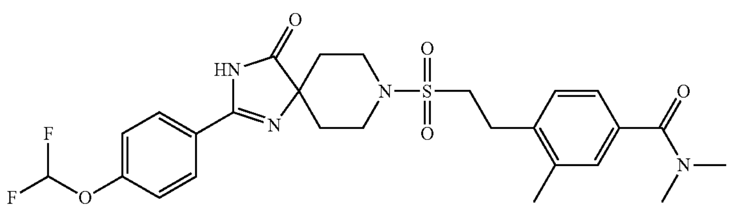 [SMILES: Cc1cc(C(=O)N(C)C)ccc1CCS(=O)(=O)N1CCC2(CC1)N=C(c1ccc(OC(F)F)cc1)NC2=O] | LCMS-C-1 | 2.38 | 549 (M + H)+ |
| 119 | 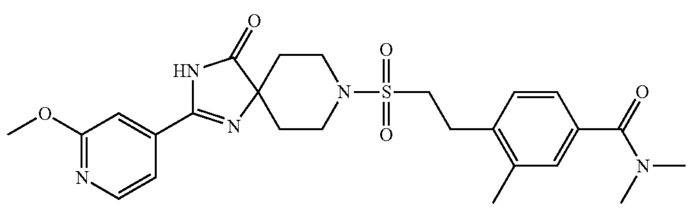 | LCMS-C-1 | 2.27 | 514 (M + H)+ |
| 120 | 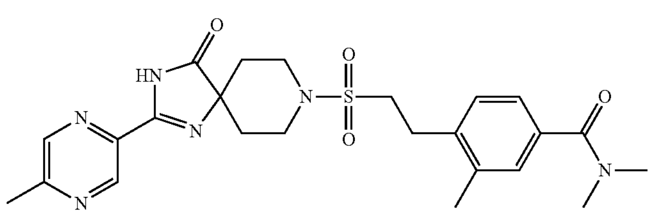 | LCMS-C-1 | 2.10 | 499 (M + H)+ |
| 121 | 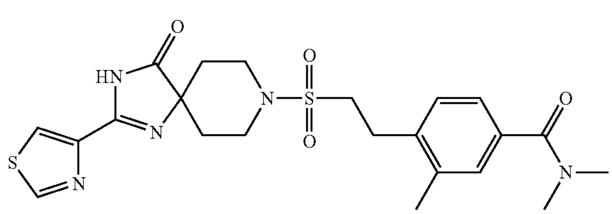 [SMILES: Cc1cc(C(=O)N(C)C)ccc1CCS(=O)(=O)N1CCC2(CC1)N=C(c1cscn1)NC2=O] | LCMS-C-1 | 1.98 | 490 (M + H)+ |

TABLE 10-continued

| Compound | Structure | LCMS or HPLC condition | Retention time (min) | MS (m/z) |
|---|---|---|---|---|
| 122 | 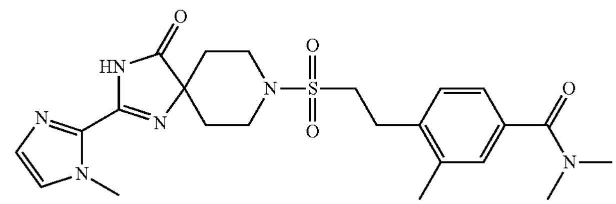 [SMILES: Cc1cc(C(=O)N(C)C)ccc1CCS(=O)(=O)N1CCC2(CC1)N=C(c1nccn1C)NC2=O] | LCMS-C-1 | 2.05 | 487 (M + H)+ |
| 123 | 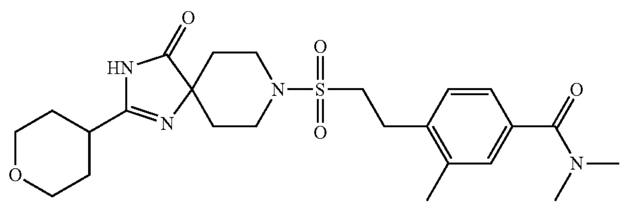 [SMILES: Cc1cc(C(=O)N(C)C)ccc1CCS(=O)(=O)N1CCC2(CC1)N=C(C1CCOCC1)NC2=O] | LCMS-C-1 | 1.95 | 491 (M + H)+ |
| 124 | 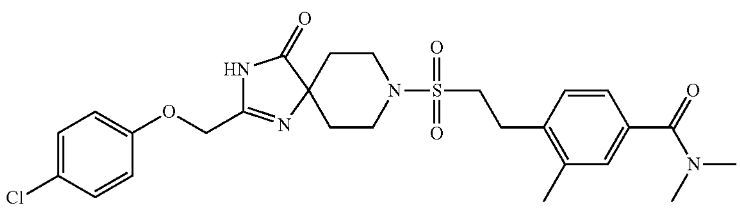 [SMILES: Cc1cc(C(=O)N(C)C)ccc1CCS(=O)(=O)N1CCC2(CC1)N=C(COc1ccc(Cl)cc1)NC2=O] | LCMS-C-1 | 2.48 | 547 (M + H)+ |
| 125 | 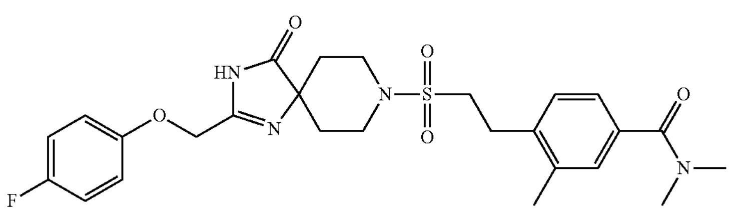 [SMILES: Cc1cc(C(=O)N(C)C)ccc1CCS(=O)(=O)N1CCC2(CC1)N=C(COc1ccc(F)cc1)NC2=O] | LCMS-C-1 | 2.32 | 531 (M + H)+ |
| 126 | 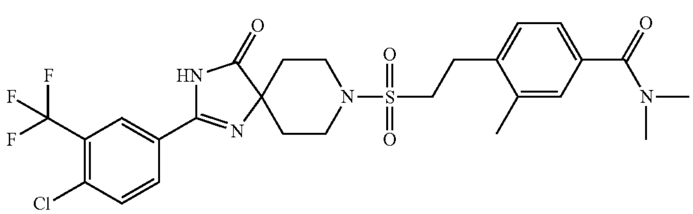 [SMILES: Cc1cc(C(=O)N(C)C)ccc1CCS(=O)(=O)N1CCC2(CC1)N=C(c1ccc(Cl)c(C(F)(F)F)c1)NC2=O] | LCMS-C-1 | 2.72 | 585 (M + H)+ |
| 127 | 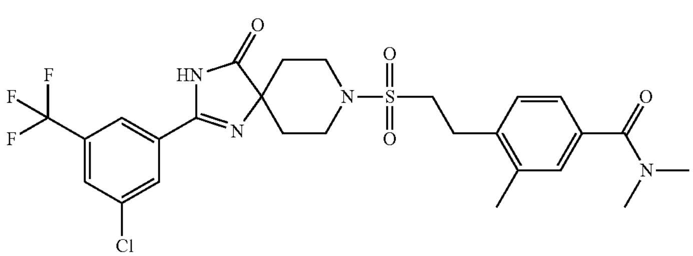 [SMILES: Cc1cc(C(=O)N(C)C)ccc1CCS(=O)(=O)N1CCC2(CC1)N=C(c1cc(Cl)cc(C(F)(F)F)c1)NC2=O] | LCMS-C-1 | 2.78 | 585 (M + H)+ |

TABLE 10-continued

| Compound | Structure | LCMS or HPLC condition | Retention time (min) | MS (m/z) |
|---|---|---|---|---|
| 128 | 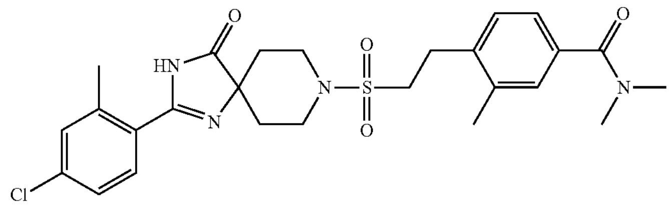 [SMILES: Cc1cc(C(=O)N(C)C)ccc1CCS(=O)(=O)N1CCC2(CC1)N=C(c1ccc(Cl)cc1C)NC2=O] | LCMS-C-1 | 2.42 | 531 (M + H)+ |
| 129 | 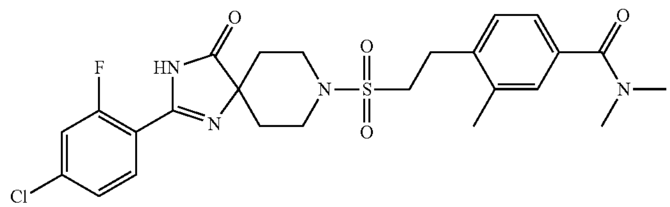 [SMILES: Cc1cc(C(=O)N(C)C)ccc1CCS(=O)(=O)N1CCC2(CC1)N=C(c1ccc(Cl)cc1F)NC2=O] | LCMS-C-1 | 2.42 | 535 (M + H)+ |
| 130 | 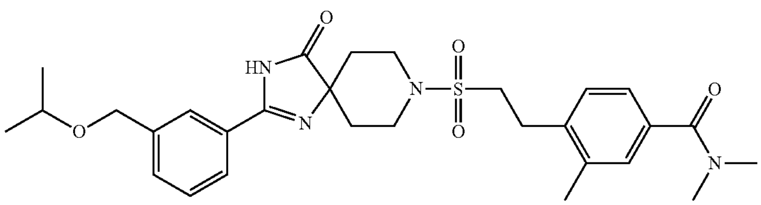 [SMILES: Cc1cc(C(=O)N(C)C)ccc1CCS(=O)(=O)N1CCC2(CC1)N=C(c1cccc(COC(C)C)c1)NC2=O] | LCMS-A-1 | 2.19 | 555 (M + H)+ |
| 131 | 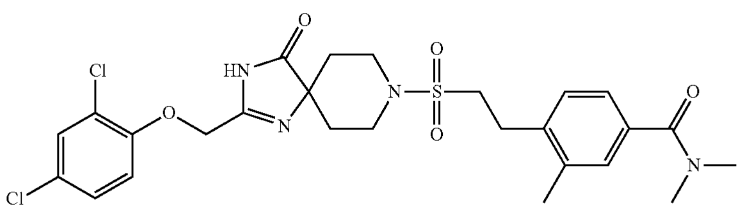 [SMILES: Cc1cc(C(=O)N(C)C)ccc1CCS(=O)(=O)N1CCC2(CC1)N=C(COc1ccc(Cl)cc1Cl)NC2=O] | LCMS-A-1 | 2.45 | 581 (M + H)+ |
| 133 | 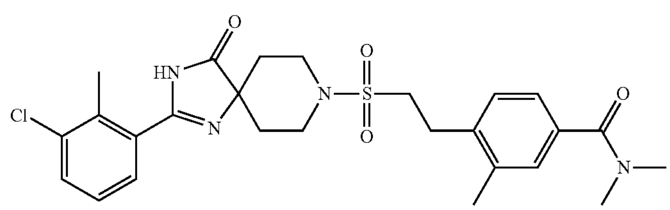 | LCMS-C-1 | 2.45 | 531 (M + H)+ |
| 134 | 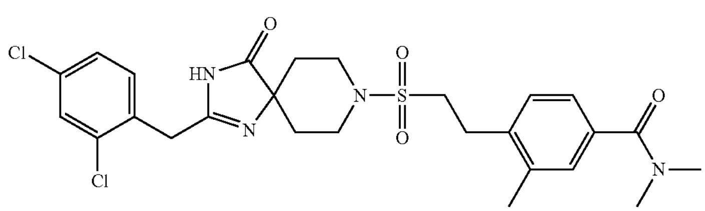 [SMILES: Cc1cc(C(=O)N(C)C)ccc1CCS(=O)(=O)N1CCC2(CC1)N=C(Cc1ccc(Cl)cc1Cl)NC2=O] | LCMS-C-1 | 2.50 | 565 (M + H)+ |
| 135 | 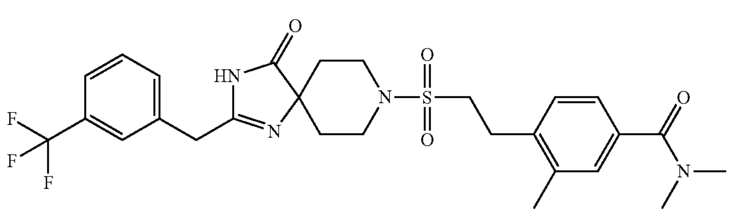 [SMILES: Cc1cc(C(=O)N(C)C)ccc1CCS(=O)(=O)N1CCC2(CC1)N=C(Cc1cccc(C(F)(F)F)c1)NC2=O] | LCMS-C-1 | 2.50 | 565 (M + H)+ |

TABLE 10-continued

| Compound | Structure | LCMS or HPLC condition | Retention time (min) | MS (m/z) |
|---|---|---|---|---|
| 136 | 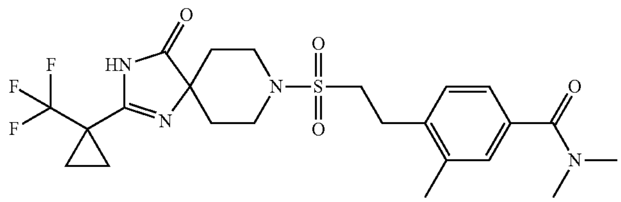 [SMILES: Cc1cc(C(=O)N(C)C)ccc1CCS(=O)(=O)N1CCC2(CC1)N=C(C1(C(F)(F)F)CC1)NC2=O] | LCMS-C-2 | 1.68 | 515 (M + H)+ |
| 137 | 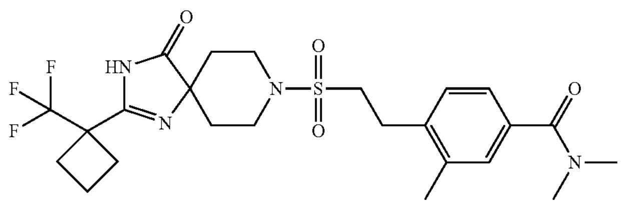 [SMILES: Cc1cc(C(=O)N(C)C)ccc1CCS(=O)(=O)N1CCC2(CC1)N=C(C1(C(F)(F)F)CCC1)NC2=O] | LCMS-C-2 | 1.78 | 529 (M + H)+ |
| 138 | 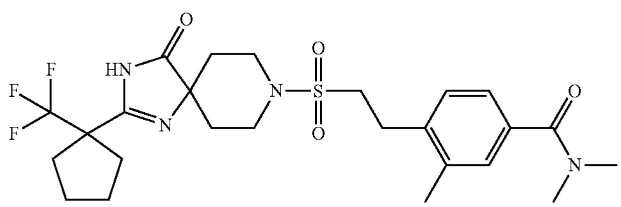 [SMILES: Cc1cc(C(=O)N(C)C)ccc1CCS(=O)(=O)N1CCC2(CC1)N=C(C1(C(F)(F)F)CCCC1)NC2=O] | LCMS-C-2 | 1.98 | 543 (M + H)+ |
| 139 | 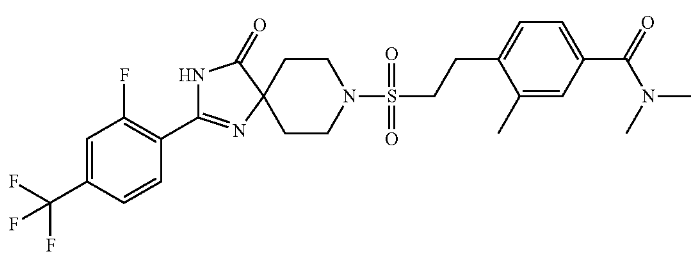 [SMILES: Cc1cc(C(=O)N(C)C)ccc1CCS(=O)(=O)N1CCC2(CC1)N=C(c1ccc(C(F)(F)F)cc1F)NC2=O] | LCMS-C-1 | 2.47 | 569 (M + H)+ |
| 140 | 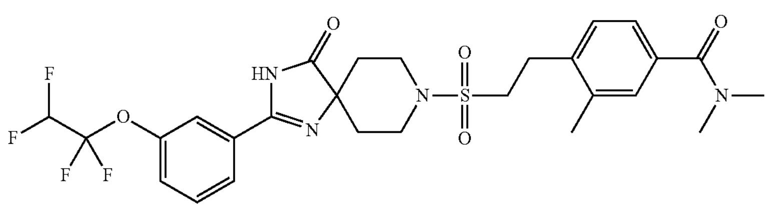 [SMILES: Cc1cc(C(=O)N(C)C)ccc1CCS(=O)(=O)N1CCC2(CC1)N=C(c1cccc(OC(F)(F)C(F)F)c1)NC2=O] | LCMS-A-1 | 2.41 | 599 (M + H)+ |
| 141 | 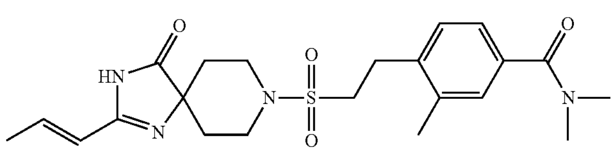 [SMILES: C/C=C/C1=NC2(CCN(S(=O)(=O)CCc3ccc(C(=O)N(C)C)cc3C)CC2)C(=O)N1] | LCMS-C-1 | 2.03 | 447 (M + H)+ |
| 142 | 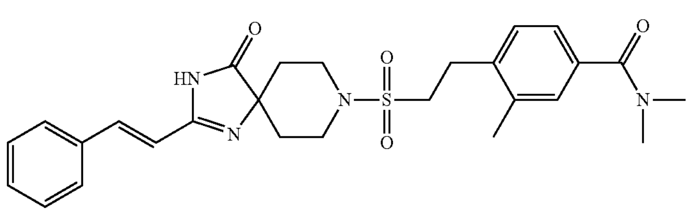 [SMILES: Cc1cc(C(=O)N(C)C)ccc1CCS(=O)(=O)N1CCC2(CC1)N=C(/C=C/c1ccccc1)NC2=O] | LCMS-A-1 | 2.00 | 509 (M + H)+ |

TABLE 10-continued

| Compound | Structure | LCMS or HPLC condition | Retention time (min) | MS (m/z) |
|---|---|---|---|---|
| 143 | 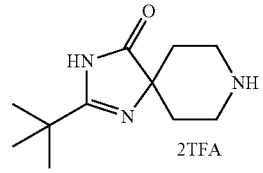 | LCMS-C-1 | 2.18 | 540 (M + H)+ |
| 144 | 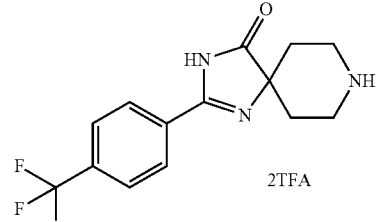 | LCMS-A-1 | 2.26 | 581 (M + H)+ |

The spiroamine reagents used in the synthesis of Compounds 74 to 85 and shown below were synthesized by operations similar to those in Reaction 7-1 and Reaction 7-2 using appropriate reagents and starting materials.

TABLE 11

| Target Compound | Spiroamine reagent | Spiroamine reagent MS (m/z) |
|---|---|---|
| 74 | 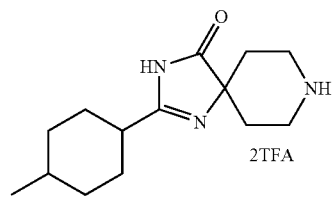 [SMILES: CC1CCC(C2=NC3(CCNCC3)C(=O)N2)CC1] | This compound was directly used in the next step (Reaction 10-6). |
| 75 | | 298 (M + H)+ |
| 76 | | 250 (M + H)+ |
| 77 | 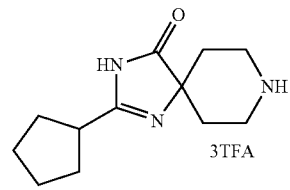 [SMILES: O=C1NC(C2CCCC2)=NC12CCNCC2] | 222 (M + H)+ |

TABLE 11-continued

| Target Compound | Spiroamine reagent | Spiroamine reagent MS (m/z) |
|---|---|---|
| 78 | 2,6-difluorophenyl spiroimidazolone-piperidine · 3TFA | 266 (M + H)+ |
| 79 | 2,6-dimethoxyphenyl spiroimidazolone-piperidine · 2TFA | 290 (M + H)+ |
| 80 | 3-methoxyphenyl spiroimidazolone-piperidine · 2TFA | 260 (M + H)+ |
| 81 | 3-chlorophenyl spiroimidazolone-piperidine · 2TFA | 264 (M + H)+ |
| 82 | 3,5-bis(trifluoromethyl)phenyl spiroimidazolone-piperidine · 2TFA | 366 (M + H)+ |
| 83 | benzyl spiroimidazolone-piperidine · 2TFA | 244 (M + H)+ |

TABLE 11-continued

| Target Compound | Spiroamine reagent | Spiroamine reagent MS (m/z) |
|---|---|---|
| 84 | 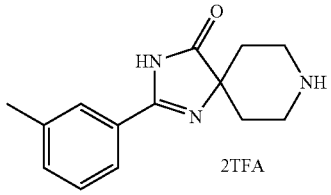 [SMILES: Cc1cccc(C2=NC3(CCNCC3)C(=O)N2)c1] 2TFA | 244 (M + H)+ |
| 85 | 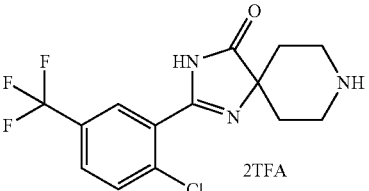 [SMILES: O=C1NC(c2cccc(C(F)(F)F)c2)=NC12CCNCC2] 2TFA | 332 (M + H)+ |

The spiroamine reagents used in the synthesis of Compounds 86 to 91 and shown below were synthesized by operations similar to those in Example 8 using appropriate reagents and starting materials.

TABLE 12

| Target Compound | Spiroamine reagent | Spiroamine reagent MS (m/z) |
|---|---|---|
| 86 | 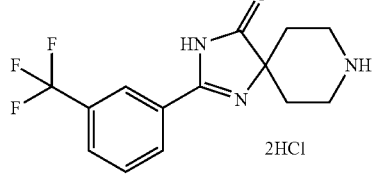 2HCl | 298 (M + H)+ |
| 87 | 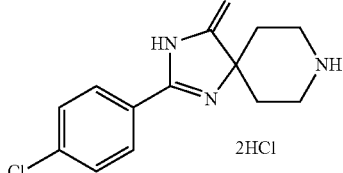 2HCl | 264 (M + H)+ |
| 88 | 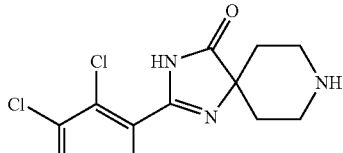 2HCl | 298 (M + H)+ |
| 89 | 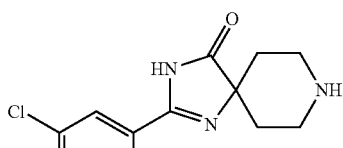 2HCl | 282 (M + H)+ |

TABLE 12-continued

| Target Compound | Spiroamine reagent | Spiroamine reagent MS (m/z) |
|---|---|---|
| 90 | 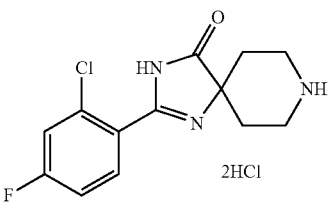 [SMILES: O=C1NC(c2ccc(F)cc2Cl)=NC12CCNCC2] 2HCl | 282 (M + H)+ |
| 91 | 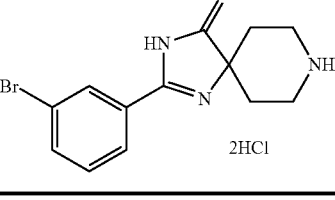 2HCl | 308 (M + H)+ |

The spiroamine reagent used in the synthesis of Compound 92 (2-(2,2-difluoro-benzo[1,3]dioxol-4-yl)-1,3,8-triaza-spiro[4.5]dec-1-en-4-one ditrifluoroacetate) was synthesized as follows.

(Reaction 10-7)

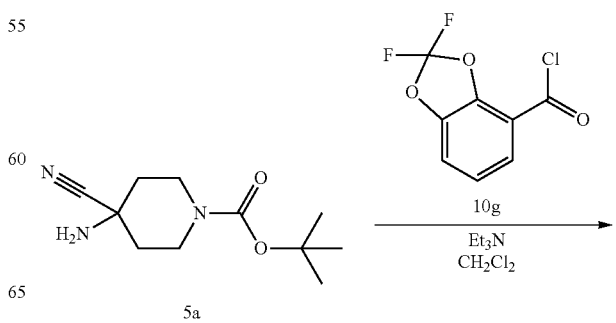

5a

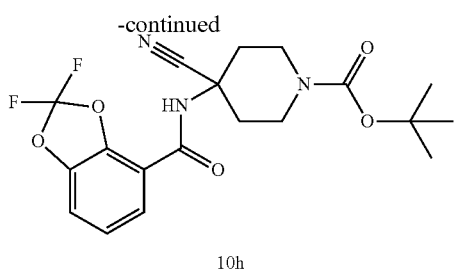

10h

4-Cyano-4-[(2,2-difluoro-benzo[1,3]dioxole-4-carbonyl)-amino]-piperidine-1-carboxylic acid tert-butyl ester was synthesized by operations similar to those in Reaction 2-3 of Example 2 using appropriate reagents and starting material.

MS (ESI) m/z=410 (M+H)+.

(Reaction 10-8)

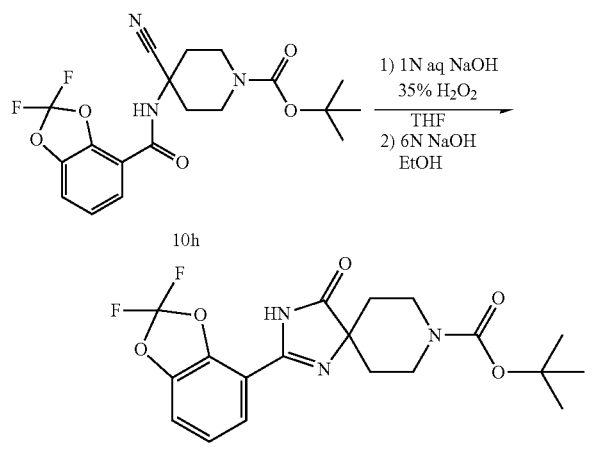

A 1 N aqueous NaOH solution (0.274 ml, 0.274 mmol) and a 35% aqueous H$_2$O$_2$ solution (0.051 ml, 0.52 mmol) were added to a solution of 4-cyano-4-[(2,2-difluoro-benzo[1,3]dioxole-4-carbonyl)-amino]-piperidine-1-carboxylic acid tert-butyl ester (56.0 mg, 0.137 mmol) in THF (0.23 ml) at room temperature. The reaction mixture was stirred at room temperature for 43 hours, and a 35% aqueous H$_2$O$_2$ solution (0.030 ml, 0.31 mmol) was then further added at room temperature. After stirring at room temperature for 48 hours, the mixture was quenched with a 1 N aqueous HCl solution (0.2 ml) and concentrated under reduced pressure. A 6 N aqueous NaOH solution (0.33 ml, 2.0 mmol) was added to a suspension of the resulting residue in EtOH (1.2 ml) at room temperature, and the mixture was stirred at room temperature for 24 hours. The reaction mixture was quenched with a saturated aqueous NH$_4$Cl solution (0.4 ml) and then concentrated under reduced pressure. The resulting residue was dissolved in ethyl acetate and washed with water, and then dried over MgSO$_4$ and concentrated under reduced pressure. The residue was purified by silica gel column chromatography (hexane/ethyl acetate=3/2) to give 2-(2,2-difluoro-benzo[1,3]dioxol-4-yl)-4-oxo-1,3,8-triaza-spiro[4.5]dec-1-ene-8-carboxylic acid tert-butyl ester (51.2 mg, 91%).

$^1$H-NMR (300 MHz) (CDCl$_3$) δ 1.50 (9H, s), 1.55 (2H, m), 1.95 (2H, m), 3.46 (2H, m), 4.02 (2H, br), 7.23-7.25 (2H, m), 7.88-7.94 (1H, m), 8.41 (1H, br s).

(Reaction 10-9)

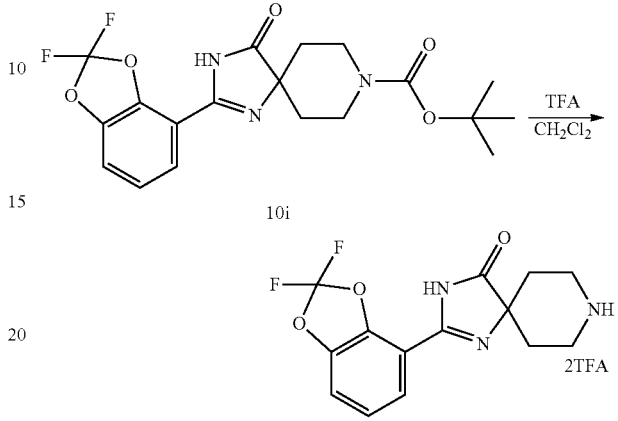

2-(2,2-Difluoro-benzo[1,3]dioxol-4-yl)-1,3,8-triaza-spiro[4.5]dec-1-en-4-one ditrifluoroacetate was synthesized by operations similar to those in Reaction 7-2 of Example 7 using appropriate reagents and starting material. (This compound was directly used in the next reaction.)

The spiroamine reagent used in the synthesis of Compound 93 (2-(3-chloro-2-fluoro-phenyl)-1,3,8-triaza-spiro[4.5]dec-1-en-4-one dihydrochloride) was synthesized as follows.

(Reaction 10-10)

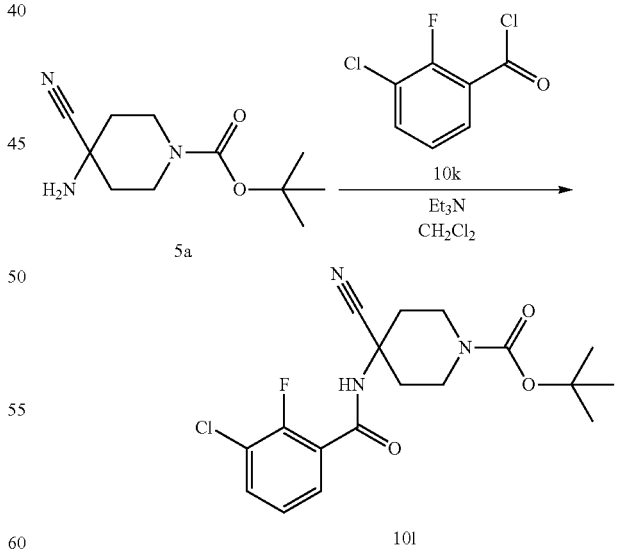

4-(3-Chloro-2-fluoro-benzoylamino)-4-cyano-piperidine-1-carboxylic acid tert-butyl ester was synthesized by operations similar to those in Reaction 2-3 of Example 2 using appropriate reagents and starting material.

MS (ESI) m/z=404 (M+Na)+.

(Reaction 10-11)

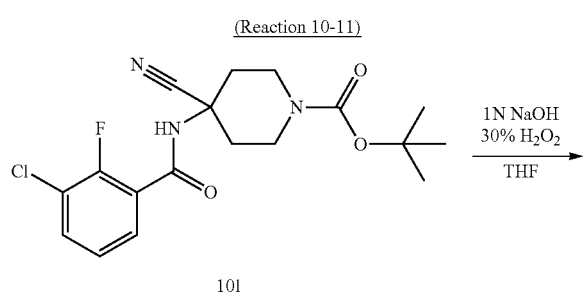

101

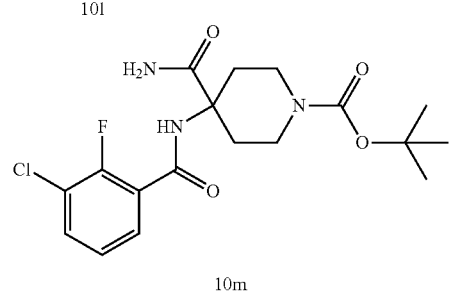

10m

1 N NaOH (8.60 ml, 8.60 mmol) and a 30% H₂O₂ solution (4.30 ml) were added to a solution of 4-(3-chloro-2-fluoro-benzoylamino)-4-cyano-piperidine-1-carboxylic acid tert-butyl ester (1.63 g, 4.28 mmol) in THF (8.60 ml) at room temperature, and the mixture was stirred at room temperature for two hours. The reaction mixture was adjusted to pH 6 by adding 2 N HCl and then extracted with ethyl acetate three times. The organic layers were sequentially washed with H₂O (×2) and saturated brine, and then dried over Na₂SO₄ and concentrated under reduced pressure. The resulting residue was triturated with H₂O, and the solid was collected by filtration. The resulting solid was washed with Et₂O and then dried under reduced pressure to give 4-carbamoyl-4-(3-chloro-2-fluoro-benzoylamino)-piperidine-1-carboxylic acid tert-butyl ester as a white powder (1.30 g, 76%).

MS (ESI) m/z=400 (M+H)+.

(Reaction 10-12)

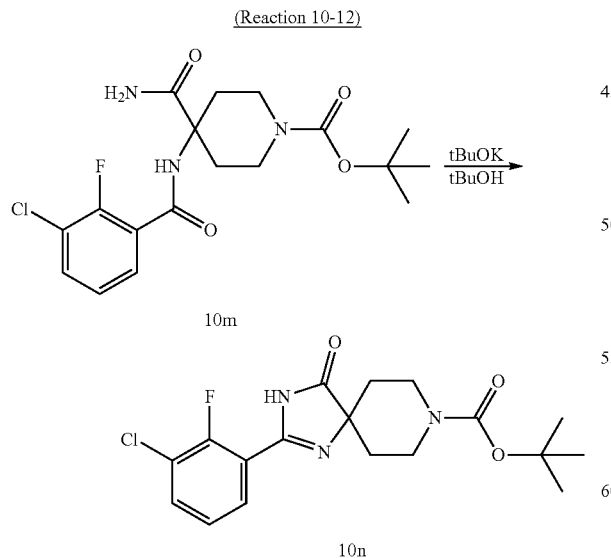

Potassium t-butoxide (1.01 g, 8.97 mmol) was added to a solution of 4-carbamoyl-4-(3-chloro-2-fluoro-benzoylamino)-piperidine-1-carboxylic acid tert-butyl ester (1.20 g, 2.99 mmol) in tBuOH (30.0 ml) at room temperature, and the mixture was stirred at 40° C. for six hours. The reaction mixture was adjusted to pH 6 by adding 2 N HCl and then extracted with AcOEt three times. The organic layers were sequentially washed with H₂O (×2) and saturated brine, and then dried over Na₂SO₄ and concentrated under reduced pressure. The residue was purified by column chromatography (hexane/AcOEt=90:10→50:50) to give 2-(3-chloro-2-fluoro-phenyl)-4-oxo-1,3,8-triaza-spiro[4.5]dec-1-ene-8-carboxylic acid tert-butyl ester as a colorless form (1.13 g, 99%).

MS (ESI) m/z=382 (M+H)+.

(Reaction 10-13)

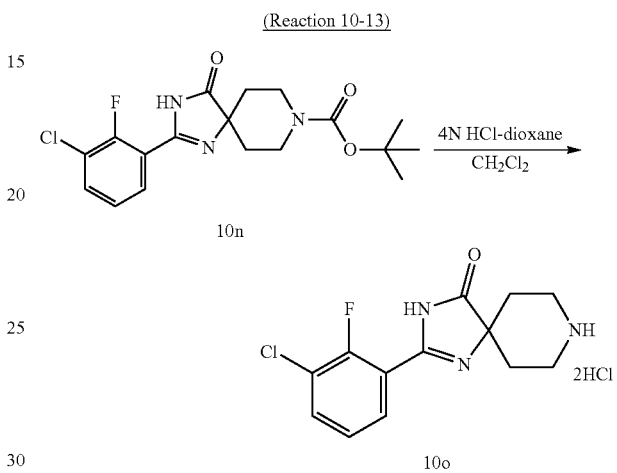

2-(3-Chloro-2-fluoro-phenyl)-1,3,8-triaza-spiro[4.5]dec-1-en-4-one dihydrochloride was synthesized by operations similar to those in Reaction 5-3 of Example 5 using appropriate reagents and starting material.

MS (ESI) m/z=282 (M+H)+.

The spiroamine reagent used in the synthesis of Compound 94 (2-[4-(1,1,2,2-tetrafluoro-ethoxy)-phenyl]-1,3,8-triaza-spiro[4.5]dec-1-en-4-one dihydrochloride) was synthesized as follows.

(Reaction 10-14)

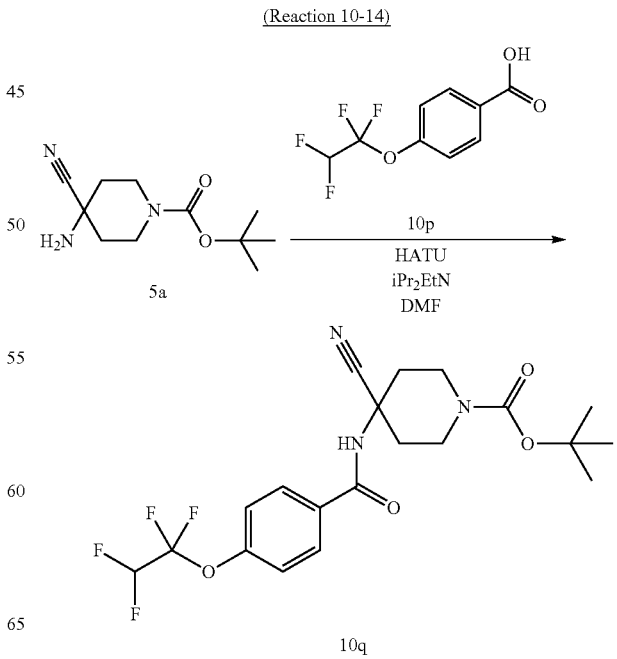

N,N,N',N'-Tetramethyl-O-(7-azabenzotriazol-1-yl)uronium hexafluorophosphate (1.60 g, 4.20 mmol) was added to a solution of 4-(1,1,2,2-tetrafluoro-ethoxy)-benzoic acid (1.00 g, 4.20 mmol), 4-amino-4-cyano-piperidine-1-carboxylic acid tert-butyl ester (995 mg, 4.42 mmol) and N,N-diisopropylethylamine (1.46 ml, 8.39 mmol) in DMF (8.8 ml) at 0° C. The mixture was gradually warmed to room temperature and stirred for 28.5 hours. An aqueous ammonium chloride solution was added to the reaction mixture, followed by extraction with ethyl acetate three times. The organic layers were sequentially washed with $H_2O$ (×2) and saturated brine, and then dried over $Na_2SO_4$ and concentrated under reduced pressure. The residue was purified by column chromatography (hexane:AcOEt=90:10→30:70) to give 4-cyano-4-[4-(1,1,2,2-tetrafluoro-ethoxy)-benzoylamino]-piperidine-1-carboxylic acid tert-butyl ester as a light brown powder (1.60 g, 86%).

MS (ESI) m/z=446 (M+H)+.

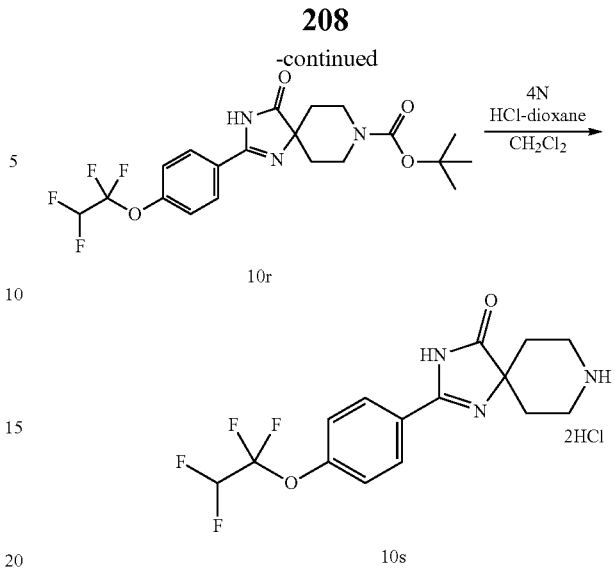

2-[4-(1,1,2,2-Tetrafluoro-ethoxy)-phenyl]-1,3,8-triazaspiro[4.5]dec-1-en-4-one dihydrochloride was synthesized by operations similar to those in Reaction 5-2 and Reaction 5-3 of Example 5 using appropriate reagents and starting material.

MS (ESI) m/z=346 (M+H)+.

The following spiroamine reagents used in the synthesis of Compounds 95 to 99 were synthesized by operations similar to those in Reaction 10-14 and Reaction 10-15 using appropriate reagents and starting materials.

TABLE 13

| Target Compound | Spiroamine reagent | Spiroamine reagent MS (m/z) |
|---|---|---|
| 95 | ![structure] | 278 (M + H)+ |
| 96 | ![structure] | 316 (M + H)+ |
| 97 | ![structure] | 245 (M + H)+ |

TABLE 13-continued

| Target Compound | Spiroamine reagent | Spiroamine reagent MS (m/z) |
|---|---|---|
| 98 | 3,4-dichlorophenyl spiroimidazolone·2HCl | 298 (M + H)+ |
| 99 | 3-(trifluoromethoxy)phenyl spiroimidazolone·2HCl | 314 (M + H)+ |

The following spiroamine reagents used in the synthesis of Compounds 100 to 114 were synthesized by operations similar to those in Reaction 10-14, Reaction 5-2 and Reaction 7-2 using appropriate reagents and starting materials.

TABLE 14

| Target Compound | Spiroamine reagent | Spiroamine reagent MS (m/z) |
|---|---|---|
| 100 | 2,4-bis(trifluoromethyl)phenyl spiroimidazolone·2TFA | 366 (M + H)+ |
| 101 | phenethyl spiroimidazolone·2TFA | 258 (M + H)+ |
| 102 | 2,4-dimethylthiazol-5-yl spiroimidazolone·2TFA | 265 (M + H)+ |
| 103 | cyclohexylmethyl spiroimidazolone·2TFA | 250 (M + H)+ |

TABLE 14-continued

| Target Compound | Spiroamine reagent | Spiroamine reagent MS (m/z) |
|---|---|---|
| 104 | 4-(trifluoromethyl)cyclohexyl-substituted imidazolone spiropiperidine, 2TFA | 304 (M + H)+ |
| 105 | 2-(trifluoromethoxy)phenyl-substituted imidazolone spiropiperidine, 2TFA | 314 (M + H)+ |
| 106 | 4-(trifluoromethoxy)phenyl-substituted imidazolone spiropiperidine, 2TFA | 314 (M + H)+ |
| 107 | 4-fluoro-3-(trifluoromethyl)phenyl-substituted imidazolone spiropiperidine, 2TFA | 315 (M + H)+ |
| 108 | 2-cyclohexylethyl-substituted imidazolone spiropiperidine, 2TFA | 264 (M + H)+ |
| 109 | 3-fluorophenyl-substituted imidazolone spiropiperidine, 2TFA | 248 (M + H)+ |
| 110 | 3-(methylsulfonyl)phenyl-substituted imidazolone spiropiperidine, 2TFA | 308 (M + H)+ |

TABLE 14-continued

| Target Compound | Spiroamine reagent | Spiroamine reagent MS (m/z) |
| --- | --- | --- |
| 111 | [2-(3-trifluoromethyl-2-methylphenyl)-1,3,8-triazaspiro[4.5]dec-1-en-4-one · 2TFA] | 312 (M + H)+ |
| 112 | [2-(5-trifluoromethyl-2-methylphenyl)-1,3,8-triazaspiro[4.5]dec-1-en-4-one · 2TFA] | 312 (M + H)+ |
| 113 | [2-(2,3-dimethylphenyl)-1,3,8-triazaspiro[4.5]dec-1-en-4-one · 2TFA] | 258 (M + H)+ |
| 114 | [2-(3-fluoro-2-methylphenyl)-1,3,8-triazaspiro[4.5]dec-1-en-4-one · 2TFA] | 262 (M + H)+ |

The following spiroamine reagents used in the synthesis of Compounds 115 to 117 were synthesized by operations similar to those in Reaction 10-14, Reaction 10-8 and Reaction 7-2 using appropriate reagents and starting materials.

TABLE 15

| Target Compound | Spiroamine reagent | Spiroamine reagent MS (m/z) |
| --- | --- | --- |
| 115 | [2-(3,5-bis-trifluoromethylphenyl... wait, 3-trifluoromethyl-5-fluorophenyl)-1,3,8-triazaspiro[4.5]dec-1-en-4-one · 2TFA] | 315 (M + H)+ |
| 116 | [2-(3-trifluoromethyl-2-fluorophenyl)-1,3,8-triazaspiro[4.5]dec-1-en-4-one · 2TFA] | 315 (M + H)+ |
| 117 | [2-(4-fluoro-3-methylphenyl)-1,3,8-triazaspiro[4.5]dec-1-en-4-one · 2TFA] | 262 (M + H)+ |

The following spiroamine reagent used in the synthesis of Compound 118 (2-(4-difluoromethoxy-phenyl)-1,3,8-triaza-spiro[4.5]dec-1-en-4-one) was synthesized by operations similar to those in Reaction 10-14, Reaction 10-8 and Reaction 5-3 using appropriate reagents and starting material.

nyl)-amino]-piperidine-1-carboxylic acid tert-butyl ester as a colorless form (901 mg, 84%).
MS (ESI) m/z=361 (M+H)+.

TABLE 16

| Target Compound | Spiroamine reagent | Spiroamine reagent MS (m/z) |
|---|---|---|
| 118 | 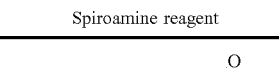 | 296 (M + H)+ |

The spiroamine reagent used in the synthesis of Compound 119 (2-(2-methoxy-pyridin-4-yl)-1,3,8-triaza-spiro[4.5]dec-1-en-4-one ditrifluoroacetate) was synthesized as follows.

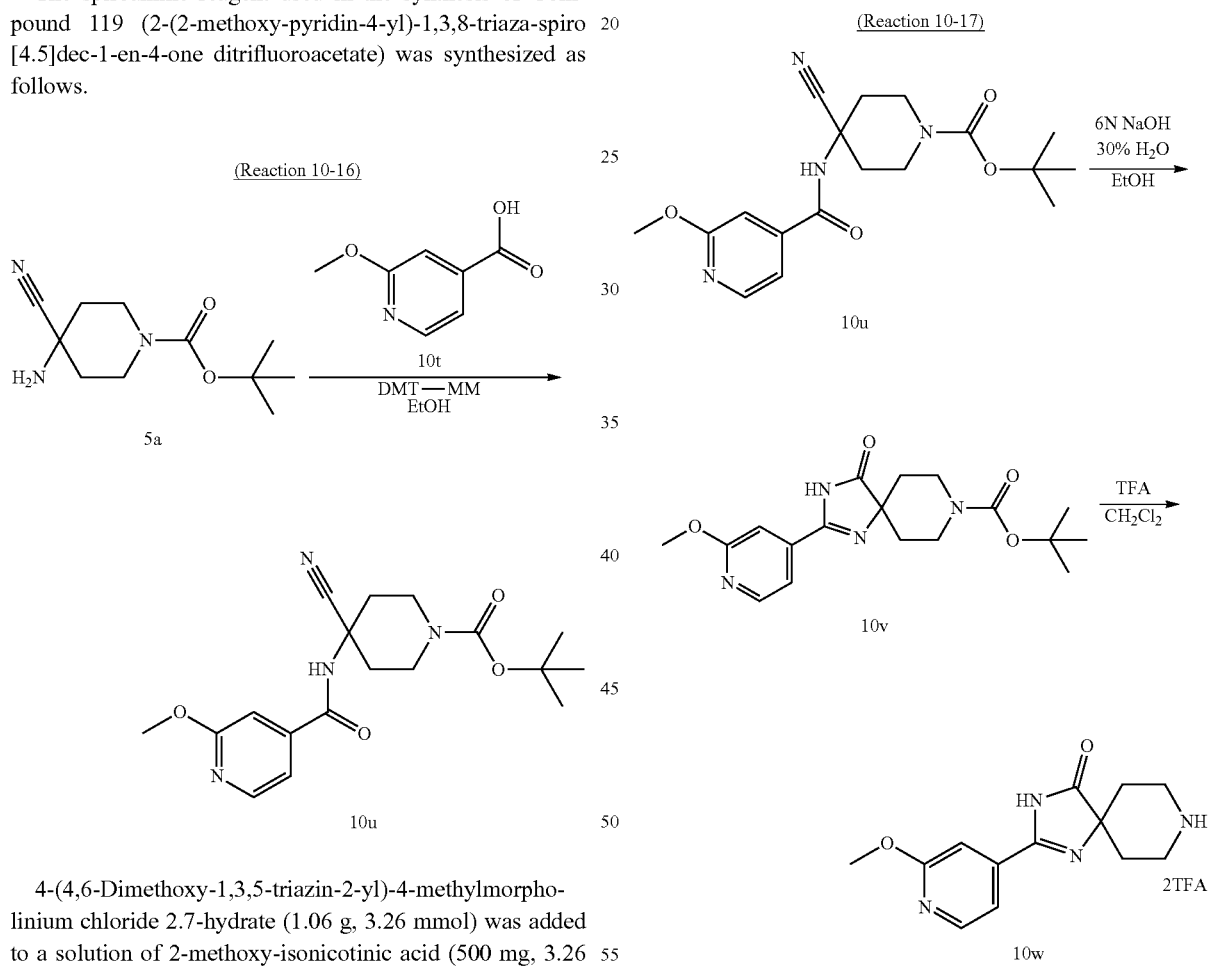

4-(4,6-Dimethoxy-1,3,5-triazin-2-yl)-4-methylmorpholinium chloride 2.7-hydrate (1.06 g, 3.26 mmol) was added to a solution of 2-methoxy-isonicotinic acid (500 mg, 3.26 mmol) and 4-amino-4-cyano-piperidine-1-carboxylic acid tert-butyl ester (669 mg, 2.97 mmol) in EtOH (8.0 ml) at room temperature, and the mixture was stirred for 46.5 hours. An aqueous NaHCO₃ solution was added to the reaction mixture, followed by extraction with AcOEt three times. The organic layers were washed with saturated brine, and then dried over anhydrous sodium sulfate and concentrated under reduced pressure. The resulting residue was purified by column chromatography (CH₂Cl₂/MeOH=99:1 to 95:5) to give 4-cyano-4-[(2-methoxy-pyridine-4-carbo- 2-(2-Methoxy-pyridin-4-yl)-1,3,8-triaza-spiro[4.5]dec-1-en-4-one ditrifluoroacetate was synthesized by operations similar to those in Reaction 5-2 and Reaction 7-2 using appropriate reagents and starting material. (This compound was directly used in the next reaction.)

The following spiroamine reagents used in the synthesis of Compounds 120 to 131 were synthesized by the procedure described in Reaction 10-16 and Reaction 10-17 using appropriate reagents and starting materials.

TABLE 17

| Target Compound | Spiroamine reagent | Spiroamine reagent MS (m/z) |
|---|---|---|
| 120 | 5-methylpyrazin-2-yl substituted 1,3,8-triazaspiro[4.5]dec-1-en-4-one, 2TFA | 246 (M + H)+ |
| 121 | thiazol-4-yl substituted 1,3,8-triazaspiro[4.5]dec-1-en-4-one, 2TFA | This compound was directly used in the next step (Reaction 10-6). |
| 122 | 1-methyl-1H-imidazol-2-yl substituted 1,3,8-triazaspiro[4.5]dec-1-en-4-one, 3TFA | 234 (M + H)+ |
| 123 | tetrahydro-2H-pyran-4-yl substituted 1,3,8-triazaspiro[4.5]dec-1-en-4-one, 2TFA | This compound was directly used in the next step (Reaction 10-6). |
| 124 | (4-chlorophenoxy)methyl substituted 1,3,8-triazaspiro[4.5]dec-1-en-4-one, 2TFA | 294 (M + H)+ |
| 125 | (4-fluorophenoxy)methyl substituted 1,3,8-triazaspiro[4.5]dec-1-en-4-one, 2TFA | 278 (M + H)+ |
| 126 | 4-chloro-2-(trifluoromethyl)phenyl substituted 1,3,8-triazaspiro[4.5]dec-1-en-4-one, 2TFA | 332 (M + H)+ |

TABLE 17-continued

| Target Compound | Spiroamine reagent | Spiroamine reagent MS (m/z) |
|---|---|---|
| 127 | (3-chloro-5-(trifluoromethyl)phenyl spiroamine, 2TFA) | 331 (M + H)+ |
| 128 | (4-chloro-2-methylphenyl spiroamine, 2TFA) | 278 (M + H)+ |
| 129 | (4-chloro-2-fluorophenyl spiroamine, 2TFA) | 282 (M + H)+ |
| 130 | (3-(isobutoxymethyl)phenyl spiroamine, 2TFA) | 302 (M + H)+ |
| 131 | (2-((2,4-dichlorophenoxy)methyl) spiroamine, 2TFA) | 328 (M + H)+ |

The following spiroamine reagent used in the synthesis of Compound 133 was synthesized by operations similar to those in Reaction 10-16, Reaction 10-8 and Reaction 5-3 using appropriate reagents and starting material.

TABLE 18

| Target Compound | Spiroamine reagent | Spiroamine reagent MS (m/z) |
|---|---|---|
| 133 | (3-chloro-2-methylphenyl spiroamine, 2HCl) | 378 (M + H)+ |

The spiroamine reagent used in the synthesis of Compound 134 (2-(2,4-dichloro-benzyl)-1,3,8-triaza-spiro[4.5]dec-1-en-4-one ditrifluoroacetate) was synthesized as follows.

(Reaction 10-18)

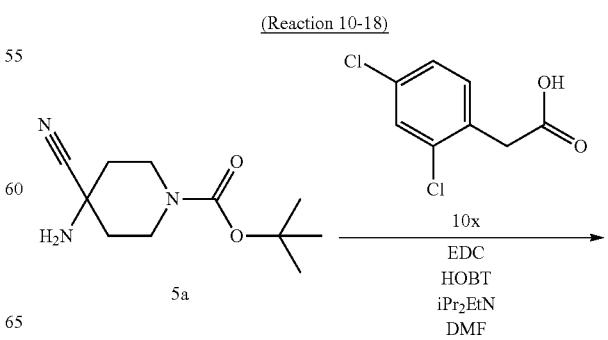

-continued

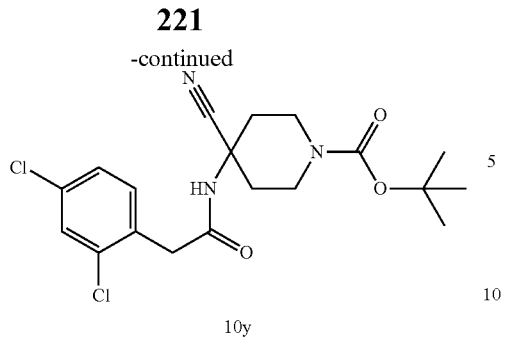

10y (2,4-Dichloro-phenyl)-acetic acid (218 mg, 1.07 mmol), 1-ethyl-3-(3'-dimethylamino-propyl)carbodiimide hydrochloride (255 mg, 1.33 mmol), 1-hydroxybenzotriazole hydrate (136 mg, 0.88 mmol) and N,N-diisopropylethylamine (0.378 ml, 2.22 mmol) were sequentially added to a solution of 4-amino-4-cyano-piperidine-1-carboxylic acid tert-butyl ester (200 mg, 0.888 mmol) in DMF (4 ml) at room temperature, and the mixture was stirred at room temperature for 16 hours. H$_2$O (20 ml) was added to the reaction mixture, followed by extraction with AcOEt (40 ml and 20 ml). The organic layers were sequentially washed with H$_2$O (20 ml), 1 N HCl (20 ml), H$_2$O (20 ml) and saturated brine (20 ml), and then dried over Na$_2$SO$_4$ and concentrated under reduced pressure. The resulting residue was purified by silica gel column chromatography (n-hexane/AcOEt) to give 4-cyano-4-[2-(2,4-dichloro-phenyl)-acetylamino]-piperidine-1-carboxylic acid tert-butyl ester as a white powder (285 mg, 78%).

$^1$H-NMR (270 MHz, CDCl$_3$) δ 1.45 (9H, s), 1.72 (2H, ddd, J=13.2, 10.7, 3.9 Hz), 2.34-2.37 (2H, m), 3.20-3.27 (2H, m), 3.68 (2H, s), 3.81-3.97 (2H, m), 5.55 (1H, s), 7.28 (1H, dd, J=7.8, 2.0 Hz), 7.30 (1H, d, 7.8 Hz), 7.45 (1H, d, J=2.0 Hz). MS (ESI) m/z=412 (M+H)+.

(Reaction 10-19)

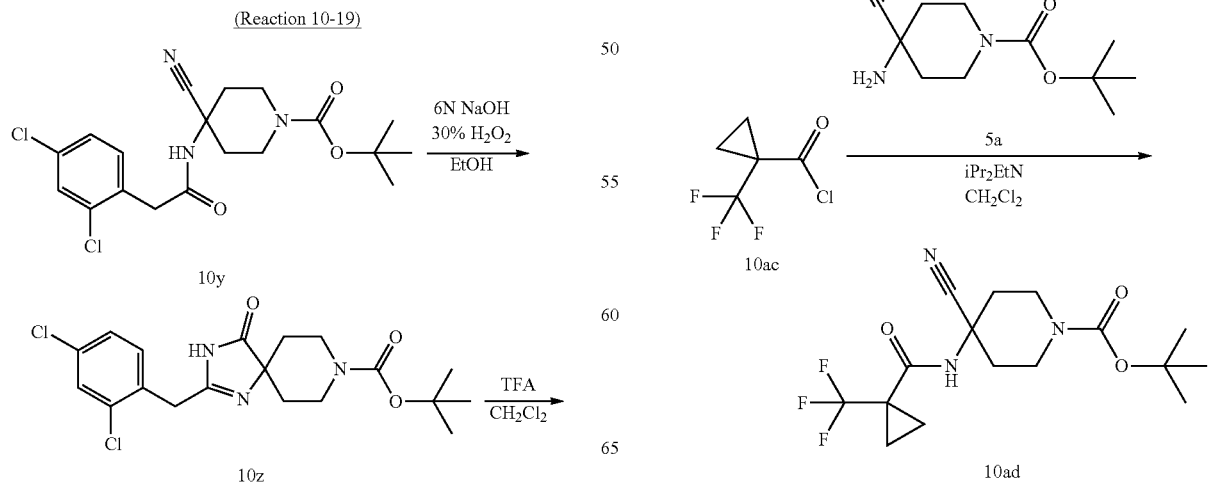

-continued

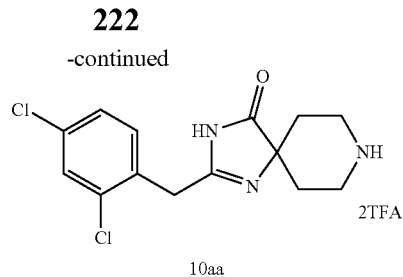

10aa 2-(2,4-Dichloro-benzyl)-1,3,8-triaza-spiro[4.5]dec-1-en-4-one ditrifluoroacetate was synthesized by operations similar to those in Reaction 5-2 and Reaction 7-2 using appropriate reagents and starting material.

MS (ESI) m/z=312 (M+H)+.

The following spiroamine reagent used in the synthesis of Compound 135 was synthesized by operations similar to those in Reaction 10-18 and Reaction 10-19 using appropriate reagents and starting material.

TABLE 19

| Target Compound | Spiroamine reagent | Spiroamine reagent MS (m/z) |
|---|---|---|
| 135 | 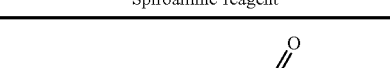 2TFA | 312 (M + H)+ |

The spiroamine reagent used in the synthesis of Compound 136 (2-(1-trifluoromethyl-cyclopropyl)-1,3,8-triaza-spiro[4.5]dec-1-en-4-one ditrifluoroacetate) was synthesized as follows.

(Reaction 10-20)

Oxalyl chloride (0.20 ml, 2.3 mmol) and dimethylformamide (8 μl) were added to a solution of 1-trifluoromethyl-cyclopropanecarboxylic acid (308 mg, 2.00 mmol) in dichloromethane (2.1 ml) at 0° C. The mixture was stirred at 0° C. for 30 minutes and then stirred at room temperature for two hours. The reaction mixture was concentrated under reduced pressure. A solution of the resulting residue in dichloromethane (1.5 ml) was added dropwise to a solution of 4-amino-4-cyanopiperidine-1-carboxylic acid tert-butyl ester (377 mg, 1.67 mmol) and diisopropylethylamine (0.42 ml, 2.4 mmol) in dichloromethane (2.0 ml) over three minutes at 0° C., and the mixture was stirred at room temperature for 13 hours. The reaction mixture was diluted with dichloromethane, and the organic layer was then washed with water, dried over MgSO$_4$ and concentrated under reduced pressure. The resulting residue was purified by silica gel column chromatography (hexane/ethyl acetate=3/1→2/1) to give 4-cyano-4-[(1-trifluoromethyl-cyclopropanecarbonyl)-amino]-piperidine-1-carboxylic acid tert-butyl ester as a colorless solid (519 mg, 86%).

$^1$H-NMR (400 MHz) (CDCl$_3$) δ 1.46 (9H, s), 1.29 (2H, dd, J=7.5 and 4.5 Hz), 1.56 (2H, m), 1.80 (2H, m), 2.40 (2H, m), 3.30 (2H, m), 3.93 (2H, br), 6.07 (1H, br s). Rf=0.62 in TLC (developer; hexane:AcOEt=1:1).

TABLE 20

| Target Compound | Spiroamine reagent | Spiroamine reagent MS (m/z) |
|---|---|---|
| 137 | 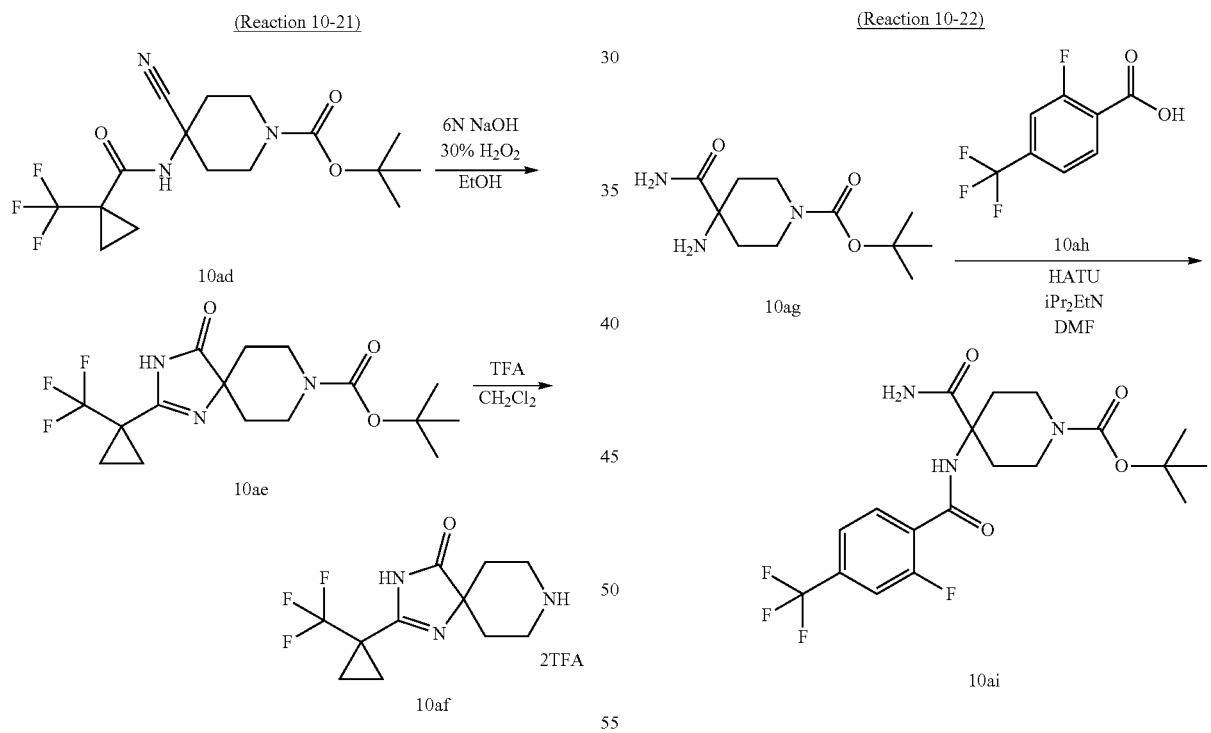 | This compound was directly used in the next step (Reaction 10-6). |
| 138 | | This compound was directly used in the next step (Reaction 10-6). |

The spiroamine reagent used in the synthesis of Compound 139 (2-(2-fluoro-4-trifluoromethyl-phenyl)-1,3,8-triaza-spiro[4.5]dec-1-en-4-one ditrifluoroacetate) was synthesized as follows.

2-(1-Trifluoromethyl-cyclopropyl)-1,3,8-triaza-spiro[4.5]dec-1-en-4-one ditrifluoroacetate was synthesized by operations similar to those in Reaction 5-2 and Reaction 7-2 using appropriate reagents and starting material. (This compound was directly used in Reaction 10-6.)

The following spiro-amine reagents used in the synthesis of Compounds 137 to 138 were synthesized by operations similar to those in Reaction 10-20 and Reaction 10-21 using appropriate reagents and starting materials. (These compounds were directly used in Reaction 10-6.)

HATU (939 mg, 2.47 mmol) and DIPEA (525 μL, 3.09 mmol) were added to a solution of 4-amino-4-carbamoyl-piperidine-1-carboxylicacid tert-butyl ester (500 mg, 2.06 mmol) and 2-fluoro-4-trifluoromethyl-benzoic acid (514 mg, 2.47 mmol) in DMF (10 mL). The mixture was stirred at room temperature for 19 hours and then quenched with a saturated aqueous ammonium chloride solution. The reaction mixture was diluted with EtOAc, and the organic layer was then washed with H$_2$O and saturated brine, dried over MgSO$_4$ and concentrated under reduced pressure. The resulting residue was triturated with n-hexane and EtOAc and then collected by filtration to give 4-carbamoyl-4-(2- fluoro-4-trifluoromethyl-benzoylamino)-piperidine-1-carboxylic acid tert-butyl ester as a white solid. This was used in the next step without further purification.

(Reaction 10-23)

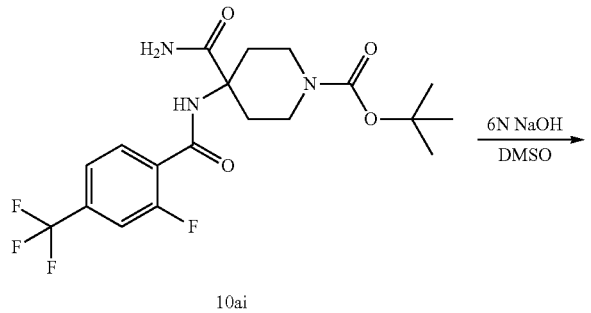

10ai

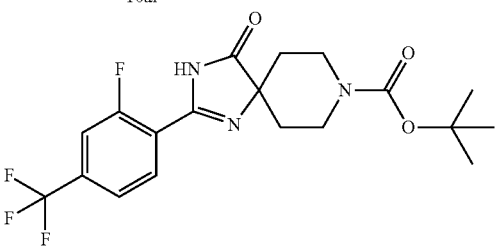

10aj

MeOH=95:5) to give 2-(2-fluoro-4-trifluoromethyl-phenyl)-4-oxo-1,3,8-triaza-spiro[4.5]dec-1-ene-8-carboxylic acid tert-butyl ester as a white solid (54.5 mg, 57%).

MS (ESI) m/z=438 (M+Na)+.

(Reaction 10-24)

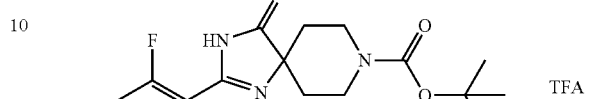

10aj

10ak

A 6 N aqueous NaOH solution (54.8 µL, 323 µmol) was added to a solution of 4-carbamoyl-4-(2-fluoro-4-trifluoromethyl-benzoylamino)-piperidine-1-carboxylic acid tert-butyl ester (100 mg, 231 µmol) in DMSO (0.3 mL), and the mixture was stirred at room temperature for 27 hours. The reaction mixture was quenched with a saturated aqueous ammonium chloride solution and then diluted with EtOAc, and the organic layer was sequentially washed with H₂O and saturated brine. The organic layer was dried over MgSO₄ and then concentrated under reduced pressure. The resulting residue was purified by column chromatography (CH₂Cl₂/

2-(2-Fluoro-4-trifluoromethyl-phenyl)-1,3,8-triaza-spiro [4.5]dec-1-en-4-one ditrifluoroacetate was synthesized by operations similar to those in Reaction 7-2 using appropriate reagents and starting material.

MS (ESI) m/z=315 (M+H)+.

The following spiro-amine reagents used in the synthesis of Compounds 140 to 143 were synthesized by operations similar to those in Reaction 10-22, Reaction 10-23 and Reaction 10-24 using appropriate reagents and starting materials.

TABLE 21

| Target Compound | Spiroamine reagent | Spiroamine reagent MS (m/z) |
|---|---|---|
| 140 | 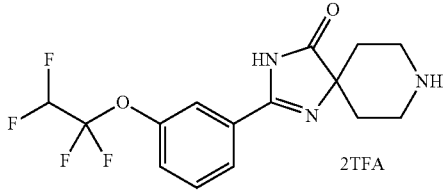 [SMILES: O=C1NC(c2cccc(OC(F)(F)C(F)F)c2)=NC12CCNCC2] | 346 (M + H)+ |
| 141 | 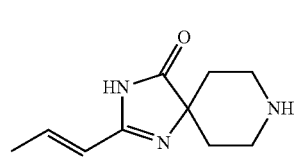 | 194 (M + H)+ |

TABLE 21-continued

| Target Compound | Spiroamine reagent | Spiroamine reagent MS (m/z) |
|---|---|---|
| 142 | | 256 (M + H)+ |
| 143 | | 287 (M + H)+ |

The spiroamine reagent used in the synthesis of Compound 144 (2-(4-methoxy-3-trifluoromethyl-phenyl)-1,3,8-triaza-spiro[4.5]dec-1-en-4-one ditrifluoroacetate) was synthesized as follows.

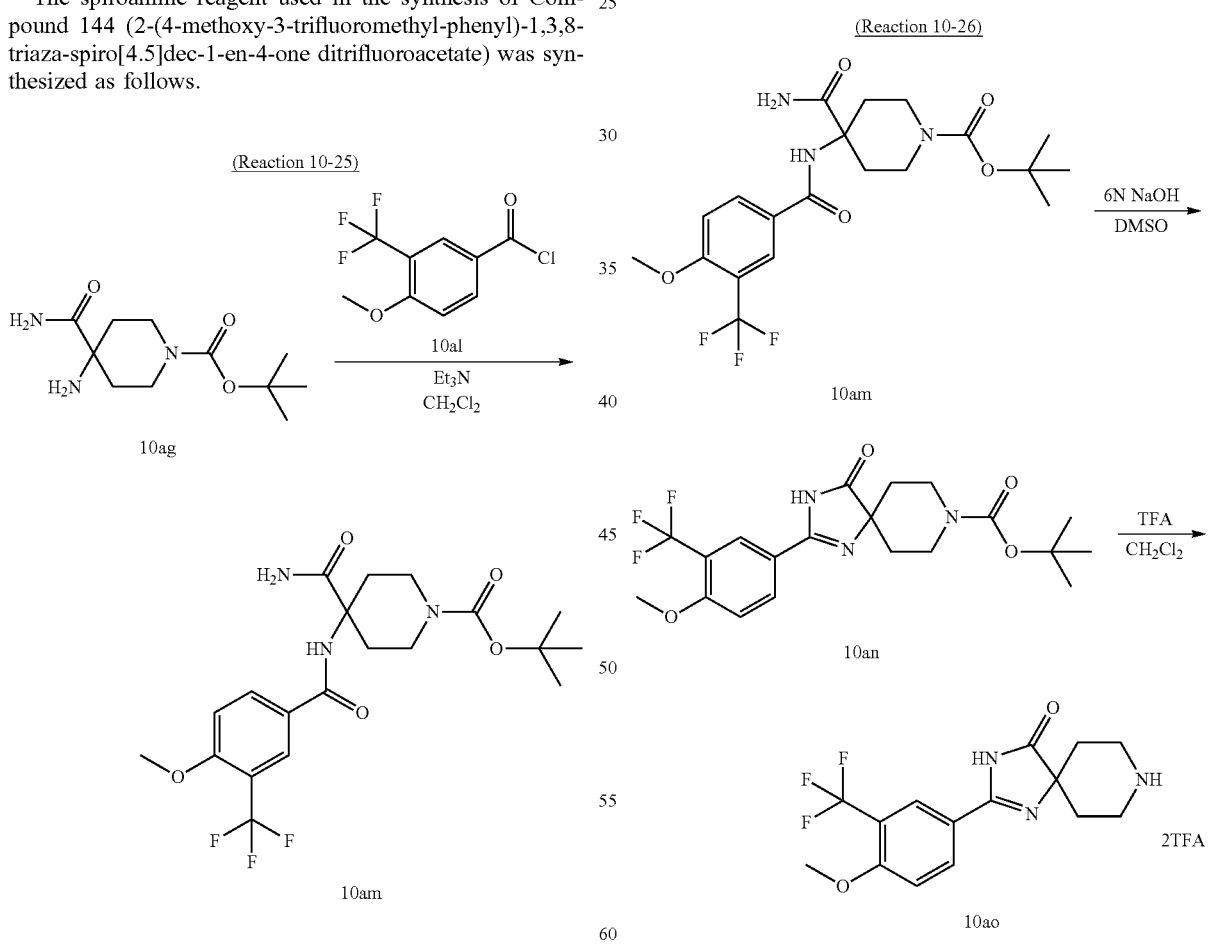

4-Carbamoyl-4-(4-methoxy-3-trifluoromethyl-benzoylamino)-piperidine-1-carboxylic acid tert-butyl ester was synthesized by operations similar to those in Reaction 2-3 using 4-amino-4-carbamoyl-piperidine-1-carboxylic acid tert-butyl ester as a starting material amine.

MS (ESI) m/z=446 (M+H)+.

2-(4-Methoxy-3-trifluoromethyl-phenyl)-1,3,8-triaza-spiro[4.5]dec-1-en-4-one ditrifluoroacetate was synthesized by operations similar to those in Reaction 10-23 and Reaction 7-2 using appropriate reagents and starting material.

MS (ESI) m/z=328 (M+H)+.

Example 11

N-{3-Methyl-4-[2-(4-oxo-2-m-tolyl-1,3,8-triaza-spiro[4.5]dec-1-ene-8-sulfonyl)-ethyl]-phenyl}-acetamide (Compound 145)

(Reaction 11-1)

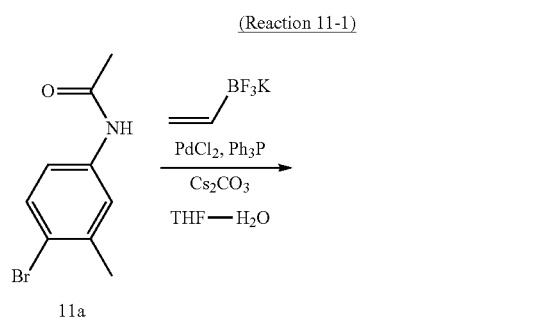

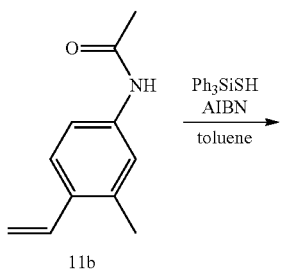

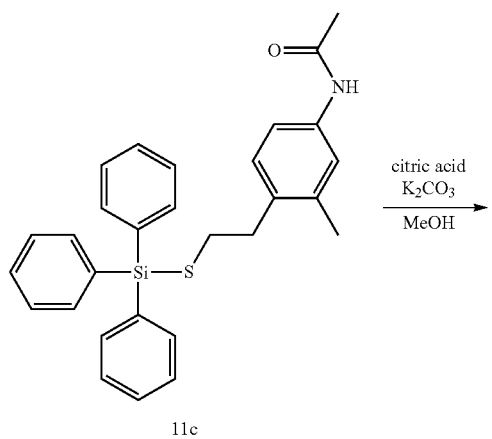

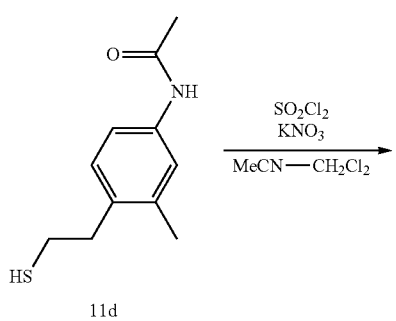

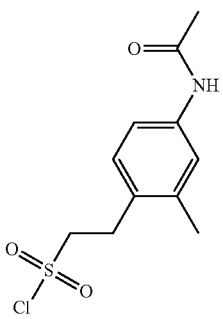

2-(4-Acetylamino-2-methyl-phenyl)-ethanesulfonyl chloride was synthesized by operations similar to those in Reaction 10-2, Reaction 10-3, Reaction 10-4 and Reaction 10-5 using appropriate reagents and starting material.

MS (ESI) m/z=276 (M+H)+.

(Reaction 11-2)

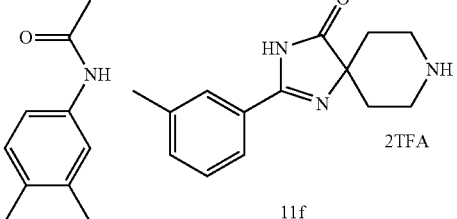

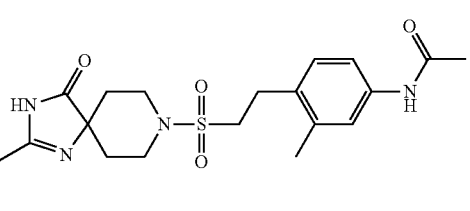

N-{3-Methyl-4-[2-(4-oxo-2-m-tolyl-1,3,8-triaza-spiro[4.5]dec-1-ene-8-sulfonyl)-ethyl]-phenyl}-acetamide was synthesized by operations similar to those in Reaction 5-4 using appropriate reagents and starting material.

MS (ESI) m/z=483 (M+H)+.

The example compounds shown below were synthesized by operations similar to those in Example 11 using appropriate reagents and starting materials.

TABLE 22
| Compound | Structure | LCMS or HPLC condition | Retention time (min) | MS (m/z) |
|---|---|---|---|---|
| 146 | 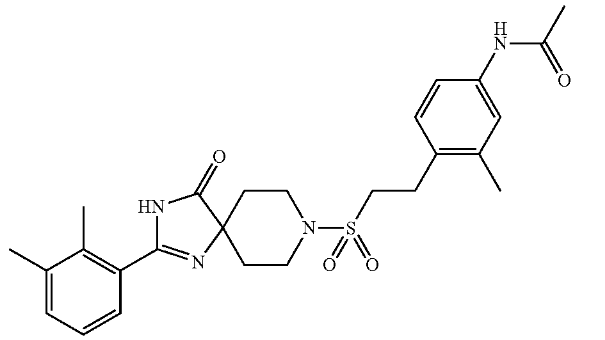 [SMILES: CC(=O)Nc1ccc(CCS(=O)(=O)N2CCC3(CC2)N=C(c2cccc(C)c2C)NC3=O)c(C)c1] | LCMS-C-1 | 2.33 | 497 (M + H)+ |
| 147 | 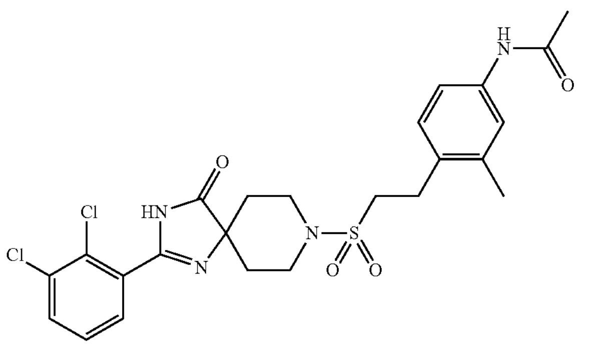 [SMILES: CC(=O)Nc1ccc(CCS(=O)(=O)N2CCC3(CC2)N=C(c2cccc(Cl)c2Cl)NC3=O)c(C)c1] | LCMS-C-1 | 2.40 | 537 (M + H)+ |
| 148 | 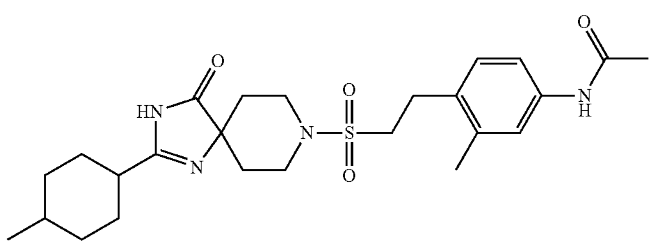 [SMILES: CC(=O)Nc1ccc(CCS(=O)(=O)N2CCC3(CC2)N=C(C2CCC(C)CC2)NC3=O)c(C)c1] | LCMS-C-1 | 2.45 | 489 (M + H)+ |
The spiroamine reagent used in the synthesis of Compound 148 (2-(4-methyl-cyclohexyl)-1,3,8-triaza-spiro[4.5]dec-1-en-4-one dihydrochloride) was synthesized as follows.
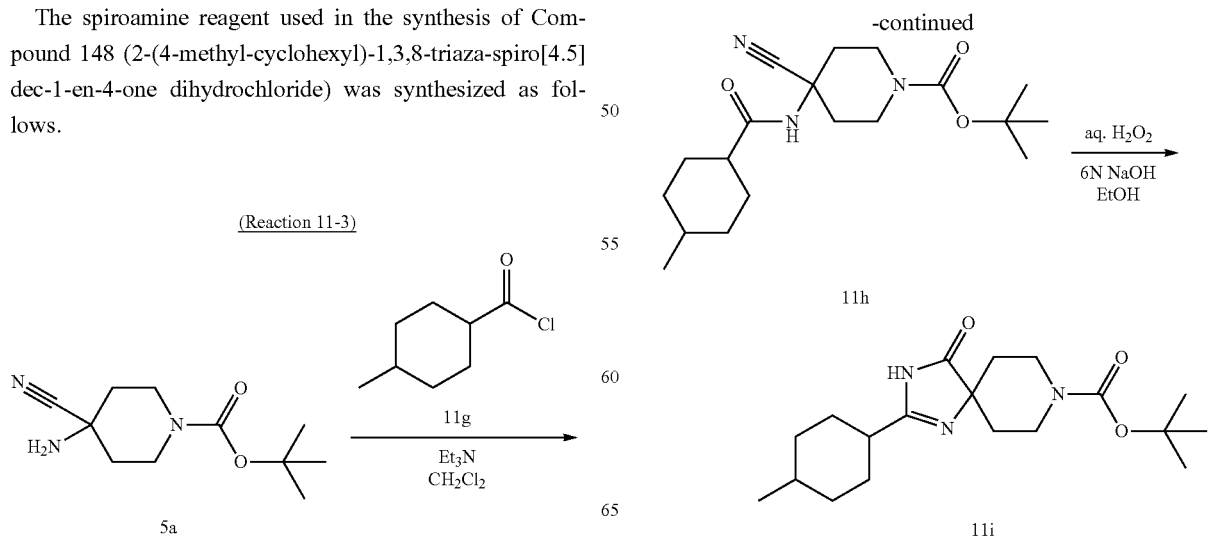
(Reaction 11-3)

2-(4-Methyl-cyclohexyl)-4-oxo-1,3,8-triaza-spiro[4.5]dec-1-ene-8-carboxylic acid tert-butyl ester was synthesized by operations similar to those in Reaction 5-1 and Reaction 5-2 using appropriate reagents and starting material.

MS (ESI) m/z=372 (M+Na)+.

(Reaction 11-4)

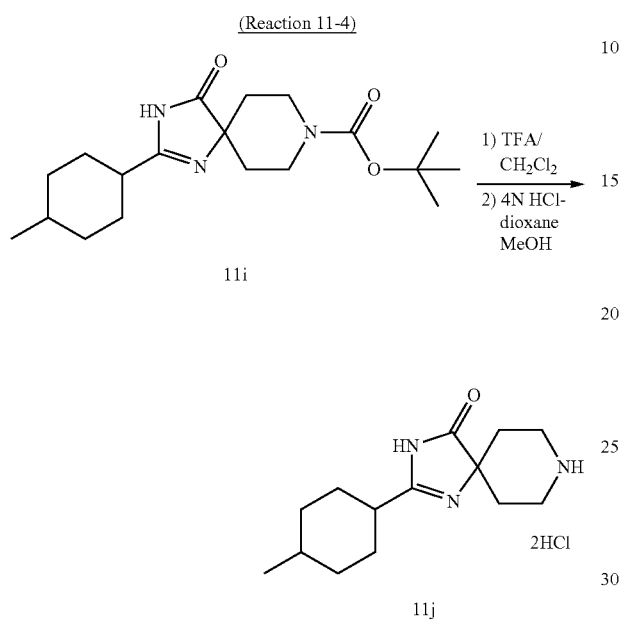

2-(4-Methyl-cyclohexyl)-1,3,8-triaza-spiro[4.5]dec-1-en-4-one dihydrochloride was synthesized by operations similar to those in Reaction 7-2 and Reaction 5-3 using appropriate reagents and starting material.

MS (ESI) m/z=250 (M+H)+.

Example 12

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 149)

(Reaction 12-1)

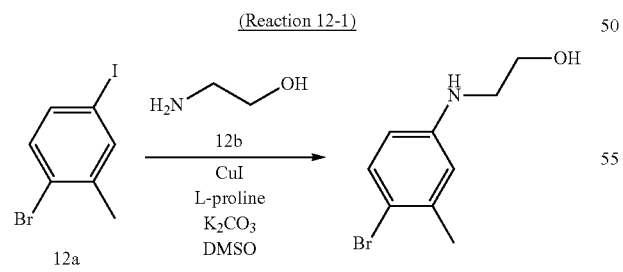

A mixture of 2-bromo-5-iodotoluene (1.60 g, 5.40 mmol), 2-aminoethanol (0.49 mL, 8.14 mmol), CuI (53.3 mg, 0.28 mmol), L-proline (63.4 mg, 0.55 mmol) and K₂CO₃ (1.49 g, 10.8 mmol) in DMSO (3.24 mL) was stirred at 60° C. for 12 hours. The reaction mixture was cooled and then diluted with AcOEt, and the organic layer was sequentially washed with H₂O and saturated brine. The organic layer was dried over Na₂SO₄ and then concentrated under reduced pressure. The resulting residue was purified by silica gel column chromatography (hexane/AcOEt=1/1) to give 2-(4-bromo-3-methyl-phenylamino)-ethanol as a brown solid (1.00 g, 81%).

MS (ESI) m/z=230, 232 (M+H)+.

(Reaction 12-2)

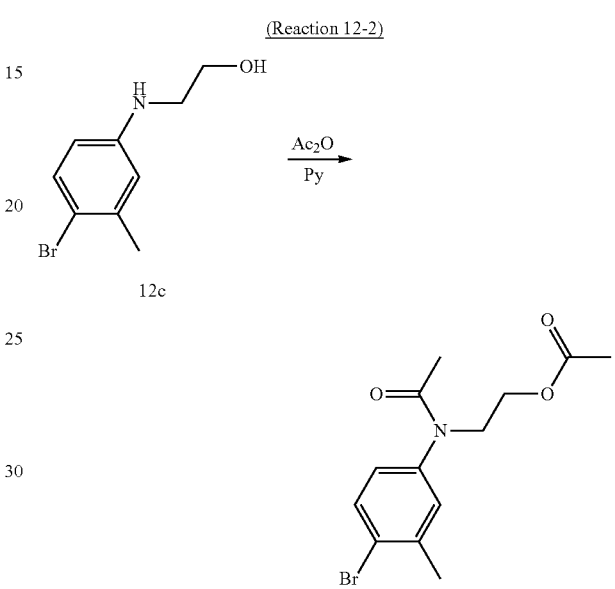

Pyridine (158.4 mL, 1.958 mol) was added to a solution of 2-(4-bromo-3-methyl-phenylamino)-ethanol (19.28 g, 83.788 mmol) in Ac₂O (158.4 mL, 1.676 mol). The mixture was stirred at room temperature for 18 hours and then concentrated under reduced pressure. The resulting residue was purified by silica gel column chromatography (CH₂Cl₂/MeOH=100/0 to 95/5) to give acetic acid 2-[acetyl-(4-bromo-3-methyl-phenyl)-amino]-ethyl ester as a brown viscous oil (21.44 g, 81%).

MS (ESI) m/z=314, 316 (M+H)+.

(Reaction 12-3)

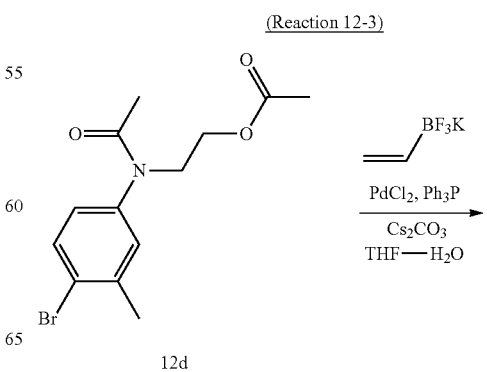

235
-continued
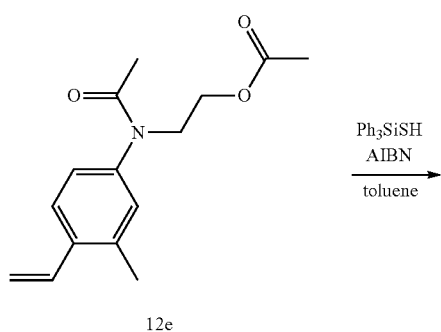
12e
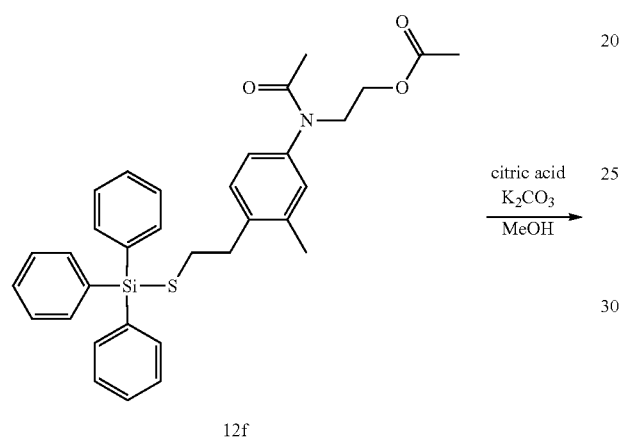
12f
236
-continued
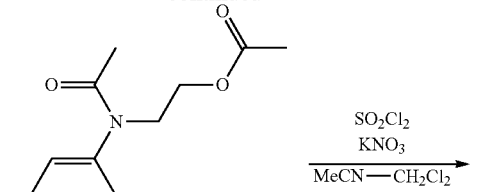
12g
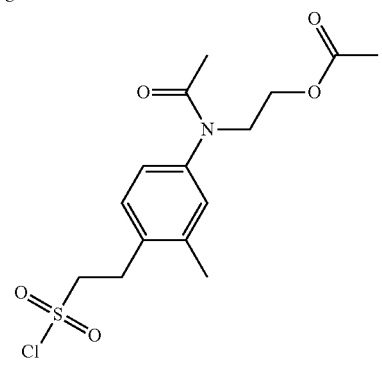
12h
Acetic acid 2-{acetyl-[4-(2-chlorosulfonyl-ethyl)-3-methyl-phenyl]-amino}-ethyl ester was synthesized by operations similar to those in Reaction 10-2, Reaction 10-3, Reaction 10-4 and Reaction 10-5 using appropriate reagents and starting material.
MS (ESI) m/z=362 (M+H)+.
(Reaction 12-4)
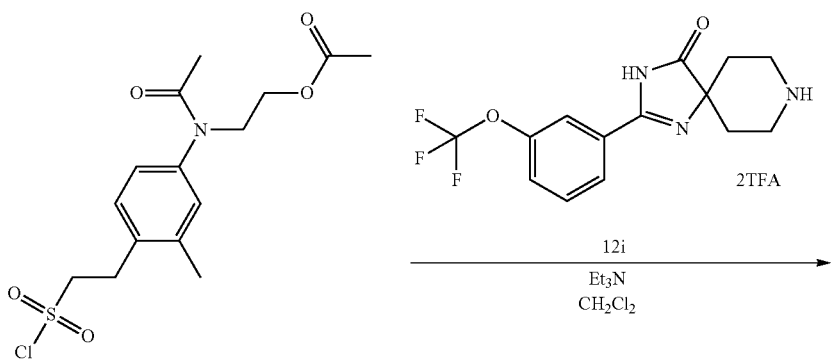
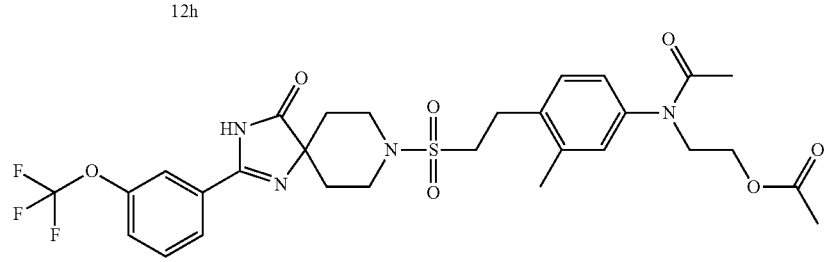
12j Acetic acid 2-[acetyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-amino]-ethyl ester was synthesized by operations similar to those in Reaction 5-4 of Example 5 using appropriate reagents and starting material.

MS (ESI) m/z=639 (M+H)+.

Example 13

Acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester (Compound 150)

(Reaction 12-5)

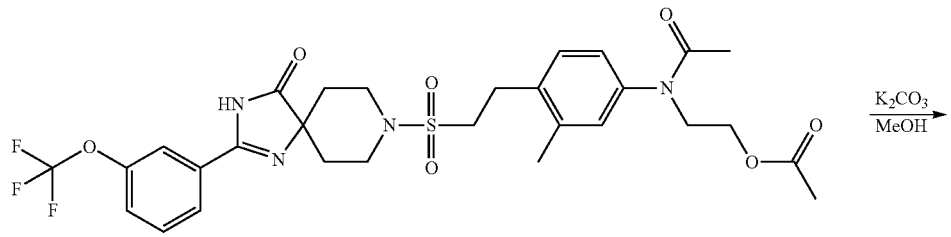

11j

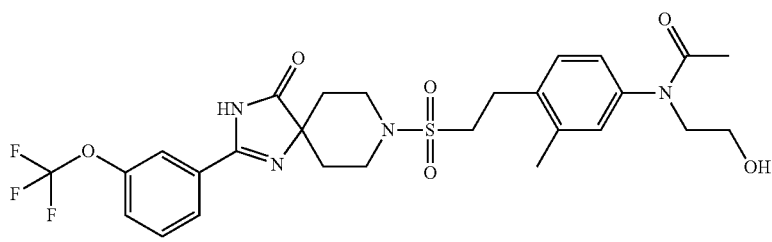

Compound 149

K$_2$CO$_3$ (9.1 mg, 66.0 μmol) was added to a solution of acetic acid 2-[acetyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-amino]-ethyl ester (28.1 mg, 44.0 μmol) in MeOH (0.5 mL). The mixture was stirred at room temperature for two hours. H$_2$O was then added and the mixture was diluted with CH$_2$Cl$_2$. The organic layer was washed with saturated brine, and then dried over MgSO$_4$ and concentrated under reduced pressure. The resulting residue was purified by column chromatography (CH$_2$Cl$_2$/MeOH=15/1) to give N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide as a white amorphous (24.0 mg, 92%).

$^1$H-NMR (400 MHz, CDCL$_3$) δ 1.71-1.75 (2H, m), 1.90 (3H, s), 2.09-2.04 (2H, m), 2.40 (3H, s), 3.16-3.24 (5H, m), 3.46-3.53 (4H, m), 3.77-3.87 (4H, m), 7.04-7.06 (2H, m), 7.24-7.26 (1H, m), 7.42-7.44 (1H, m), 7.58 (1H, t, J=8.3 Hz), 7.79-7.81 (1H, m), 7.86 (1H, m). MS (ESI) m/z=597 (M+H)+.

(Reaction 13-1)

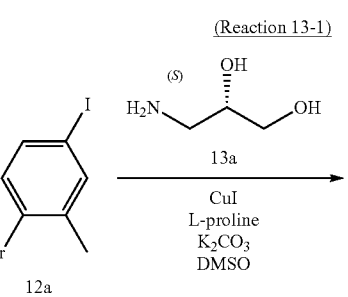

12a

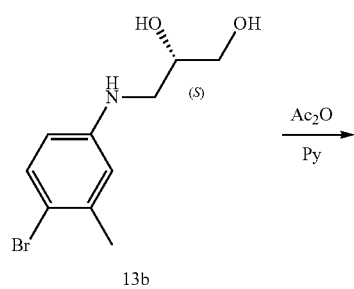

13b

239
-continued
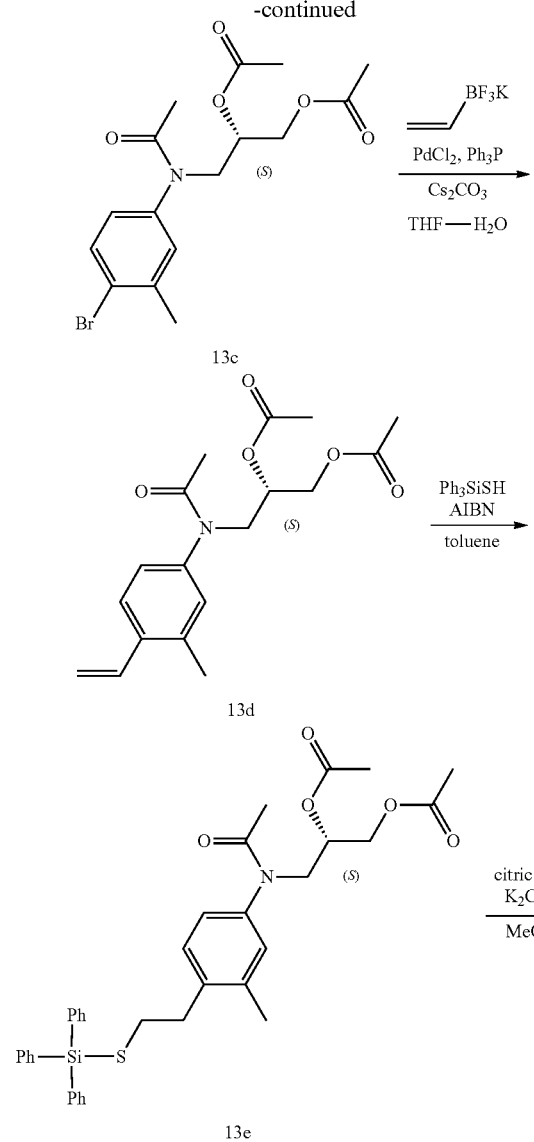
240
-continued
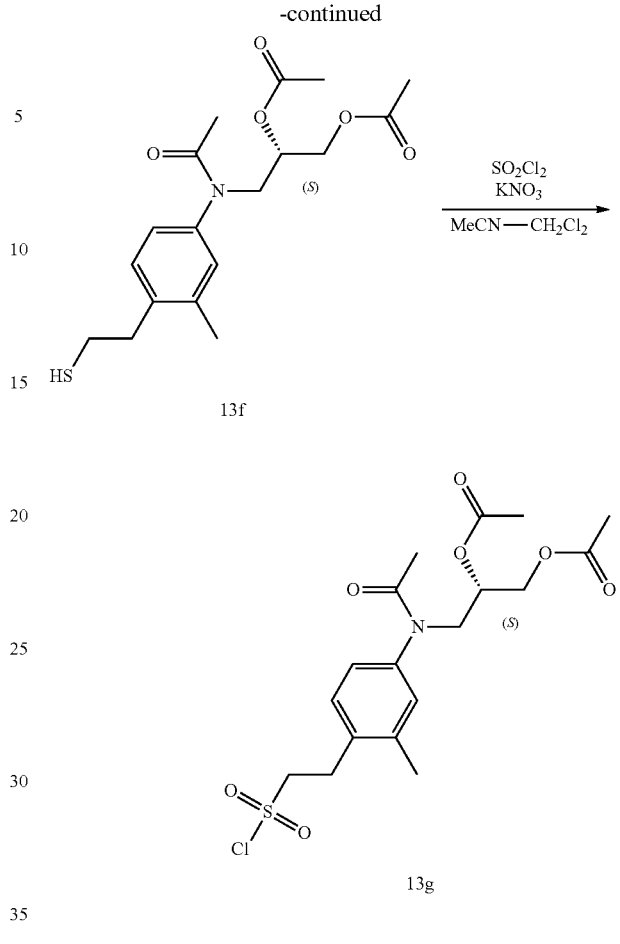
Acetic acid (S)-1-acetoxymethyl-2-{acetyl-[4-(2-chloro-sulfonyl-ethyl)-3-methyl-phenyl]-amino}-ethyl ester was synthesized by operations similar to those in Reaction 12-1, Reaction 12-2, Reaction 10-2, Reaction 10-3, Reaction 10-4 and Reaction 10-5 using appropriate reagents and starting material.
MS (ESI) m/z=434 (M+H)+.
(Reaction 13-2)
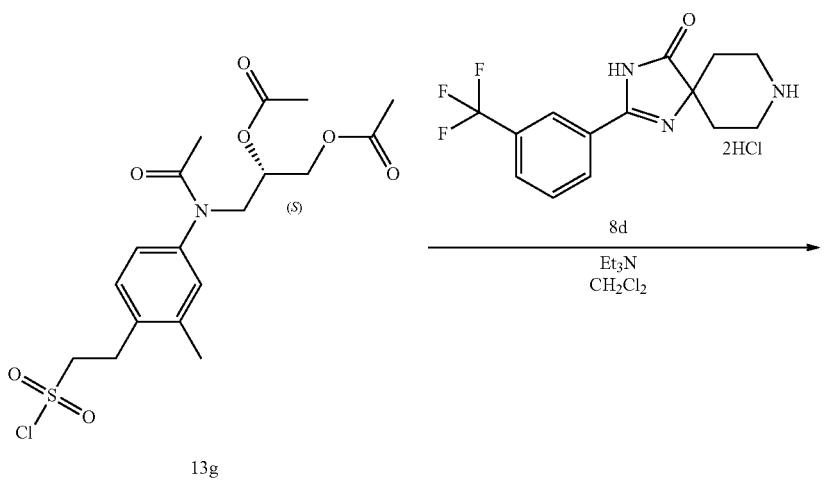

-continued

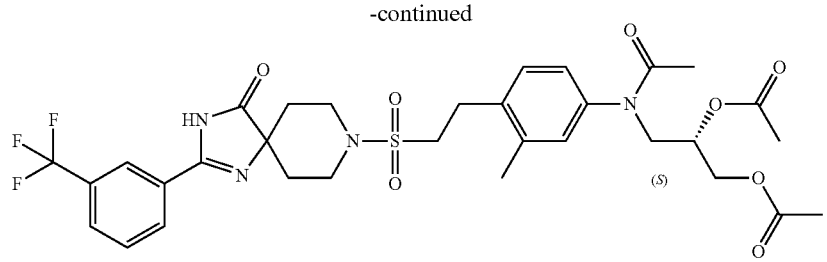

Compound 150

Acetic acid (S)-1-acetoxymethyl-2-[acetyl-(3-methyl-4-{2-[4-oxo-2-(3-trifluoromethyl-phenyl)-1,3,8-triaza-spiro[4.5]dec-1-ene-8-sulfonyl]-ethyl}-phenyl)-amino]-ethyl ester was synthesized by operations similar to those in Reaction 5-4 using appropriate reagents and starting material.

MS (ESI) m/z=695 (M+H)+.

The example compounds shown below were synthesized by operations similar to those in Example 13 using appropriate reagents and starting materials.

TABLE 23

| Compound | Structure | LCMS or HPLC condition | Retention time (min) | MS (m/z) |
|---|---|---|---|---|
| 151 | 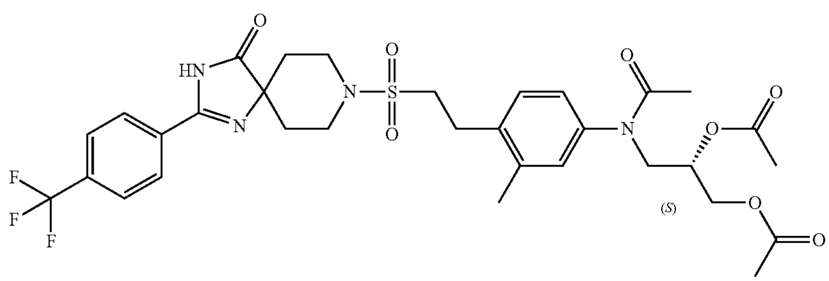 | LCMS-A-1 | 2.53 | 695 (M + H)+ |
| 152 | 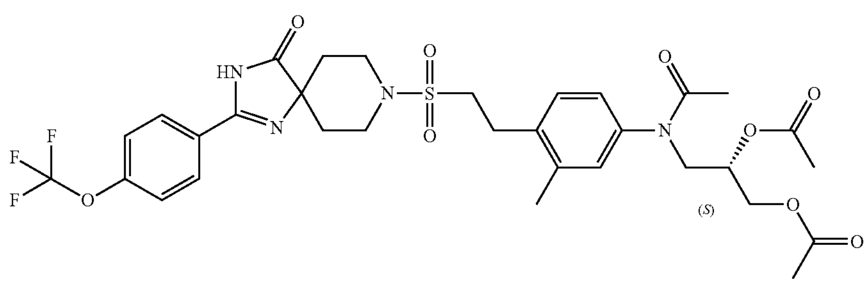 | LCMS-A-1 | 2.50 | 711 (M + H)+ |
| 153 | 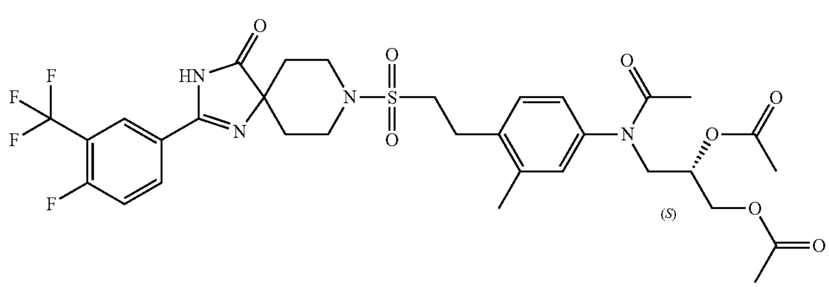 | LCMS-A-1 | 2.57 | 713 (M + H)+ |

Example 14

8-{2-[4-((S)-2,3-Dihydroxy-propylamino)-2-methyl-phenyl]-ethanesulfonyl}-2-(4-trifluoromethyl-phenyl)-1,3,8-triaza-spiro[4.5]dec-1-en-4-one (Compound 154)

(Reaction 14-1)

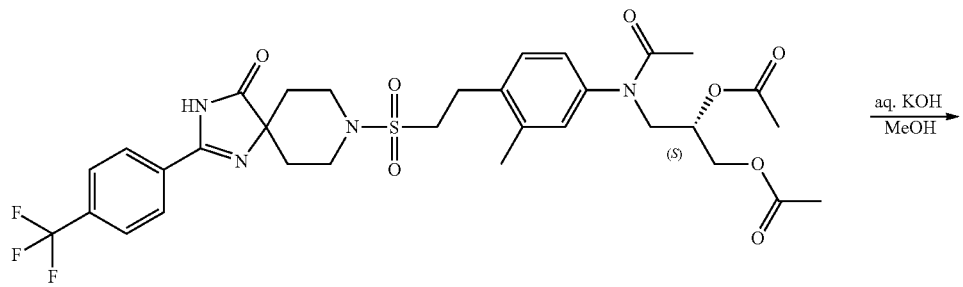

Compound 151

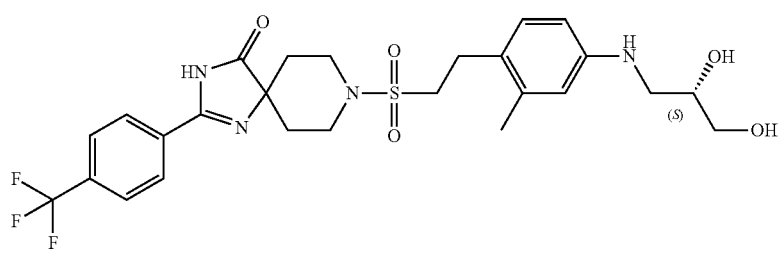

Compound 154

A 1.2 M aqueous KOH solution (0.5 mL) was added to a solution of acetic acid (S)-1-acetoxymethyl-2-[acetyl-(3-methyl-4-{2-[4-oxo-2-(4-trifluoromethyl-phenyl)-1,3,8-triaza-spiro[4.5]dec-1-ene-8-sulfonyl]-ethyl}-phenyl)-amino]-ethyl ester (40.8 mg, 0.0587 mmol) in MeOH (3 mL). The reaction mixture was stirred at 50° C. for 1.5 hours and then cooled to room temperature. Dowex 50 W×4 (237.6 mg) was added. The mixture was further stirred at room temperature for two hours and then filtered, and the organic layer was concentrated under reduced pressure. The resulting residue was purified by silica gel column chromatography (CH$_2$Cl$_2$/MeOH=10/1) to give 8-{2-[4-((S)-2,3-dihydroxy-propylamino)-2-methyl-phenyl]-ethanesulfonyl}-2-(4-trifluoromethyl-phenyl)-1,3,8-triaza-spiro[4.5]dec-1-en-4-one as a white powder (30.3 mg, 91%).

$^1$H-NMR (400 MHz, CD3OD) δ 1.72-1.75 (2H, m), 1.99-2.04 (2H, m), 2.28 (3H, s), 2.98-3.06 (3H, m), 3.19-3.28 (2H, m), 3.46-3.61 (5H, m), 3.77-3.80 (3H, m), 6.49-6.53 (2H, m), 6.98 (1H, d, J=8.3 Hz), 7.85 (2H, d, J=8.3 Hz), 8.12 (2H, d, J=8.3 Hz). MS (ESI) m/z=569 (M+H)+.

The example compound shown below was synthesized by operations similar to those in Example 14 using appropriate reagents and starting material.

TABLE 24

| Compound | Structure | LCMS or HPLC condition | Retention time (min) | MS (m/z) |
|---|---|---|---|---|
| 155 | (structure) | LCMS-A-1 | 1.93 | 569 (M + H)+ |

Example 15

8-{2-[4-((S)-2,3-Dihydroxy-propylamino)-2-methyl-phenyl]-ethanesulfonyl}-2-(4-trifluoromethoxy-phenyl)-1,3,8-triaza-spiro[4.5]dec-1-en-4-one (Compound 156)

(Reaction 15-1)

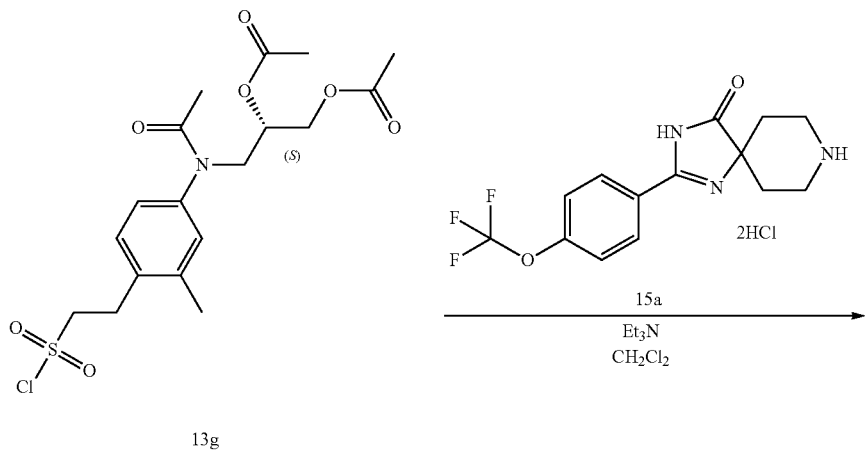

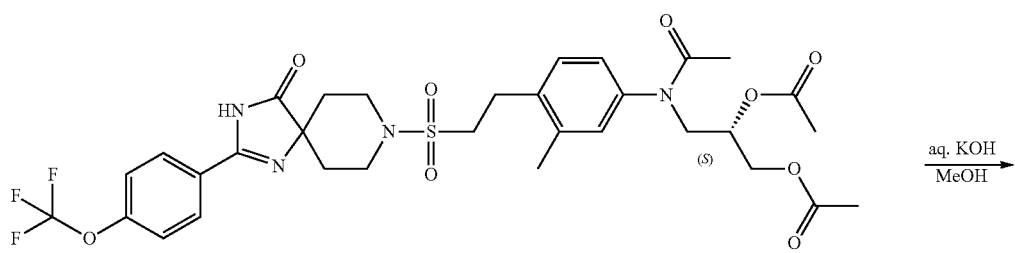

Compound 152

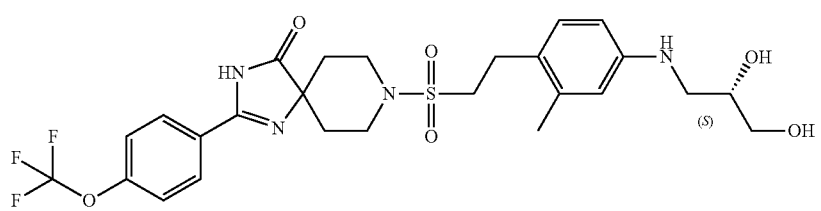

Compound 156

8-{2-[4-((S)-2,3-Dihydroxy-propylamino)-2-methyl-phenyl]-ethanesulfonyl}-2-(4-trifluoromethoxy-phenyl)-1,3,8-triaza-spiro[4.5]dec-1-en-4-one was synthesized by operations similar to those in Reaction 5-4 and Reaction 14-1 using appropriate reagents and starting material.

MS (ESI) m/z=585 (M+H)+.

The example compounds shown below were synthesized by operations similar to those in Example 15 using appropriate reagents and starting materials.

TABLE 25

| Compound | Structure | LCMS or HPLC condition | Retention time (min) | MS (m/z) |
|---|---|---|---|---|
| 157 | 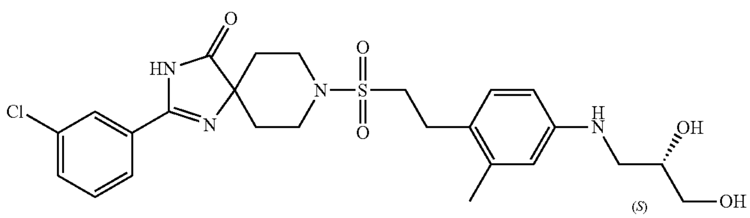 | LCMS-B-1 | 1.54 | 535 (M + H)+ |
| 158 | 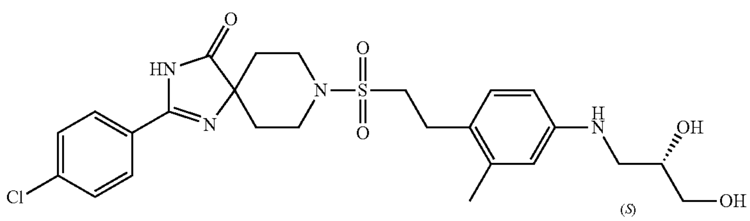 | LCMS-C-1 | 2.35 | 535 (M + H)+ |

Example 16

8-{2-[4-(2-Hydroxy-ethylamino)-2-methyl-phenyl]-ethanesulfonyl}-2-(3-trifluoromethoxy-phenyl)-1,3,8-triaza-spiro[4.5]dec-1-en-4-one (Compound 159)

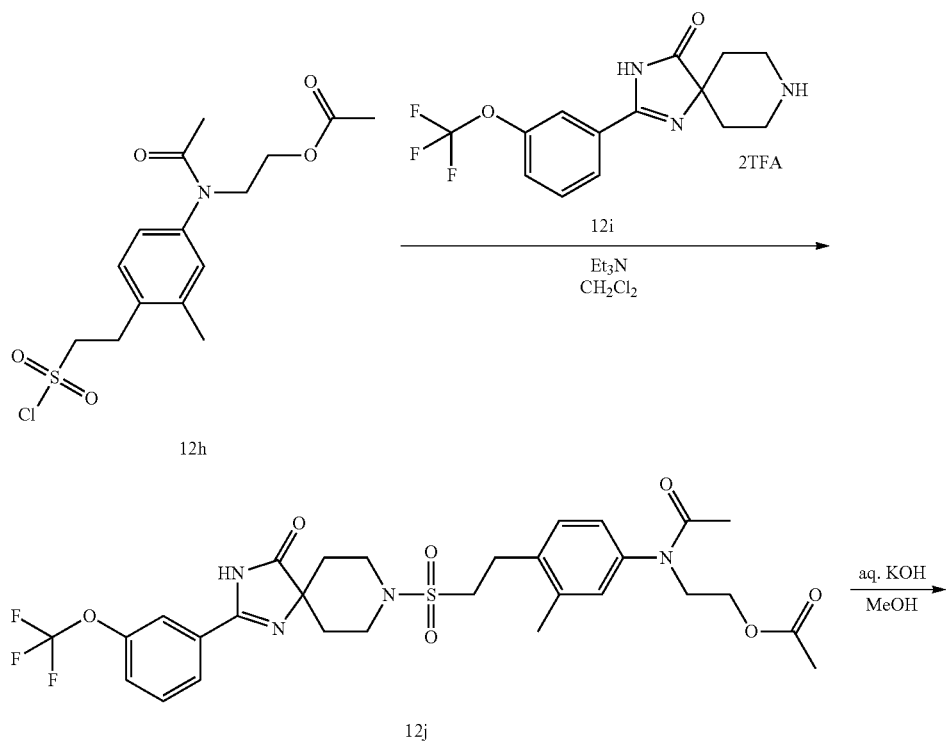

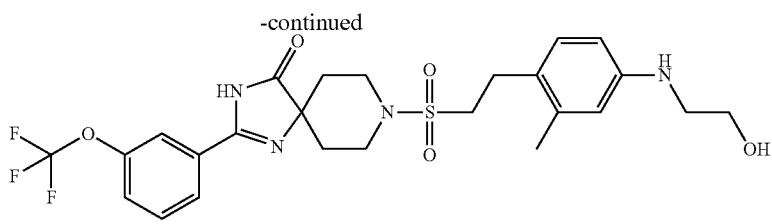

Compound 159

8-{2-[4-(2-Hydroxy-ethylamino)-2-methyl-phenyl]-ethanesulfonyl}-2-(3-trifluoromethoxy-phenyl)-1,3,8-triaza-spiro[4.5]dec-1-en-4-one was synthesized by operations similar to those in Reaction 5-4 and Reaction 14-1 using appropriate reagents and starting material.

MS (ESI) m/z=555 (M+H)+.

The example compounds shown below were synthesized by operations similar to those in Example 16 using appropriate reagents and starting materials.

NaBH$_4$ (1.45 g, 38.25 mmol) was added in small portions to a mixture of 4-bromo-3-methyl-benzonitrile (2.50 g, 12.8 mmol), NiCl$_2$ (1.65 g, 12.8 mmol) and Boc$_2$O (5.57 g, 25.5 mmol) in anhydrous MeOH (130 ml) at 0° C. The mixture was stirred at room temperature for two hours and then concentrated under reduced pressure. Ethyl acetate and water were added to the resulting residue, and the mixture was filtered through celite. The two-layer solution was separated, and the aqueous layer was then further extracted

TABLE 26

| Compound | Structure | LCMS or HPLC condition | Retention time (min) | MS (m/z) |
|---|---|---|---|---|
| 160 | 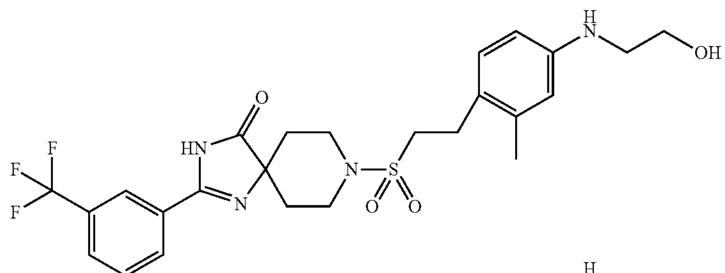 | LCMS-B-1 | 1.73 | 539 (M + H)+ |
| 161 | 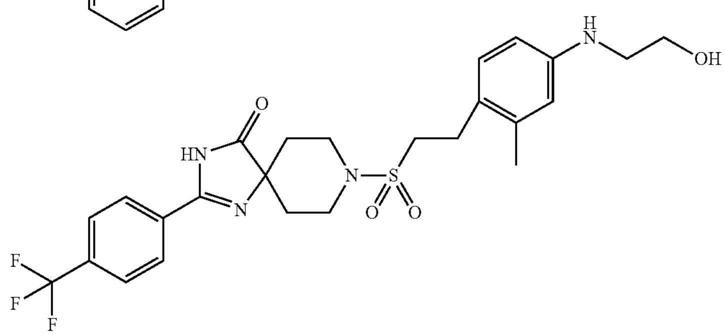 | LCMS-B-1 | 1.47 | 539 (M + H)+ |

Example 17

{4-[2-(2-tert-Butyl-4-oxo-1,3,8-triaza-spiro[4.5]dec-1-ene-8-sulfonyl)-ethyl]-3-methyl-benzyl}-carbamic acid tert-butyl ester (Compound 162)

(Reaction 17-1)

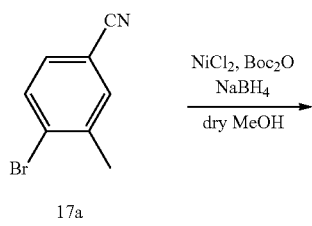

with ethyl acetate. The organic layers were combined, dried over Na$_2$SO$_4$ and concentrated under reduced pressure. The residue was purified by silica gel column chromatography (hexane/ethyl acetate=1/0→4/1) to give (4-bromo-3-methyl-benzyl)-carbamic acid tert-butyl ester as a white solid (2.42 g, 63%).

MS (ESI) m/z=322 (M+Na)+.

(Reaction 17-2)

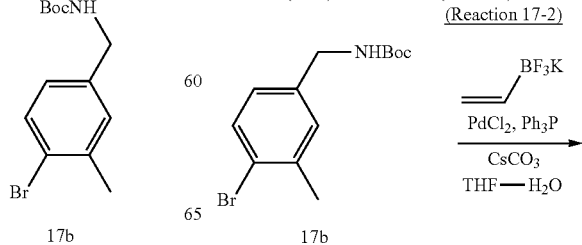

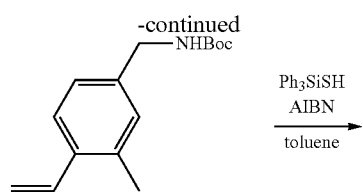

[4-(2-Chlorosulfonyl-ethyl)-3-methyl-benzyl]-carbamic acid tert-butyl ester was synthesized by operations similar to those in Reaction 10-2, Reaction 10-3, Reaction 10-4 and Reaction 10-5 using appropriate reagents and starting material.

MS (ESI) m/z=292 (M-tBu+Hx2)+.

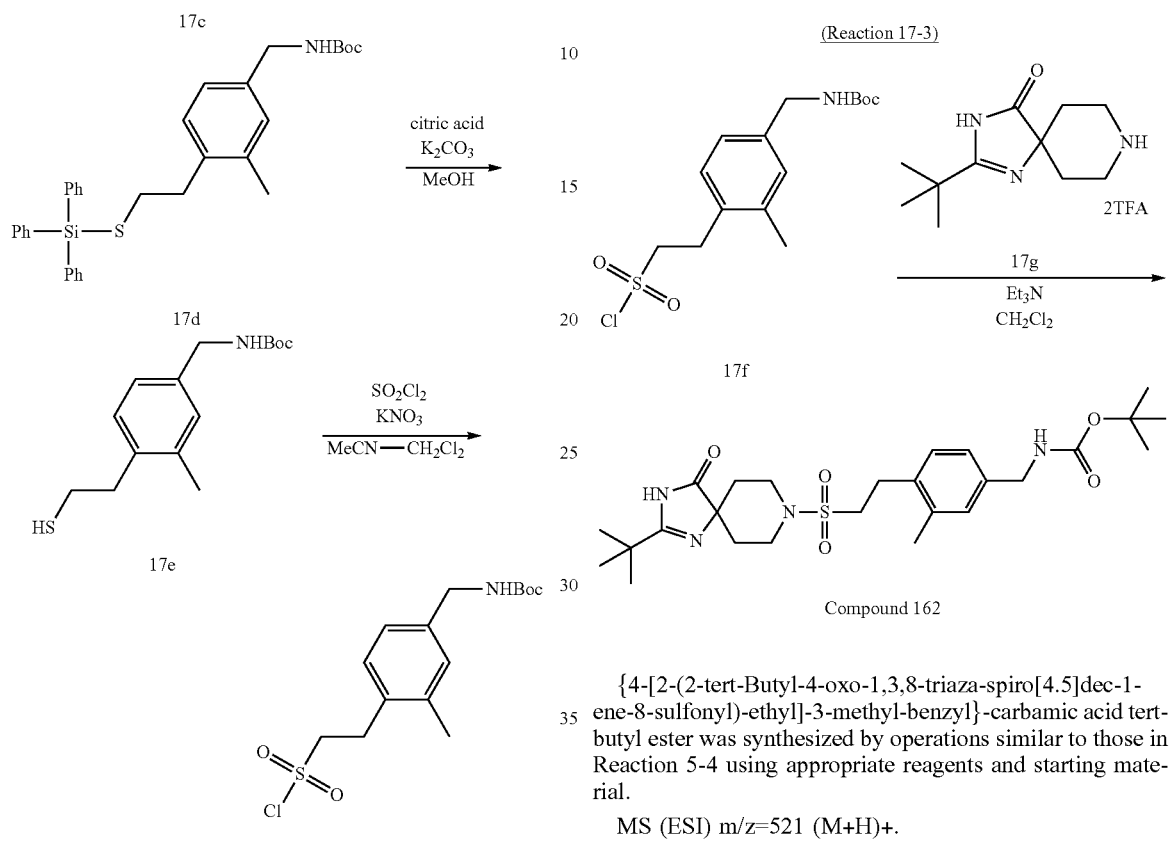

{4-[2-(2-tert-Butyl-4-oxo-1,3,8-triaza-spiro[4.5]dec-1-ene-8-sulfonyl)-ethyl]-3-methyl-benzyl}-carbamic acid tert-butyl ester was synthesized by operations similar to those in Reaction 5-4 using appropriate reagents and starting material.

MS (ESI) m/z=521 (M+H)+.

The example compounds shown below were synthesized by operations similar to those in Example 17 using appropriate reagents and starting materials.

TABLE 27

| Compound | Structure | LCMS or HPLC condition | Retention time (min) | MS (m/z) |
| --- | --- | --- | --- | --- |
| 163 | 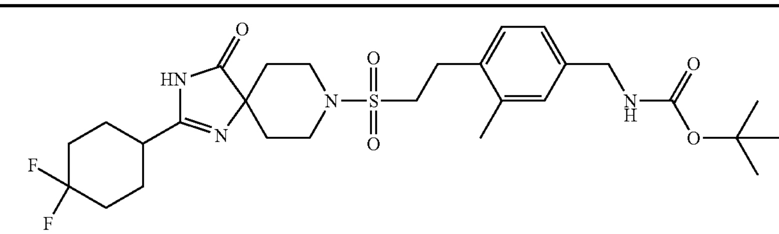 | LCMS-C-1 | 2.67 | 583 (M + H)+ |
| 164 | 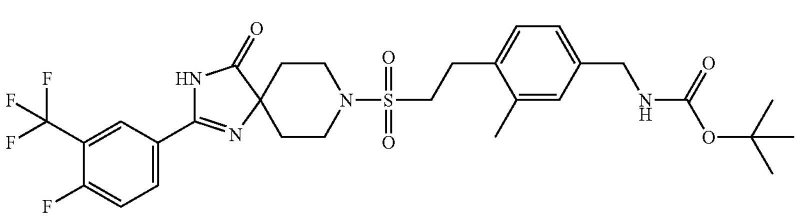 [SMILES: Cc1cc(CNC(=O)OC(C)(C)C)ccc1CCS(=O)(=O)N1CCC2(CC1)N=C(c1ccc(F)c(C(F)(F)F)c1)NC2=O] | LCMS-C-2 | 2.35 | 625 (M − H)− |

TABLE 27-continued

| Compound | Structure | LCMS or HPLC condition | Retention time (min) | MS (m/z) |
|---|---|---|---|---|
| 165 | 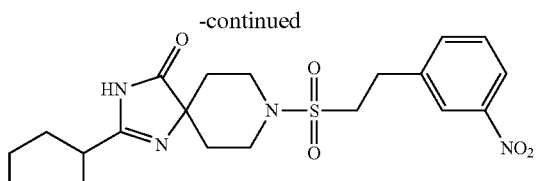 | LCMS-B-1 | 1.92 | 549 (M + H)+ |

The spiroamine reagent used in the synthesis of Compound 163 (2-(4,4-difluoro-cyclohexyl)-1,3,8-triaza-spiro[4.5]dec-1-en-4-one ditrifluoroacetate) was synthesized by operations similar to those in Reaction 10-14, Reaction 5-2 and Reaction 7-2 using appropriate reagents and starting material.

Example 18

8-[2-(3-Amino-phenyl)-ethanesulfonyl]-2-cyclohexyl-1,3,8-triaza-spiro[4.5]dec-1-en-4-one (Compound 166)

(Reaction 18-1)

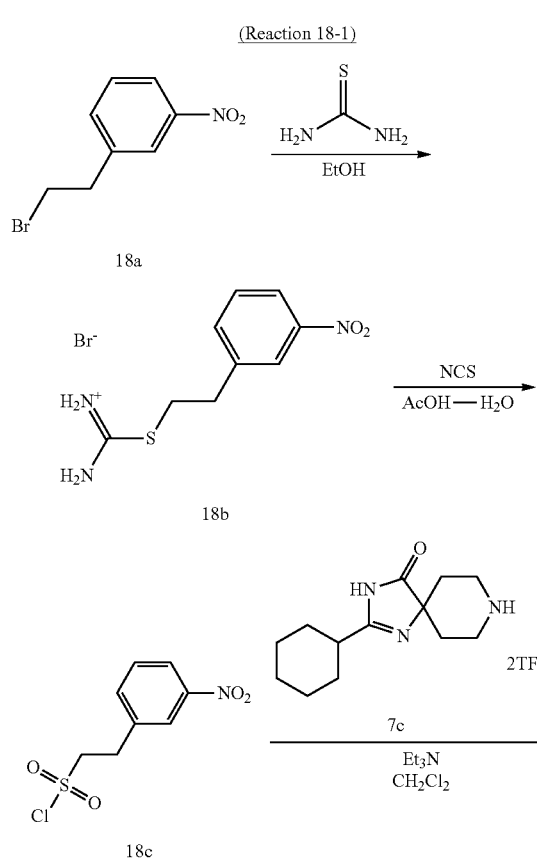

A mixture of 1-(2-bromo-ethyl)-3-nitro-benzene (4 g, 17.4 mmol) and thiourea (1.5 g, 19.1 mmol) in ethanol (20 mL) was heated under reflux for one hour. The reaction mixture was concentrated under reduced pressure to give Compound 18b as a pale yellow solid. Further, NCS (7.66 g, 57.4 mmol) was added to a mixed solution of this solid in acetic acid (43.5 ml) and $H_2O$ (14.5 ml) on an ice bath, and the mixture was stirred at 5 to 10° C. for 50 minutes. The reaction mixture was diluted with $CH_2Cl_2$, and the organic layer was then washed with water, dried over $Na_2SO_4$ and concentrated under reduced pressure. Compound 7c (5.2 g, 11.2 mmol) and $Et_3N$ (6.3 mL, 44.9 mmol) were added to a solution of the resulting Compound 18c in $CH_2Cl_2$, and the mixture was stirred at room temperature for four hours. The reaction mixture was concentrated under reduced pressure, and the residue was then purified by silica gel flash chromatography to give 2-cyclohexyl-8-[2-(3-nitro-phenyl)-ethanesulfonyl]-1,3,8-triaza-spiro[4.5]dec-1-en-4-one (18d) as a white solid (1 g, yield 20% (three steps)). This compound was directly used in the next step.

(Reaction 18-2)

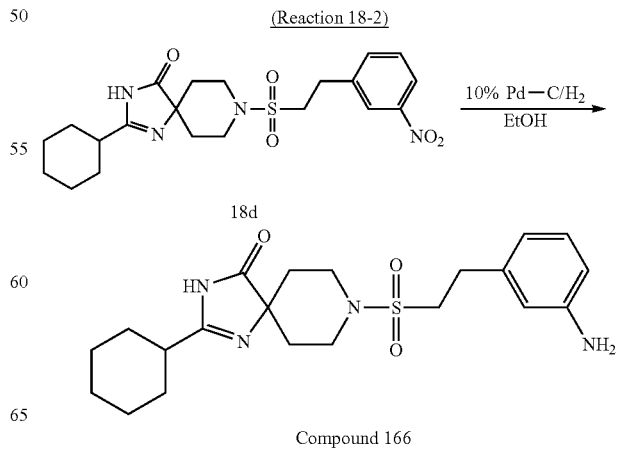

Compound 166

10% Pd—C(1 g) was added to a solution of Compound 18d (1 g, 2.23 mmol) in ethanol (10 ml), and the mixture was stirred at room temperature for two days in an $H_2$ atmosphere. The reaction mixture was filtered, and the filtrate was then concentrated under reduced pressure to give 8-[2-(3-amino-phenyl)-ethanesulfonyl]-2-cyclohexyl-1,3,8-triaza-spiro[4.5]dec-1-en-4-one (920 mg, 98%).

MS (ESI) m/z=419 (M+H)+.

Example 19

N-{4-[2-(2-Cyclohexyl-4-oxo-1,3,8-triaza-spiro[4.5]dec-1-ene-8-sulfonyl)-ethyl]-phenyl}-acetamide (Compound 167)

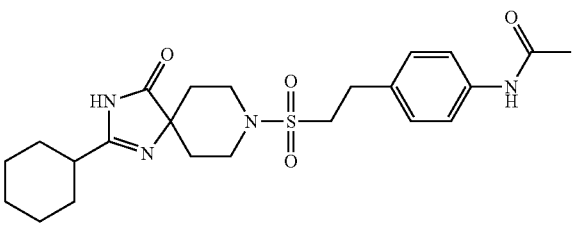

Compound 167

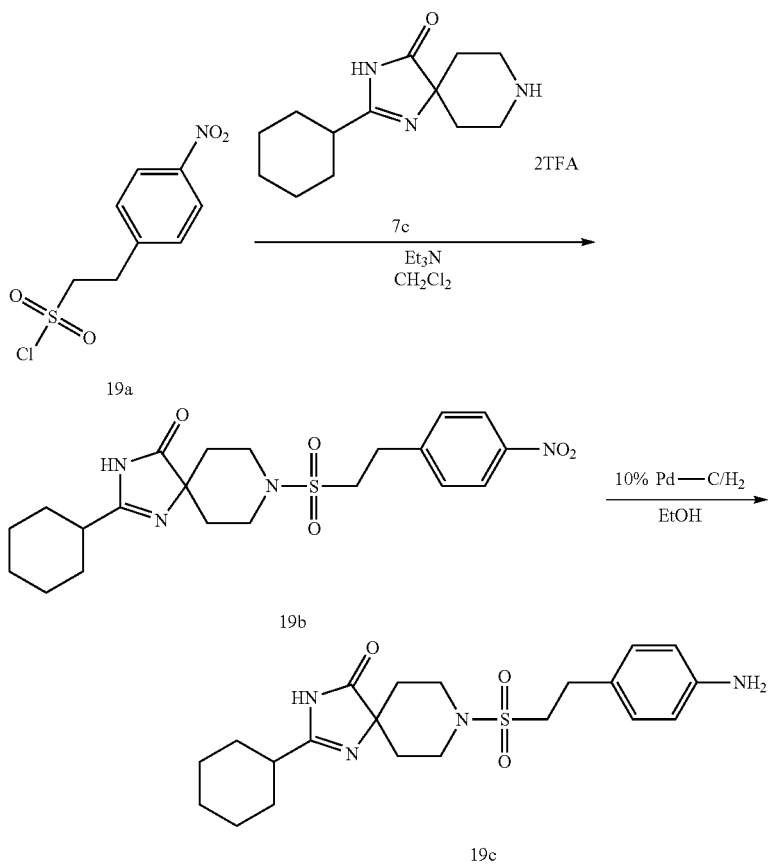

8-[2-(4-Amino-phenyl)-ethanesulfonyl]-2-cyclohexyl-1,3,8-triaza-spiro[4.5]dec-1-en-4-one was synthesized by operations similar to those in Reaction 5-4 and Reaction 18-2 using appropriate reagents and starting material. This compound was directly used in the next step.

Acetic anhydride (45 mg, 0.44 mmol) was added to a solution of 8-[2-(4-amino-phenyl)-ethanesulfonyl]-2-cyclohexyl-1,3,8-triaza-spiro[4.5]dec-1-en-4-one (92 mg, 0.22 mmol) in $CH_2Cl_2$ (5 mL). Triethylamine (55 mg, 0.5 mmol) was then added on an ice bath, and the mixture was stirred at room temperature for one hour. The reaction mixture was diluted with dichloromethane, and the organic layer was then sequentially washed with water and saturated brine and dried over $Na_2SO_4$. The organic layer was concentrated under reduced pressure, and the resulting residue was then purified by P-TLC to give N-{4-[2-(2-cyclohexyl-4-oxo-1,3,8-triaza-spiro[4.5]dec-1-ene-8-sulfonyl)-ethyl]-phenyl}-acetamide (55 mg, 54.3%).

MS (ESI) m/z=461 (M+H)+.

Example 20

3,N,N-Trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide (Compound 168)

(Reaction 20-1)

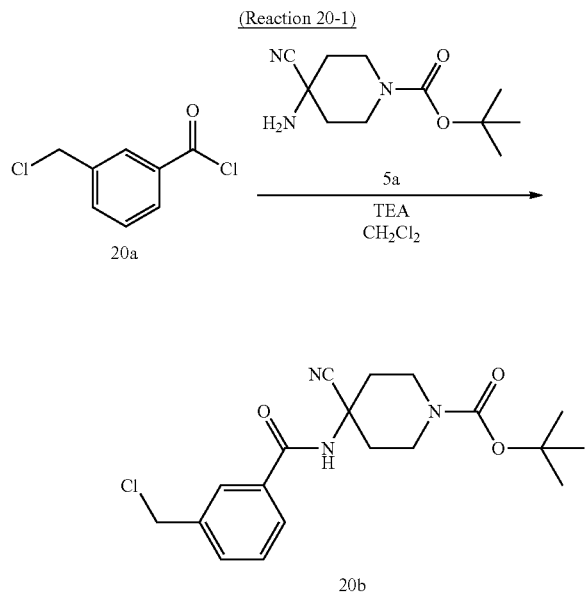

(Reaction 20-2)

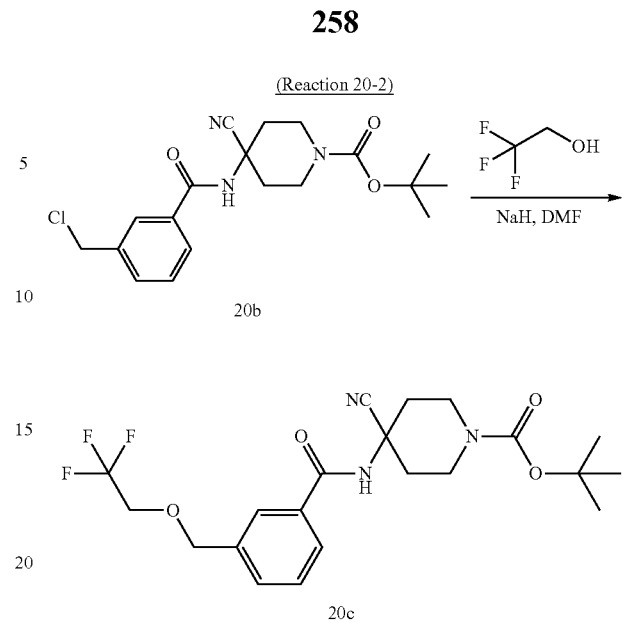

4-(3-Chloromethyl-benzoylamino)-4-cyano-piperidine-1-carboxylic acid tert-butyl ester was synthesized by operations similar to those in Reaction 2-3 using appropriate reagents and starting material.

MS (ESI) m/z=342 (M+H)+.

Sodium hydride (60% oil suspension, 191 mg, 4.77 mmol) was added to a solution of 2,2,2-trifluoro-ethanol (347 μl, 4.77 mmol) and 4-(3-chloromethyl-benzoylamino)-4-cyano-piperidine-1-carboxylic acid tert-butyl ester (600 mg, 1.59 mmol) in DMF (8 ml) at 0° C. The mixture was stirred at room temperature overnight, and then quenched with water and diluted with ethyl acetate. The organic layer was sequentially washed with a saturated aqueous NaHCO₃ solution, water (×2) and saturated brine, and then dried over Na₂SO₄ and concentrated under reduced pressure. The resulting residue was purified by silica gel column chromatography (hexane/ethyl acetate=2/1→1/2) to give 4-cyano-4-[3-(2,2,2-trifluoro-ethoxymethyl)-benzoylamino]-piperidine-1-carboxylic acid tert-butyl ester as a white solid (366 mg, 52%).

MS (ESI) m/z=442 (M+H)+.

(Reaction 20-3)

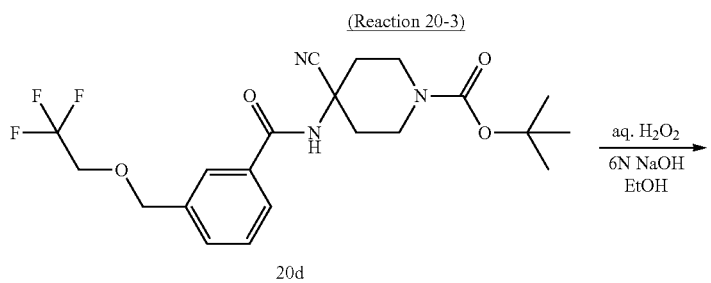

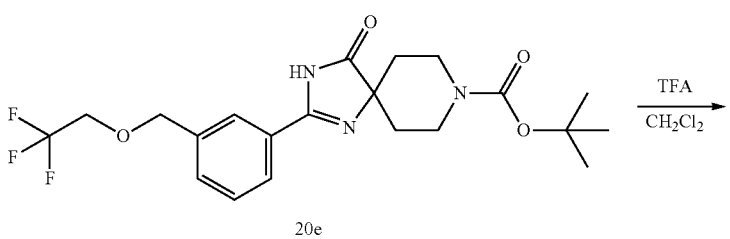

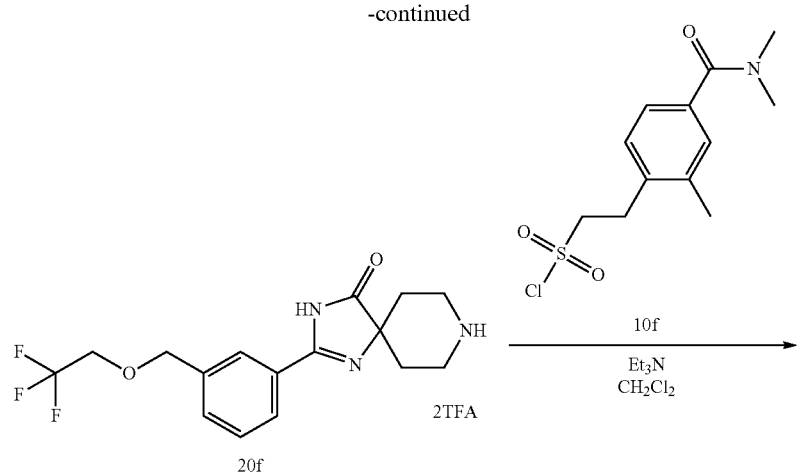

20f

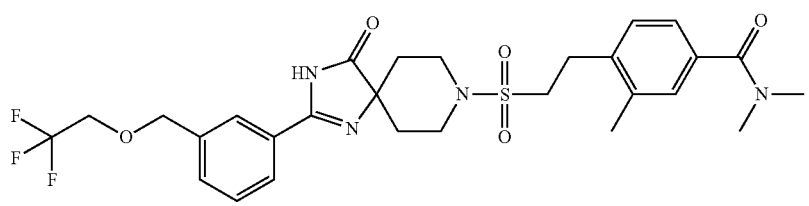

Compound 168

3,N,N-Trimethyl-4-(2-{4-oxo-2-[3-(2,2,2-trifluoro-ethoxymethyl)-phenyl]-1,3,8-triaza-spiro[4.5]dec-1-ene-8-sulfonyl}-ethyl)-benzamide was synthesized by operations similar to those in Reaction 5-2, Reaction 7-2 and Reaction 5-4 using appropriate reagents and starting material.

MS (ESI) m/z=595 (M+H)+.

The example compounds shown below were synthesized by operations similar to those in Example 20 using appropriate reagents and starting materials.

TABLE 28

| Compound | Structure | LCMS or HPLC condition | Retention time (min) | MS (m/z) |
|---|---|---|---|---|
| 169 | 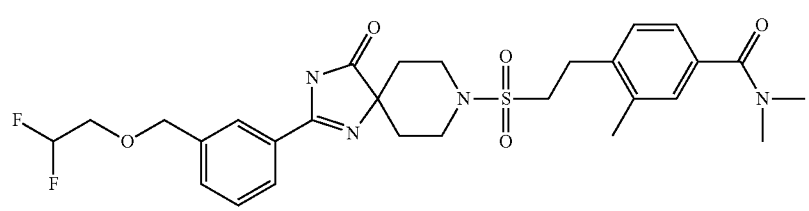 [SMILES: Cc1cc(C(=O)N(C)C)ccc1CCS(=O)(=O)N1CCC2(CC1)N=C(c1cccc(COCC(F)F)c1)NC2=O] | LCMS-C-1 | 2.23 | 577 (M + H)+ |
| 170 | 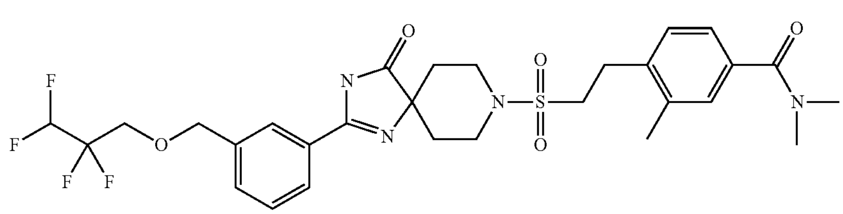 [SMILES: Cc1cc(C(=O)N(C)C)ccc1CCS(=O)(=O)N1CCC2(CC1)N=C(c1cccc(COCC(F)(F)C(F)F)c1)NC2=O] | LCMS-C-1 | 2.53 | 627 (M + H)+ |

Example 21

4-(2-{2-[3-(3,5-Dimethyl-isoxazol-4-yl)-phenyl]-4-oxo-1,3,8-triaza-spiro[4.5]dec-1-ene-8-sulfonyl}-ethyl)-3,N,N-trimethyl-benzamide (Compound 171)

(Reaction 21-1)

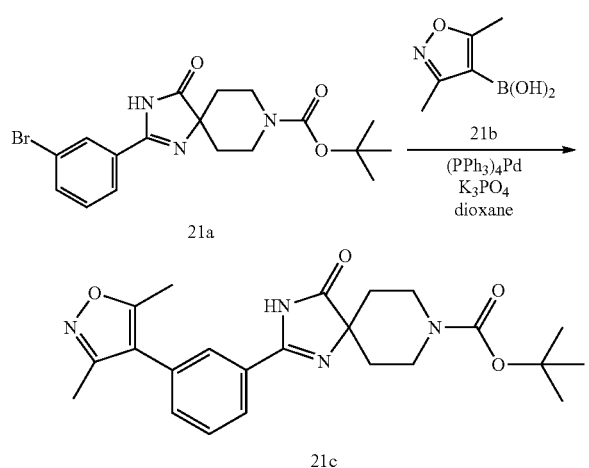

(Reaction 21-2)

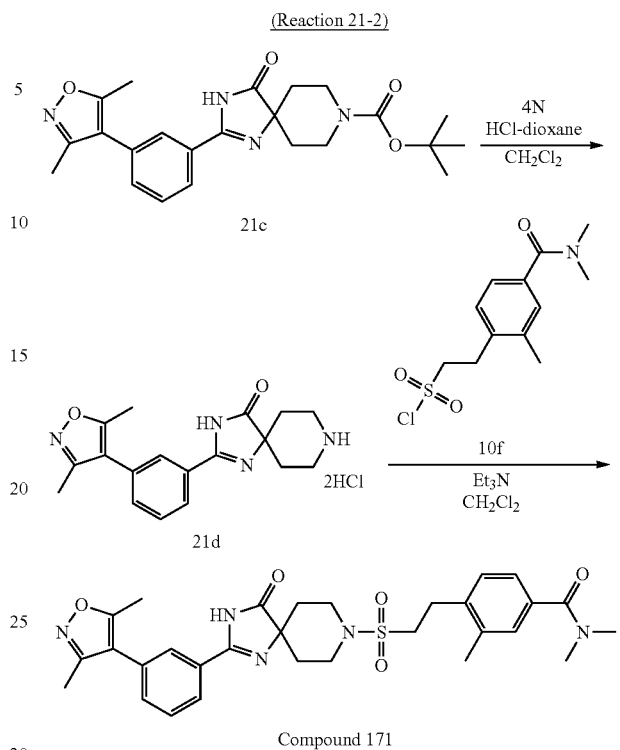

A mixture of 2-(3-bromo-phenyl)-4-oxo-1,3,8-triaza-spiro[4.5]dec-1-ene-8-carboxylic acid tert-butyl ester (100 mg, 0.245 mmol), 3,5-dimethyl-isoxazole-4-boronic acid (51.8 mg, 0.367 mmol), tetrakis-(triphenylphosphine)palladium(0) (28 mg, 0.0245 mmol) and K$_3$PO$_4$ (104 mg, 0.490 mmol) in dioxane (1.2 mL) was heated with stirring at 100° C. for one hour in a nitrogen atmosphere. The reaction mixture was cooled, and then quenched with water and extracted with ethyl acetate (×3). The organic layers were combined and sequentially washed with water (×2) and saturated brine, and then dried over sodium sulfate and concentrated under reduced pressure. The resulting residue was purified by silica gel column chromatography (n-hexane:ethyl acetate=2:1) to give 2-[3-(3,5-dimethyl-isoxazol-4-yl)-phenyl]-4-oxo-1,3,8-triaza-spiro[4.5]dec-1-ene-8-carboxylic acid tert-butyl ester as a pale yellow solid (88.3 mg, 85%).

$^1$H-NMR (400 MHz, CDCl$_3$) δ 1.51 (9H, s), 1.52-1.63 (2H, m), 1.89-2.27 (2H, m), 2.31 (3H, s), 2.45 (3H, s), 3.38-3.55 (2H, m), 3.94-4.12 (2H, m), 7.45 (1H, d, J=7.8 Hz), 7.61 (1H, dd, J=7.8, 7.8 Hz), 7.85 (1H, s), 7.92 (1H, d, J=7.8 Hz), 10.20 (1H, brs).

4-(2-{2-[3-(3,5-Dimethyl-isoxazol-4-yl)-phenyl]-4-oxo-1,3,8-triaza-spiro[4.5]dec-1-ene-8-sulfonyl}-ethyl)-3,N,N-trimethyl-benzamide was synthesized by operations similar to those in Reaction 5-3 and Reaction 5-4 using appropriate reagents and starting material.

$^1$H-NMR (400 MHz, CD3OD) δ 1.73-1.82 (2H, m), 1.98-2.07 (2H, m), 2.27 (3H, s), 2.42 (3H, s), 2.43 (3H, s), 3.00 (3H, s), 3.09 (3H, s), 3.14-3.22 (2H, m), 3.32-3.38 (2H, m), 3.45-3.55 (2H, m), 3.75-3.84 (2H, m), 7.23 (1H, d, J=7.8 Hz), 7.26 (1H, s), 7.34 (1H, d, J=7.8 Hz), 7.60 (1H, d, J=7.8 Hz), 7.66 (1H, d, J=7.8 Hz), 7.92 (1H, s), 7.99 (1H, d, J=7.8 Hz). MS (ESI) m/z=578 (M+H)+.

The example compounds shown below were synthesized by operations similar to those in Example 21 using appropriate reagents and starting materials.

TABLE 29

| Compound | Structure | LCMS or HPLC condition | Retention time (min) | MS (m/z) |
|---|---|---|---|---|
| 172 | 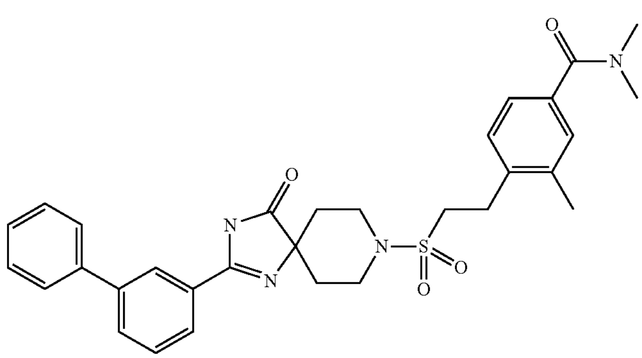 [SMILES: Cc1cc(C(=O)N(C)C)ccc1CCS(=O)(=O)N1CCC2(CC1)N=C(c1cccc(-c3ccccc3)c1)NC2=O] | LCMS-B-1 | 2.11 | 559 (M + H)+ |

TABLE 29-continued

| Compound | Structure | LCMS or HPLC condition | Retention time (min) | MS (m/z) |
|---|---|---|---|---|
| 173 | 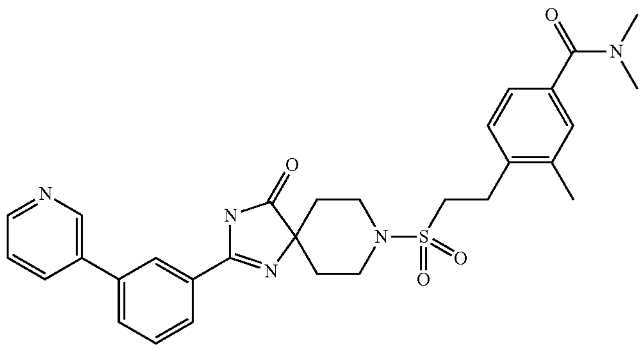 [SMILES: Cc1cc(C(=O)N(C)C)ccc1CCS(=O)(=O)N1CCC2(CC1)N=C(c1cccc(-c3cccnc3)c1)NC2=O] | LCMS-B-1 | 1.50 | 560 (M + H)+ |

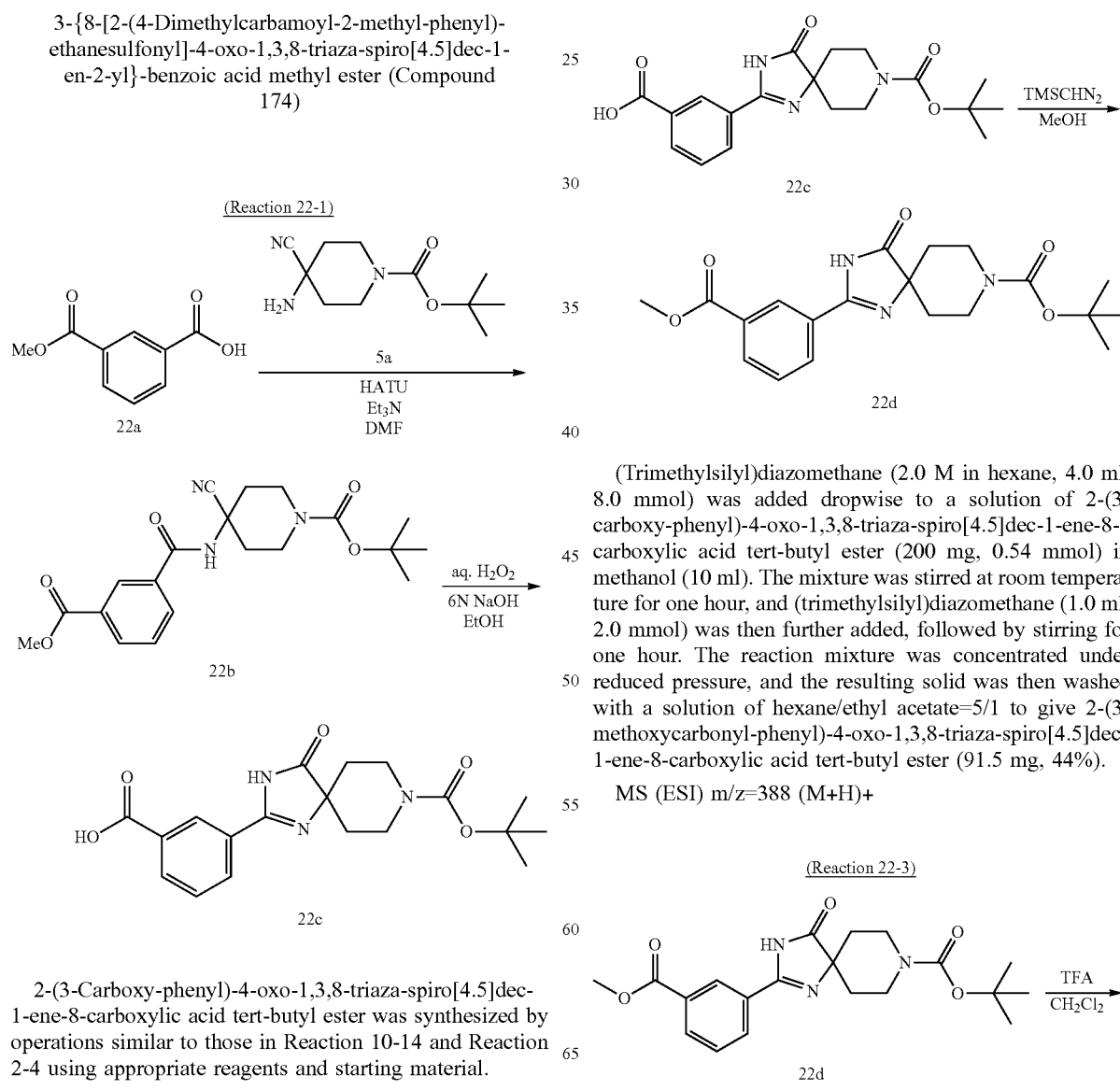

Example 22

3-{8-[2-(4-Dimethylcarbamoyl-2-methyl-phenyl)-ethanesulfonyl]-4-oxo-1,3,8-triaza-spiro[4.5]dec-1-en-2-yl}-benzoic acid methyl ester (Compound 174)

2-(3-Carboxy-phenyl)-4-oxo-1,3,8-triaza-spiro[4.5]dec-1-ene-8-carboxylic acid tert-butyl ester was synthesized by operations similar to those in Reaction 10-14 and Reaction 2-4 using appropriate reagents and starting material.

MS (ESI) m/z=374 (M+H)+.

(Trimethylsilyl)diazomethane (2.0 M in hexane, 4.0 ml, 8.0 mmol) was added dropwise to a solution of 2-(3-carboxy-phenyl)-4-oxo-1,3,8-triaza-spiro[4.5]dec-1-ene-8-carboxylic acid tert-butyl ester (200 mg, 0.54 mmol) in methanol (10 ml). The mixture was stirred at room temperature for one hour, and (trimethylsilyl)diazomethane (1.0 ml, 2.0 mmol) was then further added, followed by stirring for one hour. The reaction mixture was concentrated under reduced pressure, and the resulting solid was then washed with a solution of hexane/ethyl acetate=5/1 to give 2-(3-methoxycarbonyl-phenyl)-4-oxo-1,3,8-triaza-spiro[4.5]dec-1-ene-8-carboxylic acid tert-butyl ester (91.5 mg, 44%).

MS (ESI) m/z=388 (M+H)+

265

-continued

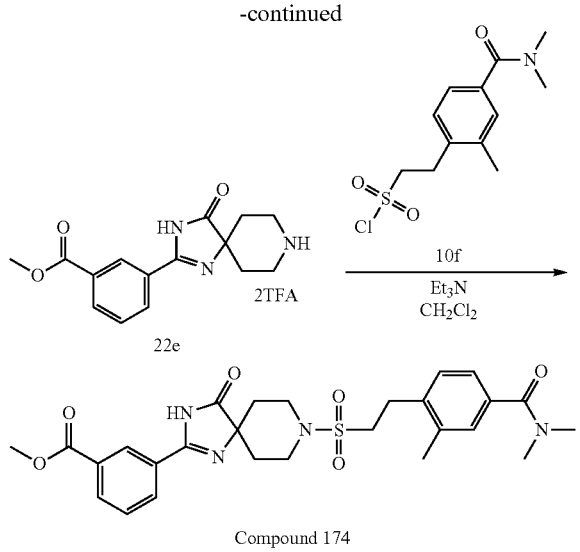

Compound 174

3-{8-[2-(4-Dimethylcarbamoyl-2-methyl-phenyl)-ethanesulfonyl]-4-oxo-1,3,8-triaza-spiro[4.5]dec-1-en-2-yl}-benzoic acid methyl ester was synthesized by operations similar to those in Reaction 4-1 and Reaction 5-4 using appropriate reagents and starting material.

MS (ESI) m/z=541 (M+H)+.

Example 23

4-(2-{2-[1-(2,4-Dichloro-phenoxy)-1-methyl-ethyl]-4-oxo-1,3,8-triaza-spiro[4.5]dec-1-ene-8-sulfonyl}-ethyl)-3,N,N-trimethyl-benzamide (Compound 175)

(Reaction 23-1)

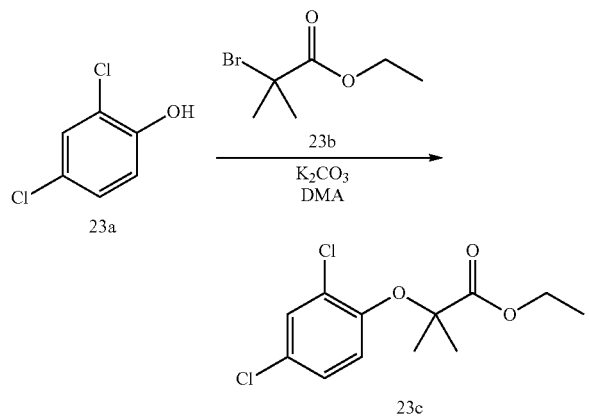

266

2,4-Dichlorophenol (448 mg, 2.75 mmol) and K$_2$CO$_3$ (775 mg, 5.61 mmol) were continuously added to 2-bromo-2-methyl-propionic acid ethyl ester (800 mg, 4.10 mmol) in N,N-dimethylacetamide (4 ml) at room temperature. The mixture was stirred at 110° C. for 14 hours, and saturated NH$_4$Cl and H$_2$O were then added, followed by extraction with AcOEt (×2). The organic layers were combined and sequentially washed with H$_2$O and saturated brine, and then dried over Na$_2$SO$_4$ and concentrated under reduced pressure. The resulting residue was purified by silica gel column chromatography (n-hexane/AcOEt) to give 2-(2,4-dichloro-phenoxy)-2-methyl-propionic acid ethyl ester (389 mg, 50%).

$^1$H-NMR (270 MHz, CDCl$_3$): δ. 1.28 (3H, t, J=7.3 Hz), 1.60 (6H, s), 4.25 (2H, q, J=7.3 Hz), 6.86 (1H, d, J=8.8 Hz), 7.10 (1H, dd, J=8.8, 2.4 Hz), 7.38 (1H, d, J=2.4 Hz).

(Reaction 23-2)

A 5 N aqueous NaOH solution (0.83 ml) was added to a solution of 2-(2,4-dichloro-phenoxy)-2-methyl-propionic acid ethyl ester (383 mg, 1.38 mmol) in MeOH (6 ml) at room temperature. The mixture was stirred at room temperature for four hours, and 1 N HCl (4.5 ml) and H$_2$O were then added, followed by extraction with AcOEt (×2). The organic layers were combined and sequentially washed with H$_2$O and saturated brine, and then dried over Na$_2$SO$_4$ and concentrated under reduced pressure to give 2-(2,4-dichloro-phenoxy)-2-methyl-propionic acid (359 mg).

$^1$H-NMR (270 MHz, DMSO-d6) δ 1.54 (6H, s), 6.94 (1H, d, J=8.8 Hz), 7.35 (1H, dd, J=8.8, 2.9 Hz), 7.60 (1H, d, J=2.4 Hz), 13.29 (1H, br.s).

(Reaction 23-3)

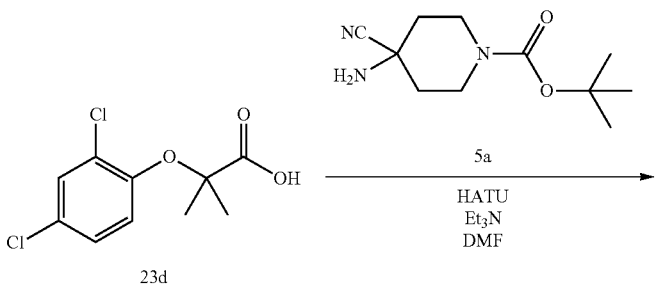

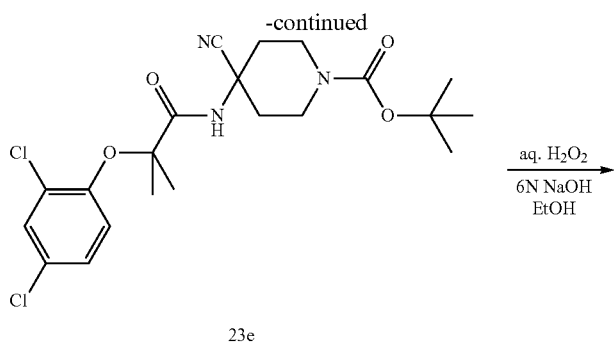

23e

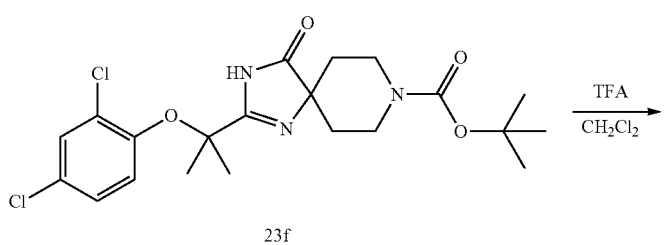

23f

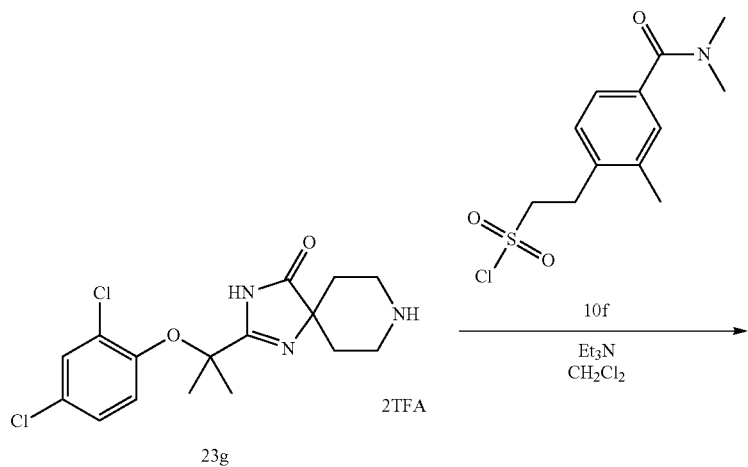

23g

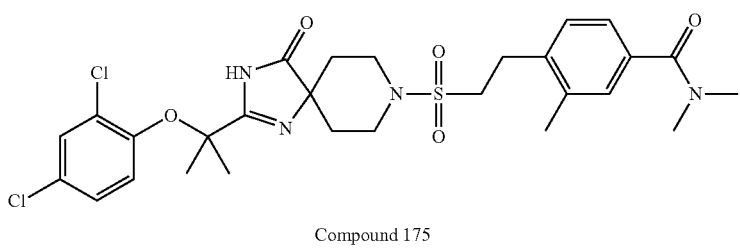

Compound 175

4-(2-{2-[1-(2,4-Dichloro-phenoxy)-1-methyl-ethyl]-4-oxo-1,3,8-triaza-spiro[4.5]dec-1-ene-8-sulfonyl}-ethyl)-3,N,N-trimethyl-benzamide was synthesized by operations similar to those in Reaction 10-14, Reaction 2-4, Reaction 7-2 and Reaction 5-4 using appropriate reagents and starting material.

MS (ESI) m/z=609 (M+H)+.

The example compound shown below was synthesized by operations similar to those in Example 23 using appropriate reagents and starting material.

TABLE 30

| Compound | Structure | LCMS or HPLC condition | Retention time (min) | MS (m/z) |
|---|---|---|---|---|
| 176 | 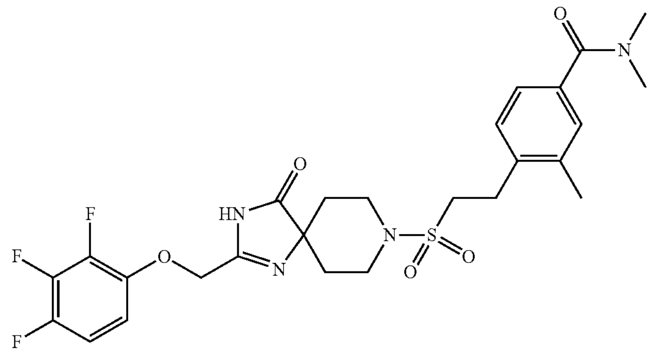 [SMILES: Cc1cc(C(=O)N(C)C)ccc1CCS(=O)(=O)N1CCC2(CC1)N=C(COc1ccc(F)c(F)c1F)NC2=O] | LCMS-C-1 | 2.42 | 567 (M + H)+ |

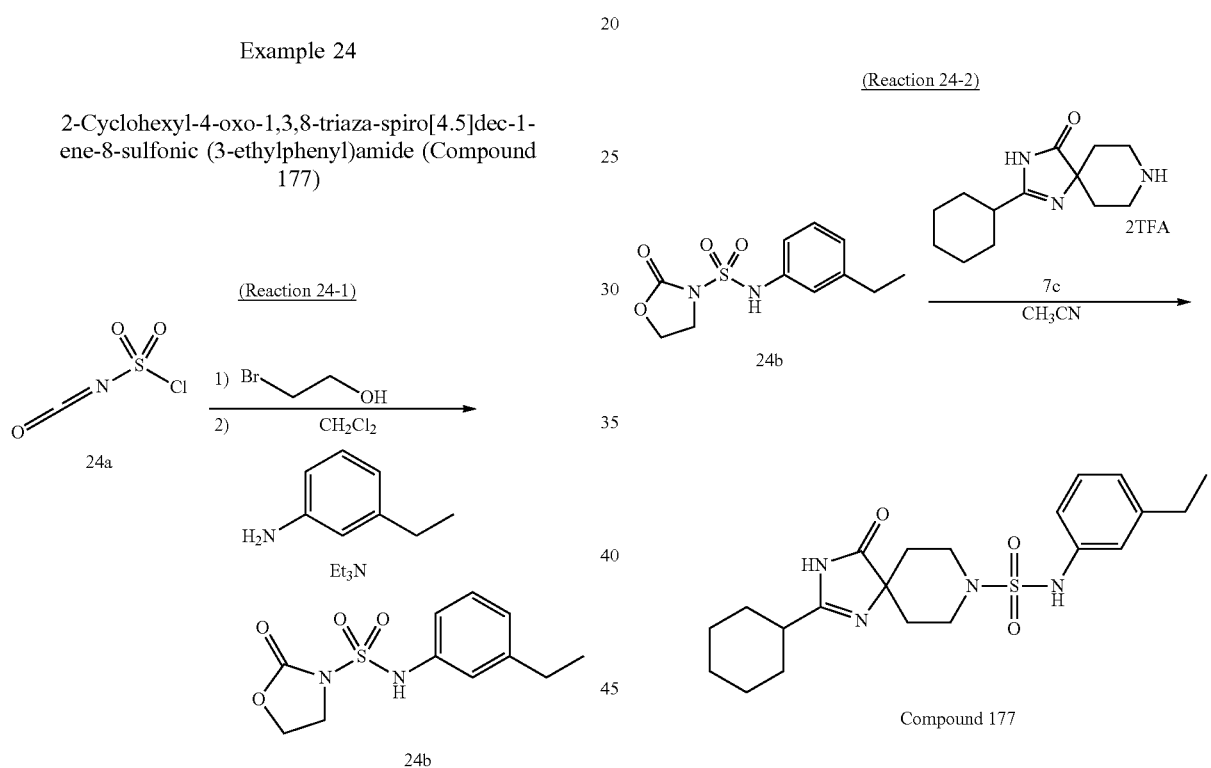

Example 24

2-Cyclohexyl-4-oxo-1,3,8-triaza-spiro[4.5]dec-1-ene-8-sulfonic (3-ethylphenyl)amide (Compound 177)

2-Bromoethanol (0.28 mL, 4.00 mmol) was added to a solution of chlorosulfonyl isocyanate (0.35 mL, 4.00 mmol) in dichloromethane (1.8 mL) at 0° C. After stirring for 90 minutes, a solution of 3-ethylaniline (0.55 mL, 4.40 mmol) and triethylamine (1.23 mL, 8.80 mmol) in dichloromethane (3.6 mL) was added. The mixture was stirred for 90 minutes and then quenched with a 2 N aqueous hydrochloric acid solution. The mixed solution was separated, and the aqueous layer was then extracted with ether. The organic layers were combined and washed with water and saturated brine, and then dried over sodium sulfate and concentrated under reduced pressure. The resulting residue was washed with ether (5 mL) to give 2-oxo-oxazolidine-3-sulfonic acid (3-ethylphenyl)amide (LCMS yield 80%).

MS (ESI) m/z=271 (M+H)+.

A solution of 2-oxo-oxazolidine-3-sulfonic acid (3-ethylphenyl)amide (92 mg, 0.340 mmol) and 2-cyclohexyl-1,3,8-triaza-spiro[4.5]dec-1-en-4-one ditrifluoroacetate (93 mg, 0.395 mmol) in acetonitrile (0.80 mL) was irradiated with microwaves (150° C., 15 min). The reaction mixture was filtered, and the resulting filtrate was then concentrated under reduced pressure. Further, the resulting residue was purified by silica gel chromatography to give 2-cyclohexyl-4-oxo-1,3,8-triaza-spiro[4.5]dec-1-ene-8-sulfonic acid (3-ethylphenyl)amide as a white amorphous (33 mg, 23%).

$^1$H-NMR (270 MHz, CDCl$_3$) δ 1.24 (3H, t, J=7.8 Hz), 1.31-1.93 (14H, m), 2.36-2.40 (1H, m), 2.64 (2H, q, J=7.8 Hz), 3.34-3.44 (2H, m), 3.69-3.76 (2H, m), 6.54 (1H, s), 6.96-7.02 (3H, m), 7.20-7.24 (1H, m), 8.27 (1H, s).

MS (ESI) m/z=419 (M+H)+.

Example 25

2-Cyclohexyl-8-[(E)-2-(1H-indol-5-yl)-ethenesulfonyl]-1,3,8-triaza-spiro[4.5]dec-1-en-4-one (Compound 178)

(Reaction 25-1)

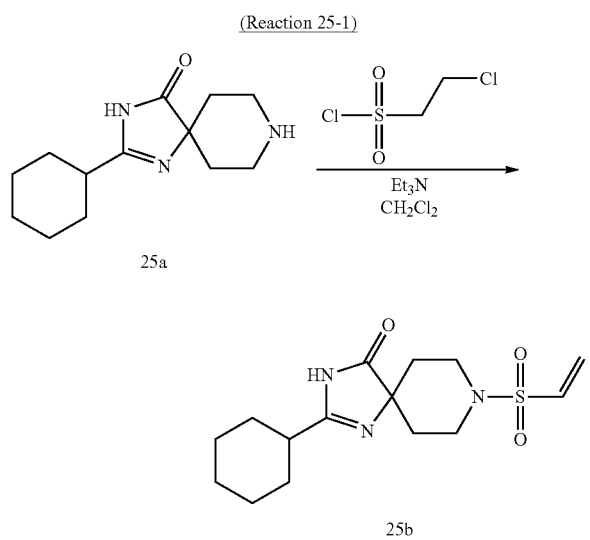

25a (Reaction 25-2)

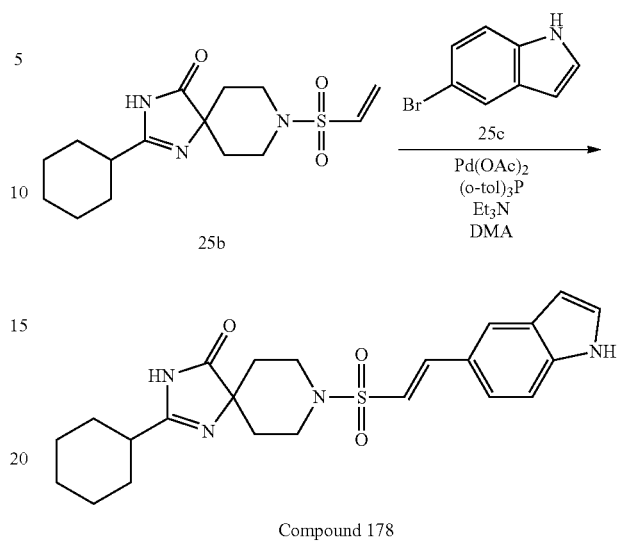

25b

Compound 178

2-Chloro-ethanesulfonyl chloride (440 µl, 4.21 mmol) was added to a solution of 2-cyclohexyl-1,3,8-triaza-spiro[4.5]dec-1-en-4-one dihydrochloride (1.50 g, 3.24 mmol) and triethylamine (2.7 ml, 19.4 mmol) in $CH_2Cl_2$ (30 ml) at room temperature in an $N_2$ atmosphere. The mixture was stirred at room temperature for 30 minutes, and then washed with water, dried over sodium sulfate and concentrated under reduced pressure. The resulting residue was triturated with AcOEt-hexane, and the solid was then collected by filtration and dried to give 2-cyclohexyl-8-ethenesulfonyl-1,3,8-triaza-spiro[4.5]dec-1-en-4-one as a colorless solid (692 mg, 66%).

$^1$H-NMR (400 MHz, CDCl$_3$) δ 1.25-1.45 (6H, m), 1.70-2.05 (8H, m), 2.40-2.47 (1H, m), 3.21-3.30 (2H, m), 3.61-3.69 (2H, m), 6.03 (1H, d, J=8.0 Hz), 6.26 (1H, d, J=16.0 Hz), 6.49 (1H, dd, J=16.0, 8.0 Hz), 8.17 (1H, brs).

MS (ESI) m/z=326 (M+H)+.

2-Cyclohexyl-8-ethenesulfonyl-1,3,8-triaza-spiro[4.5]dec-1-en-4-one (60.0 mg, 0.184 mmol), 5-bromo-indole (72.0 mg, 0.367 mmol), palladium(II) acetate (4.1 mg, 0.0183 mmol), tris(o-tolyl)phosphine (11.2 mg, 0.0368 mmol), triethylamine (0.077 ml, 0.552 mmol) and DMA (0.6 ml) were mixed in a sealed test tube in an $N_2$ atmosphere. This mixture was irradiated with microwaves (190° C., 20 min). The reaction mixture was cooled, and then quenched with saturated brine and extracted with ethyl acetate three times. The organic layers were combined, sequentially washed with water and saturated brine and concentrated under reduced pressure. The resulting residue was purified by silica gel column chromatography ($CH_2Cl_2$-MeOH) to give 2-cyclohexyl-8-[(E)-2-(1H-indol-5-yl)-ethenesulfonyl]-1,3,8-triaza-spiro[4.5]dec-1-en-4-one as a yellow form (40.6 mg, 50%).

$^1$H-NMR (270 MHz, CDCl$_3$) δ 1.20-1.45 (5H, m), 1.52-1.95 (7H, m), 1.98-2.11 (2H, m), 2.35-2.48 (1H, m), 3.20-3.31 (2H, m), 3.68-3.79 (2H, m), 6.59-6.63 (1H, m), 6.65 (1H, d, J=16 Hz), 7.25-7.28 (1H, m), 7.33-7.44 (2H, m), 7.60 (1H, d, J=16 Hz), 7.77-7.79 (1H, m), 8.33 (1H, brs), 8.37 (1H, brs). MS (ESI) m/z=441 (M+H)+.

The example compounds shown below were synthesized by operations similar to those in Example 25 using appropriate reagents and starting materials.

Compounds 179 to 203

TABLE 31

| Compound | Structure | LCMS or HPLC condition | Retention time (min) | MS (m/z) |
| --- | --- | --- | --- | --- |
| 179 | 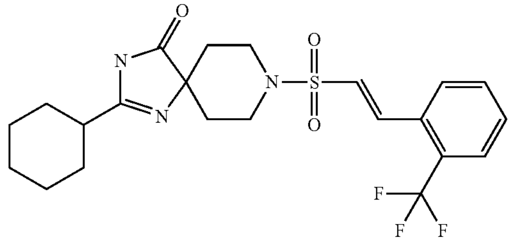 [SMILES: O=C1NC(C2CCCCC2)=NC12CCN(S(=O)(=O)/C=C/c1ccccc1C(F)(F)F)CC2] | LCMS-E-8 | 3.68 | 470 (M + H)+ |

TABLE 31-continued

| Compound | Structure | LCMS or HPLC condition | Retention time (min) | MS (m/z) |
|---|---|---|---|---|
| 180 | 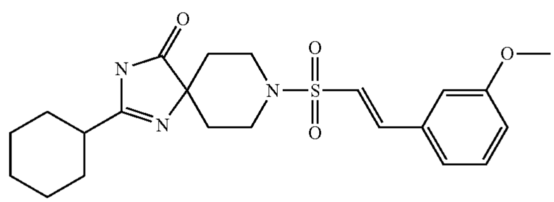 [SMILES: COc1cccc(/C=C/S(=O)(=O)N2CCC3(CC2)N=C(C2CCCCC2)NC3=O)c1] | LCMS-E-5 | 3.14 | 432 (M + H)+ |
| 181 | 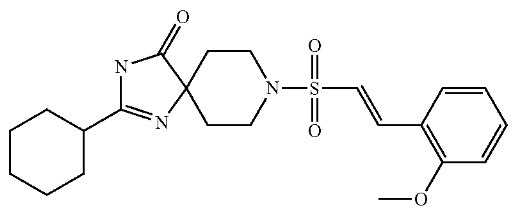 [SMILES: COc1ccccc1/C=C/S(=O)(=O)N1CCC2(CC1)N=C(C1CCCCC1)NC2=O] | LCMS-E-4 | 2.91 | 432 (M + H)+ |
| 182 | 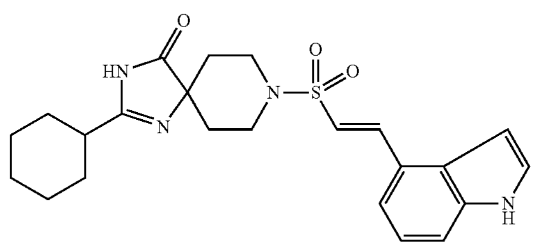 [SMILES: O=C1NC(C2CCCCC2)=NC12CCN(S(=O)(=O)/C=C/c1cccc3[nH]ccc13)CC2] | LCMS-C-1 | 2.48 | 441 (M + H)+ |
| 183 | 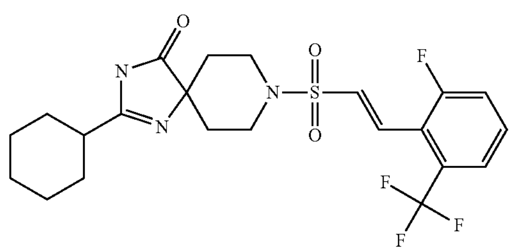 [SMILES: O=C1NC(C2CCCCC2)=NC12CCN(S(=O)(=O)/C=C/c1c(F)cccc1C(F)(F)F)CC2] | LCMS-E-6 | 1.66 | 488 (M + H)+ |
| 184 | 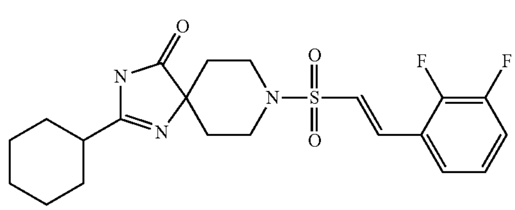 [SMILES: O=C1NC(C2CCCCC2)=NC12CCN(S(=O)(=O)/C=C/c1cccc(F)c1F)CC2] | LCMS-E-6 | 1.53 | 438 (M + H)+ |
| 185 | 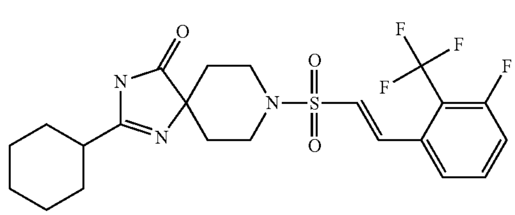 [SMILES: O=C1NC(C2CCCCC2)=NC12CCN(S(=O)(=O)/C=C/c1cccc(F)c1C(F)(F)F)CC2] | LCMS-E-6 | 1.7 | 488 (M + H)+ |

TABLE 31-continued

| Compound | Structure | LCMS or HPLC condition | Retention time (min) | MS (m/z) |
|---|---|---|---|---|
| 186 | 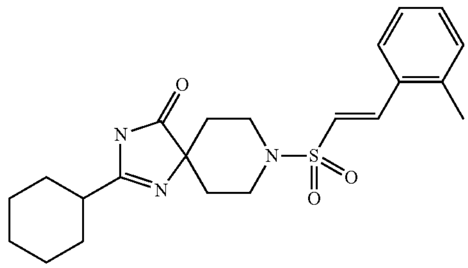 [SMILES: Cc1ccccc1/C=C/S(=O)(=O)N1CCC2(CC1)N=C(C1CCCCC1)NC2=O] | LCMS-C-1 | 2.73 | 416 (M + H)+ |
| 187 | 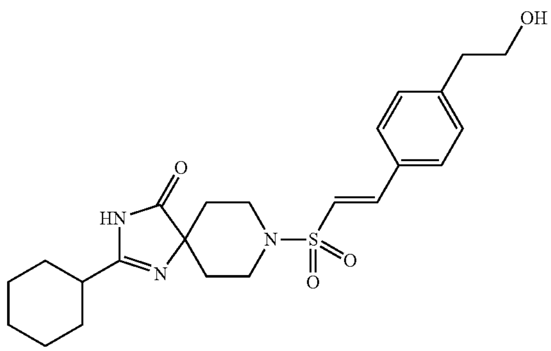 [SMILES: O=C1NC(C2CCCCC2)=NC12CCN(S(=O)(=O)/C=C/c1ccc(CCO)cc1)CC2] | LCMS-C-1 | 2.37 | 446 (M + H)+ |
| 188 | 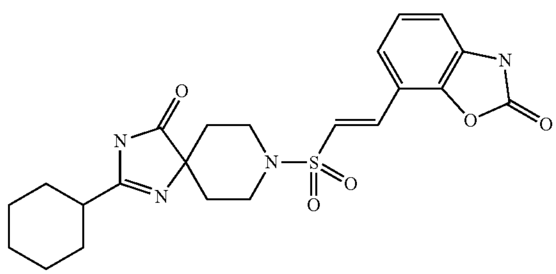 [SMILES: O=C1NC(C2CCCCC2)=NC12CCN(S(=O)(=O)/C=C/c1cccc3[nH]c(=O)oc13)CC2] | LCMS-A-1 | 1.84 | 459 (M + H)+ |
| 189 | 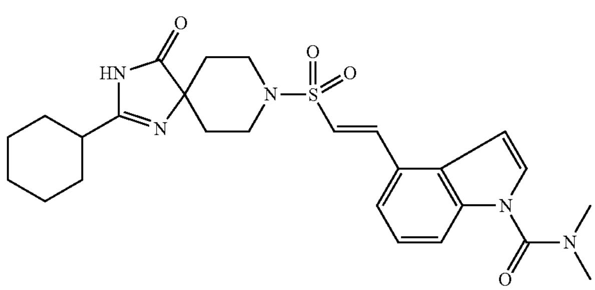 [SMILES: CN(C)C(=O)n1ccc2c(/C=C/S(=O)(=O)N3CCC4(CC3)N=C(C3CCCCC3)NC4=O)cccc21] | LCMS-C-1 | 2.53 | 512 (M + H)+ |
| 190 | 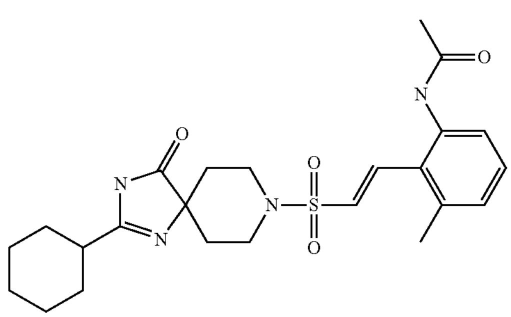 [SMILES: CC(=O)Nc1cccc(C)c1/C=C/S(=O)(=O)N1CCC2(CC1)N=C(C1CCCCC1)NC2=O] | LCMS-A-1 | 1.87 | 473 (M + H)+ |

TABLE 31-continued
| Compound | Structure | LCMS or HPLC condition | Retention time (min) | MS (m/z) |
|---|---|---|---|---|
| 191 | 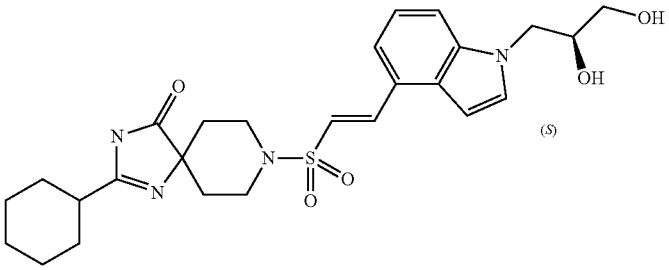 | LCMS-C-1 | 2.35 | 515 (M + H)+ |
| 192 | 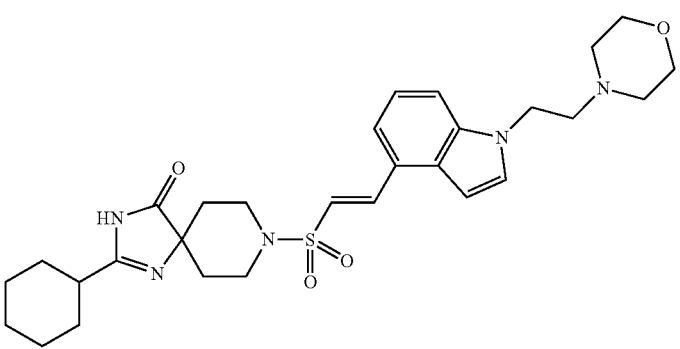 [SMILES: O=C1NC(C2CCCCC2)=NC12CCN(S(=O)(=O)/C=C/c1cccc3c1ccn3CCN1CCOCC1)CC2] | LCMS-C-1 | 2.65 | 554 (M + H)+ |
| 193 | 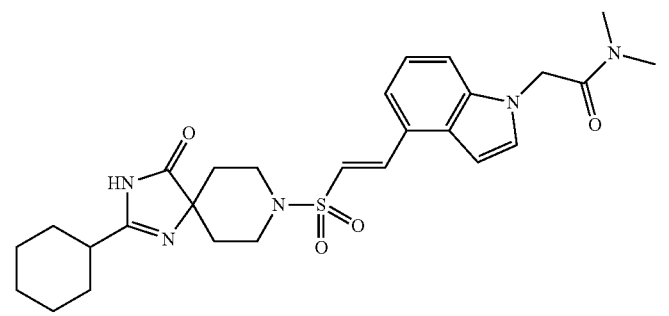 [SMILES: CN(C)C(=O)Cn1ccc2c(/C=C/S(=O)(=O)N3CCC4(CC3)N=C(C3CCCCC3)NC4=O)cccc21] | LCMS-C-1 | 2.37 | 526 (M + H)+ |
| 194 | 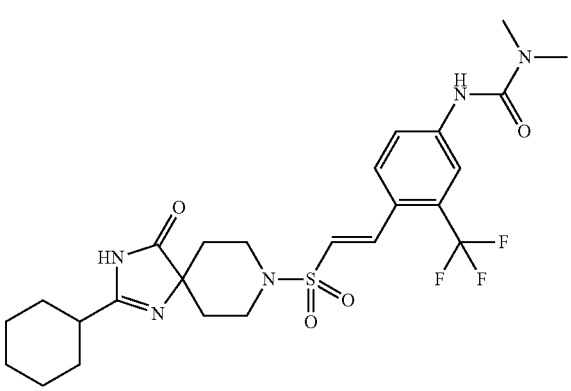 [SMILES: CN(C)C(=O)Nc1ccc(/C=C/S(=O)(=O)N2CCC3(CC2)N=C(C2CCCCC2)NC3=O)c(C(F)(F)F)c1] | LCMS-C-1 | 2.60 | 556 (M + H)+ |

TABLE 31-continued
| Compound | Structure | LCMS or HPLC condition | Retention time (min) | MS (m/z) |
|---|---|---|---|---|
| 195 | 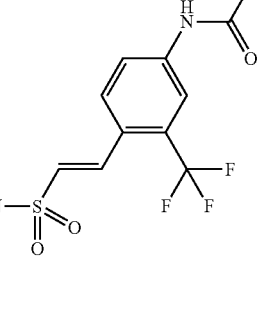 | LCMS-C-1 | 2.75 | 553 (M + H)+ |
| 196 | 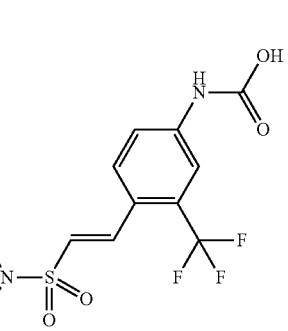 | LCMS-C-1 | 2.48 | 543 (M + H)+ |
| 197 | 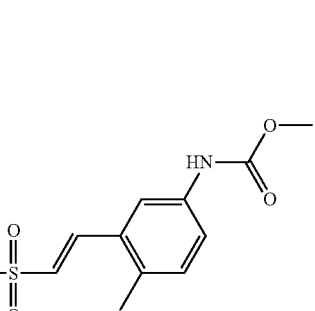 | LCMS-A-1 | 2.19 | 489 (M + H)+ |
| 198 | 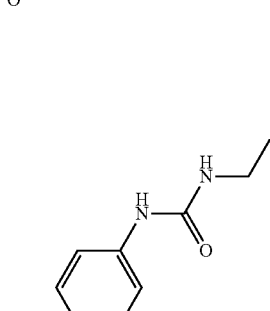 | LCMS-C-1 | 2.48 | 572 (M + H)+ |

TABLE 31-continued
| Compound | Structure | LCMS or HPLC condition | Retention time (min) | MS (m/z) |
|---|---|---|---|---|
| 199 | 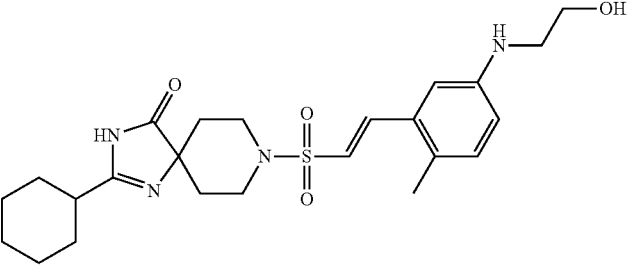 [SMILES: Cc1ccc(NCCO)cc1/C=C/S(=O)(=O)N1CCC2(CC1)N=C(C1CCCCC1)NC2=O] | LCMS-A-1 | 1.89 | 475 (M + H)+ |
| 200 | 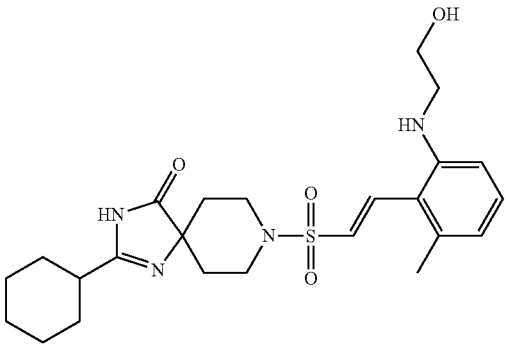 [SMILES: Cc1cccc(NCCO)c1/C=C/S(=O)(=O)N1CCC2(CC1)N=C(C1CCCCC1)NC2=O] | LCMS-A-1 | 2.09 | 475 (M + H)+ |
| 201 | 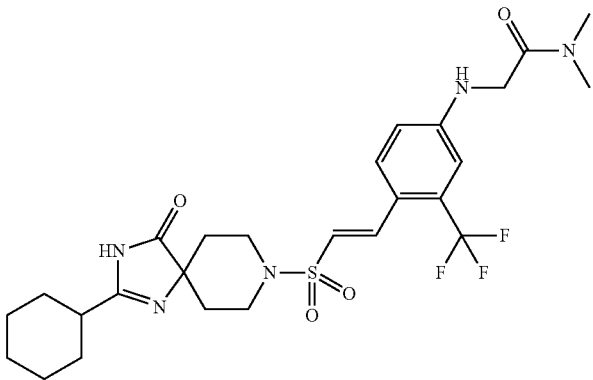 [SMILES: CN(C)C(=O)CNc1ccc(/C=C/S(=O)(=O)N2CCC3(CC2)N=C(C2CCCCC2)NC3=O)c(C(F)(F)F)c1] | LCMS-A-1 | 2.19 | 570 (M + H)+ |
| 202 | 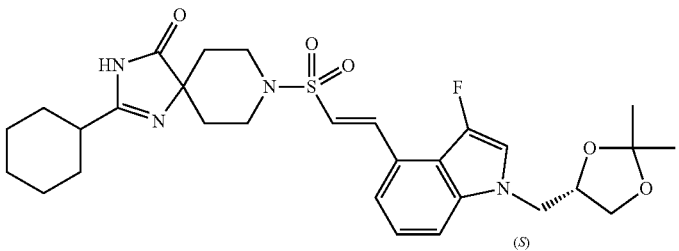 | LCMS-C-1 | 2.44 | 573 (M + H)+ |

TABLE 31-continued

| Compound | Structure | LCMS or HPLC condition | Retention time (min) | MS (m/z) |
|---|---|---|---|---|
| 203 | 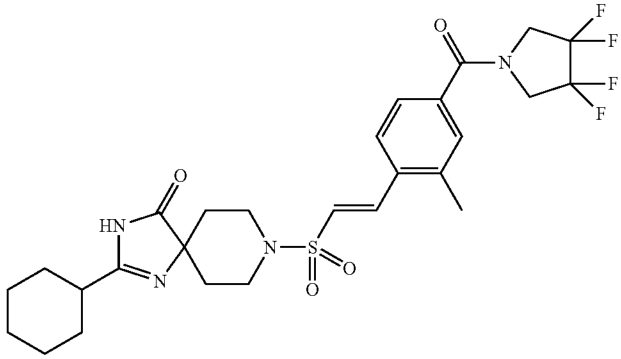 [SMILES: Cc1cc(C(=O)N2CC(F)(F)C(F)(F)C2)ccc1/C=C/S(=O)(=O)N1CCC2(CC1)N=C(C1CCCCC1)NC2=O] | LCMS-A-1 | 2.33 | 585 (M + H)+ |

The aryl bromide reagent used in the synthesis of Compound 191 ((S)-3-(4-bromo-indol-1-yl)-propane-1,2-diol) was synthesized as follows.

(Reaction 25-3)

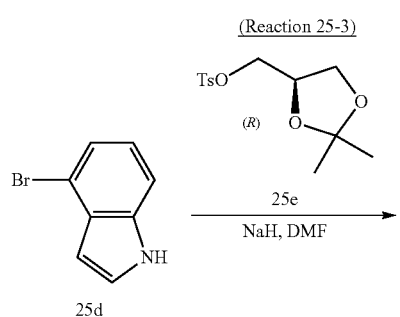

NaH (382 mg, 9.55 mmol, 60% oily suspension) was added to a solution of 4-bromo-indole (1.0 ml, 7.97 mmol) and (R)-(−)-2,2-dimethyl-1,3-dioxolan-4-ylmethyl p-toluenesulfonate (2.74 g, 9.57 mmol) in dimethylformamide (20 ml) at 0° C. The mixture was stirred at 0° C. for two hours and at room temperature for 18 hours. NaH (190 mg, 4.75 mmol, 60% oily suspension) was further added, and the mixture was stirred at room temperature for six hours. The reaction mixture was diluted with AcOEt, and the organic layer was then washed with water (×2), dried over sodium sulfate and concentrated under reduced pressure. The resulting 4-bromo-1-((S)-2,2-dimethyl-[1,3]dioxolan-4-ylmethyl)-1H-indole was used in the next step without further purification.

(Reaction 25-4)

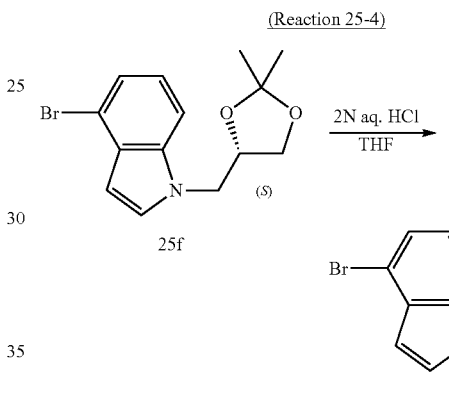

A 2 N aqueous HCl solution (15 ml) was added to a solution of the above mixture (4-bromo-1-((S)-2,2-dimethyl-[1,3]dioxolan-4-ylmethyl)-1H-indole) in tetrahydrofuran (30 ml), and the mixture was stirred at room temperature for eight hours. The reaction mixture was concentrated, and the residue was then diluted with AcOEt. This organic layer was sequentially washed with water (×2) and a saturated aqueous NaCl solution, and then dried and concentrated under reduced pressure. The resulting residue was purified by silica gel column chromatography ($CH_2Cl_2$-MeOH) to give (S)-3-(4-bromo-indol-1-yl)-propane-1,2-diol as a colorless solid (2.05 g, 95%).

MS (ESI) m/z=270, 272 (M+H)+.

The aryl bromide reagent used in the synthesis of Compound 192 (4-bromo-1-(2-morpholin-4-yl-ethyl)-1H-indole) was synthesized as follows.

(Reaction 25-5)

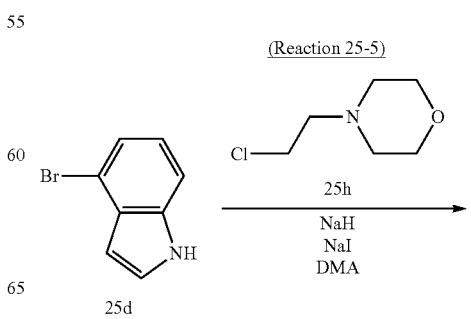

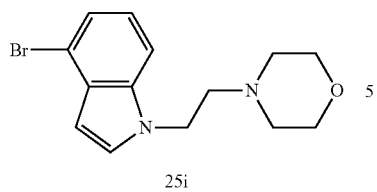

4-Bromo-1-(2-morpholin-4-yl-ethyl)-1H-indole was synthesized by operations similar to those in Reaction 25-3 using appropriate reagents and starting material.

MS (ESI) m/z=309, 311 (M+H)+.

The aryl bromide reagent used in the synthesis of Compound 193 (2-(4-bromo-indol-1-yl)-N,N-dimethyl-acetamide) was synthesized as follows.

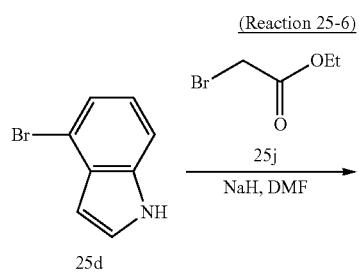

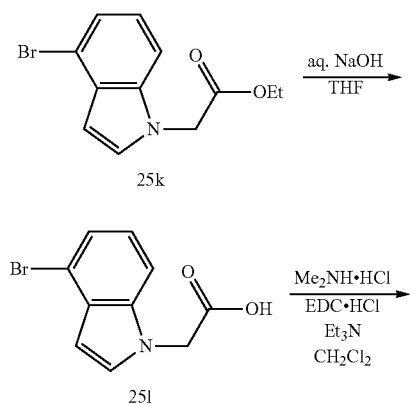

2-(4-Bromo-indol-1-yl)-N,N-dimethyl-acetamide was synthesized by operations similar to those in Reaction 25-3, Reaction 23-2 and Reaction 10-18 using appropriate reagents, solvent and starting material.

MS (ESI) m/z=281, 283 (M+H)+.

The aryl bromide reagent used in the synthesis of Compound 194 (3-(4-bromo-3-trifluoromethyl-phenyl)-1,1-dimethyl-urea was synthesized as follows.

(Reaction 25-7)

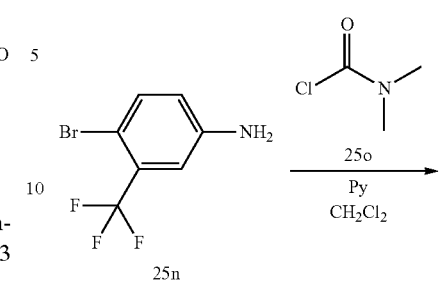

3-(4-Bromo-3-trifluoromethyl-phenyl)-1,1-dimethyl-urea was synthesized by operations similar to those in Reaction 2-3 using appropriate reagents and starting material.

MS (ESI) m/z=311, 313 (M+H)+.

The aryl bromide reagent used in the synthesis of Compound 195 (cyclopropanecarboxylic (4-bromo-3-trifluoromethyl-phenyl)-amide) was synthesized as follows.

(Reaction 25-8)

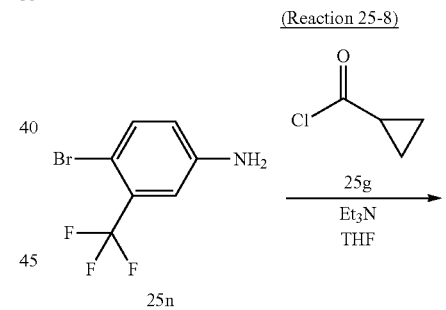

Cyclopropanecarboxylic (4-bromo-3-trifluoromethyl-phenyl)-amide was synthesized by operations similar to those in Reaction 2-3 using appropriate reagents and starting material.

MS (ESI) m/z=308, 310 (M+H)+.

The aryl bromide reagent used in the synthesis of Compound 196 (N-(4-bromo-3-trifluoromethyl-phenyl)-2-hydroxy-acetamide) was synthesized as follows.

(Reaction 25-9)

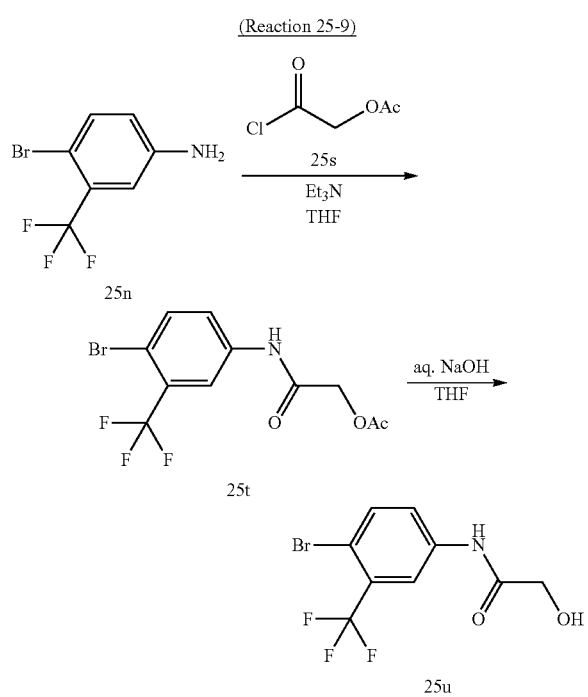

N-(4-Bromo-3-trifluoromethyl-phenyl)-2-hydroxy-acetamide was synthesized by operations similar to those in Reaction 2-3 and Reaction 23-2 using appropriate reagents and starting material.

MS (ESI) m/z=298, 300 (M+H)+.

The aryl bromide reagent used in the synthesis of Compound 197 ((3-bromo-4-methyl-phenyl)-carbamic acid methyl ester) was synthesized as follows.

(Reaction 25-10)

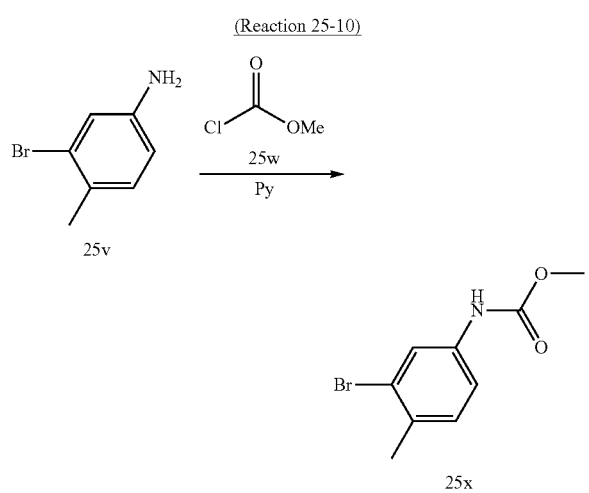

Methyl chloroformate (0.202 ml, 2.62 mmol) was added to a solution of 3-bromo-4-methyl-phenylamine (243 mg, 1.31 mmol) in pyridine (2 ml), and the mixture was stirred at room temperature overnight. H$_2$O was added to the reaction mixture, followed by extraction with AcOEt (×2). The organic layers were combined and sequentially washed with H$_2$O and saturated brine, and then dried over Na$_2$SO$_4$ and concentrated under reduced pressure. The resulting residue was purified by silica gel chromatography (n-hexane/AcOEt) to give (3-bromo-4-methyl-phenyl)-carbamic acid methyl ester (288 mg, 90%).

$^1$H-NMR (270 MHz, CDCl$_3$) δ 2.34 (3H, s), 3.77 (3H, s), 6.51 (1H, br. s), 7.14 (1H, d, J=7.2 Hz), 7.20 (1H, dd, J=7.4, 2.0 Hz), 7.63 (1H, d, J=2.0 Hz).

The aryl bromide reagent used in the synthesis of Compound 198 (1-(4-bromo-3-trifluoromethyl-phenyl)-3-(2-hydroxy-ethyl)-urea) was synthesized as follows.

(Reaction 25-11)

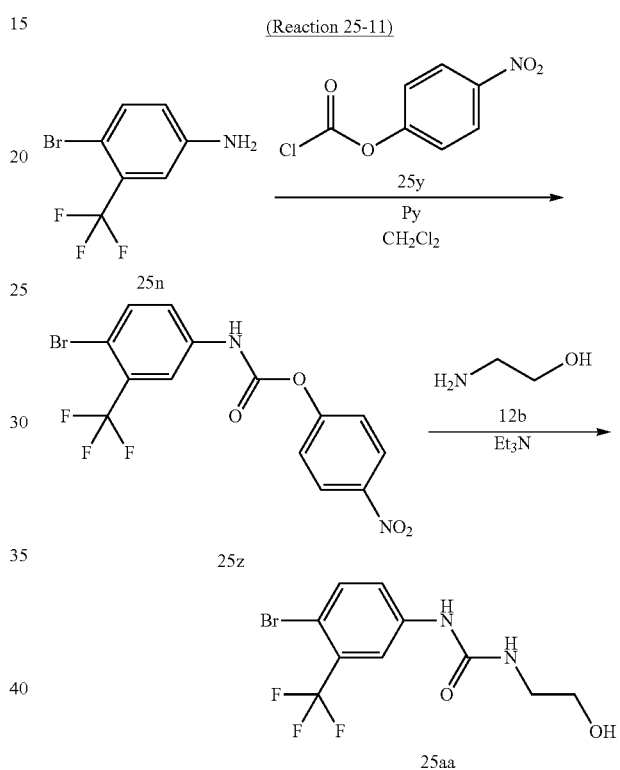

p-Nitrophenyl chloroformate (437 mg, 2.17 mmol) was added to a solution of 4-bromo-3-trifluoromethyl-aniline (400 μl, 1.67 mmol) and pyridine (202 μl, 2.50 mmol) in CH$_2$Cl$_2$ (6.2 ml) at 0° C. The mixture was stirred at 0° C. for one hour, and 2-amino-ethanol (150 μl, 2.50 mmol) was then added, followed by further stirring at 0° C. for two hours. Triethylamine (210 μl, 1.51 mmol) was added to the mixture, and the mixture was stirred at 0° C. for one hour. 1 N HCl was added to the reaction mixture, followed by extraction with CH$_2$Cl$_2$/AcOEt. The organic layer was washed with water (×2), and then dried over sodium sulfate and concentrated under reduced pressure. The residue was purified by silica gel column chromatography (CH$_2$Cl$_2$-MeOH) to give 1-(4-bromo-3-trifluoromethyl-phenyl)-3-(2-hydroxy-ethyl)-urea as a white powder (520 mg, 73%).

MS (ESI) m/z=327, 329 (M+H)+.

The aryl bromide reagent used in the synthesis of Compound 199 (2-(3-bromo-4-methyl-phenylamino)-ethanol) was synthesized as follows.

(Reaction 25-12)

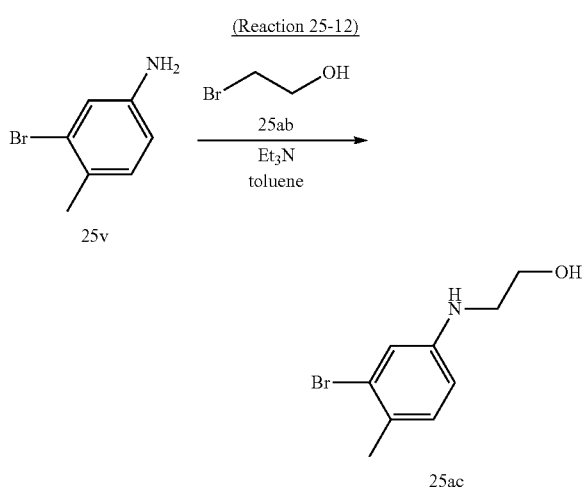

Triethylamine (0.28 mL, 2.00 mmol) and bromoethanol (0.14 mL, 1.98 mmol) were added to a solution of 3-bromo-4-methyl-phenylamine (240 mg, 1.29 mmol) in toluene (2 ml). The mixture was stirred at 100° C. overnight and $H_2O$ was then added, followed by extraction with AcOEt (×2). The organic layers were combined and sequentially washed with $H_2O$ and saturated brine, and then dried over $Na_2SO_4$ and concentrated under reduced pressure. The resulting residue was purified by silica gel column chromatography (n-hexane/AcOEt) to give 2-(3-bromo-4-methyl-phenylamino)-ethanol (185 mg, 62%).

$^1$H-NMR (270 MHz, $CDCl_3$) δ 1.68 (1H, br, OH), 2.27 (3H, s, Me), 3.26 (2H, dd, J=5.3, 5.1 Hz), 3.82 (2H, dd, J=5.3, 5.1 Hz), 3.90 (1H, br, NH), 6.52 (1H, dd, J=8.2, 2.5 Hz), 6.85 (1H, d, J=2.5 Hz), 7.01 (1H, d, J=8.2 Hz). MS (ESI) m/z=230, 232 (M+H)+.

The aryl bromide reagent used in the synthesis of Compound 200 (2-(2-bromo-3-methyl-phenylamino)-ethanol) was synthesized as follows.

(Reaction 25-13)

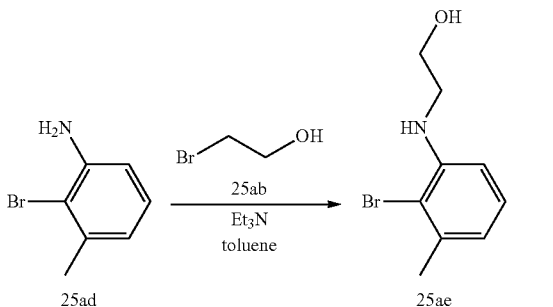

2-(2-Bromo-3-methyl-phenylamino)-ethanol was synthesized by operations similar to those in Reaction 25-12 using appropriate reagents and starting material.

MS (ESI) m/z=230, 232 (M+H)+.

The aryl bromide reagent used in the synthesis of Compound 201 (2-(4-bromo-3-trifluoromethyl-phenylamino)-N,N-dimethyl-acetamide) was synthesized as follows.

(Reaction 25-14)

2-(4-Bromo-3-trifluoromethyl-phenylamino)-N,N-dimethyl-acetamide was synthesized by operations similar to those in Reaction 25-12, Reaction 14-1 and Reaction 10-14 using appropriate reagents and starting material.

MS (ESI) m/z=325, 327 (M+H)+.

The aryl bromide reagent used in the synthesis of Compound 202 (4-bromo-1-((S)-2,2-dimethyl-[1,3]dioxolan-4-ylmethyl)-3-fluoro-1H-indole) was synthesized as follows.

(Reaction 25-15)

Diethylaminotrifluorosulfur (1.5 mL, 11.06 mmol) was added to a solution of 4-bromo-1H-indole-2,3-dione (1.0 g, 4.4 mmol) in dichloromethane (44 mL) at 0° C. The mixture was stirred at room temperature for 54 hours and then quenched with methanol-water. The organic layer and the aqueous layer were separated, and the aqueous layer was then extracted with dichloromethane. The organic layers were combined, dried over sodium sulfate and then concentrated under reduced pressure. The resulting residue was purified by silica gel column chromatography to give 4-bromo-3,3-difluoro-1,3-dihydro-indol-2-one as a yellow solid (559 mg, 51%).

MS (ESI) m/z=246 (M−H)−.

(Reaction 25-16)

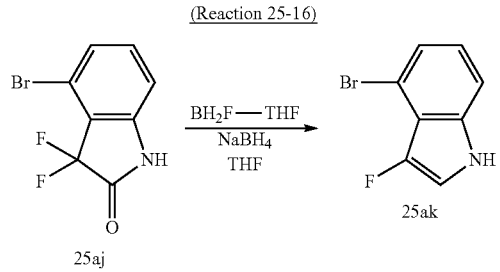

Synthesis of a 1.3 M solution of BH$_2$F in tetrahydrofuran (Reagent A): Boron trifluoride etherate (2 mL) was added dropwise to a suspension of sodium borohydride (340 mg, 4.5 mmol) in tetrahydrofuran (12 mL) at 0° C. The mixture was stirred at 0° C. for 90 minutes to give Reagent A.

Reagent A (2.85 mL, 3.709 mmol) was added dropwise to a solution of 4-bromo-3,3-difluoro-1,3-dihydro-indol-2-one (400 mg, 1.61 mmol) in tetrahydrofuran (8.1 mL) at 0° C. The mixture was stirred at 0° C. for 3.5 hours and at room temperature for 16 hours. Further, Reagent A (3.0 mL) was added to the reaction mixture, followed by stirring at room temperature for three hours. The reaction mixture was quenched with 3 M HCl (4.8 mL) and then extracted with ethyl acetate (×2). The organic layers were combined and sequentially washed with water and saturated brine, and then dried over sodium sulfate and concentrated under reduced pressure. The resulting residue was purified by silica gel column chromatography to give 4-bromo-3-fluoro-1H-indole as a yellow oil (132 mg, 38%).

MS (ESI) m/z=212 (M−H)−.

(Reaction 25-17)

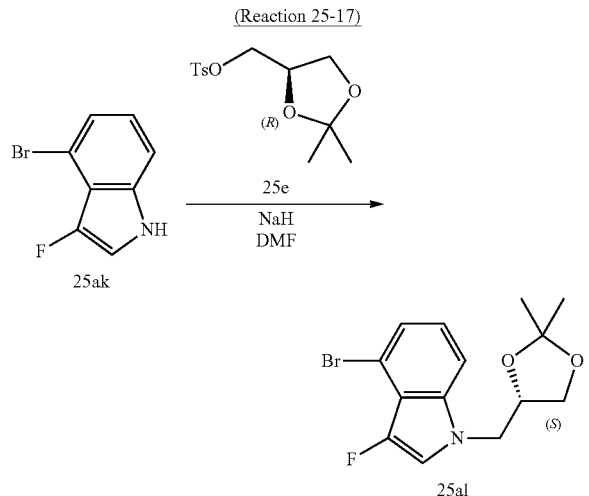

4-Bromo-1-((S)-2,2-dimethyl-[1,3]dioxolan-4-ylmethyl)-3-fluoro-1H-indole was synthesized by operations similar to those in Reaction 25-3 using appropriate reagents and starting material.

$^1$H-NMR (400 MHz, CDCl$_3$) δ 1.33 (3H, s), 1.40 (3H, s), 3.65 (1H, dd, J=5.9, 8.8 Hz), 4.04 (1H, dd, J=6.1, 8.8 Hz), 4.14 (2H, t, J=4.9 Hz), 4.37-4.42 (1H, m), 7.02-7.07 (2H, m), 7.23-7.27 (2H, m).

The aryl bromide reagent used in the synthesis of Compound 203 ((4-bromo-3-methyl-phenyl)-(3,3,4,4-tetrafluoro-pyrrolidin-1-yl)-methanone) was synthesized as follows.

(Reaction 25-18)

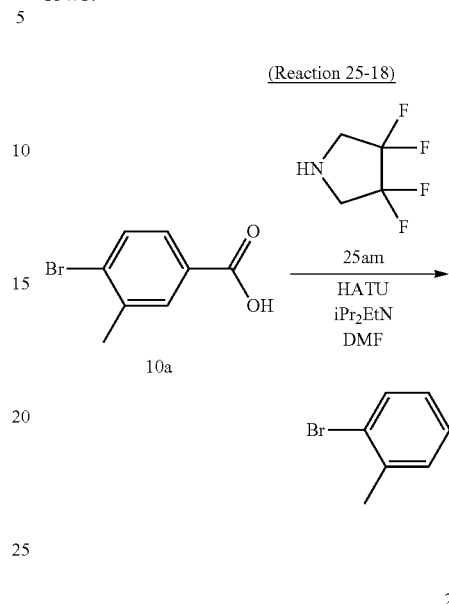

(4-Bromo-3-methyl-phenyl)-(3,3,4,4-tetrafluoro-pyrrolidin-1-yl)-methanone was synthesized by operations similar to those in Reaction 10-14 using appropriate reagents and starting material.

MS (ESI) m/z=340, 342 (M+H)+.

Example 26

N-{4-[(E)-2-(2-Cyclohexyl-4-oxo-1,3,8-triaza-spiro[4.5]dec-1-ene-8-sulfonyl)-vinyl]-3,5-dimethyl-phenyl}-acetamide (Compound 204)

(Reaction 26-1)

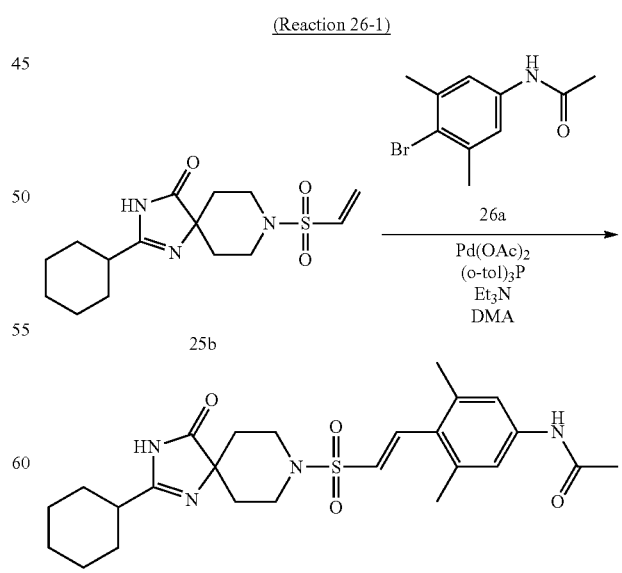

Compound 204

A mixture of 2-cyclohexyl-8-ethenesulfonyl-1,3,8-triaza-spiro[4.5]dec-1-en-4-one (100.0 mg, 0.307 mmol), N-(4-bromo-3,5-dimethyl-phenyl)-acetamide (112. mg, 0.461 mmol), palladium(II) acetate (10 mg, 0.0461 mmol), tris(o-tolyl)phosphine (28 mg, 0.0922 mmol), triethylamine (0.128 ml, 0.922 mmol) and DMA (1.5 ml) was added to a sealed test tube in an $N_2$ atmosphere. This mixture was heated with stirring at 130° C. for 13.5 hours. Palladium(II) acetate (10 mg, 0.0461 mmol), tris(o-tolyl)phosphine (28 mg, 0.0922 mmol) and triethylamine (0.128 ml, 0.922 mmol) were further added to the reaction mixture at room temperature in an $N_2$ atmosphere, and the mixture was heated with stirring at 130° C. for 14 hours. The reaction mixture was cooled and water was then added. The aqueous layer was extracted with ethyl acetate (×3). The organic layers were combined and sequentially washed with water (×2) and saturated brine, and then dried over sodium sulfate and concentrated under reduced pressure. The resulting residue was purified by silica gel column chromatography ($CH_2Cl_2$-MeOH) to give N-{4-[(E)-2-(2-cyclohexyl-4-oxo-1,3,8-triaza-spiro[4.5]dec-1-ene-8-sulfonyl)-vinyl]-3,5-dimethyl-phenyl}-acetamide (61.4 mg, 41%).

$^1$H-NMR (400 MHz, CD3OD) δ 1.20-1.57 (6H, m), 1.59-1.79 (3H, m), 1.80-2.00 (6H, m), 2.12 (3H, s), 2.39 (6H, s), 3.20-3.40 (2H, m), 3.58-3.75 (2H, m), 6.58 (1H, d, J=16 Hz), 7.35 (2H, s), 7.57 (1H, d, J=16 Hz). MS (ESI) m/z=487 (M+H)+.

The example compounds shown below were synthesized by operations similar to those in Example 26 using appropriate reagents and starting materials.

Compounds 205 to 208

TABLE 32

| Compound | Structure | LCMS or HPLC condition | Retention time (min) | MS (m/z) |
|---|---|---|---|---|
| 205 | 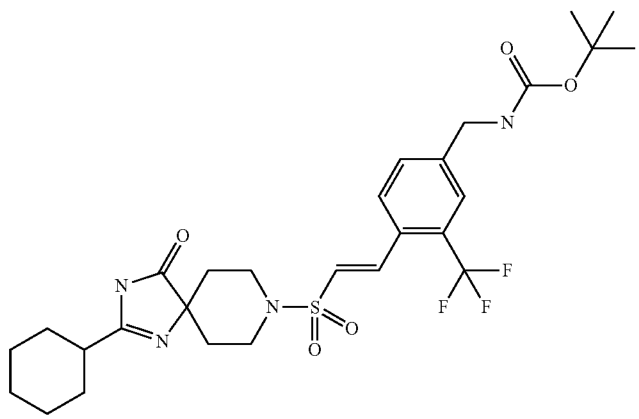 [SMILES: CC(C)(C)OC(=O)NCc1ccc(/C=C/S(=O)(=O)N2CCC3(CC2)N=C(C2CCCCC2)NC3=O)c(C(F)(F)F)c1] | LCMS-C-1 | 2.87 | 599 (M + H)+ |
| 206 | 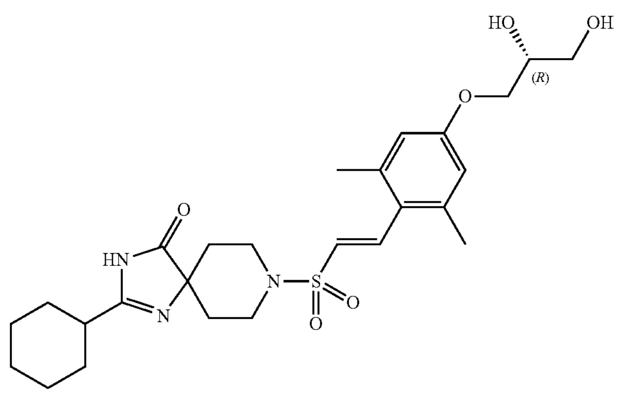 | LCMS-C-1 | 2.38 | 520 (M + H)+ |
| 207 | 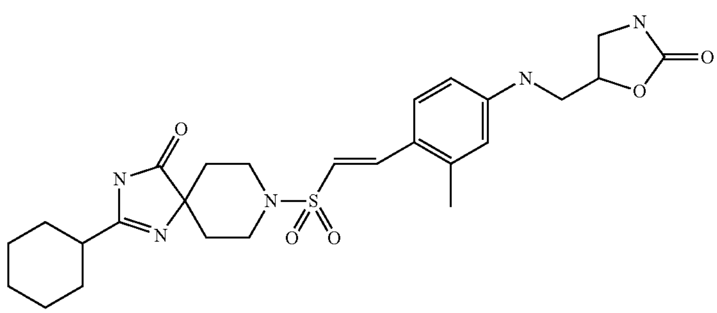 [SMILES: Cc1cc(NCC2CNC(=O)O2)ccc1/C=C/S(=O)(=O)N1CCC2(CC1)N=C(C1CCCCC1)NC2=O] | LCMS-C-1 | 2.23 | 530 (M + H)+ |

TABLE 32-continued

| Compound | Structure | LCMS or HPLC condition | Retention time (min) | MS (m/z) |
|---|---|---|---|---|
| 208 | 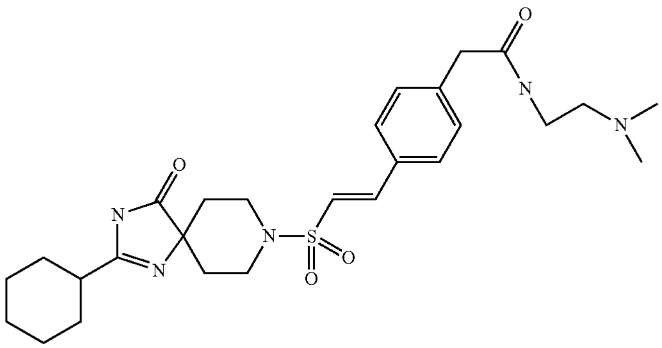 [SMILES: CN(C)CCNC(=O)Cc1ccc(/C=C/S(=O)(=O)N2CCC3(CC2)N=C(C2CCCCC2)NC3=O)cc1] | LCMS-C-1 | 2.12 | 530 (M + H)+ |

The aryl bromide reagent used in the synthesis of Compound 204 (N-(4-bromo-3,5-dimethyl-phenyl)-acetamide) was synthesized as follows.

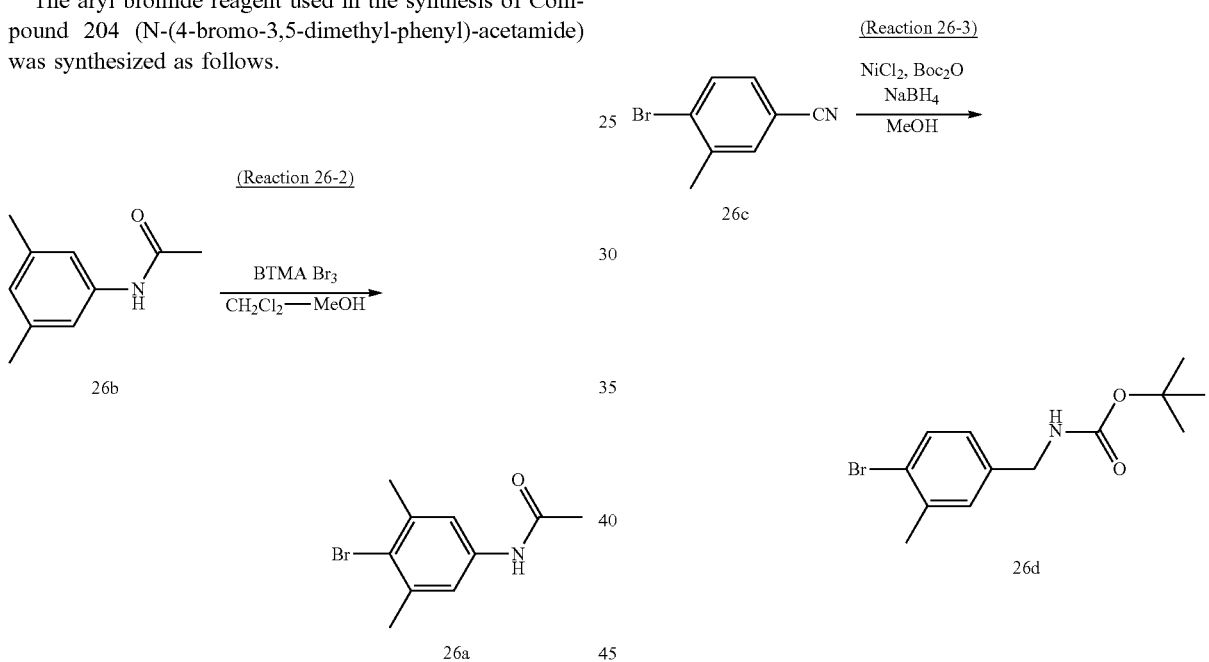

Benzyltrimethylammonium tribromide (BTMA-Br₃) (7.8 g, 20.21 mmol) was added to a solution of N-(3,5-dimethyl-phenyl)-acetamide (3.0 g, 18.38 mmol) in CH₂Cl₂/MeOH (90 ml/90 ml) at room temperature in an Ar atmosphere. The reaction mixture was stirred at room temperature for 10 minutes. The reaction mixture was concentrated under reduced pressure, and CH₂Cl₂ was then added to the resulting residue. The organic layer was washed with H₂O, and then dried over anhydrous Na₂SO₄ and concentrated under reduced pressure. The residue was purified by silica gel column chromatography (hexane:EtOAc=1:1) to give N-(4-bromo-3,5-dimethyl-phenyl)-acetamide (4.0 g, yield 90%).

MS (ESI+) m/z=242, 244 (M+H)+.

The aryl bromide reagent used in the synthesis of Compound 205 ((4-bromo-3-methyl-benzyl)-carbamic acid tert-butyl ester) was synthesized as follows.

NaBH₄ (1.45 g, 38.25 mmol) was added in small portions to a mixture of 4-bromo-3-methyl-benzonitrile (2.50 g, 12.8 mmol), NiCl₂ (1.65 g, 12.8 mmol) and Boc₂O (5.57 g, 25.5 mmol) in anhydrous MeOH (130 ml) at 0° C. The reaction mixture was stirred at room temperature for two hours and then concentrated under reduced pressure. Ethyl acetate and water were added to the resulting residue, and the mixture was filtered through celite. The organic layer and the aqueous layer were separated, and the aqueous layer was then extracted with ethyl acetate. The organic layers were combined, dried over Na₂SO₄ and then concentrated under reduced pressure. The residue was purified by silica gel column chromatography (hexane/ethyl acetate=1/0→4/1) to give (4-bromo-3-methyl-benzyl)-carbamic acid tert-butyl ester as a white solid (2.42 g, 63%).

MS (ESI) m/z=322 (M+Na)+.

The aryl bromide reagent used in the synthesis of Compound 206 ((R)-3-(4-bromo-3,5-dimethyl-phenoxy)-propane-1,2-diol) was synthesized as follows.

(Reaction 26-4)

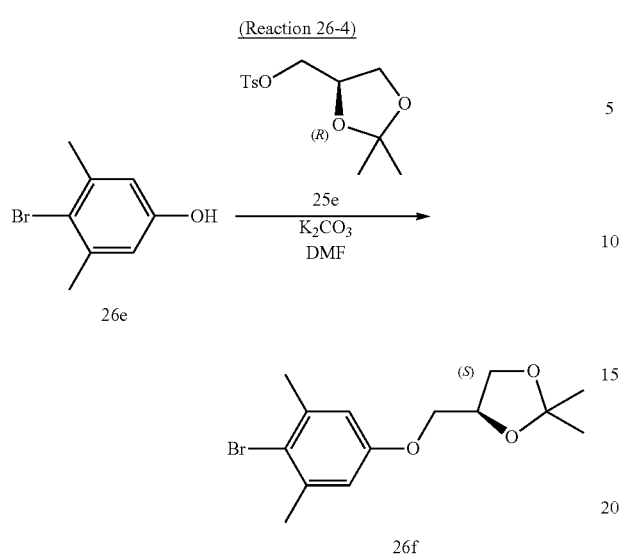

A mixture of 4-bromo-3,5-dimethyl-phenol (500 mg, 2.49 mmol), (R)-(−)-2,2-dimethyl-1,3-dioxolan-4-ylmethyl p-toluenesulfonate (856 mg, 2.99 mmol) and $K_2CO_3$ (1.03 g, 7.45 mmol) in dimethylformamide (5 ml) was stirred at 100° C. for two hours. The reaction mixture was diluted with AcOEt, and the organic layer was then washed with water (×2), dried over sodium sulfate and concentrated under reduced pressure. The resulting residue was purified by silica gel column chromatography (AcOEt-hexane) to give (S)-4-(4-bromo-3,5-dimethyl-phenoxymethyl)-2,2-dimethyl-[1,3]dioxolane as a colorless solid (749 mg, 95%).

$^1$H-NMR (400 MHz, $CDCl_3$) δ 1.40 (3H, s), 1.46 (3H, s), 2.37 (6H, s), 3.85-3.92 (2H, m), 3.98-4.03 (1H, m), 4.13-4.18 (1H, m), 4.42-4.48 (1H, m), 6.66 (2H, s).

(Reaction 26-5)

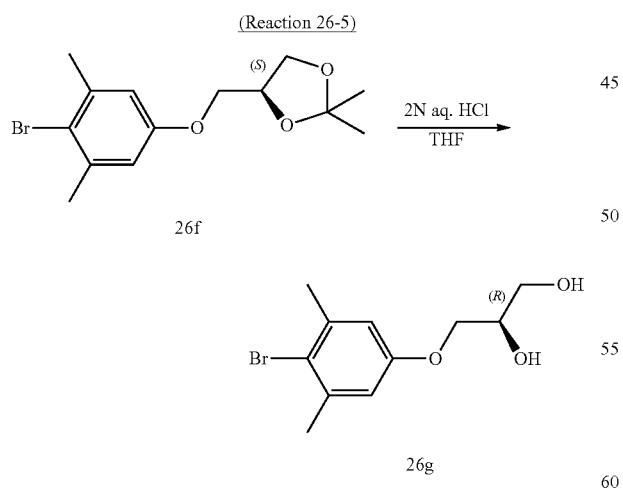

(R)-3-(4-Bromo-3,5-dimethyl-phenoxy)-propane-1,2-diol was synthesized by operations similar to those in Reaction 25-4 using appropriate reagents and starting material.

MS (ESI) m/z=275, 277 (M+H)+.

The aryl bromide reagent used in the synthesis of Compound 207 (5-[(4-bromo-3-methyl-phenylamino)-methyl]-oxazolidin-2-one) was synthesized as follows.

(Reaction 26-6)

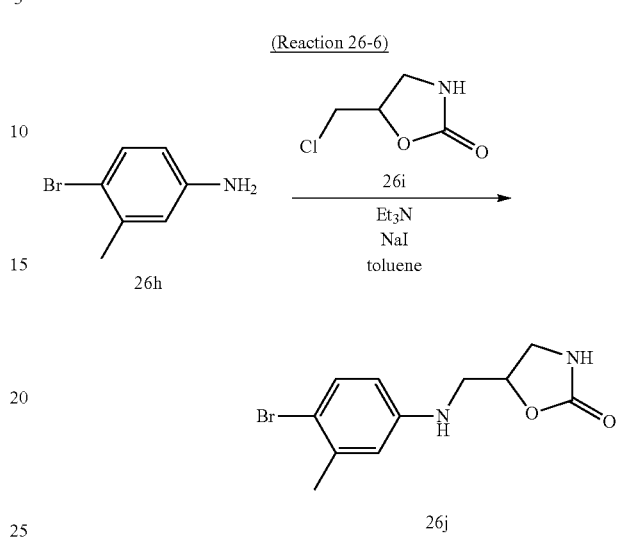

5-[(4-Bromo-3-methyl-phenylamino)-methyl]-oxazolidin-2-one was synthesized by operations similar to those in Reaction 25-12 using appropriate reagents and starting material.

MS (ESI) m/z=285, 287 (M+H)+.

The aryl bromide reagent used in the synthesis of Compound 208 (2-(4-bromo-phenyl)-N-(2-dimethylamino-ethyl) acetamide) was synthesized as follows.

(Reaction 26-7)

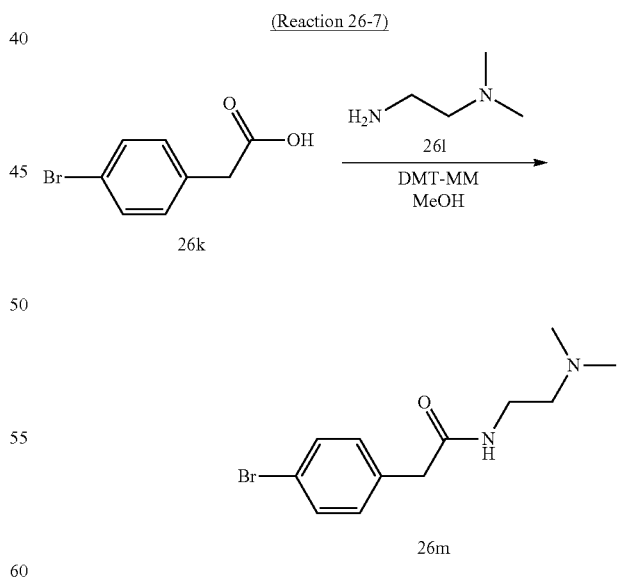

2-(4-Bromo-phenyl)-N-(2-dimethylamino-ethyl)acetamide was synthesized by operations similar to those in Reaction 10-1 using appropriate reagents and starting material.

MS (ESI) m/z=285, 287 (M+H)+.

Example 27

3-{(E)-2-[2-(4-Methyl-cyclohexyl)-4-oxo-1,3,8-triaza-spiro[4.5]dec-1-ene-8-sulfonyl]-vinyl}-benzonitrile (Compound 209)

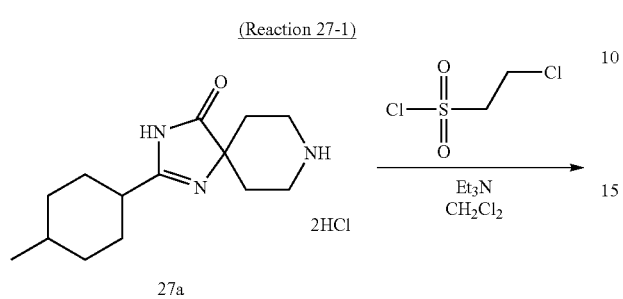

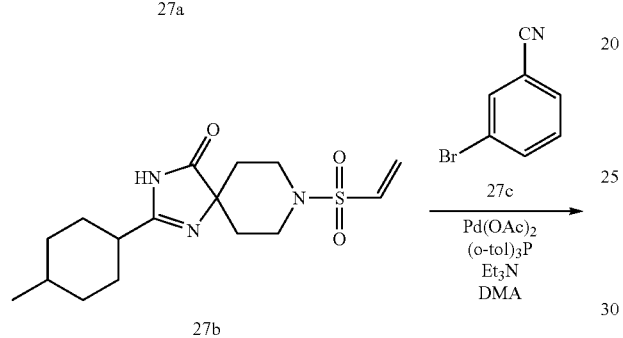

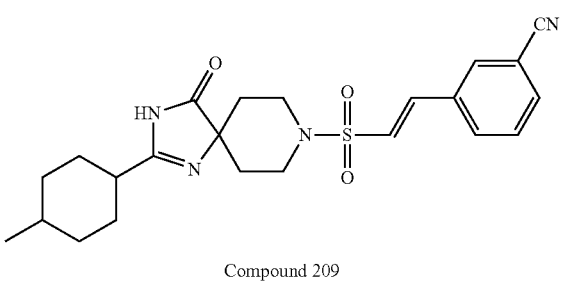

Compound 209

3-{(E)-2-[2-(4-Methyl-cyclohexyl)-4-oxo-1,3,8-triaza-spiro[4.5]dec-1-ene-8-sulfonyl]-vinyl}-benzonitrile was synthesized by operations similar to those in Reaction 25-1 and Reaction 25-2 using appropriate reagents and starting material.

MS (ESI) m/z=441 (M+H)+.

Example 28

8-{(E)-2-[4-(3,4-Dihydroxy-butoxy)-2-methyl-phenyl]-ethenesulfonyl}-2-(3-trifluoromethyl-phenyl)-1,3,8-triaza-spiro[4.5]dec-1-en-4-one (Compound 210)

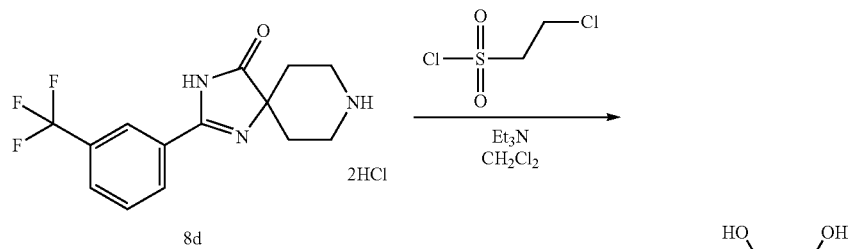

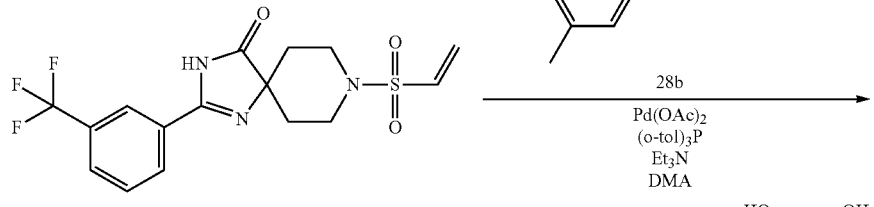

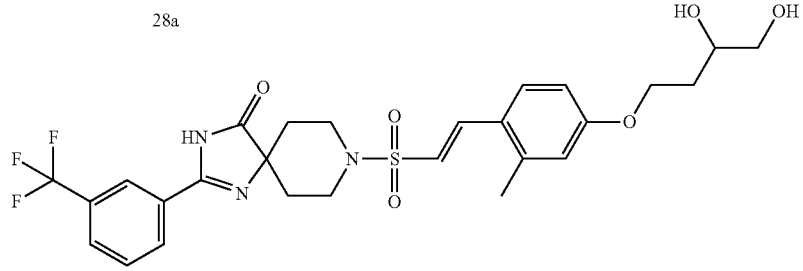

Compound 210

8-{(E)-2-[4-(3,4-Dihydroxy-butoxy)-2-methyl-phenyl]-ethenesulfonyl}-2-(3-trifluoromethyl-phenyl)-1,3,8-triazaspiro[4.5]dec-1-en-4-one was synthesized by operations similar to those in Reaction 25-1 and Reaction 25-2 using appropriate reagents and starting material.
MS (ESI) m/z=441 (M+H)+.

The example compounds shown below were synthesized by operations similar to those in Example 28 using appropriate reagents and starting materials.

Compounds 211 to 214

TABLE 33

| Compound | Structure | LCMS or HPLC condition | Retention time (min) | MS (m/z) |
| --- | --- | --- | --- | --- |
| 211 | 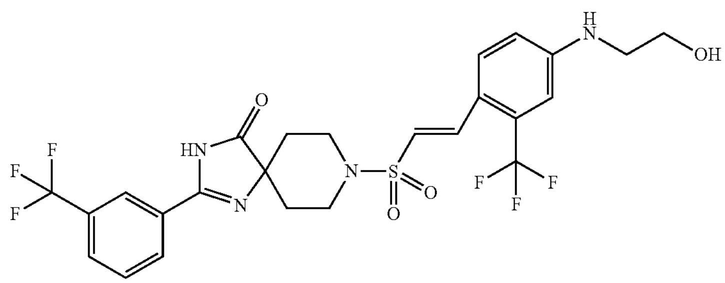 [SMILES: O=C1NC(c2cccc(C(F)(F)F)c2)=NC12CCN(S(=O)(=O)/C=C/c1ccc(NCCO)cc1C(F)(F)F)CC2] | LCMS-C-2 | 2.02 | 591 (M + H)+ |
| 212 | 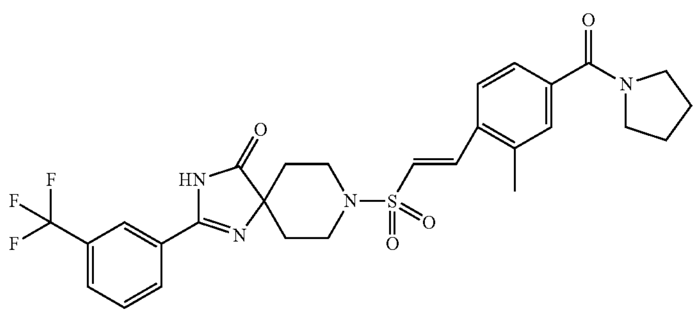 [SMILES: Cc1cc(C(=O)N2CCCC2)ccc1/C=C/S(=O)(=O)N1CCC2(CC1)N=C(c1cccc(C(F)(F)F)c1)NC2=O] | LCMS-B-1 | 2.25 | 575 (M + H)+ |
| 213 | 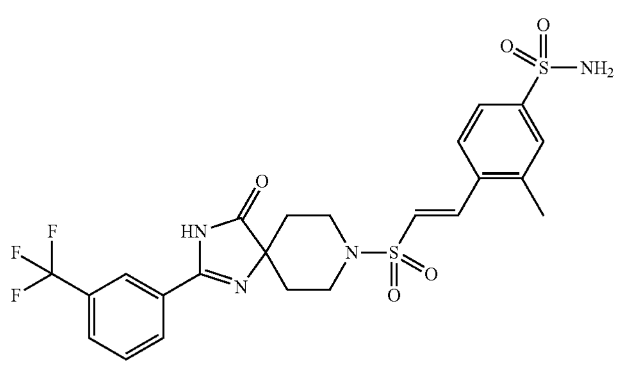 [SMILES: Cc1cc(S(N)(=O)=O)ccc1/C=C/S(=O)(=O)N1CCC2(CC1)N=C(c1cccc(C(F)(F)F)c1)NC2=O] | LCMS-C-1 | 2.37 | 557 (M + H)+ |
| 214 | 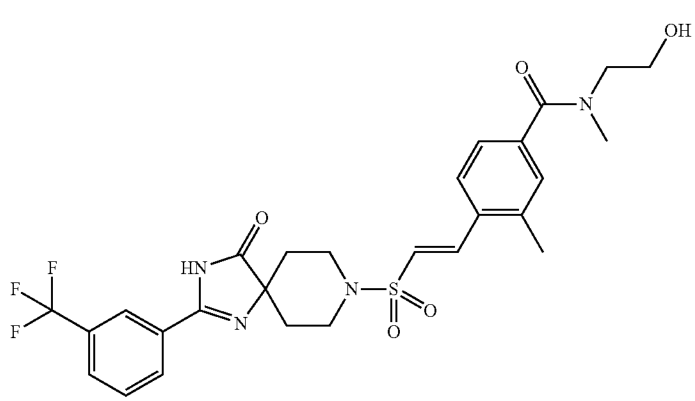 [SMILES: Cc1cc(C(=O)N(C)CCO)ccc1/C=C/S(=O)(=O)N1CCC2(CC1)N=C(c1cccc(C(F)(F)F)c1)NC2=O] | LCMS-C-1 | 2.42 | 579 (M + H)+ |

The aryl bromide reagent used in the synthesis of Compound 210 (4-(4-bromo-3-methyl-phenoxy)-butane-1,2-diol) was synthesized as follows.

(Reaction 28-2)

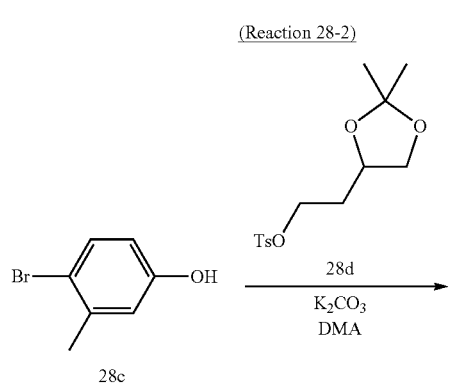

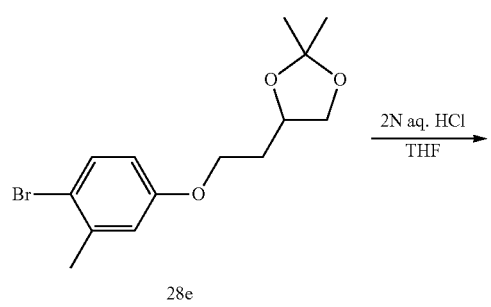

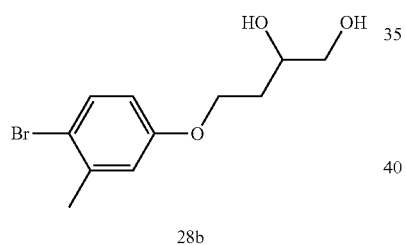

4-(4-Bromo-3-methyl-phenoxy)-butane-1,2-diol was synthesized by operations similar to those in Reaction 26-4 and Reaction 25-4 using appropriate reagents and starting material.

MS (ESI) m/z=275, 277 (M+H)+.

The aryl bromide reagent used in the synthesis of Compound 211 (2-(4-bromo-3-trifluoromethyl-phenylamino)-ethanol) was synthesized as follows.

(Reaction 28-3)

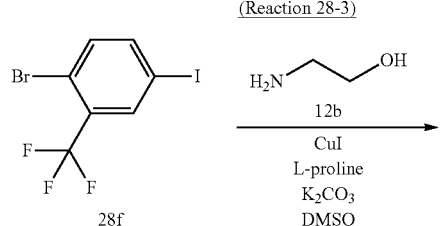

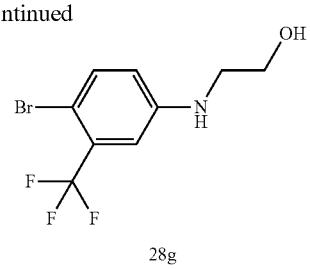

2-(4-Bromo-3-trifluoromethyl-phenylamino)-ethanol was synthesized by operations similar to those in Reaction 12-1 using appropriate reagents and starting material.

MS (ESI) m/z=284, 286 (M+H)+.

The aryl bromide reagent used in the synthesis of Compound 212 ((4-bromo-3-methyl-phenyl)-pyrrolidin-1-yl-methanone) was synthesized as follows.

(Reaction 28-4)

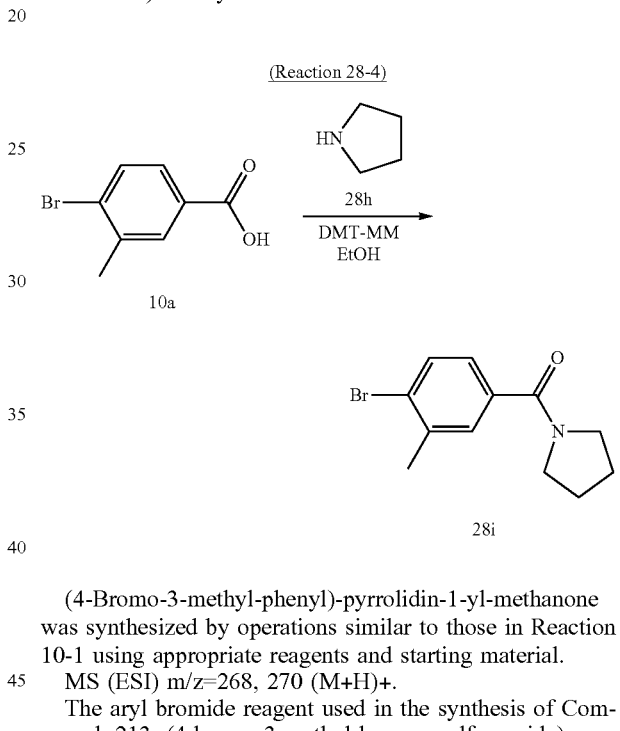

(4-Bromo-3-methyl-phenyl)-pyrrolidin-1-yl-methanone was synthesized by operations similar to those in Reaction 10-1 using appropriate reagents and starting material.

MS (ESI) m/z=268, 270 (M+H)+.

The aryl bromide reagent used in the synthesis of Compound 213 (4-bromo-3-methyl-benzenesulfonamide) was synthesized as follows.

(Reaction 28-5)

A 28% aqueous NH₃ solution (2.0 ml) was added to a solution of 4-bromo-3-methyl-benzenesulfonyl chloride (250 mg, 0.927 mmol) in THF (2.0 ml) at 0° C. The mixture was stirred at 0° C. for 6.5 hours. The reaction mixture was quenched with 1 N HCl and extracted with CH₂Cl₂. The organic layer was concentrated under reduced pressure, and the resulting residue was purified by silica gel column chromatography (CH₂Cl₂-AcOEt) to give 4-bromo-3-methyl-benzenesulfonamide as a white powder (126 mg, 54%).

MS (ESI) m/z=272, 274 (M+Na)+.

The aryl bromide reagent used in the synthesis of Compound 214 (4-bromo-N-(2-hydroxy-ethyl)-3,N-dimethyl-benzamide) was synthesized as follows.

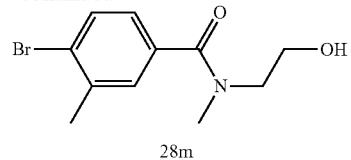

28m

4-Bromo-N-(2-hydroxy-ethyl)-3,N-dimethyl-benzamide was synthesized by operations similar to those in Reaction 10-1 using appropriate reagents and starting material.

MS (ESI) m/z=272, 274 (M+H)+.

Example 29

N-(3-Methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide (Compound 215)

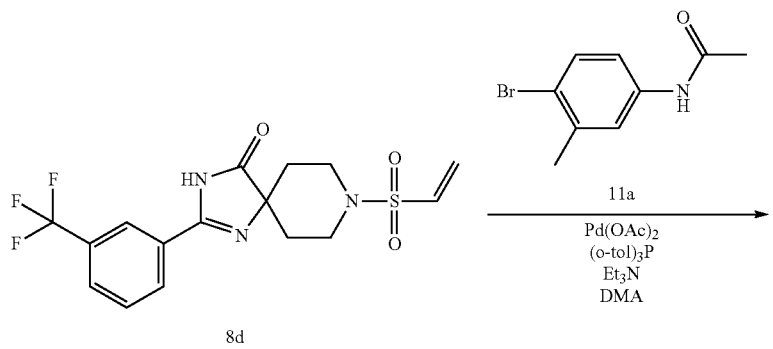

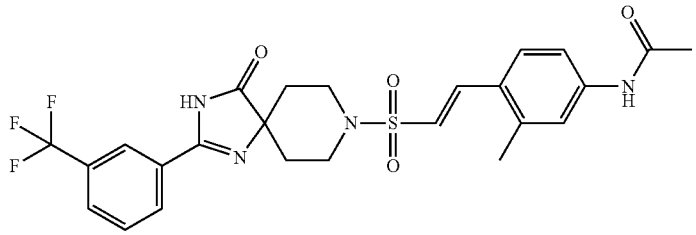

Compound 215

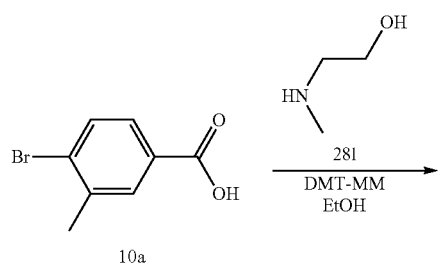

N-(3-Methyl-4-{(E)-2-[4-oxo-2-(3-trifluoromethyl-phenyl)-1,3,8-triaza-spiro[4.5]dec-1-ene-8-sulfonyl]-vinyl}-phenyl)-acetamide was synthesized by operations similar to those in Reaction 26-1 using appropriate reagents and starting material.

MS (ESI) m/z=535 (M+H)+.

The example compounds shown below were synthesized by operations similar to those in Example 29 using appropriate reagents and starting materials.

Compounds 216 to 223

TABLE 34

| Compound | Structure | LCMS or HPLC condition | Retention time (min) | MS (m/z) |
|---|---|---|---|---|
| 216 | 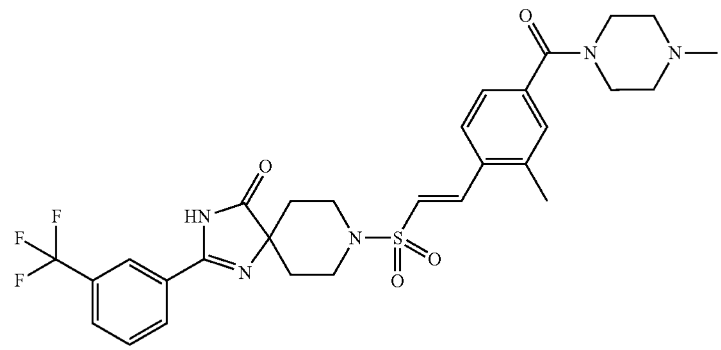 [SMILES: Cc1cc(C(=O)N2CCN(C)CC2)ccc1/C=C/S(=O)(=O)N1CCC2(CC1)N=C(c1cccc(C(F)(F)F)c1)NC2=O] | LCMS-C-1 | 2.55 | 604 (M + H)+ |
| 217 | 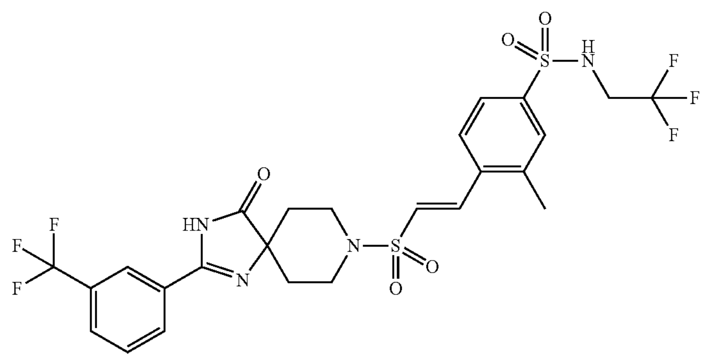 [SMILES: Cc1cc(S(=O)(=O)NCC(F)(F)F)ccc1/C=C/S(=O)(=O)N1CCC2(CC1)N=C(c1cccc(C(F)(F)F)c1)NC2=O] | LCMS-C-1 | 2.70 | 639 (M + H)+ |
| 218 | 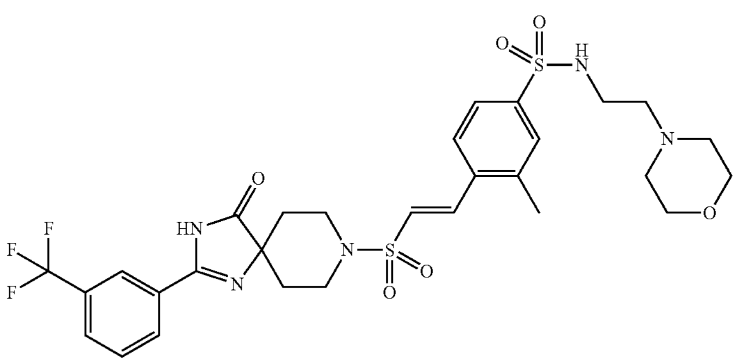 [SMILES: Cc1cc(S(=O)(=O)NCCN2CCOCC2)ccc1/C=C/S(=O)(=O)N1CCC2(CC1)N=C(c1cccc(C(F)(F)F)c1)NC2=O] | LCMS-C-1 | 2.57 | 670 (M + H)+ |
| 219 | 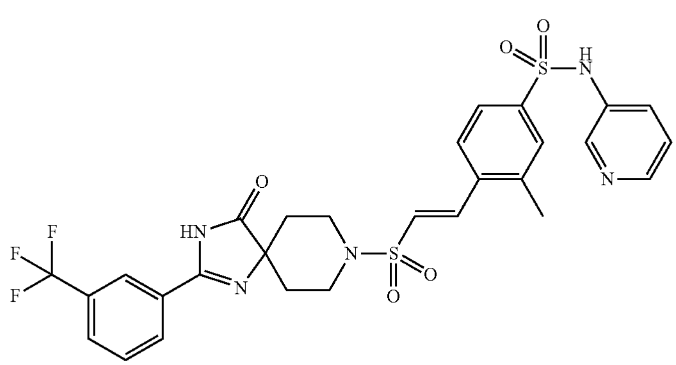 [SMILES: Cc1cc(S(=O)(=O)Nc2cccnc2)ccc1/C=C/S(=O)(=O)N1CCC2(CC1)N=C(c1cccc(C(F)(F)F)c1)NC2=O] | LCMS-C-1 | 1.95 | 634 (M + H)+ |

TABLE 34-continued
| Compound | Structure | LCMS or HPLC condition | Retention time (min) | MS (m/z) |
|---|---|---|---|---|
| 220 | 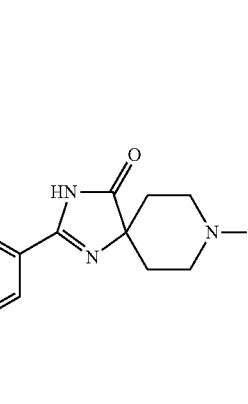 | LCMS-C-1 | 2.42 | 577 (M + H)+ |
| 221 | 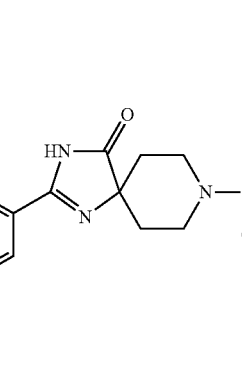 | LCMS-C-1 | 2.42 | 591 (M + H)+ |
| 222 | 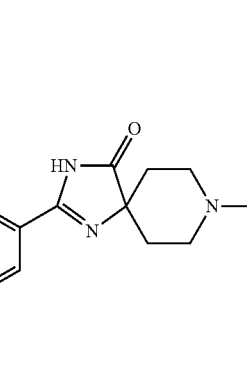 | LCMS-C-1 | 2.45 | 593 (M + H)+ |
| 223 | 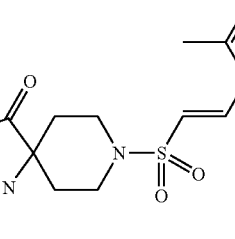 | LCMS-C-1 | 2.50 | 676 (M + H)+ |

The aryl bromide reagent used in the synthesis of Compound 216 ((4-bromo-3-methyl-phenyl)-(4-methyl-piperazin-1-yl)-methanone) was synthesized as follows.

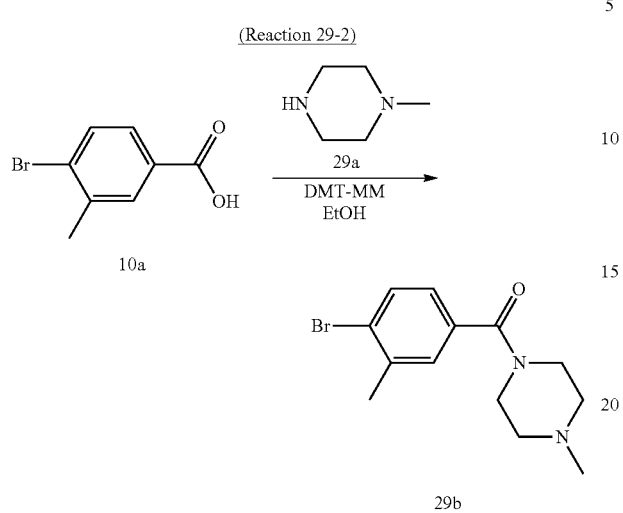

(4-Bromo-3-methyl-phenyl)-(4-methyl-piperazin-1-yl)-methanone was synthesized by operations similar to those in Reaction 10-1 using appropriate reagents and starting material.

MS (ESI) m/z=297, 299 (M+H)+.

The aryl bromide reagents used in the synthesis of Compounds 217 to 219 were synthesized by operations similar to those in Reaction 28-5 using appropriate reagents and starting materials.

TABLE 35

| Target Compound | Aryl bromide reagent | Aryl bromide reagent MS (m/z) |
|---|---|---|
| 217 | | 354, 355 (M + Na)+ |
| 218 | | 363, 365 (M + H)+ |
| 219 | | 327, 329 (M + H)+ |

The aryl bromide reagent used in the synthesis of Compound 220 ((R)-1-(4-bromo-3-methyl-phenyl)-4-hydroxy-pyrrolidin-2-one) was synthesized as follows.

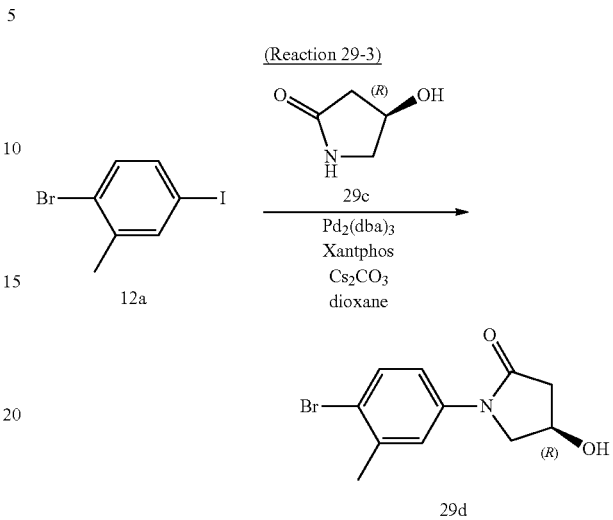

A mixture of 2-bromo-5-iodotoluene (500 mg, 1.68 mmol), (R)-4-hydroxy-pyrrolidinone (204 mg, 2.02 mmol), 4,5-bis(diphenylphosphino)-9,9-dimethylxanthene (58.5 mg, 0.101 mmol), tris(dibenzylideneacetone)-dipalladium (0)-chloroform adduct (35.0 mg, 0.034 mmol) and cesium carbonate (769 mg, 2.36 mmol) in 1,4-dioxane (degassed, 5 ml) was stirred at 110° C. overnight in a nitrogen stream. The reaction mixture was treated with H$_2$O and extracted with AcOEt (×2). The organic layers were combined and sequentially washed with H$_2$O and saturated brine, and then dried over Na$_2$SO$_4$ and concentrated under reduced pressure. The resulting residue was purified by silica gel chromatography (n-hexane/AcOEt) to give (R)-1-(4-bromo-3-methyl-phenyl)-4-hydroxy-pyrrolidin-2-one as a pale brown solid (173 mg, 38%).

$^1$H-NMR (400 MHz, DMSO-d6) δ 2.29 (1H, d, J=17.1 Hz), 2.34 (3H, s), 2.82 (1H, dd, J=17.1, 6.4 Hz), 3.57 (1H, d, J=10.3 Hz), 4.01 (1H, dd, J=10.3, 4.9 Hz), 4.36-4.40 (1H, m), 5.35 (1H, d, J=3.4 Hz, OH), 7.51 (1H, dd, J=8.8, 2.4 Hz), 7.55 (1H, d, J=8.8 Hz), 7.62 (1H, br. s). MS (ESI) m/z=270, 272 (M+H)+.

The aryl bromide reagent used in the synthesis of Compound 221 ((R)-1-(4-bromo-3-methyl-phenyl)-5-hydroxymethyl-pyrrolidin-2-one) was synthesized as follows.

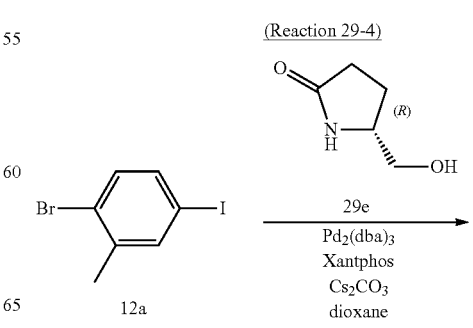

-continued

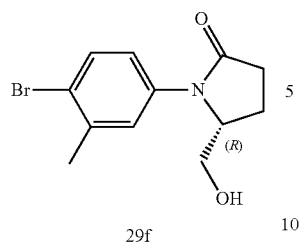

29f (R)-1-(4-Bromo-3-methyl-phenyl)-5-hydroxymethyl-pyrrolidin-2-one was synthesized by operations similar to those in Reaction 29-3 using appropriate reagents and starting material.

MS (ESI) m/z=284, 286 (M+H)+.

The aryl bromide reagent used in the synthesis of Compound 222 ((R)-3-(4-bromo-3-methyl-phenyl)-5-hydroxymethyl-oxazolidin-2-one) was synthesized as follows.

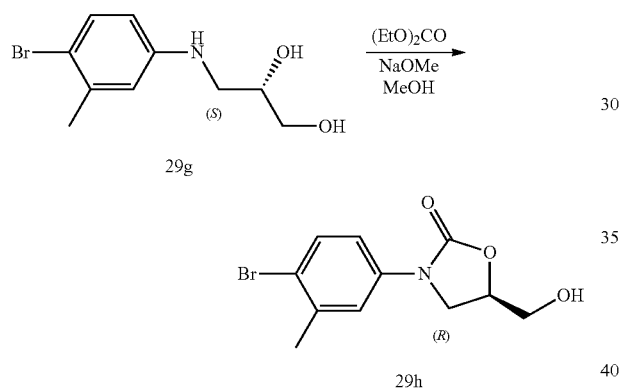

A mixture of (S)-3-(4-bromo-3-methyl-phenylamino)-propane-1,2-diol (202 mg, 0.777 mmol), diethyl carbonate (3 ml), sodium methoxide (28% in MeOH, 0.160 ml) and MeOH (4 ml) was stirred at 130° C. overnight. The reaction mixture was treated with saturated NH$_4$Cl and H$_2$O and extracted with AcOEt (×2). The organic layers were combined and sequentially washed with H$_2$O and saturated brine, and then dried over Na$_2$SO$_4$ and concentrated under reduced pressure. The resulting residue was purified by silica gel column chromatography (n-hexane/AcOEt) to give (R)-3-(4-bromo-3-methyl-phenyl)-5-hydroxymethyl-oxazolidin-2-one (170 mg, 77%).

$^1$H-NMR (400 MHz, DMSO-d6) δ 2.35 (3H, s), 3.53-3.57 (1H, m), 3.65-3.68 (1H, m), 3.82 (1H, dd, J=8.8, 6.4 Hz), 4.06 (1H, dd, J=9.3, 8.8 Hz), 4.67-4.72 (1H, m), 5.22 (1H, br. s), 7.42 (1H, dd, J=8.8, 2.9 Hz), 7.54 (1H, d, J=2.5 Hz), 7.56 (1H, d, J=8.8 Hz). MS (ESI) m/z=286, 288 (M+H)+.

The aryl bromide reagent used in the synthesis of Compound 223 ((4-bromo-3,5-dimethyl-phenyl)-[3-(3-dimethylamino-propoxy)-azetidin-1-yl]-methanone) was synthesized as follows.

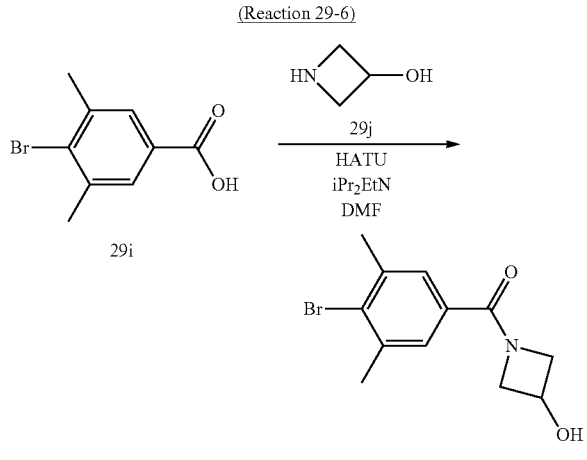

(4-Bromo-3,5-dimethyl-phenyl)-(3-hydroxy-azetidin-1-yl)-methanone was synthesized by operations similar to those in Reaction 10-14 using appropriate reagents and starting material.

MS (ESI) m/z=284, 286 (M+H)+.

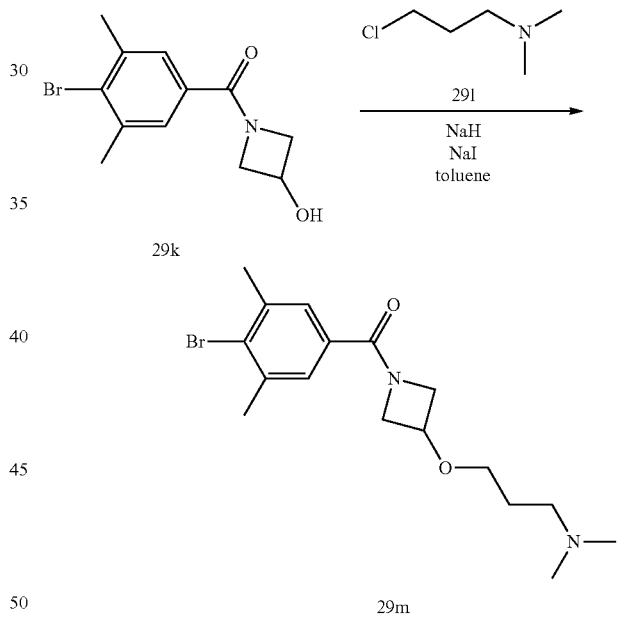

NaH (110 mg, 2.75 mmol, 60% oily suspension) and NaI (274 mg, 1.83 mmol) were added to a solution of (4-bromo-3,5-dimethyl-phenyl)-(3-hydroxy-azetidin-1-yl)-methanone (130 mg, 0.458 mmol) and (3-chloro-propyl)-dimethyl-amine (289 mg, 1.83 mmol) in toluene (1.8 ml). The mixture was stirred at 110° C. for 15 hours. The reaction mixture was diluted with AcOEt, and the organic layer was then sequentially washed with a saturated aqueous NaHCO$_3$ solution, water and a saturated aqueous NaCl solution. Further, the organic layer was dried over sodium sulfate and then concentrated under reduced pressure. The resulting residue was purified by silica gel column chromatography (n-hexane/AcOEt) to give (4-bromo-3,5-dimethyl-phenyl)-[3-(3-dimethylamino-propoxy)-azetidin-1-yl]-methanone (46 mg, 27%).

MS (ESI) m/z=369, 371 (M+H)+.

Example 30

N-(3-Hydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide (Compound 224)

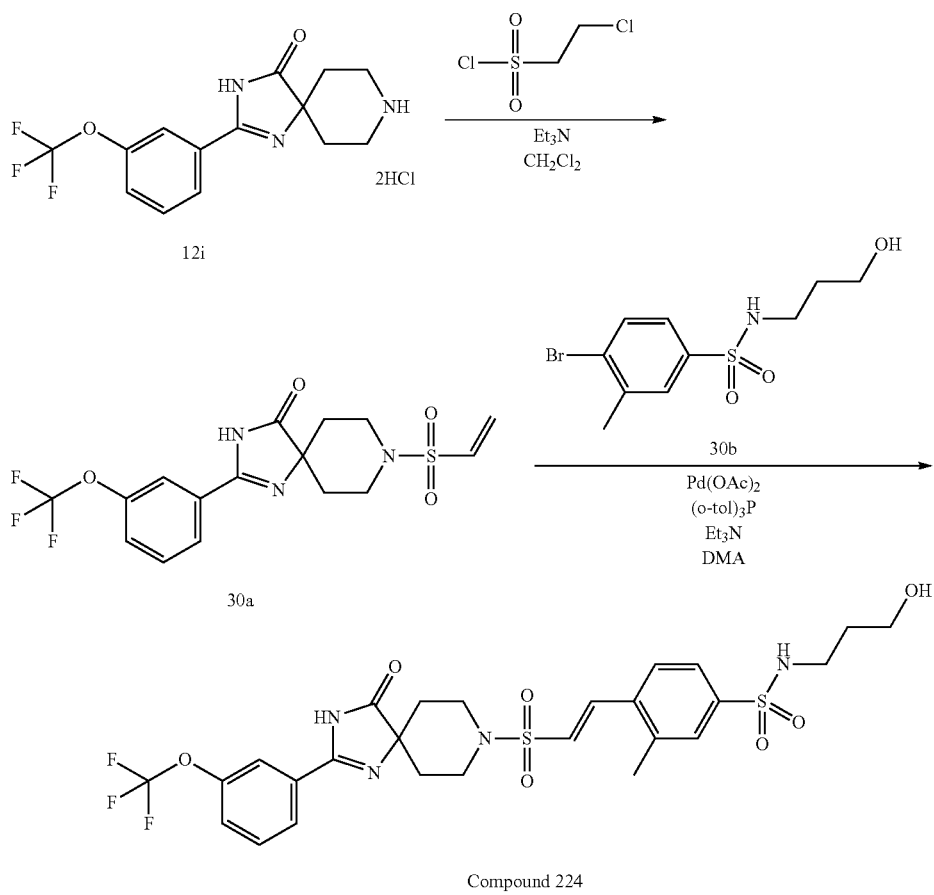

N-(3-Hydroxy-propyl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide was synthesized by operations similar to those in Reaction 25-1 and Reaction 25-2 using appropriate reagents and starting material.
MS (ESI) m/z=645 (M+H)+.

The example compound shown below was synthesized by operations similar to those in Example 30 using appropriate reagents and starting material.

Compound 225

TABLE 36

| Compound | Structure | LCMS or HPLC condition | Retention time (min) | MS (m/z) |
| --- | --- | --- | --- | --- |
| 225 | 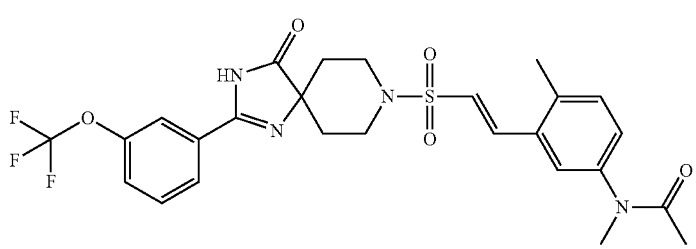 [SMILES: CC(=O)N(C)c1ccc(C)c(/C=C/S(=O)(=O)N2CCC3(CC2)N=C(c2cccc(OC(F)(F)F)c2)NC3=O)c1] | LCMS-D-1 | 3.3 | 567 (M + H)+ |

317

The aryl bromide reagent used in the synthesis of Compound 224 (4-bromo-N-(3-hydroxy-propyl)-3-methyl-benzenesulfonamide) was synthesized as follows.

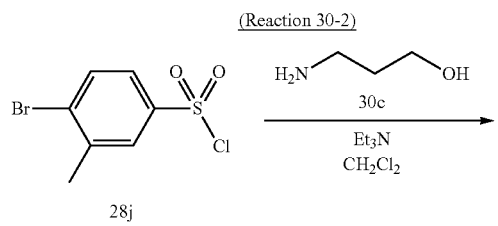

4-Bromo-N-(3-hydroxy-propyl)-3-methyl-benzenesulfonamide was synthesized by operations similar to those in Reaction 5-4 using appropriate reagents and starting material.

MS (ESI) m/z=322, 324 (M+H)+.

The aryl bromide reagent used in the synthesis of Compound 225 (N-(3-bromo-4-methyl-phenyl)-N-methyl-acetamide) was synthesized as follows.

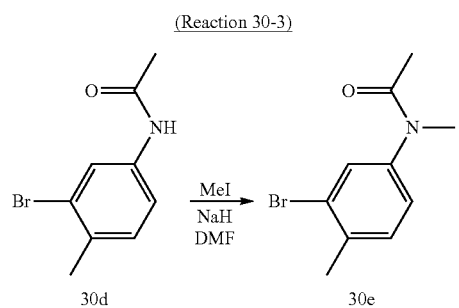

318

N-(3-Bromo-4-methyl-phenyl)-N-methyl-acetamide was synthesized by operations similar to those in Reaction 25-3 using appropriate reagents and starting material.

MS (ESI) m/z=242, 244 (M+H)+.

Example 31

8-[(E)-2-(3-Hydroxy-2-methyl-phenyl)-ethenesulfonyl]-2-(3-trifluoromethoxy-phenyl)-1,3,8-triaza-spiro[4.5]dec-1-en-4-one (Compound 226)

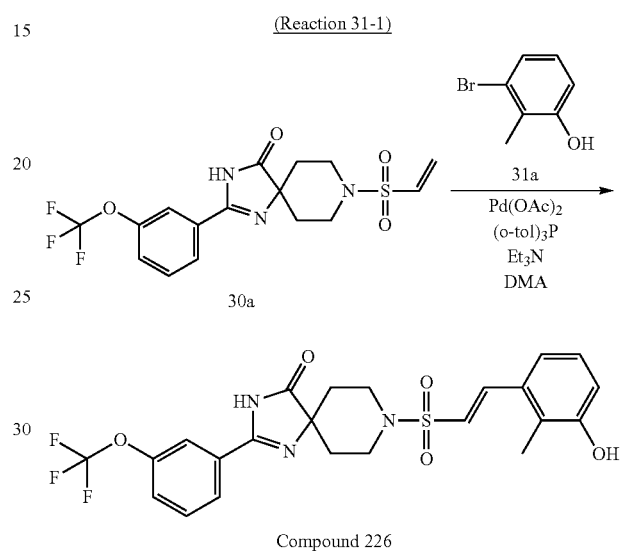

8-[(E)-2-(3-Hydroxy-2-methyl-phenyl)-ethenesulfonyl]-2-(3-trifluoromethoxy-phenyl)-1,3,8-triaza-spiro[4.5]dec-1-en-4-one was synthesized by operations similar to those in Reaction 25-2 using appropriate reagents and starting material.

MS (ESI) m/z=510 (M+H)+.

The example compounds shown below were synthesized by operations similar to those in Example 31 using appropriate reagents and starting materials.

Compounds 227 to 239

TABLE 37

| Compound | Structure | LCMS or HPLC condition | Retention time (min) | MS (m/z) |
|---|---|---|---|---|
| 227 | 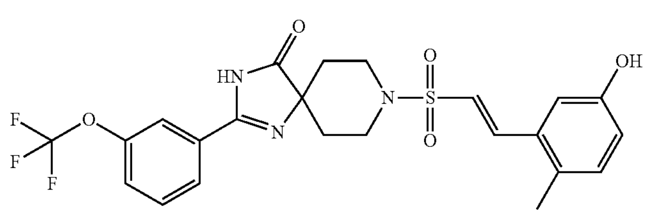 [SMILES: Cc1ccc(O)cc1/C=C/S(=O)(=O)N1CCC2(CC1)N=C(c1cccc(OC(F)(F)F)c1)NC2=O] | HPLC-A-2 | 11.5 | 510 (M + H)+ |

TABLE 37-continued

| Compound | Structure | LCMS or HPLC condition | Retention time (min) | MS (m/z) |
|---|---|---|---|---|
| 228 | 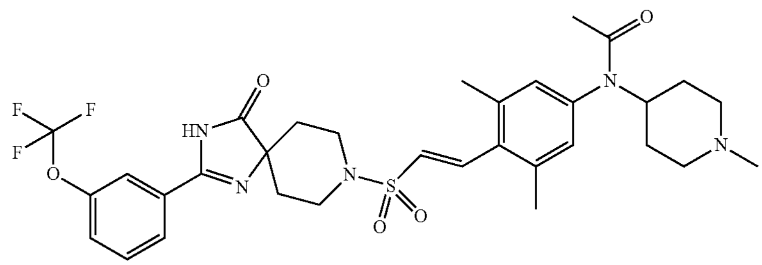 | LCMS-A-1 | 2.12 | 648 (M + H)+ |
| 229 | 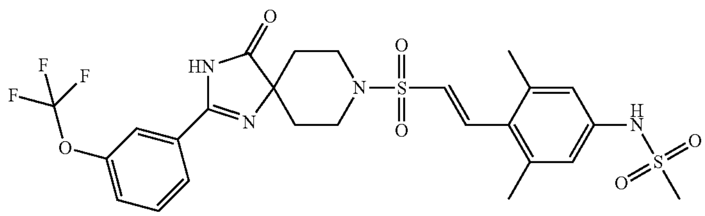 [SMILES: Cc1cc(NS(C)(=O)=O)cc(C)c1/C=C/S(=O)(=O)N1CCC2(CC1)N=C(c1cccc(OC(F)(F)F)c1)NC2=O] | LCMS-D-1 | 3.3 | 601 (M + H)+ |
| 230 | 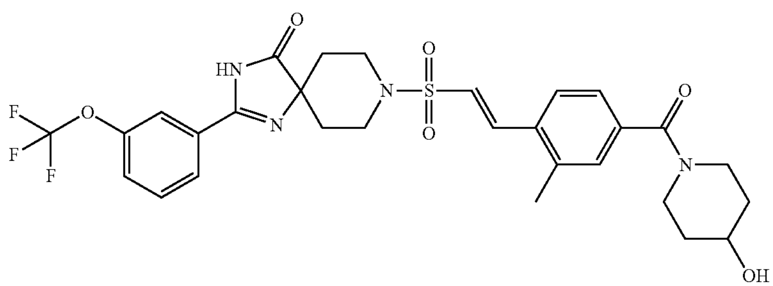 [SMILES: Cc1cc(C(=O)N2CCC(O)CC2)ccc1/C=C/S(=O)(=O)N1CCC2(CC1)N=C(c1cccc(OC(F)(F)F)c1)NC2=O] | LCMS-A-1 | 2.25 | 621 (M + H)+ |
| 231 | 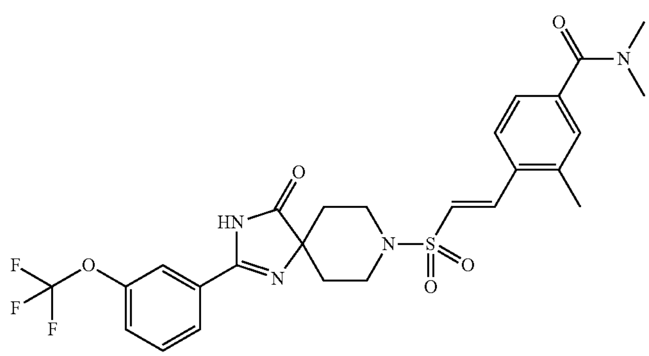 [SMILES: Cc1cc(C(=O)N(C)C)ccc1/C=C/S(=O)(=O)N1CCC2(CC1)N=C(c1cccc(OC(F)(F)F)c1)NC2=O] | LCMS-C-1 | 2.60 | 565 (M + H)+ |
| 232 | 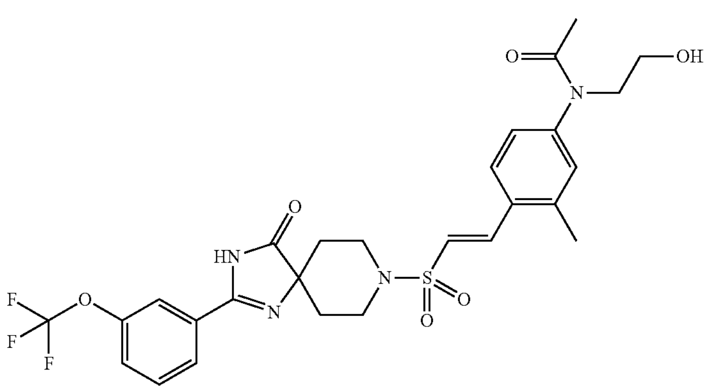 [SMILES: CC(=O)N(CCO)c1ccc(/C=C/S(=O)(=O)N2CCC3(CC2)N=C(c2cccc(OC(F)(F)F)c2)NC3=O)c(C)c1] | LCMS-C-1 | 2.52 | 595 (M + H)+ |

TABLE 37-continued

| Compound | Structure | LCMS or HPLC condition | Retention time (min) | MS (m/z) |
|---|---|---|---|---|
| 233 | 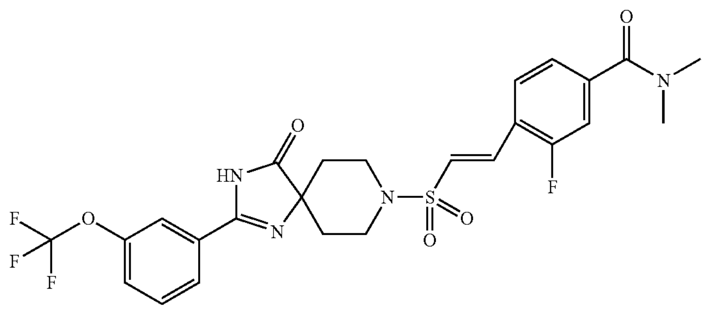 [SMILES: CN(C)C(=O)c1ccc(/C=C/S(=O)(=O)N2CCC3(CC2)N=C(c2cccc(OC(F)(F)F)c2)NC3=O)c(F)c1] | LCMS-C-1 | 2.57 | 567 (M − H)− |
| 234 | 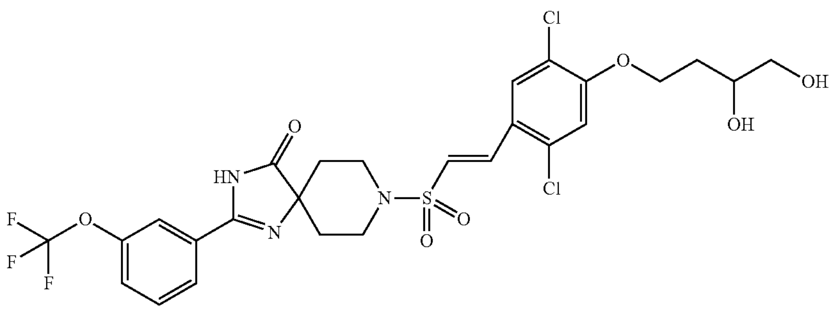 [SMILES: O=C1NC(c2cccc(OC(F)(F)F)c2)=NC12CCN(S(=O)(=O)/C=C/c1cc(Cl)c(OCCC(O)CO)cc1Cl)CC2] | LCMS-C-1 | 2.73 | 652 (M + H)+ |
| 235 | 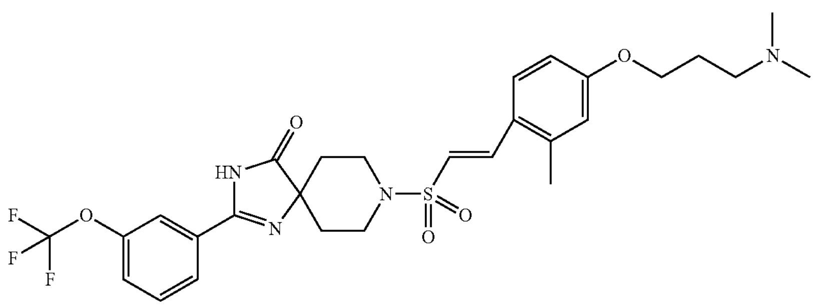 [SMILES: Cc1cc(OCCCN(C)C)ccc1/C=C/S(=O)(=O)N1CCC2(CC1)N=C(c1cccc(OC(F)(F)F)c1)NC2=O] | LCMS-C-1 | 2.67 | 595 (M + H)+ |
| 236 | 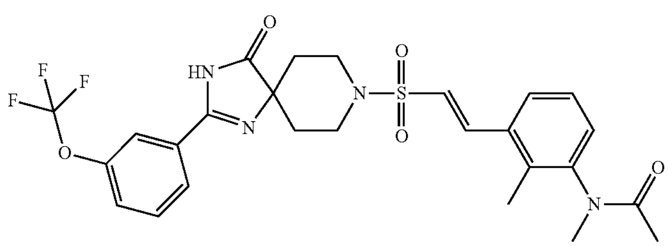 [SMILES: CC(=O)N(C)c1cccc(/C=C/S(=O)(=O)N2CCC3(CC2)N=C(c2cccc(OC(F)(F)F)c2)NC3=O)c1C] | LCMS-D-1 | 3.1 | 565 (M + H)+ |
| 237 | 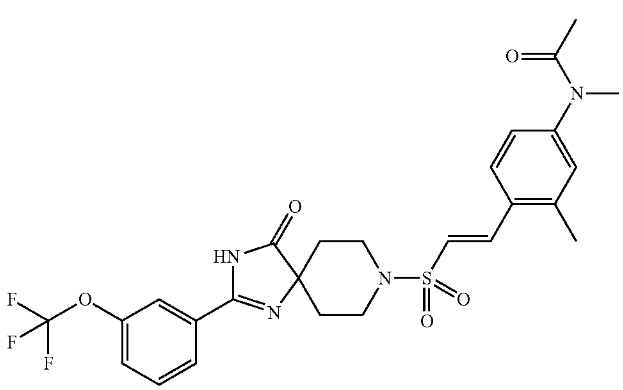 [SMILES: CC(=O)N(C)c1ccc(/C=C/S(=O)(=O)N2CCC3(CC2)N=C(c2cccc(OC(F)(F)F)c2)NC3=O)c(C)c1] | LCMS-C-1 | 2.63 | 565 (M + H)+ |

TABLE 37-continued

| Compound | Structure | LCMS or HPLC condition | Retention time (min) | MS (m/z) |
|---|---|---|---|---|
| 238 | 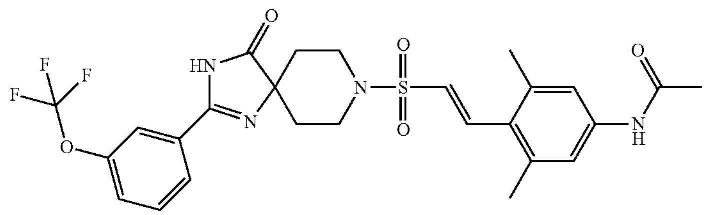 [SMILES: CC(=O)Nc1cc(C)c(/C=C/S(=O)(=O)N2CCC3(CC2)N=C(c2cccc(OC(F)(F)F)c2)NC3=O)c(C)c1] | HPLC-A-2 | 12.8 | 565 (M + H)+ |
| 239 | 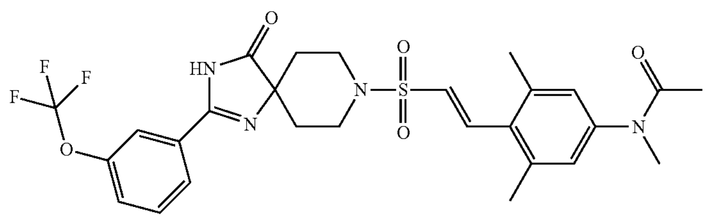 [SMILES: CC(=O)N(C)c1cc(C)c(/C=C/S(=O)(=O)N2CCC3(CC2)N=C(c2cccc(OC(F)(F)F)c2)NC3=O)c(C)c1] | HPLC-A-2 | 14.0 | 579 (M + H)+ |

The aryl bromide reagent used in the synthesis of Compound 230 ((4-bromo-3-methyl-phenyl)-(4-hydroxy-piperidin-1-yl)-methanone) was synthesized as follows.

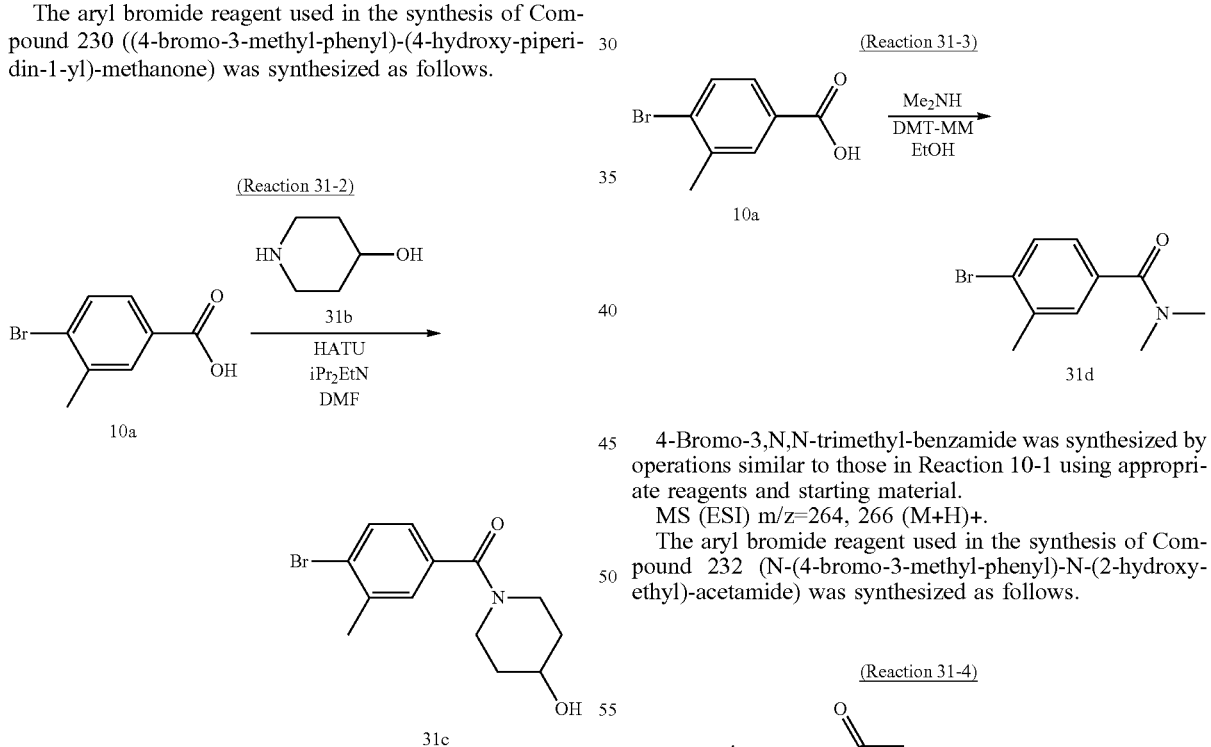

(4-Bromo-3-methyl-phenyl)-(4-hydroxy-piperidin-1-yl)-methanone was synthesized by operations similar to those in Reaction 10-14 using appropriate reagents and starting material.

MS (ESI) m/z=298, 300 (M+H)+.

The aryl bromide reagent used in the synthesis of Compound 231 (4-bromo-3,N,N-trimethyl-benzamide) was synthesized as follows.

4-Bromo-3,N,N-trimethyl-benzamide was synthesized by operations similar to those in Reaction 10-1 using appropriate reagents and starting material.

MS (ESI) m/z=264, 266 (M+H)+.

The aryl bromide reagent used in the synthesis of Compound 232 (N-(4-bromo-3-methyl-phenyl)-N-(2-hydroxyethyl)-acetamide) was synthesized as follows.

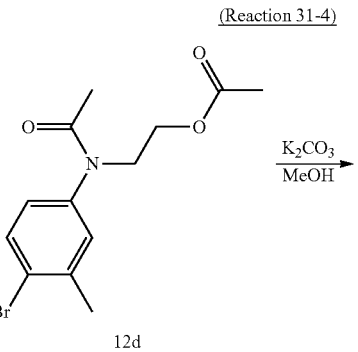

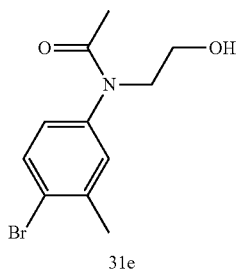

31e

N-(4-Bromo-3-methyl-phenyl)-N-(2-hydroxy-ethyl)-acetamide was synthesized by operations similar to those in Reaction 12-5 using appropriate reagents and starting material.

MS (ESI) m/z=272, 274 (M+H)+.

The aryl bromide reagent used in the synthesis of Compound 233 (4-bromo-3-fluoro-N,N-dimethyl-benzamide) was synthesized as follows.

(Reaction 31-5)

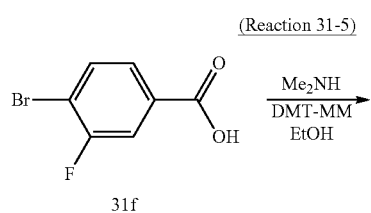

31f → 31g

4-Bromo-3-fluoro-N,N-dimethyl-benzamide was synthesized by operations similar to those in Reaction 10-1 using appropriate reagents and starting material.

MS (ESI) m/z=246, 248 (M+H)+.

The aryl bromide reagent used in the synthesis of Compound 234 (4-(4-bromo-2,5-dichloro-phenoxy)-butane-1,2-diol) was synthesized as follows.

(Reaction 31-6)

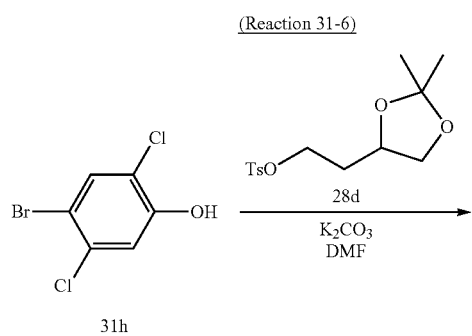

31h

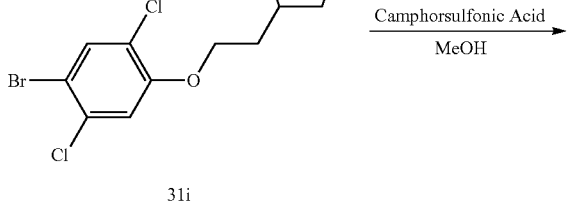

31i → 31j 4-(4-Bromo-2,5-dichloro-phenoxy)-butane-1,2-diol was synthesized by operations similar to those in Reaction 26-4 and Reaction 31-6 using appropriate reagents and starting material.

MS (ESI) m/z=351, 353 (M+H)+.

The aryl bromide reagent used in the synthesis of Compound 235 ([3-(4-bromo-3-methyl-phenoxy)-propyl]-dimethyl-amine) was synthesized as follows.

(Reaction 31-7)

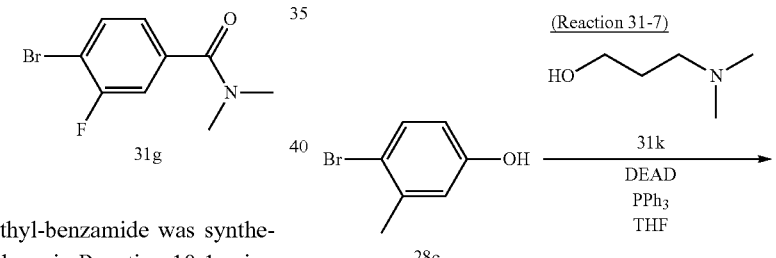

28c → 31l

3-Dimethylamino-propan-1-ol (251 µL, 2.14 mmol) and DEAD (973 µL, 2.14 mmol) were added to a solution of 4-bromo-3-methyl-phenol (200 mg, 1.07 mmol) and PPh$_3$ (561 mg, 2.14 mmol) in THF (10 mL) at 0° C. The mixture was stirred for two hours and then concentrated under reduced pressure. The resulting residue was purified by silica gel column chromatography to give [3-(4-bromo-3-methyl-phenoxy)-propyl]-dimethyl-amine (176 mg, 61%).

MS (ESI) m/z=273, 275 (M+H)+.

The aryl bromide reagent used in the synthesis of Compound 236 (N-(3-bromo-2-methyl-phenyl)-N-methyl-acetamide) was synthesized as follows.

327

(Reaction 31-8)

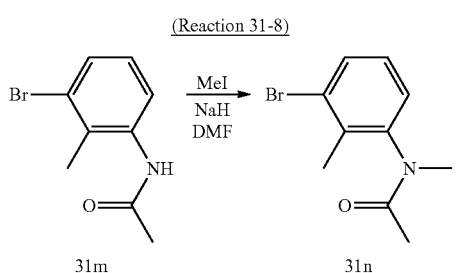

N-(3-Bromo-2-methyl-phenyl)-N-methyl-acetamide was synthesized by operations similar to those in Reaction 25-3 using appropriate reagents and starting material.

MS (ESI) m/z=242, 244 (M+H)+.

The aryl bromide reagent used in the synthesis of Compound 237 (N-(4-bromo-3-methyl-phenyl)-N-methyl-acetamide) was synthesized as follows.

(Reaction 31-9)

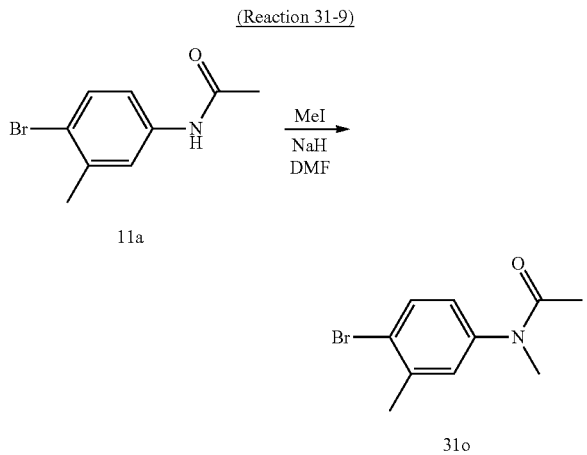

N-(4-Bromo-3-methyl-phenyl)-N-methyl-acetamide was synthesized by operations similar to those in Reaction 25-3 using appropriate reagents and starting material.

MS (ESI) m/z=264, 266 (M+H)+.

The aryl bromide reagent used in the synthesis of Compound 239 (N-(4-bromo-3,5-dimethyl-phenyl)-N-methylacetamide) was synthesized as follows.

(Reaction 31-10)

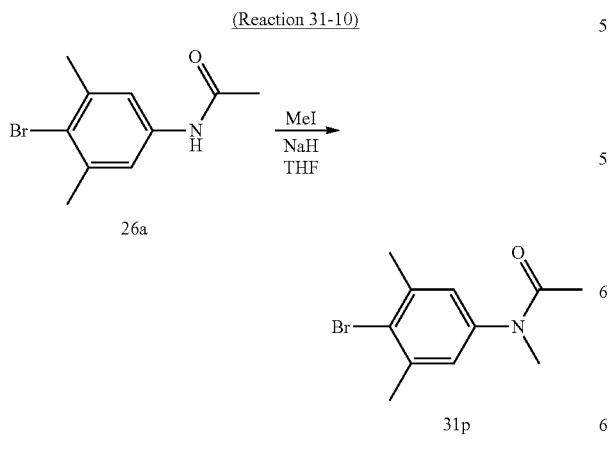

328

N-(4-Bromo-3,5-dimethyl-phenyl)-N-methyl-acetamide was synthesized by operations similar to those in Reaction 25-3 using appropriate reagents and starting material.

MS (ESI) m/z=256, 258 (M+H)+.

Example 32

2-Cycloheptyl-8-{(E)-2-[1-((S)-2,3-dihydroxy-propyl)-1H-indol-4-yl]-ethenesulfonyl}-1,3,8-triazaspiro[4.5]dec-1-en-4-one (Compound 240)

(Reaction 32-1)

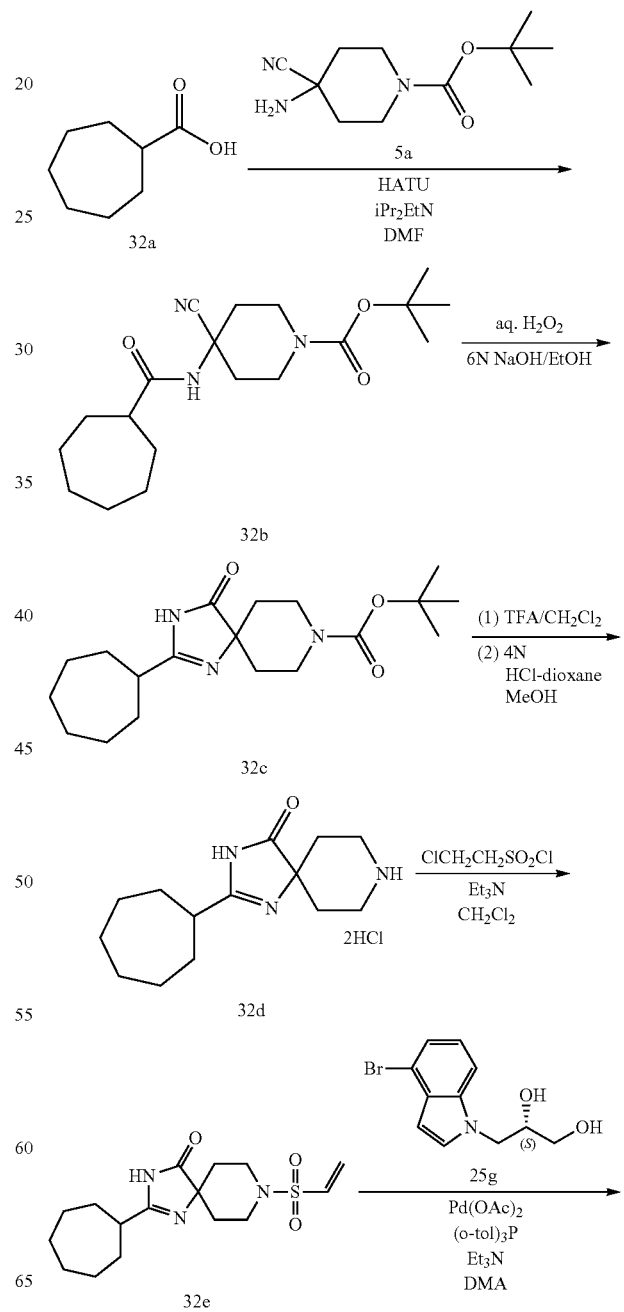

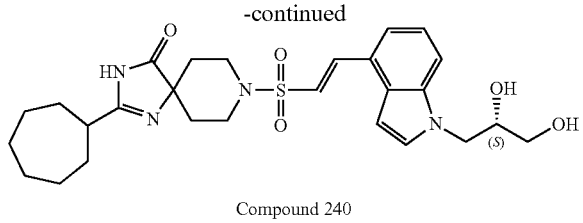

Compound 240

2-Cycloheptyl-8-{(E)-2-[1-((S)-2,3-dihydroxy-propyl)-1H-indol-4-yl]-ethenesulfonyl}-1,3,8-triaza-spiro[4.5]dec-1-en-4-one was synthesized by operations similar to those in Reaction 10-14, Reaction 1-4, Reaction 11-4, Reaction 25-1 and Reaction 25-2 using appropriate reagents and starting material.

MS (ESI) m/z=529 (M+H)+.

The example compound shown below was synthesized by operations similar to those in Example 32 using appropriate reagents and starting material.

Compound 241

TABLE 38

| Compound | Structure | LCMS or HPLC condition | Retention time (min) | MS (m/z) |
|---|---|---|---|---|
| 241 | 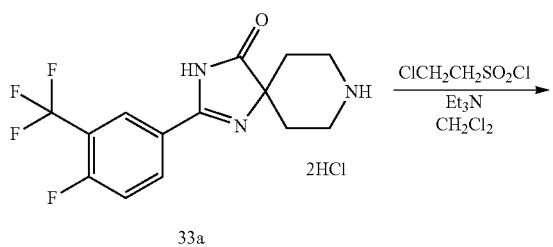 | LCMS-A-1 | 1.90 | 551 (M + H)+ |

Example 33

8-{(E)-2-[4-((R)-2,3-Dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one (Compound 242)

(Reaction 33-1)

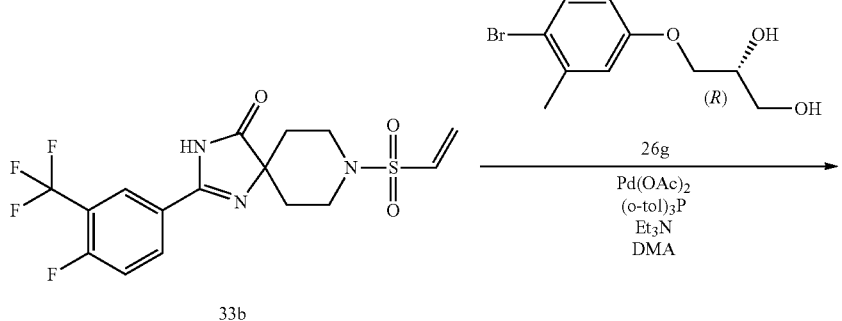

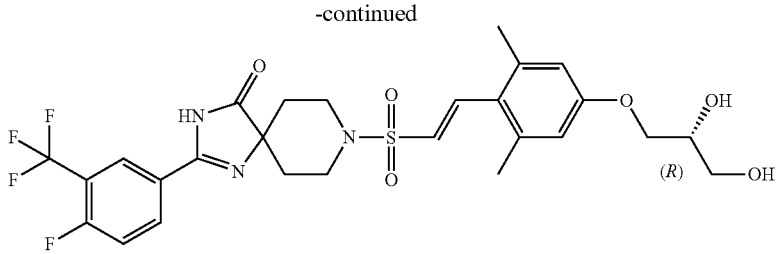

Compound 242

8-{(E)-2-[4-((R)-2,3-Dihydroxy-propoxy)-2,6-dimethyl-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 25-1 and Reaction 25-2 using appropriate reagents and starting material.
MS (ESI) m/z=600 (M+H)+.

The example compounds shown below were synthesized by operations similar to those in Example 33 using appropriate reagents and starting materials.

Compounds 243 to 246

TABLE 39

| Compound | Structure | LCMS or HPLC condition | Retention time (min) | MS (m/z) |
|---|---|---|---|---|
| 243 | 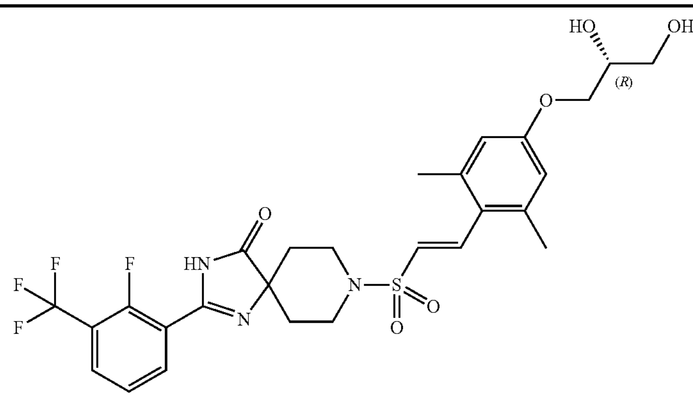 | LCMS-A-1 | 2.36 | 600 (M + H)+ |
| 244 | 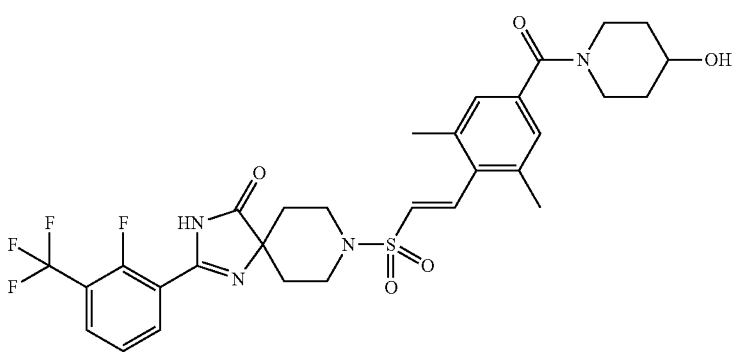 [SMILES: Cc1cc(C(=O)N2CCC(O)CC2)cc(C)c1/C=C/S(=O)(=O)N1CCC2(CC1)N=C(c1cccc(C(F)(F)F)c1F)NC2=O] | LCMS-C-1 | 2.52 | 637 (M + H)+ |
| 245 | 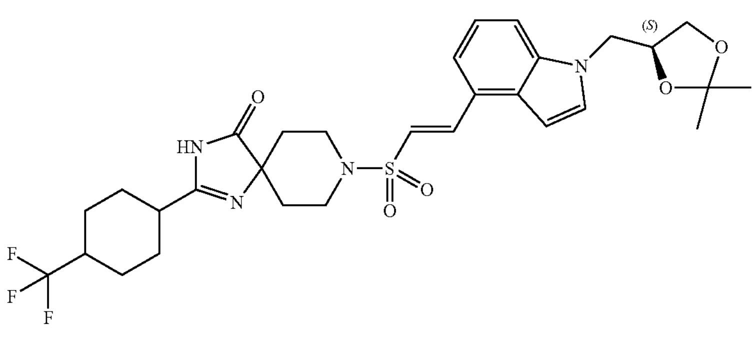 | LCMS-A-1 | 2.92 | 562 (M + H)+ |

TABLE 39-continued

| Compound | Structure | LCMS or HPLC condition | Retention time (min) | MS (m/z) |
|---|---|---|---|---|
| 246 | 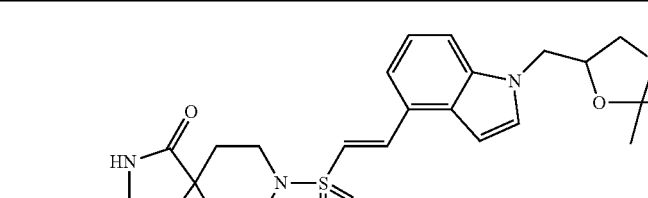 | LCMS-E-4 | 2.82 | 557 (M + H)+ |

The aryl bromide reagent used in the synthesis of Compound 244 ((4-bromo-3,5-dimethyl-phenyl)-(4-hydroxy-piperidin-1-yl)-methanone) was synthesized as follows.

(Reaction 33-2)

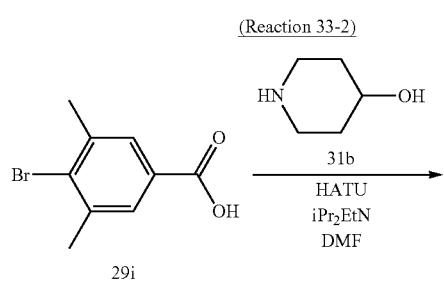

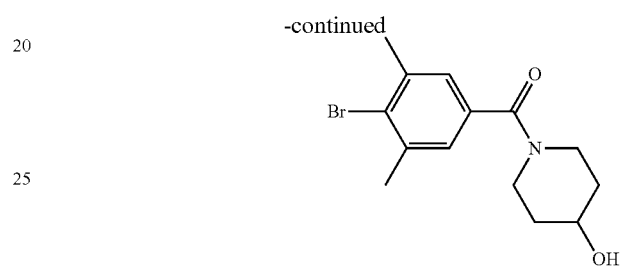

(4-Bromo-3,5-dimethyl-phenyl)-(4-hydroxy-piperidin-1-yl)-methanone was synthesized by operations similar to those in Reaction 10-14 using appropriate reagents and starting material.
MS (ESI) m/z=312, 314 (M+H)+.

Example 34

8-{(E)-2-[4-(3,4-Dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one (Compound 247)

(Reaction 34-1)

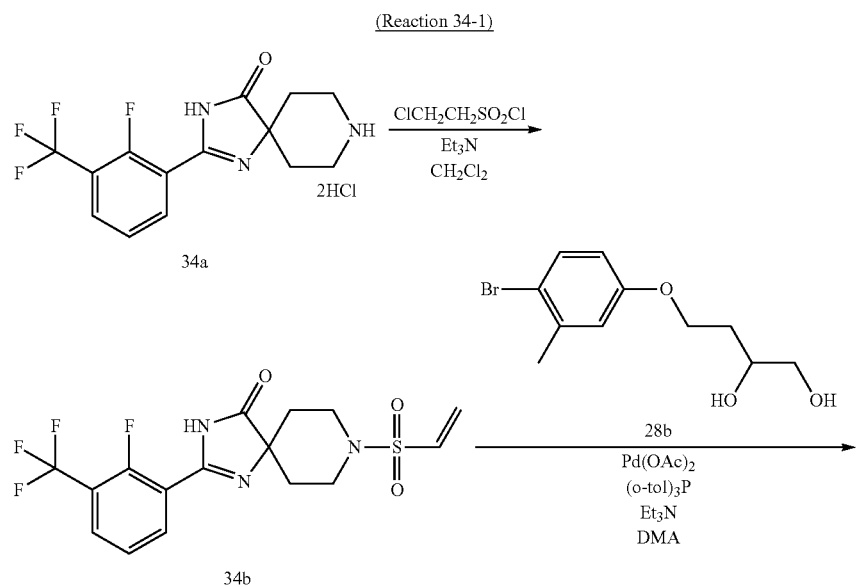

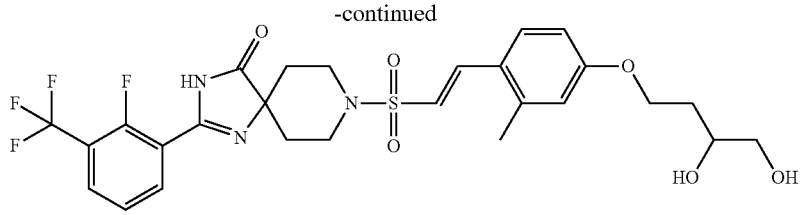

Compound 247

8-{(E)-2-[4-(3,4-Dihydroxy-butoxy)-2-methyl-phenyl]-ethenesulfonyl}-2-(2-fluoro-3-trifluoromethyl-phenyl)-1,3,8-triaza-spiro[4.5]dec-1-en-4-one was synthesized by operations similar to those in Reaction 25-1 and Reaction 26-1 using appropriate reagents and starting material.

MS (ESI) m/z=600 (M+H)+.

The example compounds shown below were synthesized by operations similar to those in Example 34 using appropriate reagents and starting materials.

Compounds 248 to 250

TABLE 40

| Compound | Structure | LCMS or HPLC condition | Retention time (min) | MS (m/z) |
|---|---|---|---|---|
| 248 | 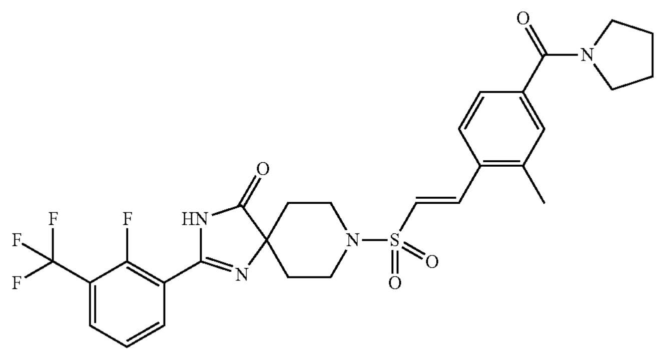 [SMILES: Cc1cc(C(=O)N2CCCC2)ccc1/C=C/S(=O)(=O)N1CCC2(CC1)N=C(c1cccc(C(F)(F)F)c1F)NC2=O] | LCMS-C-1 | 2.62 | 593 (M + H)+ |
| 249 | 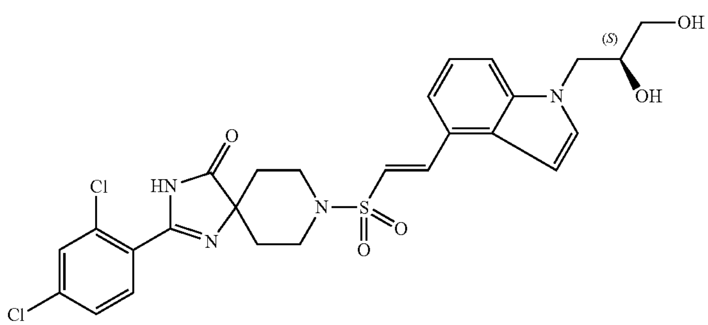 | LCMS-B-1 | 1.96 | 577 (M + H)+ |
| 250 | 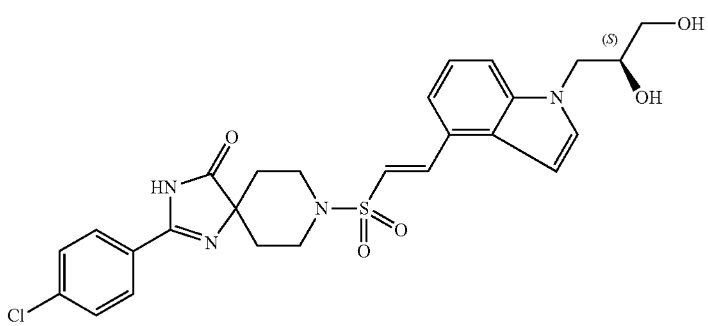 | LCMS-B-1 | 1.85 | 543 (M + H)+ |

Example 35

2-Cyclohexyl-8-[(E)-4-(1H-indol-4-yl)-but-3-ene-1-sulfonyl]-1,3,8-triaza-spiro[4.5]dec-1-en-4-one (Compound 251)

Example 36

2-Cyclohexyl-8-[(E)-5-(1H-indol-4-yl)-pent-4-ene-1-sulfonyl]-1,3,8-triaza-spiro[4.5]dec-1-en-4-one (Compound 252)

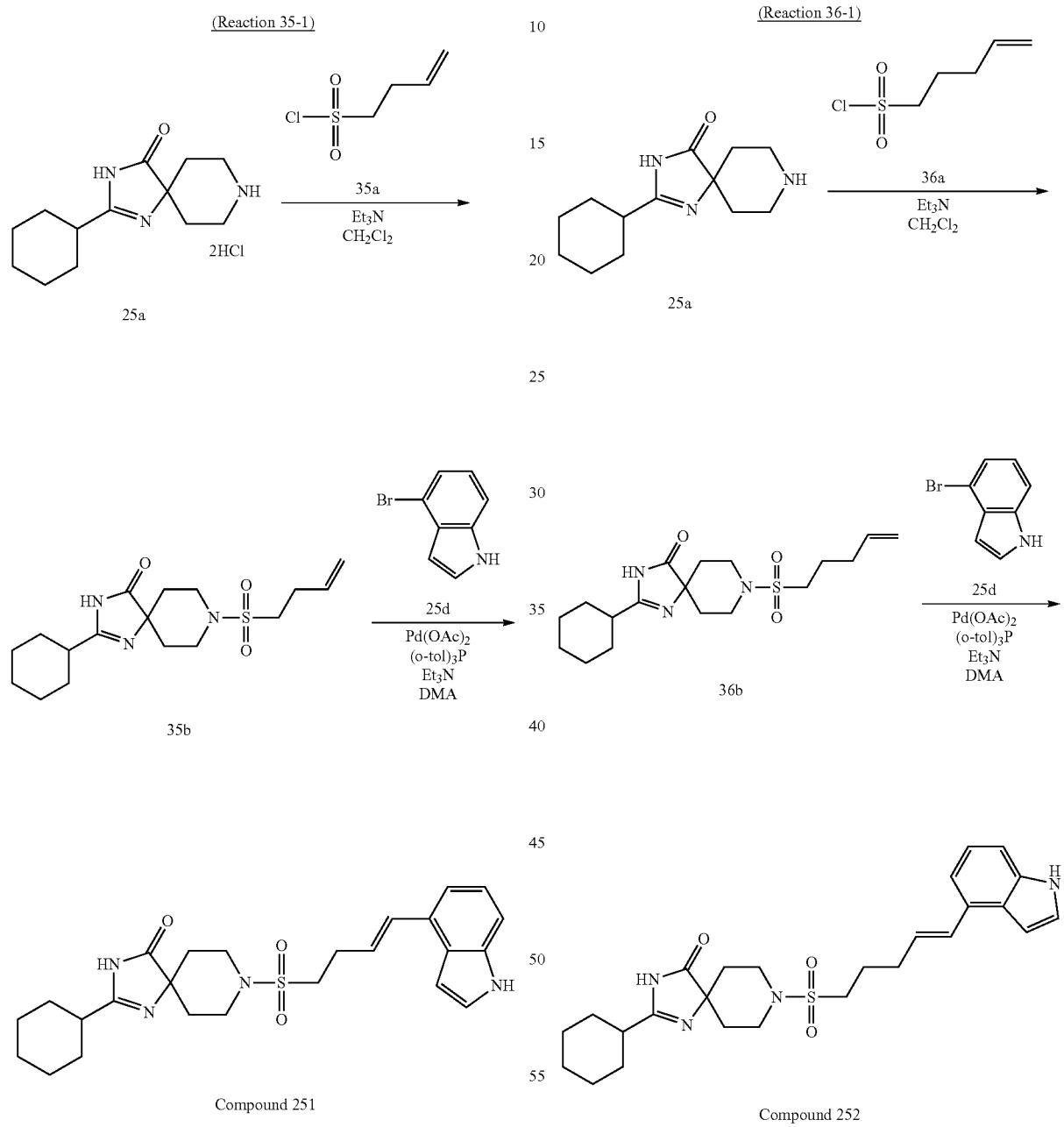

2-Cyclohexyl-8-[(E)-4-(1H-indol-4-yl)-but-3-ene-1-sulfonyl]-1,3,8-triaza-spiro[4.5]dec-1-en-4-one was synthesized by operations similar to those in Reaction 25-1 and Reaction 25-2 using appropriate reagents and starting material.

MS (ESI) m/z=469 (M+H)+.

2-Cyclohexyl-8-[(E)-5-(1H-indol-4-yl)-pent-4-ene-1-sulfonyl]-1,3,8-triaza-spiro[4.5]dec-1-en-4-one was synthesized by operations similar to those in Reaction 25-1 and Reaction 25-2 using appropriate reagents and starting material.

MS (ESI) m/z=483 (M+H)+.

Example 37
2-Cyclohexyl-8-{(E)-3-[1-((S)-2,3-dihydroxy-propyl)-1H-indol-4-yl]-prop-2-ene-1-sulfonyl}-1,3,8-triaza-spiro[4.5]dec-1-en-4-one (Compound 253)
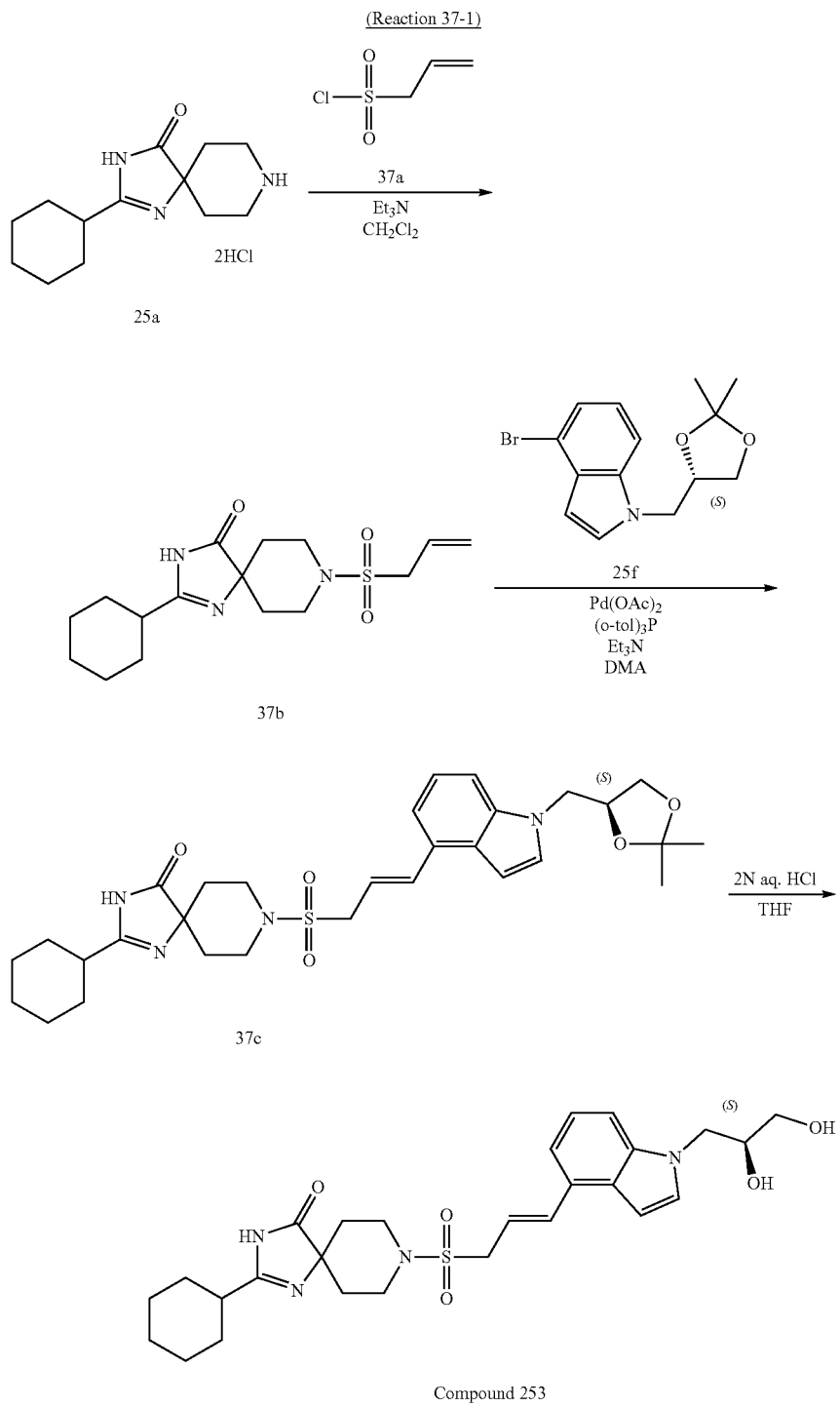
2-Cyclohexyl-8-{(E)-3-[1-((S)-2,3-dihydroxy-propyl)-1H-indol-4-yl]-prop-2-ene-1-sulfonyl}-1,3,8-triaza-spiro[4.5]dec-1-en-4-one was synthesized by operations similar to those in Reaction 25-1, Reaction 25-2 and Reaction 25-4 using appropriate reagents and starting material.
MS (ESI) m/z=529 (M+H)+.

Example 38

8-{(E)-2-[3-(3,4-Dihydroxy-butoxy)-2-methyl-phenyl]-ethenesulfonyl}-2-(3-trifluoromethoxy-phenyl)-1,3,8-triaza-spiro[4.5]dec-1-en-4-one (Compound 254)

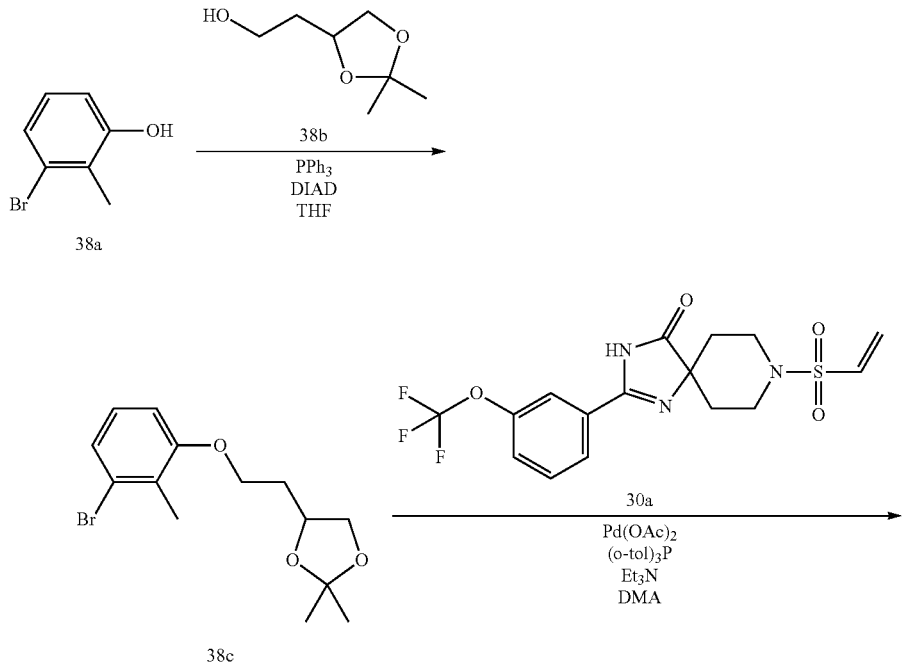

8-{(E)-2-[3-(3,4-Dihydroxy-butoxy)-2-methyl-phenyl]-ethenesulfonyl}-2-(3-trifluoromethoxy-phenyl)-1,3,8-triaza-spiro[4.5]dec-1-en-4-one was synthesized by operations similar to those in Reaction 31-7, Reaction 26-1 and Reaction 25-4 using appropriate reagents and starting material.

$^1$H-NMR (300 MHz, CDCl$_3$) δ 1.7 (2H, d, J=13.73 Hz), 1.97 (1H, brs), 2.00 (2H, m), 2.18 (2H, dt, J=3.05, 13.73 Hz), 2.30 (3H, s), 2.51 (1H, brs), 3.35 (2H, dt, J=3.05, 11.83 Hz), 3.59 (1H, m), 3.75 (1H, m), 3.80 (2H, d, J=11.83 Hz), 4.06 (1H, brs), 4.18 (2H, m), 6.66 (1H, d, J=15.64 Hz), 6.95 (1H, d, J=7.63 Hz), 7.17 (1H, t, J=7.63 Hz), 7.21 (1H, d, J=7.63 Hz), 7.42 (1H, d, J=8.01 Hz), 7.54 (1H, dd, J=7.63, 8.01 Hz), 7.75 (1H, d, J=7.63 Hz), 7.81 (1H, s), 7.81 (1H, d, J=15.64 Hz), 9.75 (1H, s). MS (ESI) m/z=598 (M+H)+.

The example compound shown below was synthesized by operations similar to those in Example 38 using appropriate reagents and starting material.

Compound 255

TABLE 41

| Compound | Structure | LCMS or HPLC condition | Retention time (min) | MS (m/z) |
|---|---|---|---|---|
| 255 | 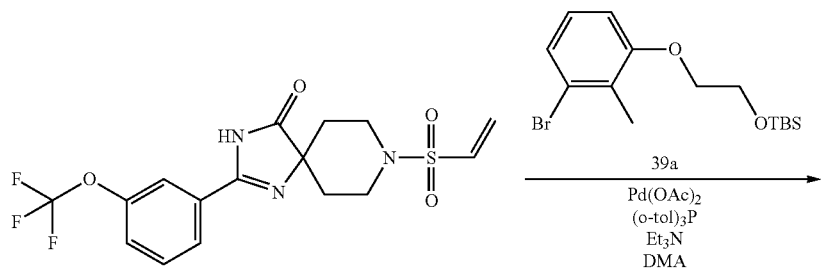 | HPLC-A-3 | 11.56 | 598 (M + H)+ |

Example 39

8-{(E)-2-[3-(2-Hydroxy-ethoxy)-2-methyl-phenyl]-ethenesulfonyl}-2-(3-trifluoromethoxy-phenyl)-1,3,8-triaza-spiro[4.5]dec-1-en-4-one (Compound 256)

(Reaction 39-1)

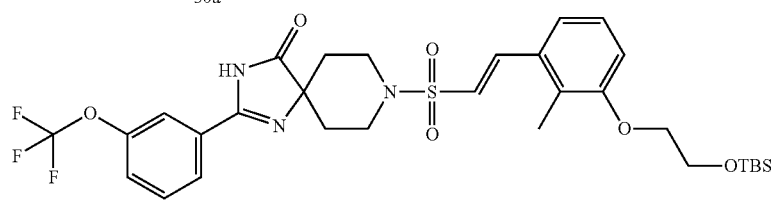

8-((E)-2-{3-[2-(tert-Butyl-dimethyl-silanyloxy)-ethoxy]-2-methyl-phenyl}-ethenesulfonyl)-2-(3-trifluoromethoxy-phenyl)-1,3,8-triaza-spiro[4.5]dec-1-en-4-one was synthesized by operations similar to those in Reaction 26-1 using appropriate reagents and starting material. This compound was used as such in the next step without purification.

(Reaction 39-2)

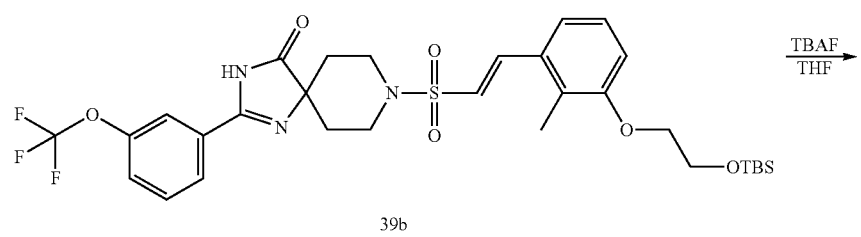

-continued

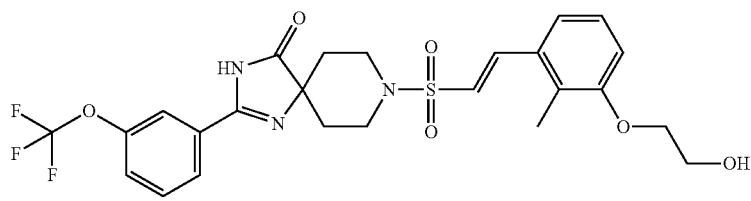

Compound 256

Tetrabutylammonium fluoride (0.11 ml, 0.11 mmol, 1 M in THF) was added to a solution of 8-((E)-2-{3-[2-(tert-Butyl-dimethyl-silanyloxy)-ethoxy]-2-methyl-phenyl}-ethenesulfonyl)-2-(3-trifluoromethoxy-phenyl)-1,3,8-triaza-spiro[4.5]dec-1-en-4-one obtained above in anhydrous THF (1 ml) at room temperature in an Ar atmosphere. The mixture was stirred at room temperature for two hours and then concentrated under reduced pressure. The resulting residue was purified by silica gel column chromatography (hexane:EtOAc=1:1) to give 8-{(E)-2-[3-(2-hydroxy-ethoxy)-2-methyl-phenyl]-ethenesulfonyl}-2-(3-trifluoromethoxy-phenyl)-1,3,8-triaza-spiro[4.5]dec-1-en-4-one (3.2 mg, yield in two steps: 48%).

$^1$H-NMR (300 MHz, DMSO-d6) δ 11.75 (1H, s), 7.99 (1H, d, J=7.5 Hz), 7.90 (1H, s), 7.63 (3H, m), 7.37 (1H, d, J=7.5 Hz), 7.23 (2H, m), 7.06 (1H, d, J=7.9 Hz), 4.85 (1H, t, J=5.6 Hz), 4.00 (2H, m), 3.74 (2H, m), 3.60 (2H, m), 3.20 (2H, m), 2.27 (3H, s), 1.88 (2H, m), 1.63 (2H, m). MS (ESI+) m/z=554 (M+H)+.

The example compounds shown below were synthesized by operations similar to those in Example 39 using appropriate reagents and starting materials.

Compounds 257 to 258

TABLE 42

| Compound | Structure | LCMS or HPLC condition | Retention time (min) | MS (m/z) |
|---|---|---|---|---|
| 257 | 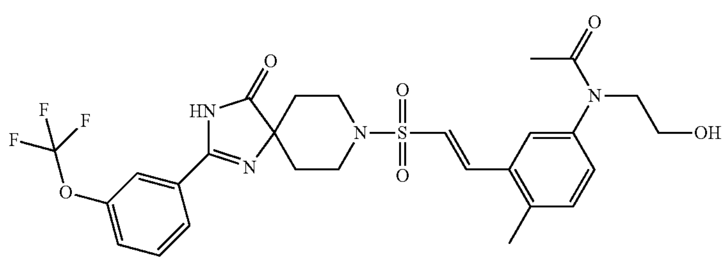 [SMILES: CC(=O)N(CCO)c1ccc(C)c(/C=C/S(=O)(=O)N2CCC3(CC2)N=C(c2cccc(OC(F)(F)F)c2)NC3=O)c1] | LCMS-D-1 | 3.1 | 595 (M + H)+ |
| 258 | 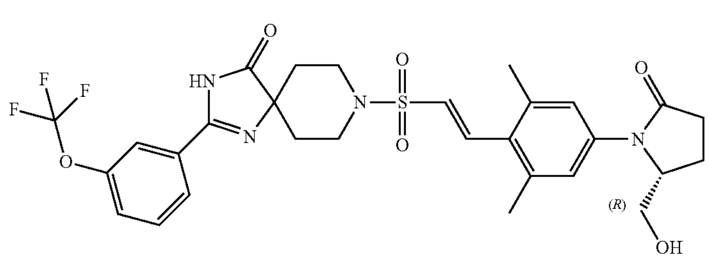 | LCMS-D-1 | 3.10 | 621 (M + H)+ |

The aryl bromide reagent used in the synthesis of Compound 257 (N-(3-bromo-4-methyl-phenyl)-N-[2-(tert-butyl-dimethyl-silanyloxy)-ethyl]-acetamide) was synthesized as follows.

(Reaction 39-3)

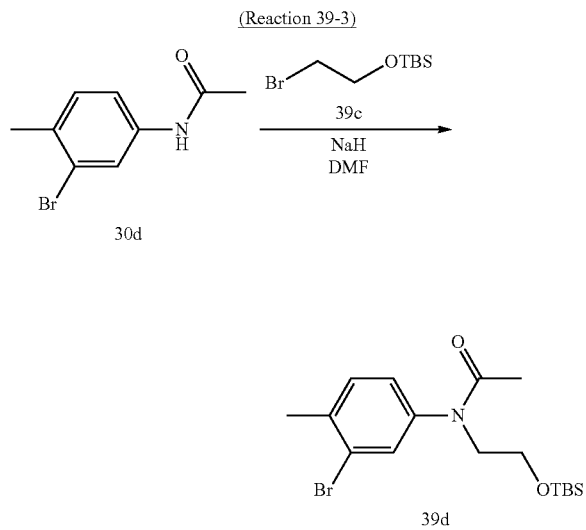

N-(3-Bromo-4-methyl-phenyl)-N-[2-(tert-butyl-dimethyl-silanyloxy)-ethyl]-acetamide was synthesized by operations similar to those in Reaction 25-3 using appropriate reagents and starting material.

MS (ESI) m/z=386, 388 (M+H)+.

The aryl bromide reagent used in the synthesis of Compound 258 ((R)-1-(4-bromo-3,5-dimethyl-phenyl)-5-(tert-butyl-dimethyl-silanyloxymethyl)-pyrrolidin-2-one) was synthesized as follows.

(Reaction 39-4)

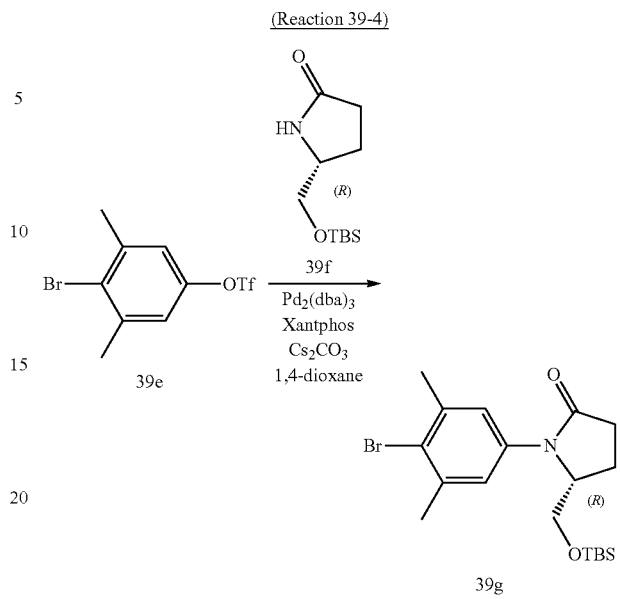

(R)-1-(4-Bromo-3,5-dimethyl-phenyl)-5-(tert-butyl-dimethyl-silanyloxymethyl)-pyrrolidin-2-one was synthesized by operations similar to those in Reaction 29-3 using appropriate reagents and starting material.

$^1$H-NMR (300 MHz, CDCl$_3$) δ −0.06 (3H, s), −0.03 (3H, s), 0.86 (9H, s), 2.10 (1H, m), 2.26 (1H, m), 2.40 (6H, s), 2.48 (1H, ddd, J=4.6, 10.3, 16.8 Hz), 2.68 (1H, ddd, J=8.0, 9.9, 17.9 Hz), 3.56 (2H, dq, J=3.8, 10.7 Hz), 4.15 (1H, m), 7.10 (2H, s).

Example 40

N-(4-{(E)-2-[2-(2-Fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide (Compound 259)

(Reaction 40-1)

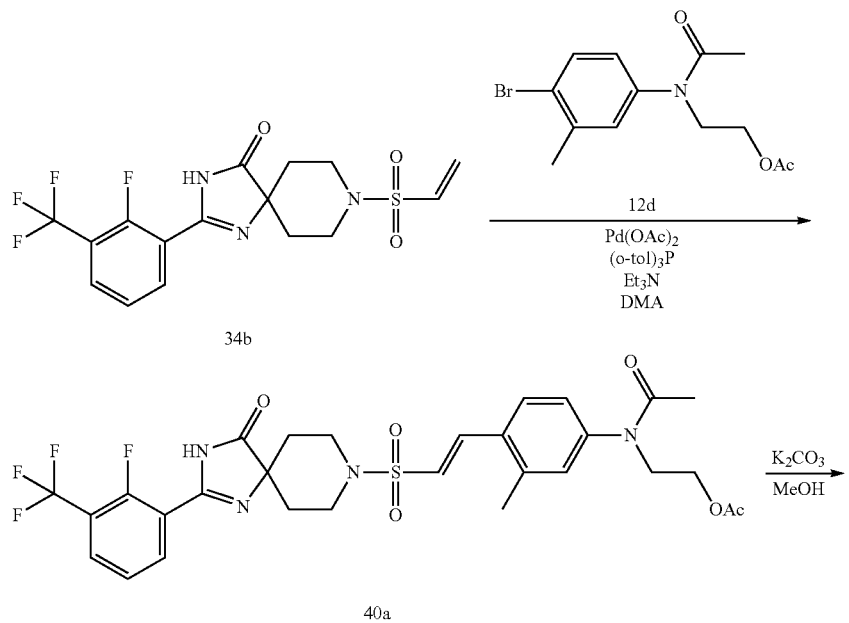

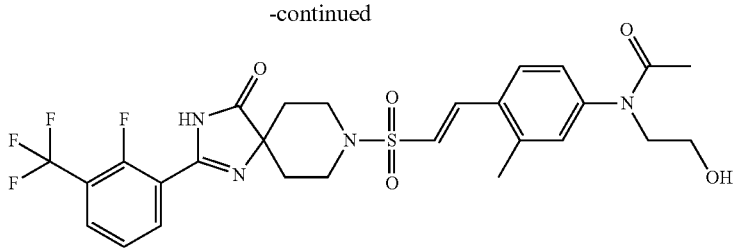

Compound 259

N-(4-{(E)-2-[2-(2-Fluoro-3-trifluoromethyl-phenyl)-4-oxo-1,3,8-triaza-spiro[4.5]dec-1-ene-8-sulfonyl]-vinyl}-3-methyl-phenyl)-N-(2-hydroxy-ethyl)-acetamide was synthesized by operations similar to those in Reaction 26-1 and Reaction 12-5 using appropriate reagents and starting material.

MS (ESI) m/z=597 (M+H)+.

Example 41

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide (Compound 260)

temperature for 3.5 hours and then quenched with a saturated aqueous sodium carbonate solution. The reaction mixture was extracted with dichloromethane, and the organic layer was then concentrated under reduced pressure to 4-(4-bromo-3-methyl-phenylamino)-piperidine-1-carboxylic acid tert-butyl ester as a white solid (586 mg, 100%). This compound was used in the next step without further purification.

$^1$H-NMR (400 MHz, CDCl$_3$) δ 1.32 (m, 2H), 1.42 (s, 9H), 2.01 (d, J=13.2 Hz, 2H), 2.31 (s, 3H), 2.92 (t, J=11.6 Hz, 2H), 3.45 (br, 2H), 4.04 (br, 1H), 6.32 (dd, J=2.4 Hz, 8.4 Hz, 1H), 6.48 (d, J=2.8 Hz, 1H), 7.28 (m, 1H). MS (ESI) m/z=369 (M+H)+.

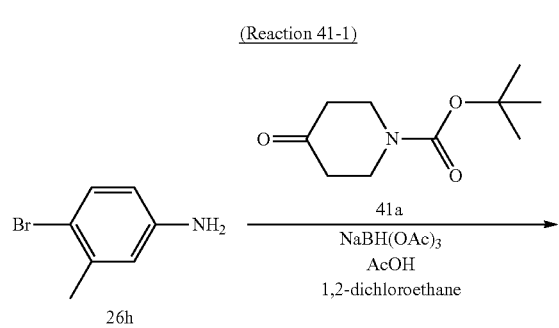

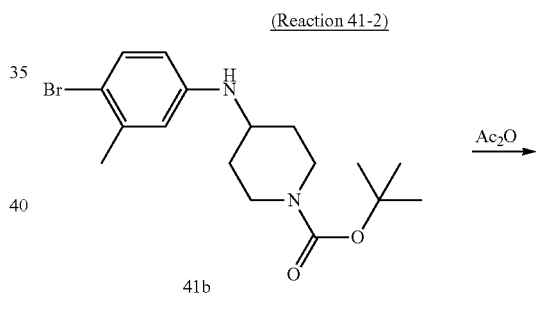

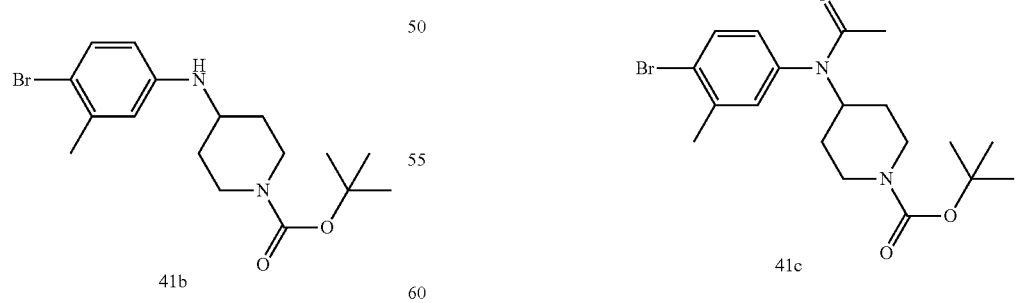

Acetic acid (4.9 eq) and sodium triacetoxyborohydride (2.0 eq) were sequentially added to a solution of 4-bromo-3-methylaniline (246 mg, 1.32 mmol) and 1-(tert-butoxycarbonyl)-4-piperidone (350 mg, 1.76 mmol) in 1,2-dichloroethane (10 ml). The mixture was stirred at room 4-[Acetyl-(4-bromo-3-methyl-phenyl)-amino]-piperidine-1-carboxylic acid tert-butyl ester was synthesized by operations similar to those in Reaction 12-2 using the compound obtained above as a starting material.

MS (ESI) m/z=411, 413 (M+H)+.

(Reaction 41-3)

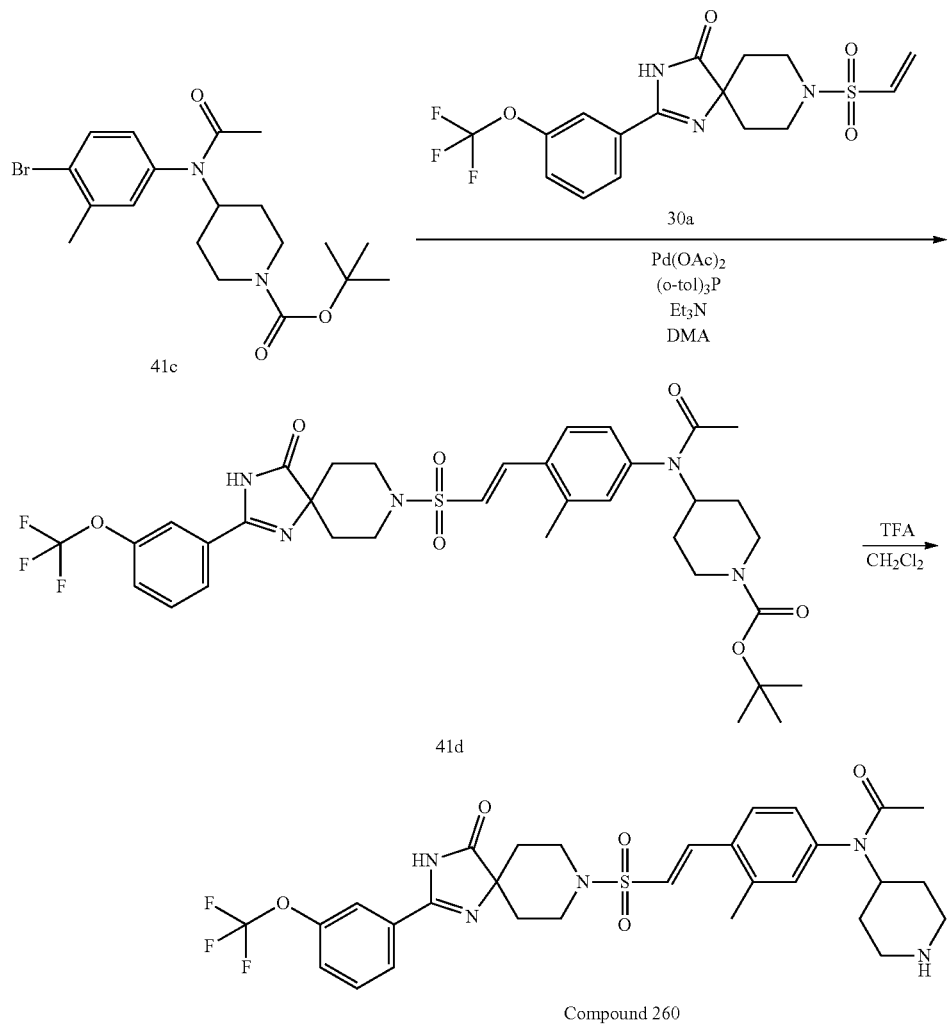

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-acetamide was synthesized by operations similar to those in Reaction 26-1 and Reaction 4-1 using appropriate reagents and starting material.

MS (ESI) m/z=634 (M+H)+.

Example 42

2-Cyclohexyl-8-[2-(2-oxo-2,3-dihydro-benzoxazol-7-yl)-ethanesulfonyl]-1,3,8-triaza-spiro[4.5]dec-1-en-4-one (Compound 261)

(Reaction 42-1)

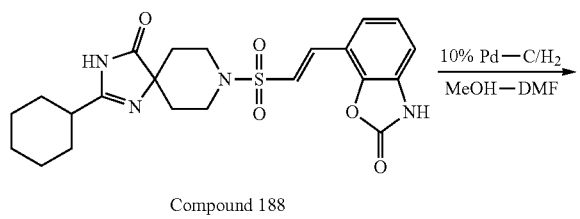

-continued

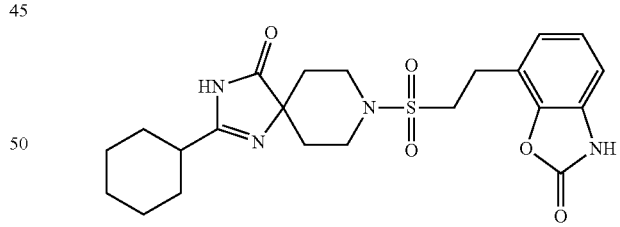

10% Pd—C(28 mg) was added to a solution of 2-cyclohexyl-8-[(E)-2-(2-oxo-2,3-dihydro-benzoxazol-7-yl)-ethenesulfonyl]-1,3,8-triaza-spiro[4.5]dec-1-en-4-one (56.6 mg, 0.123 mmol) in MeOH-DMF (4 ml, 1:1). The mixture was stirred at room temperature overnight in a hydrogen atmosphere. The reaction mixture was filtered through celite, and the filtrate was then concentrated under reduced pressure. The resulting residue was diluted with ethyl acetate, and the organic layer was then washed with water (×2), dried over anhydrous Na₂SO₄ and concentrated under reduced pressure. The residue was purified by column chromatography (silica gel, AcOEt-hexane) to give 2-cyclohexyl-8-[2-(2-oxo-2,3-dihydro-benzoxazol-7-yl)-ethanesulfonyl]-1,3,8-triaza-spiro[4.5]dec-1-en-4-one as a colorless foam (46.9 mg, 83%).

¹H-NMR (400 MHz, CDCl₃) δ 1.21-1.45 (6H, m), 1.50-1.60 (2H, m), 1.65-1.85 (4H, m), 1.90-1.96 (2H, m), 2.38-2.48 (1H, m), 3.25-3.40 (6H, m), 3.65-3.73 (2H, m), 7.01 (2H, d, J=8.0 Hz), 7.13 (1H, t, J=8 Hz), 8.59 (1H, brs), 9.03 (1H, brs). MS (ESI) m/z=461 (M+H)+.

The example compounds shown below were synthesized by operations similar to those in Example 42 using appropriate reagents and starting materials.

Compounds 262 to 267

TABLE 43

| Compound | Structure | LCMS or HPLC condition | Retention time (min) | MS (m/z) |
|---|---|---|---|---|
| 262 | 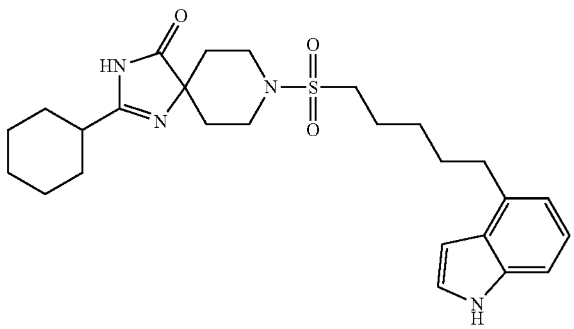 [SMILES: O=C1NC(C2CCCCC2)=NC12CCN(S(=O)(=O)CCCCCc1cccc3[nH]ccc13)CC2] | LCMS-E-5 | 3.3 | 485 (M + H)+ |
| 263 | 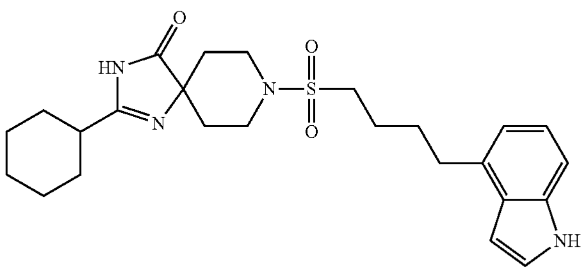 [SMILES: O=C1NC(C2CCCCC2)=NC12CCN(S(=O)(=O)CCCCc1cccc3[nH]ccc13)CC2] | LCMS-E-4 | 2.89 | 471 (M + H)+ |
| 264 | 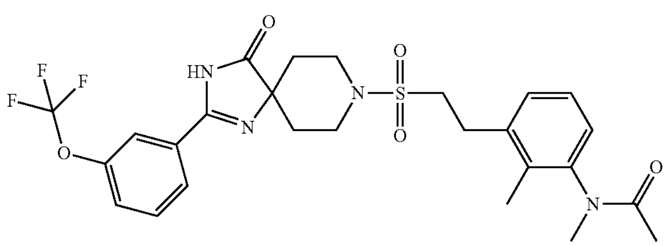 [SMILES: CC(=O)N(C)c1cccc(CCS(=O)(=O)N2CCC3(CC2)N=C(c2cccc(OC(F)(F)F)c2)NC3=O)c1C] | LCMS-D-1 | 3.1 | 567 (M + H)+ |
| 265 | 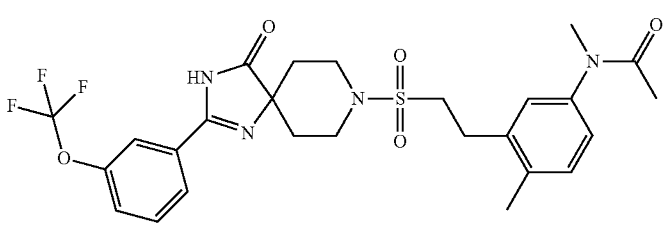 [SMILES: CC(=O)N(C)c1ccc(C)c(CCS(=O)(=O)N2CCC3(CC2)N=C(c2cccc(OC(F)(F)F)c2)NC3=O)c1] | LCMS-D-1 | 3.3 | 567 (M + H)+ |
| 266 | 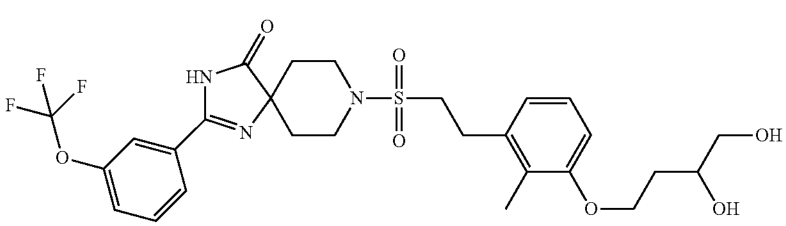 [SMILES: Cc1c(CCS(=O)(=O)N2CCC3(CC2)N=C(c2cccc(OC(F)(F)F)c2)NC3=O)cccc1OCCC(O)CO] | HPLC-A-3 | 11.35 | 600 (M + H)+ |

TABLE 43-continued

| Compound | Structure | LCMS or HPLC condition | Retention time (min) | MS (m/z) |
|---|---|---|---|---|
| 267 | 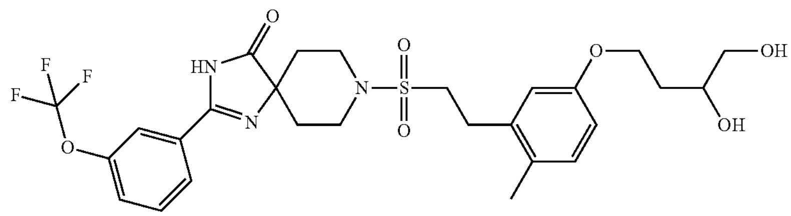 [SMILES: Cc1ccc(OCCC(O)CO)cc1CCS(=O)(=O)N1CCC2(CC1)N=C(c1cccc(OC(F)(F)F)c1)NC2=O] | HPLC-A-3 | 11.03 | 600 (M + H)+ |

Example 43

8-{2-[4-((R)-2-Hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one (Compound 268)

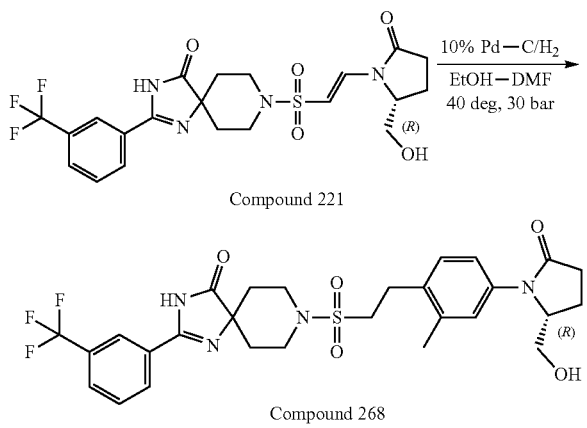

(Reaction 42-2)

Compound 221

Compound 268

The following reaction was performed by utilizing a continuous-flow hydrogenation reactor H-Cube® Type HC-2 (ThalesNano Nanotechnology Inc.).

8-{(E)-2-[4-((R)-2-Hydroxymethyl-5-oxo-pyrrolidin-1-yl)-2-methyl-phenyl]-ethenesulfonyl}-2-(3-trifluoromethyl-phenyl)-1,3,8-triaza-spiro[4.5]dec-1-en-4-one (28.5 mg, 48.3 µmol) was dissolved in EtOH/DMF 4:1 (concentration 10 mg/ml). The mixture was allowed to pass through 10% Pd/C (CatCart™) at a flow rate of 2 ml/min under the conditions of 30 bar and 40° C. in a hydrogen atmosphere, and was subjected to hydrogenation reaction. The resulting reaction solution was concentrated under reduced pressure. The residue was purified by preparative TLC (CH$_2$Cl$_2$/MeOH=20:1) to give 8-{2-[4-((R)-2-hydroxymethyl-5-oxo-pyrrolidin-1-yl)-2-methyl-phenyl]-ethanesulfonyl}-2-(3-trifluoromethyl-phenyl)-1,3,8-triaza-spiro[4.5]dec-1-en-4-one as a white powder (12.9 mg, 45%).

$^1$H-NMR (270 MHz, CDCl$_3$) δ 1.60-1.63 (2H, m), 1.83-1.89 (2H, m), 1.97-2.04 (1H, m), 2.12-2.22 (1H, m), 2.32 (3H, s), 2.28-2.36 (1H, m), 2.52-2.59 (1H, m), 2.97-3.01 (2H, m), 3.29-3.40 (6H, m), 3.67-3.70 (2H, m), 4.24-4.29 (1H, m), 4.80 (1H, t, J=5.4 Hz), 7.22-7.29 (2H, m), 7.79 (1H, br t, J=7.8 Hz), 7.98 (1H, br. d, J=7.8 Hz), 8.29 (1H, br. d, J=7.3 Hz), 8.33 (1H, br. s), 11.81 (1H, br. s). MS (ESI) m/z=593 (M+H)+.

The example compounds shown below were synthesized by operations similar to those in Example 43 using appropriate reagents and starting materials.

Compounds 269 to 302

TABLE 44

| Compound | Structure | LCMS or HPLC condition | Retention time (min) | MS (m/z) |
|---|---|---|---|---|
| 269 | 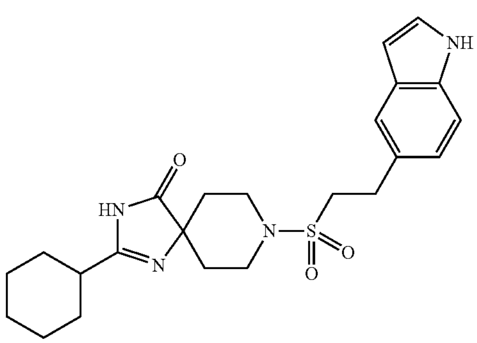 [SMILES: O=C1NC(C2CCCCC2)=NC12CCN(S(=O)(=O)CCc1ccc3[nH]ccc3c1)CC2] | LCMS-A-1 | 2.07 | 443 (M + H)+ |

TABLE 44-continued

| Compound | Structure | LCMS or HPLC condition | Retention time (min) | MS (m/z) |
|---|---|---|---|---|
| 270 | 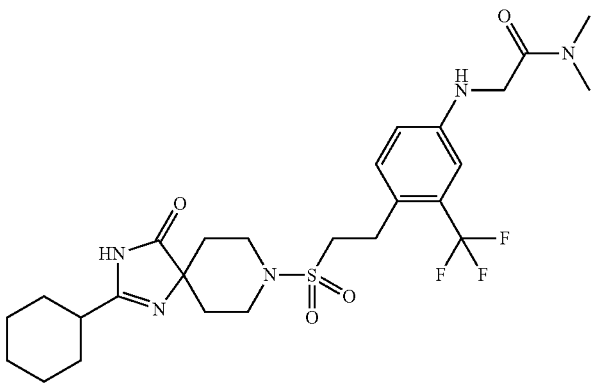 [SMILES: CN(C)C(=O)CNc1ccc(CCS(=O)(=O)N2CCC3(CC2)N=C(C2CCCCC2)NC3=O)c(C(F)(F)F)c1] | LCMS-C-1 | 2.55 | 572 (M + H)+ |
| 271 | 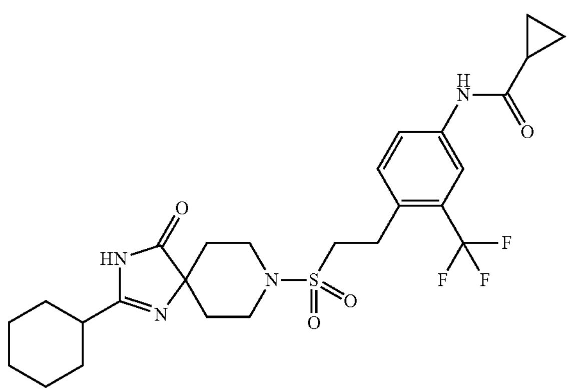 [SMILES: O=C(Nc1ccc(CCS(=O)(=O)N2CCC3(CC2)N=C(C2CCCCC2)NC3=O)c(C(F)(F)F)c1)C1CC1] | LCMS-C-1 | 2.67 | 555 (M + H)+ |
| 272 | 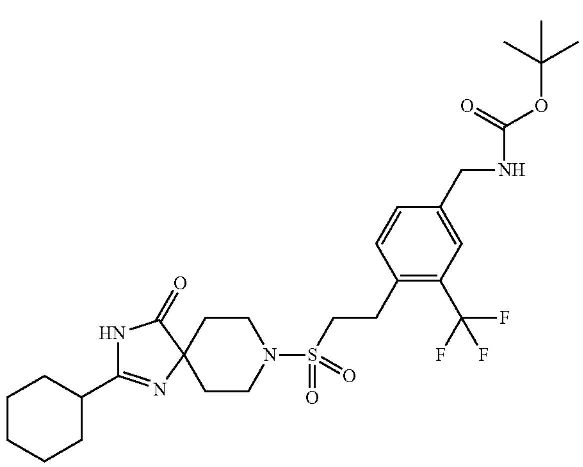 [SMILES: CC(C)(C)OC(=O)NCc1ccc(CCS(=O)(=O)N2CCC3(CC2)N=C(C2CCCCC2)NC3=O)c(C(F)(F)F)c1] | LCMS-C-1 | 2.87 | 601 (M + H)+ |

TABLE 44-continued

| Compound | Structure | LCMS or HPLC condition | Retention time (min) | MS (m/z) |
|---|---|---|---|---|
| 273 | 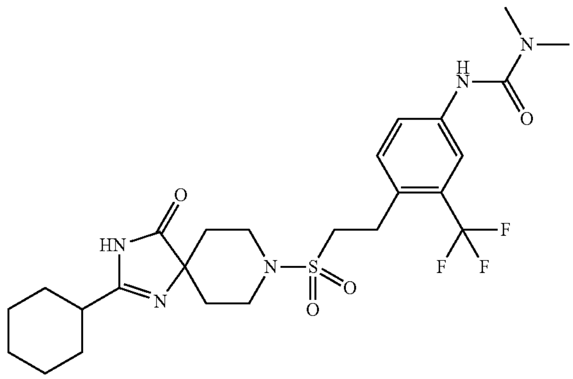 [SMILES: CN(C)C(=O)Nc1ccc(CCS(=O)(=O)N2CCC3(CC2)N=C(C2CCCCC2)NC3=O)c(C(F)(F)F)c1] | LCMS-C-1 | 2.53 | 558 (M + H)+ |
| 274 | 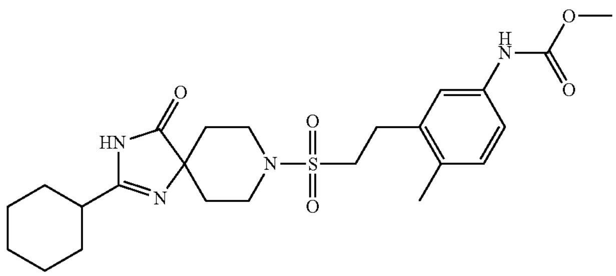 [SMILES: COC(=O)Nc1ccc(C)c(CCS(=O)(=O)N2CCC3(CC2)N=C(C2CCCCC2)NC3=O)c1] | LCMS-C-3 | 1.23 | 491 (M + H)+ |
| 275 | 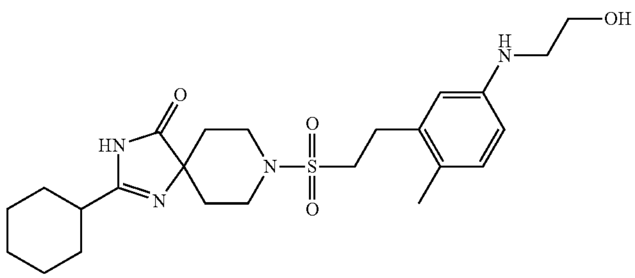 [SMILES: Cc1ccc(NCCO)cc1CCS(=O)(=O)N1CCC2(CC1)N=C(C1CCCCC1)NC2=O] | LCMS-C-3 | 1.06 | 477 (M + H)+ |
| 276 | 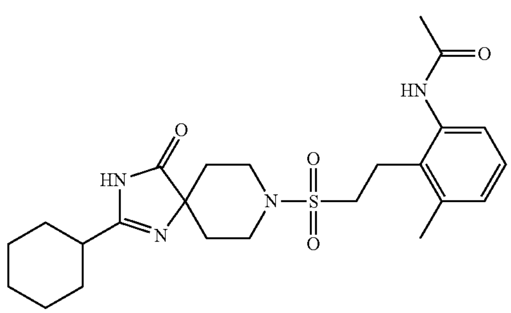 [SMILES: CC(=O)Nc1cccc(C)c1CCS(=O)(=O)N1CCC2(CC1)N=C(C1CCCCC1)NC2=O] | LCMS-C-3 | 0.86 | 475 (M + H)+ |
| 277 | 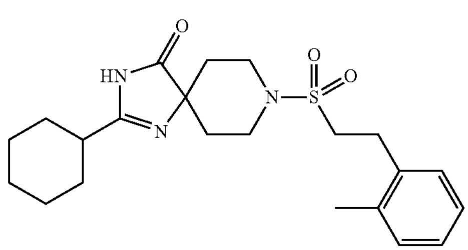 [SMILES: Cc1ccccc1CCS(=O)(=O)N1CCC2(CC1)N=C(C1CCCCC1)NC2=O] | LCMS-C-1 | 2.73 | 418 (M + H)+ |

TABLE 44-continued

| Compound | Structure | LCMS or HPLC condition | Retention time (min) | MS (m/z) |
|---|---|---|---|---|
| 278 | 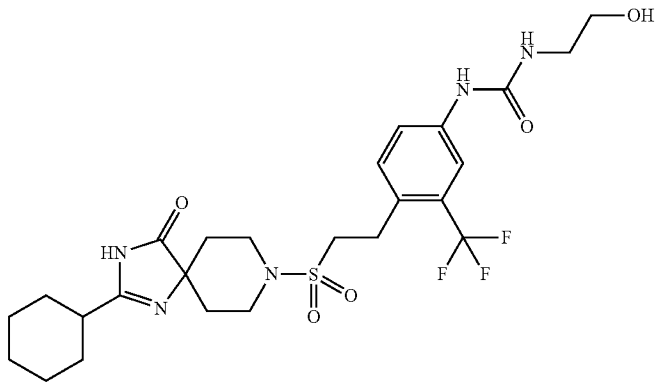 [SMILES: O=C(NCCO)Nc1ccc(CCS(=O)(=O)N2CCC3(CC2)N=C(C2CCCCC2)NC3=O)c(C(F)(F)F)c1] | LCMS-C-1 | 2.42 | 574 (M + H)+ |
| 279 | 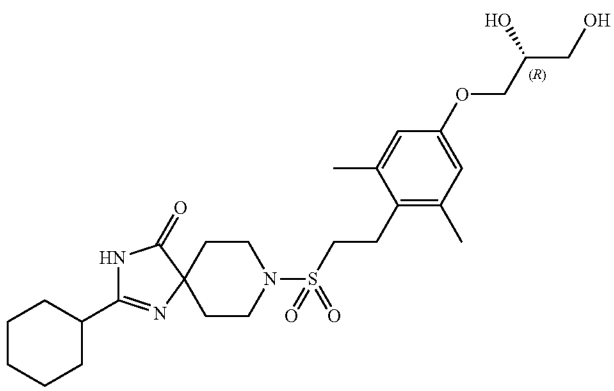 | LCMS-C-1 | 2.37 | 522 (M + H)+ |
| 280 | 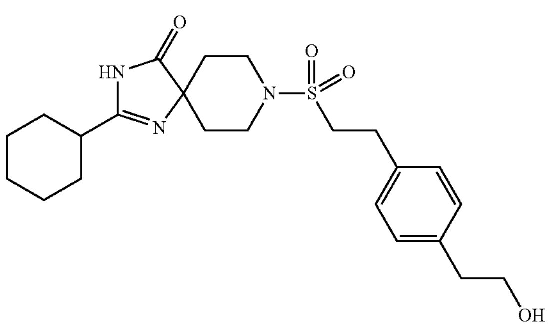 [SMILES: O=C1NC(C2CCCCC2)=NC12CCN(S(=O)(=O)CCc1ccc(CCO)cc1)CC2] | LCMS-C-1 | 2.33 | 448 (M + H)+ |
| 281 | 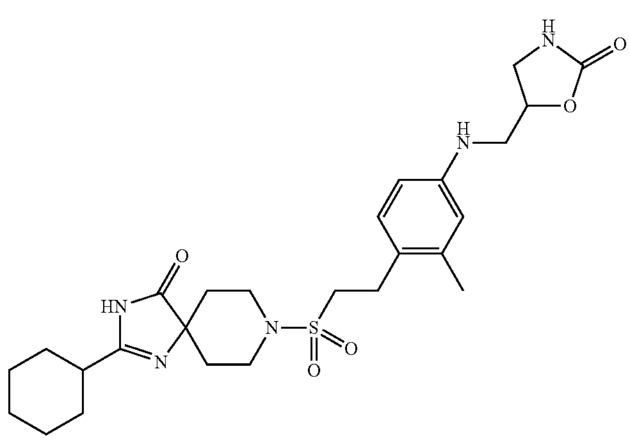 [SMILES: Cc1cc(NCC2CNC(=O)O2)ccc1CCS(=O)(=O)N1CCC2(CC1)N=C(C1CCCCC1)NC2=O] | LCMS-B-1 | 1.45 | 532 (M + H)+ |

TABLE 44-continued
| Compound | Structure | LCMS or HPLC condition | Retention time (min) | MS (m/z) |
|---|---|---|---|---|
| 282 | 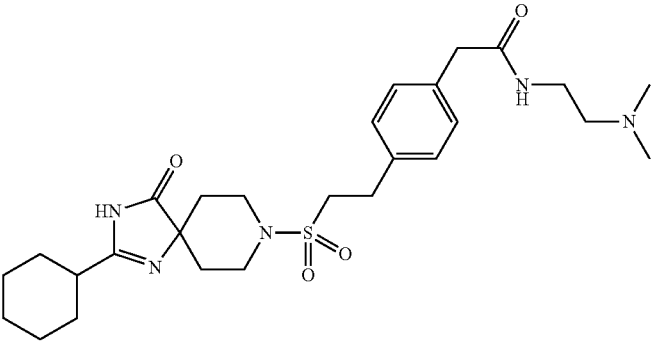 [SMILES: CN(C)CCNC(=O)Cc1ccc(CCS(=O)(=O)N2CCC3(CC2)N=C(C2CCCCC2)NC3=O)cc1] | LCMS-C-1 | 2.12 | 532 (M + H)+ |
| 283 | 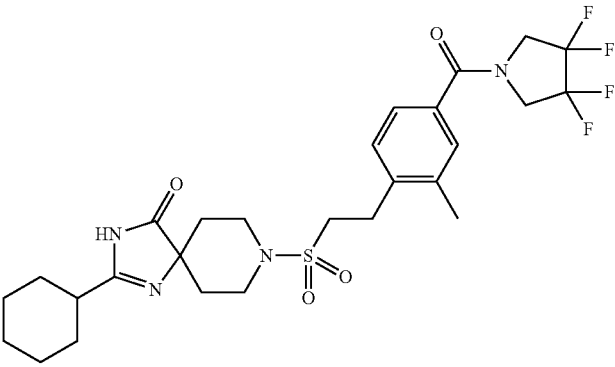 [SMILES: Cc1cc(C(=O)N2CC(F)(F)C(F)(F)C2)ccc1CCS(=O)(=O)N1CCC2(CC1)N=C(C1CCCCC1)NC2=O] | LCMS-C-1 | 2.70 | 587 (M + H)+ |
| 284 | 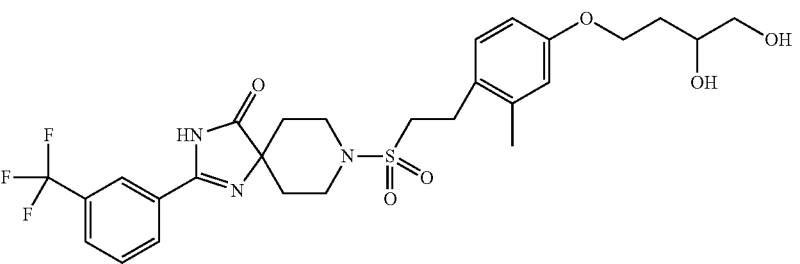 [SMILES: Cc1cc(OCCC(O)CO)ccc1CCS(=O)(=O)N1CCC2(CC1)N=C(c1cccc(C(F)(F)F)c1)NC2=O] | LCMS-C-2 | 1.85 | 584 (M + H)+ |
| 285 | 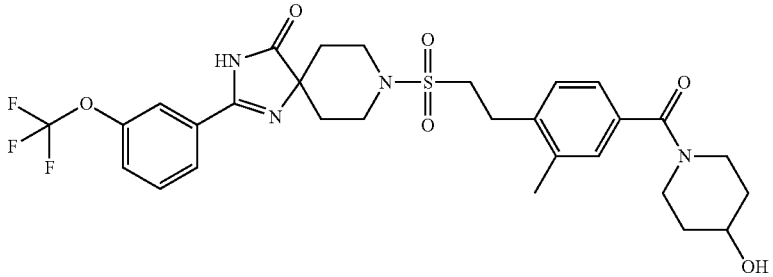 [SMILES: Cc1cc(C(=O)N2CCC(O)CC2)ccc1CCS(=O)(=O)N1CCC2(CC1)N=C(c1cccc(OC(F)(F)F)c1)NC2=O] | LCMS-A-1 | 2.23 | 623 (M + H)+ |
| 286 | 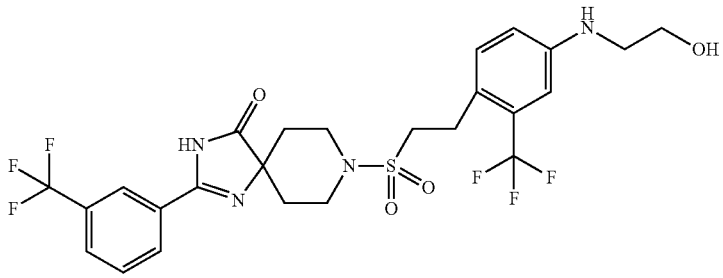 [SMILES: O=C1NC(c2cccc(C(F)(F)F)c2)=NC12CCN(S(=O)(=O)CCc1ccc(NCCO)cc1C(F)(F)F)CC2] | LCMS-C-2 | 2.03 | 593 (M + H)+ |

TABLE 44-continued
| Compound | Structure | LCMS or HPLC condition | Retention time (min) | MS (m/z) |
|---|---|---|---|---|
| 287 | 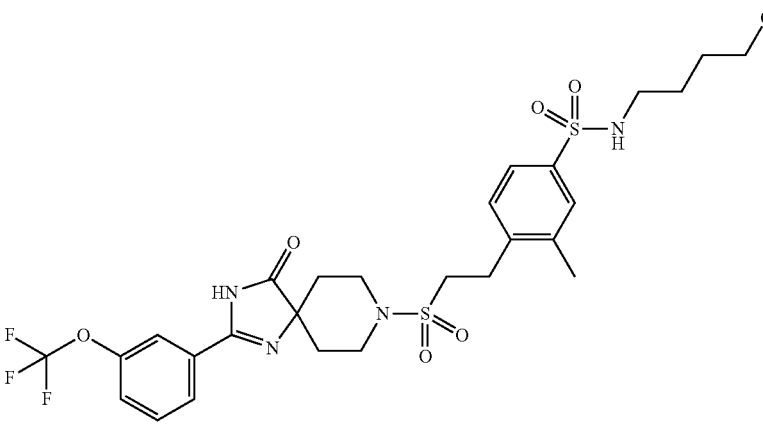 | LCMS-B-1 | 2.10 | 647 (M + H)+ |
| 288 | 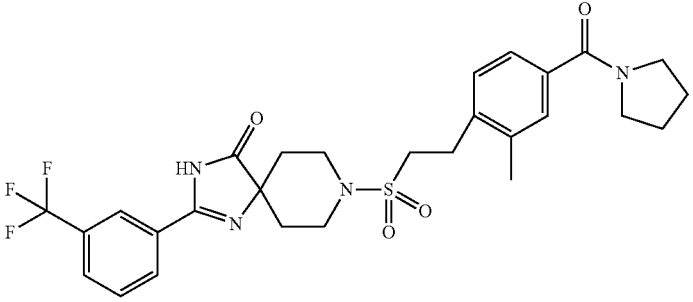 [SMILES: Cc1cc(C(=O)N2CCCC2)ccc1CCS(=O)(=O)N1CCC2(CC1)N=C(c1cccc(C(F)(F)F)c1)NC2=O] | LCMS-C-1 | 2.67 | 577 (M + H)+ |
| 289 | 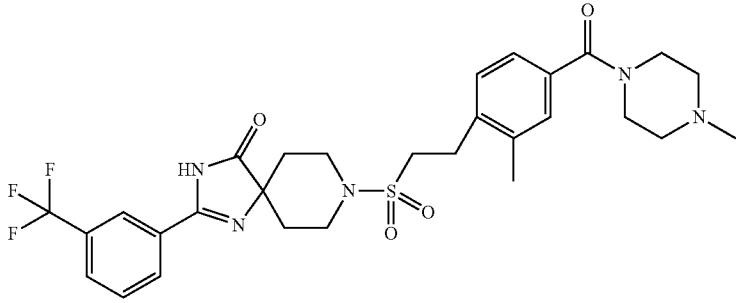 [SMILES: Cc1cc(C(=O)N2CCN(C)CC2)ccc1CCS(=O)(=O)N1CCC2(CC1)N=C(c1cccc(C(F)(F)F)c1)NC2=O] | LCMS-C-1 | 2.55 | 606 (M + H)+ |
| 290 | 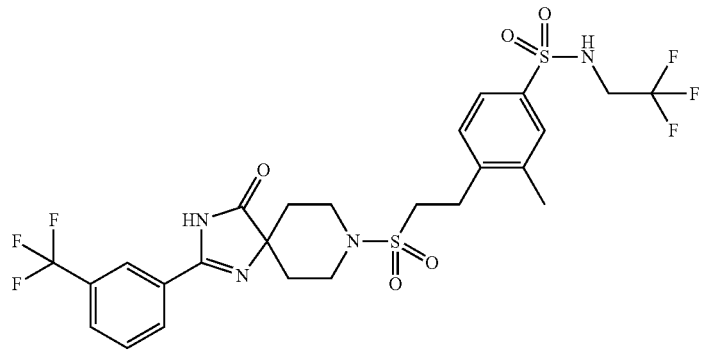 [SMILES: Cc1cc(S(=O)(=O)NCC(F)(F)F)ccc1CCS(=O)(=O)N1CCC2(CC1)N=C(c1cccc(C(F)(F)F)c1)NC2=O] | LCMS-C-1 | 2.65 | 641 (M + H)+ |

TABLE 44-continued

| Compound | Structure | LCMS or HPLC condition | Retention time (min) | MS (m/z) |
|---|---|---|---|---|
| 291 | 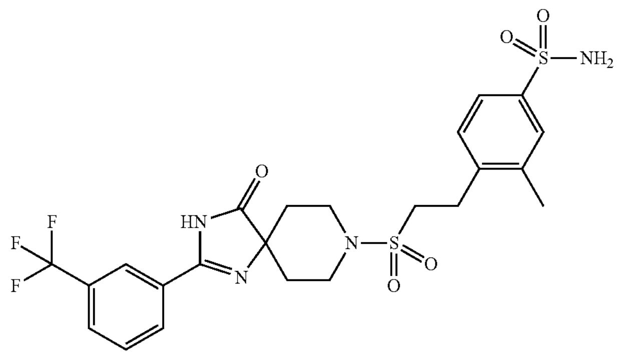 [SMILES: Cc1cc(S(N)(=O)=O)ccc1CCS(=O)(=O)N1CCC2(CC1)N=C(c1cccc(C(F)(F)F)c1)NC2=O] | LCMS-C-1 | 2.35 | 559 (M + H)+ |
| 292 | 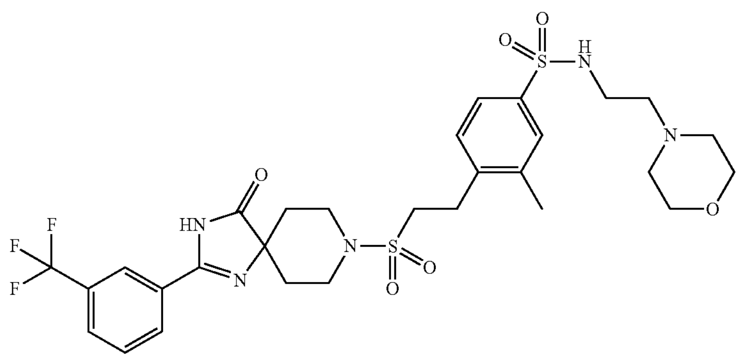 [SMILES: Cc1cc(S(=O)(=O)NCCN2CCOCC2)ccc1CCS(=O)(=O)N1CCC2(CC1)N=C(c1cccc(C(F)(F)F)c1)NC2=O] | LCMS-C-1 | 2.52 | 672 (M + H)+ |
| 293 | 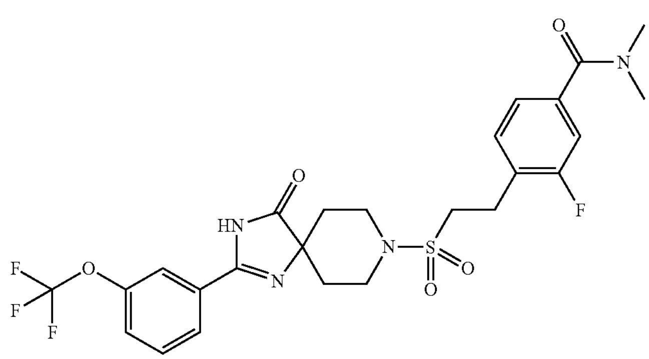 [SMILES: CN(C)C(=O)c1ccc(CCS(=O)(=O)N2CCC3(CC2)N=C(c2cccc(OC(F)(F)F)c2)NC3=O)c(F)c1] | LCMS-C-1 | 2.55 | 571 (M + H)+ |
| 294 | 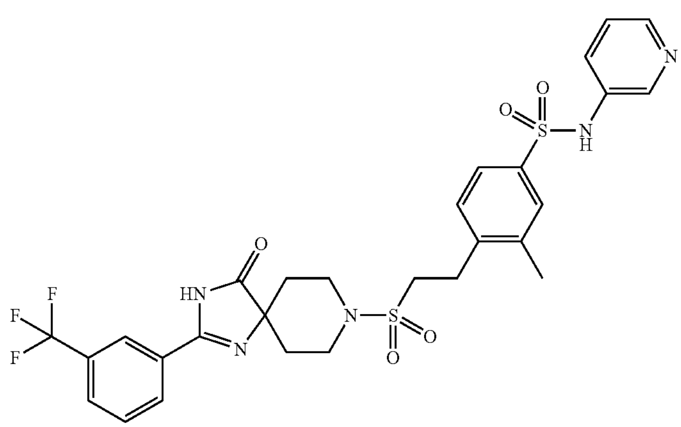 [SMILES: Cc1cc(S(=O)(=O)Nc2cccnc2)ccc1CCS(=O)(=O)N1CCC2(CC1)N=C(c1cccc(C(F)(F)F)c1)NC2=O] | LCMS-A-1 | 2.19 | 636 (M + H)+ |

TABLE 44-continued
| Compound | Structure | LCMS or HPLC condition | Retention time (min) | MS (m/z) |
|---|---|---|---|---|
| 295 | 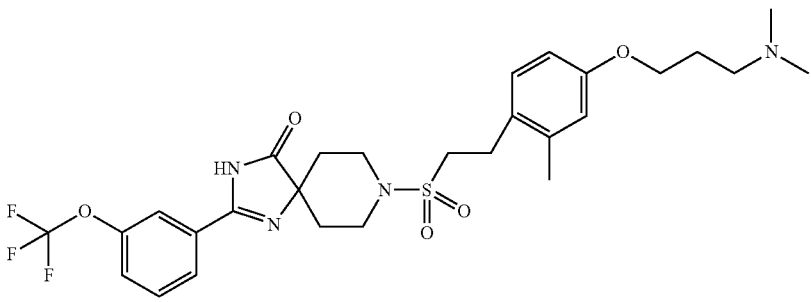 [SMILES: Cc1cc(OCCCN(C)C)ccc1CCS(=O)(=O)N1CCC2(CC1)N=C(c1cccc(OC(F)(F)F)c1)NC2=O] | LCMS-C-1 | 2.67 | 597 (M + H)+ |
| 296 | 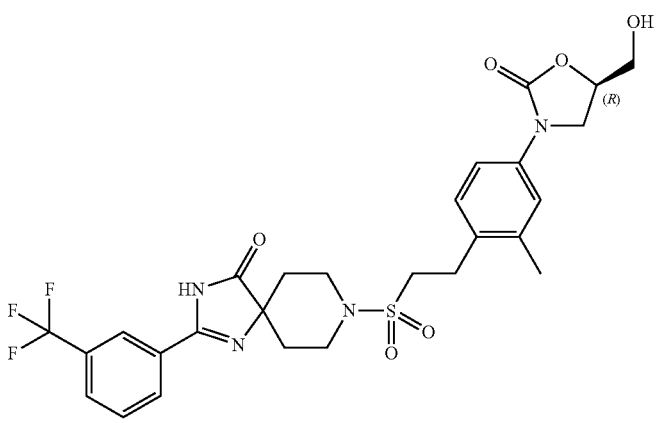 | LCMS-C-1 | 2.45 | 595 (M + H)+ |
| 297 | 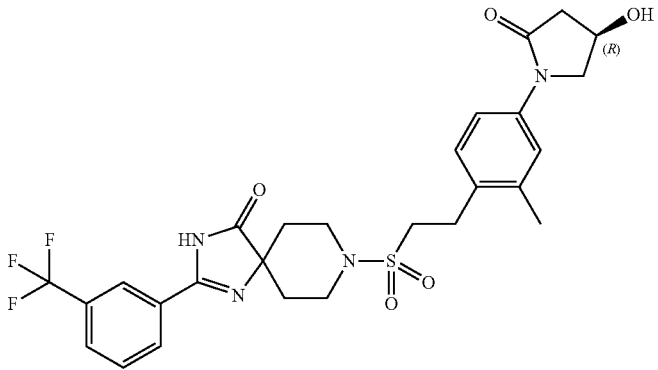 | LCMS-B-1 | 1.91 | 579 (M + H)+ |
| 298 | 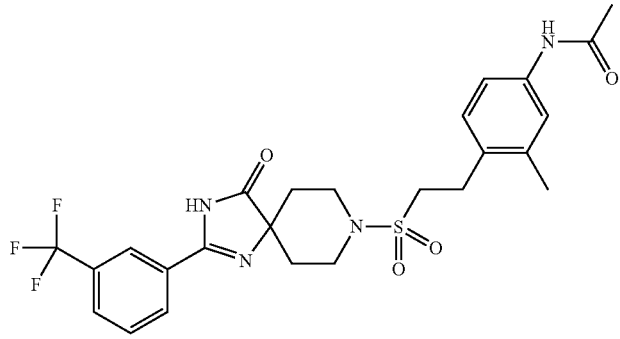 [SMILES: CC(=O)Nc1ccc(CCS(=O)(=O)N2CCC3(CC2)N=C(c2cccc(C(F)(F)F)c2)NC3=O)c(C)c1] | LCMS-C-1 | 2.52 | 537 (M + H)+ |

TABLE 44-continued
| Compound | Structure | LCMS or HPLC condition | Retention time (min) | MS (m/z) |
|---|---|---|---|---|
| 299 | 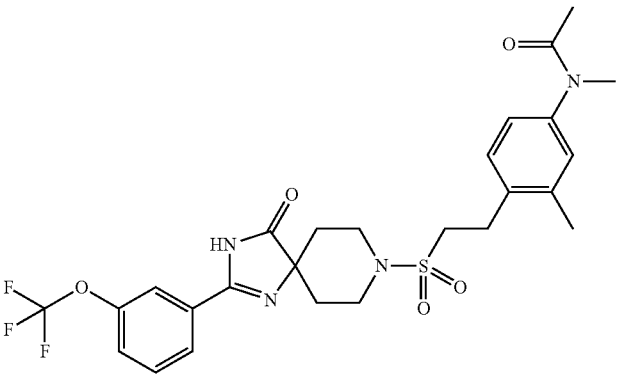 | LCMS-C-1 | 2.47 | 567 (M + H)+ |
| 300 | 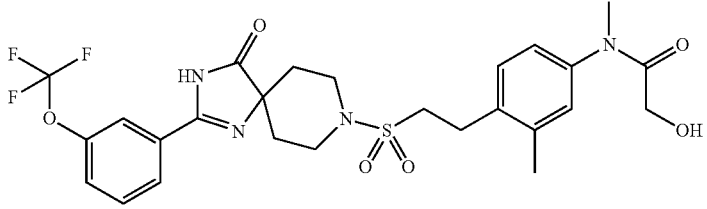 [SMILES: Cc1cc(N(C)C(=O)CO)ccc1CCS(=O)(=O)N1CCC2(CC1)N=C(c1cccc(OC(F)(F)F)c1)NC2=O] | LCMS-A-1 | 2.32 | 583 (M + H)+ |
| 301 | 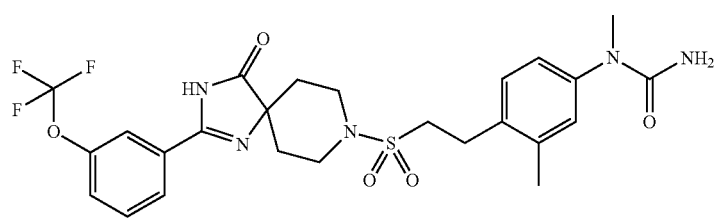 [SMILES: Cc1cc(N(C)C(N)=O)ccc1CCS(=O)(=O)N1CCC2(CC1)N=C(c1cccc(OC(F)(F)F)c1)NC2=O] | LCMS-A-1 | 2.28 | 568 (M + H)+ |
| 302 | 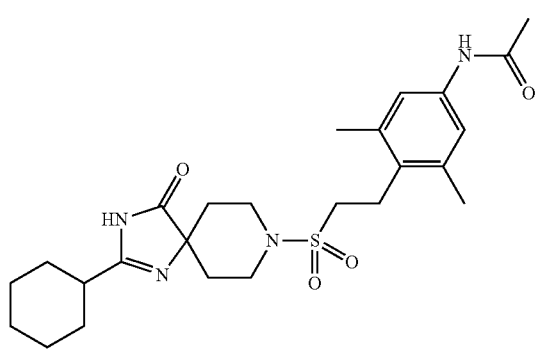 [SMILES: CC(=O)Nc1cc(C)c(CCS(=O)(=O)N2CCC3(CC2)N=C(C2CCCCC2)NC3=O)c(C)c1] | LCMS-B-1 | 1.61 | 489 (M + H)+ |

Example 44

2-Cyclohexyl-8-[2-(1H-indol-4-yl)-ethanesulfonyl]-1,3,8-triaza-spiro[4.5]dec-1-en-4-one (Compound 303)

(Reaction 44-1)

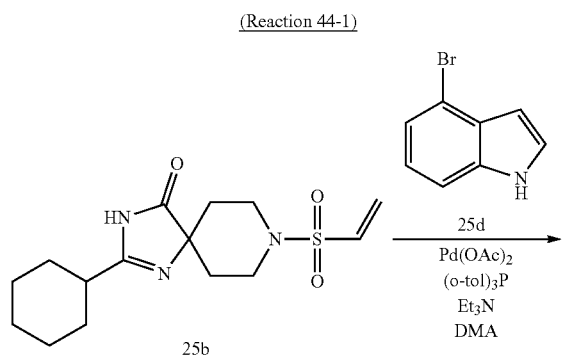

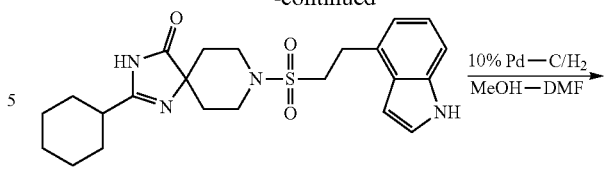

44a

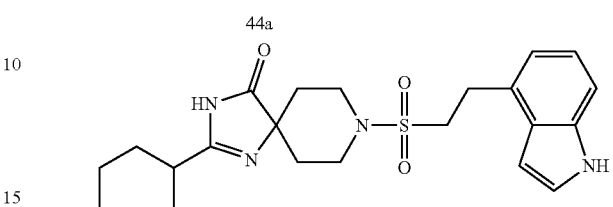

Compound 303

2-Cyclohexyl-8-[2-(1H-indol-4-yl)-ethanesulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=443 (M+H)+.

The example compounds shown below were synthesized by operations similar to those in Example 44 using appropriate reagents and starting materials.

Compounds 304 to 320

TABLE 45

| Compound | Structure | LCMS or HPLC condition | Retention time (min) | MS (m/z) |
|---|---|---|---|---|
| 304 | 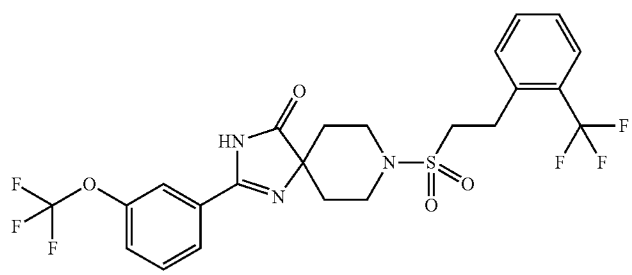 [SMILES: O=C1NC(c2cccc(OC(F)(F)F)c2)=NC12CCN(S(=O)(=O)CCc1ccccc1C(F)(F)F)CC2] | LCMS-A-1 | 2.92 | 550 (M + H)+ |
| 305 | 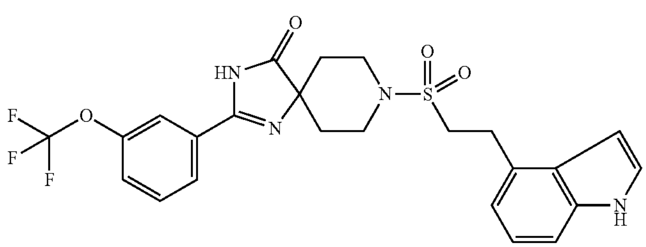 [SMILES: O=C1NC(c2cccc(OC(F)(F)F)c2)=NC12CCN(S(=O)(=O)CCc1cccc3[nH]ccc13)CC2] | LCMS-A-1 | 2.60 | 521 (M + H)+ |
| 306 | 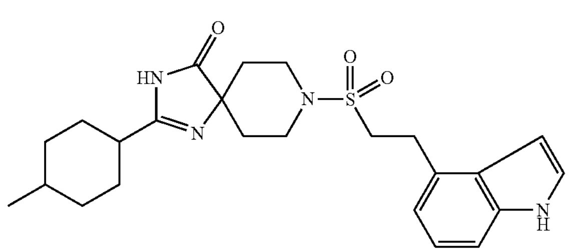 [SMILES: CC1CCC(C2=NC3(CCN(S(=O)(=O)CCc4cccc5[nH]ccc45)CC3)C(=O)N2)CC1] | LCMS-A-1 | 2.15 | 457 (M + H)+ |

TABLE 45-continued

| Compound | Structure | LCMS or HPLC condition | Retention time (min) | MS (m/z) |
| --- | --- | --- | --- | --- |
| 307 | 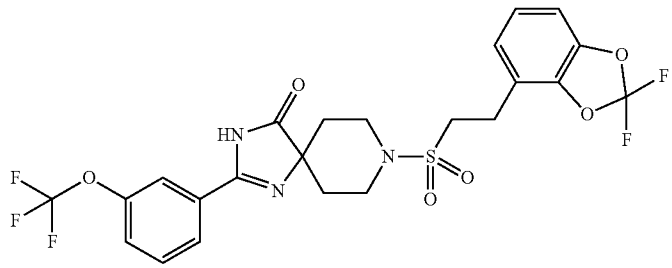 [SMILES: O=C1NC(c2cccc(OC(F)(F)F)c2)=NC12CCN(S(=O)(=O)CCc1cccc3c1OC(F)(F)O3)CC2] | LCMS-A-1 | 2.92 | 562 (M + H)+ |
| 308 | 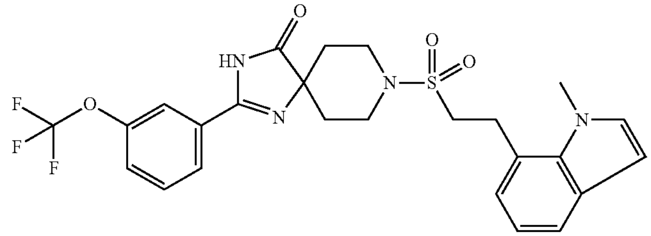 [SMILES: Cn1ccc2cccc(CCS(=O)(=O)N3CCC4(CC3)N=C(c3cccc(OC(F)(F)F)c3)NC4=O)c21] | LCMS-A-1 | 2.89 | 535 (M + H)+ |
| 309 | 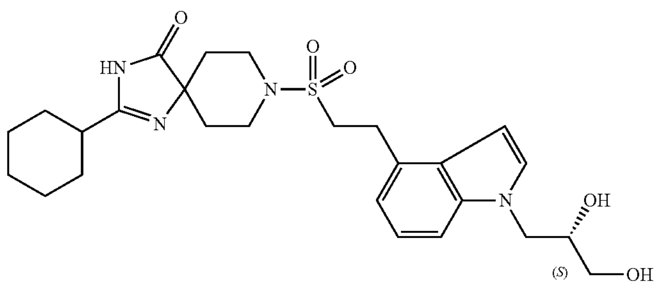 | LCMS-C-1 | 2.38 | 517 (M + H)+ |
| 310 | 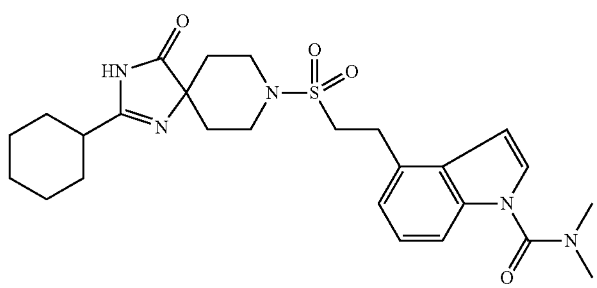 [SMILES: CN(C)C(=O)n1ccc2c(CCS(=O)(=O)N3CCC4(CC3)N=C(C3CCCCC3)NC4=O)cccc21] | LCMS-C-1 | 2.52 | 514 (M + H)+ |
| 311 | 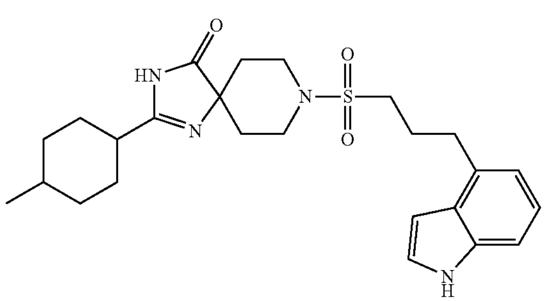 [SMILES: CC1CCC(C2=NC3(CCN(S(=O)(=O)CCCc4cccc5[nH]ccc45)CC3)C(=O)N2)CC1] | LCMS-E-7 | 1.53 | 471 (M + H)+ |

TABLE 45-continued

| Compound | Structure | LCMS or HPLC condition | Retention time (min) | MS (m/z) |
|---|---|---|---|---|
| 312 | 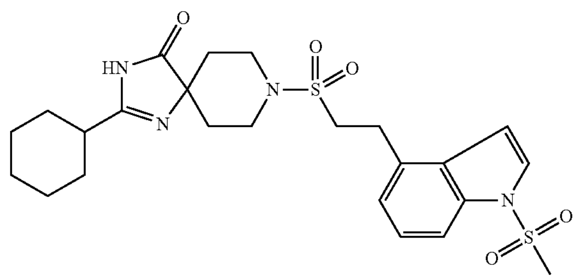 [SMILES: CS(=O)(=O)n1ccc2c(CCS(=O)(=O)N3CCC4(CC3)N=C(C3CCCCC3)NC4=O)cccc21] | LCMS-C-1 | 2.57 | 521 (M + H)+ |
| 313 | 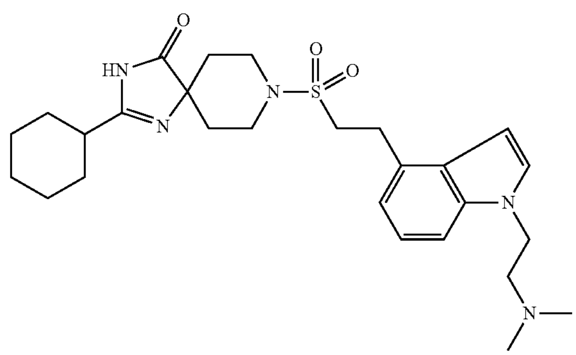 [SMILES: CN(C)CCn1ccc2c(CCS(=O)(=O)N3CCC4(CC3)N=C(C3CCCCC3)NC4=O)cccc21] | LCMS-A-1 | 1.65 | 514 (M + H)+ |
| 314 | 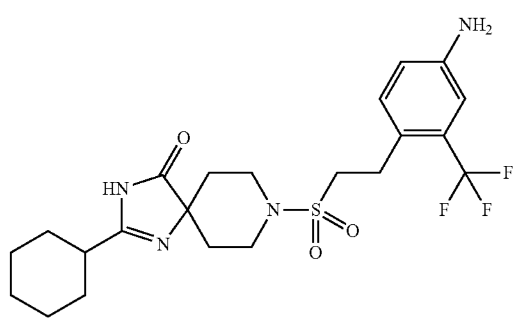 [SMILES: Nc1ccc(CCS(=O)(=O)N2CCC3(CC2)N=C(C2CCCCC2)NC3=O)c(C(F)(F)F)c1] | LCMS-C-1 | 2.48 | 487 (M + H)+ |
| 315 | 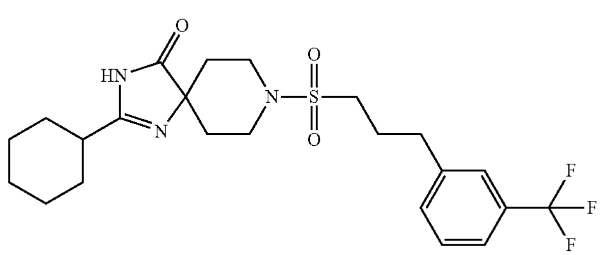 [SMILES: O=C1NC(C2CCCCC2)=NC12CCN(S(=O)(=O)CCCc1cccc(C(F)(F)F)c1)CC2] | HPLC-A-1 | 13.4 | 486 (M + H)+ |
| 316 | 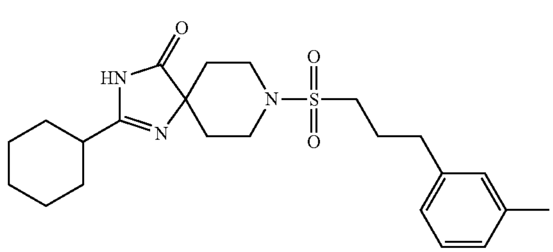 [SMILES: Cc1cccc(CCCS(=O)(=O)N2CCC3(CC2)N=C(C2CCCCC2)NC3=O)c1] | HPLC-A-2 | 11.6 | 432 (M + H)+ |

TABLE 45-continued

| Compound | Structure | LCMS or HPLC condition | Retention time (min) | MS (m/z) |
|---|---|---|---|---|
| 317 | 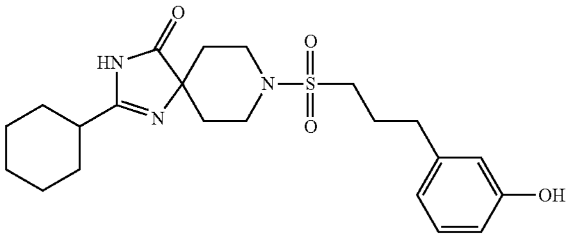 [SMILES: O=C1NC(C2CCCCC2)=NC12CCN(S(=O)(=O)CCCc1cccc(O)c1)CC2] | LCMS-D-1 | 1.8 | 434 (M + H)+ |
| 318 | 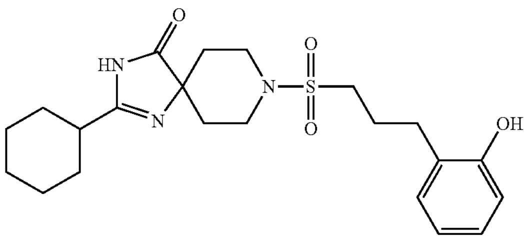 [SMILES: O=C1NC(C2CCCCC2)=NC12CCN(S(=O)(=O)CCCc1ccccc1O)CC2] | LCMS-D-1 | 3.0 | 434 (M + H)+ |
| 319 | 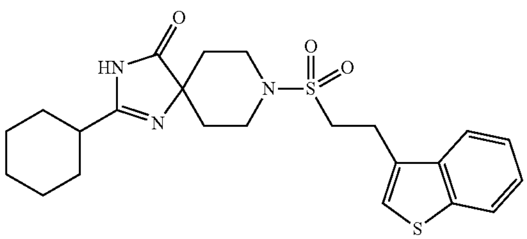 [SMILES: O=C1NC(C2CCCCC2)=NC12CCN(S(=O)(=O)CCc1csc3ccccc13)CC2] | LCMS-C-1 | 2.87 | 460 (M + H)+ |
| 320 | 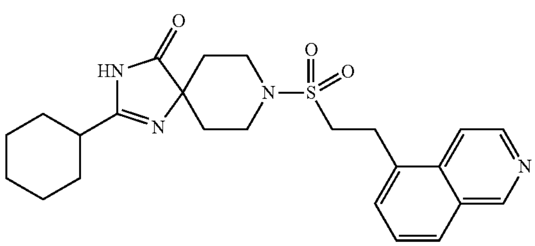 [SMILES: O=C1NC(C2CCCCC2)=NC12CCN(S(=O)(=O)CCc1cccc3cnccc13)CC2] | LCMS-A-1 | 1.49 | 455 (M + H)+ |

The aryl bromide reagent used in the synthesis of Compound 313 ([2-(4-bromo-indol-1-yl)-ethyl]-dimethyl-amine) was synthesized as follows.

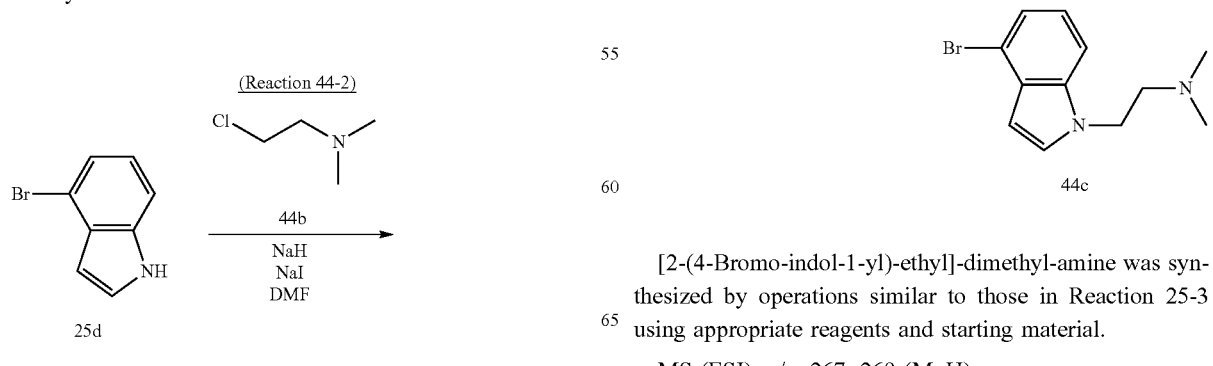

[2-(4-Bromo-indol-1-yl)-ethyl]-dimethyl-amine was synthesized by operations similar to those in Reaction 25-3 using appropriate reagents and starting material.

MS (ESI) m/z=267, 269 (M+H)+.

Example 45

2-Cyclohexyl-8-{2-[4-((S)-2,3-dihydroxy-propylamino)-2-methyl-phenyl]-ethanesulfonyl}-1,3,8-triaza-spiro[4.5]dec-1-en-4-one (Compound 321)

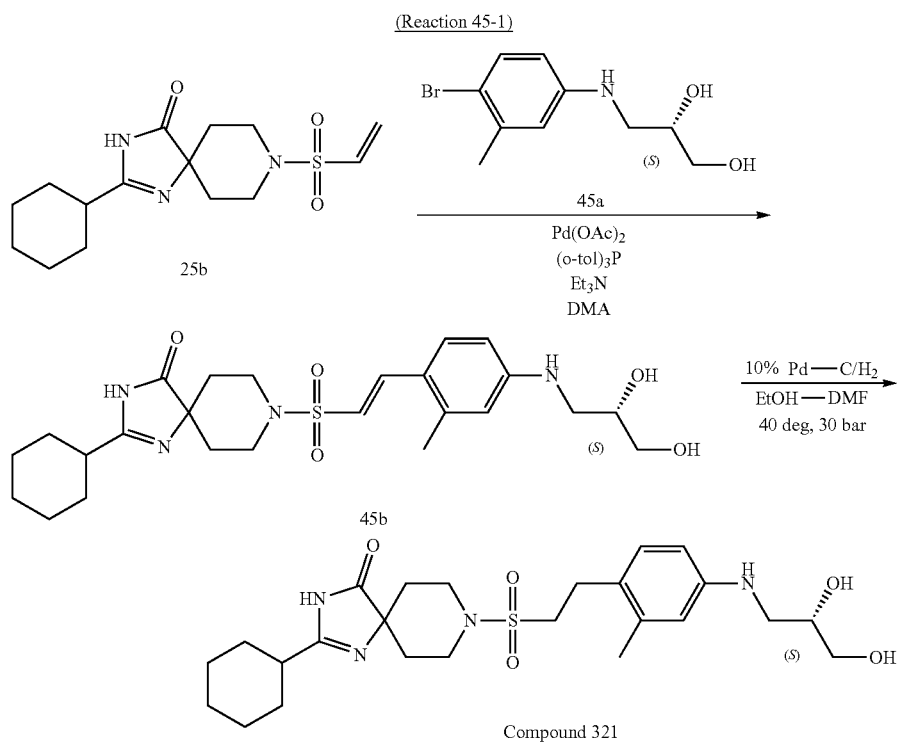

2-Cyclohexyl-8-{2-[4-((S)-2,3-dihydroxy-propylamino)-2-methyl-phenyl]-ethanesulfonyl}-1,3,8-triaza-spiro[4.5]dec-1-en-4-one was synthesized by operations similar to those in Reaction 25-2 and Reaction 42-2 using appropriate reagents and starting material.
MS (ESI) m/z=527 (M+H)+.

The example compound shown below was synthesized by operations similar to those in Example 45 using appropriate reagents and starting material.

Compound 322

TABLE 46

| Compound | Structure | LCMS or HPLC condition | Retention time (min) | MS (m/z) |
|---|---|---|---|---|
| 322 | 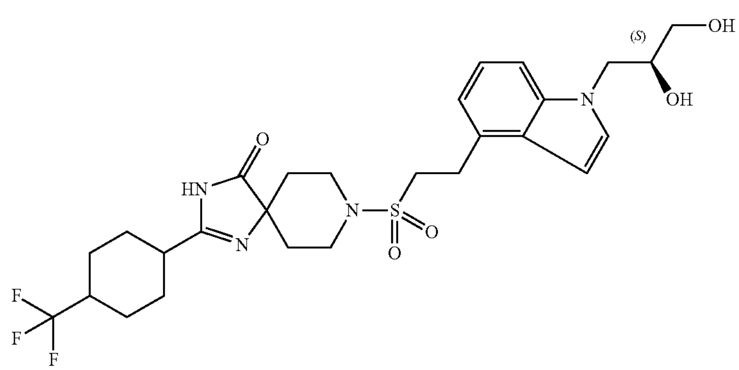 | LCMS-C-1 | 2.48 | 585 (M + H)+ |

The aryl bromide reagent used in the synthesis of Compound 321 ((S)-3-(4-bromo-3-methyl-phenylamino)-propane-1,2-diol) was synthesized as follows.

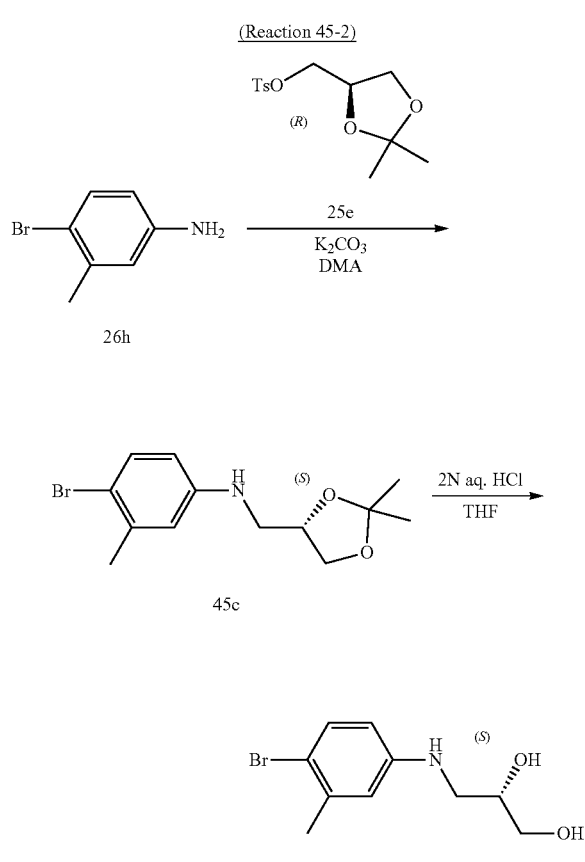

(S)-3-(4-Bromo-3-methyl-phenylamino)-propane-1,2-diol was synthesized by operations similar to those in Reaction 26-4 and Reaction 25-4 using appropriate reagents and starting material.

MS (ESI) m/z=260, 262 (M+H)+.

Example 46

2-Cyclohexyl-8-[2-(2-trifluoromethyl-phenyl)-ethanesulfonyl]-1,3,8-triaza-spiro[4.5]dec-1-en-4-one (Compound 323)

(Reaction 46-1)

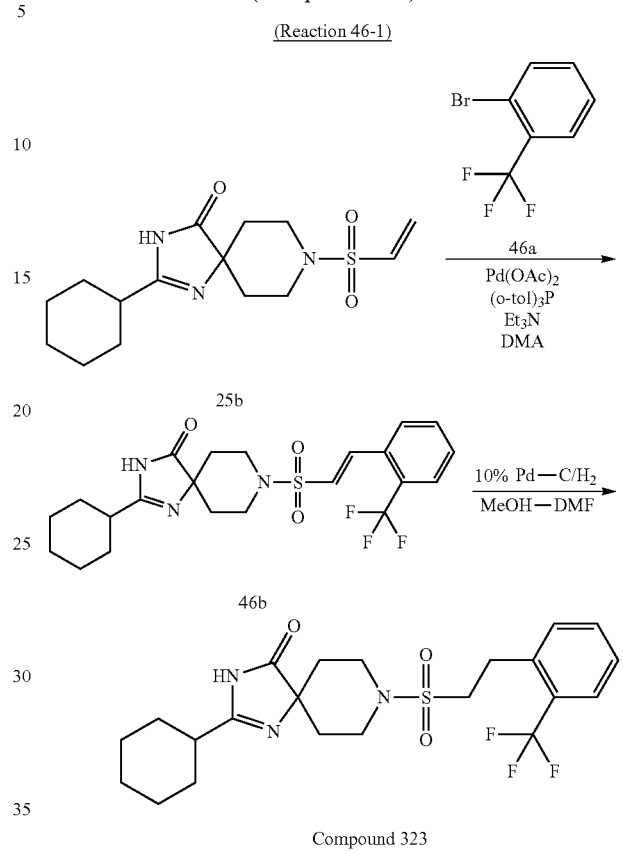

Compound 323

2-Cyclohexyl-8-[2-(2-trifluoromethyl-phenyl)-ethanesulfonyl]-1,3,8-triaza-spiro[4.5]dec-1-en-4-one was synthesized by operations similar to those in Reaction 26-1 and Reaction 42-1 using appropriate reagents and starting material.

MS (ESI) m/z=472 (M+H)+.

The example compound shown below was synthesized by operations similar to those in Example 46 using appropriate reagents and starting material.

Compound 324

TABLE 47

| Compound | Structure | LCMS or HPLC condition | Retention time (min) | MS (m/z) |
|---|---|---|---|---|
| 324 | 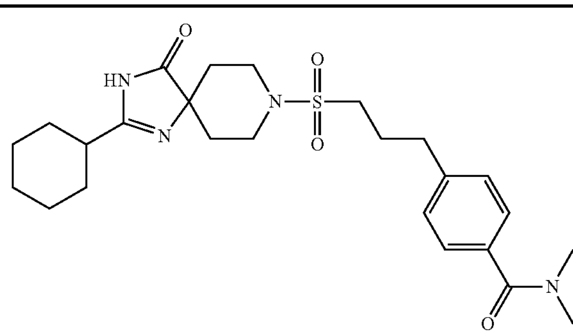 | LCMS-D-1 | 2.7 | 489 (M + H)+ |

Example 47

8-{2-[4-((R)-2,3-Dihydroxy-propoxy)-2-methyl-phenyl]-ethanesulfonyl}-2-(3-trifluoromethoxy-phenyl)-1,3,8-triaza-spiro[4.5]dec-1-en-4-one (Compound 325)

(Reaction 47-1)

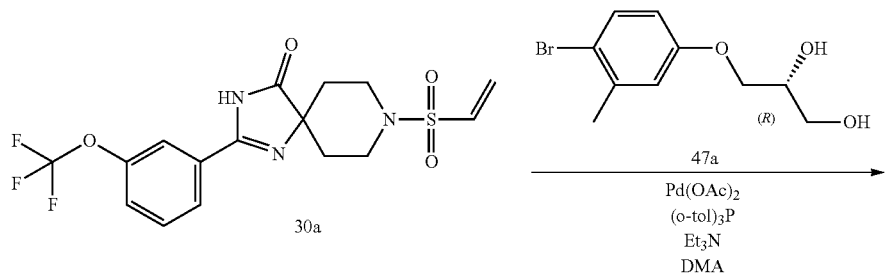

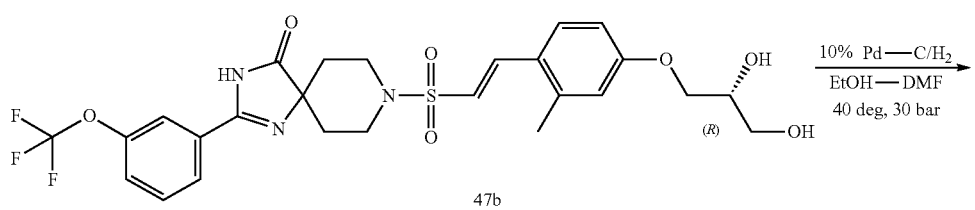

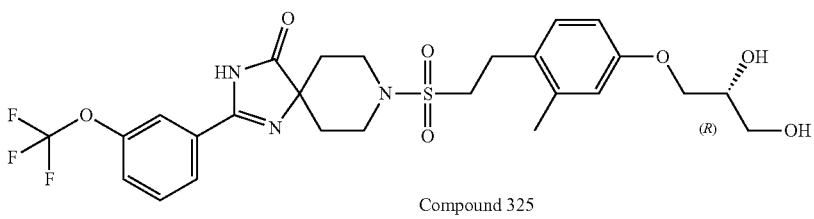

8-{2-[4-((R)-2,3-Dihydroxy-propoxy)-2-methyl-phenyl]-ethanesulfonyl}-2-(3-trifluoromethoxy-phenyl)-1,3,8-triaza-spiro[4.5]dec-1-en-4-one was synthesized by operations similar to those in Reaction 26-1 and Reaction 42-2 using appropriate reagents and starting material.

MS (ESI) m/z=586 (M+H)+.

The aryl bromide reagent used in the synthesis of Compound 325 ((R)-3-(4-bromo-3-methyl-phenoxy)-propane-1,2-diol) was synthesized as follows.

(Reaction 47-2)

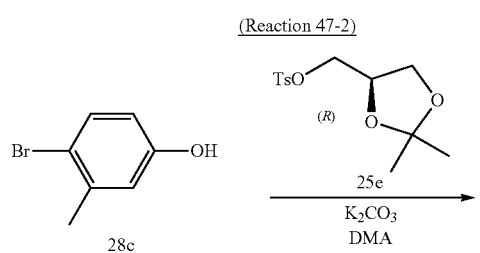

-continued

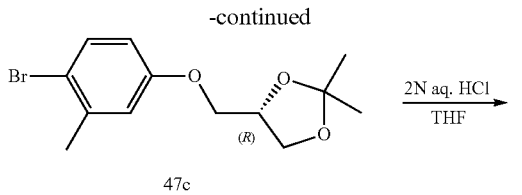

(R)-3-(4-Bromo-3-methyl-phenoxy)-propane-1,2-diol was synthesized by operations similar to those in Reaction 26-4 and Reaction 25-4 using appropriate reagents and starting material.

MS (ESI) m/z=283, 285 (M+Na)+.

Example 48

N-(2-Hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide (Compound 326)

(Reaction 48-1)

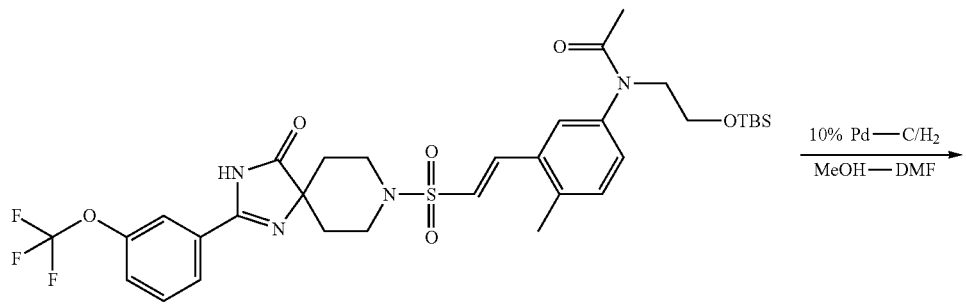

48a

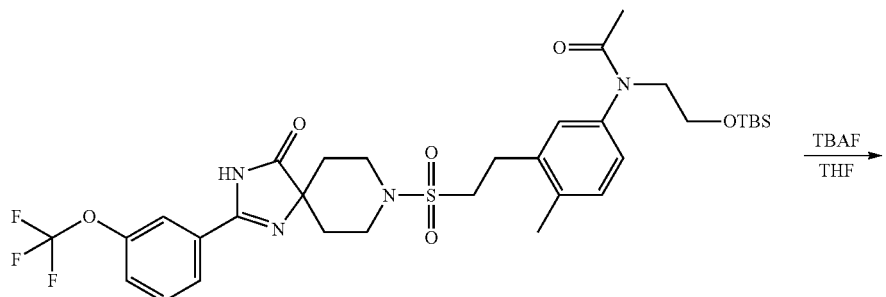

48b

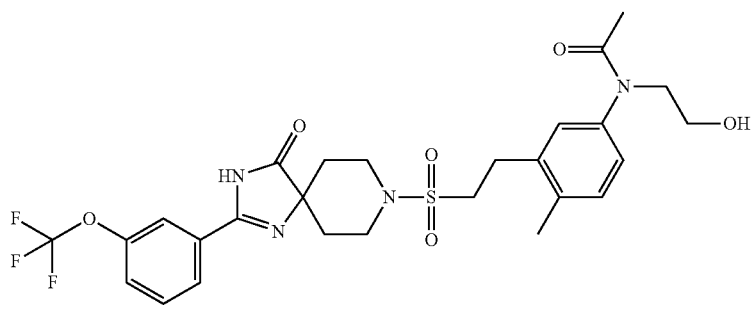

Compound 326

N-(2-Hydroxy-ethyl)-N-(4-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 42-1 and Reaction 39-2 using appropriate reagents and starting material.

MS (ESI) m/z=597 (M+H)+.

Example 49

N-(2-Hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide (Compound 327)

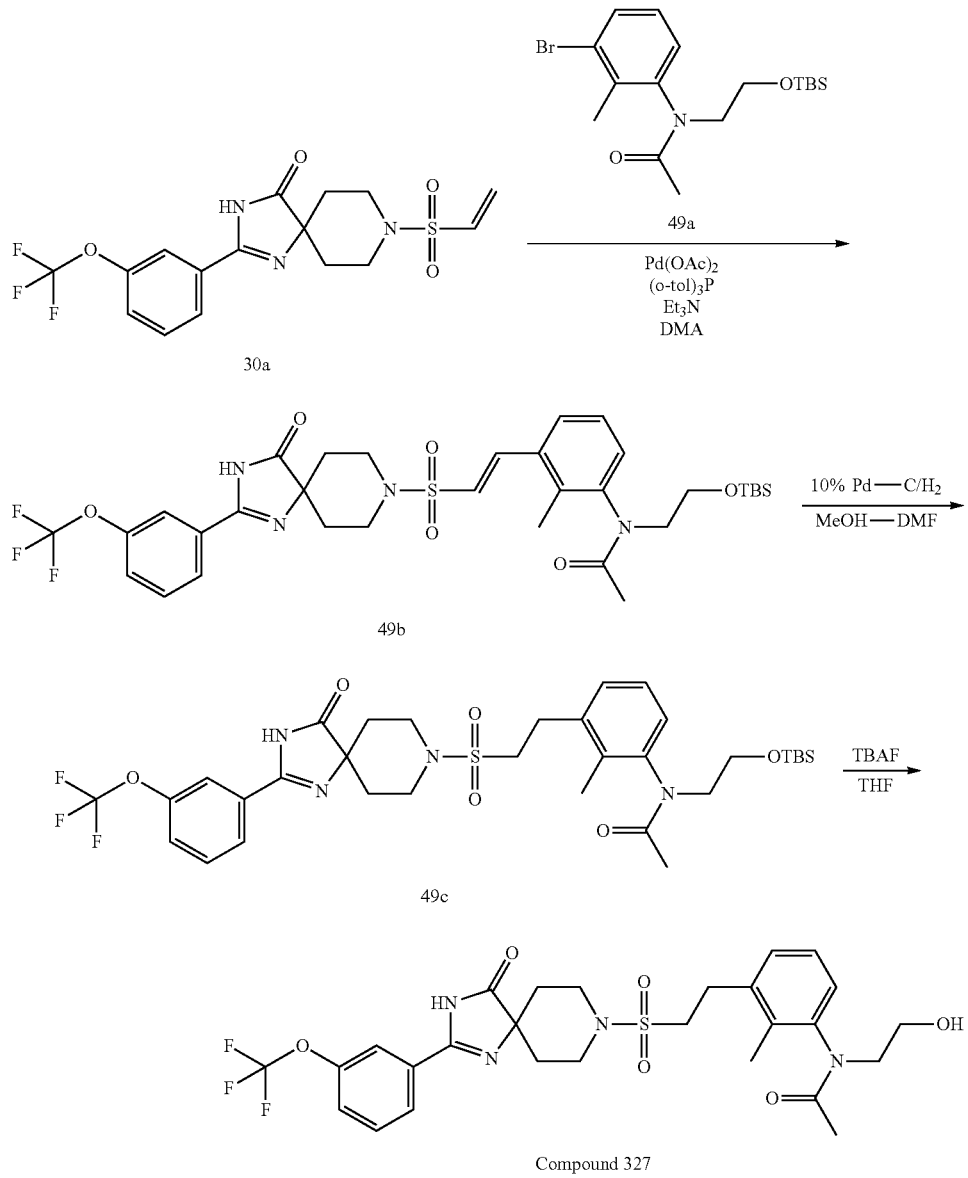

N-(2-Hydroxy-ethyl)-N-(2-methyl-3-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 26-1, Reaction 42-1 and Reaction 39-2 using appropriate reagents and starting material.

MS (ESI) m/z=597 (M+H)+.

The aryl bromide reagent used in the synthesis of Compound 327 (N-(3-bromo-2-methyl-phenyl)-N-[2-(tert-butyl-dimethyl-silanyloxy)-ethyl]-acetamide) was synthesized as follows.

(Reaction 49-2)

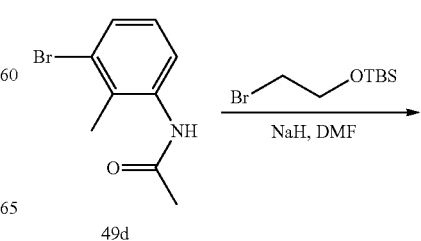

-continued

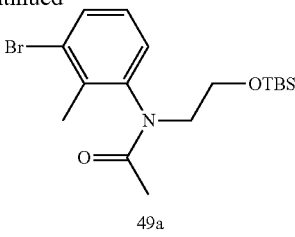

49a

N-(3-Bromo-2-methyl-phenyl)-N-[2-(tert-butyl-dimethyl-silanyloxy)-ethyl]-acetamide was synthesized by operations similar to those in Reaction 25-3 using appropriate reagents and starting material.

MS (ESI) m/z=386, 388 (M+H)+.

Example 50

8-[3-(3-Amino-phenyl)-propane-1-sulfonyl]-2-cyclohexyl-1,3,8-triaza-spiro[4.5]dec-1-en-4-one (Compound 328)

(Reaction 50-1)

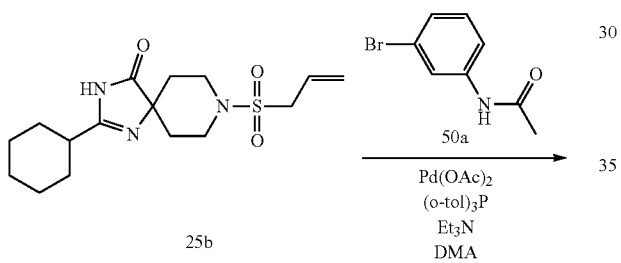


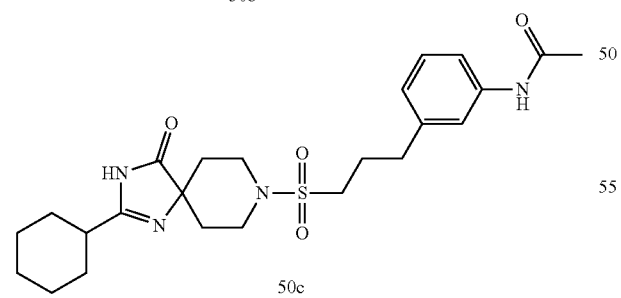

N-{3-[3-(2-Cyclohexyl-4-oxo-1,3,8-triaza-spiro[4.5]dec-1-ene-8-sulfonyl)-propyl]-phenyl}-acetamide was synthesized by operations similar to those in Reaction 26-1 and Reaction 42-1 using appropriate reagents and starting material.

MS (ESI) m/z=475 (M+H)+.

(Reaction 50-2)

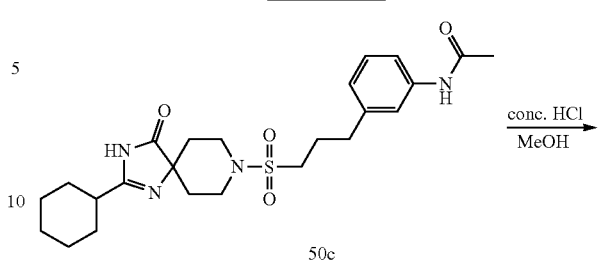

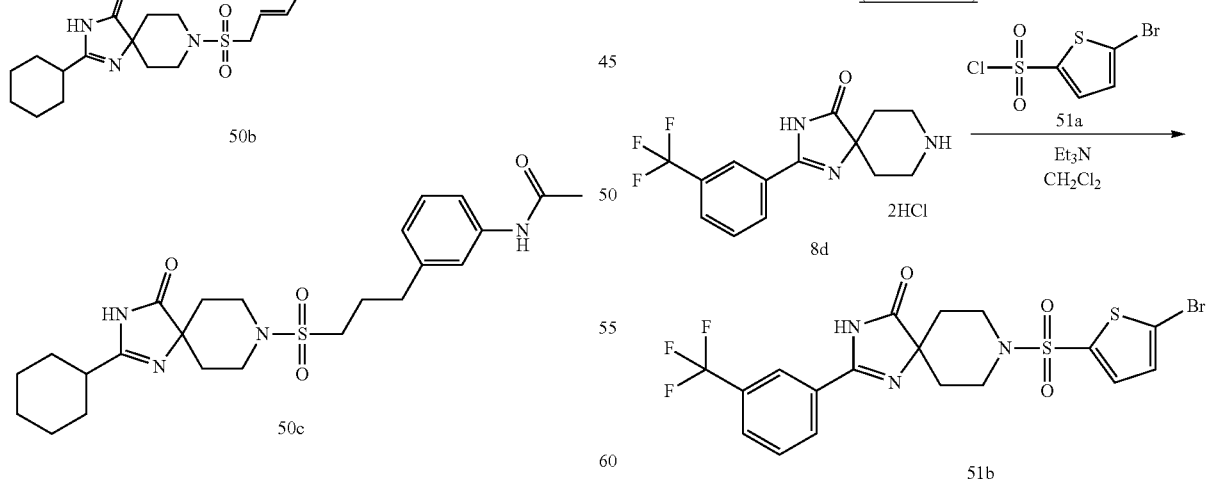

Compound 328

Conc. HCl (0.5 ml) was added to a solution of N-{3-[3-(2-cyclohexyl-4-oxo-1,3,8-triaza-spiro[4.5]dec-1-ene-8-sulfonyl)-propyl]-phenyl}-acetamide (5.0 mg, 0.0105 mmol) in MeOH (1 ml) at room temperature. The mixture was stirred at 30 to 40° C. for four hours. The reaction mixture was concentrated under reduced pressure, and the resulting residue was then purified by preparative TLC (CH$_2$Cl$_2$:MeOH=10:1) to give 8-[3-(3-amino-phenyl)-propane-1-sulfonyl]-2-cyclohexyl-1,3,8-triaza-spiro[4.5]dec-1-en-4-one (2.5 mg, yield 55%).

Example 51

N,N-Dimethyl-4-{5-[4-oxo-2-(3-trifluoromethyl-phenyl)-1,3,8-triaza-spiro[4.5]dec-1-ene-8-sulfonyl]-thiophen-2-yl}-benzamide (Compound 329)

(Reaction 51-1)

8-(5-Bromo-thiophene-2-sulfonyl)-2-(3-trifluoromethyl-phenyl)-1,3,8-triaza-spiro[4.5]dec-1-en-4-one was synthesized by operations similar to those in Reaction 5-4 using appropriate reagents and starting material.

MS (ESI) m/z=523 (M+H)+.

(Reaction 51-2)

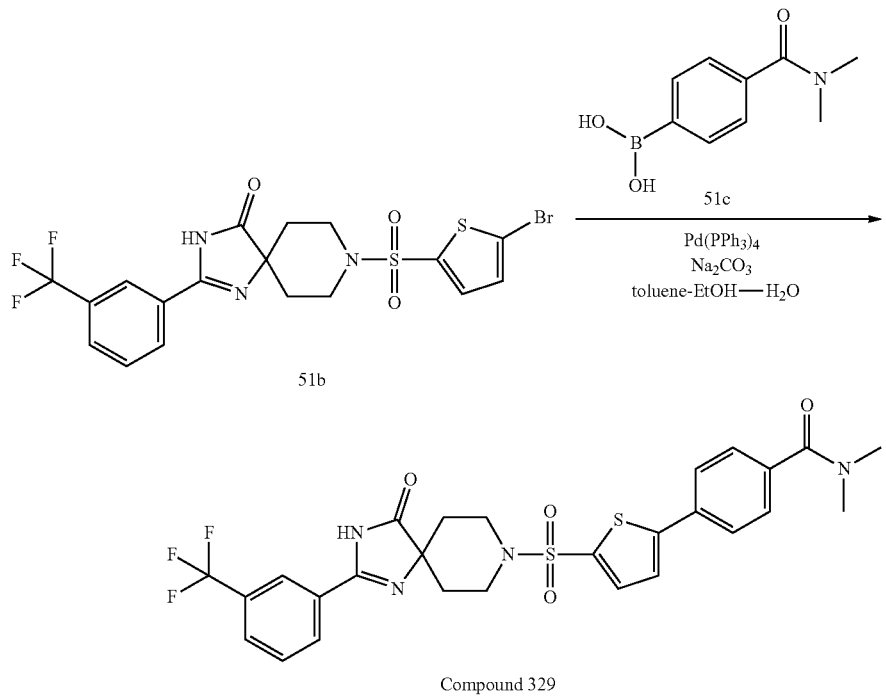

Compound 329

A mixture of 8-(5-bromo-thiophene-2-sulfonyl)-2-(3-trifluoromethyl-phenyl)-1,3,8-triaza-spiro[4.5]dec-1-en-4-one (11.1 mg, 0.0212 mmol), 4-(N,N-dimethylaminocarbonyl)phenylboronic acid (8.0 mg, 0.041 mmol), Pd(PPh$_3$)$_4$ (3.8 mg, 0.0033 mmol) and Na$_2$CO$_3$ (22.0 mg, 0.208 mmol) in toluene (0.12 ml)-EtOH (0.12 ml)-H$_2$O (0.12 ml) was stirred at 85° C. for 20 hours in a sealed test tube in an N$_2$ atmosphere. The reaction mixture was cooled to room temperature and extracted with AcOEt. The organic layer was washed with a saturated aqueous NH$_4$Cl solution, and then dried over MgSO$_4$ and concentrated under reduced pressure. The resulting residue was purified by silica gel column chromatography (AcOEt) to give N,N-dimethyl-4-{5-[4-oxo-2-(3-trifluoromethyl-phenyl)-1,3,8-triaza-spiro[4.5]dec-1-ene-8-sulfonyl]-thiophen-2-yl}-benzamide (9.7 mg, 77%).

$^1$H-NMR (300 MHz) (CDCl$_3$) δ 1.74 (2H, br d, J=13.5 Hz), 2.21 (2H, ddd, J=13.5, 11.0, and 4.0 Hz), 3.04 (3H, br s), 3.15 (3H, br s), 3.24 (2H, ddd, J=11.5, 11.0, and 3.0 Hz), 3.82 (2H, ddd, J=11.5, 4.0 and 4.0 Hz), 7.38 (1H, d, J=4.0 Hz), 7.50 (2H, d, J=8.4 Hz), 7.57 (1H, d, J=4.0 Hz), 7.60 (1H, t, J=8.1 Hz), 7.66 (2H, d, J=8.4 Hz), 7.78 (1H, d, J=8.1 Hz), 7.99 (1H, d, J=8.1 Hz), 8.12 (1H, s), 9.61 (1H, br s). MS (ESI) m/z=591 (M+H)+.

The example compounds shown below were synthesized by operations similar to those in Example 51 using appropriate reagents and starting materials.

Compounds 330 to 337

TABLE 48

| Compound | Structure | LCMS or HPLC condition | Retention time (min) | MS (m/z) |
|---|---|---|---|---|
| 330 | 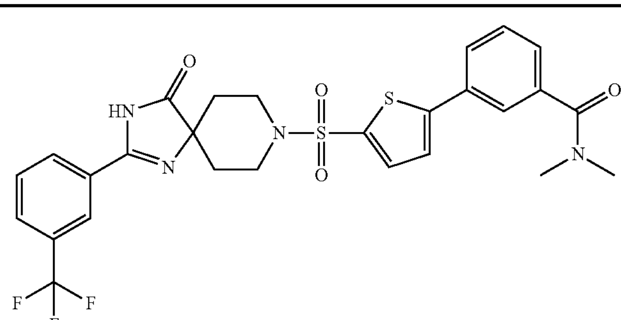 | LCMS-C-2 | 2.08 | 591 (M + H)+ |

TABLE 48-continued

| Compound | Structure | LCMS or HPLC condition | Retention time (min) | MS (m/z) |
|---|---|---|---|---|
| 331 | 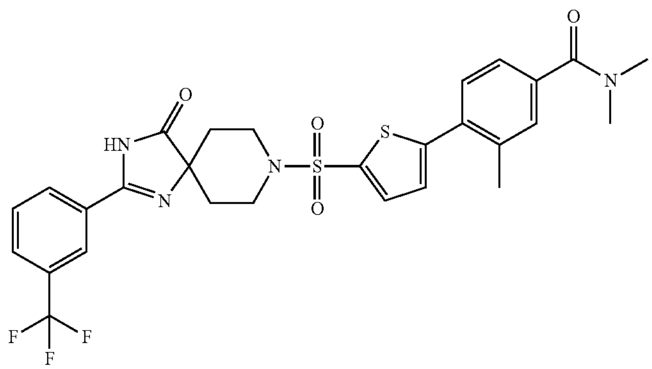 [SMILES: Cc1cc(C(=O)N(C)C)ccc1-c1ccc(S(=O)(=O)N2CCC3(CC2)N=C(c2cccc(C(F)(F)F)c2)NC3=O)s1] | LCMS-C-2 | 2.15 | 605 (M + H)+ |
| 332 | 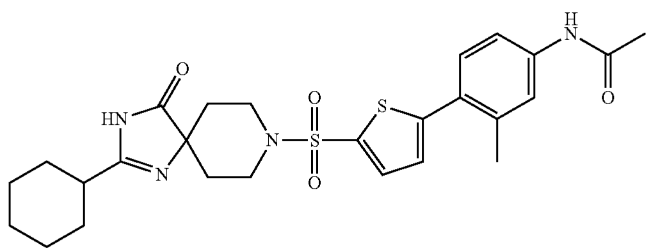 [SMILES: CC(=O)Nc1ccc(-c2ccc(S(=O)(=O)N3CCC4(CC3)N=C(C3CCCCC3)NC4=O)s2)c(C)c1] | LCMS-C-2 | 1.92 | 529 (M + H)+ |
| 333 | 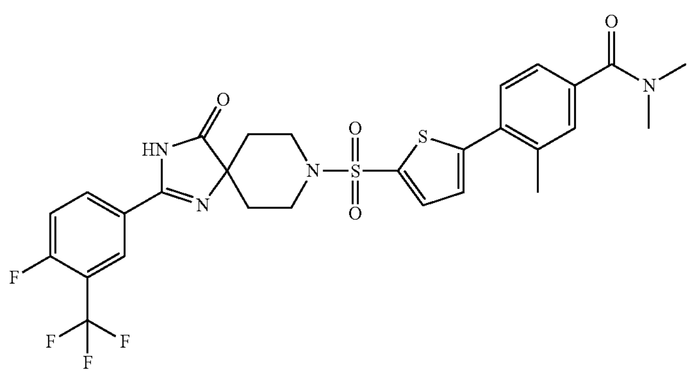 [SMILES: Cc1cc(C(=O)N(C)C)ccc1-c1ccc(S(=O)(=O)N2CCC3(CC2)N=C(c2ccc(F)c(C(F)(F)F)c2)NC3=O)s1] | LCMS-C-2 | 2.20 | 623 (M + H)+ |
| 334 | 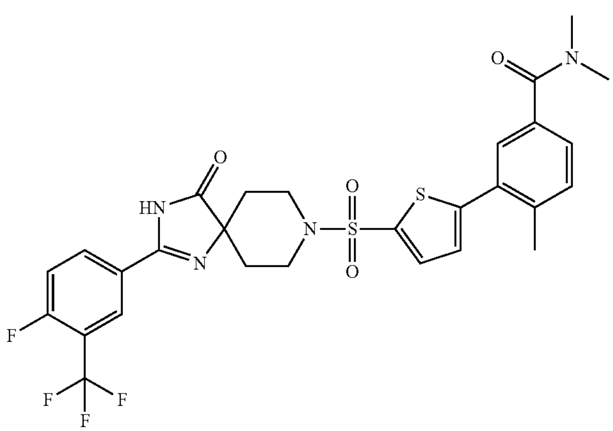 [SMILES: Cc1ccc(C(=O)N(C)C)cc1-c1ccc(S(=O)(=O)N2CCC3(CC2)N=C(c2ccc(F)c(C(F)(F)F)c2)NC3=O)s1] | LCMS-C-2 | 2.20 | 623 (M + H)+ |

TABLE 48-continued

| Compound | Structure | LCMS or HPLC condition | Retention time (min) | MS (m/z) |
|---|---|---|---|---|
| 335 | 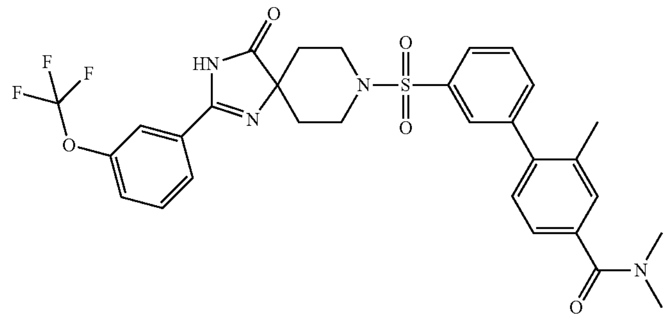 [SMILES: Cc1cc(C(=O)N(C)C)ccc1-c1cccc(S(=O)(=O)N2CCC3(CC2)N=C(c2cccc(OC(F)(F)F)c2)NC3=O)c1] | LCMS-D-1 | 3.37 | 615 (M + H)+ |
| 336 | 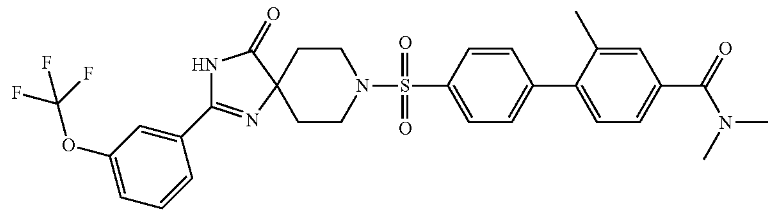 [SMILES: Cc1cc(C(=O)N(C)C)ccc1-c1ccc(S(=O)(=O)N2CCC3(CC2)N=C(c2cccc(OC(F)(F)F)c2)NC3=O)cc1] | LCMS-D-1 | 3.35 | 615 (M + H)+ |
| 337 | 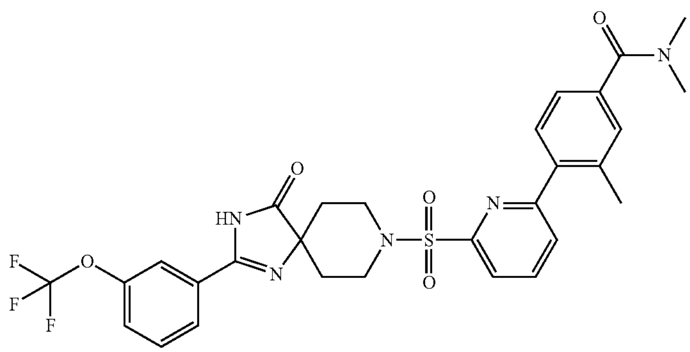 [SMILES: Cc1cc(C(=O)N(C)C)ccc1-c1cccc(S(=O)(=O)N2CCC3(CC2)N=C(c2cccc(OC(F)(F)F)c2)NC3=O)n1] | LCMS-D-1 | 3.27 | 616 (M + H)+ |

The aryl boronate reagent used in the synthesis of Compounds 331, 333, 335, 336 and 337 (3,N,N-trimethyl-4-(4,4,5,5-tetramethyl-[1,3,2]dioxaborolan-2-yl)-benzamide) was synthesized as follows.

(Reaction 51-3)

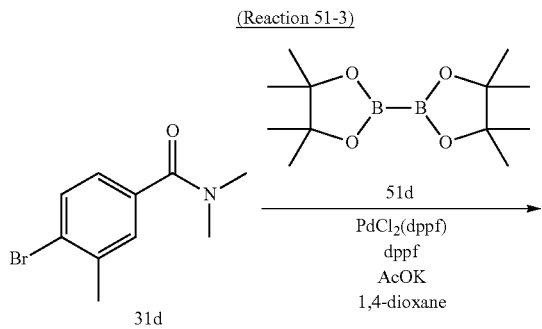

-continued

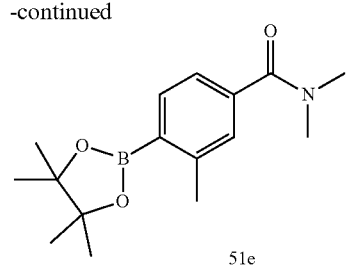

A mixture of 4-bromo-3,N,N-trimethyl-benzamide (203 mg, 0.838 mmol), 1,1'-bis(diphenylphosphino)-ferrocene (dppf) (27.9 mg, 0.0503 mmol), PdCl$_2$(dppf)-CH$_2$Cl$_2$ (41.6 mg, 0.0509 mmol), AcOK (245 mg, 2.50 mmol) and bis(pinacolato)diboron (286 mg, 1.13 mmol) in dioxane (5.5 ml) was stirred at 85° C. for six hours in a sealed test tube in an N$_2$ atmosphere. The reaction mixture was cooled to room temperature and extracted with AcOEt. The organic layer was washed with water, and then dried over MgSO$_4$ and concentrated under reduced pressure. The resulting residue was purified by silica gel column chromatography (hexane/ethyl acetate=2/1) to give 3,N,N-trimethyl-4-(4,4,5,5-tetramethyl-[1,3,2]dioxaborolan-2-yl)-benzamide (135 mg, 56%).

MS (ESI) m/z=290 (M+H)+.

The aryl boronate reagent used in the synthesis of Compound 334 (4,N,N-trimethyl-3-(4,4,5,5-tetramethyl-[1,3,2]dioxaborolan-2-yl)-benzamide) was synthesized as follows.

The aryl boronate reagent used in the synthesis of Compound 332 (N-[3-methyl-4-(4,4,5,5-tetramethyl-[1,3,2]dioxaborolan-2-yl)-phenyl]-acetamide) was synthesized as follows.

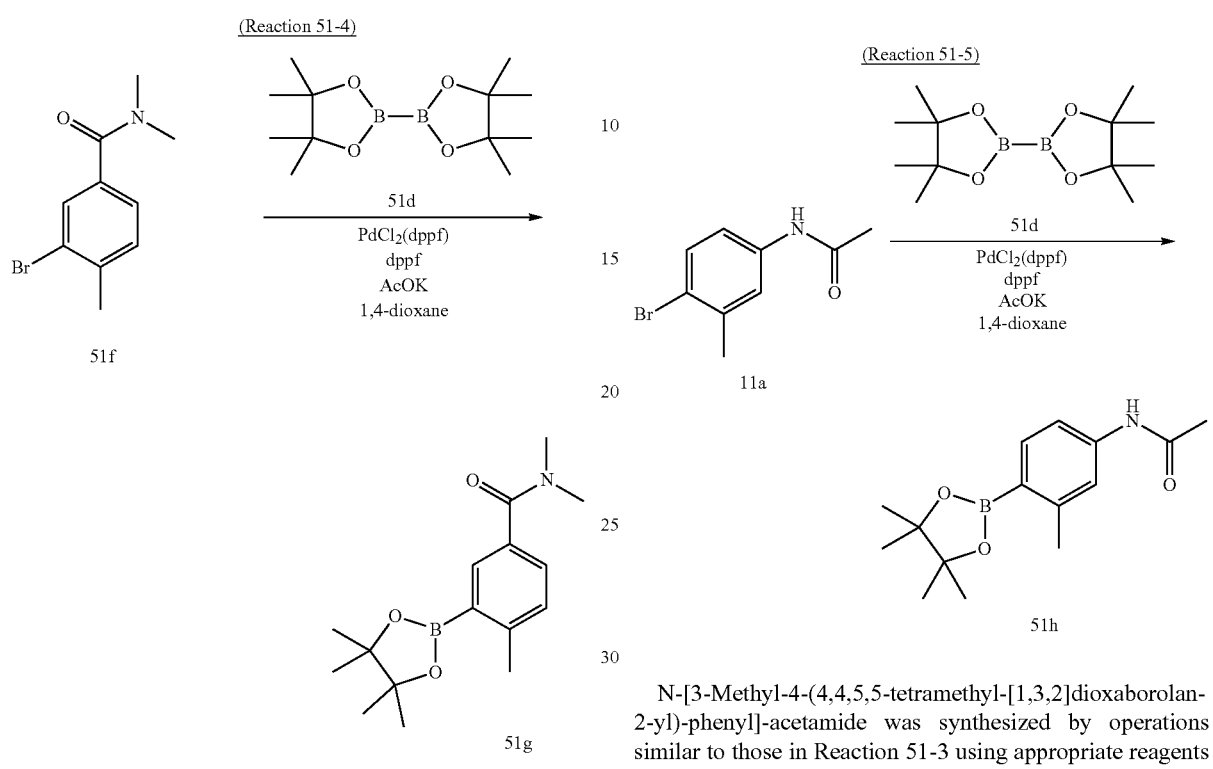

4,N,N-Trimethyl-3-(4,4,5,5-tetramethyl-[1,3,2]dioxaborolan-2-yl)-benzamide was synthesized by operations similar to those in Reaction 51-3 using appropriate reagents and starting material.

MS (ESI) m/z=242 (M+H)+.

N-[3-Methyl-4-(4,4,5,5-tetramethyl-[1,3,2]dioxaborolan-2-yl)-phenyl]-acetamide was synthesized by operations similar to those in Reaction 51-3 using appropriate reagents and starting material.

MS (ESI) m/z=276 (M+H)+.

The following aryl bromide reagents used in the synthesis of Compounds 332, 333, 334, 335, 336 and 337 were synthesized by operations similar to those in Reaction 51-1 using appropriate reagents and starting materials.

TABLE 49

| Target Compound | Aryl bromide | MS |
|---|---|---|
| 332 | (structure) | 460, 462 (M + H)+ |
| 333 334 | (structure) | 540, 542 (M + H)+ |

TABLE 49-continued

| Target Compound | Aryl bromide | MS |
|---|---|---|
| 335 | 2-(3-trifluoromethoxyphenyl)-8-[(3-bromophenyl)sulfonyl]-1,3,8-triazaspiro[4.5]dec-1-en-4-one | 532, 534 (M + H)+ |
| 336 | 2-(3-trifluoromethoxyphenyl)-8-[(4-bromophenyl)sulfonyl]-1,3,8-triazaspiro[4.5]dec-1-en-4-one | 532, 534 (M + H)+ |
| 337 | 2-(3-trifluoromethoxyphenyl)-8-[(6-bromopyridin-2-yl)sulfonyl]-1,3,8-triazaspiro[4.5]dec-1-en-4-one | 533, 535 (M + H)+ |

Example 52

2-Cyclohexyl-8-{2-[2-(3,5-dimethyl-isoxazol-4-yl)-phenyl]-ethanesulfonyl}-1,3,8-triaza-spiro[4.5]dec-1-en-4-one (Compound 338)

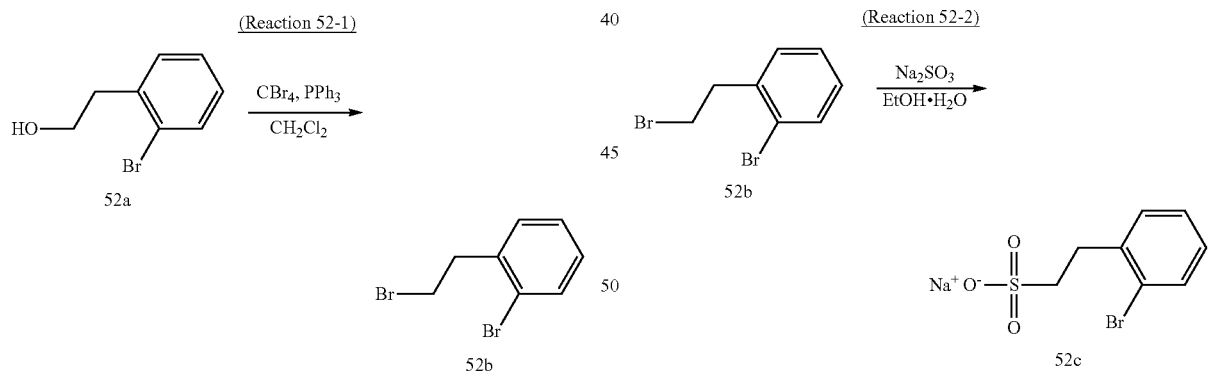

Triphenylphosphine (7.83 g, 29.8 mmol) and carbon tetrabromide (12.4 g, 37.3 mmol) were added to a solution of 2-(2-bromophenyl)ethanol (5.00 g, 24.9 mmol) in dichloromethane (123 mL). The mixture was stirred at room temperature for 15 hours, and a saturated aqueous sodium carbonate solution was then added. The organic layer and the aqueous layer were separated, and the organic layer was then concentrated under reduced pressure. The resulting residue was triturated with ethyl acetate:n-hexane (1:4, 200 mL) and then filtered, and the filtrate was concentrated under reduced pressure. The residue was purified by silica gel column chromatography to give 1-bromo-2-(2-bromoethyl)benzene as a colorless oil (6.23 g, 95%).

$^1$H-NMR (270 MHz, CDCl$_3$) δ 3.30 (2H, t, J=7.6 Hz), 3.60 (2H, t, J=7.3 Hz), 7.10-7.17 (1H, m), 7.26-7.28 (2H, m), 7.55 (1H, d, J=8.1 Hz).

A solution of 1-bromo-2-(2-bromoethyl)benzene (6.23 g, 23.6 mmol) in ethanol (20.5 mL) was added to a solution of sodium sulfite (3.12 g, 24.7 mmol) in water (25.0 mL). The mixture was heated at 100° C. for 24 hours. The reaction mixture was filtered, and the filtrate was then left to stand at 3° C. overnight. The resulting white crystals were collected by filtration and dried to give sodium 2-(2-bromo-phenyl)ethanesulfonate (4.00 g, 59%).

$^1$H-NMR (270 MHz, d$_6$-DMSO) δ 2.60-2.67 (2H, m), 2.94-3.00 (2H, m), 7.09-7.15 (1H, m), 7.25-7.33 (2H, m), 7.55 (1H, d, J=8.6 Hz).

(Reaction 52-3)

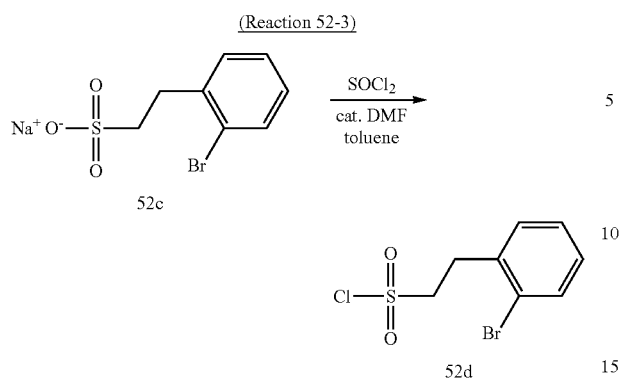

52c

N,N-Dimethylformamide (4.2 mL) and thionyl chloride (5.1 mL, 69.7 mmol) were sequentially added to a suspension of sodium 2-(2-bromo-phenyl)ethanesulfonate (4.00 g, 13.9 mmol) in toluene. The mixture was stirred at 100° C. for 66 hours and then poured into ice water. The organic layer and the aqueous layer were separated, and the aqueous layer was extracted with ether. The organic layers were combined and sequentially washed with water and saturated brine, and then dried over sodium sulfate and concentrated under reduced pressure to give 2-(2-bromophenyl)ethanesulfonyl chloride (4.10 g). This was used in the next step without further purification.

(Reaction 52-4)

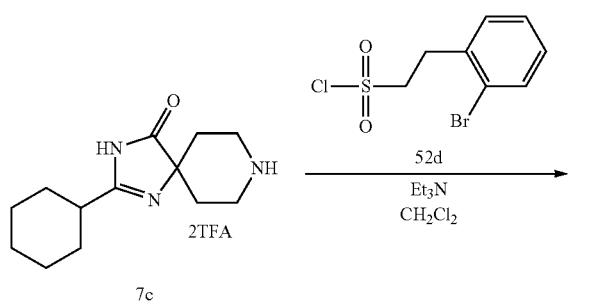

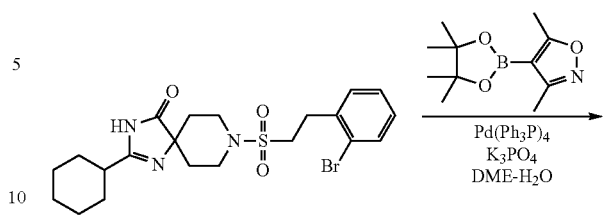

52e

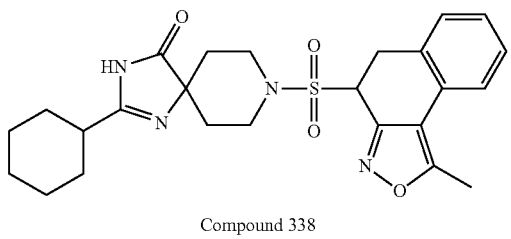

Compound 338

2-Cyclohexyl-8-{2-[2-(3,5-dimethyl-isoxazol-4-yl)-phenyl]-ethanesulfonyl}-1,3,8-triaza-spiro[4.5]dec-1-en-4-one was synthesized by operations similar to those in Reaction 5-4 and Reaction 21-1 using appropriate reagents and starting material.

MS (ESI) m/z=499 (M+H)+.

The example compounds shown below were synthesized by operations similar to those in Example 52 using appropriate reagents and starting materials.

Compounds 339 to 340

TABLE 50

| Compound | Structure | LCMS or HPLC condition | Retention time (min) | MS (m/z) |
| --- | --- | --- | --- | --- |
| 339 | 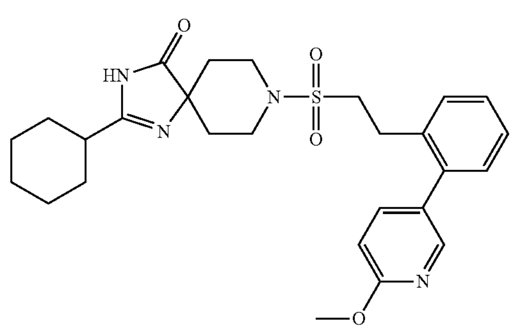 | LCMS-E-5 | 4.26 | 511 (M + H)+ |

| Compound | Structure | LCMS or HPLC condition | Retention time (min) | MS (m/z) |
|---|---|---|---|---|
| 340 | 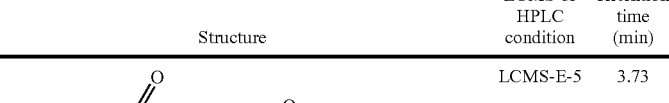 | LCMS-E-5 | 3.73 | 484 (M + H)+ |

Example 53

8-{5-[4-(3,4-Dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one (Compound 341)

(Reaction 53-1)

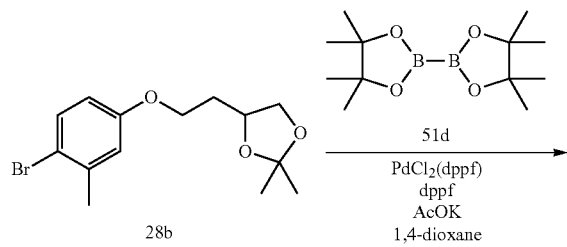

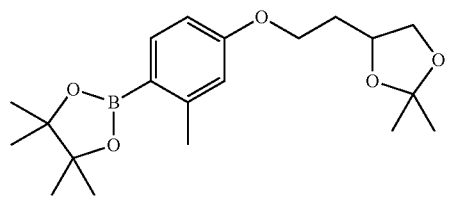

2-{4-[2-(2,2-Dimethyl-[1,3]dioxolan-4-yl)-ethoxy]-2-methyl-phenyl}-4,4,5,5-tetramethyl-[1,3,2]dioxaborolane was synthesized by operations similar to those in Reaction 51-3 using appropriate reagents and starting material.

MS (ESI) m/z=257 (M-C$_3$H$_6$O+H)+.

(Reaction 53-2)

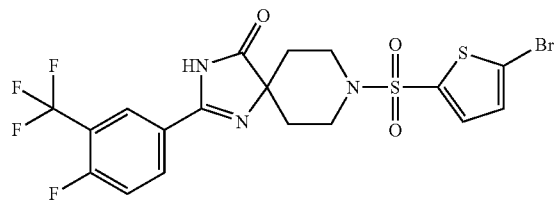 [SMILES: O=C1NC(c2ccc(F)c(C(F)(F)F)c2)=NC12CCN(S(=O)(=O)c1ccc(Br)s1)CC2]

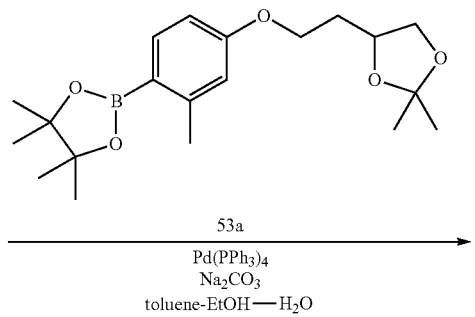

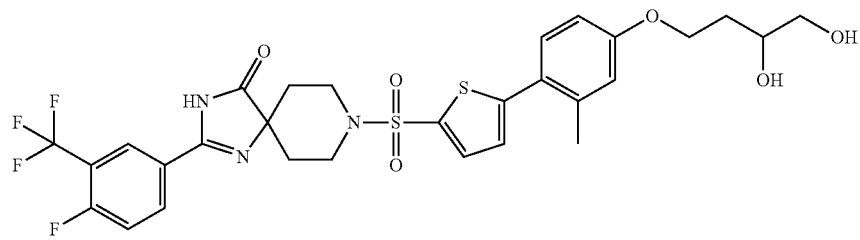

Compound 341

8-{5-[4-(3,4-Dihydroxy-butoxy)-2-methyl-phenyl]-thiophene-2-sulfonyl}-2-(4-fluoro-3-trifluoromethyl-phenyl)-1,3,8-triaza-spiro[4.5]dec-1-en-4-one was synthesized by operations similar to those in Reaction 51-2 and Reaction 25-4 using appropriate reagents and starting material.

MS (ESI) m/z=656 (M+H)+.

Example 54

N-(4-{5-[2-(4-Fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxyethyl)-acetamide (Compound 342)

(Reaction 54-1)

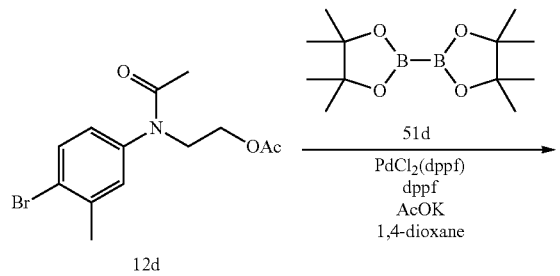

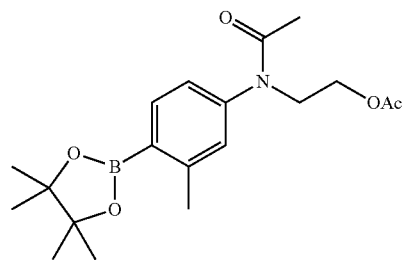

54a

Acetic acid 2-{acetyl-[3-methyl-4-(4,4,5,5-tetramethyl-[1,3,2]dioxaborolan-2-yl)-phenyl]-amino}-ethyl ester was synthesized by operations similar to those in Reaction 51-3 using appropriate reagents and starting material.

MS (ESI) m/z=315 (M+H)+.

(Reaction 54-2)

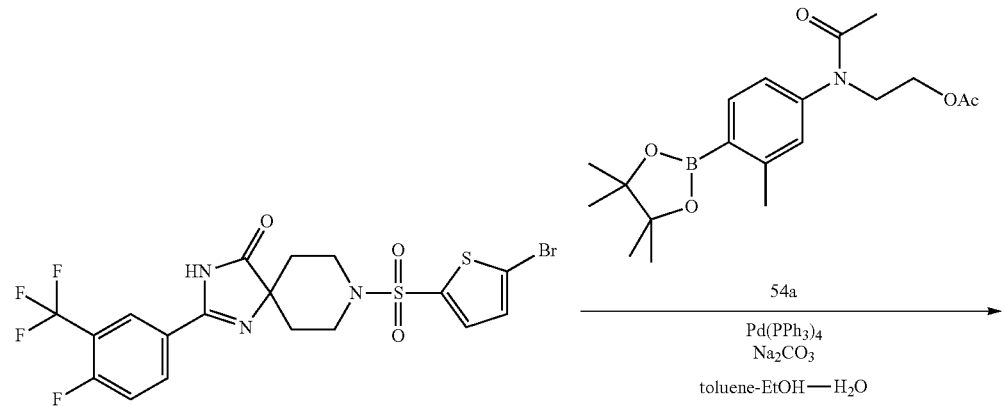

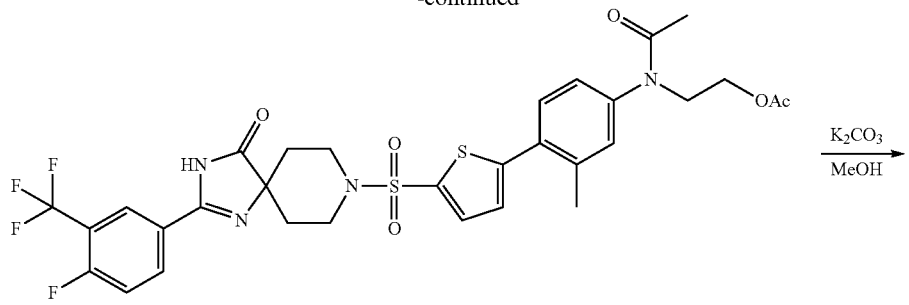

54b

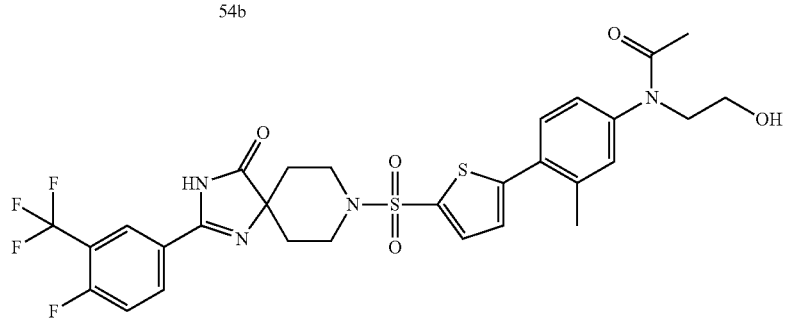

Compound 342

N-(4-{5-[2-(4-Fluoro-3-trifluoromethyl-phenyl)-4-oxo-1,3,8-triaza-spiro[4.5]dec-1-ene-8-sulfonyl]-thiophen-2-yl}-3-methyl-phenyl)-N-(2-hydroxy-ethyl)-acetamide was synthesized by operations similar to those in Reaction 51-2 and Reaction 12-5 using appropriate reagents and starting material.

MS (ESI) m/z=653 (M+H)+.

Example 55

2-Cyclohexyl-8-((E)-2-thiazol-2-yl-ethenesulfonyl)-1,3,8-triaza-spiro[4.5]dec-1-en-4-one (Compound 343)

(Reaction 55-1)

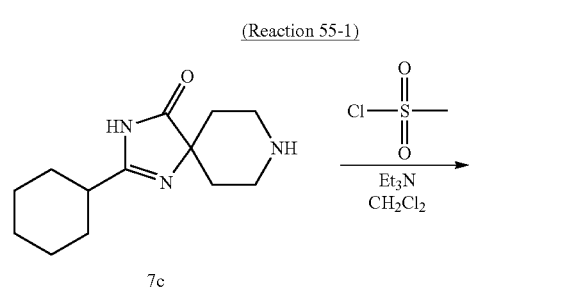

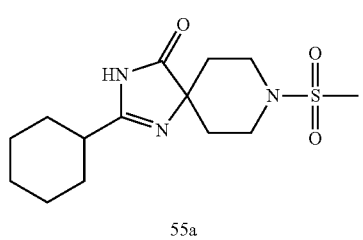

55a

2-Cyclohexyl-8-methanesulfonyl-1,3,8-triaza-spiro[4.5]dec-1-en-4-one was synthesized by operations similar to those in Reaction 5-4 using appropriate reagents and starting material.

MS (ESI) m/z=314 (M+H)+.

(Reaction 55-2)

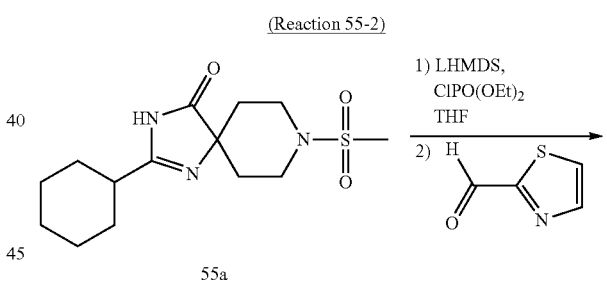

Compound 343

LHMDS (1.1 ml, 1.11 mmol) was added to a solution of 2-cyclohexyl-8-methanesulfonyl-1,3,8-triaza-spiro[4.5]dec-1-en-4-one (100 mg, 0.32 mmol) in THF (3 ml) at −20° C. in an $N_2$ atmosphere. The mixture was stirred at −20° C. for 30 minutes, and diethyl chlorophosphate (48 μl, 0.34 mmol) was then added. Further, the mixture was stirred at −20° C. for 60 minutes, and 2-thiazolecarboxyaldehyde (31 μl, 0.35 mmol) was then added. The reaction mixture was stirred at room temperature for one hour, and ethyl acetate (10 ml) and an aqueous $NH_4Cl$ solution (5 ml) were then added. The organic layer and the aqueous layer were separated, and the aqueous layer was then extracted with ethyl acetate (10 ml). The organic layers were combined and washed with saturated brine, and then dried over Na₂SO₄ and concentrated under reduced pressure. The resulting residue was recrystallized from ethyl acetate to give 2-cyclohexyl-8-((E)-2-thiazol-2-yl-ethenesulfonyl)-1,3,8-triaza-spiro[4.5]dec-1-en-4-one (87 mg, yield 67%).

¹H-NMR (300 MHz, CDCl₃) δ 8.38 (1H, s), 7.94 (1H, d, J=3.4 Hz), 7.57 (1H, d, J=15.3 Hz), 7.51 (1H, d, J=3.3 Hz), 7.11 (1H, d, J=15.3 Hz), 3.75 (2H, m), 3.31 (2H, m), 2.46-2.36 (1H, m), 2.07-1.97 (2H, m), 1.92-1.88 (2H, m), 1.83-1.80 (2H, m), 1.75-1.50 (4H, m), 1.50-1.20 (4H, m).

The example compound shown below was synthesized by operations similar to those in Example 55 using appropriate reagents and starting material.

Compound 344

TABLE 51

| Compound | Structure | LCMS or HPLC condition | Retention time (min) | MS (m/z) |
|---|---|---|---|---|
| 344 | 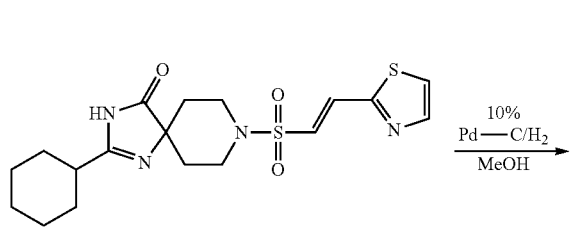 | HPLC-A-1 | 13.5 | 394 (M + H)+ |

Example 56

2-Cyclohexyl-8-(2-thiazol-2-yl-ethanesulfonyl)-1,3,8-triaza-spiro[4.5]dec-1-en-4-one (Compound 345)

Compound 343

Compound 345

2-Cyclohexyl-8-(2-thiazol-2-yl-ethanesulfonyl)-1,3,8-triaza-spiro[4.5]dec-1-en-4-one was synthesized by operations similar to those in Reaction 42-1 using appropriate reagents and starting material.

¹H-NMR (300 MHz, CDCl₃) δ 9.04 (1H, s), 7.70 (1H, d, J=3.5 Hz), 7.25 (1H, d, J=3.0 Hz), 3.75 (2H, m), 3.57-3.44 (4H, m), 3.37 (2H, m), 2.46-2.38 (1H, m), 2.01-1.90 (4H, m), 1.84-1.70 (3H, m), 1.56-1.50 (2H, m), 1.48-1.26 (5H, m). MS (ESI) m/z=411 (M+H)+.

Example 57

2-Cyclohexyl-8-[3-(4-methoxy-phenyl)-propane-1-sulfonyl]-1,3,8-triaza-spiro[4.5]dec-1-en-4-one (Compound 346)

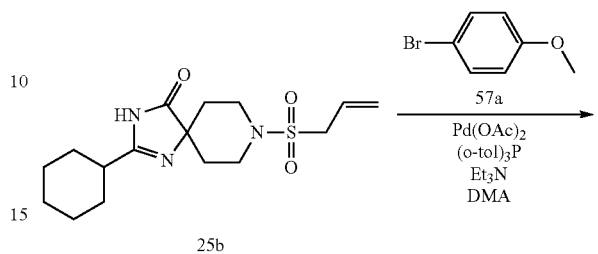

25b

-continued

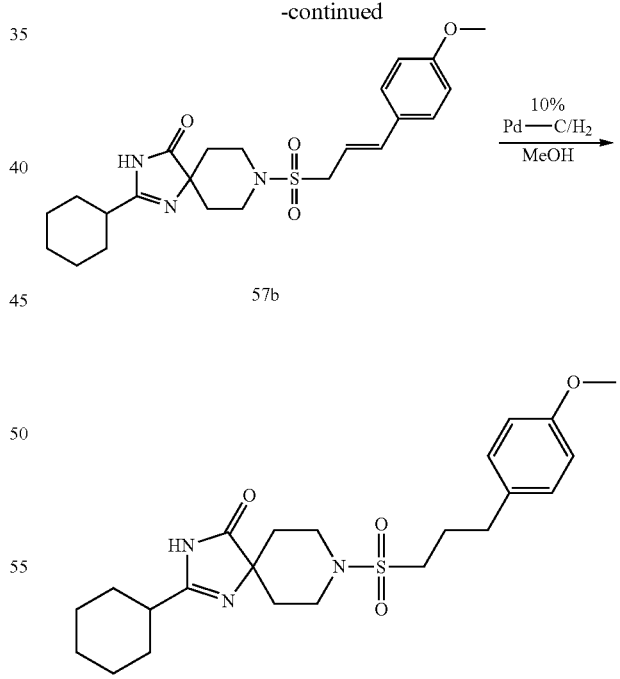

57b

Compound 346

2-Cyclohexyl-8-[3-(4-methoxy-phenyl)-propane-1-sulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=448 (M+H)+.

Example 58

N-Benzyl-2-(2-cyclohexyl-4-oxo-1,3,8-triaza-spiro[4.5]dec-1-ene-8-sulfonyl)-benzamide (Compound 347)

(Reaction 58-1)

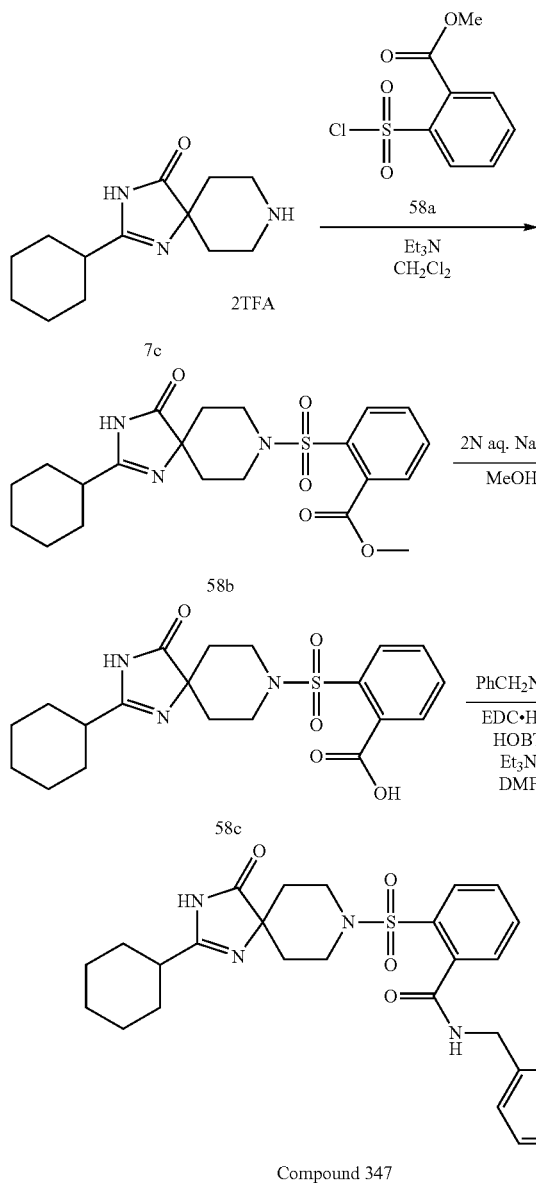

N-Benzyl-2-(2-cyclohexyl-4-oxo-1,3,8-triaza-spiro[4.5]dec-1-ene-8-sulfonyl)-benzamide was synthesized by operations similar to those in Reaction 5-4, Reaction 23-2 and Reaction 10-18 using appropriate reagents and starting material.

MS (ESI) m/z=509 (M+H)+.

Example 59

8-(3-Chloro-benzenesulfonyl)-2-[3-(morpholine-4-carbonyl)-phenyl]-1,3,8-triaza-spiro[4.5]dec-1-en-4-one (Compound 348)

(Reaction 59-1)

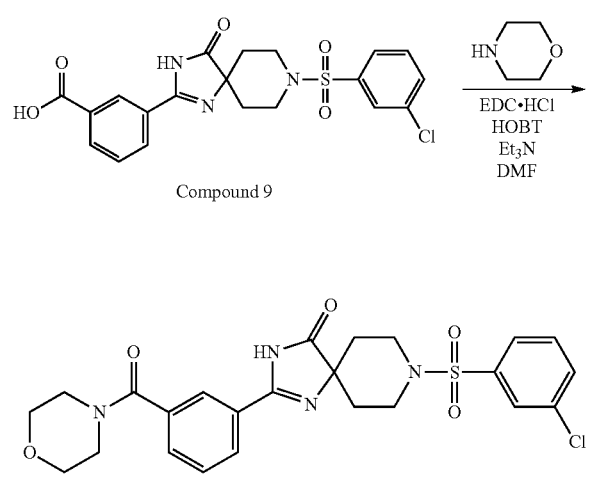

8-(3-Chloro-benzenesulfonyl)-2-[3-(morpholine-4-carbonyl)-phenyl]-1,3,8-triaza-spiro[4.5]dec-1-en-4-one was synthesized by operations similar to those in Reaction 10-18 using appropriate reagents and starting material.

MS (ESI) m/z=517 (M+H)+.

The example compounds shown below were synthesized by operations similar to those in Example 59 using appropriate reagents and starting materials.

Compounds 349 to 351

TABLE 52

| Compound | Structure | LCMS or HPLC condition | Retention time (min) | MS (m/z) |
|---|---|---|---|---|
| 349 | 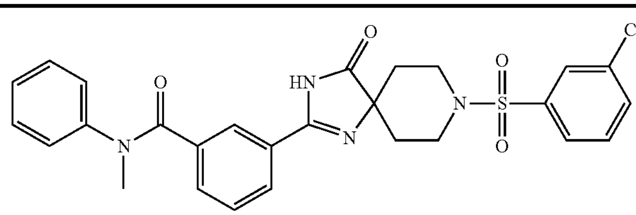 | LCMS-E-2 | 4.11 | 537 (M + H)+ |

TABLE 52-continued
| Compound | Structure | LCMS or HPLC condition | Retention time (min) | MS (m/z) |
| --- | --- | --- | --- | --- |
| 350 | ![structure] | LCMS-E-6 | 1.76 | 537 (M + H)+ |
| 351 | ![structure] | LCMS-E-6 | 1.42 | 475 (M + H)+ |
Example 60
8-{2-[4-(4-Methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one (Compound 352)
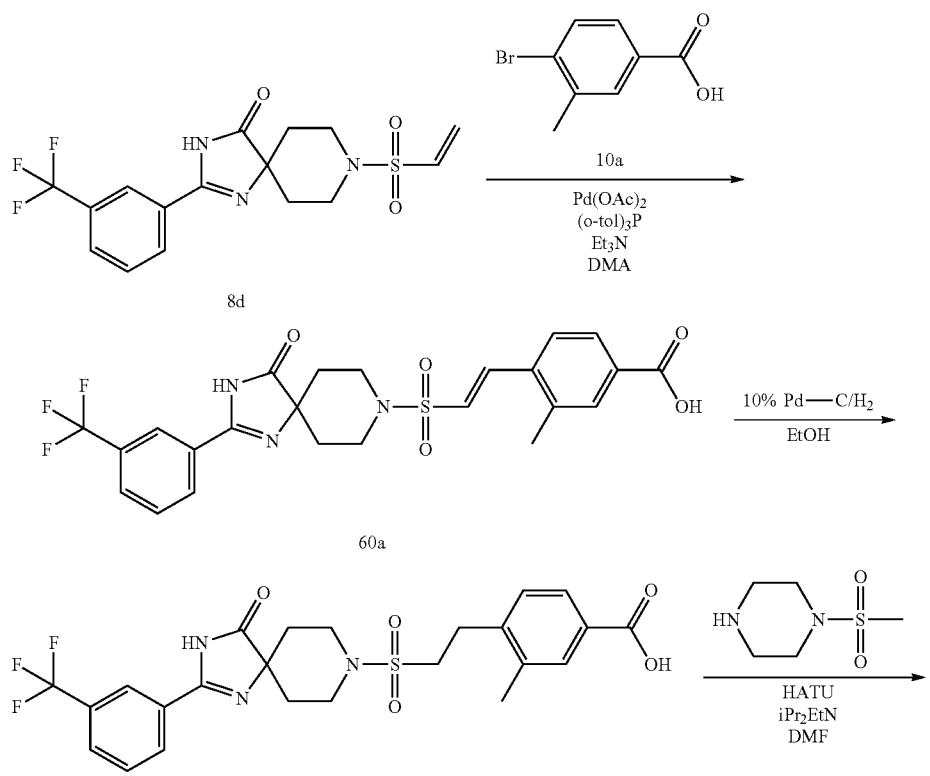

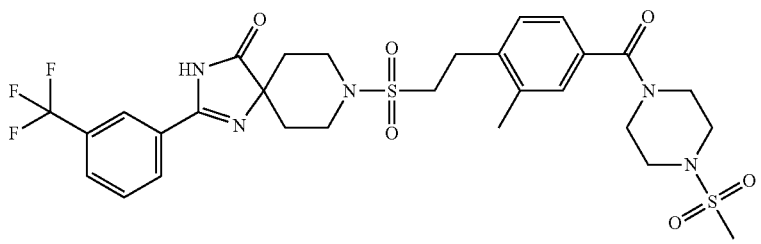

Compound 352

8-{2-[4-(4-Methanesulfonyl-piperazine-1-carbonyl)-2-methyl-phenyl]-ethanesulfonyl}-2-(3-trifluoromethyl-phenyl)-1,3,8-triaza-spiro[4.5]dec-1-en-4-one was synthesized by operations similar to those in Reaction 26-1, Reaction 18-2 and Reaction 10-14 using appropriate reagents and starting material.

MS (ESI) m/z=670 (M+H)+.

The example compounds shown below were synthesized by operations similar to those in Example 60 using appropriate reagents and starting materials.

Compounds 353 to 382

TABLE 53

| Compound | Structure | LCMS or HPLC condition | Retention time (min) | MS (m/z) |
|---|---|---|---|---|
| 353 | 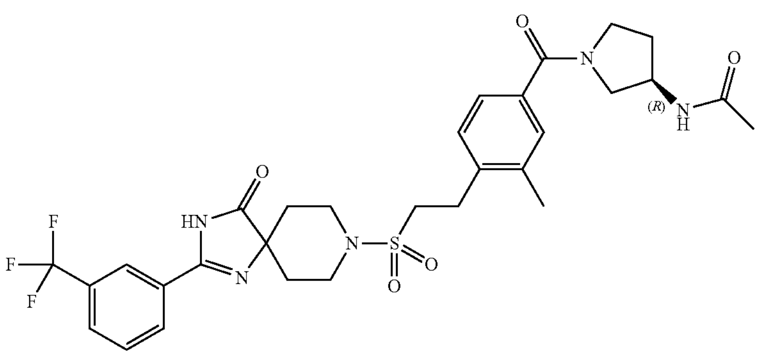 | LCMS-C-1 | 2.43 | 634 (M + H)+ |
| 354 | 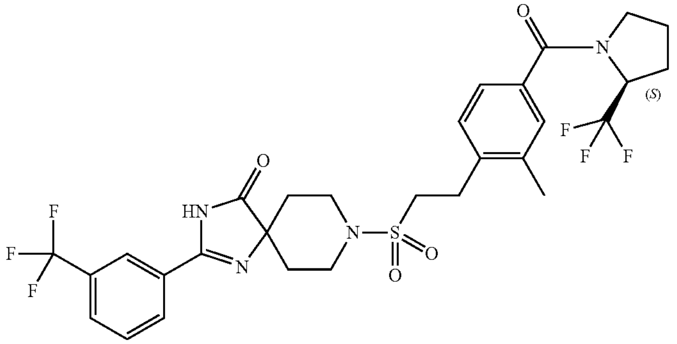 | LCMS-C-1 | 2.85 | 645 (M + H)+ |

TABLE 53-continued

| Compound | Structure | LCMS or HPLC condition | Retention time (min) | MS (m/z) |
|---|---|---|---|---|
| 355 | 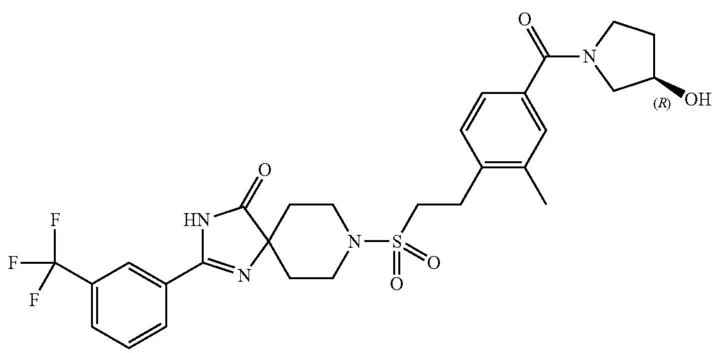 | LCMS-C-1 | 2.45 | 593 (M + H)+ |
| 356 | 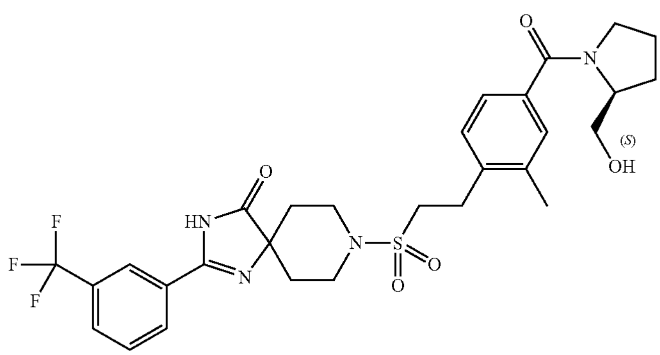 | LCMS-C-1 | 2.58 | 607 (M + H)+ |
| 357 | 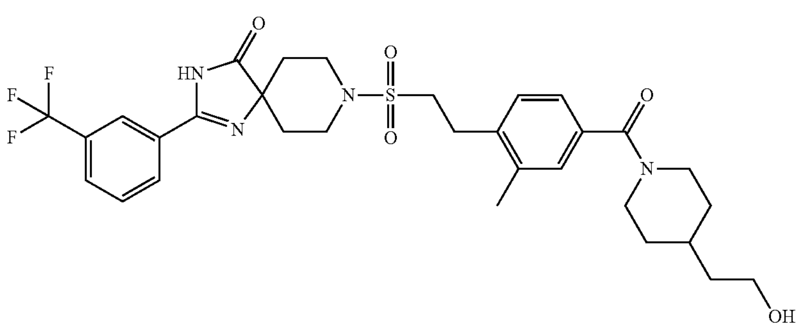 [SMILES: Cc1cc(C(=O)N2CCC(CCO)CC2)ccc1CCS(=O)(=O)N1CCC2(CC1)N=C(c1cccc(C(F)(F)F)c1)NC2=O] | LCMS-A-1 | 2.30 | 635 (M + H)+ |
| 358 | 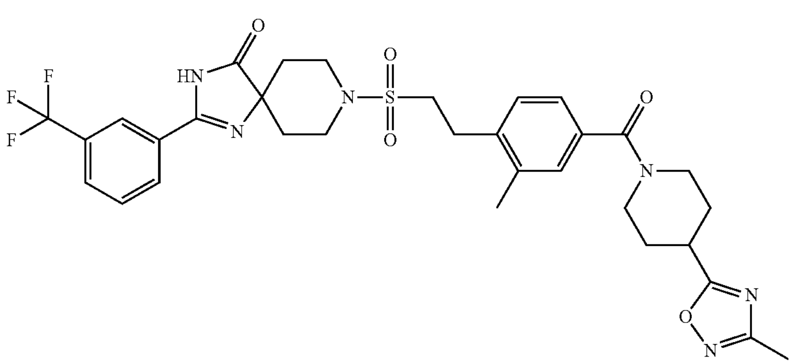 [SMILES: Cc1noc(C2CCN(C(=O)c3ccc(CCS(=O)(=O)N4CCC5(CC4)N=C(c4cccc(C(F)(F)F)c4)NC5=O)c(C)c3)CC2)n1] | LCMS-A-1 | 2.50 | 673 (M + H)+ |

TABLE 53-continued

| Compound | Structure | LCMS or HPLC condition | Retention time (min) | MS (m/z) |
|---|---|---|---|---|
| 359 | 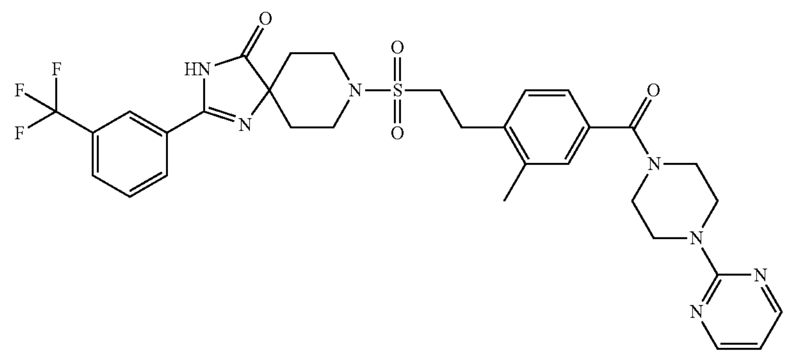 [SMILES: Cc1cc(C(=O)N2CCN(c3ncccn3)CC2)ccc1CCS(=O)(=O)N1CCC2(CC1)N=C(c1cccc(C(F)(F)F)c1)NC2=O] | LCMS-A-1 | 2.45 | 670 (M + H)+ |
| 360 | 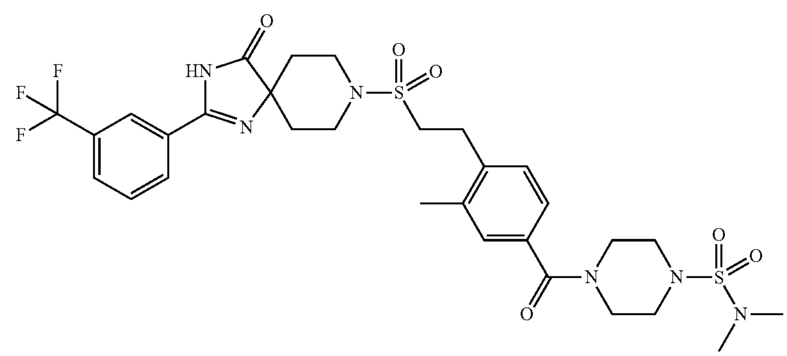 [SMILES: Cc1cc(C(=O)N2CCN(S(=O)(=O)N(C)C)CC2)ccc1CCS(=O)(=O)N1CCC2(CC1)N=C(c1cccc(C(F)(F)F)c1)NC2=O] | LCMS-C-1 | 2.58 | 699 (M + H)+ |
| 361 | 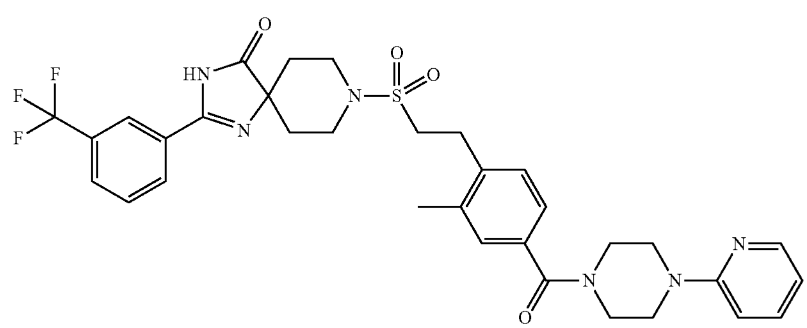 [SMILES: Cc1cc(C(=O)N2CCN(c3ccccn3)CC2)ccc1CCS(=O)(=O)N1CCC2(CC1)N=C(c1cccc(C(F)(F)F)c1)NC2=O] | LCMS-C-1 | 2.78 | 669 (M + H)+ |
| 362 | 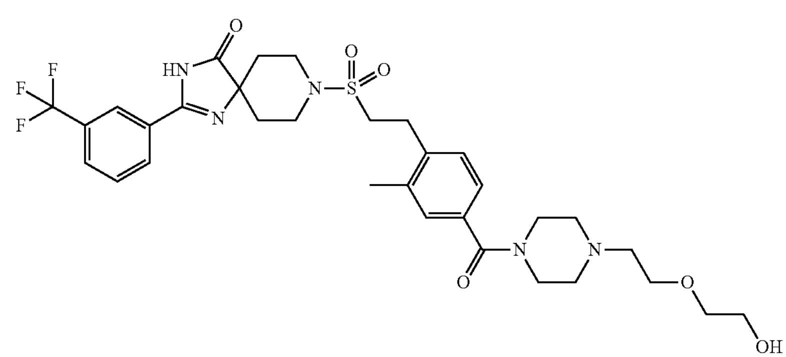 [SMILES: Cc1cc(C(=O)N2CCN(CCOCCO)CC2)ccc1CCS(=O)(=O)N1CCC2(CC1)N=C(c1cccc(C(F)(F)F)c1)NC2=O] | LCMS-C-1 | 2.47 | 680 (M + H)+ |

TABLE 53-continued

| Compound | Structure | LCMS or HPLC condition | Retention time (min) | MS (m/z) |
|---|---|---|---|---|
| 363 | 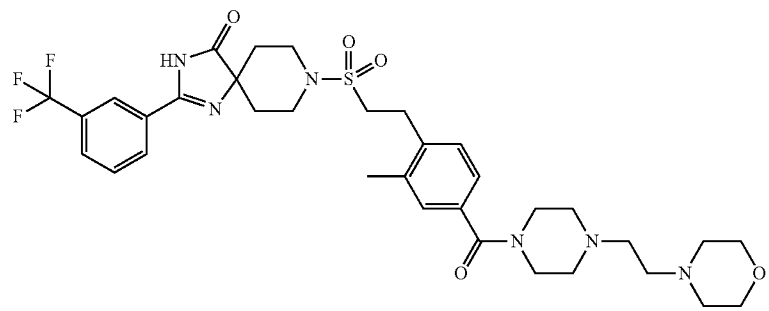 [SMILES: Cc1cc(C(=O)N2CCN(CCN3CCOCC3)CC2)ccc1CCS(=O)(=O)N1CCC2(CC1)N=C(c1cccc(C(F)(F)F)c1)NC2=O] | LCMS-C-1 | 2.53 | 705 (M + H)+ |
| 364 | 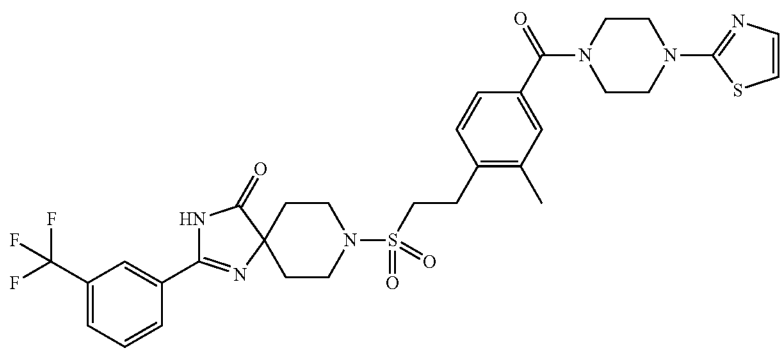 [SMILES: Cc1cc(C(=O)N2CCN(c3nccs3)CC2)ccc1CCS(=O)(=O)N1CCC2(CC1)N=C(c1cccc(C(F)(F)F)c1)NC2=O] | LCMS-C-1 | 2.72 | 675 (M + H)+ |
| 365 | 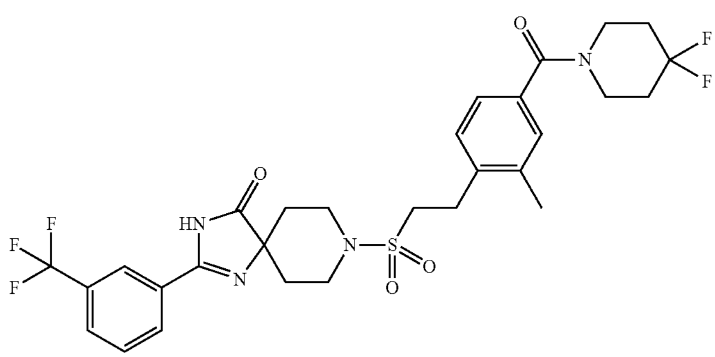 [SMILES: Cc1cc(C(=O)N2CCC(F)(F)CC2)ccc1CCS(=O)(=O)N1CCC2(CC1)N=C(c1cccc(C(F)(F)F)c1)NC2=O] | LCMS-A-1 | 2.67 | 627 (M + H)+ |
| 366 | 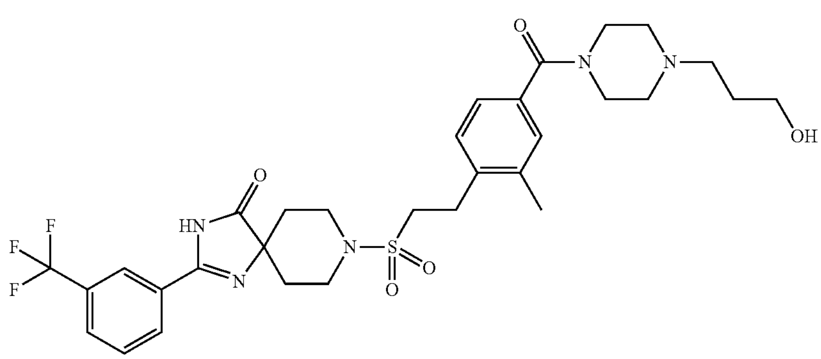 [SMILES: Cc1cc(C(=O)N2CCN(CCCO)CC2)ccc1CCS(=O)(=O)N1CCC2(CC1)N=C(c1cccc(C(F)(F)F)c1)NC2=O] | LCMS-A-1 | 1.95 | 650 (M + H)+ |

TABLE 53-continued

| Compound | Structure | LCMS or HPLC condition | Retention time (min) | MS (m/z) |
|---|---|---|---|---|
| 367 | 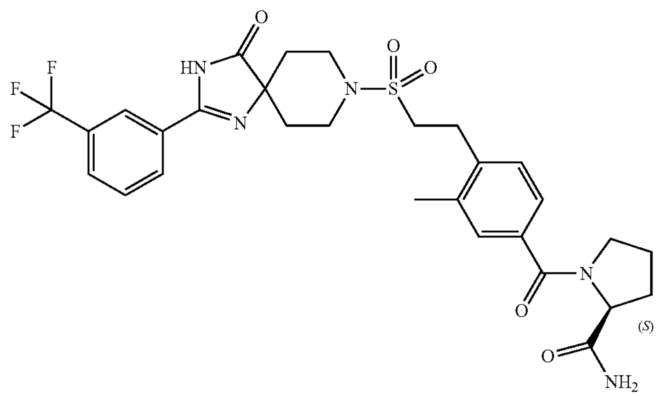 | LCMS-C-1 | 2.42 | 620 (M + H)+ |
| 368 | 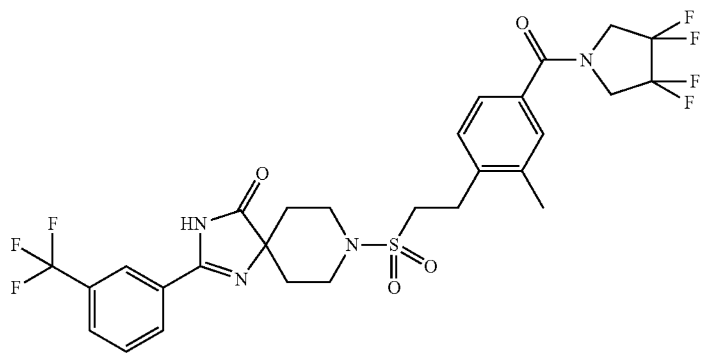 [SMILES: Cc1cc(C(=O)N2CC(F)(F)C(F)(F)C2)ccc1CCS(=O)(=O)N1CCC2(CC1)N=C(c1cccc(C(F)(F)F)c1)NC2=O] | LCMS-A-1 | 2.81 | 649 (M + H)+ |
| 369 | 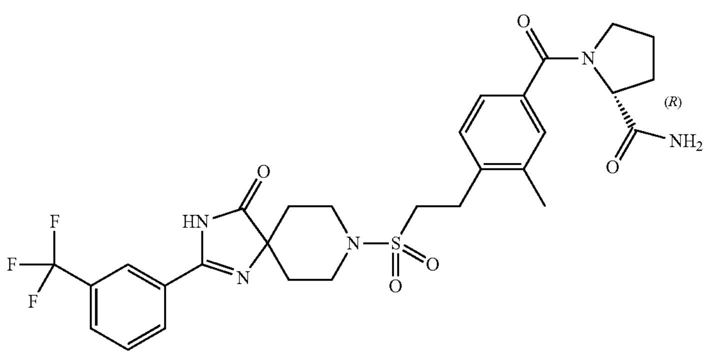 | LCMS-C-1 | 2.42 | 620 (M + H)+ |
| 370 | 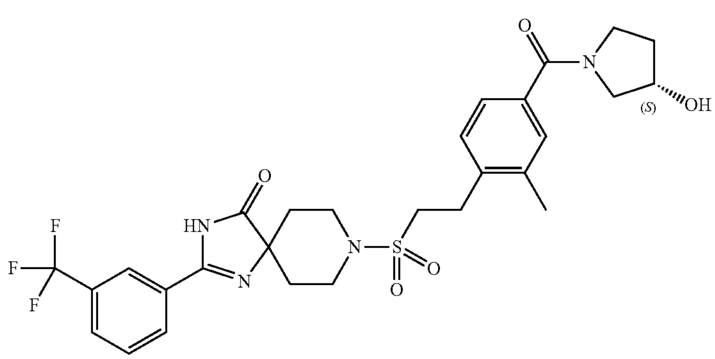 | LCMS-C-1 | 2.42 | 593 (M + H)+ |

TABLE 53-continued

| Compound | Structure | LCMS or HPLC condition | Retention time (min) | MS (m/z) |
|---|---|---|---|---|
| 371 | 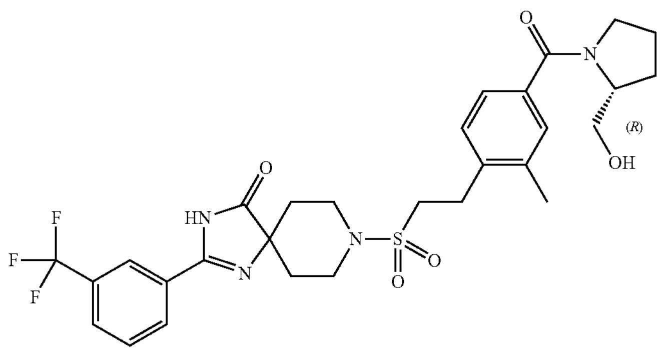 | LCMS-C-1 | 2.55 | 607 (M + H)+ |
| 372 | 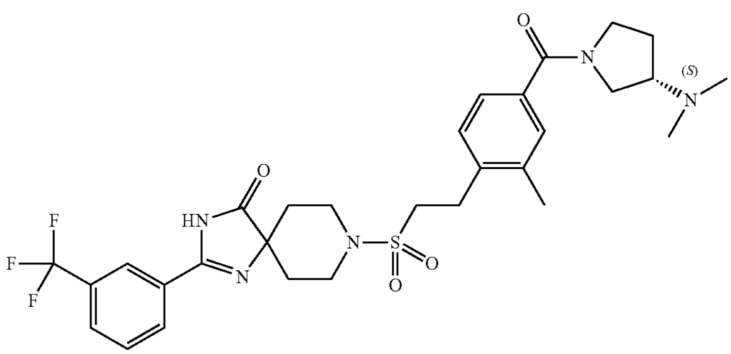 | LCMS-C-1 | 2.57 | 620 (M + H)+ |
| 373 | 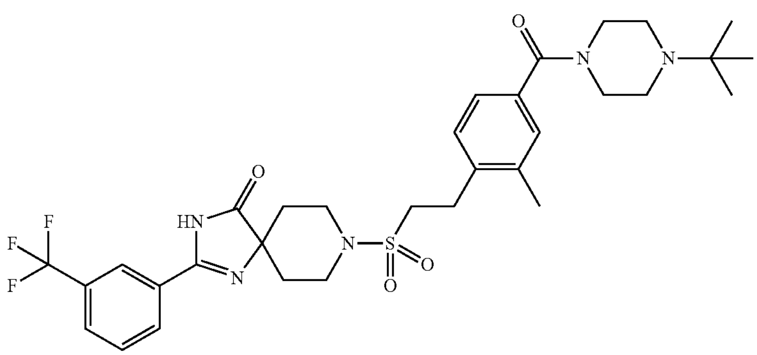 [SMILES: Cc1cc(C(=O)N2CCN(C(C)(C)C)CC2)ccc1CCS(=O)(=O)N1CCC2(CC1)N=C(c1cccc(C(F)(F)F)c1)NC2=O] | LCMS-A-1 | 2.08 | 648 (M + H)+ |
| 374 | 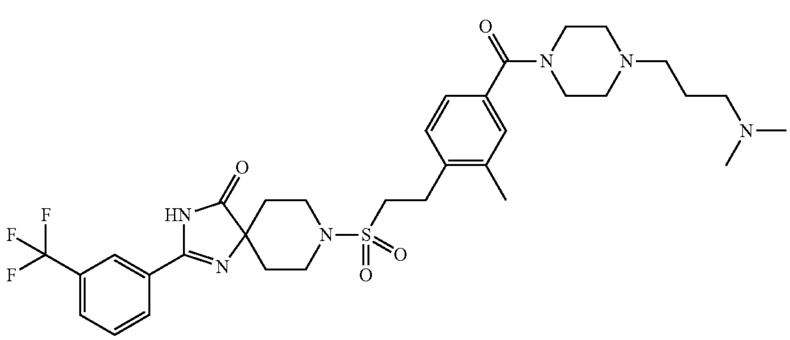 [SMILES: Cc1cc(C(=O)N2CCN(CCCN(C)C)CC2)ccc1CCS(=O)(=O)N1CCC2(CC1)N=C(c1cccc(C(F)(F)F)c1)NC2=O] | LCMS-C-1 | 2.43 | 677 (M + H)+ |

TABLE 53-continued

| Compound | Structure | LCMS or HPLC condition | Retention time (min) | MS (m/z) |
|---|---|---|---|---|
| 375 | 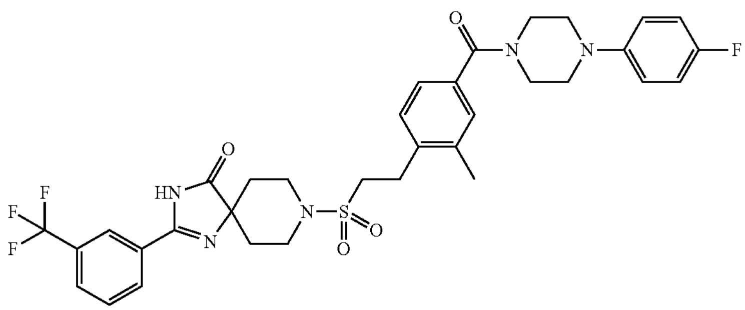 [SMILES: Cc1cc(C(=O)N2CCN(c3ccc(F)cc3)CC2)ccc1CCS(=O)(=O)N1CCC2(CC1)N=C(c1cccc(C(F)(F)F)c1)NC2=O] | LCMS-A-1 | 2.79 | 686 (M + H)+ |
| 376 | 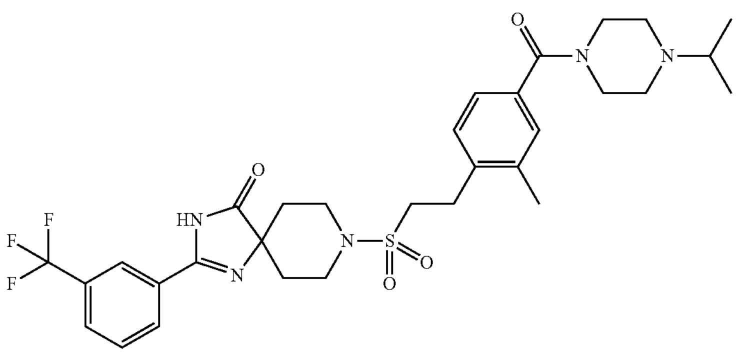 [SMILES: Cc1cc(C(=O)N2CCN(C(C)C)CC2)ccc1CCS(=O)(=O)N1CCC2(CC1)N=C(c1cccc(C(F)(F)F)c1)NC2=O] | LCMS-A-1 | 2.03 | 634 (M + H)+ |
| 377 | 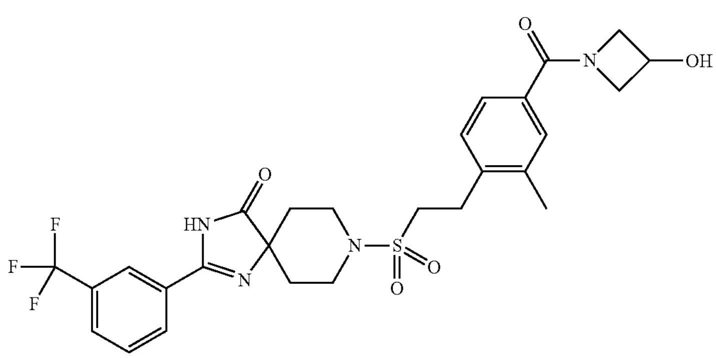 [SMILES: Cc1cc(C(=O)N2CC(O)C2)ccc1CCS(=O)(=O)N1CCC2(CC1)N=C(c1cccc(C(F)(F)F)c1)NC2=O] | LCMS-C-1 | 2.40 | 579 (M + H)+ |
| 378 | 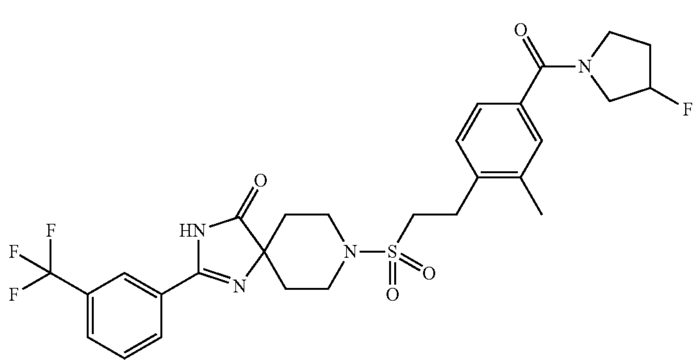 [SMILES: Cc1cc(C(=O)N2CCC(F)C2)ccc1CCS(=O)(=O)N1CCC2(CC1)N=C(c1cccc(C(F)(F)F)c1)NC2=O] | LCMS-B-1 | 2.16 | 595 (M + H)+ |

TABLE 53-continued

| Compound | Structure | LCMS or HPLC condition | Retention time (min) | MS (m/z) |
|---|---|---|---|---|
| 379 | 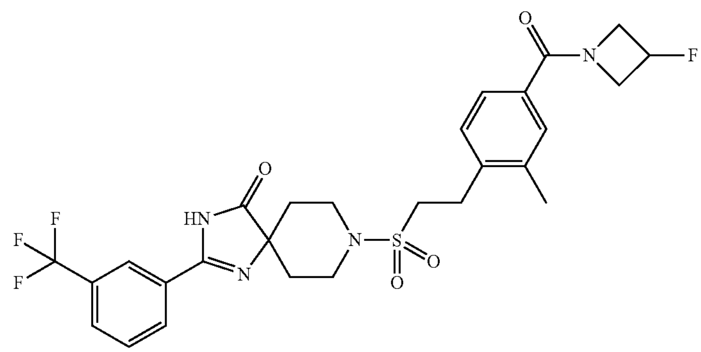 [SMILES: Cc1cc(C(=O)N2CC(F)C2)ccc1CCS(=O)(=O)N1CCC2(CC1)N=C(c1cccc(C(F)(F)F)c1)NC2=O] | LCMS-B-1 | 2.15 | 581 (M + H)+ |
| 380 | 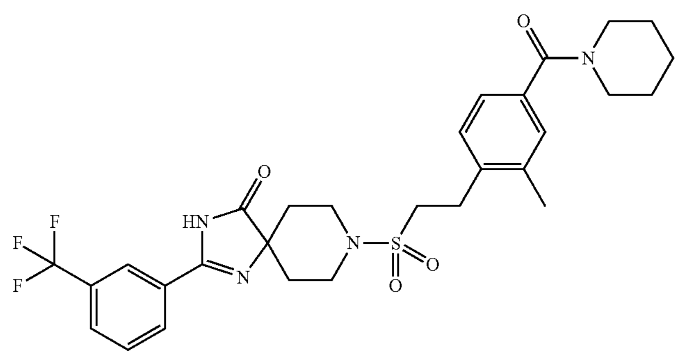 [SMILES: Cc1cc(C(=O)N2CCCCC2)ccc1CCS(=O)(=O)N1CCC2(CC1)N=C(c1cccc(C(F)(F)F)c1)NC2=O] | LCMS-B-1 | 2.38 | 591 (M + H)+ |
| 381 | 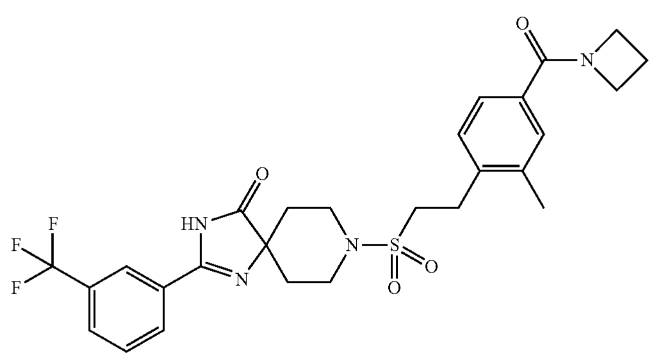 [SMILES: Cc1cc(C(=O)N2CCC2)ccc1CCS(=O)(=O)N1CCC2(CC1)N=C(c1cccc(C(F)(F)F)c1)NC2=O] | LCMS-B-1 | 2.12 | 563 (M + H)+ |
| 382 | 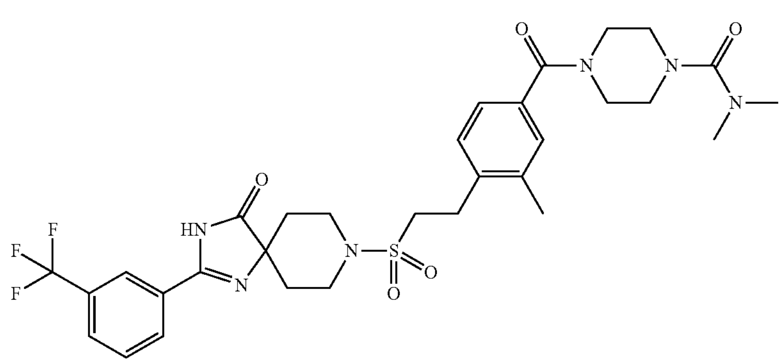 [SMILES: Cc1cc(C(=O)N2CCN(C(=O)N(C)C)CC2)ccc1CCS(=O)(=O)N1CCC2(CC1)N=C(c1cccc(C(F)(F)F)c1)NC2=O] | LCMS-C-1 | 2.52 | 663 (M + H)+ |

Example 61

3,5,N,N-Tetramethyl-4-{(E)-2-[4-oxo-2-(3-trifluoromethyl-phenyl)-1,3,8-triaza-spiro[4.5]dec-1-ene-8-sulfonyl]-vinyl}-benzamide (Compound 383)

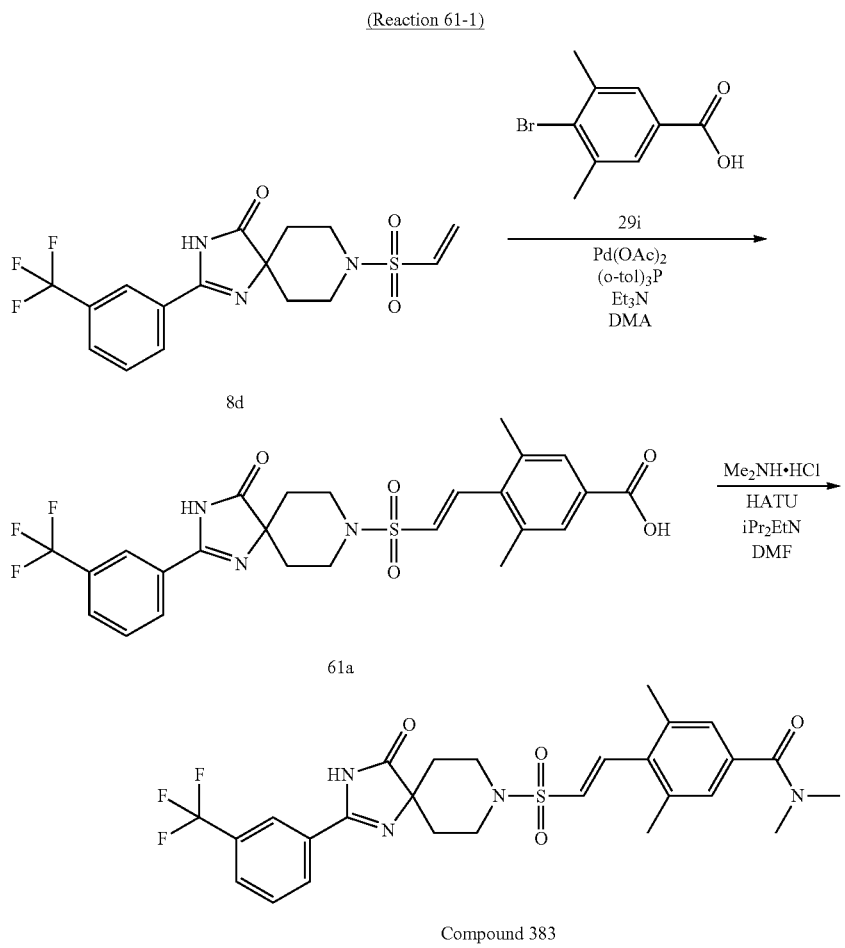

3,5,N,N-Tetramethyl-4-{(E)-2-[4-oxo-2-(3-trifluoromethyl-phenyl)-1,3,8-triaza-spiro[4.5]dec-1-ene-8-sulfonyl]-vinyl}-benzamide was synthesized by operations similar to those in Reaction 26-1 and Reaction 10-14 using appropriate reagents and starting material.

MS (ESI) m/z=563 (M+H)+.

The example compounds shown below were synthesized by operations similar to those in Example 61 using appropriate reagents and starting materials.

Compounds 384 to 393

TABLE 54

| Compound | Structure | LCMS or HPLC condition | Retention time (min) | MS (m/z) |
|---|---|---|---|---|
| 384 | 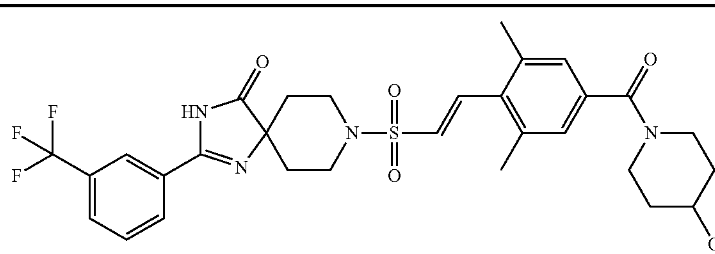 | LCMS-C-1 | 2.53 | 619 (M + H)+ |

TABLE 54-continued

| Compound | Structure | LCMS or HPLC condition | Retention time (min) | MS (m/z) |
|---|---|---|---|---|
| 385 | 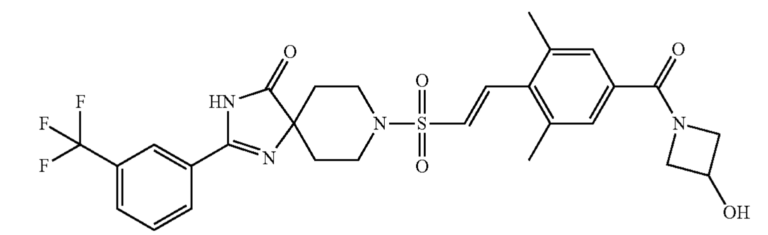 [SMILES: Cc1cc(C(=O)N2CC(O)C2)cc(C)c1/C=C/S(=O)(=O)N1CCC2(CC1)N=C(c1cccc(C(F)(F)F)c1)NC2=O] | LCMS-C-1 | 2.52 | 591 (M + H)+ |
| 386 | 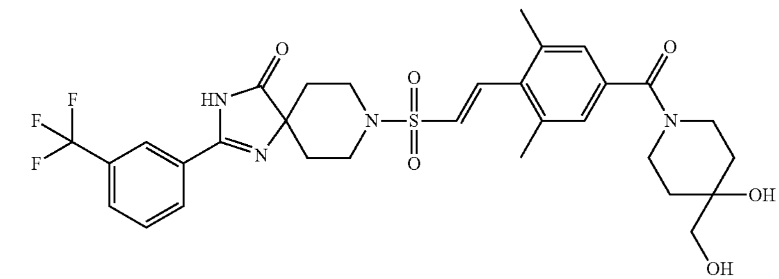 [SMILES: Cc1cc(C(=O)N2CCC(O)(CO)CC2)cc(C)c1/C=C/S(=O)(=O)N1CCC2(CC1)N=C(c1cccc(C(F)(F)F)c1)NC2=O] | LCMS-C-1 | 2.48 | 649 (M + H)+ |
| 387 | 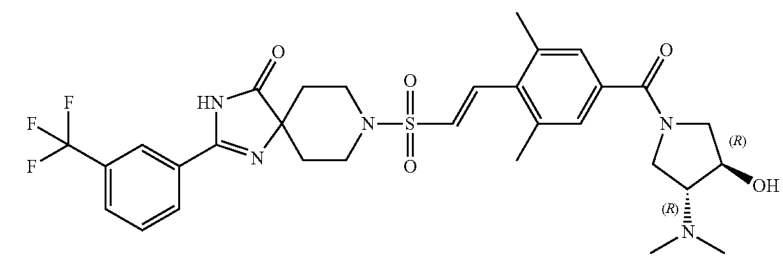 | LCMS-C-1 | 2.50 | 648 (M + H)+ |
| 388 | 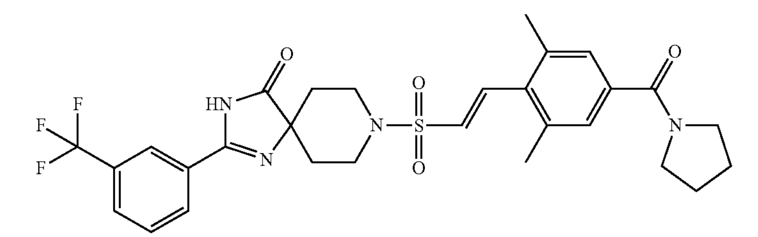 [SMILES: Cc1cc(C(=O)N2CCCC2)cc(C)c1/C=C/S(=O)(=O)N1CCC2(CC1)N=C(c1cccc(C(F)(F)F)c1)NC2=O] | LCMS-C-1 | 2.77 | 589 (M + H)+ |
| 389 | 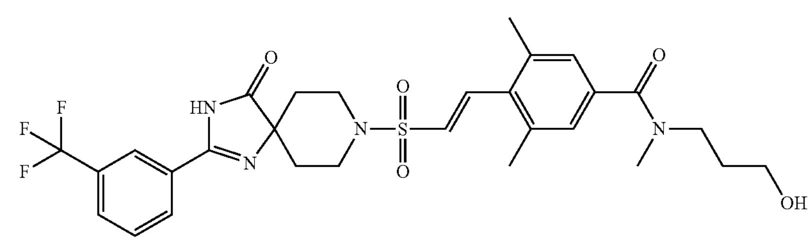 [SMILES: Cc1cc(C(=O)N(C)CCCO)cc(C)c1/C=C/S(=O)(=O)N1CCC2(CC1)N=C(c1cccc(C(F)(F)F)c1)NC2=O] | LCMS-C-1 | 2.53 | 607 (M + H)+ |
| 390 | 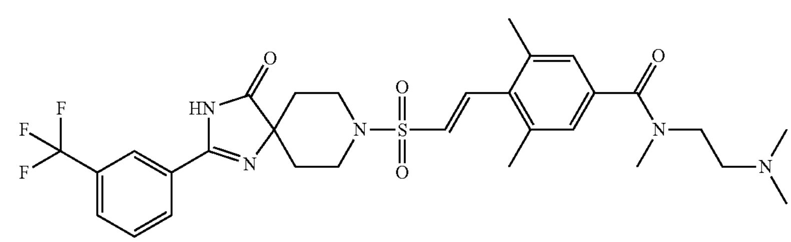 [SMILES: Cc1cc(C(=O)N(C)CCN(C)C)cc(C)c1/C=C/S(=O)(=O)N1CCC2(CC1)N=C(c1cccc(C(F)(F)F)c1)NC2=O] | LCMS-C-1 | 2.60 | 620 (M + H)+ |

TABLE 54-continued
| Compound | Structure | LCMS or HPLC condition | Retention time (min) | MS (m/z) |
|---|---|---|---|---|
| 391 | 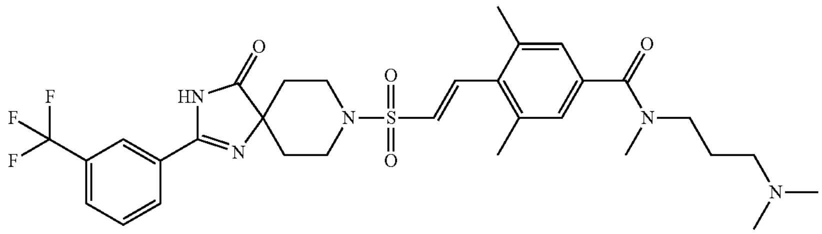 [SMILES: Cc1cc(C(=O)N(C)CCCN(C)C)cc(C)c1/C=C/S(=O)(=O)N1CCC2(CC1)N=C(c1cccc(C(F)(F)F)c1)NC2=O] | LCMS-C-1 | 2.48 | 634 (M + H)+ |
| 392 | 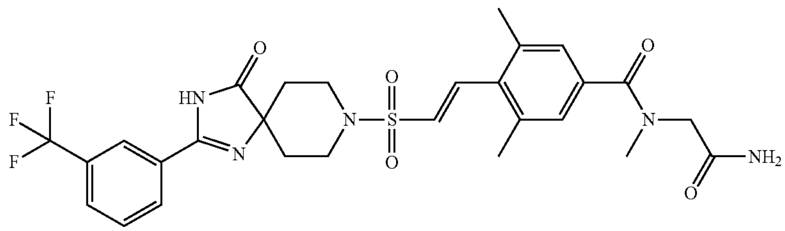 [SMILES: Cc1cc(C(=O)N(C)CC(N)=O)cc(C)c1/C=C/S(=O)(=O)N1CCC2(CC1)N=C(c1cccc(C(F)(F)F)c1)NC2=O] | LCMS-C-1 | 2.28 | 606 (M + H)+ |
| 393 | 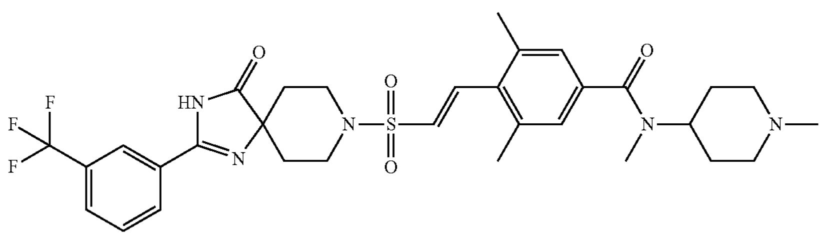 [SMILES: Cc1cc(C(=O)N(C)C2CCN(C)CC2)cc(C)c1/C=C/S(=O)(=O)N1CCC2(CC1)N=C(c1cccc(C(F)(F)F)c1)NC2=O] | LCMS-C-1 | 2.62 | 646 (M + H)+ |
Example 62
8-{(E)-2-[4-(4-Acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 394)
(Reaction 62-1)
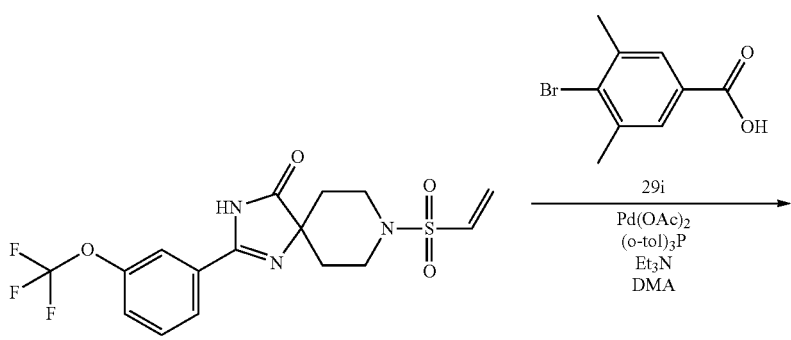

-continued

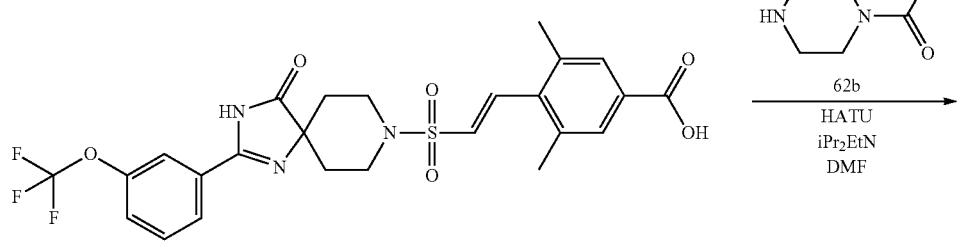

62a

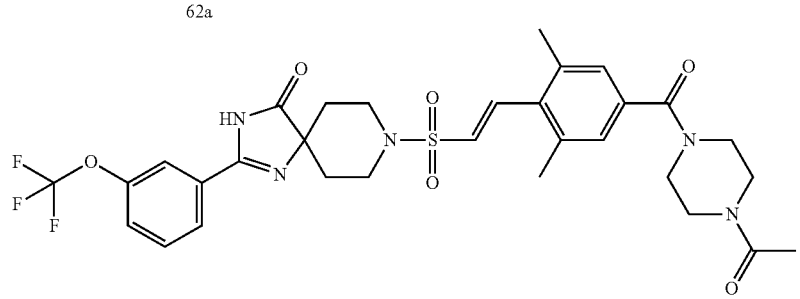

Compound 394

8-{(E)-2-[4-(4-Acetyl-piperazine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 26-1 and Reaction 10-14 using appropriate reagents and starting material.
MS (ESI) m/z=662 (M+H)+.

The example compounds shown below were synthesized by operations similar to those in Example 62 using appropriate reagents and starting materials.

Compounds 395 to 408

TABLE 55

| Compound | Structure | LCMS or HPLC condition | Retention time (min) | MS (m/z) |
|---|---|---|---|---|
| 395 | 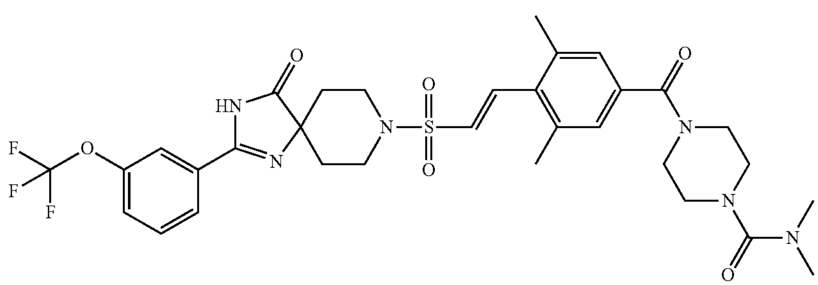 [SMILES: Cc1cc(C(=O)N2CCN(C(=O)N(C)C)CC2)cc(C)c1/C=C/S(=O)(=O)N1CCC2(CC1)N=C(c1cccc(OC(F)(F)F)c1)NC2=O] | LCMS-C-1 | 2.67 | 691 (M + H)+ |
| 396 | 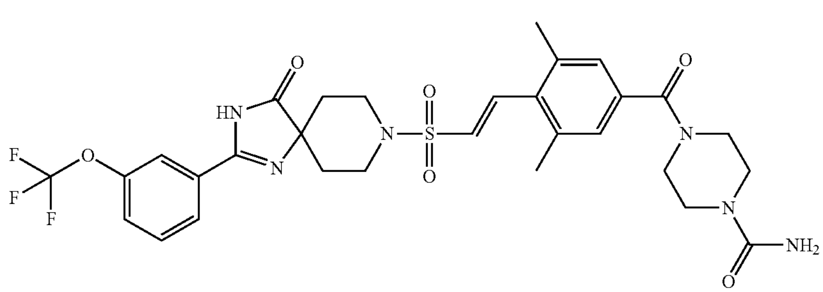 [SMILES: Cc1cc(C(=O)N2CCN(C(N)=O)CC2)cc(C)c1/C=C/S(=O)(=O)N1CCC2(CC1)N=C(c1cccc(OC(F)(F)F)c1)NC2=O] | LCMS-C-1 | 2.52 | 663 (M + H)+ |

TABLE 55-continued

| Compound | Structure | LCMS or HPLC condition | Retention time (min) | MS (m/z) |
|---|---|---|---|---|
| 397 | 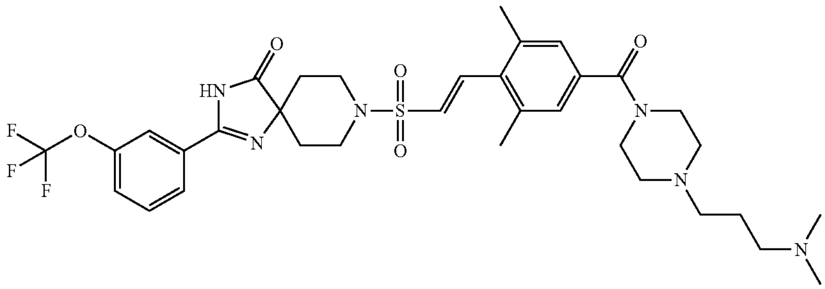 [SMILES: Cc1cc(C(=O)N2CCN(CCCN(C)C)CC2)cc(C)c1/C=C/S(=O)(=O)N1CCC2(CC1)N=C(c1cccc(OC(F)(F)F)c1)NC2=O] | LCMS-C-1 | 2.50 | 705 (M + H)+ |
| 398 | 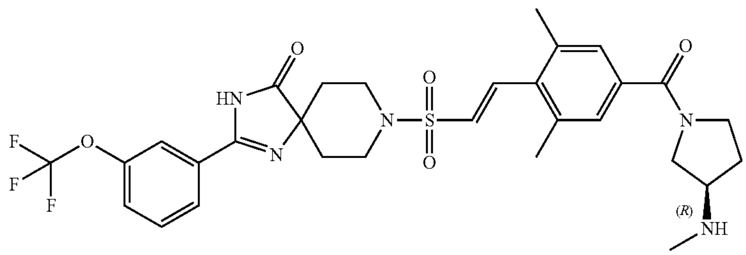 | LCMS-D-1 | 2.7 | 634 (M + H)+ |
| 399 | 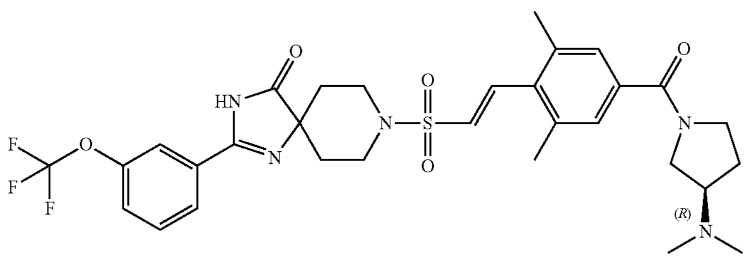 | LCMS-D-1 | 2.7 | 648 (M + H)+ |
| 400 | 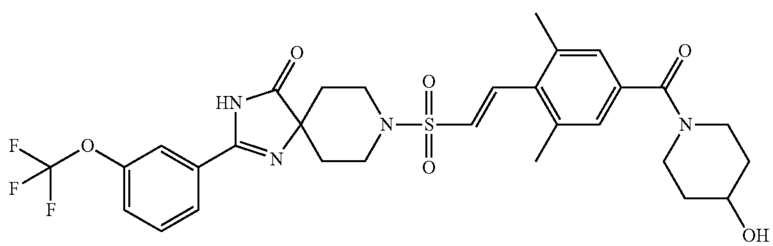 [SMILES: Cc1cc(C(=O)N2CCC(O)CC2)cc(C)c1/C=C/S(=O)(=O)N1CCC2(CC1)N=C(c1cccc(OC(F)(F)F)c1)NC2=O] | LCMS-D-1 | 3.0 | 635 (M + H)+ |
| 401 | 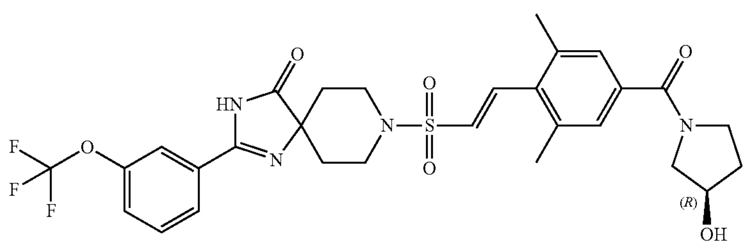 | LCMS-D-1 | 3.0 | 621 (M + H)+ |
| 402 | 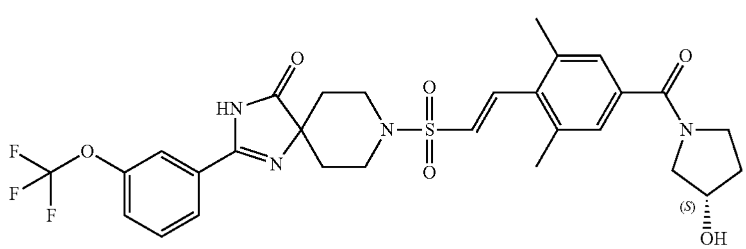 | LCMS-D-1 | 3.0 | 621 (M + H)+ |

TABLE 55-continued

| Compound | Structure | LCMS or HPLC condition | Retention time (min) | MS (m/z) |
|---|---|---|---|---|
| 403 | 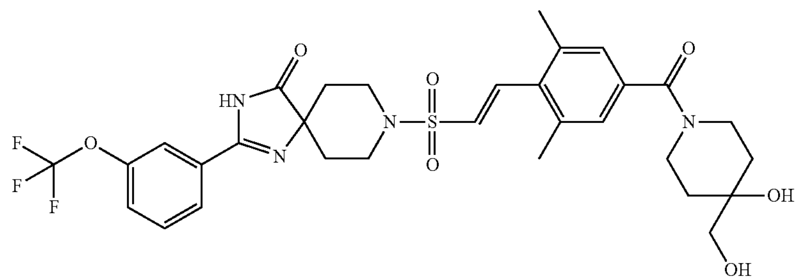 [SMILES: Cc1cc(C(=O)N2CCC(O)(CO)CC2)cc(C)c1/C=C/S(=O)(=O)N1CCC2(CC1)N=C(c1cccc(OC(F)(F)F)c1)NC2=O] | LCMS-D-1 | 2.9 | 665 (M + H)+ |
| 404 | 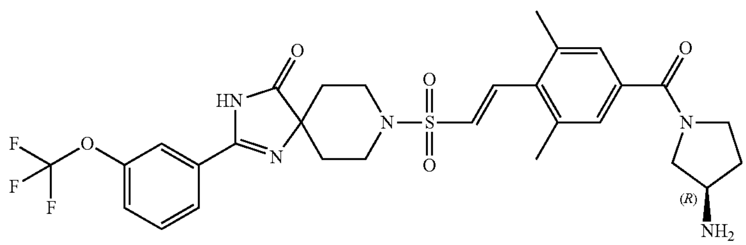 | LCMS-D-1 | 2.7 | 620 (M + H)+ |
| 405 | 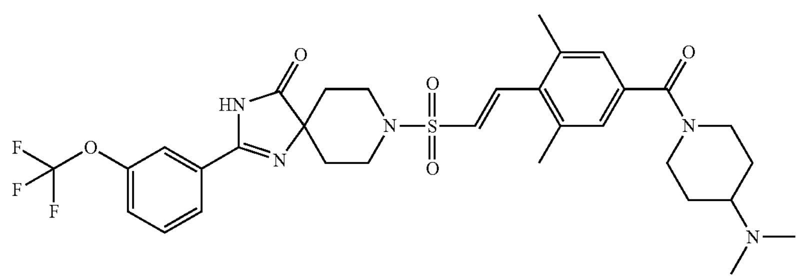 [SMILES: Cc1cc(C(=O)N2CCC(N(C)C)CC2)cc(C)c1/C=C/S(=O)(=O)N1CCC2(CC1)N=C(c1cccc(OC(F)(F)F)c1)NC2=O] | LCMS-D-1 | 2.7 | 662 (M + H)+ |
| 406 | 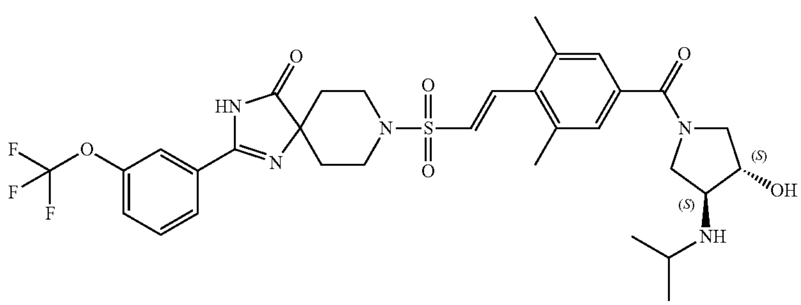 | LCMS-D-1 | 2.7 | 679 (M + H)+ |
| 407 | 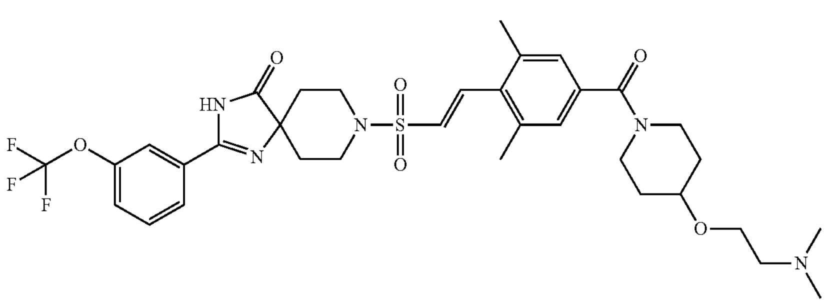 | LCMS-D-1 | 2.7 | 707 (M + H)+ |

TABLE 55-continued
| Compound | Structure | LCMS or HPLC condition | Retention time (min) | MS (m/z) |
|---|---|---|---|---|
| 408 | 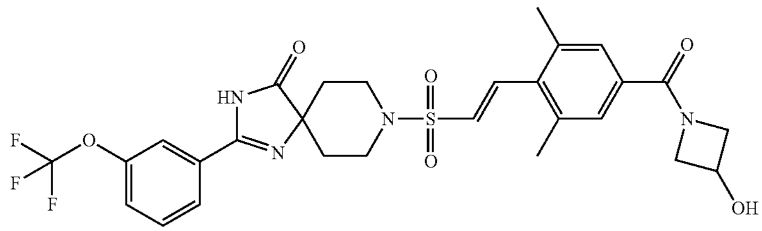 [SMILES: Cc1cc(C(=O)N2CC(O)C2)cc(C)c1/C=C/S(=O)(=O)N1CCC2(CC1)N=C(c1cccc(OC(F)(F)F)c1)NC2=O] | LCMS-D-1 | 3.0 | 607 (M + H)+ |
Example 63
2,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide (Compound 409)
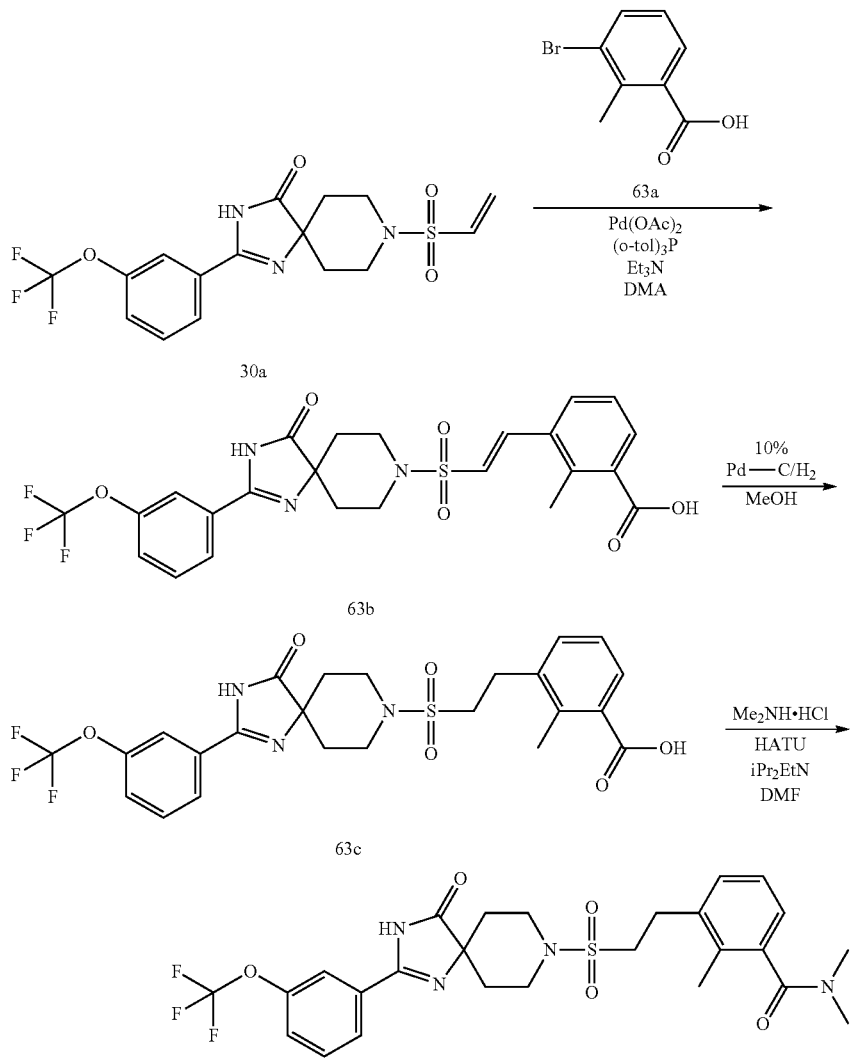
Compound 409

2,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide was synthesized by operations similar to those in Reaction 26-1, Reaction 42-1 and Reaction 10-14 using appropriate reagents and starting material.

MS (ESI) m/z=567 (M+H)+.

The example compounds shown below were synthesized by operations similar to those in Example 63 using appropriate reagents and starting materials.

Compounds 410 to 411

TABLE 56

| Compound | Structure | LCMS or HPLC condition | Retention time (min) | MS (m/z) |
|---|---|---|---|---|
| 410 | 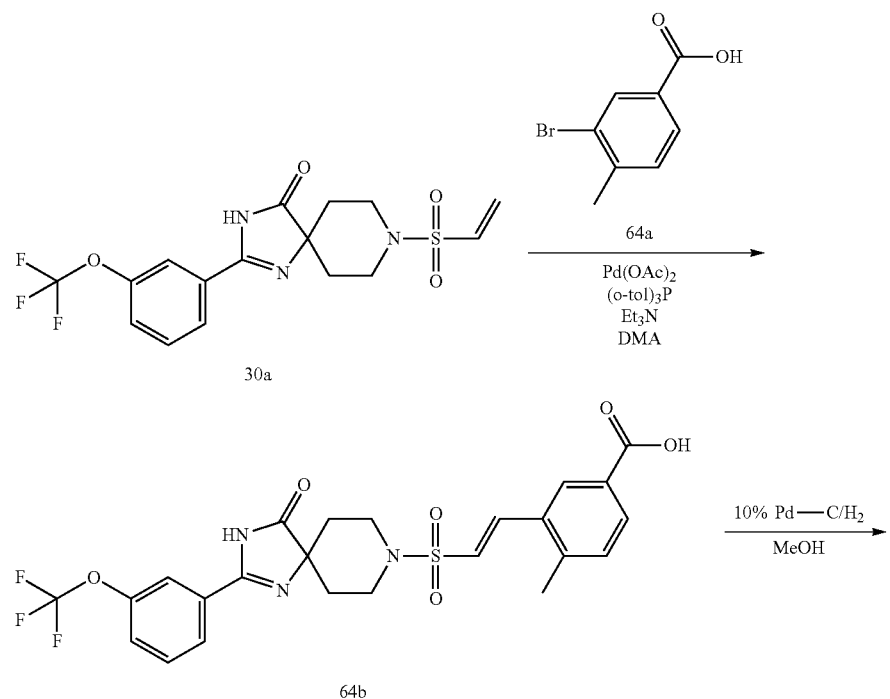 | LCMS-D-1 | 2.9 | 539 (M + H)+ |
| 411 | 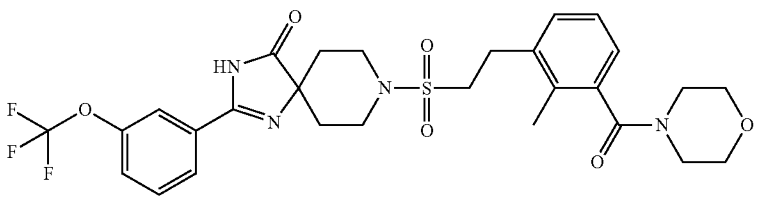 [SMILES: Cc1c(CCS(=O)(=O)N2CCC3(CC2)N=C(c2cccc(OC(F)(F)F)c2)NC3=O)cccc1C(=O)N1CCOCC1] | LCMS-D-1 | 3.1 | 609 (M + H)+ |

Example 64

4,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide (Compound 412)

(Reaction 64-1)

-continued

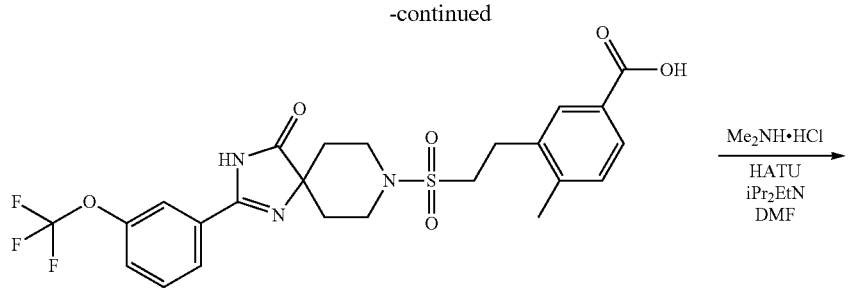

64c

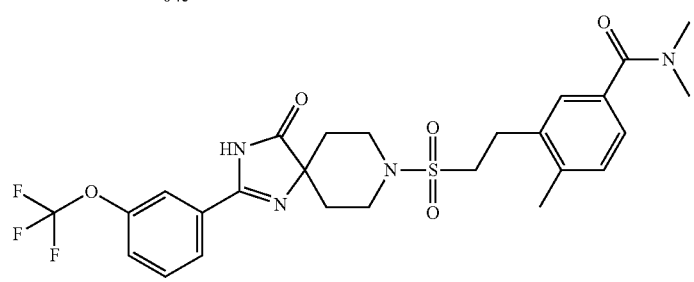

Compound 412

4,N,N-Trimethyl-3-{2-[4-oxo-2-(3-trifluoromethoxy-phenyl)-1,3,8-triaza-spiro[4.5]dec-1-ene-8-sulfonyl]-ethyl}-benzamide was synthesized by operations similar to those in Reaction 26-1, Reaction 42-1 and Reaction 10-14 using appropriate reagents and starting material.
MS (ESI) m/z=567 (M+H)+.

The example compounds shown below were synthesized by operations similar to those in Example 64 using appropriate reagents and starting materials.

Compounds 413 to 415

TABLE 57

| Compound | Structure | LCMS or HPLC condition | Retention time (min) | MS (m/z) |
|---|---|---|---|---|
| 413 | 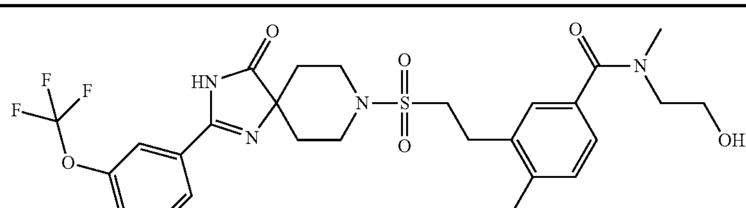 | HPLC-A-1 | 11.5 | 597 (M + H)+ |
| 414 | 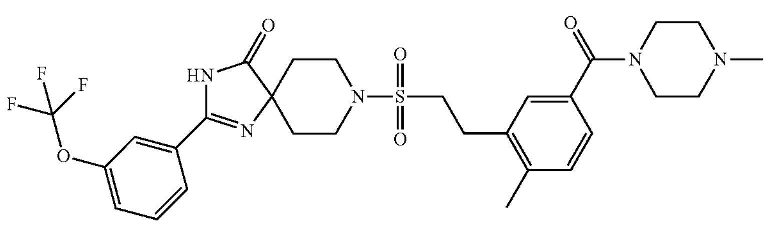 [SMILES: Cc1ccc(C(=O)N2CCN(C)CC2)cc1CCS(=O)(=O)N1CCC2(CC1)N=C(c1cccc(OC(F)(F)F)c1)NC2=O] | HPLC-A-1 | 9.4 | 311 (M + H)+ |
| 415 | 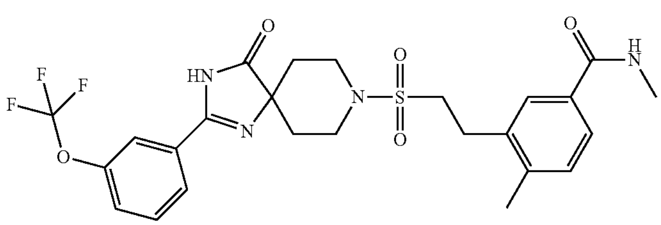 [SMILES: CNC(=O)c1ccc(C)c(CCS(=O)(=O)N2CCC3(CC2)N=C(c2cccc(OC(F)(F)F)c2)NC3=O)c1] | HPLC-A-2 | 9.5 | 553 (M + H)+ |

Example 65

8-(2-{4-[4-(2-Hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one (Compound 416)

(Reaction 65-1)

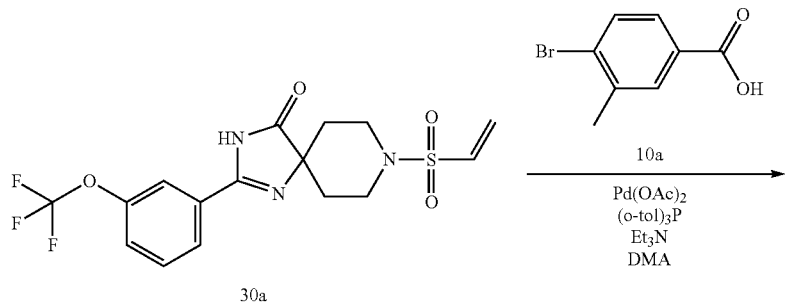

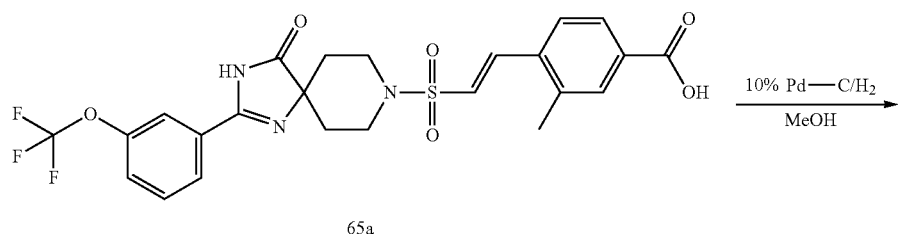

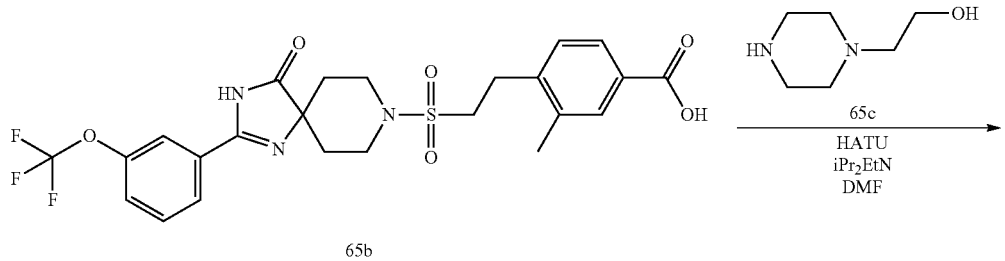

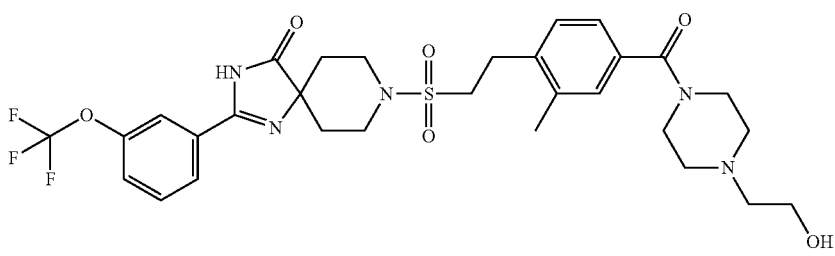

Compound 416

8-(2-{4-[4-(2-Hydroxy-ethyl)-piperazine-1-carbonyl]-2-methyl-phenyl}-ethanesulfonyl)-2-(3-trifluoromethoxy-phenyl)-1,3,8-triaza-spiro[4.5]dec-1-en-4-one was synthesized by operations similar to those in Reaction 26-1, Reaction 42-1 and Reaction 10-14 using appropriate reagents and starting material.

MS (ESI) m/z=652 (M+H)+.

The example compound shown below was synthesized by operations similar to those in Example 64 using appropriate reagents and starting material.

Compound 417

TABLE 58

| Compound | Structure | LCMS or HPLC condition | Retention time (min) | MS (m/z) |
|---|---|---|---|---|
| 417 | 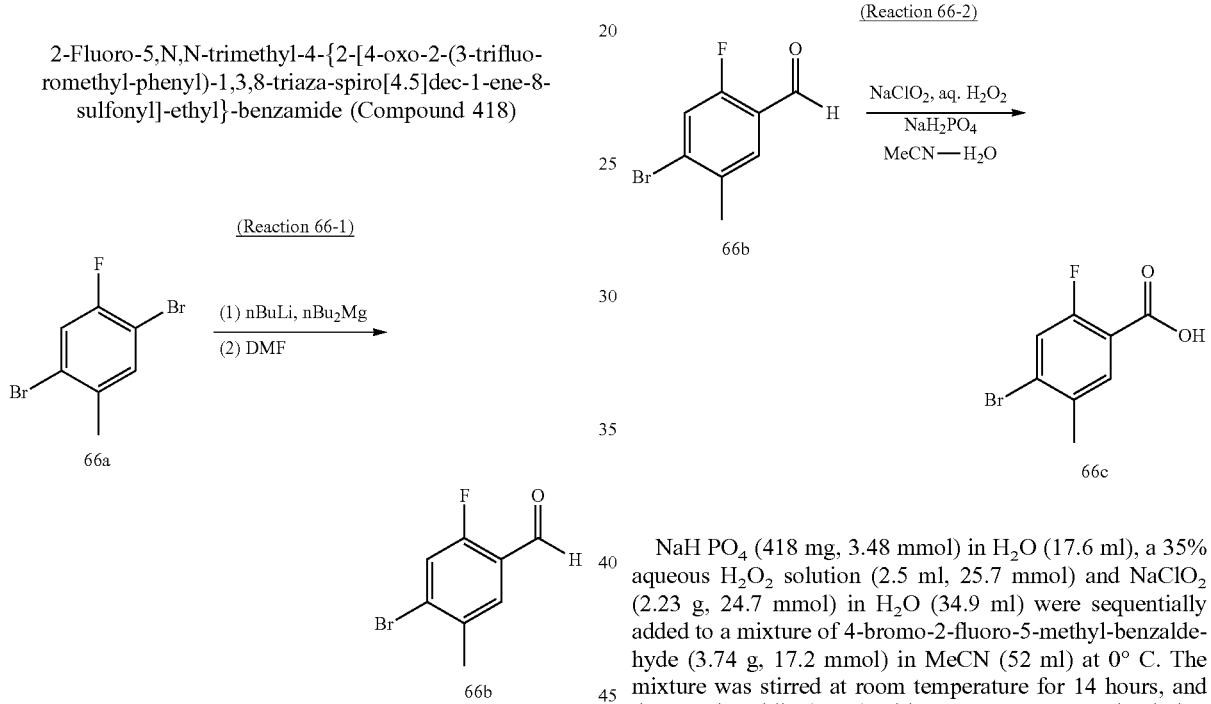 | LCMS-C-2 | 2.31 | 611 (M + H)+ |

Example 66

2-Fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide (Compound 418)

(Reaction 66-1)

(Reaction 66-2)

n-BuLi (5.0 ml, 8.0 mmol, 1.6 M in hexane) was added dropwise to a solution of n-Bu$_2$Mg (8.0 ml, 8.0 mmol, 1.0 M in heptane) at room temperature for 10 minutes. The mixture was stirred at room temperature for 15 minutes and then cooled to −10±2° C. A solution of 2,5-dibromo-4-fluorotoluene (5.466 g, 19.59 mmol) in toluene (30 ml)-THF (6 ml) was added dropwise to this mixed reaction solution over 30 minutes, and the mixture was then stirred at 0° C. for one hour. The reaction mixture was added dropwise to a solution cooled to −10° C. of DMF (2.1 ml, 27 mmol) in toluene (7.6 ml) over 15 minutes. Further, this mixture was stirred at −10 to −5° C. for 30 minutes, and then quenched with an aqueous citric acid solution (2.3 M, 16 ml, 37 mmol) and extracted with Et$_2$O. The organic layer was washed with water, and then dried over MgSO$_4$ and concentrated under reduced pressure to give 4-bromo-2-fluoro-5-methyl-benzaldehyde (3.74 g, 88%).

$^1$H-NMR (300 MHz) (CDCl$_3$) δ 2.42 (3H, s), 7.42 (1H, d, J=9.6 Hz), 7.72 (1H, d, J=7.2 Hz), 10.29 (1H, s).

NaH PO$_4$ (418 mg, 3.48 mmol) in H$_2$O (17.6 ml), a 35% aqueous H$_2$O$_2$ solution (2.5 ml, 25.7 mmol) and NaClO$_2$ (2.23 g, 24.7 mmol) in H$_2$O (34.9 ml) were sequentially added to a mixture of 4-bromo-2-fluoro-5-methyl-benzaldehyde (3.74 g, 17.2 mmol) in MeCN (52 ml) at 0° C. The mixture was stirred at room temperature for 14 hours, and then made acidic (pH 3) with a 10% aqueous HCl solution and extracted with ethyl acetate (3×100 ml). The organic layers were washed with H$_2$O (70 ml), and then dried over MgSO$_4$ and concentrated under reduced pressure to give 4-bromo-2-fluoro-5-methyl-benzoic acid as a pale orange solid (4.02 g, 100%).

$^1$H-NMR (300 MHz) (CDCl$_3$) δ 2.42 (3H, s), 7.41 (1H, d, J=9.9 Hz), 7.88 (1H, d, J=7.5 Hz). MS (ESI) m/z=231 (M−H)−.

(Reaction 66-3)

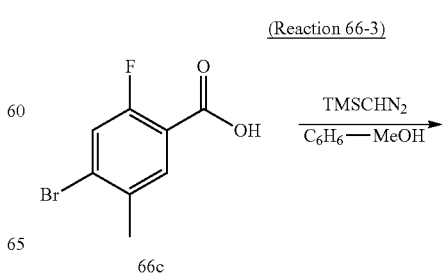

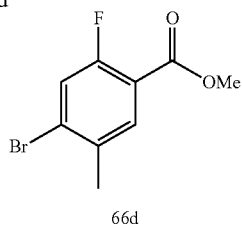

66d (Trimethylsilyl)diazomethane (4.0 ml, 8.0 mmol, 2 M in Et$_2$O) was added dropwise to a solution of 4-bromo-2-fluoro-5-methyl-benzoic acid (1.88 g, 8.05 mmol) in benzene (7.5 ml)-MeOH (5.6 ml) at 10±2° C. over 10 minutes. The mixture was stirred at room temperature for 30 minutes and then concentrated under reduced pressure. The resulting residue was purified by silica gel column chromatography (hexane/ethyl acetate=40/1) to give methyl 4-bromo-2-fluoro-5-methyl-benzoate (1.62 g, 82%).

$^1$H-NMR (300 MHz) (CDCl$_3$) δ 2.40 (3H, s), 3.93 (3H, s), 7.37 (1H, d, J=9.9 Hz), 7.80 (1H, d, J=7.8 Hz).

(Reaction 66-4)

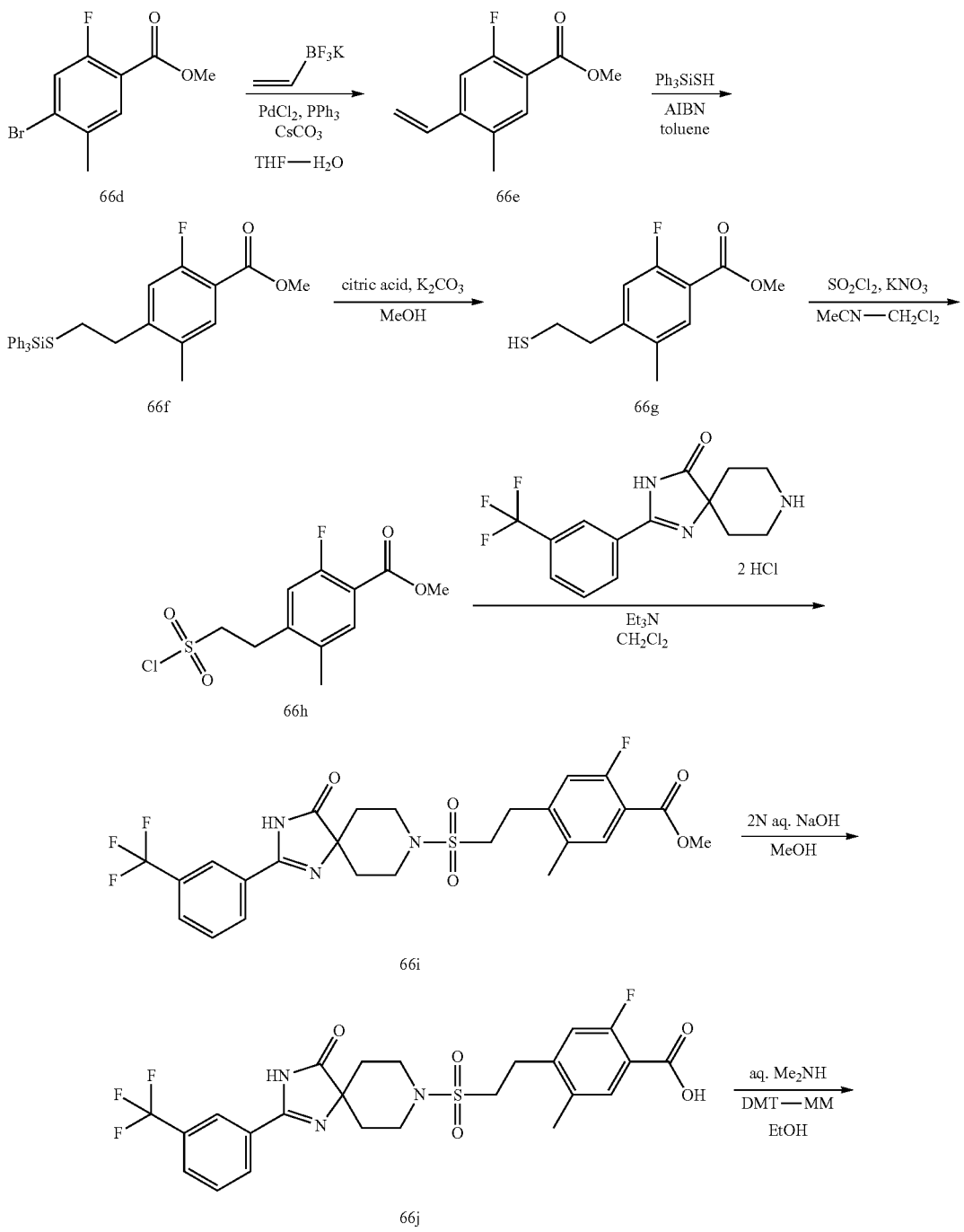

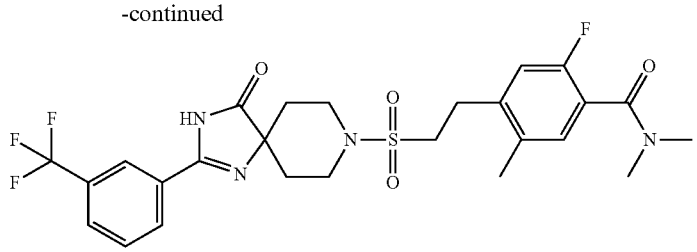

Compound 418

2-Fluoro-5,N,N-trimethyl-4-{2-[4-oxo-2-(3-trifluoromethyl-phenyl)-1,3,8-triaza-spiro[4.5]dec-1-ene-8-sulfonyl]-ethyl}-benzamide was synthesized by operations similar to those in Reaction 10-2, Reaction 10-3, Reaction 10-4, Reaction 10-5, Reaction 5-4, Reaction 23-2 and Reaction 10-1 using appropriate reagents and starting material.

MS (ESI) m/z=569 (M+H)+.

The example compound shown below was synthesized by operations similar to those in Example 66 using appropriate reagents and starting material.

Compound 419

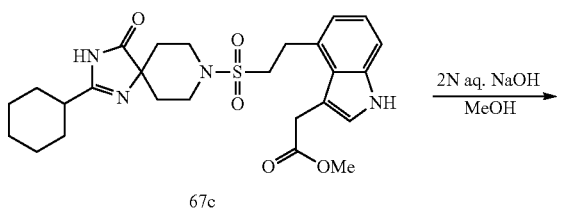

67c

TABLE 59

| Compound | Structure | LCMS or HPLC condition | Retention time (min) | MS (m/z) |
|---|---|---|---|---|
| 419 | 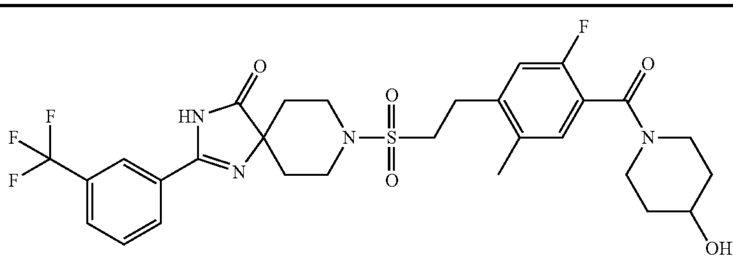 | LCMS-C-2 | 1.78 | 625 (M + H)+ |

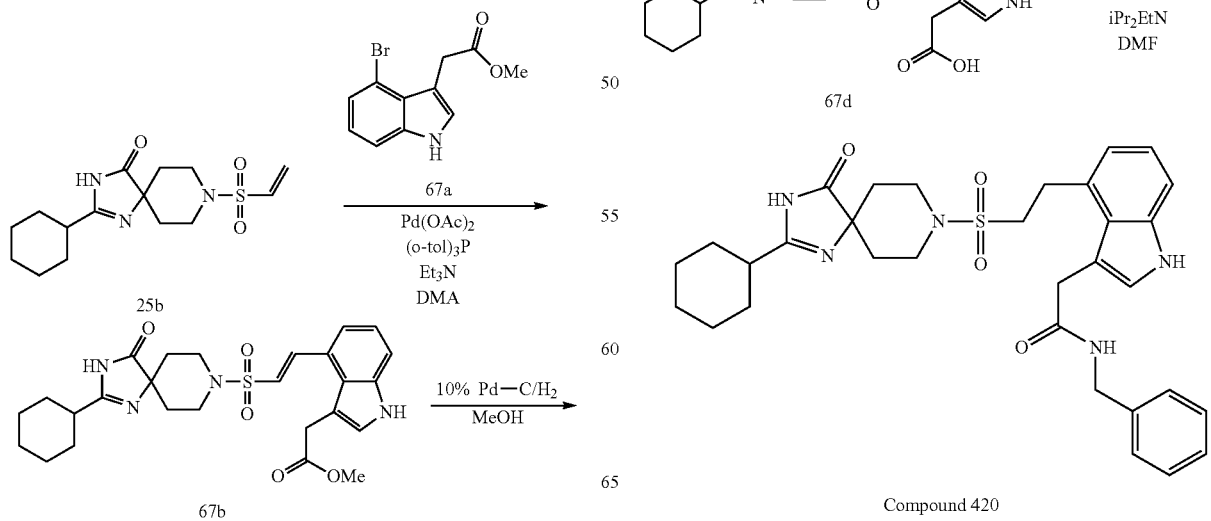

Example 67

N-Benzyl-2-{4-[2-(2-cyclohexyl-4-oxo-1,3,8-triaza-spiro[4.5]dec-1-ene-8-sulfonyl)-ethyl]-1H-indol-3-yl}-acetamide (Compound 420)

(Reaction 67-1)

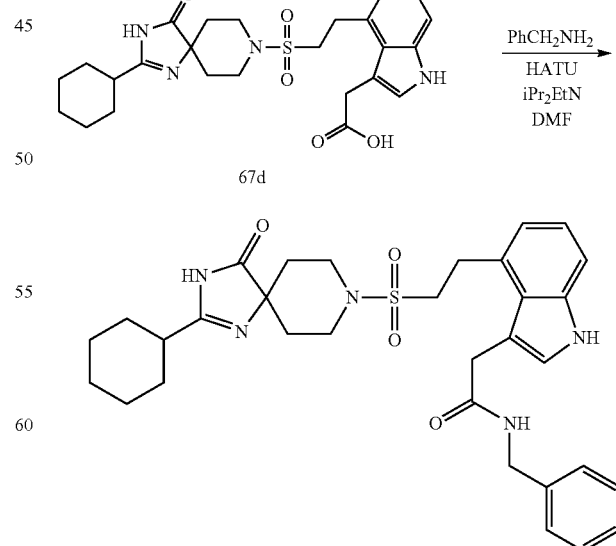

Compound 420

N-Benzyl-2-{4-[2-(2-cyclohexyl-4-oxo-1,3,8-triaza-spiro[4.5]dec-1-ene-8-sulfonyl)-ethyl]-1H-indol-3-yl}-acetamide was synthesized by operations similar to those in Reaction 25-2, Reaction 42-1, Reaction 23-2 and Reaction 10-1 using appropriate reagents and starting material.

MS (ESI) m/z=590 (M+H)+.

Example 68

2-[2-(2-Cyclohexyl-4-oxo-1,3,8-triaza-spiro[4.5]dec-1-ene-8-sulfonyl)-ethyl]-N-methyl-benzamide (Compound 421)

(Reaction 68-1)

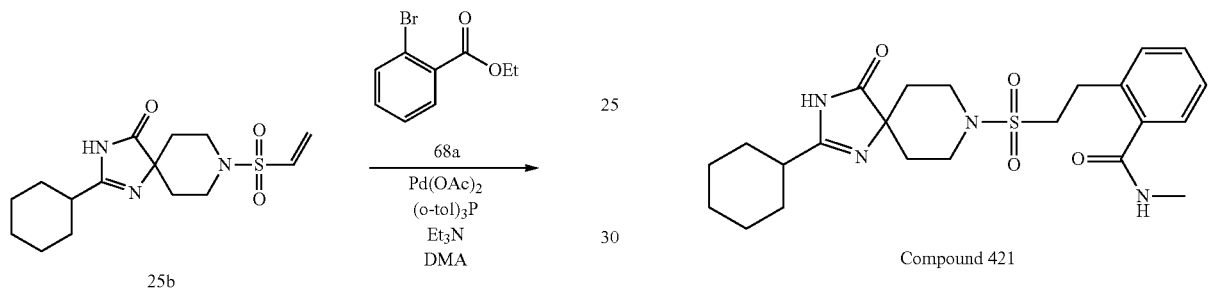

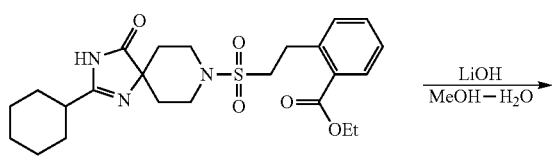

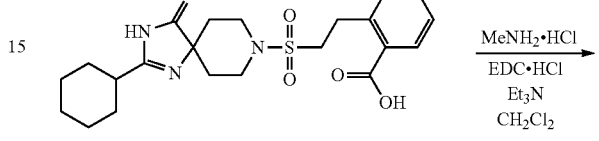

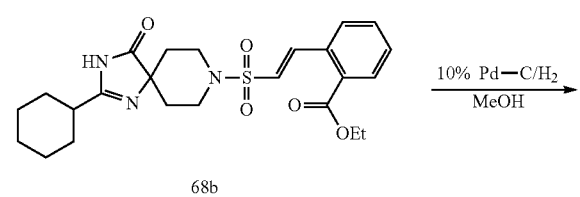

Compound 421

2-[2-(2-Cyclohexyl-4-oxo-1,3,8-triaza-spiro[4.5]dec-1-ene-8-sulfonyl)-ethyl]-N-methyl-benzamide was synthesized by operations similar to those in Reaction 25-2, Reaction 42-1, Reaction 23-2 and Reaction 10-18 using appropriate reagents and starting material.

MS (ESI) m/z=461 (M+H)+.

The example compound shown below was synthesized by operations similar to those in Example 68 using appropriate reagents and starting material.

Compound 422

TABLE 60

| Compound | Structure | LCMS or HPLC condition | Retention time (min) | MS (m/z) |
|---|---|---|---|---|
| 422 | 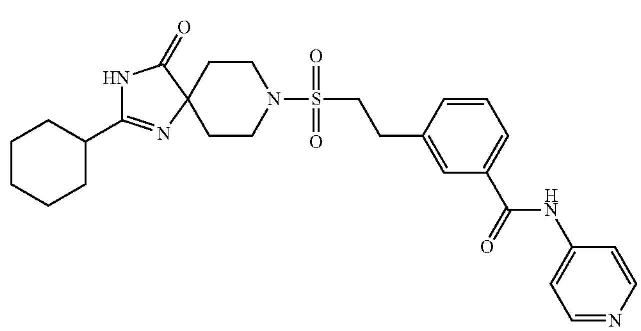 [SMILES: O=C(Nc1ccncc1)c1cccc(CCS(=O)(=O)N2CCC3(CC2)N=C(C2CCCCC2)NC3=O)c1] | LCMS-E-6 | 3.33 | 525 (M + H)+ |

Example 69

8-(3-Chloro-benzenesulfonyl)-2-[1-(3,3-dimethyl-butyryl)-piperidin-3-yl]-1,3,8-triaza-spiro[4.5]dec-1-en-4-one (Compound 423)

(Reaction 69-1)

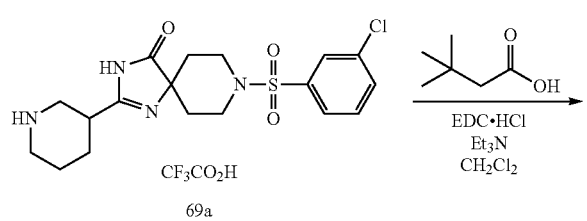

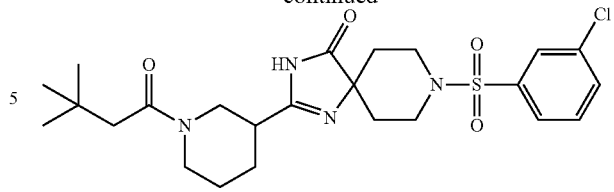

Compound 423

8-(3-Chloro-benzenesulfonyl)-2-[1-(3,3-dimethyl-butyryl)-piperidin-3-yl]-1,3,8-triaza-spiro[4.5]dec-1-en-4-one was synthesized by operations similar to those in Reaction 10-18 using appropriate reagents and starting material.

MS (ESI) m/z=509 (M+H)+.

The example compound shown below was synthesized by operations similar to those in Example 69 using appropriate reagents and starting material.

Compound 424

TABLE 61

| Compound | Structure | LCMS or HPLC condition | Retention time (min) | MS (m/z) |
|---|---|---|---|---|
| 424 | 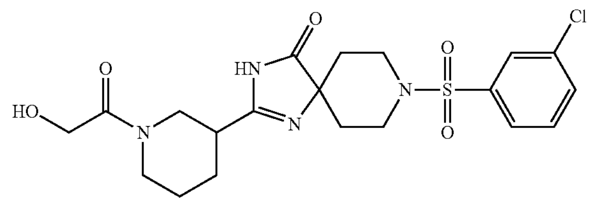 [SMILES: O=C(CO)N1CCCC(C2=NC3(CCN(S(=O)(=O)c4cccc(Cl)c4)CC3)C(=O)N2)C1] | LCMS-E-2 | 2.9 | 469 (M + H)+ |

Example 70

8-(3-Chloro-benzenesulfonyl)-2-[1-(4-chloro-benzoyl)-piperidin-3-yl]-1,3,8-triaza-spiro[4.5]dec-1-en-4-one (Compound 425)

(Reaction 70-1)

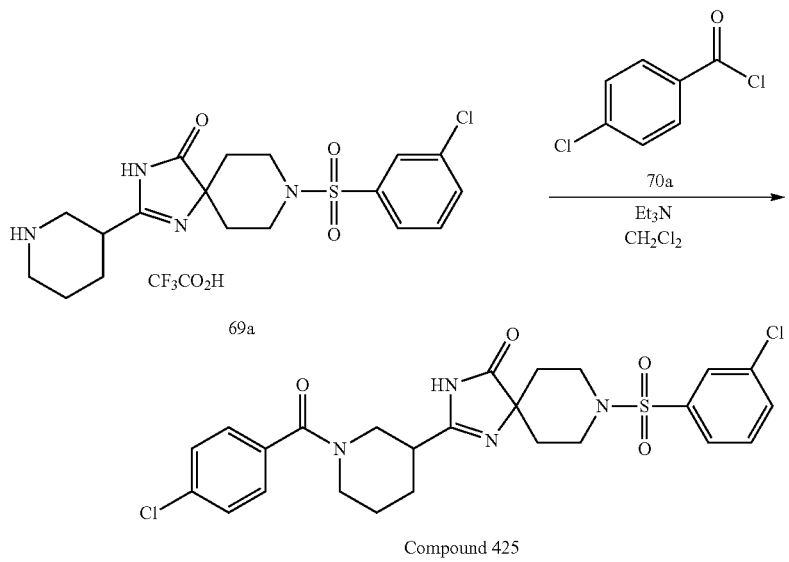

Compound 425

8-(3-Chloro-benzenesulfonyl)-2-[1-(4-chloro-benzoyl)-piperidin-3-yl]-1,3,8-triaza-spiro[4.5]dec-1-en-4-one was synthesized by operations similar to those in Reaction 2-3 using appropriate reagents and starting material.

$^1$H-NMR (400 MHz, CDCl$_3$) δ 1.36-1.67 (m, 5H), 1.84-2.06 (m, 4H), 2.66-2.84 (m, 1H), 2.90-3.10 (m, 2H), 3.16-3.34 (m, 1H), 3.41-3.55 (m, 1H), 3.55-3.67 (m, 2H), 4.04-4.27 (m, 1H), 7.23-7.29 (m, 2H), 7.30-7.37 (m, 2H), 7.43 (t, J=7.83 Hz, 1H), 7.50-7.55 (m, 1H), 7.59-7.65 (m, 1H), 7.72 (t, J=1.77 Hz, 1H). MS (ESI) m/z=549 (M+H)+.

The example compound shown below was synthesized by operations similar to those in Example 70 using appropriate reagents and starting material.

Compound 426

2-[1-(1H-Indol-5-carbonyl)-piperidin-3-yl]-8-(2-naphthalen-1-yl-ethanesulfonyl)-1,3,8-triaza-spiro[4.5]dec-1-en-4-one was synthesized by operations similar to those in Reaction 10-18 using appropriate reagents and starting material.

MS (ESI) m/z=598 (M+H)+.

The example compounds shown below were synthesized by operations similar to those in Example 72 using appropriate reagents and starting materials.

TABLE 62

| Compound | Structure | LCMS or HPLC condition | Retention time (min) | MS (m/z) |
|---|---|---|---|---|
| 426 | 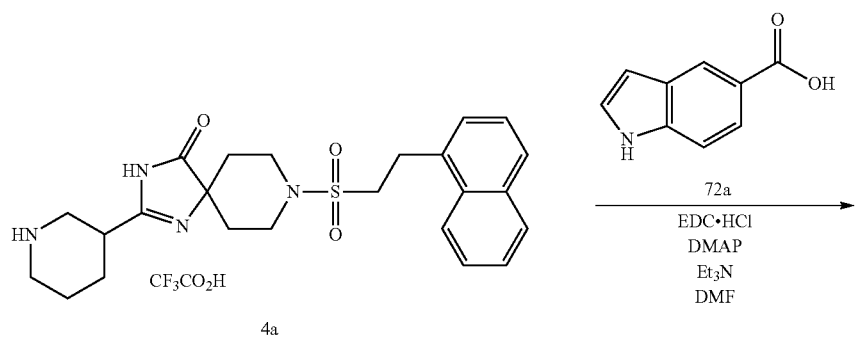 | LCMS-E-2 | 3.82 | 545 (M + H)+ |

Example 72

2-[1-(1H-Indol-5-carbonyl)-piperidin-3-yl]-8-(2-naphthalen-1-yl-ethanesulfonyl)-1,3,8-triaza-spiro[4.5]dec-1-en-4-one (Compound 428)

(Reaction 72-1)

Compound 428

Compounds 429 to 439

TABLE 63

| Compound | Structure | LCMS or HPLC condition | Retention time (min) | MS (m/z) |
|---|---|---|---|---|
| 429 | 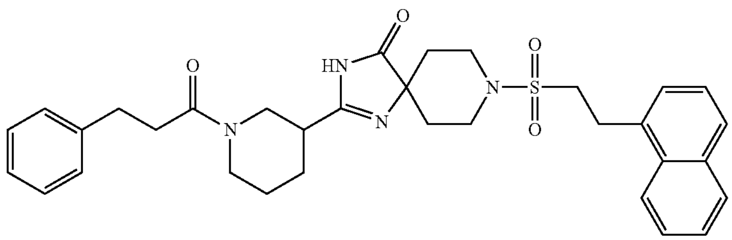 [SMILES: O=C(CCc1ccccc1)N1CCCC(C2=NC3(CCN(S(=O)(=O)CCc4cccc5ccccc45)CC3)C(=O)N2)C1] | LCMS-E-3 | 3.5 | 587 (M + H)+ |
| 430 | 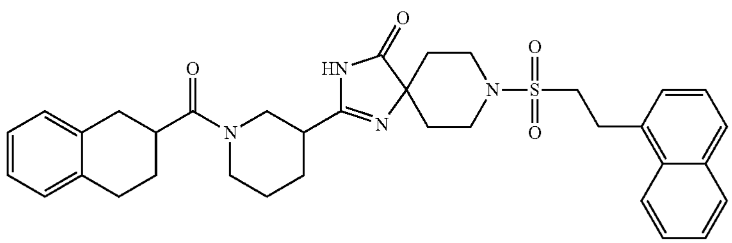 [SMILES: O=C(C1CCc2ccccc2C1)N1CCCC(C2=NC3(CCN(S(=O)(=O)CCc4cccc5ccccc45)CC3)C(=O)N2)C1] | LCMS-E-3 | 3.67 | 613 (M + H)+ |
| 431 | 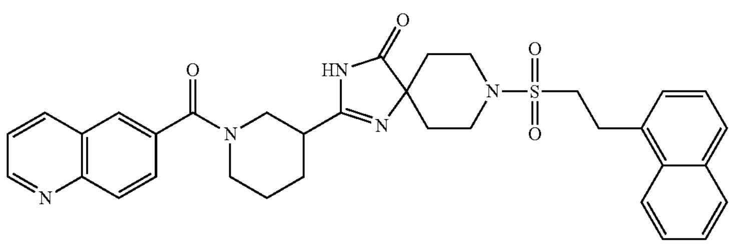 [SMILES: O=C(c1ccc2ncccc2c1)N1CCCC(C2=NC3(CCN(S(=O)(=O)CCc4cccc5ccccc45)CC3)C(=O)N2)C1] | LCMS-E-3 | 1.57 | 610 (M + H)+ |
| 432 | 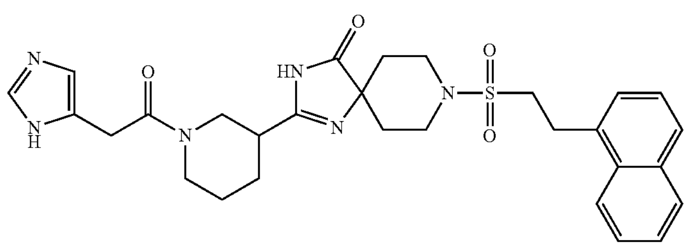 [SMILES: O=C(Cc1cnc[nH]1)N1CCCC(C2=NC3(CCN(S(=O)(=O)CCc4cccc5ccccc45)CC3)C(=O)N2)C1] | LCMS-E-2 | 2.47 | 563 (M + H)+ |
| 433 | 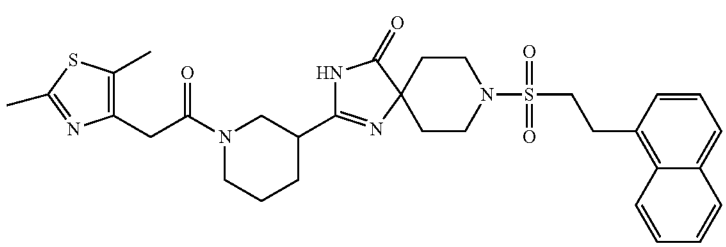 [SMILES: Cc1nc(CC(=O)N2CCCC(C3=NC4(CCN(S(=O)(=O)CCc5cccc6ccccc56)CC4)C(=O)N3)C2)c(C)s1] | LCMS-E-2 | 3.79 | 608 (M + H)+ |
| 434 | 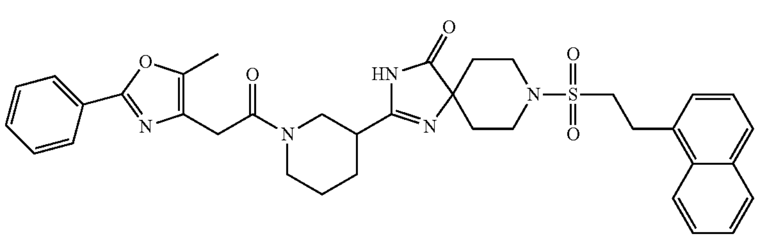 [SMILES: Cc1oc(-c2ccccc2)nc1CC(=O)N1CCCC(C2=NC3(CCN(S(=O)(=O)CCc4cccc5ccccc45)CC3)C(=O)N2)C1] | LCMS-E-2 | 4.49 | 654 (M + H)+ |

TABLE 63-continued
| Compound | Structure | LCMS or HPLC condition | Retention time (min) | MS (m/z) |
|---|---|---|---|---|
| 435 | 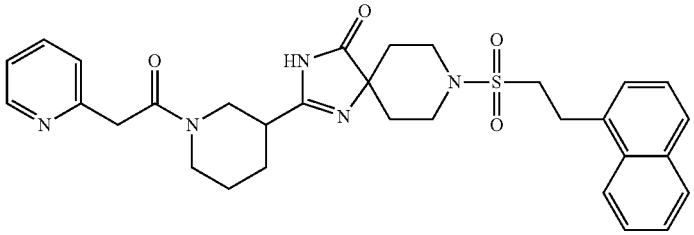 [SMILES: O=C(Cc1ccccn1)N1CCCC(C2=NC3(CCN(S(=O)(=O)CCc4cccc5ccccc45)CC3)C(=O)N2)C1] | LCMS-E-2 | 2.97 | 574 (M + H)+ |
| 436 | 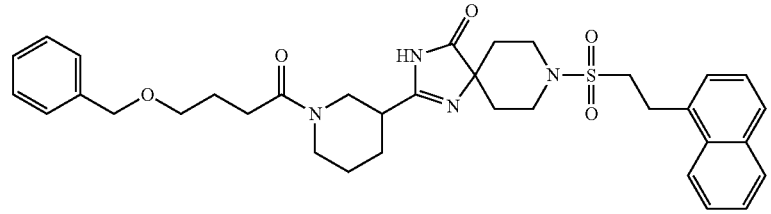 [SMILES: O=C(CCCOCc1ccccc1)N1CCCC(C2=NC3(CCN(S(=O)(=O)CCc4cccc5ccccc45)CC3)C(=O)N2)C1] | LCMS-E-2 | 4.48 | 631 (M + H)+ |
| 437 | 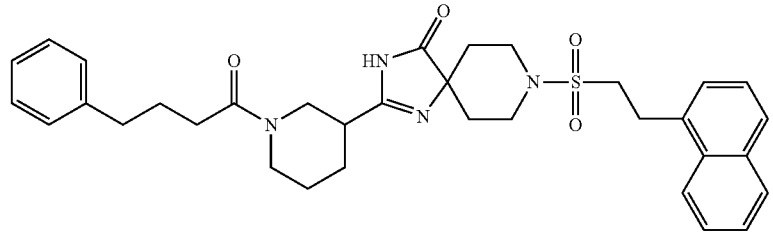 [SMILES: O=C(CCCc1ccccc1)N1CCCC(C2=NC3(CCN(S(=O)(=O)CCc4cccc5ccccc45)CC3)C(=O)N2)C1] | LCMS-E-2 | 4.57 | 601 (M + H)+ |
| 438 | 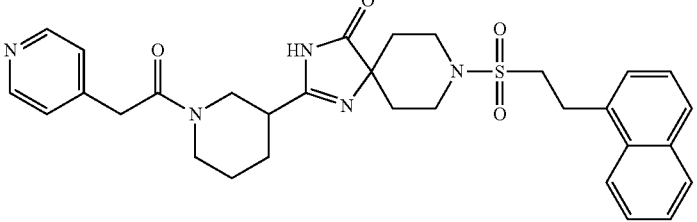 | LCMS-E-2 | 2.68 | 574 (M + H)+ |
| 439 | 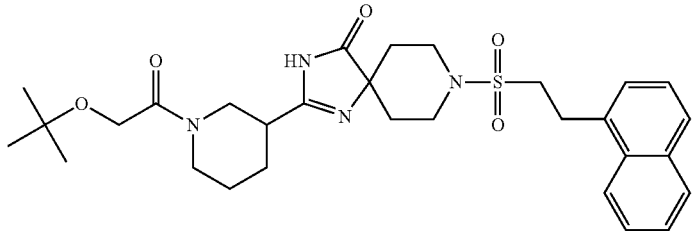 [SMILES: CC(C)(C)OCC(=O)N1CCCC(C2=NC3(CCN(S(=O)(=O)CCc4cccc5ccccc45)CC3)C(=O)N2)C1] | LCMS-E-2 | 4.02 | 569 (M + H)+ |

Example 73

8-(2-Naphthalen-1-yl-ethanesulfonyl)-2-{1-[(E)-(3-phenyl-acryloyl)]-piperidin-3-yl}-1,3,8-triaza-spiro[4.5]dec-1-en-4-one (Compound 441)

(Reaction 73-1)

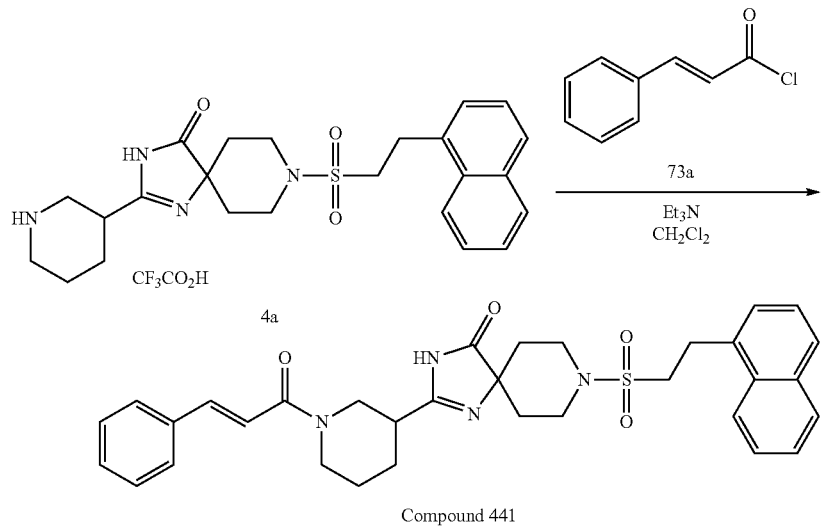

Compound 441

8-(2-Naphthalen-1-yl-ethanesulfonyl)-2-{1-[(E)-(3-phenyl-acryloyl)]-piperidin-3-yl}-1,3,8-triaza-spiro[4.5]dec-1-en-4-one was synthesized by operations similar to those in Reaction 2-3 using appropriate reagents and starting material.

MS (ESI) m/z=585 (M+H)+.

Example 74

2-[1-(2-Amino-acetyl)-piperidin-3-yl]-8-(3-chloro-benzenesulfonyl)-1,3,8-triaza-spiro[4.5]dec-1-en-4-one (Compound 442)

(Reaction 74-1)

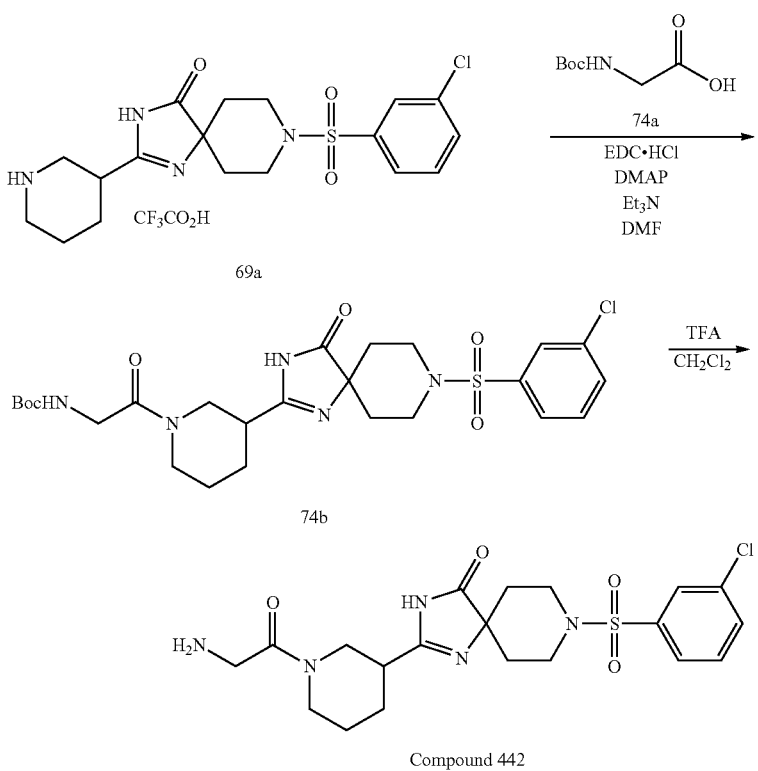

Compound 442

2-[1-(2-Amino-acetyl)-piperidin-3-yl]-8-(3-chloro-benzenesulfonyl)-1,3,8-triaza-spiro[4.5]dec-1-en-4-one was synthesized by operations similar to those in Reaction 10-18 and Reaction 4-1 using appropriate reagents and starting material.

MS (ESI) m/z=468 (M+H)+.

Example 75

8-{2-[2-Methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one (Compound 444)

8-{2-[2-Methyl-4-(3-methylamino-pyrrolidine-1-carbonyl)-phenyl]-ethanesulfonyl}-2-(3-trifluoromethyl-phenyl)-1,3,8-triaza-spiro[4.5]dec-1-en-4-one was synthesized by operations similar to those in Reaction 10-14 and Reaction 4-1 using appropriate reagents and starting material.

MS (ESI) m/z=606 (M+H)+.

The example compounds shown below were synthesized by operations similar to those in Example 75 using appropriate reagents and starting materials.

(Reaction 75-1)

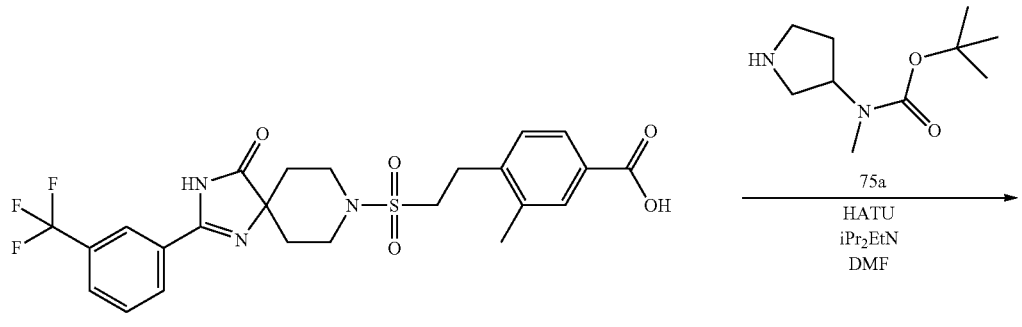

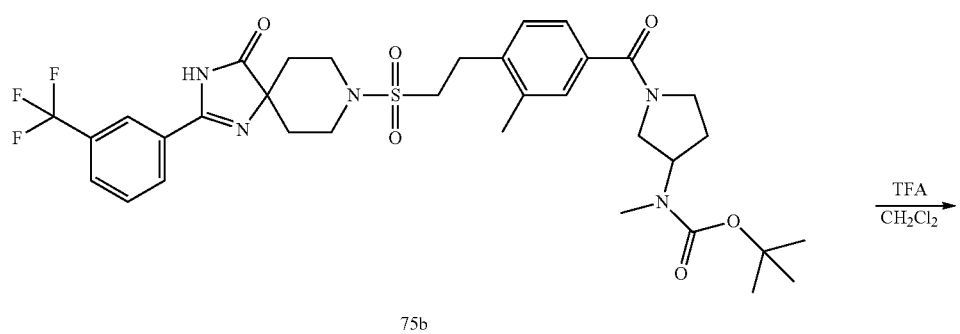

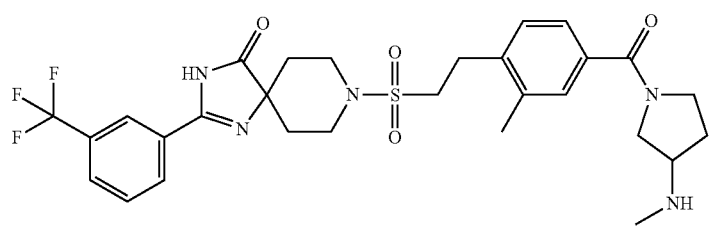

Compound 444

Compounds 445 to 446
TABLE 64
| Compound | Structure | LCMS or HPLC condition | Retention time (min) | MS (m/z) |
|---|---|---|---|---|
| 445 | 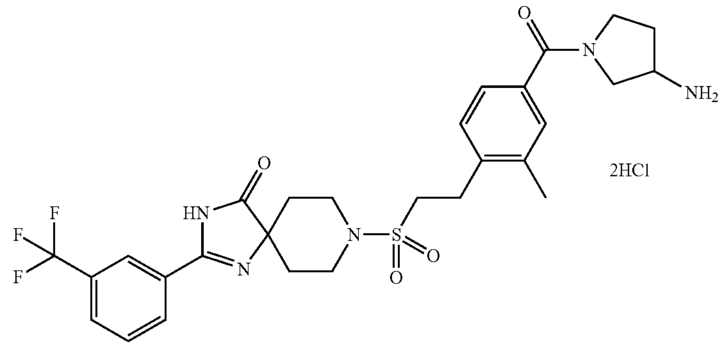 [SMILES: Cc1cc(C(=O)N2CCC(N)C2)ccc1CCS(=O)(=O)N1CCC2(CC1)N=C(c1cccc(C(F)(F)F)c1)NC2=O ; "2HCl"] | LCMS-B-1 | 1.70 | 592 (M + H)+ |
| 446 | 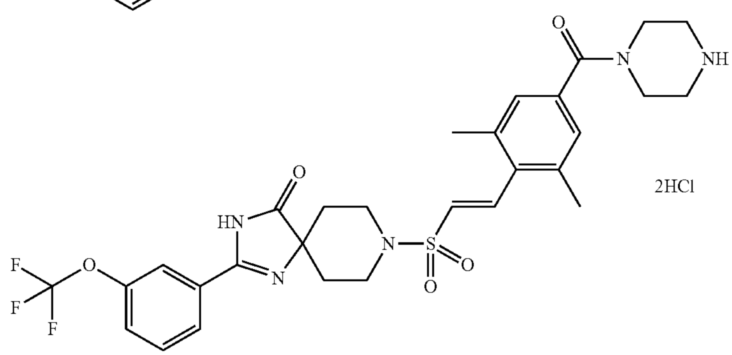 | LCMS-C-1 | 2.50 | 620 (M + H)+ |
Example 76
8-((E)-2-{4-[4-(2-Hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one (Compound 447)
(Reaction 76-1)
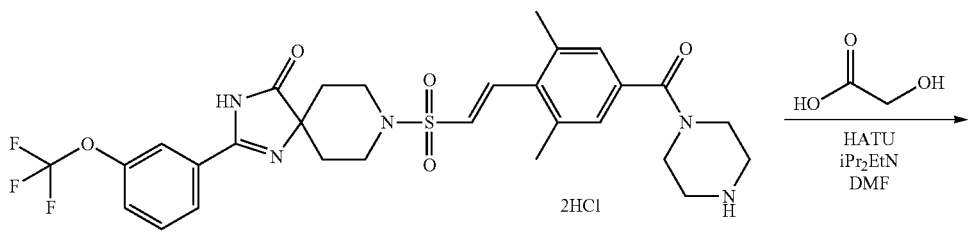
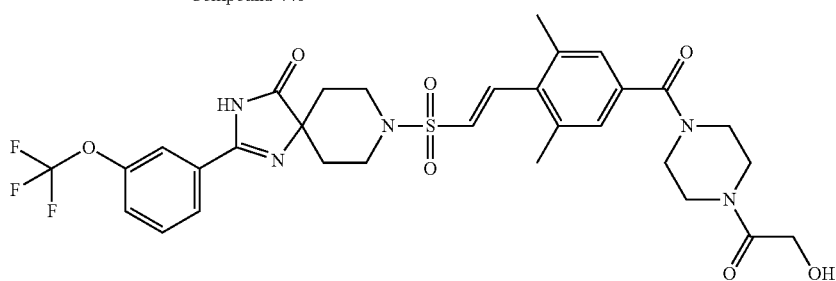
Compound 447

8-((E)-2-{4-[4-(2-Hydroxy-acetyl)-piperazine-1-carbonyl]-2,6-dimethyl-phenyl}-ethenesulfonyl)-2-(3-trifluoromethoxy-phenyl)-1,3,8-triaza-spiro[4.5]dec-1-en-4-one was synthesized by operations similar to those in Reaction 10-14 using appropriate reagents and starting material.

MS (ESI) m/z=678 (M+H)+.

The example compounds shown below were synthesized by operations similar to those in Example 76 using appropriate reagents and starting materials.

Compounds 448 to 449

TABLE 65

| Compound | Structure | LCMS or HPLC condition | Retention time (min) | MS (m/z) |
|---|---|---|---|---|
| 448 | 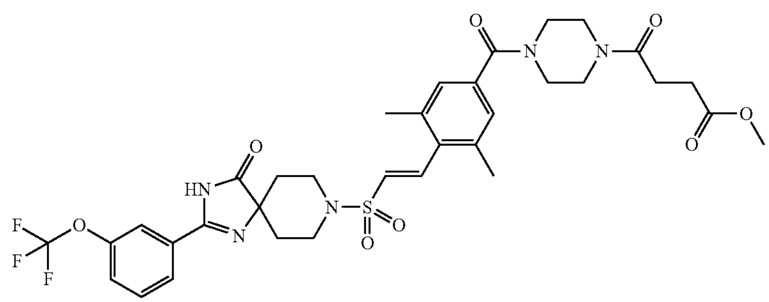 [SMILES: COC(=O)CCC(=O)N1CCN(C(=O)c2cc(C)c(/C=C/S(=O)(=O)N3CCC4(CC3)N=C(c3cccc(OC(F)(F)F)c3)NC4=O)c(C)c2)CC1] | LCMS-C-1 | 2.62 | 734 (M + H)+ |
| 449 | 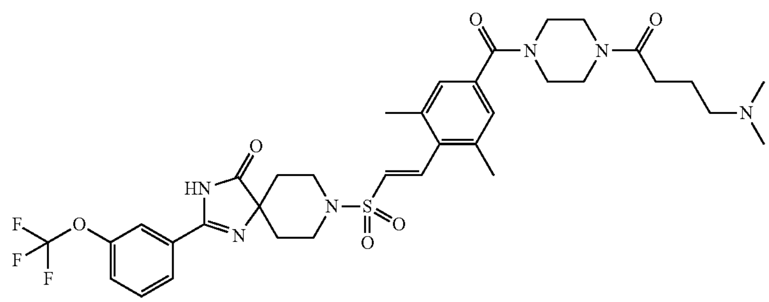 [SMILES: Cc1cc(C(=O)N2CCN(C(=O)CCCN(C)C)CC2)cc(C)c1/C=C/S(=O)(=O)N1CCC2(CC1)N=C(c1cccc(OC(F)(F)F)c1)NC2=O] | LCMS-C-1 | 2.43 | 733 (M + H)+ |

Example 77

2-Methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 450)

(Reaction 77-1)

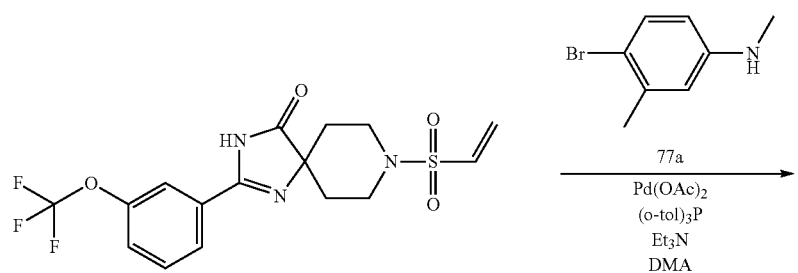

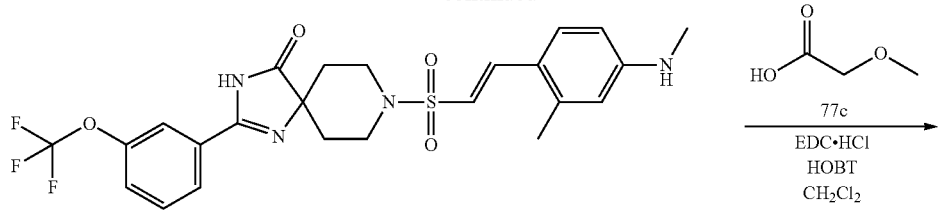

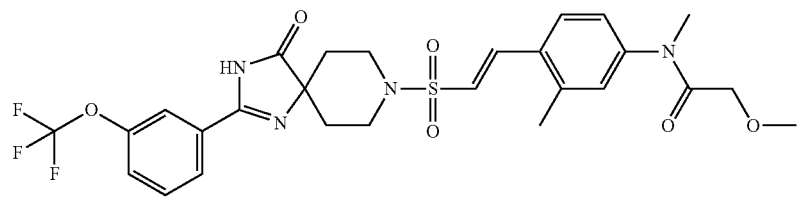

Compound 450

2-Methoxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 26-1 and Reaction 10-18 using appropriate reagents and starting material.
MS (ESI) m/z=595 (M+H)+.

Example 78

2-Hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 451)

(Reaction 78-1)

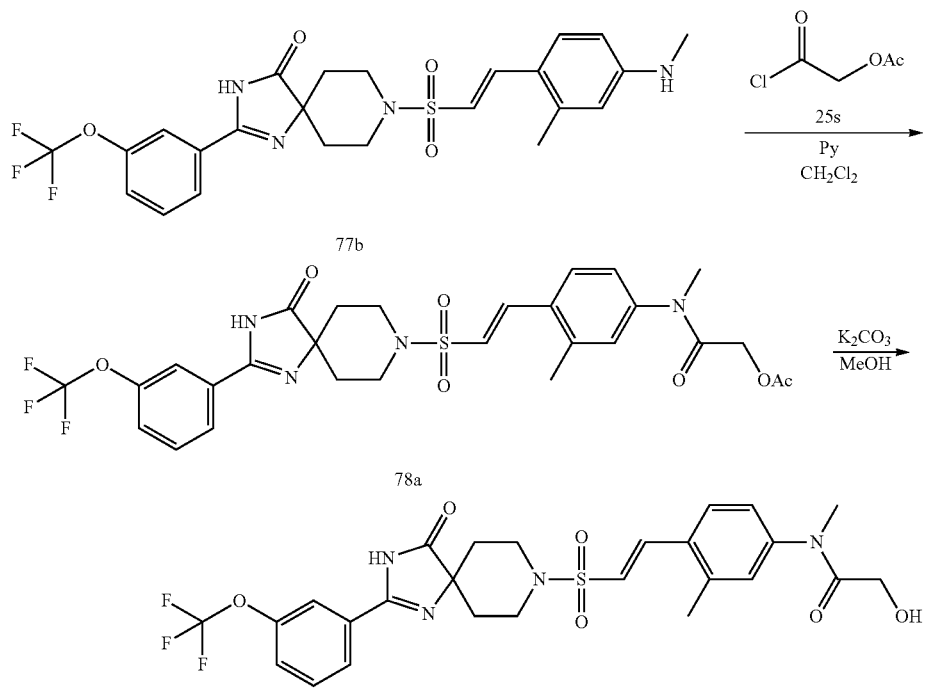

Compound 451

2-Hydroxy-N-methyl-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 2-3 and Reaction 12-5 using appropriate reagents and starting material.

MS (ESI) m/z=581 (M+H)+.

Example 79

[(3,5-Dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid (Compound 452)

(Reaction 79-1)

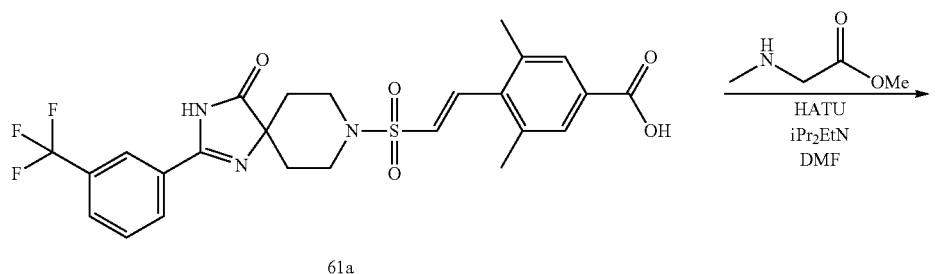

61a

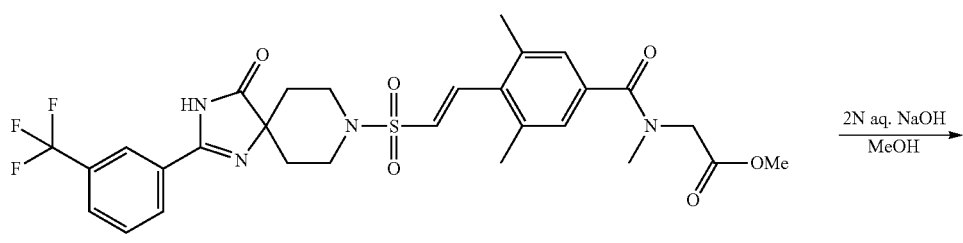

79a

Compound 452

[(3,5-Dimethyl-4-{(E)-2-[4-oxo-2-(3-trifluoromethyl-phenyl)-1,3,8-triaza-spiro[4.5]dec-1-ene-8-sulfonyl]-vinyl}-benzoyl)-methyl-amino]-acetic acid was synthesized by operations similar to those in Reaction 10-14 and Reaction 23-2 using appropriate reagents and starting material.

MS (ESI) m/z=607 (M+H)+.

Example 80

8-(3-Chloro-benzenesulfonyl)-2-[1-(3,3-dimethyl-butyl)-piperidin-3-yl]-1,3,8-triaza-spiro[4.5]dec-1-en-4-one (Compound 453)

(Reaction 80-1)

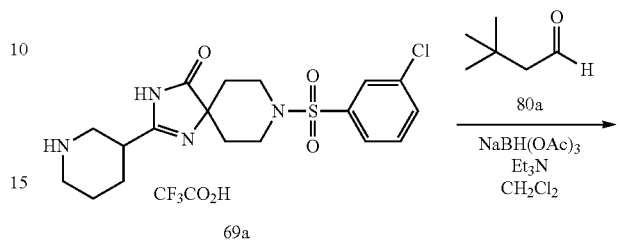

69a

-continued

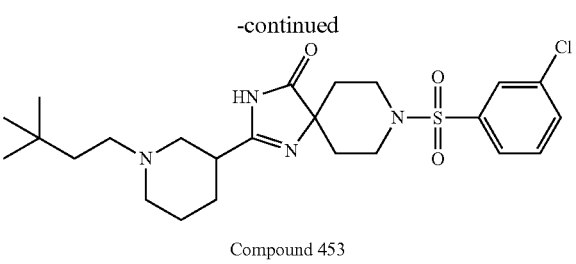

Compound 453

Triethylamine (2 eq), 3,3-dimethyl-butylaldehyde (1 eq) and sodium triacetoxyborohydride (1.5 eq) were added to a solution of 8-(3-chloro-benzenesulfonyl)-2-piperidin-3-yl-1,3,8-triaza-spiro[4.5]dec-1-en-4-one trifluoroacetate (126 mg, 0.24 mmol) in dichloromethane (5 ml). The mixture was stirred at room temperature overnight and then concentrated under reduced pressure. The resulting residue was purified by HPLC to give 8-(3-chloro-benzenesulfonyl)-2-[1-(3,3-dimethyl-butyl)-piperidin-3-yl]-1,3,8-triaza-spiro[4.5]dec-1-en-4-one (35 mg, yield 30%).

$^1$H-NMR (400 MHz, CDCl$_3$) δ 0.85 (s, 9H), 0.87-0.93 (m, 2H), 1.43-1.56 (m, 4H), 1.58-1.70 (m, 3H), 1.75-1.99 (m, 6H), 2.93-3.03 (m, 3H), 3.54-3.63 (m, 3H), 7.43 (t, J=7.83 Hz, 1H), 7.49-7.54 (m, 1H), 7.62 (d, J=7.58 Hz, 1H), 7.72 (t, J=1.77 Hz, 1H). MS (ESI) m/z=495 (M+H)+.

Example 81

3-[8-(3-Chloro-benzenesulfonyl)-4-oxo-1,3,8-triaza-spiro[4.5]dec-1-en-2-yl]-piperidine-1-carboxylic acid tert-butylamide (Compound 454)

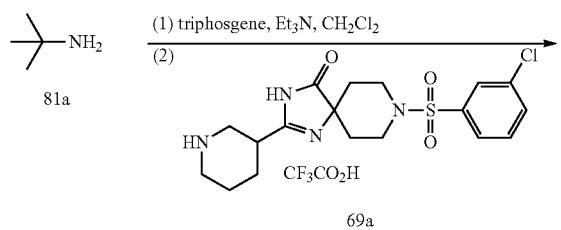

(Reaction 81-1)

81a

69a

Compound 454

A solution of triphosgene (345 mg, 1.16 mmol) in CH$_2$Cl$_2$ (7 ml) was added to a solution of tert-butylamine (331 µl, 3.14 mmol) and triethylamine (876 µl, 6.29 mmol) in CH$_2$Cl$_2$ (10 ml) at −78° C. The mixture was stirred at room temperature for 10 minutes, followed by addition of a solution of 8-(3-chloro-benzenesulfonyl)-2-piperidin-3-yl-1,3,8-triaza-spiro[4.5]dec-1-en-4-one trifluoroacetate (165 mg, 0.314 mmol) and triethylamine (876 µl, 6.29 mmol) in CH$_2$Cl$_2$ (2 ml). Further, the reaction mixture was stirred at room temperature for 10 minutes and then concentrated under reduced pressure. The resulting residue was purified by silica gel column chromatography to give 3-[8-(3-Chloro-benzenesulfonyl)-4-oxo-1,3,8-triaza-spiro[4.5]dec-1-en-2-yl]-piperidine-1-carboxylic acid tert-butylamide as a colorless oil (40 mg, yield 25%).

$^1$H-NMR (400 MHz, CDCl$_3$) δ 1.25 (s, 9H), 1.47-1.63 (m, 2H), 1.71-1.84 (m, 2H), 1.83-2.07 (m, 6H), 3.02-3.13 (m, 2H), 3.14-3.25 (m, 2H), 3.53-3.65 (m, 2H), 3.84-3.95 (m, 1H), 7.43 (t, J=7.83 Hz, 1H), 7.49-7.55 (m, 1H), 7.61 (d, J=7.83 Hz, 1H), 7.72 (t, J=1.77 Hz, 1H). MS (ESI) m/z=510 (M+H)+.

The example compound shown below was synthesized by operations similar to those in Example 81 using appropriate reagents and starting material.

Compound 455

TABLE 66

| Compound | Structure | LCMS or HPLC condition | Retention time (min) | MS (m/z) |
| --- | --- | --- | --- | --- |
| 455 | 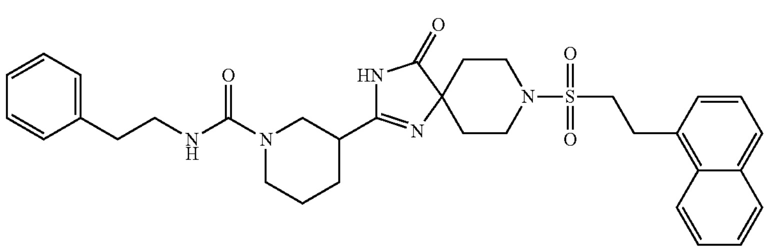 [SMILES: O=C(NCCc1ccccc1)N1CCCC(C2=NC3(CCN(S(=O)(=O)CCc4cccc5ccccc45)CC3)C(=O)N2)C1] | LCMS-E-2 | 3.34 | 602 (M + H)+ |

Example 82

8-(3-Chloro-benzenesulfonyl)-2-[1-(piperidine-1-carbonyl)-piperidin-3-yl]-1,3,8-triaza-spiro[4.5]dec-1-en-4-one (Compound 456)

(Reaction 82-1)

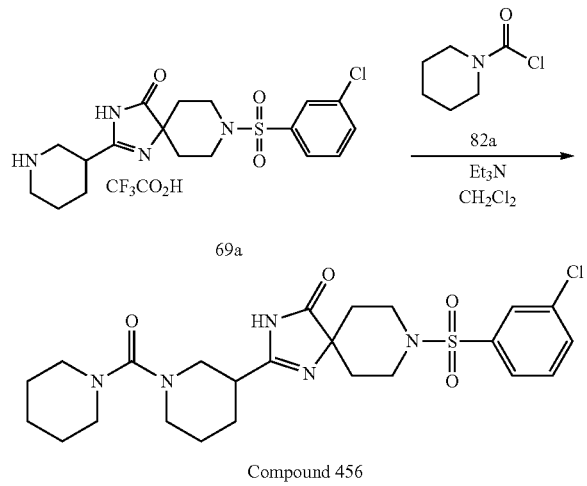

TEA (1.143 mmol, 3 eq) and piperidine-1-carbonyl chloride (0.457 mmol, 1.2 eq) were sequentially added to a mixed solution of 8-(3-chloro-benzenesulfonyl)-2-piperidin-3-yl-1,3,8-triaza-spiro[4.5]dec-1-en-4-one trifluoroacetate (200 mg, 0.38 mmol) in dichloromethane (3 ml). The resulting mixture was stirred at room temperature overnight and then concentrated under reduced pressure. The resulting residue was purified by HPLC to give 8-(3-chloro-benzenesulfonyl)-2-[1-(piperidine-1-carbonyl)-piperidin-3-yl]-1,3,8-triaza-spiro[4.5]dec-1-en-4-one (30 mg, yield 15%).

$^1$H-NMR (400 MHz, CDCl$_3$) δ 1.34-1.48 (m, 2H), 1.49-1.66 (m, 6H), 1.66-1.81 (m, 2H), 1.84-1.96 (m, 1H), 1.97-2.12 (m, 2H), 2.79-2.96 (m, 1H), 2.98-3.25 (m, 8H), 3.25-3.42 (m, 2H), 3.62-3.89 (m, 3H), 7.50 (t, J=7.83 Hz, 1H), 7.57-7.62 (m, 1H), 7.69 (d, J=7.58 Hz, 1H), 7.80 (t, J=1.77 Hz, 1H). MS (ESI) m/z=522 (M+H)+.

Example 83

3-(2-Dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea (Compound 457)

(Reaction 83-1)

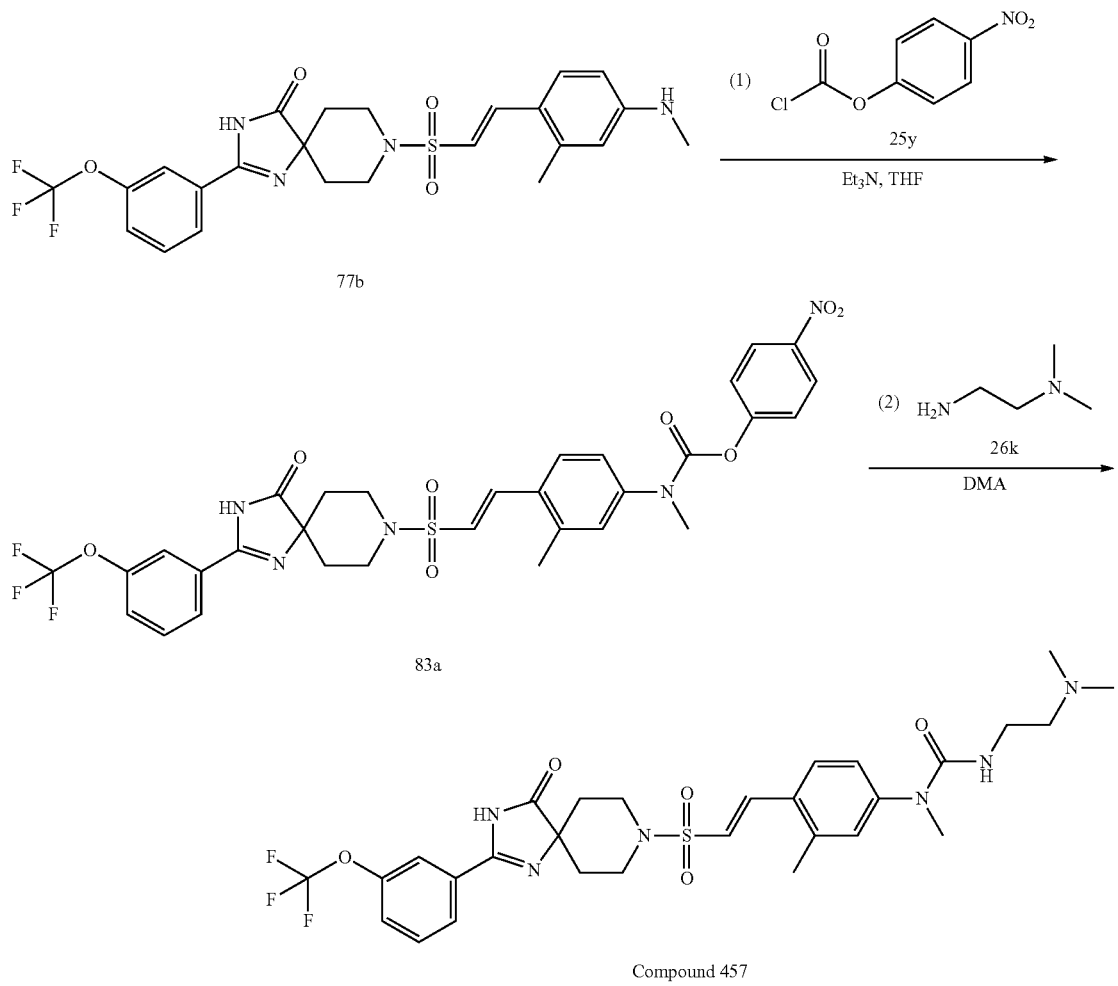

4-Nitrophenyl chloroformate (35 mg, 0.17 mmol) was added to a solution of 8-[(E)-2-(2-methyl-4-methylamino-phenyl)-ethenesulfonyl]-2-(3-trifluoromethoxy-phenyl)-1,3,8-triaza-spiro[4.5]dec-1-en-4-one (80 mg, 0.15 mmol) in THF (1 ml) at room temperature, and the mixture was then stirred at 70° C. for 30 minutes. The reaction mixture was extracted with AcOEt, and then dried over sodium sulfate and concentrated under reduced pressure. The resulting intermediate (83a) (20 mg, 0.029 mmol) was dissolved in DMA (0.1 ml), and N,N-dimethylethylenediamine (0.1 ml, 0.91 mmol) was added. The mixture was then stirred at 140° C. for one hour and at 100° C. for one hour. The resulting reaction mixture was purified by silica gel column chromatography to give 3-(2-dimethylamino-ethyl)-1-methyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea as an amorphous (12 mg, yield 66%).

$^1$H-NMR (400 MHz, DMSO-d6) δ 1.63-1.66 (m, 2H), 1.85-1.90 (m, 2H), 2.09 (s, 6H), 2.28 (t, J=6.8 Hz, 2H), 2.40 (s, 3H), 3.06-3.17 (m, 7H), 3.58-3.61 (m, 2H), 6.18 (t, J=5.8 Hz, 1H), 7.20 (d, J=8.3 Hz, 1H), 7.22 (s, 1H), 7.26 (d, J=15.6 Hz, 1H), 7.55 (d, J=15.6 Hz, 1H), 7.57-7.67 (m, 2H), 7.82 (d, J=8.3 Hz, 1H), 7.91 (br, 1H), 8.01 (br, 1H), 11.8 (br, 1H). MS (ESI) m/z=637 (M+H)+.

The example compound shown below was synthesized by operations similar to those in Example 83 using appropriate reagents and starting material.

Compound 458

TABLE 67

| Compound | Structure | LCMS or HPLC condition | Retention time (min) | MS (m/z) |
|---|---|---|---|---|
| 458 | ![structure] | LCMS-B-1 | 2.04 | 566 (M + H)+ |

Example 84

1-{3-[2-(2-Cyclohexyl-4-oxo-1,3,8-triaza-spiro[4.5]dec-1-ene-8-sulfonyl)-ethyl]-2-methyl-phenyl}-3-methyl-urea (Compound 459)

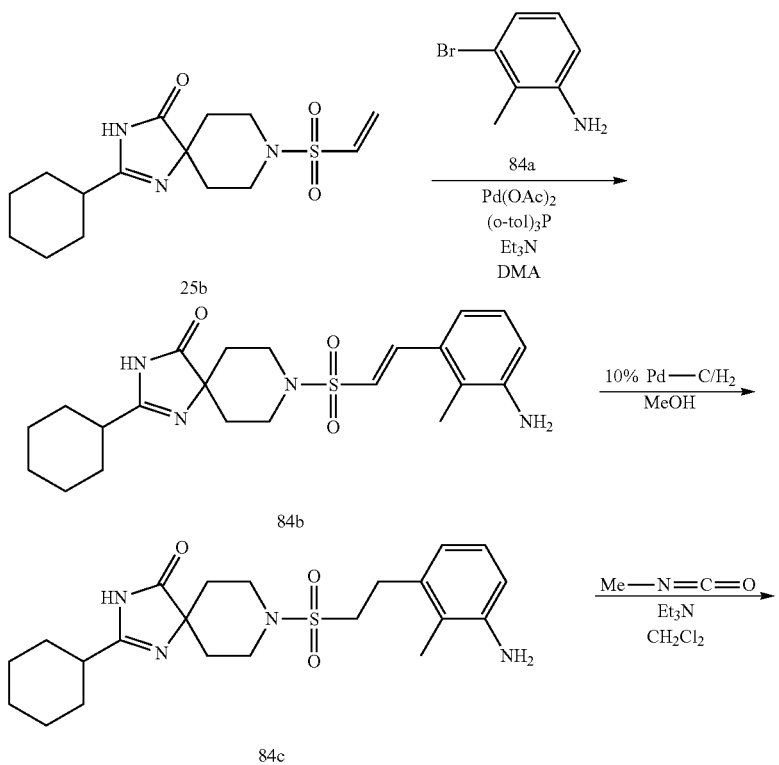

(Reaction 84-1)

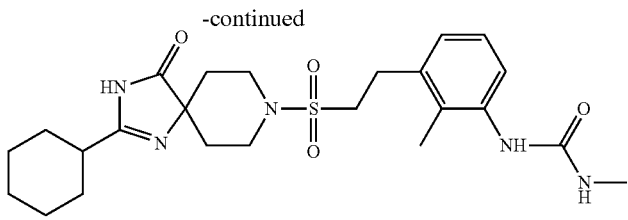

Compound 459

1-{3-[2-(2-Cyclohexyl-4-oxo-1,3,8-triaza-spiro[4.5]dec-1-ene-8-sulfonyl)-ethyl]-2-methyl-phenyl}-3-methyl-urea was synthesized by operations similar to those in Reaction 25-2, Reaction 42-1 and Reaction 84-1 using appropriate reagents and starting material.

MS (ESI) m/z=490 (M+H)+.

Example 85

3-[8-(3-Chloro-benzenesulfonyl)-4-oxo-1,3,8-triaza-spiro[4.5]dec-1-en-2-yl]-piperidine-1-carboxylic acid 2-methoxy-ethyl ester (Compound 460)

(Reaction 85-1)

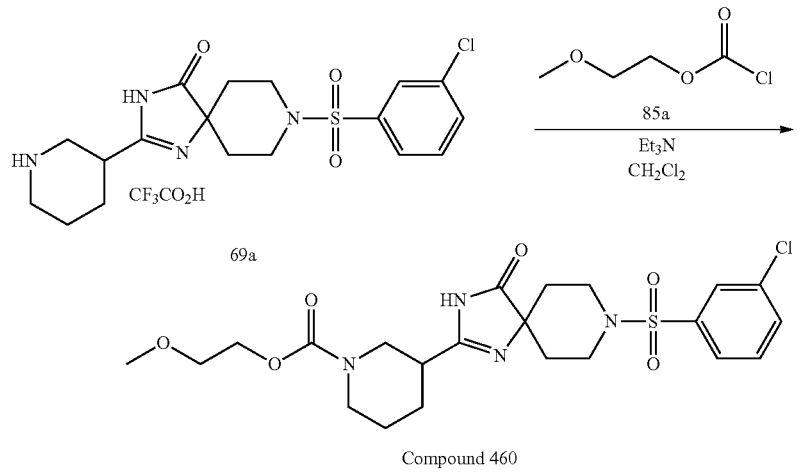

Compound 460

3-[8-(3-Chloro-benzenesulfonyl)-4-oxo-1,3,8-triaza-spiro[4.5]dec-1-en-2-yl]-piperidine-1-carboxylic acid 2-methoxy-ethyl ester was synthesized by operations similar to those in Reaction 2-3 using appropriate reagents and starting material.

$^1$H-NMR (400 MHz, CDCl$_3$) δ 1.21-1.33 (m, 2H), 1.34-1.51 (m, 3H), 1.52-1.71 (m, 2H), 1.73-2.02 (m, 3H), 2.45-2.62 (m, 1H), 2.81-2.95 (m, 3H), 3.26 (s, 3H), 3.43-3.51 (m, 2H), 3.54-3.65 (m, 2H), 3.95-4.04 (m, 1H), 4.05-4.15 (m, 2H), 7.35-7.44 (m, 1H), 7.45-7.51 (m, 1H), 7.56 (d, J=7.83 Hz, 1H), 7.66 (t, J=1.77 Hz, 1H). MS (ESI) m/z=513 (M+H)+.

The example compounds shown below were synthesized by operations similar to those in Example 85 using appropriate reagents and starting materials.

Compounds 461 to 465

TABLE 68

| Compound | Structure | LCMS or HPLC condition | Retention time (min) | MS (m/z) |
| --- | --- | --- | --- | --- |
| 461 | ![structure] | LCMS-E-6 | 1.86 | 545 (M + H)+ |

TABLE 68-continued
| Compound | Structure | LCMS or HPLC condition | Retention time (min) | MS (m/z) |
|---|---|---|---|---|
| 462 | 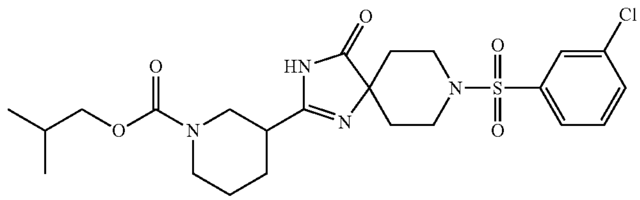 [SMILES: CC(C)COC(=O)N1CCCC(C2=NC3(CCN(S(=O)(=O)c4cccc(Cl)c4)CC3)C(=O)N2)C1] | LCMS-E-6 | 1.84 | 511 (M + H)+ |
| 463 | 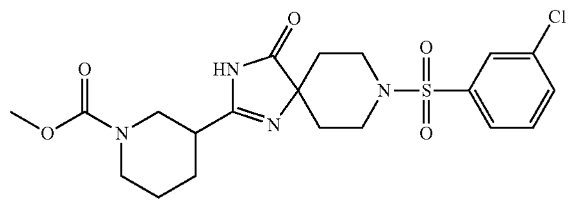 [SMILES: COC(=O)N1CCCC(C2=NC3(CCN(S(=O)(=O)c4cccc(Cl)c4)CC3)C(=O)N2)C1] | LCMS-E-6 | 1.46 | 469 (M + H)+ |
| 464 | 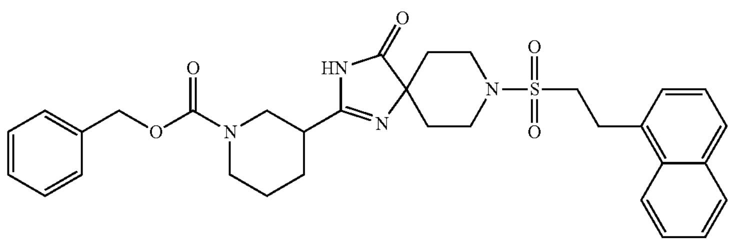 | LCMS-E-3 | 3.65 | 589 (M + H)+ |
| 465 | 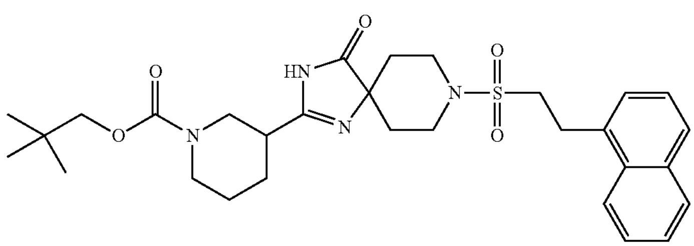 [SMILES: CC(C)(C)COC(=O)N1CCCC(C2=NC3(CCN(S(=O)(=O)CCc4cccc5ccccc45)CC3)C(=O)N2)C1] | LCMS-E-3 | 3.75 | 569 (M + H)+ |
Example 86
Methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester (Compound 466)
(Reaction 86-1)
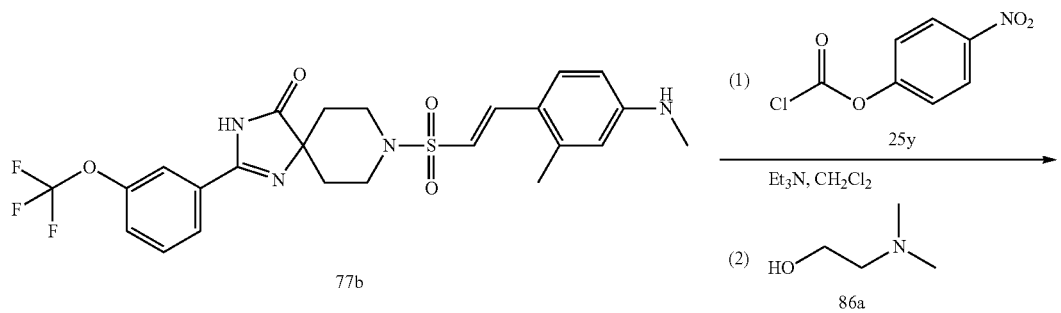

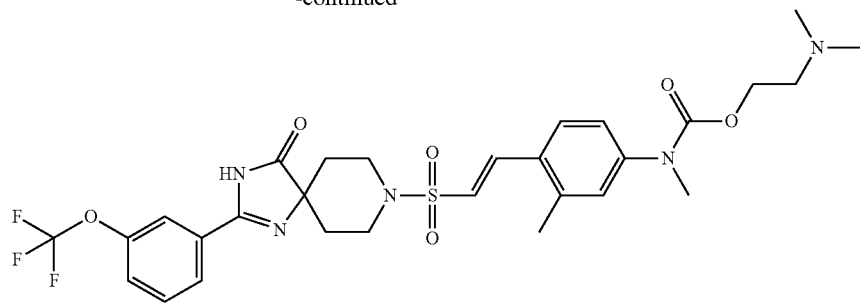

Compound 466

Methyl-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-carbamic acid 2-dimethylamino-ethyl ester was synthesized by operations similar to those in Reaction 83-1 using appropriate reagents and starting material.

MS (ESI) m/z=638 (M+H)+.

The example compound shown below was synthesized by operations similar to those in Example 86 using appropriate reagents and starting material.

Compound 467

TABLE 69

| Compound | Structure | LCMS or HPLC condition | Retention time (min) | MS (m/z) |
|---|---|---|---|---|
| 467 | 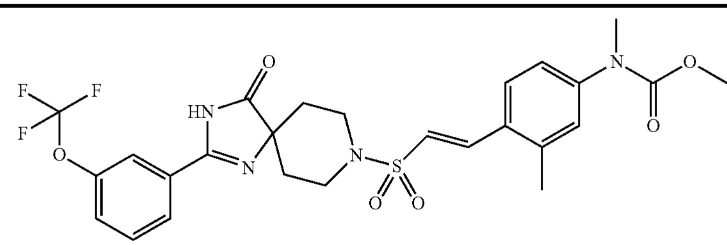 | LCMS-A-1 | 2.74 | 581 (M + H)+ |

Example 87

Methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester (Compound 468)

(Reaction 87-1)

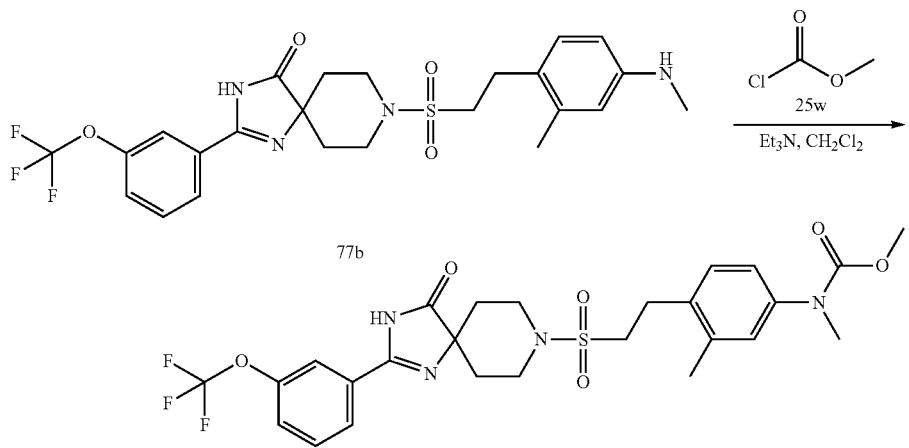

Compound 468

Methyl-(3-methyl-4-{2-[4-oxo-2-(3-trifluoromethoxy-phenyl)-1,3,8-triaza-spiro[4.5]dec-1-ene-8-sulfonyl]-ethyl}-phenyl)-carbamic acid methyl ester was synthesized by operations similar to those in Reaction 2-3 using appropriate reagents and starting material.

MS (ESI) m/z=583 (M+H)+.

Example 88

2-Cyclohexyl-8-(2-o-tolyl-ethanesulfonyl)-1,3,8-triaza-spiro[4.5]dec-1-ene-4-thione (Compound 469)

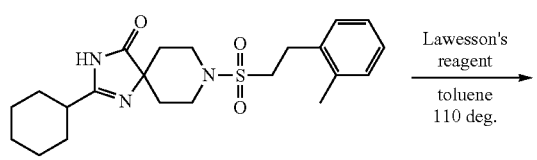

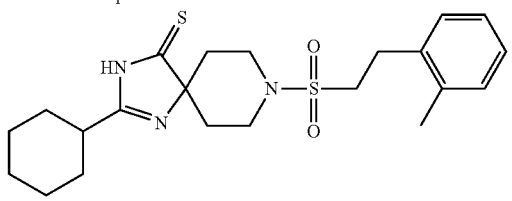

2-Cyclohexyl-8-(2-o-tolyl-ethanesulfonyl)-1,3,8-triaza-spiro[4.5]dec-1-ene-4-one (24.2 mg, 0.058 mmol), Lawesson's reagent (48.3 mg, 0.116 mmol) and toluene (1.16 ml) were added to a sealed test tube and stirred at 110° C. overnight. The reaction mixture was cooled to ambient temperature, and the solvent was then distilled off under reduced pressure. The residue was purified by column chromatography (silica gel, CH$_2$Cl$_2$-MeOH) to give 2-cyclohexyl-8-(2-o-tolyl-ethanesulfonyl)-1,3,8-triaza-spiro[4.5]dec-1-ene-4-thione (11.2 mg, 45%).

$^1$H-NMR (400 MHz, CD$_3$OD) δ 1.29-1.58 (7H, m), 1.73-2.15 (7H, m), 2.36 (3H, s), 2.55 (1H, tt, J=4, 12 Hz), 3.09-3.13 (2H, m), 3.25-3.27 (2H, m), 3.30-3.31 (2H, m), 3.80-3.83 (2H, m), 7.13-7.23 (4H, m). MS (ESI) m/z=434 (M+H)+.

Example 89

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 470)

(Reaction 89-1)

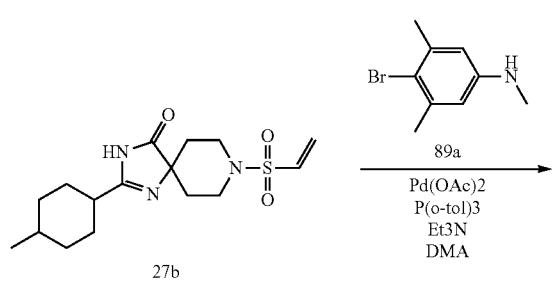

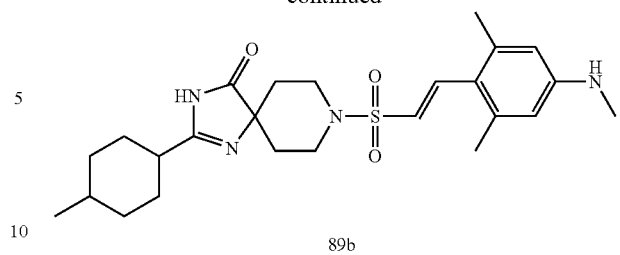

8-[2-(2,6-Dimethyl-4-methylamino-phenyl)-ethanesulfonyl]-2-(4-methyl-cyclohexyl)-1,3,8-triaza-spiro[4.5]dec-1-en-4-one was synthesized by operations similar to those in Reaction 25-2 using appropriate reagents and starting material.

MS (ESI) m/z=473 (M+H)+.

(Reaction 89-2)

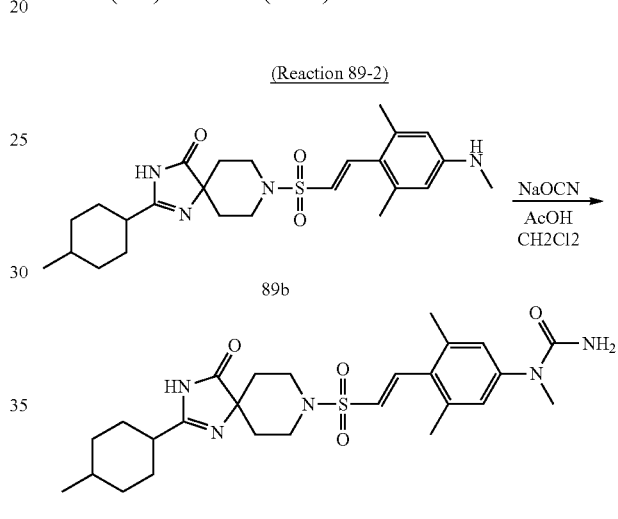

Sodium cyanate (15 mg, 0.243 mmol) was added to a solution of 8-[2-(2,6-dimethyl-4-methylamino-phenyl)-ethanesulfonyl]-2-(4-methyl-cyclohexyl)-1,3,8-triaza-spiro[4.5]dec-1-en-4-one (23 mg, 0.0487 mmol) and acetic acid (1.3 ml) in dichloromethane (0.5 ml) at room temperature, and the mixture was then stirred for two hours. The reaction mixture was diluted with dichloromethane, and the organic layer was then washed with water and a saturated aqueous sodium bicarbonate solution, dried over anhydrous sodium sulfate and concentrated under reduced pressure. The resulting residue was purified by preparative TLC (silica gel, MeOH/AcOEt/CH$_2$Cl$_2$) to give 1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (22.5 mg, 90%).

$^1$H-NMR (400 MHz, CDCl$_3$) δ 0.92 (3H, d, J=4.0 Hz), 0.95-1.1 (2H, m), 1.35-1.50 (3H, m), 1.65-1.75 (2H, m), 1.80-1.85 (2H, m), 1.90-2.00 (4H, m), 2.30-2.40 (1H, m), 2.38 (6H, s), 3.26 (3H, s), 3.35-3.45 (2H, m), 3.60-3.75 (2H, m), 4.54 (2H, brs), 6.39 (1H, d, J=16.0 Hz), 7.03 (2H, s), 7.54 (1H, d, J=16.0 Hz), 8.10 (1H, brs). MS (ESI) m/z=516 (M+H)+.

(Reaction 89-3)

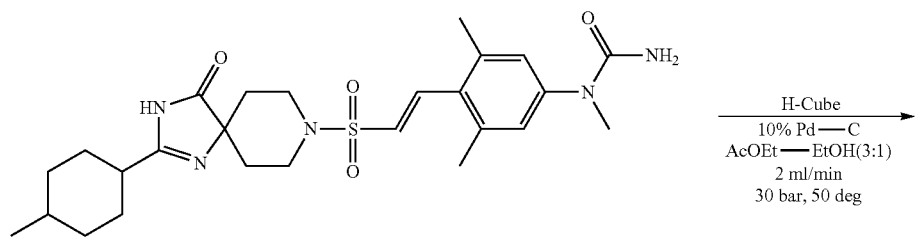

89c

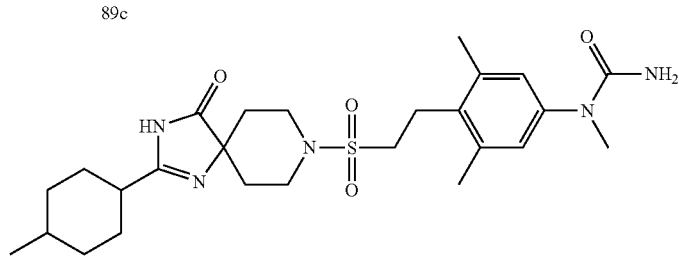

Compound 470

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 42-2 using appropriate reagents and starting material.

$^{1}$H-NMR (400 MHz, CD$_3$OD) δ 0.92 (3H, d, J=8.0 Hz), 0.95-1.06 (2H, m), 1.35-1.50 (3H, m), 1.65-1.75 (2H, m), 1.80-1.86 (2H, m), 1.88-2.00 (4H, m), 2.30-2.40 (1H, m), 2.36 (6H, s), 2.95-3.02 (2H, m), 3.15-3.22 (2H, m), 3.23 (3H, s), 3.45-3.52 (2H, m), 3.68-3.77 (2H, m), 4.47 (2H, brs), 6.95 (2H, s), 8.06 (1H, brs). MS (ESI) m/z=518 (M+H)+.

Example 90

1-(3,5-Dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea (Compound 471)

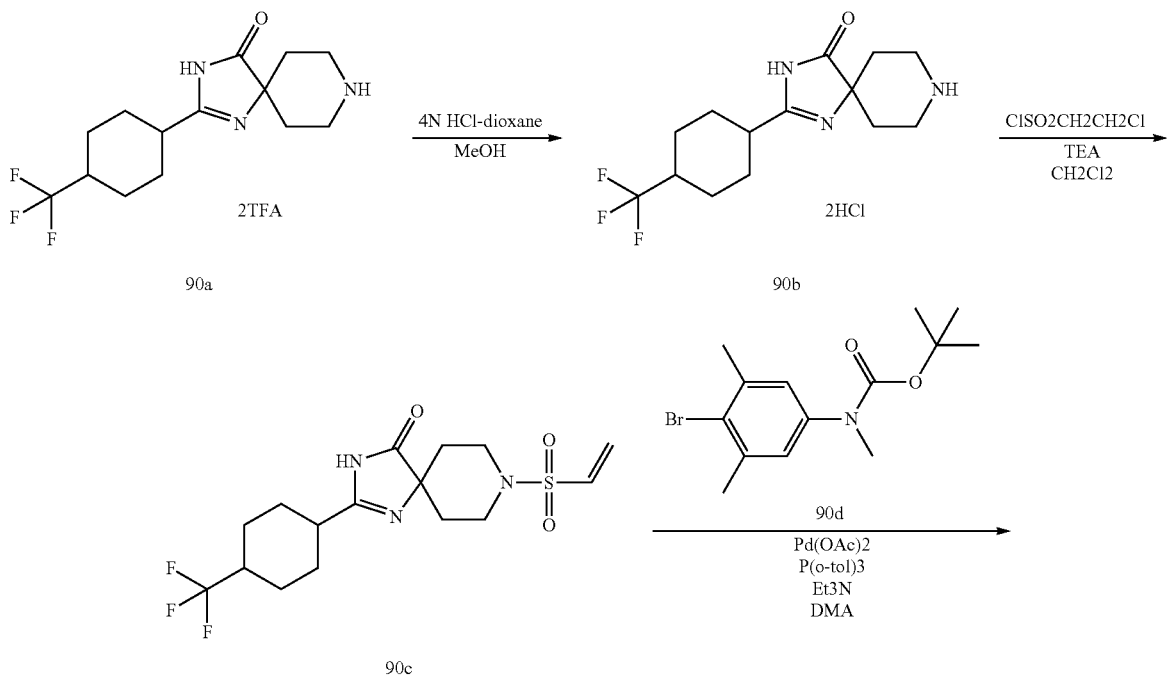

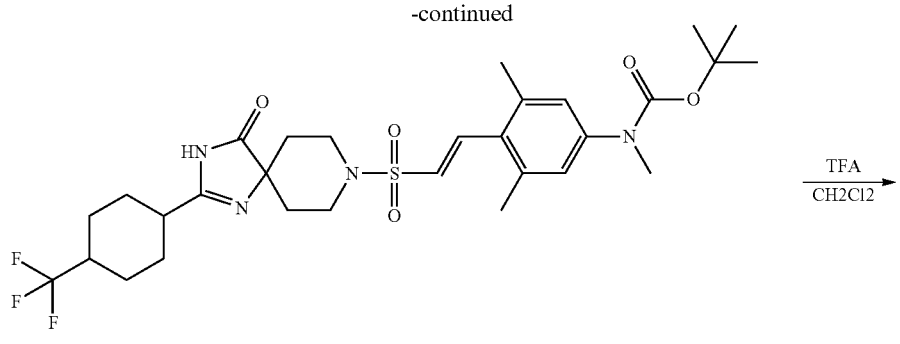

90e

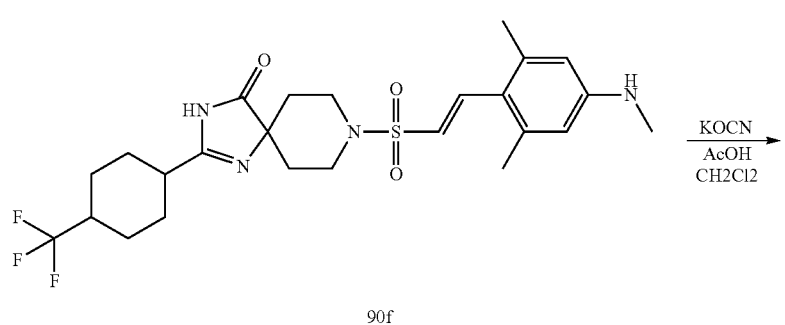

90f

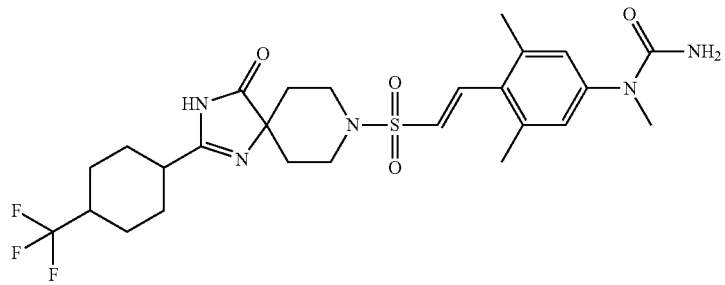

Compound 471

1-(3,5-Dimethyl-4-{(E)-2-[4-oxo-2-(4-trifluoromethyl-cyclohexyl)-1,3,8-triaza-spiro[4.5]dec-1-ene-8-sulfonyl]-vinyl}-phenyl)-1-methyl-urea was synthesized by operations similar to those in Reaction 5-3, Reaction 25-1, Reaction 26-1, Reaction 7-2 and Reaction 89-2 using appropriate reagents and starting material.

MS (ESI) m/z=570 (M+H)+.

Example 91

1-(3,5-Dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea (Compound 472)

(Reaction 91-1)

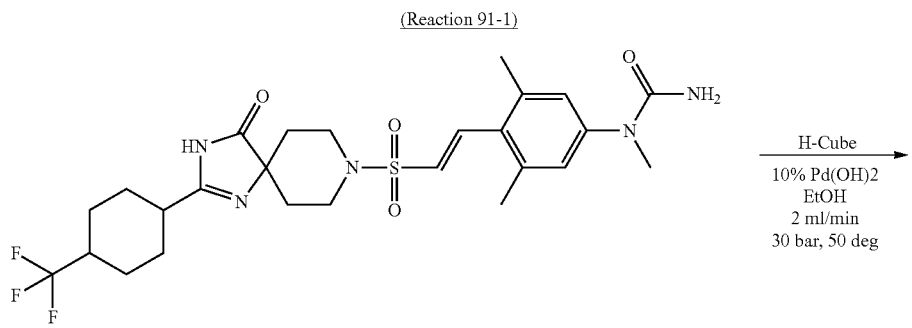

Compound 471

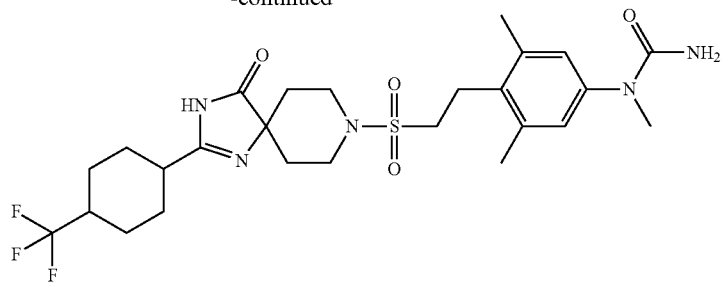

Compound 472

1-(3,5-Dimethyl-4-{2-[4-oxo-2-(4-trifluoromethyl-cyclohexyl)-1,3,8-triaza-spiro[4.5]dec-1-ene-8-sulfonyl]-ethyl}-phenyl)-1-methyl-urea was synthesized by operations similar to those in Reaction 42-2 using appropriate reagents and starting material.

MS (ESI) m/z=572 (M+H)+.

Example 92

(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 473)

(Reaction 92-1)

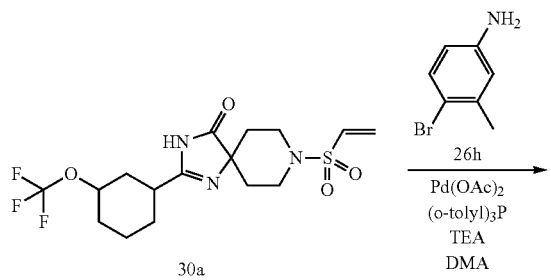

8-[(E)-2-(4-amino-2-methyl-phenyl)-ethenesulfonyl]-2-(3-trifluoromethoxy-phenyl)-1,3,8-triaza-spiro[4.5]dec-1-en-4-one was obtained by operations similar to those in Reaction 26-1 using 8-ethenesulfonyl-2-(3-trifluoromethoxy-phenyl)-1,3,8-triaza-spiro[4.5]dec-1-en-4-one as a starting material.

MS (ESI) m/z=509 (M+H)+.

(Reaction 92-2)

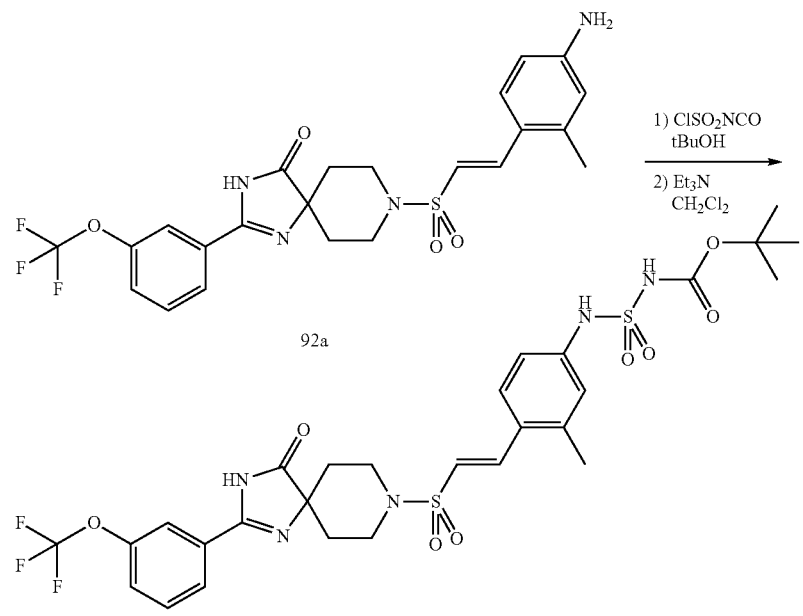

A solution of tert-butanol (71.9 mg, 0.97 mmol) in dichloromethane (1.5 ml) was added to a solution of chlorosulfonyl isocyanate (137 mg, 0.97 mmol) in dichloromethane (3 ml) with stirring under ice-cooling. The mixture was stirred at 0° C. for 10 minutes. A solution of 8-[(E)-2-(4-amino-2-methyl-phenyl)-ethenesulfonyl]-2-(3-trifluoromethoxy-phenyl)-1,3,8-triaza-spiro[4.5]dec-1-en-4-one (400 mg, 0.81 mmol) and triethylamine (164 mg, 1.62 mmol) in dichloromethane (3 ml) was then added, and the mixture was further stirred for one hour. The mixed reaction solution was quenched with water and then extracted with dichloromethane. The organic layer was washed with saturated brine, and then dried over anhydrous magnesium sulfate and concentrated under reduced pressure. The resulting residue was purified by silica gel column chromatography (ethyl acetate-hexane) to give N-(tert-butoxycarbonyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)sulfamide (334 mg, 60.0%).

$^1$H-NMR (400 MHz, CDCl$_3$) δ 1.42 (9H, s), 1.78 (2H, dt, J=14.2, 3.9 Hz), 2.04-2.14 (2H, m), 2.40 (3H, s), 3.43 (2H, ddd, J=12.7, 9.8, 2.9 Hz), 3.74 (2H, dt, J=12.2, 4.4 Hz), 6.64 (1H, d, J=15.6 Hz), 7.08-7.11 (2H, m), 7.38 (1H, d, J=8.3 Hz), 7.48-7.54 (2H, m), 7.68 (1H, d, J=15.1 Hz), 7.73 (1H, d, J=7.8 Hz), 7.76 (1H, s), 9.62 (1H, s);

MS (ESI) m/z=688 (M+H)+.

(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was obtained by operations similar to those in Reaction 4-1 using N-(tert-butoxycarbonyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)sulfamide as a starting material.

MS (ESI) m/z=588 (M+H)+.

Example 93

1-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (Compound 474)

(Reaction 93-1)

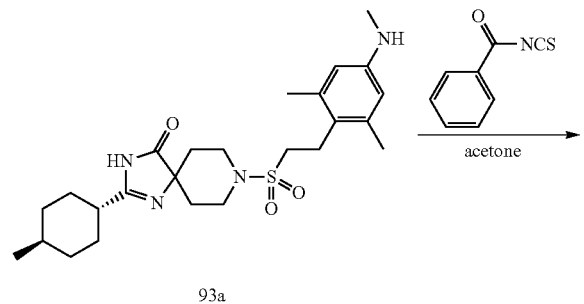

93a (Reaction 92-3)

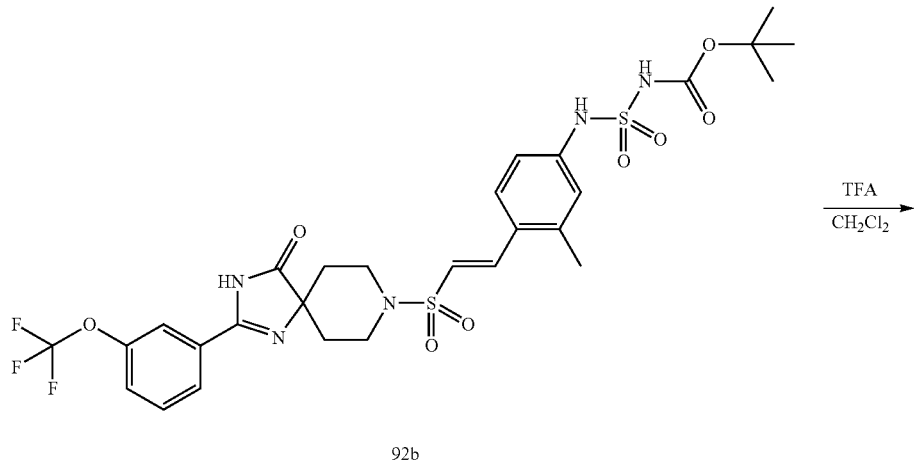

92b

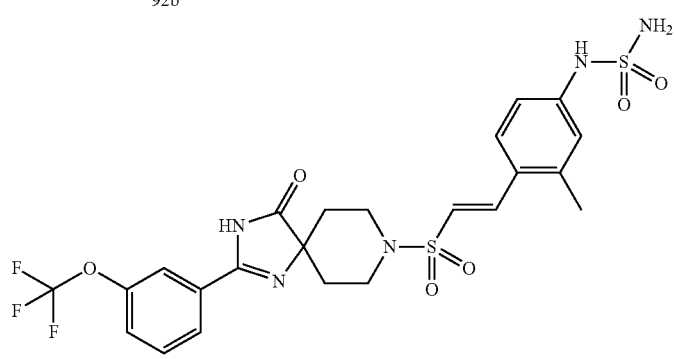

Compound 473

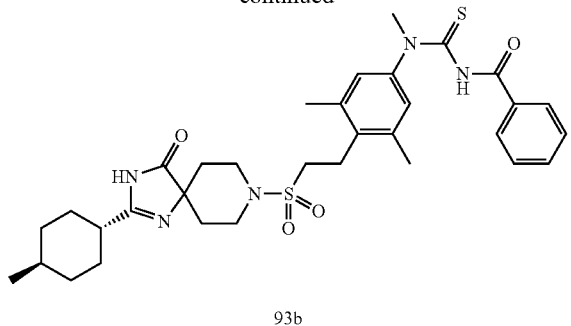

93b

Benzoyl isothiocyanate (37.8 mg, 0.23 mmol) was added to a solution of 8-[2-(2,6-dimethyl-4-methylamino-phenyl)-ethanesulfonyl]-2-(4-methyl-cyclohexyl)-1,3,8-triaza-spiro[4.5]dec-1-en-4-one (100 mg, 0.21 mmol) in acetone (3 ml) in a nitrogen stream. The mixture was heated under reflux for one hour and then concentrated under reduced pressure. The resulting residue was purified by silica gel column chromatography (dichloromethane-methanol) to give 3-benzoyl-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (140 mg).

$^1$H-NMR (400 MHz, CDCl$_3$) δ 0.92 (3H, d, J=6.8 Hz), 0.94-1.07 (2H, m), 1.32-1.46 (3H, m), 1.52-1.64 (2H, m), 1.82 (2H, dd, J=13.7, 2.4 Hz), 1.90-2.00 (4H, m), 2.28-2.33 (1H, m), 2.35 (6H, s), 2.90-3.00 (2H, m), 3.08-3.16 (2H, m), 3.36-3.45 (2H, m), 3.64-3.78 (5H, m), 7.01 (2H, s), 7.37-7.62 (5H, m);

MS (ESI) m/z=638 (M+H)+.

Hydrazine monohydrate (55 mg, 1.1 mmol) was added to a solution of 3-benzoyl-1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (140 mg, 0.22 mmol) in ethanol (7 ml). The mixture was stirred at room temperature for 15 hours and then concentrated under reduced pressure. The resulting residue was purified by silica gel column chromatography (dichloromethane-methanol) to give 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (119 mg).

$^1$H-NMR (400 MHz, CDCl$_3$) δ 0.92 (3H, d, J=6.3 Hz), 1.00 (2H, ddd, J=25.4, 13.7, 2.9 Hz), 1.32-1.47 (3H, m), 1.59-1.68 (2H, m), 1.82 (2H, dd, J=10.7, 3.4 Hz), 1.90-1.98 (4H, m), 2.28-2.35 (1H, m), 2.35 (6H, s), 2.95-3.02 (2H, m), 3.15-3.22 (2H, m), 3.45 (2H, ddd, J=12.2, 9.3, 3.4 Hz), 3.55 (3H, s), 3.74 (2H, dt, J=13.1, 4.4 Hz), 5.63 (1H, brs), 6.94 (2H, s), 8.14 (1H, s);

MS (ESI) m/z=534 (M+H)+.

(Reaction 93-2)

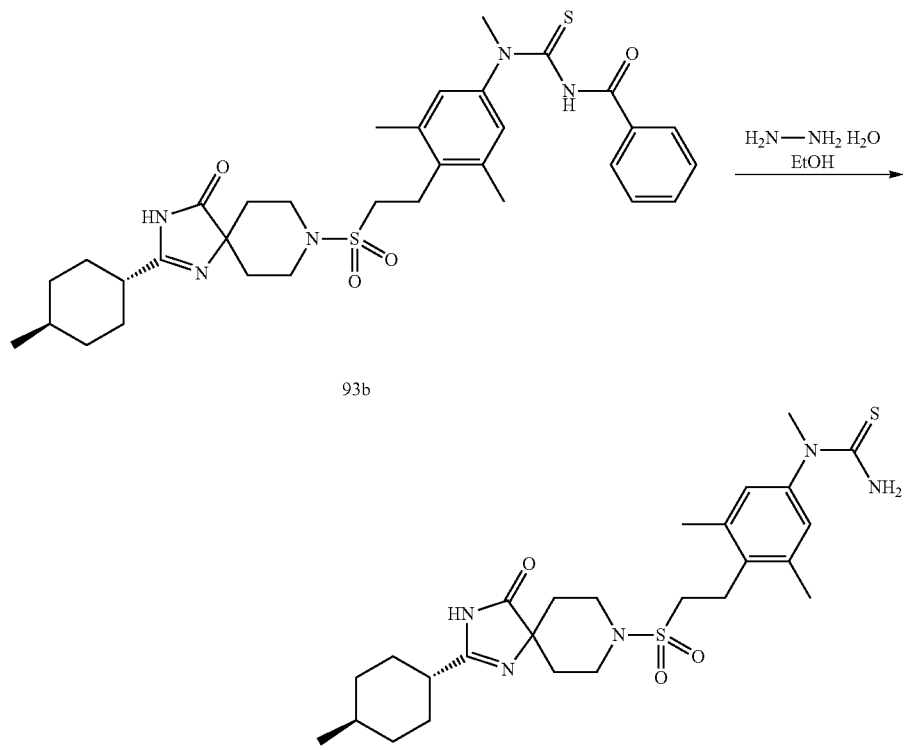

Compound 474

Example 94

8-{2-[2,6-Dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one (Compound 475)

(Reaction 94-1)

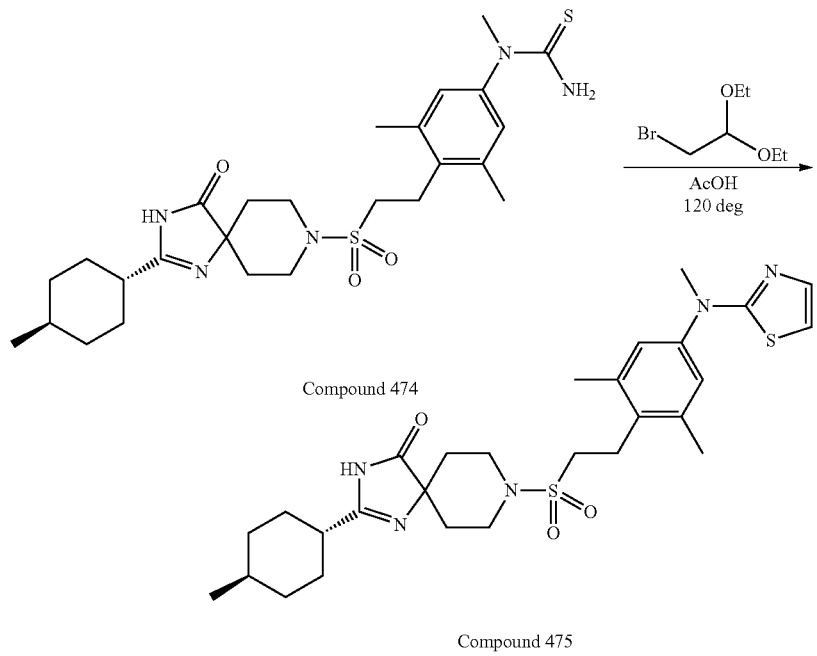

Bromoacetaldehyde diethylacetal (44.2 mg, 0.224 mmol) was added to a solution of 1-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-thiourea (100 mg, 0.187 mmol) in acetic acid (2 ml) in a nitrogen stream. The mixture was heated under reflux for two hours and then concentrated under reduced pressure. The resulting residue was diluted with dichloromethane, and the organic layer was then sequentially washed with a saturated aqueous sodium bicarbonate solution and saturated brine and dried over anhydrous magnesium sulfate. The organic layer was concentrated, and the resulting residue was then purified by silica gel column chromatography (dichloromethane-methanol) to give 8-{2-[2,6-Dimethyl-4-(methyl-thiazol-2-yl-amino)-phenyl]-ethanesulfonyl}-2-(4-methyl-cyclohexyl)-1,3,8-triaza-spiro[4.5]dec-1-en-4-one (7.1 mg).

$^1$H-NMR (400 MHz, CDCl$_3$) δ 0.92 (3H, d, J=6.8 Hz), 0.95-1.07 (2H, m), 1.33-1.48 (3H, m), 1.56-1.67 (2H, m), 1.82 (2H, d, J=11.2 Hz), 1.91-2.03 (4H, m), 2.29-2.35 (1H, m), 2.37 (6H, s), 2.99-3.06 (2H, m), 3.14-3.21 (2H, m), 3.43 (2H, ddd, J=12.7, 9.3, 2.9 Hz), 3.49 (3H, s), 3.77 (2H, dt, J=12.2, 4.4 Hz), 6.48 (1H, d, J=3.4 Hz), 7.06 (2H, s), 7.22 (1H, d, J=3.4 Hz), 8.33 (1H, s);

MS (ESI) m/z=558 (M+H)+.

Example 95

The example compounds shown below were obtained by operations similar to those in Reaction 25-2 using appropriate reagents and starting materials.

Compounds 476 to 503

TABLE 70

| Target Compound | Structure | LCMS condition | Retention time (min) | MS (m/z) |
| --- | --- | --- | --- | --- |
| 476 | 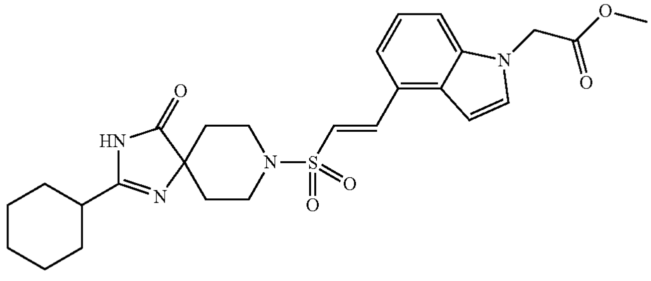 [SMILES: COC(=O)Cn1ccc2c(/C=C/S(=O)(=O)N3CCC4(CC3)N=C(C3CCCCC3)NC4=O)cccc21] | LCMS-C-1 | 2.53 | 513 (M + H)+ |

TABLE 70-continued

| Target Compound | Structure | LCMS condition | Retention time (min) | MS (m/z) |
| --- | --- | --- | --- | --- |
| 477 | 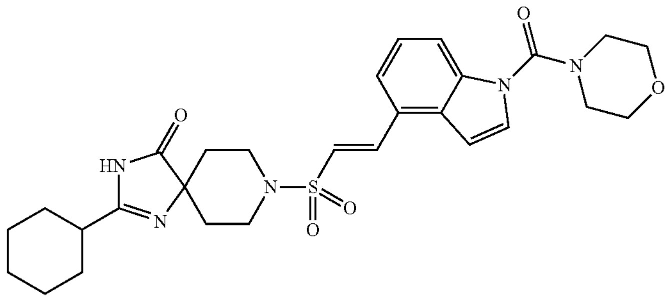 [SMILES: O=C(N1CCOCC1)n1ccc2c(/C=C/S(=O)(=O)N3CCC4(CC3)N=C(C3CCCCC3)NC4=O)cccc21] | LCMS-C-1 | 2.55 | 554 (M + H)+ |
| 478 | 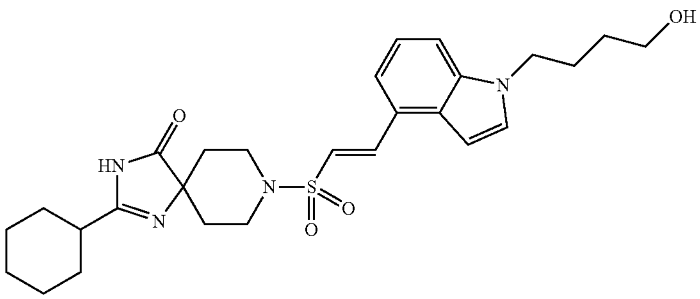 | LCMS-C-1 | 2.62 | 513 (M + H)+ |
| 479 | 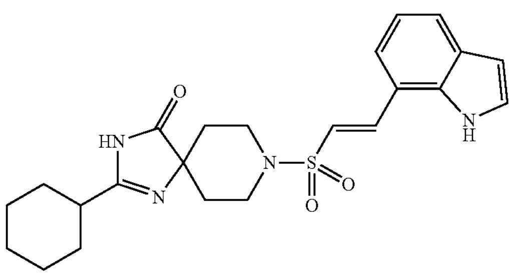 [SMILES: O=C1NC(C2CCCCC2)=NC12CCN(S(=O)(=O)/C=C/c1cccc3cc[nH]c13)CC2] | LCMS-A-1 | 2.25 | 441 (M + H)+ |
| 480 | 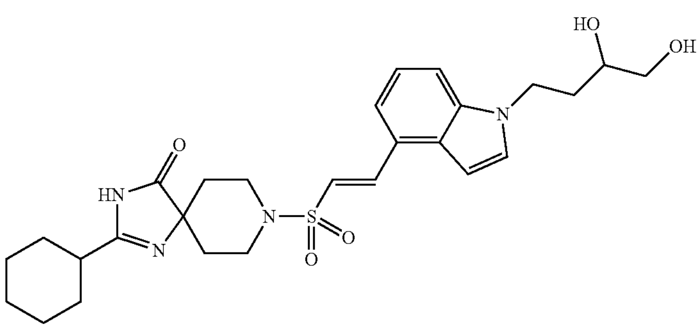 [SMILES: O=C1NC(C2CCCCC2)=NC12CCN(S(=O)(=O)/C=C/c1cccc3c1ccn3CCC(O)CO)CC2] | LCMS-C-1 | 2.42 | 529 (M + H)+ |
| 481 | 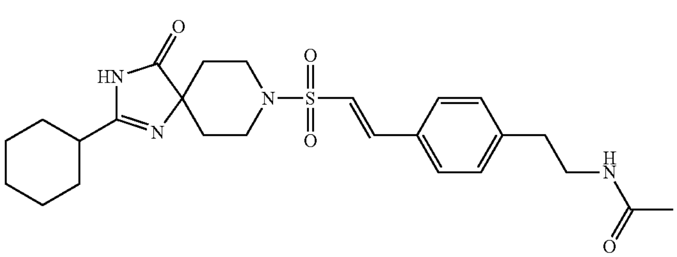 [SMILES: CC(=O)NCCc1ccc(/C=C/S(=O)(=O)N2CCC3(CC2)N=C(C2CCCCC2)NC3=O)cc1] | LCMS-C-1 | 2.30 | 485 (M − H)− |

TABLE 70-continued

| Target Compound | Structure | LCMS condition | Retention time (min) | MS (m/z) |
|---|---|---|---|---|
| 482 | 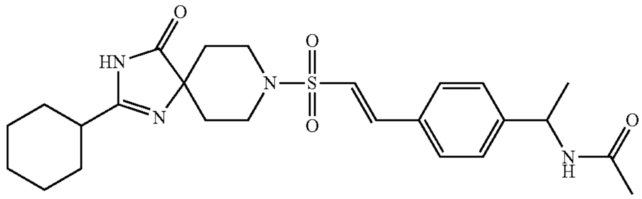 [SMILES: CC(=O)NC(C)c1ccc(/C=C/S(=O)(=O)N2CCC3(CC2)N=C(C2CCCCC2)NC3=O)cc1] | LCMS-C-1 | 2.30 | 485 (M − H)− |
| 483 | 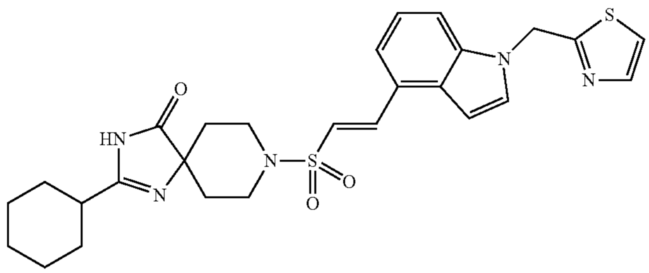 [SMILES: O=C1NC(C2CCCCC2)=NC12CCN(S(=O)(=O)/C=C/c1cccc3c1ccn3Cc1nccs1)CC2] | LCMS-C-1 | 2.62 | 536 (M − H)− |
| 484 | 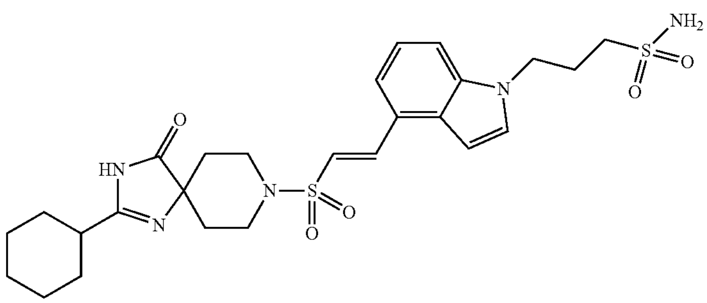 [SMILES: NS(=O)(=O)CCCn1ccc2c(/C=C/S(=O)(=O)N3CCC4(CC3)N=C(C3CCCCC3)NC4=O)cccc21] | LCMS-C-1 | 2.38 | 562 (M + H)+ |
| 485 | 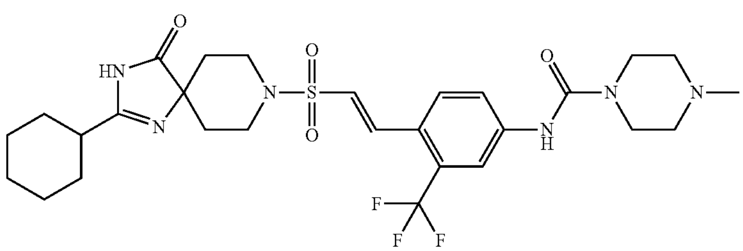 [SMILES: CN1CCN(C(=O)Nc2ccc(/C=C/S(=O)(=O)N3CCC4(CC3)N=C(C3CCCCC3)NC4=O)c(C(F)(F)F)c2)CC1] | LCMS-C-1 | 2.68 | 611 (M + H)+ |
| 486 | 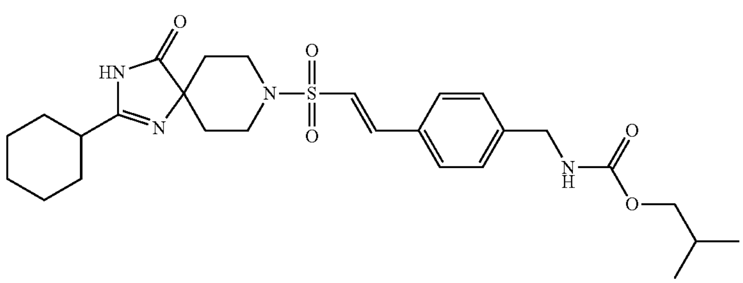 [SMILES: CC(C)COC(=O)NCc1ccc(/C=C/S(=O)(=O)N2CCC3(CC2)N=C(C2CCCCC2)NC3=O)cc1] | LCMS-C-1 | 2.75 | 529 (M − H)− |
| 487 | 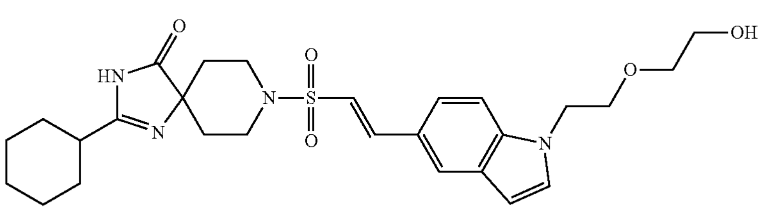 [SMILES: O=C1NC(C2CCCCC2)=NC12CCN(S(=O)(=O)/C=C/c1ccc3c(ccn3CCOCCO)c1)CC2] | LCMS-A-1 | 2.00 | 529 (M + H)+ |

TABLE 70-continued

| Target Compound | Structure | LCMS condition | Retention time (min) | MS (m/z) |
|---|---|---|---|---|
| 488 | 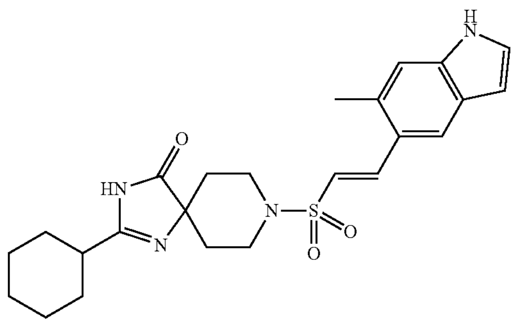 [SMILES: Cc1cc2[nH]ccc2cc1/C=C/S(=O)(=O)N1CCC2(CC1)N=C(C1CCCCC1)NC2=O] | LCMS-A-1 | 2.17 | 455 (M + H)+ |
| 489 | 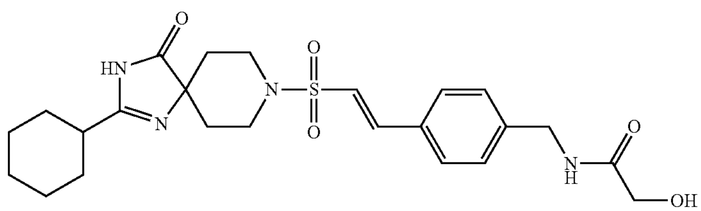 [SMILES: O=C(CO)NCc1ccc(/C=C/S(=O)(=O)N2CCC3(CC2)N=C(C2CCCCC2)NC3=O)cc1] | LCMS-C-1 | 2.30 | 489 (M + H)+ |
| 490 | 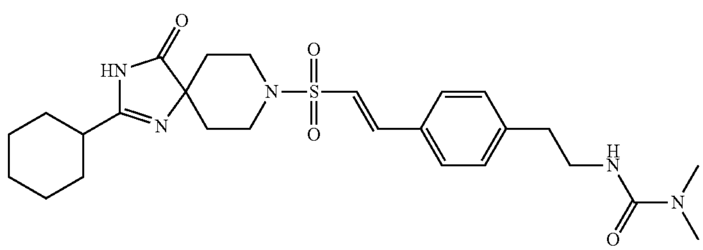 [SMILES: CN(C)C(=O)NCCc1ccc(/C=C/S(=O)(=O)N2CCC3(CC2)N=C(C2CCCCC2)NC3=O)cc1] | LCMS-C-1 | 2.38 | 516 (M + H)+ |
| 491 | 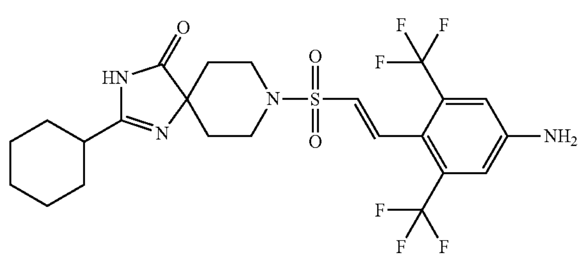 [SMILES: Nc1cc(C(F)(F)F)c(/C=C/S(=O)(=O)N2CCC3(CC2)N=C(C2CCCCC2)NC3=O)c(C(F)(F)F)c1] | LCMS-C-1 | 2.68 | 551 (M − H)− |
| 492 | 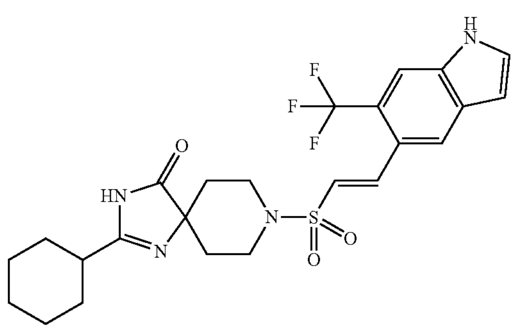 [SMILES: O=C1NC(C2CCCCC2)=NC12CCN(S(=O)(=O)/C=C/c1cc3cc[nH]c3cc1C(F)(F)F)CC2] | LCMS-A-1 | 2.30 | 509 (M + H)+ |

TABLE 70-continued

| Target Compound | Structure | LCMS condition | Retention time (min) | MS (m/z) |
|---|---|---|---|---|
| 493 | 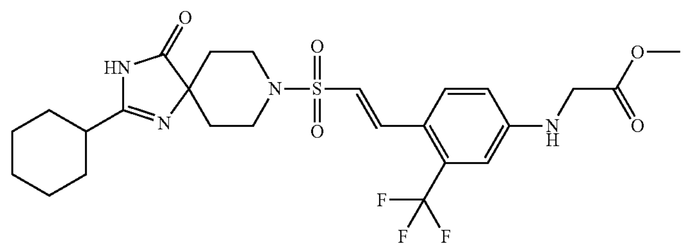 [SMILES: COC(=O)CNc1ccc(/C=C/S(=O)(=O)N2CCC3(CC2)N=C(C2CCCCC2)NC3=O)c(C(F)(F)F)c1] | LCMS-C-1 | 2.65 | 557 (M + H)+ |
| 494 | 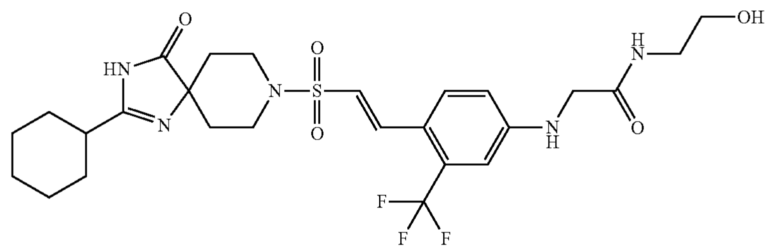 [SMILES: O=C(CNc1ccc(/C=C/S(=O)(=O)N2CCC3(CC2)N=C(C2CCCCC2)NC3=O)c(C(F)(F)F)c1)NCCO] | LCMS-A-1 | 1.90 | 586 (M + H)+ |
| 495 | 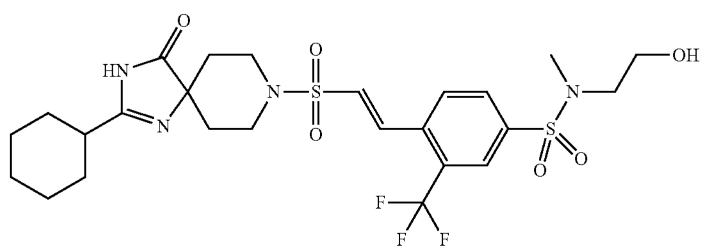 [SMILES: CN(CCO)S(=O)(=O)c1ccc(/C=C/S(=O)(=O)N2CCC3(CC2)N=C(C2CCCCC2)NC3=O)c(C(F)(F)F)c1] | LCMS-C-1 | 2.60 | 607 (M + H)+ |
| 496 | 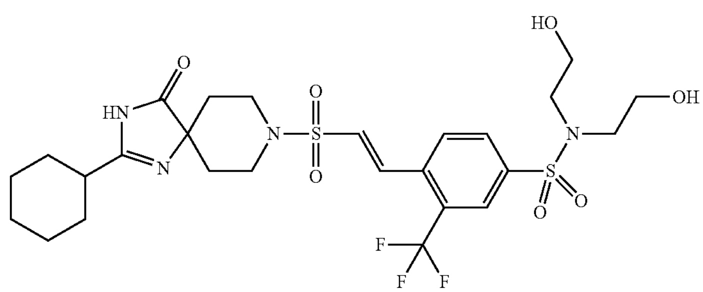 [SMILES: O=C1NC(C2CCCCC2)=NC12CCN(S(=O)(=O)/C=C/c1ccc(S(=O)(=O)N(CCO)CCO)cc1C(F)(F)F)CC2] | LCMS-C-1 | 2.48 | 637 (M + H)+ |
| 497 | 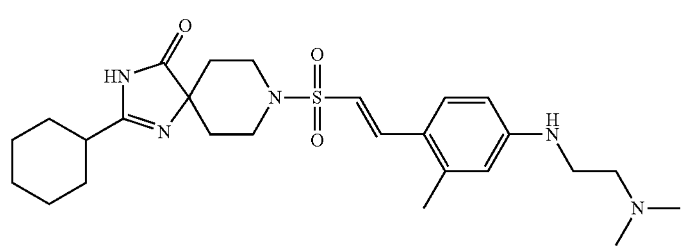 [SMILES: Cc1cc(NCCN(C)C)ccc1/C=C/S(=O)(=O)N1CCC2(CC1)N=C(C1CCCCC1)NC2=O] | LCMS-C-1 | 2.32 | 502 (M + H)+ |

TABLE 70-continued

| Target Compound | Structure | LCMS condition | Retention time (min) | MS (m/z) |
|---|---|---|---|---|
| 498 | 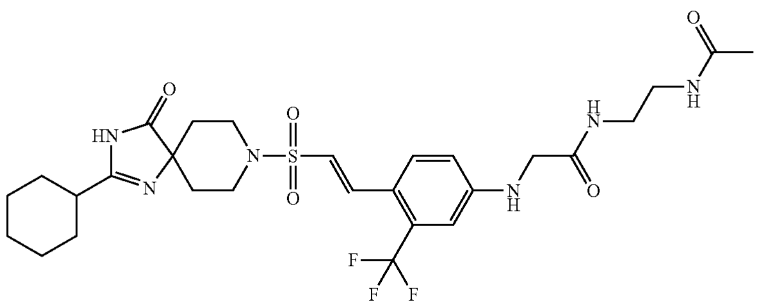 [SMILES: CC(=O)NCCNC(=O)CNc1ccc(/C=C/S(=O)(=O)N2CCC3(CC2)N=C(C2CCCCC2)NC3=O)c(C(F)(F)F)c1] | LCMS-C-1 | 2.37 | 627 (M + H)+ |
| 499 | 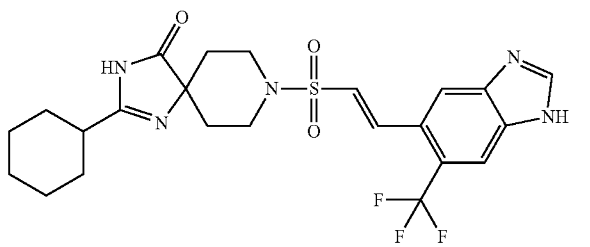 [SMILES: O=C1NC(C2CCCCC2)=NC12CCN(S(=O)(=O)/C=C/c1cc3nc[nH]c3cc1C(F)(F)F)CC2] | LCMS-C-1 | 2.55 | 510 (M + H)+ |
| 500 | 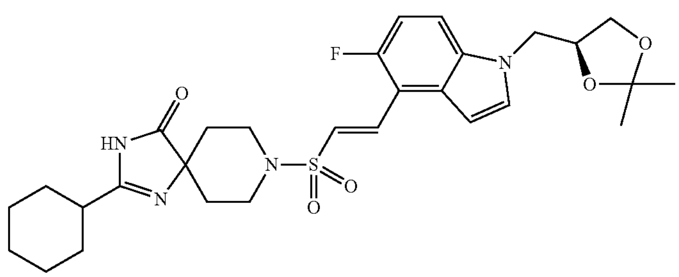 [SMILES: CC1(C)OC[C@H](Cn2ccc3c(/C=C/S(=O)(=O)N4CCC5(CC4)N=C(C4CCCCC4)NC5=O)c(F)ccc32)O1] | LCMS-A-1 | 2.35 | 573 (M + H)+ |
| 501 | 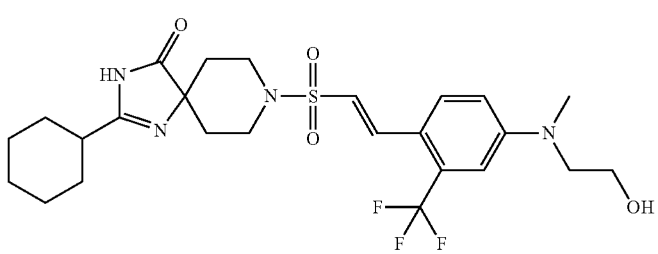 [SMILES: CN(CCO)c1ccc(/C=C/S(=O)(=O)N2CCC3(CC2)N=C(C2CCCCC2)NC3=O)c(C(F)(F)F)c1] | LCMS-A-1 | 2.14 | 543 (M + H)+ |
| 502 | 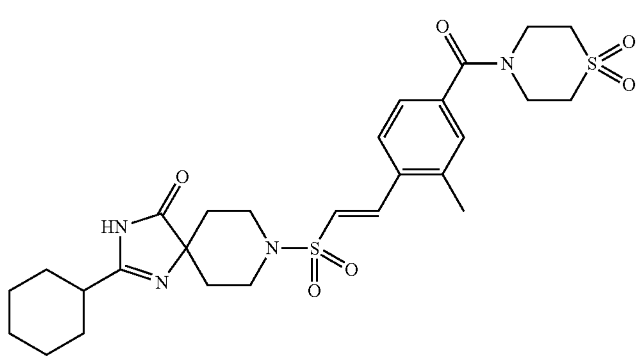 [SMILES: Cc1cc(C(=O)N2CCS(=O)(=O)CC2)ccc1/C=C/S(=O)(=O)N1CCC2(CC1)N=C(C1CCCCC1)NC2=O] | LCMS-C-1 | 2.18 | 577 (M + H)+ |

TABLE 70-continued

| Target Compound | Structure | LCMS condition | Retention time (min) | MS (m/z) |
|---|---|---|---|---|
| 503 | 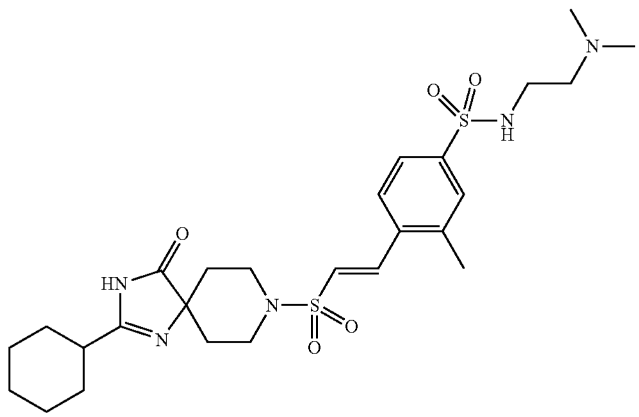 [SMILES: Cc1cc(S(=O)(=O)NCCN(C)C)ccc1/C=C/S(=O)(=O)N1CCC2(CC1)N=C(C1CCCCC1)NC2=O] | LCMS-C-1 | 2.28 | 566 (M + H)+ |

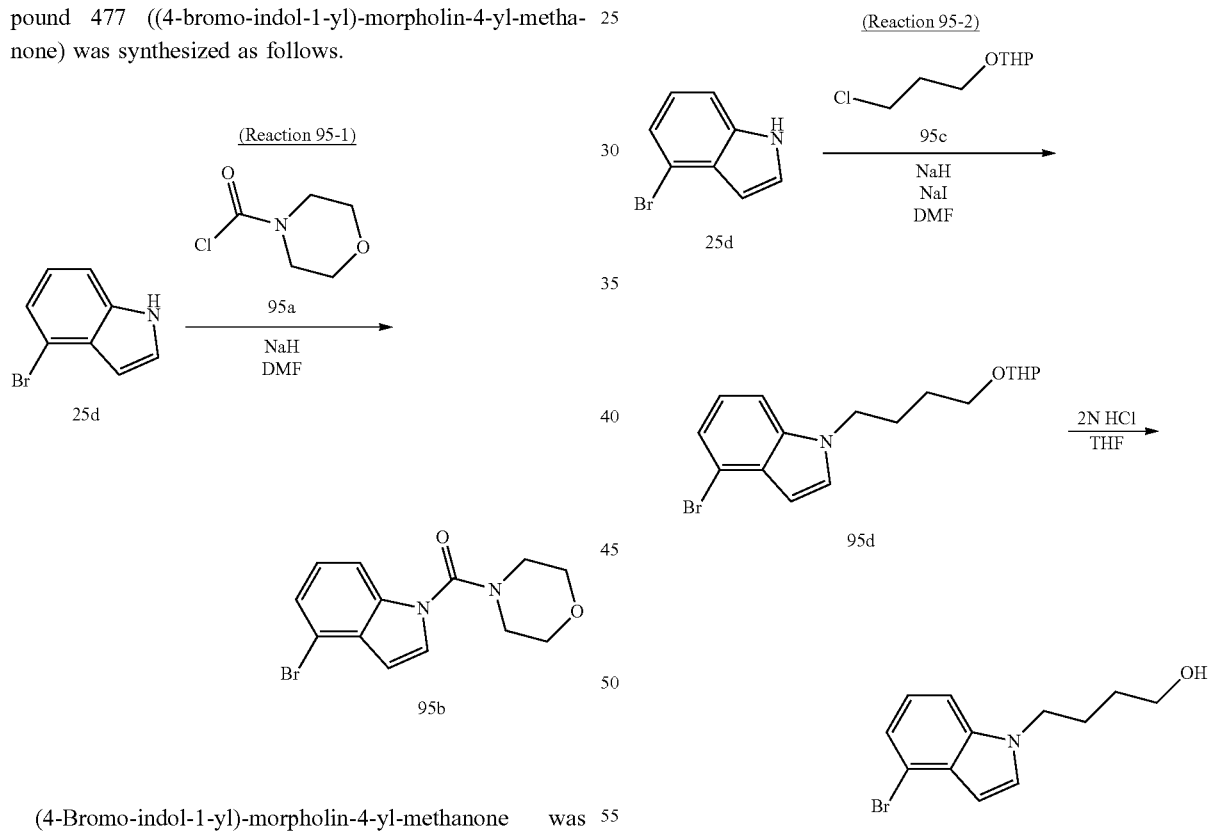

The aryl bromide reagent used in the synthesis of Compound 477 ((4-bromo-indol-1-yl)-morpholin-4-yl-methanone) was synthesized as follows.

(4-Bromo-indol-1-yl)-morpholin-4-yl-methanone was synthesized by operations similar to those in Reaction 25-3 using appropriate reagents and starting material.

$^1$H-NMR (400 MHz, CDCl$_3$) δ 3.61 (4H, t, J=4.8 Hz), 3.78 (4H, t, J=4.8 Hz), 6.69 (1H, d, J=3.6 Hz), 7.17 (1H, t, J=7.9 Hz), 7.35 (2H, d, J=3.6 Hz), 7.38 (2H, d, J=7.9 Hz), 7.65 (1H, d, J=7.9 Hz).

The aryl bromide reagent used in the synthesis of Compound 478 (4-(4-bromo-indol-1-yl)-butan-1-ol) was synthesized as follows.

4-(4-Bromo-indol-1-yl)-butan-1-ol was synthesized by operations similar to those in Reaction 29-7 and Reaction 25-4 using appropriate reagents and starting material.

MS (ESI) m/z=268, 270 (M+H)+.

The aryl bromide reagent used in the synthesis of Compound 480 (4-(4-bromo-indol-1-yl)-butane-1,2-diol) was synthesized as follows.

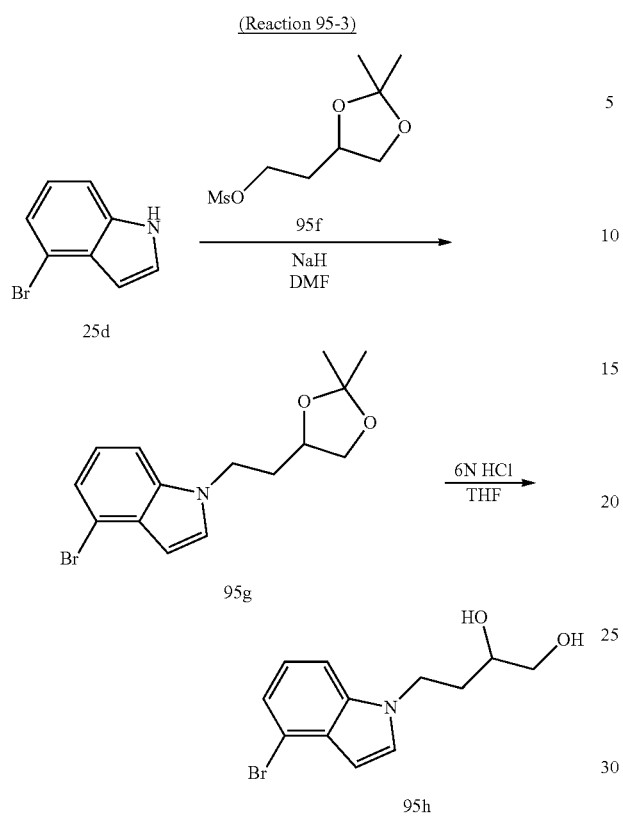

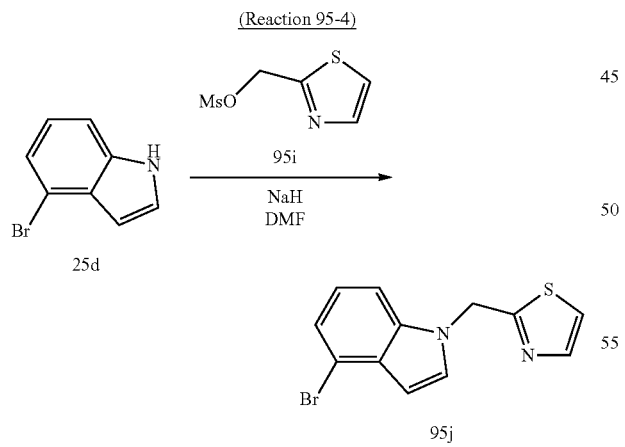

4-(4-Bromo-indol-1-yl)-butane-1,2-diol was synthesized by operations similar to those in Reaction 25-3 and Reaction 25-4 using appropriate reagents and starting material.

MS (ESI) m/z=284, 286 (M+H)+.

The aryl bromide reagent used in the synthesis of Compound 483 (4-bromo-1-thiazol-2-ylmethyl-1H-indole) was synthesized as follows.

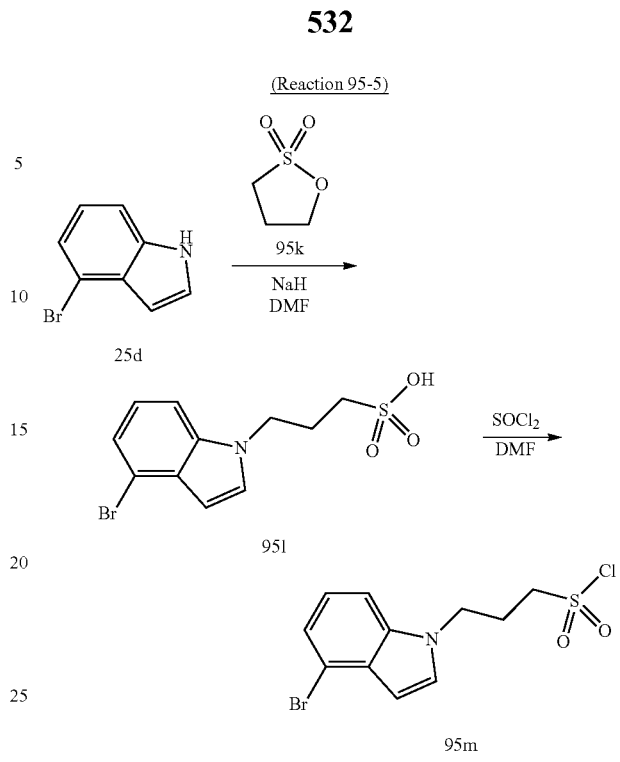

4-Bromo-1-thiazol-2-ylmethyl-1H-indole was synthesized by operations similar to those in Reaction 25-3 using appropriate reagents and starting material.

MS (ESI) m/z=293, 295 (M+H)+.

The aryl bromide reagent used in the synthesis of Compound 484 (3-(4-bromo-indol-1-yl)-propane-1-sulfonic amide) was synthesized as follows.

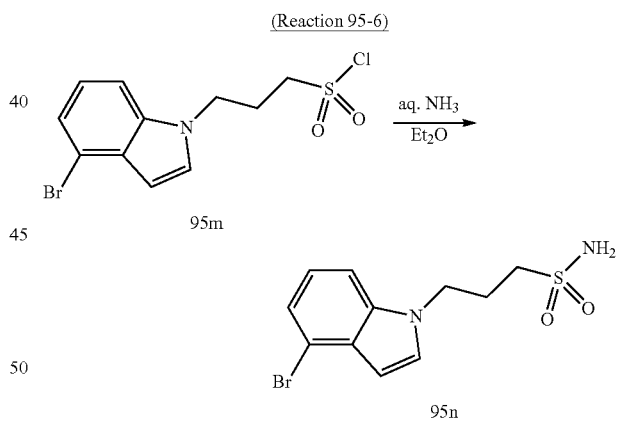

3-(4-Bromo-indol-1-yl)-propane-1-sulfonyl chloride was synthesized as a crude product by operations similar to those in Reaction 25-3 and Reaction 52-3 using 4-bromoindole (0.20 ml, 1.59 mmol) as a starting material and using THF as a solvent.

3-(4-Bromo-indol-1-yl)-propane-1-sulfonyl chloride obtained as a crude product was all dissolved in diethyl ether (3.0 ml). A 28% aqueous ammonia solution (3.0 ml) was then added dropwise and the mixture was stirred at room temperature for 2.5 hours. Water was added to the reaction system, followed by extraction with ethyl acetate. The organic layer was washed with water and saturated brine and then concentrated under reduced pressure. The resulting residue was purified by silica gel column chromatography (dichloromethane-ethyl acetate) to give 3-(4-bromo-indol-1-yl)-propane-1-sulfonic amide (55.6 mg, 11% in three steps).

MS (ESI) m/z=317, 319 (M+H)+.

The aryl bromide reagent used in the synthesis of Compound 485 (4-methyl-piperazine-1-carboxylic (4-bromo-3-trifluoromethyl-phenyl)-amide) was synthesized as follows.

(Reaction 95-7)

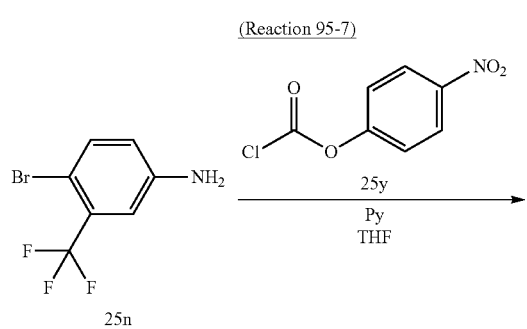

25n

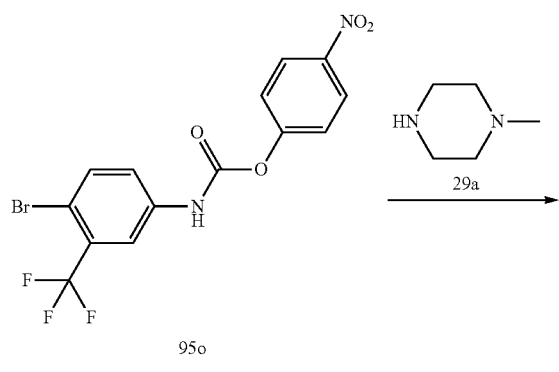

95o

95p

4-Methyl-piperazine-1-carboxylic (4-bromo-3-trifluoromethyl-phenyl)-amide was synthesized by operations similar to those in Reaction 25-11 using appropriate reagents and starting material.

MS (ESI) m/z=366, 368 (M+H)+.

The aryl bromide reagent used in the synthesis of Compound 486 ((4-bromo-benzyl)-carbamic acid isobutyl ester) was synthesized as follows.

(Reaction 95-8)

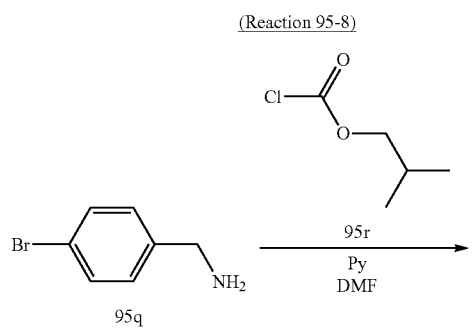

95q

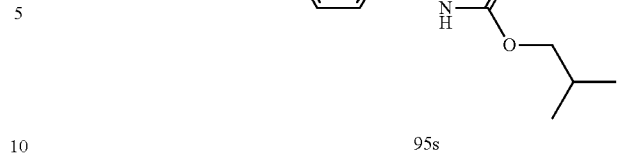

95s (4-Bromo-benzyl)-carbamic acid isobutyl ester was synthesized by operations similar to those in Reaction 25-10 using appropriate reagents and starting material.

MS (ESI) m/z=286, 288 (M+H)+.

The aryl bromide reagent used in the synthesis of Compound 487 (2-[2-(5-bromo-indol-1-yl)-ethoxy]-ethanol) was synthesized as follows.

(Reaction 95-9)

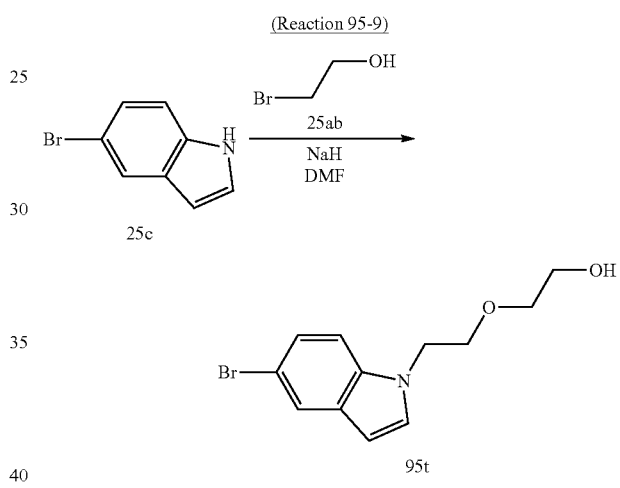

25c

95t

2-[2-(5-Bromo-indol-1-yl)-ethoxy]-ethanol was synthesized by operations similar to those in Reaction 25-3 using appropriate reagents and starting material.

$^1$H-NMR (270 MHz, CDCl$_3$) δ 7.74 (1H, d, J=1.6 Hz), 7.28 (1H, dd, J=8.7, 1.8 Hz), 7.23 (1H, d, J=8.6 Hz), 7.15 (1H, d, J=3.1 Hz), 6.44 (1H, d, J=3.1 Hz), 4.29 (2H, t, J=5.4 Hz), 3.79 (2H, t, J=5.4 Hz), 3.65-3.59 (2H, m), 3.48-3.44 (2H, m), 1.67 (1H, t, J=6.1 Hz).

The aryl bromide reagent used in the synthesis of Compound 488 (5-bromo-6-methyl-1H-indole) was synthesized as follows.

(Reaction 95-10)

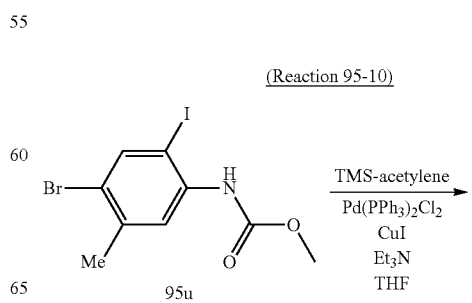

95u

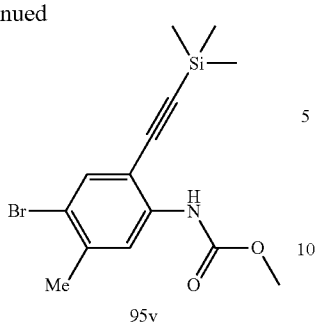

95v (4-Bromo-2-iodo-5-methyl-phenyl)-carbamic acid methyl ester (605 mg, 1.64 mmol) was dissolved in THF (6 ml). (Trimethylsilyl)acetylene (0.70 ml, 4.95 mmol), copper iodide (33.5 mg, 0.175 mmol), Pd(PPh$_3$)$_2$Cl$_2$ (56.5 mg, 0.081 mmol) and triethylamine (0.690 ml, 4.95 mmol) were added and the mixture was stirred at room temperature for four hours. Water was added to the reaction system, followed by extraction with ethyl acetate. The organic layer was washed with water and saturated brine, dried over anhydrous sodium sulfate and concentrated under reduced pressure. The resulting residue was purified by silica gel column chromatography (n-hexane-ethyl acetate) to give (4-bromo-5-methyl-2-trimethylsilanylethynyl-phenyl)-carbamic acid methyl ester (548 mg, 98%).

MS (ESI) m/z=340 (M+H)+.

(Reaction 95-11)

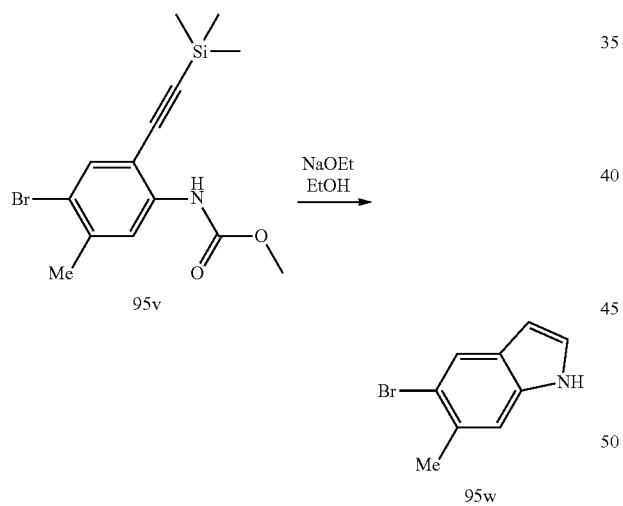

(4-Bromo-5-methyl-2-trimethylsilanylethynyl-phenyl)-carbamic acid methyl ester (506 mg, 1.49 mmol) was dissolved in ethanol (6 ml). Sodium ethoxide (20% solution in ethanol, 1.17 ml, 2.97 mmol) was added and the mixture was stirred at 70° C. overnight. The reaction solution was poured into ice water, and 1 N hydrochloric acid and saturated brine were added to this mixture, followed by extraction with ethyl acetate. The organic layer was washed with water and saturated brine, dried over anhydrous sodium sulfate and concentrated under reduced pressure. The resulting residue was purified by silica gel column chromatography (n-hexane-ethyl acetate) to give 5-bromo-6-methyl-1H-indole (207 mg, 66%).

$^1$H-NMR (270 MHz, CDCl$_3$) δ 8.04 (1H, br s), 7.81 (1H, s), 7.27 (1H, s), 7.16-7.14 (1H, m), 6.46-6.43 (1H, m), 2.49 (3H, s).

The aryl bromide reagent used in the synthesis of Compound 489 (N-(4-bromo-benzyl)-2-hydroxy-acetamide) was synthesized as follows.

(Reaction 9-12)

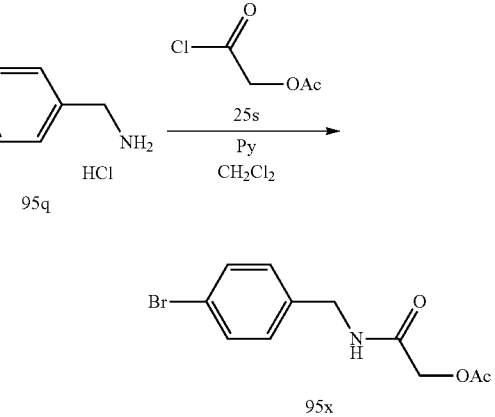

Acetic acid (4-bromo-benzylcarbamoyl)-methyl ester was synthesized as a crude product by operations similar to those in Reaction 2-3 using 4-bromobenzylamine hydrochloride (200 mg, 0.899 mmol) as a starting material and using pyridine as a base.

(Reaction 95-13)

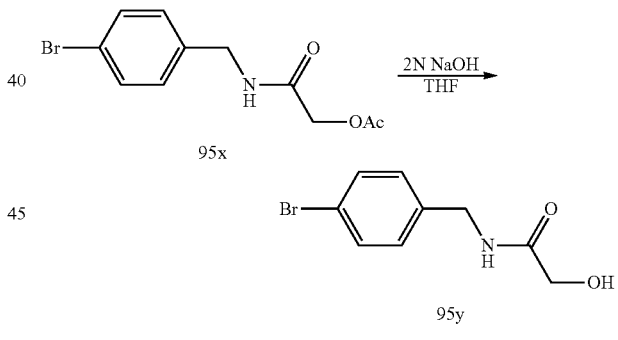

Acetic acid (4-bromo-benzylcarbamoyl)-methyl ester obtained as a crude product was all dissolved in THF (2.0 ml). A 2 N aqueous sodium hydroxide solution (2.0 ml) was then added and the mixture was stirred at room temperature for five hours. Water was added to the reaction system, followed by extraction with ethyl acetate. The organic layer was washed with saturated brine and then concentrated under reduced pressure. The resulting residue was purified by silica gel column chromatography (dichloromethane-methanol) to give N-(4-bromo-benzyl)-2-hydroxy-acetamide (56.0 mg, 25% for two steps).

MS (ESI) m/z=244, 246 (M+H)+.

The aryl bromide reagent used in the synthesis of Compound 490 (3-[2-(4-bromo-phenyl)-ethyl]-1,1-dimethylurea) was synthesized as follows.

(Reaction 95-14)

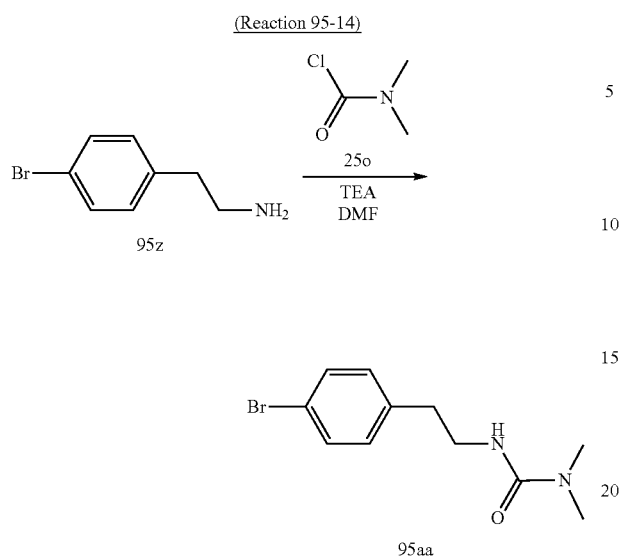

3-[2-(4-Bromo-phenyl)-ethyl]-1,1-dimethyl-urea was synthesized by operations similar to those in Reaction 82-1 using appropriate reagents and starting material.

MS (ESI) m/z=271, 273 (M+H)+.

The aryl bromide reagent used in the synthesis of Compound 492 (5-bromo-6-trifluoromethyl-1H-indole) was synthesized as follows.

(Reaction 95-15)

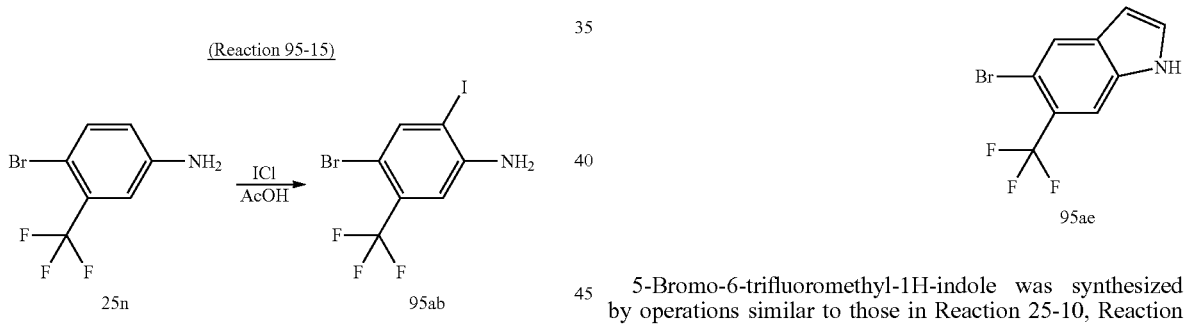

4-Bromo-3-trifluoromethyl-phenylamine (1.00 g, 4.17 mmol) was dissolved in acetic acid (5 ml). Iodine monochloride (1 M solution in dichloromethane, 5 ml) was added and the mixture was stirred at 60° C. overnight. The reaction solution was poured into a mixture of ice and a saturated aqueous sodium bicarbonate solution and then extracted with ethyl acetate. The organic layer was washed with an aqueous sodium bicarbonate solution, an aqueous sodium thiosulfate solution, water and saturated brine, dried over anhydrous sodium sulfate and concentrated under reduced pressure. The resulting residue was purified by silica gel column chromatography (n-hexane-ethyl acetate) to give 4-bromo-2-iodo-5-trifluoromethyl-phenylamine (889 mg, 58%).

$^1$H-NMR (270 MHz, CDCl$_3$) δ 7.92 (1H, s), 7.00 (1H, s), 4.31 (2H, br s).

(Reaction 95-16)

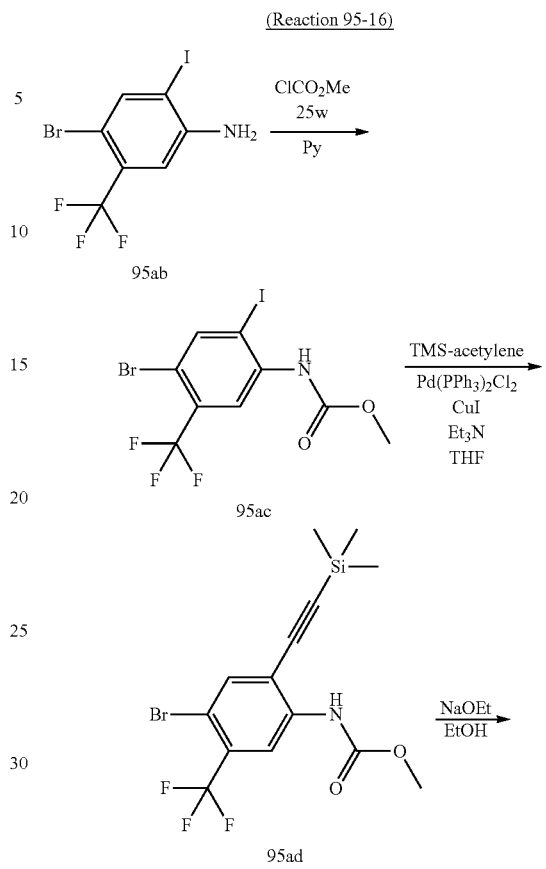

5-Bromo-6-trifluoromethyl-1H-indole was synthesized by operations similar to those in Reaction 25-10, Reaction 95-10 and Reaction 95-11 using appropriate reagents and starting material.

$^1$H-NMR (270 MHz, CDCl$_3$) δ 8.41 (1H, s), 7.96 (1H, s), 7.78 (1H, s), 7.38-7.36 (1H, m), 6.57-6.54 (1H, m).

The aryl bromide reagent used in the synthesis of Compound 493 ((4-bromo-3-trifluoromethyl-phenylamino)-acetic acid methyl ester) was synthesized as follows.

(Reaction 95-17)

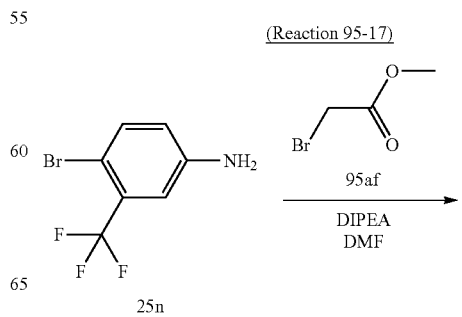

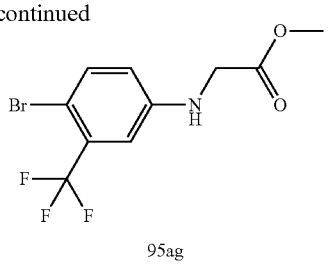

95ag

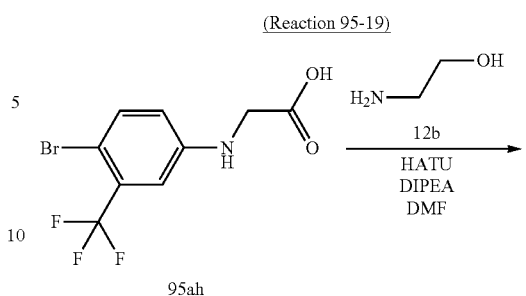

N,N-Diisopropylethylamine (1.22 ml, 7.00 mmol) and methyl bromoacetate (1.00 g, 6.54 mmol) were sequentially added to a solution of 4-bromo-3-(trifluoromethyl)aniline (1.40 g, 5.83 mmol) in DMF (10 ml), and the mixture was heated with stirring at 80° C. for 25 hours. The reaction mixture was cooled and water was then added, followed by extraction with ethyl acetate. The organic layer was sequentially washed with water and saturated brine, and then dried over $MgSO_4$ and concentrated under reduced pressure. The resulting residue was triturated with hexane:dichloromethane=9:1 to give (4-bromo-3-trifluoromethyl-phenylamino)-acetic acid methyl ester (1.22 g, 67%).

MS (ESI) m/z=312, 314 (M+H)+

The aryl bromide reagent used in the synthesis of Compound 494 (2-(4-bromo-3-trifluoromethyl-phenylamino)-N-(2-hydroxy-ethyl)-acetamide) was synthesized as follows.

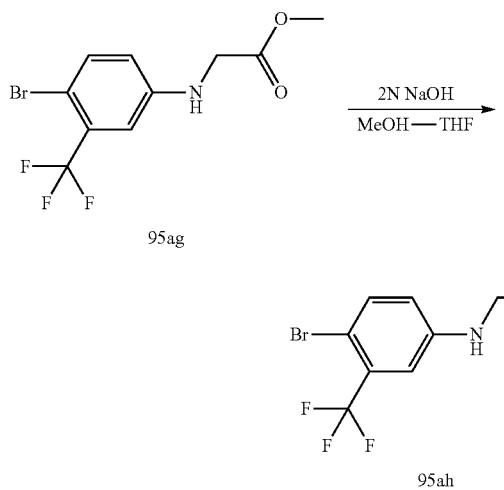

A 2 N aqueous NaOH solution (15.0 ml, 30.0 mmol) was added to a solution of (4-bromo-3-trifluoromethyl-phenylamino)-acetic acid methyl ester (4.30 g, 13.8 mmol) in methanol-THF (6:1, 35.0 ml), and the mixture was stirred at room temperature for 18 hours. The reaction mixture was made acidic with hydrochloric acid and extracted with ethyl acetate. The organic layer was sequentially washed with water and saturated brine, and then dried over $MgSO_4$ and concentrated under reduced pressure to give (4-bromo-3-trifluoromethyl-phenylamino)-acetic acid (4.03 g, 98%).

MS (ESI) m/z=298, 300 (M+H)+

2-(4-Bromo-3-trifluoromethyl-phenylamino)-N-(2-hydroxy-ethyl)-acetamide was synthesized by operations similar to those in Reaction 10-14 using appropriate reagents and starting material.

$^1$H-NMR (CDCl$_3$) δ 2.11 (1H, t, J=5.1 Hz), 3.48 (2H, q, J=5.2 Hz), 3.73 (2H, q, J=5.2 Hz), 3.84 (2H, d, J=5.4 Hz), 4.51-4.57 (1H, m), 6.61 (1H, dd, J=8.7, 2.9 Hz), 6.72 (1H, s), 6.93 (1H, d, J=2.9 Hz), 7.49 (1H, d, J=8.7 Hz).

The aryl bromide reagent used in the synthesis of Compound 495 (4-bromo-N-(2-hydroxy-ethyl)-N-methyl-3-trifluoromethyl-benzenesulfonamide) was synthesized as follows.

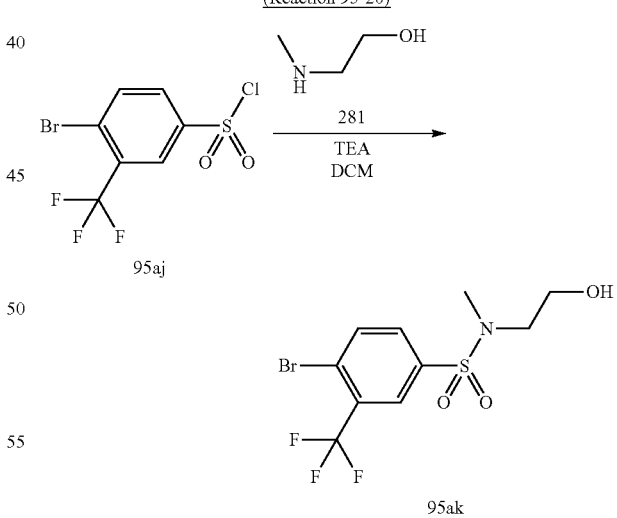

4-Bromo-N-(2-hydroxy-ethyl)-N-methyl-3-trifluoromethyl-benzenesulfonamide was synthesized by operations similar to those in Reaction 5-4 using appropriate reagents and starting material.

MS (ESI) m/z=362, 364 (M+H)+.

The aryl bromide reagent used in the synthesis of Compound 496 (4-bromo-N,N-bis-(2-hydroxy-ethyl)-3-trifluoromethyl-benzenesulfonamide) was synthesized as follows.

(Reaction 95-21)

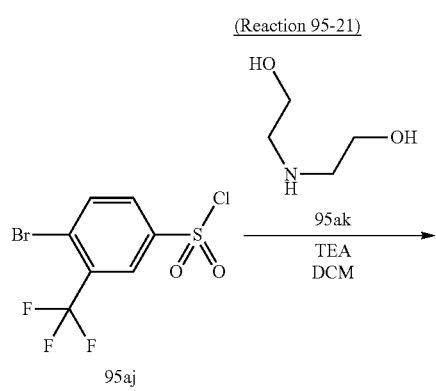

4-Bromo-N,N-bis-(2-hydroxy-ethyl)-3-trifluoromethyl-benzenesulfonamide was synthesized by operations similar to those in Reaction 5-4 using appropriate reagents and starting material.

MS (ESI) m/z=392, 394 (M+H)+.

The aryl bromide reagent used in the synthesis of Compound 497 (N'-(4-bromo-3-methyl-phenyl)-N,N-dimethyl-ethane-1,2-diamine) was synthesized as follows.

(Reaction 95-22)

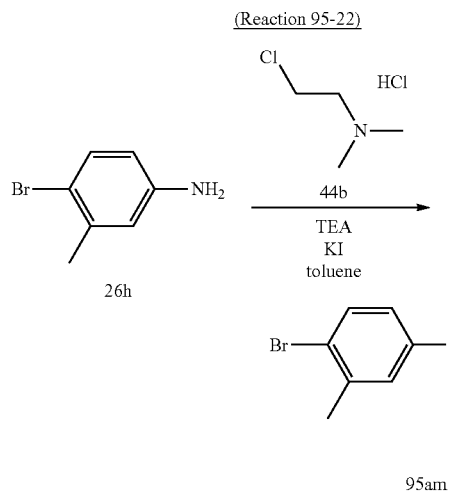

2-Chloro-N,N-dimethylethylamine hydrochloride (372 mg, 2.58 mmol), potassium iodide (428 mg, 2.58 mmol) and triethylamine (0.719 ml, 5.16 mmol) were added to a solution of 4-bromo-3-methylaniline (400 mg, 2.15 mmol) in toluene (5.0 ml), and the mixture was heated with stirring at 110° C. for 17 hours. The reaction mixture was cooled and water was then added, followed by extraction with ethyl acetate. The organic layer was sequentially washed with water and saturated brine and then concentrated under reduced pressure. The resulting residue was purified by silica gel column chromatography (dichloromethane-methanol) to give N'-(4-bromo-3-methyl-phenyl)-N,N-dimethyl-ethane-1,2-diamine (100 mg, 18%).

MS (ESI) m/z=257, 259 (M+H)+.

The aryl bromide reagent used in the synthesis of Compound 498 (N-(2-acetylamino-ethyl)-2-(4-bromo-3-trifluoromethyl-phenylamino)-acetamide) was synthesized as follows.

(Reaction 95-23)

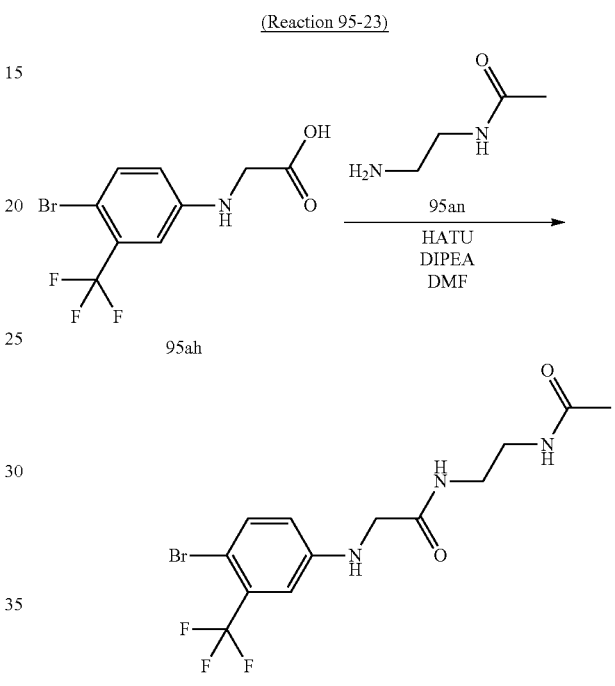

N-(2-Acetylamino-ethyl)-2-(4-bromo-3-trifluoromethyl-phenylamino)-acetamide was synthesized by operations similar to those in Reaction 10-14 using appropriate reagents and starting material.

MS (ESI) m/z=382, 384 (M+H)+.

The aryl bromide reagent used in the synthesis of Compound 499 (5-bromo-6-trifluoromethyl-1H-benzimidazole) was synthesized as follows.

(Reaction 95-24)

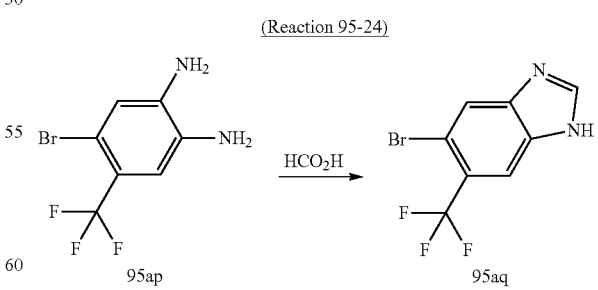

4-Bromo-5-trifluoromethyl-benzene-1,2-diamine (200 mg, 0.785 mmol) was dissolved in formic acid (3 ml), and the mixture was stirred at 120° C. for six hours. The reaction solution was concentrated, and water was added to the resulting residue, followed by extraction with ethyl acetate.

The organic layer was washed with water and saturated brine, dried over anhydrous sodium sulfate and concentrated under reduced pressure to give 5-bromo-6-trifluoromethyl-1H-benzimidazole (201 mg) as a crude compound.

MS (ESI) m/z=265 (M+H)+.

The aryl bromide reagent used in the synthesis of Compound 500 (4-bromo-1-((S)-2,2-dimethyl-[1,3]dioxolan-4-ylmethyl)-5-fluoro-1H-indole) was synthesized as follows.

(Reaction 95-25)

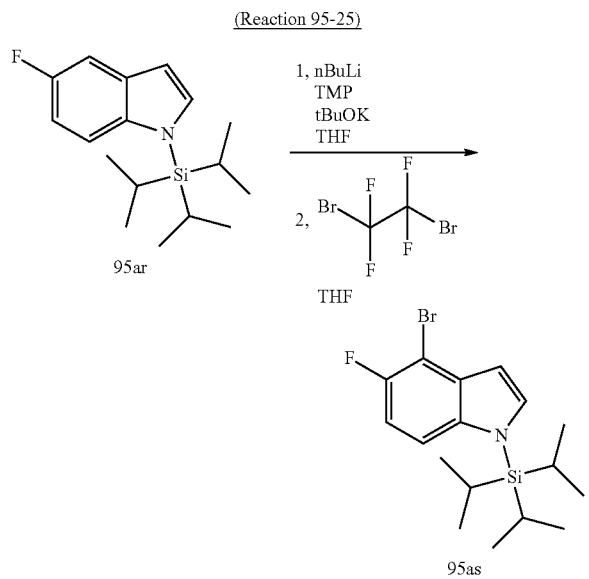

A solution of n-butyllithium (2.1 mL, 3.39 mmol) in tetrahydrofuran (6.8 mL) was cooled to −78° C., and 2,2,6,6-tetramethylpiperidine (0.57 mL, 3.39 mmol) and a 1.0 M solution of potassium t-butoxide in tetrahydrofuran (3.4 mL, 3.39 mmol) were added. After stirring for 15 minutes, a solution of 5-fluoro-1-triisopropylsilanyl-1H-indole (494 mg, 1.70 mmol) in tetrahydrofuran (5 ml) was added dropwise, and the mixture was stirred at −78° C. for 2.5 hours. 1,2-Dibromo-1,1,2,2-tetrafluoroethane (38 mL, 0.319 mmol) was added, and the mixture was warmed to −40° C. over 35 minutes and further warmed to 22° C. over 12 hours. Silica gel (17 g) was added and the solvent was then distilled off. The residue was subjected to silica gel column chromatography to give a pale yellow oily substance (380 mg) as a mixture of 4-bromo-5-fluoro-1-triisopropylsilanyl-1H-indole:5-fluoro-1-triisopropylsilanyl-1H-indole=1:1.1.

$^1$H-NMR (CDCl$_3$) δ 7.37-7.33 (2H, m), 6.94 (1H, dd, J=9.0, 4.5 Hz), 6.68 (1H, d, J=3.9 Hz), 1.71-1.63 (3H, m), 1.14 (18H, d, J=7.3 Hz).

(Reaction 95-26)

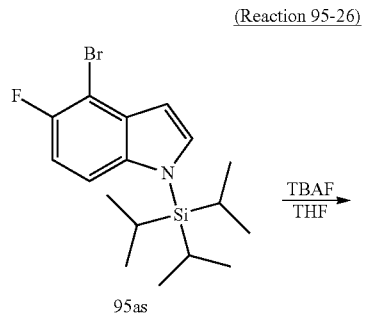

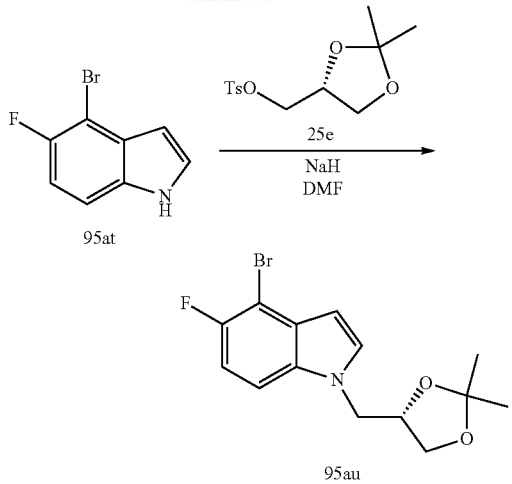

4-Bromo-1-((S)-2,2-dimethyl-[1,3]dioxolan-4-ylmethyl)-5-fluoro-1H-indole was synthesized by operations similar to those in Reaction 39-2 and Reaction 25-3 using appropriate reagents and starting material.

MS (ESI) m/z=328, 330 (M+H)+.

The aryl bromide reagent used in the synthesis of Compound 501 (2-[(4-bromo-3-trifluoromethyl-phenyl)-methyl-amino]-ethanol) was synthesized as follows.

(Reaction 95-27)

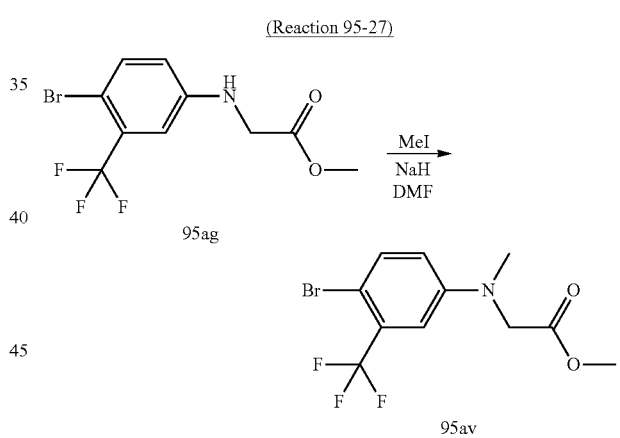

[(4-Bromo-3-trifluoromethyl-phenyl)-methyl-amino]-acetic acid methyl ester was synthesized by operations similar to those in Reaction 25-3 using appropriate reagents and starting material.

MS (ESI) m/z=326, 328 (M+H)+.

(Reaction 95-28)

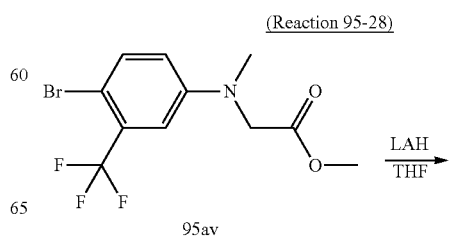

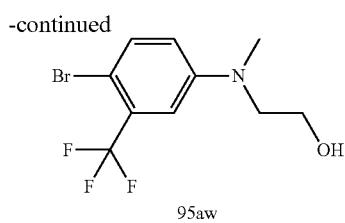

A solution of [(4-bromo-3-trifluoromethyl-phenyl)-methyl-amino]-acetic acid methyl ester (77.6 mg, 0.238 mmol) in THF (1.0 ml) was added dropwise to a suspension of lithium aluminum hydride (372 mg, 2.58 mmol) in THF (1.5 ml) at 0° C. The mixture was stirred for 14 hours while gradually warming from 0° C. to room temperature. A 2 N aqueous HCl solution was added to the reaction mixture, followed by extraction with ethyl acetate. The organic layer was sequentially washed with water and saturated brine and then concentrated under reduced pressure. The resulting residue was purified by silica gel column chromatography (dichloromethane-ethyl acetate) to give 2-[(4-bromo-3-trifluoromethyl-phenyl)-methyl-amino]-ethanol (58.0 mg, 82%).

MS (ESI) m/z=298, 300 (M+H)+.

The aryl bromide reagent used in the synthesis of Compound 502 ((4-bromo-3-methyl-phenyl)-(1,1-dioxo-1λ$^6$-thiomorpholin-4-yl)-methanone) was synthesized as follows.

(Reaction 95-29)

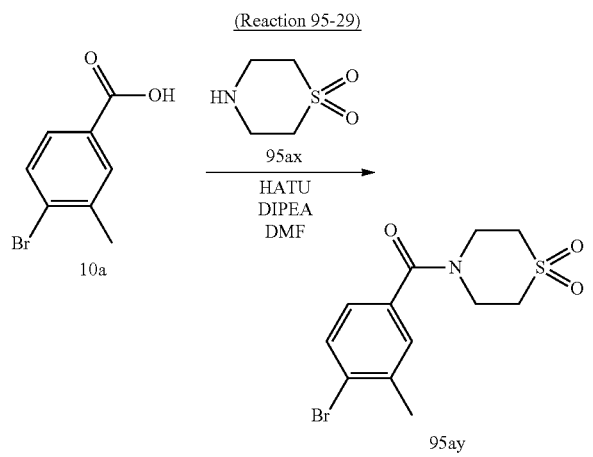

(4-Bromo-3-methyl-phenyl)-(1,1-dioxo-1λ$^6$-thiomorpholin-4-yl)-methanone was synthesized by operations similar to those in Reaction 10-14 using appropriate reagents and starting material.

MS (ESI) m/z=332, 334 (M+H)+.

The aryl bromide reagent used in the synthesis of Compound 503 (4-bromo-N-(2-dimethylamino-ethyl)-3-methyl-benzenesulfonamide) was synthesized as follows.

(Reaction 95-30)

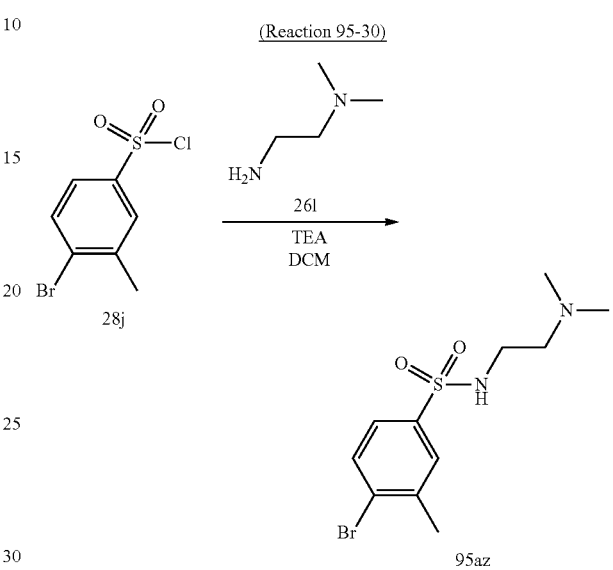

4-Bromo-N-(2-dimethylamino-ethyl)-3-methyl-benzenesulfonamide was synthesized by operations similar to those in Reaction 5-4 using appropriate reagents and starting material.

MS (ESI) m/z=321, 323 (M+H)+.

Example 96

The example compounds shown below were obtained by operations similar to those in Reaction 25-2 using appropriate reagents and starting materials.

Compounds 504 to 523

TABLE 71

| Target Compound | Structure | LCMS condition | Retention time (min) | MS (m/z) |
|---|---|---|---|---|
| 504 | 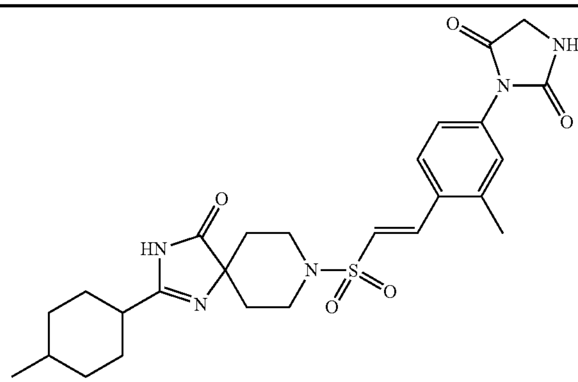 | LCMS-C-1 | 2.4 | 528 (M + H)+ |

TABLE 71-continued

| Target Compound | Structure | LCMS condition | Retention time (min) | MS (m/z) |
|---|---|---|---|---|
| 505 | 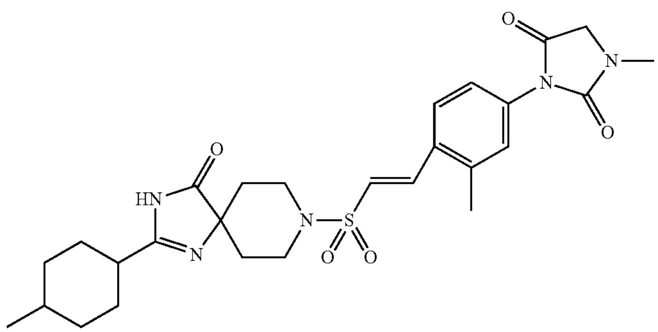 | LCMS-C-1 | 2.47 | 542 (M + H)+ |
| 506 | 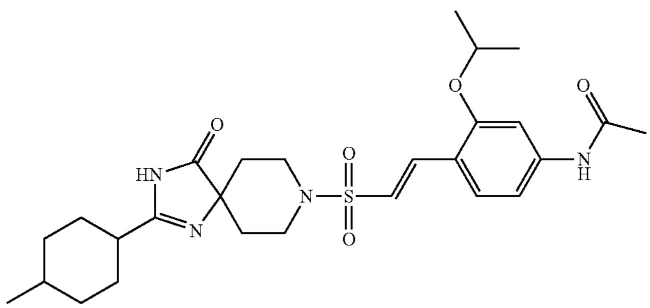 [SMILES: CC(=O)Nc1ccc(/C=C/S(=O)(=O)N2CCC3(CC2)N=C(C2CCC(C)CC2)NC3=O)c(OC(C)C)c1] | LCMS-D-1 | 1.91 | 531 (M + H)+ |
| 507 | 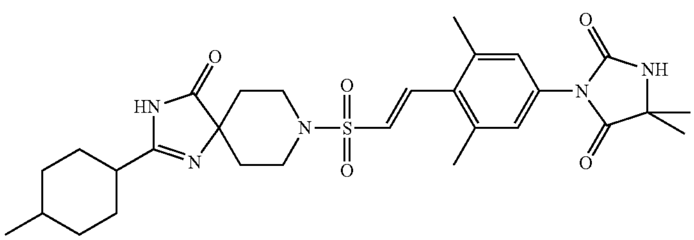 | LCMS-D-1 | 1.9 | 570 (M + H)+ |
| 508 | 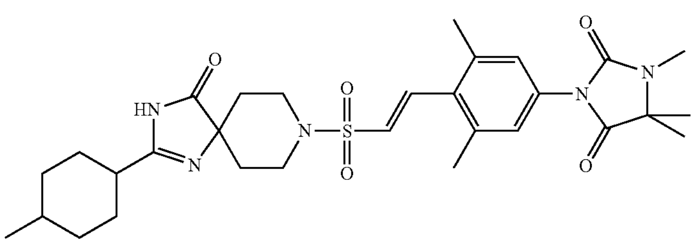 | LCMS-D-1 | 1.98 | 584 (M + H)+ |
| 509 | 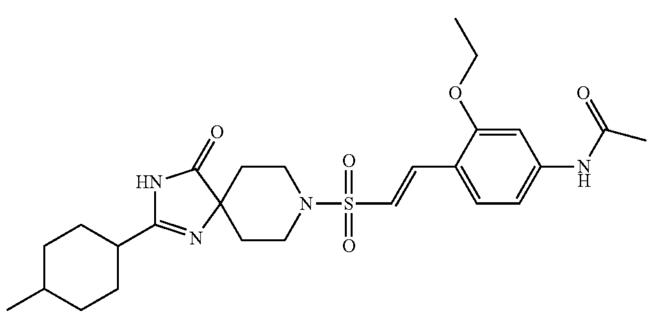 [SMILES: CCOc1cc(NC(C)=O)ccc1/C=C/S(=O)(=O)N1CCC2(CC1)N=C(C1CCC(C)CC1)NC2=O] | LCMS-D-1 | 1.9 | 517 (M + H)+ |

TABLE 71-continued
| Target Compound | Structure | LCMS condition | Retention time (min) | MS (m/z) |
|---|---|---|---|---|
| 510 | 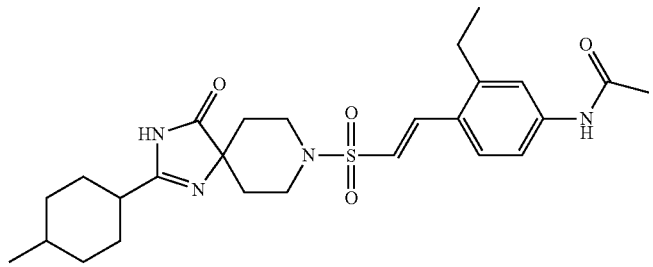 [SMILES: CCc1cc(NC(C)=O)ccc1/C=C/S(=O)(=O)N1CCC2(CC1)N=C(C1CCC(C)CC1)NC2=O] | LCMS-D-1 | 1.82 | 501 (M + H)+ |
| 511 | 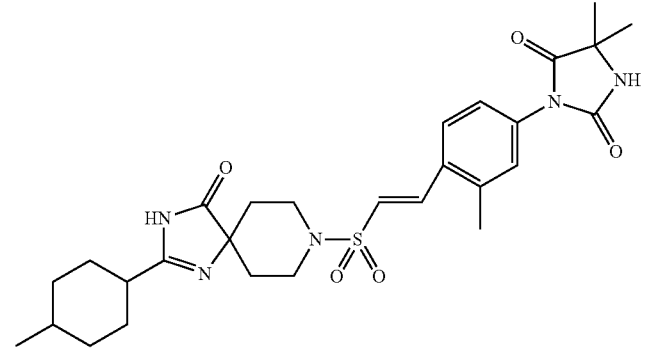 | LCMS-F-1 | 0.92 | 556 (M + H)+ |
| 512 | 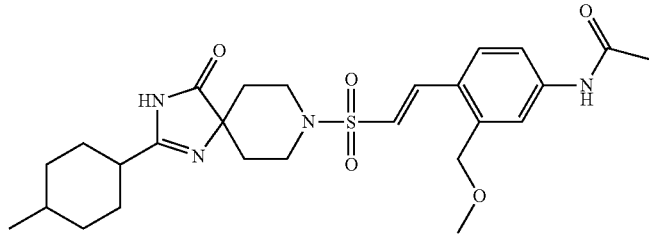 [SMILES: COCc1cc(NC(C)=O)ccc1/C=C/S(=O)(=O)N1CCC2(CC1)N=C(C1CCC(C)CC1)NC2=O] | LCMS-D-1 | 1.84 | 517 (M + H)+ |
| 513 | 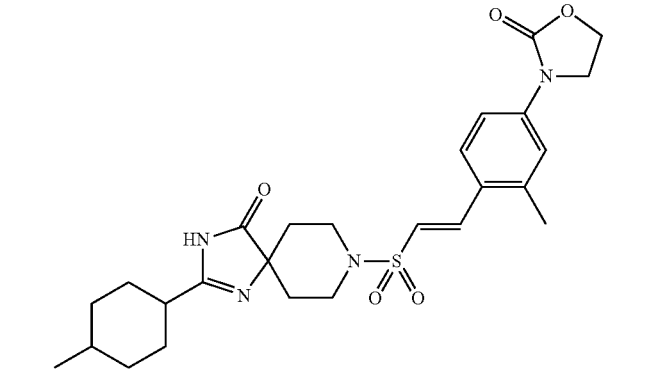 [SMILES: Cc1cc(N2CCOC2=O)ccc1/C=C/S(=O)(=O)N1CCC2(CC1)N=C(C1CCC(C)CC1)NC2=O] | LCMS-C-1 | 2.47 | 515 (M + H)+ |
| 514 | 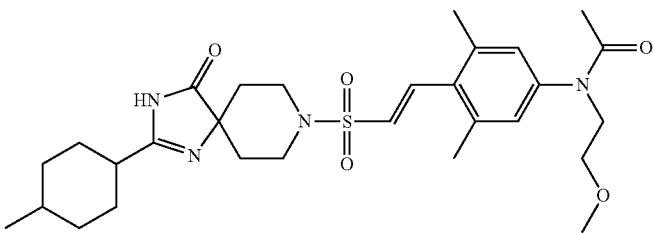 [SMILES: COCCN(C(C)=O)c1cc(C)c(/C=C/S(=O)(=O)N2CCC3(CC2)N=C(C2CCC(C)CC2)NC3=O)c(C)c1] | LCMS-D-1 | 2.09 | 559 (M + H)+ |

TABLE 71-continued

| Target Compound | Structure | LCMS condition | Retention time (min) | MS (m/z) |
|---|---|---|---|---|
| 515 | 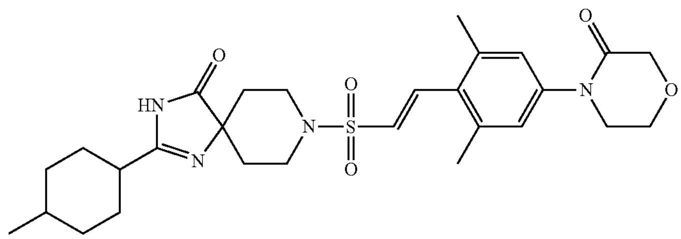 [SMILES: Cc1cc(N2CCOCC2=O)cc(C)c1/C=C/S(=O)(=O)N1CCC2(CC1)N=C(C1CCC(C)CC1)NC2=O] | LCMS-D-1 | 1.83 | 543 (M + H)+ |
| 516 | 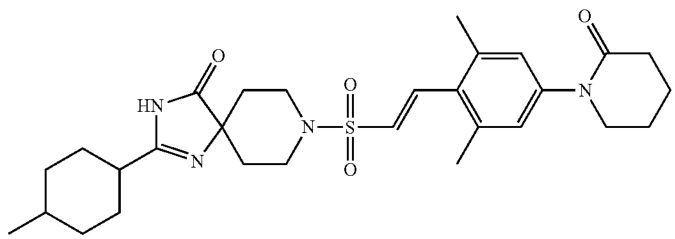 [SMILES: Cc1cc(N2CCCCC2=O)cc(C)c1/C=C/S(=O)(=O)N1CCC2(CC1)N=C(C1CCC(C)CC1)NC2=O] | LCMS-D-1 | 2.22 | 541 (M + H)+ |
| 517 | 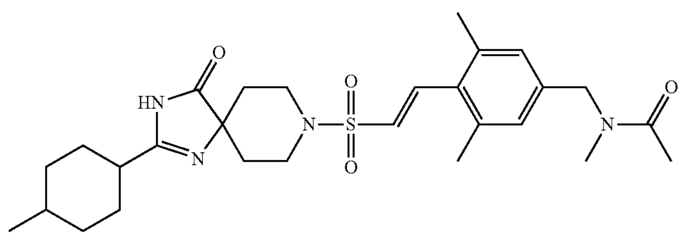 | LCMS-D-1 | 2.23 | 529 (M + H)+ |
| 518 | 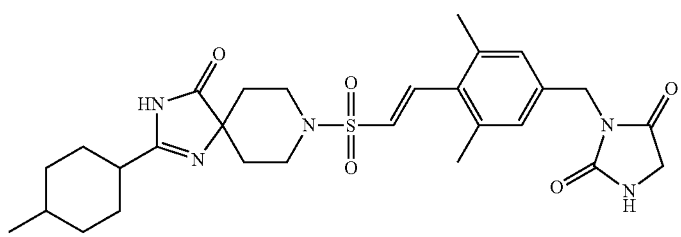 [SMILES: Cc1cc(CN2C(=O)CNC2=O)cc(C)c1/C=C/S(=O)(=O)N1CCC2(CC1)N=C(C1CCC(C)CC1)NC2=O] | LCMS-D-1 | 2.13 | 556 (M + H)+ |
| 519 | 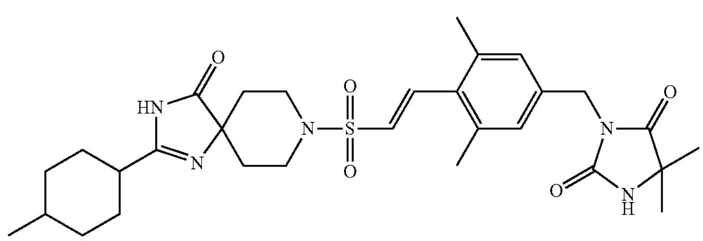 | LCMS-D-1 | 2.4 | 584 (M + H)+ |
| 520 | 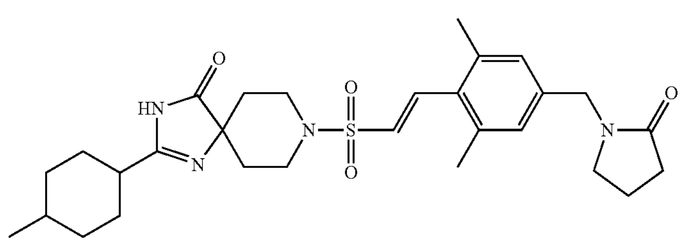 [SMILES: Cc1cc(CN2CCCC2=O)cc(C)c1/C=C/S(=O)(=O)N1CCC2(CC1)N=C(C1CCC(C)CC1)NC2=O] | LCMS-D-1 | 2.28 | 541 (M + H)+ |

TABLE 71-continued

| Target Compound | Structure | LCMS condition | Retention time (min) | MS (m/z) |
|---|---|---|---|---|
| 521 | 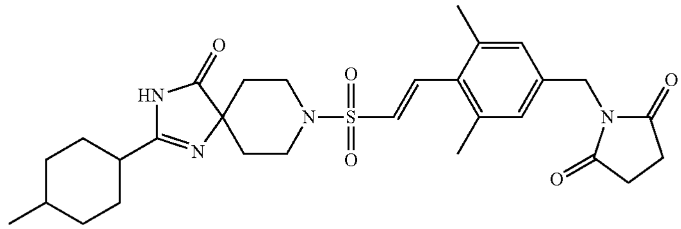 [SMILES: Cc1cc(CN2C(=O)CCC2=O)cc(C)c1/C=C/S(=O)(=O)N1CCC2(CC1)N=C(C1CCC(C)CC1)NC2=O] | LCMS-D-1 | 2.27 | 555 (M + H)+ |
| 522 | 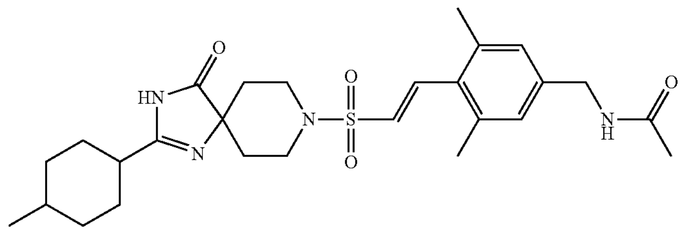 | LCMS-D-1 | 2.45 | 515 (M + H)+ |
| 523 | 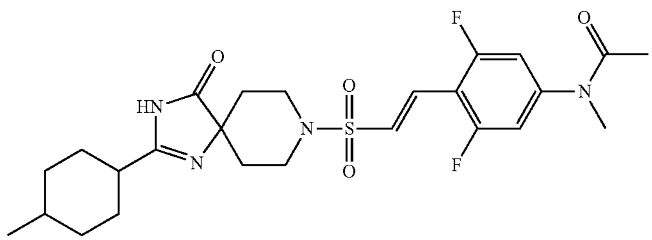 [SMILES: CC(=O)N(C)c1cc(F)c(/C=C/S(=O)(=O)N2CCC3(CC2)N=C(C2CCC(C)CC2)NC3=O)c(F)c1] | LCMS-D-1 | 2.33 | 523 (M + H)+ |

The aryl bromide reagent used in the synthesis of Compound 504 (3-(4-bromo-3-methyl-phenyl)-imidazolidine-2,4-dione) was synthesized as follows.

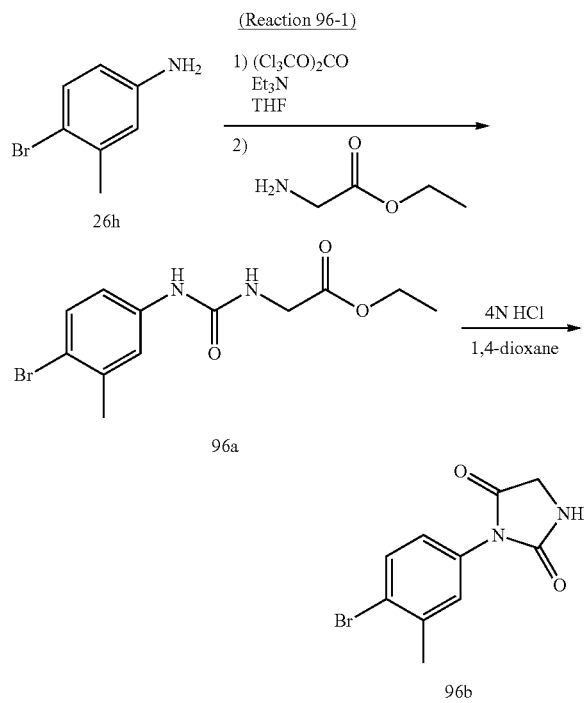

(Reaction 96-1)

Triethylamine (20 ml, 145 mmol) and 4-bromo-3-methyl-phenylamine (4.49 g, 24.14 mmol) were added to a solution of triphosgene (1.0 ml, 8.05 mmol) in THF (70 ml) at 0° C., and the mixture was stirred at the same temperature for 40 minutes. Further, the reaction mixture was warmed to room temperature and stirred at the same temperature for one hour. Water was added to the reaction solution, and the mixture was then concentrated under reduced pressure, followed by extraction with ethyl acetate. The organic phase was sequentially washed with water and saturated brine and then concentrated under reduced pressure to give [3-(4-bromo-3-methyl-phenyl)-ureido]-acetic acid ethyl ester (5.07 g) as a crude product. This crude product was used in the next reaction without purification.

4 N HCl-dioxane (7.5 ml, 30 mmol) was added to a solution of the crude product [3-(4-bromo-3-methyl-phenyl)-ureido]-acetic acid ethyl ester (5.07 g) in dioxane (60 ml), and the mixture was heated with stirring at 80° C. for 17 hours. The reaction mixture was cooled to room temperature and then concentrated under reduced pressure, and water was added, followed by extraction with ethyl acetate. The organic phase was washed with saturated brine and then concentrated under reduced pressure. The resulting residue was purified by silica gel column chromatography to give 3-(4-bromo-3-methyl-phenyl)-imidazolidine-2,4-dione (2.40 g, 37%).

MS (ESI) m/z=269, 271 (M+H)+.

The aryl bromide reagent used in the synthesis of Compound 505 (3-(4-bromo-3-methyl-phenyl)-1-methyl-imidazolidine-2,4-dione) was synthesized as follows.

(Reaction 96-2)

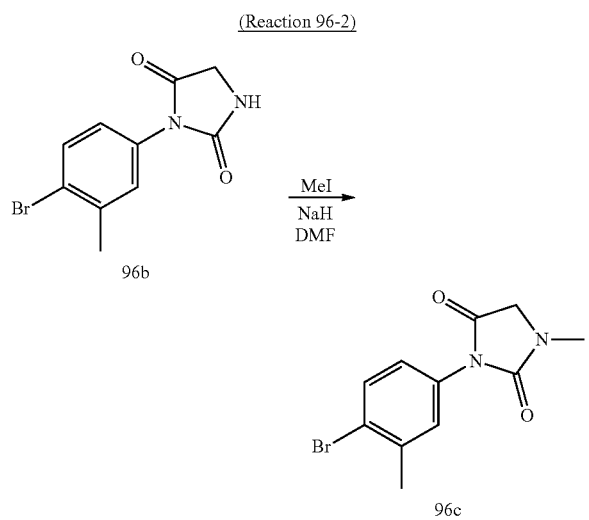

(3-(4-Bromo-3-methyl-phenyl)-1-methyl-imidazolidine-2,4-dione was synthesized by operations similar to those in Reaction 25-3 using appropriate reagents and starting material.

MS (ESI) m/z=283, 285 (M+H)+.

The aryl bromide reagent used in the synthesis of Compound 506 (N-(4-bromo-3-isopropoxyphenyl)acetamide) was synthesized as follows.

(Reaction 96-3)

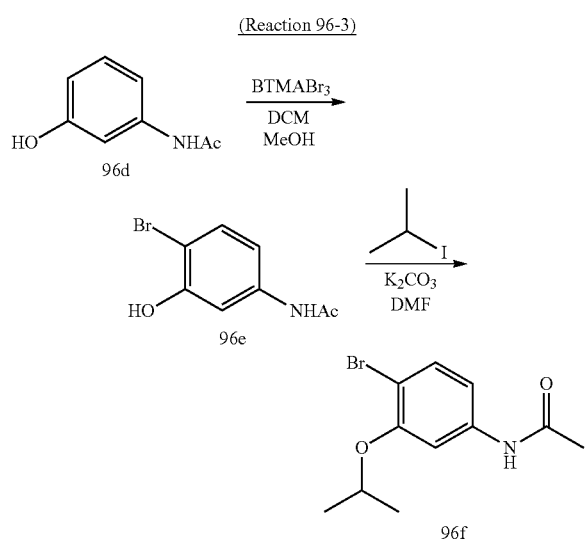

N-(4-Bromo-3-isopropoxyphenyl)acetamide was synthesized by operations similar to those in Reaction 26-2 and Reaction 26-4 using appropriate reagents and starting material.

$^1$H-NMR (CDCl$_3$) δ 7.64 (d, 1H, J=2.29 Hz), 7.42 (d, 1H, J=8.39 Hz), 7.15 (brs, 1H), 6.72 (dd, 1H, J=8.39 Hz, J=2.29 Hz), 4.57 (m, 1H, J=6.1 Hz), 2.17 (s, 3H), 1.38 (d, 6H, J=6.1 Hz).

The aryl bromide reagents used in the synthesis of Compound 507 and Compound 508 (3-(4-bromo-3,5-dimethyl-phenyl)-5,5-dimethylimidazolidine-2,4-dione and 3-(4-bromo-3,5-dimethylphenyl)-1,5,5-trimethylimidazolidine-2,4-dione) were synthesized as follows.

(Reaction 96-4)

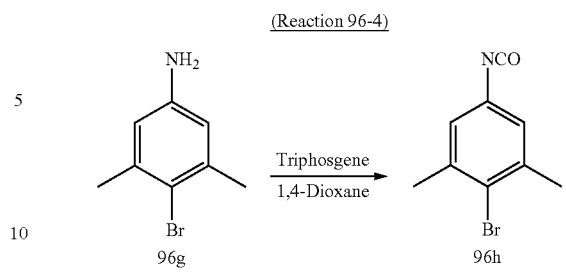

Triphosgene (2.23 g, 7.52 mmol) was added to a solution of 4-bromo-3,5-dimethyl-phenylamine (4.3 g, 21.49 mmol) in dioxane (71 ml). After stirring at 100° C. for 15 hours, water was added to the reaction solution. After extraction with ethyl acetate, the organic phase was sequentially washed with water and saturated brine and concentrated under reduced pressure to give 2-bromo-5-isocyanato-1,3-dimethylbenzene (2.0 g, 41%).

MS (ESI) m/z=226, 228 (M+H)+.

(Reaction 96-5)

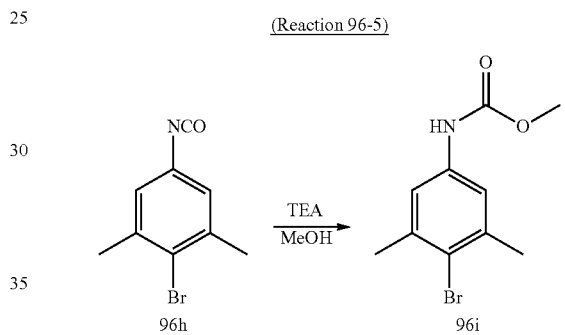

Triethylamine (1.8 ml, 13.27 mmol) was added dropwise to a solution of 2-bromo-5-isocyanato-1,3-dimethylbenzene (2.0 g, 8.84 mmol) in anhydrous methanol (30 ml) at 0° C. The reaction solution was gradually warmed to room temperature and stirred for one hour. The reaction solution was concentrated under reduced pressure, and the residue was diluted with ethyl acetate. The organic layer was then sequentially washed with water and saturated brine and concentrated under reduced pressure. The residue was purified by silica gel column chromatography (hexane-ethyl acetate) to give methyl(4-bromo-3,5-dimethylphenyl)carbamate (1.8 g, 79%).

MS (ESI) m/z=258, 260 (M+H)+.

(Reaction 96-6)

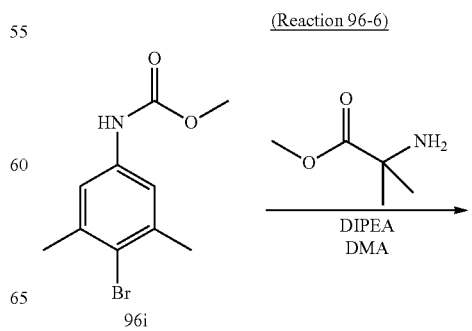

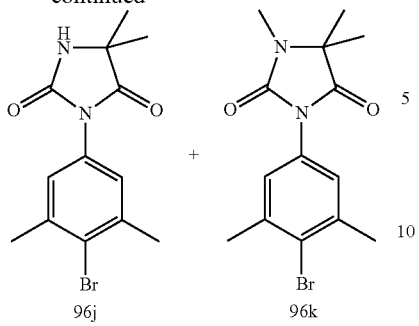

+

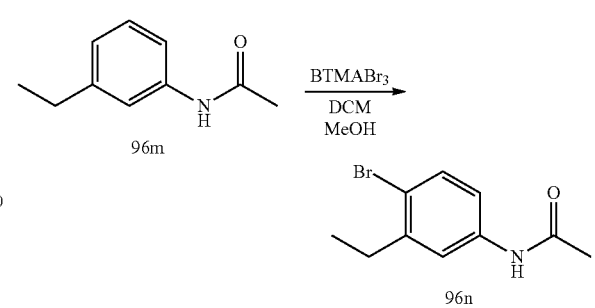

α-Aminoisobutyric acid methyl ester (3.2 g, 20.92 mmol) and N,N-diisopropylethylamine (6.1 ml, 34.86 mmol) were added to a solution of methyl (4-bromo-3,5-dimethylphenyl)carbamate (900 mg, 3.48 mmol) in anhydrous DMA (17.5 ml, 0.2 M). After irradiation with microwaves at 170° C. for 30 minutes, water was added to the reaction solution, followed by extraction with ethyl acetate. The organic phase was sequentially washed with water and saturated brine and concentrated under reduced pressure. The residue was purified by silica gel column chromatography (hexane-ethyl acetate) to give 3-(4-bromo-3,5-dimethylphenyl)-5,5-dimethylimidazolidine-2,4-dione (304 mg, 28%)

MS (ESI) m/z=311, 313 (M+H)+ and 3-(4-bromo-3,5-dimethylphenyl)-1,5,5-trimethylimidazolidine-2,4-dione (245 mg, 23%).

MS (ESI) m/z=325, 327 (M+H)+

The aryl bromide reagent used in the synthesis of Compound 509 (N-(4-bromo-3-ethoxyphenyl)acetamide) was synthesized as follows.

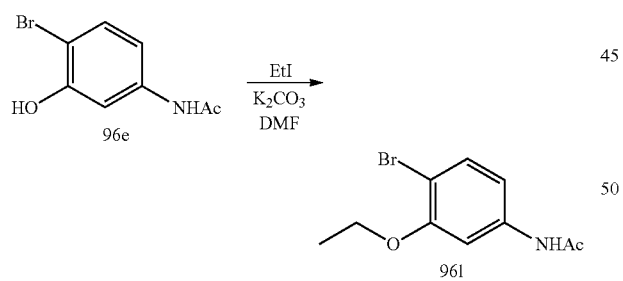

N-(4-Bromo-3-ethoxyphenyl)acetamide was synthesized by operations similar to those in Reaction 26-4 using appropriate reagents and starting material.

$^1$H-NMR (CDCl$_3$) δ 7.48 (d, 1H, J=2.29 Hz), 7.42 (d, 1H, J=8.39 Hz), 7.22 (brs, 1H), 6.72 (dd, 1H, J=8.39 Hz, J=2.29 Hz), 4.10 (q, 2H, J=6.87 Hz), 2.17 (s, 3H), 1.46 (t, 3H, J=6.87 Hz).

The aryl bromide reagent used in the synthesis of Compound 510 (N-(4-bromo-3-ethylphenyl)acetamide) was synthesized as follows.

N-(4-Bromo-3-ethylphenyl)acetamide was synthesized by operations similar to those in Reaction 26-2 using appropriate reagents and starting material.

$^1$H-NMR (CDCl$_3$) δ 7.44 (d, 1H, J=8.39 Hz), 7.39 (d, 1H, J=2.29 Hz), 7.23 (dd, 1H, J=8.39 Hz, J=2.29 Hz), 7.17 (brs, 1H), 2.72 (q, 2H, J=7.25 Hz), 2.17 (s, 3H), 1.21 (t, 3H, J=7.25 Hz).

The aryl bromide reagent used in the synthesis of Compound 511 (3-(4-bromo-3-methyl-phenyl)-5,5-dimethylimidazolidine-2,4-dione) was synthesized as follows.

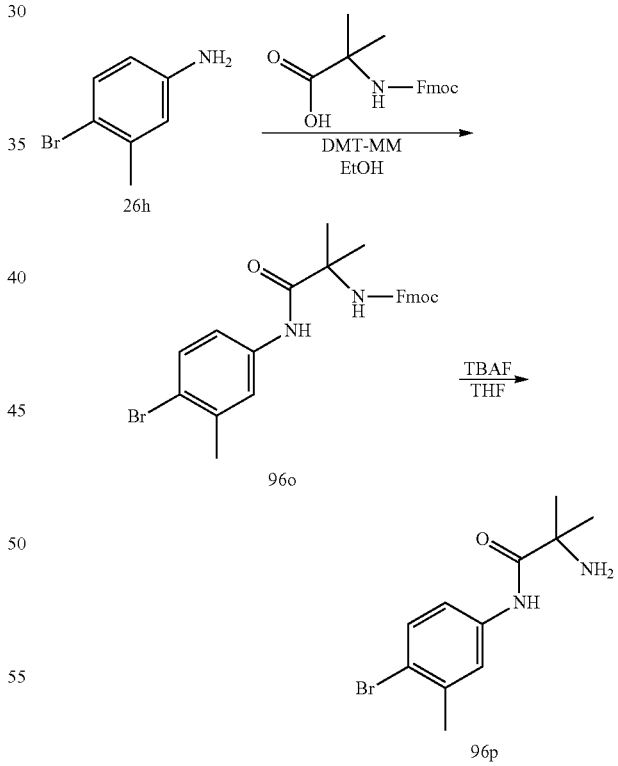

2-Amino-N-(4-bromo-3-methyl-phenyl)-2-methyl-propionamide was synthesized by operations similar to those in Reaction 10-1 and Reaction 39-2 using appropriate reagents and starting material.

$^1$H-NMR (CDCl$_3$) δ 1.46 (6H, s), 2.37 (3H, s), 7.29 (1H, dd, J=8.8, 2.4 Hz), 7.44 (1H, d, J=8.8 Hz), 7.59 (1H, d, J=2.4 Hz), 9.84 (1H, br s).

(Reaction 96-10)

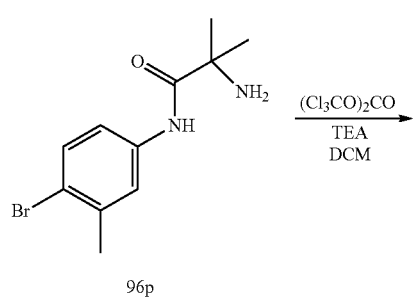

96p

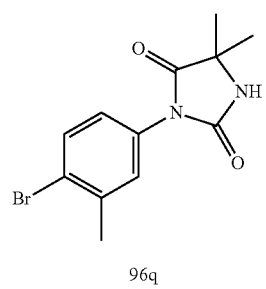

96q

Bis(trichloromethyl) carbonate (50.6 mg, 0.171 mmol) was added to a solution of 2-amino-N-(4-bromo-3-methyl-phenyl)-2-methyl-propionamide (132 mg, 0.487 mmol) and triethylamine (0.204 ml, 1.46 mmol) in dichloromethane (5.0 ml) at 0° C., and the mixture was stirred for 21 hours while gradually warming to room temperature. An aqueous ammonium chloride solution was added to the reaction mixture, followed by extraction with dichloromethane. The resulting residue was purified by silica gel column chromatography (dichloromethane-ethyl acetate) to give 3-(4-bromo-3-methyl-phenyl)-5,5-dimethyl-imidazolidine-2,4-dione (146 mg, 88%).

MS (ESI) m/z=297, 299 (M+H)+.

The aryl bromide reagent used in the synthesis of Compound 512 (N-(4-bromo-3-methoxymethyl-phenyl)-acetamide) was synthesized as follows.

(Reaction 96-11)

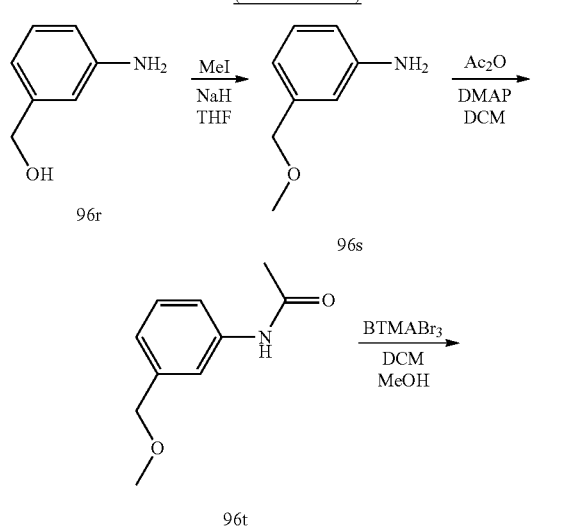

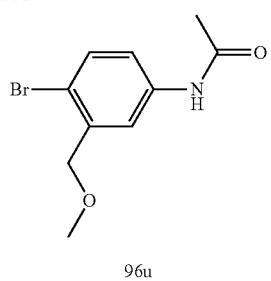

96u

N-(4-Bromo-3-methoxymethyl-phenyl)-acetamide was synthesized by operations similar to those in Reaction 20-2, Reaction 19-2 and Reaction 26-2 using appropriate reagents and starting material.

$^1$H-NMR (CDCl$_3$) δ 7.12 (t, 1H, J=7.8 Hz), 6.70 (m, 2H), 6.60 (dd, 1H, J=7.5 Hz, 2.1 Hz), 4.42 (s, 2H), 3.53 (s, 3H), 2.08 (s, 3H).

The aryl bromide reagent used in the synthesis of Compound 513 (3-(4-bromo-3-methyl-phenyl)-oxazolidin-2-one) was synthesized as follows.

(Reaction 96-12)

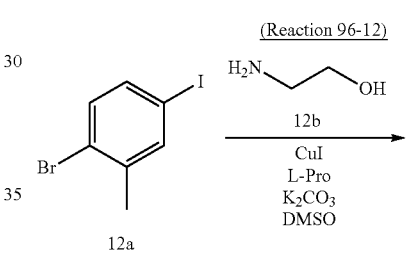

12c 2-(4-Bromo-3-methyl-phenylamino)-ethanol was synthesized by operations similar to those in Reaction 12-1 using appropriate reagents and starting material.

MS (ESI) m/z=230, 232 (M+H)+.

(Reaction 96-13)

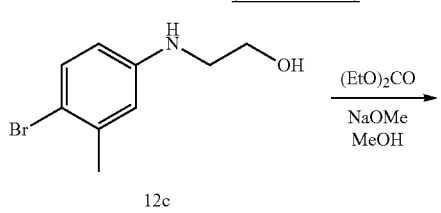

12c

-continued

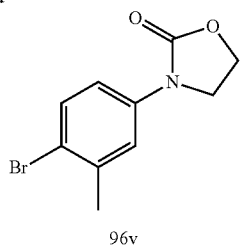

96v

Diethyl carbonate (18 ml) and a 28% solution of sodium methoxide in methanol (1.1 ml, 5.70 mmol) were added to 2-(4-bromo-3-methyl-phenylamino)-ethanol (1.21 g, 5.27 mmol), and the mixture was heated with stirring at 110° C. for 15 hours. Further, methanol (16 ml) was added to the reaction solution, and the mixture was heated with stirring at 110° C. for one hour. An aqueous ammonium chloride solution was added to the reaction mixture, followed by extraction with ethyl acetate. The organic phase was sequentially washed with water and saturated brine and concentrated under reduced pressure. The resulting residue was triturated with hexane to give 3-(4-bromo-3-methyl-phenyl)-oxazolidin-2-one (989 mg, 73%).

MS (ESI) m/z=256, 258 (M+H)+.

The aryl bromide reagent used in the synthesis of Compound 514 (N-(4-bromo-3,5-dimethyl-phenyl)-N-(2-methoxy-ethyl)-acetamide) was synthesized as follows.

(Reaction 96-14)

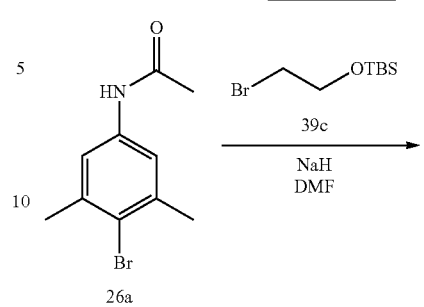

26a

26a

96w

N-(4-Bromo-3,5-dimethyl-phenyl)-N-(2-methoxy-ethyl)-acetamide was synthesized by operations similar to those in Reaction 25-3 using appropriate reagents and starting material.

MS (ESI) m/z=300, 302 (M+H)+.

The aryl bromide reagent used in the synthesis of Compound 515 (4-(4-bromo-3,5-dimethyl-phenyl)-morpholin-3-one) was synthesized as follows.

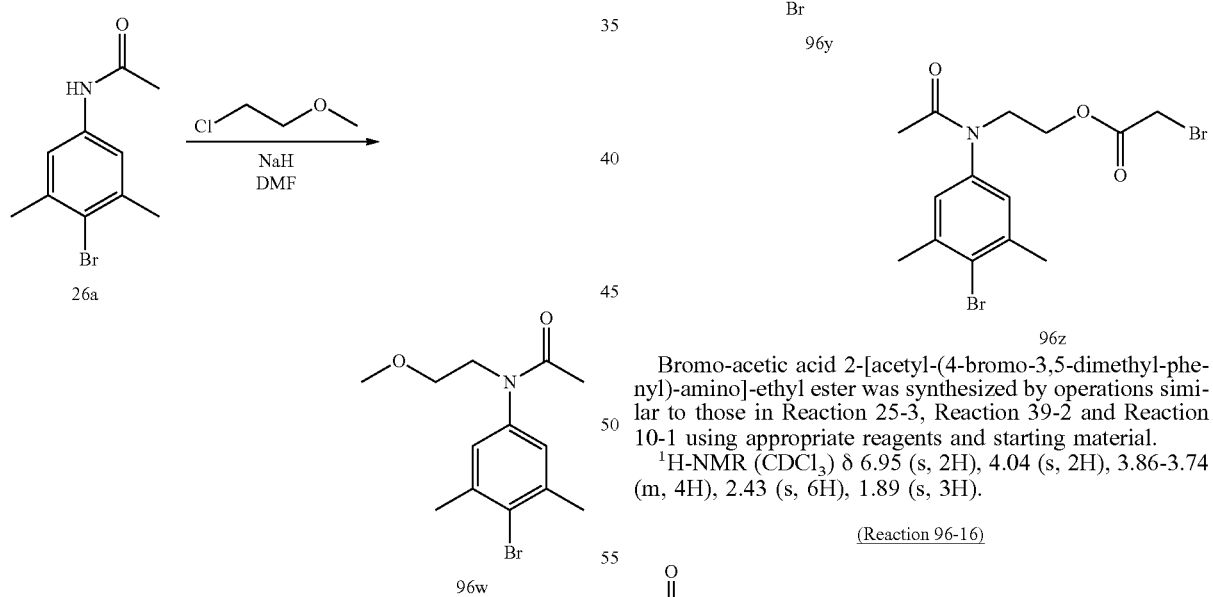

96z

Bromo-acetic acid 2-[acetyl-(4-bromo-3,5-dimethyl-phenyl)-amino]-ethyl ester was synthesized by operations similar to those in Reaction 25-3, Reaction 39-2 and Reaction 10-1 using appropriate reagents and starting material.

$^1$H-NMR (CDCl$_3$) δ 6.95 (s, 2H), 4.04 (s, 2H), 3.86-3.74 (m, 4H), 2.43 (s, 6H), 1.89 (s, 3H).

(Reaction 96-16)

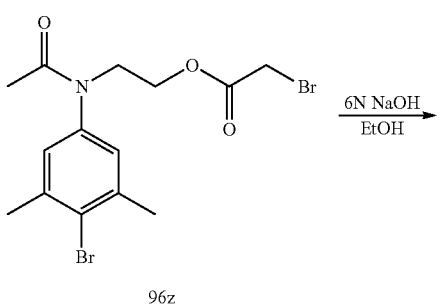

96z

-continued

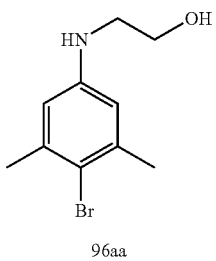

96aa

6 N NaOH (1.5 ml) was added to a solution of bromoacetic acid 2-[acetyl-(4-bromo-3,5-dimethyl-phenyl)-amino]-ethyl ester (302 mg, 0.74 mmol) in EtOH (6 ml). The reaction solution was heated under reflux overnight, cooled to room temperature and then diluted with ethyl acetate. The organic phase was sequentially washed with water and saturated brine and concentrated under reduced pressure. The resulting residue was purified by silica gel column chromatography (hexane-ethyl acetate) to give 2-(4-bromo-3,5-dimethyl-phenylamino)-ethanol (181 mg, 68%).

$^1$H-NMR (CDCl$_3$) δ 6.41 (s, 2H), 3.82 (t, 2H, J=5.1 Hz), 3.27 (t, 2H, J=5.1 Hz), 2.34 (s, 6H).

(Reaction 96-17)

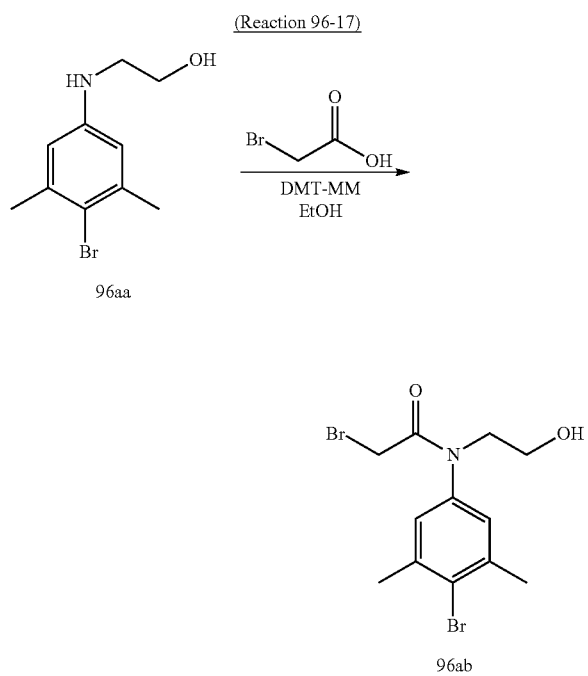

96aa

96ab

2-Bromo-N-(4-bromo-3,5-dimethyl-phenyl)-N-(2-hydroxy-ethyl)acetamide was synthesized by operations similar to those in Reaction 10-1 using appropriate reagents and starting material.

$^1$H-NMR (CDCl$_3$) δ 7.01 (s, 2H), 3.89-3.78 (m, 6H), 2.44 (s, 6H).

(Reaction 96-18)

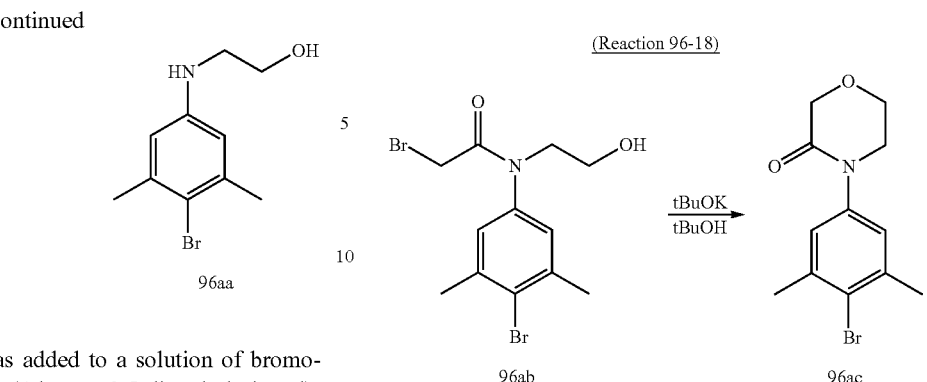

96ab

96ac

Potassium t-butoxide (53 mg, 0.44 mmol) was added to a solution of 2-bromo-N-(4-bromo-3,5-dimethyl-phenyl)-N-(2-hydroxy-ethyl)-acetamide (147 mg, 0.40 mmol) in t-BuOH (2 ml), and the mixture was heated under reflux overnight. The reaction solution was cooled to room temperature and water was then added, followed by extraction with ethyl acetate. The organic phase was washed with saturated brine and then concentrated under reduced pressure. The resulting residue was purified by silica gel column chromatography (hexane-ethyl acetate) to give 4-(4-bromo-3,5-dimethyl-phenyl)-morpholin-3-one (100%).

$^1$H-NMR (CDCl$_3$) δ 7.05 (s, 2H), 4.33 (s, 2H), 4.02 (t, 2H, J=5.0 Hz), 3.72 (t, 2H, J=5.0 Hz), 2.42 (s, 6H).

The aryl bromide reagent used in the synthesis of Compound 516 (1-(4-bromo-3,5-dimethylphenyl)piperidin-2-one) was synthesized as follows.

(Reaction 96-19)

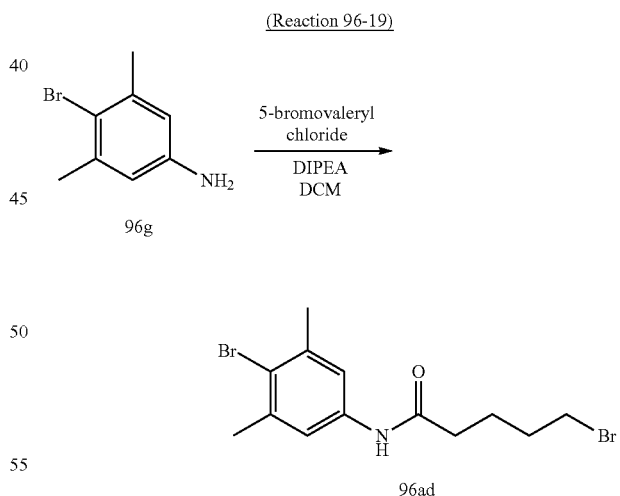

96g

96ad

5-Bromo-pentanoic (4-bromo-3,5-dimethyl-phenyl)-amide was synthesized by operations similar to those in Reaction 2-3 using appropriate reagents and starting material.

$^1$H-NMR (CDCl$_3$) δ 7.25 (s, 2H), 7.19 (brs, 1H), 3.43 (t, 2H, J=6.49 Hz), 2.37 (t, 2H, J=6.87 Hz), 2.37 (s, 6H), 1.9 (m, 4H).

(Reaction 96-20)

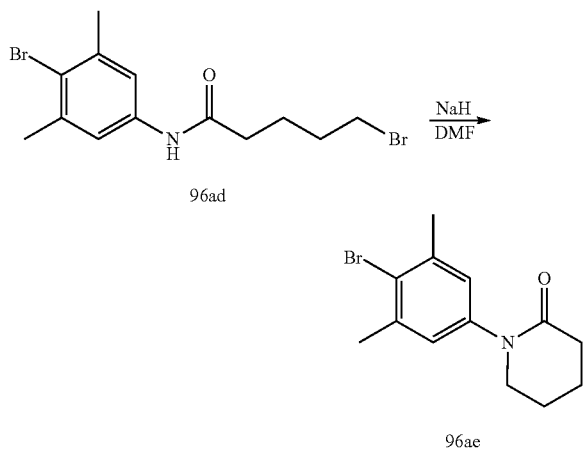

Sodium hydride (37 mg, 0.925 mmol) was added to a solution of 5-bromo-pentanoic (4-bromo-3,5-dimethyl-phenyl-amide (320 mg, 0.881 mmol) in DMF (8 ml) at 0° C., and the mixture was stirred at room temperature for two days. The reaction solution was diluted with ethyl acetate, and the organic layer was sequentially washed with water and saturated brine and concentrated under reduced pressure. The resulting residue was purified by silica gel column chromatography (dichloromethane-ethyl acetate) to give 1-(4-bromo-3,5-dimethylphenyl)piperidin-2-one (240 mg, 97%).

$^1$H-NMR (CDCl$_3$) δ 6.97 (s, 2H), 3.58 (t, 2H, J=6.87 Hz), 2.55 (t, 2H, J=6.87 Hz), 2.40 (s, 6H), 1.93 (m, 4H).

The aryl bromide reagent used in the synthesis of Compound 517 (N-(4-bromo-3,5-dimethyl-benzyl)-N-methyl-acetamide) was synthesized as follows.

(Reaction 96-21)

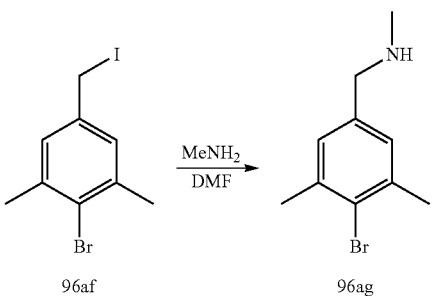

Methylamine (12.3 ml, 24.60 mmol, 2.0 M solution in methanol) was added dropwise to a solution of 2-bromo-5-iodomethyl-1,3-dimethyl-benzene (400 mg, 1.23 mmol) in anhydrous DMF (12 ml), and the mixture was stirred at room temperature for two days. The reaction solution was concentrated under reduced pressure, and the residue was diluted with ethyl acetate. The organic layer was then sequentially washed with water and saturated brine and concentrated under reduced pressure. The resulting residue was purified by silica gel column chromatography (dichloromethane-methanol) to give 1-(4-bromo-3,5-dimethylphenyl)-N-methylmethanamine (280 mg, 100%).

MS (ESI) m/z=228, 230 (M+H)+.

(Reaction 96-22)

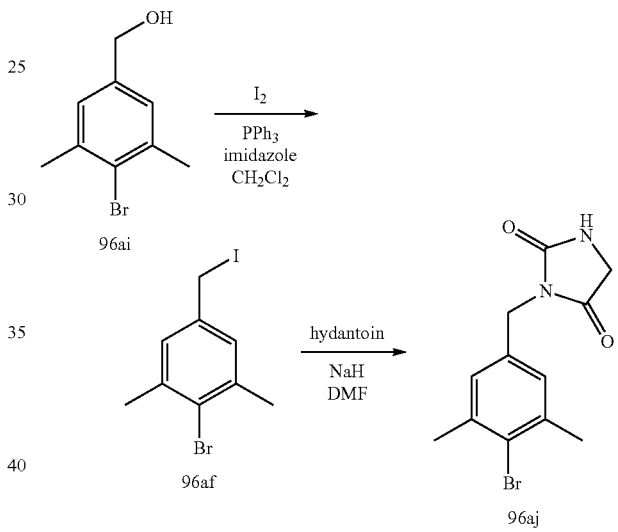

N-(4-Bromo-3,5-dimethyl-benzyl)-N-methyl-acetamide was synthesized by operations similar to those in Reaction 2-3 using appropriate reagents and starting material.

MS (ESI) m/z=270, 272 (M+H)+.

The aryl bromide reagent used in the synthesis of Compound 518 (3-(4-bromo-3,5-dimethyl-benzyl)-imidazolidine-2,4-dione) was synthesized as follows.

(Reaction 96-23)

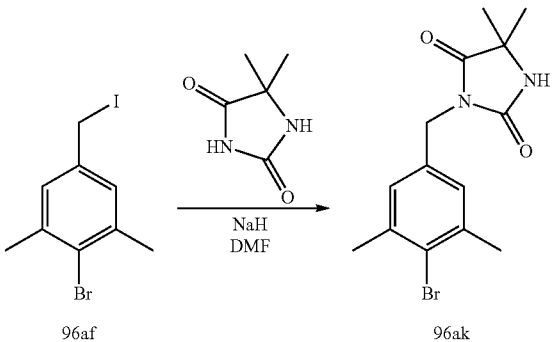

3-(4-Bromo-3,5-dimethyl-benzyl)-imidazolidine-2,4-dione was synthesized by operations similar to those in Reaction 52-1 (using iodine as a reagent) and Reaction 25-3 using appropriate reagents and starting material.

$^1$H-NMR (CDCl$_3$) δ 7.10 (s, 2H), 5.63 (s, 1H), 4.55 (s, 2H), 3.97 (d, 2H, J=1.14 Hz), 2.38 (s, 6H).

The aryl bromide reagent used in the synthesis of Compound 519 (3-(4-bromo-3,5-dimethyl-benzyl)-5,5-dimethyl-imidazolidine-2,4-dione) was synthesized as follows.

(Reaction 96-24)

3-(4-Bromo-3,5-dimethyl-benzyl)-5,5-dimethyl-imidazolidine-2,4-dione was synthesized by operations similar to those in Reaction 25-3 using appropriate reagents and starting material.

MS (ESI) m/z=325, 327 (M+H)+.

The aryl bromide reagent used in the synthesis of Compound 520 (1-(4-bromo-3,5-dimethyl-benzyl)-pyrrolidin-2-one) was synthesized as follows.

(Reaction 96-25)

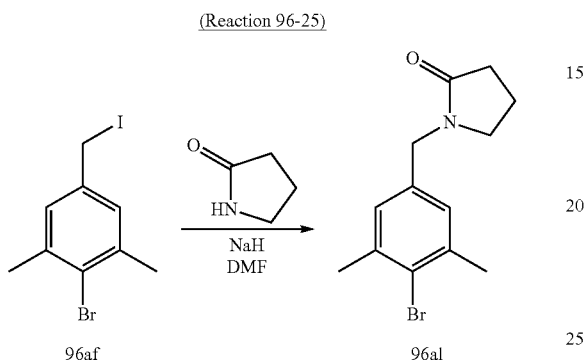

1-(4-Bromo-3,5-dimethyl-benzyl)-pyrrolidin-2-one was synthesized by operations similar to those in Reaction 25-3 using appropriate reagents and starting material.

$^1$H-NMR (CDCl$_3$) δ 6.94 (s, 2H), 4.33 (s, 2H), 3.25 (t, 2H, J=7.24 Hz), 2.44 (t, 2H, J=8.01 Hz), 2.38 (s, 6H), 2.04-1.93 (m, 2H).

The aryl bromide reagent used in the synthesis of Compound 521 (1-(4-bromo-3,5-dimethyl-benzyl)-pyrrolidine-2,5-dione) was synthesized as follows.

(Reaction 96-26)

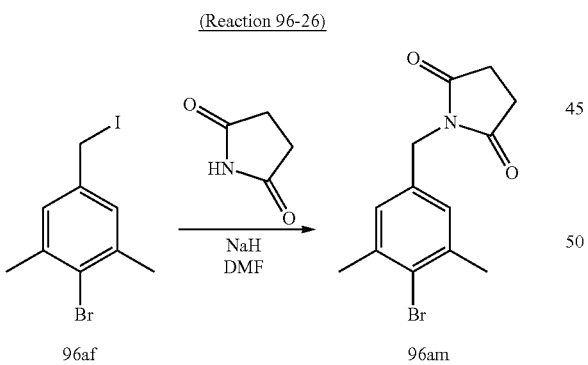

1-(4-Bromo-3,5-dimethyl-benzyl)-pyrrolidine-2,5-dione was synthesized by operations similar to those in Reaction 25-3 using appropriate reagents and starting material.

$^1$H-NMR (CDCl$_3$) δ 7.09 (s, 2H), 4.54 (s, 2H), 2.70 (s, 4H), 2.37 (s, 6H).

The aryl bromide reagent used in the synthesis of Compound 522 (N-(4-bromo-3,5-dimethyl-benzyl)-acetamide) was synthesized as follows.

(Reaction 96-27)

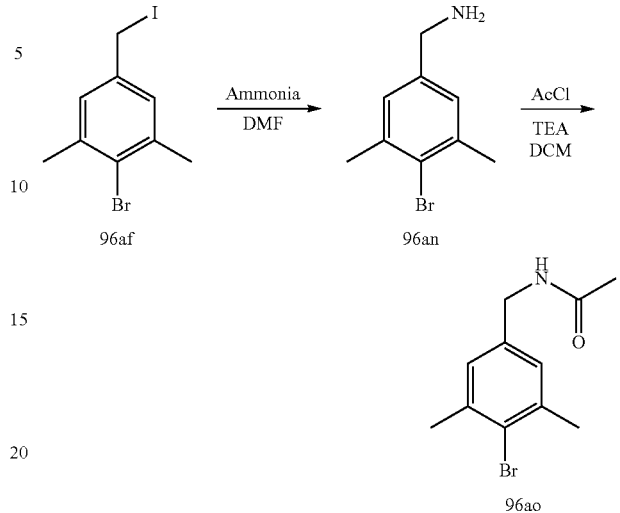

N-(4-Bromo-3,5-dimethyl-benzyl)-acetamide was synthesized by operations similar to those in Reaction 96-21 and Reaction 2-3 using appropriate reagents and starting material.

MS (ESI) m/z=256, 258 (M+H)+.

The aryl bromide reagent used in the synthesis of Compound 523 (N-(4-bromo-3,5-difluoro-phenyl)-N-methyl-acetamide) was synthesized as follows.

(Reaction 96-28)

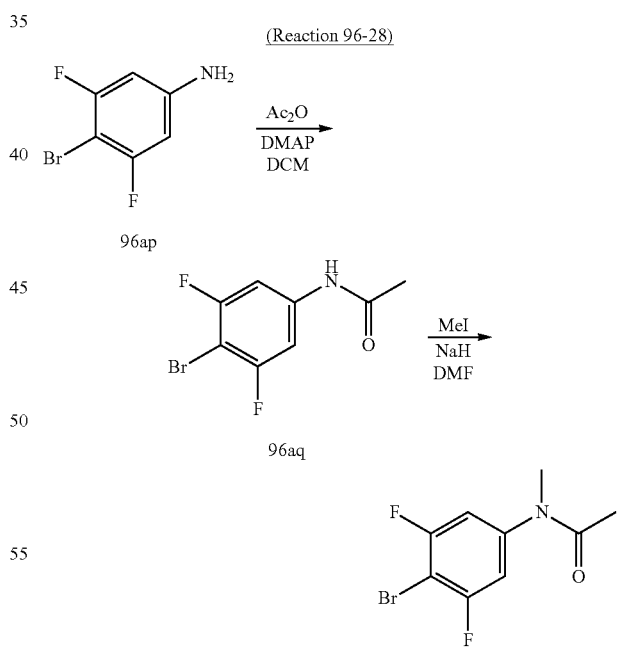

N-(4-Bromo-3,5-difluoro-phenyl)-N-methyl-acetamide was synthesized by operations similar to those in Reaction 19-2 and Reaction 25-3 using appropriate reagents and starting material.

MS (ESI) m/z=264, 266 (M+H)+.

Example 97

The example compounds shown below were obtained by operations similar to those in Reaction 25-2 using appropriate reagents and starting materials.

Compounds 524 to 525

TABLE 72

| Target Compound | Structure | LCMS condition | Retention time (min) | MS (m/z) |
|---|---|---|---|---|
| 524 | (structure) | LCMS-B-1 | 2.03 | 577 (M + H)+ |
| 525 | (structure) | LCMS-F-1 | 0.98 | 690 (M + H)+ |

The aryl bromide reagent used in the synthesis of Compound 525 ([(S)-1-(4-bromo-3-methyl-phenylcarbamoyl)-2-carbamoyl-ethyl]-carbamic acid tert-butyl ester) was synthesized as follows.

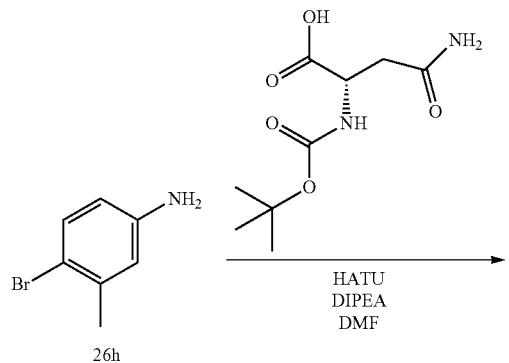

[(S)-1-(4-Bromo-3-methyl-phenylcarbamoyl)-2-carbamoyl-ethyl]-carbamic acid tert-butyl ester was synthesized by operations similar to those in Reaction 10-14 using appropriate reagents and starting material.

MS (ESI) m/z=400 (M+H)+.

Example 98

The example compounds shown below were obtained by operations similar to those in Reaction 25-2 using appropriate reagents and starting materials.

Compounds 526 to 534
TABLE 73
| Target Compound | Structure | LCMS condition | Retention time (min) | MS (m/z) |
|---|---|---|---|---|
| 526 | 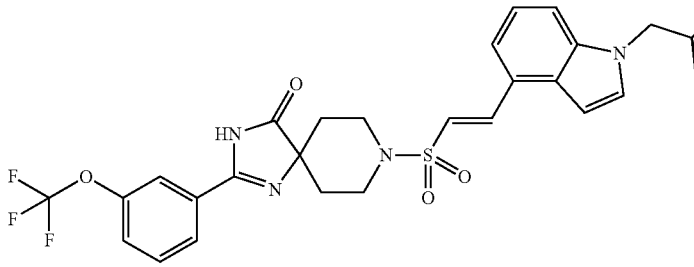 | LCMS-B-1 | 2.5 | 593 (M + H)+ |
| 527 | 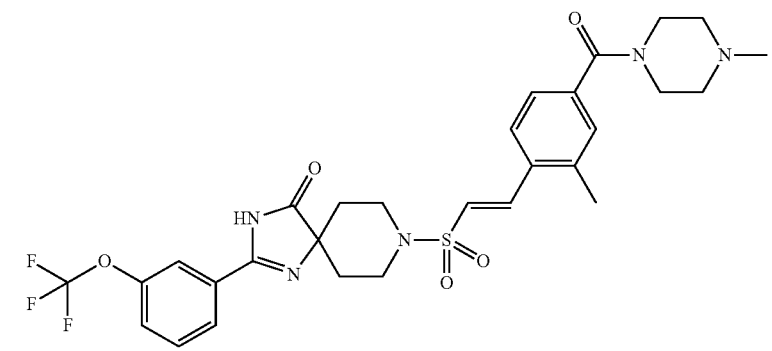 [SMILES: Cc1cc(C(=O)N2CCN(C)CC2)ccc1/C=C/S(=O)(=O)N1CCC2(CC1)N=C(c1cccc(OC(F)(F)F)c1)NC2=O] | LCMS-C-1 | 2.6 | 620 (M + H)+ |
| 528 | 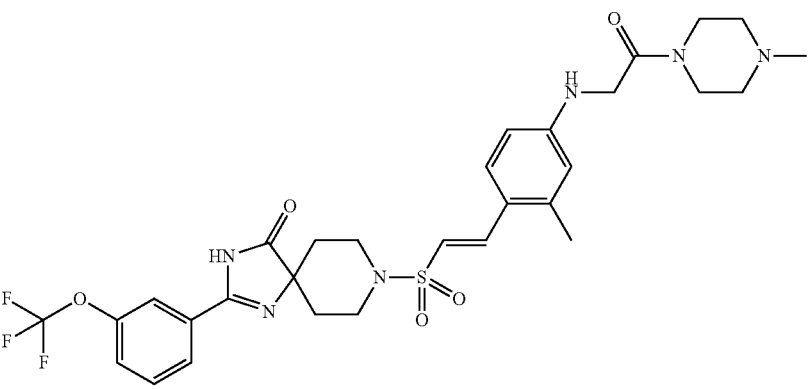 [SMILES: Cc1cc(NCC(=O)N2CCN(C)CC2)ccc1/C=C/S(=O)(=O)N1CCC2(CC1)N=C(c1cccc(OC(F)(F)F)c1)NC2=O] | LCMS-C-1 | 2.65 | 649 (M + H)+ |
| 529 | 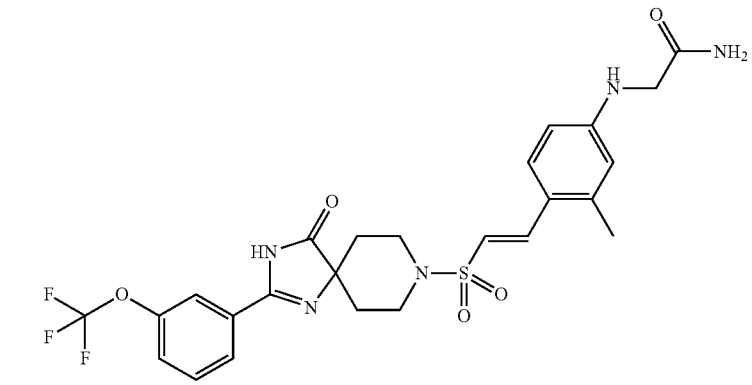 [SMILES: Cc1cc(NCC(N)=O)ccc1/C=C/S(=O)(=O)N1CCC2(CC1)N=C(c1cccc(OC(F)(F)F)c1)NC2=O] | LCMS-C-1 | 2.45 | 566 (M + H)+ |

TABLE 73-continued
| Target Compound | Structure | LCMS condition | Retention time (min) | MS (m/z) |
|---|---|---|---|---|
| 530 | 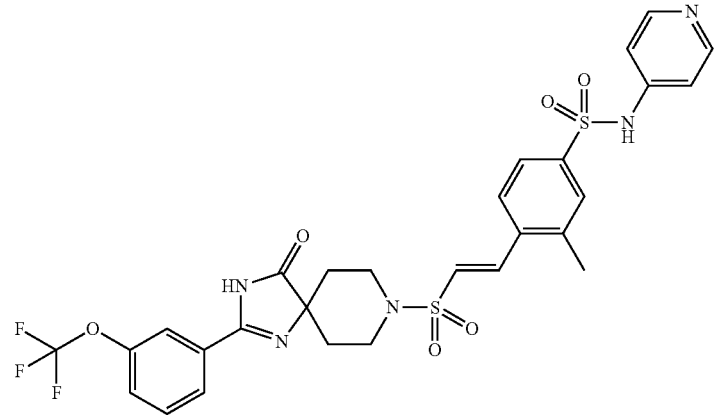 [SMILES: Cc1cc(S(=O)(=O)Nc2ccncc2)ccc1/C=C/S(=O)(=O)N1CCC2(CC1)N=C(c1cccc(OC(F)(F)F)c1)NC2=O] | LCMS-C-1 | 2.38 | 650 (M + H)+ |
| 531 | 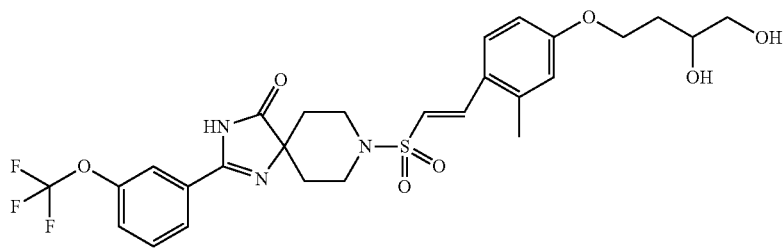 [SMILES: Cc1cc(OCCC(O)CO)ccc1/C=C/S(=O)(=O)N1CCC2(CC1)N=C(c1cccc(OC(F)(F)F)c1)NC2=O] | LCMS-C-1 | 2.63 | 598 (M + H)+ |
| 532 | 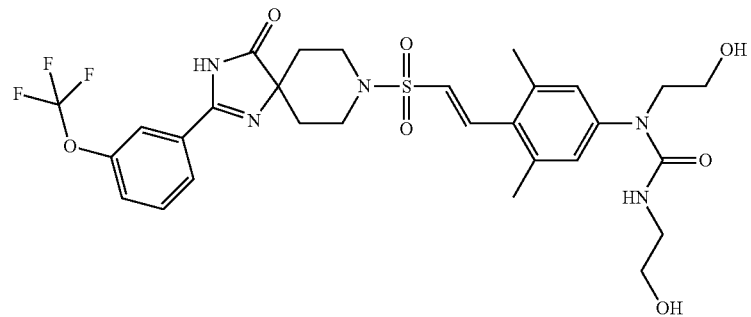 [SMILES: Cc1cc(N(CCO)C(=O)NCCO)cc(C)c1/C=C/S(=O)(=O)N1CCC2(CC1)N=C(c1cccc(OC(F)(F)F)c1)NC2=O] | LCMS-D-1 | 2.16 | 654 (M + H)+ |
| 533 | 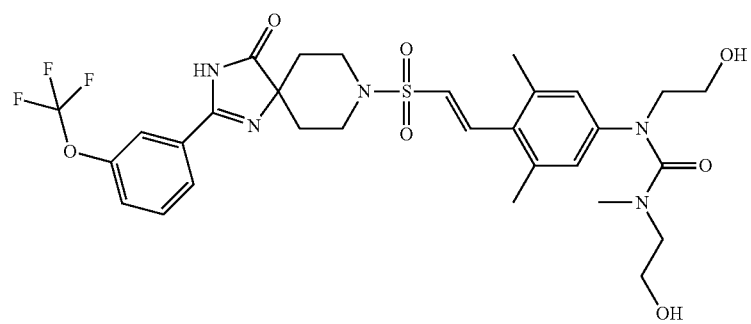 [SMILES: Cc1cc(N(CCO)C(=O)N(C)CCO)cc(C)c1/C=C/S(=O)(=O)N1CCC2(CC1)N=C(c1cccc(OC(F)(F)F)c1)NC2=O] | LCMS-D-1 | 2.35 | 668 (M + H)+ |

TABLE 73-continued

| Target Compound | Structure | LCMS condition | Retention time (min) | MS (m/z) |
|---|---|---|---|---|
| 534 | 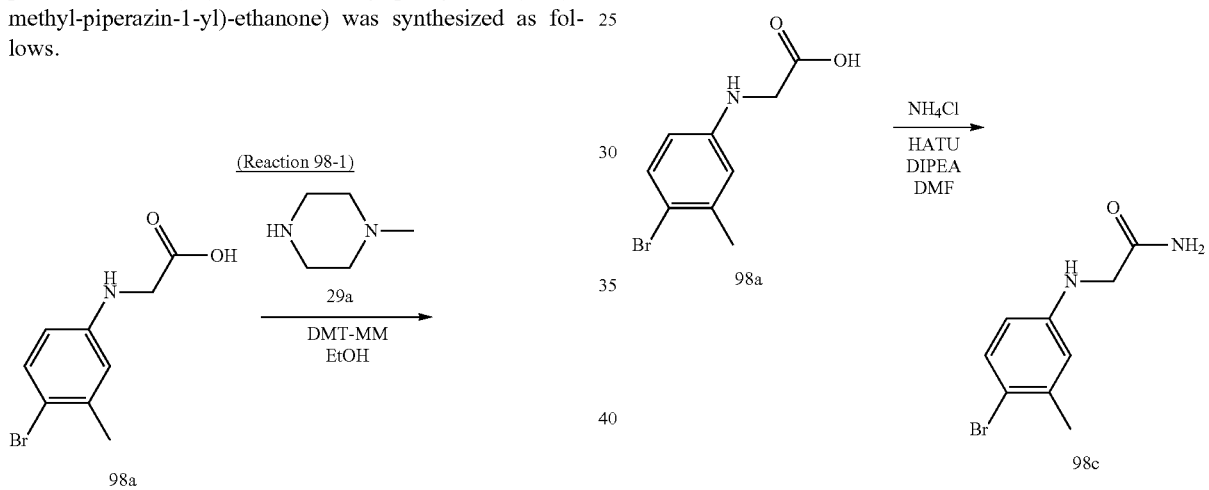 | LCMS-D-1 | 3.1 | 685 (M + H)+ |

The aryl bromide reagent used in the synthesis of Compound 528 (2-(4-bromo-3-methyl-phenylamino)-1-(4-methyl-piperazin-1-yl)-ethanone) was synthesized as follows.

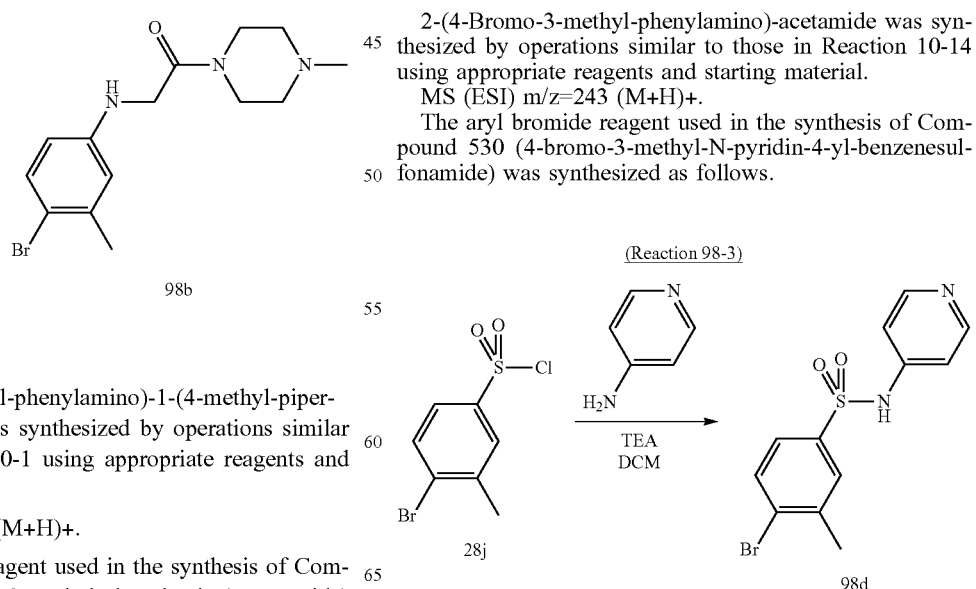

2-(4-Bromo-3-methyl-phenylamino)-1-(4-methyl-piperazin-1-yl)-ethanone was synthesized by operations similar to those in Reaction 10-1 using appropriate reagents and starting material.

MS (ESI) m/z=326 (M+H)+.

The aryl bromide reagent used in the synthesis of Compound 529 (2-(4-bromo-3-methyl-phenylamino)-acetamide) was synthesized as follows.

2-(4-Bromo-3-methyl-phenylamino)-acetamide was synthesized by operations similar to those in Reaction 10-14 using appropriate reagents and starting material.

MS (ESI) m/z=243 (M+H)+.

The aryl bromide reagent used in the synthesis of Compound 530 (4-bromo-3-methyl-N-pyridin-4-yl-benzenesulfonamide) was synthesized as follows.

4-Bromo-3-methyl-N-pyridin-4-yl-benzenesulfonamide was synthesized by operations similar to those in Reaction 5-4 using appropriate reagents and starting material.

MS (ESI) m/z=327 (M+H)+.

The aryl bromide reagent used in the synthesis of Compound 532 (1-(4-bromo-3,5-dimethylphenyl)-1,3-bis(2-hydroxyethyl)urea) was synthesized as follows.

(Reaction 98-4)

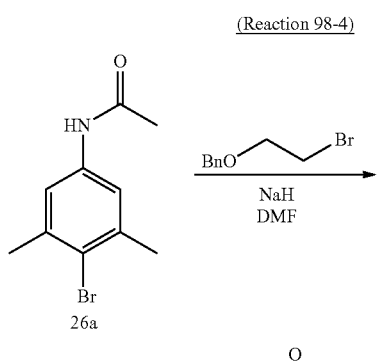

26a

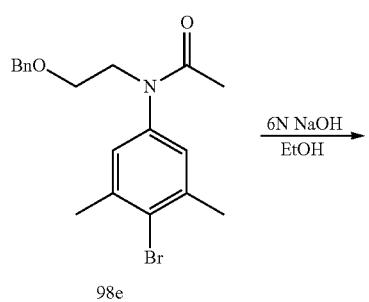

98e

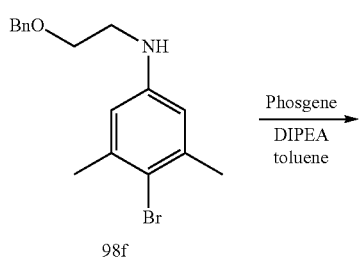

98f

N-(2-(Benzyloxy)ethyl)-4-bromo-3,5-dimethylaniline was synthesized by operations similar to those in Reaction 25-3 and Reaction 96-16 using appropriate reagents and starting material.

$^1$H-NMR (300 MHz, CDCl$_3$) δ 2.32 (s, 6H), 3.27 (t, J=5.39 Hz, 2H), 3.68 (t, J=5.37 Hz, 2H), 3.95 (brs, 1H), 4.54 (s, 2H), 6.37 (s, 2H), 7.25-7.38 (m, 5H).

(Reaction 98-5)

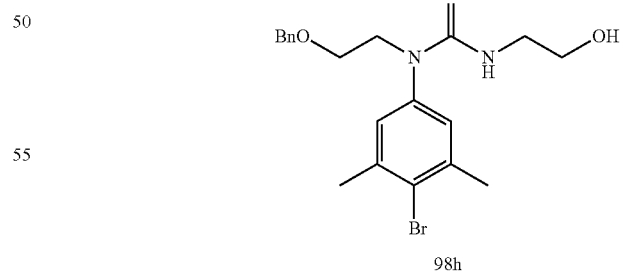

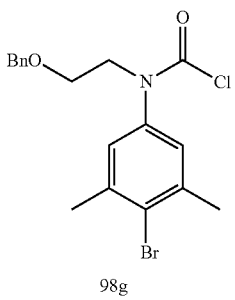

98g

Phosgene (3.5 ml, 6.64 mmol, 20% solution in toluene) and N,N-diisopropylethylamine (1.2 ml, 6.64 mmol) were added to a solution of N-(2-(benzyloxy)ethyl)-4-bromo-3,5-dimethylaniline (740 mg, 2.21 mmol) in anhydrous toluene (11 ml) at 0° C. The reaction solution was gradually warmed to room temperature and stirred at the same temperature for three hours. Water was added to the reaction mixture, followed by extraction with ethyl acetate. The organic phase was sequentially washed with water and saturated brine and concentrated under reduced pressure. The resulting residue was purified by silica gel column chromatography (dichloromethane) to give N-(2-(benzyloxy)ethyl)-N-(4-bromo-3,5-dimethylphenyl)carbamic acid chloride (860 mg, 98%).

$^1$H-NMR (300 MHz, CDCl$_3$) δ 2.36 (s, 6H), 3.67 (t, J=5.42 Hz, 2H), 3.89 (t, J=4.95 Hz, 2H), 4.50 (s, 2H), 6.95 (s, 2H), 7.27-7.38 (m, 5H).

(Reaction 98-6)

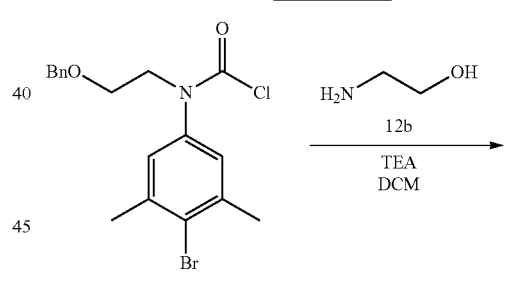

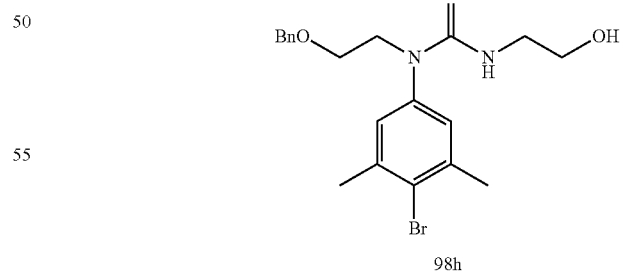

98h 1-(2-(Benzyloxy)ethyl)-1-(4-bromo-3,5-dimethylphenyl)-3-(2-hydroxyethyl)urea was synthesized by operations similar to those in Reaction 82-1 using appropriate reagents and starting material.

MS (ESI) m/z=421, 423 (M+H)+.

(Reaction 98-7)

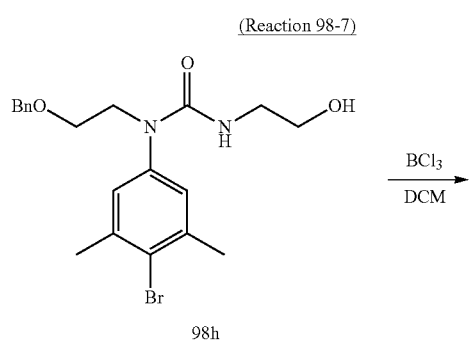

98h

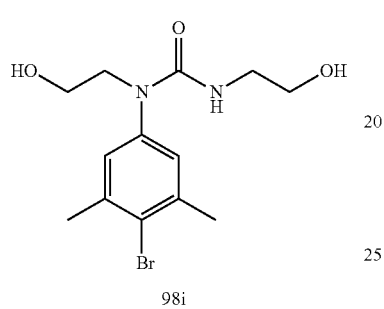

98i

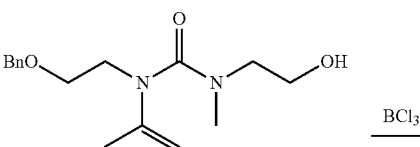

98j

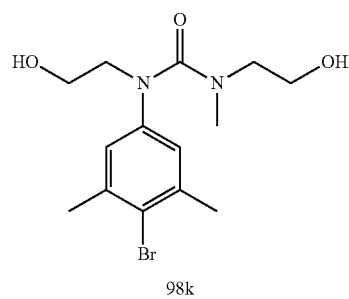

98k

Boron trichloride (0.93 ml, 0.93 mmol, 1.0 M solution in dichloromethane) was added to a solution of 1-(2-(benzyloxy)ethyl)-1-(4-bromo-3,5-dimethylphenyl)-3-(2-hydroxyethyl)urea (98 mg, 0.23 mmol) in anhydrous dichloromethane (4.6 ml) at −78° C., and the mixture was stirred at the same temperature for two hours. A saturated aqueous sodium bicarbonate solution was added to the reaction mixture, followed by extraction with ethyl acetate. The organic phase was sequentially washed with water and saturated brine and concentrated under reduced pressure. The resulting residue was purified by silica gel column chromatography (dichloromethane-methanol) to give 1-(4-bromo-3,5-dimethylphenyl)-1,3-bis(2-hydroxyethyl)urea (64 mg, 83%).

$^1$H-NMR (300 MHz, CDCl$_3$) δ 2.43 (s, 6H), 2.94 (t, J 5.11 Hz, 1H), 3.33 (q, J=5.23 Hz, 2H), 3.60 (t, J=4.78 Hz, 1H), 3.66 (q, J=4.91 Hz, 2H), 3.71-3.81 (m, 4H), 4.73 (brs, 1H), 7.01 (s, 2H).

The aryl bromide reagent used in the synthesis of Compound 533 (1-(4-bromo-3,5-dimethyl-phenyl)-1,3-bis-(2-hydroxy-ethyl)-3-methyl-urea) was synthesized as follows.

1-(4-Bromo-3,5-dimethyl-phenyl)-1,3-bis-(2-hydroxyethyl)-3-methyl-urea was synthesized by operations similar to those in Reaction 82-1 and Reaction 98-7 using appropriate reagents and starting material.

MS (ESI) m/z=345, 347 (M+H)+.

The aryl bromide reagent used in the synthesis of Compound 534 (N-(4-bromo-3,5-dimethyl-phenyl)-N-(tetrahydro-pyran-4-yl)-methanesulfonamide) was synthesized as follows.

(Reaction 98-9)

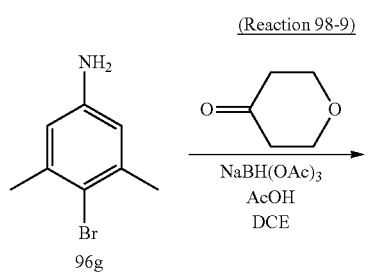

96g (Reaction 98-8)

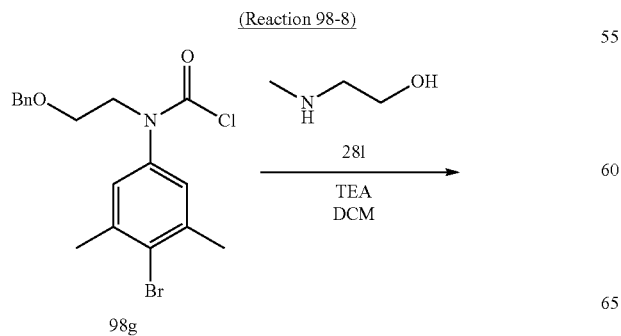

98g

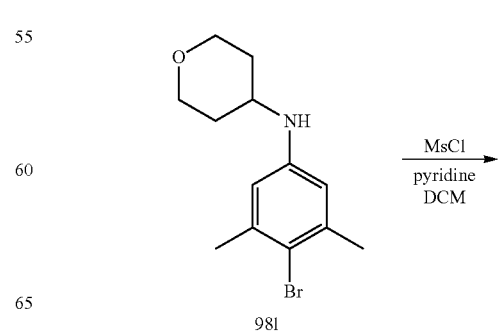

98l

581
-continued

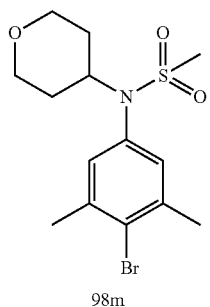

98m

N-(4-Bromo-3,5-dimethyl-phenyl)-N-(tetrahydro-pyran-4-yl)-methanesulfonamide was synthesized by operations similar to those in Reaction 41-1 and Reaction 6-1 using appropriate reagents and starting material.

MS (ESI) m/z=362, 364 (M+H)+.

Example 99

The example compound shown below was obtained by operations similar to those in Reaction 25-2 using appropriate reagents and starting material.

Compound 535

TABLE 74

| Target Compound | Structure | LCMS condition | Retention time (min) | MS (m/z) |
|---|---|---|---|---|
| 535 | ![structure] | LCMS-C-1 | 2.52 | 637 (M + H)+ |

Example 100

3-{3-Methyl-4-[(E)-2-(2-nonyl-4-oxo-1,3,8-triaza-spiro[4.5]dec-1-ene-8-sulfonyl)-vinyl]-phenyl}-imidazolidine-2,4-dione (Compound 536)

(Reaction 100-1)

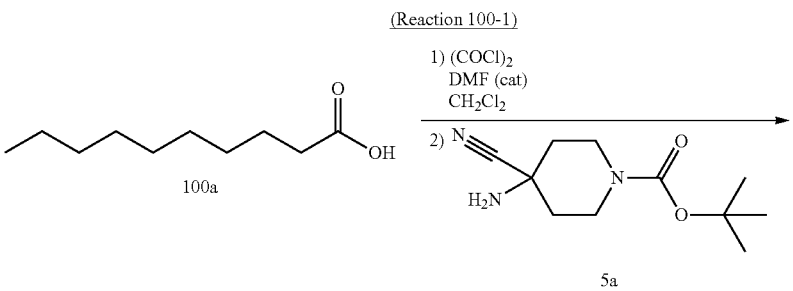

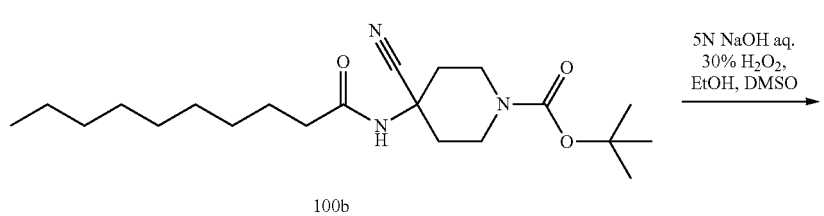

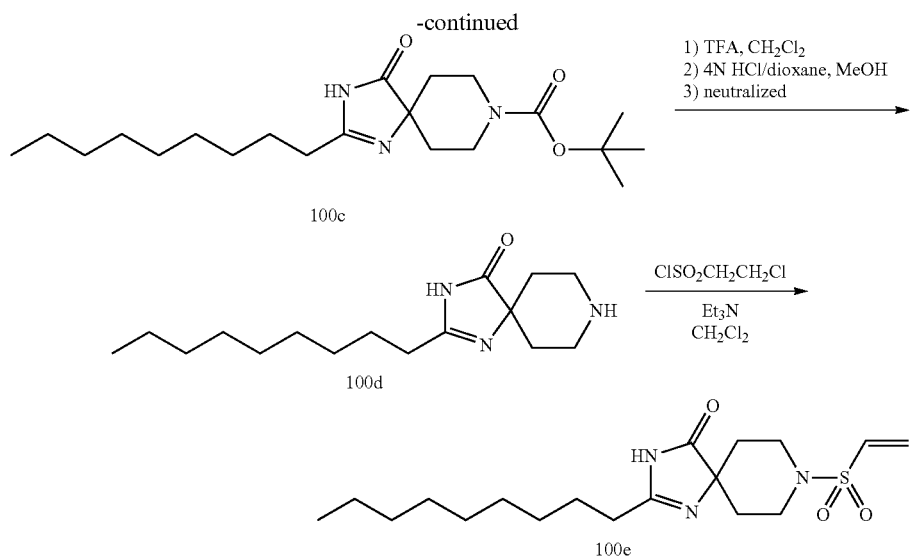

8-Ethenesulfonyl-2-nonyl-1,3,8-triaza-spiro[4.5]dec-1-en-4-one was synthesized by operations similar to those in Reaction 10-20, Reaction 1-4, Reaction 4-1, Reaction 5-3 and reaction 25-1 using appropriate reagents and starting material.

MS (ESI) m/z=370 (M+H)+.

3-{3-Methyl-4-[(E)-2-(2-nonyl-4-oxo-1,3,8-triaza-spiro[4.5]dec-1-ene-8-sulfonyl)-vinyl]-phenyl}-imidazolidine-2,4-dione was synthesized by operations similar to those in Reaction 25-2 using appropriate reagents and starting material.

MS (ESI) m/z=558 (M+H)+.

The example compounds shown below were synthesized by operations similar to those in Reaction 100-2 using appropriate reagents and starting materials.

(Reaction 100-2)

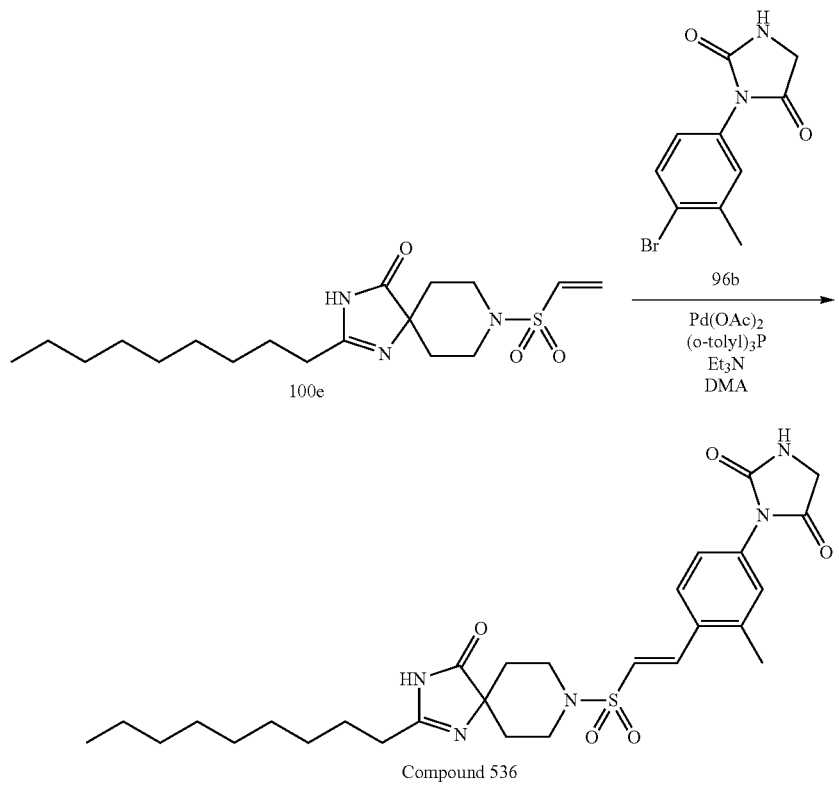

Compounds 537 to Compound 539

TABLE 75

| Target Compound | Structure | LCMS condition | Retention time (min) | MS (m/z) |
|---|---|---|---|---|
| 537 | 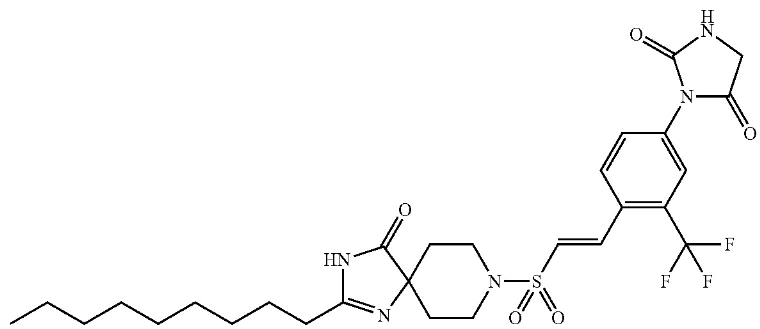 [SMILES: CCCCCCCCCC1=NC2(CCN(S(=O)(=O)/C=C/c3ccc(N4C(=O)CNC4=O)cc3C(F)(F)F)CC2)C(=O)N1] | LCMS-A-1 | 2.63 | 612 (M + H)+ |
| 538 | 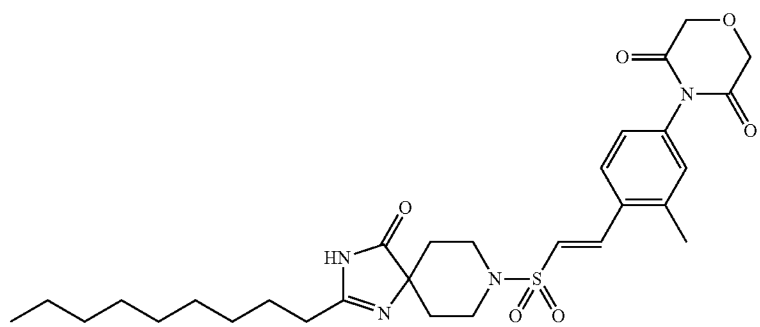 [SMILES: CCCCCCCCCC1=NC2(CCN(S(=O)(=O)/C=C/c3ccc(N4C(=O)COCC4=O)cc3C)CC2)C(=O)N1] | LCMS-A-1 | 2.6 | 573 (M + H)+ |
| 539 | 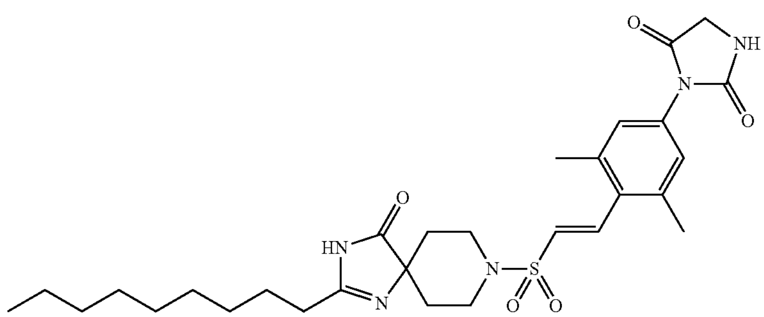 [SMILES: CCCCCCCCCC1=NC2(CCN(S(=O)(=O)/C=C/c3c(C)cc(N4C(=O)CNC4=O)cc3C)CC2)C(=O)N1] | LCMS-A-1 | 2.43 | 572 (M + H)+ |

The aryl bromide reagent used in the synthesis of Compound 537 (3-(4-bromo-3-trifluoromethyl-phenyl)-imidazolidine-2,4-dione) was synthesized as follows.

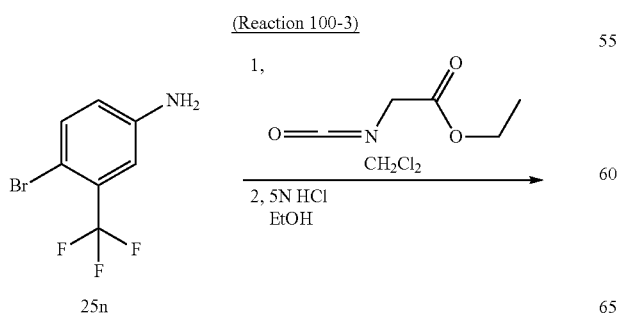

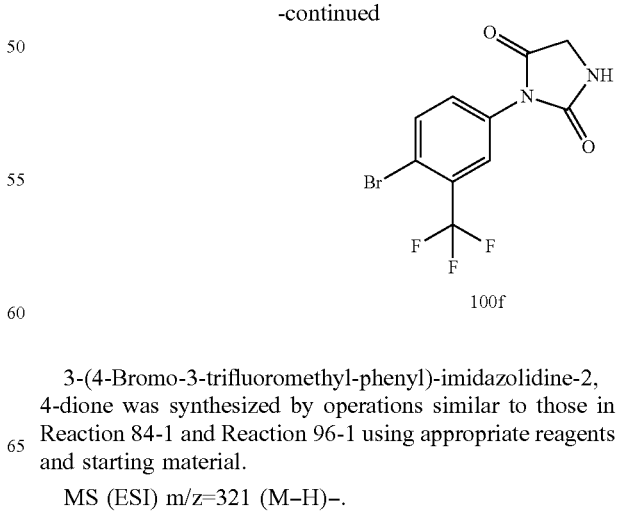

3-(4-Bromo-3-trifluoromethyl-phenyl)-imidazolidine-2,4-dione was synthesized by operations similar to those in Reaction 84-1 and Reaction 96-1 using appropriate reagents and starting material.

MS (ESI) m/z=321 (M−H)−.

The aryl bromide reagent used in the synthesis of Compound 538 (4-(4-bromo-3-methyl-phenyl)-morpholine-3,5-dione) was synthesized as follows.

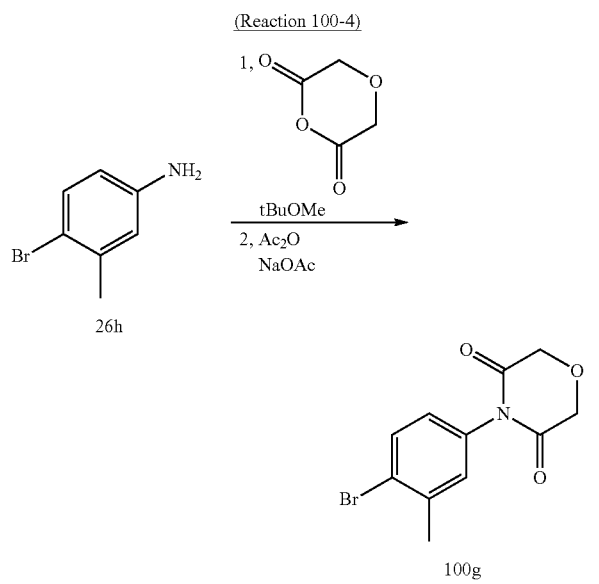

(Reaction 100-4)

26h

100g

[1,4]Dioxane-2,6-dione (312 mg, 2.69 mmol) was added to a solution of 4-bromo-3-methyl-phenylamine (500 mg, 2.69 mmol) in tBuOMe (7.0 ml), and the mixture was stirred at room temperature overnight. The reaction solution was concentrated under reduced pressure. Acetic anhydride (4.0 ml, 42.3 mmol) and sodium acetate (35 mg, 0.427 mmol) were added to the resulting residue, and the mixture was heated with stirring at 60° C. for three hours. Water was added to the reaction solution, and collection by filtration and trituration with water gave 4-(4-bromo-3-methyl-phenyl)-morpholine-3,5-dione (577 mg, 73%).

MS (ESI) m/z=284, 286 (M+H)+.

The aryl bromide reagent used in the synthesis of Compound 539 (3-(4-bromo-3,5-dimethyl-phenyl)-imidazolidine-2,4-dione) was synthesized as follows.

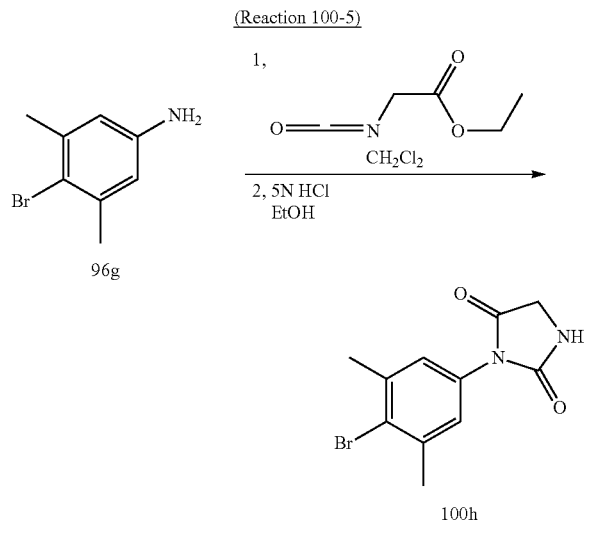

(Reaction 100-5)

96g

100h 3-(4-Bromo-3,5-dimethyl-phenyl)-imidazolidine-2,4-dione was synthesized by operations similar to those in Reaction 84-1 and Reaction 96-1 using appropriate reagents and starting material.

MS (ESI) m/z=283, 285 (M+H)+.

Example 101

5,5-Dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione (Compound 540)

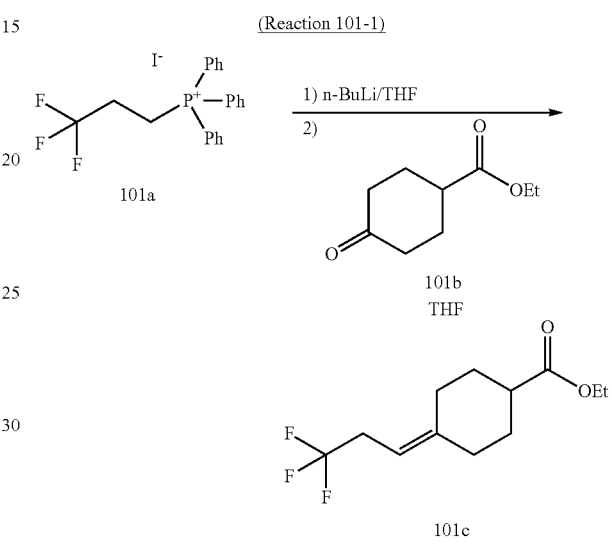

(Reaction 101-1)

101a

101b
THF

101c n-Butyllithium (1.6 M solution in hexane, 26 ml, 41.6 mmol) was added to a solution of triphenyl-(3,3,3-trifluoro-propyl)-phosphonium iodide (20.25 g, 41.64 mmol) in THF (141 ml) at −78° C. over 13 minutes, and the mixture was stirred at the same temperature for 20 minutes. A solution of 4-oxo-cyclohexanecarboxylic acid ethyl ester (6.56 g, 38.54 mmol) in THF (22 ml) was added to the reaction solution at −78° C. over 17 minutes, and the mixture was stirred at the same temperature for one hour. A 50% saturated aqueous ammonium chloride solution was added, followed by extraction with dichloromethane. The organic layer was then dried over MgSO₄ and concentrated under reduced pressure. The resulting residue was purified by silica gel column chromatography (hexane-ethyl acetate) to give ethyl 4-(3,3,3-trifluoro-propylidene)-cyclohexanecarboxylate (9.25 g, 96%).

¹H-NMR (400 MHz, CDCl₃) δ 1.25 (3H, t, J=7.1 Hz), 1.57 (2H, m), 1.90 (1H, m), 2.01 (2H, m), 2.11 (1H, m), 2.31 (1H, m), 2.49 (2H, m), 2.80 (2H, m), 4.13 (2H, t, J=7.1 Hz), 5.15 (1H, t, J=7.6 Hz).

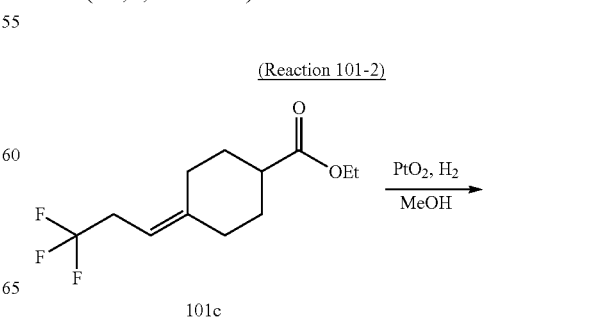

(Reaction 101-2)

101c

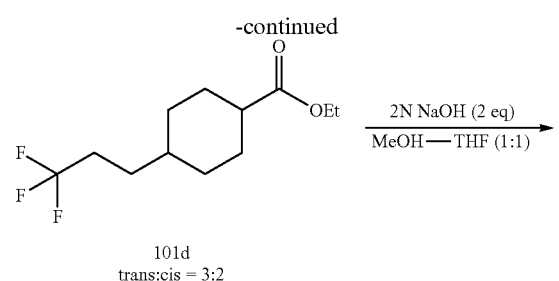

101d
trans:cis = 3:2

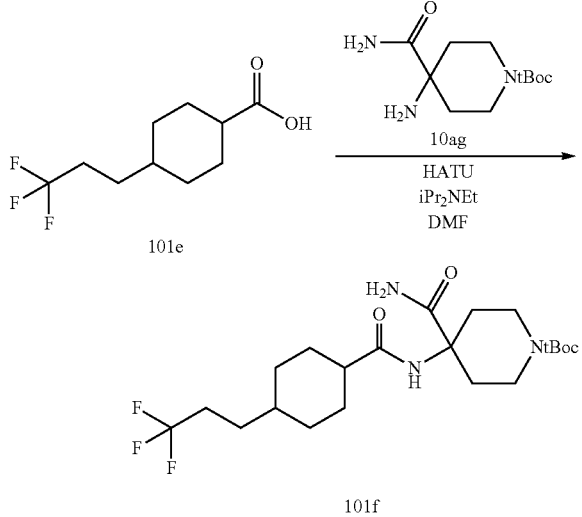

101e

101f

4-Carbamoyl-4-{[4-(3,3,3-trifluoro-propyl)-cyclohexanecarbonyl]-amino}-piperidine-1-carboxylic acid tert-butyl ester was synthesized by operations similar to those in Reaction 18-2 (using PtO₂ as a catalyst), Reaction 95-18 and Reaction 10-14 using appropriate reagents and starting material.

¹H-NMR (400 MHz, CDCl₃) δ 0.98 (2H, m), 1.25-1.70 (9H, m), 1.45 (9H, s), 1.88 (4H, m), 2.10 (3H, m), 3.08 (2H, m), 3.81 (2H, m), 5.30 (1H, br), 5.40 (1H, s), 7.15 (1H, br).

(Reaction 101-3)

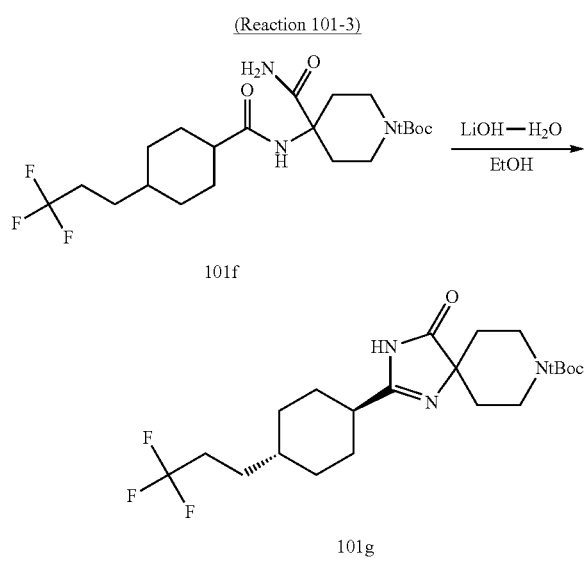

101f

101g

LiOH·H₂O (1.55 g, 36.9 mmol) was added to a solution of 4-carbamoyl-4-{[4-(3,3,3-trifluoro-propyl)-cyclohexanecarbonyl]-amino}-piperidine-1-carboxylic acid tert-butyl ester (5.53 g, 12.3 mmol) in ethanol (123 mL), and the mixture was stirred at 85° C. for two hours. A 50% saturated aqueous ammonium chloride solution was added to the reaction mixture, followed by extraction with ethyl acetate. The organic layer was then dried over MgSO₄ and concentrated under reduced pressure. The resulting residue was purified by reprecipitation with hexane-ethyl acetate=3:1 to give 4-oxo-2-[4-(3,3,3-trifluoro-propyl)-cyclohexyl]-1,3,8-triaza-spiro[4.5]dec-1-ene-8-carboxylic acid tert-butyl ester (4.88 g, 92%).

¹H-NMR (400 MHz, CDCl₃) δ 1.05 (2H, m,), 1.25-1.60 (7H, m), 1.45 (9H, s), 1.81 (2H, m), 1.90 (2H, m), 2.02 (2H, m), 2.11 (2H, m), 2.36 (1H, m), 3.40 (2H, m), 3.90 (2H, m), 8.10 (1H, br).

(Reaction 101-4)

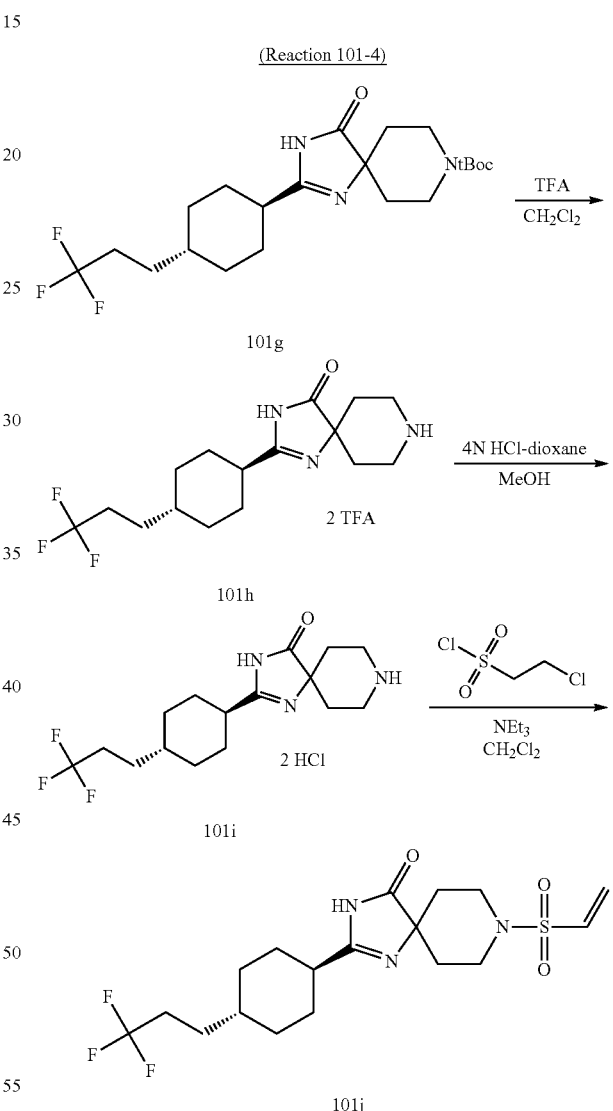

101g

101h

101i

101j

8-Ethenesulfonyl-2-[4-(3,3,3-trifluoro-propyl)-cyclohexyl]-1,3,8-triaza-spiro[4.5]dec-1-en-4-one was synthesized by operations similar to those in Reaction 4-1, Reaction 5-3 and Reaction 25-1 using appropriate reagents and starting material.

¹H-NMR (400 MHz, CDCl₃) δ 1.05 (2H, m,), 1.25-1.70 (7H, m), 1.89 (2H, m), 2.00 (4H, m), 2.11 (2H, m), 2.39 (1H, m), 3.25 (2H, m), 3.67 (2H, m), 6.03 (1H, d, J=10.0 Hz), 6.26 (1H, d, J=16.0 Hz), 6.03 (1H, dd, J=16.0 and 10.0 Hz), 8.50 (1H, br).

(Reaction 101-5)

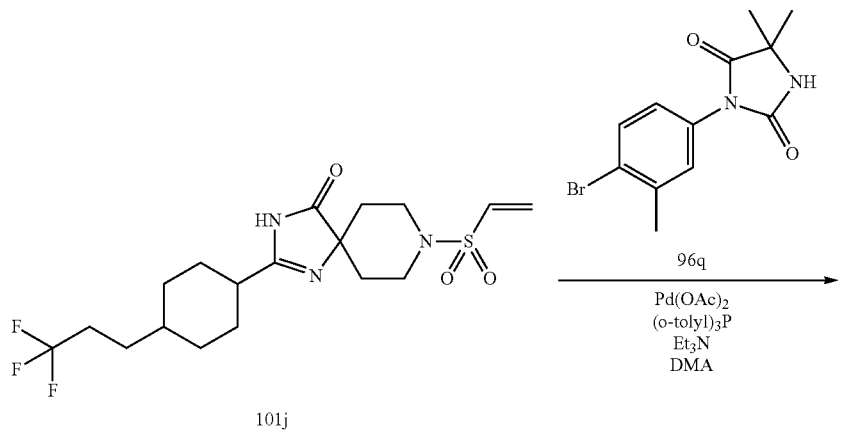

101j

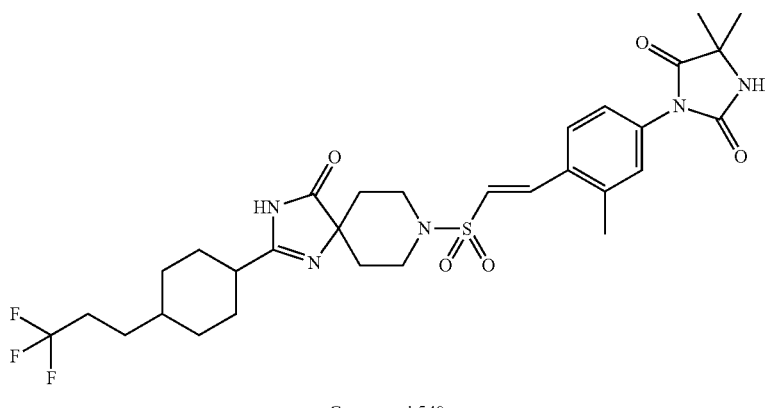

Compound 540

5,5-Dimethyl-3-[3-methyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-imidazolidine-2,4-dione was synthesized by operations similar to those in Reaction 25-2 using appropriate reagents and starting material.
MS (ESI) m/z=638 (M+H)+.

The example compounds shown below were synthesized by operations similar to those in Example 101 using appropriate reagents and starting materials.

Compounds 541 to Compound 559

TABLE 76

| Target Compound | Structure | LCMS condition | Retention time (min) | MS (m/z) |
|---|---|---|---|---|
| 541 | 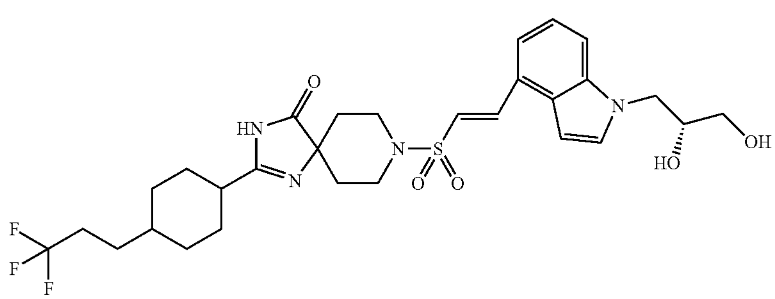 [SMILES: O=C1NC(C2CCC(CCC(F)(F)F)CC2)=NC12CCN(S(=O)(=O)/C=C/c1cccc3c1ccn3C[C@@H](O)CO)CC2] | LCMS-F-1 | 0.94 | 611 (M + H)+ |

TABLE 76-continued
| Target Compound | Structure | LCMS condition | Retention time (min) | MS (m/z) |
|---|---|---|---|---|
| 542 | 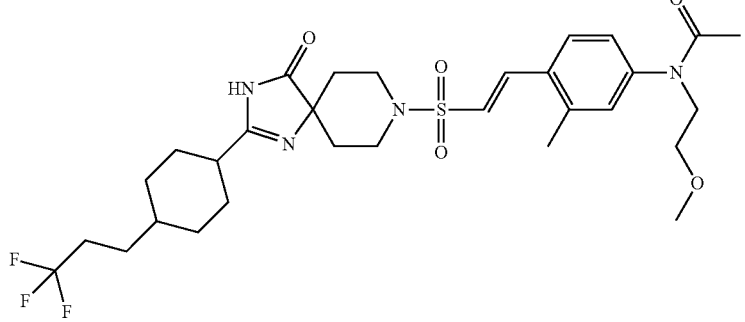 | LCMS-D-1 | 2.30 | 627 (M + H)+ |
| 543 | 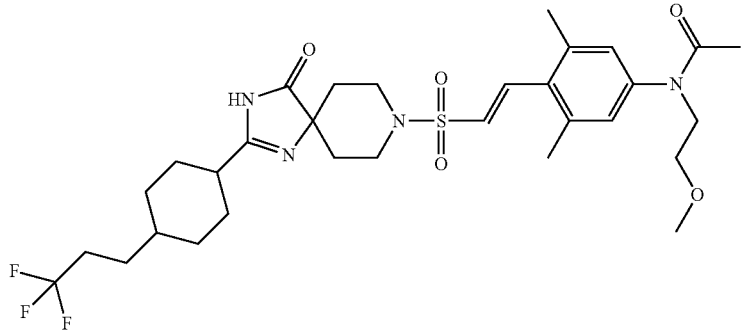 [SMILES: COCCN(C(C)=O)c1cc(C)c(/C=C/S(=O)(=O)N2CCC3(CC2)N=C(C2CCC(CCC(F)(F)F)CC2)NC3=O)c(C)c1] | LCMS-D-1 | 2.42 | 641 (M + H)+ |
| 544 | 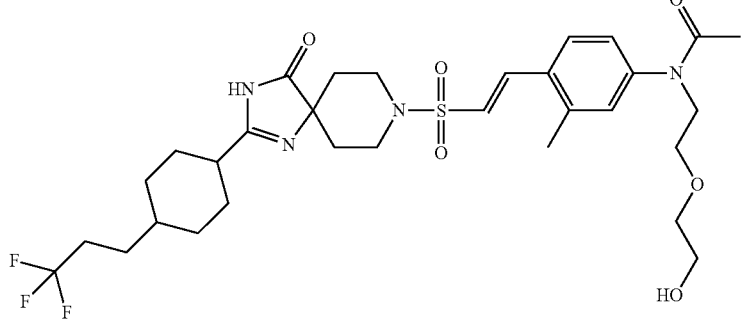 | LCMS-D-1 | 2.11 | 657 (M + H)+ |
| 545 | 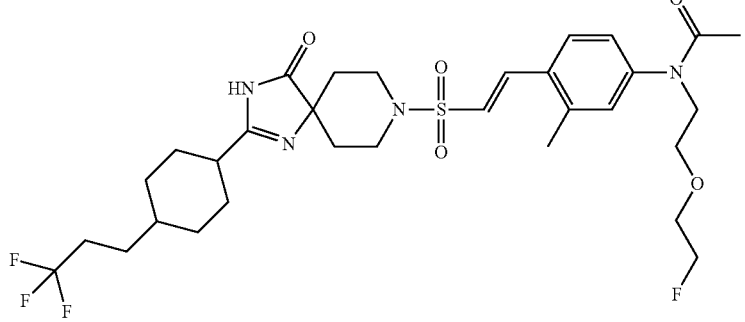 | LCMS-D-1 | 2.30 | 659 (M + H)+ |

TABLE 76-continued

| Target Compound | Structure | LCMS condition | Retention time (min) | MS (m/z) |
|---|---|---|---|---|
| 546 | 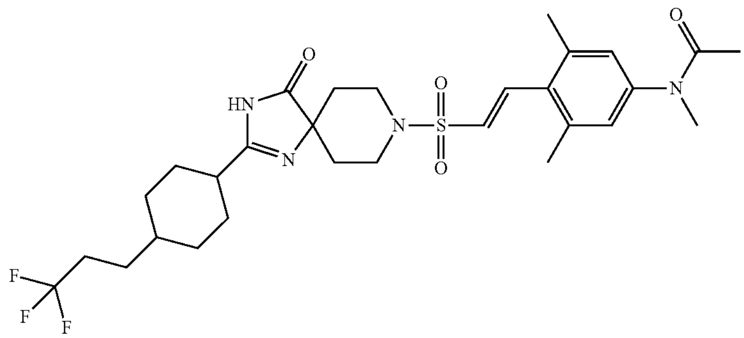 [SMILES: CC(=O)N(C)c1cc(C)c(/C=C/S(=O)(=O)N2CCC3(CC2)N=C(C2CCC(CCC(F)(F)F)CC2)NC3=O)c(C)c1] | LCMS-D-1 | 1.56 | 597 (M + H)+ |
| 547 | 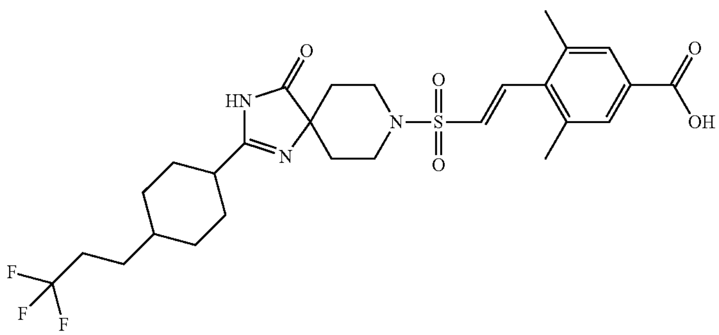 [SMILES: Cc1cc(C(=O)O)cc(C)c1/C=C/S(=O)(=O)N1CCC2(CC1)N=C(C1CCC(CCC(F)(F)F)CC1)NC2=O] | LCMS-D-1 | 2.45 | 570 (M + H)+ |
| 548 | 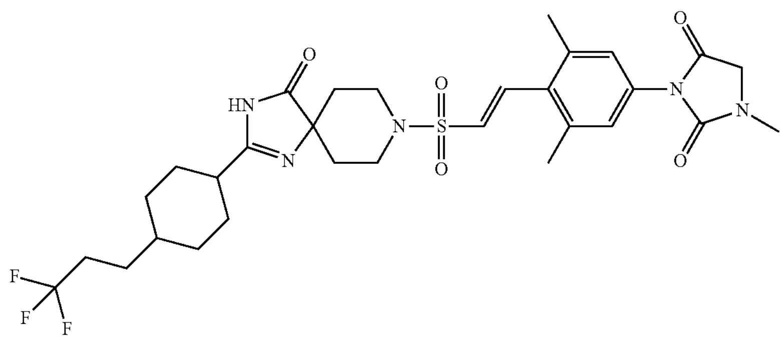 [SMILES: Cc1cc(N2C(=O)CN(C)C2=O)cc(C)c1/C=C/S(=O)(=O)N1CCC2(CC1)N=C(C1CCC(CCC(F)(F)F)CC1)NC2=O] | LCMS-D-1 | 2.13 | 638 (M + H)+ |
| 549 | 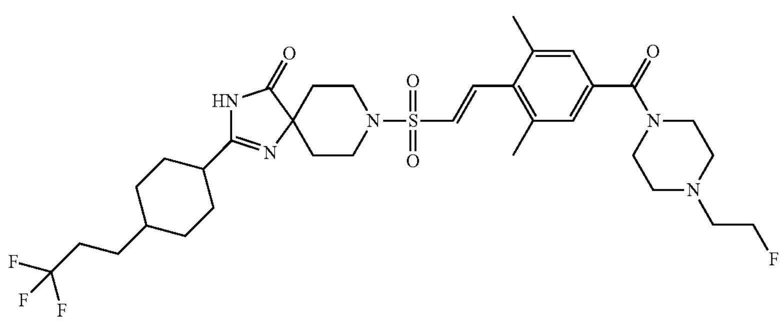 [SMILES: Cc1cc(C(=O)N2CCN(CCF)CC2)cc(C)c1/C=C/S(=O)(=O)N1CCC2(CC1)N=C(C1CCC(CCC(F)(F)F)CC1)NC2=O] | LCMS-D-1 | 1.63 | 684 (M + H)+ |

TABLE 76-continued

| Target Compound | Structure | LCMS condition | Retention time (min) | MS (m/z) |
|---|---|---|---|---|
| 550 | 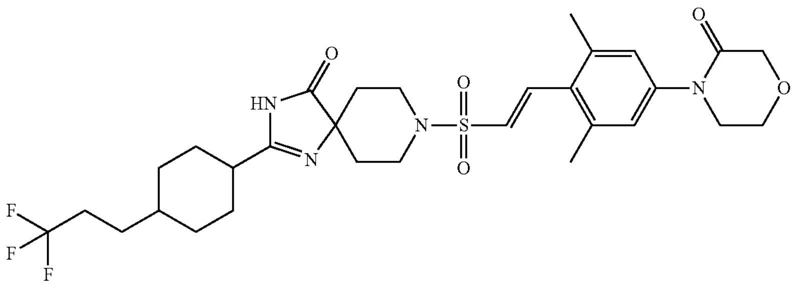 [SMILES: Cc1cc(N2CCOCC2=O)cc(C)c1/C=C/S(=O)(=O)N1CCC2(CC1)N=C(C1CCC(CCC(F)(F)F)CC1)NC2=O] | LCMS-D-1 | 2.23 | 625 (M + H)+ |
| 551 | 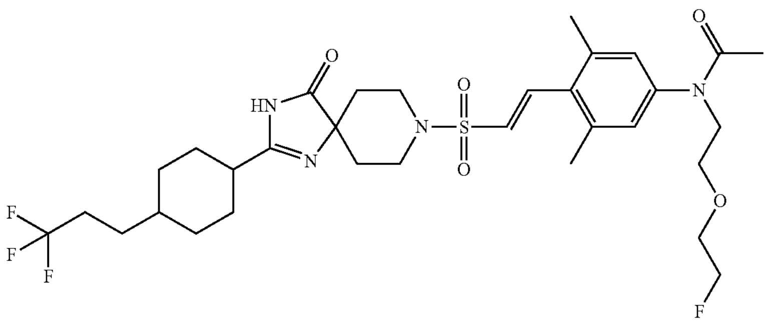 | LCMS-D-1 | 2.55 | 673 (M + H)+ |
| 552 | 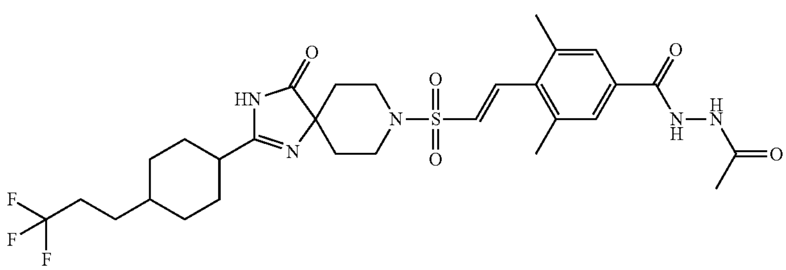 [SMILES: CC(=O)NNC(=O)c1cc(C)c(/C=C/S(=O)(=O)N2CCC3(CC2)N=C(C2CCC(CCC(F)(F)F)CC2)NC3=O)c(C)c1] | LCMS-D-1 | 2.02 | 626 (M + H)+ |
| 553 | 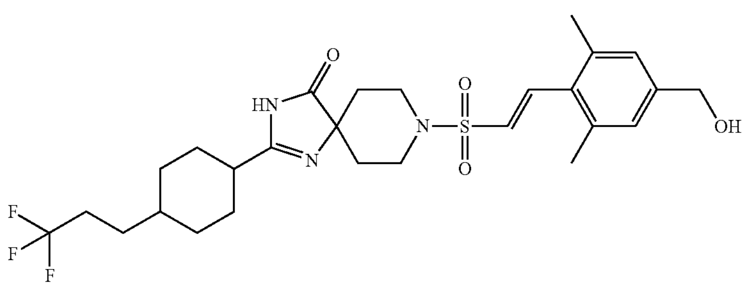 | LCMS-D-1 | 2.40 | 556 (M + H)+ |
| 554 | 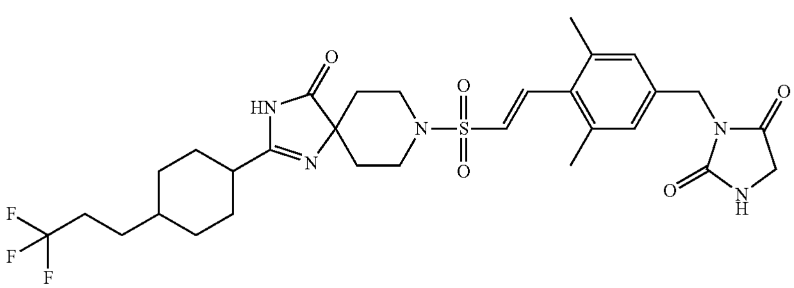 | LCMS-D-1 | 2.45 | 638 (M + H)+ |

TABLE 76-continued

| Target Compound | Structure | LCMS condition | Retention time (min) | MS (m/z) |
|---|---|---|---|---|
| 555 | 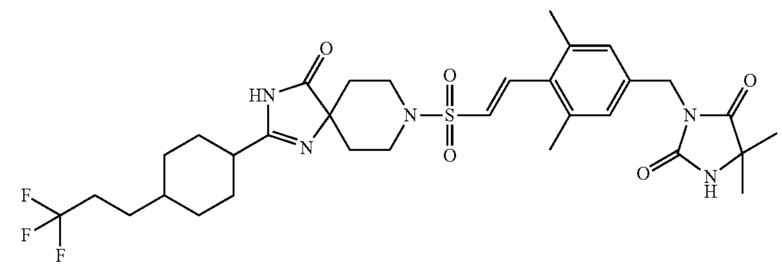 [SMILES: Cc1cc(CN2C(=O)NC(C)(C)C2=O)cc(C)c1/C=C/S(=O)(=O)N1CCC2(CC1)N=C(C1CCC(CCC(F)(F)F)CC1)NC2=O] | LCMS-D-1 | 2.67 | 666 (M + H)+ |
| 556 | 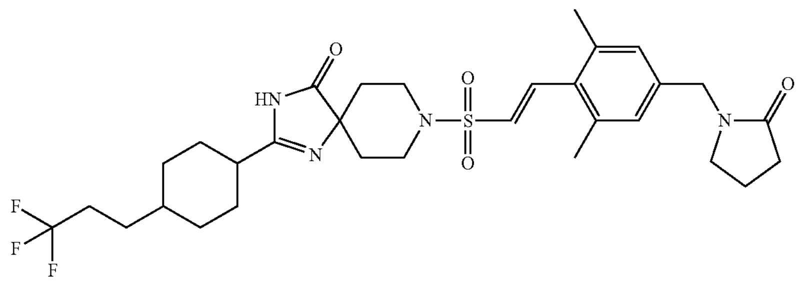 | LCMS-D-1 | 2.58 | 623 (M + H)+ |
| 557 | 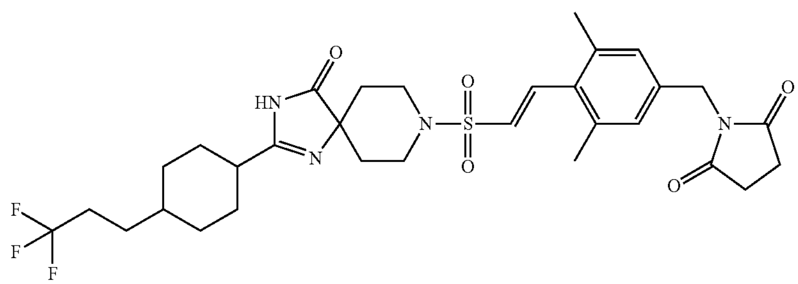 [SMILES: Cc1cc(CN2C(=O)CCC2=O)cc(C)c1/C=C/S(=O)(=O)N1CCC2(CC1)N=C(C1CCC(CCC(F)(F)F)CC1)NC2=O] | LCMS-D-1 | 2.42 | 637 (M + H)+ |
| 558 | 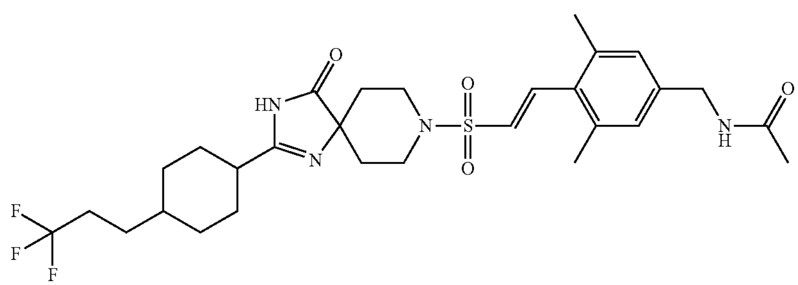 [SMILES: CC(=O)NCc1cc(C)c(/C=C/S(=O)(=O)N2CCC3(CC2)N=C(C2CCC(CCC(F)(F)F)CC2)NC3=O)c(C)c1] | LCMS-D-1 | 2.78 | 597 (M + H)+ |
| 559 | 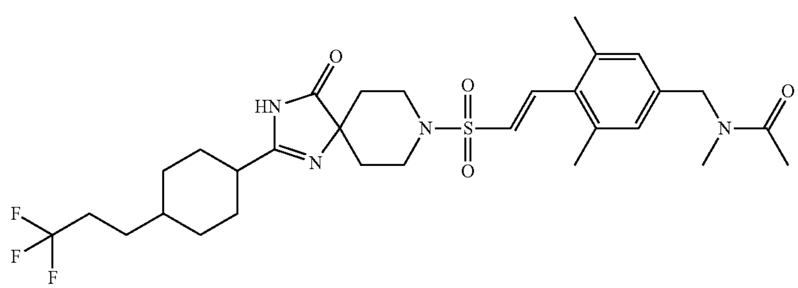 | LCMS-D-1 | 2.45 | 611 (M + H)+ |

The aryl bromide reagent used in the synthesis of Compound 542 (N-(4-bromo-3-methyl-phenyl)-N-(2-methoxy-ethyl)-acetamide) was synthesized as follows.

(Reaction 101-6)

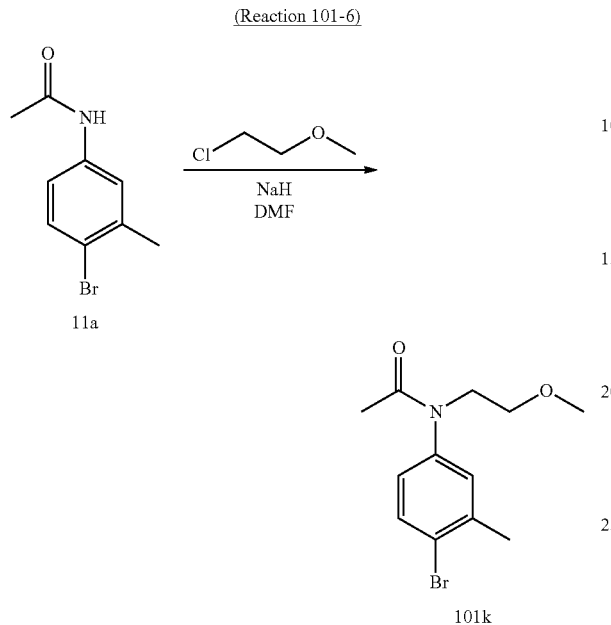

(N-(4-Bromo-3-methyl-phenyl)-N-(2-methoxy-ethyl)-acetamide was synthesized by operations similar to those in Reaction 25-3 using appropriate reagents and starting material.

MS (ESI) m/z=286, 288 (M+H)+.

The aryl bromide reagent used in the synthesis of Compound 543 (N-(4-bromo-3,5-dimethyl-phenyl)-N-(2-methoxy-ethyl)-acetamide) was synthesized as follows.

(Reaction 101-7)

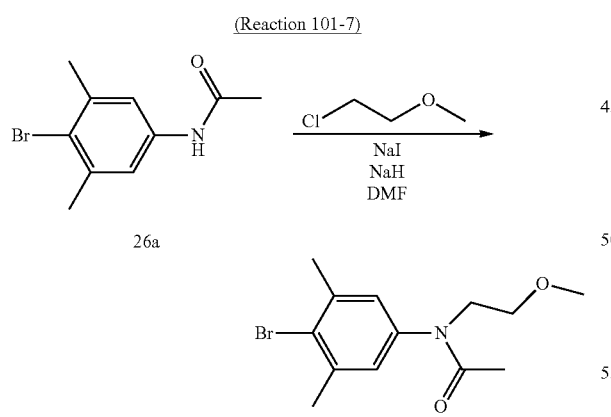

N-(4-Bromo-3,5-dimethyl-phenyl)-N-(2-methoxy-ethyl)-acetamide was synthesized by operations similar to those in Reaction 25-3 using appropriate reagents and starting material.

$^1$H-NMR (CDCl$_3$) δ 6.93 (s, 2H), 3.82 (t, 2H, J=5.7 Hz), 3.49 (t, 2H, J=5.7 Hz), 3.30 (s, 2H), 2.42 (s, 6H), 1.85 (s, 3H).

The aryl bromide reagent used in the synthesis of Compound 544 (N-(4-bromo-3-methyl-phenyl)-N-[2-(2-hydroxy-ethoxy)-ethyl]-acetamide) was synthesized as follows.

(Reaction 101-8)

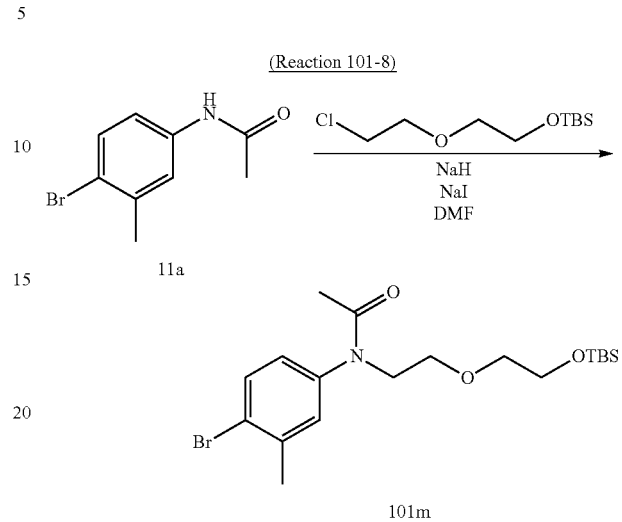

Sodium hydride (60% oil suspension, 100 mg, 2.63 mmol) was added to a solution of 4-bromo-3-methylphenylacetamide (500 mg, 2.19 mmol), tert-butyl-[2-(2-chloroethoxy)-ethoxy]-dimethyl-silane (excess) and sodium iodide (324 mg, 2.19 mmol) in dimethylformamide (20 ml). The mixture was heated with stirring at 100° C. for 17 hours. The reaction solution was cooled and then concentrated. The resulting residue was purified by silica gel column chromatography (ethyl acetate-hexane) to give N-(4-bromo-3-methyl-phenyl)-N-{2-[2-(tert-butyl-dimethyl-silanyloxy)-ethoxy]-ethyl}-acetamide (555 mg, 65%).

$^1$H-NMR (CDCl$_3$) δ 0.04 (s, 6H), 0.87 (s, 9H), 1.83 (s, 3H), 2.39 (s, 3H), 3.40-3.50 (m, 2H), 3.49-3.66 (m, 2H), 3.63-3.77 (m, 2H), 3.73-3.89 (m, 2H), 6.76-7.00 (m, 1H), 6.98-7.16 (m, 1H), 7.38-7.63 (m, 1H).

(Reaction 101-9)

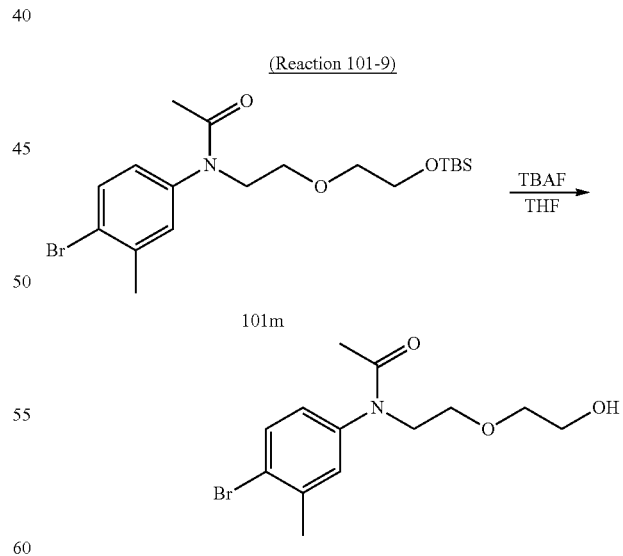

N-(4-Bromo-3-methyl-phenyl)-N-[2-(2-hydroxy-ethoxy)-ethyl]-acetamide was synthesized by operations similar to those in Reaction 39-2 using appropriate reagents and starting material.

MS (ESI) m/z=316, 318 (M+H)+.

The aryl bromide reagent used in the synthesis of Compound 545 (N-(4-bromo-3-methyl-phenyl)-N-[2-(2-fluoro-ethoxy)-ethyl]-acetamide) was synthesized as follows.

(Reaction 101-10)

N-(4-Bromo-3-methyl-phenyl)-N-[2-(2-fluoro-ethoxy)-ethyl]-acetamide was synthesized by operations similar to those in Reaction 25-15 using appropriate reagents and starting material.

MS (ESI) m/z=318, 320 (M+H)+.

The aryl bromide reagent used in the synthesis of Compound 548 (3-(4-bromo-3,5-dimethyl-phenyl)-1-methyl-imidazolidine-2,4-dione) was synthesized as follows.

(Reaction 101-11)

3-(4-Bromo-3,5-dimethyl-phenyl)-1-methyl-imidazolidine-2,4-dione was synthesized by operations similar to those in Reaction 96-6 using appropriate reagents and starting material.

MS (ESI) m/z=297, 299 (M+H)+.

The aryl bromide reagent used in the synthesis of Compound 549 ((4-bromo-3,5-dimethyl-phenyl)-[4-(2-fluoro-ethyl)-piperazin-1-yl]-methanone) was synthesized as follows.

(Reaction 101-12)

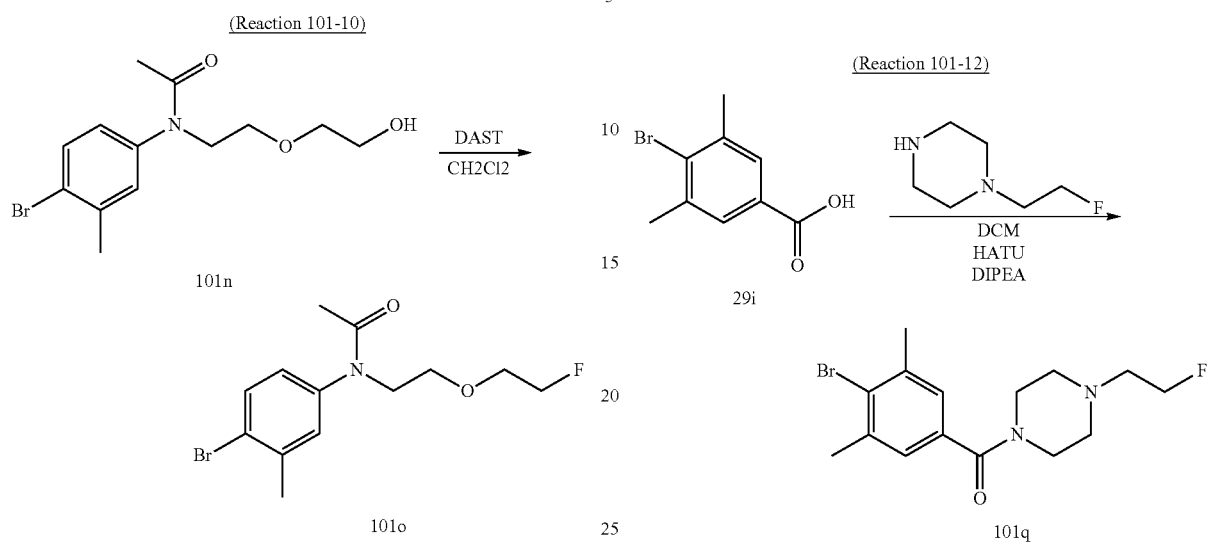

(4-Bromo-3,5-dimethyl-phenyl)-[4-(2-fluoro-ethyl)-piperazin-1-yl]-methanone was synthesized by operations similar to those in Reaction 10-14 using appropriate reagents and starting material.

$^1$H-NMR (CDCl$_3$) δ 7.10 (s, 2H), 4.66 (t, 1H, J=4.96 Hz), 4.51 (t, 1H, J=4.96 Hz), 3.79 (s, 2H), 3.47 (s, 2H), 2.79 (t, 1H, J=4.96 Hz), 2.70 (t, 1H, J=4.96 Hz), 2.56 (brs, 4H), 2.43 (s, 6H).

The aryl bromide reagent used in the synthesis of Compound 551 (N-(4-bromo-3,5-dimethyl-phenyl)-N-[2-(2-fluoroethoxy)ethyl]acetamide) was synthesized as follows.

(Reaction 101-13)

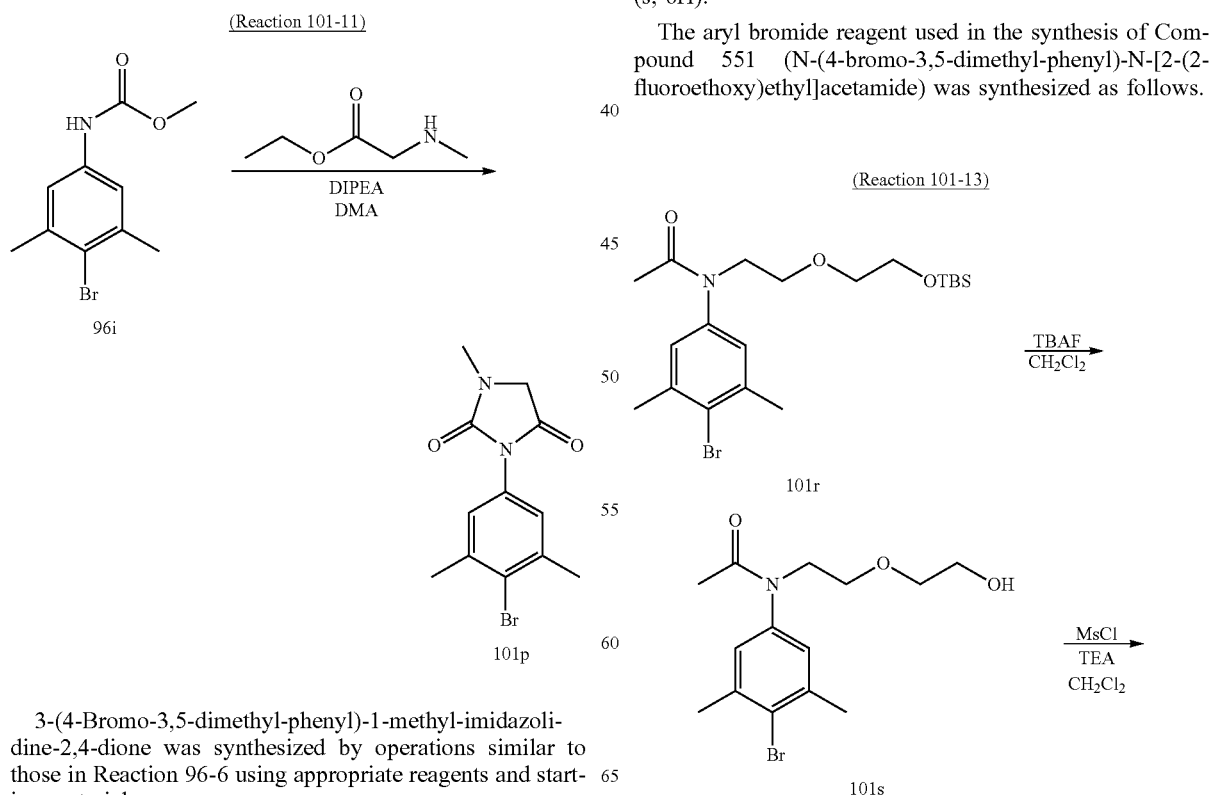

605

-continued

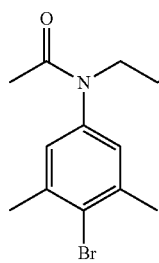

101t

2-[2-[Acetyl-(4-bromo-3,5-dimethyl-phenyl)amino]ethoxy]ethyl methanesulfonate was synthesized by operations similar to those in Reaction 39-2 and Reaction 5-4 using appropriate reagents and starting material.

MS (ESI) m/z=408, 410 (M+H)+.

(Reaction 101-14)

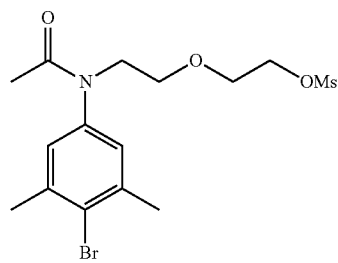

Potassium fluoride (180 mg, 3.11 mmol) was added to a solution of 2-[2-[acetyl-(4-bromo-3,5-dimethyl-phenyl)amino]ethoxy]ethyl methanesulfonate (254 mg, 0.622 mmol) in PEG200 (2 ml), and the mixture was irradiated with microwaves at 100° C. for 10 minutes. The reaction solution was diluted with ethyl acetate, and the organic layer was sequentially washed with water and saturated brine and concentrated under reduced pressure. The resulting residue was purified by silica gel column chromatography (hexane-ethyl acetate) to give N-(4-bromo-3,5-dimethyl-phenyl)-N-[2-(2-fluoroethoxy)ethyl]acetamide (144 mg, 70%).

MS (ESI) m/z=332, 334 (M+H)+.

The aryl bromide reagent used in the synthesis of Compound 552 (N'-(4-bromo-3,5-dimethyl-benzoyl)-hydrazinecarboxylic acid tert-butyl ester) was synthesized as follows.

606

(Reaction 101-15)

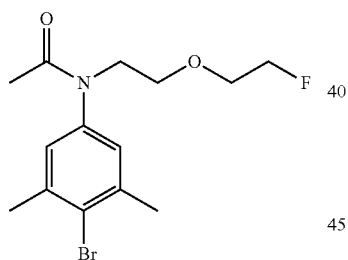

N'-(4-Bromo-3,5-dimethyl-benzoyl)-hydrazinecarboxylic acid tert-butyl ester was synthesized by operations similar to those in Reaction 10-14 using appropriate reagents and starting material.

MS (ESI) m/z=343, 345 (M+H)+.

Example 102

3-(4-{(E)-2-[2-(4-Butyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 560)

(Reaction 102-1)

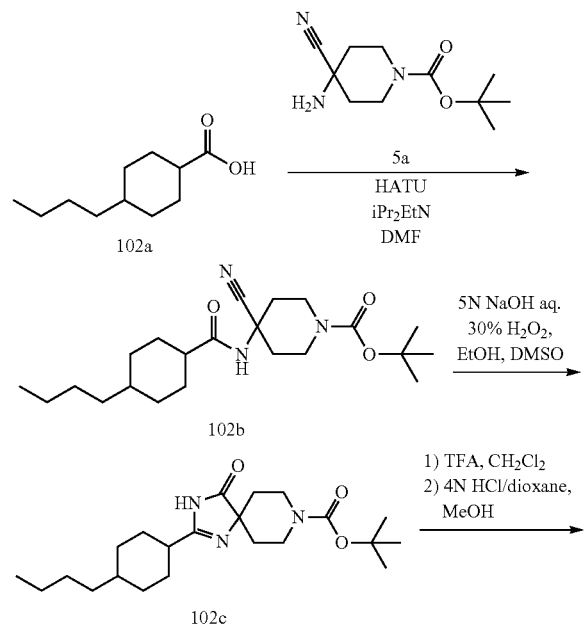

-continued

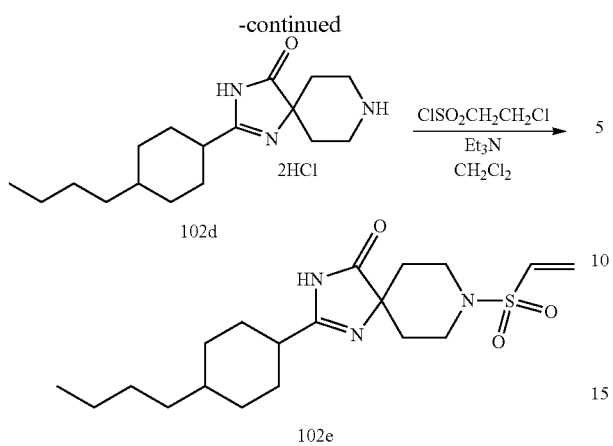

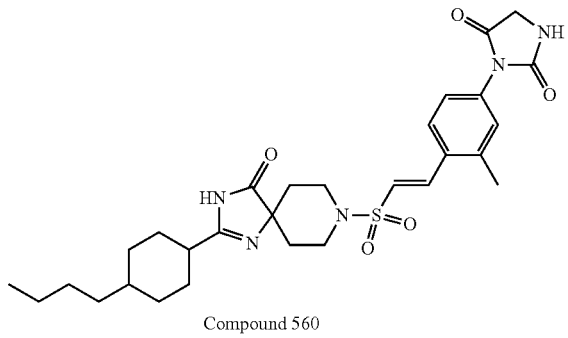

Compound 560

2-(4-Butyl-cyclohexyl)-8-ethenesulfonyl-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.

MS (ESI) m/z=382 (M+H)+.

3-(4-{(E)-2-[2-(4-Butyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 25-2 using appropriate reagents and starting material.

MS (ESI) m/z=570 (M+H)+.

The example compounds shown below were synthesized by operations similar to those in Reaction 102-2 using appropriate reagents and starting materials.

(Reaction 102-2)

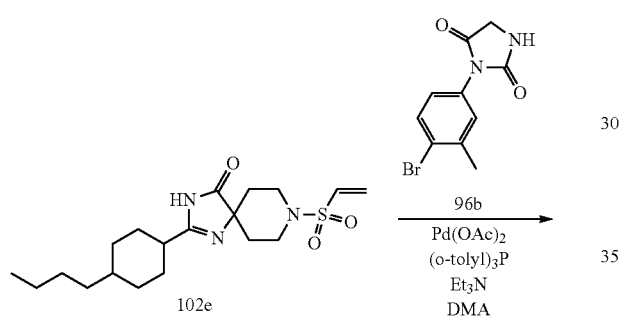

Compounds 561 to Compound 562

TABLE 77

| Target Compound | Structure | LCMS condition | Retention time (min) | MS (m/z) |
|---|---|---|---|---|
| 561 | 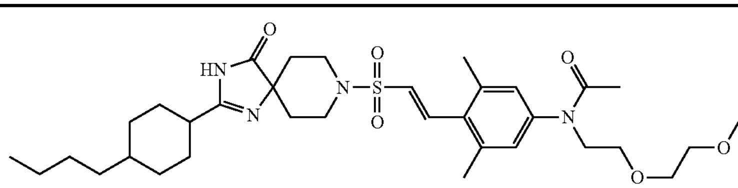 | LCMS-D-1 | 2.17 | 645 (M + H)+ |
| 562 | 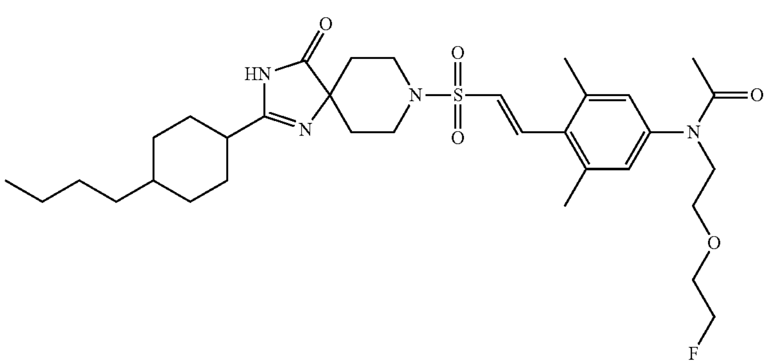 [SMILES: CCCCC1CCC(C2=NC3(CCN(S(=O)(=O)/C=C/c4c(C)cc(N(CCOCCF)C(C)=O)cc4C)CC3)C(=O)N2)CC1] | LCMS-D-1 | 3.25 | 633 (M + H)+ |

The aryl bromide reagent used in the synthesis of Compound 561 (N-(4-bromo-3,5-dimethyl-phenyl)-N-[2-(2-methoxy-ethoxy)-ethyl]-acetamide) was synthesized as follows.

(Reaction 102-3)

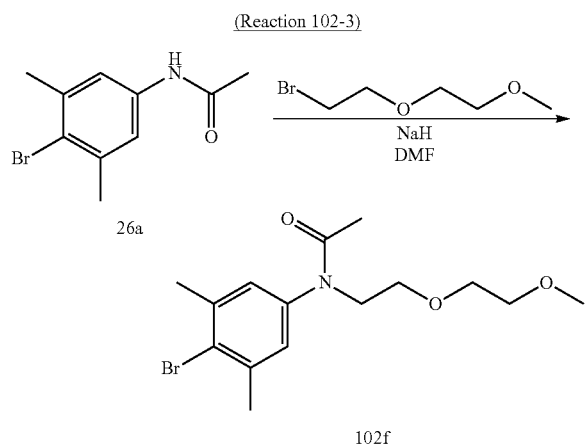

N-(4-Bromo-3,5-dimethyl-phenyl)-N-[2-(2-methoxy-ethoxy)-ethyl]-acetamide was synthesized by operations similar to those in Reaction 25-3 using appropriate reagents and starting material.
MS (ESI) m/z=334, 336 (M+H)+.

Example 103

3-(4-{(E)-2-[2-(4-Isopropyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 563)

(Reaction 103-1)

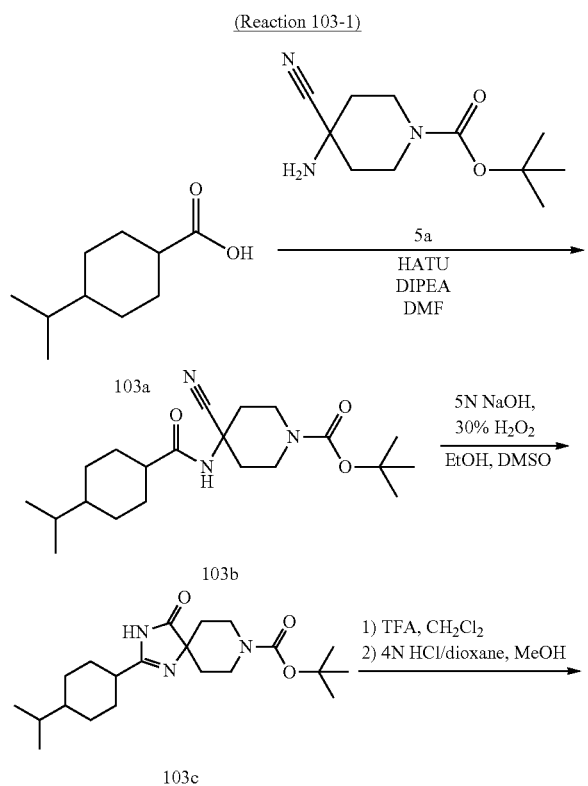

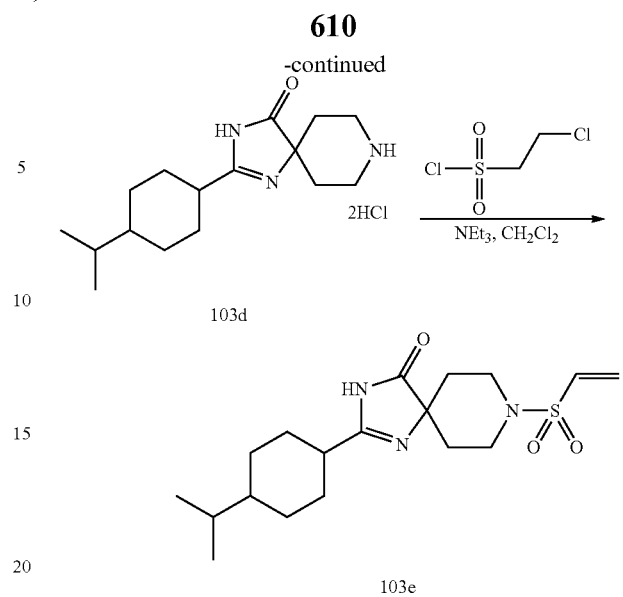

8-Ethenesulfonyl-2-(4-isopropyl-cyclohexyl)-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.
MS (ESI) m/z=368 (M+H)+.

(Reaction 103-2)

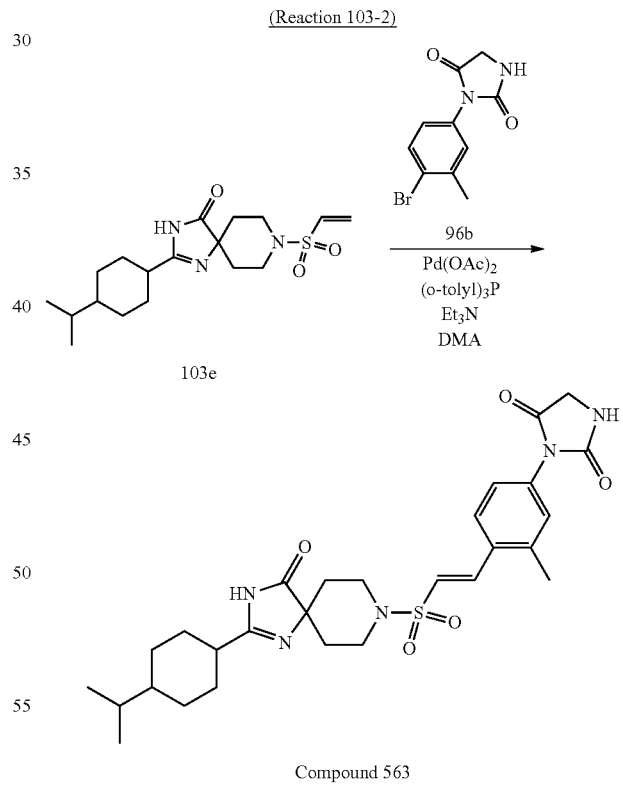

Compound 563

3-(4-{(E)-2-[2-(4-Isopropyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 25-2 using appropriate reagents and starting material.
MS (ESI) m/z=556 (M+H)+.

The example compound shown below was synthesized by operations similar to those in Reaction 103-2 using appropriate reagents and starting material.

Compound 564

TABLE 78

| Target Compound | Structure | LCMS condition | Retention time (min) | MS (m/z) |
|---|---|---|---|---|
| 564 | 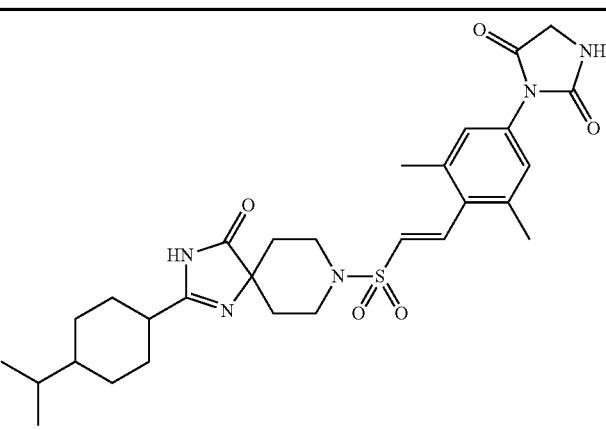 | LCMS-C-1 | 2.72 | 570 (M + H)+ |

Example 104

The example compounds shown below were obtained by operations similar to those in Reaction 26-1 using appropriate reagents and starting materials.

Compounds 565 to 574

TABLE 79

| Target Compound | Structure | LCMS condition | Retention time (min) | MS (m/z) |
|---|---|---|---|---|
| 565 | 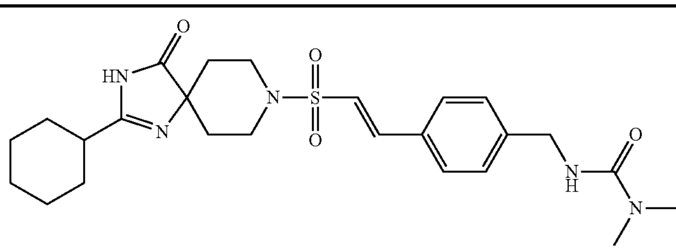 | LCMS-C-1 | 2.25 | 502 (M + H)+ |
| 566 | 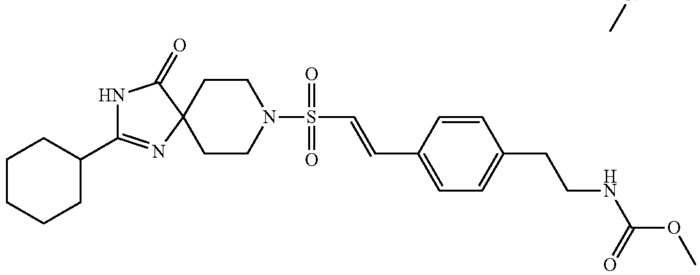 | LCMS-C-1 | 2.47 | 503 (M + H)+ |
| 567 | 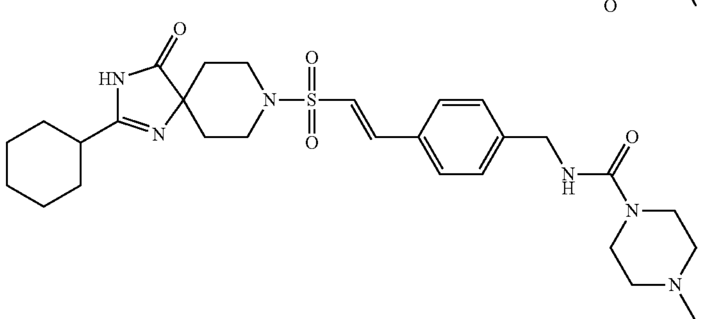 | LCMS-C-1 | 2.28 | 555 (M − H)− |

TABLE 79-continued

| Target Compound | Structure | LCMS condition | Retention time (min) | MS (m/z) |
|---|---|---|---|---|
| 568 | 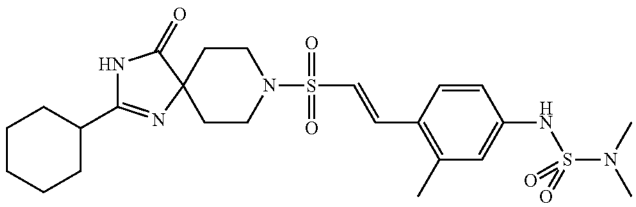 [SMILES: Cc1cc(NS(=O)(=O)N(C)C)ccc1/C=C/S(=O)(=O)N1CCC2(CC1)N=C(C1CCCCC1)NC2=O] | LCMS-C-1 | 2.43 | 538 (M + H)+ |
| 569 | 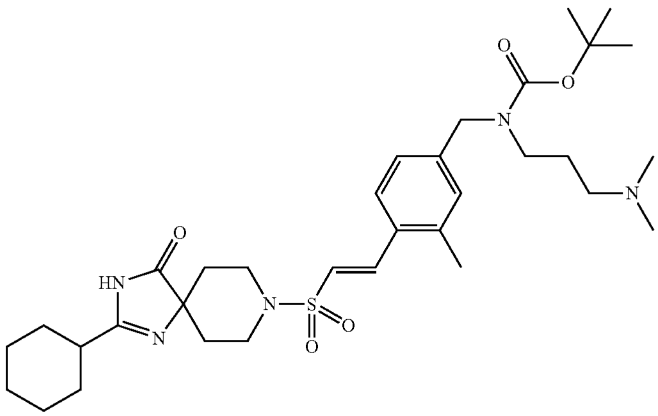 [SMILES: Cc1cc(CN(CCCN(C)C)C(=O)OC(C)(C)C)ccc1/C=C/S(=O)(=O)N1CCC2(CC1)N=C(C1CCCCC1)NC2=O] | LCMS-C-1 | 2.8 | 628 (M − H)− |
| 570 | 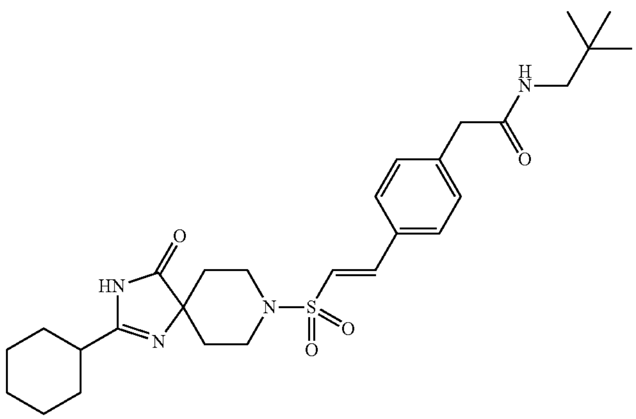 [SMILES: CC(C)(C)CNC(=O)Cc1ccc(/C=C/S(=O)(=O)N2CCC3(CC2)N=C(C2CCCCC2)NC3=O)cc1] | LCMS-C-1 | 2.6 | 527 (M − H)− |
| 571 | 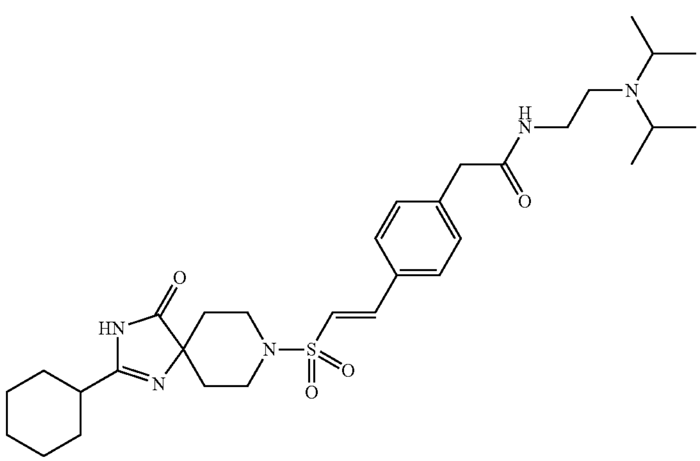 [SMILES: CC(C)N(CCNC(=O)Cc1ccc(/C=C/S(=O)(=O)N2CCC3(CC2)N=C(C2CCCCC2)NC3=O)cc1)C(C)C] | LCMS-C-1 | 2.17 | 584 (M − H)− |

TABLE 79-continued

| Target Compound | Structure | LCMS condition | Retention time (min) | MS (m/z) |
|---|---|---|---|---|
| 572 | 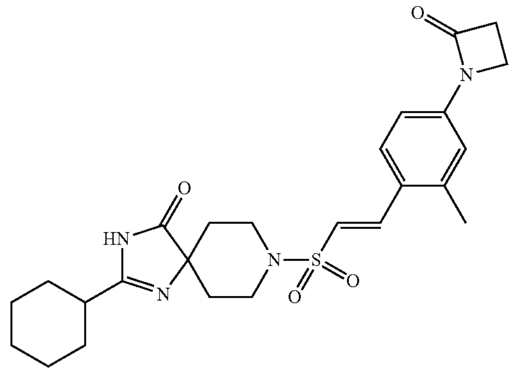 [SMILES: Cc1cc(N2CCC2=O)ccc1/C=C/S(=O)(=O)N1CCC2(CC1)N=C(C1CCCCC1)NC2=O] | LCMS-C-1 | 2.47 | 485 (M + H)+ |
| 573 | 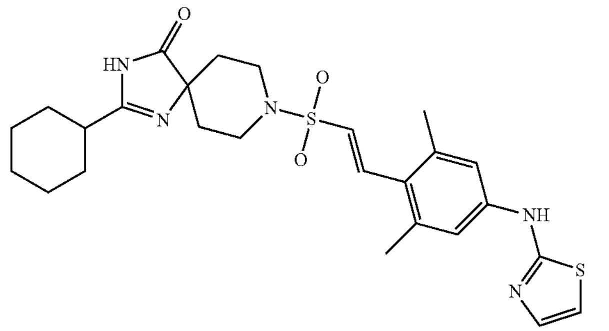 [SMILES: Cc1cc(Nc2nccs2)cc(C)c1/C=C/S(O)(O)N1CCC2(CC1)N=C(C1CCCCC1)NC2=O] | LCMS-D-1 | 2.82 | 528 (M + H)+ |
| 574 | 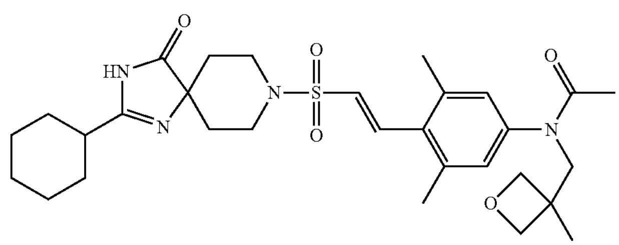 [SMILES: CC(=O)N(CC1(C)COC1)c1cc(C)c(/C=C/S(=O)(=O)N2CCC3(CC2)N=C(C2CCCCC2)NC3=O)c(C)c1] | LCMS-D-1 | 2.82 | 571 (M + H)+ |

The aryl bromide reagent used in the synthesis of Compound 567 (4-methyl-piperazine-1-carboxylic acid 4-bromo-benzylamide) was synthesized as follows.

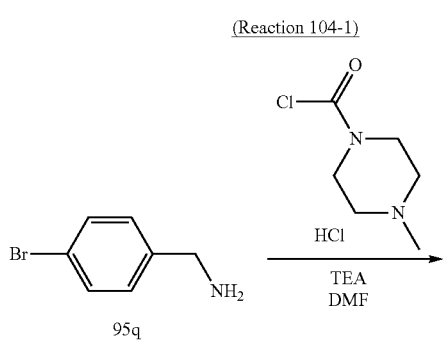

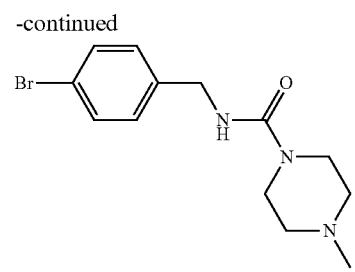

4-Methyl-piperazine-1-carboxylic acid 4-bromo-benzylamide was synthesized by operations similar to those in Reaction 82-1 using appropriate reagents and starting material.

MS (ESI) m/z=312 (M+H)+.

The aryl bromide reagent used in the synthesis of Compound 568 (N'-(4-bromo-3-methyl-phenyl)-N,N-dimethylsulfamide) was synthesized as follows.

(Reaction 104-2)

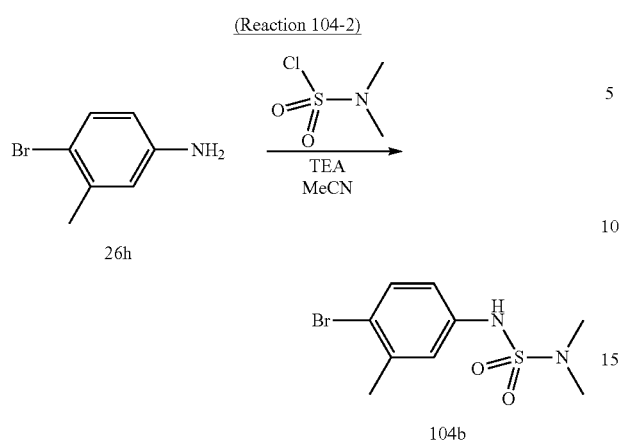

N'-(4-Bromo-3-methyl-phenyl)-N,N-dimethyl-sulfamide was synthesized by operations similar to those in Reaction 82-1 using appropriate reagents and starting material.

MS (ESI) m/z=293 (M+H)+.

The aryl bromide reagent used in the synthesis of Compound 569 ((4-bromo-3-methyl-benzyl)-(3-dimethylamino-propyl)-carbamic acid tert-butyl ester) was synthesized as follows.

(Reaction 104-3)

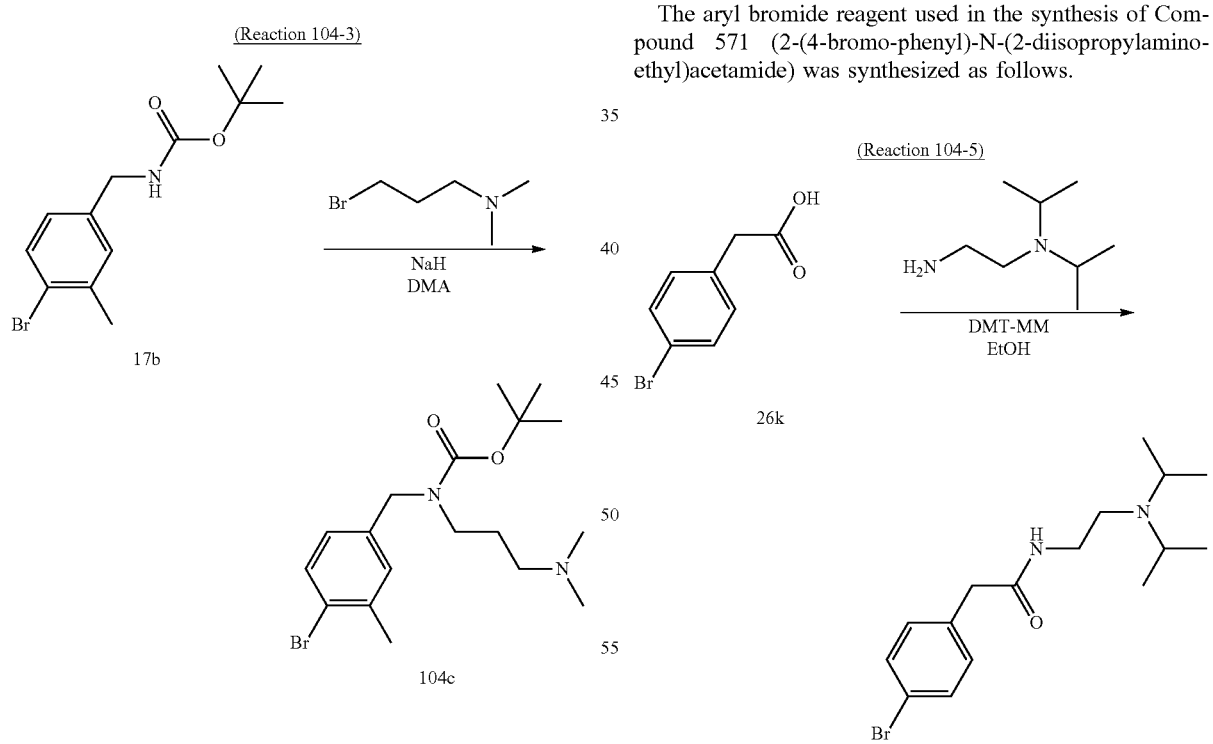

(4-Bromo-3-methyl-benzyl)-(3-dimethylamino-propyl)-carbamic acid tert-butyl ester was synthesized by operations similar to those in Reaction 25-3 using appropriate reagents and starting material.

MS (ESI) m/z=385, 387 (M+H)+.

The aryl bromide reagent used in the synthesis of Compound 570 (2-(4-bromo-phenyl)-N-(2,2-dimethyl-propyl)-acetamide) was synthesized as follows.

(Reaction 104-4)

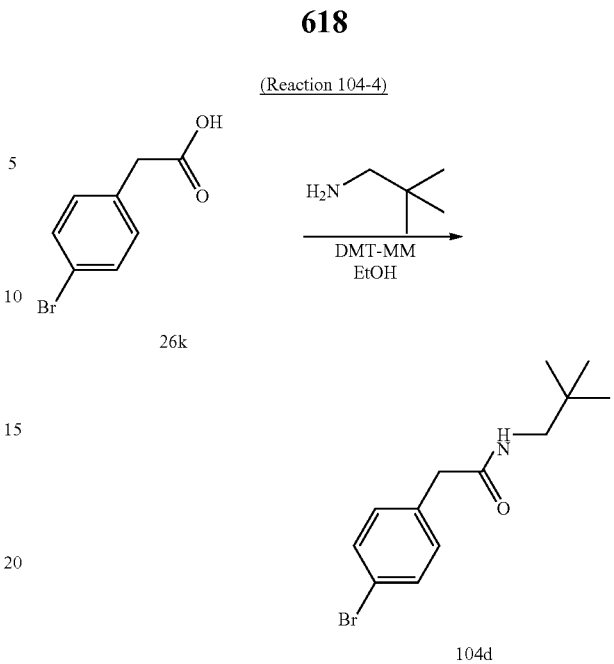

2-(4-Bromo-phenyl)-N-(2,2-dimethyl-propyl)-acetamide was synthesized by operations similar to those in Reaction 10-1 using appropriate reagents and starting material.

MS (ESI) m/z=285, 287 (M+H)+.

The aryl bromide reagent used in the synthesis of Compound 571 (2-(4-bromo-phenyl)-N-(2-diisopropylamino-ethyl)acetamide) was synthesized as follows.

(Reaction 104-5)

2-(4-Bromo-phenyl)-N-(2-diisopropylamino-ethyl)acetamide was synthesized by operations similar to those in Reaction 10-1 using appropriate reagents and starting material.

MS (ESI) m/z=342, 344 (M+H)+.

The aryl bromide reagent used in the synthesis of Compound 572 (1-(4-bromo-3-methyl-phenyl)-azetidin-2-one) was synthesized as follows.

(Reaction 104-6)

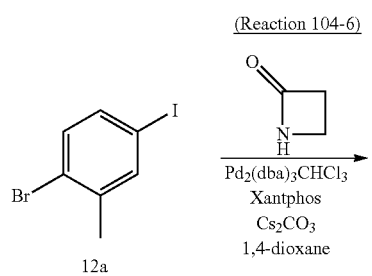

1-(4-Bromo-3-methyl-phenyl)-azetidin-2-one was synthesized by operations similar to those in Reaction 29-3 using appropriate reagents and starting material.

MS (ESI) m/z=240, 242 (M+H)+.

The aryl bromide reagent used in the synthesis of Compound 573 ((4-bromo-3,5-dimethyl-phenyl)-thiazol-2-yl-amine) was synthesized as follows.

(Reaction 104-7)

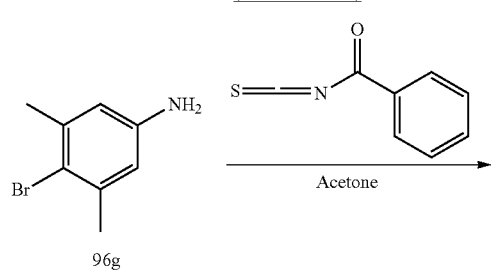

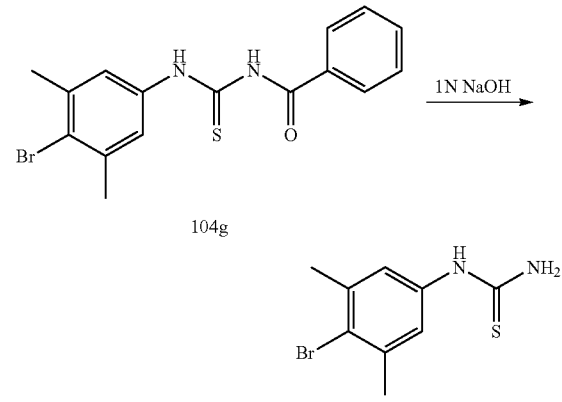

A solution of 4-bromo-3,5-dimethyl-phenylamine (200 mg) and benzoyl isothiocyanate (0.14 ml) in acetone (2 ml) was heated under reflux for 30 minutes. After cooling the reaction solution, a 1 N aqueous sodium hydroxide solution (2.19 ml) was added and the mixture was stirred at 50° C. for 12 hours. The mixture was extracted with dichloromethane, and the organic layer was then dried over anhydrous sodium sulfate and concentrated under reduced pressure. The resulting residue was triturated with hexane to give (4-bromo-3,5-dimethyl-phenyl)-thiourea (146 mg, 57%).

$^1$H-NMR (300 MHz, DMSO-d6) δ 9.62 (1H, s), 7.8-7.2 (2H, br), 7.19 (2H, s), 2.32 (6H, s).

(Reaction 104-8)

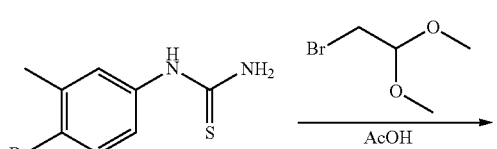

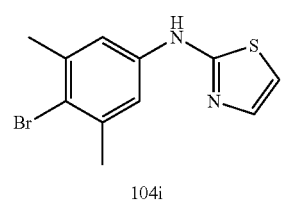

(4-Bromo-3,5-dimethyl-phenyl)-thiazol-2-yl-amine was synthesized by operations similar to those in Reaction 94-1 using appropriate reagents and starting material.

MS (ESI) m/z=285 (M+H)+.

The aryl bromide reagent used in the synthesis of Compound 574 (N-(4-bromo-3,5-dimethyl-phenyl)-N-(3-methyl-oxetan-3-ylmethyl)-acetamide) was synthesized as follows.

(Reaction 104-9)

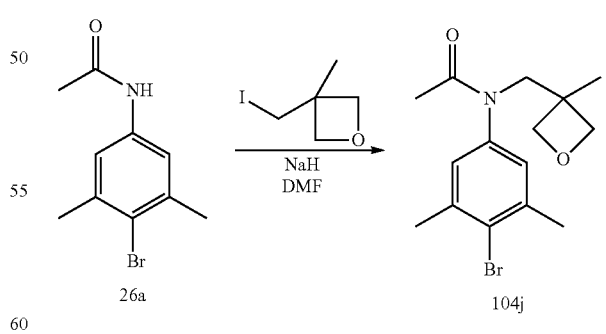

N-(4-Bromo-3,5-dimethyl-phenyl)-N-(3-methyl-oxetan-3-ylmethyl)-acetamide was synthesized by operations similar to those in Reaction 25-3 using appropriate reagents and starting material.

MS (ESI) m/z=326, 328 (M+H)+.

Example 105

3-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione (Compound 575)

(Reaction 105-1)

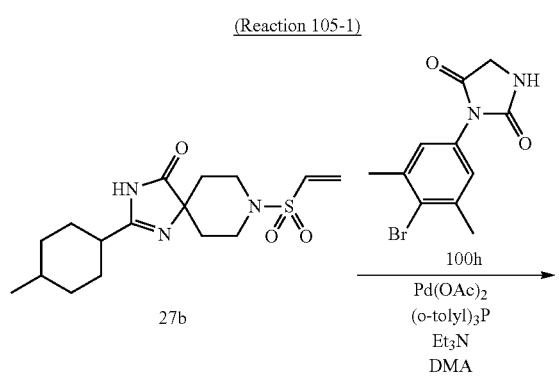

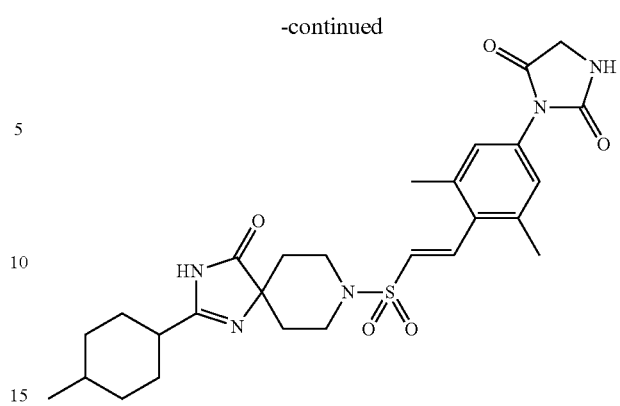

Compound 575

3-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-imidazolidine-2,4-dione was synthesized by operations similar to those in Reaction 26-1 using appropriate reagents and starting material.

MS (ESI) m/z=542 (M+H)+.

The example compounds shown below were synthesized by operations similar to those in Example 105 using appropriate reagents and starting materials.

Compounds 576 to Compound 589

TABLE 80

| Target Compound | Structure | LCMS condition | Retention time (min) | MS (m/z) |
|---|---|---|---|---|
| 576 | 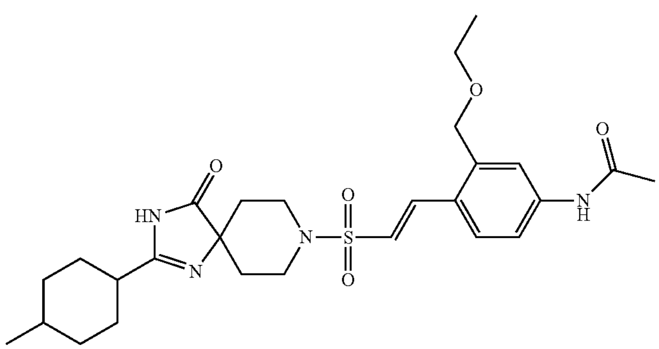 [SMILES: CCOCc1cc(NC(C)=O)ccc1/C=C/S(=O)(=O)N1CCC2(CC1)N=C(C1CCC(C)CC1)NC2=O] | LCMS-D-1 | 2.82 | 531 (M + H)+ |
| 577 | 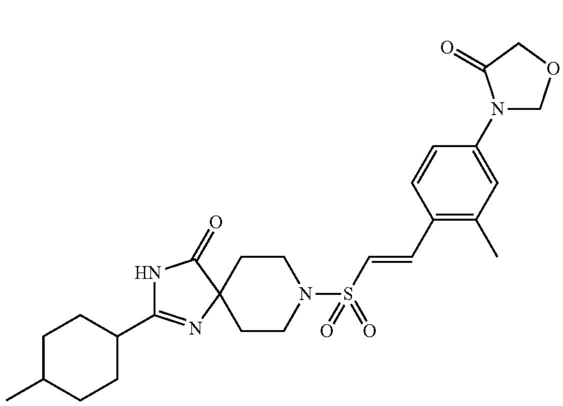 [SMILES: Cc1cc(N2COCC2=O)ccc1/C=C/S(=O)(=O)N1CCC2(CC1)N=C(C1CCC(C)CC1)NC2=O] | LCMS-C-1 | 2.62 | 515 (M + H)+ |

TABLE 80-continued
| Target Compound | Structure | LCMS condition | Retention time (min) | MS (m/z) |
|---|---|---|---|---|
| 578 | 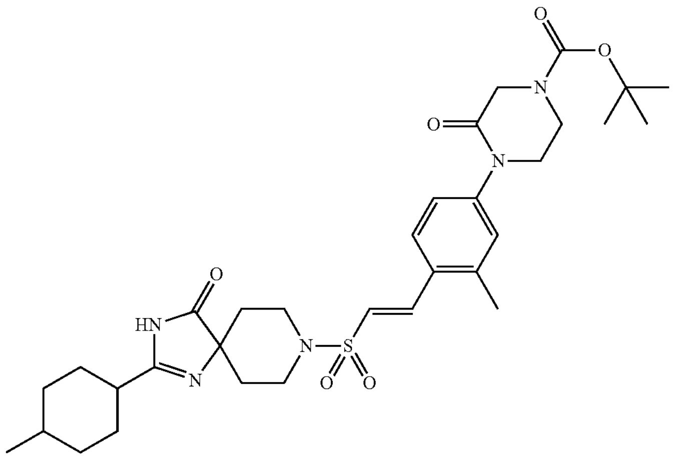 [SMILES: Cc1cc(N2CCN(C(=O)OC(C)(C)C)CC2=O)ccc1/C=C/S(=O)(=O)N1CCC2(CC1)N=C(C1CCC(C)CC1)NC2=O] | LCMS-A-1 | 2.44 | 628 (M + H)+ |
| 579 | 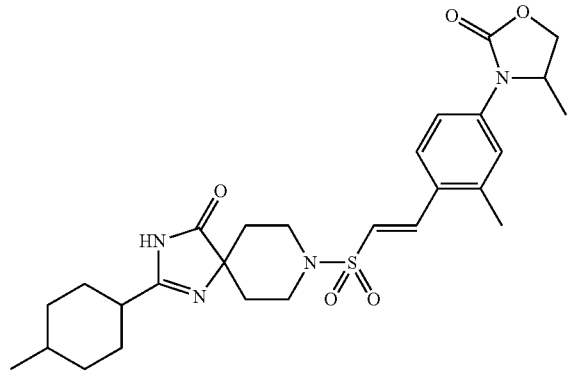 | LCMS-A-1 | 2.23 | 529 (M + H)+ |
| 580 | 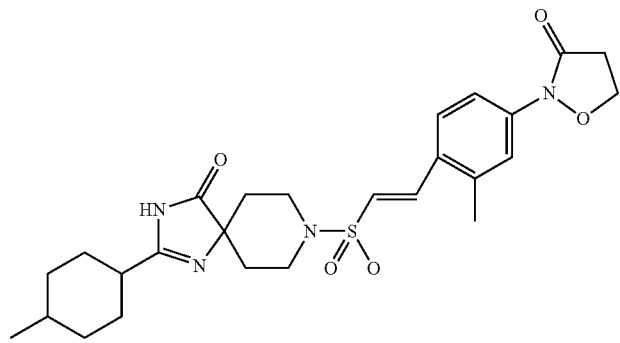 | LCMS-C-1 | 2.72 | 515 (M + H)+ |
| 581 | 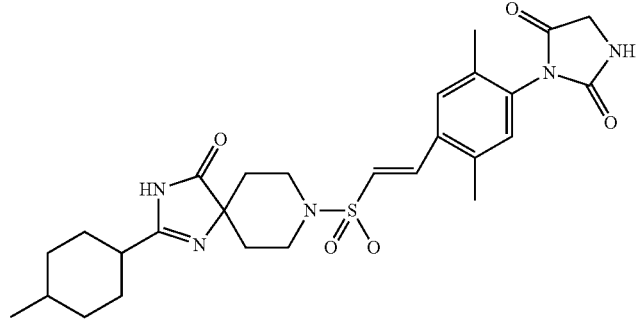 | LCMS-C-1 | 2.42 | 542 (M + H)+ |

TABLE 80-continued

| Target Compound | Structure | LCMS condition | Retention time (min) | MS (m/z) |
|---|---|---|---|---|
| 582 | 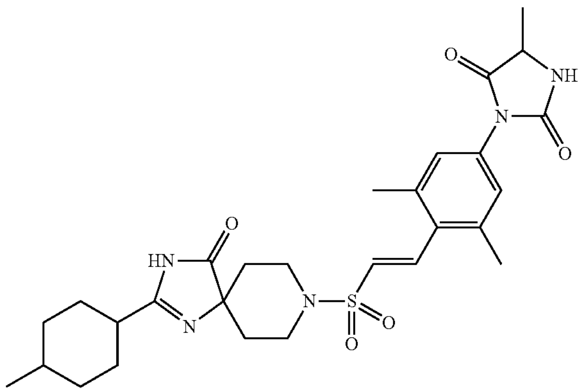 [SMILES: Cc1cc(N2C(=O)NC(C)C2=O)cc(C)c1/C=C/S(=O)(=O)N1CCC2(CC1)N=C(C1CCC(C)CC1)NC2=O] | LCMS-A-1 | 2.05 | 556 (M + H)+ |
| 583 | 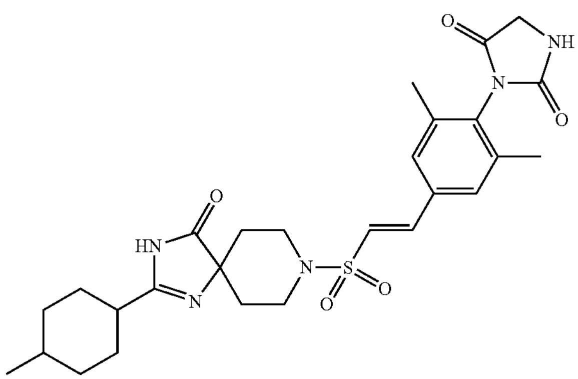 [SMILES: Cc1cc(/C=C/S(=O)(=O)N2CCC3(CC2)N=C(C2CCC(C)CC2)NC3=O)cc(C)c1N1C(=O)CNC1=O] | LCMS-A-1 | 1.95 | 542 (M + H)+ |
| 584 | 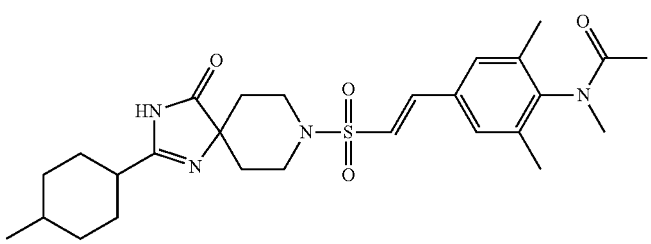 [SMILES: CC(=O)N(C)c1c(C)cc(/C=C/S(=O)(=O)N2CCC3(CC2)N=C(C2CCC(C)CC2)NC3=O)cc1C] | LCMS-D-1 | 1.93 | 515 (M + H)+ |
| 585 | 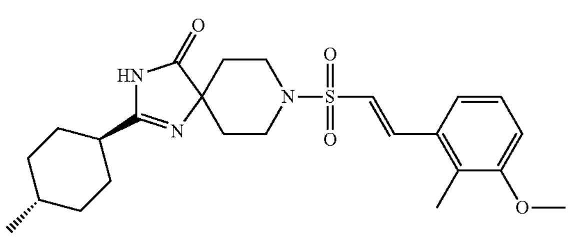 | LCMS-F-1 | 1.05 | 460 (M + H)+ |

… TABLE 80-continued

| Target Compound | Structure | LCMS condition | Retention time (min) | MS (m/z) |
|---|---|---|---|---|
| 586 | 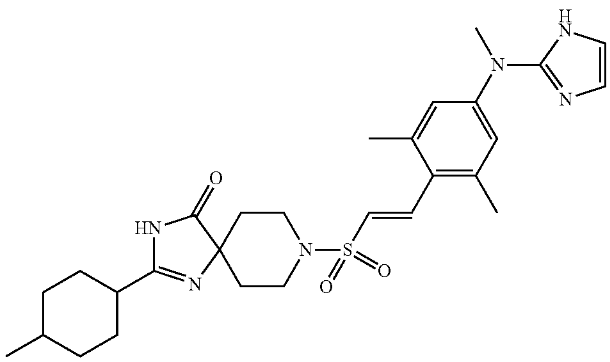 [SMILES: Cc1cc(N(C)c2ncc[nH]2)cc(C)c1/C=C/S(=O)(=O)N1CCC2(CC1)N=C(C1CCC(C)CC1)NC2=O] | LCMS-A-1 | 1.83 | 539 (M + H)+ |
| 587 | 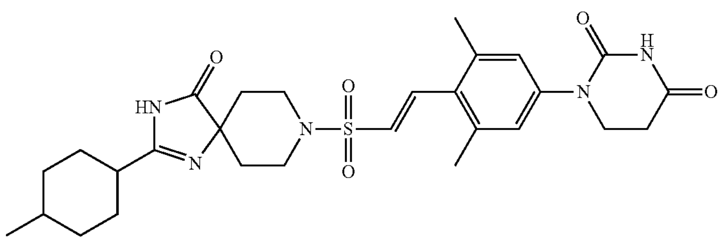 | LCMS-D-1 | 2.02 | 556 (M + H)+ |
| 588 | 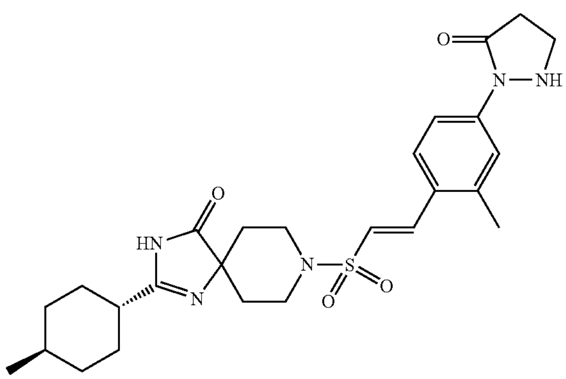 [SMILES: Cc1cc(N2NCCC2=O)ccc1/C=C/S(=O)(=O)N1CCC2(CC1)N=C([C@H]1CC[C@H](C)CC1)NC2=O] | LCMS-C-1 | 2.53 | 515 (M + H)+ |
| 589 | 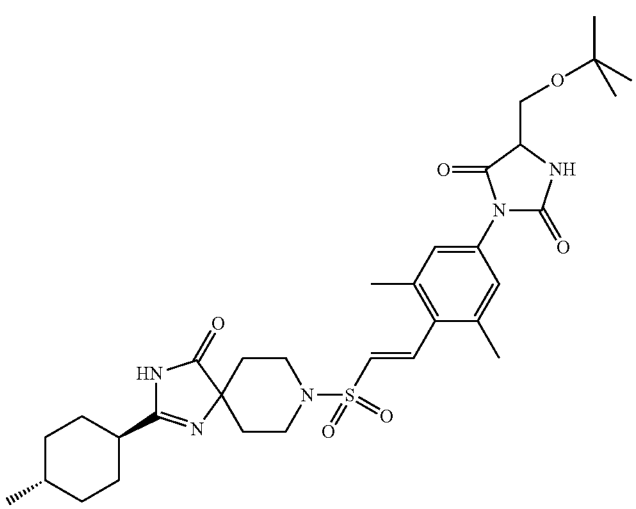 [SMILES: Cc1cc(N2C(=O)NC(COC(C)(C)C)C2=O)cc(C)c1/C=C/S(=O)(=O)N1CCC2(CC1)N=C([C@H]1CC[C@H](C)CC1)NC2=O] | LCMS-C-1 | 2.83 | 628 (M + H)+ |

The aryl bromide reagent used in the synthesis of Compound 577 (3-(4-bromo-3-methyl-phenyl)-oxazolidin-4-one) was synthesized as follows.

(Reaction 105-2)

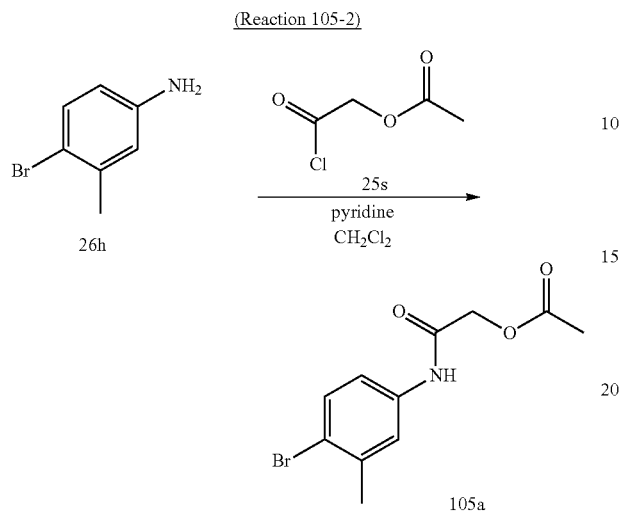

Acetic acid chlorocarbonylmethyl ester (1.73 ml) was added to a solution of 4-bromo-3-methyl-phenylamine (2.0 g, 10.7 mmol) and pyridine (5.21 ml) in dichloromethane (20 ml), and the mixture was stirred at 40° C. for 2.5 hours. The mixture was cooled, and then quenched with water and extracted with dichloromethane. The organic layer was sequentially washed with water and saturated brine, and then dried over anhydrous sodium sulfate and concentrated under reduced pressure to give acetic acid (4-bromo-3-methyl-phenylcarbamoyl)-methyl ester (3.19 g).

$^1$H-NMR (400 MHz, CDCl$_3$) δ 2.24 (3H, s), 2.39 (3H, s), 4.68 (2H, s), 7.22-7.25 (1H, m), 7.46-7.50 (2H, m), 7.70 (1H, brs).

(Reaction 105-3)

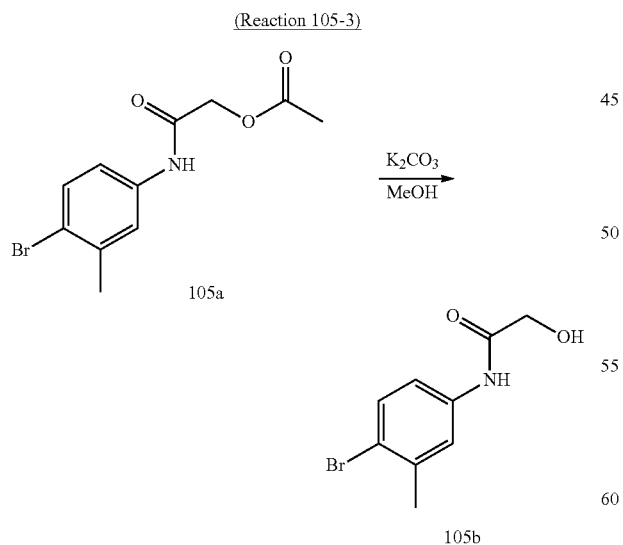

N-(4-Bromo-3-methyl-phenyl)-2-hydroxy-acetamide was synthesized by operations similar to those in Reaction 12-5 using appropriate reagents and starting material.
MS (ESI) m/z=244, 246 (M+H)+.

(Reaction 105-4)

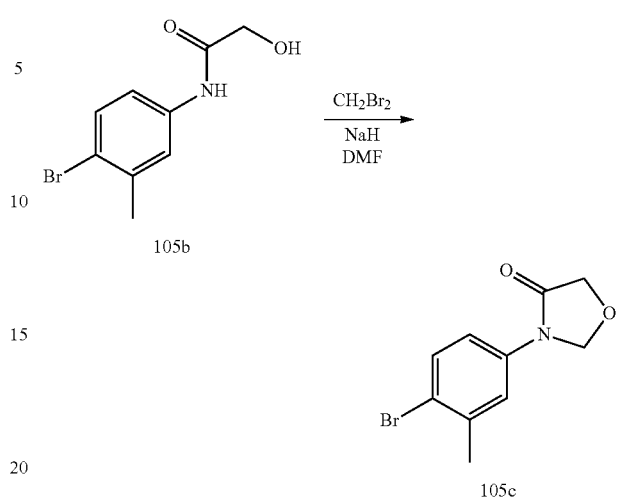

Sodium hydride (81 mg, 1.80 mmol) was added to a solution of N-(4-bromo-3-methyl-phenyl)-2-hydroxy-acetamide (200 mg, 0.819 mmol) in DMF (4.0 ml), and the mixture was stirred at room temperature for 50 minutes. Further, dibromomethane (0.114 ml, 1.64 mmol) was added to the reaction solution, and the mixture was heated with stirring at 110° C. for two hours. Cooling to room temperature and subsequent purification by silica gel column chromatography (hexane-ethyl acetate) gave 3-(4-bromo-3-methyl-phenyl)-oxazolidin-4-one (45 mg, 21%).
MS (ESI) m/z=256, 258 (M+H)+.

The aryl bromide reagent used in the synthesis of Compound 578 (4-(4-bromo-3-methyl-phenyl)-3-oxo-piperazine-1-carboxylic acid tert-butyl ester) was synthesized as follows.

(Reaction 105-5)

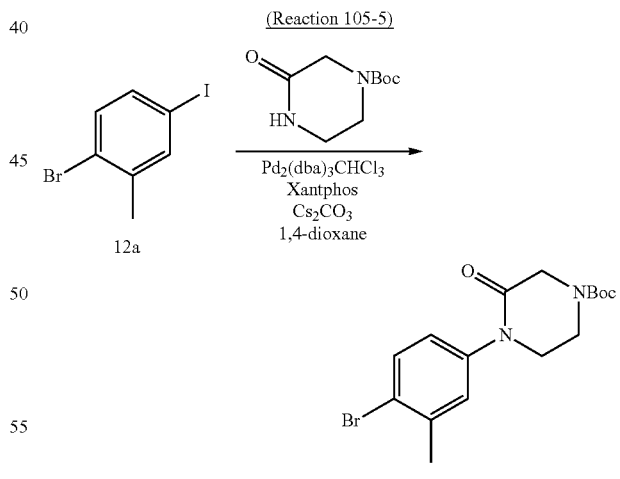

4-(4-Bromo-3-methyl-phenyl)-3-oxo-piperazine-1-carboxylic acid tert-butyl ester was synthesized by operations similar to those in Reaction 29-3 using appropriate reagents and starting material.
MS (ESI) m/z=369, 371 (M+H)+.

The aryl bromide reagent used in the synthesis of Compound 579 (3-(4-bromo-3-methyl-phenyl)-4-methyl-oxazolidin-2-one) was synthesized as follows.

(Reaction 105-6)

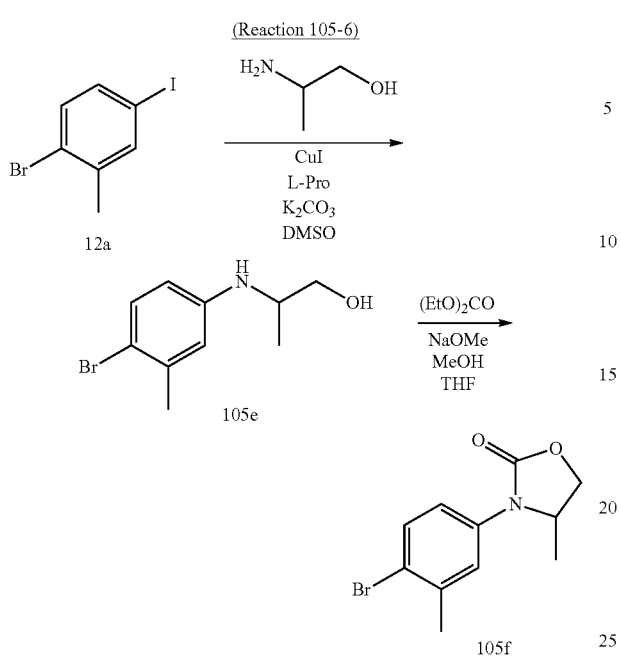

3-(4-Bromo-3-methyl-phenyl)-4-methyl-oxazolidin-2-one was synthesized by operations similar to those in Reaction 12-1 and Reaction 96-13 using appropriate reagents and starting material.

MS (ESI) m/z=270, 272 (M+H)+.

The aryl bromide reagent used in the synthesis of Compound 580 (2-(4-bromo-3-methyl-phenyl)-isoxazolidin-3-one) was synthesized as follows.

(Reaction 105-7)

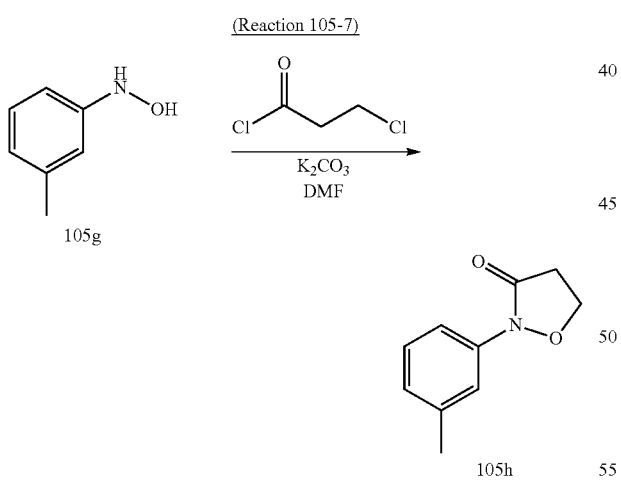

3-Chloro-propionyl (157 μL, 1.65 mmol) was added to a mixture of N-m-tolyl-hydroxylamine (235 mg, 1.69 mmol) and potassium carbonate (223 mg, 1.69 mmol) in N,N-dimethylformamide (1.7 mL) at −10° C. The mixture was stirred at room temperature for 2.5 hours, and water and ethyl acetate were then added. The organic layer and the aqueous layer were separated, and the aqueous layer was repeatedly extracted with ethyl acetate three times. The organic layers were combined, washed with water twice and saturated brine, and then concentrated under reduced pressure. The resulting residue was purified by silica gel column chromatography to give 2-m-tolyl-isoxazolidin-3-one as a pale yellow solid (213 mg, 73%).

MS (ESI) m/z=178 (M+H)+.

(Reaction 105-8)

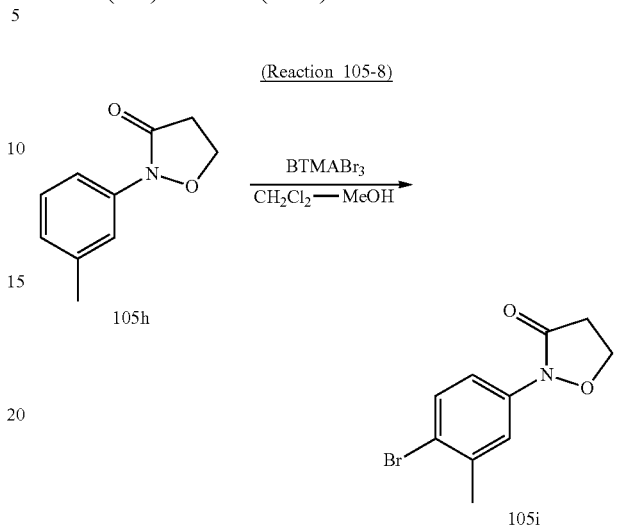

2-(4-Bromo-3-methyl-phenyl)-isoxazolidin-3-one was synthesized by operations similar to those in Reaction 26-2 using appropriate reagents and starting material.

MS (ESI) m/z=297, 299 (M+H)+.

The aryl iodide reagent used in the synthesis of Compound 581 (3-(4-iodo-2,5-dimethyl-phenyl)-imidazolidine-2,4-dione) was synthesized as follows.

(Reacton 105-9)

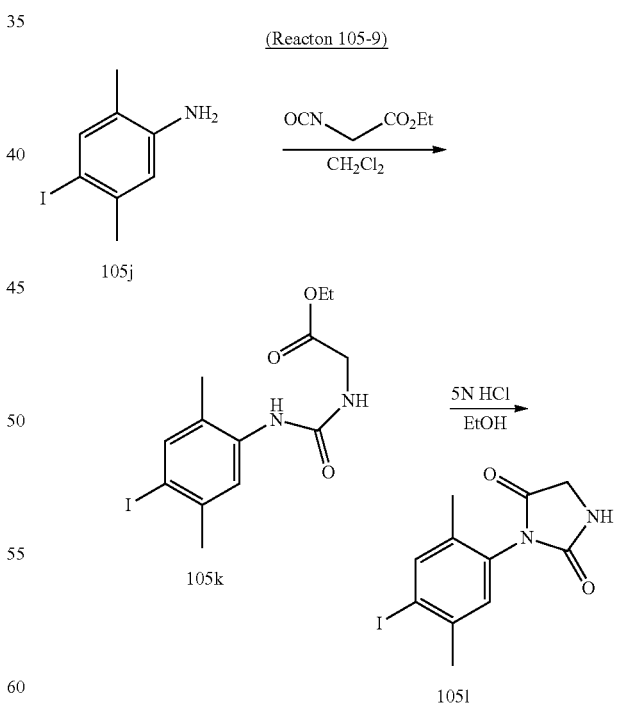

3-(4-Iodo-2,5-dimethyl-phenyl)-imidazolidine-2,4-dione was synthesized by operations similar to those in Reaction 84-1 and Reaction 96-1 using appropriate reagents and starting material.

MS (ESI) m/z=331 (M+H)+.

The aryl bromide reagent used in the synthesis of Compound 582 (3-(4-bromo-3,5-dimethyl-phenyl)-5-methyl-imidazolidine-2,4-dione) was synthesized as follows.

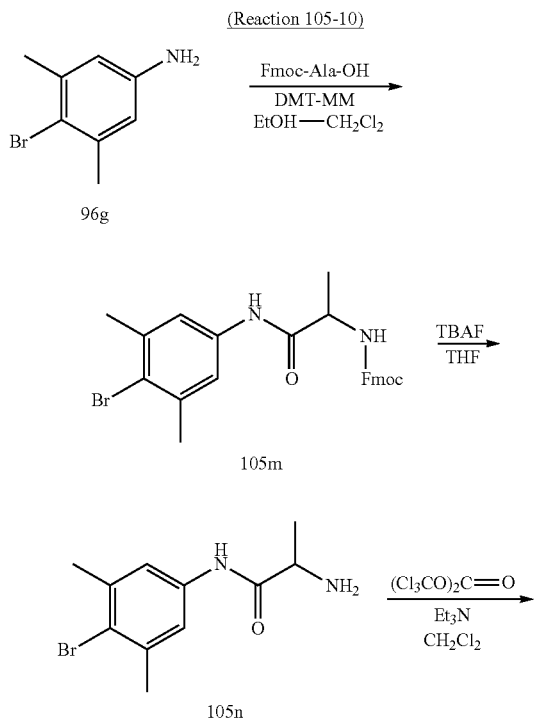

3-(4-Bromo-3,5-dimethyl-phenyl)-5-methyl-imidazolidine-2,4-dione was synthesized by operations similar to those in Reaction 10-1, Reaction 39-2 and Reaction 96-10 using appropriate reagents and starting material.

MS (ESI) m/z=297, 299 (M+H)+.

The aryl bromide reagent used in the synthesis of Compound 583 (3-(4-bromo-2,6-dimethyl-phenyl)-imidazolidine-2,4-dione) was synthesized as follows.

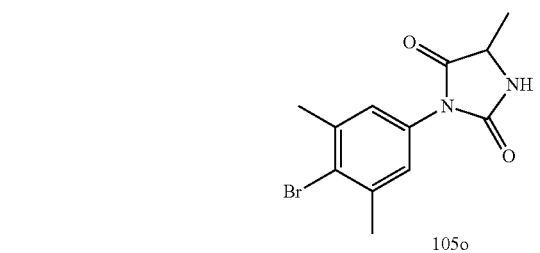

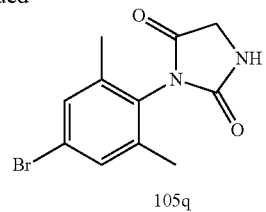

Ethyl isocyanatoacetate (581 mg, 4.50 mmol) and N,N-diisopropylethylamine (426 mg, 1.65 mmol) were added to a solution of 4-bromo-2,6-dimethylaniline (600 mg, 3.00 mmol) in toluene (6 ml) with stirring in a nitrogen stream, and the mixture was heated with stirring at 120° C. After 30 minutes, the reaction solution was brought to room temperature, and the precipitate was collected by filtration, washed with toluene and then dried under reduced pressure. The resulting solid was suspended in toluene (6 ml). DBU (68.4 mg, 2.25 mmol) was added and the mixture was heated with stirring at 120° C. After 30 minutes, the reaction solution was brought to room temperature and diluted with ethyl acetate, and the organic layer was washed with a 1 N aqueous hydrochloric acid solution and saturated brine. The organic layer was dried over anhydrous magnesium sulfate, and the magnesium sulfate was then removed by filtration. The filtrate was concentrated under reduced pressure. The residue was subjected to column chromatography (hexane-ethyl acetate) to give 3-(4-bromo-2,6-dimethyl-phenyl)-imidazolidine-2,4-dione (570 mg, 67%).

MS (ESI) m/z=283, 285 (M+H)+.

The aryl bromide reagent used in the synthesis of Compound 584 (N-(4-bromo-2,6-dimethyl-phenyl)-N-methyl-acetamide) was synthesized as follows.

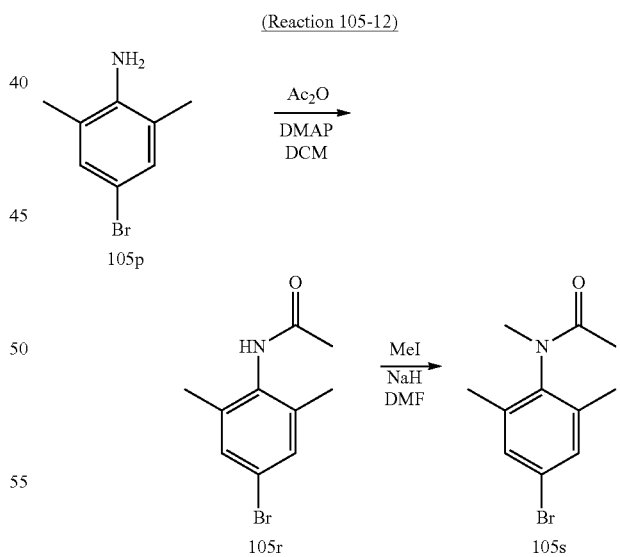

N-(4-Bromo-2,6-dimethyl-phenyl)-N-methyl-acetamide was synthesized by operations similar to those in Reaction 19-2 (using DMAP as a base) and Reaction 25-3 using appropriate reagents and starting material.

MS (ESI) m/z=256, 258 (M+H)+.

The aryl bromide reagent used in the synthesis of Compound 586 ((4-bromo-3,5-dimethyl-phenyl)-(1H-imidazol-2-yl)-methyl-amine) was synthesized as follows.

(Reaction 105-13)

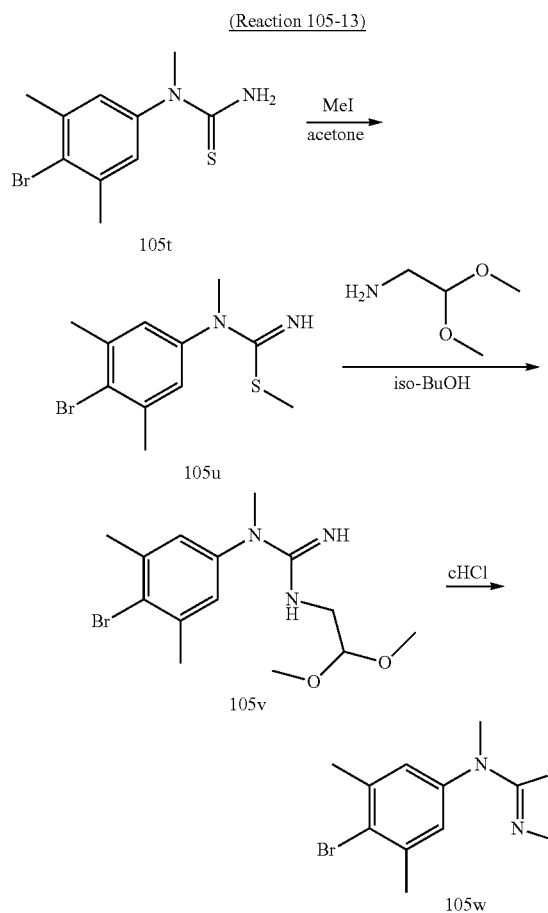

Iodomethane (260 mg, 9.15 mmol) was added to a solution of 1-(4-bromo-3,5-dimethyl-phenyl)-1-methyl-thiourea (500 mg, 1.83 mmol) in acetone (10 ml) with stirring in a nitrogen stream, and the mixture was heated with stirring at 50° C. for two hours. The reaction solution was concentrated under reduced pressure, and a mixture of the resulting residue and aminoacetaldehyde dimethylacetal (250 mg, 2.38 mmol) in iso-BuOH (8.3 ml) was then heated under reflux for four hours. The reaction mixture was concentrated under reduced pressure. Concentrated hydrochloric acid (3 ml) was then added to the resulting residue, and the mixture was heated with stirring at 90° C. for 30 minutes. The reaction mixture was cooled and then adjusted to pH 10 with a 2 N aqueous sodium hydroxide solution, followed by extraction with dichloromethane. The organic layer was dried over anhydrous magnesium sulfate and then concentrated under reduced pressure. The residue was purified by silica gel column chromatography (dichloromethane-methanol) to give (4-bromo-3,5-dimethyl-phenyl)-(1H-imidazol-2-yl)-methyl-amine (145 mg, 28%).

$^1$H-NMR (400 MHz, DMSO-d6) δ 2.30 (6H, s), 3.25 (3H, s), 6.71 (1H, s), 6.83 (2H, s), 6.87 (1H, s).

MS (ESI) m/z=280 (M+H)+.

The aryl bromide reagent used in the synthesis of Compound 587 (1-(4-bromo-3,5-dimethyl-phenyl)-dihydro-pyrimidine-2,4-dione) was synthesized as follows.

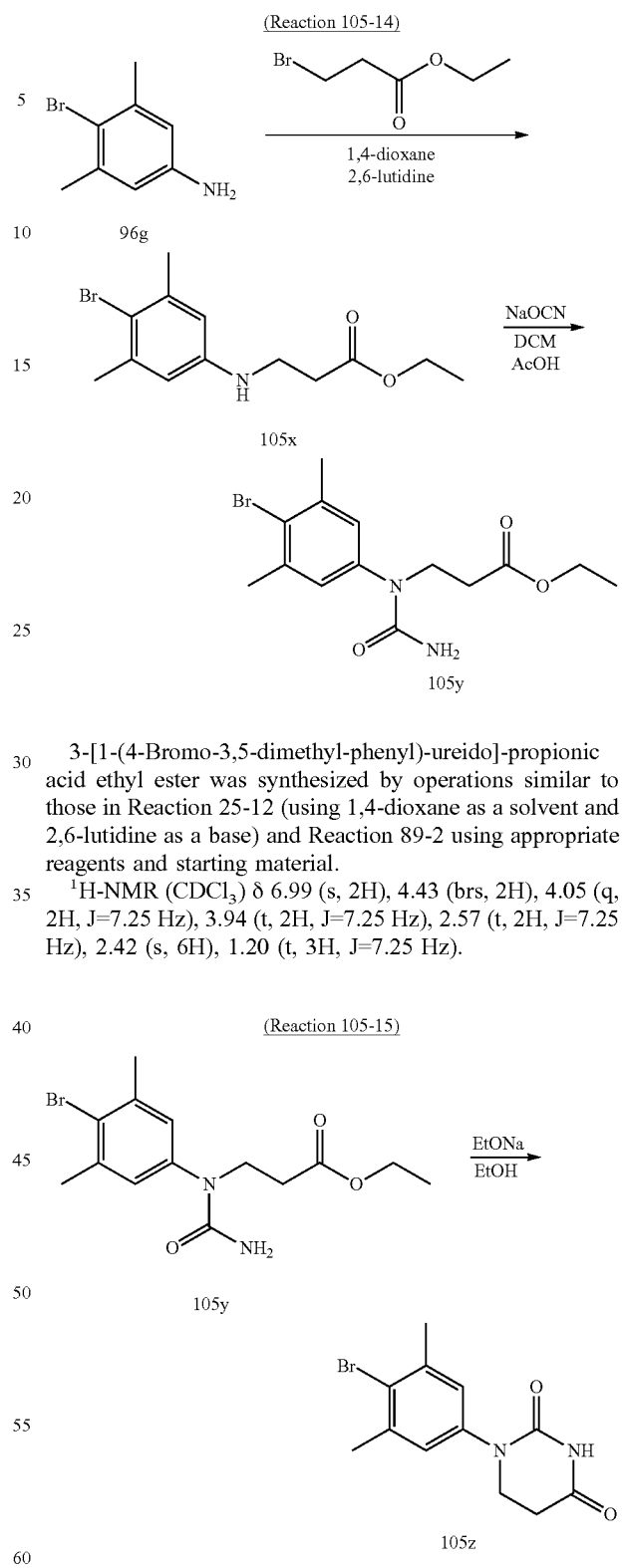

3-[1-(4-Bromo-3,5-dimethyl-phenyl)-ureido]-propionic acid ethyl ester was synthesized by operations similar to those in Reaction 25-12 (using 1,4-dioxane as a solvent and 2,6-lutidine as a base) and Reaction 89-2 using appropriate reagents and starting material.

$^1$H-NMR (CDCl$_3$) δ 6.99 (s, 2H), 4.43 (brs, 2H), 4.05 (q, 2H, J=7.25 Hz), 3.94 (t, 2H, J=7.25 Hz), 2.57 (t, 2H, J=7.25 Hz), 2.42 (s, 6H), 1.20 (t, 3H, J=7.25 Hz).

A solution of sodium ethoxide (15.7 mg, 0.033 mmol) in ethanol (0.1 ml) was added to a solution of 3-[1-(4-bromo-3,5-dimethyl-phenyl)-ureido]-propionic acid ethyl ester (11.4 mg, 0.033 mmol) in ethanol (0.9 ml), and the mixture was stirred at room temperature for 24 hours. The mixture was adjusted to pH 4 with 1 N hydrochloric acid and then extracted with dichloromethane. The organic layer was dried over anhydrous magnesium sulfate and then concentrated under reduced pressure. The resulting residue was purified by silica gel column chromatography (dichloromethane-ethyl acetate) to give 1-(4-bromo-3,5-dimethyl-phenyl)-di-hydro-pyrimidine-2,4-dione (9.8 mg, 99%).

$^1$H-NMR (CDCl$_3$) δ 7.59 (s, 1H), 7.03 (s, 2H), 3.83 (t, 2H, J=6.49 Hz), 2.83 (t, 2H, J=6.49 Hz), 2.42 (s, 6H).

The aryl bromide reagent used in the synthesis of Compound 588 (2-(4-bromo-3-methyl-phenyl)-pyrazolidin-3-one) was synthesized as follows.

(Reaction 105-16)

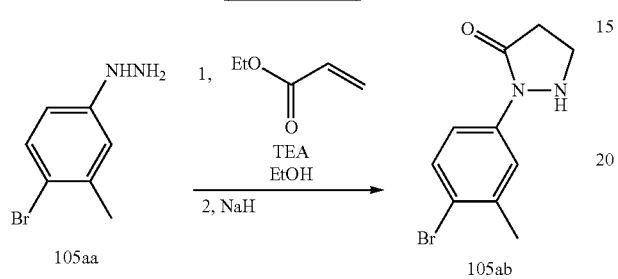

Triethylamine (625 μL, 13.1 mmol) and acrylic acid ethyl ester (1.82 mL, 5.74 mmol) were added to a solution of (4-bromo-3-methyl-phenyl)-hydrazine (1.05 g, 5.22 mmol) in EtOH (26.1 mL) at room temperature in a nitrogen atmosphere, and the mixture was stirred at 80° C. for 18 hours. The reaction solution was cooled, and 50% NaH (501 mg, 10.4 mmol) was then added to the reaction solution at 0° C. The mixture was stirred at 0° C. for 30 minutes, and 50% NaH (251 mg, 5.20 mmol) was then further added, followed by further stirring for 30 minutes. The reaction mixture was quenched with a saturated aqueous ammonium chloride solution and extracted with ethyl acetate three times. The organic layers were combined and washed with a mixed solution of water:saturated brine (1:1). After separation, the organic layer was dried over sodium sulfate and concentrated under reduced pressure. The resulting residue was purified by silica gel column chromatography (hexane-ethyl acetate) to give 2-(4-bromo-3-methyl-phenyl)-pyrazolidin-3-one as a brown form (684 mg, 60%).

MS (ESI) m/z=255, 257 (M+H)+.

The aryl bromide reagent used in the synthesis of Compound 589 (3-(4-bromo-3,5-dimethyl-phenyl)-5-tert-butoxymethyl-imidazolidine-2,4-dione) was synthesized as follows.

(Reaction 105-17)

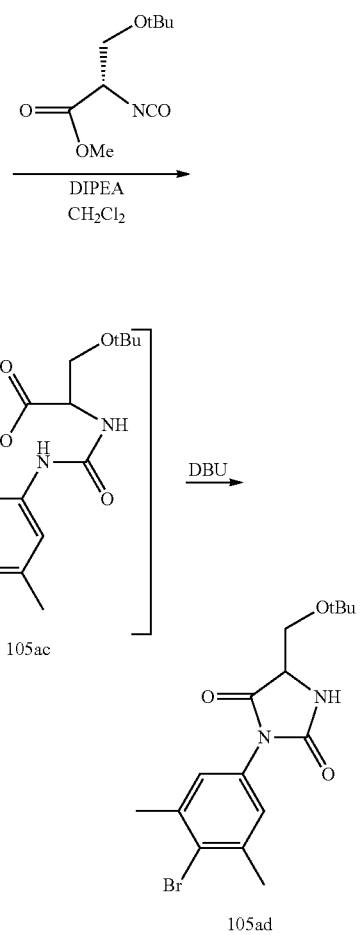

3-(4-Bromo-3,5-dimethyl-phenyl)-5-tert-butoxymethyl-imidazolidine-2,4-dione was synthesized by operations similar to those in Reaction 105-11 using appropriate reagents and starting material.

MS (ESI) m/z=367, 369 (M–H)–.

Example 106

N,N-Dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide (Compound 590)

(Reaction 106-1)

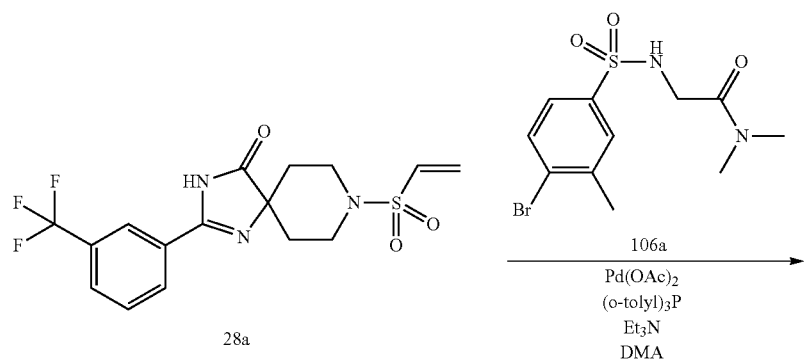

-continued

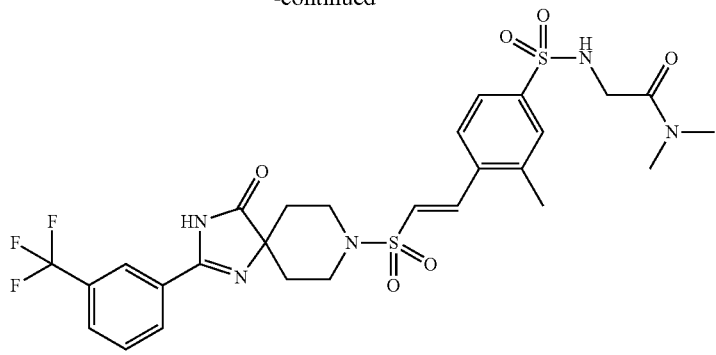

Compound 590

N,N-Dimethyl-2-(3-methyl-4-{(E)-2-[4-oxo-2-(3-trifluoromethyl-phenyl)-1,3,8-triaza-spiro[4.5]dec-1-ene-8-sulfonyl]-vinyl}-benzenesulfonylamino)-acetamide was synthesized by operations similar to those in Reaction 26-1 using appropriate reagents and starting material.

MS (ESI) m/z=642 (M+H)+.

The example compounds shown below were synthesized by operations similar to those in Example 106 using appropriate reagents and starting materials.

Compounds 591 to Compound 595

TABLE 81

| Target Compound | Structure | LCMS condition | Retention time (min) | MS (m/z) |
|---|---|---|---|---|
| 591 | 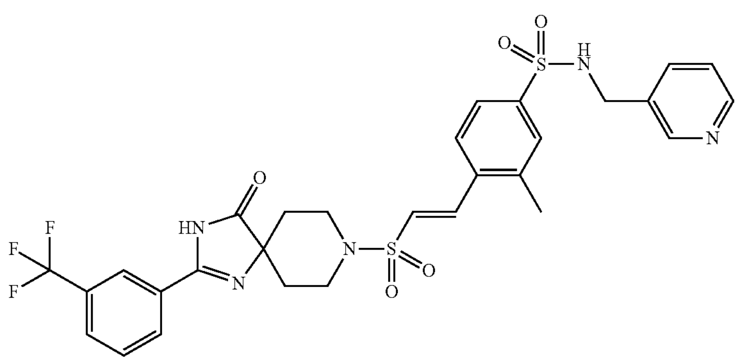 [SMILES: Cc1cc(S(=O)(=O)NCc2cccnc2)ccc1/C=C/S(=O)(=O)N1CCC2(CC1)N=C(c1cccc(C(F)(F)F)c1)NC2=O] | LCMS-C-1 | 2.57 | 648 (M + H)+ |
| 592 | 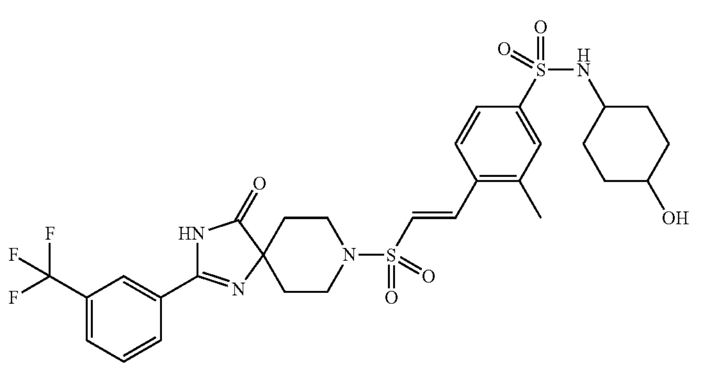 [SMILES: Cc1cc(S(=O)(=O)NC2CCC(O)CC2)ccc1/C=C/S(=O)(=O)N1CCC2(CC1)N=C(c1cccc(C(F)(F)F)c1)NC2=O] | LCMS-C-1 | 2.48 | 655 (M + H)+ |

TABLE 81-continued
| Target Compound | Structure | LCMS condition | Retention time (min) | MS (m/z) |
|---|---|---|---|---|
| 593 | 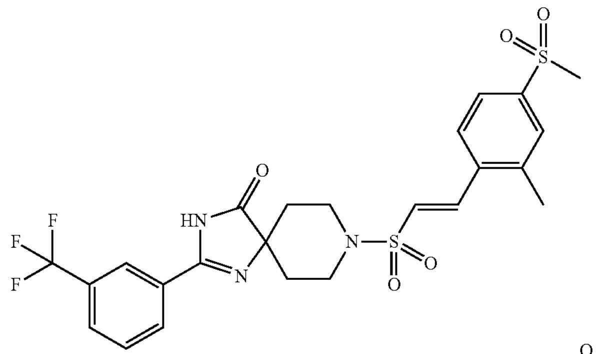 | LCMS-C-1 | 2.48 | 556 (M + H)+ |
| 594 | 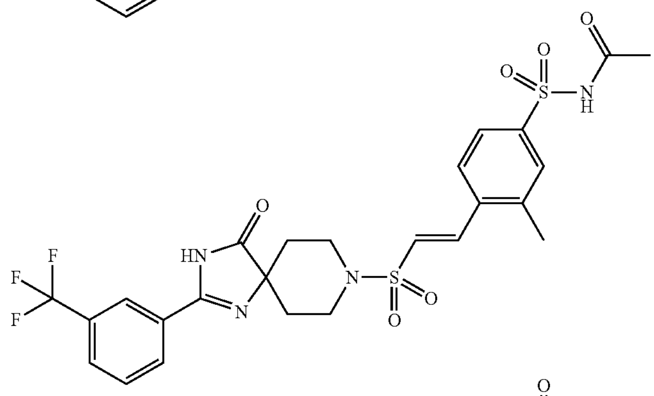 | LCMS-A-1 | 2.43 | 599 (M + H)+ |
| 595 | 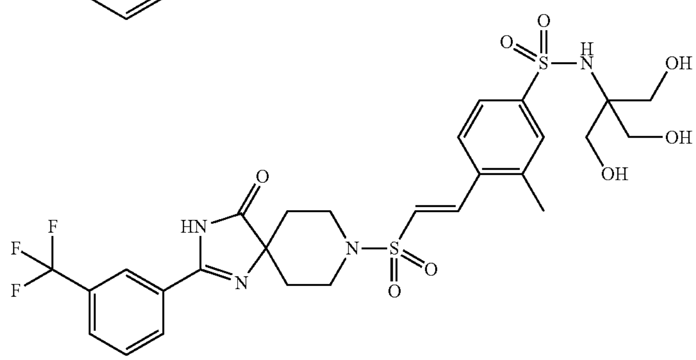 | LCMS-C-1 | 2.35 | 661 (M + H)+ |
The aryl bromide reagent used in the synthesis of Compound 590 (2-(4-bromo-3-methyl-benzenesulfonylamino)-N,N-dimethyl-acetamide) was synthesized as follows.
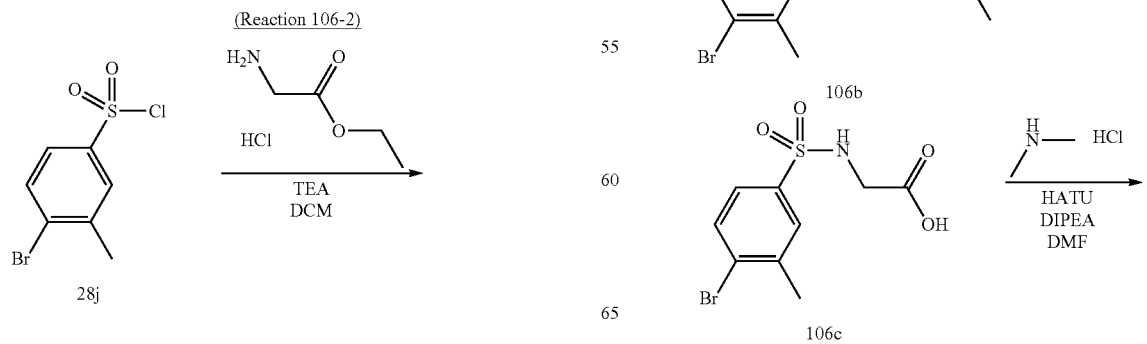

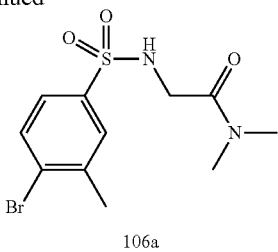

106a 2-(4-Bromo-3-methyl-benzenesulfonylamino)-N,N-dimethyl-acetamide was synthesized by operations similar to those in Reaction 5-4, Reaction 95-18 and Reaction 10-14 using appropriate reagents and starting material.

MS (ESI) m/z=335, 337 (M+H)+.

The aryl bromide reagent used in the synthesis of Compound 591 (4-bromo-3-methyl-N-pyridin-3-ylmethyl-benzenesulfonamide) was synthesized as follows.

(Reaction 106-3)

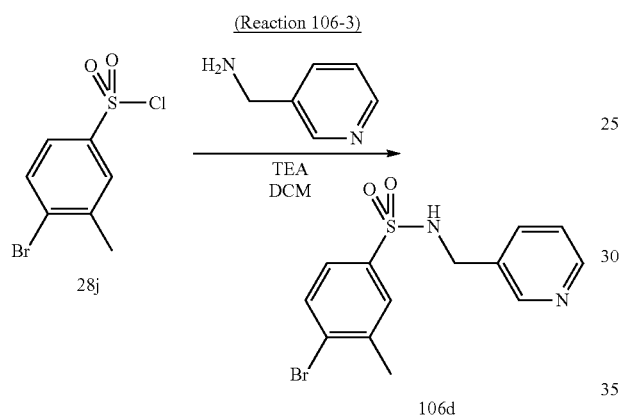

4-Bromo-3-methyl-N-pyridin-3-ylmethyl-benzenesulfonamide was synthesized by operations similar to those in Reaction 5-4 using appropriate reagents and starting material.

MS (ESI) m/z=341, 343 (M+H)+.

The aryl bromide reagent used in the synthesis of Compound 592 (4-bromo-N-(4-hydroxy-cyclohexyl)-3-methyl-benzenesulfonamide) was synthesized as follows.

(Reaction 106-4)

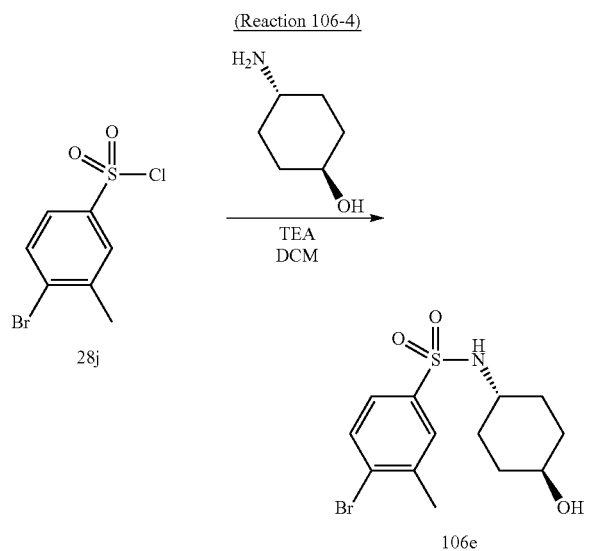

4-Bromo-N-(4-hydroxy-cyclohexyl)-3-methyl-benzenesulfonamide was synthesized by operations similar to those in Reaction 5-4 using appropriate reagents and starting material.

MS (ESI) m/z=348, 350 (M+H)+.

The aryl bromide reagent used in the synthesis of Compound 594 (N-acetyl-4-bromo-3-methyl-benzenesulfonamide) was synthesized as follows.

(Reaction 106-5)

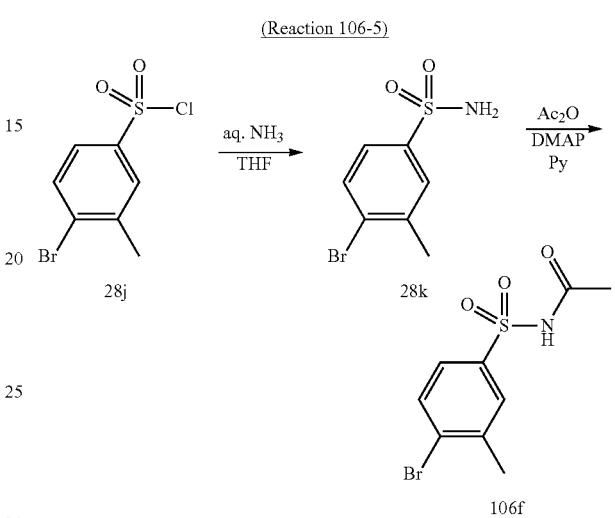

N-Acetyl-4-bromo-3-methyl-benzenesulfonamide was synthesized by operations similar to those in Reaction 95-6 and Reaction 12-2 using appropriate reagents and starting material.

MS (ESI) m/z=292, 294 (M+H)+.

The aryl bromide reagent used in the synthesis of Compound 595 (4-bromo-N-(2-hydroxy-1,1-bis-hydroxymethyl-ethyl)-3-methyl-benzenesulfonamide) was synthesized as follows.

(Reaction 106-6)

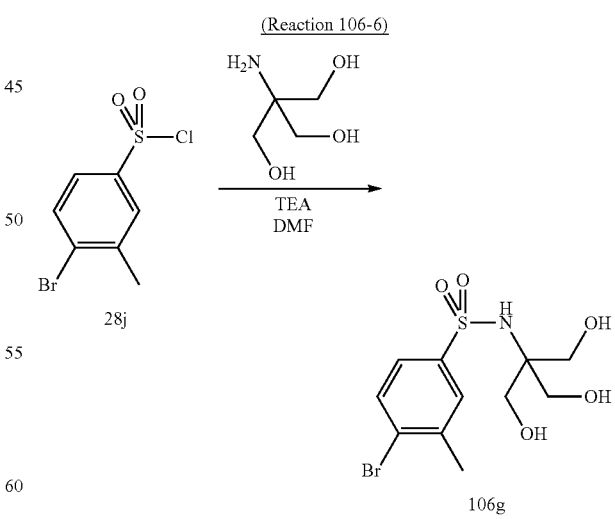

4-Bromo-N-(2-hydroxy-1,1-bis-hydroxymethyl-ethyl)-3-methyl-benzenesulfonamide was synthesized by operations similar to those in Reaction 5-4 using appropriate reagents and starting material.

MS (ESI) m/z=354, 356 (M+H)+.

Example 107

N-(1-Benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide (Compound 596)

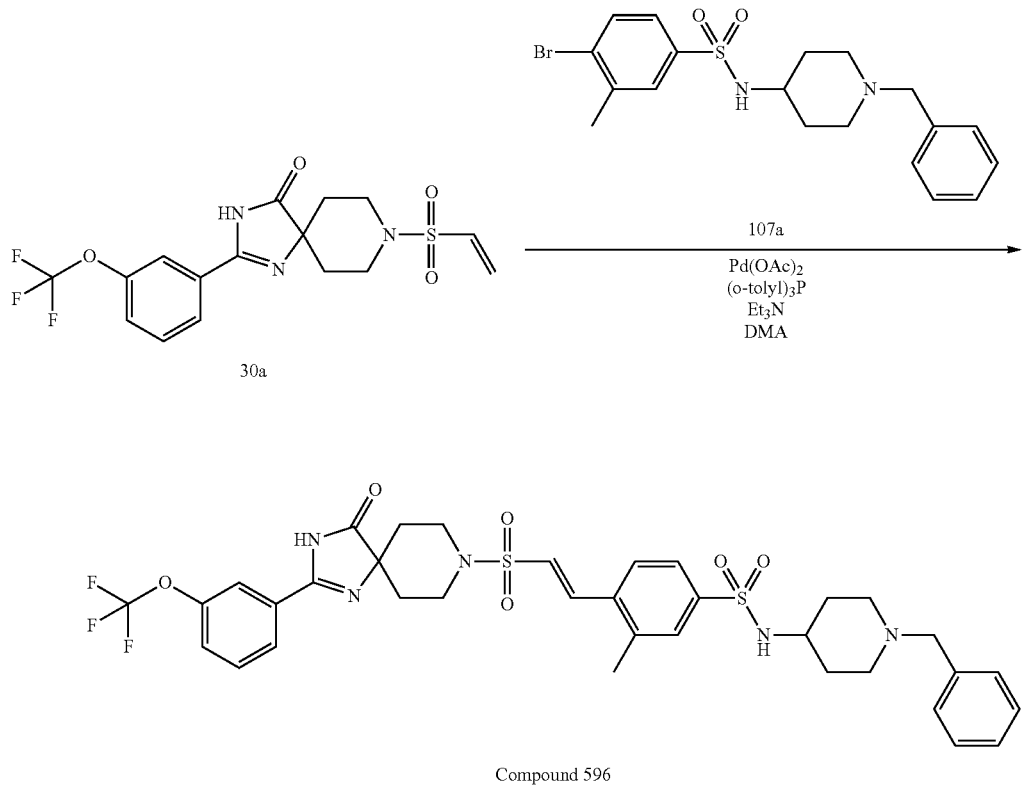

N-(1-Benzyl-piperidin-4-yl)-3-methyl-4-{(E)-2-[4-oxo-2-(3-trifluoromethoxy-phenyl)-1,3,8-triaza-spiro[4.5]dec-1-ene-8-sulfonyl]-vinyl}-benzenesulfonamide was synthesized by operations similar to those in Reaction 26-1 using appropriate reagents and starting material.
MS (ESI) m/z=746 (M+H)+.

The example compounds shown below were synthesized by operations similar to those in Example 107 using appropriate reagents and starting materials.

Compounds 597 to Compound 618

TABLE 82

| Target Compound | Structure | LCMS condition | Retention time (min) | MS (m/z) |
|---|---|---|---|---|
| 597 | (structure shown) | LCMS-C-1 | 2.58 | 593 (M + H)+ |

TABLE 82-continued
| Target Compound | Structure | LCMS condition | Retention time (min) | MS (m/z) |
|---|---|---|---|---|
| 598 | 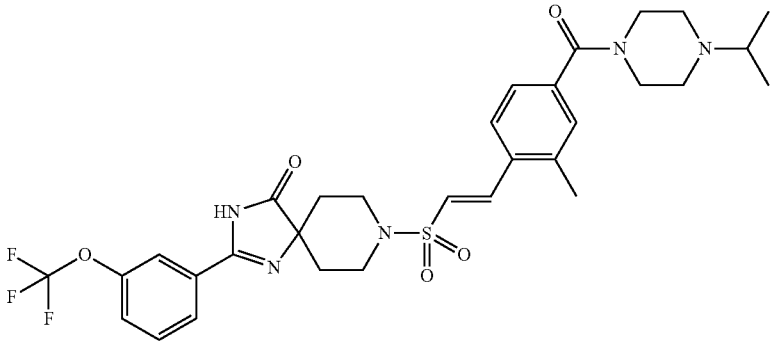 | LCMS-C-1 | 2.77 | 648 (M + H)+ |
| 599 | 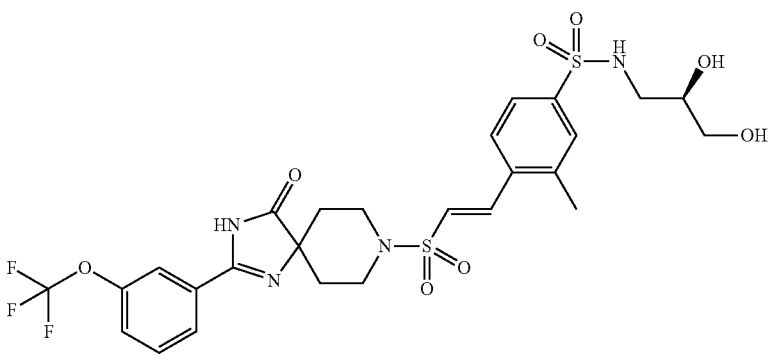 [SMILES: Cc1cc(S(=O)(=O)NC[C@@H](O)CO)ccc1/C=C/S(=O)(=O)N1CCC2(CC1)N=C(c1cccc(OC(F)(F)F)c1)NC2=O] | LCMS-C-1 | 2.45 | 647 (M + H)+ |
| 600 | 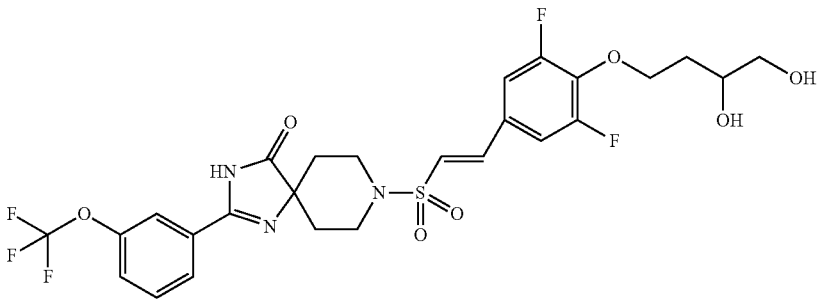 [SMILES: O=C1NC(c2cccc(OC(F)(F)F)c2)=NC12CCN(S(=O)(=O)/C=C/c1cc(F)c(OCCC(O)CO)c(F)c1)CC2] | LCMS-C-1 | 2.6 | 620 (M + H)+ |
| 601 | 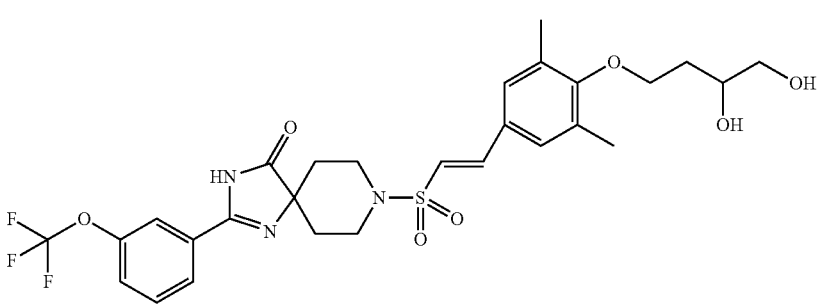 [SMILES: Cc1cc(/C=C/S(=O)(=O)N2CCC3(CC2)N=C(c2cccc(OC(F)(F)F)c2)NC3=O)cc(C)c1OCCC(O)CO] | LCMS-C-1 | 2.67 | 612 (M + H)+ |

TABLE 82-continued

| Target Compound | Structure | LCMS condition | Retention time (min) | MS (m/z) |
|---|---|---|---|---|
| 602 | 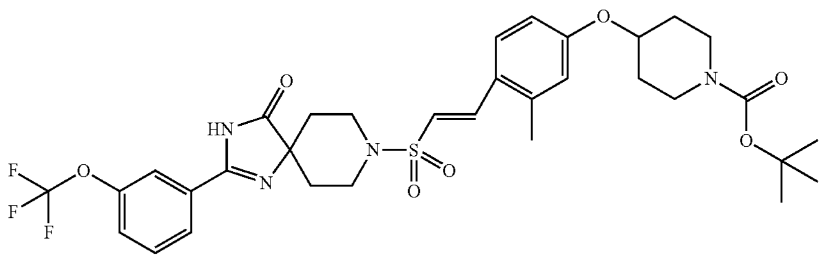 [SMILES: Cc1cc(OC2CCN(C(=O)OC(C)(C)C)CC2)ccc1/C=C/S(=O)(=O)N1CCC2(CC1)N=C(c1cccc(OC(F)(F)F)c1)NC2=O] | LCMS-C-1 | 3.17 | 693 (M + H)+ |
| 603 | 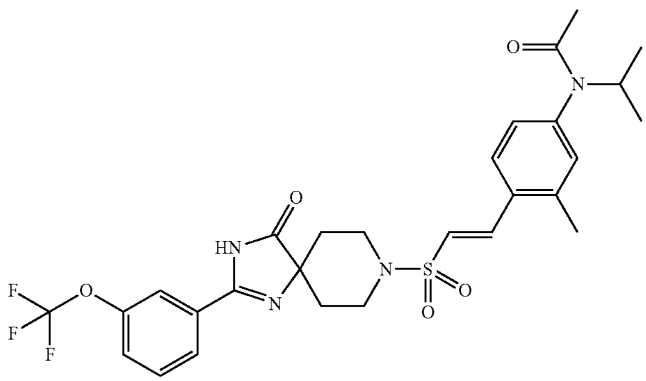 [SMILES: CC(=O)N(c1ccc(/C=C/S(=O)(=O)N2CCC3(CC2)N=C(c2cccc(OC(F)(F)F)c2)NC3=O)c(C)c1)C(C)C] | LCMS-B-1 | 2.4 | 593 (M + H)+ |
| 604 | 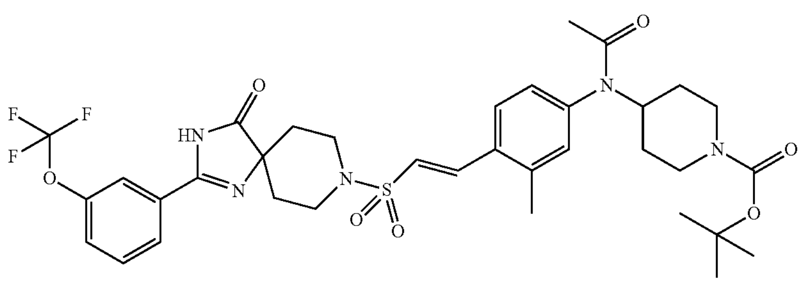 [SMILES: CC(=O)N(c1ccc(/C=C/S(=O)(=O)N2CCC3(CC2)N=C(c2cccc(OC(F)(F)F)c2)NC3=O)c(C)c1)C1CCN(C(=O)OC(C)(C)C)CC1] | LCMS-A-1 | 2.85 | 734 (M + H)+ |
| 605 | 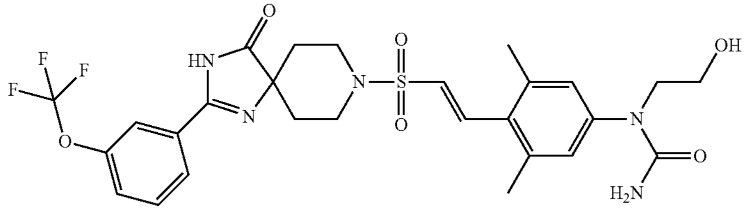 [SMILES: Cc1cc(N(CCO)C(N)=O)cc(C)c1/C=C/S(=O)(=O)N1CCC2(CC1)N=C(c1cccc(OC(F)(F)F)c1)NC2=O] | LCMS-D-1 | 2.97 | 610 (M + H)+ |
| 606 | 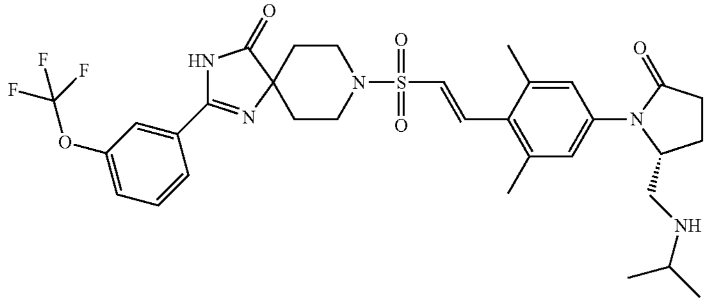 [SMILES: Cc1cc(N2C(=O)CC[C@@H]2CNC(C)C)cc(C)c1/C=C/S(=O)(=O)N1CCC2(CC1)N=C(c1cccc(OC(F)(F)F)c1)NC2=O] | LCMS-D-1 | 1.8 | 662 (M + H)+ |

TABLE 82-continued

| Target Compound | Structure | LCMS condition | Retention time (min) | MS (m/z) |
|---|---|---|---|---|
| 607 | 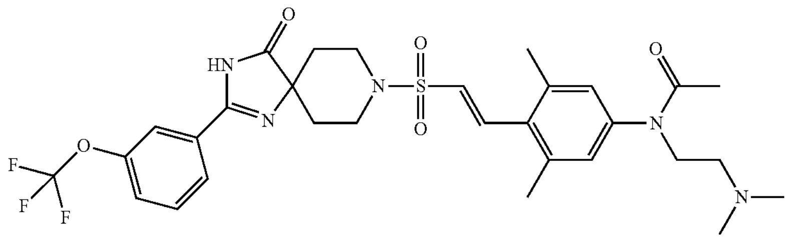 [SMILES: CC(=O)N(CCN(C)C)c1cc(C)c(/C=C/S(=O)(=O)N2CCC3(CC2)N=C(c2cccc(OC(F)(F)F)c2)NC3=O)c(C)c1] | LCMS-D-1 | 2.32 | 636 (M + H)+ |
| 608 | 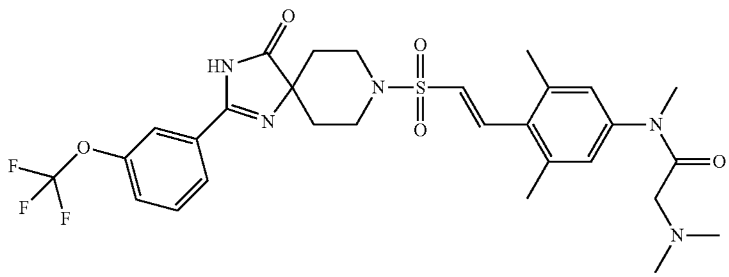 [SMILES: Cc1cc(N(C)C(=O)CN(C)C)cc(C)c1/C=C/S(=O)(=O)N1CCC2(CC1)N=C(c1cccc(OC(F)(F)F)c1)NC2=O] | LCMS-D-1 | 2.78 | 622 (M + H)+ |
| 609 | 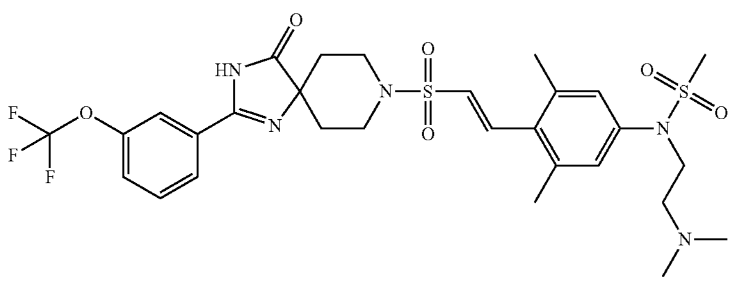 [SMILES: Cc1cc(N(CCN(C)C)S(C)(=O)=O)cc(C)c1/C=C/S(=O)(=O)N1CCC2(CC1)N=C(c1cccc(OC(F)(F)F)c1)NC2=O] | LCMS-D-1 | 1.82 | 672 (M + H)+ |
| 610 | 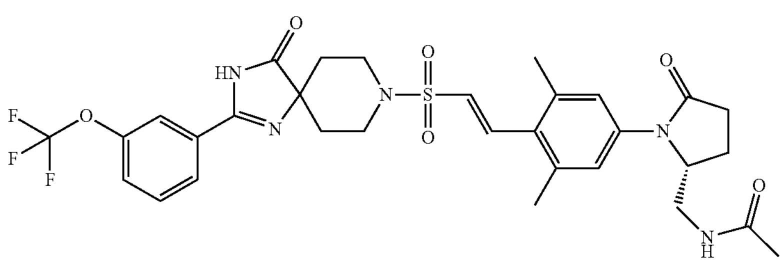 [SMILES: CC(=O)NC[C@H]1CCC(=O)N1c1cc(C)c(/C=C/S(=O)(=O)N2CCC3(CC2)N=C(c2cccc(OC(F)(F)F)c2)NC3=O)c(C)c1] | LCMS-D-1 | 3.03 | 662 (M + H)+ |
| 611 | 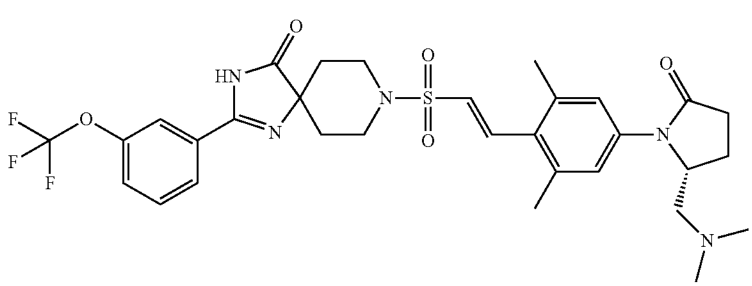 [SMILES: Cc1cc(N2C(=O)CC[C@@H]2CN(C)C)cc(C)c1/C=C/S(=O)(=O)N1CCC2(CC1)N=C(c1cccc(OC(F)(F)F)c1)NC2=O] | LCMS-D-1 | 2.7 | 648 (M + H)+ |

TABLE 82-continued

| Target Compound | Structure | LCMS condition | Retention time (min) | MS (m/z) |
|---|---|---|---|---|
| 612 | 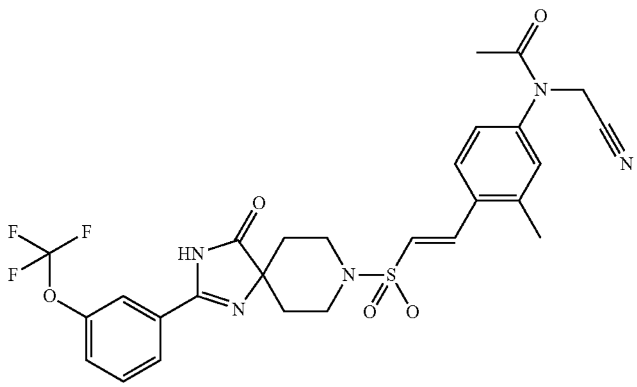 | LCMS-C-1 | 2.55 | 590 (M + H)+ |
| 613 | 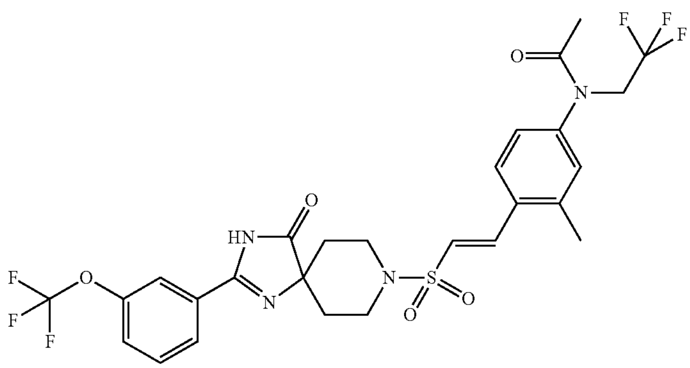 [SMILES: CC(=O)N(CC(F)(F)F)c1ccc(/C=C/S(=O)(=O)N2CCC3(CC2)N=C(c2cccc(OC(F)(F)F)c2)NC3=O)c(C)c1] | LCMS-C-1 | 2.8 | 633 (M + H)+ |
| 614 | 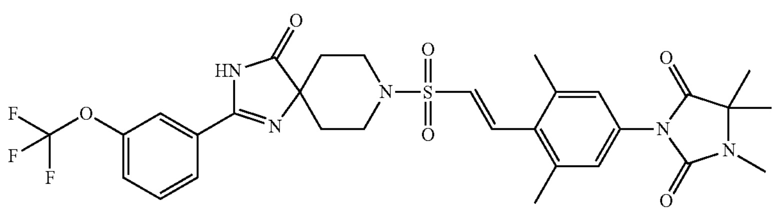 [SMILES: Cc1cc(N2C(=O)N(C)C(C)(C)C2=O)cc(C)c1/C=C/S(=O)(=O)N1CCC2(CC1)N=C(c1cccc(OC(F)(F)F)c1)NC2=O] | LCMS-D-1 | 3.43 | 648 (M + H)+ |
| 615 | 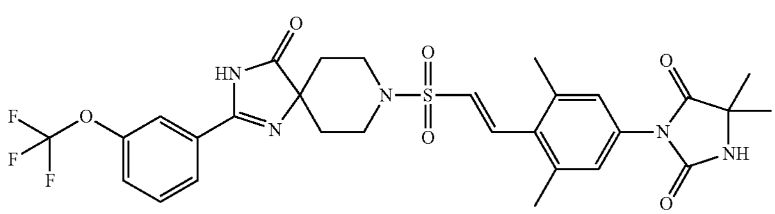 [SMILES: Cc1cc(N2C(=O)NC(C)(C)C2=O)cc(C)c1/C=C/S(=O)(=O)N1CCC2(CC1)N=C(c1cccc(OC(F)(F)F)c1)NC2=O] | LCMS-D-1 | 3.27 | 634 (M + H)+ |
| 616 | 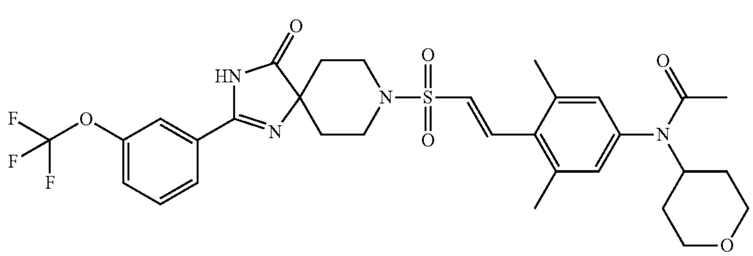 [SMILES: CC(=O)N(c1cc(C)c(/C=C/S(=O)(=O)N2CCC3(CC2)N=C(c2cccc(OC(F)(F)F)c2)NC3=O)c(C)c1)C1CCOCC1] | LCMS-D-1 | 2.15 | 649 (M + H)+ |

TABLE 82-continued

| Target Compound | Structure | LCMS condition | Retention time (min) | MS (m/z) |
|---|---|---|---|---|
| 617 | 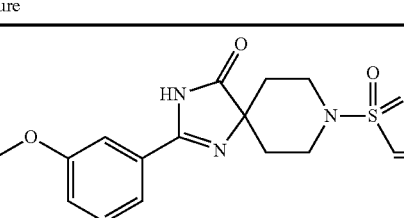 | LCMS-F-1 | 0.93 | 593 (M + H)+ |
| 618 | 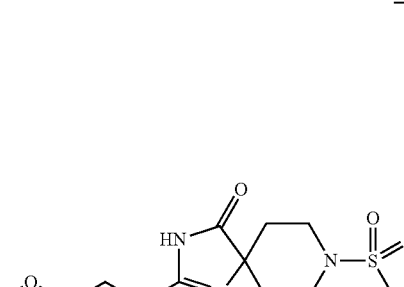 | LCMS-F-1 | 0.9 | 592 (M + H)+ |

The aryl bromide reagent used in the synthesis of Compound 596 (N-(1-benzyl-piperidin-4-yl)-4-bromo-3-methyl-benzenesulfonamide) was synthesized as follows.

The aryl bromide reagent used in the synthesis of Compound 597 ((S)-3-(5-bromo-indol-1-yl)-propane-1,2-diol) was synthesized as follows.

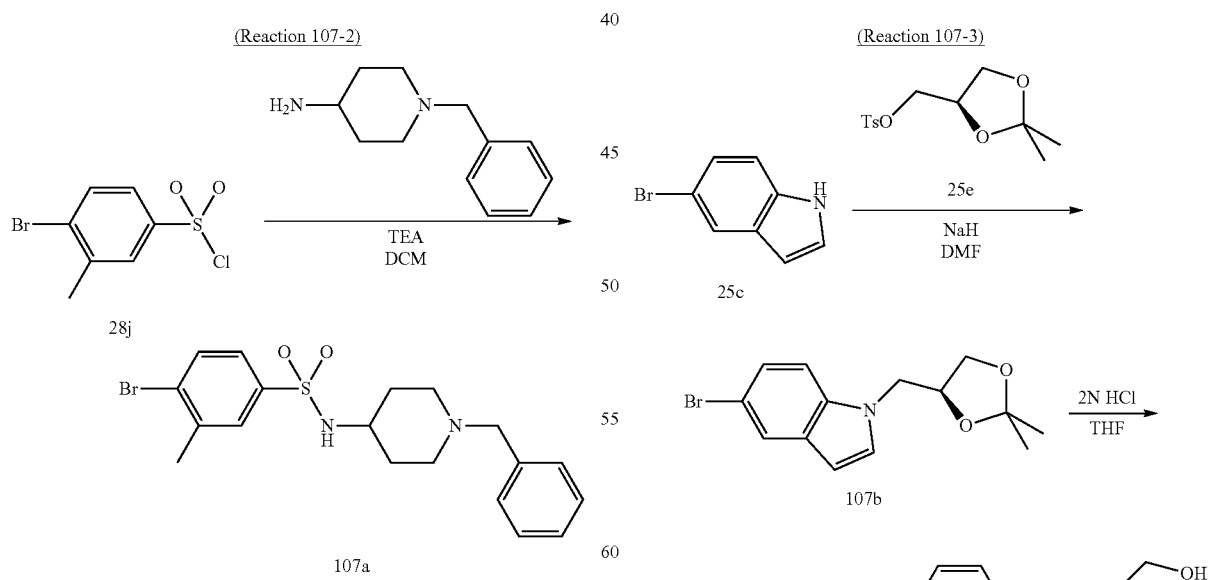

N-(1-Benzyl-piperidin-4-yl)-4-bromo-3-methyl-benzenesulfonamide was synthesized by operations similar to those in Reaction 5-4 using appropriate reagents and starting material.

MS (ESI) m/z=423, 425 (M+H)+.

(S)-3-(5-Bromo-indol-1-yl)-propane-1,2-diol was synthesized by operations similar to those in Reaction 25-3 and Reaction 25-4 using appropriate reagents and starting material.

MS (ESI) m/z=270, 272 (M+H)+.

The aryl bromide reagent used in the synthesis of Compound 598 ((4-bromo-3-methyl-phenyl)-(4-isopropyl-piperazin-1-yl)-methanone) was synthesized as follows.

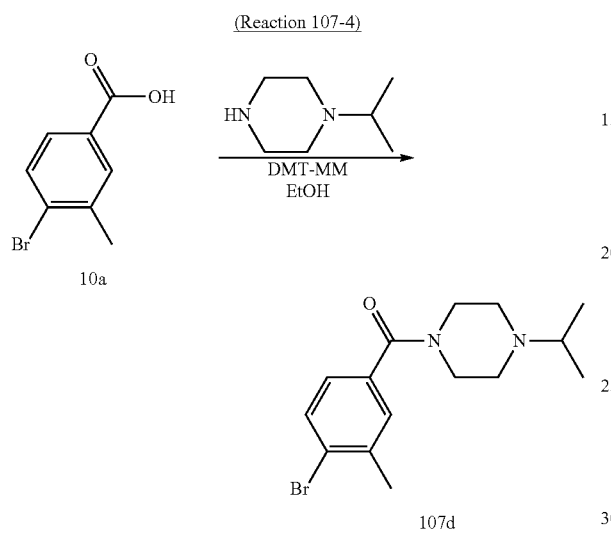

(4-Bromo-3-methyl-phenyl)-(4-isopropyl-piperazin-1-yl)-methanone was synthesized by operations similar to those in Reaction 10-1 using appropriate reagents and starting material.

MS (ESI) m/z=325, 327 (M+H)+.

The aryl bromide reagent used in the synthesis of Compound 599 (4-bromo-N—((R)-2,3-dihydroxy-propyl)-3-methyl-benzenesulfonamide) was synthesized as follows.

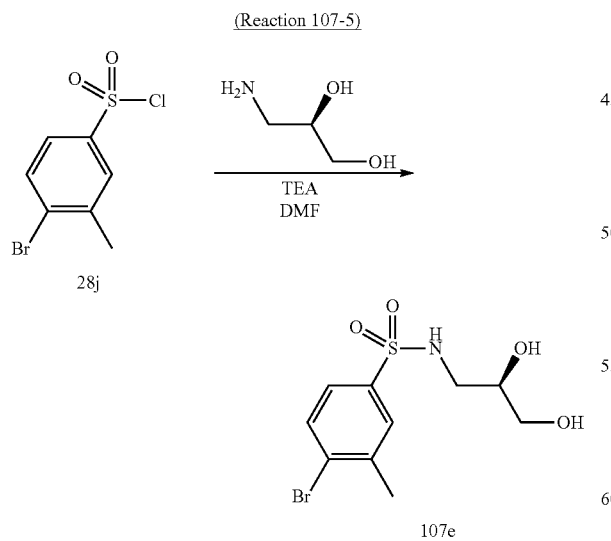

4-Bromo-N—((R)-2,3-dihydroxy-propyl)-3-methyl-benzenesulfonamide was synthesized by operations similar to those in Reaction 5-4 using appropriate reagents and starting material.

MS (ESI) m/z=324, 326 (M+H)+.

The aryl bromide reagent used in the synthesis of Compound 600 (4-(4-bromo-2,6-difluoro-phenoxy)-butane-1,2-diol) was synthesized as follows.

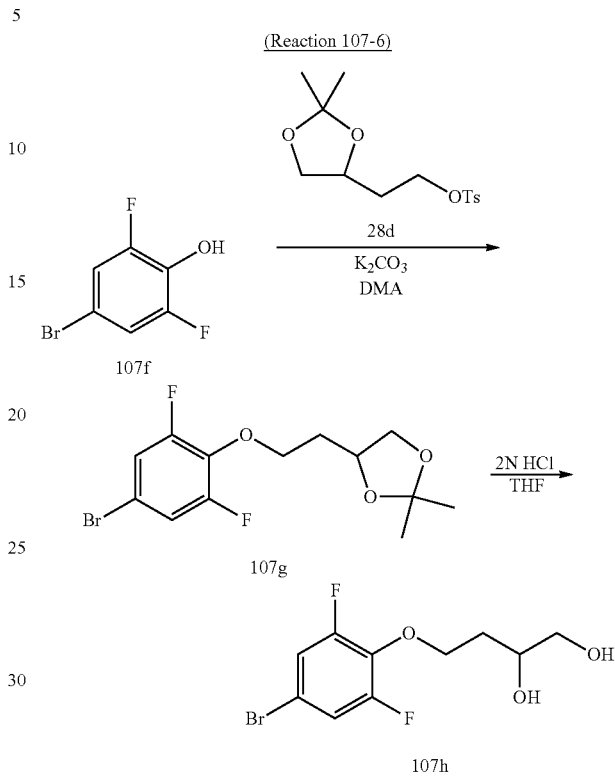

4-(4-Bromo-2,6-difluoro-phenoxy)-butane-1,2-diol was synthesized by operations similar to those in Reaction 23-1 and Reaction 25-4 using appropriate reagents and starting material.

$^1$H-NMR (400 MHz, CDCl$_3$) δ 1.90-1.94 (2H, m), 3.57 (1H, dd, J=12.0, 8.0 Hz), 3.74 (1H, dd, J=12.0, 4.0 Hz), 4.06-4.26 (1H, m), 4.26-4.33 (2H, m), 7.07-7.12 (2H, m).

The aryl bromide reagent used in the synthesis of Compound 601 (4-(4-bromo-2,6-dimethyl-phenoxy)-butane-1,2-diol) was synthesized as follows.

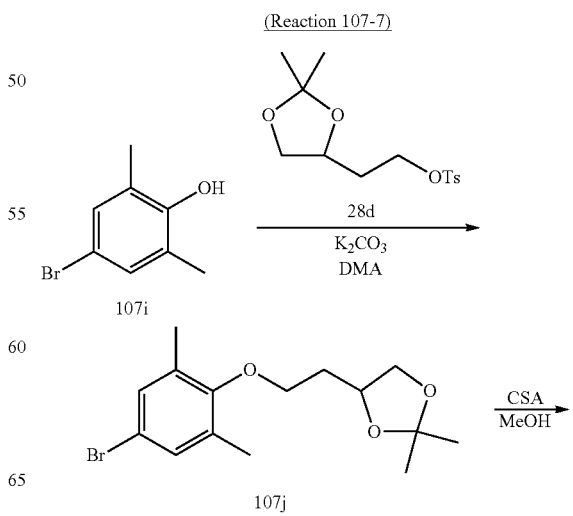

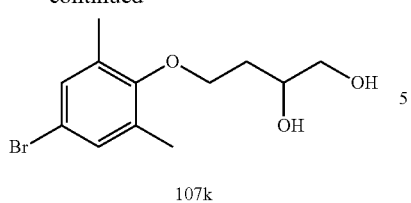

107k 4-(4-Bromo-2,6-dimethyl-phenoxy)-butane-1,2-diol was synthesized by operations similar to those in Reaction 23-1 and Reaction 31-6 using appropriate reagents and starting material.

¹H-NMR (400 MHz, CD₃OD) δ 1.77-1.82 (1H, m), 2.00-2.09 (1H, m), 2.45 (6H, s), 3.50-3.54 (2H, m) 3.84-3.95 (3H, m).

The aryl bromide reagent used in the synthesis of Compound 602 (4-(4-bromo-3-methyl-phenoxy)-piperidine-1-carboxylic acid tert-butyl ester) was synthesized as follows.

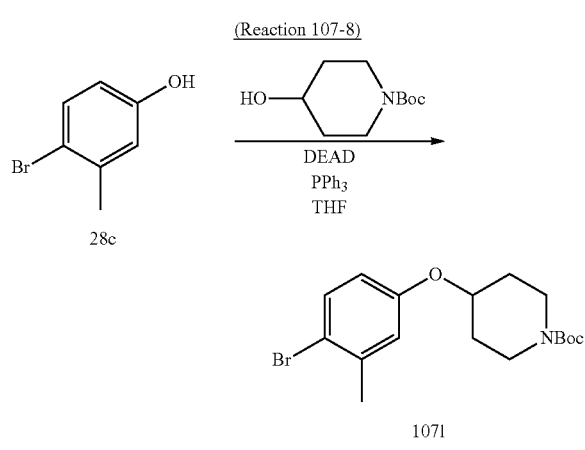

4-(4-Bromo-3-methyl-phenoxy)-piperidine-1-carboxylic acid tert-butyl ester was synthesized by operations similar to those in Reaction 31-7 using appropriate reagents and starting material.

¹H-NMR (400 MHz, CDCl₃) δ 1.50 (9H, s), 1.68-1.76 (2H, m), 1.87-1.92 (2H, m), 2.35 (1H, s), 3.30-3.36 (2H, m), 3.64-3.71 (2H, m), 4.38-4.43 (1H, m), 6.61 (1H, dd, J=8.0, 4.0 Hz), 6.81 (1H, d, J=4.0 Hz), 7.39 (1H, d, J=8.0 Hz).

The aryl bromide reagent used in the synthesis of Compound 603 (N-(4-bromo-3-methyl-phenyl)-N-isopropyl-acetamide) was synthesized as follows.

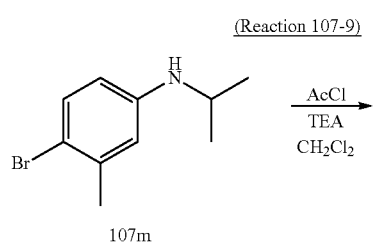

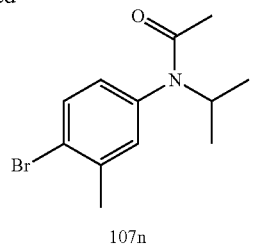

107n

N-(4-Bromo-3-methyl-phenyl)-N-isopropyl-acetamide was synthesized by operations similar to those in Reaction 2-3 using appropriate reagents and starting material.

MS (ESI) m/z=270, 272 (M+H)+.

The aryl bromide reagent used in the synthesis of Compound 604 (4-[acetyl-(4-bromo-3-methyl-phenyl)-amino]-piperidine-1-carboxylic acid tert-butyl ester) was synthesized as follows.

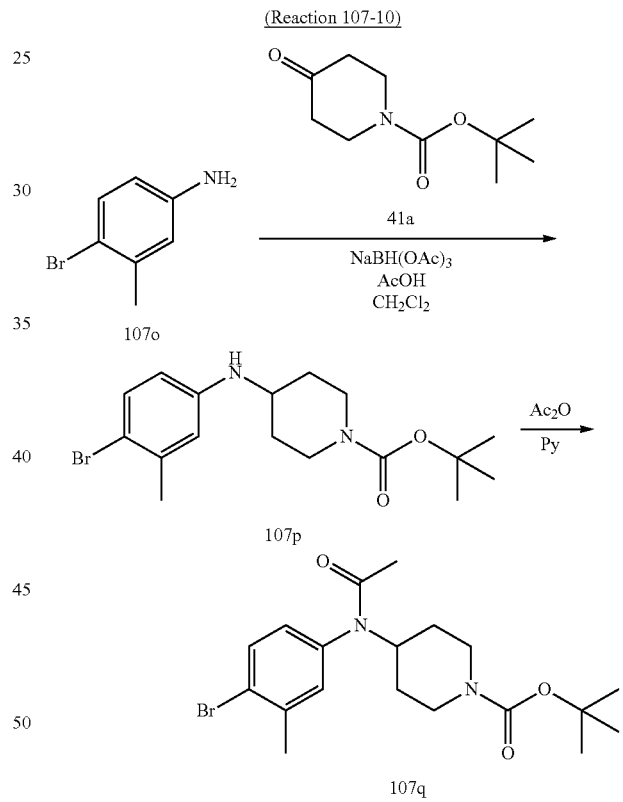

4-[Acetyl-(4-bromo-3-methyl-phenyl)-amino]-piperidine-1-carboxylic acid tert-butyl ester was synthesized by operations similar to those in Reaction 41-1 and Reaction 12-2 using appropriate reagents and starting material.

¹H-NMR (400 MHz, CDCl₃) δ 1.13-1.30 (2H, m), 1.40 (9H, s), 1.70-1.80 (2H, m), 1.76 (3H, s), 2.42 (3H, s), 2.72-2.84 (2H, m), 4.07-4.20 (2H, m), 4.70-4.80 (1H, m), 6.77 (1H, dd, J=2.8, 8.4 Hz), 6.94 (1H, d, J=2.8 Hz), 7.57 (1H, d, J=8.4 Hz).

The aryl bromide reagent used in the synthesis of Compound 605 (1-(4-bromo-3,5-dimethyl-phenyl)-1-(2-hydroxy-ethyl)-urea) was synthesized as follows.

(Reaction 107-11)

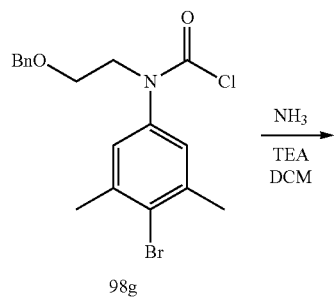

98g

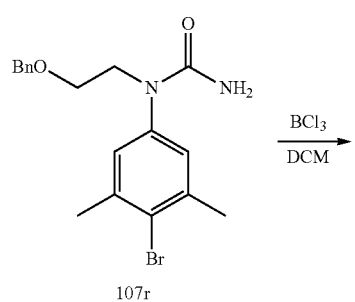

107r

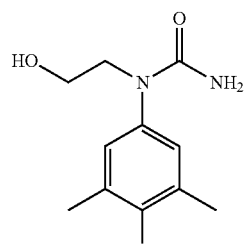

107s 1-(4-Bromo-3,5-dimethyl-phenyl)-1-(2-hydroxy-ethyl)-urea was synthesized by operations similar to those in Reaction 82-1 and Reaction 98-7 using appropriate reagents and starting material.

MS (ESI) m/z=287, 289 (M+H)+.

The aryl bromide reagent used in the synthesis of Compound 606 ((R)-1-(4-bromo-3,5-dimethyl-phenyl)-5-(isopropylamino-methyl)-pyrrolidin-2-one) was synthesized as follows.

(Reaction 107-12)

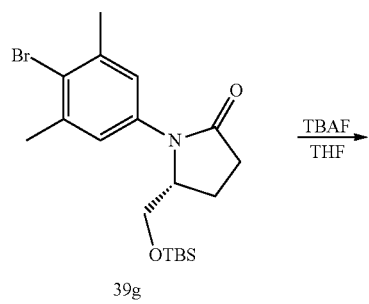

39g

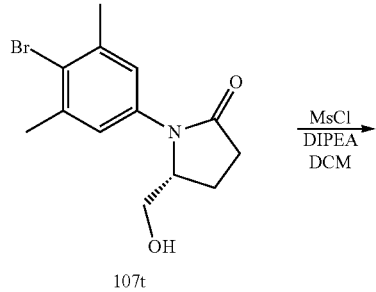

107t

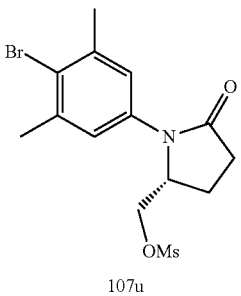

107u

Methanesulfonic acid (R)-1-(4-bromo-3,5-dimethyl-phenyl)-5-oxo-pyrrolidin-2-ylmethyl ester was synthesized by operations similar to those in Reaction 39-2 and Reaction 5-4 using appropriate reagents and starting material.

$^1$H-NMR (CDCl$_3$) δ 7.12 (s, 2H), 4.43 (m, 1H), 4.19 (m, 2H), 2.93 (s, 3H), 2.70 (m, 1H), 2.60 (m, 1H), 2.41 (s, 6H), 2.40 (m, 1H), 2.16 (m, 1H).

(Reaction 107-13)

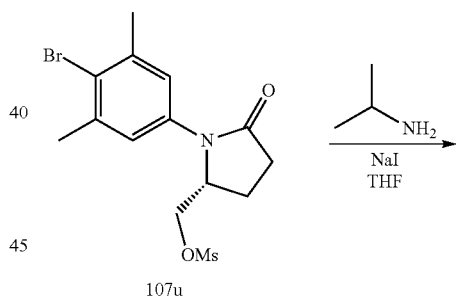

107u

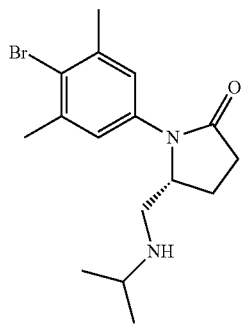

107v

Sodium iodide (catalytic amount) and isopropylamine (1.37 g, 23 mmol) were added to a solution of methanesulfonic acid (R)-1-(4-bromo-3,5-dimethyl-phenyl)-5-oxo-pyrrolidin-2-ylmethyl ester (150 mg, 0.399 mmol) in THF (3 ml) at room temperature, and the mixture was heated with stirring at 70° C. for 1.5 days. After cooling to room temperature, the reaction solution was concentrated under reduced pressure. The resulting residue was purified by silica gel column chromatography (dichloromethane-methanol) to give (R)-1-(4-bromo-3,5-dimethyl-phenyl)-5-(isopropylamino-methyl)-pyrrolidin-2-one (83 mg, 61%).

$^1$H-NMR (CDCl$_3$) δ 7.12 (s, 2H), 4.23 (m, 1H), 2.67 (m, 4H), 2.53 (m, 1H), 2.41 (s, 6H), 2.30 (m, 1H), 2.03 (m, 1H), 0.97 (dd, 6H, J=2.67 Hz, J=6.1 Hz).

The aryl bromide reagent used in the synthesis of Compound 607 (N-(4-bromo-3,5-dimethyl-phenyl)-N-(2-dimethylamino-ethyl)-acetamide) was synthesized as follows.

(Reaction 107-14)

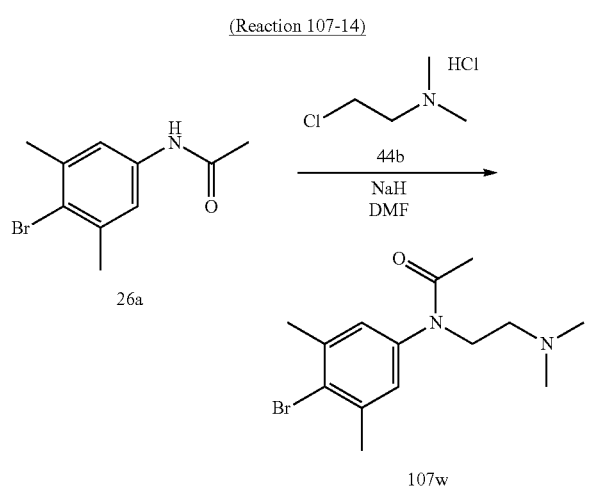

N-(4-Bromo-3,5-dimethyl-phenyl)-N-(2-dimethylamino-ethyl)-acetamide was synthesized by operations similar to those in Reaction 25-3 using appropriate reagents and starting material.

MS (ESI) m/z=313, 315 (M+H)+.

The aryl bromide reagent used in the synthesis of Compound 608 (N-(4-bromo-3,5-dimethyl-phenyl)-2-dimethylamino-N-methyl-acetamide) was synthesized as follows.

(Reaction 107-15)

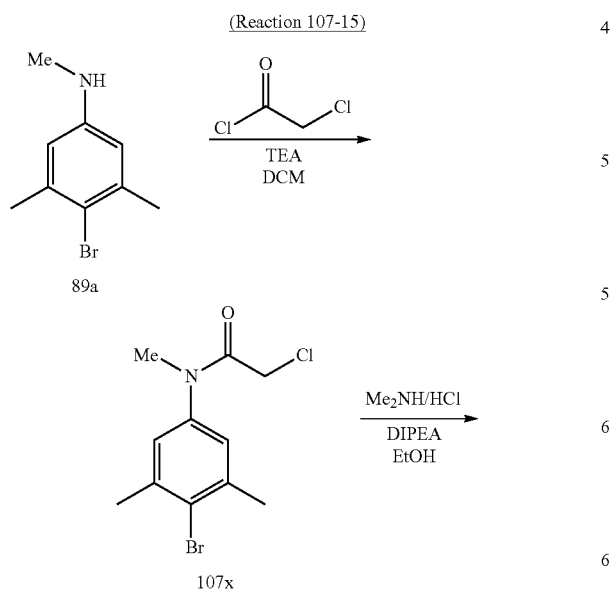

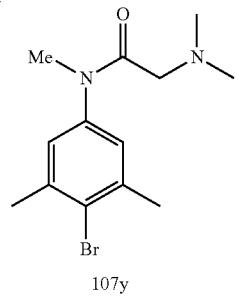

N-(4-Bromo-3,5-dimethyl-phenyl)-2-dimethylamino-N-methyl-acetamide was synthesized by operations similar to those in Reaction 2-3 and Reaction 95-17 using appropriate reagents and starting material.

MS (ESI) m/z=299, 301 (M+H)+.

The aryl bromide reagent used in the synthesis of Compound 609 (N-(4-bromo-3,5-dimethyl-phenyl)-N-(2-dimethylamino-ethyl)-methanesulfonamide) was synthesized as follows.

(Reaction 107-16)

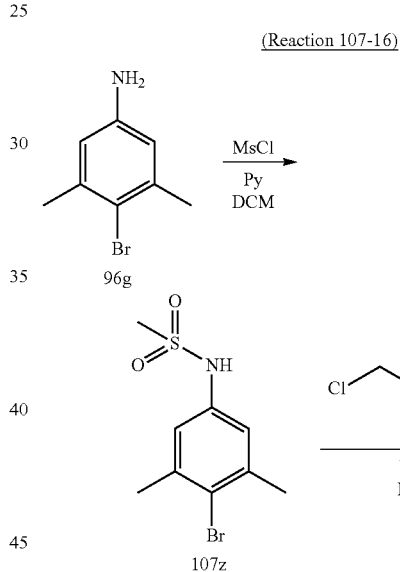

N-(4-Bromo-3,5-dimethyl-phenyl)-N-(2-dimethylamino-ethyl)-methanesulfonamide was synthesized by operations similar to those in Reaction 6-1 and Reaction 25-3 using appropriate reagents and starting material.

MS (ESI) m/z=349, 351 (M+H)+.

The aryl bromide reagent used in the synthesis of Compound 610 ((R)-5-(aminomethyl)-1-(4-bromo-3,5-dimethyl-phenyl)pyrrolidin-2-one) was synthesized as follows.

(Reaction 107-17)

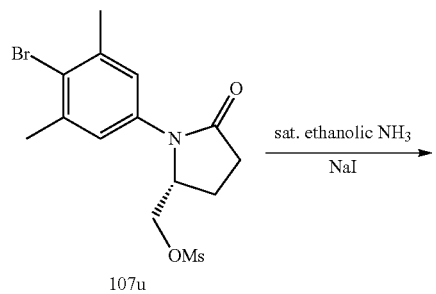

(R)-5-(Aminomethyl)-1-(4-bromo-3,5-dimethylphenyl) pyrrolidin-2-one was synthesized by operations similar to those in Reaction 107-13 using appropriate reagents and starting material.

$^1$H-NMR (CDCl$_3$) δ 7.10 (s, 2H), 4.20 (m, 1H), 2.80 (m, 2H), 2.60 (m, 2H), 2.41 (s, 6H), 2.30 (m, 1H), 2.03 (m, 1H).

The aryl bromide reagent used in the synthesis of Compound 611 ((R)-1-(4-bromo-3,5-dimethyl-phenyl)-5-dimethylaminomethyl-pyrrolidin-2-one) was synthesized as follows.

(Reaction 107-18)

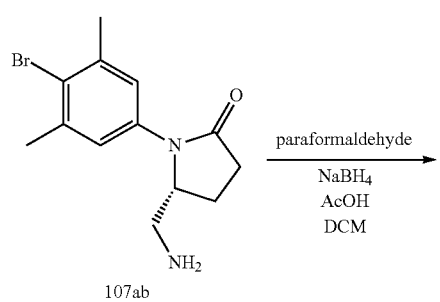

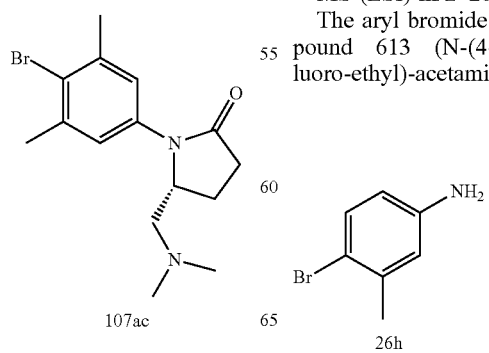

(R)-1-(4-Bromo-3,5-dimethyl-phenyl)-5-dimethylaminomethyl-pyrrolidin-2-one was synthesized by operations similar to those in Reaction 80-1 using appropriate reagents and starting material.

$^1$H-NMR (CDCl$_3$) δ 7.14 (s, 2H), 4.22 (m, 1H), 2.58 (m, 2H), 2.4 (s, 6H), 2.37 (m, 2H), 2.28 (m, 1H), 2.23 (s, 6H), 2.10 (m, 1H).

The aryl bromide reagent used in the synthesis of Compound 612 (N-(4-bromo-3-methyl-phenyl)-N-cyanomethyl-acetamide) was synthesized as follows.

(Reaction 107-19)

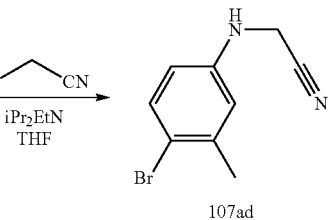

(4-Bromo-3-methyl-phenylamino)-acetonitrile was synthesized by operations similar to those in Reaction 95-17 using appropriate reagents and starting material.

$^1$H-NMR (CDCl$_3$) δ 2.36 (3H, s), 3.86-3.93 (1H, m), 4.09 (2H, d, J=7.8 Hz), 6.43 (1H, dd, J=8.8, 3.8 Hz), 6.60 (1H, d, J=3.8 Hz), 7.38 (1H, d, J=8.8 Hz).

(Reaction 107-20)

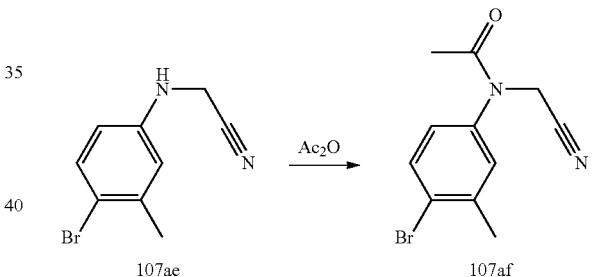

Acetic anhydride (4.99 ml) was added to (4-bromo-3-methyl-phenylamino)-acetonitrile (594 mg, 2.64 mmol), and the mixture was heated with stirring at 115° C. for one hour. The reaction solution was cooled and then concentrated under reduced pressure. The resulting residue was purified by silica gel column chromatography (hexane-ethyl acetate) to give N-(4-bromo-3-methyl-phenyl)-N-cyanomethyl-acetamide (697 mg, 99%).

MS (ESI) m/z=267, 269 (M+H)+.

The aryl bromide reagent used in the synthesis of Compound 613 (N-(4-bromo-3-methyl-phenyl)-N-(2,2,2-trifluoro-ethyl)-acetamide) was synthesized as follows.

(Reaction 107-21)

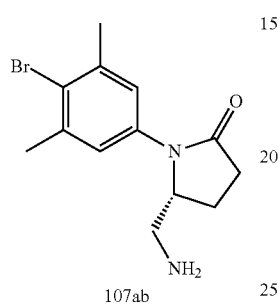

-continued

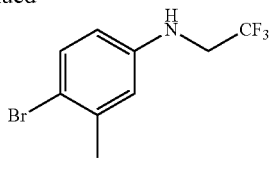

107ag

Potassium carbonate (2.50 g, 18.1 mmol) and trifluoro-methanesulfonic acid 2,2,2-trifluoro-ethyl ester (2.36 ml, 16.4 mmol) were added to a solution of 4-bromo-3-methylaniline (1.68 g, 9.03 mmol) in MeCN (39.0 ml) at room temperature, and the mixture was stirred at 80° C. overnight. The reaction mixture was concentrated under reduced pressure, and the resulting residue was then purified by silica gel column chromatography (hexane-ethyl acetate) to give (4-bromo-3-methyl-phenyl)-(2,2,2-trifluoro-ethyl)-amine (2.20 g, 91%).

MS (ESI) m/z=268, 270 (M+H)+.

(Reaction 107-22)

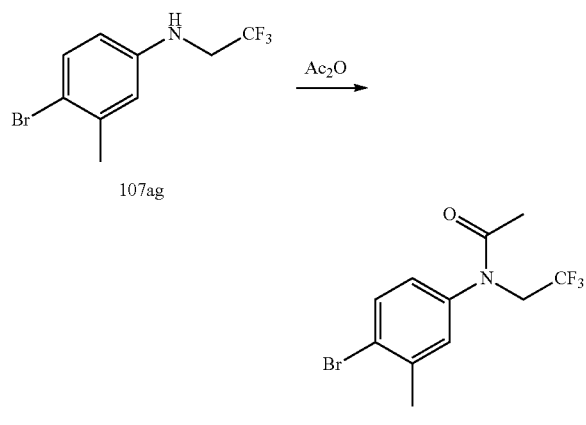

N-(4-Bromo-3-methyl-phenyl)-N-(2,2,2-trifluoro-ethyl)-acetamide was synthesized by operations similar to those in Reaction 107-20 using appropriate reagents and starting material.

MS (ESI) m/z=310, 312 (M+H)+.

The aryl bromide reagent used in the synthesis of Compound 616 (N-(4-bromo-3,5-dimethyl-phenyl)-N-(tetrahydro-pyran-4-yl)-acetamide) was synthesized as follows.

(Reaction 107-23)

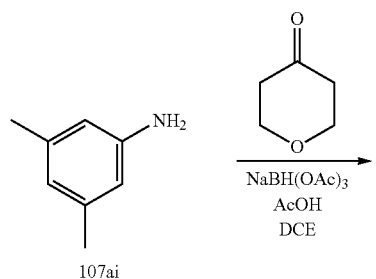

107ai

-continued

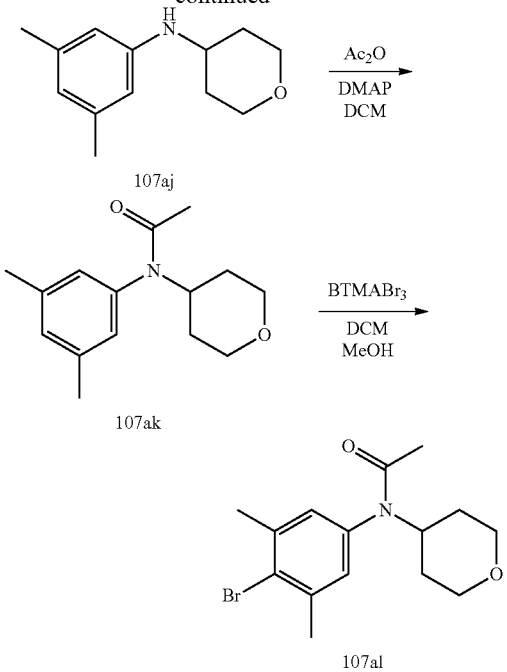

N-(4-Bromo-3,5-dimethyl-phenyl)-N-(tetrahydro-pyran-4-yl)-acetamide was synthesized by operations similar to those in Reaction 41-1, Reaction 19-2 (using DMAP as a base) and Reaction 26-2 using appropriate reagents and starting material.

MS (ESI) m/z=326, 328 (M+H)+.

The aryl bromide reagent used in the synthesis of Compound 617 (4-(4-bromo-3-methyl-phenyl)-morpholin-3-one) was synthesized as follows.

(Reaction 107-24)

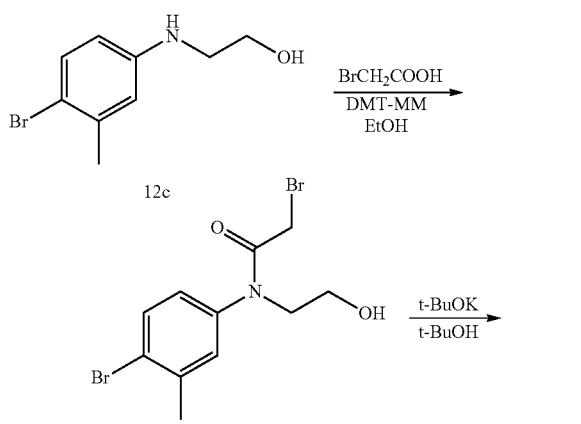

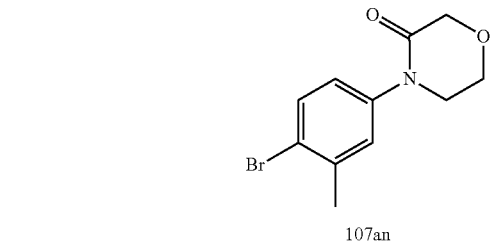

107an

669

4-(4-Bromo-3-methyl-phenyl)-morpholin-3-one was synthesized by operations similar to those in Reaction 10-1 and Reaction 96-18 using appropriate reagents and starting material.

MS (ESI) m/z=270, 272 (M+H)+.

Example 108

2-(4-Fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one (Compound 619)

(Reaction 108-1)

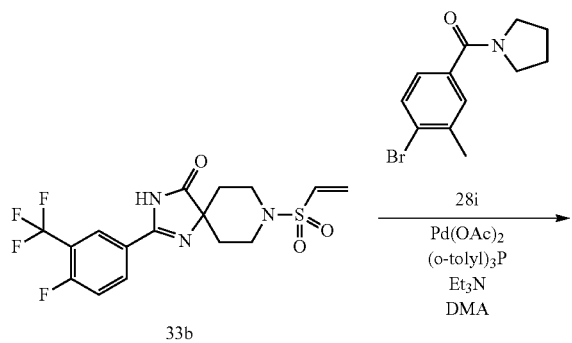

670

-continued

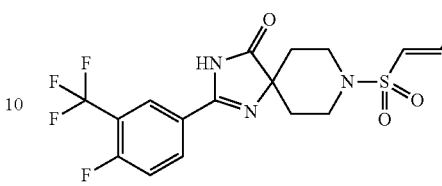

Compound 619

2-(4-Fluoro-3-trifluoromethyl-phenyl)-8-{(E)-2-[2-methyl-4-(pyrrolidine-1-carbonyl)-phenyl]-ethenesulfonyl}-1,3,8-triaza-spiro[4.5]dec-1-en-4-one was synthesized by operations similar to those in Reaction 26-1 using appropriate reagents and starting material.

MS (ESI) m/z=593 (M+H)+.

The example compounds shown below were synthesized by operations similar to those in Example 108 using appropriate reagents and starting materials.

Compounds 620 to Compound 621

TABLE 83

| Target Compound | Structure | LCMS condition | Retention time (min) | MS (m/z) |
|---|---|---|---|---|
| 620 | 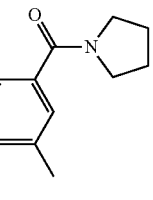 | LCMS-C-1 | 2.48 | 609 (M + H)+ |
| 621 | 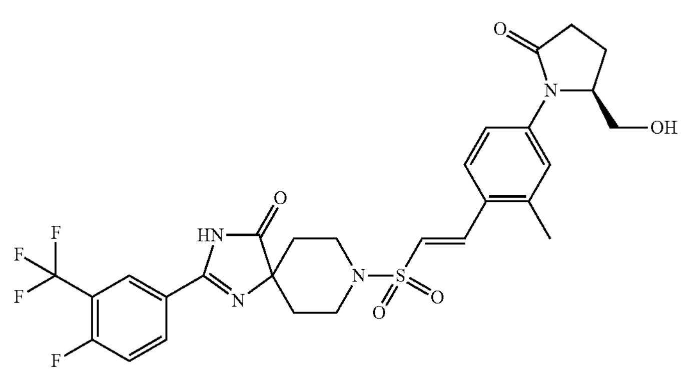 [SMILES: Cc1cc(N2C(=O)CC[C@H]2CO)ccc1/C=C/S(=O)(=O)N1CCC2(CC1)N=C(c1ccc(F)c(C(F)(F)F)c1)NC2=O] | LCMS-C-1 | 2.43 | 609 (M + H)+ |

The aryl bromide reagent used in the synthesis of Compound 621 ((S)-1-(4-bromo-3-methyl-phenyl)-5-hydroxymethyl-pyrrolidin-2-one) was synthesized as follows.

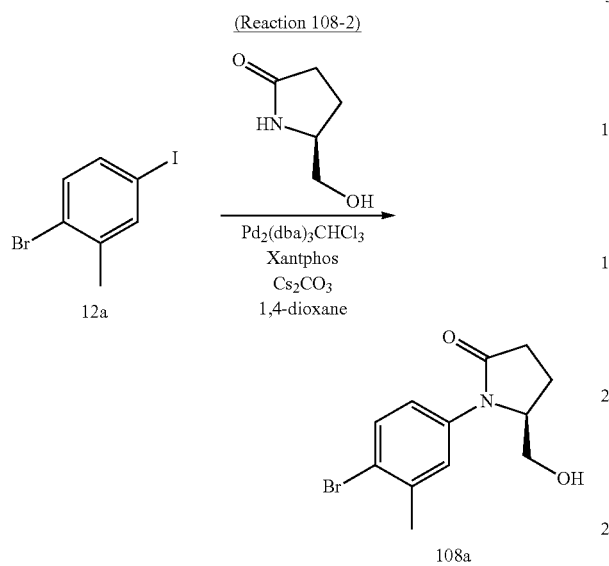

(Reaction 108-2)

(S)-1-(4-Bromo-3-methyl-phenyl)-5-hydroxymethyl-pyrrolidin-2-one was synthesized by operations similar to those in Reaction 29-3 using appropriate reagents and starting material.
MS (ESI) m/z=284 (M+H)+.

Example 109

8-{(E)-2-[1-((S)-2,3-Dihydroxy-propyl)-1H-indol-4-yl]-ethenesulfonyl}-2-(9,9,9-trifluoro-nonyl)-1,3,8-triaza-spiro[4.5]dec-1-en-4-one (Compound 622)

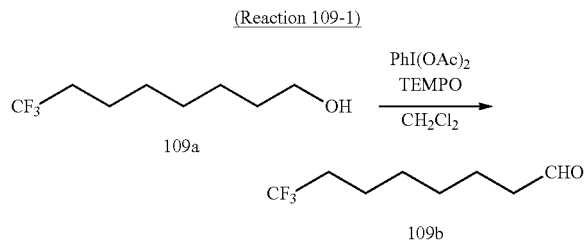

(Reaction 109-1)

2,2,6,6-Tetramethylpiperidine 1-oxyl (202 mg, 1.29 mmol) and (diacetoxyiodo)benzene (3.33 g, 10.4 mmol) were added to a solution of 8,8,8-trifluoro-octanol (~8.63 mmol) in dichloromethane (34.5 mL) at 0° C. in an $N_2$ atmosphere, and the mixture was stirred at 0° C. for five minutes and at room temperature for 1.5 hours. The reaction solution was diluted with dichloromethane (200 mL), and the organic layer was sequentially washed with a saturated aqueous sodium sulfite solution (100 mL), a saturated aqueous sodium bicarbonate solution (100 mL) and saturated brine (100 mL). The organic layer was dried over sodium sulfate and then concentrated under reduced pressure. The resulting residue was purified by silica gel column chromatography (hexane-ethyl acetate) to give 8,8,8-trifluoro-octanal as a colorless oily substance (310 mg, two steps, 20%).
$^1$H-NMR (400 MHz, CDCl$_3$) δ 1.35-1.50 (4H, br-m), 1.58-1.62 (2H, br-m), 1.68-1.73 (2H, br-m), 2.05-2.17 (2H, br-m), 2.49 (2H, t, J=7.1 Hz), 9.82 (1H, s).
$^{19}$F-NMR (376 MHz, CDCl$_3$) δ −66.3 (3F, s).

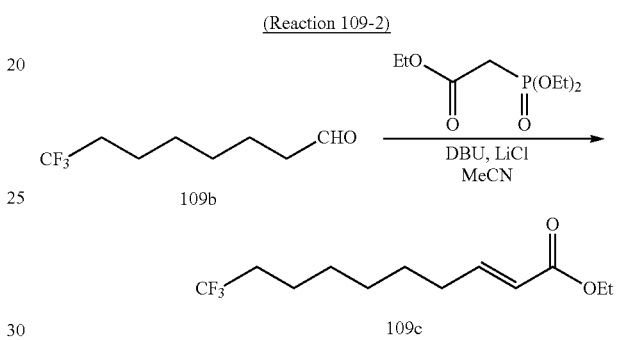

(Reaction 109-2)

1,8-Diazabicyclo[5.4.0]undec-7-ene (436 μL, 2.92 mmol) was added to a solution of (diethoxy-phosphoryl)-acetic acid ethyl ester (633 μL, 2.43 mmol) and lithium chloride (144 mg, 3.41 mmol) in acetonitrile (20.0 mL) at 0° C., and the mixture was stirred at 0° C. for 10 minutes. A solution of 8,8,8-trifluoro-octanal (2.43 mmol) in acetonitrile (4.3 mL) was added dropwise to the reaction solution at 0° C., and the mixture was stirred for 10 minutes. Thereafter, the reaction mixture was stirred at room temperature for one hour and diluted with methyl tert-butyl ether (200 mL). The organic layer was sequentially washed with a saturated aqueous ammonium chloride solution (30 mL), H$_2$O (30 mL) and saturated brine (30 mL), dried over sodium sulfate and concentrated under reduced pressure. The resulting residue was purified by silica gel column chromatography (hexane-ethyl acetate) to give (E)-10,10,10-trifluoro-dec-2-enoic acid ethyl ester as a colorless oily substance (426.6 mg, 70%).
$^1$H-NMR (400 MHz, CDCl$_3$) δ 1.29 (3H, t, J=7.2 Hz), 1.31-1.41 (4H, m), 1.41-1.49 (2H, m), 1.51-1.59 (2H, m), 1.99-2.12 (2H, m), 2.20 (2H, ddd, J=14.5, 7.2, 1.5 Hz), 4.18 (2H, q, J=7.1 Hz), 5.81 (1H, dt, J=15.7, 1.6 Hz), 6.95 (1H, dt, J=15.6, 7.0 Hz).
$^{19}$F-NMR (376 MHz, CDCl$_3$) δ −66.4 (3F, s).

(Reaction 109-3)

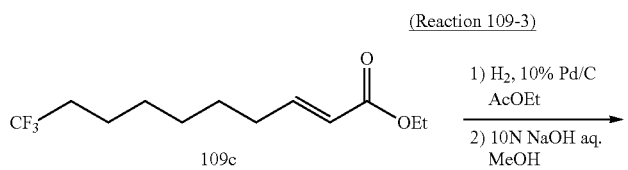

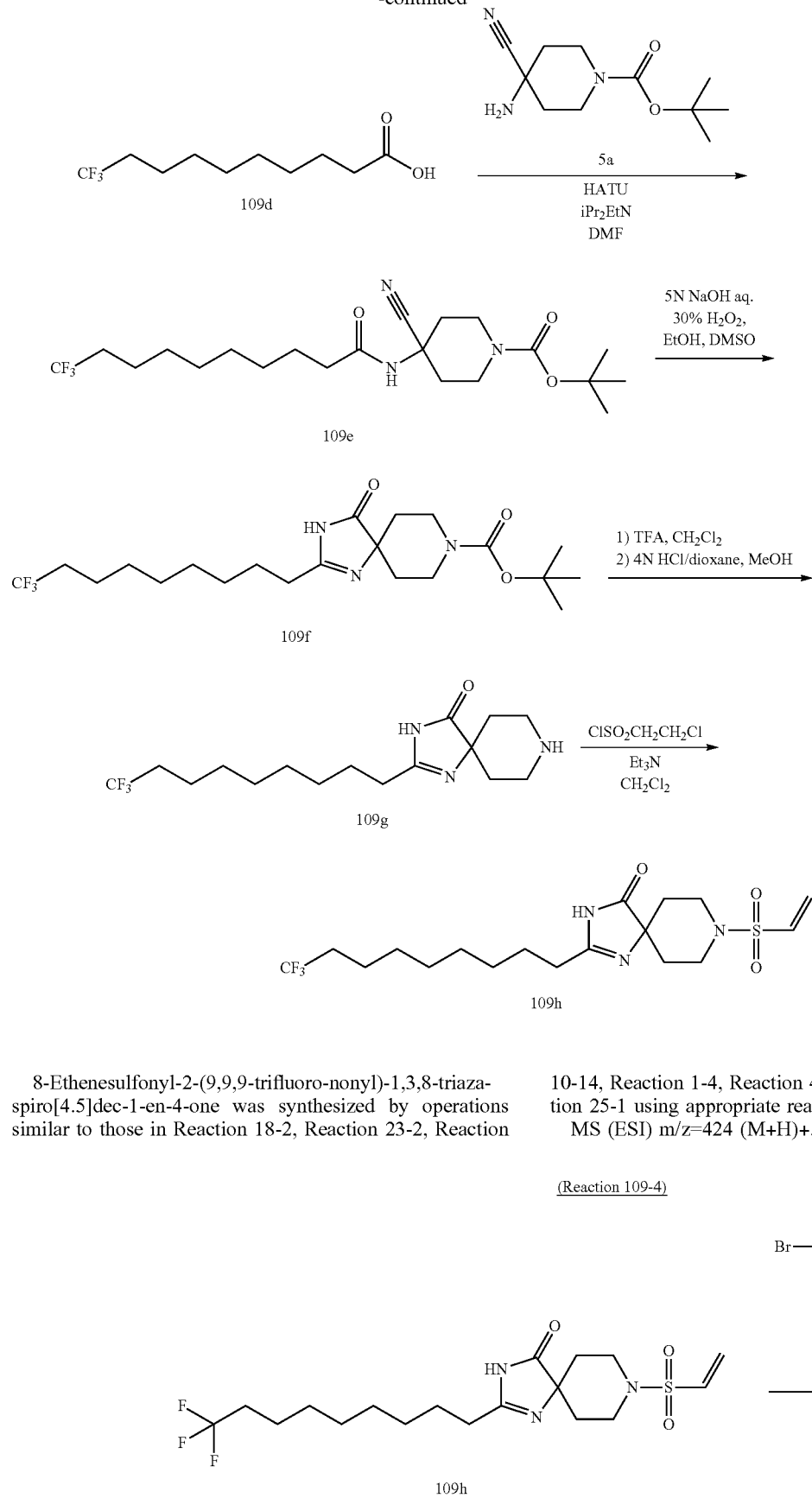
8-Ethenesulfonyl-2-(9,9,9-trifluoro-nonyl)-1,3,8-triaza-spiro[4.5]dec-1-en-4-one was synthesized by operations similar to those in Reaction 18-2, Reaction 23-2, Reaction 10-14, Reaction 1-4, Reaction 4-1, Reaction 5-3 and Reaction 25-1 using appropriate reagents and starting material.
MS (ESI) m/z=424 (M+H)+.
(Reaction 109-4)

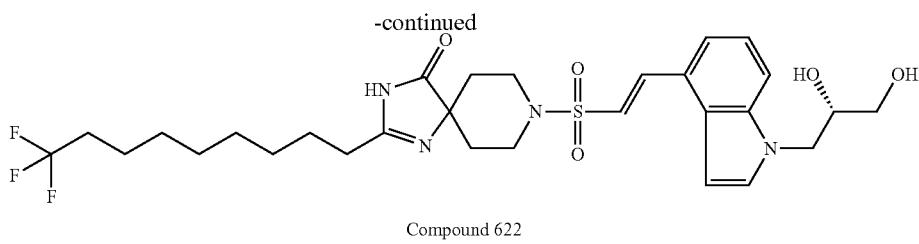

Compound 622

8-{(E)-2-[1-((S)-2,3-Dihydroxy-propyl)-1H-indol-4-yl]-ethenesulfonyl}-2-(9,9,9-trifluoro-nonyl)-1,3,8-triaza-spiro[4.5]dec-1-en-4-one was synthesized by operations similar to those in Reaction 26-1 using appropriate reagents and starting material.

MS (ESI) m/z=613 (M+H)+.

Example 110

8-{(E)-2-[1-((S)-2,3-Dihydroxy-propyl)-1H-indol-4-yl]-ethenesulfonyl}-2-(8,8,9,9,9-pentafluoro-nonyl)-1,3,8-triaza-spiro[4.5]dec-1-en-4-one (Compound 623)

(Reaction 110-1)

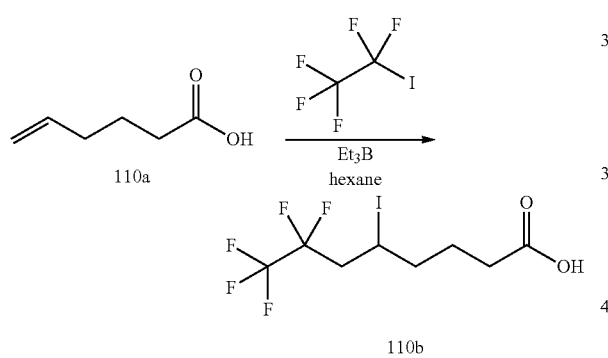

Triethylborane (43.8 mL, 438 mmol) and 1,1,1,2,2-pentafluoro-2-iodo-ethane (8.52 mL, 657 mmol) were added to a solution of hex-5-enoic acid (5.21 mL, 438 mmol) in hexane (219 mL) at room temperature, and the mixture was stirred at room temperature for five days. The reaction solution was concentrated under reduced pressure, and the resulting residue was purified by silica gel column chromatography (hexane-ethyl acetate) to give 7,7,8,8,8-pentafluoro-5-iodo-octanoic acid (purity 80%) as a colorless oily substance (2.63 g, 17%).

$^1$H-NMR (400 MHz, CDCl$_3$) δ 1.72-1.82 (1H, m), 1.83-1.92 (2H, m), 1.86-1.98 (1H, m), 2.36-2.46 (2H, m), 2.67-2.96 (2H, m), 4.65-4.34 (1H, m).

(Reaction 110-2)

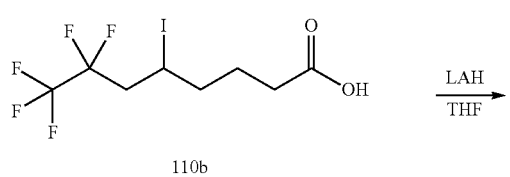

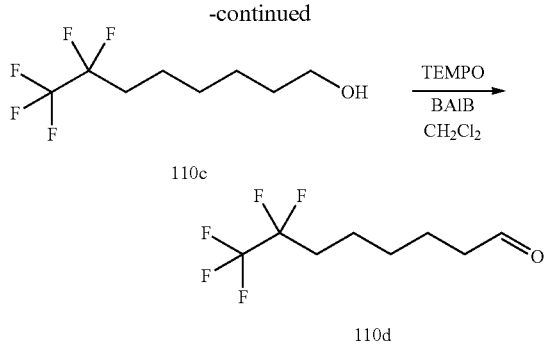

7,7,8,8,8-Pentafluoro-octanal was synthesized by operations similar to those in Reaction 95-28 and Reaction 109-1 using appropriate reagents and starting material. This was used in the next reaction without complete purification.

(Reaction 110-3)

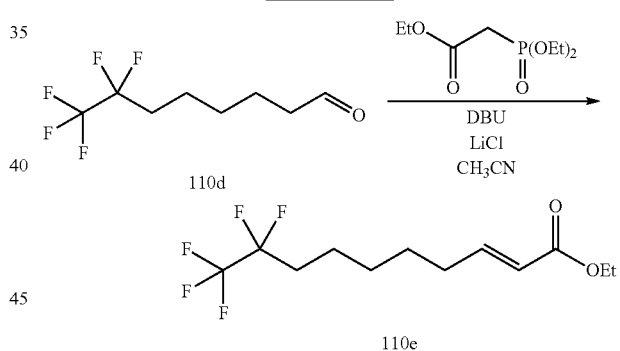

1,8-Diazabicyclo[5.4.0]undec-7-ene (1.08 mL, 7.26 mmol) was added to a solution of (diethoxy-phosphoryl)-acetic acid ethyl ester (1.57 mL, 7.87 mmol) and lithium chloride (359 mg, 8.47 mmol) in acetonitrile (60.5 mL) at 0° C., and the mixture was stirred at 0° C. for 10 minutes. A solution of 7,7,8,8,8-pentafluoro-octanal (1.32 g, 6.05 mmol) in acetonitrile (20.5 mL) was added dropwise to the reaction solution at 0° C., and the mixture was stirred for 10 minutes. Thereafter, the reaction mixture was stirred at room temperature for one hour and diluted with methyl tert-butyl ether (300 mL). The organic layer was sequentially washed with 2 N hydrochloric acid (50 mL), H$_2$O (50 mL) and saturated brine (50 mL), dried over sodium sulfate and concentrated under reduced pressure. The resulting residue was purified by silica gel column chromatography (hexane-ethyl acetate) to give (E)-9,9,10,10,10-pentafluoro-dec-2-enoic acid ethyl ester (purity 80%) as a colorless oily substance (49.7 mg, 47%).

¹H-NMR (400 MHz, CDCl₃) δ 1.29 (3H, t, J=7.2 Hz), 1.37-1.44 (1H, m), 1.46-1.52 (1H, m), 1.56-1.68 (2H, m), 1.93-2.08 (2H, m), 2.18-2.26 (2H, m), 4.19 (2H, q, J=7.2 Hz), 5.79-5.86 (1H, m), 6.88-6.98 (1H, m).
(Reaction 110-4)
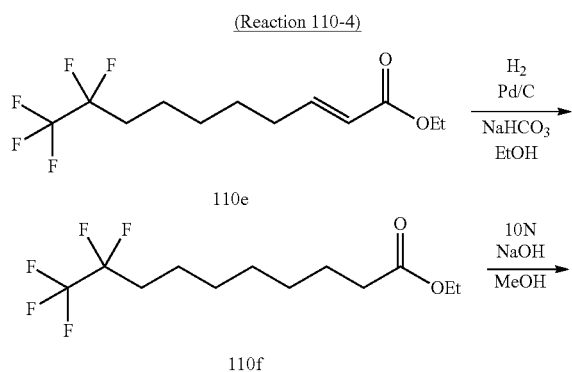
9,9,10,10,10-Pentafluoro-decanoic acid was synthesized by operations similar to those in Reaction 18-2 and Reaction 95-18 using appropriate reagents and starting material.
¹H-NMR (400 MHz, CDCl₃) δ 1.31-1.44 (6H, br-m), 1.53-1.68 (4H, m), 1.92-2.08 (2H, br-m), 2.36 (2H, t, J=7.6 Hz).
(Reaction 110-5)
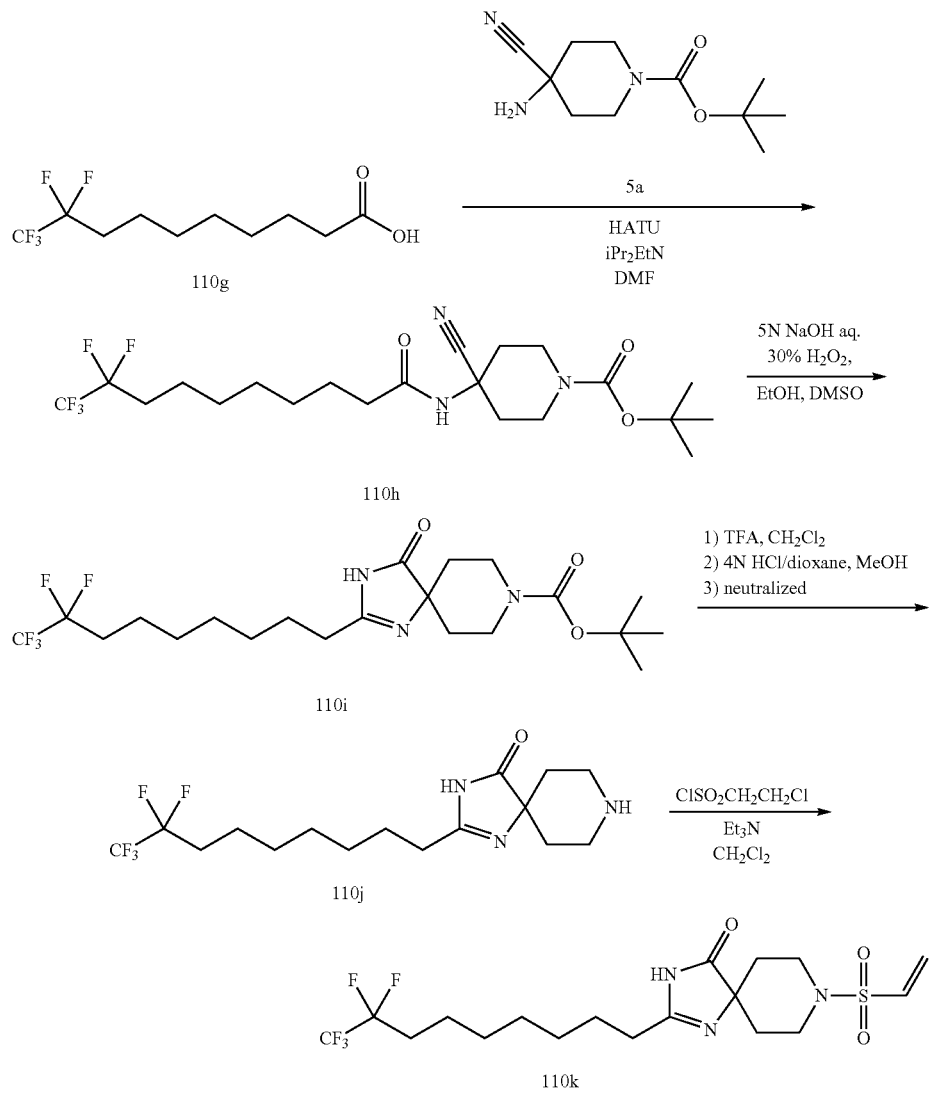

8-Ethenesulfonyl-2-(8,8,9,9,9-pentafluoro-nonyl)-1,3,8-triaza-spiro[4.5]dec-1-en-4-one was synthesized by operations similar to those in Reaction 10-14, Reaction 1-4, Reaction 4-1, Reaction 5-3 and Reaction 25-1 using appropriate reagents and starting material.

MS (ESI) m/z=460 (M+H)+.

(Reaction 110-6)

Compound 623

8-{(E)-2-[1-((S)-2,3-Dihydroxy-propyl)-1H-indol-4-yl]-ethenesulfonyl}-2-(8,8,9,9,9-pentafluoro-nonyl)-1,3,8-triaza-spiro[4.5]dec-1-en-4-one was synthesized by operations similar to those in Reaction 26-1 using appropriate reagents and starting material.

MS (ESI) m/z=649 (M+H)+.

Example 111

1-(4-{(E)-2-[2-(4-Ethyl-cyclohexyl)-4-oxo-1,3,8-triaza-spiro[4.5]dec-1-ene-8-sulfonyl]-vinyl}-3-methyl-phenyl)-imidazolidine-2,4-dione (Compound 624)

(Reaction 111-1)

-continued

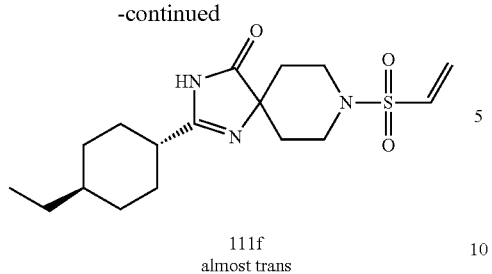

111f
almost trans

8-Ethenesulfonyl-2-(4-ethyl-cyclohexyl)-1,3,8-triaza-spiro[4.5]dec-1-en-4-one was synthesized by operations similar to those in Reaction 10-14, Reaction 10-11, Reaction 10-12, Reaction 4-1, Reaction 5-3 and Reaction 25-1 using appropriate reagents and starting material.

MS (ESI) m/z=352 (M−H)−.

(Reaction 111-2)

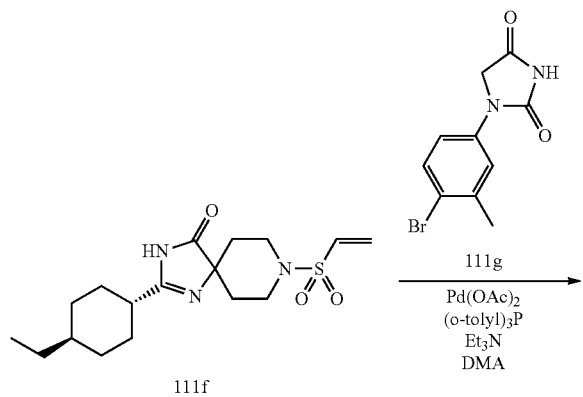

-continued

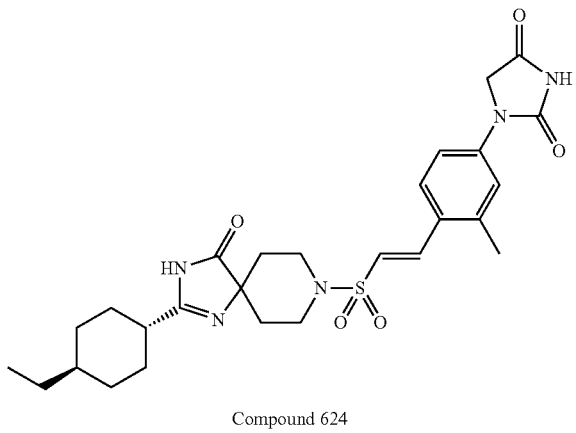

Compound 624

1-(4-{(E)-2-[2-(4-Ethyl-cyclohexyl)-4-oxo-1,3,8-triaza-spiro[4.5]dec-1-ene-8-sulfonyl]-vinyl}-3-methyl-phenyl)-imidazolidine-2,4-dione was synthesized by operations similar to those in Reaction 26-1 using appropriate reagents and starting material.

MS (ESI) m/z=542 (M+H)+.

The example compounds shown below were synthesized by operations similar to those in Reaction 111-2 using appropriate reagents and starting materials.

Compounds 625 to Compound 626

TABLE 84

| Target Compound | Structure | LCMS condition | Retention time (min) | MS (m/z) |
|---|---|---|---|---|
| 625 | 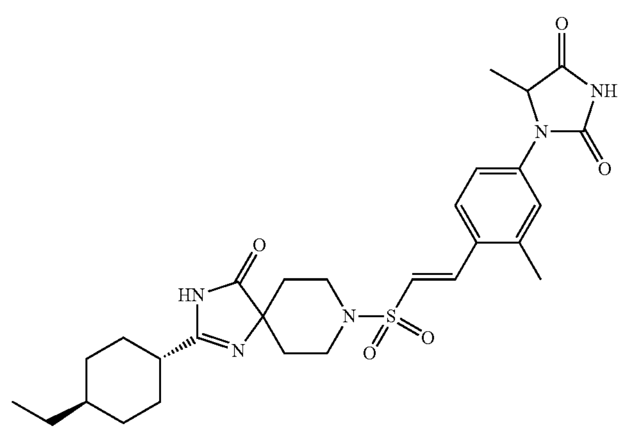 | LCMS-C-1 | 2.7 | 556 (M + H)+ |

TABLE 84-continued

| Target Compound | Structure | LCMS condition | Retention time (min) | MS (m/z) |
|---|---|---|---|---|
| 626 | 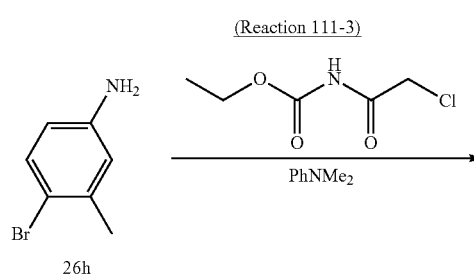 | LCMS-C-1 | 2.73 | 571 (M + H)+ |

The aryl bromide reagent used in the synthesis of Compound 624 (1-(4-bromo-3-methyl-phenyl)-imidazolidine-2,4-dione) was synthesized as follows.

(Reaction 111-3)

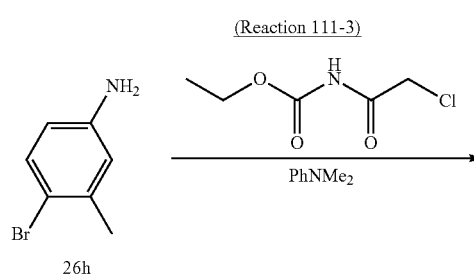

(Reaction 111-4)

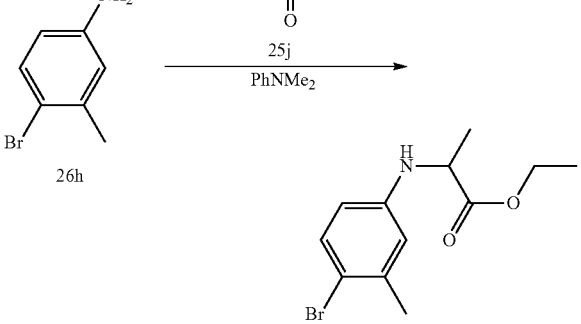

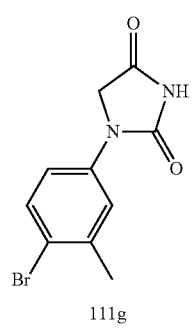

(2-Chloro-acetyl)-carbamic acid ethyl ester (356 mg, 2.15 mmol) was added to 4-bromo-3-methyl-phenylamine (400 mg, 2.15 mmol) and dimethylphenylamine (273 μL, 2.15 mmol) at room temperature. The mixture was stirred at 130° C. for five hours, and the reaction solution was then cooled. The precipitate was collected by filtration and washed with CH$_3$CN to give 1-(4-bromo-3-methyl-phenyl)-imidazolidine-2,4-dione as a colorless solid (314 mg, 54%).

MS (ESI) m/z=267, 269 (M+H)+.

The aryl bromide reagent used in the synthesis of Compound 625 (1-(4-bromo-3-methyl-phenyl)-5-methyl-imidazolidine-2,4-dione) was synthesized as follows.

2-Bromo-propionic acid ethyl ester (973 mg, 5.22 mmol) was added to 4-bromo-3-methyl-phenylamine (1.00 g, 5.37 mmol) and dimethylphenylamine (682 μL, 5.37 mmol) at room temperature, and the mixture was stirred at 60° C. for 15 hours. The reaction solution was then cooled and concentrated under reduced pressure. The resulting residue was purified by silica gel column chromatography (hexane-ethyl acetate) to give 2-(4-bromo-3-methyl-phenylamino)-propionic acid ethyl ester as a yellow form (1.38 g, 90%).

MS (ESI) m/z=286, 288 (M+H)+.

(Reaction 111-5)

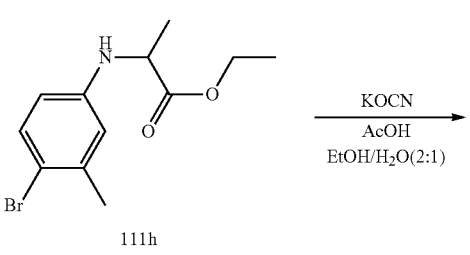

685

-continued

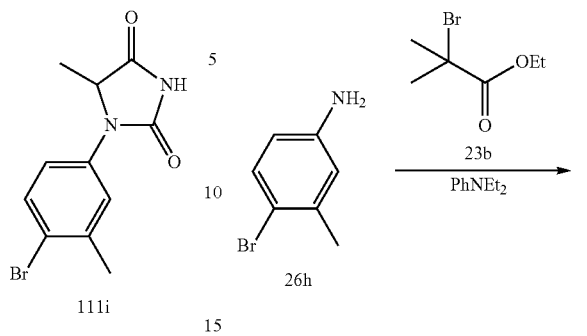

111i

KOCN (326 mg, 4.02 mmol) was added to a mixed solution of 2-(4-bromo-3-methyl-phenylamino)-propionic acid ethyl ester (383 mg, 1.34 mmol) in EtOH (5.30 mL) and H$_2$O (2.68 mL). The mixture was stirred at room temperature for three hours and at 60° C. for 11 hours, and AcOH (1 mL) was then added, followed by further stirring for two hours. KOCN (163 mg, 2.01 mmol) was added, followed by further stirring for three hours. The reaction solution was cooled. H$_2$O (50 mL) was added to the reaction solution at room temperature, and this aqueous layer was then extracted with ethyl acetate (20 mL×3). The organic layers were concentrated under reduced pressure, and the resulting residue was purified by silica gel column chromatography (dichloromethane-methanol) to give 1-(4-bromo-3-methyl-phenyl)-5-methyl-imidazolidine-2,4-dione as a yellow form (134 mg, 35%).

MS (ESI) m/z=283, 285 (M+H)+.

The aryl bromide reagent used in the synthesis of Compound 626 (1-(4-bromo-3-methyl-phenyl)-5,5-dimethyl-imidazolidine-2,4-dione) was synthesized as follows.

686

(Reaction 111-6)

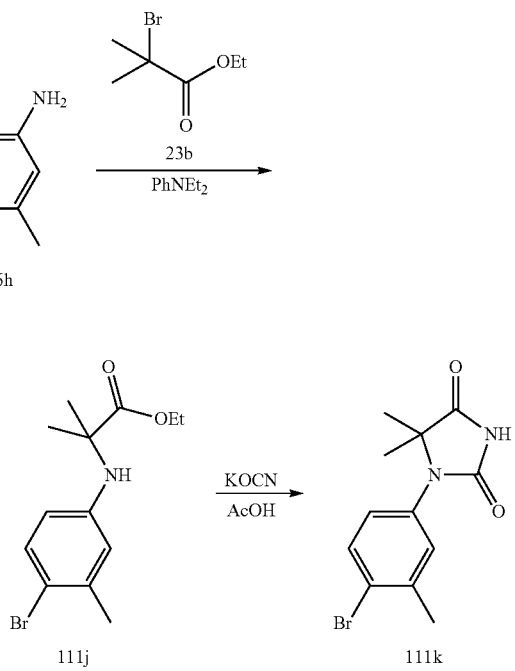

1-(4-Bromo-3-methyl-phenyl)-5,5-dimethyl-imidazolidine-2,4-dione was synthesized by operations similar to those in Reaction 111-4 and Reaction 111-5 using appropriate reagents and starting material.

MS (ESI) m/z=297, 299 (M+H)+.

Example 112

8-{(E)-2-[4-(3,4-Dihydroxy-butoxy)-2,6-dimethyl-phenyl]-ethenesulfonyl}-2-nonyl-1,3,8-triaza-spiro[4.5]dec-1-en-4-one (Compound 627)

(Reaction 112-1)

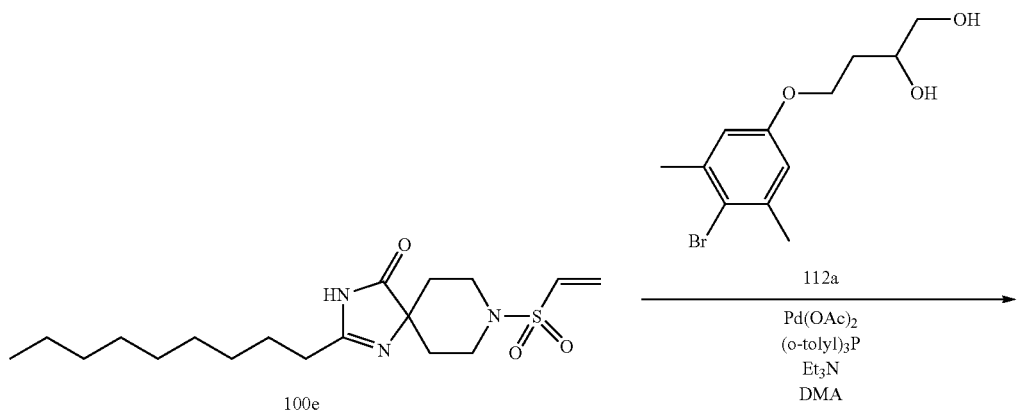

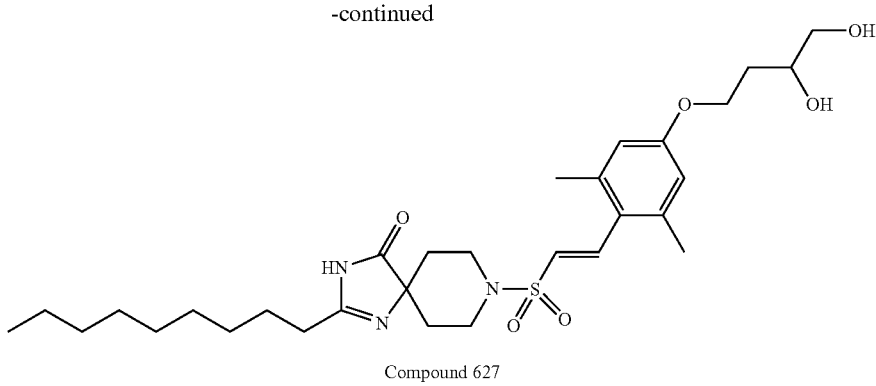

Compound 627

8-{(E)-2-[4-(3,4-Dihydroxy-butoxy)-2,6-dimethyl-phenyl]-ethenesulfonyl}-2-nonyl-1,3,8-triaza-spiro[4.5]dec-1-en-4-one was synthesized by operations similar to those in Reaction 26-1 using appropriate reagents and starting material.

MS (ESI) m/z=578 (M+H)+.

The example compound shown below was synthesized by operations similar to those in Example 112 using appropriate reagents and starting material.

Compound 628

TABLE 85

| Target Compound | Structure | LCMS condition | Retention time (min) | MS (m/z) |
|---|---|---|---|---|
| 628 | 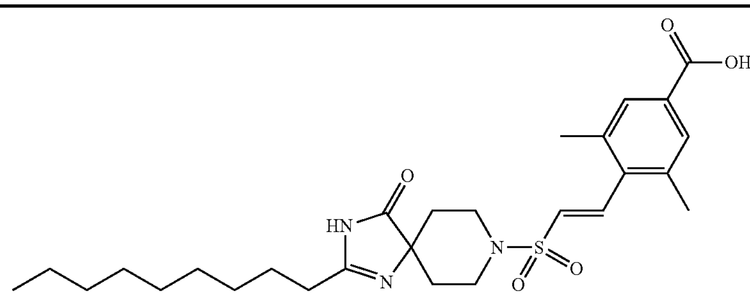 | LCMS-F-1 | 0.96 | 518 (M + H)+ |

Example 113

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide (Compound 629)

(Reaction 113-1)

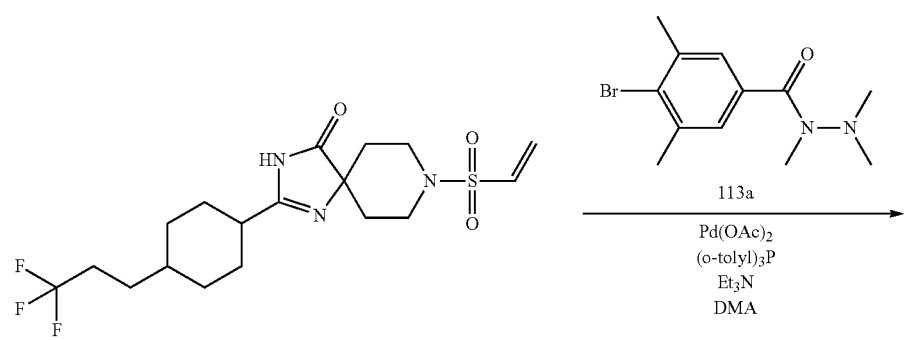

-continued

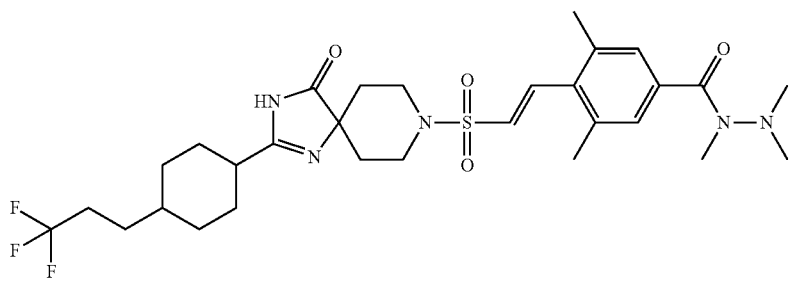

Compound 629

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid trimethylhydrazide was synthesized by operations similar to those in Reaction 26-1 using appropriate reagents and starting material.

MS (ESI) m/z=626 (M+H)+.

The example compound shown below was synthesized by operations similar to those in Example 113 using appropriate reagents and starting material.

Compound 630

-continued

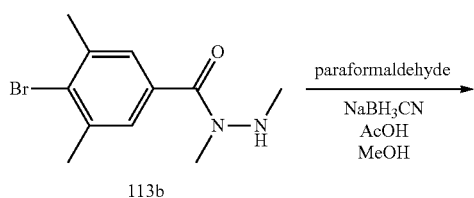

TABLE 86

| Target Compound | Structure | LCMS condition | Retention time (min) | MS (m/z) |
|---|---|---|---|---|
| 630 | 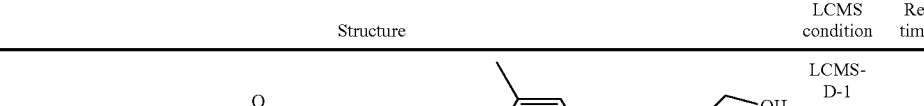 | LCMS-D-1 | 2.37 | 639 (M + H)+ |

The aryl bromide reagent used in the synthesis of Compound 629 (4-bromo-3,5-dimethyl-benzoic acid trimethylhydrazide) was synthesized as follows.

(Reaction 113-2)

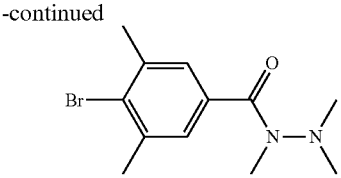

-continued

4-Bromo-3,5-dimethyl-benzoic acid trimethylhydrazide was synthesized by operations similar to those in Reaction 10-14 and Reaction 41-1 using appropriate reagents and starting material.

$^1$H-NMR (CDCl$_3$) δ 7.20 (s, 2H), 3.02 (s, 2H), 2.48 (s, 6H), 2.42 (s, 6H).

The aryl bromide reagent used in the synthesis of Compound 630 ((R)-3-(5-bromo-4,6-dimethyl-indol-1-yl)-propane-1,2-diol) was synthesized as follows.

(Reaction 113-3)

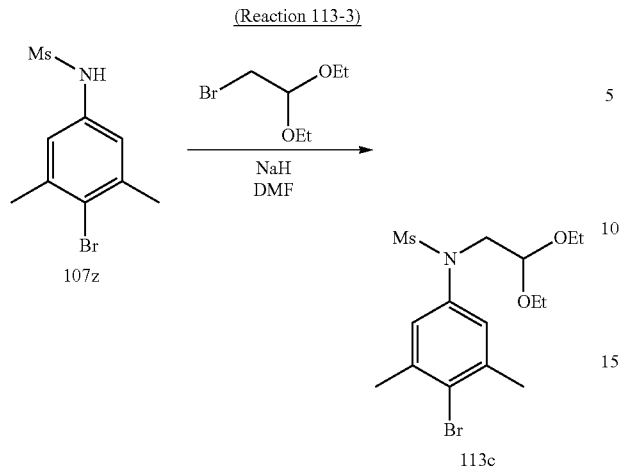

N-(4-Bromo-3,5-dimethyl-phenyl)-N-(2,2-diethoxy-ethyl)-methanesulfonamide was synthesized by operations similar to those in Reaction 25-3 using appropriate reagents and starting material.

¹H-NMR (CDCl₃) δ 7.06 (s, 2H), 4.57 (t, 1H, J=5.72 Hz), 3.71 (d, 2H, J=5.72 Hz), 3.64 (m, 2H), 3.49 (m, 2H), 2.95 (s, 3H), 2.40 (s, 6H), 1.15 (t, 6H, J=7.24 Hz).

(Reaction 113-4)

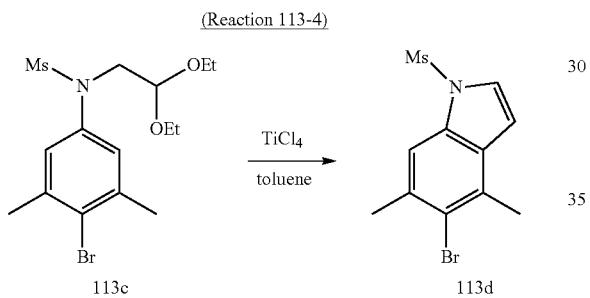

A 1 M solution of titanium(IV) chloride in dichloroethane (5.3 ml, 5.3 mmol) was added to a solution of N-(4-bromo-3,5-dimethyl-phenyl)-N-(2,2-diethoxy-ethyl)-methanesulfonamide (2.09 g, 5.3 mmol) in toluene (17 ml) at room temperature, and the mixture was heated with stirring at 100° C. for two hours. An aqueous sodium bicarbonate solution was added to the reaction solution, followed by extraction with ethyl acetate. The organic phase was washed with saturated brine and concentrated under reduced pressure. The resulting residue was purified by silica gel column chromatography (hexane-ethyl acetate) to give 5-bromo-4,6-dimethyl-1-methanesulfonyl-indole (1.28 g, 80%).

¹H-NMR (CDCl₃) δ 7.66 (s, 1H), 7.37 (d, 1H, J=3.81 Hz), 6.69 (dd, 1H, J=3.81, 0.76 Hz), 3.07 (s, 3H), 2.57 (d, 6H, J=13.73 Hz).

(Reaction 113-5)

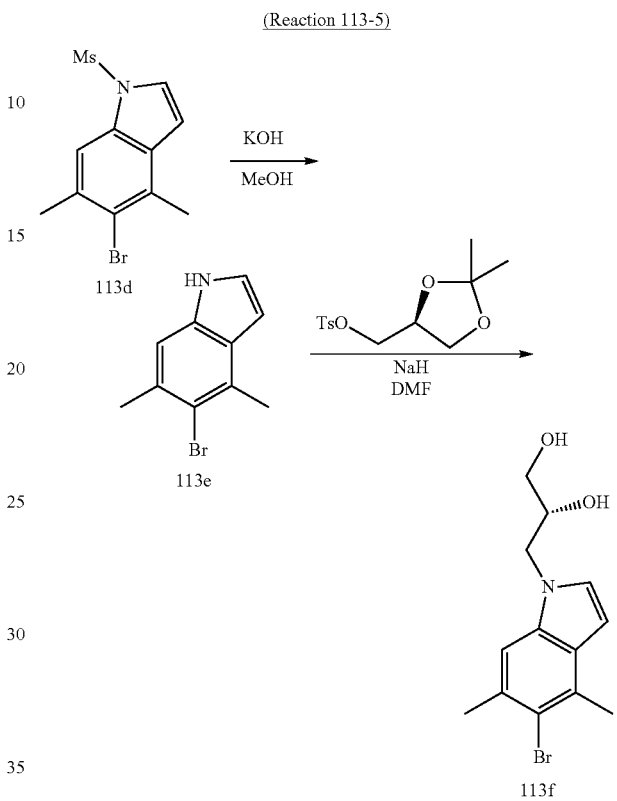

(R)-3-(5-Bromo-4,6-dimethyl-indol-1-yl)-propane-1,2-diol was synthesized by operations similar to those in Reaction 14-1 and Reaction 25-3 using appropriate reagents and starting material.

MS (ESI) m/z=298, 300 (M+H)+.

Example 114

3-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-imidazolidine-2,4-dione (Compound 631)

(Reaction 114-1)

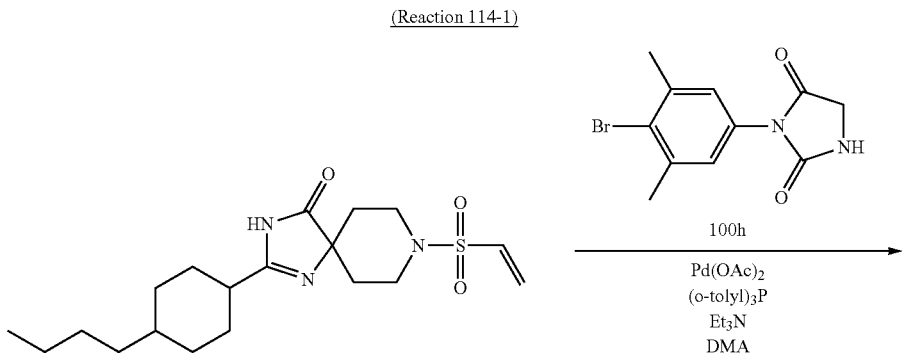

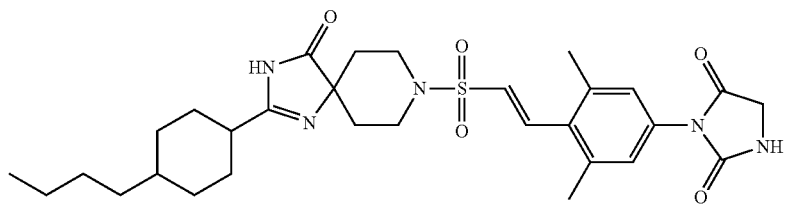

Compound 631

3-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-imidazolidine-2,4-dione was synthesized by operations similar to those in Reaction 26-1 using appropriate reagents and starting material.

MS (ESI) m/z=584 (M+H)+.

The example compound shown below was synthesized by operations similar to those in Example 114 using appropriate reagents and starting material.

Compound 632

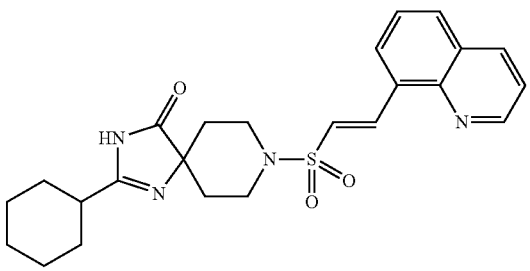 [SMILES: CN1CCCc2c(/C=C/S(=O)(=O)N3CCC4(CC3)N=C(C3CCCCC3)NC4=O)cccc21]

Compound 633

TABLE 87

| Target Compound | Structure | LCMS condition | Retention time (min) | MS (m/z) |
|---|---|---|---|---|
| 632 | (structure shown) | LCMS-D-1 | 3.22 | 627 (M + H)+ |

Example 115

2-Cyclohexyl-8-((E)-2-quinolin-8-yl-ethenesulfonyl)-1,3,8-triaza-spiro[4.5]dec-1-en-4-one (Compound 633)

(Reaction 115-1)

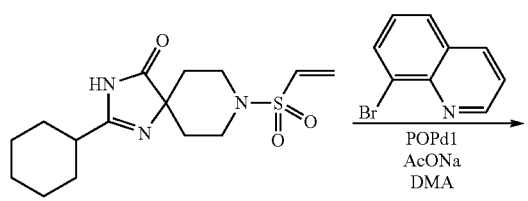

2-Cyclohexyl-8-ethenesulfonyl-1,3,8-triaza-spiro[4.5]dec-1-en-4-one (20 mg, 61.5 μmol), 8-bromoquinoline (19 mg, 91.3 μmol), POPd1 (Combiphos, 2.9 mg, 3.1 μmol) and sodium acetate (7.6 mg, 92.6 μmol) in dimethylacetamide (0.6 ml) were mixed in a sealed vessel in a nitrogen atmosphere. This mixture was irradiated in a microwave apparatus (190° C., 40 min). The reaction mixture was cooled, and then quenched with water and extracted with ethyl acetate. The organic layer was washed with saturated brine, and then dried over anhydrous sodium sulfate and concentrated under reduced pressure. The resulting residue was purified by silica gel column chromatography to give 2-cyclohexyl-8-((E)-2-quinolin-8-yl-ethenesulfonyl)-1,3,8-triaza-spiro[4.5]dec-1-en-4-one (15.3 mg, 16%).

MS (ESI) m/z=453 (M+H)+.

The example compound shown below was synthesized by operations similar to those in Example 115 using appropriate reagents and starting material.

Compound 634

TABLE 88

| Target Compound | Structure | LCMS condition | Retention time (min) | MS (m/z) |
|---|---|---|---|---|
| 634 | 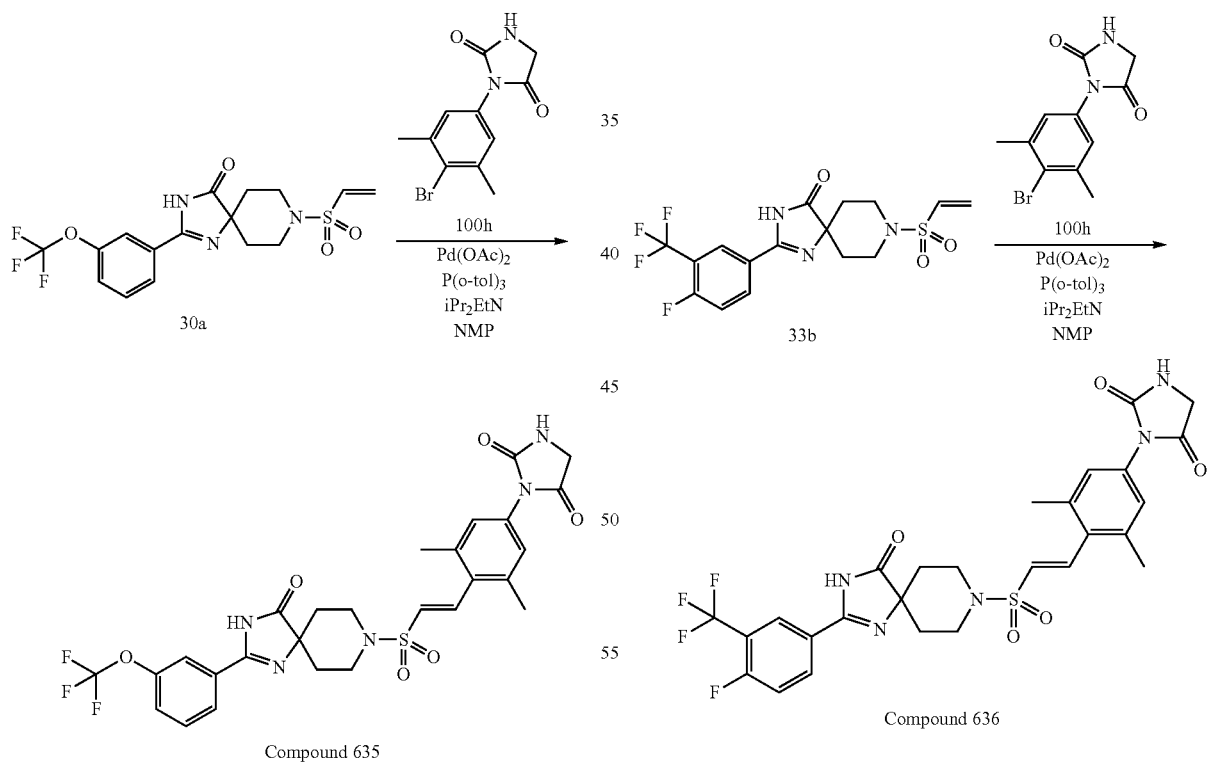 | LCMS-C-1 | 2.3 | 457 (M + H)+ |

Example 116

3-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione (Compound 635)

(Reaction 116-1)

3-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-imidazolidine-2,4-dione was synthesized by operations similar to those in Reaction 26-1 (using NMP as a solvent) using appropriate reagents and starting material.

MS (ESI) m/z=606 (M+H)+.

Example 117

3-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione (Compound 636)

(Reaction 117-1)

Compound 636

3-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-imidazolidine-2,4-dione was synthesized by operations similar to those in Reaction 26-1 (using NMP as a solvent) using appropriate reagents and starting material.

MS (ESI) m/z=608 (M+H)+.

Example 118

2-Cyclohexyl-8-[(E)-2-(2-methyl-1H-indol-4-yl)-ethenesulfonyl]-1,3,8-triaza-spiro[4.5]dec-1-en-4-one (Compound 637)

(Reaction 118-1)

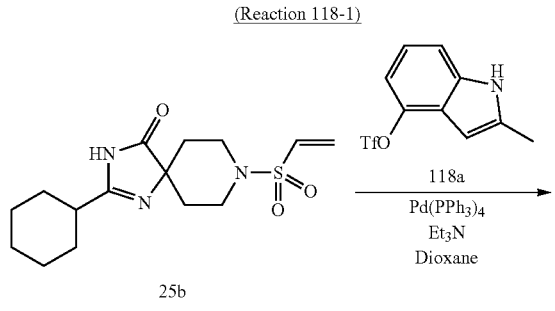

quenched with water and extracted with ethyl acetate. The organic layer was washed with saturated brine, and then dried over anhydrous sodium sulfate and concentrated under reduced pressure. The resulting residue was purified by silica gel column chromatography to give 2-cyclohexyl-8-[(E)-2-(2-methyl-1H-indol-4-yl)-ethenesulfonyl]-1,3,8-triaza-spiro[4.5]dec-1-en-4-one (19.3 mg, 14%).

MS (ESI) m/z=455 (M+H)+.

The example compound shown below was synthesized by operations similar to those in Example 118 using appropriate reagents and starting material.

Compound 638

TABLE 89

| Target Compound | Structure | LCMS condition | Retention time (min) | MS (m/z) |
|---|---|---|---|---|
| 638 | 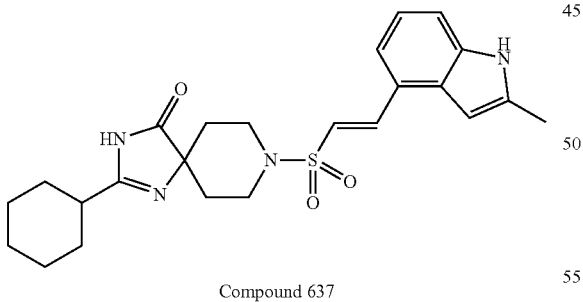 | LCMS-A-1 | 1.99 | 471 (M + H)+ |

-continued

Compound 637

A mixture of 2-cyclohexyl-8-ethenesulfonyl-1,3,8-triaza-spiro[4.5]dec-1-en-4-one (100 mg, 0.307 mmol), trifluoromethanesulfonic acid 2-methyl-1H-indol-4-yl ester (129 mg, 0.462 mmol), tetrakistriphenylphosphine palladium(0) (35 mg, 30.2 µmol) and triethylamine (130 µL, 0.933 mmol) in 1,4-dioxane (1.5 ml) was heated with stirring at 100° C. for 18 hours. The reaction mixture was cooled, and then Toluene-4-sulfonic acid 1-methyl-1,2,3,4-tetrahydro-quinolin-5-yl ester used in the synthesis of Compound 638 was synthesized as follows.

(Reaction 118-2)

118b

699

-continued

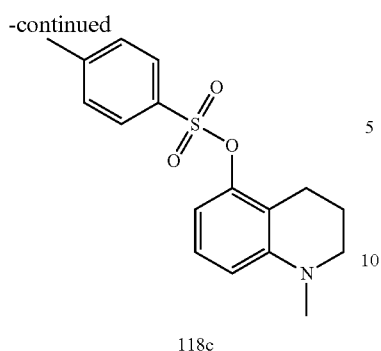

118c

Toluene-4-sulfonic acid 1-methyl-1,2,3,4-tetrahydro-quinolin-5-yl ester was synthesized by operations similar to those in Reaction 25-3 using appropriate reagents and starting material.

$^1$H-NMR (270 MHz, CDCl$_3$) δ 1.92-2.02 (2H, m), 2.75-2.82 (2H, m), 2.92 (3H, s), 3.22-3.28 (2H, m), 6.50-6.55 (2H, m), 7.03-7.10 (1H, dd, J=8.1, 8.1 Hz).

Example 119

8-{(E)-2-[4-(3,4-Dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one
(Compound 639)

700

8-Ethenesulfonyl-2-(4-fluoro-3-trifluoromethyl-phenyl)-1,3,8-triaza-spiro[4.5]dec-1-en-4-one (57.6 mg, 0.142 mmol), 4-(4-bromo-3,5-dimethyl-phenoxy)-butane-1,2-diol (49.3 mg, 0.170 mmol), bis(dibenzylideneacetone)palladium(0) (8 mg, 0.014 mmol) and tri-tert-butylphosphine tetrafluoroborate (4 mg, 0.014 mmol) were placed in a vial. NMP (0.5 ml) and N-methyldicyclohexylamine (36.1 μl, 0.170 mmol) were sequentially added in a nitrogen atmosphere, and the mixture was heated with stirring at 100° C. for 2.5 hours. A saturated aqueous NH$_4$Cl solution was added to the reaction mixture, followed by extraction with ethyl acetate. The organic layer was sequentially washed with water and saturated brine and then concentrated under reduced pressure. The resulting residue was purified by thin layer chromatography (ethyl acetate:dichloromethane:methanol=10:10:1) to give 8-{(E)-2-[4-(3,4-dihydroxy-butoxy)-2,6-dimethyl-phenyl]-ethenesulfonyl}-2-(4-fluoro-3-trifluoromethyl-phenyl)-1,3,8-triaza-spiro[4.5]dec-1-en-4-one (42.8 mg, 49%).

MS (ESI) m/z=614 (M+H)+.

The example compounds shown below were synthesized by operations similar to those in Example 119 using appropriate reagents and starting materials.

(Reaction 119-1)

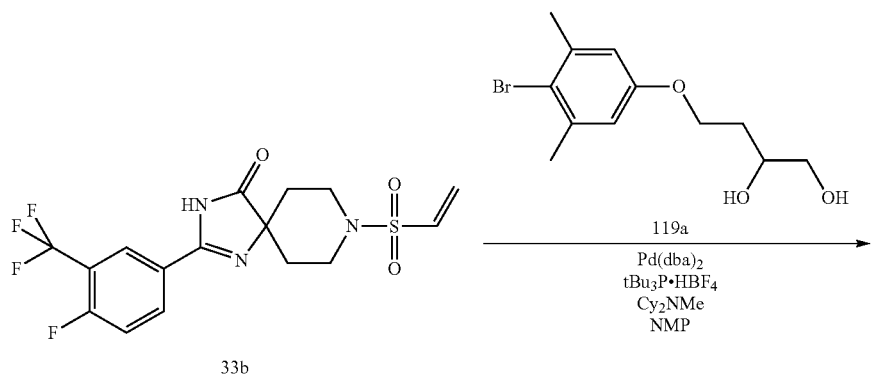

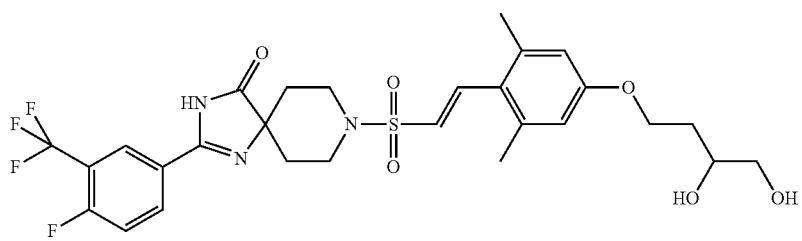

Compound 639

Compounds 640 to Compound 644

TABLE 90

| Target Compound | Structure | LCMS condition | Retention time (min) | MS (m/z) |
|---|---|---|---|---|
| 640 | 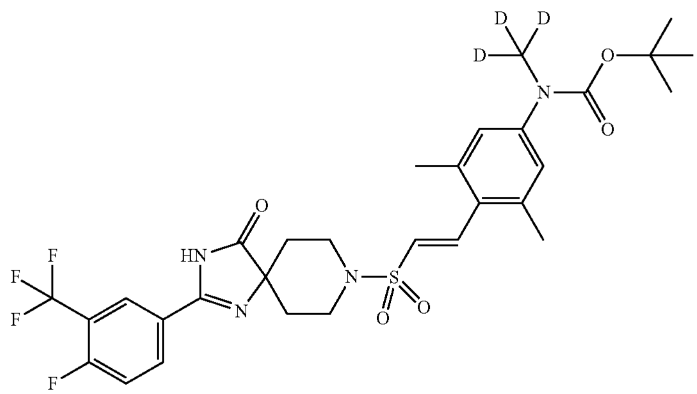 [SMILES: [2H]C([2H])([2H])N(C(=O)OC(C)(C)C)c1cc(C)c(/C=C/S(=O)(=O)N2CCC3(CC2)N=C(c2ccc(F)c(C(F)(F)F)c2)NC3=O)c(C)c1] | LCMS-F-1 | 1.13 | 642 (M + H)+ |
| 641 | 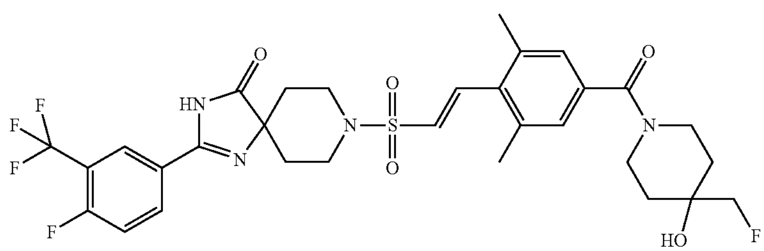 | LCMS-F-1 | 0.99 | 699 (M + H)+ |
| 642 | 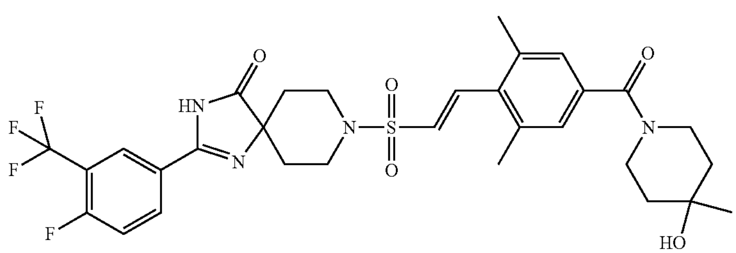 [SMILES: Cc1cc(C(=O)N2CCC(C)(O)CC2)cc(C)c1/C=C/S(=O)(=O)N1CCC2(CC1)N=C(c1ccc(F)c(C(F)(F)F)c1)NC2=O] | LCMS-C-1 | 2.7 | 651 (M + H)+ |
| 643 | 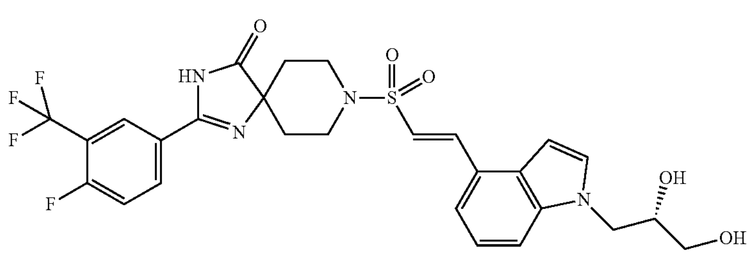 [SMILES: O=C1NC(c2ccc(F)c(C(F)(F)F)c2)=NC12CCN(S(=O)(=O)/C=C/c1cccc3c1ccn3C[C@H](O)CO)CC2] | LCMS-C-1 | 2.6 | 595 (M + H)+ |
| 644 | 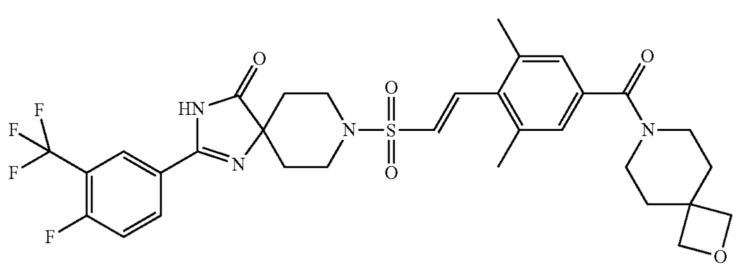 [SMILES: Cc1cc(C(=O)N2CCC3(CC2)COC3)cc(C)c1/C=C/S(=O)(=O)N1CCC2(CC1)N=C(c1ccc(F)c(C(F)(F)F)c1)NC2=O] | LCMS-F-1 | 1 | 663 (M + H)+ |

The aryl bromide reagent used in the synthesis of Compound 640 ((4-bromo-3,5-dimethyl-phenyl)-[1,1,1-²H₃]methyl-carbamic acid tert-butyl ester) was synthesized as follows.

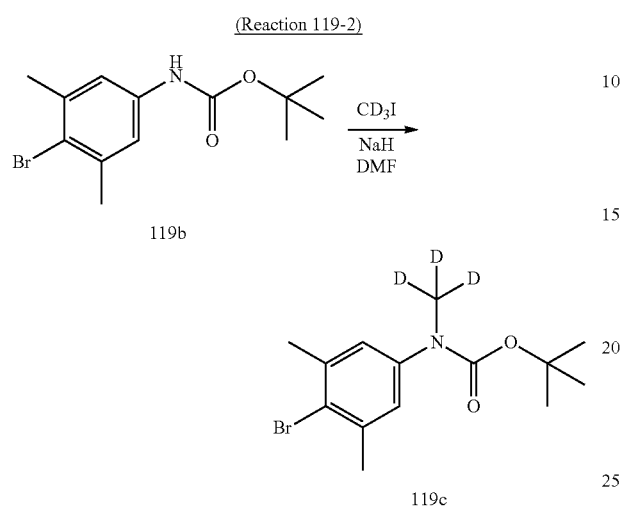

(4-Bromo-3,5-dimethyl-phenyl)-[1,1,1-²H₃]methyl-carbamic acid tert-butyl ester was synthesized by operations similar to those in Reaction 25-3 using appropriate reagents and starting material.

MS (ESI) m/z=317 (M+H)+.

The aryl bromide reagent used in the synthesis of Compound 641 ((4-bromo-3,5-dimethyl-phenyl)-(4-fluoromethyl-4-hydroxy-piperidin-1-yl)-methanone) was synthesized as follows.

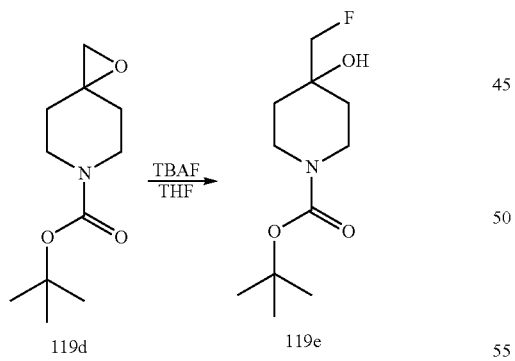

Tetrabutylammonium fluoride (1.0 M in THF, 5.6 ml, 5.6 mmol) was added to a solution of 1-oxa-6-aza-spiro[2.5]octane-6-carboxylic acid tert-butyl ester (400 mg, 1.87 mmol) in tetrahydrofuran (5 ml), and the mixture was heated under reflux for 36 hours. The reaction solution was cooled and then concentrated under reduced pressure. The resulting residue was purified by silica gel column chromatography (ethyl acetate-hexane) to give 4-fluoromethyl-4-hydroxy-piperidine-1-carboxylic acid tert-butyl ester (87 mg, 19%).

¹H-NMR (CDCl₃) δ 1.46 (s, 9H), 2.93-3.31 (m, 2H), 3.69-3.94 (m, 2H), 4.14 (s, 1H), 4.30 (s, 1H).

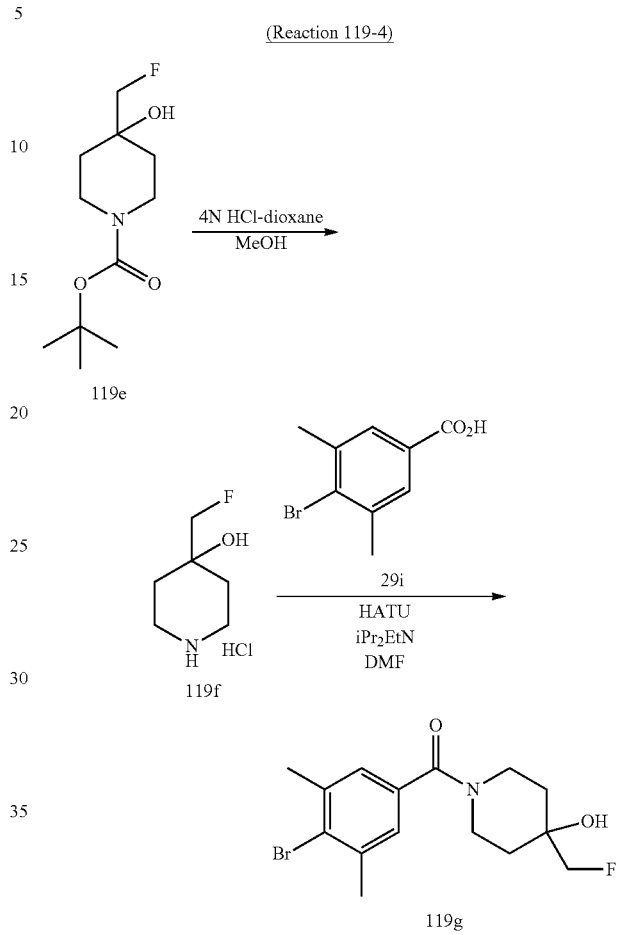

(4-Bromo-3,5-dimethyl-phenyl)-(4-fluoromethyl-4-hydroxy-piperidin-1-yl)-methanone was synthesized by operations similar to those in Reaction 5-3 and Reaction 10-14 using appropriate reagents and starting material.

MS (ESI) m/z=344, 346 (M+H)+.

The aryl bromide reagent used in the synthesis of Compound 642 ((4-bromo-3,5-dimethyl-phenyl)-(4-hydroxy-4-methyl-piperidin-1-yl)-methanone) was synthesized as follows.

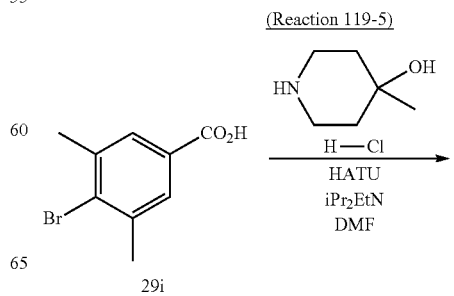

705
-continued

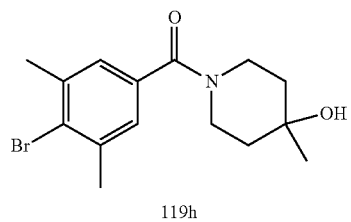

119h (4-Bromo-3,5-dimethyl-phenyl)-(4-hydroxy-4-methyl-piperidin-1-yl)-methanone was synthesized by operations similar to those in Reaction 10-14 using appropriate reagents and starting material.

MS (ESI) m/z=326, 328 (M+H)+.

The aryl bromide reagent used in the synthesis of Compound 644 ((4-bromo-3,5-dimethyl-phenyl)-(2-oxa-7-aza-spiro[3.5]non-7-yl)-methanone) was synthesized as follows.

(Reaction 119-6)

29i

→ HATU
iPr₂EtN
DMF

119i (4-Bromo-3,5-dimethyl-phenyl)-(2-oxa-7-aza-spiro[3.5]non-7-yl)-methanone was synthesized by operations similar to those in Reaction 10-14 using appropriate reagents and starting material.

MS (ESI) m/z=338, 340 (M+H)+.

706

Example 120

2-Cyclohexyl-8-[2-(1,2,3,4-tetrahydro-quinolin-5-yl)-ethanesulfonyl]-1,3,8-triaza-spiro[4.5]dec-1-en-4-one (Compound 645)

(Reaction 120-1)

25b → Pd(OAc)₂
(o-tolyl)₃P
Et₃N
DMA

→ 10% Pd—C/H₂
MeOH—DMF

120a

Compound 645

2-Cyclohexyl-8-[2-(1,2,3,4-tetrahydro-quinolin-5-yl)-ethanesulfonyl]-1,3,8-triaza-spiro[4.5]dec-1-en-4-one was synthesized by operations similar to those in Reaction 25-2 and Reaction 42-1 using appropriate reagents and starting material.

MS (ESI) m/z=459 (M+H)+.

The example compounds shown below were synthesized by operations similar to those in Example 120 using appropriate reagents and starting materials.

Compounds 646 to Compound 652

TABLE 91

| Target Compound | Structure | LCMS condition | Retention time (min) | MS (m/z) |
|---|---|---|---|---|
| 646 | 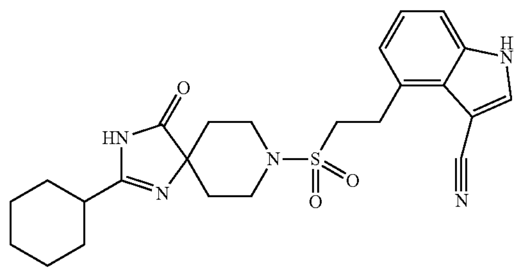 [SMILES: N#Cc1c[nH]c2cccc(CCS(=O)(=O)N3CCC4(CC3)N=C(C3CCCCC3)NC4=O)c12] | LCMS-C-1 | 2.42 | 468 (M + H)+ |
| 647 | 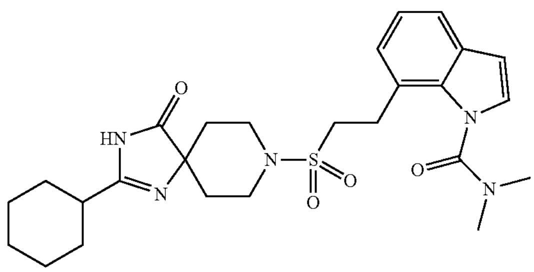 [SMILES: CN(C)C(=O)n1ccc2cccc(CCS(=O)(=O)N3CCC4(CC3)N=C(C3CCCCC3)NC4=O)c21] | LCMS-C-1 | 2.60 | 514 (M + H)+ |
| 648 | 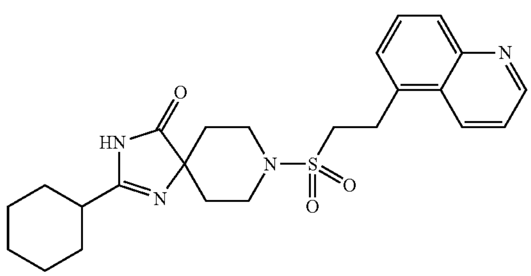 [SMILES: O=C1NC(C2CCCCC2)=NC12CCN(S(=O)(=O)CCc1cccc3ncccc13)CC2] | LCMS-C-1 | 2.47 | 455 (M + H)+ |
| 649 | 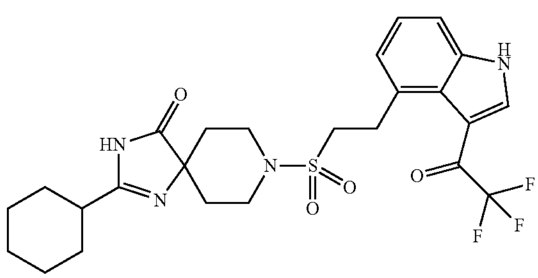 [SMILES: O=C(c1c[nH]c2cccc(CCS(=O)(=O)N3CCC4(CC3)N=C(C3CCCCC3)NC4=O)c12)C(F)(F)F] | LCMS-C-1 | 2.70 | 539 (M + H)+ |
| 650 | 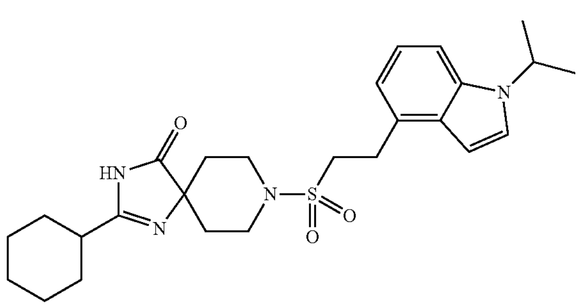 [SMILES: CC(C)n1ccc2c(CCS(=O)(=O)N3CCC4(CC3)N=C(C3CCCCC3)NC4=O)cccc21] | LCMS-C-1 | 2.88 | 485 (M + H)+ |

TABLE 91-continued

| Target Compound | Structure | LCMS condition | Retention time (min) | MS (m/z) |
|---|---|---|---|---|
| 651 | 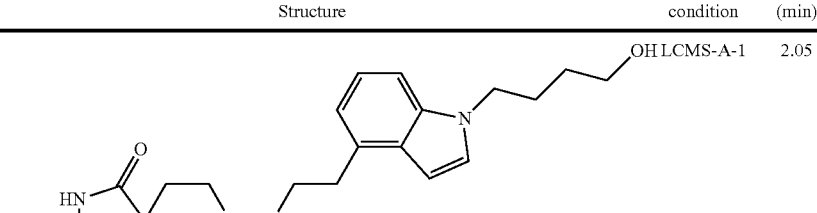 | LCMS-A-1 | 2.05 | 515 (M + H)+ |
| 652 | 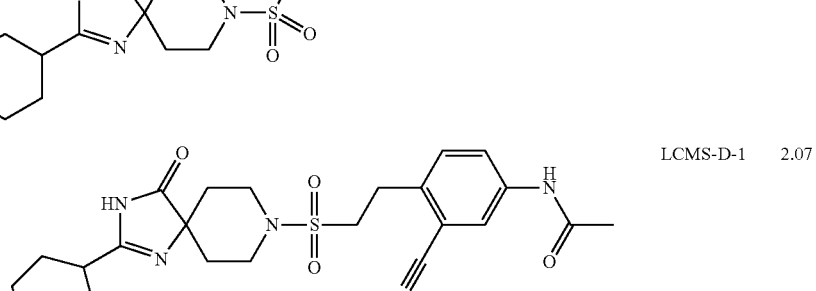 | LCMS-D-1 | 2.07 | 486 (M + H)+ |

The aryl bromide reagent used in the synthesis of Compound 647 ((7-bromo-indole-1-carboxylic acid dimethylamide) was synthesized as follows.

(Reaction 120-2)

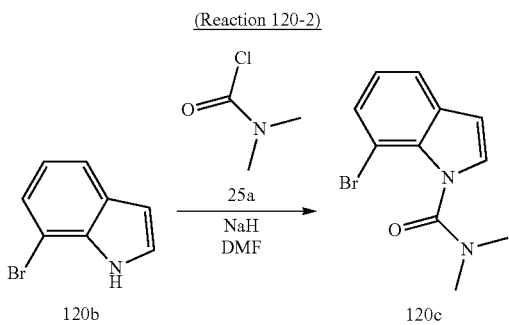

7-Bromo-indole-1-carboxylic acid dimethylamide was synthesized by operations similar to those in Reaction 25-3 using appropriate reagents and starting material.

MS (ESI) m/z=267, 269 (M+H)+.

The aryl bromide reagent used in the synthesis of Compound 649 (1-(4-bromo-1H-indol-3-yl)-2,2,2-trifluoro-ethanone) was synthesized as follows.

(Reaction 120-3)

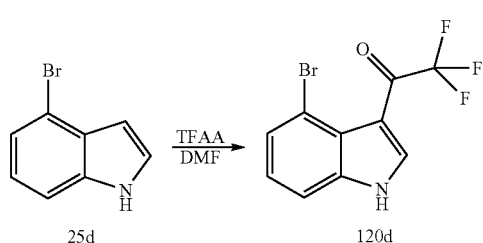

Trifluoroacetic anhydride (850 µL, 6.12 mmol) was added to a solution of 4-bromoindole (1.00 g, 5.10 mmol) in N,N-dimethylformamide (2.0 mL), and the mixture was stirred at room temperature for 1.5 hours. Water was added, followed by extraction with a mixed solvent of ethyl acetate:hexane=4:1. The organic layers were combined, washed with a saturated aqueous sodium bicarbonate solution, water and saturated brine and dried over sodium sulfate, and the solvent was then distilled off. The residue was purified by silica gel column chromatography to give 1-(4-bromo-1H-indol-3-yl)-2,2,2-trifluoro-ethanone (353 mg, 24%).

MS (ESI) m/z=292 (M+H)+.

The aryl bromide reagent used in the synthesis of Compound 650 (4-bromo-1-isopropyl-1H-indole) was synthesized as follows.

(Reaction 120-4)

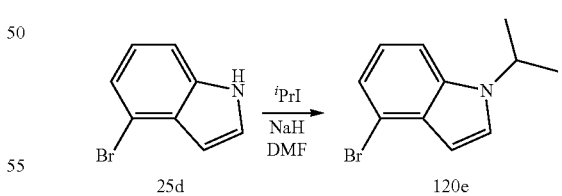

4-Bromo-1-isopropyl-1H-indole was synthesized by operations similar to those in Reaction 25-3 using appropriate reagents and starting material.

MS (ESI) m/z=238, 240 (M+H)+.

The aryl bromide reagent used in the synthesis of Compound 651 (4-(4-bromo-indol-1-yl)-butan-1-ol) was synthesized as follows.

(Reaction 120-5)

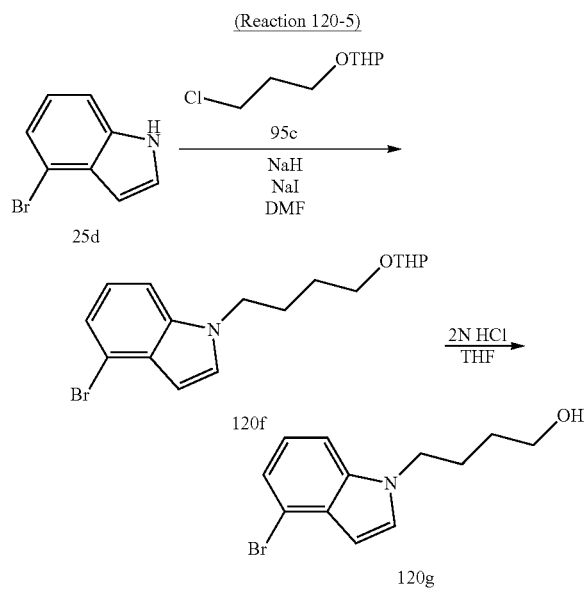

4-(4-Bromo-indol-1-yl)-butan-1-ol was synthesized by operations similar to those in Reaction 25-3 and Reaction 25-4 using appropriate reagents and starting material.

MS (ESI) m/z=268, 270 (M+H)+.

The aryl bromide reagent used in the synthesis of Compound 652 (N-(4-bromo-3-cyano-phenyl)-acetamide) was synthesized as follows.

(Reaction 120-6)

N-(4-Bromo-3-cyano-phenyl)-acetamide was synthesized by operations similar to those in Reaction 19-2 (using DMAP as a base) using appropriate reagents and starting material.

$^1$H-NMR (DMSO-d6) δ 10.39 (s, 1H), 8.18 (d, 1H, J 2.28 Hz), 7.79 (d, 1H, J=8.74 Hz), 7.70 (dd, 1H, J 9.15, 2.67 Hz), 2.07 (s, 3H).

Example 121

8-(2-Isoquinolin-5-yl-ethanesulfonyl)-2-(3-trifluoromethoxy-phenyl)-1,3,8-triaza-spiro[4.5]dec-1-en-4-one (Compound 653)

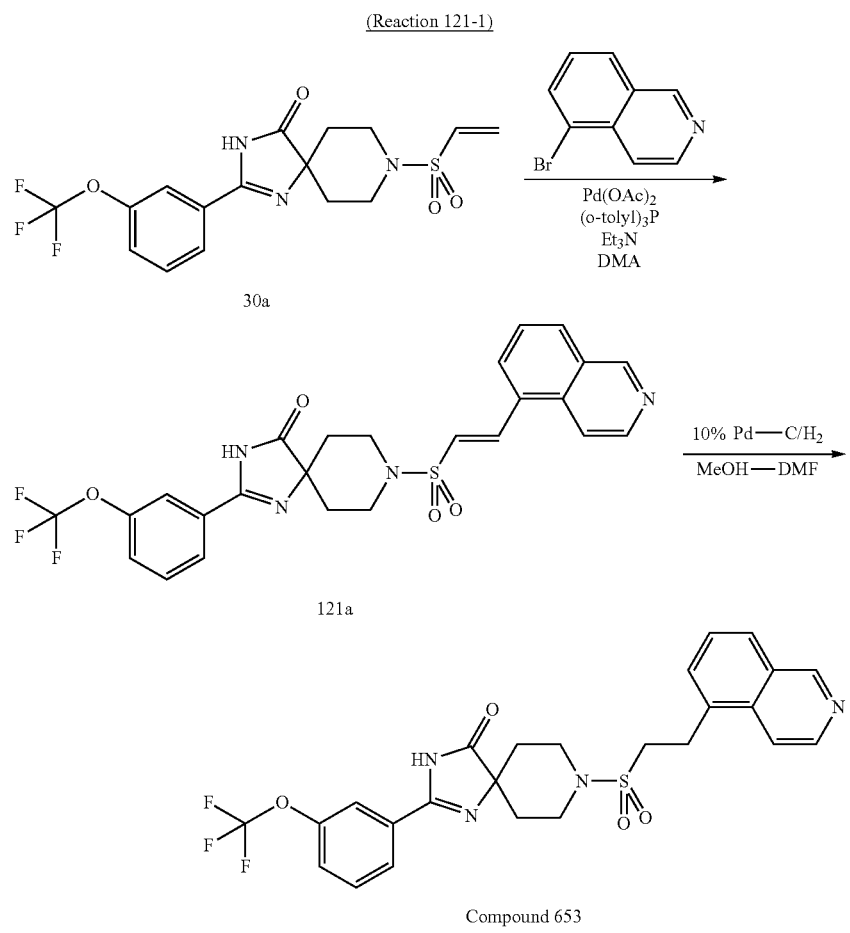

8-(2-Isoquinolin-5-yl-ethanesulfonyl)-2-(3-trifluoromethoxy-phenyl)-1,3,8-triaza-spiro[4.5]dec-1-en-4-one was synthesized by operations similar to those in Reaction 25-2 and Reaction 42-1 using appropriate reagents and starting material.

MS (ESI) m/z=533 (M+H)+.

The example compound shown below was synthesized by operations similar to those in Example 121 using appropriate reagents and starting material.

Compound 654

TABLE 92

| Target Compound | Structure | LCMS condition | Retention time (min) | MS (m/z) |
|---|---|---|---|---|
| 654 | 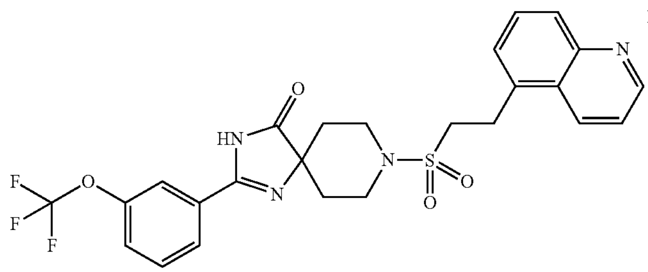 [SMILES: O=C1NC(c2cccc(OC(F)(F)F)c2)=NC12CCN(S(=O)(=O)CCc1cccc3ncccc13)CC2] | LCMS-A-1 | 2.02 | 533 (M + H)+ |

Example 122

N-(3-Methoxy-4-{2-[2-(4-methyl-cyclohexyl)-4-oxo-1,3,8-triaza-spiro[4.5]dec-1-ene-8-sulfonyl]-ethyl}-phenyl)-acetamide (Compound 655)

(Reaction 122-1)

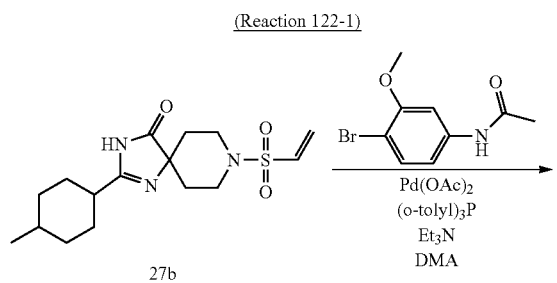

27b

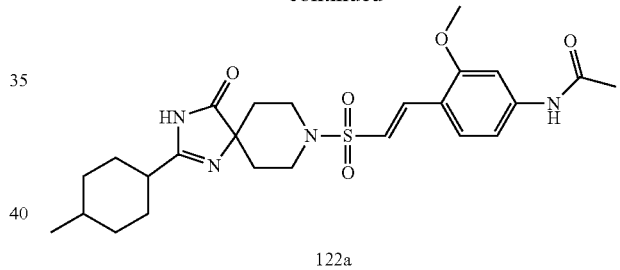

122a

N-(3-Methoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide was synthesized by operations similar to those in Reaction 25-2 using appropriate reagents and starting material.

MS (ESI) m/z=503 (M+H)+.

(Reaction 122-2)

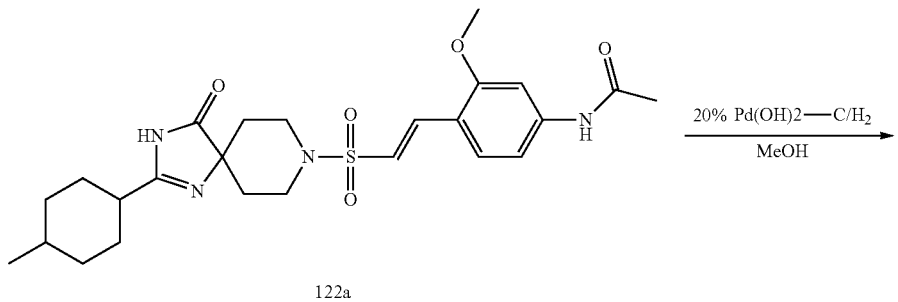

122a

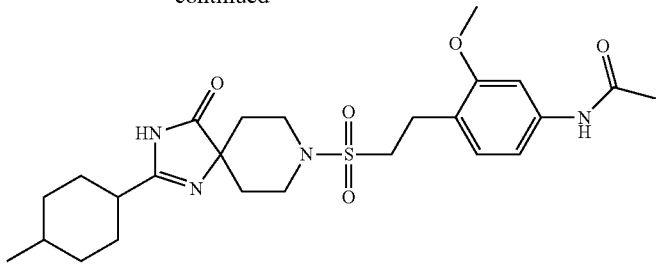

Compound 655

20% Pd(OH)2-C (30 mg) was placed into a solution of N-(3-methoxy-4-{(E)-2-[2-(4-methyl-cyclohexyl)-4-oxo-1,3,8-triaza-spiro[4.5]dec-1-ene-8-sulfonyl]-vinyl}-phenyl)-acetamide (31 mg, 0.0617 mmol) in methanol (5 ml), and the atmosphere was replaced with hydrogen. The mixture was stirred at room temperature for 16 hours. The reaction mixture was filtered, and the filtrate was then concentrated under reduced pressure. The resulting residue was purified by silica gel column chromatography (dichloromethane-ethyl acetate) to give N-(3-methoxy-4-{2-[2-(4-methyl-cyclohexyl)-4-oxo-1,3,8-triaza-spiro[4.5]dec-1-ene-8-sulfonyl]-ethyl}-phenyl)-acetamide (20 mg).

MS (ESI) m/z=505 (M+H)+.

The example compound shown below was synthesized by operations similar to those in Example 122 using appropriate reagents and starting material.

Compound 656

-continued

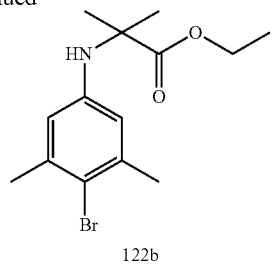

122b

Ethyl-2-bromoisobutyric acid (3.7 ml, 24.99 mmol) and sodium bicarbonate (630 mg, 7.49 mmol) were added to 4-bromo-3,5-dimethyl-aniline (500 mg, 2.49 mmol), and the mixture was irradiated with microwaves at 130° C. for 15 minutes. The reaction mixture was diluted with ethyl acetate, and the organic layer was sequentially washed with water and saturated brine and concentrated under reduced pressure. The resulting residue was purified by silica gel

TABLE 93

| Target Compound | Structure | LCMS condition | Retention time (min) | MS (m/z) |
|---|---|---|---|---|
| 656 | 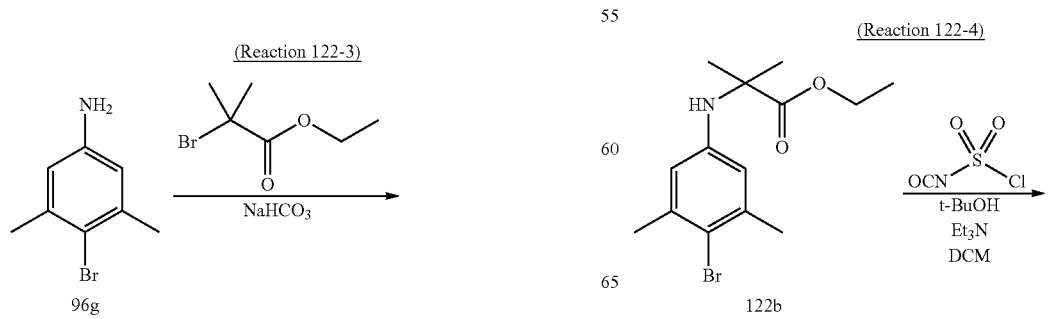 | LCMS-D-1 | 1.7 | 608 (M + H)+ |

The aryl bromide reagent used in the synthesis of Compound 656 (5-(4-bromo-3,5-dimethyl-phenyl)-4,4-dimethyl-1,1-dioxo-1λ⁶-[1,2,5]thiadiazolidin-3-one) was synthesized as follows.

column chromatography (hexane-ethyl acetate) to give ethyl 2-[(4-bromo-3,5-dimethyl-phenyl)amino]-2-methyl-propanoate (230 mg, 29%).

MS (ESI) m/z=314, 316 (M+H)+.

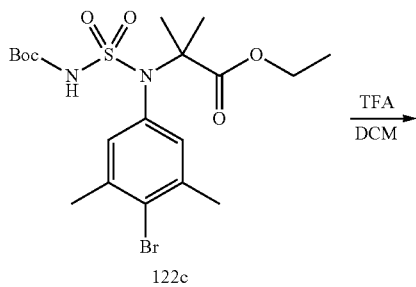

122c

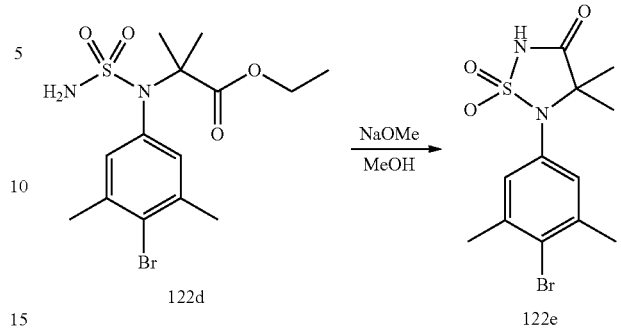

(Reaction 122-5)

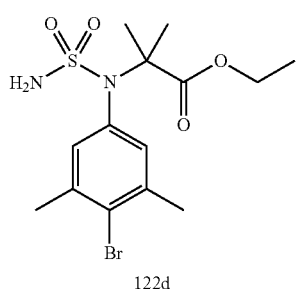

122d

Ethyl 2-[N-(4-bromo-3,5-dimethyl-phenyl)-N-sulfamoyl-amino]-2-methyl-propanoate was synthesized by operations similar to those in Reaction 92-2 and Reaction 7-2 using appropriate reagents and starting material.

MS (ESI) m/z=505 (M+H)+.

A 2 M solution of sodium methoxide in methanol (4 ml, 8 mmol) was added to a solution of ethyl 2-[N-(4-bromo-3,5-dimethyl-phenyl)-N-sulfamoyl-amino]-2-methyl-propanoate (100 mg, 0.254 mmol) in methanol (12 ml), and the mixture was irradiated with microwaves at 65° C. for 10 minutes. The reaction mixture was diluted with ethyl acetate, and the organic layer was sequentially washed with water and saturated brine and concentrated under reduced pressure to give 5-(4-bromo-3,5-dimethyl-phenyl)-4,4-dimethyl-1,1-dioxo-1$\lambda^6$-[1,2,5]thiadiazolidin-3-one (80 mg, 90%).

$^1$H-NMR (CDCl$_3$) δ 7.23 (s, 2H), 2.48 (s, 6H), 1.31 (s, 6H).

Example 123

8-{2-[2-Methyl-4-(3-oxo-morpholin-4-yl)-phenyl]-ethanesulfonyl}-2-nonyl-1,3,8-triaza-spiro[4.5]dec-1-en-4-one (Compound 657)

(Reaction 123-1)

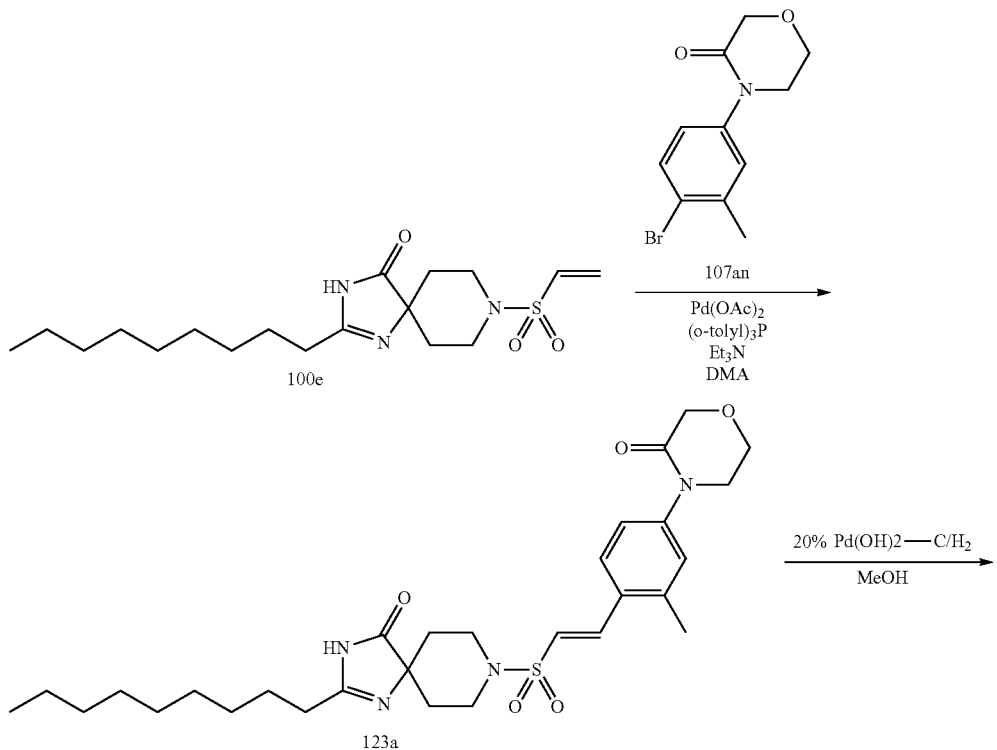

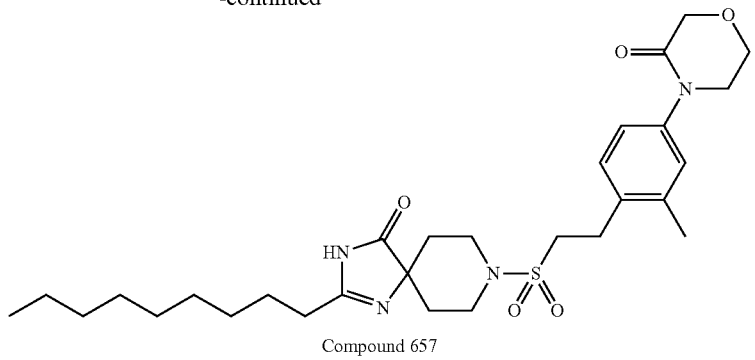
Compound 657
8-{2-[2-Methyl-4-(3-oxo-morpholin-4-yl)-phenyl]-ethanesulfonyl}-2-nonyl-1,3,8-triaza-spiro[4.5]dec-1-en-4-one was synthesized by operations similar to those in Reaction 25-2 and Reaction 122-2 using appropriate reagents and starting material.
MS (ESI) m/z=561 (M+H)+.
Example 124
{4-[2-(2-Cyclohexyl-4-oxo-1,3,8-triaza-spiro[4.5]dec-1-ene-8-sulfonyl)-ethyl]-benzyl}-carbamic acid isobutyl ester (Compound 658)
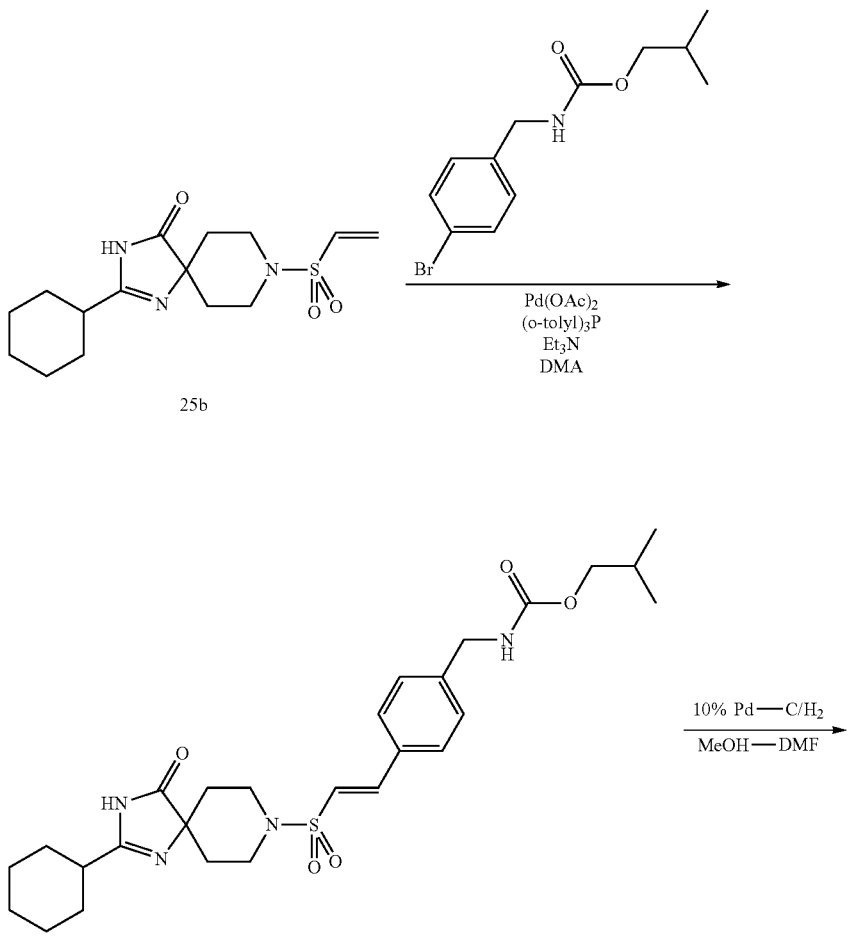

-continued

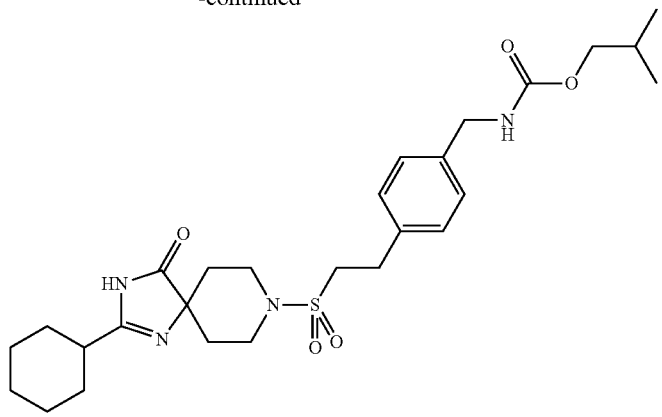

Compound 658

{4-[2-(2-Cyclohexyl-4-oxo-1,3,8-triaza-spiro[4.5]dec-1-ene-8-sulfonyl)-ethyl]-benzyl}-carbamic acid isobutyl ester was synthesized by operations similar to those in Reaction 25-2 and Reaction 42-2 using appropriate reagents and starting material.

MS (ESI) m/z=533 (M+H)+.

The example compounds shown below were synthesized by operations similar to those in Example 124 using appropriate reagents and starting materials.

Compounds 659 to Compound 664

TABLE 94

| Target Compound | Structure | LCMS condition | Retention time (min) | MS (m/z) |
|---|---|---|---|---|
| 659 | 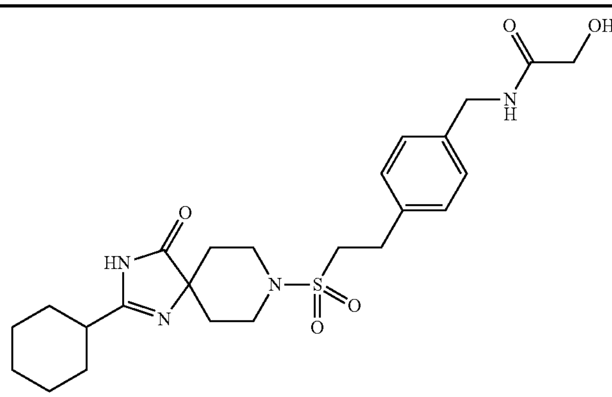 | LCMS-A-1 | 1.62 | 491 (M + H)+ |
| 660 | 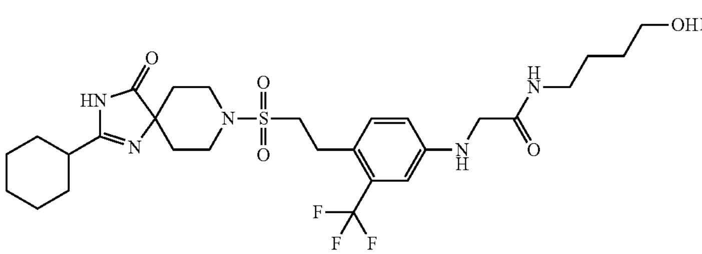 [SMILES: O=C(CNc1ccc(CCS(=O)(=O)N2CCC3(CC2)N=C(C2CCCCC2)NC3=O)c(C(F)(F)F)c1)NCCCCO] | LCMS-C-1 | 2.40 | 616 (M + H)+ |
| 661 | 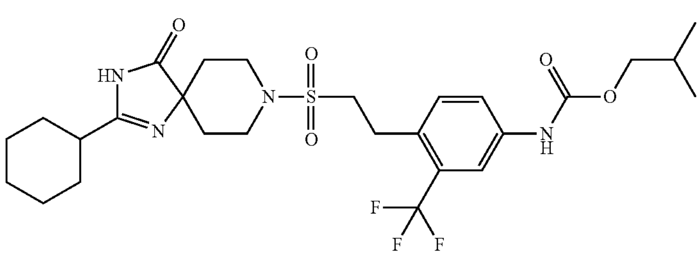 [SMILES: CC(C)COC(=O)Nc1ccc(CCS(=O)(=O)N2CCC3(CC2)N=C(C2CCCCC2)NC3=O)c(C(F)(F)F)c1] | LCMS-C-1 | 2.98 | 587 (M + H)+ |

TABLE 94-continued

| Target Compound | Structure | LCMS condition | Retention time (min) | MS (m/z) |
|---|---|---|---|---|
| 662 | 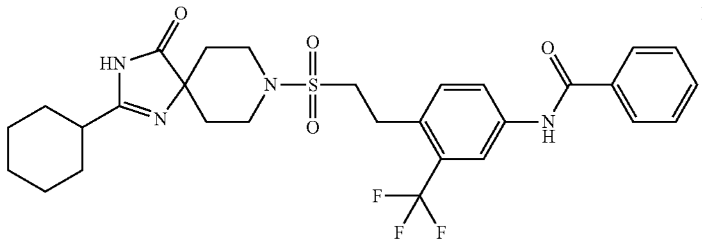 [SMILES: O=C(Nc1ccc(CCS(=O)(=O)N2CCC3(CC2)N=C(C2CCCCC2)NC3=O)c(C(F)(F)F)c1)c1ccccc1] | LCMS-C-1 | 2.82 | 591 (M + H)+ |
| 663 | 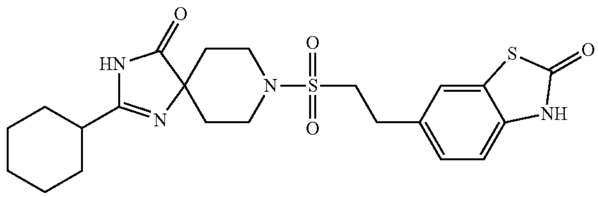 [SMILES: O=C1NC(C2CCCCC2)=NC12CCN(S(=O)(=O)CCc1ccc3[nH]c(=O)sc3c1)CC2] | LCMS-C-1 | 2.37 | 477 (M + H)+ |
| 664 | 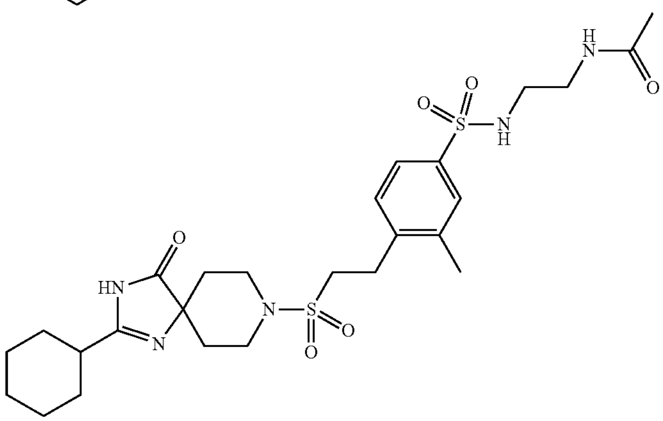 | LCMS-C-1 | 2.20 | 582 (M + H)+ |

The aryl bromide reagent used in the synthesis of Compound 658 ((4-bromo-benzyl)-carbamic acid isobutyl ester) was synthesized as follows.

(Reaction 124-2)

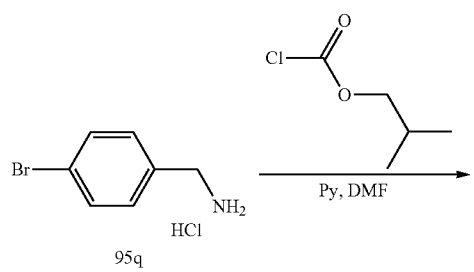

Isobutyl chloroformate (0.152 ml, 1.17 mmol) was added to a solution of 4-bromo-benzylamine hydrochloride (200 mg, 0.899 mmol) and pyridine (0.182 ml, 2.25 mmol) in DMF (2.0 ml), and the mixture was stirred at room temperature for 1.5 hours. A 1 N aqueous HCl solution was added to the reaction mixture, followed by extraction with ethyl acetate. The organic layer was sequentially washed with water and saturated brine and then concentrated under reduced pressure. The resulting residue was purified by silica gel column chromatography (dichloromethane-ethyl acetate) to give (4-bromo-benzyl)-carbamic acid isobutyl ester (180 mg, 70%).

MS (ESI) m/z=286, 288 (M+H)+.

The aryl bromide reagent used in the synthesis of Compound 660 (2-(4-bromo-3-trifluoromethyl-phenylamino)-N-(4-hydroxy-butyl)-acetamide) was synthesized as follows.

(Reaction 124-3)

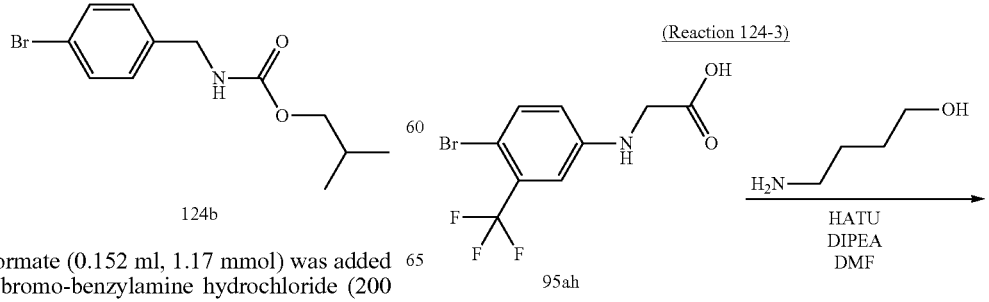

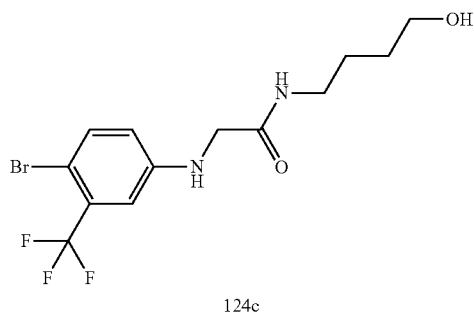

2-(4-Bromo-3-trifluoromethyl-phenylamino)-N-(4-hydroxy-butyl)-acetamide was synthesized by operations similar to those in Reaction 10-14 using appropriate reagents and starting material.

MS (ESI) m/z=369 (M+H)+.

The aryl bromide reagent used in the synthesis of Compound 661 ((4-bromo-3-trifluoromethyl-phenyl)-carbamic acid isobutyl ester) was synthesized as follows.

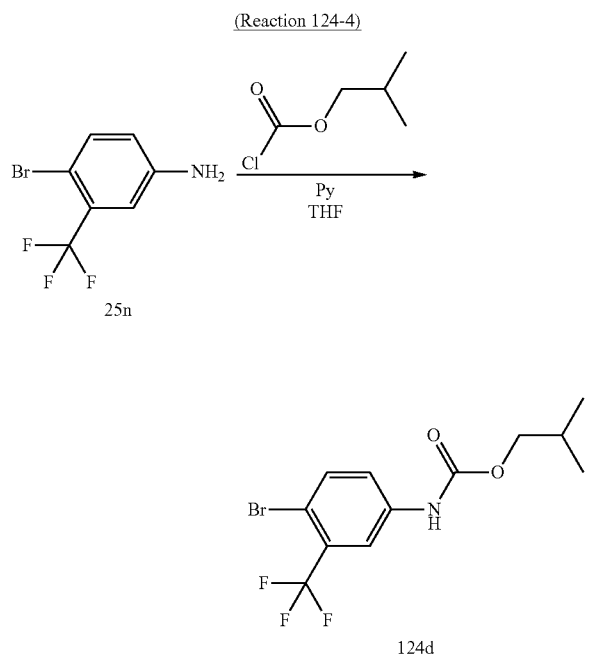

(4-Bromo-3-trifluoromethyl-phenyl)-carbamic acid isobutyl ester was synthesized by operations similar to those in Reaction 124-2 using appropriate reagents and starting material.

MS (ESI) m/z=338 (M−H)−.

The aryl bromide reagent used in the synthesis of Compound 662 (N-(4-bromo-3-trifluoromethyl-phenyl)-benzamide) was synthesized as follows.

N-(4-Bromo-3-trifluoromethyl-phenyl)-benzamide was synthesized by operations similar to those in Reaction 2-3 using appropriate reagents and starting material.

MS (ESI) m/z=344 (M+H)+.

The aryl bromide reagent used in the synthesis of Compound 664 (N-[2-(4-bromo-3-methyl-benzenesulfonylamino)-ethyl]-acetamide) was synthesized as follows.

N-[2-(4-Bromo-3-methyl-benzenesulfonylamino)-ethyl]-acetamide was synthesized by operations similar to those in Reaction 5-4 using appropriate reagents and starting material.

MS (ESI) m/z=335 (M+H)+.

Example 125
N-(2-Dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide (Compound 665)
(Reaction 125-1)
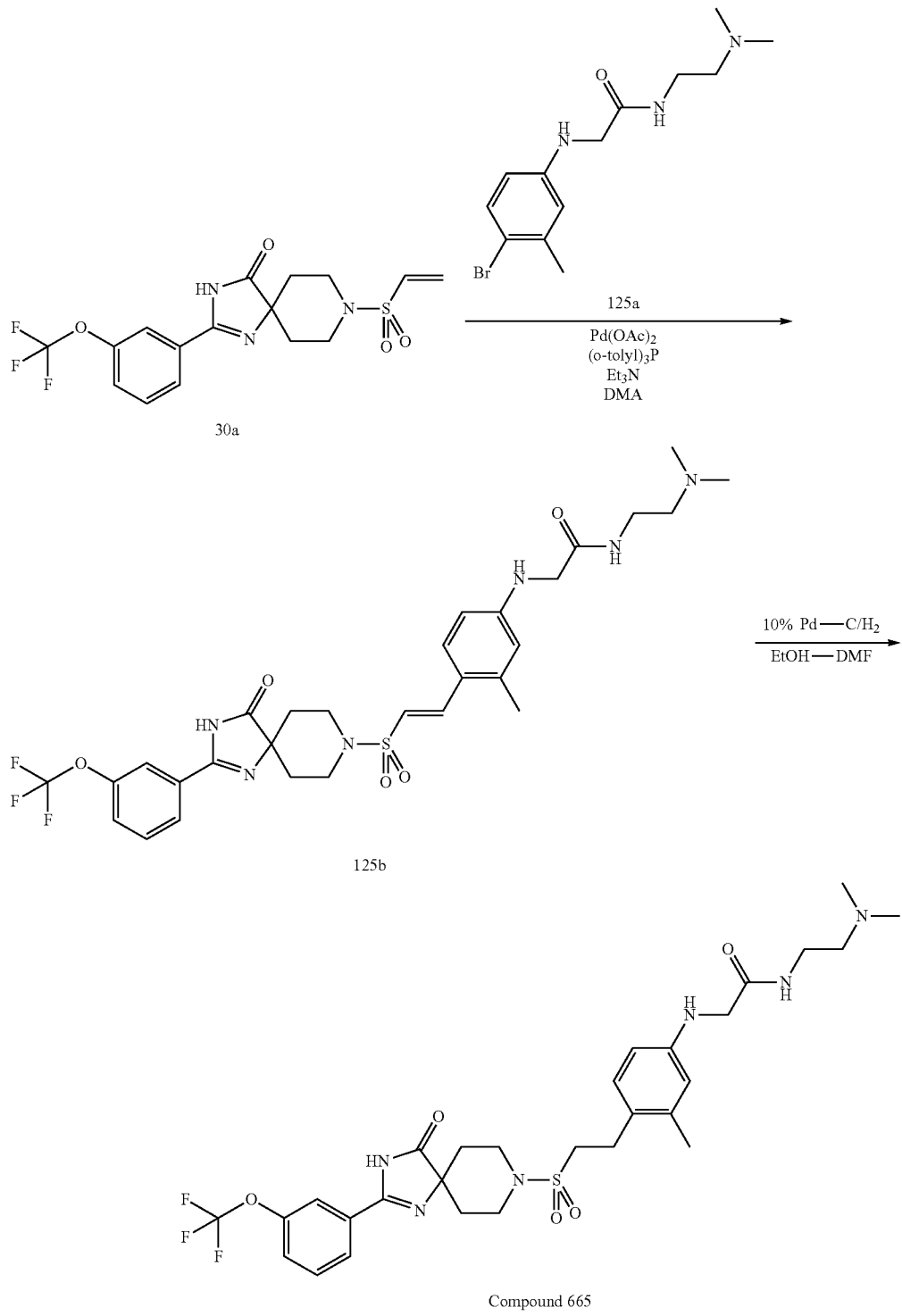
Compound 665

N-(2-Dimethylamino-ethyl)-2-(3-methyl-4-{2-[4-oxo-2-(3-trifluoromethoxy-phenyl)-1,3,8-triaza-spiro[4.5]dec-1-ene-8-sulfonyl]-ethyl}-phenylamino)-acetamide was synthesized by operations similar to those in Reaction 25-2 and Reaction 42-2 using appropriate reagents and starting material.

MS (ESI) m/z=639 (M+H)+.

The example compound shown below was synthesized by operations similar to those in Example 125 using appropriate reagents and starting material.

Compound 666

TABLE 95

| Target Compound | Structure | LCMS condition | Retention time (min) | MS (m/z) |
|---|---|---|---|---|
| 666 | 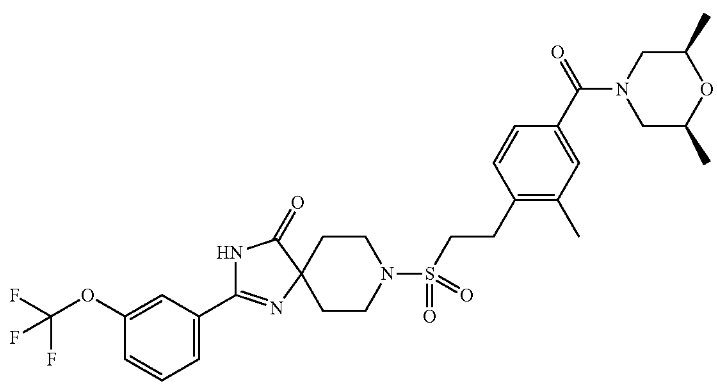 [SMILES: Cc1cc(C(=O)N2C[C@@H](C)O[C@@H](C)C2)ccc1CCS(=O)(=O)N1CCC2(CC1)N=C(c1cccc(OC(F)(F)F)c1)NC2=O] | LCMS-A-1 | 2.60 | 637 (M + H)+ |

The aryl bromide reagent used in the synthesis of Compound 666 ((4-bromo-3-methyl-phenyl)-(cis-2,6-dimethyl-morpholin-4-yl)-methanone) was synthesized as follows.

(Reaction 125-2)

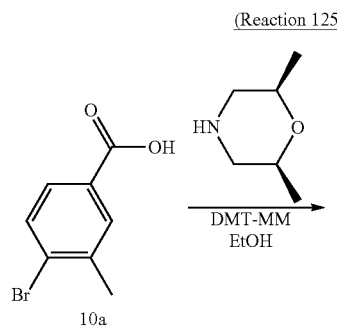

-continued

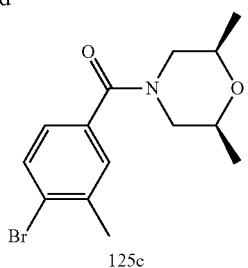

125c (4-Bromo-3-methyl-phenyl)-(cis-2,6-dimethyl-morpholin-4-yl)-methanone was synthesized by operations similar to those in Reaction 10-1 using appropriate reagents and starting material.

MS (ESI) m/z=312, 314 (M+H)+.

Example 126
N-(2,2,3,3,4,4,4-Heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide (Compound 667)
(Reaction 126-1)
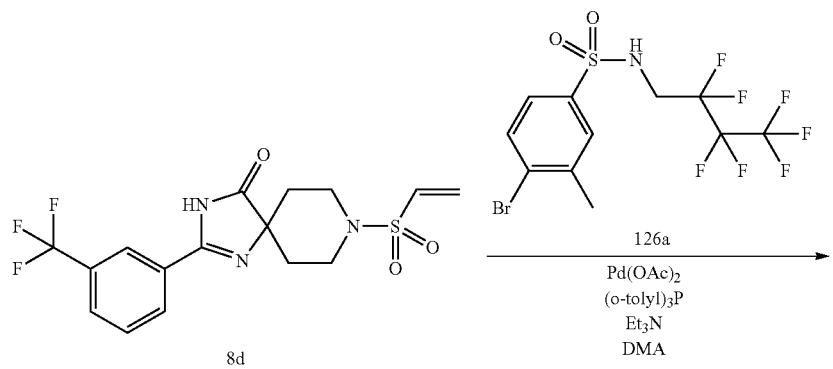
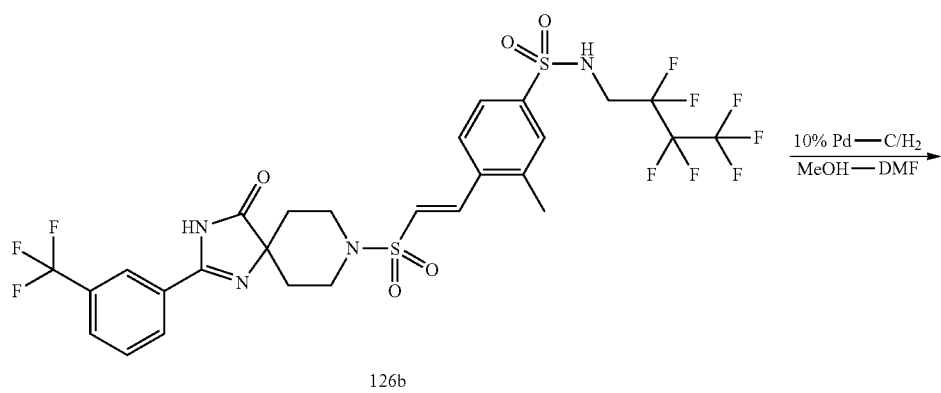
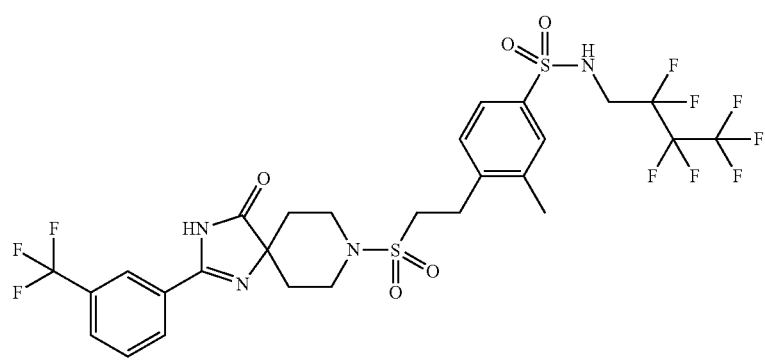
Compound 667

733

N-(2,2,3,3,4,4,4-Heptafluoro-butyl)-3-methyl-4-{2-[4-oxo-2-(3-trifluoromethyl-phenyl)-1,3,8-triaza-spiro[4.5]dec-1-ene-8-sulfonyl]-ethyl}-benzenesulfonamide was synthesized by operations similar to those in Reaction 26-1 and Reaction 42-1 using appropriate reagents and starting material.

MS (ESI) m/z=741 (M+H)+.

The aryl bromide reagent used in the synthesis of Compound 667 (4-bromo-N-(2,2,3,3,4,4,4-heptafluoro-butyl)-3-methyl-benzenesulfonamide) was synthesized as follows.

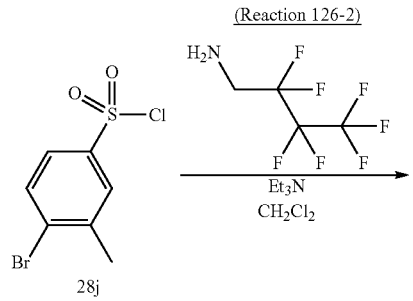

(Reaction 126-2)

734

-continued

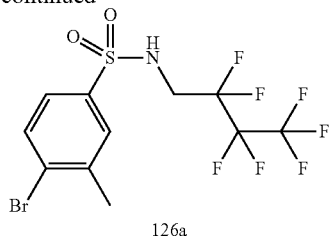

126a

4-Bromo-N-(2,2,3,3,4,4,4-heptafluoro-butyl)-3-methyl-benzenesulfonamide was synthesized by operations similar to those in Reaction 5-4 using appropriate reagents and starting material.

MS (ESI) m/z=454, 456 (M+Na)+.

Example 127

8-[2-(3-Methoxy-2-methyl-phenyl)-ethanesulfonyl]-2-(4-methyl-cyclohexyl)-1,3,8-triaza-spiro[4.5]dec-1-en-4-one (Compound 668)

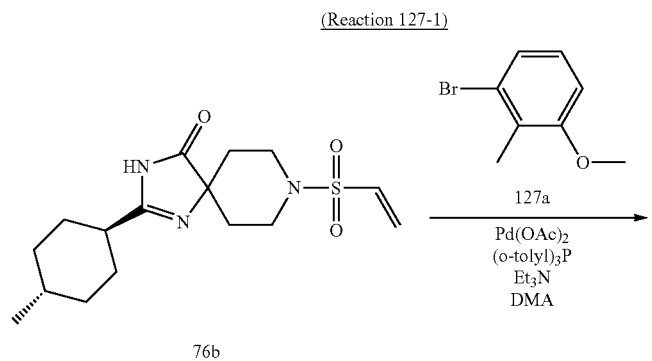

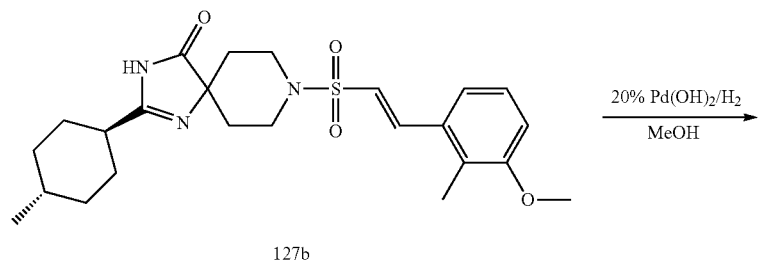

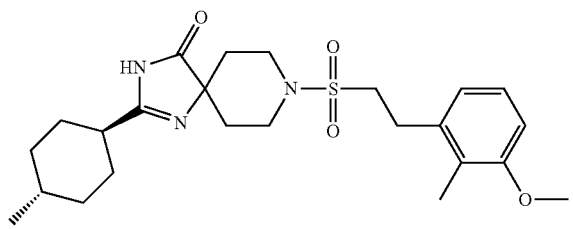

Compound 668

8-[2-(3-Methoxy-2-methyl-phenyl)-ethanesulfonyl]-2-(4-methyl-cyclohexyl)-1,3,8-triaza-spiro[4.5]dec-1-en-4-one was synthesized by operations similar to those in Reaction 26-1 and Reaction 122-2 using appropriate reagents and starting material.

MS (ESI) m/z=462 (M+H)+.

The example compound shown below was synthesized by operations similar to those in Example 127 using appropriate reagents and starting material.

Compound 669

(Reaction 127-3)

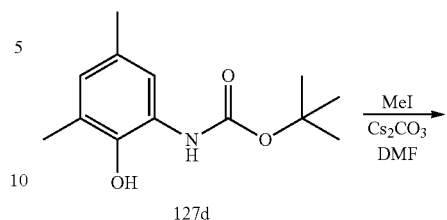

127d

TABLE 96

| Target Compound | Structure | LCMS condition | Retention time (min) | MS (m/z) |
|---|---|---|---|---|
| 669 | 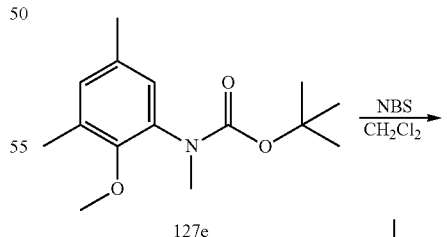 | LCMS-F-1 | 1.1 | 605 (M + H)+ |

The aryl bromide reagent used in the synthesis of Compound 669 ((4-bromo-2-methoxy-3,5-dimethyl-phenyl)-methyl-carbamic acid tert-butyl ester) was synthesized as follows.

(Reaction 127-2)

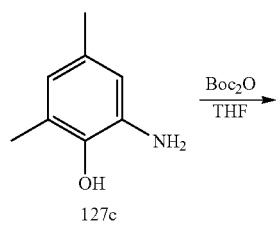

127c

127d

Di-tert-butyl dicarbonate (1.32 ml, 5.75 mmol) was added to a solution of 2-amino-4,6-dimethyl-phenol (731.8 mg, 5.335 mmol) in THF (3.7 ml), and the mixture was stirred at room temperature for five hours. The reaction mixture was concentrated under reduced pressure, and the resulting residue was then purified by silica gel column chromatography (hexane-ethyl acetate) to give (2-hydroxy-3,5-dimethyl-phenyl)-carbamic acid tert-butyl ester as a red purple solid (1.234 g, 97%).

$^1$H-NMR (300 MHz, CDCl$_3$) δ 1.52 (9H, s), 2.21 (3H, s), 2.24 (3H, s), 6.54 (1H, br), 6.71 (1H, s), 6.76 (1H, s), 7.74 (1H, br).

-continued

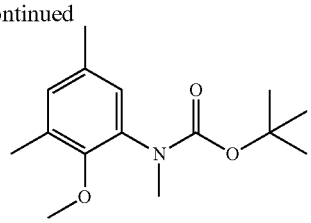

127e (2-Methoxy-3,5-dimethyl-phenyl)-methyl-carbamic acid tert-butyl ester was synthesized by operations similar to those in Reaction 26-4 (using cesium carbonate as a base) using appropriate reagents and starting material.

$^1$H-NMR (400 MHz, CDCl$_3$) δ 1.30-1.56 (9H, br), 2.24 (3H, s), 2.25 (3H, s), 3.16 (3H, s), 3.69 (3H, s), 6.76 (1H, br), 6.87 (1H, s).

(Reaction 127-4)

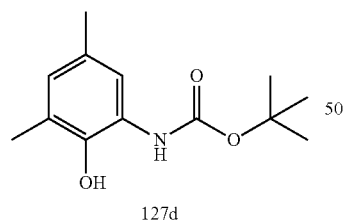

127e

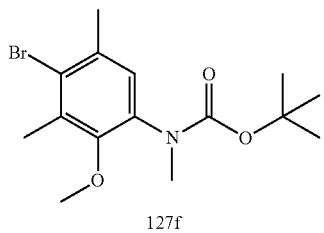

127f

N-Bromosuccinimide (326 mg, 1.83 mmol) was added to a solution of (2-methoxy-3,5-dimethyl-phenyl)-methyl-carbamic acid tert-butyl ester (456 mg, 1.72 mmol) in dichloromethane (1.8 ml) at 0° C., and the mixture was stirred at room temperature for 50 minutes. The reaction mixture was diluted with dichloromethane and adjusted to pH 9 and washed with water and a 1 N aqueous NaOH solution (1 ml), and the organic layer was dried over MgSO$_4$ and concentrated under reduced pressure. The resulting residue was purified by silica gel column chromatography (hexane-ethyl acetate) to give (4-bromo-2-methoxy-3,5-dimethyl-phenyl)-methyl-carbamic acid tert-butyl ester as a colorless solid (545 mg, 92%).

$^1$H-NMR (400 MHz, CDCl$_3$) δ 1.30-1.56 (9H, br), 2.35 (3H, s), 2.37 (3H, s), 3.14 (3H, s), 3.69 (3H, s), 6.82-7.07 (1H, br).

Example 128

8-{2-[4-((S)-2-Hydroxymethyl-5-oxo-pyrrolidin-1-yl)-2-methyl-phenyl]-ethanesulfonyl}-2-nonyl-1,3,8-triaza-spiro[4.5]dec-1-en-4-one (Compound 670)

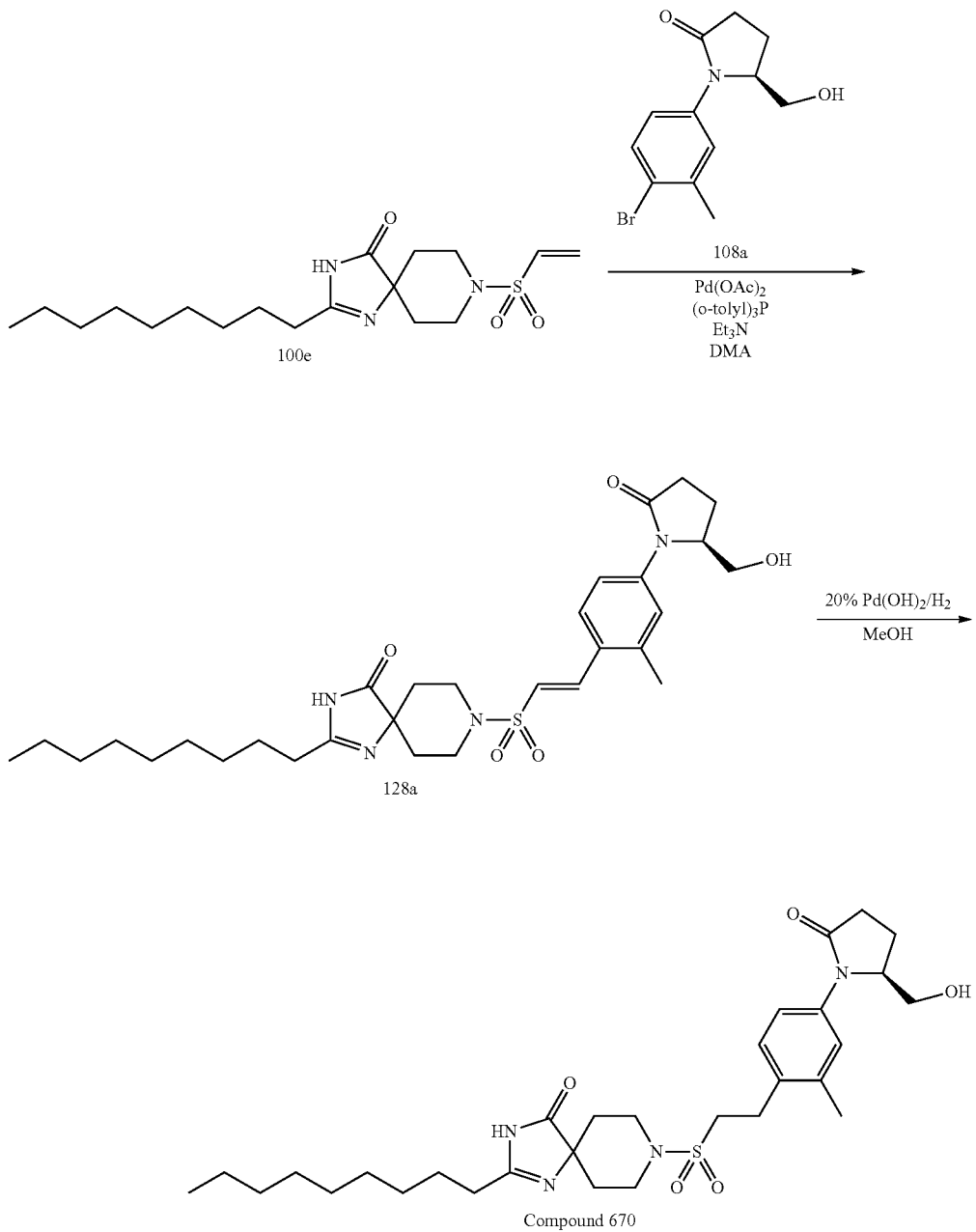

8-{2-[4-((S)-2-Hydroxymethyl-5-oxo-pyrrolidin-1-yl)-2-methyl-phenyl]-ethanesulfonyl}-2-nonyl-1,3,8-triaza-spiro[4.5]dec-1-en-4-one was synthesized by operations similar to those in Reaction 26-1 and Reaction 122-2 using appropriate reagents and starting material.

MS (ESI) m/z=575 (M+H)+.

Example 129

8-[2-(5,7-Dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one (Compound 671)

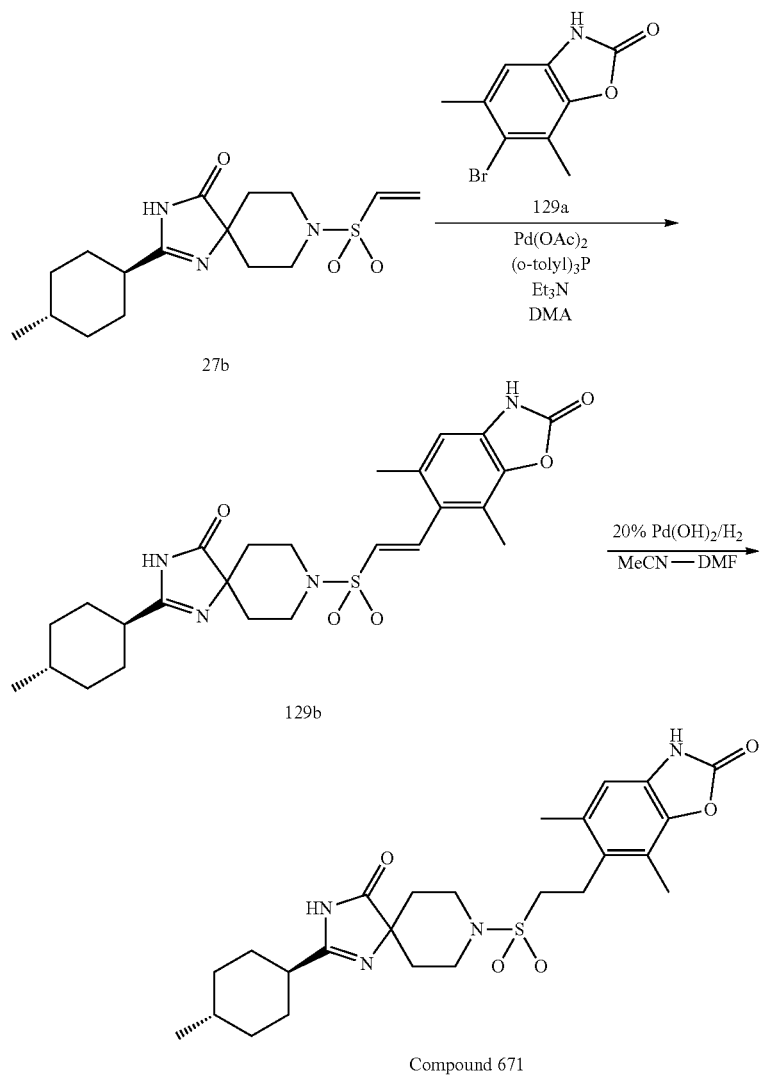

The aryl bromide reagent used in the synthesis of Compound 129 (6-bromo-5,7-dimethyl-3H-benzoxazol-2-one) was synthesized as follows.

(Reaction 129-2)

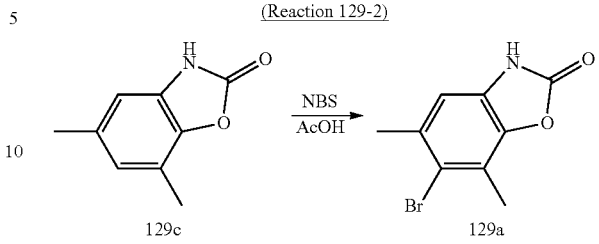

8-[2-(5,7-Dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one was synthesized by operations similar to those in Reaction 26-1 and Reaction 122-2 (using MeCN-DMF as a solvent) using appropriate reagents and starting material.

MS (ESI) m/z=503 (M+H)+.

6-Bromo-5,7-dimethyl-3H-benzoxazol-2-one was synthesized by operations similar to those in Reaction 127-4 (using acetic acid as a solvent) using appropriate reagents and starting material.

MS (ESI) m/z=242, 244 (M+H)+.

Example 130
(2-{4-[2-(2-Cyclohexyl-4-oxo-1,3,8-triaza-spiro[4.5]dec-1-ene-8-sulfonyl)-ethyl]-phenyl}-ethyl)-carbamic acid methyl ester (Compound 672)
(Reaction 130-1)
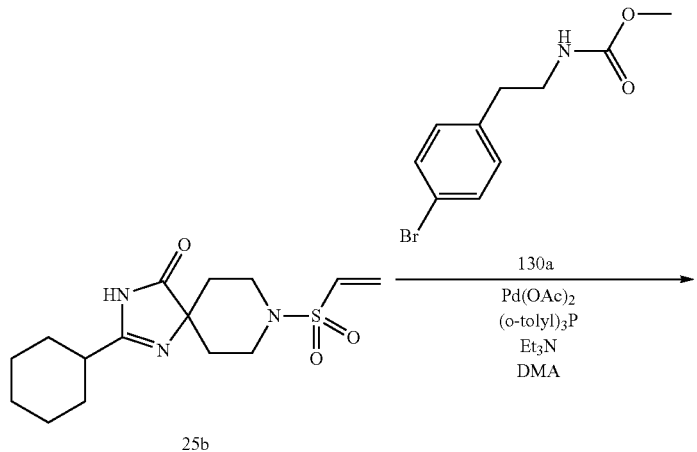
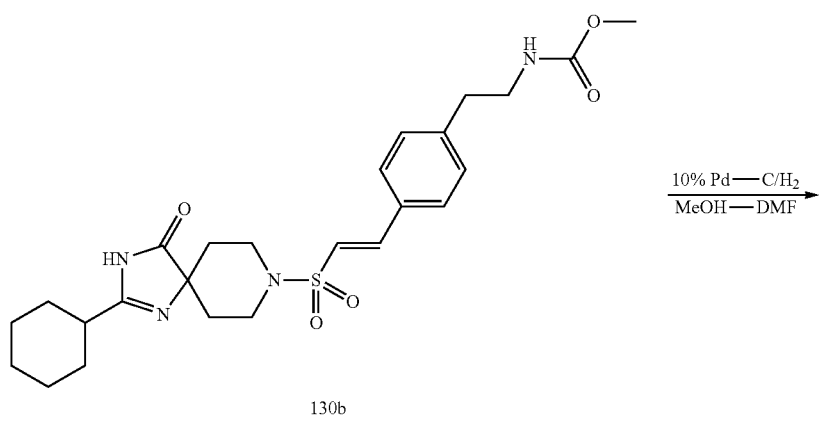
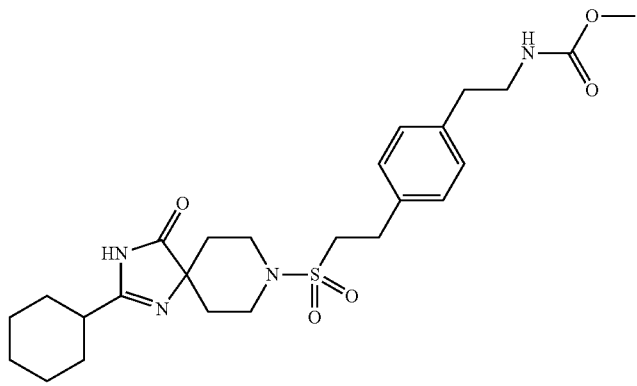
Compound 672

(2-{4-[2-(2-Cyclohexyl-4-oxo-1,3,8-triaza-spiro[4.5]dec-1-ene-8-sulfonyl)-ethyl]-phenyl}-ethyl)-carbamic acid methyl ester was synthesized by operations similar to those in Reaction 26-1 and Reaction 42-2 using appropriate reagents and starting material.

MS (ESI) m/z=505 (M+H)+.

The example compound shown below was synthesized by operations similar to those in Example 130 using appropriate reagents and starting material.

Compound 673

TABLE 97

| Target Compound | Structure | LCMS condition | Retention time (min) | MS (m/z) |
|---|---|---|---|---|
| 673 | 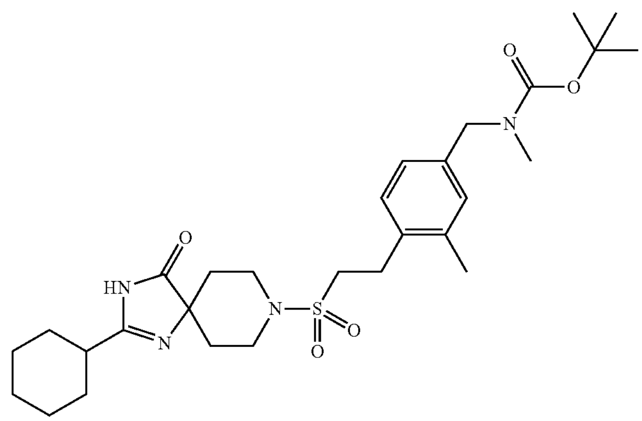 [SMILES: Cc1cc(CN(C)C(=O)OC(C)(C)C)ccc1CCS(=O)(=O)N1CCC2(CC1)N=C(C1CCCCC1)NC2=O] | LCMS-C-1 | 2.93 | 559 (M − H)− |

The aryl bromide reagent used in the synthesis of Compound 673 ((4-bromo-3-methyl-benzyl)-methyl-carbamic acid tert-butyl ester) was synthesized as follows.

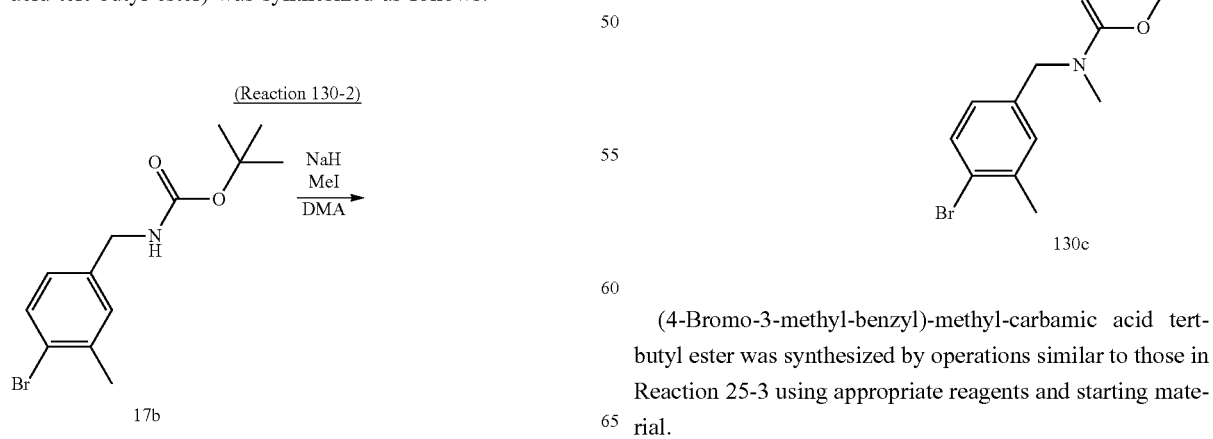

(4-Bromo-3-methyl-benzyl)-methyl-carbamic acid tert-butyl ester was synthesized by operations similar to those in Reaction 25-3 using appropriate reagents and starting material.

MS (ESI) m/z=336, 338 (M+Na)+.

Example 131
8-(2-{4-[3-(2-Hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one (Compound 674)
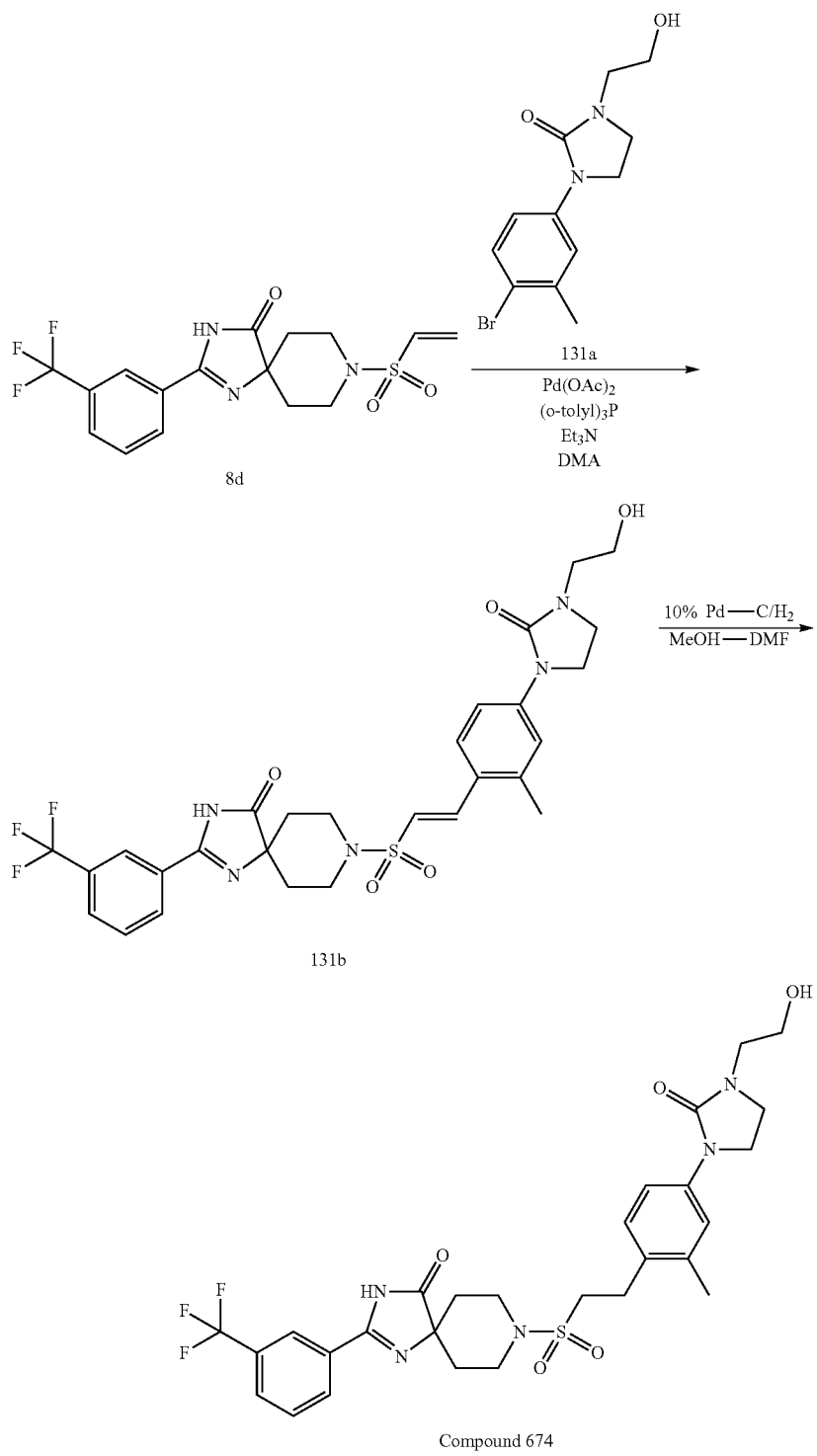

747

8-(2-{4-[3-(2-Hydroxy-ethyl)-2-oxo-imidazolidin-1-yl]-2-methyl-phenyl}-ethanesulfonyl)-2-(3-trifluoromethyl-phenyl)-1,3,8-triaza-spiro[4.5]dec-1-en-4-one was synthesized by operations similar to those in Reaction 26-1 and Reaction 42-2 using appropriate reagents and starting material.

MS (ESI) m/z=608 (M+H)+.

The aryl bromide reagent used in the synthesis of Compound 674 (1-(4-bromo-3-methyl-phenyl)-3-(2-hydroxy-ethyl)-imidazolidin-2-one) was synthesized as follows.

748

-continued

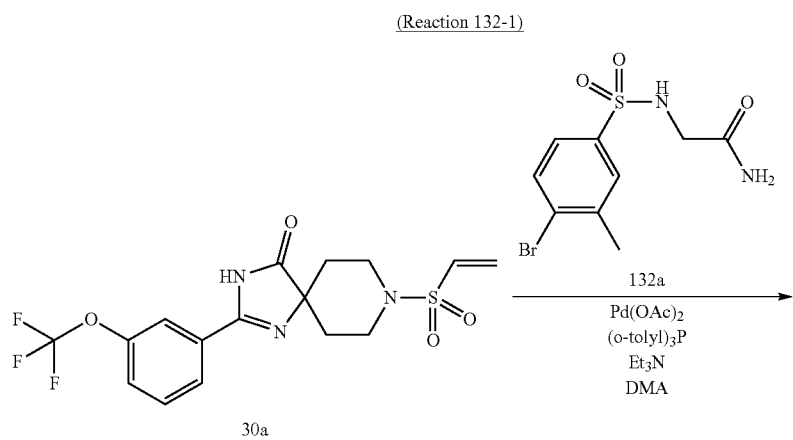

1-(4-Bromo-3-methyl-phenyl)-3-(2-hydroxy-ethyl)-imidazolidin-2-one was synthesized by operations similar to those in Reaction 29-3 using appropriate reagents and starting material.

MS (ESI) m/z=299, 301 (M+H)+.

Example 132

2-(3-Methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide (Compound 675)

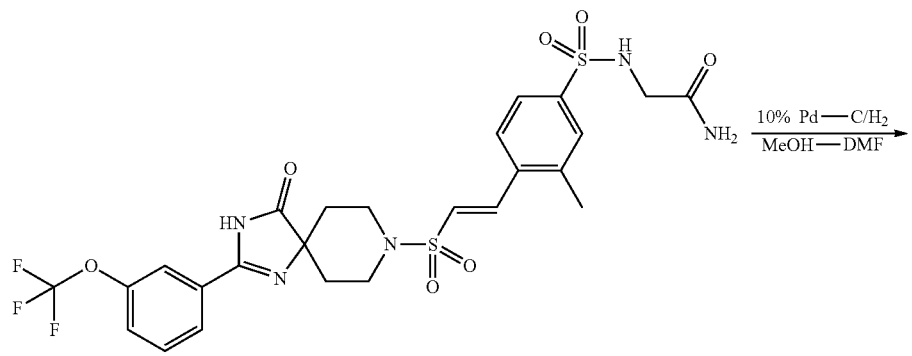

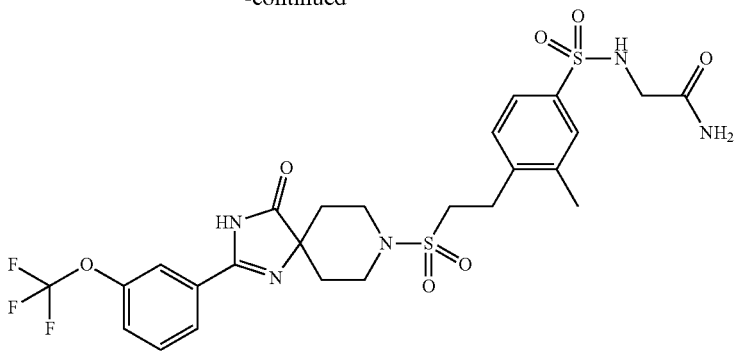

Compound 675

2-(3-Methyl-4-{2-[4-oxo-2-(3-trifluoromethoxy-phenyl)-1,3,8-triaza-spiro[4.5]dec-1-ene-8-sulfonyl]-ethyl}-benzenesulfonylamino)-acetamide was synthesized by operations similar to those in Reaction 26-1 and Reaction 42-2 using appropriate reagents and starting material.

MS (ESI) m/z=632 (M+H)+.

The example compound shown below was synthesized by operations similar to those in Example 132 using appropriate reagents and starting material.

Compound 676

TABLE 98

| Target Compound | Structure | LCMS condition | Retention time (min) | MS (m/z) |
|---|---|---|---|---|
| 676 | 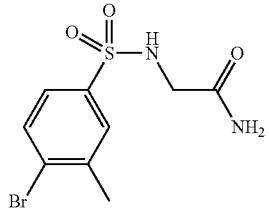 | LCMS-C-1 | 2.70 | 614 (M + H)+ |

The aryl bromide reagent used in the synthesis of Compound 675 (2-(4-bromo-3-methyl-benzenesulfonylamino)-acetamide) was synthesized as follows.

(Reaction 132-2)

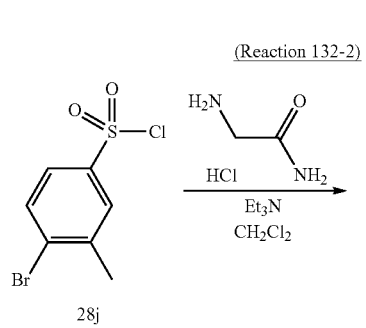

2-(4-Bromo-3-methyl-benzenesulfonylamino)-acetamide was synthesized by operations similar to those in Reaction 5-4 using appropriate reagents and starting material.

MS (ESI) m/z=307, 309 (M+H)+.

Example 133

3-(4-{2-[2-(4-Butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione (Compound 677)

(Reaction 133-1)

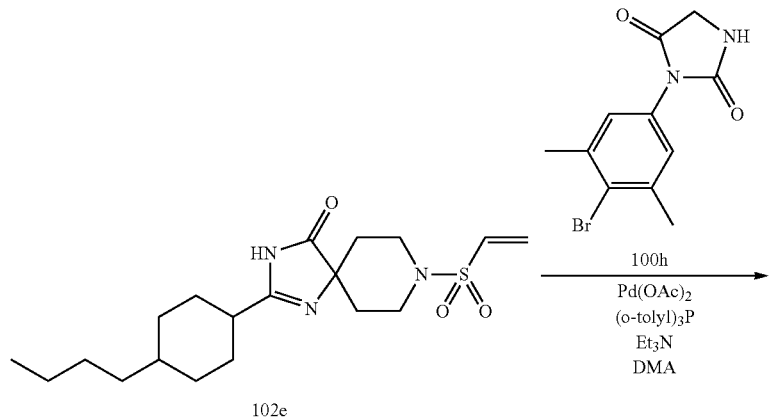

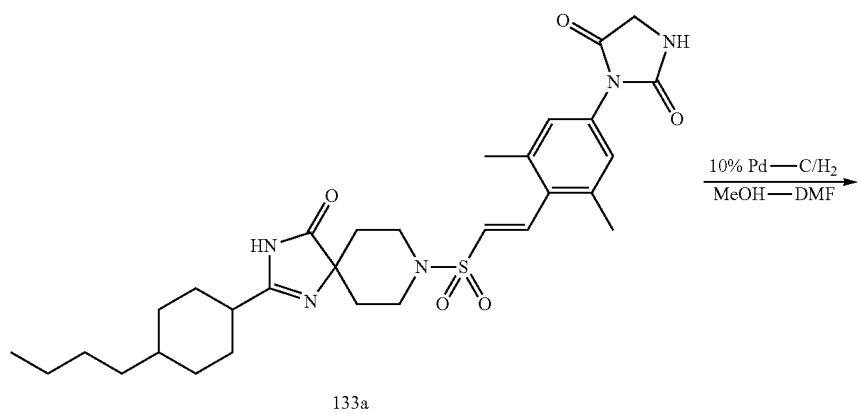

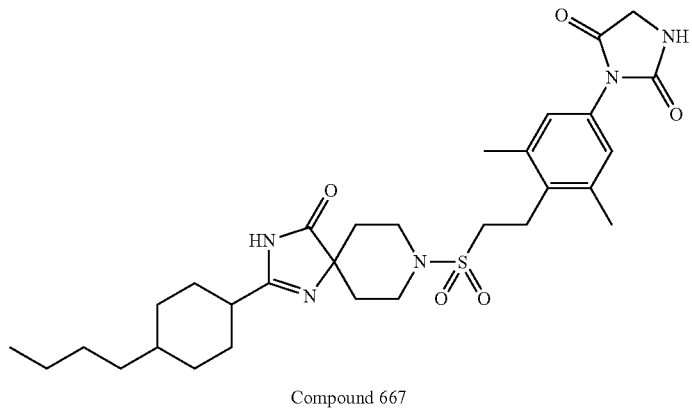

Compound 667

3-(4-{2-[2-(4-Butyl-cyclohexyl)-4-oxo-1,3,8-triaza-spiro[4.5]dec-1-ene-8-sulfonyl]-ethyl}-3,5-dimethyl-phenyl)-imidazolidine-2,4-dione was synthesized by operations similar to those in Reaction 26-1 and Reaction 42-2 using appropriate reagents and starting material.

MS (ESI) m/z=586 (M+H)+.

Example 134
N-Cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 678)
(Reaction 134-1)
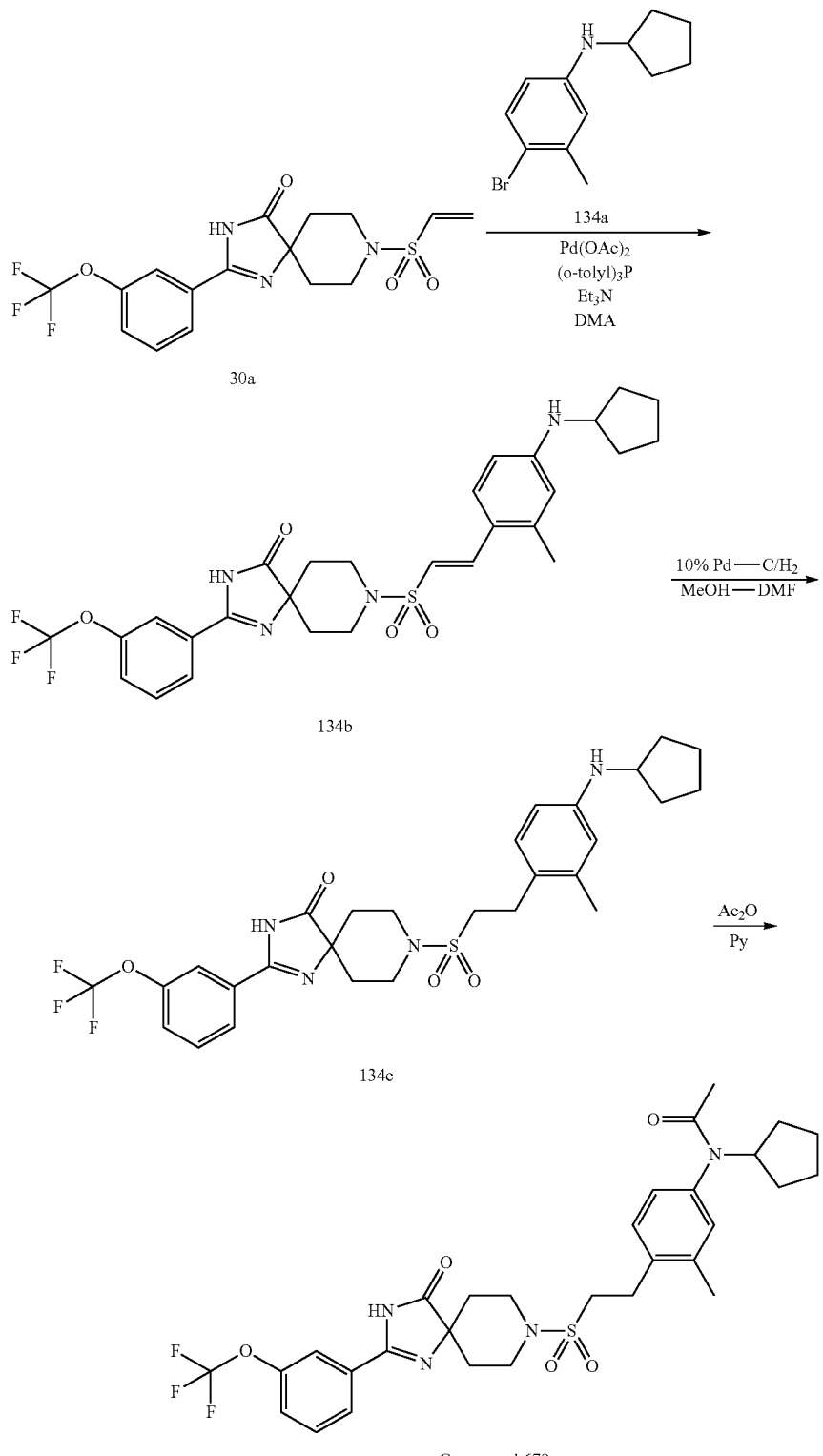

N-Cyclopentyl-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 26-1, Reaction 42-2 and Reaction 12-2 using appropriate reagents and starting material.

MS (ESI) m/z=621 (M+H)+.

The aryl bromide reagent used in the synthesis of Compound 678 ((4-bromo-3-methyl-phenyl)-cyclopentyl-amine) was synthesized as follows.

(4-Bromo-3-methyl-phenyl)-cyclopentyl-amine was synthesized by operations similar to those in Reaction 41-1 using appropriate reagents and starting material.

MS (ESI) m/z=254, 256 (M+H)+.

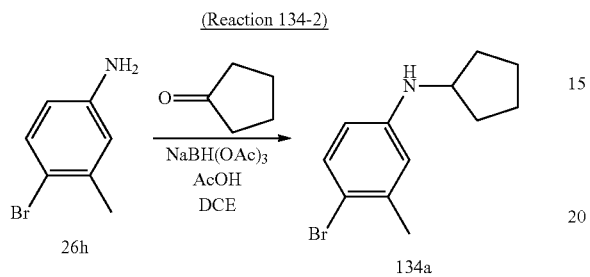

(Reaction 134-2)

Example 135

1-(2,3-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 679)

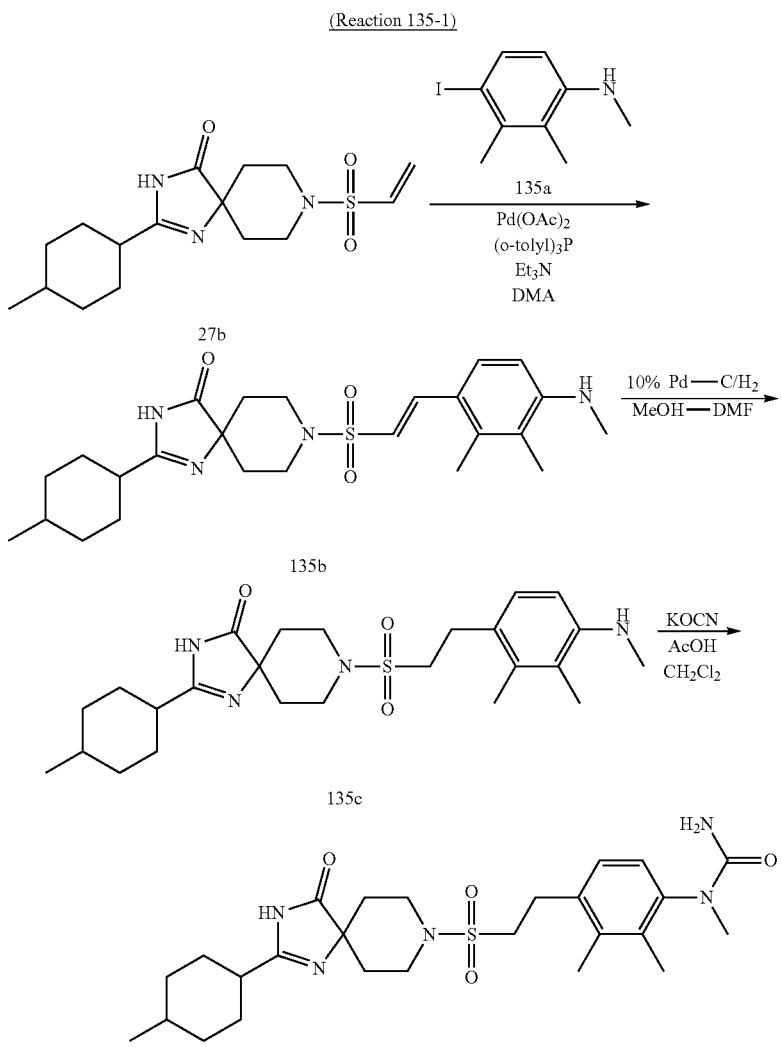

1-(2,3-Dimethyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1, Reaction 42-2 and Reaction 89-2 using appropriate reagents and starting material.

MS (ESI) m/z=518 (M+H)+.

The example compound shown below was synthesized by operations similar to those in Example 135 using appropriate reagents and starting material.

Compound 680

TABLE 99

| Target Compound | Structure | LCMS condition | Retention time (min) | MS (m/z) |
|---|---|---|---|---|
| 680 | 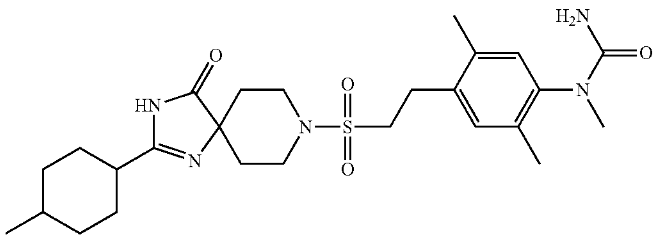 [SMILES: Cc1cc(N(C)C(N)=O)c(C)cc1CCS(=O)(=O)N1CCC2(CC1)N=C(C1CCC(C)CC1)NC2=O] | LCMS-C-1 | 2.58 | 518 (M + H)+ |

The aryl iodide reagent used in the synthesis of Compound 679 (4-iodo-N,2,3-trimethyl-aniline) was synthesized as follows.

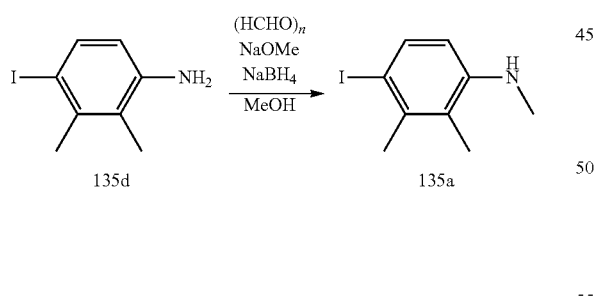

A 28% solution of sodium methoxide in methanol (0.694 ml, 6.07 mmol) was added to a solution of 4-iodo-2,3-dimethyl-aniline (500 mg, 2.02 mmol) and paraformaldehyde (121 mg, 4.05 mmol) in methanol (8.0 ml), and the mixture was stirred at room temperature for 17 hours. Sodium borohydride (153 mg, 4.05 mmol) was further added, and the mixture was stirred at room temperature for four hours. A 1 N aqueous NaOH solution was added to the reaction mixture, followed by extraction with dichloromethane. The resulting residue was purified by silica gel column chromatography (hexane-ethyl acetate) to give 4-iodo-N,2,3-trimethyl-aniline (146 mg, 88%).

MS (ESI) m/z=262 (M+H)+.

The aryl iodide reagent used in the synthesis of Compound 680 ((4-iodo-2,5-dimethyl-phenyl)-methyl-amine) was synthesized as follows.

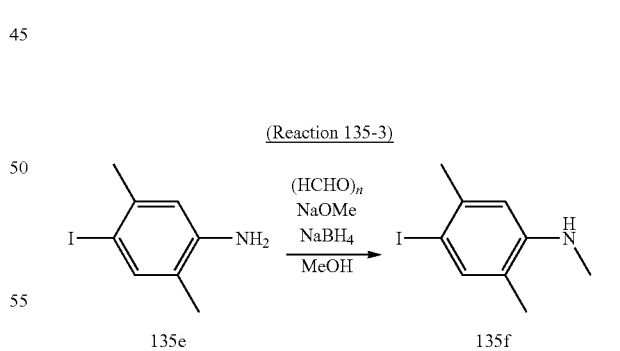

(4-Iodo-2,5-dimethyl-phenyl)-methyl-amine was synthesized by operations similar to those in Reaction 135-2 using appropriate reagents and starting material.

MS (ESI) m/z=262 (M+H)+.

Example 136
{4-[2-(2-Cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester (Compound 681)
(Reaction 136-1)
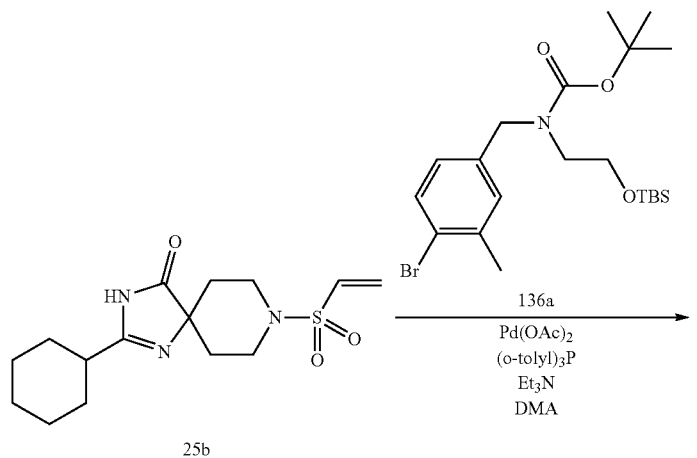
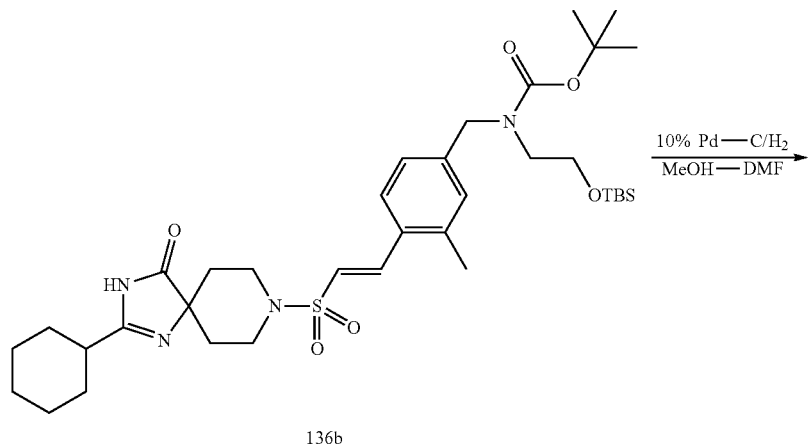
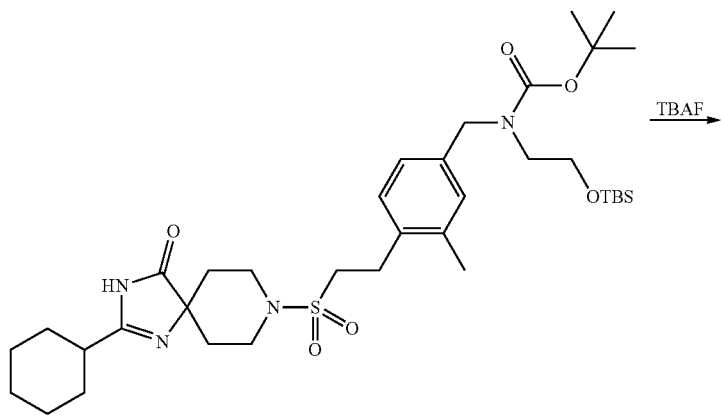

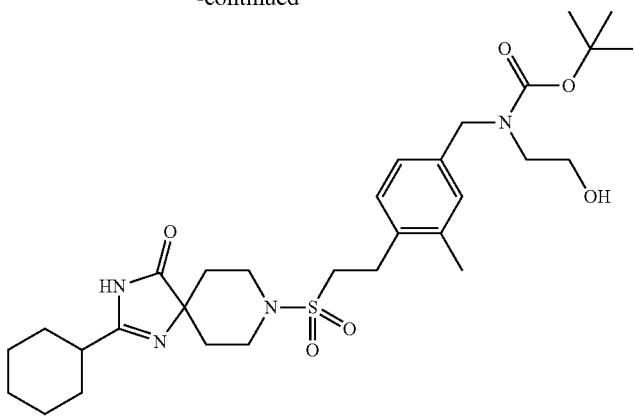

Compound 681

{4-[2-(2-Cyclohexyl-4-oxo-1,3,8-triaza-spiro[4.5]dec-1-ene-8-sulfonyl)-ethyl]-3-methyl-benzyl}-(2-hydroxy-ethyl)-carbamic acid tert-butyl ester was synthesized by operations similar to those in Reaction 26-1, Reaction 42-2 and Reaction 39-2 using appropriate reagents and starting material.

MS (ESI) m/z=589 (M−H)−.

The aryl bromide reagent used in the synthesis of Compound 681 ((4-bromo-3-methyl-benzyl)-[2-(tert-butyl-dimethyl-silanyloxy)-ethyl]-carbamic acid tert-butyl ester) was synthesized as follows.

(Reaction 136-2)

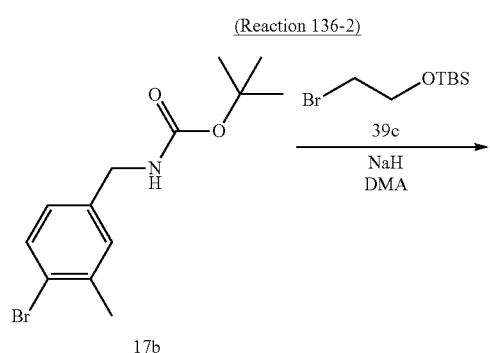

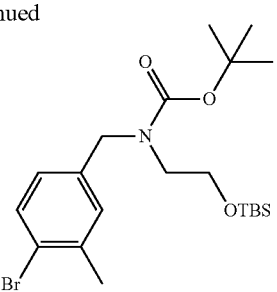

136a (4-Bromo-3-methyl-benzyl)-[2-(tert-butyl-dimethyl-silanyloxy)-ethyl]-carbamic acid tert-butyl ester was synthesized by operations similar to those in Reaction 25-3 using appropriate reagents and starting material.

MS (ESI) m/z=472, 474 (M+H)+.

Example 137

1-(3-Methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 682)

(Reaction 137-1)

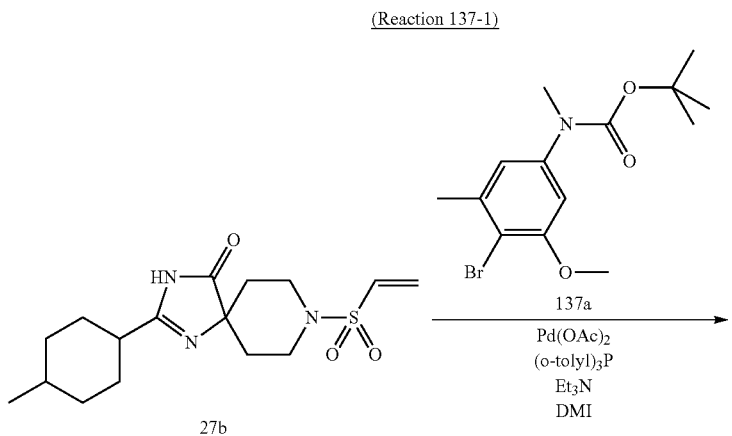

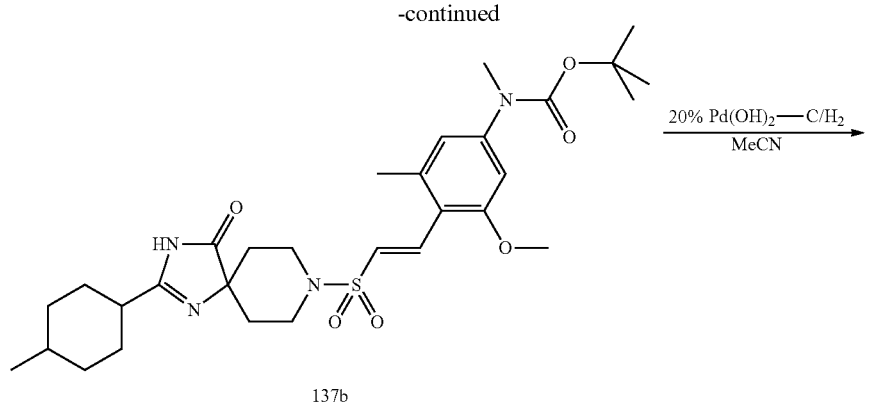
137b
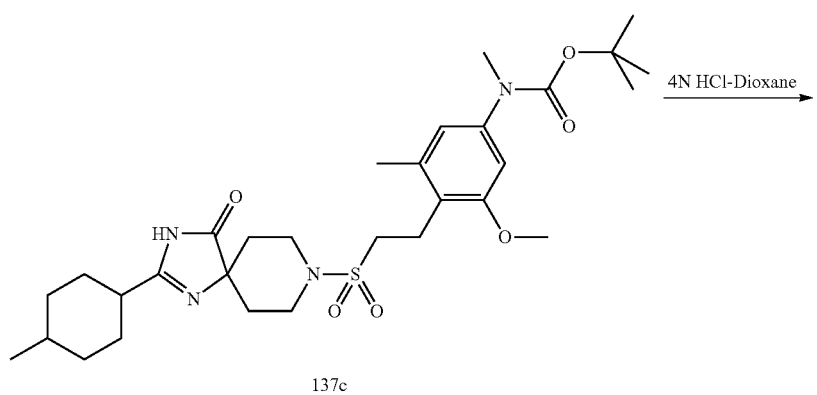
137c
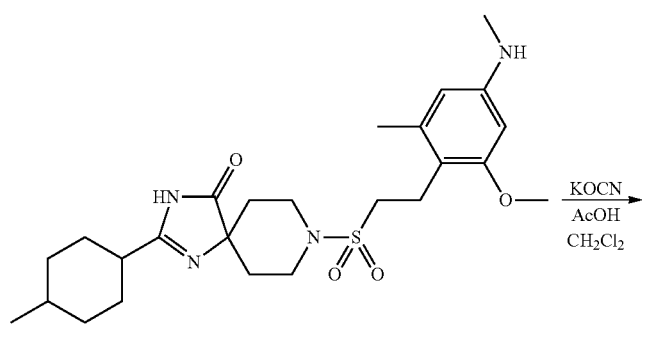
137d
Compound 682
1-(3-Methoxy-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1 (using DMI as a solvent), Reaction 122-2 (using acetonitrile as a solvent), Reaction 5-3 and Reaction 89-2 (using KOCN as a reagent) using appropriate reagents and starting material.
MS (ESI) m/z=534 (M+H)+.

The aryl bromide reagent used in the synthesis of Compound 682 ((4-bromo-3-methoxy-5-methyl-phenyl)-methyl-carbamic acid tert-butyl ester) was synthesized as follows.

(Reaction 137-2)

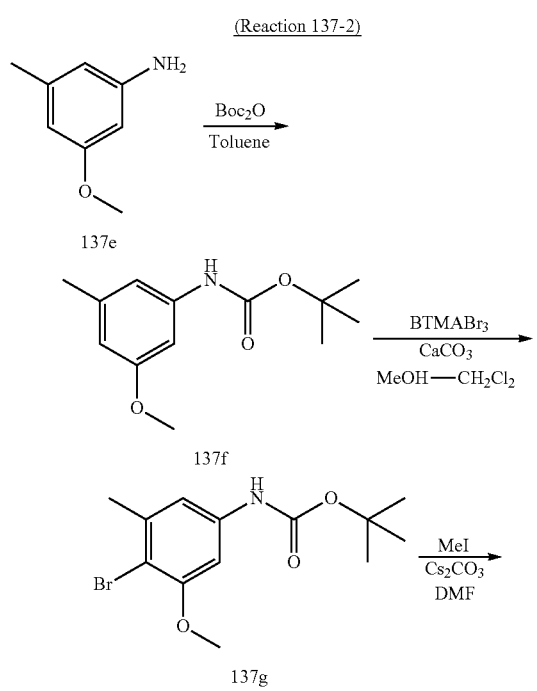

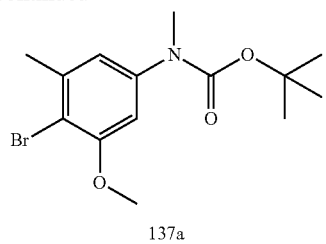

(4-Bromo-3-methoxy-5-methyl-phenyl)-methyl-carbamic acid tert-butyl ester was synthesized by operations similar to those in Reaction 127-2 (using toluene as a solvent), Reaction 26-2 and Reaction 26-4 (using cesium carbonate as a base) using appropriate reagents and starting material.

$^1$H-NMR (400 MHz, CDCl$_3$) δ 1.50 (9H, s), 2.42 (3H, s), 3.26 (3H, s), 3.90 (3H, s), 6.71 (1H, d, J=4.0 Hz), 6.77 (1H, J=4.0 Hz).

Example 138

1-(3-Chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea (Compound 683)

(Reaction 138-1)

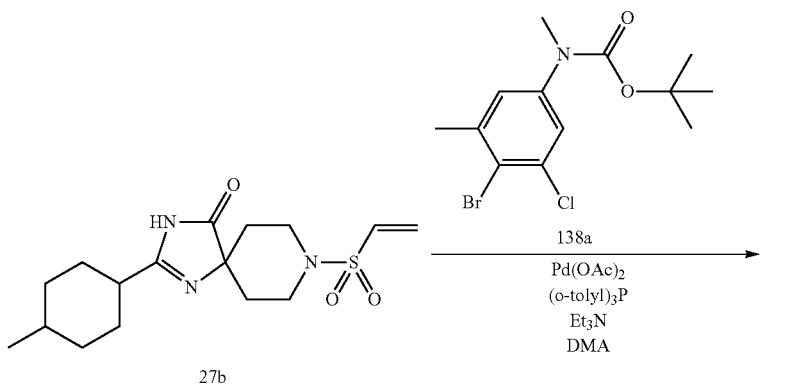

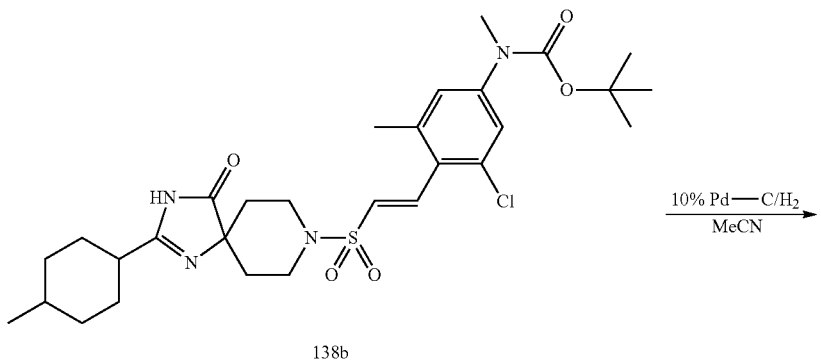

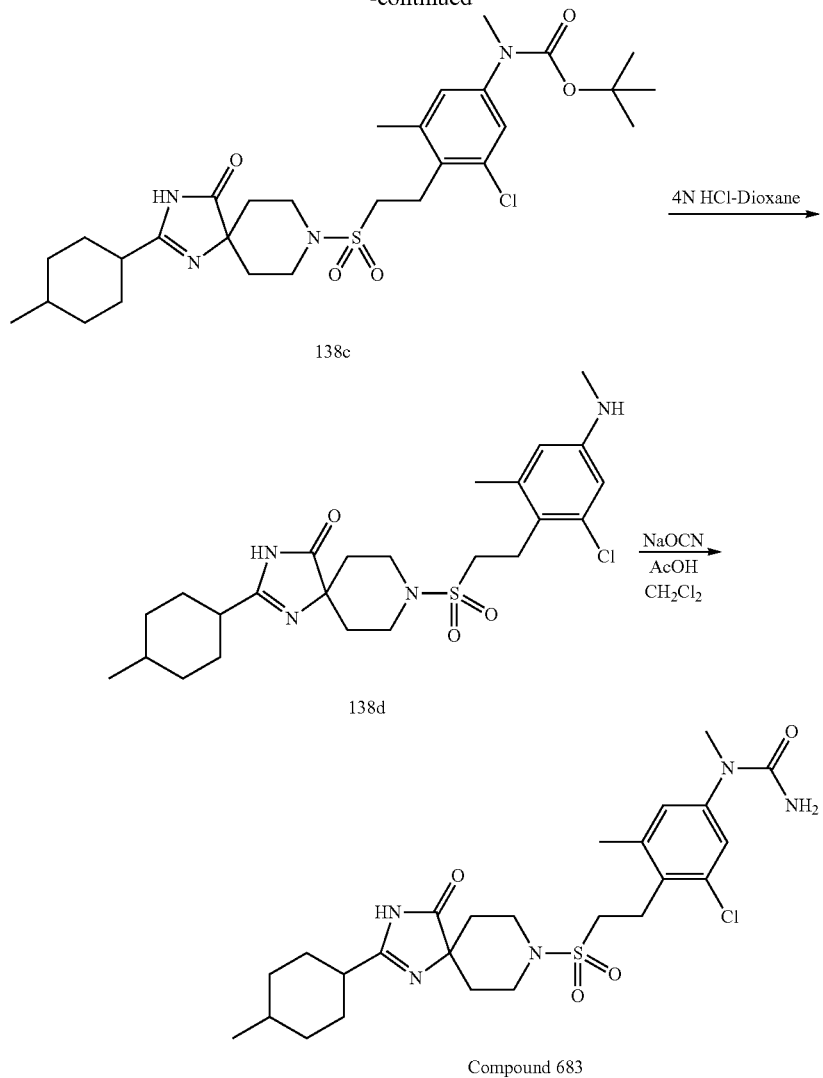

1-(3-Chloro-5-methyl-4-{2-[2-(4-methyl-cyclohexyl)-4-oxo-1,3,8-triaza-spiro[4.5]dec-1-ene-8-sulfonyl]-ethyl}-phenyl)-1-methyl-urea was synthesized by operations similar to those in Reaction 26-1, Reaction 42-1, Reaction 5-3 and Reaction 89-2 using appropriate reagents and starting material.

MS (ESI) m/z=538 (M+H)+.

The aryl bromide reagent used in the synthesis of Compound 683 ((4-bromo-3-chloro-5-methyl-phenyl)-methyl-carbamic acid tert-butyl ester) was synthesized as follows.

(Reaction 138-2)

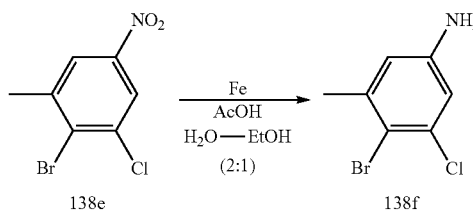

Iron (2.34 g, 41.8 mmol) and acetic acid (0.80 mL, 14.0 mmol) were added to a mixed solution of 2-bromo-1-chloro-3-methyl-5-nitro-benzene (3.50 g, 14.0 mmol) in ethanol (15 mL)-water (31 mL) at room temperature. The mixture was stirred at 100° C. for one hour, and a saturated aqueous sodium bicarbonate solution was then added at 0° C. The mixture was filtered through celite, and the filtrate was washed with ethyl acetate and water. The filtrate was concentrated under reduced pressure. Ethyl acetate was then added, and the organic layer and the aqueous layer were separated. The aqueous layer was repeatedly extracted with ethyl acetate three times, and the organic layers were then dried over sodium sulfate. The resulting residue was concentrated under reduced pressure to give 4-bromo-3-chloro-5-methyl-phenylamine as a pale brown solid (3.01 g, 98%).

MS (ESI) m/z=220, 222 (M+H)+.

769

(Reaction 138-3)

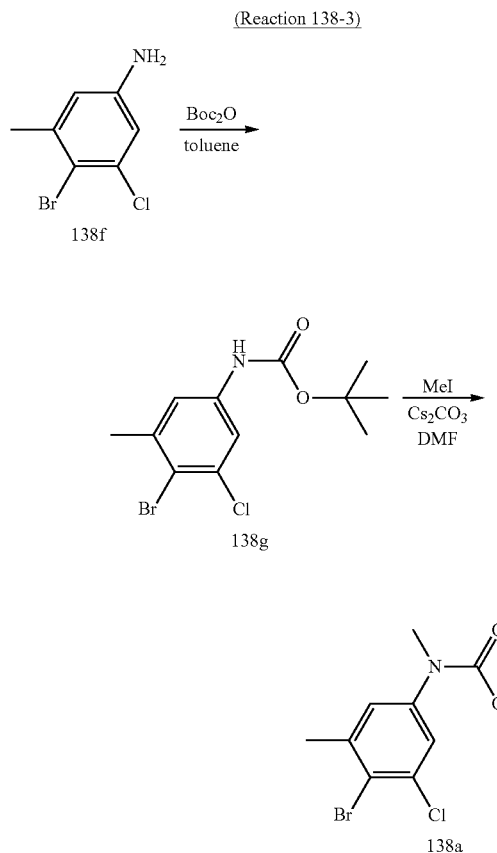

(4-Bromo-3-chloro-5-methyl-phenyl)-methyl-carbamic acid tert-butyl ester was synthesized by operations similar to those in Reaction 127-2 (using toluene as a solvent) and Reaction 26-4 (using cesium carbonate as a base) using appropriate reagents and starting material.

$^1$H-NMR (400 MHz, CDCl$_3$) δ 1.46 (9H, s), 2.44 (3H, s), 3.22 (3H, s), 7.06 (1H, d, J=2.4 Hz), 7.23 (1H, d, J=2.4 Hz).

The example compound shown below was synthesized by operations similar to those in Example 138 using appropriate reagents and starting material.

Compound 684

770

Example 139

5,7-Dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione (Compound 685)

(Reaction 139-1)

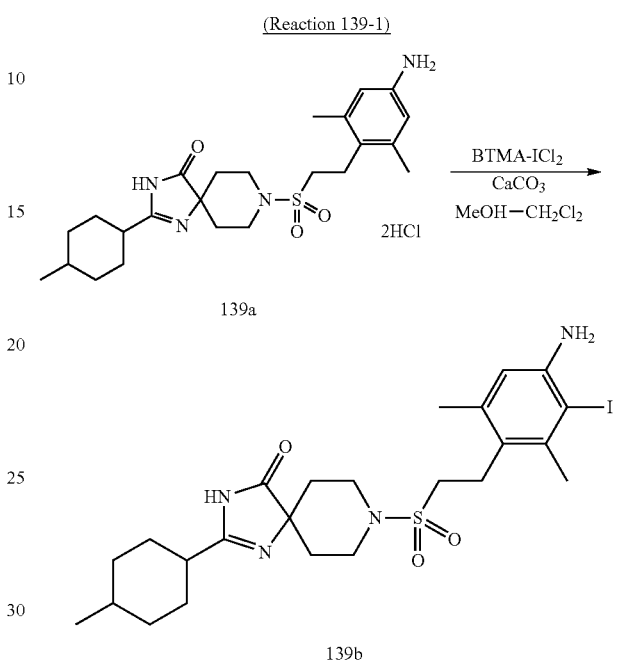

Benzyltrimethylammonium dichloroiodate (324 mg, 0.930 mmol) was added to a mixture of 8-[2-(4-amino-2,6-dimethyl-phenyl)-ethanesulfonyl]-2-(4-methyl-cyclohexyl)-1,3,8-triaza-spiro[4.5]dec-1-en-4-one dihydrochloride (530 mg, 1.03 mmol) and calcium carbonate (517 mg, 5.17 mmol) in methanol (6 mL)-dichloromethane (15 mL) at room temperature. The mixture was stirred at room temperature for 22 hours, and an aqueous sodium bicarbonate solution and ethyl acetate were then added. The organic layer and the aqueous layer were separated, and the aqueous layer was repeatedly extracted with ethyl acetate three times. The organic layers were combined and washed with saturated brine, and the insoluble matter was then filtered off through celite. The filtrate was concentrated under reduced

TABLE 100

| Target Compound | Structure | LCMS condition | Retention time (min) | MS (m/z) |
|---|---|---|---|---|
| 684 | | LCMS-F-1 | 0.94 | 548 (M + H)+ | pressure, and the resulting residue was purified by silica gel column chromatography to give 8-[2-(4-amino-3-iodo-2,6-dimethyl-phenyl)-ethanesulfonyl]-2-(4-methyl-cyclohexyl)-1,3,8-triaza-spiro[4.5]dec-1-en-4-one as a pale yellow solid (337 mg, 62%).

MS (ESI) m/z=587 (M+H)+.

(Reaction 139-2)

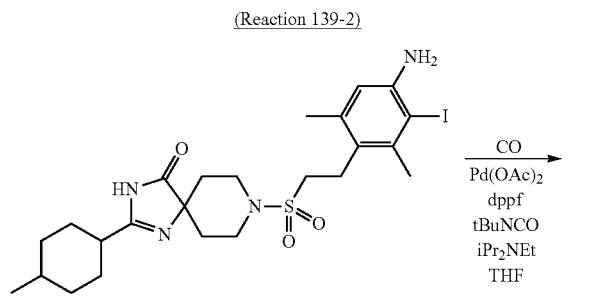

A mixture of 8-[2-(4-amino-3-iodo-2,6-dimethyl-phenyl)-ethanesulfonyl]-2-(4-methyl-cyclohexyl)-1,3,8-triaza-spiro[4.5]dec-1-en-4-one (15 mg, 0.0256 mmol), palladium acetate (1.1 mg, 5.11 μmol), 1,1'-bis(diphenylphosphino)ferrocene (2.2 mg, 5.11 μmol), tert-butyl isocyanate (12 μL, 0.0767 mmol) and N,N-diisopropylethylamine (13 μL, 0.0767 mmol) in tetrahydrofuran (1 mL) was heated with stirring for 12 hours in a pressure bottle sealed under the conditions of 4 atm and 80° C. in a carbon monoxide atmosphere. After returning to room temperature, palladium acetate (2.2 mg, 10.22 μmol), 1,1'-bis(diphenylphosphino)ferrocene (4.4 mg, 10.22 μmol), tert-butyl isocyanate (24 μL, 0.153 mmol) and N,N-diisopropylethylamine (26 μL, 0.153 mmol) were added to the reaction solution, and the mixture was heated with stirring for 14 hours in a pressure bottle sealed under the conditions of 4 atm and 80° C. in a carbon monoxide atmosphere. After returning to room temperature, the reaction solution was concentrated under reduced pressure, and the resulting residue was purified by preparative TLC to give 3-tert-butyl-5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione as a pale yellow solid (3.3 mg, 22%).

MS (ESI) m/z=586 (M+H)+.

(Reaction 139-3)

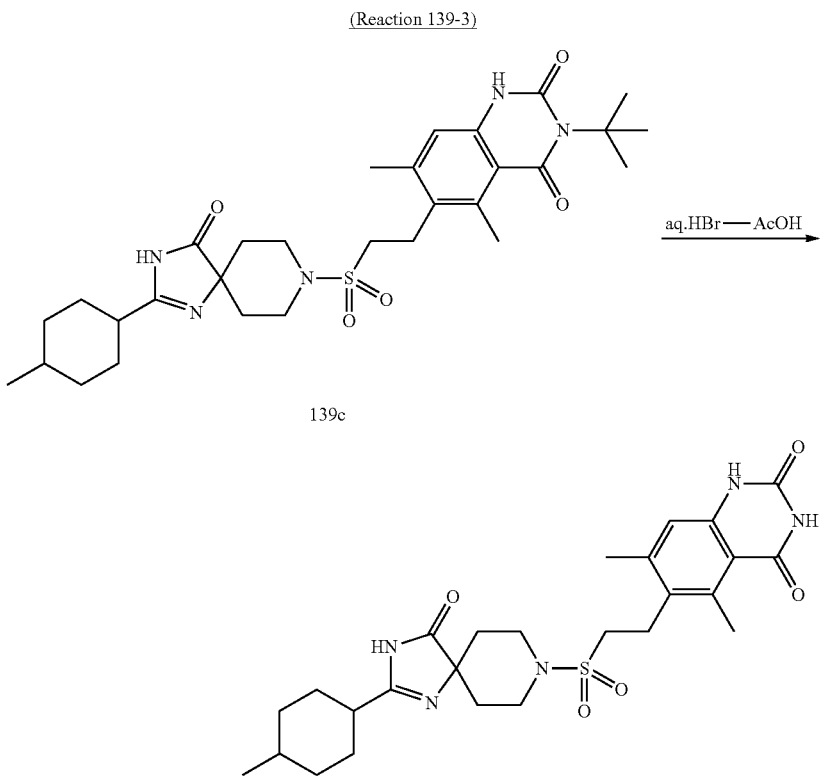

An aqueous hydrogen bromide solution (80 μL) was added to a mixed solution of 3-tert-butyl-5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione (3.3 mg, 3.41 μmol) in acetic acid (80 μL), and the mixture was heated with stirring at 100° C. for one hour. The reaction solution was returned to room temperature and then concentrated under reduced pressure, and the resulting residue was purified by preparative TLC to give 5,7-dimethyl-6-{2-[2-(4-methyl-cyclohexyl)-4-oxo-1,3,8-triaza-spiro[4.5]dec-1-ene-8-sulfonyl]-ethyl}-1H-quinazoline-2,4-dione as a pale yellow solid (1.2 mg, 44%).

MS (ESI) m/z=530 (M+H)+.

Example 140

8-{(E)-2-[1-(2-Amino-ethyl)-1H-indol-4-yl]-ethenesulfonyl}-2-cyclohexyl-1,3,8-triaza-spiro[4.5]dec-1-en-4-one (Compound 686)

8-{(E)-2-[1-(2-Amino-ethyl)-1H-indol-4-yl]-ethenesulfonyl}-2-cyclohexyl-1,3,8-triaza-spiro[4.5]dec-1-en-4-one was synthesized by operations similar to those in Reaction 25-2 and Reaction 7-2 using appropriate reagents and starting material.

MS (ESI) m/z=484 (M+H)+.

The aryl bromide reagent used in the synthesis of Compound 686 ([2-(4-bromo-indol-1-yl)-ethyl]-carbamic acid tert-butyl ester) was synthesized as follows.

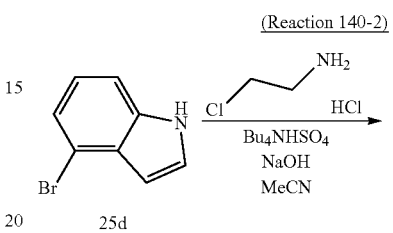

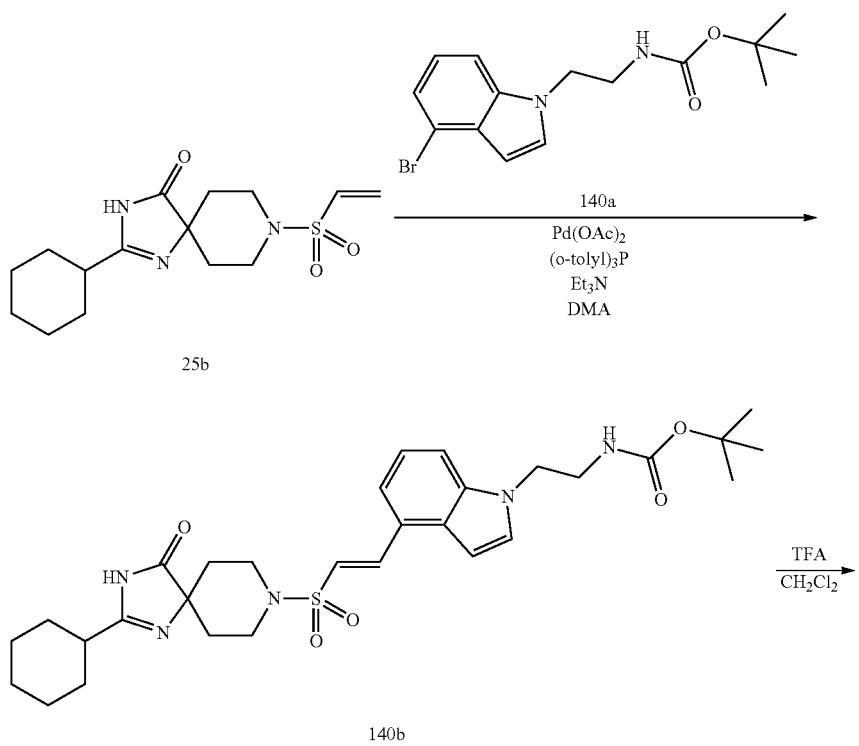

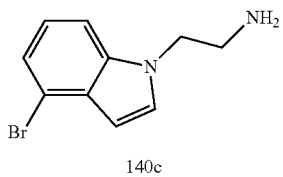

140c

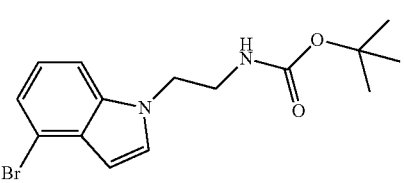

140a

Tetrabutylammonium hydrogen sulfate (41.0 mg, 0.121 mmol) and sodium hydroxide (210 mg, 5.25 mmol) were added to a solution of 4-bromo-1H-indole (0.30 ml, 2.39 mmol) in acetonitrile (0.80 mL), and the mixture was stirred at room temperature for 20 minutes. Subsequently, 2-chloroethylamine hydrochloride (334 mg, 2.88 mmol) was added and the mixture was heated with stirring at 100° C. for seven hours. After cooling, water was added to the reaction mixture, followed by extraction with ethyl acetate. The organic layer was sequentially washed with water and saturated brine and then concentrated under reduced pressure. The resulting residue was purified by silica gel column chromatography (dichloromethane-methanol) to give 2-(4-bromo-indol-1-yl)-ethylamine (222 mg, 39%).

MS (ESI) m/z=239, 241 (M+H)+.

(Reaction 140-3)

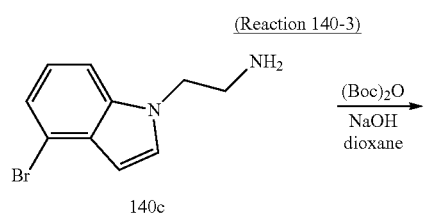

140c

A 2 N aqueous NaOH solution (0.47 ml, 0.94 mmol) and di-tert-butyl dicarbonate (223 mg, 1.02 mmol) were sequentially added to a solution of 2-(4-bromo-indol-1-yl)-ethylamine (222 mg, 0.928 mmol) in dioxane (0.47 ml), and the mixture was stirred at room temperature for 19 hours. Water was added to the reaction mixture, followed by extraction with ethyl acetate. The organic layer was washed with saturated brine and then concentrated under reduced pressure. The resulting residue was purified by silica gel column chromatography (dichloromethane only) to give [2-(4-bromo-indol-1-yl)-ethyl]-carbamic acid tert-butyl ester (292 mg, 93%).

MS (ESI) m/z=361, 363 (M+Na)+.

The example compound shown below was synthesized by operations similar to those in Example 140 using appropriate reagents and starting material.

Compound 687

TABLE 101

| Target Compound | Structure | LCMS condition | Retention time (min) | MS (m/z) |
|---|---|---|---|---|
| 687 | 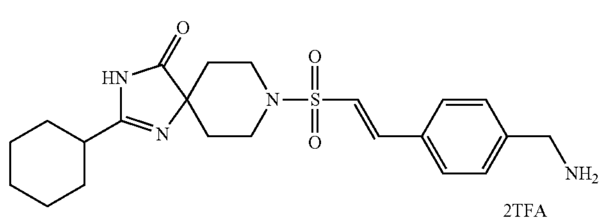 [SMILES: NCc1ccc(/C=C/S(=O)(=O)N2CCC3(CC2)N=C(C2CCCCC2)NC3=O)cc1 ; "2TFA"] | LCMS-C-1 | 1.98 | 431 (M + H)+ |

Example 141

(S)-2-Amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide (Compound 688)

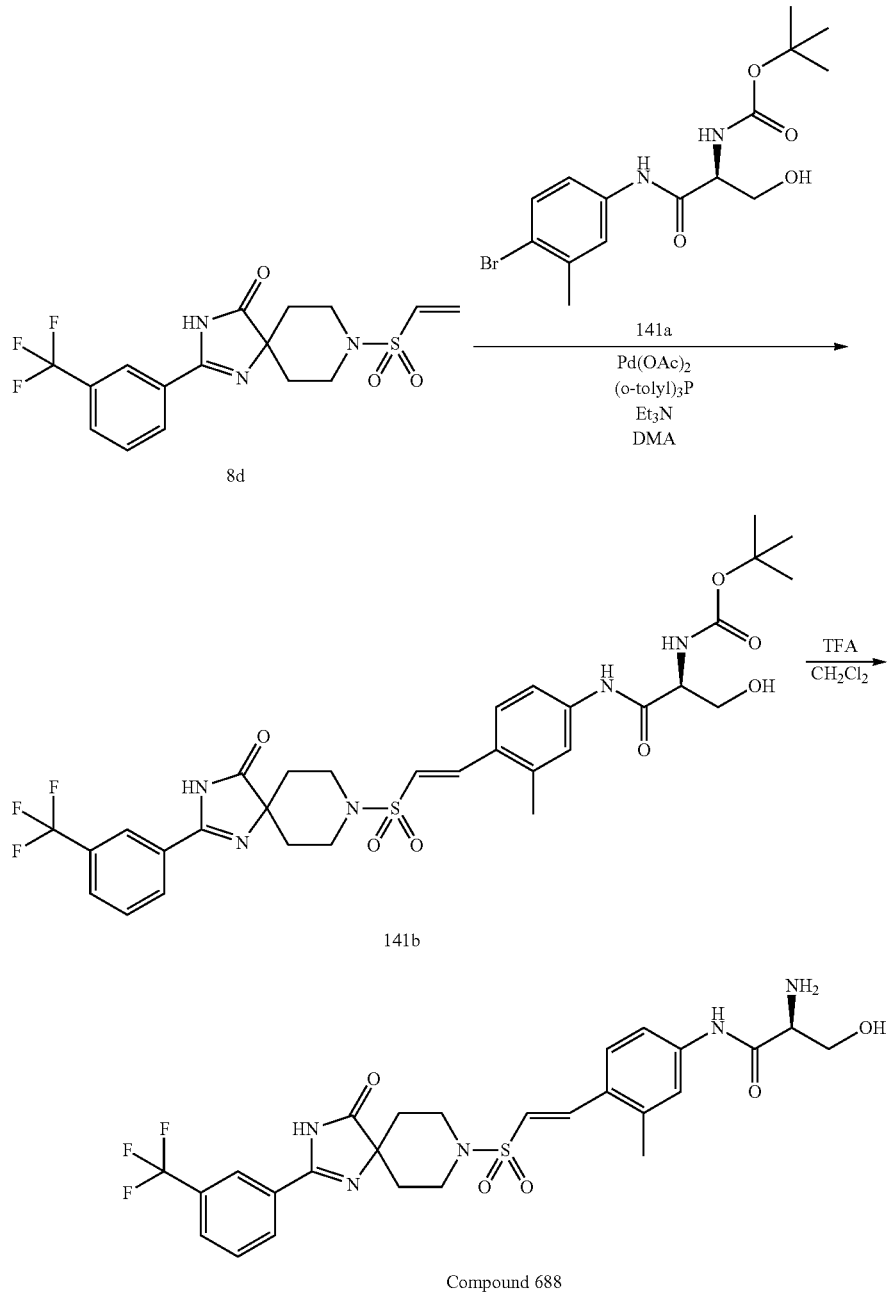

(S)-2-Amino-3-hydroxy-N-(3-methyl-4-{(E)-2-[4-oxo-2-(3-trifluoromethyl-phenyl)-1,3,8-triaza-spiro[4.5]dec-1-ene-8-sulfonyl]-vinyl}-phenyl)-propionamide was synthesized by operations similar to those in Reaction 25-2 and Reaction 7-2 using appropriate reagents and starting material.

MS (ESI) m/z=580 (M+H)+.

The aryl bromide reagent used in the synthesis of Compound 688 ([(S)-1-(4-bromo-3-methyl-phenylcarbamoyl)-2-hydroxy-ethyl]-carbamic acid tert-butyl ester) was synthesized as follows.

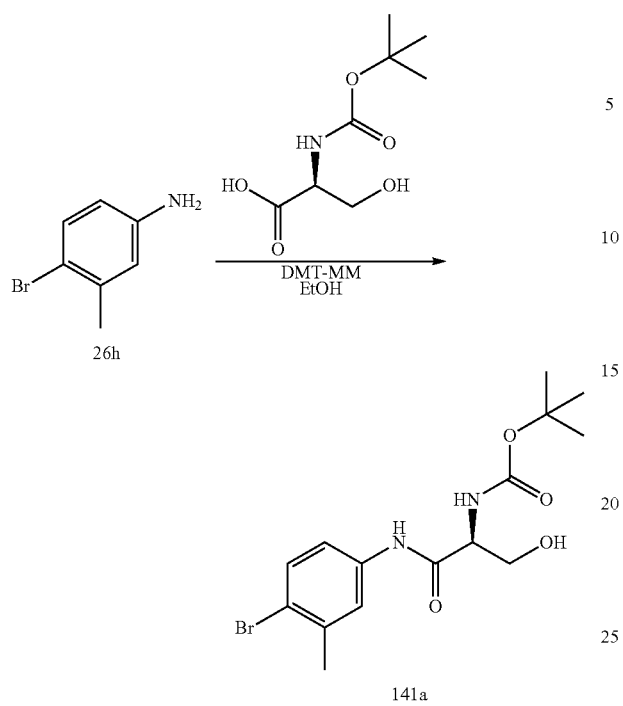

[(S)-1-(4-Bromo-3-methyl-phenylcarbamoyl)-2-hydroxy-ethyl]-carbamic acid tert-butyl ester was synthesized by operations similar to those in Reaction 10-1 using appropriate reagents and starting material.

MS (ESI) m/z=317, 219 (M-tBu+H+H)+.

Example 142

N-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methanesulfonamide (Compound 689)

(Reaction 142-1)

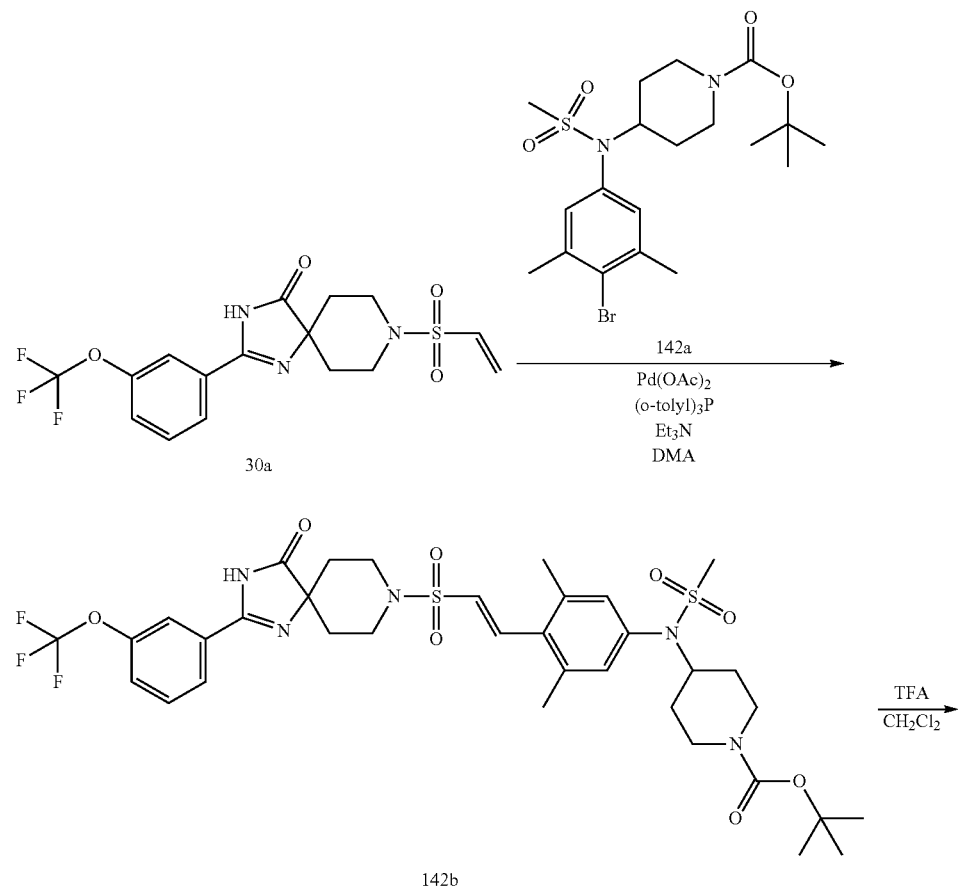

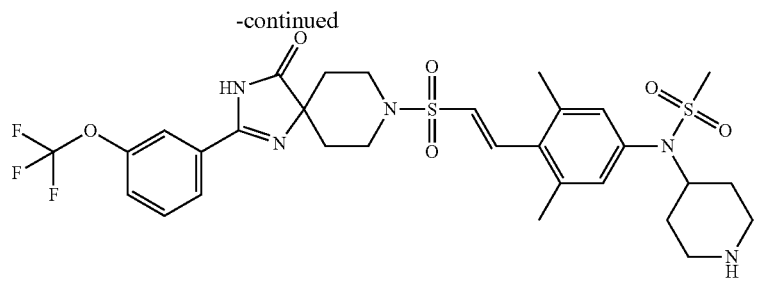

Compound 689

N-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-piperidin-4-yl-methanesulfonamide was synthesized by operations similar to those in Reaction 26-1 and Reaction 7-2 using appropriate reagents and starting material.

MS (ESI) m/z=684 (M+H)+.

The aryl bromide reagent used in the synthesis of Compound 142 (4-[(4-bromo-3,5-dimethyl-phenyl)-methanesulfonyl-amino]-piperidine-1-carboxylic acid tert-butyl ester) was synthesized as follows.

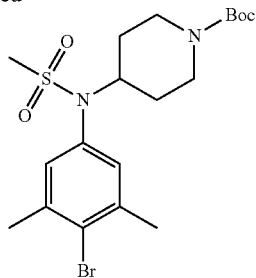

142a

4-[(4-Bromo-3,5-dimethyl-phenyl)-methanesulfonyl-amino]-piperidine-1-carboxylic acid tert-butyl ester was synthesized by operations similar to those in Reaction 41-1 and Reaction 6-1 using appropriate reagents and starting material.

MS (ESI) m/z=461, 463 (M+H)+.

(Reaction 142-2)

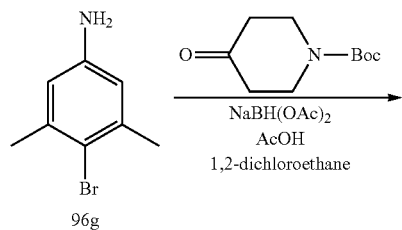

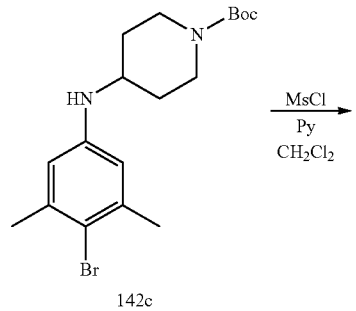

Example 143

8-[(E)-2-(2,6-Dimethyl-4-methylamino-phenyl)-ethenesulfonyl]-2-(9,9,9-trifluoro-nonyl)-1,3,8-triaza-spiro[4.5]dec-1-en-4-one (Compound 690)

(Reaction 143-1)

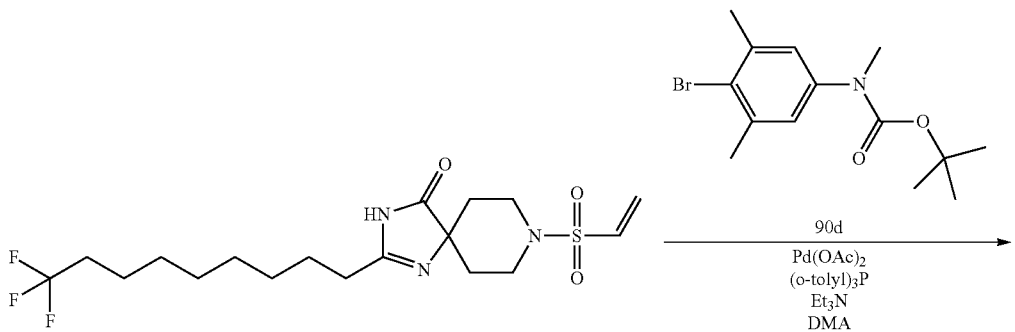

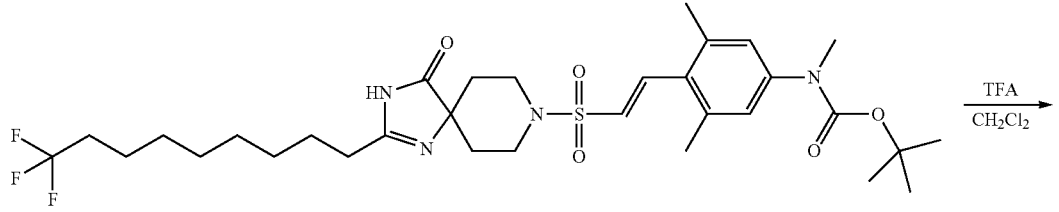

143a


Compound 690

8-[(E)-2-(2,6-Dimethyl-4-methylamino-phenyl)-ethenesulfonyl]-2-(9,9,9-trifluoro-nonyl)-1,3,8-triaza-spiro[4.5]dec-1-en-4-one was synthesized by operations similar to those in Reaction 26-1 and Reaction 7-2 using appropriate reagents and starting material.

MS (ESI) m/z=557 (M+H)+.

The aryl bromide reagent used in the synthesis of Compound 690 ((4-bromo-3,5-dimethyl-phenyl)-methyl-carbamic acid tert-butyl ester) was synthesized as follows.

(Reaction 143-2)

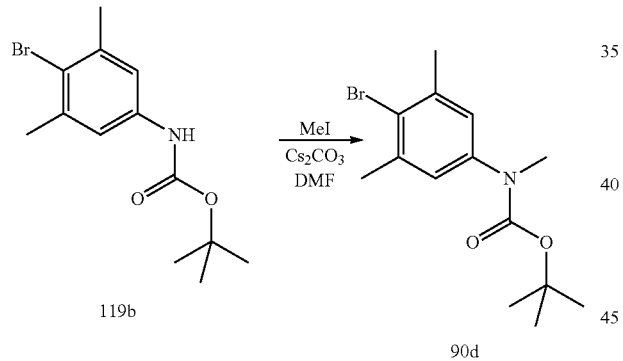

Iodomethane (20.5 ml, 329 mmol) was added to a solution of (4-bromo-3,5-dimethyl-phenyl)-carbamic acid tert-butyl ester (47.5 g, 158 mmol) and cesium carbonate (80.6 g, 247 mmol) in DMF (165 ml) at room temperature, and the mixture was stirred for 27 hours. Further, cesium carbonate (26.9 g, 82.6 mmol) and iodomethane (20.5 ml, 329 mmol) were added at room temperature, and the mixture was further stirred for three days. An aqueous ammonium chloride solution was added to the reaction mixture, followed by extraction with ethyl acetate. The organic layer was sequentially washed with water and saturated brine and then concentrated under reduced pressure. The resulting residue was purified by silica gel column chromatography (hexane-ethyl acetate) to give (4-bromo-3,5-dimethyl-phenyl)-methyl-carbamic acid tert-butyl ester (9.34 g, 92%).

MS (ESI) m/z=258, 260 (M-tBu+H+H)+.

Example 144

8-[(E)-2-(2,6-Dimethyl-4-methylamino-phenyl)-ethenesulfonyl]-2-(8,8,9,9,9-pentafluoro-nonyl)-1,3,8-triaza-spiro[4.5]dec-1-en-4-one (Compound 691)

(Reaction 144-1)

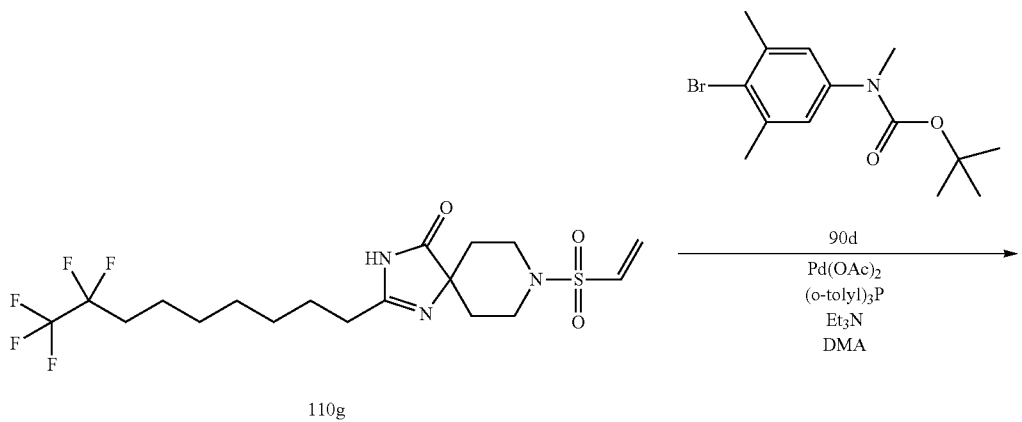

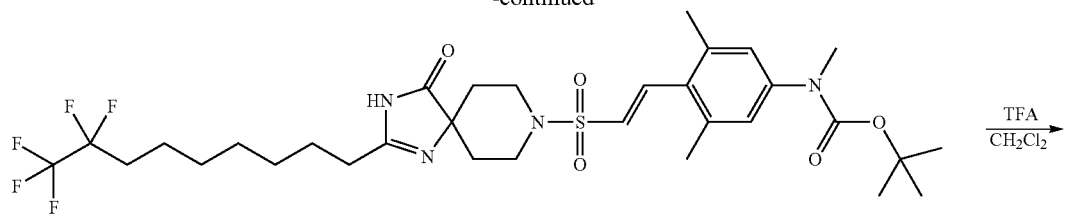
144a
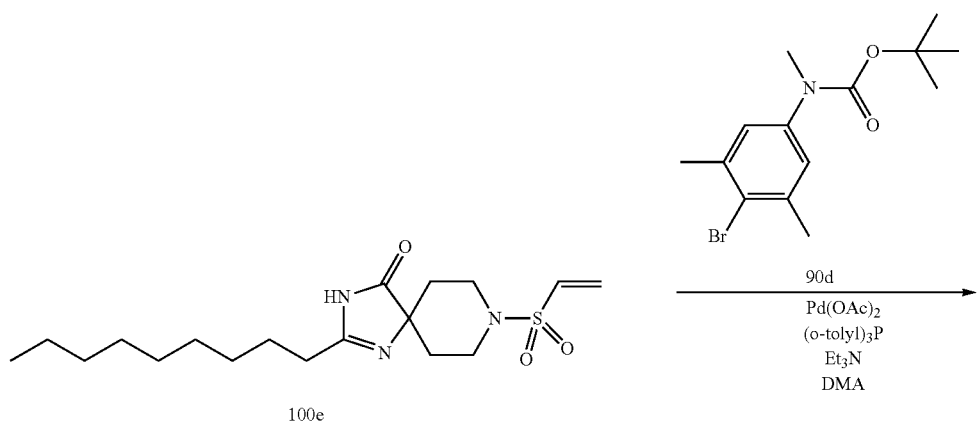
Compound 691
8-[(E)-2-(2,6-Dimethyl-4-methylamino-phenyl)-ethene-sulfonyl]-2-(8,8,9,9,9-pentafluoro-nonyl)-1,3,8-triaza-spiro[4.5]dec-1-en-4-one was synthesized by operations similar to those in Reaction 26-1 and Reaction 7-2 using appropriate reagents and starting material.
MS (ESI) m/z=593 (M+H)+.
Example 145
1-{3,5-Dimethyl-4-[(E)-2-(2-nonyl-4-oxo-1,3,8-triaza-spiro[4.5]dec-1-ene-8-sulfonyl)-vinyl]-phenyl}-1-methyl-urea (Compound 692)
(Reaction 145-1)
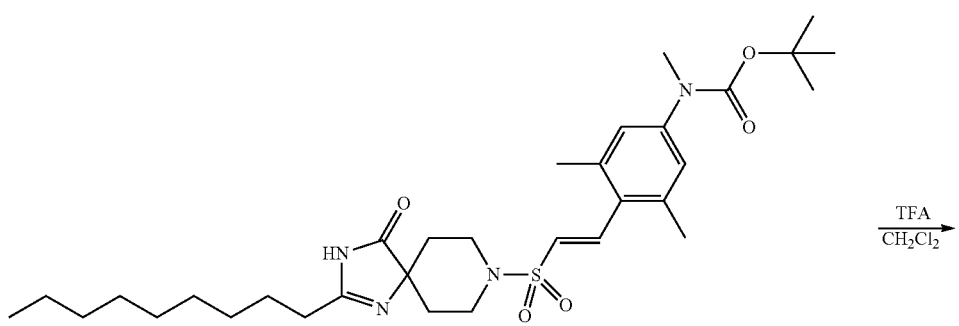
145a

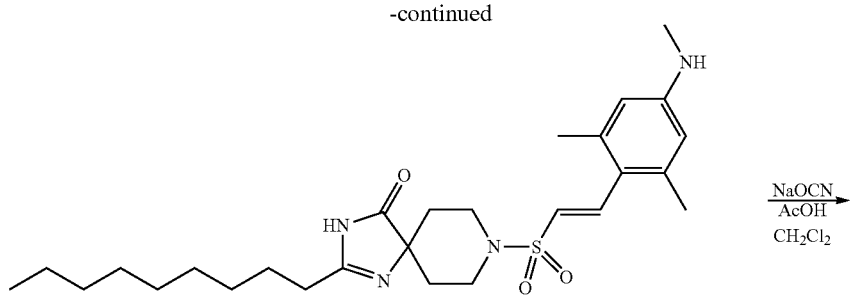

145b

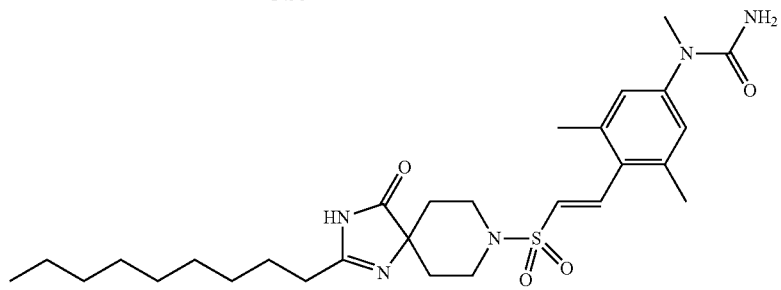

Compound 692

1-{3,5-Dimethyl-4-[(E)-2-(2-nonyl-4-oxo-1,3,8-triaza-spiro[4.5]dec-1-ene-8-sulfonyl)-vinyl]-phenyl}-1-methyl-urea was synthesized by operations similar to those in Reaction 25-2, Reaction 7-2 and Reaction 89-2 using appropriate reagents and starting material.

MS (ESI) m/z=546 (M+H)+.

Example 146

1-(2-Methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 693)

(Reaction 146-1)

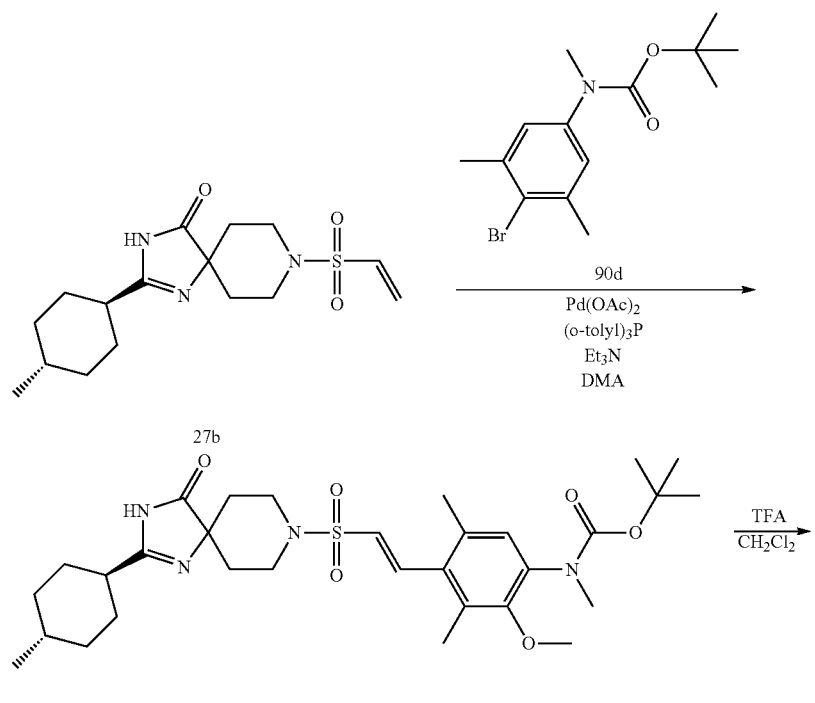

-continued

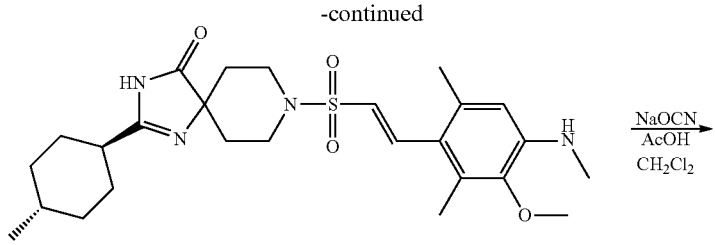

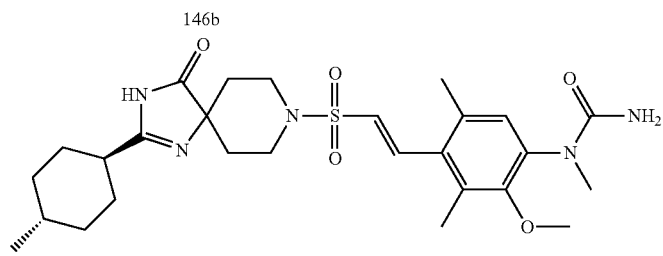

Compound 693

1-(2-Methoxy-3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1, Reaction 7-2 and Reaction 89-2 using appropriate reagents and starting material.

MS (ESI) m/z=546 (M+H)+.

Example 147

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea (Compound 694)

(Reaction 147-1)

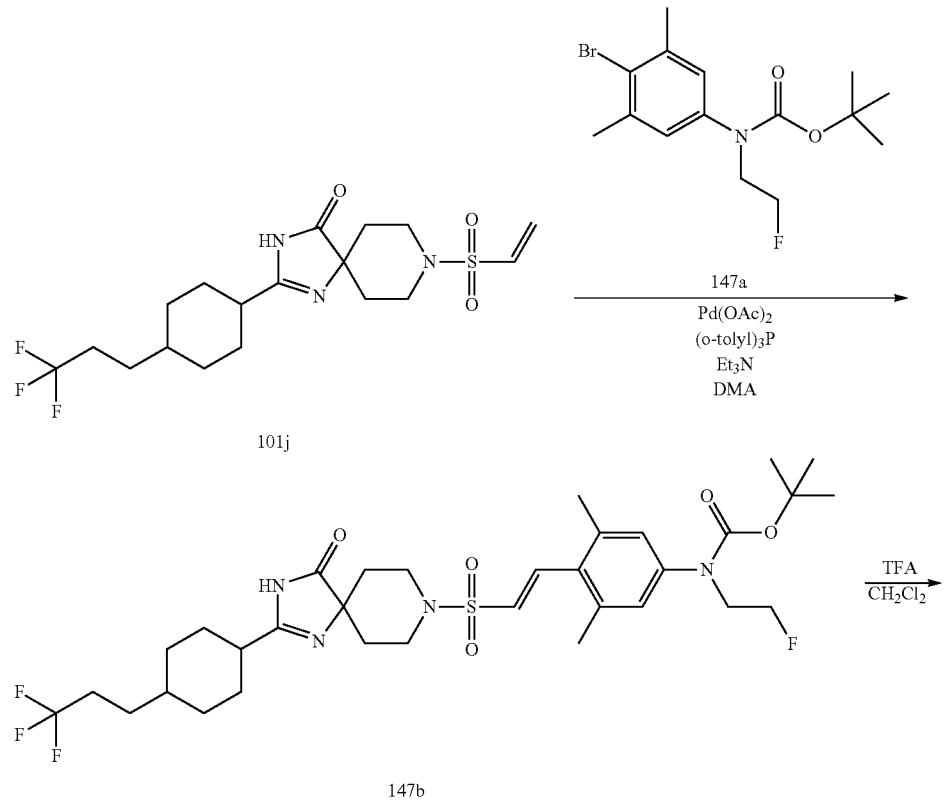

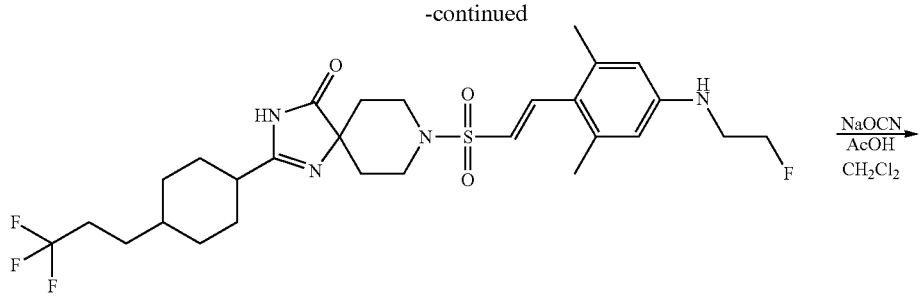

147c

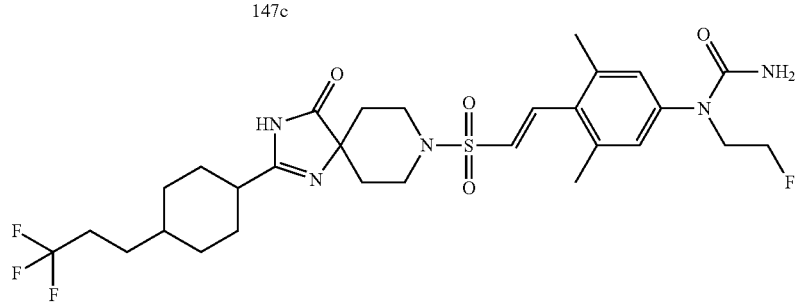

Compound 694

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-(2-fluoro-ethyl)-urea was synthesized by operations similar to those in Reaction 26-1, Reaction 7-2 and Reaction 89-2 using appropriate reagents and starting material.

MS (ESI) m/z=630 (M+H)+.

The aryl bromide reagent used in the synthesis of Compound 694 ((4-bromo-3,5-dimethyl-phenyl)-(2-fluoro-ethyl)-carbamic acid tert-butyl ester) was synthesized as follows.

(Reaction 147-2)

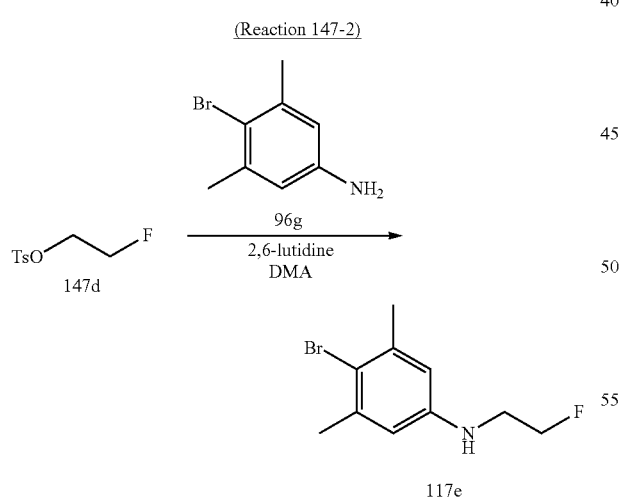

A solution of 4-bromo-3,5-dimethyl-phenylamine (400 mg, 2 mmol), toluene-4-sulfonic acid 2-fluoro-ethyl ester (567 mg, 2.6 mmol) and 2,6-lutidine (429 mg, 4.0 mmol) in DMA (5 ml) was heated with stirring at 120° C. for four hours. The mixture was quenched with water and then extracted with ethyl acetate. The organic layer was sequentially washed with water and saturated brine and then concentrated under reduced pressure. The resulting residue was purified by silica gel column chromatography (ethyl acetate-hexane) to give (4-bromo-3,5-dimethyl-phenyl)-(2-fluoro-ethyl)-amine (262 mg, 53%).

$^1$H-NMR (CDCl$_3$) δ 6.39 (s, 2H), 4.68 (t, 1H, J=4.96 Hz), 4.52 (t, 1H, J=4.96 Hz), 3.92 (brd, 1H), 3.45 (t, 1H, J=4.96 Hz), 3.36 (t, 1H, J=4.96 Hz), 2.34 (s, 3H).

(Reaction 147-3)

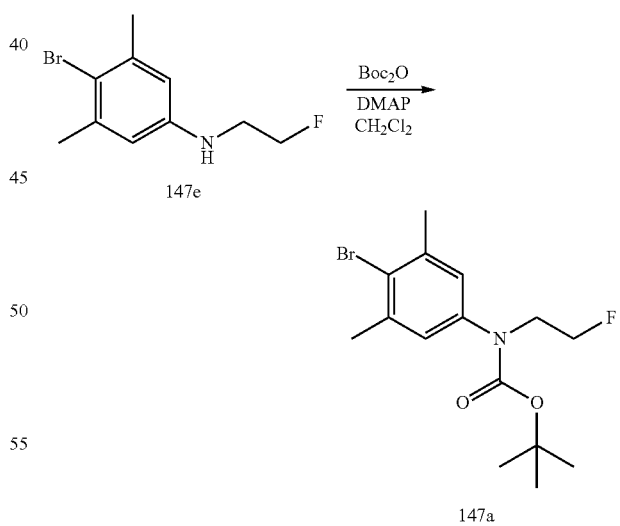

(4-Bromo-3,5-dimethyl-phenyl)-(2-fluoro-ethyl)-carbamic acid tert-butyl ester was synthesized by operations similar to those in Reaction 19-2 (using DMAP as a base) using appropriate reagents and starting material.

$^1$H-NMR (CDCl$_3$) δ 6.97 (s, 2H), 4.64 (t, 1H, J=4.96 Hz), 4.48 (t, 1H, J=4.96 Hz), 3.9 (t, 1H, J=4.96 Hz), 3.82 (t, 1H, J=4.96 Hz), 2.39 (s, 6H), 1.45 (s, 9H).

Example 148
1-(3-Chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 695)
(Reaction 148-1)
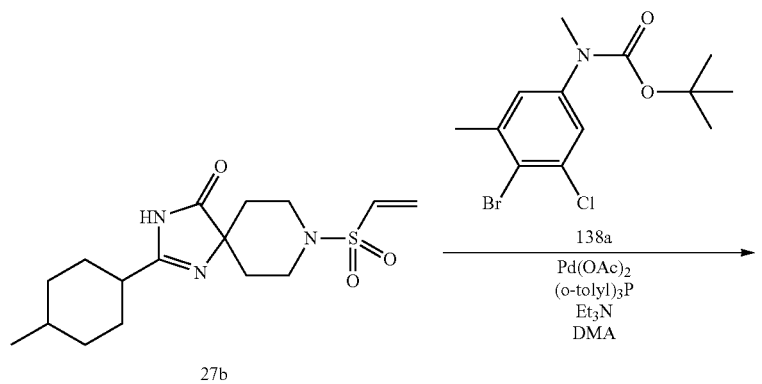
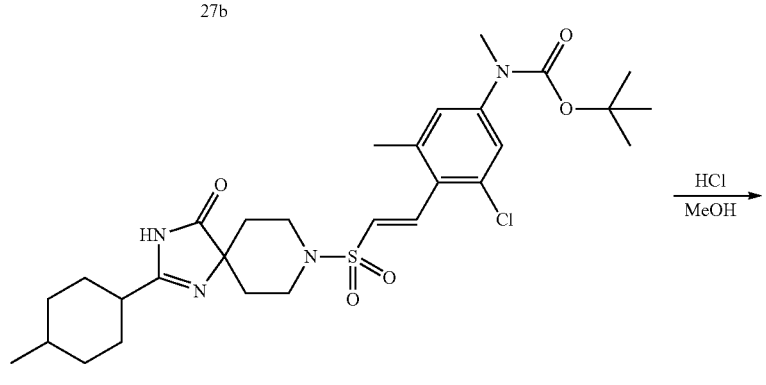
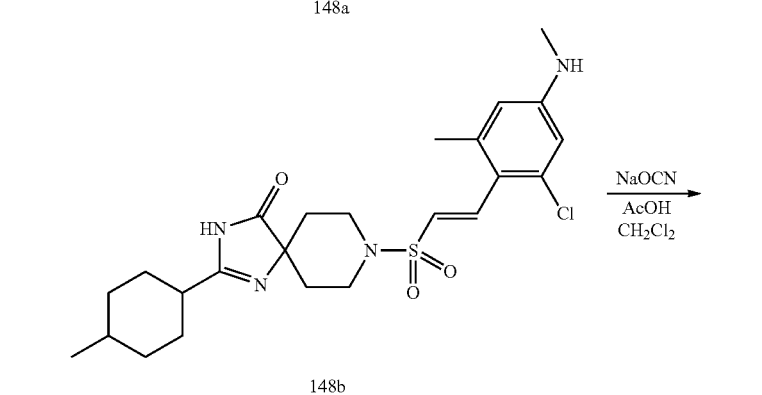
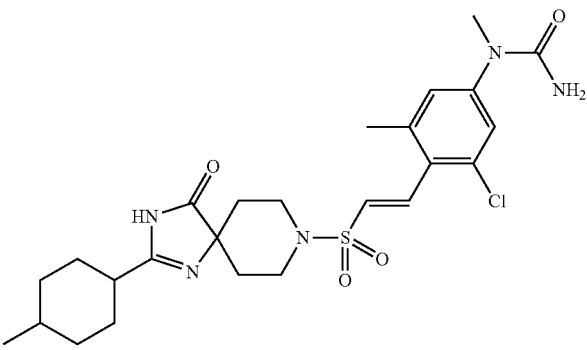
Compound 695

795

1-(3-Chloro-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1, Reaction 50-2 and Reaction 89-2 using appropriate reagents and starting material.

MS (ESI) m/z=630 (M+H)+.

796

Example 149

1-[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea (Compound 696)

(Reaction 149-1)

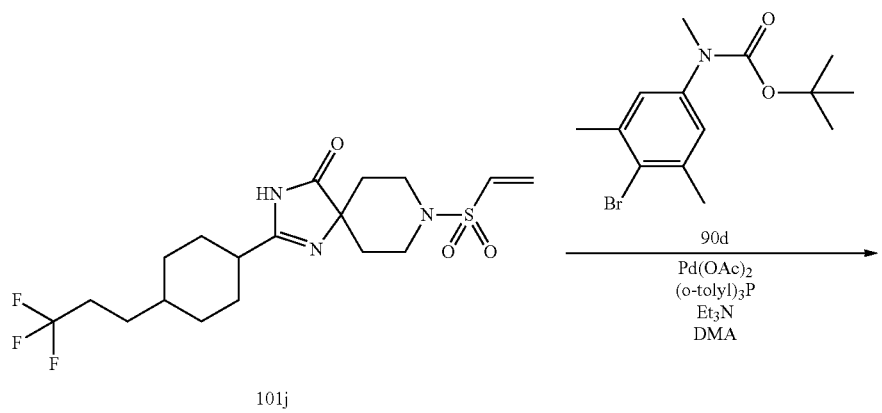

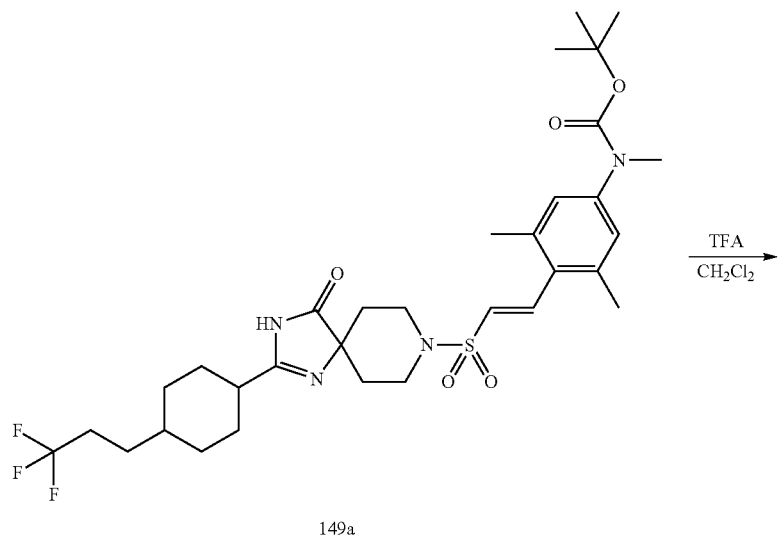

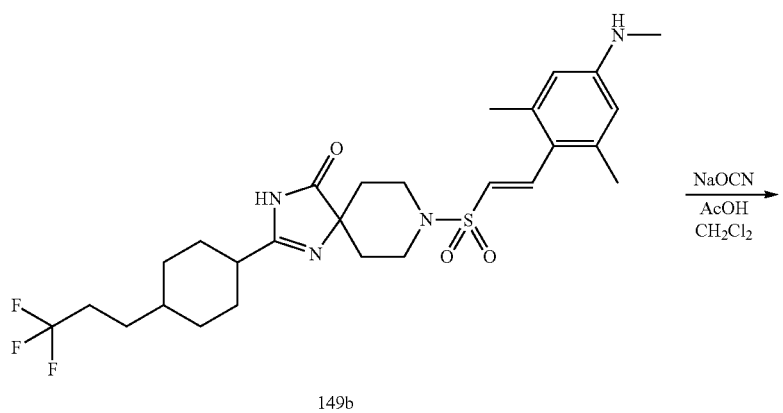

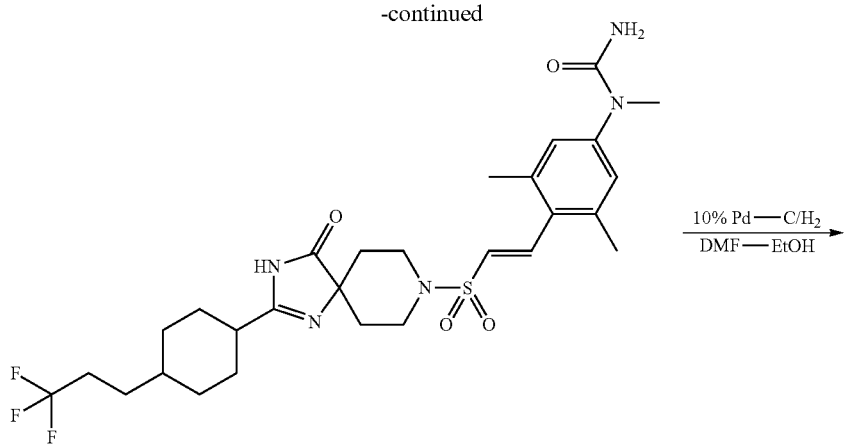

149c

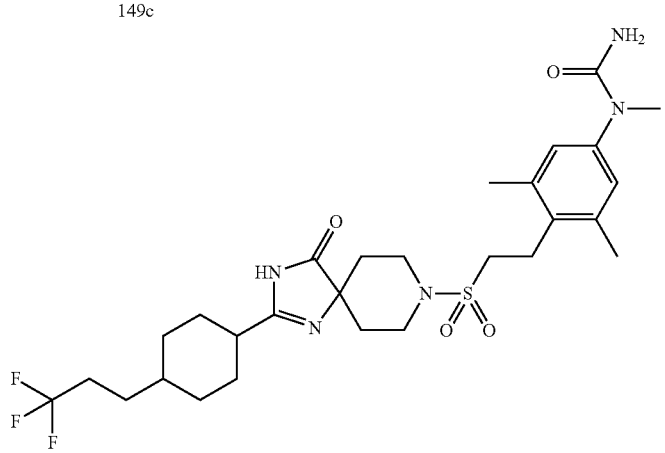

Compound 696

1-[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-1-methyl-urea was synthesized by operations similar to those in Reaction 25-2, Reaction 7-2, Reaction 89-2 and Reaction 42-2 using appropriate reagents and starting material.

MS (ESI) m/z=600 (M+H)+.

Example 150

8-{(E)-2-[4-((R)-2,3-Dihydroxy-propoxy)-2,6-dimethyl-phenyl]-ethenesulfonyl}-2-[4-(3,3,3-trifluoropropyl)-cyclohexyl]-1,3,8-triaza-spiro[4.5]dec-1-en-4-one (Compound 697)

(Reaction 150-1)

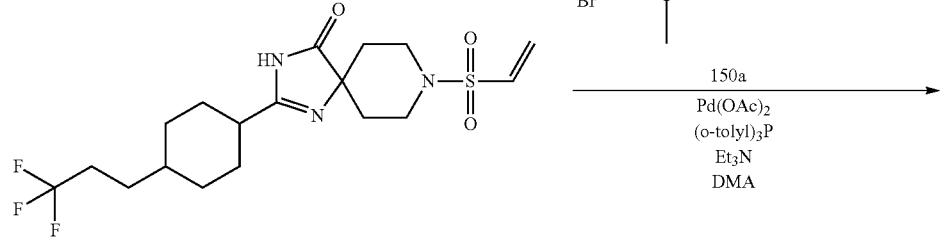

101j

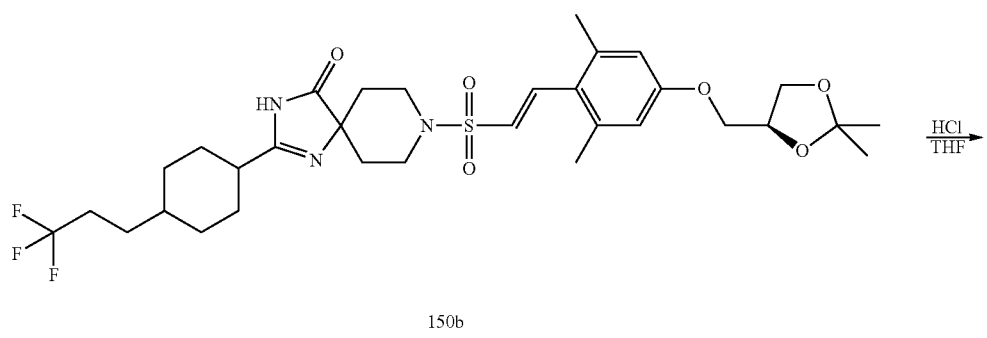

150b

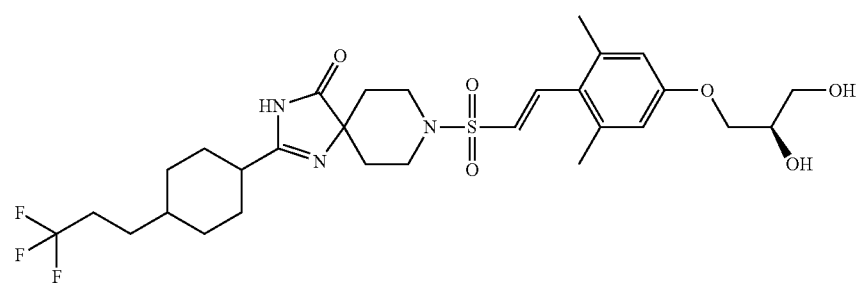

Compound 697

8-{(E)-2-[4-((R)-2,3-Dihydroxy-propoxy)-2,6-dimethyl-phenyl]-ethenesulfonyl}-2-[4-(3,3,3-trifluoro-propyl)-cyclohexyl]-1,3,8-triaza-spiro[4.5]dec-1-en-4-one was synthesized by operations similar to those in Reaction 25-2 and Reaction 25-4 using appropriate reagents and starting material.

MS (ESI) m/z=616 (M+H)+.

The example compound shown below was synthesized by operations similar to those in Example 150 using appropriate reagents and starting material.

Compound 698

TABLE 102

| Target Compound | Structure | LCMS condition | Retention time (min) | MS (m/z) |
|---|---|---|---|---|
| 698 | 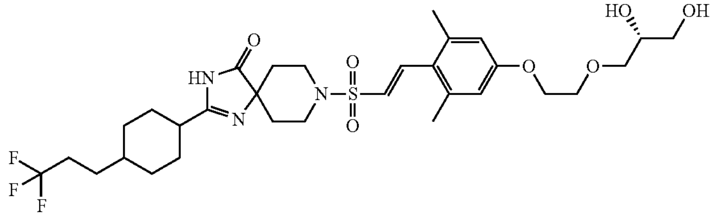 [SMILES: Cc1cc(OCCOC[C@H](O)CO)cc(C)c1/C=C/S(=O)(=O)N1CCC2(CC1)N=C(C1CCC(CCC(F)(F)F)CC1)NC2=O] | LCMS-D-1 | 2.56 | 660 (M + H)+ |

Example 151

N-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide (Compound 699)

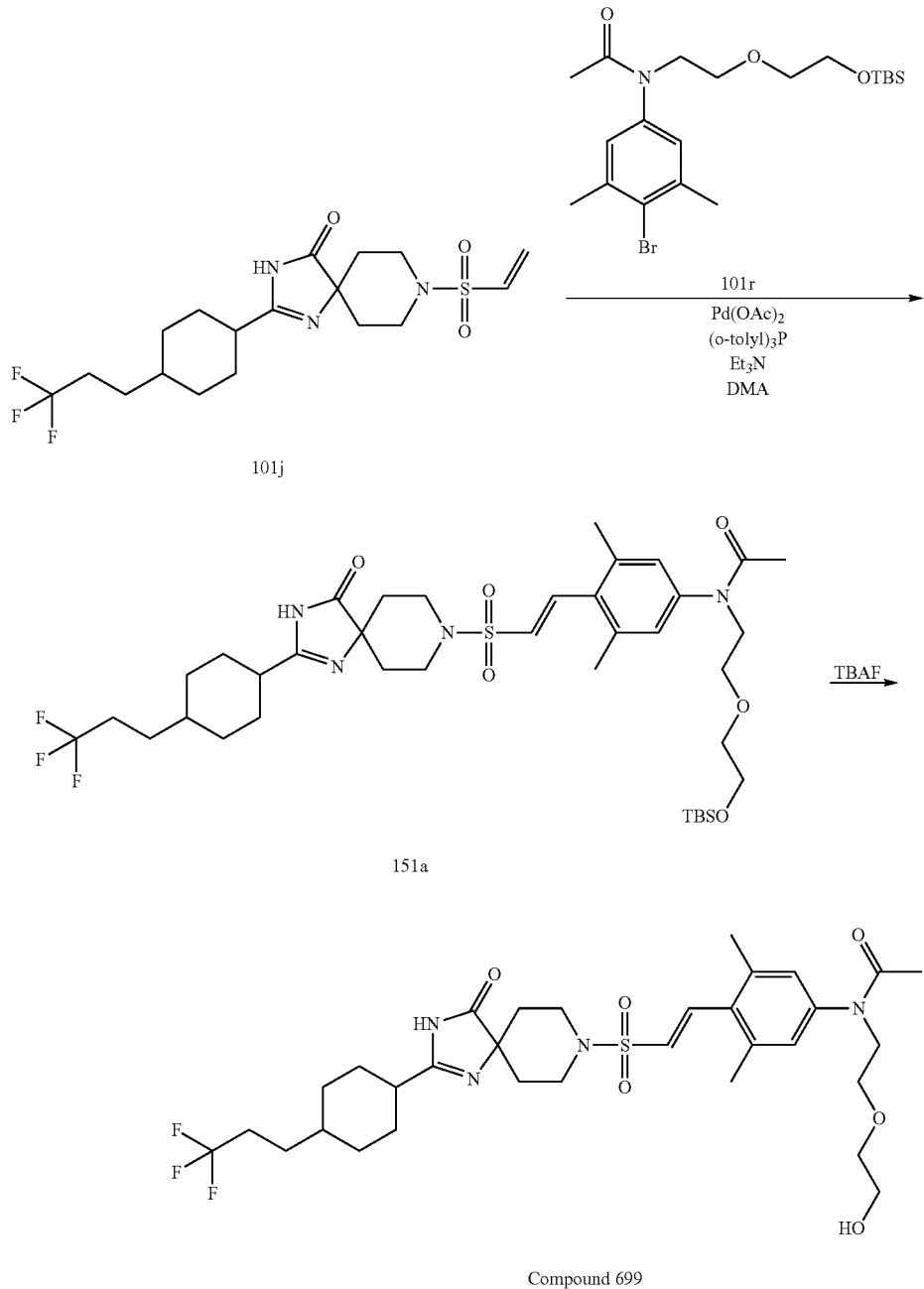

N-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-N-[2-(2-hydroxy-ethoxy)-ethyl]-acetamide was synthesized by operations similar to those in Reaction 25-2 and Reaction 39-2 using appropriate reagents and starting material.

MS (ESI) m/z=671 (M+H)+.

The aryl bromide reagent used in the synthesis of Compound 699 (N-(4-bromo-3,5-dimethyl-phenyl)-N-{2-[2-(tert-butyl-dimethyl-silanyloxy)-ethoxy]-ethyl}-acetamide) was synthesized as follows.

803

(Reaction 151-2)

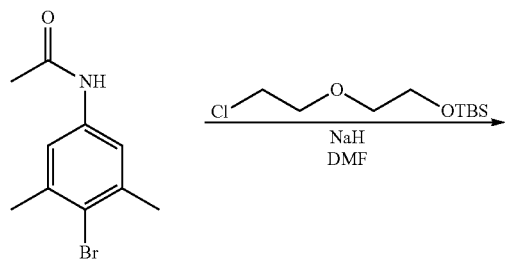

804

N-(4-Bromo-3,5-dimethyl-phenyl)-N-{2-[2-(tert-butyl-dimethyl-silanyloxy)-ethoxy]-ethyl}-acetamide was synthesized by operations similar to those in Reaction 25-3 using appropriate reagents and starting material.

$^1$H-NMR (CDCl$_3$) δ 6.95 (s, 2H), 3.81 (dd, 2H, J=6.10, 5.72 Hz), 3.70 (dd, 2H, J=4.95, 5.34 Hz), 3.58 (dd, 2H, J=5.72, 6.10 Hz), 3.46 (dd, 2H, J=5.72, 4.95 Hz), 2.41 (s, 6H), 1.83 (s, 3H), 0.86 (s, 9H).

Example 152

N-[2-(2-Hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide (Compound 700)

(Reaction 152-1)

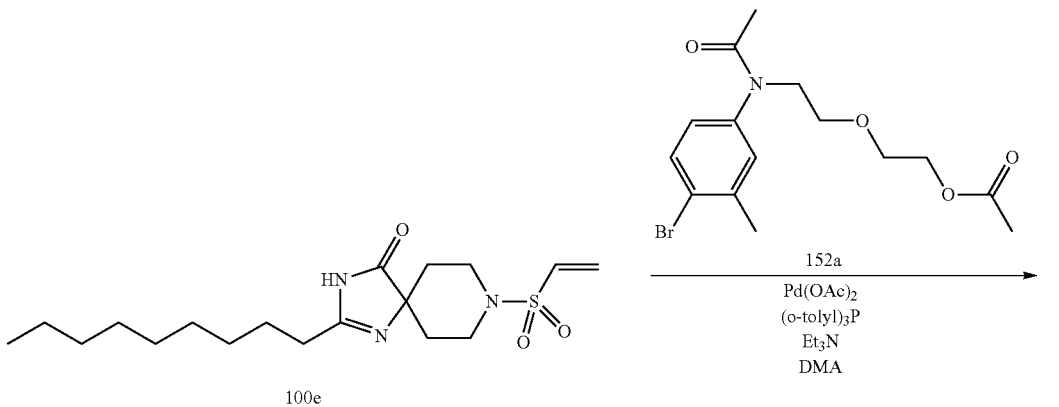

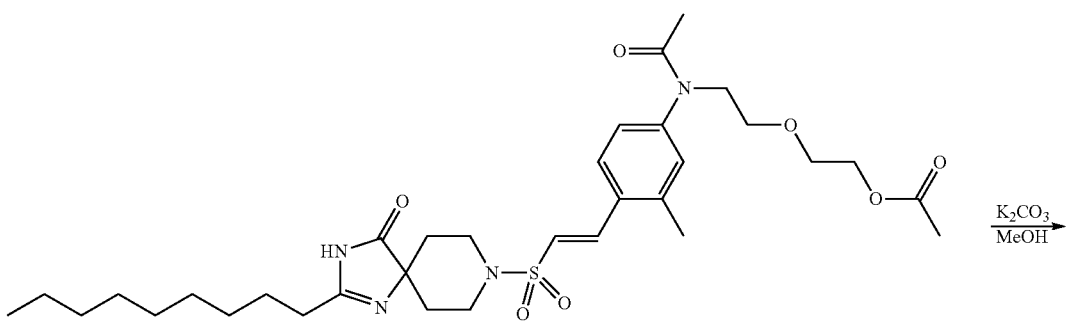

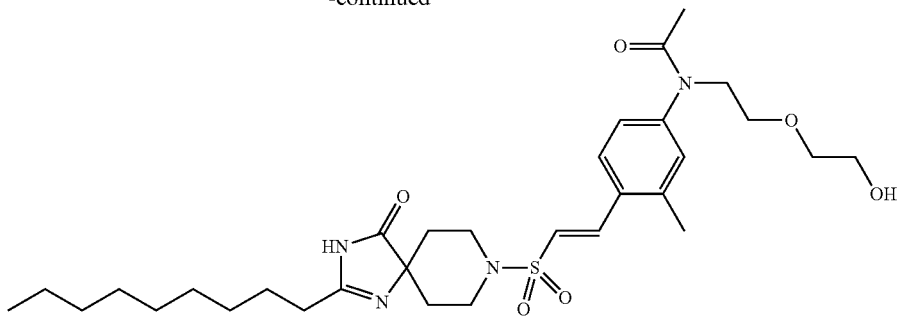

Compound 700

N-[2-(2-Hydroxy-ethoxy)-ethyl]-N-{3-methyl-4-[(E)-2-(2-nonyl-4-oxo-1,3,8-triaza-spiro[4.5]dec-1-ene-8-sulfonyl)-vinyl]-phenyl}-acetamide was synthesized by operations similar to those in Reaction 25-2 and Reaction 12-5 using appropriate reagents and starting material.

MS (ESI) m/z=605 (M+H)+.

The example compound shown below was synthesized by operations similar to those in Example 152 using appropriate reagents and starting material.

Compound 701

TABLE 103

| Target Compound | Structure | LCMS condition | Retention time (min) | MS (m/z) |
|---|---|---|---|---|
| 701 | 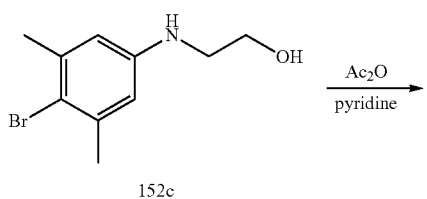 | LCMS-A-1 | 2.44 | 575 (M + H)+ |

The aryl bromide reagent used in the synthesis of Compound 701 (acetic acid 2-[acetyl-(4-bromo-3,5-dimethyl-phenyl)-amino]-ethyl ester) was synthesized as follows.

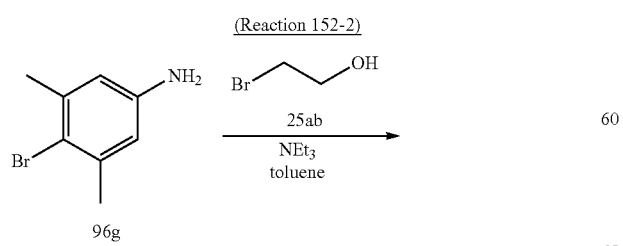

-continued

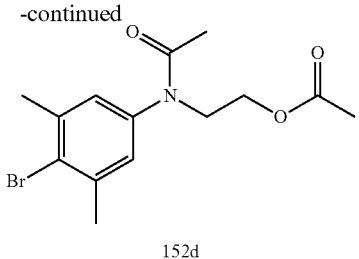

152d

Acetic acid 2-[acetyl-(4-bromo-3,5-dimethyl-phenyl)-amino]-ethyl ester was synthesized by operations similar to those in Reaction 25-12 and Reaction 12-2 using appropriate reagents and starting material.

MS (ESI) m/z=328, 330 (M+H)+.

Example 153

2-Cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one (Compound 702)

(Reaction 153-1)

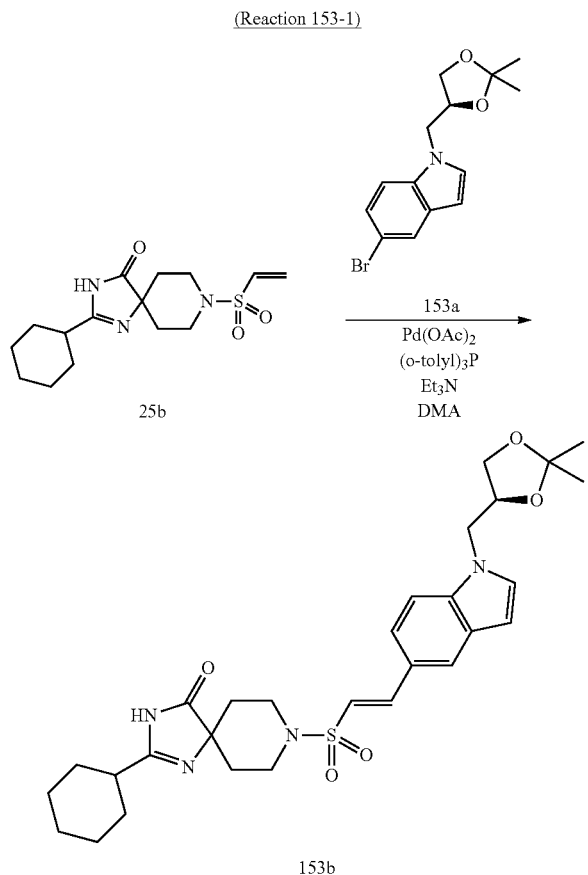

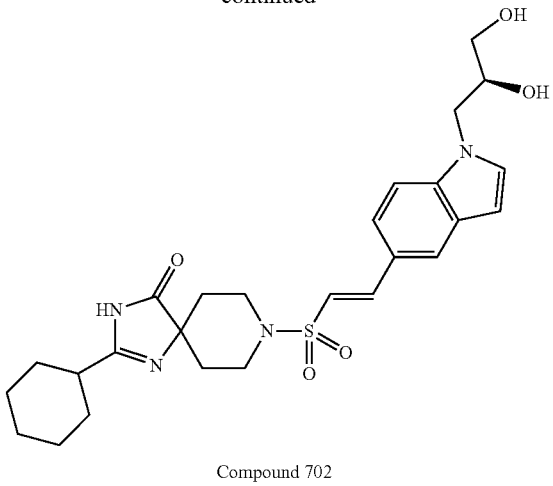

Compound 702

2-Cyclohexyl-8-{(E)-2-[1-((S)-2,2-dimethyl-[1,3]dioxolan-4-ylmethyl)-1H-indol-5-yl]-ethenesulfonyl}-1,3,8-triaza-spiro[4.5]dec-1-en-4-one (41.9 mg, 0.0755 mmol) was dissolved in a methylene chloride-methanol mixed solution (1:1, 1.5 ml). Trifluoroacetic acid (0.35 ml) was added and the mixture was stirred for two days. A saturated aqueous sodium bicarbonate solution and water were added to the reaction solution, followed by extraction with ethyl acetate. The organic layer was washed with water and saturated brine, dried over anhydrous sodium sulfate and concentrated under reduced pressure. The resulting residue was purified by P-TLC (ethyl acetate-methanol) to give 2-cyclohexyl-8-{(E)-2-[1-((S)-2,3-dihydroxy-propyl)-1H-indol-5-yl]-ethenesulfonyl}-1,3,8-triaza-spiro[4.5]dec-1-en-4-one (33.4 mg, 86%).

MS (ESI) m/z=515 (M+H)+.

The aryl bromide reagent used in the synthesis of Compound 702 (5-bromo-1-((S)-2,2-dimethyl-[1,3]dioxolan-4-ylmethyl)-1H-indole) was synthesized as follows.

2-Cyclohexyl-8-{(E)-2-[1-((S)-2,2-dimethyl-[1,3]dioxolan-4-ylmethyl)-1H-indol-5-yl]-ethenesulfonyl}-1,3,8-triaza-spiro[4.5]dec-1-en-4-one was synthesized by operations similar to those in Reaction 25-2 using appropriate reagents and starting material.

MS (ESI) m/z=555 (M+H)+.

(Reaction 153-2)

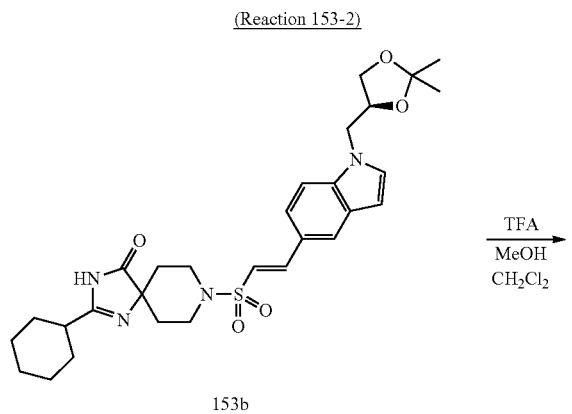

(Reaction 153-3)

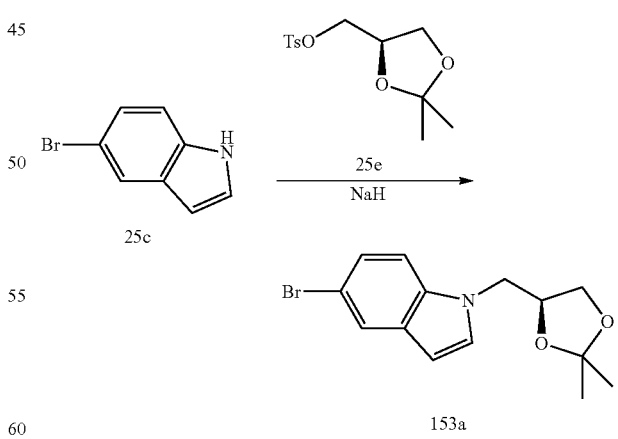

5-Bromo-1-((S)-2,2-dimethyl-[1,3]dioxolan-4-ylmethyl)-1H-indole was synthesized by operations similar to those in Reaction 25-3 using appropriate reagents and starting material.

MS (ESI) m/z=310 (M+H)+.

Example 154

8-((E)-2-{1-[2-((S)-2,3-Dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one (Compound 704)

(Reaction 154-1)

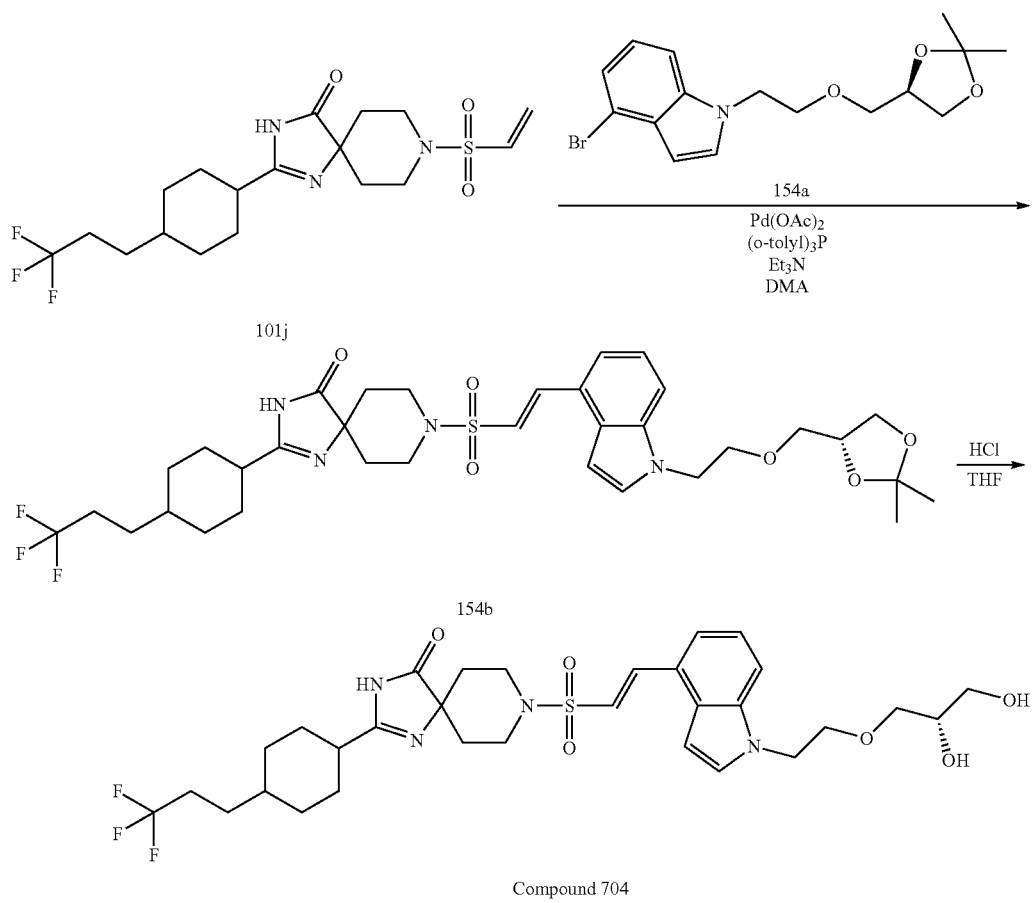

8-((E)-2-{1-[2-((S)-2,3-Dihydroxy-propoxy)-ethyl]-1H-indol-4-yl}-ethenesulfonyl)-2-[4-(3,3,3-trifluoro-propyl)-cyclohexyl]-1,3,8-triaza-spiro[4.5]dec-1-en-4-one was synthesized by operations similar to those in Reaction 26-1 and Reaction 25-4 using appropriate reagents and starting material.

MS (ESI) m/z=655 (M+H)+.

The example compounds shown below were synthesized by operations similar to those in Example 154 using appropriate reagents and starting materials.

Compounds 705 to Compound 706

TABLE 104

| Target Compound | Structure | LCMS condition | Retention time (min) | MS (m/z) |
| --- | --- | --- | --- | --- |
| 705 | 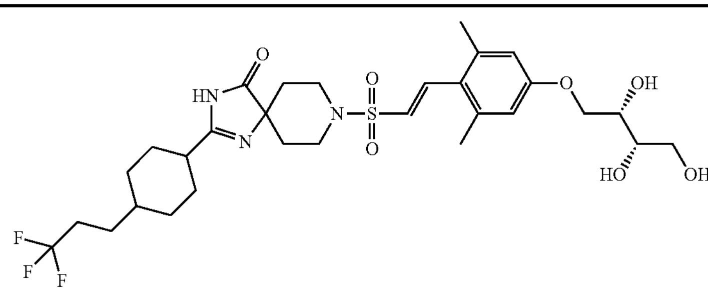 | LCMS-D-1 | 2.14 | 646 (M + H)+ |

TABLE 104-continued

| Target Compound | Structure | LCMS condition | Retention time (min) | MS (m/z) |
|---|---|---|---|---|
| 706 | 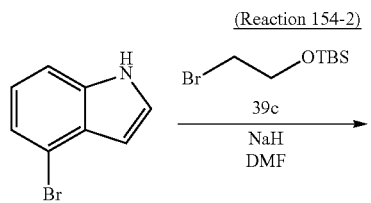 | LCMS-D-1 | 2.15 | 685 (M + H)+ |

The aryl bromide reagent used in the synthesis of Compound 704 (4-bromo-1-[2-((R)-2,2-dimethyl-[1,3]dioxolan-4-ylmethoxy)-ethyl]-1H-indole) was synthesized as follows.

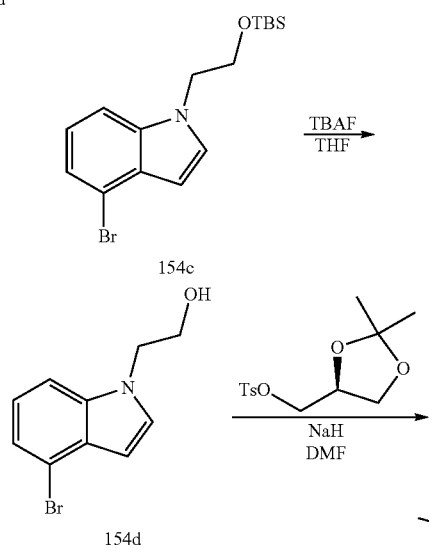

4-Bromo-1-[2-((R)-2,2-dimethyl-[1,3]dioxolan-4-ylmethoxy)-ethyl]-1H-indole was synthesized by operations similar to those in Reaction 25-3, Reaction 39-2 and Reaction 20-2 using appropriate reagents and starting material.

MS (ESI) m/z=354,356 (M+H)+.

The aryl bromide reagent used in the synthesis of Compound 705 ([(4S,5S)-5-(4-bromo-3,5-dimethyl-phenoxymethyl)-2,2-dimethyl-[1,3]dioxolan-4-ylmethoxy]-tert-butyl-dimethyl-silane) was synthesized as follows.

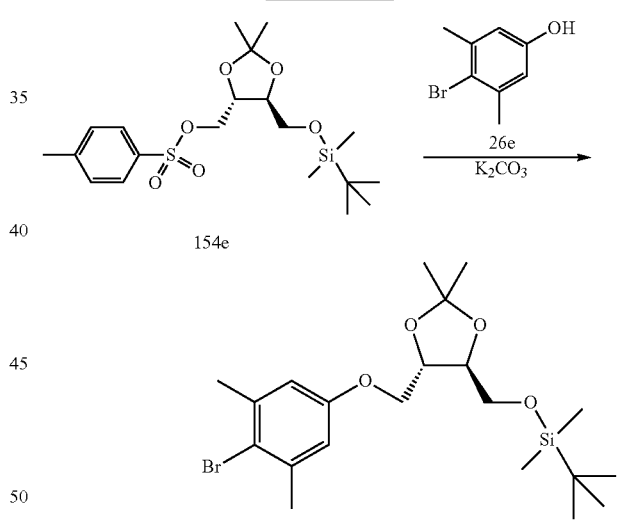

[(4S,5S)-5-(4-Bromo-3,5-dimethyl-phenoxymethyl)-2,2-dimethyl-[1,3]dioxolan-4-ylmethoxy]-tert-butyl-dimethyl-silane was synthesized by operations similar to those in Reaction 26-4 using appropriate reagents and starting material.

$^1$H-NMR (CDCl$_3$) δ 6.67 (s, 2H), 4.27 (m, 1H), 4.13-3.73 (m, 5H), 2.36 (s, 6H), 1.44 (s, 3H), 1.43 (s, 3H), 0.88 (s, 9H), 0.06 (s, 6H).

The aryl bromide reagent used in the synthesis of Compound 706 ({(4S,5S)-5-[2-(4-bromo-indol-1-yl)-ethoxymethyl]-2,2-dimethyl-[1,3]dioxolan-4-yl}-methanol) was synthesized as follows.

813

(Reaction 154-4)

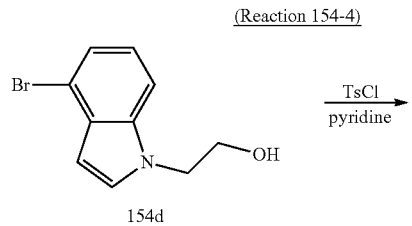

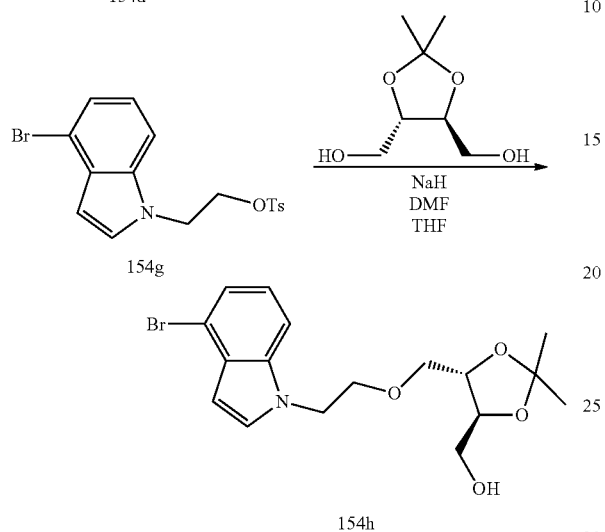

{(4S,5S)-5-[2-(4-Bromo-indol-1-yl)-ethoxymethyl]-2,2-dimethyl-[1,3]dioxolan-4-yl}-methanol was synthesized by operations similar to those in Reaction 6-1 and Reaction 20-2 using appropriate reagents and starting material.

¹H-NMR (CDCl₃) δ 7.28 (m, 2H), 7.20 (d, 1H, J=3.3 Hz), 7.06 (t, 1H, J=7.8 Hz), 6.55 (d, 1H, J=3.0 Hz), 4.30 (t, 2H, J=5.4 Hz), 3.94 (m, 1H), 3.84-3.41 (m, 7H), 1.91 (br s, 1H), 1.39 (s, 3H), 1.36 (s, 3H).

Example 155

N—((S)-2,3-Dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide (Compound 707)

(Reaction 155-1)

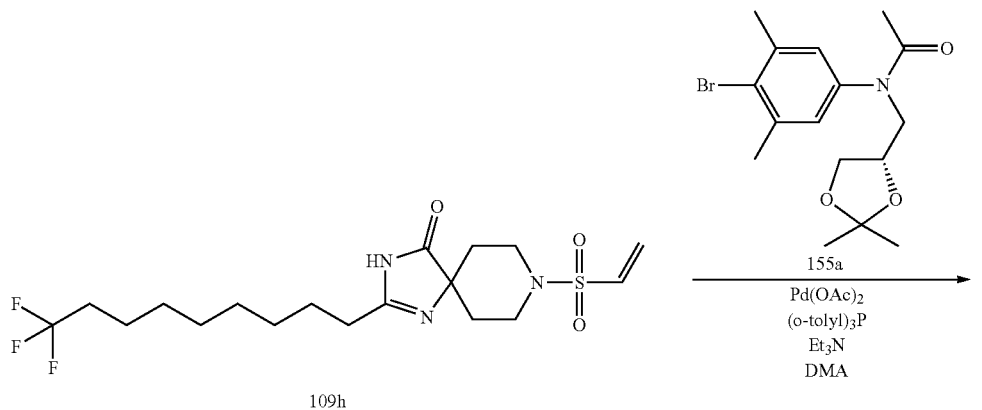

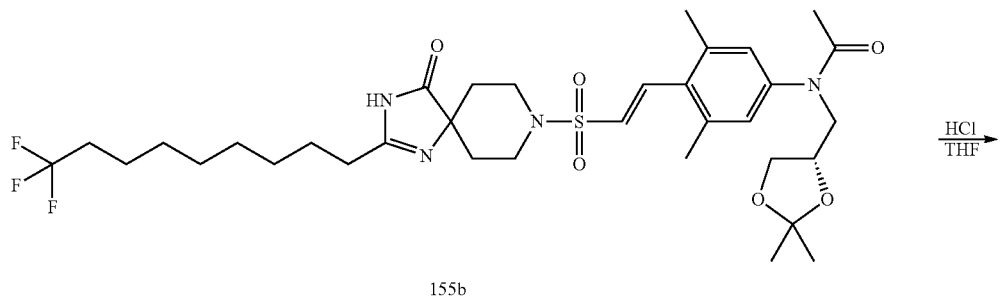

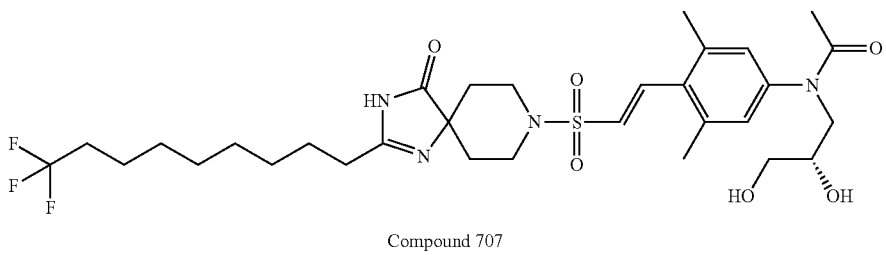

Compound 707

N—((S)-2,3-Dihydroxy-propyl)-N-(3,5-dimethyl-4-{(E)-2-[4-oxo-2-(9,9,9-trifluoro-nonyl)-1,3,8-triaza-spiro[4.5]dec-1-ene-8-sulfonyl]-vinyl}-phenyl)-acetamide was synthesized by operations similar to those in Reaction 26-1 and reaction 25-4 using appropriate reagents and starting material.

MS (ESI) m/z=659 (M+H)+.

Example 156

{4-[(E)-2-(2-Cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester (Compound 708)

(Reaction 156-1)

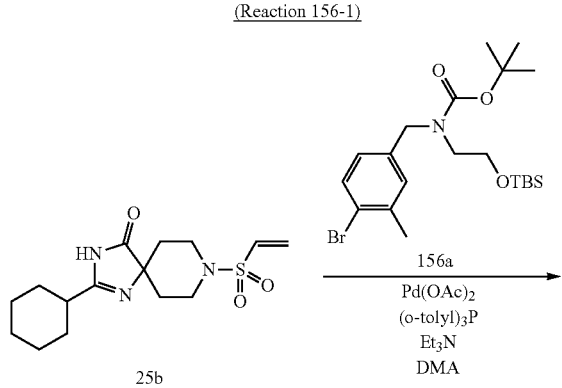

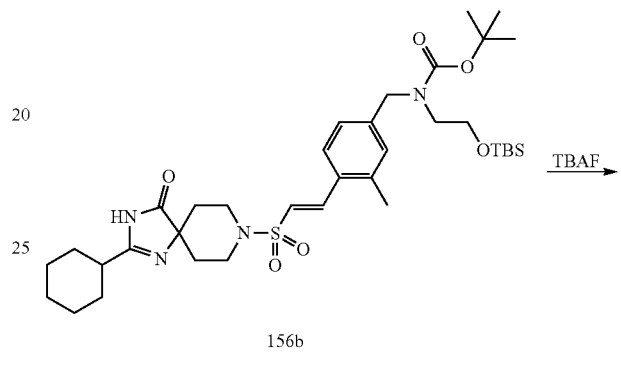

Compound 708

{4-[(E)-2-(2-Cyclohexyl-4-oxo-1,3,8-triaza-spiro[4.5]dec-1-ene-8-sulfonyl)-vinyl]-3-methyl-benzyl}-(2-hydroxy-ethyl)-carbamic acid tert-butyl ester was synthesized by operations similar to those in Reaction 26-1 and Reaction 39-2 using appropriate reagents and starting material.

MS (ESI) m/z=589 (M+H)+.

The example compounds shown below were synthesized by operations similar to those in Example 156 using appropriate reagents and starting materials.

Compounds 709 to Compound 710

TABLE 105

| Target Compound | Structure | LCMS condition | Retention time (min) | MS (m/z) |
|---|---|---|---|---|
| 709 | 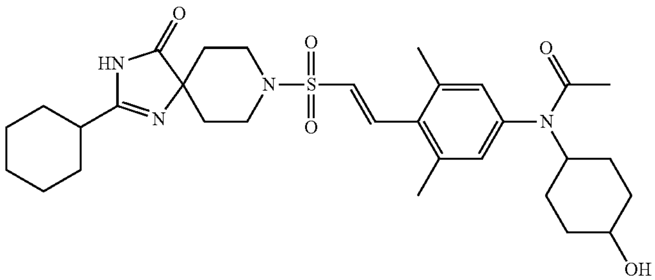 [SMILES: CC(=O)N(c1cc(C)c(/C=C/S(=O)(=O)N2CCC3(CC2)N=C(C2CCCCC2)NC3=O)c(C)c1)C1CCC(O)CC1] | LCMS-D-1 | 2.34 | 585 (M + H)+ |
| 710 | 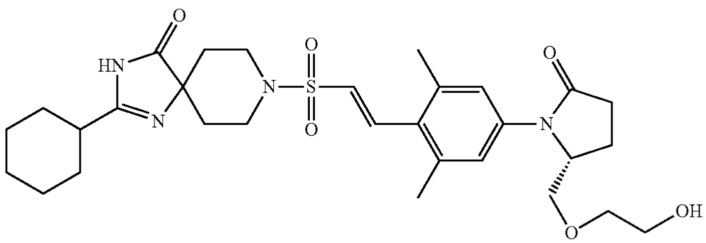 [SMILES: Cc1cc(N2C(=O)CC[C@@H]2COCCO)cc(C)c1/C=C/S(=O)(=O)N1CCC2(CC1)N=C(C1CCCCC1)NC2=O] | LCMS-D-1 | 2.53 | 587 (M + H)+ |

The aryl bromide reagent used in the synthesis of Compound 708 ((4-bromo-3-methyl-benzyl)-[2-(tert-butyl-dimethyl-silanyloxy)-ethyl]-carbamic acid tert-butyl ester) was synthesized as follows.

The aryl bromide reagent used in the synthesis of Compound 709 (N-(4-bromo-3,5-dimethyl-phenyl)-N-[4-(tert-butyl-dimethyl-silanyloxy)-cyclohexyl]-acetamide) was synthesized as follows.

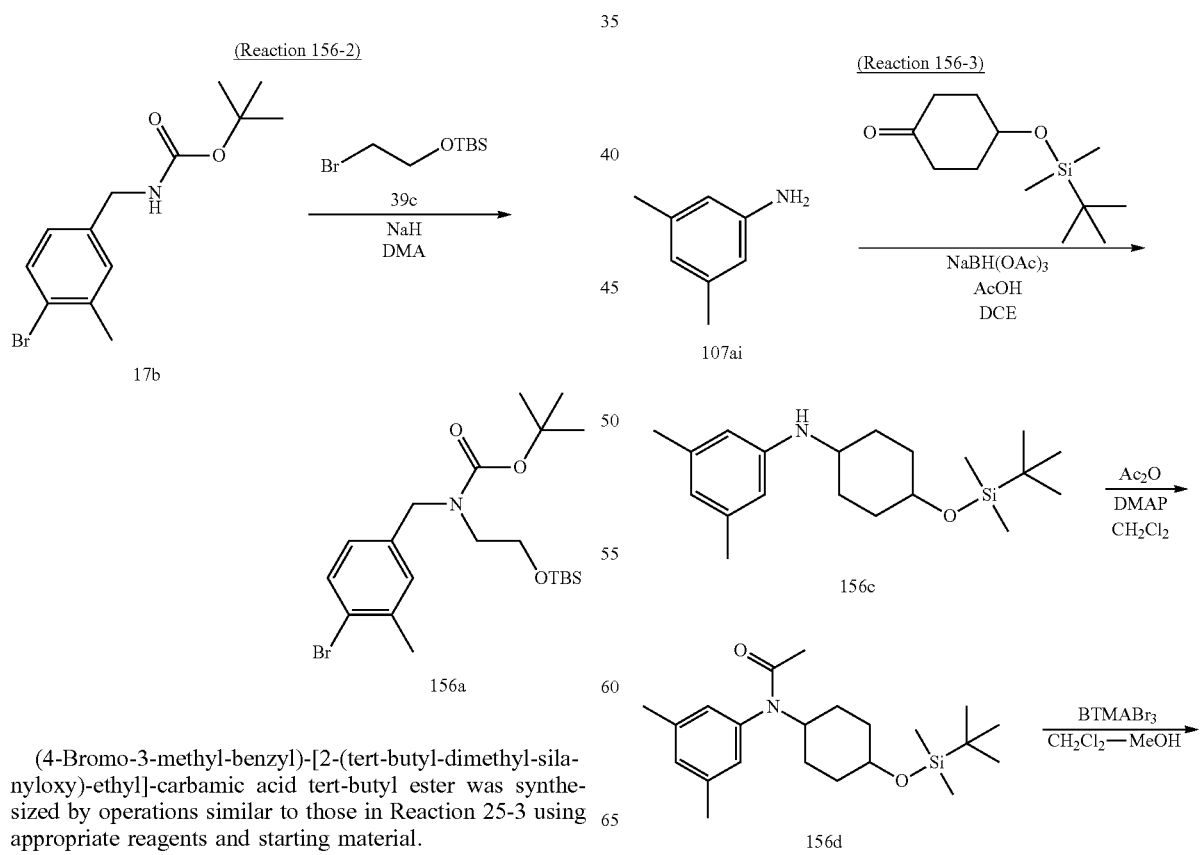

(4-Bromo-3-methyl-benzyl)-[2-(tert-butyl-dimethyl-silanyloxy)-ethyl]-carbamic acid tert-butyl ester was synthesized by operations similar to those in Reaction 25-3 using appropriate reagents and starting material.

MS (ESI) m/z=472, 474 (M+H)+.

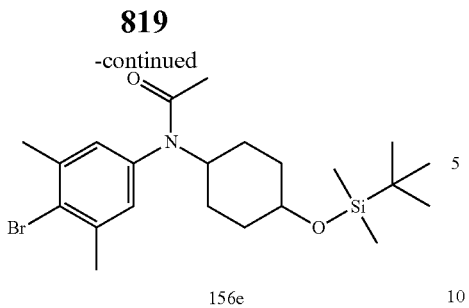

156e

N-(4-Bromo-3,5-dimethyl-phenyl)-N-[4-(tert-butyl-dimethyl-silanyloxy)-cyclohexyl]-acetamide was synthesized by operations similar to those in Reaction 41-1, Reaction 19-2 (using DMAP as a base) and Reaction 26-2 using appropriate reagents and starting material.

MS (ESI) m/z=454, 456 (M+H)+.

The aryl bromide reagent used in the synthesis of Compound 710 ((R)-1-(4-bromo-3,5-dimethyl-phenyl)-5-[2-(tert-butyl-dimethyl-silanyloxy)-ethoxymethyl]-pyrrolidin-2-one) was synthesized as follows.

(Reaction 156-4)

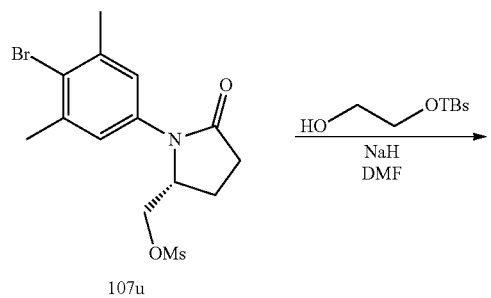

107u

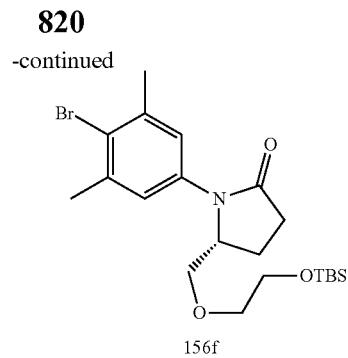

156f (R)-1-(4-Bromo-3,5-dimethyl-phenyl)-5-[2-(tert-butyl-dimethyl-silanyloxy)-ethoxymethyl]-pyrrolidin-2-one was synthesized by operations similar to those in Reaction 20-2 using appropriate reagents and starting material.

$^1$H-NMR (CDCl$_3$) δ 7.07 (s, 2H), 4.19 (m, 1H), 3.64 (t, 2H, J=4.96 Hz), 3.44 (m, 2H), 3.40 (t, 2H, J=4.96 Hz), 2.52 (m, 2H), 2.36 (s, 6H), 2.17 (m, 2H), 0.87 (s, 9H), 0.04 (s, 6H).

Example 157

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutyl-amide (Compound 711)

(Reaction 157-1)

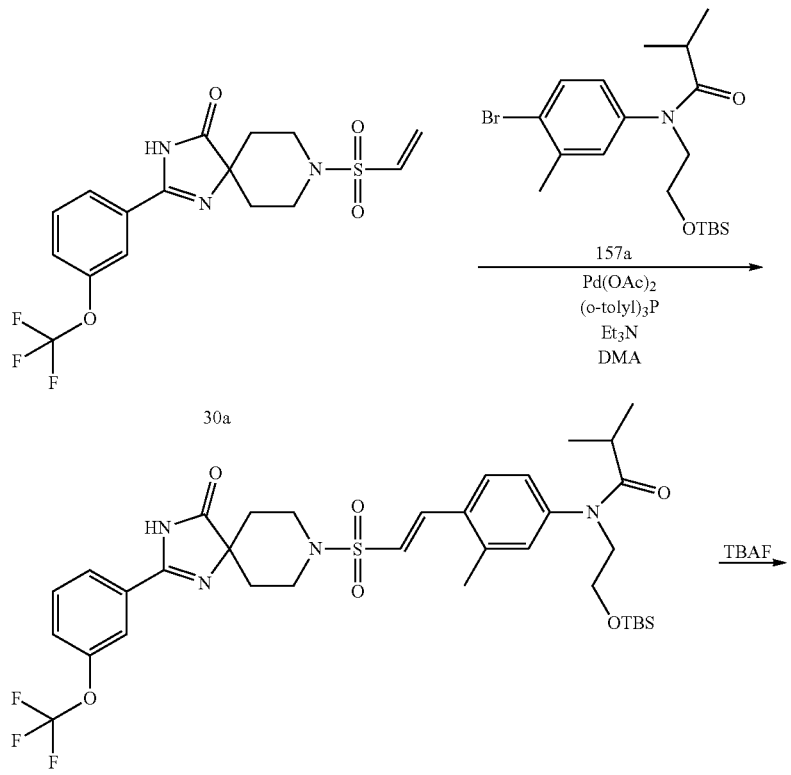

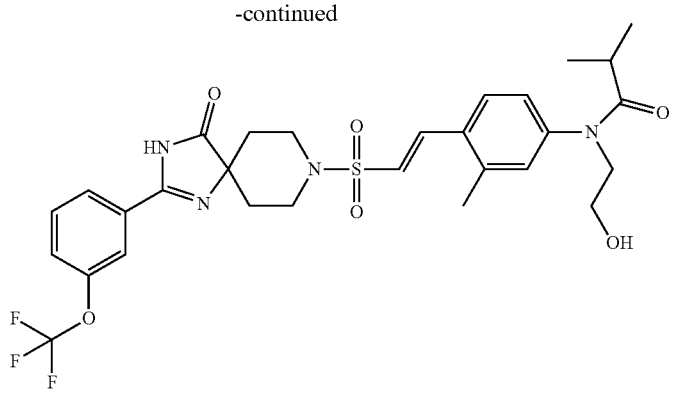

Compound 711

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-isobutylamide was synthesized by operations similar to those in Reaction 26-1 and Reaction 39-2 using appropriate reagents and starting material.

MS (ESI) m/z=623 (M+H)+.

The example compounds shown below were synthesized by operations similar to those in Example 157 using appropriate reagents and starting materials.

Compounds 712 to Compound 715

TABLE 106

| Target compound | Structure | LCMS condition | Retention time (min) | MS (m/z) |
|---|---|---|---|---|
| 712 | 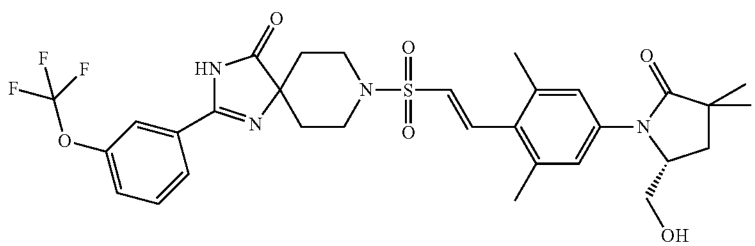 [SMILES: Cc1cc(N2C(=O)C(C)(C)C[C@@H]2CO)cc(C)c1/C=C/S(=O)(=O)N1CCC2(CC1)N=C(c1cccc(OC(F)(F)F)c1)NC2=O] | LCMS-D-1 | 2.90 | 649 (M + H)+ |
| 713 | 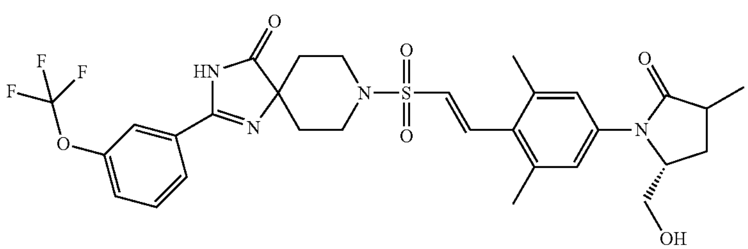 [SMILES: Cc1cc(N2C(=O)C(C)C[C@@H]2CO)cc(C)c1/C=C/S(=O)(=O)N1CCC2(CC1)N=C(c1cccc(OC(F)(F)F)c1)NC2=O] | LCMS-D-1 | 2.90 | 635 (M + H)+ |
| 714 | 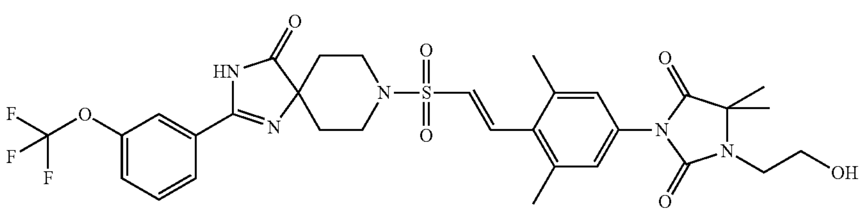 [SMILES: Cc1cc(N2C(=O)N(CCO)C(C)(C)C2=O)cc(C)c1/C=C/S(=O)(=O)N1CCC2(CC1)N=C(c1cccc(OC(F)(F)F)c1)NC2=O] | LCMS-D-1 | 3.20 | 678 (M + H)+ |

TABLE 106-continued

| Target compound | Structure | LCMS condition | Retention time (min) | MS (m/z) |
|---|---|---|---|---|
| 715 | 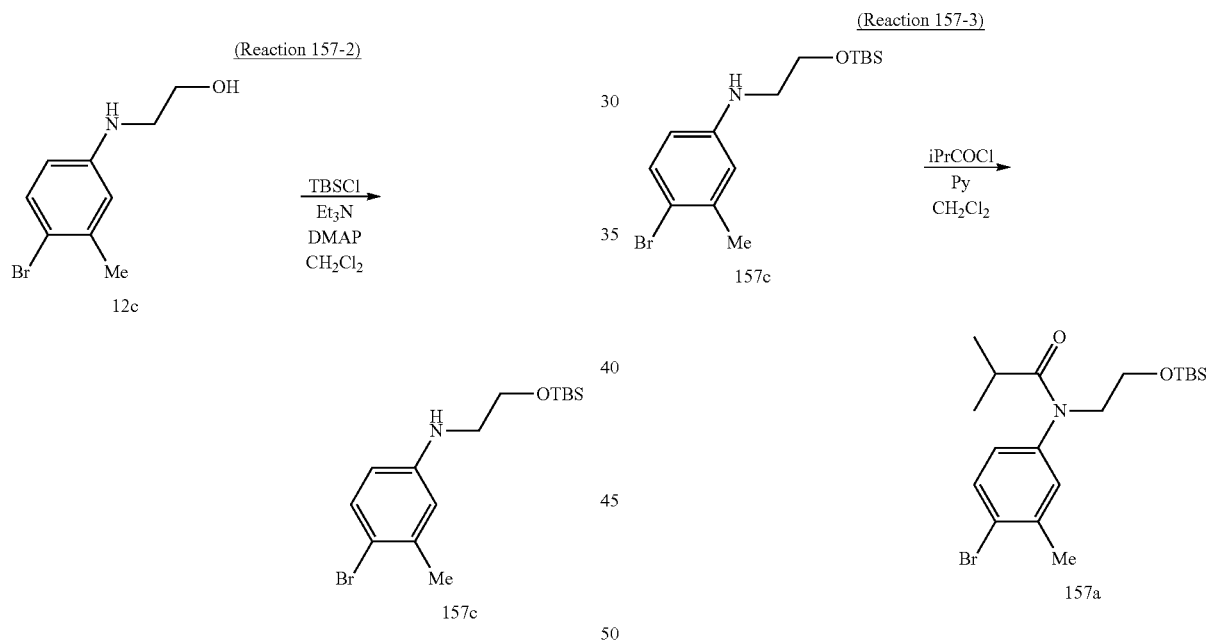 | LCMS-D-1 | 3.30 | 699 (M + H)+ |

The aryl bromide reagent used in the synthesis of Compound 711 (N-(4-bromo-3-methyl-phenyl)-N-[2-(tert-butyl-dimethyl-silanyloxy)-ethyl]-isobutylamide) was synthesized as follows.

$^1$H-NMR (300 MHz, CDCl$_3$) δ 0.08 (6H, s), 0.91 (9H, s), 2.32 (3H, s), 3.18 (2H, dd, J=5.7 and 5.1 Hz), 3.80 (2H, t, J=5.1 Hz), 4.01 (1H, dull t, J=5.7 Hz), 6.34 (1H, dd, J=8.7, 2.5 Hz), 6.51 (1H, d, J=2.5 Hz), 7.27 (1H, d, J=8.7 Hz).

Triethylamine (0.39 ml, 2.80 mmol), dimethylaminopyridine (13 mg, 0.11 mmol) and tert-butyl-dimethyl-chlorosilane (319 mg, 2.11 mmol) were added to a solution of 2-(4-bromo-3-methyl-phenylamino)-ethanol (430 mg, 1.87 mmol) in dichloromethane (3.8 ml) at room temperature, and the mixture was stirred at room temperature for 24 hours. The reaction mixture was diluted with dichloromethane, and the organic layer was washed with water, dried over MgSO$_4$ and concentrated under reduced pressure. The resulting residue was purified by silica gel column chromatography (hexane-ethyl acetate) to give (4-bromo-3-methyl-phenyl)-[2-(tert-butyl-dimethyl-silanyloxy)-ethyl]-amine (629 mg, 98%).

N-(4-Bromo-3-methyl-phenyl)-N-[2-(tert-butyl-dimethyl-silanyloxy)-ethyl]-isobutylamide was synthesized by operations similar to those in Reaction 105-2 using appropriate reagents and starting material.

$^1$H-NMR (300 MHz, CDCl$_3$) δ 0.04 (6H, s), 0.87 (9H, s), 1.02 (6H, d, J=6.6 Hz), 2.41 (3H, s), 2.47 (1H, sept, J=6.6 Hz), 3.74 (4H, s), 6.92 (1H, dd, J=8.4, 2.3 Hz), 7.13 (1H, d, J=2.3 Hz), 7.53 (1H, d, J=8.4 Hz).

The aryl bromide reagents used in the synthesis of Compound 712 and Compound 713 ((R)-1-(4-bromo-3,5-dimethylphenyl)-5-(tert-butyl-dimethyl-silanyloxymethyl)-3,3-dimethylpyrrolidin-2-one and (R)-1-(4-bromo-3,5-dimethyl-phenyl)-5-(tert-butyl-dimethyl-silanyloxymethyl)-3-methyl-pyrrolidin-2-one) were synthesized as follows.

(Reaction 157-4)

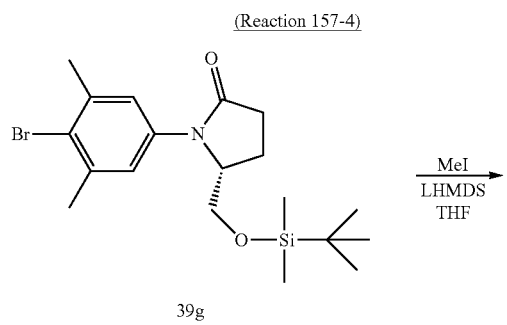

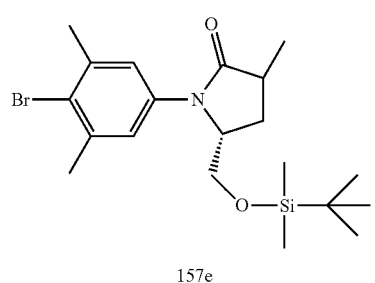

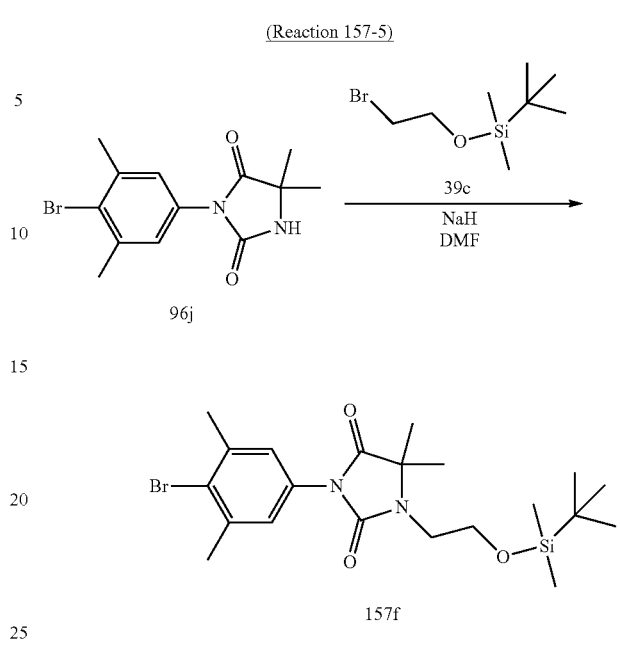

(3-(4-Bromo-3,5-dimethyl-phenyl)-1-[2-(tert-butyl-dimethyl-silanyloxy)-ethyl]-5,5-dimethyl-imidazolidine-2,4-dione was synthesized by operations similar to those in Reaction 25-3 using appropriate reagents and starting material.

$^1$H-NMR (CDCl$_3$) δ 7.11 (s, 2H), 3.85 (t, 2H, d=6.0 Hz), 3.43 (t, 2H, d=6.0 Hz), 2.42 (s, 6H), 1.49 (s, 6H), 0.90 (s, 9H), 0.07 (s, 6H).

The aryl bromide reagent used in the synthesis of Compound 715 (N-(4-bromo-3,5-dimethyl-phenyl)-N-[4-(tert-butyl-dimethyl-silanyloxy)-cyclohexyl]-methanesulfonamide) was synthesized as follows.

1 M LHMDS (0.61 ml, 0.61 mmol) was added dropwise to a solution of (R)-1-(4-bromo-3,5-dimethylphenyl)-5-(((tert-butyldimethylsilyl)oxy)-methyl)pyrrolidin-2-one (119 mg, 0.29 mmol) in THF (2.4 ml) at −78° C. in a nitrogen atmosphere, and the mixture was stirred at −78° C. for 15 minutes. A solution of iodomethane (38 μL, 0.62 mmol) in THF (0.5 ml) was added at −78° C., and the mixture was stirred at −78° C. for 15 minutes, warmed to room temperature and further stirred for three hours. A saturated aqueous ammonium chloride solution was added to the reaction mixture, and the mixture was diluted with dichloromethane. The organic layer was washed with saturated brine, and then dried over MgSO$_4$ and concentrated under reduced pressure. The resulting residue was purified by silica gel column chromatography (hexane-ethyl acetate) to give a mixture of (R)-1-(4-bromo-3,5-dimethylphenyl)-5-(tert-butyl-dimethyl-silanyloxymethyl)-3,3-dimethylpyrrolidin-2-one (minor) and (R)-1-(4-bromo-3,5-dimethyl-phenyl)-5-(tert-butyl-dimethyl-silanyloxymethyl)-3-methyl-pyrrolidin-2-one (major) (629 mg, 98%). This was used in Heck reaction without complete separation and purification.

The aryl bromide reagent used in the synthesis of Compound 714 ((3-(4-bromo-3,5-dimethyl-phenyl)-1-[2-(tert-butyl-dimethyl-silanyloxy)-ethyl]-5,5-dimethyl-imidazolidine-2,4-dione) was synthesized as follows.

(Reaction 157-6)

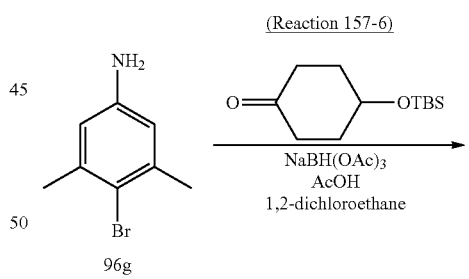

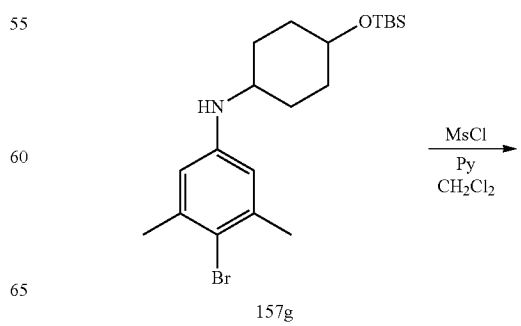

827

-continued

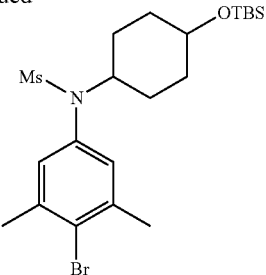

157h

N-(4-Bromo-3,5-dimethyl-phenyl)-N-[4-(tert-butyl-dimethyl-silanyloxy)-cyclohexyl]-methanesulfonamide was

828 synthesized by operations similar to those in Reaction 41-1 and Reaction 6-1 using appropriate reagents and starting material.

MS (ESI) m/z=490, 492 (M+H)+.

Example 158

N-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide (Compound 716)

(Reaction 158-1)

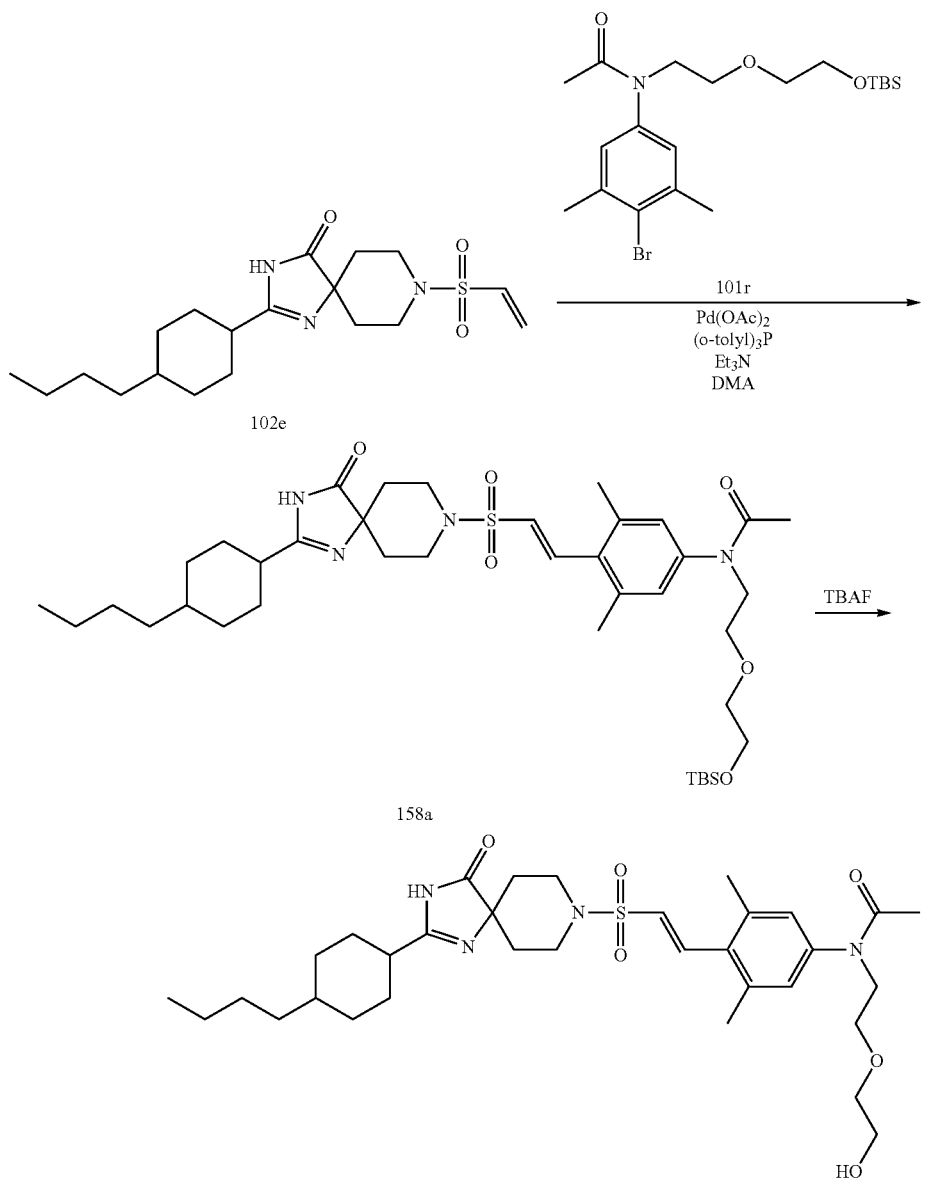

Compound 716

N-(4-{(E)-2-[2-(4-Butyl-cyclohexyl)-4-oxo-1,3,8-triaza-spiro[4.5]dec-1-ene-8-sulfonyl]-vinyl}-3,5-dimethyl-phenyl)-N-[2-(2-hydroxy-ethoxy)-ethyl]-acetamide was synthesized by operations similar to those in Reaction 26-1 and Reaction 39-2 using appropriate reagents and starting material.

MS (ESI) m/z=631 (M+H)+.

The aryl bromide reagent used in the synthesis of Compound 716 (N-(4-bromo-3,5-dimethyl-phenyl)-N-{2-[2-(tert-butyl-dimethyl-silanyloxy)-ethoxy]-ethyl}-acetamide) was synthesized as follows.

(Reaction 158-2)

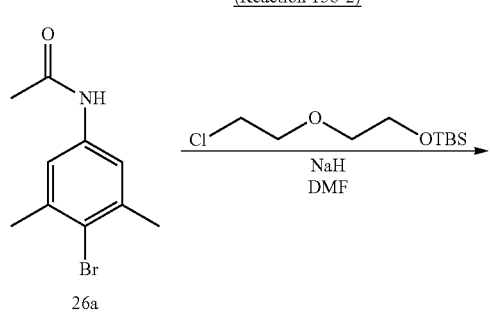

26a

-continued

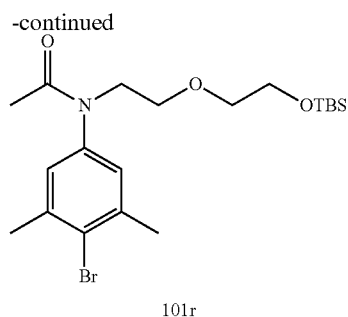

101r

N-(4-Bromo-3,5-dimethyl-phenyl)-N-{2-[2-(tert-butyl-dimethyl-silanyloxy)-ethoxy]-ethyl}-acetamide was synthesized by operations similar to those in Reaction 25-3 using appropriate reagents and starting material.

$^1$H-NMR (CDCl$_3$) δ 6.95 (s, 2H), 3.81 (dd, 2H, J=6.10, 5.72 Hz), 3.70 (dd, 2H, J=4.95, 5.34 Hz), 3.58 (dd, 2H, J=5.72, 6.10 Hz), 3.46 (dd, 2H, J=5.72, 4.95 Hz), 2.41 (s, 6H), 1.83 (s, 3H), 0.86 (s, 9H).

Example 159

N-(2-Fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide (Compound 717)

(Reaction 159-1)

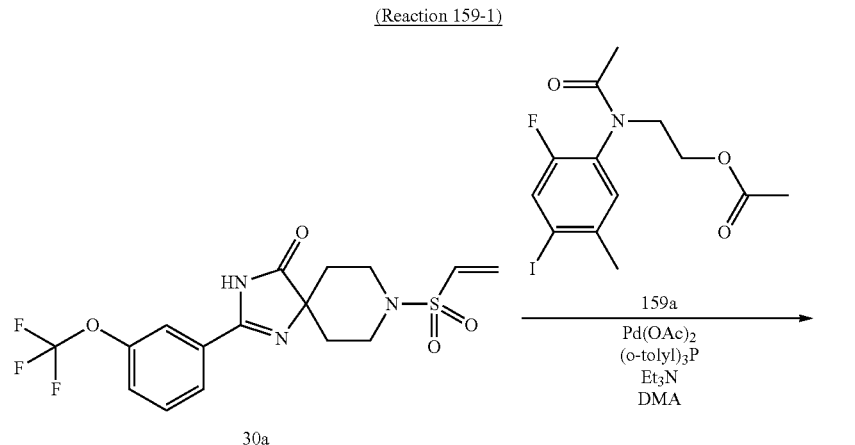

30a

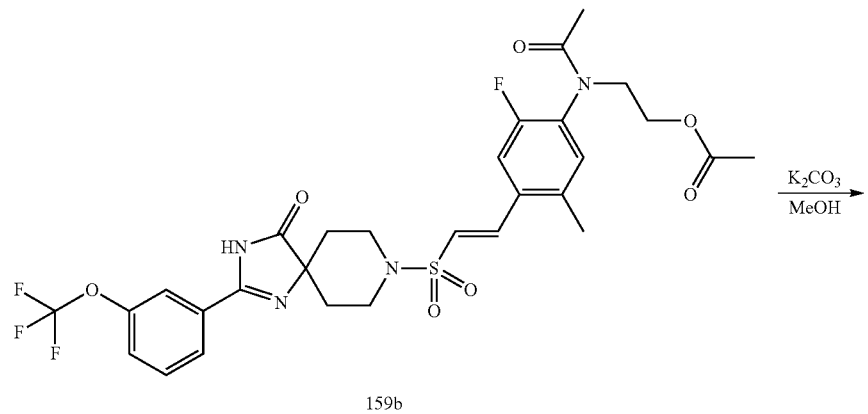

159b

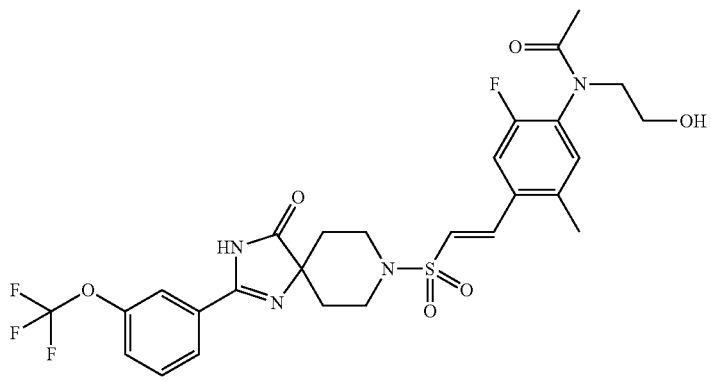

Compound 717

N-(2-Fluoro-5-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-(2-hydroxy-ethyl)-acetamide was synthesized by operations similar to those in Reaction 26-1 and Reaction 12-5 using appropriate reagents and starting material.

MS (ESI) m/z=613 (M+H)+.

The aryl iodide reagent used in the synthesis of Compound 717 (acetic acid 2-[acetyl-(2-fluoro-4-iodo-5-methyl-phenyl)-amino]-ethyl ester) was synthesized as follows.

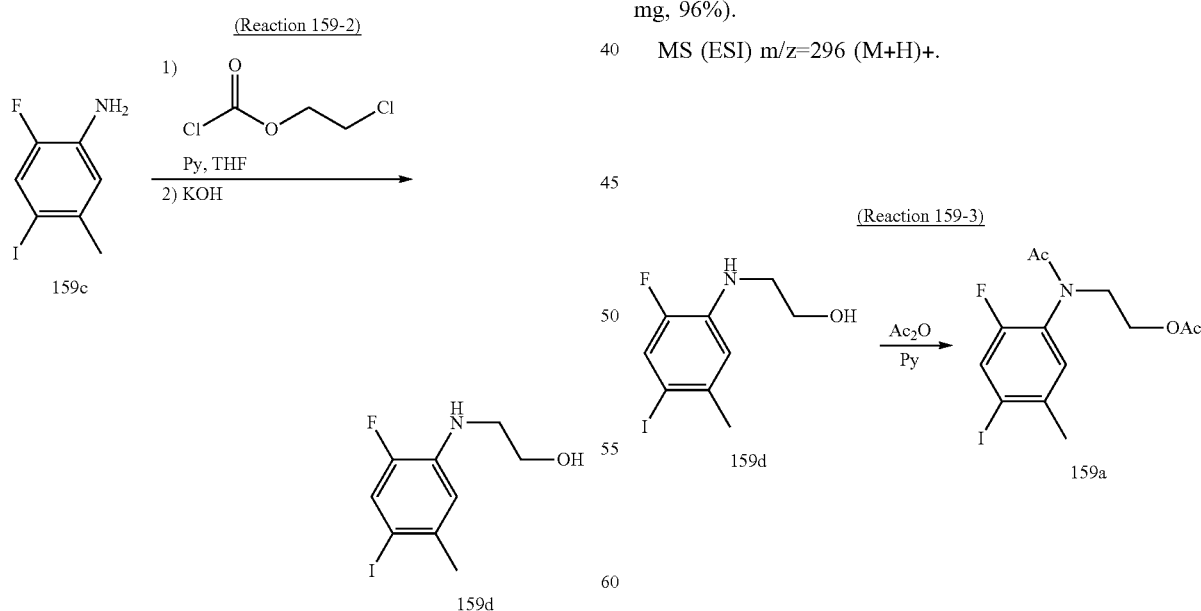

Pyridine (0.87 mL, 10.78 mmol) was added to a solution of 2-fluoro-4-iodo-5-methyl-phenylamine (1082.9 mg, 4.314 mmol) in THF (10.8 mL). 2-Chloroethyl chloroformate (0.47 mL, 4.53 mmol) was then added dropwise and the mixture was stirred overnight. Potassium hydroxide (968.2 mg, 17.25 mmol) and ethanol (10.8 mL) were subsequently added, and the mixture was heated under reflux overnight. The reaction mixture was then quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure. The resulting residue was purified by silica gel column chromatography to give 2-(2-fluoro-4-iodo-5-methyl-phenylamino)-ethanol as a pale brown solid (1217.0 mg, 96%).

MS (ESI) m/z=296 (M+H)+.

Acetic acid 2-[acetyl-(2-fluoro-4-iodo-5-methyl-phenyl)-amino]-ethyl ester was synthesized by operations similar to those in Reaction 12-2 using appropriate reagents and starting material.

MS (ESI) m/z=402 (M+Na)+.

Example 160

N-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide (Compound 718)

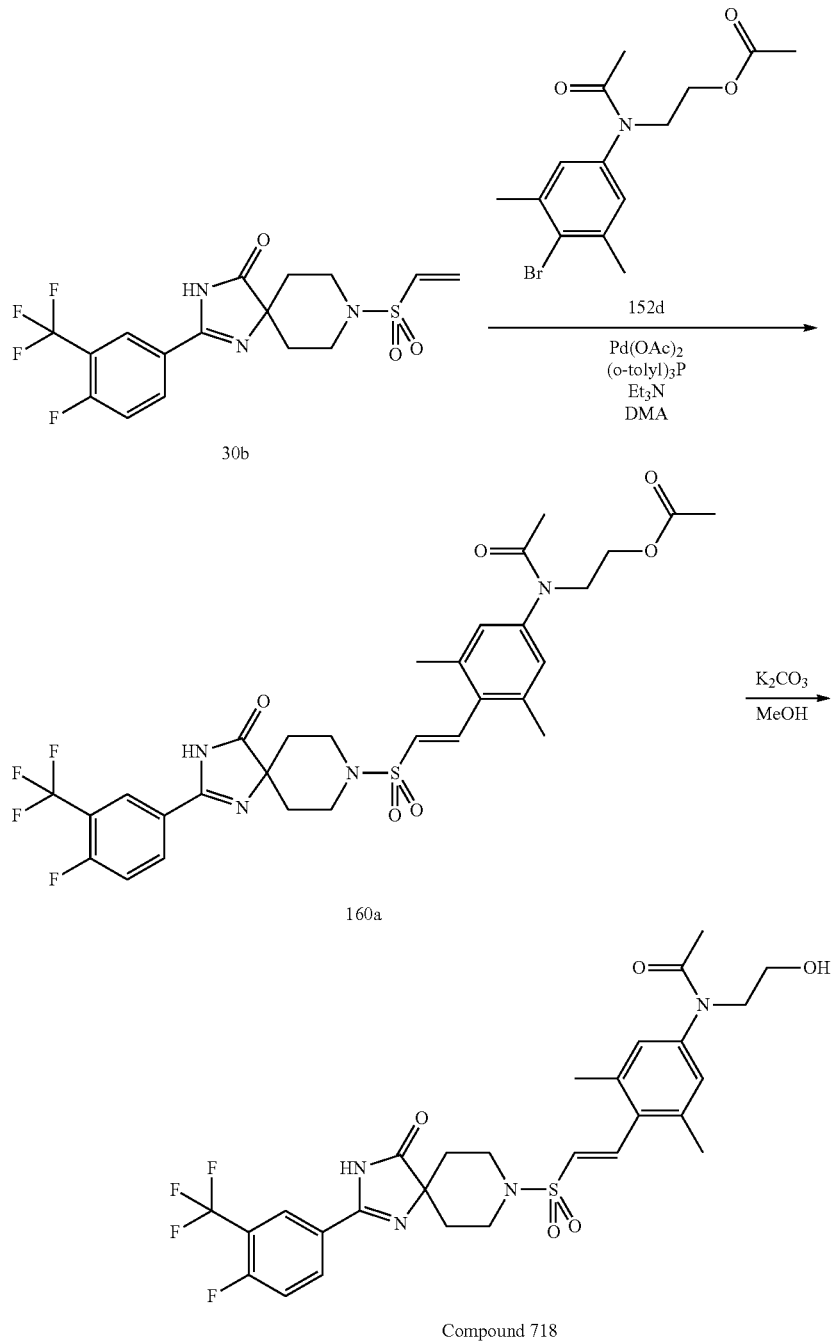

N-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-N-(2-hydroxy-ethyl)-acetamide was synthesized by operations similar to those in Reaction 26-1 and Reaction 12-5 using appropriate reagents and starting material.

MS (ESI) m/z=611 (M+H)+.

Example 161

N-(2-Hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (Compound 719)

(Reaction 161-1)

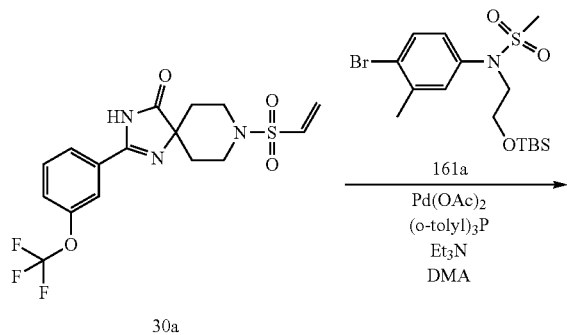

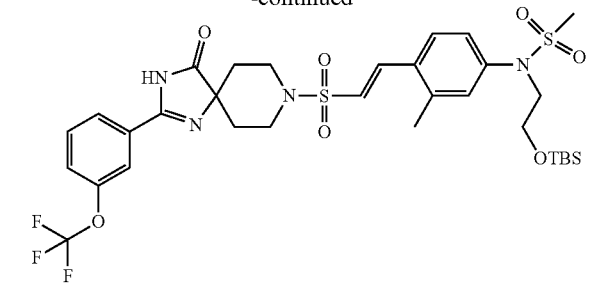

161b

N-[2-(tert-Butyl-dimethyl-silanyloxy)-ethyl]-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide was synthesized by operations similar to those in Reaction 26-1 using appropriate reagents and starting material.

$^1$H-NMR (300 MHz, CDCl$_3$) δ 0.04 (6H, s), 0.87 (9H, s), 1.70 (2H, m), 2.21 (2H, m), 2.44 (3H, s), 3.02 (3H, s), 3.32 (2H, m), 3.71 (2H, t, J=5.7 Hz), 3.81 (4H, m), 6.67 (1H, J=15.3 Hz), 7.27 (2H, m), 7.42 (1H, m), 7.56 (2H, m), 7.71 (1H, d, J=15.3 Hz), 7.80 (1H, d, J=8.0 Hz), 7.84 (1H, s), 10.24 (1H, brs).

(Reaction 161-2)

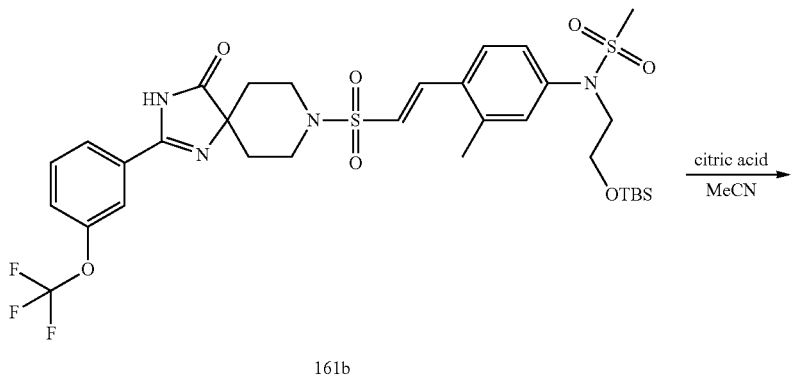

161b

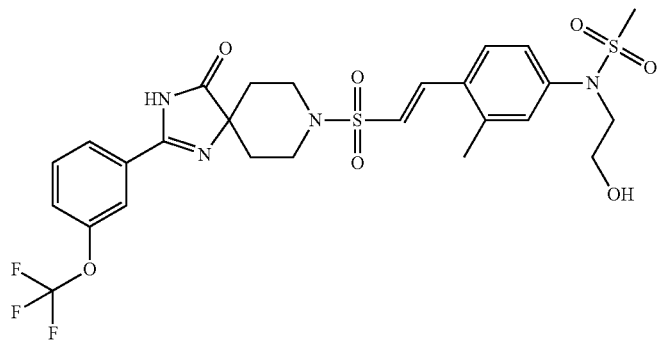

Compound 719

A 10% aqueous citric acid solution (0.14 ml, 0.067 mmol) was added to a solution of N-[2-(tert-butyl-dimethyl-silanyloxy)-ethyl]-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (14.3 mg, 0.0192 mmol) in acetonitrile (0.2 ml), and the mixture was stirred at 60° C. for 2.5 hours. The reaction mixture was diluted with ethyl acetate, and the organic layer was washed with an aqueous sodium bicarbonate solution, dried over MgSO$_4$ and concentrated under reduced pressure. The resulting residue was purified by silica gel column chromatography (ethyl acetate) to give N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-methanesulfonamide (12.5 mg, 100%).

MS (ESI) m/z=631 (M+H)+.

The aryl bromide reagent used in the synthesis of Compound 719 (N-(4-bromo-3-methyl-phenyl)-N-[2-(tert-butyl-dimethyl-silanyloxy)-ethyl]-methanesulfonamide) was synthesized as follows.

(Reaction 161-3)

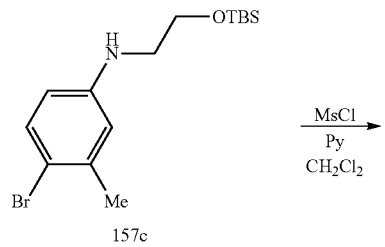

157c

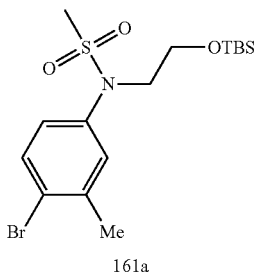

161a

N-(4-Bromo-3-methyl-phenyl)-N-[2-(tert-butyl-dimethyl-silanyloxy)-ethyl]-methanesulfonamide was synthesized by operations similar to those in Reaction 6-1 using appropriate reagents and starting material.

$^1$H-NMR (300 MHz, CDCl$_3$) δ 0.04 (6H, s), 0.87 (9H, s), 2.40 (3H, s), 2.96 (3H, s), 3.68 (2H, m), 3.75 (2H, m), 7.05 (1H, ddd, J=8.5, 2.5, 0.6 Hz), 7.25 (1H, d, J=2.5 Hz), 7.54 (1H, d, J=8.5 Hz).

Example 162

N-(2-Hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide (Compound 720)

(Reaction 162-1)

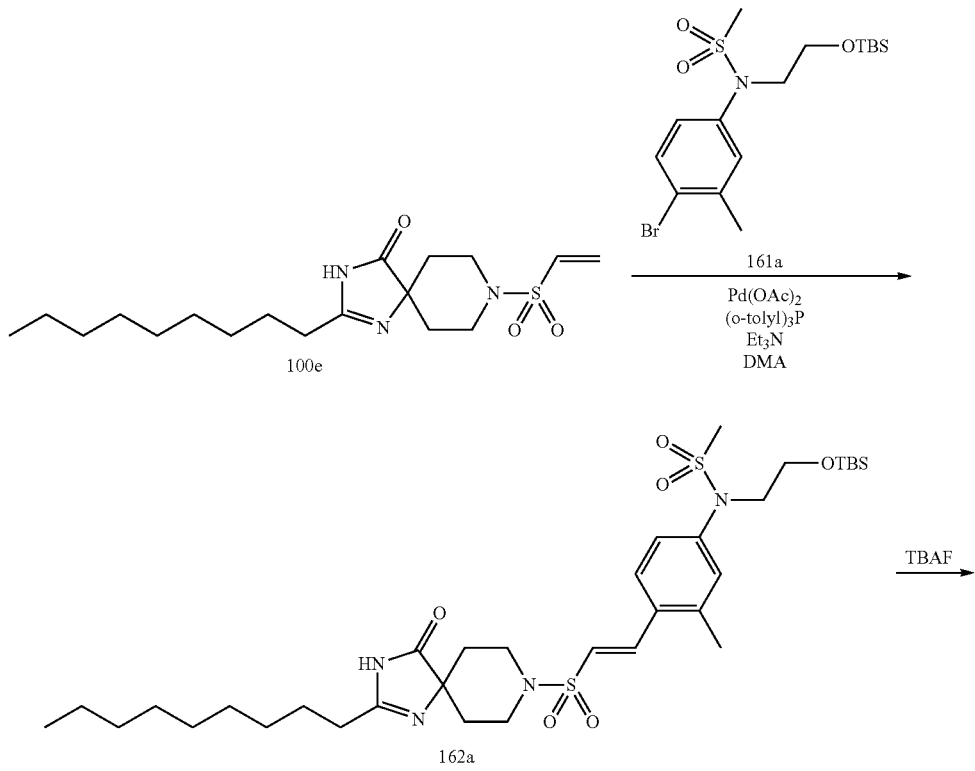

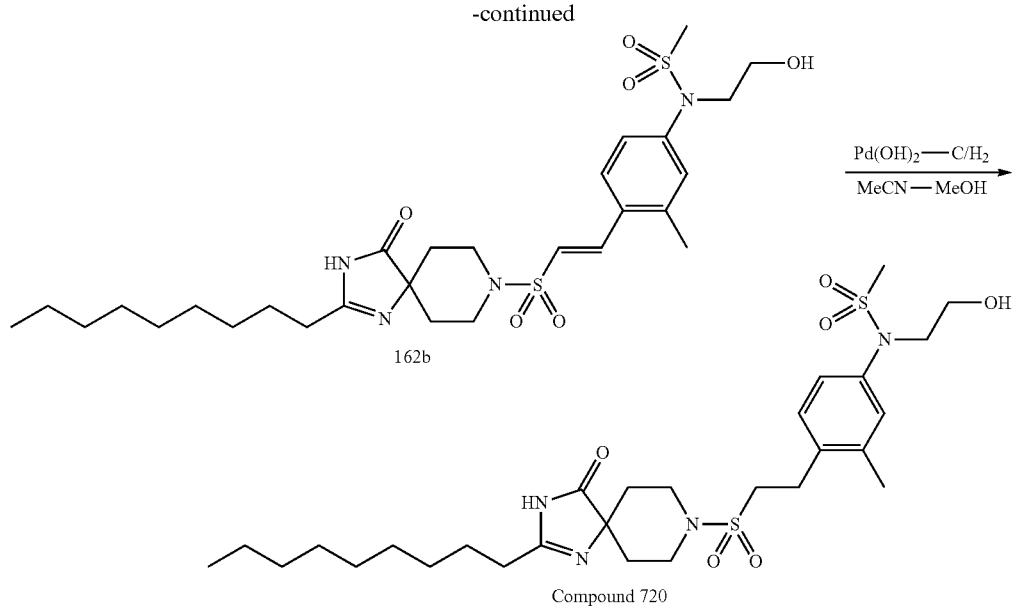

N-(2-Hydroxy-ethyl)-N-{3-methyl-4-[2-(2-nonyl-4-oxo-1,3,8-triaza-spiro[4.5]dec-1-ene-8-sulfonyl)-ethyl]-phenyl}-methanesulfonamide was synthesized by operations similar to those in Reaction 26-1, Reaction 39-2 and Reaction 122-2 using appropriate reagents and starting material.

MS (ESI) m/z=599 (M+H)+.

Example 163

N-(4-{2-[2-(4-Fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide (Compound 721)

(Reaction 163-1)

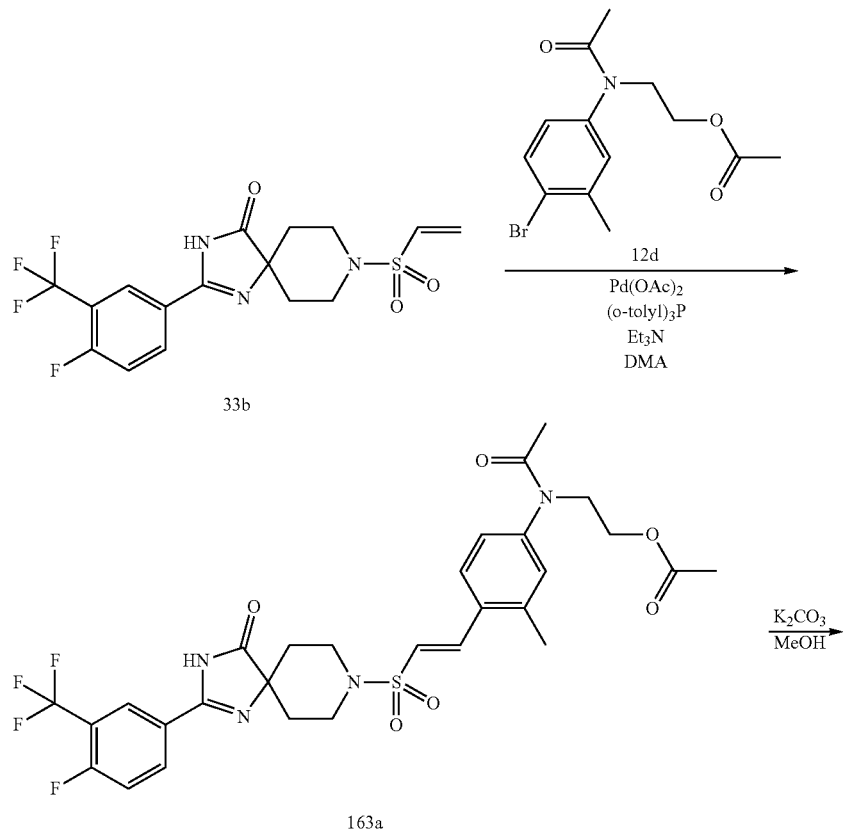

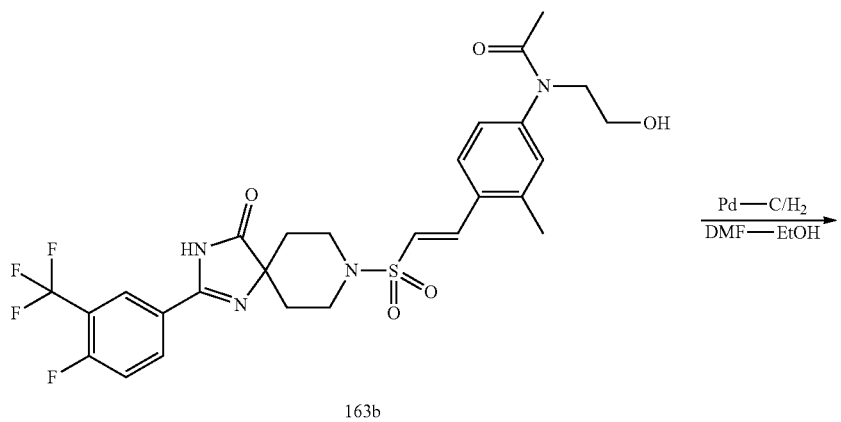

163b

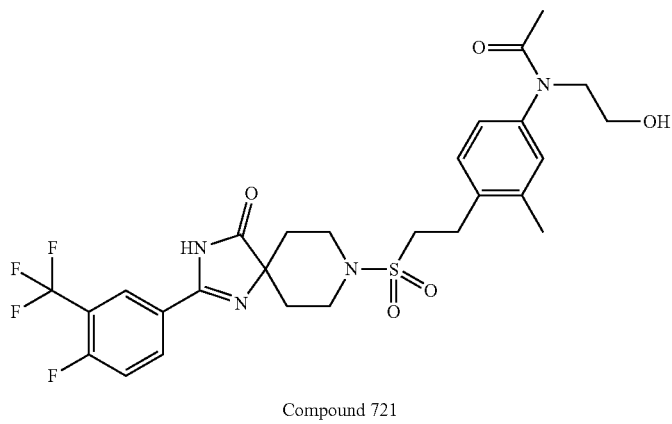

Compound 721

N-(4-{2-[2-(4-Fluoro-3-trifluoromethyl-phenyl)-4-oxo-1,3,8-triaza-spiro[4.5]dec-1-ene-8-sulfonyl]-ethyl}-3-methyl-phenyl)-N-(2-hydroxy-ethyl)-acetamide was synthesized by operations similar to those in Reaction 26-1, Reaction 12-5 and Reaction 42-2 using appropriate reagents and starting material.

MS (ESI) m/z=599 (M+H)+.

Example 164

2-Hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 722)

(Reaction 164-1)

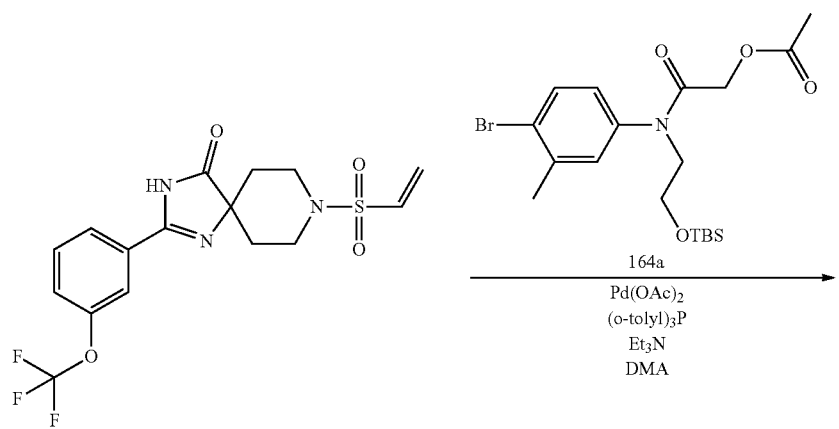

30a

843

-continued

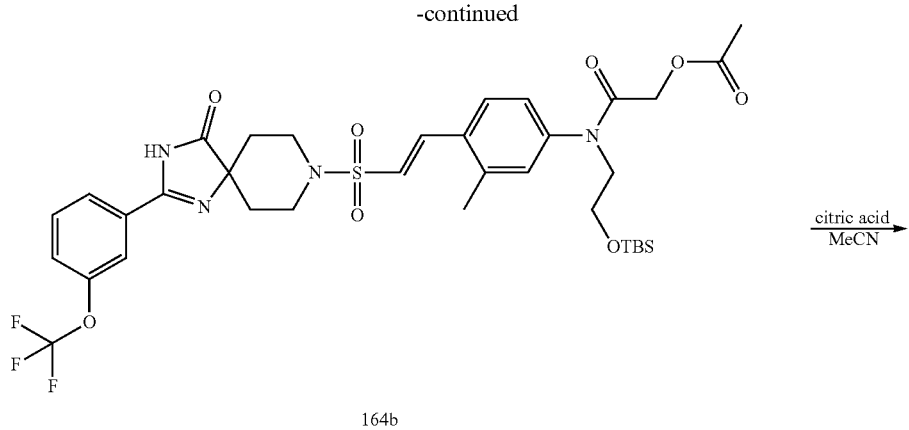

164b

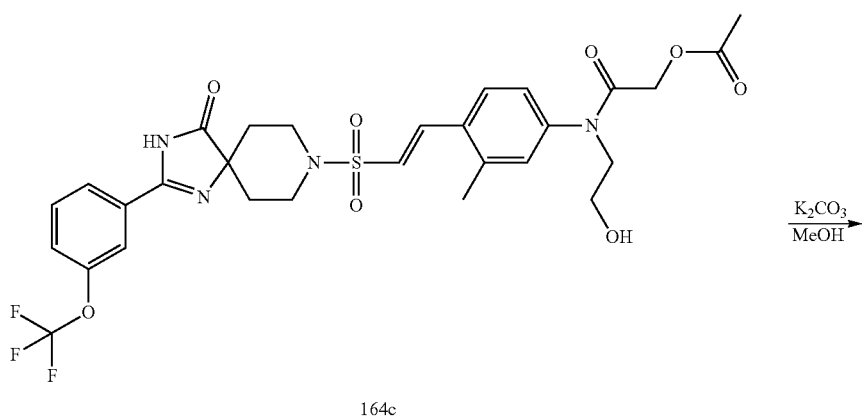

164c

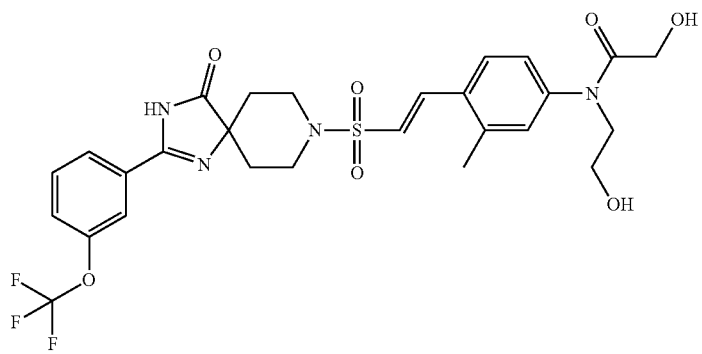

Compound 722

2-Hydroxy-N-(2-hydroxy-ethyl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide was synthesized by operations similar to those in Reaction 26-1, Reaction 161-2 and Reaction 12-5 using appropriate reagents and starting material.

MS (ESI) m/z=611 (M+H)+.

The aryl bromide reagent used in the synthesis of Compound 722 (acetic acid {(4-bromo-3-methyl-phenyl)-[2-(tert-butyl-dimethyl-silanyloxy)-ethyl]-carbamoyl}-methyl ester) was synthesized as follows.

(Reaction 164-2)

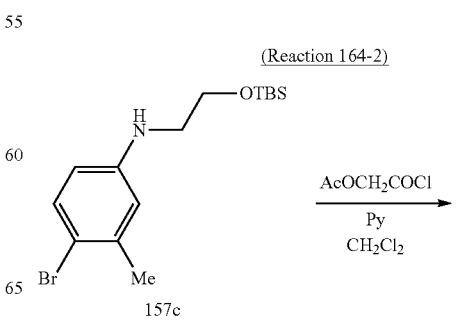

157c

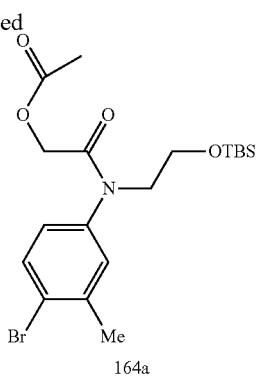

164a

Acetic acid {(4-bromo-3-methyl-phenyl)-[2-(tert-butyl-dimethyl-silanyloxy)-ethyl]-carbamoyl}-methyl ester was synthesized by operations similar to those in Reaction 105-2 using appropriate reagents and starting material.

$^1$H-NMR (300 MHz, CDCl$_3$) δ 0.03 (6H, s), 0.86 (9H, s), 2.13 (3H, s), 2.41 (3H, s), 3.76 (4H, s), 4.36 (2H, s), 6.99 (1H, dd, J=8.4, 2.4 Hz), 7.19 (1H, d, J=2.4 Hz), 7.56 (1H, d, J=8.4 Hz).

Example 165

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea (Compound 723)

(Reaction 165-1)

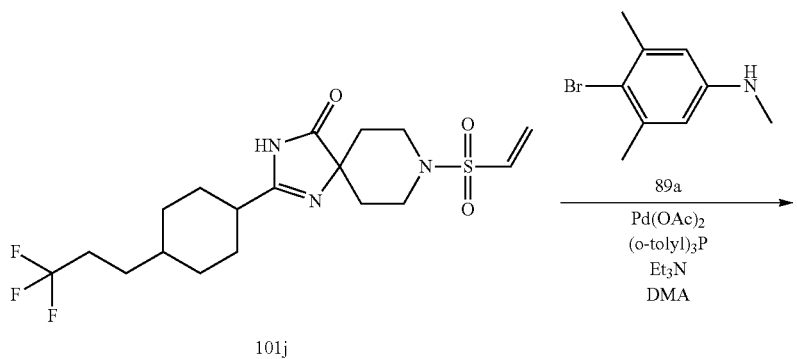

101j

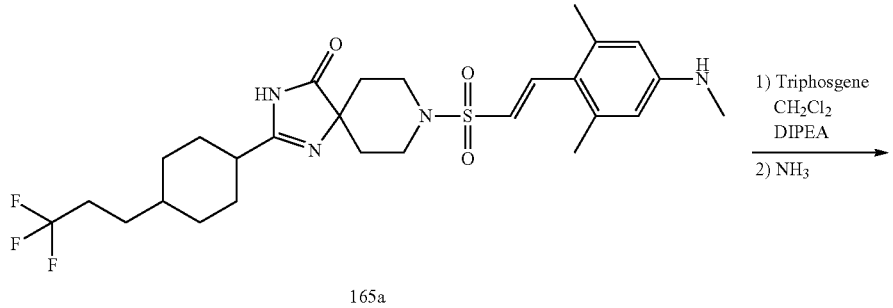

165a

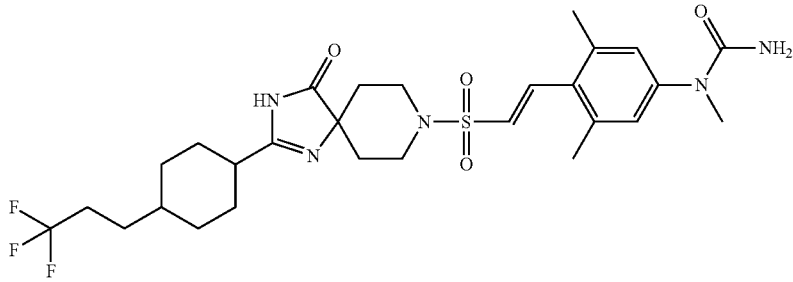

Compound 723

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-methyl-urea was synthesized by operations similar to those in Reaction 26-1 and Reaction 81-1 using appropriate reagents and starting material.

MS (ESI) m/z=598 (M+H)+.

Example 166

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea (Compound 724)

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-phenyl]-1-[2-(2-hydroxy-ethoxy)-ethyl]-urea was synthesized by operations similar to those in Reaction 25-2 and Reaction 81-1 using appropriate reagents and starting material.

MS (ESI) m/z=672 (M+H)+.

The example compound shown below was synthesized by operations similar to those in Example 166 using appropriate reagents and starting material.

(Reaction 166-1)

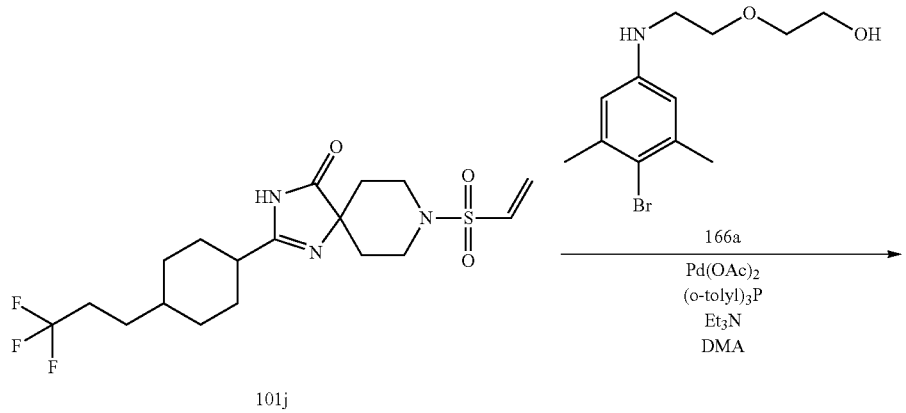

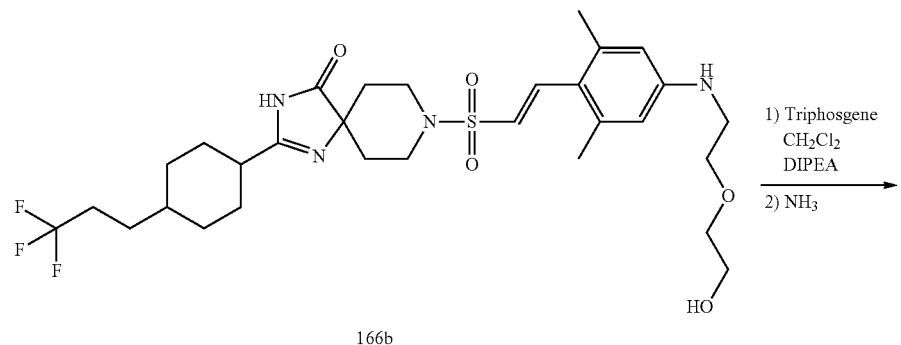

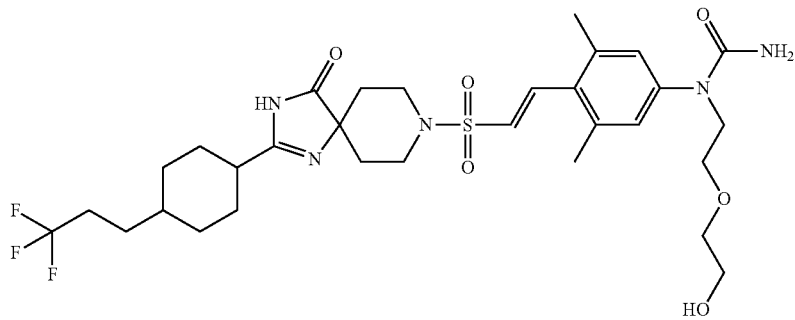

Compound 724

Compound 725

TABLE 107

| Target Compound | Structure | LCMS condition | Retention time (min) | MS (m/z) |
|---|---|---|---|---|
| 725 | 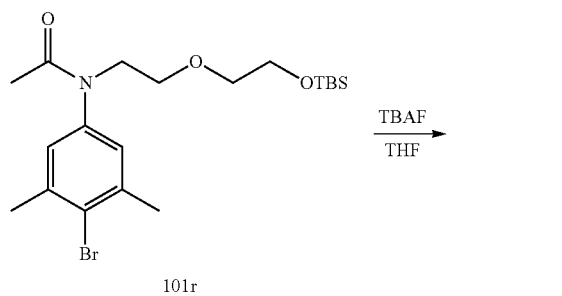 | LCMS-D-1 | 2.32 | 642 (M + H)+ |

The aryl bromide reagent used in the synthesis of Compound 724 (2-[2-(4-bromo-3,5-dimethyl-phenylamino)-ethoxy]-ethanol) was synthesized as follows.

The aryl bromide reagent used in the synthesis of Compound 725 ((4-bromo-3,5-dimethyl-phenyl)-(2-methoxy-ethyl)-amine) was synthesized as follows.

(Reaction 166-2)

(Reaction 166-3)

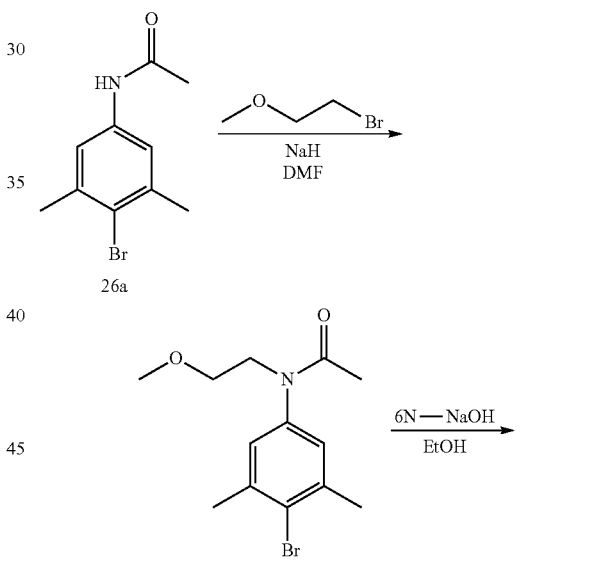

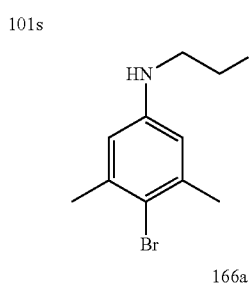

2-[2-(4-Bromo-3,5-dimethyl-phenylamino)-ethoxy]-ethanol was synthesized by operations similar to those in Reaction 39-2 and Reaction 96-16 using appropriate reagents and starting material.

MS (ESI) m/z=288, 290 (M+H)+.

(4-Bromo-3,5-dimethyl-phenyl)-(2-methoxy-ethyl)-amine was synthesized by operations similar to those in Reaction 25-3 and Reaction 96-16 using appropriate reagents and starting material.

MS (ESI) m/z=258, 260 (M+H)+.

Example 167

1-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea (Compound 726)

(Reaction 167-1)

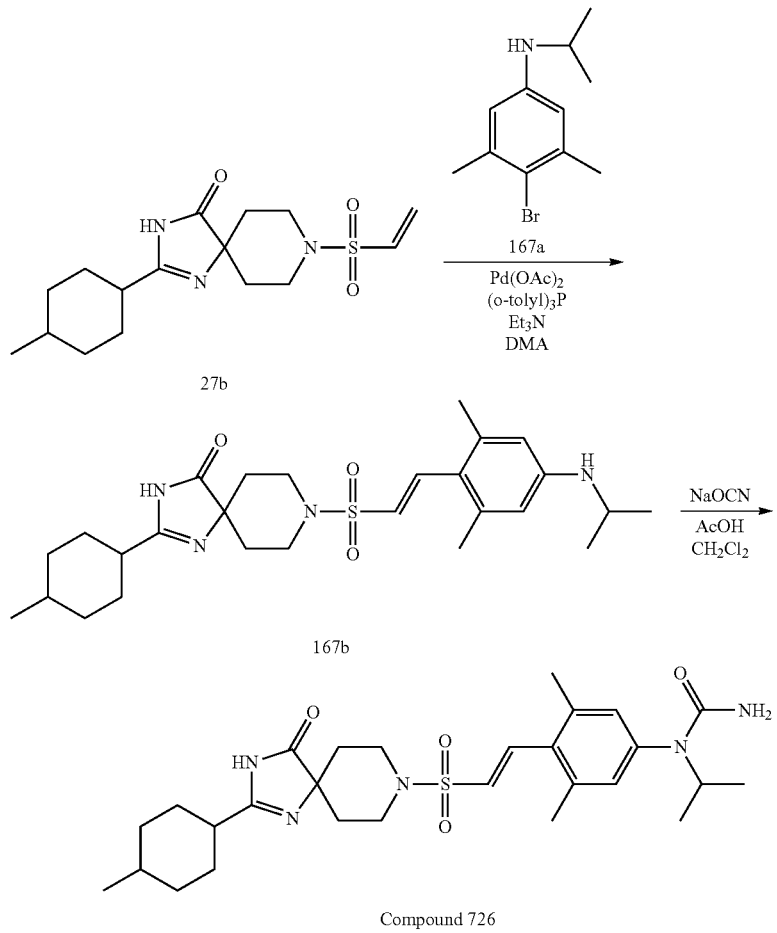

1-(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-1-isopropyl-urea was synthesized by operations similar to those in Reaction 25-2 and Reaction 89-2 using appropriate reagents and starting material.

MS (ESI) m/z=544 (M+H)+.

The example compound shown below was synthesized by operations similar to those in Example 167 using appropriate reagents and starting material.

Compound 727

TABLE 108

| Target compound | Structure | LCMS condition | Retention time (min) | MS (m/z) |
|---|---|---|---|---|
| 727 | 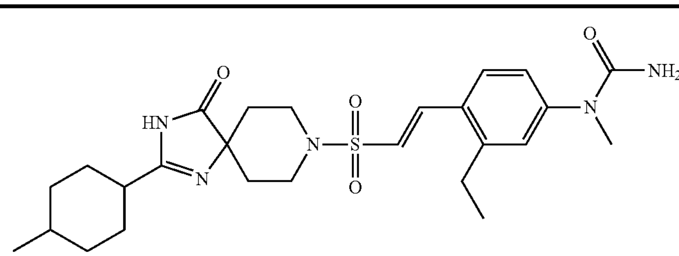 | LCMS-D-1 | 2.68 | 516 (M + H)+ |

853

The aryl bromide reagent used in the synthesis of Compound 726 ((4-bromo-3,5-dimethyl-phenyl)-isopropyl-amine) was synthesized as follows.

(Reaction 167-2)

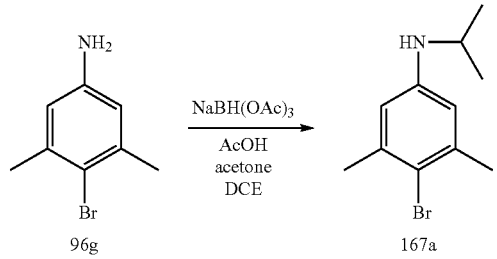

(4-Bromo-3,5-dimethyl-phenyl)-isopropyl-amine was synthesized by operations similar to those in Reaction 41-1 using appropriate reagents and starting material.

$^1$H-NMR (CDCl$_3$) δ 6.33 (s, 2H), 3.57 (q, 1H, J=6.6 Hz), 2.32 (s, 6H), 1.18 (d, 6H, J=6.6 Hz).

The aryl bromide reagent used in the synthesis of Compound 727 ((4-bromo-3-ethyl-phenyl)-methyl-amine) was synthesized as follows.

(Reaction 167-3)

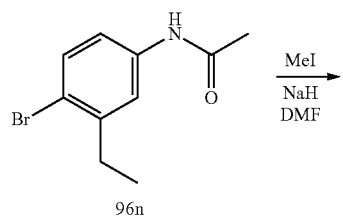

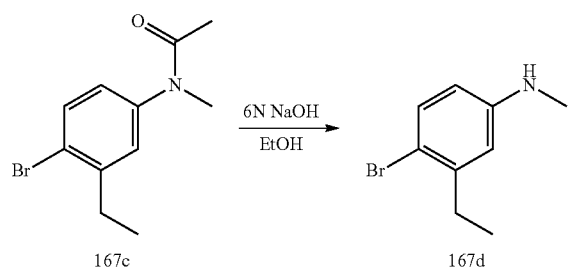

(4-Bromo-3-ethyl-phenyl)-methyl-amine was synthesized by operations similar to those in Reaction 25-3 and Reaction 96-16 using appropriate reagents and starting material.

MS (ESI) m/z=214, 216 (M+H)+.

854

Example 168

1-(3-Methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea (Compound 728)

(Reaction 168-1)

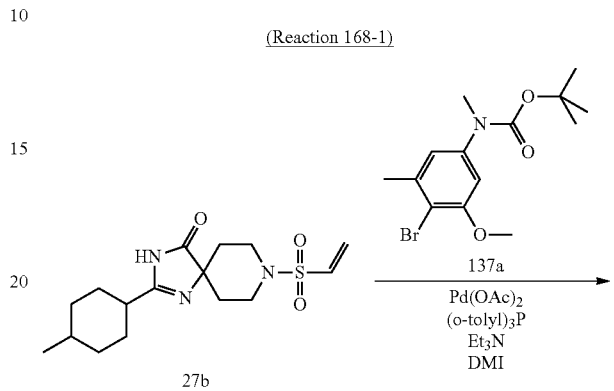

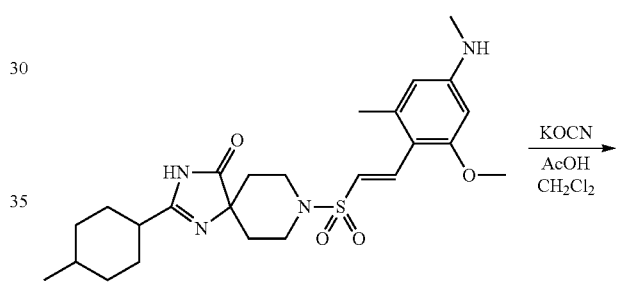

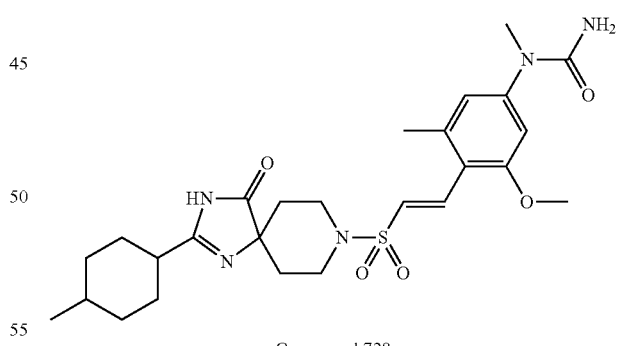

Compound 728

1-(3-Methoxy-5-methyl-4-{(E)-2-[2-(4-methyl-cyclohexyl)-4-oxo-1,3,8-triaza-spiro[4.5]dec-1-ene-8-sulfonyl]-vinyl}-phenyl)-1-methyl-urea was synthesized by operations similar to those in Reaction 26-1 (using DMI as a solvent) and Reaction 89-2 (using KOCN as a reagent) using appropriate reagents and starting material.

MS (ESI) m/z=532 (M+H)+.

Example 169

1-Cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea (Compound 729)

(Reaction 169-1)

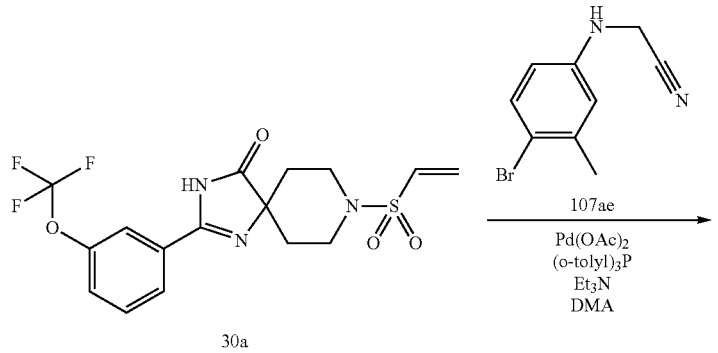

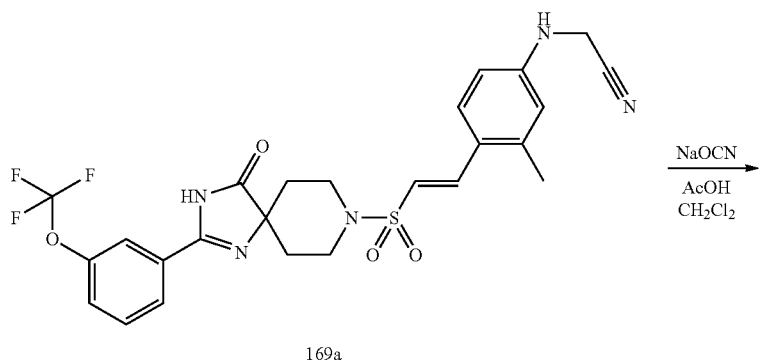

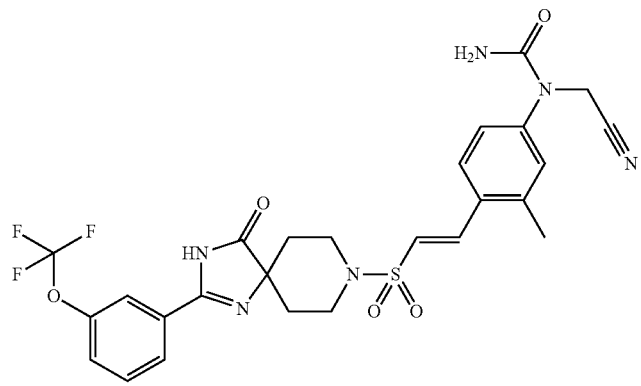

Compound 729

1-Cyanomethyl-1-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-urea was synthesized by operations similar to those in Reaction 26-1 and Reaction 89-2 using appropriate reagents and starting material.

MS (ESI) m/z=591 (M+H)+.

The example compound shown below was synthesized by operations similar to those in Example 169 using appropriate reagents and starting material.

Compound 730
TABLE 109
| Target Compound | Structure | LCMS condition | Retention time (min) | MS (m/z) |
|---|---|---|---|---|
| 730 | 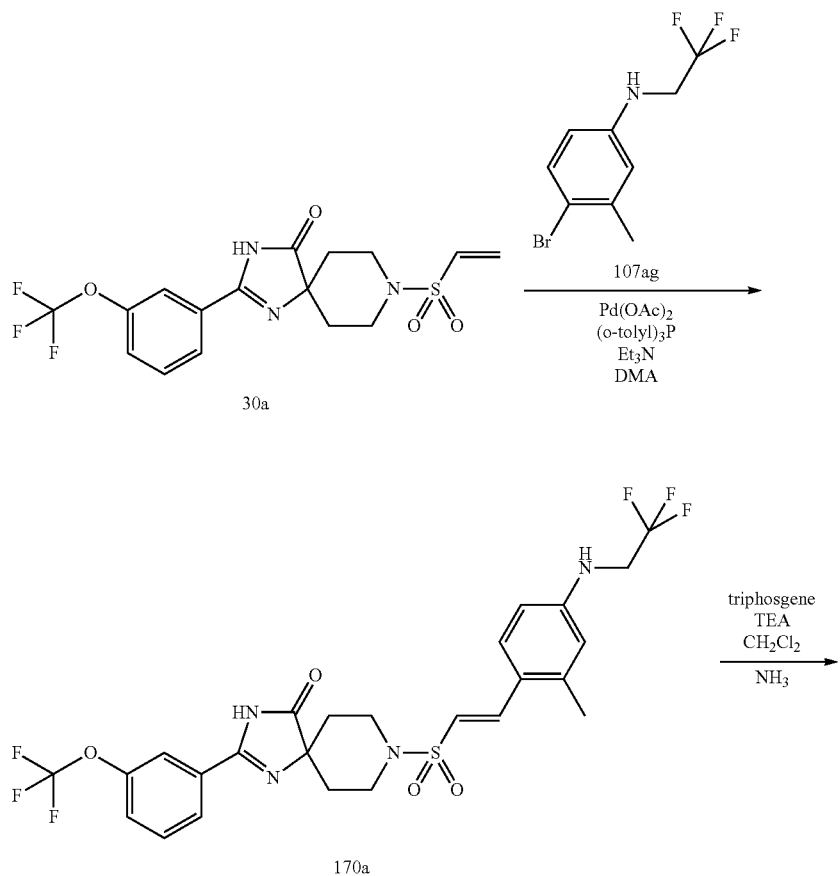 | LCMS-B-1 | 2.36 | 620 (M + H)+ |
Example 170
1-(3-Methyl-4-{(E)-2-[4-oxo-2-(3-trifluoromethoxyphenyl)-1,3,8-triaza-spiro[4.5]dec-1-ene-8-sulfonyl]-vinyl}-phenyl)-1-(2,2,2-trifluoro-ethyl)-urea (Compound 731)
(Reaction 170-1)

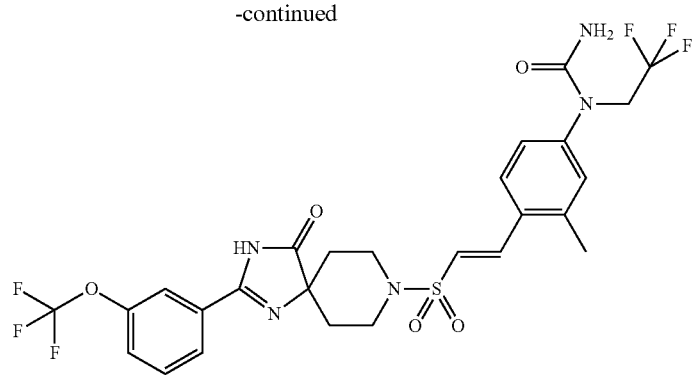

Compound 731

1-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-1-(2,2,2-trifluoro-ethyl)-urea was synthesized by operations similar to those in Reaction 26-1 and Reaction 81-1 using appropriate reagents and starting material.

MS (ESI) m/z=634 (M+H)+.

Example 171

1-(4-{2-[2-(4-Ethyl-cyclohexyl)-4-oxo-1,3,8-triaza-spiro[4.5]dec-1-ene-8-sulfonyl]-ethyl}-3,5-dimethyl-phenyl)-1-methyl-urea (Compound 732)

(Reaction 171-1)

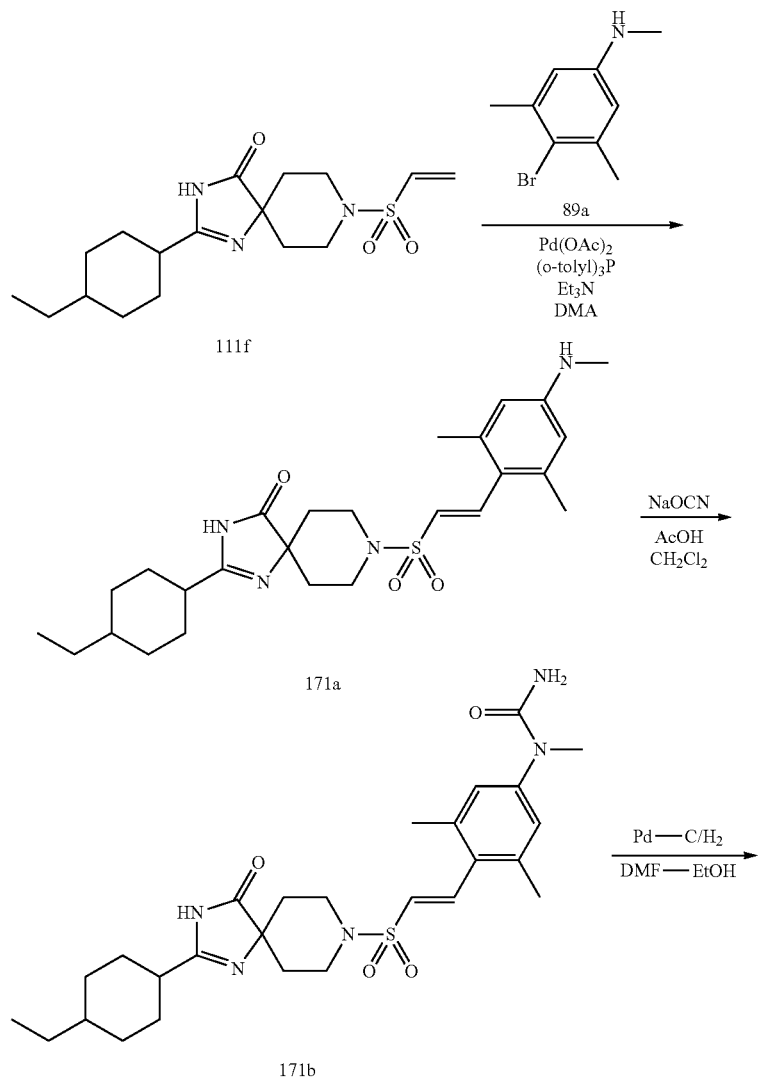

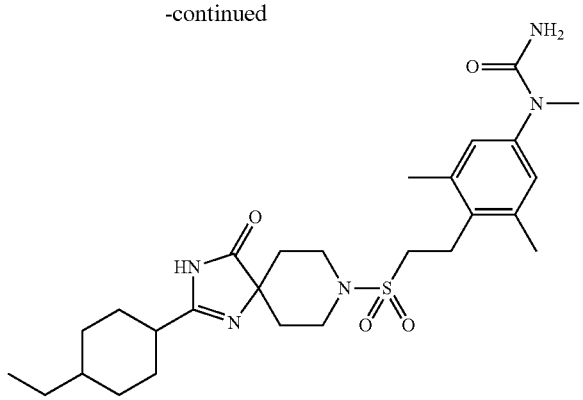

Compound 732

1-(4-{2-[2-(4-Ethyl-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 25-2, Reaction 89-2 and Reaction 42-2 using appropriate reagents and starting material.

MS (ESI) m/z=532 (M+H)+.

Example 172

1-((S)-2,3-Dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea (Compound 733)

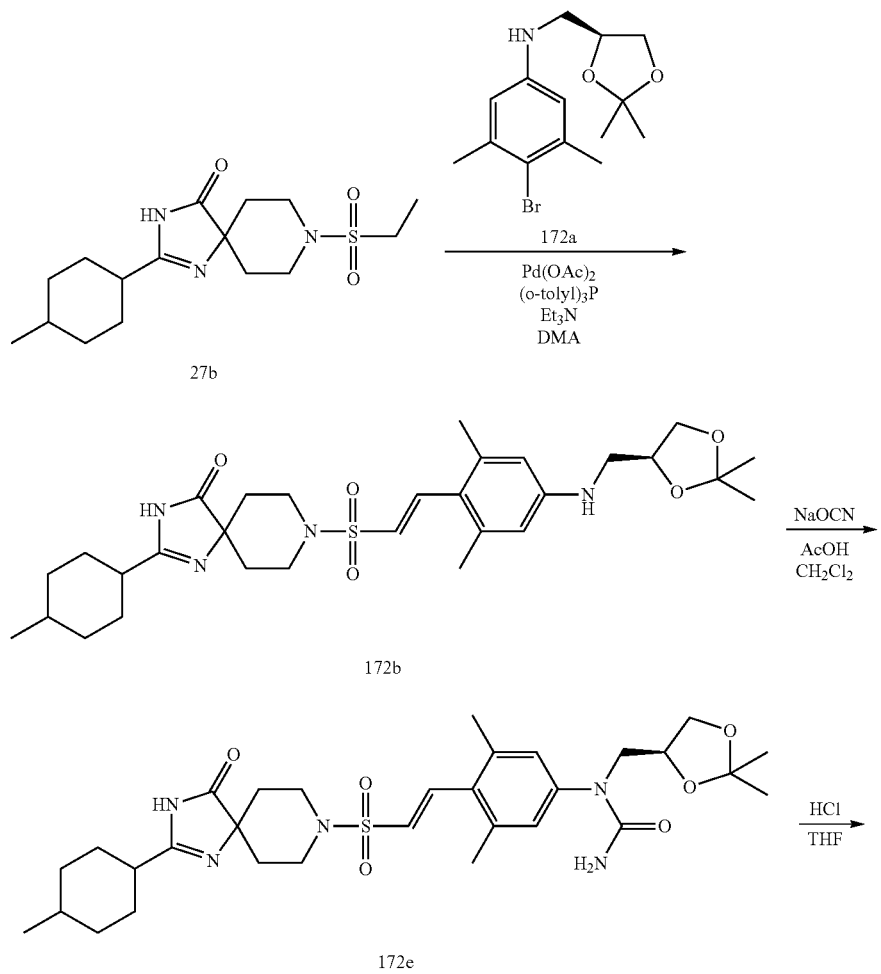

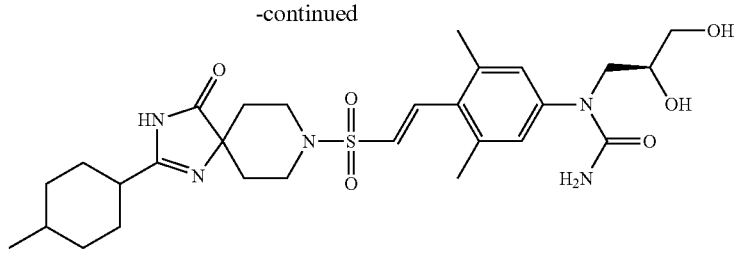

Compound 733

1-((S)-2,3-Dihydroxy-propyl)-1-(3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-urea was synthesized by operations similar to those in Reaction 25-2, Reaction 89-2 and Reaction 25-4 using appropriate reagents and starting material.

MS (ESI) m/z=576 (M+H)+.

The aryl bromide reagent used in the synthesis of Compound 733 ((4-bromo-3,5-dimethyl-phenyl)-((S)-2,2-dimethyl-[1,3]dioxolan-4-ylmethyl)-amine) was synthesized as follows.

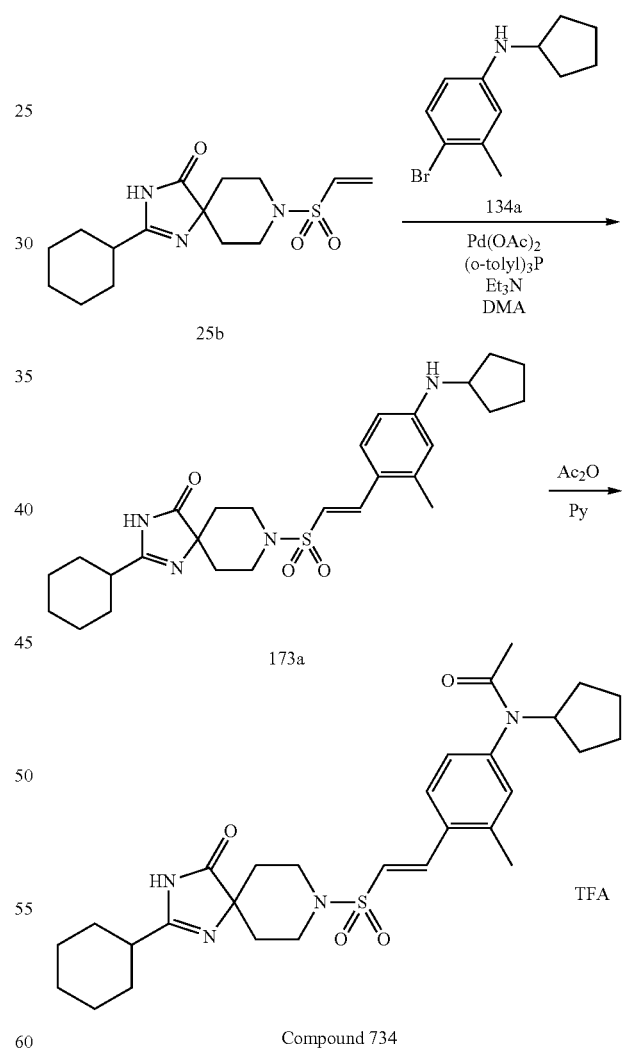

(4-Bromo-3,5-dimethyl-phenyl)-((S)-2,2-dimethyl-[1,3]dioxolan-4-ylmethyl)-amine was synthesized by operations similar to those in Reaction 96-16 using appropriate reagents and starting material.

¹H-NMR (CDCl₃) δ 6.39 (s, 2H), 4.34 (m, 1H), 4.09 (dd, 1H, J=8.2, 6.3 Hz), 3.75 (dd, 1H, J=8.2, 6.3 Hz), 3.29-3.11 (m, 2H), 2.33 (s, 6H), 1.45 (s, 3H), 1.37 (s, 3H).

Example 173

N-{4-[(E)-2-(2-Cyclohexyl-4-oxo-1,3,8-triaza-spiro[4.5]dec-1-ene-8-sulfonyl)-vinyl]-3-methyl-phenyl}-N-cyclopentyl-acetamide trifluoroacetate (Compound 734)

(Reaction 173-1)

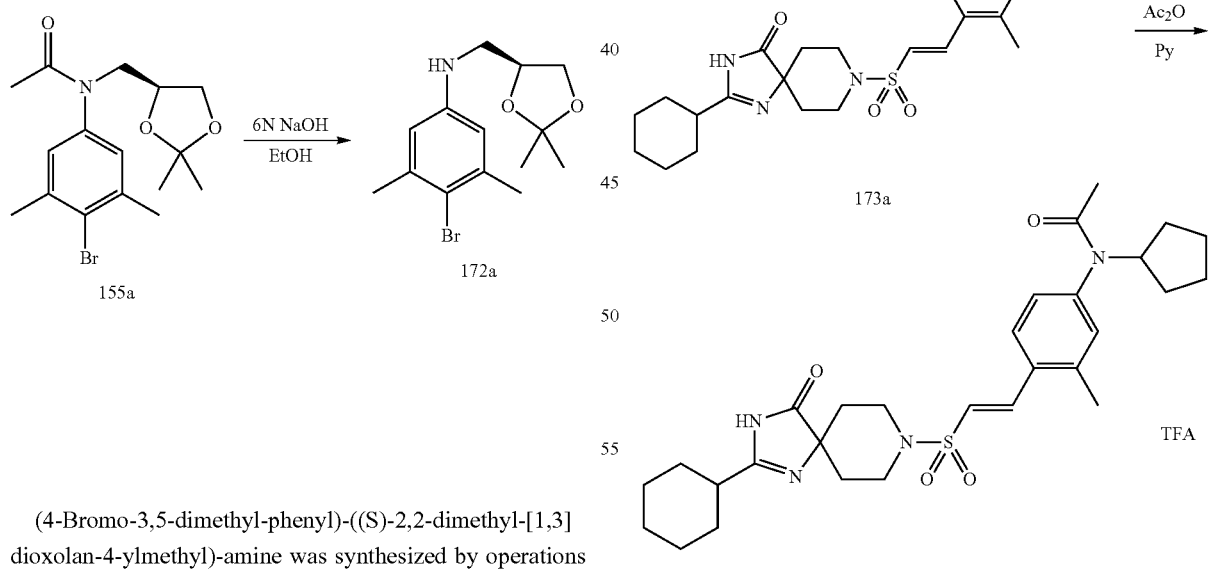

Compound 734

N-{4-[(E)-2-(2-Cyclohexyl-4-oxo-1,3,8-triaza-spiro[4.5]dec-1-ene-8-sulfonyl)-vinyl]-3-methyl-phenyl}-N-cyclopentyl-acetamide trifluoroacetate was synthesized by operations similar to those in Reaction 26-1 and Reaction 12-2 (using HPLC for purification) using appropriate reagents and starting material.

MS (ESI) m/z=541 (M+H)+.

Example 174

(S)-2-Amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide (Compound 735)

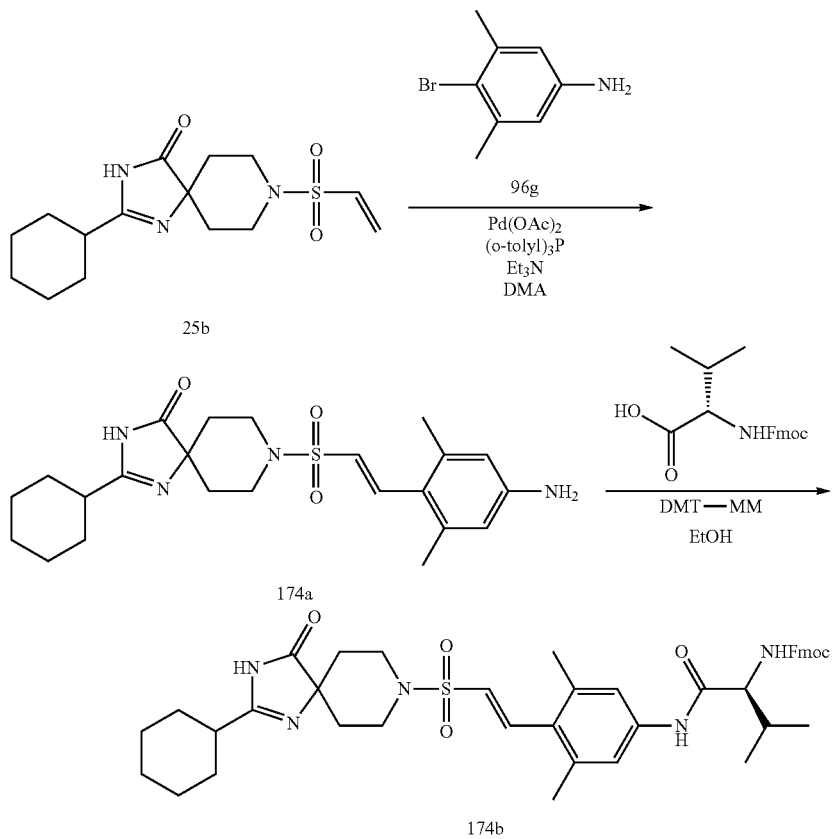

((S)-1-{4-[(E)-2-(2-Cyclohexyl-4-oxo-1,3,8-triaza-spiro[4.5]dec-1-ene-8-sulfonyl)-vinyl]-3,5-dimethyl-phenylcarbamoyl}-2-methyl-propyl)-carbamic acid 9H-fluoren-9-ylmethyl ester was synthesized by operations similar to those in Reaction 26-1 and Reaction 10-1 using appropriate reagents and starting material.

MS (ESI) m/z=766 (M+H)+.

(Reaction 174-2)

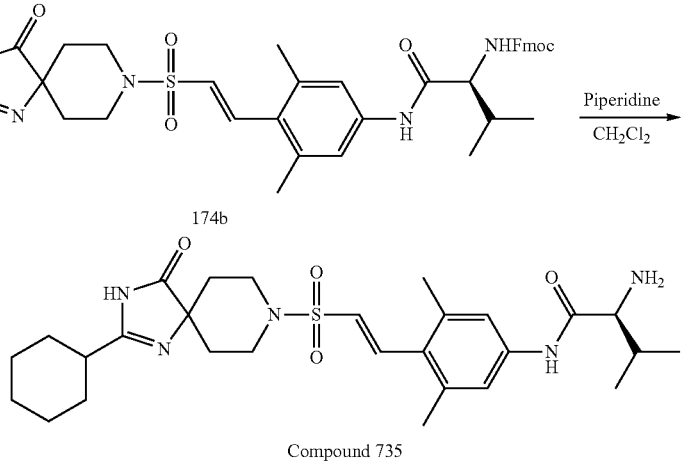

Piperidine (1 ml) was added to a solution of ((S)-1-{4-[(E)-2-(2-cyclohexyl-4-oxo-1,3,8-triaza-spiro[4.5]dec-1-ene-8-sulfonyl)-vinyl]-3,5-dimethyl-phenylcarbamoyl}-2-methyl-propyl)-carbamic acid 9H-fluoren-9-ylmethyl ester (84 mg, 0.11 mmol) in dichloromethane (4 ml), and the mixture was stirred at room temperature for three hours. The reaction mixture was quenched with water and then extracted with ethyl acetate. The organic layer was sequentially washed with water and saturated brine, and then dried over anhydrous magnesium sulfate and concentrated under reduced pressure. The resulting residue was purified by silica gel column chromatography to give (S)-2-amino-N-{4-[(E)-2-(2-cyclohexyl-4-oxo-1,3,8-triaza-spiro[4.5]dec-1-ene-8-sulfonyl)-vinyl]-3,5-dimethyl-phenyl}-3-methyl-butylamide (20 mg, 33%).

MS (ESI) m/z=544 (M+H)+.

Example 175

2-{4-[(E)-2-(2-Cyclohexyl-4-oxo-1,3,8-triaza-spiro[4.5]dec-1-ene-8-sulfonyl)-vinyl]-indol-1-yl}-N-pyridin-4-yl-acetamide (Compound 736)

(Reaction 175-1)

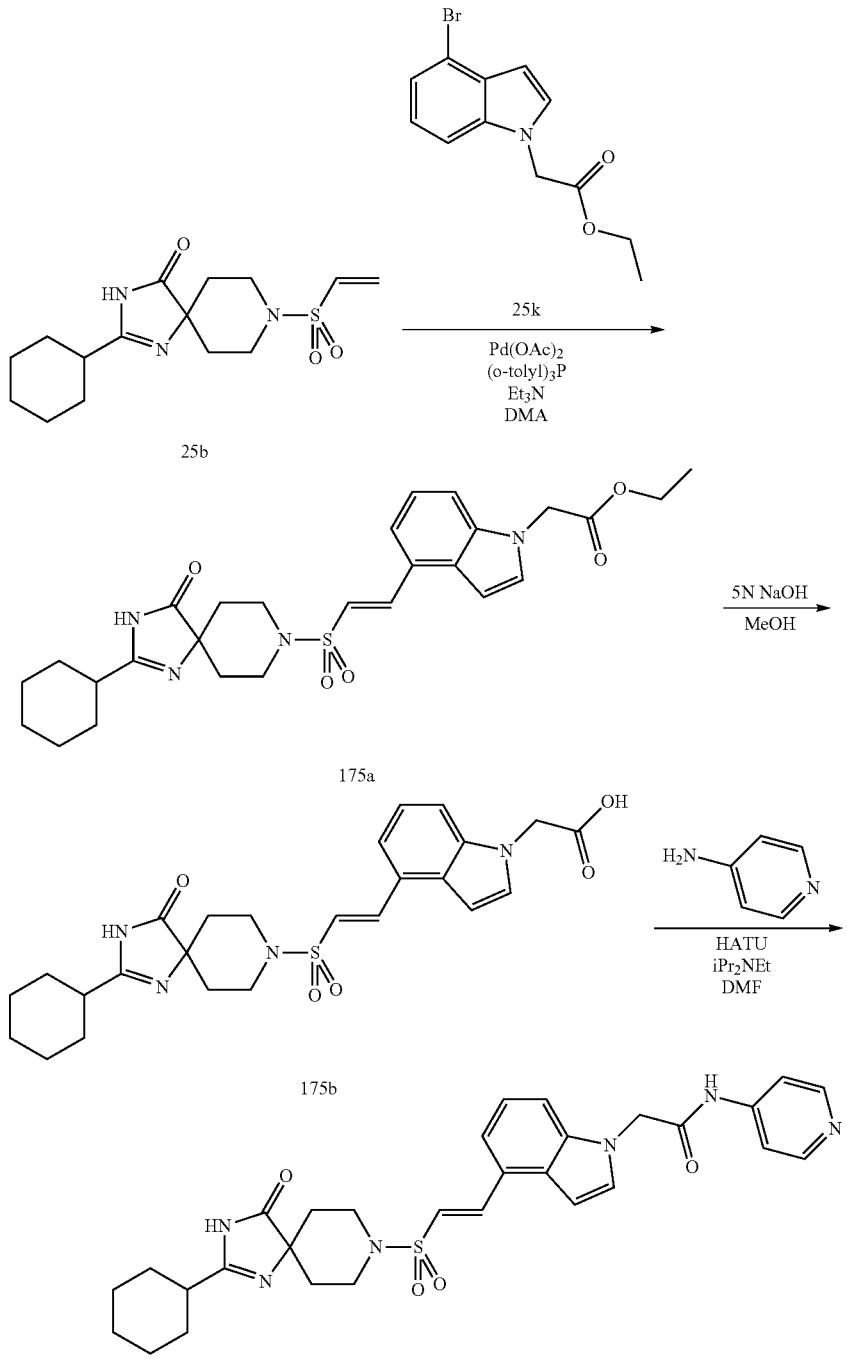

Compound 736

2-{4-[(E)-2-(2-Cyclohexyl-4-oxo-1,3,8-triaza-spiro[4.5]dec-1-ene-8-sulfonyl)-vinyl]-indol-1-yl}-N-pyridin-4-yl-acetamide was synthesized by operations similar to those in Reaction 25-2, Reaction 23-2 and Reaction 10-22 using appropriate reagents and starting material.

MS (ESI) m/z=575 (M+H)+.

The aryl bromide reagent used in the synthesis of Compound 736 ((4-bromo-indol-1-yl)-acetic acid ethyl ester) was synthesized as follows.

(Reaction 175-2)

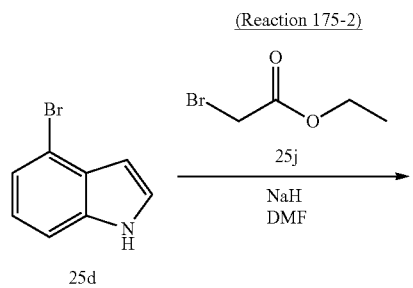

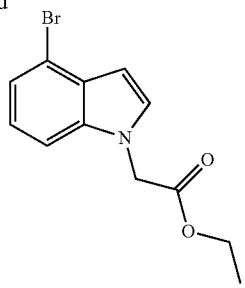

(4-Bromo-indol-1-yl)-acetic acid ethyl ester was synthesized by operations similar to those in Reaction 25-3 using appropriate reagents and starting material.

MS (ESI) m/z=282 (M+H)+.

Example 176

2-(3-Methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide (Compound 737)

(Reaction 176-1)

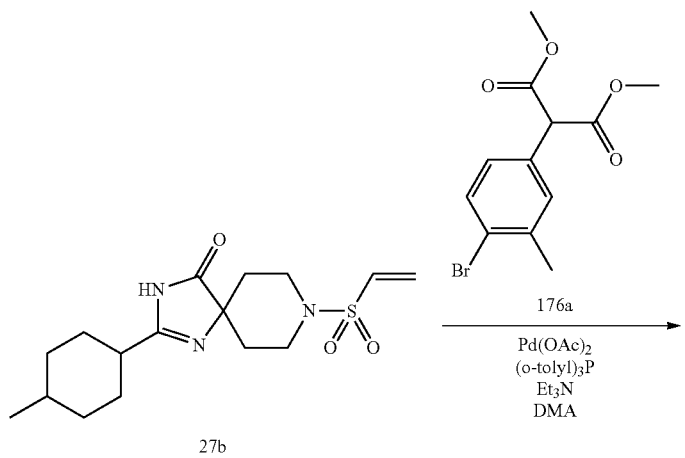

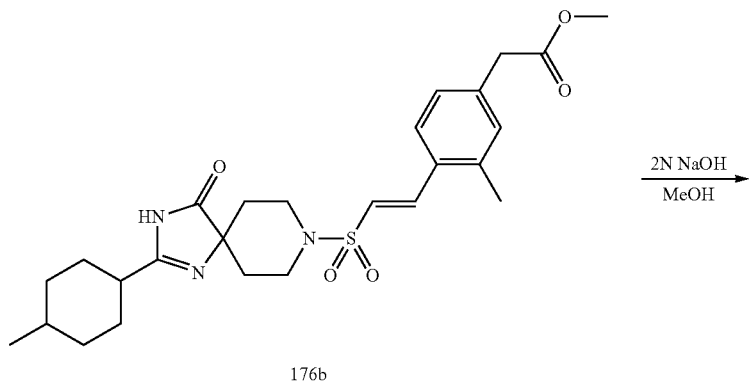

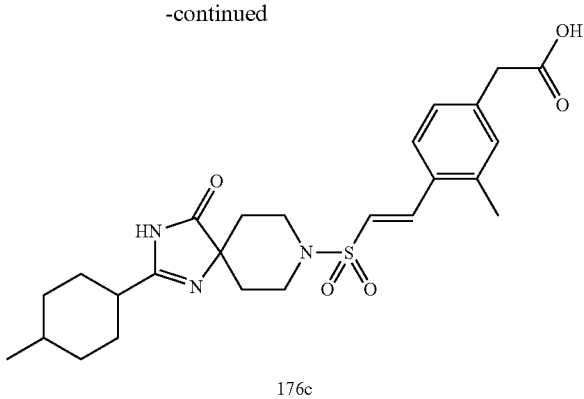

176c (3-Methyl-4-{(E)-2-[2-(4-methyl-cyclohexyl)-4-oxo-1,3, 8-triaza-spiro[4.5]dec-1-ene-8-sulfonyl]-vinyl}-phenyl)-acetic acid was synthesized by operations similar to those in Reaction 25-2 and Reaction 23-2 using appropriate reagents and starting material.

MS (ESI) m/z=488 (M+H)+.

(Reaction 176-2)

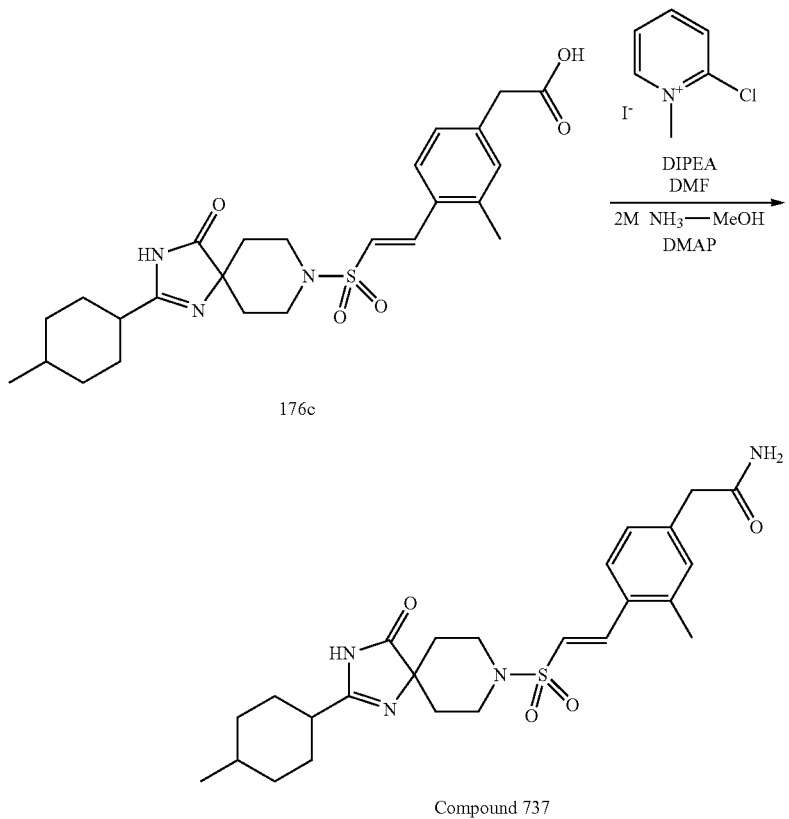

176c

Compound 737

N,N-Diisopropylethylamine (31.4 μL, 0.185 mmol) and 2-chloro-1-methylpyridinium iodide (18.9 mg, 0.074 mmol) were added to a solution of (3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetic acid (30.0 mg, 0.062 mmol) in dichloromethane (0.5 mL) and DMF (0.1 mL), and the mixture was stirred for 10 minutes. A 2.0 M ammonia-methanol solution (0.15 mL, 0.308 mmol) and DMAP (0.8 mg, 0.006 mmol) were then added, and the mixture was stirred overnight. The reaction mixture was then quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure. The resulting residue was purified by silica gel column chromatography to give 2-(3-methyl-4-{(E)-2-[2-(4-methyl-cyclohexyl)-4-oxo-1,3,8-triaza-spiro [4.5]dec-1-ene-8-sulfonyl]-vinyl}-phenyl)-acetamide as a white powder (18.3 mg, 61%).

MS (ESI) m/z=487 (M+H)+.

The aryl bromide reagent used in the synthesis of Compound 737 (2-(4-bromo-3-methyl-phenyl)-malonic acid dimethyl ester) was synthesized as follows.

(Reaction 176-3)

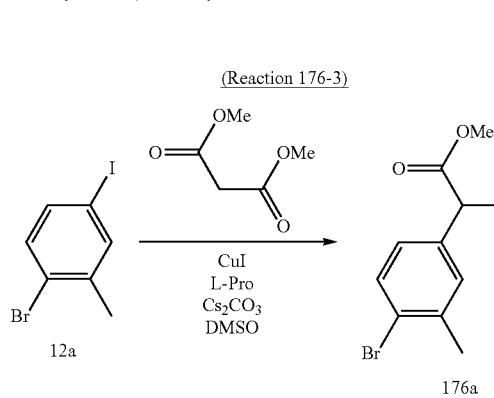

2-(4-Bromo-3-methyl-phenyl)-malonic acid dimethyl ester was synthesized by operations similar to those in Reaction 12-1 using appropriate reagents and starting material.

MS (ESI) m/z=302 (M+H)+.

Example 177

2-Cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one (Compound 738)

(Reaction 177-1)

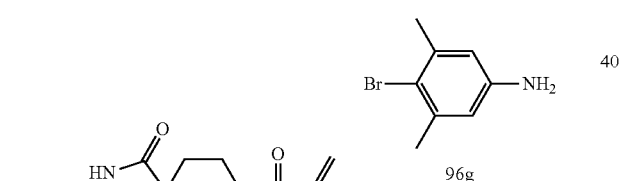

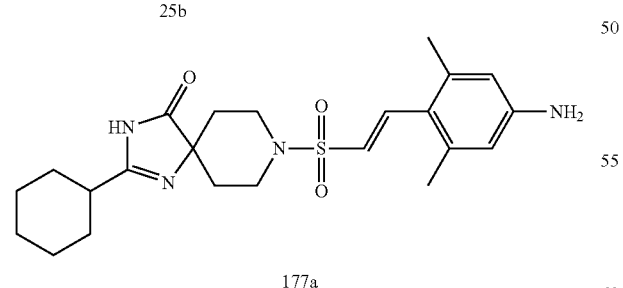

8-[(E)-2-(4-Amino-2,6-dimethyl-phenyl)vinyl]sulfonyl-3-cyclohexyl-2,4,8-triazaspiro[4.5]dec-3-en-1-one was synthesized by operations similar to those in Reaction 26-1 using appropriate reagents and starting material.

MS (ESI) m/z=445 (M+H)+.

(Reaction 177-2)

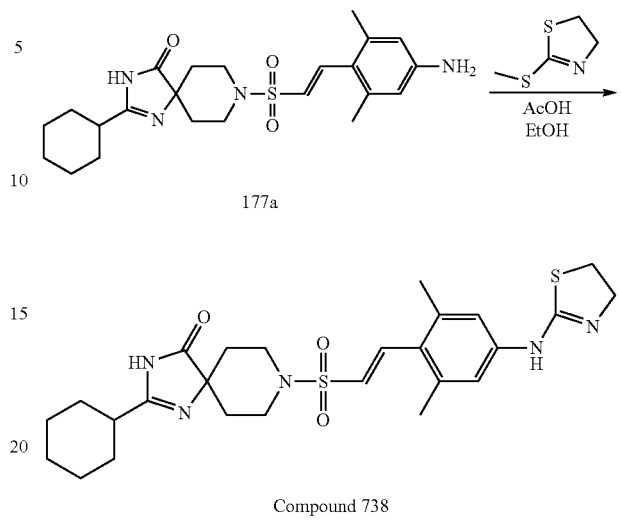

2-(Methylthio)-2-thiazoline (19 µL, 0.17 mmol) and acetic acid (1.2 ml) were added to a solution of 8-[(E)-2-(4-amino-2,6-dimethyl-phenyl)vinyl]sulfonyl-3-cyclohexyl-2,4,8-triazaspiro[4.5]dec-3-en-1-one (74 mg, 0.16 mmol) in EtOH (2.5 ml) at room temperature, and the mixture was heated with stirring at 80° C. for 16 hours. The reaction solution was diluted with ethyl acetate, and the organic layer was then sequentially washed with water and saturated brine and concentrated under reduced pressure. The residue was purified by silica gel column chromatography (ethyl acetate) to give 2-cyclohexyl-8-{(E)-2-[4-(4,5-dihydro-thiazol-2-ylamino)-2,6-dimethyl-phenyl]-ethenesulfonyl}-1,3,8-triaza-spiro[4.5]dec-1-en-4-one (46.1 mg, 52%).

MS (ESI) m/z=530 (M+H)+.

Example 178

2-Cyclohexyl-8-{(E)-2-[2-methyl-4-(3-methyl-oxetan-3-ylmethoxy)-phenyl]-ethenesulfonyl}-1,3,8-triazaspiro[4.5]dec-1-en-4-one (Compound 739)

(Reaction 178-1)

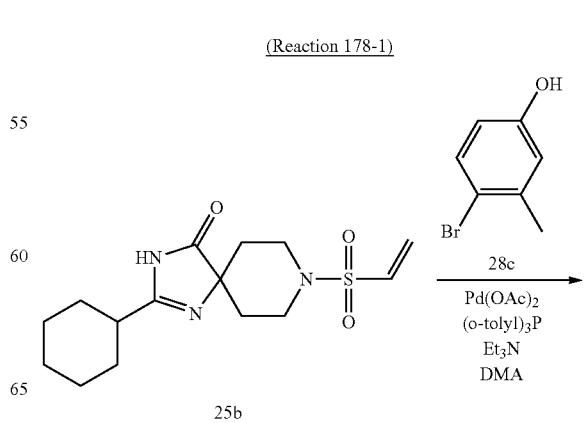

876

Example 179

1-(3,5-Dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea (Compound 740) and 1-(3,5-dimethyl-4-{1-methyl-2-[2-(4-methyl-cyclohexyl)-4-oxo-1,3,8-triaza-spiro[4.5]dec-1-ene-8-sulfonyl]-vinyl}-phenyl)-1-methyl-urea (Compound 741)

(Reaction 179-1)

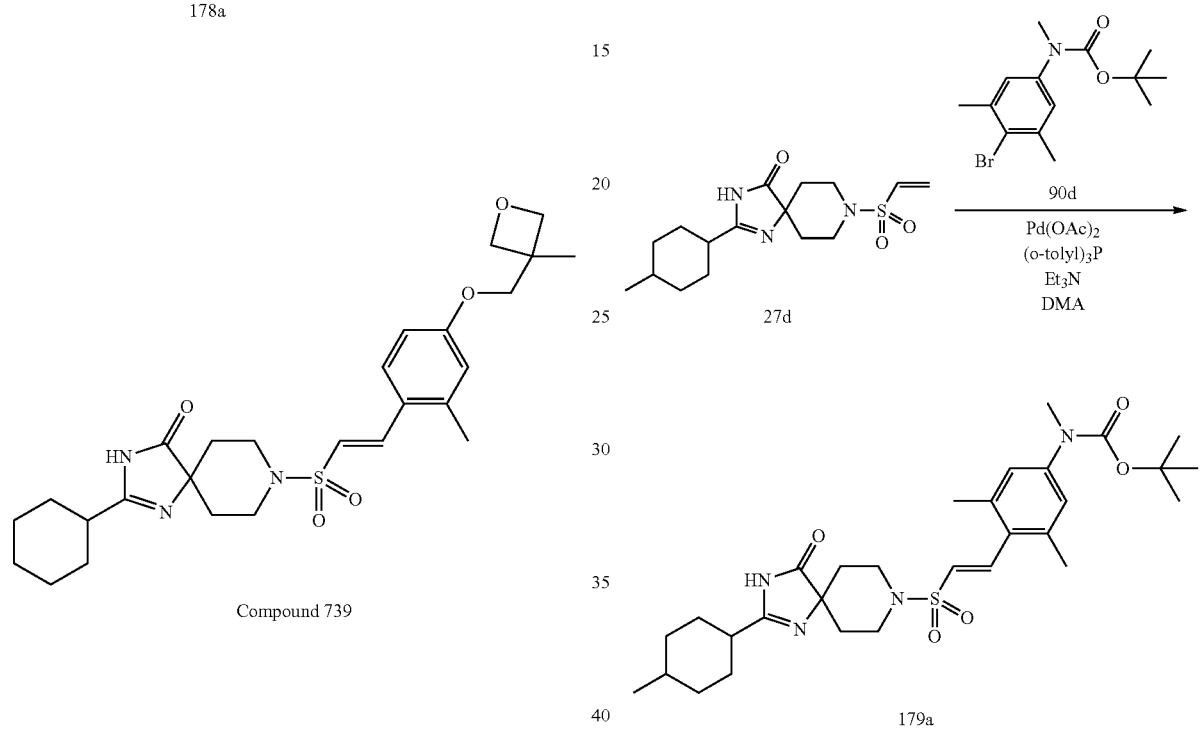

(3,5-Dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester was synthesized by operations similar to those in Reaction 26-1 using appropriate reagents and starting material.

MS (ESI) m/z=573 (M+H)+.

(Reaction 179-2)

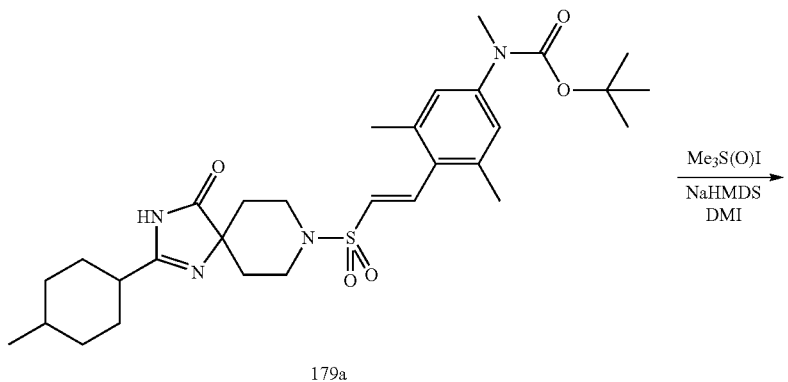

875

-continued

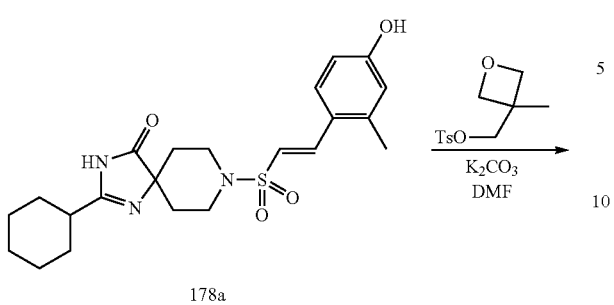

178a

Compound 739

2-Cyclohexyl-8-{(E)-2-[2-methyl-4-(3-methyl-oxetan-3-ylmethoxy)-phenyl]-ethenesulfonyl}-1,3,8-triaza-spiro[4.5]dec-1-en-4-one was synthesized by operations similar to those in Reaction 25-2 and Reaction 26-4 using appropriate reagents and starting material.

MS (ESI) m/z=516 (M+H)+.

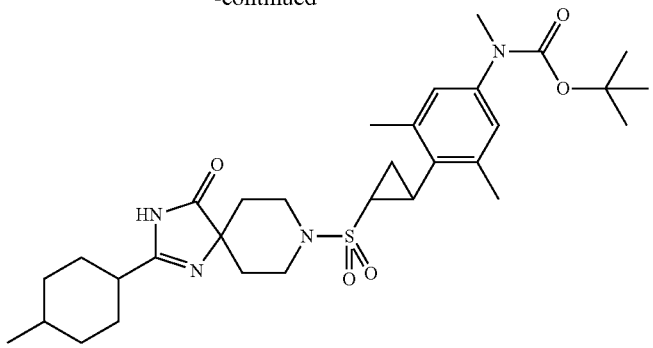

179b

A 1 M solution of sodium bis(trimethylsilyl)amide in tetrahydrofuran (0.31 mL, 0.306 mmol) was added to a mixture of trimethylsulfoxonium iodide (29 mg, 0.131 mmol) in 1,3-dimethyl-2-imidazolidinone (2 mL) at room temperature. The reaction solution was stirred at room temperature for 0.5 hour. A mixed solution of (3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester (50 mg, 0.0873 mmol) in 1,3-dimethyl-2-imidazolidinone (2 mL) was then added at room temperature, and the mixture was heated with stirring at 50° C. for 15 hours. After returning to room temperature, an aqueous ammonium chloride solution and ethyl acetate were added to the reaction solution. The organic layer and the aqueous layer were separated, and the aqueous layer was repeatedly extracted with ethyl acetate three times. The organic layers were combined, washed with water twice and saturated brine, and then concentrated under reduced pressure. The resulting residue was purified by silica gel column chromatography to give a mixture of (3,5-dimethyl-4-{2-[2-(4-methyl-cyclohexyl)-4-oxo-1,3,8-triaza-spiro[4.5]dec-1-ene-8-sulfonyl]-cyclopropyl}-phenyl)-methyl-carbamic acid tert-butyl ester. This mixture was used in the next reaction as such without further purification.

MS (ESI) m/z=587 (M+H)+.

(Reaction 179-3)

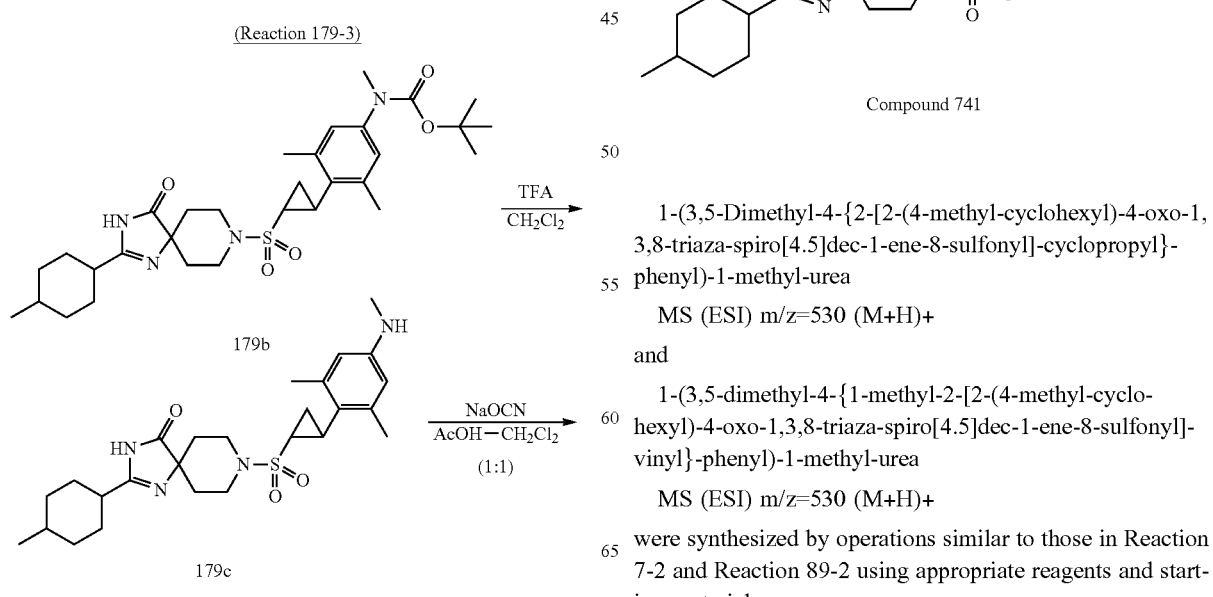

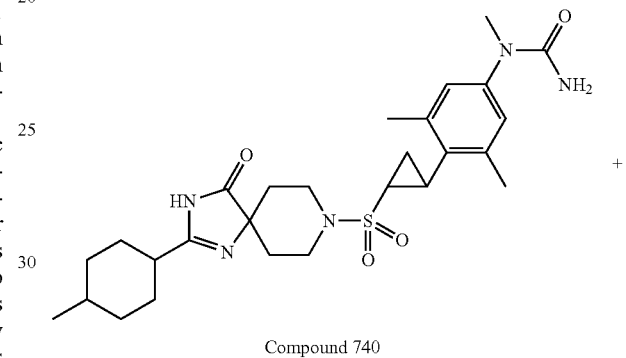

Compound 740

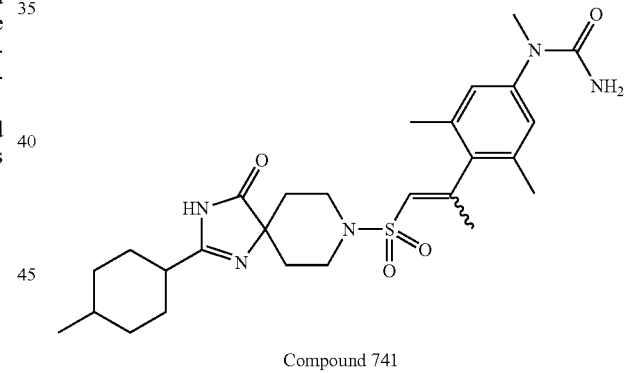

Compound 741

1-(3,5-Dimethyl-4-{2-[2-(4-methyl-cyclohexyl)-4-oxo-1,3,8-triaza-spiro[4.5]dec-1-ene-8-sulfonyl]-cyclopropyl}-phenyl)-1-methyl-urea MS (ESI) m/z=530 (M+H)+ and 1-(3,5-dimethyl-4-{1-methyl-2-[2-(4-methyl-cyclohexyl)-4-oxo-1,3,8-triaza-spiro[4.5]dec-1-ene-8-sulfonyl]-vinyl}-phenyl)-1-methyl-urea MS (ESI) m/z=530 (M+H)+ were synthesized by operations similar to those in Reaction 7-2 and Reaction 89-2 using appropriate reagents and starting material.

Example 180
N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 742)
(Reaction 180-1)
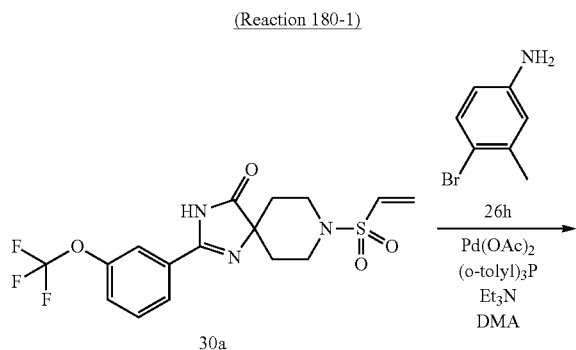
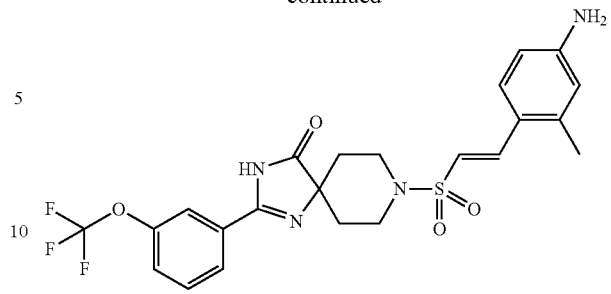
8-[(E)-2-(4-Amino-2-methyl-phenyl)-ethenesulfonyl]-2-(3-trifluoromethoxy-phenyl)-1,3,8-triaza-spiro[4.5]dec-1-en-4-one was synthesized by operations similar to those in Reaction 26-1 using appropriate reagents and starting material.
MS (ESI) m/z=509 (M+H)+
(Reaction 180-2)
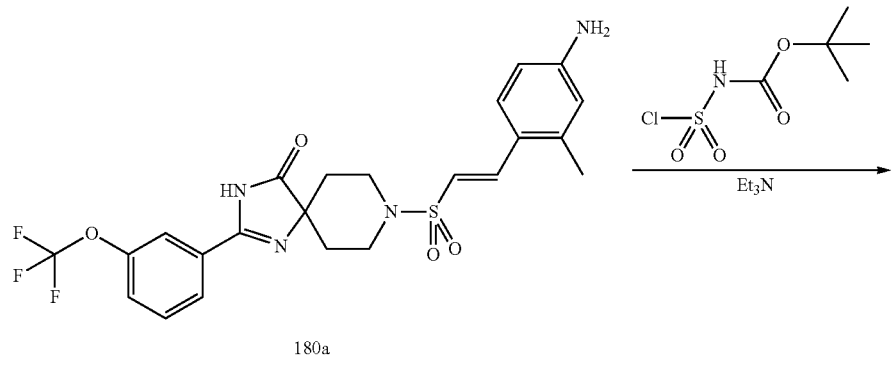
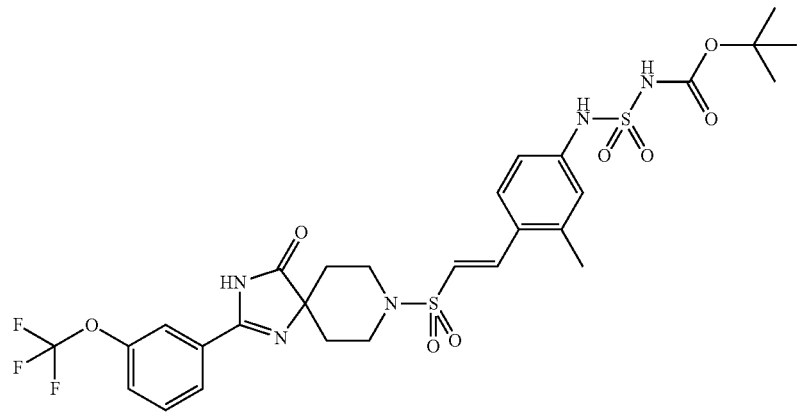

A solution of tBuOH (71.9 mg, 0.97 mmol) in dichloromethane (1.5 ml) was added to a solution of chlorosulfonyl isocyanate (137 mg, 0.97 mmol) in dichloromethane (3 ml) with stirring under ice-cooling. The mixture was stirred at 0° C. for 10 minutes and then added to a solution of 8-[(E)-2-(4-amino-2-methyl-phenyl)-ethenesulfonyl]-2-(3-trifluoromethoxy-phenyl)-1,3,8-triaza-spiro[4.5]dec-1-en-4-one (400 mg, 0.81 mmol) and triethylamine (164 mg, 1.62 mmol) in dichloromethane (3 ml). The mixture was stirred for one hour, and then quenched with water and extracted with dichloromethane. The organic layer was washed with saturated brine, and then dried over anhydrous magnesium sulfate and concentrated under reduced pressure. The resulting residue was purified by silica gel column chromatography (ethyl acetate-hexane) to give N-tert-butoxycarbonyl-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (334 mg, 60%).

$^1$H-NMR (400 MHz, CDCl$_3$) δ 1.42 (9H, s), 1.78 (2H, dt, J=14.2, 3.9 Hz), 2.04-2.14 (2H, m), 2.40 (3H, s), 3.43 (2H, ddd, J=12.7, 9.8, 2.9 Hz), 3.74 (2H, dt, J=12.2, 4.4 Hz), 6.64 (1H, d, J=15.6 Hz), 7.08-7.11 (2H, m), 7.38 (1H, d, J=8.3 Hz), 7.48-7.54 (2H, m), 7.68 (1H, d, J=15.1 Hz), 7.73 (1H, d, J=7.8 Hz), 7.76 (1H, s), 9.62 (1H, s);

MS (ESI) m/z=668 (M+H)+.

(Reaction 180-3)

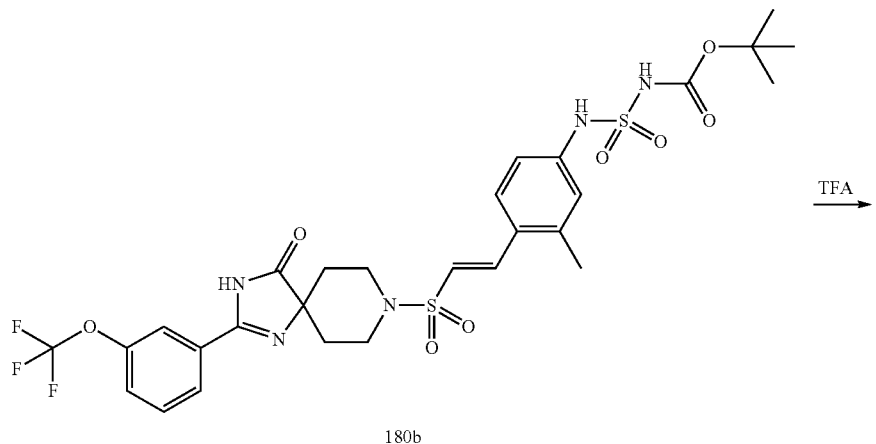

180b

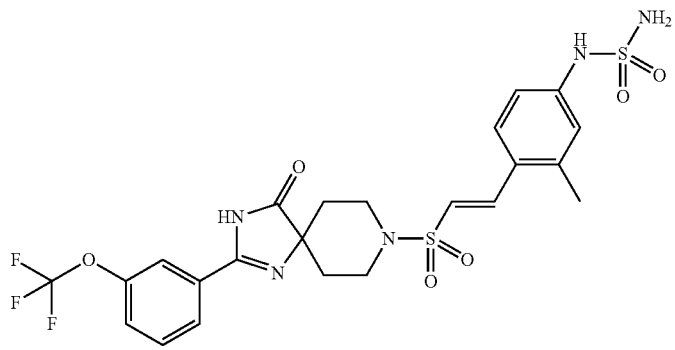

Compound 742

N-(3-Methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was synthesized by operations similar to those in Reaction 4-1 using appropriate reagents and starting material.

MS (ESI) m/z=588 (M+H)+.

Example 181
N-(3-Hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide (Compound 743)
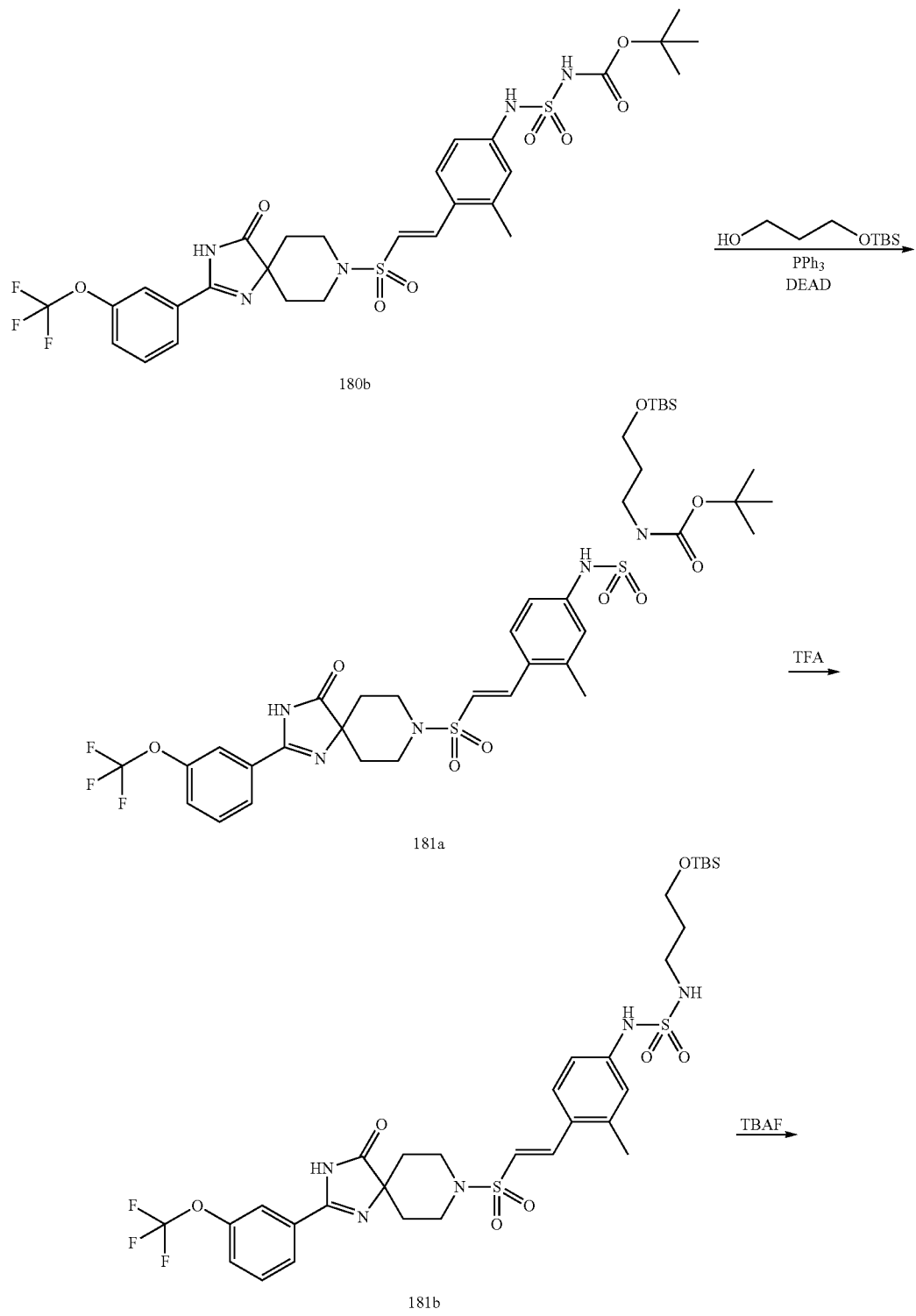

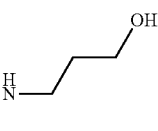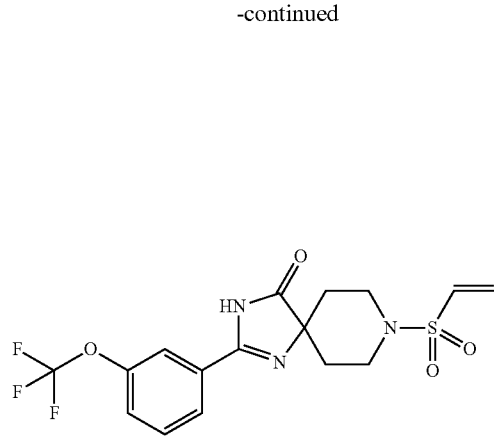

Compound 743

N-(3-Hydroxy-propyl)-N'-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-sulfamide was synthesized by operations similar to those in Reaction 31-7, Reaction 4-1 and Reaction 39-2 using appropriate reagents and starting material.

MS (ESI) m/z=646 (M+H)+.

Example 182

N-Methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide (Compound 744)

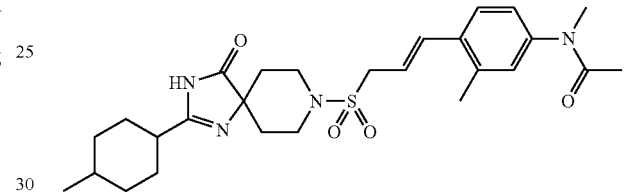

Compound 744

N-Methyl-N-(3-methyl-4-{(E)-3-[2-(4-methyl-cyclohexyl)-4-oxo-1,3,8-triaza-spiro[4.5]dec-1-ene-8-sulfonyl]-propenyl}-phenyl)-acetamide was synthesized by operations similar to those in Reaction 5-4, Reaction 55-2 and Reaction 26-1 using appropriate reagents and starting material.

MS (ESI) m/z=515 (M+H)+.

Example 183

2-Cyclohexyl-8-[2-(2-methyl-1H-indol-4-yl)-ethanesulfonyl]-1,3,8-triaza-spiro[4.5]dec-1-en-4-one (Compound 745)

(Reaction 182-1)

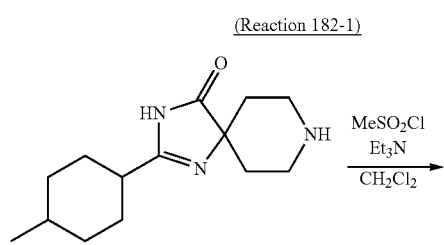

11j

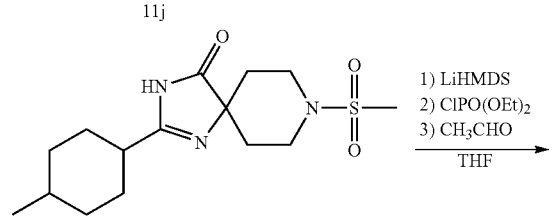

182a (Reaction 183-1)

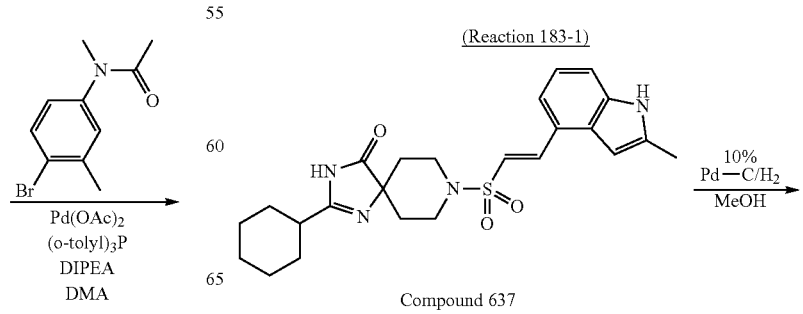

Compound 637

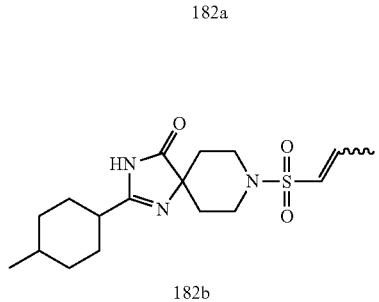

182b

2-Cyclohexyl-8-[2-(2-methyl-1H-indol-4-yl)-ethanesulfonyl]-1,3,8-triaza-spiro[4.5]dec-1-en-4-one (Compound 745) was obtained by operations similar to those in Reaction 18-2 using Compound 637 as a starting material.

MS (ESI) m/z=457 (M+H)+.

The example compounds shown below were obtained by operations similar to those in Example 183 using appropriate solvents (methanol or dimethylformamide or a methanol-dimethylformamide mixed solution) and starting compounds.

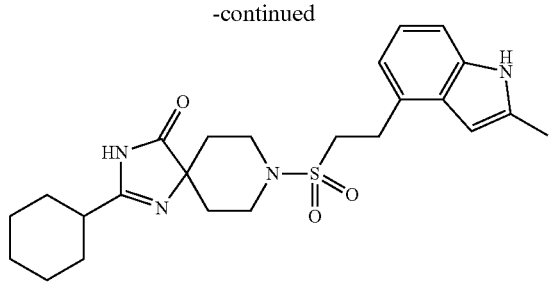

Compound 745

Compounds 746 to Compound 749

TABLE 110

| Starting Compound | Target Compound | Structure | LCMS condition | Retention time (min) | MS (m/z) |
|---|---|---|---|---|---|
| 526 | 746 | 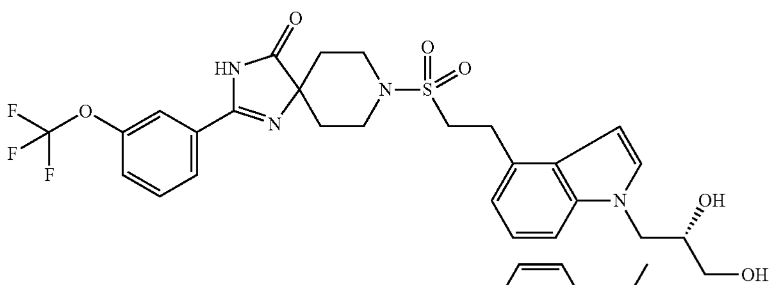 | LCMS-C-1 | 2.58 | 595 (M + H)+ |
| 638 | 747 | 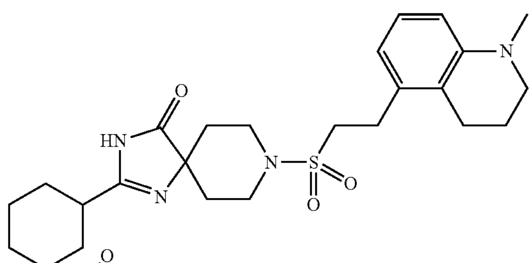 | LCMS-A-1 | 1.40 | 473 (M + H)+ |
| 480 | 748 | 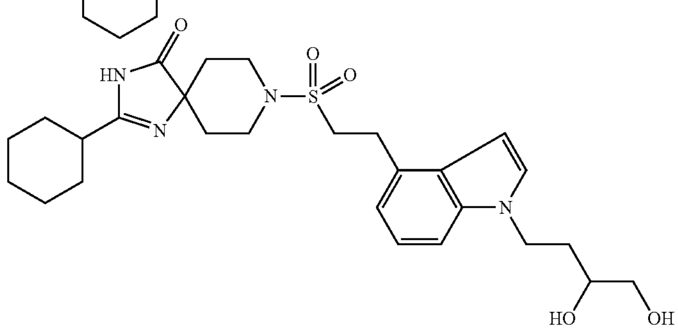 | LCMS-C-1 | 2.43 | 531 (M + H)+ |
| 583 | 749 | 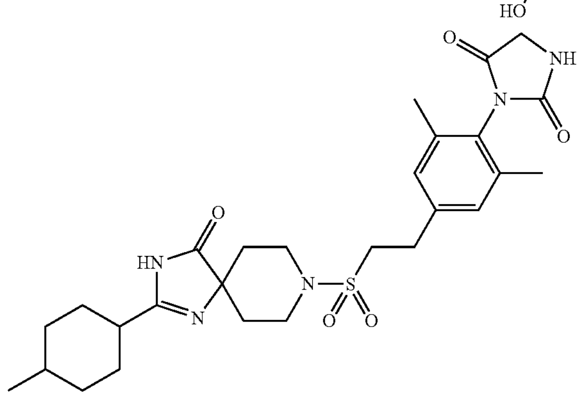 | LCMS-A-1 | 1.91 | 544 (M + H)+ |

Example 184

2-(3-Methyl-4-{2-[2-(4-methyl-cyclohexyl)-4-oxo-1,3,8-triaza-spiro[4.5]dec-1-ene-8-sulfonyl]-ethyl}-phenyl)-acetamide (Compound 750)

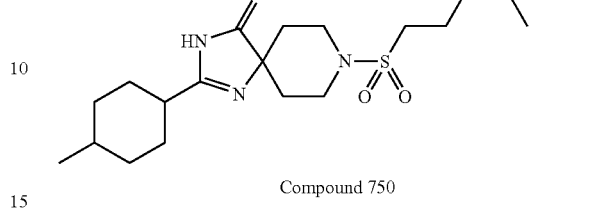

Compound 750

(Reaction 184-1)

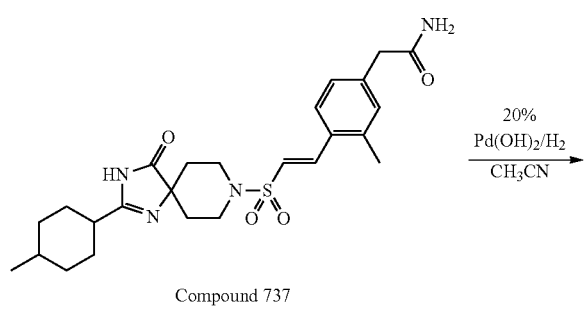

Compound 737

20% palladium hydroxide (7.4 mg) was added to a solution of Compound 737 (14.7 mg, 0.030 mmol) in acetonitrile (1.0 mL), and the mixture was stirred at room temperature for one hour in a hydrogen atmosphere. The reaction mixture was filtered through celite, and the filtrate was concentrated under reduced pressure. The resulting residue was then purified by silica gel column chromatography to give 2-(3-methyl-4-{2-[2-(4-methyl-cyclohexyl)-4-oxo-1,3,8-triaza-spiro[4.5]dec-1-ene-8-sulfonyl]-ethyl}-phenyl)-acetamide (Compound 750) as a white powder (10.6 mg, 72%).

The example compounds shown below were obtained by operations similar to those in Example 184 using appropriate solvents (acetonitrile or methanol or an acetonitrile-methanol mixed solution) and starting compounds.

Compounds 751 to Compound 834

TABLE 111

| Starting Compound | Target Compound | Structure | LCMS condition | Retention time (min) | MS (m/z) |
|---|---|---|---|---|---|
| 509 | 751 | 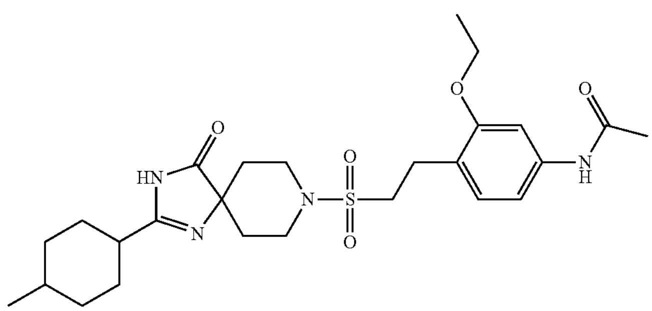 | LCMS-D-1 | 2.57 | 519 (M + H)+ |
| 510 | 752 | 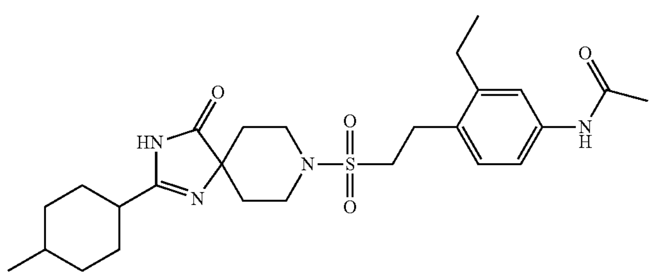 | LCMS-D-1 | 2.53 | 503 (M + H)+ |

TABLE 111-continued

| Starting Compound | Target Compound | Structure | LCMS condition | Retention time (min) | MS (m/z) |
|---|---|---|---|---|---|
| 576 | 753 | 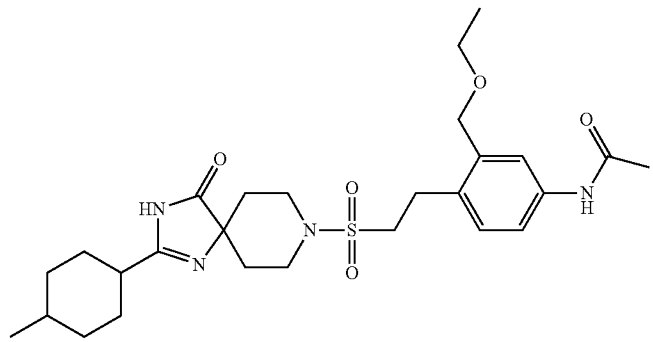 [SMILES: CCOCc1cc(NC(C)=O)ccc1CCS(=O)(=O)N1CCC2(CC1)N=C(C1CCC(C)CC1)NC2=O] | LCMS-D-1 | 2.48 | 533 (M + H)+ |
| 512 | 754 | 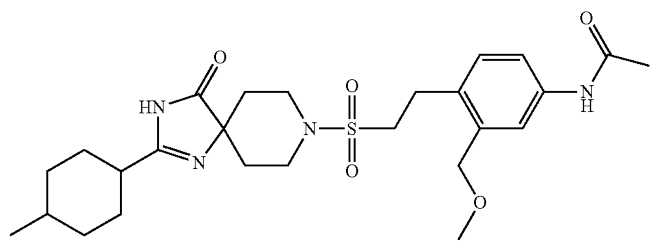 [SMILES: COCc1cc(NC(C)=O)ccc1CCS(=O)(=O)N1CCC2(CC1)N=C(C1CCC(C)CC1)NC2=O] | LCMS-D-1 | 2.33 | 519 (M + H)+ |
| 542 | 755 | 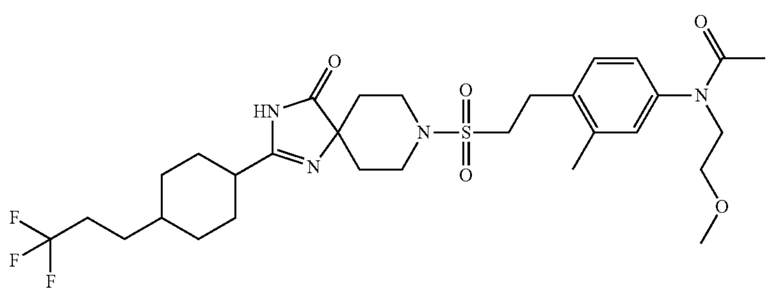 | LCMS-D-1 | 2.30 | 629 (M + H)+ |
| 543 | 756 | 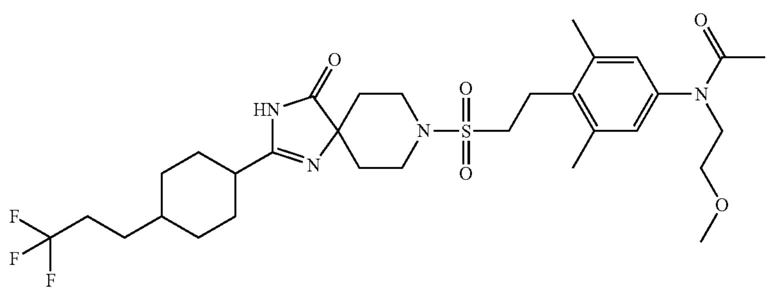 | LCMS-D-1 | 2.43 | 643 (M + H)+ |
| 545 | 757 | 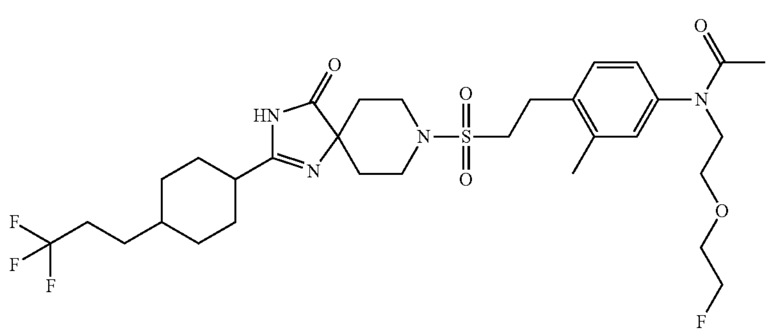 | LCMS-D-1 | 2.30 | 661 (M + H)+ |

TABLE 111-continued

| Starting Compound | Target Compound | Structure | LCMS condition | Retention time (min) | MS (m/z) |
|---|---|---|---|---|---|
| 544 | 758 | 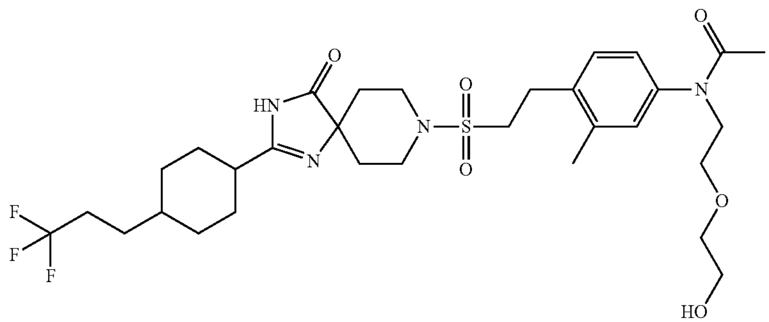 [SMILES: CC(=O)N(CCOCCO)c1ccc(CCS(=O)(=O)N2CCC3(CC2)N=C(C2CCC(CCC(F)(F)F)CC2)NC3=O)c(C)c1] | LCMS-D-1 | 2.11 | 659 (M + H)+ |
| 546 | 759 | 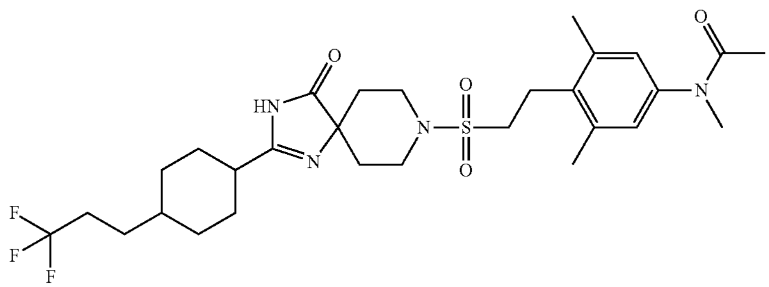 [SMILES: CC(=O)N(C)c1cc(C)c(CCS(=O)(=O)N2CCC3(CC2)N=C(C2CCC(CCC(F)(F)F)CC2)NC3=O)c(C)c1] | LCMS-D-1 | 1.56 | 599 (M + H)+ |
| 548 | 760 | 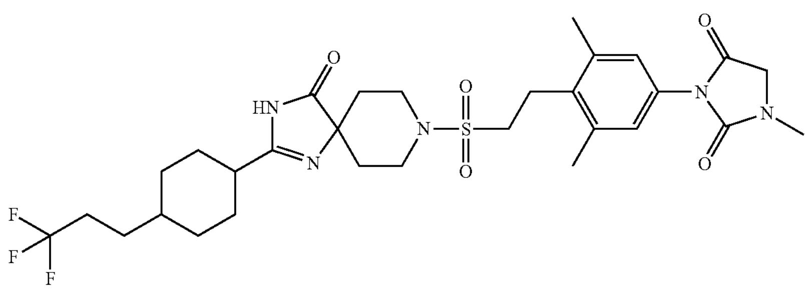 [SMILES: Cc1cc(N2C(=O)CN(C)C2=O)cc(C)c1CCS(=O)(=O)N1CCC2(CC1)N=C(C1CCC(CCC(F)(F)F)CC1)NC2=O] | LCMS-D-1 | 2.08 | 640 (M + H)+ |
| 549 | 761 | 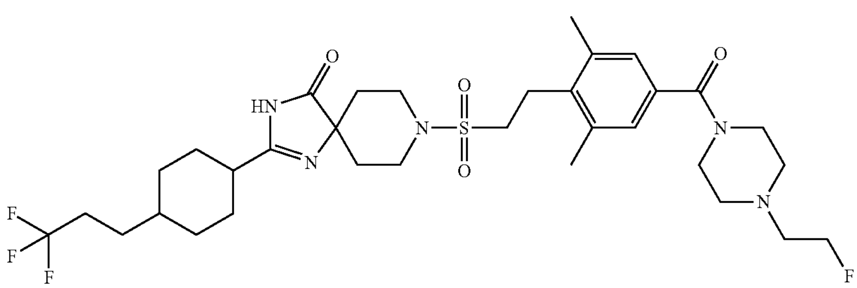 [SMILES: Cc1cc(C(=O)N2CCN(CCF)CC2)cc(C)c1CCS(=O)(=O)N1CCC2(CC1)N=C(C1CCC(CCC(F)(F)F)CC1)NC2=O] | LCMS-D-1 | 1.62 | 686 (M + H)+ |
| 550 | 764 | 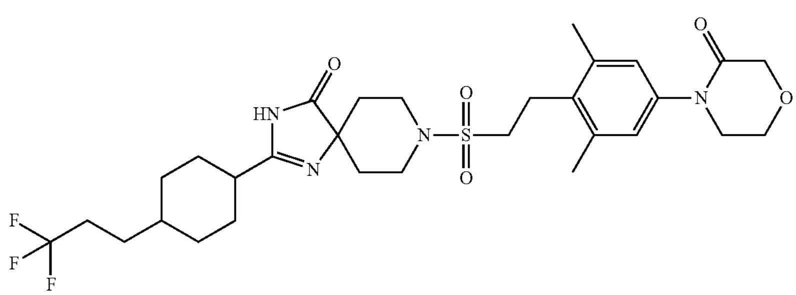 [SMILES: Cc1cc(N2CCOCC2=O)cc(C)c1CCS(=O)(=O)N1CCC2(CC1)N=C(C1CCC(CCC(F)(F)F)CC1)NC2=O] | LCMS-D-1 | 2.22 | 627 (M + H)+ |

TABLE 111-continued

| Starting Compound | Target Compound | Structure | LCMS condition | Retention time (min) | MS (m/z) |
|---|---|---|---|---|---|
| 515 | 765 | 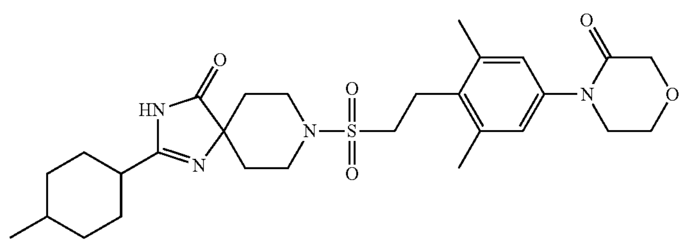 [SMILES: Cc1cc(N2CCOCC2=O)cc(C)c1CCS(=O)(=O)N1CCC2(CC1)N=C(C1CCC(C)CC1)NC2=O] | LCMS-D-1 | 1.80 | 545 (M + H)+ |
| 551 | 766 | 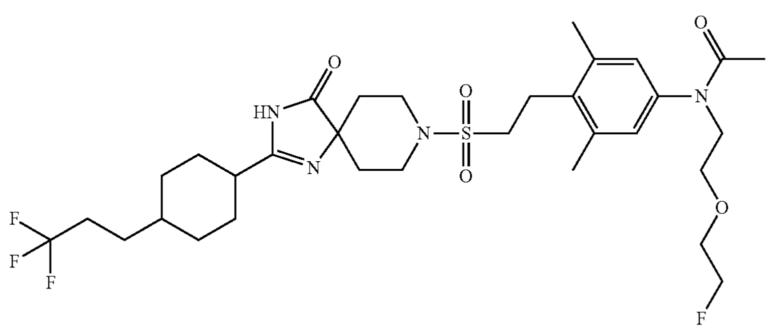 [SMILES: CC(=O)N(CCOCCF)c1cc(C)c(CCS(=O)(=O)N2CCC3(CC2)N=C(C2CCC(CCC(F)(F)F)CC2)NC3=O)c(C)c1] | LCMS-D-1 | 2.42 | 675 (M + H)+ |
| 582 | 767 | 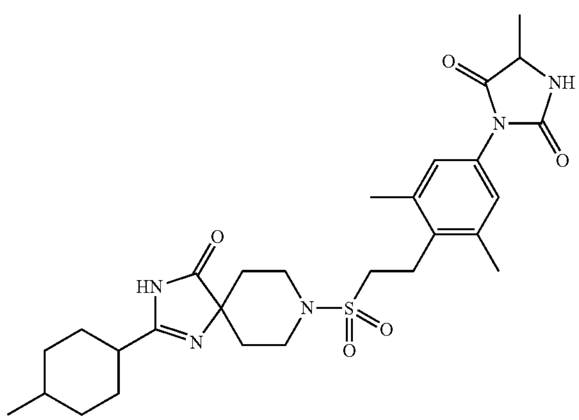 [SMILES: Cc1cc(N2C(=O)NC(C)C2=O)cc(C)c1CCS(=O)(=O)N1CCC2(CC1)N=C(C1CCC(C)CC1)NC2=O] | LCMS-A-1 | 2.03 | 558 (M + H)+ |
| 547 | 768 | 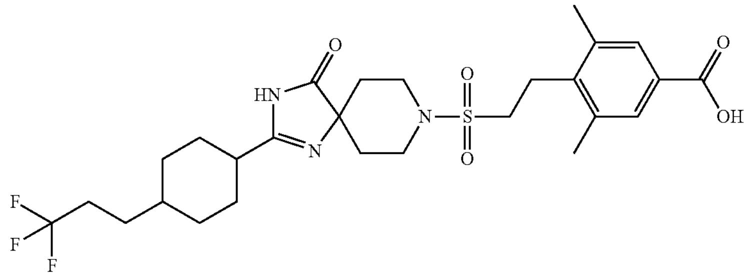 [SMILES: Cc1cc(C(=O)O)cc(C)c1CCS(=O)(=O)N1CCC2(CC1)N=C(C1CCC(CCC(F)(F)F)CC1)NC2=O] | LCMS-D-1 | 2.57 | 572 (M + H)+ |

TABLE 111-continued

| Starting Compound | Target Compound | Structure | LCMS condition | Retention time (min) | MS (m/z) |
|---|---|---|---|---|---|
| 552 | 769 | | LCMS-D-1 | 2.03 | 628 (M + H)+ |
| 553 | 770 | 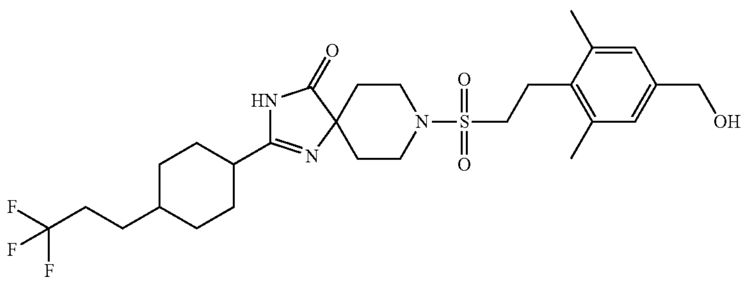 [SMILES: Cc1cc(CO)cc(C)c1CCS(=O)(=O)N1CCC2(CC1)N=C(C1CCC(CCC(F)(F)F)CC1)NC2=O] | LCMS-D-1 | 2.38 | 558 (M + H)+ |
| 516 | 771 | 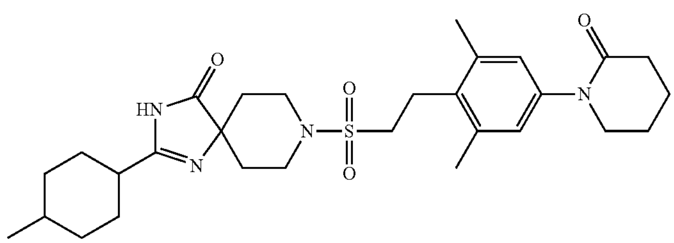 [SMILES: Cc1cc(N2CCCCC2=O)cc(C)c1CCS(=O)(=O)N1CCC2(CC1)N=C(C1CCC(C)CC1)NC2=O] | LCMS-D-1 | 2.58 | 543 (M + H)+ |
| 554 | 772 | 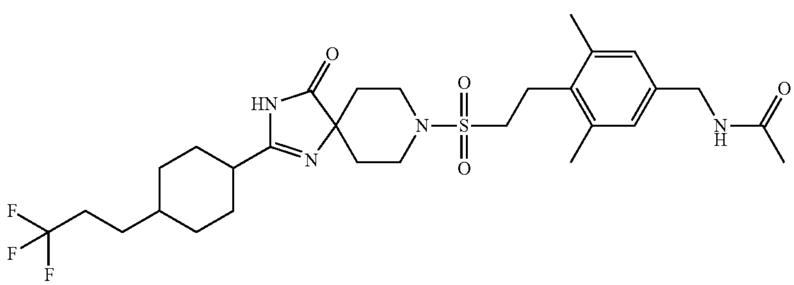 [SMILES: CC(=O)NCc1cc(C)c(CCS(=O)(=O)N2CCC3(CC2)N=C(C2CCC(CCC(F)(F)F)CC2)NC3=O)c(C)c1] | LCMS-D-1 | 2.47 | 599 (M + H)+ |
| 552 | 773 | | LCMS-D-1 | 2.08 | 517 (M + H)+ |

TABLE 111-continued

| Starting Compound | Target Compound | Structure | LCMS condition | Retention time (min) | MS (m/z) |
|---|---|---|---|---|---|
| 554 | 774 | 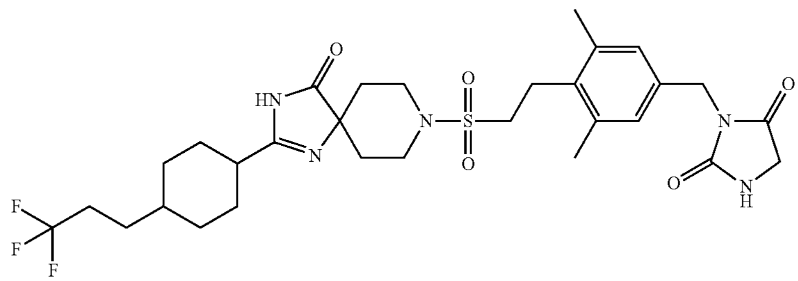 [SMILES: Cc1cc(CN2C(=O)CNC2=O)cc(C)c1CCS(=O)(=O)N1CCC2(CC1)N=C(C1CCC(CCC(F)(F)F)CC1)NC2=O] | LCMS-D-1 | 2.32 | 640 (M + H)+ |
| 555 | 775 | 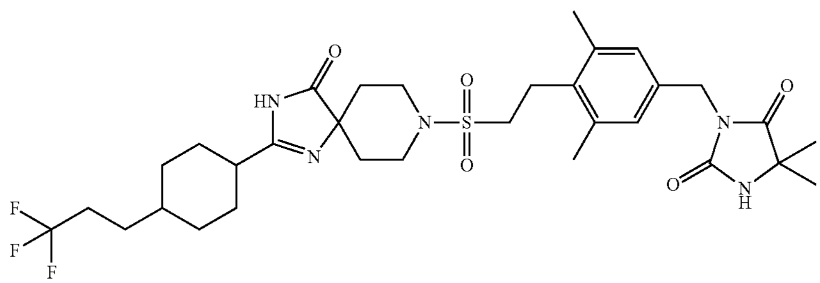 [SMILES: Cc1cc(CN2C(=O)NC(C)(C)C2=O)cc(C)c1CCS(=O)(=O)N1CCC2(CC1)N=C(C1CCC(CCC(F)(F)F)CC1)NC2=O] | LCMS-D-1 | 2.57 | 668 (M + H)+ |
| 556 | 776 | 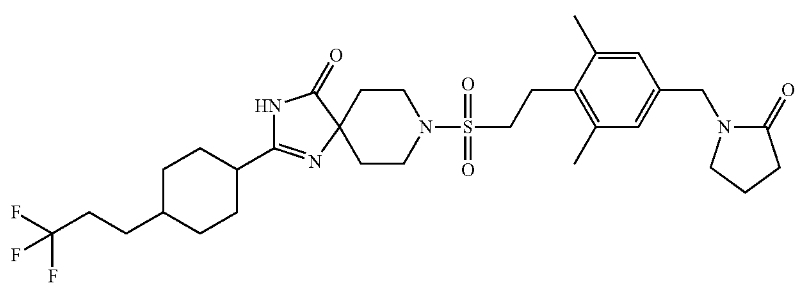 [SMILES: Cc1cc(CN2CCCC2=O)cc(C)c1CCS(=O)(=O)N1CCC2(CC1)N=C(C1CCC(CCC(F)(F)F)CC1)NC2=O] | LCMS-D-1 | 2.50 | 625 (M + H)+ |
| 557 | 777 | 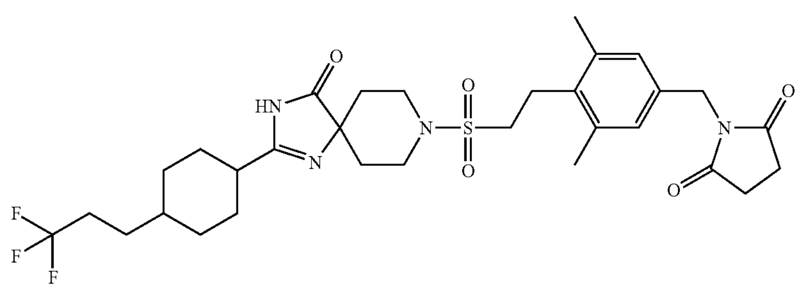 [SMILES: Cc1cc(CN2C(=O)CCC2=O)cc(C)c1CCS(=O)(=O)N1CCC2(CC1)N=C(C1CCC(CCC(F)(F)F)CC1)NC2=O] | LCMS-D-1 | 2.45 | 639 (M + H)+ |
| 581 | 778 | 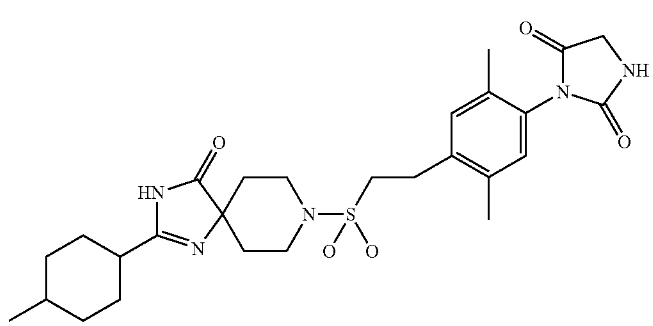 [SMILES: Cc1cc(N2C(=O)CNC2=O)c(C)cc1CCS(O)(O)N1CCC2(CC1)N=C(C1CCC(C)CC1)NC2=O] | LCMS-D-1 | 2.42 | 544 (M + H)+ |

TABLE 111-continued

| Starting Compound | Target Compound | Structure | LCMS condition | Retention time (min) | MS (m/z) |
|---|---|---|---|---|---|
| 518 | 779 | 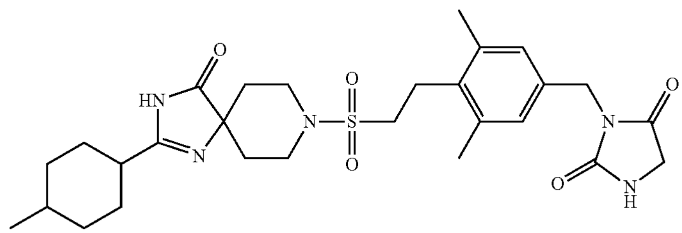 [SMILES: Cc1cc(CN2C(=O)CNC2=O)cc(C)c1CCS(=O)(=O)N1CCC2(CC1)N=C(C1CCC(C)CC1)NC2=O] | LCMS-D-1 | 1.93 | 558 (M + H)+ |
| 519 | 780 | 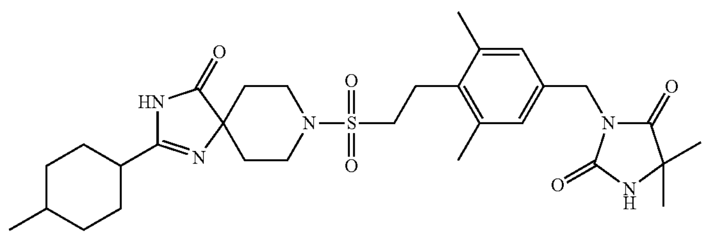 | LCMS-D-1 | 2.20 | 586 (M + H)+ |
| 520 | 781 | 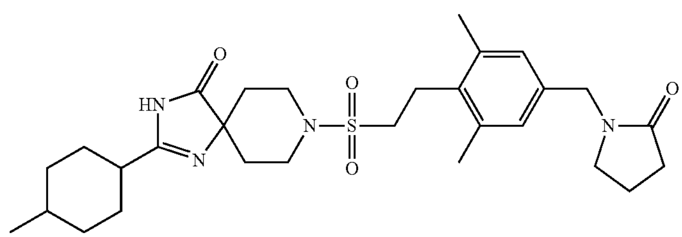 [SMILES: Cc1cc(CN2CCCC2=O)cc(C)c1CCS(=O)(=O)N1CCC2(CC1)N=C(C1CCC(C)CC1)NC2=O] | LCMS-D-1 | 2.10 | 543 (M + H)+ |
| 557 | 782 | 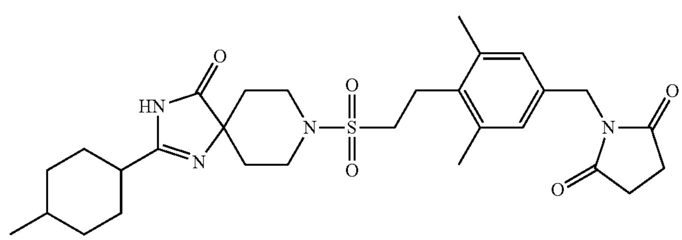 | LCMS-D-1 | 1.98 | 557 (M + H)+ |
| 584 | 783 | 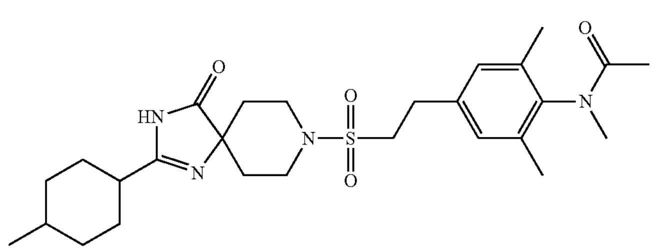 [SMILES: CC(=O)N(C)c1c(C)cc(CCS(=O)(=O)N2CCC3(CC2)N=C(C2CCC(C)CC2)NC3=O)cc1C] | LCMS-D-1 | 1.96 | 517 (M + H)+ |
| 559 | 784 | 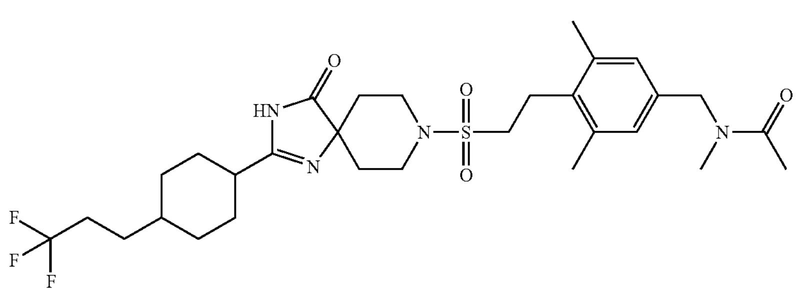 [SMILES: CC(=O)N(C)Cc1cc(C)c(CCS(=O)(=O)N2CCC3(CC2)N=C(C2CCC(CCC(F)(F)F)CC2)NC3=O)c(C)c1] | LCMS-D-1 | 2.47 | 613 (M + H)+ |

TABLE 111-continued

| Starting Compound | Target Compound | Structure | LCMS condition | Retention time (min) | MS (m/z) |
|---|---|---|---|---|---|
| 517 | 785 | 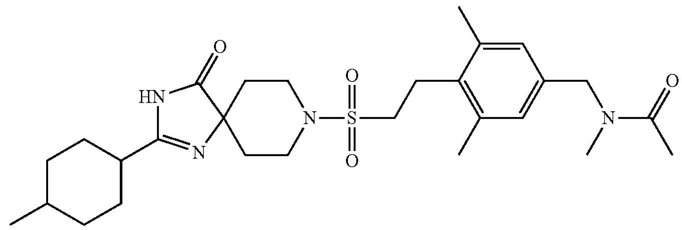 [SMILES: CC(=O)N(C)Cc1cc(C)c(CCS(=O)(=O)N2CCC3(CC2)N=C(C2CCC(C)CC2)NC3=O)c(C)c1] | LCMS-D-1 | 2.10 | 531 (M + H)+ |
| 587 | 786 | 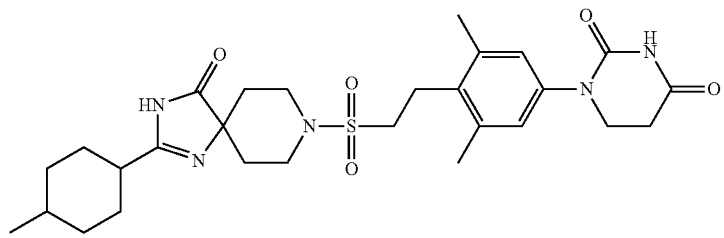 [SMILES: Cc1cc(N2CCC(=O)NC2=O)cc(C)c1CCS(=O)(=O)N1CCC2(CC1)N=C(C1CCC(C)CC1)NC2=O] | LCMS-D-1 | 1.72 | 558 (M + H)+ |
| 629 | 787 | 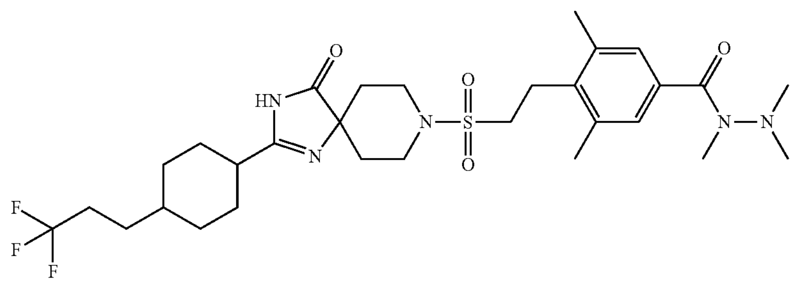 [SMILES: Cc1cc(C(=O)N(C)N(C)C)cc(C)c1CCS(=O)(=O)N1CCC2(CC1)N=C(C1CCC(CCC(F)(F)F)CC1)NC2=O] | LCMS-D-1 | 2.40 | 628 (M + H)+ |
| 623 | 788 | 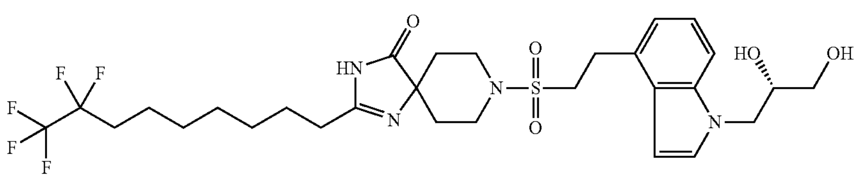 [SMILES: O=C1NC(CCCCCCCC(F)(F)C(F)(F)F)=NC12CCN(S(=O)(=O)CCc1cccc3c1ccn3C[C@H](O)CO)CC2] | LCMS-C-1 | 2.85 | 651 (M + H)+ |
| 622 | 789 | 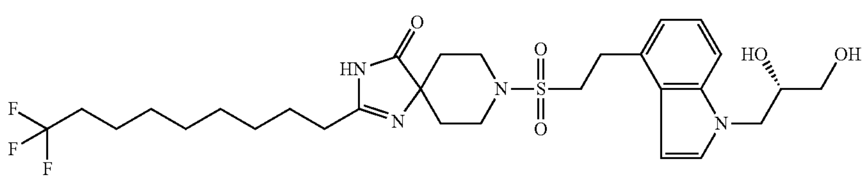 [SMILES: O=C1NC(CCCCCCCCC(F)(F)F)=NC12CCN(S(=O)(=O)CCc1cccc3c1ccn3C[C@H](O)CO)CC2] | LCMS-C-1 | 2.80 | 615 (M + H)+ |
| 536 | 790 | 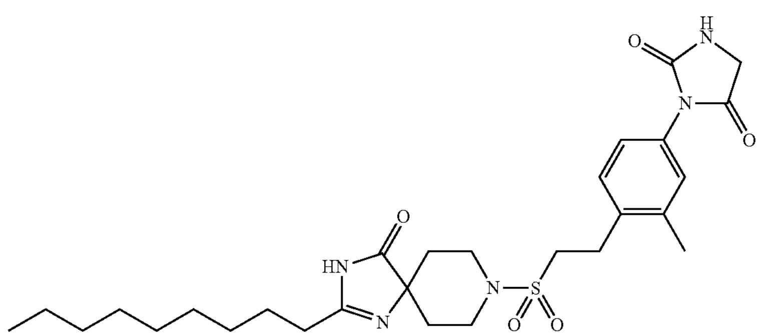 [SMILES: CCCCCCCCCC1=NC2(CCN(S(=O)(=O)CCc3ccc(N4C(=O)CNC4=O)cc3C)CC2)C(=O)N1] | LCMS-C-1 | 2.82 | 560 (M + H)+ |

TABLE 111-continued
| Starting Compound | Target Compound | Structure | LCMS condition | Retention time (min) | MS (m/z) |
|---|---|---|---|---|---|
| 630 | 791 | 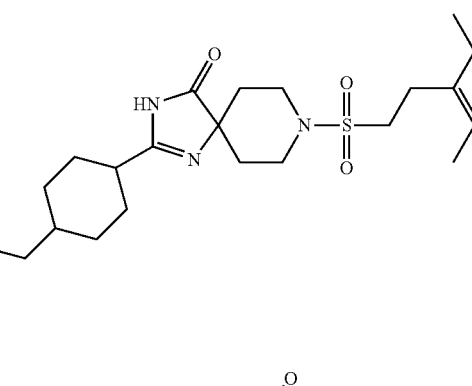 | LCMS-D-1 | 2.45 | 641 (M + H)+ |
| 618 | 792 | 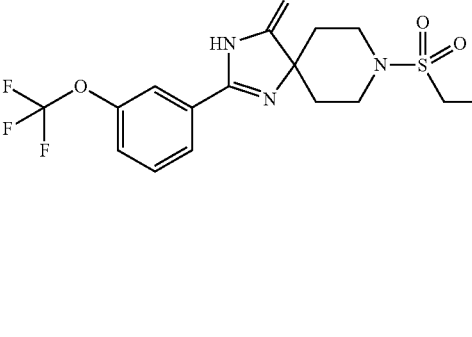 | LCMS-F-1 | 0.89 | 594 (M + H)+ |
| 617 | 793 | 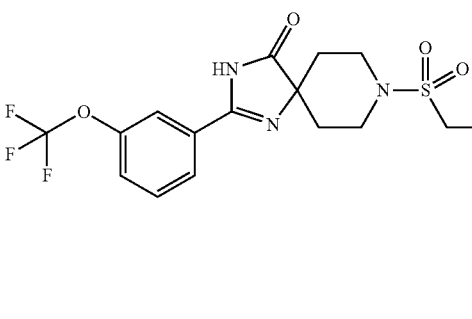 | LCMS-F-1 | 0.93 | 595 (M + H)+ |
| 718 | 794 | 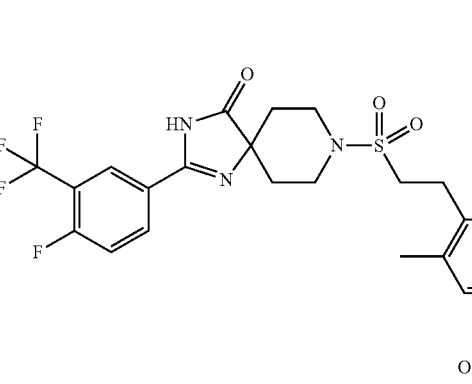 | LCMS-F-1 | 0.94 | 613 (M + H)+ |

TABLE 111-continued

| Starting Compound | Target Compound | Structure | LCMS condition | Retention time (min) | MS (m/z) |
|---|---|---|---|---|---|
| 537 | 795 | 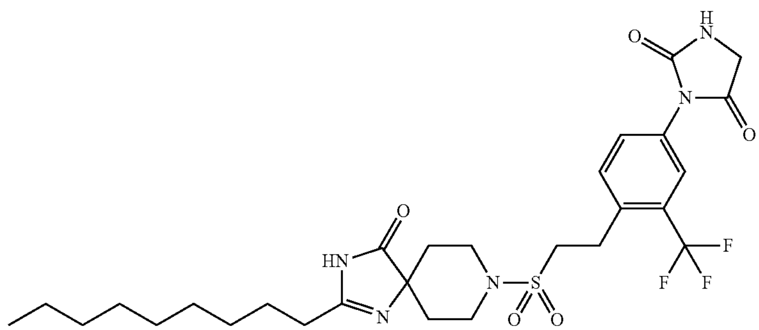 [SMILES: CCCCCCCCCC1=NC2(CCN(S(=O)(=O)CCc3ccc(N4C(=O)CNC4=O)cc3C(F)(F)F)CC2)C(=O)N1] | LCMS-A-1 | 2.53 | 614 (M + H)+ |
| 628 | 796 | 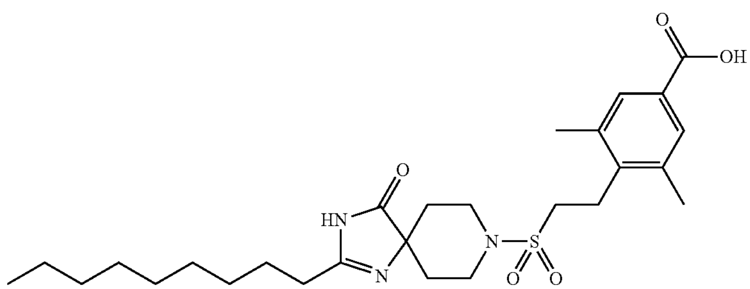 [SMILES: CCCCCCCCCC1=NC2(CCN(S(=O)(=O)CCc3c(C)cc(C(=O)O)cc3C)CC2)C(=O)N1] | LCMS-F-1 | 0.96 | 520 (M + H)+ |
| 535 | 797 | 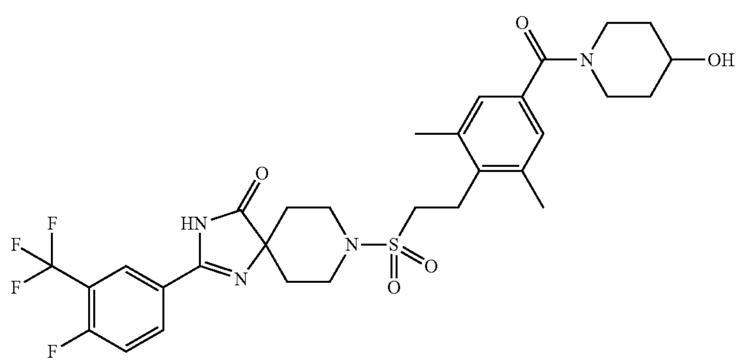 [SMILES: Cc1cc(C(=O)N2CCC(O)CC2)cc(C)c1CCS(=O)(=O)N1CCC2(CC1)N=C(c1ccc(F)c(C(F)(F)F)c1)NC2=O] | LCMS-F-1 | 0.94 | 639 (M + H)+ |
| 627 | 798 | 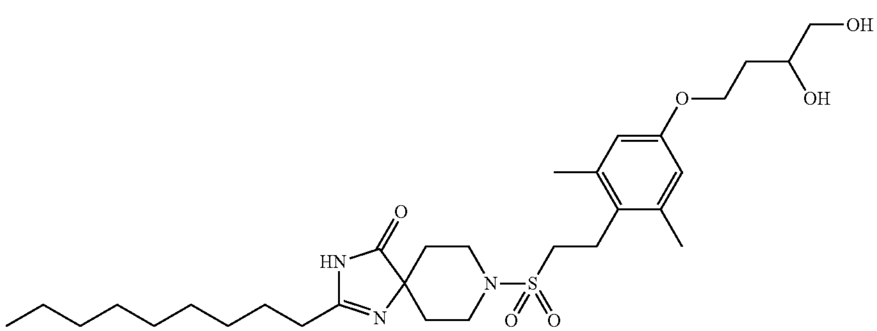 [SMILES: CCCCCCCCCC1=NC2(CCN(S(=O)(=O)CCc3c(C)cc(OCCC(O)CO)cc3C)CC2)C(=O)N1] | LCMS-A-1 | 2.43 | 580 (M + H)+ |

TABLE 111-continued

| Starting Compound | Target Compound | Structure | LCMS condition | Retention time (min) | MS (m/z) |
|---|---|---|---|---|---|
| 635 | 799 | 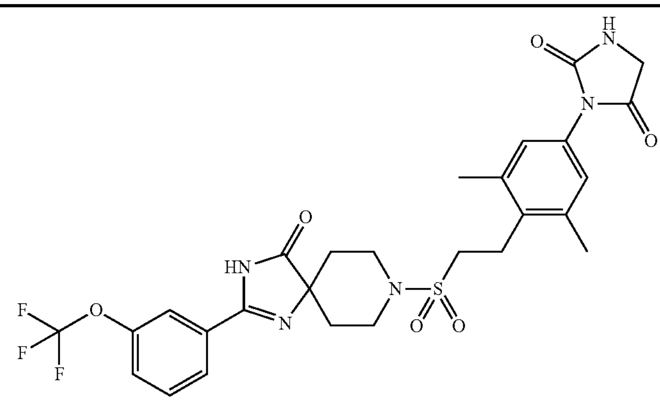 | LCMS-F-1 | 0.91 | 608 (M + H)+ |
| 636 | 800 | 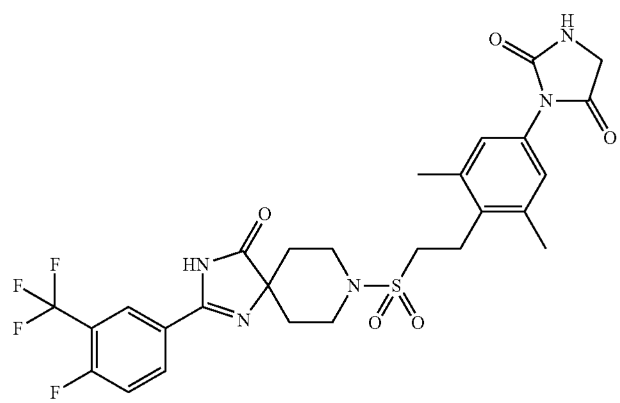 [SMILES: Cc1cc(N2C(=O)CNC2=O)cc(C)c1CCS(=O)(=O)N1CCC2(CC1)N=C(c1ccc(F)c(C(F)(F)F)c1)NC2=O] | LCMS-F-1 | 0.91 | 610 (M + H)+ |
| 639 | 801 | 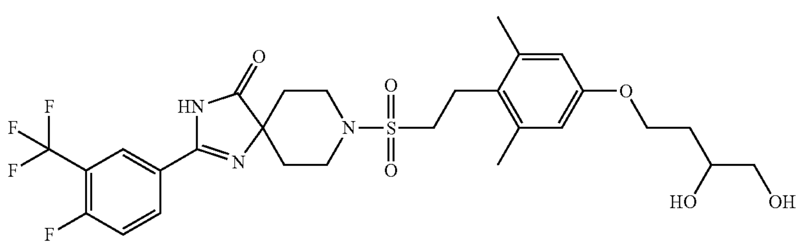 [SMILES: Cc1cc(OCCC(O)CO)cc(C)c1CCS(=O)(=O)N1CCC2(CC1)N=C(c1ccc(F)c(C(F)(F)F)c1)NC2=O] | LCMS-F-1 | 0.99 | 616 (M + H)+ |
| 641 | 802 | 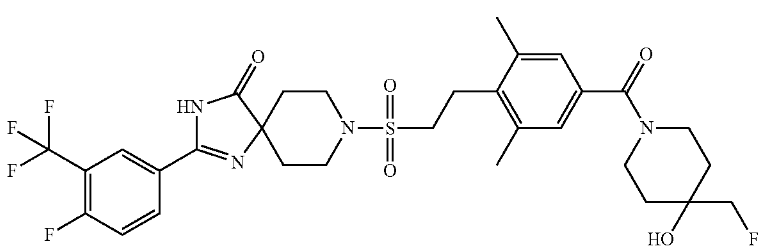 [SMILES: Cc1cc(C(=O)N2CCC(O)(CF)CC2)cc(C)c1CCS(=O)(=O)N1CCC2(CC1)N=C(c1ccc(F)c(C(F)(F)F)c1)NC2=O] | LCMS-F-1 | 0.99 | 671 (M + H)+ |
| 642 | 803 | 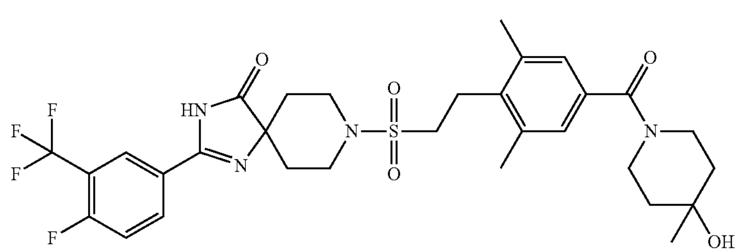 [SMILES: Cc1cc(C(=O)N2CCC(C)(O)CC2)cc(C)c1CCS(=O)(=O)N1CCC2(CC1)N=C(c1ccc(F)c(C(F)(F)F)c1)NC2=O] | LCMS-F-1 | 1.00 | 653 (M + H)+ |

TABLE 111-continued

| Starting Compound | Target Compound | Structure | LCMS condition | Retention time (min) | MS (m/z) |
|---|---|---|---|---|---|
| 644 | 804 | 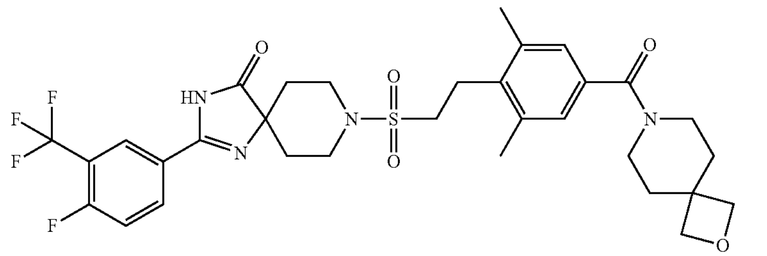 [SMILES: Cc1cc(C(=O)N2CCC3(CC2)COC3)cc(C)c1CCS(=O)(=O)N1CCC2(CC1)N=C(c1ccc(F)c(C(F)(F)F)c1)NC2=O] | LCMS-F-1 | 1.00 | 665 (M + H)+ |
| 506 | 812 | 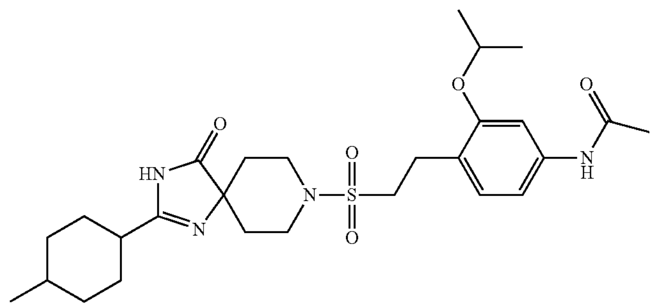 | LCMS-D-1 | 2.20 | 533 (M + H)+ |
| 692 | 817 | 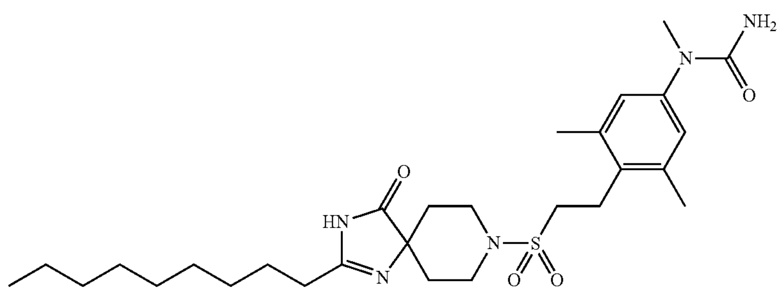 [SMILES: CCCCCCCCCC1=NC2(CCN(S(=O)(=O)CCc3c(C)cc(N(C)C(N)=O)cc3C)CC2)C(=O)N1] | LCMS-A-1 | 2.47 | 548 (M + H)+ |
| 694 | 818 | 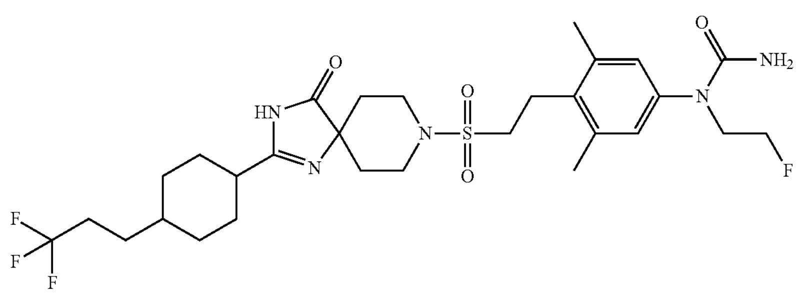 [SMILES: Cc1cc(N(CCF)C(N)=O)cc(C)c1CCS(=O)(=O)N1CCC2(CC1)N=C(C1CCC(CCC(F)(F)F)CC1)NC2=O] | LCMS-D-1 | 2.37 | 632 (M + H)+ |
| 699 | 820 | 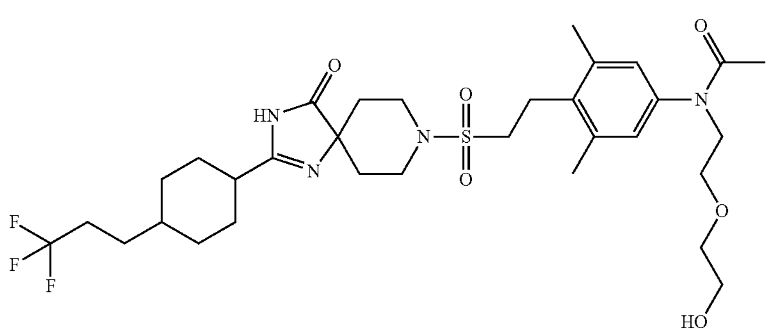 [SMILES: CC(=O)N(CCOCCO)c1cc(C)c(CCS(=O)(=O)N2CCC3(CC2)N=C(C2CCC(CCC(F)(F)F)CC2)NC3=O)c(C)c1] | LCMS-D-1 | 2.25 | 673 (M + H)+ |

TABLE 111-continued

| Starting Compound | Target Compound | Structure | LCMS condition | Retention time (min) | MS (m/z) |
|---|---|---|---|---|---|
| 697 | 821 | 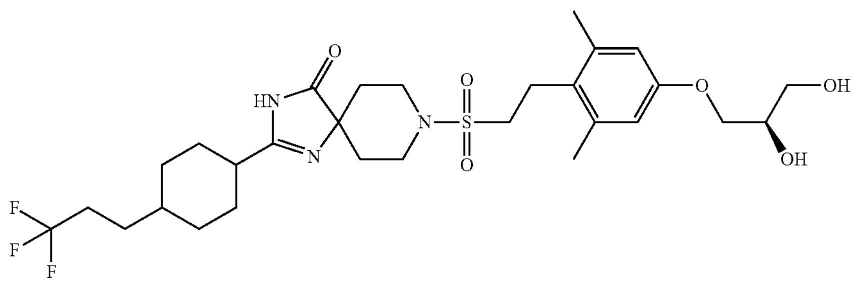 [SMILES: Cc1cc(OC[C@H](O)CO)cc(C)c1CCS(=O)(=O)N1CCC2(CC1)N=C(C1CCC(CCC(F)(F)F)CC1)NC2=O] | LCMS-D-1 | 2.21 | 618 (M + H)+ |
| 704 | 822 | 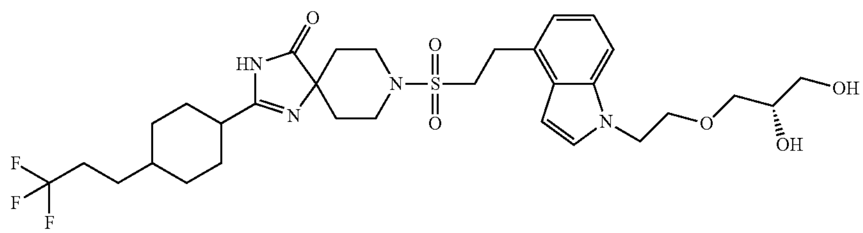 [SMILES: O=C1NC(C2CCC(CCC(F)(F)F)CC2)=NC12CCN(S(=O)(=O)CCc1cccc3c1ccn3CCOC[C@@H](O)CO)CC2] | LCMS-D-1 | 2.28 | 657 (M + H)+ |
| 706 | 823 | 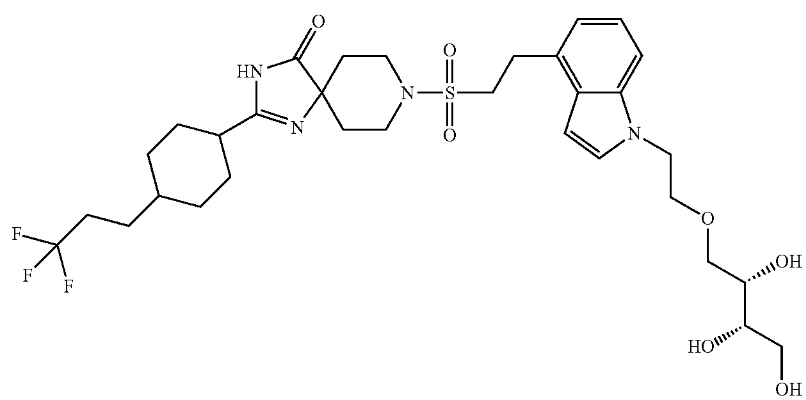 [SMILES: O=C1NC(C2CCC(CCC(F)(F)F)CC2)=NC12CCN(S(=O)(=O)CCc1cccc3c1ccn3CCOC[C@H](O)[C@@H](O)CO)CC2] | LCMS-D-1 | 2.25 | 687 (M + H)+ |
| 707 | 824 | 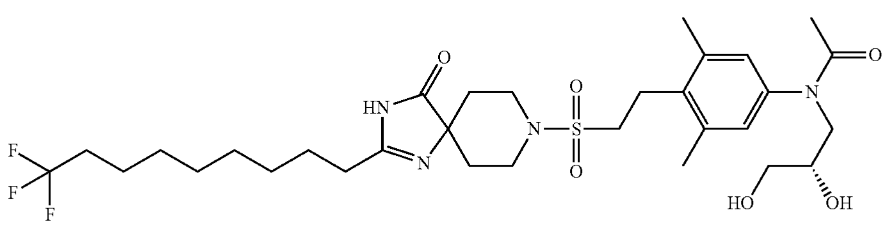 [SMILES: CC(=O)N(C[C@H](O)CO)c1cc(C)c(CCS(=O)(=O)N2CCC3(CC2)N=C(CCCCCCCCC(F)(F)F)NC3=O)c(C)c1] | LCMS-D-1 | 2.40 | 661 (M + H)+ |
| 700 | 825 | 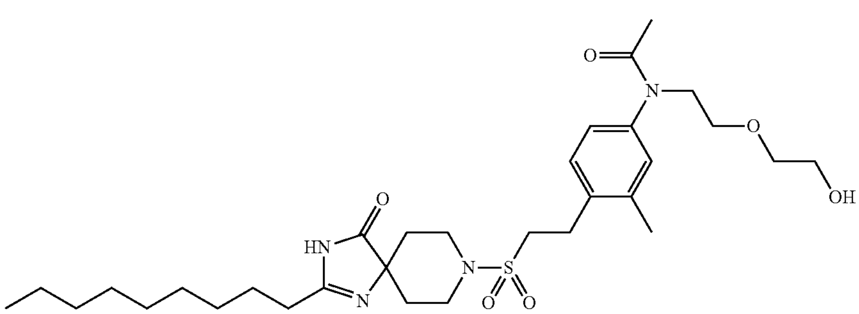 [SMILES: CCCCCCCCCC1=NC2(CCN(S(=O)(=O)CCc3ccc(N(CCOCCO)C(C)=O)cc3C)CC2)C(=O)N1] | LCMS-A-1 | 2.35 | 607 (M + H)+ |

TABLE 111-continued

| Starting Compound | Target Compound | Structure | LCMS condition | Retention time (min) | MS (m/z) |
|---|---|---|---|---|---|
| 724 | 826 | 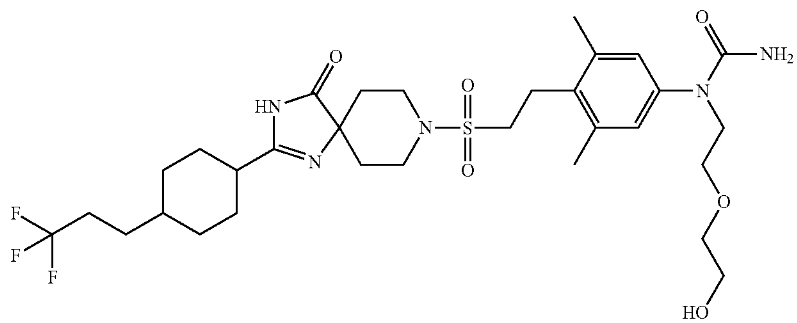 [SMILES: Cc1cc(N(CCOCCO)C(N)=O)cc(C)c1CCS(=O)(=O)N1CCC2(CC1)N=C(C1CCC(CCC(F)(F)F)CC1)NC2=O] | LCMS-D-1 | 2.12 | 674 (M + H)+ |
| 725 | 827 | 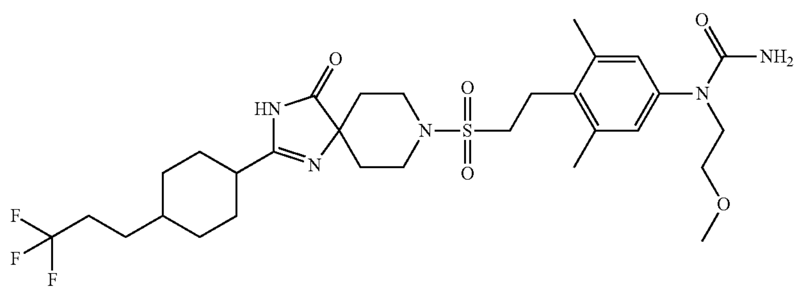 [SMILES: COCCN(C(N)=O)c1cc(C)c(CCS(=O)(=O)N2CCC3(CC2)N=C(C2CCC(CCC(F)(F)F)CC2)NC3=O)c(C)c1] | LCMS-D-1 | 2.37 | 644 (M + H)+ |
| 726 | 828 | 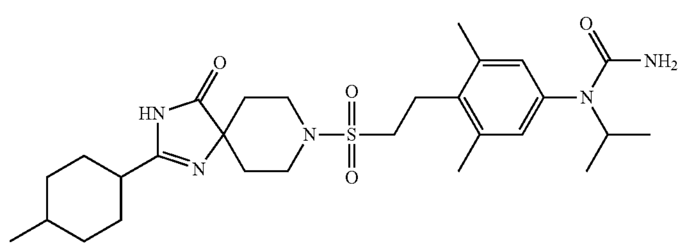 [SMILES: Cc1cc(N(C(N)=O)C(C)C)cc(C)c1CCS(=O)(=O)N1CCC2(CC1)N=C(C1CCC(C)CC1)NC2=O] | LCMS-D-1 | 2.32 | 546 (M + H)+ |
| 727 | 829 | 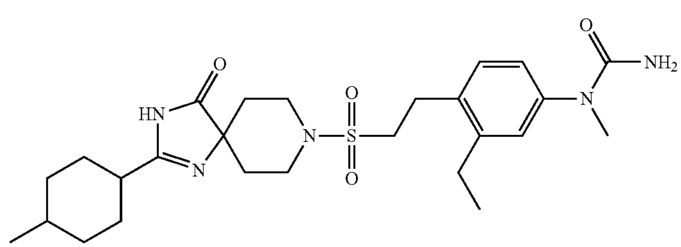 | LCMS-D-1 | 2.68 | 518 (M + H)+ |
| 733 | 830 | 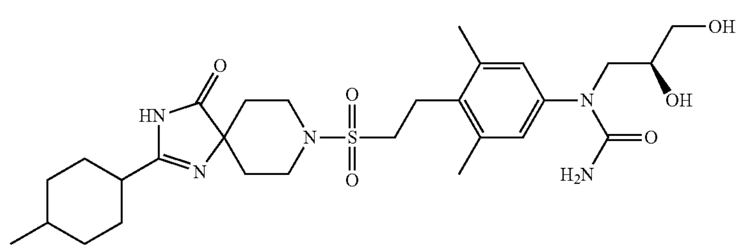 [SMILES: Cc1cc(N(C[C@H](O)CO)C(N)=O)cc(C)c1CCS(=O)(=O)N1CCC2(CC1)N=C(C1CCC(C)CC1)NC2=O] | LCMS-D-1 | 1.52 | 578 (M + H)+ |

TABLE 111-continued

| Starting Compound | Target Compound | Structure | LCMS condition | Retention time (min) | MS (m/z) |
|---|---|---|---|---|---|
| 403 | 831 | 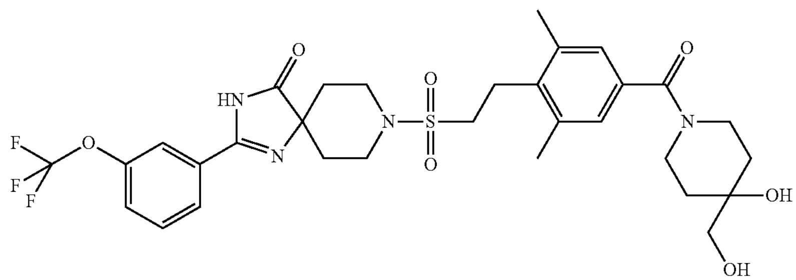 [SMILES: Cc1cc(C(=O)N2CCC(O)(CO)CC2)cc(C)c1CCS(=O)(=O)N1CCC2(CC1)N=C(c1cccc(OC(F)(F)F)c1)NC2=O] | LCMS-F-1 | 0.91 | 667 (M + H)+ |
| 539 | 832 | 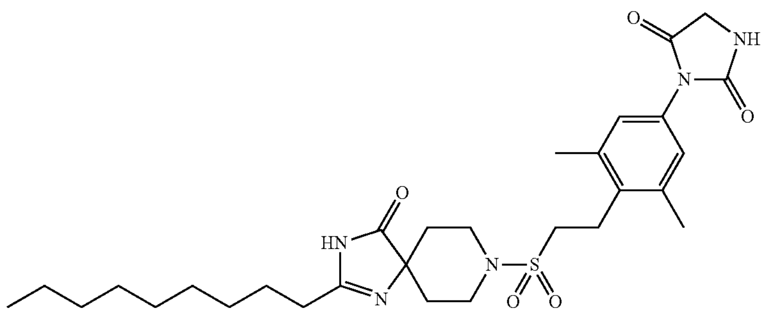 [SMILES: CCCCCCCCCC1=NC2(CCN(S(=O)(=O)CCc3c(C)cc(N4C(=O)CNC4=O)cc3C)CC2)C(=O)N1] | LCMS-A-1 | 2.43 | 574 (M + H)+ |
| 589 | 833 | 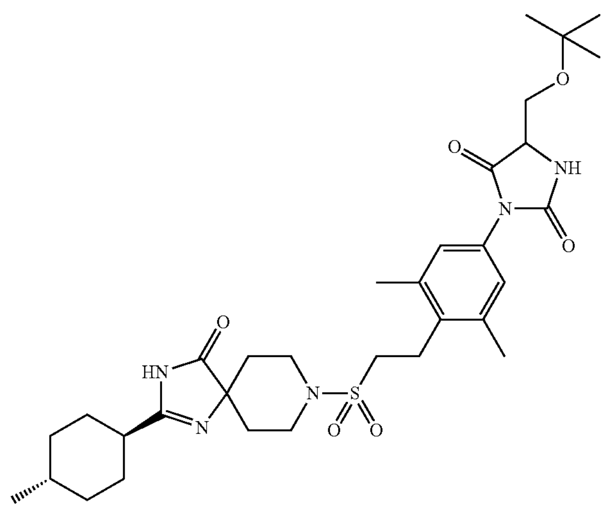 [SMILES: Cc1cc(N2C(=O)NC(COC(C)(C)C)C2=O)cc(C)c1CCS(=O)(=O)N1CCC2(CC1)N=C([C@H]1CC[C@H](C)CC1)NC2=O] | LCMS-B-2 | 4.38 | 631 (M + H)+ |
| 588 | 834 | 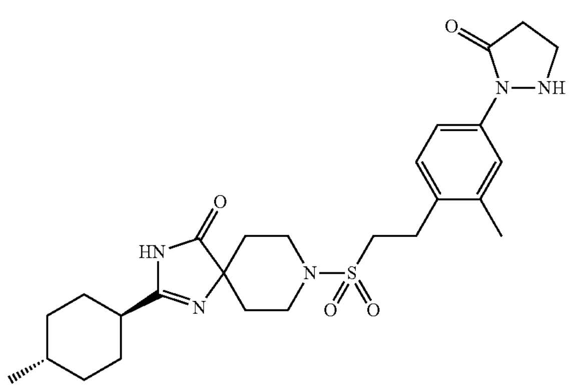 [SMILES: Cc1cc(N2NCCC2=O)ccc1CCS(=O)(=O)N1CCC2(CC1)N=C([C@H]1CC[C@H](C)CC1)NC2=O] | LCMS-C-1 | 2.47 | 517 (M + H)+ |

Example 185

2-Cyclohexyl-8-[2-(1H-indol-7-yl)-ethanesulfonyl]-1,3,8-triaza-spiro[4.5]dec-1-en-4-one (Compound 835)

(Reaction 185-1)

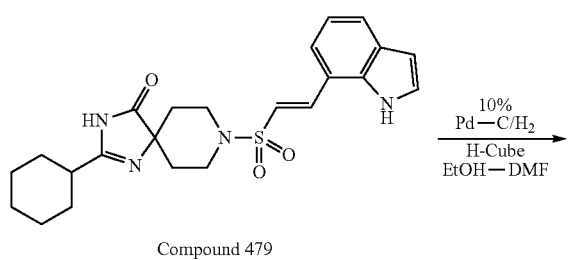

Compound 479

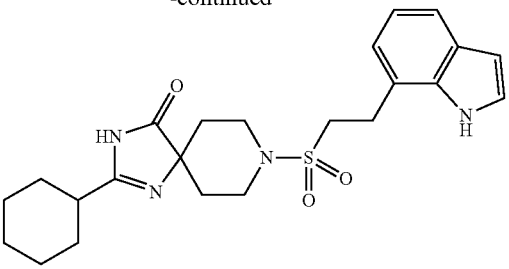

Compound 835

2-Cyclohexyl-8-[2-(1H-indol-7-yl)-ethanesulfonyl]-1,3,8-triaza-spiro[4.5]dec-1-en-4-one (Compound 835) was obtained by operations similar to those in Reaction 42-2 using Compound 479 as a starting material.

MS (ESI) m/z=443 (M+H)+.

The example compounds shown below were obtained by operations similar to those in Example 185 using appropriate solvents (an ethanol-dimethylformamide mixed solution or ethanol) and starting compounds.

Compounds 836 to Compound 879

TABLE 112

| Starting Compound | Target Compound | Structure | LCMS condition | Retention time (min) | MS (m/z) |
|---|---|---|---|---|---|
| 492 | 836 | 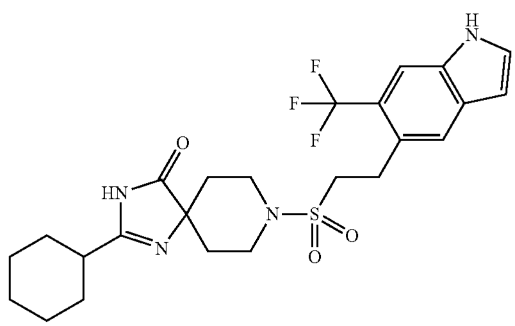 | LCMS-A-1 | 2.25 | 511 (M + H)+ |
| 488 | 837 | 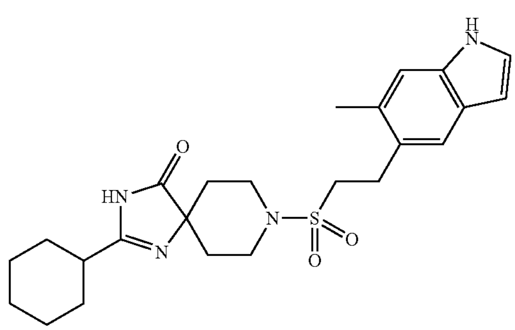 [SMILES: Cc1cc2[nH]ccc2cc1CCS(=O)(=O)N1CCC2(CC1)N=C(C1CCCCC1)NC2=O] | LCMS-A-1 | 2.12 | 457 (M + H)+ |

TABLE 112-continued

| Starting Compound | Target Compound | Structure | LCMS condition | Retention time (min) | MS (m/z) |
|---|---|---|---|---|---|
| 487 | 838 | 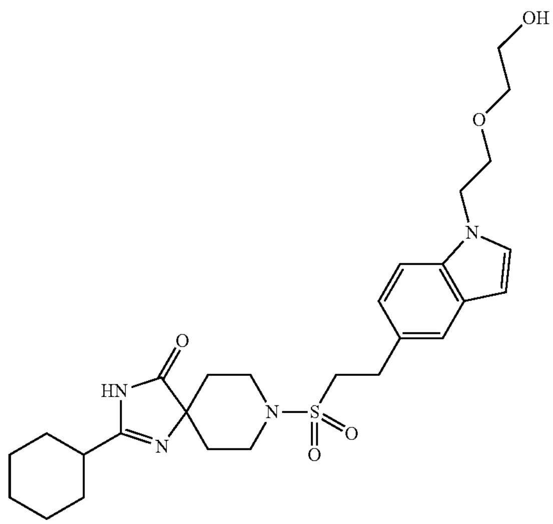 [SMILES: O=C1NC(C2CCCCC2)=NC12CCN(S(=O)(=O)CCc1ccc3c(ccn3CCOCCO)c1)CC2] | LCMS-A-1 | 1.95 | 531 (M + H)+ |
| 499 | 839 | 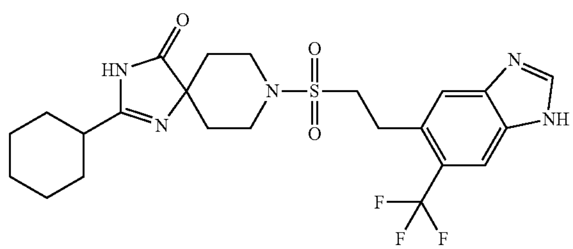 [SMILES: O=C1NC(C2CCCCC2)=NC12CCN(S(=O)(=O)CCc1cc3nc[nH]c3cc1C(F)(F)F)CC2] | LCMS-A-1 | 1.66 | 512 (M + H)+ |
| 524 | 840 | 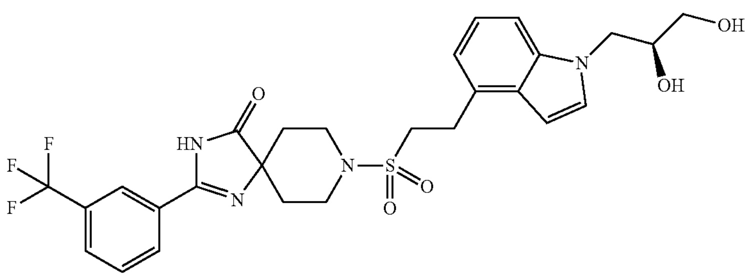 [SMILES: O=C1NC(c2cccc(C(F)(F)F)c2)=NC12CCN(S(=O)(=O)CCc1cccc3c1ccn3C[C@H](O)CO)CC2] | LCMS-A-1 | 2.25 | 579 (M + H)+ |
| 502 | 841 | 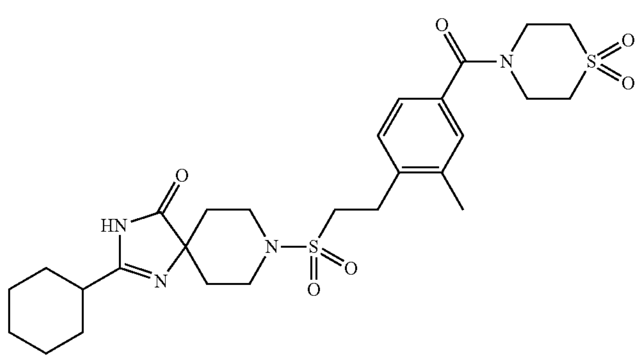 [SMILES: Cc1cc(C(=O)N2CCS(=O)(=O)CC2)ccc1CCS(=O)(=O)N1CCC2(CC1)N=C(C1CCCCC1)NC2=O] | LCMS-C-1 | 2.15 | 579 (M + H)+ |

TABLE 112-continued
| Starting Compound | Target Compound | Structure | LCMS condition | Retention time (min) | MS (m/z) |
|---|---|---|---|---|---|
| 497 | 842 | 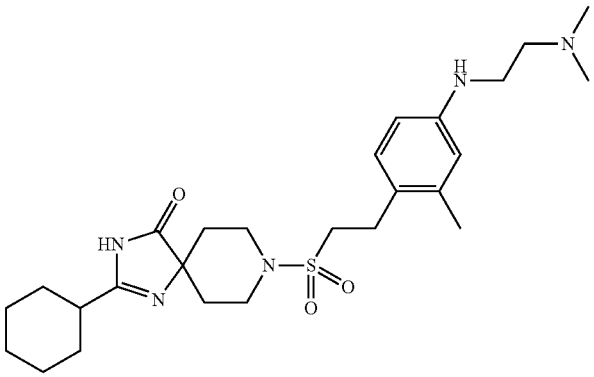 [SMILES: Cc1cc(NCCN(C)C)ccc1CCS(=O)(=O)N1CCC2(CC1)N=C(C1CCCCC1)NC2=O] | LCMS-C-1 | 2.22 | 504 (M + H)+ |
| 527 | 843 | 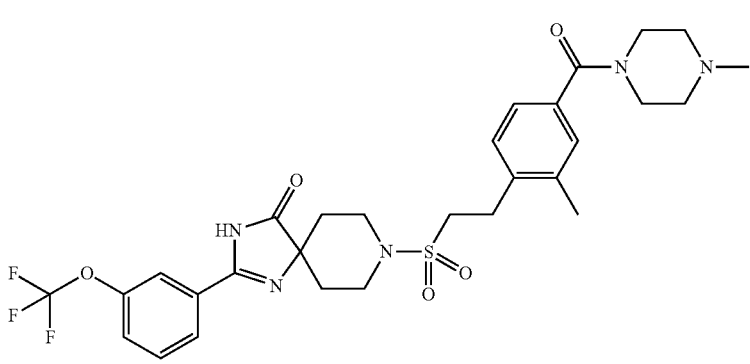 [SMILES: Cc1cc(C(=O)N2CCN(C)CC2)ccc1CCS(=O)(=O)N1CCC2(CC1)N=C(c1cccc(OC(F)(F)F)c1)NC2=O] | LCMS-C-1 | 2.63 | 622 (M + H)+ |
| 844 | 844 | 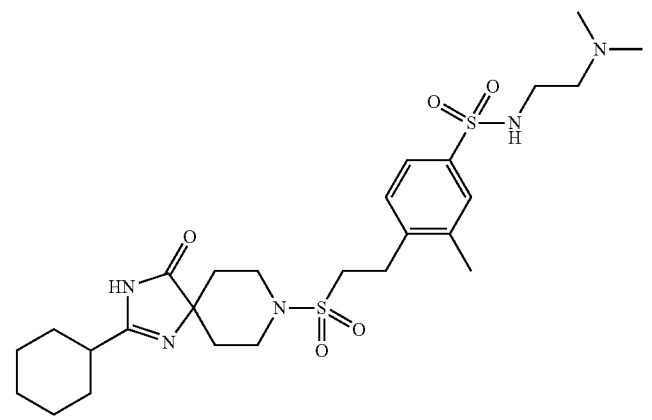 [SMILES: Cc1cc(S(=O)(=O)NCCN(C)C)ccc1CCS(=O)(=O)N1CCC2(CC1)N=C(C1CCCCC1)NC2=O] | LCMS-C-1 | 2.20 | 568 (M + H)+ |
| 528 | 845 | 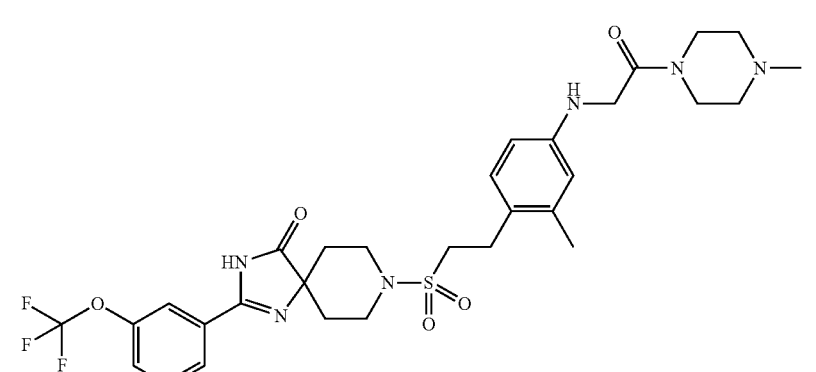 | LCMS-C-1 | 2.58 | 651 (M + H)+ |

TABLE 112-continued

| Starting Compound | Target Compound | Structure | LCMS condition | Retention time (min) | MS (m/z) |
|---|---|---|---|---|---|
| 530 | 846 | 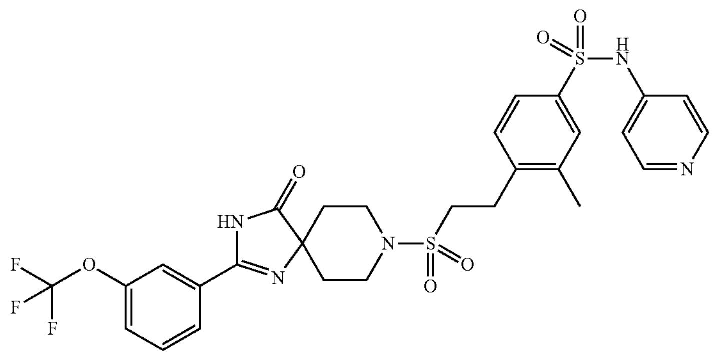 [SMILES: Cc1cc(S(=O)(=O)Nc2ccncc2)ccc1CCS(=O)(=O)N1CCC2(CC1)N=C(c1cccc(OC(F)(F)F)c1)NC2=O] | LCMS-C-1 | 2.37 | 652 (M + H)+ |
| 529 | 847 | 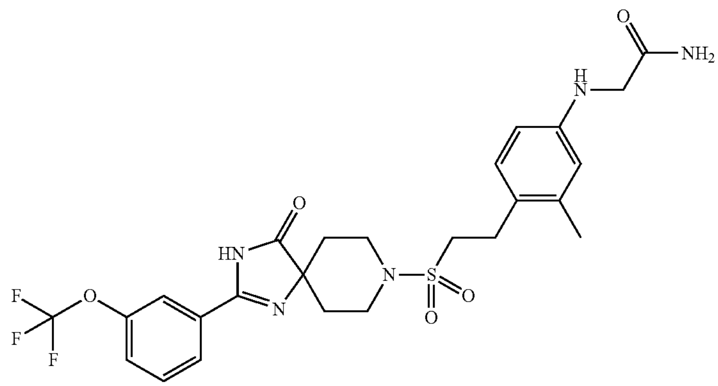 [SMILES: Cc1cc(NCC(N)=O)ccc1CCS(=O)(=O)N1CCC2(CC1)N=C(c1cccc(OC(F)(F)F)c1)NC2=O] | LCMS-C-1 | 2.48 | 568 (M + H)+ |
| 596 | 848 | 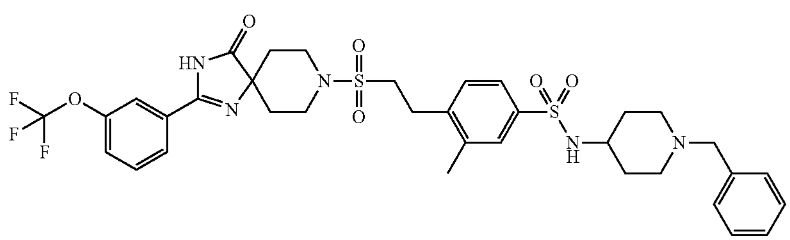 [SMILES: Cc1cc(S(=O)(=O)NC2CCN(Cc3ccccc3)CC2)ccc1CCS(=O)(=O)N1CCC2(CC1)N=C(c1cccc(OC(F)(F)F)c1)NC2=O] | LCMS-C-1 | 2.90 | 748 (M + H)+ |
| 598 | 849 | 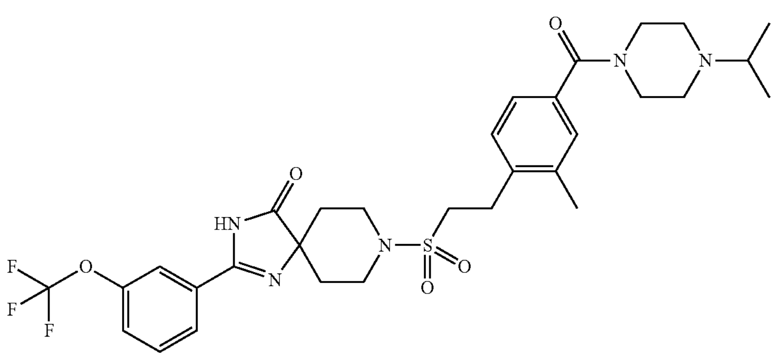 [SMILES: Cc1cc(C(=O)N2CCN(C(C)C)CC2)ccc1CCS(=O)(=O)N1CCC2(CC1)N=C(c1cccc(OC(F)(F)F)c1)NC2=O] | LCMS-C-1 | 2.77 | 650 (M + H)+ |
| 597 | 850 | 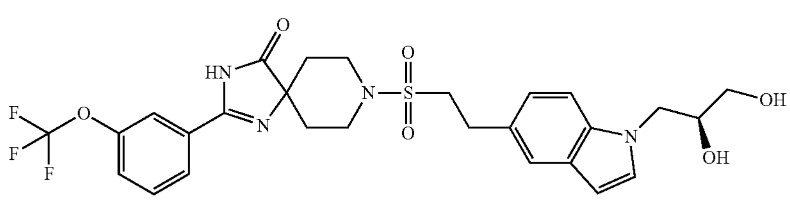 [SMILES: O=C1NC(c2cccc(OC(F)(F)F)c2)=NC12CCN(S(=O)(=O)CCc1ccc3c(ccn3C[C@H](O)CO)c1)CC2] | LCMS-C-1 | 2.58 | 595 (M + H)+ |

TABLE 112-continued

| Starting Compound | Target Compound | Structure | LCMS condition | Retention time (min) | MS (m/z) |
|---|---|---|---|---|---|
| 599 | 851 | 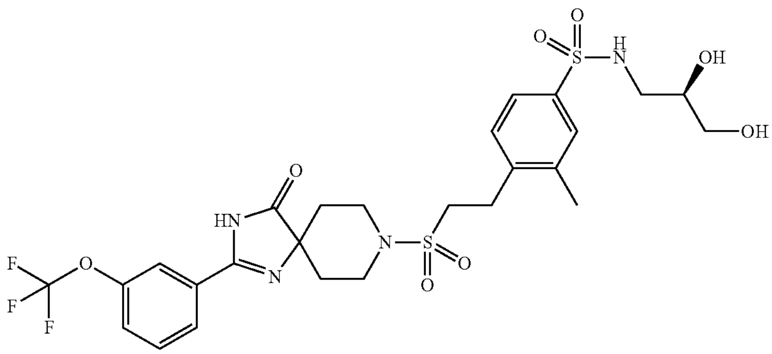 [SMILES: Cc1cc(S(=O)(=O)NC[C@@H](O)CO)ccc1CCS(=O)(=O)N1CCC2(CC1)N=C(c1cccc(OC(F)(F)F)c1)NC2=O] | LCMS-C-1 | 2.42 | 649 (M + H)+ |
| 591 | 852 | 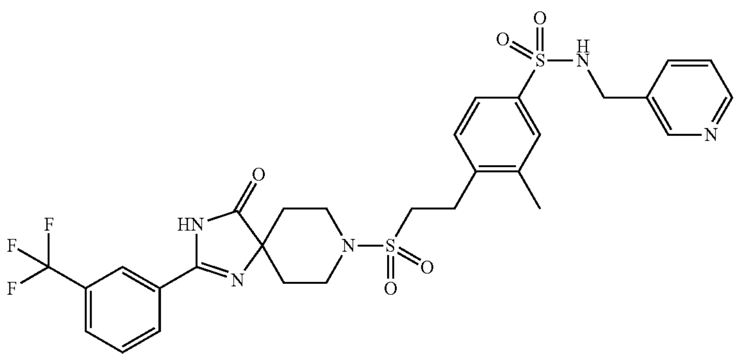 [SMILES: Cc1cc(S(=O)(=O)NCc2cccnc2)ccc1CCS(=O)(=O)N1CCC2(CC1)N=C(c1cccc(C(F)(F)F)c1)NC2=O] | LCMS-C-1 | 2.53 | 650 (M + H)+ |
| 592 | 853 | 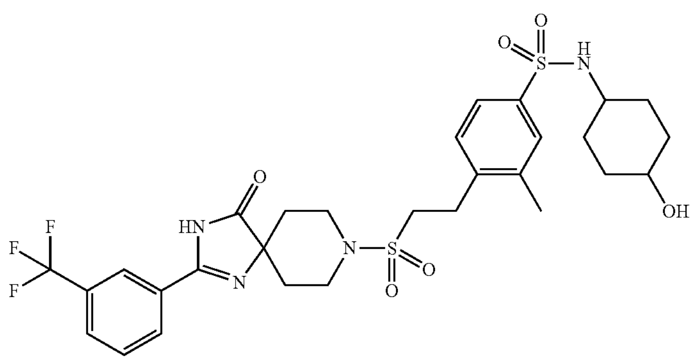 [SMILES: Cc1cc(S(=O)(=O)NC2CCC(O)CC2)ccc1CCS(=O)(=O)N1CCC2(CC1)N=C(c1cccc(C(F)(F)F)c1)NC2=O] | LCMS-C-1 | 2.43 | 657 (M + H)+ |
| 595 | 854 | 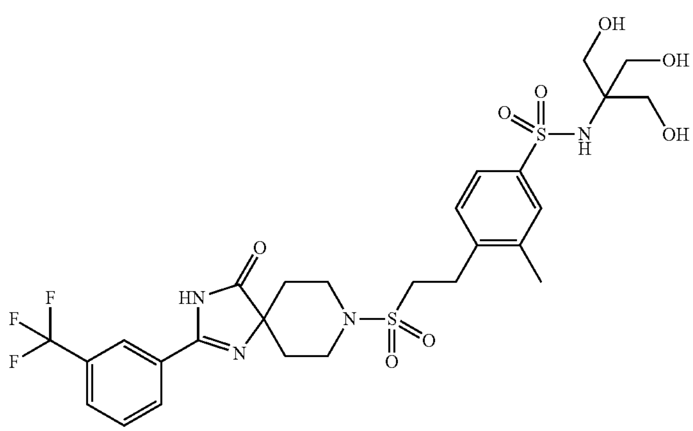 [SMILES: Cc1cc(S(=O)(=O)NC(CO)(CO)CO)ccc1CCS(=O)(=O)N1CCC2(CC1)N=C(c1cccc(C(F)(F)F)c1)NC2=O] | LCMS-C-1 | 2.35 | 663 (M + H)+ |

TABLE 112-continued

| Starting Compound | Target Compound | Structure | LCMS condition | Retention time (min) | MS (m/z) |
|---|---|---|---|---|---|
| 601 | 855 | 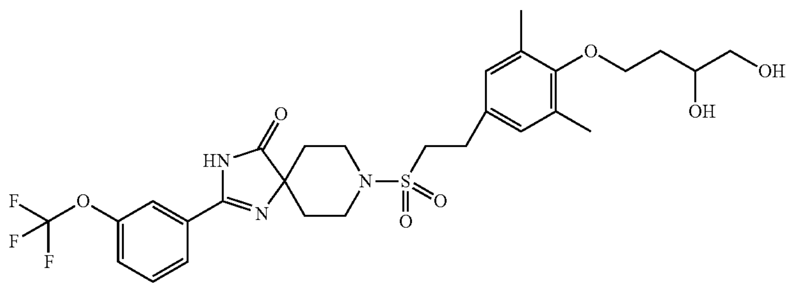 [SMILES: Cc1cc(CCS(=O)(=O)N2CCC3(CC2)N=C(c2cccc(OC(F)(F)F)c2)NC3=O)cc(C)c1OCCC(O)CO] | LCMS-C-1 | 2.68 | 614 (M + H)+ |
| 619 | 856 | 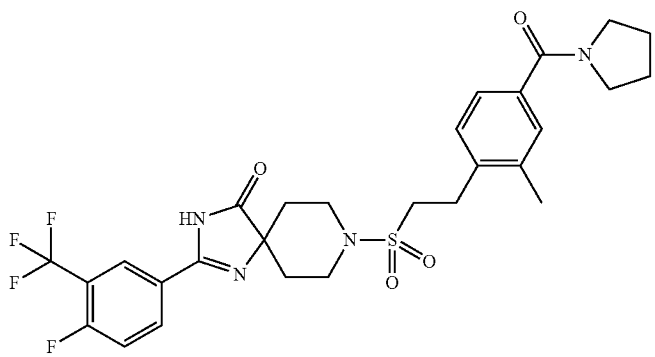 [SMILES: Cc1cc(C(=O)N2CCCC2)ccc1CCS(=O)(=O)N1CCC2(CC1)N=C(c1ccc(F)c(C(F)(F)F)c1)NC2=O] | LCMS-C-1 | 2.72 | 595 (M + H)+ |
| 620 | 857 | 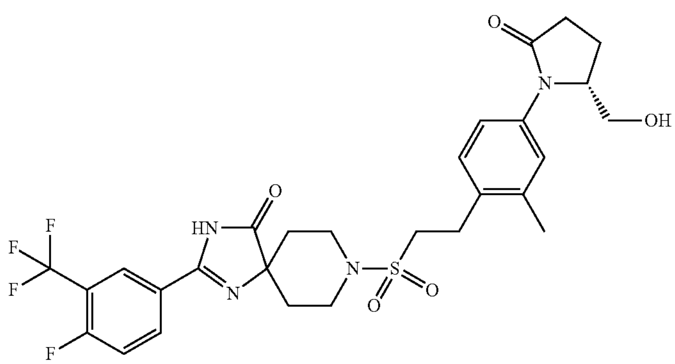 [SMILES: Cc1cc(N2C(=O)CC[C@@H]2CO)ccc1CCS(=O)(=O)N1CCC2(CC1)N=C(c1ccc(F)c(C(F)(F)F)c1)NC2=O] | LCMS-B-1 | 1.95 | 611 (M + H)+ |
| 621 | 858 | 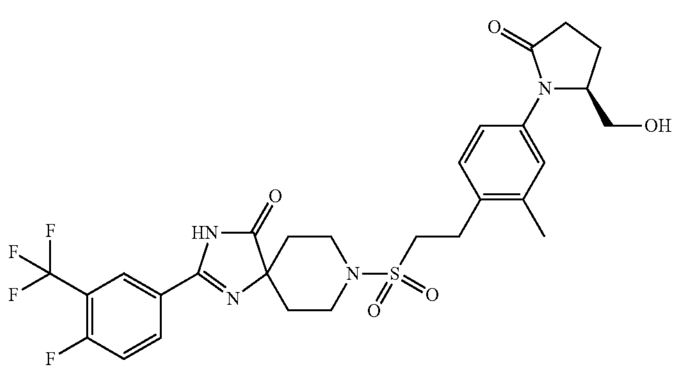 [SMILES: Cc1cc(N2C(=O)CC[C@H]2CO)ccc1CCS(=O)(=O)N1CCC2(CC1)N=C(c1ccc(F)c(C(F)(F)F)c1)NC2=O] | LCMS-C-1 | 2.47 | 611 (M + H)+ |

TABLE 112-continued
| Starting Compound | Target Compound | Structure | LCMS condition | Retention time (min) | MS (m/z) |
|---|---|---|---|---|---|
| 602 | 859 | 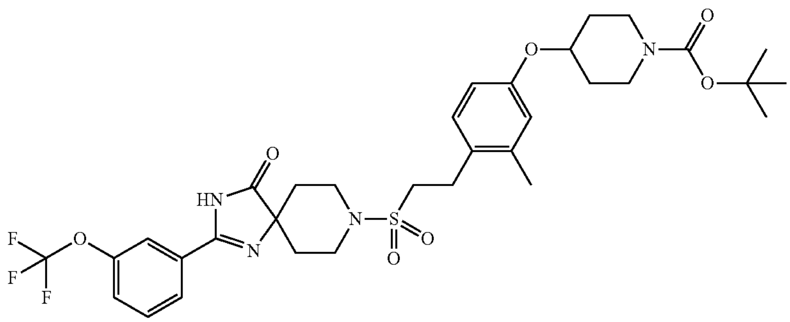 [SMILES: Cc1cc(OC2CCN(C(=O)OC(C)(C)C)CC2)ccc1CCS(=O)(=O)N1CCC2(CC1)N=C(c1cccc(OC(F)(F)F)c1)NC2=O] | LCMS-C-1 | 3.15 | 695 (M + H)+ |
| 600 | 860 | 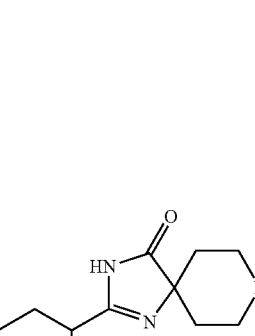 | LCMS-C-1 | 2.58 | 622 (M + H)+ |
| 572 | 861 | 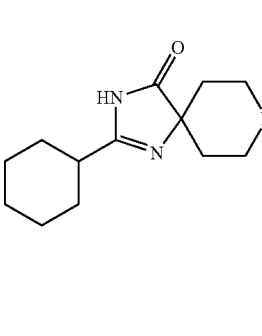 | LCMS-C-1 | 2.47 | 487 (M + H)+ |
| 505 | 862 | 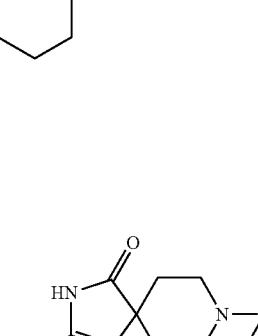 | LCMS-C-1 | 2.45 | 544 (M + H)+ |

TABLE 112-continued

| Starting Compound | Target Compound | Structure | LCMS condition | Retention time (min) | MS (m/z) |
|---|---|---|---|---|---|
| 511 | 863 | 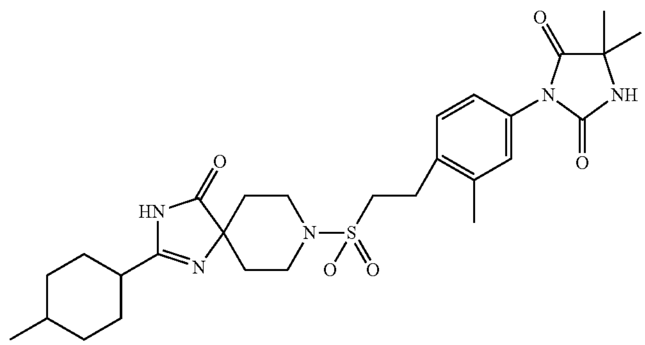 | LCMS-F-1 | 0.93 | 558 (M + H)+ |
| 540 | 864 | 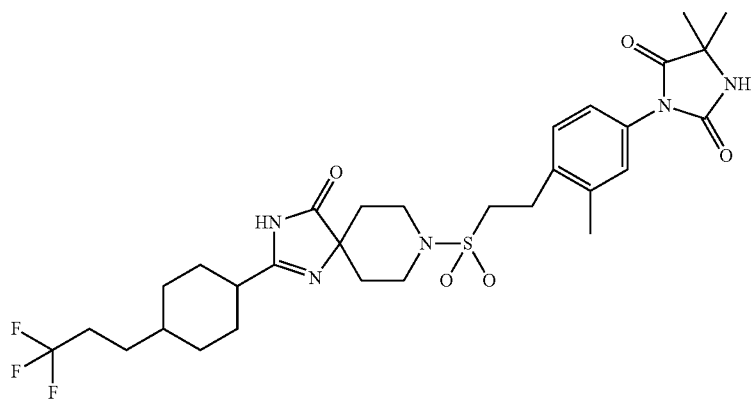 [SMILES: Cc1cc(N2C(=O)NC(C)(C)C2=O)ccc1CCS(O)(O)N1CCC2(CC1)N=C(C1CCC(CCC(F)(F)F)CC1)NC2=O] | LCMS-F-1 | 0.96 | 640 (M + H)+ |
| 513 | 865 | 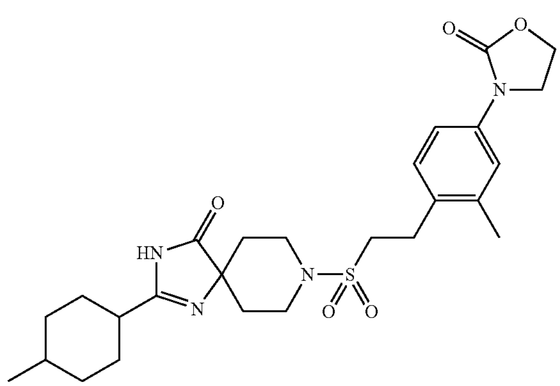 [SMILES: Cc1cc(N2CCOC2=O)ccc1CCS(=O)(=O)N1CCC2(CC1)N=C(C1CCC(C)CC1)NC2=O] | LCMS-C-1 | 2.55 | 517 (M + H)+ |
| 577 | 866 | 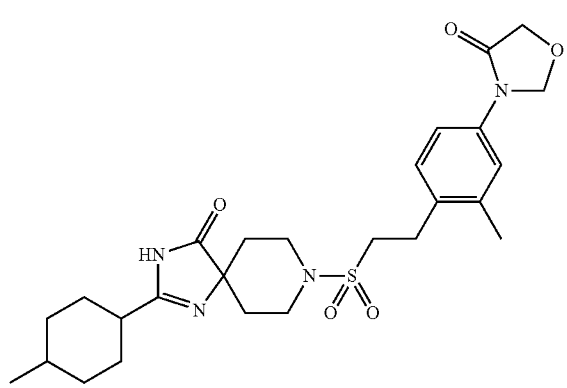 [SMILES: Cc1cc(N2COCC2=O)ccc1CCS(=O)(=O)N1CCC2(CC1)N=C(C1CCC(C)CC1)NC2=O] | LCMS-C-1 | 2.60 | 517 (M + H)+ |

TABLE 112-continued

| Starting Compound | Target Compound | Structure | LCMS condition | Retention time (min) | MS (m/z) |
|---|---|---|---|---|---|
| 541 | 867 | 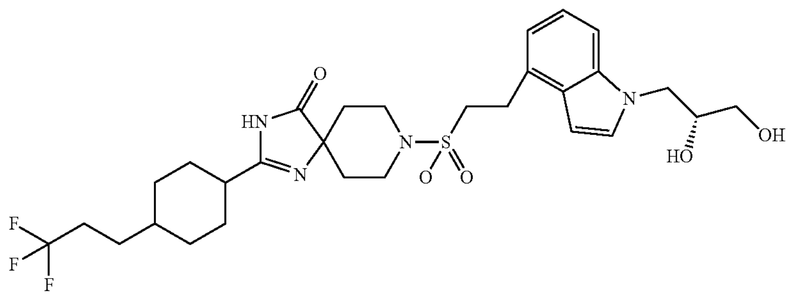 | LCMS-F-1 | 0.96 | 613 (M + H)+ |
| 586 | 868 | 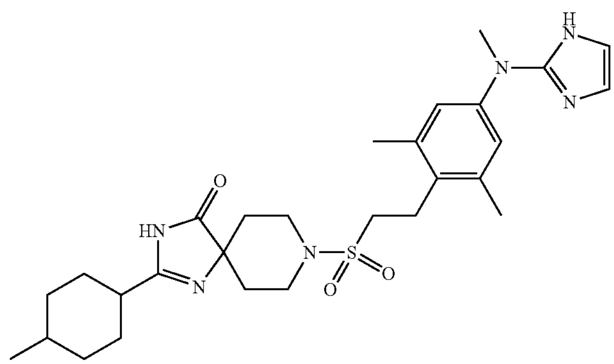 [SMILES: Cc1cc(N(C)c2ncc[nH]2)cc(C)c1CCS(=O)(=O)N1CCC2(CC1)N=C(C1CCC(C)CC1)NC2=O] | LCMS-A-1 | 1.84 | 541 (M + H)+ |
| 507 | 869 | 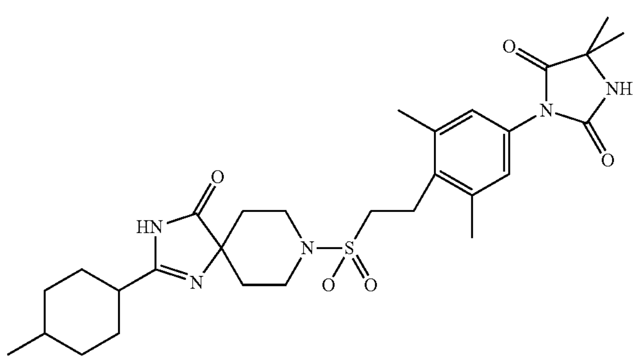 | LCMS-F-1 | 0.96 | 572 (M + H)+ |
| 1185 | 870 | 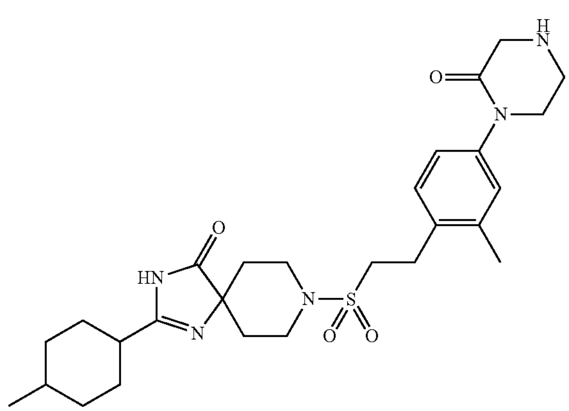 [SMILES: Cc1cc(N2CCNCC2=O)ccc1CCS(=O)(=O)N1CCC2(CC1)N=C(C1CCC(C)CC1)NC2=O] | LCMS-A-1 | 1.65 | 530 (M + H)+ |

TABLE 112-continued

| Starting Compound | Target Compound | Structure | LCMS condition | Retention time (min) | MS (m/z) |
|---|---|---|---|---|---|
| 702 | 872 | 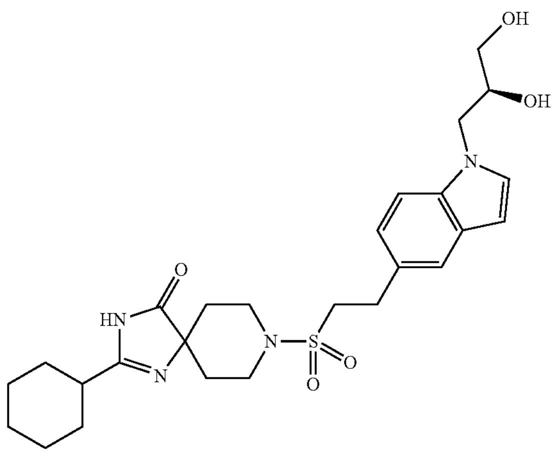 [SMILES: O=C1NC(C2CCCCC2)=NC12CCN(S(=O)(=O)CCc1ccc3c(ccn3C[C@H](O)CO)c1)CC2] | LCMS-C-1 | 2.30 | 517 (M + H)+ |
| 717 | 873 | 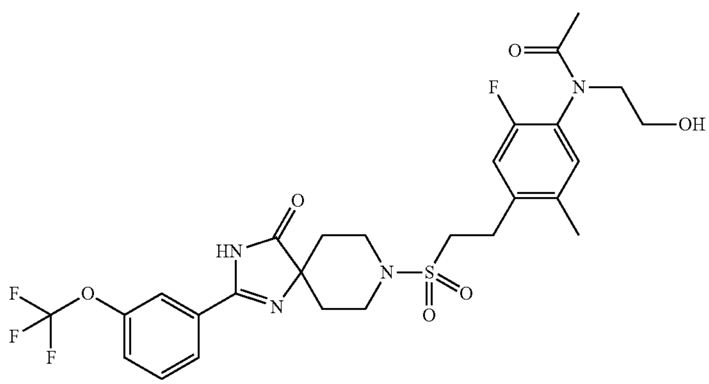 [SMILES: CC(=O)N(CCO)c1cc(C)c(CCS(=O)(=O)N2CCC3(CC2)N=C(c2cccc(OC(F)(F)F)c2)NC3=O)cc1F] | LCMS-B-1 | 2.04 | 615 (M + H)+ |
| 473 | 874 | 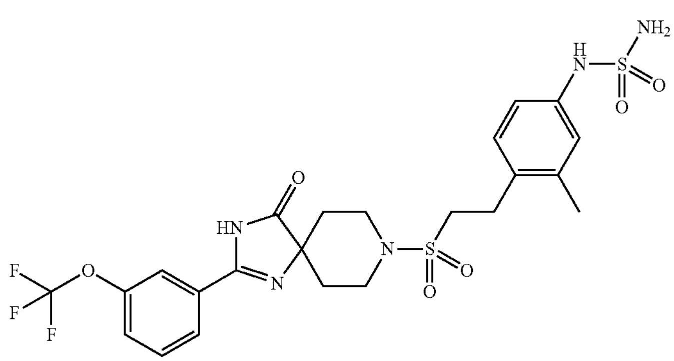 [SMILES: Cc1cc(NS(N)(=O)=O)ccc1CCS(=O)(=O)N1CCC2(CC1)N=C(c1cccc(OC(F)(F)F)c1)NC2=O] | LCMS-C-1 | 2.42 | 590 (M + H)+ |

TABLE 112-continued
| Starting Compound | Target Compound | Structure | LCMS condition | Retention time (min) | MS (m/z) |
|---|---|---|---|---|---|
| 743 | 875 | 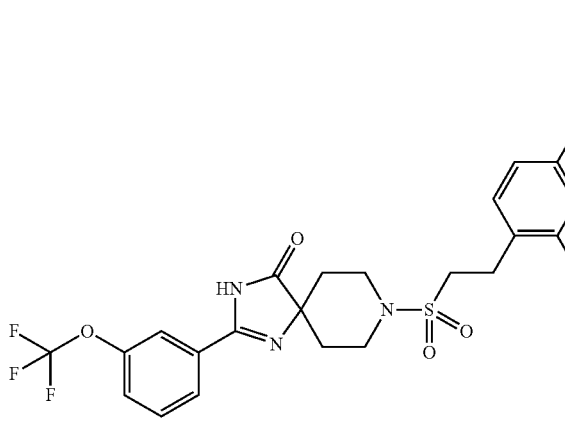 | LCMS-C-1 | 2.43 | 648 (M + H)+ |
| 729 | 876 | 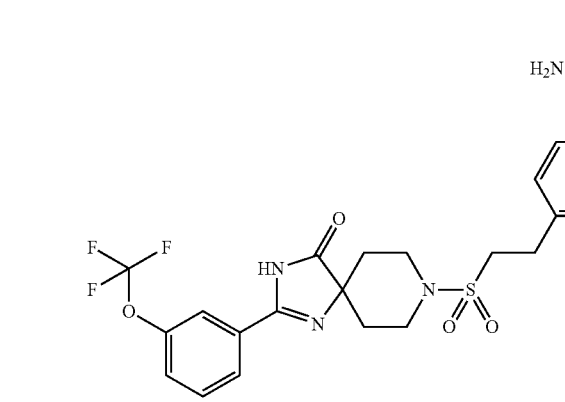 | LCMS-C-1 | 2.20 | 580 (M + H)+ |
| 731 | 877 | 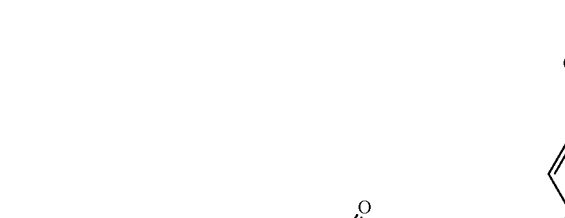 | LCMS-C-1 | 2.70 | 636 (M + H)+ |

TABLE 112-continued
| Starting Compound | Target Compound | Structure | LCMS condition | Retention time (min) | MS (m/z) |
|---|---|---|---|---|---|
| 624 | 878 | 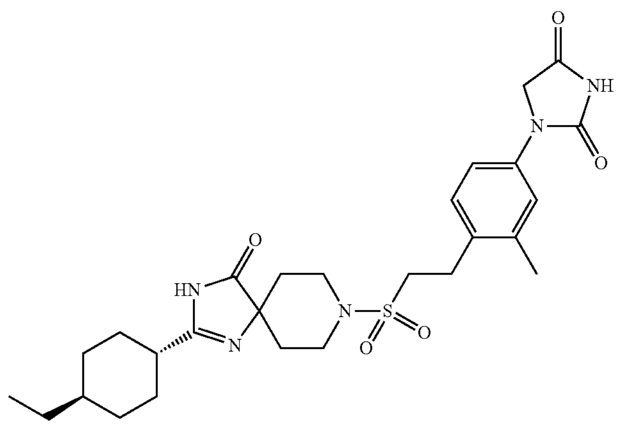 [SMILES: CC[C@H]1CC[C@H](C2=NC3(CCN(S(=O)(=O)CCc4ccc(N5CC(=O)NC5=O)cc4C)CC3)C(=O)N2)CC1] | LCMS-C-1 | 2.65 | 544 (M + H)+ |
| 625 | 879 | 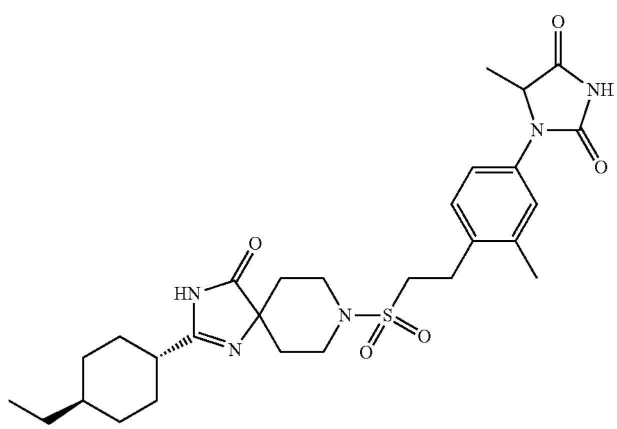 [SMILES: CC[C@H]1CC[C@H](C2=NC3(CCN(S(=O)(=O)CCc4ccc(N5C(=O)NC(=O)C5C)cc4C)CC3)C(=O)N2)CC1] | LCMS-C-1 | 2.68 | 558 (M + H)+ |
Example 186
3-(4-{2-[2-(4-Butyl-cyclohexyl)-4-oxo-1,3,8-triaza-spiro[4.5]dec-1-ene-8-sulfonyl]-ethyl}-3-methyl-phenyl)-imidazolidine-2,4-dione (Compound 880)
(Reaction 186-1)
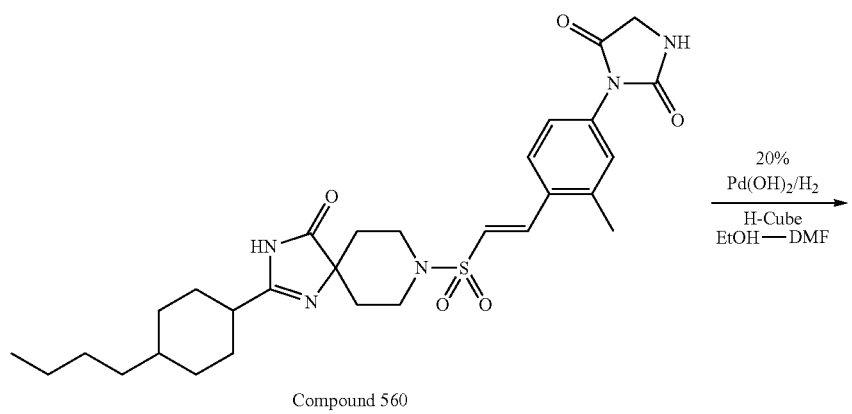
Compound 560

-continued

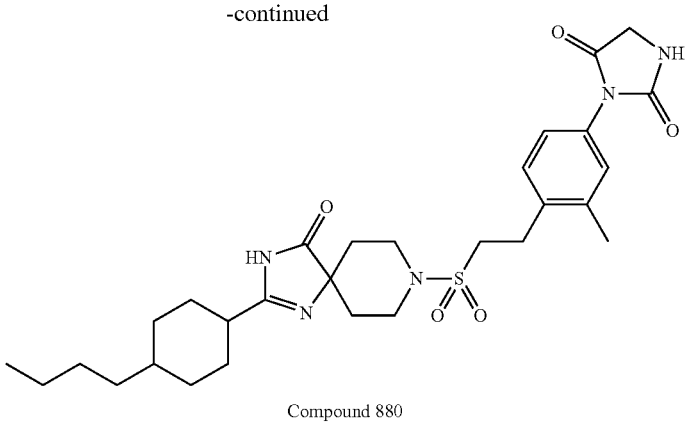

Compound 880

3-(4-{2-[2-(4-Butyl-cyclohexyl)-4-oxo-1,3,8-triaza-spiro[4.5]dec-1-ene-8-sulfonyl]-ethyl}-3-methyl-phenyl)-imidazolidine-2,4-dione (Compound 880) was obtained by operations similar to those in Reaction 91-1 using Compound 560 as a starting material.

MS (ESI) m/z=572 (M+H)+.

The example compounds shown below were obtained by operations similar to those in Example 186 using appropriate solvents (an ethanol-dimethylformamide mixed solution or ethanol) and starting compounds.

Compounds 881 to Compound 887

TABLE 113

| Starting Compound | Target Compound | Structure | LCMS condition | Retention time (min) | MS (m/z) |
|---|---|---|---|---|---|
| 504 | 881 | 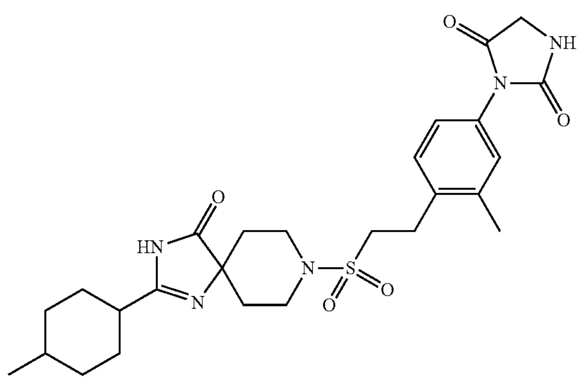 [SMILES: Cc1cc(N2C(=O)CNC2=O)ccc1CCS(=O)(=O)N1CCC2(CC1)N=C(C1CCC(C)CC1)NC2=O] | LCMS-C-1 | 2.33 | 530 (M + H)+ |
| 563 | 882 | 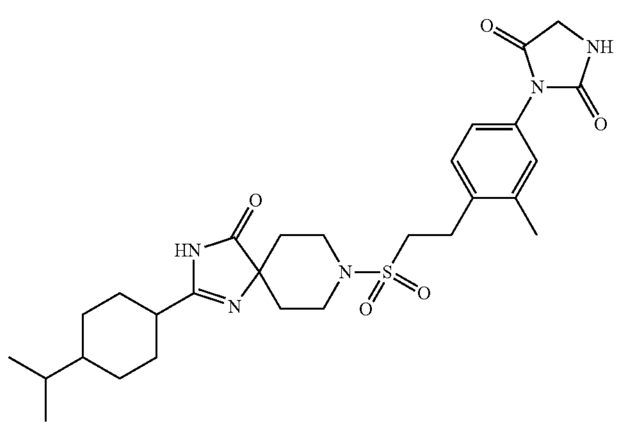 [SMILES: Cc1cc(N2C(=O)CNC2=O)ccc1CCS(=O)(=O)N1CCC2(CC1)N=C(C1CCC(C(C)C)CC1)NC2=O] | LCMS-C-1 | 2.67 | 558 (M + H)+ |

TABLE 113-continued
| Starting Compound | Target Compound | Structure | LCMS condition | Retention time (min) | MS (m/z) |
|---|---|---|---|---|---|
| 575 | 883 | 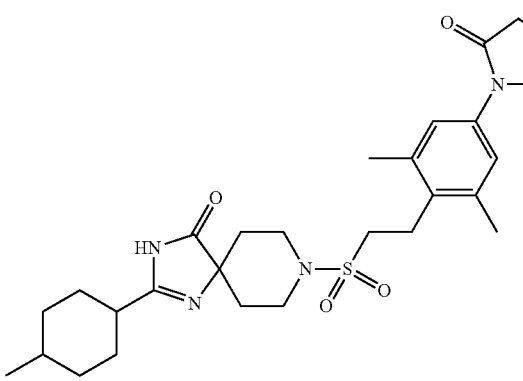 | LCMS-C-1 | 2.43 | 544 (M + H)+ |
| 564 | 884 | 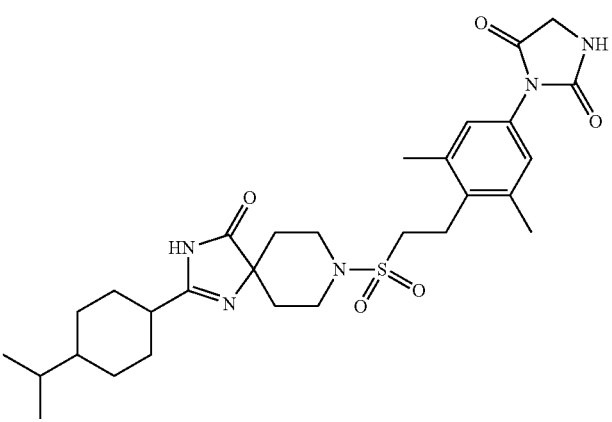 [SMILES: Cc1cc(N2C(=O)CNC2=O)cc(C)c1CCS(=O)(=O)N1CCC2(CC1)N=C(C1CCC(C(C)C)CC1)NC2=O] | LCMS-C-1 | 2.70 | 572 (M + H)+ |
| 508 | 885 | 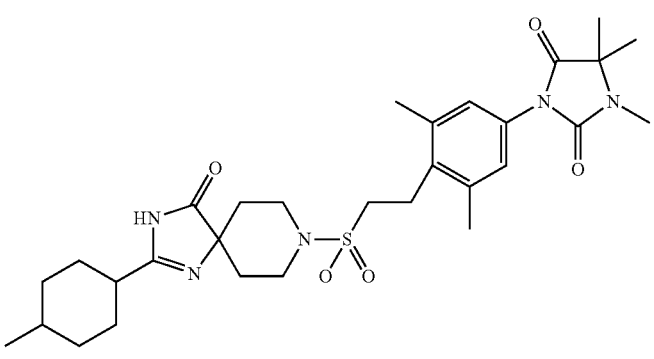 | LCMS-F-1 | 0.97 | 586 (M + H)+ |
| 688 | 886 | 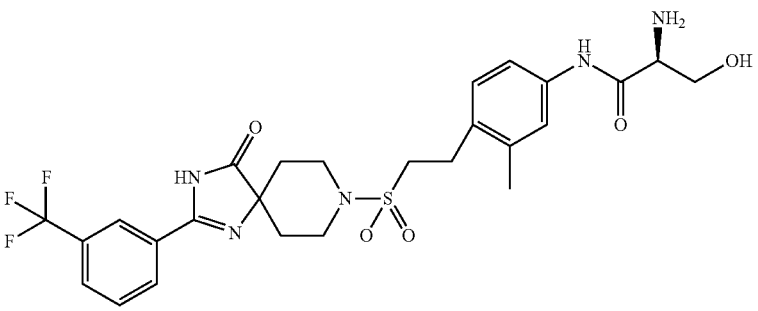 | LCMS-F-1 | 0.86 | 582 (M + H)+ |

TABLE 113-continued

| Starting Compound | Target Compound | Structure | LCMS condition | Retention time (min) | MS (m/z) |
|---|---|---|---|---|---|
| 626 | 887 | 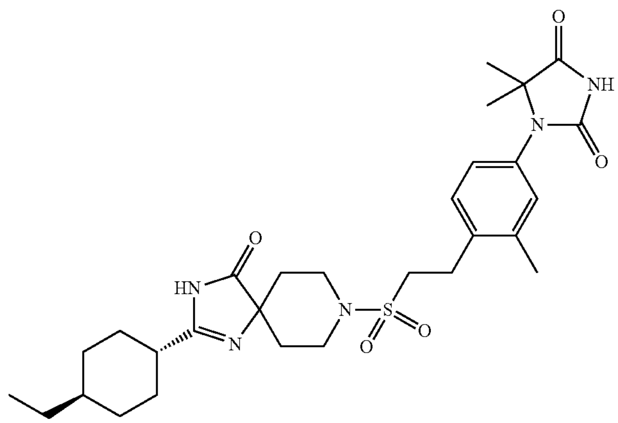 [SMILES: CC[C@H]1CC[C@H](C2=NC3(CCN(S(=O)(=O)CCc4ccc(N5C(=O)NC(=O)C5(C)C)cc4C)CC3)C(=O)N2)CC1] | LCMS-C-1 | 2.70 | 572 (M + H)+ |

Example 187

3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide (Compound 888)

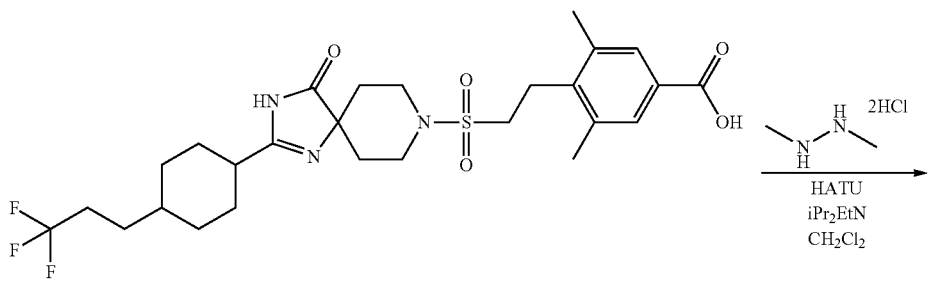

Compound 768

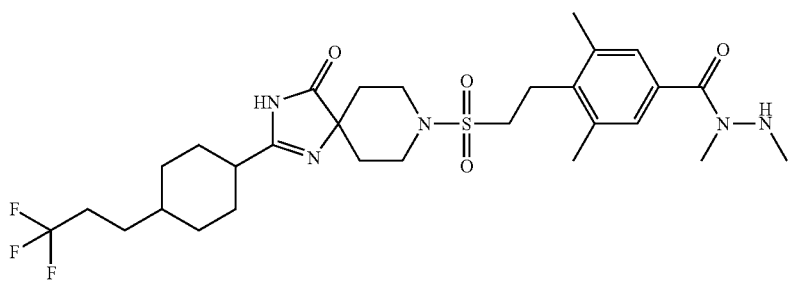

Compound 888

3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzoic acid N,N'-dimethyl-hydrazide (Compound 888) was obtained by operations similar to those in Reaction 10-14 using Compound 768 as a starting material and using dichloromethane as a solvent.

MS (ESI) m/z=614 (M+H)+.

Example 188

8-{2-[2-Methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride (Compound 889)

(Reaction 188-1)

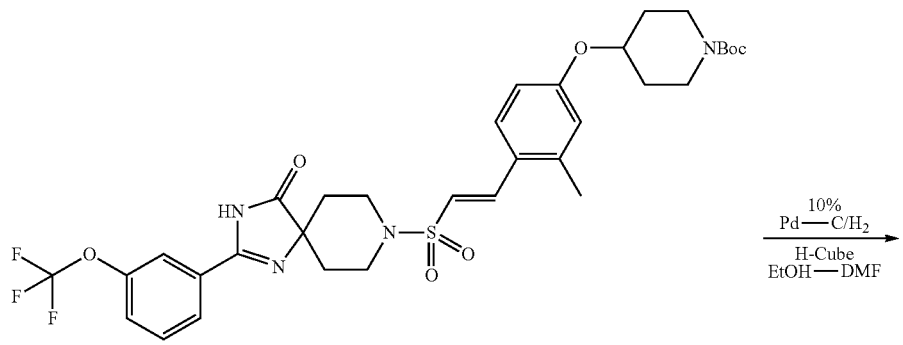

Compound 602

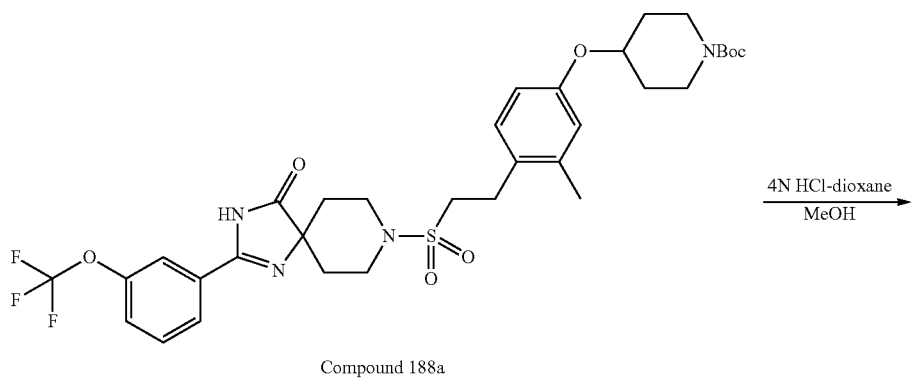

Compound 188a

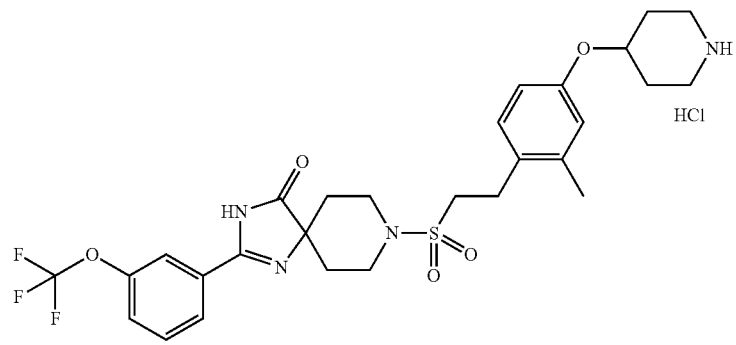

Compound 889

8-{2-[2-Methyl-4-(piperidin-4-yloxy)-phenyl]-ethanesulfonyl}-2-(3-trifluoromethoxy-phenyl)-1,3,8-triaza-spiro[4.5]dec-1-en-4-one hydrochloride (Compound 889) was obtained by operations similar to those in Reaction 42-2 and Reaction 5-3 using Compound 602 as a starting material.

MS (ESI) m/z=595 (M+H)+.

Example 189

4-{2-[2-(4,4-Difluoro-cyclohexyl)-4-oxo-1,3,8-tri-aza-spiro[4.5]dec-1-ene-8-sulfonyl]-ethyl}-3,N,N-trimethyl-benzamide (Compound 890)

(Reaction 189-1)

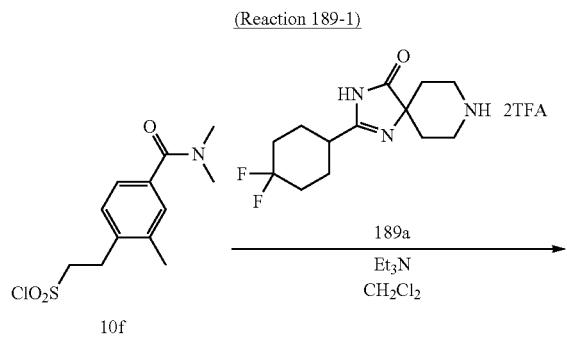

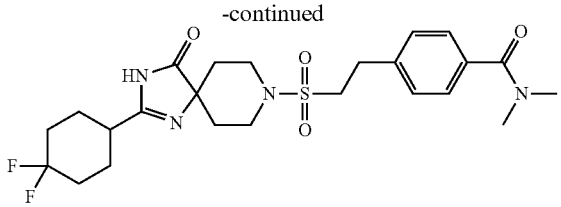

Compound 890

4-{2-[2-(4,4-Difluoro-cyclohexyl)-4-oxo-1,3,8-triaza-spiro[4.5]dec-1-ene-8-sulfonyl]-ethyl}-3,N,N-trimethyl-benzamide was synthesized by operations similar to those in Reaction 5-4 using appropriate reagents and starting material.

MS (ESI) m/z=523 (M−H)−.

The example compounds shown below were synthesized by operations similar to those in Reaction 189-1 using appropriate reagents and starting materials.

Compounds 891 to 901

TABLE 114

| Compound | Structure | LCMS condition | Retention time (min) | MS (m/z) |
|---|---|---|---|---|
| 891 | 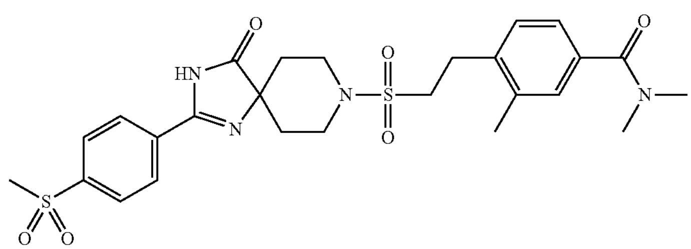 | LCMS-C-1 | 2.07 | 561 (M + H)+ |
| 892 | 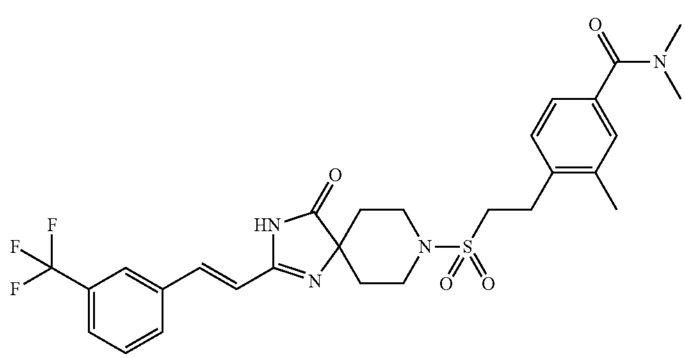 [SMILES: Cc1cc(C(=O)N(C)C)ccc1CCS(=O)(=O)N1CCC2(CC1)N=C(/C=C/c1cccc(C(F)(F)F)c1)NC2=O] | LCMS-A-1 | 2.28 | 577 (M + H)+ |
| 893 | 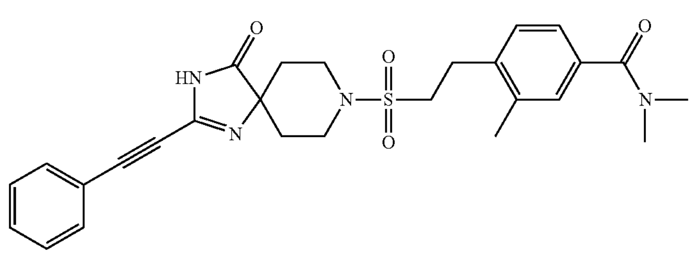 [SMILES: Cc1cc(C(=O)N(C)C)ccc1CCS(=O)(=O)N1CCC2(CC1)N=C(C#Cc1ccccc1)NC2=O] | LCMS-C-1 | 2.42 | 507 (M + H)+ |

TABLE 114-continued

| Compound | Structure | LCMS condition | Retention time (min) | MS (m/z) |
|---|---|---|---|---|
| 894 | 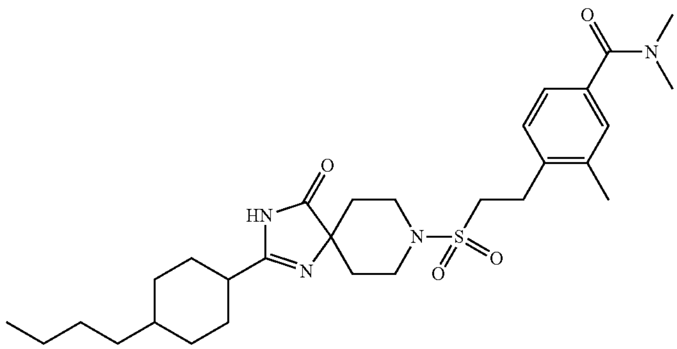 [SMILES: CCCCC1CCC(C2=NC3(CCN(S(=O)(=O)CCc4ccc(C(=O)N(C)C)cc4C)CC3)C(=O)N2)CC1] | LCMS-C-1 | 2.93 | 545 (M + H)+ |
| 895 | 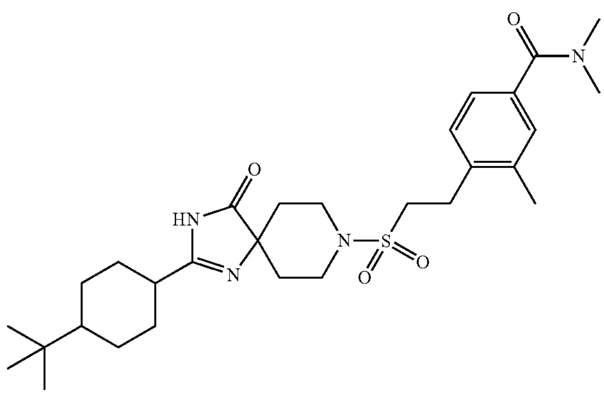 [SMILES: Cc1cc(C(=O)N(C)C)ccc1CCS(=O)(=O)N1CCC2(CC1)N=C(C1CCC(C(C)(C)C)CC1)NC2=O] | LCMS-C-1 | 2.85 | 545 (M + H)+ |
| 896 | 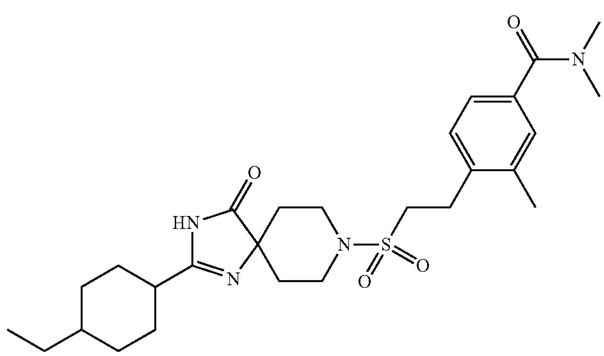 [SMILES: CCC1CCC(C2=NC3(CCN(S(=O)(=O)CCc4ccc(C(=O)N(C)C)cc4C)CC3)C(=O)N2)CC1] | LCMS-C-1 | 2.63 | 517 (M + H)+ |
| 897 | 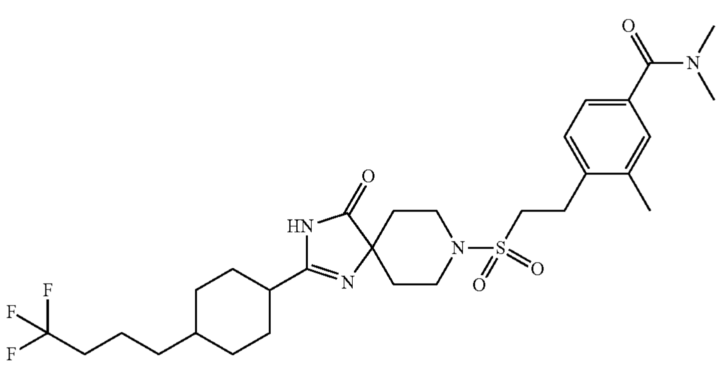 [SMILES: Cc1cc(C(=O)N(C)C)ccc1CCS(=O)(=O)N1CCC2(CC1)N=C(C1CCC(CCCC(F)(F)F)CC1)NC2=O] | LCMS-B-2 | 4.91 | 599 (M + H)+ |

TABLE 114-continued

| Compound | Structure | LCMS condition | Retention time (min) | MS (m/z) |
|---|---|---|---|---|
| 898 | 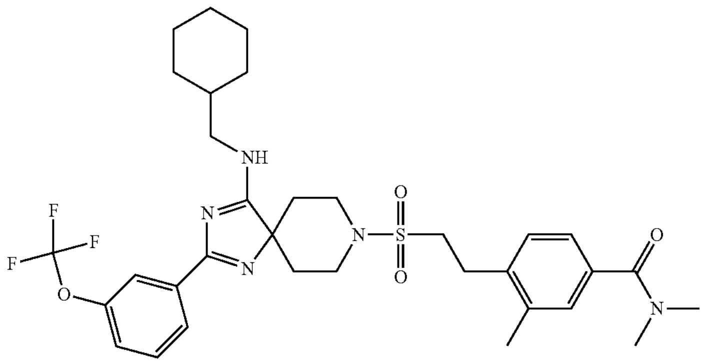 [SMILES: Cc1cc(C(=O)N(C)C)ccc1CCS(=O)(=O)N1CCC2(CC1)N=C(c1cccc(OC(F)(F)F)c1)N=C2NCC1CCCCC1] | LCMS-C-2 | 2.88 | 660 (M − H)− |
| 899 | 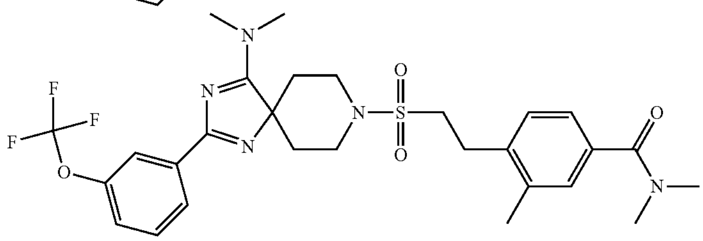 | LCMS-A-1 | 2.24 | 594 (M + H)+ |
| 900 | 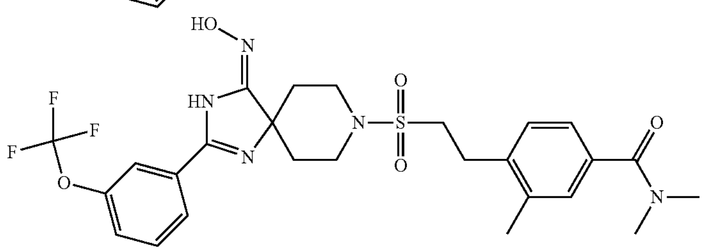 | LCMS-C-2 | 1.93 | 582 (M + H)+ |
| 901 | 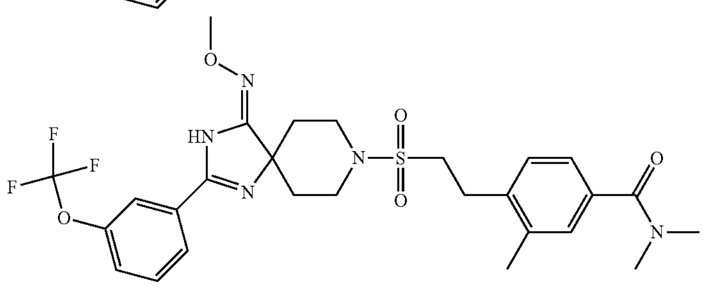 | LCMS-C-2 | 2.33 | 594 (M − H)− |

The spiroamine reagents used in the synthesis of Compounds 890, 891, 895 and 897 and shown below were synthesized by operations similar to those in Reaction 10-14, Reaction 1-4 and Reaction 4-1 using appropriate reagents and Compound 5a as a starting material.

TABLE 115

| Target Compound | Spiroamine reagent | Spiroamine reagent MS (m/z) |
|---|---|---|
| 890 | | 272 (M + H)+ |

TABLE 115-continued

| Target Compound | Spiroamine reagent | Spiroamine reagent MS (m/z) |
|---|---|---|
| 891 | 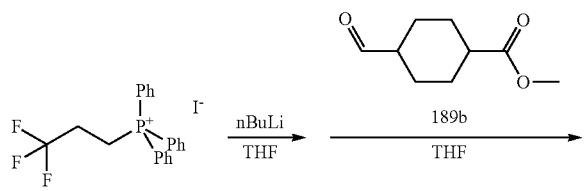 2TFA | 308 (M + H)+ |
| 895 | (structure shown) 2TFA | 292 (M + H)+ |
| 897 | (structure shown) 2TFA | 346 (M + H)+ |

The carboxylic acid necessary for the synthesis of the spiroamine reagent used for Compound 897 (4-(4,4,4-trifluoro-but-1-enyl)-cyclohexanecarboxylic acid methyl ester) was synthesized by the method shown below.

(Reaction 189-2)

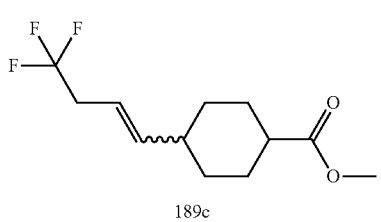

A 1.6 M solution of n-butyllithium in hexane (2.5 mL) was added dropwise to a suspension of triphenyl-(3,3,3-trifluoro-propyl)-phosphonium iodide (1.90 g, 3.91 mmol) in tetrahydrofuran (14 mL) at 0° C. The mixture was stirred at 0° C. for 35 minutes, and a solution of 4-formyl-cyclohexanecarboxylic acid methyl ester (605 mg, 3.55 mmol) in tetrahydrofuran (8.0 mL) was then added dropwise to the reaction solution at −78° C. The mixture was stirred for 45 minutes, and a saturated aqueous ammonium chloride solution was then added, followed by extraction with tert-butyl methyl ether. The organic layer was washed with water and a saturated aqueous sodium chloride solution and washed with sodium sulfate. After concentration, the residue was purified by silica gel column chromatography to give 4-(4,4,4-trifluoro-but-1-enyl)-cyclohexanecarboxylic acid methyl ester (657 mg, 67%) as a colorless oily substance and geometric isomer mixture.

$^1$H-NMR (CDCl$_3$) δ 5.69 (1.0H, t, J=10.4 Hz), 5.51 (0.2H, dt, J=13.7, 2.9 Hz), 5.32 (1.2H, tt, J=9.2, 3.3 Hz), 3.69 (2.8H, dd, J=3.0, 2.6 Hz), 3.67 (0.6H, d, J=0.6 Hz), 2.90-2.78 (2.5H, m), 2.59-2.54 (1.0H, m), 2.40-2.31 (1.0H, m), 2.25-2.20 (0.5H, m), 2.06-1.98 (2.6H, m), 1.75-1.13 (8.0H, m).

(Reaction 189-3)

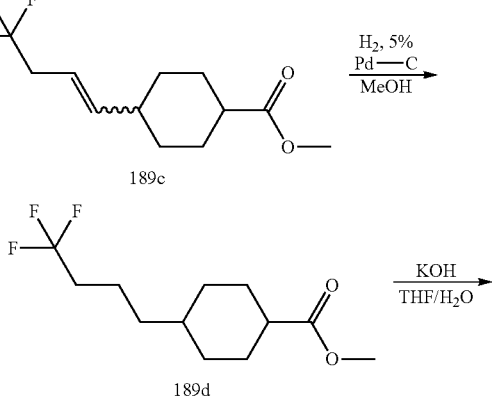

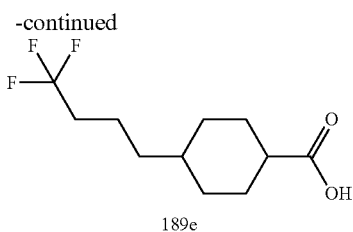

189e 4-(4,4,4-Trifluorobutyl)-cyclohexanecarboxylic acid was synthesized by operations similar to those in Reaction 18-2 and Reaction 95-18 (using potassium hydroxide as a base) using appropriate reagents and starting material. This was used as such in the next reaction.

The spiroamine reagent used in the synthesis of Compound 892 (2-[(E)-2-(3-trifluoromethyl-phenyl)-vinyl]-1,3,8-triaza-spiro[4.5]dec-1-en-4-one dihydrochloride) was synthesized by the method shown below.

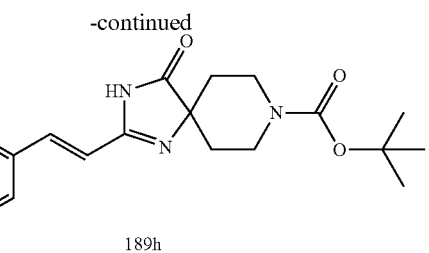

189h

A 6 N aqueous sodium hydroxide solution was added to a solution of 4-carbamoyl-4-[(E)-3-(3-trifluoromethyl-phenyl)-acryloylamino]-piperidine-1-carboxylic acid tert-butyl ester (961 mg, 2.27 mmol) in ethanol (20 ml), and the mixture was stirred at room temperature for 22 hours. The reaction solution was quenched with saturated ammonium chloride and then extracted with ethyl acetate. The organic layer was sequentially washed with water and saturated brine, and then dried over anhydrous magnesium sulfate and concentrated under reduced pressure. The resulting residue was purified by silica gel column chromatography to give 4-oxo-2-[(E)-2-(3-trifluoromethyl-phenyl)-vinyl]-1,3,8-triaza-spiro[4.5]dec-1-ene-8-carboxylic acid tert-butyl ester (706 mg, 73%).

MS (ESI) m/z=422 (M–H)–.

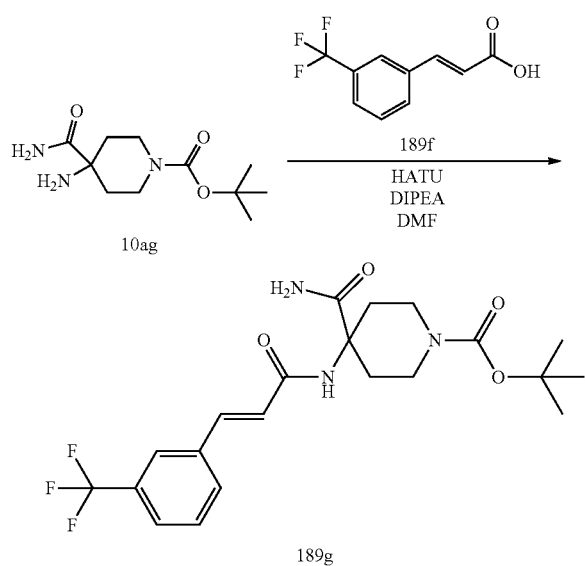

4-Carbamoyl-4-[(E)-3-(3-trifluoromethyl-phenyl)-acryloylamino]-piperidine-1-carboxylic acid tert-butyl ester was synthesized by operations similar to those in Reaction 10-14 using appropriate reagents and starting material.

MS (ESI) m/z=440 (M–H)–.

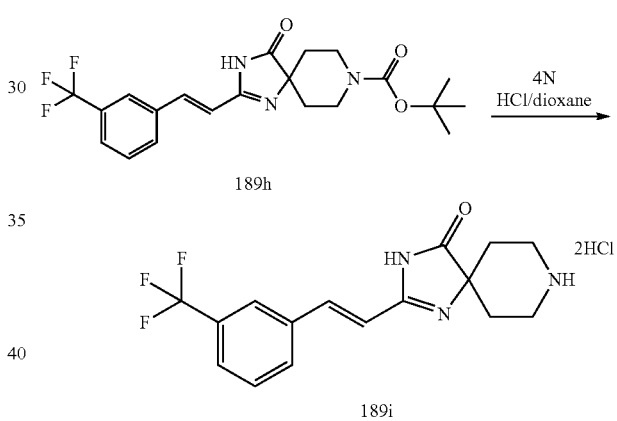

2-[(E)-2-(3-Trifluoromethyl-phenyl)-vinyl]-1,3,8-triaza-spiro[4.5]dec-1-en-4-one dihydrochloride was synthesized by operations similar to those in Reaction 5-3 using appropriate reagents and starting material.

MS (ESI) m/z=324 (M+H)+.

The spiroamine reagent used in the synthesis of Compound 893 (2-phenylethynyl-1,3,8-triaza-spiro[4.5]dec-1-en-4-one ditrifluoroacetate) was synthesized by the method shown below.

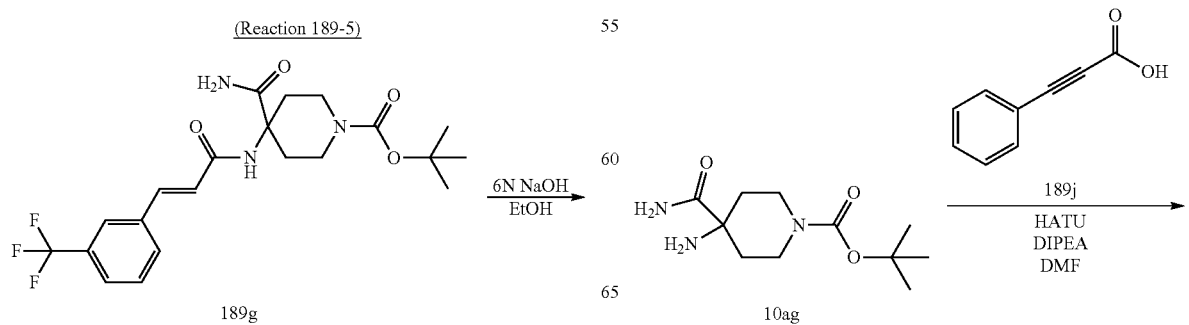

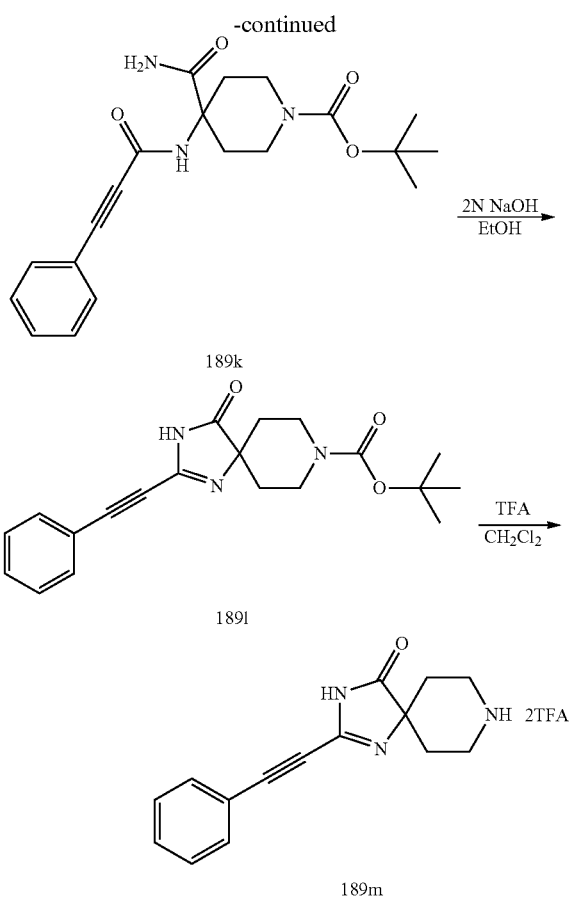

189k

189l

189m

2-Phenylethynyl-1,3,8-triaza-spiro[4.5]dec-1-en-4-one ditrifluoroacetate was synthesized by operations similar to those in Reaction 10-14, Reaction 189-5 and Reaction 4-1 using appropriate reagents and starting material.

MS (ESI) m/z=254 (M+H)+.

The spiroamine reagent used in the synthesis of Compound 898 (cyclohexylmethyl-[2-(3-trifluoromethoxy-phenyl)-1,3,8-triaza-spiro[4.5]deca-1,3-dien-4-yl]-amine ditrifluoroacetate) was synthesized as follows.

(Reaction 189-8)

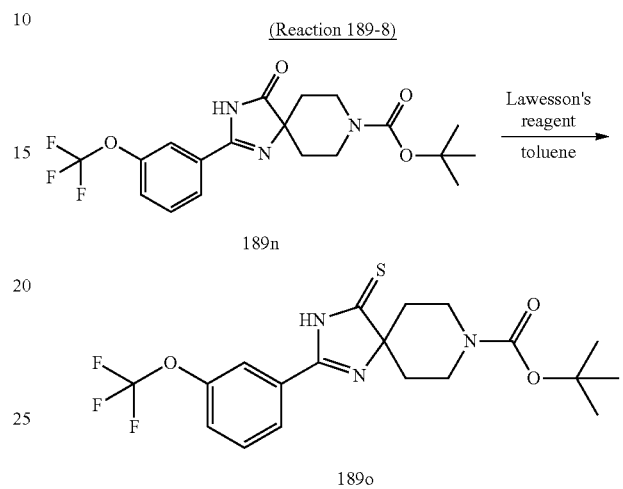

189n

189o

4-Thioxo-2-(3-trifluoromethoxy-phenyl)-1,3,8-triaza-spiro[4.5]dec-1-ene-8-carboxylic acid tert-butyl ester was synthesized by operations similar to those in Reaction 88-1 using appropriate reagents and starting material.

$^1$H-NMR (400 MHz, CDCl$_3$) δ 1.42 (2H, dull d, J=16.0 Hz), 1.50 (9H, s), 2.14 (2H, td, J=16.0, 4.0 Hz), 3.33 (2H, br), 4.18 (2H, br), 7.44 (1H, m), 7.58 (1H, t, J=8.0 Hz), 7.79 (1H, d, J=8.0 Hz), 7.82 (1H, s), 10.30 (1H, br).

(Reaction 189-9)

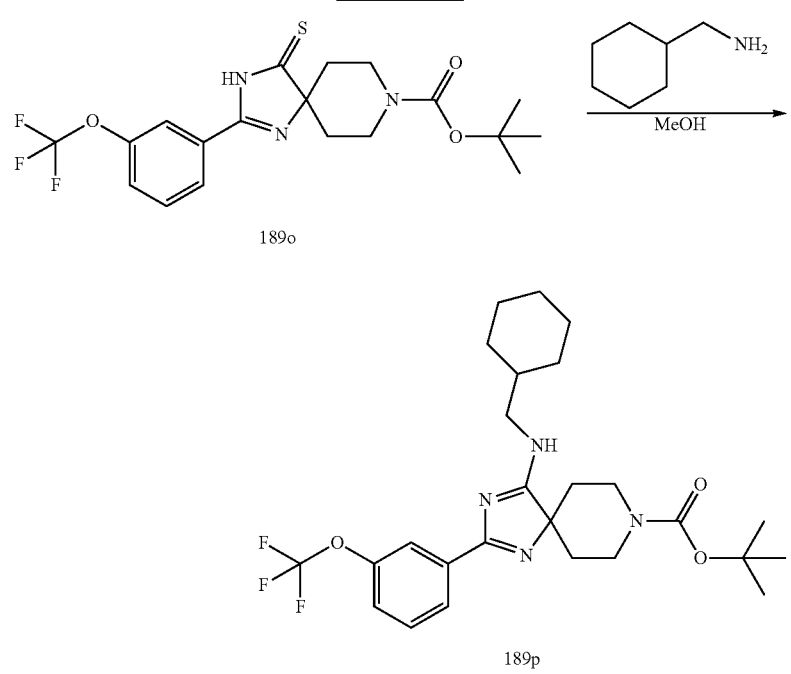

189o

189p

965

Cyclohexyl-methylamine (0.044 ml, 0.34 mmol) was added to a solution of 4-thioxo-2-(3-trifluoromethoxy-phenyl)-1,3,8-triaza-spiro[4.5]dec-1-ene-8-carboxylic acid tert-butyl ester (14.6 mg, 0.0340 mmol) in methanol (0.1 ml), and the mixture was stirred at 60° C. for 24 hours and at 70° C. for 11 hours. The reaction mixture was concentrated under reduced pressure, and the resulting residue was purified by silica gel column chromatography (hexane-ethyl acetate) to give 4-(cyclohexylmethyl-amino)-2-(3-trifluoromethoxy-phenyl)-1,3,8-triaza-spiro[4.5]deca-1,3-diene-8-carboxylic acid tert-butyl ester (16.3 mg, 94%).

$^1$H-NMR (400 MHz, CDCl$_3$) δ 1.02 (2H, m), 1.24 (3H, m), 1.44 (2H, d, J=13.2 Hz), 1.50 (9H, s), 1.65 (4H, m), 1.76 (4H, m), 3.40 (4H, m), 4.17 (2H, br), 5.12 (1H, br), 7.28 (1H, m), 7.44 (1H, t, J=8.0 Hz), 7.08 (1H, dull s), 8.16 (1H, m).

(Reaction 189-10)

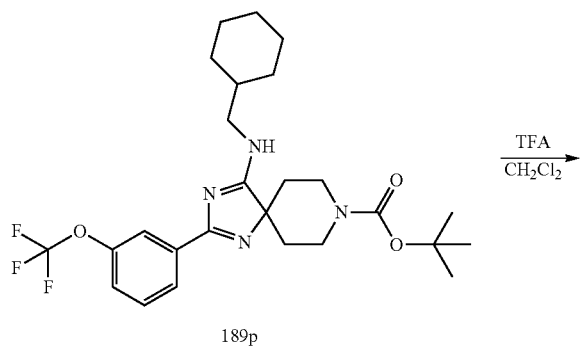

189p

189q

Cyclohexylmethyl-[2-(3-trifluoromethoxy-phenyl)-1,3,8-triaza-spiro[4.5]deca-1,3-dien-4-yl]-amine ditrifluoroacetate was synthesized by operations similar to those in Reaction 4-1 using appropriate reagents and starting material.

MS (ESI) m/z=255 (M+H)+.

The spiroamine reagents used in the synthesis of Compounds 899 to 901 and shown below were synthesized by operations similar to those in Reaction 189-9 and Reaction 189-10 using appropriate reagents and starting materials.

TABLE 116

| Target Compound | Spiroamine reagent | Spiroamine reagent $^1$H-NMR |
|---|---|---|
| 899 | | $^1$H NMR (400 MHz, CDCl$_3$) δ: 2.06 (4H, m), 3.24 (2H, m), 3.60 (3H, s), 3.70 (3H, s), 4.10 (2H, br), 7.60 (1H, d, J = 8Hz), 7.65 (1H, t, J = 8 Hz), 8.32 (1H, s), 8.49 (1H, d, J = 8 Hz). |
| 900 | | This was used in the next reaction without purification. |
| 901 | | This was used in the next reaction without purification. |

Example 190

4-(2-{2-[4-(2-Methoxy-ethyl)-cyclohexyl]-4-oxo-1,3,8-triaza-spiro[4.5]dec-1-ene-8-sulfonyl}-ethyl)-3,N,N-trimethyl-benzamide (Compound 902)

(Reaction 190-1)

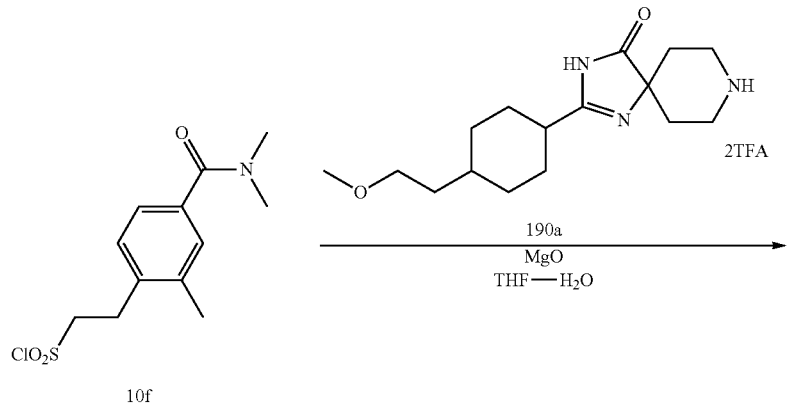

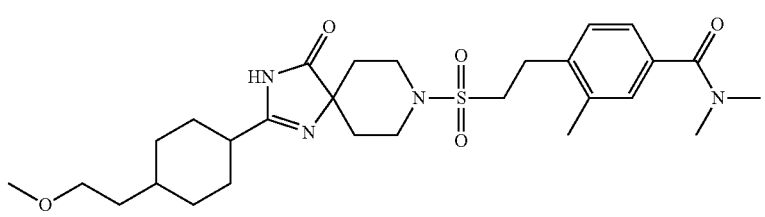

Compound 902

2-(4-Dimethylcarbamoyl-2-methyl-phenyl)-ethanesulfonyl chloride (22.2 mg) was added to a solution of 2-[4-(2-methoxy-ethyl)-cyclohexyl]-1,3,8-triaza-spiro[4.5]dec-1-en-4-one ditrifluoroacetate (63.9 µmol) and magnesium oxide (20 mg) in tetrahydrofuran-water (4:1 (v/v), 640 µL), and the mixture was stirred at room temperature for 30 minutes. 2-(4-Dimethylcarbamoyl-2-methyl-phenyl)-ethanesulfonyl chloride (22.2 mg) was further added and the mixture was stirred for one hour. The reaction mixture was quenched with water and extracted with dichloromethane. The organic layer was concentrated, and the resulting residue was purified by silica gel column chromatography (ethyl acetate-hexane) to give 4-(2-{2-[4-(2-methoxy-ethyl)-cyclohexyl]-4-oxo-1,3,8-triaza-spiro[4.5]dec-1-ene-8-sulfonyl}-ethyl)-3,N,N-trimethyl-benzamide (32.7 mg, 94%).

MS (ESI) m/z=547 (M+H)+.

The spiroamine reagent used in the synthesis of Compound 902 and shown below (2-[4-(2-methoxy-ethyl)-cyclohexyl]-1,3,8-triaza-spiro[4.5]dec-1-en-4-one ditrifluoroacetate) was synthesized by operations similar to those in Reaction 10-14, Reaction 1-4 and Reaction 4-1 using appropriate reagents and Compound 5a as a starting material.

TABLE 117

| Target Compound | Spiroamine reagent | Spiroamine reagent MS (m/z) |
|---|---|---|
| 902 | (structure shown: 2-[4-(2-methoxy-ethyl)-cyclohexyl]-1,3,8-triaza-spiro[4.5]dec-1-en-4-one · 2TFA) | 294 (M + H)+ |

The carboxylic acid (4-(2-methoxy-ethyl)-cyclohexanecarboxylic acid) necessary for the synthesis of the spiroamine reagent used for Compound 902 (2-[4-(2-methoxy-ethyl)-cyclohexyl]-1,3,8-triaza-spiro[4.5]dec-1-en-4-one ditrifluoroacetate) was synthesized by the method shown below.

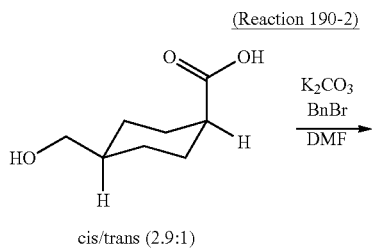

(Reaction 190-2)

cis/trans (2.9:1)
190b

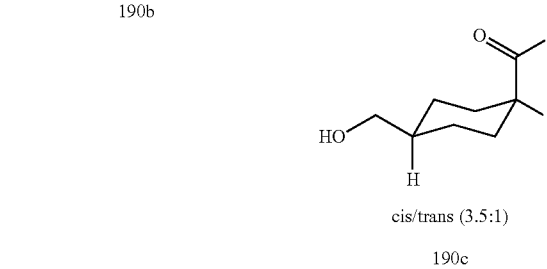

cis/trans (3.5:1)
190c

Potassium carbonate (2.61 g, 18.9 mmol) and benzyl bromide (2.24 mL, 18.9 mmol) were added to a solution of 4-hydroxymethyl-cyclohexanecarboxylic acid (cis-trans=2.9:1 mixture) (2.49 g, 15.7 mmol) in DMF (31.5 mL) at room temperature, and the mixture was stirred at 60° C. for one hour. The reaction solution was cooled, and H₂O (60 mL) was then added to the reaction solution, followed by extraction with hexane:ethyl acetate (2:1) (300 mL) twice. The organic layers were dried over sodium sulfate and concentrated under reduced pressure. The resulting residue was purified by silica gel column chromatography (hexane-ethyl acetate) to give 4-hydroxymethyl-cyclohexanecarboxylic acid benzyl ester (cis-trans=3.5:1 mixture) as a colorless oily substance (3.79 g, 97%).

MS (ESI) m/z=249 (M+H)+.

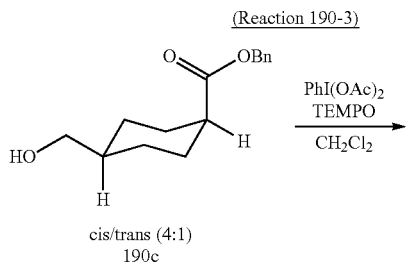

(Reaction 190-3)

cis/trans (4:1)
190c

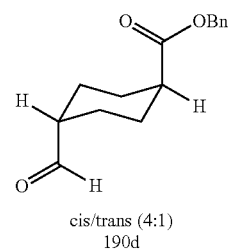

cis/trans (4:1)
190d 2,2,6,6-Tetramethylpiperidine 1-oxyl (309 mg, 1.98 mmol) and (diacetoxyiodo)benzene (7.01 g, 21.8 mmol) were added to a solution of 4-hydroxymethyl-cyclohexanecarboxylic acid benzyl ester (cis-trans=4:1 mixture) (4.91 g, 19.8 mmol) at 0° C. in an N₂ atmosphere, and the mixture was stirred at 0° C. for one hour and at room temperature for seven hours. The reaction solution was diluted with dichloromethane (200 mL), and the organic layer was sequentially washed with a saturated aqueous sodium sulfite solution (100 mL), a saturated aqueous sodium bicarbonate solution (100 mL) and saturated brine (100 mL). The organic layer was dried over sodium sulfate and then concentrated under reduced pressure. The resulting residue was purified by silica gel column chromatography (hexane-ethyl acetate) to give 4-formyl-cyclohexanecarboxylic acid benzyl ester (cis-trans=4:1 mixture) as a colorless oily substance (4.44 g, 91%).

MS (ESI) m/z=247 (M+H)+.

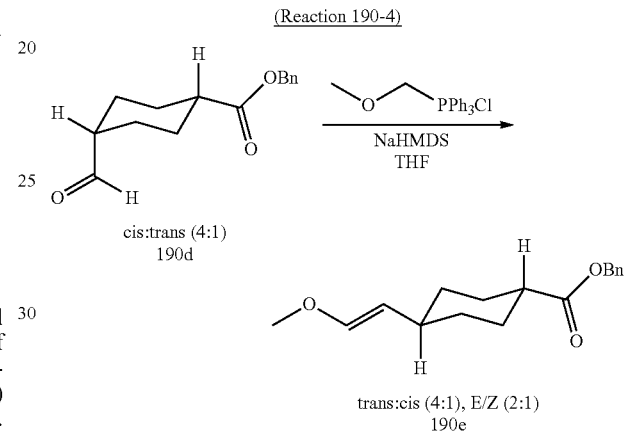

(Reaction 190-4)

cis:trans (4:1)
190d trans:cis (4:1), E/Z (2:1)
190e

NaHMDS (1.0 M in THF) (466 μL, 466 μmol) was added to a solution of methoxymethyltriphenylphosphonium chloride (160 mg, 466 μmol) in tetrahydrofuran (3.88 mL) at 0° C. in an N₂ atmosphere, and the mixture was stirred at 0° C. for one hour. A solution of 4-formyl-cyclohexanecarboxylic acid benzyl ester (cis-trans=4:1 mixture) (95.6 mg, 388 μmol) in tetrahydrofuran (2.00 mL) was added dropwise to the reaction solution at 0° C., and the mixture was stirred for 30 minutes. Thereafter, the reaction mixture was stirred at room temperature for 20 hours and quenched with a saturated aqueous ammonium chloride solution (5 mL). H₂O (20 mL) was then added, followed by extraction with dichloromethane (50 mL). The organic layer was dried over sodium sulfate and concentrated under reduced pressure. The resulting residue was purified by silica gel column chromatography (hexane-ethyl acetate) to give 4-(2-methoxy-vinyl)-cyclohexanecarboxylic acid benzyl ester (trans-cis=4:1 and E-Z=2:1 mixture) as a yellow oily substance (49.7 mg, 47%).

MS (ESI) m/z=275 (M+H)+.

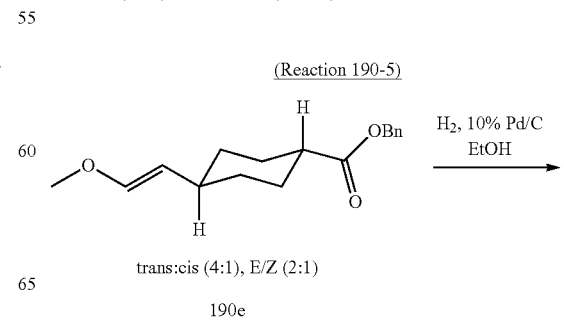

(Reaction 190-5)

trans:cis (4:1), E/Z (2:1)
190e

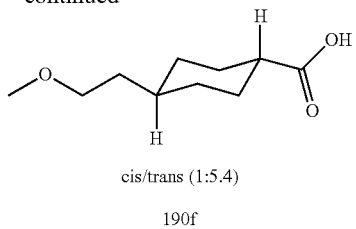

cis/trans (1:5.4)

190f 4-(2-Methoxy-ethyl)-cyclohexanecarboxylic acid was synthesized by operations similar to those in Reaction 18-2 using appropriate reagents and starting material.

$^1$H-NMR (400 MHz, CDCl$_3$) δ 0.89-1.02 (2H, ddd, J=3.8, 13.2, 24.9 Hz), 1.30-1.62 (5H, m), 1.79-1.85 (2H, br-m), 1.92-2.04 (2H, br-m), 2.25 (0.8H, tt, J=3.4, 12.2 Hz), 2.58 (0.2H, quintet, J=4.9 Hz), 3.32 (0.6H, s), 3.33 (2.4H, s), 3.41 (2H, t, J=6.8 Hz).

Example 191

N-{4-[2-(2-Cyclopentyl-4-oxo-1,3,8-triaza-spiro [4.5]dec-1-ene-8-sulfonyl)-ethyl]-3-methyl-phenyl}-acetamide (Compound 903)

(Reaction 191-1)

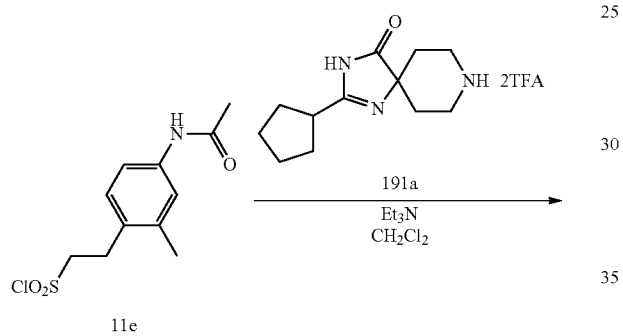

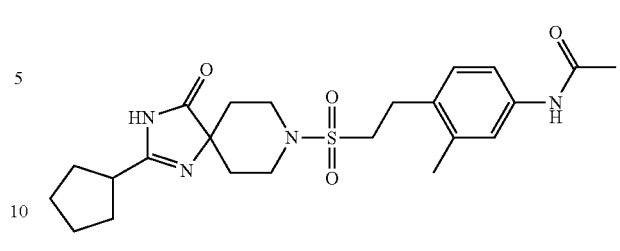

Compound 903

N-{4-[2-(2-Cyclopentyl-4-oxo-1,3,8-triaza-spiro[4.5] dec-1-ene-8-sulfonyl)-ethyl]-3-methyl-phenyl}-acetamide was synthesized by operations similar to those in Reaction 5-4 using appropriate reagents and starting material.

MS (ESI) m/z=461 (M+H)+.

The example compounds shown below were synthesized by operations similar to those in Reaction 191-1 using appropriate reagents and starting materials.

Compounds 904 to 916

TABLE 118

| Compound | Structure | LCMS condition | Retention time (min) | MS (m/z) |
|---|---|---|---|---|
| 904 | 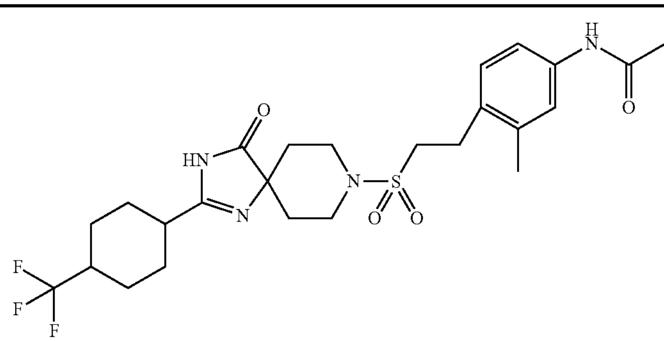 | LCMS-C-1 | 2.45 | 543 (M + H)+ |
| 905 | 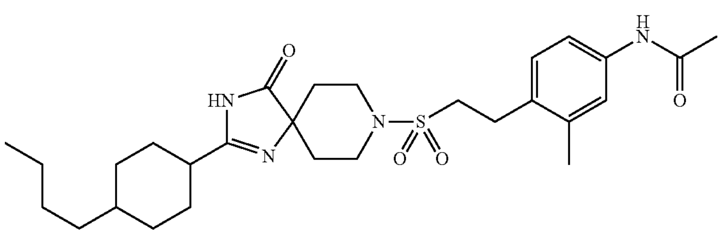 [SMILES: CCCCC1CCC(C2=NC3(CCN(S(=O)(=O)CCc4ccc(NC(C)=O)cc4C)CC3)C(=O)N2)CC1] | LCMS-C-1 | 2.85 | 531 (M + H)+ |

TABLE 118-continued

| Compound | Structure | LCMS condition | Retention time (min) | MS (m/z) |
|---|---|---|---|---|
| 906 | 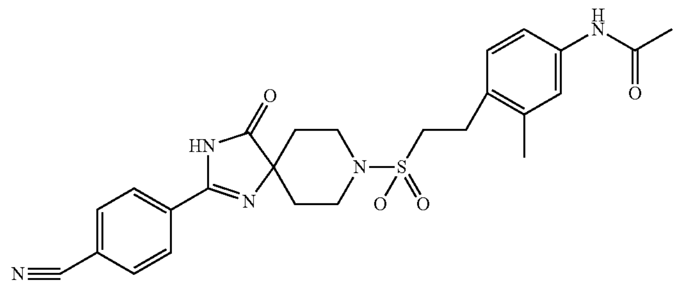 | LCMS-A-1 | 2.05 | 494 (M + H)+ |
| 907 | 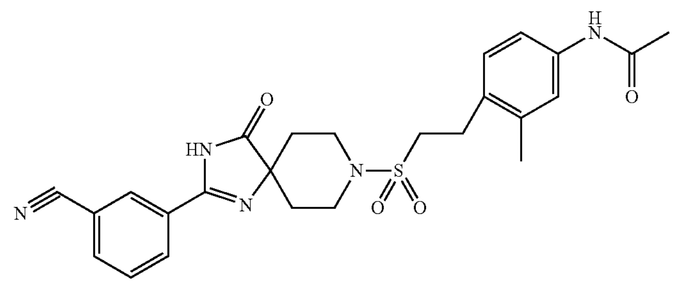 [SMILES: CC(=O)Nc1ccc(CCS(=O)(=O)N2CCC3(CC2)N=C(c2cccc(C#N)c2)NC3=O)c(C)c1] | LCMS-A-1 | 2.05 | 494 (M + H)+ |
| 908 | 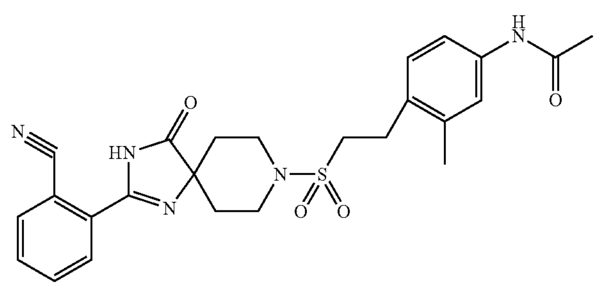 [SMILES: CC(=O)Nc1ccc(CCS(=O)(=O)N2CCC3(CC2)N=C(c2ccccc2C#N)NC3=O)c(C)c1] | LCMS-A-1 | 1.99 | 494 (M + H)+ |
| 909 | 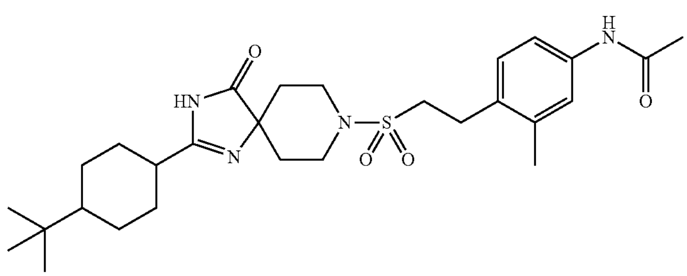 [SMILES: CC(=O)Nc1ccc(CCS(=O)(=O)N2CCC3(CC2)N=C(C2CCC(C(C)(C)C)CC2)NC3=O)c(C)c1] | LCMS-C-1 | 2.85 | 531 (M + H)+ |
| 910 | 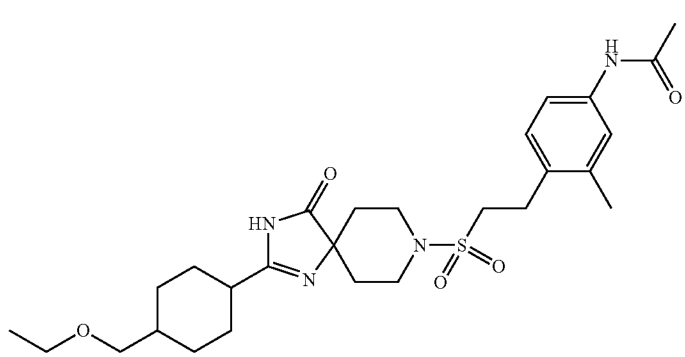 [SMILES: CCOCC1CCC(C2=NC3(CCN(S(=O)(=O)CCc4ccc(NC(C)=O)cc4C)CC3)C(=O)N2)CC1] | LCMS-C-1 | 2.38 | 533 (M + H)+ |

TABLE 118-continued

| Compound | Structure | LCMS condition | Retention time (min) | MS (m/z) |
|---|---|---|---|---|
| 911 | 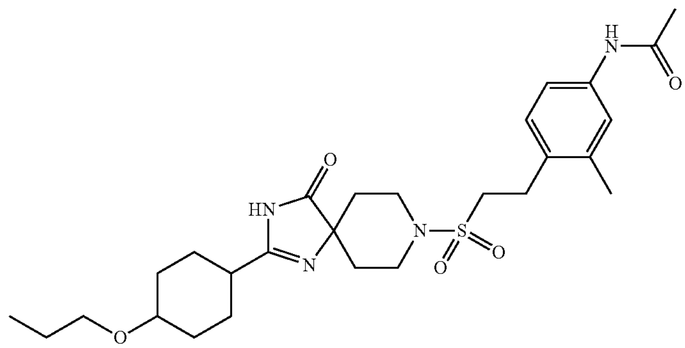 [SMILES: CCCOC1CCC(C2=NC3(CCN(S(=O)(=O)CCc4ccc(NC(C)=O)cc4C)CC3)C(=O)N2)CC1] | LCMS-C-1 | 2.48 | 533 (M + H)+ |
| 912 | 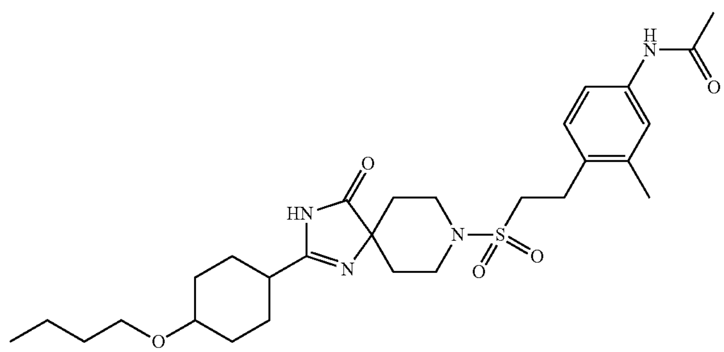 [SMILES: CCCCOC1CCC(C2=NC3(CCN(S(=O)(=O)CCc4ccc(NC(C)=O)cc4C)CC3)C(=O)N2)CC1] | LCMS-C-1 | 2.6 | 547 (M + H)+ |
| 913 | 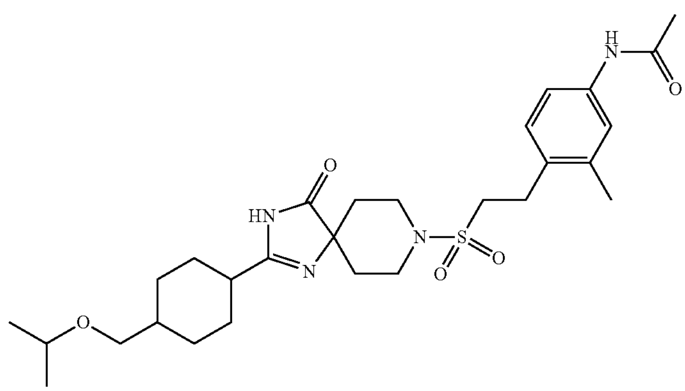 [SMILES: CC(=O)Nc1ccc(CCS(=O)(=O)N2CCC3(CC2)N=C(C2CCC(COC(C)C)CC2)NC3=O)c(C)c1] | LCMS-C-1 | 2.52 | 547 (M + H)+ |
| 914 | 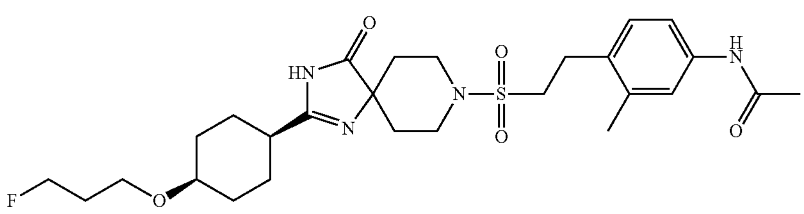 [SMILES: CC(=O)Nc1ccc(CCS(=O)(=O)N2CCC3(CC2)N=C([C@H]2CC[C@@H](OCCCF)CC2)NC3=O)c(C)c1] | LCMS-C-2 | 1.68 | 551 (M + H)+ |
| 915 | 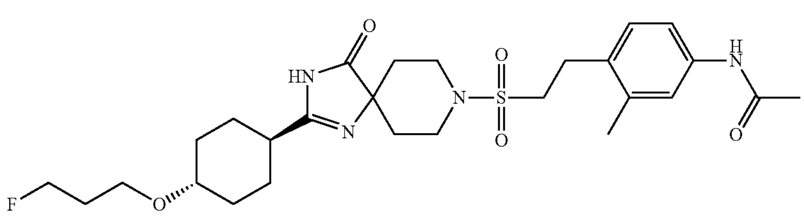 [SMILES: CC(=O)Nc1ccc(CCS(=O)(=O)N2CCC3(CC2)N=C([C@H]2CC[C@H](OCCCF)CC2)NC3=O)c(C)c1] | LCMS-C-2 | 1.65 | 551 (M + H)+ |

TABLE 118-continued

| Compound | Structure | LCMS condition | Retention time (min) | MS (m/z) |
|---|---|---|---|---|
| 916 | 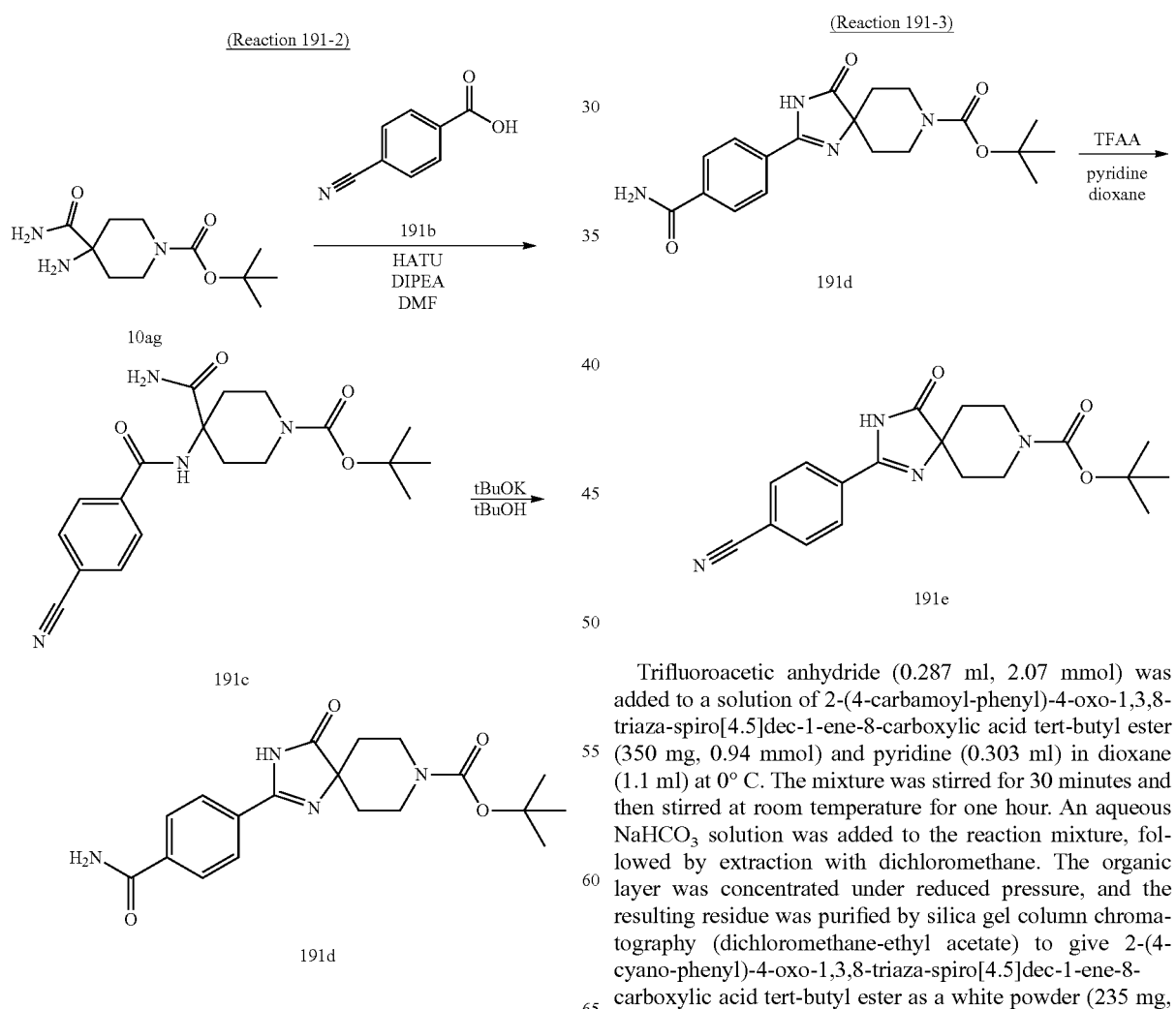 | LCMS-C-2 | 1.85 | 551 (M + H)+ |

The spiroamine reagent used in the synthesis of Compound 906 (4-(4-oxo-1,3,8-triaza-spiro[4.5]dec-1-en-2-yl)-benzonitrile dihydrochloride) was synthesized by the following method.

(Reaction 191-2)

10ag

191c

191d 2-(4-Carbamoyl-phenyl)-4-oxo-1,3,8-triaza-spiro[4.5]dec-1-ene-8-carboxylic acid tert-butyl ester was synthesized by operations similar to those in Reaction 10-14 and Reaction 10-12 using appropriate reagents and starting material.

MS (ESI) m/z=373 (M+H)+.

(Reaction 191-3)

191d

191e

Trifluoroacetic anhydride (0.287 ml, 2.07 mmol) was added to a solution of 2-(4-carbamoyl-phenyl)-4-oxo-1,3,8-triaza-spiro[4.5]dec-1-ene-8-carboxylic acid tert-butyl ester (350 mg, 0.94 mmol) and pyridine (0.303 ml) in dioxane (1.1 ml) at 0° C. The mixture was stirred for 30 minutes and then stirred at room temperature for one hour. An aqueous NaHCO₃ solution was added to the reaction mixture, followed by extraction with dichloromethane. The organic layer was concentrated under reduced pressure, and the resulting residue was purified by silica gel column chromatography (dichloromethane-ethyl acetate) to give 2-(4-cyano-phenyl)-4-oxo-1,3,8-triaza-spiro[4.5]dec-1-ene-8-carboxylic acid tert-butyl ester as a white powder (235 mg, 71%).

MS (ESI) m/z=353 (M–H)–.

(Reaction 191-4)

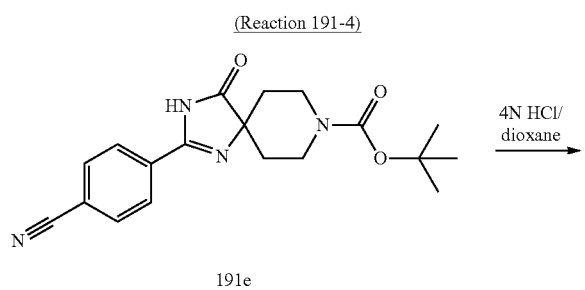

4-(4-Oxo-1,3,8-triaza-spiro[4.5]dec-1-en-2-yl)-benzonitrile dihydrochloride was synthesized by operations similar to those in Reaction 5-3 using appropriate reagents and starting material.

MS (ESI) m/z=255 (M+H)+.

The spiroamine reagents used in the synthesis of Compounds 907 to 908 and shown below were synthesized by operations similar to those in Reaction 10-14, Reaction 10-12 and Reaction 5-3 using appropriate reagents and Compound 10ag as a starting material.

TABLE 119

| Target Compound | Spiroamine reagent | Spiroamine reagent MS (m/z) |
|---|---|---|
| 907 | (3-cyanophenyl spiroamine · 2HCl) | 255 (M + H)+ |
| 908 | (2-cyanophenyl spiroamine · 2HCl) | 255 (M + H)+ |

The spiroamine reagents used in the synthesis of Compounds 910, 911, 912 and 913 and shown below were synthesized by operations similar to those in Reaction 10-14, Reaction 1-4 and Reaction 4-1 using appropriate reagents and Compound 5a as a starting material.

TABLE 120

| Target Compound | Spiroamine reagent | Spiroamine reagent MS (m/z) or ¹H-NMR |
|---|---|---|
| 910 | (ethoxymethyl-cyclohexyl spiroamine · 2TFA) | 292 (M − H)− |

TABLE 120-continued

| Target Compound | Spiroamine reagent | Spiroamine reagent MS (m/z) or ¹H-NMR |
|---|---|---|
| 911 | (structure with propoxy-cyclohexyl group, 2TFA) | 292 (M − H)− |
| 912 | (structure with butoxy-cyclohexyl group, 2TFA) | 306 (M − H)− |
| 913 | (structure with isopropoxymethyl-cyclohexyl group, 2TFA) | 306 (M − H)− |
| 916 | (structure with 3,3-difluoropropenyl-cyclohexyl group, 2TFA) | ¹H-NMR (400MHz, CD₃OD) δ 1.24-1.33 (2H, m), 1.56-1.64 (2H, m), 1.93-1.96 (4H, m), 2.06-2.13 (5H, m), 2.50-2.70(1H, m), 3.34-3.42 (2H, m), 3.51-3.57 (2H, m), 5.61-5.70(1H, m), 5.96-6.25 (2H, m) |

The carboxylic acid necessary for the synthesis of the spiroamine reagent used for Compound 910 (4-ethoxymethyl-cyclohexanecarboxylic acid) was synthesized by the method shown below.

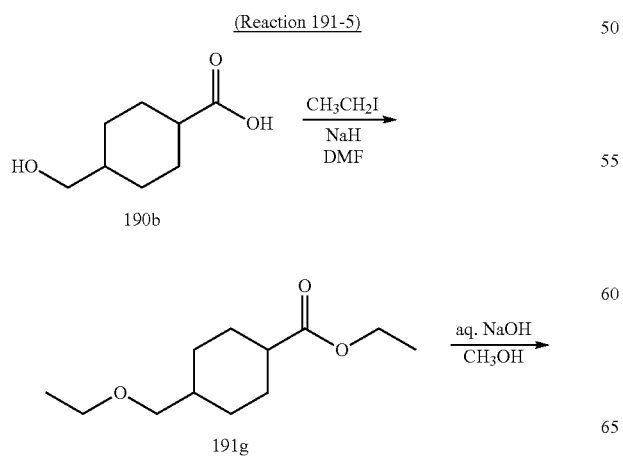

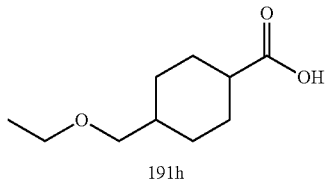

4-Ethoxymethyl-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 911 (4-propoxy-cyclohexanecarboxylic acid) was synthesized by the method shown below.

(Reaction 191-6)

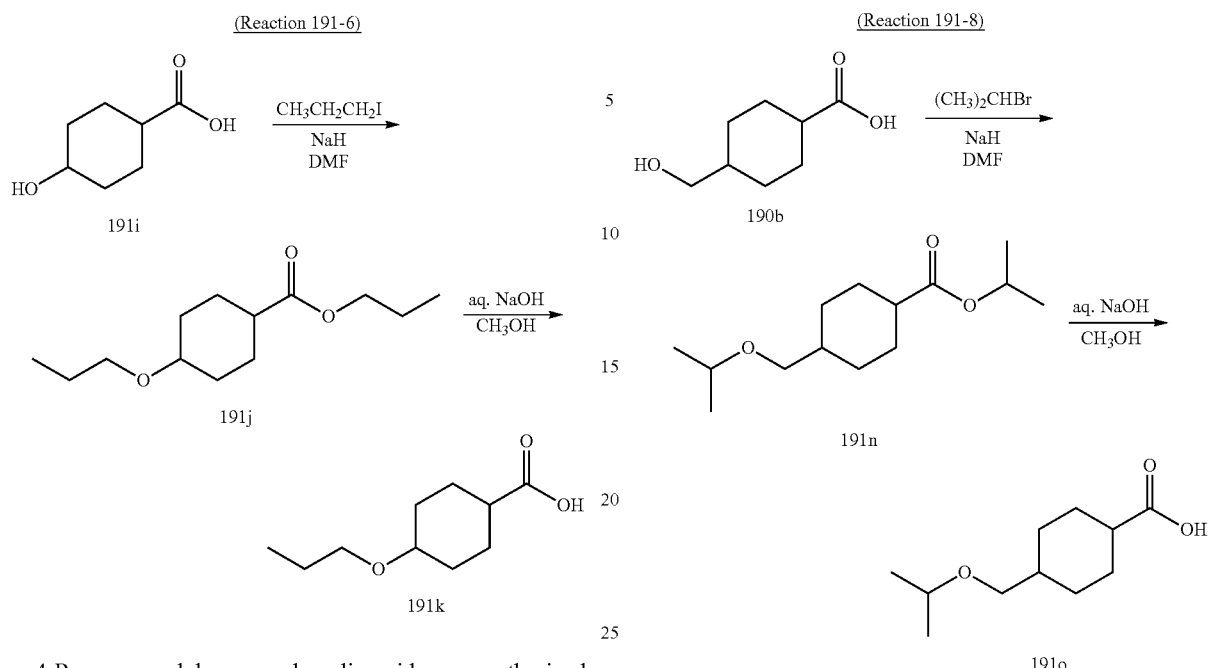

4-Propoxy-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 912 (4-butoxy-cyclohexanecarboxylic acid) was synthesized by the method shown below.

(Reaction 191-7)

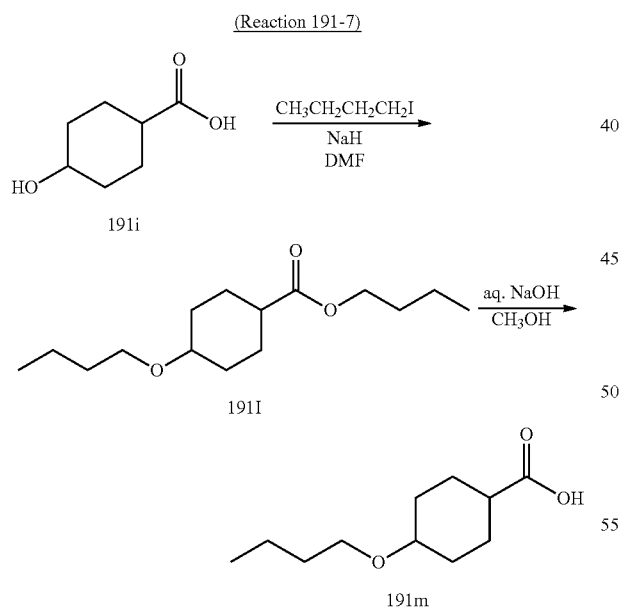

4-Butoxy-cyclohexanecarboxylic acid was synthesized by operations similar to those in Reaction 20-2 and Reaction 95-18 using appropriate reagents and starting material. This was used as such in the next reaction.

The carboxylic acid necessary for the synthesis of the spiroamine reagent used for Compound 913 (4-isopropoxymethyl-cyclohexanecarboxylic acid) was synthesized by the method shown below.

(Reaction 191-8)

4-Isopropoxymethyl-cyclohexanecarboxylic acid was synthesized by operations similar to those in Reaction 20-2 and Reaction 95-18 using appropriate reagents and starting material. This was used as such in the next reaction.

The spiroamine reagent used in the synthesis of Compound 914 (2-[4-(3-fluoro-propoxy)-cyclohexyl]-1,3,8-triaza-spiro[4.5]dec-1-en-4-one ditrifluoroacetate) was synthesized by the following method.

(Reaction 191-9)

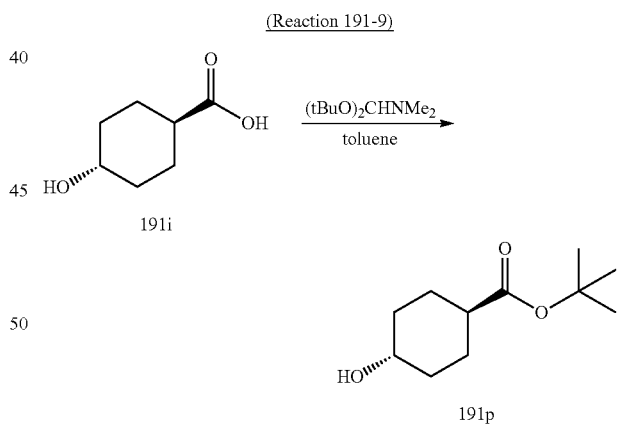

N,N-Dimethylformamide di-tert-butyl acetal (7.4 ml, 31 mmol) was added to a solution of trans-4-hydroxy-cyclohexanecarboxylic acid (1.484 g, 10.29 mmol) in toluene (8.5 ml), and the mixture was stirred at 80° C. for 25 hours. The reaction mixture was diluted with ether, and the organic layer was sequentially washed with water, an aqueous sodium bicarbonate solution and saturated brine, dried over MgSO$_4$ and concentrated under reduced pressure. The resulting residue was purified by silica gel column chromatography (hexane-ethyl acetate) to give trans-4-hydroxy-cyclohexanecarboxylic acid tert-butyl ester as a colorless solid (838 m, 41%).

¹H-NMR (400 MHz, CDCl₃) δ 1.28 (2H, m), 1.43 (9H, s), 1.45 (2H, m), 1.99 (4H, m), 2.14 (1H, m), 3.60 (1H, m).

(Reaction 191-10)

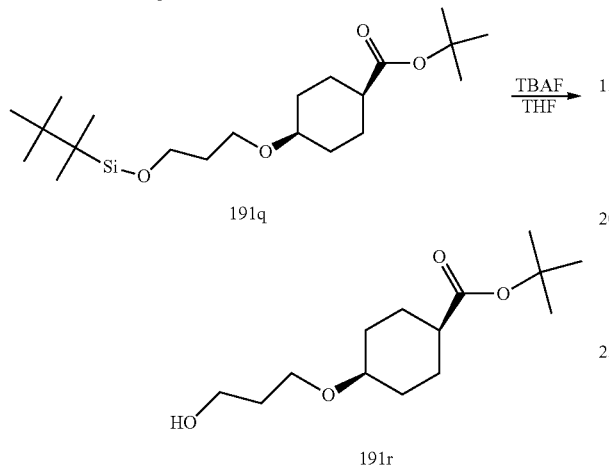

cis-4-(3-Hydroxy-propoxy)-cyclohexanecarboxylic acid tert-butyl ester was obtained by operations similar to those in Reaction 20-2 and Reaction 39-2 using the compound obtained above and appropriate reagents.

¹H-NMR (400 MHz, CDCl₃) δ 1.43 (9H, s), 1.53 (2H, m), 1.62 (2H, m), 1.83 (6H, m), 2.25 (1H, m), 2.60 (1H, t, J=5.4 Hz), 3.46 (1H, m), 3.61 (2H, t, J=5.9 Hz), 3.79 (2H, q, J=5.4 Hz).

(Reaction 191-11)

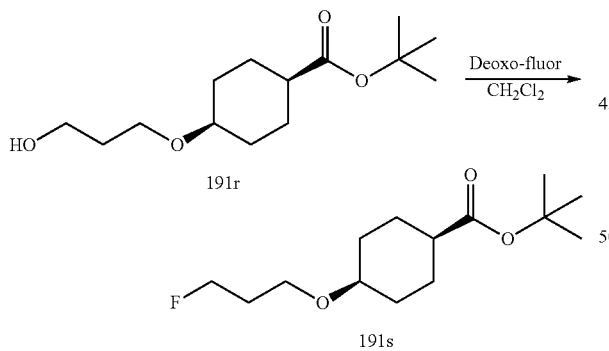

Deoxo-Fluor (5 mg, 0.02 mmol) was added to a solution of cis-4-(3-hydroxy-propoxy)-cyclohexanecarboxylic acid tert-butyl ester (3.9 mg, 0.015 mmol) in dichloromethane (0.1 ml), and the mixture was stirred at room temperature for two hours. An aqueous sodium bicarbonate solution was added to the reaction mixture, followed by extraction with dichloromethane. The organic layer was then dried over MgSO₄ and concentrated under reduced pressure. The resulting residue was purified by silica gel column chromatography (hexane-ethyl acetate) to give cis-4-(3-fluoro-propoxy)-cyclohexanecarboxylic acid tert-butyl ester (3.1 mg, 79%).

¹H-NMR (400 MHz, CDCl₃) δ 1.44 (9H, s), 1.51 (2H, m), 1.60 (2H, m), 1.79 (2H, m), 1.94 (2H, m), 2.25 (1H, m), 2.60 (1H, t, J=5.4 Hz), 3.43 (1H, m), 3.51 (2H, t, J 6.1 Hz), 4.56 (2H, dt, J=47.4, 5.9 Hz).

(Reaction 191-12)

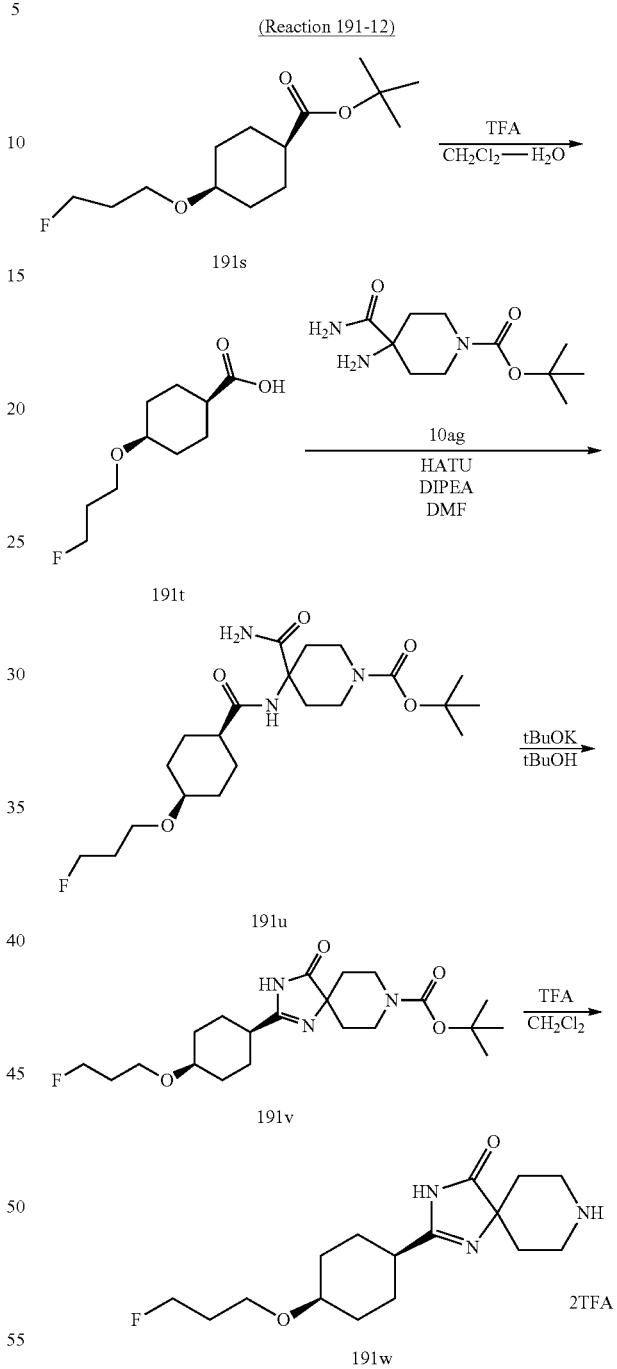

2-[4-(3-Fluoro-propoxy)-cyclohexyl]-1,3,8-triaza-spiro[4.5]dec-1-en-4-one ditrifluoroacetate was synthesized by operations similar to those in Reaction 4-1 (further adding water), Reaction 10-14, Reaction 10-12 and Reaction 4-1 using appropriate reagents and starting material. This was used as such in the next reaction.

The spiroamine reagent used in the synthesis of Compound 915 and shown below was synthesized by operations similar to those in Reaction 10-14, Reaction 10-12 and Reaction 4-1 using appropriate reagents and Compound 10ag as a starting material.

TABLE 121

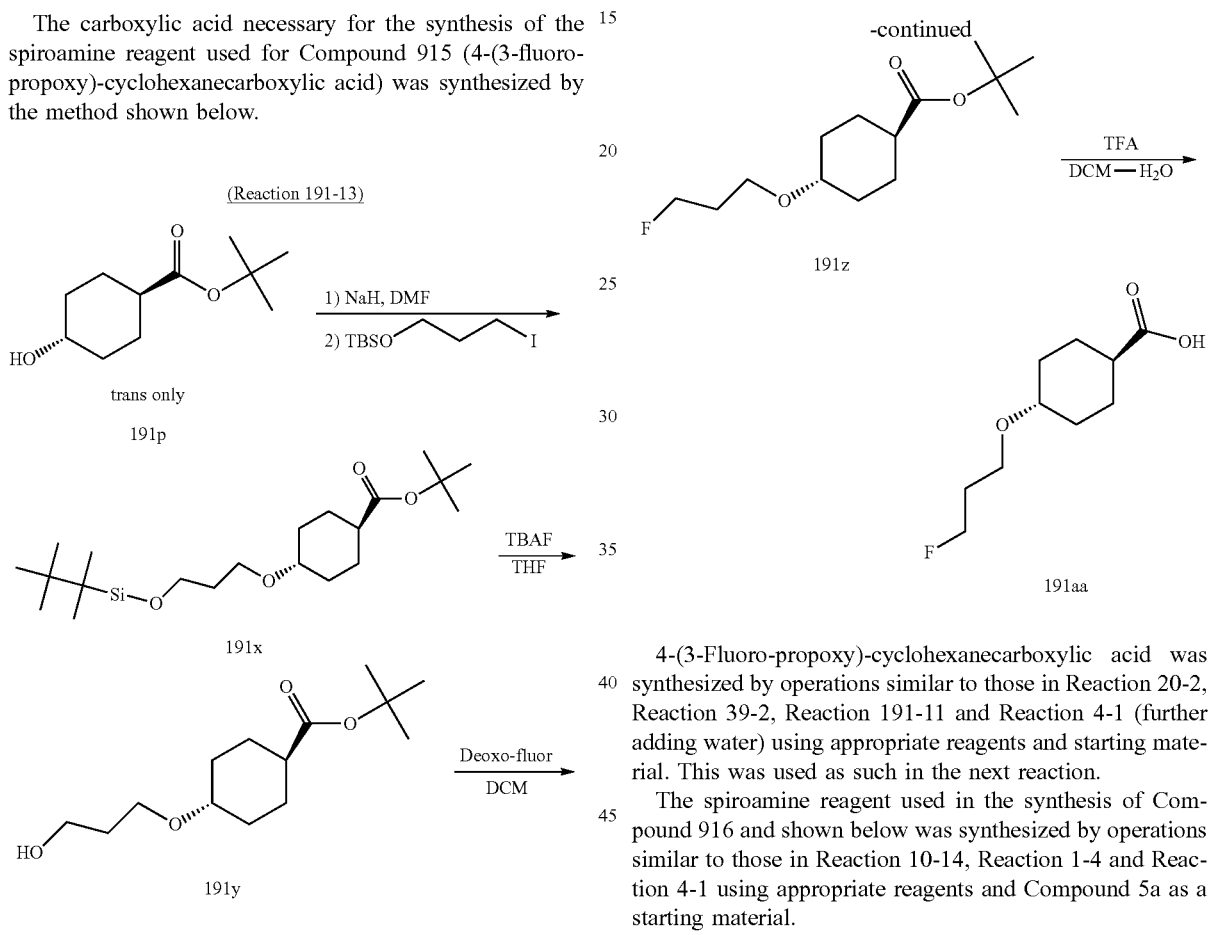

The carboxylic acid necessary for the synthesis of the spiroamine reagent used for Compound 915 (4-(3-fluoropropoxy)-cyclohexanecarboxylic acid) was synthesized by the method shown below.

4-(3-Fluoro-propoxy)-cyclohexanecarboxylic acid was synthesized by operations similar to those in Reaction 20-2, Reaction 39-2, Reaction 191-11 and Reaction 4-1 (further adding water) using appropriate reagents and starting material. This was used as such in the next reaction.

The spiroamine reagent used in the synthesis of Compound 916 and shown below was synthesized by operations similar to those in Reaction 10-14, Reaction 1-4 and Reaction 4-1 using appropriate reagents and Compound 5a as a starting material.

TABLE 122

The carboxylic acid necessary for the synthesis of the spiroamine reagent used for Compound 916 (4-((E)-3,3-difluoro-propenyl)-cyclohexanecarboxylic acid) was synthesized by the method shown below.

(Reaction 191-14)

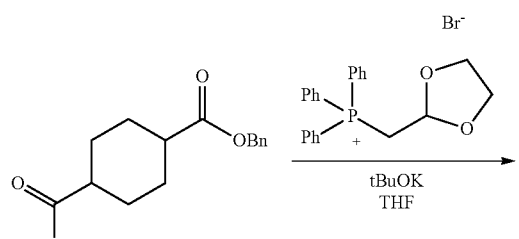

190d

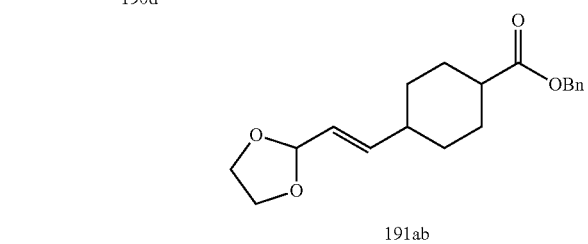

191ab

Potassium t-butoxide (68.3 mg, 609 μmol) was added to a solution of (1,3-dioxolan-2-ylmethyl)-triphenylphosphonium bromide (267 mg, 609 μmol) in THF (2.0 ml) at 0° C., and the mixture was stirred at 0° C. for 1.5 hours in an N₂ atmosphere. A solution of 4-formyl-cyclohexanecarboxylic acid benzyl ester (50.0 mg, 203 μmol) in THF (1.5 ml) was added to the reaction mixture at 0° C., and the mixture was stirred at room temperature for 1.5 hours. Thereafter, the reaction mixture was quenched by adding a saturated aqueous ammonium chloride solution at 0° C. and then extracted with ethyl acetate three times. The organic layers were sequentially washed with H₂O (×2) and saturated brine, and then dried over MgSO₄ and concentrated under reduced pressure. The residue was used in the next step without further purification.

(Reaction 191-15)

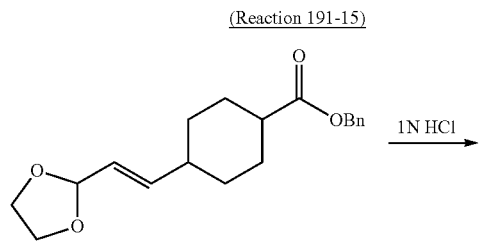

191ab

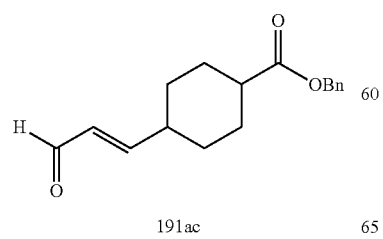

191ac

1 N hydrochloric acid (406 μl, 406 μl) was added to a solution of the residue obtained in Reaction 191-14 in THF (2.0 ml) at 0° C., and the mixture was stirred at room temperature for 4.5 hours. The reaction solution was quenched by adding a saturated aqueous sodium bicarbonate solution at 0° C. and then extracted with ethyl acetate three times. The organic layers were sequentially washed with H₂O (×2) and saturated brine, and then dried over MgSO₄ and concentrated under reduced pressure. The residue was purified by column chromatography (hexane-ethyl acetate) to give 4-((E)-3-oxo-propenyl)-cyclohexanecarboxylic acid benzyl ester as a colorless oil (38.2 mg, 69%).

MS (ESI) m/z=273 (M+H)+.

(Reaction 191-16)

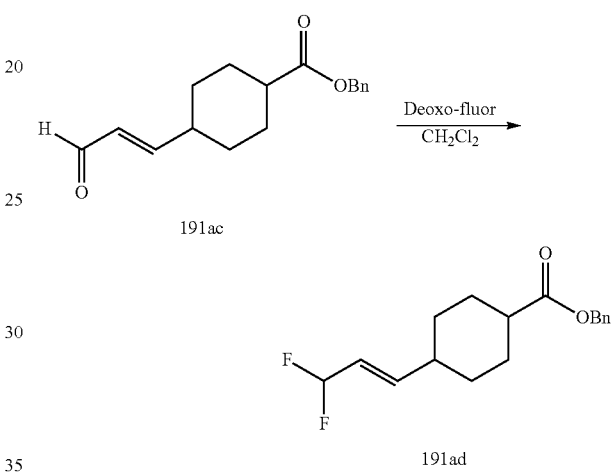

191ac

191ad 4-((E)-3,3-Difluoro-propenyl)-cyclohexanecarboxylic acid benzyl ester was synthesized by operations similar to those in Reaction 191-11 using appropriate reagents and starting material.

¹H-NMR (400 MHz, CDCl₃) δ 1.46-1.52 (2H, m), 1.61-1.67 (3H, m), 1.88-2.30 (4H, m), 2.60-2.70 (1H, m), 5.58-5.64 (1H, m), 5.88-6.17 (2H, m).

(Reaction 191-17)

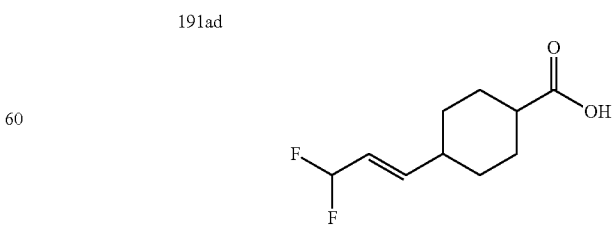

191ad

191ae 4-((E)-3,3-Difluoro-propenyl)-cyclohexanecarboxylic acid was synthesized by operations similar to those in Reaction 95-18 using appropriate reagents and starting material.

$^1$H-NMR (400 MHz, CDCl$_3$) δ 1.46-1.52 (2H, m), 1.61-1.67 (3H, m), 1.88-2.30 (4H, m), 2.60-2.70 (1H, m), 5.58-5.64 (1H, m), 5.88-6.17 (2H, m).

Example 192

N-{4-[2-(2-Cycloheptyl-4-oxo-1,3,8-triaza-spiro[4.5]dec-1-ene-8-sulfonyl)-ethyl]-3-methyl-phenyl}-acetamide (Compound 917)

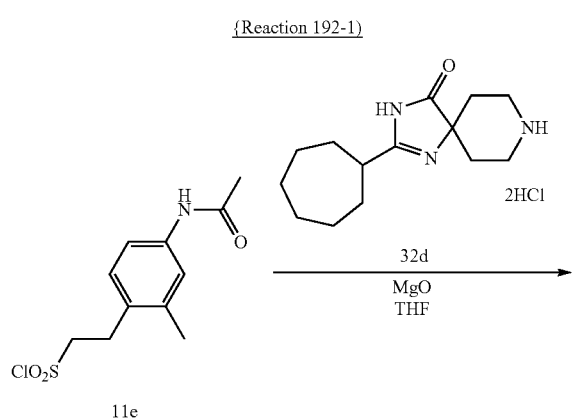

{Reaction 192-1}

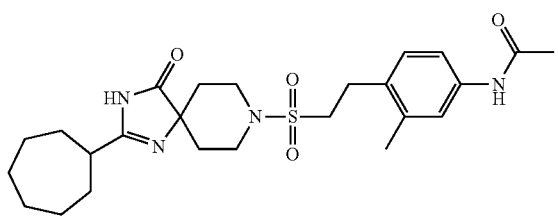

Compound 917

N-{4-[2-(2-Cycloheptyl-4-oxo-1,3,8-triaza-spiro[4.5]dec-1-ene-8-sulfonyl)-ethyl]-3-methyl-phenyl}-acetamide was synthesized by operations similar to those in Reaction 190-1 using appropriate reagents and starting material.

MS (ESI) m/z=489 (M+H)+.

The example compounds shown below were synthesized by operations similar to those in Reaction 192-1 using appropriate reagents and starting materials.

Compounds 918 to 919

TABLE 123

| Compound | Structure | LCMS condition | Retention time (min) | MS (m/z) |
|---|---|---|---|---|
| 918 | 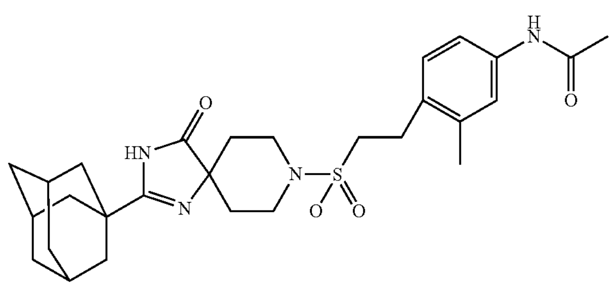 | LCMS-C-1 | 2.65 | 527 (M + H)+ |
| 919 | 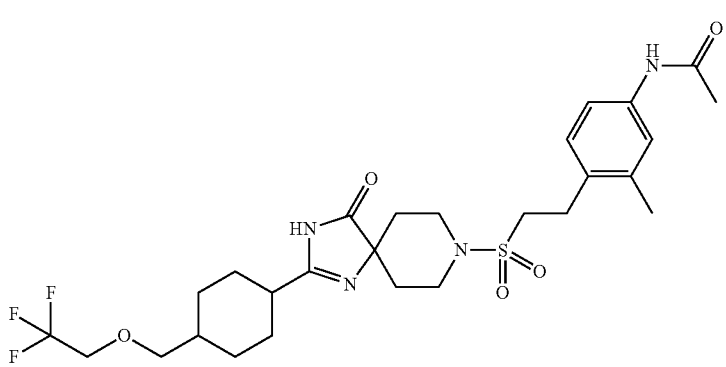 [SMILES: CC(=O)Nc1ccc(CCS(=O)(=O)N2CCC3(CC2)N=C(C2CCC(COCC(F)(F)F)CC2)NC3=O)c(C)c1] | LCMS-B-1 | 2.03 | 587 (M + H)+ |

The spiroamine reagent used in the synthesis of Compound 918 (2-adamantan-1-yl-1,3,8-triaza-spiro[4.5]dec-1-en-4-one ditrifluoroacetate) was synthesized by the following method.

(Reaction 192-2)

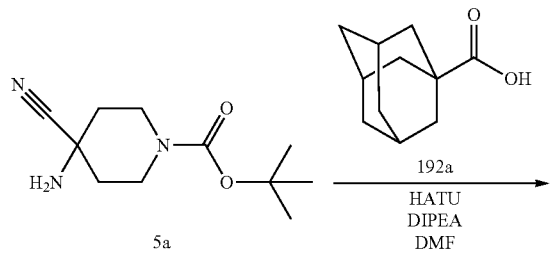

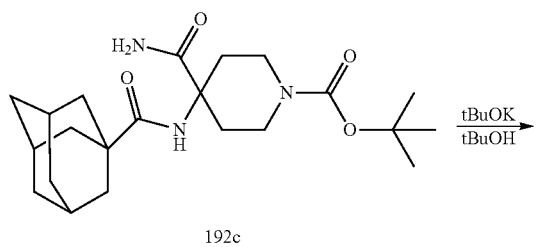

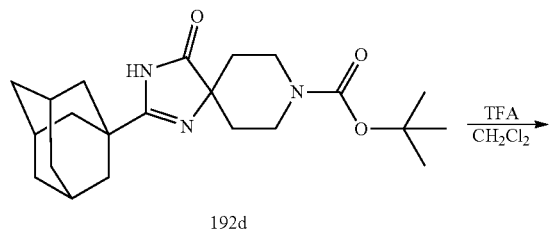

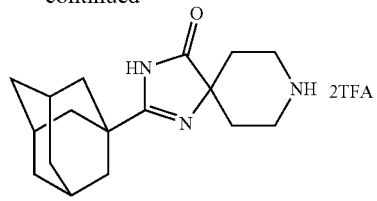

192e

2-Adamantan-1-yl-1,3,8-triaza-spiro[4.5]dec-1-en-4-one ditrifluoroacetate was synthesized by operations similar to those in Reaction 10-14, Reaction 10-11, Reaction 10-12 and Reaction 4-1 using appropriate reagents and starting material.

MS (ESI) m/z=288 (M+H)+.

The spiroamine reagent used in the synthesis of Compound 919 was synthesized by operations similar to those in Reaction 10-14, Reaction 1-4 and Reaction 4-1 using appropriate reagents and Compound 5a as a starting material.

TABLE 124

| Target Compound | Spiroamine reagent | Spiroamine reagent MS (m/z) |
|---|---|---|
| 919 | 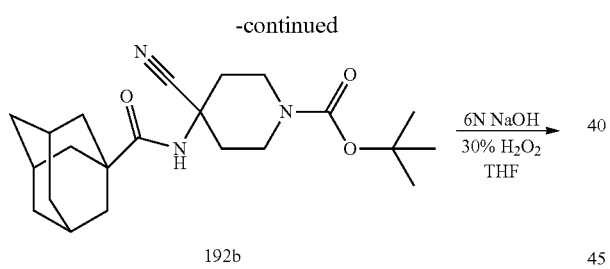 | 348 (M + H)+ |

The carboxylic acid necessary for the synthesis of the spiroamine reagent used for Compound 919 (4-(2,2,2-trifluoro-ethoxymethyl)-cyclohexanecarboxylic acid) was synthesized by the method shown below.

(Reaction 192-3)

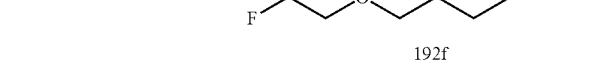

192f 2,2,2-Trifluoro-ethanol (288 μL, 4.03 mmol) was added to a mixed solution of 4-hydroxymethyl-cyclohexanecarboxylic acid benzyl ester (100 mg, 0.403 mmol), 1,1'-azobis(N,N-dimethylformamide) (139 mg, 0.805 mmol) and tributylphosphine (199 μL, 0.805 mmol) in toluene (1.2 mL) at 0° C. The mixture was stirred at 65° C. for 1.5 hours and then concentrated under reduced pressure. The resulting residue was purified by silica gel column chromatography to give 4-(2,2,2-trifluoro-ethoxymethyl)-cyclohexanecarboxylic acid benzyl ester as a colorless liquid (126 mg, 95%).

¹H-NMR (400 MHz, CDCl₃) δ 0.94-1.06 (0.4H, m), 1.23-1.47 (1.8H, m), 1.40-1.52 (0.4H, m), 1.55-1.68 (3.2H, m), 1.69-1.80 (0.8H, m), 1.82-1.91 (0.4H, m), 1.97-2.08 (2H, m), 2.25-2.34 (0.2H, m), 2.58-2.65 (0.8H, m) 3.41 (0.4H, d, J=6.8 Hz), 3.43 (1.6H, d, J=6.8 Hz), 3.78 (2H, q, J=8.8 Hz), 5.11 (0.4H, s), 5.13 (1.6H, s), 7.29-7.40 (5H, m).

(Reaction 192-4)

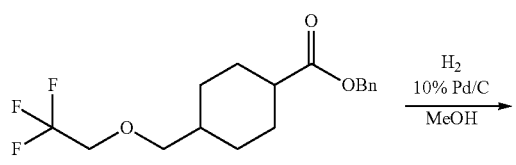

192f

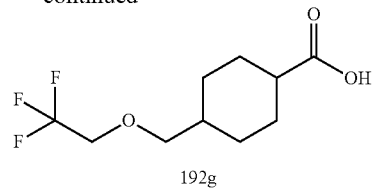

192g 4-(2,2,2-Trifluoro-ethoxymethyl)-cyclohexanecarboxylic acid was synthesized by operations similar to those in Reaction 18-2 using appropriate reagents and starting material.

¹H-NMR (400 MHz, CDCl₃) δ 0.96-2.23 (9H, m), 2.30-2.90 (1H, m), 3.37-3.49 (2H, m), 3.79 (2H, q, J=8.8 Hz), 9.56 (1H, brs).

Example 193

N-[4-(2-{2-[4-(4-Chloro-phenyl)-cyclohexyl]-4-oxo-1,3,8-triaza-spiro[4.5]dec-1-ene-8-sulfonyl}-ethyl)-3-methyl-phenyl]-acetamide (Compound 920)

(Reaction 193-1)

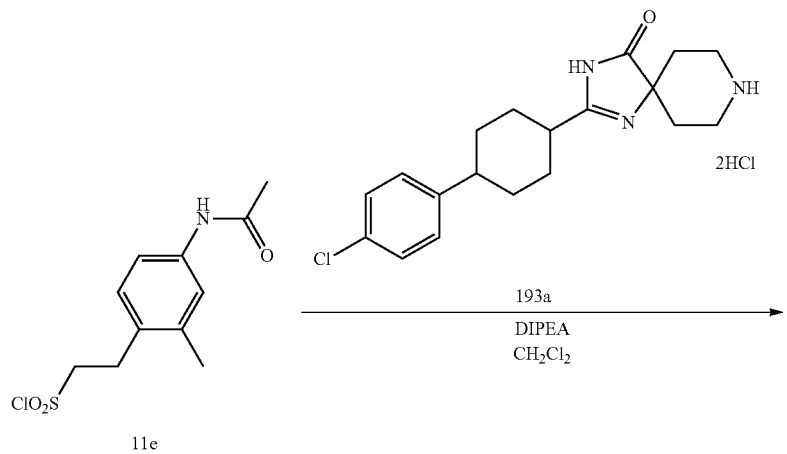

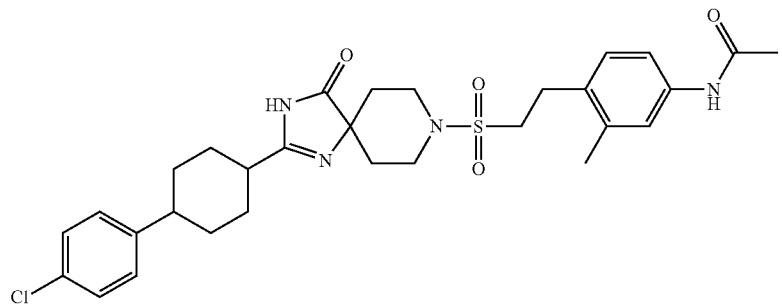

Compound 920

N-[4-(2-{2-[4-(4-Chloro-phenyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 5-4 using appropriate reagents and starting material.

MS (ESI) m/z=586 (M+H)+.

The example compounds shown below were synthesized by operations similar to those in Reaction 193-1 using appropriate reagents and starting materials.

Compounds 921 to 926

TABLE 125

| Compound | Structure | LCMS condition | Retention time (min) | MS (m/z) |
|---|---|---|---|---|
| 921 | 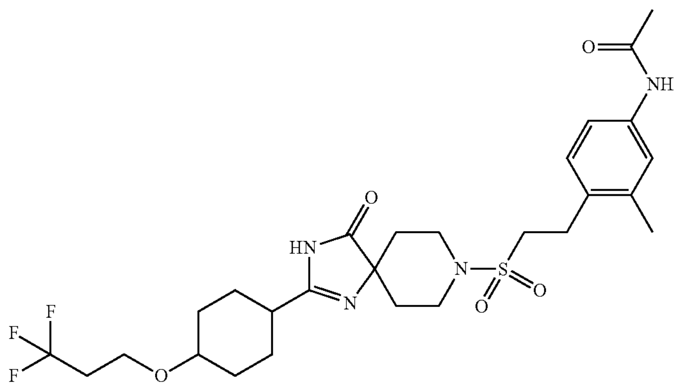 [SMILES: CC(=O)Nc1ccc(CCS(=O)(=O)N2CCC3(CC2)N=C(C2CCC(OCCC(F)(F)F)CC2)NC3=O)c(C)c1] | LCMS-B-1 | 1.79 | 587 (M + H)+ |
| 922 | 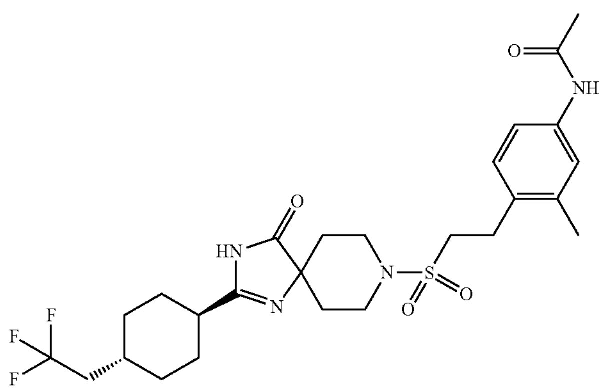 [SMILES: CC(=O)Nc1ccc(CCS(=O)(=O)N2CCC3(CC2)N=C([C@H]2CC[C@H](CC(F)(F)F)CC2)NC3=O)c(C)c1] | LCMS-C-1 | 2.53 | 557 (M + H)+ |
| 923 | 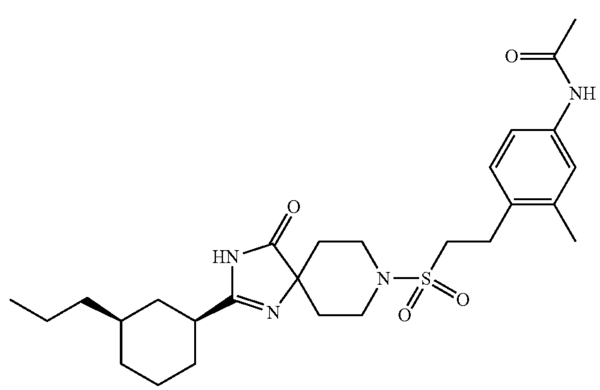 [SMILES: CCC[C@@H]1CCC[C@H](C2=NC3(CCN(S(=O)(=O)CCc4ccc(NC(C)=O)cc4C)CC3)C(=O)N2)C1] | LCMS-C-1 | 2.78 | 517 (M + H)+ |

TABLE 125-continued

| Compound | Structure | LCMS condition | Retention time (min) | MS (m/z) |
| --- | --- | --- | --- | --- |
| 924 | 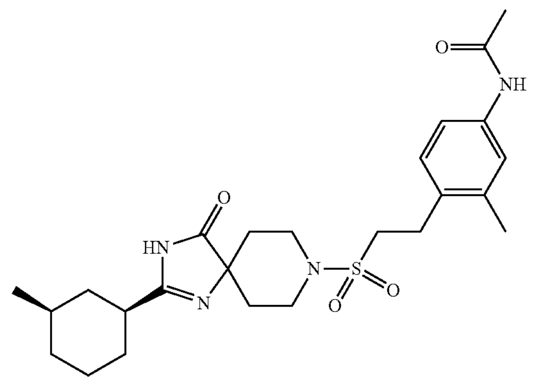 [SMILES: CC(=O)Nc1ccc(CCS(=O)(=O)N2CCC3(CC2)N=C([C@H]2CCC[C@@H](C)C2)NC3=O)c(C)c1] | LCMS-C-1 | 2.48 | 489 (M + H)+ |
| 925 | 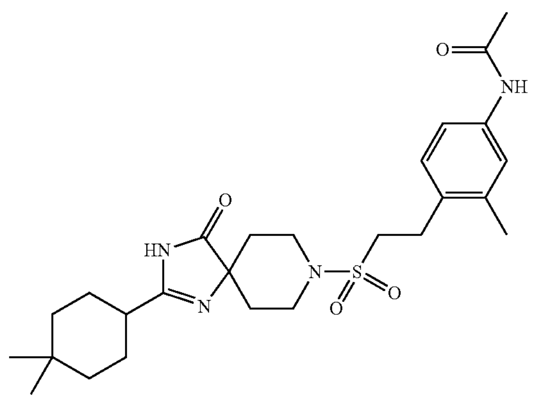 [SMILES: CC(=O)Nc1ccc(CCS(=O)(=O)N2CCC3(CC2)N=C(C2CCC(C)(C)CC2)NC3=O)c(C)c1] | LCMS-C-1 | 2.63 | 503 (M + H)+ |
| 926 | 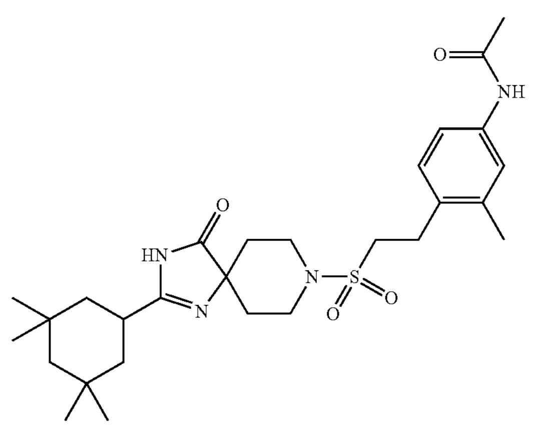 [SMILES: CC(=O)Nc1ccc(CCS(=O)(=O)N2CCC3(CC2)N=C(C2CC(C)(C)CC(C)(C)C2)NC3=O)c(C)c1] | LCMS-C-1 | 2.85 | 531 (M + H)+ |

The spiroamine reagents used in the synthesis of Compounds 920 and 921 and shown below were synthesized by operations similar to those in Reaction 10-14, Reaction 1-4 and Reaction 4-1 using appropriate reagents and Compound 5a as a starting material.

TABLE 126

| Target Compound | Spiroamine reagent | Spiroamine reagent MS (m/z) |
|---|---|---|
| 920 | 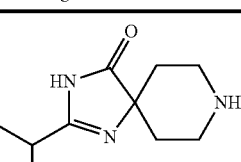 2TFA | 346 (M + H)+ |
| 921 | 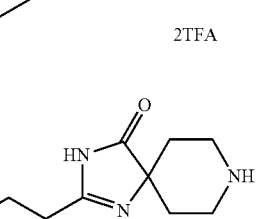 2TFA | 348 (M + H)+ |

The carboxylic acid necessary for the synthesis of the spiroamine reagent used for Compound 921 (4-(3,3,3-trifluoro-propoxy)-cyclohexanecarboxylic acid) was synthesized by the method shown below.

(Reaction 193-2)

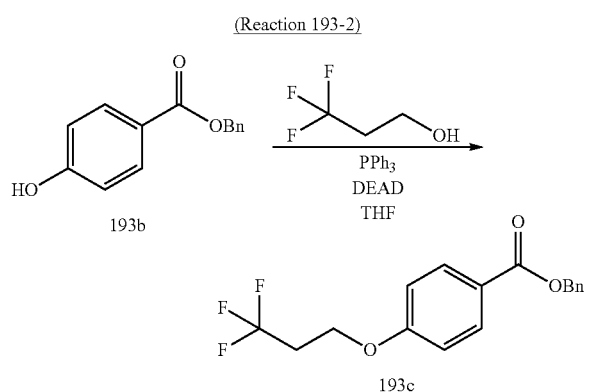

4-(3,3,3-Trifluoro-propoxy)-benzoic acid benzyl ester was synthesized by operations similar to those in Reaction 31-7 using appropriate reagents and starting material.

$^1$H-NMR (400 MHz, CDCl$_3$) δ 2.63 (2H, qt, J=10.4, 6.8 Hz), 4.23 (2H, t, J=6.0 Hz), 5.32 (2H, s), 6.90 (1H, d, J=8.8 Hz), 7.30-7.43 (5H, m), 8.02 (1H, d, J=8.8 Hz).

(Reaction 193-3)

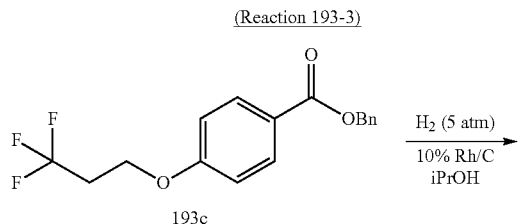

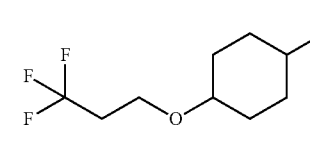

cis:trans = 4:1

193d

10% Rh—C (14.7 mg) was added to a solution of 4-(3,3,3-trifluoro-propoxy)-benzoic acid benzyl ester (147.3 mg, 0.454 mmol) in iPrOH (1.5 mL). The hydrogen pressure was adjusted to 5 atm, and the mixture was then heated with stirring at 80° C. overnight. The reaction mixture was filtered through celite, and the filtrate was then diluted with ethyl acetate. A saturated aqueous sodium bicarbonate solution was added, and the organic layer and the aqueous layer were separated. The aqueous layer was adjusted to pH 1 with 1 N hydrochloric acid and then extracted with ethyl acetate. The organic layers were sequentially washed with water and saturated brine, and then dried over anhydrous Na$_2$SO$_4$ and concentrated under reduced pressure to give 4-(3,3,3-trifluoro-propoxy)-cyclohexanecarboxylic acid as a colorless transparent oily substance (70.2 mg, 64%).

$^1$H-NMR (400 MHz, CDCl$_3$) δ 1.19-2.08 (8H, m), 2.27-2.43 (3H, m), 3.23 (0.2H, tt, J=11.2, 4.0 Hz), 3.45-3.49 (0.8H, m), 3.59 (1.6H, t, J=6.8 Hz), 3.66 (0.4H, t, J=6.8 Hz).

The spiroamine reagent used in the synthesis of Compound 922 (2-[4-(2,2,2-trifluoro-ethyl)-cyclohexyl]-1,3,8-triaza-spiro[4.5]dec-1-en-4-one ditrifluoroacetate) was synthesized by the method shown below.

(Reaction 193-4)

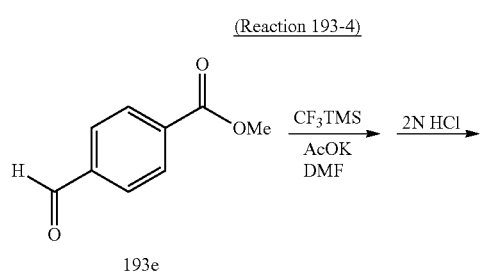

DMF (10 mL) was added to a reaction vessel containing 4-formyl-benzoic acid methyl ester (501.1 mg, 3.053 mmol) and potassium acetate (15.0 mg, 0.153 mmol), and the mixture was cooled to 0° C. Trimethyl(trifluoromethyl) silane (0.96 mL, 6.105 mmol) was added dropwise and the mixture was stirred for 50 minutes. 2 N hydrochloric acid (10 mL) was then added to the reaction mixture, and the mixture was stirred at room temperature overnight and then diluted with ethyl acetate. A saturated aqueous sodium bicarbonate solution was added, and the organic layer and the aqueous layer were separated. The organic layer was sequentially washed with water and saturated brine, and then dried over anhydrous $Na_2SO_4$ and concentrated under reduced pressure. The resulting residue was purified by silica gel column chromatography to give 4-(2,2,2-trifluoro-1-hydroxy-ethyl)-benzoic acid methyl ester (680.8 mg, 95%).

$^1$H-NMR (400 MHz, $CDCl_3$) δ 2.63 (1H, d, J=5.2 Hz), 3.92 (3H, s), 5.06-5.12 (1H, m), 7.55 (2H, d, J=8.4 Hz), 8.07 (2H, d, J=8.4 Hz).

(Reaction 193-5)

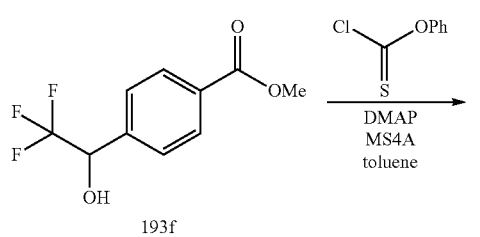

Toluene (26 mL) was added to a reaction vessel containing 4-(2,2,2-trifluoro-1-hydroxy-ethyl)-benzoic acid methyl ester (607.2 mg, 2.593 mmol), DMAP (633.6 mg, 5.186 mmol) and Molecular Sieve 4 A (916.1 mg). Phenyl chlorothioxoformate (0.54 mL, 3.889 mmol) was added dropwise and the mixture was stirred overnight. The reaction mixture was filtered through celite, and the filtrate was then concentrated under reduced pressure. The resulting residue was purified by silica gel column chromatography to give 4-(2,2,2-trifluoro-1-phenoxythiocarbonyloxy-ethyl)-benzoic acid methyl ester as a colorless oily substance (900.5 mg, 94%).

$^1$H-NMR (400 MHz, $CDCl_3$) δ 3.93 (3H, s), 6.62 (1H, q, J=6.4 Hz), 7.06-7.09 (2H, m), 7.27-7.31 (1H, m), 7.38-7.42 (2H, m), 7.60 (2H, d, J=8.4 Hz), 8.11 (2H, d, J=8.4 Hz).

(Reaction 193-6)

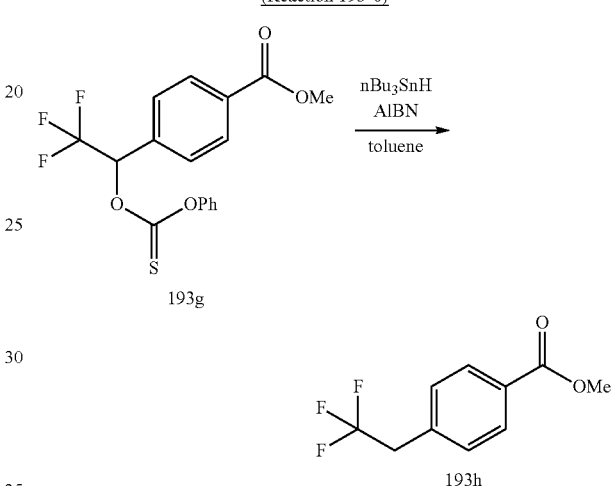

4-(2,2,2-Trifluoro-1-phenoxythiocarbonyloxy-ethyl)-benzoic acid methyl ester (462.8 mg, 1.25 mmol) and AIBN (41.0 mg, 0.25 mmol) were dissolved in ultrasonically degassed toluene (12.5 mL). Tri-n-butyltin hydride (0.50 mL, 1.874 mmol) was added and the mixture was heated with stirring at 80° C. for two hours. The reaction solution was concentrated under reduced pressure, and the resulting residue was purified by silica gel column chromatography to give 4-(2,2,2-trifluoro-ethyl)-benzoic acid methyl ester as white crystals (254.6 mg, 93%).

$^1$H-NMR (400 MHz, $CDCl_3$) δ 3.41 (2H, q, J=10.8 Hz), 3.91 (3H, s), 7.36 (2H, d, J=8.4 Hz), 8.02 (2H, d, J=8.4 Hz).

(Reaction 193-7)

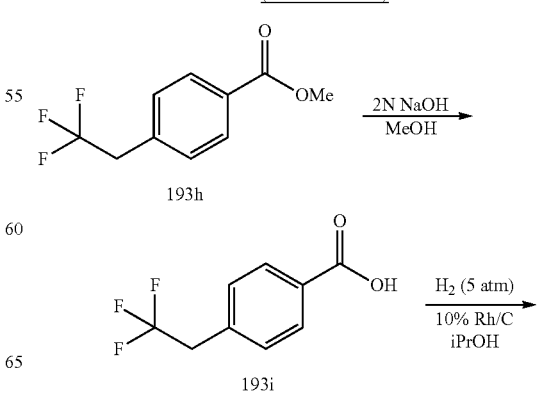

1005

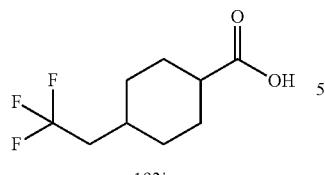

193j 4-(2,2,2-Trifluoro-ethyl)-cyclohexanecarboxylic acid was synthesized by operations similar to those in Reaction 95-18 and Reaction 193-3 using appropriate reagents and starting material.

$^1$H-NMR (400 MHz, CDCl$_3$) δ 1.03-2.08 (11H, m), 2.28 (0.33H, tt, J=12.0, 3.2 Hz), 2.61-2.64 (0.66H, m).

(Reaction 193-8)

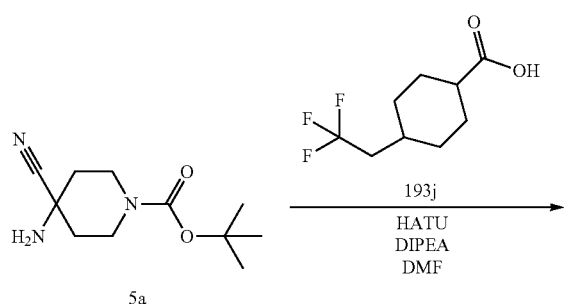

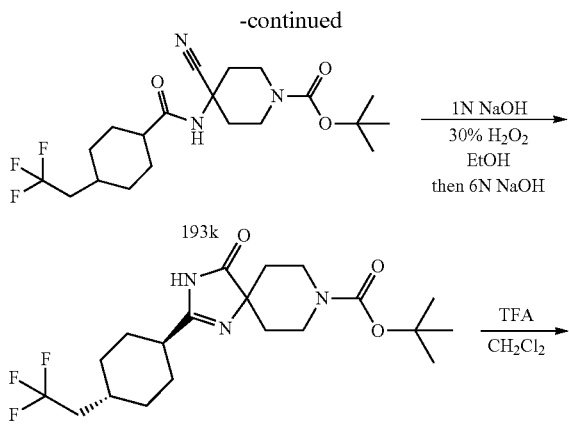

1006 almost trans

193m

2-[4-(2,2,2-Trifluoro-ethyl)-cyclohexyl]-1,3,8-triaza-spiro[4.5]dec-1-en-4-one ditrifluoroacetate was synthesized by operations similar to those in Reaction 10-14, Reaction 10-8 and Reaction 4-1 using appropriate reagents and starting material.

MS (ESI) m/z=318 (M+H)+.

The spiroamine reagent used in the synthesis of Compound 923 and shown below was synthesized by operations similar to those in Reaction 10-14, Reaction 10-8 and Reaction 4-1 using appropriate reagents and Compound 5a as a starting material.

TABLE 127

| Target Compound | Spiroamine reagent | Spiroamine reagent MS (m/z) |
|---|---|---|
| 923 | (structure with 2TFA) | 278 (M + H)+ |

The carboxylic acid necessary for the synthesis of the spiroamine reagent used for Compound 923 (3-propyl-cyclohexanecarboxylic acid) was synthesized by the method shown below.

(Reaction 193-9)

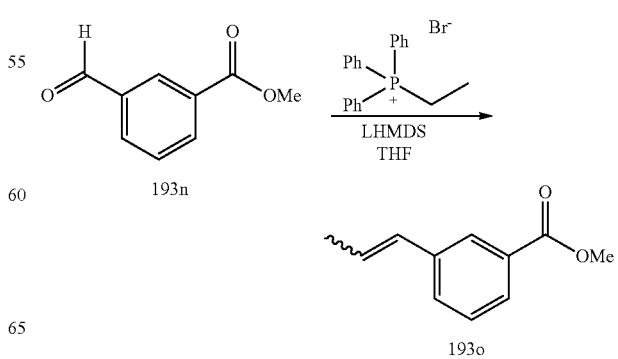

A suspension solution of ethyltriphenylphosphonium bromide (1079.3 mg, 2.907 mmol) in THF (10 mL) was cooled to 0° C. LHMDS (2.781 mL, 2.781 mmol, 1.0 M in THF) was added dropwise, and the mixture was stirred for 30 minutes. A solution of 3-formyl-benzoic acid methyl ester (415.0 mg, 2.528 mmol) in THF (2.5 mL) was then added dropwise, and the mixture was stirred for 10 minutes and then stirred at room temperature overnight. The reaction mixture was quenched by adding a saturated aqueous ammonium chloride solution and then extracted with ethyl acetate. The organic layer was sequentially washed with water and saturated brine, and then dried over anhydrous $Na_2SO_4$ and concentrated under reduced pressure. The resulting residue was purified by silica gel column chromatography to give 3-propenyl-benzoic acid methyl ester as a yellow transparent oily substance (218.2 mg, 49%).

$^1$H-NMR (400 MHz, $CDCl_3$) δ 1.89-1.92 (3H, m), 3.92 (1H, s), 3.93 (2H, s), 5.86 (0.66H, dq, J=11.6, 7.2 Hz), 6.32 (0.33H, dq, J=15.6, 6.4 Hz), 6.41-6.47 (1H, m), 7.34-7.43 (1H, m), 7.47-7.51 (1H, m), 7.84-7.90 (1H, m), 7.97-8.01 (1H, m).

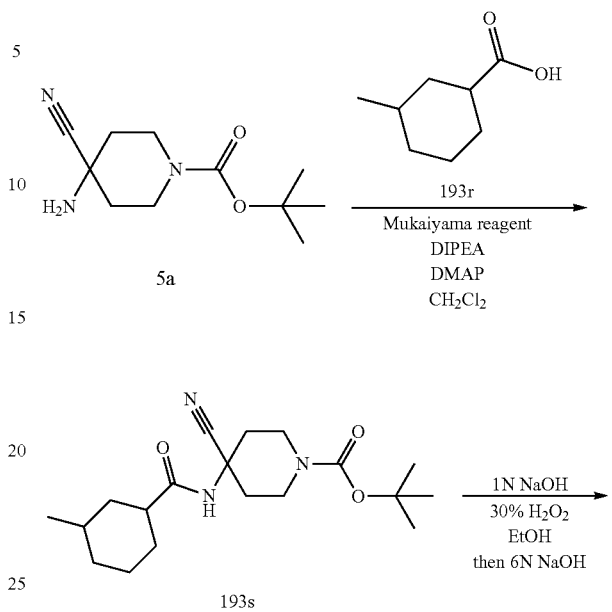

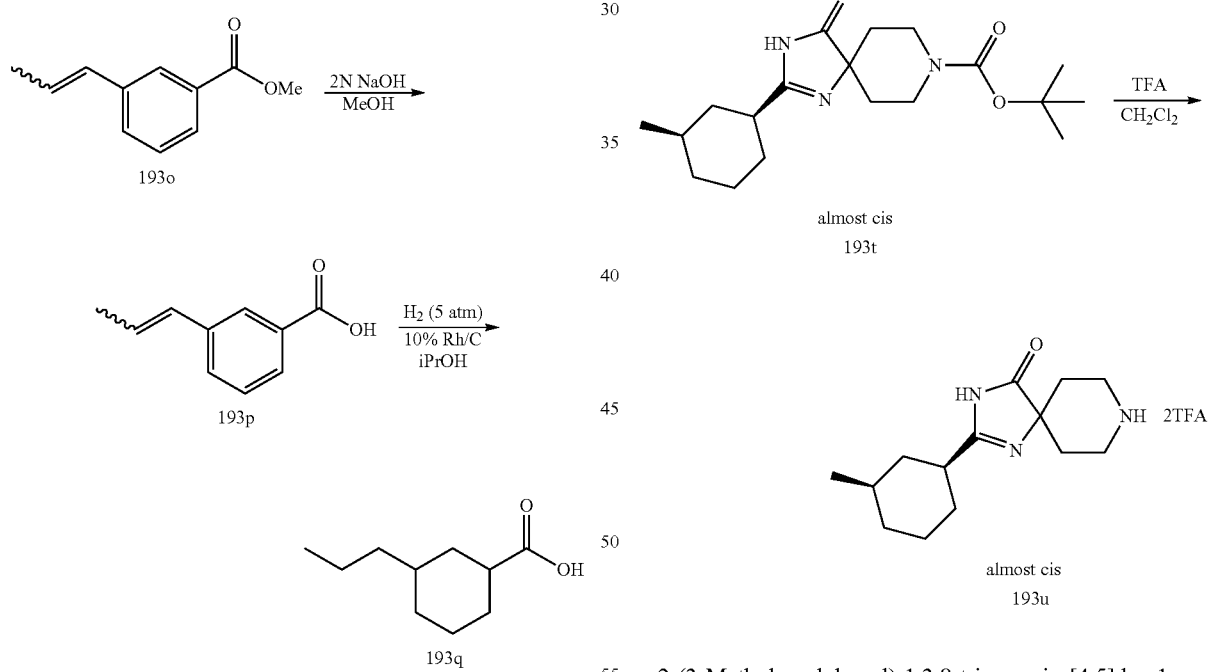

3-Propyl-cyclohexanecarboxylic acid was synthesized by operations similar to those in Reaction 95-18 and Reaction 193-3 using appropriate reagents and starting material.

$^1$H-NMR (400 MHz, $CDCl_3$) δ 0.80-2.05 (16H, m), 2.33 (0.6H, tt, J=12.4, 3.2 Hz), 2.67-2.70 (0.4H, m).

The spiroamine reagent used in the synthesis of Compound 924 (2-(3-methyl-cyclohexyl)-1,3,8-triaza-spiro[4.5]dec-1-en-4-one ditrifluoroacetate) was synthesized by the method shown below.

2-(3-Methyl-cyclohexyl)-1,3,8-triaza-spiro[4.5]dec-1-en-4-one ditrifluoroacetate was synthesized by operations similar to those in Reaction 176-2, Reaction 10-8 and Reaction 4-1 using appropriate reagents and starting material.

MS (ESI) m/z=250 (M+H)+.

The spiroamine reagents used in the synthesis of Compounds 925 and 926 and shown below were synthesized by operations similar to those in Reaction 10-14, Reaction 10-8 and Reaction 4-1 using appropriate reagents and starting materials.

TABLE 128

| Target Compound | Spiroamine reagent | Spiroamine reagent MS (m/z) |
|---|---|---|
| 925 | | 264 (M + H)+ |
| 926 | | 292 (M + H)+ |

The carboxylic acid necessary for the synthesis of the spiroamine reagent used for Compound 926 (3,3,5,5-tetramethyl-cyclohexanecarboxylic acid) was synthesized by the method shown below.

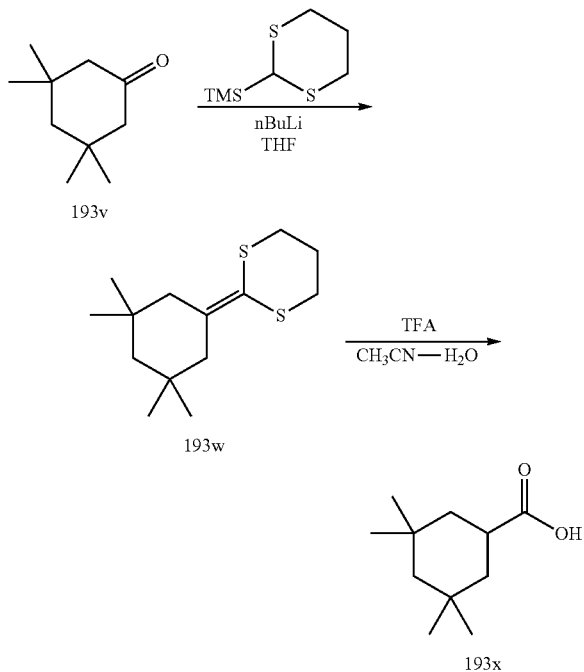

A solution of [1,3]dithian-2-yl-trimethyl-silane (566.4 mg, 2.944 mmol) in THF (6 mL) was cooled to 0° C. nBuLi (1.78 mL, 2.845 mmol, 1.6 M in n-hexane) was added dropwise and then the mixture was stirred for 10 minutes. The reaction solution was cooled to −78° C. A solution of 3,3,5,5-tetramethyl-cyclohexanone (302.7 mg, 1.962 mmol) in THF (2 mL) was then added dropwise, and the mixture was stirred for two hours. The reaction mixture was quenched by adding a saturated aqueous ammonium chloride solution and extracted with ethyl acetate. The organic layer was sequentially washed with water and saturated brine, and then dried over anhydrous $Na_2SO_4$ and concentrated under reduced pressure.

The resulting residue was dissolved in acetonitrile (2.1 mL). Water (0.52 mL) and trifluoroacetic acid (0.51 mL) were added and the mixture was heated with stirring at 65° C. for three hours. The reaction solution was cooled to room temperature. A 30% aqueous hydrogen peroxide solution (3.2 mL) was then added and the mixture was heated with stirring at 80° C. for one hour. The reaction solution was cooled to room temperature, and a 5 M aqueous sodium hydroxide solution (15.7 mL) was then added, followed by extraction with ether. A saturated aqueous sodium bicarbonate solution was added, and the organic layer and the aqueous layer were separated. The aqueous layer was adjusted to pH 1 with 2 N hydrochloric acid and then extracted with ethyl acetate. The organic layers were sequentially washed with water and saturated brine, and then dried over anhydrous $Na_2SO_4$ and concentrated under reduced pressure to give 3,3,5,5-tetramethyl-cyclohexanecarboxylic acid as a white powder (342.3 mg, 95% in two steps).

$^1$H-NMR (400 MHz, $CDCl_3$) δ 0.93 (6H, s), 1.01 (6H, s), 1.06-1.28 (4H, m), 1.68-1.71 (2H, m), 2.65 (1H, tt, J=12.8, 3.2 Hz).

Example 194

N-[4-(2-{2-[4-(2-Methoxy-ethyl)-cyclohexyl]-4-oxo-1,3,8-triaza-spiro[4.5]dec-1-ene-8-sulfonyl}-ethyl)-3-methyl-phenyl]-acetamide (Compound 927)

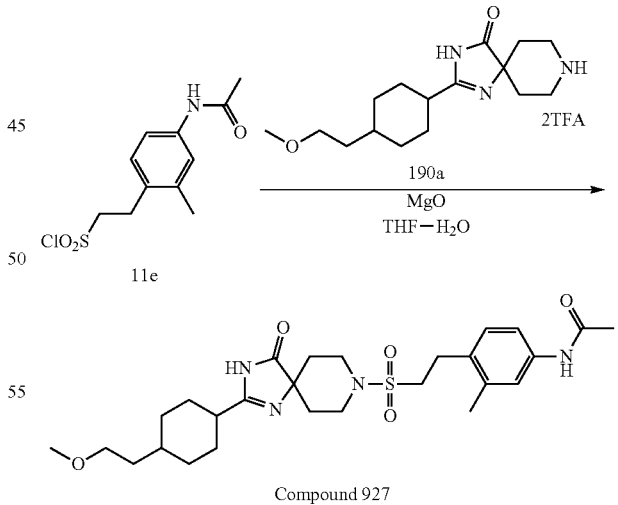

Compound 927

N-[4-(2-{2-[4-(2-Methoxy-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 190-1 using appropriate reagents and starting material.

MS (ESI) m/z=533 (M+H)+.

Example 195

[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester
(Compound 928)

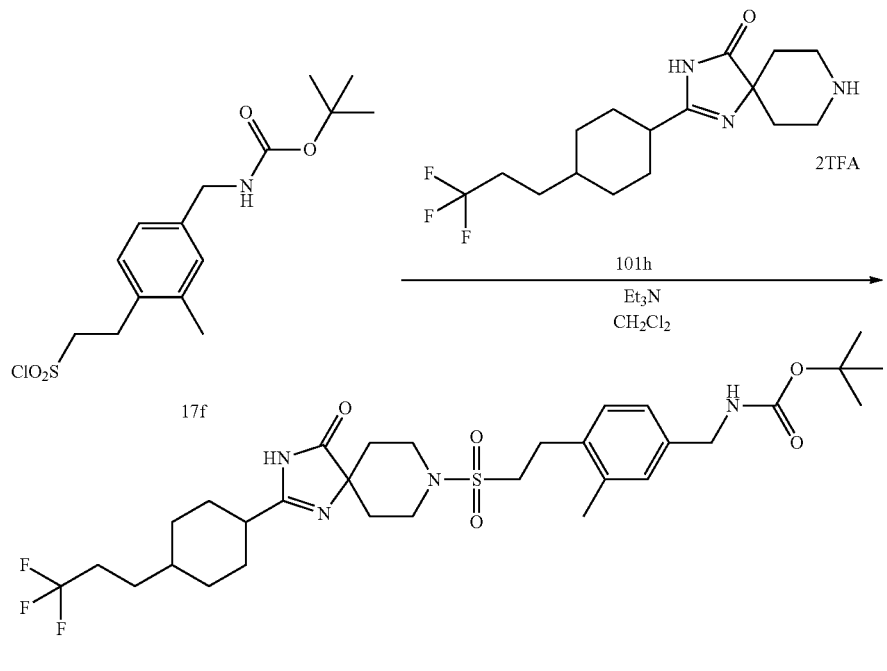

[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-carbamic acid tert-butyl ester was synthesized by operations similar to those in Reaction 5-4 using appropriate reagents and starting material.

MS (ESI) m/z=643 (M+H)+.

Example 196

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide
(Compound 929)

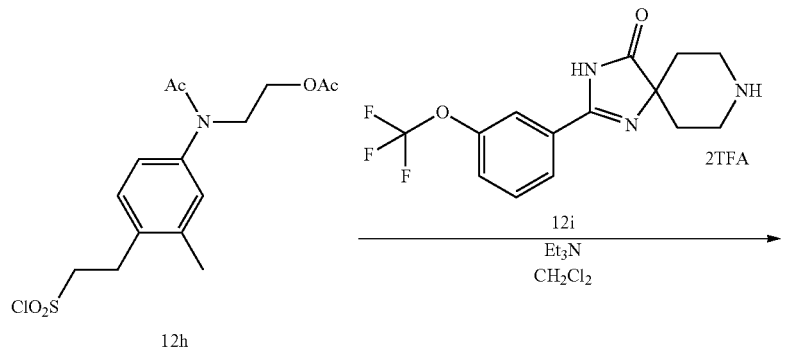

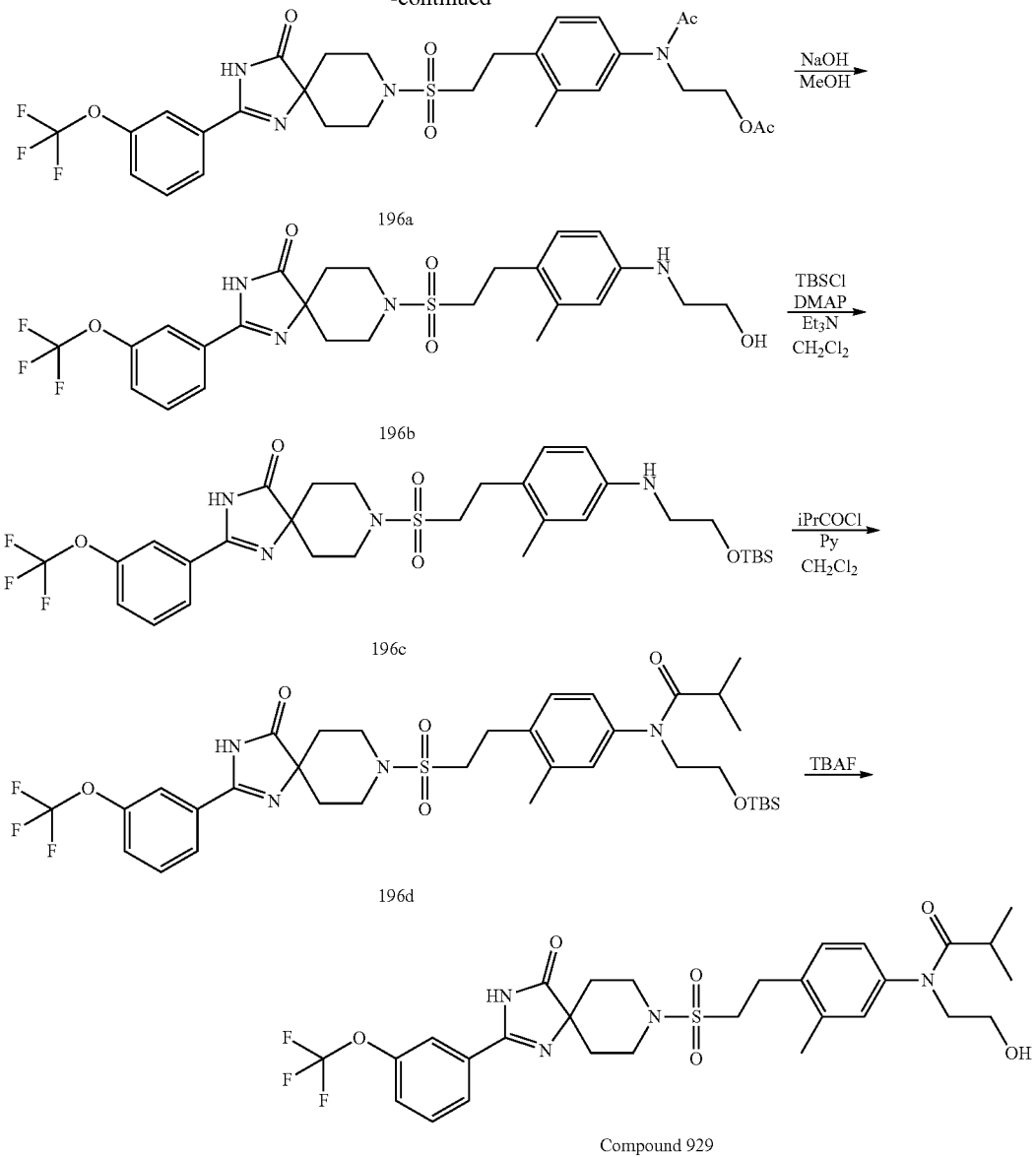

N-(2-Hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-isobutylamide was synthesized by operations similar to those in Reaction 5-4, Reaction 96-16, Reaction 157-2, Reaction 105-2 and Reaction 39-2 using appropriate reagents and starting material.

MS (ESI) m/z=625 (M+H)+.

Example 197

2-Hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide (Compound 930)

(Reaction 197-1)

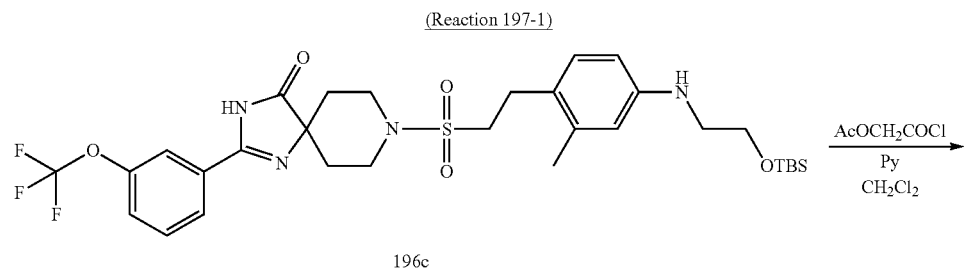

-continued

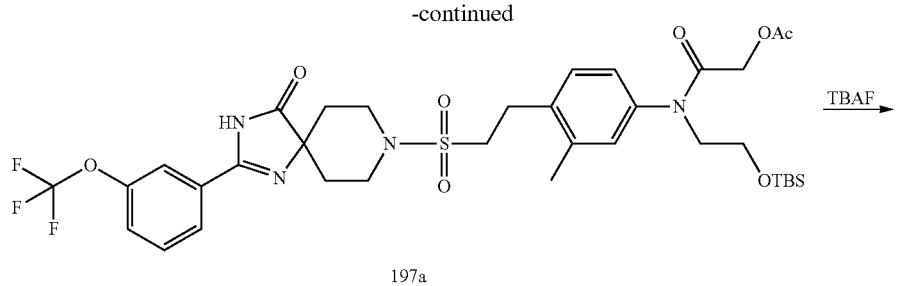

197a

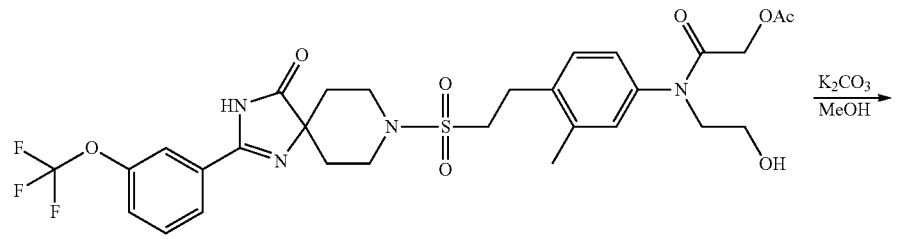

197b

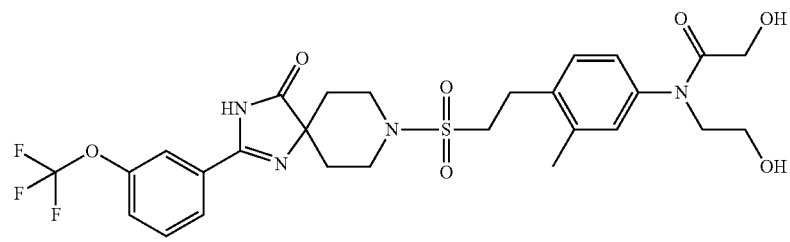

Compound 930

2-Hydroxy-N-(2-hydroxy-ethyl)-N-(3-methyl-4-{2-[4-oxo-2-(3-trifluoromethoxy-phenyl)-1,3,8-triaza-spiro[4.5]dec-1-ene-8-sulfonyl]-ethyl}-phenyl)-acetamide was synthesized by operations similar to those in Reaction 105-2, Reaction 39-2 and Reaction 12-5 using appropriate reagents and starting material.

MS (ESI) m/z=613 (M+H)+.

Example 198

N-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide (Compound 931)

(Reaction 198-1)

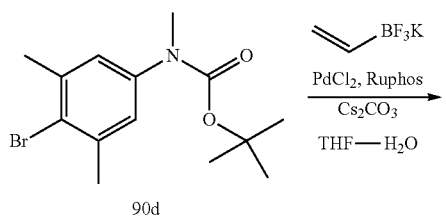

90d

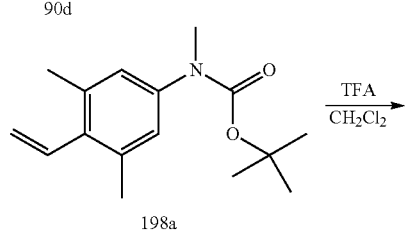

198a

-continued

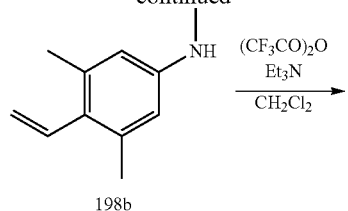

198b

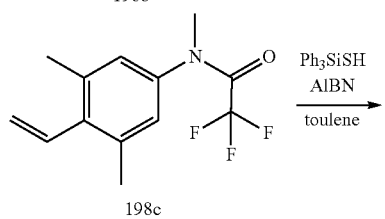

198c

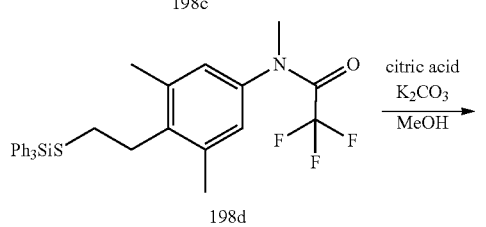

198d

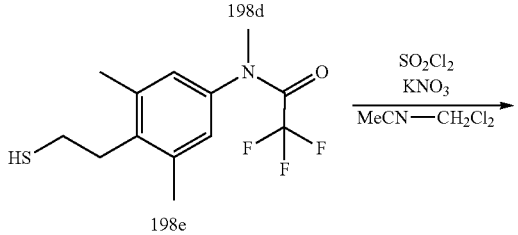

198e

1017

-continued

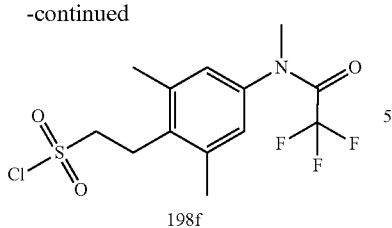

198f

2-{2,6-Dimethyl-4-[methyl-(2,2,2-trifluoro-acetyl)-amino]-phenyl}-ethanesulfonyl chloride was synthesized by operations similar to those in Reaction 10-2, Reaction 4-1, Reaction 19-2, Reaction 10-3, Reaction 10-4 and Reaction 10-5 using appropriate reagents and starting material.

MS (ESI) m/z=358 (M+H)+.

(Reaction 198-2)

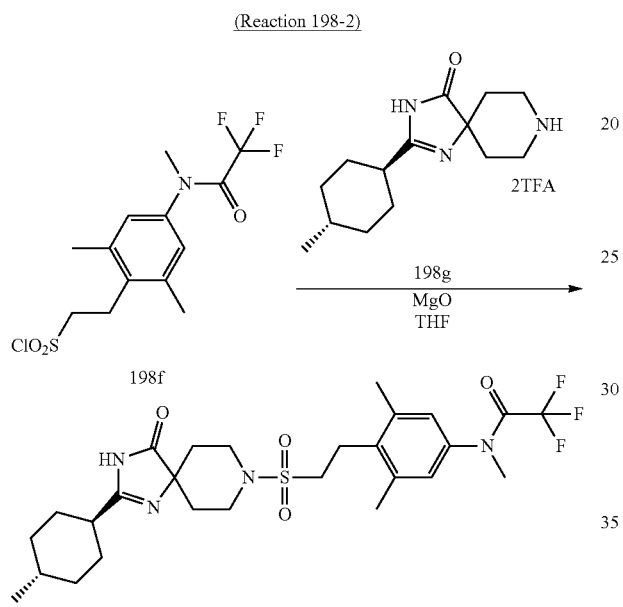

Compound 931

N-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide was synthesized by operations similar to those in Reaction 190-1 using appropriate reagents and starting material.

MS (ESI) m/z=571 (M+H)+.

1018

Example 199

N-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide (Compound 932)

(Reaction 199-1)

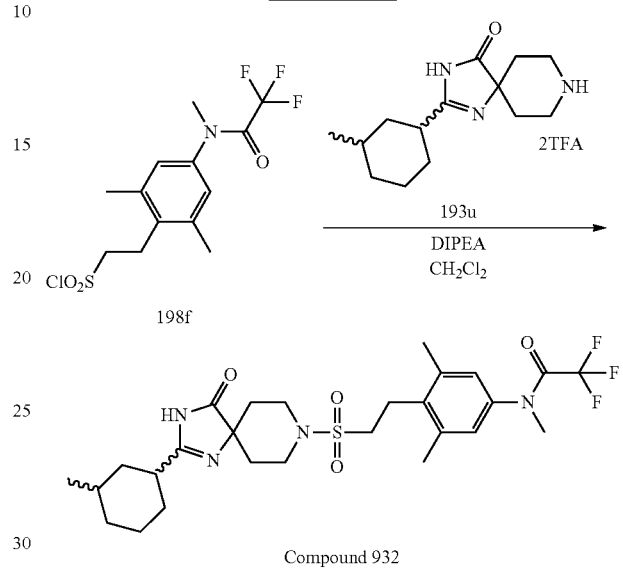

Compound 932

N-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide was synthesized by operations similar to those in Reaction 5-4 using appropriate reagents and starting material.

MS (ESI) m/z=571 (M+H)+.

The example compound shown below was synthesized by operations similar to those in Reaction 199-1 using appropriate reagents and starting material.

Compound 933

TABLE 129

| Compound | Structure | LCMS condition | Retention time (min) | MS (m/z) |
|---|---|---|---|---|
| 933 | 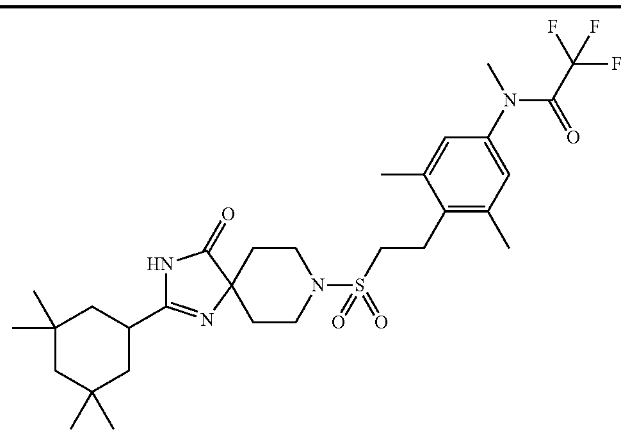 | LCMS-C-1 | 3.13 | 613 (M + H)+ |

Example 200

1-{4-[2-(2-Cycloheptyl-4-oxo-1,3,8-triaza-spiro[4.5]
dec-1-ene-8-sulfonyl)-ethyl]-3,5-dimethyl-phenyl}-
1-methyl-urea (Compound 934)

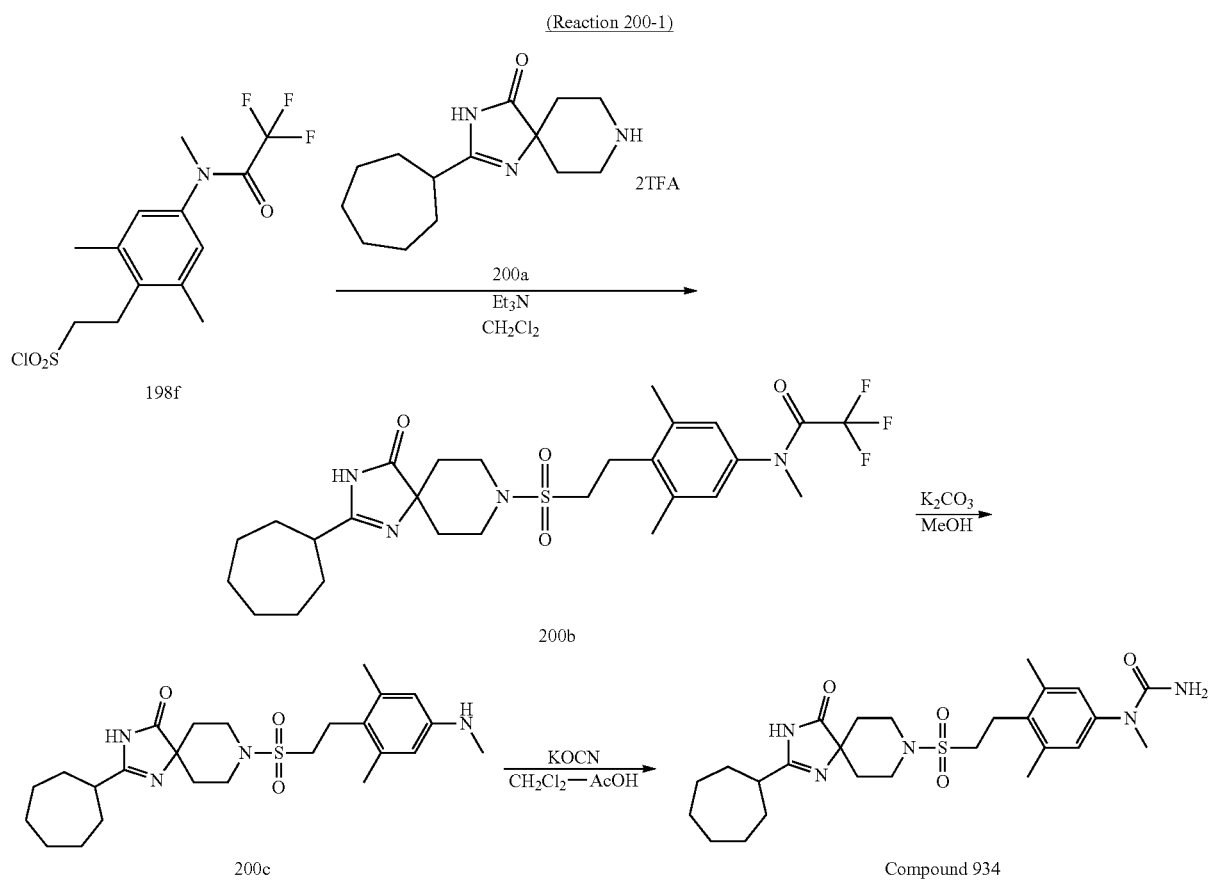

1-{4-[2-(2-Cycloheptyl-4-oxo-1,3,8-triaza-spiro[4.5]dec-1-ene-8-sulfonyl)-ethyl]-3,5-dimethyl-phenyl}-1-methyl-urea was synthesized by operations similar to those in Reaction 5-4, Reaction 12-5 and Reaction 89-2 (using KOCN) using appropriate reagents and starting material.
MS (ESI) m/z=518 (M+H)+.

The example compounds shown below were synthesized by operations similar to those in Reaction 200-1 using appropriate reagents and starting materials.

Compounds 935, 938 and 941

TABLE 130

| Compound | Structure | LCMS condition | Retention time (min) | MS (m/z) |
|---|---|---|---|---|
| 935 | 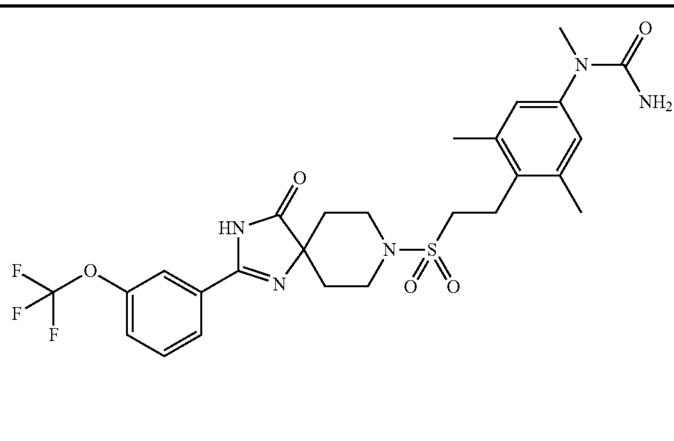 | LCMS-A-1 | 2.35 | 582 (M + H)+ |

TABLE 130-continued

| Compound | Structure | LCMS condition | Retention time (min) | MS (m/z) |
|---|---|---|---|---|
| 938 | 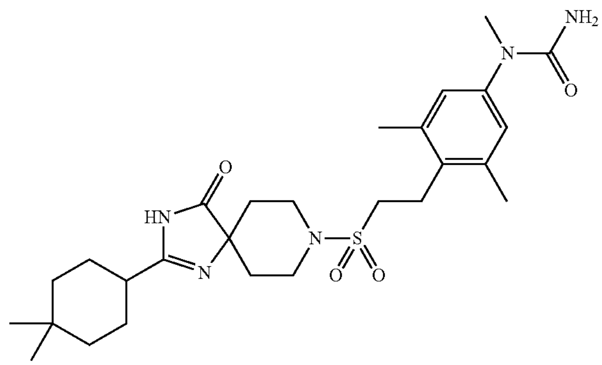 [SMILES: Cc1cc(N(C)C(N)=O)cc(C)c1CCS(=O)(=O)N1CCC2(CC1)N=C(C1CCC(C)(C)CC1)NC2=O] | LCMS-C-1 | 2.70 | 532 (M + H)+ |
| 941 | 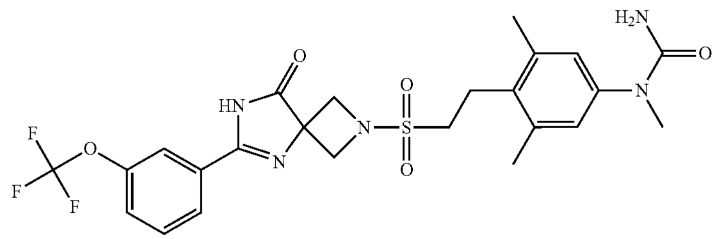 [SMILES: Cc1cc(N(C)C(N)=O)cc(C)c1CCS(=O)(=O)N1CC2(C1)N=C(c1cccc(OC(F)(F)F)c1)NC2=O] | LCMS-F-1 | 0.93 | 554 (M + H)+ |

The spiroamine reagent used in the synthesis of Compound 941 (6-(3-trifluoromethoxy-phenyl)-2,5,7-triazaspiro[3.4]oct-5-en-8-one ditrifluoroacetate) was synthesized as follows.

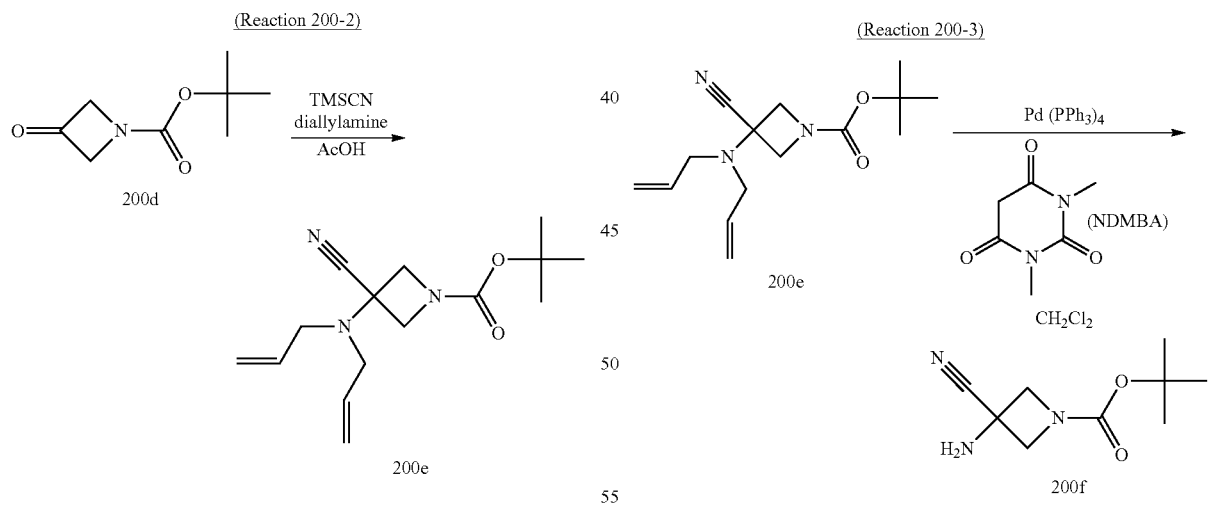

Diallylamine (0.31 ml, 2.5 mmol) and trimethylsilylnitrile (0.155 ml, 1.25 mmol) were added to a solution of 3-oxo-azetidine-1-carboxylic acid tert-butyl ester (171 mg, 1.00 mmol) in acetic acid (1.7 ml, 30 mmol), and the mixture was stirred at 60° C. for four hours. A Saturated aqueous sodium bicarbonate solution (11.5 ml) was added to the reaction mixture, followed by extraction with ethyl acetate. The organic layer was then dried over MgSO4 and concentrated under reduced pressure. The resulting residue was purified by silica gel column chromatography (hexane-ethyl acetate) to give 3-cyano-3-diallylamino-azetidine-1-carboxylic acid tert-butyl ester (212 mg, 76%).

$^1$H-NMR (400 MHz, CDCl$_3$) δ 1.45 (9H, s), 3.10 (4H, d, J=7.0 Hz), 4.01 (2H, d, J=8.6 Hz), 4.09 (2H, d, J=8.6 Hz), 5.19 (1H, d, J=10.2 Hz), 5.30 (1H, d, J=17.0 Hz), 5.82 (1H, m).

A solution of 3-cyano-3-diallylamino-azetidine 1-carboxylic acid tert-butyl ester (143.5 mg, 0.5174 mmol), 1,3-dimethylbarbituric acid (242.5 mg, 1.553 mmol) and tetrakis(triphenylphosphine)palladium(0) (30.3 mg, 0.0262 mmol) in dichloromethane (1.3 ml) was stirred at 40° C. for five hours. A saturated aqueous sodium bicarbonate solution was added to the reaction mixture, followed by extraction with ethyl acetate. The organic layer was then dried over MgSO4 and concentrated under reduced pressure. The resulting residue was purified by silica gel column chromatography (hexane-ethyl acetate) to give 3-amino-3-cyano-azetidine-1-carboxylic acid tert-butyl ester (98 mg, 96%).

$^1$H-NMR (400 MHz, CDCl$_3$) δ 1.44 (9H, s), 2.03 (2H, br), 3.88 (2H, d, J=8.8 Hz), 4.34 (2H, d, J=8.8 Hz).

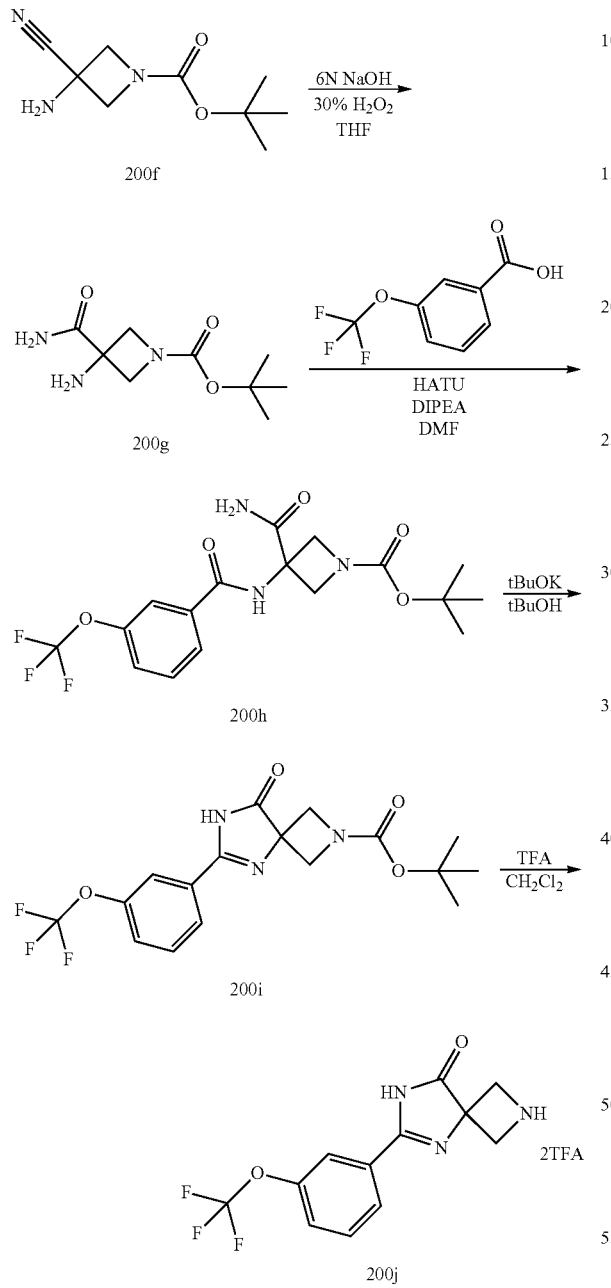

6-(3-Trifluoromethoxy-phenyl)-2,5,7-triaza-spiro[3.4]oct-5-en-8-one ditrifluoroacetate was synthesized by operations similar to those in Reaction 10-11, Reaction 10-14, Reaction 10-12 and Reaction 4-1 using appropriate reagents and starting material.

$^1$H-NMR (400 MHz, CDCl$_3$) δ 4.31 (2H, d, J=12.0 Hz), 4.40 (2H, d, J=12.0 Hz), 7.56 (1H, d, J=8.2 Hz), 7.66 (1H, t, J=8.2 Hz), 7.95 (1H, d, J=8.2 Hz), 7.96 (1H, s).

Example 201

1-[3,5-Dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea (Compound 936) and 1-[2-chloro-3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea (Compound 937)

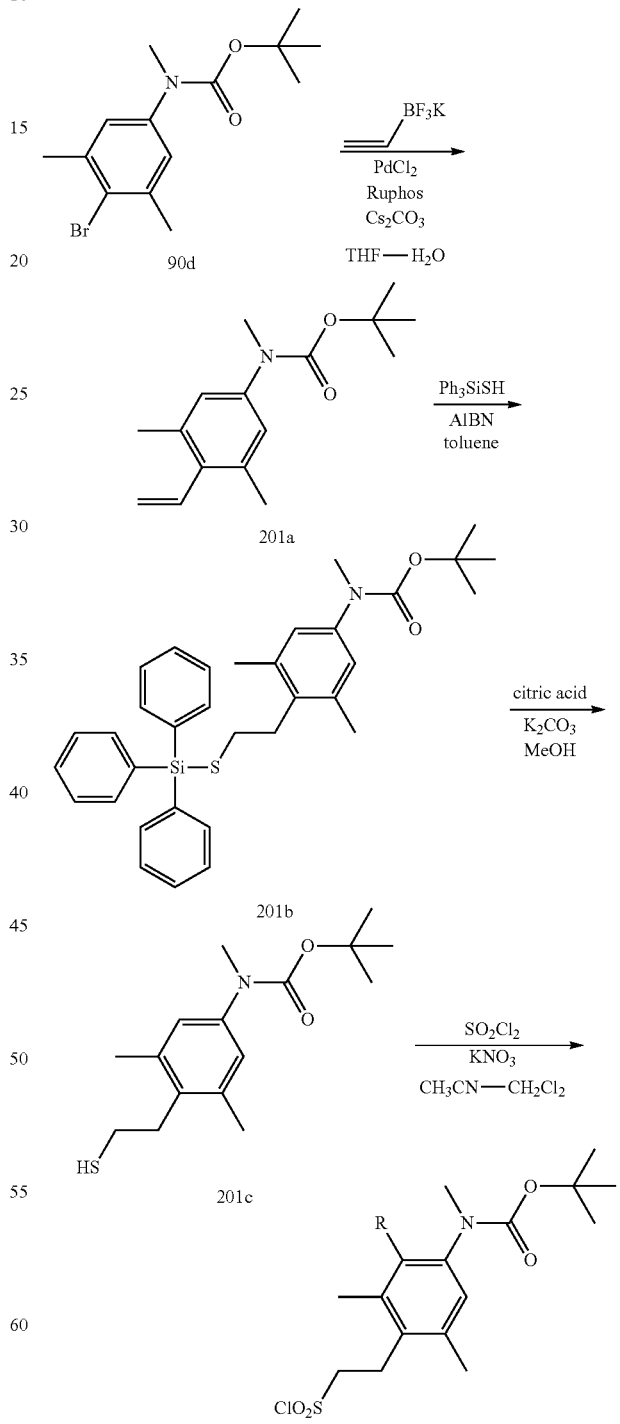

A mixture of [4-(2-chlorosulfonyl-ethyl)-3,5-dimethyl-phenyl]-methyl-carbamic acid tert-butyl ester and [2-chloro-4-(2-chlorosulfonyl-ethyl)-3,5-dimethyl-phenyl]-methyl-carbamic acid tert-butyl ester was synthesized by operations similar to those in Reaction 10-2 (using RuPhos as a ligand), Reaction 10-3, Reaction 10-4 and Reaction 10-5 using appropriate reagents and starting material.
(R═H:R═Cl=0.6:0.4)
$^1$H-NMR (400 MHz, CDCl$_3$) δ 1.32-1.54 (9H, m), 2.32-2.47 (6H, m), 3.08-3.25 (3H, m), 3.29-3.44 (2H, m), 3.60-3.74 (2H, m), 6.96 (1.6H, m).

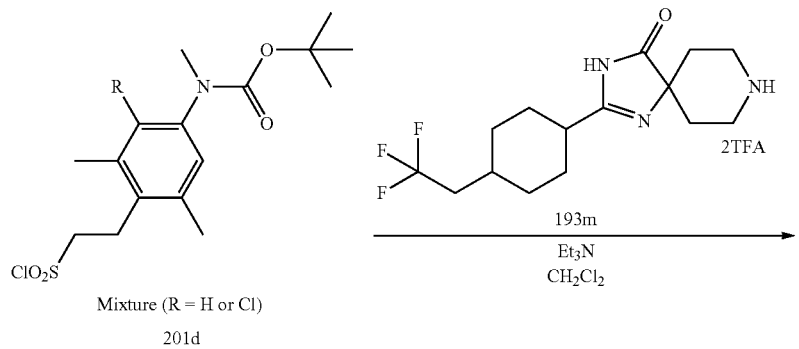

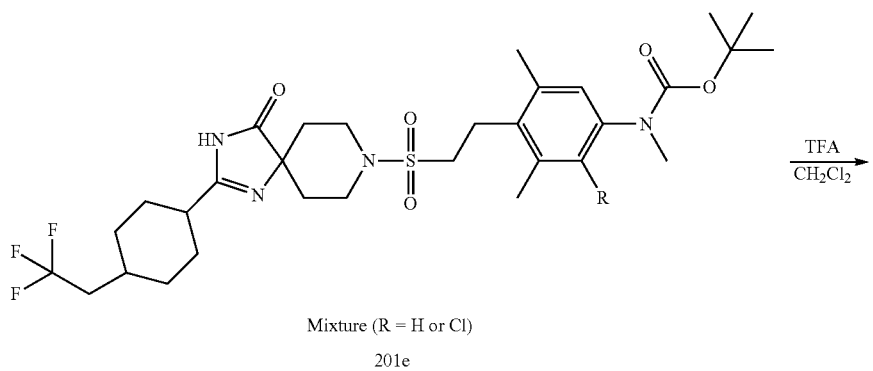

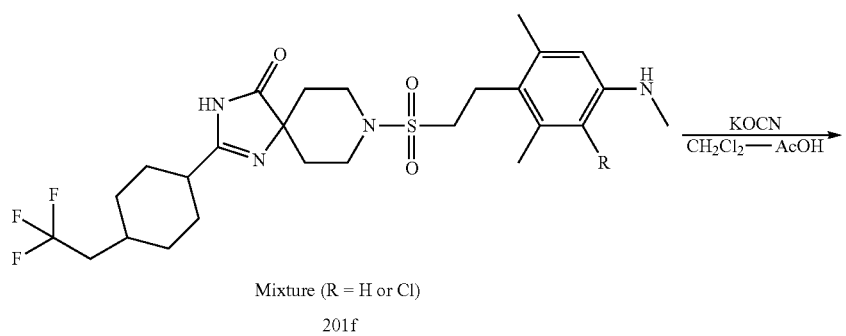

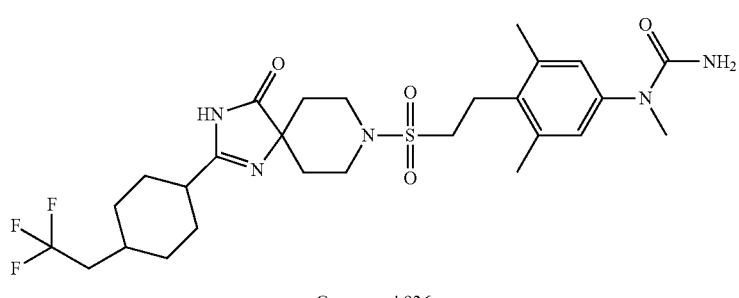

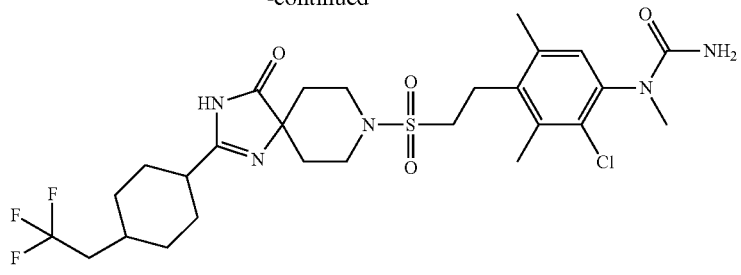

Compound 937

1-[3,5-Dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea MS (ESI) m/z=586 (M+H)+ and

1-[2-chloro-3,5-dimethyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-1-methyl-urea MS (ESI) m/z=620 (M+H)+ were obtained by operations similar to those in Reaction 5-4, Reaction 4-1 and Reaction 89-2 (using KOCN) using the starting material obtained above and appropriate reagents.

Example 202

1-[3,5-Dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea (Compound 939)

(Reaction 202-1)

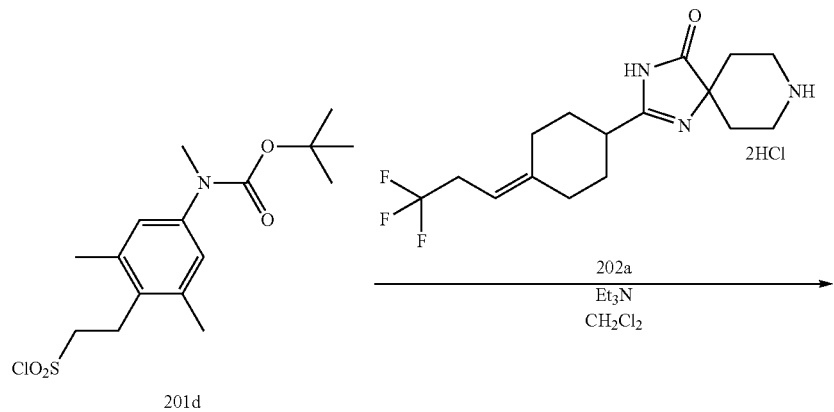

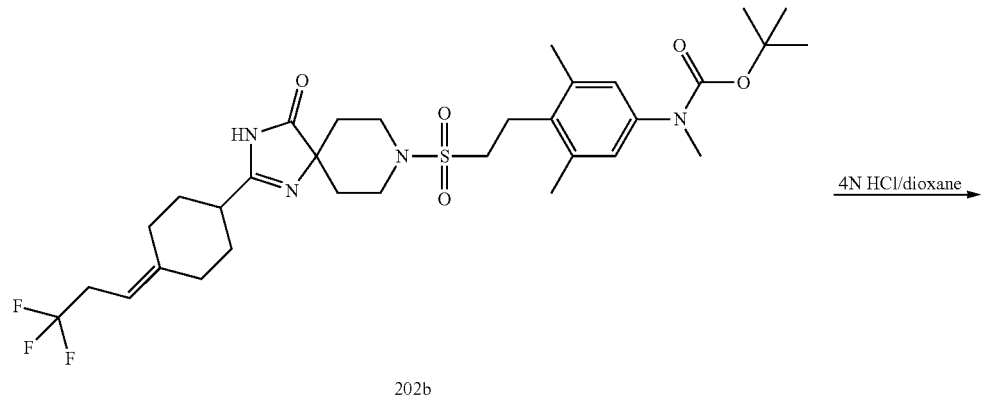

-continued

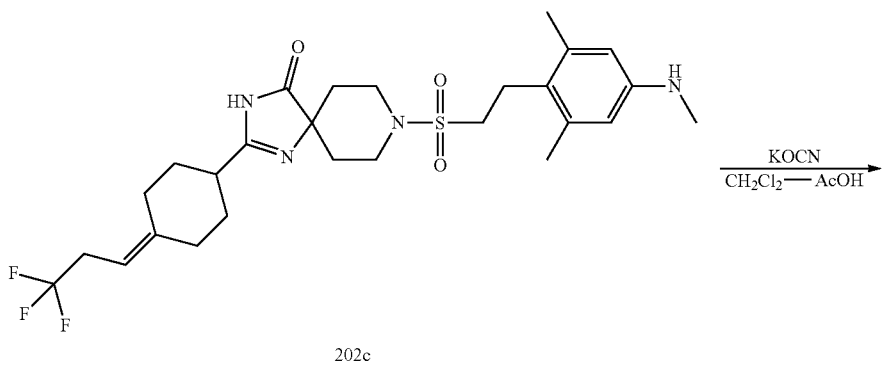

202c

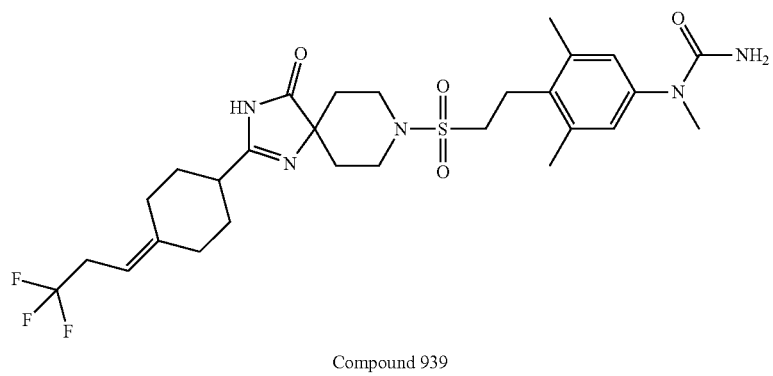

Compound 939

1-[3,5-Dimethyl-4-(2-{4-oxo-2-[4-(3,3,3-trifluoro-propylidene)-cyclohexyl]-1,3,8-triaza-spiro[4.5]dec-1-ene-8-sulfonyl}-ethyl)-phenyl]-1-methyl-urea was synthesized by operations similar to those in Reaction 5-4, Reaction 5-3 and Reaction 89-2 (using KOCN) using appropriate reagents and starting material.

MS (ESI) m/z=598 (M+H)+.

The example compound shown below was synthesized by operations similar to those in Reaction 202-1 using appropriate reagents and starting material.

Compound 940

TABLE 131

| Compound | Structure | LCMS condition | Retention time (min) | MS (m/z) |
|---|---|---|---|---|
| 940 | 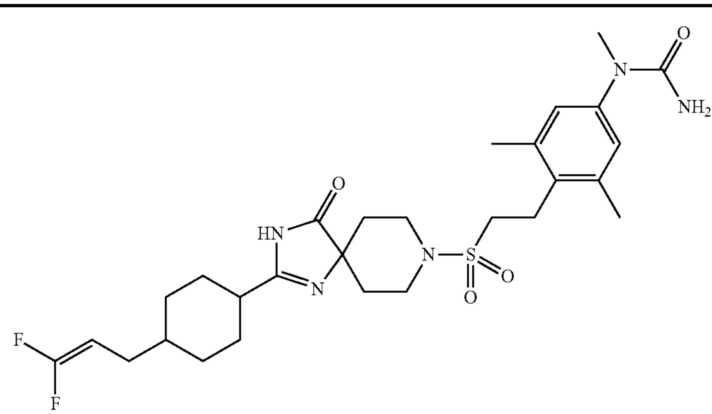 | LCMS-B-1 | 1.91 | 580 (M + H)+ |

1031

The spiroamine reagent used in the synthesis of Compound 939 (2-[4-(3,3,3-trifluoro-propylidene)-cyclohexyl]-1,3,8-triaza-spiro[4.5]dec-1-en-4-one dihydrochloride) was synthesized as follows.

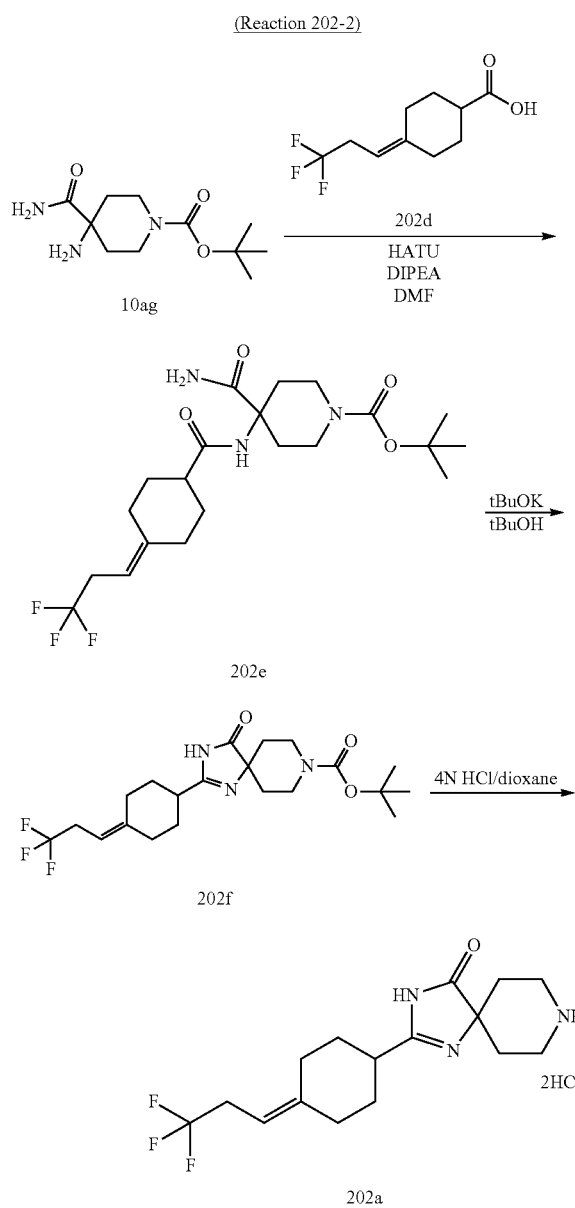

2-[4-(3,3,3-Trifluoro-propylidene)-cyclohexyl]-1,3,8-triaza-spiro[4.5]dec-1-en-4-one dihydrochloride was synthesized by operations similar to those in Reaction 10-14, Reaction 10-12 and Reaction 5-3 using appropriate reagents and starting material.

MS (ESI) m/z=330 (M+H)+.

The spiroamine reagent used in the synthesis of Compound 940 and shown below was synthesized by operations similar to those in Reaction 10-14, Reaction 10-12 and Reaction 5-3 using appropriate reagents and Compound 10ag as a starting material.

1032

TABLE 132

| Target Compound | Spiroamine reagent | Spiroamine reagent MS (m/z) |
|---|---|---|
| 940 | 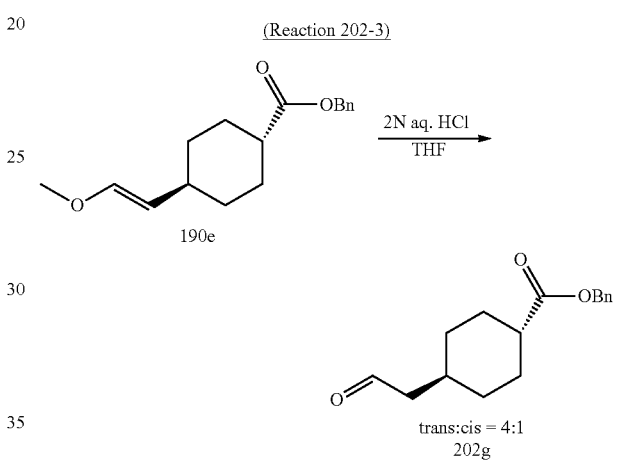 | 312 (M + H)+ |

The carboxylic acid derivative necessary for the synthesis of the spiroamine reagent used in the synthesis of Compound 940 (4-(3,3-difluoro-allyl)-cyclohexanecarboxylic acid) was synthesized in the following manner.

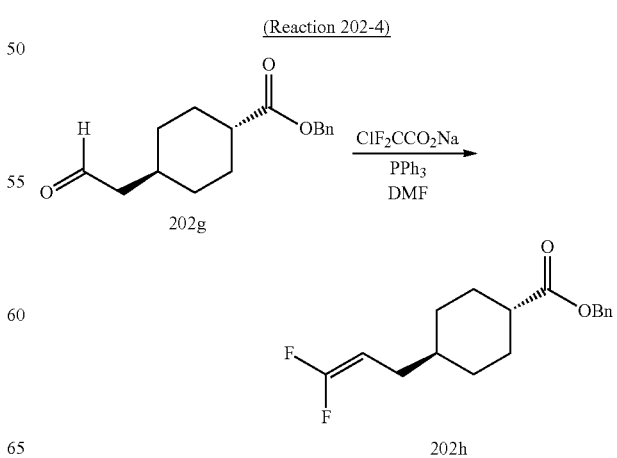

4-(2-Oxo-ethyl)-cyclohexanecarboxylic acid benzyl ester (trans:cis=4:1) was synthesized by operations similar to those in Reaction 25-4 using appropriate reagents and starting material.

$^1$H-NMR (400 MHz, CDCl$_3$) δ 1.04 (1.6H, m), 1.30 (0.4H, m), 1.51 (1.6H, m), 1.62 (0.8H, m), 1.84 (1.6H, m), 1.89 (0.8H, m), 2.10 (2.2H, m), 2.32 (2.8H, m), 2.60 (0.2H, m), 5.11 (1.6H, s), 5.13 (0.4H, s), 7.35 (5H, m), 9.75 (0.2H, t, J=2.0 Hz), 9.76 (0.8H, t, J=2.0 Hz).

A solution of 4-(2-oxo-ethyl)-cyclohexanecarboxylic acid benzyl ester (trans:cis=4:1) (21.4 mg, 0.082 mmol) in dimethylformamide (0.3 ml) was added to a solution of sodium chlorodifluoroacetate (34.1 mg, 0.224 mmol) and triphenylphosphine (59.9 mg, 0.228 mmol) in dimethylformamide (0.41 ml) at 90 to 95° C. over five minutes, and the mixture was stirred at 130° C. for four hours. Sodium chlorodifluoroacetate (34.0 mg, 0.22 mmol) was then added to the reaction mixture at the same temperature, and the mixture was further stirred for two hours. The reaction mixture was diluted with ether, and the organic layer was washed with water, dried over MgSO$_4$ and concentrated under reduced pressure. The resulting residue was purified by silica gel column chromatography (hexane-ethyl acetate) to give 4-(3,3-difluoro-allyl)-cyclohexanecarboxylic acid benzyl ester (trans:cis=4:1) (14.1 m, 58%).

$^1$H-NMR (400 MHz, CDCl$_3$) δ 0.95 (1.6H, m), 1.26 (0.4H, m), 1.44 (1.6H, m), 1.55 (0.8H, m), 1.81 (1.6H, m), 1.87 (2.2H, m), 2.20 (2H, m), 2.28 (0.8H, m), 2.60 (0.2H, m), 4.09 (0.2H, dtd, J=25.4, 8.3, 2.9 Hz), 4.12 (0.8H, dtd, J=25.4, 7.8, 2.9 Hz), 5.11 (1.6H, s), 5.13 (0.4H, s), 7.34 (5H, m).

(Reaction 202-5)

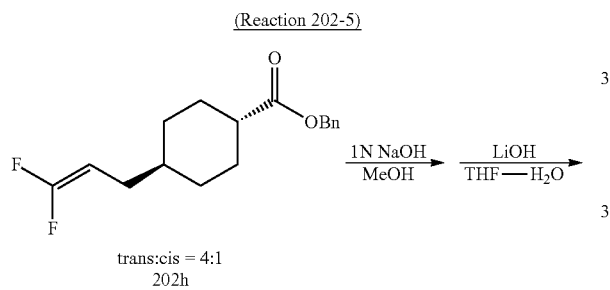

trans:cis = 4:1
202h

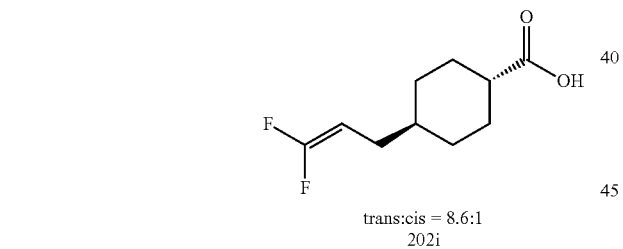

trans:cis = 8.6:1
202i

A 1 N aqueous NaOH solution (0.084 ml, 0.084 mmol) was added to a solution of 4-(3,3-difluoro-allyl)-cyclohexanecarboxylic acid benzyl ester (trans:cis=4:1) (14.1 mg, 0.0478 mmol) in methanol (1.0 mL). The mixture was stirred at room temperature for 1.5 hours, and then adjusted to pH 6 with a 1 N aqueous HCl solution and concentrated under reduced pressure. The resulting residue was adjusted to pH 3 with dilute hydrochloric acid and extracted with dichloromethane, and the organic layer was dried over MgSO$_4$ and concentrated under reduced pressure. The resulting residue was dissolved in THF (0.2 ml)-H$_2$O (0.2 ml), and LiOH.H$_2$O (7.7 mg, 0.18 mmol) was added. The mixture was stirred at room temperature for three hours, and then adjusted to pH 3 with a 1 N aqueous HCl solution and extracted with dichloromethane. The organic layer was then dried over MgSO$_4$ and concentrated under reduced pressure. The resulting residue was purified by column chromatography (hexane-ethyl acetate) to give 4-(3,3-difluoro-allyl)-cyclohexanecarboxylic acid (8.3 g, 86%).

$^1$H-NMR (400 MHz, CDCl$_3$) δ 0.97 (1.8H, m), 1.27 (0.4H, m), 1.43 (1.8H, m), 1.58 (1H, m), 1.82 (2H, m), 1.88 (2H, m), 2.03 (2H, m), 2.25 (0.9H, m), 2.61 (0.1H, m), 4.13 (1H, dtd, J=25.4, 7.8, 2.9 Hz).

Example 203

N-(4-{(E)-1-Fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide
(Compound 942)

(Reaction 203-1)

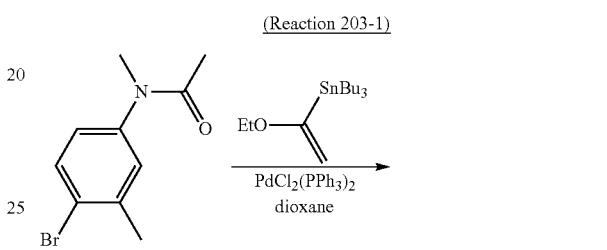

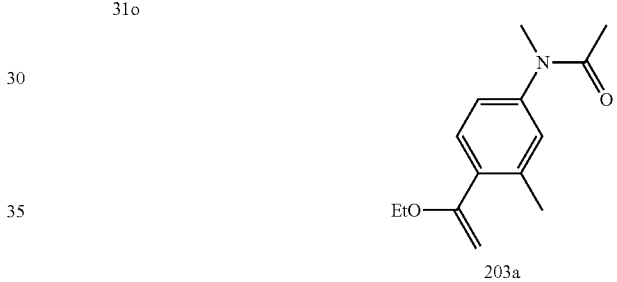

203a

Tributyl(1-ethoxyvinyl)tin (1.07 mmol, 3.18 mmol) and dichlorobis(triphenylphosphine)palladium(II) (101 mg, 0.145 mmol) were added to a solution of N-(4-bromo-3-methylphenyl)-N-methylacetamide (700 mg, 2.89 mmol) in 1,4-dioxane (7 mL), and the mixture was heated with stirring at 90° C. for 12 hours in a nitrogen stream. The reaction mixture was cooled and then filtered through celite. The solution was concentrated under reduced pressure, and the residue was then silica gel column chromatography (hexane-ethyl acetate) to give N-[4-(1-ethoxy-vinyl)-3-methyl-phenyl]-N-methyl-acetamide (440 mg, 65%).

MS (ESI) m/z=234 (M+H)+.

(Reaction 203-2)

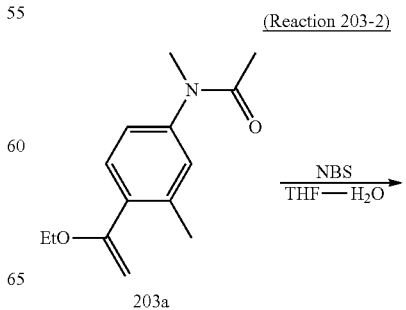

203a

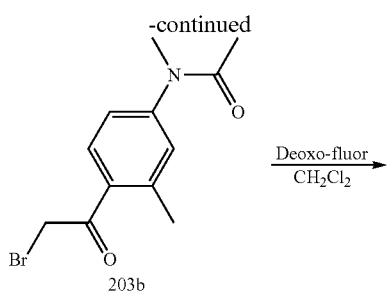

N-[4-(2-Bromo-1,1-difluoroethyl)-3-methylphenyl]-N-methylacetamide was synthesized by operations similar to those in Reaction 127-4 and Reaction 191-11 using appropriate reagents and starting material.

MS (ESI) m/z=306, 308 (M+H)+.

(Reaction 203-3)

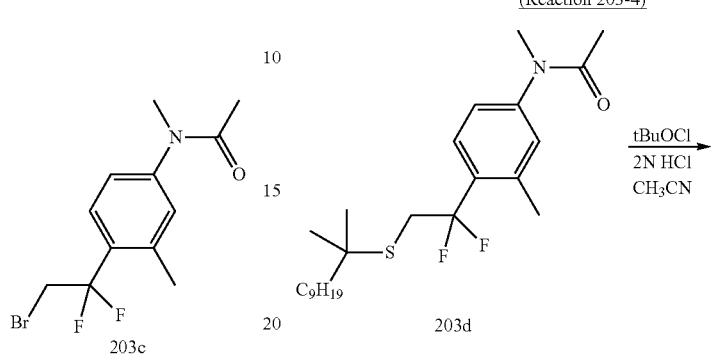

t-Dodecanethiol (0.227 mL, 0.96 mmol) was added to a solution of potassium t-butoxide (108 mg, 0.96 mmol) in DMF (2 mL), and the mixture was stirred at room temperature. A solution of N-[4-(2-bromo-1,1-difluoroethyl)-3-methylphenyl]-N-methylacetamide (245 mg, 0.800 mmol) in DMF (2 mL) was added to the mixture which was then stirred at room temperature for one hour. Saturated NH₄Cl was added to the reaction mixture, followed by extraction with ethyl acetate. The organic layer was washed with saturated brine, and then dried over MgSO₄ and concentrated under reduced pressure. The resulting residue was purified by silica gel column chromatography (hexane-ethyl acetate) to give N-{4-[2-(1,1-dimethyldecylsulfanyl)-1,1-difluoro-ethyl]-3-methylphenyl}-N-methylacetamide (287 mg, 84%).

MS (ESI) m/z=428 (M+H)+.

(Reaction 203-4)

2 N HCl (0.4 mL) was added to a solution of N-{4-[2-(1,1-dimethyldecylsulfanyl)-1,1-difluoro-ethyl]-3-methylphenyl}-N-methylacetamide (102 mg, 0.239 mmol) in MeCN (1 mL) at 0° C. After stirring for five minutes, t-butyl hypochlorite (0.135 mL, 1.20 mmol) was added in small portions at −10° C. The mixture was stirred for 15 minutes, and saturated NH₄Cl was then added, followed by extraction with ethyl acetate. The organic layer was washed with saturated brine. The organic layer was dried over MgSO₄ and then concentrated under reduced pressure to give a mixture containing 2-[4-(acetylmethylamino)-2-methylphenyl]-2,2-difluoroethanesulfonyl chloride (121 mg).

$^1$H-NMR (400 MHz, CDCl₃) δ 7.72 (1H, s), 7.62 (1H, m), 7.30 (1H, m), 4.47-4.57 (2H, m), 3.18 (3H, s), 2.49-2.53 (3H, m), 1.80 and 1.82 (3H, s).

(Reaction 203-5)

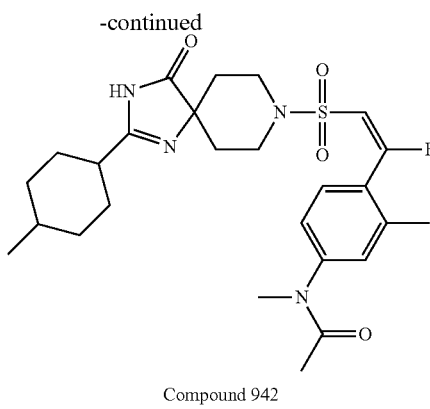

Compound 942

N-(4-{(E)-1-Fluoro-2-[2-(4-methyl-cyclohexyl)-4-oxo-1,3,8-triaza-spiro[4.5]dec-1-ene-8-sulfonyl]-vinyl}-3-methyl-phenyl)-N-methyl-acetamide was synthesized by operations similar to those in Reaction 6-1 using appropriate reagents and the starting material obtained above.

MS (ESI) m/z=519 (M+H)+.

Example 204

3-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione (Compound 943)

(Reaction 204-1)

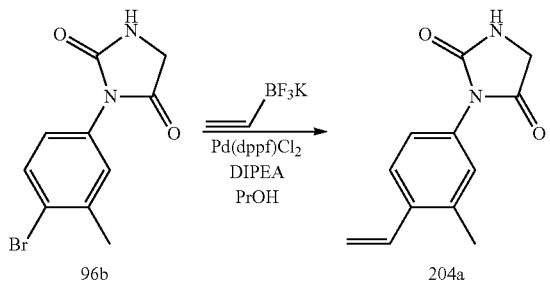

Potassium vinyltrifluoroborate (356 mg, 242 µmol), ethyldiisopropylamine (48 µl, 279 µmol) and [1,1'-bis(diphenylphosphino)ferrocene]dichloropalladium dichloromethane adduct (15.1 mg, 18.6 µmol) were added to a solution of 3-(4-bromo-3-methyl-phenyl)-imidazolidine-2,4-dione (50 mg, 186 µmol) in n-PrOH (372 µL) at room temperature in an $N_2$ atmosphere. The mixture was stirred at 100° C. for 1.5 hours, and the reaction solution was then cooled. The reaction solution was concentrated under reduced pressure. The resulting residue was purified by silica gel column chromatography (dichloromethane-methanol) to give 3-(3-methyl-4-vinyl-phenyl)-imidazolidine-2,4-dione as a yellow brown form (33 mg, 82%).

MS (ESI) m/z=217 (M+H)+.

(Reaction 204-2)

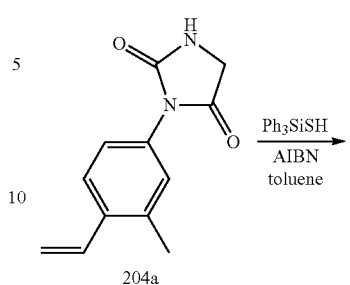

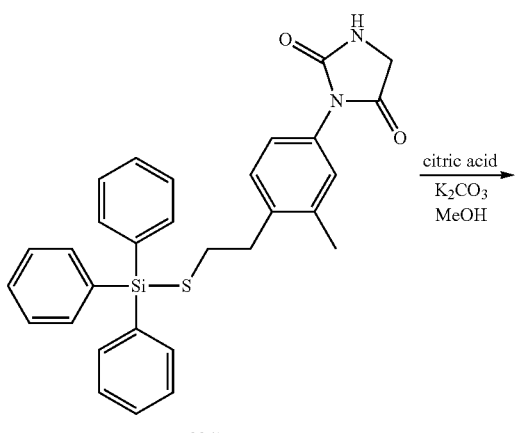

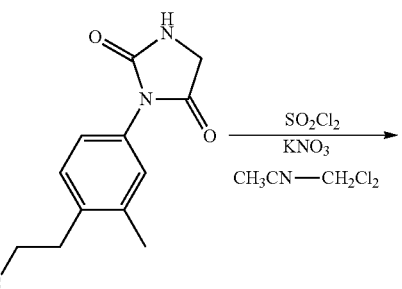

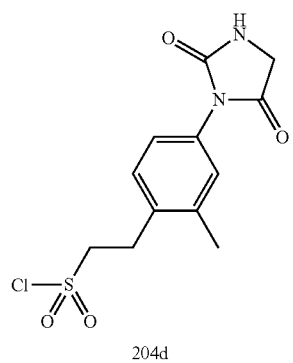

2-[4-(2,5-Dioxo-imidazolidin-1-yl)-2-methyl-phenyl]-ethanesulfonyl chloride was synthesized by operations similar to those in Reaction 10-3, Reaction 10-4 and Reaction 10-5 using appropriate reagents and starting material.

MS (ESI) m/z=317, 319 (M+H)+.

(Reaction 204-3)

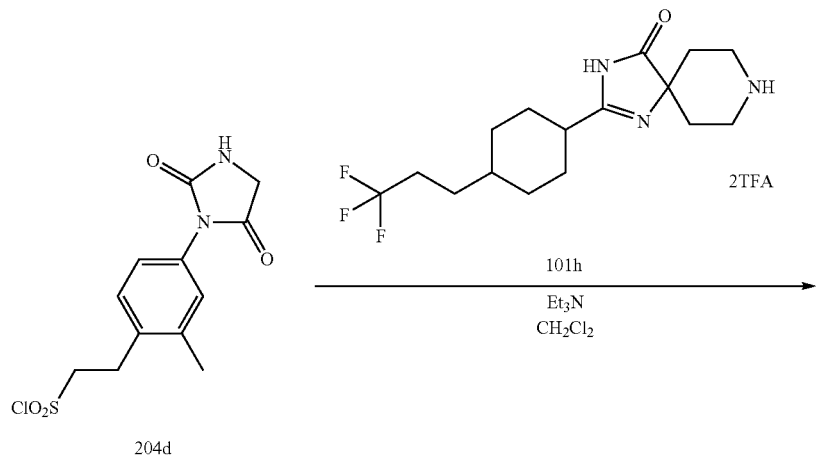

Compound 943

3-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-phenyl]-imidazolidine-2,4-dione was synthesized by operations similar to those in Reaction 5-4 using appropriate reagents and the starting material obtained above.

MS (ESI) m/z=612 (M+H)+.

The example compounds shown below were synthesized by operations similar to those in Reaction 204-3 using appropriate reagents and starting materials.

Compounds 944 to 947

TABLE 133

| Compound | Structure | LCMS condition | Retention time (min) | MS (m/z) |
|---|---|---|---|---|
| 944 | 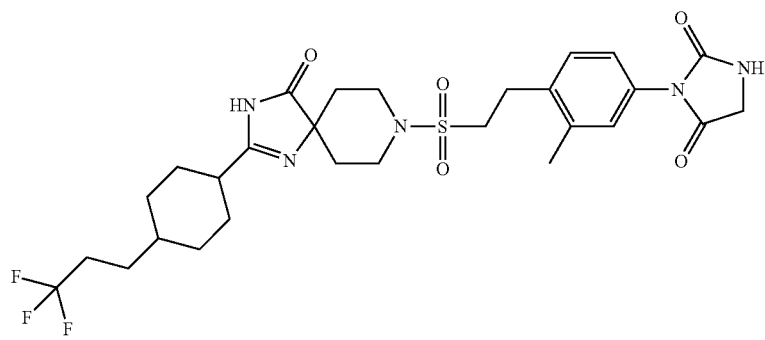 | LCMS-F-1 | 0.95 | 626 (M + H)+ |

TABLE 133-continued

| Compound | Structure | LCMS condition | Retention time (min) | MS (m/z) |
| --- | --- | --- | --- | --- |
| 945 | 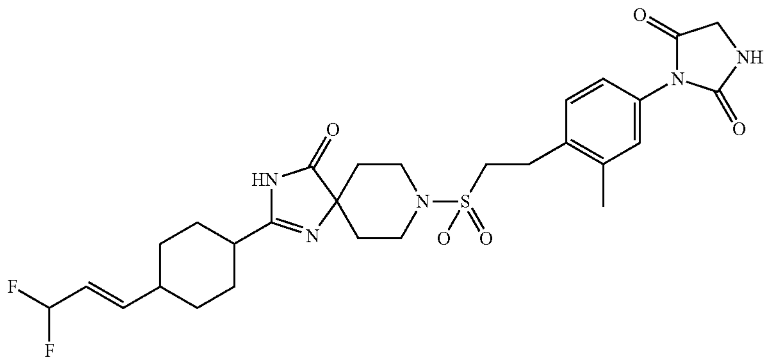 | LCMS-F-1 | 0.85 | 592 (M + H)+ |
| 946 | 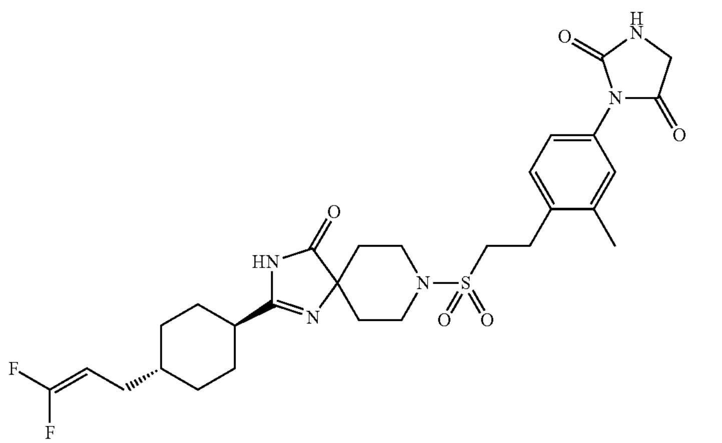 [SMILES: Cc1cc(N2C(=O)CNC2=O)ccc1CCS(=O)(=O)N1CCC2(CC1)N=C([C@H]1CC[C@H](CC=C(F)F)CC1)NC2=O] | LCMS-B-1 | 1.85 | 592 (M + H)+ |
| 947 | 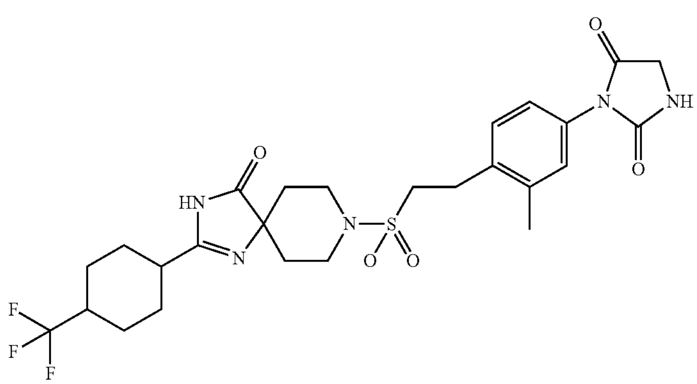 | LCMS-F-1 | 0.84 | 584 (M + H)+ |

Example 205

3-[3-Methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione (Compound 948)

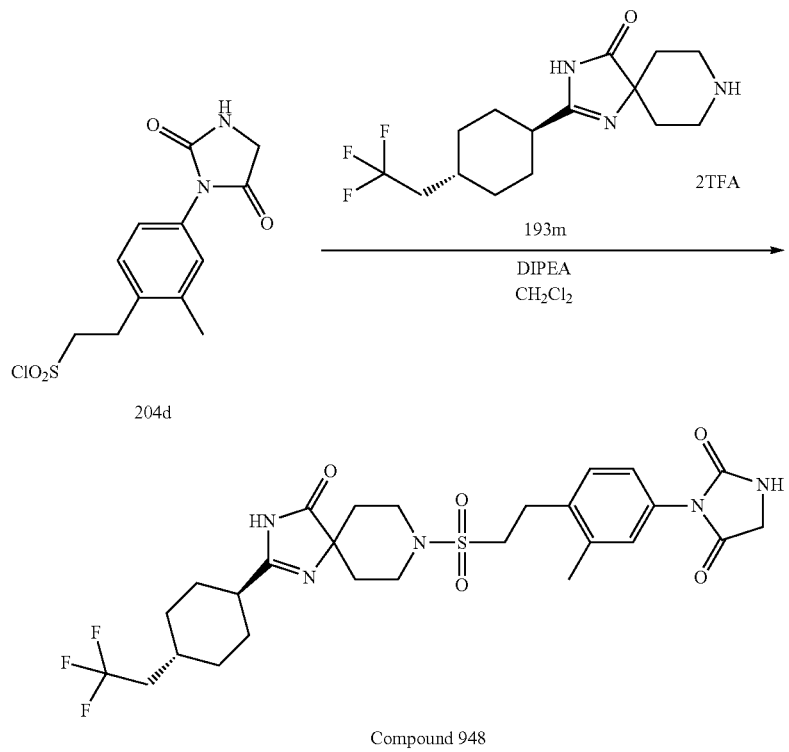

3-[3-Methyl-4-(2-{4-oxo-2-[4-(2,2,2-trifluoro-ethyl)-cyclohexyl]-1,3,8-triaza-spiro[4.5]dec-1-ene-8-sulfonyl}-ethyl)-phenyl]-imidazolidine-2,4-dione was synthesized by operations similar to those in Reaction 5-4 using appropriate reagents and starting material.
MS (ESI) m/z=598 (M+H)+.

The example compounds shown below were synthesized by operations similar to those in Reaction 205-1 using appropriate reagents and starting materials.

Compounds 949 to 952

TABLE 134

| Compound | Structure | LCMS condition | Retention time (min) | MS (m/z) |
|---|---|---|---|---|
| 949 | 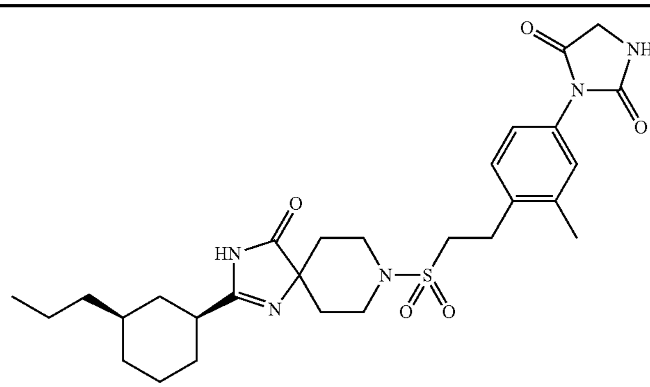 | LCMS-A-1 | 2.16 | 558 (M + H)+ |

TABLE 134-continued

| Compound | Structure | LCMS condition | Retention time (min) | MS (m/z) |
|---|---|---|---|---|
| 950 | 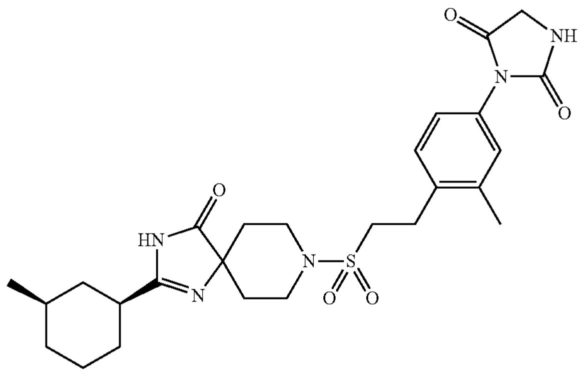 [SMILES: Cc1cc(N2C(=O)CNC2=O)ccc1CCS(=O)(=O)N1CCC2(CC1)N=C([C@H]1CCC[C@@H](C)C1)NC2=O] | LCMS-C-1 | 2.35 | 530 (M + H)+ |
| 951 | 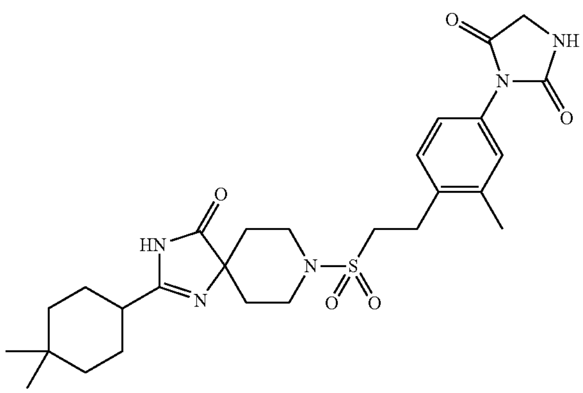 [SMILES: Cc1cc(N2C(=O)CNC2=O)ccc1CCS(=O)(=O)N1CCC2(CC1)N=C(C1CCC(C)(C)CC1)NC2=O] | LCMS-C-1 | 2.52 | 544 (M + H)+ |
| 952 | 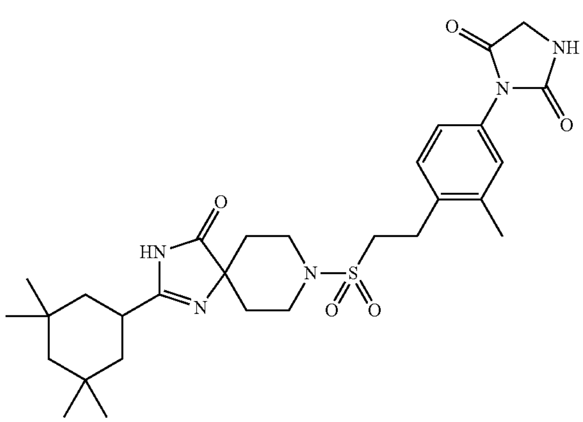 [SMILES: Cc1cc(N2C(=O)CNC2=O)ccc1CCS(=O)(=O)N1CCC2(CC1)N=C(C1CC(C)(C)CC(C)(C)C1)NC2=O] | LCMS-C-1 | 2.73 | 572 (M + H)+ |

Example 206

N-(2-Chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide (Compound 953) and N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide (Compound 954)

(Reaction 206-1)

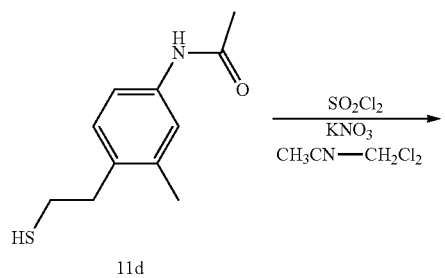

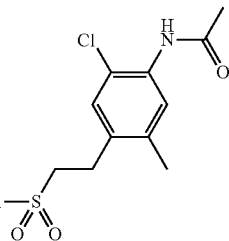
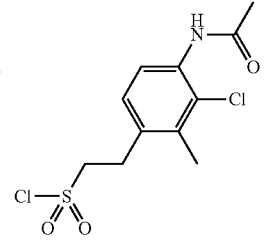

Mixture 206a

A sulfonyl chloride reagent (a mixture of 2-(4-acetylamino-5-chloro-2-methyl-phenyl)-ethanesulfonyl chloride and 2-(4-acetylamino-3-chloro-2-methyl-phenyl)-ethanesulfonyl chloride) was synthesized by operations similar to those in Reaction 10-5 using appropriate reagents and starting material.

MS (ESI) m/z=310, 312, 314 (M+H)+.

(Reaction 206-2)

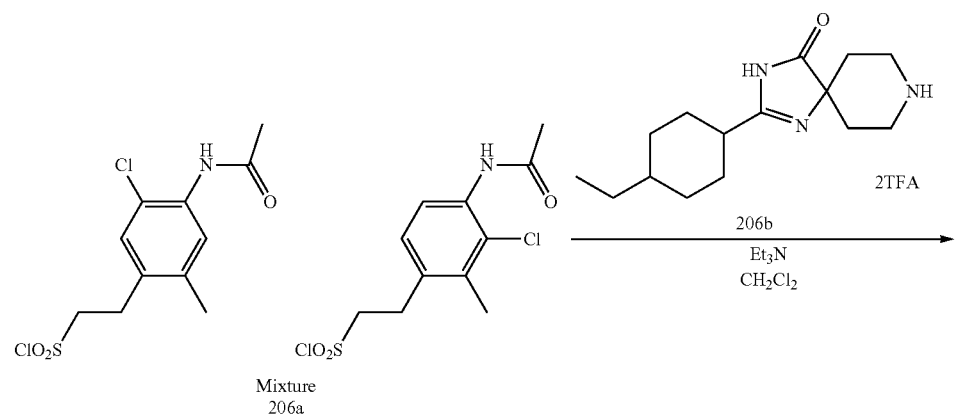

Mixture 206a

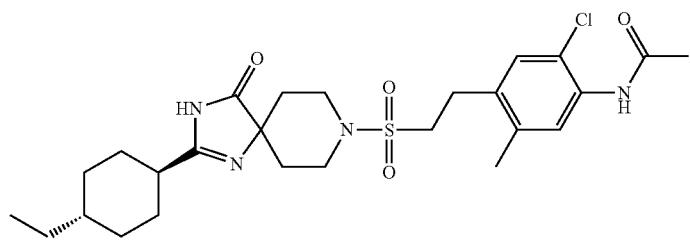

Compound 953

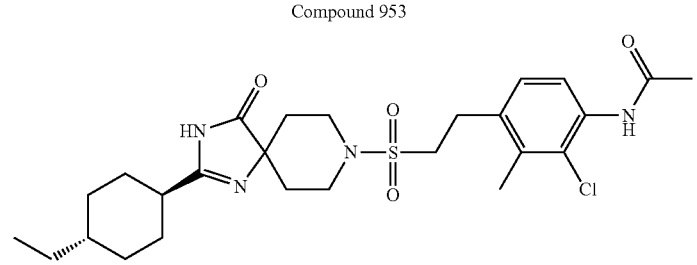

Compound 954

N-(2-Chloro-4-{2-[2-(4-ethyl-cyclohexyl)-4-oxo-1,3,8-triaza-spiro[4.5]dec-1-ene-8-sulfonyl]-ethyl}-5-methyl-phenyl)-acetamide MS (ESI) m/z=537 (M+H)+ and

N-(2-chloro-4-{2-[2-(4-ethyl-cyclohexyl)-4-oxo-1,3,8-triaza-spiro[4.5]dec-1-ene-8-sulfonyl]-ethyl}-3-methyl-phenyl)-acetamide MS (ESI) m/z=537 (M+H)+ were obtained by operations similar to those in Reaction 5-4 using appropriate reagents and the starting material obtained above.

Example 207

N-[4-(2-{2-[4-(3,3-Difluoro-propyl)-cyclohexyl]-4-oxo-1,3,8-triaza-spiro[4.5]dec-1-ene-8-sulfonyl}-ethyl)-3-methyl-phenyl]-acetamide (Compound 955)

N-[4-(2-{2-[4-(3,3-Difluoro-propyl)-cyclohexyl]-4-oxo-1,3,8-triaza-spiro[4.5]dec-1-ene-8-sulfonyl}-ethyl)-3-methyl-phenyl]-acetamide (Compound 955) was obtained by operations similar to those in Reaction 18-2 using Compound as a starting material.

MS (ESI) m/z=553 (M+H)+.

The example compound shown below was obtained by operations similar to those in Reaction 207-1 using an appropriate starting compound.

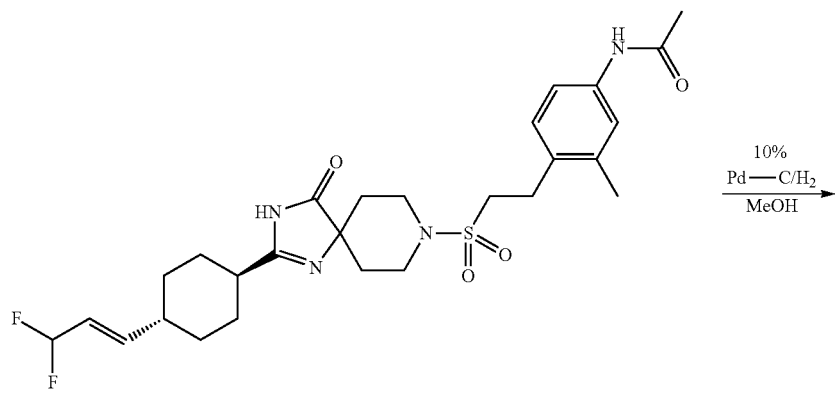

Compound 916

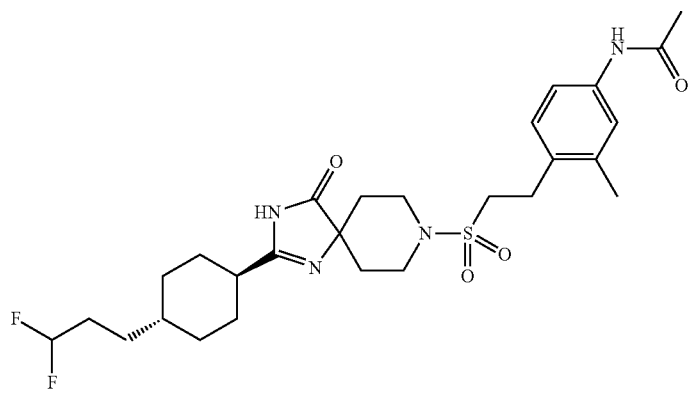

Compound 955

Compound 956

TABLE 135

| Raw material Compound | Target Compound | Structure | LCMS condition | Retention time (min) | MS (m/z) |
|---|---|---|---|---|---|
| 945 | 956 | 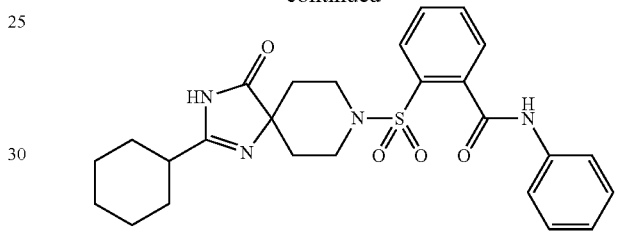 | LCMS-F-1 | 0.87 | 594 (M + H)+ |

Example 208

2-(2-Cyclohexyl-4-oxo-1,3,8-triaza-spiro[4.5]dec-1-ene-8-sulfonyl)-N-phenyl-benzamide (Compound 957)

(Reaction 208-1)

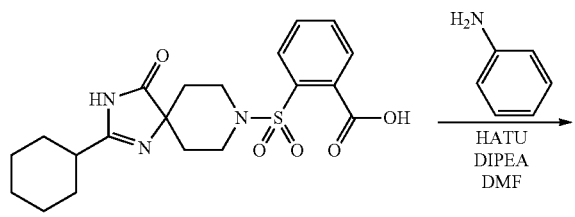

Compound 957

2-(2-Cyclohexyl-4-oxo-1,3,8-triaza-spiro[4.5]dec-1-ene-8-sulfonyl)-N-phenyl-benzamide was synthesized by operations similar to those in Reaction 10-14 using appropriate reagents and starting material.

MS (ESI) m/z=495 (M+H)+.

Example 209

8-(2-{2-Methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one (Compound 958)

(Reaction 209-1)

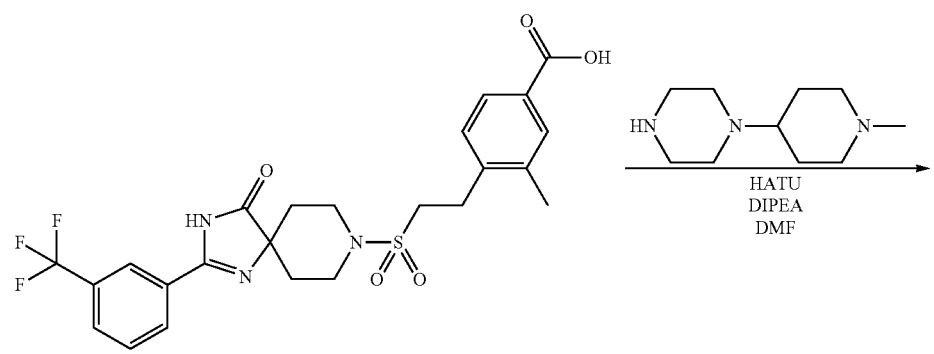

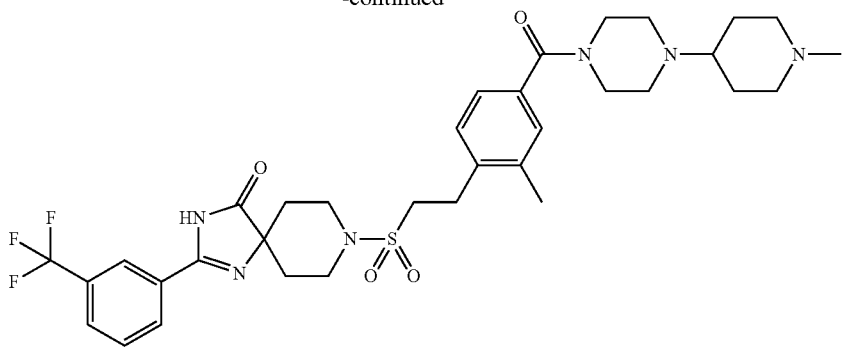

Compound 958

8-(2-{2-Methyl-4-[4-(1-methyl-piperidin-4-yl)-piperazine-1-carbonyl]-phenyl}-ethanesulfonyl-2-(3-trifluoromethyl-phenyl)-1,3,8-triaza-spiro[4.5]dec-1-en-4-one was synthesized by operations similar to those in Reaction 10-14 using appropriate reagents and starting material.

MS (ESI) m/z=689 (M+H)+.

Example 210

8-{(E)-2-[4-((R)-3-Fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 959)

(Reaction 210-1)

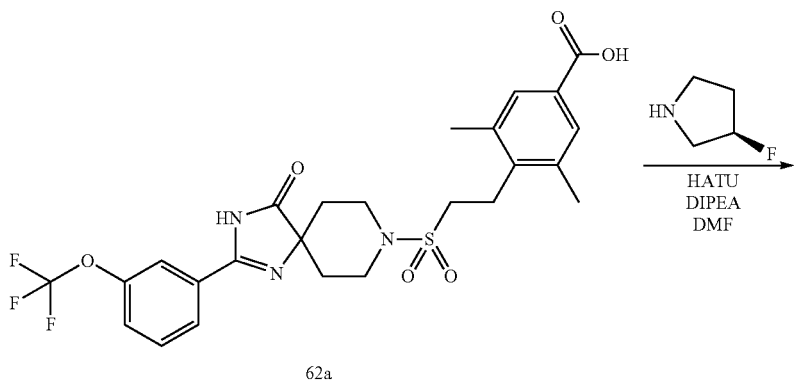

62a

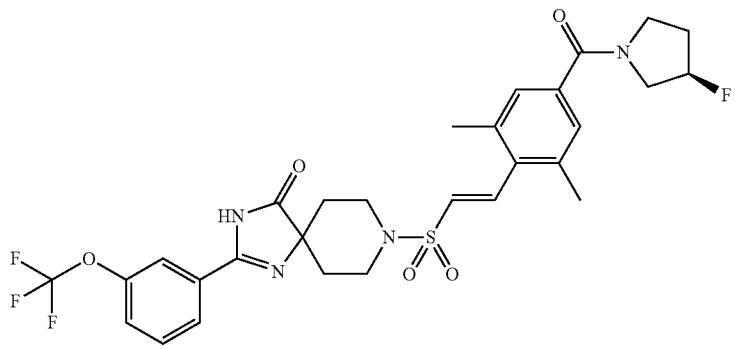

Compound 959

8-{(E)-2-[4-((R)-3-Fluoro-pyrrolidine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 10-14 using appropriate reagents and starting material.

MS (ESI) m/z=623 (M+H)+.

The example compounds shown below were synthesized by operations similar to those in Reaction 210-1 using appropriate reagents and starting materials.

Compounds 960 to 962

TABLE 136

| Compound | Structure | LCMS condition | Retention time (min) | MS (m/z) |
|---|---|---|---|---|
| 960 | 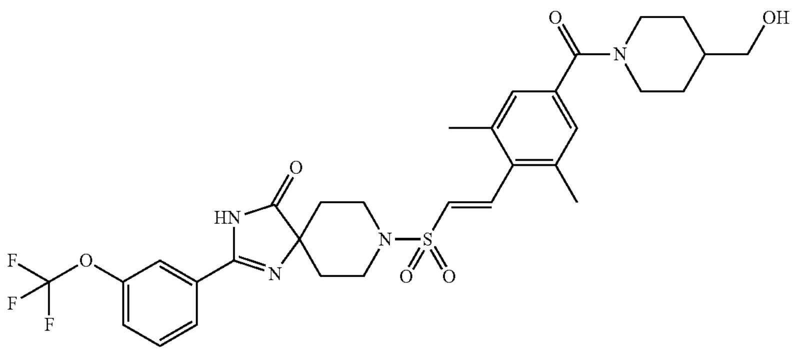 [SMILES: Cc1cc(C(=O)N2CCC(CO)CC2)cc(C)c1/C=C/S(=O)(=O)N1CCC2(CC1)N=C(c1cccc(OC(F)(F)F)c1)NC2=O] | LCMS-B-1 | 2.15 | 649 (M + H)+ |
| 961 | 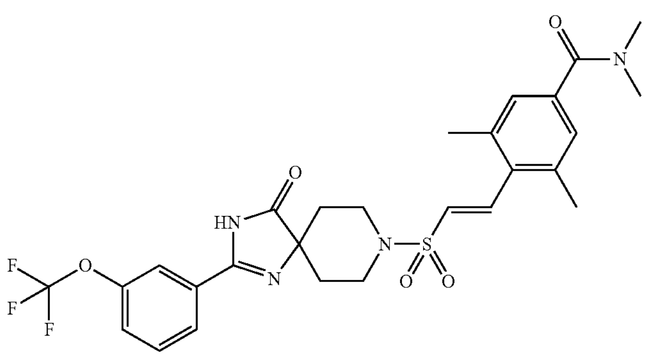 [SMILES: Cc1cc(C(=O)N(C)C)cc(C)c1/C=C/S(=O)(=O)N1CCC2(CC1)N=C(c1cccc(OC(F)(F)F)c1)NC2=O] | LCMS-C-1 | 2.72 | 579 (M + H)+ |
| 962 | 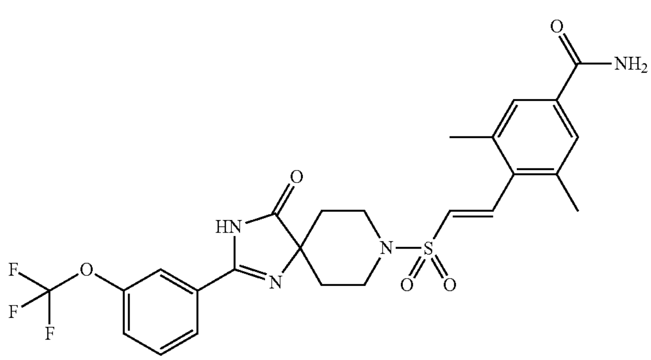 [SMILES: Cc1cc(C(N)=O)cc(C)c1/C=C/S(=O)(=O)N1CCC2(CC1)N=C(c1cccc(OC(F)(F)F)c1)NC2=O] | LCMS-C-1 | 2.62 | 551 (M + H)+ |

Example 211

8-{(E)-2-[4-(3-Fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one (Compound 963)

(Reaction 211-1)

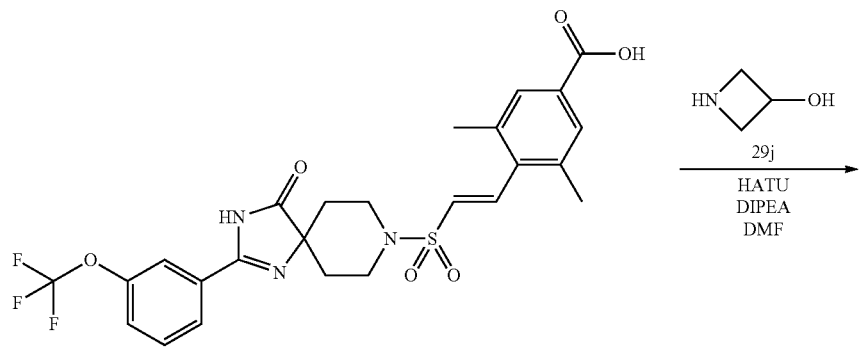

62a

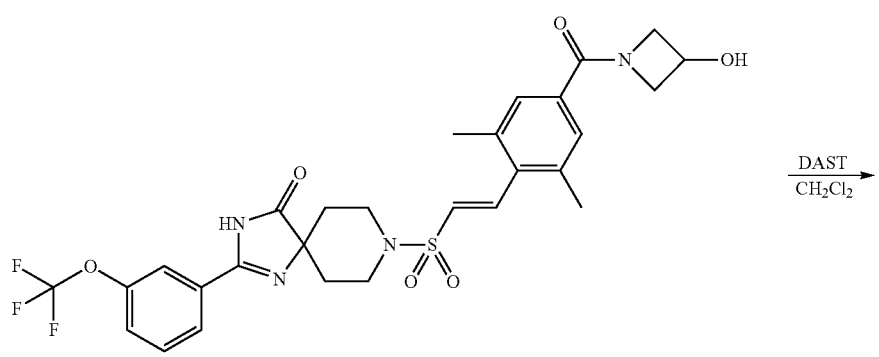

211a

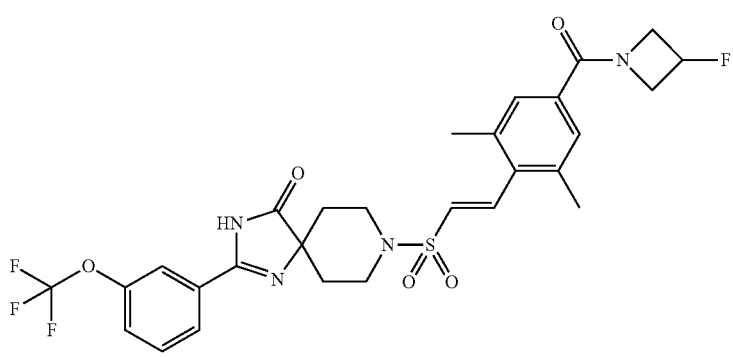

Compound 963

8-{(E)-2-[4-(3-Fluoro-azetidine-1-carbonyl)-2,6-dimethyl-phenyl]-ethenesulfonyl}-2-(3-trifluoromethoxy-phenyl)-1,3,8-triaza-spiro[4.5]dec-1-en-4-one was synthesized by operations similar to those in Reaction 10-14 and Reaction 25-15 using appropriate reagents and starting material.

MS (ESI) m/z=609 (M+H)+.

Example 212

8-{2-[4-(4-Hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one (Compound 964)

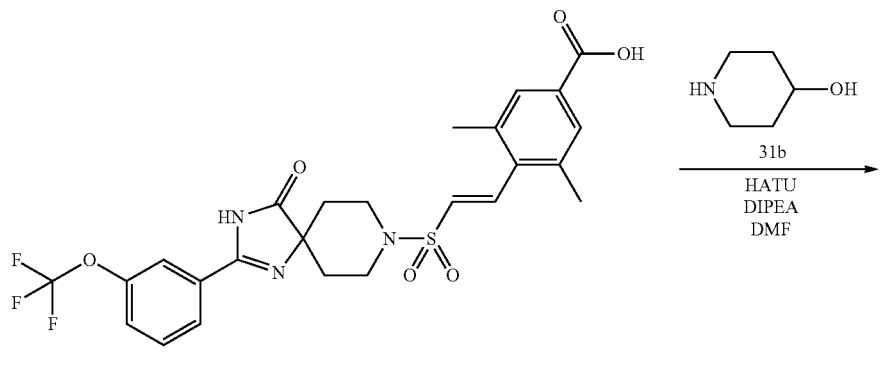

62a

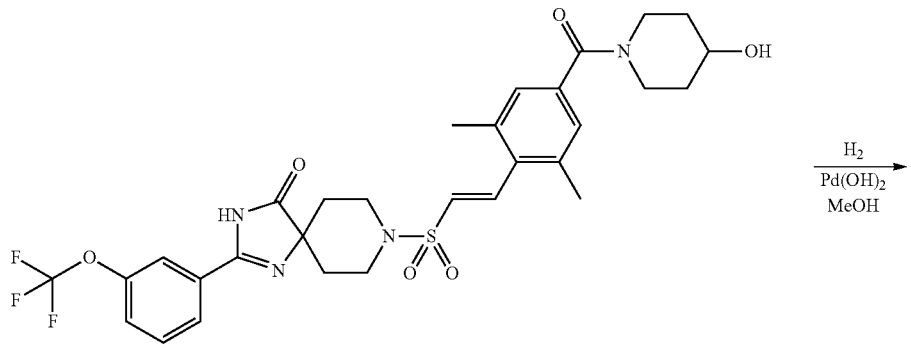

212a

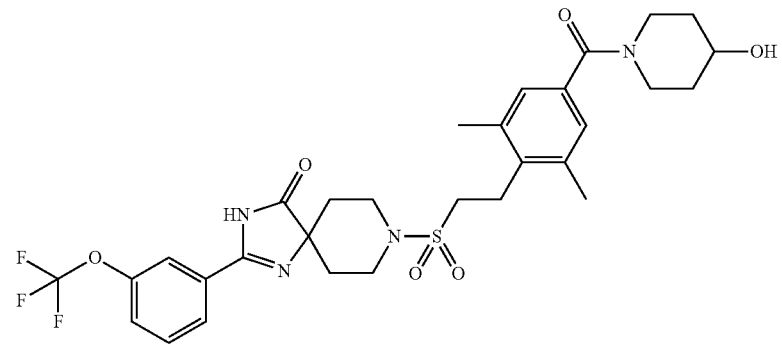

Compound 964

8-{2-[4-(4-Hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one was synthesized by operations similar to those in Reaction 10-14 and Reaction 122-2 using appropriate reagents and starting material.

MS (ESI) m/z=637 (M+H)+.

The example compounds shown below were synthesized by operations similar to those in Reaction 212-1 using appropriate reagents and starting materials.

Compounds 965 to 966

TABLE 137

| Compound | Structure | LCMS condition | Retention time (min) | MS (m/z) |
|---|---|---|---|---|
| 965 | 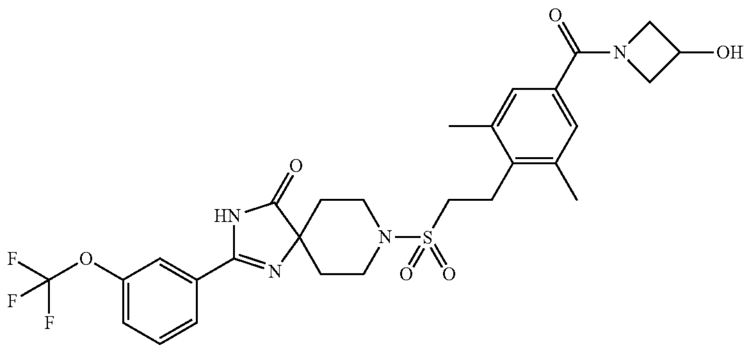 [SMILES: Cc1cc(C(=O)N2CC(O)C2)cc(C)c1CCS(=O)(=O)N1CCC2(CC1)N=C(c1cccc(OC(F)(F)F)c1)NC2=O] | LCMS-F-1 | 0.91 | 609 (M + H)+ |
| 966 | 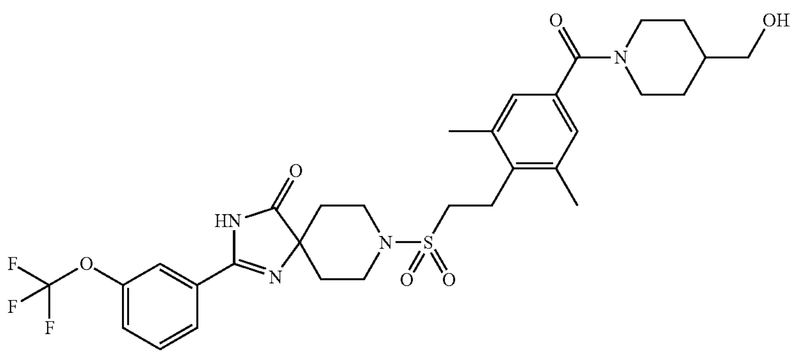 [SMILES: Cc1cc(C(=O)N2CCC(CO)CC2)cc(C)c1CCS(=O)(=O)N1CCC2(CC1)N=C(c1cccc(OC(F)(F)F)c1)NC2=O] | LCMS-F-1 | 0.94 | 651 (M + H)+ |

Example 213

8-{(E)-2-[2,6-Dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one (Compound 967)

(Reaction 213-1)

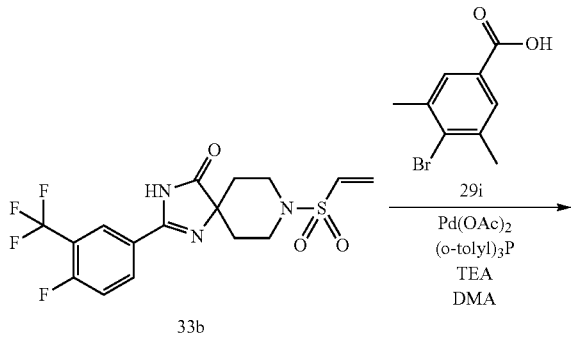

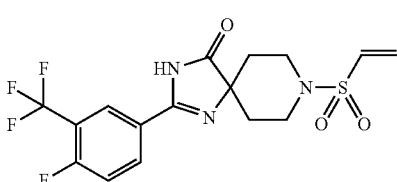

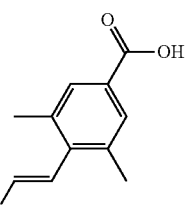

213a

4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-benzoic acid was synthesized by operations similar to those in Reaction 26-1 using appropriate reagents and starting material.

MS (ESI) m/z=554 (M+H)+.

(Reaction 213-2)

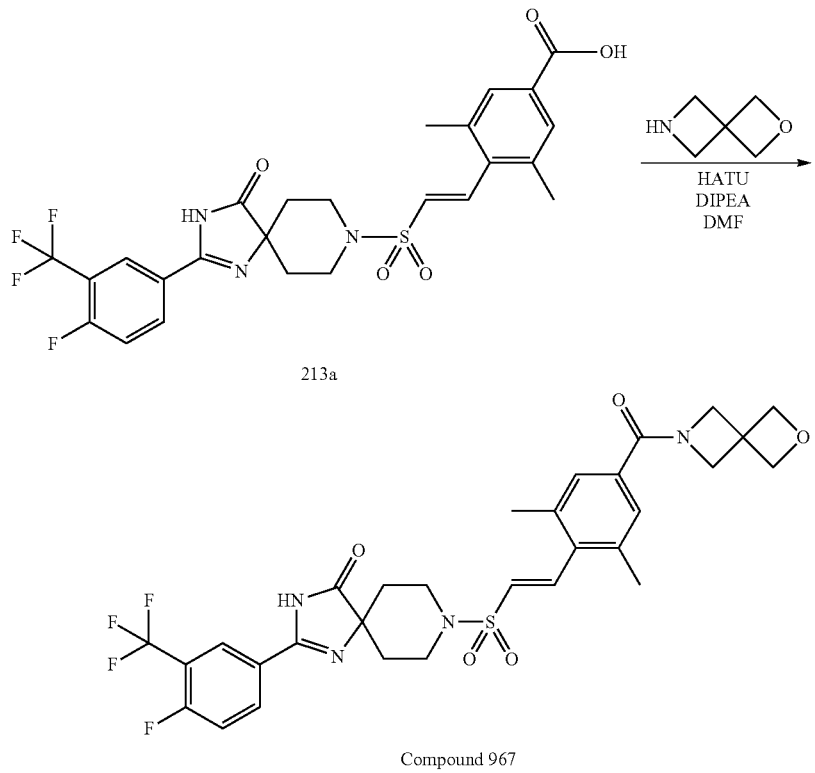

Compound 967

8-{(E)-2-[2,6-Dimethyl-4-(2-oxa-6-aza-spiro[3.3]heptane-6-carbonyl)-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 10-14 using appropriate reagents and starting material.
MS (ESI) m/z=635 (M+H)+.

Example 214

8-{(E)-2-[2,6-Dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one (Compound 968)

(Reaction 214-1)

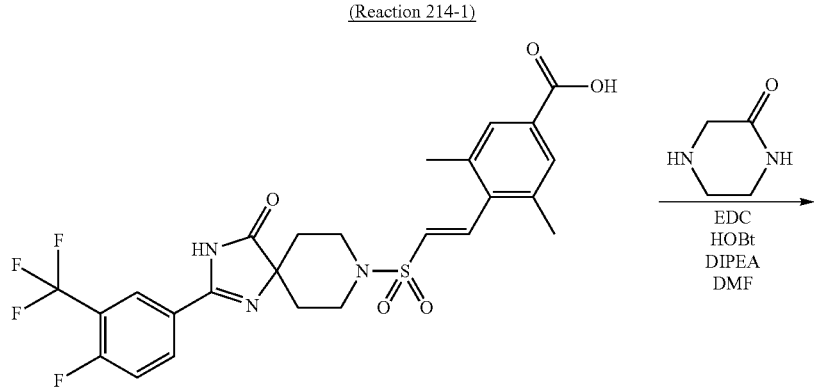

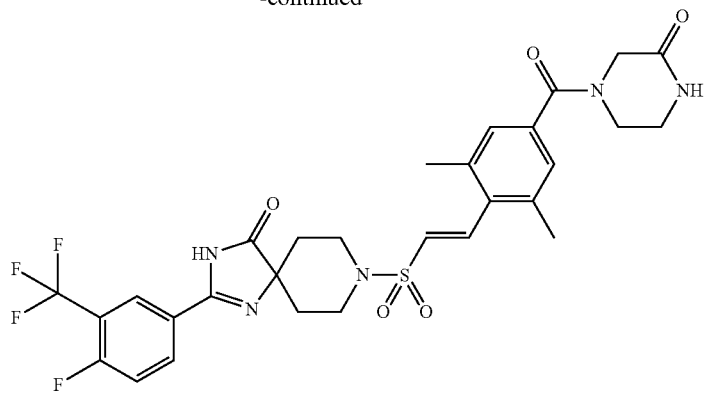

Compound 968

8-{(E)-2-[2,6-Dimethyl-4-(3-oxo-piperazine-1-carbonyl)-phenyl]-ethenesulfonyl}-2-(4-fluoro-3-trifluoromethyl-phenyl)-1,3,8-triaza-spiro[4.5]dec-1-en-4-one was synthesized by operations similar to those in Reaction 10-18 using appropriate reagents and starting material.
MS (ESI) m/z=636 (M+H)+.

The example compounds shown below were synthesized by operations similar to those in Reaction 214-1 using appropriate reagents and starting materials.

Compounds 969 to 972

TABLE 138

| Compound | Structure | LCMS condition | Retention time (min) | MS (m/z) |
|---|---|---|---|---|
| 969 | 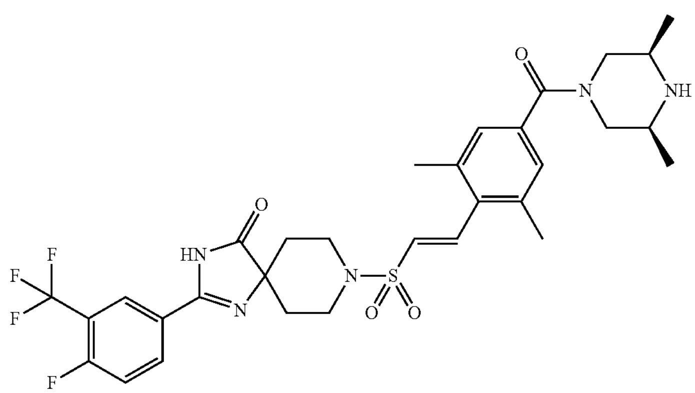 [SMILES: Cc1cc(C(=O)N2C[C@@H](C)N[C@@H](C)C2)cc(C)c1/C=C/S(=O)(=O)N1CCC2(CC1)N=C(c1ccc(F)c(C(F)(F)F)c1)NC2=O] | LCMS-C-1 | 2.67 | 650 (M + H)+ |
| 970 | 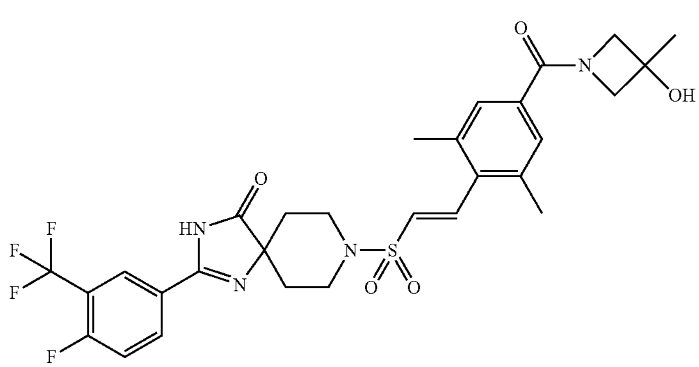 [SMILES: Cc1cc(C(=O)N2CC(C)(O)C2)cc(C)c1/C=C/S(=O)(=O)N1CCC2(CC1)N=C(c1ccc(F)c(C(F)(F)F)c1)NC2=O] | LCMS-C-1 | 2.67 | 623 (M + H)+ |

TABLE 138-continued
| Compound | Structure | LCMS condition | Retention time (min) | MS (m/z) |
| --- | --- | --- | --- | --- |
| 971 | 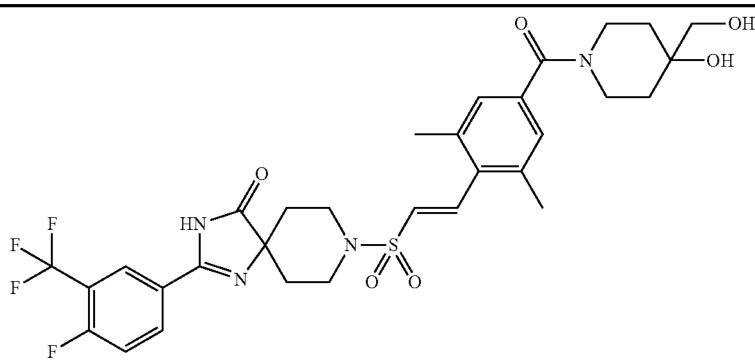 | LCMS-C-1 | 2.55 | 667 (M + H)+ |
| 972 | 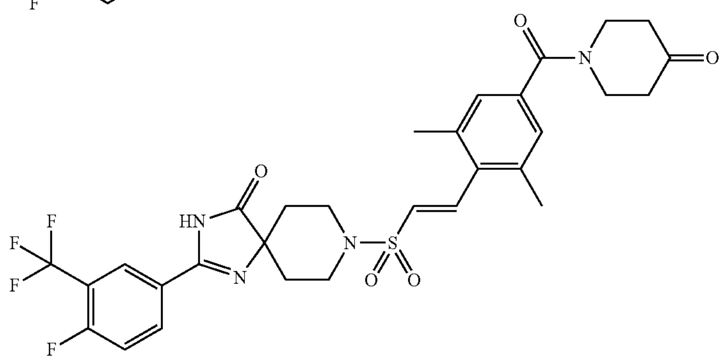 | LCMS-G-1 | 1.10 | 635 (M + H)+ |
Example 215
2-[4-(3,3-Difluoro-allyl)-cyclohexyl]-8-{2-[4-(4-fluoro-4-hydroxymethyl-piperidine-1-carbonyl)-2-methyl-phenyl]-ethanesulfonyl}-1,3,8-triaza-spiro[4.5]dec-1-en-4-one
Compound 973
(Reaction 215-1)
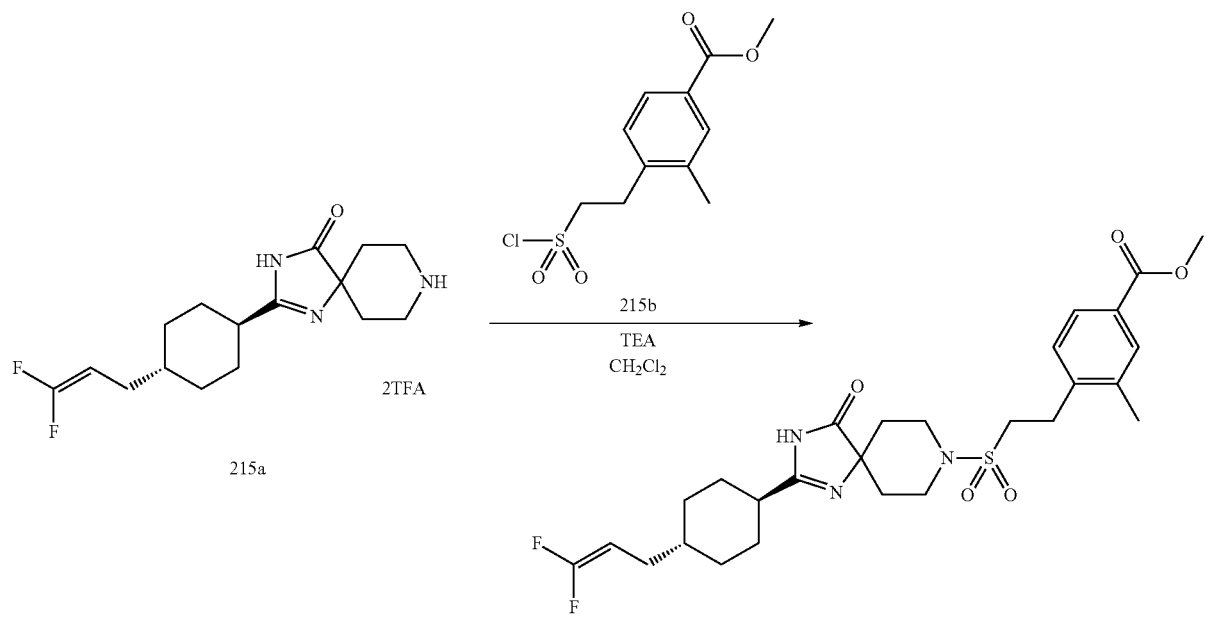

4-(2-{2-[4-(3,3-Difluoro-allyl)-cyclohexyl]-4-oxo-1,3,8-triaza-spiro[4.5]dec-1-ene-8-sulfonyl}-ethyl)-3-methyl-benzoic acid methyl ester was synthesized by operations similar to those in Reaction 5-4 using appropriate reagents and starting material.

MS (ESI) m/z=552 (M+H)+.

stirred at room temperature for two days. The reaction mixture was diluted with tert-butyl methyl ether and then adjusted to pH 1 with 2 N hydrochloric acid, followed by extraction with ethyl acetate. The organic layer was concentrated under reduced pressure, and the resulting residue

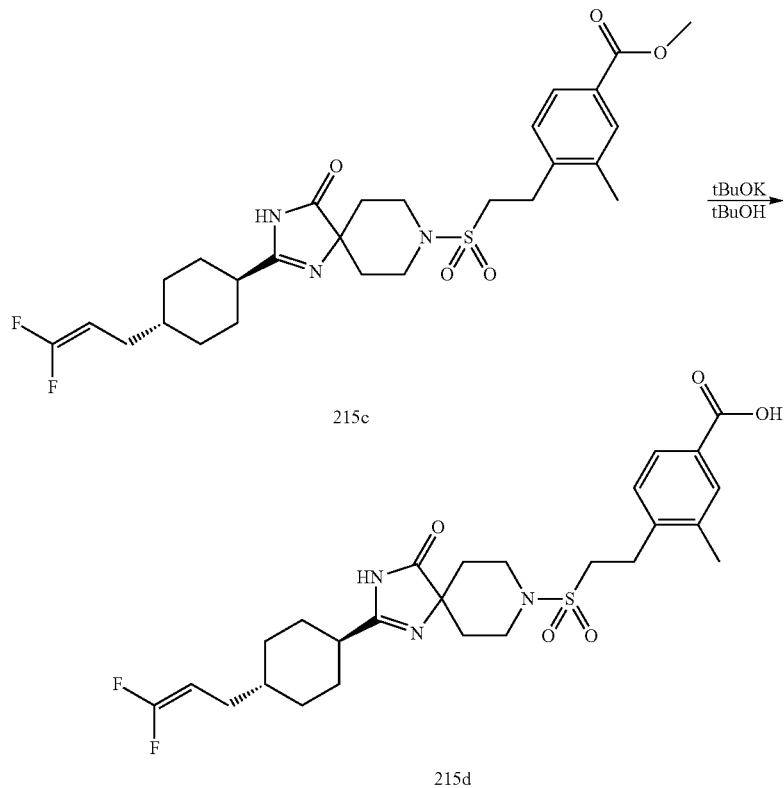

Potassium t-butoxide (15.6 mg) was added to a solution of 4-(2-{2-[4-(3,3-difluoro-allyl)-cyclohexyl]-4-oxo-1,3,8-triaza-spiro[4.5]dec-1-ene-8-sulfonyl}-ethyl)-3-methyl-benzoic acid methyl ester (25.6 mg, 46.4 µmol) in t-butanol (464 µL) and tetrahydrofuran (464 µL), and the mixture was was then dried to give 4-(2-{2-[4-(3,3-difluoro-allyl)-cyclohexyl]-4-oxo-1,3,8-triaza-spiro[4.5]dec-1-ene-8-sulfonyl}-ethyl)-3-methyl-benzoic acid (27.5 mg, 91%).

MS (ESI) m/z=538 (M+H)+.

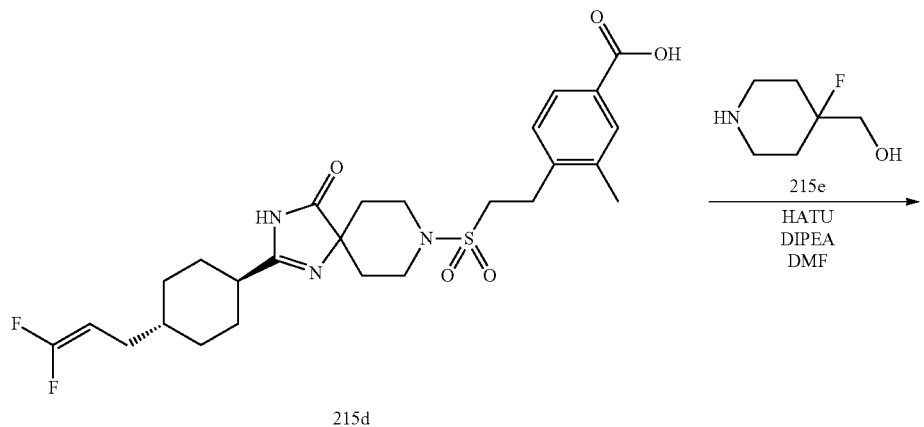

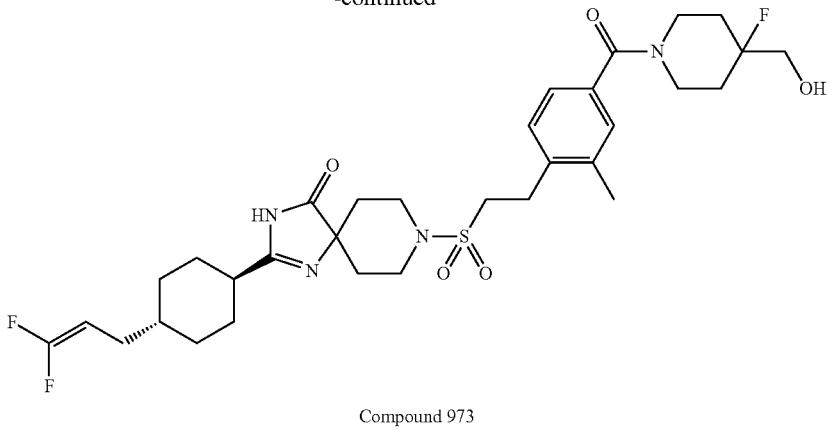

Compound 973

2-[4-(3,3-Difluoro-allyl)-cyclohexyl]-8-{2-[4-(4-fluoro-4-hydroxymethyl-piperidine-1-carbonyl)-2-methyl-phenyl]-ethanesulfonyl}-1,3,8-triaza-spiro[4.5]dec-1-en-4-one was synthesized by operations similar to those in Reaction 10-14 using appropriate reagents and starting material.

MS (ESI) m/z=653 (M+H)+.

The example compound shown below was synthesized by operations similar to those in Reaction 215-3 using appropriate reagents and starting material.

Compound 974

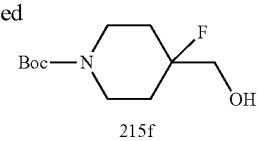

215f

1-Oxa-6-aza-spiro[2.5]octane-6-carboxylic acid tert-butyl ester (144 mg, 679 μmol), triethylamine (1.10 mL, 6.79 mmol) and triethylamine trihydrofluoride (2.85 mL, 20.4 mmol) were mixed in a sealed test tube. This mixture was

TABLE 139

| Compound | Structure | LCMS condition | Retention time (min) | MS (m/z) |
|---|---|---|---|---|
| 974 | (see structure above) | LCMS-B-1 | 1.93 | 653 (M + H)+ |

The amine reagent used for Compound 973 ((4-fluoro-piperidin-4-yl)-methanol hydrochloride) was synthesized by the following method.

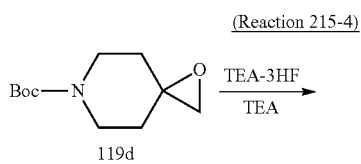

stirred at 120° C. for 6.5 hours. The reaction mixture was cooled, and then quenched with a 2 N aqueous NaOH solution and extracted with ethyl acetate three times. The organic layers were combined, washed with saturated brine, dried over sodium sulfate and concentrated under reduced pressure. The resulting residue was purified by silica gel column chromatography (hexane-AcOEt) to give 4-fluoro-4-hydroxymethyl-piperidine-1-carboxylic acid tert-butyl ester (24.9 mg, 16%).

$^1$H-NMR (400 MHz, CDCl$_3$) δ 1.44-1.64 (2H, m), 1.82-1.96 (2H, m), 3.04-3.17 (2H, m), 3.61 (2H, d, J=20.0 Hz), 3.84-3.98 (2H, br-m).

(Reaction 215-5)

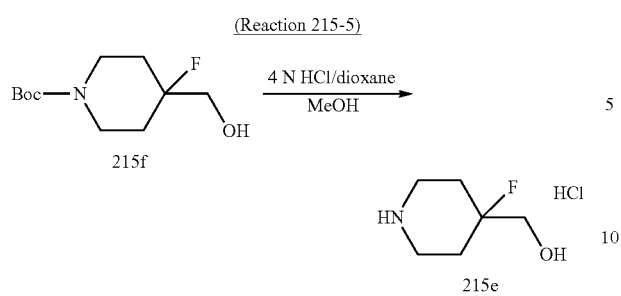

A 4 N solution of hydrochloric acid in 1,4-dioxane (213 μL) was added to a solution of 4-fluoro-4-hydroxymethyl-piperidine-1-carboxylic acid tert-butyl ester (24.9 mg, 0.107 μmol) in MeOH (213 μL) at room temperature, and the mixture was stirred at room temperature for two hours. The reaction solution was concentrated under reduced pressure to give (4-fluoro-piperidin-4-yl)-methanol hydrochloride as a brown form (19.6 mg).

$^1$H-NMR (400 MHz, CD$_3$OD) δ 1.80-2.08 (2H, m), 2.10-2.20 (2H, m), 3.17-3.30 (2H, m), 3.30-3.45 (2H, m), 3.63 (2H, d, J=19.6 Hz).

The sulfonyl chloride reagent used for Compound 973 (4-(2-chlorosulfonyl-ethyl)-3-methyl-benzoic acid methyl ester) was synthesized by the following method.

(Reaction 215-6)

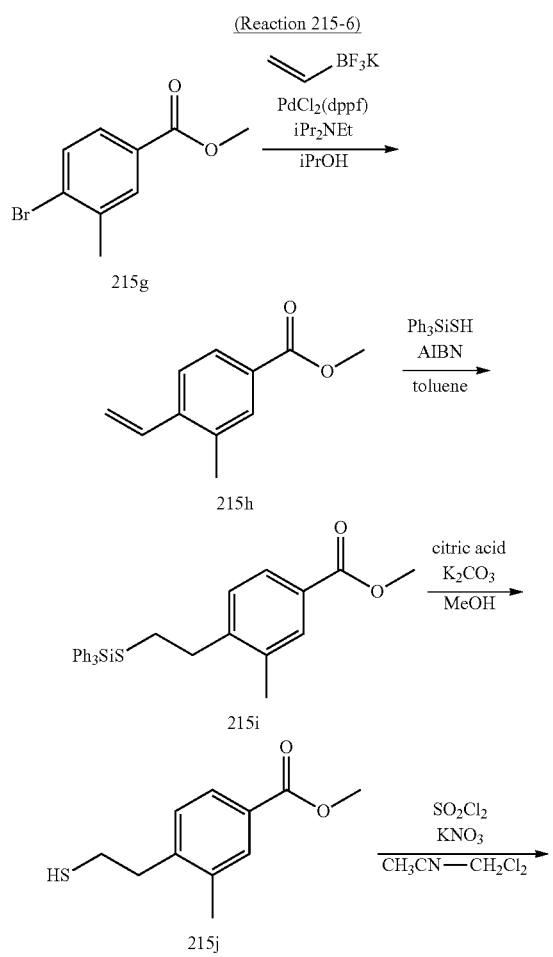

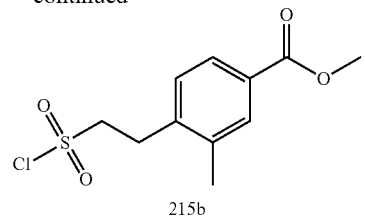

4-(2-Chlorosulfonyl-ethyl)-3-methyl-benzoic acid methyl ester was synthesized by operations similar to those in Reaction 10-2, Reaction 10-3, Reaction 10-4 and Reaction 10-5 using appropriate reagents and starting material.

MS (ESI) m/z=299 (M+Na)+.

Example 216

2-(4-Ethyl-cyclohexyl)-8-(2-{4-[4-(2-fluoro-ethyl)-piperazine-1-carbonyl]-2-methyl-phenyl}-ethanesulfonyl)-1,3,8-triaza-spiro[4.5]dec-1-en-4-one (Compound 975)

(Reaction 216-1)

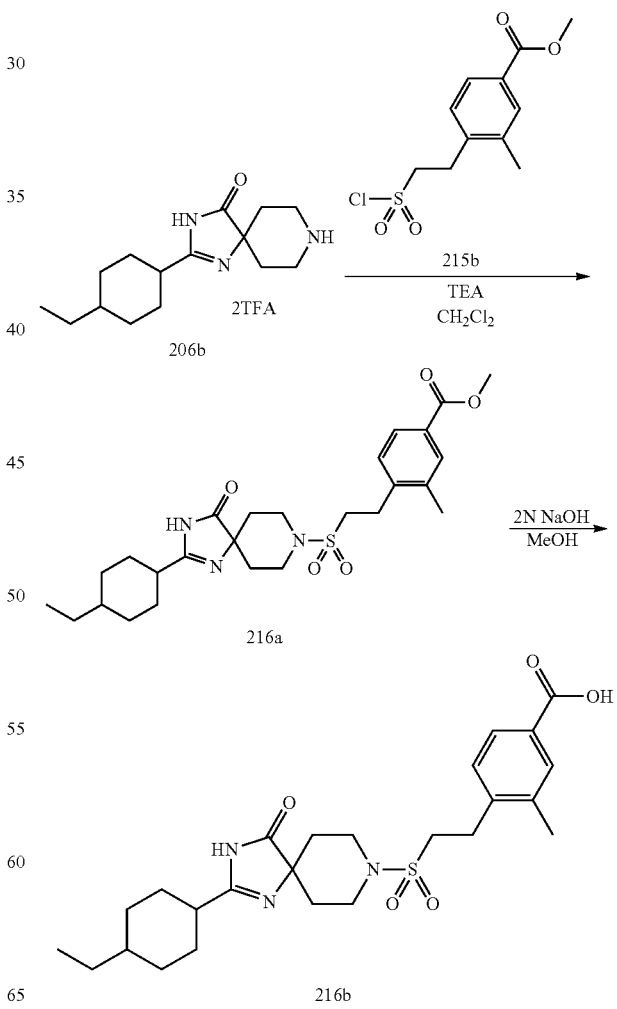

4-{2-[2-(4-Ethyl-cyclohexyl)-4-oxo-1,3,8-triaza-spiro[4.5]dec-1-ene-8-sulfonyl]-ethyl}-3-methyl-benzoic acid was synthesized by operations similar to those in Reaction 5-4 and Reaction 95-18 using appropriate reagents and starting material.

MS (ESI) m/z=490 (M+H)+.

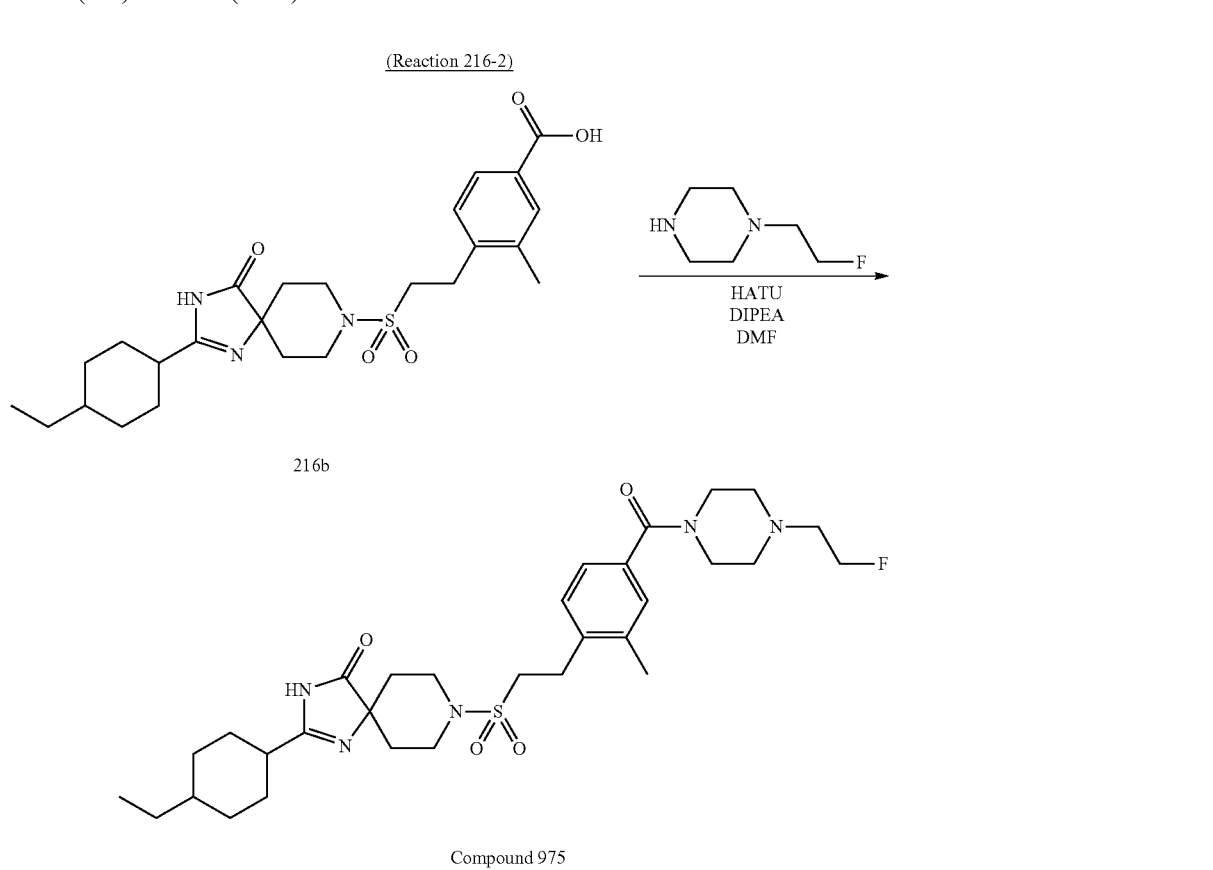

2-(4-Ethyl-cyclohexyl)-8-(2-{4-[4-(2-fluoro-ethyl)-piperazine-1-carbonyl]-2-methyl-phenyl}-ethanesulfonyl)-1,3,8-triaza-spiro[4.5]dec-1-en-4-one was synthesized by operations similar to those in Reaction 10-14 using appropriate reagents and starting material.

MS (ESI) m/z=604 (M+H)+.

The example compound shown below was synthesized by operations similar to those in Reaction 216-2 using appropriate reagents and starting material.

Compound 976

TABLE 140

| Compound | Structure | LCMS condition | Retention time (min) | MS (m/z) |
|---|---|---|---|---|
| 976 | 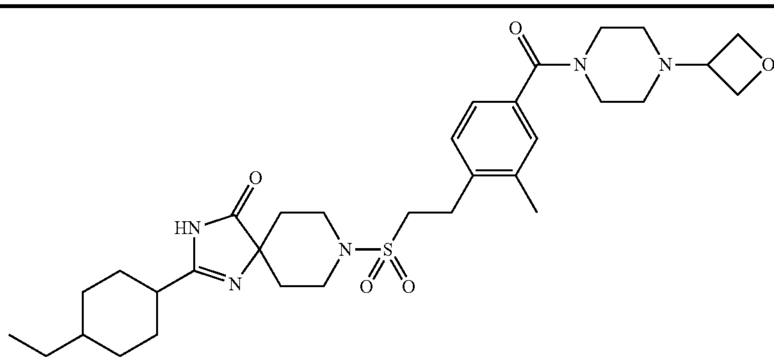 | LCMS-A-1 | 1.81 | 614 (M + H)+ |

1077

The amine reagent used for Compound 976 (1-oxetan-3-yl-piperazine) was synthesized by the following method.

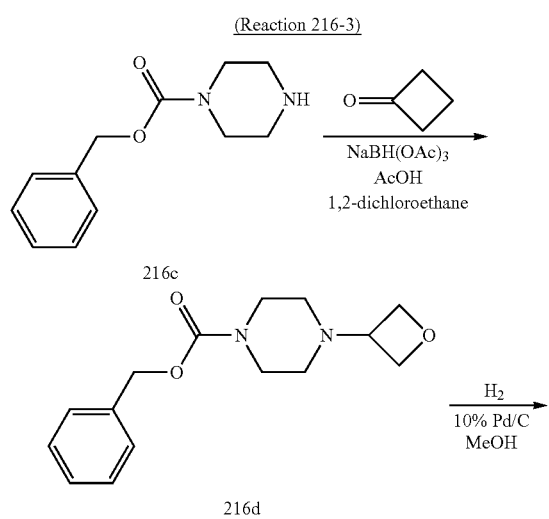

1078

-continued

1-Oxetan-3-yl-piperazine was synthesized by operations similar to those in Reaction 41-1 and Reaction 18-2 using appropriate reagents and starting material.

$^1$H-NMR (400 MHz, CDCl$_3$) δ 2.27 (4H, br s), 2.89-2.91 (4H, m), 3.42-3.48 (1H, m), 4.58-4.65 (4H, m).

Example 217

8-{2-[2-Methyl-4-(pyrrolidine-1-carbonyl)-phenyl]-ethanesulfonyl}-2-nonyl-1,3,8-triaza-spiro[4.5]dec-1-en-4-one (Compound 977)

(Reaction 217-1)

3-Methyl-4-[2-(2-nonyl-4-oxo-1,3,8-triaza-spiro[4.5]dec-1-ene-8-sulfonyl)-ethyl]-benzoic acid was synthesized by operations similar to those in Reaction 5-4 and Reaction 95-18 using appropriate reagents and starting material.

MS (ESI) m/z=506 (M+H)+.

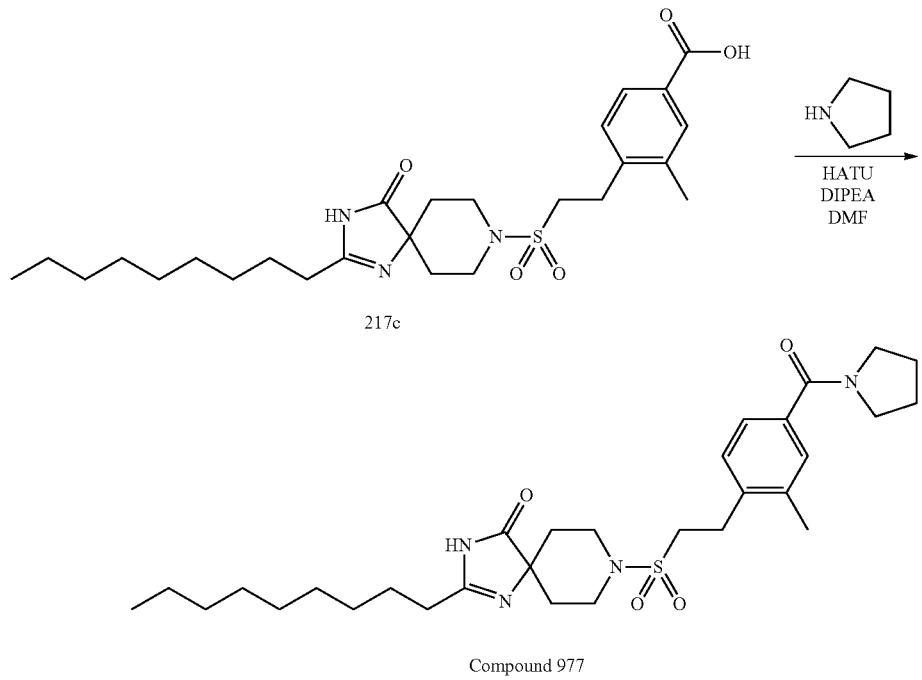

8-{2-[2-Methyl-4-(pyrrolidine-1-carbonyl)-phenyl]-ethanesulfonyl}-2-nonyl-1,3,8-triaza-spiro[4.5]dec-1-en-4-one was synthesized by operations similar to those in Reaction 10-14 using appropriate reagents and starting material.

MS (ESI) m/z=559 (M+H)+.

The example compounds shown below were synthesized by operations similar to those in Reaction 217-2 using appropriate reagents and starting materials.

Compounds 978 to 979

TABLE 141

| Compound | Structure | LCMS condition | Retention time (min) | MS (m/z) |
|---|---|---|---|---|
| 978 | 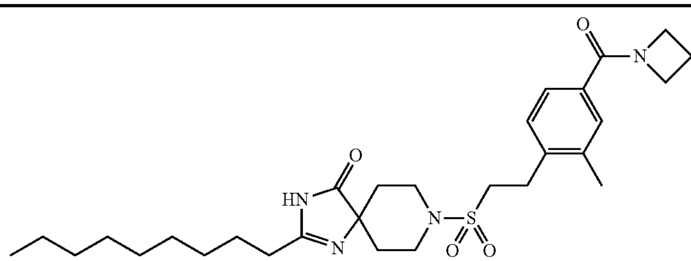 | LCMS-A-1 | 2.47 | 545 (M + H)+ |
| 979 | 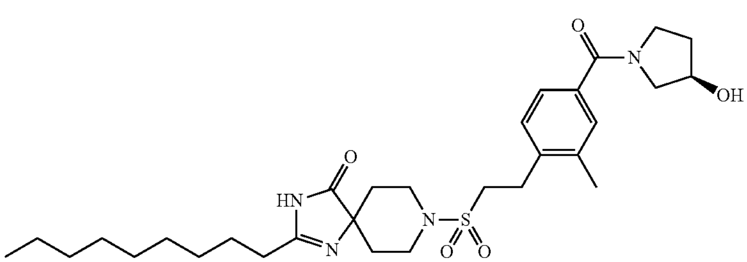 [SMILES: CCCCCCCCCC1=NC2(CCN(S(=O)(=O)CCc3ccc(C(=O)N4CC[C@@H](O)C4)cc3C)CC2)C(=O)N1] | LCMS-A-1 | 2.29 | 575 (M + H)+ |

Example 218
8-{2-[2,6-Dimethyl-4-(pyrrolidine-1-carbonyl)-phenyl]-ethanesulfonyl}-2-nonyl-1,3,8-triaza-spiro[4.5]dec-1-en-4-one (Compound 980)
(Reaction 218-1)
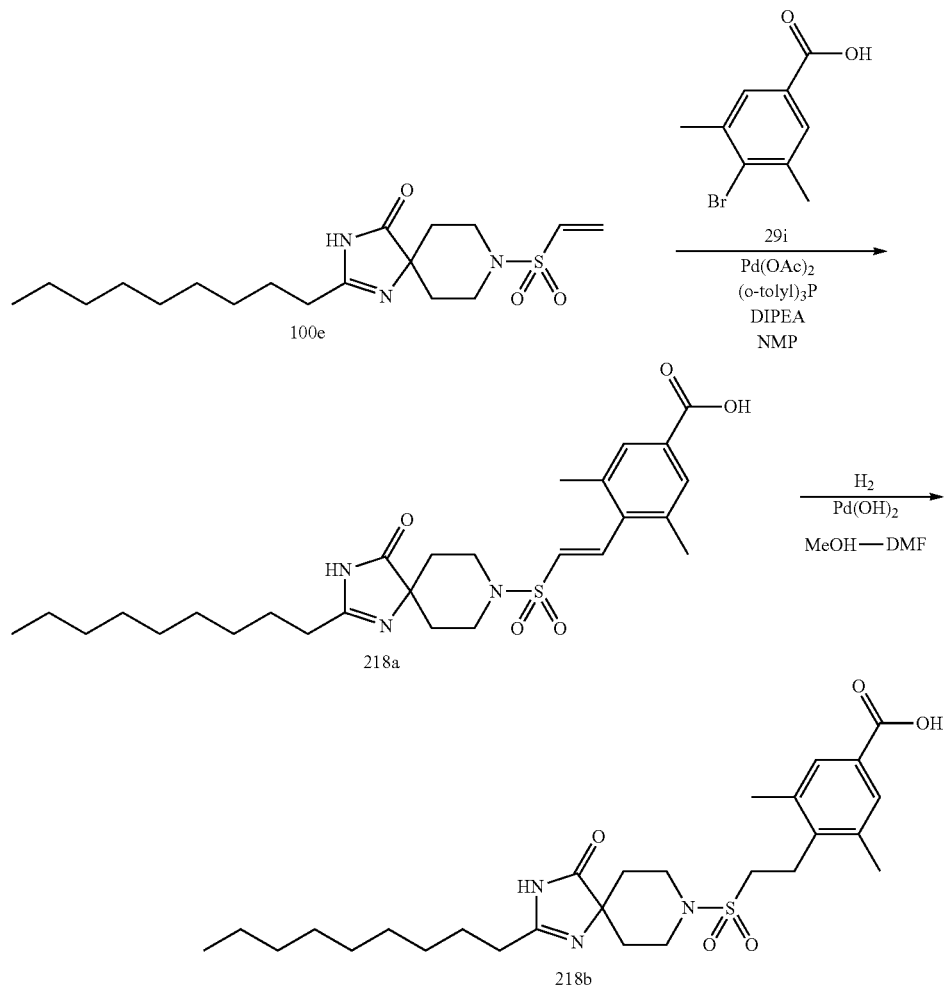
3,5-Dimethyl-4-[2-(2-nonyl-4-oxo-1,3,8-triaza-spiro[4.5]dec-1-ene-8-sulfonyl)-ethyl]-benzoic acid was synthesized by operations similar to those in Reaction 26-1 and Reaction 122-2 using appropriate reagents and starting material.
MS (ESI) m/z=520 (M+H)+.
(Reaction 218-2)
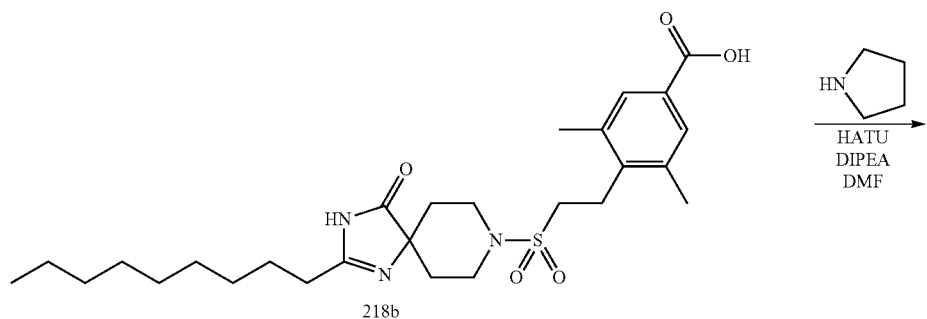

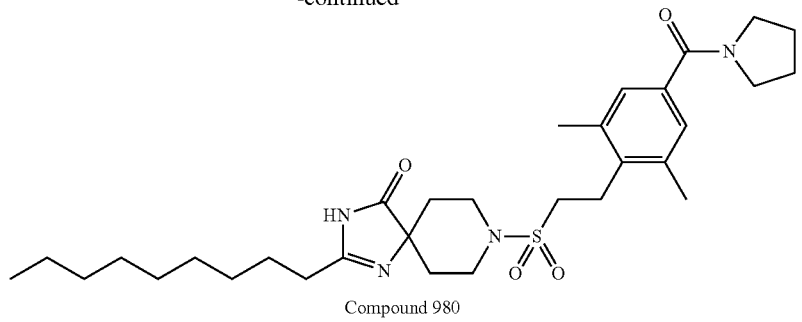

Compound 980

8-{2-[2,6-Dimethyl-4-(pyrrolidine-1-carbonyl)-phenyl]-ethanesulfonyl}-2-nonyl-1,3,8-triaza-spiro[4.5]dec-1-en-4-one was synthesized by operations similar to those in Reaction 10-14 using appropriate reagents and starting material.

MS (ESI) m/z=573 (M+H)+.

The example compounds shown below were synthesized by operations similar to those in Reaction 218-2 using appropriate reagents and starting materials.

Compounds 981 to 986

TABLE 142

| Compound | Structure | LCMS condition | Retention time (min) | MS (m/z) |
|---|---|---|---|---|
| 981 | 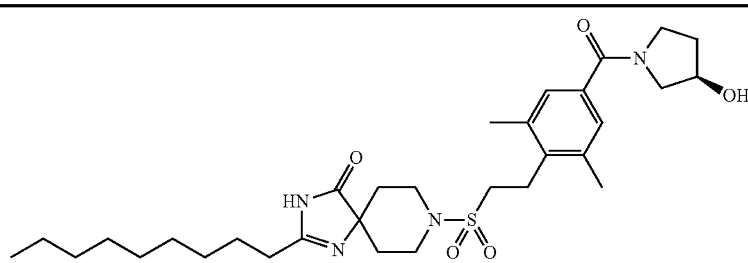 | LCMS-F-1 | 1.03 | 589 (M + H)+ |
| 982 | 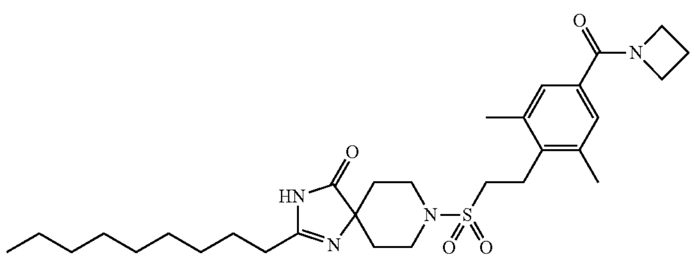 [SMILES: CCCCCCCCCC1=NC2(CCN(S(=O)(=O)CCc3c(C)cc(C(=O)N4CCC4)cc3C)CC2)C(=O)N1] | LCMS-F-1 | 1.09 | 559 (M + H)+ |
| 983 | 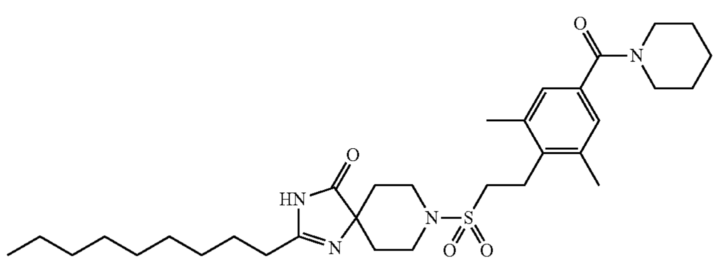 [SMILES: CCCCCCCCCC1=NC2(CCN(S(=O)(=O)CCc3c(C)cc(C(=O)N4CCCCC4)cc3C)CC2)C(=O)N1] | LCMS-F-1 | 1.13 | 587 (M + H)+ |
| 984 | 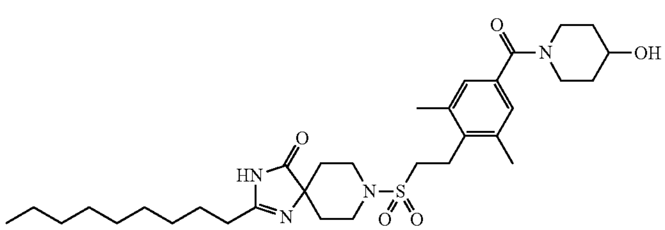 [SMILES: CCCCCCCCCC1=NC2(CCN(S(=O)(=O)CCc3c(C)cc(C(=O)N4CCC(O)CC4)cc3C)CC2)C(=O)N1] | LCMS-F-1 | 1.04 | 603 (M + H)+ |

TABLE 142-continued
| Compound | Structure | LCMS condition | Retention time (min) | MS (m/z) |
|---|---|---|---|---|
| 985 | 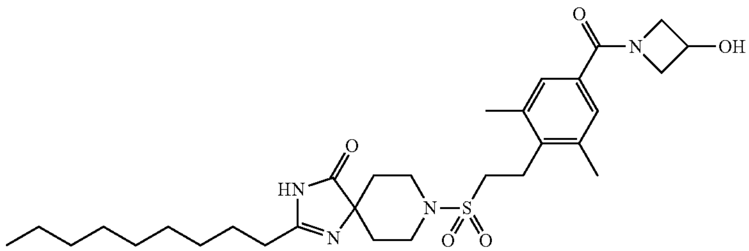 [SMILES: CCCCCCCCCC1=NC2(CCN(S(=O)(=O)CCc3c(C)cc(C(=O)N4CC(O)C4)cc3C)CC2)C(=O)N1] | LCMS-F-1 | 1.03 | 575 (M + H)+ |
| 986 | 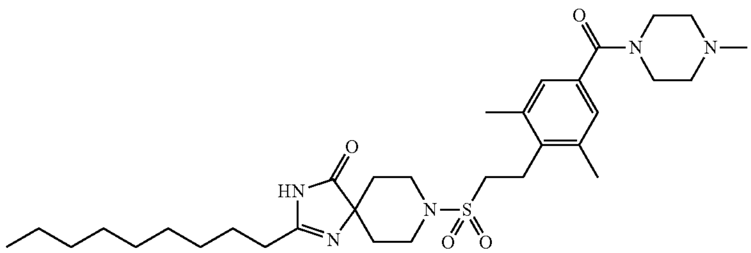 [SMILES: CCCCCCCCCC1=NC2(CCN(S(=O)(=O)CCc3c(C)cc(C(=O)N4CCN(C)CC4)cc3C)CC2)C(=O)N1] | LCMS-F-1 | 1.08 | 602 (M + H)+ |
Example 219
N,N-Dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide (Compound 987)
(Reaction 219-1)
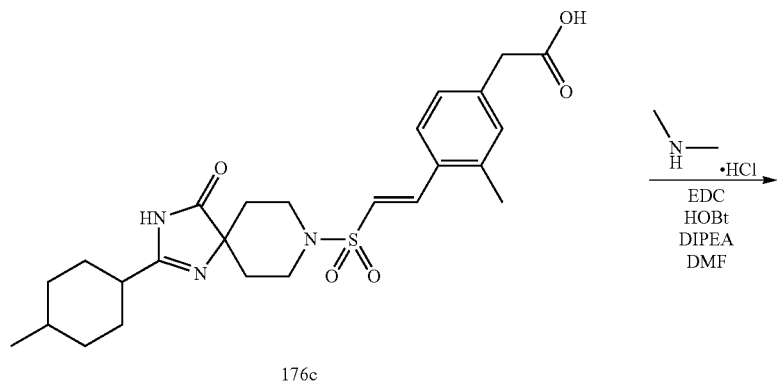
176c
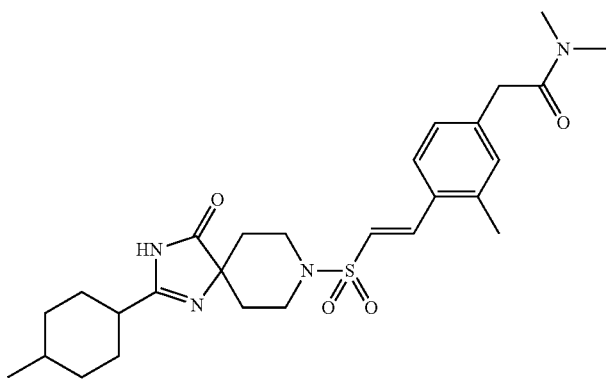
Compound 987

N,N-Dimethyl-2-(3-methyl-4-{(E)-2-[2-(4-methyl-cyclohexyl)-4-oxo-1,3,8-triaza-spiro[4.5]dec-1-ene-8-sulfonyl]-vinyl}-phenyl)-acetamide was synthesized by operations similar to those in Reaction 10-18 using appropriate reagents and starting material.

MS (ESI) m/z=515 (M+H)+.

The example compound shown below was synthesized by operations similar to those in Reaction 219-1 using appropriate reagents and starting material.

Compound 988

TABLE 143

| Compound | Structure | LCMS condition | Retention time (min) | MS (m/z) |
|---|---|---|---|---|
| 988 | 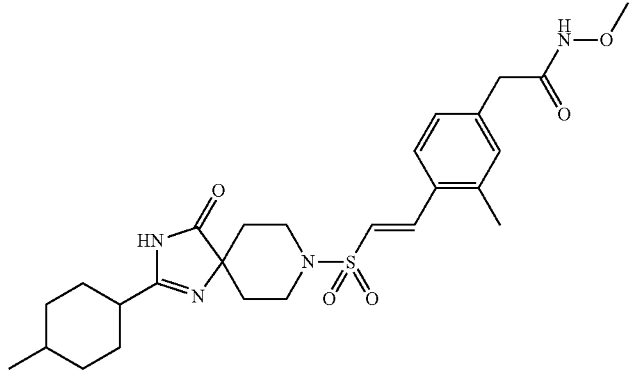 | LCMS-C-1 | 2.47 | 517 (M + H)+ |

Example 220

8-{(E)-2-[4-(4-Hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one (Compound 989)

(Reaction 220-1)

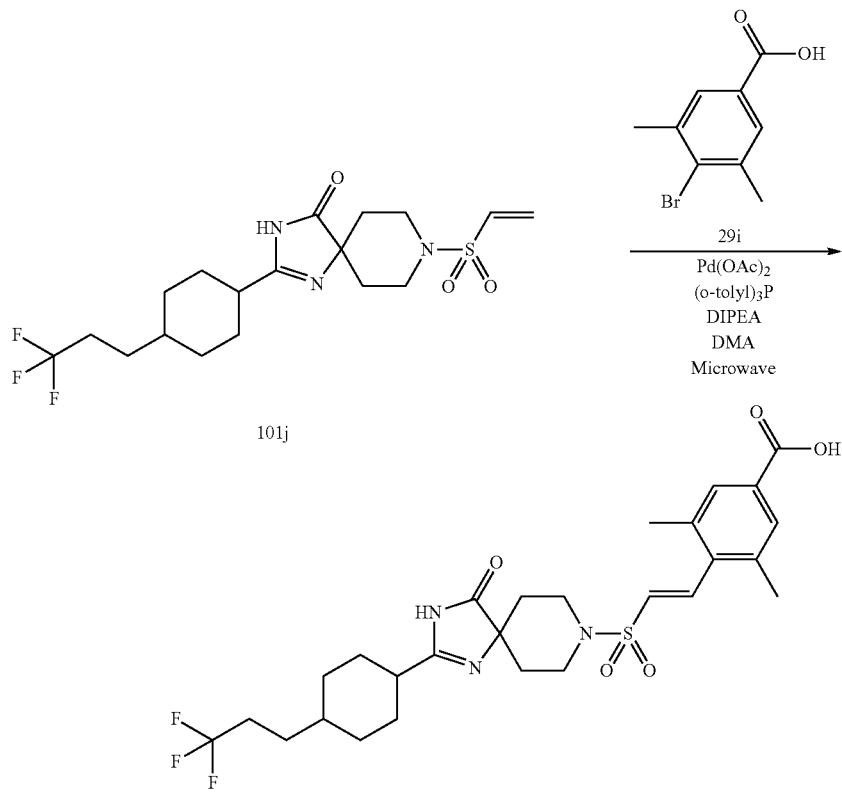

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid was synthesized by operations similar to those in Reaction 25-2 using appropriate reagents and starting material.

MS (ESI) m/z=570 (M+H)+.

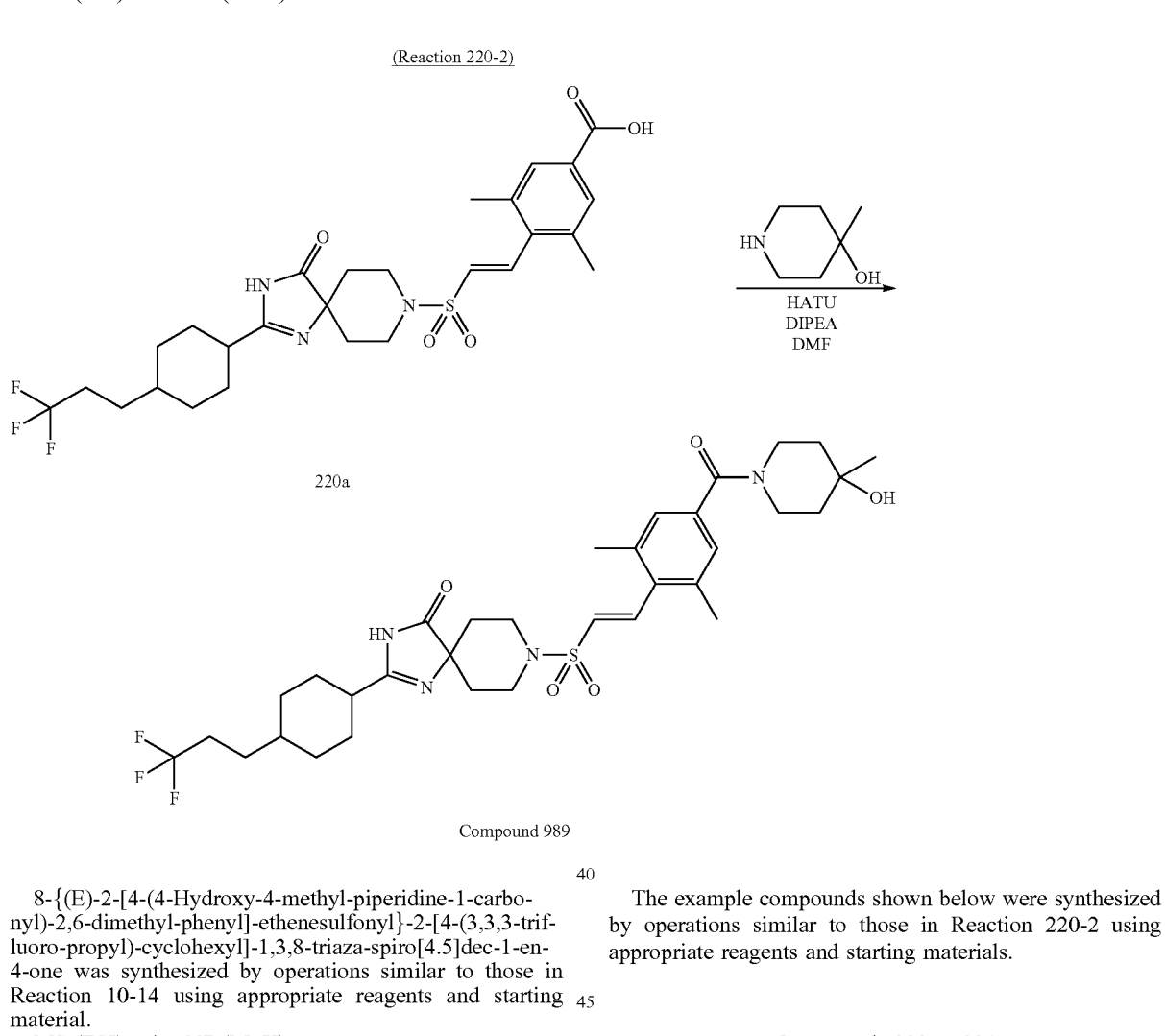

8-{(E)-2-[4-(4-Hydroxy-4-methyl-piperidine-1-carbonyl)-2,6-dimethyl-phenyl]-ethenesulfonyl}-2-[4-(3,3,3-trifluoro-propyl)-cyclohexyl]-1,3,8-triaza-spiro[4.5]dec-1-en-4-one was synthesized by operations similar to those in Reaction 10-14 using appropriate reagents and starting material.

MS (ESI) m/z=667 (M+H)+.

The example compounds shown below were synthesized by operations similar to those in Reaction 220-2 using appropriate reagents and starting materials.

Compounds 990 to 994

TABLE 144

| Compound | Structure | LCMS condition | Retention time (min) | MS (m/z) |
|---|---|---|---|---|
| 990 | 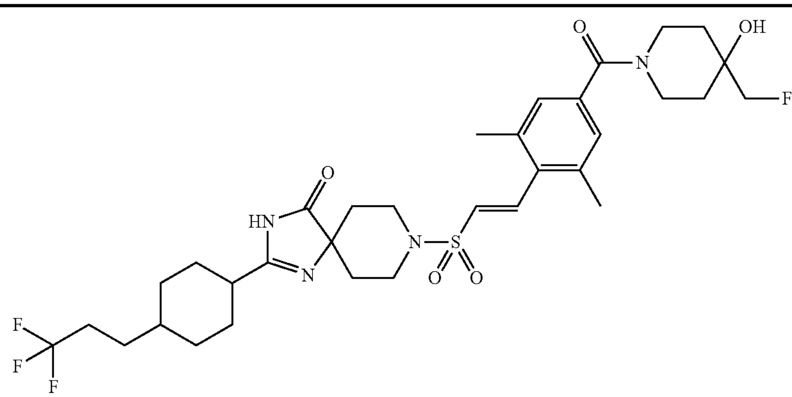 | LCMS-D-1 | 2.28 | 685 (M + H)+ |

TABLE 144-continued

| Compound | Structure | LCMS condition | Retention time (min) | MS (m/z) |
|---|---|---|---|---|
| 991 | 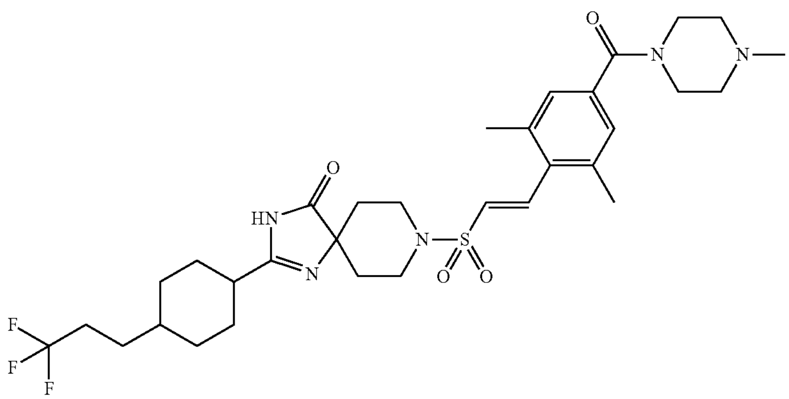 [SMILES: Cc1cc(C(=O)N2CCN(C)CC2)cc(C)c1/C=C/S(=O)(=O)N1CCC2(CC1)N=C(C1CCC(CCC(F)(F)F)CC1)NC2=O] | LCMS-D-1 | 1.60 | 652 (M + H)+ |
| 992 | 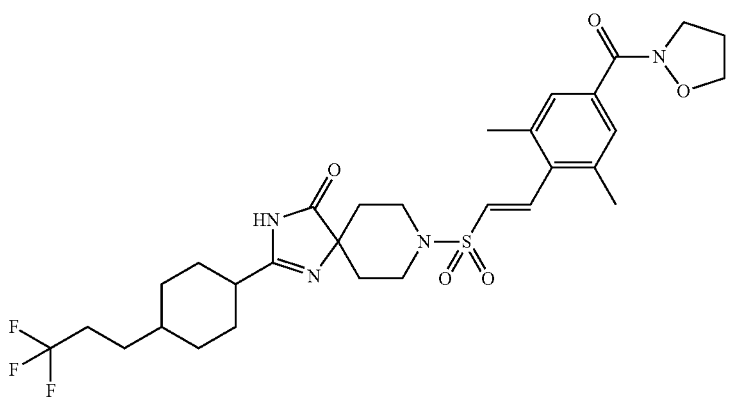 [SMILES: Cc1cc(C(=O)N2CCCO2)cc(C)c1/C=C/S(=O)(=O)N1CCC2(CC1)N=C(C1CCC(CCC(F)(F)F)CC1)NC2=O] | LCMS-D-1 | 2.57 | 625 (M + H)+ |
| 993 | 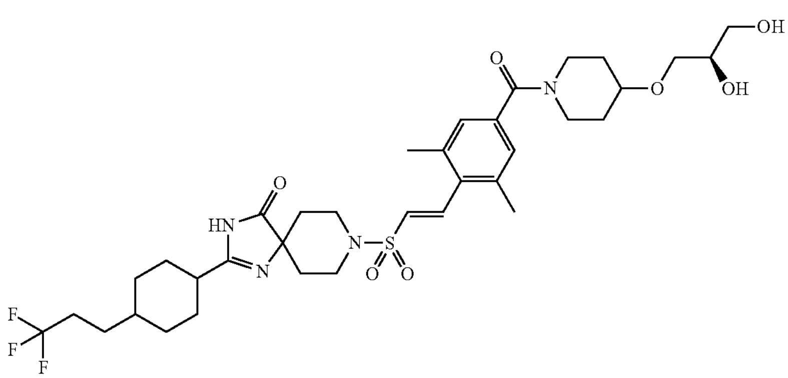 [SMILES: Cc1cc(C(=O)N2CCC(OC[C@H](O)CO)CC2)cc(C)c1/C=C/S(=O)(=O)N1CCC2(CC1)N=C(C1CCC(CCC(F)(F)F)CC1)NC2=O] | LCMS-D-1 | 1.88 | 727 (M + H)+ |
| 994 | 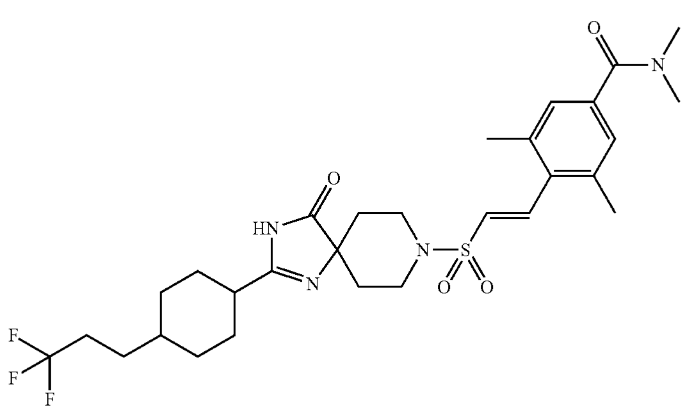 [SMILES: Cc1cc(C(=O)N(C)C)cc(C)c1/C=C/S(=O)(=O)N1CCC2(CC1)N=C(C1CCC(CCC(F)(F)F)CC1)NC2=O] | LCMS-D-1 | 1.87 | 597 (M + H)+ |

The amine reagent used for Compound 993 ((R)-3-(piperidin-4-yloxy)-propane-1,2-diol hydrochloride) was synthesized by the following method.

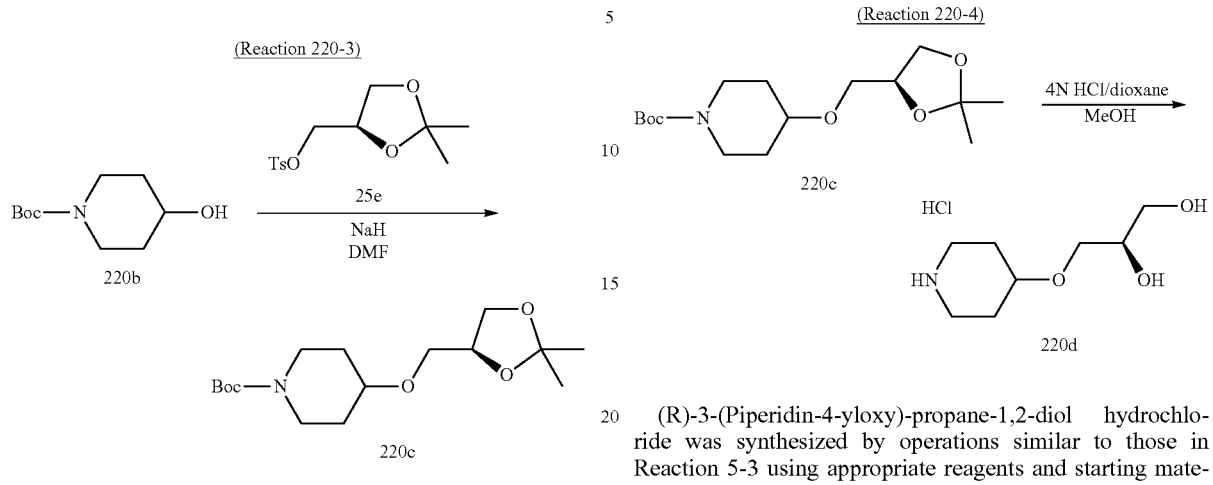

4-((S)-2,2-Dimethyl-[1,3]dioxolan-4-ylmethoxy)-piperidine-1-carboxylic acid tert-butyl ester was synthesized by operations similar to those in Reaction 25-3 using appropriate reagents and starting material.

¹H-NMR (CDCl₃) δ 1.35 (s, 3H), 1.41 (s, 3H), 1.44 (s, 9H), 1.48-1.53 (m, 2H), 1.75-1.87 (m, 2H), 2.95-3.15 (m, 2H), 3.39-3.50 (m, 2H), 3.51-3.58 (m, 2H), 3.67-3.80 (m, 2H), 4.00-4.09 (m, 1H), 4.17-4.32 (m, 1H).

(R)-3-(Piperidin-4-yloxy)-propane-1,2-diol hydrochloride was synthesized by operations similar to those in Reaction 5-3 using appropriate reagents and starting material. This was used in the next reaction without purification.

Example 221

8-{2-[2,6-Dimethyl-4-(4-methyl-piperazine-1-carbonyl)-phenyl]-ethanesulfonyl}-2-[4-(3,3,3-trifluoropropyl)-cyclohexyl]-1,3,8-triaza-spiro[4.5]dec-1-en-4-one (Compound 995)

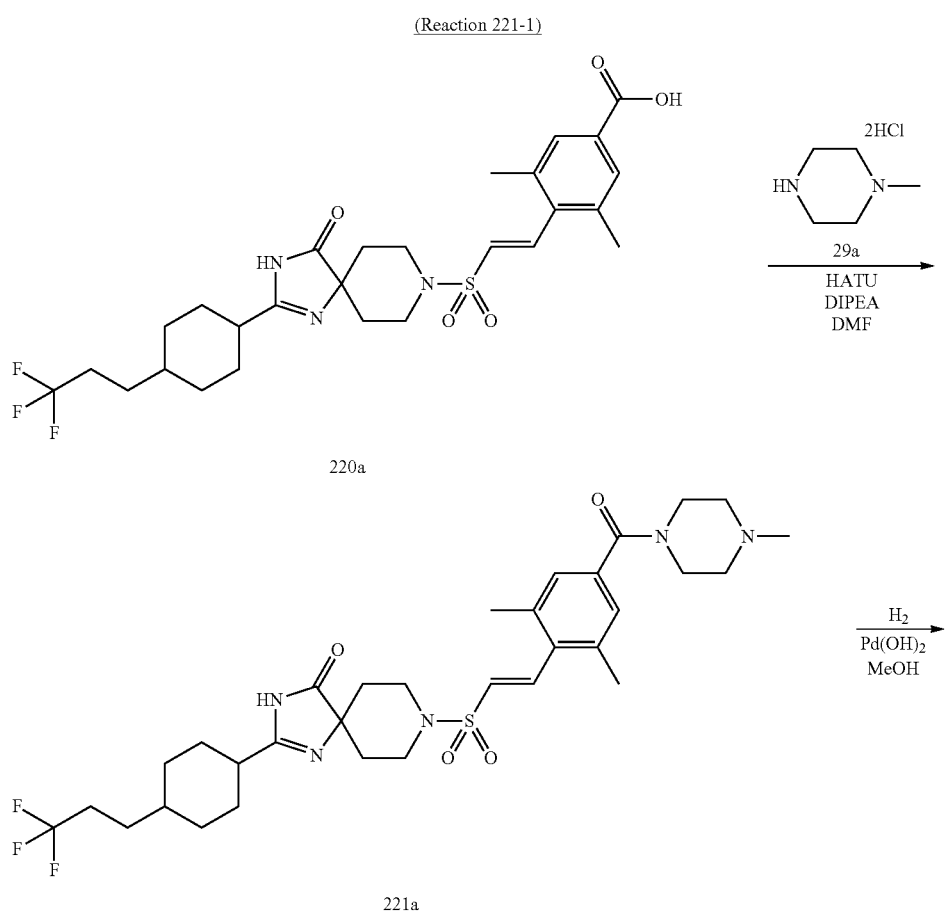

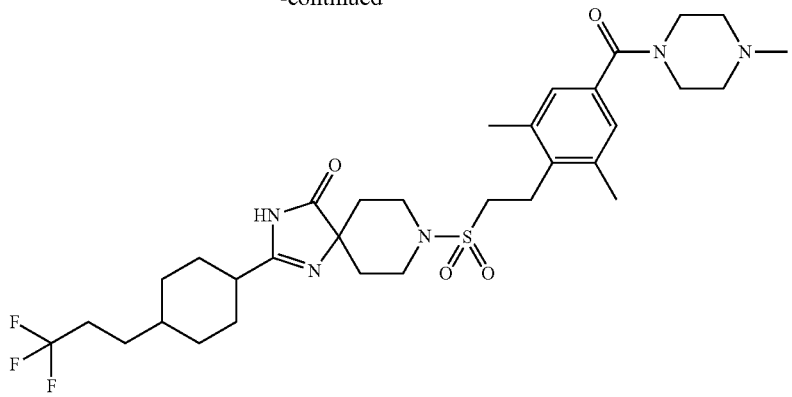

Compound 995

8-{2-[2,6-Dimethyl-4-(4-methyl-piperazine-1-carbonyl)-phenyl]-ethanesulfonyl}-2-[4-(3,3,3-trifluoro-propyl)-cyclohexyl]-1,3,8-triaza-spiro[4.5]dec-1-en-4-one was synthesized by operations similar to those in Reaction 10-14 and Reaction 122-2 using appropriate reagents and starting material.

MS (ESI) m/z=654 (M+H)+.

Example 222

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide (Compound 996)

(Reaction 222-1)

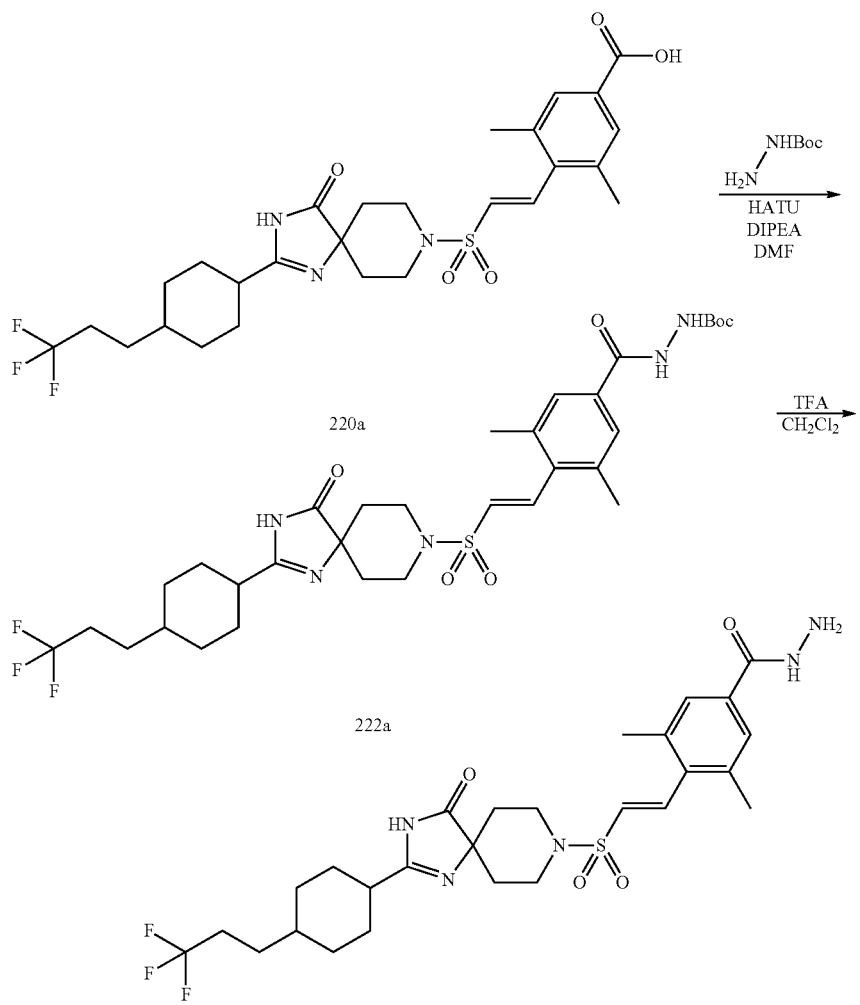

Compound 996

3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzoic acid hydrazide was synthesized by operations similar to those in Reaction 10-14 and Reaction 4-1 using appropriate reagents and starting material.

MS (ESI) m/z=584 (M+H)+.

The example compound shown below was synthesized by operations similar to those in Reaction 222-1 using appropriate reagents and starting material.

Compound 997

TABLE 145

| Compound | Structure | LCMS condition | Retention time (min) | MS (m/z) |
|---|---|---|---|---|
| 997 | 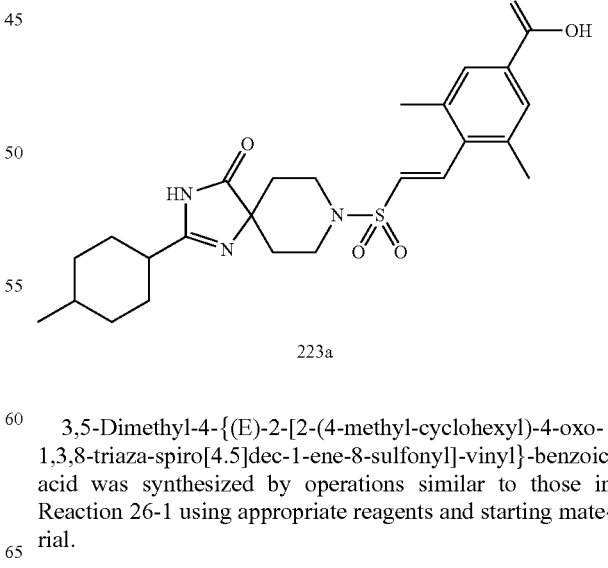 | LCMS-D-1 | 2.12 | 624 (M + H)+ |

Example 223

N-Methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide (Compound 998)

(Reaction 223-1)

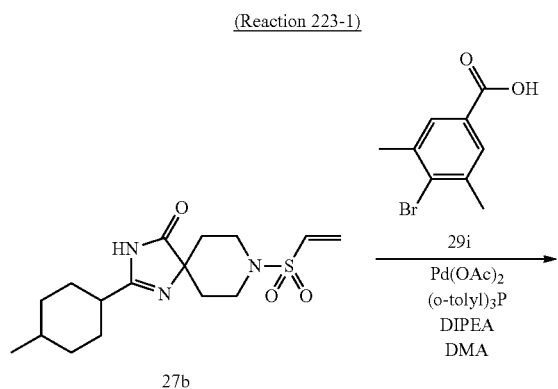

3,5-Dimethyl-4-{(E)-2-[2-(4-methyl-cyclohexyl)-4-oxo-1,3,8-triaza-spiro[4.5]dec-1-ene-8-sulfonyl]-vinyl}-benzoic acid was synthesized by operations similar to those in Reaction 26-1 using appropriate reagents and starting material.

MS (ESI) m/z=488 (M+H)+.

(Reaction 223-2)

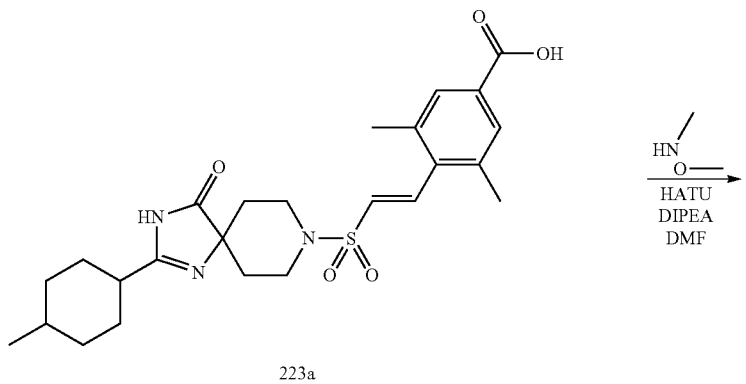

223a

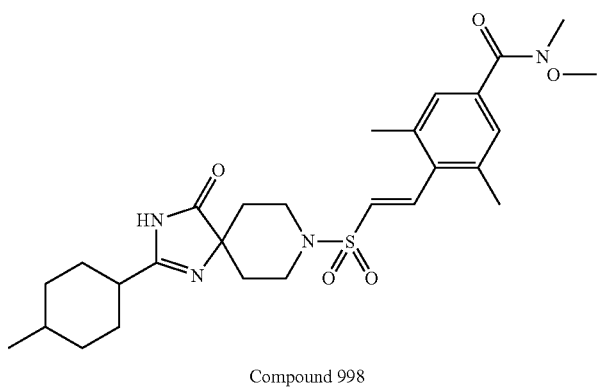

Compound 998

N-Methoxy-3,5,N-trimethyl-4-{(E)-2-[2-(4-methyl-cyclohexyl)-4-oxo-1,3,8-triaza-spiro[4.5]dec-1-ene-8-sulfonyl]-vinyl}-benzamide was synthesized by operations similar to those in Reaction 10-14 using appropriate reagents and starting material.

MS (ESI) m/z=531 (M+H)+.

The example compounds shown below were synthesized by operations similar to those in Reaction 223-2 using appropriate reagents and starting materials.

Compounds 999 to 1003

TABLE 146

| Compound | Structure | LCMS condition | Retention time (min) | MS (m/z) |
|---|---|---|---|---|
| 999 | 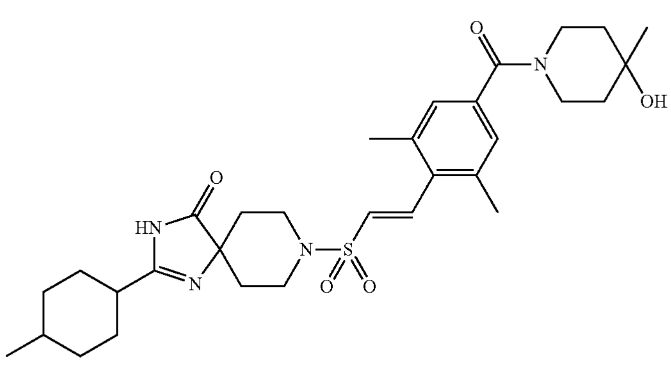 [SMILES: Cc1cc(C(=O)N2CCC(C)(O)CC2)cc(C)c1/C=C/S(=O)(=O)N1CCC2(CC1)N=C(C1CCC(C)CC1)NC2=O] | LCMS-D-1 | 1.99 | 585 (M + H)+ |

TABLE 146-continued
| Compound | Structure | LCMS condition | Retention time (min) | MS (m/z) |
|---|---|---|---|---|
| 1000 | 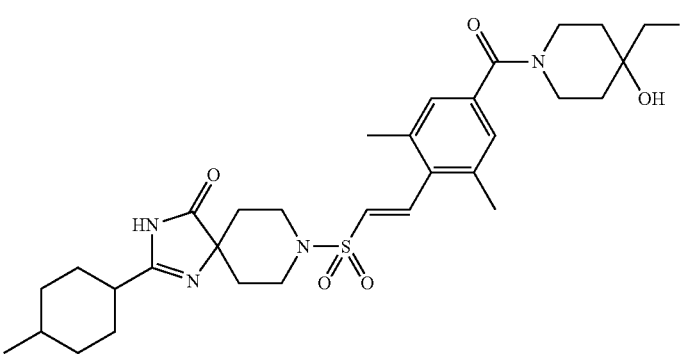 | LCMS-D-1 | 1.96 | 603 (M + H)+ |
| 1001 | 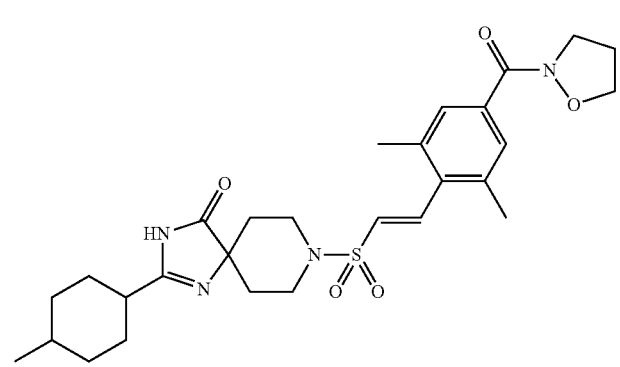 [SMILES: Cc1cc(C(=O)N2CCCO2)cc(C)c1/C=C/S(=O)(=O)N1CCC2(CC1)N=C(C1CCC(C)CC1)NC2=O] | LCMS-D-1 | 2.48 | 543 (M + H)+ |
| 1002 | 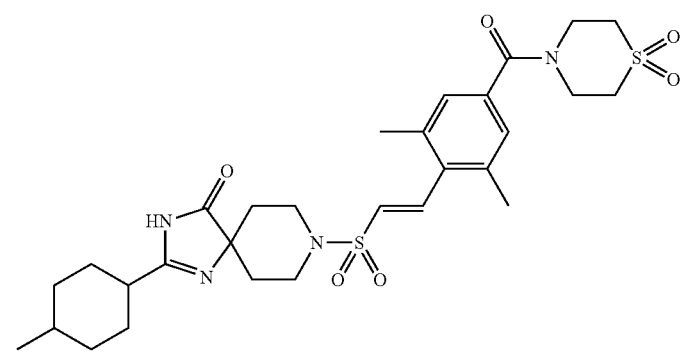 [SMILES: Cc1cc(C(=O)N2CCS(=O)(=O)CC2)cc(C)c1/C=C/S(=O)(=O)N1CCC2(CC1)N=C(C1CCC(C)CC1)NC2=O] | LCMS-D-1 | 1.67 | 605 (M + H)+ |
| 1003 | 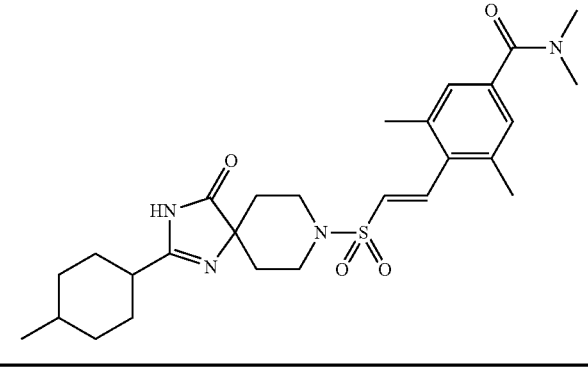 | LCMS-D-1 | 1.91 | 515 (M + H)+ |

Example 224
8-{2-[2,6-Dimethyl-4-(pyrazolidine-1-carbonyl)-phenyl]-ethanesulfonyl}-2-(4-methyl-cyclohexyl)-1,3,8-triaza-spiro[4.5]dec-1-en-4-one
(Reaction 224-1)
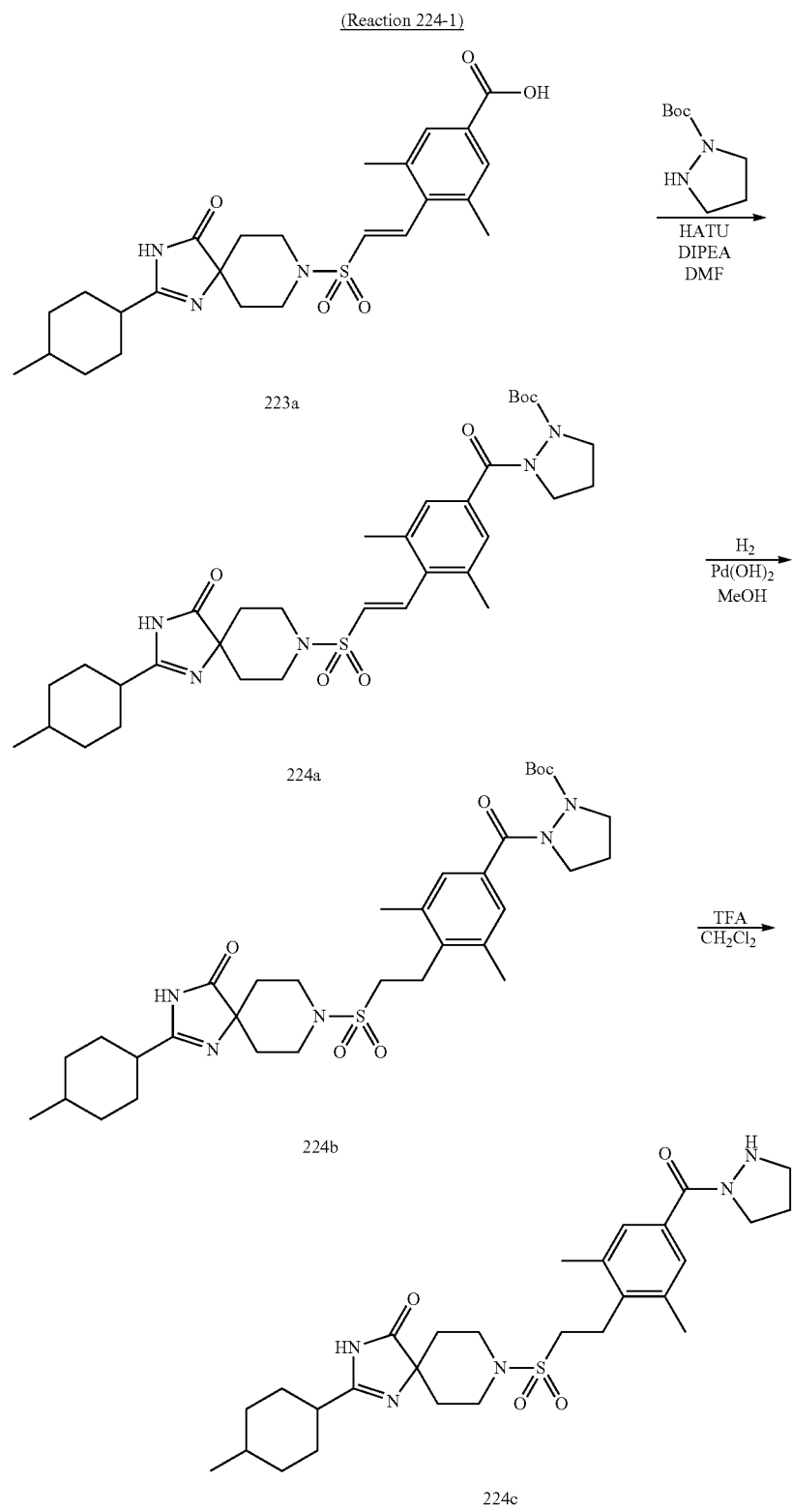

8-{2-[2,6-Dimethyl-4-(pyrazolidine-1-carbonyl)-phenyl]-ethanesulfonyl}-2-(4-methyl-cyclohexyl)-1,3,8-triaza-spiro[4.5]dec-1-en-4-one was synthesized by operations similar to those in Reaction 10-14, Reaction 122-2 and Reaction 4-1 using appropriate reagents and starting material.

MS (ESI) m/z=544 (M+H)+.

Example 225

8-{(E)-2-[2,6-Dimethyl-4-(pyrazolidine-1-carbonyl)-phenyl]-ethenesulfonyl}-2-(4-methyl-cyclohexyl)-1,3,8-triaza-spiro[4.5]dec-1-en-4-one 8-{(E)-2-[2,6-Dimethyl-4-(pyrazolidine-1-carbonyl)-phenyl]-ethenesulfonyl}-2-(4-methyl-cyclohexyl)-1,3,8-triaza-spiro[4.5]dec-1-en-4-one was synthesized by operations similar to those in Reaction 10-14 and Reaction 4-1 using appropriate reagents and starting material.

MS (ESI) m/z=542 (M+H)+.

Example 226

2-Cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one (Compound 1006)

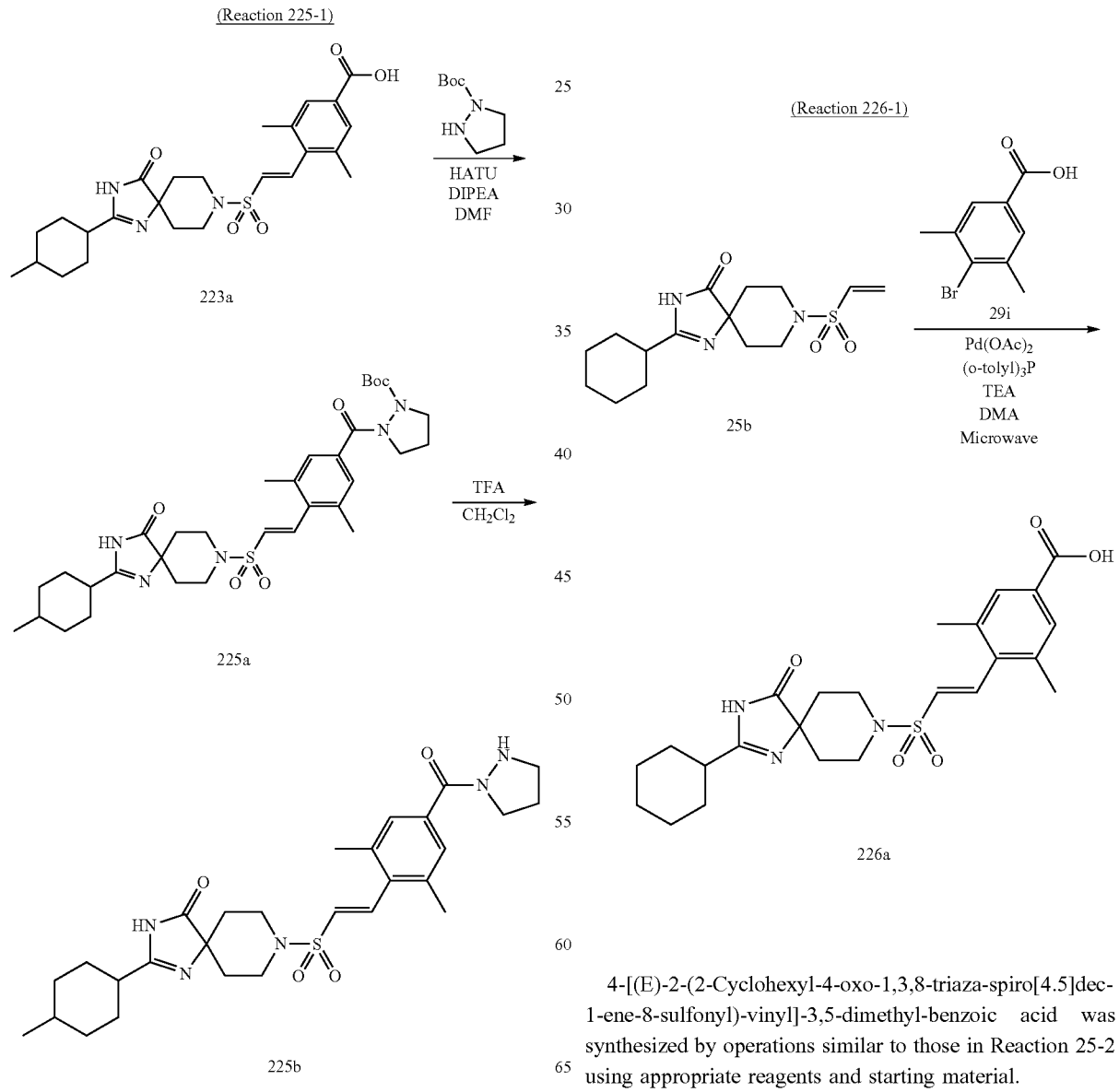

4-[(E)-2-(2-Cyclohexyl-4-oxo-1,3,8-triaza-spiro[4.5]dec-1-ene-8-sulfonyl)-vinyl]-3,5-dimethyl-benzoic acid was synthesized by operations similar to those in Reaction 25-2 using appropriate reagents and starting material.

MS (ESI) m/z=474 (M+H)+.

(Reaction 226-2)

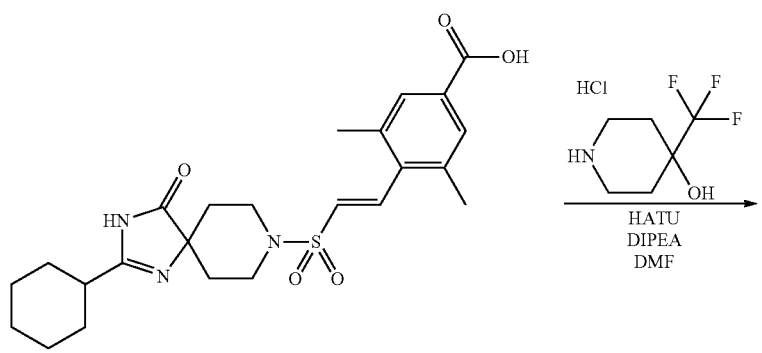

226a

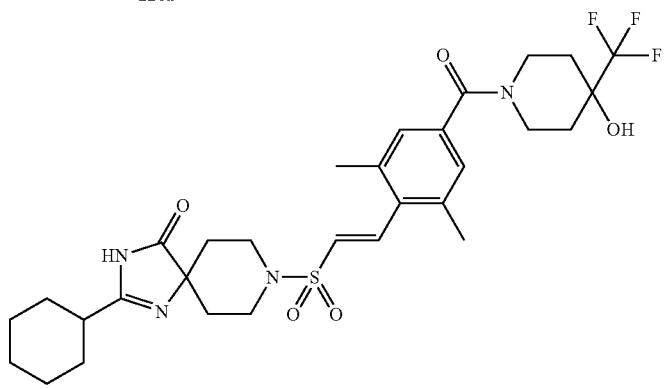

Compound 1006

2-Cyclohexyl-8-{(E)-2-[4-(4-hydroxy-4-trifluoromethyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 using appropriate reagents and starting material.

MS (ESI) m/z=625 (M+H)+.

Example 227

2-Cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one (Compound 1007)

(Reaction 227-1)

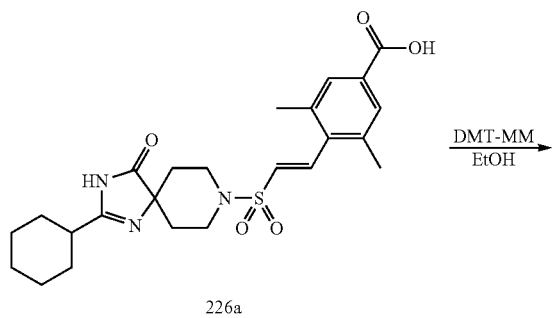

226a

-continued

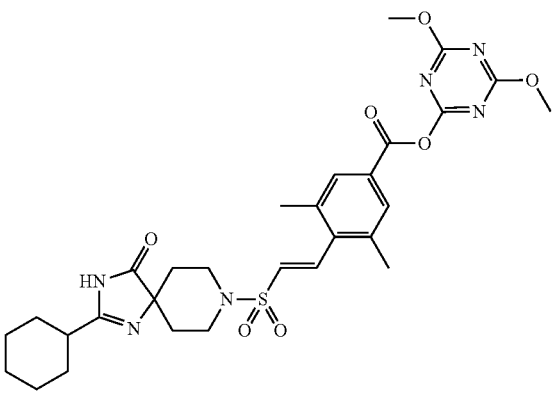

227a

DMT-MM (181 mg, 0.50 mmol) was added to a solution of 4-[(E)-2-(2-cyclohexyl-4-oxo-1,3,8-triaza-spiro[4.5]dec-1-ene-8-sulfonyl)-vinyl]-3,5-dimethyl-benzoic acid (160 mg, 0.33 mmol) in anhydrous ethanol (3.3 ml), and the mixture was stirred at room temperature for 15 hours. The mixture was concentrated under reduced pressure, and the resulting residue was then purified by silica gel column chromatography (dichloromethane-methanol) to give 4-[(E)-2-(2-cyclohexyl-4-oxo-1,3,8-triaza-spiro[4.5]dec-1-ene-8-sulfonyl)-vinyl]-3,5-dimethyl-benzoic acid 4,6-dimethoxy-[1,3,5]triazin-2-yl ester (109 mg, 53%).

MS (ESI) m/z=613 (M+H)+.

(Reaction 227-2)

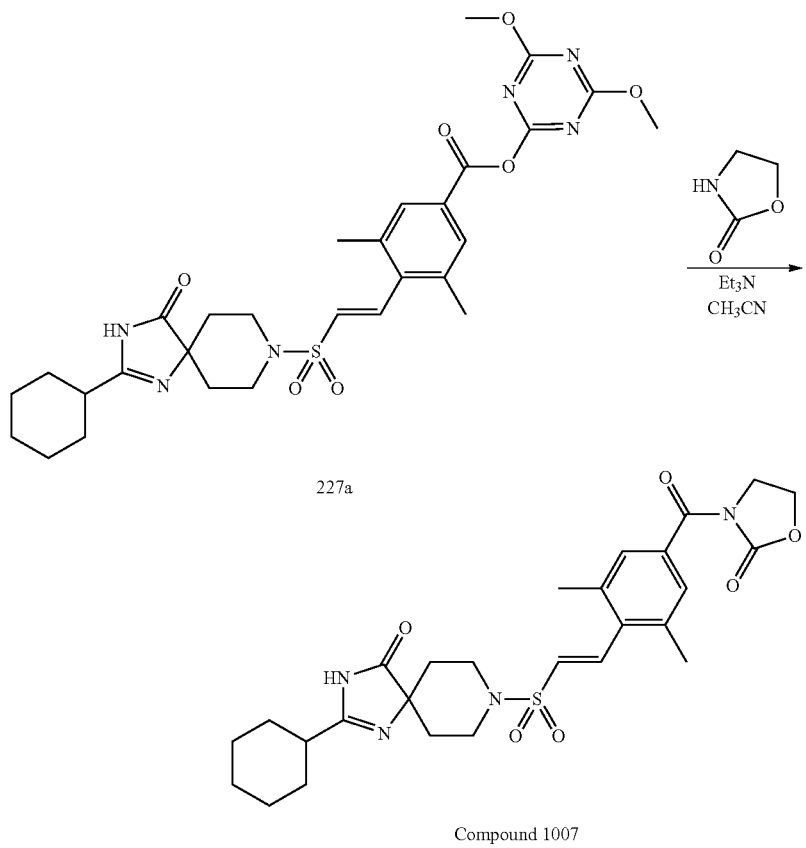

Oxazolidin-2-one (47 mg, 0.53 mmol) was added to a solution of 4-[(E)-2-(2-cyclohexyl-4-oxo-1,3,8-triaza-spiro[4.5]dec-1-ene-8-sulfonyl)-vinyl]-3,5-dimethyl-benzoic acid 4,6-dimethoxy-[1,3,5]triazin-2-yl ester (109 mg, 0.17 mmol) and triethylamine (0.12 ml, 0.88 mmol) in anhydrous acetonitrile (1 ml), and the mixture was heated with stirring at 80° C. for 15 hours. The mixture was cooled and water was then added, followed by extraction with ethyl acetate. The organic layer was washed with water and saturated brine, and then dried over anhydrous magnesium sulfate and concentrated under reduced pressure. The resulting residue was purified by silica gel column chromatography (dichloromethane-methanol) to give 2-cyclohexyl-8-{(E)-2-[2,6-dimethyl-4-(2-oxo-oxazolidine-3-carbonyl)-phenyl]-ethenesulfonyl}-1,3,8-triaza-spiro[4.5]dec-1-en-4-one (31 mg, 32%).

MS (ESI) m/z=543 (M+H)+.

Example 228

2-(4-Butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one (Compound 1008)

(Reaction 228-1)

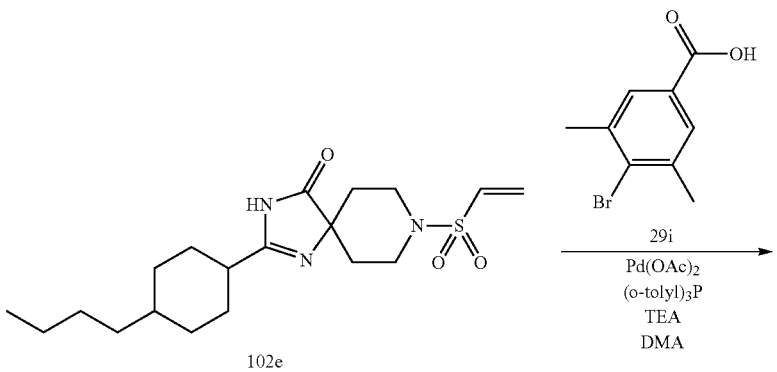

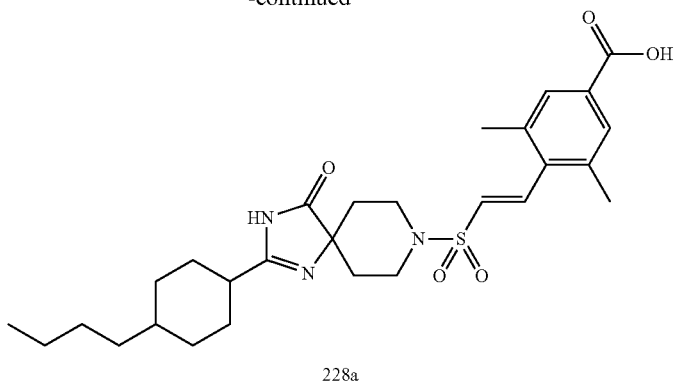

4-{(E)-2-[2-(4-Butyl-cyclohexyl)-4-oxo-1,3,8-triaza-spiro[4.5]dec-1-ene-8-sulfonyl]-vinyl}-3,5-dimethyl-benzoic acid was synthesized by operations similar to those in Reaction 26-1 using appropriate reagents and starting material.

MS (ESI) m/z=530 (M+H)+.

(Reaction 228-2)

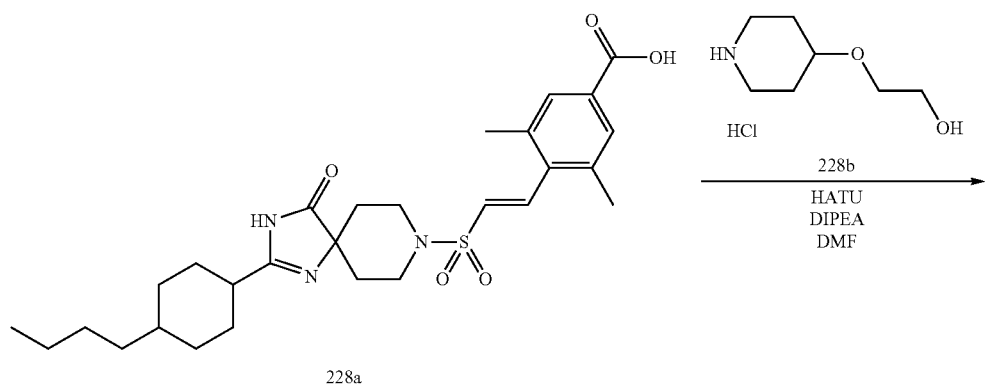

2-(4-Butyl-cyclohexyl)-8-((E)-2-{4-[4-(2-hydroxy-ethoxy)-piperidine-1-carbonyl]-2,6-dimethyl-phenyl}-ethenesulfonyl)-1,3,8-triaza-spiro[4.5]dec-1-en-4-one was synthesized by operations similar to those in Reaction 10-14 using appropriate reagents and starting material.

MS (ESI) m/z=657 (M+H)+.

The amine reagent used for Compound 1008 (2-(piperidin-4-yloxy)-ethanol hydrochloride) was synthesized by the following method.

(Reaction 228-3)

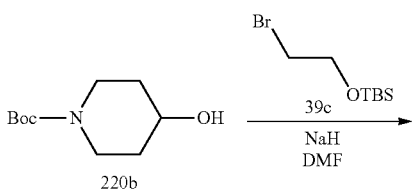

1113
-continued

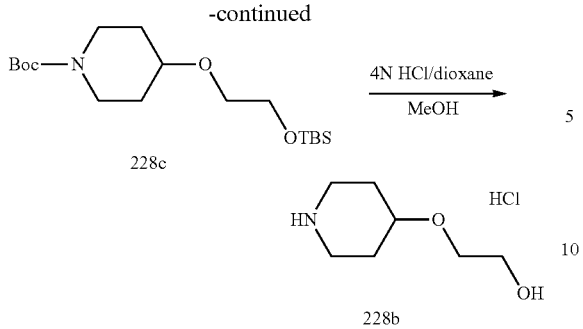

2-(Piperidin-4-yloxy)-ethanol hydrochloride was synthesized by operations similar to those in Reaction 20-2 and Reaction 5-3 using appropriate reagents and starting material.

$^1$H-NMR (300 MHz, DMSO-d6) δ 1.50-1.62 (m, 2H), 1.80-1.89 (m, 2H), 2.87-2.93 (m, 2H), 3.10-3.16 (m, 2H), 3.69-3.76 (m, 1H), 5.00 (s, 1H), 8.74-8.90 (m, 2H).

The example compound shown below was synthesized by operations similar to those in Reaction 228-2 using appropriate reagents and starting material.

Compound 1009

1114
-continued

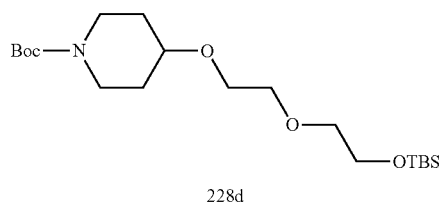

4-{2-[2-(tert-Butyl-dimethyl-silanyloxy)-ethoxy]-ethoxy}-piperidine-1-carboxylic acid tert-butyl ester was synthesized by operations similar to those in Reaction 20-2 using appropriate reagents and starting material.

$^1$H-NMR (300 MHz, CDCl$_3$) δ 0.07 (s, 6H), 0.89 (s, 9H), 1.43-1.59 (m, 11H), 1.79-1.88 (m, 2H), 2.99-3.13 (m, 2H), 3.44-3.52 (m, 1H), 3.54-3.59 (m, 2H), 3.60-3.68 (s, 4H), 3.72-3.84 (m, 4H).

TABLE 147

| Compound | Structure | LCMS condition | Retention time (min) | MS (m/z) |
|---|---|---|---|---|
| 1009 | 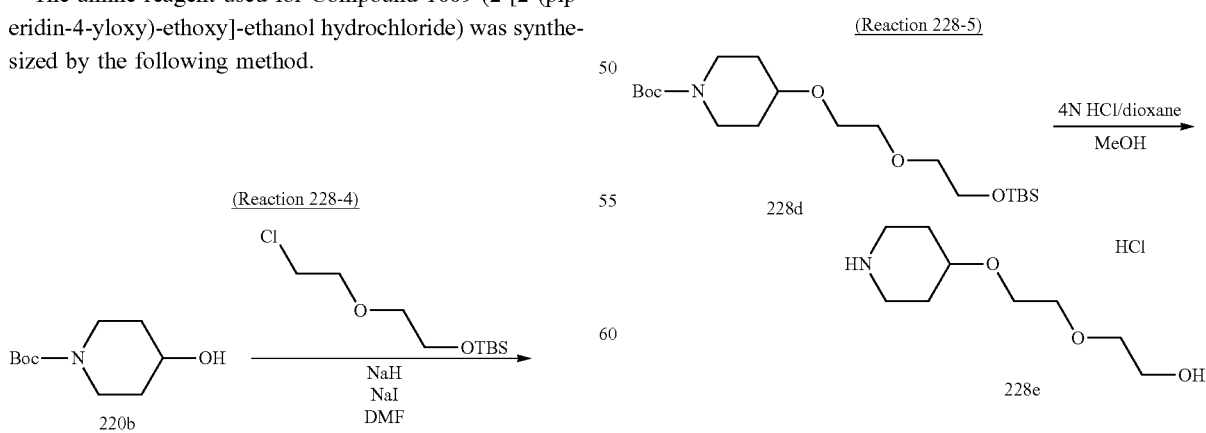 | LCMS-D-1 | 242 | 701 (M + H)+ |

The amine reagent used for Compound 1009 (2-[2-(piperidin-4-yloxy)-ethoxy]-ethanol hydrochloride) was synthesized by the following method.

2-[2-(Piperidin-4-yloxy)-ethoxy]-ethanol hydrochloride was synthesized by operations similar to those in Reaction 5-3 using appropriate reagents and starting material. This was used in the next reaction without purification.

Example 229

8-((E)-2-{4-[4-((R)-2,3-Dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one (Compound 1010)

(Reaction 229-1)

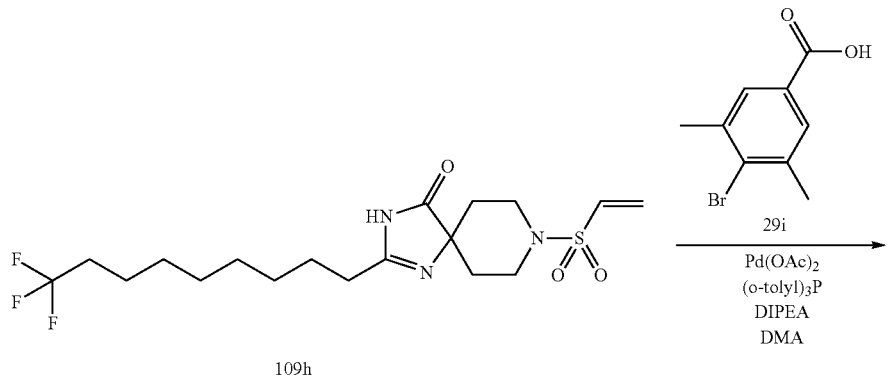

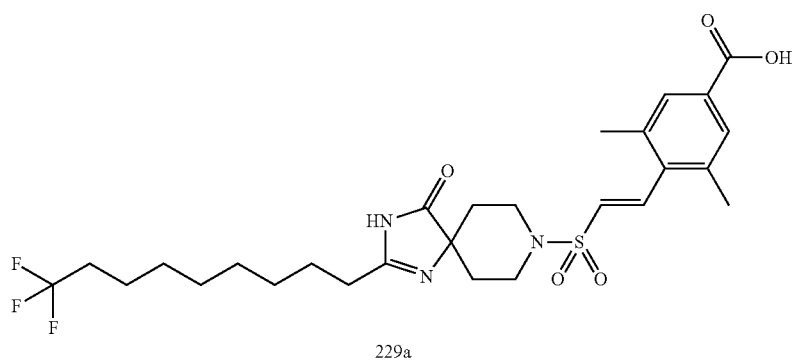

3,5-Dimethyl-4-((E)-2-{4-oxo-2-[4-(9,9,9-trifluoro-nonyl)-cyclohexyl]-1,3,8-triaza-spiro[4.5]dec-1-ene-8-sulfonyl}-vinyl)-benzoic acid was synthesized by operations similar to those in Reaction 26-1 using appropriate reagents and starting material.

MS (ESI) m/z=572 (M+H)+.

(Reaction 229-2)

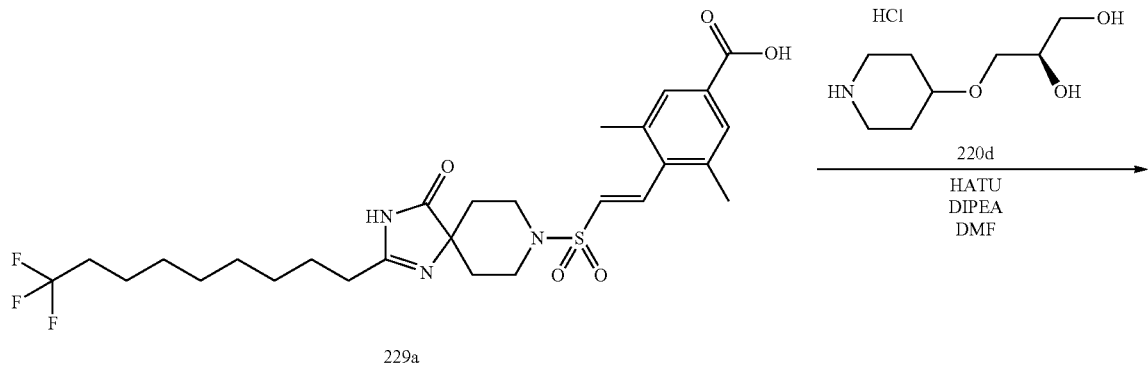

-continued

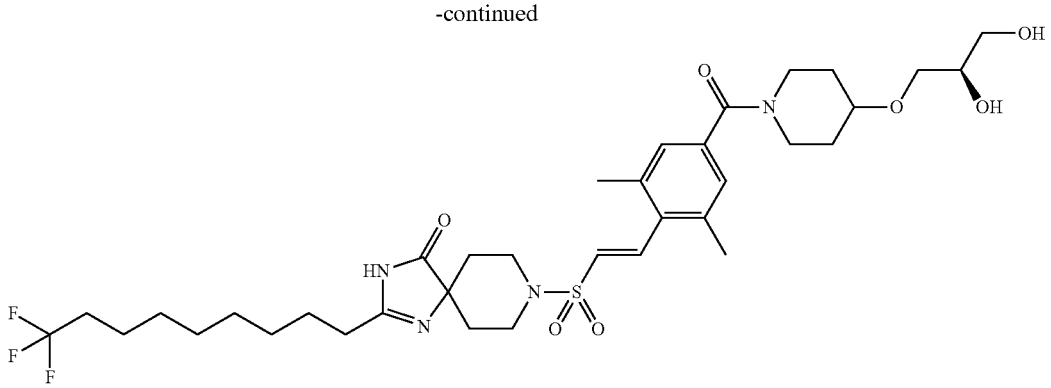

Compound 1010

8-((E)-2-{4-[4-((R)-2,3-Dihydroxy-propoxy)-piperidine-1-carbonyl]-2,6-dimethyl-phenyl}-ethenesulfonyl)-2-(9,9,9-trifluoro-nonyl)-1,3,8-triaza-spiro[4.5]dec-1-en-4-one was synthesized by operations similar to those in Reaction 10-14 using appropriate reagents and starting material.
MS (ESI) m/z=729 (M+H)+.

Example 230

2-Amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide (Compound 1011)

(Reaction 230-1)

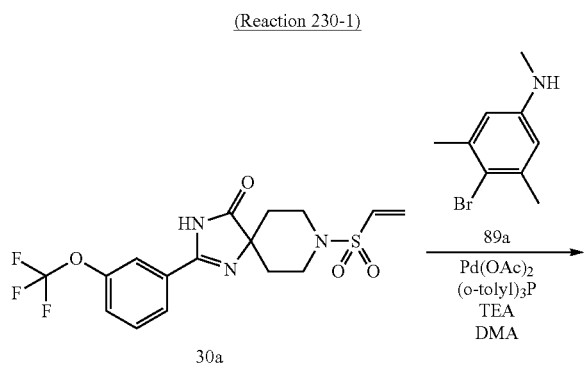

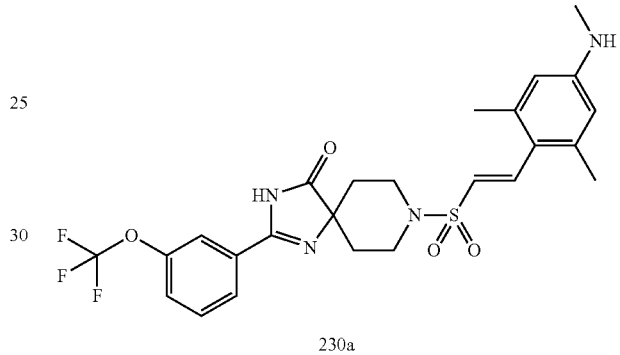

230a

8-[(E)-2-(2,6-Dimethyl-4-methylamino-phenyl)-ethenesulfonyl]-2-(3-trifluoromethoxy-phenyl)-1,3,8-triaza-spiro[4.5]dec-1-en-4-one was synthesized by operations similar to those in Reaction 26-1 using appropriate reagents and starting material.
MS (ESI) m/z=537 (M+H)+.

(Reaction 230-2)

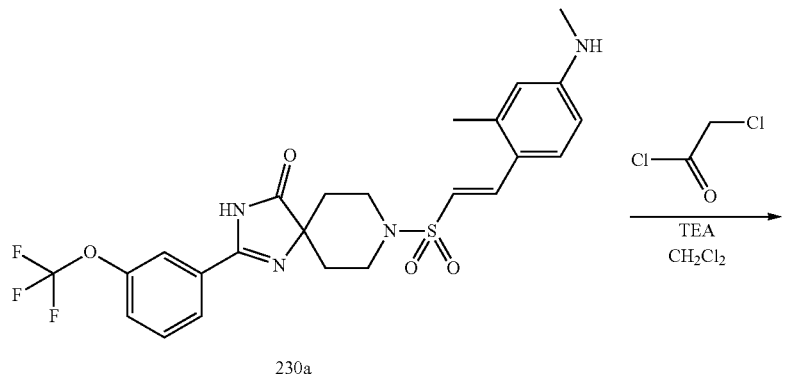

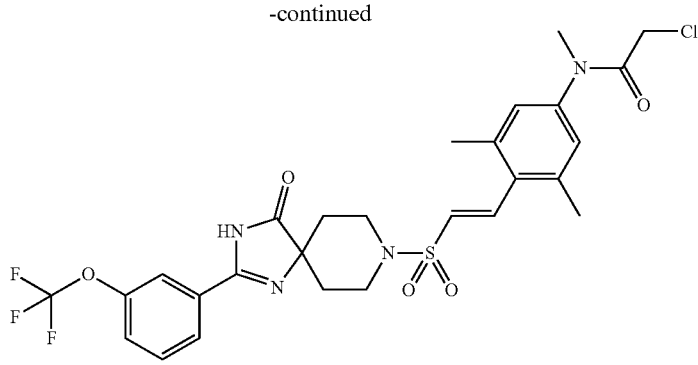

230b

2-Chloro-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide was synthesized by operations similar to those in Reaction 2-3 using appropriate reagents and starting material.

MS (ESI) m/z=613 (M+H)+.

(Reaction 230-3)

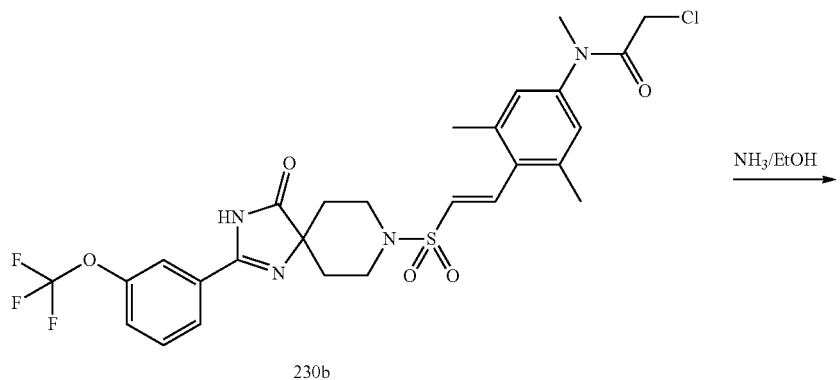

230b

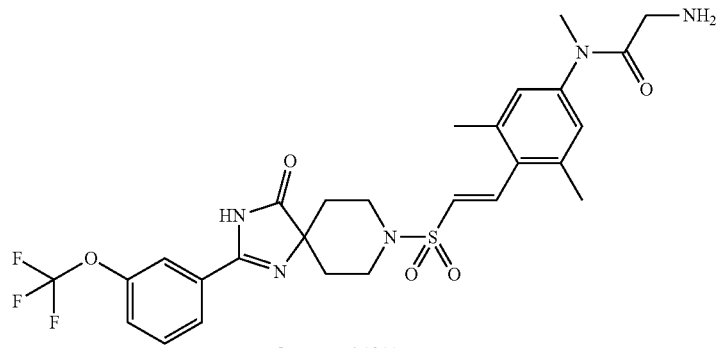

Compound 1011

Ammonia (6 N solution in ethanol, 0.3 ml) was added to a solution of 2-chloro-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide (38 mg, 0.06 mmol) in anhydrous ethanol (0.5 ml), and the mixture was stirred at 50 to 60° C. for five hours. The mixed solution was concentrated under reduced pressure, and the resulting residue was then purified by silica gel column chromatography (dichloromethane) to give 2-amino-N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-acetamide (11 mg, 31%).

MS (ESI) m/z=594 (M+H)+.

Example 231

(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester (Compound 1012)

(Reaction 231-1)

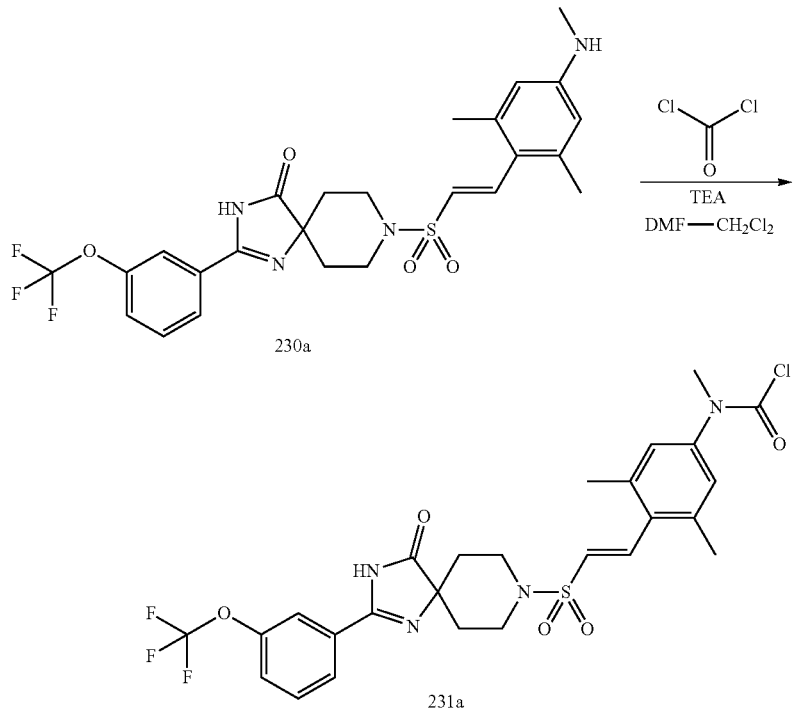

Phosgene (20% solution in toluene, 35 µL, 67 µmol) was added to a mixed solution of 8-[(E)-2-(2,6-dimethyl-4-methylamino-phenyl)-ethenesulfonyl]-2-(3-trifluoromethoxy-phenyl)-1,3,8-triaza-spiro[4.5]dec-1-en-4-one (30 mg, 56 µmol) and triethylamine (15 µL, 84 µmol) in dichloromethane (1.5 ml) and dimethylformamide (0.5 ml) at 0° C. The mixture was stirred at room temperature for three hours, and then quenched with water and extracted with ethyl acetate. The organic layer was sequentially washed with water and saturated brine, and then dried over anhydrous sodium sulfate and concentrated under reduced pressure. The resulting residue was purified by silica gel column chromatography (dichloromethane-ethyl acetate) to give N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-chloroformamide (28 mg, 85%).

MS (ESI) m/z=599 (M+H)+.

(Reaction 231-2)

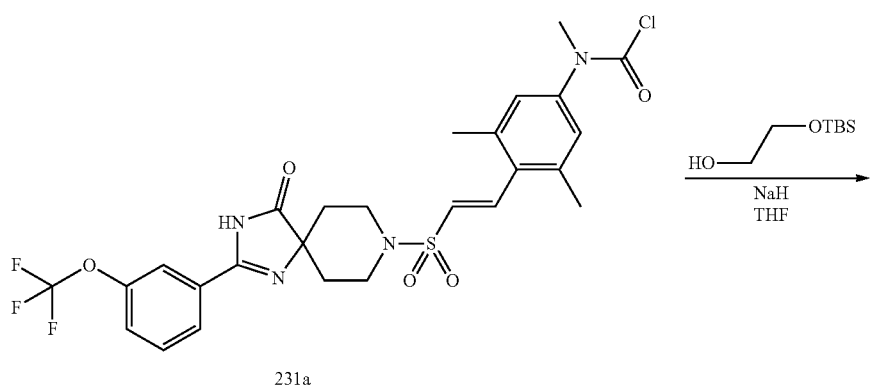

-continued

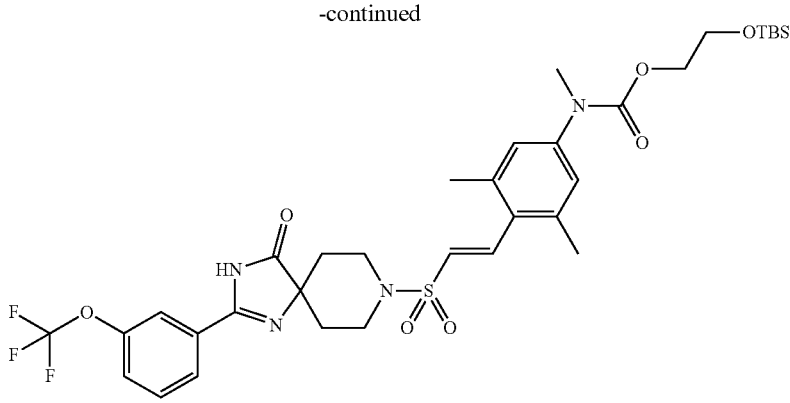

231ba

Sodium hydride (60% oil suspension, 5.6 mg, 0.14 mmol) was added to a solution of N-(3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-N-methyl-chloroformamide (30 mg, 50.1 µmol) in tetrahydrofuran (1.0 ml) at 0° C., and the mixture was stirred for 15 minutes. 2-(tert-Butyl-dimethyl-silanyloxy)-ethanol (30 µL, 0.14 mmol) was then added and the mixture was stirred at 40° C. for two hours. The mixture was cooled, and then quenched with water and extracted with ethyl acetate. The organic layer was sequentially washed with water and saturated brine, and then dried over anhydrous sodium sulfate and concentrated under reduced pressure. The resulting residue was purified by silica gel column chromatography (dichloromethane-ethyl acetate) to give (3,5-dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-(tert-butyl-dimethyl-silanyloxy)-ethyl ester (29 mg, 78%).

MS (ESI) m/z=739 (M+H)+.

(Reaction 231-3)

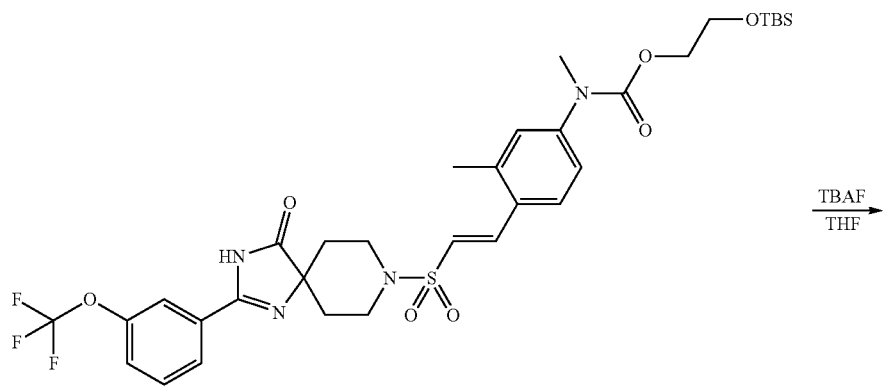

230a

TBAF
THF

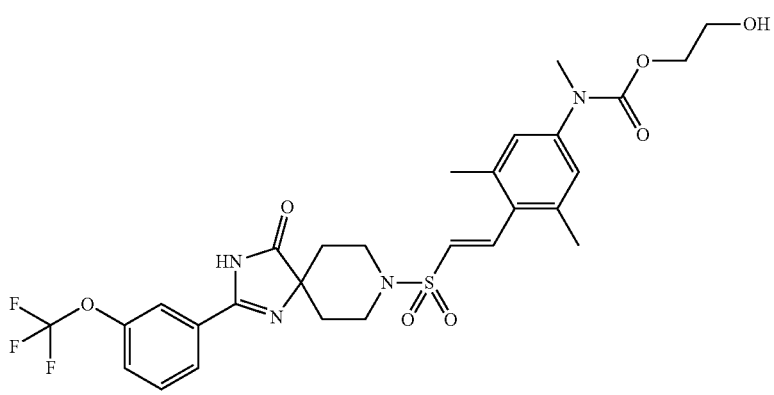

Compound 1012

(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-methyl-carbamic acid 2-hydroxy-ethyl ester was synthesized by operations similar to those in Reaction 39-2 using appropriate reagents and starting material.
MS (ESI) m/z=625 (M+H)+.

Example 232

1-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea
(Compound 1013)

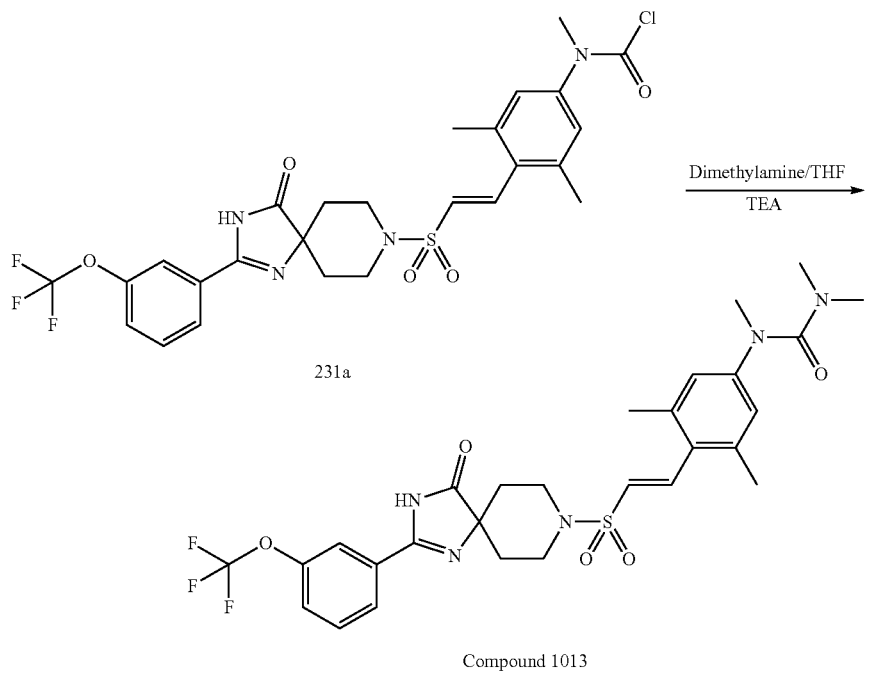

1-(3,5-Dimethyl-4-{(E)-2-[4-oxo-2-(3-trifluoromethoxy-phenyl)-1,3,8-triaza-spiro[4.5]dec-1-ene-8-sulfonyl]-vinyl}-phenyl)-1,3,3-trimethyl-urea was synthesized by operations similar to those in Reaction 231-2 using appropriate reagents and starting material.
MS (ESI) m/z=608 (M+H)+.

The example compounds shown below were synthesized by operations similar to those in Reaction 232-1 using appropriate reagents and starting materials.

Compounds 1014 to 1015

TABLE 148

| Compound | Structure | LCMS condition | Retention time (min) | MS (m/z) |
|---|---|---|---|---|
| 1014 | 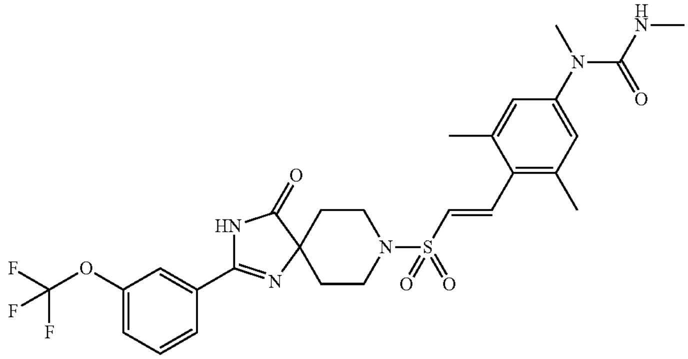 [SMILES: CNC(=O)N(C)c1cc(C)c(/C=C/S(=O)(=O)N2CCC3(CC2)N=C(c2cccc(OC(F)(F)F)c2)NC3=O)c(C)c1] | LCMS-D-1 | 3.02 | 594 (M + H)+ |

TABLE 148-continued

| Compound | Structure | LCMS condition | Retention time (min) | MS (m/z) |
| --- | --- | --- | --- | --- |
| 1015 | 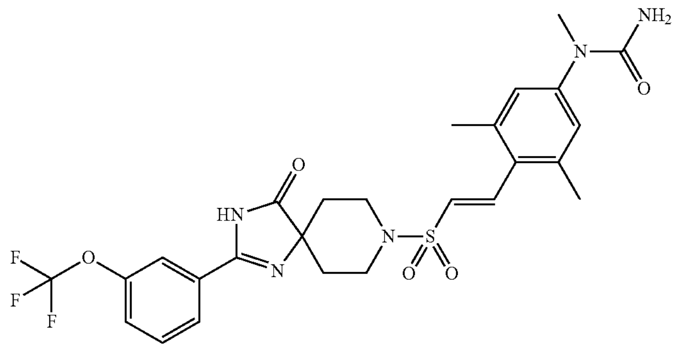 [SMILES: Cc1cc(N(C)C(N)=O)cc(C)c1/C=C/S(=O)(=O)N1CCC2(CC1)N=C(c1cccc(OC(F)(F)F)c1)NC2=O] | LCMS-D-1 | 2.92 | 580 (M + H)+ |

Example 233

8-[(E)-2-(2,6-Dimethyl-4-methylamino-phenyl)-ethenesulfonyl]-2-(3-trifluoromethylsulfanyl-phenyl)-1,3,8-triaza-spiro[4.5]dec-1-en-4-one (Compound 1016)

(Reaction 233-1)

{4-[(E)-2-(1,4-Dioxa-8-aza-spiro[4.5]decane-8-sulfonyl)-vinyl]-3,5-dimethyl-phenyl}-methyl-carbamic acid tert-butyl ester was synthesized by operations similar to those in Reaction 25-1 and Reaction 26-1 using appropriate reagents and starting material.

MS (ESI) m/z=467 (M+H)+.

(Reaction 233-2)

Trifluoroacetic acid (5.3 ml, 71.79 mmol) was added to a solution of {4-[(E)-2-(1,4-dioxa-8-aza-spiro[4.5]decane-8-sulfonyl)-vinyl]-3,5-dimethyl-phenyl}-methyl-carbamic acid tert-butyl ester (670 mg, 1.43 mmol) in acetone-water (8.0 ml-8.0 ml) at room temperature, and the mixture was heated with stirring at 50° C. for 18 hours. The mixed reaction solution was cooled and then concentrated under reduced pressure. The residue was neutralized by adding a saturated aqueous sodium bicarbonate solution and extracted with ethyl acetate. The organic layer was sequentially washed with water and saturated brine, and then dried over Na$_2$SO$_4$ and concentrated under reduced pressure. The resulting residue was purified by silica gel column chromatography (ethyl acetate-hexane) to give 1-[(E)-2-(N,2,6-trimethylaniline)-ethenesulfonyl]-piperidin-4-one (364 mg, 78%).

MS (ESI) m/z=323 (M+H)+.

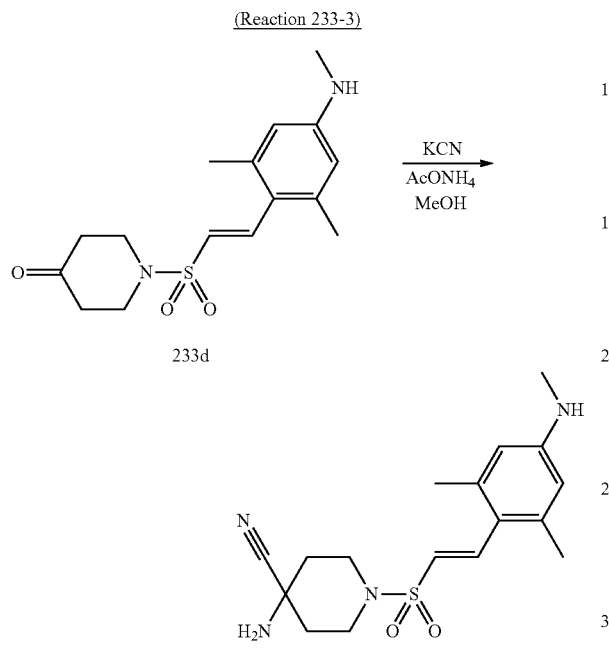

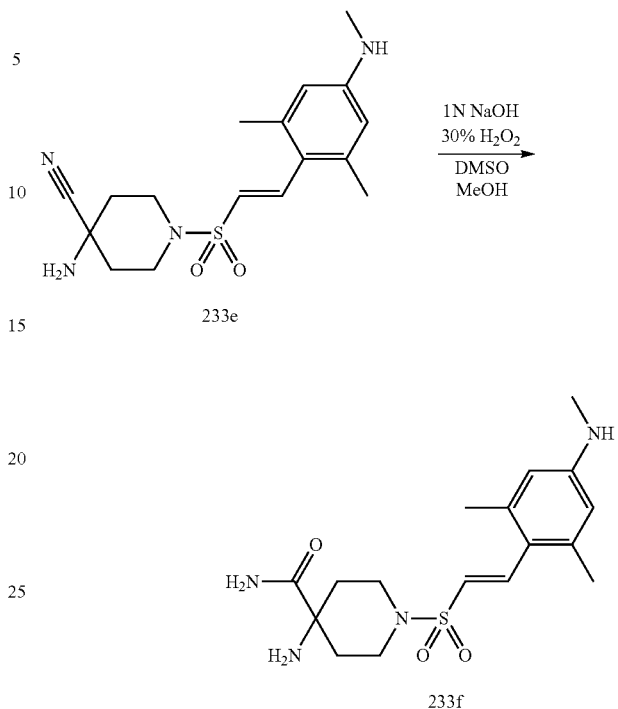

Ammonium acetate (686 mg, 8.91 mmol) and potassium cyanide (541 mg, 8.31 mmol) were added to a solution of 1-[(E)-2-(2,6-dimethyl-4-methylamino-phenyl)-ethenesulfonyl]-piperidin-4-one (1.91 g, 5.94 mmol) in MeOH (20 ml), and the mixture was heated with stirring at 60° C. for three hours. The mixed reaction solution was cooled and a saturated aqueous $NaHCO_3$ solution was then added, followed by extraction with ethyl acetate. The organic layer was sequentially washed with water and saturated brine, and then dried over $Na_2SO_4$ and concentrated under reduced pressure. The resulting residue was triturated with hexane:$CH_2Cl_2$=7:3 to give 4-amino-1-[(E)-2-(2,6-dimethyl-4-methylamino-phenyl)-ethenesulfonyl]-piperidine-4-carbonitrile (1.86 g, 89%).

MS (ESI) m/z=349 (M+H)+.

DMSO (0.9 ml, 12.8 mmol), a 1 N aqueous NaOH solution (1.06 ml, 1.06 mmol) and 30% aqueous hydrogen peroxide (0.72 ml, 6.40 mmol) were sequentially added to a solution of 4-amino-1-[(E)-2-(2,6-dimethyl-4-methylamino-phenyl)-ethenesulfonyl]-piperidine-4-carbonitrile (1.85 g, 5.33 mmol) in MeOH (30 ml) at 0° C., and the mixture was stirred at room temperature for 2.5 hours. A saturated $Na_2S_2O_3$ solution was added to the reaction mixture, and the precipitated solid was obtained by suction filtration. The resulting solid was washed with water, dissolved in a $CH_2Cl_2$-MeOH (3:2) solution, dried over $Na_2SO_4$ and concentrated under reduced pressure. The resulting residue was triturated with hexane:$CH_2Cl_2$=4:1 to give 4-amino-1-[(E)-2-(2,6-dimethyl-4-methylamino-phenyl)-ethenesulfonyl]-piperidine-4-carboxylic amide (1.36 g, 70%).

MS (ESI) m/z=367 (M+H)+.

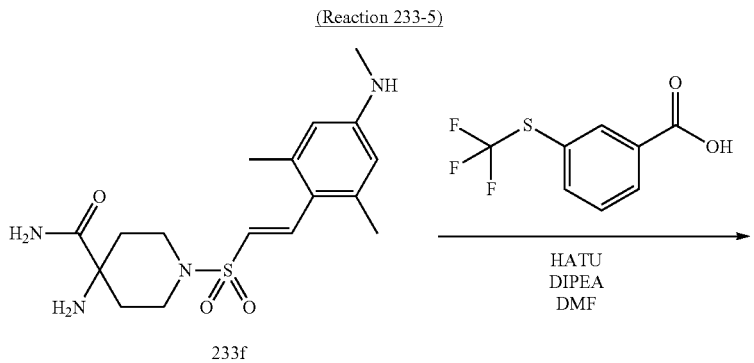

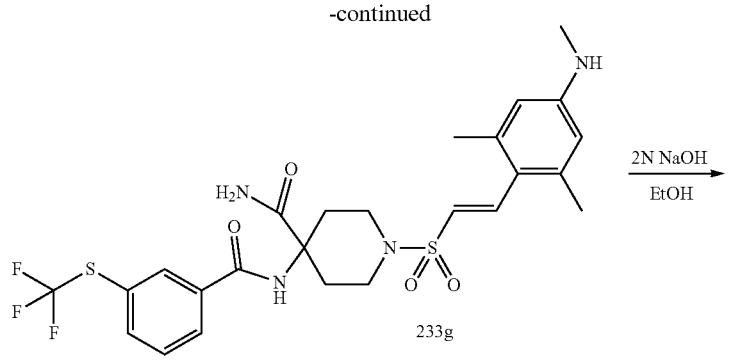

233g

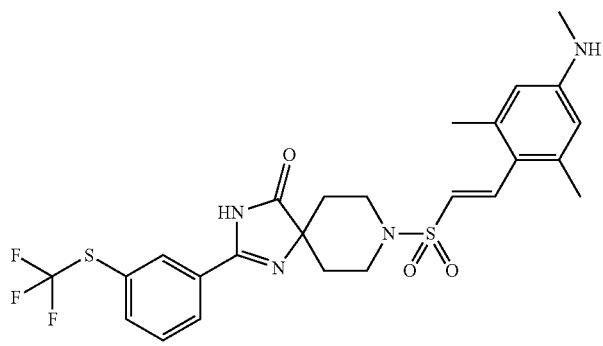

Compound 1016

8-[(E)-2-(2,6-Dimethyl-4-methylamino-phenyl)-ethene-sulfonyl]-2-(3-trifluoromethylsulfanyl-phenyl)-1,3,8-triaza-spiro[4.5]dec-1-en-4-one was synthesized by operations similar to those in Reaction 10-14 and Reaction 189-5 using appropriate reagents and starting material.

MS (ESI) m/z=553 (M+H)+.

Example 234

1-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea (Compound 1017)

(Reaction 234-1)

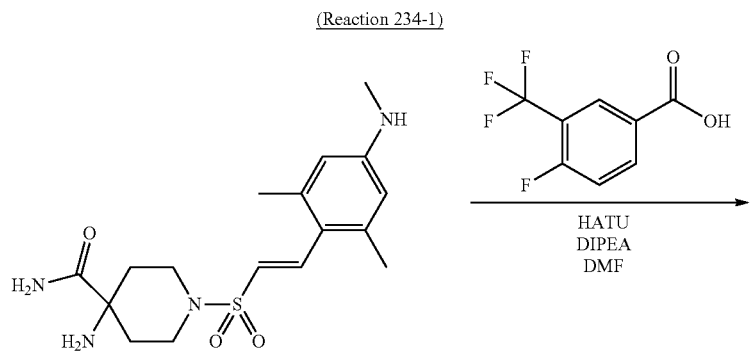

233f

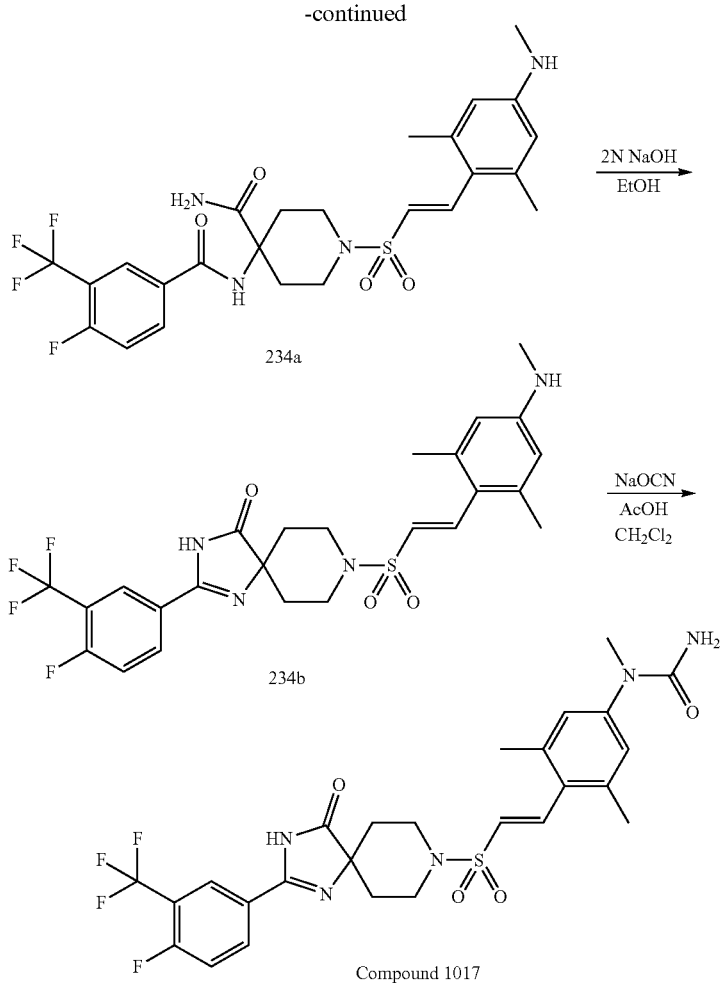

1-(4-{(E)-2-[2-(4-Fluoro-3-trifluoromethyl-phenyl)-4-oxo-1,3,8-triaza-spiro[4.5]dec-1-ene-8-sulfonyl]-vinyl}-3,5-dimethyl-phenyl)-1-methyl-urea was synthesized by operations similar to those in Reaction 10-14, Reaction 189-5 and Reaction 89-2 using appropriate reagents and starting material.

MS (ESI) m/z=582 (M+H)+.

The example compounds shown below were synthesized by operations similar to those in Reaction 234-1 using appropriate reagents and starting materials.

Compounds 1018 to 1021

TABLE 149

| Compound | Structure | LCMS condition | Retention time (min) | MS (m/z) |
|---|---|---|---|---|
| 1018 | 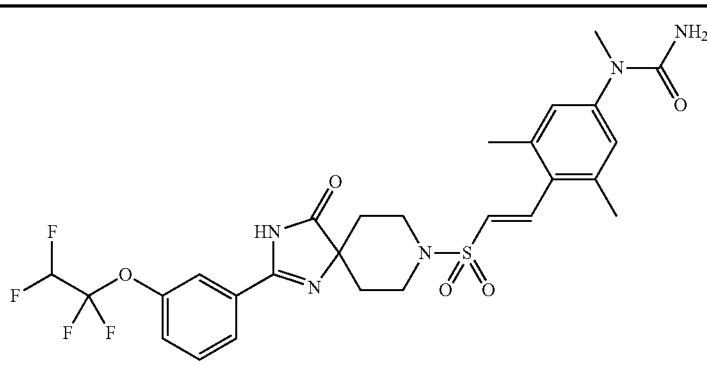 | LCMS-F-1 | 0.95 | 612 (M + H)+ |

TABLE 149-continued
| Compound | Structure | LCMS condition | Retention time (min) | MS (m/z) |
|---|---|---|---|---|
| 1019 | 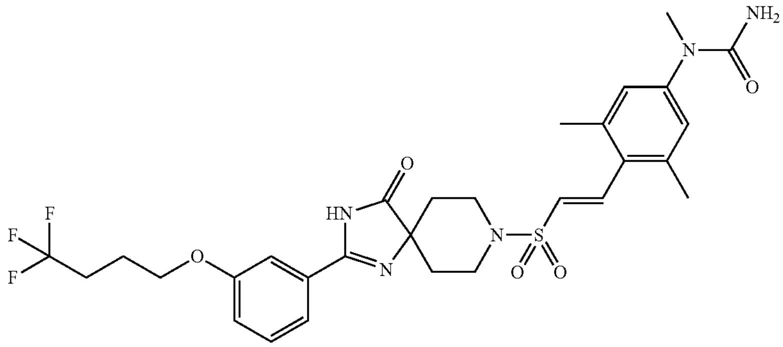 [SMILES: Cc1cc(N(C)C(N)=O)cc(C)c1/C=C/S(=O)(=O)N1CCC2(CC1)N=C(c1cccc(OCCCC(F)(F)F)c1)NC2=O] | LCMS-F-1 | 0.99 | 622 (M + H)+ |
| 1020 | 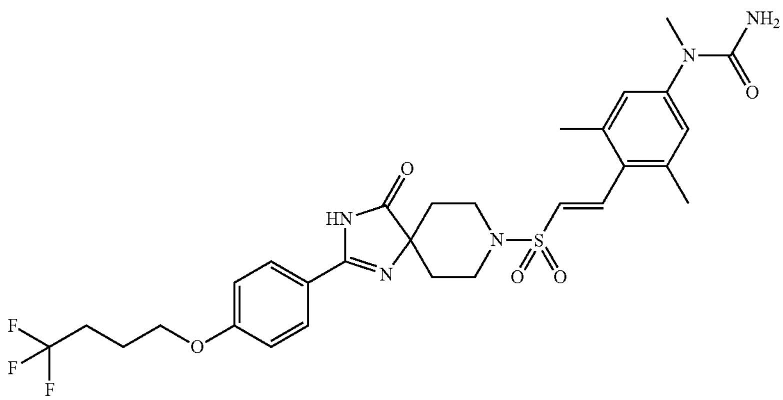 [SMILES: Cc1cc(N(C)C(N)=O)cc(C)c1/C=C/S(=O)(=O)N1CCC2(CC1)N=C(c1ccc(OCCCC(F)(F)F)cc1)NC2=O] | LCMS-F-1 | 0.97 | 622 (M + H)+ |
| 1021 | 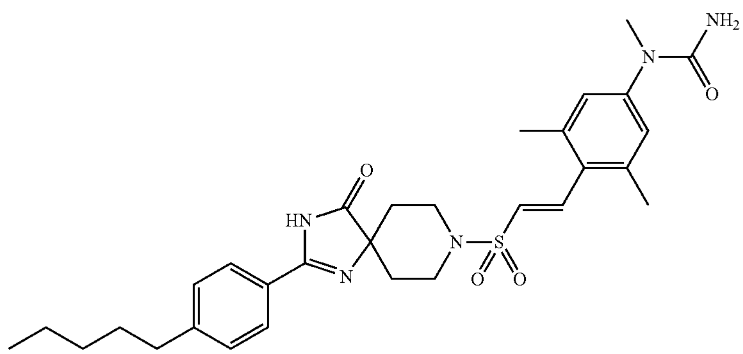 [SMILES: CCCCCc1ccc(C2=NC3(CCN(S(=O)(=O)/C=C/c4c(C)cc(N(C)C(N)=O)cc4C)CC3)C(=O)N2)cc1] | LCMS-F-1 | 1.04 | 566 (M + H)+ |
The carboxylic acid reagent used in the synthesis of Compound 1019 (3-(4,4,4-trifluoro-butoxy)-benzoic acid) was synthesized by the following method.
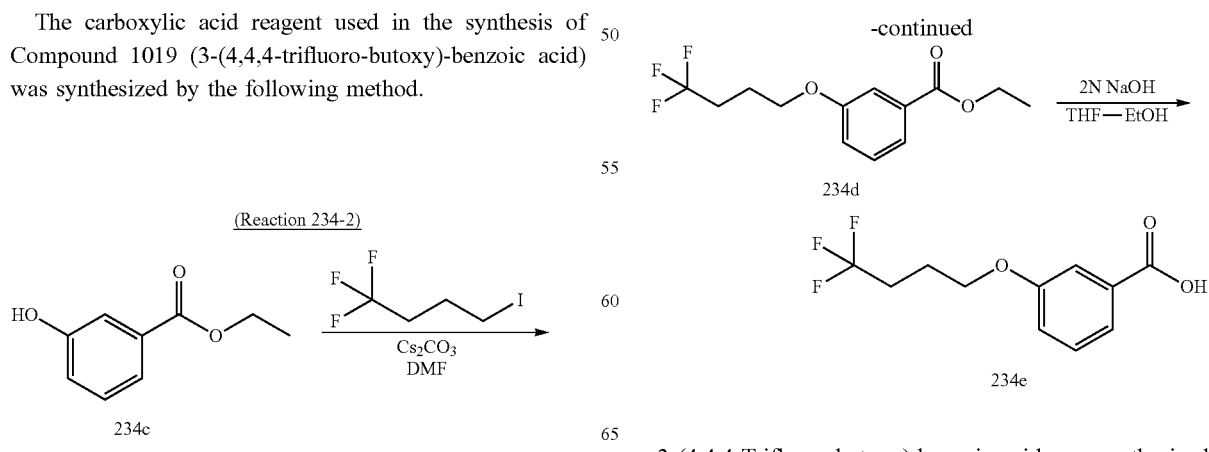
3-(4,4,4-Trifluoro-butoxy)-benzoic acid was synthesized by operations similar to those in Reaction 26-4 (using Cs₂CO₃ as a base) and Reaction 189-5 using appropriate reagents and starting material.

MS (ESI) m/z=247 (M−H)−.

The carboxylic acid reagent used in the synthesis of Compound 1020 (4-(4,4,4-trifluoro-butoxy)-benzoic acid) was synthesized by the following method.

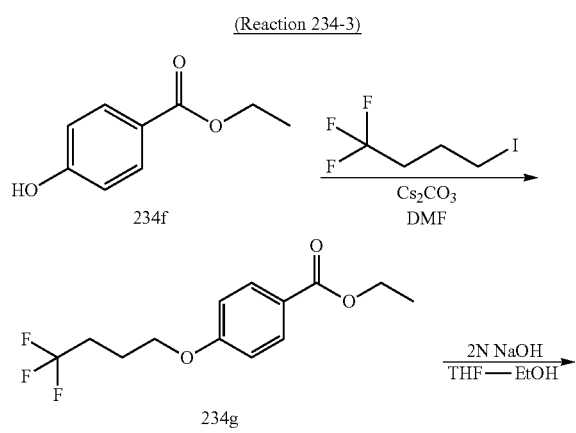

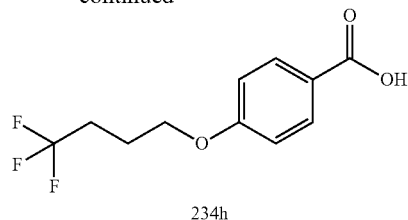

4-(4,4,4-Trifluoro-butoxy)-benzoic acid was synthesized by operations similar to those in Reaction 26-4 (using Cs₂CO₃ as a base) and Reaction 189-5 using appropriate reagents and starting material.

MS (ESI) m/z=249 (M+H)+.

Example 235

1-(3,5-Dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea (Compound 1022)

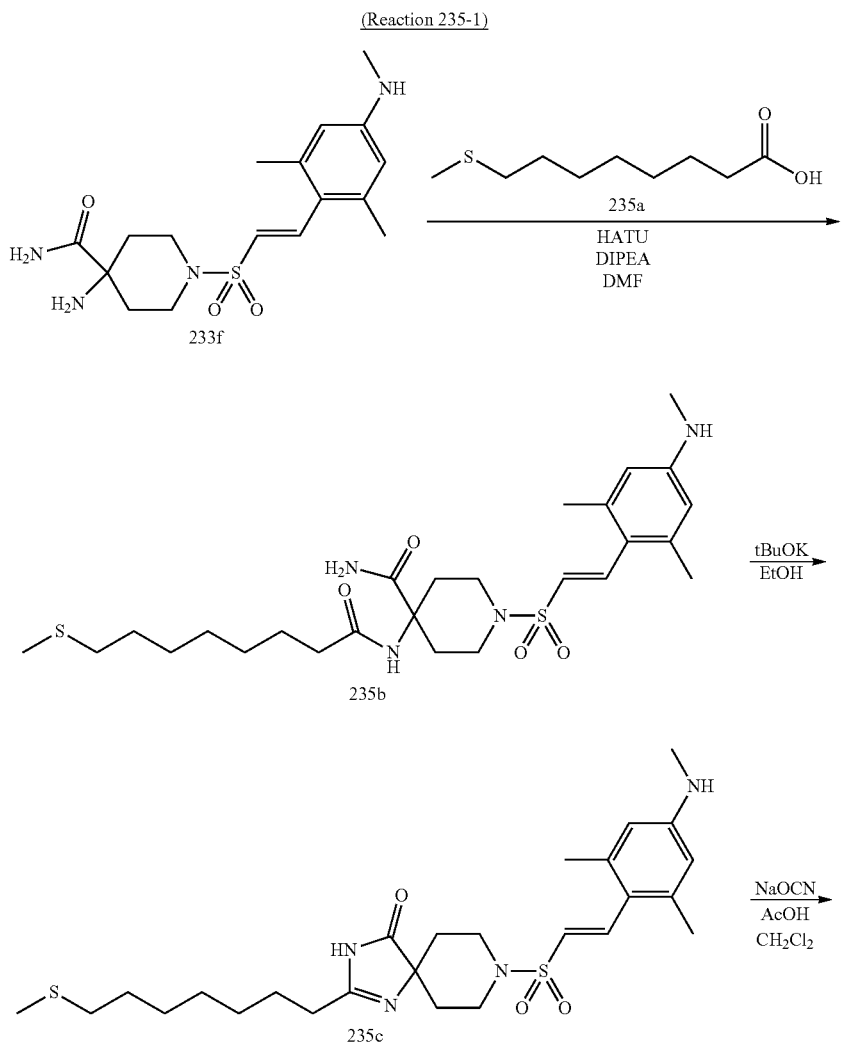

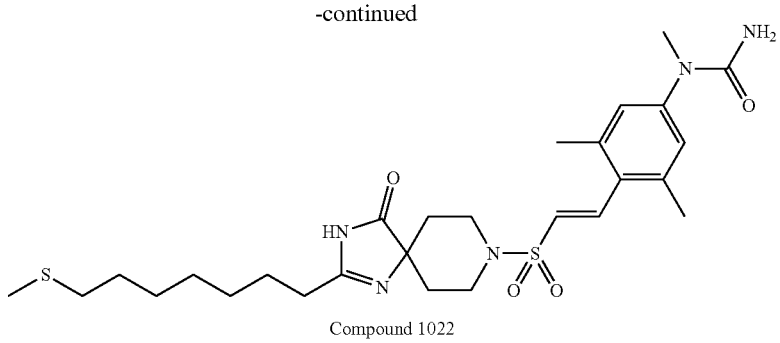

Compound 1022

1-(3,5-Dimethyl-4-{(E)-2-[2-(7-methylsulfanyl-heptyl)-4-oxo-1,3,8-triaza-spiro[4.5]dec-1-ene-8-sulfonyl]-vinyl}-phenyl)-1-methyl-urea was synthesized by operations similar to those in Reaction 10-14, Reaction 10-12 and Reaction 89-2 using appropriate reagents and starting material.

MS (ESI) m/z=564 (M+H)+.

The carboxylic acid reagent used in the synthesis of Compound 1022 (8-(methylthio)octanoic acid) was synthesized by the following method.

(Reaction 235-2)

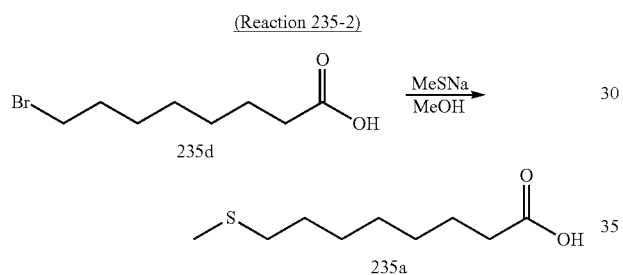

Sodium thiomethoxide (942 mg, 13.44 mmol) was added to a solution of 8-bromooctanoic acid (500 mg, 2.24 mmol) in methanol (5.6 mL), and the mixture was heated under reflux overnight. The reaction mixture was concentrated under reduced pressure, adjusted to pH 1 by adding 1 N hydrochloric acid and then extracted with ethyl acetate. The organic layer was washed with saturated brine, and then dried over $MgSO_4$ and concentrated under reduced pressure. The resulting residue was purified by silica gel column chromatography (dichloromethane:methanol=20:1) to give 8-(methylthio)octanoic acid as a colorless oily substance (426.5 mg, 100%).

$^1$H-NMR (300 MHz, $CDCl_3$) δ 1.31-1.41 (m, 6H), 1.54-1.66 (m, 4H), 2.09 (s, 3H), 2.35 (t, 2H, J=7.2 Hz), 2.48 (t, 2H, J=7.2 Hz).

Example 236

1-[3,5-Dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea (Compound 1023)

(Reaction 236-1)

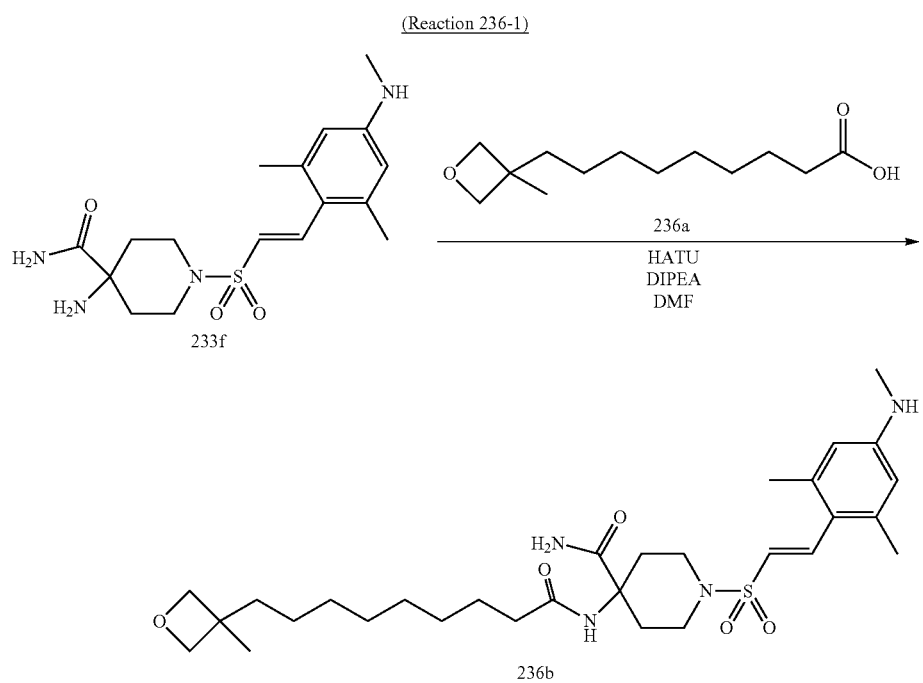

1-[(E)-2-(2,6-Dimethyl-4-methylamino-phenyl)-ethene-sulfonyl]-4-[9-(3-methyl-oxetan-3-yl)-nonanoylamino]-piperidine-4-carboxylic amide was synthesized by operations similar to those in Reaction 10-14 using appropriate reagents and starting material. This was used in the next reaction without purification.

(Reaction 236-2)

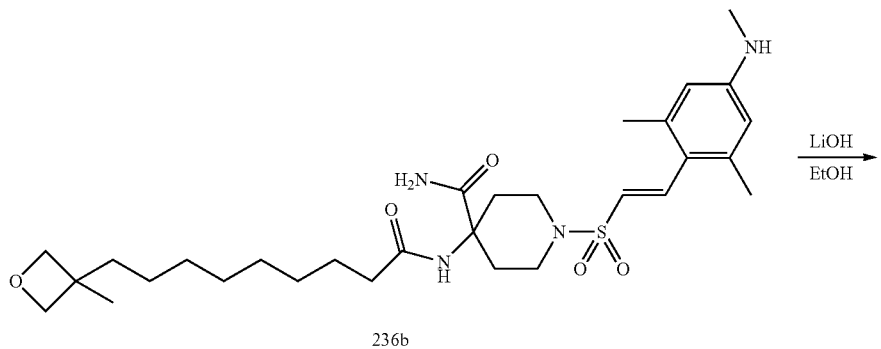

236b

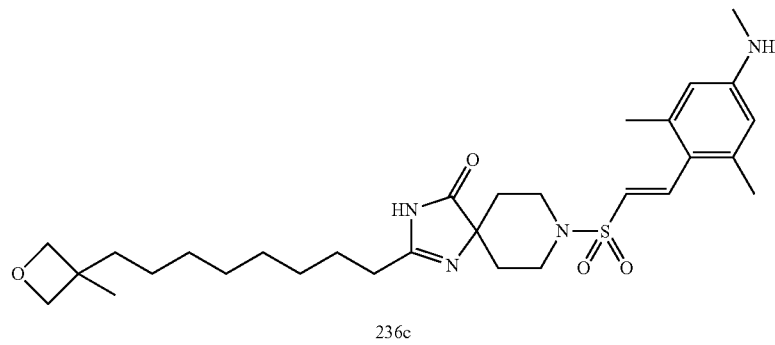

236c

LiOH.H$_2$O (16.6 mg, 0.396 mmol) was added to a solution of 1-[(E)-2-(2,6-dimethyl-4-methylamino-phenyl)-ethenesulfonyl]-4-[9-(3-methyl-oxetan-3-yl)-nonanoylamino]-piperidine-4-carboxylic amide (96 mg, 0.098 mmol) in ethanol (1.0 mL), and the mixture was stirred at 50° C. for two hours. A 50% saturated aqueous ammonium chloride solution was added to the reaction mixture, followed by extraction with ethyl acetate. The organic layer was then dried over MgSO$_4$ and concentrated under reduced pressure. The resulting residue was purified by silica gel column chromatography (ethyl acetate) to give 8-[(E)-2-(2,6-Dimethyl-4-methylamino-phenyl)-ethenesulfonyl]-2-[8-(3-methyl-oxetan-3-yl)-octyl]-1,3,8-triaza-spiro[4.5]dec-1-en-4-one (54.8 mg, 100%).

$^1$H-NMR (400 MHz, CD$_3$OD) δ 1.26 (3H, s), 1.34 (10H, m), 1.63 (6H, m), 1.95 (2H, m), 2.37 (6H, s), 2.44 (2H, m), 2.77 (3H, s), 3.15 (2H, m), 3.63 (2H, m), 4.31 (2H, d, J=5.6 Hz), 4.40 (2H, d, J=5.6 Hz), 6.34 (1H, d, J=15.6 Hz), 6.34 (2H, s), 7.63 (1H, d, J=15.6 Hz).

(Reaction 236-3)

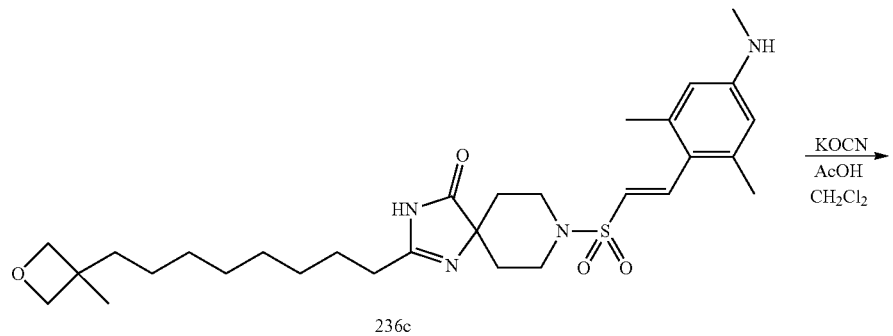

236c

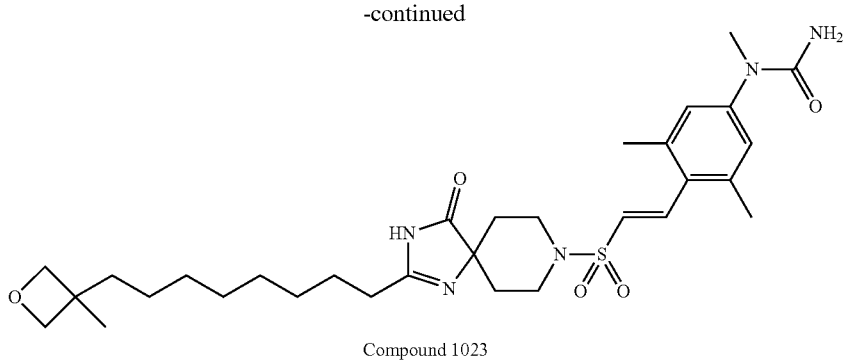

Compound 1023

1-[3,5-Dimethyl-4-((E)-2-{2-[8-(3-methyl-oxetan-3-yl)-octyl]-4-oxo-1,3,8-triaza-spiro[4.5]dec-1-ene-8-sulfonyl}-vinyl)-phenyl]-1-methyl-urea was synthesized by operations similar to those in Reaction 89-2 (using KOCN) using appropriate reagents and starting material.

MS (ESI) m/z=602 (M+H)+.

The carboxylic acid reagent used in the synthesis of Compound 1023 (9-(3-methyl-oxetan-3-yl)-nonanoic acid) was synthesized by the following method.

(Reaction 236-4)

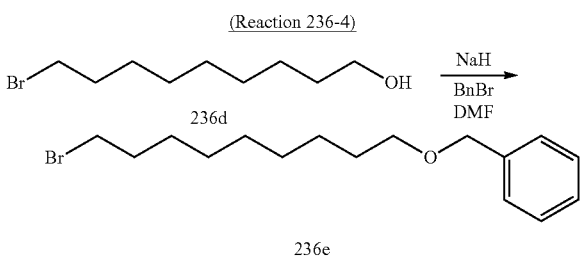

(9-Bromo-nonyloxymethyl)-benzene was synthesized by operations similar to those in Reaction 20-2 using appropriate reagents and starting material.

$^1$H-NMR (400 MHz, CDCl$_3$) δ 1.25-1.45 (10H, m), 1.61 (2H, m), 1.85 (2H, m), 3.40 (2H, t, J=6.8 Hz), 3.46 (2H, t, J=6.8 Hz), 4.50 (2H, s), 7.27-7.35 (5H, m).

(Reaction 236-5)

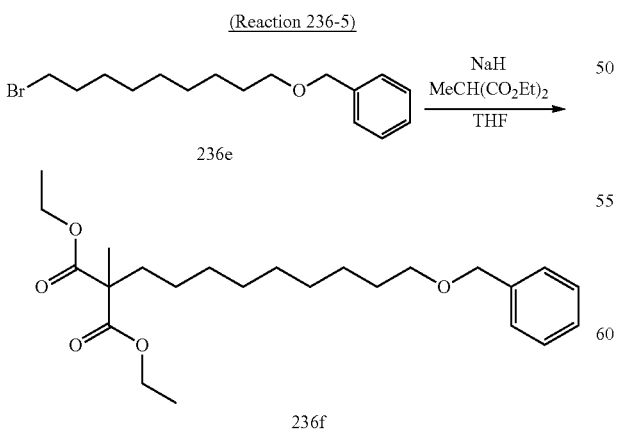

Methyl-malonic acid diethyl ester (0.850 ml, 4.99 mmol) was added to a suspension of sodium hydride (55% oily suspension, 139.5 mg, 3.197 mmol) in THF (0.8 ml) over seven minutes under ice-cooling, and the mixture was stirred until foaming was terminated at room temperature (for about 25 minutes). A solution of (9-bromo-nonyloxymethyl)-benzene (593 mg, 1.89 mmol) in THF (0.12 ml) was added to the reaction solution at room temperature over 15 minutes, and the mixture was then stirred at 90° C. for five hours. The reaction mixture was diluted with ether and water was then added, followed by extraction with ether. The organic layer was dried over MgSO$_4$ and concentrated under reduced pressure. The resulting residue was purified by silica gel column chromatography (hexane/ethyl acetate=30/1→20/1) to give 2-(9-benzyloxy-nonyl)-2-methyl-malonic acid diethyl ester (735 mg, 96%).

$^1$H-NMR (400 MHz, CDCl$_3$) δ 1.24 (6H, t, J=6.8 Hz), 1.27 (12H, m), 1.39 (3H, s), 1.60 (2H, m), 1.83 (2H, m), 3.46 (2H, t, J=6.8 Hz), 4.20 (4H, m), 4.50 (2H, s), 7.27-7.34 (5H, m).

(Reaction 236-6)

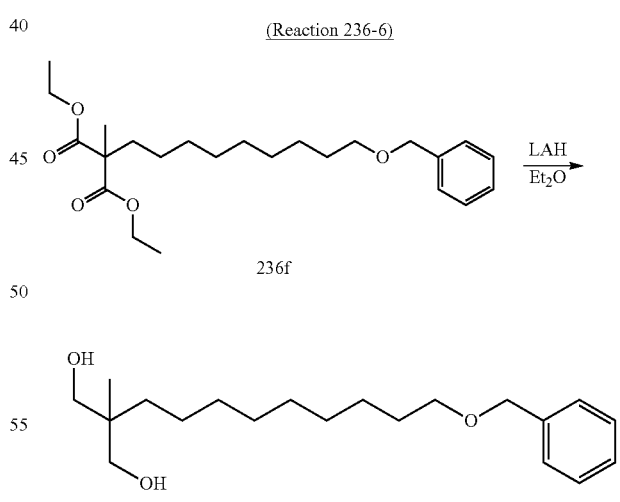

2-(9-Benzyloxy-nonyl)-2-methyl-propane-1,3-diol was synthesized by operations similar to those in Reaction 95-28 using appropriate reagents and starting material.

$^1$H-NMR (400 MHz, CDCl$_3$) δ 0.82 (3H, s), 1.28 (14H, m), 1.61 (2H, m), 2.14 (2H, t, J=4.2 Hz), 3.46 (2H, t, J=6.6 Hz), 3.54 (4H, m), 4.50 (2H, s), 7.27-7.35 (5H, m).

(Reaction 236-7)

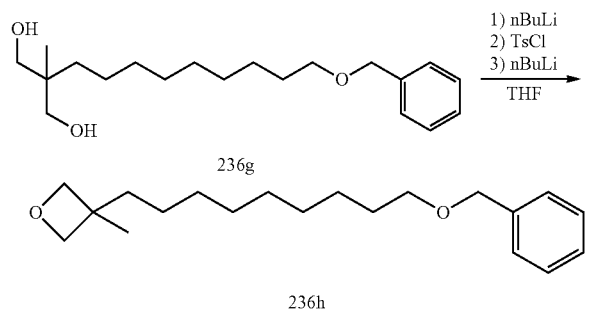

n-Butyllithium (2.6 M solution in hexane, 0.295 ml, 0.767 mmol) was added to a solution of 2-(9-benzyloxy-nonyl)-2-methyl-propane-1,3-diol (221 mg, 0.686 mmol) in THF (5.1 ml) at 0° C. over three minutes, and the mixture was then stirred at the same temperature for 30 minutes. A solution of TsCl (138 mg, 0.723 mmol) in THF (0.91 ml) was added to the reaction solution at 0° C. over eight minutes, and the mixture was then stirred at the same temperature for one hour. n-Butyllithium (2.6 M solution in hexane, 0.295 ml, 0.767 mmol) was added dropwise to the reaction mixture at 0° C., and the mixture was then stirred at 60° C. for six hours. The reaction mixture was diluted with ether and water was then added, followed by extraction with ether. The organic layer was dried over MgSO₄ and concentrated under reduced pressure. The resulting residue was purified by silica gel column chromatography (hexane/ethyl acetate=15/1) to give 3-(9-benzyloxy-nonyl)-3-methyl-oxetane (188 mg, 90%).

¹H-NMR (400 MHz, CDCl₃) δ 1.27 (3H, s), 1.29 (12H, m), 1.61 (4H, m), 3.47 (2H, t, J=6.6 Hz), 4.32 (2H, d, J=5.4 Hz), 4.41 (2H, d, J=5.4 Hz), 4.50 (2H, s), 7.27-7.35 (5H, m).

(Reaction 236-8)

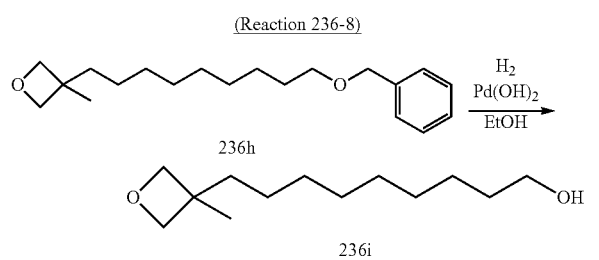

9-(3-Methyl-oxetan-3-yl)-nonan-1-ol was synthesized by operations similar to those in Reaction 122-2 using appropriate reagents and starting material.

¹H-NMR (400 MHz, CDCl₃) δ 1.27 (3H, s), 1.29 (12H, m), 1.59 (4H, m), 3.64 (2H, t, J=6.6 Hz), 4.33 (2H, d, J=5.8 Hz), 4.41 (2H, d, J=5.8 Hz).

(Reaction 236-9)

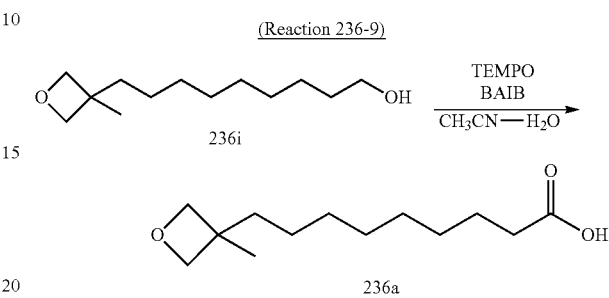

TEMPO (3.4 mg, 0.022 mmol) and iodobenzene diacetate (69.7 mg, 0.216 mmol) were added to a solution of 9-(3-methyl-oxetan-3-yl)-nonan-1-ol (21 mg, 0.098 mmol) in acetonitrile (0.2 ml)-water (0.1 ml) at room temperature, and the mixture was stirred at the same temperature for two hours. Water (0.1 ml) was then added to the reaction mixture at room temperature, and the mixture was stirred at the same temperature for one hour. A 10% aqueous citric acid solution (0.45 ml) was added to the reaction mixture, followed by extraction with ethyl acetate. The organic layer was sequentially washed with water, a 10% aqueous sodium thiosulfate solution and saturated brine, dried over MgSO₄ and concentrated under reduced pressure to give 9-(3-methyl-oxetan-3-yl)-nonanoic acid (22 mg, 100%).

¹H-NMR (400 MHz, CDCl₃) δ 1.27 (3H, s), 1.31 (10H, m), 1.63 (4H, m), 2.35 (2H, t, J=7.6 Hz), 4.33 (2H, d, J=5.4 Hz), 4.42 (2H, d, J=5.4 Hz).

The example compounds shown below were synthesized by operations similar to those in Reaction 236-1, Reaction 236-2 and Reaction 236-3 using appropriate reagents and starting materials.

Compounds 1024 to 1027

TABLE 150

| Compound | Structure | LCMS condition | Retention time (min) | MS (m/z) |
|---|---|---|---|---|
| 1024 | 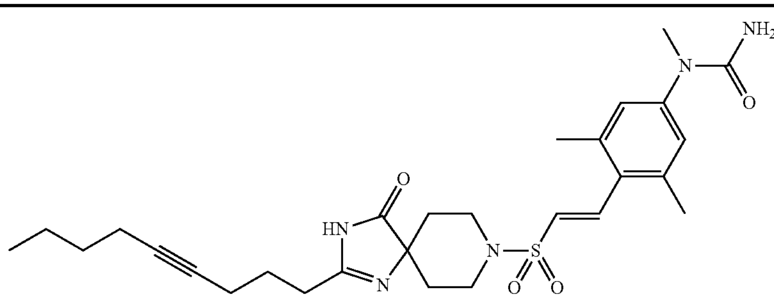 | LCMS-C-2 | 1.97 | 542 (M + H)+ |

TABLE 150-continued

| Compound | Structure | LCMS condition | Retention time (min) | MS (m/z) |
|---|---|---|---|---|
| 1025 | 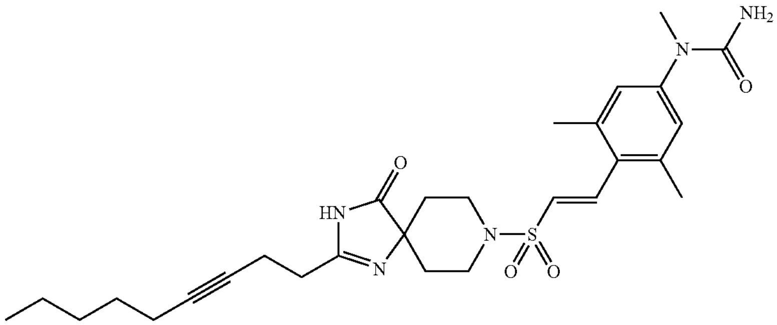 [SMILES: CCCCCC#CCCC1=NC2(CCN(S(=O)(=O)/C=C/c3c(C)cc(N(C)C(N)=O)cc3C)CC2)C(=O)N1] | LCMS-F-1 | 1.01 | 542 (M + H)+ |
| 1026 | 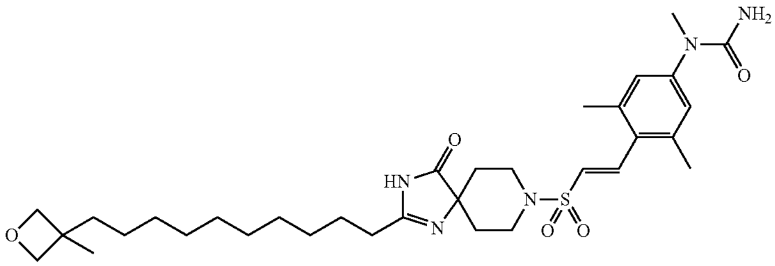 [SMILES: Cc1cc(N(C)C(N)=O)cc(C)c1/C=C/S(=O)(=O)N1CCC2(CC1)N=C(CCCCCCCCCCC1(C)COC1)NC2=O] | LCMS-C-2 | 2.13 | 630 (M + H)+ |
| 1027 | 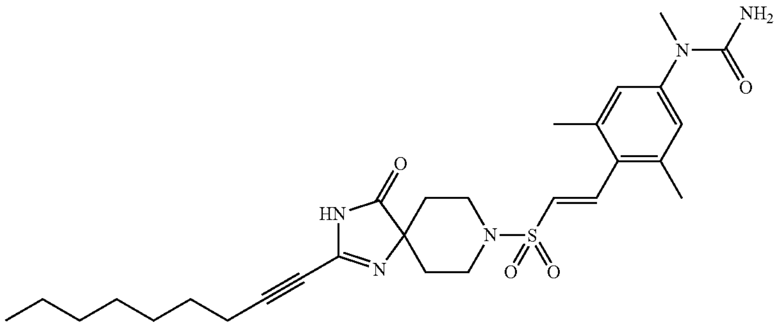 [SMILES: CCCCCCCC#CC1=NC2(CCN(S(=O)(=O)/C=C/c3c(C)cc(N(C)C(N)=O)cc3C)CC2)C(=O)N1] | LCMS-C-2 | 2.22 | 540 (M − H)− |

The carboxylic acid reagent used in the synthesis of Compound 1024 (dec-5-ynoic acid) was synthesized by the following method.

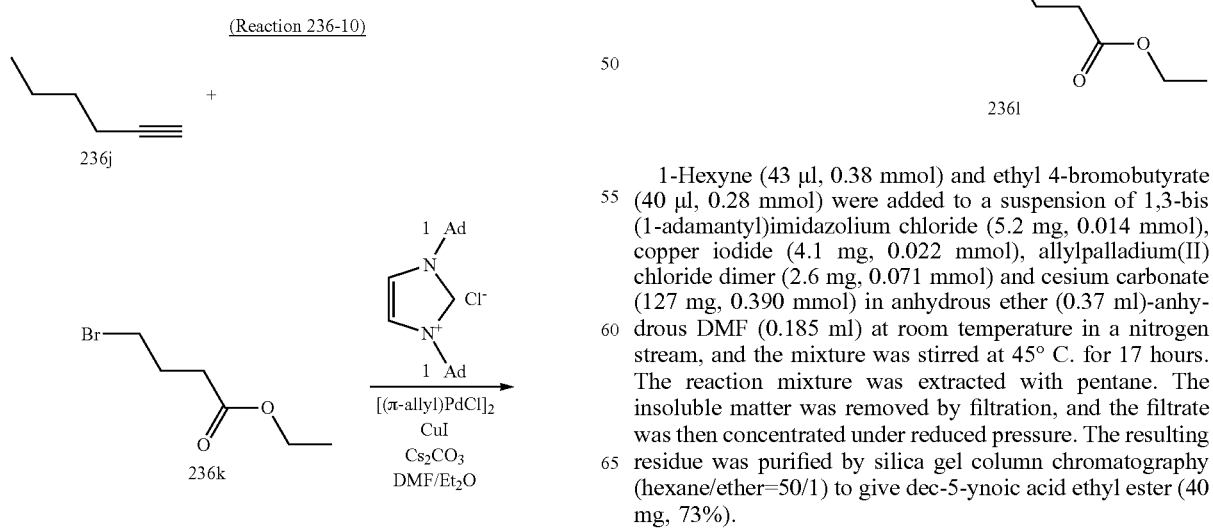

(Reaction 236-10)

1-Hexyne (43 μl, 0.38 mmol) and ethyl 4-bromobutyrate (40 μl, 0.28 mmol) were added to a suspension of 1,3-bis(1-adamantyl)imidazolium chloride (5.2 mg, 0.014 mmol), copper iodide (4.1 mg, 0.022 mmol), allylpalladium(II) chloride dimer (2.6 mg, 0.071 mmol) and cesium carbonate (127 mg, 0.390 mmol) in anhydrous ether (0.37 ml)-anhydrous DMF (0.185 ml) at room temperature in a nitrogen stream, and the mixture was stirred at 45° C. for 17 hours. The reaction mixture was extracted with pentane. The insoluble matter was removed by filtration, and the filtrate was then concentrated under reduced pressure. The resulting residue was purified by silica gel column chromatography (hexane/ether=50/1) to give dec-5-ynoic acid ethyl ester (40 mg, 73%).

¹H-NMR (400 MHz, CDCl₃) δ 0.90 (3H, t, J=7.2 Hz), 1.26 (3H, t, J=7.2 Hz), 1.42 (4H, m), 1.80 (2H, m), 2.14 (2H, m), 2.22 (2H, m), 2.42 (2H, t, J=7.6 Hz), 4.13 (2H, q, J=7.2 Hz).

(Reaction 236-11)

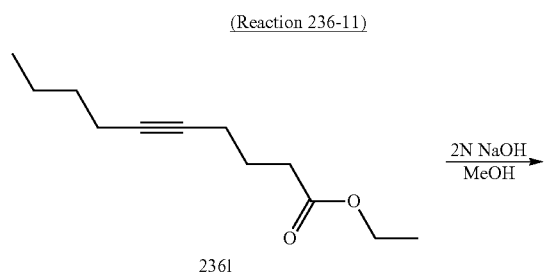

236l

 2N NaOH / MeOH

236m

Dec-5-ynoic acid was synthesized by operations similar to those in Reaction 189-5 using appropriate reagents and starting material.

¹H-NMR (400 MHz, CDCl₃) δ 0.91 (3H, t, J=7.2 Hz), 1.43 (4H, m), 1.82 (2H, m), 2.15 (2H, m), 2.25 (2H, m), 2.50 (2H, t, J=7.2 Hz).

The carboxylic acid reagent used in the synthesis of Compound 1025 (dec-4-ynoic acid) was synthesized by the following method.

(Reaction 236-12)

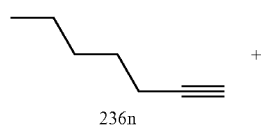

236n

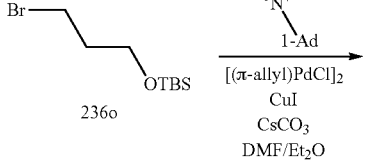

236o

[(π-allyl)PdCl]₂
CuI
CsCO₃
DMF/Et₂O

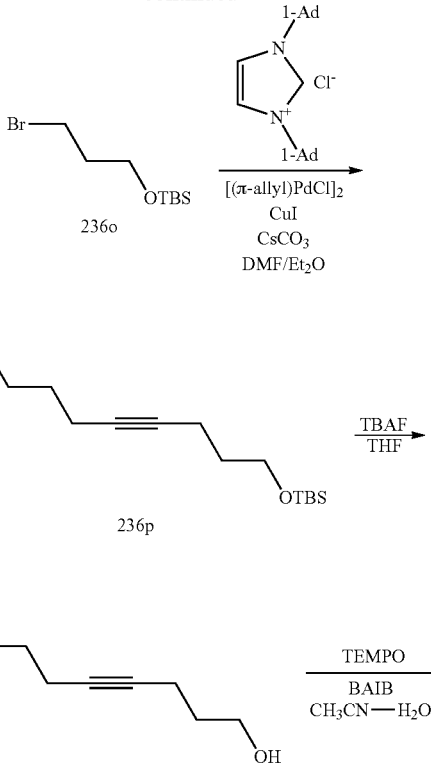

236p

TBAF / THF

236q

TEMPO
BAIB
CH₃CN—H₂O

236r

Dec-4-ynoic acid was synthesized by operations similar to those in Example 236-10, Reaction 39-2 and Reaction 236-9 using appropriate reagents and starting material.

¹H-NMR (400 MHz, CDCl₃) δ 0.89 (3H, t, J=6.8 Hz), 1.32 (4H, m), 1.47 (2H, m), 2.13 (2H, m), 2.49 (2H, m), 2.57 (2H, m).

The carboxylic acid reagent used in the synthesis of Compound 1026 (11-(3-methyl-oxetan-3-yl)-undecanoic acid) was synthesized by the following method.

(Reaction 236-13)

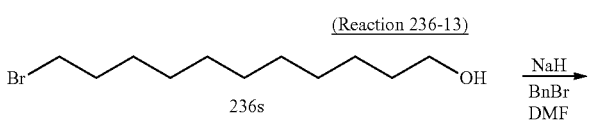

236s

NaH
BnBr
DMF

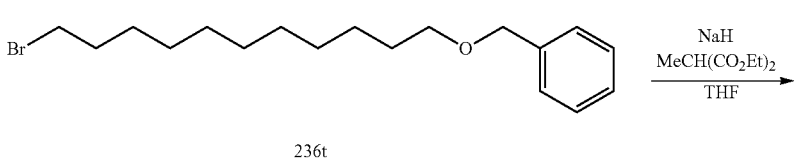

236t

NaH
MeCH(CO₂Et)₂
THF

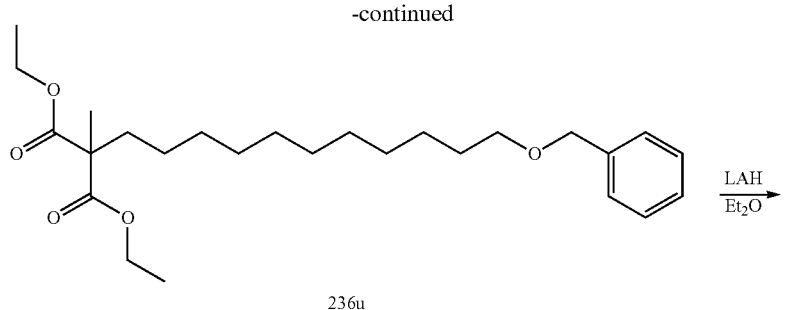

236u

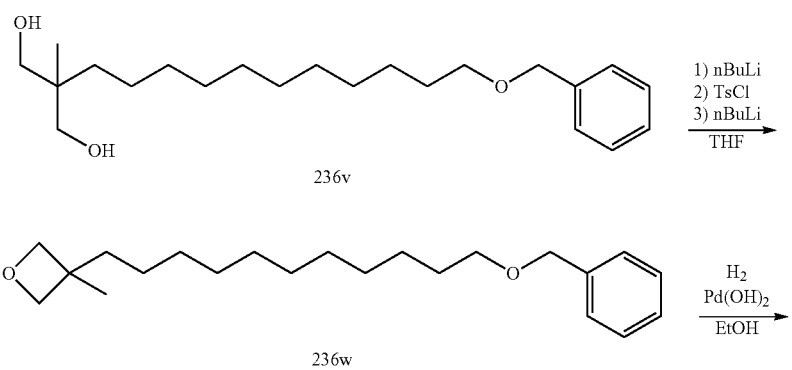

236v

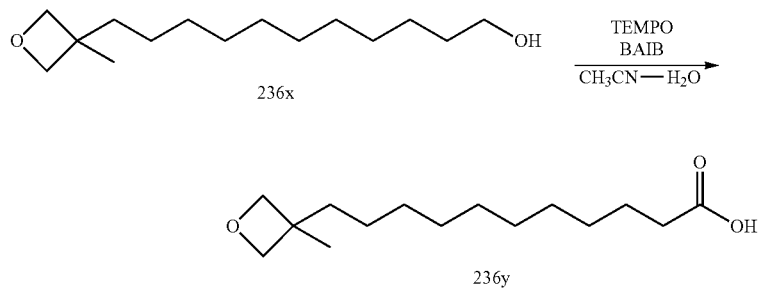

236w

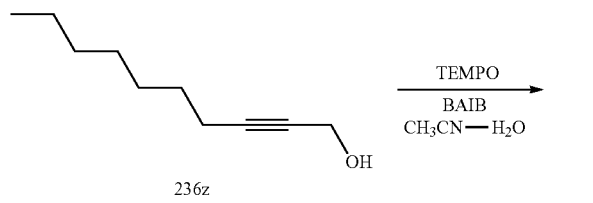

236x

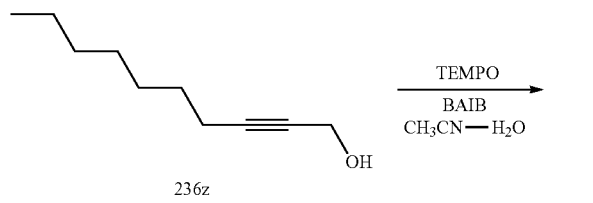

236y 11-(3-Methyl-oxetan-3-yl)-undecanoic acid was synthesized by operations similar to those in Reaction 20-2, Reaction 236-5, Reaction 95-28, Reaction 236-7, Reaction 122-2 and Reaction 236-9 using appropriate reagents and starting material.

$^1$H-NMR (400 MHz, CDCl$_3$) δ 1.27 (3H, s), 1.28 (14H, m), 1.62 (4H, m), 2.35 (2H, t, J=7.6 Hz), 4.34 (2H, d, J=5.6 Hz), 4.43 (2H, d, J=5.6 Hz).

The carboxylic acid reagent used in the synthesis of Compound 1027 (dec-2-ynoic acid) was synthesized by the following method.

(Reaction 236-14)

236z

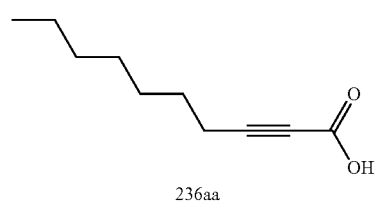

236aa

Dec-2-ynoic acid was synthesized by operations similar to those in Reaction 236-9 using appropriate reagents and starting material.

$^1$H-NMR (400 MHz, CDCl$_3$) δ 0.88 (3H, t, J=7.2 Hz), 1.28 (6H, m), 1.40 (2H, m), 1.59 (2H, m), 2.35 (2H, t, J=7.2 Hz).

Example 237
1-(4-{2-[2-(4-Fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea (Compound 1028)
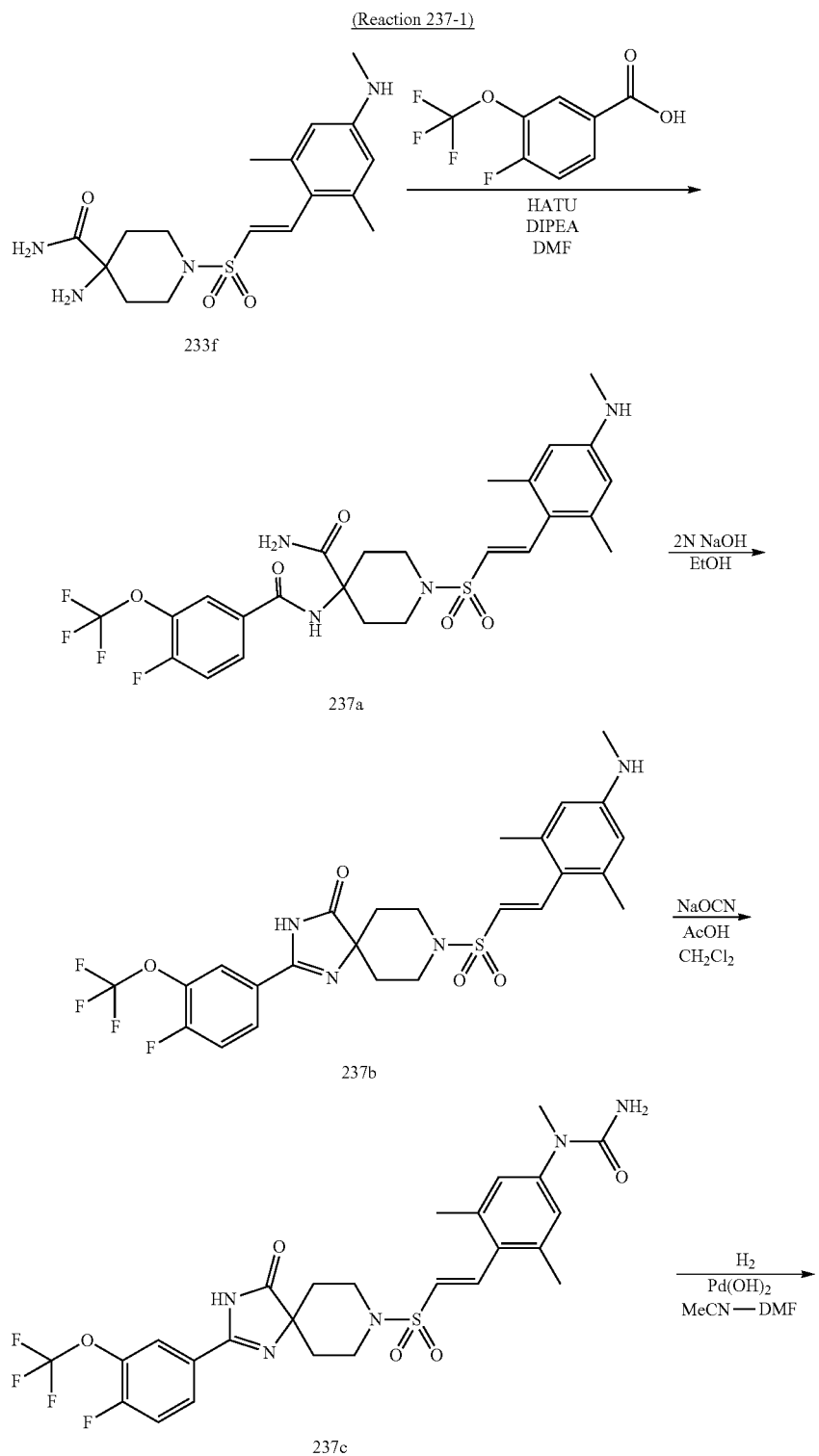

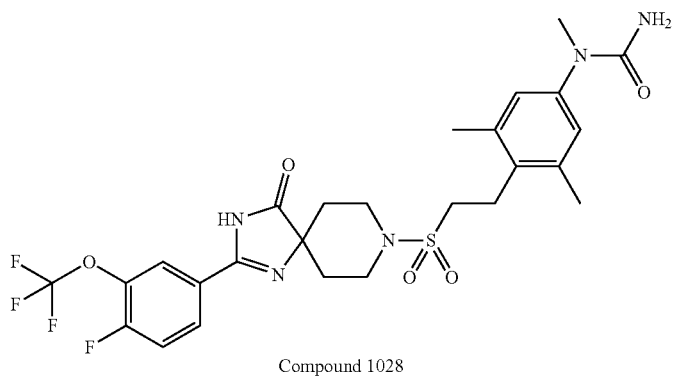

Compound 1028

1-(4-{2-[2-(4-Fluoro-3-trifluoromethoxy-phenyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 189-5, Reaction 89-2 and Reaction 184-1 using appropriate reagents and starting material.
MS (ESI) m/z=600 (M+H)+.

The example compounds shown below were synthesized by operations similar to those in Reaction 237-1 using appropriate reagents and starting materials.

Compounds 1029 to 1030

TABLE 151

| Compound | Structure | LCMS condition | Retention time (min) | MS (m/z) |
|---|---|---|---|---|
| 1029 | 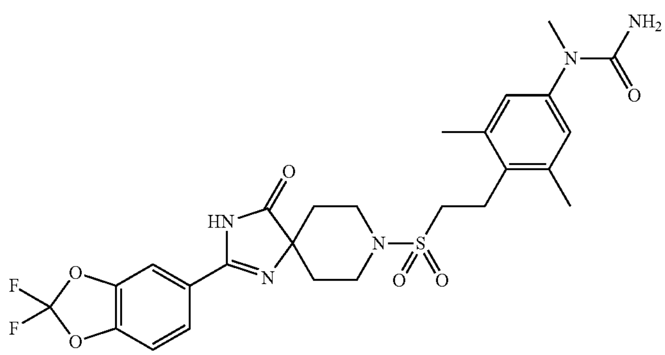 [SMILES: Cc1cc(N(C)C(N)=O)cc(C)c1CCS(=O)(=O)N1CCC2(CC1)N=C(c1ccc3c(c1)OC(F)(F)O3)NC2=O] | LCMS-F-1 | 0.95 | 578 (M + H)+ |
| 1030 | 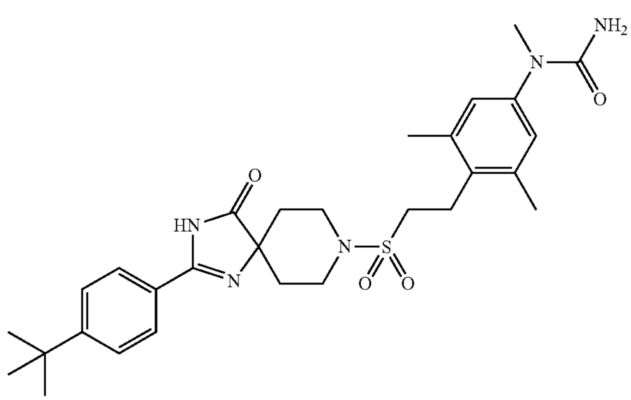 [SMILES: Cc1cc(N(C)C(N)=O)cc(C)c1CCS(=O)(=O)N1CCC2(CC1)N=C(c1ccc(C(C)(C)C)cc1)NC2=O] | LCMS-F-1 | 0.99 | 554 (M + H)+ |

Example 238

1-[3,5-Dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea (Compound 1031)

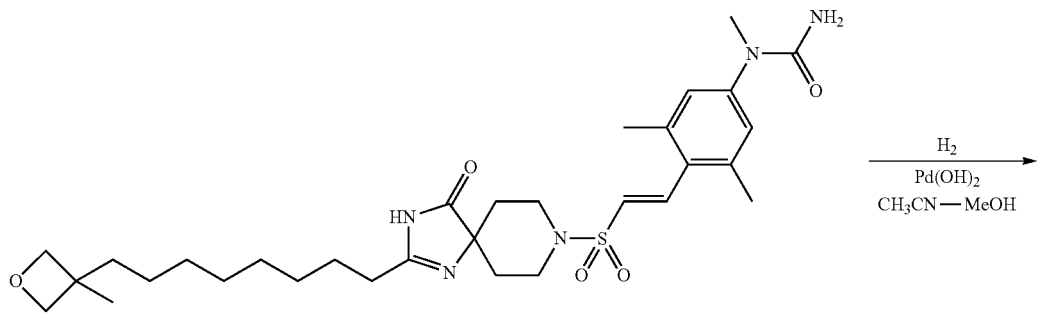

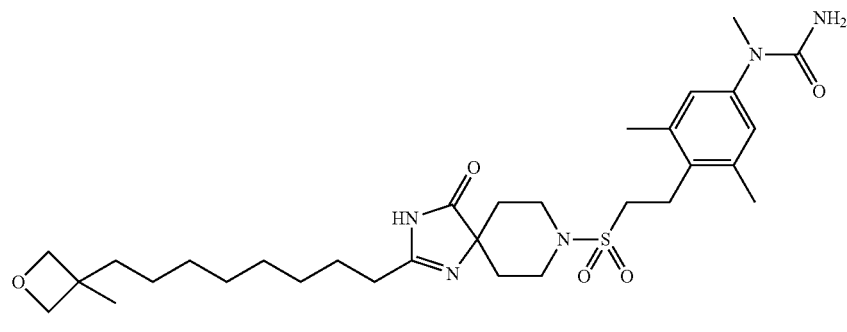

1-[3,5-Dimethyl-4-(2-{2-[8-(3-methyl-oxetan-3-yl)-octyl]-4-oxo-1,3,8-triaza-spiro[4.5]dec-1-ene-8-sulfonyl}-ethyl)-phenyl]-1-methyl-urea was synthesized by operations similar to those in Reaction 184-1 using appropriate reagents and starting material.

MS (ESI) m/z=604 (M+H)+.

The example compound shown below was synthesized by operations similar to those in Reaction 238-1 using appropriate reagents and starting material.

Compound 1032

TABLE 152

| Compound | Structure | LCMS condition | Retention time (min) | MS (m/z) |
|---|---|---|---|---|
| 1032 | 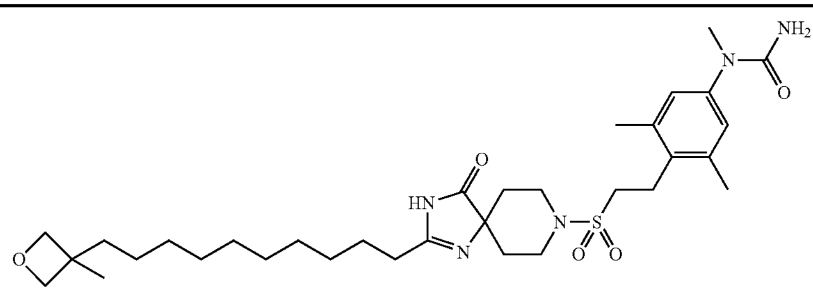 | LCMS-C-2 | 2.13 | 630 (M −H)− |

Example 239

2-(8-{2-[4-(tert-Butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester (Compound 1033)

(Reaction 239-1)

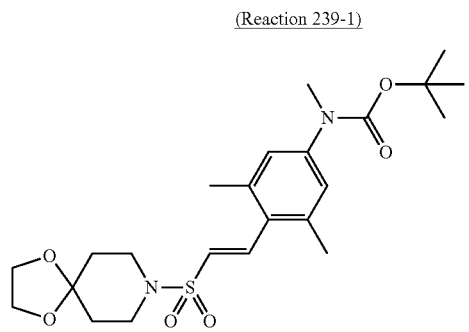

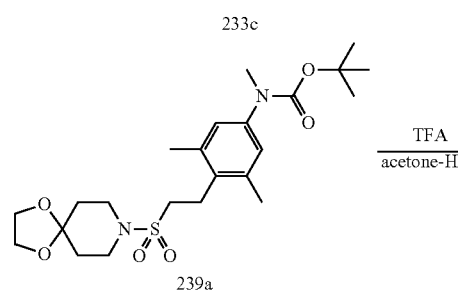

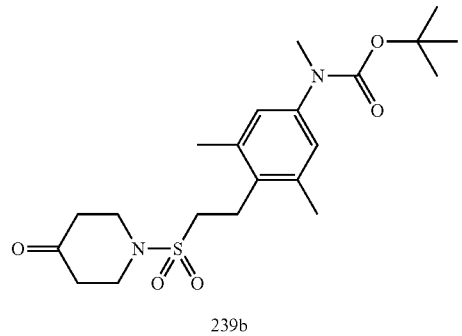

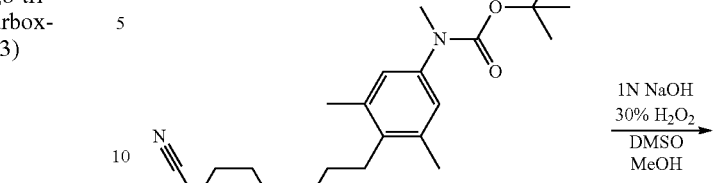

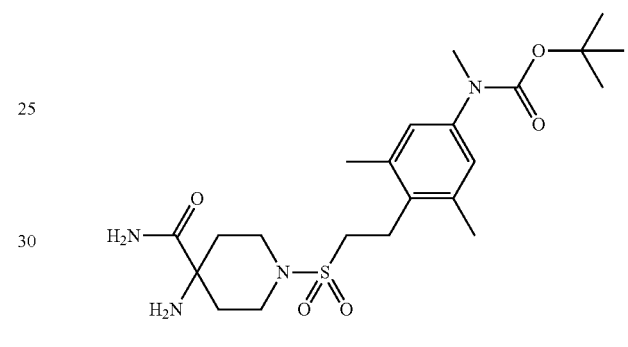

{4-[2-(4-Amino-4-carbamoyl-piperidine-1-sulfonyl)-ethyl]-3,5-dimethyl-phenyl}-methyl-carbamic acid tert-butyl ester was synthesized by operations similar to those in Reaction 184-1, Reaction 233-2, Reaction 19-2, Reaction 233-3 and Reaction 233-4 using appropriate reagents and starting material.

MS (ESI) m/z=469 (M+H)+.

(Reaction 239-2)

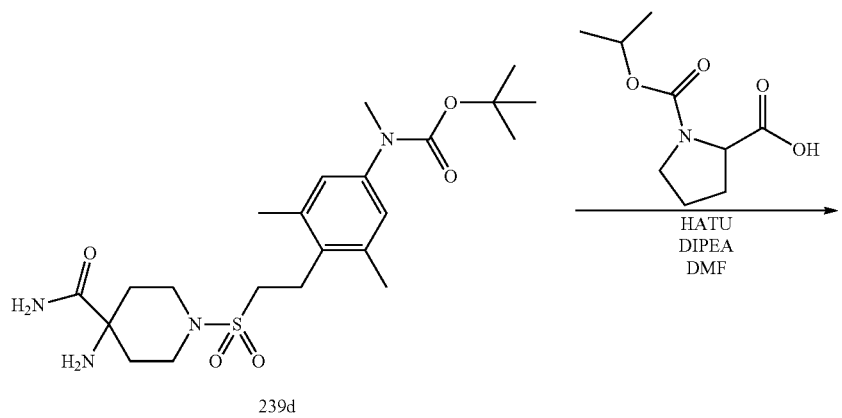

-continued

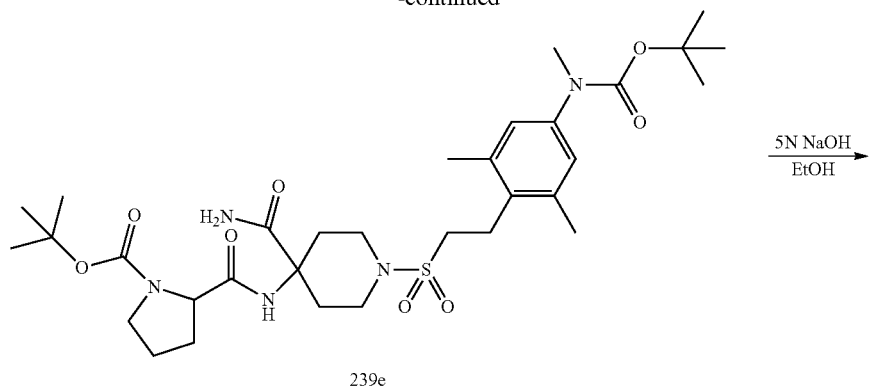

239e

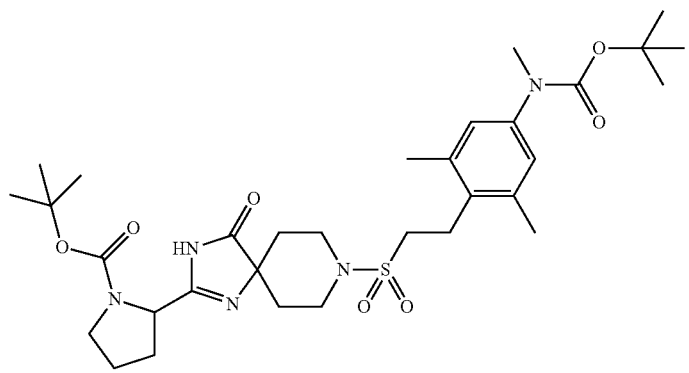

Compound 1033

2-(8-{2-[4-(tert-Butoxycarbonyl-methyl-amino)-2,6-dimethyl-phenyl]-ethanesulfonyl}-4-oxo-1,3,8-triaza-spiro[4.5]dec-1-en-2-yl)-pyrrolidine-1-carboxylic acid tert-butyl ester was synthesized by operations similar to those in Reaction 10-14 and Reaction 189-5 using appropriate reagents and starting material.

MS (ESI) m/z=648 (M+H)+.

The example compound shown below was synthesized by operations similar to those in Reaction 239-2 using appropriate reagents and starting material.

Compound 1034

TABLE 153

| Compound | Structure | LCMS condition | Retention time (min) | MS (m/z) |
|---|---|---|---|---|
| 1034 | 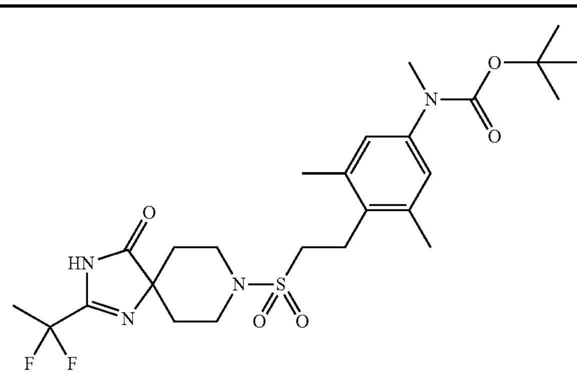 | LCMS-F-1 | 1.01 | 541 (M − H)− |

Example 240
8-[2-(2,6-Dimethyl-4-methylamino-phenyl)-ethane-sulfonyl]-2-(8,8,9,9,9-pentafluoro-nonyl)-1,3,8-tri-aza-spiro[4.5]dec-1-en-4-one (Compound 1035)
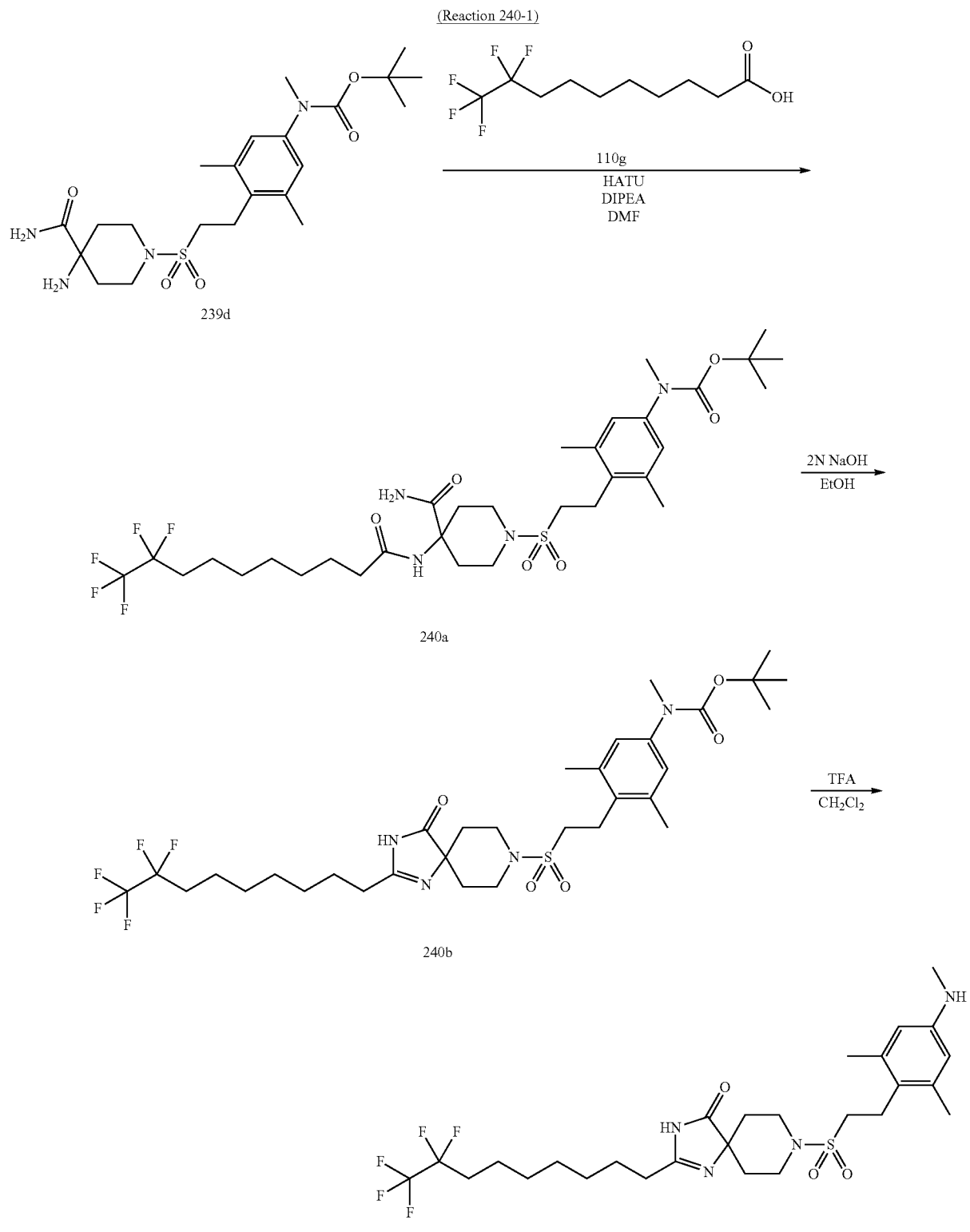

8-[2-(2,6-Dimethyl-4-methylamino-phenyl)-ethanesulfonyl]-2-(8,8,9,9,9-pentafluoro-nonyl)-1,3,8-triaza-spiro[4.5]dec-1-en-4-one was synthesized by operations similar to those in Reaction 10-14, Reaction 189-5 and Reaction 4-1 using appropriate reagents and starting material.

MS (ESI) m/z=595 (M+H)+.

The example compound shown below was synthesized by operations similar to those in Reaction 240-1 using appropriate reagents and starting material.

Compound 1036

TABLE 154

| Compound | Structure | LCMS condition | Retention time (min) | MS (m/z) |
|---|---|---|---|---|
| 1036 | 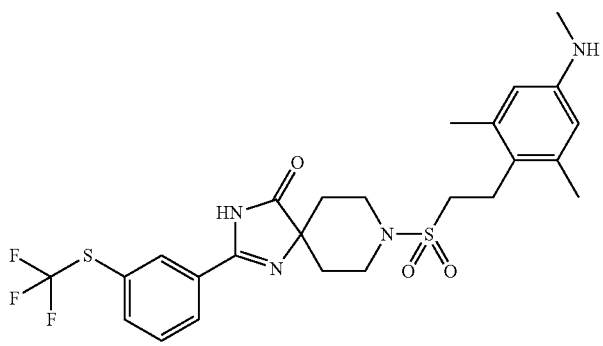 [SMILES: CNc1cc(C)c(CCS(=O)(=O)N2CCC3(CC2)N=C(c2cccc(SC(F)(F)F)c2)NC3=O)c(C)c1] | LCMS-C-1 | 2.93 | 555 (M + H)+ |

Example 241

8-[2-(2,6-Dimethyl-4-methylamino-phenyl)-ethanesulfonyl]-2-(4-isopropylidene-cyclohexyl)-1,3,8-triaza-spiro[4.5]dec-1-en-4-one (Compound 1037)

(Reaction 241-1)

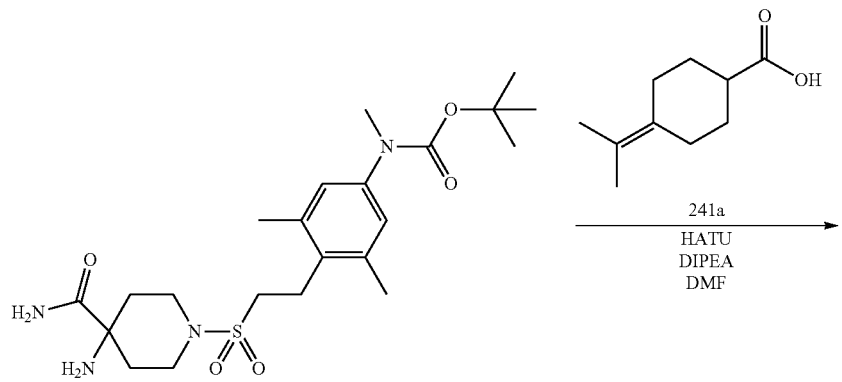

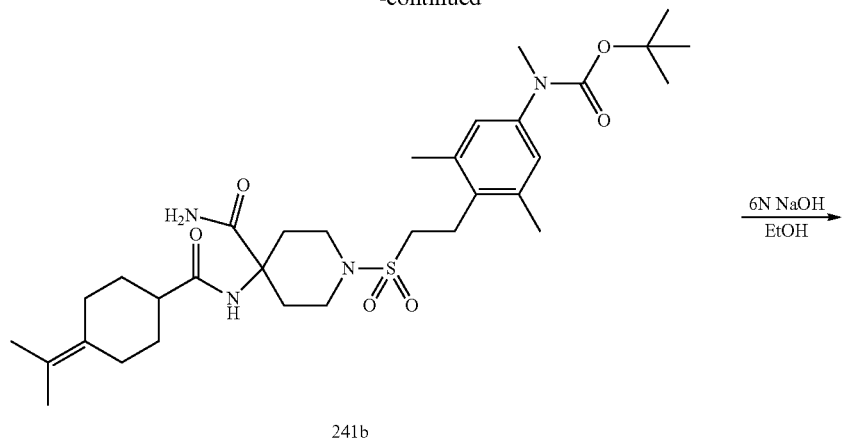
241b
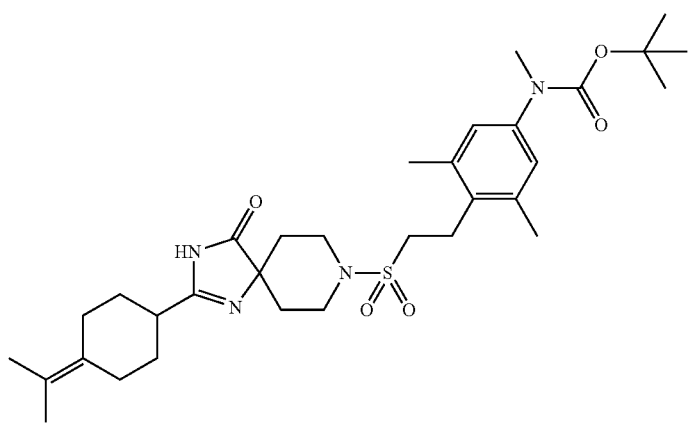
241c
(4-{2-[2-(4-Isopropylidene-cyclohexyl)-4-oxo-1,3,8-tri-aza-spiro[4.5]dec-1-ene-8-sulfonyl]-ethyl}-3,5-dimethyl-phenyl)-methyl-carbamic acid tert-butyl ester was synthesized by operations similar to those in Reaction 10-14 and Reaction 189-5 using appropriate reagents and starting material.
MS (ESI) m/z=601 (M+H)+.
(Reaction 241-2)
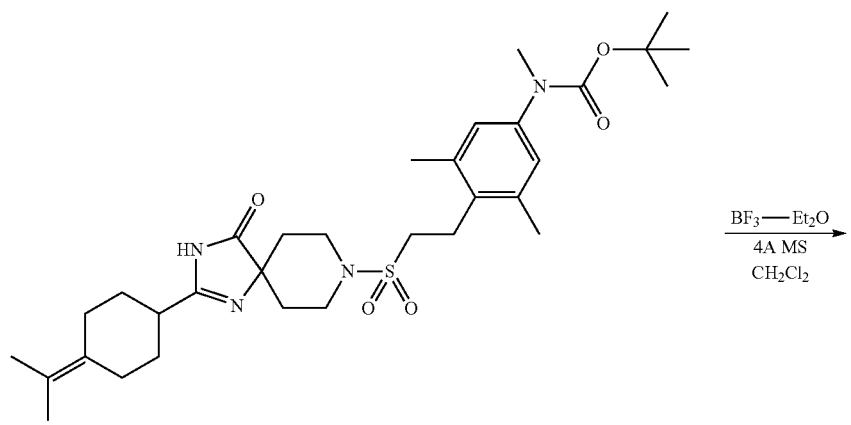
241c

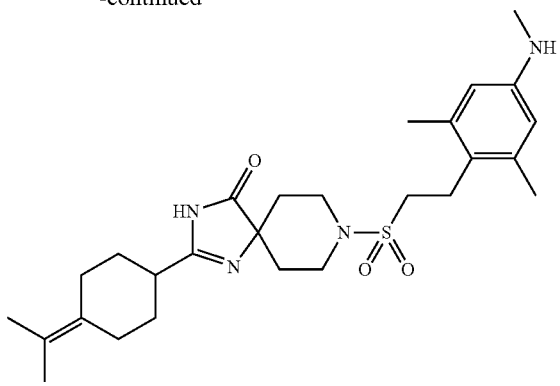

Compound 1037

About 40 4 AMS beads were added to a solution of (4-{2-[2-(4-isopropylidene-cyclohexyl)-4-oxo-1,3,8-triaza-spiro[4.5]dec-1-ene-8-sulfonyl]-ethyl}-3,5-dimethyl-phenyl)-methyl-carbamic acid tert-butyl ester (85.7 mg, 143 μmol) in dichloromethane (1.4 ml), and the mixture was stirred at room temperature for 10 minutes. Thereafter, BF$_3$.Et$_2$O (90.2 μl, 715 μmol) was added to the reaction mixture at 0° C., and the mixture was stirred at room temperature for three hours. The reaction mixture was quenched by adding triethylamine and diluted with ethyl acetate. The organic layer was then washed with a saturated aqueous sodium bicarbonate solution and water, and then dried over MgSO$_4$ and concentrated under reduced pressure. The resulting residue was purified by silica gel column chromatography (dichloromethane/methanol=100/0→92/8) to give 8-[2-(2,6-dimethyl-4-methylamino-phenyl)-ethane-sulfonyl]-2-(4-isopropylidene-cyclohexyl)-1,3,8-triaza-spiro[4.5]dec-1-en-4-one (66.0 mg, 92%).

MS (ESI) m/z=501 (M+H)+.

The carboxylic acid reagent used in the synthesis of Compound 1037 (4-isopropylidene-cyclohexanecarboxylic acid) was synthesized by the following method.

(Reaction 241-3)

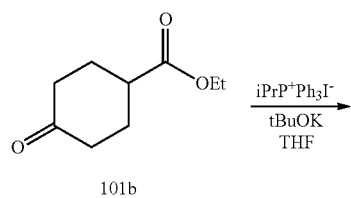

4-Isopropylidene-cyclohexanecarboxylic acid was synthesized by operations similar to those in Reaction 191-14 and Reaction 189-5 using appropriate reagents and starting material.

MS (ESI) m/z=169 (M+H)+.

Example 242

1-[3,5-Dimethyl-4-(2-{4-oxo-2-[3-(1,1,2,2-tetra-fluoro-ethoxy)-phenyl]-1,3,8-triaza-spiro[4.5]dec-1-ene-8-sulfonyl}-ethyl)-phenyl]-1-methyl-urea (Compound 1038)

(Reaction 242-1)

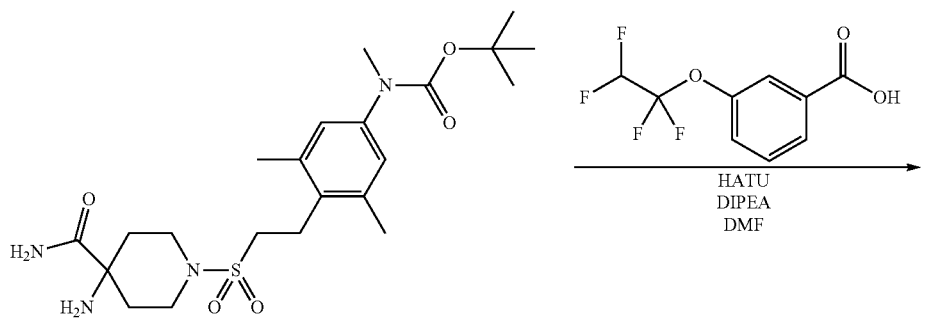

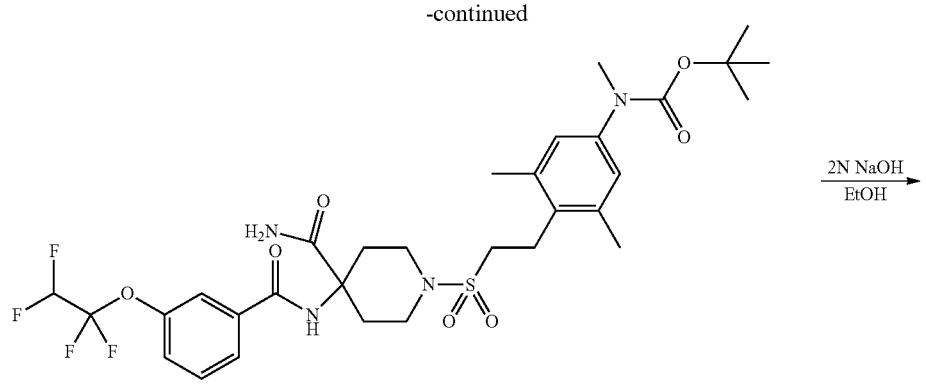
242a
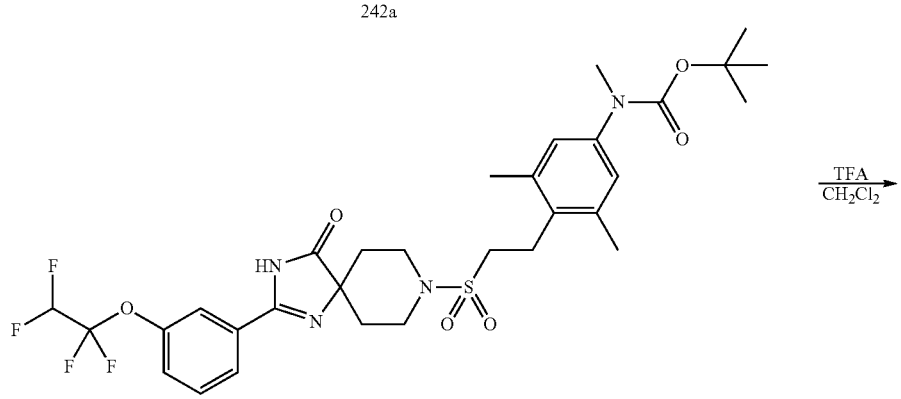
242b
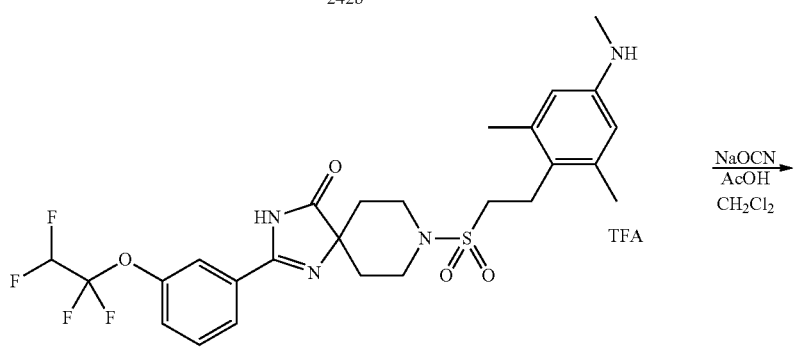
242c
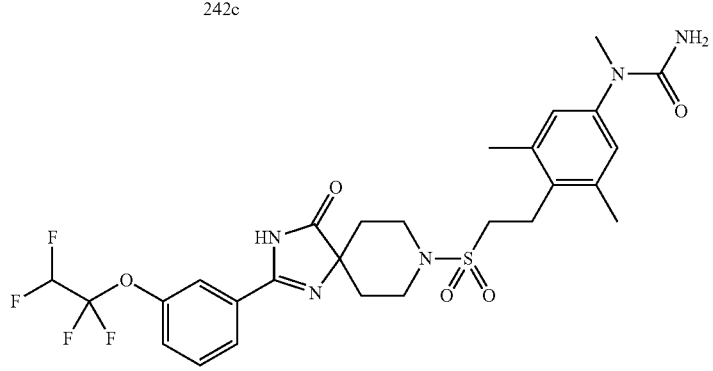
Compound 1038
1-[3,5-Dimethyl-4-(2-{4-oxo-2-[3-(1,1,2,2-tetrafluoro-ethoxy)-phenyl]-1,3,8-triaza-spiro[4.5]dec-1-ene-8-sulfonyl}-ethyl)-phenyl]-1-methyl-urea was synthesized by operations similar to those in Reaction 10-14, Reaction 189-5, Reaction 4-1 and Reaction 89-2 using appropriate reagents and starting material.
MS (ESI) m/z=614 (M+H)+.

Example 243
1-(3,5-Dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea (Compound 1039)
(Reaction 243-1)
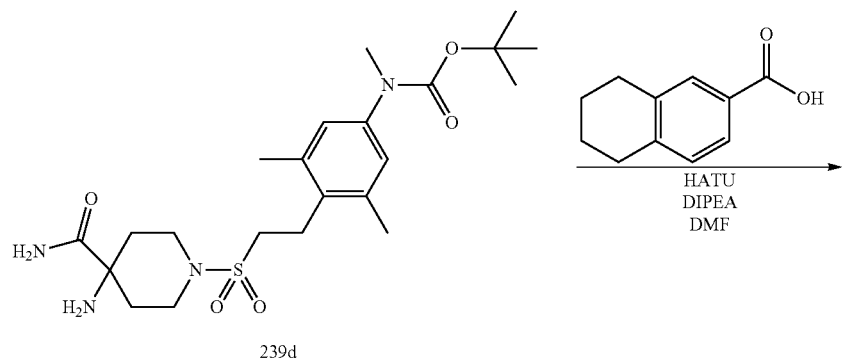
239d
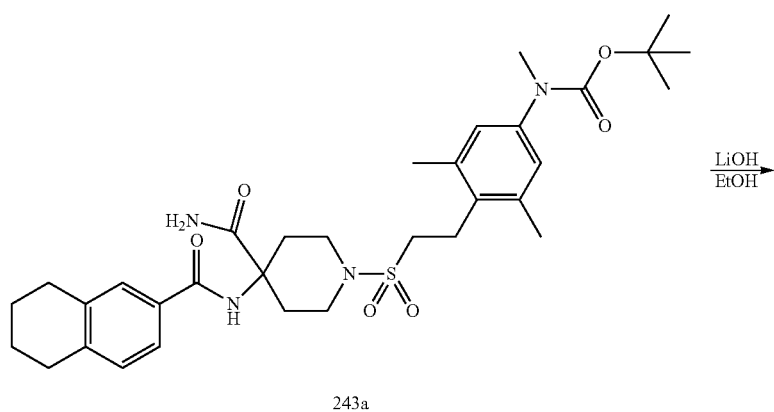
243a
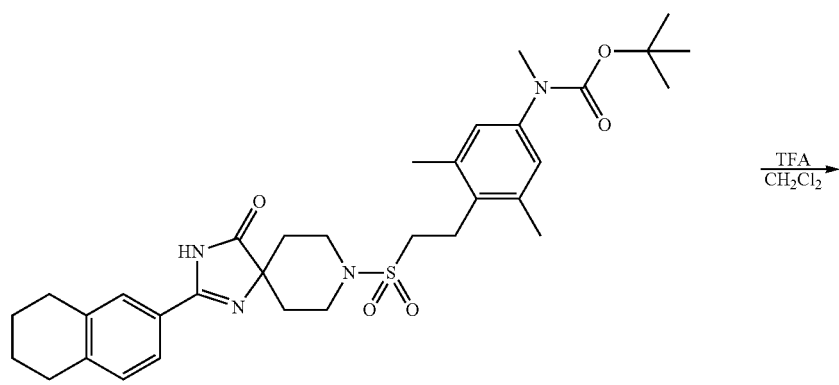
243b

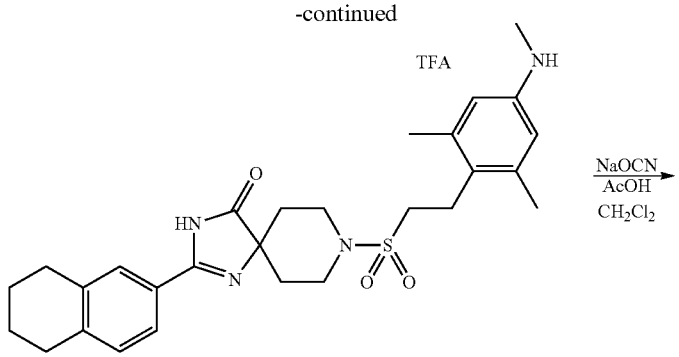

243c

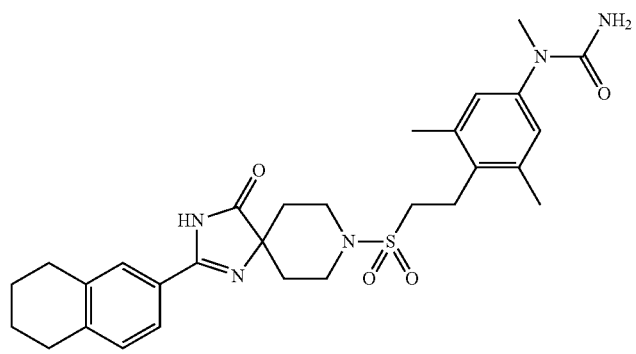

Compound 1039

1-(3,5-Dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea was synthesized by operations similar to those in Reaction 10-14, Reaction 236-2, Reaction 4-1 and Reaction 89-2 using appropriate reagents and starting material.

MS (ESI) m/z=552 (M+H)+.

The example compounds shown below were synthesized by operations similar to those in Reaction 243-1 using appropriate reagents and starting materials.

Compounds 1040 to 1042

TABLE 155

| Compound | Structure | LCMS condition | Retention time (min) | MS (m/z) |
|---|---|---|---|---|
| 1040 | 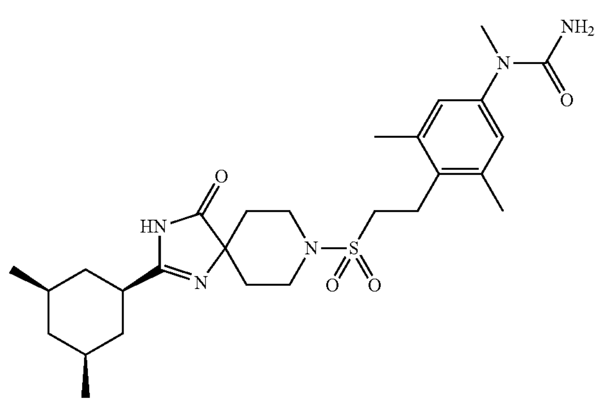 [SMILES: Cc1cc(N(C)C(N)=O)cc(C)c1CCS(=O)(=O)N1CCC2(CC1)N=C([C@@H]1C[C@H](C)C[C@H](C)C1)NC2=O] | LCMS-A-1 | 2.06 | 532 (M + H)+ |

TABLE 155-continued
| Compound | Structure | LCMS condition | Retention time (min) | MS (m/z) |
|---|---|---|---|---|
| 1041 | 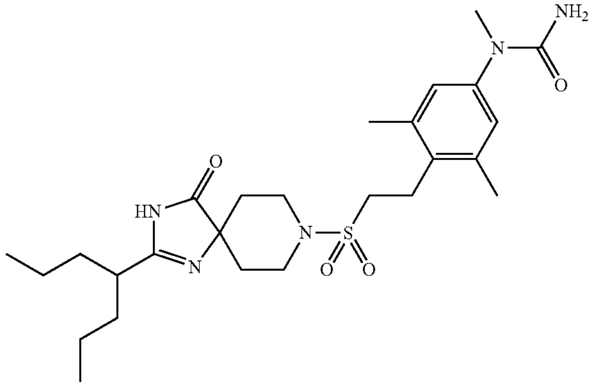 [SMILES: CCCC(CCC)C1=NC2(CCN(S(=O)(=O)CCc3c(C)cc(N(C)C(N)=O)cc3C)CC2)C(=O)N1] | LCMS-A-1 | 2.00 | 520 (M + H)+ |
| 1042 | 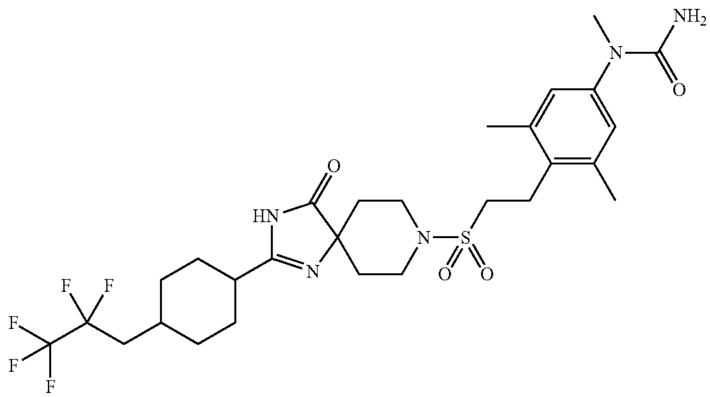 [SMILES: Cc1cc(N(C)C(N)=O)cc(C)c1CCS(=O)(=O)N1CCC2(CC1)N=C(C1CCC(CC(F)(F)C(F)(F)F)CC1)NC2=O] | LCMS-A-1 | 2.26 | 636 (M + H)+ |
The carboxylic acid reagent used in the synthesis of Compound 1042 (4-(2,2,3,3,3-pentafluoro-propyl)-cyclohexanecarboxylic acid) was synthesized by the following method.
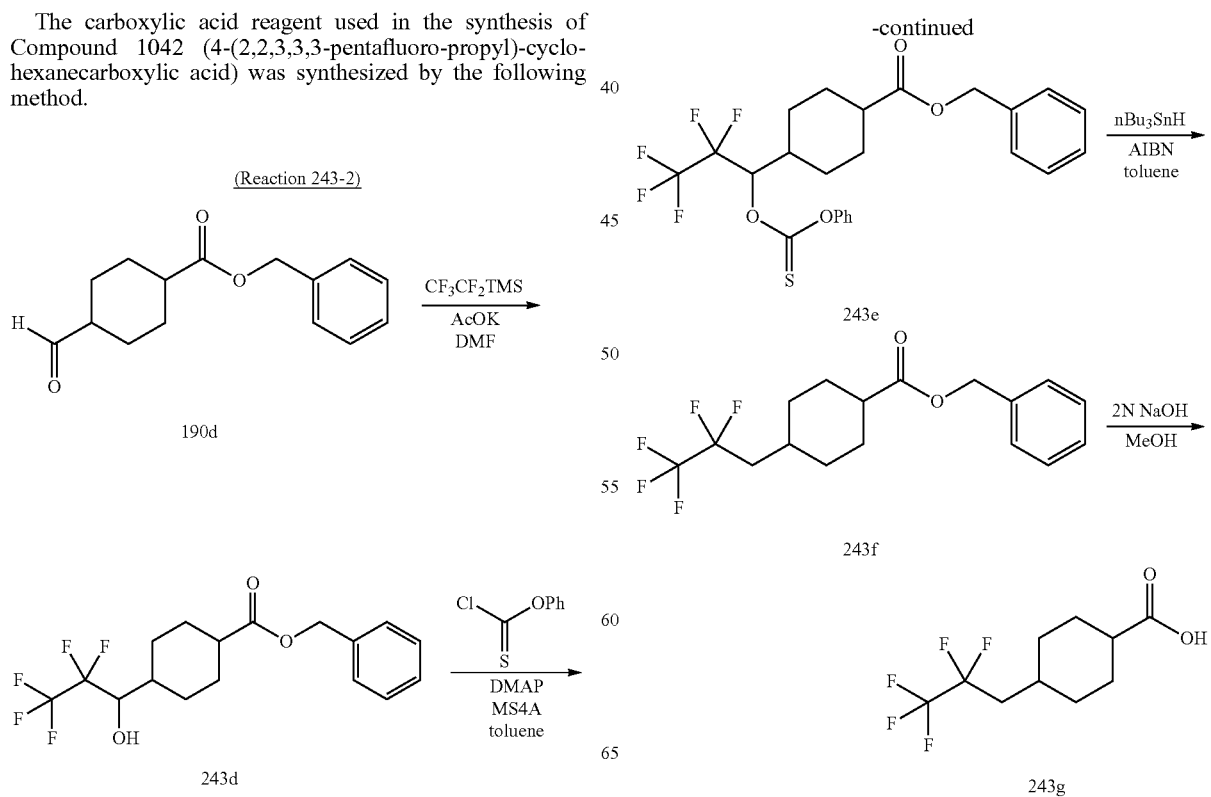

1181
4-(2,2,3,3,3-Pentafluoro-propyl)-cyclohexanecarboxylic acid was synthesized by operations similar to those in Reaction 193-4, Reaction 193-5, Reaction 193-6 and Reaction 95-18 using appropriate reagents and starting material.
$^1$H-NMR (400 MHz, CDCl$_3$) δ 2.64 (0.6H, qui, J=4.9 Hz), 2.29 (0.4H, tt, J=12.2, 3.4 Hz), 2.09-1.06 (11H, m). (cis/trans=ca 6:4)
1182
Example 244
1-(3,5-Dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea (Compound 1043)
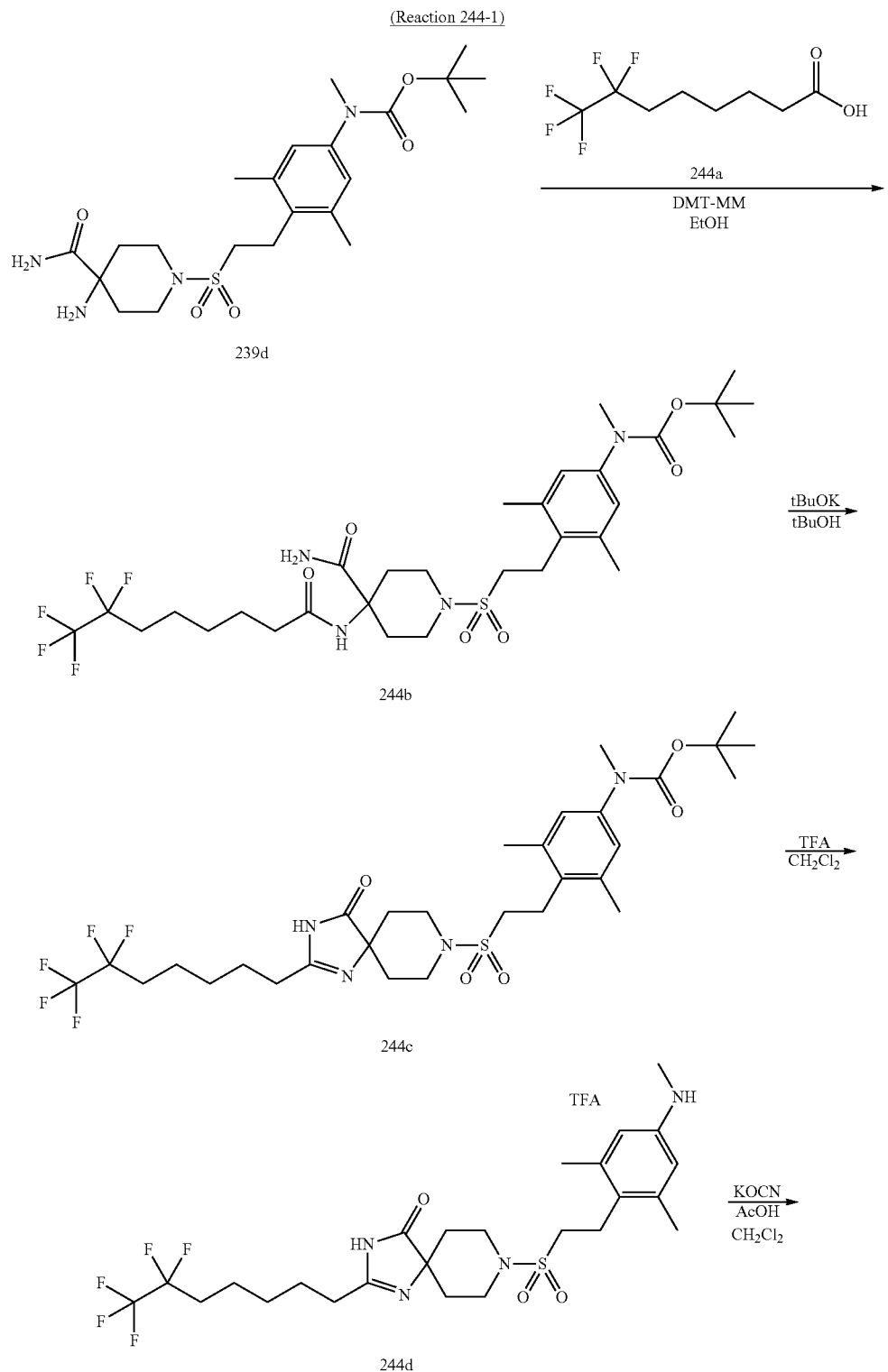

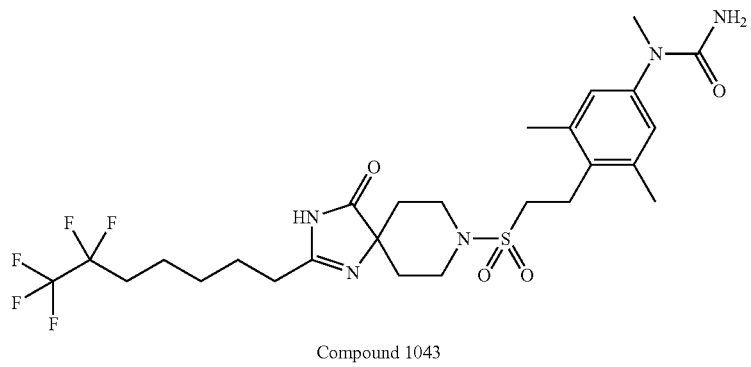

Compound 1043

1-(3,5-Dimethyl-4-{2-[4-oxo-2-(6,6,7,7,7-pentafluoro-heptyl)-1,3,8-triaza-spiro[4.5]dec-1-ene-8-sulfonyl]-ethyl}-phenyl)-1-methyl-urea was synthesized by operations similar to those in Reaction 10-1, Reaction 10-12, Reaction 4-1 and Reaction 89-2 (using KOCN) using appropriate reagents and starting material.

MS (ESI) m/z=610 (M+H)+.

The carboxylic acid reagent used in the synthesis of Compound 1043 (7,7,8,8,8-pentafluoro-octanoic acid) was synthesized by the following method.

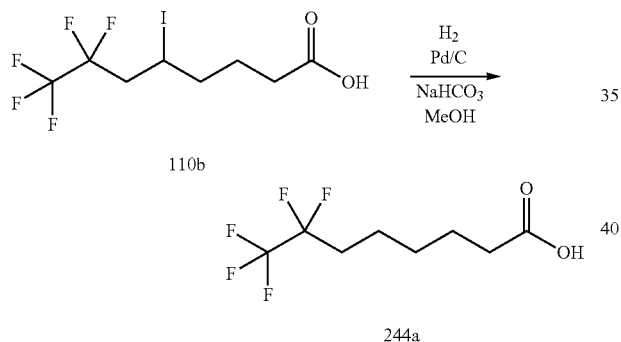

7,7,8,8,8-Pentafluoro-octanoic acid was synthesized by operations similar to those in Reaction 18-2 using appropriate reagents and starting material.

¹H-NMR (400 MHz, CDCl₃) δ 1.42-1.48 (2H, m), 1.57-1.73 (4H, m), 2.03 (2H, tt, J=6.8, 18.2 Hz), 2.39 (2H, t, J=7.4 Hz).

Example 245

N-(3,5-Dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide (Compound 1044) and 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea (Compound 1045)

(Reaction 245-1)

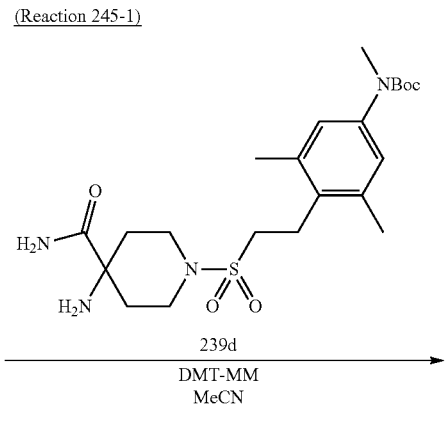

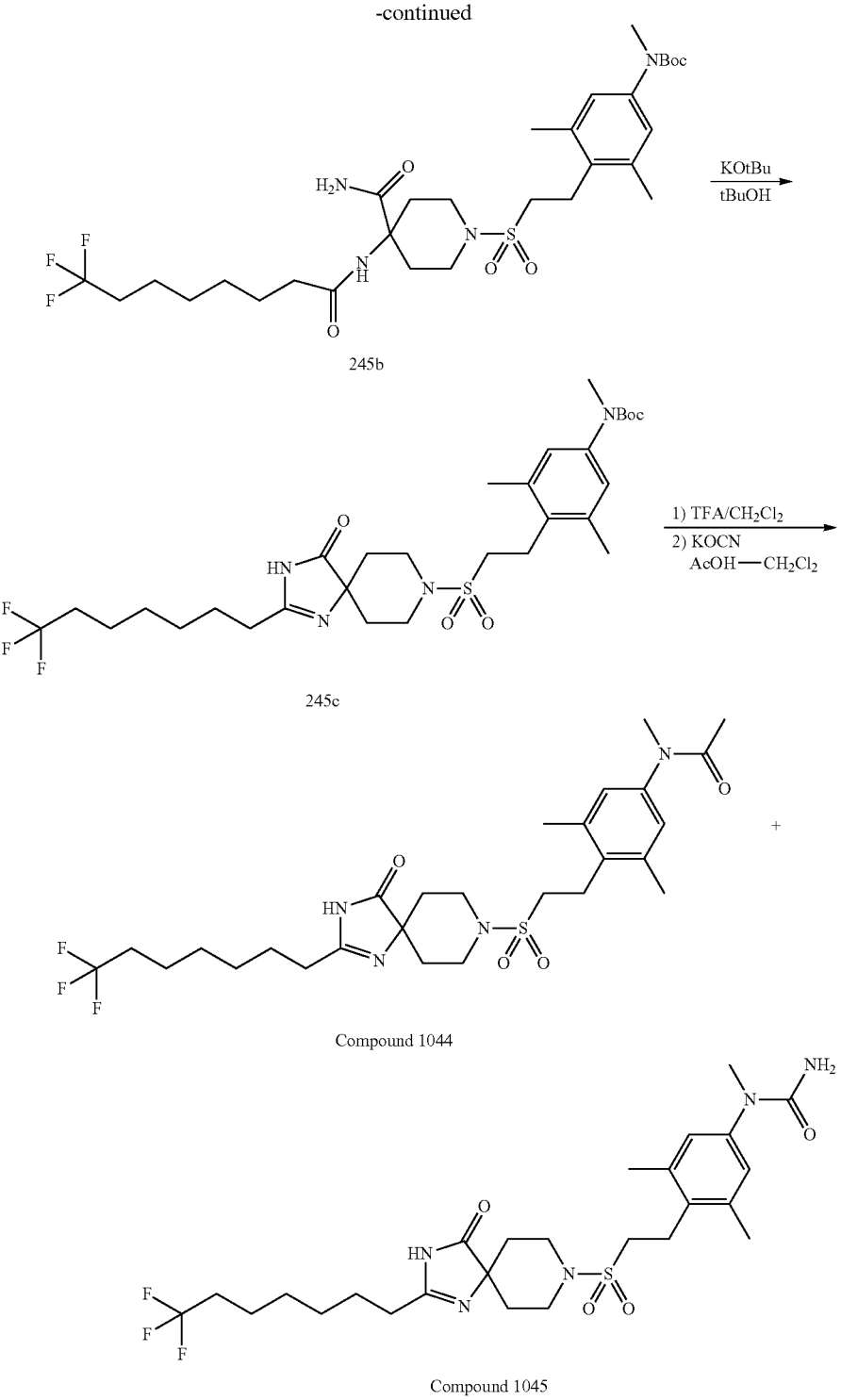

N-(3,5-Dimethyl-4-{2-[4-oxo-2-(7,7,7-trifluoro-heptyl)-1,3,8-triaza-spiro[4.5]dec-1-ene-8-sulfonyl]-ethyl}-phenyl)-N-methyl-acetamide MS (ESI) m/z=573 (M+H)+ and 1-(3,5-dimethyl-4-{2-[4-oxo-2-(7,7,7-trifluoro-heptyl)-1,3,8-triaza-spiro[4.5]dec-1-ene-8-sulfonyl]-ethyl}-phenyl)-1-methyl-urea MS (ESI) m/z=574 (M+H)+ were synthesized by operations similar to those in Reaction 10-1, Reaction 10-12, Reaction 4-1 and Reaction 89-2 (using KOCN) using appropriate reagents and starting material.

The carboxylic acid reagent used in the synthesis of Compound 1044 and Compound 1045 (8,8,8-trifluoro-octanoic acid) was synthesized by the following method.

1187

(Reaction 245-2)

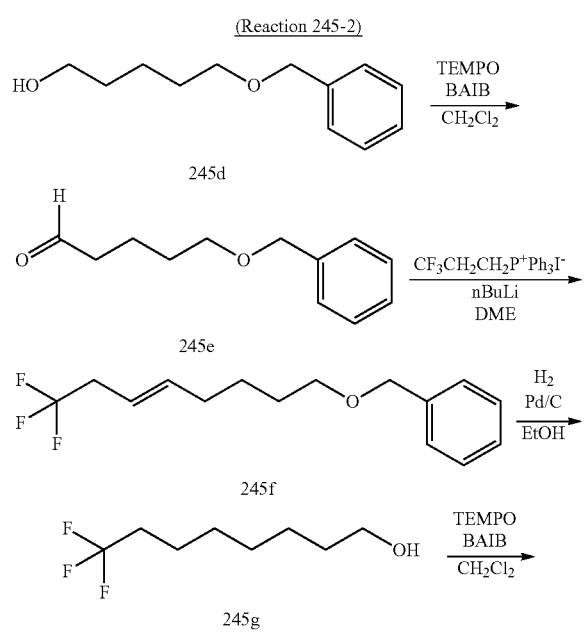

1188

-continued

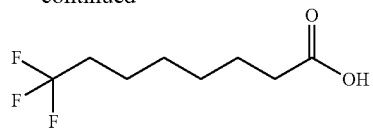
245a 8,8,8-Trifluoro-octanoic acid was synthesized by operations similar to those in Reaction 109-1, Reaction 101-1, Reaction 18-2 and Reaction 109-1 using appropriate reagents and starting material.

$^1$H-NMR (400 MHz, CDCl$_3$) δ 1.32-1.46 (4H, br-m), 1.52-1.68 (2H, m), 1.66-1.72 (2H, m), 2.00-2.14 (2H, m), 2.38 (2H, t, J=7.2 Hz).

The example compounds shown below were synthesized by operations similar to those in Reaction 245-1 using appropriate reagents and starting materials.

Compounds 1046 to Compound 1047

TABLE 156

| Compound | Structure | LCMS condition | Retention time (min) | MS (m/z) |
|---|---|---|---|---|
| 1046 | 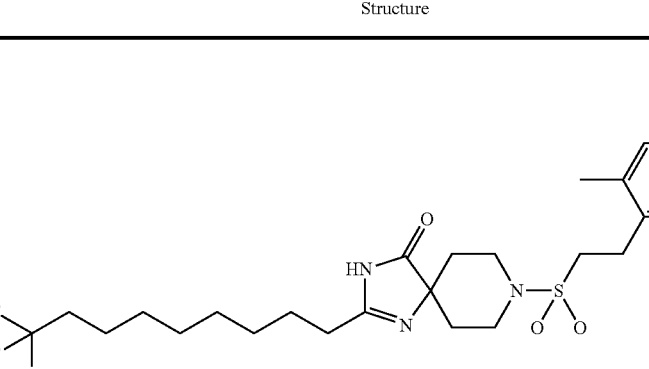 | LCMS-B-1 | 2.03 | 602 (M + H)+ |
| 1047 | 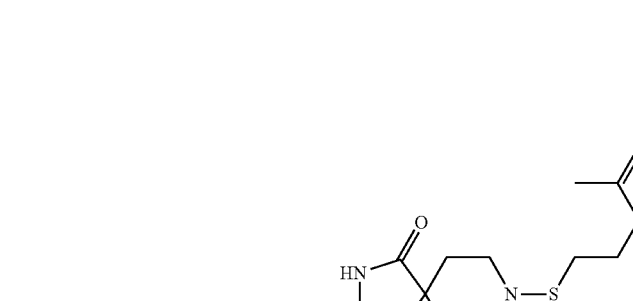 | LCMS-B-1 | 2.16 | 601 (M + H)+ |

Example 246
1-[3,5-Dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea (Compound 1048)
(Reaction 246-1)
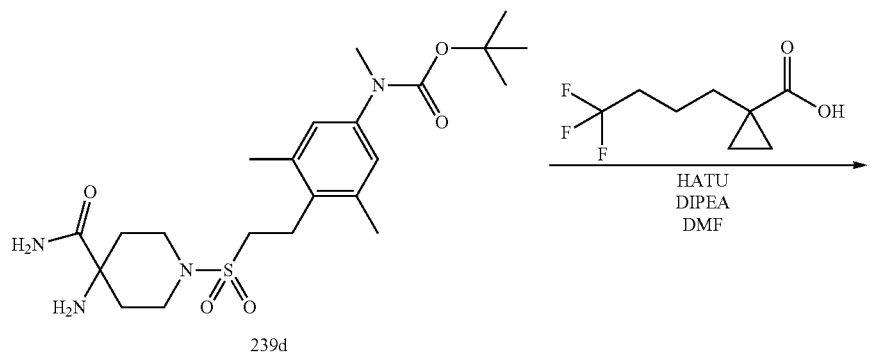
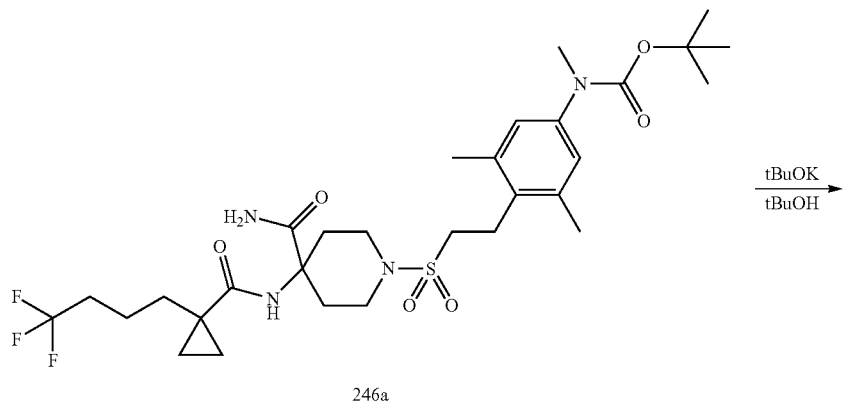
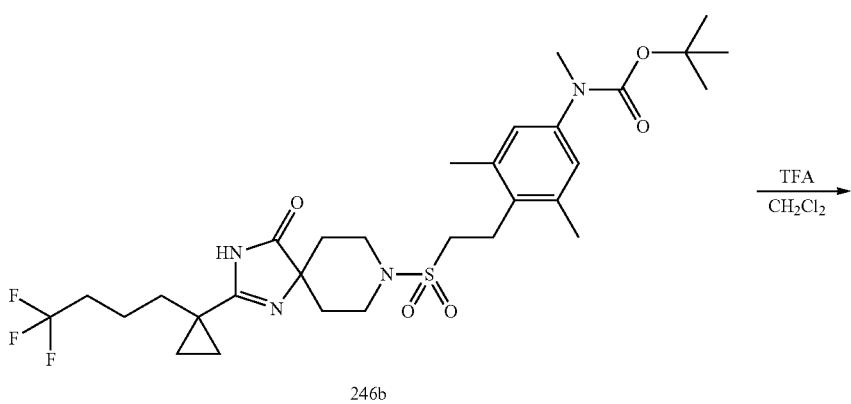
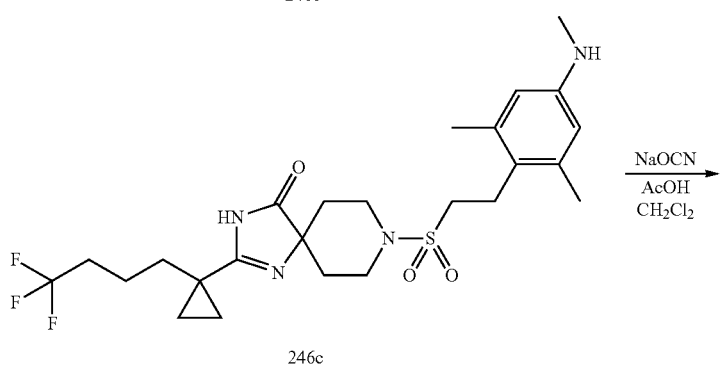

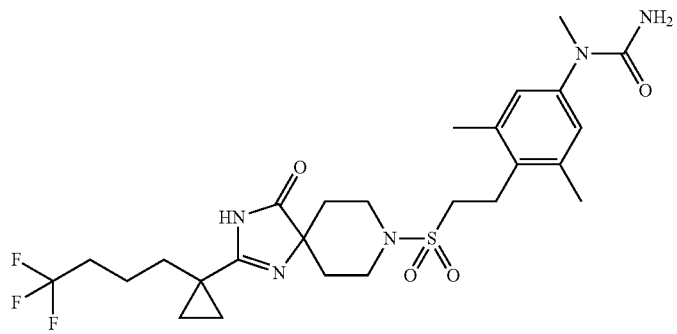

Compound 1048

1-[3,5-Dimethyl-4-(2-{4-oxo-2-[1-(4,4,4-trifluoro-butyl)-cyclopropyl]-1,3,8-triaza-spiro[4.5]dec-1-ene-8-sulfonyl}-ethyl)-phenyl]-1-methyl-urea was synthesized by operations similar to those in Reaction 10-14, Reaction 10-12, Reaction 4-1 and Reaction 89-2 (using KOCN) using appropriate reagents and starting material.

MS (ESI) m/z=572 (M+H)+.

Example 247

1-(3,5-Dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea (Compound 1050)

(Reaction 247-1)

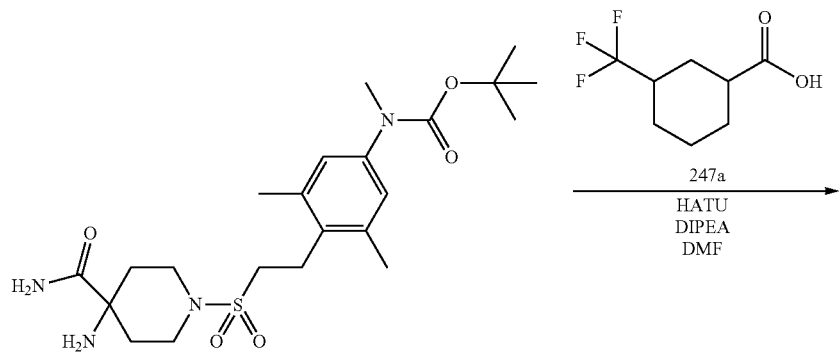

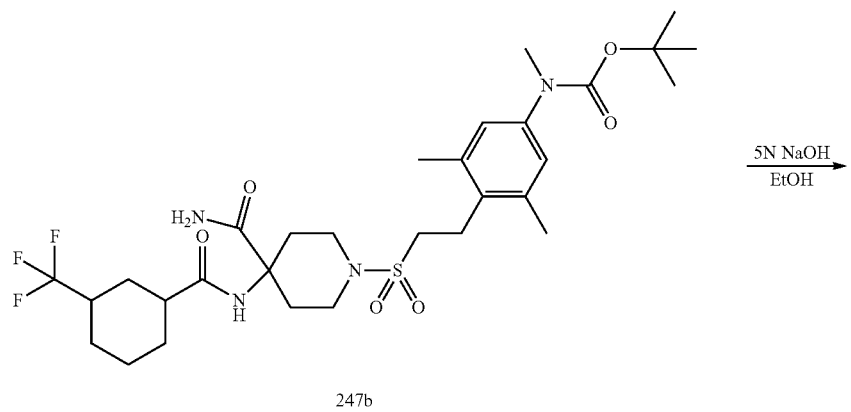

-continued

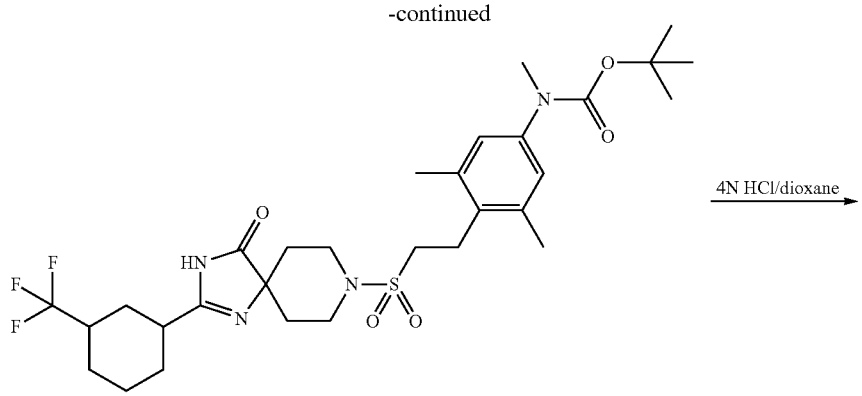

247c

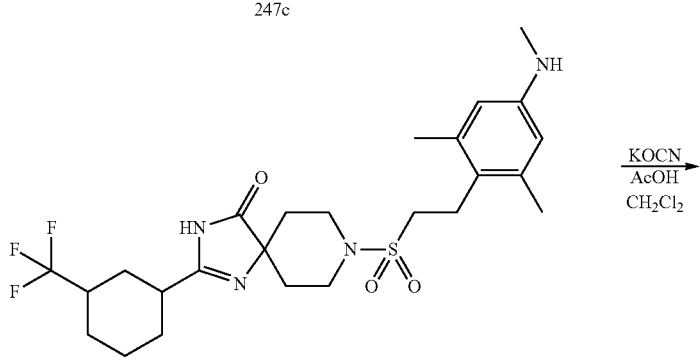

247d

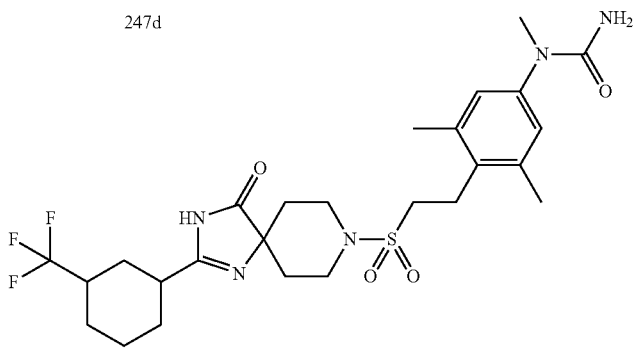

Compound 1050

1-(3,5-Dimethyl-4-{2-[4-oxo-2-(3-trifluoromethyl-cyclohexyl)-1,3,8-triaza-spiro[4.5]dec-1-ene-8-sulfonyl]-ethyl}-phenyl)-1-methyl-urea was synthesized by operations similar to those in Reaction 10-14, Reaction 189-5, Reaction 5-3 and Reaction 89-2 using appropriate reagents and starting material.

MS (ESI) m/z=572 (M+H)+.

The carboxylic acid reagent used in the synthesis of Compound 1050 (3-trifluoromethyl-cyclohexanecarboxylic acid) was synthesized by the following method.

(Reaction 247-2)

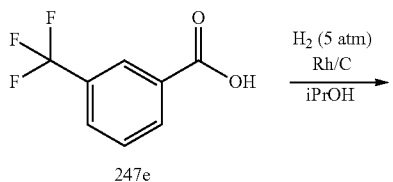

247e

-continued

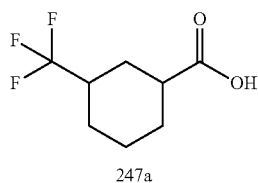

247a

3-Trifluoromethyl-cyclohexanecarboxylic acid was synthesized by operations similar to those in Reaction 193-3 using appropriate reagents and starting material.

$^1$H-NMR (400 MHz, CDCl$_3$) δ 1.22-2.40 (9.57H, m), 2.88 (0.43H, m) (cis:trans=1.3:1)

The example compounds shown below were synthesized by operations similar to those in Reaction 247-1 using appropriate reagents and starting materials.

Compounds 1051 to 1058

TABLE 157

| Compound | Structure | LCMS condition | Retention time (min) | MS (m/z) |
|---|---|---|---|---|
| 1051 | 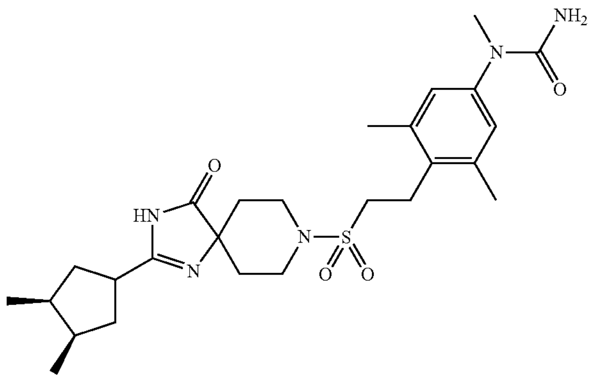 [SMILES: Cc1cc(N(C)C(N)=O)cc(C)c1CCS(=O)(=O)N1CCC2(CC1)N=C(C1C[C@@H](C)[C@@H](C)C1)NC2=O] | LCMS-F-1 | 0.93 | 518 (M + H)+ |
| 1052 | 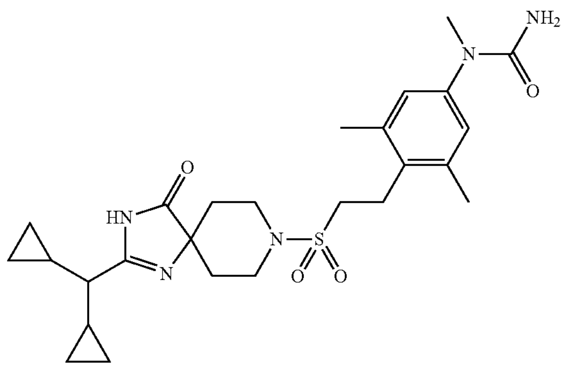 [SMILES: Cc1cc(N(C)C(N)=O)cc(C)c1CCS(=O)(=O)N1CCC2(CC1)N=C(C(C1CC1)C1CC1)NC2=O] | LCMS-F-1 | 0.87 | 516 (M + H)+ |
| 1053 | 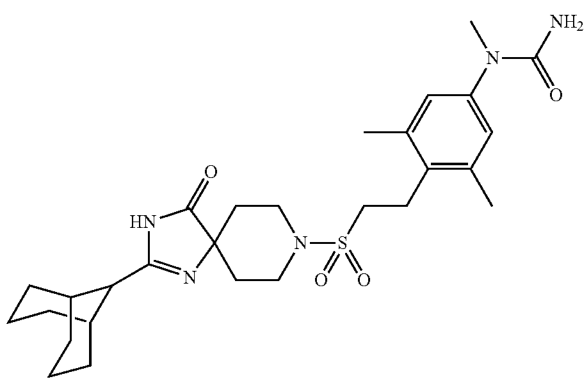 | LCMS-F-1 | 0.99 | 544 (M + H)+ |
| 1054 | 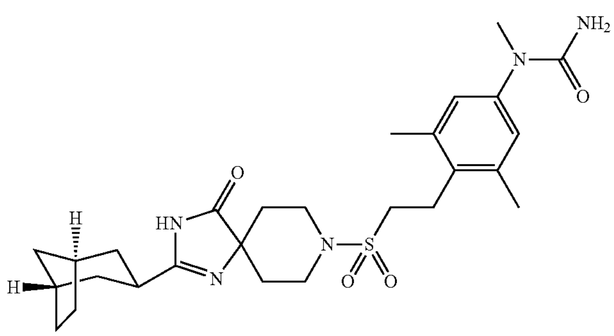 [SMILES: Cc1cc(N(C)C(N)=O)cc(C)c1CCS(=O)(=O)N1CCC2(CC1)N=C(C1C[C@H]3CC[C@@H](C1)C3)NC2=O] | LCMS-F-1 | 0.93 | 530 (M + H)+ |

TABLE 157-continued

| Compound | Structure | LCMS condition | Retention time (min) | MS (m/z) |
|---|---|---|---|---|
| 1055 | 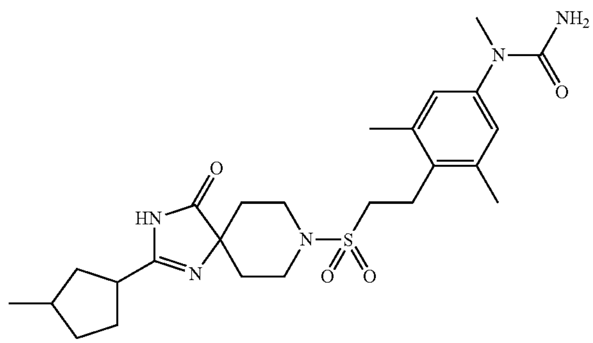 [SMILES: Cc1cc(N(C)C(N)=O)cc(C)c1CCS(=O)(=O)N1CCC2(CC1)N=C(C1CCC(C)C1)NC2=O] | LCMS-F-1 | 0.89 | 504 (M + H)+ |
| 1056 | 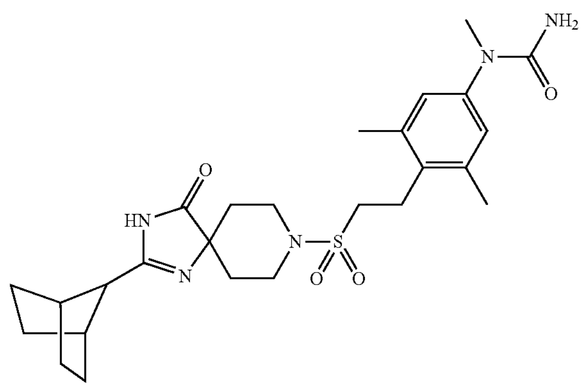 [SMILES: Cc1cc(N(C)C(N)=O)cc(C)c1CCS(=O)(=O)N1CCC2(CC1)N=C(C1C3CCC1CC3)NC2=O] | LCMS-F-1 | 0.91 | 516 (M + H)+ |
| 1057 | 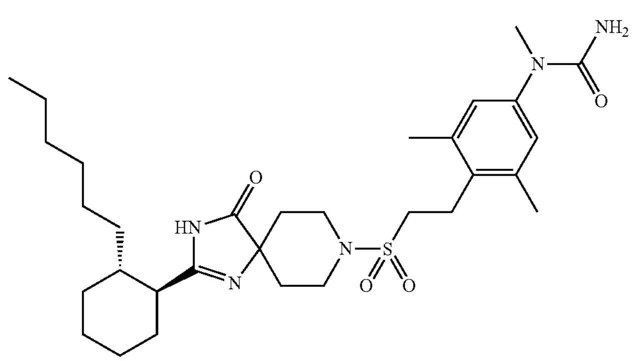 [SMILES: CCCCCC[C@H]1CCCC[C@@H]1C1=NC2(CCN(S(=O)(=O)CCc3c(C)cc(N(C)C(N)=O)cc3C)CC2)C(=O)N1] | LCMS-F-1 | 1.08 | 588 (M + H)+ |
| 1058 | 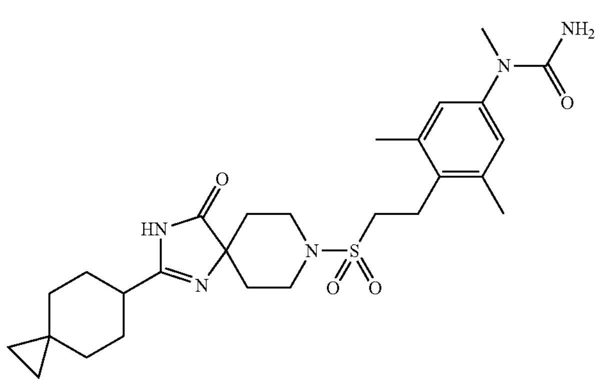 [SMILES: Cc1cc(N(C)C(N)=O)cc(C)c1CCS(=O)(=O)N1CCC2(CC1)N=C(C1CCC3(CC1)CC3)NC2=O] | LCMS-F-1 | 0.94 | 530 (M + H)+ |

The carboxylic acid reagent used in the synthesis of Compound 1051 (cis-3,4-dimethyl-cyclopentanecarboxylic acid) was synthesized by the following method.

(Reaction 247-3)

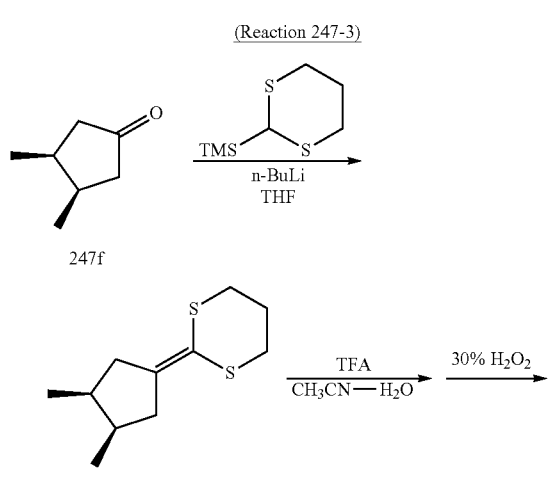

247f

247g

247h cis-3,4-Dimethyl-cyclopentanecarboxylic acid was synthesized by operations similar to those in Reaction 193-12 using appropriate reagents and starting material.

$^1$H-NMR (400 MHz, CDCl$_3$) δ 0.85 (3H, d, J=7.0 Hz), 0.89 (3H, d, J=7.0 Hz), 1.58-1.68 (2H, m), 2.00-2.15 (4H, m), 2.78 (0.4H, dd, J=17.2, 8.8 Hz), 2.92-3.00 (0.6H, m) (cis:trans=6:4).

The carboxylic acid reagent used in the synthesis of Compound 1052 (dicyclopropyl-acetic acid) was synthesized by the following method.

(Reaction 247-4)

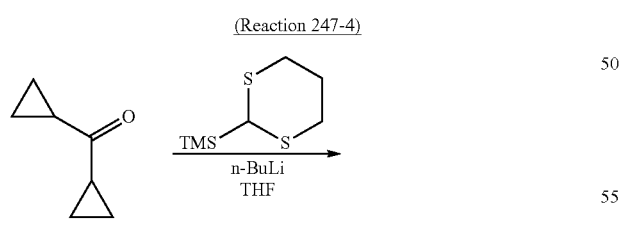

247i

247j

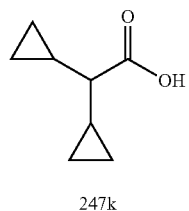

247k

Dicyclopropyl-acetic acid was synthesized by operations similar to those in Reaction 193-12 using appropriate reagents and starting material.

$^1$H-NMR (400 MHz, CDCl$_3$) δ 0.24-0.33 (4H, m), 0.48-0.52 (2H, m), 0.58-0.62 (2H, m), 1.05-1.10 (3H, m).

The carboxylic acid reagent used in the synthesis of Compound 1053 (bicyclo[3.3.1]nonane-9-carboxylic acid) was synthesized by the following method.

(Reaction 247-5)

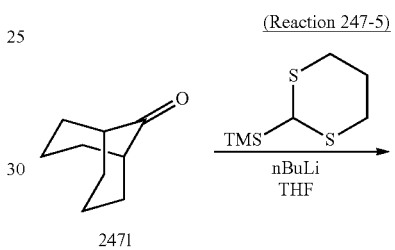

247l

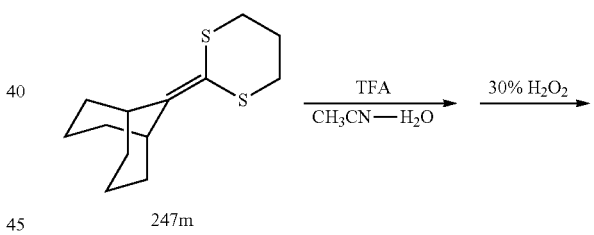

247m

247n

Bicyclo[3.3.1]nonane-9-carboxylic acid was synthesized by operations similar to those in Reaction 193-12 using appropriate reagents and starting material.

$^1$H-NMR (400 MHz, CDCl$_3$) δ 1.48-1.63 (4H, m), 1.70-1.80 (2H, m), 1.83-1.96 (6H, m), 2.33 (2H, br), 2.46 (1H, br).

The carboxylic acid reagent used in the synthesis of Compound 1057 (2-hexyl-cyclohexanecarboxylic acid) was synthesized by the following method.

(Reaction 247-6)

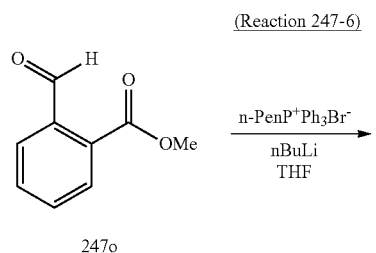

247o

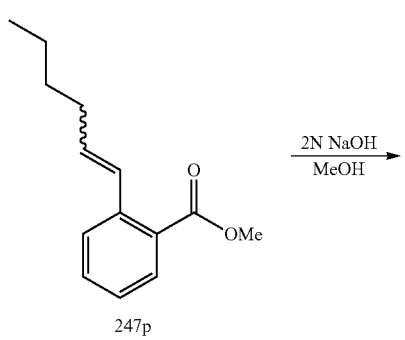

247p

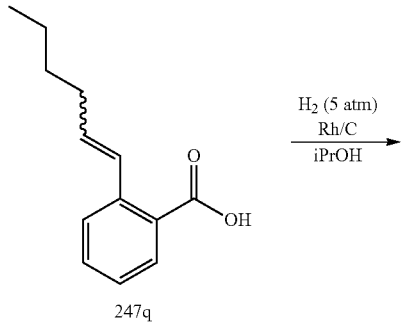

247q

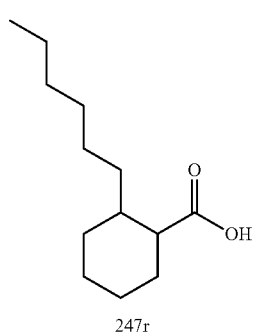

247r

2-Hexyl-cyclohexanecarboxylic acid was synthesized by operations similar to those in Reaction 101-1, Reaction 95-18 and Reaction 193-3 using appropriate reagents and starting material.

$^1$H-NMR (400 MHz, CDCl$_3$) δ 0.88 (3H, t, J=7.2 Hz), 1.20-1.55 (13H, m), 1.60-1.90 (6H, m), 2.56-2.59 (1H, m).

The carboxylic acid reagent used in the synthesis of Compound 1058 (spiro[2.5]octane-6-carboxylic acid) was synthesized by the following method.

(Reaction 247-7)

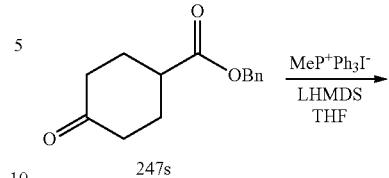

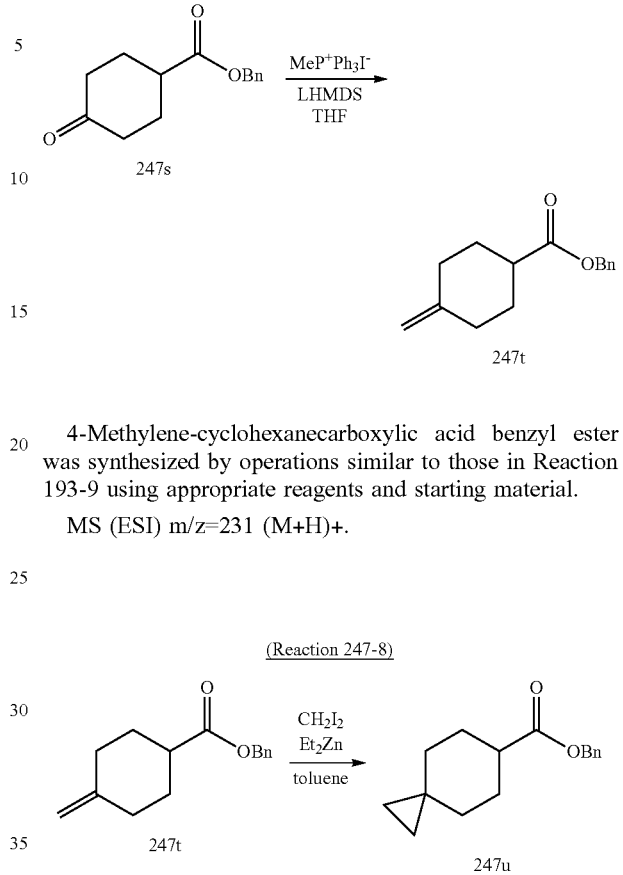

4-Methylene-cyclohexanecarboxylic acid benzyl ester was synthesized by operations similar to those in Reaction 193-9 using appropriate reagents and starting material.

MS (ESI) m/z=231 (M+H)+.

(Reaction 247-8)

Et$_2$Zn (1.08 M solution in hexane, 5.23 ml, 5.65 mmol) was added to a solution of 4-methylene-cyclohexanecarboxylic acid benzyl ester (86.3 mg, 375 μmol) in toluene (1.4 ml), and the mixture was stirred at room temperature for 30 minutes. CH$_2$I$_2$ (500 μl, 6.22 mmol) was added to the reaction mixture at 0° C., and the mixture was stirred at 60° C. for 28 hours. Thereafter, Et$_2$Zn (1.08 M solution in hexane, 2.60 ml, 2.22 mmol) and CH$_2$I$_2$ (260 μl, 3.23 mmol) were added to the reaction mixture, and the mixture was stirred at 60° C. for four days. Further, Et$_2$Zn (1.08 M solution in hexane, 2.60 ml, 2.22 mmol) and CH$_2$I$_2$ (500 μl, 6.22 mmol) were added to the reaction mixture, and the mixture was stirred at 60° C. for one day. The reaction mixture was quenched by adding a 1% aqueous HCl solution and diluted with ethyl acetate and Et$_2$O. The organic layer was then washed with a 1% aqueous HCl solution, a saturated aqueous sodium bicarbonate solution and saturated brine, and then dried over MgSO$_4$ and concentrated under reduced pressure. The resulting residue was purified by silica gel column chromatography (hexane/ethyl acetate=100/0→65/35) to give spiro[2.5]octane-6-carboxylic acid benzyl ester (70.6 mg, 77%).

$^1$H-NMR (400 MHz, CDCl$_3$) δ 0.19-0.22 (2H, m), 0.26-0.30 (2H, m), 0.94-1.00 (2H, m), 1.60-1.72 (4H, m), 1.90-1.95 (2H, m), 2.37-2.42 (1H, m), 5.12 (2H, s), 7.30-7.38 (5H, m).

1203
(Reaction 247-9)
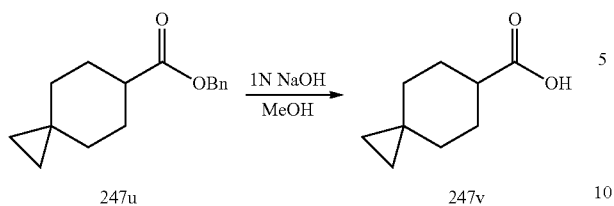
Spiro[2.5]octane-6-carboxylic acid was synthesized by operations similar to those in Reaction 95-18 using appropriate reagents and starting material.
1204
$^1$H-NMR (400 MHz, CDCl$_3$) δ 0.19-0.24 (2H, m), 0.28-0.30 (2H, m), 0.97-1.03 (2H, m), 1.60-1.72 (4H, m), 1.92-1.95 (2H, m), 2.35-2.42 (1H, m).
Example 248
1-(4-{2-[2-(4-Difluoromethylene-cyclohexyl)-4-oxo-1,3,8-triaza-spiro[4.5]dec-1-ene-8-sulfonyl]-ethyl}-3,5-dimethyl-phenyl)-1-methyl-urea (Compound 1059)
(Reaction 248-1)
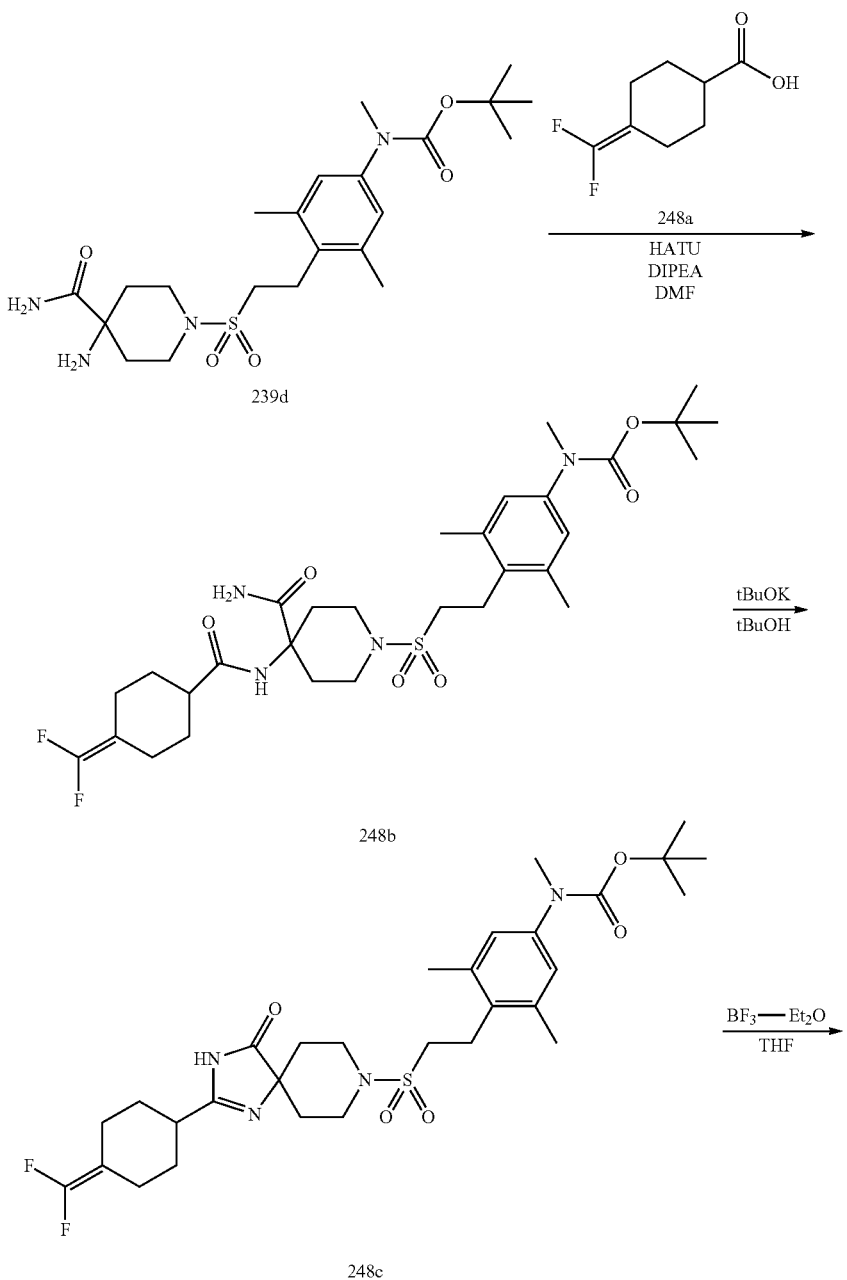

-continued

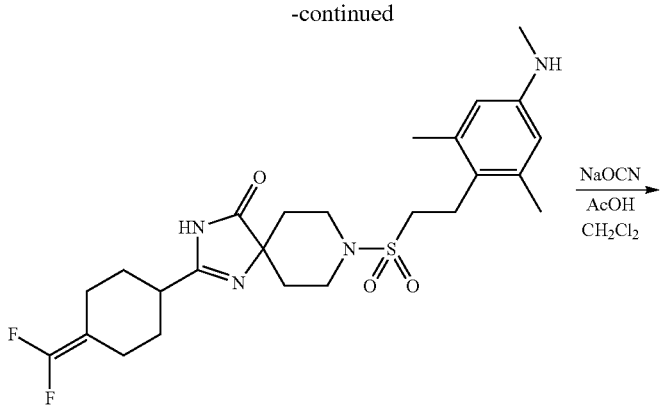

248d

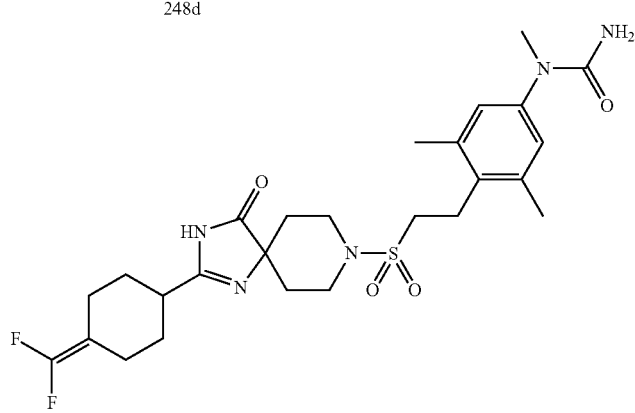

Compound 1059

1-(4-{2-[2-(4-Difluoromethylene-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 10-12, Reaction 241-2 and Reaction 89-2 using appropriate reagents and starting material.

MS (ESI) m/z=552 (M+H)+.

The carboxylic acid reagent used in the synthesis of Compound 1059 (4-difluoromethylene-cyclohexanecarboxylic acid) was synthesized by the following method.

(Reaction 248-2)

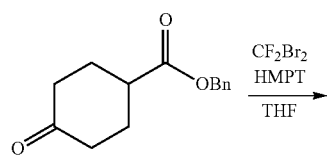

247s

HMPT (7.40 ml, 39.5 mmol) was added to a solution of 4-oxo-cyclohexanecarboxylic acid benzyl ester (1.50 g, 6.59 mmol) and $CF_2Br_2$ (1.8 ml, 19.8 mmol) in THF (30 ml) at 0° C., and the reaction mixture was stirred at room temperature for 22 hours. Water was added, followed by extraction with ethyl acetate. The organic layer was then dried over $MgSO_4$ and concentrated under reduced pressure. The resulting residue was purified by silica gel column chromatography (hexane/ethyl acetate=100/0→75/25) to give 4-difluoromethylene-cyclohexanecarboxylic acid benzyl ester (166 mg, 9%).

$^1$H-NMR (400 MHz, $CDCl_3$) δ 1.57 (2H, ddd, J=12, 12, 4 Hz), 1.80-1.90 (2H, m), 1.97-2.05 (2H, m), 2.43-2.49 (3H, m), 5.12 (2H, s), 7.32-7.40 (5H, m).

(Reaction 248-3)

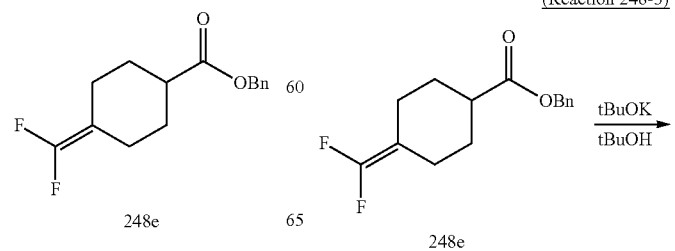

248e    248e

-continued

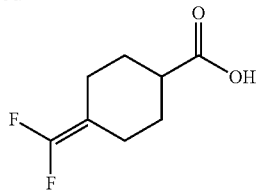

248a

4-Difluoromethylene-cyclohexanecarboxylic acid was synthesized by operations similar to those in Reaction 215-2 using appropriate reagents and starting material.

$^1$H-NMR (400 MHz, CDCl$_3$) δ 1.52-1.63 (2H, m), 1.85-1.94 (2H, m), 1.97-2.05 (2H, m), 2.43-2.49 (3H, m).

Example 249

N-[4-(2-{2-[4-(2,2-Difluoro-ethyl)-cyclohexyl]-4-oxo-1,3,8-triaza-spiro[4.5]dec-1-ene-8-sulfonyl}-ethyl)-3-methyl-phenyl]-acetamide (Compound 1060)

(Reaction 249-1)

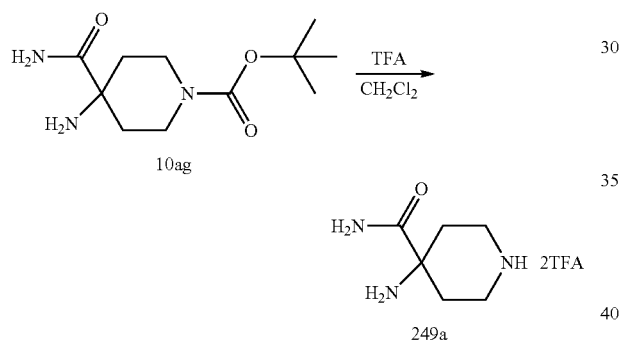

Trifluoroacetic acid (6.17 mL, 83.0 mmol) was added to a solution of 4-amino-4-carbamoyl-piperidine-1-carboxylic acid tert-butyl ester (2.02 g, 8.30 mmol) in dichloromethane (16.6 mL), and the mixture was stirred at room temperature for 1.5 hours. The reaction solution was concentrated under reduced pressure. The residue was dissolved in methanol (2.00 mL), repeatedly concentrated under reduced pressure twice and dried under reduced pressure to give 4-amino-piperidine-4-carboxylic amide 2TFA salt as a colorless substance (3.25 g).

$^1$H-NMR (400 MHz, CD$_3$OD) δ 2.10-2.19 (2H, br-m), 2.56-2.65 (2H, m), 3.34-3.45 (4H, m).

(Reaction 249-2)

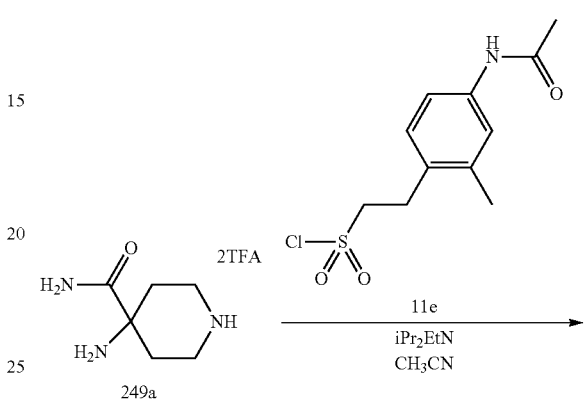

1-[2-(4-Acetylamino-2-methyl-phenyl)-ethanesulfonyl]-4-amino-piperidine-4-carboxylic amide was synthesized by operations similar to those in Reaction 5-4 using appropriate reagents and starting material.

MS (ESI) m/z=383 (M+H)+.

(Reaction 249-3)

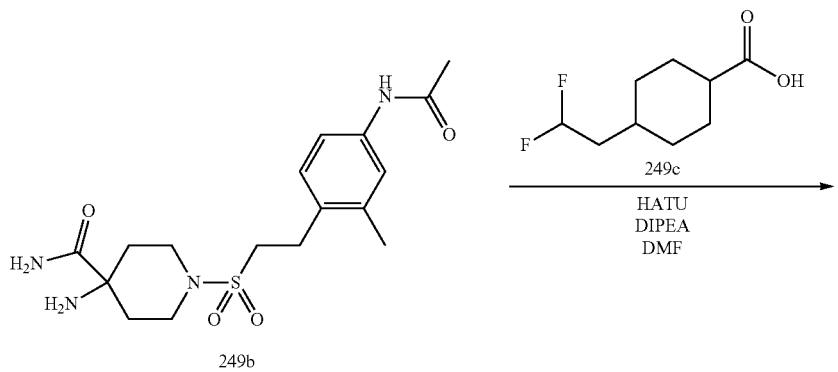

-continued

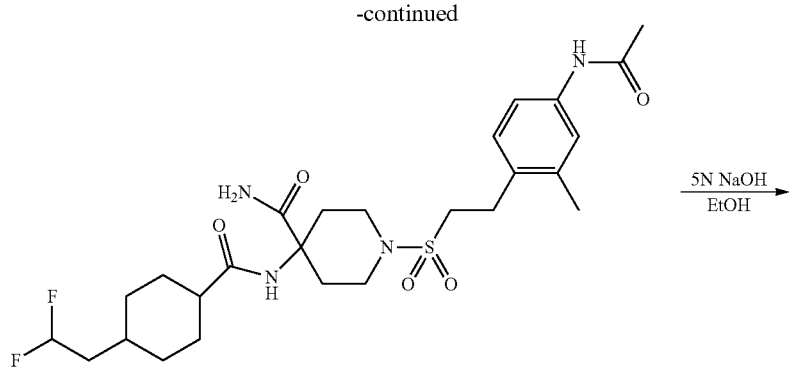

249d

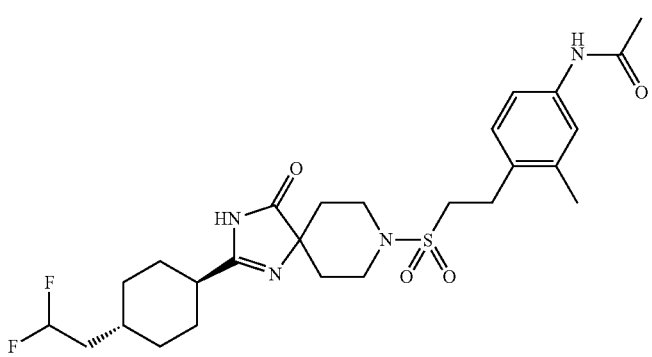 [SMILES: CC(=O)Nc1ccc(CCS(=O)(=O)N2CCC3(CC2)N=C([C@H]2CC[C@H](CCF)CC2)NC3=O)c(C)c1]

Compound 1060

N-[4-(2-{2-[4-(2,2-Difluoro-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 189-5 using appropriate reagents and starting material.

MS (ESI) m/z=539 (M+H)+.

The carboxylic acid reagent used in the synthesis of Compound 1060 (4-(2,2-difluoro-ethyl)-cyclohexanecarboxylic acid) was synthesized by the following method.

(Reaction 249-4)

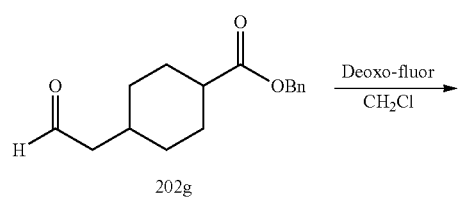

202g

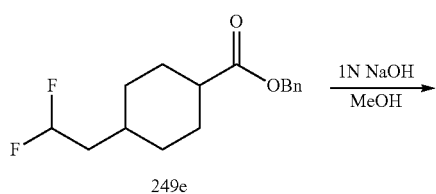

249e

-continued

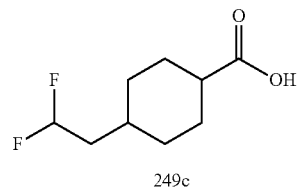

249c 4-(2,2-Difluoro-ethyl)-cyclohexanecarboxylic acid was synthesized by operations similar to those in Reaction 191-11 and Reaction 95-18 using appropriate reagents and starting material.

$^{1}$H-NMR (400 MHz, CDCl$_3$) δ 1.00-2.04 (11H, m), 2.27 (0.25H, tt, J=12.4, 3.2 Hz), 2.60-2.64 (0.75H, m), 5.68-6.01 (1H, m) (cis:trans=3:1).

The example compounds shown below were synthesized by operations similar to those in Reaction 249-3 using appropriate reagents and starting materials.

1211

Compounds 1061 to 1063

TABLE 158

| Compound | Structure | LCMS condition | Retention time (min) | MS (m/z) |
|---|---|---|---|---|
| 1061 | 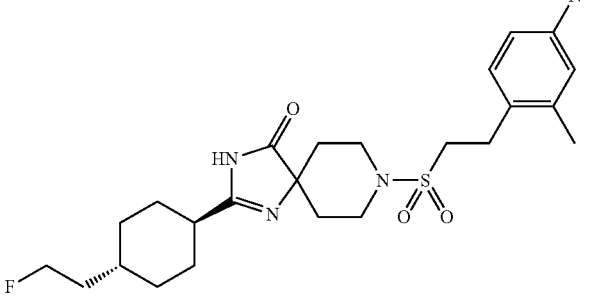 | LCMS-C-1 | 2.40 | 521 (M + H)+ |
| 1062 | 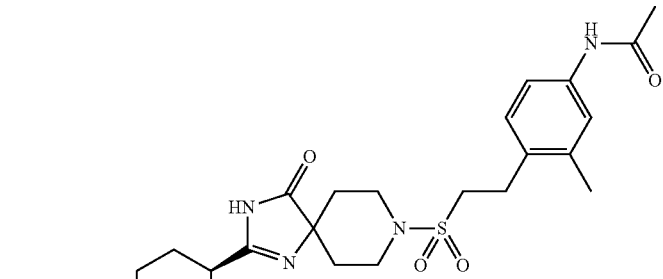 | LCMS-B-1 | 1.98 | 549 (M + H)+ |
| 1063 | 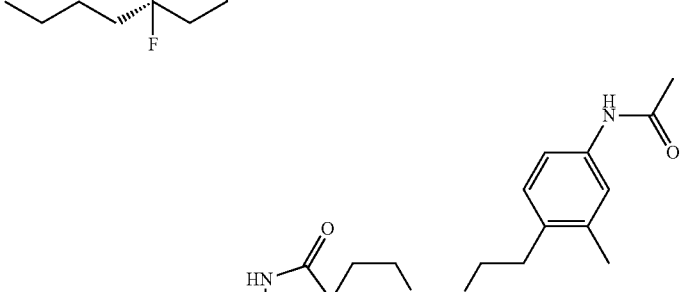 | LCMS-B-1 | 1.76 | 533 (M + H)+ |

1212

The carboxylic acid reagent used in the synthesis of Compound 1061 (4-(2-fluoro-ethyl)-cyclohexanecarboxylic acid) was synthesized by the following method.

(Reaction 249-5)

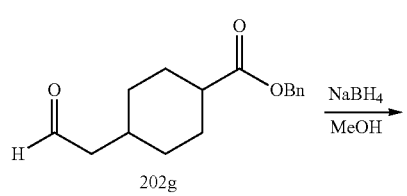

202g

-continued

249f

Sodium borohydride (89 mg, 2.35 mmol) was added to a solution of 4-(2-oxo-ethyl)-cyclohexanecarboxylic acid benzyl ester (306 mg, 1.18 mmol) in methanol (6 ml) at 0° C. The mixture was stirred at 0° C. for one hour, and then quenched with a saturated aqueous ammonium chloride solution and extracted with ethyl acetate. The organic layer was sequentially washed with water and saturated brine, and then dried over anhydrous sodium sulfate and concentrated under reduced pressure. The resulting residue was purified by silica gel column chromatography to give 4-(2-hydroxy-ethyl)-cyclohexanecarboxylic acid benzyl ester (299 mg).

¹H-NMR (400 MHz, CDCl₃) δ 1.20-1.32 (2H, m), 1.40-1.63 (9H, m), 1.95-2.05 (2H, m), 2.25-2.33 (0.2H, m), 2.55-2.62 (0.8H, m), 3.67 (1.6H, t, J=6.8 Hz), 3.69 (0.4H, t, J=6.4 Hz), 7.30-7.40 (5H, m) (cis:trans=4:1).

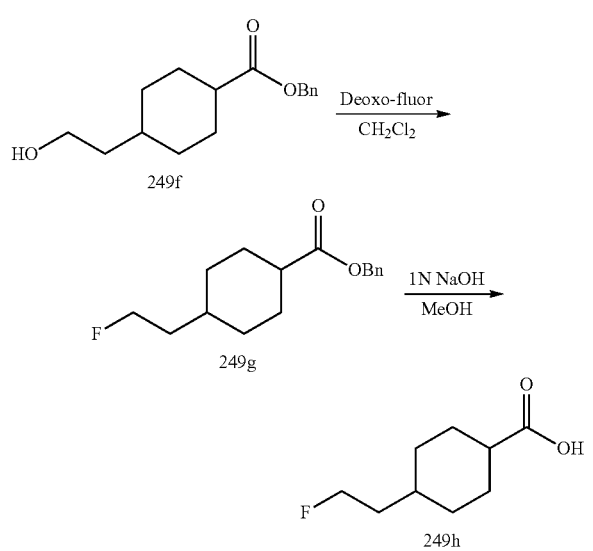

4-(2-Fluoro-ethyl)-cyclohexanecarboxylic acid was synthesized by operations similar to those in Reaction 191-11 and Reaction 95-18 using appropriate reagents and starting material.

¹H-NMR (400 MHz, CDCl₃) δ 0.93-2.03 (11H, m), 2.26 (0.2H, tt, J=12.0, 3.2 Hz), 2.57-2.62 (0.8H, m), 4.39-4.56 (2H, m) (cis:trans=4:1).

The carboxylic acid reagent used in the synthesis of Compound 1062 (4-butyl-4-fluoro-cyclohexanecarboxylic acid) was synthesized by the following method.

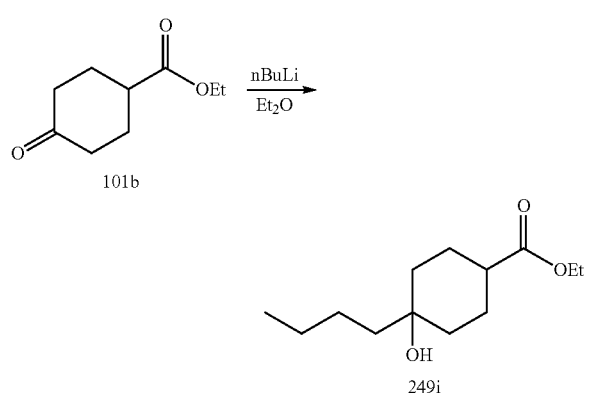

A 2.6 M solution of n-BuLi in THF (681 μl, 1.77 mmol) was added to a solution of 4-oxo-cyclohexanecarboxylic acid ethyl ester (186 μl, 1.18 mmol) in Et₂O (4.0 ml) at −60° C. in an N₂ atmosphere, and the mixture was stirred at −60° C. for four hours. The reaction mixture was quenched by adding water and then diluted with ethyl acetate. The organic layer was washed with water, and then dried over MgSO₄ and concentrated under reduced pressure. The resulting residue was used in the next step without purification.

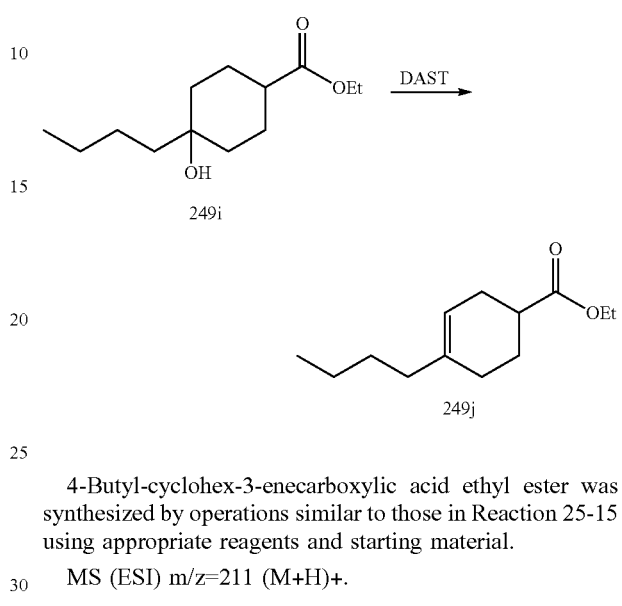

4-Butyl-cyclohex-3-enecarboxylic acid ethyl ester was synthesized by operations similar to those in Reaction 25-15 using appropriate reagents and starting material.

MS (ESI) m/z=211 (M+H)+.

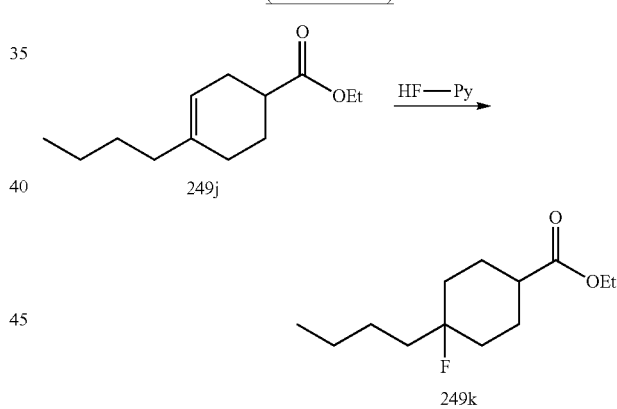

HF.Py (0.5 ml) was added to 4-butyl-cyclohex-3-enecarboxylic acid ethyl ester (43.0 mg, 205 μmol) at room temperature, and the reaction mixture was stirred at room temperature for two hours. The reaction mixture was diluted by adding dichloromethane and then quenched by adding a saturated aqueous sodium bicarbonate solution and solid sodium bicarbonate at 0° C. The organic layer was washed with 2 N HCl, and then dried over MgSO₄ and concentrated under reduced pressure. The resulting residue was purified by silica gel column chromatography (hexane/ethyl acetate=100/0→97/3) to give 4-butyl-4-fluoro-cyclohexanecarboxylic acid ethyl ester (22.5 mg, 48%, cis:trans=1:3).

¹H-NMR (400 MHz, CDCl₃) δ 0.91 (3H, t, J=8.0 Hz), 1.25 (3H, t, J=8.0 Hz), 1.28-1.38 (6H, m), 1.51-1.84 (6H, m), 1.84-2.00 (2H, m), 2.20-2.26 (0.75H, m), 2.48-2.54 (0.25H, m), 4.10-4.16 (2H, m).

1215

(Reaction 249-10)

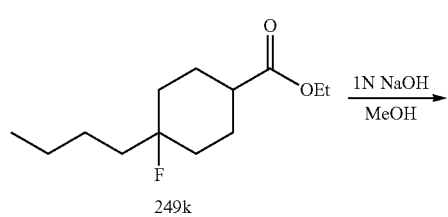

4-Butyl-4-fluoro-cyclohexanecarboxylic acid was synthesized by operations similar to those in Reaction 95-18 using appropriate reagents and starting material.

$^1$H-NMR (400 MHz, CDCl$_3$) δ 0.91 (3H, t, J=7.0 Hz), 1.25-1.46 (6H, m), 1.50-1.62 (2H, m), 1.69-2.05 (6H, m), 2.25-2.35 (0.75H, m), 2.58-2.70 (0.25H, m).

The carboxylic acid reagent used in the synthesis of Compound 1063 (4-((E)-3-fluoro-propenyl)-cyclohexanecarboxylic acid) was synthesized by the following method.

(Reaction 249-11)

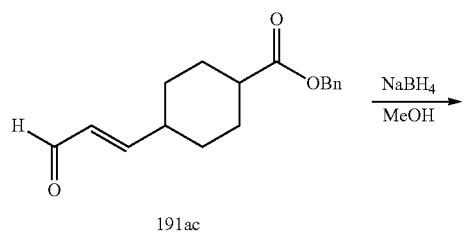

1216

-continued

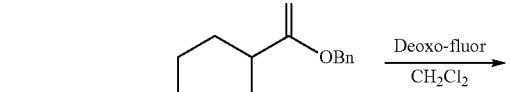

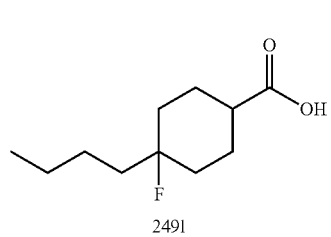

4-((E)-3-Fluoro-propenyl)-cyclohexanecarboxylic acid was synthesized by operations similar to those in Reaction 249-5, Reaction 191-11 and Reaction 95-18 using appropriate reagents and starting material. This was used in the next step without complete purification.

Example 250

N-[4-(2-{2-[4-(3-Fluoro-propyl)-cyclohexyl]-4-oxo-1,3,8-triaza-spiro[4.5]dec-1-ene-8-sulfonyl}-ethyl)-3-methyl-phenyl]-acetamide (Compound 1064)

and N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide (Compound 1065)

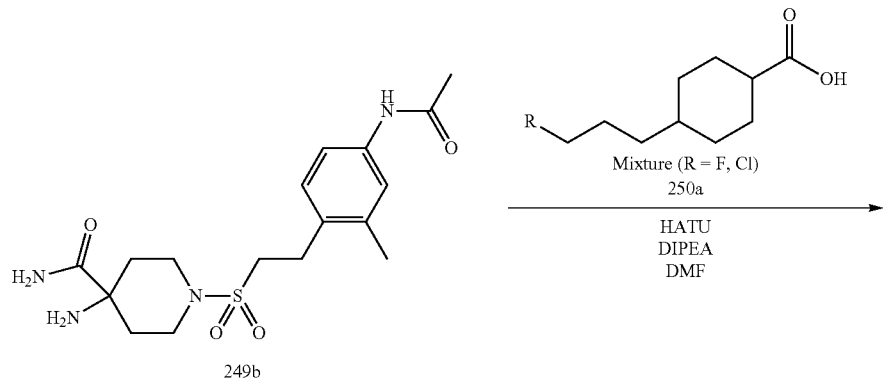

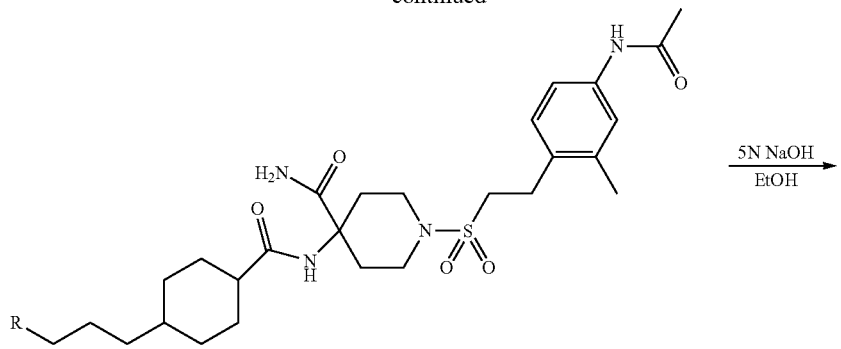

Mixture (R = F, Cl)
250b

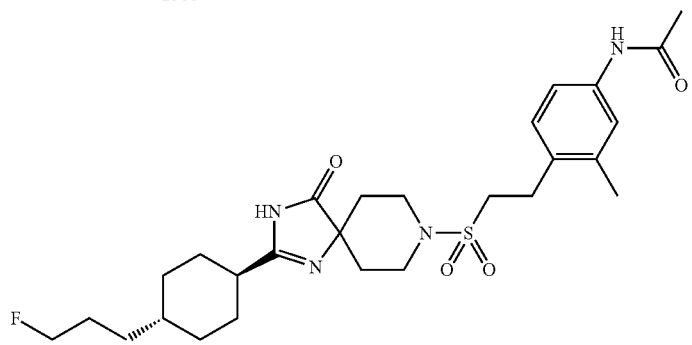

Compound 1064

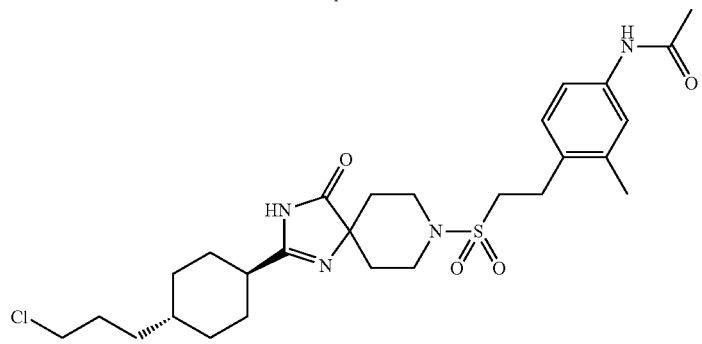

Compound 1065

N-[4-(2-{2-[4-(3-Fluoro-propyl)-cyclohexyl]-4-oxo-1,3,8-triaza-spiro[4.5]dec-1-ene-8-sulfonyl}-ethyl)-3-methyl-phenyl]-acetamide MS (ESI) m/z=535 (M+H)+ and N-[4-(2-{2-[4-(3-chloro-propyl)-cyclohexyl]-4-oxo-1,3,8-triaza-spiro[4.5]dec-1-ene-8-sulfonyl}-ethyl)-3-methyl-phenyl]-acetamide MS (ESI) m/z=551 (M+H)+ were synthesized by operations similar to those in Reaction 10-14 and Reaction 189-5 using appropriate reagents and starting material.

The carboxylic acid reagent used in the synthesis of Compound 1064 and Compound 1065 (a mixture of 4-(3-fluoro-propyl)-cyclohexanecarboxylic acid and 4-(3-chloro-propyl)-cyclohexanecarboxylic acid) was synthesized by the following method.

(Reaction 250-2)

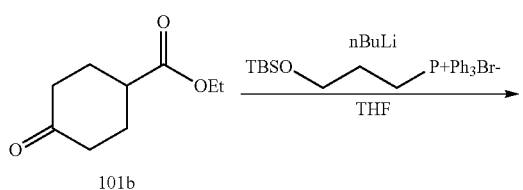

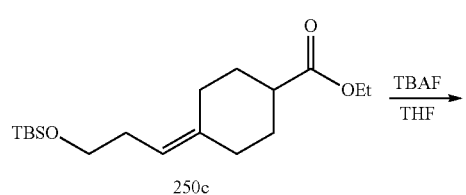

1219

1220

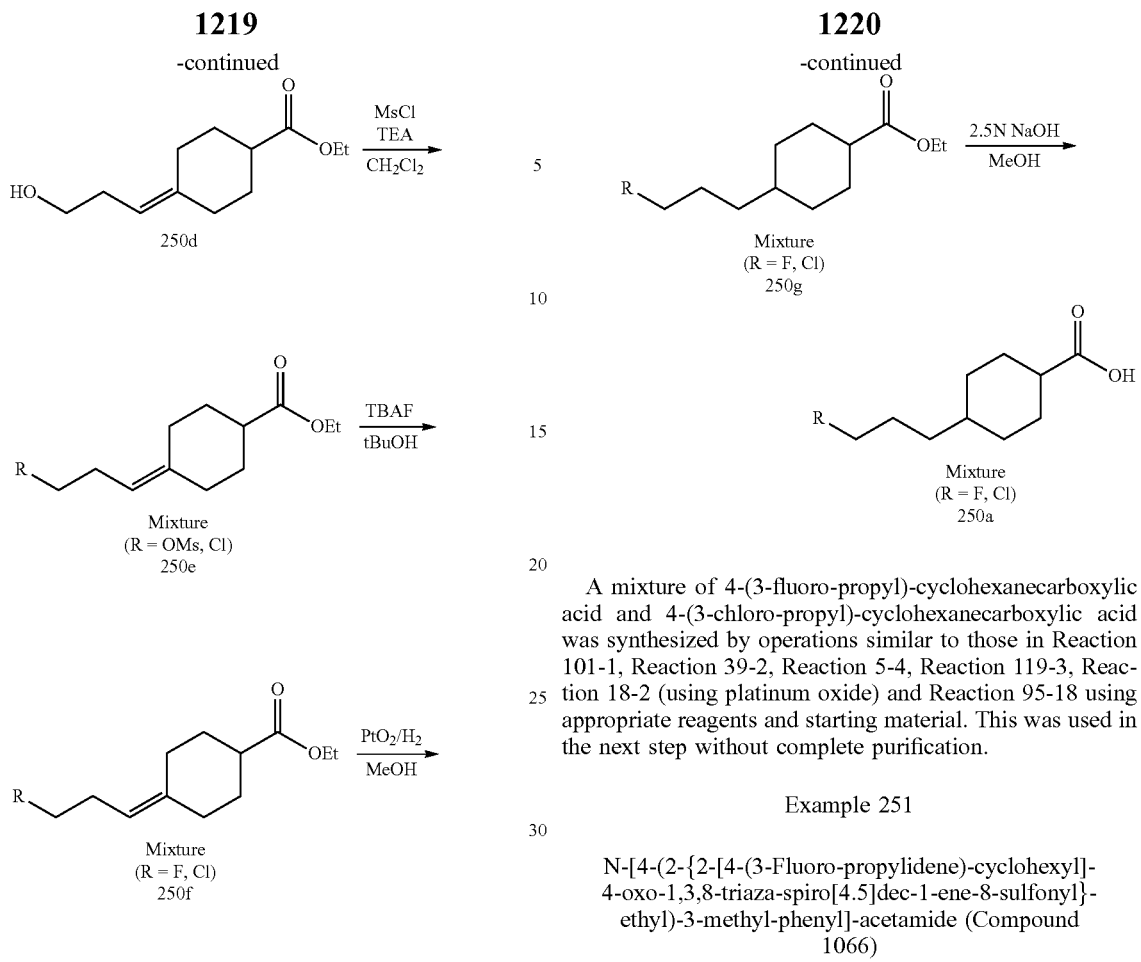

A mixture of 4-(3-fluoro-propyl)-cyclohexanecarboxylic acid and 4-(3-chloro-propyl)-cyclohexanecarboxylic acid was synthesized by operations similar to those in Reaction 101-1, Reaction 39-2, Reaction 5-4, Reaction 119-3, Reaction 18-2 (using platinum oxide) and Reaction 95-18 using appropriate reagents and starting material. This was used in the next step without complete purification.

Example 251

N-[4-(2-{2-[4-(3-Fluoro-propylidene)-cyclohexyl]-4-oxo-1,3,8-triaza-spiro[4.5]dec-1-ene-8-sulfonyl}-ethyl)-3-methyl-phenyl]-acetamide (Compound 1066)

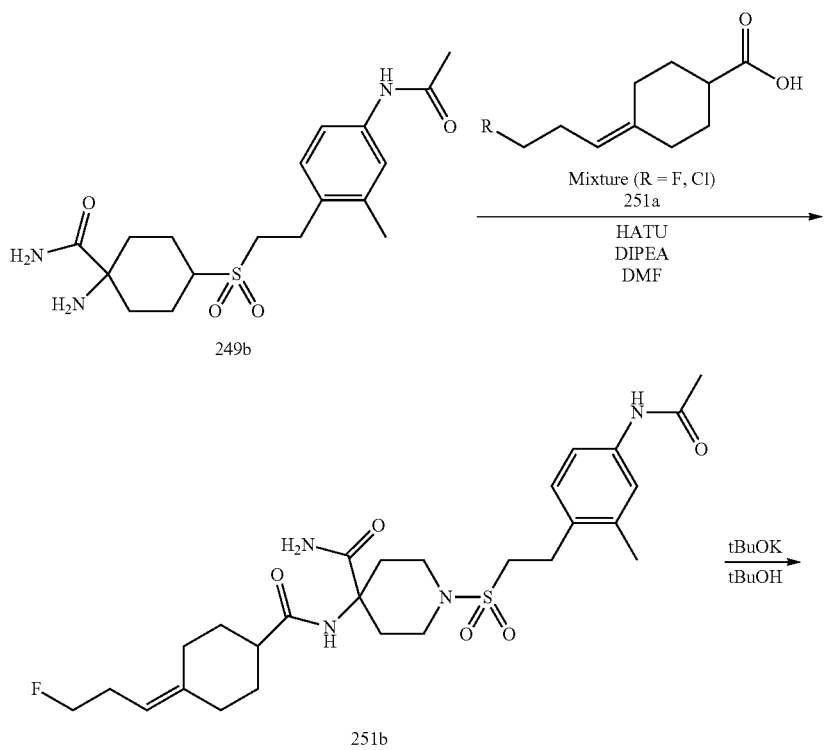

-continued

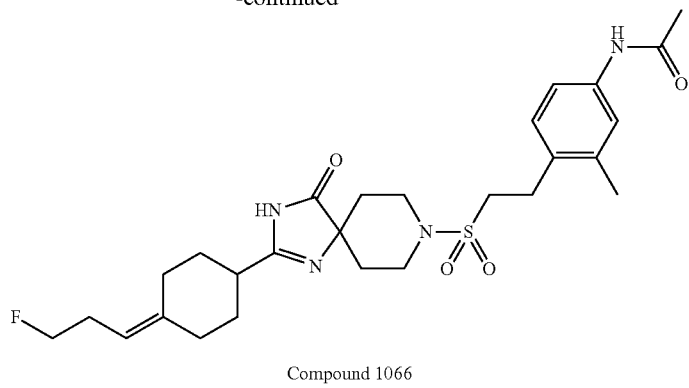

Compound 1066

N-[4-(2-{2-[4-(3-Fluoro-propylidene)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 10-12 using appropriate reagents and starting material.

MS (ESI) m/z=533 (M+H)+.

The example compounds shown below were synthesized by operations similar to those in Reaction 251-1 using appropriate reagents and starting materials.

Compounds 1067 to 1077

TABLE 159

| Compound | Structure | LCMS condition | Retention time (min) | MS (m/z) |
|---|---|---|---|---|
| 1067 | 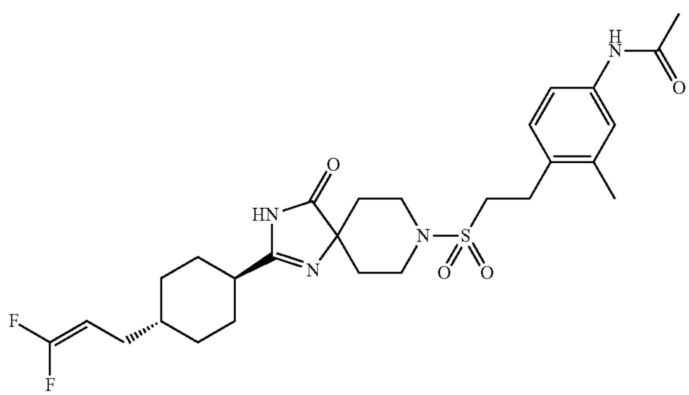 [SMILES: CC(=O)Nc1ccc(CCS(=O)(=O)N2CCC3(CC2)N=C([C@H]2CC[C@H](CC=C(F)F)CC2)NC3=O)c(C)c1] | LCMS-C-2 | 2.00 | 551 (M + H)+ |
| 1068 | 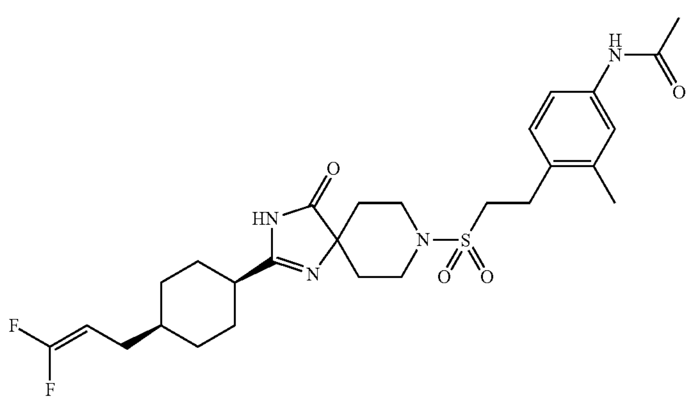 [SMILES: CC(=O)Nc1ccc(CCS(=O)(=O)N2CCC3(CC2)N=C([C@H]2CC[C@@H](CC=C(F)F)CC2)NC3=O)c(C)c1] | LCMS-C-2 | 2.03 | 551 (M + H)+ |

TABLE 159-continued

| Compound | Structure | LCMS condition | Retention time (min) | MS (m/z) |
|---|---|---|---|---|
| 1069 | 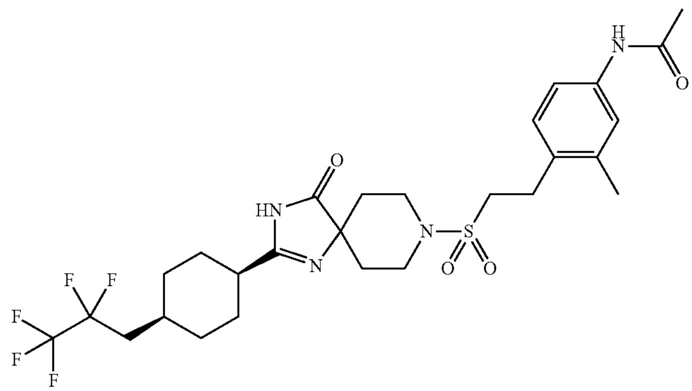 [SMILES: CC(=O)Nc1ccc(CCS(=O)(=O)N2CCC3(CC2)N=C([C@H]2CC[C@@H](CC(F)(F)C(F)(F)F)CC2)NC3=O)c(C)c1] | LCMS-C-2 | 2.08 | 607 (M + H)+ |
| 1070 | 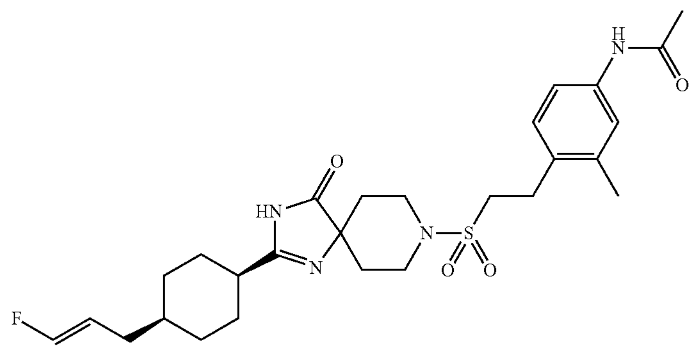 [SMILES: CC(=O)Nc1ccc(CCS(=O)(=O)N2CCC3(CC2)N=C([C@H]2CC[C@@H](C/C=C/F)CC2)NC3=O)c(C)c1] | LCMS-B-1 | 1.84 | 533 (M + H)+ |
| 1071 | 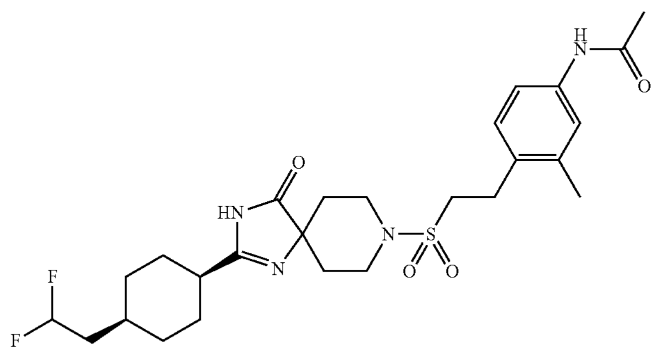 [SMILES: CC(=O)Nc1ccc(CCS(=O)(=O)N2CCC3(CC2)N=C([C@H]2CC[C@@H](CC(F)F)CC2)NC3=O)c(C)c1] | LCMS-C-1 | 2.43 | 539 (M + H)+ |
| 1072 | 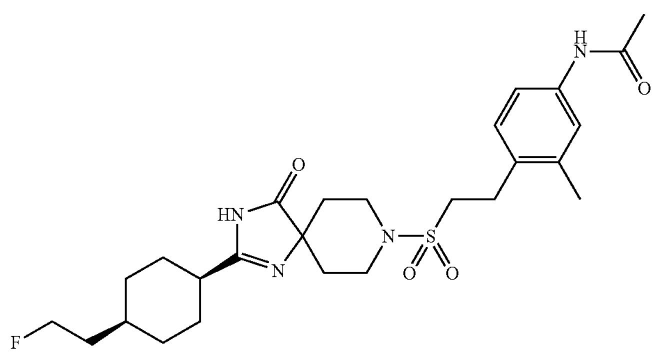 [SMILES: CC(=O)Nc1ccc(CCS(=O)(=O)N2CCC3(CC2)N=C([C@H]2CC[C@@H](CCF)CC2)NC3=O)c(C)c1] | LCMS-C-1 | 2.40 | 521 (M + H)+ |

TABLE 159-continued

| Compound | Structure | LCMS condition | Retention time (min) | MS (m/z) |
|---|---|---|---|---|
| 1073 | 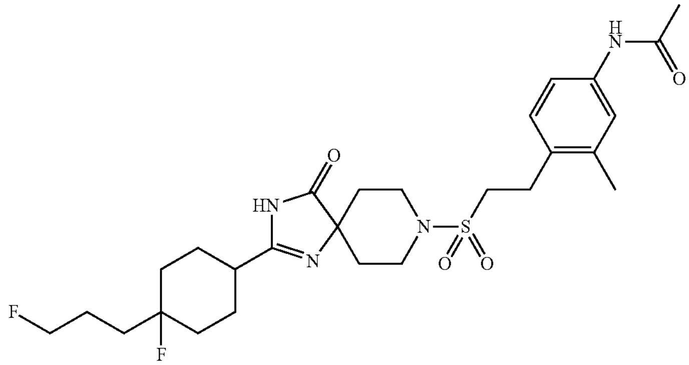 [SMILES: CC(=O)Nc1ccc(CCS(=O)(=O)N2CCC3(CC2)N=C(C2CCC(F)(CCCF)CC2)NC3=O)c(C)c1] | LCMS-F-1 | 0.87 | 553 (M + H)+ |
| 1074 | 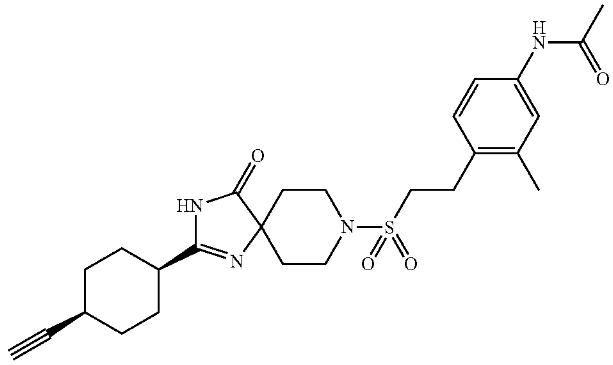 [SMILES: C#C[C@H]1CC[C@@H](C2=NC3(CCN(S(=O)(=O)CCc4ccc(NC(C)=O)cc4C)CC3)C(=O)N2)CC1] | LCMS-B-1 | 1.63 | 499 (M + H)+ |
| 1075 | 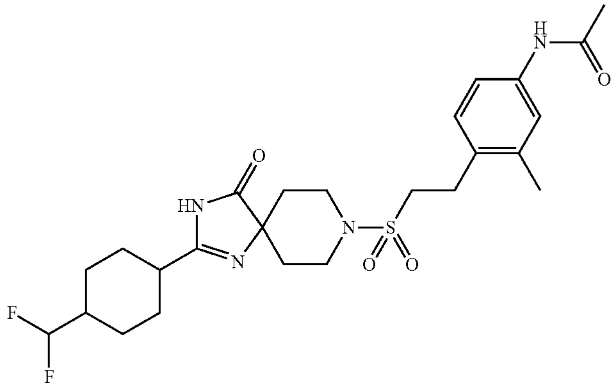 [SMILES: CC(=O)Nc1ccc(CCS(=O)(=O)N2CCC3(CC2)N=C(C2CCC(C(F)F)CC2)NC3=O)c(C)c1] | LCMS-F-1 | 0.85 | 525 (M + H)+ |
| 1076 | 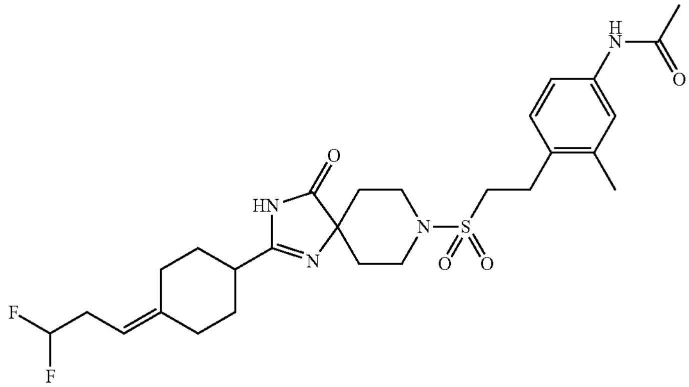 [SMILES: CC(=O)Nc1ccc(CCS(=O)(=O)N2CCC3(CC2)N=C(C2CCC(=CCC(F)F)CC2)NC3=O)c(C)c1] | LCMS-B-1 | 1.79 | 551 (M + H)+ |

TABLE 159-continued

| Compound | Structure | LCMS condition | Retention time (min) | MS (m/z) |
|---|---|---|---|---|
| 1077 | 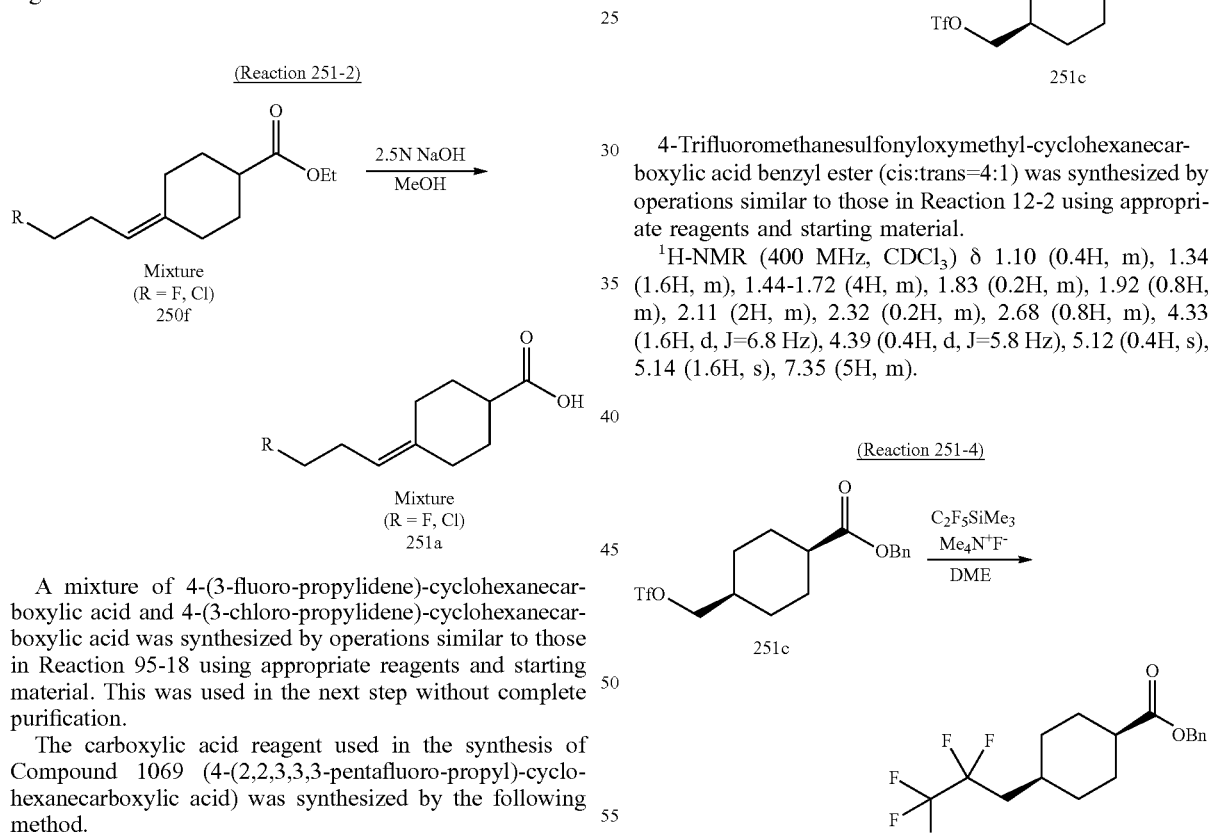 | LCMS-F-1 | 0.91 | 535 (M + H)+ |

The carboxylic acid reagent used in the synthesis of Compound 1066 (a mixture of 4-(3-fluoro-propylidene)-cyclohexanecarboxylic acid and 4-(3-chloro-propylidene)-cyclohexanecarboxylic acid) was synthesized by the following method.

(Reaction 251-2)

A mixture of 4-(3-fluoro-propylidene)-cyclohexanecarboxylic acid and 4-(3-chloro-propylidene)-cyclohexanecarboxylic acid was synthesized by operations similar to those in Reaction 95-18 using appropriate reagents and starting material. This was used in the next step without complete purification.

The carboxylic acid reagent used in the synthesis of Compound 1069 (4-(2,2,3,3,3-pentafluoro-propyl)-cyclohexanecarboxylic acid) was synthesized by the following method.

(Reaction 251-3)

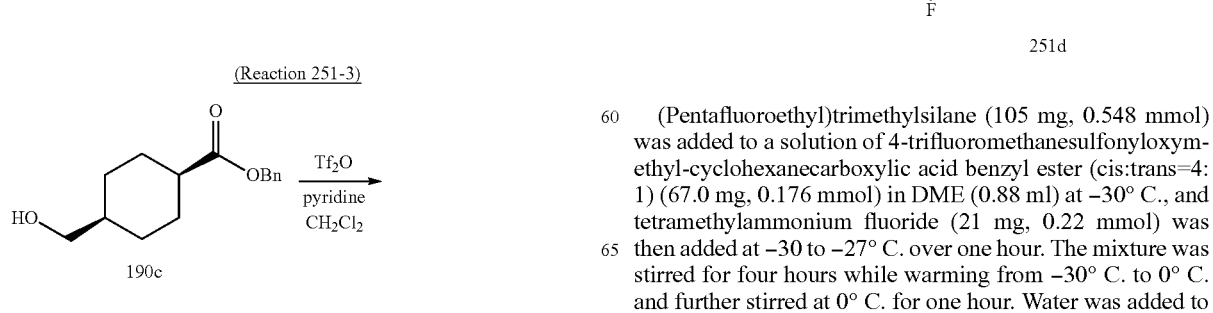

4-Trifluoromethanesulfonyloxymethyl-cyclohexanecarboxylic acid benzyl ester (cis:trans=4:1) was synthesized by operations similar to those in Reaction 12-2 using appropriate reagents and starting material.

$^1$H-NMR (400 MHz, CDCl$_3$) δ 1.10 (0.4H, m), 1.34 (1.6H, m), 1.44-1.72 (4H, m), 1.83 (0.2H, m), 1.92 (0.8H, m), 2.11 (2H, m), 2.32 (0.2H, m), 2.68 (0.8H, m), 4.33 (1.6H, d, J=6.8 Hz), 4.39 (0.4H, d, J=5.8 Hz), 5.12 (0.4H, s), 5.14 (1.6H, s), 7.35 (5H, m).

(Reaction 251-4)

(Pentafluoroethyl)trimethylsilane (105 mg, 0.548 mmol) was added to a solution of 4-trifluoromethanesulfonyloxymethyl-cyclohexanecarboxylic acid benzyl ester (cis:trans=4:1) (67.0 mg, 0.176 mmol) in DME (0.88 ml) at −30° C., and tetramethylammonium fluoride (21 mg, 0.22 mmol) was then added at −30 to −27° C. over one hour. The mixture was stirred for four hours while warming from −30° C. to 0° C. and further stirred at 0° C. for one hour. Water was added to the reaction mixture, followed by extraction with dichloromethane. The organic layer was then dried over MgSO$_4$ and concentrated under reduced pressure. The resulting residue was purified by silica gel column chromatography (hexane/ethyl acetate=150/1) to give 4-(2,2,3,3,3-pentafluoro-propyl)-cyclohexanecarboxylic acid benzyl ester (cis:trans=11:1) (11.4 mg, 18%).

$^1$H-NMR (400 MHz, CDCl$_3$) δ 1.32-1.75 (6H, m), 1.80-2.10 (5H, m), 2.26 (0.08H, m), 2.61 (0.92H, m), 5.13 (2H, s), 7.35 (5H, m).

(Reaction 251-5)

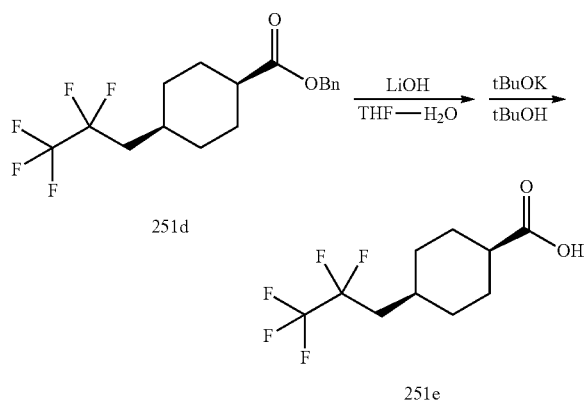

LiOH.H$_2$O (3.8 mg, 0.091 mmol) was added to a solution of 4-(2,2,3,3,3-pentafluoro-propyl)-cyclohexanecarboxylic acid benzyl ester (cis:trans=11:1) (11.4 mg, 0.0325 mmol) in THF (0.15 ml)-H$_2$O (0.15 mL). The mixture was stirred at room temperature for 16 hours, and then adjusted to pH 2 with a 1 N aqueous HCl solution and extracted with dichloromethane. The organic layer was dried over MgSO$_4$ and concentrated under reduced pressure. The resulting residue was dissolved in tert-butanol (0.4 ml), and potassium tert-butoxide (10 mg, 0.089 mmol) was added. The mixture was stirred at room temperature for two hours, and then adjusted to pH 3 with a 1 N aqueous HCl solution and extracted with dichloromethane. The organic layer was then dried over MgSO$_4$ and concentrated under reduced pressure. The resulting residue was purified by column chromatography (hexane/ethyl acetate=5/1) to give 4-(2,2,3,3,3-pentafluoro-propyl)-cyclohexanecarboxylic acid (cis:trans=9:1) (8.5 mg, 100%).

$^1$H-NMR (400 MHz, CDCl$_3$) δ 1.11 (0.2H, m), 1.30-1.78 (5.8H, m), 1.83-2.10 (5H, m), 2.26 (0.1H, m), 2.64 (0.9H, m).

The carboxylic acid reagent used in the synthesis of Compound 1070 (4-((E)-3-fluoro-allyl)-cyclohexanecarboxylic acid) was synthesized by the following method.

(Reaction 251-6)

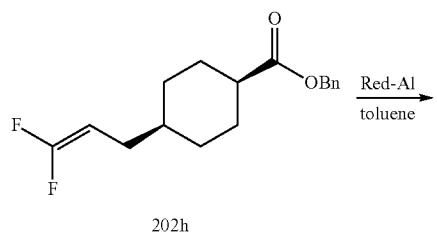

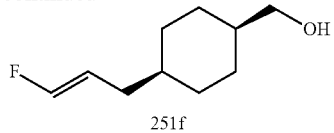

A 3.3 M Red-Al solution in toluene (0.25 ml, 0.82 mmol) was added to a solution of 4-(3,3-difluoro-allyl)-cyclohexanecarboxylic acid benzyl ester (cis:trans=5.4:1) (42.8 mg, 0.145 mmol) in toluene (0.12 mL), and the mixture was stirred at 85° C. for 17 hours. The reaction mixture was poured into ice water, adjusted to pH 3 with a 4 N aqueous H$_2$SO$_4$ solution and extracted with ether. The organic layer was dried over MgSO$_4$ and concentrated under reduced pressure to give [4-((E)-3-fluoro-allyl)-cyclohexyl]-methanol (25.0 mg, 100%).

$^1$H-NMR (400 MHz, CDCl$_3$) δ 0.92 (0.84H, m), 1.20-1.84 (9.16H, m), 1.87 (1.68H, dd, J=7.8, 6.8 Hz), 2.10 (0.32H, t, J=7.3 Hz), 3.45 (0.32H, d, J=5.8 Hz), 3.54 (1.68H, d, J=6.8 Hz), 5.31 (1H, m), 6.47 (1H, dd, J=86.0, 11.0 Hz).

(Reaction 251-7)

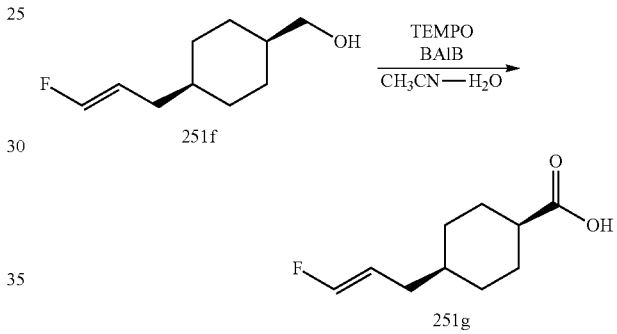

4-((E)-3-Fluoro-allyl)-cyclohexanecarboxylic acid was synthesized by operations similar to those in Reaction 109-1 using appropriate reagents and starting material.

$^1$H-NMR (400 MHz, CDCl$_3$) δ 0.80-2.10 (11H, m), 2.26 (0.15H, m), 2.61 (0.85H, m), 4.71 (0.16H, dm, J=40.6 Hz), 5.30 (0.84H, m), 6.47 (1H, dd, J=86.0, 11.0 Hz) (cis:trans=85:15).

The carboxylic acid reagent used in the synthesis of Compound 1073 (4-fluoro-4-(3-fluoro-propyl)-cyclohexanecarboxylic acid) was synthesized by the following method.

(Reaction 251-8)

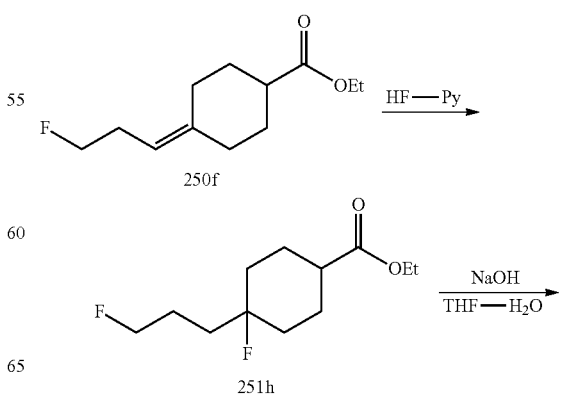

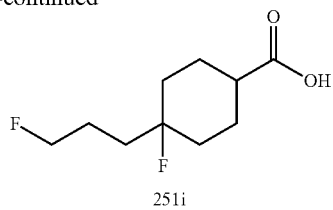

4-Fluoro-4-(3-fluoro-propyl)-cyclohexanecarboxylic acid was synthesized by operations similar to those in Reaction 249-9 and Reaction 95-18 using appropriate reagents and starting material.

$^1$H-NMR (400 MHz, CDCl$_3$) δ 2.36-2.17 (3H, m), 2.05-1.66 (8H, m), 1.47-1.25 (2H, m).

The carboxylic acid reagent used in the synthesis of Compound 1074 (4-ethynyl-cyclohexanecarboxylic acid) was synthesized by the following method.

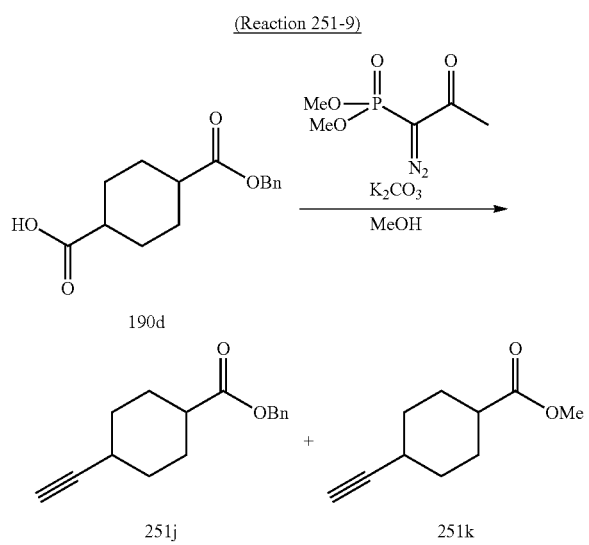

Dimethyl (1-diazo-2-oxopropyl)phosphonate (Bestmann reagent) (450 mg, 2.34 mmol) was added to a mixture of 4-formyl-cyclohexanecarboxylic acid benzyl ester (390 mg, 1.58 mmol) and potassium carbonate (323 mg, 2.34 mmol) in methanol (10 mL) at 0° C. and the mixture was stirred for five hours. Further, the reaction solution was stirred at room temperature for two hours. A saturated aqueous ammonium chloride solution and ethyl acetate were then added at 0° C., and the organic layer and the aqueous layer were separated. The aqueous layer was repeatedly extracted with ethyl acetate three times, and the organic layers were then combined, washed with saturated brine and then concentrated under reduced pressure. The resulting residue was purified by silica gel column chromatography to give a mixture of 4-ethynyl-cyclohexanecarboxylic acid methyl ester and 4-ethynyl-cyclohexanecarboxylic acid benzyl ester as a colorless liquid (220 mg, 78%).

$^1$H-NMR (400 MHz, CDCl$_3$) δ 1.34-1.48 (1.6H, m), 1.48-1.62 (1H, m), 1.65-1.87 (2.6H, m), 1.87-2.10 (3.8H, m), 2.20-2.42 (1.4H, m), 2.65-2.75 (0.6H, m), 3.66 (1.1H, s), 3.68 (1.4H, s), 5.10 (0.05H, s), 5.13 (0.3H, s), 7.29-7.40 (0.9H, m) (Me:Bn=0.85:0.15, cis:trans=0.6:0.4).

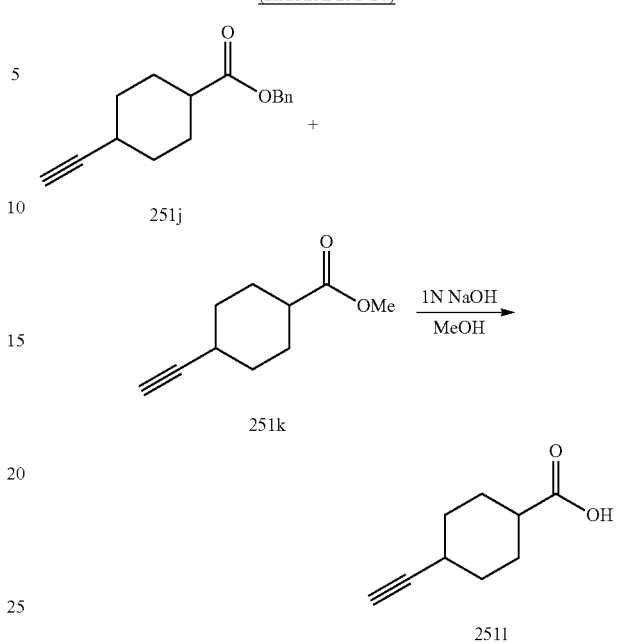

4-Ethynyl-cyclohexanecarboxylic acid was synthesized by operations similar to those in Reaction 95-18 using appropriate reagents and starting material.

$^1$H-NMR (400 MHz, CD$_3$OD) δ 1.37-1.50 (1.3H, m), 1.53-1.67 (1.6H, m), 1.67-1.82 (2.8H, m), 1.82-2.05 (2.5H, m), 2.18-2.38 (2.1H, m), 2.62-2.73 (0.7H, m).

The carboxylic acid reagent used in the synthesis of Compound 1077 (4-(2-fluoro-propyl)-cyclohexanecarboxylic acid) was synthesized by the following method.

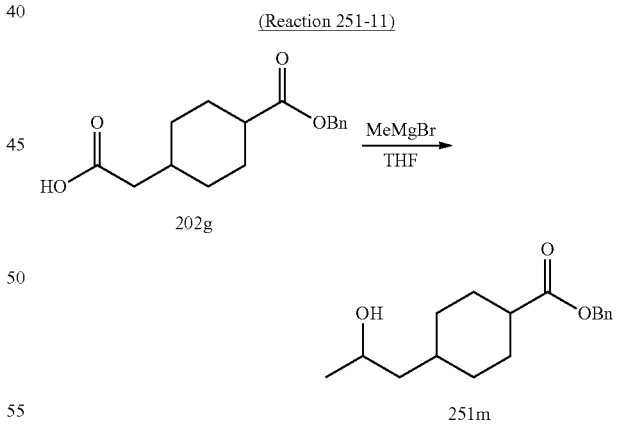

Methylmagnesium bromide (1 M solution in THF, 0.526 ml, 0.526 mmol) was added dropwise to 4-(2-oxo-ethyl)-cyclohexanecarboxylic acid benzyl ester (114 mg, 0.439 mmol) in THF (2.2 mL) at −78° C., and the mixture was stirred at the same temperature for 30 minutes. Water was added to the reaction mixture at the same temperature and extracted with ethyl acetate. The organic layer was sequentially washed with a saturated aqueous ammonium chloride solution, water and saturated brine and then concentrated under reduced pressure. The resulting residue was purified by silica gel column chromatography (hexane-ethyl acetate) to give 4-(2-hydroxy-propyl)-cyclohexanecarboxylic acid benzyl ester (80.7 mg, 67%).

$^1$H-NMR (300 MHz, CDCl$_3$) δ 1.18 (3H, d, J=6.1 Hz), 1.22-1.49 (5H, m), 1.50-1.67 (6H, m), 1.95-2.05 (2H, m), 2.58 (1H, dt, J=9.1, 4.9 Hz), 3.82-3.94 (1H, m), 5.13 (2H, s), 7.29-7.39 (5H, m);

MS (ESI) m/z=259 (M−H$_2$O+H)+.

(Reaction 251-12)

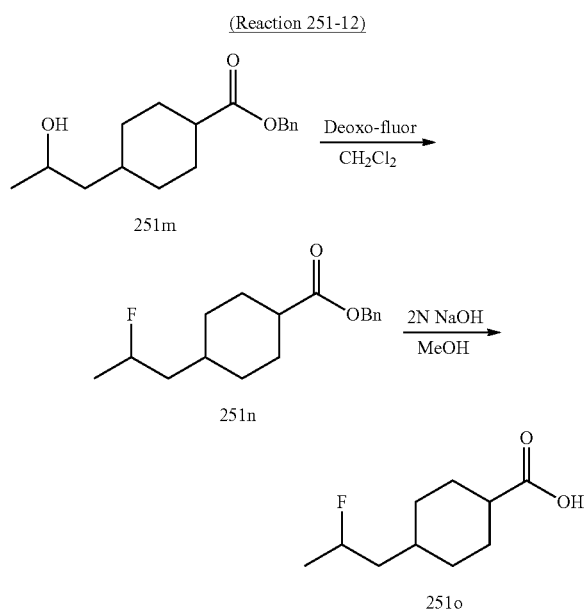

4-(2-Fluoro-propyl)-cyclohexanecarboxylic acid was synthesized by operations similar to those in Reaction 191-11 and Reaction 95-18 using appropriate reagents and starting material.

$^1$H-NMR (400 MHz, CDCl$_3$) δ 1.23-2.07 (11H, m), 1.31 (3H, dd, J=23.9, 7.0 Hz), 2.55-2.64 (1H, m), 4.63-4.87 (1H, m).

Example 252

N-[4-(2-{2-[4-(1-Fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide (Compound 1078)

(Reaction 252-1)

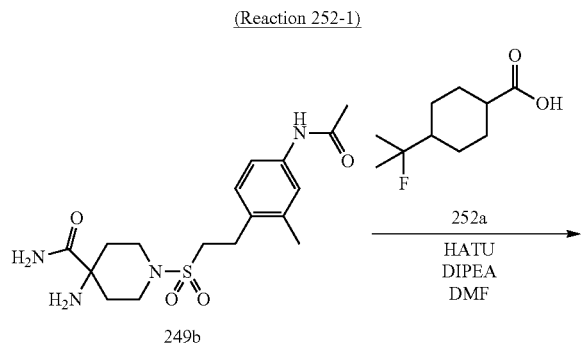

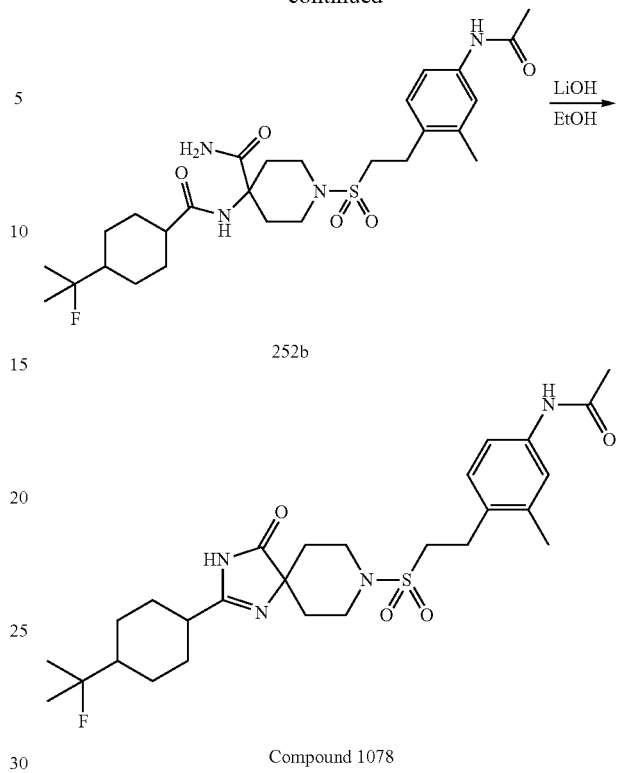

N-[4-(2-{2-[4-(1-Fluoro-1-methyl-ethyl)-cyclohexyl]-4-oxo-1,3,8-triaza-spiro[4.5]dec-1-ene-8-sulfonyl}-ethyl)-3-methyl-phenyl]-acetamide was synthesized by operations similar to those in Reaction 10-14 and Reaction 101-3 using appropriate reagents and starting material.

MS (ESI) m/z=535 (M+H)+.

The carboxylic acid reagent used in the synthesis of Compound 1078 (4-(1-fluoro-1-methyl-ethyl)-cyclohexanecarboxylic acid) was synthesized by the following method.

(Reaction 252-2)

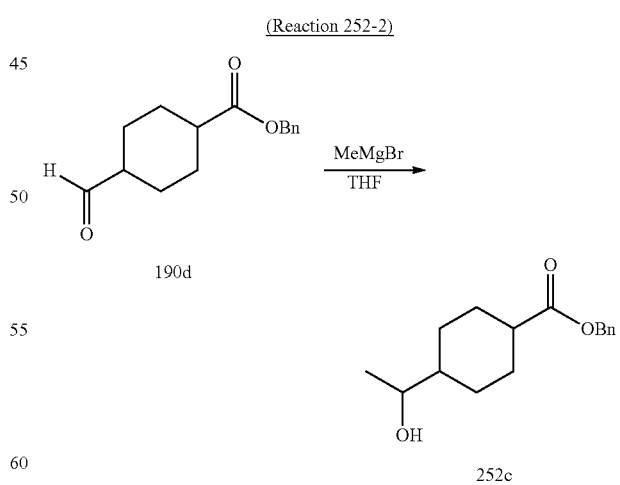

4-(1-Hydroxy-ethyl)-cyclohexanecarboxylic acid benzyl ester was synthesized by operations similar to those in Reaction 251-11 using appropriate reagents and starting material.

MS (ESI) m/z=263 (M+H)+.

(Reaction 252-3)

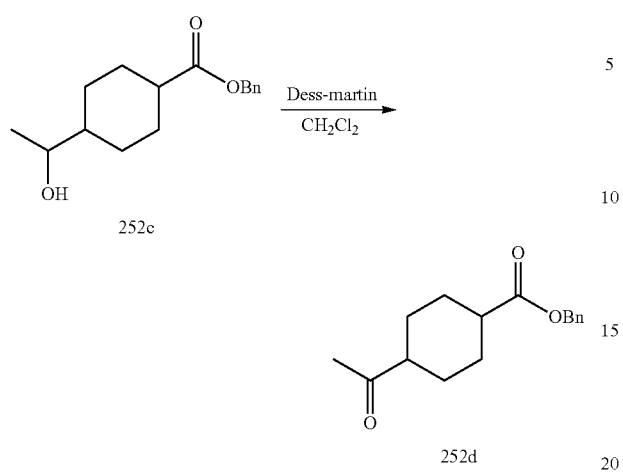

Dess-Martin reagent (151 mg, 0.355 mmol) was added to a solution of 4-(1-hydroxy-ethyl)-cyclohexanecarboxylic acid benzyl ester (71.6 mg, 0.273 mmol) in anhydrous dichloromethane (0.91 ml) at 0° C. The mixture was stirred at the same temperature for 10 minutes, and further warmed to room temperature and stirred for 4.5 hours. An aqueous sodium thiosulfate solution was added to the reaction solution, followed by extraction with dichloromethane. The organic phase was concentrated under reduced pressure, and the resulting residue was purified by silica gel column chromatography (hexane-ethyl acetate) to give 4-acetyl-cyclohexanecarboxylic acid benzyl ester (60.2 mg, 85%).

MS (ESI) m/z=261 (M+H)+.

(Reaction 252-4)

4-(1-Fluoro-1-methyl-ethyl)-cyclohexanecarboxylic acid was synthesized by operations similar to those in Reaction 251-11, Reaction 191-11 and Reaction 95-18 using appropriate reagents and starting material.

$^1$H-NMR (300 MHz, CD$_3$OD) δ 1.20-1.32 (2H, m), 1.24 (6H, d, J=21.9 Hz), 1.45-1.58 (3H, m), 1.62-1.70 (2H, m), 2.17-2.26 (2H, m), 2.60-2.65 (1H, m).

Example 253

N-(4-{2-[2-(4-Butylidene-cyclohexyl)-4-oxo-1,3,8-triaza-spiro[4.5]dec-1-ene-8-sulfonyl]-ethyl}-3-methyl-phenyl)-acetamide (Compound 1079)

(Reaction 253-1)

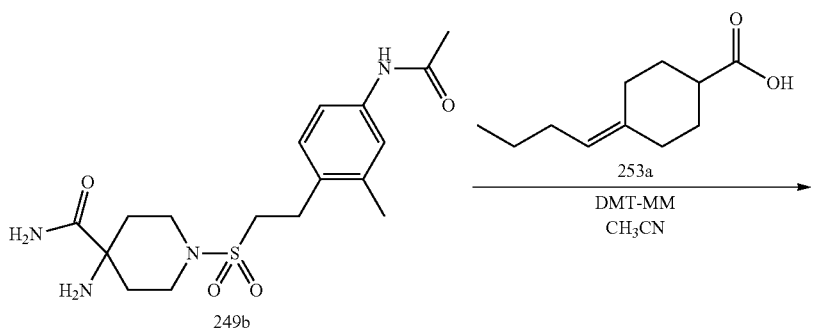

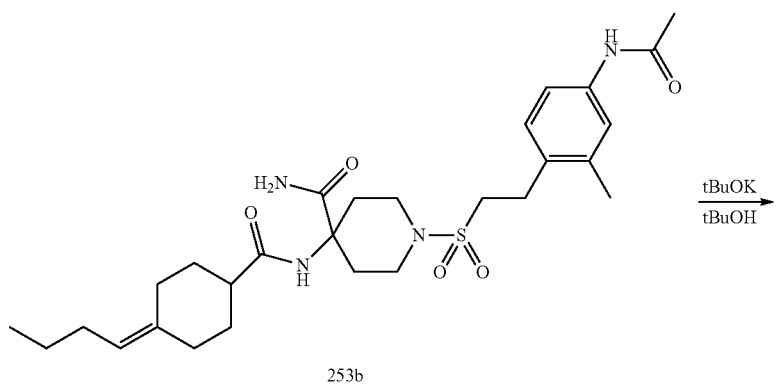

253b

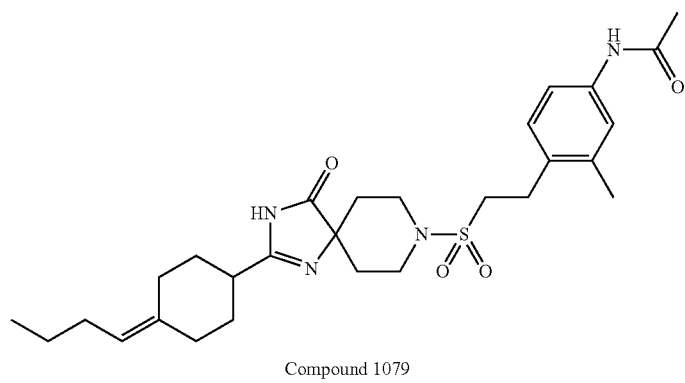

Compound 1079

N-(4-{2-[2-(4-Butylidene-cyclohexyl)-4-oxo-1,3,8-tri-aza-spiro[4.5]dec-1-ene-8-sulfonyl]-ethyl}-3-methyl-phenyl)-acetamide was synthesized by operations similar to those in Reaction 10-1 and Reaction 10-12 using appropriate reagents and starting material.

MS (ESI) m/z=529 (M+H)+.

The carboxylic acid reagent used in the synthesis of Compound 1079 (4-butylidene-cyclohexanecarboxylic acid) was synthesized by the following method.

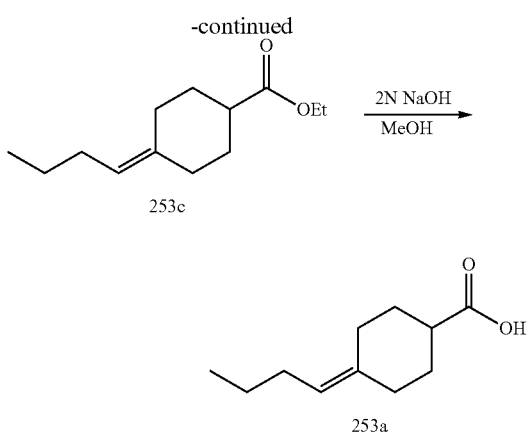

253c

253a

4-Butylidene-cyclohexanecarboxylic acid was synthesized by operations similar to those in Reaction 191-14 and Reaction 95-18 using appropriate reagents and starting material.

$^1$H-NMR (400 MHz, CDCl$_3$) δ 0.88 (3H, t, J=7.3 Hz), 1.28-1.40 (2H, m), 1.42-1.62 (2H, m), 1.77-1.88 (1H, m), 1.89-2.12 (5H, m), 2.20-2.29 (1H, m), 2.46-2.55 (1H, m), 2.55-2.63 (1H, m), 5.14 (1H, t, J=7.3 Hz).

(Reaction 253-2)

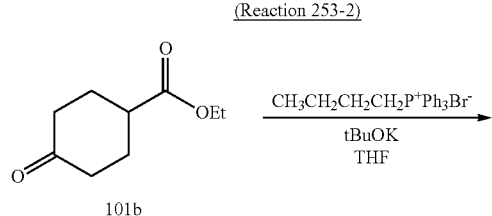

101b

Example 254

N-[3-Methyl-4-(2-{4-oxo-2-[4-(2,2,3,3,3-pentafluoro-propyl)-cyclohexyl]-1,3,8-triaza-spiro[4.5]dec-1-ene-8-sulfonyl}-ethyl)-phenyl]-acetamide (Compound 1080)

(Reaction 254-1)

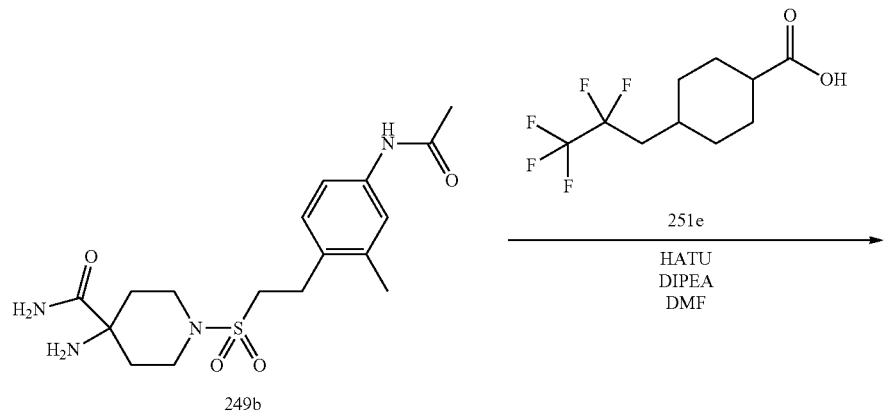

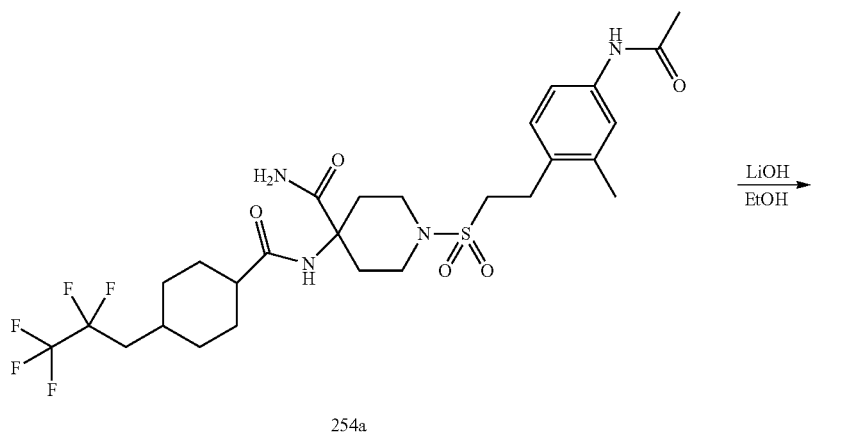

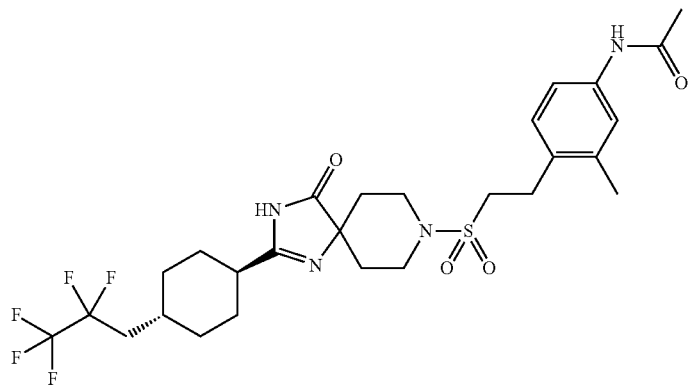

Compound 1080

N-[3-Methyl-4-(2-{4-oxo-2-[4-(2,2,3,3,3-pentafluoropropyl)-cyclohexyl]-1,3,8-triaza-spiro[4.5]dec-1-ene-8-sulfonyl}-ethyl)-phenyl]-acetamide was synthesized by operations similar to those in Reaction 10-14 and Reaction 101-3 using appropriate reagents and starting material.

MS (ESI) m/z=607 (M+H)+.

Example 255
1-{3,5-Dimethyl-4-[2-(2-non-4-ynyl-4-oxo-1,3,8-triaza-spiro[4.5]dec-1-ene-8-sulfonyl)-ethyl]-phenyl}-1-methyl-urea (Compound 1081)
(Reaction 255-1)
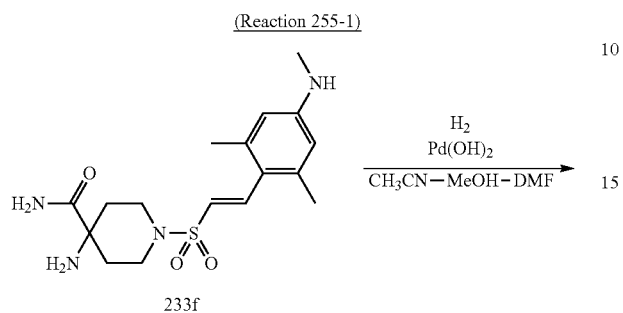
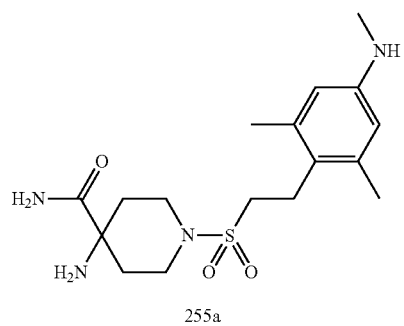
4-Amino-1-[2-(2,6-dimethyl-4-methylamino-phenyl)-ethanesulfonyl]-piperidine-4-carboxylic amide was synthesized by operations similar to those in Reaction 184-1 using appropriate reagents and starting material.
MS (ESI) m/z=369 (M+H)+.
(Reaction 255-2)
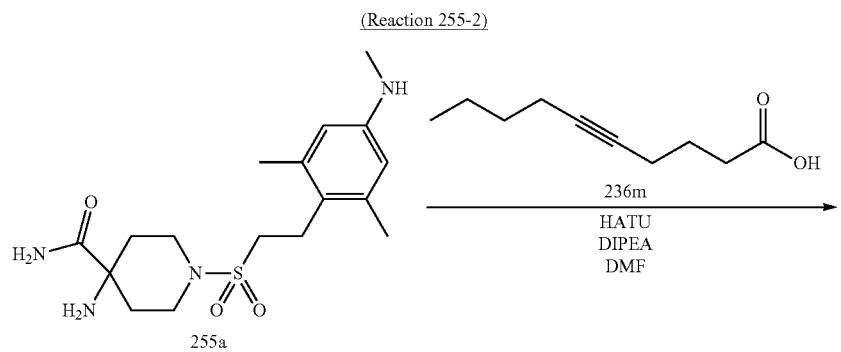
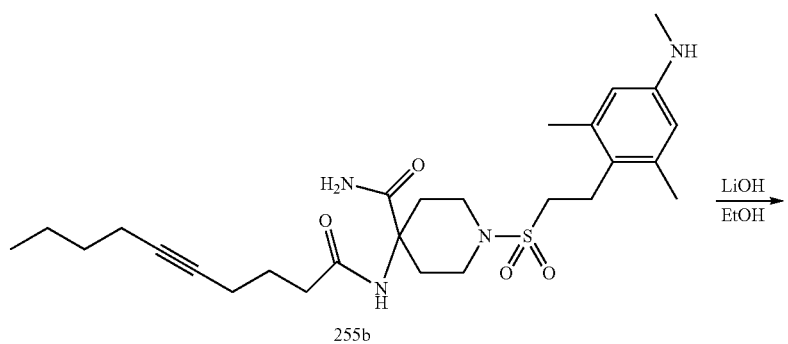
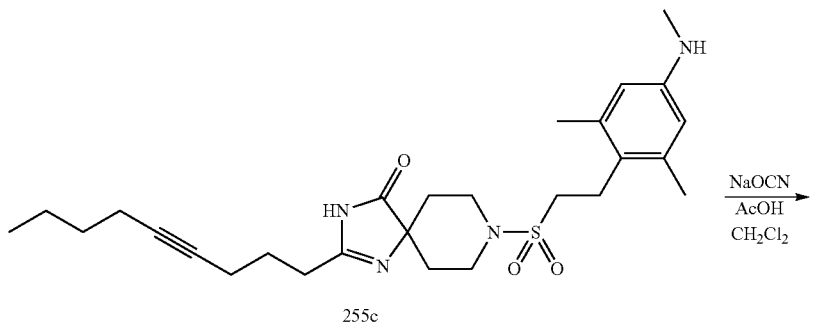

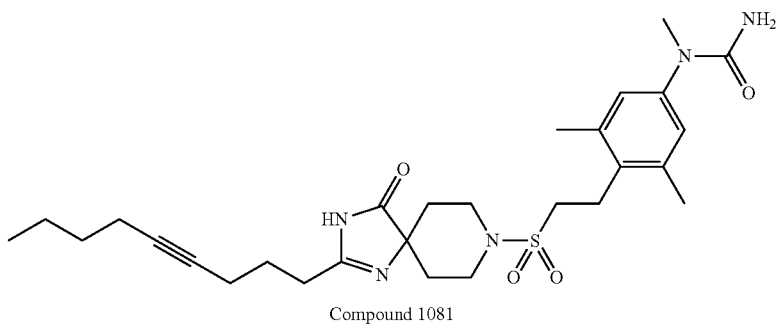

Compound 1081

1-{3,5-Dimethyl-4-[2-(2-non-4-ynyl-4-oxo-1,3,8-triaza-spiro[4.5]dec-1-ene-8-sulfonyl)-ethyl]-phenyl}-1-methyl-urea was synthesized by operations similar to those in Reaction 10-14, Reaction 101-3 and Reaction 89-2 using appropriate reagents and starting material.

MS (ESI) m/z=544 (M+H)+.

The example compounds shown below were synthesized by operations similar to those in Reaction 255-2 using appropriate reagents and starting materials.

Compounds 1082 to 1083

TABLE 160

| Compound | Structure | LCMS condition | Retention time (min) | MS (m/z) |
|---|---|---|---|---|
| 1082 | 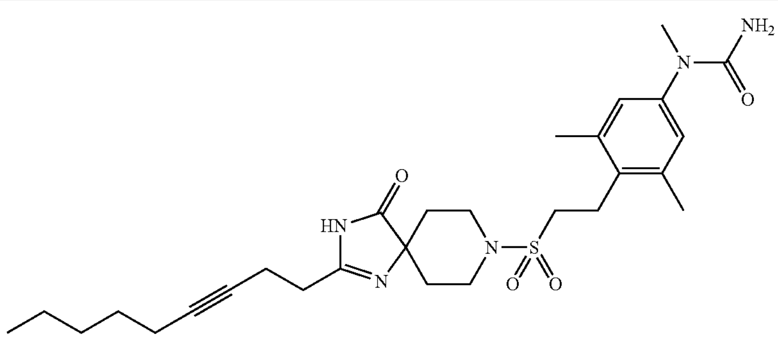 [SMILES: CCCCCC#CCCC1=NC2(CCN(S(=O)(=O)CCc3c(C)cc(N(C)C(N)=O)cc3C)CC2)C(=O)N1] | LCMS-F-1 | 1.01 | 544 (M + H)+ |
| 1083 | 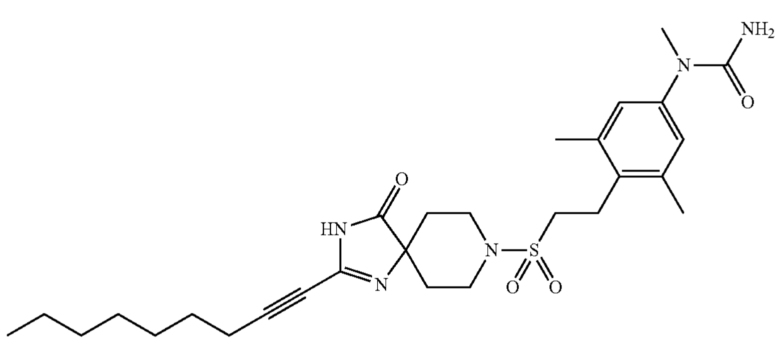 [SMILES: CCCCCCCC#CC1=NC2(CCN(S(=O)(=O)CCc3c(C)cc(N(C)C(N)=O)cc3C)CC2)C(=O)N1] | LCMS-C-2 | 2.27 | 544 (M + H)+ |

Example 256

1-(3,5-Dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea (Compound 1084)

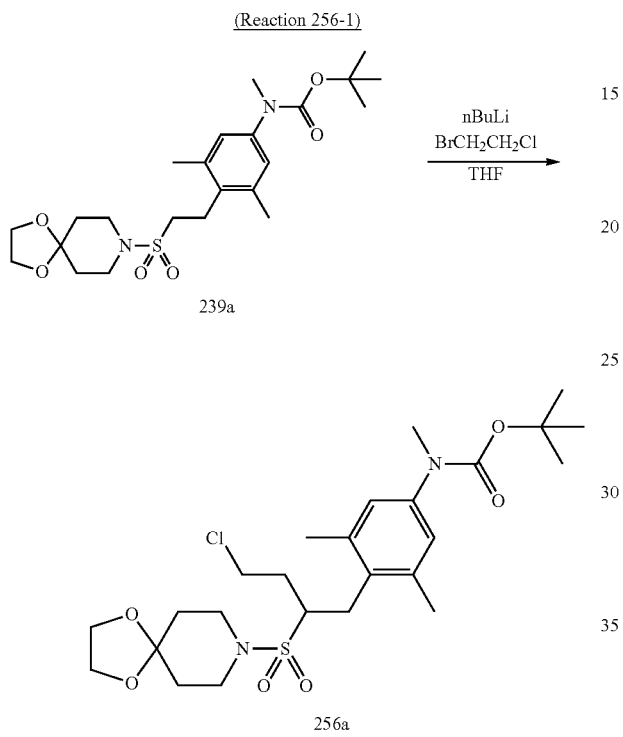

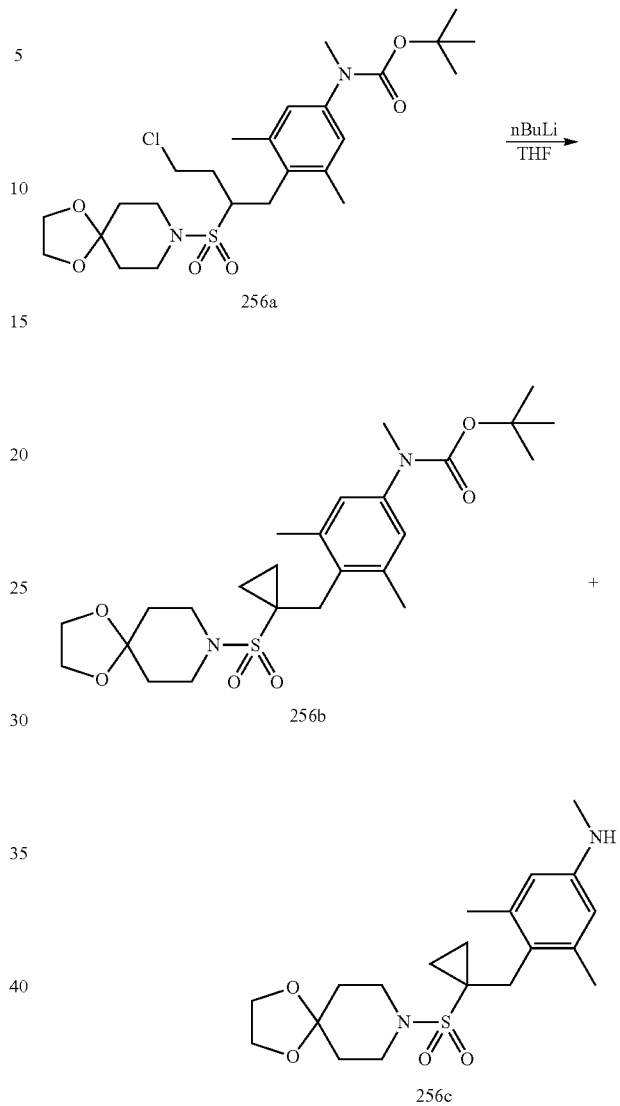

n-Butyllithium (1.6 M solution in hexane, 0.58 ml, 0.93 mmol) was added to a solution of {4-[2-(1,4-dioxa-8-aza-spiro[4.5]decane-8-sulfonyl)-ethyl]-3,5-dimethyl-phenyl}-methyl-carbamic acid tert-butyl ester (195.7 mg, 0.4176 mmol) in THF (4.2 ml) at −78° C. over six minutes, and the mixture was stirred at the same temperature for 20 minutes. 1-Bromo-2-chloro-ethane (105 μl, 1.26 mmol) was added to the reaction solution at −78° C. within 10 minutes. The mixture was then stirred while warming from −78° C. to 0° C. over one hour, and further stirred at room temperature for one hour. A 50% saturated aqueous ammonium chloride solution was added, followed by extraction with ethyl acetate. The organic layer was then dried over MgSO$_4$ and concentrated under reduced pressure. The resulting residue was purified by silica gel column chromatography (hexane/ethyl acetate=5/2) to give {4-[4-chloro-2-(1,4-dioxa-8-aza-spiro[4.5]decane-8-sulfonyl)-butyl]-3,5-dimethyl-phenyl}-methyl-carbamic acid tert-butyl ester (133 mg, 60%).

$^1$H-NMR (400 MHz, CDCl$_3$) δ 1.44 (9H, s), 1.80 (4H, t, J=6.0 Hz), 1.85 (1H, m), 2.28 (1H, m), 2.33 (6H, s), 3.00 (1H, dd, J=14.0, 11.6 Hz), 3.18 (1H, dd, J=14.0, 4.4 Hz), 3.22 (3H, s), 3.33 (1H, m), 3.52 (4H, t, J=6.0 Hz), 3.60 (2H, m), 3.98 (4H, s), 6.92 (2H, s).

n-Butyllithium (1.6 M solution in hexane, 345 μl, 0.552 mmol) was added to a solution of {4-[4-chloro-2-(1,4-dioxa-8-aza-spiro[4.5]decane-8-sulfonyl)-butyl]-3,5-dimethyl-phenyl}-methyl-carbamic acid tert-butyl ester (115.0 mg, 0.2165 mmol) in THF (3.0 ml) at −78° C. over three minutes. The mixture was stirred at the same temperature for five minutes, and then warmed and further stirred at room temperature for one hour. A 50% saturated aqueous ammonium chloride solution was added, followed by extraction with ethyl acetate. The organic layer was then dried over MgSO$_4$ and concentrated under reduced pressure. The resulting residue was purified by silica gel column chromatography (hexane/ethyl acetate=2/1) to give {4-[1-(1,4-dioxa-8-aza-spiro[4.5]decane-8-sulfonyl)-cyclopropylmethyl]-3,5-dimethyl-phenyl}-methyl-carbamic acid tert-butyl ester and {4-[1-(1,4-dioxa-8-aza-spiro[4.5]decane-8-sulfonyl)-cyclopropylmethyl]-3,5-dimethyl-phenyl}-methyl-amine as a mixture (46.0 mg, 43% and 19.6 mg, 23%). This was used in the next reaction without complete purification.

(Reaction 256-3)

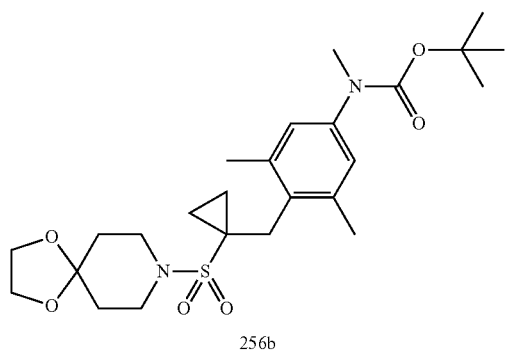

256b

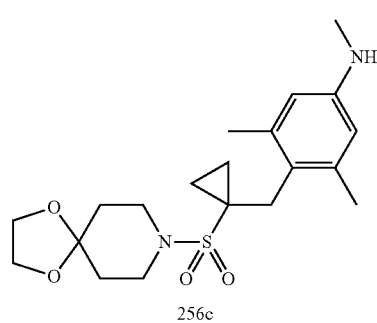

256c

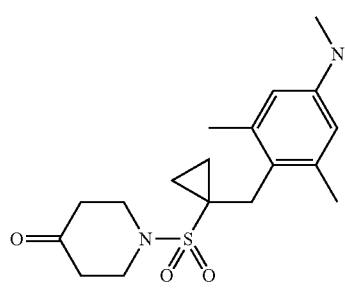

256d (Reaction 256-4)

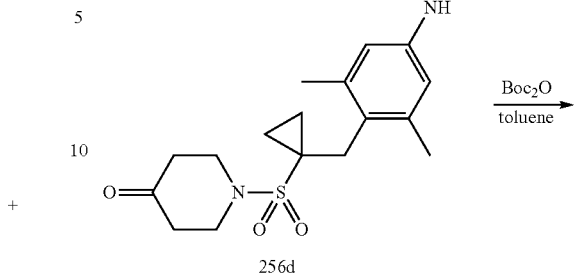

256d

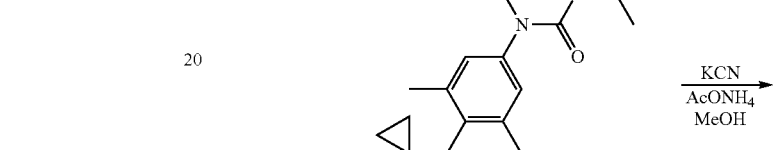

256e

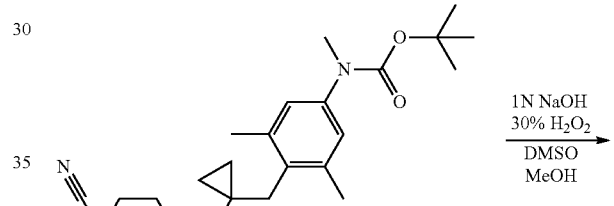

256f

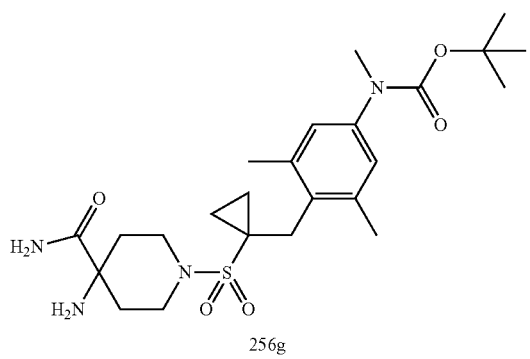

256g

A 5 N aqueous HCl solution (2.0 ml, 10 mmol) was added to a solution of a mixture of {4-[1-(1,4-dioxa-8-aza-spiro [4.5]decane-8-sulfonyl)-cyclopropylmethyl]-3,5-dimethyl-phenyl}-methyl-carbamic acid tert-butyl ester (54.7 mg, 0.111 mmol) and {4-[1-(1,4-dioxa-8-aza-spiro[4.5]decane-8-sulfonyl)-cyclopropylmethyl]-3,5-dimethyl-phenyl}-methyl-amine (23.1 mg, 0.0585 mmol) in EtOH (2.0 mL), and the mixture was stirred at 80° C. for two hours. The reaction mixture was neutralized by adding a 5 N aqueous NaOH solution (1.9 ml) and then extracted with ethyl acetate. The organic layer was dried over MgSO$_4$ and concentrated under reduced pressure to give 1-[1-(2,6-dimethyl-4-methylamino-benzyl)-cyclopropanesulfonyl]-4-piperidinone (58.8 mg, 99%).

$^1$H-NMR (400 MHz, CDCl$_3$) δ 0.44 (2H, m), 1.21 (2H, m), 2.22 (6H, s), 2.60 (4H, t, J=6.0 Hz), 2.79 (3H, s), 3.27 (2H, s), 3.78 (4H, t, J=6.0 Hz), 3.99 (4H, s), 6.28 (2H, s).

{4-[1-(4-Amino-4-carbamoyl-piperidine-1-sulfonyl)-cyclopropylmethyl]-3,5-dimethyl-phenyl}-methyl-carbamic acid tert-butyl ester was synthesized by operations similar to those in Reaction 127-2 (using toluene as a solvent), Reaction 233-3 and Reaction 233-4 using appropriate reagents and starting material.

$^1$H-NMR (400 MHz, CDCl$_3$) δ 0.37 (2H, m), 1.19 (2H, m), 1.45 (9H, s), 1.59 (2H, m), 2.24 (2H, m), 2.30 (6H, s), 3.20 (3H, s), 3.36 (2H, s), 3.43 (2H, ddd, J=13.0, 9.6 and 3.2 Hz), 3.77 (2H, ddd, J=13.0, 5.2 and 4.8 Hz), 5.39 (1H, br), 6.89 (2H, s), 7.27 (1H, br).

(Reaction 256-5)
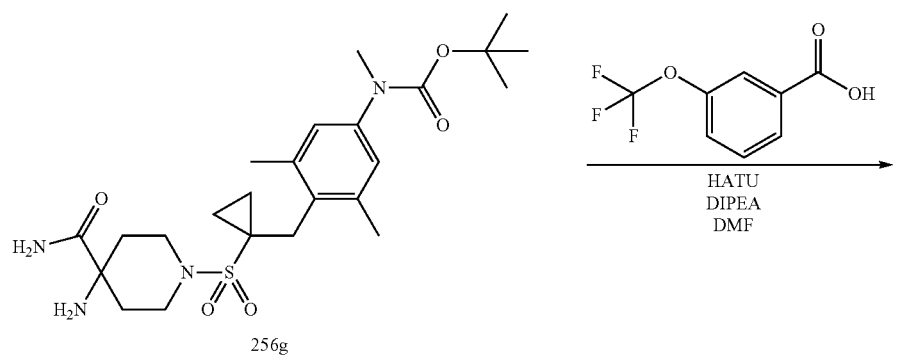
256g
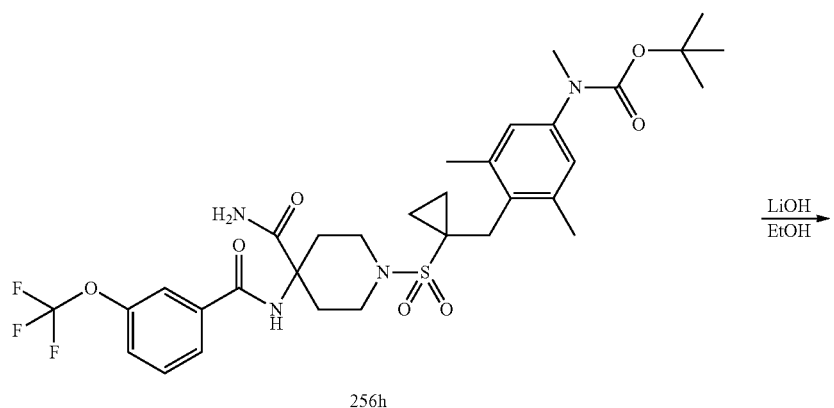
256h
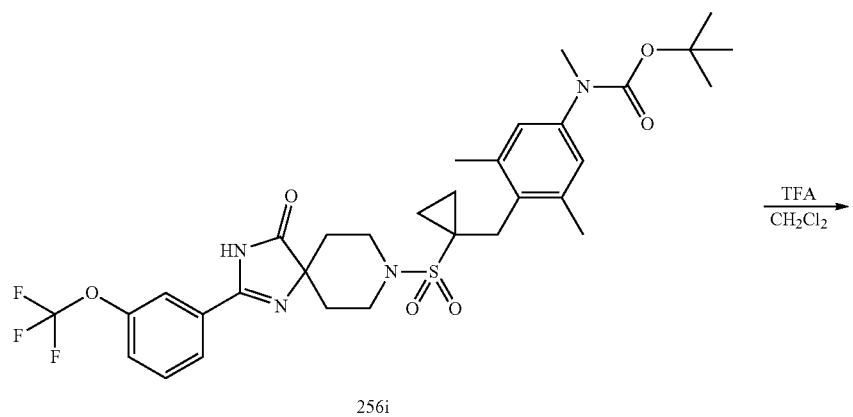
256i
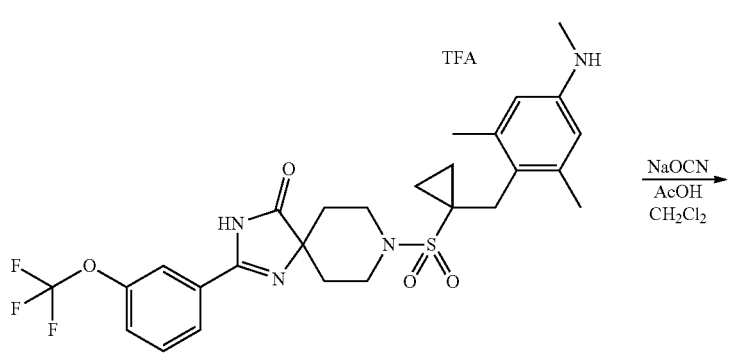
256j

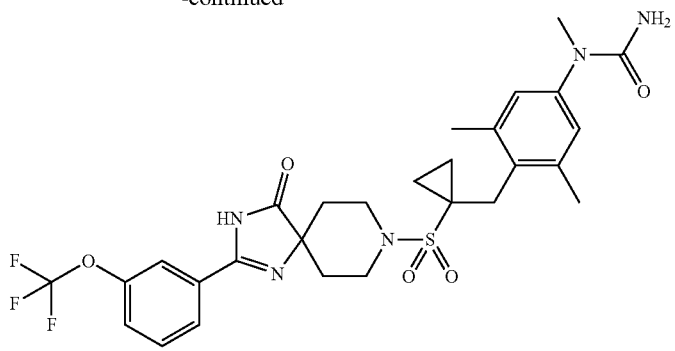

Compound 1084

1-(3,5-Dimethyl-4-{1-[4-oxo-2-(3-trifluoromethoxy-phenyl)-1,3,8-triaza-spiro[4.5]dec-1-ene-8-sulfonyl]-cyclopropylmethyl}-phenyl)-1-methyl-urea was synthesized by operations similar to those in Reaction 10-14, Reaction 101-3, Reaction 4-1 and Reaction 89-2 using appropriate reagents and starting material.

MS (ESI) m/z=608 (M+H)+.

Example 257

1-(4-{2,2-Difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea (Compound 1085)

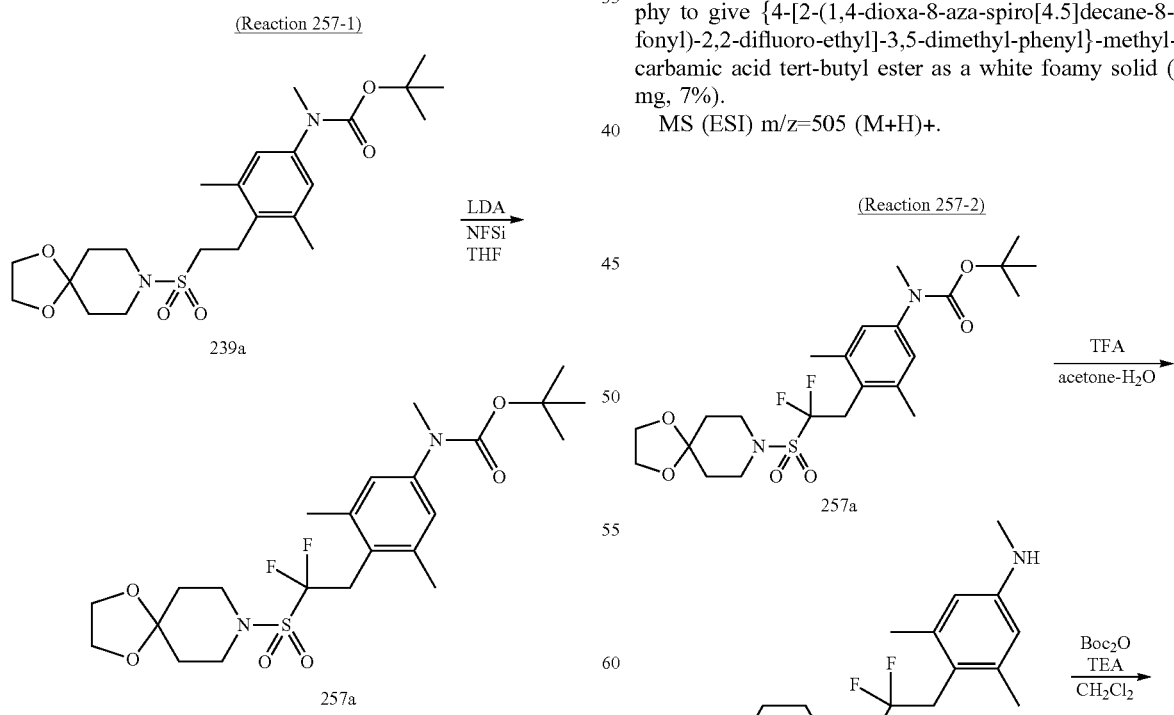

n-Butyllithium (1.54 M solution in hexane, 5.6 ml, 8.67 mmol) was added to a solution of diisopropyl-amine (1.45 mL, 10.4 mmol) in tetrahydrofuran (30 mL) at 0° C., and the mixture was stirred for 20 minutes. The reaction solution was brought to −78° C., and a solution of {4-[2-(1,4-dioxa-8-aza-spiro[4.5]decane-8-sulfonyl)-ethyl]-3,5-dimethyl-phenyl}-methyl-carbamic acid tert-butyl ester (2.71 g, 5.78 mmol) in tetrahydrofuran (10 mL) was then added dropwise slowly. The reaction solution was stirred at −78° C. for 0.5 hour, and N-fluorobenzenesulfonimide (2.73 g, 8.67 mmol) was then added at −78° C., followed by stirring for one hour. A saturated aqueous ammonium chloride solution was added to the reaction solution at −78° C., and the mixture was brought to room temperature. Ethyl acetate was then added, and the organic layer and the aqueous layer were separated. The aqueous layer was repeatedly extracted with ethyl acetate three times. The organic layers were then combined and washed with saturated brine, and then dried over sodium sulfate and concentrated under reduced pressure. The resulting residue was purified by silica gel column chromatography to give {4-[2-(1,4-dioxa-8-aza-spiro[4.5]decane-8-sulfonyl)-2,2-difluoro-ethyl]-3,5-dimethyl-phenyl}-methyl-carbamic acid tert-butyl ester as a white foamy solid (205 mg, 7%).

MS (ESI) m/z=505 (M+H)+.

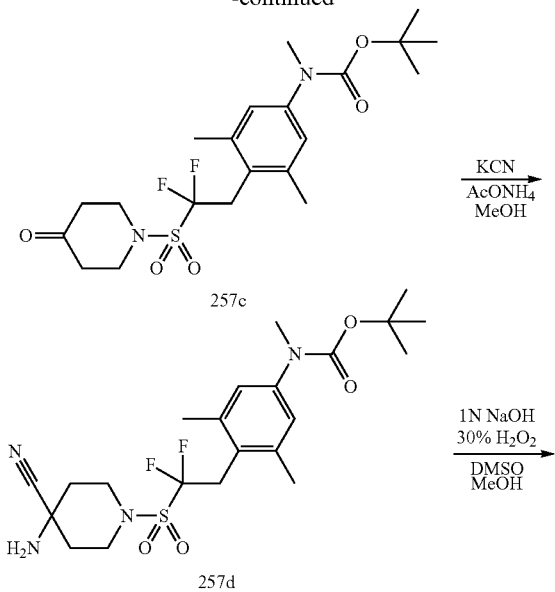
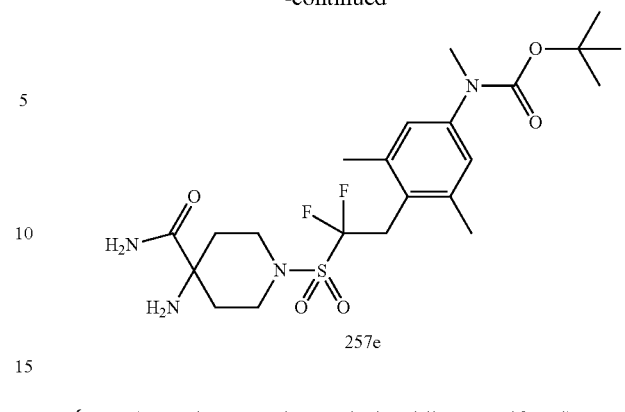
{4-[2-(4-Amino-4-carbamoyl-piperidine-1-sulfonyl)-2,2-difluoro-ethyl]-3,5-dimethyl-phenyl}-methyl-carbamic acid tert-butyl ester was synthesized by operations similar to those in Reaction 233-2, Reaction 19-2, Reaction 233-3 and Reaction 233-4 using appropriate reagents and starting material.
MS (ESI) m/z=505 (M+H)+.
(Reaction 257-3)
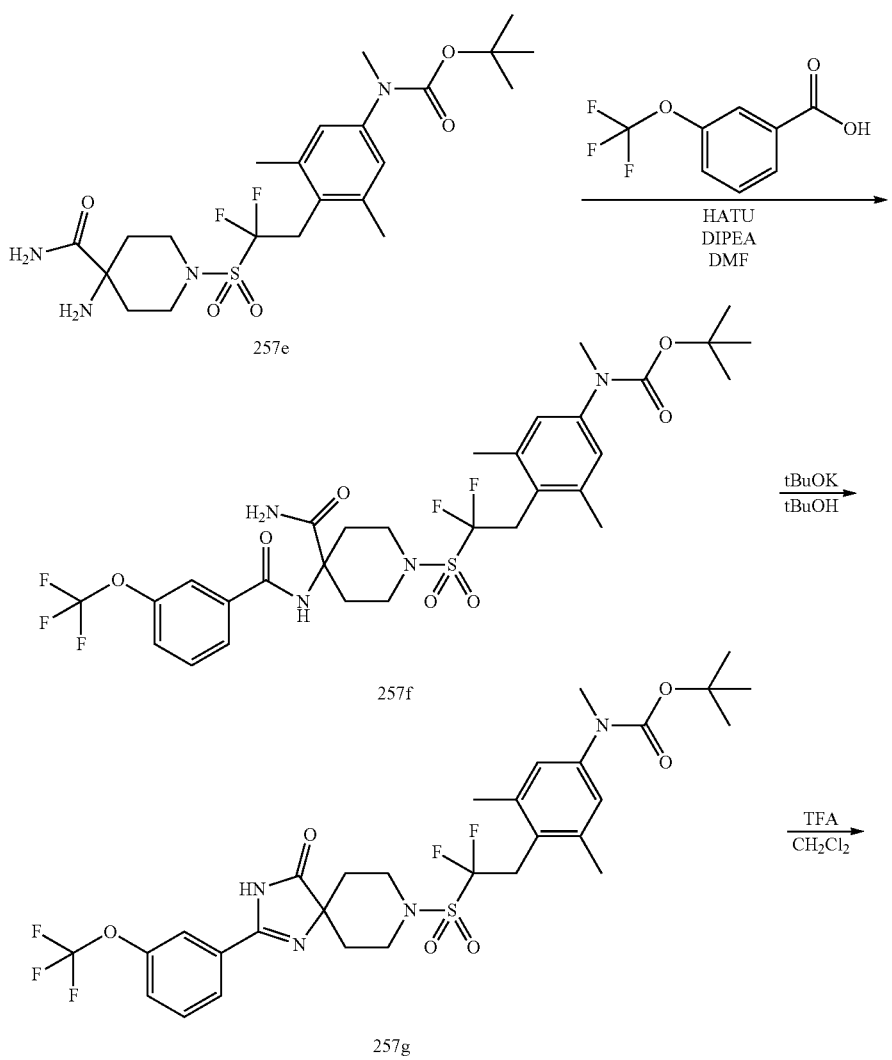

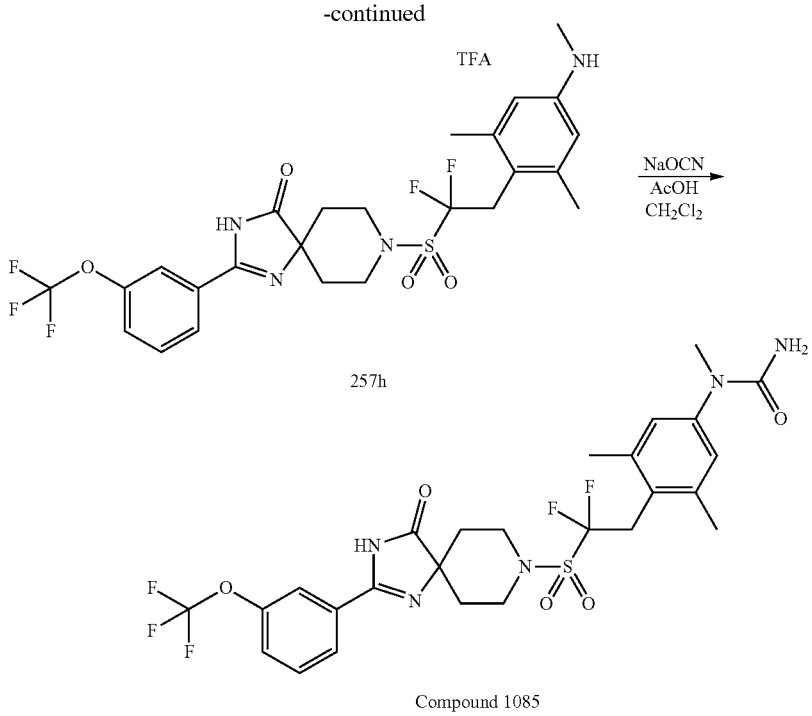

257h

Compound 1085

1-(4-{2,2-Difluoro-2-[4-oxo-2-(3-trifluoromethoxy-phenyl)-1,3,8-triaza-spiro[4.5]dec-1-ene-8-sulfonyl]-ethyl}-3,5-dimethyl-phenyl)-1-methyl-urea was synthesized by operations similar to those in Reaction 10-14, Reaction 10-12, Reaction 4-1 and Reaction 89-2 using appropriate reagents and starting material.

MS (ESI) m/z=618 (M+H)+.

Example 258

1-{4-[2,2-Difluoro-2-(2-nonyl-4-oxo-1,3,8-triaza-spiro[4.5]dec-1-ene-8-sulfonyl)-ethyl]-3,5-dimethyl-phenyl}-1-methyl-urea (Compound 1086)

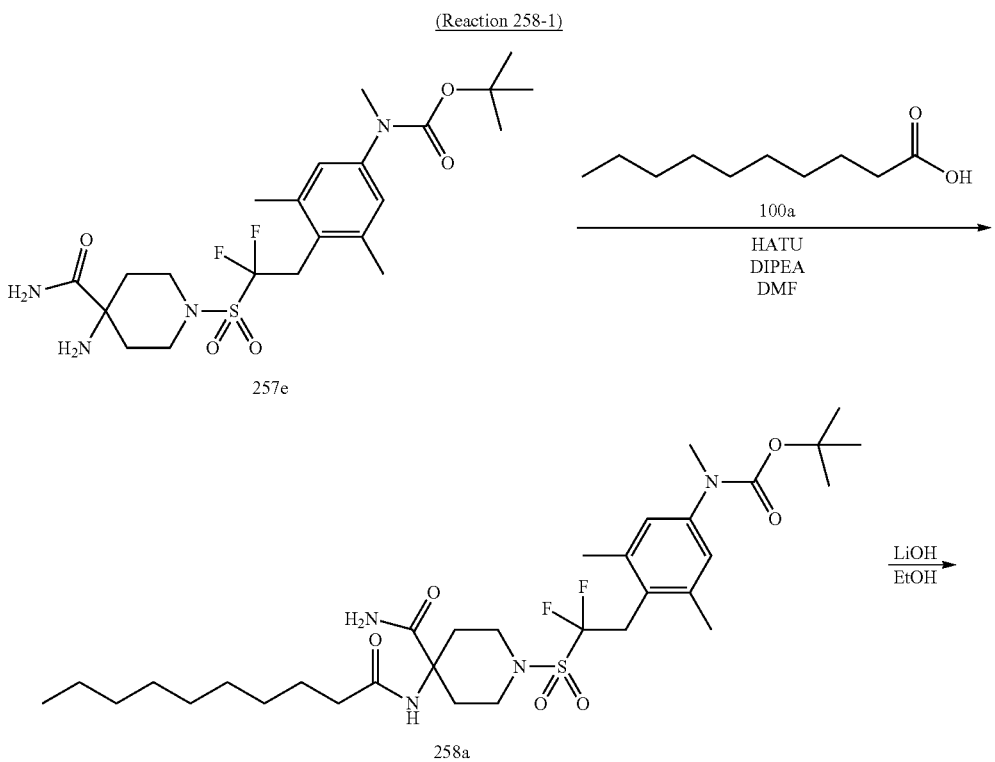

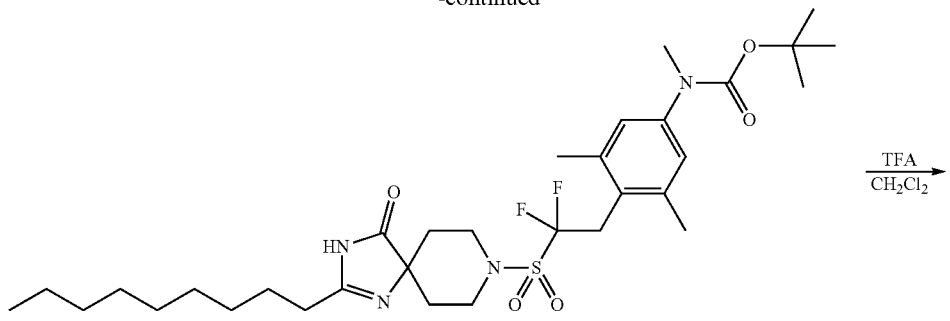

258b

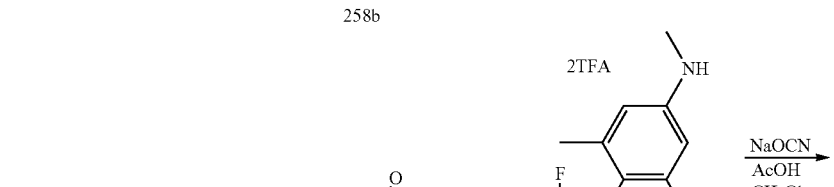

258c

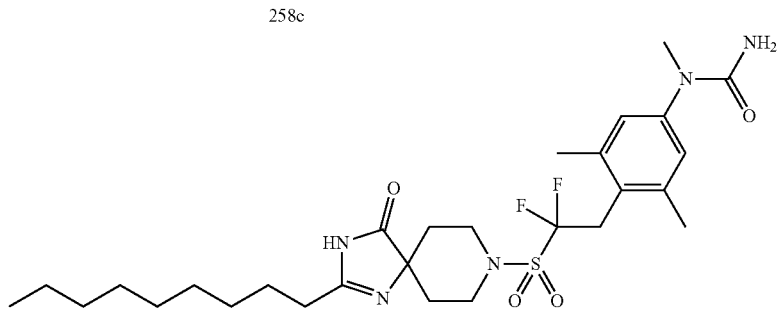

Compound 1086

1-{4-[2,2-Difluoro-2-(2-nonyl-4-oxo-1,3,8-triaza-spiro[4.5]dec-1-ene-8-sulfonyl)-ethyl]-3,5-dimethyl-phenyl}-1-methyl-urea was synthesized by operations similar to those in Reaction 10-14, Reaction 101-3, Reaction 4-1 and Reaction 89-2 using appropriate reagents and starting material.
MS (ESI) m/z=584 (M+H)+.

Example 259

1-{3,5-Dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea (Compound 1087)

(Reaction 259-1)

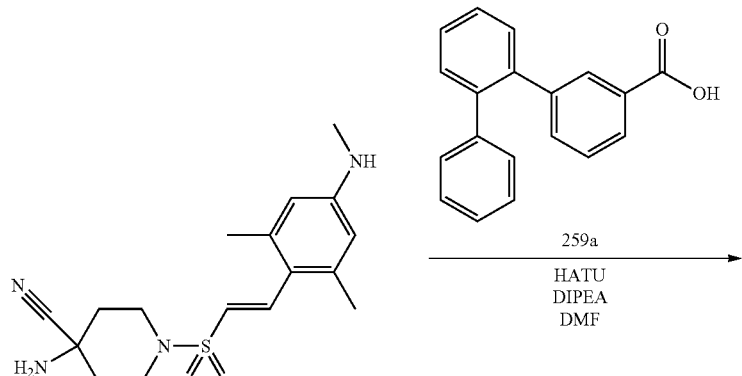

233e

-continued
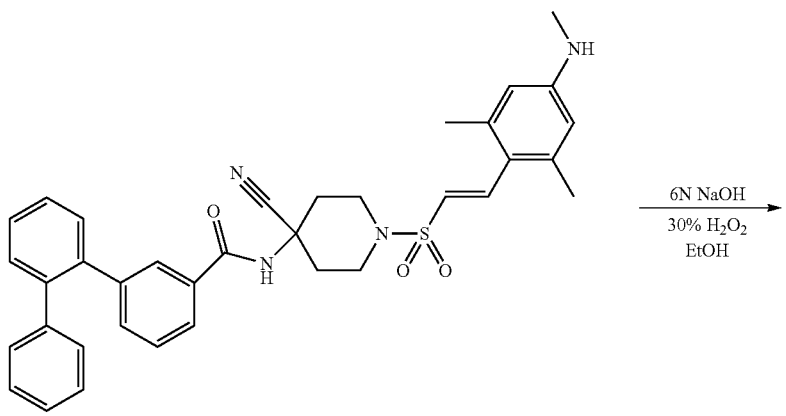
259b
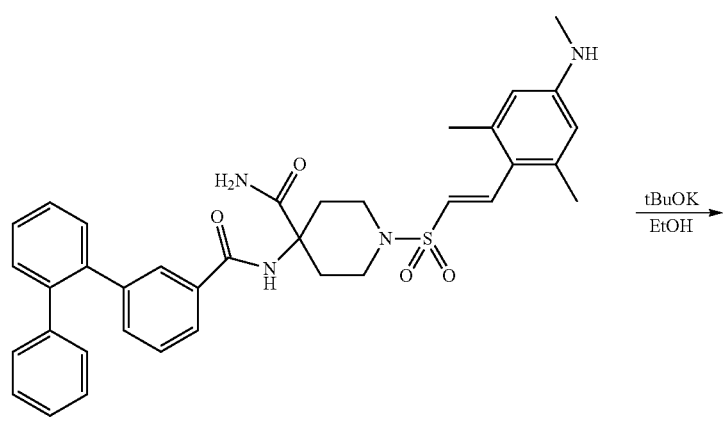
259c
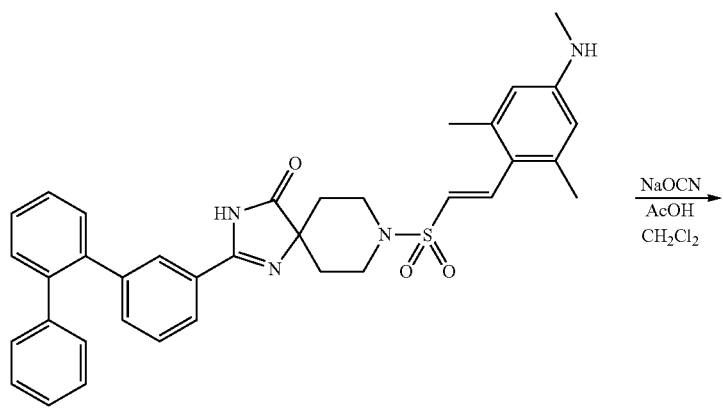
259d

-continued

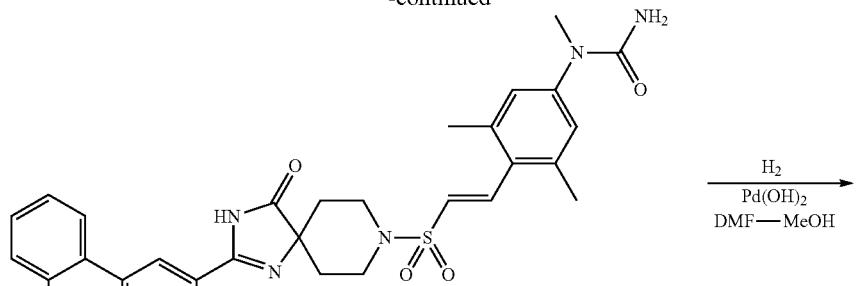

259e

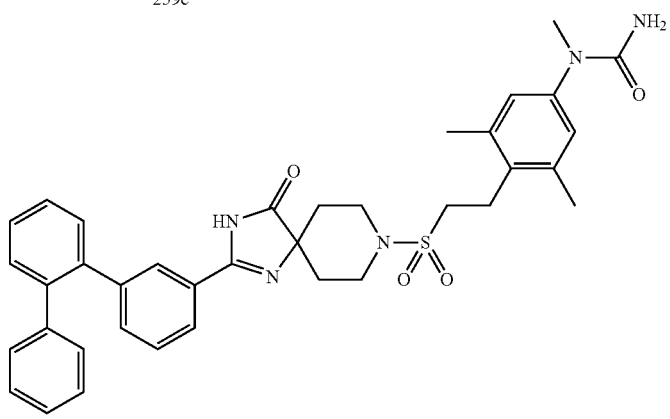

Compound 1087

1-{3,5-Dimethyl-4-[2-(4-oxo-2-[1,1';2',1"]terphenyl-3-yl-1,3,8-triaza-spiro[4.5]dec-1-ene-8-sulfonyl)-ethyl]-phenyl}-1-methyl-urea was synthesized by operations similar to those in Reaction 10-14, Reaction 10-11, Reaction 10-12 (using ethanol as a solvent), Reaction 89-2 and Reaction 122-2 using appropriate reagents and starting material.

MS (ESI) m/z=650 (M+H)+.

The carboxylic acid reagent used in the synthesis of Compound 1087 ([1,1';2',1"]terphenyl-3"-carboxylic acid) was synthesized by the following method.

(Reaction 259-2)

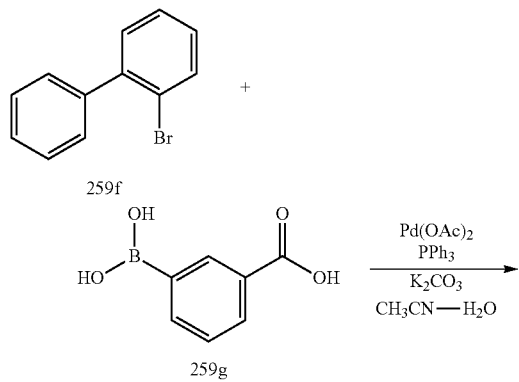

-continued

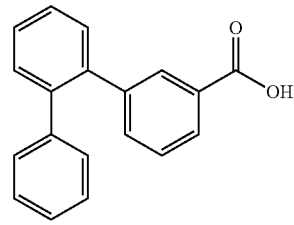

259a

3-Boronobenzoic acid (300 mg, 1.81 mmol), palladium acetate (40.4 mg, 0.18 mmol), triphenylphosphine (94.6 mg, 0.36 mmol) and potassium carbonate (374.6 mg, 2.71 mmol) were added to a solution of 2-bromo-1,1'-biphenyl (0.3 ml, 1.81 mmol) in acetonitrile (10 mL)-water (2.5 ml), and the mixture was heated with stirring at 100° C. overnight. The reaction mixture was cooled and then filtered through celite, and the filtrate was concentrated under reduced pressure. The resulting residue was purified by silica gel column chromatography (hexane:ethyl acetate=1:1) to give [1,1';2',1"]terphenyl-3"-carboxylic acid (191 mg, 39%).

MS (ESI) m/z=275 (M+H)+.

Example 260
1-[3,5-Dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea (Compound 1088)
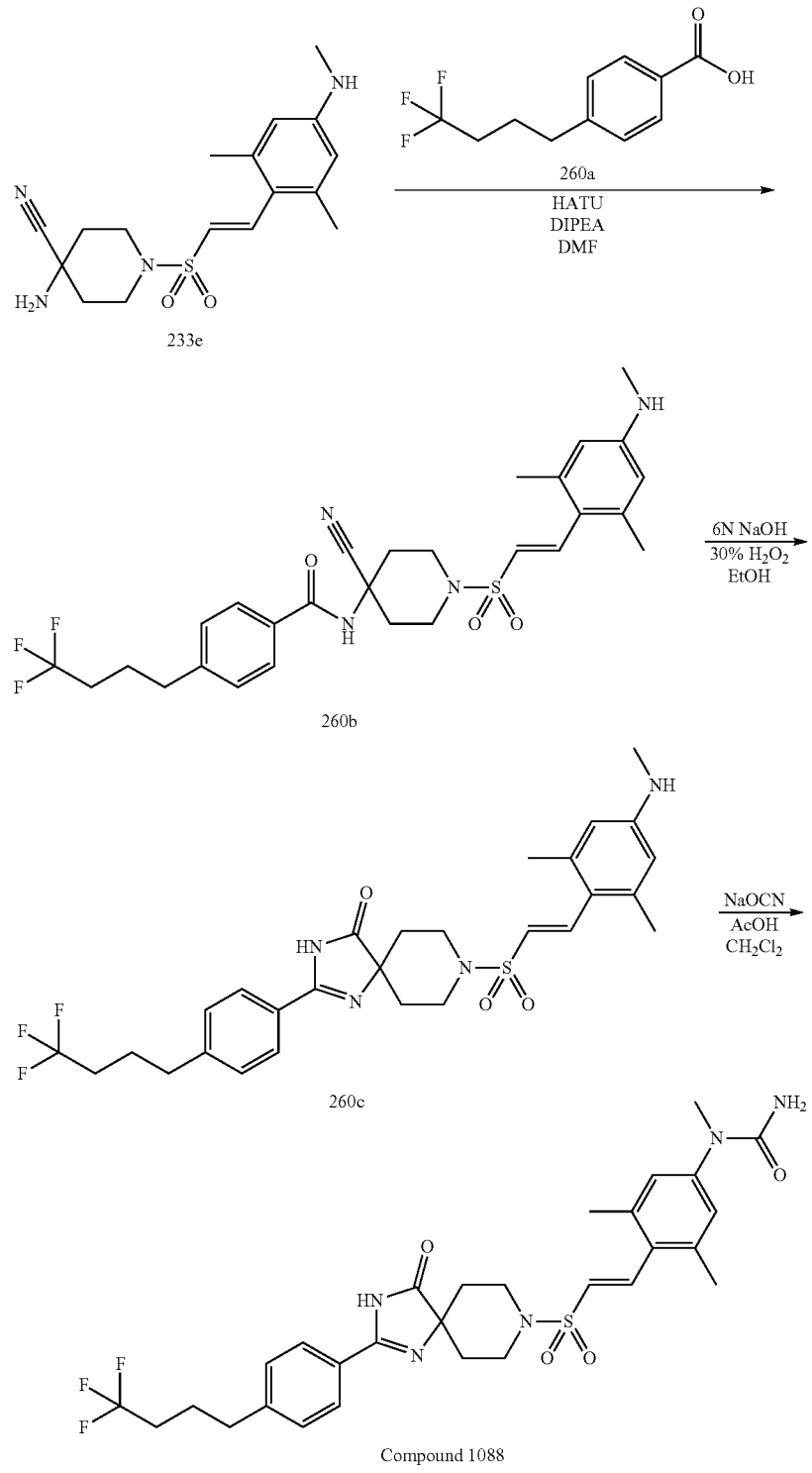

1-[3,5-Dimethyl-4-((E)-2-{4-oxo-2-[4-(4,4,4-trifluoro-butyl)-phenyl]-1,3,8-triaza-spiro[4.5]dec-1-ene-8-sulfonyl}-vinyl)-phenyl]-1-methyl-urea was synthesized by operations similar to those in Reaction 10-14, Reaction 1-4 and Reaction 89-2 using appropriate reagents and starting material.

MS (ESI) m/z=606 (M+H)+.

The carboxylic acid reagent used in the synthesis of Compound 1088 (4-(4,4,4-trifluoro-butyl)-benzoic acid) was synthesized by the following method.

4-(4,4,4-Trifluoro-butyl)-benzoic acid was synthesized by operations similar to those in Reaction 191-14, Reaction 18-2 and Reaction 95-18 using appropriate reagents and starting material.

MS (ESI) m/z=233 (M+H)+.

The example compound shown below was synthesized by operations similar to those in Reaction 260-1 using appropriate reagents and starting material.

Compound 1089

TABLE 161

| Compound | Structure | LCMS condition | Retention time (min) | MS (m/z) |
|---|---|---|---|---|
| 1089 | 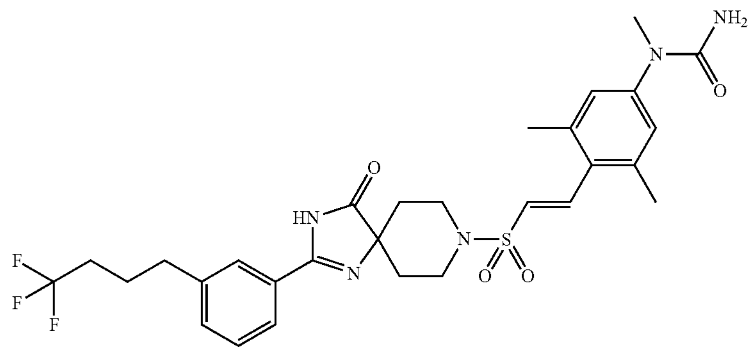 [SMILES: Cc1cc(N(C)C(N)=O)cc(C)c1/C=C/S(=O)(=O)N1CCC2(CC1)N=C(c1cccc(CCCC(F)(F)F)c1)NC2=O] | LCMS-D-1 | 2.63 | 606 (M + H)+ |

The carboxylic acid reagent used in the synthesis of Compound 1089 (3-(4,4,4-trifluoro-butyl)-benzoic acid) was synthesized by the following method.

(Reaction 260-2)

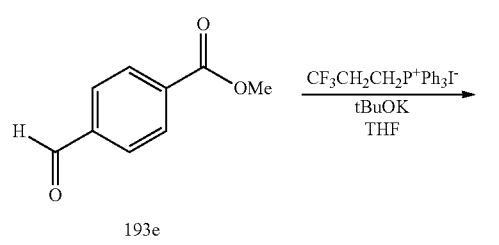

193e

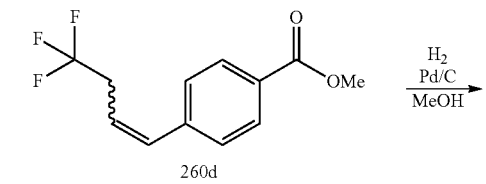

260d

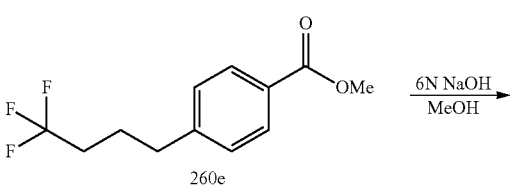

260e

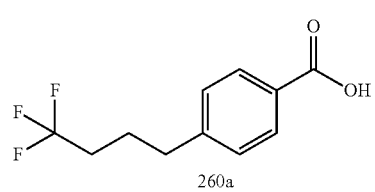

260a (Reaction 260-3)

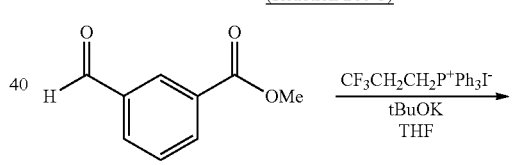

193n

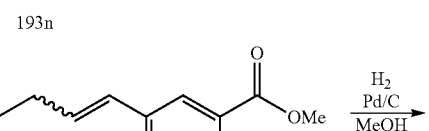

260f

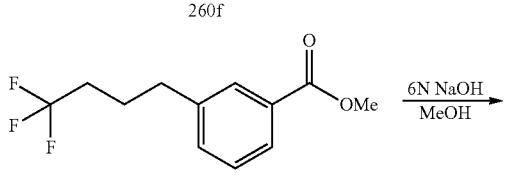

260g

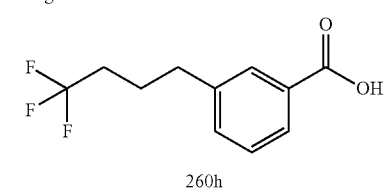

260h 3-(4,4,4-Trifluoro-butyl)-benzoic acid was synthesized by operations similar to those in Reaction 191-14, Reaction 18-2 and Reaction 95-18 using appropriate reagents and starting material.

MS (ESI) m/z=233 (M+H)+.

Example 261

1-(3,5-Dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea (Compound 1090)

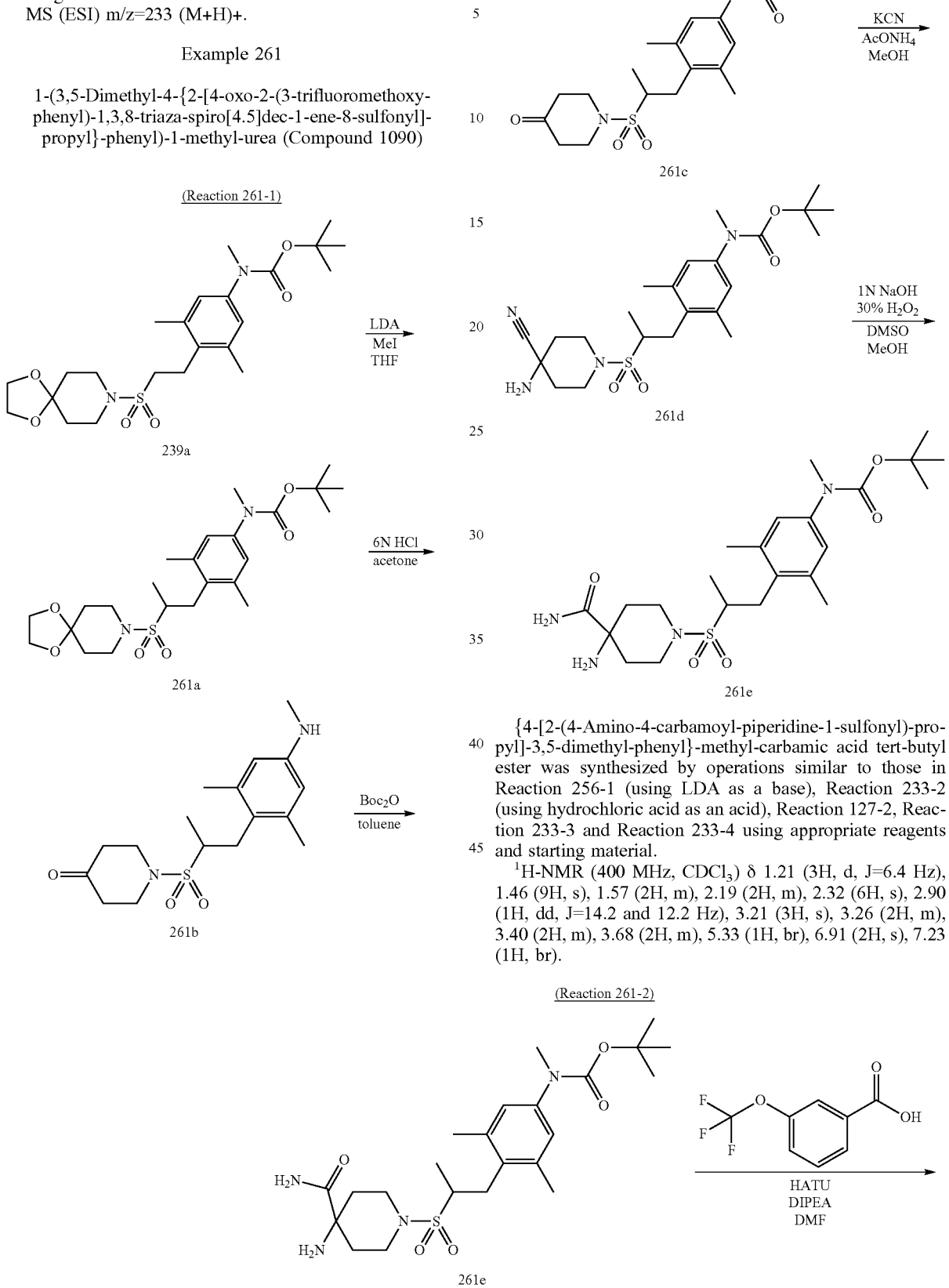

{4-[2-(4-Amino-4-carbamoyl-piperidine-1-sulfonyl)-propyl]-3,5-dimethyl-phenyl}-methyl-carbamic acid tert-butyl ester was synthesized by operations similar to those in Reaction 256-1 (using LDA as a base), Reaction 233-2 (using hydrochloric acid as an acid), Reaction 127-2, Reaction 233-3 and Reaction 233-4 using appropriate reagents and starting material.

$^1$H-NMR (400 MHz, CDCl$_3$) δ 1.21 (3H, d, J=6.4 Hz), 1.46 (9H, s), 1.57 (2H, m), 2.19 (2H, m), 2.32 (6H, s), 2.90 (1H, dd, J=14.2 and 12.2 Hz), 3.21 (3H, s), 3.26 (2H, m), 3.40 (2H, m), 3.68 (2H, m), 5.33 (1H, br), 6.91 (2H, s), 7.23 (1H, br).

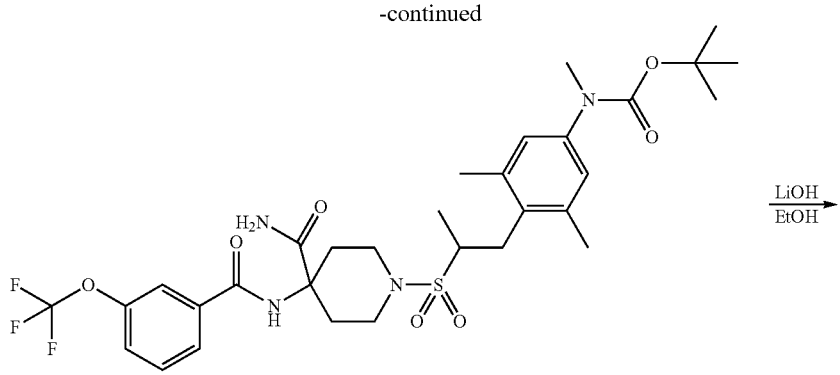
261f
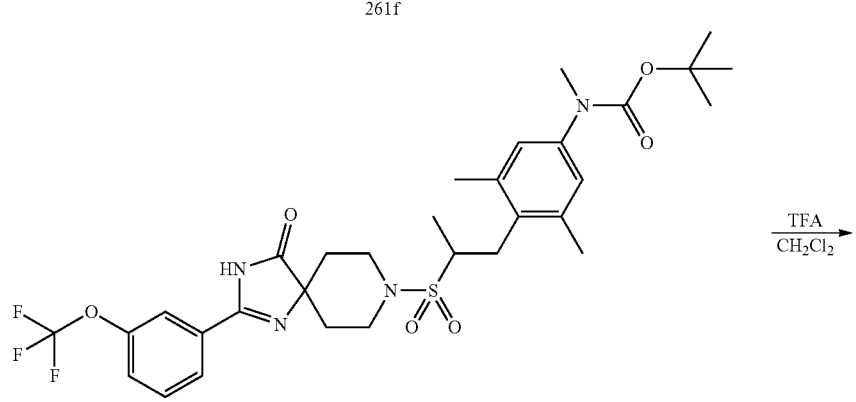
261g
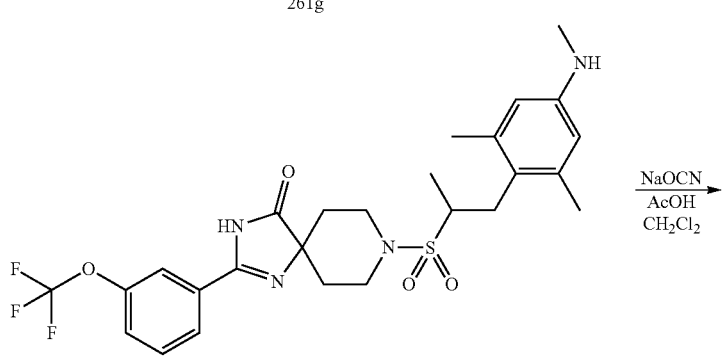
261h
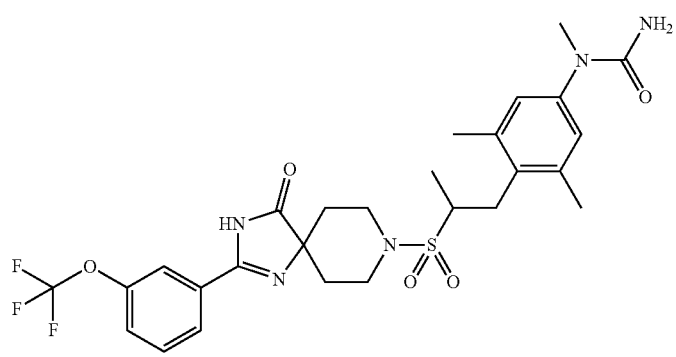
Compound 1090
1-(3,5-Dimethyl-4-{2-[4-oxo-2-(3-trifluoromethoxy-phenyl)-1,3,8-triaza-spiro[4.5]dec-1-ene-8-sulfonyl]-propyl}-phenyl)-1-methyl-urea was synthesized by operations similar to those in Reaction 10-14, Reaction 101-3, Reaction 4-1 and Reaction 89-2 using appropriate reagents and starting material.
MS (ESI) m/z=596 (M+H)+.

Example 262

2-[4-Fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one (Compound 1091)

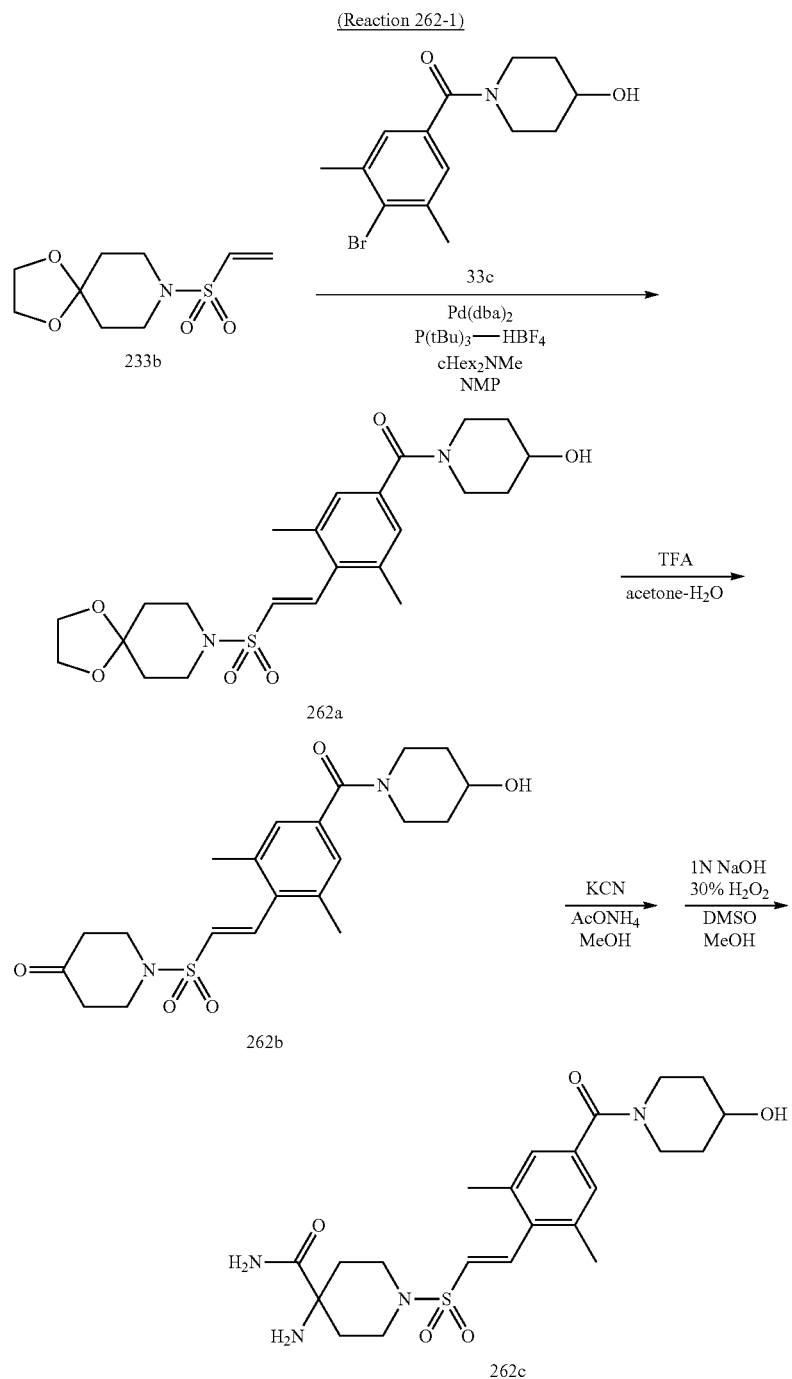

4-Amino-1-{(E)-2-[4-(4-hydroxy-piperidine-1-carbonyl)-2,6-dimethyl-phenyl]-ethenesulfonyl}-piperidine-4-carboxylic amide was synthesized by operations similar to those in Reaction 119-1, Reaction 233-2, Reaction 233-3 and Reaction 233-4 using appropriate reagents and starting material.

MS (ESI) m/z=465 (M+H)+.

(Reaction 262-2)

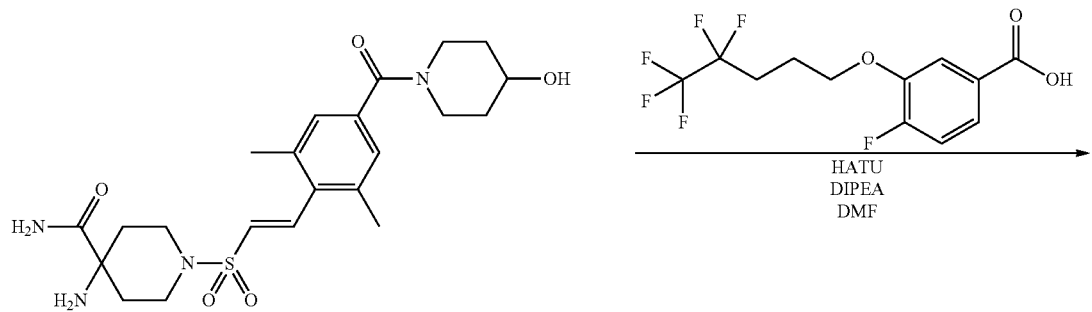

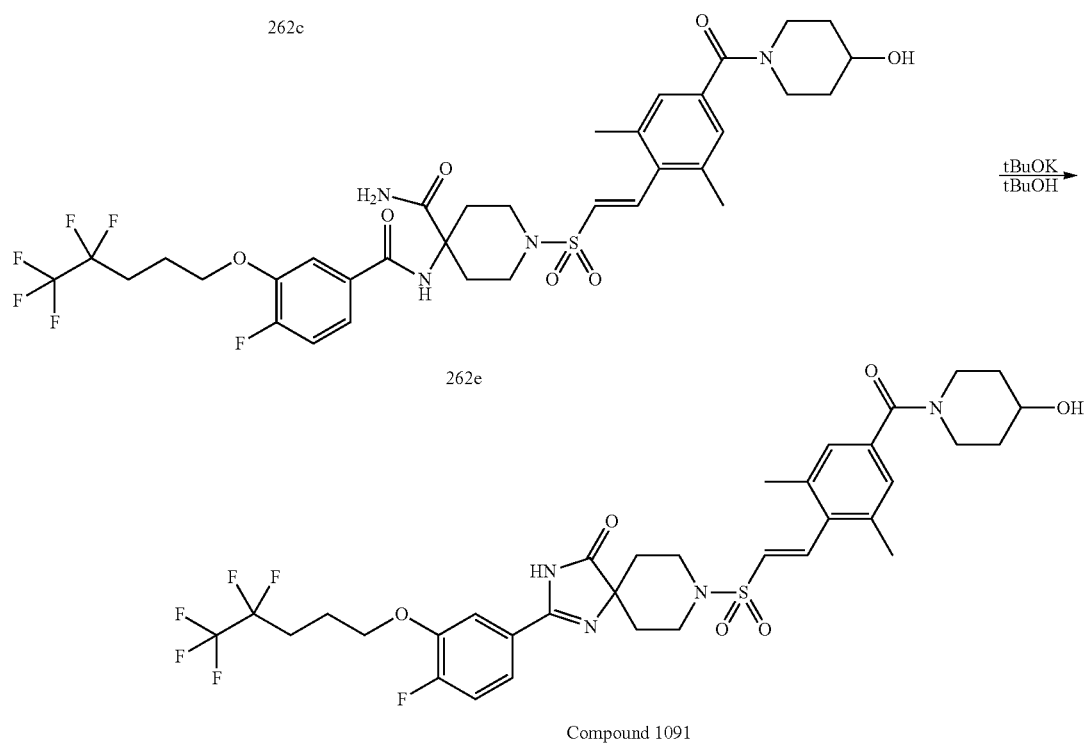

Compound 1091

2-[4-Fluoro-3-(4,4,5,5,5-pentafluoro-pentyloxy)-phenyl]-8-{(E)-2-[4-(4-hydroxy-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=745 (M+H)+.

The carboxylic acid reagent used in the synthesis of Compound 1091 (4-fluoro-3-(4,4,5,5,5-pentafluoro-pentyloxy)-benzoic acid) was synthesized by the following method.

(Reaction 262-3)

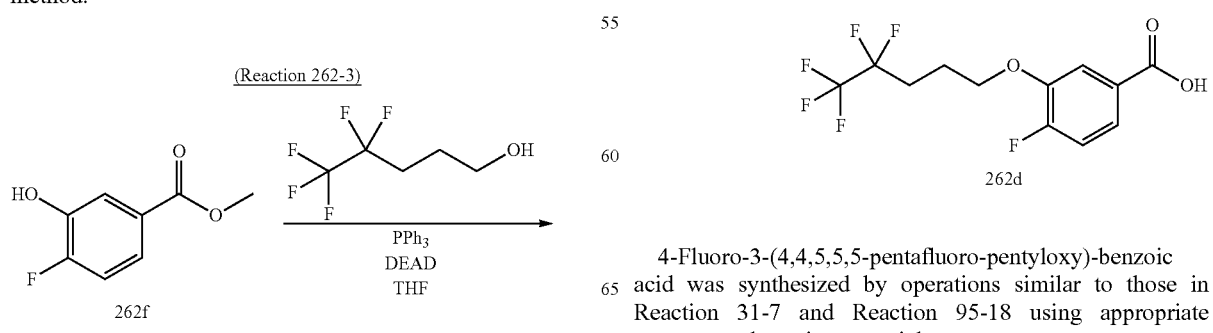

4-Fluoro-3-(4,4,5,5,5-pentafluoro-pentyloxy)-benzoic acid was synthesized by operations similar to those in Reaction 31-7 and Reaction 95-18 using appropriate reagents and starting material.

1H-NMR (400 MHz, CD₃OD) δ 0.21-0.14 (2H, m), 2.30-2.42 (2H, m), 4.19 (2H, t, J=6.0 Hz), 7.20 (1H, dd, J=10.8, 8.4 Hz), 7.64-7.68 (1H, m), 7.72 (1H, dd, J=8.4, 2.0 Hz).

Example 263

2-[4-Fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one (Compound 1092)

(Reaction 263-1)

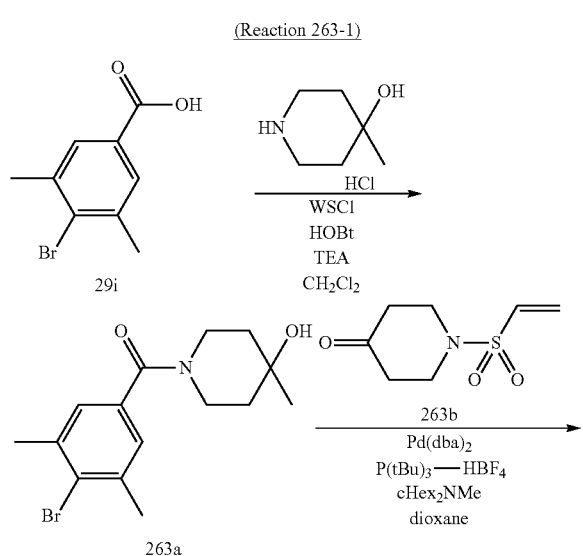

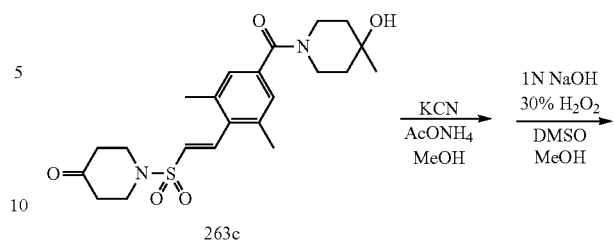

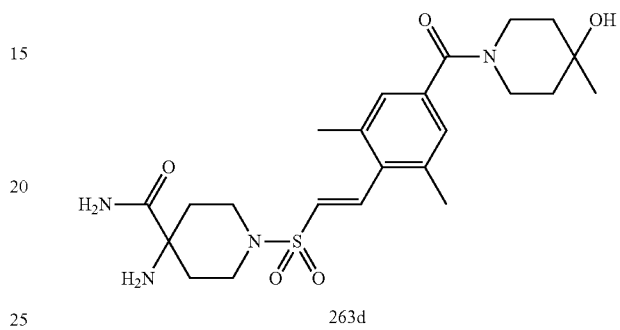

4-Amino-1-{(E)-2-[4-(4-hydroxy-4-methyl-piperidine-1-carbonyl)-2,6-dimethyl-phenyl]-ethenesulfonyl}-piperidine-4-carboxylic amide was synthesized by operations similar to those in Reaction 10-18, Reaction 119-1, Reaction 233-3 and Reaction 233-4 using appropriate reagents and starting material.

MS (ESI) m/z=479 (M+H)+.

(Reaction 263-2)

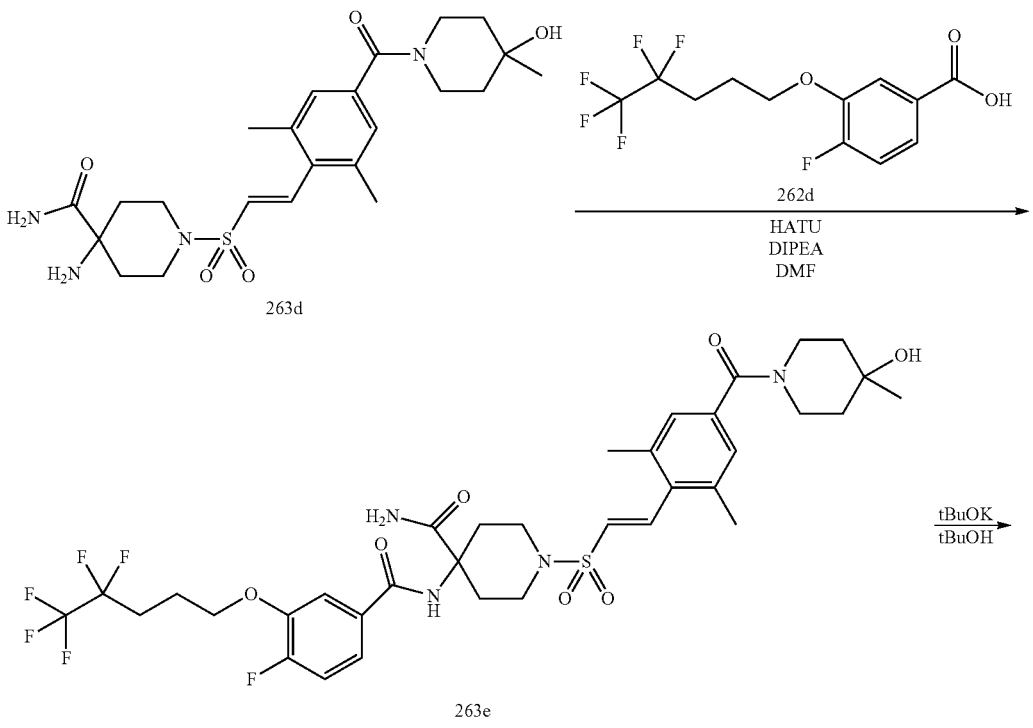

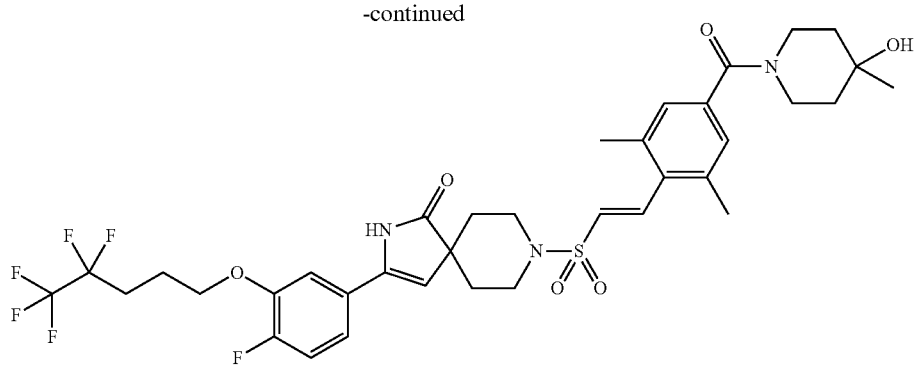

Compound 1092

2-[4-Fluoro-3-(4,4,5,5,5-pentafluoro-pentyloxy)-phenyl]-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=759 (M+H)+.

The example compounds shown below were synthesized by operations similar to those in Reaction 263-2 using appropriate reagents and starting materials.

Compounds 1093 to 1099

TABLE 162

| Compound | Structure | LCMS condition | Retention time (min) | MS (m/z) |
|---|---|---|---|---|
| 1093 | 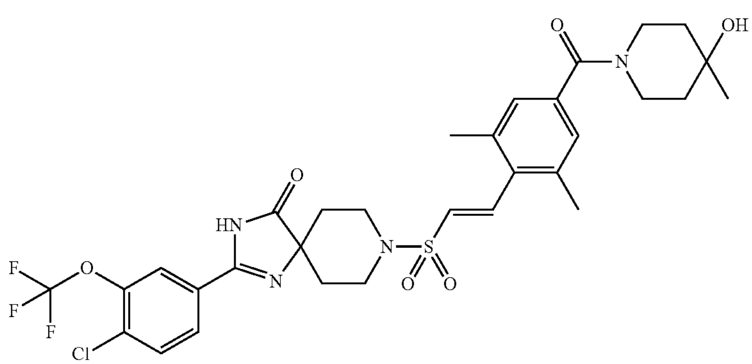 [SMILES: Cc1cc(C(=O)N2CCC(C)(O)CC2)cc(C)c1/C=C/S(=O)(=O)N1CCC2(CC1)N=C(c1ccc(Cl)c(OC(F)(F)F)c1)NC2=O] | LCMS-F-1 | 1.03 | 683 (M + H)+ |
| 1094 | 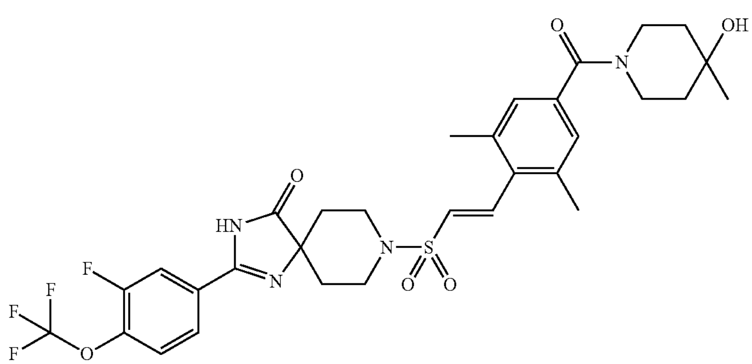 [SMILES: Cc1cc(C(=O)N2CCC(C)(O)CC2)cc(C)c1/C=C/S(=O)(=O)N1CCC2(CC1)N=C(c1ccc(OC(F)(F)F)c(F)c1)NC2=O] | LCMS-F-1 | 1.01 | 667 (M + H)+ |

TABLE 162-continued

| Compound | Structure | LCMS condition | Retention time (min) | MS (m/z) |
|---|---|---|---|---|
| 1095 | 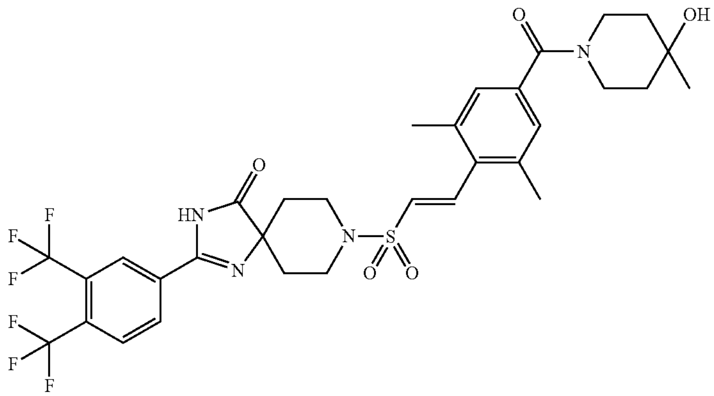 [SMILES: Cc1cc(C(=O)N2CCC(C)(O)CC2)cc(C)c1/C=C/S(=O)(=O)N1CCC2(CC1)N=C(c1ccc(C(F)(F)F)c(C(F)(F)F)c1)NC2=O] | LCMS-F-1 | 1.03 | 701 (M + H)+ |
| 1096 | 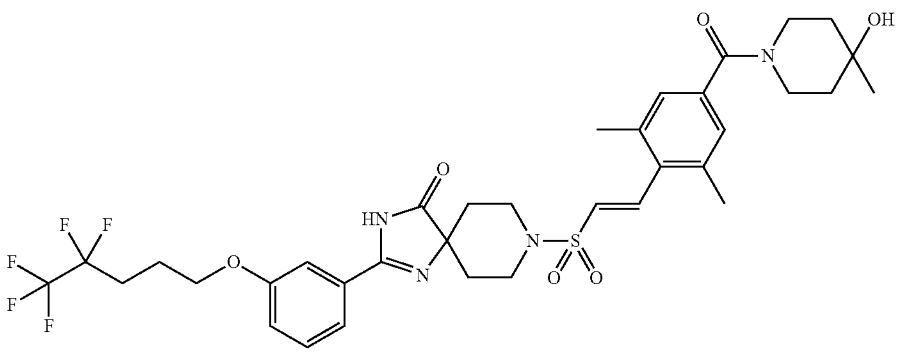 [SMILES: Cc1cc(C(=O)N2CCC(C)(O)CC2)cc(C)c1/C=C/S(=O)(=O)N1CCC2(CC1)N=C(c1cccc(OCCCC(F)(F)C(F)(F)F)c1)NC2=O] | LCMS-F-1 | 1.05 | 741 (M + H)+ |
| 1097 | 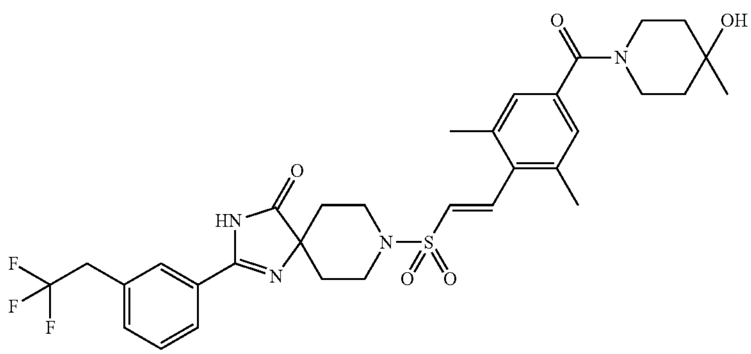 [SMILES: Cc1cc(C(=O)N2CCC(C)(O)CC2)cc(C)c1/C=C/S(=O)(=O)N1CCC2(CC1)N=C(c1cccc(CC(F)(F)F)c1)NC2=O] | LCMS-C-1 | 2.60 | 647 (M + H)+ |
| 1098 | 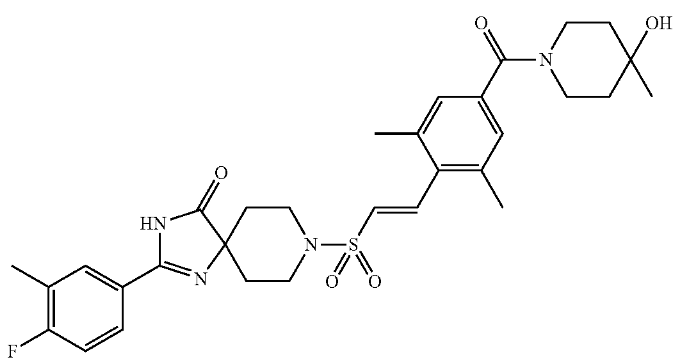 [SMILES: Cc1cc(C2=NC3(CCN(S(=O)(=O)/C=C/c4c(C)cc(C(=O)N5CCC(C)(O)CC5)cc4C)CC3)C(=O)N2)ccc1F] | LCMS-C-1 | 2.60 | 597 (M + H)+ |

TABLE 162-continued

| Compound | Structure | LCMS condition | Retention time (min) | MS (m/z) |
|---|---|---|---|---|
| 1099 | 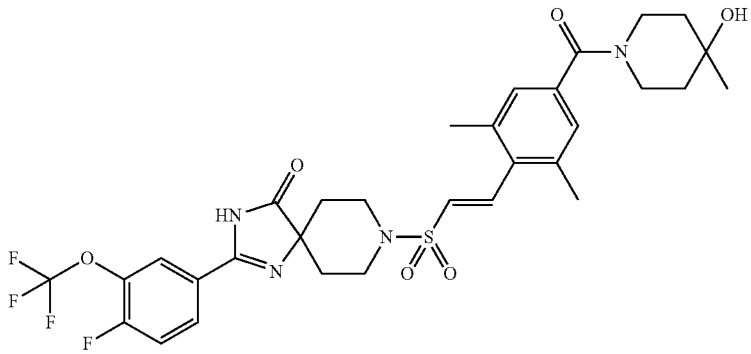 | LCMS-F-1 | 1.01 | 667 (M + H)+ |

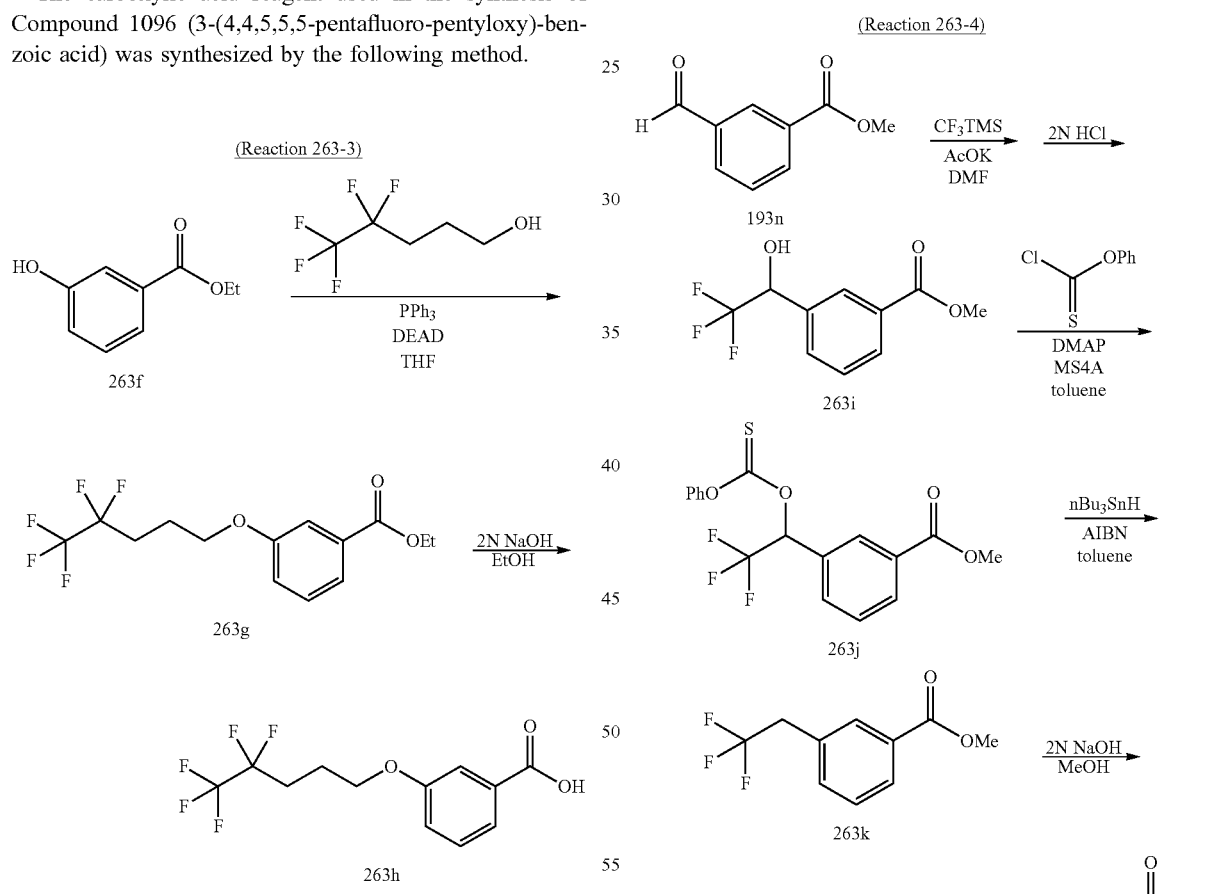

The carboxylic acid reagent used in the synthesis of Compound 1096 (3-(4,4,5,5,5-pentafluoro-pentyloxy)-benzoic acid) was synthesized by the following method.

(Reaction 263-3)

263f

263g

263h 3-(4,4,5,5,5-Pentafluoro-pentyloxy)-benzoic acid was synthesized by operations similar to those in Reaction 31-7 and Reaction 95-18 using appropriate reagents and starting material.

MS (ESI) m/z=297 (M–H)–.

The carboxylic acid reagent used in the synthesis of Compound 1097 (3-(2,2,2-trifluoro-ethyl)-benzoic acid) was synthesized by the following method.

(Reaction 263-4)

193n

263i

263j

263k

263l 3-(2,2,2-Trifluoro-ethyl)-benzoic acid was synthesized by operations similar to those in Reaction 193-4, Reaction 193-5, Reaction 193-6 and Reaction 95-18 using appropriate reagents and starting material.

$^1$H-NMR (400 MHz, CDCl$_3$) δ 3.43 (2H, q, J=10.8 Hz), 3.93 (3H, s), 7.43-7.51 (2H, m), 7.99-8.04 (2H, m).

Example 264

8-{(E)-2-[4-(4-Hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one (Compound 1100)

(Reaction 264-1)

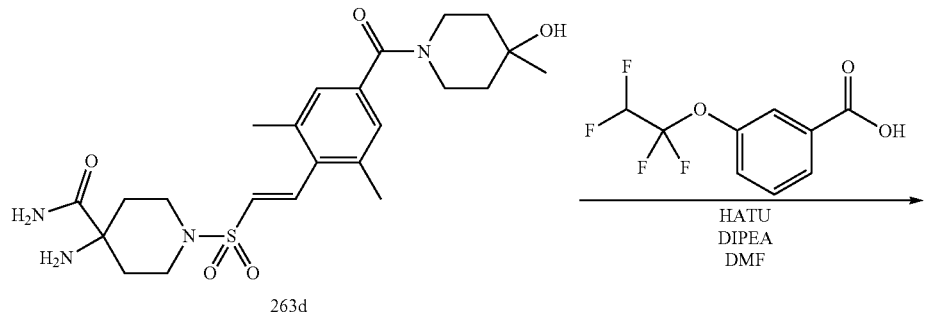

263d

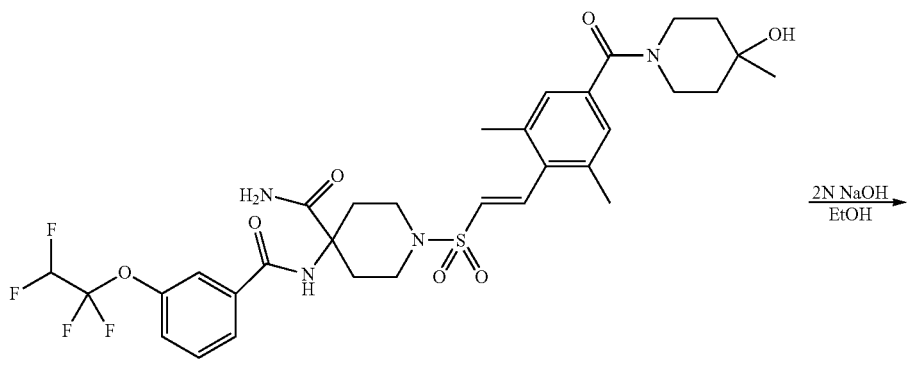

264a

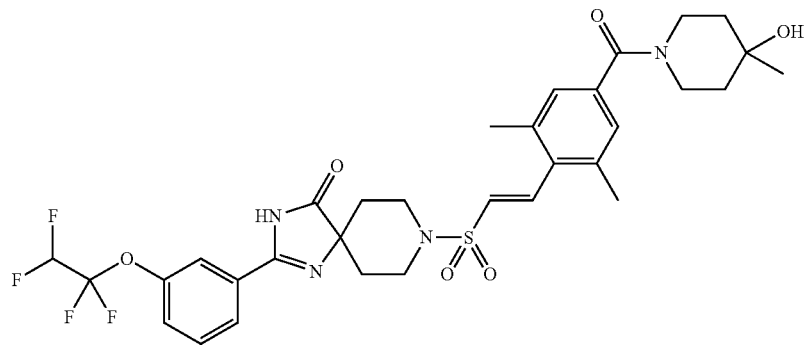

Compound 1100

8-{(E)-2-[4-(4-Hydroxy-4-methyl-piperidine-1-carbonyl)-2,6-dimethyl-phenyl]-ethenesulfonyl}-2-[3-(1,1,2,2-tetrafluoro-ethoxy)-phenyl]-1,3,8-triaza-spiro[4.5]dec-1-en-4-one was synthesized by operations similar to those in Reaction 10-14 and Reaction 189-5 using appropriate reagents and starting material.

MS (ESI) m/z=681 (M+H)+.

Example 265

8-{1,1-Difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one (Compound 1101)

(Reaction 265-1)

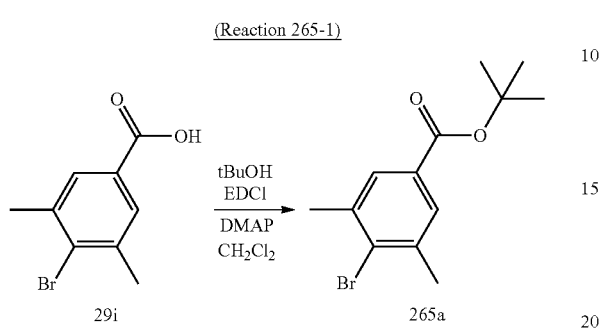

Dehydrated tert-butanol (0.19 ml, 2.0 mmol), 4-dimethylaminopyridine (81 mg, 0.67 mmol) and EDCI (255 mg, 1.33 mmol) were added to a solution of 4-bromo-3,5-dimethyl-benzoic acid (123 mg, 0.535 mmol) in dichloromethane (1.0 ml) at 0° C., and the mixture was stirred at room temperature for 25 hours. The reaction mixture was diluted with dichloromethane, and the organic layer was washed with water, dried over MgSO$_4$ and concentrated under reduced pressure. The resulting residue was purified by silica gel column chromatography (hexane/ethyl acetate=100/1→50/1) to give 4-bromo-3,5-dimethyl-benzoic acid tert-butyl ester (106 mg, 70%).

$^1$H-NMR (400 MHz, CDCl$_3$) δ 1.58 (9H, s), 2.45 (6H, s), 7.66 (2H, s).

(Reaction 265-2)

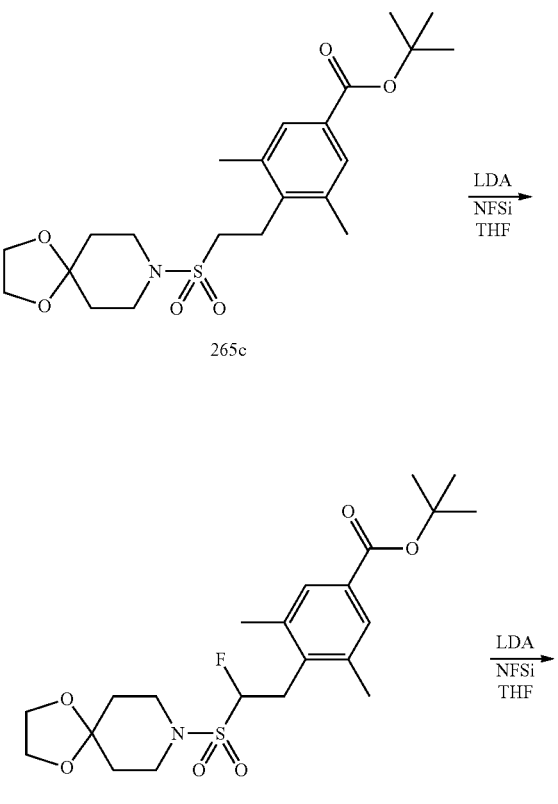

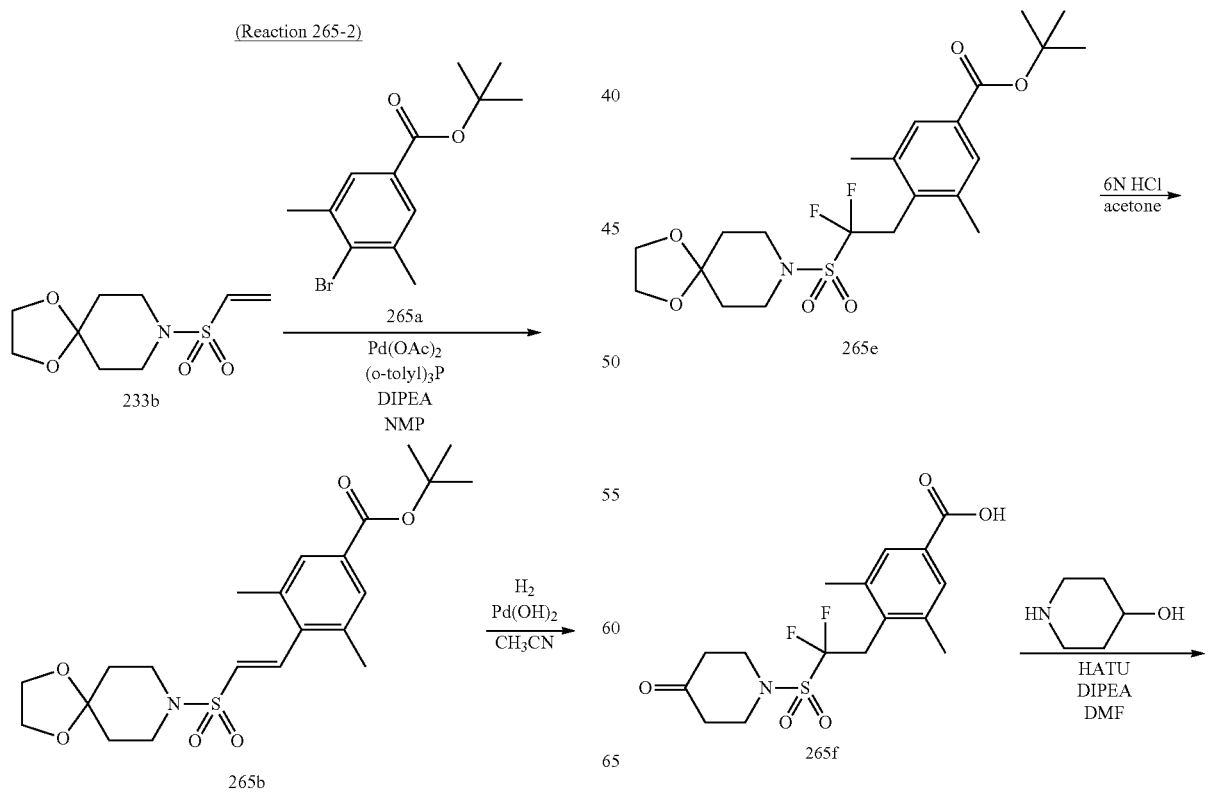

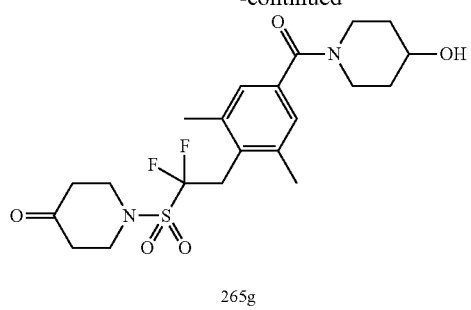

265g

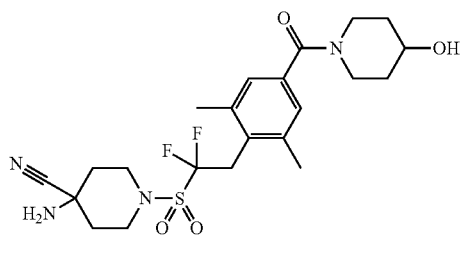

265h

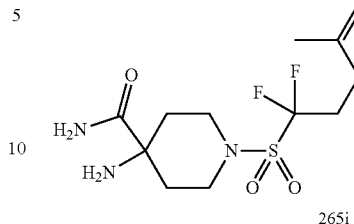

265i

4-Amino-1-{1,1-difluoro-2-[4-(4-hydroxy-piperidine-1-carbonyl)-2,6-dimethyl-phenyl]-ethanesulfonyl}-piperidine-4-carboxylic amide was synthesized by operations similar to those in Reaction 26-1, Reaction 184-1, Reaction 257-1, Reaction 257-1, Reaction 233-2, Reaction 10-14, Reaction 233-3 and Reaction 233-4 using appropriate reagents and starting material.

$^1$H-NMR (400 MHz, CDCl$_3$) δ 1.07 (2H, br), 1.53 (2H, m), 1.84 and 1.95 (each 1H, br), 2.21 (2H, m), 2.36 (6H, s), 3.21 and 3.33 (each 1H, br), 3.48 (2H, m), 3.68 (2H, dd, J=20.4 and 18.4 Hz), 3.70 (1H, br), 3.86 (2H, m), 3.97 (1H, m), 4.20 (1H, br), 5.33 (1H, br), 7.07 (2H, s), 7.19 (1H, br).

(Reaction 265-3)

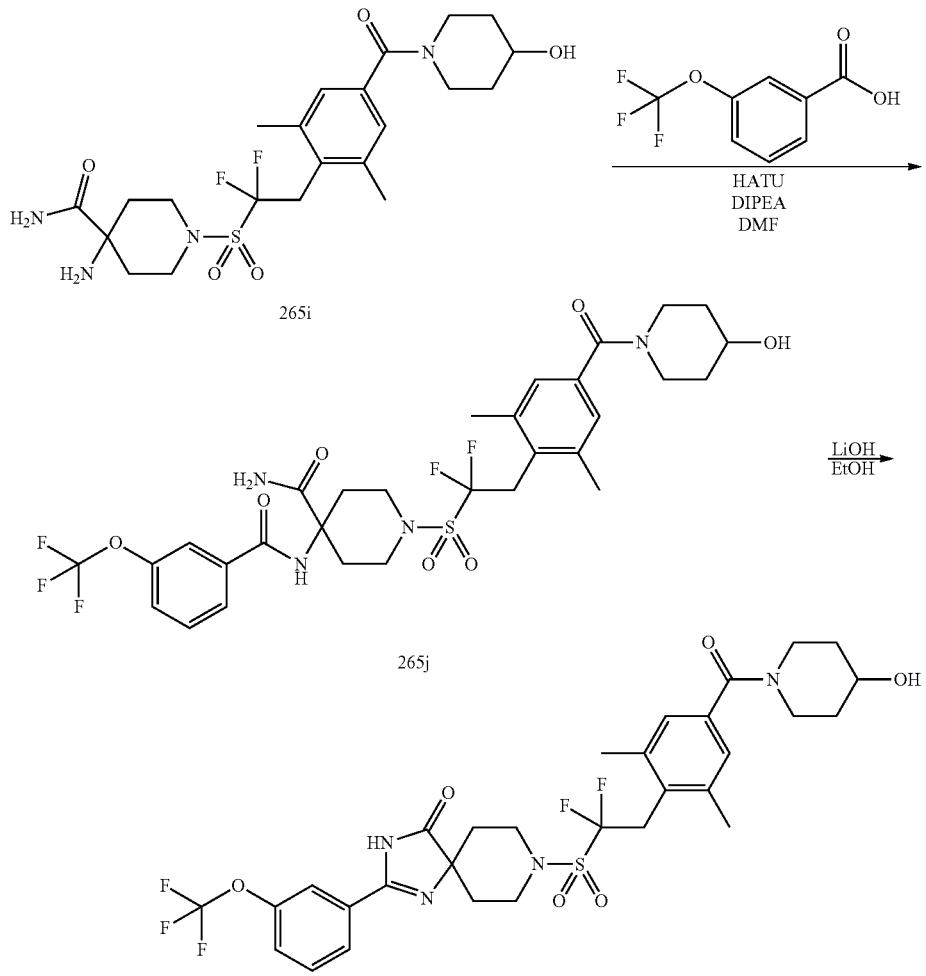

Compound 1101

8-{1,1-Difluoro-2-[4-(4-hydroxy-piperidine-1-carbonyl)-2,6-dimethyl-phenyl]-ethanesulfonyl}-2-(3-trifluoromethoxy-phenyl)-1,3,8-triaza-spiro[4.5]dec-1-en-4-one was synthesized by operations similar to those in Reaction 10-14 and Reaction 101-3 using appropriate reagents and starting material.

MS (ESI) m/z=673 (M+H)+.

Example 266

2-(4-Fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one (Compound 1102)

(Reaction 266-1)

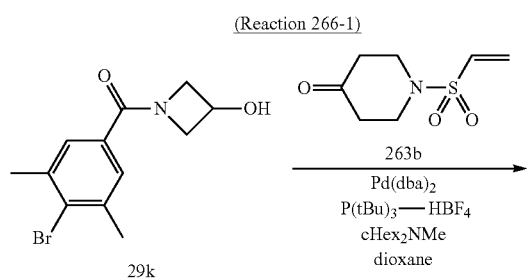

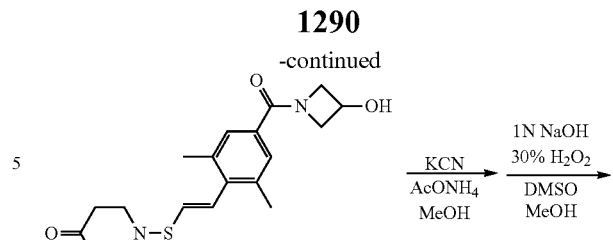

4-Amino-1-{(E)-2-[4-(3-hydroxy-azetidine-1-carbonyl)-2,6-dimethyl-phenyl]-ethenesulfonyl}-piperidine-4-carboxylic amide was synthesized by operations similar to those in Reaction 119-1, Reaction 233-3 and Reaction 233-4 using appropriate reagents and starting material.

MS (ESI) m/z=437 (M+H)+.

(Reaction 266-2)

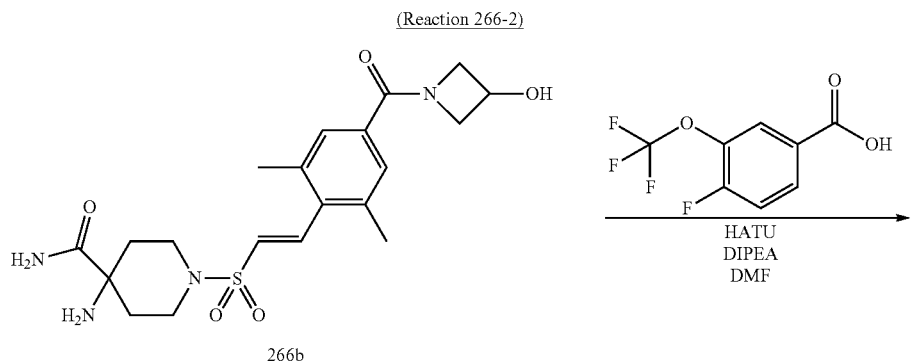

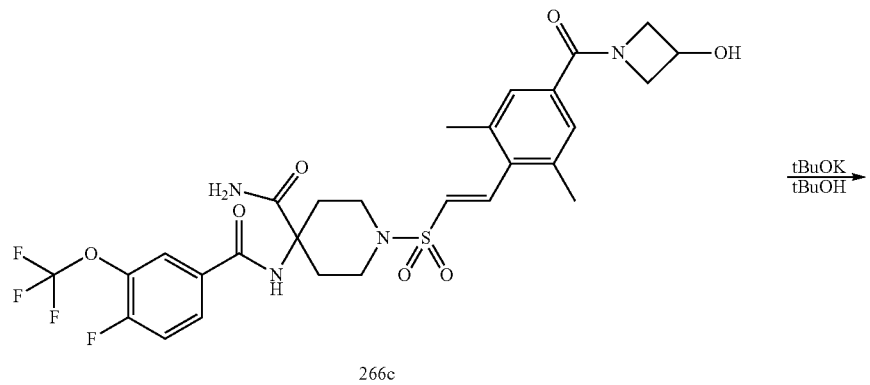

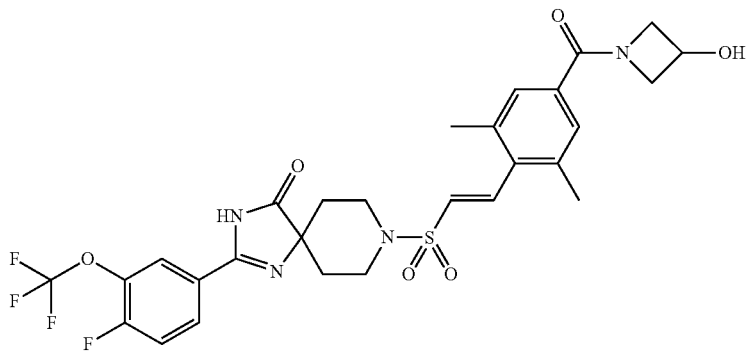

Compound 1102

2-(4-Fluoro-3-trifluoromethoxy-phenyl)-8-{(E)-2-[4-(3-hydroxy-azetidine-1-carbonyl)-2,6-dimethyl-phenyl]-ethenesulfonyl}-1,3,8-triaza-spiro[4.5]dec-1-en-4-one was synthesized by operations similar to those in Reaction 10-14 and Reaction 10-12 using appropriate reagents and starting material.

MS (ESI) m/z=625 (M+H)+.

Example 267

8-{(E)-2-[4-((R)-2,3-Dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one (Compound 1103)

(Reaction 267-1)

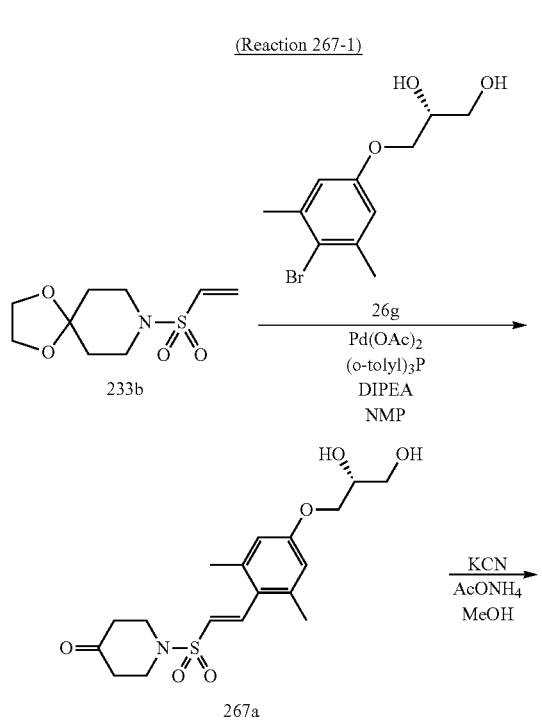

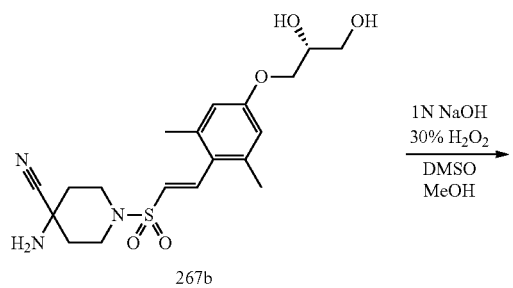

4-Amino-1-{(E)-2-[4-((R)-2,3-dihydroxy-propoxy)-2,6-dimethyl-phenyl]-ethenesulfonyl}-piperidine-4-carboxylic amide was synthesized by operations similar to those in Reaction 26-1, Reaction 233-3 and Reaction 233-4 using appropriate reagents and starting material.

MS (ESI) m/z=428 (M+H)+.

(Reaction 267-2)
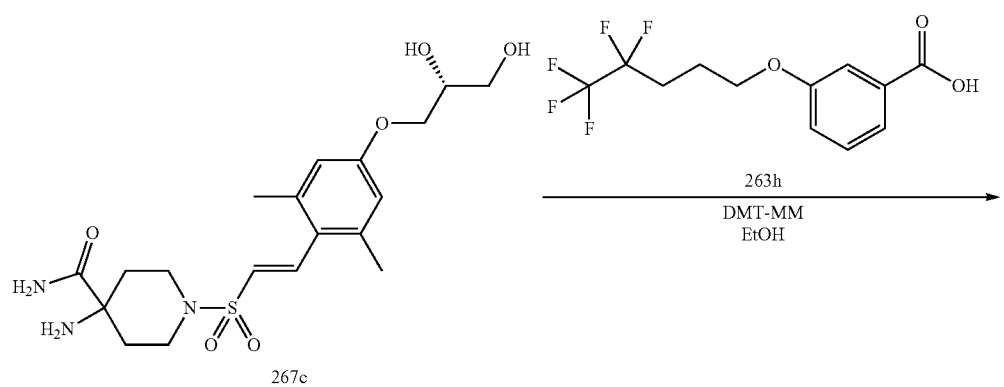
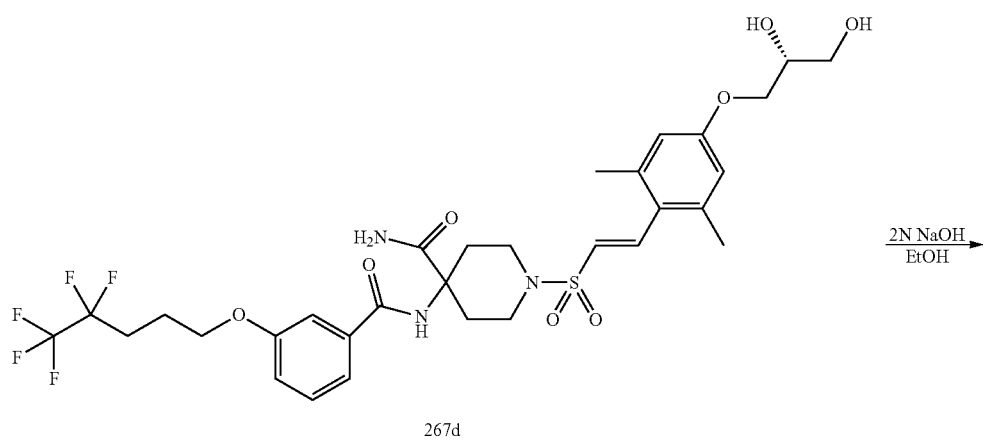
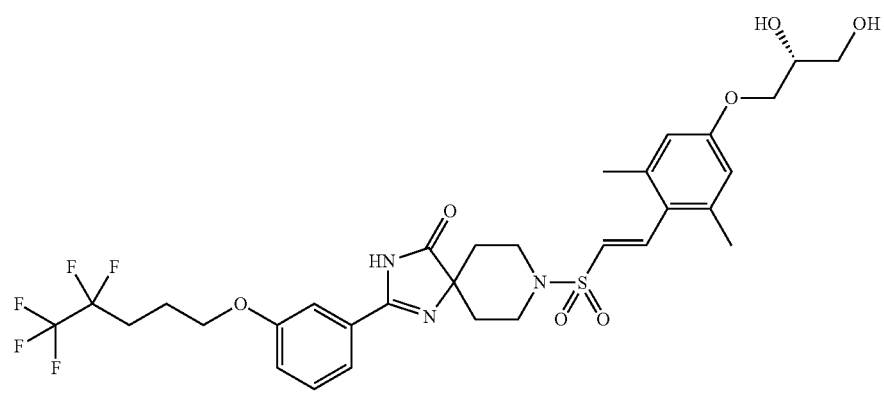
Compound 1103
8-{(E)-2-[4-((R)-2,3-Dihydroxy-propoxy)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one was synthesized by operations similar to those in Reaction 10-1 and Reaction 189-5 using appropriate reagents and starting material.
MS (ESI) m/z=690 (M+H)+.

Example 268

6-(4-Methyl-cyclohexyl)-2-(2-naphthalen-1-yl-ethanesulfonyl)-2,5,7-triaza-spiro[3.4]oct-5-en-8-one (Compound 1104)

(Reaction 268-1)

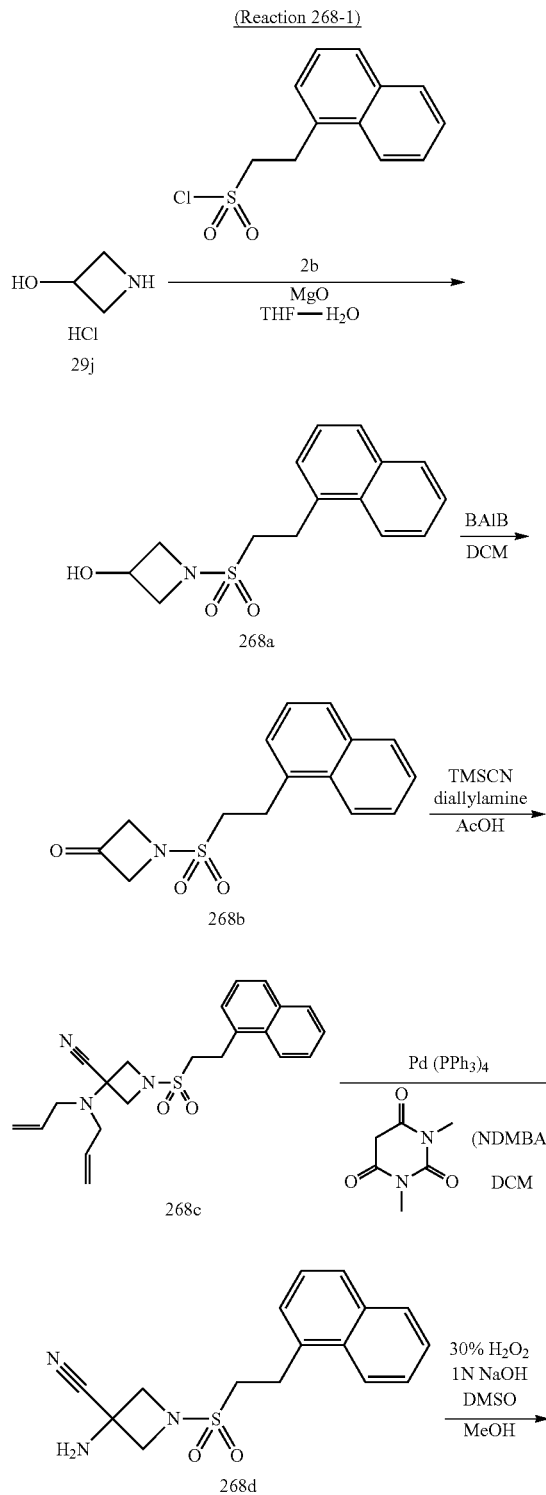

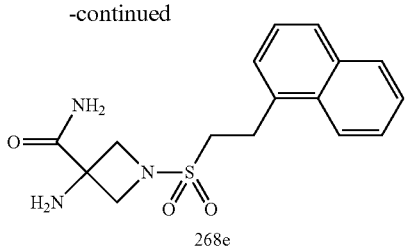

3-Amino-1-(2-naphthalen-1-yl-ethanesulfonyl)-azetidine-3-carboxylic amide was synthesized by operations similar to those in Reaction 190-1, Reaction 109-1, Reaction 200-2, Reaction 200-3 and Reaction 233-4 using appropriate reagents and starting material.

MS (ESI) m/z=334 (M+H)+.

(Reaction 268-2)

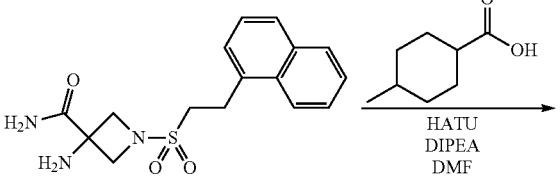

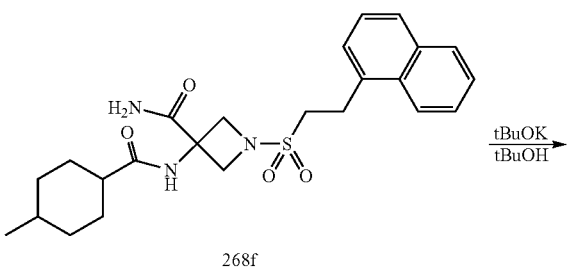

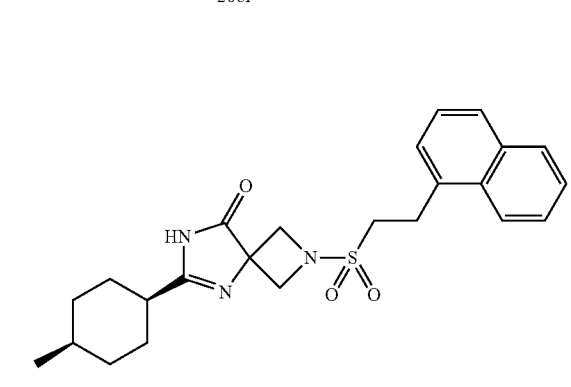

Compound 1104

6-(4-Methyl-cyclohexyl)-2-(2-naphthalen-1-yl-ethanesulfonyl)-2,5,7-triaza-spiro[3.4]oct-5-en-8-one was synthesized by operations similar to those in Reaction 10-14 and Reaction 10-12 using appropriate reagents and starting material.

MS (ESI) m/z=440 (M+H)+.

Example 269

8-[(E)-2-(2,6-Dimethyl-4-methylamino-phenyl)-ethenesulfonyl]-2-(11-hydroxy-undecyl)-1,3,8-tri-aza-spiro[4.5]dec-1-en-4-one

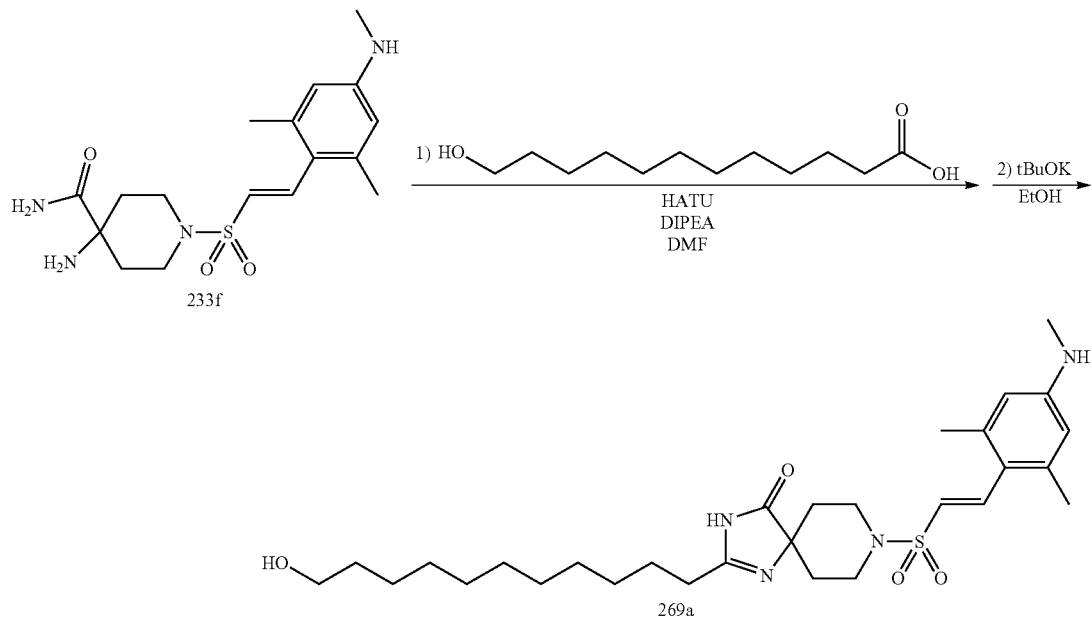

HATU (57 mg, 0.149 mmol) was added to a solution of 12-hydroxy-dodecanoic acid (33 mg, 0.149 mol), 4-amino-1-[(E)-2-(2,6-dimethyl-4-methylamino-phenyl)-ethenesulfonyl]-piperidine-4-carboxylic amide (50 mg, 0.136 mmol) and diisopropylethylamine (71 μL, 0.47 mmol) in DMF (1.3 ml) at 0° C., and the mixture was stirred at room temperature for 1.5 hours. Ethanol (2.6 ml) and potassium t-butoxide (76 mg, 0.678 mmol) were added to the reaction mixture, and the mixture was heated with stirring at 70° C. for three hours. The reaction mixture was quenched with a saturated aqueous ammonium chloride solution, and water was then added, followed by extraction with ethyl acetate. The organic layer was sequentially washed with water and saturated brine, and then dried over anhydrous sodium sulfate and concentrated under reduced pressure. The resulting residue was purified by silica gel column chromatography (dichloromethane-methanol) to give 8-[(E)-2-(2,6-dimethyl-4-methylamino-phenyl)-ethenesulfonyl]-2-(11-hydroxy-undecyl)-1,3,8-triaza-spiro[4.5]dec-1-en-4-one (58.7 mg, 79%).

MS (ESI) m/z=547 (M+H)+.

The example compounds shown below were synthesized by operations similar to those in Reaction 269-1 using appropriate reagents and starting materials.

Compounds 1106 to 1107

TABLE 163

| Compound | Structure | LCMS condition | Retention time (min) | MS (m/z) |
|---|---|---|---|---|
| 1106 | 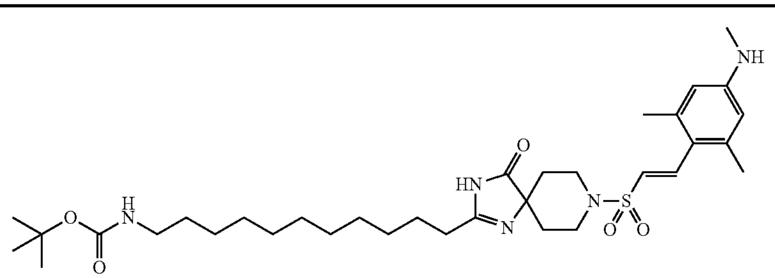 | LCMS-C-1 | 3.12 | 646 (M + H)+ |

TABLE 163-continued
| Compound | Structure | LCMS condition | Retention time (min) | MS (m/z) |
|---|---|---|---|---|
| 1107 | 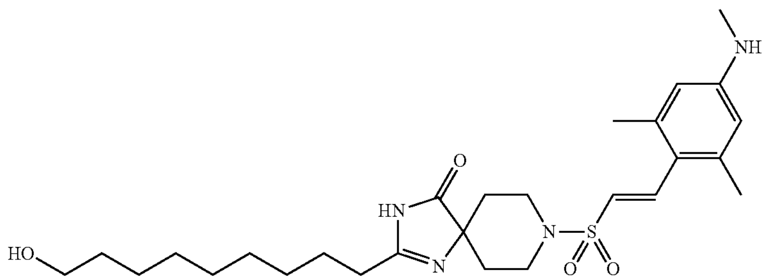 [SMILES: CNc1cc(C)c(/C=C/S(=O)(=O)N2CCC3(CC2)N=C(CCCCCCCCCO)NC3=O)c(C)c1] | LCMS-G-1 | 0.93 | 519 (M + H)+ |
Example 270
1-(3,5-Dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea (Compound 1108)
Reaction 270-1
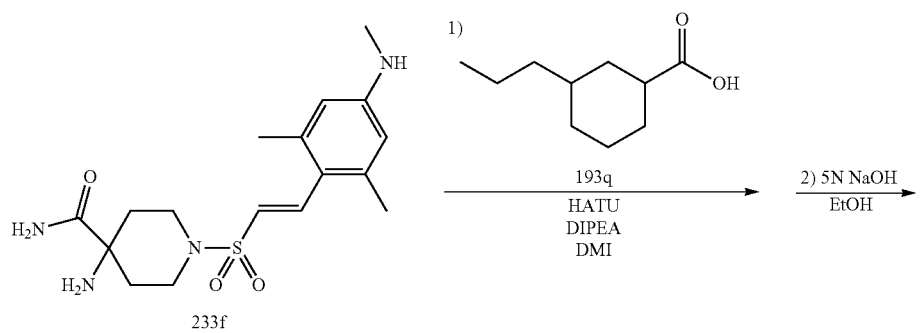
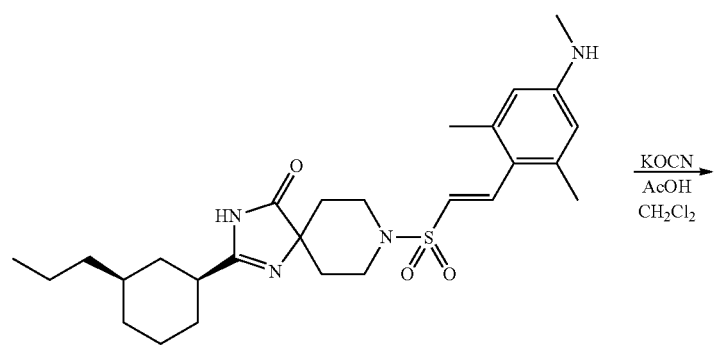

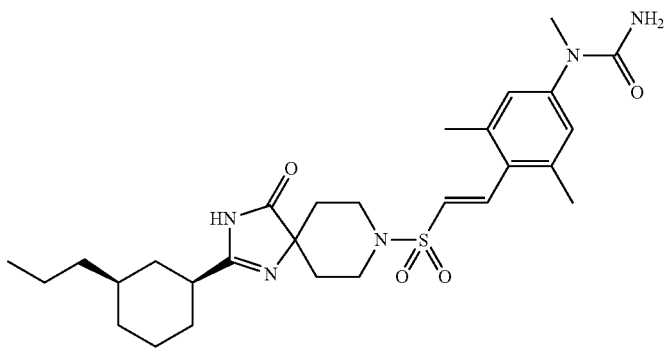

Compound 1108

1-(3,5-Dimethyl-4-{(E)-2-[4-oxo-2-((1S,3R)-3-propyl-cyclohexyl)-1,3,8-triaza-spiro[4.5]dec-1-ene-8-sulfonyl]-vinyl}-phenyl)-1-methyl-urea was synthesized by operations similar to those in Reaction 269-1 and Reaction 89-2 (using KOCN) using appropriate reagents and starting material.

MS (ESI) m/z=544 (M+H)+.

The example compounds shown below were synthesized by operations similar to those in Reaction 270-1 using appropriate reagents and starting materials.

Compounds 1109 to 1113

TABLE 164

| Compound | Structure | LCMS condition | Retention time (min) | MS (m/z) |
|---|---|---|---|---|
| 1109 | 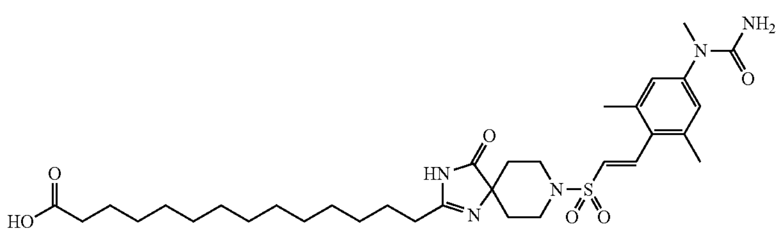 [SMILES: Cc1cc(N(C)C(N)=O)cc(C)c1/C=C/S(=O)(=O)N1CCC2(CC1)N=C(CCCCCCCCCCCCCC(=O)O)NC2=O] | LCMS-C-1 | 2.72 | 646 (M + H)+ |
| 1110 | 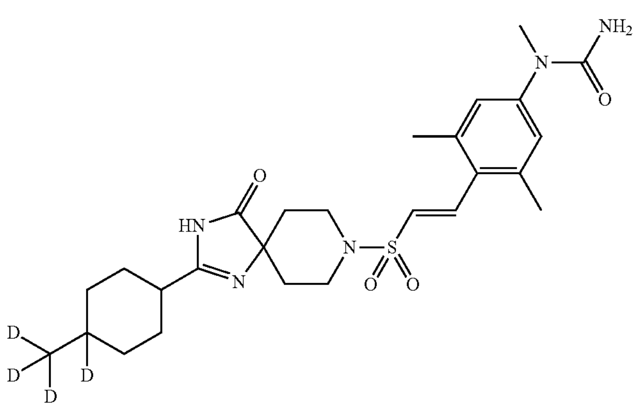 [SMILES: [2H]C([2H])([2H])C1([2H])CCC(C2=NC3(CCN(S(=O)(=O)/C=C/c4c(C)cc(N(C)C(N)=O)cc4C)CC3)C(=O)N2)CC1] | LCMS-F-1 | 0.93 | 520 (M + H)+ |

TABLE 164-continued

| Compound | Structure | LCMS condition | Retention time (min) | MS (m/z) |
|---|---|---|---|---|
| 1111 | 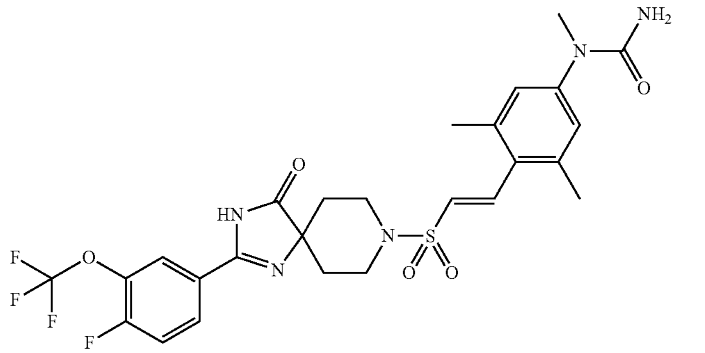 [SMILES: Cc1cc(N(C)C(N)=O)cc(C)c1/C=C/S(=O)(=O)N1CCC2(CC1)N=C(c1ccc(F)c(OC(F)(F)F)c1)NC2=O] | LCMS-F-1 | 0.93 | 598 (M + H)+ |
| 1112 | 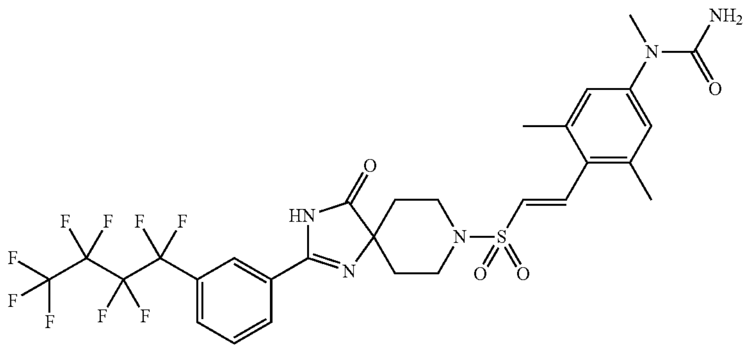 [SMILES: Cc1cc(N(C)C(N)=O)cc(C)c1/C=C/S(=O)(=O)N1CCC2(CC1)N=C(c1cccc(C(F)(F)C(F)(F)C(F)(F)C(F)(F)F)c1)NC2=O] | LCMS-F-1 | 1.03 | 714 (M + H)+ |
| 1113 | 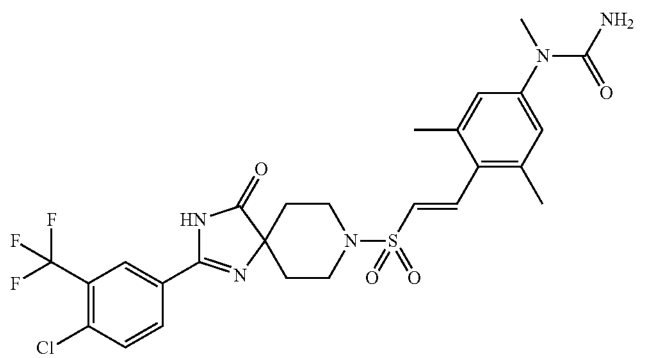 [SMILES: Cc1cc(N(C)C(N)=O)cc(C)c1/C=C/S(=O)(=O)N1CCC2(CC1)N=C(c1ccc(Cl)c(C(F)(F)F)c1)NC2=O] | LCMS-F-1 | 0.99 | 598 (M + H)+ |

The carboxylic acid reagent used in the synthesis of Compound 1110 (4-[1,1,1-²H₃]methyl-[4-²H₁]cyclohexanecarboxylic acid) was synthesized by the following method.

(Reaction 270-2)

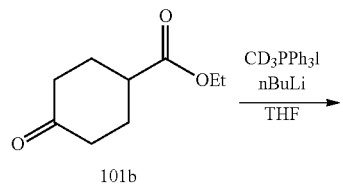

-continued

270b

4-[1,1,1-²H₃]Methylene-cyclohexanecarboxylic acid ethyl ester was synthesized by operations similar to those in Reaction 101-1 using appropriate reagents and starting material.

$^1$H-NMR (400 MHz, CDCl$_3$) δ 1.25 (3H, t, J=7.2 Hz), 1.52-1.64 (2H, m), 1.95-2.10 (4H, m), 2.34 (2H, ddd, J=13.6, 4.4, 4.4 Hz), 2.44 (1H, dddd, J=10.8, 10.8, 3.6, 3.6 Hz), 4.13 (2H, q, J=7.6 Hz).

(Reaction 270-3)

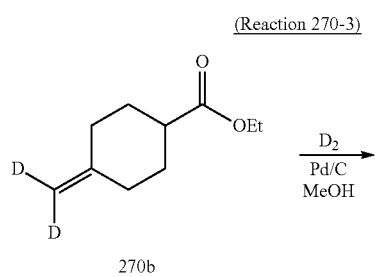

20% w/w Pd/C (2.6 mg) was added to a solution of 4-[1,1,1-²H₃]methylene-cyclohexanecarboxylic acid ethyl ester (26.0 mg, 153 μmol) in MeOH (1 ml) in an N₂ atmosphere. After deuterium substitution, the reaction mixture was stirred at room temperature for one hour. The reaction mixture was filtered through celite, and the filtrate was concentrated under reduced pressure to give 4-[1,1,1-²H₃]methyl-[4-²H₁]cyclohexanecarboxylic acid ethyl ester. This was used in the next step without further purification.

(Reaction 270-4)

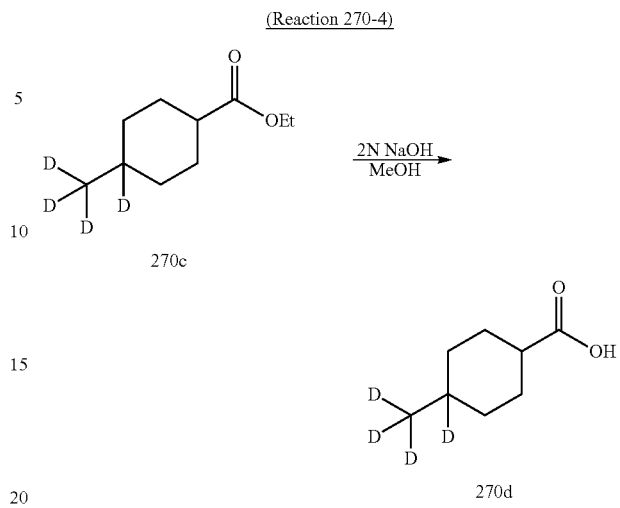

4-[1,1,1-²H₃]Methyl-[4-²H₁]cyclohexanecarboxylic acid was synthesized by operations similar to those in Reaction 95-18 using appropriate reagents and starting material. This was used in the next step without further purification.

Example 271

1-(3,5-Dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea (Compound 1114)

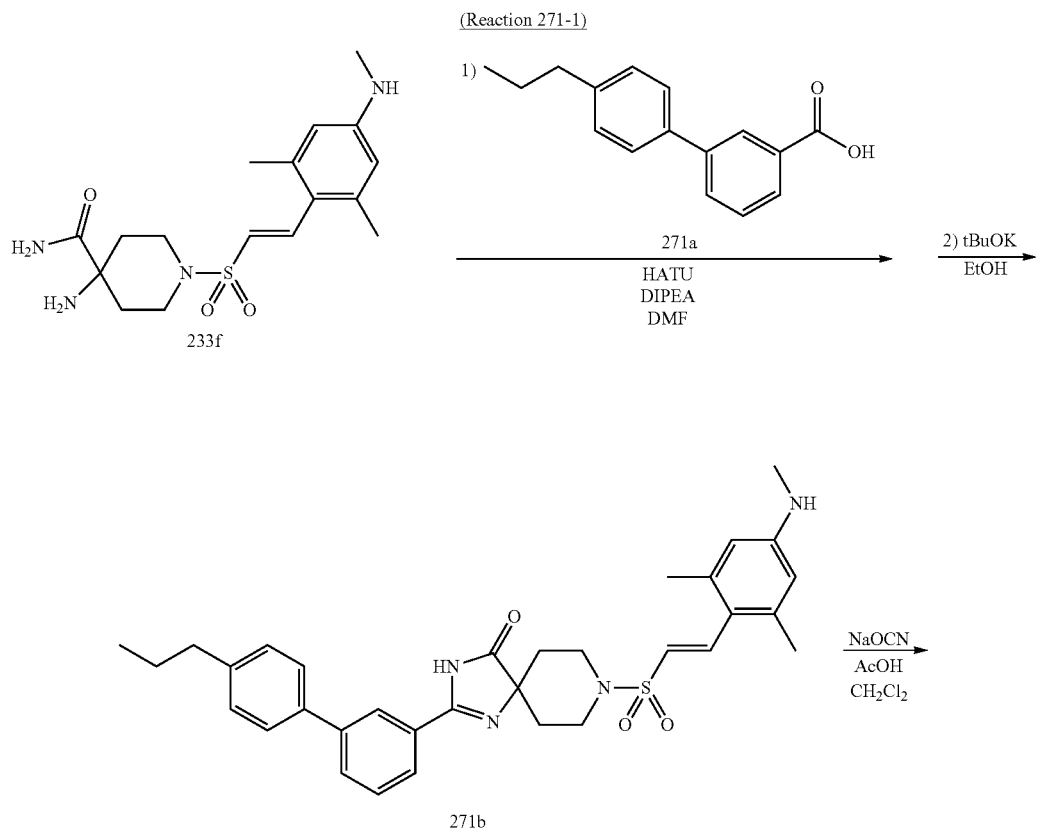

1307

-continued

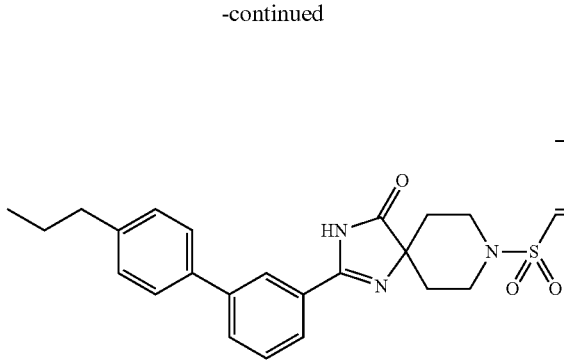

Compound 1114

1-(3,5-Dimethyl-4-{(E)-2-[4-oxo-2-(4'-propyl-biphenyl-3-yl)-1,3,8-triaza-spiro[4.5]dec-1-ene-8-sulfonyl]-vinyl}-phenyl)-1-methyl-urea was synthesized by operations similar to those in Reaction 269-1 and Reaction 89-2 using appropriate reagents and starting material.

MS (ESI) m/z=614 (M+H)+.

The carboxylic acid reagent used in the synthesis of Compound 1114 (4'-propyl-biphenyl-3-carboxylic acid) was synthesized by the following method.

(Reaction 271-2)

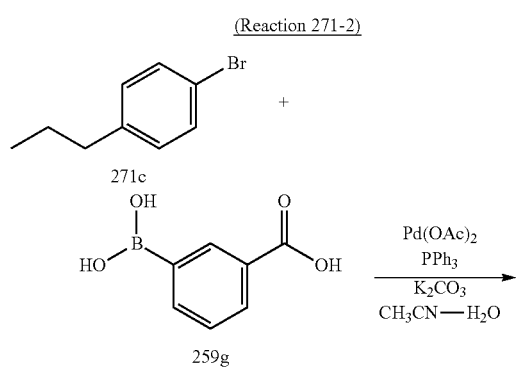

1308

-continued

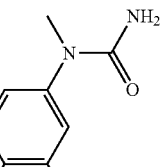

271a

4'-Propyl-biphenyl-3-carboxylic acid was synthesized by operations similar to those in Reaction 259-2 using appropriate reagents and starting material.

MS (ESI) m/z=241 (M+H)+.

The example compounds shown below were synthesized by operations similar to those in Reaction 259-1 using appropriate reagents and starting materials.

Compounds 1115 to 1130

TABLE 165

| Compound | Structure | LCMS condition | Retention time (min) | MS (m/z) |
|---|---|---|---|---|
| 1115 | 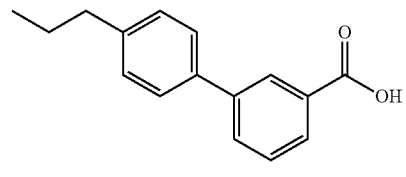 | LCMS-D-1 | 1.84 | 548 (M + H)+ |

TABLE 165-continued

| Compound | Structure | LCMS condition | Retention time (min) | MS (m/z) |
|---|---|---|---|---|
| 1116 | 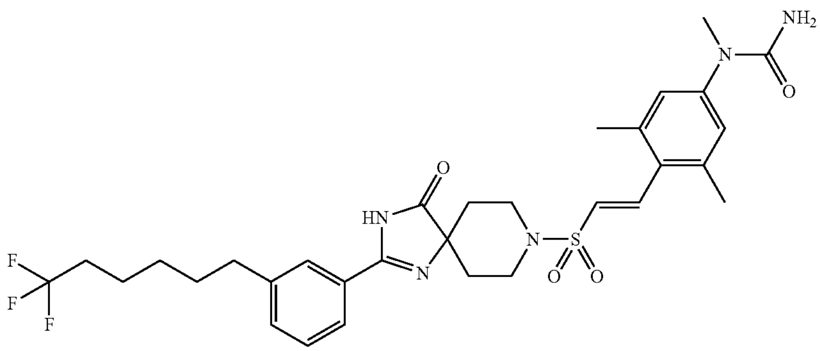 [SMILES: Cc1cc(N(C)C(N)=O)cc(C)c1/C=C/S(=O)(=O)N1CCC2(CC1)N=C(c1cccc(CCCCCC(F)(F)F)c1)NC2=O] | LVMS-D-1 | 2.82 | 634 (M + H)+ |
| 1117 | 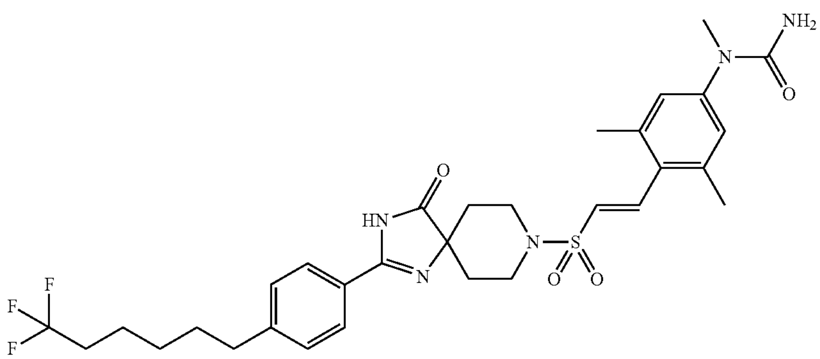 [SMILES: Cc1cc(N(C)C(N)=O)cc(C)c1/C=C/S(=O)(=O)N1CCC2(CC1)N=C(c1ccc(CCCCCC(F)(F)F)cc1)NC2=O] | LCMS-D-1 | 2.75 | 634 (M + H)+ |
| 1118 | 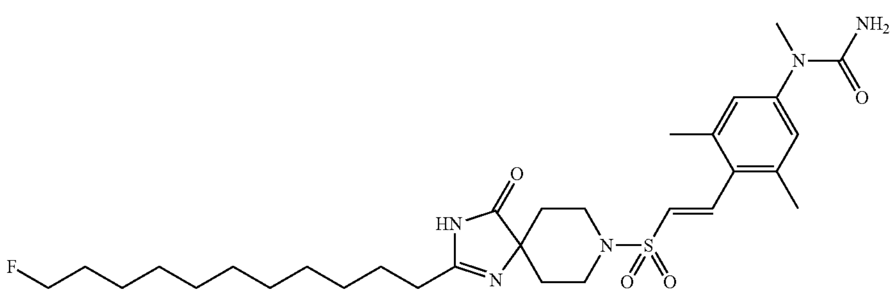 [SMILES: Cc1cc(N(C)C(N)=O)cc(C)c1/C=C/S(=O)(=O)N1CCC2(CC1)N=C(CCCCCCCCCCCF)NC2=O] | LCMS-F-1 | 1.07 | 592 (M + H)+ |
| 1119 | 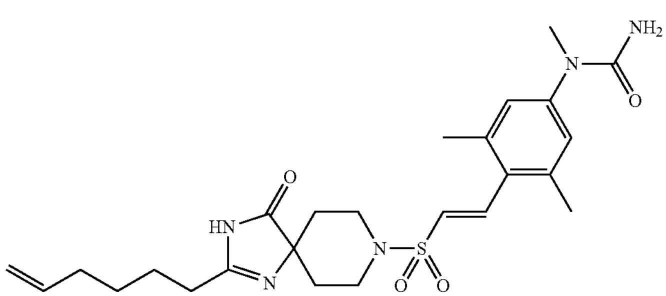 [SMILES: C=CCCCCC1=NC2(CCN(S(=O)(=O)/C=C/c3c(C)cc(N(C)C(N)=O)cc3C)CC2)C(=O)N1] | LCMS-F-1 | 0.92 | 502 (M + H)+ |

TABLE 165-continued

| Compound | Structure | LCMS condition | Retention time (min) | MS (m/z) |
|---|---|---|---|---|
| 1120 | 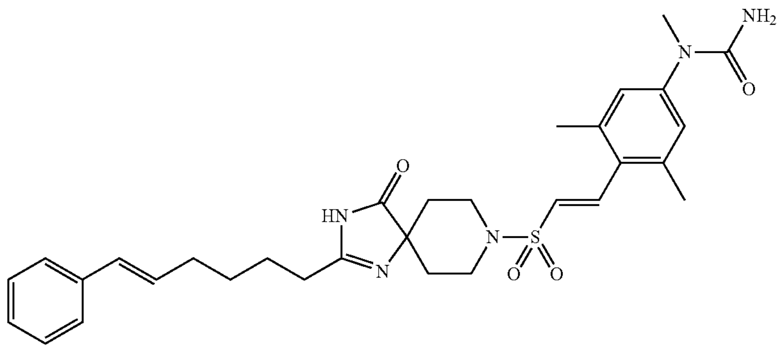 [SMILES: Cc1cc(N(C)C(N)=O)cc(C)c1/C=C/S(=O)(=O)N1CCC2(CC1)N=C(CCCC/C=C/c1ccccc1)NC2=O] | LCMS-F-1 | 1.02 | 578 (M + H)+ |
| 1121 | 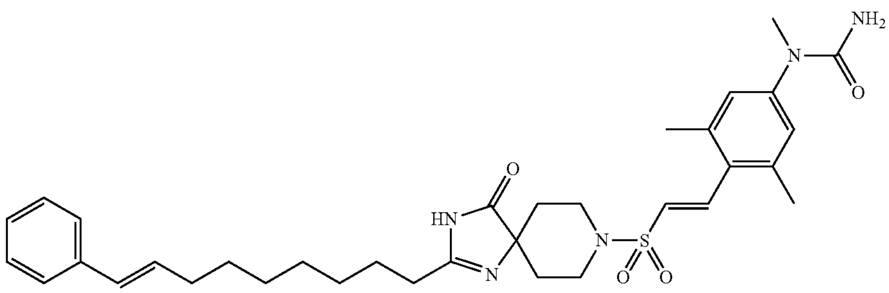 [SMILES: Cc1cc(N(C)C(N)=O)cc(C)c1/C=C/S(=O)(=O)N1CCC2(CC1)N=C(CCCCCCC/C=C/c1ccccc1)NC2=O] | LCMS-F-1 | 1.11 | 620 (M + H)+ |
| 1122 | 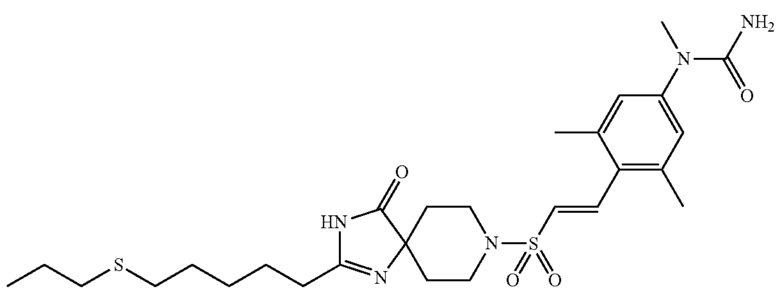 [SMILES: CCCSCCCCCC1=NC2(CCN(S(=O)(=O)/C=C/c3c(C)cc(N(C)C(N)=O)cc3C)CC2)C(=O)N1] | LCMS-D-1 | 1.75 | 564 (M + H)+ |
| 1123 | 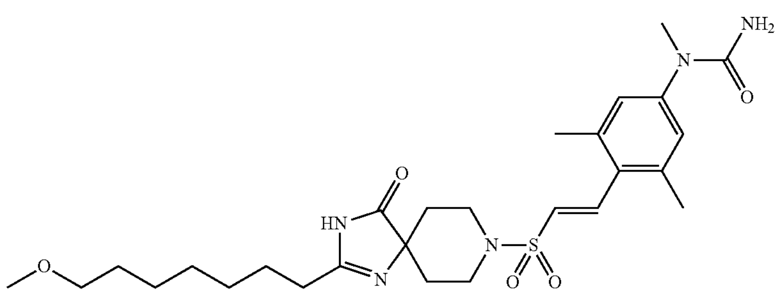 [SMILES: COCCCCCCCC1=NC2(CCN(S(=O)(=O)/C=C/c3c(C)cc(N(C)C(N)=O)cc3C)CC2)C(=O)N1] | LCMS-D-1 | 1.81 | 548 (M + H)+ |
| 1124 | 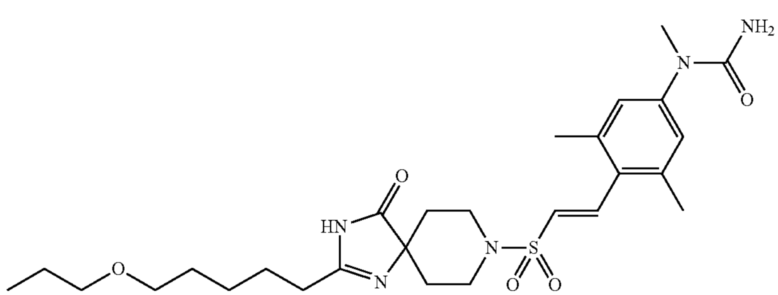 | LCMS-D-1 | 1.98 | 548 (M + H)+ |

TABLE 165-continued

| Compound | Structure | LCMS condition | Retention time (min) | MS (m/z) |
|---|---|---|---|---|
| 1125 | 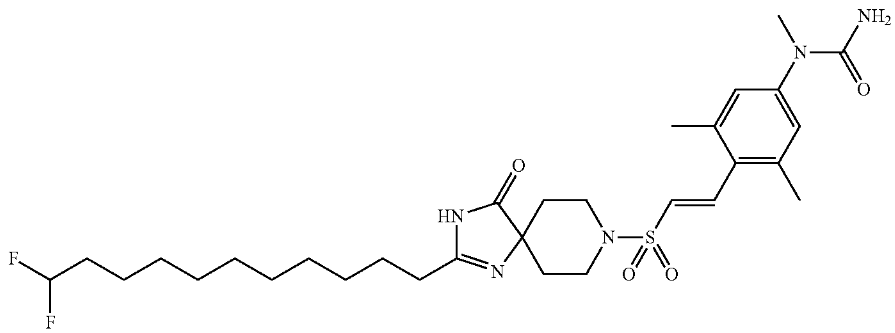 [SMILES: Cc1cc(N(C)C(N)=O)cc(C)c1/C=C/S(=O)(=O)N1CCC2(CC1)N=C(CCCCCCCCCCC(F)F)NC2=O] | LCMS-F-1 | 1.05 | 610 (M + H)+ |
| 1126 | 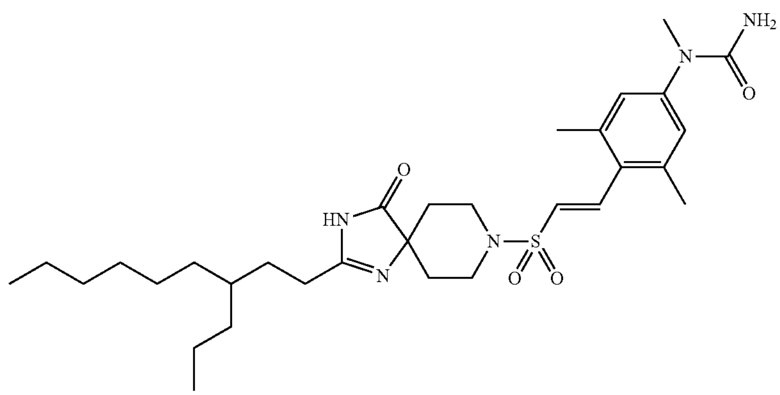 [SMILES: CCCCCCC(CCC)CCC1=NC2(CCN(S(=O)(=O)/C=C/c3c(C)cc(N(C)C(N)=O)cc3C)CC2)C(=O)N1] | LCMS-D-1 | 2.48 | 588 (M + H)+ |
| 1127 | 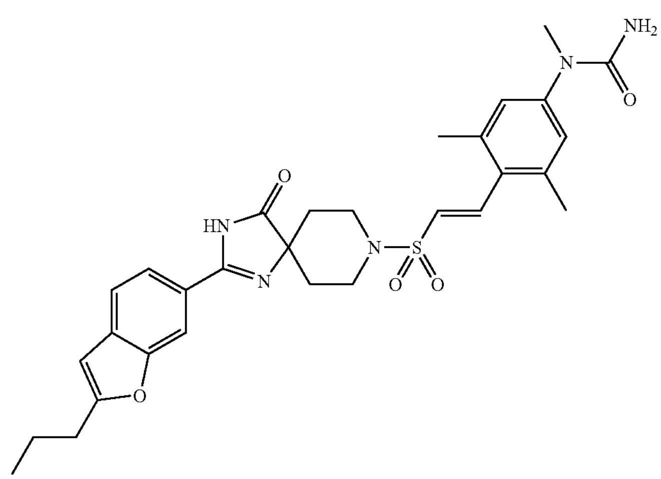 [SMILES: CCCc1cc2ccc(C3=NC4(CCN(S(=O)(=O)/C=C/c5c(C)cc(N(C)C(N)=O)cc5C)CC4)C(=O)N3)cc2o1] | LCMS-D-1 | 2.12 | 578 (M + H)+ |

TABLE 165-continued

| Compound | Structure | LCMS condition | Retention time (min) | MS (m/z) |
|---|---|---|---|---|
| 1128 | 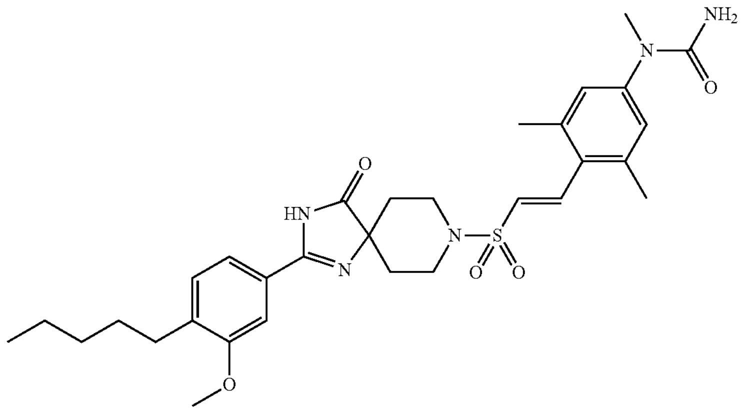 [SMILES: CCCCCc1ccc(C2=NC3(CCN(S(=O)(=O)/C=C/c4c(C)cc(N(C)C(N)=O)cc4C)CC3)C(=O)N2)cc1OC] | LCMS-D-1 | 2.98 | 596 (M + H)+ |
| 1129 | 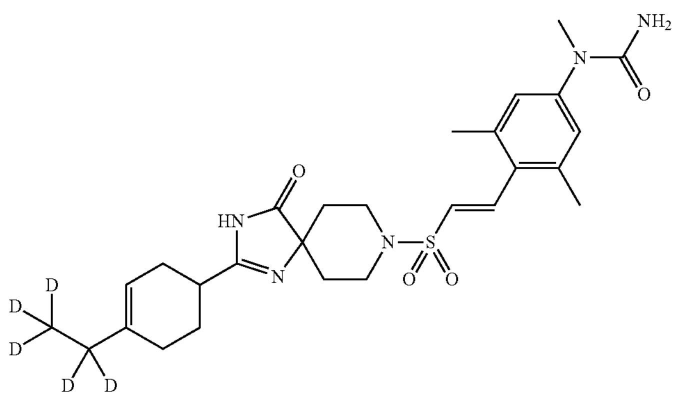 [SMILES: [2H]C([2H])([2H])C([2H])([2H])C1=CCC(C2=NC3(CCN(S(=O)(=O)/C=C/c4c(C)cc(N(C)C(N)=O)cc4C)CC3)C(=O)N2)CC1] | LCMS-F-1 | 0.95 | 533 (M + H)+ |
| 1130 | 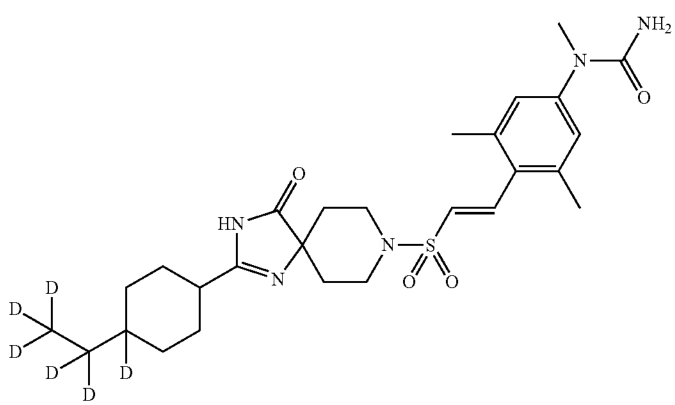 [SMILES: [2H]C([2H])([2H])C([2H])([2H])C1([2H])CCC(C2=NC3(CCN(S(=O)(=O)/C=C/c4c(C)cc(N(C)C(N)=O)cc4C)CC3)C(=O)N2)CC1] | LCMS-F-1 | 0.97 | 536 (M + H)+ |

The carboxylic acid reagent used in the synthesis of Compound 1115 (7-ethoxy-heptanoic acid) was synthesized by the following method.

(Reaction 271-3)

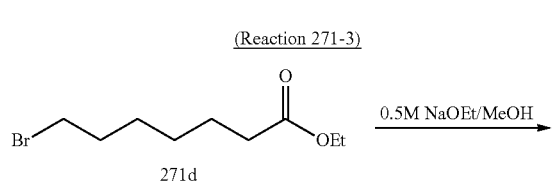

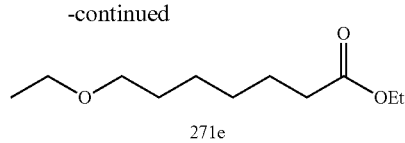

0.5 M sodium ethoxide (1.6 ml, 4.31 mmol) was added to a solution of ethyl 7-bromoheptanoate (300 mg, 1.44 mmol) in ethanol (7.0 ml), and the mixture was heated under reflux for two hours. The reaction mixture was concentrated under reduced pressure, and the resulting residue was then purified by silica gel column chromatography (hexane:ethyl acetate=10:1) to give ethyl 7-ethoxyheptanoate (102.4 mg, 40%).

¹H-NMR (300 MHz, DMSO-d6) δ 1.18 (t, 3H, J=7.3 Hz), 1.24 (t, 3H, J=7.3 Hz), 1.29-1.38 (m, 4H), 1.52-1.68 (m, 4H), 2.28 (t, 2H, J=7.6 Hz), 3.45-3.51 (m, 4H), 4.05-4.17 (m, 2H).

(Reaction 271-4)

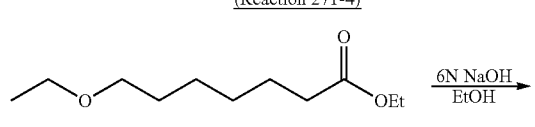

7-Ethoxy-heptanoic acid was synthesized by operations similar to those in Reaction 95-18 using appropriate reagents and starting material.

¹H-NMR (300 MHz, DMSO-d6) δ 1.13 (m, 3H), 1.35 (m, 4H), 1.58 (m, 4H), 2.23 (m, 2H), 3.49 (m, 4H), 12.36 (s, 1H).

The carboxylic acid reagent used in the synthesis of Compound 1116 (3-(6,6,6-trifluoro-hexyl)-benzoic acid) was synthesized by the following method.

(Reaction 271-5)

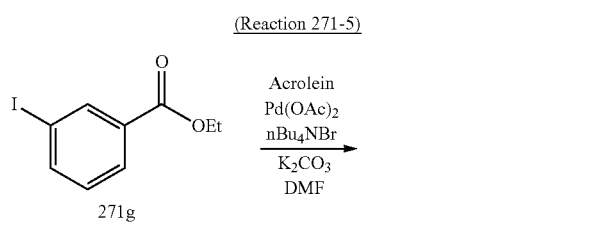

Acrolein (180 μl, 2.71 mmol), tetrabutylammonium bromide (385 mg, 1.19 mmol), palladium acetate (5 mmol %) and potassium carbonate (450 mg, 3.26 mmol) were added to a solution of methyl 3-iodobenzoate (300 mg, 1.08 mmol) in DMF (6.0 ml), and the mixture was heated with stirring at 80° C. for two hours. The reaction mixture was cooled to room temperature and then diluted with ethyl acetate, and the organic layer was washed with water and saturated brine. The organic layer was concentrated under reduced pressure, and the resulting residue was then purified by silica gel column chromatography (hexane:ethyl acetate=8:1) to give ethyl 3-(3-oxoprop-1-en-1-yl)benzoate as a white solid (280 mg, 96%).

MS (ESI) m/z=205 (M+H)+.

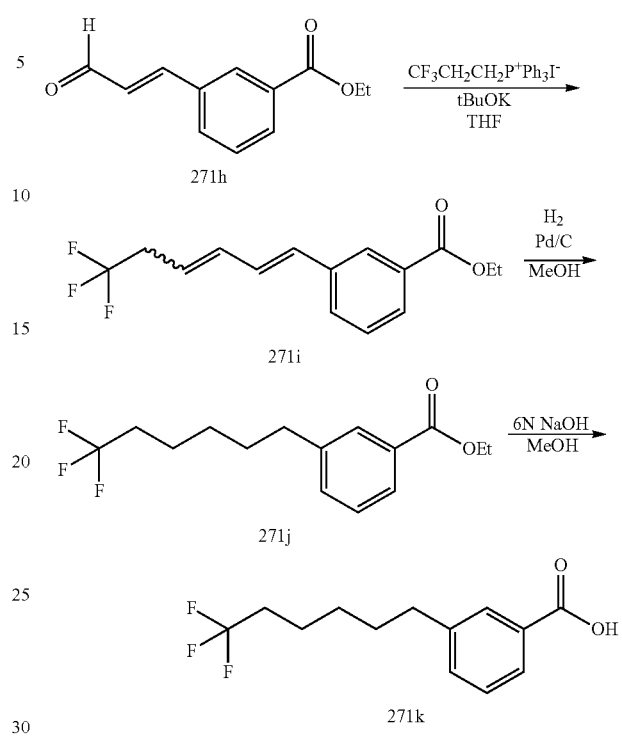

3-(6,6,6-Trifluoro-hexyl)-benzoic acid was synthesized by operations similar to those in Reaction 191-14, Reaction 18-2 and Reaction 95-18 using appropriate reagents and starting material.

MS (ESI) m/z=261 (M+H)+.

The carboxylic acid reagent used in the synthesis of Compound 1117 (4-(6,6,6-trifluoro-hexyl)-benzoic acid) was synthesized by the following method.

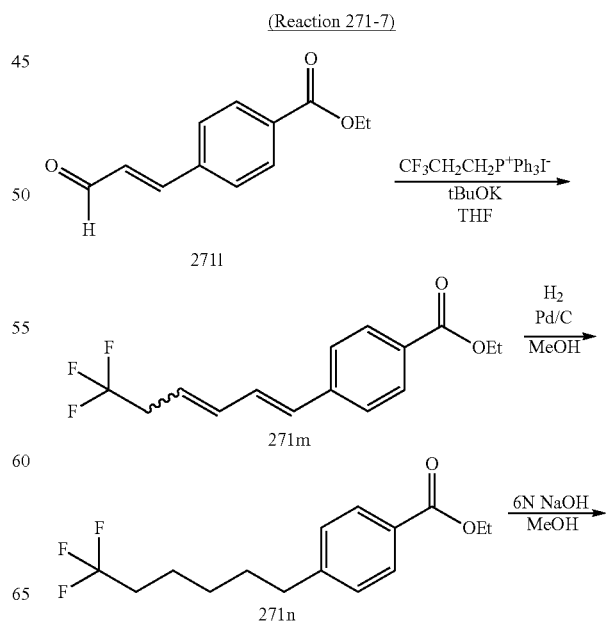

-continued

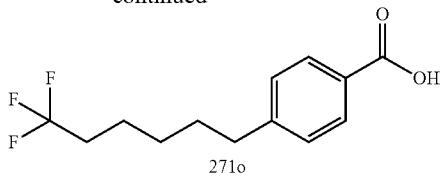

4-(6,6,6-Trifluoro-hexyl)-benzoic acid was synthesized by operations similar to those in Reaction 191-14, Reaction 18-2 and Reaction 95-18 using appropriate reagents and starting material.

MS (ESI) m/z=261 (M+H)+.

The carboxylic acid reagent used in the synthesis of Compound 1120 ((E)-7-phenyl-hept-6-enoic acid) was synthesized by the following method.

(Reaction 271-8)

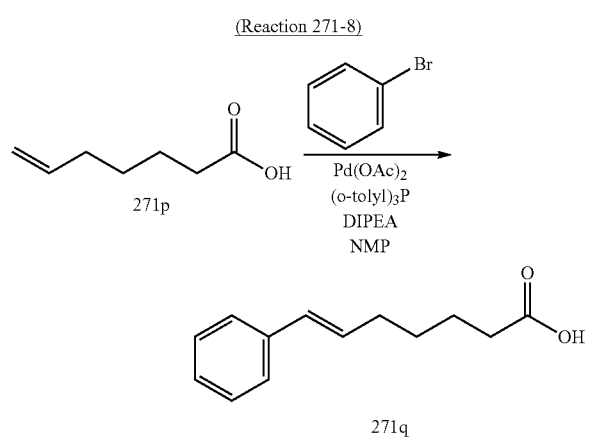

(E)-7-Phenyl-hept-6-enoic acid was synthesized by operations similar to those in Reaction 26-1 (using NMP as a solvent) using appropriate reagents and starting material.

MS (ESI) m/z=203 (M−H)−.

The carboxylic acid reagent used in the synthesis of Compound 1121 ((E)-10-phenyl-dec-9-enoic acid) was synthesized by the following method.

(Reaction 271-9)

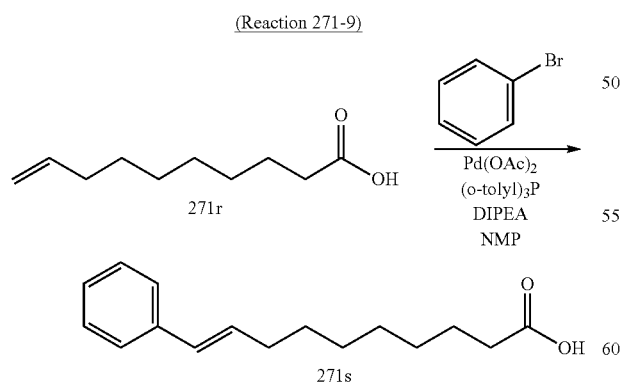

(E)-10-Phenyl-dec-9-enoic acid was synthesized by operations similar to those in Reaction 26-1 (using NMP as a solvent) using appropriate reagents and starting material.

MS (ESI) m/z=245 (M−H)−.

The carboxylic acid reagent used in the synthesis of Compound 1122 (6-propylsulfanyl-hexanoic acid) was synthesized by the following method.

(Reaction 271-10)

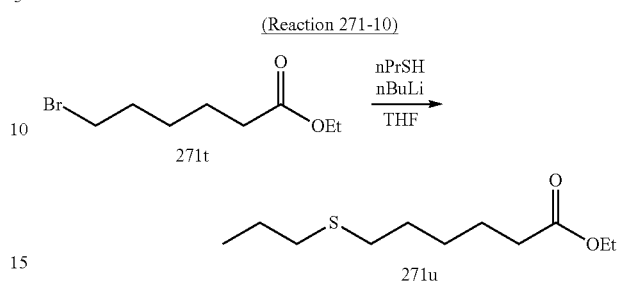

A solution of propanethiol (0.609 ml, 6.72 mmol) in anhydrous THF (10 ml) was cooled to −10° C. in a nitrogen atmosphere. 2 M nBuLi (4.03 ml, 8.07 mmol) was added dropwise and the mixture was then stirred for 10 minutes. A solution of ethyl 6-bromohexanoate in anhydrous THF (5 ml) was then added and the mixture was stirred for 40 minutes. The reaction mixture was quenched by adding water and then extracted with ethyl acetate. The organic layer was washed with water and saturated brine and dried over sodium sulfate. The organic layer was concentrated under reduced pressure, and the resulting residue was then purified by silica gel column chromatography (hexane:ethyl acetate=15:1) to give ethyl 6-(propylthio)hexanoate as a colorless oily substance (1.46 g, 100%).

$^1$H-NMR (300 MHz, CDCl$_3$) δ 0.98 (t, 3H, J=7.6 Hz), 1.25 (t, 3H, J=7.2 Hz), 1.46-1.36 (m, 2H), 1.69-1.54 (m, 6H), 2.30 (t, 2H, J=7.2 Hz), 2.49 (dd, 4H, J=7.2, 14.3 Hz), 4.12 (dd, 2H, J=7.2, 14.1 Hz).

(Reaction 271-11)

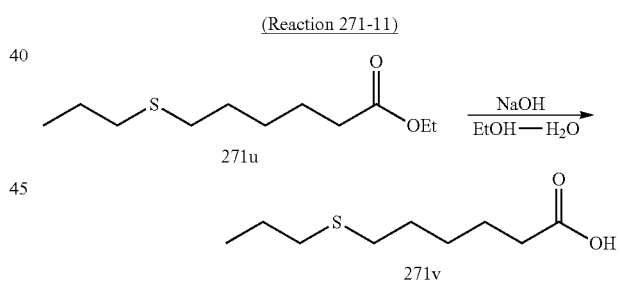

6-Propylsulfanyl-hexanoic acid was synthesized by operations similar to those in Reaction 95-18 using appropriate reagents and starting material.

$^1$H-NMR (300 MHz, DMSO-d6) δ 0.92 (m, 3H), 1.34 (m, 2H), 1.51 (m, 6H), 2.19 (m, 2H), 2.45 (m, 4H).

The carboxylic acid reagent used in the synthesis of Compound 1123 (8-methoxy-octanoic acid) was synthesized by the following method.

(Reaction 271-12)

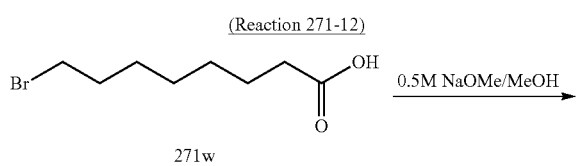

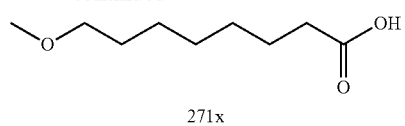
271x

8-Methoxy-octanoic acid was synthesized by operations similar to those in Reaction 271-3 using appropriate reagents and starting material.

$^1$H-NMR (300 MHz, CDCl$_3$) δ 1.39 (m, 6H), 1.69 (m, 4H), 2.13 (s, 1H), 2.42 (m, 2H), 3.33 (s, 3H), 3.39 (m, 2H).

The carboxylic acid reagent used in the synthesis of Compound 1124 (6-propoxy-hexanoic acid) was synthesized by the following method.

(Reaction 271-13)

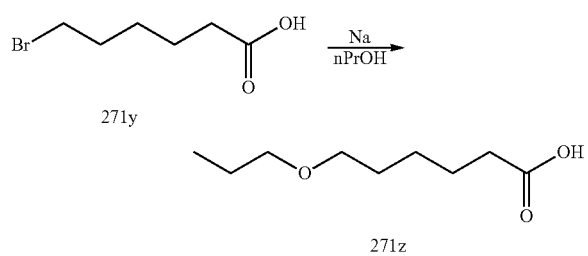

Sodium (354 mg, 15.38 mmol) was added to a solution of 6-bromohexanoic acid (300 mg, 1.54 mmol) in propyl alcohol (15 ml), and the mixture was heated under reflux for two hours. The reaction mixture was cooled to room temperature and then concentrated under reduced pressure. The resulting residue was purified by silica gel column chromatography (dichloromethane:methanol=30:1) to give 6-propoxy-hexanoic acid (209 mg, 78%).

$^1$H-NMR (300 MHz, CDCl$_3$) δ 0.88 (m, 3H), 1.37 (m, 2H), 1.62 (m, 6H), 2.44 (m, 2H), 3.52 (m, 4H).

The carboxylic acid reagent used in the synthesis of Compound 1126 (4-propyl-decanoic acid) was synthesized by the following method.

(Reaction 271-14)

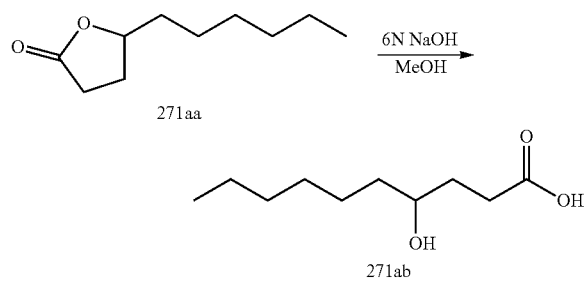

4-Hydroxy-decanoic acid was synthesized by operations similar to those in Reaction 95-18 using appropriate reagents and starting material. This was used in the next step without complete purification.

(Reaction 271-15)

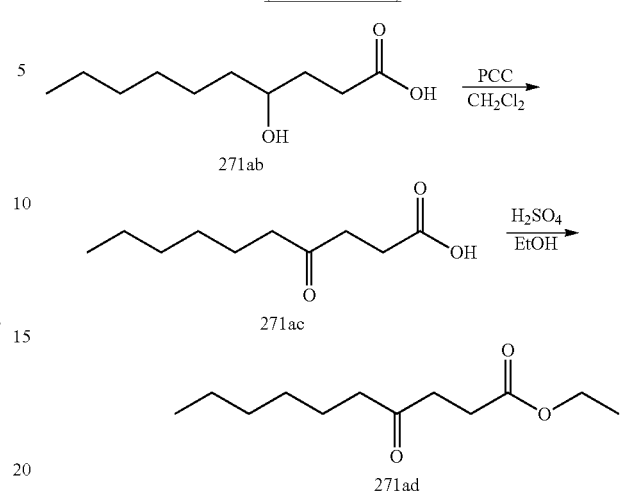

PCC (1.2 g, 2.71 mmol) was added to a solution of 4-hydroxydecanoic acid (830 mg, 4.4 mmol) in dichloromethane (30 ml), and the mixture was stirred at room temperature for five hours. The reaction mixture was adjusted to pH 1 by adding 1 N hydrochloric acid and then extracted with ethyl acetate. The organic layer was washed with water and saturated brine and then concentrated under reduced pressure. The resulting residue was then dissolved in ethanol (15 ml). Five drops of sulfuric acid were added and the mixture was stirred at 80° C. for 18 hours. The reaction mixture was concentrated under reduced pressure, and the resulting residue was purified by silica gel column chromatography (hexane:ethyl acetate=2:1) to give ethyl 4-oxodecanoate (440 mg, 46% in two steps).

$^1$H-NMR (300 MHz, CDCl$_3$) δ 0.86 (t, 3H, J=7.2 Hz), 1.26 (m, 9H), 1.57 (m, 2H), 2.43 (t, 2H, J=7.2 Hz), 2.56 (m, 2H), 2.70 (m, 2H), 4.11 (dt, 2H, J=7.2, 7.2 Hz).

(Reaction 271-16)

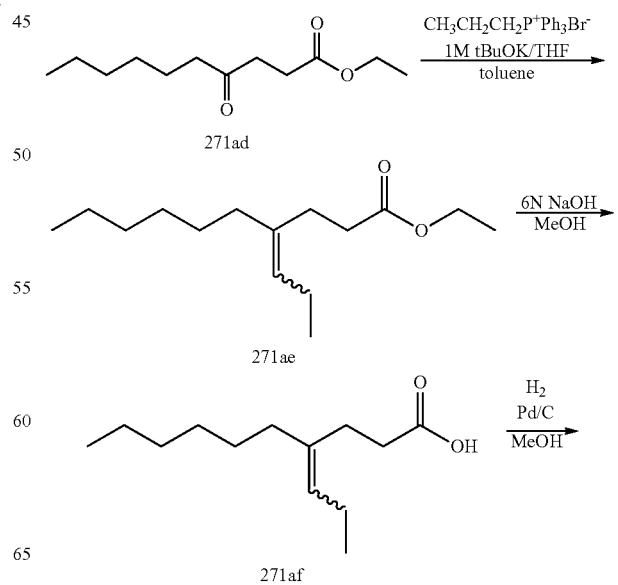

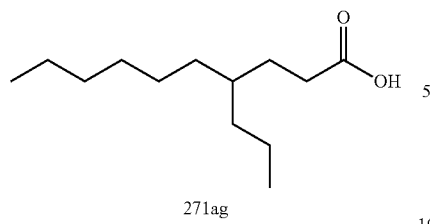

271ag

4-Propyl-decanoic acid was synthesized by operations similar to those in Reaction 191-14, Reaction 95-18 and Reaction 18-2 using appropriate reagents and starting material.

$^1$H-NMR (300 MHz, CDCl$_3$) δ 0.88 (m, 6H), 1.27 (m, 15H), 2.38 (m, 2H), 2.61 (m, 2H), 8.91 (br, 1H).

The carboxylic acid reagent used in the synthesis of Compound 1127 (2-propyl-benzofuran-6-carboxylic acid) was synthesized by the following method.

(Reaction 271-17)

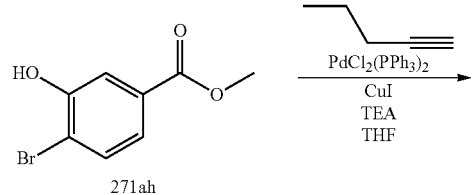

271ah

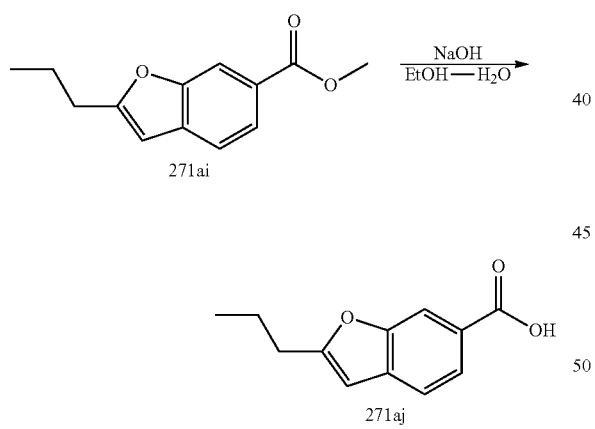

271ai

271aj

2-Propyl-benzofuran-6-carboxylic acid was synthesized by operations similar to those in Reaction 95-10 (using PdCl$_2$(PPh$_3$)$_2$ as a catalyst) and Reaction 95-18 using appropriate reagents and starting material.

$^1$H-NMR (300 MHz, CDCl$_3$) δ 1.02 (m, 3H), 1.80 (m, 2H), 2.79 (m, 2H), 6.46 (s, 1H), 7.53 (m, 1H), 7.96 (m, 1H), 8.16 (s, 1H).

The carboxylic acid reagent used in the synthesis of Compound 1128 (3-methoxy-4-pentyl-benzoic acid) was synthesized by the following method.

(Reaction 271-18)

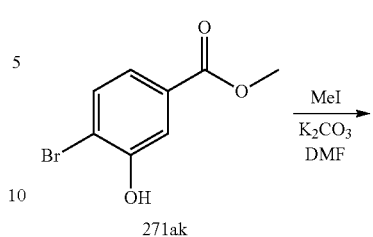

271ak

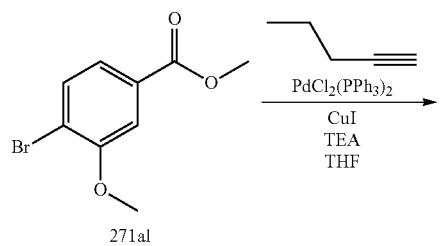

271al

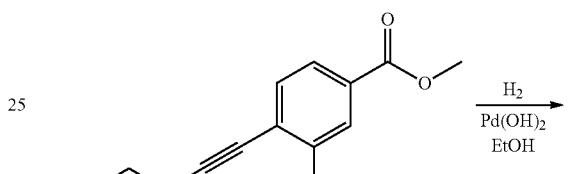

271am

271an

271ao

3-Methoxy-4-pentyl-benzoic acid was synthesized by operations similar to those in Reaction 26-4, Reaction 95-10 (using PdCl$_2$(PPh$_3$)$_2$ as a catalyst), Reaction 122-2 and Reaction 95-18 using appropriate reagents and starting material.

MS (ESI) m/z=223 (M+H)+.

A mixture of the carboxylic acid reagent used in the synthesis of the compound 1129 (4-([1,1,2,2,2-$^2$H$_5$]ethyl)-cyclohex-3-enecarboxylic acid)

and the carboxylic acid reagent used in the synthesis of the compound 1130 (4-([1,1,2,2,2-$^2$H$_5$]ethyl)-[4-$^2$H]-cyclohexanecarboxylic acid)

was synthesized by the following method.

(Reaction 271-19)

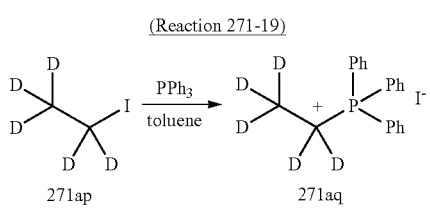

A solution of iodo-ethane-d5 (3.00 g, 18.6 mmol) and triphenylphosphine (14.6 mg, 55.8 mmol) in toluene (15 ml) was stirred at 110° C. for 21 hours. The reaction mixture was filtered, and the solid was washed with toluene and dried to give [1,1,2,2,2-²H₅]ethyltriphenylphosphonium iodide as a white solid (7.85 g, 100%). This was used in the next reaction without complete purification.

(Reaction 271-20)

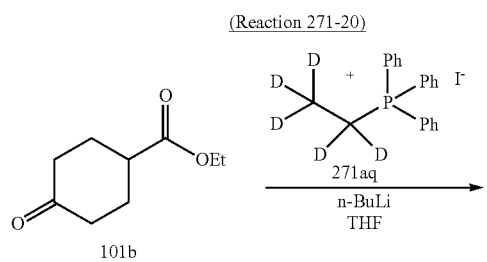

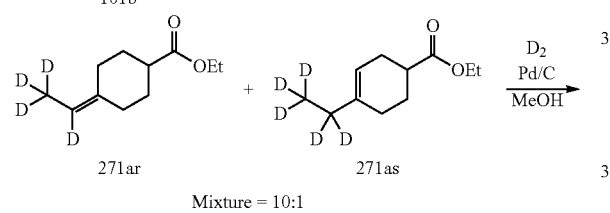

Mixture = 10:1

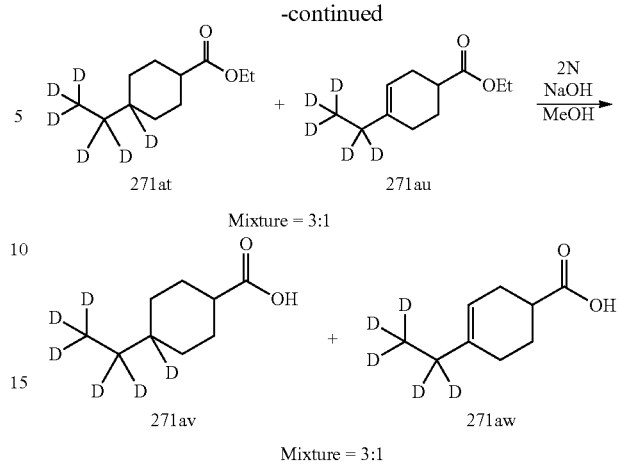

4-([1,1,2,2,2-²H₅]Ethyl)-cyclohex-3-enecarboxylic acid and 4-([1,1,2,2,2-²H₅]ethyl)-[4-²H]-cyclohexanecarboxylic acid were synthesized as a mixture by operations similar to those in Reaction 101-1, Reaction 18-2 and Reaction 95-18 using appropriate reagents and starting material. This was used in the next step without complete purification.

Example 272

12-(8-{(E)-2-[2,6-Dimethyl-4-(1-methyl-ureido)-phenyl]-ethenesulfonyl}-4-oxo-1,3,8-triaza-spiro [4.5]dec-1-en-2-yl)-dodecanoic acid (Compound 1131)

and 12-(8-{(E)-2-[2,6-dimethyl-4-(1-methyl-ureido)-phenyl]-ethenesulfonyl}-4-oxo-1,3,8-triaza-spiro [4.5]dec-1-en-2-yl)-dodecanoic acid ethyl ester (Compound 1132)

(Reaction 272-1)

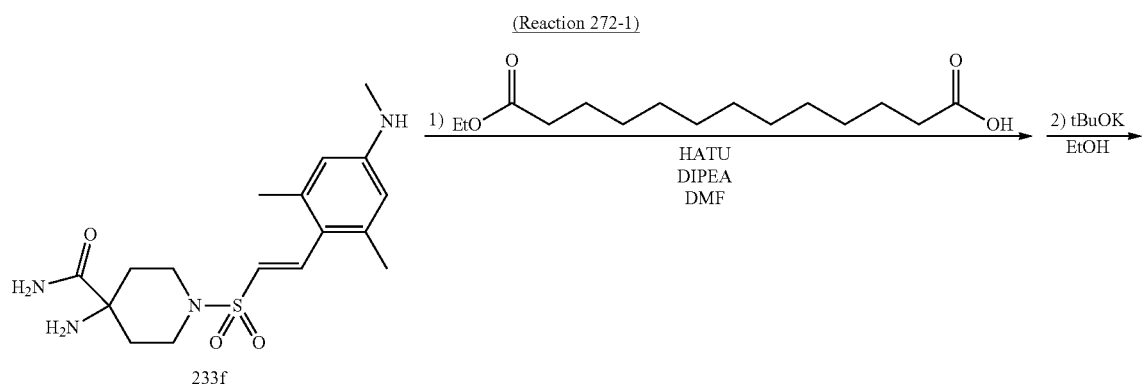

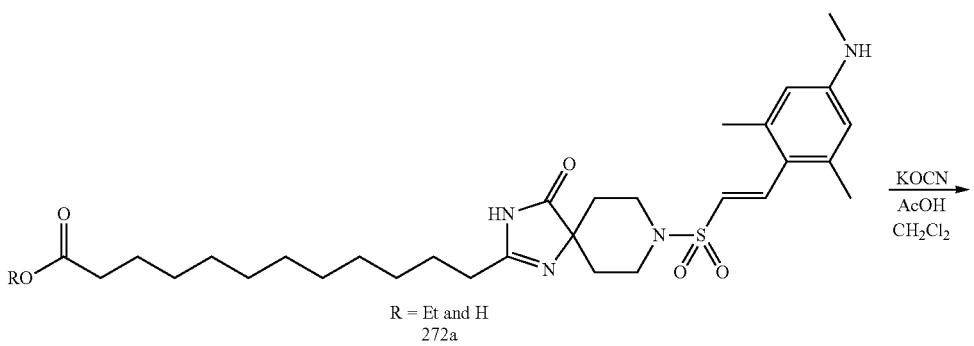

-continued

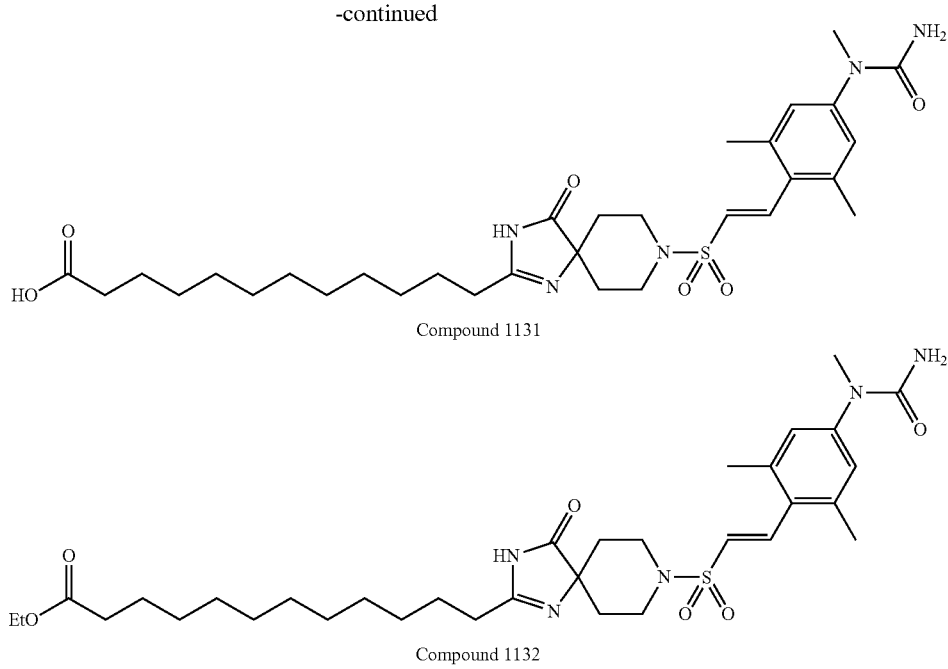

Compound 1131

Compound 1132

12-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-dodecanoic acid MS (ESI) m/z=618 (M+H)+ and 12-(8-{(E)-2-[2,6-dimethyl-4-(1-methyl-ureido)-phenyl]-ethenesulfonyl}-4-oxo-1,3,8-triaza-spiro[4.5]dec-1-en-2-yl)-dodecanoic acid ethyl ester MS (ESI) m/z=646 (M+H)+ were synthesized by operations similar to those in Reaction 269-1 and Reaction 89-2 (using KOCN) using appropriate reagents and starting material.

Example 273

1-(3,5-Dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate (Compound 1133) and 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate (Compound 1134)

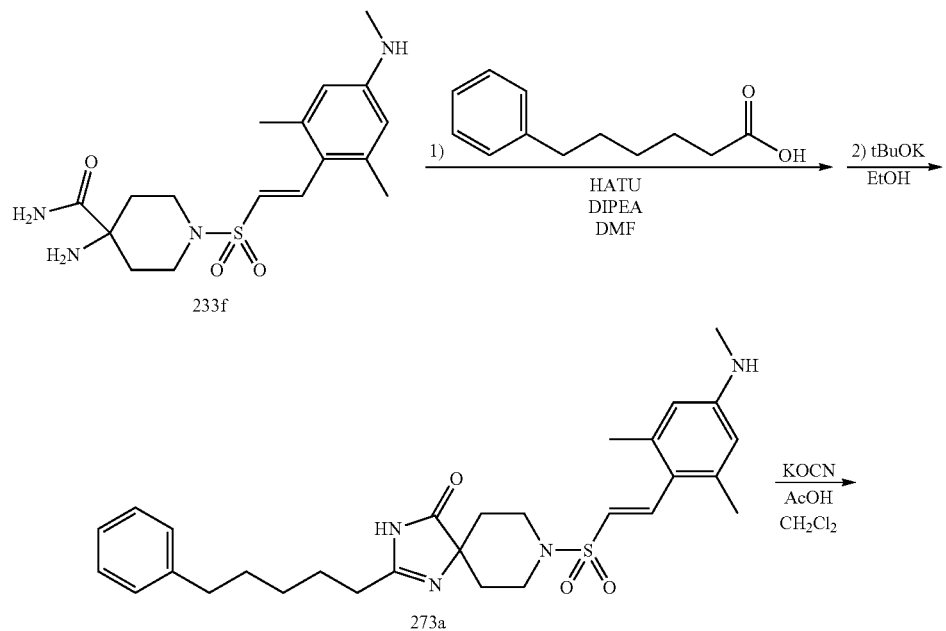

(Reaction 273-1)

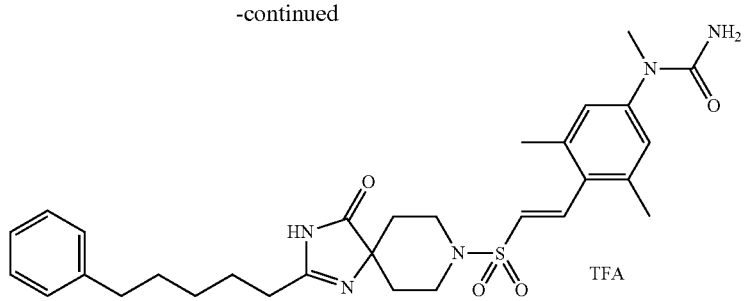

Compound 1133

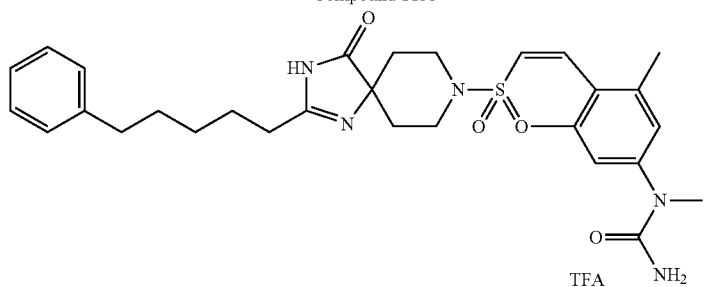

Compound 1134

1-(3,5-Dimethyl-4-{(E)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate MS (ESI) m/z=566 (M+H)+ and 1-(3,5-dimethyl-4-{(Z)-2-[4-oxo-2-(5-phenyl-pentyl)-1,3,8-triaza-spiro[4.5]dec-1-ene-8-sulfonyl]-vinyl}-phenyl)-1-methyl-urea trifluoroacetate MS (ESI) m/z=566 (M+H)+ were synthesized by operations similar to those in Reaction 269-1 and Reaction 89-2 (using KOCN) using appropriate reagents and starting material.

Example 274

1-[3,5-Dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea (Compound 1135)

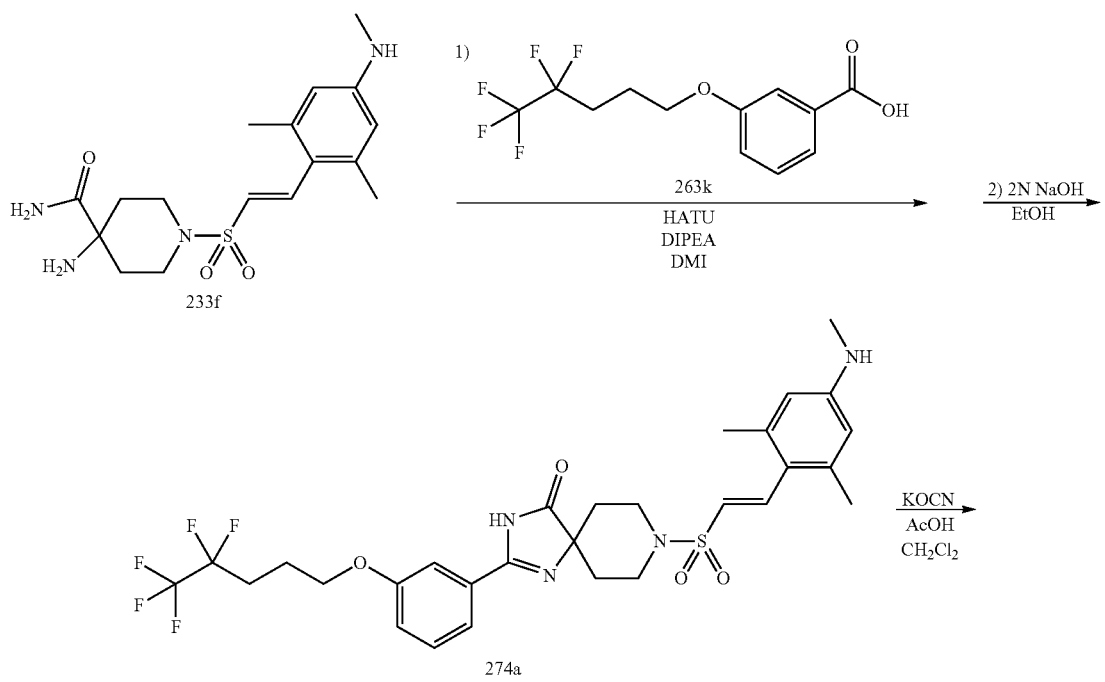

(Reaction 274-1)

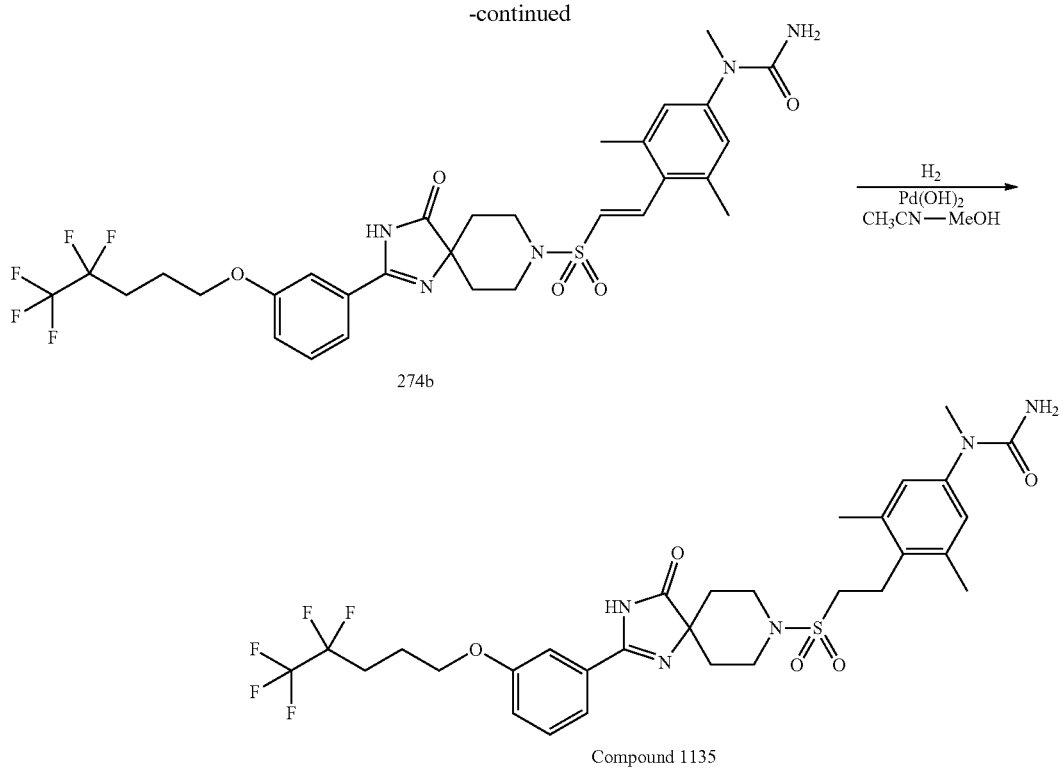

1-[3,5-Dimethyl-4-(2-{4-oxo-2-[3-(4,4,5,5,5-pentafluoro-pentyloxy)-phenyl]-1,3,8-triaza-spiro[4.5]dec-1-ene-8-sulfonyl}-ethyl)-phenyl]-1-methyl-urea was synthesized by operations similar to those in Reaction 269-1, Reaction 89-2 (using KOCN) and Reaction 184-1 using appropriate reagents and starting material.

MS (ESI) m/z=674 (M+H)+.

Example 275

1-(3,5-Dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea (Compound 1136)

(Reaction 275-1)

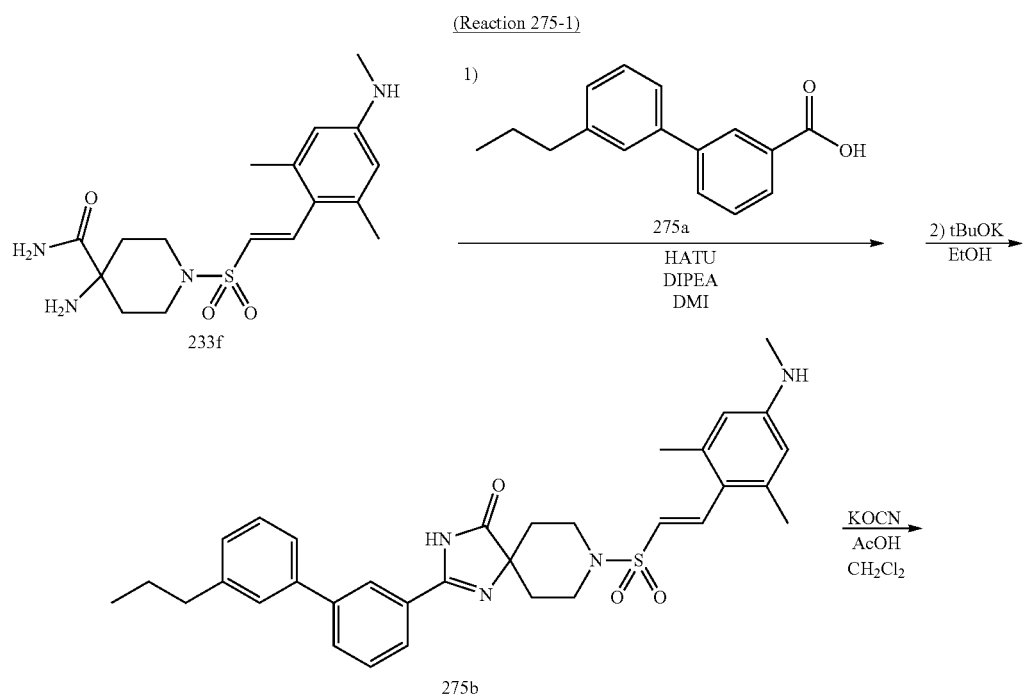

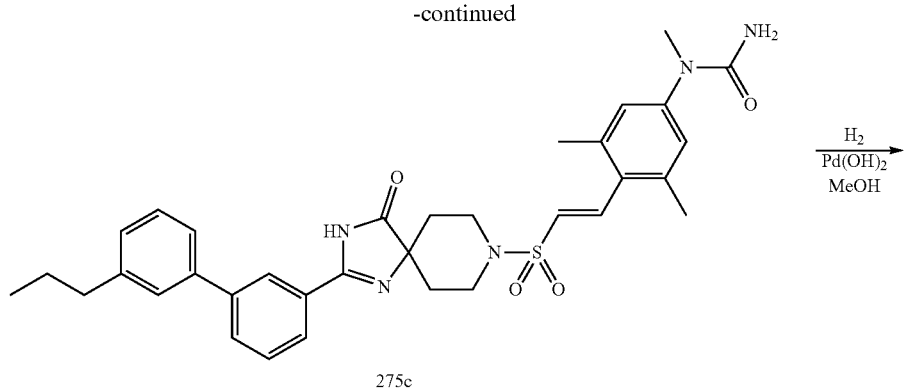

275c

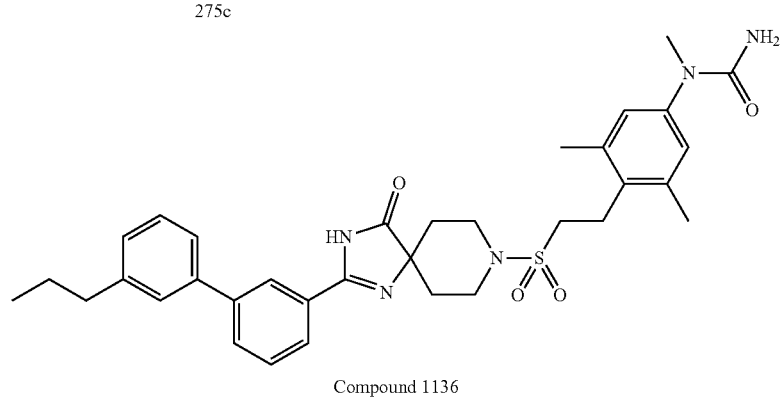

Compound 1136

1-(3,5-Dimethyl-4-{2-[4-oxo-2-(3'-propyl-biphenyl-3-yl)-1,3,8-triaza-spiro[4.5]dec-1-ene-8-sulfonyl]-ethyl}-phenyl)-1-methyl-urea was synthesized by operations similar to those in Reaction 269-1, Reaction 89-2 (using KOCN) and Reaction 184-1 using appropriate reagents and starting material.

MS (ESI) m/z=616 (M+H)+.

The carboxylic acid reagent used in the synthesis of Compound 1136 (3'-propyl-biphenyl-3-carboxylic acid) was synthesized by the following method.

(Reaction 275-2)

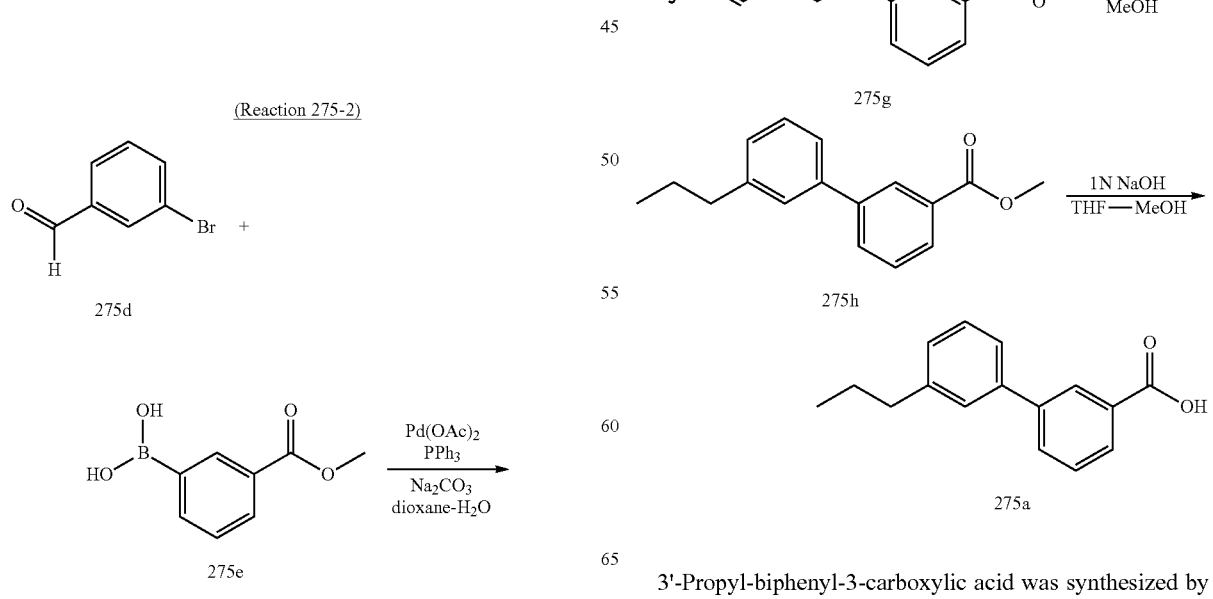

3'-Propyl-biphenyl-3-carboxylic acid was synthesized by operations similar to those in Reaction 259-2, Reaction 191-14, Reaction 18-2 and Reaction 95-18 using appropriate reagents and starting material.
$^1$H-NMR (300 MHz, CDCl$_3$) δ 8.36 (t, 1H, J=1.5 Hz), 8.10 (dt, 1H, J=7.6, 1.5 Hz), 7.85 (dt, 1H, J=7.6, 1.5 Hz), 7.56 (t, 1H, J=7.6 Hz), 7.46 (dt, 1H, J=7.3, 1.5 Hz), 7.45 (d, 1H, J=7.3 Hz), 7.39 (t, 1H, J=7.3 Hz), 7.23 (dt, 1H, J=7.3, 1.5 Hz), 2.68 (t, 2H, J=7.6 Hz), 1.71 (m, 2H), 0.99 (t, 3H, J=7.6 Hz).
Example 276
1-(3,5-Dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea (Compound 1137)
(Reaction 276-1)
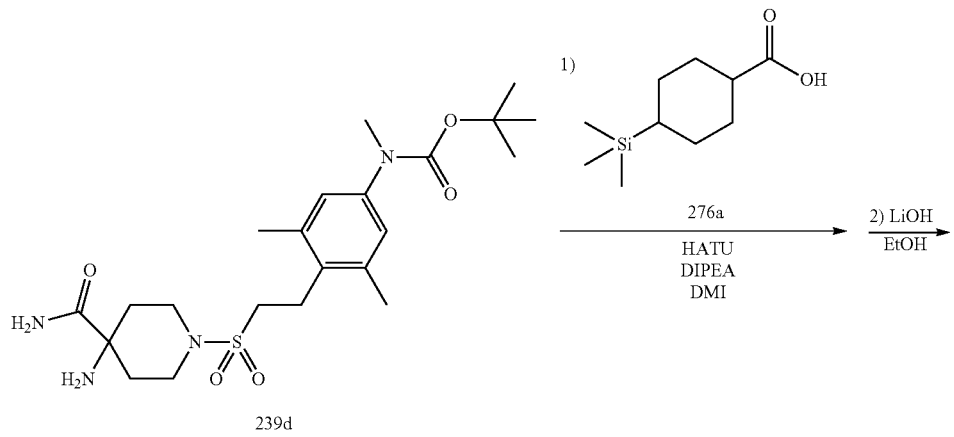
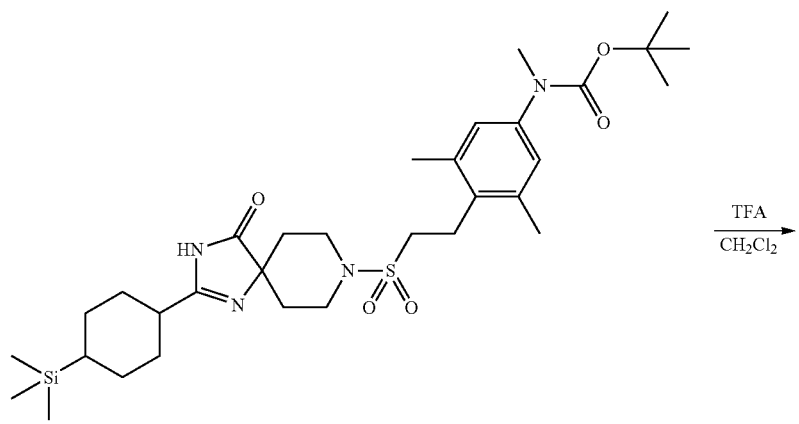
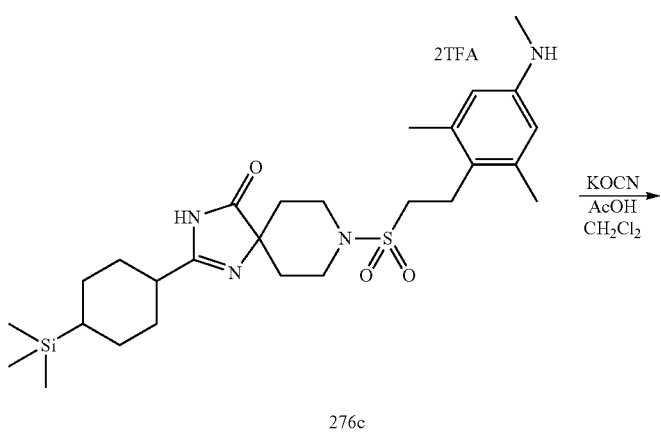

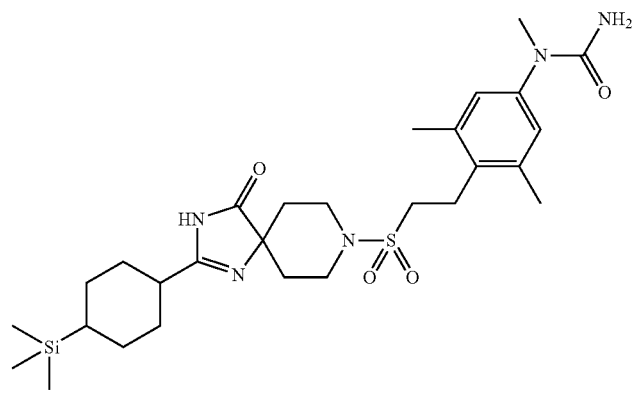

Compound 1137

1-(3,5-Dimethyl-4-{2-[4-oxo-2-(4-trimethylsilanyl-cyclohexyl)-1,3,8-triaza-spiro[4.5]dec-1-ene-8-sulfonyl]-ethyl}-phenyl)-1-methyl-urea was synthesized by operations similar to those in Reaction 269-1 (using LiOH), Reaction 4-1 and Reaction 89-2 (using KOCN) using appropriate reagents and starting material.

MS (ESI) m/z=576 (M+H)+.

The carboxylic acid reagent used in the synthesis of Compound 1137 (4-trimethylsilanyl-cyclohexanecarboxylic acid) was synthesized by the following method.

(Reaction 276-2)

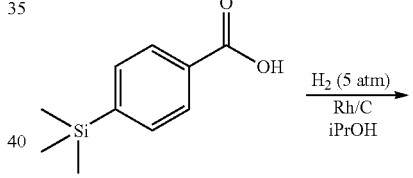

276d → 276e

1-Bromo-4-trimethylsilyl-benzene (0.426 ml, 2.18 mmol) was dissolved in THF (20 ml), and n-butyllithium (1.59 M solution in n-hexane, 1.51 ml, 1.40 mmol) was added dropwise at −78° C. After stirring for 20 minutes, crushed dry ice (excess) was added. The reaction solution was stirred at room temperature for one hour, and 1 M hydrochloric acid and water were then added, followed by extraction with ethyl acetate. The organic layer was washed with water and saturated brine, dried over anhydrous sodium sulfate and concentrated under reduced pressure. The resulting residue was purified by silica gel column chromatography (n-hexane/ethyl acetate) to give 4-trimethylsilanyl-benzoic acid (363 mg, 86%).

¹H-NMR (400 MHz, DMSO-D₆) δ 12.93 (1H, br s), 7.91 (2H, d, J=8.3 Hz), 7.65 (2H, d, J=7.8 Hz), 0.27 (9H, t, J=3.4 Hz).

(Reaction 276-3)

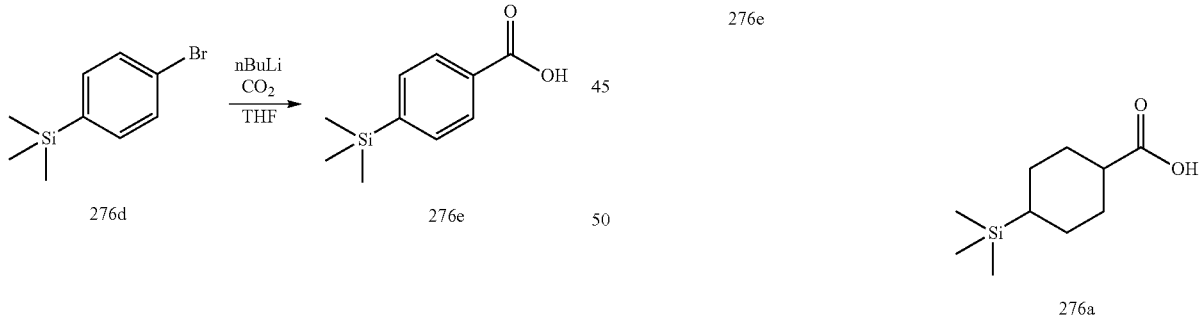

276e → 276a

4-Trimethylsilanyl-cyclohexanecarboxylic acid was synthesized by operations similar to those in Reaction 193-3 using appropriate reagents and starting material.

¹H-NMR (400 MHz, CDCl₃) δ 2.73-2.66 (0.6H, m), 2.33 (0.4H, tt, J=11.0, 3.7 Hz), 2.15-0.58 (8H, m), −0.06 (9H, s) (cis:trans=ca 6:4).

The example compounds shown below were synthesized by operations similar to those in Reaction 276-1 using appropriate reagents and starting materials.

Compounds 1138 to 1142

TABLE 166

| Compound | Structure | LCMS condition | Retention time (min) | MS (m/z) |
|---|---|---|---|---|
| 1138 | 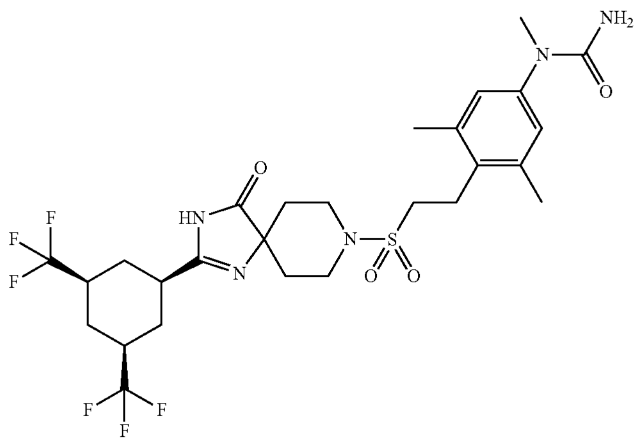 [SMILES: Cc1cc(N(C)C(N)=O)cc(C)c1CCS(=O)(=O)N1CCC2(CC1)N=C([C@H]1C[C@@H](C(F)(F)F)C[C@@H](C(F)(F)F)C1)NC2=O] | LCMS-A-1 | 2.44 | 640 (M + H)+ |
| 1139 | 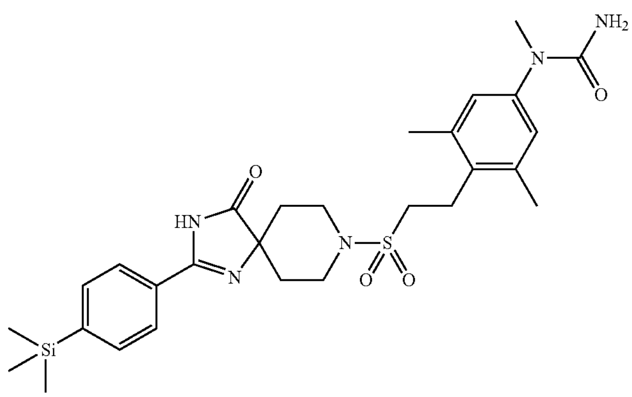 [SMILES: Cc1cc(N(C)C(N)=O)cc(C)c1CCS(=O)(=O)N1CCC2(CC1)N=C(c1ccc([Si](C)(C)C)cc1)NC2=O] | LCMS-A-1 | 2.47 | 570 (M + H)+ |
| 1140 | 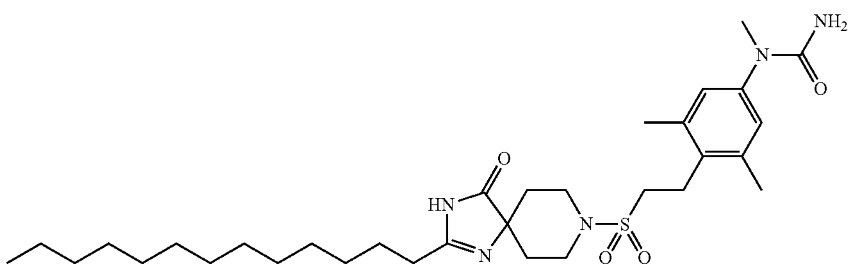 [SMILES: CCCCCCCCCCCCCC1=NC2(CCN(S(=O)(=O)CCc3c(C)cc(N(C)C(N)=O)cc3C)CC2)C(=O)N1] | LCMS-A-1 | 2.94 | 604 (M + H)+ |
| 1141 | 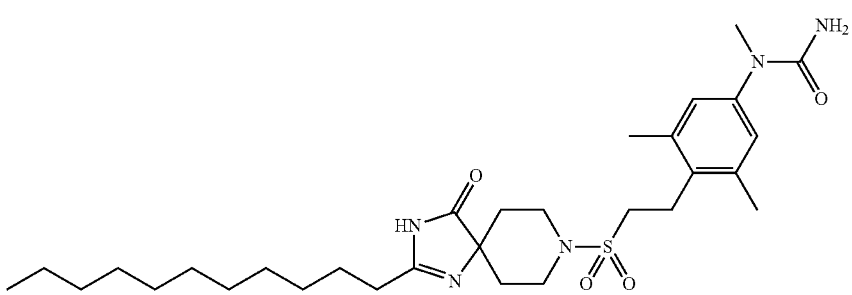 [SMILES: CCCCCCCCCCCC1=NC2(CCN(S(=O)(=O)CCc3c(C)cc(N(C)C(N)=O)cc3C)CC2)C(=O)N1] | LCMS-A-1 | 2.66 | 576 (M + H)+ |

TABLE 166-continued

| Compound | Structure | LCMS condition | Retention time (min) | MS (m/z) |
|---|---|---|---|---|
| 1142 | 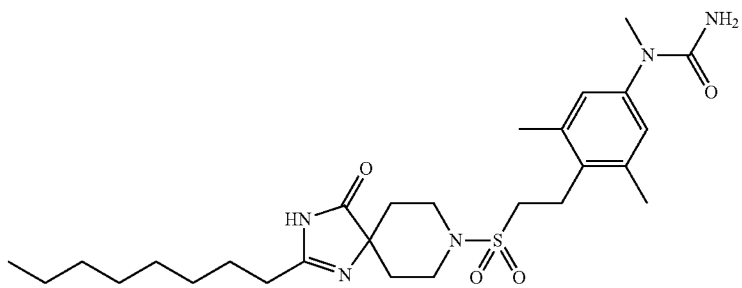 [SMILES: CCCCCCCCC1=NC2(CCN(S(=O)(=O)CCc3c(C)cc(N(C)C(N)=O)cc3C)CC2)C(=O)N1] | LCMS-A-1 | 2.31 | 534 (M + H)+ |

The carboxylic acid reagent used in the synthesis of Compound 1138 (3,5-bis-trifluoromethyl-cyclohexanecarboxylic acid) was synthesized by the following method.

(Reaction 276-4)

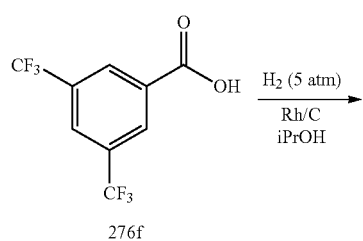

3,5-Bis-trifluoromethyl-cyclohexanecarboxylic acid was synthesized by operations similar to those in Reaction 193-3 using appropriate reagents and starting material.

$^1$H-NMR (400 MHz, CDCl$_3$) δ 2.51-2.41 (1H, m), 2.35-2.27 (2H, m), 2.24-2.12 (3H, m), 1.52-1.42 (2H, m), 1.41-1.30 (1H, m).

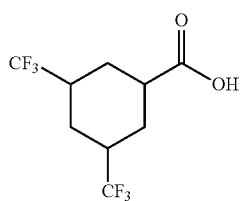

Example 277

1-(4-{2-[2-((1S,3R)-3-Hexyl-cyclohexyl)-4-oxo-1,3,8-triaza-spiro[4.5]dec-1-ene-8-sulfonyl]-ethyl}-3,5-dimethyl-phenyl)-1-methyl-urea (Compound 1143)

(Reaction 277-1)

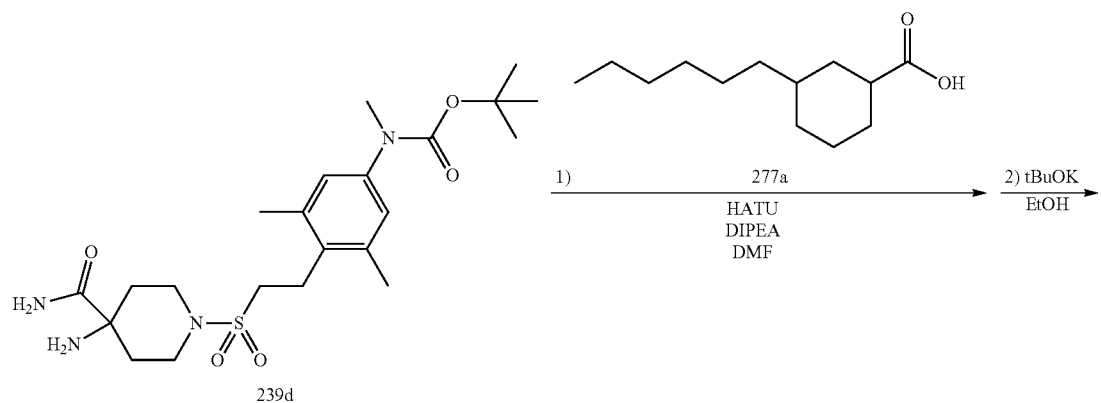

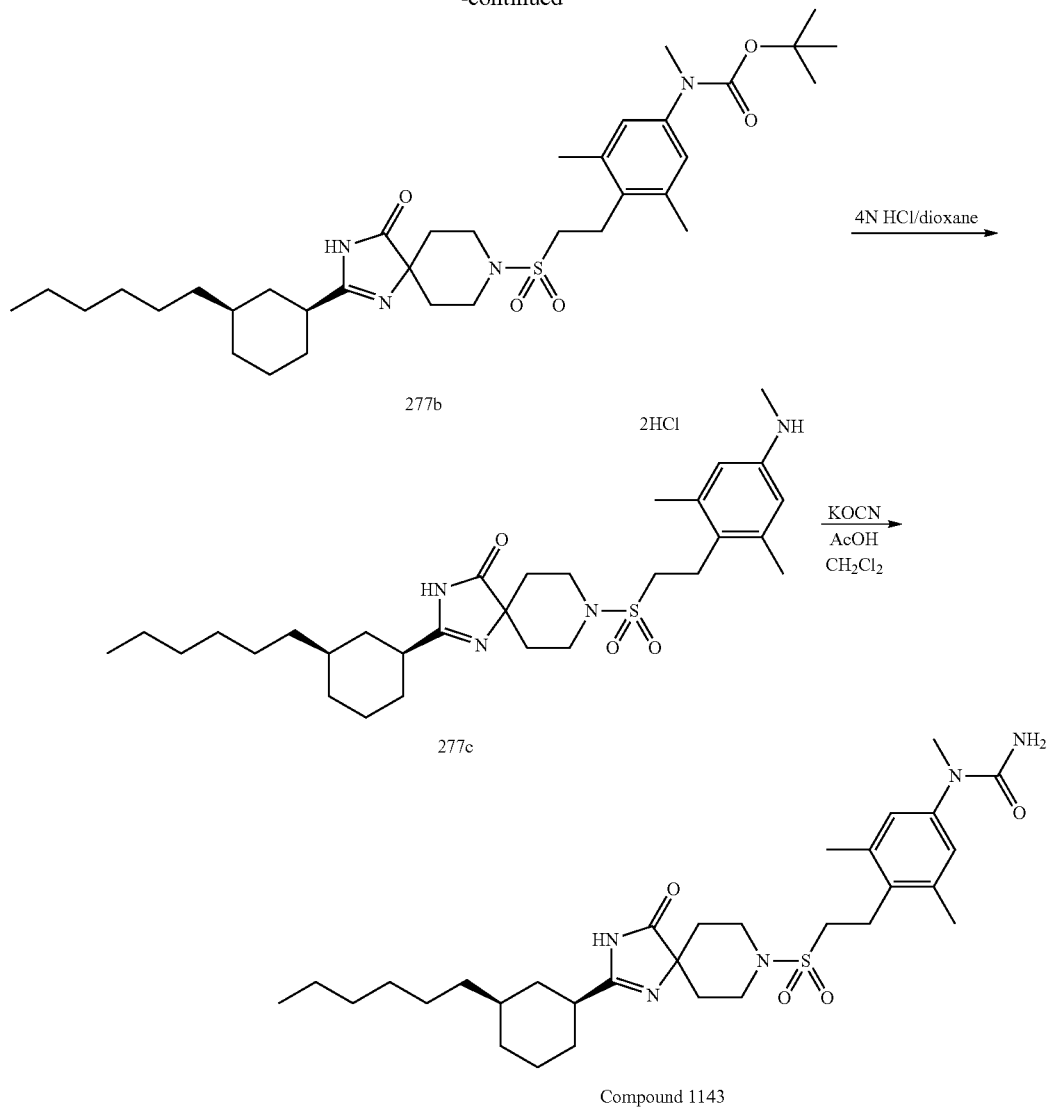

277b

277c

Compound 1143

1-(4-{2-[2-((1S,3R)-3-Hexyl-cyclohexyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 269-1, Reaction 5-3 and Reaction 89-2 (using KOCN) using appropriate reagents and starting material.

MS (ESI) m/z=588 (M+H)+.

The carboxylic acid reagent used in the synthesis of Compound 1143 (3-hexyl-cyclohexanecarboxylic acid) was synthesized by the following method.

(Reaction 277-2)

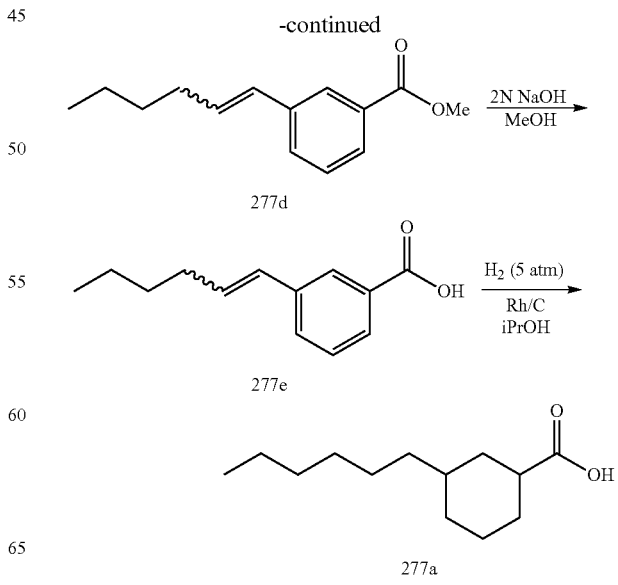

193n

277d

277e

277a

3-Hexyl-cyclohexanecarboxylic acid was synthesized by operations similar to those in Reaction 101-1, Reaction 95-18 and Reaction 193-3 using appropriate reagents and starting material.

¹H-NMR (400 MHz, CDCl₃) δ 0.84-2.03 (22H, m), 2.32 (0.6H, tt, J=11.6, 2.8 Hz), 2.67-2.68 (0.4H, m) (cis:trans=3:2).

The example compounds shown below were synthesized by operations similar to those in Reaction 277-1 using appropriate reagents and starting materials.

Compounds 1144 to 1149

TABLE 167

| Compound | Structure | LCMS condition | Retention time (min) | MS (m/z) |
|---|---|---|---|---|
| 1144 | 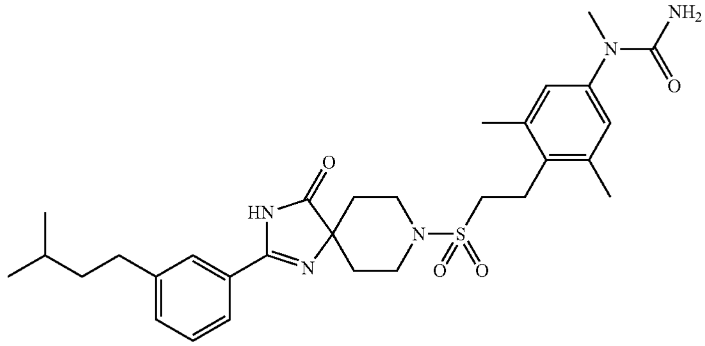 [SMILES: Cc1cc(N(C)C(N)=O)cc(C)c1CCS(=O)(=O)N1CCC2(CC1)N=C(c1cccc(CCC(C)C)c1)NC2=O] | LCMS-C-1 | 2.93 | 568 (M + H)+ |
| 1145 | 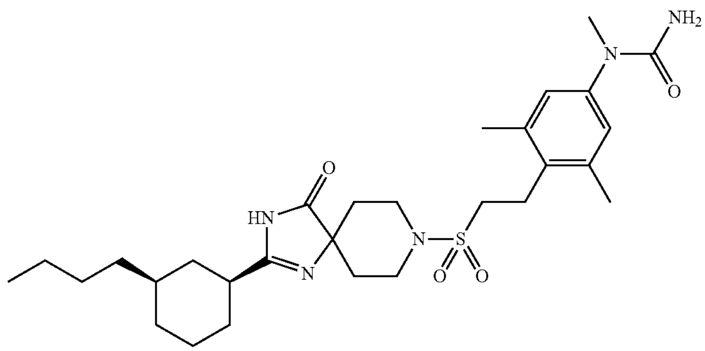 [SMILES: CCCC[C@@H]1CCC[C@H](C2=NC3(CCN(S(=O)(=O)CCc4c(C)cc(N(C)C(N)=O)cc4C)CC3)C(=O)N2)C1] | LCMS-C-1 | 2.93 | 560 (M + H)+ |
| 1146 | 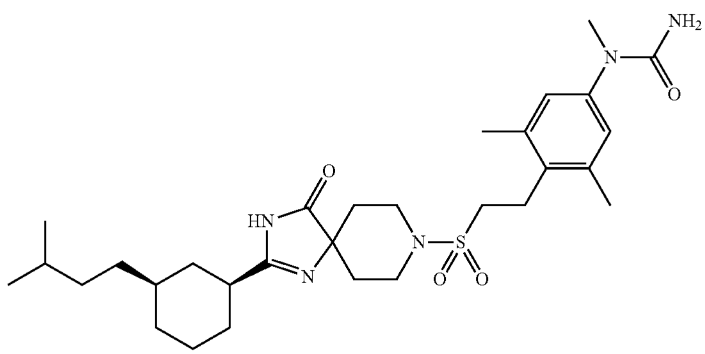 [SMILES: Cc1cc(N(C)C(N)=O)cc(C)c1CCS(=O)(=O)N1CCC2(CC1)N=C([C@H]1CCC[C@@H](CCC(C)C)C1)NC2=O] | LCMS-C-1 | 3.03 | 574 (M + H)+ |
| 1147 | 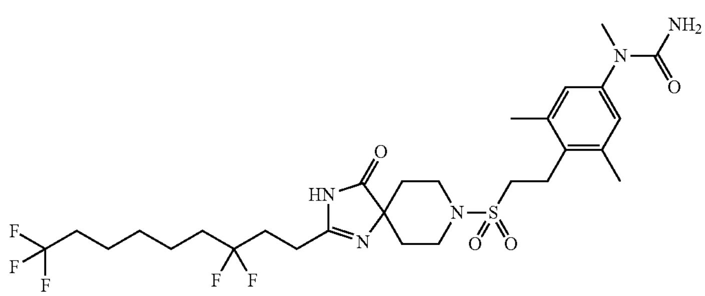 [SMILES: Cc1cc(N(C)C(N)=O)cc(C)c1CCS(=O)(=O)N1CCC2(CC1)N=C(CCC(F)(F)CCCCCC(F)(F)F)NC2=O] | LCMS-F-1 | 0.98 | 638 (M + H)+ |

TABLE 167-continued

| Compound | Structure | LCMS condition | Retention time (min) | MS (m/z) |
|---|---|---|---|---|
| 1148 | 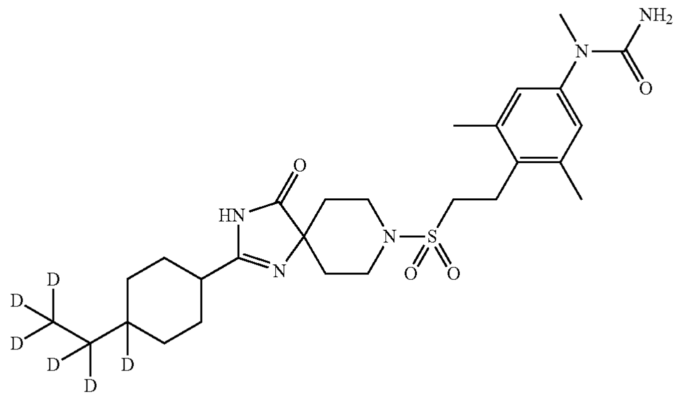 [SMILES: [2H]C([2H])([2H])C([2H])([2H])C1([2H])CCC(C2=NC3(CCN(S(=O)(=O)CCc4c(C)cc(N(C)C(N)=O)cc4C)CC3)C(=O)N2)CC1] | LCMS-F-1 | 0.97 | 538 (M + H)+ |
| 1149 | 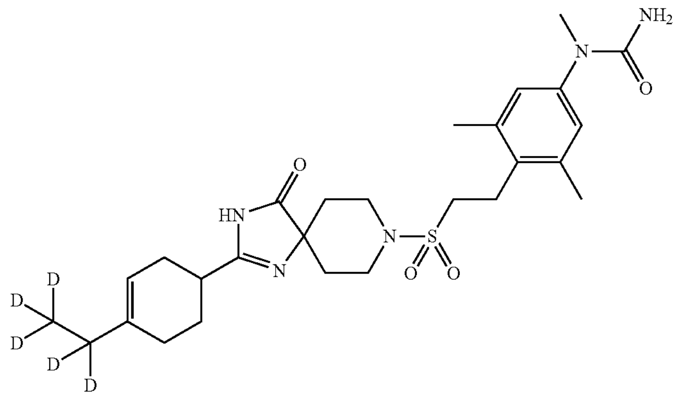 [SMILES: [2H]C([2H])([2H])C([2H])([2H])C1=CCC(C2=NC3(CCN(S(=O)(=O)CCc4c(C)cc(N(C)C(N)=O)cc4C)CC3)C(=O)N2)CC1] | LCMS-F-1 | 0.95 | 535 (M + H)+ |

The carboxylic acid reagent used in the synthesis of Compound 1144 (3-(3-methyl-butyl)-benzoic acid) was synthesized by the following method.

(Reaction 277-3)

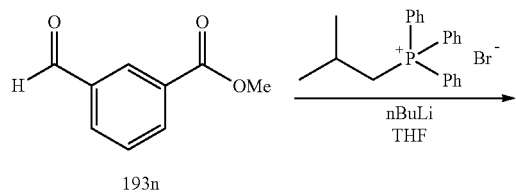

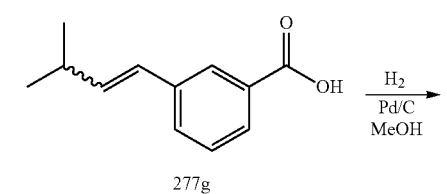

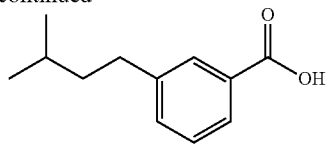

3-(3-Methyl-butyl)-benzoic acid was synthesized by operations similar to those in Reaction 101-1, Reaction 95-18 and Reaction 18-2 using appropriate reagents and starting material.

MS (ESI) m/z=191 (M−H)−.

The carboxylic acid reagent used in the synthesis of Compound 1145 (3-butyl-cyclohexanecarboxylic acid) was synthesized by the following method.

(Reaction 277-4)

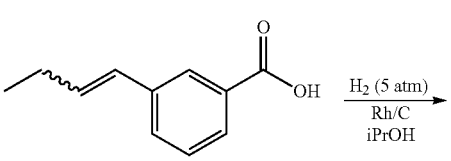

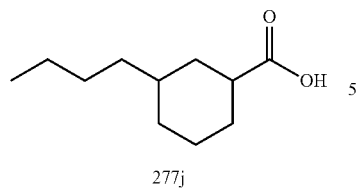

277j

3-Butyl-cyclohexanecarboxylic acid was synthesized by operations similar to those in Reaction 193-3 using appropriate reagents and starting material.

$^1$H-NMR (400 MHz, CDCl$_3$) δ 0.84-2.03 (18H, m), 2.33 (0.6H, m), 2.68 (0.4H, m) (cis:trans=3:2).

The carboxylic acid reagent used in the synthesis of Compound 1146 (3-(3-methyl-butyl)-cyclohexanecarboxylic acid) was synthesized by the following method.

(Reaction 277-5)

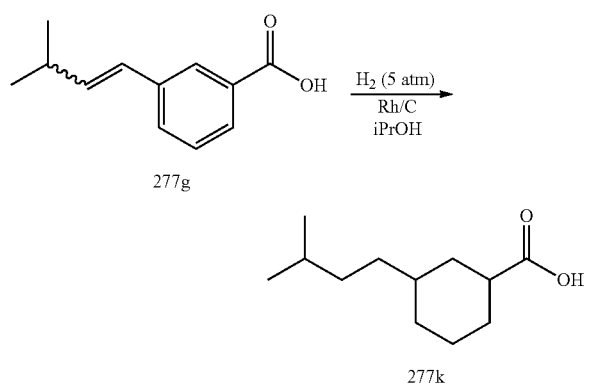

3-(3-Methyl-butyl)-cyclohexanecarboxylic acid was synthesized by operations similar to those in Reaction 193-3 using appropriate reagents and starting material.

$^1$H-NMR (400 MHz, CDCl$_3$) δ 0.81-2.04 (20H, m), 2.33 0.66H, tt, J=12.0, 3.2 Hz), 2.67-2.68 (0.33H, m) (cis:trans=2:1).

The carboxylic acid reagent used in the synthesis of Compound 1147 (4,4,10,10,10-pentafluoro-decanoic acid) was synthesized by the following method.

(Reaction 277-6)

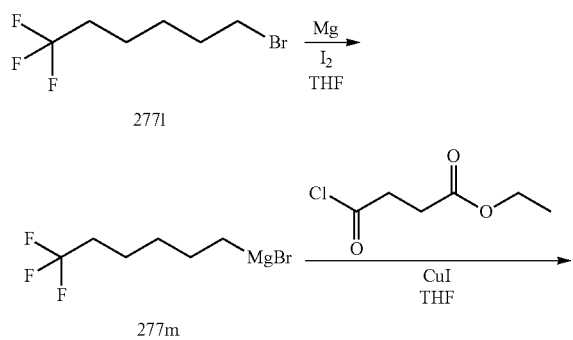

One piece of I$_2$ was added to a solution of magnesium (204 mg, 8.40 mmol) in THF (5 ml) in a nitrogen atmosphere, and the reaction mixture was stirred at 45° C. for 20 minutes. A solution of 6-bromo-1,1,1-trifluoro-hexane (1.53 g, 7.00 mmol) in THF (2 ml) was added and the reaction mixture was stirred at 45° C. for one hour to give Compound 277m (0.875 M solution in THF).

This Compound 277m (0.875 M solution in THF, 5.71 ml, 5.00 mmol) was added dropwise to succinylethyl chloride (1.00 g, 5.00 mmol) and CuI (57.9 mg, 304 µmol) in THF (17 ml) at 0° C. The reaction mixture was stirred at 0° C. for 30 minutes. The reaction mixture was quenched with a saturated aqueous ammonium chloride solution and diluted with ethyl acetate. The organic layer was then washed with a saturated aqueous sodium bicarbonate solution, water and saturated brine, and then dried over MgSO$_4$ and concentrated under reduced pressure. The resulting residue was purified by silica gel column chromatography (hexane/ethyl acetate=100/0→80/20) to give 10,10,10-trifluoro-4-oxo-decanoic acid ethyl ester (926 mg, 69%).

MS (ESI) m/z=269 (M+H)+.

(Reaction 277-7)

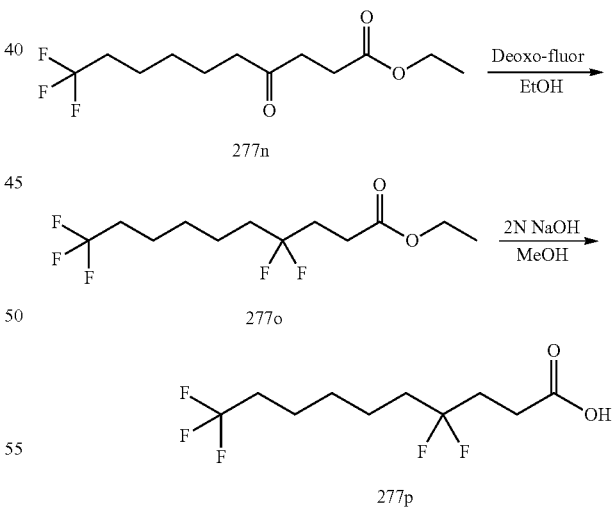

4,4,10,10,10-Pentafluoro-decanoic acid was synthesized by operations similar to those in Reaction 191-11 and Reaction 95-18 using appropriate reagents and starting material.

$^1$H-NMR (400 MHz, CDCl$_3$) δ 1.41-1.45 (2H, m), 1.50-1.64 (4H, m), 1.79-1.92 (2H, m), 2.02-2.25 (4H, m), 2.58-2.62 (2H, m).

Example 278
1-(4-{2-[2-(4-Chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea (Compound 1150)
(Reaction 278-1)
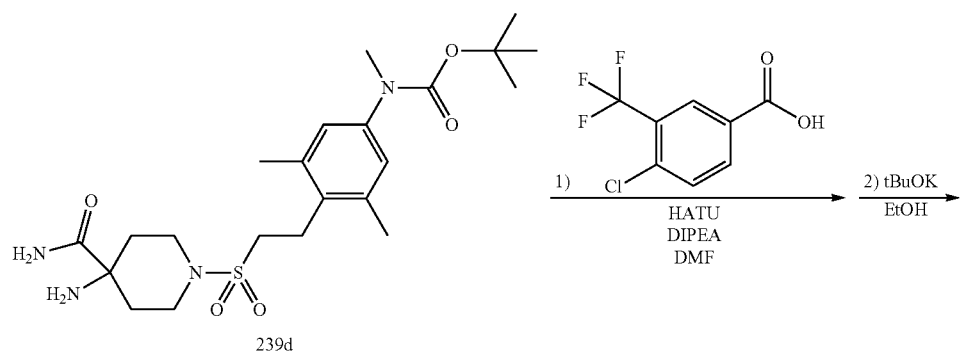
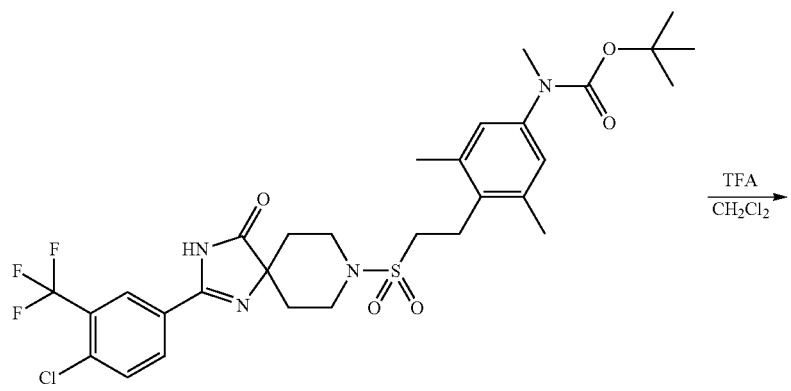
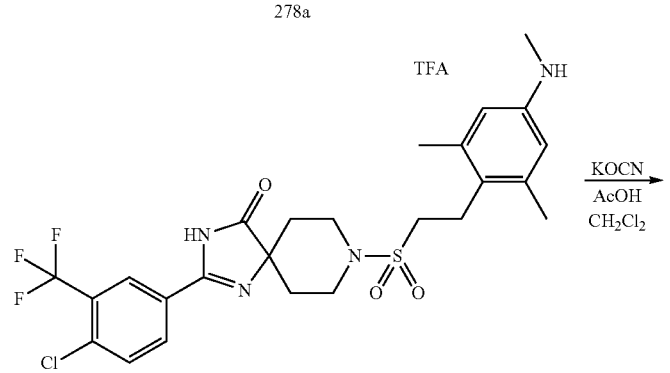
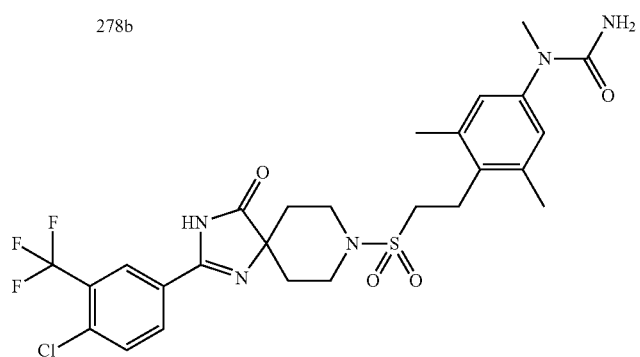
Compound 1150

1353

1-(4-{2-[2-(4-Chloro-3-trifluoromethyl-phenyl)-4-oxo-1,3,8-triaza-spiro[4.5]dec-1-ene-8-sulfonyl]-ethyl}-3,5-dimethyl-phenyl)-1-methyl-urea was synthesized by operations similar to those in Reaction 269-1, Reaction 4-1 and Reaction 89-2 (using KOCN) using appropriate reagents and starting material.

MS (ESI) m/z=600 (M+H)+.

1354

Example 279

1-(3,5-Dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea (Compound 1151)

(Reaction 279-1)

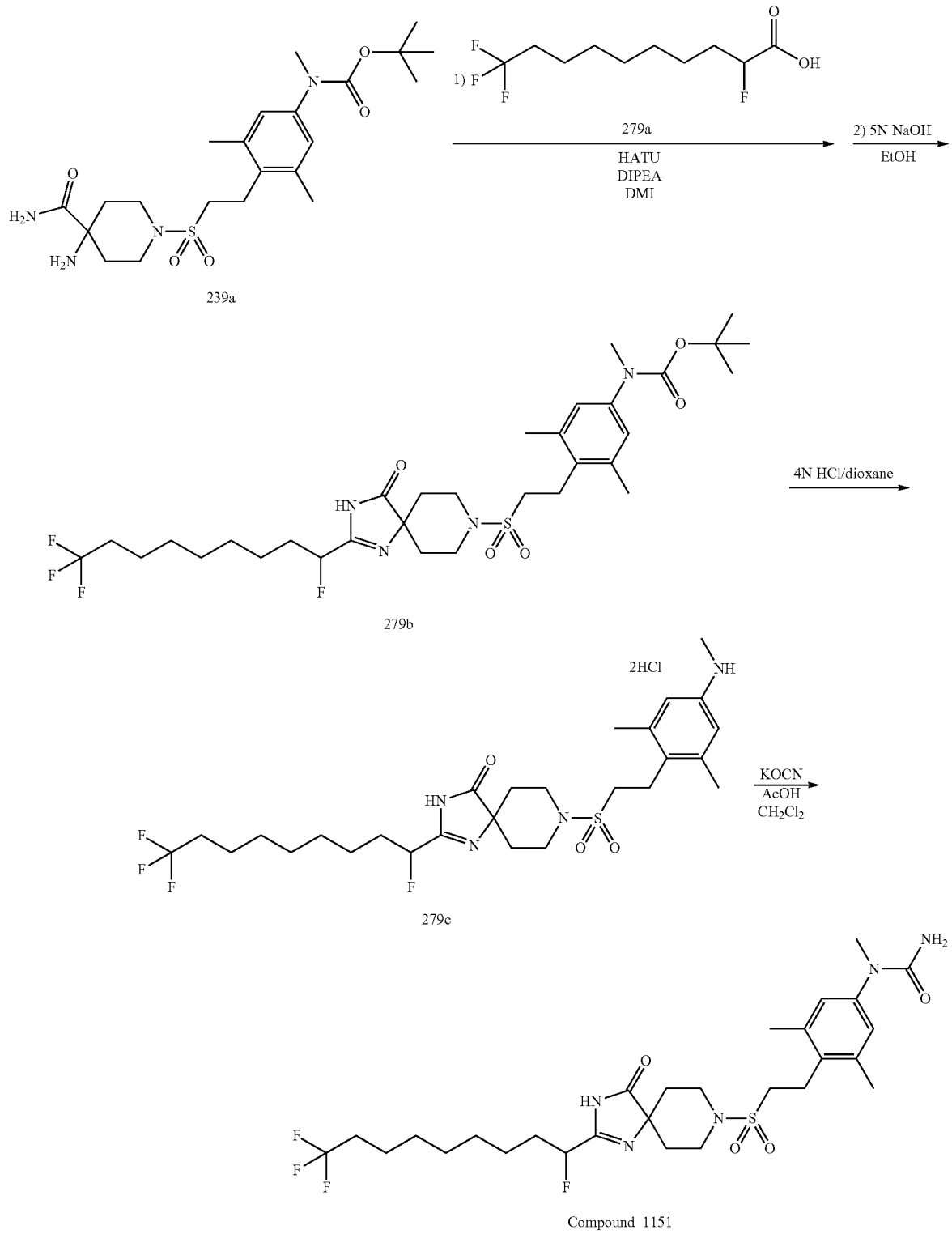

1-(3,5-Dimethyl-4-{2-[4-oxo-2-(1,9,9,9-tetrafluoro-nonyl)-1,3,8-triaza-spiro[4.5]dec-1-ene-8-sulfonyl]-ethyl}-phenyl)-1-methyl-urea was synthesized by operations similar to those in Reaction 269-1, Reaction 5-3 and Reaction 89-2 (using KOCN) using appropriate reagents and starting material.

MS (ESI) m/z=620 (M+H)+.

The carboxylic acid reagent used in the synthesis of Compound 1151 (2,10,10,10-tetrafluoro-decanoic acid) was synthesized by the following method.

(Reaction 279-2)

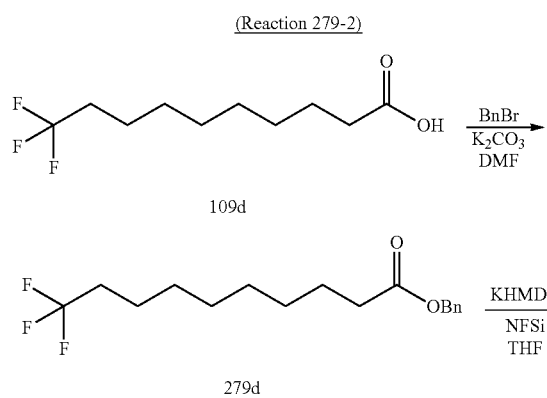

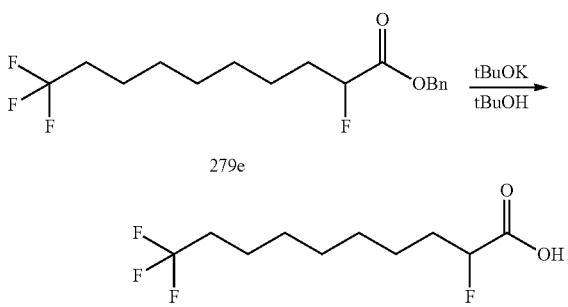

2,10,10,10-Tetrafluoro-decanoic acid was synthesized by operations similar to those in Reaction 26-4, Reaction 257-1 (using KHMDS as a base) and Reaction 215-2 using appropriate reagents and starting material.

$^1$H-NMR (400 MHz, CDCl$_3$) δ 1.30-1.40 (6H, m), 1.49-1.57 (4H, m), 1.90-2.13 (4H, m), 4.97 (1H, ddd, J=48.8, 5.2, 5.2 Hz).

Example 280

1-(3,5-Dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea (Compound 1152)

(Reaction 280-1)

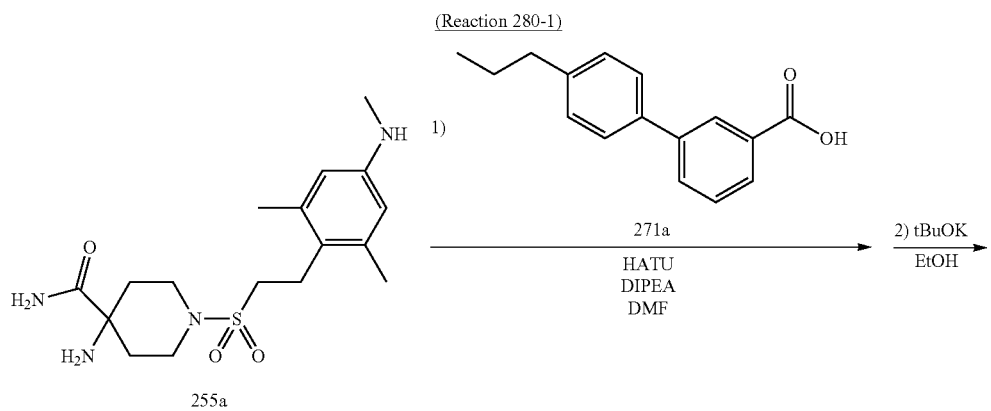

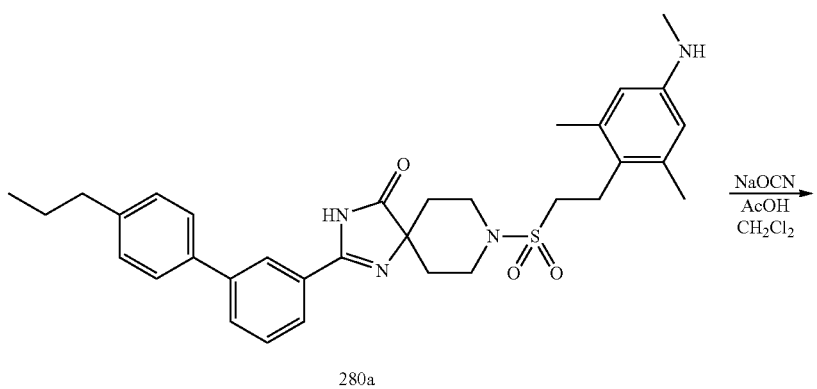

-continued

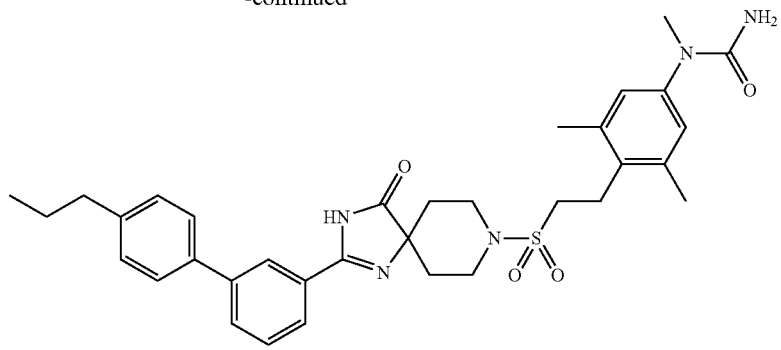

Compound 1152

1-(3,5-Dimethyl-4-{2-[4-oxo-2-(4'-propyl-biphenyl-3-yl)-1,3,8-triaza-spiro[4.5]dec-1-ene-8-sulfonyl]-ethyl}-phenyl)-1-methyl-urea was synthesized by operations similar to those in Reaction 269-1 and Reaction 89-2 using appropriate reagents and starting material.
MS (ESI) m/z=616 (M+H)+.

The example compounds shown below were synthesized by operations similar to those in Reaction 280-1 using appropriate reagents and starting materials.

Compounds 1153 to 1156

TABLE 168

| Compound | Structure | LCMS condition | Retention time (min) | MS (m/z) |
|---|---|---|---|---|
| 1153 | 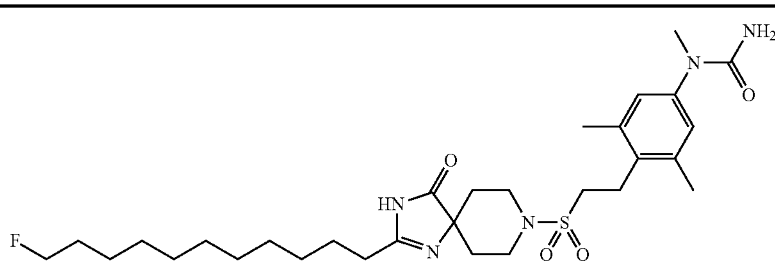 | LCMS-F-1 | 1.08 | 594 (M + H)+ |
| 1154 | 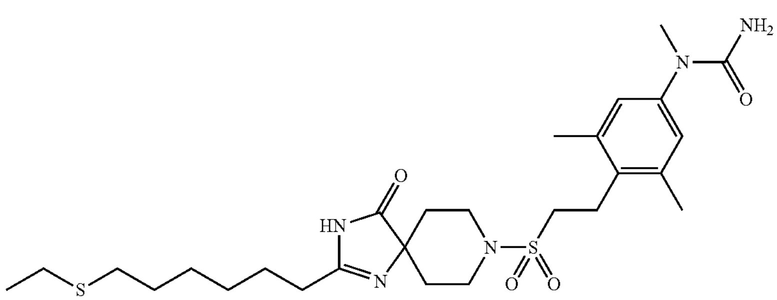 | LCMS-D-1 | 1.72 | 566 (M + H)+ |
| 1155 | 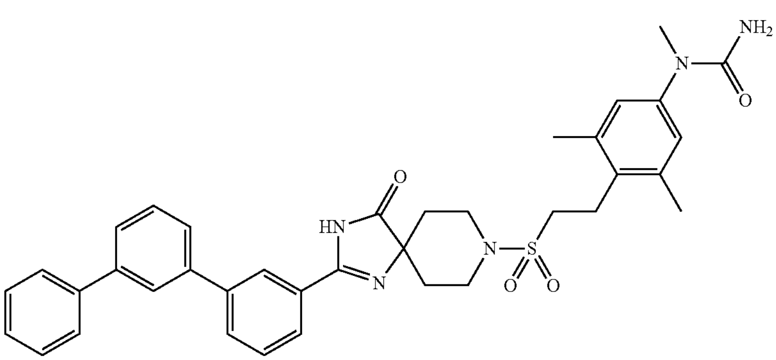 [SMILES: Cc1cc(N(C)C(N)=O)cc(C)c1CCS(=O)(=O)N1CCC2(CC1)N=C(c1cccc(-c3cccc(-c4ccccc4)c3)c1)NC2=O] | LCMS-D-1 | 3.12 | 650 (M + H)+ |

TABLE 168-continued

| Compound | Structure | LCMS condition | Retention time (min) | MS (m/z) |
|---|---|---|---|---|
| 1156 | 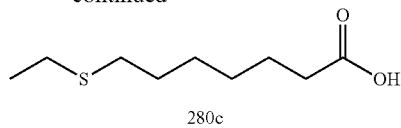 | LCMS-F-1 | 1.05 | 612 (M + H)+ |

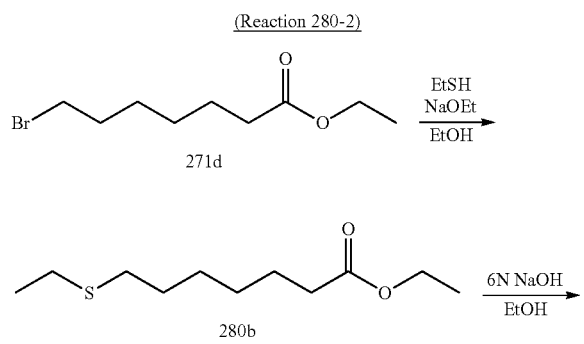

The carboxylic acid reagent used in the synthesis of Compound 1154 (7-ethylsulfanyl-heptanoic acid) was synthesized by the following method.

7-Ethylsulfanyl-heptanoic acid was synthesized by operations similar to those in Reaction 271-10 (using NaOEt as a base) and Reaction 95-18 using appropriate reagents and starting material.

$^1$H-NMR (300 MHz, DMSO-d6) δ 1.24 (m, 3H), 1.39 (m, 4H), 1.56 (m, 4H), 2.24 (m, 2H), 2.49 (m, 4H), 12.05 (s, 1H).

Example 281

1-{3,5-Dimethyl-4-[(E)-2-(4-oxo-2-[1,1';3',1'']terphenyl-3-yl-1,3,8-triaza-spiro[4.5]dec-1-ene-8-sulfonyl)-vinyl]-phenyl}-1-methyl-urea (Compound 1157)

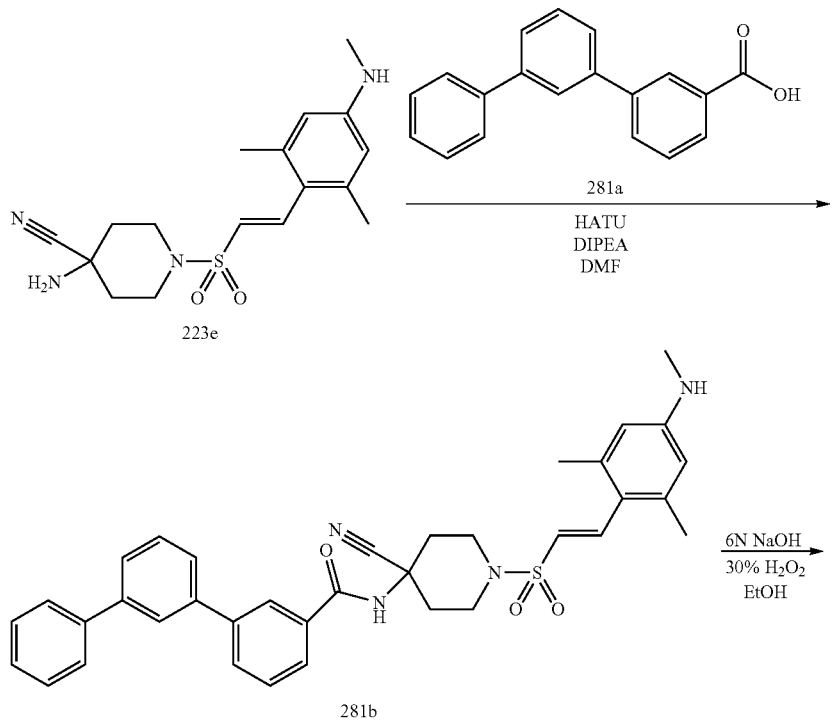

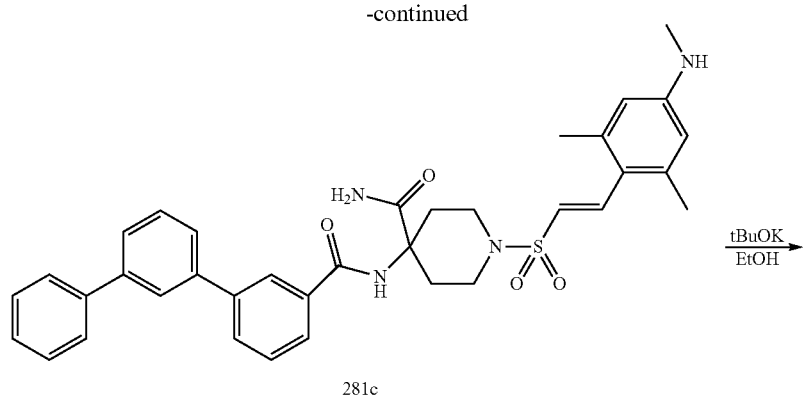

281c

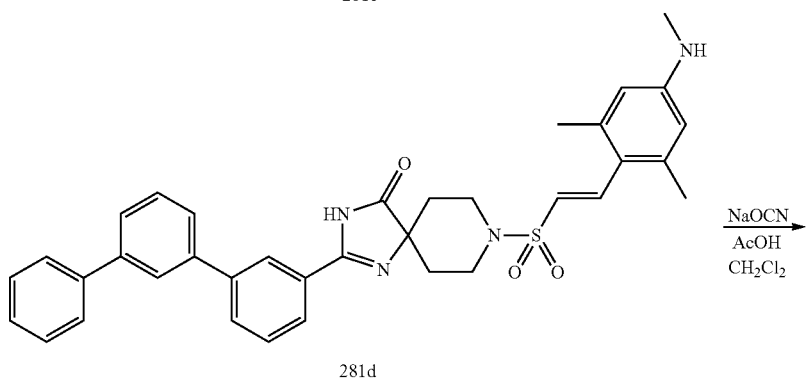

281d

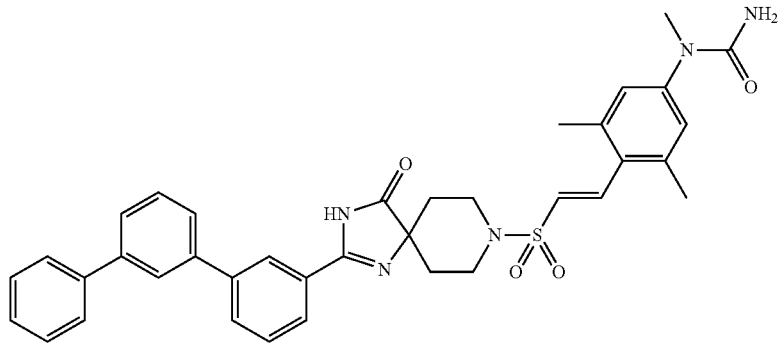

Compound 1157

1-{3,5-Dimethyl-4-[(E)-2-(4-oxo-2-[1,1';3',1"]terphenyl-3-yl-1,3,8-triaza-spiro[4.5]dec-1-ene-8-sulfonyl)-vinyl]-phenyl}-1-methyl-urea was synthesized by operations similar to those in Reaction 10-14, Reaction 10-11, Reaction 10-12 (using ethanol as a solvent) and Reaction 89-2 using appropriate reagents and starting material.

MS (ESI) m/z=648 (M+H)+.

The carboxylic acid reagent used in the synthesis of Compound 1157 ([1,1';3',1"]terphenyl-3-carboxylic acid) was synthesized by the following method.

(Reaction 281-2)

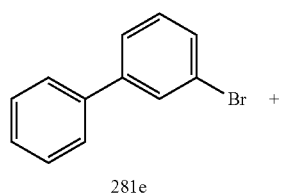

281e

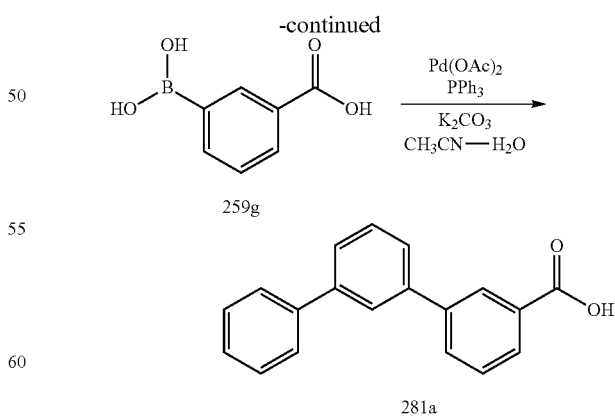

[1,1';3',1"]Terphenyl-3-carboxylic acid was synthesized by operations similar to those in Reaction 259-2 using appropriate reagents and starting material.

MS (ESI) m/z=275 (M+H)+.

Example 282

8-{(E)-2-[4-(4-Hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one (Compound 1158)

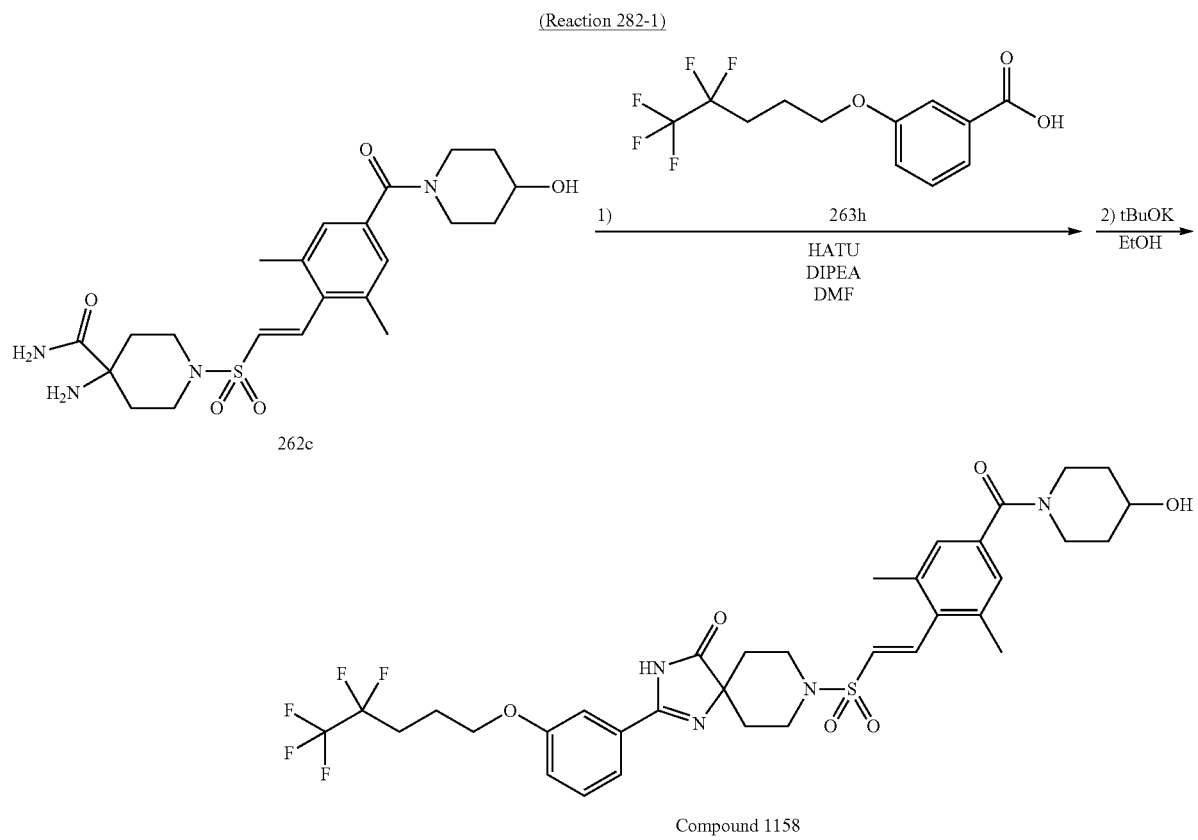

8-{(E)-2-[4-(4-Hydroxy-piperidine-1-carbonyl)-2,6-dimethyl-phenyl]-ethenesulfonyl}-2-[3-(4,4,5,5,5-pentafluoro-pentyloxy)-phenyl]-1,3,8-triaza-spiro[4.5]dec-1-en-4-one was synthesized by operations similar to those in Reaction 269-1 using appropriate reagents and starting material.
MS (ESI) m/z=727 (M+H)+.

The example compounds shown below were synthesized by operations similar to those in Reaction 282-1 using appropriate reagents and starting materials.

Compounds 1159 to 1160

TABLE 169

| Compound | Structure | LCMS condition | Retention time (min) | MS (m/z) |
|---|---|---|---|---|
| 1159 | 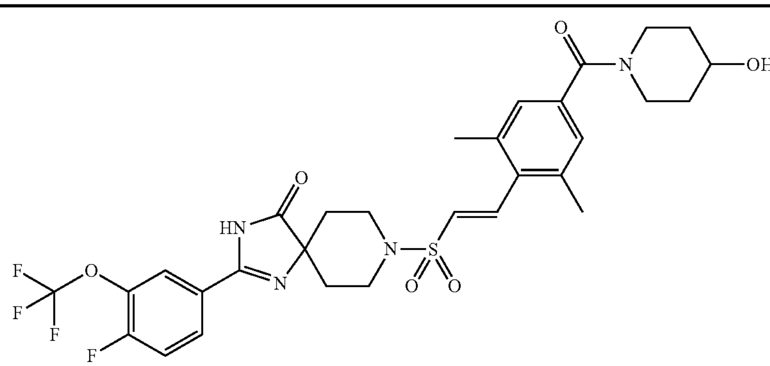 | LCMS-B-1 | 2.16 | 653 (M + H)+ |

TABLE 169-continued
| Compound | Structure | LCMS condition | Retention time (min) | MS (m/z) |
|---|---|---|---|---|
| 1160 | 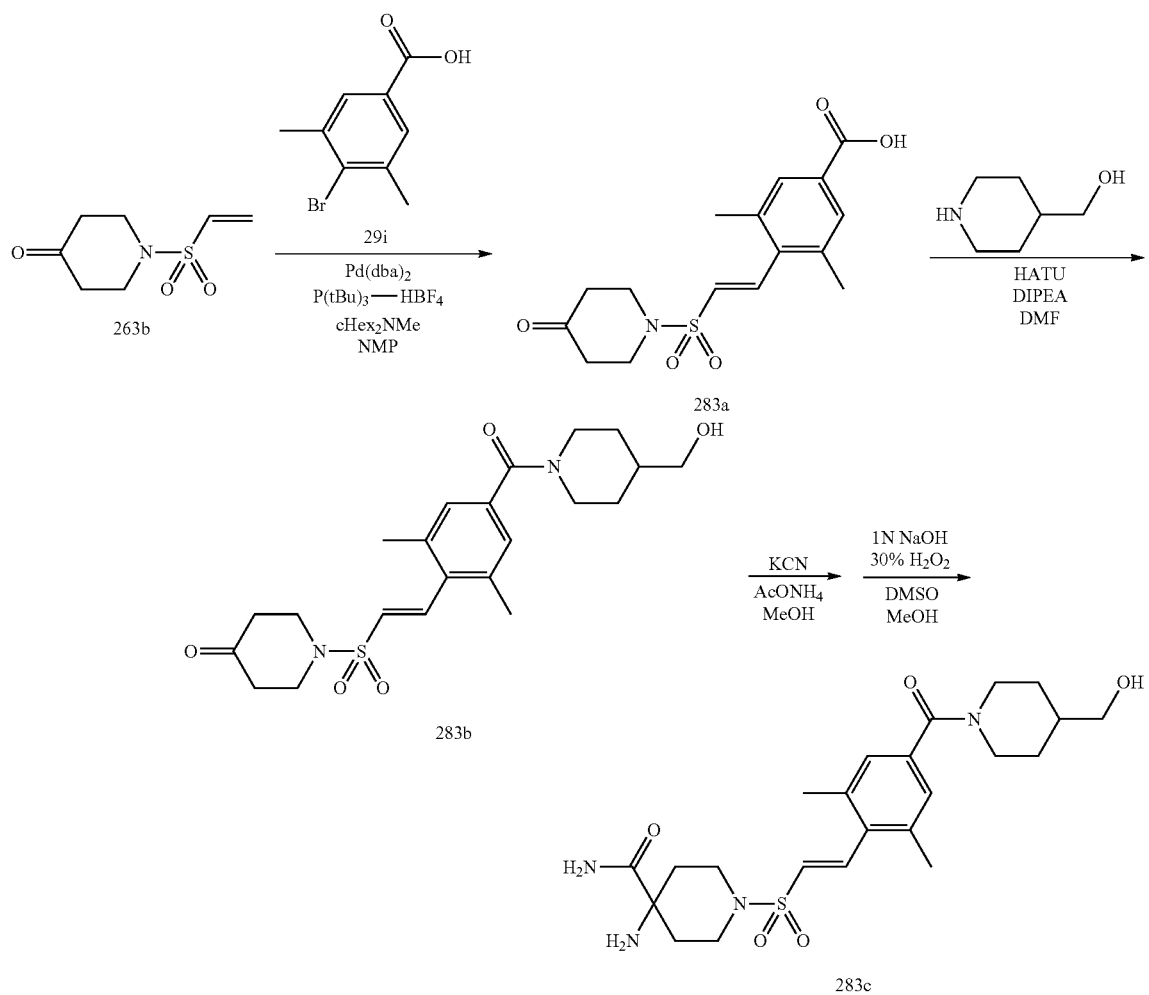 | LCMS-B-1 | 2.02 | 631 (M + H)+ |
Example 283
2-(4-Fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one (Compound 1161)
(Reaction 283-1)

4-Amino-1-{(E)-2-[4-(4-hydroxymethyl-piperidine-1-carbonyl)-2,6-dimethyl-phenyl]-ethenesulfonyl}-piperidine-4-carboxylic amide was synthesized by operations similar to those in Reaction 119-1, Reaction 10-14, Reaction 233-3 and Reaction 233-4 using appropriate reagents and starting material.

MS (ESI) m/z=479 (M+H)+.

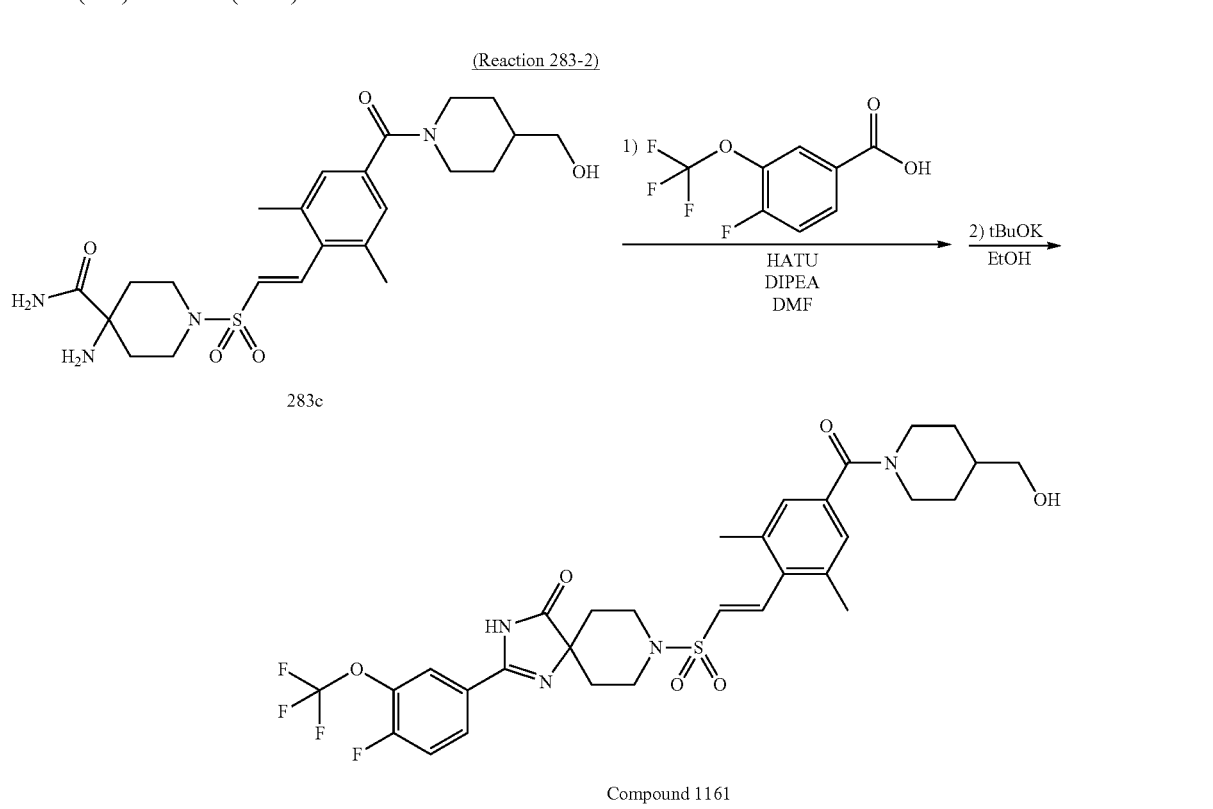

2-(4-Fluoro-3-trifluoromethoxy-phenyl)-8-{(E)-2-[4-(4-hydroxymethyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 269-1 using appropriate reagents and starting material.

MS (ESI) m/z=667 (M+H)+.

The example compound shown below was synthesized by operations similar to those in Reaction 283-2 using appropriate reagents and starting material.

Compound 1162

TABLE 170

| Compound | Structure | LCMS condition | Retention time (min) | MS (m/z) |
|---|---|---|---|---|
| 1162 | 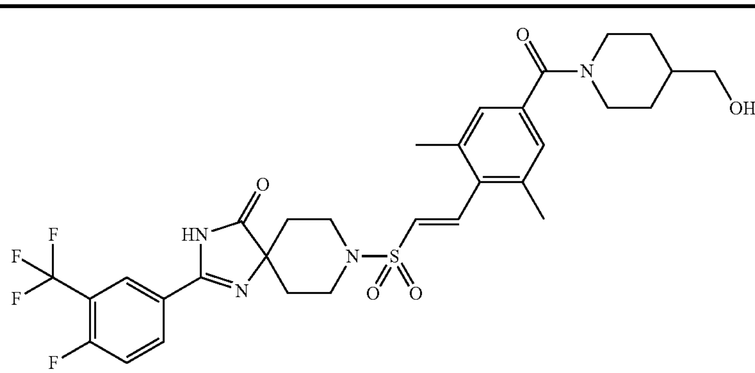 | LCQ-A-1 | 2.51 | 651 (M + H)+ |

Example 284

2-(2,2-Difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one (Compound 1163)

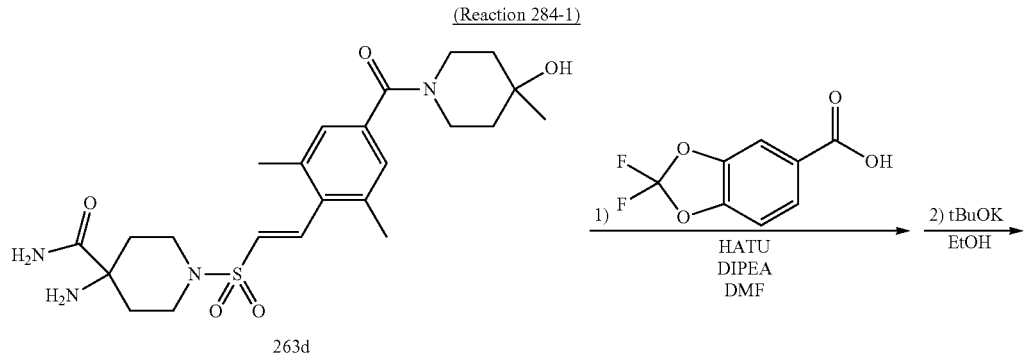

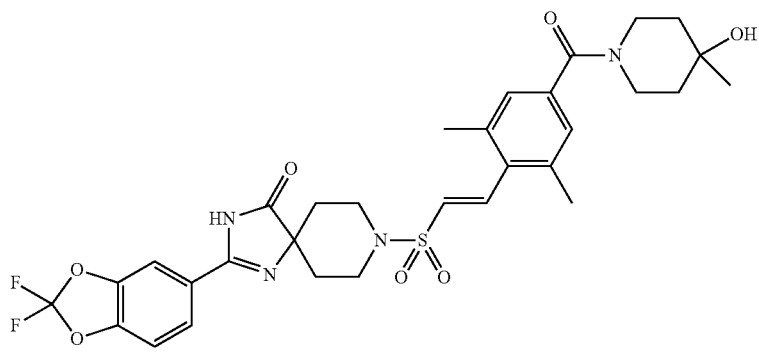 [SMILES: Cc1cc(C(=O)N2CCC(O)CC2)cc(C)c1/C=C/S(=O)(=O)N1CCC2(CC1)N=C(c1ccc3c(c1)OC(F)(F)O3)NC2=O]

Compound 1163

2-(2,2-Difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one was synthesized by operations similar to those in Reaction 269-1 using appropriate reagents and starting material.

MS (ESI) m/z=645 (M+H)+.

Example 285

8-{(E)-2-[4-((R)-2,3-Dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one (Compound 1164)

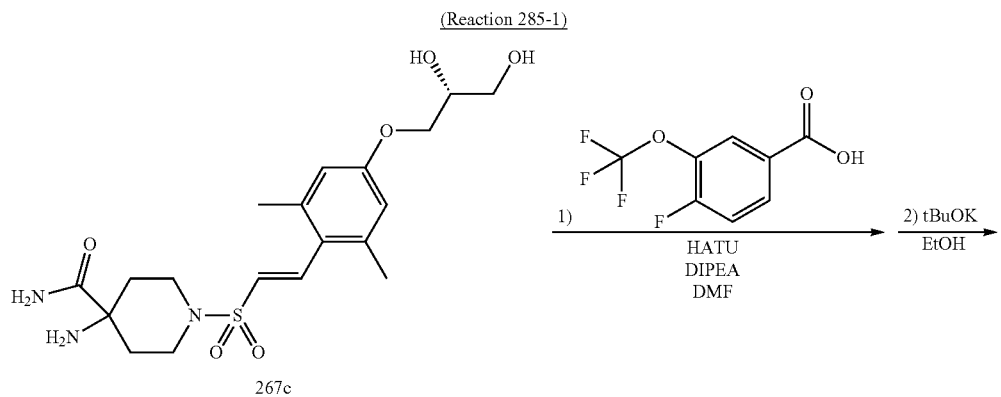

-continued

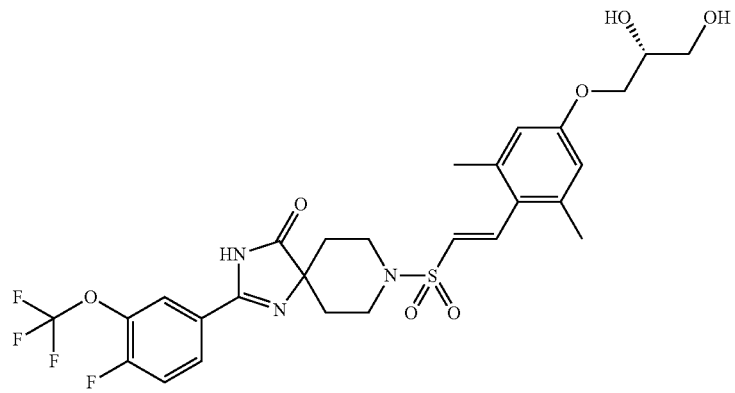

Compound 1164

8-{(E)-2-[4-((R)-2,3-Dihydroxy-propoxy)-2,6-dimethyl-phenyl]-ethenesulfonyl}-2-(4-fluoro-3-trifluoromethoxy-phenyl)-1,3,8-triaza-spiro[4.5]dec-1-en-4-one was synthesized by operations similar to those in Reaction 269-1 using appropriate reagents and starting material.

MS (ESI) m/z=616 (M+H)+.

The example compound shown below was synthesized by operations similar to those in Reaction 285-1 using appropriate reagents and starting material.

Compound 1165

TABLE 171

| Compound | Structure | LCMS condition | Retention time (min) | MS (m/z) |
|---|---|---|---|---|
| 1165 | 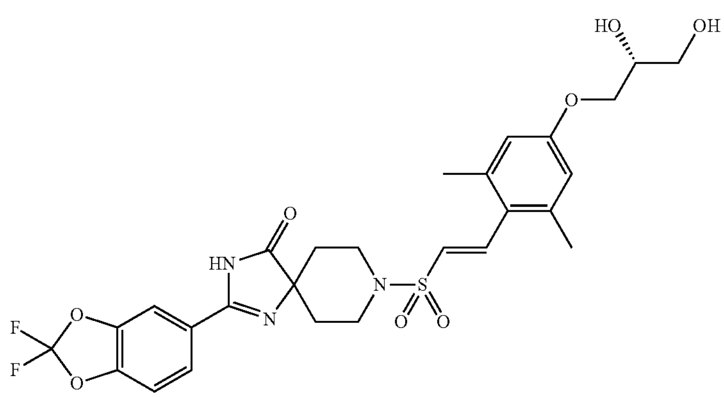 [SMILES: Cc1cc(OC[C@H](O)CO)cc(C)c1/C=C/S(=O)(=O)N1CCC2(CC1)N=C(c1ccc3c(c1)OC(F)(F)O3)NC2=O] | LCMS-F-1 | 0.94 | 594 (M + H)+ |

Example 286

8-{(E)-2-[4-(3,4-Dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one (Compound 1166)

(Reaction 286-1)

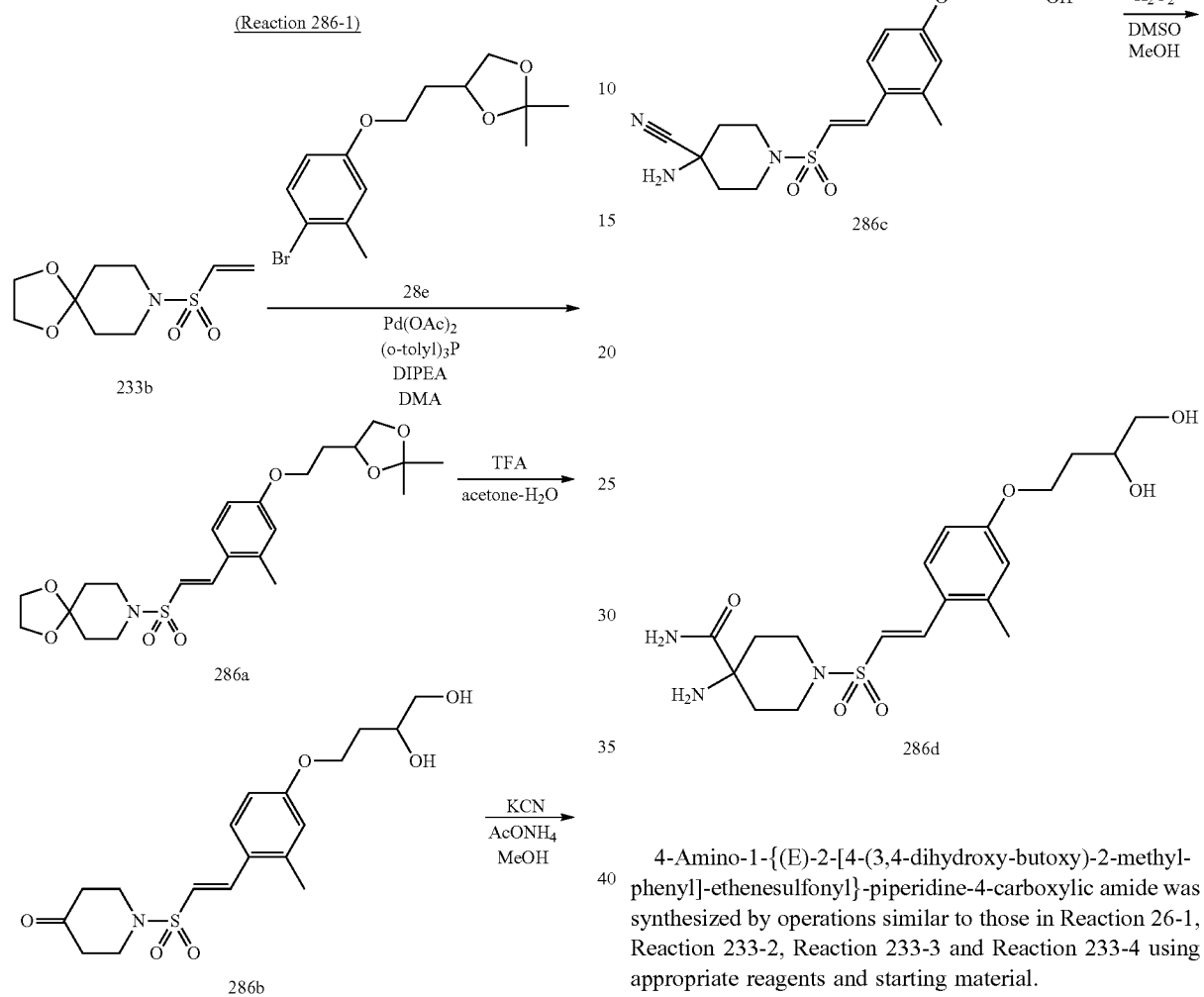

4-Amino-1-{(E)-2-[4-(3,4-dihydroxy-butoxy)-2-methyl-phenyl]-ethenesulfonyl}-piperidine-4-carboxylic amide was synthesized by operations similar to those in Reaction 26-1, Reaction 233-2, Reaction 233-3 and Reaction 233-4 using appropriate reagents and starting material.

MS (ESI) m/z=428 (M+H)+.

(Reaction 286-2)

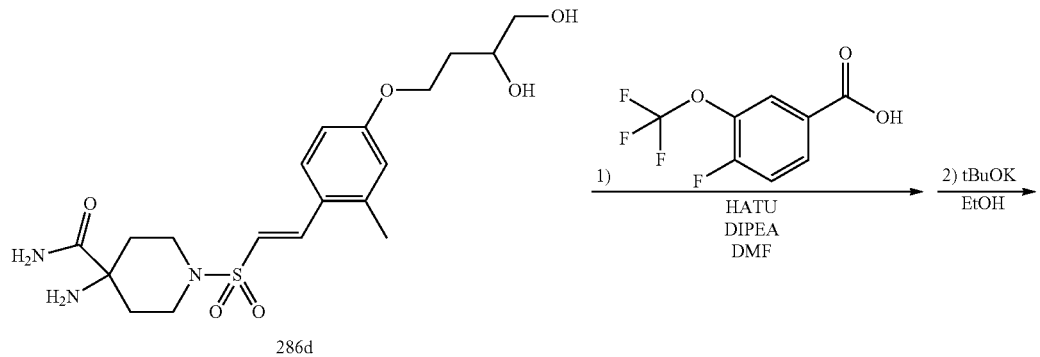

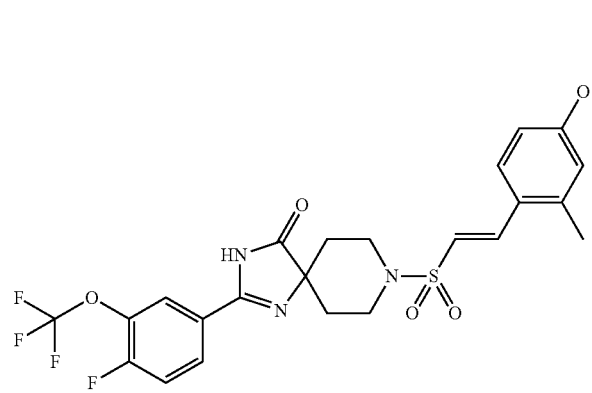

Compound 1166

8-{(E)-2-[4-(3,4-Dihydroxy-butoxy)-2-methyl-phenyl]-ethenesulfonyl}-2-(4-fluoro-3-trifluoromethoxy-phenyl)-1,3,8-triaza-spiro[4.5]dec-1-en-4-one was synthesized by operations similar to those in Reaction 269-1 using appropriate reagents and starting material.

MS (ESI) m/z=616 (M+H)+.

The example compounds shown below were synthesized by operations similar to those in Reaction 286-2 using appropriate reagents and starting materials.

Compound 1167

TABLE 172

| Compound | Structure | LCMS condition | Retention time (min) | MS (m/z) |
|---|---|---|---|---|
| 1167 | 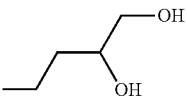 | LCMS-C-1 | 2.60 | 594 (M + H)+ |

Example 287

{4-[(E)-2-(2-Cyclohexyl-4-oxo-1,3,8-triaza-spiro[4.5]dec-1-ene-8-sulfonyl)-vinyl]-indol-1-yl}-acetic acid (Compound 1168)

(Reaction 287-1)

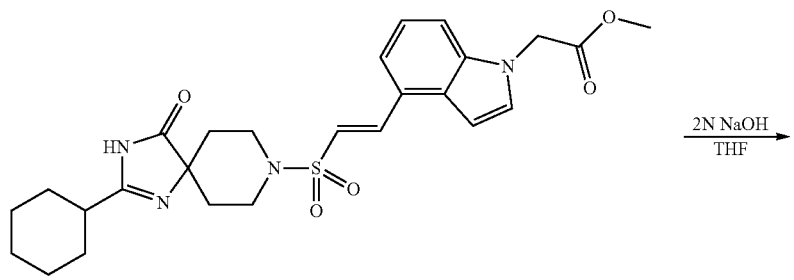

Compound 476

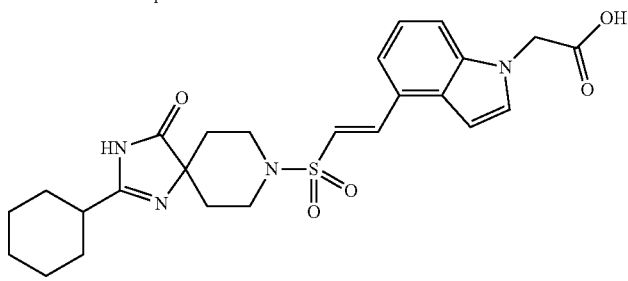

Compound 1168

{4-[(E)-2-(2-Cyclohexyl-4-oxo-1,3,8-triaza-spiro[4.5]dec-1-ene-8-sulfonyl)-vinyl]-indol-1-yl}-acetic acid (Compound 1168) was obtained by operations similar to those in Reaction 95-18 using Compound 476 as a starting material.

MS (ESI) m/z=499 (M+H)+.

The example compounds shown below were obtained by operations similar to those in Reaction 287-1 using appropriate starting compounds.

TABLE 173

| Raw material Compound | Target Compound | Structure | LCMS condition | Retention time (min) | MS (m/z) |
|---|---|---|---|---|---|
| 504 | 1169 | 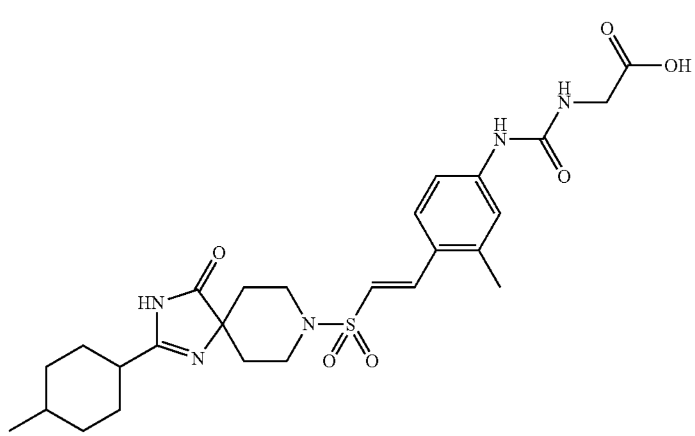 [SMILES: Cc1cc(NC(=O)NCC(=O)O)ccc1/C=C/S(=O)(=O)N1CCC2(CC1)N=C(C1CCC(C)CC1)NC2=O] | LCMS-A-1 | 1.94 | 546 (M + H)+ |

TABLE 173-continued
| Raw material Compound | Target Compound | Structure | LCMS condition | Retention time (min) | MS (m/z) |
|---|---|---|---|---|---|
| 1347 | 1170 | 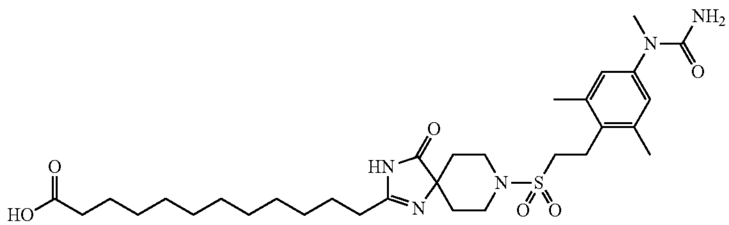 [SMILES: Cc1cc(N(C)C(N)=O)cc(C)c1CCS(=O)(=O)N1CCC2(CC1)N=C(CCCCCCCCCCCC(=O)O)NC2=O] | LCMS-C-1 | 2.52 | 620 (M + H)+ |
Example 288
10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic acid (Compound 1171)
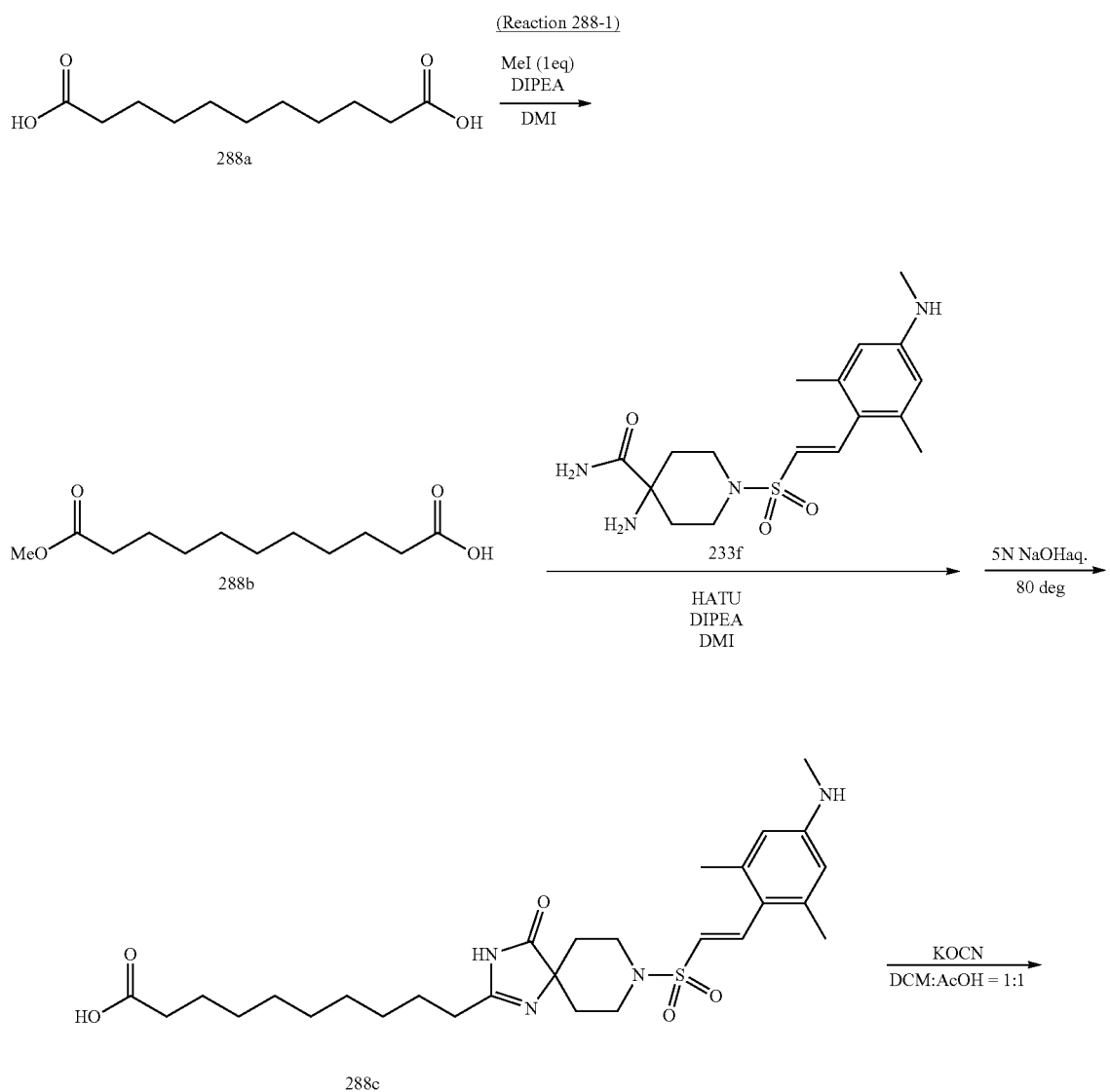

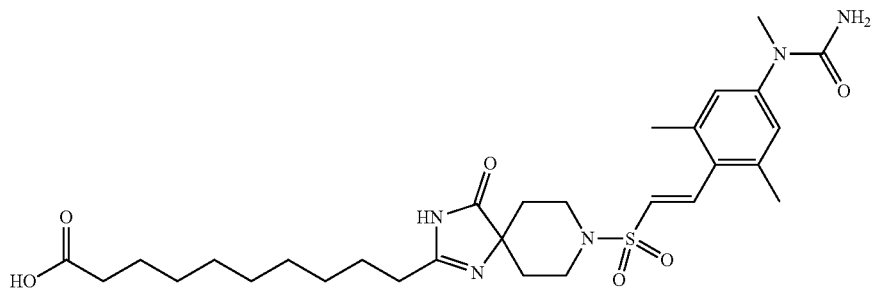

Compound 1171

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic acid (Compound 1171) was obtained by operations similar to those in Reaction 95-17 (using DMI as a solvent), Reaction 269-1 and Reaction 89-2 (using KOCN as a reagent) using appropriate reagents and starting material.

MS (ESI) m/z=590 (M+H)+.

Example 289

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic amide (Compound 1172)

(Reaction 289-1)

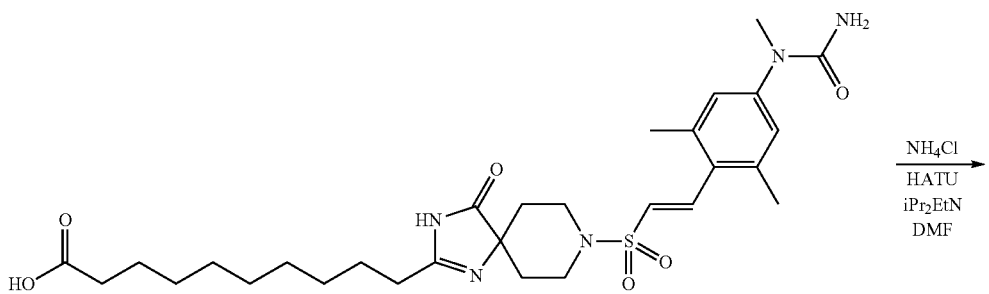

Compound 1171

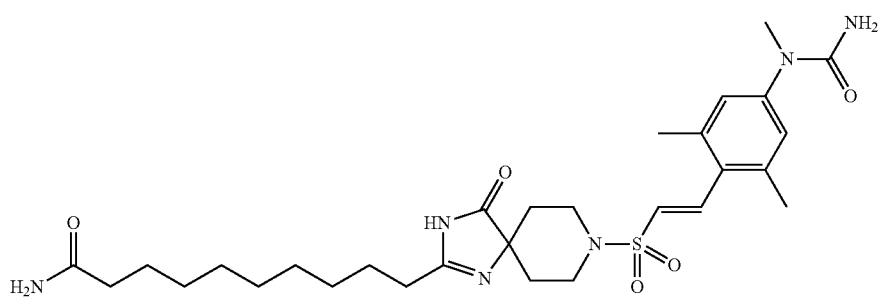

Compound 1172

10-(8-{(E)-2-[2,6-Dimethyl-4-(1-methyl-ureido)-phenyl]-ethenesulfonyl}-4-oxo-1,3,8-triaza-spiro[4.5]dec-1-en-2-yl)-decanoic amide was obtained by operations similar to those in Reaction 10-14 using Compound 1171 as a starting material.

MS (ESI) m/z=589 (M+H)+.

The example compounds shown below were obtained by operations similar to those in Reaction 289-1 using appropriate starting compounds.

TABLE 174

| Raw material Compound | Target Compound | Structure | LCMS condition | Retention time (min) | MS (m/z) |
|---|---|---|---|---|---|
| 1131 | 1173 | 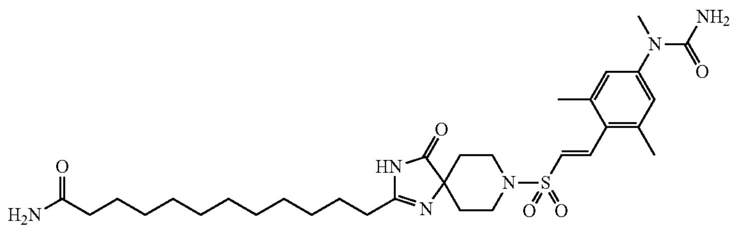 [SMILES: Cc1cc(N(C)C(N)=O)cc(C)c1/C=C/S(=O)(=O)N1CCC2(CC1)N=C(CCCCCCCCCCCC(N)=O)NC2=O] | LCMS-A-1 | 2.12 | 617 (M + H)+ |
| 1170 | 1174 | 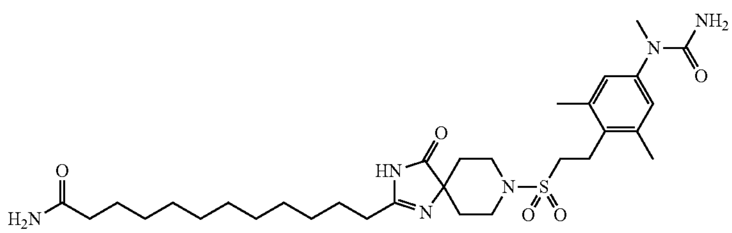 [SMILES: Cc1cc(N(C)C(N)=O)cc(C)c1CCS(=O)(=O)N1CCC2(CC1)N=C(CCCCCCCCCCCC(N)=O)NC2=O] | LCMS-A-1 | 2.10 | 619 (M + H)+ |
| 1109 | 1175 | 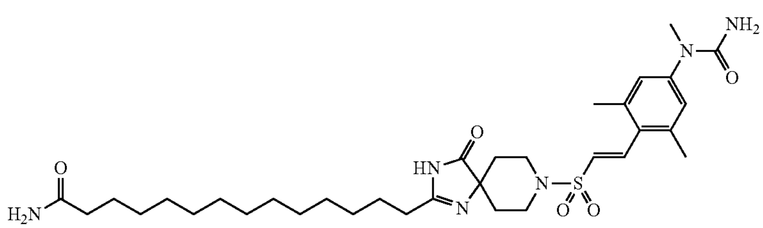 [SMILES: Cc1cc(N(C)C(N)=O)cc(C)c1/C=C/S(=O)(=O)N1CCC2(CC1)N=C(CCCCCCCCCCCCCC(N)=O)NC2=O] | LCMS-C-1 | 2.82 | 645 (M + H)+ |
| 1350 | 1176 | 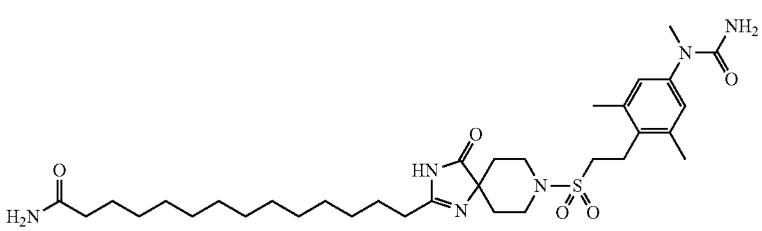 [SMILES: Cc1cc(N(C)C(N)=O)cc(C)c1CCS(=O)(=O)N1CCC2(CC1)N=C(CCCCCCCCCCCCCC(N)=O)NC2=O] | LCMS-C-1 | 2.80 | 647 (M + H)+ |

Example 290

8-[2-(2-Amino-5,7-dimethyl-benzoxazol-6-yl)-ethanesulfonyl]-2-(4-methyl-cyclohexyl)-1,3,8-triaza-spiro[4.5]dec-1-en-4-one (Compound 1178)

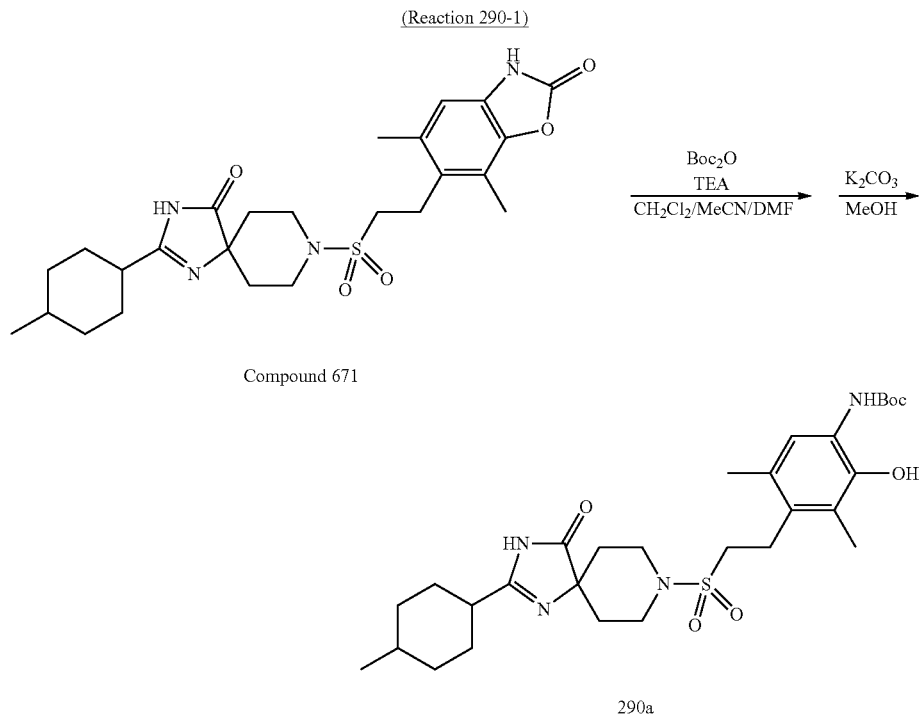

Triethylamine (34.7 µL, 249 µmol) and di-tert-butyl dicarbonate (32.6 mg, 149 µmol) were added to a solution of 8-[2-(5,7-dimethyl-2-oxo-2,3-dihydro-benzoxazol-6-yl)-ethanesulfonyl]-2-(4-methyl-cyclohexyl)-1,3,8-triaza-spiro[4.5]dec-1-en-4-one (25 mg, 49.7 µmol) in dichloromethane/acetonitrile/DMF (1:1:1) (1.0 mL) at room temperature, and the mixture was stirred at room temperature for three hours. The reaction solution was concentrated under reduced pressure, and the resulting residue was dissolved in methanol (1.0 mL) without purification. Potassium carbonate (34.3 mg, 249 µmol) was added to the solution, and the mixture was stirred at room temperature for two hours. H$_2$O (3 mL) was added, followed by extraction with dichloromethane (10 mL) twice. The organic layers were dried over sodium sulfate and concentrated under reduced pressure. The resulting residue was purified by PTLC (CH$_2$Cl$_2$-MeOH) to give (2-hydroxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-carbamic acid tert-butyl ester as a yellow substance (7.0 mg, 24%).

MS (ESI) m/z=577, 579 (M+H)+.

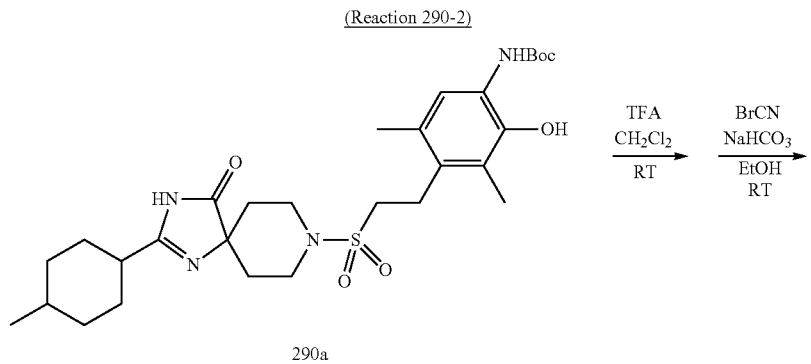

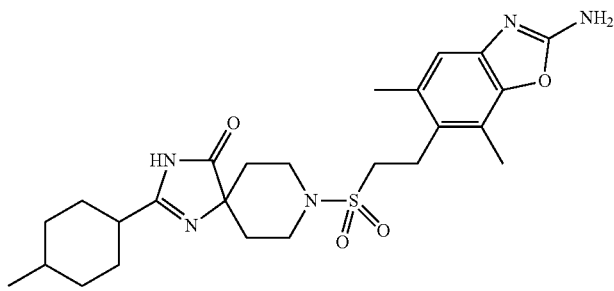

Compound 1178

A mixed solution of (2-hydroxy-3,5-dimethyl-4-{2-[2-(4-methyl-cyclohexyl)-4-oxo-1,3,8-triaza-spiro[4.5]dec-1-ene-8-sulfonyl]-ethyl}-phenyl)-carbamic acid tert-butyl ester (7.0 mg, 12.1 μmol) and dichloromethane/TFA (2:1) (750 μL) was prepared and stirred at room temperature for one hour. The reaction solution was concentrated under reduced pressure, and the resulting residue was dissolved in ethanol (1.00 mL) without purification. Bromocyanide (3.9 mg, 36.3 μmol) and sodium bicarbonate (6.1 mg, 72.6 μmol) were added to the solution, and the mixture was stirred at room temperature for five hours. H$_2$O (2 mL) were added, followed by extraction with ethyl acetate (10 mL) twice. The organic layers were dried over sodium sulfate and concentrated under reduced pressure. The resulting residue was purified by PTLC (CH$_2$Cl$_2$-MeOH-DMF) to give 8-[2-(2-amino-5,7-dimethyl-benzoxazol-6-yl)-ethanesulfonyl]-2-(4-methyl-cyclohexyl)-1,3,8-triaza-spiro[4.5]dec-1-en-4-one as a yellow substance (0.7 mg, 9%).

$^1$H-NMR (400 MHz, CDCl$_3$) δ 0.87 (3H, d, J=8.0 Hz), 0.85-1.01 (2H, m), 1.20-1.52 (5H, m), 1.68-1.78 (4H, br-m), 1.82-1.90 (2H, br-m), 2.24 (1H, tt, J=3.6, 12.0 Hz), 2.31 (3H, s), 2.33 (3H, s), 2.90-3.06 (2H, br-m), 3.11-3.19 (2H, br-m), 3.20-3.38 (2H, br-m), 3.60-3.68 (2H, br-m), 6.87 (1H, s), 7.24 (2H, s), 10.83 (1H, s).

Example 291

2-Cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one (Compound 1179)

(Reaction 291-1)

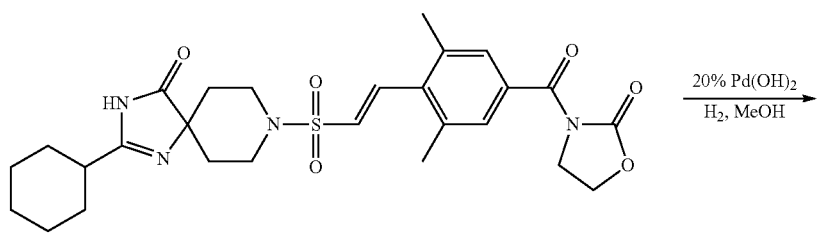

Compound 1007

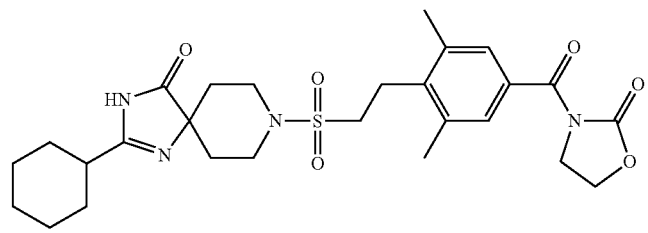

Compound 1179

2-Cyclohexyl-8-{2-[2,6-dimethyl-4-(2-oxo-oxazolidine-3-carbonyl)-phenyl]-ethanesulfonyl}-1,3,8-triaza-spiro[4.5]dec-1-en-4-one (Compound 1179) was obtained by operations similar to those in Reaction 122-2 using Compound as a starting material.

MS (ESI) m/z=545 (M+H)+.

The example compounds shown below were obtained by operations similar to those in Reaction 291-1 using appropriate solvents (acetonitrile or methanol or an acetonitrile-methanol mixed solution) and starting compounds.

TABLE 175

| Raw material Compound | Target Compound | Structure | LCMS condition | Retention time (min) | MS (m/z) |
|---|---|---|---|---|---|
| 998 | 1180 | 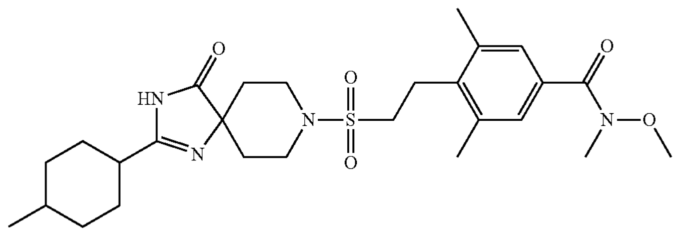 | LCMS-D-1 | 2.02 | 533 (M + H)+ |
| 992 | 1181 | 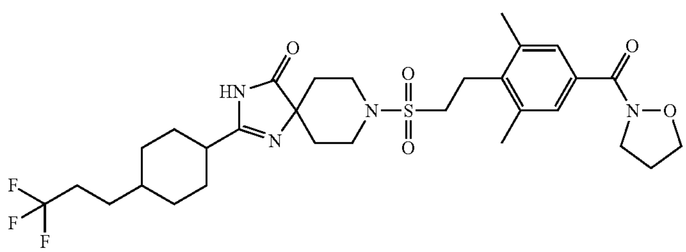 [SMILES: Cc1cc(C(=O)N2CCCO2)cc(C)c1CCS(=O)(=O)N1CCC2(CC1)N=C(C1CCC(CCC(F)(F)F)CC1)NC2=O] | LCMS-D-1 | 2.77 | 627 (M + H)+ |
| 1001 | 1182 | 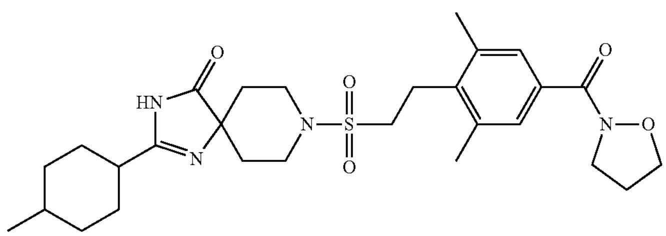 [SMILES: Cc1cc(C(=O)N2CCCO2)cc(C)c1CCS(=O)(=O)N1CCC2(CC1)N=C(C1CCC(C)CC1)NC2=O] | LCMS-D-1 | 1.93 | 545 (M + H)+ |
| 1002 | 1183 | 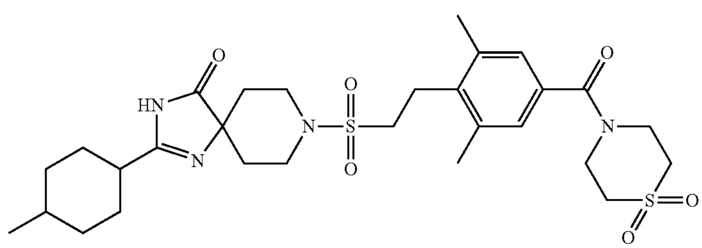 [SMILES: Cc1cc(C(=O)N2CCS(=O)(=O)CC2)cc(C)c1CCS(=O)(=O)N1CCC2(CC1)N=C(C1CCC(C)CC1)NC2=O] | LCMS-D-1 | 1.72 | 607 (M + H)+ |
| 1010 | 1184 | TFA | LCMS-D-1 | 2.31 | 731 (M + H)+ |

Example 292

2-(3,4-Dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one (Compound 1185)

(Reaction 292-1)

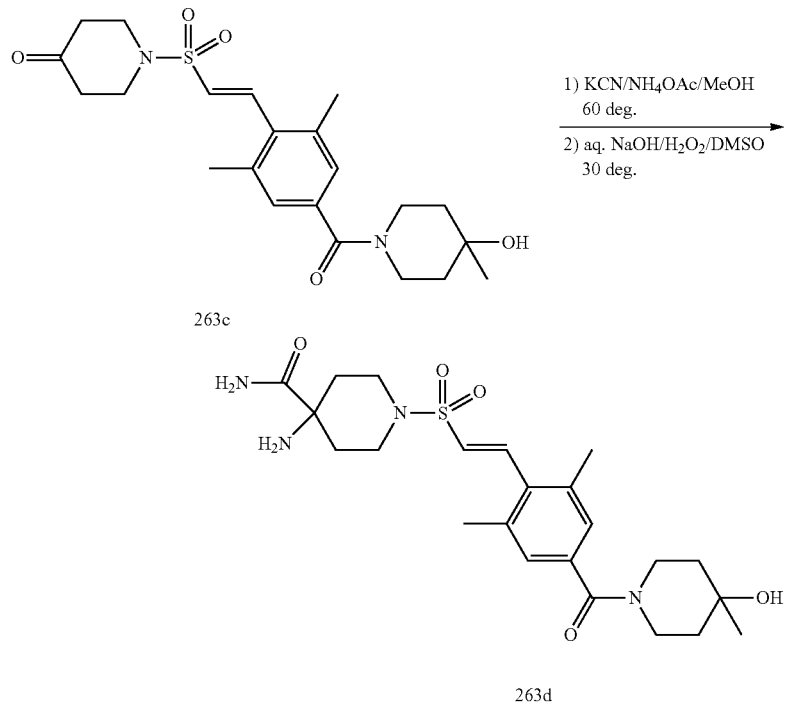

4-Amino-1-{(E)-2-[4-(4-hydroxy-4-methyl-piperidine-1-carbonyl)-2,6-dimethyl-phenyl]-ethenesulfonyl}-piperidine-4-carboxylic amide was obtained by operations similar to those in Reaction 233-3 and Reaction 233-4 using appropriate reagents and starting material.

MS (ESI) m/z=479 (M+H)+.

(Reaction 292-2)

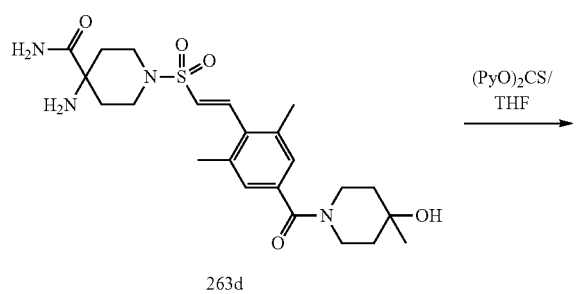

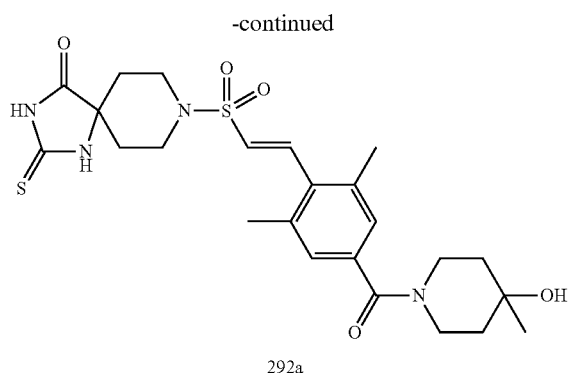

Di(2-pyridyl)thionocarbonate (0.97 g, 4.2 mmol) was added to a solution of 4-amino-1-{(E)-2-[4-(4-hydroxy-4-methyl-piperidine-1-carbonyl)-2,6-dimethyl-phenyl]-ethenesulfonyl}-piperidine-4-carboxylic amide (1.82 g, 3.8 mmol) in THF (7.6 ml), and the mixture was stirred at 50° C. for one hour. The reaction mixture was purified by column chromatography (amine-loaded silica gel, dichloromethane/methanol=99:1→88:12) to give 8-{(E)-2-[4-(4-hydroxy-4-methyl-piperidine-1-carbonyl)-2,6-dimethyl-phenyl]-ethenesulfonyl}-2-thioxo-1,3,8-triaza-spiro[4.5]decan-4-one as a colorless solid (1.55 g, 78%).

MS (ESI) m/z=521 (M+H)+.

(Reaction 292-3)

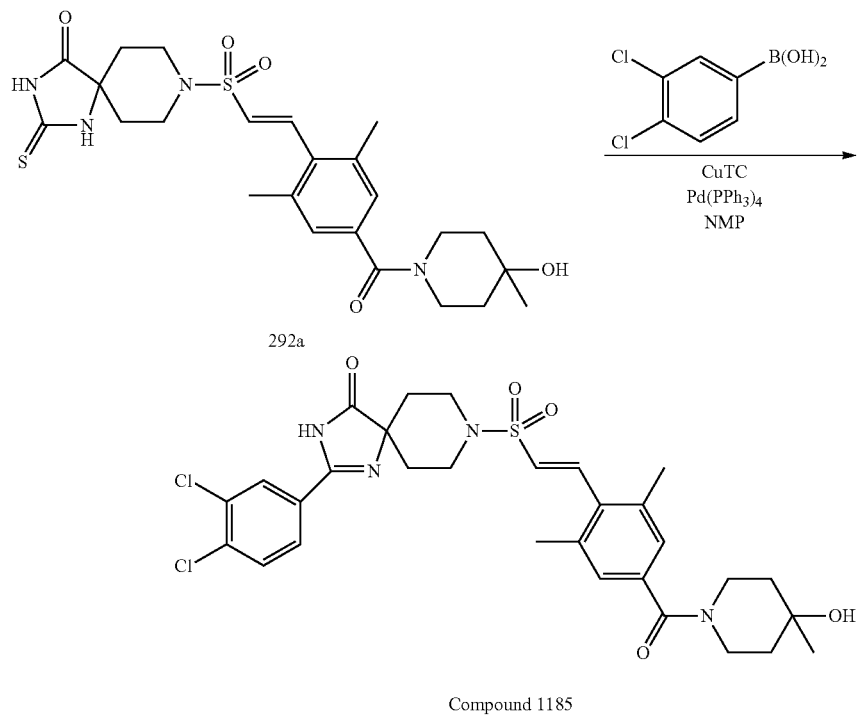

Compound 1185

A solution of 8-{(E)-2-[4-(4-hydroxy-4-methyl-piperidine-1-carbonyl)-2,6-dimethyl-phenyl]-ethenesulfonyl}-2-thioxo-1,3,8-triaza-spiro[4.5]decan-4-one (25 mg, 0.048 mmol), 3,4-dichlorophenylboronic acid (27.5 mg, 0.144 mmol), palladium tetrakistriphenylphosphine (11.1 mg, 0.0096 mmol) and CuTC (36.8 mg, 0.192 mmol) in NMP (0.1 mL) was heated with stirring at 80° C. for 30 minutes in a nitrogen atmosphere. After cooling to room temperature, N-acetylcysteine (33 mg, 0.2 mmol) was added to the reaction mixture. The reaction mixture was purified by silica gel column chromatography (NH silica gel, methylene chloride:methanol=100:0→90:10) to give 2-(3,4-dichloro-phenyl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one as a white solid (13.4 mg, 44%).

MS (ESI) m/z=633 (M+H)+.

The example compounds shown below were obtained by operations similar to those in Reaction 292-3 using appropriate starting compounds.

Compounds 1186 to Compound 1238

TABLE 176

| Target Compound | Structure | LCMS condition | Retention time (min) | MS (m/z) |
|---|---|---|---|---|
| 1186 | 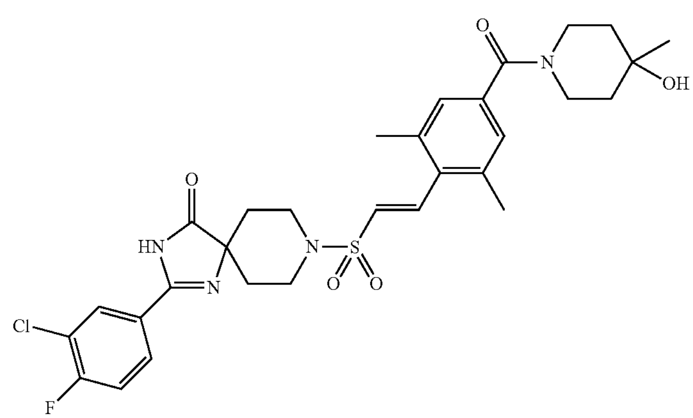 [SMILES: Cc1cc(C(=O)N2CCC(C)(O)CC2)cc(C)c1/C=C/S(=O)(=O)N1CCC2(CC1)N=C(c1ccc(F)c(Cl)c1)NC2=O] | LCMS-F-2 | 0.72 | 617 (M + H)+ |

TABLE 176-continued

| Target Compound | Structure | LCMS condition | Retention time (min) | MS (m/z) |
|---|---|---|---|---|
| 1187 | 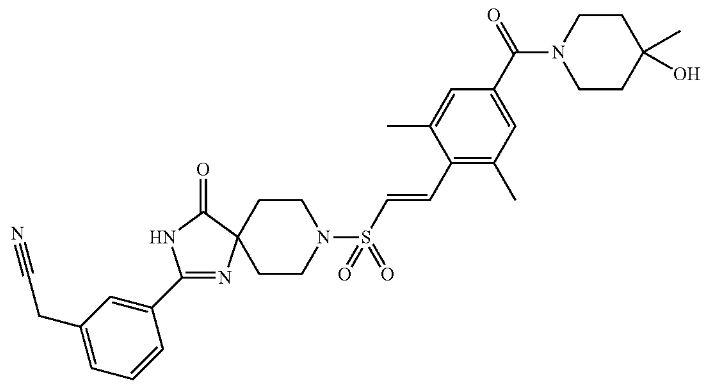 [SMILES: Cc1cc(C(=O)N2CCC(C)(O)CC2)cc(C)c1/C=C/S(=O)(=O)N1CCC2(CC1)N=C(c1cccc(CC#N)c1)NC2=O] | LCMS-F-2 | 0.63 | 604 (M + H)+ |
| 1188 | 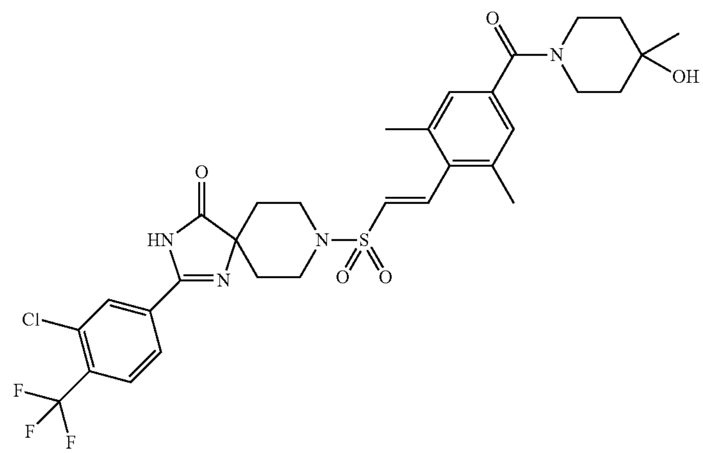 [SMILES: Cc1cc(C(=O)N2CCC(C)(O)CC2)cc(C)c1/C=C/S(=O)(=O)N1CCC2(CC1)N=C(c1ccc(C(F)(F)F)c(Cl)c1)NC2=O] | LCMS-F-2 | 0.79 | 667 (M + H)+ |
| 1189 | 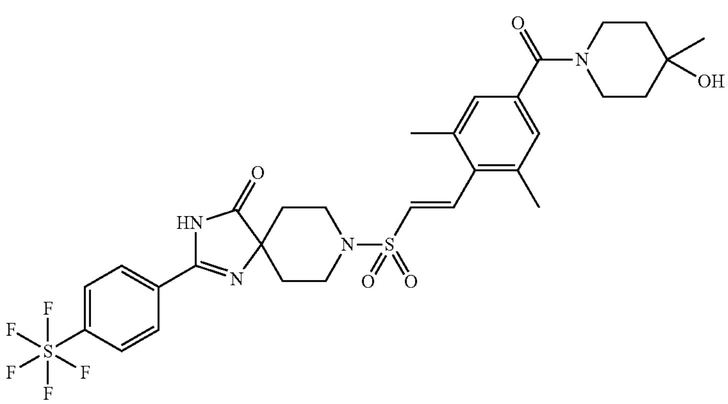 [SMILES: Cc1cc(C(=O)N2CCC(C)(O)CC2)cc(C)c1/C=C/S(=O)(=O)N1CCC2(CC1)N=C(c1ccc(S(F)(F)(F)(F)F)cc1)NC2=O] | LCMS-F-2 | 0.77 | 691 (M + H)+ |
| 1190 | 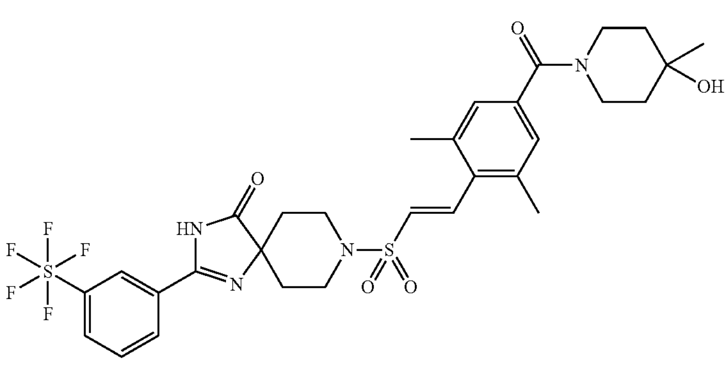 [SMILES: Cc1cc(C(=O)N2CCC(C)(O)CC2)cc(C)c1/C=C/S(=O)(=O)N1CCC2(CC1)N=C(c1cccc(S(F)(F)(F)(F)F)c1)NC2=O] | LCMS-F-2 | 0.76 | 691 (M + H)+ |

TABLE 176-continued

| Target Compound | Structure | LCMS condition | Retention time (min) | MS (m/z) |
|---|---|---|---|---|
| 1191 | 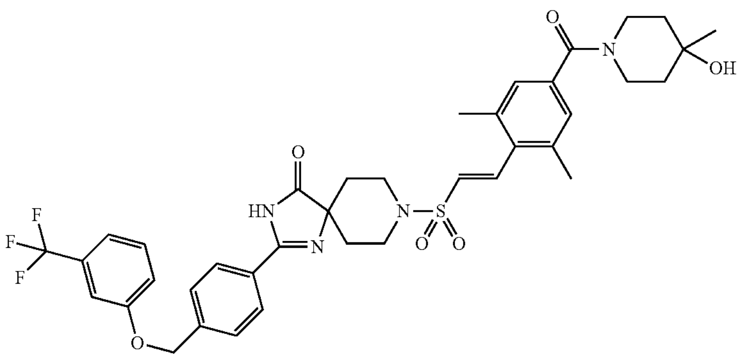 [SMILES: Cc1cc(C(=O)N2CCC(C)(O)CC2)cc(C)c1/C=C/S(=O)(=O)N1CCC2(CC1)N=C(c1ccc(COc3cccc(C(F)(F)F)c3)cc1)NC2=O] | LCMS-F-2 | 0.84 | 739 (M + H)+ |
| 1192 | 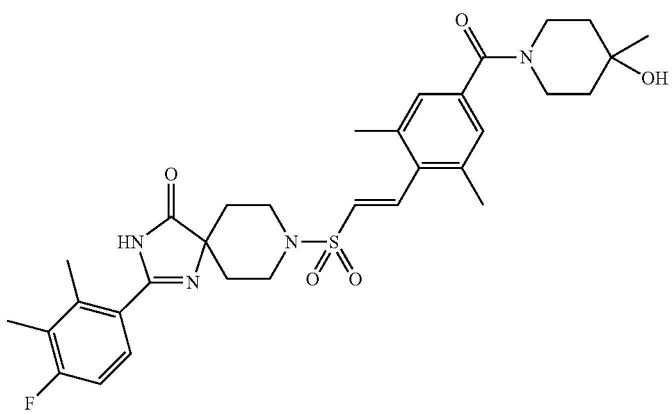 | LCMS-F-2 | 0.69 | 611 (M + H)+ |
| 1193 | 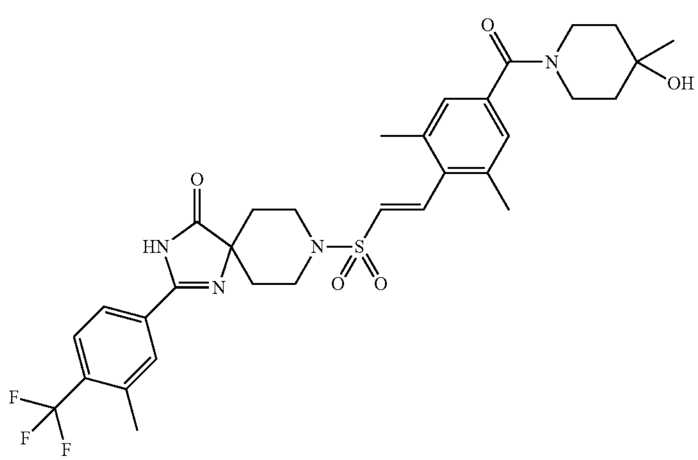 [SMILES: Cc1cc(C2=NC3(CCN(S(=O)(=O)/C=C/c4c(C)cc(C(=O)N5CCC(C)(O)CC5)cc4C)CC3)C(=O)N2)ccc1C(F)(F)F] | LCMS-F-2 | 0.78 | 647 (M + H)+ |

TABLE 176-continued

| Target Compound | Structure | LCMS condition | Retention time (min) | MS (m/z) |
|---|---|---|---|---|
| 1194 | 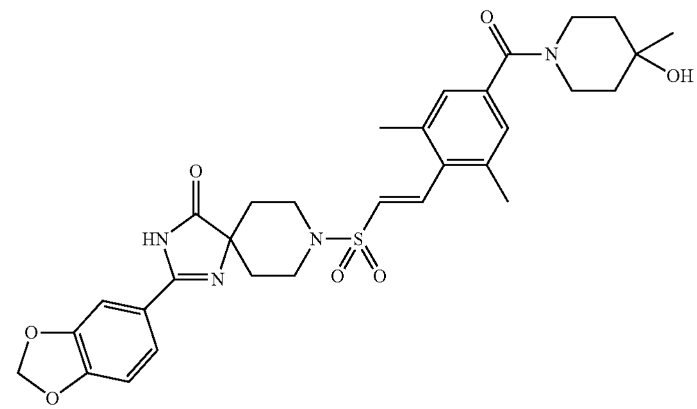 [SMILES: Cc1cc(C(=O)N2CCC(C)(O)CC2)cc(C)c1/C=C/S(=O)(=O)N1CCC2(CC1)N=C(c1ccc3c(c1)OCO3)NC2=O] | LCMS-F-2 | 0.61 | 609 (M + H)+ |
| 1195 | 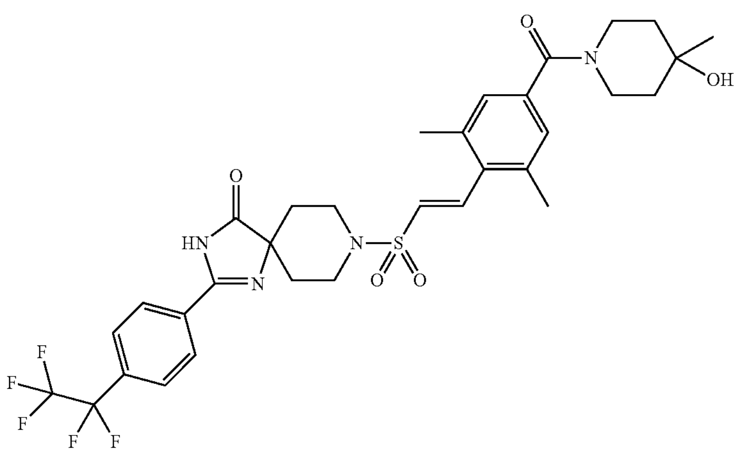 [SMILES: Cc1cc(C(=O)N2CCC(C)(O)CC2)cc(C)c1/C=C/S(=O)(=O)N1CCC2(CC1)N=C(c1ccc(C(F)(F)C(F)(F)F)cc1)NC2=O] | LCMS-F-2 | 0.79 | 683 (M + H)+ |
| 1196 | 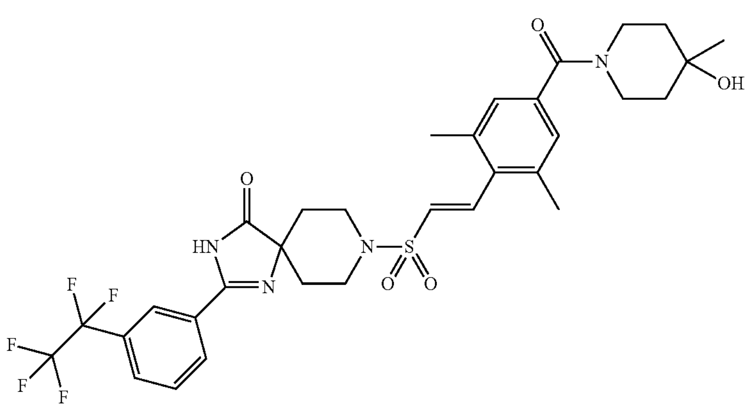 [SMILES: Cc1cc(C(=O)N2CCC(C)(O)CC2)cc(C)c1/C=C/S(=O)(=O)N1CCC2(CC1)N=C(c1cccc(C(F)(F)C(F)(F)F)c1)NC2=O] | LCMS-F-2 | 0.78 | 683 (M + H)+ |

TABLE 176-continued
| Target Compound | Structure | LCMS condition | Retention time (min) | MS (m/z) |
|---|---|---|---|---|
| 1197 | 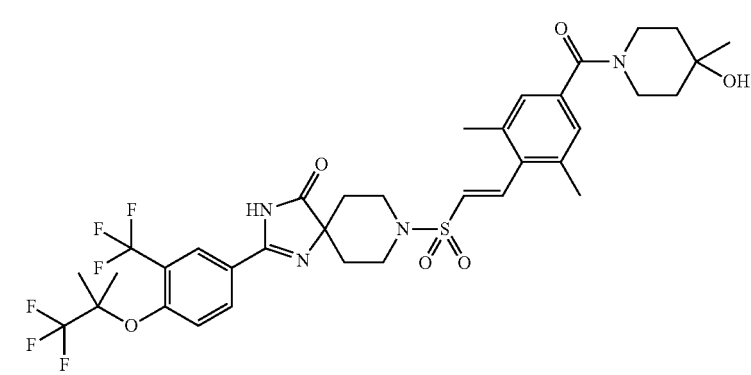 [SMILES: Cc1cc(C(=O)N2CCC(C)(O)CC2)cc(C)c1/C=C/S(=O)(=O)N1CCC2(CC1)N=C(c1ccc(OC(C)(C)C(F)(F)F)c(C(F)(F)F)c1)NC2=O] | LCMS-F-2 | 0.84 | 759 (M + H)+ |
| 1198 | 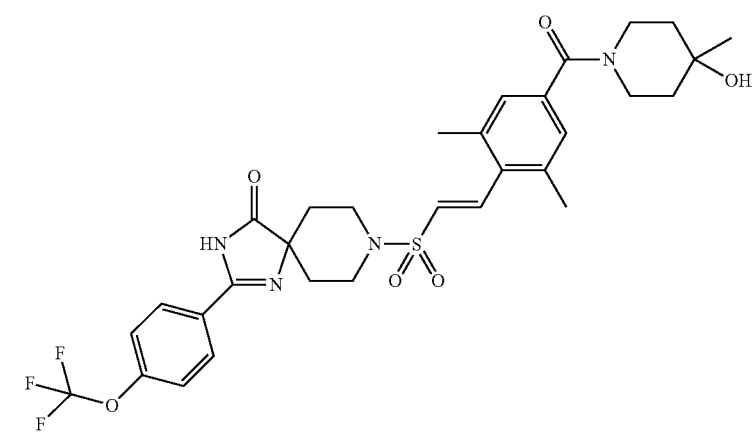 [SMILES: Cc1cc(C(=O)N2CCC(C)(O)CC2)cc(C)c1/C=C/S(=O)(=O)N1CCC2(CC1)N=C(c1ccc(OC(F)(F)F)cc1)NC2=O] | LCMS-G-1 | 1.11 | 649 (M + H)+ |
| 1199 | 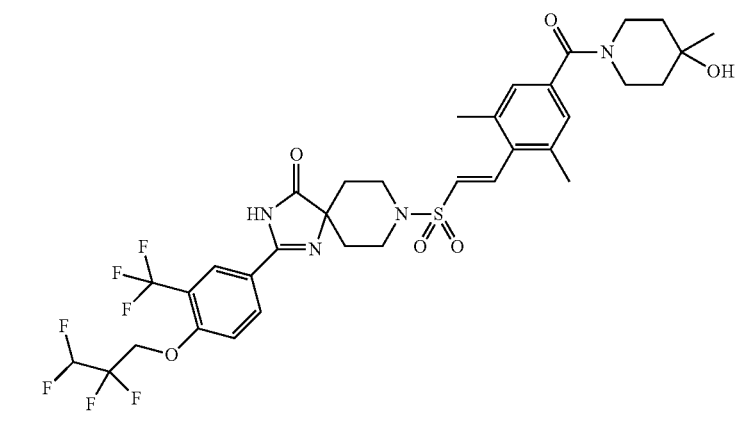 [SMILES: Cc1cc(C(=O)N2CCC(C)(O)CC2)cc(C)c1/C=C/S(=O)(=O)N1CCC2(CC1)N=C(c1ccc(OCC(F)(F)C(F)F)c(C(F)(F)F)c1)NC2=O] | LCMS-G-1 | 1.10 | 763 (M + H)+ |

TABLE 176-continued
| Target Compound | Structure | LCMS condition | Retention time (min) | MS (m/z) |
|---|---|---|---|---|
| 1200 | 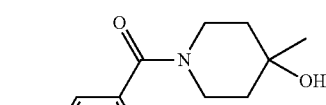 | LCMS G-1 | 1.10 | 731 (M + H)+ |
| 1201 | 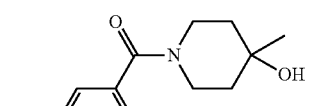 | LCMS-G-1 | 1.13 | 729 (M + H)+ |
| 1202 | 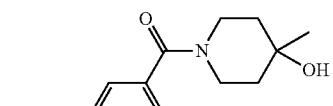 | LCMS-G-1 | 1.15 | 809 (M + H)+ |

TABLE 176-continued

| Target Compound | Structure | LCMS condition | Retention time (min) | MS (m/z) |
|---|---|---|---|---|
| 1203 | 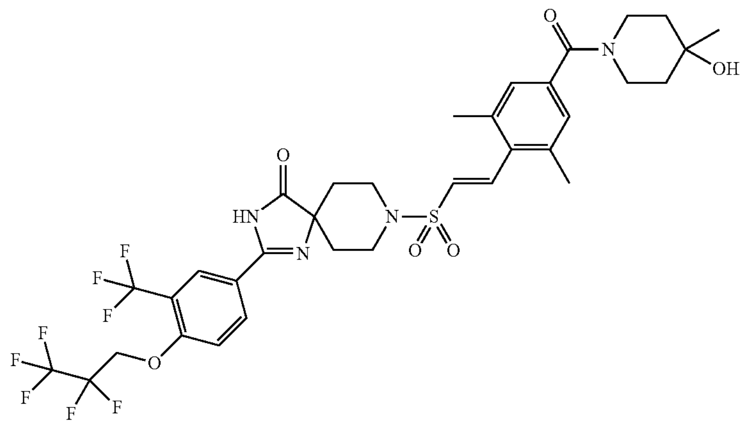 [SMILES: Cc1cc(C(=O)N2CCC(C)(O)CC2)cc(C)c1/C=C/S(=O)(=O)N1CCC2(CC1)N=C(c1ccc(OCC(F)(F)C(F)(F)F)c(C(F)(F)F)c1)NC2=O] | LCMS-G-1 | 1.17 | 781 (M + H)+ |
| 1204 | 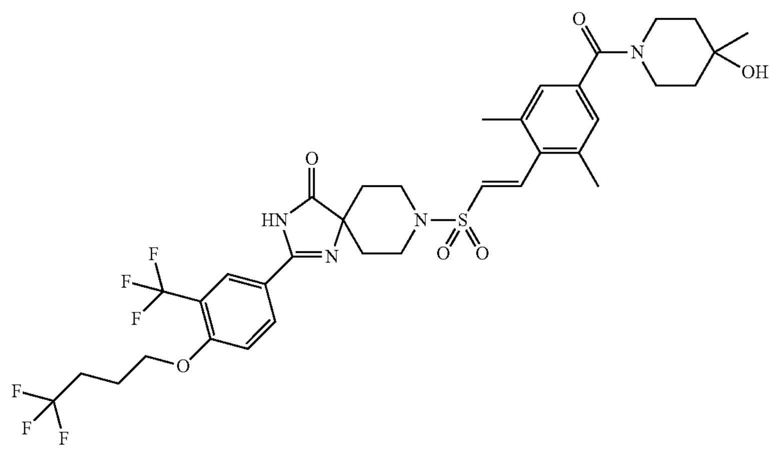 [SMILES: Cc1cc(C(=O)N2CCC(C)(O)CC2)cc(C)c1/C=C/S(=O)(=O)N1CCC2(CC1)N=C(c1ccc(OCCCC(F)(F)F)c(C(F)(F)F)c1)NC2=O] | LCMS-G-1 | 1.15 | 759 (M + H)+ |
| 1205 | 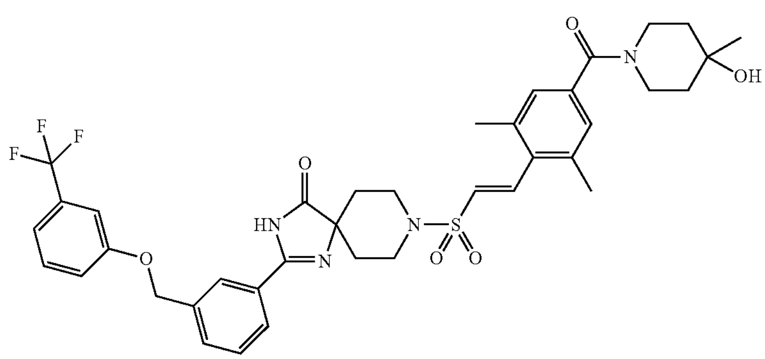 [SMILES: Cc1cc(C(=O)N2CCC(C)(O)CC2)cc(C)c1/C=C/S(=O)(=O)N1CCC2(CC1)N=C(c1cccc(COc3cccc(C(F)(F)F)c3)c1)NC2=O] | LCMS-G-1 | 1.13 | 739 (M + H)+ |
| 1206 | 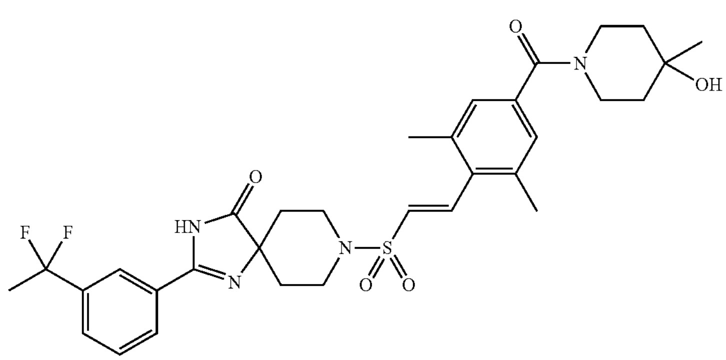 [SMILES: Cc1cc(C(=O)N2CCC(C)(O)CC2)cc(C)c1/C=C/S(=O)(=O)N1CCC2(CC1)N=C(c1cccc(C(C)(F)F)c1)NC2=O] | LCMS-G-1 | 1.09 | 629 (M + H)+ |

TABLE 176-continued

| Target Compound | Structure | LCMS condition | Retention time (min) | MS (m/z) |
|---|---|---|---|---|
| 1207 | 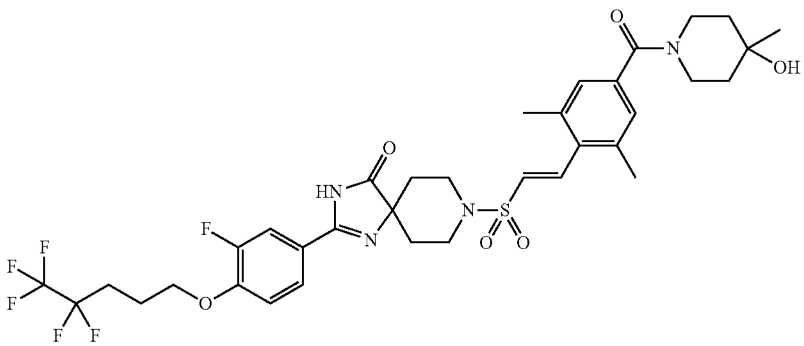 [SMILES: Cc1cc(C(=O)N2CCC(C)(O)CC2)cc(C)c1/C=C/S(=O)(=O)N1CCC2(CC1)N=C(c1ccc(OCCCC(F)(F)C(F)(F)F)c(F)c1)NC2=O] | LCMS-G-1 | 1.17 | 759 (M + H)+ |
| 1208 | 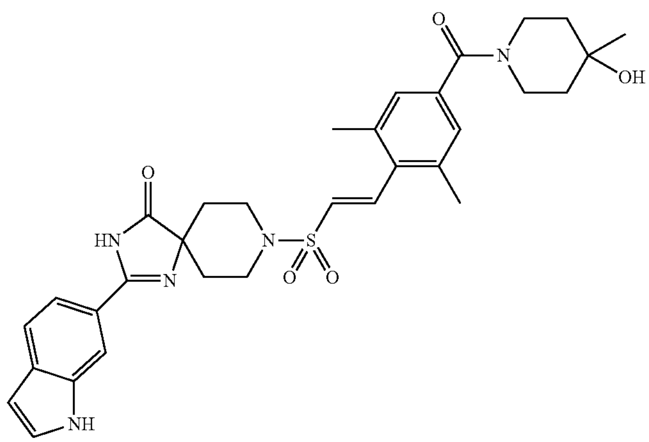 [SMILES: Cc1cc(C(=O)N2CCC(C)(O)CC2)cc(C)c1/C=C/S(=O)(=O)N1CCC2(CC1)N=C(c1ccc3cc[nH]c3c1)NC2=O] | LCMS-F-2 | 0.57 | 604 (M + H)+ |
| 1209 | 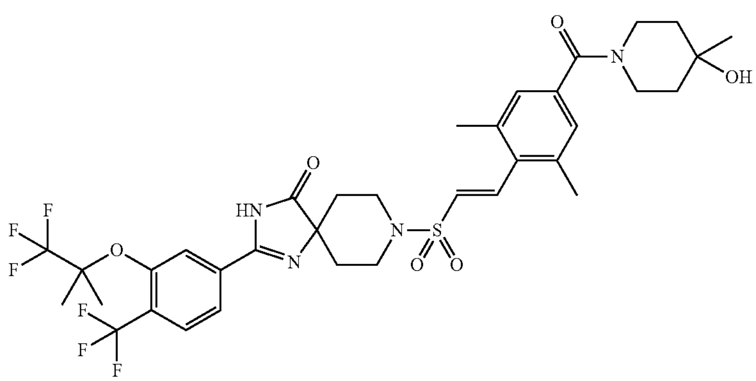 [SMILES: Cc1cc(C(=O)N2CCC(C)(O)CC2)cc(C)c1/C=C/S(=O)(=O)N1CCC2(CC1)N=C(c1ccc(C(F)(F)F)c(OC(C)(C)C(F)(F)F)c1)NC2=O] | LCMS-F-2 | 0.86 | 759 (M + H)+ |
| 1210 | 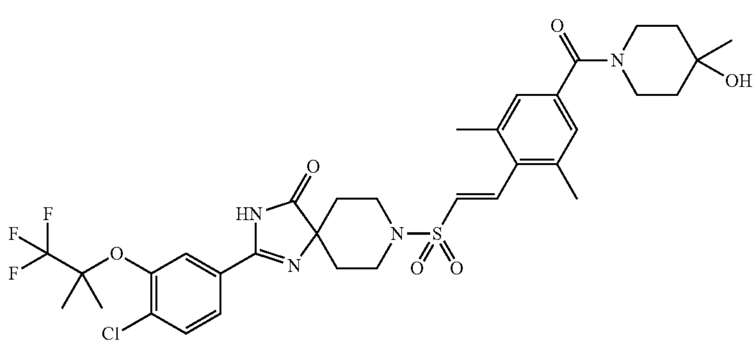 [SMILES: Cc1cc(C(=O)N2CCC(C)(O)CC2)cc(C)c1/C=C/S(=O)(=O)N1CCC2(CC1)N=C(c1ccc(Cl)c(OC(C)(C)C(F)(F)F)c1)NC2=O] | LCMS-F-2 | 0.83 | 725 (M + H)+ |

TABLE 176-continued

| Target Compound | Structure | LCMS condition | Retention time (min) | MS (m/z) |
|---|---|---|---|---|
| 1211 | 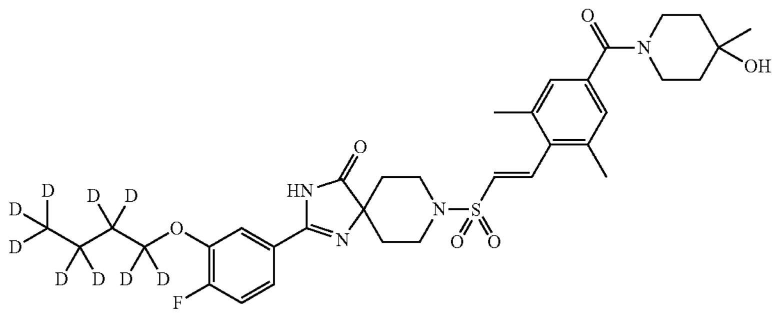 [SMILES: [2H]C([2H])([2H])C([2H])([2H])C([2H])([2H])C([2H])([2H])Oc1cc(C2=NC3(CCN(S(=O)(=O)/C=C/c4c(C)cc(C(=O)N5CCC(C)(O)CC5)cc4C)CC3)C(=O)N2)ccc1F] | LCMS-F-2 | 0.80 | 664 (M + H)+ |
| 1212 | 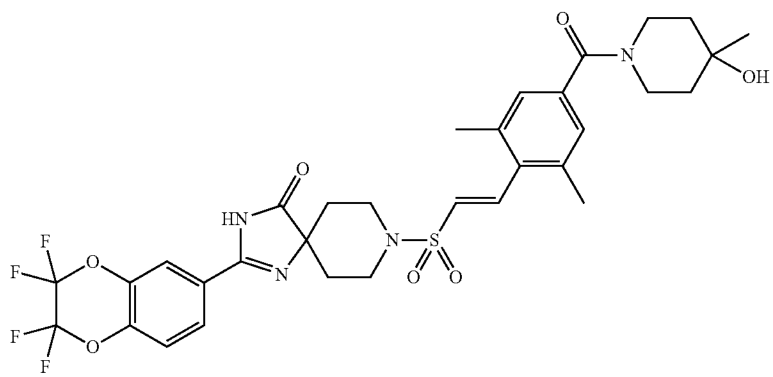 [SMILES: Cc1cc(C(=O)N2CCC(C)(O)CC2)cc(C)c1/C=C/S(=O)(=O)N1CCC2(CC1)N=C(c1ccc3c(c1)OC(F)(F)C(F)(F)O3)NC2=O] | LCMS-F-2 | 0.81 | 695 (M + H)+ |
| 1213 | 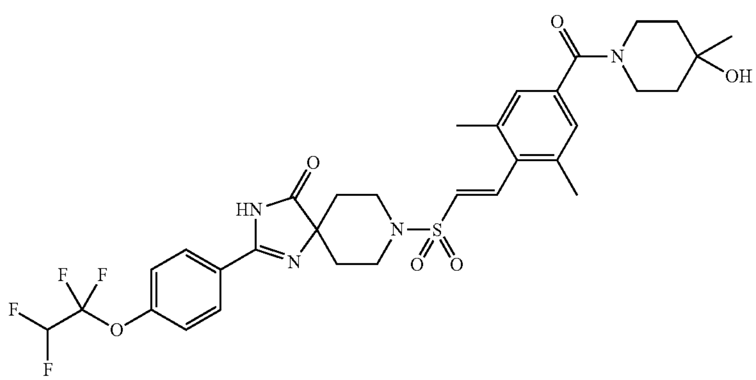 [SMILES: Cc1cc(C(=O)N2CCC(C)(O)CC2)cc(C)c1/C=C/S(=O)(=O)N1CCC2(CC1)N=C(c1ccc(OC(F)(F)C(F)F)cc1)NC2=O] | LCMS-F-2 | 0.74 | 681 (M + H)+ |
| 1214 | 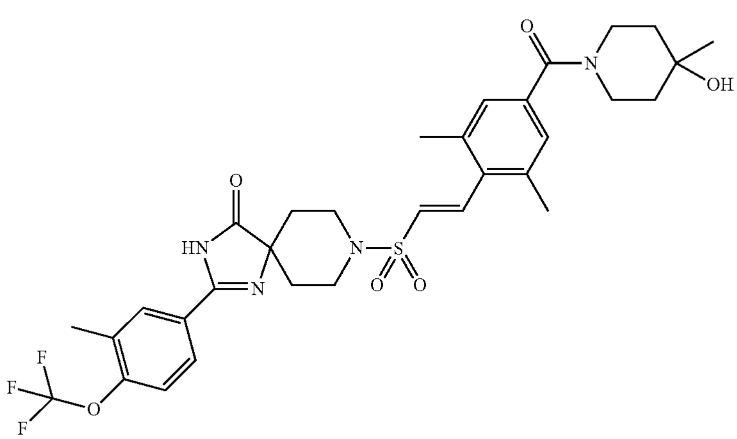 [SMILES: Cc1cc(C2=NC3(CCN(S(=O)(=O)/C=C/c4c(C)cc(C(=O)N5CCC(C)(O)CC5)cc4C)CC3)C(=O)N2)ccc1OC(F)(F)F] | LCMS-F-2 | 0.79 | 663 (M + H)+ |

TABLE 176-continued

| Target Compound | Structure | LCMS condition | Retention time (min) | MS (m/z) |
|---|---|---|---|---|
| 1215 | 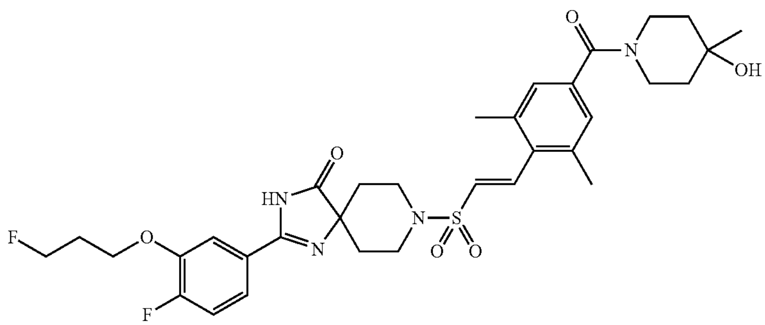 [SMILES: Cc1cc(C(=O)N2CCC(C)(O)CC2)cc(C)c1/C=C/S(=O)(=O)N1CCC2(CC1)N=C(c1ccc(F)c(OCCCF)c1)NC2=O] | LCMS-F-2 | 0.72 | 659 (M + H)+ |
| 1216 | 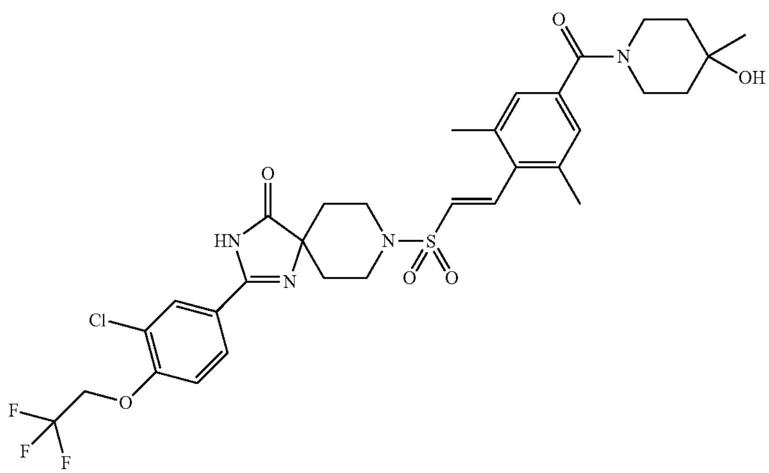 [SMILES: Cc1cc(C(=O)N2CCC(C)(O)CC2)cc(C)c1/C=C/S(=O)(=O)N1CCC2(CC1)N=C(c1ccc(OCC(F)(F)F)c(Cl)c1)NC2=O] | LCMS-G-1 | 1.09 | 697 (M + H)+ |
| 1217 | 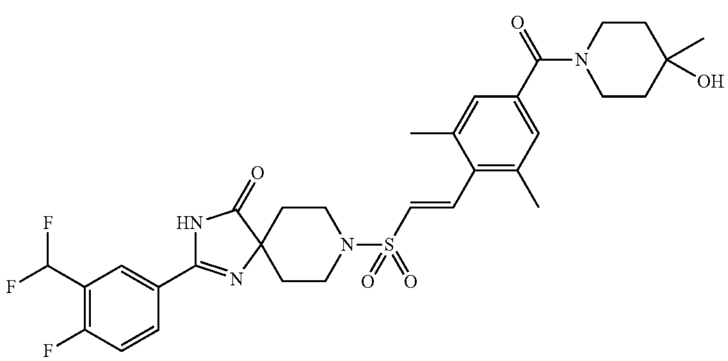 [SMILES: Cc1cc(C(=O)N2CCC(C)(O)CC2)cc(C)c1/C=C/S(=O)(=O)N1CCC2(CC1)N=C(c1ccc(F)c(C(F)F)c1)NC2=O] | LCMS-F-2 | 0.72 | 633 (M + H)+ |
| 1218 | 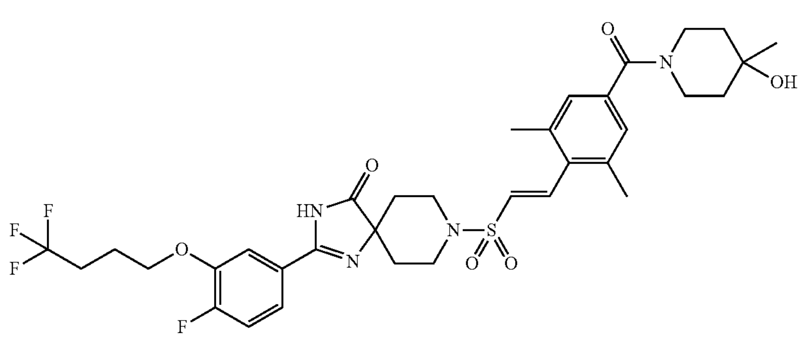 [SMILES: Cc1cc(C(=O)N2CCC(C)(O)CC2)cc(C)c1/C=C/S(=O)(=O)N1CCC2(CC1)N=C(c1ccc(F)c(OCCCC(F)(F)F)c1)NC2=O] | LCMS-F-2 | 0.79 | 709 (M + H)+ |

TABLE 176-continued

| Target Compound | Structure | LCMS condition | Retention time (min) | MS (m/z) |
|---|---|---|---|---|
| 1219 | 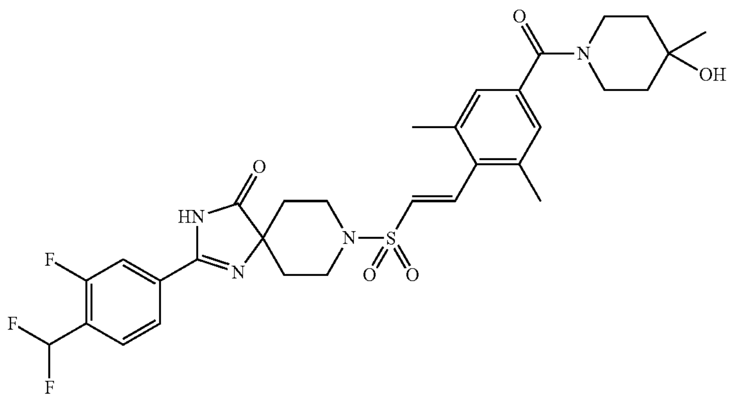 [SMILES: Cc1cc(C(=O)N2CCC(C)(O)CC2)cc(C)c1/C=C/S(=O)(=O)N1CCC2(CC1)N=C(c1ccc(C(F)F)c(F)c1)NC2=O] | LCMS-F-2 | 0.72 | 633 (N + H)+ |
| 1220 | 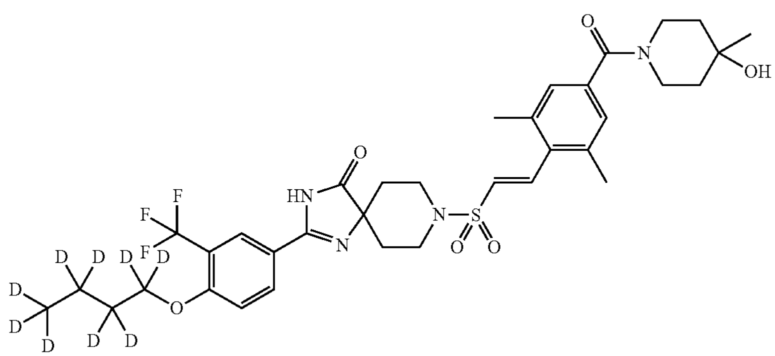 [SMILES: [2H]C([2H])([2H])C([2H])([2H])C([2H])([2H])C([2H])([2H])Oc1ccc(C2=NC3(CCN(S(=O)(=O)/C=C/c4c(C)cc(C(=O)N5CCC(C)(O)CC5)cc4C)CC3)C(=O)N2)cc1C(F)(F)F] | LCMS-F-2 | 0.86 | 714 (M + H)+ |
| 1221 | 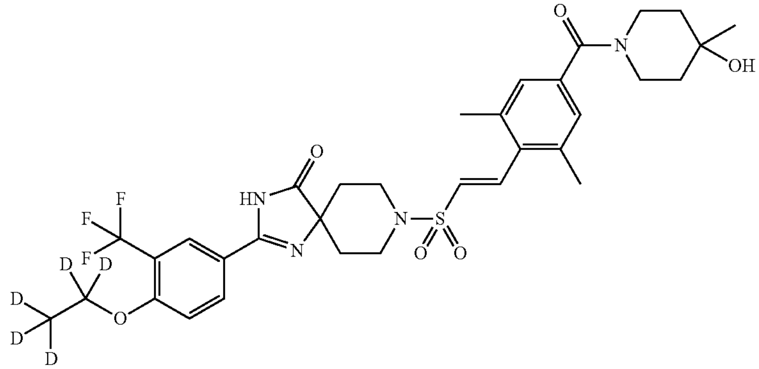 [SMILES: [2H]C([2H])([2H])C([2H])([2H])Oc1ccc(C2=NC3(CCN(S(=O)(=O)/C=C/c4c(C)cc(C(=O)N5CCC(C)(O)CC5)cc4C)CC3)C(=O)N2)cc1C(F)(F)F] | LCMS-F-2 | 0.76 | 682 (M + H)+ |

TABLE 176-continued

| Target Compound | Structure | LCMS condition | Retention time (min) | MS (m/z) |
|---|---|---|---|---|
| 1222 | 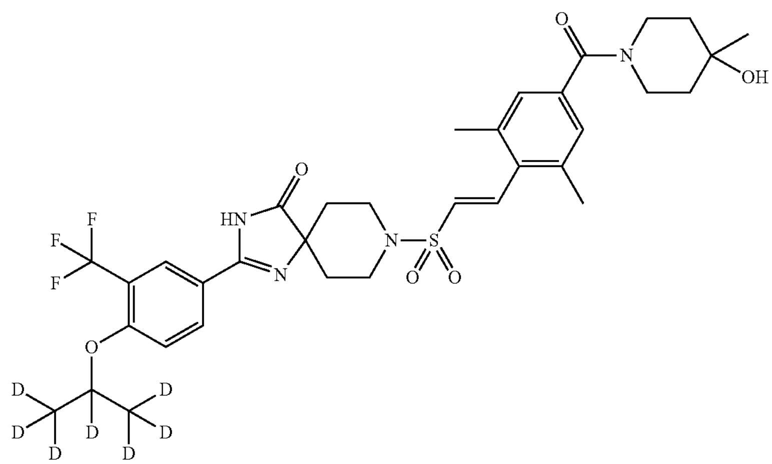 [SMILES: [2H]C([2H])([2H])C([2H])(Oc1ccc(C2=NC3(CCN(S(=O)(=O)/C=C/c4c(C)cc(C(=O)N5CCC(C)(O)CC5)cc4C)CC3)C(=O)N2)cc1C(F)(F)F)C([2H])([2H])[2H]] | LCMS-F-2 | 0.80 | 698 (M + H)+ |
| 1223 | 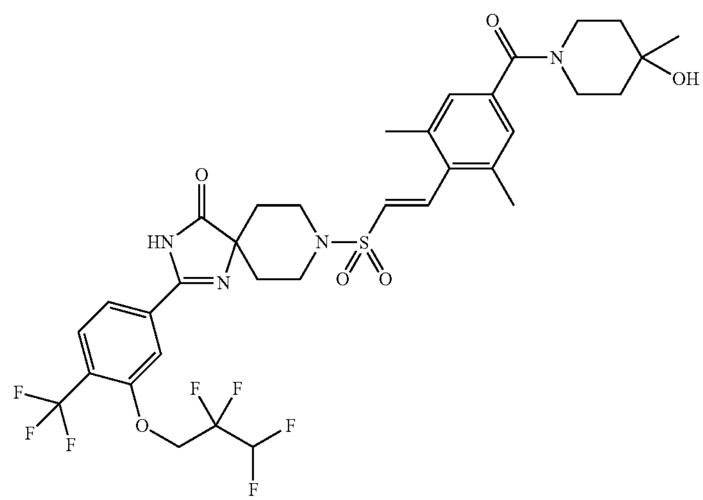 [SMILES: Cc1cc(C(=O)N2CCC(C)(O)CC2)cc(C)c1/C=C/S(=O)(=O)N1CCC2(CC1)N=C(c1ccc(C(F)(F)F)c(OCC(F)(F)C(F)F)c1)NC2=O] | LCMS-F-2 | 0.83 | 763 (M + H)+ |
| 1224 | 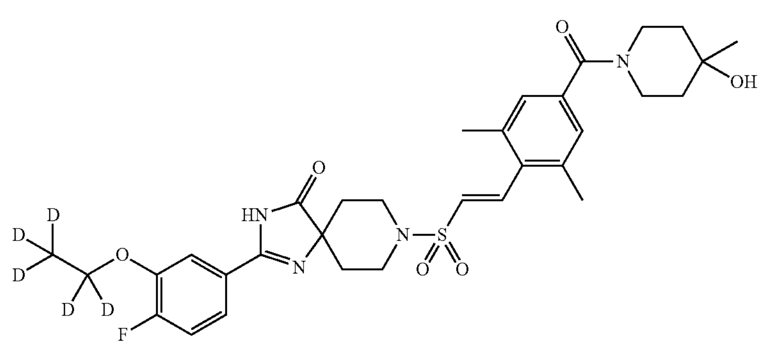 [SMILES: [2H]C([2H])([2H])C([2H])([2H])Oc1cc(C2=NC3(CCN(S(=O)(=O)/C=C/c4c(C)cc(C(=O)N5CCC(C)(O)CC5)cc4C)CC3)C(=O)N2)ccc1F] | LCMS-F-2 | 0.71 | 632 (M + H)+ |

TABLE 176-continued

| Target Compound | Structure | LCMS condition | Retention time (min) | MS (m/z) |
|---|---|---|---|---|
| 1225 | 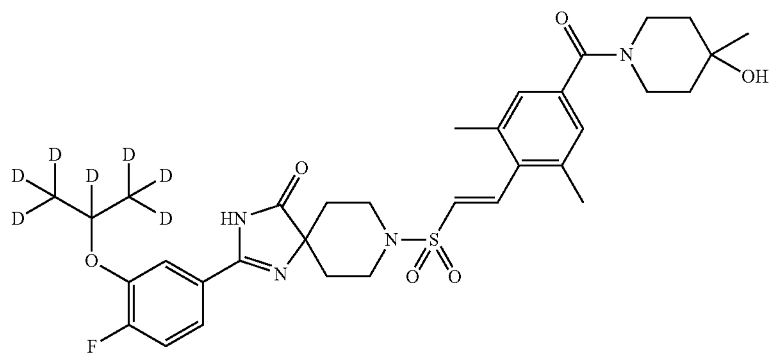 [SMILES: [2H]C([2H])([2H])C([2H])(Oc1cc(C2=NC3(CCN(S(=O)(=O)/C=C/c4c(C)cc(C(=O)N5CCC(C)(O)CC5)cc4C)CC3)C(=O)N2)ccc1F)C([2H])([2H])[2H]] | LCMS-F-2 | 0.74 | 648 (M + H)+ |
| 1226 | 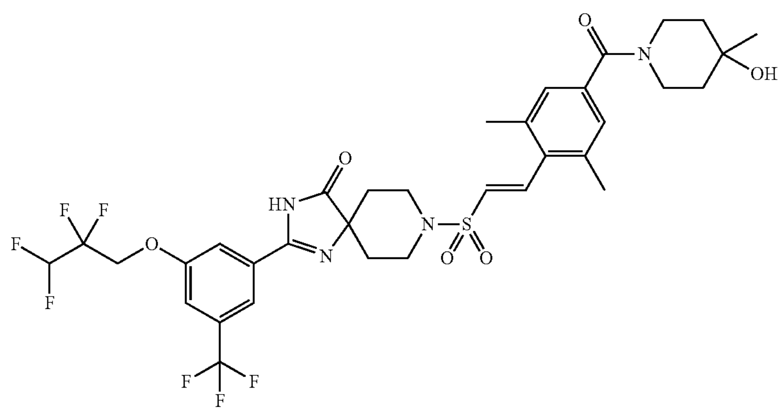 [SMILES: Cc1cc(C(=O)N2CCC(C)(O)CC2)cc(C)c1/C=C/S(=O)(=O)N1CCC2(CC1)N=C(c1cc(OCC(F)(F)C(F)F)cc(C(F)(F)F)c1)NC2=O] | LCMS-F-2 | 0.83 | 763 (M + H)+ |
| 1227 | 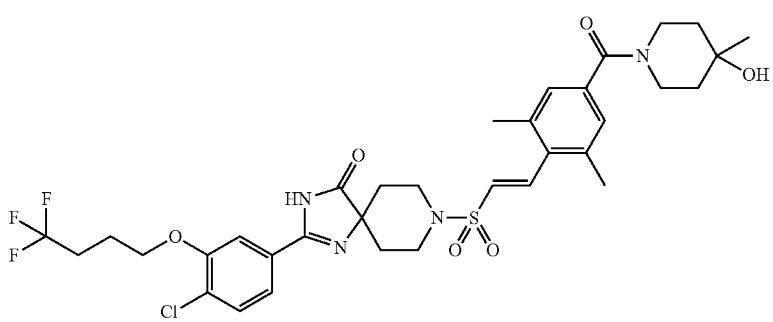 [SMILES: Cc1cc(C(=O)N2CCC(C)(O)CC2)cc(C)c1/C=C/S(=O)(=O)N1CCC2(CC1)N=C(c1ccc(Cl)c(OCCCC(F)(F)F)c1)NC2=O] | LCMS-F-2 | 0.84 | 725 (M + H)+ |
| 1228 | 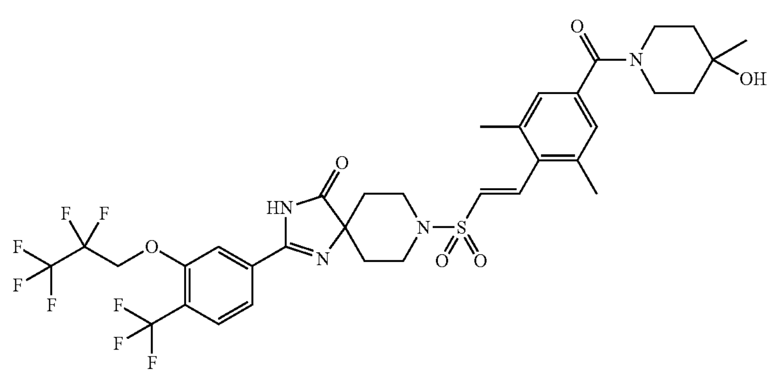 [SMILES: Cc1cc(C(=O)N2CCC(C)(O)CC2)cc(C)c1/C=C/S(=O)(=O)N1CCC2(CC1)N=C(c1ccc(C(F)(F)F)c(OCC(F)(F)C(F)(F)F)c1)NC2=O] | LCMS-F-2 | 0.87 | 781 (M + H)+ |

TABLE 176-continued

| Target Compound | Structure | LCMS condition | Retention time (min) | MS (m/z) |
|---|---|---|---|---|
| 1229 | 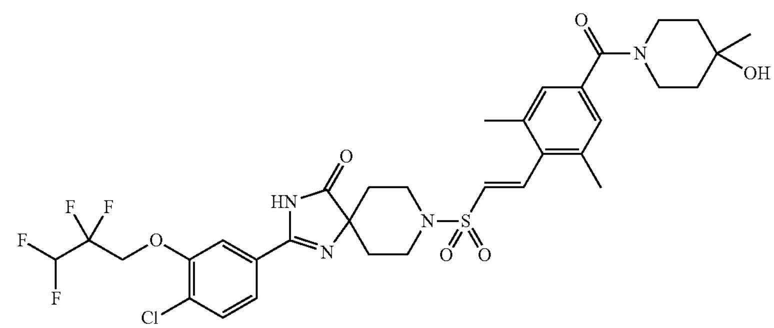 [SMILES: Cc1cc(C(=O)N2CCC(C)(O)CC2)cc(C)c1/C=C/S(=O)(=O)N1CCC2(CC1)N=C(c1ccc(Cl)c(OCC(F)(F)C(F)F)c1)NC2=O] | LCMS-F-2 | 0.79 | 729 (M + H)+ |
| 1230 | 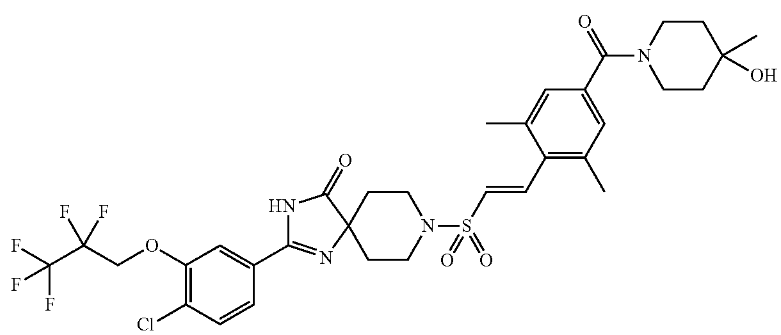 | LCMS-F-2 | 0.84 | 747 (M + H)+ |
| 1231 | 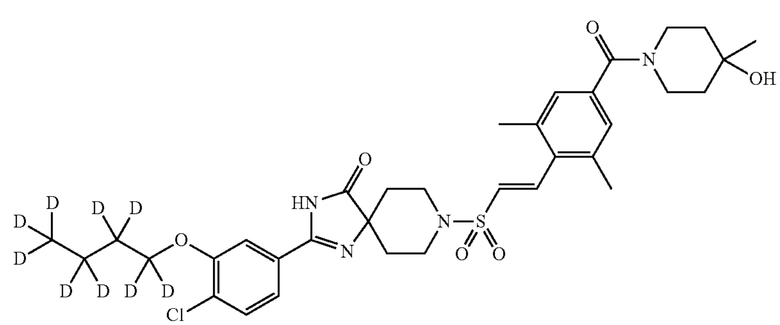 | LCMS-F-2 | 0.85 | 681 (M + H)+ |
| 1232 | 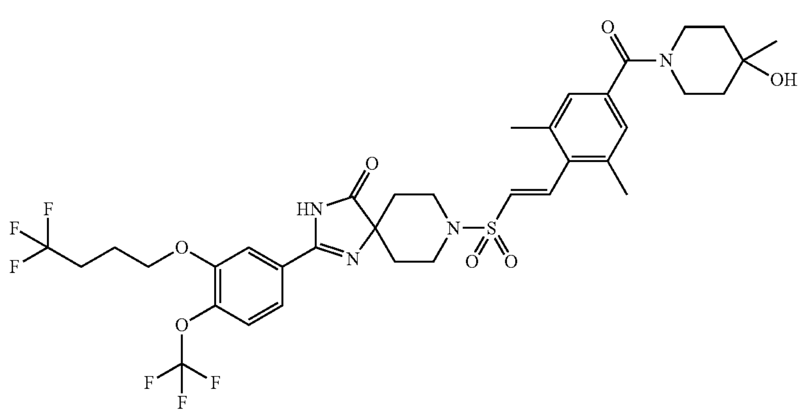 [SMILES: Cc1cc(C(=O)N2CCC(C)(O)CC2)cc(C)c1/C=C/S(=O)(=O)N1CCC2(CC1)N=C(c1ccc(OC(F)(F)F)c(OCCCC(F)(F)F)c1)NC2=O] | LCMS-F-2 | 0.87 | 775 (M + H)+ |

TABLE 176-continued

| Target Compound | Structure | LCMS condition | Retention time (min) | MS (m/z) |
|---|---|---|---|---|
| 1233 | 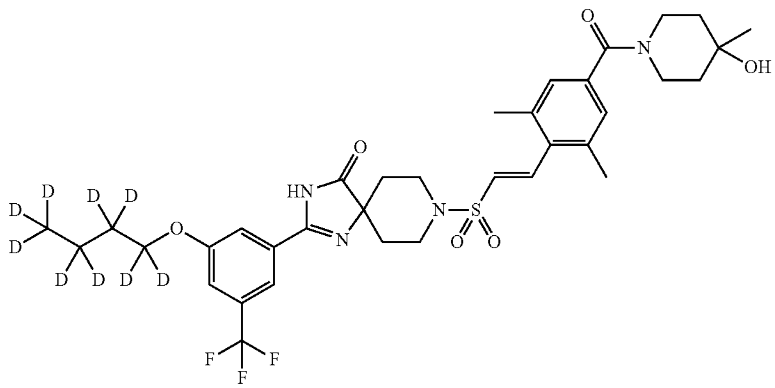 [SMILES: [2H]C([2H])([2H])C([2H])([2H])C([2H])([2H])C([2H])([2H])Oc1cc(C2=NC3(CCN(S(=O)(=O)/C=C/c4c(C)cc(C(=O)N5CCC(C)(O)CC5)cc4C)CC3)C(=O)N2)cc(C(F)(F)F)c1] | LCMS-F-2 | 0.90 | 714 (M + H)+ |
| 1234 | 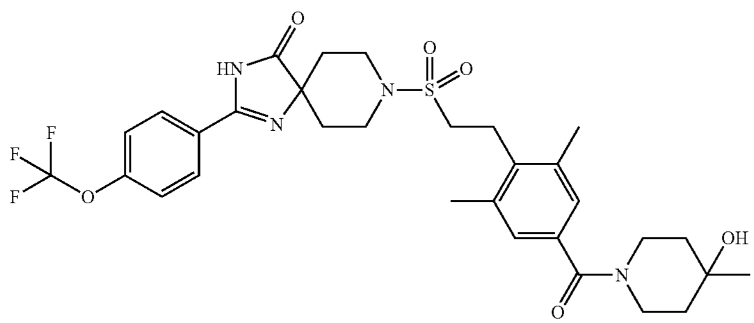 [SMILES: Cc1cc(C(=O)N2CCC(C)(O)CC2)cc(C)c1CCS(=O)(=O)N1CCC2(CC1)N=C(c1ccc(OC(F)(F)F)cc1)NC2=O] | LCMS-G-1 | 1.10 | 651 (M + H)+ |
| 1235 | 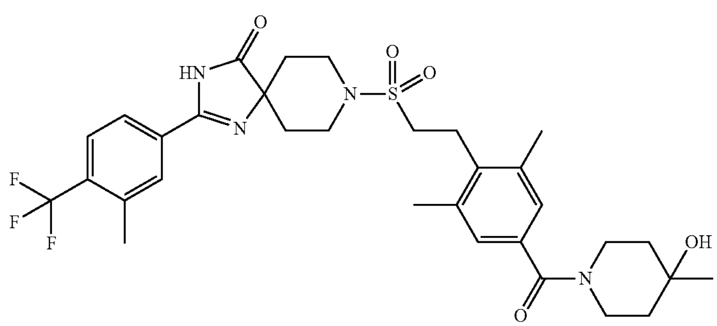 [SMILES: Cc1cc(C2=NC3(CCN(S(=O)(=O)CCc4c(C)cc(C(=O)N5CCC(C)(O)CC5)cc4C)CC3)C(=O)N2)ccc1C(F)(F)F] | LCMS-G-1 | 1.13 | 649 (M + H)+ |
| 1236 | 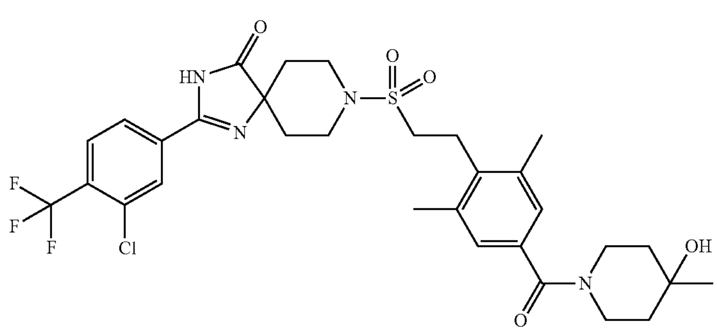 | LCMS-G-1 | 1.15 | 669 (M + H)+ |

TABLE 176-continued

| Target Compound | Structure | LCMS condition | Retention time (min) | MS (m/z) |
|---|---|---|---|---|
| 1237 | 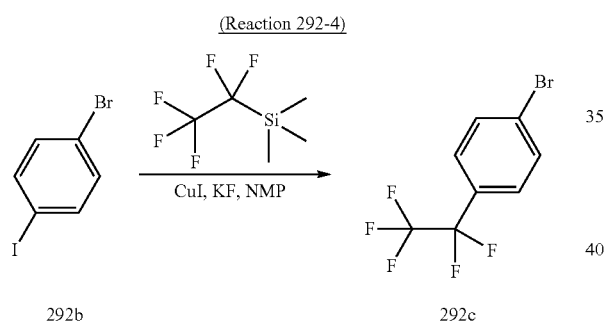 | LCMS-C-1 | 2.63 | 593 (M + H)+ |
| 1238 | 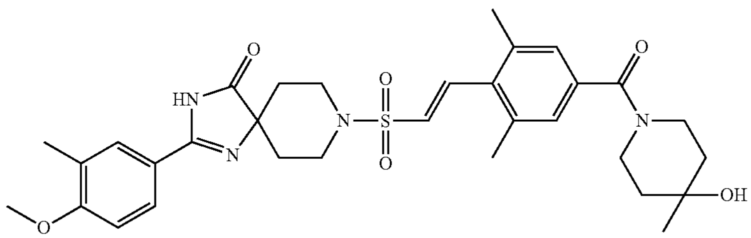 [SMILES: COc1ccc(C2=NC3(CCN(S(=O)(=O)/C=C/c4c(C)cc(C(=O)N5CCC(C)(O)CC5)cc4C)CC3)C(=O)N2)cc1C] | LCMS-C-1 | 2.58 | 609 (M + H)+ |

The arylboronic acid reagent used in the synthesis of Compound 1195 (4-pentafluoroethylphenylboronic acid) was synthesized by the following method.

(Reaction 292-4)


A solution of 4-bromo-iodobenzene (500 mg, 1.77 mmol), trimethylsilylpentafluoroethane (679 mg, 3.53 mmol), copper iodide (672 mg, 3.53 mmol) and potassium fluoride (205 mg, 3.53 mmol) in N-methylpyrolidone (1.0 mL) was heated with stirring at 100° C. for three hours in a sealed reaction vessel. After cooling to room temperature, the reaction mixture was purified by silica gel column chromatography (hexane:ethyl acetate=20:1) to give 1-bromo-4-pentafluoroethylbenzene as a colorless liquid (253 mg, 52%).

$^1$H-NMR (270 MHz, CDCl$_3$) δ 7.46 (2H, d, J=8.6 Hz), 7.65 (2H, d, J=8.6 Hz).

(Reaction 292-5)

A 1.5 M solution of n-butyllithium in tetrahydrofuran (0.57 mL) was added to a solution of 1-bromo-4-pentafluoroethylbenzene (180 mg, 0.65 mmol) in diethyl ether (1.0 mL) at −78° C., and the mixture was stirred for 20 minutes. Thereafter, trimethyl borate (101 mg, 3.28 mmol) was added and the mixture was stirred at −78° C. for 10 minutes and at room temperature for 30 minutes. 6 N aqueous hydrochloric acid (200 μL) was added to the reaction mixture, and the reaction was terminated. The mixture was then purified by silica gel column chromatography to give 4-pentafluoroethylphenylboronic acid as a white solid (111 mg, 71%).

$^1$H-NMR (400 MHz, CDCl$_3$) δ 7.87 (2H, d, J=8.0 Hz), 7.64 (2H, d, J=8.0 Hz), 4.61 (s, 2H).

The arylboronic acid reagent used in the synthesis of Compound 1196 (3-pentafluoroethylphenylboronic acid) was synthesized by the following method.

(Reaction 292-6)

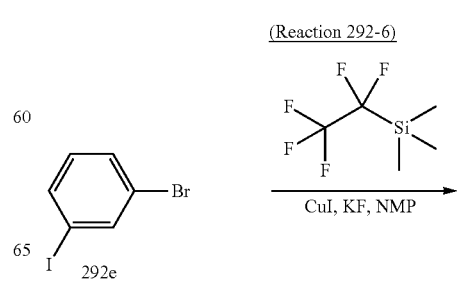

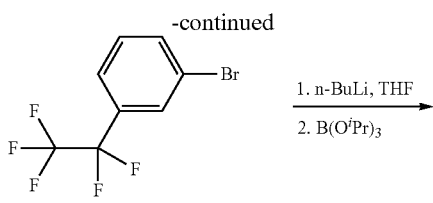

3-Pentafluoroethylphenylboronic acid was obtained by operations similar to those in Reaction 292-4 and Reaction 292-5 using 1-bromo-3-iodo-benzene as a starting material.
MS (ESI) m/z=239 (M–H)–.

The arylboronic acid reagent used in the synthesis of Compound 1197 (4-(2,2,2-trifluoro-1,1-dimethyl-ethoxy)-3-trifluoromethylphenylboronic acid) was synthesized by the following method.

(Reaction 292-7)

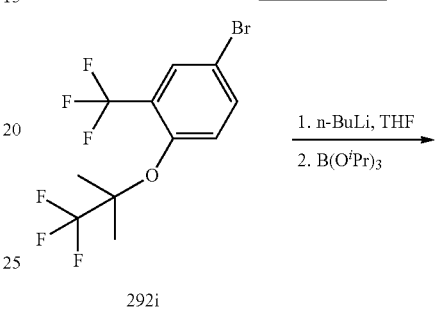

Potassium tert-butoxide (236 mg, 2.1 mmol) was added to a solution of 5-bromo-2-fluorobenzotrifluoride (485 mg, 2.0 mmol) and 2-trifluoromethyl-2-propanol (0.24 mL, 2.2 mmol) in DMI (0.5 mL) at room temperature, and the mixture was stirred at 100° C. for two hours. The reaction solution was purified by silica gel column chromatography to give 4-bromo-1-(2,2,2-trifluoro-1,1-dimethyl-ethoxy)-2-trifluoromethyl-benzene (349 mg, 50%).

$^1$H-NMR (400 MHz, CDCl$_3$) δ 7.73 (1H, d, J=2.4 Hz), 7.59 (1H, dd, J=2.4, 8.9 Hz), 7.14 (1H, d, J=8.9 Hz), 1.53 (s, 6H).

(Reaction 292-8)

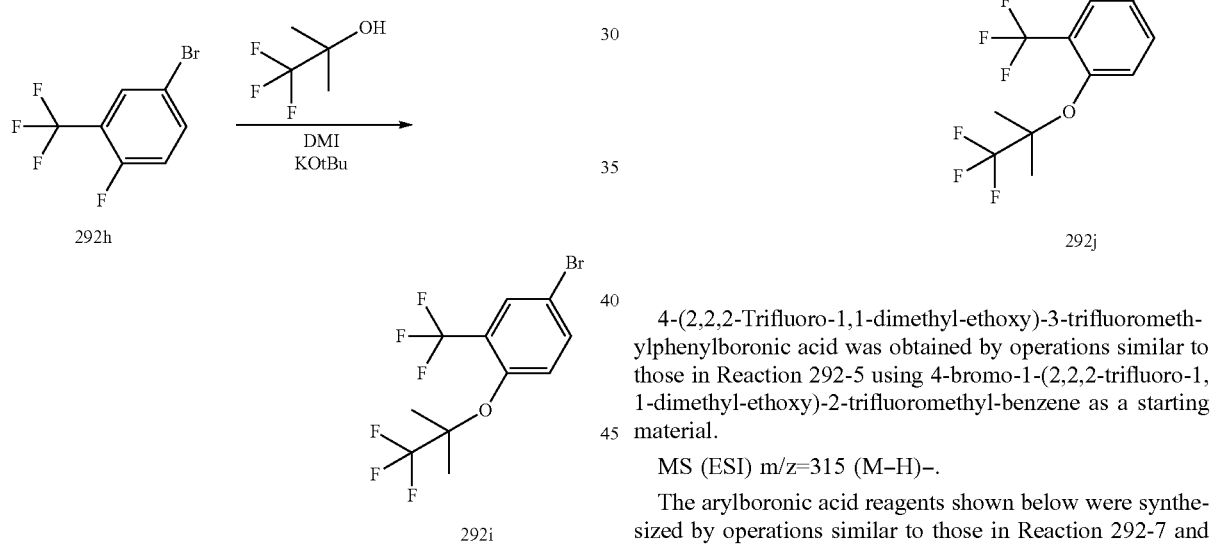

4-(2,2,2-Trifluoro-1,1-dimethyl-ethoxy)-3-trifluoromethylphenylboronic acid was obtained by operations similar to those in Reaction 292-5 using 4-bromo-1-(2,2,2-trifluoro-1,1-dimethyl-ethoxy)-2-trifluoromethyl-benzene as a starting material.

MS (ESI) m/z=315 (M–H)–.

The arylboronic acid reagents shown below were synthesized by operations similar to those in Reaction 292-7 and Reaction 292-5 using appropriate starting compounds and used in the synthesis of the compounds in Table 176.

TABLE 177

| Target Compound | Raw material | Arylboronic acid structure | MS (m/z) |
|---|---|---|---|
| 1199 | (structure) | (structure) | 319 (M – H)– |

TABLE 177-continued
| Target Compound | Raw material | Arylboronic acid structure | MS (m/z) |
|---|---|---|---|
| 1200 |  | 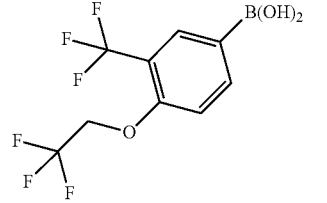 [SMILES: OB(O)c1ccc(OCC(F)(F)F)c(C(F)(F)F)c1] | 287 (M − H)− |
| 1201 | 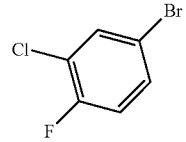 | 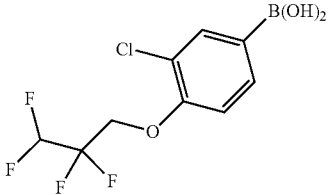 [SMILES: OB(O)c1ccc(OCC(F)(F)C(F)F)c(Cl)c1] | 285 (M − H)− |
| 1202 | 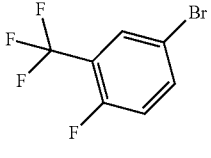 | 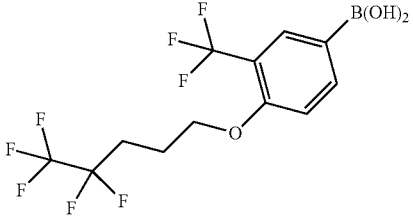 [SMILES: OB(O)c1ccc(OCCCC(F)(F)C(F)(F)F)c(C(F)(F)F)c1] | 365 (M − H)− |
| 1203 | 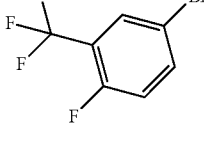 | 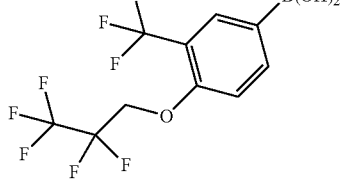 | 337 (M − H)− |
| 1204 | 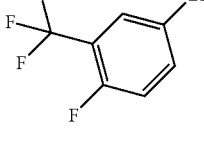 | 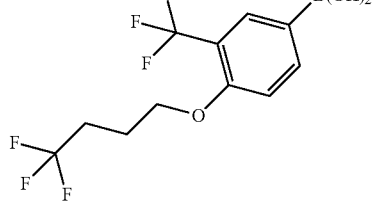 | 315 (M − H)− |
| 1216 | 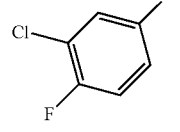 | 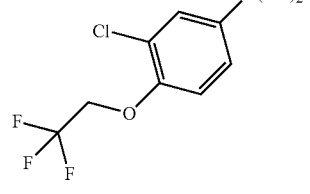 | 253 (M − H)− |
| 1220 | 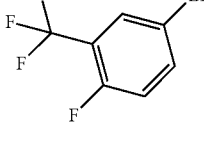 | 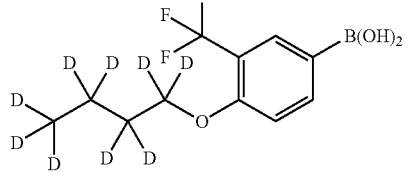 | 270 (M − H)− |

TABLE 177-continued

| Target Compound | Raw material | Arylboronic acid structure | MS (m/z) |
|---|---|---|---|
| 1221 | 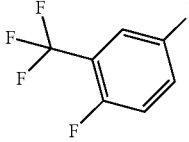 | 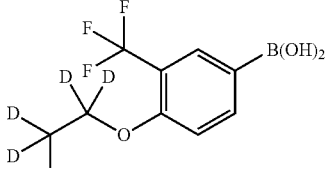 | 238 (M − H)− |
| 1222 | 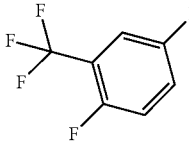 | 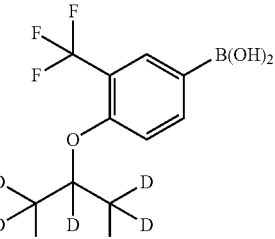 | 254 (M − H)− |
| 1232 | 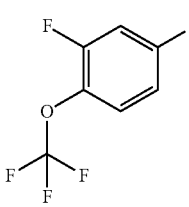 | 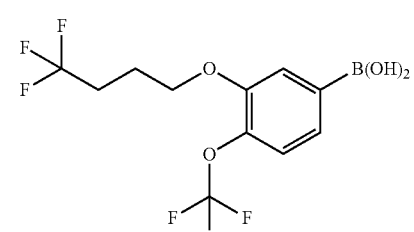 | 331 (M − H)− |

The arylboronic acid reagents shown below were synthesized by operations similar to those in Reaction 292-5 using appropriate starting compounds and used in the synthesis of the compounds in Table 176.

TABLE 178

| Target Compound | Raw material | Arylboronic acid structure | MS (m/z) |
|---|---|---|---|
| 1214 | 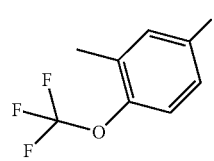 | 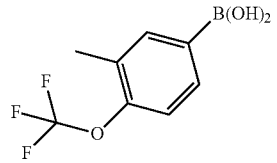 | 219 (M − H)− |
| 1217 | 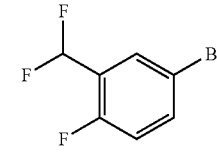 | 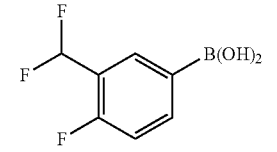 [SMILES: OB(O)c1ccc(F)c(C(F)F)c1] | 189 (M − H)− |
| 1219 | 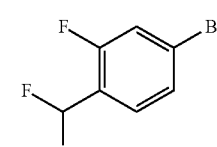 | 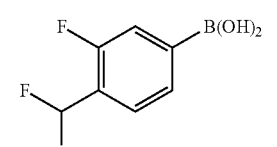 | 189 (M − H)− |

The arylboronic acid reagent used in the synthesis of Compound 1229 (4-chloro-3-(2,2,3,3-tetrafluoro-propoxy)-phenylboronic acid) was synthesized by the following method.

(Reaction 292-9)

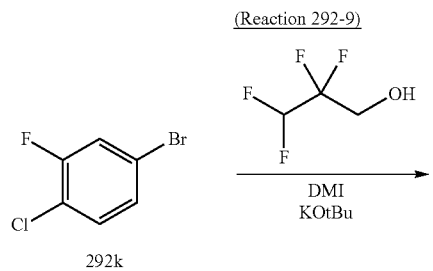

292k

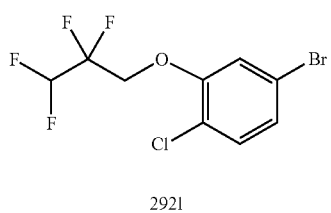

292l

4-Bromo-1-chloro-2-(2,2,3,3-tetrafluoro-propoxy)-benzene was obtained by operations similar to those in Reaction 292-7 using appropriate starting compound and reagents.

$^1$H-NMR (400 MHz, CDCl$_3$) δ 7.27 (1H, d, J=8.3 Hz), 7.15 (1H, dd, J=2.0, 8.3 Hz), 7.07 (1H, d, J=2.0 Hz), 6.15 (1H, dt, J=5.4, 53.2 Hz), 4.39 (2H, t, J=11.2 Hz).

(Reaction 292-10)

A 1.5 M solution of n-butyllithium in tetrahydrofuran (0.99 mL) was added to a solution of 4-bromo-1-chloro-2-(2,2,3,3-tetrafluoro-propoxy)-benzene (434 mg, 1.35 mmol) and triisopropyl borate (382 mg, 2.03 mmol) in anhydrous tetrahydrofuran (2.0 mL) at −78° C., and the mixture was stirred for 10 minutes. The reaction mixture was warmed to room temperature and stirred for 30 minutes. 6 N aqueous hydrochloric acid was then added to the reaction mixture, and the reaction was terminated, followed by extraction with ethyl acetate. The organic layer was dried over anhydrous sodium sulfate and concentrated under reduced pressure. The residue was treated with a mixed solution of dichloromethane and hexane to give 4-chloro-3-(2,2,3,3-tetrafluoro-propoxy)-phenylboronic acid as a white solid (246 mg, 64%).

MS (ESI) m/z=285 (M−H)−.

The arylboronic acid reagents shown below were synthesized by operations similar to those in Reaction 292-7 and Reaction 292-10 using appropriate starting compounds and used in the synthesis of the compounds in Table 176.

TABLE 179

| Target Compound | Raw material | Arylboronic acid structure | MS (m/z) |
|---|---|---|---|
| 1226 | (structure) | (structure) | 319 (M − H)− |
| 1227 | (structure) | (structure) | 281 (M − H)− |
| 1228 | (structure) | (structure) | 337 (M − H)− |

TABLE 179-continued

| Target Compound | Raw material | Arylboronic acid structure | MS (m/z) |
|---|---|---|---|
| 1230 | | | 303 (M − H)− |
| 1231 | | | 236 (M − H)− |
| 1233 | | | 270 (M − H)− |

The arylboronic acid reagent used in the synthesis of Compound 1213 (4-(1,1,2,2-tetrafluoro-ethoxy)phenylboronic acid) was synthesized by the following method.

(Reaction 292-11)

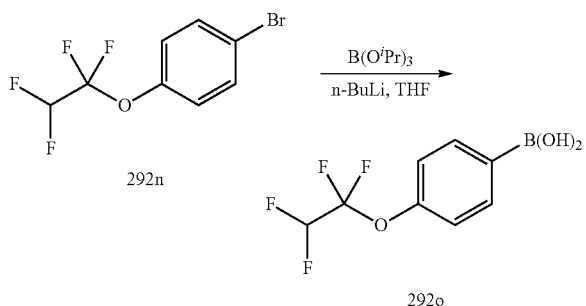

4-(1,1,2,2-Tetrafluoro-ethoxy)phenylboronic acid was obtained by operations similar to those in Reaction 292-10 using appropriate starting compound and reagents.

MS (ESI) m/z=237 (M−H)−.

The arylboronic acid reagent used in the synthesis of Compound 1223 (3-(2,2,3,3-tetrafluoro-propoxy)-4-trifluoromethylphenylboronic acid) was synthesized by the following method.

(Reaction 292-12)

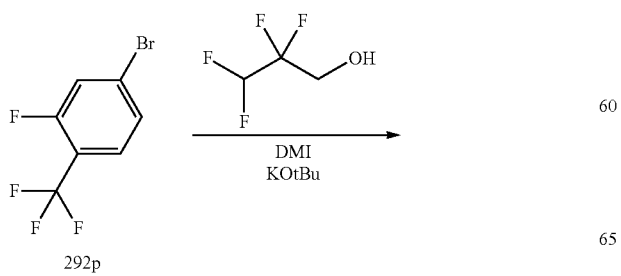

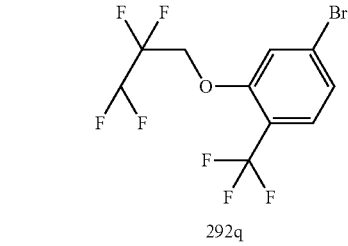

4-Bromo-2-(2,2,3,3-tetrafluoro-propoxy)-1-trifluoromethyl-benzene was obtained by operations similar to those in Reaction 292-7 using appropriate starting compound and reagents.

$^1$H-NMR (400 MHz, CDCl$_3$) δ 7.74 (1H, d, J=2.4 Hz), 7.65 (1H, dd, J=2.4, 8.8 Hz), 6.88 (1H, d, J=8.8 Hz), 6.06 (1H, dt, J=5.4, 53.2 Hz), 4.40 (2H, t, J=11.2 Hz).

(Reaction 292-13)

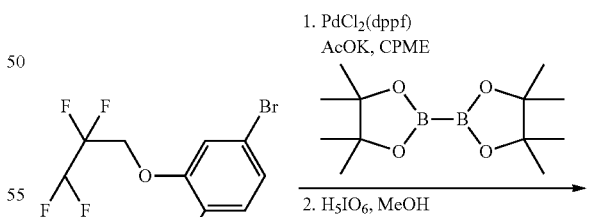

A solution of 4-bromo-2-(2,2,3,3-tetrafluoro-propoxy)-1-trifluoromethyl-benzene (482 mg, 1.36 mmol), pinacol diborane (379 mg, 1.49 mmol), palladium dichloride-diphenylphosphinoferrocene (111 mg, 0.136 mmol) and potassium acetate (400 mg, 4.08 mmol) in cyclopentyl methyl ether (2.41 mL) was heated with stirring at 115° C. for one hour in a nitrogen atmosphere. After cooling to room temperature, water (1 mL) was added to the reaction mixture, and the upper cyclopentyl methyl ether layer was extracted. Methanol (1 mL) was added to the organic layer. Periodic acid (1.24 g, 5.44 mmol) was added at 0° C., and the mixture was warmed to room temperature and stirred for one hour. Water was added to the reaction mixture, followed by extraction with ethyl acetate. The organic layer was dried over anhydrous sodium sulfate and concentrated under reduced pressure. The residue was purified by silica gel column chromatography (hexane:ethyl acetate=3:1→1:1) and further treated with hexane to give 3-(2,2,3,3-tetrafluoro-propoxy)-4-trifluoromethylphenylboronic acid as a pale brown solid (260 mg, 60%).

MS (ESI) m/z=319 (M–H)–.

The arylboronic acid reagents shown below were synthesized by operations similar to those in Reaction 292-7 and Reaction 292-13 using appropriate starting compounds and used in the synthesis of the compounds in Table 176.

Toluene was added to a mixture of 5-bromo-2-fluorophenol (382 mg, 2.0 mmol), ethanol-$d^5$ (0.104 mL, 2.0 mmol) and N,N,N',N'-tetramethylazodicarboxamide (465 mg, 2.7 mmol). Tributylphosphine (0.622 mL, 2.5 mmol) was added at 0° C. and the mixture was stirred for 14 hours. The reaction solution was purified by silica gel column chromatography to give 4-bromo-2-[1,1,2,2,2-$^2H_5$]ethoxy-1-fluorobenzene (416 mg, 93%).

$^1$H-NMR (400 MHz, CDCl$_3$) δ 7.07 (1H, dd, J=2.1, 7.4 Hz), 7.00 (1H, ddd, J=2.1, 4.1, 8.4 Hz), 6.94 (1H, dd, J=8.4, 10.7 Hz).

(Reaction 292-15)

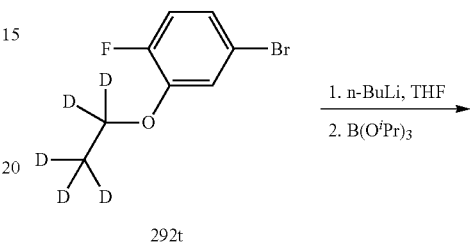

TABLE 180

| Target Compound | Raw material | Arylboronic acid structure | MS (m/z) |
|---|---|---|---|
| 1209 | ![F,F,F,CF3-phenyl-Br] | ![arylboronic acid with CF3 group] | 315 (M – H)– |
| 1210 | ![F,Cl-phenyl-Br] | ![arylboronic acid with Cl group] | 281 (M – H)– |

The arylboronic acid reagent used in the synthesis of Compound 1224 (4-bromo-3-[1,1,2,2,2-$^2H_5$]ethoxy-1-fluorophenylboronic acid) was synthesized by the following method.

(Reaction 292-14)

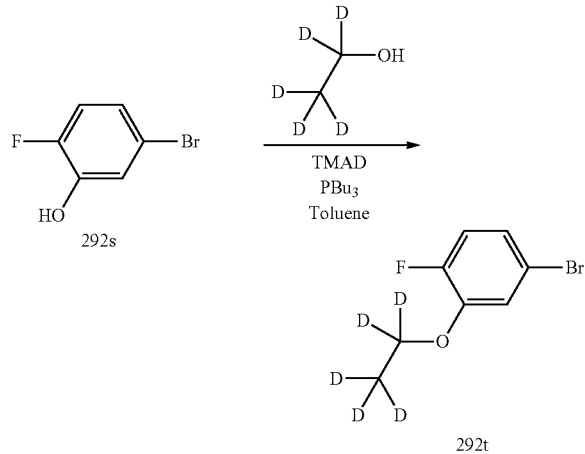

-continued

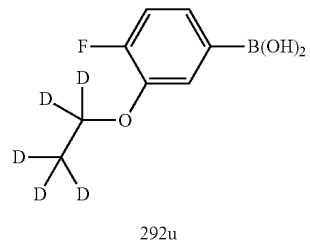

4-Bromo-3-[1,1,2,2,2-$^2H_5$]ethoxy-1-fluorophenylboronic acid was obtained by operations similar to those in Reaction 292-5 using 4-bromo-2-[1,1,2,2,2-$^2H_5$]ethoxy-1-fluoro-benzene as a starting material.

MS (ESI) m/z=188 (M–H)–.

The arylboronic acid reagents shown below were synthesized by operations similar to those in Reaction 292-14 and Reaction 292-5 using appropriate starting compounds and used in the synthesis of the compounds in Table 176.

TABLE 181

| Target Compound | Raw material | Arylboronic acid structure | MS (m/z) |
|---|---|---|---|
| 1207 | 4-bromo-2-fluorophenol (F, HO, Br) | 3-fluoro-4-(4,4,5,5,5-pentafluoropentyloxy)phenylboronic acid | 315 (M − H)− |
| 1211 | 5-bromo-2-fluorophenol (HO, Br, F) | deuterated propoxy-fluorophenylboronic acid (d7) | 220 (M − H)− |
| 1218 | 5-bromo-2-fluorophenol (HO, Br, F) | 3-(4,4,5,5,5-pentafluoropentyloxy)-4-fluorophenylboronic acid | 265 (M − H)− |
| 1225 | 5-bromo-2-fluorophenol (HO, Br, F) | deuterated isopropoxy-fluorophenylboronic acid (d7) | 204 (M − H)− |

The arylboronic acid reagent used in the synthesis of Compound 1215 (3-fluoro-4-(3-fluoro-propoxy)phenylboronic acid) was synthesized by the following method.

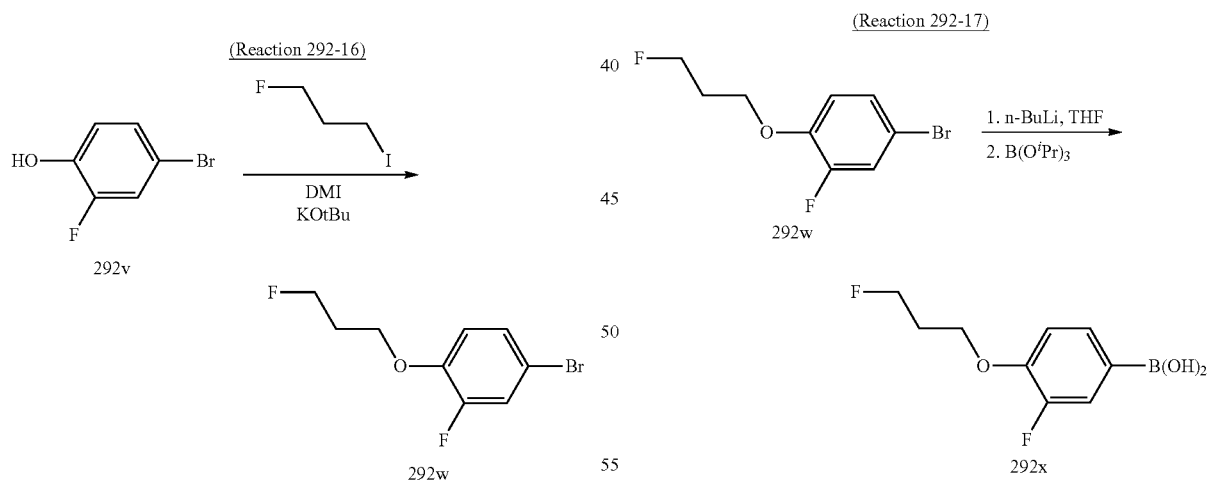

4-Bromo-2-fluorophenol (382 mg, 2.0 mmol) was dissolved in DMI (0.5 mL), and potassium tert-butoxide (224 mg, 2.0 mmol) was added at room temperature. 1-Iodo-3-fluoropropane (376 mg, 2.0 mmol) was added to the reaction solution, and the mixture was heated to 60° C. and stirred for six hours. The reaction solution was purified by silica gel column chromatography to give 4-bromo-2-fluoro-1-(3-fluoro-propoxy)-benzene (410 mg, 82%).

$^1$H-NMR (400 MHz, CDCl$_3$) δ 7.10 (1H, dd, J=2.1, 7.4 Hz), 7.03 (1H, ddd, J=2.4, 3.9, 8.6 Hz), 6.95 (1H, dd, J=8.7, 10.7 Hz), 4.66 (2H, dt, J=5.6, 46.9 Hz), 4.15 (2H, t, J=6.1 Hz), 2.20 (2H, ddt, J=5.8, 5.8, 26.1 Hz).

3-Fluoro-4-(3-fluoro-propoxy)phenylboronic acid was obtained by operations similar to those in Reaction 292-5 using 4-bromo-2-fluoro-1-(3-fluoro-propoxy)-benzene as a starting material.

MS (ESI) m/z=215 (M−H)−.

The arylboronic acid reagent used in the synthesis of Compound 1212 (2,2,3,3-tetrafluoro-2,3-dihydro-benzo[1,4]dioxin-6-yl-boronic acid) was synthesized by the following method.

1439

(Reaction 292-18)

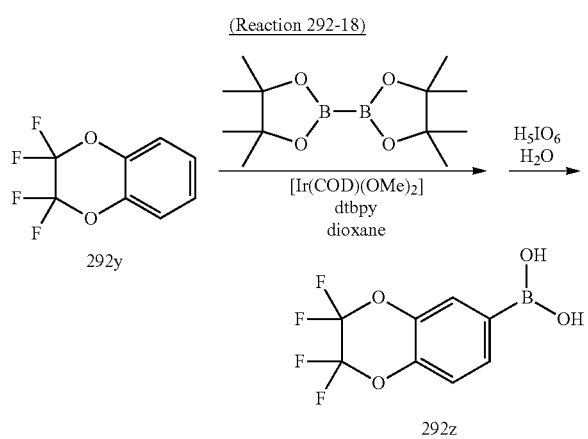

2,2,3,3-Tetrafluoro-1,4-benzodioxane (484 mg), bis(pinacolato)diboron (295 mg), [Ir(COD)(OMe)]₂ (15.4 mg) and 4,4'di-tert-butyl-2,2'-dipyridyl (12.5 mg) were mixed. 1,4-Dioxane (0.5 mL) was added in a nitrogen atmosphere and stirred at 100° C. for two hours. MeOH (0.5 mL) was added to the reaction solution, and metaperiodic acid (1.06 g) was added in four portions under ice-cooling. Water was added to the reaction solution, followed by extraction with ethyl acetate and concentration. The resulting mixture was purified by silica gel column chromatography to give 2,2,3,3-tetrafluoro-2,3-dihydro-benzo[1,4]dioxin-6-yl-boronic acid (230 mg, 39%).

MS (ESI) m/z=251 (M−H)−.

Example 293

2-(4-Fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one (Compound 1239)

(Reaction 293-1)

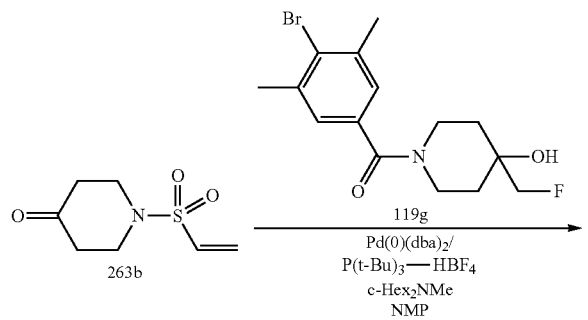

1440

-continued

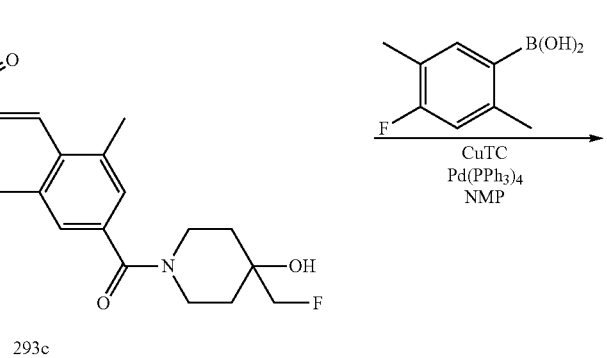

8-{(E)-2-[4-(4-Fluoromethyl-4-hydroxy-piperidine-1-carbonyl)-2,6-dimethyl-phenyl]-ethenesulfonyl}-2-thioxo-1,3,8-triaza-spiro[4.5]decan-4-one was obtained by operations similar to those in Reaction 119-1, Reaction 233-3, Reaction 233-4 and Reaction 292-2 using 1-ethenesulfonyl-piperidin-4-one as a starting material.

MS (ESI) m/z=539 (M+H)+.

(Reaction 293-2)

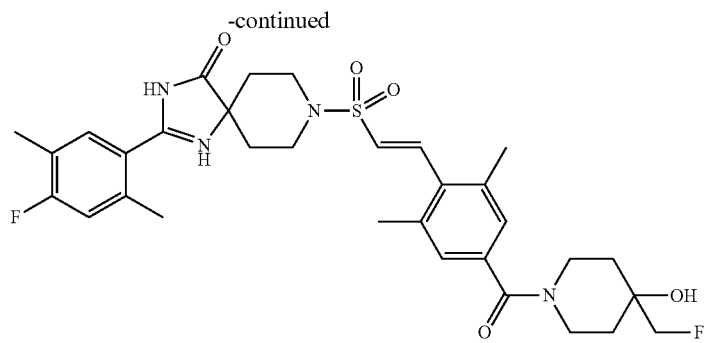

Compound 1239

2-(4-Fluoro-2,5-dimethyl-phenyl)-8-{(E)-2-[4-(4-fluoromethyl-4-hydroxy-piperidine-1-carbonyl)-2,6-dimethyl-phenyl]-ethenesulfonyl}-1,3,8-triaza-spiro[4.5]dec-1-en-4-one was obtained by operations similar to those in Reaction using 8-{(E)-2-[4-(4-fluoromethyl-4-hydroxy-piperidine-1-carbonyl)-2,6-dimethyl-phenyl]-ethenesulfonyl}-2-thioxo-1,3,8-triaza-spiro[4.5]decan-4-one as a starting material.

MS (ESI) m/z=629 (M+H)+.

The example compounds shown below were obtained by operations similar to those in Reaction 293-2 using appropriate starting compounds.

Compounds 1240 to 1281

TABLE 182

| Target Compound | Structure | LCMS condition | Retention time (min) | MS (m/z) |
|---|---|---|---|---|
| 1240 | 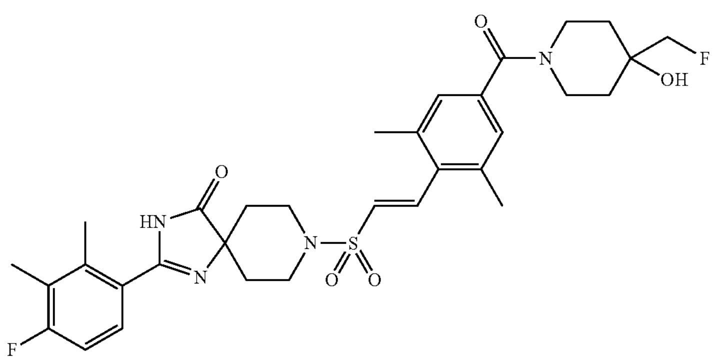 [SMILES: Cc1cc(C(=O)N2CCC(O)(CF)CC2)cc(C)c1/C=C/S(=O)(=O)N1CCC2(CC1)N=C(c1ccc(F)c(C)c1C)NC2=O] | LCMS-F-1 | 0.94 | 629 (M + H)+ |
| 1241 | 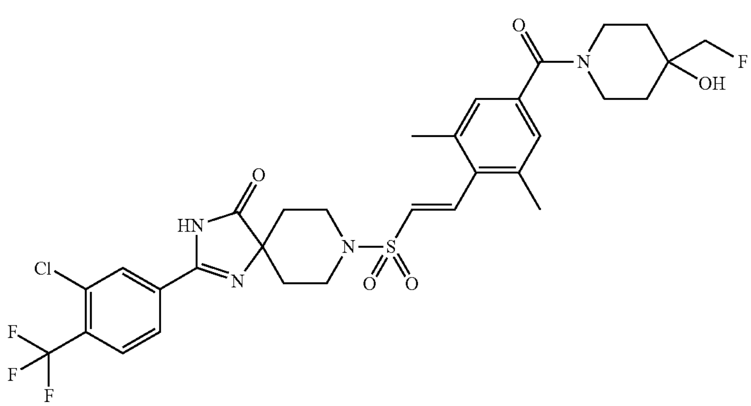 [SMILES: Cc1cc(C(=O)N2CCC(O)(CF)CC2)cc(C)c1/C=C/S(=O)(=O)N1CCC2(CC1)N=C(c1ccc(C(F)(F)F)c(Cl)c1)NC2=O] | LCMS-B-1 | 2.38 | 686 (M + H)+ |

TABLE 182-continued

| Target Compound | Structure | LCMS condition | Retention time (min) | MS (m/z) |
|---|---|---|---|---|
| 1242 | 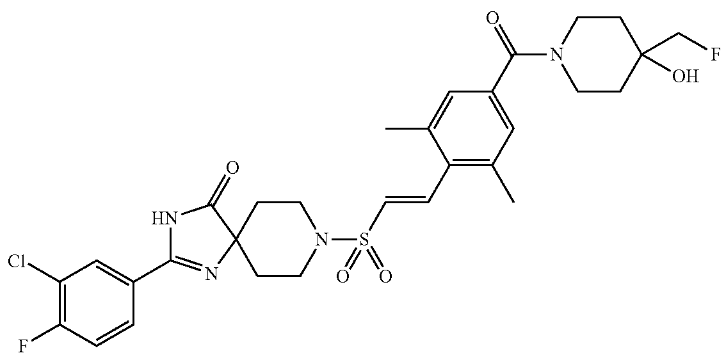 | LCMS-F-1 | 0.73 | 636 (M + H)+ |
| 1243 | 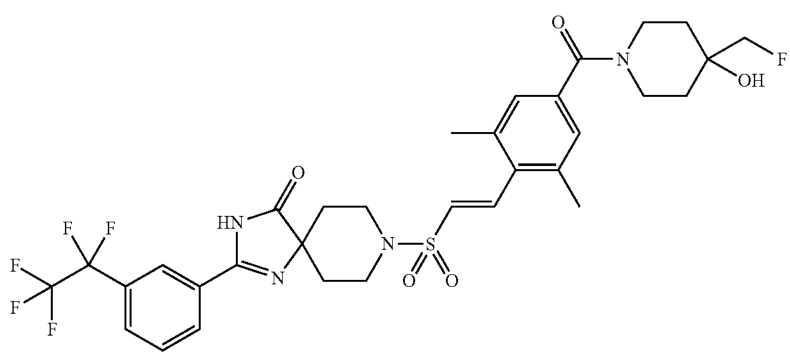 [SMILES: Cc1cc(C(=O)N2CCC(O)(CF)CC2)cc(C)c1/C=C/S(=O)(=O)N1CCC2(CC1)N=C(c1cccc(C(F)(F)C(F)(F)F)c1)NC2=O] | LCMS-F-1 | 1.01 | 701 (M + H)+ |
| 1244 | 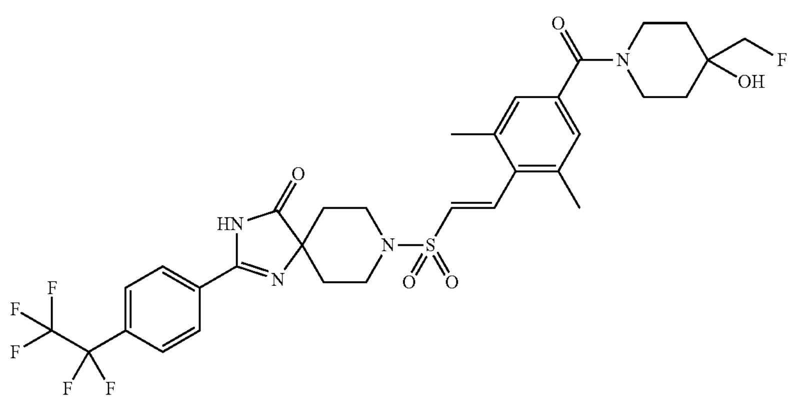 [SMILES: Cc1cc(C(=O)N2CCC(O)(CF)CC2)cc(C)c1/C=C/S(=O)(=O)N1CCC2(CC1)N=C(c1ccc(C(F)(F)C(F)(F)F)cc1)NC2=O] | LCMS-F-1 | 1.02 | 701 (M + H)+ |
| 1245 | 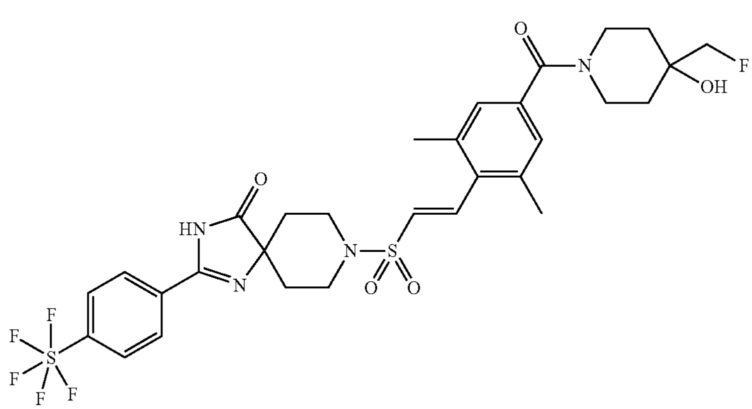 [SMILES: Cc1cc(C(=O)N2CCC(O)(CF)CC2)cc(C)c1/C=C/S(=O)(=O)N1CCC2(CC1)N=C(c1ccc(S(F)(F)(F)(F)F)cc1)NC2=O] | LCMS-F-1 | 1.01 | 709 (M + H)+ |

TABLE 182-continued

| Target Compound | Structure | LCMS condition | Retention time (min) | MS (m/z) |
|---|---|---|---|---|
| 1246 | 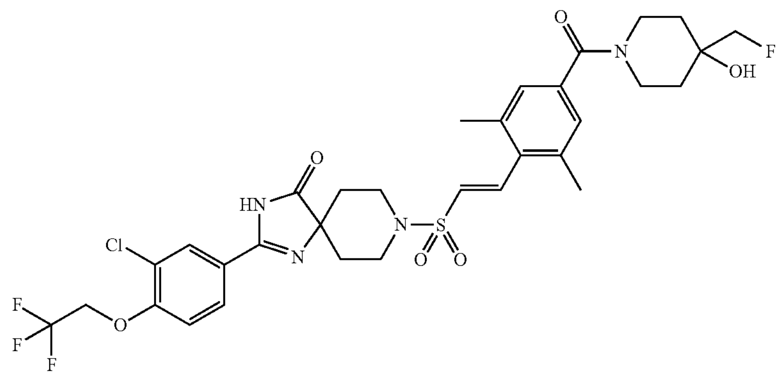 | LCMS-F-1 | 1.00 | 715 (M + H)+ |
| 1247 | 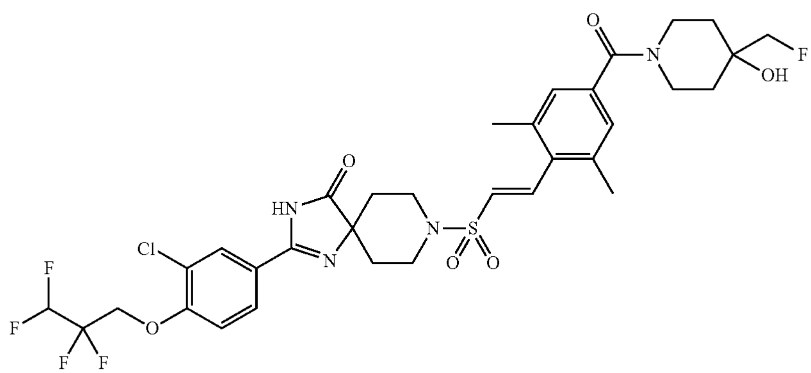 [SMILES: Cc1cc(C(=O)N2CCC(O)(CF)CC2)cc(C)c1/C=C/S(=O)(=O)N1CCC2(CC1)N=C(c1ccc(OCC(F)(F)C(F)F)c(Cl)c1)NC2=O] | LCMS-F-1 | 1.01 | 747 (M + H)+ |
| 1248 | 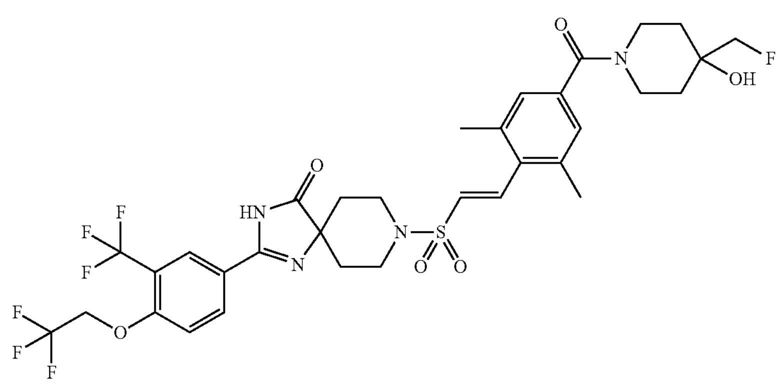 [SMILES: Cc1cc(C(=O)N2CCC(O)(CF)CC2)cc(C)c1/C=C/S(=O)(=O)N1CCC2(CC1)N=C(c1ccc(OCC(F)(F)F)c(C(F)(F)F)c1)NC2=O] | LCMS-F-1 | 1.01 | 749 (M + H)+ |
| 1249 | 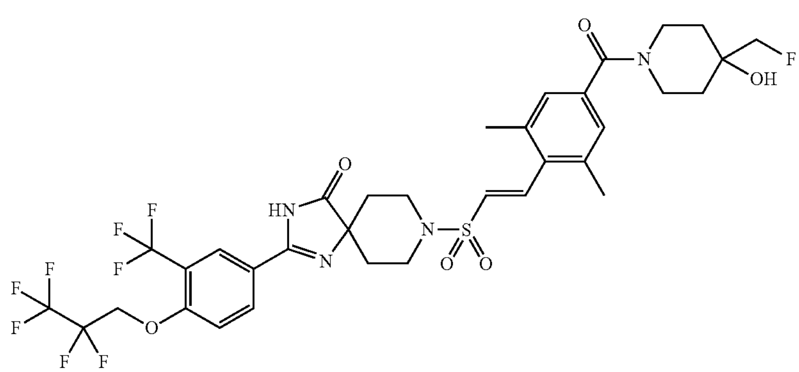 [SMILES: Cc1cc(C(=O)N2CCC(O)(CF)CC2)cc(C)c1/C=C/S(=O)(=O)N1CCC2(CC1)N=C(c1ccc(OCC(F)(F)C(F)(F)F)c(C(F)(F)F)c1)NC2=O] | LCMS-B-1 | 2.48 | 799 (M + H)+ |

TABLE 182-continued
| Target Compound | Structure | LCMS condition | Retention time (min) | MS (m/z) |
|---|---|---|---|---|
| 1250 | 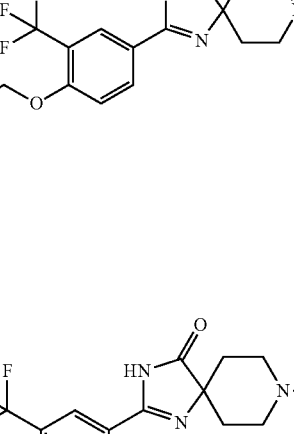 | LCMS-B-1 | 2.41 | 777 (M + H)+ |
| 1251 | 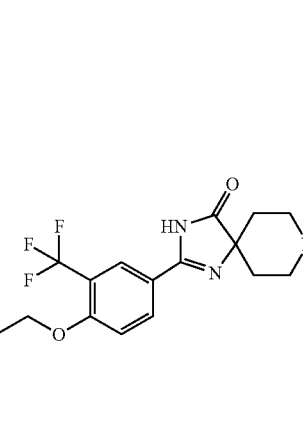 | LCMS-F-1 | 1.00 | 781 (M + H)+ |
| 1252 | 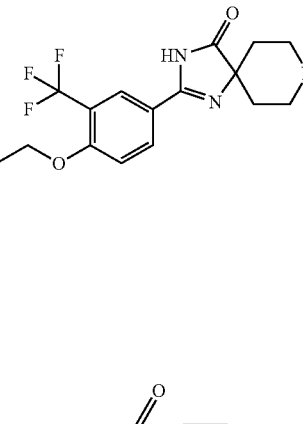 | LCMS-F-1 | 1.06 | 827 (M + H)+ |
| 1253 | 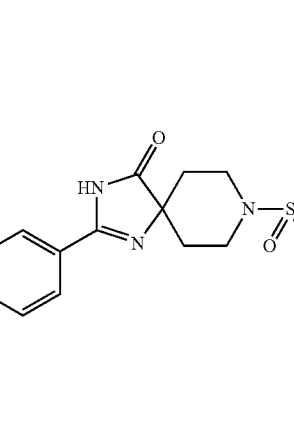 | LCMS-F-1 | 0.99 | 700 (M + H)+ |

TABLE 182-continued

| Target Compound | Structure | LCMS condition | Retention time (min) | MS (m/z) |
|---|---|---|---|---|
| 1254 | 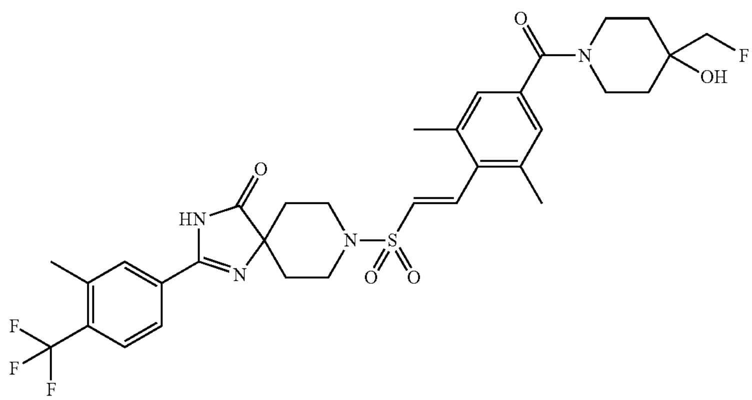 [SMILES: Cc1cc(C2=NC3(CCN(S(=O)(=O)/C=C/c4c(C)cc(C(=O)N5CCC(O)(CF)CC5)cc4C)CC3)C(=O)N2)ccc1C(F)(F)F] | LCMS-F-1 | 1.00 | 665 (M + H)+ |
| 1255 | 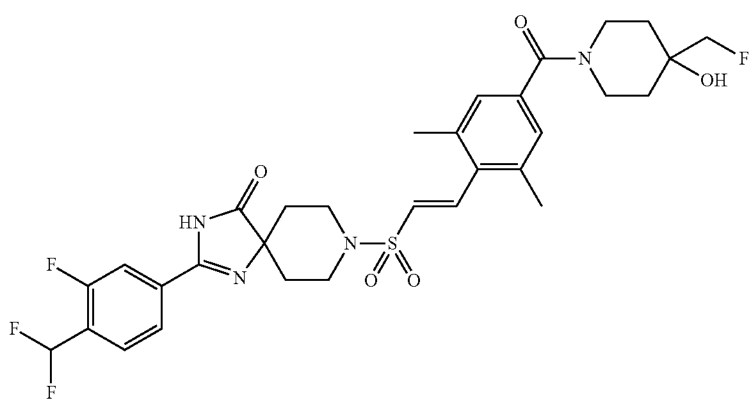 [SMILES: Cc1cc(C(=O)N2CCC(O)(CF)CC2)cc(C)c1/C=C/S(=O)(=O)N1CCC2(CC1)N=C(c1ccc(C(F)F)c(F)c1)NC2=O] | LCMS-F-1 | 0.93 | 651 (M + H)+ |
| 1256 | 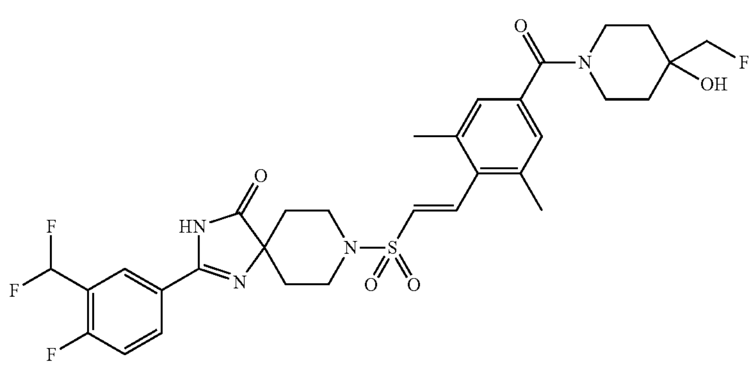 [SMILES: Cc1cc(C(=O)N2CCC(O)(CF)CC2)cc(C)c1/C=C/S(=O)(=O)N1CCC2(CC1)N=C(c1ccc(F)c(C(F)F)c1)NC2=O] | LCMS-F-1 | 0.92 | 651 (M + H)+ |
| 1257 | 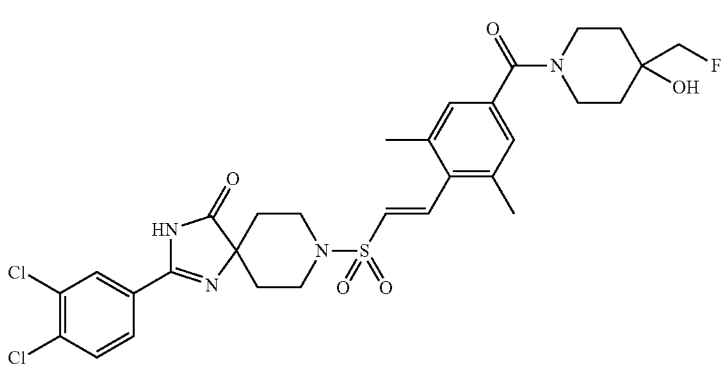 [SMILES: Cc1cc(C(=O)N2CCC(O)(CF)CC2)cc(C)c1/C=C/S(=O)(=O)N1CCC2(CC1)N=C(c1ccc(Cl)c(Cl)c1)NC2=O] | LCMS-F-1 | 1.00 | 651 (M + H)+ |

TABLE 182-continued

| Target Compound | Structure | LCMS condition | Retention time (min) | MS (m/z) |
|---|---|---|---|---|
| 1258 | 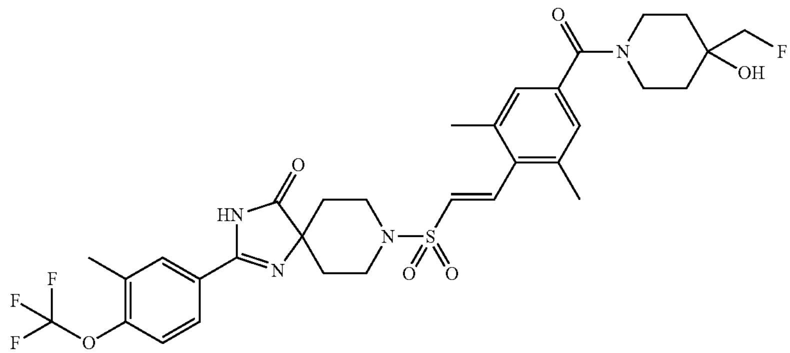 [SMILES: Cc1cc(C2=NC3(CCN(S(=O)(=O)/C=C/c4c(C)cc(C(=O)N5CCC(O)(CF)CC5)cc4C)CC3)C(=O)N2)ccc1OC(F)(F)F] | LCMS-F-1 | 1.01 | 681 (M + H)+ |
| 1259 | 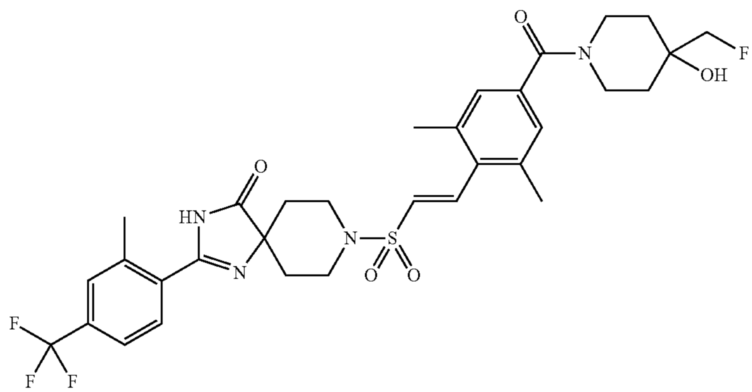 [SMILES: Cc1cc(C(F)(F)F)ccc1C1=NC2(CCN(S(=O)(=O)/C=C/c3c(C)cc(C(=O)N4CCC(O)(CF)CC4)cc3C)CC2)C(=O)N1] | LCMS-F-1 | 0.96 | 665 (M + H)+ |
| 1260 | 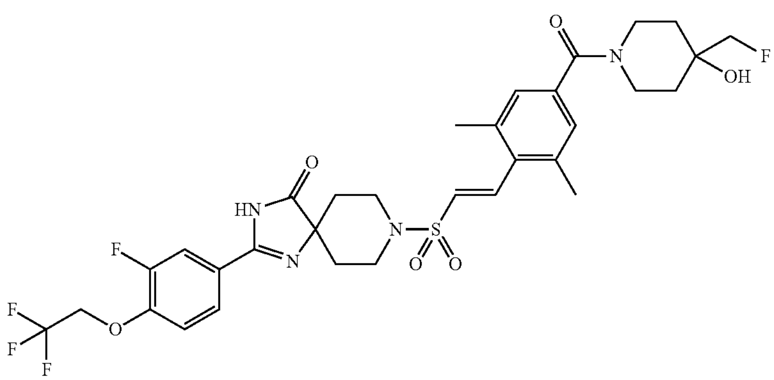 [SMILES: Cc1cc(C(=O)N2CCC(O)(CF)CC2)cc(C)c1/C=C/S(=O)(=O)N1CCC2(CC1)N=C(c1ccc(OCC(F)(F)F)c(F)c1)NC2=O] | LCMS-F-1 | 0.95 | 699 (M + H)+ |
| 1261 | 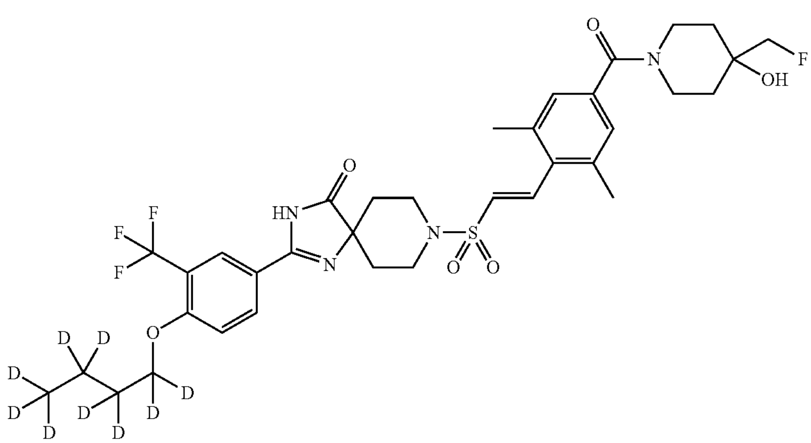 [SMILES: [2H]C([2H])([2H])C([2H])([2H])C([2H])([2H])C([2H])([2H])Oc1ccc(C2=NC3(CCN(S(=O)(=O)/C=C/c4c(C)cc(C(=O)N5CCC(O)(CF)CC5)cc4C)CC3)C(=O)N2)cc1C(F)(F)F] | LCMS-F-1 | 1.04 | 732 (M + H)+ |

TABLE 182-continued

| Target Compound | Structure | LCMS condition | Retention time (min) | MS (m/z) |
|---|---|---|---|---|
| 1262 | 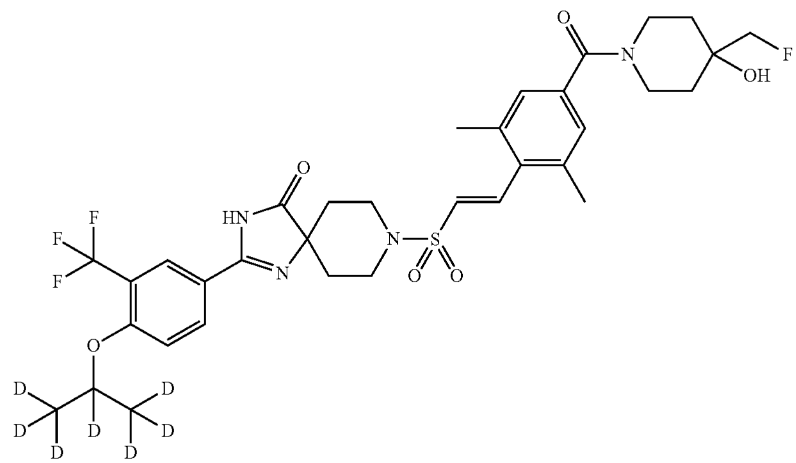 [SMILES: [2H]C([2H])([2H])C([2H])(Oc1ccc(C2=NC3(CCN(S(=O)(=O)/C=C/c4c(C)cc(C(=O)N5CCC(O)(CF)CC5)cc4C)CC3)C(=O)N2)cc1C(F)(F)F)C([2H])([2H])[2H]] | LCMS-F-1 | 1.01 | 716 (M + H)+ |
| 1263 | 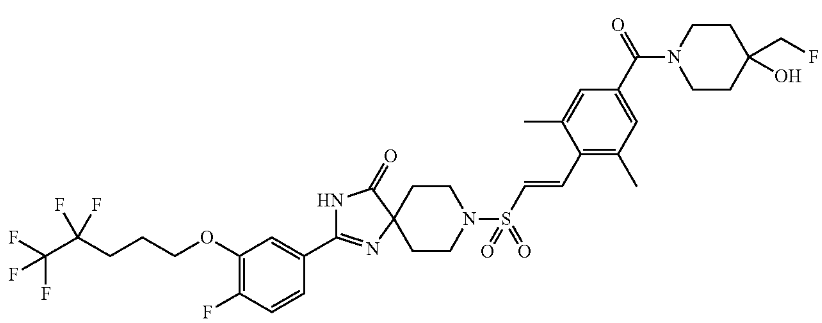 [SMILES: Cc1cc(C(=O)N2CCC(O)(CF)CC2)cc(C)c1/C=C/S(=O)(=O)N1CCC2(CC1)N=C(c1ccc(F)c(OCCCC(F)(F)C(F)(F)F)c1)NC2=O] | LCMS-F-1 | 1.05 | 777 (M + H)+ |
| 1264 | 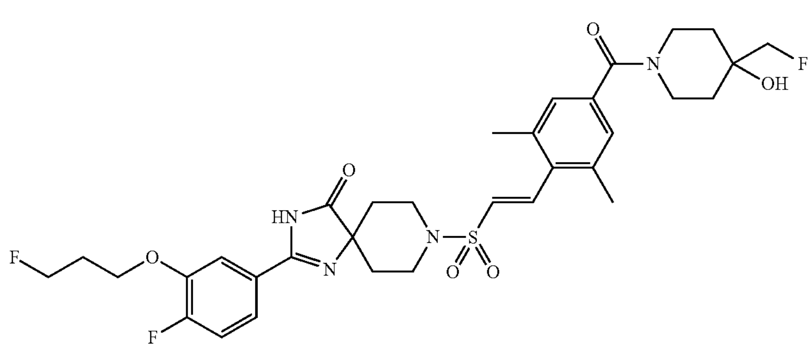 [SMILES: Cc1cc(C(=O)N2CCC(O)(CF)CC2)cc(C)c1/C=C/S(=O)(=O)N1CCC2(CC1)N=C(c1ccc(F)c(OCCCF)c1)NC2=O] | LCMS-F-1 | 0.95 | 677 (M + H)+ |

TABLE 182-continued

| Target Compound | Structure | LCMS condition | Retention time (min) | MS (m/z) |
|---|---|---|---|---|
| 1265 | 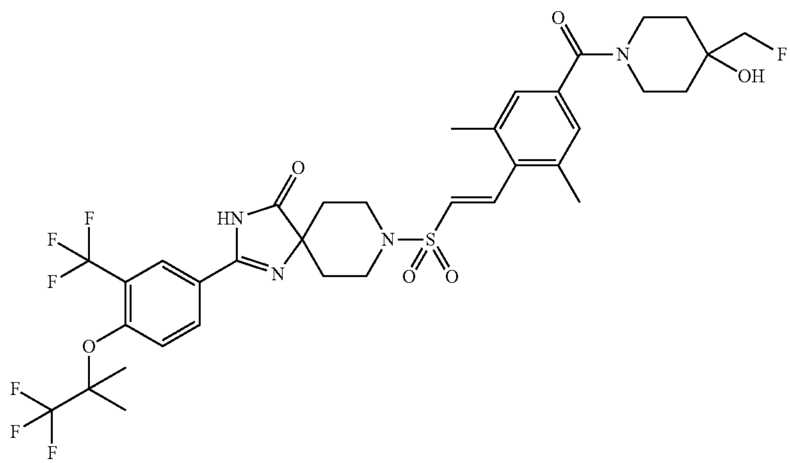 [SMILES: Cc1cc(C(=O)N2CCC(O)(CF)CC2)cc(C)c1/C=C/S(=O)(=O)N1CCC2(CC1)N=C(c1ccc(OC(C)(C)C(F)(F)F)c(C(F)(F)F)c1)NC2=O] | LCMS-F-1 | 1.04 | 777 (M + H)+ |
| 1266 | 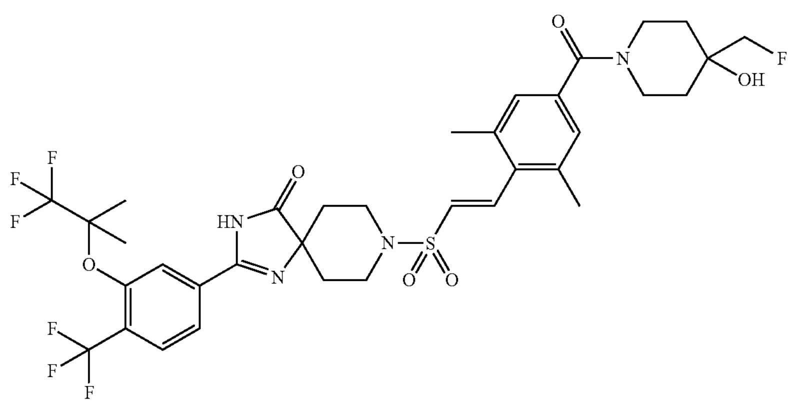 [SMILES: Cc1cc(C(=O)N2CCC(O)(CF)CC2)cc(C)c1/C=C/S(=O)(=O)N1CCC2(CC1)N=C(c1ccc(C(F)(F)F)c(OC(C)(C)C(F)(F)F)c1)NC2=O] | LCMS-F-1 | 1.04 | 777 (M + H)+ |
| 1267 | 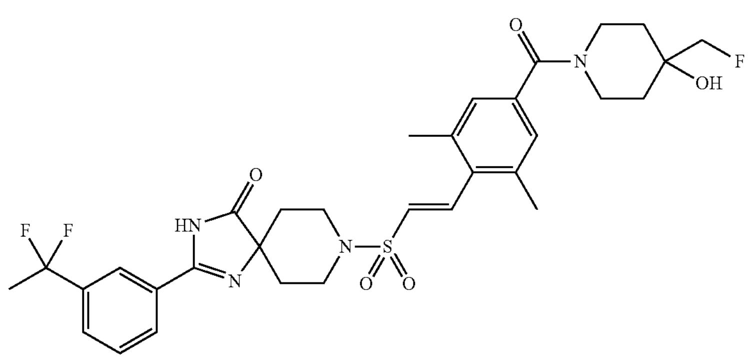 [SMILES: Cc1cc(C(=O)N2CCC(O)(CF)CC2)cc(C)c1/C=C/S(=O)(=O)N1CCC2(CC1)N=C(c1cccc(C(C)(F)F)c1)NC2=O] | LCMS-F-1 | 0.93 | 647 (M + H)+ |
| 1268 | 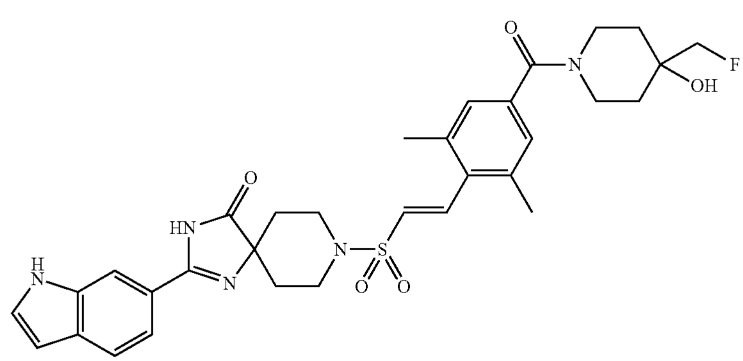 [SMILES: Cc1cc(C(=O)N2CCC(O)(CF)CC2)cc(C)c1/C=C/S(=O)(=O)N1CCC2(CC1)N=C(c1ccc3cc[nH]c3c1)NC2=O] | LCMS-F-1 | 0.88 | 622 (M + H)+ |

TABLE 182-continued

| Target Compound | Structure | LCMS condition | Retention time (min) | MS (m/z) |
|---|---|---|---|---|
| 1269 | 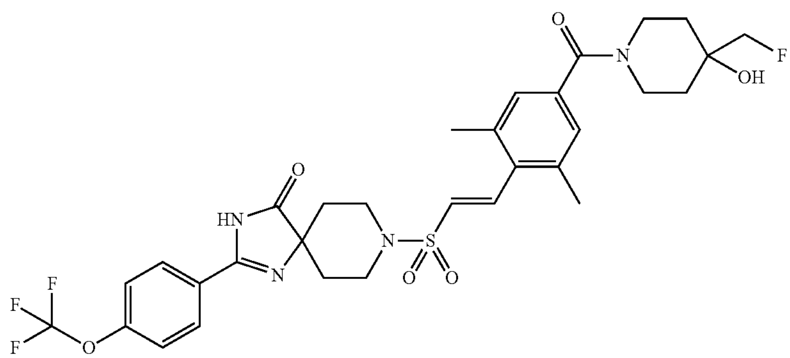 [SMILES: Cc1cc(C(=O)N2CCC(O)(CF)CC2)cc(C)c1/C=C/S(=O)(=O)N1CCC2(CC1)N=C(c1ccc(OC(F)(F)F)cc1)NC2=O] | LCMS-F-1 | 0.98 | 667 (M + H)+ |
| 1270 | 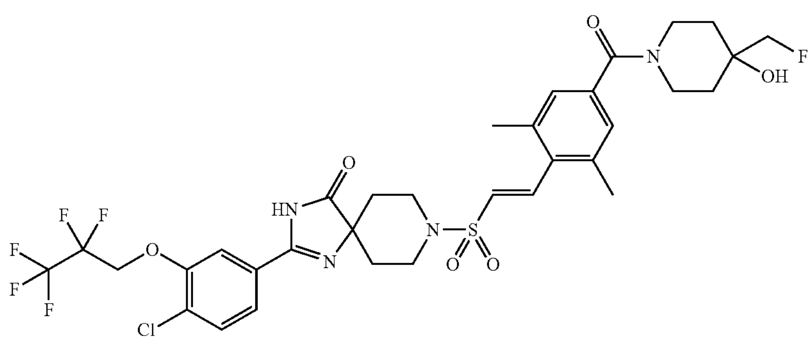 [SMILES: Cc1cc(C(=O)N2CCC(O)(CF)CC2)cc(C)c1/C=C/S(=O)(=O)N1CCC2(CC1)N=C(c1ccc(Cl)c(OCC(F)(F)C(F)(F)F)c1)NC2=O] | LCMS-F-1 | 1.04 | 765 (M + H)+ |
| 1271 | 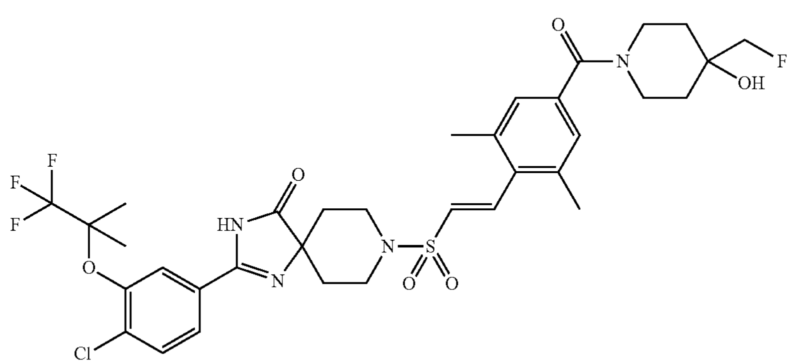 [SMILES: Cc1cc(C(=O)N2CCC(O)(CF)CC2)cc(C)c1/C=C/S(=O)(=O)N1CCC2(CC1)N=C(c1ccc(Cl)c(OC(C)(C)C(F)(F)F)c1)NC2=O] | LCMS-F-1 | 1.04 | 743 (M + H)+ |
| 1272 | 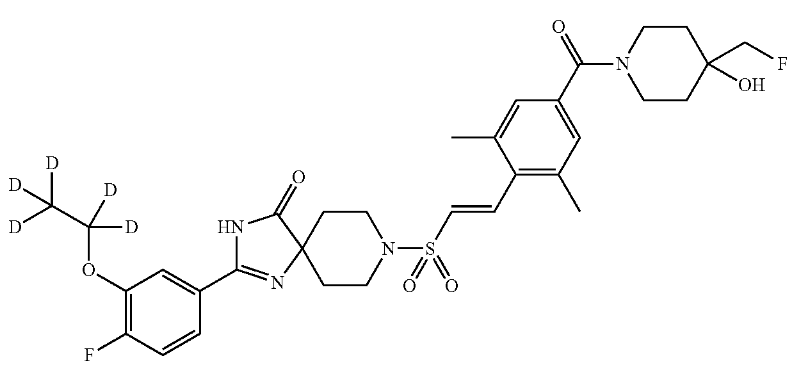 [SMILES: [2H]C([2H])([2H])C([2H])([2H])Oc1cc(C2=NC3(CCN(S(=O)(=O)/C=C/c4c(C)cc(C(=O)N5CCC(O)(CF)CC5)cc4C)CC3)C(=O)N2)ccc1F] | LCMS-F-1 | 0.95 | 650 (M + H)+ |

TABLE 182-continued

| Target Compound | Structure | LCMS condition | Retention time (min) | MS (m/z) |
|---|---|---|---|---|
| 1273 | 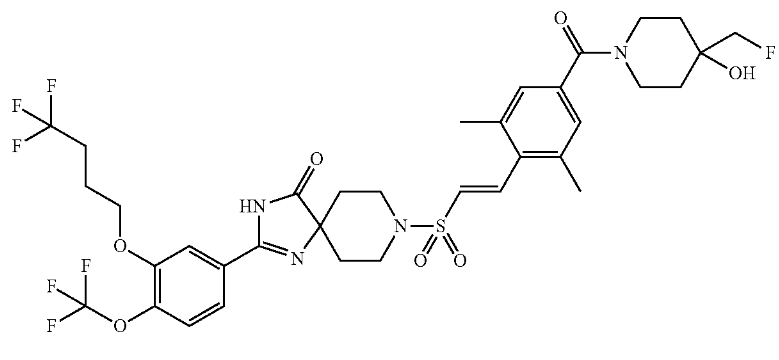 [SMILES: Cc1cc(C(=O)N2CCC(O)(CF)CC2)cc(C)c1/C=C/S(=O)(=O)N1CCC2(CC1)N=C(c1ccc(OC(F)(F)F)c(OCCCC(F)(F)F)c1)NC2=O] | LCMS F-1 | 1.06 | 793 (M + H)+ |
| 1274 | 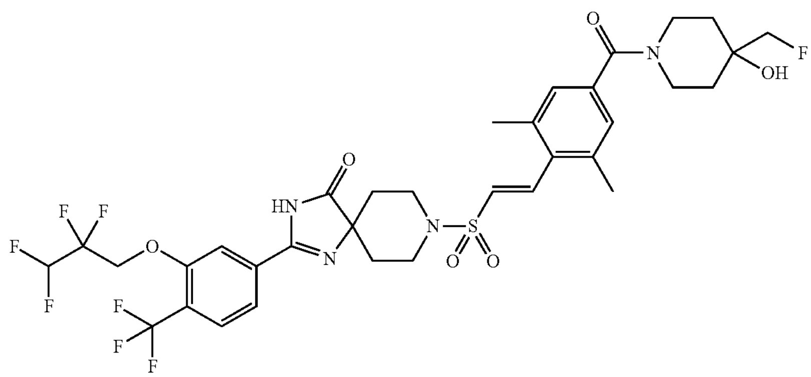 [SMILES: Cc1cc(C(=O)N2CCC(O)(CF)CC2)cc(C)c1/C=C/S(=O)(=O)N1CCC2(CC1)N=C(c1ccc(C(F)(F)F)c(OCC(F)(F)C(F)F)c1)NC2=O] | LCMS-F-1 | 1.02 | 781 (M + H)+ |
| 1275 | 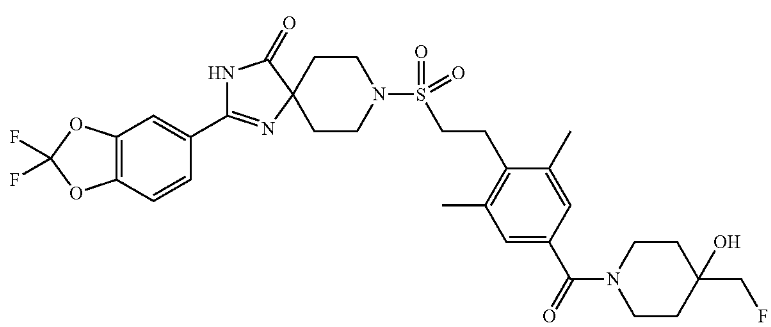 [SMILES: Cc1cc(C(=O)N2CCC(O)(CF)CC2)cc(C)c1CCS(=O)(=O)N1CCC2(CC1)N=C(c1ccc3c(c1)OC(F)(F)O3)NC2=O] | LCMS-G-1 | 1.11 | 665 (M + H)+ |
| 1276 | 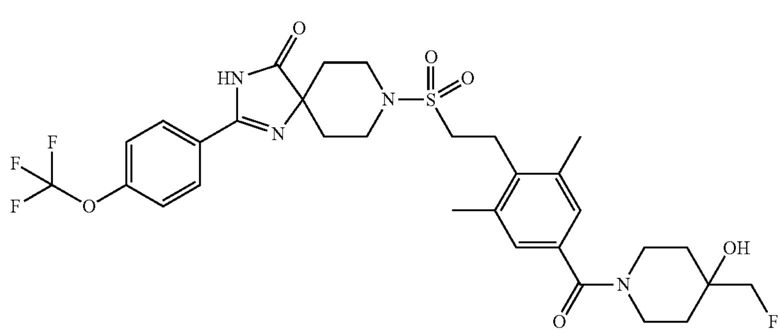 [SMILES: Cc1cc(C(=O)N2CCC(O)(CF)CC2)cc(C)c1CCS(=O)(=O)N1CCC2(CC1)N=C(c1ccc(OC(F)(F)F)cc1)NC2=O] | LCMS-G-1 | 1.11 | 669 (M + H)+ |

TABLE 182-continued

| Target Compound | Structure | LCMS condition | Retention time (min) | MS (m/z) |
|---|---|---|---|---|
| 1277 | 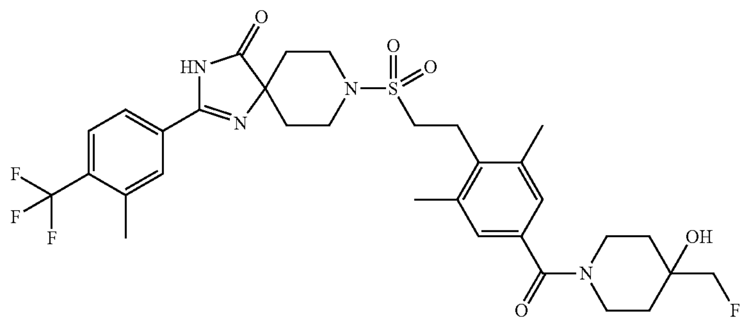 [SMILES: Cc1cc(C2=NC3(CCN(S(=O)(=O)CCc4c(C)cc(C(=O)N5CCC(O)(CF)CC5)cc4C)CC3)C(=O)N2)ccc1C(F)(F)F] | LCMS-G-1 | 1.13 | 667 (M + H)+ |
| 1278 | 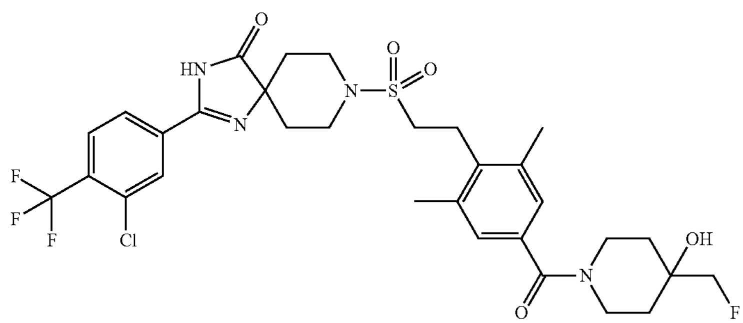 | LCMS-G-1 | 1.16 | 687 (M + H)+ |
| 1279 | 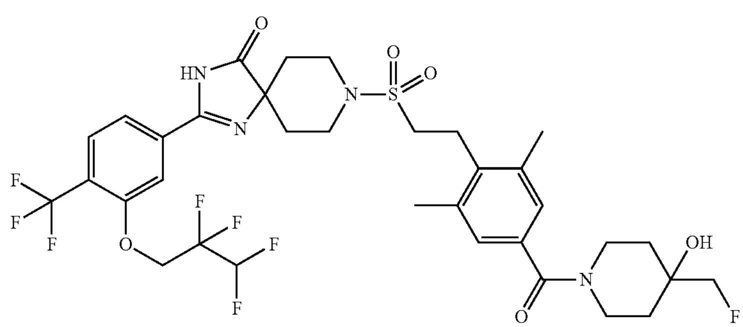 [SMILES: Cc1cc(C(=O)N2CCC(O)(CF)CC2)cc(C)c1CCS(=O)(=O)N1CCC2(CC1)N=C(c1ccc(C(F)(F)F)c(OCC(F)(F)C(F)F)c1)NC2=O] | LCMS-G-1 | 1.17 | 783 (M + H)+ |
| 1280 | 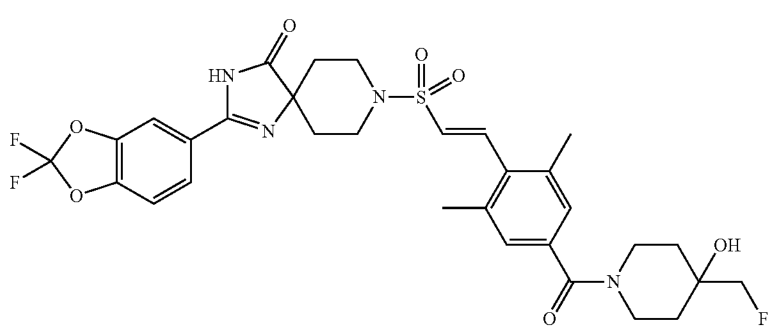 [SMILES: Cc1cc(C(=O)N2CCC(O)(CF)CC2)cc(C)c1/C=C/S(=O)(=O)N1CCC2(CC1)N=C(c1ccc3c(c1)OC(F)(F)O3)NC2=O] | LCMS-G-1 | 1.11 | 663 (M + H)+ |

TABLE 182-continued

| Target Compound | Structure | LCMS condition | Retention time (min) | MS (m/z) |
|---|---|---|---|---|
| 1281 | 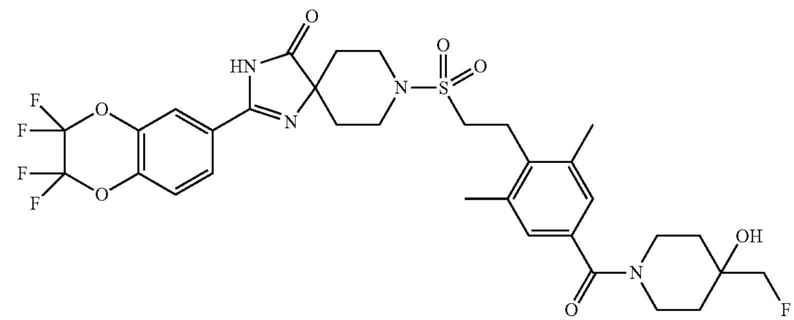 [SMILES: Cc1cc(C(=O)N2CCC(O)(CF)CC2)cc(C)c1CCS(=O)(=O)N1CCC2(CC1)N=C(c1ccc3c(c1)OC(F)(F)C(F)(F)O3)NC2=O] | LCMS-F-1 | 1.03 | 715 (M + H)+ |

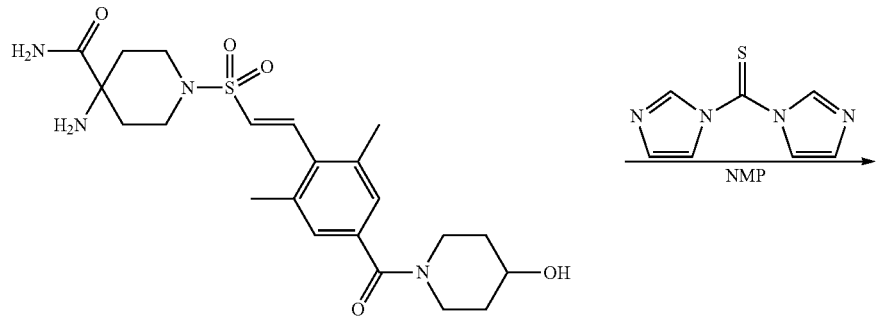

Example 294

[3-(8-{(E)-2-[4-(4-Hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile (Compound 1282)

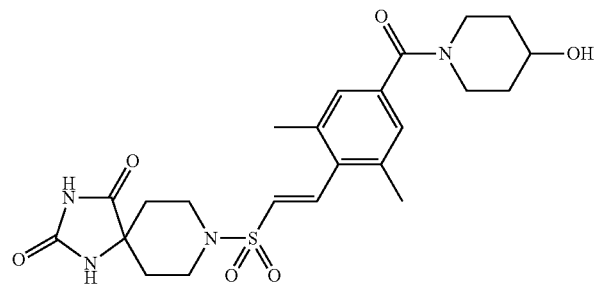

8-{(E)-2-[4-(4-Hydroxy-piperidine-1-carbonyl)-2,6-dimethyl-phenyl]-ethenesulfonyl}-2-thioxo-1,3,8-triaza-spiro[4.5]decan-4-one was obtained by operations similar to those in Reaction 292-2 (using 1,1'-thiocarbonyldiimidazole) using appropriate reagents and starting material.

MS (ESI) m/z=507 (M+H)+.

(Reaction 294-2)

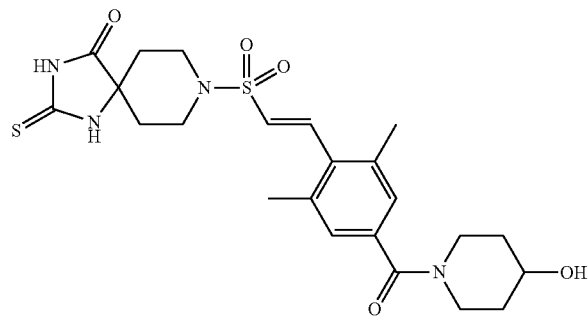

294a

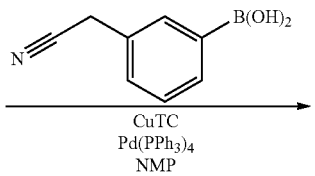

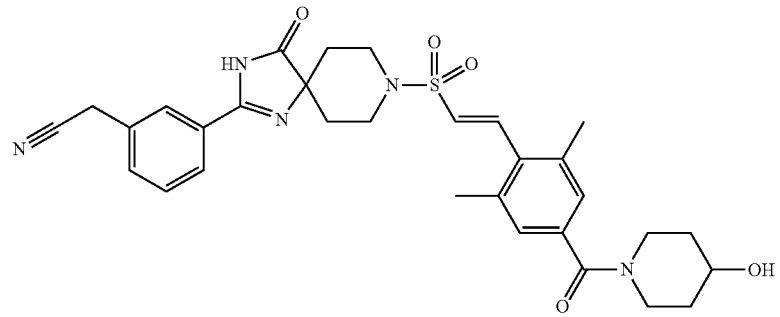

Compound 1282

[3-(8-{(E)-2-[4-(4-Hydroxy-piperidine-1-carbonyl)-2,6-dimethyl-phenyl]-ethenesulfonyl}-4-oxo-1,3,8-triaza-spiro[4.5]dec-1-en-2-yl)-phenyl]-acetonitrile was obtained by operations similar to those in Reaction 292-3 using 8-{(E)-2-[4-(4-hydroxy-piperidine-1-carbonyl)-2,6-dimethyl-phenyl]-ethenesulfonyl}-2-thioxo-1,3,8-triaza-spiro[4.5]decan-4-one as a starting material.

MS (ESI) m/z=590 (M+H)+.

Example 295

8-{(E)-2-[2-Methyl-4-(piperidin-4-yloxy)-phenyl]-ethenesulfonyl}-2-(3-trifluoromethoxy-phenyl)-1,3,8-triaza-spiro[4.5]dec-1-en-4-one trifluoroacetate
(Compound 1283)

(Reaction 295-1)

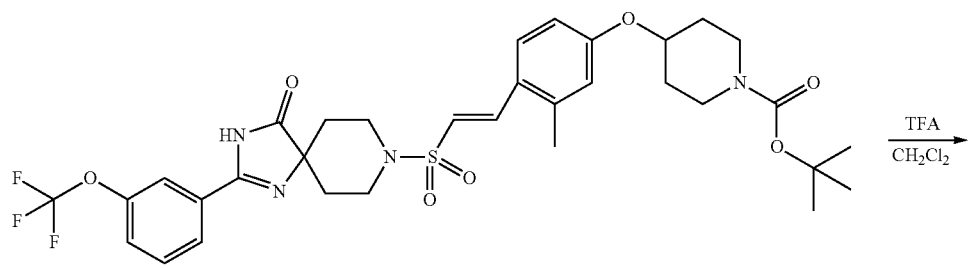

Compound 602

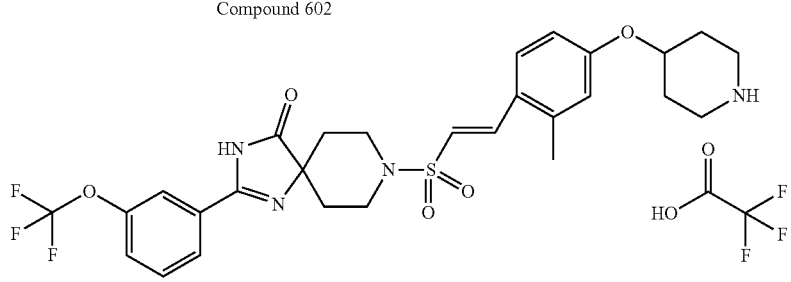

Compound 1283

1467

8-{(E)-2-[2-Methyl-4-(piperidin-4-yloxy)-phenyl]-ethenesulfonyl}-2-(3-trifluoromethoxy-phenyl)-1,3,8-triazaspiro[4.5]dec-1-en-4-one trifluoroacetate (Compound 1283) was obtained by operations similar to those in Reaction 4-1 using Compound 602 as a starting material.

MS (ESI) m/z=593 (M+H)+.

1468

The example compounds shown below were obtained by operations similar to those in Reaction 295-1 using appropriate starting compounds. Compound 1285 was obtained as a free form by desalination post-treatment.

Compounds 1284 to Compound 1285

TABLE 183

| Starting Compound | Target Compound | Structure | LCMS condition | Retention time (min) | MS (m/z) |
|---|---|---|---|---|---|
| 928 | 1284 | 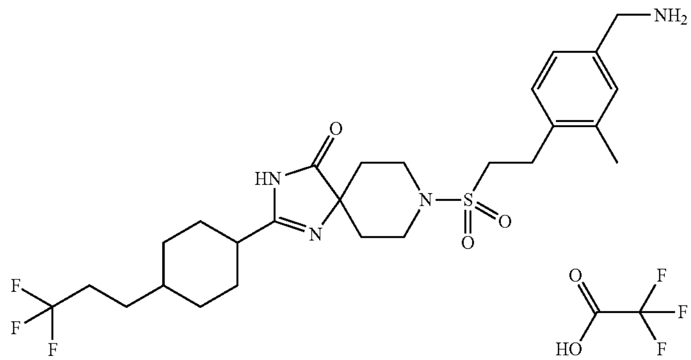 [SMILES: Cc1cc(CN)ccc1CCS(=O)(=O)N1CCC2(CC1)N=C(C1CCC(CCC(F)(F)F)CC1)NC2=O ; O=C(O)C(F)(F)F] | LCMS-B-1 | 1.67 | 543 (M + H)+ |
| 578 | 1285 | 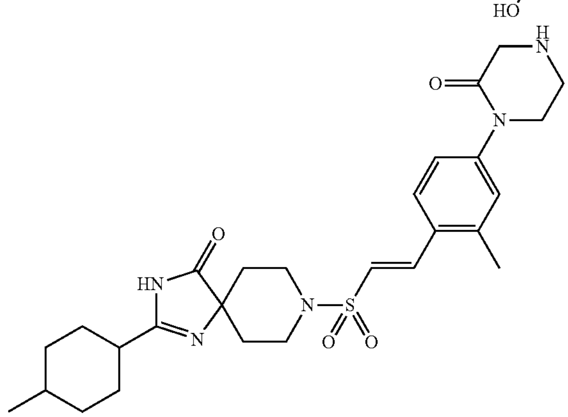 | LCMS-A-1 | 1.69 | 528 (M + H)+ |

Example 296

8-[2-(2,6-Dimethyl-4-methylamino-phenyl)-ethanesulfonyl]-2-pyrrolidin-2-yl-1,3,8-triaza-spiro[4.5]dec-1-en-4-one dihydrochloride (Compound 1286)

(Reaction 296-1)

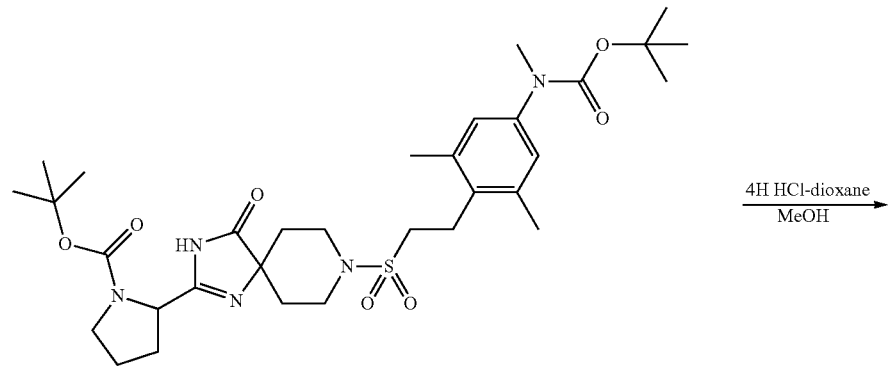

Compound 1033

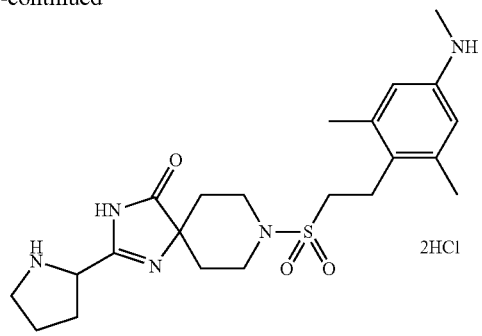

Compound 1286

8-[2-(2,6-Dimethyl-4-methylamino-phenyl)-ethanesulfonyl]-2-pyrrolidin-2-yl-1,3,8-triaza-spiro[4.5]dec-1-en-4-one dihydrochloride (Compound 1286) was obtained by operations similar to those in Reaction 5-3 using Compound 1033 as a starting material.

MS (ESI) m/z=448 (M+H)+.

The example compounds shown below were obtained by operations similar to those in Reaction 296-1 using appropriate starting compounds.

Compounds 1287 to Compound 1288

TABLE 184

| Starting Compound | Target Compound | Structure | LCMS condition | Retention time (min) | MS (m/z) |
|---|---|---|---|---|---|
| 1034 | 1287 | 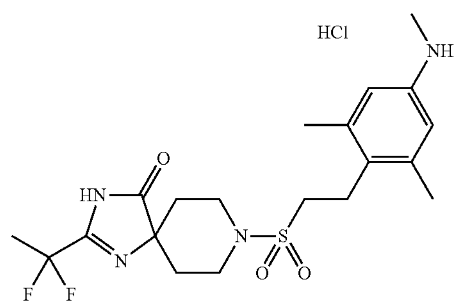 [SMILES: CNc1cc(C)c(CCS(=O)(=O)N2CCC3(CC2)N=C(C(C)(F)F)NC3=O)c(C)c1 ; Cl] | LCMS-B-1 | 1.44 | 443 (M + H)+ |
| 640 | 1288 | 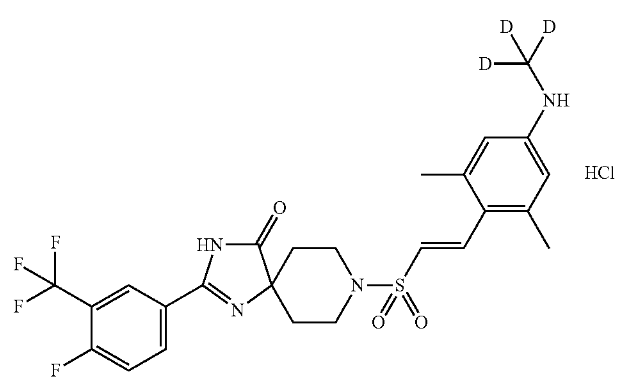 [SMILES: [2H]C([2H])([2H])Nc1cc(C)c(/C=C/S(=O)(=O)N2CCC3(CC2)N=C(c2ccc(F)c(C(F)(F)F)c2)NC3=O)c(C)c1 ; Cl] | LCMS-F-1 | 1.05 | 542 (M + H)+ |

Example 297

8-[(E)-2-(2,6-Dimethyl-4-methylaminomethyl-phenyl)-ethenesulfonyl]-2-(4-methyl-cyclohexyl)-1,3,8-triaza-spiro[4.5]dec-1-en-4-one (Compound 1289)

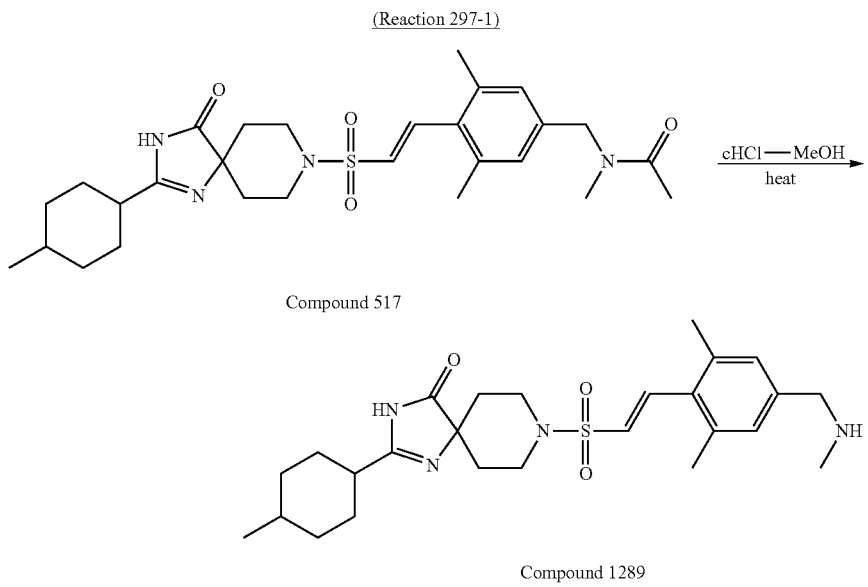

Compound 517

Compound 1289

8-[(E)-2-(2,6-Dimethyl-4-methylaminomethyl-phenyl)-ethenesulfonyl]-2-(4-methyl-cyclohexyl)-1,3,8-triaza-spiro[4.5]dec-1-en-4-one (Compound 1289) was obtained by operations similar to those in Reaction 50-2 (conversion to a free form by post-treatment) using Compound 517 as a starting material.
MS (ESI) m/z=487 (M+H)+.

The example compounds shown below were obtained by operations similar to those in Reaction 297-1 using appropriate starting compounds.

Compounds 1290 to Compound 1292

TABLE 185

| Starting Compound | Target Compound | Structure | LCMS condition | Retention time (min) | MS (m/z) |
|---|---|---|---|---|---|
| 558 | 1290 | 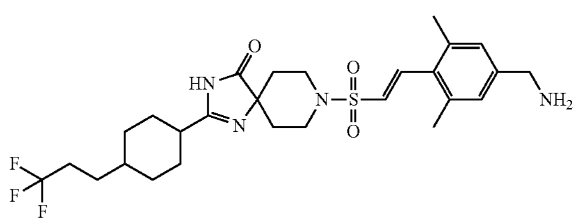 [SMILES: Cc1cc(CN)cc(C)c1/C=C/S(=O)(=O)N1CCC2(CC1)N=C(C1CCC(CCC(F)(F)F)CC1)NC2=O] | LCMS-D-1 | 2.27 | 555 (M + H)+ |
| 522 | 1291 | 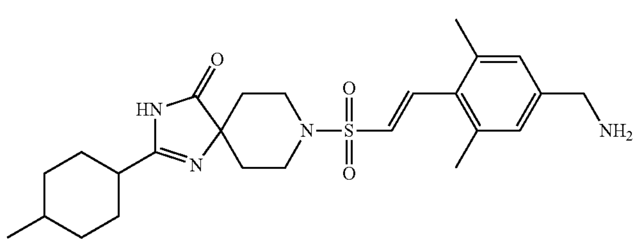 [SMILES: Cc1cc(CN)cc(C)c1/C=C/S(=O)(=O)N1CCC2(CC1)N=C(C1CCC(C)CC1)NC2=O] | LCMS-D-1 | 1.93 | 473 (M + H)+ |

| Starting Compound | Target Compound | Structure | LCMS condition | Retention time (min) | MS (m/z) |
|---|---|---|---|---|---|
| 559 | 1292 | 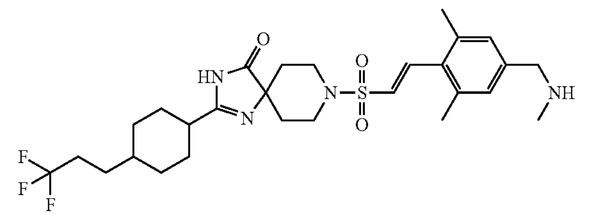 [SMILES: CNCc1cc(C)c(/C=C/S(=O)(=O)N2CCC3(CC2)N=C(C2CCC(CCC(F)(F)F)CC2)NC3=O)c(C)c1] | LCMS-D-1 | 1.77 | 569 (M + H)+ |

Example 298

8-[2-(4-Amino-3-chloro-2-methyl-phenyl)-ethane-sulfonyl]-2-(4-ethyl-cyclohexyl)-1,3,8-triaza-spiro[4.5]dec-1-en-4-one (Compound 1293)

(Reaction 298-1)

8-[2-(4-Amino-3-chloro-2-methyl-phenyl)-ethanesulfonyl]-2-(4-ethyl-cyclohexyl)-1,3,8-triaza-spiro[4.5]dec-1-en-4-one (Compound 1293) was obtained by operations similar to those in Reaction 12-5 using Compound 954 as a starting material.

MS (ESI) m/z=495 (M+H)+.

Example 299

N-(1-Acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 1294)

(Reaction 299-1)

1475

N-(1-Acetyl-piperidin-4-yl)-N-(3-methyl-4-{(E)-2-[4-oxo-2-(3-trifluoromethoxy-phenyl)-1,3,8-triaza-spiro[4.5]dec-1-ene-8-sulfonyl]-vinyl}-phenyl)-acetamide (Compound 1294) was obtained by operations similar to those in Reaction 4-1 and Reaction 12-2 using Compound 604 as a starting material.

MS (ESI) m/z=676 (M+H)+.

Example 300

8-{2-[4-(4,5-Dihydro-thiazol-2-ylamino)-2-methyl-phenyl]-ethanesulfonyl}-2-(4-ethyl-cyclohexyl)-1,3,8-triaza-spiro[4.5]dec-1-en-4-one (Compound 1295)

1476

8-{2-[4-(4,5-Dihydro-thiazol-2-ylamino)-2-methyl-phenyl]-ethanesulfonyl}-2-(4-ethyl-cyclohexyl)-1,3,8-triaza-spiro[4.5]dec-1-en-4-one (Compound 1295) was obtained by operations similar to those in Reaction 12-5, Reaction 18-2 and Reaction 177-2 using Compound 953 as a starting material.

MS (ESI) m/z=546 (M+H)+.

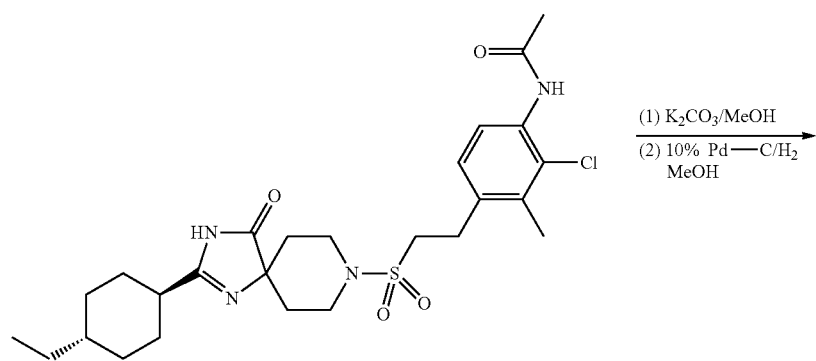

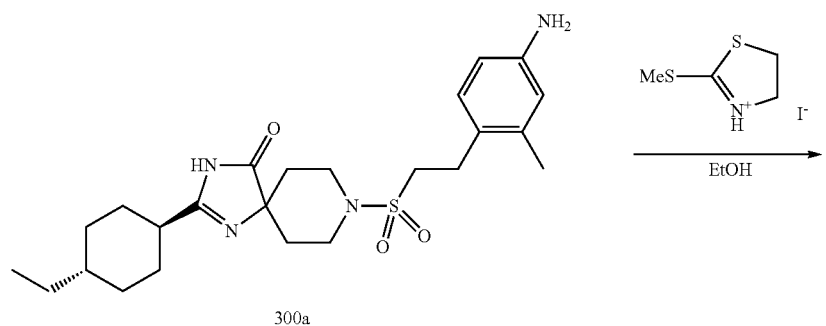

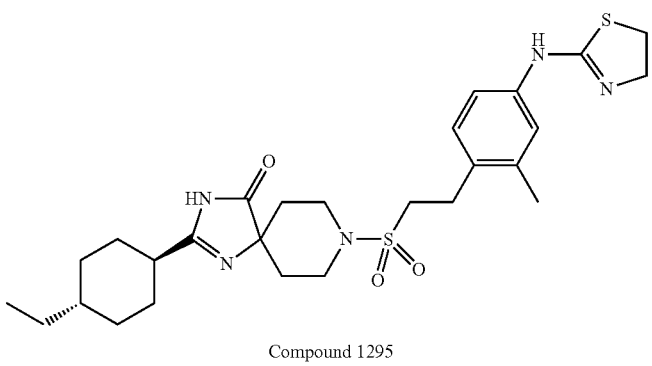

Example 301

N-[4-(2-{2-[4-(4-Fluoro-butyl)-cyclohexyl]-4-oxo-1,3,8-triaza-spiro[4.5]dec-1-ene-8-sulfonyl}-ethyl)-3-methyl-phenyl]-acetamide (Compound 1296)

(Reaction 301-1)

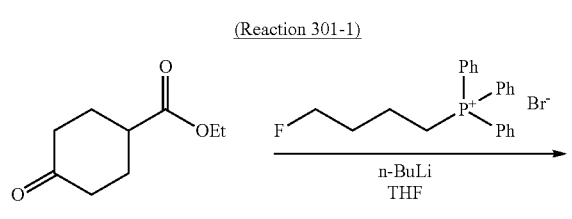

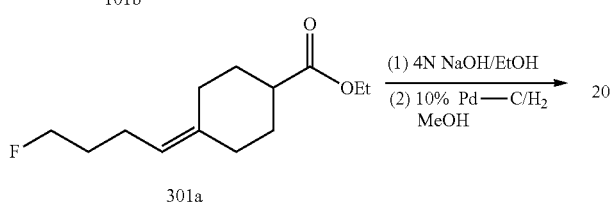

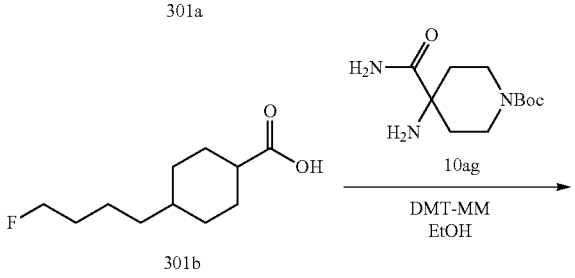

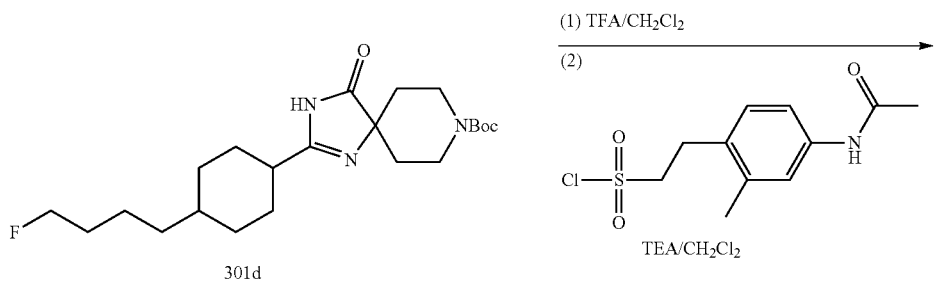

2-[4-(4-Fluoro-butyl)-cyclohexyl]-4-oxo-1,3,8-triaza-spiro[4.5]dec-1-ene-8-carboxylic acid tert-butyl ester was obtained by operations similar to those in Reaction 101-1, Reaction 23-2, Reaction 18-2, Reaction 10-1 and Reaction 189-5 using 4-oxo-cyclohexanecarboxylic acid ethyl ester as a starting material.

$^1$H-NMR (400 MHz, CDCl$_3$) δ 0.97-1.05 (1H, m), 1.23-1.35 (4H, m), 1.35-1.50 (3, m), 1.47 (9H, s), 1.60-1.75 (4H, m), 1.75-1.85 (2H, m), 1.85-1.95 (2H, m), 1.95-2.05 (2H, m), 2.35-2.45 (1H, m), 3.35-3.45 (2H, m), 3.90-4.05 (2H, m), 4.35-4.42 (1H, m), 4.45-4.52 (1H, m), 8.85 (1H, s).

(Reaction 301-2)

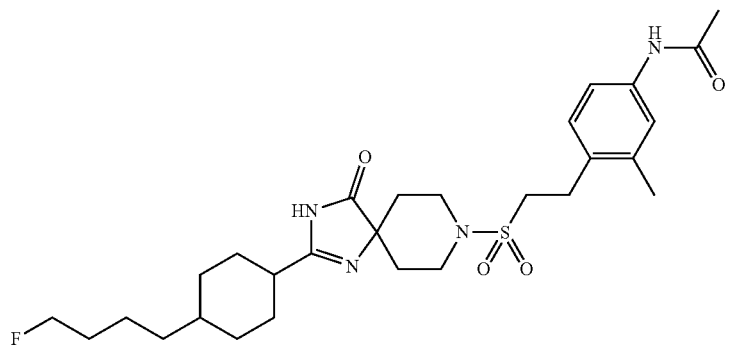

Compound 1296

N-[4-(2-{2-[4-(4-Fluoro-butyl)-cyclohexyl]-4-oxo-1,3,8-triaza-spiro[4.5]dec-1-ene-8-sulfonyl}-ethyl)-3-methyl-phenyl]-acetamide (Compound 1296) was obtained by operations similar to those in Reaction 4-1 and Reaction 5-4 using 2-[4-(4-fluoro-butyl)-cyclohexyl]-4-oxo-1,3,8-triaza-spiro[4.5]dec-1-ene-8-carboxylic acid tert-butyl ester as a starting material.

MS (ESI) m/z=549 (M+H)+.

Example 302

1-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-1-methyl-urea (Compound 1297)

1-(3,5-Dimethyl-4-{2-[2-(3-methyl-cyclohexyl)-4-oxo-1,3,8-triaza-spiro[4.5]dec-1-ene-8-sulfonyl]-ethyl}-phenyl)-1-methyl-urea (Compound 1297) was obtained by operations similar to those in Reaction 12-5 and Reaction 89-2 (using KOCN) using Compound 932 as a starting material.

MS (ESI) m/z=518 (M+H)+.

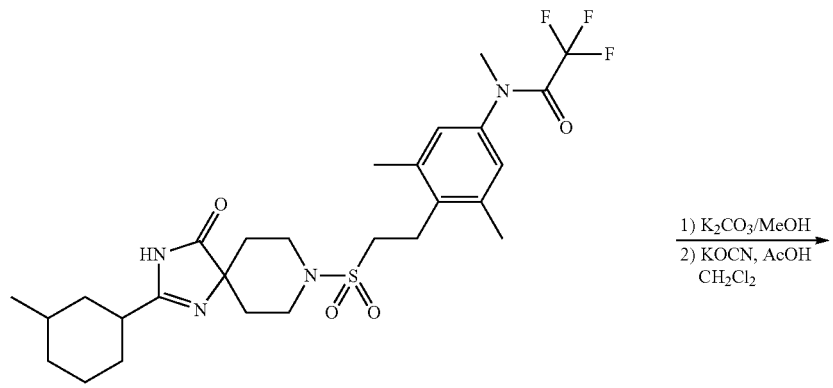

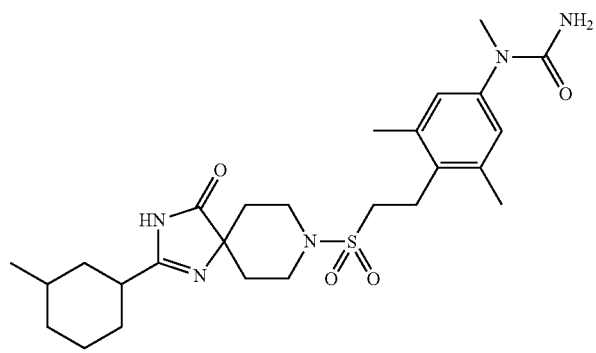

Example 303

1-(3,5-Dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea (Compound 1298)

(Reaction 303-1)

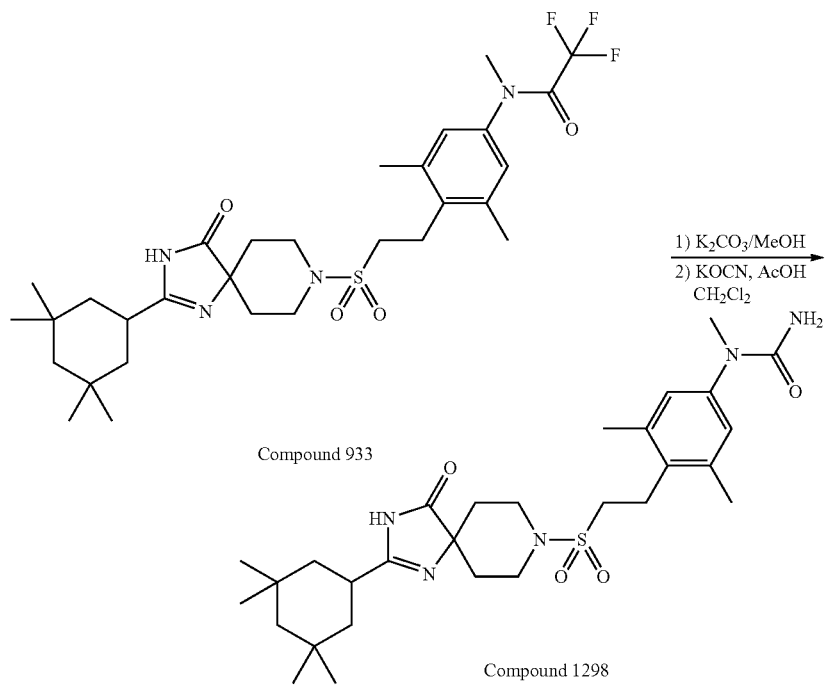

1-(3,5-Dimethyl-4-{2-[4-oxo-2-(3,3,5,5-tetramethyl-cyclohexyl)-1,3,8-triaza-spiro[4.5]dec-1-ene-8-sulfonyl]-ethyl}-phenyl)-1-methyl-urea (Compound 1298) was obtained by operations similar to those in Reaction 12-5 and Reaction 89-2 (using KOCN) using Compound 933 as a starting material.

MS (ESI) m/z=560 (M+H)+.

Example 304

3-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione (Compound 1299)

(Reaction 304-1)

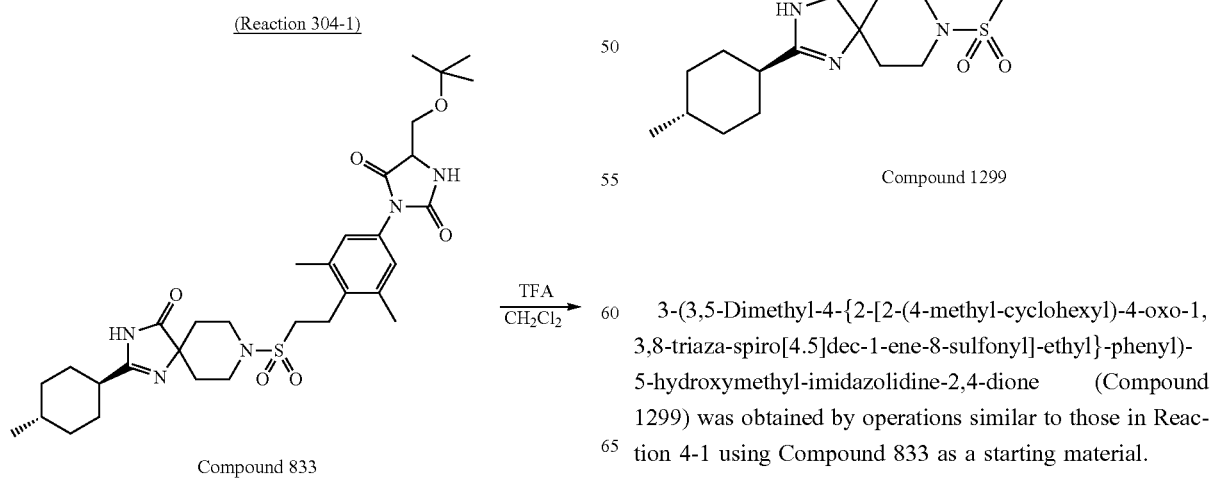

3-(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-5-hydroxymethyl-imidazolidine-2,4-dione (Compound 1299) was obtained by operations similar to those in Reaction 4-1 using Compound 833 as a starting material.

MS (ESI) m/z=574 (M+H)+.

Example 305

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea (Compound 1300)

(Reaction 305-1)

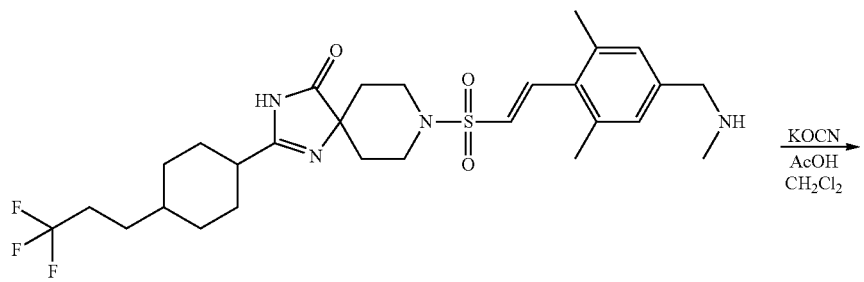

Compound 1193

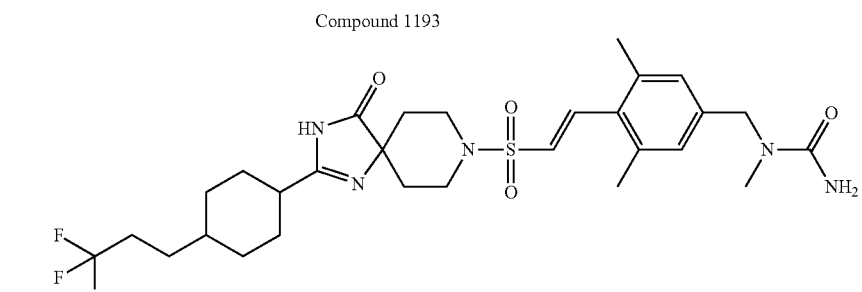

Compound 1300

1-[3,5-Dimethyl-4-((E)-2-{4-oxo-2-[4-(3,3,3-trifluoro-propyl)-cyclohexyl]-1,3,8-triaza-spiro[4.5]dec-1-ene-8-sulfonyl}-vinyl)-benzyl]-1-methyl-urea (Compound 1300) was obtained by operations similar to those in Reaction 89-2 (using KOCN) using Compound 1193 as a starting material.
MS (ESI) m/z=612 (M+H)+.

The example compounds shown below were obtained by operations similar to those in Reaction 305-1 using appropriate starting compounds.

Compounds 1301 to Compound 1312

TABLE 186

| Starting Compound | Target Compound | Structure | LCMS condition | Retention time (min) | MS (m/z) |
|---|---|---|---|---|---|
| 1289 | 1301 | 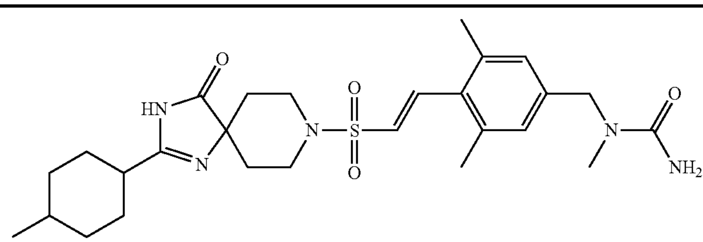 | LCMS-D-1 | 1.97 | 530 (M + H)+ |
| 1035 | 1302 | 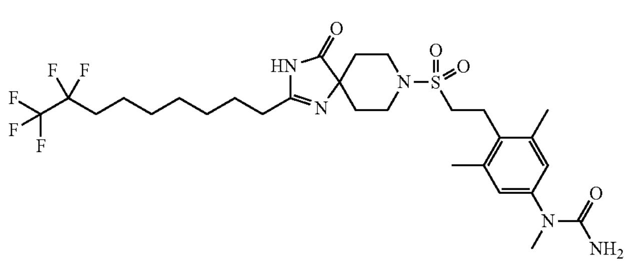 [SMILES: Cc1cc(N(C)C(N)=O)cc(C)c1CCS(=O)(=O)N1CCC2(CC1)N=C(CCCCCCCC(F)(F)C(F)(F)F)NC2=O] | LCMS-F-1 | 1.01 | 638 (M + H)+ |

TABLE 186-continued

| Starting Compound | Target Compound | Structure | LCMS condition | Retention time (min) | MS (m/z) |
|---|---|---|---|---|---|
| 691 | 1303 | 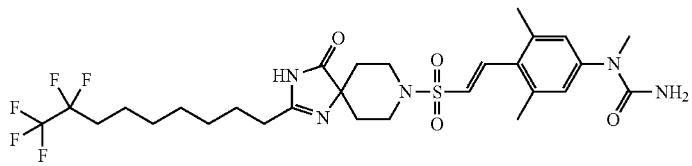 [SMILES: Cc1cc(N(C)C(N)=O)cc(C)c1/C=C/S(=O)(=O)N1CCC2(CC1)N=C(CCCCCCCC(F)(F)C(F)(F)F)NC2=O] | LCMS-F-1 | 1.01 | 636 (M + H)+ |
| 690 | 1304 | 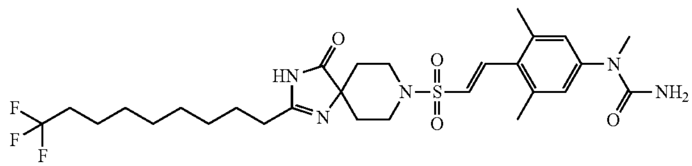 [SMILES: Cc1cc(N(C)C(N)=O)cc(C)c1/C=C/S(=O)(=O)N1CCC2(CC1)N=C(CCCCCCCCC(F)(F)F)NC2=O] | LCMS-F-1 | 1.00 | 600 (M + H)+ |
| 1016 | 1305 | 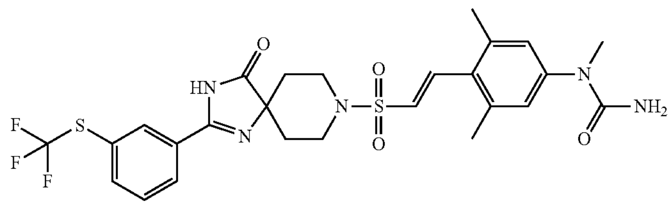 [SMILES: Cc1cc(N(C)C(N)=O)cc(C)c1/C=C/S(=O)(=O)N1CCC2(CC1)N=C(c1cccc(SC(F)(F)F)c1)NC2=O] | LCMS-C-1 | 2.75 | 596 (M + H)+ |
| 1036 | 1306 | 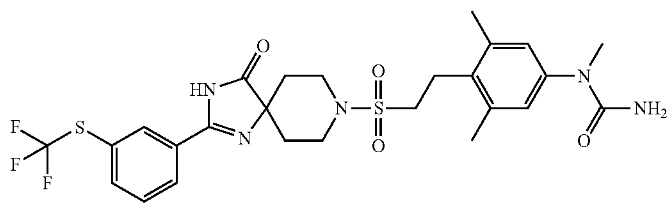 [SMILES: Cc1cc(N(C)C(N)=O)cc(C)c1CCS(=O)(=O)N1CCC2(CC1)N=C(c1cccc(SC(F)(F)F)c1)NC2=O] | LCMS-F-1 | 0.98 | 598 (M + H)+ |
| 1105 | 1307 | 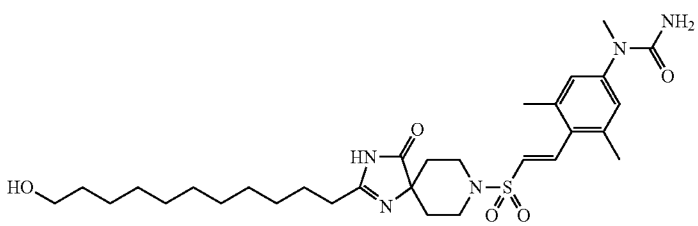 [SMILES: Cc1cc(N(C)C(N)=O)cc(C)c1/C=C/S(=O)(=O)N1CCC2(CC1)N=C(CCCCCCCCCCCO)NC2=O] | LCMS-C-1 | 2.70 | 590 (M + H)+ |
| 1106 | 1308 | 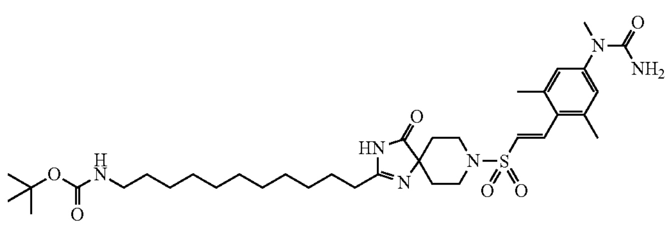 [SMILES: Cc1cc(N(C)C(N)=O)cc(C)c1/C=C/S(=O)(=O)N1CCC2(CC1)N=C(CCCCCCCCCCCNC(=O)OC(C)(C)C)NC2=O] | LCMS-C-1 | 2.98 | 689 (M + H)+ |
| 1107 | 1309 | 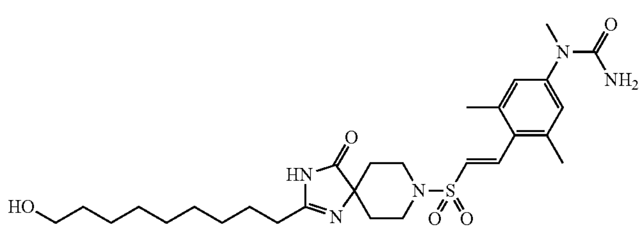 [SMILES: Cc1cc(N(C)C(N)=O)cc(C)c1/C=C/S(=O)(=O)N1CCC2(CC1)N=C(CCCCCCCCCO)NC2=O] | LCMS-F-1 | 0.92 | 562 (M + H)+ |

TABLE 186-continued
| Starting Compound | Target Compound | Structure | LCMS condition | Retention time (min) | MS (m/z) |
|---|---|---|---|---|---|
| 1037 | 1310 | 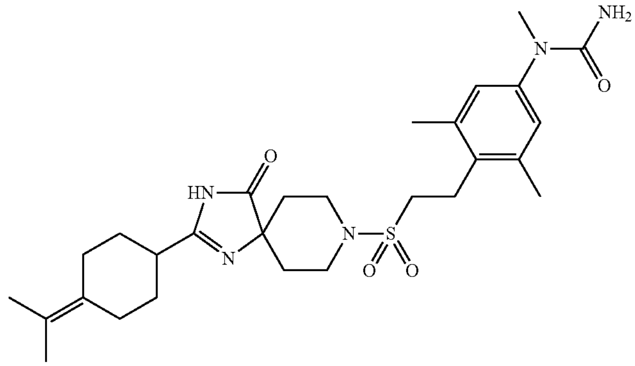 [SMILES: CC(C)=C1CCC(C2=NC3(CCN(S(=O)(=O)CCc4c(C)cc(N(C)C(N)=O)cc4C)CC3)C(=O)N2)CC1] | LCMS-A-1 | 2.10 | 544 (M + H)+ |
| 1287 | 1311 | 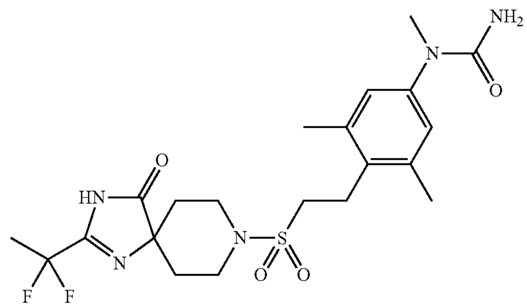 [SMILES: Cc1cc(N(C)C(N)=O)cc(C)c1CCS(=O)(=O)N1CCC2(CC1)N=C(C(C)(F)F)NC2=O] | LCMS-B-1 | 1.71 | 486 (M + H)+ |
| 1288 | 1312 | 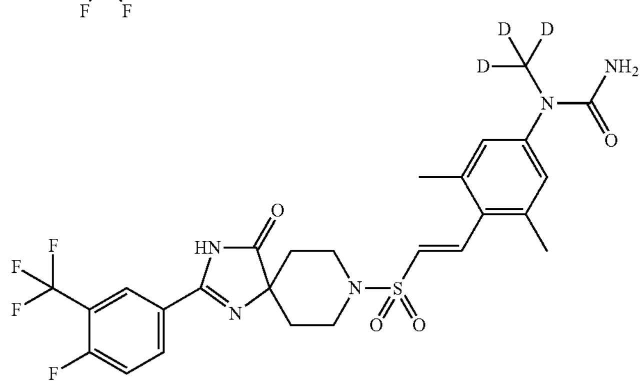 | LCMS-F-1 | 0.99 | 585 (M + H)+ |
Example 306
[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea (Compound 1313)
(Reaction 306-1)
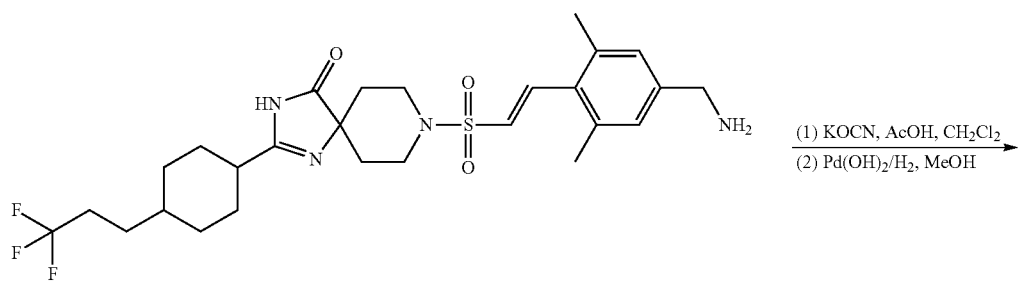
Compound 1290

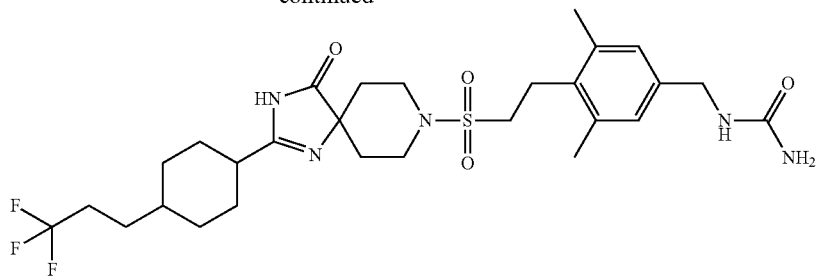

Compound 1313

[3,5-Dimethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-urea (Compound 1313) was obtained by operations similar to those in Reaction 89-2 (using KOCN) and Reaction 122-2 using Compound 1290 as a starting material.

MS (ESI) m/z=600 (M+H)+.

The example compound shown below was obtained by operations similar to those in Reaction 306-1 using an appropriate starting compound.

Compound 1314

TABLE 187

| Starting Compound | Target Compound | Structure | LCMS condition | Retention time (min) | MS (m/z) |
|---|---|---|---|---|---|
| 1291 | 1314 | 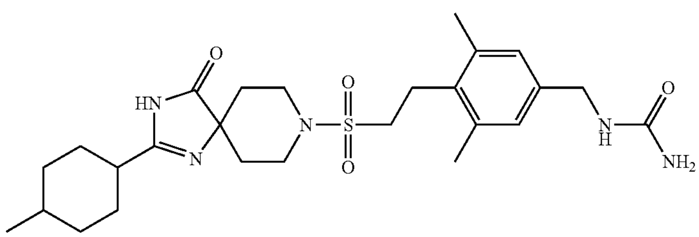 [SMILES: Cc1cc(CNC(N)=O)cc(C)c1CCS(=O)(=O)N1CCC2(CC1)N=C(C1CCC(C)CC1)NC2=O] | LCMS-D-1 | 1.78 | 518 (M + H)+ |

Example 307

1-(4-{(E)-2-[2-(11-Amino-undecyl)-4-oxo-1,3,8-triaza-spiro[4.5]dec-1-ene-8-sulfonyl]-vinyl}-3,5-dimethyl-phenyl)-1-methyl-urea (Compound 1315)

(Reaction 307-1)

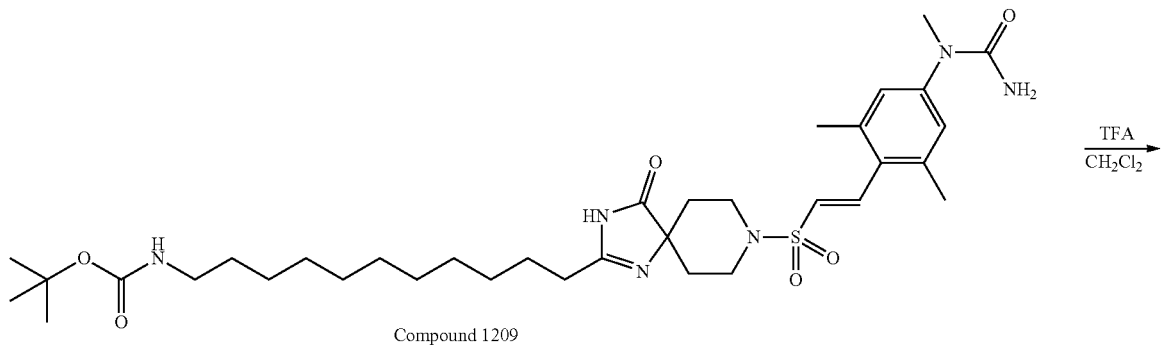

Compound 1209

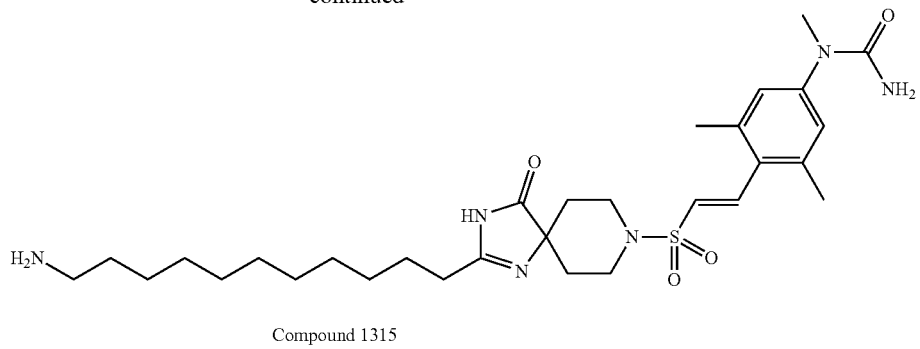

Compound 1315

1-(4-{(E)-2-[2-(11-Amino-undecyl)-4-oxo-1,3,8-triaza-spiro[4.5]dec-1-ene-8-sulfonyl]-vinyl}-3,5-dimethyl-phenyl)-1-methyl-urea (Compound 1315) was obtained by operations similar to those in Reaction 4-1 using Compound 1209 as a starting material.

MS (ESI) m/z=589 (M+H)+.

le;3qExample 308

1-[3,5-Dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea (Compound 1316)

five minutes in a nitrogen stream. The reaction mixture was quenched with a saturated aqueous sodium bicarbonate solution and then extracted with ethyl acetate. The organic layer was dried over anhydrous sodium sulfate and then concentrated under reduced pressure. The resulting residue was purified by column chromatography (silica gel, $CH_2Cl_2$-MeOH) to give 1-[3,5-dimethyl-4-((E)-2-{4-oxo-2-[5-(propane-1-sulfinyl)-pentyl]-1,3,8-triaza-spiro[4.5]dec-1-ene-8-sulfonyl}-vinyl)-phenyl]-1-methyl-urea (64 mg).

$^1$H-NMR (300 MHz, $CDCl_3$) δ 8.77 (s, 1H), 7.55 (d, 1H, J=15.6 Hz), 7.02 (s, 2H), 6.38 (d, 1H, J=15.6 Hz), 4.50 (s, 2H), 3.71-3.64 (m, 2H), 3.41-3.32 (m, 2H), 3.26 (s, 3H), (Reaction 308-1)

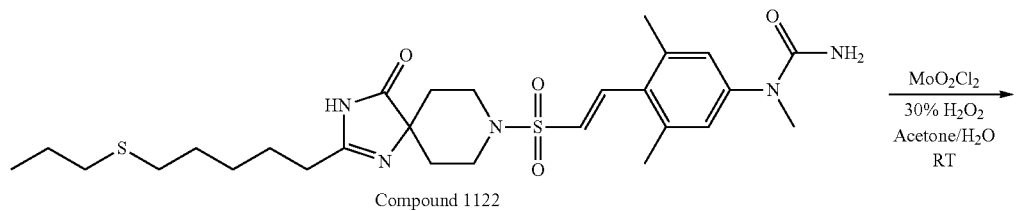

Compound 1122

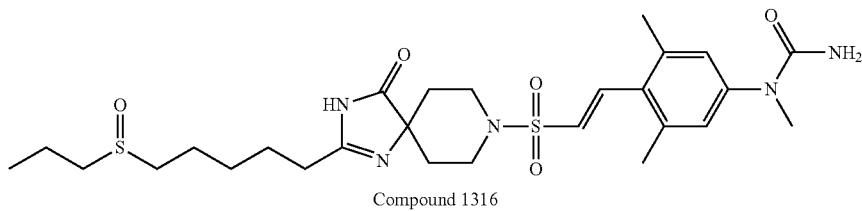

Compound 1316

30% aqueous hydrogen peroxide (0.013 ml) was added to a mixed solution of (E)-1-(3,5-dimethyl-4-(2-((4-oxo-2-(5-(propylthio)pentyl)-1,3,8-triazaspiro[4.5]dec-1-en-8-yl)sulfonyl)vinyl)phenyl)-1-methyl-urea (55 mg) and molybdenum(IV) dichloride dioxide (3 mg) in acetone (1.5 ml)-water (0.5 ml), and the mixture was stirred at room temperature for 2.76-2.54 (m, 4H), 2.52-2.43 (m, 2H), 2.38 (s, 6H), 2.00-1.61 (m, 12H), 1.09 (t, 3H, J=7.4 Hz).

MS (ESI) m/z=580 (M+H)+.

The example compound shown below was obtained by operations similar to those in Reaction 308-1 using an appropriate starting compound.

Compound 1317

TABLE 188

| Starting Compound | Target Compound | Structure | LCMS condition | Retention time (min) | MS (m/z) |
|---|---|---|---|---|---|
| 1154 | 1317 | 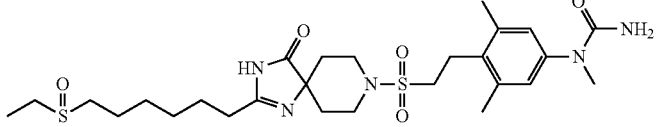 | LCMS-D-1 | 1.42 | 582 (M + H)+ |

Example 309

1-[3,5-Dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea (Compound 1318)

(Reaction 309-1)

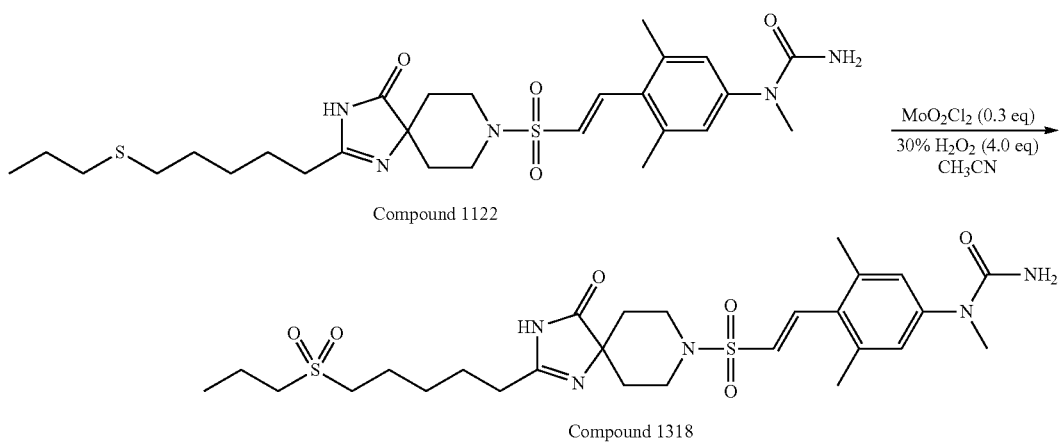

30% aqueous hydrogen peroxide (0.047 ml) was added to a mixed solution of (E)-1-(3,5-dimethyl-4-(2-((4-oxo-2-(5-(propylthio)pentyl)-1,3,8-triazaspiro[4.5]dec-1-en-8-yl)sulfonyl)vinyl)phenyl)-1-methylurea (61 mg) and molybdenum(IV) dichloride dioxide (6.5 mg) in acetonitrile (1 ml), and the mixture was stirred at room temperature for two hours in a nitrogen stream. The reaction mixture was quenched with a saturated aqueous sodium bicarbonate solution and then extracted with ethyl acetate. The organic layer was dried over anhydrous sodium sulfate and then concentrated under reduced pressure. The resulting residue was purified by column chromatography (silica gel, $CH_2Cl_2$-MeOH) to give 1-[3,5-dimethyl-4-((E)-2-{4-oxo-2-[5-(propane-1-sulfonyl)-pentyl]-1,3,8-triaza-spiro[4.5]dec-1-ene-8-sulfonyl}-vinyl)-phenyl]-1-methyl-urea (64 mg).

$^1$H-NMR (300 MHz, CDCl$_3$) δ 8.96 (s, 1H), 7.54 (d, 1H, J=15.6 Hz), 7.02 (s, 2H), 6.39 (d, 1H, J=15.6 Hz), 4.68 (s, 2H), 3.68-3.61 (m, 2H), 3.45-3.37 (m, 2H), 3.25 (s, 3H), 2.98-2.91 (m, 4H), 2.48 (t, 2H, J=7.4 Hz), 2.37 (s, 6H), 1.98-1.84 (m, 6H), 1.81-1.70 (m, 4H), 1.66-1.57 (m, 2H), 1.09 (t, 3H, J=7.4 Hz).

MS (ESI) m/z=596 (M+H)+.

The example compounds shown below were obtained by operations similar to those in Reaction 309-1 using appropriate starting compounds.

Compounds 1319 to Compound 1320

TABLE 189

| Starting Compound | Target Compound | Structure | LCMS condition | Retention time (min) | MS (m/z) |
|---|---|---|---|---|---|
| 1022 | 1319 | 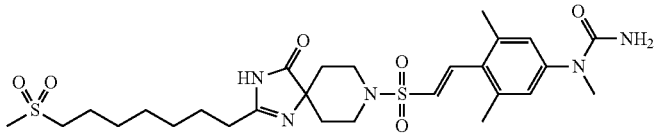 [SMILES: Cc1cc(N(C)C(N)=O)cc(C)c1/C=C/S(=O)(=O)N1CCC2(CC1)N=C(CCCCCCCS(C)(=O)=O)NC2=O] | LCMS-D-1 | 1.52 | 596 (M + H)+ |

TABLE 189-continued

| Starting Compound | Target Compound | Structure | LCMS condition | Retention time (min) | MS (m/z) |
|---|---|---|---|---|---|
| 1154 | 1320 | 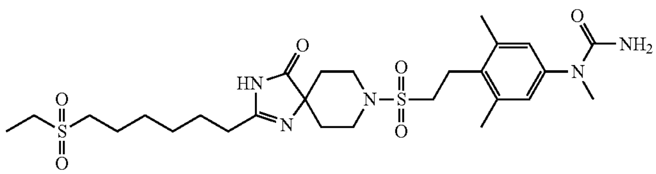 [SMILES: CCS(=O)(=O)CCCCCCC1=NC2(CCN(S(=O)(=O)CCc3c(C)cc(N(C)C(N)=O)cc3C)CC2)C(=O)N1] | LCMS-D-1 | 1.49 | 598 (M + H)+ |

Example 310

1-(4-{(E)-2-[2-(9,9-Difluoro-nonyl)-4-oxo-1,3,8-triaza-spiro[4.5]dec-1-ene-8-sulfonyl]-vinyl}-3,5-dimethyl-phenyl)-1-methyl-urea (Compound 1321)

(Reaction 310-1)

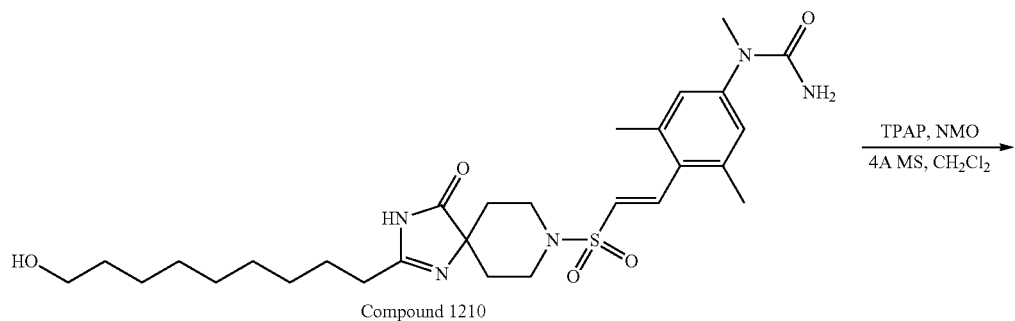

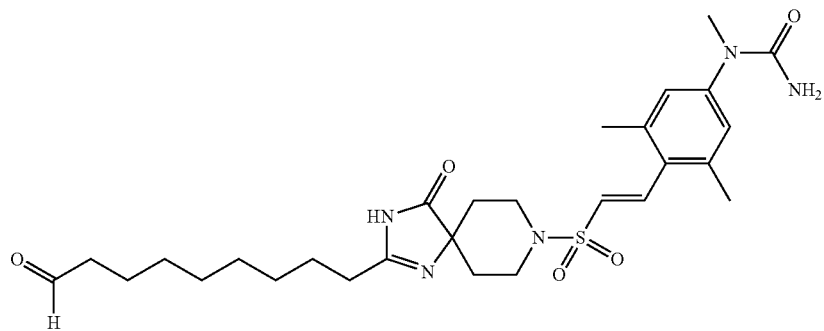

NMO (22.0 mg, 0.192 mmol), Molecular Sieves 4 A (25.0 mg) and TPAP (0.700 mg, 0.00213 mmol) were added to a solution of 1-(4-{2-[2-(9-hydroxy-nonyl)-4-oxo-1,3,8-triaza-spiro[4.5]dec-1-ene-8-sulfonyl]-ethyl}-3,5-dimethyl-phenyl)-1-methyl-urea (24.0 mg, 0.0426 mmol) in $CH_2Cl_2$ (850 µl) at room temperature. The mixture was stirred at room temperature for one hour and then filtered through celite, and the filtrate was concentrated under reduced pressure. The residue was purified by silica gel chromatography to give 1-(3,5-dimethyl-4-{(E)-2-[4-oxo-2-(9-oxo-nonyl)-1,3,8-triaza-spiro[4.5]dec-1-ene-8-sulfonyl]-vinyl}-phenyl)-1-methyl-urea (17.0 mg, 71%).

MS (ESI) m/z=562 (M+H)+.

(Reaction 310-2)

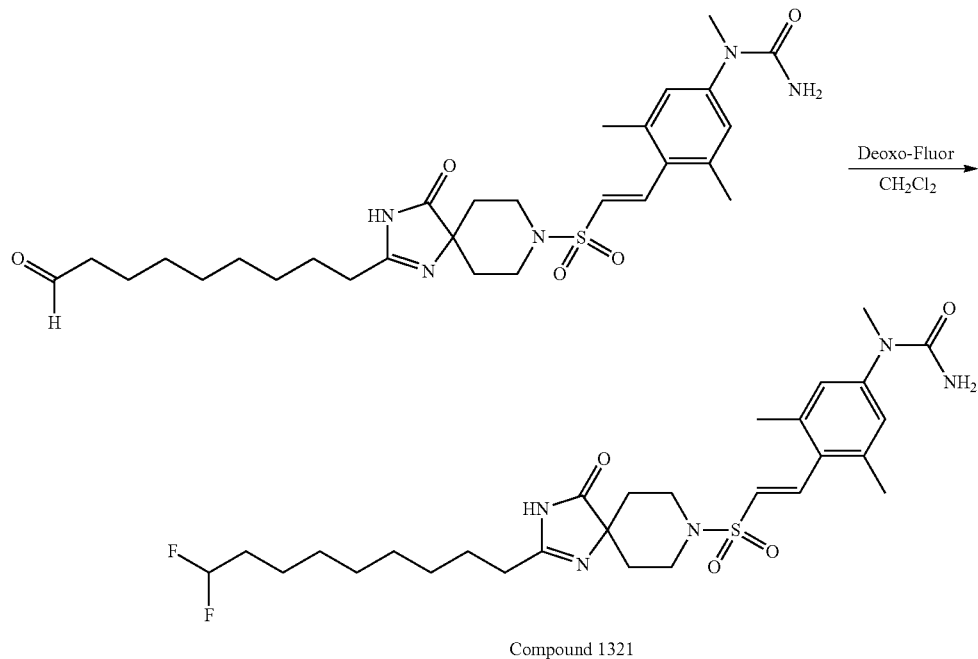

Compound 1321

1-(4-{(E)-2-[2-(9,9-Difluoro-nonyl)-4-oxo-1,3,8-triaza-spiro[4.5]dec-1-ene-8-sulfonyl]-vinyl}-3,5-dimethyl-phenyl)-1-methyl-urea (Compound 1321) was obtained by operations similar to those in Reaction 191-11 using 1-(3,5-dimethyl-4-{(E)-2-[4-oxo-2-(9-oxo-nonyl)-1,3,8-triaza-spiro[4.5]dec-1-ene-8-sulfonyl]-vinyl}-phenyl)-1-methyl-urea as a starting material.

MS (ESI) m/z=582 (M+H)+.

Example 311

1-(4-{2-[2-(9-Hydroxy-nonyl)-4-oxo-1,3,8-triaza-spiro[4.5]dec-1-ene-8-sulfonyl]-ethyl}-3,5-dimethyl-phenyl)-1-methyl-urea (Compound 1322)

(Reaction 311-1)

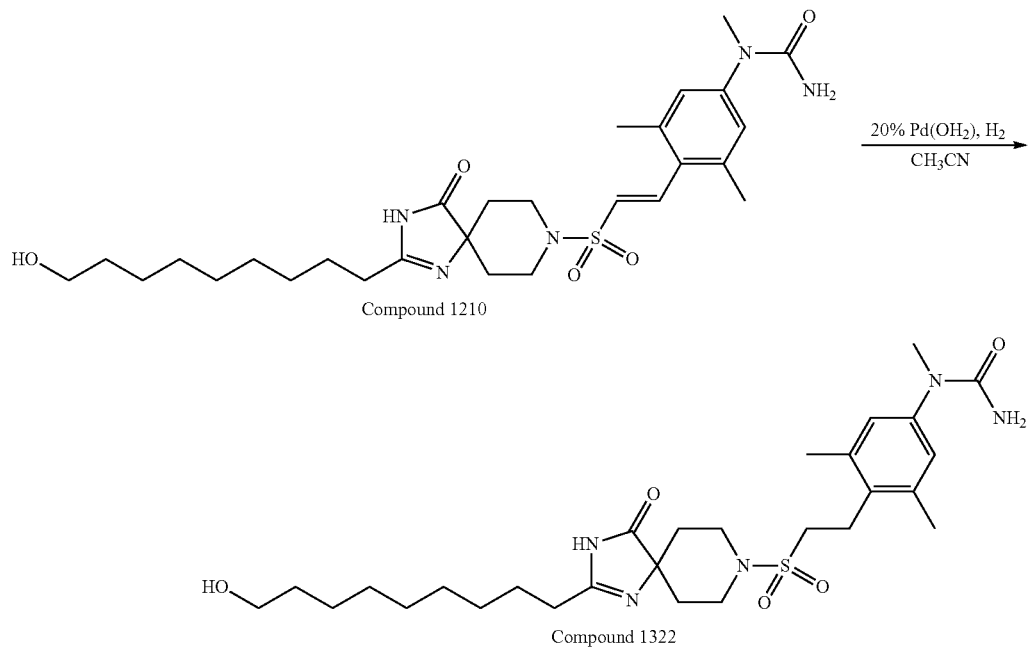

Compound 1210

Compound 1322

1499

1-(4-{2-[2-(9-Hydroxy-nonyl)-4-oxo-1,3,8-triaza-spiro[4.5]dec-1-ene-8-sulfonyl]-ethyl}-3,5-dimethyl-phenyl)-1-methyl-urea (Compound 1322) was obtained by operations similar to those in Reaction 184-1 using Compound 1210 as a starting material and acetonitrile as a solvent.

MS (ESI) m/z=564 (M+H)+.

Example 312

1-(4-{2-[2-(9,9-Difluoro-nonyl)-4-oxo-1,3,8-triaza-spiro[4.5]dec-1-ene-8-sulfonyl]-ethyl}-3,5-dimethyl-phenyl)-1-methyl-urea (Compound 1323)

1500

1-(4-{2-[2-(9,9-Difluoro-nonyl)-4-oxo-1,3,8-triaza-spiro[4.5]dec-1-ene-8-sulfonyl]-ethyl}-3,5-dimethyl-phenyl)-1-methyl-urea (Compound 1323) was obtained by operations similar to those in Reaction 310-1 and Reaction 191-11 using Compound 1260 as a starting material.

MS (ESI) m/z=584 (M+H)+.

(Reaction 312-1)

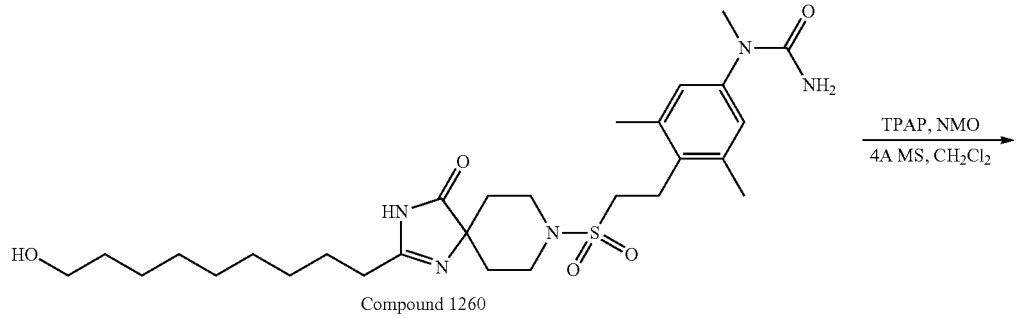

Compound 1260

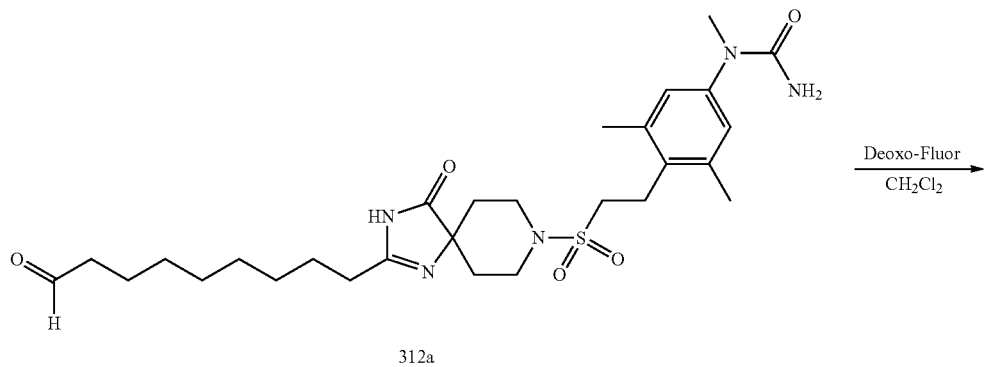

312a

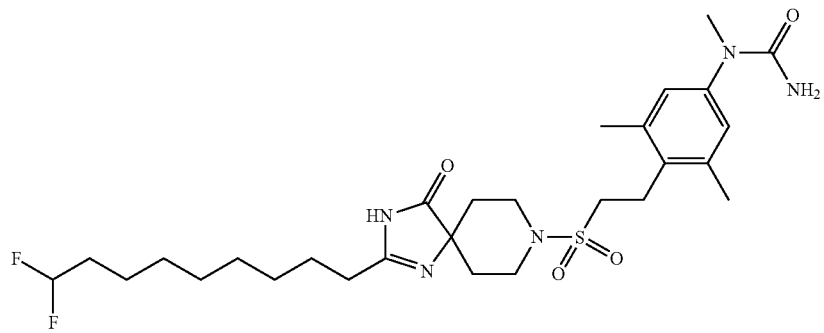

Compound 1323

Example 313

1-(4-{2-[2-(9-Amino-nonyl)-4-oxo-1,3,8-triaza-spiro[4.5]dec-1-ene-8-sulfonyl]-ethyl}-3,5-dimethyl-phenyl)-1-methyl-urea (Compound 1324)

1-(4-{2-[2-(9-Amino-nonyl)-4-oxo-1,3,8-triaza-spiro[4.5]dec-1-ene-8-sulfonyl]-ethyl}-3,5-dimethyl-phenyl)-1-methyl-urea (Compound 1324) was obtained by operations similar to those in Reaction 310-1 and Reaction 80-1 (using NaBH$_3$CN as a reducing agent and methanol as a solvent) using Compound 1260 as a starting material.

MS (ESI) m/z=563 (M+H)+.

(Reaction 313-1)

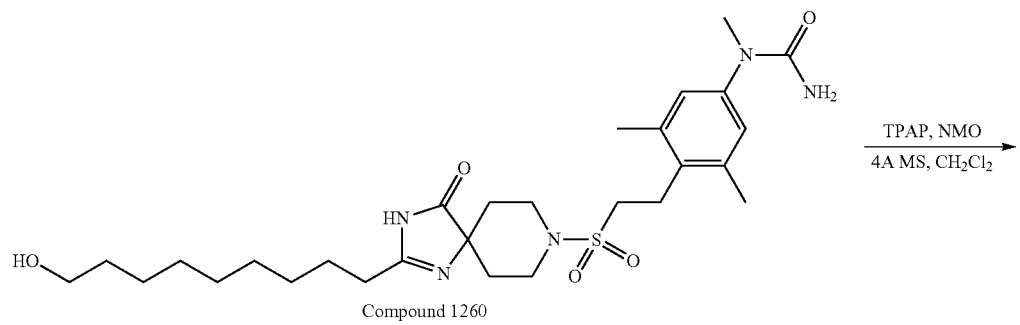

Compound 1260

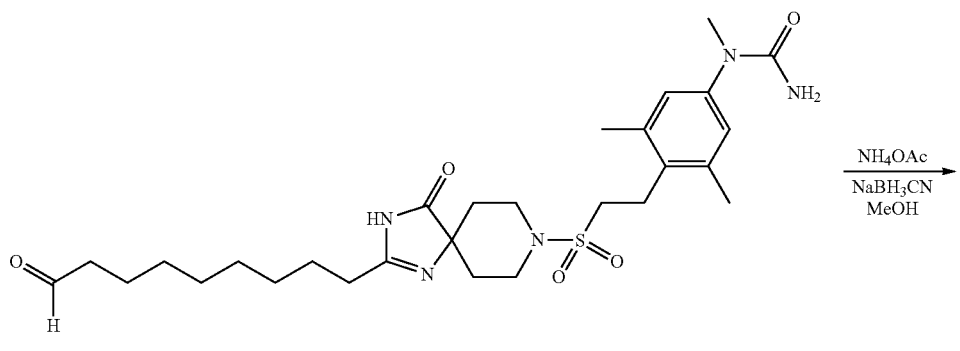

313a

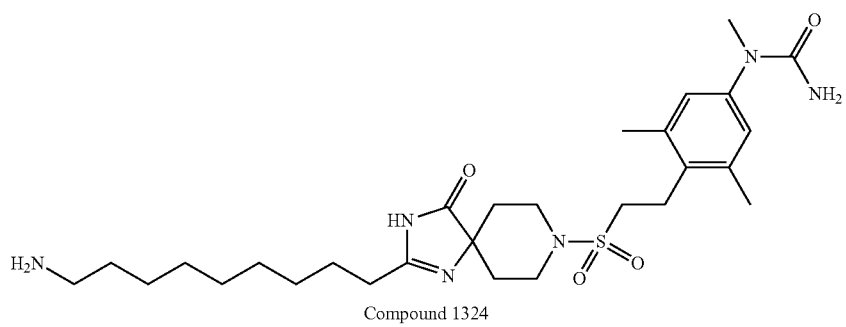

Compound 1324

Example 314

1-(4-{(E)-2-[2-(9-Fluoro-nonyl)-4-oxo-1,3,8-triaza-spiro[4.5]dec-1-ene-8-sulfonyl]-vinyl}-3,5-dimethyl-phenyl)-1-methyl-urea (Compound 1325) and 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea (Compound 1326)

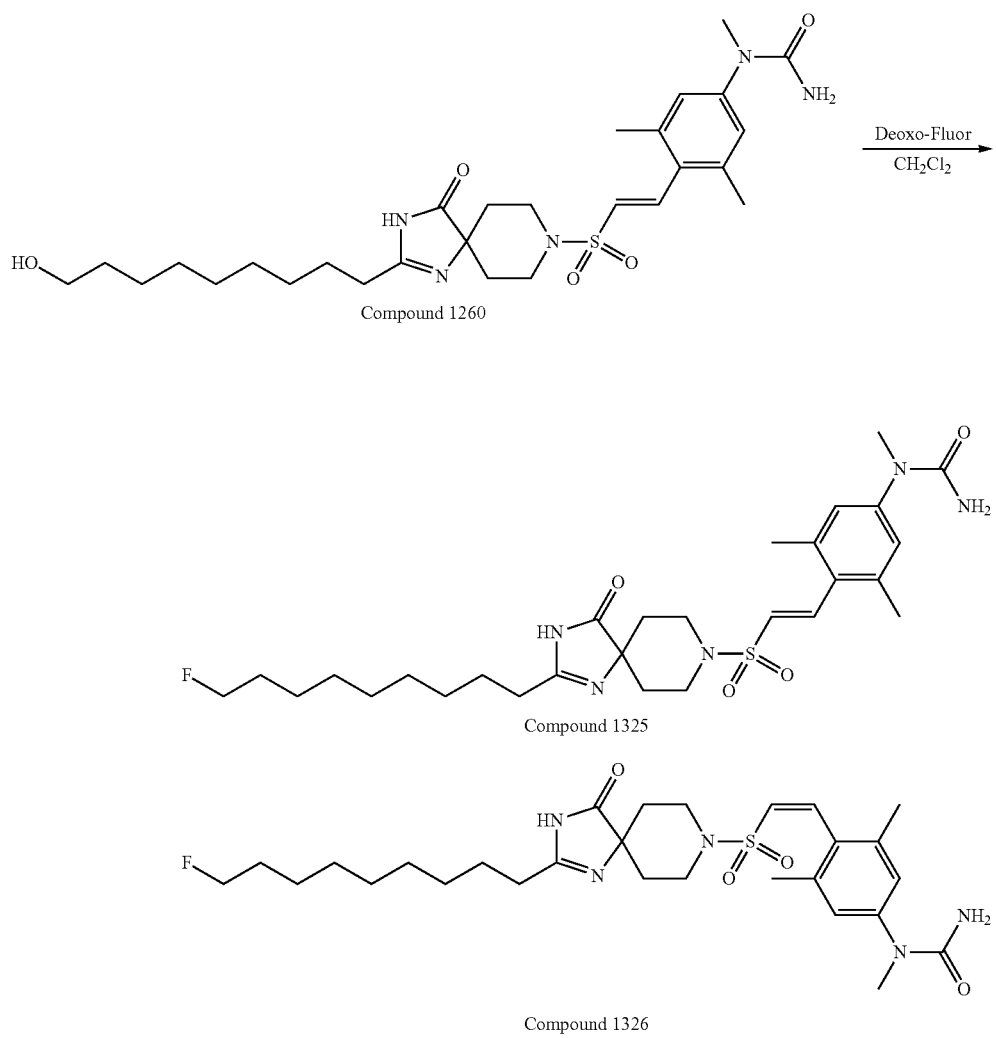

(Reaction 314-1)

Compound 1260

Compound 1325

Compound 1326

1-(4-{(E)-2-[2-(9-Fluoro-nonyl)-4-oxo-1,3,8-triaza-spiro[4.5]dec-1-ene-8-sulfonyl]-vinyl}-3,5-dimethyl-phenyl)-1-methyl-urea (Compound 1325)

MS (ESI) m/z=564 (M+H)+ and 1-(4-{(Z)-2-[2-(9-fluoro-nonyl)-4-oxo-1,3,8-triaza-spiro[4.5]dec-1-ene-8-sulfonyl]-vinyl}-3,5-dimethyl-phenyl)-1-methyl-urea (Compound 1326)

MS (ESI) m/z=564 (M+H)+ were obtained by operations similar to those in Reaction 191-11 using Compound 1260 as a starting material.

Example 315

1-(4-{2-[2-(9-Fluoro-nonyl)-4-oxo-1,3,8-triaza-spiro[4.5]dec-1-ene-8-sulfonyl]-ethyl}-3,5-dimethyl-phenyl)-1-methyl-urea (Compound 1327)

(Reaction 315-1)

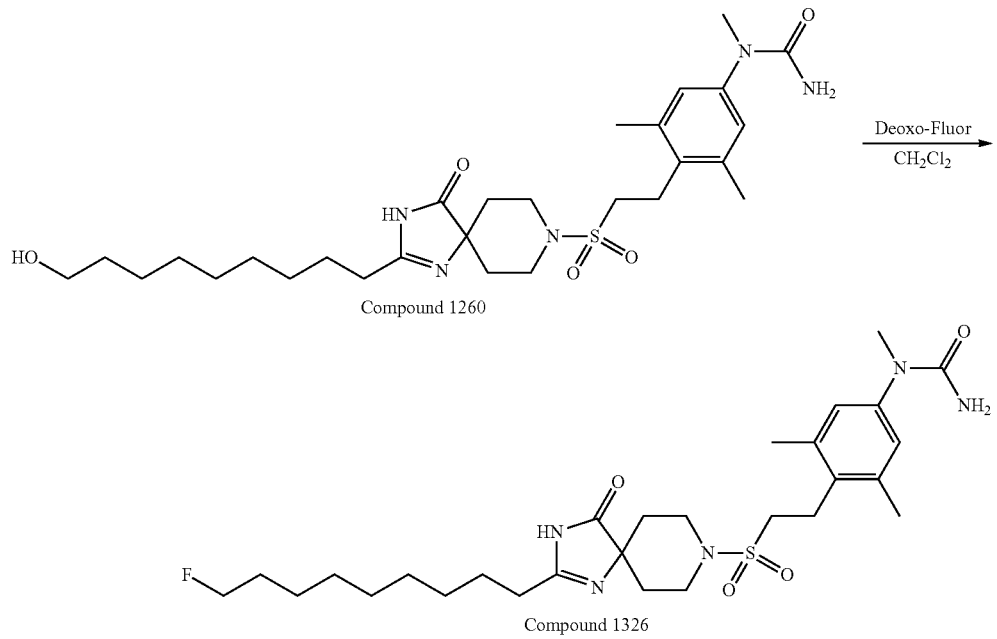

Compound 1260

Compound 1326

1-(4-{2-[2-(9-Fluoro-nonyl)-4-oxo-1,3,8-triaza-spiro[4.5]dec-1-ene-8-sulfonyl]-ethyl}-3,5-dimethyl-phenyl)-1-methyl-urea (Compound 1327) was obtained by operations similar to those in Reaction 191-11 using Compound 1260 as a starting material.

MS (ESI) m/z=566 (M+H)+.

Example 316

8-{2-[4-((R)-2,3-Dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one (Compound 1328)

(Reaction 316-1)

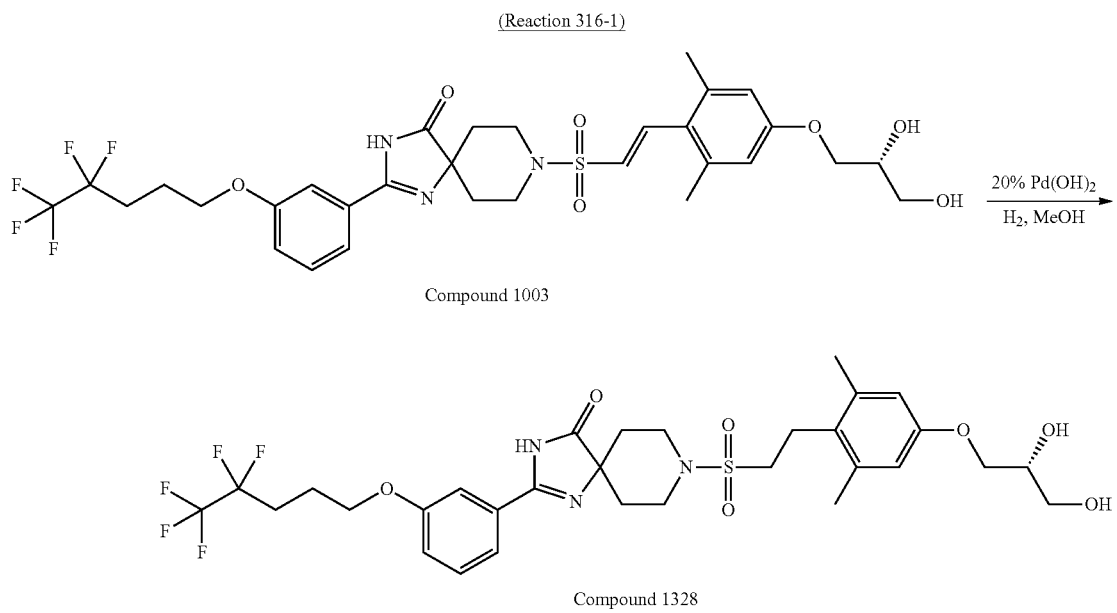

Compound 1003

Compound 1328

8-{2-[4-((R)-2,3-Dihydroxy-propoxy)-2,6-dimethyl-phenyl]-ethanesulfonyl}-2-[3-(4,4,5,5,5-pentafluoro-pentyloxy)-phenyl]-1,3,8-triaza-spiro[4.5]dec-1-en-4-one (Compound 1328) was obtained by operations similar to those in Reaction 122-2 using Compound 1003 as a starting material.

MS (ESI) m/z=692 (M+H)+.

The example compounds shown below were obtained by operations similar to those in Reaction 316-1 using appropriate solvents (acetonitrile or methanol or an acetonitrile-methanol mixed solution) and starting compounds.

Compounds 1329 to Compound 1364

TABLE 190

| Starting Compound | Target Compound | Structure | LCMS condition | Retention time (min) | MS (m/z) |
|---|---|---|---|---|---|
| 1164 | 1329 | 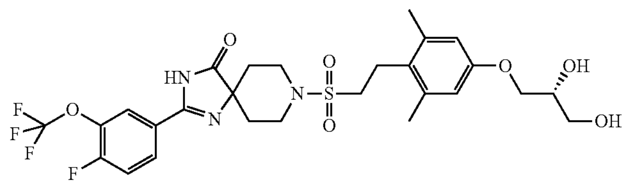 [SMILES: Cc1cc(OC[C@H](O)CO)cc(C)c1CCS(=O)(=O)N1CCC2(CC1)N=C(c1ccc(F)c(OC(F)(F)F)c1)NC2=O] | LCMS-F-1 | 0.95 | 618 (M + H)+ |
| 1165 | 1330 | 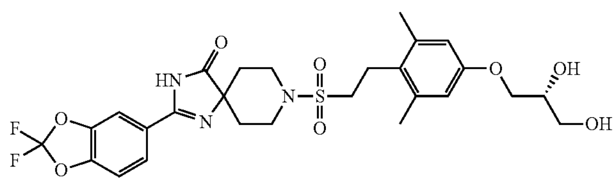 [SMILES: Cc1cc(OC[C@H](O)CO)cc(C)c1CCS(=O)(=O)N1CCC2(CC1)N=C(c1ccc3c(c1)OC(F)(F)O3)NC2=O] | LCMS-F-1 | 0.93 | 596 (M + H)+ |
| 1167 | 1331 | 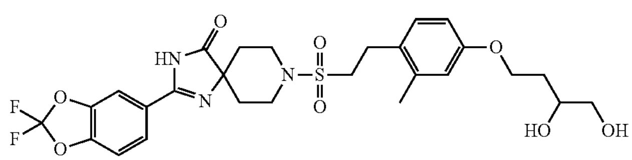 [SMILES: Cc1cc(OCCC(O)CO)ccc1CCS(=O)(=O)N1CCC2(CC1)N=C(c1ccc3c(c1)OC(F)(F)O3)NC2=O] | LCMS-F-1 | 0.94 | 596 (M + H)+ |
| 1166 | 1332 | 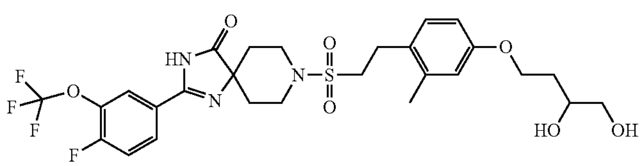 [SMILES: Cc1cc(OCCC(O)CO)ccc1CCS(=O)(=O)N1CCC2(CC1)N=C(c1ccc(F)c(OC(F)(F)F)c1)NC2=O] | LCMS-F-1 | 0.96 | 618 (M + H)+ |
| 1160 | 1333 | 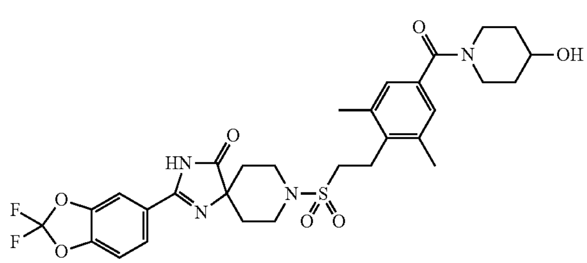 [SMILES: Cc1cc(C(=O)N2CCC(O)CC2)cc(C)c1CCS(=O)(=O)N1CCC2(CC1)N=C(c1ccc3c(c1)OC(F)(F)O3)NC2=O] | LCMS-F-1 | 0.93 | 633 (M + H)+ |
| 1159 | 1334 | 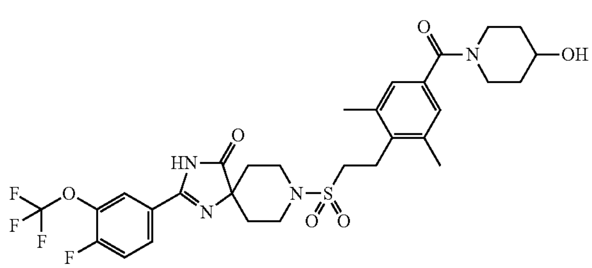 [SMILES: Cc1cc(C(=O)N2CCC(O)CC2)cc(C)c1CCS(=O)(=O)N1CCC2(CC1)N=C(c1ccc(F)c(OC(F)(F)F)c1)NC2=O] | LCMS-F-1 | 0.95 | 655 (M + H)+ |

TABLE 190-continued

| Starting Compound | Target Compound | Structure | LCMS condition | Retention time (min) | MS (m/z) |
|---|---|---|---|---|---|
| 1099 | 1335 | 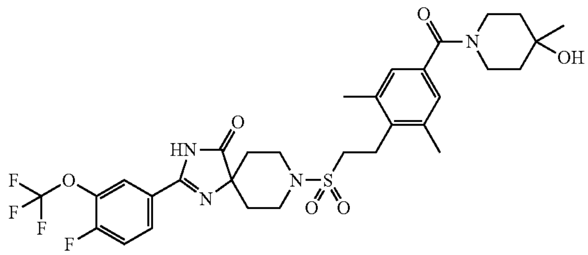 [SMILES: Cc1cc(C(=O)N2CCC(C)(O)CC2)cc(C)c1CCS(=O)(=O)N1CCC2(CC1)N=C(c1ccc(F)c(OC(F)(F)F)c1)NC2=O] | LCMS-F-1 | 1.01 | 669 (M + H)+ |
| 1163 | 1336 | 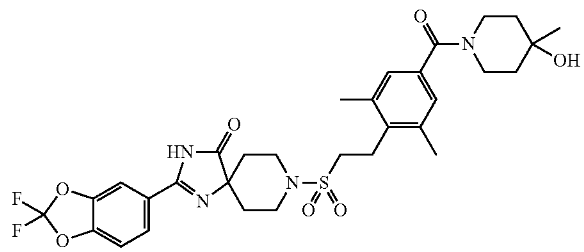 [SMILES: Cc1cc(C(=O)N2CCC(C)(O)CC2)cc(C)c1CCS(=O)(=O)N1CCC2(CC1)N=C(c1ccc3c(c1)OC(F)(F)O3)NC2=O] | LCMS-F-1 | 1.00 | 647 (M + H)+ |
| 1102 | 1337 | 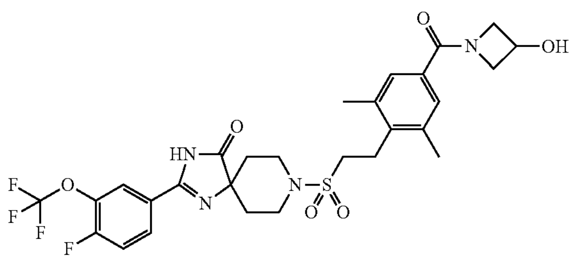 [SMILES: Cc1cc(C(=O)N2CC(O)C2)cc(C)c1CCS(=O)(=O)N1CCC2(CC1)N=C(c1ccc(F)c(OC(F)(F)F)c1)NC2=O] | LCMS-F-1 | 0.96 | 627 (M + H)+ |
| 1019 | 1338 | 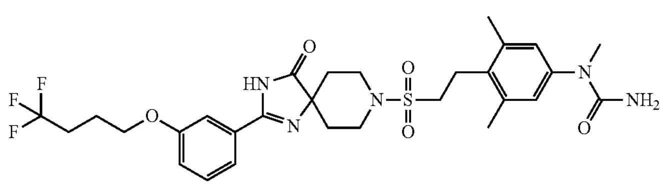 [SMILES: Cc1cc(N(C)C(N)=O)cc(C)c1CCS(=O)(=O)N1CCC2(CC1)N=C(c1cccc(OCCCC(F)(F)F)c1)NC2=O] | LCMS-F-1 | 0.98 | 624 (M + H)+ |
| 1020 | 1339 | 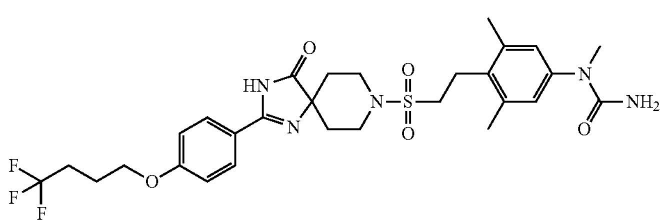 [SMILES: Cc1cc(N(C)C(N)=O)cc(C)c1CCS(=O)(=O)N1CCC2(CC1)N=C(c1ccc(OCCCC(F)(F)F)cc1)NC2=O] | LCMS-F-1 | 0.97 | 624 (M + H)+ |
| 1133 | 1340 | 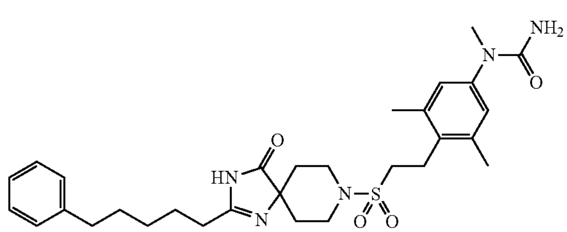 [SMILES: Cc1cc(N(C)C(N)=O)cc(C)c1CCS(=O)(=O)N1CCC2(CC1)N=C(CCCCCc1ccccc1)NC2=O] | LCMS-F-1 | 1.01 | 568 (M + H)+ |

TABLE 190-continued

| Starting Compound | Target Compound | Structure | LCMS condition | Retention time (min) | MS (m/z) |
|---|---|---|---|---|---|
| 1112 | 1341 | 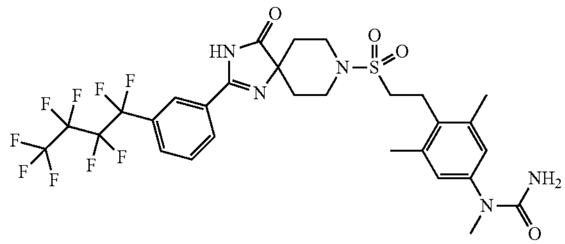 [SMILES: Cc1cc(N(C)C(N)=O)cc(C)c1CCS(=O)(=O)N1CCC2(CC1)N=C(c1cccc(C(F)(F)C(F)(F)C(F)(F)C(F)(F)F)c1)NC2=O] | LCMS-F-1 | 1.07 | 716 (M + H)+ |
| 1021 | 1342 | 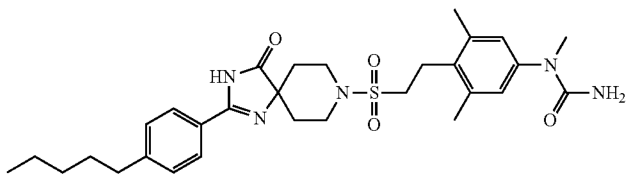 [SMILES: CCCCCc1ccc(C2=NC3(CCN(S(=O)(=O)CCc4c(C)cc(N(C)C(N)=O)cc4C)CC3)C(=O)N2)cc1] | LCMS-F-1 | 1.06 | 568 (M + H)+ |
| 1108 | 1343 | 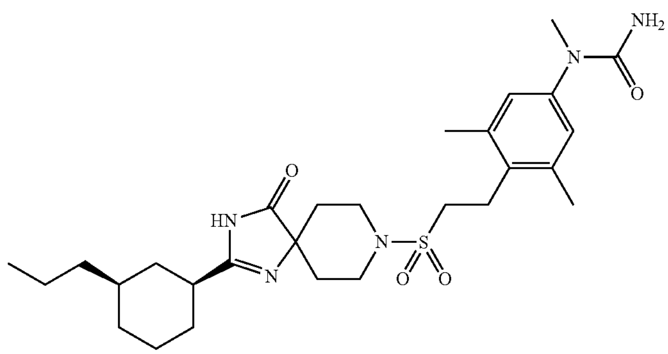 [SMILES: CCC[C@@H]1CCC[C@H](C2=NC3(CCN(S(=O)(=O)CCc4c(C)cc(N(C)C(N)=O)cc4C)CC3)C(=O)N2)C1] | LCMS-F-1 | 1.01 | 546 (M + H)+ |
| 1115 | 1344 | 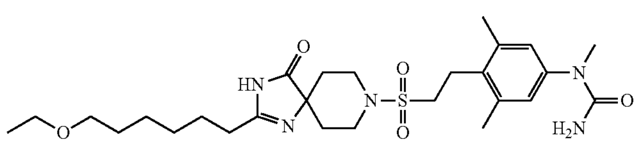 [SMILES: CCOCCCCCCC1=NC2(CCN(S(=O)(=O)CCc3c(C)cc(N(C)C(N)=O)cc3C)CC2)C(=O)N1] | LCMS-D-1 | 1.76 | 550 (M + H)+ |
| 1116 | 1345 | 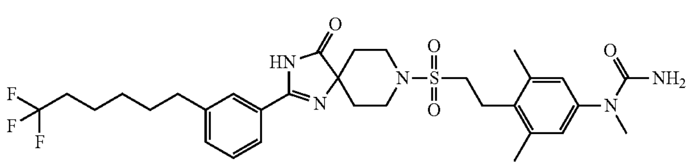 [SMILES: Cc1cc(N(C)C(N)=O)cc(C)c1CCS(=O)(=O)N1CCC2(CC1)N=C(c1cccc(CCCCCC(F)(F)F)c1)NC2=O] | LCMS-D-1 | 2.82 | 636 (M + H)+ |
| 1117 | 1346 | 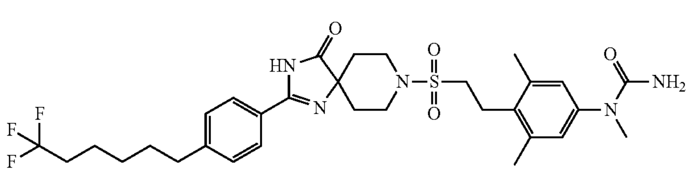 [SMILES: Cc1cc(N(C)C(N)=O)cc(C)c1CCS(=O)(=O)N1CCC2(CC1)N=C(c1ccc(CCCCCC(F)(F)F)cc1)NC2=O] | LCMS-D-1 | 2.73 | 636 (M + H)+ |
| 1132 | 1347 | 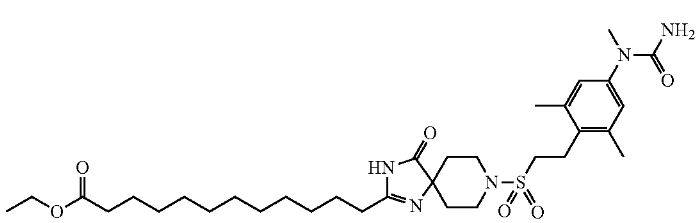 [SMILES: CCOC(=O)CCCCCCCCCCCC1=NC2(CCN(S(=O)(=O)CCc3c(C)cc(N(C)C(N)=O)cc3C)CC2)C(=O)N1] | LCMS-C-1 | 3.02 | 648 (M + H)+ |

TABLE 190-continued
| Starting Compound | Target Compound | Structure | LCMS condition | Retention time (min) | MS (m/z) |
|---|---|---|---|---|---|
| 1121 | 1348 | 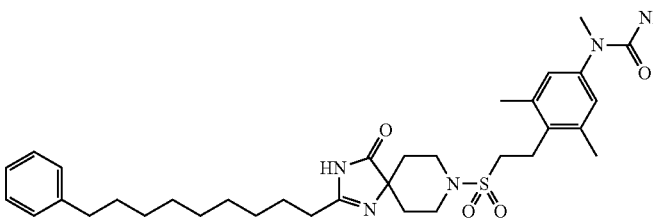 | LCMS-C-1 | 3.17 | 624 (M + H)+ |
| 1120 | 1349 | 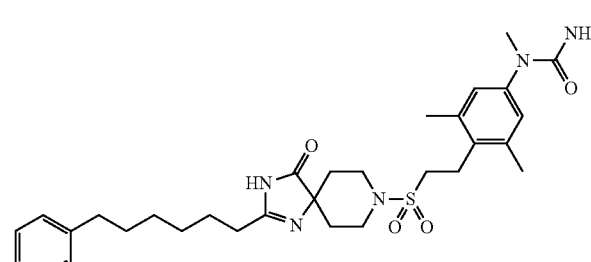 | LCMS-C-1 | 2.87 | 582 (M + H)+ |
| 1109 | 1350 | 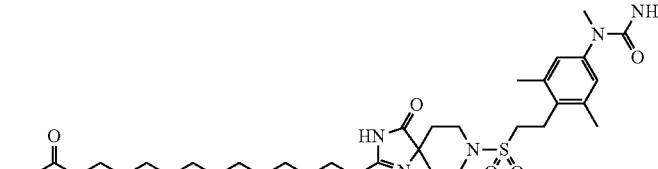 | LCMS-C-1 | 2.73 | 648 (M + H)+ |
| 1123 | 1351 | 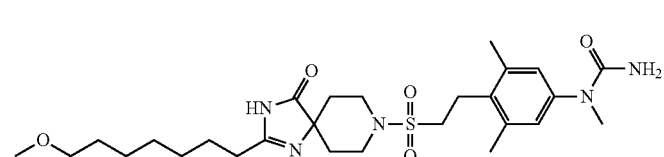 | LCMS-D-1 | 1.77 | 550 (M + H)+ |
| 1124 | 1352 | 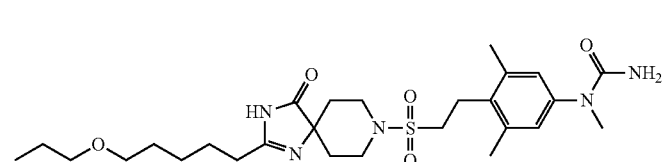 | LCMS-D-1 | 1.58 | 550 (M + H)+ |
| 1126 | 1353 | 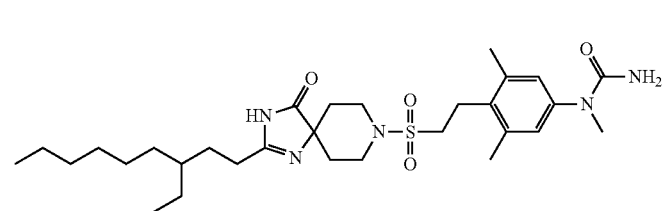 | LCMS-D-1 | 2.45 | 590 (M + H)+ |
| 1128 | 1354 | 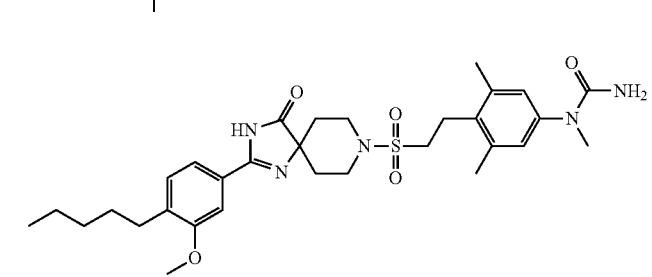 | LCMS-D-1 | 2.98 | 598 (M + H)+ |

TABLE 190-continued

| Starting Compound | Target Compound | Structure | LCMS condition | Retention time (min) | MS (m/z) |
|---|---|---|---|---|---|
| 1127 | 1355 | 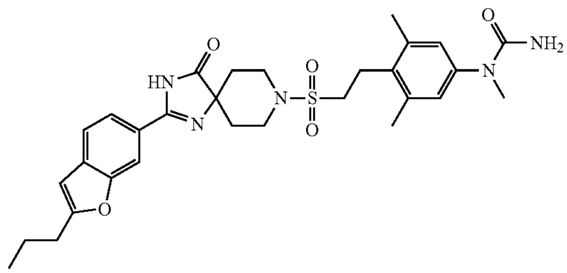 [SMILES: CCCc1cc2ccc(C3=NC4(CCN(S(=O)(=O)CCc5c(C)cc(N(C)C(N)=O)cc5C)CC4)C(=O)N3)cc2o1] | LCMS-D-1 | 2.10 | 580 (M + H)+ |
| 1318 | 1356 | 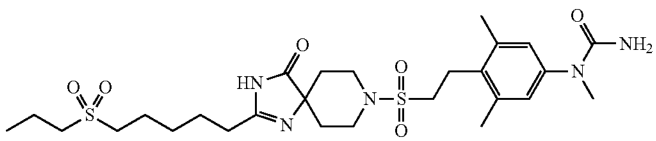 [SMILES: CCCS(=O)(=O)CCCCCC1=NC2(CCN(S(=O)(=O)CCc3c(C)cc(N(C)C(N)=O)cc3C)CC2)C(=O)N1] | LCMS-D-1 | 1.55 | 598 (M + H)+ |
| 1319 | 1357 | 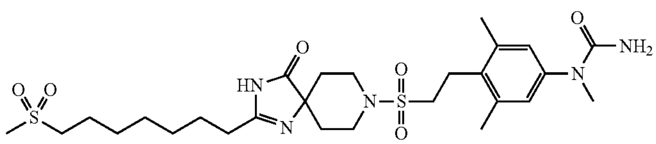 [SMILES: Cc1cc(N(C)C(N)=O)cc(C)c1CCS(=O)(=O)N1CCC2(CC1)N=C(CCCCCCCS(C)(=O)=O)NC2=O] | LCMS-D-1 | 1.52 | 598 (M + H)+ |
| 1088 | 1358 | 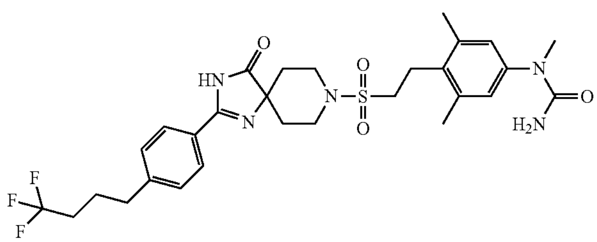 [SMILES: Cc1cc(N(C)C(N)=O)cc(C)c1CCS(=O)(=O)N1CCC2(CC1)N=C(c1ccc(CCCC(F)(F)F)cc1)NC2=O] | LCMS-D-1 | 2.40 | 608 (M + H)+ |
| 1089 | 1359 | 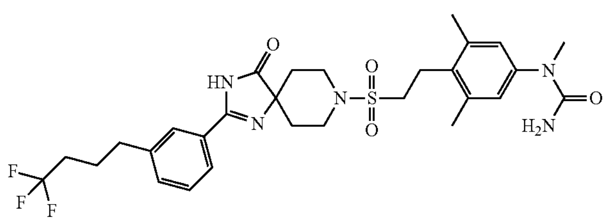 [SMILES: Cc1cc(N(C)C(N)=O)cc(C)c1CCS(=O)(=O)N1CCC2(CC1)N=C(c1cccc(CCCC(F)(F)F)c1)NC2=O] | LCMS-D-1 | 2.48 | 608 (M + H)+ |
| 1308 | 1360 | 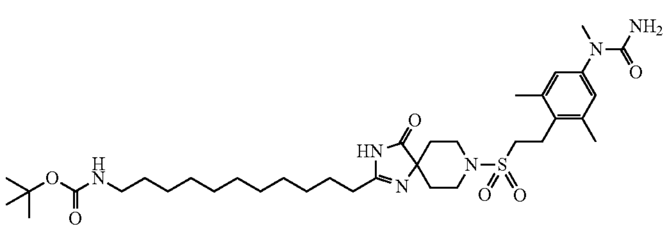 [SMILES: Cc1cc(N(C)C(N)=O)cc(C)c1CCS(=O)(=O)N1CCC2(CC1)N=C(CCCCCCCCCCCNC(=O)OC(C)(C)C)NC2=O] | LCMS-C-1 | 2.98 | 691 (M + H)+ |
| 1307 | 1361 | 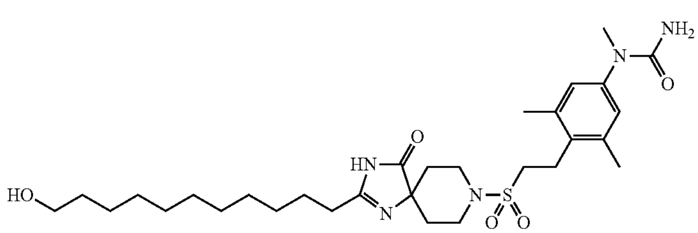 [SMILES: Cc1cc(N(C)C(N)=O)cc(C)c1CCS(=O)(=O)N1CCC2(CC1)N=C(CCCCCCCCCCCO)NC2=O] | LCMS-C-1 | 2.68 | 592 (M + H)+ |

TABLE 190-continued
| Starting Compound | Target Compound | Structure | LCMS condition | Retention time (min) | MS (m/z) |
|---|---|---|---|---|---|
| 1171 | 1362 | 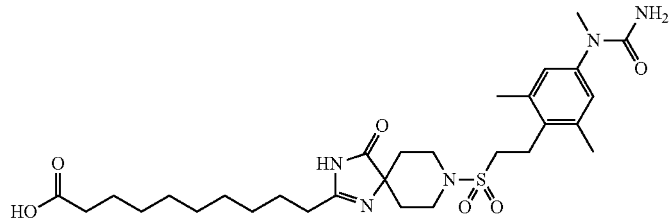 [SMILES: Cc1cc(N(C)C(N)=O)cc(C)c1CCS(=O)(=O)N1CCC2(CC1)N=C(CCCCCCCCCC(=O)O)NC2=O] | LCMS-F-1 | 0.85 | 592 (M + H)+ |
| 1172 | 1363 | 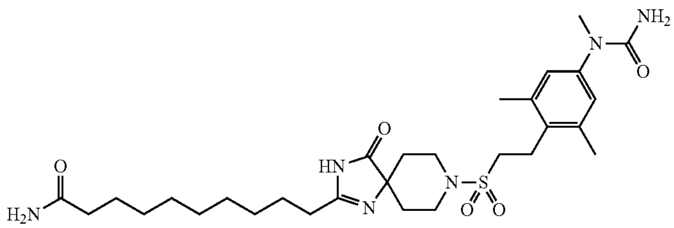 [SMILES: Cc1cc(N(C)C(N)=O)cc(C)c1CCS(=O)(=O)N1CCC2(CC1)N=C(CCCCCCCCCC(N)=O)NC2=O] | LCMS-F-1 | 0.88 | 591 (M + H)+ |
| 1110 | 1364 | 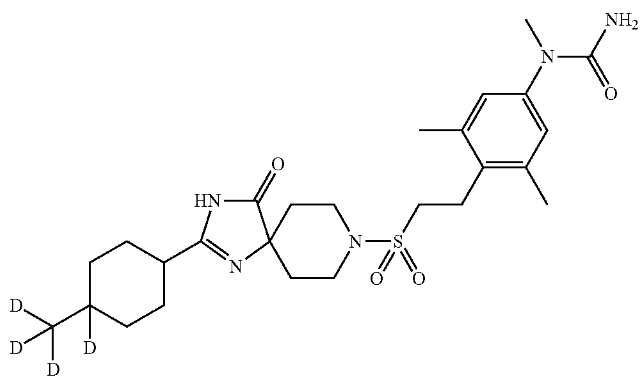 [SMILES: [2H]C([2H])([2H])C1([2H])CCC(C2=NC3(CCN(S(=O)(=O)CCc4c(C)cc(N(C)C(N)=O)cc4C)CC3)C(=O)N2)CC1] | LCMS-F-1 | 0.93 | 522 (M + H)+ |
Example 317
1-(3,5-Dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea (Compound 1365)
(Reaction 317-1)
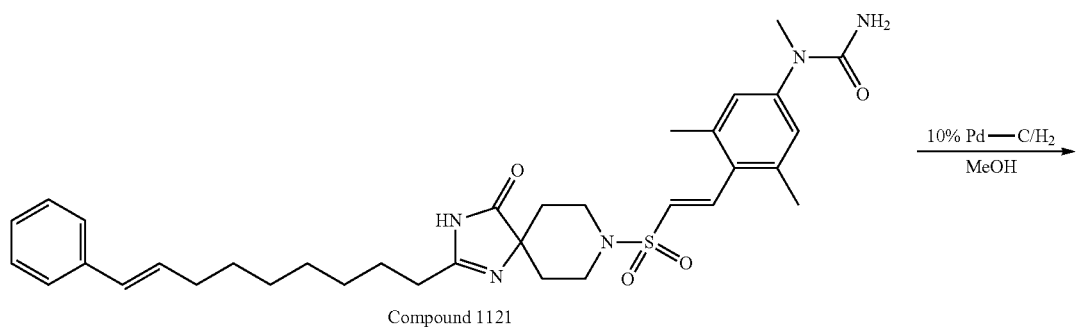

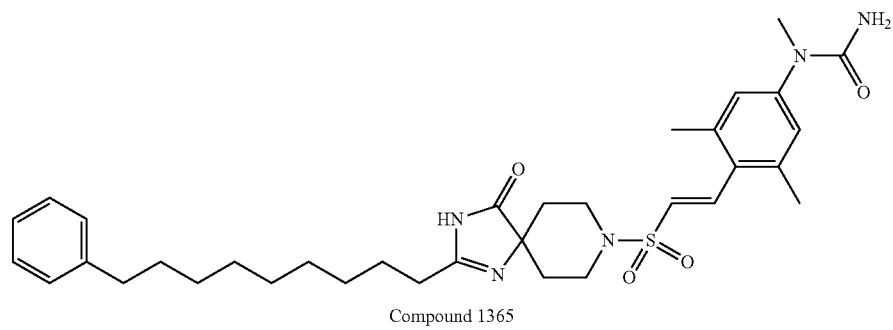

Compound 1365

1-(3,5-Dimethyl-4-{(E)-2-[4-oxo-2-(9-phenyl-nonyl)-1,3,8-triaza-spiro[4.5]dec-1-ene-8-sulfonyl]-vinyl}-phenyl)-1-methyl-urea (Compound 1365) was obtained by operations similar to those in Reaction 18-2 using Compound 1121 as a starting material.

MS (ESI) m/z=622 (M+H)+.

Example 318

1-(4-{2-[2-(11-Amino-undecyl)-4-oxo-1,3,8-triaza-spiro[4.5]dec-1-ene-8-sulfonyl]-ethyl}-3,5-dimethyl-phenyl)-1-methyl-urea (Compound 1366)

1-(4-{2-[2-(11-Amino-undecyl)-4-oxo-1,3,8-triaza-spiro[4.5]dec-1-ene-8-sulfonyl]-ethyl}-3,5-dimethyl-phenyl)-1-methyl-urea (Compound 1366) was obtained by operations similar to those in Reaction 4-1 using Compound 1360 as a starting material.

MS (ESI) m/z=591 (M+H)+.

(Reaction 318-1)

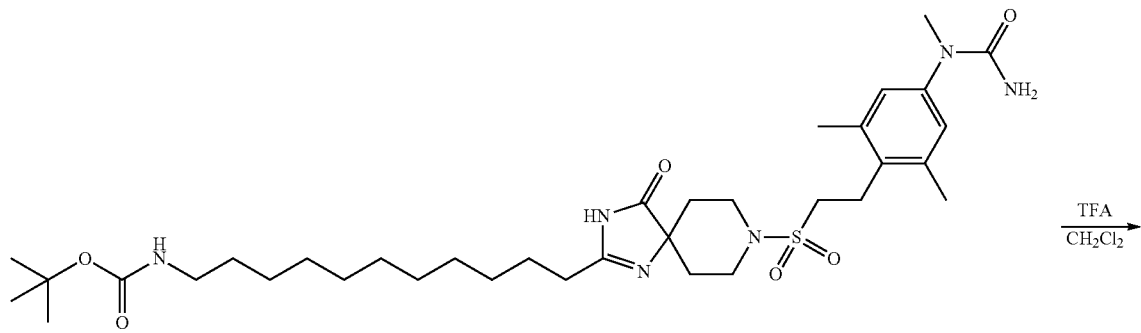

Compound 1360

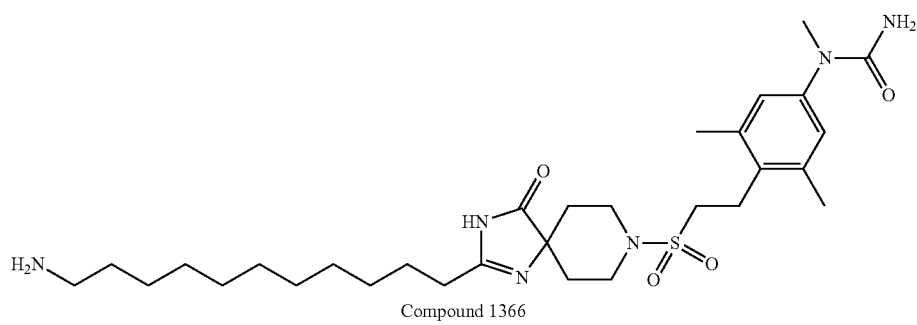

Compound 1366

Example 319

3-[(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione (Compound 1367)

(Reaction 319-1)

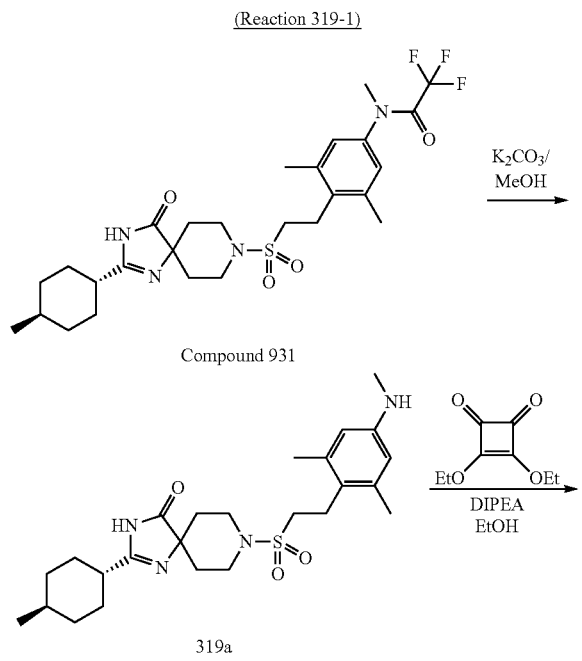

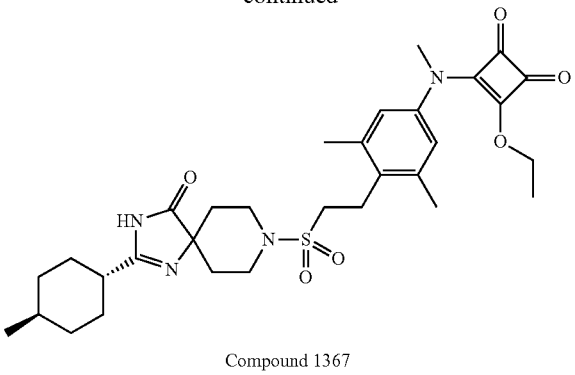

Compound 1367

3-[(3,5-Dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-4-ethoxy-cyclobut-3-ene-1,2-dione (Compound 1367) was obtained by operations similar to those in Reaction 12-5 and Reaction 95-17 (using ethanol as a solvent) using N-(3,5-dimethyl-4-{2-[2-(4-methyl-cyclohexyl)-4-oxo-1,3,8-triaza-spiro[4.5]dec-1-ene-8-sulfonyl]-ethyl}-phenyl)-2,2,2-trifluoro-N-methyl-acetamide as a starting material.

MS (ESI) m/z=599 (M+H)+.

Example 320

3-Amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1368)

(Reaction 320-1)

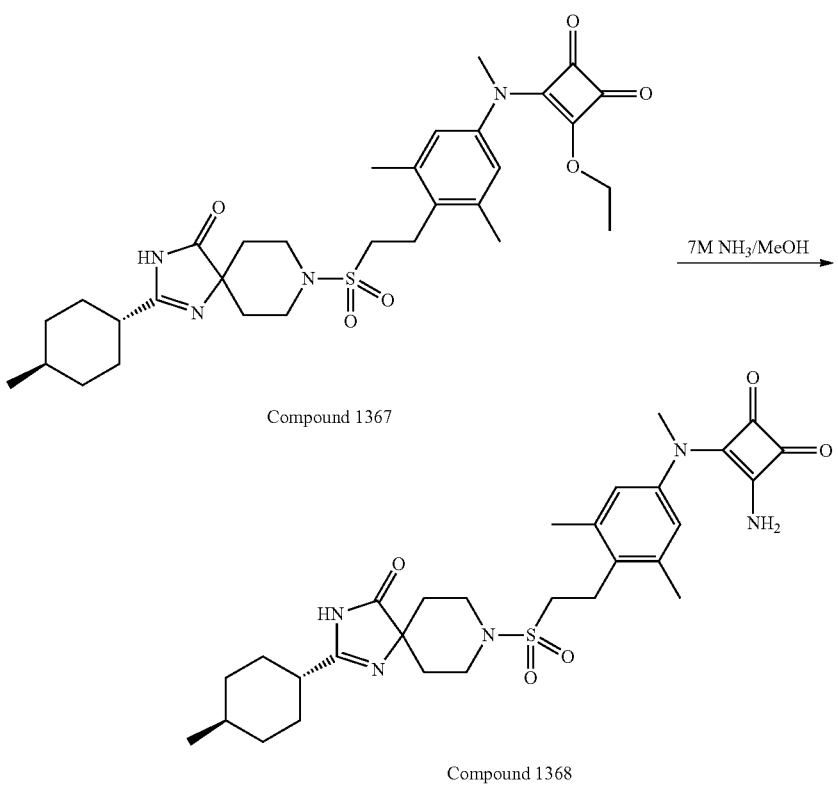

3-Amino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1368) was obtained by operations similar to those in Reaction 230-3 using Compound 1367 as a starting material.

MS (ESI) m/z=570 (M+H)+.

Example 321

3-Dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1369)

3-Dimethylamino-4-[(3,5-dimethyl-4-{2-[2-(4-methyl-cyclohexyl)-4-oxo-1,3,8-triaza-spiro[4.5]dec-1-ene-8-sulfonyl]-ethyl}-phenyl)-methyl-amino]-cyclobut-3-ene-1,2-dione (Compound 1369) was obtained by operations similar to those in Reaction 230-3 using Compound 1367 as a starting material.

MS (ESI) m/z=598 (M+H)+.

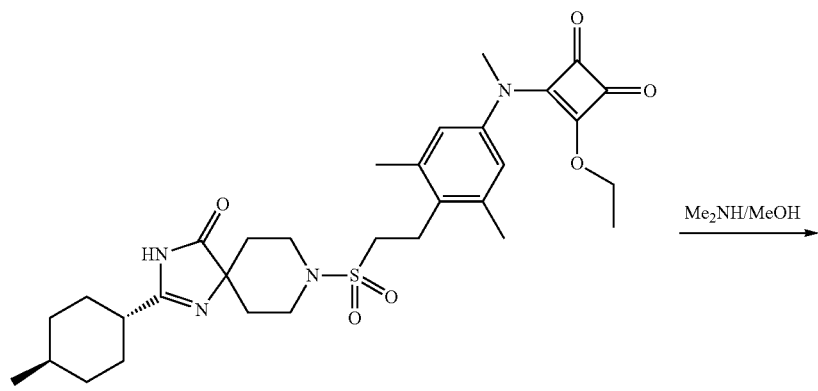

Compound 1367

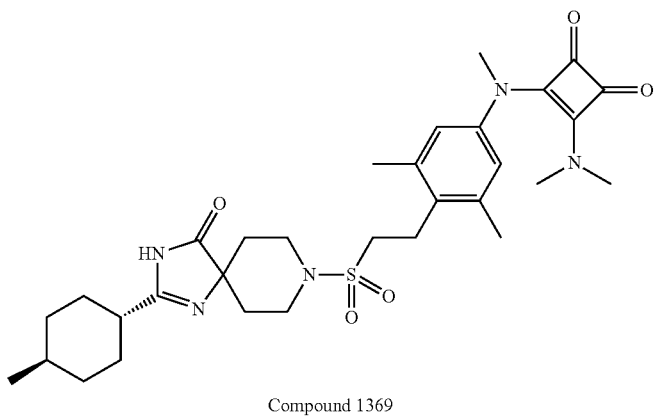

Compound 1369

Example 322

N-(4-{2-[2-(4-Ethynyl-cyclohexyl)-4-oxo-1,3,8-triaza-spiro[4.5]dec-1-ene-8-sulfonyl]-ethyl}-3-methyl-phenyl)-acetamide (Compound 1370)

(Reaction 322-1)

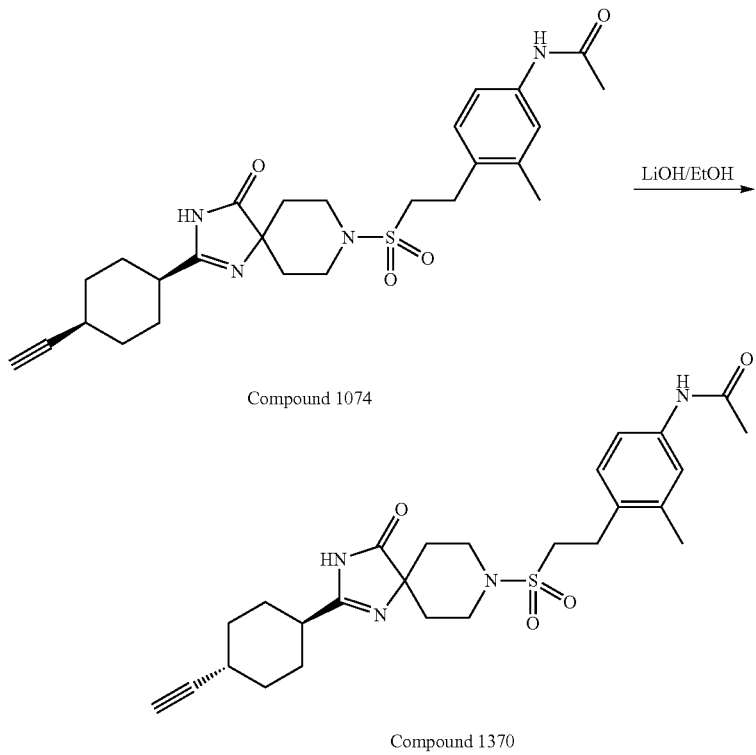

Lithium hydroxide monohydrate (4.3 mg, 0.102 mmol) was added to a mixed solution of N-(4-{2-[2-(4-ethynyl-cyclohexyl)-4-oxo-1,3,8-triaza-spiro[4.5]dec-1-ene-8-sulfonyl]-ethyl}-3-methyl-phenyl)-acetamide (17 mg, 0.0341 mmol) in ethanol (1.25 mL) at room temperature. The mixture was stirred at 60° C. for 14 hours and then concentrated under reduced pressure. The resulting residue was purified by silica gel column chromatography to give N-(4-{2-[2-(4-ethynyl-cyclohexyl)-4-oxo-1,3,8-triaza-spiro[4.5]-dec-1-ene-8-sulfonyl]-ethyl}-3-methyl-phenyl)-acetamide as a white solid (17 mg, 99%).

MS (ESI) m/z=499 (M+H)+.

Example 323

1-(4-{2-[4-[(E)-Hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea (Compound 1371)

(Reaction 323-1)

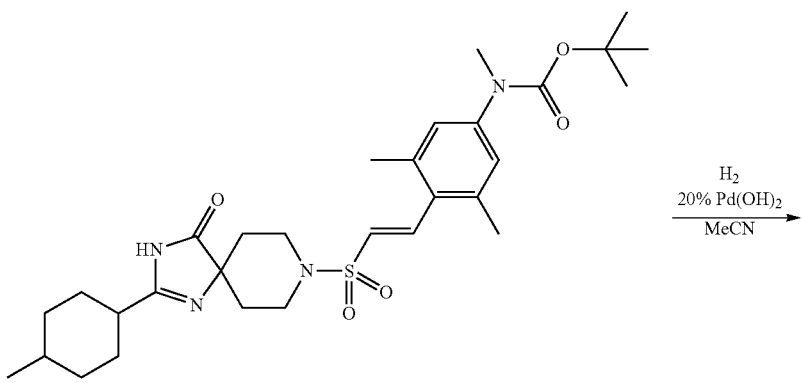

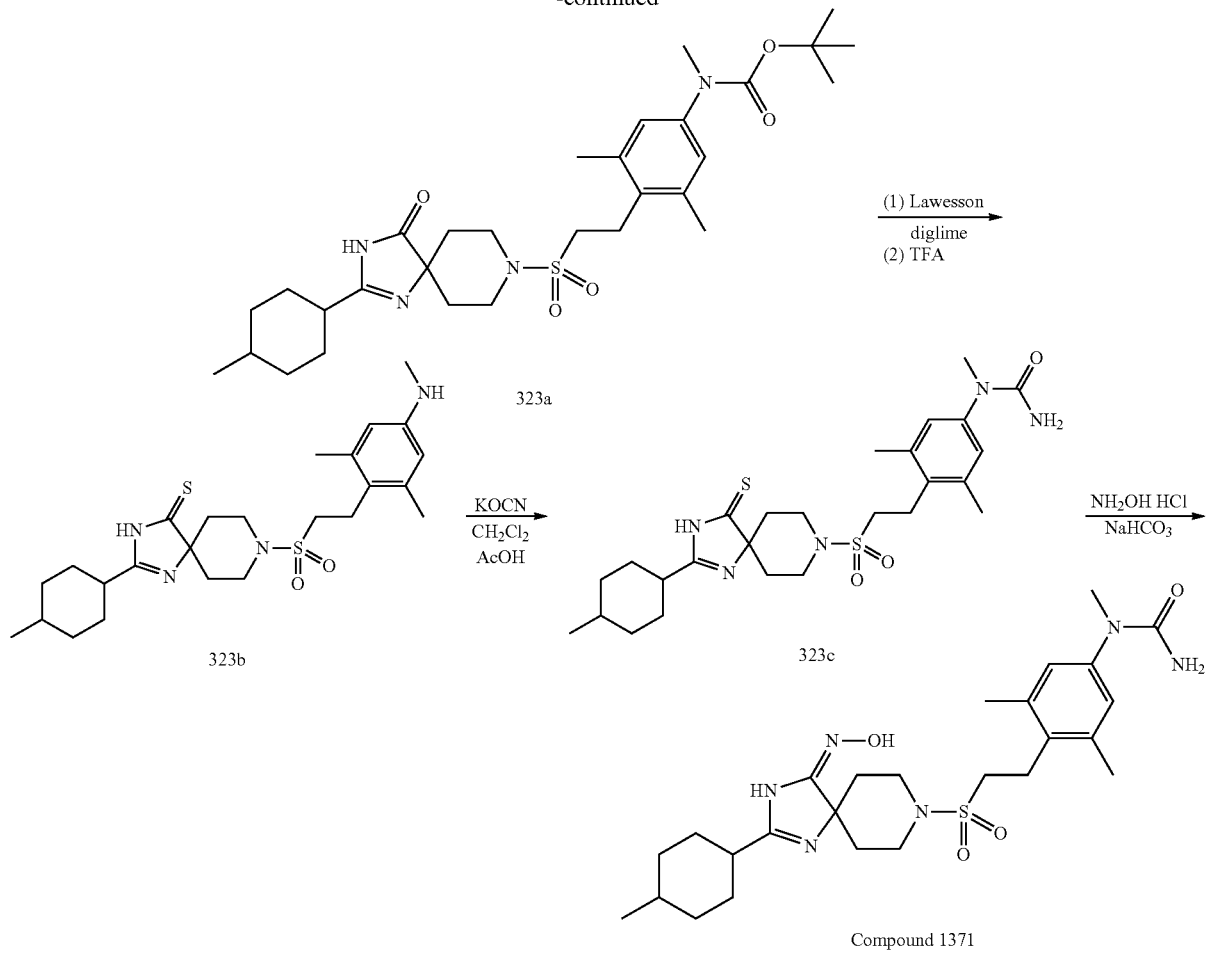

1-(4-{2-[4-[(E)-Hydroxyimino]-2-(4-methyl-cyclohexyl)-1,3,8-triaza-spiro[4.5]dec-1-ene-8-sulfonyl]-ethyl}-3,5-dimethyl-phenyl)-1-methyl-urea (Compound 1371) was obtained by operations similar to those in Reaction 184-1, Reaction 88-1, Reaction 89-2 (using KOCN) and Reaction 189-9 using 3,5-dimethyl-4-{(E)-2-[2-(4-methyl-cyclohexyl)-4-oxo-1,3,8-triaza-spiro[4.5]dec-1-ene-8-sulfonyl]-vinyl}-phenyl)-methyl-carbamic acid tert-butyl ester as a starting material.

MS (ESI) m/z=533 (M+H)+.

Example 324

2-(4-Methyl-cyclohexyl)-4-oxo-1,3,8-triaza-spiro[4.5]dec-1-ene-8-sulfonic acid 2-methyl-benzylamide (Compound 1372)

(Reaction 324-1)

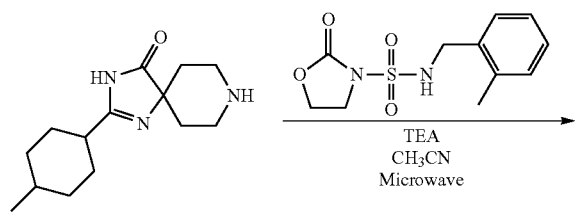

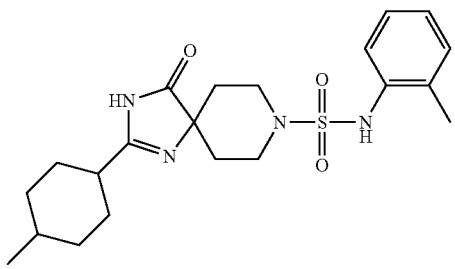

2-(4-Methyl-cyclohexyl)-4-oxo-1,3,8-triaza-spiro[4.5]dec-1-ene-8-sulfonic acid 2-methyl-benzylamide (Compound 1372) was obtained by operations similar to those in Reaction 24-2 using 2-(4-methyl-cyclohexyl)-1,3,8-triaza-spiro[4.5]dec-1-en-4-one as a starting material.

MS (ESI) m/z=433 (M+H)+.

Example 325

2-(4-Methyl-cyclohexyl)-4-oxo-1,3,8-triaza-spiro[4.5]dec-1-ene-8-sulfonic (2-o-tolyl-ethyl)-amide (Compound 1373)

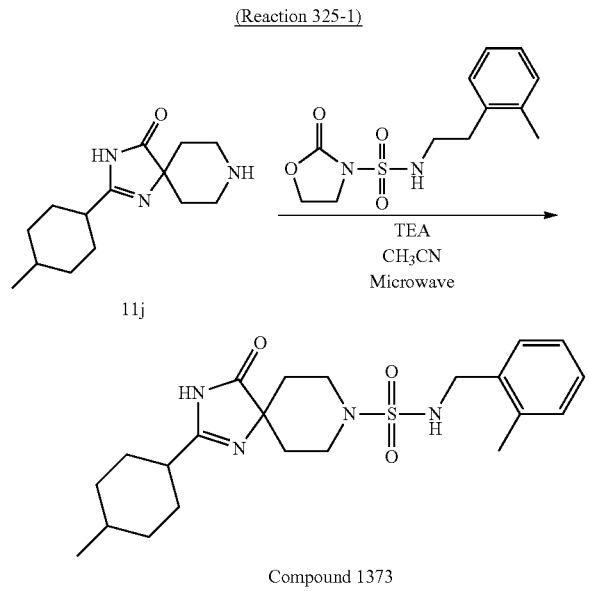

2-(4-Methyl-cyclohexyl)-4-oxo-1,3,8-triaza-spiro[4.5]dec-1-ene-8-sulfonic (2-o-tolyl-ethyl)-amide (Compound 1373) was obtained by operations similar to those in Reaction 24-2 using 2-(4-methyl-cyclohexyl)-1,3,8-triaza-spiro[4.5]dec-1-en-4-one as a starting material.

MS (ESI) m/z=448 (M+H)+.

Example 326

2-Cyclohexyl-8-{2-[1-((S)-2,3-dihydroxy-propyl)-1H-indol-4-yl]-2-hydroxy-ethanesulfonyl}-1,3,8-triaza-spiro[4.5]dec-1-en-4-one (Compound 1374)

(Reaction 326-1)

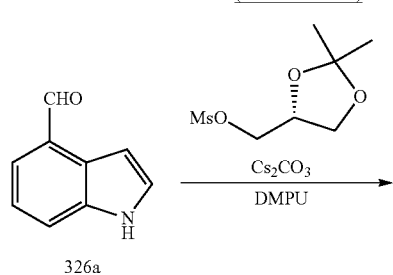

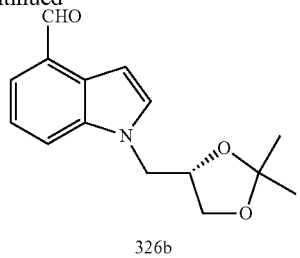

1H-Indole-4-carbaldehyde (1.81 g, 12.5 mmol) and cesium carbonate (8.15 g, 25.0 mmol) were added to a solution of methanesulfonic acid (R)-2,2-dimethyl-[1,3]dioxolan-4-yl methyl ester (3.40 g, 16.1 mmol) in 1,3-dimethyl-3,4,5,6-tetrahydro-2(1H)-pyrimidinone (30.8 mL), and the mixture was stirred at 90° C. for 40 hours. Water was added, followed by extraction with hexane:ethyl acetate (1:4). The organic layer was washed with water four times and then dried over sodium sulfate. After concentration, the residue was purified by silica gel column chromatography to give 1-((S)-2,2-dimethyl-[1,3]dioxolan-4-ylmethyl)-1H-indole-4-carbaldehyde (2.88 g, 88%) as a yellow oily substance.

MS (ESI) m/z=260 (M+H)+.

(Reaction 326-2)

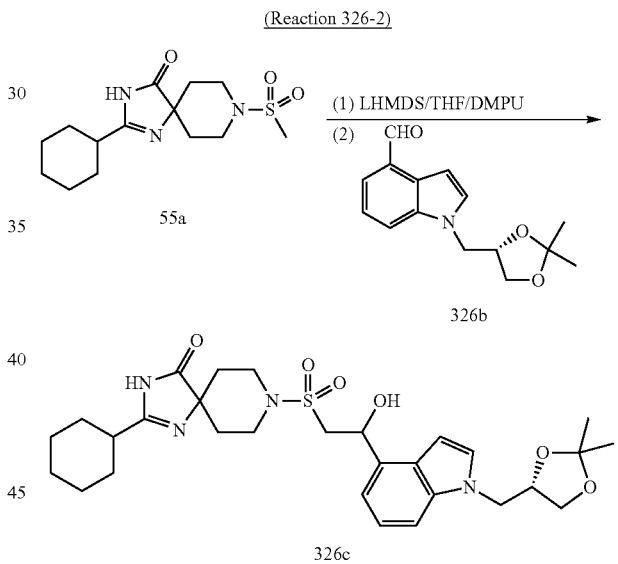

A suspension of 2-cyclohexyl-8-methanesulfonyl-1,3,8-triaza-spiro[4.5]dec-1-en-4-one (100 mg, 0.319 mmol) in 1,3-dimethyl-3,4,5,6-tetrahydro-2(1H)-pyrimidinone (0.66 mL) was cooled to 0° C. A 1 M solution of lithium hexamethyldisilazide in tetrahydrofuran (0.989 ml) was then added and the mixture was stirred at room temperature for 30 minutes. After cooling again to 0° C., a solution of 1-((S)-2,2-dimethyl-[1,3]dioxolan-4-ylmethyl)-1H-indole-4-carbaldehyde (87 mg, 0.335 mmol) in tetrahydrofuran (0.4 mL) was added and the mixture was stirred at 0° C. for five hours. Water was added and the aqueous layer was extracted with ethyl acetate. The organic layer was washed with water and then dried over sodium sulfate. After concentration, the residue was purified by silica gel column chromatography to give 2-cyclohexyl-8-{2-[1-((S)-2,2-dimethyl-[1,3]dioxolan-4-ylmethyl)-1H indol-4-yl]-2-hydroxy-ethanesulfonyl}-1,3,8-triaza-spiro[4.5]dec-1-en-4-one (113 mg, 62%) as a pale yellow solid.

MS (ESI) m/z=573 (M+H)+.

(Reaction 326-3)

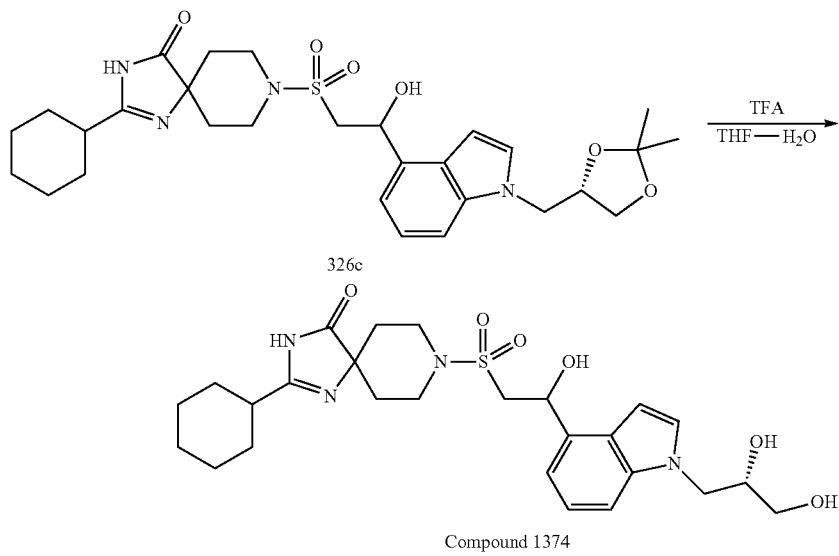

2-Cyclohexyl-8-{2-[1-((5)-2,3-dihydroxy-propyl)-1H-indol-4-yl]-2-hydroxy-ethanesulfonyl}-1,3,8-triaza-spiro[4.5]dec-1-en-4-one (Compound 1374) was synthesized by operations similar to those in Reaction 4-1 using appropriate reagents and starting material.

MS (ESI) m/z=573, 533 (M+H)+.

Example 327

2-Cyclohexyl-8-(2-oxo-2-o-tolyl-ethanesulfonyl)-1,3,8-triaza-spiro[4.5]dec-1-en-4-one (Compound 1375)

(Reaction 327-1)

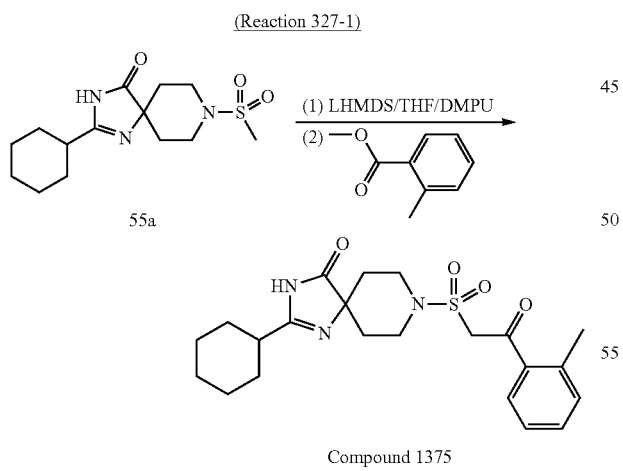

2-Cyclohexyl-8-(2-oxo-2-o-tolyl-ethanesulfonyl)-1,3,8-triaza-spiro[4.5]dec-1-en-4-one (Compound 1375) was obtained by operations similar to those in Reaction 326-2 using 2-cyclohexyl-8-methanesulfonyl-1,3,8-triaza-spiro[4.5]dec-1-en-4-one as a starting material.

MS (ESI) m/z=432 (M+H)+.

Example 328

2-Cyclohexyl-8-(2-o-tolyl-ethynesulfonyl)-1,3,8-triaza-spiro[4.5]dec-1-en-4-one (Compound 1376)

(Reaction 328-1)

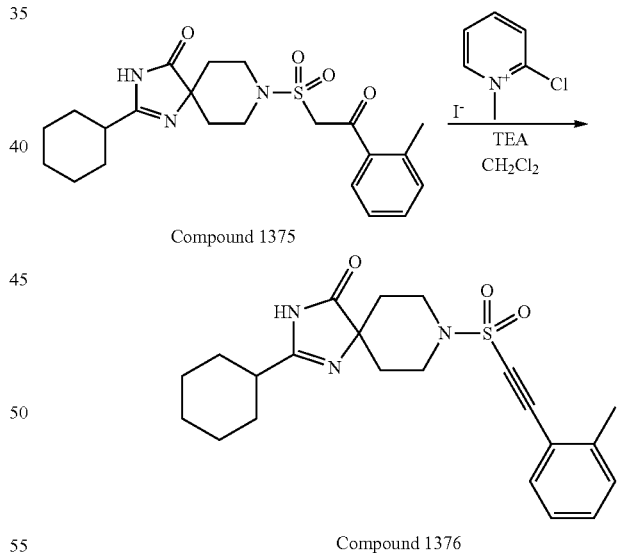

2-Chloro-1-methyl-pyridinium iodide (18 mg, 0.070 mmol) and triethylamine (0.28 mL, 1.98 mmol) were added to a solution of 2-cyclohexyl-8-(2-oxo-2-o-tolyl-ethanesulfonyl)-1,3,8-triaza-spiro[4.5]dec-1-en-4-one (20 mg, 0.046 mmol) in methylene chloride (1.0 mL), and the mixture was stirred at room temperature for 19 hours. 2-Chloro-1-methylpyridinium iodide (18 mg, 0.070 mmol) and triethylamine (0.28 mL, 1.98 mmol) were further added, and the mixture was stirred at room temperature for five hours. A 1 M aqueous sodium hydroxide solution was added to the reaction mixture, and the mixture was stirred at room temperature for 20 minutes. The aqueous layer was extracted with methylene chloride, and the organic layer was washed with a 1 M aqueous sodium hydroxide solution, water and saturated brine and dried over sodium sulfate. The organic layer was concentrated, and the residue was then silica gel column chromatography to give 2-cyclohexyl-8-(2-o-tolyl-ethynesulfonyl)-1,3,8-triaza-spiro[4.5]dec-1-en-4-one (15 mg, 79%) as a white solid.

$^1$H-NMR (CDCl$_3$) δ 8.39 (1H, s), 7.60 (1H, dd, J=7.6, 1.2 Hz), 7.38 (1H, td, J=7.6, 1.4 Hz), 7.28-7.16 (2H, m), 3.80-3.75 (2H, m), 3.42-3.36 (2H, m), 2.52 (3H, s), 2.46-2.38 (1H, m), 2.14-2.07 (2H, m), 1.94-1.56 (8H, m), 1.47-1.22 (6H, m);

MS (ESI) m/z=414 (M+H)+.

Example 329

2-Cyclohexyl-8-[2-(1H-indol-4-yl)-ethynesulfonyl]-1,3,8-triaza-spiro[4.5]dec-1-en-4-one (Compound 1377)

2-Cyclohexyl-8-[2-(1H-indol-4-yl)-ethynesulfonyl]-1,3,8-triaza-spiro[4.5]dec-1-en-4-one (Compound 1377) was obtained by operations similar to those in Reaction 326-2 and Reaction 328-1 using 2-cyclohexyl-8-methanesulfonyl-1,3,8-triaza-spiro[4.5]dec-1-en-4-one as a starting material.

MS (ESI) m/z=439 (M+H)+.

(Reaction 329-1)

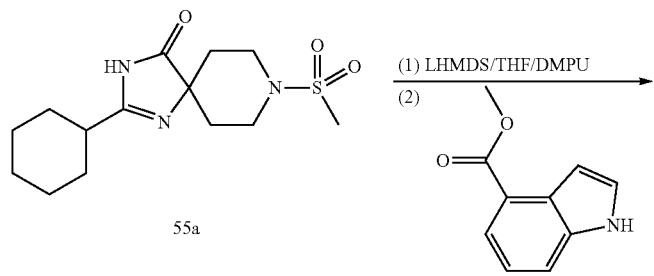

55a

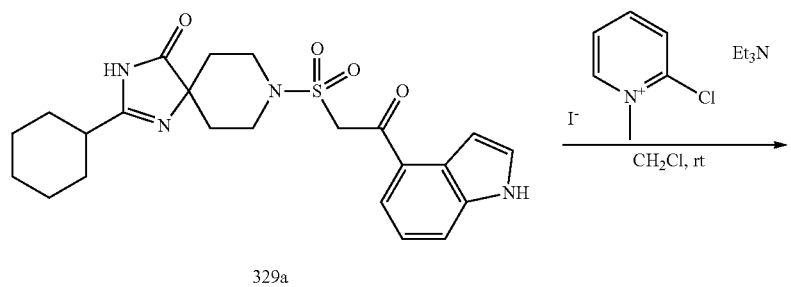

329a

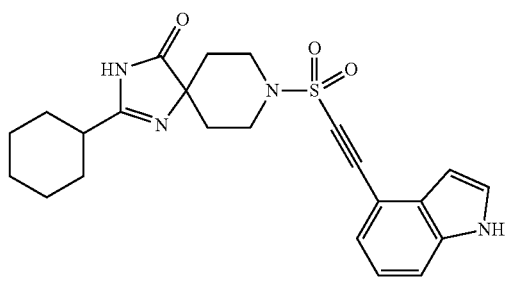

Compound 1377

Example 330

3,5,N,N-Tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide (Compound 1378)

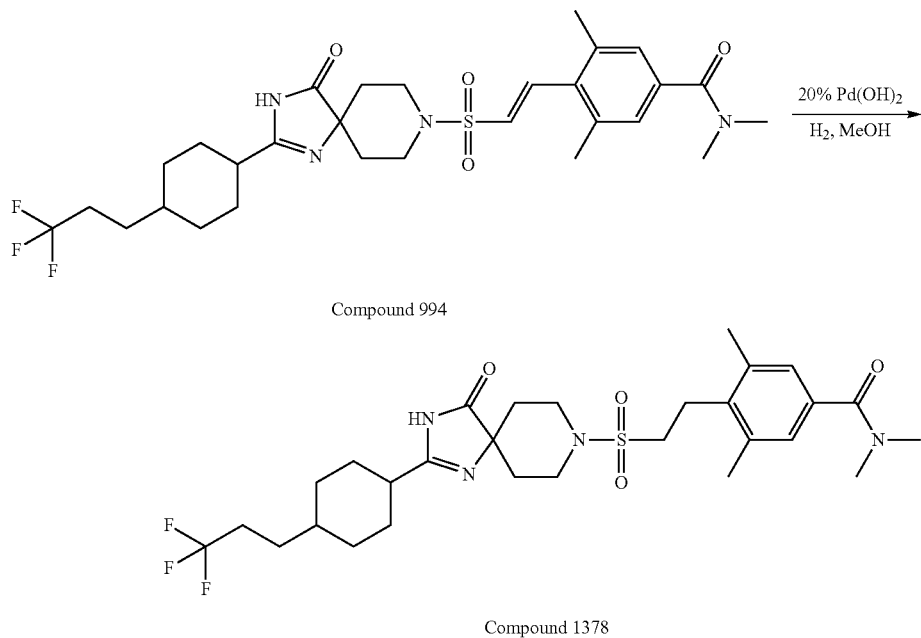

Compound 994

Compound 1378

3,5,N,N-Tetramethyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzamide (Compound 1378) was obtained by operations similar to those in Reaction 122-2 using Compound 994 as a starting material.

MS (ESI) m/z=599 (M+H)+.

The example compounds shown below were obtained by operations similar to those in Reaction 330-1 using appropriate solvents (acetonitrile or methanol or an acetonitrile-methanol mixed solution) and starting compounds.

Compounds 1379 to Compound 1391

TABLE 191

| Starting Compound | Target Compound | Structure | LCMS condition | Retention time (min) | MS (m/z) |
|---|---|---|---|---|---|
| 1003 | 1379 | 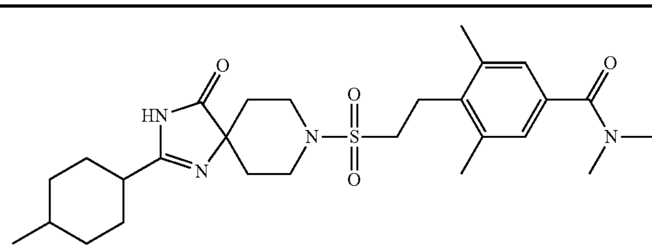 | LCMS-D-1 | 1.91 | 517 (M + H)+ |
| 989 | 1380 | 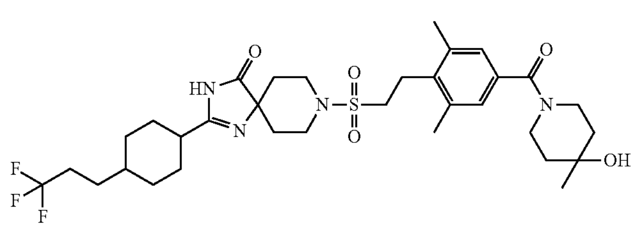 [SMILES: Cc1cc(C(=O)N2CCC(C)(O)CC2)cc(C)c1CCS(=O)(=O)N1CCC2(CC1)N=C(C1CCC(CCC(F)(F)F)CC1)NC2=O] | LCMS-D-1 | 2.31 | 669 (M + H)+ |

TABLE 191-continued

| Starting Compound | Target Compound | Structure | LCMS condition | Retention time (min) | MS (m/z) |
|---|---|---|---|---|---|
| 990 | 1381 | 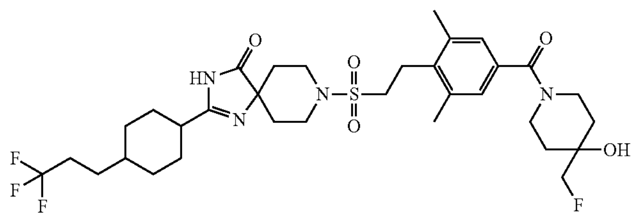 [SMILES: Cc1cc(C(=O)N2CCC(O)(CF)CC2)cc(C)c1CCS(=O)(=O)N1CCC2(CC1)N=C(C1CCC(CCC(F)(F)F)CC1)NC2=O] | LCMS-D-1 | 2.26 | 687 (M + H)+ |
| 999 | 1382 | 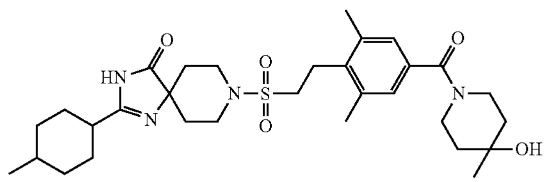 [SMILES: Cc1cc(C(=O)N2CCC(C)(O)CC2)cc(C)c1CCS(=O)(=O)N1CCC2(CC1)N=C(C1CCC(C)CC1)NC2=O] | LCMS-C-1 | 2.62 | 585 (M + H)+ |
| 1000 | 1383 | 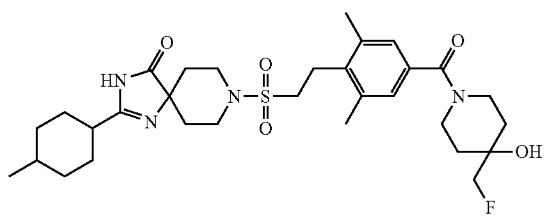 [SMILES: Cc1cc(C(=O)N2CCC(O)(CF)CC2)cc(C)c1CCS(=O)(=O)N1CCC2(CC1)N=C(C1CCC(C)CC1)NC2=O] | LCMS-D-1 | 2.88 | 605 (M + H)+ |
| 993 | 1384 | 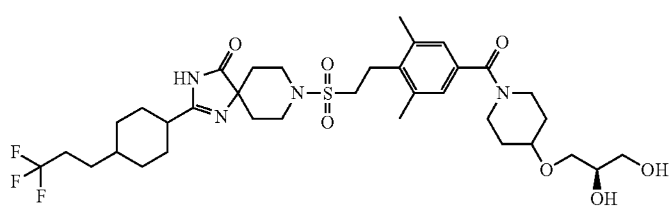 [SMILES: Cc1cc(C(=O)N2CCC(OC[C@H](O)CO)CC2)cc(C)c1CCS(=O)(=O)N1CCC2(CC1)N=C(C1CCC(CCC(F)(F)F)CC1)NC2=O] | LCMS-D-1 | 2.17 | 729 (M + H)+ |
| 996 | 1385 | 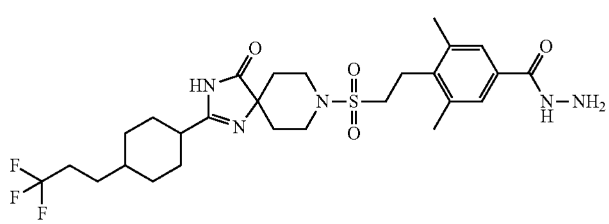 [SMILES: Cc1cc(C(=O)NN)cc(C)c1CCS(=O)(=O)N1CCC2(CC1)N=C(C1CCC(CCC(F)(F)F)CC1)NC2=O] | LCMS-D-1 | 1.87 | 586 (M + H)+ |
| 997 | 1386 | 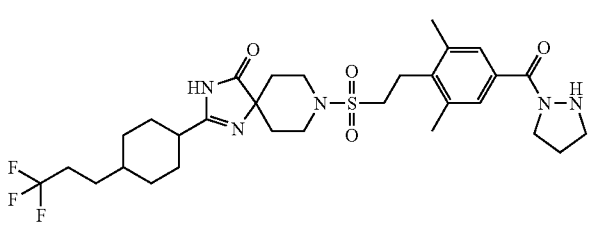 [SMILES: Cc1cc(C(=O)N2CCCN2)cc(C)c1CCS(=O)(=O)N1CCC2(CC1)N=C(C1CCC(CCC(F)(F)F)CC1)NC2=O] | LCMS-D-1 | 2.00 | 626 (M + H)+ |

TABLE 191-continued

| Starting Compound | Target Compound | Structure | LCMS condition | Retention time (min) | MS (m/z) |
|---|---|---|---|---|---|
| 987 | 1387 | 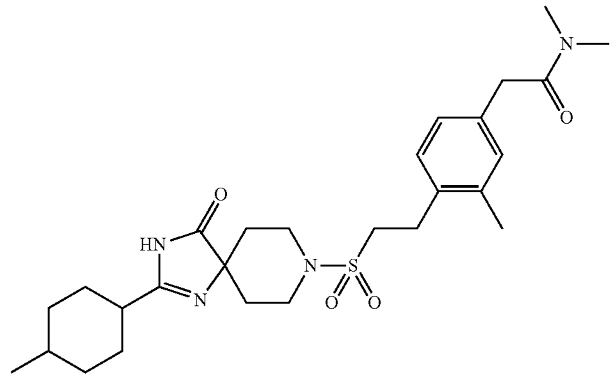 | LCMS-F-1 | 0.94 | 517 (M + H)+ |
| 988 | 1388 | 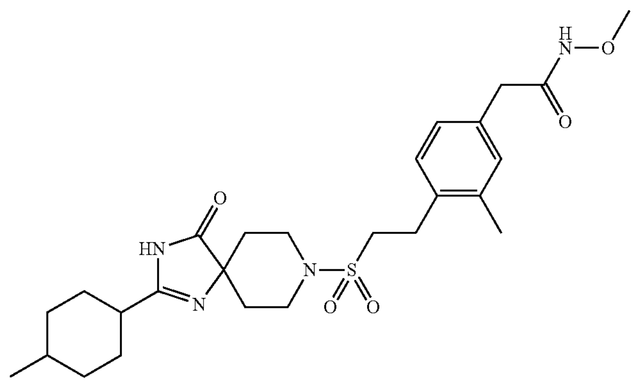 | LCMS-F-1 | 0.90 | 519 (M + H)+ |
| 1300 | 1389 | 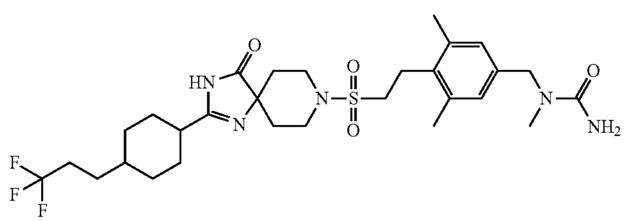 [SMILES: Cc1cc(CN(C)C(N)=O)cc(C)c1CCS(=O)(=O)N1CCC2(CC1)N=C(C1CCC(CCC(F)(F)F)CC1)NC2=O] | LCMS-D-1 | 2.37 | 614 (M + H)+ |
| 1301 | 1390 | 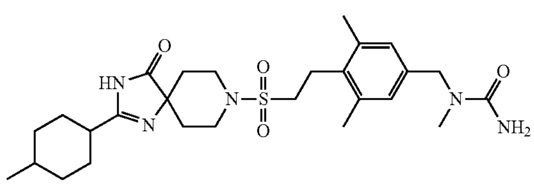 [SMILES: Cc1cc(CN(C)C(N)=O)cc(C)c1CCS(=O)(=O)N1CCC2(CC1)N=C(C1CCC(C)CC1)NC2=O] | LCMS-D-1 | 1.95 | 532 (M + H)+ |
| 1312 | 1391 | 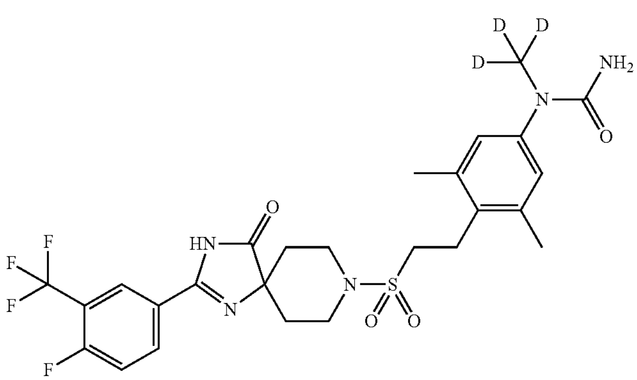 [SMILES: [2H]C([2H])([2H])N(C(N)=O)c1cc(C)c(CCS(=O)(=O)N2CCC3(CC2)N=C(c2ccc(F)c(C(F)(F)F)c2)NC3=O)c(C)c1] | LCMS-F-1 | 0.98 | 587 (M + H)+ |

Example 331
2-Cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one (Compound 1392) and 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one (Compound 1393)
(Reaction 331-1)
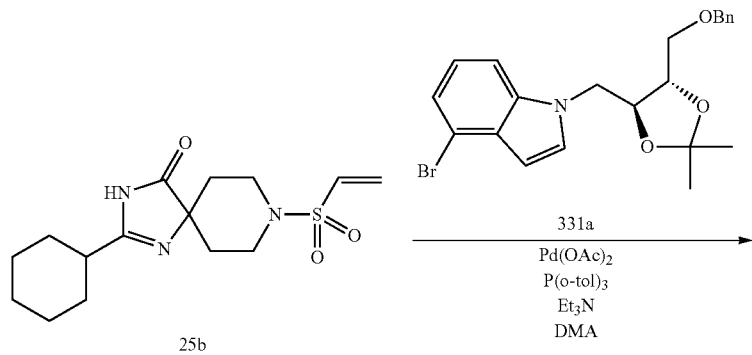
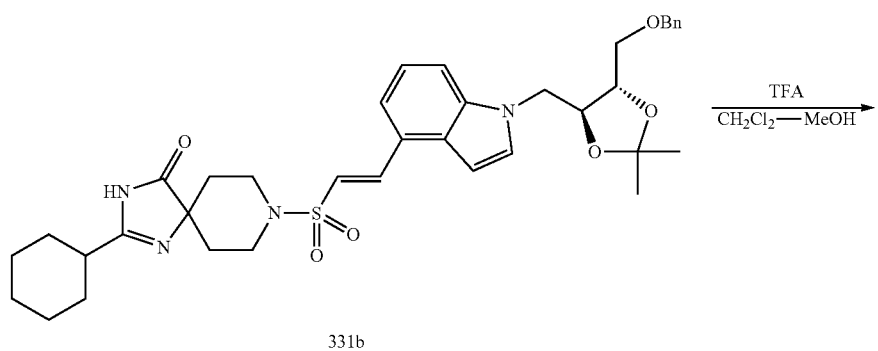
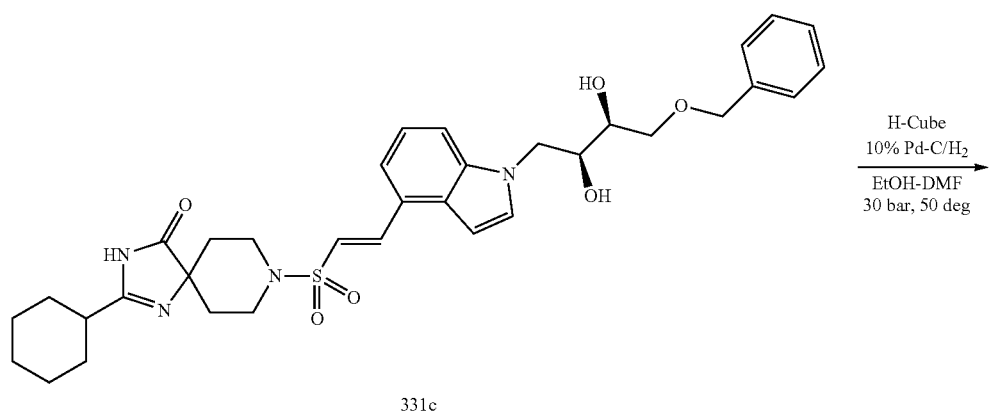

-continued

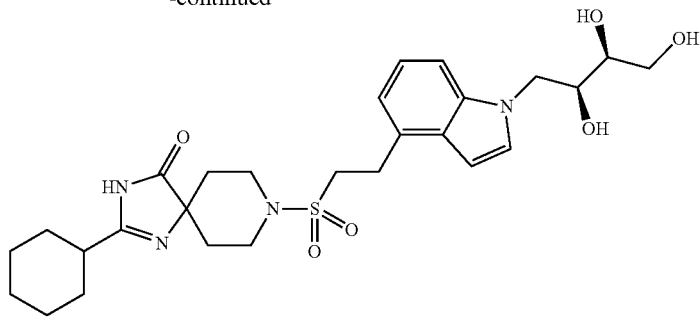

Compound 1392

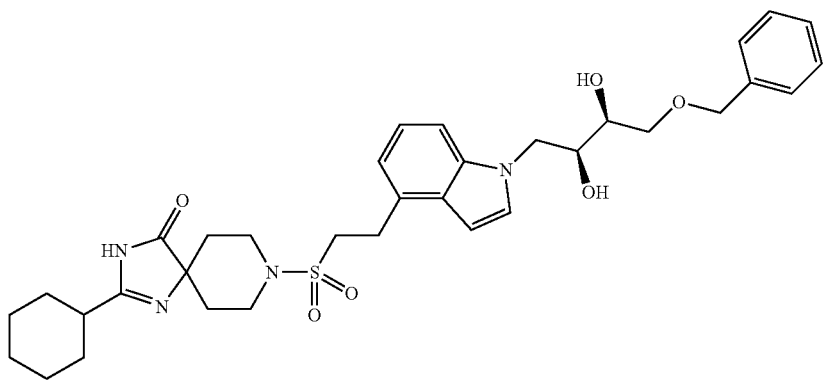

Compound 1393

2-Cyclohexyl-8-{2-[1-((2S,3S)-2,3,4-trihydroxy-butyl)-1H-indol-4-yl]-ethanesulfonyl}-1,3,8-triaza-spiro[4.5]dec-1-en-4-one (Compound 1392)

MS (ESI) m/z=547 (M+H)+ and 8-{2-[1-((2S,3S)-4-benzyloxy-2,3-dihydroxy-butyl)-1H-indol-4-yl]-ethanesulfonyl}-2-cyclohexyl-1,3,8-triaza-spiro[4.5]dec-1-en-4-one (Compound 1393)

MS (ESI) m/z=637 (M+H)+ were obtained by operations similar to those in Reaction 26-1, Reaction 4-1 and Reaction 42-2 using 2-cyclohexyl-8-ethenesulfonyl-1,3,8-triaza-spiro[4.5]dec-1-en-4-one as a starting material.

Example 332

N-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide (Compound 1394)

(Reaction 332-1)

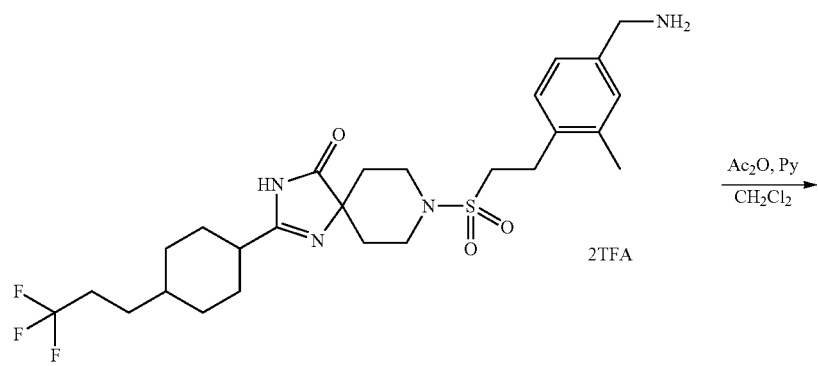

Compound 1284

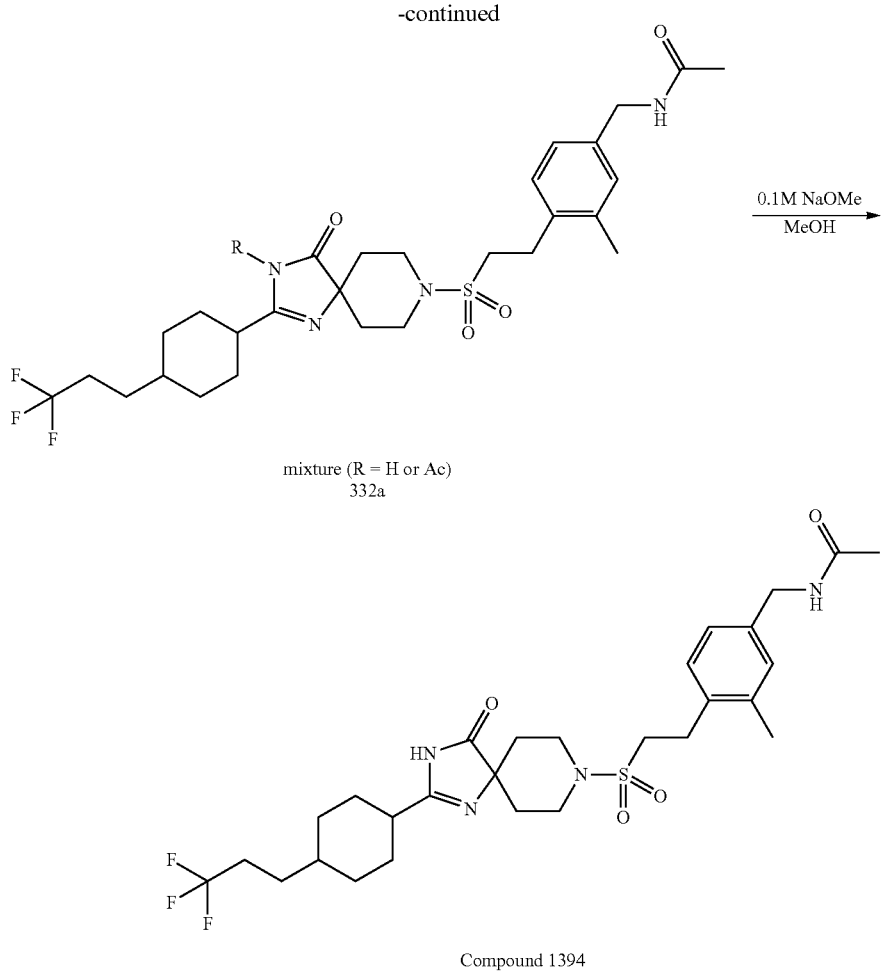

mixture (R = H or Ac)
332a

Compound 1394

N-[3-Methyl-4-(2-{4-oxo-2-[4-(3,3,3-trifluoro-propyl)-cyclohexyl]-1,3,8-triaza-spiro[4.5]dec-1-ene-8-sulfonyl}-ethyl)-benzyl]-acetamide (Compound 1394) was obtained by operations similar to those in Reaction 12-2 and Reaction 14-1 (using NaOMe as a base) using Compound 1284 as a starting material.

MS (ESI) m/z=585 (M+H)+.

Example 333

3,N,N-Trimethyl-4-{2-[4-oxo-2-(3-trifluoromethyl-phenylamino)-1,3,8-triaza-spiro[4.5]dec-1-ene-8-sulfonyl]-ethyl}-benzamide (Compound 1395)

(Reaction 333-1)

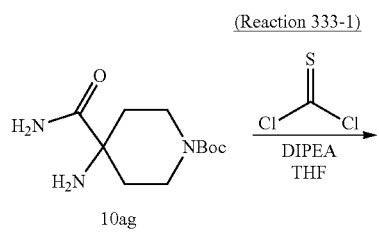

-continued

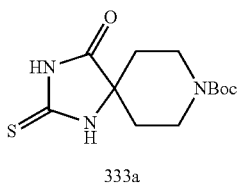

333a

N,N-Diisopropylethylamine (1.67 ml, 9.84 mmol) was added to a solution of 4-amino-4-carbamoyl-piperidine-1-carboxylic acid tert-butyl ester (1.0 g, 4.1 mmol) in THF (10 ml) at 0° C., and thiophosgene (0.376 ml, 4.9 mmol) was further added dropwise slowly. The reaction solution was warmed to room temperature and stirred overnight. A 10% aqueous citric acid solution was added to the reaction mixture, followed by extraction with ethyl acetate. The organic layers were combined and dried over magnesium sulfate, and the solvent was then distilled off. The residue was purified by silica gel column chromatography to give 4-oxo-2-thioxo-1,3,8-triaza-spiro[4.5]decane-8-carboxylic acid tert-butyl ester (944 mg, 81%).

MS (ESI) m/z=284 (M–H)–.

(Reaction 333-2)

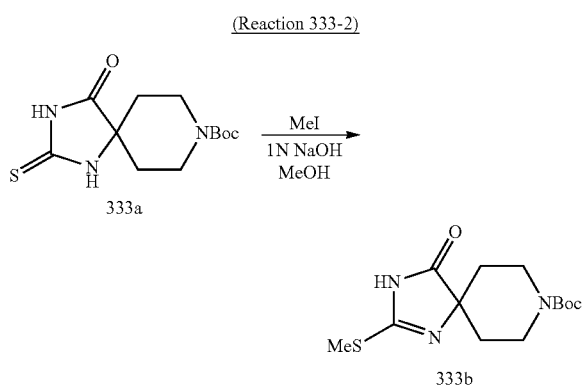

Iodomethane (0.329 ml, 5.28 mmol) and a 1 N aqueous NaOH solution (3.3 ml, 3.3 mmol) were sequentially added to a solution of 4-oxo-2-thioxo-1,3,8-triaza-spiro[4.5]decane-8-carboxylic acid tert-butyl ester (944 mg, 3.3 mmol) in methanol (33 ml) at room temperature, and the mixture was stirred at the same temperature overnight. Water was added to the reaction mixture, followed by extraction with ethyl acetate. The organic layers were combined and dried over magnesium sulfate, and the solvent was then distilled off. The residue was purified by silica gel column chromatography to give 2-methylsulfanyl-4-oxo-1,3,8-triaza-spiro[4.5]dec-1-ene-8-carboxylic acid tert-butyl ester (762 mg, 77%).

MS (ESI) m/z=322 (M+Na)+.

(Reaction 333-3)

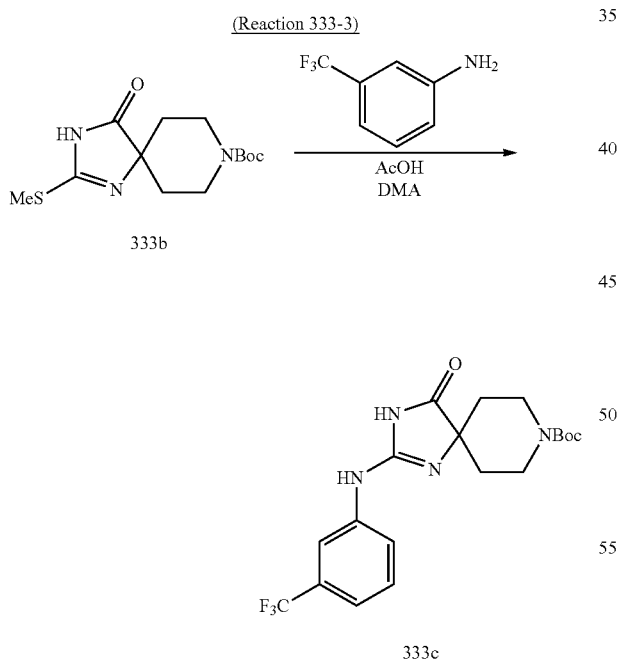

Acetic acid (0.275 ml, 4.8 mmol) was added to a solution of 2-methylsulfanyl-4-oxo-1,3,8-triaza-spiro[4.5]dec-1-ene-8-carboxylic acid tert-butyl ester (72 mg, 0.24 mmol) and m-trifluoromethylaniline (0.150 ml, 1.2 mmol) in DMA (1.0 ml), and the mixture was irradiated with microwaves at 150° C. for 20 minutes. A saturated aqueous sodium bicarbonate solution was added to the reaction mixture, followed by extraction with ethyl acetate. The organic layers were combined, washed with saturated brine and dried over magnesium sulfate, and the solvent was then distilled off. The residue was purified by silica gel column chromatography to give 4-oxo-2-(3-trifluoromethyl-phenylamino)-1,3,8-triaza-spiro[4.5]dec-1-ene-8-carboxylic acid tert-butyl ester (50 mg, 51%).

MS (ESI) m/z=313 (M-(Boc+H)+H)+.

(Reaction 333-4)

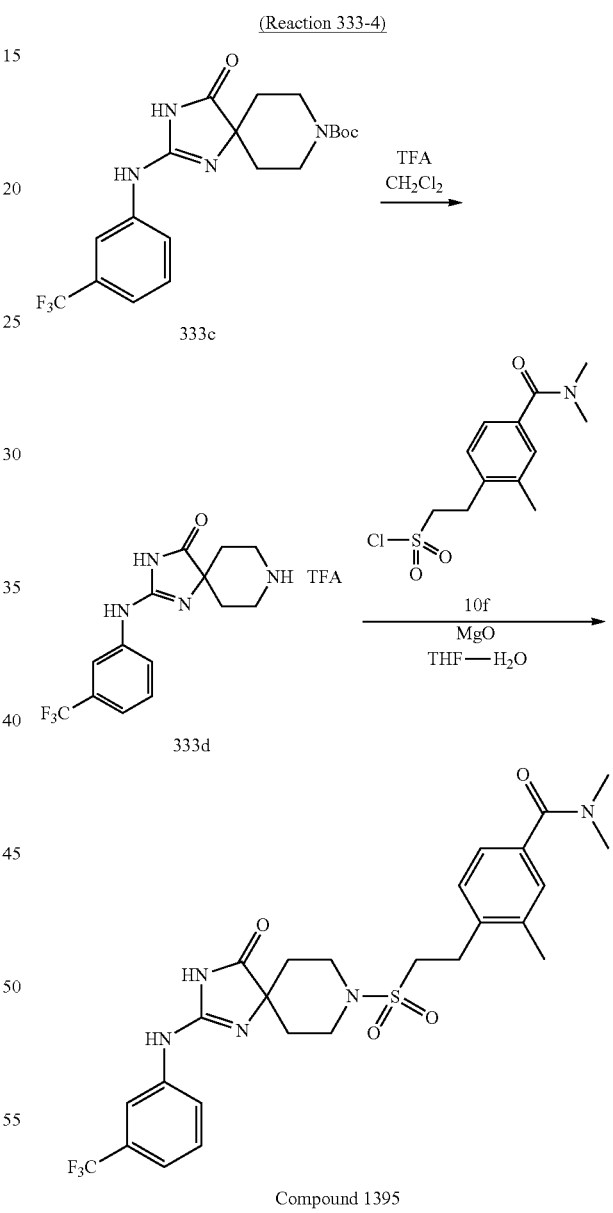

Compound 1395

3,N,N-Trimethyl-4-{2-[4-oxo-2-(3-trifluoromethyl-phenylamino)-1,3,8-triaza-spiro[4.5]dec-1-ene-8-sulfonyl]-ethyl}-benzamide was synthesized by operations similar to those in Reaction 4-1 and Reaction 190-1 using appropriate reagents and starting material.

MS (ESI) m/z=566 (M+H)+.

Example 334

3,N,N-Trimethyl-4-{2-[4-oxo-2-(4-trifluoromethyl-phenylamino)-1,3,8-triaza-spiro[4.5]dec-1-ene-8-sulfonyl]-ethyl}-benzamide (Compound 1396)

(Reaction 334-1)

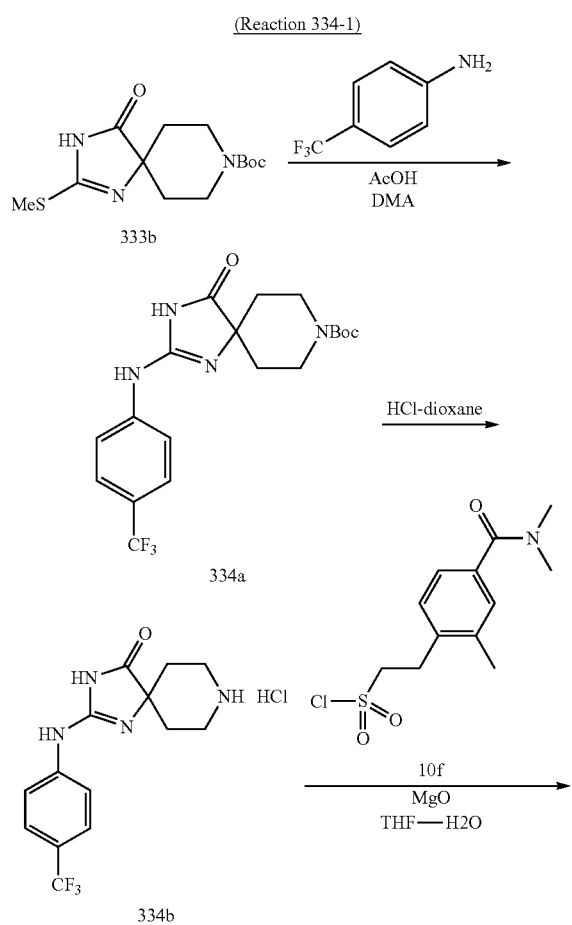

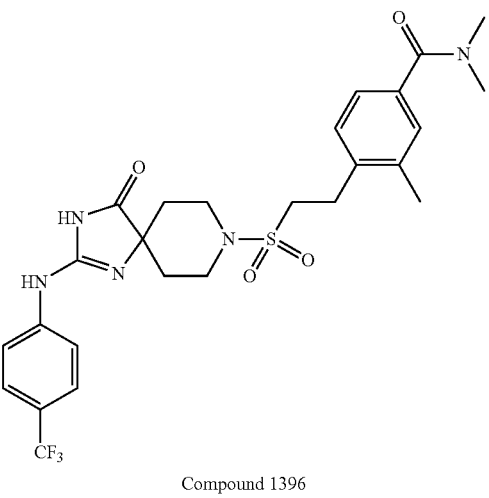

Compound 1396

3,N,N-Trimethyl-4-{2-[4-oxo-2-(4-trifluoromethyl-phenylamino)-1,3,8-triaza-spiro[4.5]dec-1-ene-8-sulfonyl]-ethyl}-benzamide was synthesized by operations similar to those in Reaction 333-3, Reaction 5-3 and Reaction 190-1 using appropriate reagents and starting material.

MS (ESI) m/z=566 (M+H)+.

The example compounds shown below were synthesized by operations similar to those in Reaction 334-1 using appropriate reagents and starting materials.

Compounds 1397 to Compound 1400

TABLE 192

| Target Compound | Structure | LCMS condition | Retention time (min) | MS (m/z) |
|---|---|---|---|---|
| 1397 | 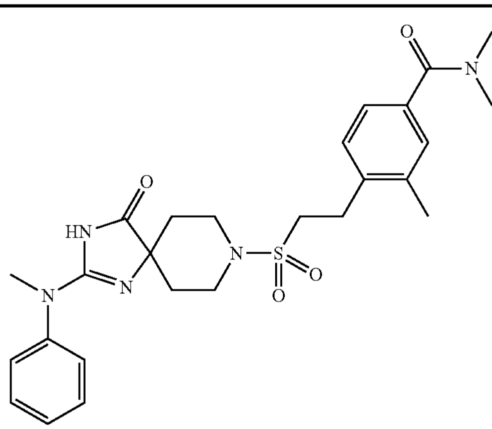 | LCMS-C-1 | 2.08 | 510 (M − H)− |

TABLE 192-continued

| Target Compound | Structure | LCMS condition | Retention time (min) | MS (m/z) |
|---|---|---|---|---|
| 1398 | 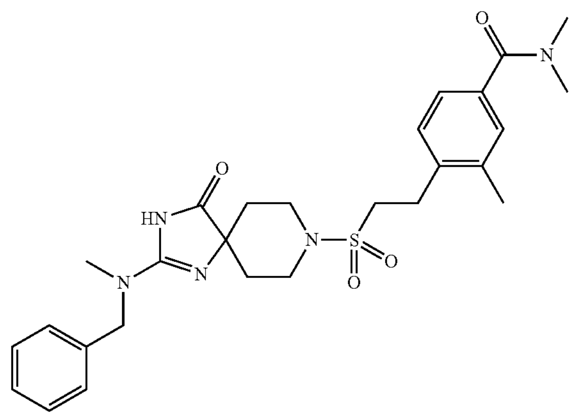 [SMILES: Cc1cc(C(=O)N(C)C)ccc1CCS(=O)(=O)N1CCC2(CC1)N=C(N(C)Cc1ccccc1)NC2=O] | LCMS-C-1 | 2.20 | 524 (M − H)− |
| 1399 | 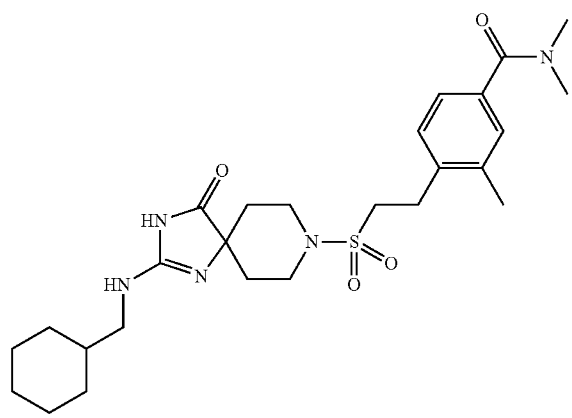 [SMILES: Cc1cc(C(=O)N(C)C)ccc1CCS(=O)(=O)N1CCC2(CC1)N=C(NCC1CCCCC1)NC2=O] | LCMS-C-1 | 2.17 | 518 (M + H)+ |
| 1400 | 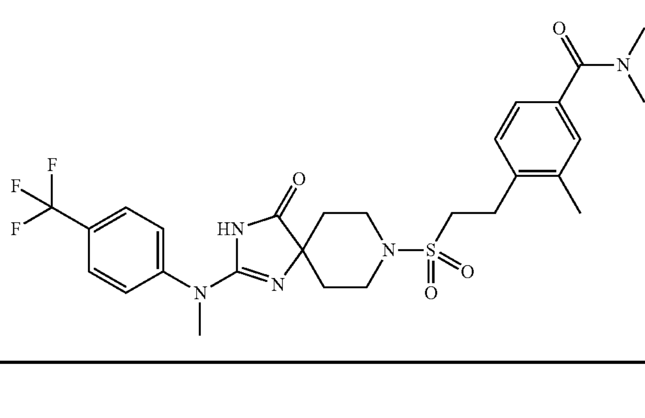 | LCMS-B-1 | 1.83 | 580 (M + H)+ |

Example 335

N-(3-Methyl-4-{2-[4-oxo-2-(4-trifluoromethyl-phenylamino)-1,3,8-triaza-spiro[4.5]dec-1-ene-8-sulfonyl]-ethyl}-phenyl)-acetamide (Compound 1401)

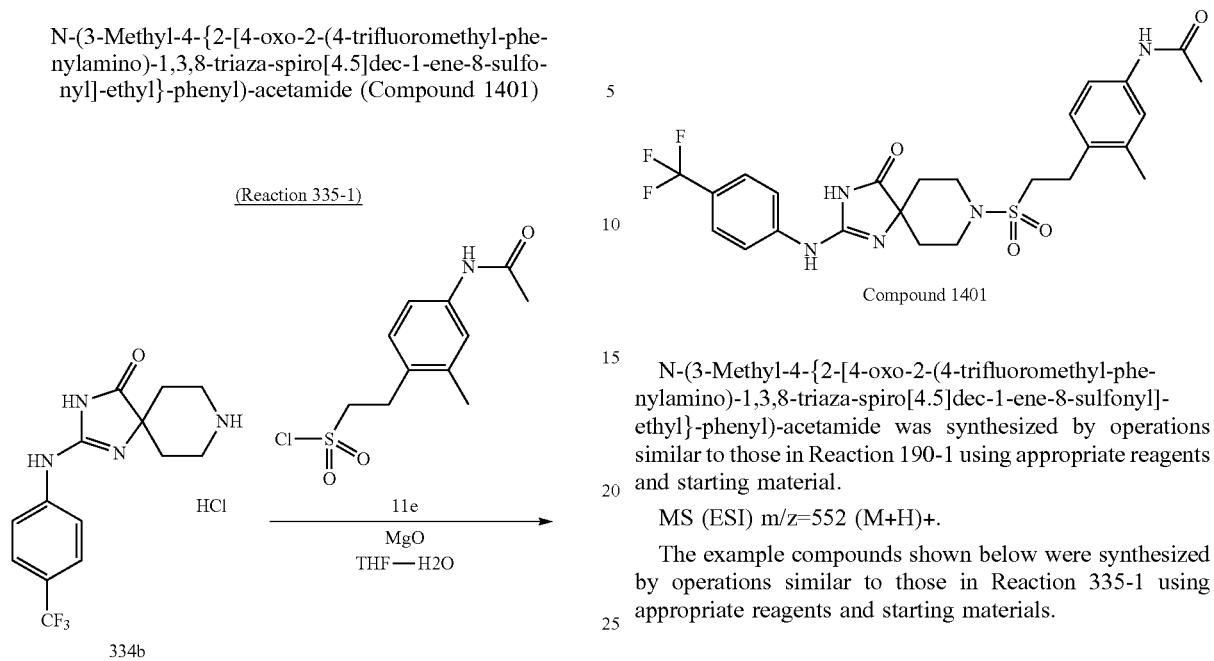

N-(3-Methyl-4-{2-[4-oxo-2-(4-trifluoromethyl-phenylamino)-1,3,8-triaza-spiro[4.5]dec-1-ene-8-sulfonyl]-ethyl}-phenyl)-acetamide was synthesized by operations similar to those in Reaction 190-1 using appropriate reagents and starting material.

MS (ESI) m/z=552 (M+H)+.

The example compounds shown below were synthesized by operations similar to those in Reaction 335-1 using appropriate reagents and starting materials.

Compound 1402

TABLE 193

| Target Compound | Structure | LCMS condition | Retention time (min) | MS (m/z) |
|---|---|---|---|---|
| 1402 | 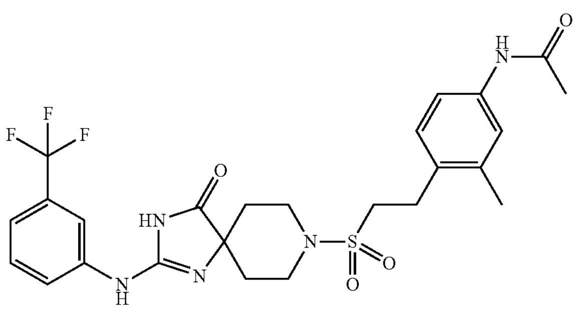 [SMILES: CC(=O)Nc1ccc(CCS(=O)(=O)N2CCC3(CC2)N=C(Nc2cccc(C(F)(F)F)c2)NC3=O)c(C)c1] | LCMS-B-1 | 1.85 | 552 (M + H)+ |

Example 336

4-{2-[2-(4-Butyl-piperidin-1-yl)-4-oxo-1,3,8-triaza-spiro[4.5]dec-1-ene-8-sulfonyl]-ethyl}-3,N,N-trimethyl-benzamide (Compound 1403)

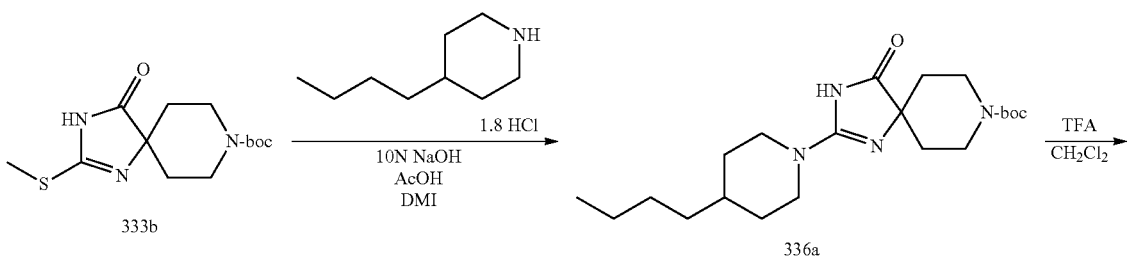

-continued

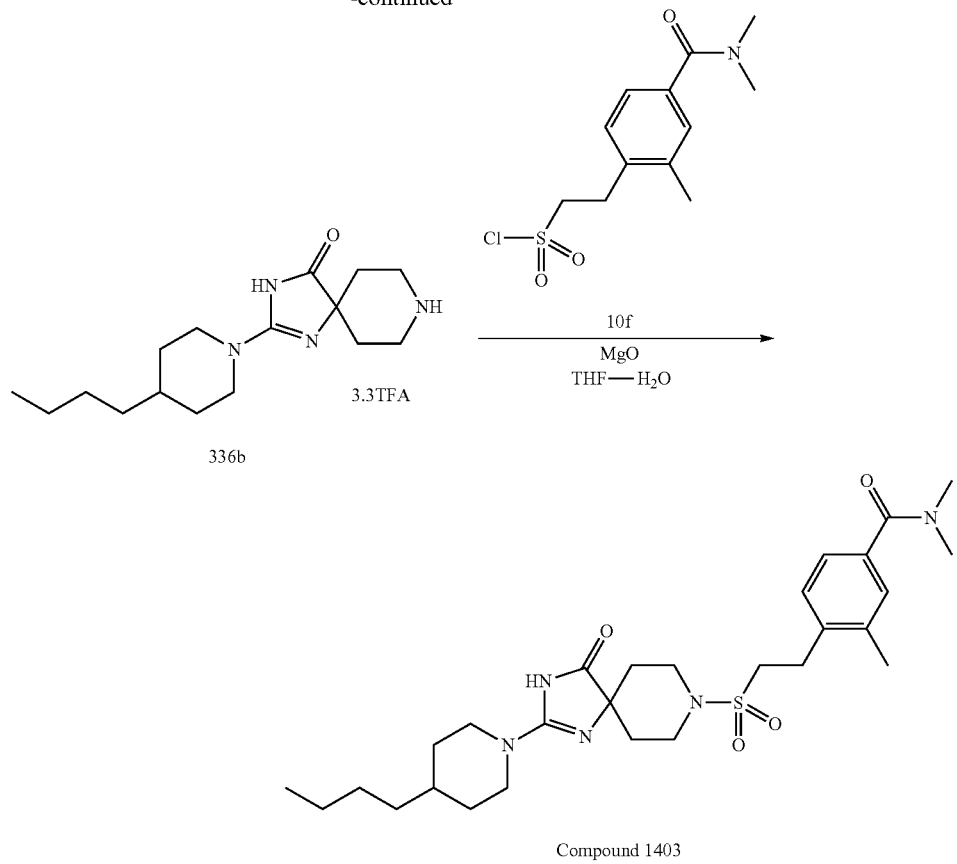

Acetic acid (0.115 ml, 1.336 mmol) and 2-methylsulfanyl-4-oxo-1,3,8-triaza-spiro[4.5]dec-1-ene-8-carboxylic acid tert-butyl ester (20 mg, 0.0668 mmol) were added to a solution of 4-butyl-piperidine hydrochloride (41 mg, 0.200 mmol) and a 10N aqueous sodium hydroxide solution (0.036 ml, 0.360 mmol) in DMI (0.3 ml), and the mixture was stirred at 110° C. overnight. The reaction mixture was purified by silica gel column chromatography to give a mixture of 2-(4-butyl-piperidin-1-yl)-4-oxo-1,3,8-triaza-spiro[4.5]dec-1-ene-8-carboxylic acid tert-butyl ester (22.3 mg).

4-{2-[2-(4-Butyl-piperidin-1-yl)-4-oxo-1,3,8-triaza-spiro[4.5]dec-1-ene-8-sulfonyl]-ethyl}-3,N,N-trimethyl-benzamide (23.0 mg, 63% in three steps) was synthesized by operations similar to those in Reaction 4-1 and Reaction 190-1 using this mixture as a starting material.

MS (ESI) m/z=546 (M+H)+.

The example compounds shown below were synthesized by operations similar to those in Reaction 336-1 using appropriate reagents and starting materials.

Compound 1404

TABLE 194

| Target Compound | Structure | LCMS condition | Retention time (min) | MS (m/z) |
|---|---|---|---|---|
| 1404 | 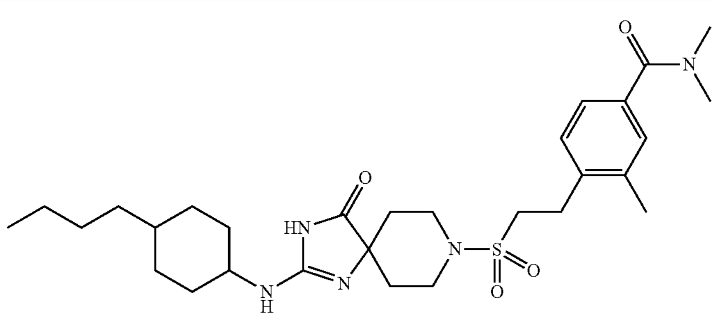 [SMILES: CCCCC1CCC(NC2=NC3(CCN(S(=O)(=O)CCc4ccc(C(=O)N(C)C)cc4C)CC3)C(=O)N2)CC1] | LCMS-B-1 | 2.24 | 560 (M + H)+ |

Example 337

4-{2-[2-(3-But-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (Compound 1405)

(Reaction 337-1)

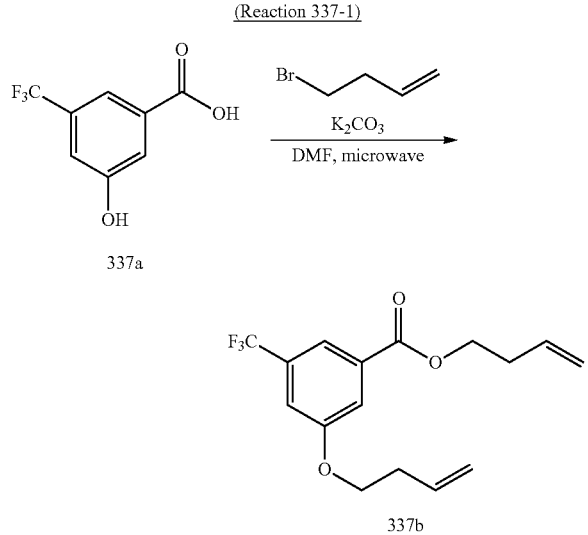

3-Hydroxy-5-trifluoromethyl-benzoic acid (2.17 g, 10.6 mmol), potassium carbonate (8.73 g, 63.2 mmol) and 4-bromo-1-butene (4.34 ml, 43.7 mmol) were dissolved in DMF (21 ml), and this mixture was irradiated in a microwave apparatus (100° C., 60 min). The reaction solution was poured into a cooled aqueous dilute hydrochloric acid solution, followed by extraction with ethyl acetate. The organic layer was washed with water and saturated brine, dried over anhydrous sodium sulfate and then concentrated under reduced pressure. The resulting crude product was purified by silica gel column chromatography to give 3-but-3-enyloxy-5-trifluoromethyl-benzoic acid but-3-enyl ester (2.64 g, 80%).

$^1$H-NMR (400 MHz, CDCl$_3$) δ 7.86 (1H, s), 7.71 (1H, s), 7.31 (1H, s), 5.95-5.81 (2H, m), 5.22-5.11 (4H, m), 4.40 (2H, t, J=6.6 Hz), 4.10 (2H, t, J=6.6 Hz), 2.60-2.51 (4H, m).

(Reaction 337-2)

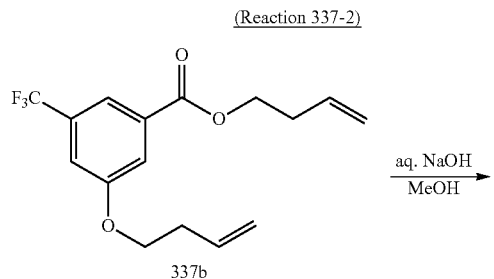

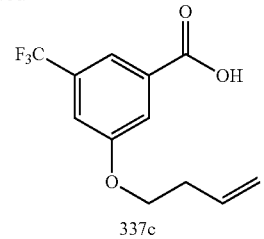

3-But-3-enyloxy-5-trifluoromethyl-benzoic acid but-3-enyl ester (2.64 g, 8.39 mmol) was dissolved in methanol. A 5 N aqueous sodium hydroxide solution (5.1 ml, 25.2 mmol) was added and the mixture was stirred at room temperature for two hours. The reaction solution was cooled, quenched with 2 N hydrochloric acid (20 ml, 40 mmol) and then extracted with ethyl acetate. The organic layer was washed with water and saturated brine, and then dried over anhydrous sodium sulfate and concentrated under reduced pressure. The resulting residue was purified by silica gel column chromatography to give 3-but-3-enyloxy-5-trifluoromethyl-benzoic acid (2.13 g, 98%).

$^1$H-NMR (400 MHz, CDCl$_3$) δ 7.95 (1H, s), 7.78 (1H, s), 7.38 (1H, s), 5.96-5.86 (1H, m), 5.23-5.14 (2H, m), 4.12 (2H, t, J=6.6 Hz), 2.59 (2H, q, J=6.5 Hz).

(Reaction 337-3)

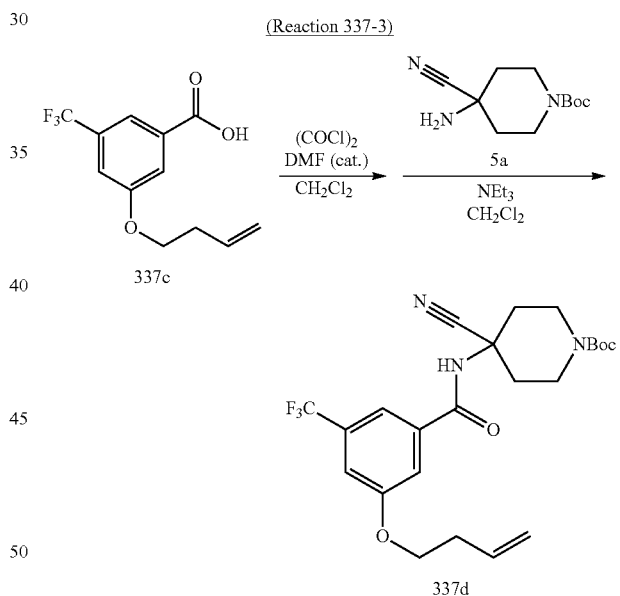

DMF (one drop) was added to a solution of 3-but-3-enyloxy-5-trifluoromethyl-benzoic acid (1.73 g, 6.65 mmol) in methylene chloride (6.8 ml). Oxalyl dichloride (0.566 ml, 6.60 mmol) was then added dropwise under ice-cooling, and the mixture was stirred at room temperature for three hours.

The reaction solution obtained above was added dropwise to a solution of 4-amino-4-cyano-piperidine-1-carboxylic acid tert-butyl ester (1.49 g, 6.65 mmol) and triethylamine (1.85 ml, 13.3 mmol) in methylene chloride (10 ml) under ice-cooling, and the mixture was stirred at room temperature for two hours. The reaction solution was cooled and water and 2 N hydrochloric acid were then sequentially added, followed by extraction with methylene chloride. The organic layer was dried over anhydrous sodium sulfate and then concentrated under reduced pressure to give 4-(3-but-3-enyloxy-5-trifluoromethyl-benzoylamino)-4-cyano-piperidine-1-carboxylic acid tert-butyl ester as a crude product (3.0 g). This compound was used in the next reaction without further purification.

MS (ESI) m/z=368 (M-Boc+H)+;

HPLC retention time: 3.32 min (analysis condition LCMS-A-1).

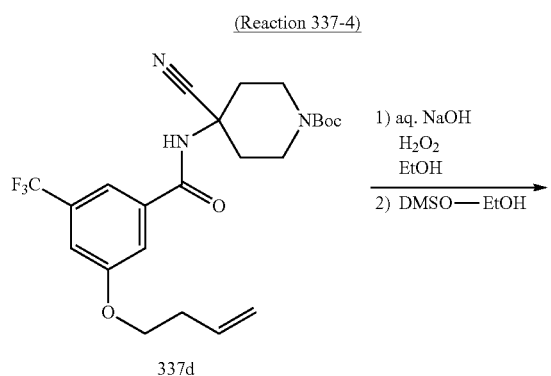

(Reaction 337-4)

337d

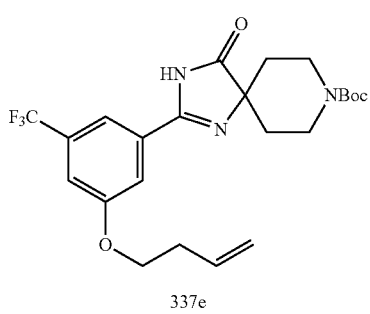

337e 4-(3-But-3-enyloxy-5-trifluoromethyl-benzoylamino)-4-cyano-piperidine-1-carboxylic acid tert-butyl ester (3.0 g) was dissolved in ethanol, and a 5 N aqueous sodium hydroxide solution (6.9 ml, 34.5 mmol) and a 30% aqueous hydrogen peroxide solution (3 ml) were added. After stirring at room temperature for two hours, DMSO (19 ml) was added to the reaction solution, and the mixture was stirred at 50° C. for four hours. The reaction solution was cooled, and then quenched with a saturated aqueous ammonium chloride solution and extracted with ethyl acetate. The organic layer was sequentially washed with a saturated aqueous ammonium chloride solution, water and saturated brine, and then dried over anhydrous sodium sulfate and concentrated under reduced pressure. The resulting residue was purified by silica gel column chromatography to give 2-(3-but-3-enyloxy-5-trifluoromethyl-phenyl)-4-oxo-1,3,8-triaza-spiro[4.5]dec-1-ene-8-carboxylic acid tert-butyl ester (2.39 g, 67% in two steps).

$^1$H-NMR (400 MHz, CDCl$_3$) δ 10.10 (1H, s), 7.76 (1H, s), 7.63 (1H, s), 7.32 (1H, s), 5.96-5.86 (1H, m), 5.24-5.15 (2H, m), 4.15 (2H, t, J=6.6 Hz), 4.01 (2H, s), 3.52 (2H, t, J=11.2 Hz), 2.60 (2H, q, J=6.7 Hz), 1.96-1.89 (2H, m), 1.65-1.55 (2H, m), 1.50 (9H, s);

MS (ESI) m/z=368 (M-Boc+H)+, 412 (M-tBu+H)+.

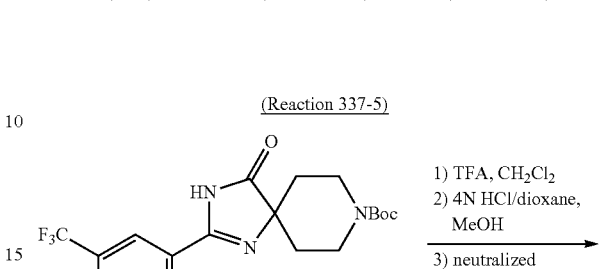

(Reaction 337-5)

337e

337f

Trifluoroacetic acid (27 ml) was added to a solution of 2-(3-but-3-enyloxy-5-trifluoromethyl-phenyl)-4-oxo-1,3,8-triaza-spiro[4.5]dec-1-ene-8-carboxylic acid tert-butyl ester (2.39 g, 5.12 mmol) in methylene chloride (54 ml), and the mixture was stirred at room temperature for 1.5 hours. The reaction solution was concentrated under reduced pressure with azeotropic distillation with toluene, and the resulting residue (trifluoroacetate) was then dissolved in methanol (50 ml). A 4 N solution of hydrochloric acid in dioxane (16 ml) was added and the mixture was concentrated under reduced pressure. The resulting residue was dissolved in a mixed solution of ethyl acetate (100 ml)-ethanol (5 ml), followed by washing with a 1 N aqueous K$_3$PO$_4$ solution. The organic layer was dried over anhydrous sodium sulfate and then concentrated under reduced pressure to give 2-(3-but-3-enyloxy-5-trifluoromethyl-phenyl)-1,3,8-triaza-spiro[4.5]dec-1-en-4-one (1.92 g). This compound was used in the next reaction without further purification.

$^1$H-NMR (CDCl$_3$) δ 7.73 (1H, s), 7.63 (1H, s), 7.29 (1H, s), 5.97-5.87 (1H, m), 5.21 (2H, d, J=17.1 Hz), 5.15 (2H, d, J=10.3 Hz), 4.15 (2H, t, J=6.8 Hz), 3.25-3.10 (4H, m), 2.60 (2H, q, J=6.7 Hz), 1.95-1.85 (2H, m), 1.60-1.57 (2H, m);

MS(ESI) m/z=368 (M+H)+.

(Reaction 337-6)

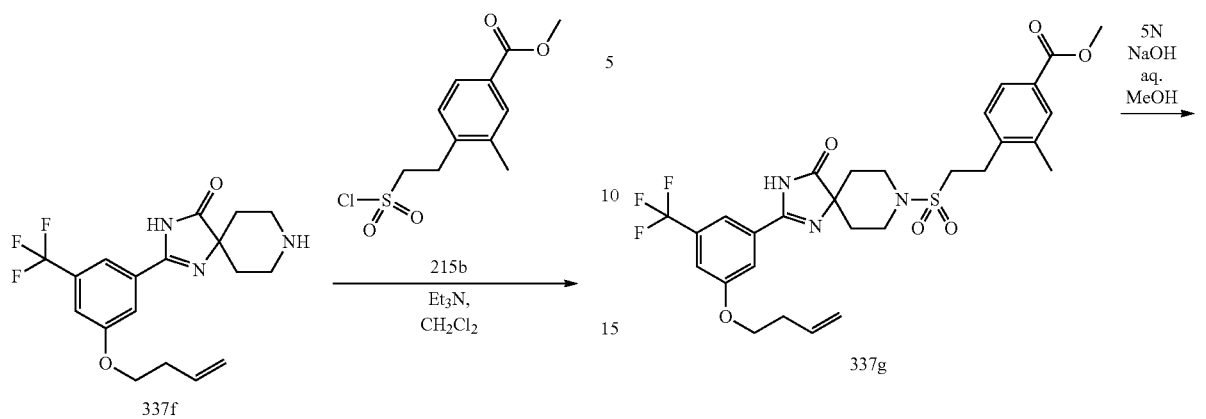

(Reaction 337-7)

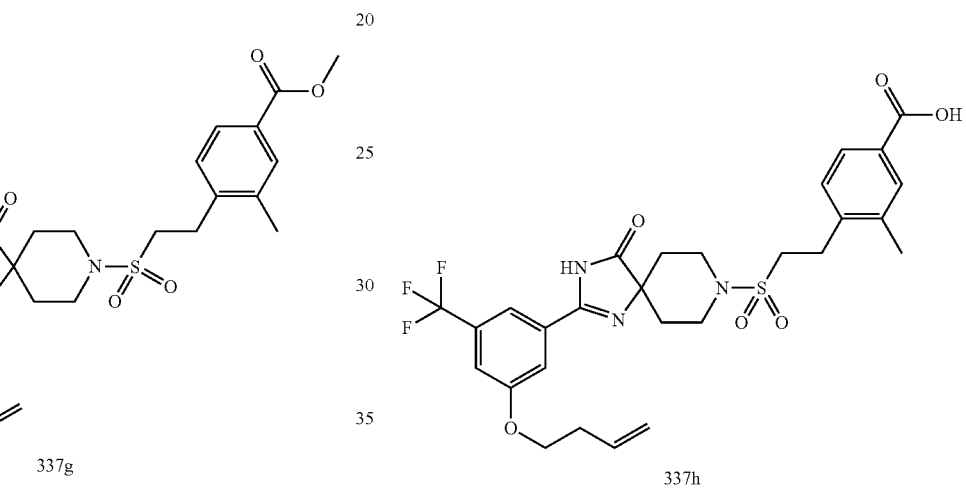

Triethylamine (1.27 ml, 9.11 mmol) and 4-(2-chlorosulfonyl-ethyl)-3-methyl-benzoic acid methyl ester (1.01 g, 3.65 mmol) were added to a solution of 2-(3-but-3-enyloxy-5-trifluoromethyl-phenyl)-1,3,8-triaza-spiro[4.5]dec-1-en-4-one (1.40 g, 3.83 mmol) in methylene chloride (35 ml) at 0° C. The mixture was stirred at room temperature for two hours, and then quenched with a saturated aqueous ammonium chloride solution and extracted with ethyl acetate. The organic layer was washed with water and saturated brine, dried over anhydrous sodium sulfate and then concentrated under reduced pressure to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid methyl ester (2.10 g). This compound was used in the next reaction without further purification.

$^1$H-NMR (400 MHz, CDCl$_3$) δ 7.87 (1H, s), 7.85-7.84 (1H, m), 7.68 (1H, s), 7.57 (1H, s), 7.31 (1H, s), 7.26-7.25 (1H, m), 5.96-5.85 (1H, m), 5.22-5.17 (2H, m), 4.14 (2H, t, J=6.6 Hz), 3.91 (3H, s), 3.83 (2H, td, J=8.2, 3.9 Hz), 3.54-3.49 (2H, m), 3.25-3.15 (4H, m), 2.60 (1H, q, J=6.7 Hz), 2.42 (3H, s), 2.13-2.06 (2H, m), 1.77-1.73 (2H, m);

MS (ESI) m/z=608 (M+H)+.

A 5 N aqueous sodium hydroxide solution (6.6 ml, 33 mmol) was added to a solution of 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid methyl ester (2.10 g) in methanol (22 ml), and the mixture was stirred at room temperature for two hours. The reaction solution was cooled and then quenched with 2 N hydrochloric acid (25 ml), followed by extraction with ethyl acetate. The organic layer was washed with water and saturated brine, dried over anhydrous sodium sulfate and then concentrated under reduced pressure to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid (1.78 g).

$^1$H-NMR (400 MHz, CD$_3$OD) δ 7.85-7.74 (3H, m), 7.41-7.32 (3H, m), 5.99-5.89 (1H, m), 5.19 (1H, dd, J=17.3, 1.7 Hz), 5.11 (1H, dd, J=10.3, 2.0 Hz), 4.17 (2H, t, J=6.6 Hz), 3.84-3.76 (2H, m), 3.56-3.46 (2H, m), 3.41-3.17 (4H, m), 2.58 (2H, q, J=6.7 Hz), 2.44 (3H, s), 2.07-1.97 (2H, m), 1.78-1.69 (2H, m);

MS (ESI) m/z=594 (M+H)+.

(Reaction 337-8)

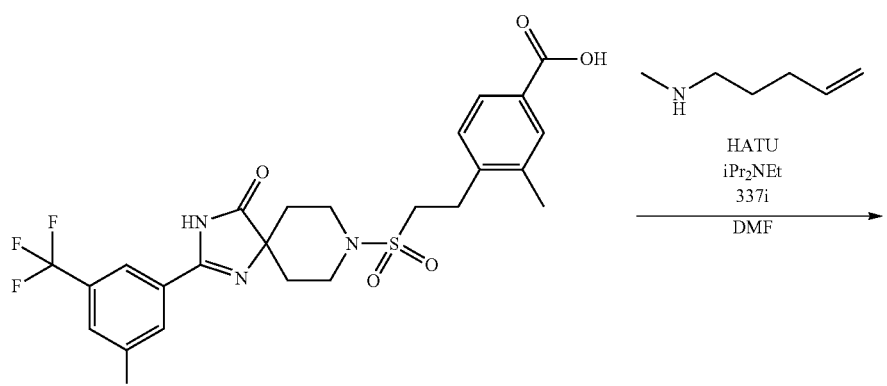

337g

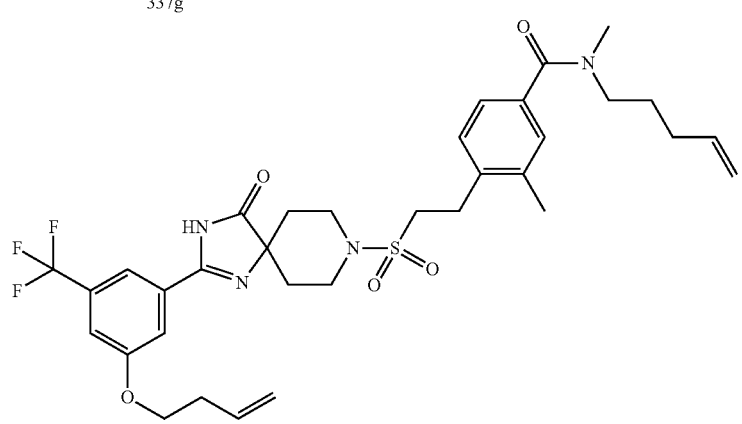

Compound 1405

HATU (194 mg, 0.510 mmol), N,N-diisopropylethylamine (143 μL) and methyl-pent-4-enyl-amine (80 mg) were added to a solution of 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid (200 mg, 0.337 mmol) in DMF (3 ml), and the mixture was stirred at room temperature overnight. A saturated aqueous ammonium chloride solution was added to the reaction solution, followed by extraction with ethyl acetate. The organic layer was washed with water and saturated brine, and then dried over anhydrous sodium sulfate and concentrated under reduced pressure. The resulting residue was purified by silica gel column chromatography to give 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (192 mg, 84%).

MS (ESI) m/z=675 (M+H)+;

HPLC retention time: 3.13 min (analysis condition LCMS-A-1).

Methyl-pent-4-enyl-amine used in the above Reaction 337-8 was synthesized by the following method (Angewandte Chemie, International Edition (2004), 43(41), 5542-5546).

(Reaction 337-9)

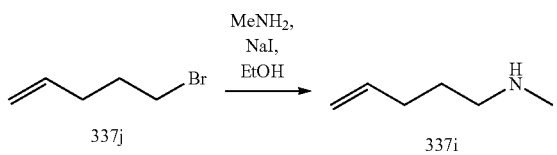

A 40% solution of methylamine in methanol (2.74 ml, 26.8 mmol) and NaI (20 mg, 0.134 mmol) were added to a solution of 5-bromo-1-butene (318 μL, 2.68 mmol) in ethanol (2 ml), and the mixture was stirred at 60° C. overnight in a sealed tube. The reaction solution was cooled and concentrated hydrochloric acid (2.4 ml) was then added. The mixture was concentrated under reduced pressure. The resulting residue was washed with tert-butyl methyl ether and then made basic with a 5 N aqueous sodium hydroxide solution under ice-cooling, followed by extraction with tert-butyl methyl ether (×3). The organic layers were dried over anhydrous sodium sulfate and then concentrated under reduced pressure to give methyl-pent-4-enyl-amine (80 mg, 30% as an object).

$^1$H-NMR (400 MHz, CDCl$_3$) δ 5.88-5.77 (1H, m), 5.05-4.99 (1H, m), 4.98-4.93 (1H, m), 2.58 (2H, t, J=7.1 Hz), 2.43 (3H, s), 2.12-2.03 (2H, m), 1.62-1.49 (2H, m).

Example 338

Compound 1406

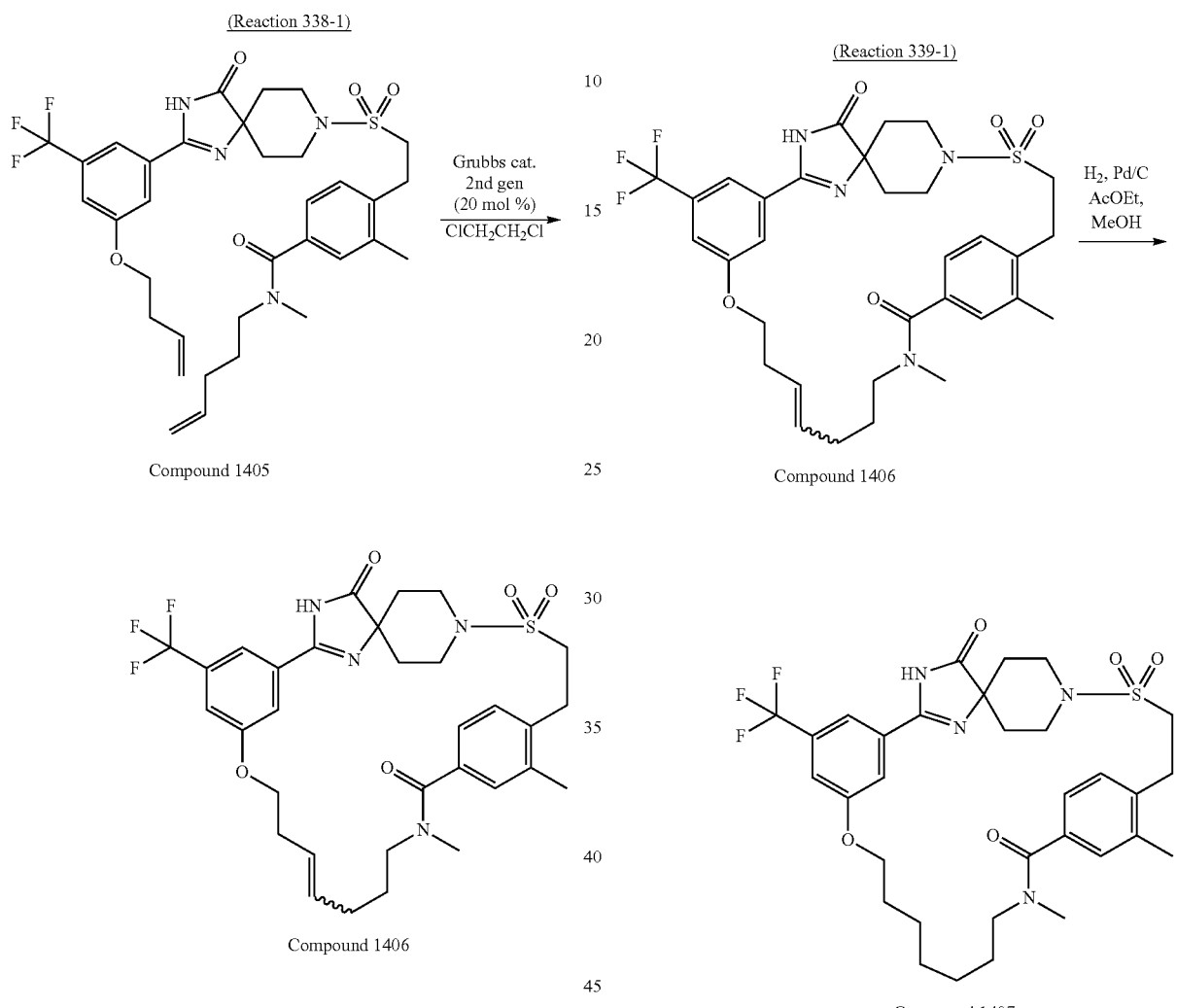

Example 339

Compound 1407

Grubbs catalyst $2^{nd}$ generation (44 mg, 0.0519 mmol) was added to a solution of 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-pent-4-enyl-benzamide (175 mg, 0.259 mmol) in 1,2-dichloroethane (260 ml), and the mixture was stirred at 40° C. overnight in an argon stream. The reaction solution was concentrated under reduced pressure, and the resulting residue was then purified by silica gel column chromatography to give a macrocyclic olefin compound (Compound 1406) (157 mg, 94%).

$^1$H-NMR (400 MHz, CDCl$_3$) δ 9.76 (0.2H, s), 9.59 (0.8H, s), 8.19 (1H, s), 8.12 (1H, s), 7.35-7.10 (4H, m), 5.61-5.48 (2H, m), 4.20 (0.8H, t, J=5.4 Hz), 4.09 (0.2H, t, J=5.1 Hz), 3.67-3.05 (10H, m), 3.03 (0.6H, s), 2.98 (2.4H, s), 2.65-2.48 (2H, m), 2.47 (2.4H, s), 2.41 (0.6H, s), 2.33-2.18 (2H, m), 1.80-1.22 (6H, m);

MS (ESI) m/z=647 (M+H)+.

10% Pd—C (50% wet) (14.4 mg) was added to a macrocyclic olefin compound (Compound 1406) (36 mg, 0.0551 mmol) in a mixed solvent of methanol and ethyl acetate (1:10, 5.5 ml), and the mixture was stirred overnight in a hydrogen atmosphere. The reaction solution was filtered through celite, and the filtrate was then concentrated. The resulting residue was purified by P-TLC (CH$_2$Cl$_2$-MeOH) to give a saturated macrocyclic compound (Compound 1407) (30 mg, 94%).

$^1$H-NMR (400 MHz, CD$_3$OD) δ 7.93 (1H, s), 7.66 (1H, s), 7.40-7.35 (2H, m), 7.26-7.18 (2H, m), 4.07 (2H, t, J=5.4 Hz), 3.81 (2H, br d, J=11.7 Hz), 3.48-3.13 (8H, m), 3.06 (3H, s), 2.44 (3H, s), 2.13-1.10 (14H, m);

MS (ESI) m/z=649 (M+H)+.

Example 340

Compound 1408

(Reaction 340-1)

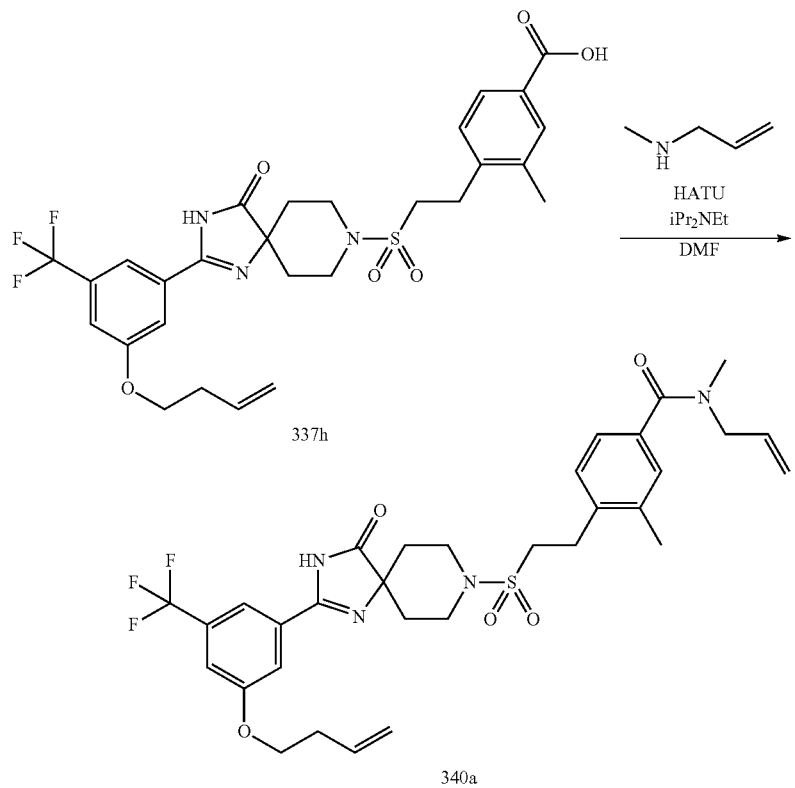

N-Allyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and allyl-methyl-amine as starting materials.

MS (ESI) m/z=647 (M+H)+;

HPLC retention time: 2.95 min (analysis condition LCMS-A-1).

(Reaction 340-2)

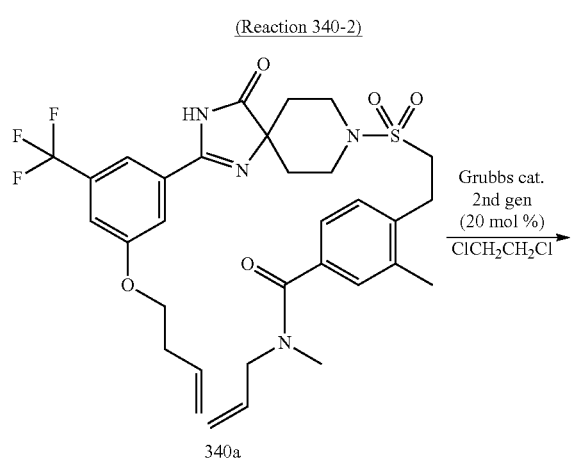

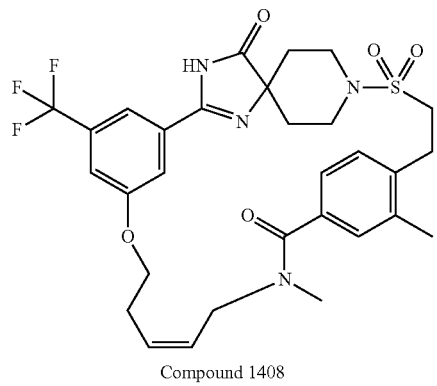

Compound 1408

A macrocyclic olefin compound (Compound 1408) was obtained by the same method as in Reaction 338-1 using N-allyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide (151 mg, 0.233 mmmol) as a starting material.

MS (ESI) m/z=619 (M+H)+;

HPLC retention time: 2.69 min (analysis condition LCMS-A-1).

Example 341
Compound 1409
(Reaction 341-1)
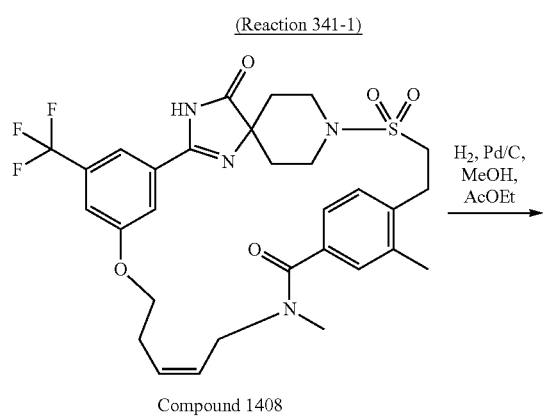
Compound 1408
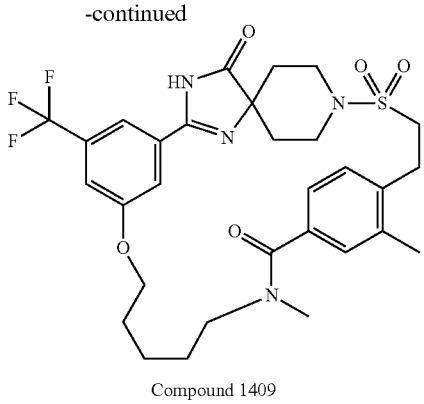
Compound 1409
A saturated macrocyclic compound (Compound 1409) was obtained by the same method as in Reaction 339-1 using a macrocyclic olefin compound (Compound 1408) as a starting material.
MS (ESI) m/z=621 (M+H)+;
HPLC retention time: 2.72 min (analysis condition LCMS-A-1).
Example 342
Compounds 1410 and Compound 1411
(Reaction 342-1)
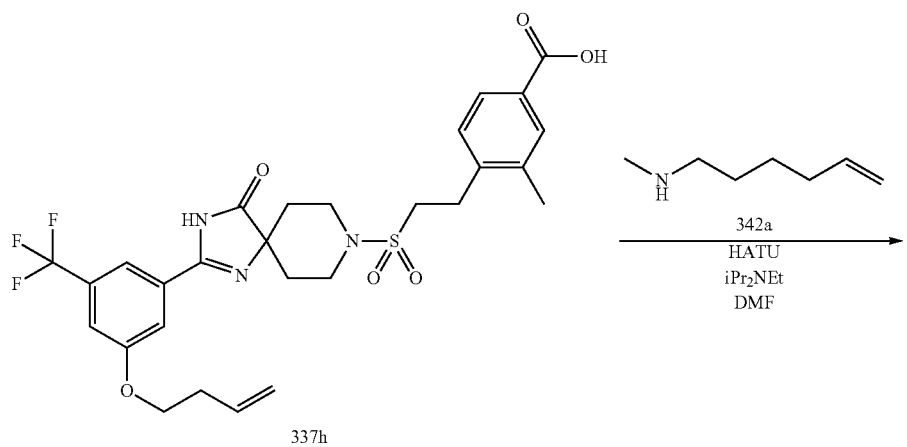
337h
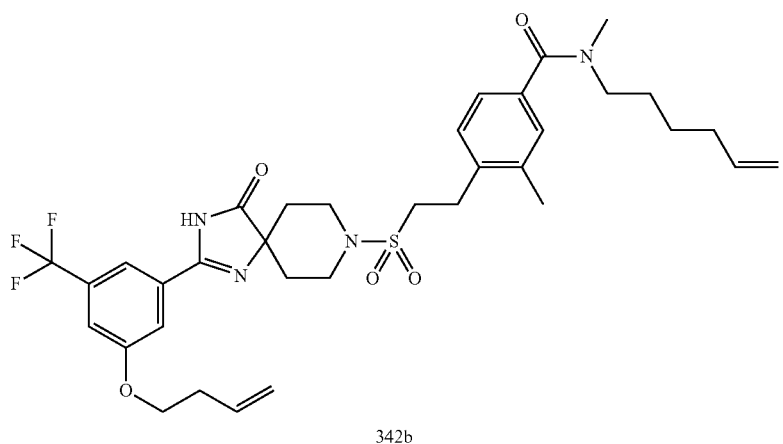
342b 4-{2-[2-(3-But-3-enyloxy-5-trifluoromethyl-phenyl)-4-oxo-1,3,8-triaza-spiro[4.5]dec-1-ene-8-sulfonyl]-ethyl}-N-hex-5-enyl-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and hex-5-enyl-methyl-amine as starting materials.

MS (ESI) m/z=689 (M+H)+;

HPLC retention time: 3.32 min (analysis condition LCMS-A-1).

Hex-5-enyl-methyl-amine used in the above Reaction 342-1 was synthesized in the following manner.

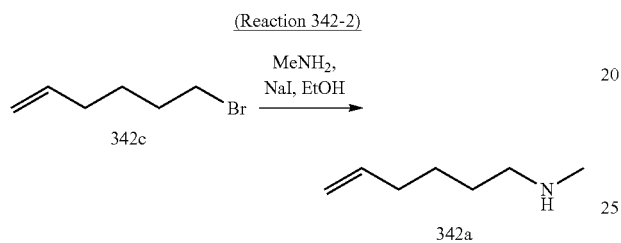

Hex-5-enyl-methyl-amine was obtained by the same method as in Reaction 337-9 using 6-bromo-1-hexene (437 mg, 2.68 mmol) as a raw material.

$^1$H-NMR (400 MHz, CDCl$_3$) δ 5.86-5.76 (1H, m), 5.03-4.93 (2H, m), 2.57 (2H, t, J=7.0 Hz), 2.43 (3H, s), 2.10-2.04 (2H, m), 1.54-1.38 (4H, m).

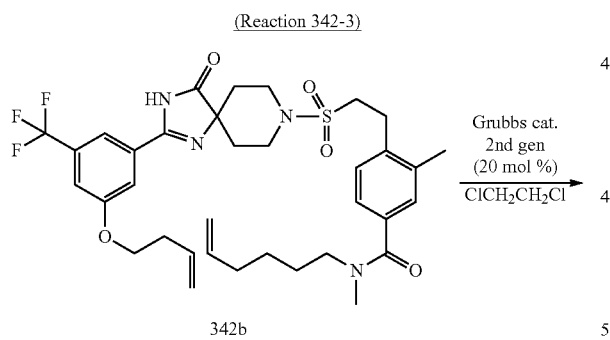

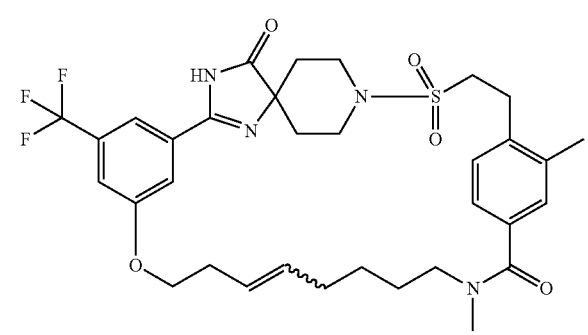

A macrocyclic olefin compound (Compound 1410, E/Z=98:2) and a macrocyclic olefin compound (Compound 1411, E/Z=59:41) were obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-N-hex-5-enyl-3,N-dimethyl-benzamide as a starting material.

Compound 1410

MS (ESI) m/z=661 (M+H)+; HPLC retention time: 3.09 min (analysis condition LCMS-A-1).

Compound 1411

MS (ESI) m/z=661 (M+H)+;

HPLC retention time: 3.08 min (analysis condition LCMS-A-1).

Example 343

Compound 1412

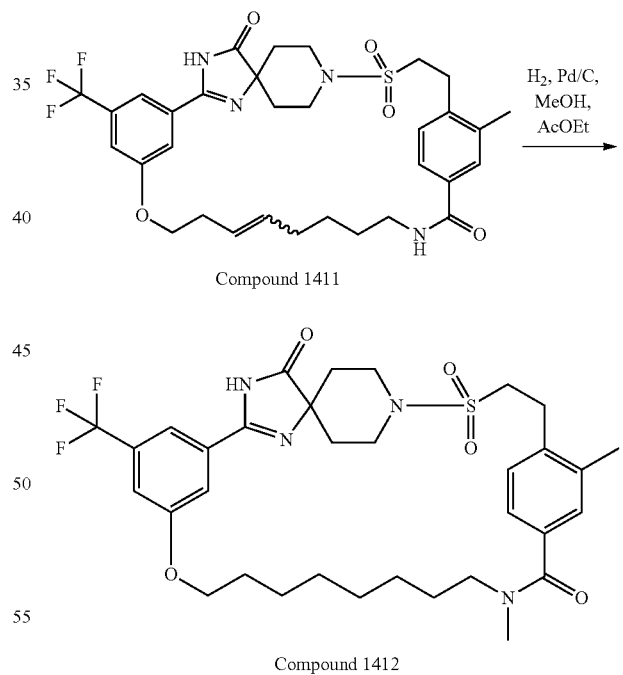

A saturated macrocyclic compound (Compound 1412) was obtained by the same method as in Reaction 339-1 using a macrocyclic olefin compound (Compound 1411) as a starting material.

MS (ESI) m/z=663 (M+H)+;

HPLC retention time: 3.22 min (analysis condition LCMS-A-1).

Example 344

Compounds 1413 and Compound 1414

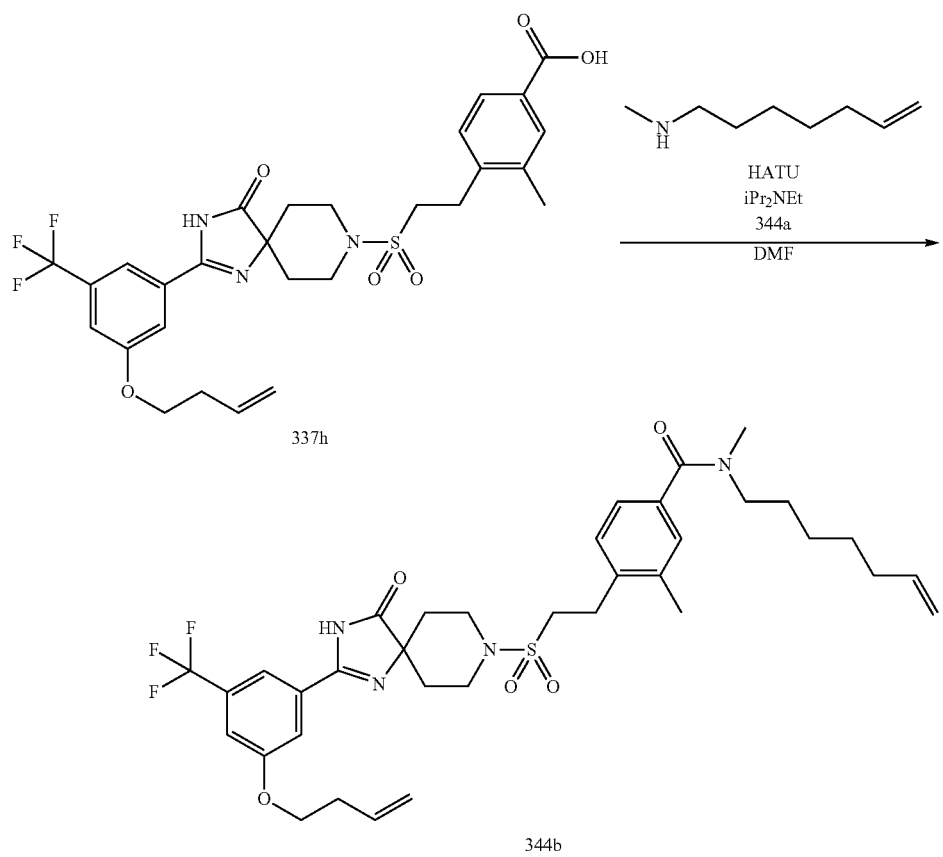

4-{2-[2-(3-But-3-enyloxy-5-trifluoromethyl-phenyl)-4-oxo-1,3,8-triaza-spiro[4.5]dec-1-ene-8-sulfonyl]-ethyl}-N-hept-6-enyl-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and hept-6-enyl-methyl-amine as starting materials.

MS (ESI) m/z=703 (M+H)+;

HPLC retention time: 3.45 min (analysis condition LCMS-A-1).

Hept-6-enyl-methyl-amine used in the above Reaction 344-1 was synthesized as follows.

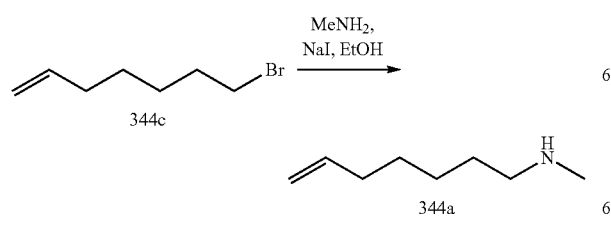

Hept-6-enyl-methyl-amine was obtained by the same method as in Reaction 337-9 using 7-bromo-1-heptene as a raw material.

$^1$H-NMR (CDCl$_3$) δ 5.86-5.76 (1H, m), 5.02-4.97 (1H, m), 4.95-4.92 (1H, m), 2.56 (2H, t, J=7.1 Hz), 2.43 (3H, s), 2.05 (2H, q, J=7.0 Hz), 1.52-1.29 (6H, m).

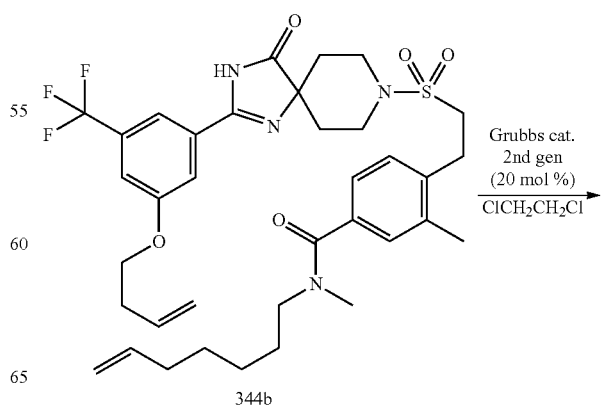

1575

-continued

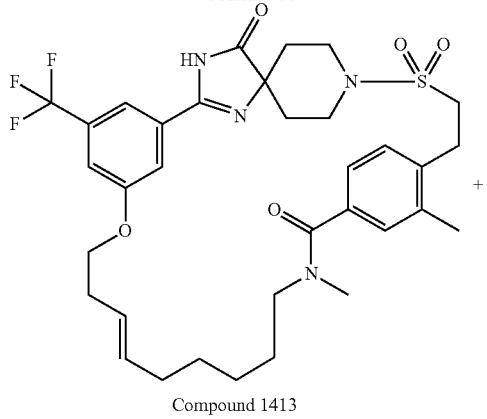

Compound 1413

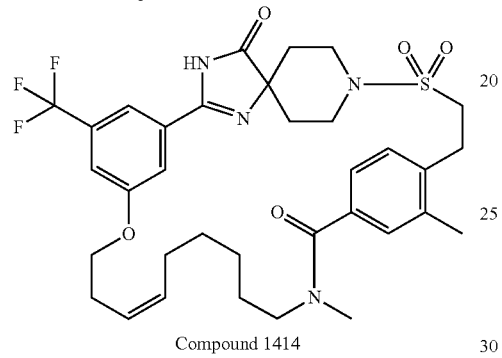

Compound 1414

A macrocyclic olefin compound (E/Z mixture) was obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-N-hept-6-enyl-3,N-dimethyl-benzamide as a starting material. This mixture was purified by HPLC to give Compound 1413 (E/Z=97:3) and Compound 1414 (E/Z=10:90).

Compound 1413

MS (ESI) m/z=675 (M+H)+; HPLC retention time: 3.20 min (analysis condition LCMS-A-1).

Compound 1414

MS (ESI) m/z=675 (M+H)+;
HPLC retention time: 3.18 min (analysis condition LCMS-A-1).

1576

Example 345

Compound 1415

(Reaction 345-1)

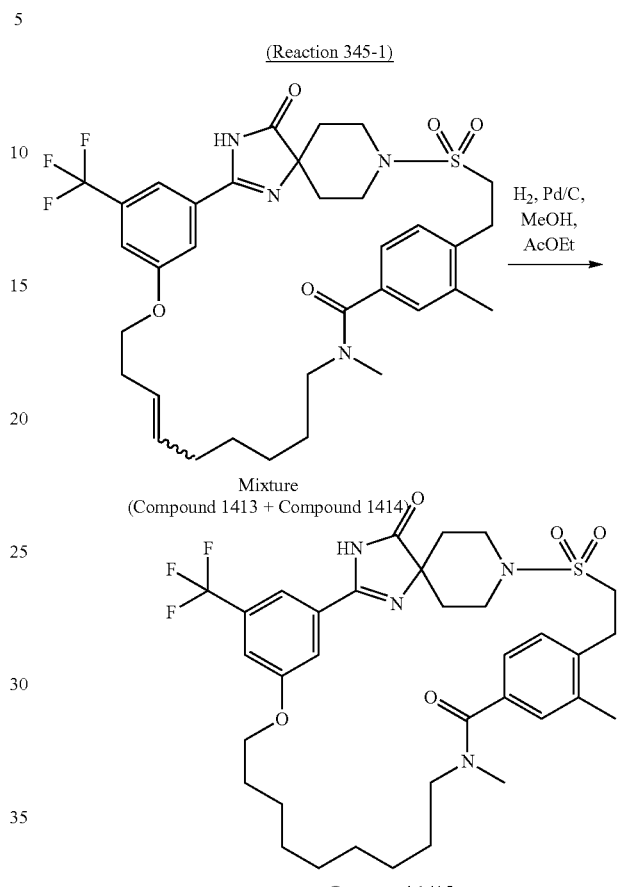

A saturated macrocyclic compound (Compound 1415) was obtained by the same method as in Reaction 339-1 using a macrocyclic olefin compound (a mixture of Compound 1413 and Compound 1414) as a starting material.

MS (ESI) m/z=677 (M+H)+;
HPLC retention time: 3.34 min (analysis condition LCMS-A-1).

Example 346

Compounds 1416 and Compound 1417

(Reaction 346-1)

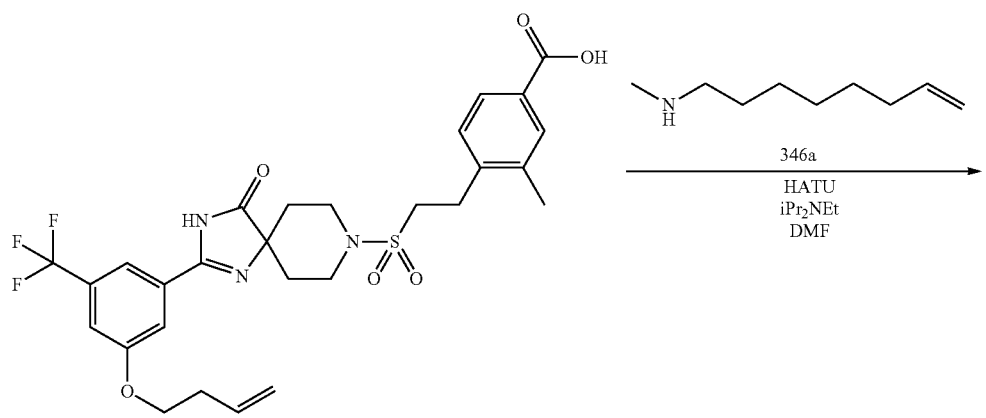

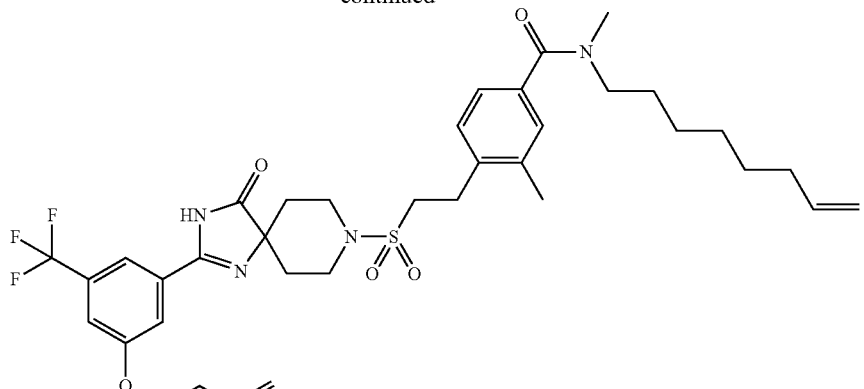

346b

4-{2-[2-(3-But-3-enyloxy-5-trifluoromethyl-phenyl)-4-oxo-1,3,8-triaza-spiro[4.5]dec-1-ene-8-sulfonyl]-ethyl}-3,N-dimethyl-N-oct-7-enyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and methyl-oct-7-enyl-amine as starting materials.

MS (ESI) m/z=717 (M+H)+;

HPLC retention time: 3.55 min (analysis condition LCMS-A-1)

Methyl-oct-7-enyl-amine used in the above Reaction 346-1 was synthesized as follows.

(Reaction 346-2)

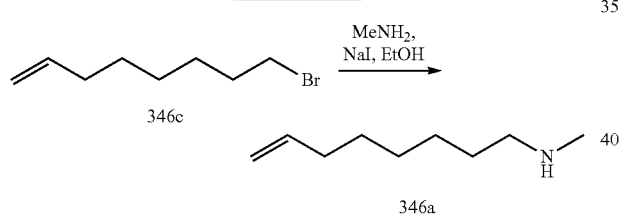

Methyl-oct-7-enyl-amine was obtained by the same method as in Reaction 337-9 using 8-bromo-1-octene as a raw material.

$^1$H-NMR (400 MHz, CDCl$_3$) δ 5.86-5.76 (1H, m), 5.02-4.96 (1H, m), 4.95-4.91 (1H, m), 2.56 (2H, t, J=7.1 Hz), 2.43 (3H, s), 2.07-2.01 (2H, m), 1.50-1.30 (8H, m).

(Reaction 346-3)

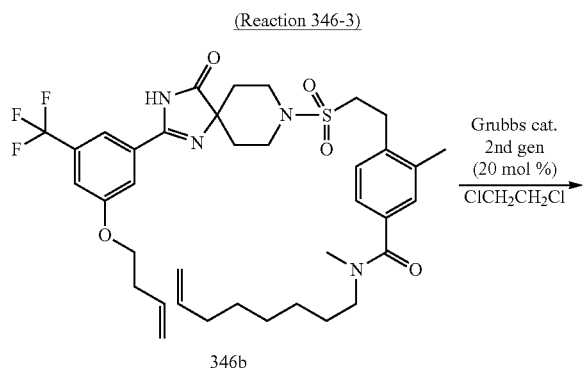

346b

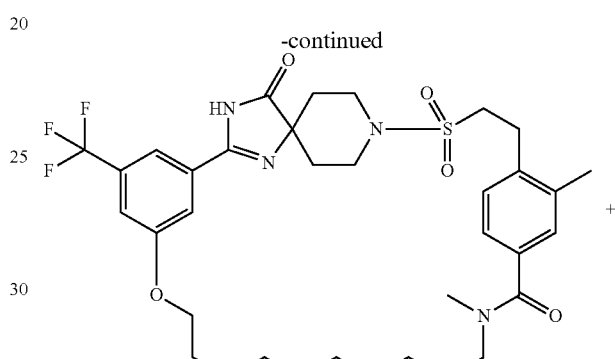

Compound 1416

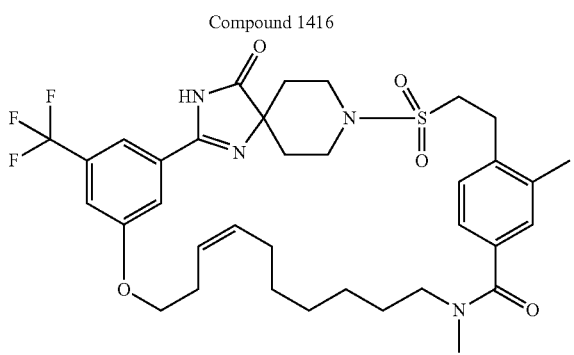

Compound 1417

A macrocyclic olefin compound (E/Z mixture) was obtained by the same method as in Reaction 338-1 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-N-oct-7-enyl-benzamide as a starting material. The resulting mixture was purified by HPLC (MeOH/MeCN/H$_2$O) to give Compound 1416 (E/Z=96:4) and Compound 1417 (E/Z=19:81).

Compound 1416

MS (ESI) m/z=689 (M+H)+;
HPLC retention time: 3.38 min (analysis condition LCMS-A-1).

Compound 1417

MS (ESI) m/z=689 (M+H)+;
HPLC retention time: 3.26 min (analysis condition LCMS-A-1).

Example 347
Compound 1418
(Reaction 347-1)
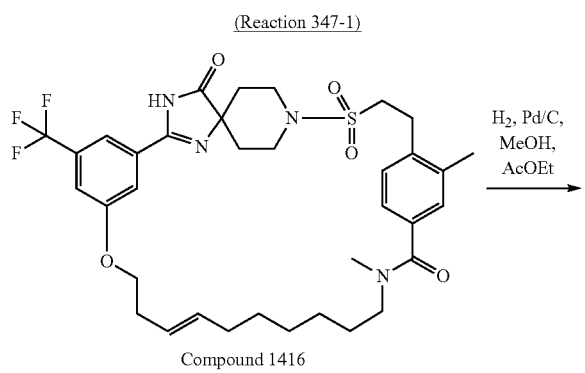
Compound 1416
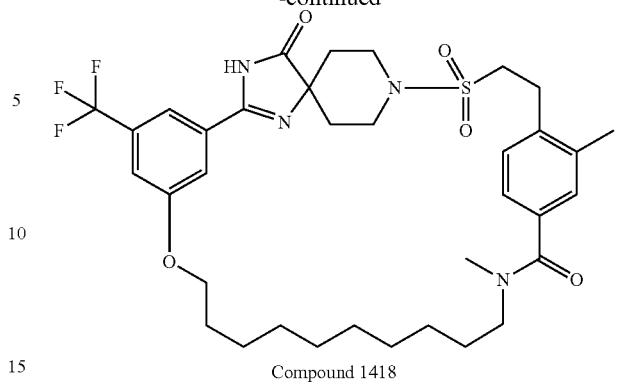
Compound 1418
A saturated macrocyclic compound (Compound 1418) was obtained by the same method as in Reaction 339-1 using a macrocyclic olefin compound (Compound 1416) as a starting material.
MS (ESI) m/z=691 (M+H)+;
HPLC retention time: 3.56 min (analysis condition LCMS-A-1).
Example 348
Compound 1419
(Reaction 348-1)
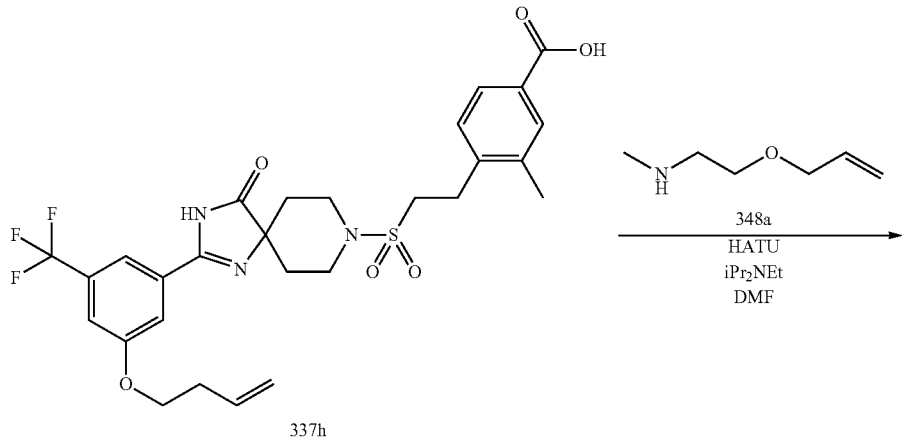
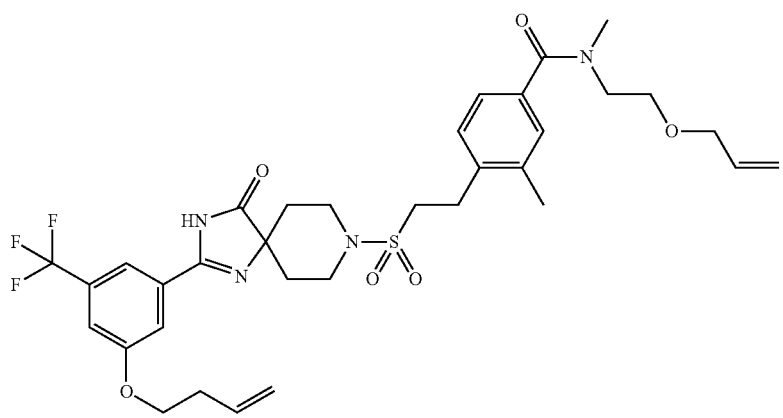
Compound 1419

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and (2-allyloxy-ethyl)-methyl-amine as starting materials.

MS (ESI) m/z=691 (M+H)+;

HPLC retention time: 3.08 min (analysis condition LCMS-A-1).

(2-Allyloxy-ethyl)-methyl-amine used in the above Reaction 348-1 was synthesized in the following manner.

(Reaction 348-2)

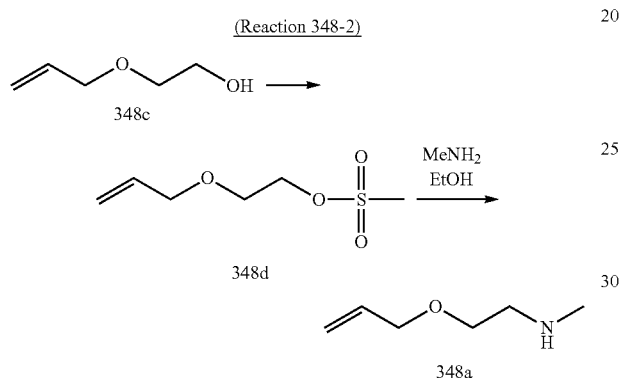

(2-Allyloxy-ethyl)-methyl-amine was obtained by the same method as in Reaction 337-9 using, as a starting material, methanesulfonic acid 2-allyloxy-ethyl ester synthesized from 2-allyloxy-ethanol by the method described in Journal of Organic Chemistry (2006), 71(21), 8183-8189.

$^1$H-NMR (400 MHz, CDCl$_3$) δ 5.97-5.87 (1H, m), 5.30-5.24 (1H, m), 5.20-5.17 (1H, m), 4.00 (2H, br d, J=5.9 Hz), 3.55 (2H, t, J=5.4 Hz), 2.76 (2H, t, J=5.1 Hz), 2.45 (3H, s).

Example 349

Compound 1420

(Reaction 349-1)

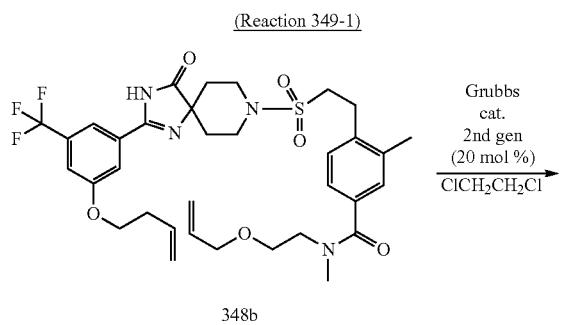

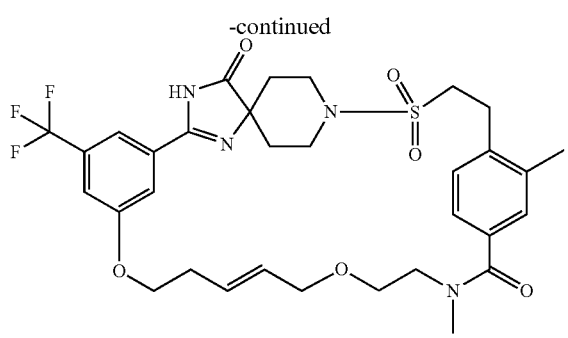

Compound 1420

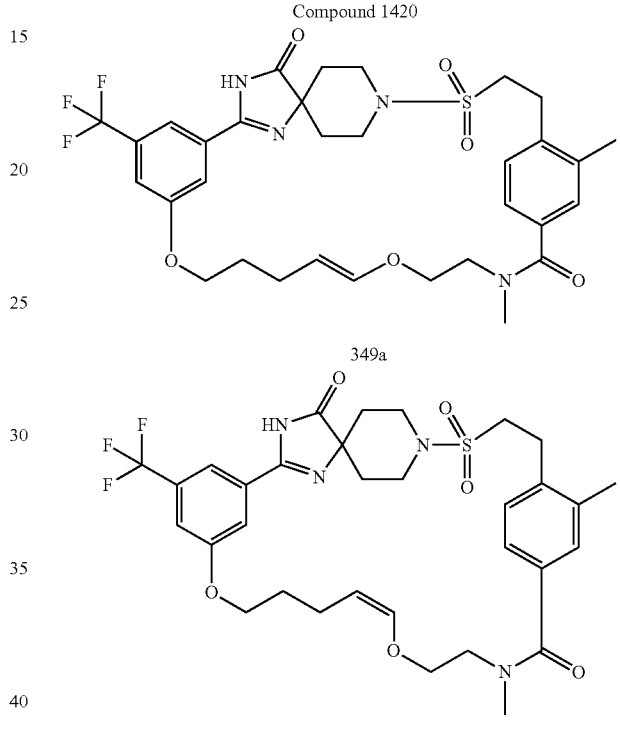

A macrocyclic olefin compound (Compound 1420) and its isomer A (349a) and isomer B (349b) were obtained by the same method as in Reaction 338-1 using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide as a starting material.

Compound 1420

MS (ESI) m/z=663 (M+H)+;

HPLC retention time: 2.84 min (analysis condition LCMS-A-1).

Isomer A (349a)

MS (ESI) m/z=663 (M+H)+

HPLC retention time: 2.77 min (analysis condition LCMS-A-1).

Isomer B (349b)

MS (ESI) m/z=663 (M+H)+

HPLC retention time: 2.96 min (analysis condition LCMS-A-1).

Example 350
Compound 1421
(Reaction 350-1)
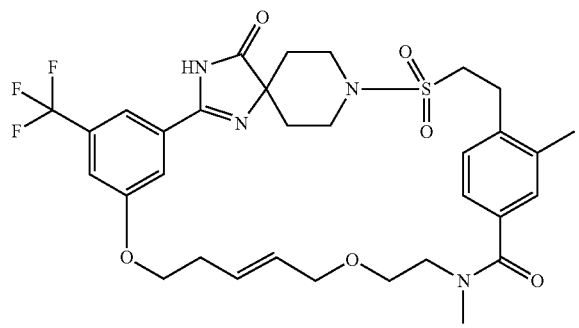
Compound 1420
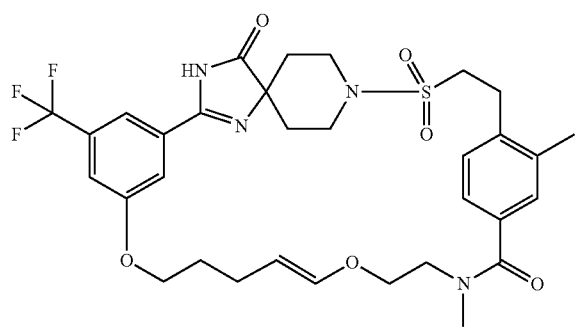
349a
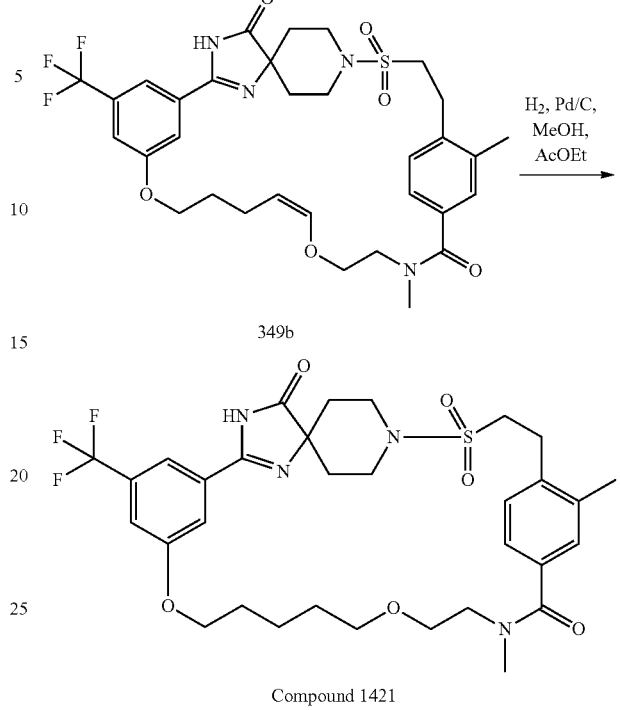
349b
Compound 1421
A saturated macrocyclic compound (Compound 1421) was obtained by the same method as in Reaction 339-1 using macrocyclic olefin mixture (Compounds 1420, 349a and 349b) as a starting material.
MS (ESI) m/z=665 (M+H)+; HPLC retention time: 2.95 min (analysis condition LCMS-A-1).
Example 351
Compounds 1422 and Compound 1423
(Reaction 351-1)
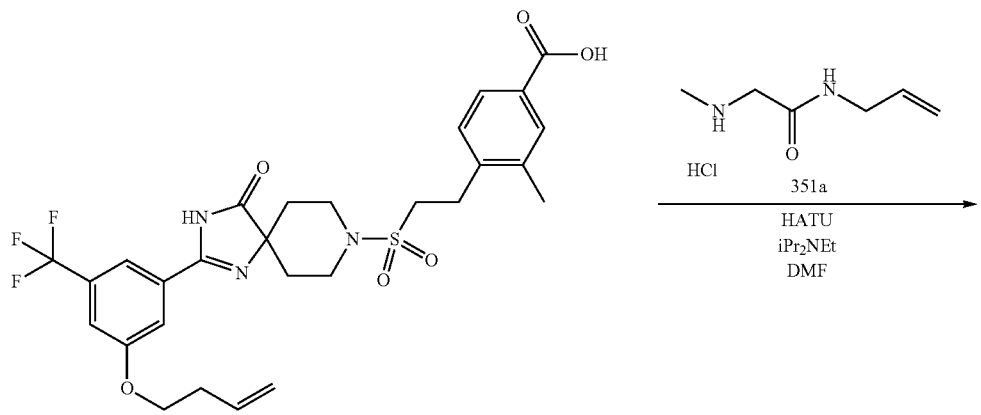
337h

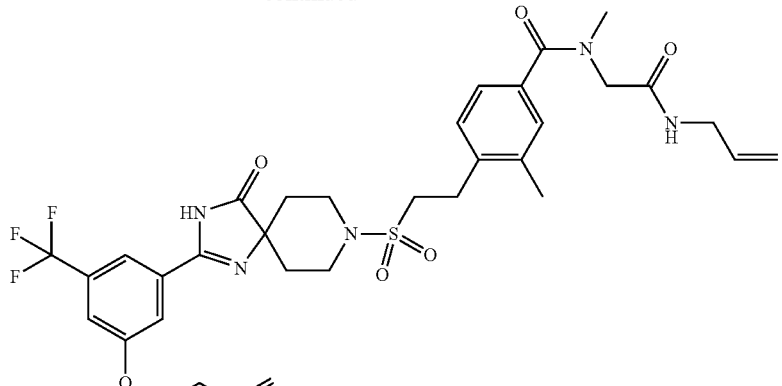

351b

N-Allylcarbamoylmethyl-4-{2-[2-(3-but-3-enyloxy-5-tri-fluoromethyl-phenyl)-4-oxo-1,3,8-triaza-spiro[4.5]dec-1-ene-8-sulfonyl]-ethyl}-3,N-dimethyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and N-allyl-2-methylamino-acetamide hydrochloride as starting materials.

MS (ESI) m/z=704 (M+H)+;

HPLC retention time: 2.80 min (analysis condition LCMS-A-1).

N-Allyl-2-methylamino-acetamide hydrochloride used in the above reaction was synthesized by the following method.

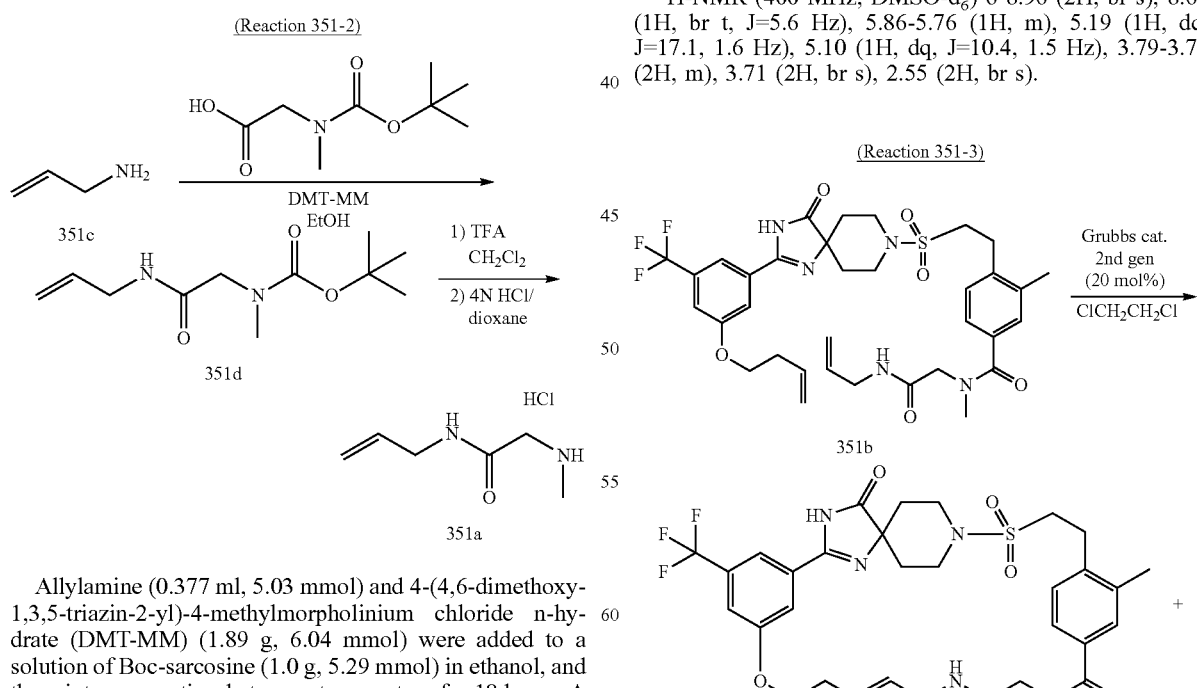

Allylamine (0.377 ml, 5.03 mmol) and 4-(4,6-dimethoxy-1,3,5-triazin-2-yl)-4-methylmorpholinium chloride n-hydrate (DMT-MM) (1.89 g, 6.04 mmol) were added to a solution of Boc-sarcosine (1.0 g, 5.29 mmol) in ethanol, and the mixture was stirred at room temperature for 18 hours. A saturated aqueous sodium bicarbonate solution and water were added to the reaction solution, followed by extraction with ether. The organic layer was washed with water and saturated brine, dried over anhydrous sodium sulfate and then concentrated under reduced pressure to give allylcarbamoylmethyl-methyl-carbamic acid tert-butyl ester (712 mg).

$^1$H-NMR (400 MHz, CDCl$_3$) δ 6.27 (0.5H, br s), 6.02 (0.5H, br s), 5.88-5.79 (1H, m), 5.18 (1H, br d, J=17.6 Hz), 5.15 (1H, br d, J=11.2 Hz), 3.91 (2H, br t, J=5.6 Hz), 3.88 (2H, s), 2.95 (3H, s), 1.47 (9H, s).

Trifluoroacetic acid (7 ml) was added to a solution of the resulting allylcarbamoylmethyl-methyl-carbamic acid tert-butyl ester in methylene chloride (14 ml), and the mixture was stirred at room temperature for three hours. The reaction solution was concentrated under reduced pressure, and 4 N hydrochloric acid-dioxane was then added to the resulting residue. The mixture was concentrated under reduced pressure again to give N-allyl-2-methylamino-acetamide hydrochloride (577 mg). This was used in the next reaction without complete purification.

$^1$H-NMR (400 MHz, DMSO-d$_6$) δ 8.96 (2H, br s), 8.68 (1H, br t, J=5.6 Hz), 5.86-5.76 (1H, m), 5.19 (1H, dq, J=17.1, 1.6 Hz), 5.10 (1H, dq, J=10.4, 1.5 Hz), 3.79-3.75 (2H, m), 3.71 (2H, br s), 2.55 (2H, br s).

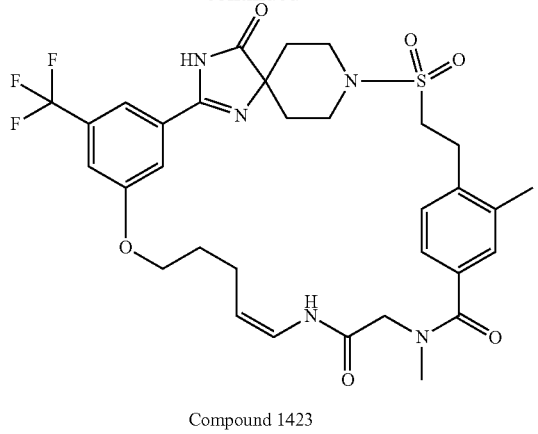

Compound 1423

A macrocyclic olefin compound (Compound 1422) and its isomer (Compound 1423) were obtained by the same method as in Reaction 338-1 using N-allylcarbamoylmethyl-4-{2-[2-(3-but-3-enyloxy-5-trifluoromethyl-phenyl)-4-oxo-1,3,8-triaza-spiro[4.5]dec-1-ene-8-sulfonyl]-ethyl}-3,N-dimethyl-benzamide as a starting material.

Compound 1422

MS (ESI) m/z=676 (M+H)+;
HPLC retention time: 2.47 min (analysis condition LCMS-A-1).

Compound 1423

MS (ESI) m/z=676 (M+H)+;
HPLC retention time: 2.61 min (analysis condition LCMS-A-1).

Example 352

Compound 1424

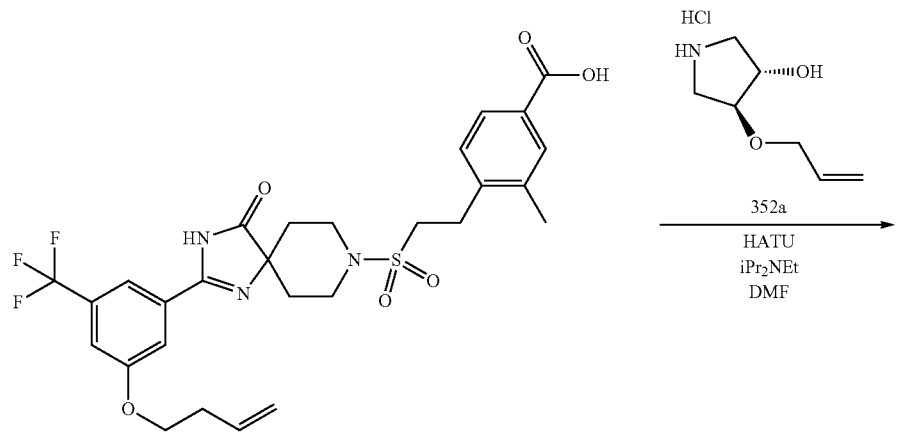

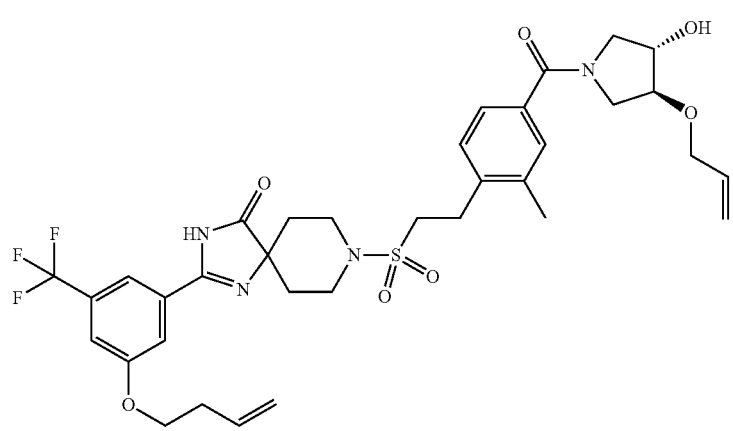

1589

8-{2-[4-((3S,4S)-3-Allyloxy-4-hydroxy-pyrrolidine-1-carbonyl)-2-methyl-phenyl]-ethanesulfonyl}-2-(3-but-3-enyloxy-5-trifluoromethyl-phenyl)-1,3,8-triaza-spiro[4.5]dec-1-en-4-one were obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and (3S,4S)-4-allyloxy-pyrrolidin-3-ol hydrochloride as starting materials.

MS (ESI) m/z=719 (M+H)+;

HPLC retention time: 2.81 min (analysis condition LCMS-A-1).

(3S,4S)-4-Allyloxy-pyrrolidin-3-ol hydrochloride used in the above reaction was synthesized by the following method.

(Reaction 352-2)

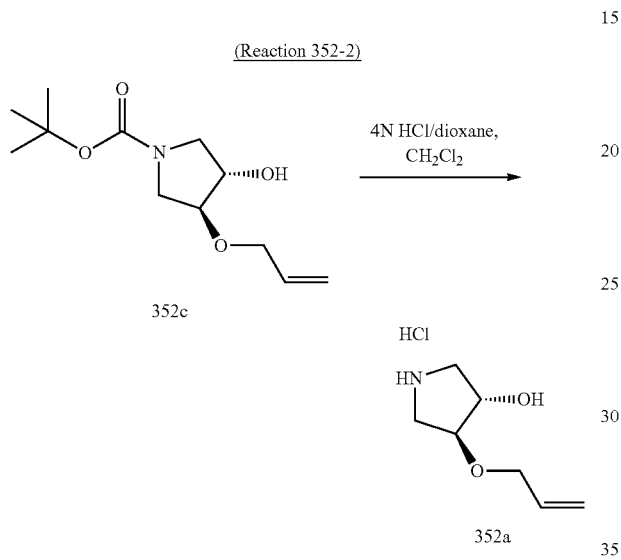

(3S,4S)-3-Allyloxy-4-hydroxy-pyrrolidine-1-carboxylic acid tert-butyl ester synthesized by the method described in the patent literature (DE4234330) (139 mg, 0.57 mmol) was dissolved in methylene chloride (2.4 ml). A 4 N solution of hydrochloric acid in dioxane (0.628 ml, 2.45 mmol) was added and the mixture was stirred at room temperature for two hours. The reaction solution was concentrated under reduced pressure to give (3S,4S)-4-allyloxy-pyrrolidin-3-ol hydrochloride (105 mg). This was used in the next reaction without further purification.

$^1$H-NMR (400 MHz, DMSO-$d_6$) δ 9.43 (2H, br s), 5.93-5.83 (1H, m), 5.72 (1H, br d, J=2.4 Hz), 5.28 (1H, dq, J=17.3, 1.8 Hz), 5.17 (1H, dq, J=10.5, 1.5 Hz), 4.26 (1H, br s), 4.04-4.02 (2H, m), 3.95 (1H, d, J=4.4 Hz), 3.32-3.06 (4H, m).

(Reaction 352-3)

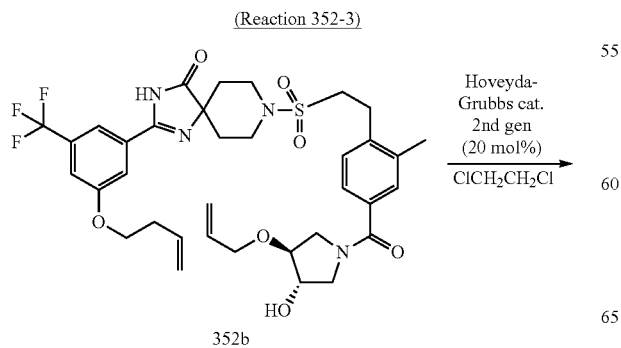

1590

-continued

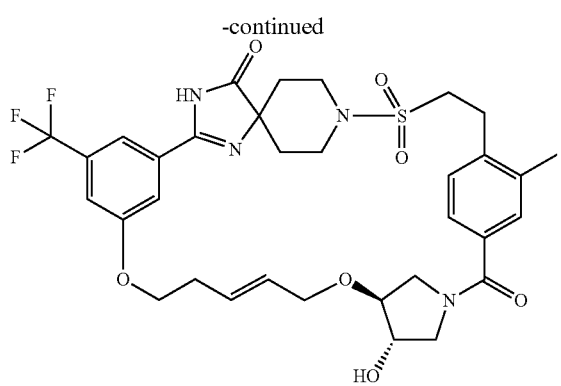

Compound 1424

A macrocyclic olefin compound (Compound 1424) was obtained by the same method as in Reaction 338-1 (using Hoveyda-Grubbs 2$^{nd}$ generation as a catalyst) using 8-{2-[4-((3S,4S)-3-allyloxy-4-hydroxy-pyrrolidine-1-carbonyl)-2-methyl-phenyl]-ethanesulfonyl}-2-(3-but-3-enyloxy-5-trifluoromethyl-phenyl)-1,3,8-triaza-spiro[4.5]dec-1-en-4-one (106 mg, 0.148 mmmol) as a starting material.

MS (ESI) m/z=691 (M+H)+;

HPLC retention time: 2.48 min (analysis condition LCMS-A-1).

Example 353

Compound 1425

(Reaction 353-1)

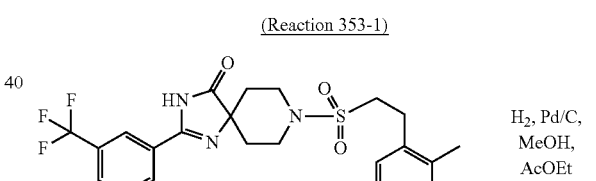

Compound 1424

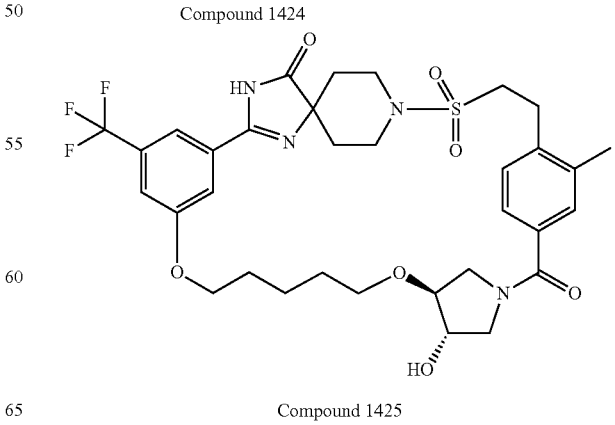

Compound 1425

A saturated macrocyclic compound (Compound 1425) was obtained by the same method as in Reaction 339-1 using a macrocyclic olefin compound (Compound 1424) as a starting material.

MS (ESI) m/z=693 (M+H)+;

HPLC retention time: 2.54 min (analysis condition LCMS-A-1).

Example 354

Compound 1426

(Reaction 354-1)

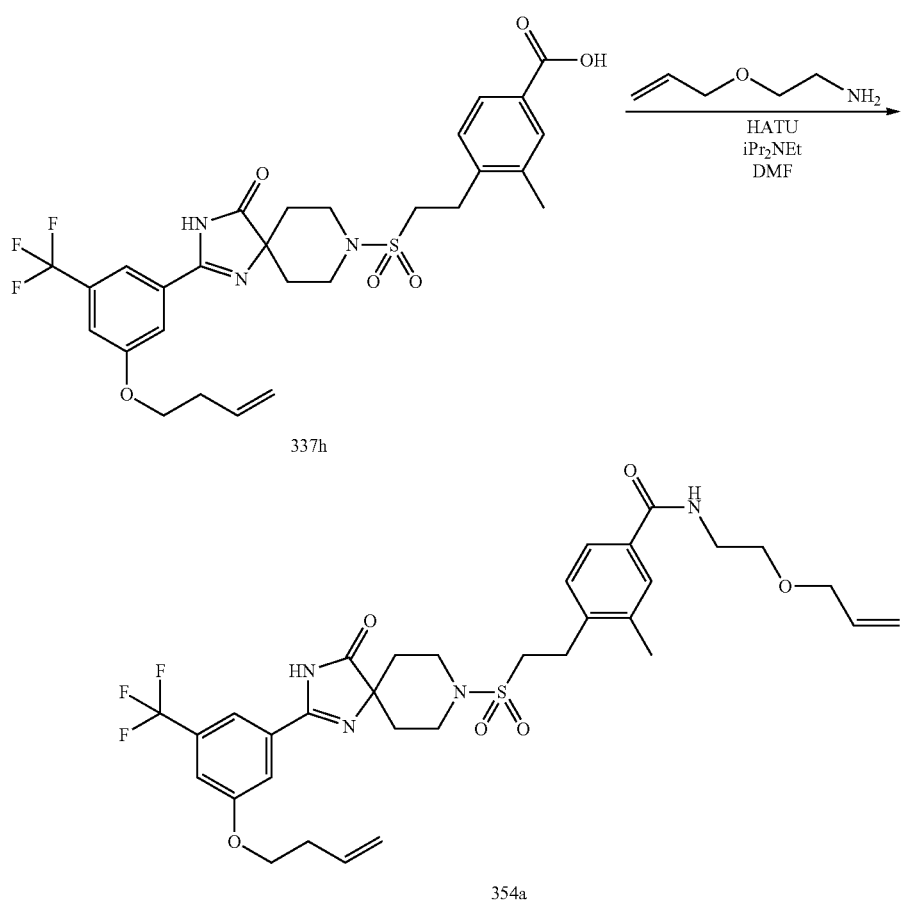

337h

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and 2-allyloxy-ethylamine as starting materials.

MS (ESI) m/z=677 (M+H)+;

HPLC retention time: 1.08 min (analysis condition LCMS-F-1).

(Reaction 354-2)

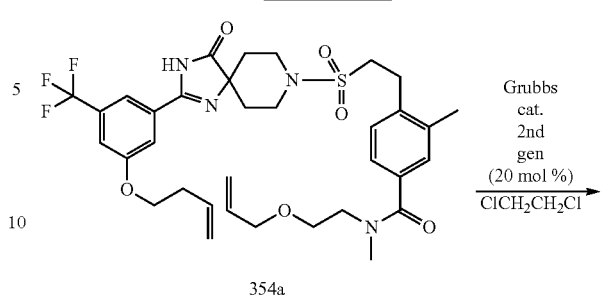

354a

-continued

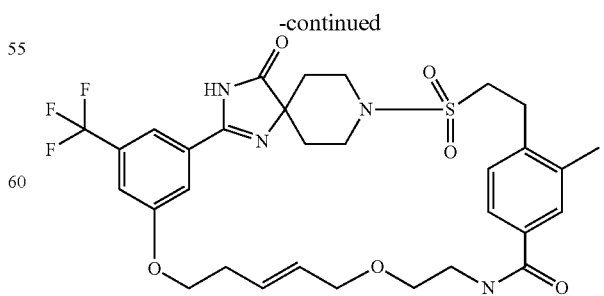

Compound 1426

1593

A macrocyclic olefin compound (Compound 1426) was obtained by the same method as in Reaction 338-1 using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzamide as a starting material.

MS (ESI) m/z=649 (M+H)+;

HPLC retention time: 2.83 min (analysis condition LCMS-C-1).

Example 355

Compound 1427

(Reaction 355-1)

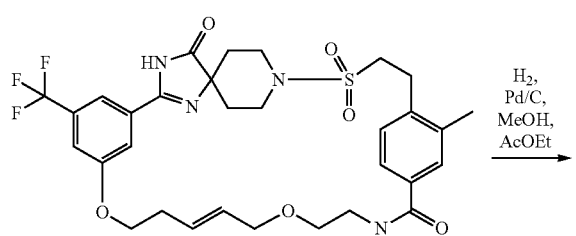

Compound 1426

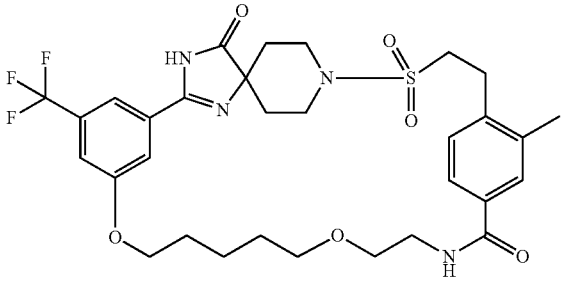

Compound 1427

A saturated macrocyclic compound (Compound 1427) was obtained by the same method as in Reaction 339-1 using a macrocyclic olefin compound (Compound 1426) as a starting material.

MS (ESI) m/z=651 (M+H)+;

HPLC retention time: 1.07 min (analysis condition LCMS-F-1).

Example 356

Compound 1428

(Reaction 356-1)

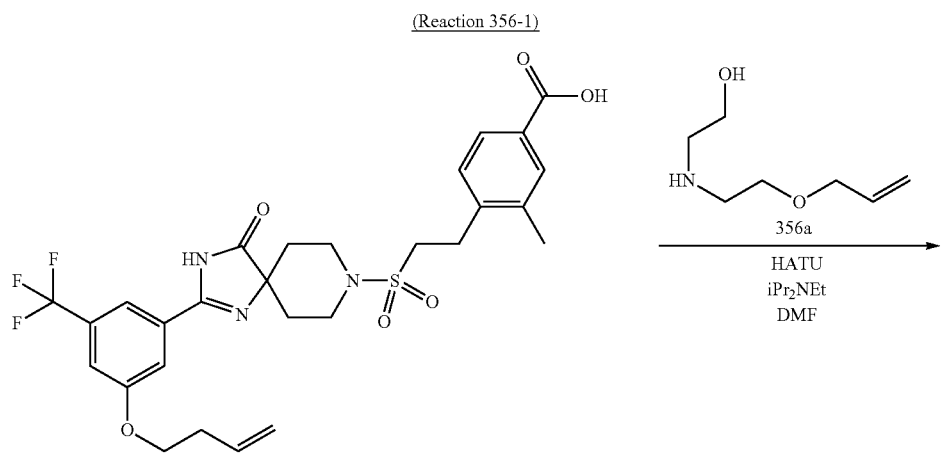

337h

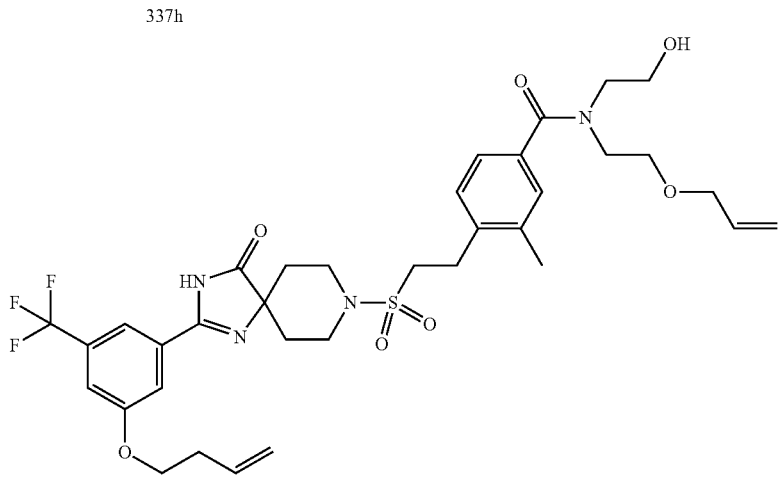

356b

N-(2-Allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-N-(2-hydroxy-ethyl)-3-methyl-benzamide was obtained by the same method as in Reaction 337-8 using 4-{2-[2-(3-but-3-enyloxy-5-trifluoromethyl-phenyl)-4-oxo-1,3,8-triaza-spiro[4.5]dec-1-ene-8-sulfonyl]-ethyl}-3-methyl-benzoic acid and 2-(2-allyloxy-ethylamino)-ethanol as starting materials.

MS (ESI) m/z=721 (M+H)+;

HPLC retention time: 1.05 min (analysis condition LCMS-F-1).

2-(2-Allyloxy-ethylamino)-ethanol used in the above Reaction 356-1 was synthesized by the following method.

(Reaction 356-2)

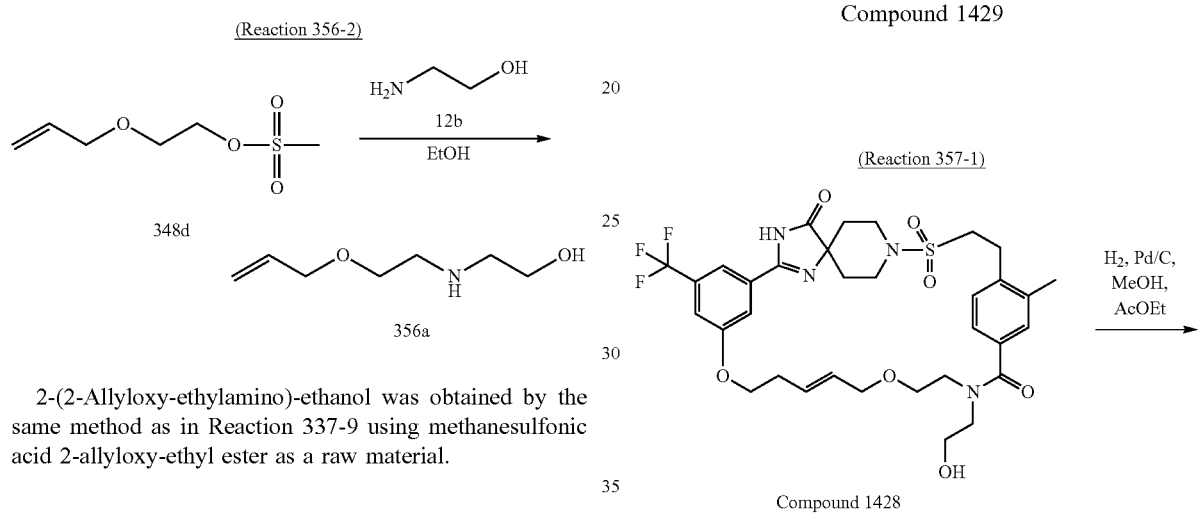

2-(2-Allyloxy-ethylamino)-ethanol was obtained by the same method as in Reaction 337-9 using methanesulfonic acid 2-allyloxy-ethyl ester as a raw material.

(Reaction 356-3)

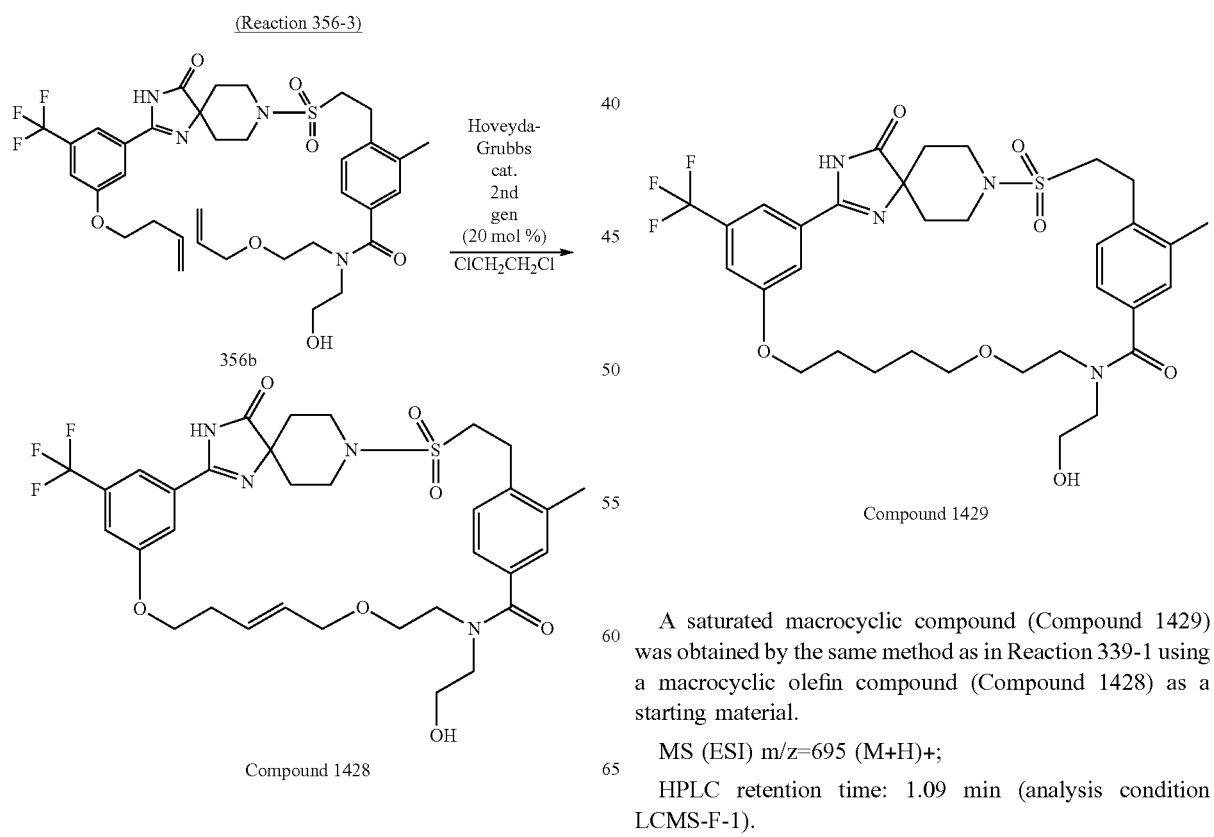

A macrocyclic olefin compound (Compound 1428) was obtained by the same method as in Reaction 338-1 (using Hoveyda-Grubbs $2^{nd}$ generation as a catalyst) using N-(2-allyloxy-ethyl)-4-{2-[2-(3-but-3-enyloxy-5-trifluoromethyl-phenyl)-4-oxo-1,3,8-triaza-spiro[4.5]dec-1-ene-8-sulfonyl]-ethyl}-N-(2-hydroxy-ethyl)-3-methyl-benzamide as a starting material.

MS (ESI) m/z=693 (M+H)+;

HPLC retention time: 1.06 min (analysis condition LCMS-F-1).

Example 357

Compound 1429

A saturated macrocyclic compound (Compound 1429) was obtained by the same method as in Reaction 339-1 using a macrocyclic olefin compound (Compound 1428) as a starting material.

MS (ESI) m/z=695 (M+H)+;

HPLC retention time: 1.09 min (analysis condition LCMS-F-1).

Example 358

Compound 1430

(Reaction 358-1)

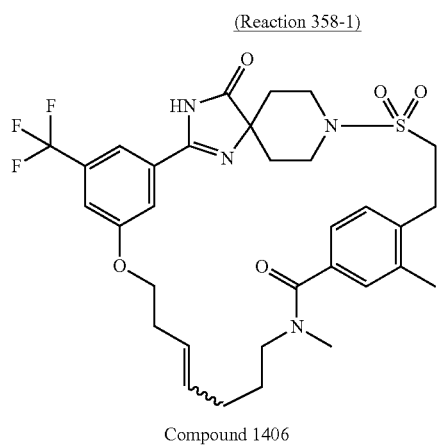

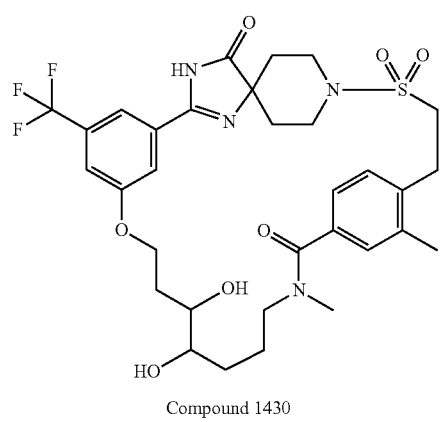

Compound 1430

A macrocyclic olefin compound (Compound 1406) (20 mg, 0.031 mmol) was dissolved in THF (1 ml). Microcapsulated osmium tetroxide (7.1 mg; 0.79 mg, 3.1 μmoL as osmium tetroxide) and 30% aqueous hydrogen peroxide (0.028 ml) were added and the mixture was stirred at 0° C. for 4.5 hours and at room temperature for three hours. An aqueous sodium sulfite solution was added to the reaction solution, followed by extraction with ethyl acetate. The organic layer was washed with water and saturated brine, and then dried over anhydrous sodium sulfate and concentrated under reduced pressure. The resulting residue was purified by P-TLC to give a macrocyclic diol compound (Compound 1430, 2 mg, 10%).

MS (ESI) m/z=681 (M+H)+;

HPLC retention time: 2.22 min (analysis condition LCMS-F-1).

Example 359

Compound 1431

(Reaction 359-1)

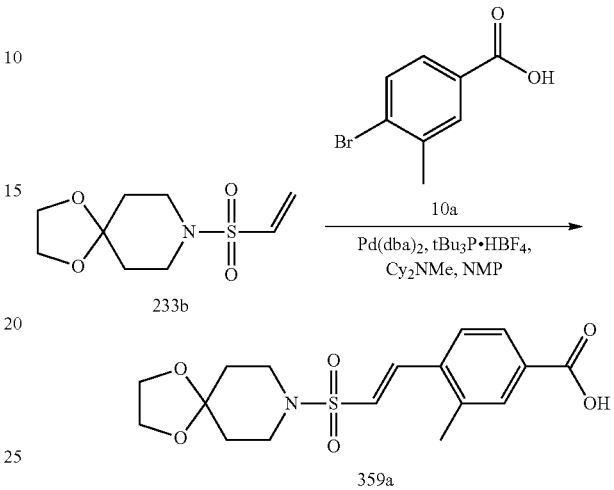

Dicyclohexyl-methyl-amine (34.2 ml, 162.8 mmol) was added to a solution of 8-ethenesulfonyl-1,4-dioxa-8-aza-spiro[4.5]decane (17.3 g, 74.01 mmol), 4-bromo-3-methyl-benzoic acid (19.1 g, 88.82 mmol), Pd(dba)₂ (4.26 g, 7.40 mmol) and tri-t-butylphosphonium tetrafluoroborate (2.15 g, 7.40 mmol) in NMP (70.0 ml), and the mixture was stirred at 100° C. for one hour in a nitrogen atmosphere. The reaction solution was cooled to room temperature and then diluted with ethyl acetate, and the organic layer was washed with a 1 M aqueous hydrochloric acid solution and saline. The organic layer was allowed to stand for a while, and the precipitated solid was filtered off. The resulting solid was washed with ethyl acetate to give 4-[(E)-2-(1,4-dioxa-8-aza-spiro[4.5]decane-8-sulfonyl)-vinyl]-3-methyl-benzoic acid as a gray solid (25.6 g, 94.1%).

MS (ESI) m/z=368 (M+H)+;

HPLC retention time: 0.61 min (analysis condition LCMS-F-1).

(Reaction 359-2)

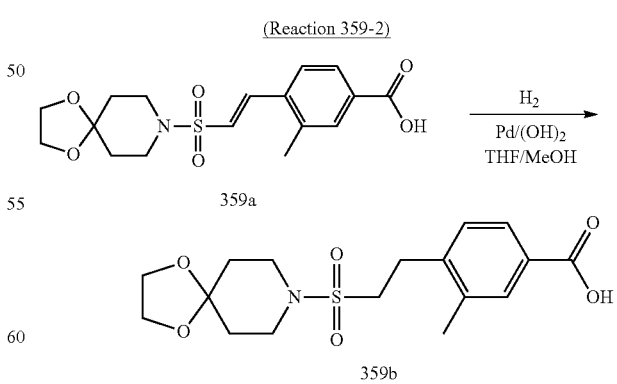

Pd(OH)₂—C(20.0 g) was added to a solution of 4-[(E)-2-(1,4-dioxa-8-aza-spiro[4.5]decane-8-sulfonyl)-vinyl]-3-methyl-benzoic acid (20.0 g, 54.43 mmol) in THF (600 ml)-methanol (200 ml), and the mixture was stirred at room temperature overnight in a hydrogen atmosphere. The reaction mixture was filtered through celite, and the filtrate was then concentrated under reduced pressure to give 4-[2-(1,4-dioxa-8-aza-spiro[4.5]decane-8-sulfonyl)-ethyl]-3-methyl-benzoic acid as a white solid (18.23 g, 90.7%).

MS (ESI) m/z=370 (M+H)+;
HPLC retention time: 1.85 min (analysis condition LCMS-B-1).

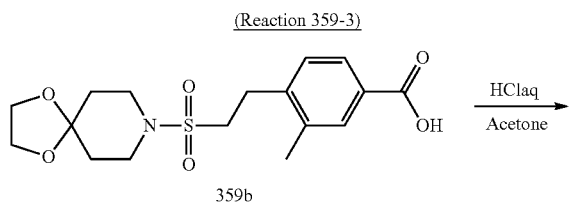

A 6 M aqueous hydrochloric acid solution (217.9 ml, 1307.4 mmol) was slowly added to a suspension of 4-[2-(1,4-dioxa-8-aza-spiro[4.5]decane-8-sulfonyl)-ethyl]-3-methyl-benzoic acid (16.1 g, 43.58 mmol) in acetone (485 ml) at 0° C., and the mixture was warmed to room temperature and stirred overnight. The reaction mixture was filtered off, and the filtrate was then concentrated under reduced pressure. The precipitated solid was filtered off again. The solids filtered off were combined and dried to give 3-methyl-4-[2-(4-oxo-piperidine-1-sulfonyl)-ethyl]-benzoic acid as a white solid (13.62 g, 91.8%).

MS (ESI) m/z=326 (M+H)+;
HPLC retention time: 1.57 min (analysis condition LCMS-B-1).

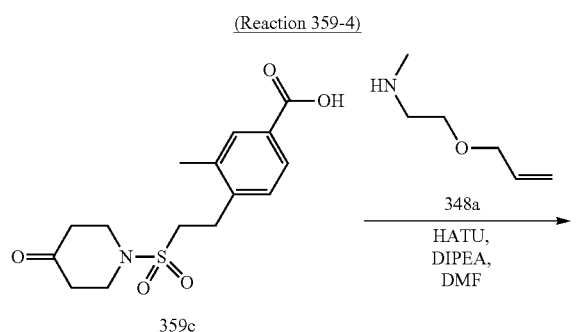

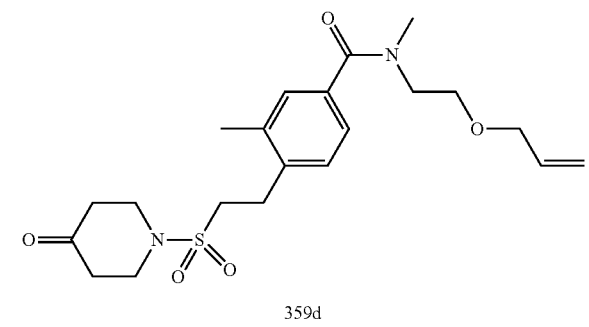

HATU (91 mg, 0.239 mmol) was added to a solution of 3-methyl-4-[2-(4-oxo-piperidine-1-sulfonyl)-ethyl]-benzoic acid (50 mg, 0.154 mmol), (2-allyloxy-ethyl)-methyl-amine (36 mg, 0.312 mmol) and diisopropylethylamine (0.065 ml, 0.384 mmol) in DMF (0.5 ml), and the mixture was stirred at room temperature overnight. Water (12 ml) and 1 N hydrochloric acid (1.5 ml) were added to the reaction solution, followed by extraction with ethyl acetate. The organic layer was sequentially washed with 0.1 N hydrochloric acid, water and saturated brine, and then dried over anhydrous sodium sulfate and concentrated under reduced pressure. The resulting residue was purified by silica gel column chromatography (hexane-ethyl acetate) to give N-(2-allyloxy-ethyl)-3,N-dimethyl-4-[2-(4-oxo-piperidine-1-sulfonyl)-ethyl]-benzamide (76 mg, 100%).

MS (ESI) m/z=423 (M+H)+;
HPLC retention time: 2.15 min (analysis condition LCMS-C-1).

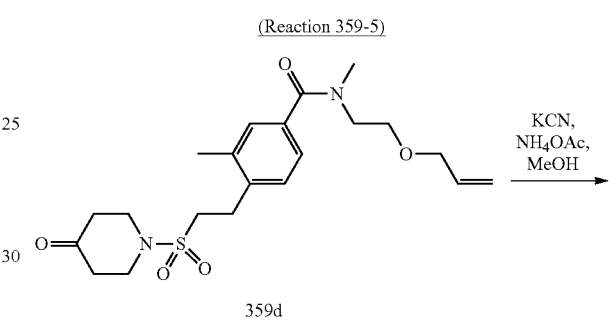

Potassium cyanide (382 mg, 5.87 mmol) and ammonium acetate (513 mg, 6.65 mmol) were added to a solution of N-(2-allyloxy-ethyl)-3,N-dimethyl-4-[2-(4-oxo-piperidine-1-sulfonyl)-ethyl]-benzamide (1.65 g, 3.91 mmol) in methanol (20 ml), and the mixture was stirred at 65° C. for three hours. Sodium bicarbonate (290 mg) was added to the reaction solution, and the mixture was then concentrated under reduced pressure. Water was added to the resulting residue, followed by extraction with methylene chloride. The organic layer was washed with saturated brine, dried over anhydrous sodium sulfate and concentrated under reduced pressure to give N-(2-allyloxy-ethyl)-4-[2-(4- amino-4-cyano-piperidine-1-sulfonyl)-ethyl]-3,N-dimethyl-benzamide (1.57 g) as a crude compound.

A 1 N aqueous sodium hydroxide solution (1.41 ml) and 30% aqueous hydrogen peroxide (0.95 ml) were added to a solution of the resulting N-(2-allyloxy-ethyl)-4-[2-(4-amino-4-cyano-piperidine-1-sulfonyl)-ethyl]-3,N-dimethyl-benzamide in methanol (24 ml)-DMSO (1.3 ml), and the mixture was stirred at room temperature for one hour. A 10% (w/w) aqueous sodium sulfite solution (2.64 ml) was added to the reaction solution, and the mixture was stirred at room temperature for 40 minutes. The precipitated insoluble matter was then removed by filtration. The resulting filtrate was concentrated under reduced pressure to give 1-(2-{4-[(2-allyloxy-ethyl)-methyl-carbamoyl]-2-methyl-phenyl}-ethanesulfonyl)-4-amino-piperidine-4-carboxylic amide (2.13 g). This was used in the next reaction without further purification.

MS (ESI) m/z=467 (M+H)+;

HPLC retention time: 1.59 min (analysis condition LCMS-A-1).

$^1$H-NMR (400 MHz, CDCl$_3$) δ 7.77-7.70 (3H, m), 7.48-7.32 (5H, m), 5.27 (2H, s);

MS (ESI) m/z=295 (M–H)–;

HPLC retention time: 2.37 min (analysis condition LCMS-C-1).

10% Pd/C (590 mg) was added to 3-benzyloxy-4-trifluoromethyl-benzoic acid in a methanol-ethyl acetate mixed solvent (1:1), and the mixture was stirred at room temperature for two days in a hydrogen atmosphere. The reaction solution was filtered through celite, and the filtrate was then concentrated under reduced pressure. The resulting residue was purified by silica gel column chromatography (n-hexane-ethyl acetate) to give 3-hydroxy-4-trifluoromethyl-benzoic acid (582 mg, 86%).

$^1$H-NMR (400 MHz, DMSO-d$_6$) δ 13.26 (1H, br s), 10.94 (1H, br s), 7.63 (1H, d, J=8.3 Hz), 7.59 (1H, s), 7.46 (1H, d, J=8.8 Hz);

MS (ESI) m/z=205 (M–H)–;

HPLC retention time: 1.15 min (analysis condition LCMS-C-1).

(Reaction 359-6)

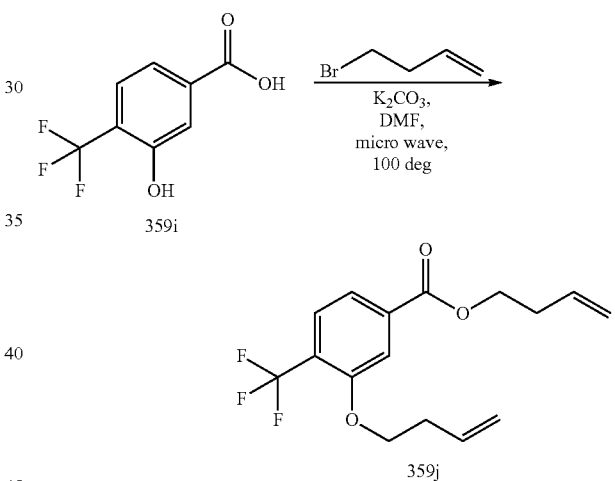

Potassium tert-butoxide (816 mg, 7.28 mmol) was added to a solution of 3-fluoro-4-trifluoromethyl-benzoic acid (682 mg, 3.28 mmol) and benzyl alcohol (471 mg, 4.36 mmol) in DMSO (7.3 ml), and the mixture was stirred at room temperature for 16 hours. The reaction solution was made acidic by adding concentrated hydrochloric acid, and the precipitated insoluble matter was then filtered off. The resulting solid was washed with water and then dried to give 3-benzyloxy-4-trifluoromethyl-benzoic acid as a crude compound.

3-But-3-enyloxy-4-trifluoromethyl-benzoic acid but-3-enyl ester was obtained by the same method as in Reaction 337-1 using 3-hydroxy-4-trifluoromethyl-benzoic acid as a raw material.

$^1$H-NMR (400 MHz, CDCl$_3$) δ 7.66-7.61 (3H, m), 5.98-5.81 (2H, m), 5.22-5.15 (2H, m), 5.14-5.10 (2H, m), 4.40 (2H, t, J=6.8 Hz), 4.16 (2H, t, J=6.6 Hz), 2.62-2.51 (4H, m).

(Reaction 359-8)

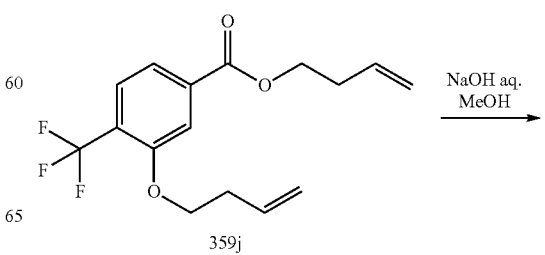

-continued

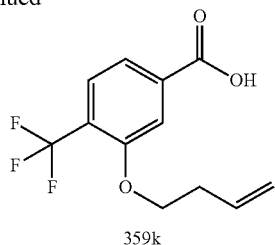

359k

3-But-3-enyloxy-4-trifluoromethyl-benzoic acid was obtained by the same method as in Reaction 337-2 using 3-but-3-enyloxy-4-trifluoromethyl-benzoic acid but-3-enyl ester as a raw material.

$^1$H-NMR (400 MHz, CD$_3$OD) δ 7.73 (1H, br s), 7.68 (2H, br s), 6.00-5.90 (1H, m), 5.21-5.15 (1H, m), 5.11-5.08 (1H, m), 4.19 (2H, t, J=6.6 Hz), 2.60-2.55 (2H, m).

Potassium tert-butoxide (302 mg, 2.69 mmol) was added to a solution of the resulting 1-(2-{4-[(2-allyloxy-ethyl)-methyl-carbamoyl]-2-methyl-phenyl}-ethanesulfonyl)-4-(3-but-3-enyloxy-4-trifluoromethyl-benzoylamino)-piperidine-4-carboxylic amide in ethanol (6 ml), and the mixture was stirred at 80° C. for 30 minutes. A saturated aqueous ammonium chloride solution, water and saturated brine were sequentially added to the reaction solution, followed by extraction with ethyl acetate. The organic layer was washed with saturated brine, and then dried over anhydrous sodium sulfate and concentrated under reduced pressure. The resulting residue was purified by silica gel column chromatography to give N-(2-allyloxy-ethyl)-4-{2-[2-(3-but-3-enyloxy-4-trifluoromethyl-phenyl)-4-oxo-1,3,8-triaza-spiro[4.5]dec-1-ene-8-sulfonyl]-ethyl}-3,N-dimethyl-benzamide (176 mg).

MS (ESI) m/z=691 (M+H)+;

HPLC retention time: 3.03 min (analysis condition LCMS-C-1).

(Reaction 359-9)

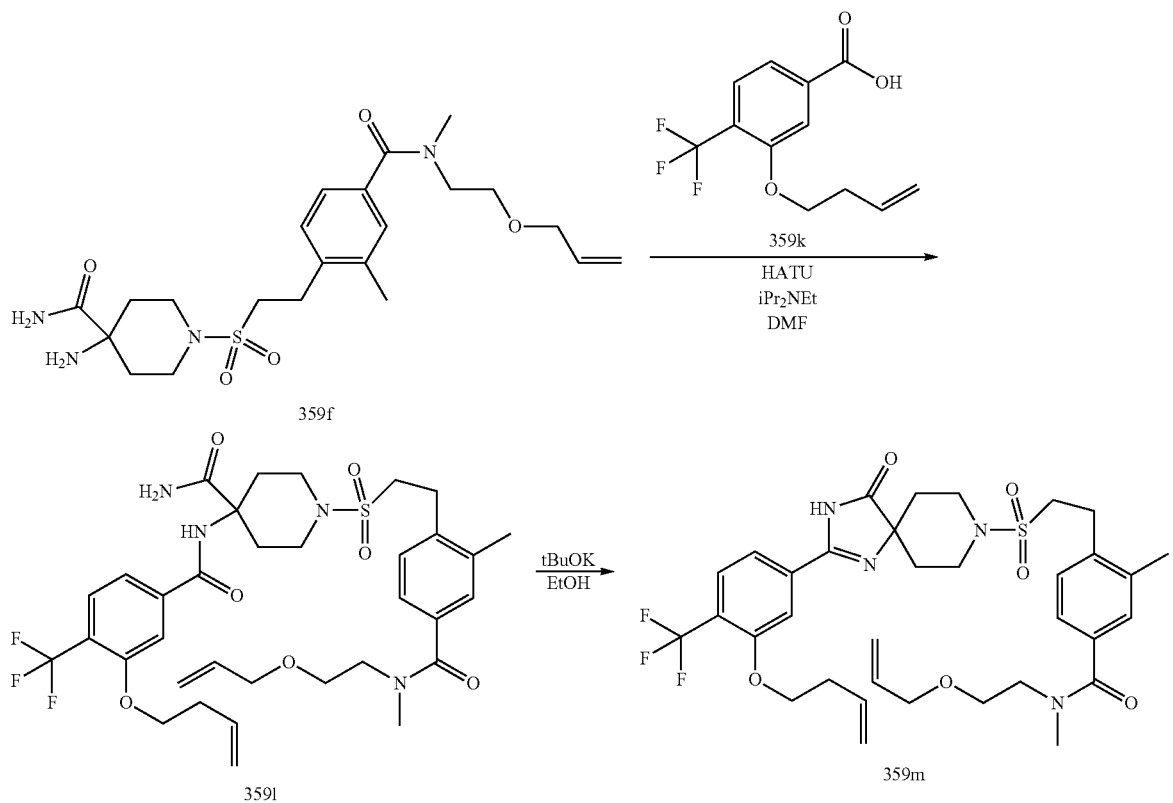

HATU (245 mg, 0.644 mmol) was added to a solution of 1-(2-{4-[(2-allyloxy-ethyl)-methyl-carbamoyl]-2-methyl-phenyl}-ethanesulfonyl)-4-amino-piperidine-4-carboxylic amide (250 mg), 3-but-3-enyloxy-4-trifluoromethyl-benzoic acid (155 mg, 0.596 mmol) and diisopropylethylamine (0.140 ml, 0.812 mmol) in DMF (5 ml), and the mixture was stirred at room temperature for 1.5 hours. Water was added to the reaction solution, followed by extraction with ethyl acetate. The organic layer was washed with water and saturated brine, and then dried over anhydrous sodium sulfate and concentrated under reduced pressure to give 1-(2-{4-[(2-allyloxy-ethyl)-methyl-carbamoyl]-2-methyl-phenyl}-ethanesulfonyl)-4-(3-but-3-enyloxy-4-trifluoromethyl-benzoylamino)-piperidine-4-carboxylic amide as a crude compound (381 mg).

(Reaction 359-10)

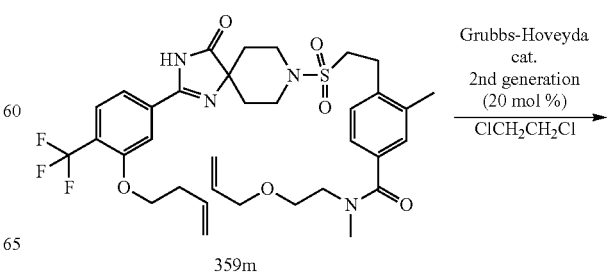

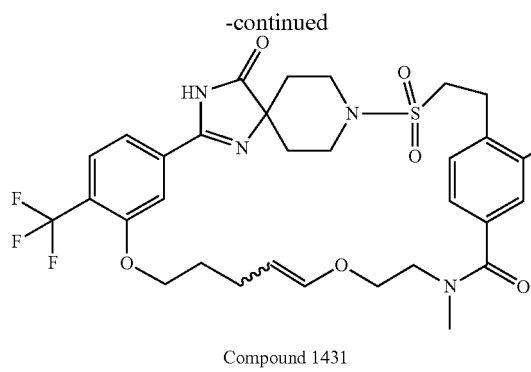

Compound 1431

A macrocyclic olefin compound (Compound 1431) (E/Z=1:2) was obtained by the same method as in Reaction 338-1 (using Hoveyda-Grubbs 2$^{nd}$ generation as a catalyst) using N-(2-allyloxy-ethyl)-4-{2-[2-(3-but-3-enyloxy-4-trifluoromethyl-phenyl)-4-oxo-1,3,8-triaza-spiro[4.5]dec-1-ene-8-sulfonyl]-ethyl}-3,N-dimethyl-benzamide as a starting material.

MS (ESI) m/z=663 (M+H)+;

HPLC retention time: 2.90 min (analysis condition LCMS-C-1).

Example 360

Compound 1432

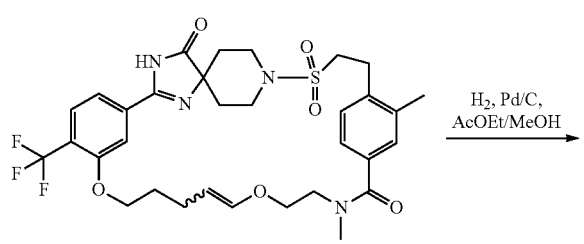

Compound 1432

A saturated macrocyclic compound (Compound 1432) was obtained by the same method as in Reaction 339-1 using a macrocyclic olefin compound (Compound 1431) as a starting material.

MS (ESI) m/z=665 (M+H)+;

HPLC retention time: 1.06 min (analysis condition LCMS-C-1).

Example 361

Compound 1433

(Reaction 361-1)

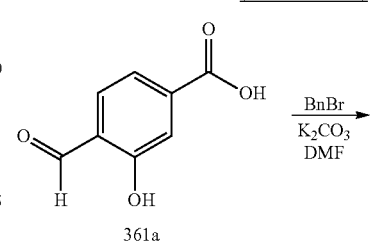

361a

361b

Benzyl bromide (2.17 ml, 18.3 mmol) was added to a solution of 4-formyl-3-hydroxy-benzoic acid (1.01 g, 6.10 mmol) and potassium carbonate (3.37 g, 24.4 mmol) in DMF (10 ml), and the mixture was stirred at 50° C. for five hours. The reaction solution was poured into ice water and extracted with ethyl acetate. The organic layer was washed with water and saturated brine, and then dried over anhydrous sodium sulfate and concentrated under reduced pressure. The resulting residue was purified by silica gel column chromatography (hexane-ethyl acetate) to give 3-benzyloxy-4-formyl-benzoic acid benzyl ester (2.01 g, 95%).

$^1$H-NMR (400 MHz, CDCl$_3$) δ 10.58 (1H, s), 7.89 (1H, d, J=8.3 Hz), 7.78 (1H, d, J=1.5 Hz), 7.73 (1H, br d, J=8.3 Hz), 7.46-7.35 (10H, m), 5.38 (2H, s), 5.24 (2H, s).

(Reaction 361-2)

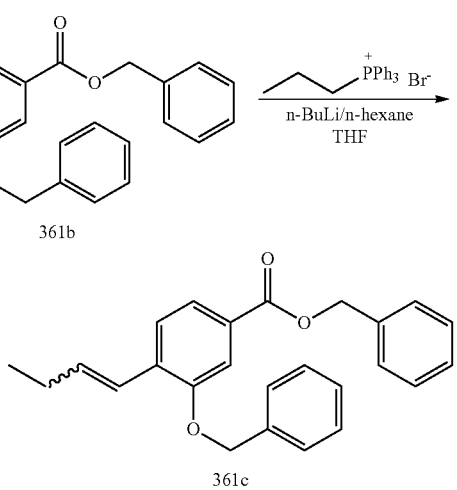

361b

361c n-Butyllithium (1.65 M solution in n-hexane, 4.22 ml, 6.92 mmol) was added dropwise to a solution of triphenyln-propyl-phosphonium bromide (2.91 g, 7.54 mmol) in THF (49 ml) at 0° C., and the mixture was stirred for 30 minutes. Further, a solution of 3-benzyloxy-4-formyl-benzoic acid benzyl ester (2.01 g, 5.80 mmol) in THF (4.9 ml) was added dropwise and then the mixture was stirred at 0° C. for 30 minutes and at room temperature for 16 hours. A saturated aqueous ammonium chloride solution, water and saturated brine were added to the reaction solution, and this mixture was extracted with ethyl acetate. The organic layer was washed with water and saturated brine, and then dried over anhydrous sodium sulfate and concentrated under reduced pressure. The resulting residue was purified by silica gel column chromatography (n-hexane-ethyl acetate) to give 3-benzyloxy-4-((E/Z)-but-1-enyl)-benzoic acid benzyl ester (E/Z=2:3, 1.74 g, 80%).

$^1$H-NMR (400 MHz, CDCl$_3$) δ 7.68-7.60 (2H, m), 7.50-7.30 (11H, m), 6.79 (0.4H, d, J=16.1 Hz), 6.57 (0.6H, d, J=11.7 Hz), 6.40 (0.4H, dt, J=16.0, 6.6 Hz), 5.78 (0.6H, dt, J=13.7, 5.9 Hz), 5.36 (1.2H, s), 5.35 (0.8H, s), 5.14 (0.8H, s), 5.14 (1.2H, s), 2.32-2.22 (2H, m), 1.09 (1.2H, t, J=7.3 Hz), 1.04 (1.8H, t, J=7.6 Hz).

(Reaction 361-3)

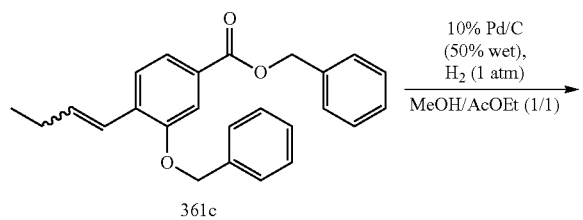

10% Pd/C (174 mg) was added to 3-benzyloxy-4-((E/Z)-but-1-enyl)-benzoic acid benzyl ester (1.74 g, 4.67 mmol) in a methanol-ethyl acetate mixed solvent (1:1), and the mixture was stirred at room temperature for 21 hours in a hydrogen atmosphere. The reaction solution was filtered through celite, and the filtrate was then concentrated under reduced pressure to give 4-butyl-3-hydroxy-benzoic acid (922 mg) as a crude compound.

$^1$H-NMR (400 MHz, CD$_3$OD) δ 7.42-7.39 (2H, m), 7.14-7.11 (1H, m), 2.64 (2H, t, J=7.6 Hz), 1.62-1.54 (2H, m), 1.42-1.33 (2H, m), 0.94 (3H, t, J=7.3 Hz).

(Reaction 361-4)

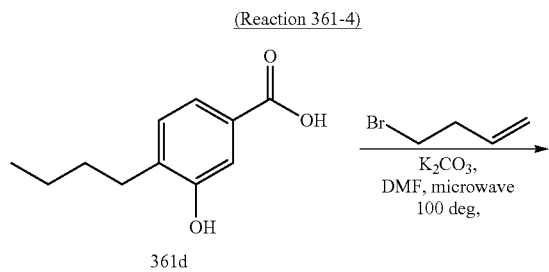

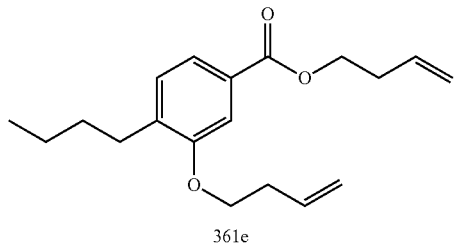

3-But-3-enyloxy-4-butyl-benzoic acid but-3-enyl ester was obtained by the same method as in Reaction 337-1 using 4-butyl-3-hydroxy-benzoic acid as a raw material.

$^1$H-NMR (400 MHz, CDCl$_3$) δ 7.56 (1H, dd, J=7.8, 1.5 Hz), 7.47 (1H, d, J=1.5 Hz), 7.17 (1H, d, J=7.3 Hz), 5.97-5.82 (2H, m), 5.21-5.14 (2H, m), 5.13-5.08 (2H, m), 4.35 (2H, t, J=6.8 Hz), 4.07 (2H, t, J=6.3 Hz), 2.64 (2H, t, J=7.8 Hz), 2.60-2.49 (4H, m), 1.60-1.52 (2H, m), 1.40-1.30 (2H, m), 0.92 (3H, t, J=7.3 Hz).

(Reaction 361-5)

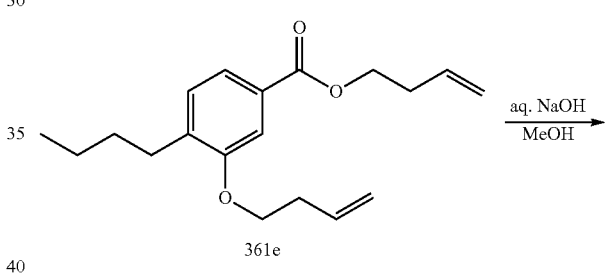

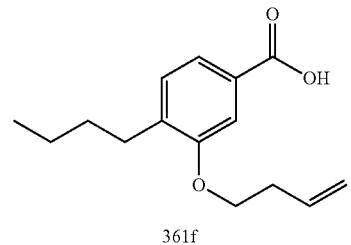

3-But-3-enyloxy-4-butyl-benzoic acid (243 mg, 93%) was obtained by the same method as in Reaction 337-2 using 3-but-3-enyloxy-4-butyl-benzoic acid but-3-enyl ester (318 mg, 1.05 mmol) as a raw material.

$^1$H-NMR (400 MHz, CD$_3$OD) δ 7.53 (1H, dd, J=7.6, 1.7 Hz), 7.50 (1H, d, J=1.5 Hz), 7.19 (1H, d, J=7.8 Hz), 6.01-5.91 (1H, m), 5.21-5.15 (1H, m), 5.11-5.07 (1H, m), 4.08 (2H, t, J=6.1 Hz), 2.65 (2H, t, J=7.6 Hz), 2.59-2.54 (2H, m), 1.61-1.53 (2H, m), 1.40-1.31 (2H, m), 0.94 (3H, t, J=7.3 Hz).

(Reaction 361-6)

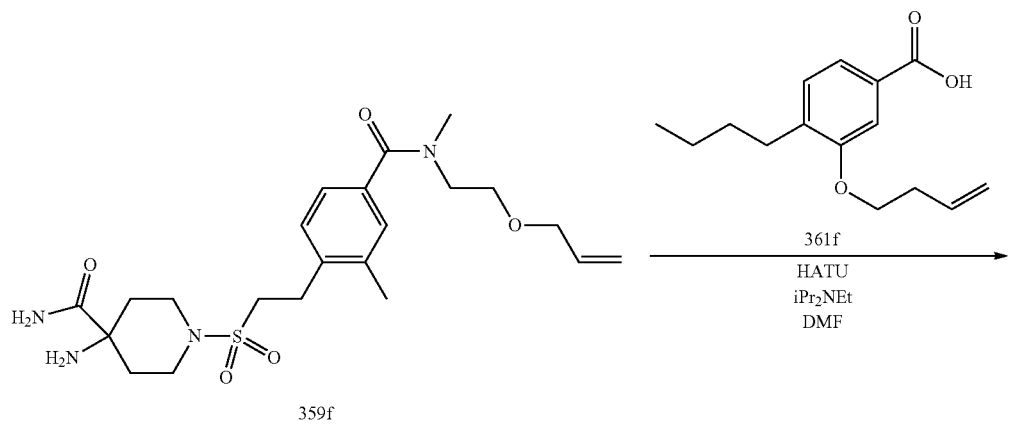

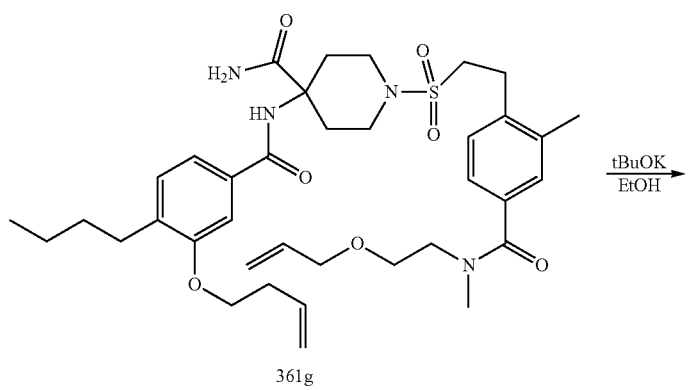

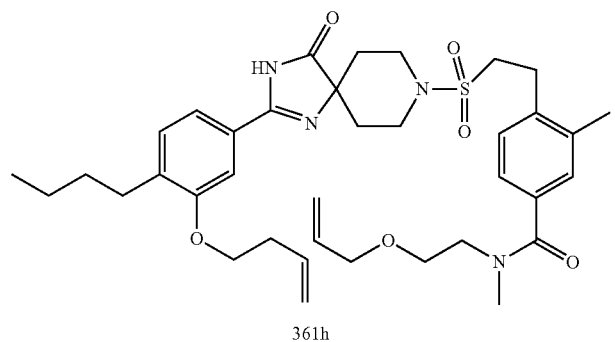

N-(2-Allyloxy-ethyl)-4-{2-[2-(3-but-3-enyloxy-4-butyl-phenyl)-4-oxo-1,3,8-triaza-spiro[4.5]dec-1-ene-8-sulfonyl]-ethyl}-3,N-dimethyl-benzamide was obtained by the same method as in Reaction 359-9 using 3-but-3-enyloxy-4-butyl-benzoic acid (117 mg, 0.471 mmol) and 1-(2-{4-[(2-allyloxy-ethyl)-methyl-carbamoyl]-2-methyl-phenyl}-ethane-sulfonyl)-4-amino-piperidine-4-carboxylic amide as starting materials.

MS (ESI) m/z=677 (M−H)−;

HPLC retention time: 3.23 min (analysis condition LCMS-C-1).

(Reaction 361-7)

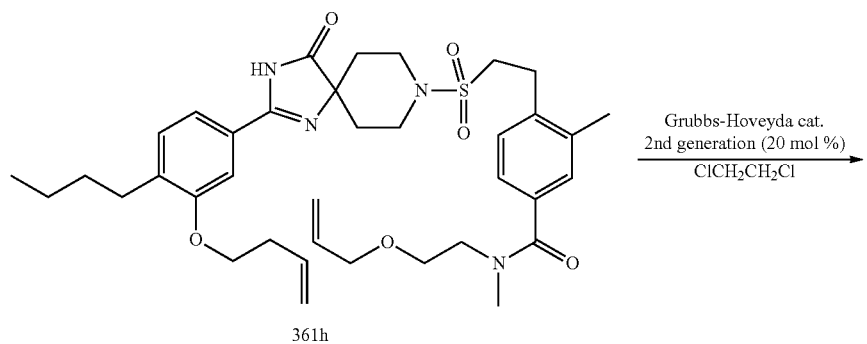

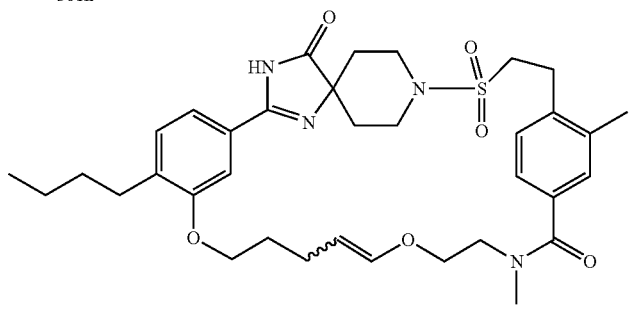

Compound 1433

A macrocyclic olefin compound (Compound 1433) (E/Z=1:2) was obtained by the same method as in Reaction 338-1 (using Hoveyda-Grubbs $2^{nd}$ generation as a catalyst) using N-(2-allyloxy-ethyl)-4-{2-[2-(3-but-3-enyloxy-4-butyl-phenyl)-4-oxo-1,3,8-triaza-spiro[4.5]dec-1-ene-8-sulfonyl]-ethyl}-3,N-dimethyl-benzamide as a starting material.

MS (ESI) m/z=651 (M+H)+;

HPLC retention time: 3.13 min (analysis condition LCMS-C-1).

Example 362

Compound 1434

(Reaction 362-1)

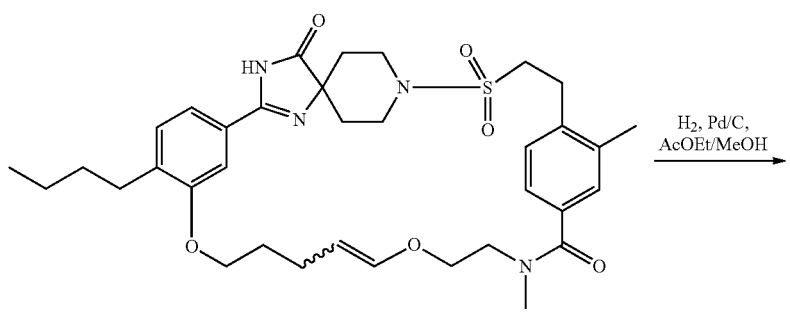

Compound 1433

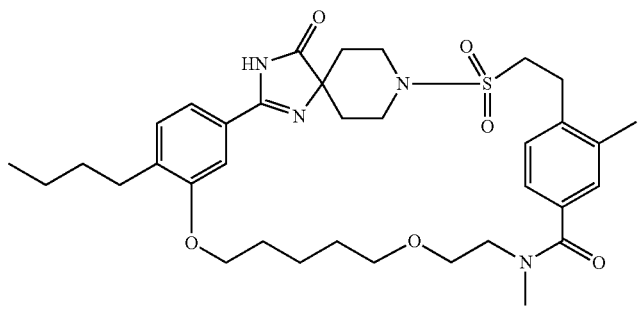

Compound 1434

A saturated macrocyclic compound (Compound 1434) was obtained by the same method as in Reaction 339-1 using a macrocyclic olefin compound (Compound 1433) as a starting material.

MS (ESI) m/z=653 (M+H)+;

HPLC retention time: 1.12 min (analysis condition LCMS-F-1).

Example 363

Compound 1435

(Reaction 363-1)

3-But-3-enyloxy-benzoic acid but-3-enyl ester was obtained by the same method as in Reaction 337-1 using 3-hydroxy-benzoic acid as a raw material.

$^{1}$H-NMR (400 MHz, CDCl$_{3}$) δ 7.62 (1H, br d, J=7.8 Hz), 7.55 (1H, br s), 7.33 (1H, t, J=8.1 Hz), 7.09 (1H, br d, J=8.3 Hz), 5.96-5.82 (2H, m), 5.20-5.10 (4H, m), 4.37 (2H, t, J=6.8 Hz), 4.06 (2H, t, J=6.8 Hz), 2.60-2.50 (4H, m).

(Reaction 363-2)

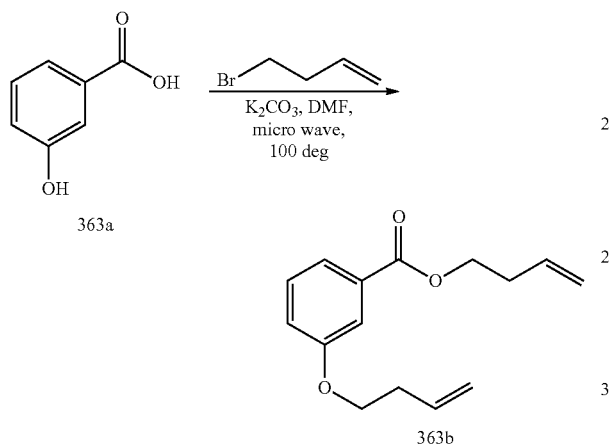

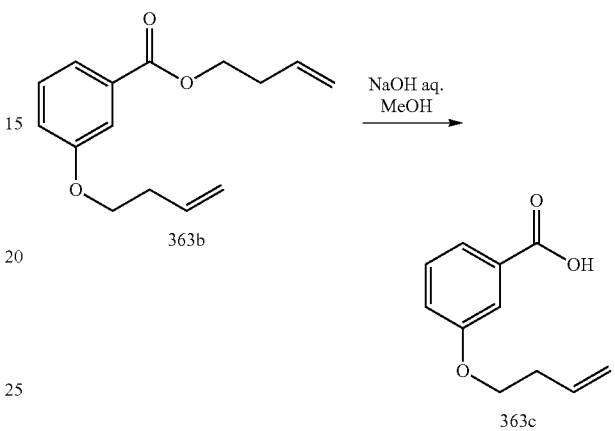

3-But-3-enyloxy-benzoic acid was obtained by the same method as in Reaction 337-2 using 3-but-3-enyloxy-benzoic acid but-3-enyl ester as a raw material.

$^{1}$H-NMR (400 MHz, CD$_{3}$OD) δ 7.61-7.58 (1H, m), 7.53-7.52 (1H, m), 7.36 (1H, t, J=8.1 Hz), 7.15-7.12 (1H, m), 5.99-5.88 (1H, m), 5.20-5.14 (1H, m), 5.11-5.07 (1H, m), 4.06 (2H, t, J=6.6 Hz), 2.57-2.51 (2H, m).

(Reaction 363-3)

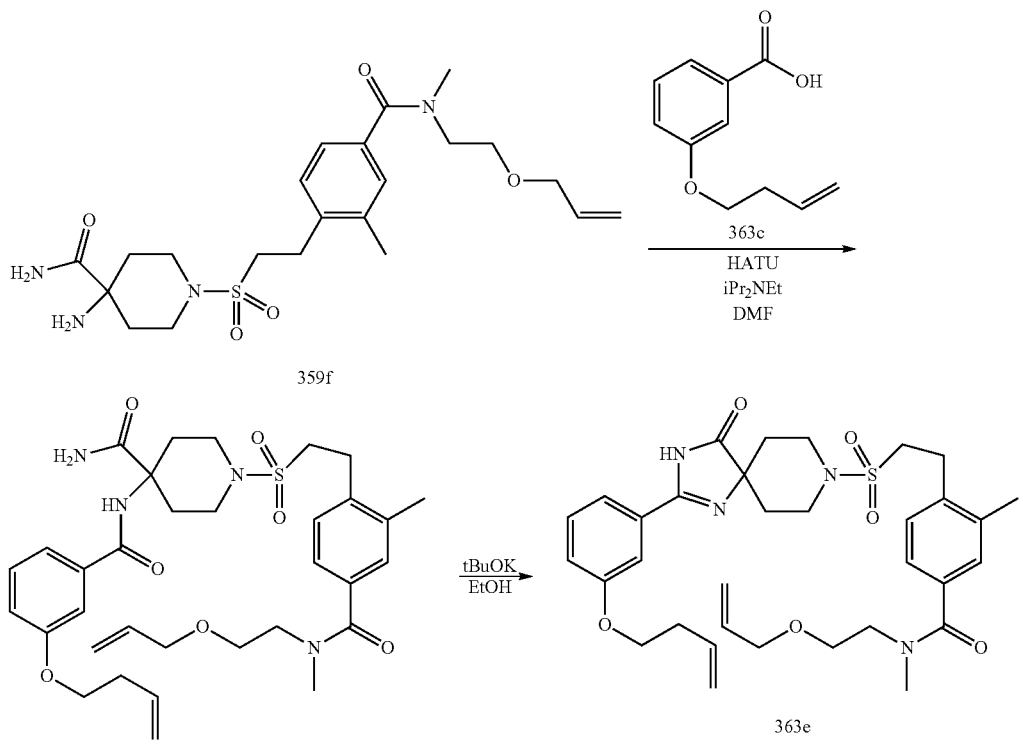

N-(2-Allyloxy-ethyl)-4-{2-[2-(3-but-3-enyloxy-phenyl)-4-oxo-1,3,8-triaza-spiro[4.5]dec-1-ene-8-sulfonyl]-ethyl}-3,N-dimethyl-benzamide was obtained by the same method as in Reaction 359-9 using 3-but-3-enyloxy-benzoic acid and 1-(2-{4-[(2-allyloxy-ethyl)-methyl-carbamoyl]-2-methyl-phenyl}-ethanesulfonyl)-4-amino-piperidine-4-carboxylic amide as starting materials.

MS (ESI) m/z=621 (M–H)–;

HPLC retention time: 2.85 min (analysis condition LCMS-C-1).

(Reaction 363-4)

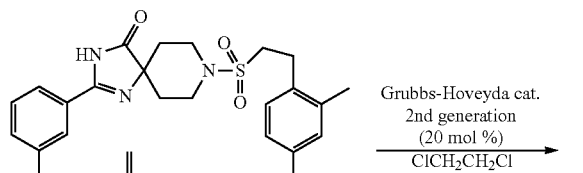

A macrocyclic olefin compound (Compound 1435) E/Z=1:2) was obtained by the same method as in Reaction 338-1 (using Hoveyda-Grubbs $2^{nd}$ generation as a catalyst) using N-(2-allyloxy-ethyl)-4-{2-[2-(3-but-3-enyloxy-phenyl)-4-oxo-1,3,8-triaza-spiro[4.5]dec-1-ene-8-sulfonyl]-ethyl}-3,N-dimethyl-benzamide as a starting material.

MS (ESI) m/z=595 (M+H)+;

HPLC retention time: 2.70 min (analysis condition LCMS-C-1).

Example 364

Compound 1436

(Reaction 364-1)

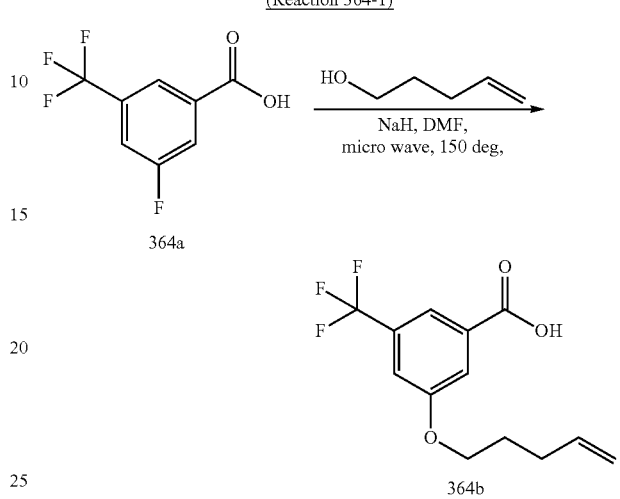

A solution of 3-fluoro-5-trifluoromethyl-benzoic acid (400 mg, 1.92 mmol) in DMF (2 ml) was added dropwise to a suspension of sodium hydride (60% oily, 235 mg, 5.88 mmol) and pent-4-en-1-ol (506 mg, 5.88 mmol) in DMF (12 ml), and the mixture was stirred at 60° C. Further, this mixture was irradiated in a microwave apparatus (150° C., 20 min). The reaction solution was poured into 0.2 N aqueous hydrochloric acid and then extracted with ethyl acetate. The organic layer was washed with saturated brine, and then dried over anhydrous sodium sulfate and concentrated under reduced pressure. The resulting residue was purified by silica gel column chromatography (hexane-ethyl acetate) to give 3-pent-4-enyloxy-5-trifluoromethyl-benzoic acid (290 mg, 55%).

$^1$H-NMR (CDCl$_3$) δ 7.94 (1H, s), 7.77 (1H, s), 7.37 (1H, s), 5.91-5.81 (1H, m), 5.11-5.06 (1H, m), 5.05-5.02 (1H, m), 4.07 (2H, t, J=6.3 Hz), 2.30-2.24 (2H, m), 1.97-1.90 (2H, m);

MS (ESI) m/z=273 (M–H)–;

HPLC retention time: 2.50 min (analysis condition LCMS-C-1).

(Reaction 364-2)

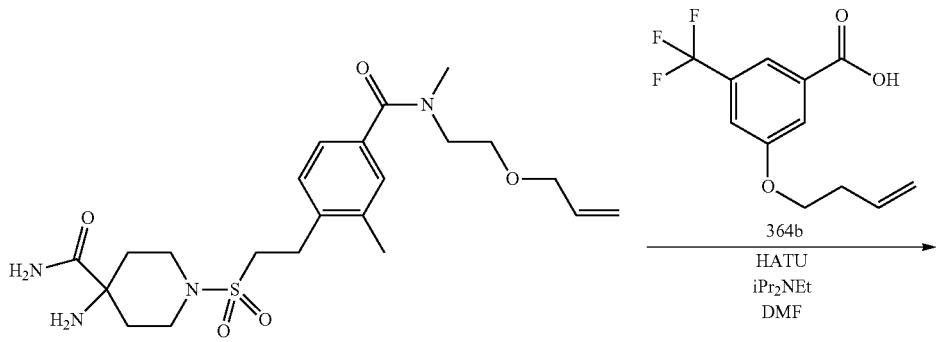

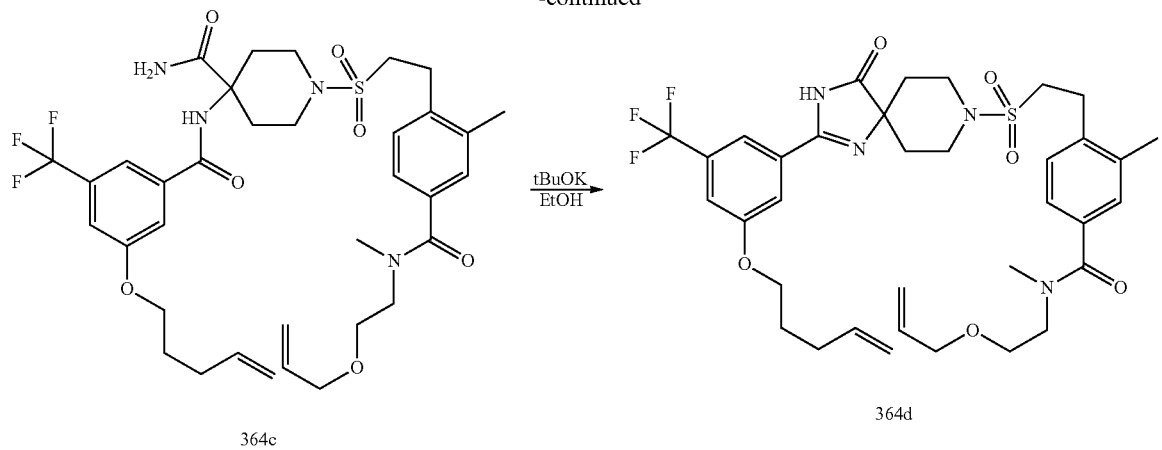

364c      364d

N-(2-Allyloxy-ethyl)-3,N-dimethyl-4-{2-[4-oxo-2-(3-pent-4-enyloxy-5-trifluoromethyl-phenyl)-1,3,8-triaza-spiro[4.5]dec-1-ene-8-sulfonyl]-ethyl}-benzamide was obtained by the same method as in Reaction 359-9 using 3-pent-4-enyloxy-5-trifluoromethyl-benzoic acid and 1-(2-{4-[(2-allyloxy-ethyl)-methyl-carbamoyl]-2-methyl-phenyl}-ethanesulfonyl)-4-amino-piperidine-4-carboxylic amide as starting materials.

MS (ESI) m/z=705 (M+H)+

HPLC retention time: 1.12 min (analysis condition LCMS-F-1).

(Reaction 364-3)

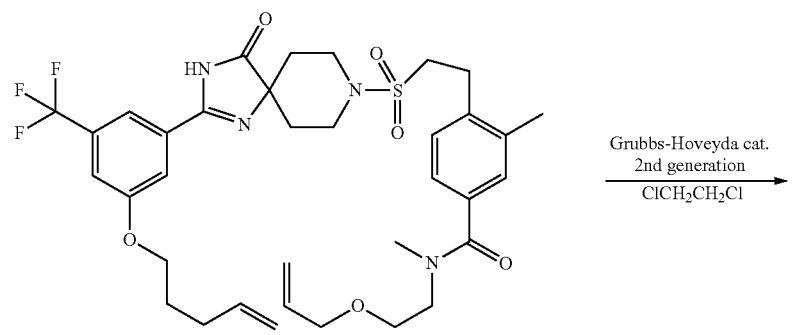

364d

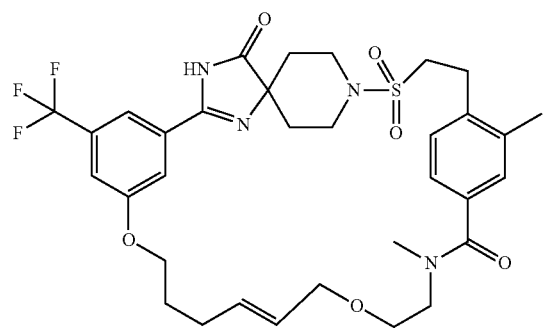

Compound 1436

1619

A macrocyclic olefin compound (Compound 1436) was obtained by the same method as in Reaction 338-1 (using Hoveyda-Grubbs 2nd generation as a catalyst) using N-(2-allyloxy-ethyl)-3,N-dimethyl-4-{2-[4-oxo-2-(3-pent-4-enyloxy-5-trifluoromethyl-phenyl)-1,3,8-triaza-spiro[4.5]dec-1-ene-8-sulfonyl]-ethyl}-benzamide as a starting material.

MS (ESI) m/z=677 (M+H)+;

HPLC retention time: 1.07 min (analysis condition LCMS-F-1).

Example 365

Compound 1437

(Reaction 365-1)

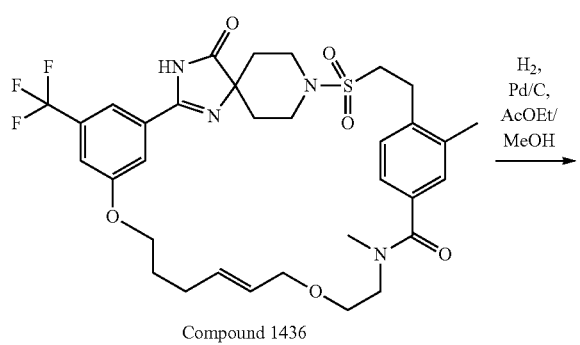

Compound 1436

Compound 1437

A saturated macrocyclic compound (Compound 1437) was obtained by the same method as in Reaction 339-1 using a macrocyclic olefin compound (Compound 1436) as a starting material.

MS (ESI) m/z=679 (M+H)+;

HPLC retention time: 1.11 min (analysis condition LCMS-F-1).

Example 366

Compound 1438

(Reaction 366-1)

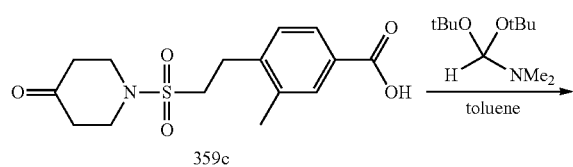

359c

1620

-continued

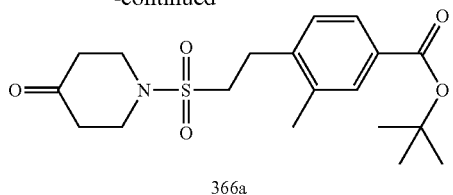

366a

3-Methyl-4-[2-(4-oxo-piperidine-1-sulfonyl)-ethyl]-benzoic acid (1.23 g, 3.78 mmol) was suspended in toluene (20.0 ml). Di-tert-butoxymethyl-dimethyl-amine (3.63 ml, 15.12 mmol) was added and the mixture was stirred at 80° C. for 30 minutes. Thereafter, di-tert-butoxymethyl-dimethyl-amine (2.70 ml, 11.34 mmol) was added again and the mixture was stirred at 80° C. for 30 minutes. After completion of the reaction, the reaction solution was left to cool and diluted with ethyl acetate. The organic layer was then washed with an aqueous sodium bicarbonate solution and saline. The organic layer was dried over anhydrous magnesium sulfate and then concentrated under reduced pressure. The resulting residue was purified by column chromatography (hexane:ethyl acetate) to give 3-methyl-4-[2-(4-oxopiperidine-1-sulfonyl)-ethyl]-benzoic acid tert-butyl ester as a white solid (1.01 g, 70.0%).

MS (ESI) m/z=382 (M+H)+;

HPLC retention time: 2.54 min (analysis condition LCMS-B-1)

(Reaction 366-2)

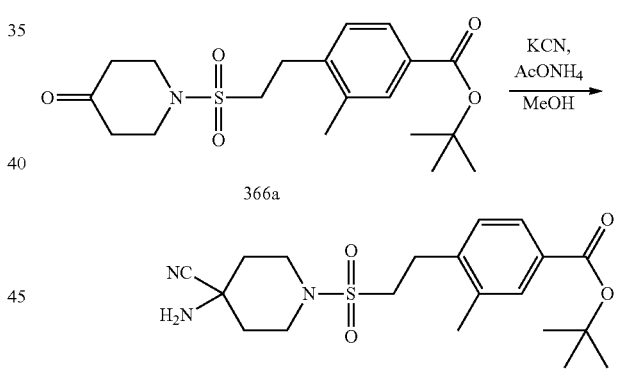

366a

366b

3-Methyl-4-[2-(4-oxo-piperidine-1-sulfonyl)-ethyl]-benzoic acid tert-butyl ester (969.2 mg, 2.54 mmol), ammonium acetate (469.9 mg, 6.10 mmol) and potassium cyanide (330.9 mg, 5.08 mmol) were dissolved in methanol (12.0 ml), and the mixture was stirred at 65° C. for one hour. After completion of the reaction, the mixture was left to cool and an aqueous sodium bicarbonate solution was added, followed by extraction with ethyl acetate. The organic layer was washed with saline, and then dried over anhydrous magnesium sulfate and concentrated under reduced pressure to give 4-[2-(4-amino-4-cyano-piperidine-1-sulfonyl)-ethyl]-3-methyl-benzoic acid tert-butyl ester as an amorphous (1.07 g).

MS (ESI) m/z=408 (M+H)+;

HPLC retention time: 2.54 min (analysis condition LCMS-F-1).

(Reaction 366-3)

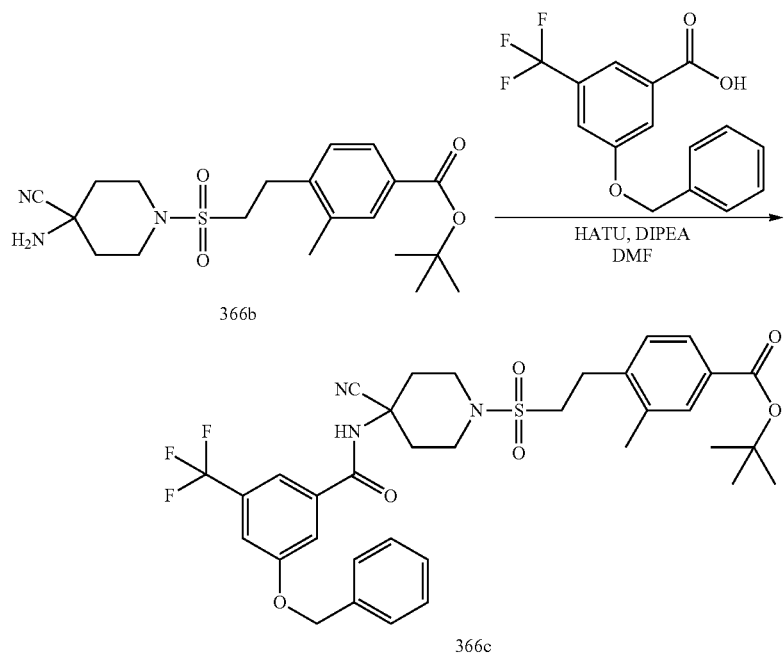

4-[2-(4-Amino-4-cyano-piperidine-1-sulfonyl)-ethyl]-3-methyl-benzoic acid tert-butyl ester (500.0 mg, 1.23 mmol), 3-benzyloxy-5-trifluoromethyl-benzoic acid (436.1 mg, 1.47 mmol) and DIPEA (0.321 ml, 1.85 mmol) were dissolved in DMF (5.50 ml). HATU (561.2 mg, 1.47 mmol) was added and the mixture was stirred at room temperature for one hour. The reaction solution was diluted with diethyl ether, and the organic layer was washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (hexane-ethyl acetate) to give 4-{2-[4-(3-benzyloxy-5-trifluoromethyl-benzoylamino)-4-cyano-piperidine-1-sulfonyl]-ethyl}-3-methyl-benzoic acid tert-butyl ester as a yellow amorphous (796.2 mg, 94.4% in two steps).

MS (ESI) m/z=685 (M+H)+;

HPLC retention time: 1.16 min (analysis condition LCMS-F-1).

(Reaction 366-4)

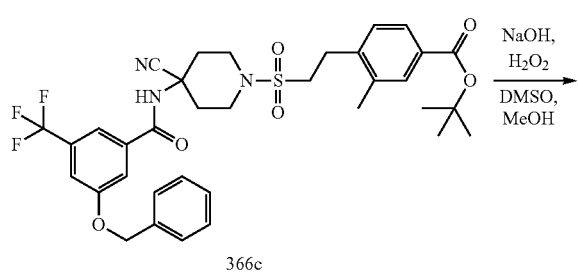

-continued

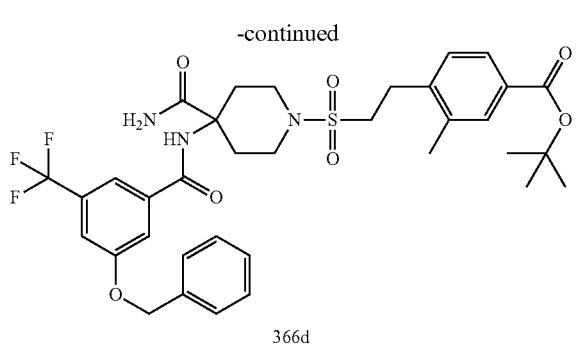

4-{2-[4-(3-Benzyloxy-5-trifluoromethyl-benzoylamino)-4-cyano-piperidine-1-sulfonyl]-ethyl}-3-methyl-benzoic acid tert-butyl ester (1.40 g, 2.04 mmol) was dissolved in DMSO (0.188 ml, 2.65 mmol) and methanol (7.00 ml). A 1 M aqueous sodium hydroxide solution (0.204 ml, 0.204 mmol) and aqueous hydrogen peroxide (30%, 0.265 ml, 2.65 mmol) were added under ice-cooling. The mixture was warmed to room temperature and stirred as such for two hours. After completion of the reaction, an aqueous sodium thiosulfate solution and an aqueous ammonium chloride solution were added, followed by extraction with ethyl acetate. The organic layer was washed with saline, dried over anhydrous magnesium sulfate and then concentrated under reduced pressure to give 4-{2-[4-(3-benzyloxy-5-trifluoromethyl-benzoylamino)-4-carbamoyl-piperidine-1-sulfonyl]-ethyl}-3-methyl-benzoic acid tert-butyl ester as a pale yellow amorphous (1.48 g).

MS (ESI) m/z=704 (M+H)+;

HPLC retention time: 1.15 min (analysis condition LCMS-F-1).

(Reaction 366-5)

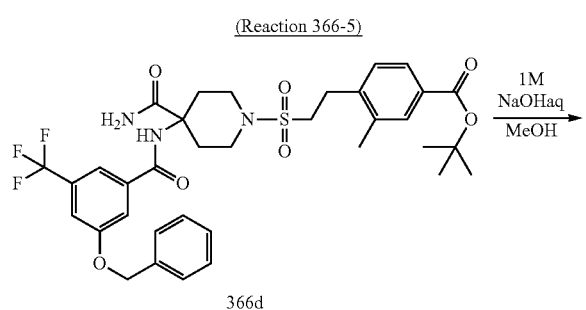

366d

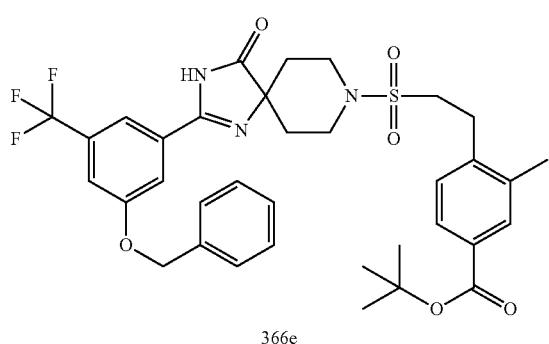

366e

4-{2-[4-(3-Benzyloxy-5-trifluoromethyl-benzoylamino)-4-carbamoyl-piperidine-1-sulfonyl]-ethyl}-3-methyl-benzoic acid tert-butyl ester (1.23 g, 1.75 mmol) was dissolved in methanol (17.5 ml). A 1 M aqueous sodium hydroxide solution (1.75 ml, 1.75 mmol) was added and the mixture was stirred at 60° C. for six hours. After completion of the reaction, the reaction solution was left to cool and an aqueous ammonium chloride solution was added, followed by extraction with ethyl acetate. The organic layer was washed with saline, dried over anhydrous magnesium sulfate and then concentrated under reduced pressure. The residue obtained by concentration was purified by column chromatography (hexane:ethyl acetate) to give 4-{2-[2-(3-benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester as a pale yellow amorphous (952.1 mg, yield in two steps: 79.3%).

MS (ESI) m/z=686 (M+H)+;

HPLC retention time: 1.19 min (analysis condition LCMS-F-1).

(Reaction 366-6)

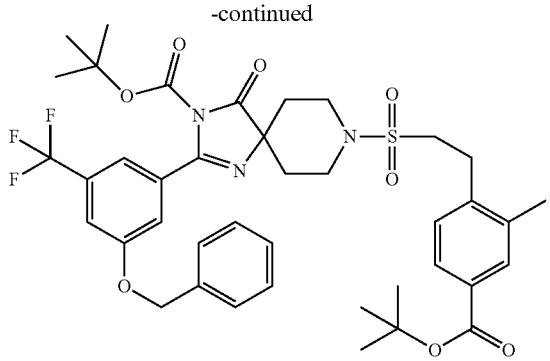

366g

4-{2-[2-(3-Benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester (1.14 g, 1.66 mmol) was dissolved in THF (8.0 ml). DMAP (60.8 mg, 0.498 mmol) and di-tert-butyl dicarbonate (725.6 mg, 3.32 mmol) were added and the mixture was stirred at room temperature for one hour. Thereafter, di-tert-butyl dicarbonate (181.0 mg, 0.830 mmol) was further added and the mixture was stirred at room temperature for 30 minutes. After completion of the reaction, the reaction solution was diluted with ethyl acetate, and the organic layer was washed with saline. The organic layer was dried over anhydrous magnesium sulfate and then concentrated under reduced pressure. The resulting residue was purified by column chromatography (hexane:ethyl acetate) to give 2-(3-benzyloxy-5-trifluoromethyl-phenyl)-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester as a white solid (1.11 g, 85.1%).

MS (ESI) m/z=786 (M+H)+;

HPLC retention time: 1.20 min (analysis condition LCMS-F-1).

(Reaction 366-7)

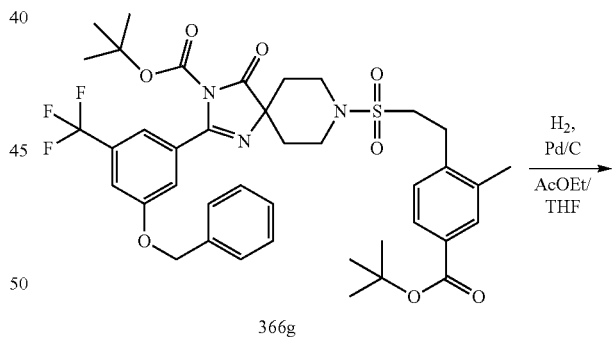

366g

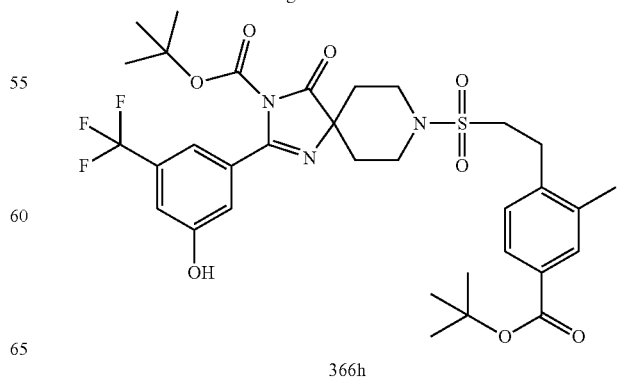

366h 2-(3-Benzyloxy-5-trifluoromethyl-phenyl)-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (1.11 g, 1.41 mmol) was dissolved in ethyl acetate (45.0 ml)-THF (15.0 ml). Pd—C (222 mg) was added and the mixture was stirred at room temperature and for one hour in a hydrogen atmosphere. After completion of the reaction, the black solid was filtered off through celite, and the filtrate was concentrated under reduced pressure to give 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester as an amorphous (1.01 g, 100%).

$^1$H-NMR (400 MHz, CDCl$_3$) δ 7.80-7.82 (2H, m), 7.22-7.24 (4H, m), 6.83 (1H, br), 3.68-3.74 (2H, m), 3.11-3.27 (6H, m), 2.50 (3H, s), 2.05-2.14 (2H, m), 1.63-1.71 (2H, m), 1.38 (9H, s);

MS (ESI) m/z=696 (M+H)+;

HPLC retention time: 1.13 min (analysis condition LCMS-F-1).

(Reaction 366-8)

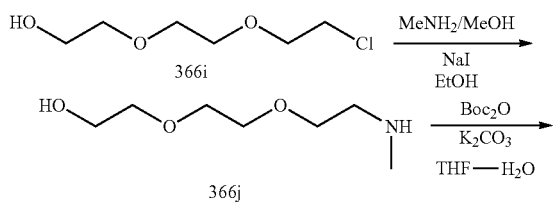

2-[2-(2-Chloro-ethoxy)-ethoxy]-ethanol (2.00 mL, 13.8 mmol) was dissolved in ethanol (14.0 mL). A solution of methylamine in methanol (40%, 14.0 mL, 138 mmol) and sodium iodide (103 mg, 0.67 mmol) were added, and the mixture was stirred at 60° C. for 18 hours and then stirred at 75° C. for seven hours in a nitrogen atmosphere. The reaction solution was concentrated under reduced pressure to give 2-[2-(2-methylamino-ethoxy)-ethoxy]-ethanol as a crude product.

2-[2-(2-Methylamino-ethoxy)-ethoxy]-ethanol was dissolved in THF (6.88 mL)-water (6.88 mL). Di-tert-butyl dicarbonate (9.01 g, 41.3 mmol) and potassium carbonate (5.71 g, 41.3 mmol) were added at 0° C., and the mixture was stirred at room temperature for 15 hours. A 1 M aqueous hydrochloric acid solution was added to the reaction solution, followed by extraction with ethyl acetate. The organic layer was washed with saturated aqueous sodium bicarbonate and saturated brine, and then dried over sodium sulfate and concentrated under reduced pressure. The resulting residue was purified by silica gel column chromatography (hexane-ethyl acetate) to give {2-[2-(2-hydroxy-ethoxy)-ethoxy]-ethyl}-methyl-carbamic acid tert-butyl ester (1.53 g, 42%).

$^1$H-NMR (CDCl$_3$) δ 3.74-3.72 (2H, m), 3.67-3.60 (8H, m), 3.42-3.39 (2H, br m), 2.91 (3H, s), 1.45 (9H, s).

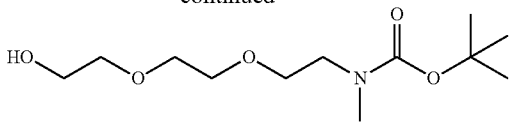

366k (Reaction 366-9)

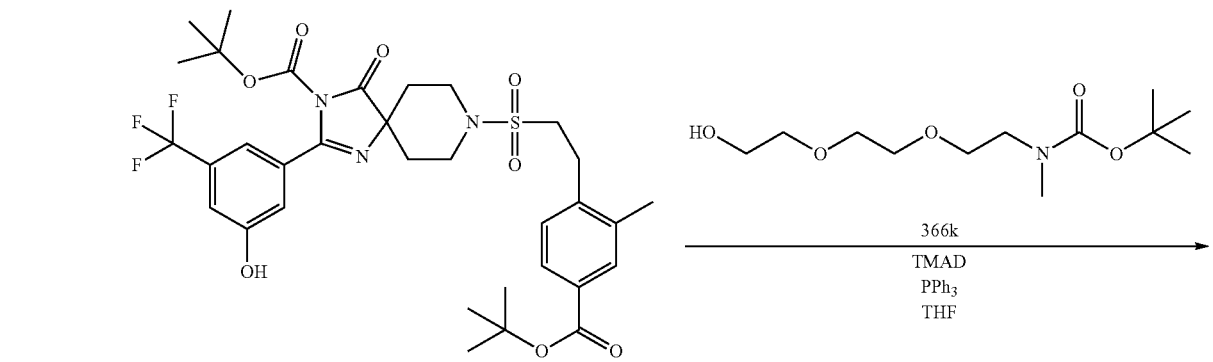

366h

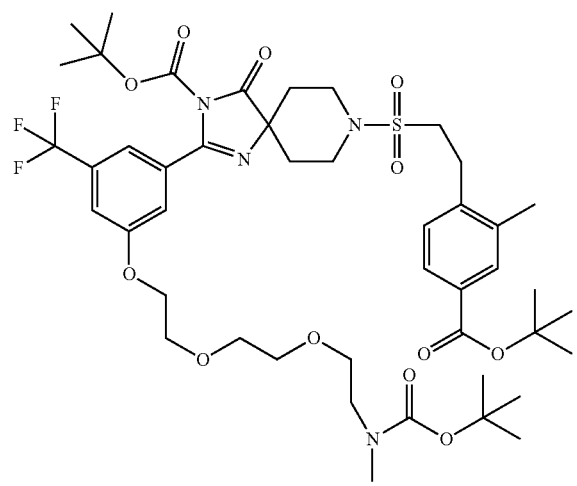

366l

8-[2-(4-tert-Butoxycarbonyl-2-methyl-phenyl)-ethane-sulfonyl]-2-(3-hydroxy-5-trifluoromethyl-phenyl)-4-oxo-1,3,8-triaza-spiro[4.5]dec-1-ene-3-carboxylic acid tert-butyl ester (30.0 mg, 43.1 µmol), {2-[2-(2-hydroxy-ethoxy)-ethoxy]-ethyl}-methyl-carbamic acid tert-butyl ester (22.7 mg, 86.2 µmol) and triphenylphosphine (22.6 mg, 86.2 µmol) were dissolved in THF (0.22 mL). TMAD (14.8 mg, 86.2 µmol) was added and the mixture was stirred at 60° C. for 30 minutes in a nitrogen atmosphere. The reaction solution was concentrated under reduced pressure, and the resulting residue was then purified by silica gel column chromatography (hexane-ethyl acetate) to give 2-[3-(2-{2-[2-(tert-butoxycarbonyl-methyl-amino)-ethoxy]-ethoxy}-ethoxy)-5-trifluoromethyl-phenyl]-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (37.4 mg, 86%).

MS (ESI) m/z=941 (M+H)+;

HPLC retention time: 1.18 min (analysis condition LCMS-F-1).

(Reaction 366-10)

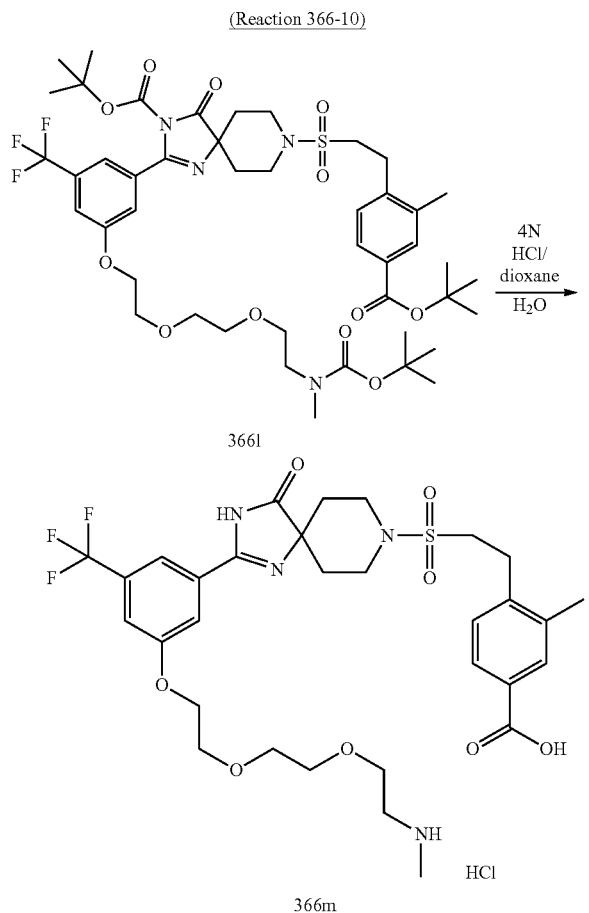

366m

2-[3-(2-{2-[2-(tert-Butoxycarbonyl-methyl-amino)-ethoxy]-ethoxy}-ethoxy)-5-trifluoromethyl-phenyl]-8-[2-(4-tert-butoxycarbonyl-2-methyl-phenyl)-ethanesulfonyl]-4-oxo-1,3,8-triaza-spiro[4.5]dec-1-ene-3-carboxylic acid tert-butyl ester (37.4 mg, 39.7 µmol) was dissolved in 4 N hydrochloric acid-dioxane (0.79 mL). Water (14.3 µL, 795 µmol) was added and the mixture was stirred at room temperature for three hours. The reaction solution was concentrated under reduced pressure to give 3-methyl-4-{2-[2-(3-{2-[2-(2-methylamino-ethoxy)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride (28.0 mg, 98%).

MS (ESI) m/z=685 (M+H)+;

HPLC retention time: 1.88 min (analysis condition LCMS-B-1).

(Reaction 366-11)

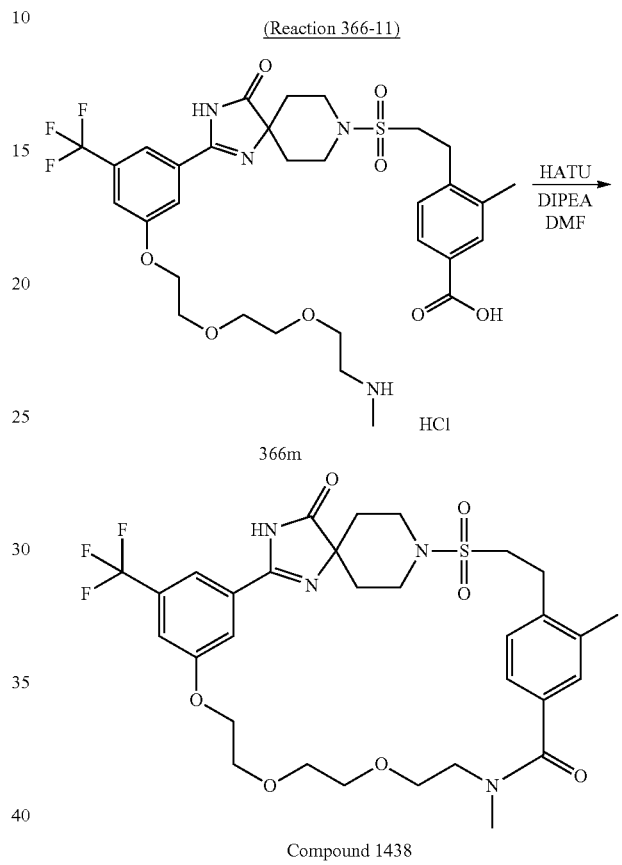

Compound 1438

3-Methyl-4-{2-[2-(3-{2-[2-(2-methylamino-ethoxy)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride (26.0 mg, 36.1 µmol) was dissolved in DMF (7.21 mL). DIPEA (62.8 µL, 361 µmol) and HATU (68.6 mg, 180 µmol) were added and the mixture was stirred at 70° C. for two hours. A 3 M aqueous hydrochloric acid solution was added to the reaction solution, followed by extraction with ethyl acetate. The organic layer was washed with water, saturated aqueous sodium bicarbonate and saturated brine, and then dried over sodium sulfate and concentrated under reduced pressure. The resulting residue was purified by silica gel column chromatography (dichloromethane-ethyl acetate) to give a saturated macrocyclic compound (Compound 1438) (20.8 mg, 87%).

$^{1}$H-NMR (CD$_3$OD) δ 7.93 (1H, s), 7.88 (1H, s), 7.61 (1H, s), 7.32 (1H, s), 7.25-7.22 (2H, m), 7.14 (1H, d, J=7.4 Hz), 4.15 (2H, t, J=5.4 Hz), 3.78-3.35 (16H, m), 3.11-3.06 (2H, m), 2.97 (3H, s), 2.37 (3H, s), 1.98 (2H, td, J=13.0, 4.0 Hz), 1.56 (2H, d, J=12.9 Hz);

MS (ESI) m/z=667 (M+H)+;

HPLC retention time: 2.25 min (analysis condition LCMS-B-1).

Example 367

Compound 1439

(Reaction 367-1)

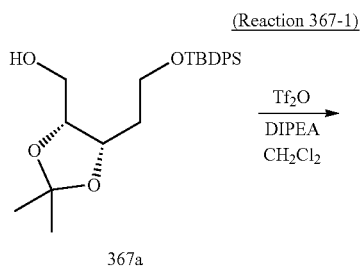

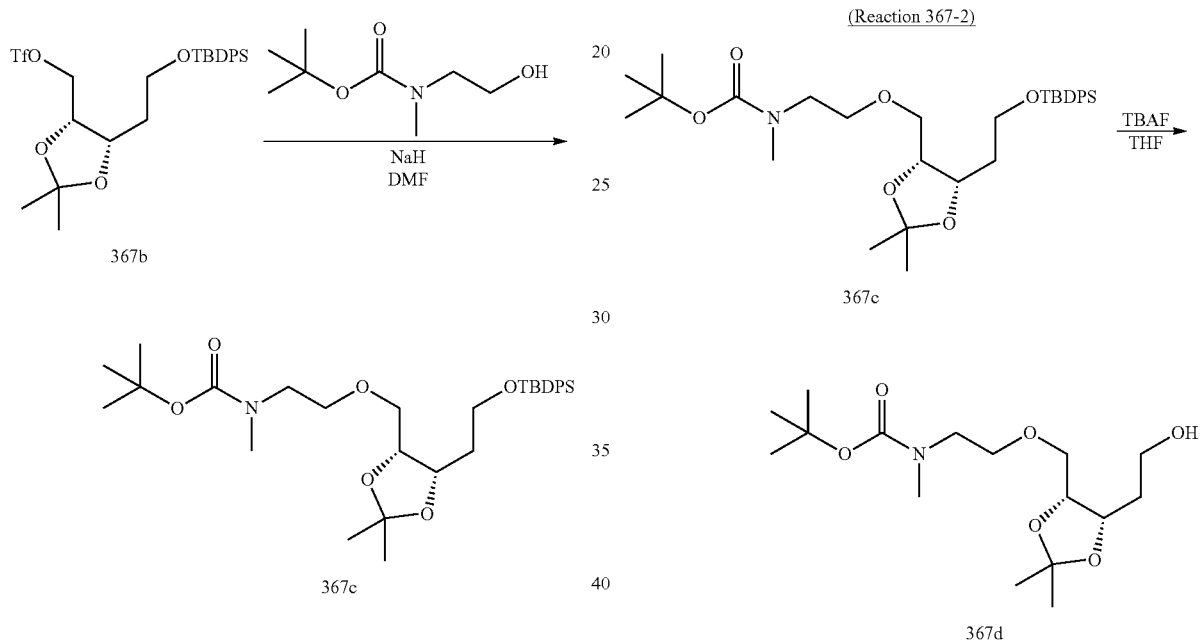

{(4R,5S)-5-[2-(tert-Butyl-diphenyl-silanyloxy)-ethyl]-2,2-dimethyl-[1,3]dioxolan-4-yl}-methanol (159 mg, 0.38 mmol) was dissolved in dichloromethane (1.15 mL). Diisopropylethylamine (200 µL, 1.15 mmol) and Tf₂O (77.4 µL, 0.46 mmol) were added at 0° C., and the mixture was stirred at room temperature for one hour in a nitrogen atmosphere. Saturated aqueous ammonium chloride was added to the reaction solution, followed by extraction with ethyl acetate. The organic layer was washed with saturated aqueous sodium bicarbonate and saturated brine, dried over sodium sulfate and filtered. The filtrate was concentrated under reduced pressure to give trifluoro-methanesulfonic acid (4R,5S)-5-[2-(tert-butyl-diphenyl-silanyloxy)-ethyl]-2,2-dimethyl-[1,3]dioxolan-4-ylmethyl ester as a crude product.

(2-Hydroxy-ethyl)-methyl-carbamic acid tert-butyl ester (73.9 mg, 0.42 mmol) was dissolved in THF (1.15 mL). Sodium hydride (50%, 22.1 mg, 0.46 mmol) was added at 0° C. and the mixture was stirred at 0° C. for 10 minutes in a nitrogen atmosphere. Trifluoro-methanesulfonic acid (4R,5S)-5-[2-(tert-butyl-diphenyl-silanyloxy)-ethyl]-2,2-dimethyl-[1,3]dioxolan-4-ylmethyl ester was added to the reaction solution, and the mixture was stirred at room temperature for two hours in a nitrogen atmosphere. Saturated aqueous ammonium chloride was added to the reaction solution, followed by extraction with ethyl acetate. The organic layer was washed with saturated aqueous sodium bicarbonate and saturated brine, dried over sodium sulfate and filtered, and the filtrate was concentrated under reduced pressure. The resulting residue was purified by silica gel column chromatography (hexane-ethyl acetate) to give (2-{(4R,5S)-5-[2-(tert-butyl-diphenyl-silanyloxy)-ethyl]-2,2-dimethyl-[1,3]dioxolan-4-ylmethoxy}-ethyl)-methyl-carbamic acid tert-butyl ester (82.2 mg, 38%).

MS (ESI) m/z=572 (M+H)+;

HPLC retention time: 1.27 min (analysis condition LCMS-F-1).

(2-{(4R,5S)-5-[2-(tert-Butyl-diphenyl-silanyloxy)-ethyl]-2,2-dimethyl-[1,3]dioxolan-4-ylmethoxy}-ethyl)-methyl-carbamic acid tert-butyl ester (82.2 mg, 0.14 mmol) was dissolved in THF (0.19 mL). TBAF (1.0 M solution in THF, 0.19 mL, 0.19 mmol) was added at 0° C. and the mixture was stirred at room temperature for one hour in a nitrogen atmosphere. Saturated aqueous ammonium chloride was added to the reaction solution, followed by extraction with ethyl acetate. The organic layer was washed with saturated aqueous sodium bicarbonate and saturated brine, and then dried over sodium sulfate and concentrated under reduced pressure. The resulting residue was purified by silica gel column chromatography (hexane-ethyl acetate) to give {2-[(4R,5S)-5-(2-hydroxy-ethyl)-2,2-dimethyl-[1,3]dioxolan-4-ylmethoxy]-ethyl}-methyl-carbamic acid tert-butyl ester (41.7 mg, 88%).

¹H-NMR (CDCl₃) δ 4.34-4.31 (1H, m), 4.25 (1H, q, J=6.1 Hz), 3.84-3.74 (2H, m), 3.54-3.47 (6H, m), 2.90 (3H, s), 2.46 (1H, dd, J=7.8, 3.3 Hz), 1.82-1.78 (2H, br m), 1.45-1.44 (12H, m), 1.35 (3H, s).

(Reaction 367-3)

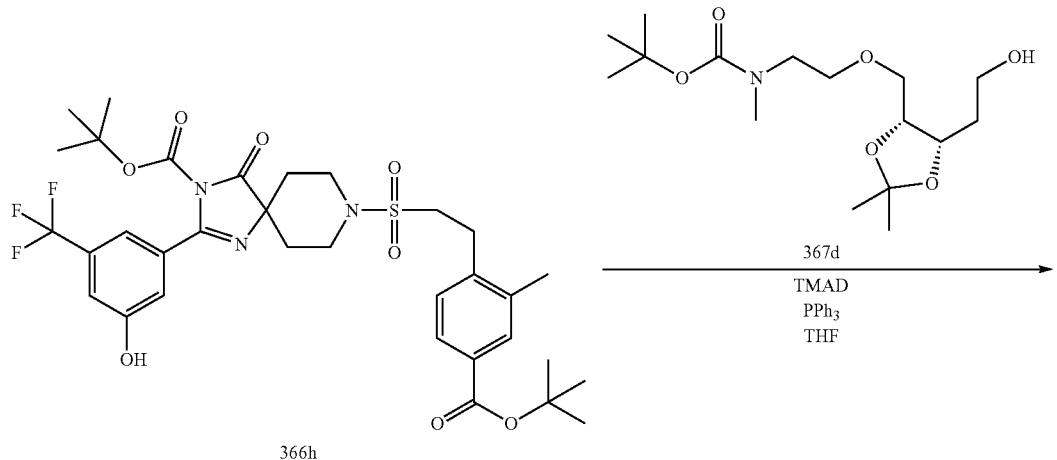

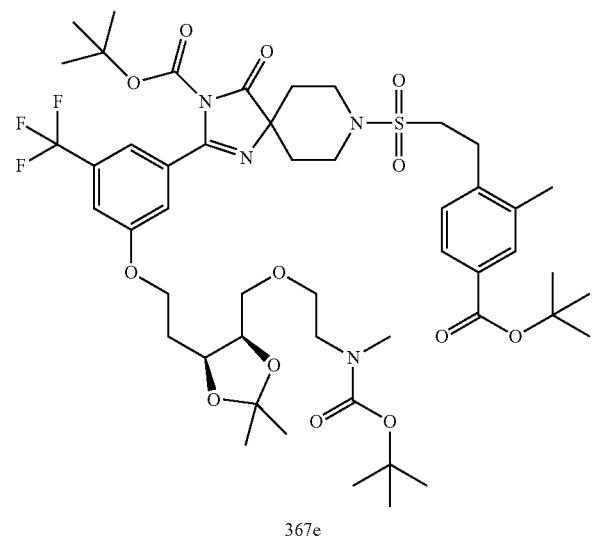

2-(3-(2-((4S,5R)-5-((2-(tert-Butoxycarbonyl(methyl)amino)ethoxy)methyl)-2,2-dimethyl-1,3-dioxolan-4-yl)ethoxy)-5-(trifluoromethyl)phenyl)-8-(4-(tert-butoxycarbonyl)-2-methylphenethylsulfonyl)-4-oxo-1,3,8-triazaspiro[4.5]dec-1-ene-3-carboxylic acid tert-butyl ester was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and {2-[(4R,5S)-5-(2-hydroxy-ethyl)-2,2-dimethyl-[1,3]dioxolan-4-ylmethoxy]-ethyl}-methyl-carbamic acid tert-butyl ester as starting materials.

MS (ESI) m/z=1012 (M+H)+;

HPLC retention time: 1.21 min (analysis condition LCMS-F-1).

(Reaction 367-4)

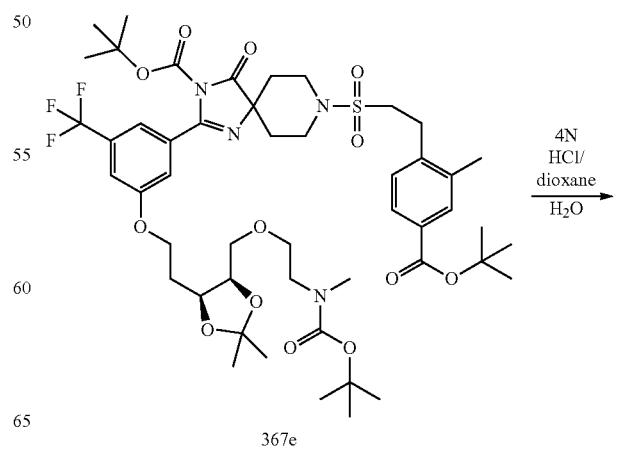

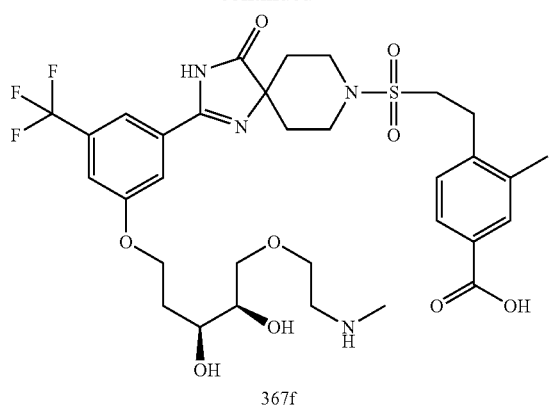
367f

4-[2-(2-{3-[(3S,4R)-3,4-Dihydroxy-5-(2-methylamino-ethoxy)-pentyloxy]-5-trifluoromethyl-phenyl}-4-oxo-1,3,8-triaza-spiro[4.5]dec-1-ene-8-sulfonyl)-ethyl]-3-methyl-benzoic acid hydrochloride was obtained by the same method as in Reaction 366-10 using 2-(3-(2-((4S,5R)-5-((2-(tert-butoxycarbonyl(methyl)amino)ethoxy)methyl)-2,2-dimethyl-1,3-dioxolan-4-yl)ethoxy)-5-(trifluoromethyl)phenyl)-8-(4-(tert-butoxycarbonyl)-2-methylphenethylsulfonyl)-4-oxo-1,3,8-triazaspiro[4.5]dec-1-ene-3-carboxylic acid tert-butyl ester as a starting material.

MS (ESI) m/z=729 (M+H)+;

HPLC retention time: 0.80 min (analysis condition LCMS-F-1).

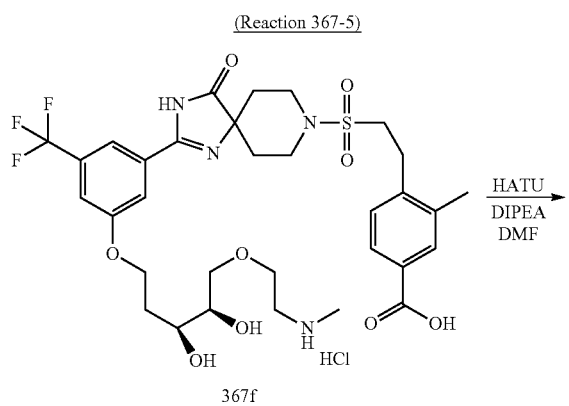
Compound 1439

A saturated macrocyclic compound (Compound 1439) was obtained by the same method as in Reaction 366-11 using 4-[2-(2-{3-[(3S,4R)-3,4-dihydroxy-5-(2-methyl-amino-ethoxy)-pentyloxy]-5-trifluoromethyl-phenyl}-4-oxo-1,3,8-triaza-spiro[4.5]dec-1-ene-8-sulfonyl)-ethyl]-3-methyl-benzoic acid hydrochloride as a starting material.

MS (ESI) m/z=697 (M+H)+;

HPLC retention time: 0.92 min (analysis condition LCMS-F-1).

Example 368

Compound 1440

(Reaction 368-1)

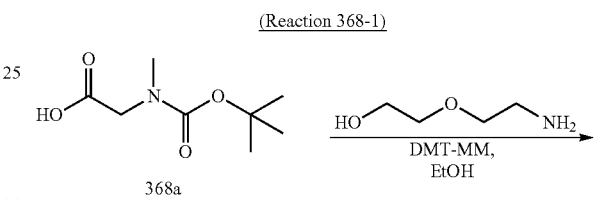
368a

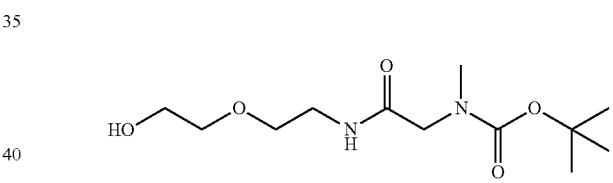
368b

BOC-sarcosine (900 mg, 4.76 mmol) was dissolved in ethanol (10 ml). 2-(2-Aminoethoxy)ethanol (0.477 ml, 4.76 mmol) and 4-(4,6-dimethoxy-1,3,5-triazin-2-yl)-4-methyl-morpholinium chloride n-hydrate (DMT-MM) (1.79 g, 5.71 mmol) were added and the mixture was stirred at room temperature overnight. The reaction solution was concentrated under reduced pressure, and water was added to the resulting residue, followed by extraction with ethyl acetate. The organic layer was washed with water and saturated brine, dried over anhydrous sodium sulfate and concentrated under reduced pressure. The resulting residue was subjected to silica gel column chromatography (dichloromethane-methanol) to give {[2-(2-hydroxy-ethoxy)-ethylcarbamoyl]-methyl}-methyl-carbamic acid tert-butyl ester. This was used in the next reaction without complete purification.

(Reaction 368-2)

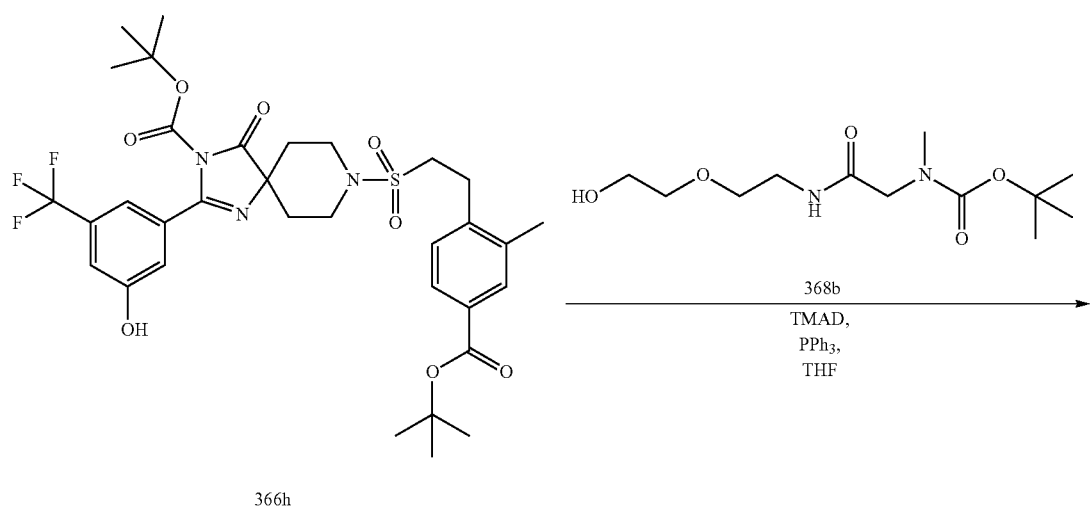

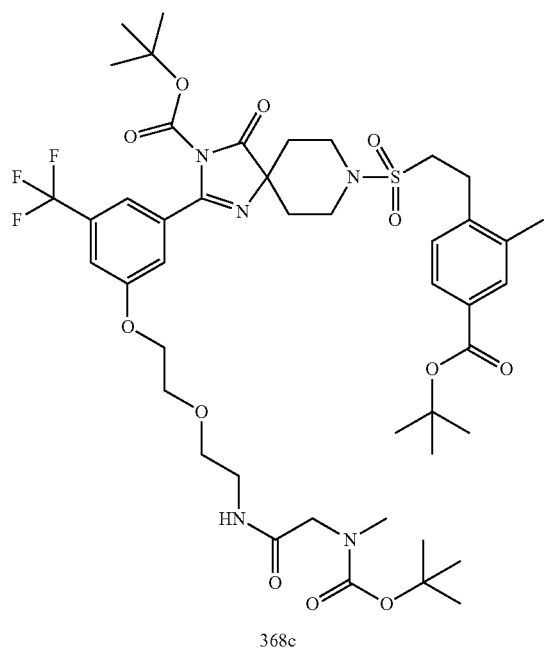

8-[2-(4-tert-Butoxycarbonyl-2-methyl-phenyl)-ethanesulfonyl]-2-[3-(2-{2-[2-(tert-butoxycarbonyl-methyl-amino)-acetylamino]-ethoxy}-ethoxy)-5-trifluoromethyl-phenyl]-4-oxo-1,3,8-triaza-spiro[4.5]dec-1-ene-3-carboxylic acid tert-butyl ester was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and {[2-(2-hydroxyethoxy)-ethylcarbamoyl]-methyl}-methyl-carbamic acid tert-butyl ester as starting materials. This was used in the next reaction without complete purification.

(Reaction 368-3)

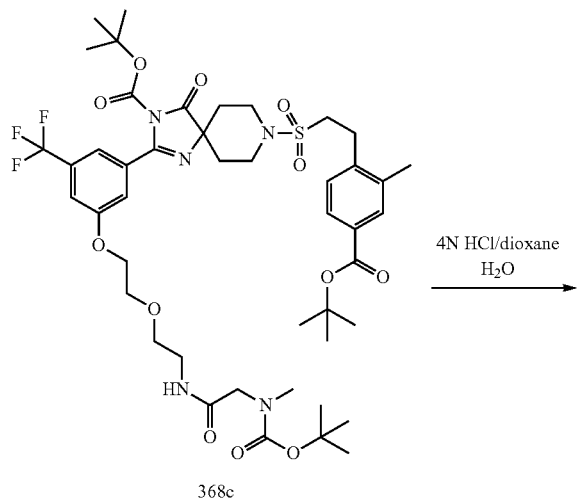

368c

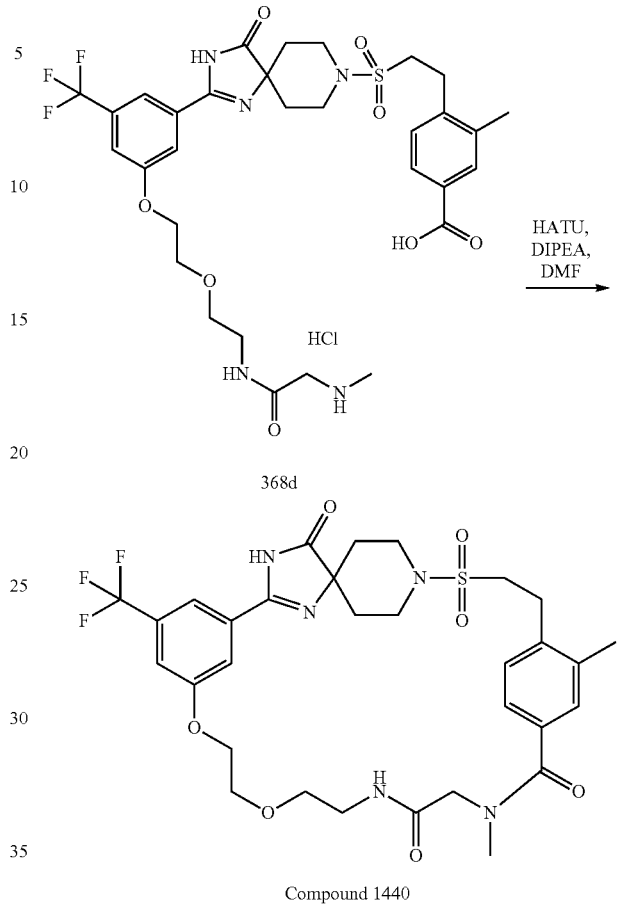

368d

3-Methyl-4-{2-[2-(3-{2-[2-(2-methylamino-acety-lamino)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride was obtained by the same method as in Reaction 366-10 using 8-[2-(4-tert-butoxycarbonyl-2-methyl-phenyl)-ethanesulfonyl]-2-[3-(2-{2-[2-(tert-butoxy-carbonyl-methyl-amino)-acetylamino]-ethoxy}-ethoxy)-5-trifluoromethyl-phenyl]-4-oxo-1,3,8-triaza-spiro[4.5]dec-1-ene-3-carboxylic acid tert-butyl ester (13 mg, 0.0136 mmol) as a starting material. This was used in the next reaction without complete purification.

Compound 1440

A saturated macrocyclic compound (Compound 1440) was obtained by the same method as in Reaction 366-11 using 3-methyl-4-{2-[2-(3-{2-[2-(2-methylamino-acety-lamino)-ethoxy]-ethoxy}-5-trifluoromethyl-phenyl)-4-oxo-1,3,8-triaza-spiro[4.5]dec-1-ene-8-sulfonyl]-ethyl}-benzoic acid hydrochloride as a starting material.

MS (ESI) m/z=680 (M+H)+;
HPLC retention time: 0.89 min (analysis condition LCMS-F-1).

Example 369

Compound 1441

(Reaction 369-1)

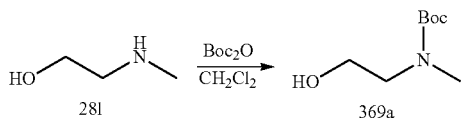

A mixture of 2-(methylamino)ethanol (5.2 g, 69.2 mmol) and tert-butyl dicarbonate (15.8 g, 72.7 mmol) in methylene chloride (200 mL) was stirred at room temperature for 16 hours. The reaction mixture was diluted with methylene chloride, and the organic layer was then washed with water, dried over MgSO₄ and concentrated under reduced pressure. The resulting residue was purified by silica gel column chromatography to give (2-hydroxyethyl)methylcarbamic acid 1,1-dimethylethyl ester (12.1 g, yield 100%).

¹H-NMR (400 MHz, CDCl₃) δ 1.47 (9H, m), 2.91 (3H, s), 3.39-3.41 (2H, m), 3.72-3.76 (2H, m).

(Reaction 369-2)

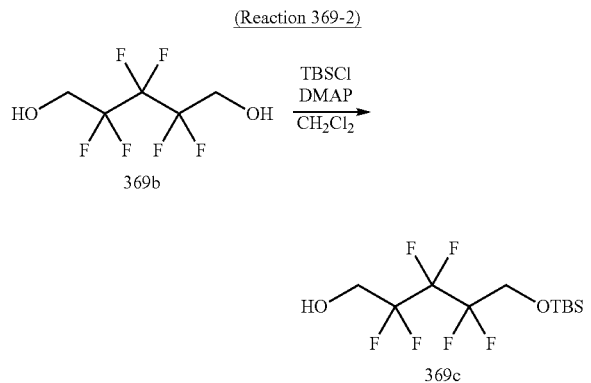

4-Dimethylaminopyridine (634 mg, 5.2 mmol) was added to a solution of 2,2,3,3,4,4-hexafluoro-pentane-1,5-diol (1 g, 4.7 mmol) and tert-butyldimethylsilyl chloride (708 mg, 4.7 mmol) in methylene chloride (10 ml), and the mixture was stirred at room temperature for 16 hours. The reaction mixture was concentrated under reduced pressure, and the residue was then purified by silica gel column chromatography to give 5-(tert-butyl-dimethyl-silanyloxy)-2,2,3,3,4,4-hexafluoro-pentan-1-ol (770 mg, 50%).

¹H-NMR (400 MHz, CDCl₃) δ 0.10 (6H, s), 0.90 (9H, m), 4.07-4.11 (4H, m).

(Reaction 369-3)

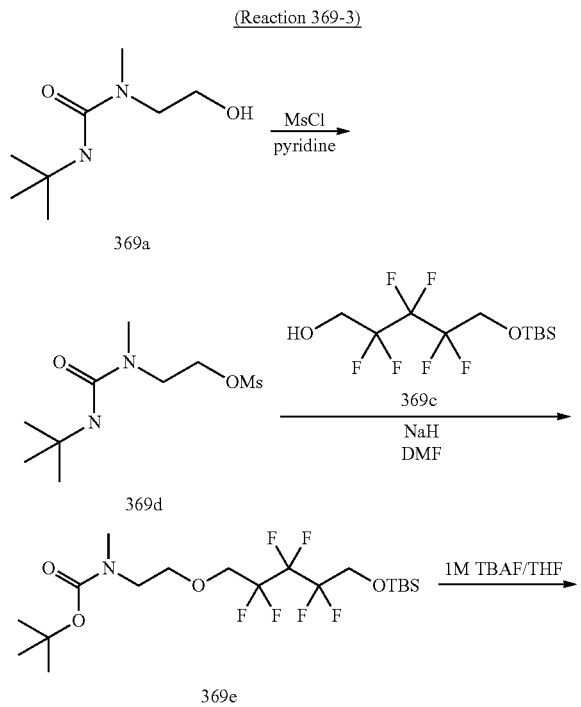

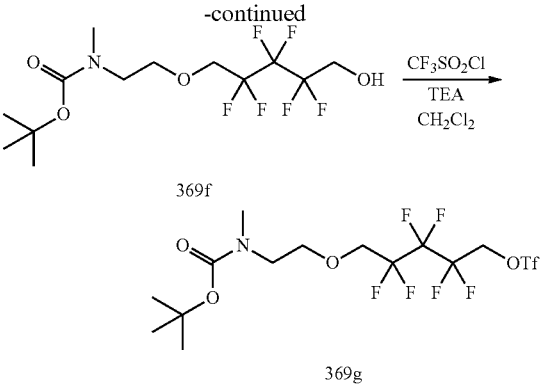

(2-Hydroxyethyl)methylcarbamic acid 1,1-dimethylethyl ester (350 mg, 2.0 mmol) was dissolved in pyridine (2 ml). Mesyl chloride (0.229 ml, 2.1 mmol) was added at room temperature, and the mixture was stirred at room temperature for 30 minutes. The reaction mixture was diluted with methylene chloride, and the organic layer was washed with a saturated aqueous sodium bicarbonate solution, dried over MgSO₄ and concentrated under reduced pressure to give methanesulfonic acid 2-(tert-butoxycarbonyl-methyl-amino)-ethyl ester. This was used in the next reaction without complete purification.

5-(tert-Butyl-dimethyl-silanyloxy)-2,2,3,3,4,4-hexafluoro-pentan-1-ol (400 mg, 1.23 mmol) was dissolved in dimethylformamide (2 ml). Sodium hydride (51.5 mg, 1.29 mmol) was added at room temperature, and the mixture was stirred at room temperature for 30 minutes. A solution of methanesulfonic acid 2-(tert-butoxycarbonyl-methyl-amino)-ethyl ester obtained above in dimethylformamide (0.5 ml) was then added at room temperature, and the mixture was stirred at room temperature overnight. The reaction mixture was extracted with ethyl acetate, and the organic layer was then washed with water, dried over MgSO₄ and concentrated under reduced pressure. The resulting residue was purified by silica gel column chromatography to give {2-[5-(tert-butyl-dimethyl-silanyloxy)-2,2,3,3,4,4-hexafluoro-pentyloxy]-ethyl}-methyl-carbamic acid tert-butyl ester. This was used in the next reaction without complete purification.

{2-[5-(tert-Butyl-dimethyl-silanyloxy)-2,2,3,3,4,4-hexafluoro-pentyloxy]-ethyl}-methyl-carbamic acid tert-butyl ester obtained above was dissolved in a 1 M solution of tetrabutylammonium fluoride in tetrafuran (0.2 mL), and the mixture was reacted at room temperature for one hour. The reaction mixture was concentrated under reduced pressure, and the residue was then purified by silica gel column chromatography to give [2-(2,2,3,3,4,4-hexafluoro-5-hydroxy-pentyloxy)-ethyl]-methyl-carbamic acid tert-butyl ester (70 mg). This was used in the next reaction without complete purification.

[2-(2,2,3,3,4,4-Hexafluoro-5-hydroxy-pentyloxy)-ethyl]-methyl-carbamic acid tert-butyl ester obtained above was dissolved in methylene chloride (0.5 ml). Triethylamine (0.0528 ml, 0.38 mmol) and trifluoromethanesulfonyl chloride (0.0212 ml, 0.20 mmol) were added at room temperature, and the mixture was stirred at room temperature for 64 hours. The reaction mixture was extracted with ethyl acetate, and the organic layer was washed with saturated brine, dried over MgSO₄ and concentrated under reduced pressure. The resulting residue was purified by silica gel column chromatography to give Trifluoro-methanesulfonic acid 5-[2-(tert-butoxycarbonyl-methyl-amino)-ethoxy]-2,2,3,3,4,4-hexafluoro-pentyl ester (66 mg).

1641

¹H-NMR (400 MHz, CDCl₃) δ 1.44 (9H, s), 2.89 (3H, s), 3.35-3.42 (m, 2H), 3.65-3.72 (m, 2H), 3.90-3.94 (m, 2H), 4.73-4.83 (m, 2H).

(Reaction 369-4)

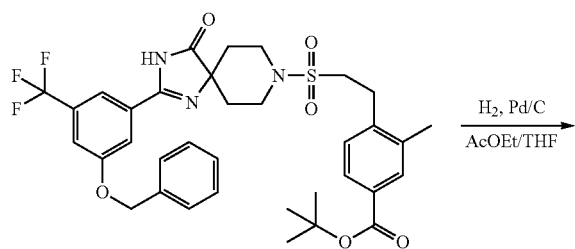

366e

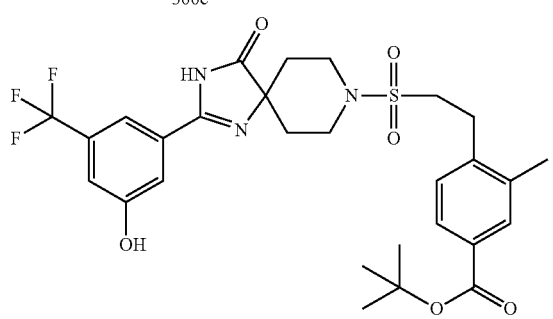

369h

1642

4-{2-[2-(3-Benzyloxy-5-trifluoromethyl-phenyl)-4-oxo-1,3,8-triaza-spiro[4.5]dec-1-ene-8-sulfonyl]-ethyl}-3-methyl-benzoic acid tert-butyl ester (952.0 mg, 1.39 mmol) was dissolved in ethyl acetate (15.0 ml)-THF (5.0 ml). Pd—C(190.4 mg) was added and the mixture was stirred at room temperature for one hour in a hydrogen atmosphere. After completion of the reaction, the precipitated solid was dissolved by adding dichloromethane and methanol, and the remaining black solid was then filtered off through celite. The filtrate was concentrated under reduced pressure to give 4-{2-[2-(3-hydroxy-5-trifluoromethyl-phenyl)-4-oxo-1,3,8-triaza-spiro[4.5]dec-1-ene-8-sulfonyl]-ethyl}-3-methyl-benzoic acid tert-butyl ester as a white solid (776.2 mg, 93.8%).

¹H-NMR (400 MHz, DMSO-d6) δ 11.7 (1H, br), 10.6 (1H, br), 7.66-7.80 (4H, m), 7.39 (1H, d, J8.0 Hz), 7.25 (1H, s), 3.59-3.70 (2H, m), 3.27-3.43 (4H, m), 3.04-3.08 (2H, m), 2.39 (3H, s), 1.79-1.88 (2H, m), 1.59 (2H, m), 1.55 (9H, s);

MS (ESI) m/z=596 (M+H)+;

HPLC retention time: 1.12 min (analysis condition LCMS-F-1).

(Reaction 369-5)

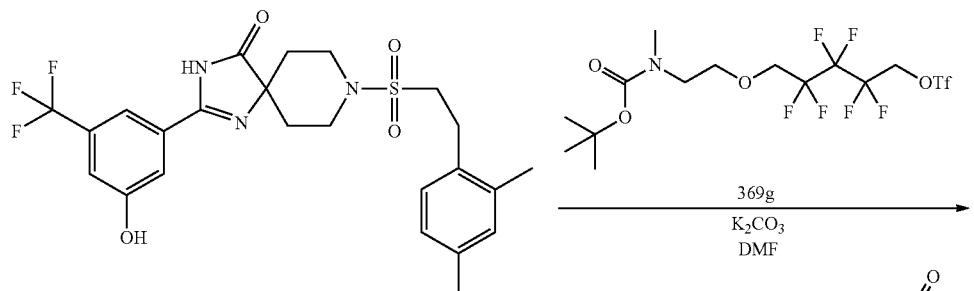

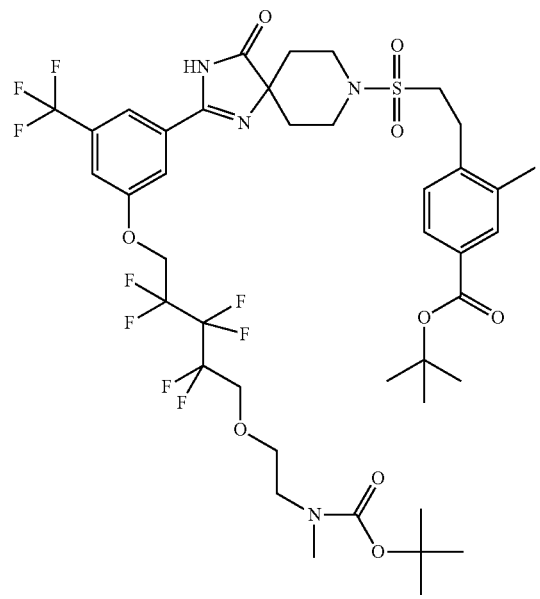

369i

4-{2-[2-(3-Hydroxy-5-trifluoromethyl-phenyl)-4-oxo-1,3,8-triaza-spiro[4.5]dec-1-ene-8-sulfonyl]-ethyl}-3-methyl-benzoic acid tert-butyl ester (77.0 mg, 0.13 mmol) and trifluoro-methanesulfonic acid 5-[2-(tert-butoxycarbonyl-methyl-amino)-ethoxy]-2,2,3,3,4,4-hexafluoro-pentyl ester (58.0 mg, 0.13 mmol) were dissolved in DMF (1 ml). Potassium carbonate (53.8 mg, 0.39 mmol) was added and the mixture was stirred at 60° C. overnight. The reaction mixture was extracted with ethyl acetate, and the organic layer was then washed with saturated brine, dried over MgSO₄ and concentrated under reduced pressure. The resulting residue was purified by silica gel column chromatography to give 4-{2-[2-(3-{5-[2-(tert-butoxycarbonyl-methyl-amino)-ethoxy]-2,2,3,3,4,4-hexafluoro-pentyloxy}-5-trifluoromethyl-phenyl)-4-oxo-1,3,8-triaza-spiro[4.5]dec-1-ene-8-sulfonyl]-ethyl}-3-methyl-benzoic acid tert-butyl ester (57 mg, 46%).

MS (ESI) m/z=947 (M+H)+.

4-{2-[2-(3-{5-[2-(tert-Butoxycarbonyl-methyl-amino)-ethoxy]-2,2,3,3,4,4-hexafluoro-pentyloxy}-5-trifluoromethyl-phenyl)-4-oxo-1,3,8-triaza-spiro[4.5]dec-1-ene-8-sulfonyl]-ethyl}-3-methyl-benzoic acid tert-butyl ester (56 mg, 0.059 mmol) was dissolved in water (0.1 ml) and 4 N hydrochloric acid-dioxane (1 ml), and the mixture was stirred at room temperature for 30 minutes. The reaction mixture was concentrated under reduced pressure, and the residue was then dissolved in DMF (5 ml). Triethylamine (0.053 ml, 0.384 mmol) and O-(benzotriazol-1-yl)-N,N,N',N'-tetramethyluronium hexafluorophosphate (144 mg, 0.384 mmol) were added at room temperature, and the mixture was heated with stirring at 70° C. for two hours. The reaction mixture was extracted with ethyl acetate, and the organic layer was washed with water, dried over MgSO₄ and concentrated under reduced pressure. The resulting residue was purified by silica gel column chromatography to give a saturated macrocyclic compound (Compound 1441) (12 mg, 21%).

(Reaction 369-6)

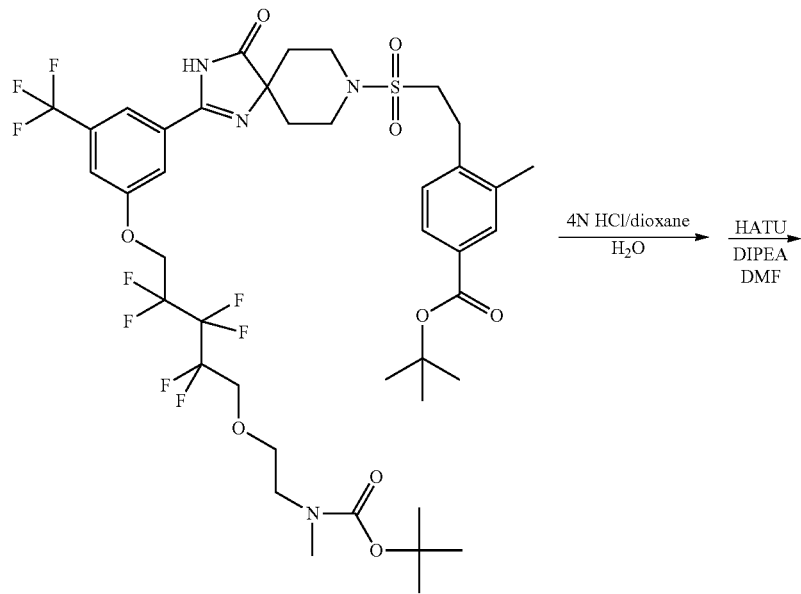

369i

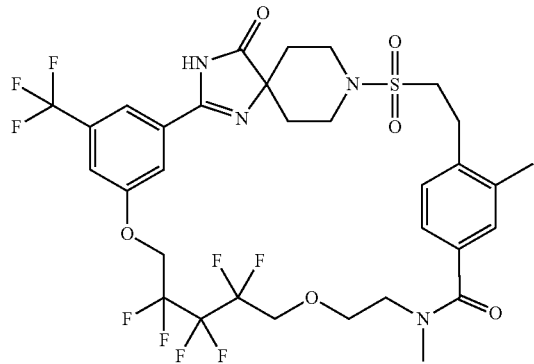

Compound 1441

MS (ESI) m/z=773 (M+H)+;
HPLC retention time: 6.52 min (analysis condition LCMS-A-2).

Example 370

Compound 1442

(Reaction 370-1)

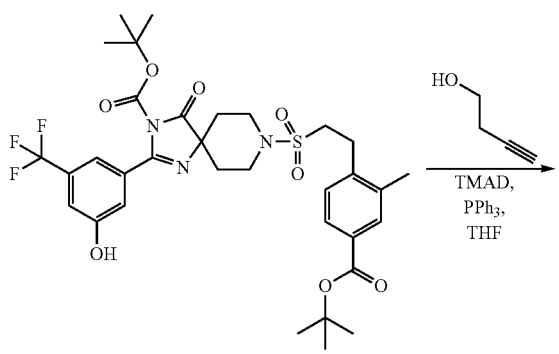

366h

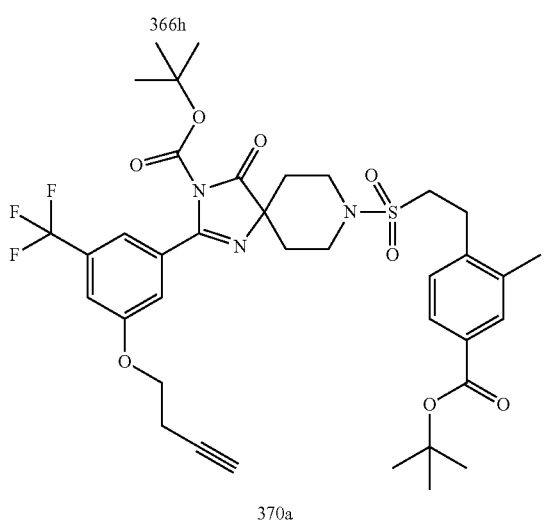

370a

8-[2-(4-tert-Butoxycarbonyl-2-methyl-phenyl)-ethanesulfonyl]-2-(3-but-3-ynyloxy-5-trifluoromethyl-phenyl)-4-oxo-1,3,8-triaza-spiro[4.5]dec-1-ene-3-carboxylic acid tert-butyl ester (37.9 mg, 71%) was obtained by the same method as in Reaction 366-9 using 8-[2-(4-tert-butoxycarbonyl-2-methyl-phenyl)-ethanesulfonyl]-2-(3-hydroxy-5-trifluoromethyl-phenyl)-4-oxo-1,3,8-triaza-spiro[4.5]dec-1-ene-3-carboxylic acid tert-butyl ester and 3-butyn-1-ol as starting materials.
MS (ESI) m/z=592 (M-Boc-tBu)+;
HPLC retention time: 3.79 min (analysis condition LCMS-A-1).

(Reaction 370-2)

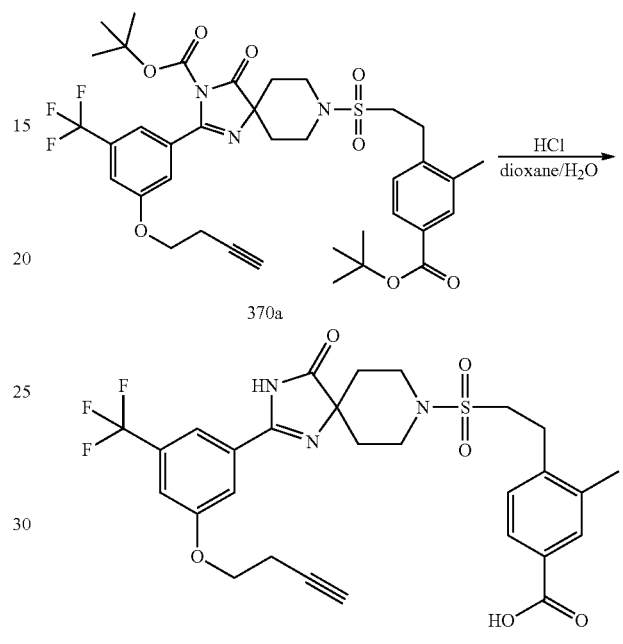

370a

370b

4 M hydrochloric acid-dioxane (1.80 ml) and water (0.0173 ml, 0.960 mmol) were added to 8-[2-(4-tert-butoxycarbonyl-2-methyl-phenyl)-ethanesulfonyl]-2-(3-but-3-ynyloxy-5-trifluoromethyl-phenyl)-4-oxo-1,3,8-triaza-spiro[4.5]dec-1-ene-3-carboxylic acid tert-butyl ester (35.9 mg, 0.048 mmol), and the mixture was stirred at room temperature for five hours. The reaction solution was concentrated under reduced pressure to give 4-{2-[2-(3-but-3-ynyloxy-5-trifluoromethyl-phenyl)-4-oxo-1,3,8-triaza-spiro[4.5]dec-1-ene-8-sulfonyl]-ethyl}-3-methyl-benzoic acid as a white solid.
MS (ESI) m/z=592 (M+H)+;
HPLC retention time: 0.91 min (analysis condition LCMS-F-1).

(Reaction 370-3)

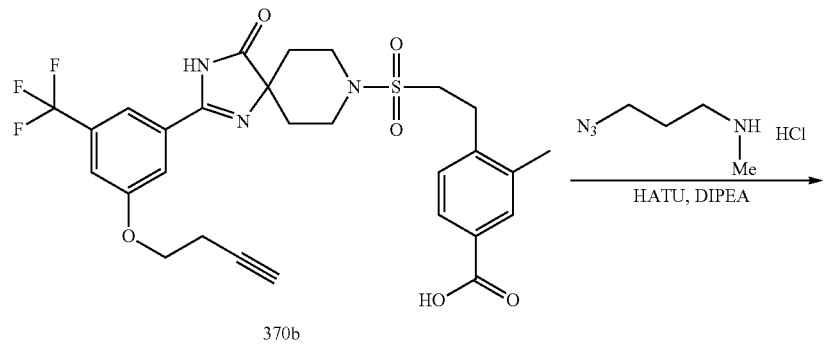

370b

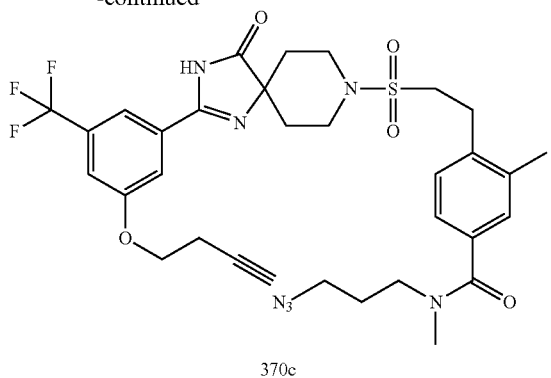

370c

4-{2-[2-(3-But-3-ynyloxy-5-trifluoromethyl-phenyl)-4-oxo-1,3,8-triaza-spiro[4.5]dec-1-ene-8-sulfonyl]-ethyl}-3-methyl-benzoic acid, (3-azido-propyl)-methyl-amine hydrochloride (15.3 mg, 0.101 mmol) and DIPEA (0.044 ml, 0.255 mmol) were dissolved in DMF (0.400 ml). HATU (0.038 mg, 0.101 mmol) was added and the mixture was stirred at room temperature for one hour. The reaction solution was diluted with ethyl acetate, and the organic layer was then washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (dichloromethane-ethyl acetate) to give N-(3-azido-propyl)-4-{2-[2-(3-but-3-ynyloxy-5-trifluoromethyl-phenyl)-4-oxo-1,3,8-triaza-spiro[4.5]dec-1-ene-8-sulfonyl]-ethyl}-3,N-dimethyl-benzamide as a colorless oily substance.

MS (ESI) m/z=688 (M+H)+;

HPLC retention time: 1.05 min (analysis condition LCMS-F-1).

(Reaction 370-4)

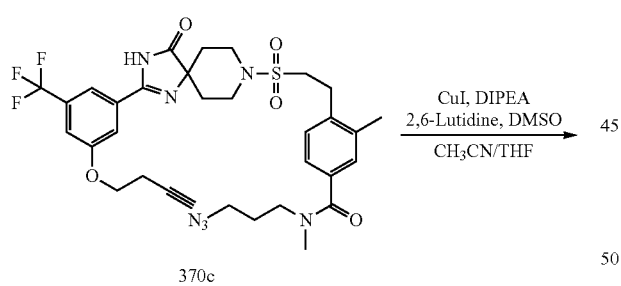

Compound 1442

N-(3-Azido-propyl)-4-{2-[2-(3-but-3-ynyloxy-5-trifluoromethyl-phenyl)-4-oxo-1,3,8-triaza-spiro[4.5]dec-1-ene-8-sulfonyl]-ethyl}-3,N-dimethyl-benzamide was dissolved in acetonitrile (17.0 ml)-THF (4.0 ml). DMSO (0.022 ml), DIPEA (0.012 ml, 0.069 mmol), 2,6-lutidine (0.0053 ml, 0.046 mmol) and copper(I) iodide (13.2 mg, 0.069 mmol) were added, and the mixture was stirred at room temperature overnight. Thereafter, copper(I) iodide (13.2 mg, 0.069 mmol) was further added and the mixture was stirred at room temperature for one hour. The reaction solution was concentrated under reduced pressure. Ethyl acetate was added and the precipitated solid was filtered off. The filtrate was washed with a 1 M aqueous hydrochloric acid solution, an aqueous sodium bicarbonate solution and saline. The organic layer was dried over anhydrous magnesium sulfate and then concentrated under reduced pressure. The resulting residue was purified by column chromatography (dichloromethane-ethyl acetate and dichloromethane-methanol) to give a macrocyclic compound (Compound 1442) as a white solid (3.2 mg, 20.2% in three steps).

MS (ESI) m/z=688 (M+H)+;

HPLC retention time: 0.94 min (analysis condition LCMS-F-1).

Example 371

Compound 1443

(Reaction 371-1)

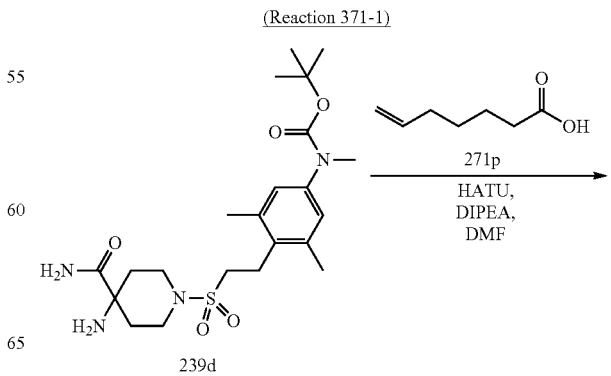

239d

-continued

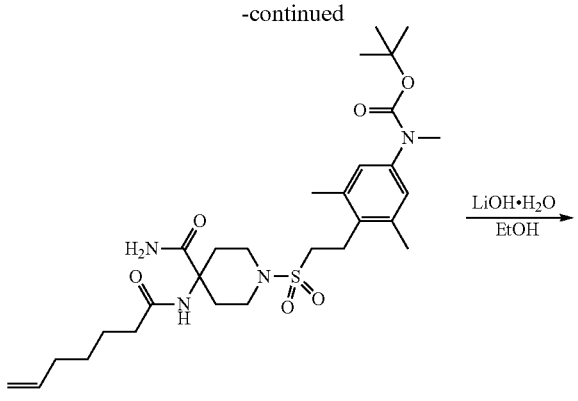

371a

LiOH·H₂O / EtOH

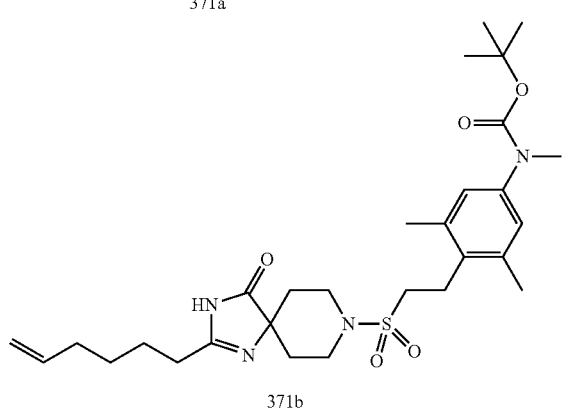

371b

{4-[2-(4-Carbamoyl-4-hept-6-enoylamino-piperidine-1-sulfonyl)-ethyl]-3,5-dimethyl-phenyl}-methyl-carbamic acid tert-butyl ester was obtained as a crude compound by the same method as in Reaction 359-9 using hept-6-enoic acid and {4-[2-(4-amino-4-carbamoyl-piperidine-1-sulfonyl)-ethyl]-3,5-dimethyl-phenyl}-methyl-carbamic acid tert-butyl ester as starting materials.

MS (ESI) m/z=579 (M+H)+;

HPLC retention time: 2.49 min (analysis condition LCMS-B-1).

{4-[2-(4-Carbamoyl-4-hept-6-enoylamino-piperidine-1-sulfonyl)-ethyl]-3,5-dimethyl-phenyl}-methyl-carbamic acid tert-butyl ester obtained above (Crude compound, 1.00 g) was dissolved in ethanol. Lithium hydroxide monohydrate (188 mg, 4.48 mmol) was added and the mixture was stirred at 40° C. for 19 hours. A saturated aqueous ammonium chloride solution and water were added to the reaction solution, followed by extraction with ethyl acetate. The organic layer was washed with water and saturated brine, and then dried over anhydrous sodium sulfate and concentrated under reduced pressure. The resulting residue was purified by silica gel column chromatography to give {4-[2-(2-hex-5-enyl-4-oxo-1,3,8-triaza-spiro[4.5]dec-1-ene-8-sulfonyl)-ethyl]-3,5-dimethyl-phenyl}-methyl-carbamic acid tert-butyl ester (821 mg, 1.47 mmol).

¹H-NMR (400 MHz, CDCl₃) δ 7.85 (1H, br s), 6.92 (2H, s), 5.83-5.73 (1H, m), 5.04-4.96 (2H, m), 3.80-3.74 (2H, m), 3.45-3.38 (2H, m), 3.22 (3H, s), 3.16-3.12 (2H, m), 3.01-2.97 (2H, m), 2.44 (2H, t, J=7.6 Hz), 2.34 (6H, s), 2.10 (2H, q, J=7.2 Hz), 2.02-1.95 (2H, m), 1.71-1.59 (4H, m), 1.46 (9H, s);

MS (ESI) m/z=561 (M+H)+;

HPLC retention time: 2.61 min (analysis condition LCMS-A-1).

(Reaction 371-2)

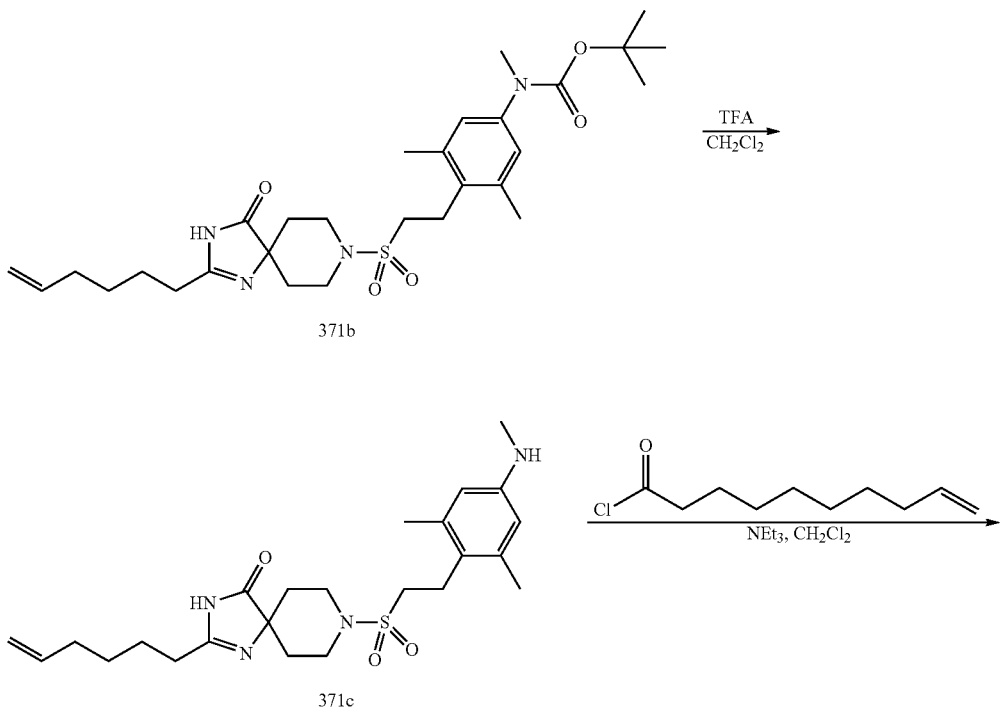

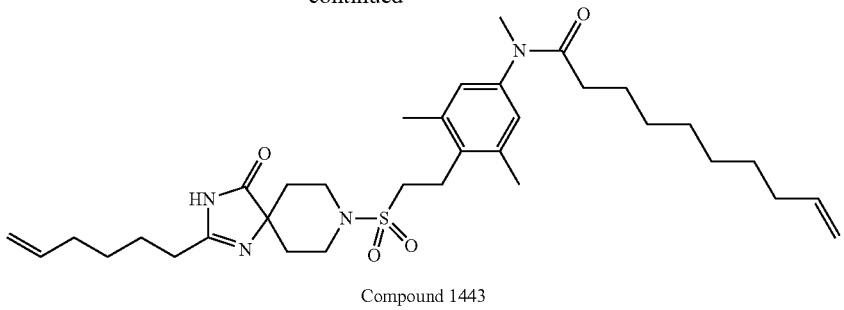

Compound 1443

{4-[2-(2-Hex-5-enyl-4-oxo-1,3,8-triaza-spiro[4.5]dec-1-ene-8-sulfonyl)-ethyl]-3,5-dimethyl-phenyl}-methyl-carbamic acid tert-butyl ester (820 mg, 1.46 mmol) was dissolved in methylene chloride (16 ml). Trifluoroacetic acid (10 ml) was added and the mixture was stirred at room temperature for two hours. The reaction solution was concentrated, and a saturated aqueous sodium bicarbonate solution was added to the residue. This mixture was extracted with methylene chloride. The organic layer was dried over anhydrous sodium sulfate and then concentrated under reduced pressure to give 8-[2-(2,6-dimethyl-4-methyl-amino-phenyl)-ethanesulfonyl]-2-hex-5-enyl-1,3,8-triaza-spiro[4.5]dec-1-en-4-one (686 mg) as a crude compound.

The resulting crude product 8-[2-(2,6-dimethyl-4-methylamino-phenyl)-ethanesulfonyl]-2-hex-5-enyl-1,3,8-triaza-spiro[4.5]dec-1-en-4-one (160 mg, 0.35 mmol) was dissolved in methylene chloride. 9-Decenoyl chloride (0.35 mmol) (prepared by allowing oxalyl chloride and a catalytic amount of DMF to act on 9-decenoic acid in methylene chloride) and triethylamine (0.195 ml, 1.4 mmol) were added, and the mixture was stirred at room temperature for 17 hours. A saturated aqueous ammonium chloride solution and water were added to the reaction solution, and the resulting mixture was extracted with ethyl acetate. The organic layer was washed with water and saturated brine, dried over anhydrous sodium sulfate and then concentrated under reduced pressure. The resulting residue was purified by silica gel column chromatography to give dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide (Compound 1443) (100 mg, 48% in two steps).

MS (ESI) m/z=613 (M+H)+;
HPLC retention time: 5.80 min (analysis condition LCMS-C-1).

Example 372

Compound 1444

A macrocyclic olefin compound (Compound 1444) was obtained by the same method as in Reaction 338-1 using dec-9-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide as a starting material.

MS (ESI) m/z=585 (M+H)+;
HPLC retention time: 5.15 min (analysis condition LCMS-B-2).

Example 373

Compound 1445

(Reaction 372-1)

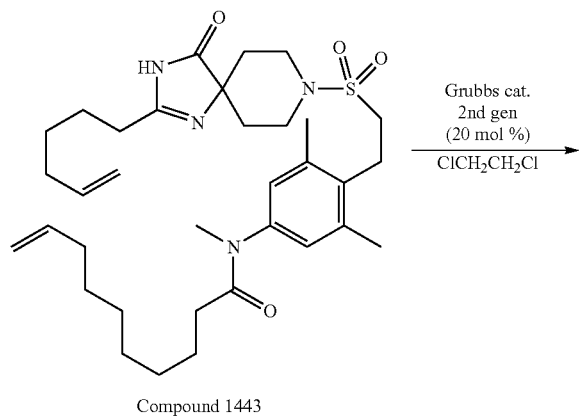

Compound 1443

(Reaction 373-1)

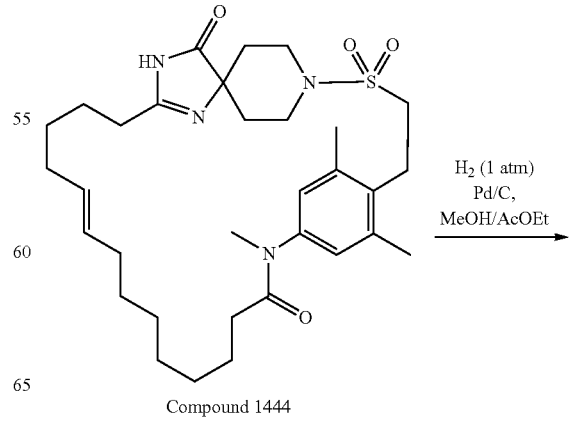

Compound 1444

1653
-continued

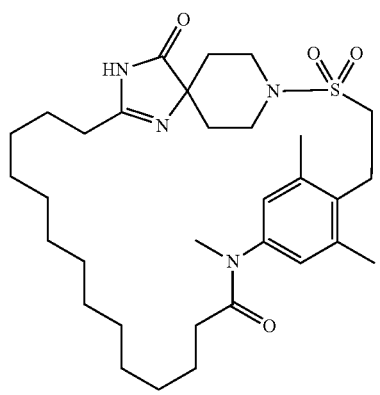

Compound 1445

A saturated macrocyclic compound (Compound 1445) was obtained by the same method as in Reaction 339-1 using a macrocyclic olefin compound (Compound 1444) as a starting material.

MS (ESI) m/z=587 (M+H)+;

HPLC retention time: 2.70 min (analysis condition LCMS-A-1).

Example 374

Compound 1446

1654

Hept-6-enoic acid {4-[2-(2-hex-5-enyl-4-oxo-1,3,8-tri-aza-spiro[4.5]dec-1-ene-8-sulfonyl)-ethyl]-3,5-dimethyl-phenyl}-methyl-amide (Compound 1446) was obtained by the same method as in Reaction 371-2 using 6-heptenoic acid and 8-[2-(2,6-dimethyl-4-methylamino-phenyl)-ethanesulfonyl]-2-hex-5-enyl-1,3,8-triaza-spiro[4.5]dec-1-en-4-one as starting materials.

MS (ESI) m/z=571 (M+H)+;

HPLC retention time: 2.49 min (analysis condition LCMS-A-1).

Example 375

Compound 1447

(Reaction 375-1)

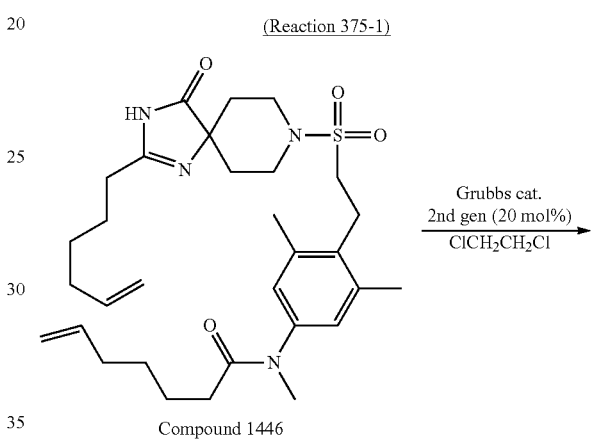

Compound 1446

(Reaction 374-1)

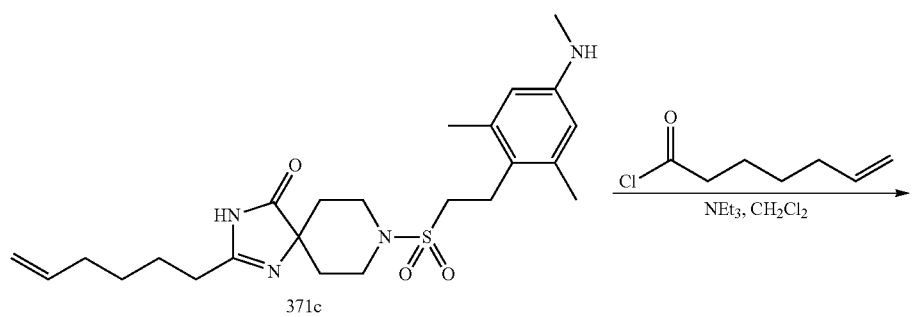

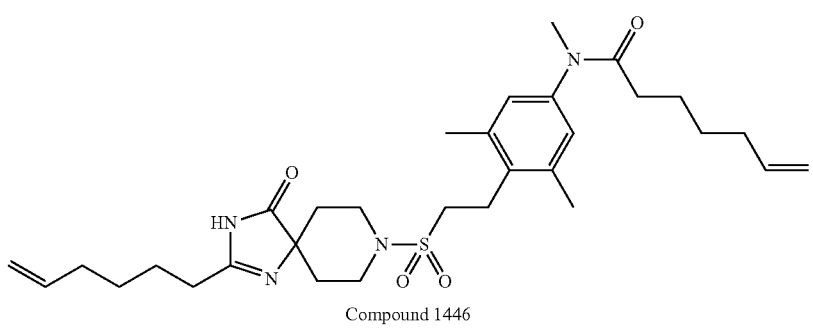

Compound 1446

1655

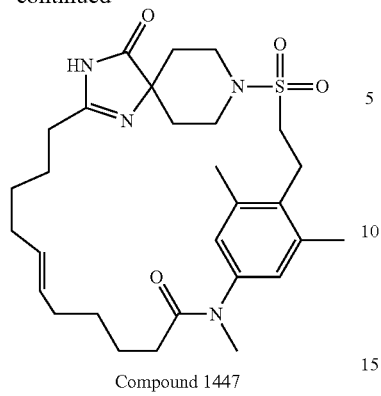
Compound 1447

A macrocyclic olefin compound (Compound 1447) was obtained by the same method as in Reaction 338-1 using hept-6-enoic acid {4-[2-(2-hex-5-enyl-4-oxo-1,3,8-triaza-spiro[4.5]dec-1-ene-8-sulfonyl)-ethyl]-3,5-dimethyl-phenyl}-methyl-amide as a starting material.

MS (ESI) m/z=543 (M+H)+;

HPLC retention time: 2.25 min (analysis condition LCMS-A-1).

Example 376

Compound 1448

(Reaction 376-1)

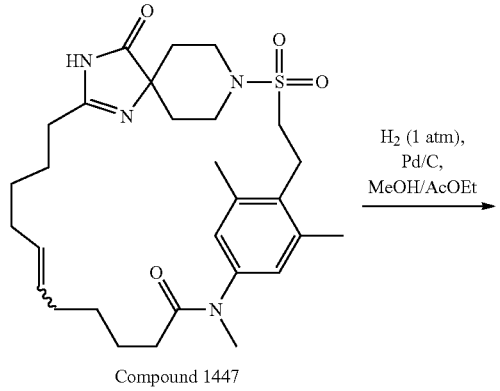

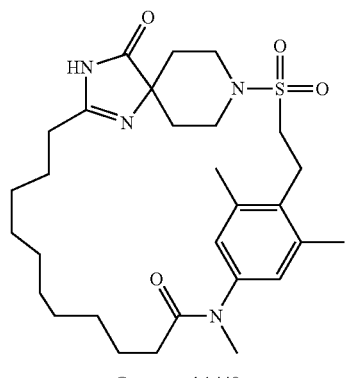
Compound 1448

1656

A saturated macrocyclic compound (Compound 1448) was obtained by the same method as in Reaction 339-1 using a macrocyclic olefin compound (Compound 1447) as a starting material.

MS (ESI) m/z=545 (M+H)+;

HPLC retention time: 2.34 min (analysis condition LCMS-A-1).

Example 377

Compound 1449

(Reaction 377-1)

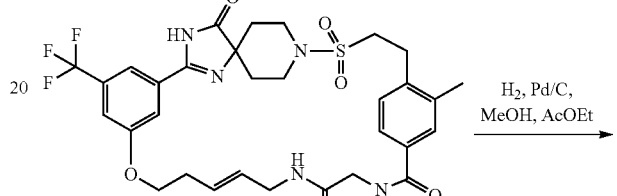
Compound 1422

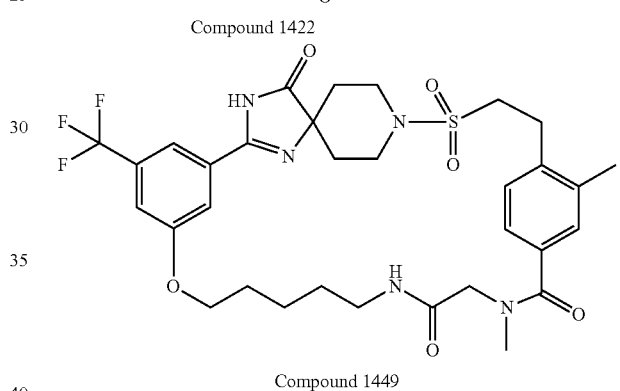
Compound 1449

A saturated macrocyclic compound (Compound 1449) was obtained by the same method as in Reaction 339-1 using a macrocyclic olefin compound (Compound 1422) as a starting material.

MS (ESI) m/z=678 (M+H)+;

HPLC retention time: 2.50 min (analysis condition LCMS-A-1).

Biological Experimental Example

Experimental Example A

In Vitro cAMP Signal Activity of Compounds in Human PTH1 Receptor

Materials and Method
(Peptides)

Human PTH(1-34) and calcitonin were purchased from Peptide Institute, Inc. (Osaka, Japan), dissolved in 10 mM acetic acid to 1 mM and stored in a −80° C. freezer.

(Cell Culture)

Cells were cultured in Dulbecco's modified Eagle's medium (DMEM) supplemented with 10% fetal bovine serum (Hyclone), 100 units/ml penicillin G and 100 μg/ml streptomycin sulfate (Invitrogen Corp) at 37° C. in a humidified atmosphere containing 5% $CO_2$.

cAMP signal transduction analysis utilized LLC-PK1 cells not expressing the PTH1 receptor, and HKRK-B7 cells, that is, LLC-PK1 cells overexpressing the human PTH1 receptor at $9.5 \times 10^5$ receptors/cell (Takasu et al., J. Bone. Miner. Res. 14:11-20, 1999).

(cAMP Stimulation)

HKRK-B7 or LLC-PK1 cells were seeded in a 96-well plate at $1 \times 10^5$ cells/well and incubated overnight. On the following day, 50 µl of cAMP assay buffer (DMEM, 2 mM IBMX, 0.2 mg/ml bovine serum albumin, 35 mM Hepes-NaOH, pH 7.4) containing human PTH(1-34) or Compound was added and the plate was placed in a 37° C. incubator. The cells were incubated for 20 minutes. After removing the medium, the cells were washed with 100 µl of cAMP assay buffer once. The plate was placed on dry ice powder to freeze the cells and then removed from the dry ice. The cells were lysed with 40 µl of 50 mM HCl and frozen again on dry ice. The amount of intracellular cAMP produced was measured using a commercially available cAMP EIA kit (Biotrack cAMP EIA system, GE health care).

The compounds of the present invention demonstrated a significant cAMP response in HKRK-B7 cells. Table 195 shows percentage values obtained by dividing the amount of cAMP produced by the compound of the present invention in HKRK-B7 cells at $1 \times 10^{-3}$ M (*at $3 \times 10^{-4}$ M for Compound 15) by the amount of cAMP produced by hPTH(1-34) as a positive control at 100 nM. The degree of cAMP response in LLC-PK1 cells was lower than the degree in HKRK-B7 cells.

TABLE 195

| Compound | cAMP production activity (%) |
|---|---|
| 1 | 42 |
| 2 | 1.0 |
| 3 | 20 |
| 4 | 11 |
| 5 | 2.5 |
| 6 | 4.2 |
| 7 | 13 |
| 8 | 2.6 |
| 10 | 2.4 |
| 11 | 16 |
| 12 | 12 |
| 13 | 31 |
| 14 | 38 |
| 15 | 1.8* |
| 16 | 41 |
| 17 | 39 |
| 18 | 44 |
| 19 | 35 |
| 20 | 38 |
| 21 | 42 |
| 22 | 43 |
| 23 | 41 |
| 24 | 18 |
| 25 | 18 |
| 26 | 36 |
| 27 | 42 |
| 28 | 31 |
| 29 | 28 |
| 30 | 26 |
| 31 | 41 |
| 32 | 26 |
| 33 | 4.4 |
| 34 | 16 |
| 35 | 56 |
| 36 | 3.5 |
| 37 | 54 |
| 38 | 52 |
| 39 | 25 |
| 40 | 19 |

TABLE 195-continued

| Compound | cAMP production activity (%) |
|---|---|
| 41 | 21 |
| 42 | 27 |
| 43 | 39 |
| 44 | 25 |
| 45 | 22 |
| 46 | 17 |
| 47 | 45 |
| 48 | 25 |
| 49 | 29 |
| 50 | 26 |
| 51 | 38 |
| 52 | 23 |
| 53 | 33 |
| 54 | 35 |
| 55 | 55 |
| 56 | 55 |
| 57 | 35 |
| 58 | 39 |
| 59 | 56 |
| 60 | 34 |
| 61 | 43 |
| 62 | 56 |
| 63 | 51 |
| 64 | 45 |
| 65 | 65 |
| 66 | 57 |
| 67 | 53 |
| 68 | 51 |
| 69 | 61 |
| 70 | 31 |
| 71 | 3.7 |
| 72 | 1.5 |
| 73 | 66 |
| 74 | 48 |
| 75 | 75 |
| 76 | 73 |
| 77 | 69 |
| 78 | 31 |
| 79 | 8.2 |
| 80 | 71 |
| 81 | 57 |
| 82 | 65 |
| 83 | 41 |
| 84 | 51 |
| 85 | 76 |
| 86 | 66 |
| 87 | 6.7 |
| 88 | 97 |
| 89 | 96 |
| 90 | 88 |
| 91 | 73 |
| 92 | 97 |
| 93 | 111 |
| 94 | 62 |
| 95 | 76 |
| 96 | 70 |
| 97 | 4.3 |
| 98 | 75 |
| 99 | 80 |
| 100 | 61 |
| 101 | 49 |
| 102 | 23 |
| 103 | 80 |
| 104 | 79 |
| 105 | 78 |
| 106 | 94 |
| 107 | 110 |
| 108 | 62 |
| 109 | 62 |
| 110 | 25 |
| 111 | 93 |
| 112 | 77 |
| 113 | 111 |
| 114 | 105 |
| 115 | 81 |
| 116 | 94 |
| 117 | 61 |

TABLE 195-continued

| Compound | cAMP production activity (%) |
|---|---|
| 118 | 73 |
| 119 | 60 |
| 120 | 3.1 |
| 121 | 5.8 |
| 122 | 3.0 |
| 123 | 23 |
| 124 | 64 |
| 125 | 62 |
| 126 | 79 |
| 127 | 72 |
| 128 | 57 |
| 129 | 3.7 |
| 130 | 65 |
| 131 | 72 |
| 133 | 82 |
| 134 | 77 |
| 135 | 67 |
| 136 | 72 |
| 137 | 50 |
| 138 | 49 |
| 139 | 64 |
| 140 | 77 |
| 141 | 32 |
| 142 | 63 |
| 143 | 4.5 |
| 144 | 59 |
| 145 | 129 |
| 146 | 122 |
| 147 | 105 |
| 148 | 79 |
| 149 | 56 |
| 150 | 62 |
| 151 | 53 |
| 152 | 47 |
| 153 | 59 |
| 154 | 82 |
| 155 | 45 |
| 156 | 64 |
| 157 | 70 |
| 158 | 62 |
| 159 | 96 |
| 160 | 65 |
| 161 | 69 |
| 162 | 43 |
| 163 | 41 |
| 164 | 45 |
| 165 | 37 |
| 166 | 56 |
| 167 | 44 |
| 168 | 69 |
| 169 | 71 |
| 170 | 77 |
| 171 | 36 |
| 172 | 102 |
| 173 | 71 |
| 174 | 68 |
| 175 | 73 |
| 176 | 74 |
| 177 | 28 |
| 178 | 29 |
| 179 | 49 |
| 180 | 60 |
| 181 | 19 |
| 182 | 38 |
| 183 | 68 |
| 184 | 37 |
| 185 | 33 |
| 186 | 51 |
| 187 | 12 |
| 188 | 70 |
| 189 | 54 |
| 190 | 61 |
| 191 | 57 |
| 192 | 52 |
| 193 | 65 |
| 194 | 56 |
| 195 | 36 |

TABLE 195-continued

| Compound | cAMP production activity (%) |
|---|---|
| 196 | 66 |
| 197 | 41 |
| 198 | 31 |
| 199 | 46 |
| 200 | 37 |
| 201 | 56 |
| 202 | 27 |
| 203 | 25 |
| 204 | 110 |
| 205 | 47 |
| 206 | 70 |
| 207 | 36 |
| 208 | 22 |
| 209 | 24 |
| 210 | 79 |
| 211 | 60 |
| 212 | 59 |
| 213 | 74 |
| 214 | 84 |
| 215 | 81 |
| 216 | 84 |
| 217 | 41 |
| 218 | 72 |
| 219 | 60 |
| 220 | 80 |
| 221 | 103 |
| 222 | 43 |
| 223 | 85 |
| 224 | 54 |
| 225 | 47 |
| 226 | 83 |
| 227 | 87 |
| 228 | 8.3 |
| 229 | 68 |
| 230 | 66 |
| 231 | 96 |
| 232 | 69 |
| 233 | 13 |
| 234 | 78 |
| 235 | 49 |
| 236 | 40 |
| 237 | 74 |
| 238 | 90 |
| 239 | 80 |
| 240 | 49 |
| 241 | 44 |
| 242 | 75 |
| 243 | 80 |
| 244 | 83 |
| 245 | 34 |
| 246 | 39 |
| 247 | 81 |
| 248 | 66 |
| 249 | 71 |
| 250 | 62 |
| 251 | 28 |
| 252 | 28 |
| 253 | 54 |
| 254 | 97 |
| 255 | 64 |
| 256 | 67 |
| 257 | 42 |
| 258 | 87 |
| 259 | 67 |
| 260 | 24 |
| 261 | 70 |
| 262 | 26 |
| 263 | 41 |
| 264 | 69 |
| 265 | 55 |
| 266 | 81 |
| 267 | 42 |
| 268 | 99 |
| 269 | 43 |
| 270 | 55 |
| 271 | 57 |
| 272 | 67 |

TABLE 195-continued

| Compound | cAMP production activity (%) |
|---|---|
| 273 | 55 |
| 274 | 74 |
| 275 | 72 |
| 276 | 63 |
| 277 | 38 |
| 278 | 59 |
| 279 | 67 |
| 280 | 57 |
| 281 | 92 |
| 282 | 29 |
| 283 | 63 |
| 284 | 82 |
| 285 | 65 |
| 286 | 54 |
| 287 | 58 |
| 288 | 82 |
| 289 | 99 |
| 290 | 76 |
| 291 | 66 |
| 292 | 58 |
| 293 | 38 |
| 294 | 106 |
| 295 | 95 |
| 296 | 65 |
| 297 | 91 |
| 298 | 63 |
| 299 | 83 |
| 300 | 73 |
| 301 | 72 |
| 302 | 95 |
| 303 | 76 |
| 304 | 47 |
| 305 | 73 |
| 306 | 45 |
| 307 | 58 |
| 308 | 72 |
| 309 | 72 |
| 310 | 76 |
| 311 | 67 |
| 312 | 49 |
| 313 | 63 |
| 314 | 68 |
| 315 | 26 |
| 316 | 20 |
| 317 | 62 |
| 318 | 52 |
| 319 | 31 |
| 320 | 33 |
| 321 | 55 |
| 322 | 75 |
| 323 | 53 |
| 324 | 30 |
| 325 | 61 |
| 326 | 76 |
| 327 | 84 |
| 328 | 41 |
| 329 | 33 |
| 330 | 23 |
| 331 | 55 |
| 332 | 90 |
| 333 | 87 |
| 334 | 34 |
| 335 | 28 |
| 336 | 28 |
| 337 | 17 |
| 338 | 60 |
| 339 | 66 |
| 340 | 67 |
| 341 | 62 |
| 342 | 93 |
| 343 | 13 |
| 344 | 35 |
| 345 | 21 |
| 346 | 28 |
| 347 | 23 |
| 348 | 5.6 |
| 349 | 11 |

TABLE 195-continued

| Compound | cAMP production activity (%) |
|---|---|
| 350 | 5.5 |
| 351 | 7.4 |
| 352 | 19 |
| 353 | 120 |
| 354 | 27 |
| 355 | 84 |
| 356 | 78 |
| 357 | 78 |
| 358 | 71 |
| 359 | 65 |
| 360 | 62 |
| 361 | 82 |
| 362 | 97 |
| 363 | 67 |
| 364 | 78 |
| 365 | 81 |
| 366 | 85 |
| 367 | 50 |
| 368 | 38 |
| 369 | 43 |
| 370 | 66 |
| 371 | 72 |
| 372 | 51 |
| 373 | 70 |
| 374 | 79 |
| 375 | 57 |
| 376 | 74 |
| 377 | 64 |
| 378 | 60 |
| 379 | 59 |
| 380 | 75 |
| 381 | 72 |
| 382 | 36 |
| 383 | 72 |
| 384 | 61 |
| 385 | 94 |
| 386 | 86 |
| 387 | 97 |
| 388 | 84 |
| 389 | 75 |
| 390 | 22 |
| 391 | 26 |
| 392 | 83 |
| 393 | 44 |
| 394 | 59 |
| 395 | 88 |
| 396 | 85 |
| 397 | 126 |
| 398 | 52 |
| 399 | 64 |
| 400 | 76 |
| 401 | 83 |
| 402 | 85 |
| 403 | 51 |
| 404 | 88 |
| 405 | 7.7 |
| 406 | 100 |
| 407 | 49 |
| 408 | 117 |
| 409 | 55 |
| 410 | 96 |
| 411 | 54 |
| 412 | 54 |
| 413 | 56 |
| 414 | 69 |
| 415 | 56 |
| 416 | 66 |
| 417 | 97 |
| 418 | 84 |
| 419 | 96 |
| 420 | 31 |
| 421 | 68 |
| 422 | 14 |
| 423 | 42 |
| 424 | 2.5 |
| 425 | 17 |
| 426 | 16 |

TABLE 195-continued

| Compound | cAMP production activity (%) |
|---|---|
| 428 | 8.8 |
| 429 | 38 |
| 430 | 23 |
| 431 | 14 |
| 432 | 5.1 |
| 433 | 18 |
| 434 | 25 |
| 435 | 17 |
| 436 | 28 |
| 437 | 45 |
| 438 | 14 |
| 439 | 33 |
| 441 | 24 |
| 442 | 2.5 |
| 444 | 46 |
| 445 | 83 |
| 446 | 49 |
| 447 | 89 |
| 448 | 64 |
| 449 | 94 |
| 450 | 56 |
| 451 | 96 |
| 452 | 58 |
| 453 | 16 |
| 454 | 19 |
| 455 | 31 |
| 456 | 28 |
| 457 | 25 |
| 458 | 77 |
| 459 | 55 |
| 460 | 18 |
| 461 | 51 |
| 462 | 47 |
| 463 | 28 |
| 464 | 54 |
| 465 | 66 |
| 466 | 23 |
| 467 | 60 |
| 468 | 90 |
| 469 | 47 |
| 470 | 90 |
| 471 | 111 |
| 472 | 104 |
| 474 | 89 |
| 475 | 84 |
| 476 | 61 |
| 477 | 31 |
| 478 | 33 |
| 479 | 15 |
| 480 | 44 |
| 481 | 59 |
| 482 | 38 |
| 483 | 41 |
| 484 | 47 |
| 485 | 7.7 |
| 486 | 59 |
| 487 | 49 |
| 488 | 48 |
| 489 | 37 |
| 490 | 26 |
| 491 | 58 |
| 492 | 37 |
| 493 | 50 |
| 494 | 66 |
| 495 | 21 |
| 496 | 24 |
| 497 | 38 |
| 498 | 53 |
| 499 | 40 |
| 500 | 61 |
| 501 | 59 |
| 502 | 14 |
| 503 | 67 |
| 504 | 60 |
| 505 | 61 |
| 506 | 83 |
| 507 | 43 |

TABLE 195-continued

| Compound | cAMP production activity (%) |
|---|---|
| 508 | 24 |
| 509 | 70 |
| 510 | 57 |
| 511 | 29 |
| 512 | 49 |
| 513 | 33 |
| 514 | 75 |
| 515 | 113 |
| 516 | 73 |
| 517 | 58 |
| 518 | 68 |
| 519 | 72 |
| 520 | 28 |
| 521 | 55 |
| 522 | 82 |
| 523 | 89 |
| 524 | 90 |
| 525 | 14 |
| 526 | 83 |
| 527 | 93 |
| 528 | 55 |
| 529 | 68 |
| 530 | 18 |
| 531 | 69 |
| 532 | 80 |
| 533 | 69 |
| 534 | 39 |
| 535 | 83 |
| 536 | 72 |
| 537 | 3.9 |
| 538 | 133 |
| 539 | 80 |
| 540 | 22 |
| 541 | 79 |
| 542 | 66 |
| 543 | 76 |
| 544 | 80 |
| 545 | 86 |
| 546 | 75 |
| 547 | 52 |
| 548 | 88 |
| 549 | 86 |
| 550 | 124 |
| 551 | 92 |
| 552 | 64 |
| 553 | 80 |
| 554 | 82 |
| 555 | 40 |
| 556 | 19 |
| 557 | 50 |
| 558 | 74 |
| 559 | 72 |
| 560 | 66 |
| 561 | 52 |
| 562 | 74 |
| 563 | 69 |
| 564 | 68 |
| 565 | 45 |
| 566 | 19 |
| 567 | 24 |
| 568 | 39 |
| 569 | 4.2 |
| 570 | 66 |
| 571 | 39 |
| 572 | 36 |
| 573 | 35 |
| 574 | 42 |
| 575 | 57 |
| 576 | 95 |
| 577 | 74 |
| 578 | 13 |
| 579 | 55 |
| 580 | 25 |
| 581 | 75 |
| 582 | 104 |
| 583 | 85 |
| 584 | 24 |

TABLE 195-continued

| Compound | cAMP production activity (%) |
|---|---|
| 585 | 39 |
| 586 | 82 |
| 587 | 53 |
| 588 | 77 |
| 589 | 22 |
| 590 | 70 |
| 591 | 34 |
| 592 | 87 |
| 593 | 28 |
| 594 | 69 |
| 595 | 63 |
| 596 | 40 |
| 597 | 51 |
| 598 | 74 |
| 599 | 59 |
| 600 | 67 |
| 601 | 64 |
| 602 | 3.0 |
| 603 | 69 |
| 604 | 21 |
| 605 | 54 |
| 606 | 28 |
| 607 | 6.5 |
| 608 | 20 |
| 609 | 46 |
| 610 | 85 |
| 611 | 82 |
| 612 | 62 |
| 613 | 44 |
| 614 | 25 |
| 615 | 46 |
| 616 | 94 |
| 617 | 96 |
| 618 | 121 |
| 619 | 61 |
| 620 | 112 |
| 621 | 80 |
| 622 | 134 |
| 623 | 123 |
| 624 | 36 |
| 625 | 47 |
| 626 | 53 |
| 627 | 5.3 |
| 628 | 48 |
| 629 | 87 |
| 630 | 4.1 |
| 631 | 65 |
| 632 | 51 |
| 633 | 37 |
| 634 | 29 |
| 635 | 93 |
| 636 | 88 |
| 637 | 38 |
| 638 | 46 |
| 639 | 101 |
| 640 | 26 |
| 641 | 85 |
| 642 | 87 |
| 643 | 94 |
| 644 | 75 |
| 645 | 55 |
| 646 | 99 |
| 647 | 104 |
| 648 | 61 |
| 649 | 40 |
| 650 | 55 |
| 651 | 54 |
| 652 | 63 |
| 653 | 67 |
| 654 | 50 |
| 655 | 74 |
| 656 | 14 |
| 657 | 124 |
| 658 | 84 |
| 659 | 46 |
| 660 | 60 |
| 661 | 45 |

TABLE 195-continued

| Compound | cAMP production activity (%) |
|---|---|
| 662 | 23 |
| 663 | 27 |
| 664 | 77 |
| 665 | 54 |
| 666 | 51 |
| 667 | 40 |
| 668 | 40 |
| 669 | 58 |
| 670 | 123 |
| 671 | 81 |
| 672 | 47 |
| 673 | 27 |
| 674 | 68 |
| 675 | 68 |
| 676 | 69 |
| 677 | 69 |
| 678 | 86 |
| 679 | 65 |
| 680 | 101 |
| 681 | 55 |
| 682 | 81 |
| 683 | 74 |
| 684 | 101 |
| 685 | 46 |
| 686 | 22 |
| 687 | 25 |
| 688 | 55 |
| 689 | 27 |
| 690 | 86 |
| 691 | 69 |
| 692 | 101 |
| 693 | 103 |
| 694 | 77 |
| 695 | 78 |
| 696 | 132 |
| 697 | 60 |
| 698 | 62 |
| 699 | 101 |
| 700 | 121 |
| 701 | 140 |
| 702 | 84 |
| 704 | 68 |
| 705 | 76 |
| 706 | 90 |
| 707 | 124 |
| 708 | 38 |
| 709 | 58 |
| 710 | 76 |
| 711 | 64 |
| 712 | 16 |
| 713 | 55 |
| 714 | 36 |
| 715 | 20 |
| 716 | 62 |
| 717 | 111 |
| 718 | 74 |
| 719 | 77 |
| 720 | 82 |
| 721 | 92 |
| 722 | 60 |
| 723 | 95 |
| 724 | 74 |
| 725 | 58 |
| 726 | 75 |
| 727 | 52 |
| 728 | 87 |
| 729 | 45 |
| 730 | 74 |
| 731 | 54 |
| 732 | 45 |
| 733 | 104 |
| 734 | 47 |
| 735 | 32 |
| 736 | 16 |
| 737 | 96 |
| 738 | 79 |
| 739 | 47 |

TABLE 195-continued

| Compound | cAMP production activity (%) |
|---|---|
| 740 | 123 |
| 741 | 91 |
| 742 | 50 |
| 743 | 54 |
| 744 | 19 |
| 745 | 67 |
| 746 | 120 |
| 747 | 55 |
| 748 | 61 |
| 749 | 77 |
| 750 | 87 |
| 751 | 83 |
| 752 | 79 |
| 753 | 104 |
| 754 | 89 |
| 755 | 74 |
| 756 | 79 |
| 757 | 79 |
| 758 | 98 |
| 759 | 79 |
| 760 | 93 |
| 761 | 104 |
| 764 | 124 |
| 765 | 101 |
| 766 | 88 |
| 767 | 83 |
| 768 | 79 |
| 769 | 55 |
| 770 | 105 |
| 771 | 80 |
| 772 | 69 |
| 773 | 86 |
| 774 | 80 |
| 775 | 70 |
| 776 | 79 |
| 777 | 71 |
| 778 | 57 |
| 779 | 53 |
| 780 | 48 |
| 781 | 30 |
| 782 | 14 |
| 783 | 50 |
| 784 | 84 |
| 785 | 92 |
| 786 | 57 |
| 787 | 81 |
| 788 | 142 |
| 789 | 157 |
| 790 | 88 |
| 791 | 6.1 |
| 792 | 110 |
| 793 | 124 |
| 794 | 76 |
| 795 | 97 |
| 796 | 64 |
| 797 | 88 |
| 798 | 101 |
| 799 | 7.1 |
| 800 | 77 |
| 801 | 103 |
| 802 | 100 |
| 803 | 103 |
| 804 | 78 |
| 812 | 105 |
| 817 | 111 |
| 818 | 79 |
| 820 | 98 |
| 821 | 82 |
| 822 | 99 |
| 823 | 103 |
| 824 | 140 |
| 825 | 114 |
| 826 | 90 |
| 827 | 78 |
| 828 | 92 |
| 829 | 79 |
| 830 | 73 |
| 831 | 4.7 |
| 832 | 84 |
| 833 | 34 |
| 834 | 76 |
| 835 | 50 |
| 836 | 56 |
| 837 | 66 |
| 838 | 75 |
| 839 | 57 |
| 840 | 98 |
| 841 | 45 |
| 842 | 81 |
| 843 | 77 |
| 844 | 86 |
| 845 | 68 |
| 846 | 47 |
| 847 | 71 |
| 848 | 77 |
| 849 | 124 |
| 850 | 82 |
| 851 | 83 |
| 852 | 58 |
| 853 | 63 |
| 854 | 80 |
| 855 | 82 |
| 856 | 81 |
| 857 | 89 |
| 858 | 100 |
| 859 | 26 |
| 860 | 50 |
| 861 | 36 |
| 862 | 55 |
| 863 | 67 |
| 864 | 100 |
| 865 | 8.9 |
| 866 | 47 |
| 867 | 71 |
| 868 | 77 |
| 869 | 65 |
| 870 | 63 |
| 872 | 109 |
| 873 | 77 |
| 874 | 61 |
| 875 | 65 |
| 876 | 22 |
| 877 | 35 |
| 878 | 25 |
| 879 | 70 |
| 880 | 68 |
| 881 | 48 |
| 882 | 70 |
| 883 | 56 |
| 884 | 59 |
| 885 | 58 |
| 886 | 68 |
| 887 | 58 |
| 888 | 86 |
| 889 | 26 |
| 890 | 61 |
| 891 | 8.6 |
| 892 | 51 |
| 893 | 14 |
| 894 | 85 |
| 895 | 90 |
| 896 | 83 |
| 897 | 85 |
| 898 | 4.3 |
| 899 | 12 |
| 900 | 90 |
| 901 | 1.9 |
| 902 | 67 |
| 903 | 56 |
| 904 | 69 |
| 905 | 75 |
| 906 | 78 |
| 907 | 85 |
| 908 | 74 |

TABLE 195-continued

| Compound | cAMP production activity (%) |
|---|---|
| 909 | 78 |
| 910 | 64 |
| 911 | 71 |
| 912 | 98 |
| 913 | 81 |
| 914 | 68 |
| 915 | 61 |
| 916 | 59 |
| 917 | 69 |
| 918 | 63 |
| 919 | 68 |
| 920 | 70 |
| 921 | 59 |
| 922 | 84 |
| 923 | 84 |
| 924 | 76 |
| 925 | 69 |
| 926 | 102 |
| 927 | 80 |
| 928 | 51 |
| 929 | 76 |
| 930 | 92 |
| 931 | 72 |
| 932 | 66 |
| 933 | 60 |
| 934 | 87 |
| 935 | 112 |
| 936 | 98 |
| 937 | 120 |
| 938 | 97 |
| 939 | 111 |
| 940 | 86 |
| 941 | 21 |
| 942 | 31 |
| 943 | 74 |
| 944 | 71 |
| 945 | 77 |
| 946 | 102 |
| 947 | 89 |
| 948 | 68 |
| 949 | 92 |
| 950 | 59 |
| 951 | 93 |
| 952 | 95 |
| 953 | 77 |
| 954 | 81 |
| 955 | 79 |
| 956 | 87 |
| 957 | 17 |
| 958 | 49 |
| 959 | 77 |
| 960 | 84 |
| 961 | 92 |
| 962 | 86 |
| 963 | 16 |
| 964 | 119 |
| 965 | 115 |
| 966 | 82 |
| 967 | 44 |
| 968 | 69 |
| 969 | 45 |
| 970 | 112 |
| 971 | 83 |
| 972 | 89 |
| 973 | 112 |
| 974 | 111 |
| 975 | 74 |
| 976 | 73 |
| 977 | 80 |
| 978 | 91 |
| 979 | 145 |
| 980 | 85 |
| 981 | 106 |
| 982 | 96 |
| 983 | 91 |
| 984 | 133 |
| 985 | 120 |

TABLE 195-continued

| Compound | cAMP production activity (%) |
|---|---|
| 986 | 96 |
| 987 | 54 |
| 988 | 50 |
| 989 | 86 |
| 990 | 87 |
| 991 | 64 |
| 992 | 65 |
| 993 | 64 |
| 994 | 87 |
| 995 | 98 |
| 996 | 85 |
| 997 | 74 |
| 998 | 92 |
| 999 | 61 |
| 1000 | 86 |
| 1001 | 64 |
| 1002 | 50 |
| 1003 | 67 |
| 1006 | 52 |
| 1007 | 20 |
| 1008 | 73 |
| 1009 | 70 |
| 1010 | 96 |
| 1011 | 17 |
| 1012 | 87 |
| 1013 | 48 |
| 1014 | 84 |
| 1015 | 83 |
| 1016 | 92 |
| 1017 | 101 |
| 1018 | 109 |
| 1019 | 72 |
| 1020 | 81 |
| 1021 | 137 |
| 1022 | 105 |
| 1023 | 92 |
| 1024 | 66 |
| 1025 | 114 |
| 1026 | 68 |
| 1027 | 82 |
| 1028 | 75 |
| 1029 | 104 |
| 1030 | 115 |
| 1031 | 111 |
| 1032 | 88 |
| 1033 | 22 |
| 1034 | 54 |
| 1035 | 77 |
| 1036 | 82 |
| 1037 | 87 |
| 1038 | 111 |
| 1039 | 103 |
| 1040 | 111 |
| 1041 | 38 |
| 1042 | 102 |
| 1043 | 99 |
| 1044 | 86 |
| 1045 | 106 |
| 1046 | 101 |
| 1047 | 82 |
| 1048 | 96 |
| 1050 | 92 |
| 1051 | 85 |
| 1052 | 62 |
| 1053 | 70 |
| 1054 | 80 |
| 1055 | 84 |
| 1056 | 94 |
| 1057 | 100 |
| 1058 | 133 |
| 1059 | 116 |
| 1060 | 58 |
| 1061 | 55 |
| 1062 | 65 |
| 1063 | 72 |
| 1064 | 73 |
| 1065 | 83 |

TABLE 195-continued

| Compound | cAMP production activity (%) |
|---|---|
| 1066 | 83 |
| 1067 | 69 |
| 1068 | 68 |
| 1069 | 79 |
| 1070 | 69 |
| 1071 | 60 |
| 1072 | 54 |
| 1073 | 66 |
| 1074 | 66 |
| 1075 | 69 |
| 1076 | 88 |
| 1077 | 74 |
| 1078 | 74 |
| 1079 | 91 |
| 1080 | 81 |
| 1081 | 53 |
| 1082 | 22 |
| 1083 | 113 |
| 1084 | 13 |
| 1085 | 100 |
| 1086 | 151 |
| 1087 | 97 |
| 1088 | 95 |
| 1089 | 99 |
| 1090 | 118 |
| 1091 | 118 |
| 1092 | 89 |
| 1093 | 100 |
| 1094 | 100 |
| 1095 | 105 |
| 1096 | 93 |
| 1097 | 90 |
| 1098 | 88 |
| 1099 | 91 |
| 1100 | 76 |
| 1101 | 110 |
| 1102 | 10 |
| 1103 | 5.4 |
| 1104 | 16 |
| 1106 | 58 |
| 1107 | 24 |
| 1108 | 99 |
| 1109 | 29 |
| 1110 | 92 |
| 1111 | 79 |
| 1112 | 76 |
| 1113 | 99 |
| 1114 | 95 |
| 1115 | 140 |
| 1116 | 106 |
| 1117 | 88 |
| 1118 | 79 |
| 1119 | 136 |
| 1120 | 124 |
| 1121 | 118 |
| 1122 | 150 |
| 1123 | 122 |
| 1124 | 119 |
| 1125 | 93 |
| 1126 | 106 |
| 1127 | 91 |
| 1128 | 119 |
| 1129 | 102 |
| 1130 | 100 |
| 1131 | 96 |
| 1132 | 80 |
| 1133 | 113 |
| 1134 | 50 |
| 1135 | 84 |
| 1136 | 112 |
| 1137 | 82 |
| 1138 | 77 |
| 1139 | 86 |
| 1140 | 55 |
| 1141 | 83 |
| 1142 | 68 |
| 1143 | 78 |
| 1144 | 124 |
| 1145 | 102 |
| 1146 | 107 |
| 1147 | 112 |
| 1148 | 100 |
| 1149 | 98 |
| 1150 | 107 |
| 1151 | 105 |
| 1152 | 0.8 |
| 1153 | 106 |
| 1154 | 115 |
| 1155 | 83 |
| 1156 | 77 |
| 1157 | 44 |
| 1158 | 103 |
| 1159 | 87 |
| 1160 | 84 |
| 1161 | 84 |
| 1162 | 112 |
| 1163 | 101 |
| 1164 | 4.7 |
| 1165 | 4.3 |
| 1166 | 144 |
| 1167 | 115 |
| 1168 | 27 |
| 1169 | 50 |
| 1170 | 24 |
| 1171 | 28 |
| 1172 | 73 |
| 1173 | 85 |
| 1174 | 91 |
| 1175 | 81 |
| 1176 | 82 |
| 1178 | 84 |
| 1179 | 65 |
| 1180 | 73 |
| 1181 | 98 |
| 1182 | 109 |
| 1183 | 90 |
| 1184 | 108 |
| 1185 | 102 |
| 1186 | 110 |
| 1187 | 75 |
| 1188 | 99 |
| 1189 | 104 |
| 1190 | 108 |
| 1191 | 66 |
| 1192 | 100 |
| 1193 | 86 |
| 1194 | 62 |
| 1195 | 82 |
| 1196 | 76 |
| 1197 | 74 |
| 1198 | 88 |
| 1199 | 77 |
| 1200 | 73 |
| 1201 | 77 |
| 1202 | 91 |
| 1203 | 90 |
| 1204 | 83 |
| 1205 | 83 |
| 1206 | 88 |
| 1207 | 112 |
| 1208 | 65 |
| 1209 | 94 |
| 1210 | 86 |
| 1211 | 99 |
| 1212 | 96 |
| 1213 | 80 |
| 1214 | 79 |
| 1215 | 74 |
| 1216 | 61 |
| 1217 | 68 |
| 1218 | 90 |
| 1219 | 67 |
| 1220 | 80 |
| 1221 | 75 |

TABLE 195-continued

| Compound | cAMP production activity (%) |
|---|---|
| 1222 | 77 |
| 1223 | 54 |
| 1224 | 88 |
| 1225 | 90 |
| 1226 | 51 |
| 1227 | 77 |
| 1228 | 68 |
| 1229 | 56 |
| 1230 | 64 |
| 1231 | 88 |
| 1232 | 106 |
| 1233 | 78 |
| 1234 | 114 |
| 1235 | 98 |
| 1236 | 99 |
| 1237 | 96 |
| 1238 | 73 |
| 1239 | 91 |
| 1240 | 95 |
| 1241 | 101 |
| 1242 | 106 |
| 1243 | 77 |
| 1244 | 96 |
| 1245 | 115 |
| 1246 | 85 |
| 1247 | 70 |
| 1248 | 81 |
| 1249 | 62 |
| 1250 | 67 |
| 1251 | 56 |
| 1252 | 72 |
| 1253 | 81 |
| 1254 | 87 |
| 1255 | 66 |
| 1256 | 72 |
| 1257 | 98 |
| 1258 | 116 |
| 1259 | 101 |
| 1260 | 81 |
| 1261 | 99 |
| 1262 | 90 |
| 1263 | 73 |
| 1264 | 77 |
| 1265 | 89 |
| 1266 | 96 |
| 1267 | 74 |
| 1268 | 33 |
| 1269 | 92 |
| 1270 | 61 |
| 1271 | 92 |
| 1272 | 71 |
| 1273 | 81 |
| 1274 | 81 |
| 1275 | 89 |
| 1276 | 140 |
| 1277 | 95 |
| 1278 | 95 |
| 1279 | 113 |
| 1280 | 74 |
| 1281 | 95 |
| 1282 | 63 |
| 1283 | 18 |
| 1284 | 2.5 |
| 1285 | 67 |
| 1286 | 35 |
| 1287 | 64 |
| 1288 | 54 |
| 1289 | 17 |
| 1290 | 6.3 |
| 1291 | 48 |
| 1292 | 14 |
| 1293 | 84 |
| 1294 | 76 |
| 1295 | 73 |
| 1296 | 64 |
| 1297 | 98 |
| 1298 | 117 |
| 1299 | 87 |
| 1300 | 81 |
| 1301 | 49 |
| 1302 | 95 |
| 1303 | 102 |
| 1304 | 107 |
| 1305 | 138 |
| 1306 | 159 |
| 1307 | 116 |
| 1308 | 102 |
| 1309 | 109 |
| 1310 | 104 |
| 1311 | 79 |
| 1312 | 105 |
| 1313 | 87 |
| 1314 | 78 |
| 1315 | 76 |
| 1316 | 2.9 |
| 1317 | 3.4 |
| 1318 | 19 |
| 1319 | 5.8 |
| 1320 | 10 |
| 1321 | 63 |
| 1322 | 80 |
| 1323 | 78 |
| 1324 | 1.0 |
| 1325 | 113 |
| 1326 | 84 |
| 1327 | 92 |
| 1328 | 93 |
| 1329 | 85 |
| 1330 | 9.2 |
| 1331 | 96 |
| 1332 | 119 |
| 1333 | 109 |
| 1334 | 116 |
| 1335 | 97 |
| 1336 | 133 |
| 1337 | 44 |
| 1338 | 84 |
| 1339 | 86 |
| 1340 | 84 |
| 1341 | 83 |
| 1342 | 114 |
| 1343 | 98 |
| 1344 | 94 |
| 1345 | 107 |
| 1346 | 113 |
| 1347 | 87 |
| 1348 | 95 |
| 1349 | 98 |
| 1350 | 22 |
| 1351 | 100 |
| 1352 | 78 |
| 1353 | 111 |
| 1354 | 128 |
| 1355 | 118 |
| 1356 | 14 |
| 1357 | 13 |
| 1358 | 153 |
| 1359 | 165 |
| 1360 | 121 |
| 1361 | 104 |
| 1362 | 48 |
| 1363 | 80 |
| 1364 | 84 |
| 1365 | 108 |
| 1366 | 103 |
| 1367 | 58 |
| 1368 | 83 |
| 1369 | 30 |
| 1370 | 64 |
| 1371 | 84 |
| 1372 | 36 |
| 1373 | 44 |
| 1374 | 33 |
| 1375 | 23 |

TABLE 195-continued

| Compound | cAMP production activity (%) |
|---|---|
| 1376 | 42 |
| 1377 | 35 |
| 1378 | 116 |
| 1379 | 86 |
| 1380 | 109 |
| 1381 | 102 |
| 1382 | 93 |
| 1383 | 96 |
| 1384 | 78 |
| 1385 | 92 |
| 1386 | 92 |
| 1387 | 68 |
| 1388 | 59 |
| 1389 | 67 |
| 1390 | 69 |
| 1391 | 116 |
| 1392 | 89 |
| 1393 | 84 |
| 1394 | 82 |
| 1395 | 68 |
| 1396 | 133 |
| 1397 | 24 |
| 1398 | 77 |
| 1399 | 20 |
| 1400 | 49 |
| 1401 | 73 |
| 1402 | 69 |
| 1403 | 66 |
| 1404 | 64 |
| 1405 | 51 |
| 1406 | 7.3 |
| 1407 | 6.6 |
| 1408 | 5.1 |
| 1409 | 13 |
| 1410 | 51 |
| 1411 | 38 |
| 1412 | 7.2 |
| 1413 | 57 |
| 1414 | 47 |
| 1415 | 49 |
| 1416 | 48 |
| 1417 | 49 |
| 1418 | 36 |
| 1419 | 70 |
| 1420 | 20 |
| 1421 | 49 |
| 1422 | 15 |
| 1423 | 17 |
| 1424 | 29 |
| 1425 | 32 |
| 1426 | 5.4 |
| 1427 | 72 |
| 1428 | 67 |
| 1429 | 8.9 |
| 1430 | 13 |
| 1431 | 15 |
| 1432 | 18 |
| 1433 | 38 |
| 1434 | 54 |
| 1435 | 19 |
| 1436 | 54 |
| 1437 | 57 |
| 1438 | 40 |
| 1439 | 18 |
| 1440 | 10 |
| 1441 | 5.0 |
| 1442 | 9.3 |
| 1443 | 61 |
| 1444 | 12 |
| 1445 | 62 |
| 1446 | 88 |
| 1447 | 15 |
| 1448 | 9.4 |
| 1449 | 18 |

INDUSTRIAL APPLICABILITY

The present invention provides a compound having a PTH-like effect. The present invention also provides a medicine for the prevention and/or treatment of osteoporosis, fracture, osteomalacia, arthritis, thrombocytopenia, hypoparathyroidism, hyperphosphatemia, tumoral calcinosis or the like, or stem cell mobilization.

The invention claimed is:
1. A compound represented by the following general formula (1):

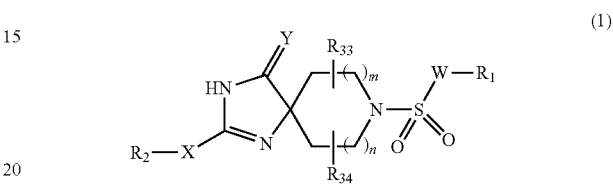

(1)

wherein:
W is selected from:
1) C1-C6 alkylene optionally substituted with a fluorine atom,
2) C2-C6 alkenylene, and
3) thiophene,
X is a single bond,
Y is an oxygen atom,
m is 1;
n is 1;
$R_1$ is represented by formula (3) or formula (4):

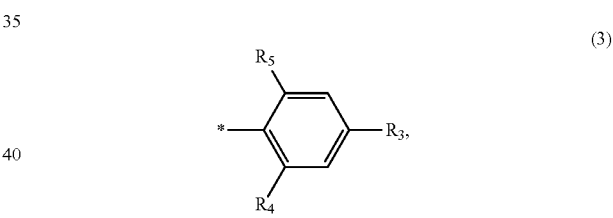

(3)

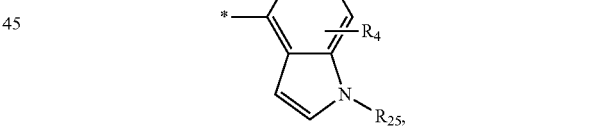

(4)

$R_3$ is selected from:
1) —$CONR_7R_8$,
2) —$OR_9$,
3) —$NR_9R_{10}$,
4) —$N(R_9)COR_{11}$,
5) —$N(R_9)SO_2R_{12}$,
6) —$SO_2R_{15}$,
7) C1-C2 alkyl optionally substituted with a group(s) independently selected from —$COR_{16}$ and —$NR_{13}R_{14}$,
$R_4$ is selected from:
1) a halogen atom,
2) cyano,
3) C1-C10 alkyl optionally substituted with a group(s) independently selected from hydroxycarbonyl, C1-C10 alkoxycarbonyl and aminocarbonyl,
4) C1-C10 haloalkyl,
5) C1-C10 alkoxy, $R_5$ is selected from a hydrogen atom, a halogen atom, C1-C10 alkyl, C1-C10 haloalkyl and C1-C10 alkoxy;

$R_7$ is selected from:
1) hydrogen,
2) C1-C10 alkyl optionally substituted with a group(s) independently selected from amino and C1-C10 alkylamino,
3) C1-C10 hydroxyalkyl,
4) C1-C10 haloalkyl,
5) C1-C10 heteroalkyl,
6) C1-C10 heteroalkyl optionally substituted with a group(s) selected from a hydroxyl group, C1-C10 alkylamino and C2-C10 alkenyl,
7) aryl,
8) heteroaryl,
9) aryl C1-C10 alkyl,
10) a heterocycle optionally substituted with C1-C10 alkyl,
11) —(CH$_2$)$_L$COR$_{16}$ (wherein L represents an integer of 1 to 4),
12) C1-C10 alkoxy,
13) C2-C10 alkenyl and
14) —NR$_{40}$R$_{41}$;

$R_{40}$ and $R_{41}$ are independently selected from hydrogen, C1-C10 alkyl and C1-C10 alkylcarbonyl, or $R_{40}$ and $R_{41}$ may be bonded to each other to form a ring selected from azetidinyl, pyrrolidinyl, piperidinyl, piperazinyl and morpholinyl, and the heterocycle is optionally substituted with C1-C10 alkyl;

$R_8$ is selected from hydrogen and C1-C10 alkyl optionally substituted with a halogen atom(s) and/or a hydroxyl group(s);

$R_7$ and $R_8$ may be bonded to form a 4- to 7-membered heterocycle optionally containing an additional element(s) or group(s) independently selected from O, N, S, SO and SO$_2$, and the heterocycle optionally contains carbonyl, and the heterocycle is optionally substituted with a substituent(s) independently selected from:
1) a halogen atom,
2) C1-C10 alkyl optionally having C1-C10 alkylamino as a substituent(s),
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) selected from a halogen atom, a hydroxyl group, amino and C1-C10 alkylamino,
8) C1-C10 heteroalkyl optionally substituted with a group(s) independently selected from a halogen atom, a hydroxyl group, amino and C1-C10 alkylamino,
9) a heterocycle optionally substituted with C1-C10 alkyl,
10) heteroaryl optionally substituted with C1-C10 alkyl,
11) heterocyclyl C1-C10 alkyl,
12) —COR$_{16}$,
13) —NR$_{19}$R$_{20}$,
14) —SO$_2$R$_{21}$,
15) C1-C10 alkoxy-C1-C10 alkyl optionally having a hydroxyl group(s) as a substituent(s) and
16) C1-C10 hydroxyalkyloxy, wherein the hydrogen atom of the hydroxyl group is optionally replaced by C1-C10 hydroxyalkyl, and the heterocycle may further form a spiro ring together with a 4- to 6-membered heterocycle, and the bonded 4- to 6-membered heterocycle optionally contains O and N as ring-forming elements in addition to carbon atoms, and the carbon atom(s) may be oxidized to form carbonyl, and the 4- to 6-membered heterocycle is optionally further substituted with C1-C10 alkyl;

$R_{16}$ is selected from:
1) a hydroxyl group,
2) C1-C10 alkoxy,
3) NR$_{17}$R$_{18}$ and
4) C1-C10 alkyl optionally substituted with a substituent(s) selected from a halogen atom, a hydroxyl group, C1-C10 alkoxycarbonyl or C1-C10 alkylamino;

$R_{17}$ is selected from:
1) hydrogen,
2) C1-C10 alkyl optionally substituted with a group(s) selected from aryl, amino, C1-C10 alkylamino, C1-C10 alkylcarbonylamino and a hydroxyl group,
3) heteroaryl and
4) C1-C10 alkoxy;

$R_{18}$ is selected from hydrogen, C1-C10 alkyl and C1-C10 hydroxyalkyl;

$R_{17}$ and $R_{18}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl;

$R_{19}$ is selected from hydrogen, C1-C10 alkyl, C1-C10 haloalkyl, C1-C10 alkylcarbonyl, C1-C10 hydroxyalkyl, C1-C10 aminoalkyl, C1-C10 alkoxycarbonyl and C1-C10 heteroalkyl;

$R_{20}$ is selected from hydrogen and C1-C10 alkyl;

$R_{19}$ and $R_{20}$ may be bonded to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{21}$ is selected from:
1) C1-C10 alkyl optionally substituted with aryl,
2) amino,
3) C1-C10 alkylamino and
4) aryl optionally substituted with C1-C10 alkyl;

$R_9$ is selected from:
1) hydrogen,
2) C1-C10 alkyl optionally substituted with a group(s) independently selected from $R_{23}$,
3) cycloalkyl optionally substituted with a halogen atom(s) or a hydroxyl group(s),
4) a heterocycle optionally substituted with a group(s) independently selected from C1-C10 alkyl, C1-C10 alkylcarbonyl, C1-C10 alkoxy, C1-C10 alkoxycarbonyl, amino and a halogen atom,
5) C1-C10 heteroalkyl optionally substituted with a group(s) independently selected from a halogen atom and a hydroxyl group,
6) heteroaryl optionally substituted with a group(s) selected from C1-C10 alkyl, C1-C10 alkylcarbonyl, C1-C10 alkoxycarbonyl and a halogen atom and
7) cycloalkenyl optionally substituted with a group(s) selected from C1-C10 alkoxy, C1-C10 alkylamino, amino, a hydroxyl group and a halogen atom, wherein the cycloalkenyl optionally contains a carbonyl group;

$R_{23}$ is independently selected from:
1) a halogen atom,
2) a hydroxyl group,
3) a C1-C10 alkylcarbonyloxy group,
4) —COR$_{16}$,
5) amino, 6) C1-C10 alkylamino,
7) a heterocycle optionally substituted with a group(s) selected from C1-C10 alkyl, C1-C10 alkylcarbonyl, C1-C10 alkoxycarbonyl and a halogen atom and
8) cyano;

$R_{10}$ is selected from:
1) hydrogen and
2) C1-C10 alkyl optionally substituted with a group(s) selected from a halogen atom, a hydroxyl group and aryl;

$R_9$ and $R_{10}$ may be bonded to form a 4- to 7-membered heterocycle optionally containing an additional element(s) or group(s) independently selected from N, O, S, SO, $SO_2$, carbonyl and thiocarbonyl, and the heterocycle is optionally substituted with a substituent(s) independently selected from $R_{24}$;

$R_{24}$ is independently selected from:
1) a halogen atom,
2) C1-C10 alkyl optionally substituted with a group(s) independently selected from C1-C10 alkylamino and C1-C10 alkylcarbonylamino,
3) C1-C10 haloalkyl,
4) a hydroxyl group,
5) C1-C10 hydroxyalkyl,
6) C1-C10 alkoxy optionally substituted with a group(s) independently selected from a halogen atom, a hydroxyl group, amino and C1-C10 alkylamino,
7) aryl optionally substituted with a group(s) independently selected from a halogen atom, a hydroxyl group, amino and C1-C10 alkylamino,
8) C1-C10 heteroalkyl optionally substituted with 1 to 2 groups independently selected from a halogen atom, a hydroxyl group, amino and C1-C10 alkylamino,
9) —$COR_{16}$, and
10) —$NR_{19}R_{20}$;

$R_{11}$ is selected from:
1) C1-C10 alkyl optionally substituted with 1 to 3 substituents independently selected from:
   i) a hydroxyl group,
   ii) —$NR_{17}R_{18}$,
   iii) a C1-C10 alkoxy group,
   iv) a halogen atom,
   v) C1-C10 alkoxycarbonyl, and
   vi) aminocarbonyl,
2) aryl or aryl C1-C10 alkyl,
3) cycloalkyl optionally substituted with a halogen atom(s),
4) a heterocycle optionally substituted with a group(s) selected from C1-C10 alkyl,
5) C1-C10 alkoxy, wherein the alkyl group is optionally substituted with a group(s) independently selected from C1-C10 alkylcarbonylamino, amino, C1-C10 alkylamino and a hydroxyl group,
6) amino,
7) C1-C10 alkylamino, wherein the alkyl group is optionally substituted with a group(s) independently selected from C1-C10 alkylcarbonylamino, amino, C1-C10 alkylamino, hydroxycarbonyl and a hydroxyl group and
8) C2-C10 alkenyl;

$R_{12}$ is selected from:
1) C1-C10 alkyl,
2) amino and
3) C1-C10 alkylamino, wherein the alkyl group is optionally substituted with a group(s) independently selected from amino, C1-C10 alkylamino and a hydroxyl group;

$R_{13}$ is selected from:
1) hydrogen,
2) C1-C10 alkyl,
3) C1-C10 alkylcarbonyl, wherein the alkyl is optionally substituted with a hydroxyl group(s),
4) C1-C10 alkoxycarbonyl,
5) aminocarbonyl,
6) C1-C10 alkylaminocarbonyl and
7) heterocyclic carbonyl optionally substituted with C1-C10 alkyl;

$R_{14}$ is selected from:
1) hydrogen and
2) C1-C10 alkyl optionally substituted with a group(s) independently selected from a halogen atom, a hydroxyl group, amino and C1-C10 alkylamino;

$R_{13}$ and $R_{14}$ may be bonded to form a 4- to 7-membered heterocycle optionally containing an additional element(s) or group(s) independently selected from O, N, S, SO and $SO_2$, and the heterocycle optionally contains carbonyl, and the heterocycle is optionally substituted with C1-C10 alkyl;

$R_{15}$ is selected from:
1) C1-C10 alkyl and
2) —$NR_{35}R_{36}$;

$R_{35}$ is selected from:
1) hydrogen,
2) C1-C10 alkyl optionally substituted with a group(s) independently selected from:
   i) a halogen atom,
   ii) a hydroxyl group,
   iii) C1-C10 alkylcarbonylamino,
   iv) —$COR_{16}$,
   v) amino,
   vi) C1-C10 alkylamino,
   vii) C1-C10 alkoxy optionally substituted with a halogen atom(s),
   viii) heteroaryl optionally substituted with a C1-C10 alkyl group(s) and
   ix) a heterocycle,
3) aryl optionally substituted with a group(s) independently selected from a halogen atom, a hydroxyl group, amino and C1-C10 alkylamino,
4) cycloalkyl optionally substituted with a group(s) independently selected from a halogen atom and a hydroxyl group,
5) a heterocycle optionally substituted with a group(s) independently selected from C1-C10 alkyl, a halogen atom and aryl C1-C10 alkyl,
6) heteroaryl optionally substituted with C1-C10 alkyl and
7) C1-C10 alkylcarbonyl;

$R_{36}$ is selected from:
1) hydrogen and
2) C1-C10 alkyl optionally substituted with a group(s) independently selected from a halogen atom, a hydroxyl group and aryl;

$R_{35}$ and $R_{36}$ may be bonded to each other to form a ring selected from azetidinyl, pyrrolidinyl, piperidinyl, piperazinyl and morpholinyl, and the ring is optionally substituted with a group(s) selected independently of each other from C1-C10 alkyl and a halogen atom;

$R_{25}$ is selected from:
1) C1-C10 heteroalkyl optionally substituted with a hydroxyl group(s), and
2) C1-C10 alkyl optionally substituted with a hydroxyl group(s), R₂ is selected from:
1) C1-C10 alkyl optionally substituted with a halogen atom(s), wherein the alkyl group is optionally further substituted with a substituent(s) independently selected from R₄₂,
2) cycloalkyl substituted with a group(s) independently selected from:
   i) a halogen atom,
   ii) C2-C10 alkenyl or C1-C10 alkyl,
   iii) aryl optionally substituted with a group(s) independently selected from C1-C10 alkyl, a halogen atom and C1-C10 alkoxy,
   iv) cycloalkyl,
   v) C2-C10 haloalkenyl or C1-C10 haloalkyl,
   vi) C1-C10 alkylidene, wherein the alkylidene is bonded to the cycloalkyl by a double bond and the alkylidene is optionally substituted with a halogen atom(s),
   vii) C1-C10 alkoxy optionally substituted with a halogen atom(s),
   viii) C1-C10 alkyl substituted with C1-C10 alkoxy, wherein the alkyl and/or the alkyl in the alkoxy is optionally substituted with a halogen atom(s), and
   x) —Si(CH₃)₃,
3) cyclohexyl, and
4) aryl optionally substituted with a group(s) independently selected from R₄₄,
with the proviso that when W is 1) C1-C6 alkylene optionally substituted with a fluorine atom, or 2) C2-C6 alkenylene, R₂ is not 3) cyclohexyl, or 4) aryl optionally substituted with a group(s) independently selected from R₄₄,
R₄₄ is selected from:
1) a halogen atom,
2) cyano,
3) C1-C10 alkyl optionally substituted with a group(s) independently selected from:
   i) a hydroxyl group,
   ii) —OR₂₆,
   iii) cyano,
   iv) aryloxy optionally substituted with a group(s) independently selected from a halogen atom, C1-C10 alkyl optionally substituted with a halogen atom(s) or C1-C10 alkoxy optionally substituted with a halogen atom(s),
4) C1-C10 haloalkyl,
5) cycloalkyl optionally substituted with a group(s) independently selected from a halogen atom and C1-C10 haloalkyl,
6) C1-C10 alkoxy optionally substituted with a halogen atom(s) or a C2-C6 alkenyl group(s),
7) —COR₃₀,
8) C1-C10 heteroalkyl optionally substituted with a halogen atom(s),
9) aryl optionally substituted with a substituent(s) independently selected from:
   i) C1-C10 alkyl,
   ii) aryl,
10) heteroaryl optionally substituted with a C1-C10 alkyl group(s),
11) —SO₂R₄₃,
12) C1-C10 alkylthio optionally substituted with a halogen atom(s),
13) —Si(R₄₃)₃ and
14) —SF₅;

R₄₂ is selected from:
1) hydrogen,
2) aryl optionally substituted with a group(s) independently selected from C1-C10 alkyl optionally substituted with halogen, a halogen atom and C1-C10 alkoxy,
4) C1-C10 alkoxycarbonyl,
7) C1-C10 alkoxycarbonylamino,
9) a hydroxyl group and
10) oxetane, tetrahydrofuran or tetrahydropyran optionally substituted with C1-C10 alkyl;
11) C4-C7 cycloalkyl,
12) C1-C10 alkoxy;
R₄₃ represents a C1-C10 alkyl group;
R₂₆ is aryl, or C1-C10 alkyl optionally substituted with a halogen atom(s);
R₃₀ is selected from a hydroxyl group, C1-C10 alkoxy and —NR₃₁R₃₂;
R₃₁ and R₃₂ are independently selected from:
1) hydrogen,
2) C1-C10 alkyl optionally substituted with aryl and
3) aryl;
R₃₁ and R₃₂ may be bonded to form a ring selected from azetidinyl, pyrrolidinyl, piperidinyl, piperazinyl and morpholinyl, and the ring is optionally substituted with a group(s) selected independently of each other from C1-C10 alkyl, a halogen atom and C1-C10 alkoxycarbonyl; and
R₃₃ and R₃₄ are hydrogen, or a pharmacologically acceptable salt thereof.

2. The compound or a pharmacologically acceptable salt thereof according to claim 1, wherein
W is
1) C1-C6 alkylene optionally substituted with a fluorine atom, or
2) C2-C6 alkenylene,
R₂ is selected from:
C1-C10 alkyl optionally substituted with a halogen atom(s), wherein the alkyl group is optionally further substituted with a substituent(s) independently selected from R₄₂, and
R₄₂ is selected from:
1) hydrogen,
2) aryl optionally substituted with a group(s) independently selected from C1-C10 alkyl optionally substituted with halogen, a halogen atom and C1-C10 alkoxy,
4) C1-C10 alkoxycarbonyl,
7) C1-C10 alkoxycarbonylamino,
9) a hydroxyl group,
10) oxetane, tetrahydrofuran or tetrahydropyran optionally substituted with C1-C10 alkyl;
11) C4-C7 cycloalkyl, and
12) C1-C10 alkoxy.

3. The compound or a pharmacologically acceptable salt thereof according to claim 1, wherein
W is
1) C1-C6 alkylene optionally substituted with a fluorine atom, or
2) C2-C6 alkenylene,
R₂ is selected from:
cycloalkyl substituted with a group(s) independently selected from:
   i) a halogen atom,
   ii) C2-C10 alkenyl or C1-C10 alkyl,
   iii) aryl optionally substituted with a group(s) independently selected from C1-C10 alkyl, a halogen atom and C1-C10 alkoxy,
   iv) cycloalkyl, v) C2-C10 haloalkenyl or C1-C10 haloalkyl,
vi) C1-C10 alkylidene, wherein the alkylidene is bonded to the cycloalkyl by a double bond and the alkylidene is optionally substituted with a halogen atom(s),
vii) C1-C10 alkoxy optionally substituted with a halogen atom(s),
viii) C1-C10 alkyl substituted with C1-C10 alkoxy, wherein the alkyl and/or the alkyl in the alkoxy is optionally substituted with a halogen atom(s),
x) —Si(CH$_3$)$_3$.

4. The compound or a pharmacologically acceptable salt thereof according to claim 1, wherein
W is thiophene,
R$_2$ is selected from:
3) cyclohexyl, and
4) aryl optionally substituted with a group(s) independently selected from R$_{44}$.

5. A compound selected from the group consisting of:
(266) 8-{2-[3-(3,4-dihydroxy-butoxy)-2-methyl-phenyl]-ethanesulfonyl}-2-(3-trifluoromethoxy-phenyl)-1,3,8-triaza-spiro[4.5]dec-1-en-4-one;
(850) 8-{2-[1-((S)-2,3-dihydroxy-propyl)-1H-indol-5-yl]-ethanesulfonyl}-2-(3-trifluoromethoxy-phenyl)-1,3,8-triaza-spiro[4.5]dec-1-en-4-one;
(1024) 1-{3,5-dimethyl-4-[(E)-2-(2-non-4-ynyl-4-oxo-1,3,8-triaza-spiro[4.5]dec-1-ene-8-sulfonyl)-vinyl]-phenyl}-1-methyl-urea;
(1029) 1-(4-{2-[2-(2,2-difluoro-benzo[1,3]dioxol-5-yl)-4-oxo-1,3,8-triaza-spiro[4.5]dec-1-ene-8-sulfonyl]-ethyl}-3,5-dimethyl-phenyl)-1-methyl-urea;
(1039) 1-(3,5-dimethyl-4-{2-[4-oxo-2-(5,6,7,8-tetrahydro-naphthalen-2-yl)-1,3,8-triaza-spiro[4.5]dec-1-ene-8-sulfonyl]-ethyl}-phenyl)-1-methyl-urea;
(1058) 1-{3,5-dimethyl-4-[2-(4-oxo-2-spiro[2.5]oct-6-yl-1,3,8-triaza-spiro[4.5]dec-1-ene-8-sulfonyl)-ethyl]-phenyl}-1-methyl-urea;
(1081) 1-{3,5-dimethyl-4-[2-(2-non-4-ynyl-4-oxo-1,3,8-triaza-spiro[4.5]dec-1-ene-8-sulfonyl)-ethyl]-phenyl}-1-methyl-urea;
(1120) 1-(3,5-dimethyl-4-{(E)-2-[4-oxo-2-((E)-6-phenyl-hex-5-enyl)-1,3,8-triaza-spiro[4.5]dec-1-ene-8-sulfonyl]-vinyl}-phenyl)-1-methyl-urea;
(1121) 1-(3,5-dimethyl-4-{(E)-2-[4-oxo-2-((E)-9-phenyl-non-8-enyl)-1,3,8-triaza-spiro[4.5]dec-1-ene-8-sulfonyl]-vinyl}-phenyl)-1-methyl-urea;
(1127) 1-(3,5-dimethyl-4-{(E)-2-[4-oxo-2-(2-propyl-benzofuran-6-yl)-1,3,8-triaza-spiro[4.5]dec-1-ene-8-sulfonyl]-vinyl}-phenyl)-1-methyl-urea;
(1129) 1-(4-{(E)-2-[2-(4-[1,1,2,2,2-$^2$H$_5$]ethyl-cyclohex-3-enyl)-4-oxo-1,3,8-triaza-spiro[4.5]dec-1-ene-8-sulfonyl]-vinyl}-3,5-dimethyl-phenyl)-1-methyl-urea;
(1149) 1-(4-{2-[2-(4-[1,1,2,2,2-$^2$H$_5$]ethyl-cyclohex-3-enyl)-4-oxo-1,3,8-triaza-spiro[4.5]dec-1-ene-8-sulfonyl]-ethyl}-3,5-dimethyl-phenyl)-1-methyl-urea;
(1154) 1-(4-{2-[2-(6-ethylsulfanyl-hexyl)-4-oxo-1,3,8-triaza-spiro[4.5]dec-1-ene-8-sulfonyl]-ethyl}-3,5-dimethyl-phenyl)-1-methyl-urea;
(1163) 2-(2,2-difluoro-benzo[1,3]dioxol-5-yl)-8-{(E)-2-[4-(4-hydroxy-4-methyl-piperidine-1-carbonyl)-2,6-dimethyl-phenyl]-ethenesulfonyl}-1,3,8-triaza-spiro[4.5]dec-1-en-4-one;
(1212) 8-{(E)-2-[4-(4-hydroxy-4-methyl-piperidine-1-carbonyl)-2,6-dimethyl-phenyl]-ethenesulfonyl}-2-(2,2,3,3-tetrafluoro-2,3-dihydro-benzo[1,4]dioxin-6-yl)-1,3,8-triaza-spiro[4.5]dec-1-en-4-one;
(1281) 8-{2-[4-(4-fluoromethyl-4-hydroxy-piperidine-1-carbonyl)-2,6-dimethyl-phenyl]-ethanesulfonyl}-2-(2,2,3,3-tetrafluoro-2,3-dihydro-benzo[1,4]dioxin-6-yl)-1,3,8-triaza-spiro[4.5]dec-1-en-4-one;
(1330) 2-(2,2-difluoro-benzo[1,3]dioxol-5-yl)-8-{2-[4-((R)-2,3-dihydroxy-propoxy)-2,6-dimethyl-phenyl]-ethanesulfonyl}-1,3,8-triaza-spiro[4.5]dec-1-en-4-one;
(1333) 2-(2,2-difluoro-benzo[1,3]dioxol-5-yl)-8-{2-[4-(4-hydroxy-piperidine-1-carbonyl)-2,6-dimethyl-phenyl]-ethanesulfonyl}-1,3,8-triaza-spiro[4.5]dec-1-en-4-one;
(1336) 2-(2,2-difluoro-benzo[1,3]dioxol-5-yl)-8-{2-[4-(4-hydroxy-4-methyl-piperidine-1-carbonyl)-2,6-dimethyl-phenyl]-ethanesulfonyl}-1,3,8-triaza-spiro[4.5]dec-1-en-4-one;
(1355) 1-(3,5-dimethyl-4-{2-[4-oxo-2-(2-propyl-benzofuran-6-yl)-1,3,8-triaza-spiro[4.5]dec-1-ene-8-sulfonyl]-ethyl}-phenyl)-1-methyl-urea;
and a pharmacologically acceptable salt thereof.

6. A pharmaceutical composition comprising the compound or a pharmacologically acceptable salt thereof according to claim 1 as an active ingredient.

7. A pharmaceutical composition for activating intracellular cAMP response, comprising the compound or a pharmacologically acceptable salt thereof according to claim 1 as an active ingredient.

* * * * *